US012709615B2

(12) United States Patent
Park et al.

(10) Patent No.: US 12,709,615 B2

(45) Date of Patent: Aug. 18, 2026

(54) ORGANIC LIGHT EMITTING DEVICE

(71) Applicant: LG CHEM, LTD., Seoul (KR)

(72) Inventors: Seulchan Park, Daejeon (KR); Sang Duk Suh, Daejeon (KR); Min Woo Jung, Daejeon (KR); Jungha Lee, Daejeon (KR); Su Jin Han, Daejeon (KR); Sunghyun Hwang, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 954 days.

(21) Appl. No.: 17/918,002

(22) PCT Filed: Jul. 15, 2021

(86) PCT No.: PCT/KR2021/009129

§ 371 (c)(1),
(2) Date: Oct. 10, 2022

(87) PCT Pub. No.: WO2022/015084

PCT Pub. Date: Jan. 20, 2022

(65) Prior Publication Data

US 2023/0172065 A1 Jun. 1, 2023

(30) Foreign Application Priority Data

Jul. 15, 2020 (KR) ........................ 10-2020-0087740
Jul. 15, 2021 (KR) ........................ 10-2021-0092665

(51) Int. Cl.
*C07D 487/04* (2006.01)
*C07D 209/86* (2006.01)
(Continued)

(52) U.S. Cl.
CPC ......... *C07D 487/04* (2013.01); *C07D 209/86* (2013.01); *C07D 405/04* (2013.01);
(Continued)

(58) Field of Classification Search
CPC ............ H10K 2101/90; H10K 85/654; H10K 85/6572; H10K 85/6574; H10K 85/6576; H10K 50/11
See application file for complete search history.

(56) References Cited

U.S. PATENT DOCUMENTS

2004/0251816 A1 12/2004 Leo et al.
2013/0248849 A1 9/2013 Feldman et al.
(Continued)

FOREIGN PATENT DOCUMENTS

CN 110734446 1/2020
KR 10-2000-0051826 8/2000
(Continued)

*Primary Examiner* — Vu A Nguyen

(74) *Attorney, Agent, or Firm* — Bryan Cave Leighton Paisner LLP

(57) ABSTRACT

Provided is an organic light emitting device comprising: an anode, a cathode, a light emitting layer between the anode and the cathode, an electron inhibition layer between the anode and the light emitting layer, and a hole transport layer between the electron inhibition layer and the anode, wherein the light emitting layer comprises a compound of the following Chemical Formula 1, a compound of the following Chemical Formula 2, and a compound of the following Chemical Formula 3 as defined in the specification:

[Chemical Formula 1]

(Continued)

-continued

[Chemical Formula 2]

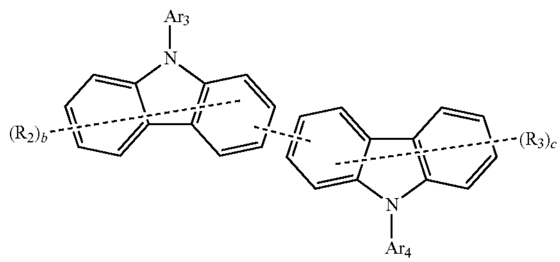

[Chemical Formula 3]

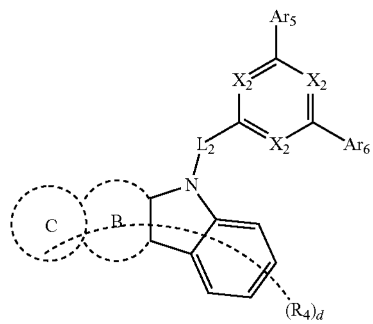

having improved driving voltage, efficiency, and lifetime.

15 Claims, 1 Drawing Sheet

(51) Int. Cl.

| | |
|---|---|
| ***C07D 405/04*** | (2006.01) |
| ***C07D 405/14*** | (2006.01) |
| ***C07D 409/14*** | (2006.01) |
| ***C09K 11/06*** | (2006.01) |
| ***H10K 50/11*** | (2023.01) |
| ***H10K 85/60*** | (2023.01) |
| ***H10K 101/00*** | (2023.01) |

(52) U.S. Cl.

CPC ......... *C07D 405/14* (2013.01); *C07D 409/14* (2013.01); *C09K 11/06* (2013.01); *H10K 85/654* (2023.02); *H10K 85/6572* (2023.02); *H10K 85/6574* (2023.02); *H10K 85/6576* (2023.02); *C07B 2200/05* (2013.01); *C09K 2211/1018* (2013.01); *H10K 50/11* (2023.02); *H10K 2101/90* (2023.02)

(56) References Cited

U.S. PATENT DOCUMENTS

| | | | | |
|---|---|---|---|---|
| 2017/0098778 | A1 | 4/2017 | Oh et al. | |
| 2019/0040314 | A1 | 2/2019 | Ito et al. | |
| 2019/0214571 | A1 | 7/2019 | Huh et al. | |
| 2020/0079735 | A1 | 3/2020 | Ma et al. | |
| 2020/0111969 | A1 * | 4/2020 | No ...................... | C07D 403/14 |
| 2020/0119285 | A1 | 4/2020 | No et al. | |
| 2020/0203631 | A1 | 6/2020 | Gao et al. | |
| 2020/0212312 | A1 | 7/2020 | Kang et al. | |
| 2020/0381629 | A1 | 12/2020 | No et al. | |
| 2023/0284526 | A1 | 9/2023 | Kai et al. | |

FOREIGN PATENT DOCUMENTS

| | | | |
|---|---|---|---|
| KR | 10-2017-0086211 | | 7/2017 |
| KR | 10-2018-0111558 | | 10/2018 |
| KR | 10-2019-0007789 | | 1/2019 |
| KR | 10-2019-0010693 | | 1/2019 |
| KR | 10-1959821 | | 3/2019 |
| KR | 20190089764 | | 7/2019 |
| KR | 10-2020-0030480 | | 3/2020 |
| KR | 10-2020-0072227 | | 6/2020 |
| KR | 10-2020-0082020 | | 7/2020 |
| WO | 2003-012890 | A2 | 2/2003 |
| WO | 2017170812 | | 10/2017 |
| WO | 2018-182259 | | 10/2018 |
| WO | 2020-122622 | | 6/2020 |
| WO | 2022004709 | | 1/2022 |

* cited by examiner

[FIG. 1]
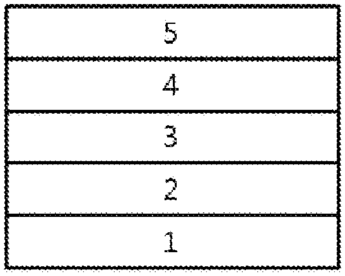
[FIG. 2]
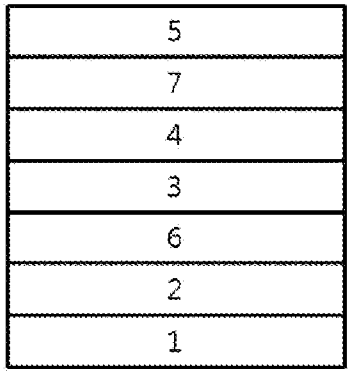

ORGANIC LIGHT EMITTING DEVICE

CROSS-REFERENCE TO RELATED APPLICATION(S)

This application is a National Stage Application of International Application No. PCT/KR2021/009129 filed on Jul. 15, 2021, which claims priority to and the benefit of Korean Patent Application No. 10-2020-0087740 filed on Jul. 15, 2020 and Korean Patent Application No. 10-2021-0092665 filed on Jul. 15, 2021 in the Korean Intellectual Property Office, the disclosures of which are incorporated herein by reference in their entirety.

TECHNICAL FIELD

The present disclosure relates to an organic light emitting device having improved driving voltage, efficiency and lifetime.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

In the organic light emitting devices as described above, there is a continuing need for the development of an organic light emitting device having improved driving voltage, efficiency and lifetime.

PRIOR ART LITERATURE

Patent Literature (Patent Literature 1) Korean Unexamined Patent Publication No. 10-2000-0051826

BRIEF DESCRIPTION

Technical Problem

The present disclosure relates to an organic light emitting device having improved driving voltage, efficiency and lifetime.

Technical Solution

The present disclosure provides the following organic light emitting device:

An organic light emitting device comprising:
- an anode,
- a cathode,
- a light emitting layer between the anode and the cathode,
- an electron inhibition layer between the anode and the light emitting layer, and
- a hole transport layer between the electron inhibition layer and the anode,
- wherein the light emitting layer comprises a compound of the following Chemical Formula 1, a compound of the following Chemical Formula 2, and a compound of the following Chemical Formula 3:

[Chemical Formula 1]

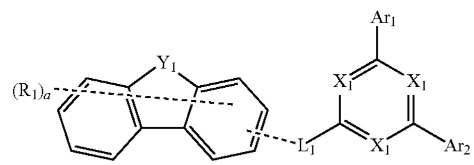

wherein in Chemical Formula 1:
- $Y_1$ is O or S;
- each $X_1$ is independently CH or N, provided that at least one of $X_1$ is N;
- $L_1$ is a direct bond, a substituted or unsubstituted $C_{6-60}$ arylene, or a substituted or unsubstituted $C_{2-60}$ heteroarylene containing any one or more selected from the group consisting of N, O and S;
- $Ar_1$ and $Ar_2$ are each independently a substituted or unsubstituted $C_{6-60}$ aryl, or a substituted or unsubstituted $C_{2-60}$ heteroaryl containing any one or more selected from the group consisting of N, O and S;
- $R_1$ is hydrogen, deuterium, a substituted or unsubstituted $C_{6-60}$ alkyl, a substituted or unsubstituted $C_{6-60}$ aryl, or a substituted or unsubstituted $C_{2-60}$ heteroaryl containing any one or more selected from the group consisting of N, O and S; and
- a is an integer of 1 to 7;

[Chemical Formula 2]

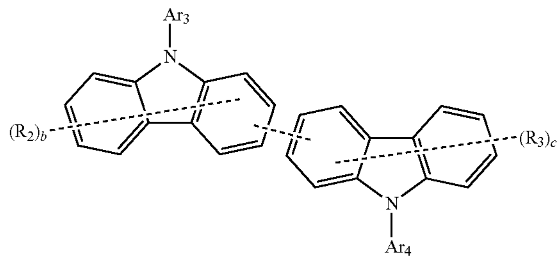

wherein in Chemical Formula 2:
- $Ar_3$ and $Ar_4$ are each independently a substituted or unsubstituted $C_{6-60}$ aryl, or a substituted or unsubstituted $C_{2-60}$ heteroaryl containing any one or more selected from the group consisting of N, O and S;
- $R_2$ and $R_3$ are each independently hydrogen, deuterium, a substituted or unsubstituted $C_{6-60}$ aryl, or a substituted or unsubstituted $C_{2-60}$ heteroaryl containing any one or more selected from the group consisting of N, O and S; and b and c are each independently an integer of 1 to 7;

[Chemical Formula 3]

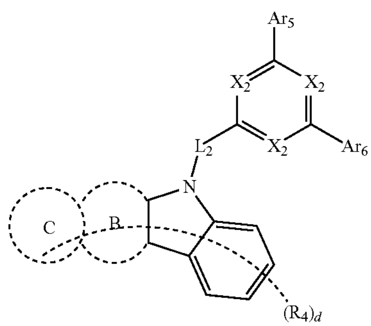

wherein in Chemical Formula 3:

B is a benzene ring fused with two adjacent pentagonal rings;

each $X_2$ is independently CH or N, provided that at least one of $X_2$ is N;

$L_2$ is a direct bond, a substituted or unsubstituted $C_{6-60}$ arylene, or a substituted or unsubstituted $C_{2-60}$ heteroarylene containing any one or more selected from the group consisting of N, O and S;

$Ar_5$ and $Ar_6$ are each independently a substituted or unsubstituted $C_{6-60}$ aryl, or a substituted or unsubstituted $C_{2-60}$ heteroaryl containing any one or more selected from the group consisting of N, O and S; and C is the following Chemical Formula 4-1 or 4-2:

[Chemical Formula 4-1]

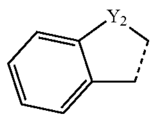

[Chemical Formula 4-2]

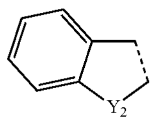

wherein in Chemical Formulas 4-1 and 4-2:

the dotted line is a bond that is fused with B;

$Y_2$ is CRR', $C(CH_3)_2$, O, S, or $NAr_7$;

wherein R and R' are each independently a substituted or unsubstituted $C_{6-60}$ alkyl, or a substituted or unsubstituted $C_{6-60}$ aryl;

$Ar_7$ is a substituted or unsubstituted $C_{6-60}$ aryl, or a substituted or unsubstituted $C_{2-60}$ heteroaryl containing any one or more selected from the group consisting of N, O and S;

$R_4$ is hydrogen, deuterium, a substituted or unsubstituted $C_{6-60}$ aryl, or a substituted or unsubstituted $C_{2-60}$ heteroaryl containing any one or more selected from the group consisting of N, O and S; and d is an integer of 1 to 10.

Advantageous Effects

The above-mentioned organic light emitting device has excellent driving voltage, efficiency and lifetime.

BRIEF DESCRIPTION OF THE DRAWINGS

FIG. 1 shows an example of an organic light emitting device comprising a substrate 1, an anode 2, an electron inhibition layer 3, a light emitting layer 4, and a cathode 5.

FIG. 2 shows an example of an organic light emitting device comprising a substrate 1, an anode 2, a hole transport layer 6, an electron inhibition layer 3, a light emitting layer 4, an electron transport layer 7, and a cathode 5.

DETAILED DESCRIPTION

Hereinafter, embodiments of the present disclosure will be described in more detail to assist in the understanding of the invention.

As used herein, the notation  or  means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heteroaryl containing at least one of N, O and S atoms, or being unsubstituted or substituted with a substituent to which two or more substituents of the above-exemplified substituents are connected. For example, "a substituent in which two or more substituents are connected" can be a biphenyl group. Namely, a biphenyl group can be an aryl group, or it can also be interpreted as a substituent in which two phenyl groups are connected.

In the present disclosure, the carbon number of a carbonyl group is not particularly limited, but is preferably 1 to 40. Specifically, the carbonyl group can be a compound having the following structural formulas, but is not limited thereto:

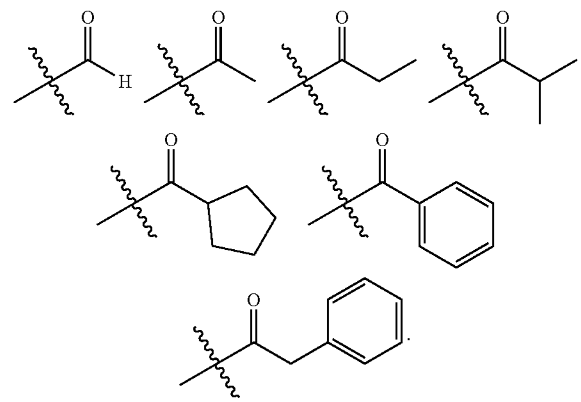

In the present disclosure, an ester group can have a structure in which oxygen of the ester group can be substituted by a straight-chain, branched, or cyclic alkyl group having 1 to 25 carbon atoms, or an aryl group having 6 to 25 carbon atoms. Specifically, the ester group can be a compound having the following structural formulas, but is not limited thereto:

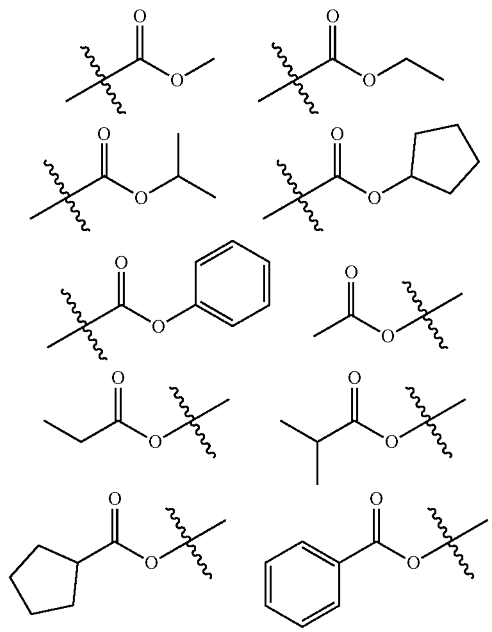

In the present disclosure, the carbon number of an imide group is not particularly limited, but is preferably 1 to 25. Specifically, the imide group can be a compound having the following structural formulas, but is not limited thereto:

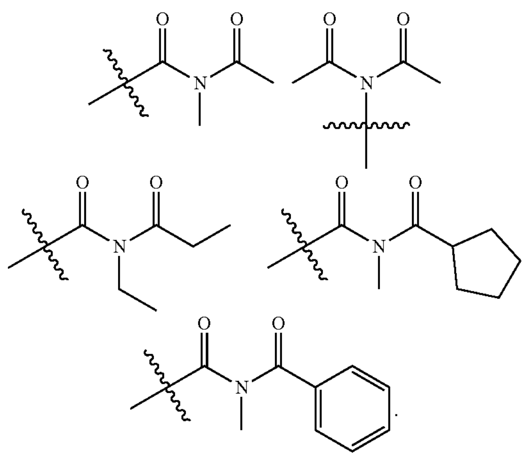

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group can be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, aryl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The aryl group can be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, and the like, but is not limited thereto.

In the present disclosure, the fluorenyl group can be substituted, and two substituents can be linked with each other to form a spiro structure. In the case where the fluorenyl group is substituted,

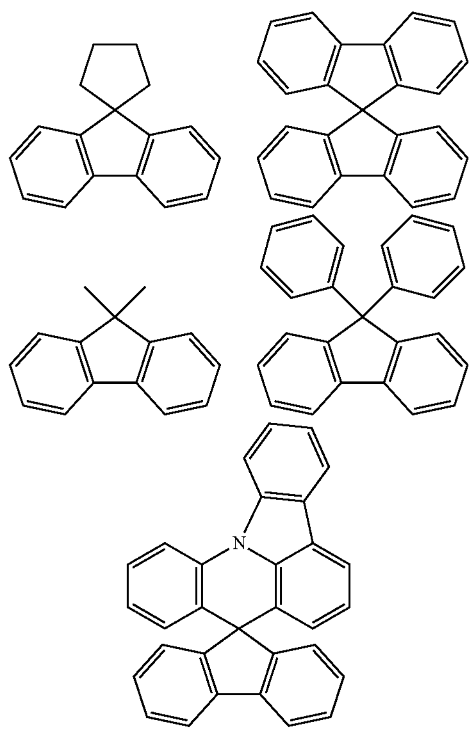

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

Hereinafter, the present disclosure will be described in detail for each configuration.

Anode and Cathode

The anode and cathode used in the present disclosure mean electrodes used in an organic light emitting device.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Light Emitting Layer

The light emitting layer used in the present disclosure means a layer that can emit light in the visible light region by combining holes and electrons transported from the anode and the cathode. Generally, the light emitting layer includes a host material and a dopant material The host material can further include a fused aromatic ring derivative, a heterocycle-containing compound or the like. In the present disclosure, a compound of the following Chemical Formula 1, a compound of the following Chemical Formula 2, and a compound of the following Chemical Formula 3 are mixed and used as the host material.

Specifically, a host material containing Chemical Formula 1 in which pyridine, pyrimidine, or triazine is bonded to dibenzofuran or dibenzothiophene via a linker; Chemical Formula 2 of the biscarbazole series; and Chemical Formula 3 of the indolocarbazole series can be applied as a green host of the light emitting layer.

Furthermore, the organic light emitting device, to which the above three types of compounds are applied as a host material of the light emitting layer, can exhibit improved driving voltage (low voltage), high efficiency, and long lifetime characteristics, as compared to the case where 3 types of compounds completely different from the above 3 types are mixed and used as a host material (3 types of hosts are applied), the case where any one or two of the above three types of compounds is changed to another compound (3 types of hosts are applied), and the case where only one or two of the above three types of compounds are used as the host material of the light emitting layer (one or two types of hosts are applied).

Hereinafter, the three types of compounds will be described in detail.

The Chemical Formula 1 can be any one of the following Chemical Formulas 1-1 to 1-4:

[Chemical Formula 1-1]

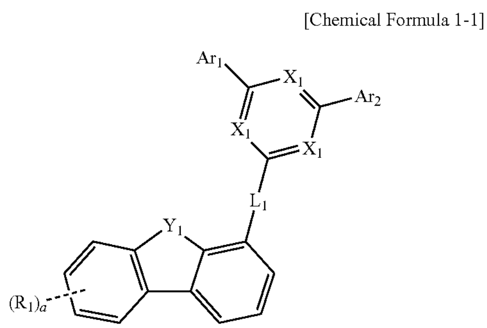

[Chemical Formula 1-2]

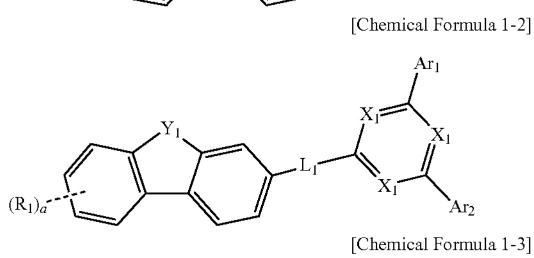

[Chemical Formula 1-3]

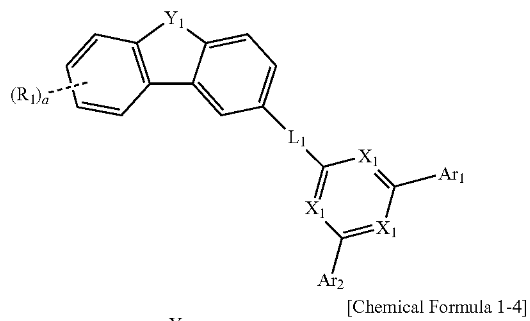

[Chemical Formula 1-4]

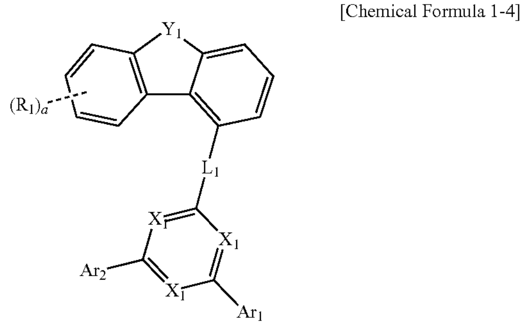

wherein in Chemical Formulas 1-1 to 1-4, $Y_1$, $X_1$, $L_1$, $Ar_1$, $Ar_2$, $R_1$, and a are as defined above; and $Y_1$ is O or S.

Each $X_1$ is independently CH or N, provided that at least one of $X_1$ is N, For example, two of $X_1$ are N and the remaining one is CH; or all of $X_1$ can be N.

The $L_1$ is a direct bond, a substituted or unsubstituted $C_{6-30}$ arylene, or a substituted or unsubstituted $C_{2-30}$ heteroarylene containing any one or more selected from the group consisting of N, O and S. For example, $L_1$ can be a direct bond.

$Ar_1$ and $Ar_2$ can be each independently a substituted or unsubstituted $C_{6-30}$ aryl, or a substituted or unsubstituted $C_{2-30}$ heteroaryl containing any one or more selected from the group consisting of N, O and S. For example, $Ar_1$ and $Ar_2$ can be each independently phenyl, biphenylyl, dibenzofuranyl, dibenzothiophenyl, carbazol-9-yl, or (phenyl)carbazol-9-yl, with the $Ar_1$ and $Ar_2$ being each independently unsubstituted or substituted with at least one deuterium.

$R_1$ can be hydrogen, deuterium, a substituted or unsubstituted $C_{6-30}$ alkyl, a substituted or unsubstituted $C_{6-30}$ aryl, or a substituted or unsubstituted $C_{2-30}$ heteroaryl containing any one or more selected from the group consisting of N, O and S. For example, $R_1$ can be phenyl, biphenylyl, (phenyl)biphenylyl, terphenylyl, naphthyl, phenanthrenyl, triphenylenyl, dimethylfluorenyl, spirobifluorenyl, dibenzofuranyl, dibenzothiophenyl, carbazol-9-yl, (phenyl)carbazol-9-yl, (diphenyl)carbazol-9-yl, 9-phenyl-9H-carbazolyl, 12-phenyl-11,12-dihydroindolo[2,3-a]carbazol-11-yl, or 1,1-dimethyl-1,3-dihydroindeno[2,1-b]carbazol-3-yl, with the $R_1$ being unsubstituted or substituted with at least one deuterium.

a can be an integer of 1 to 7, and for example, it can be 1.

Representative examples of the compound of Chemical Formula 1 are as follows:

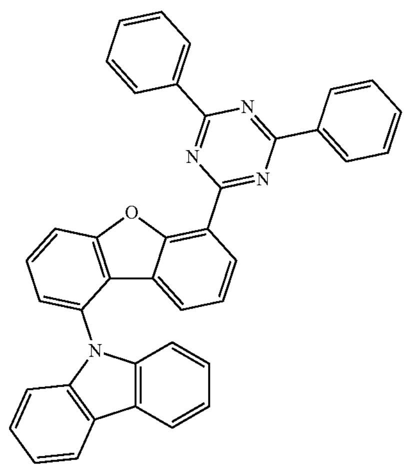

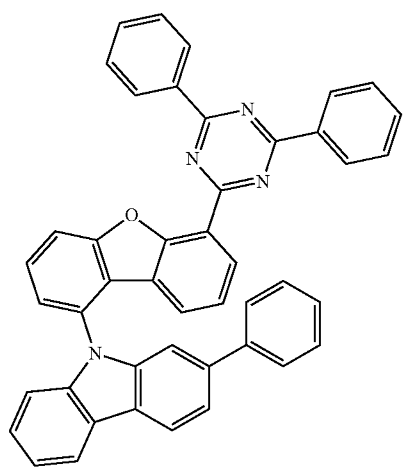

-continued
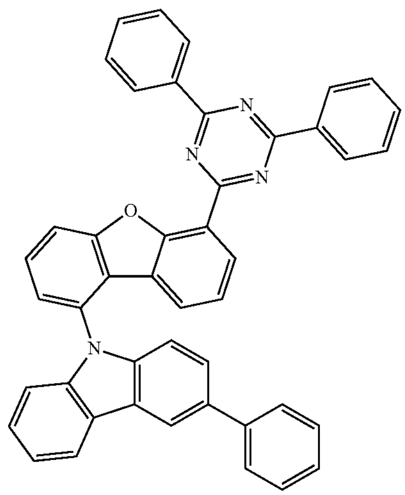
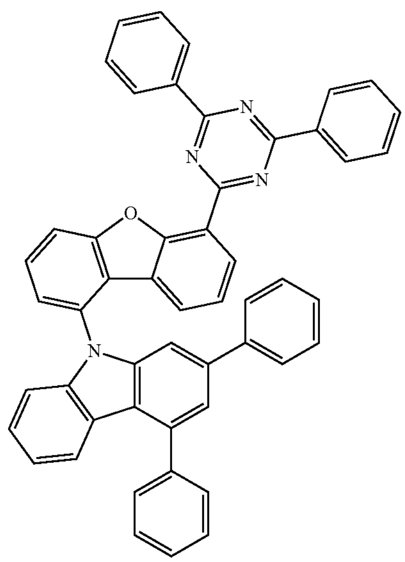
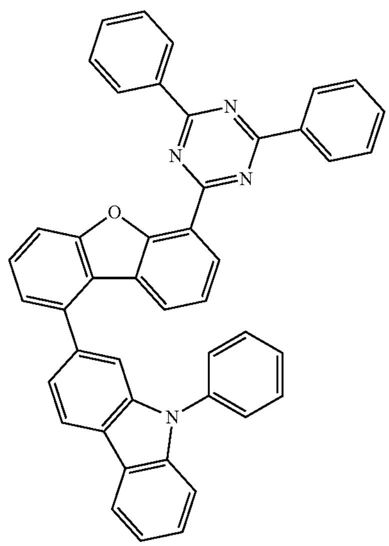
-continued
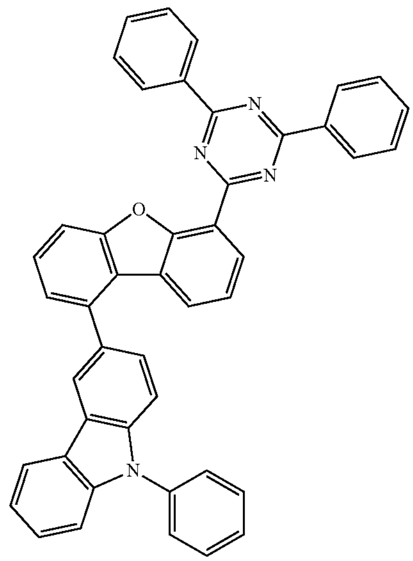
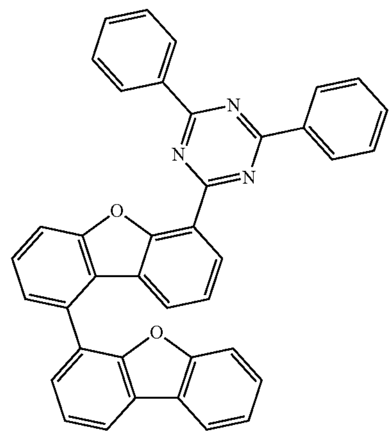
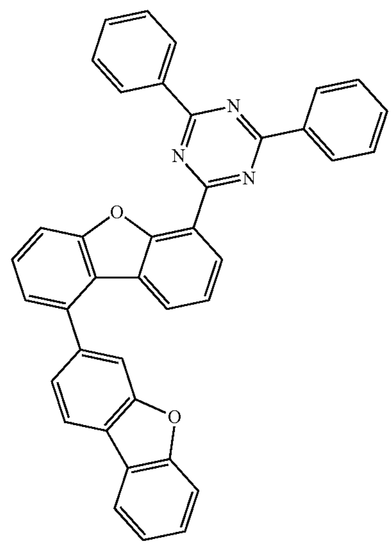

-continued
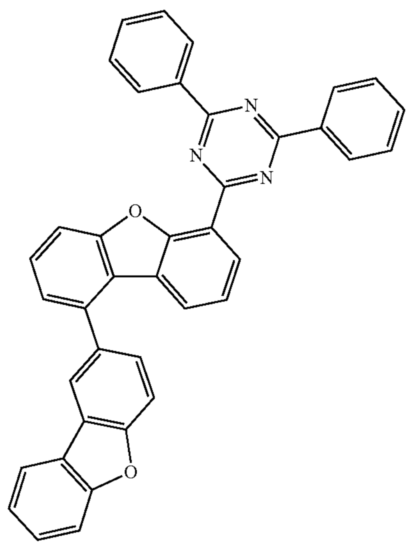
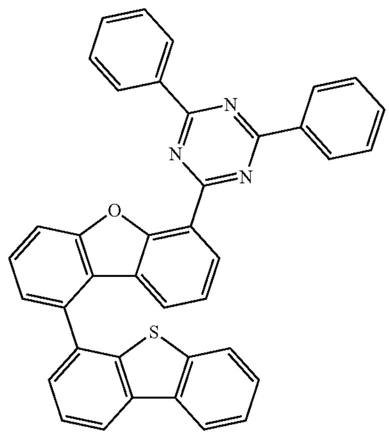
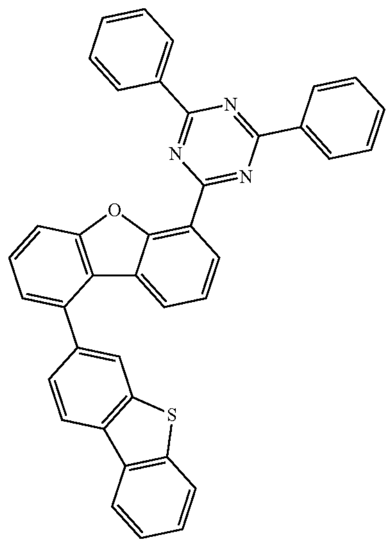
-continued
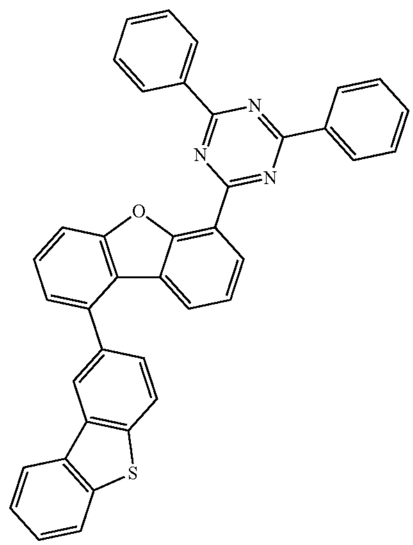
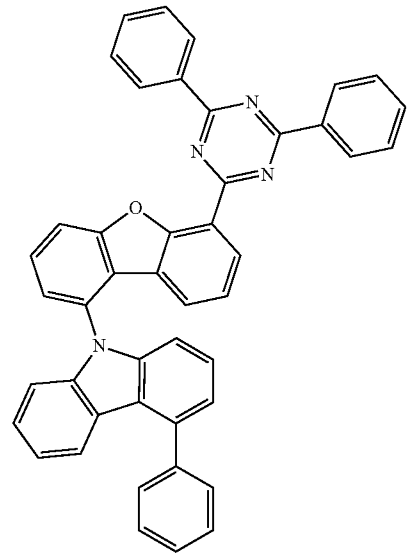
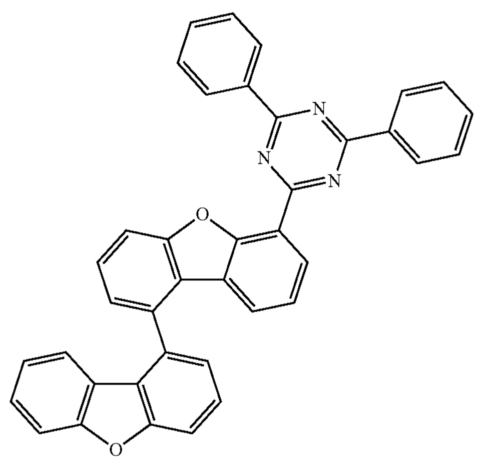

-continued
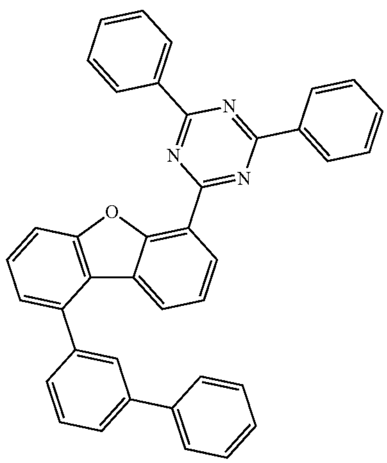
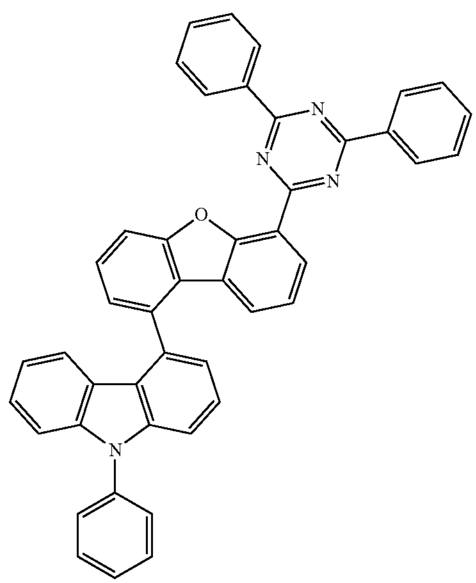
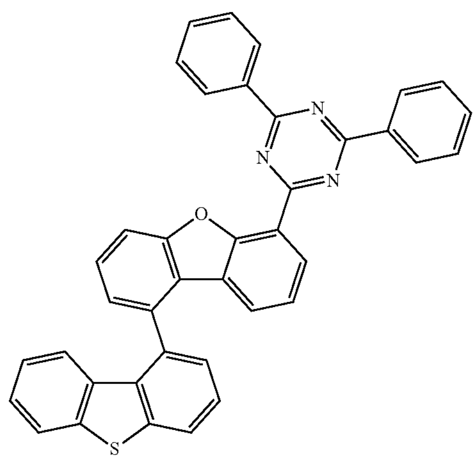
-continued
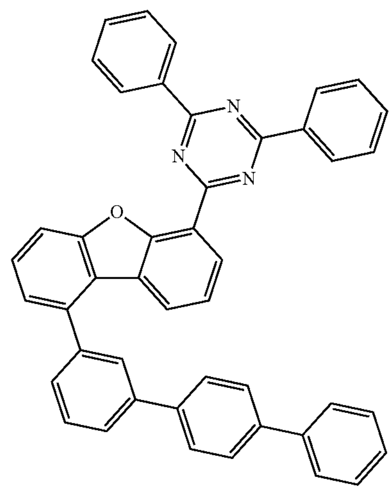
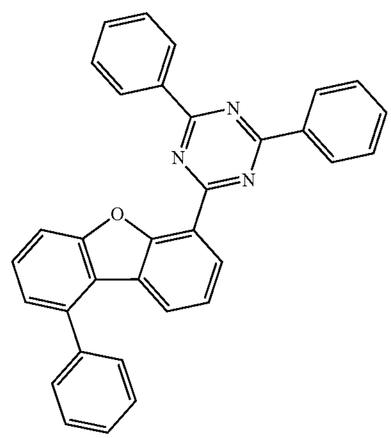
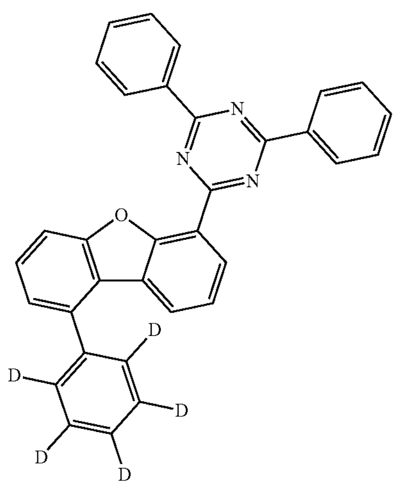

-continued
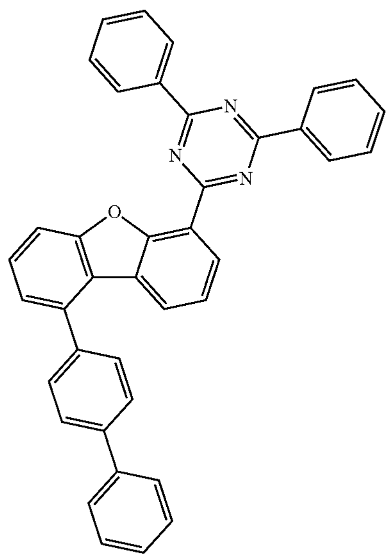
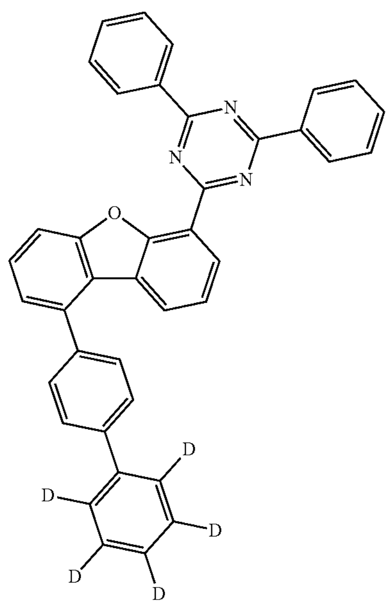
-continued
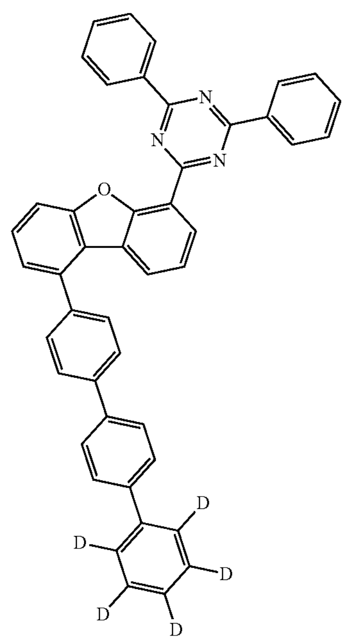
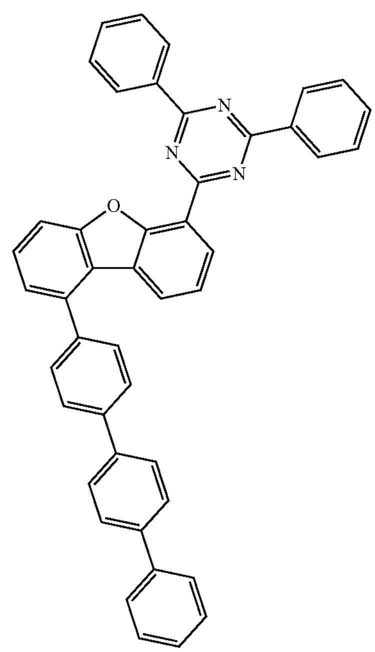

-continued
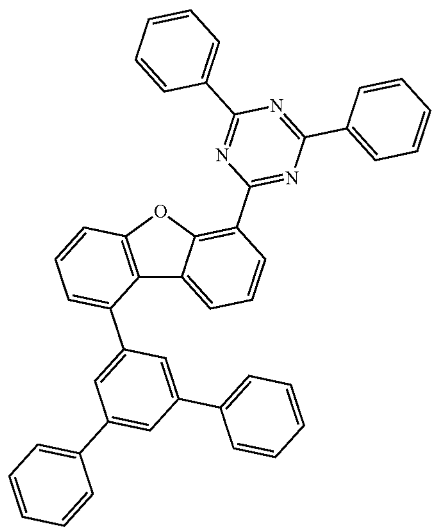
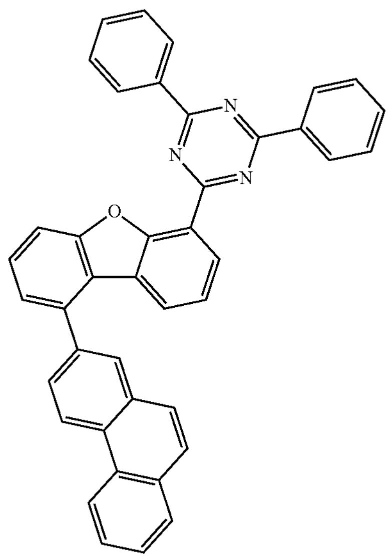
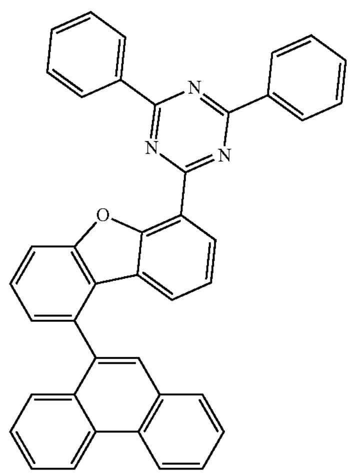
-continued
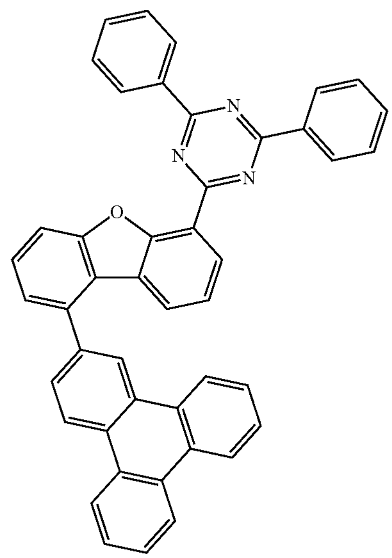
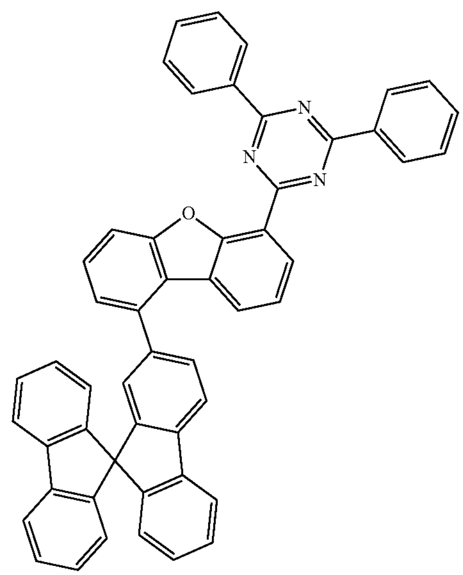
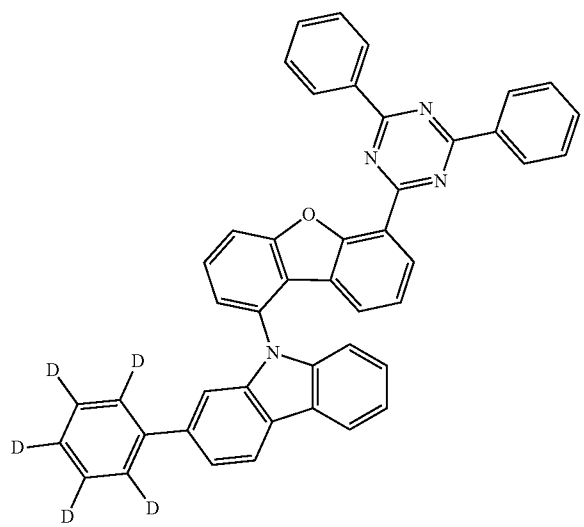

-continued
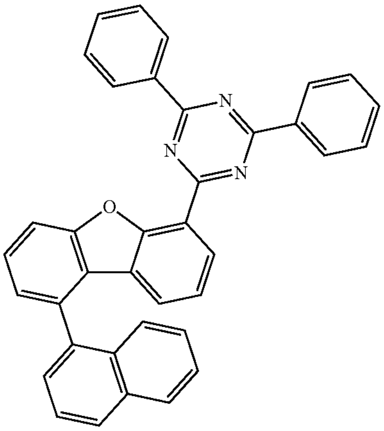
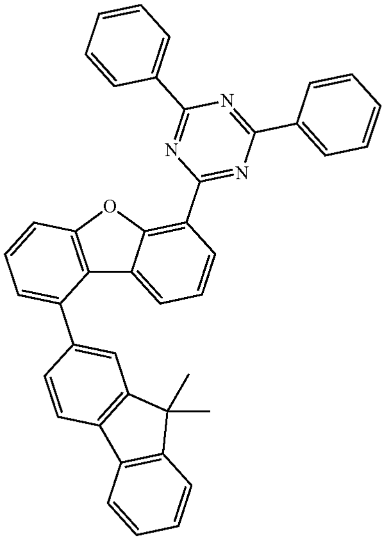
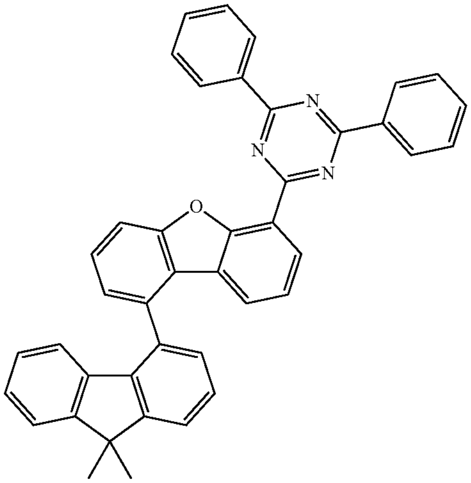
-continued
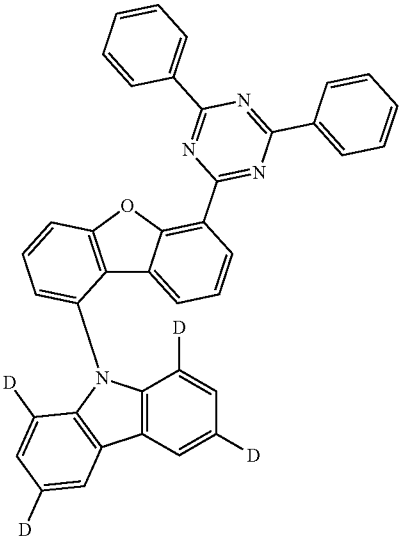
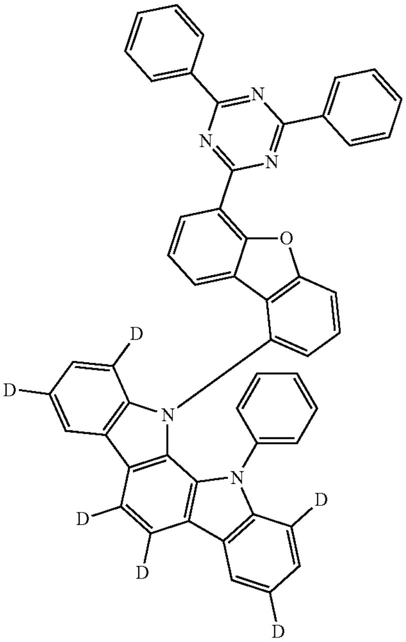

-continued
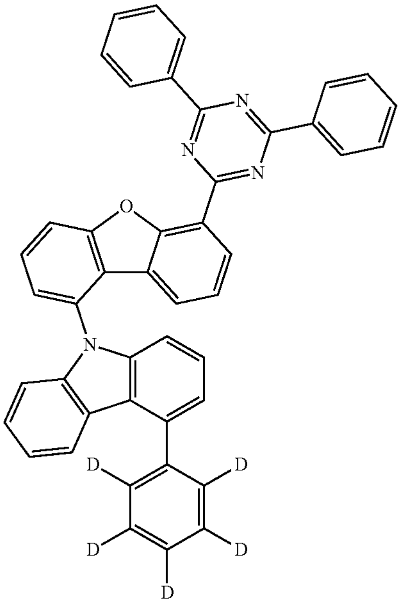
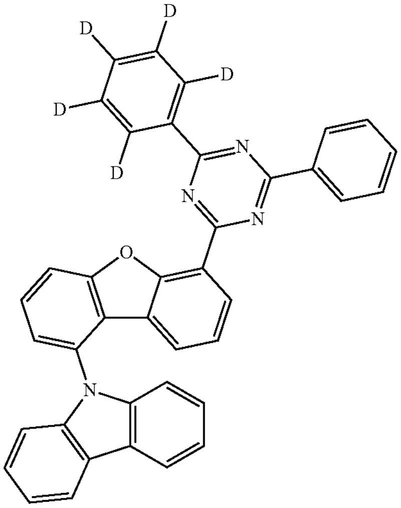
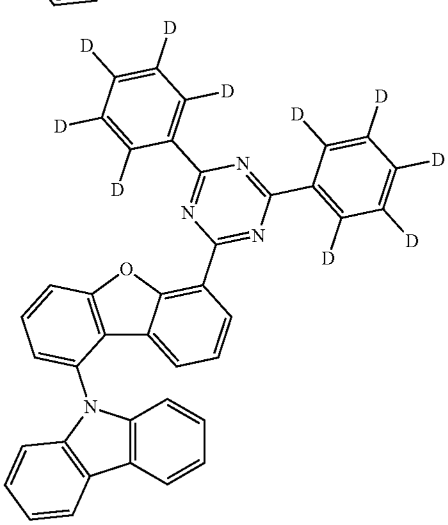
-continued
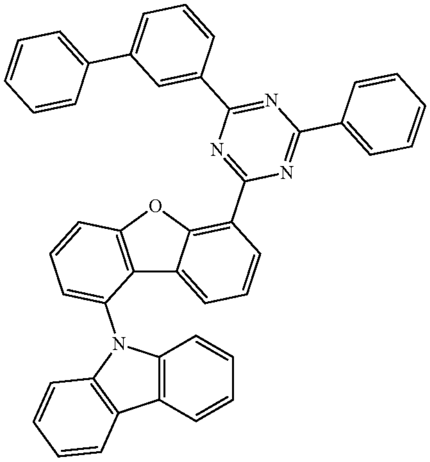
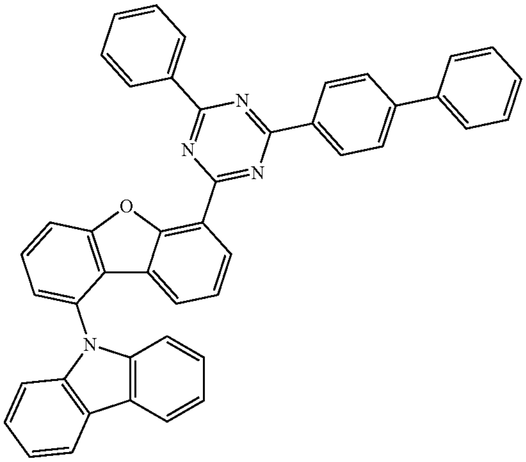
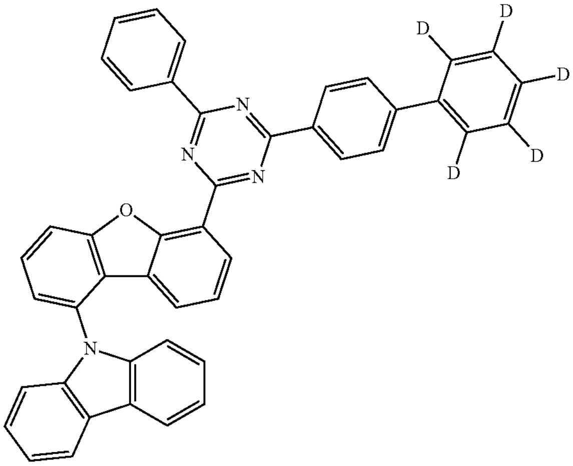

-continued
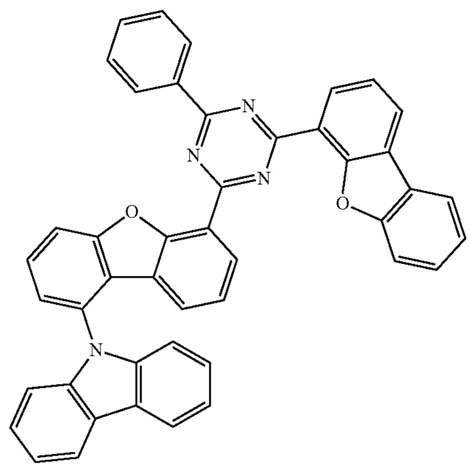
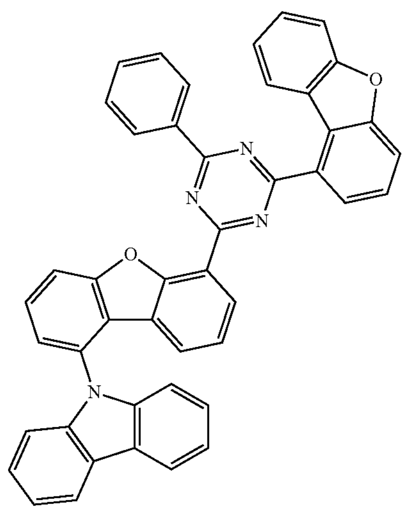
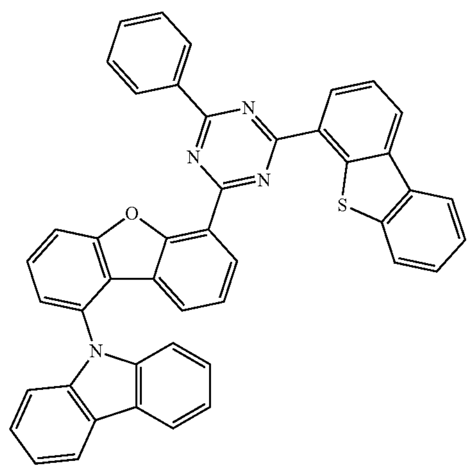
-continued
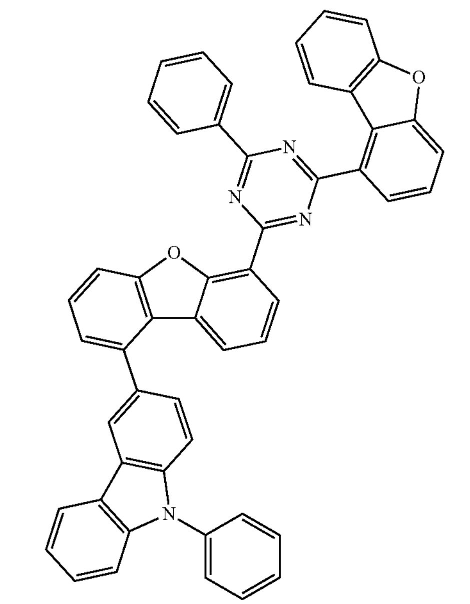
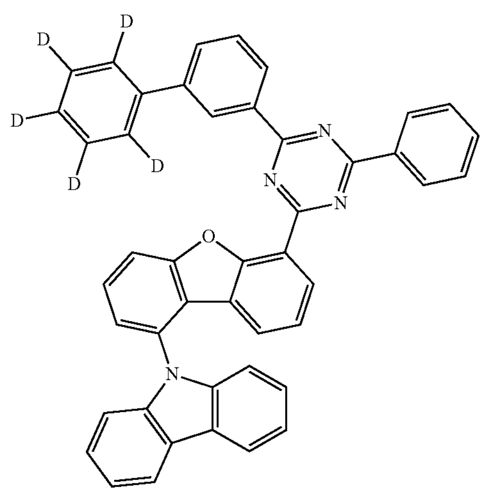
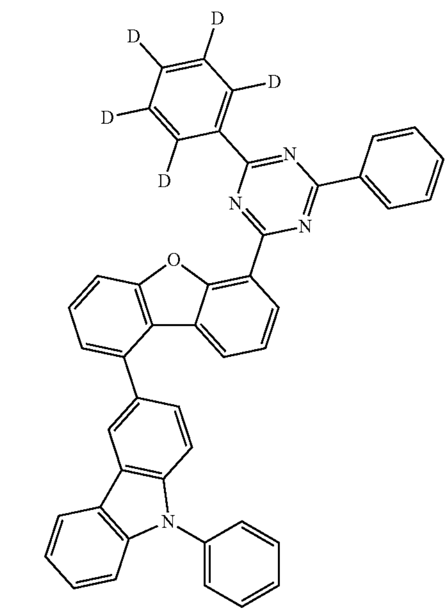

-continued
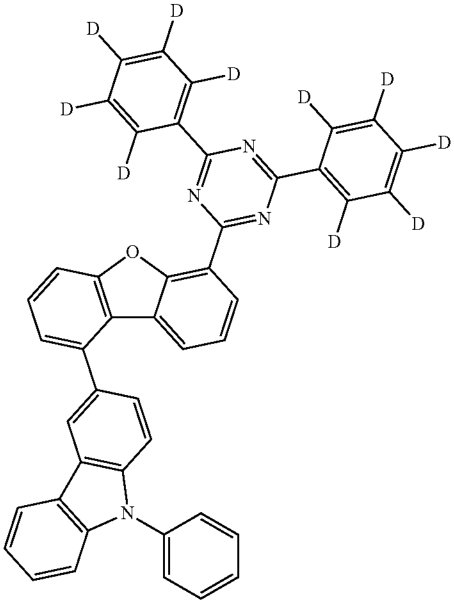
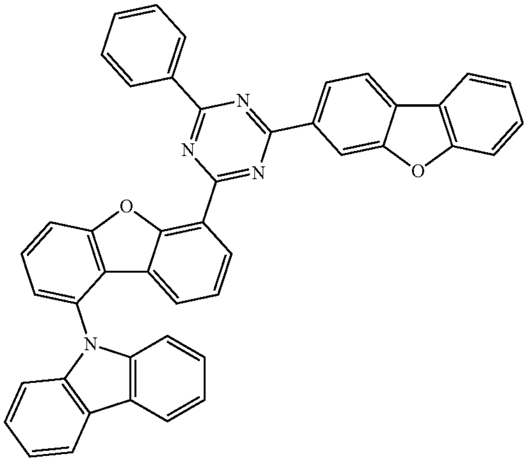
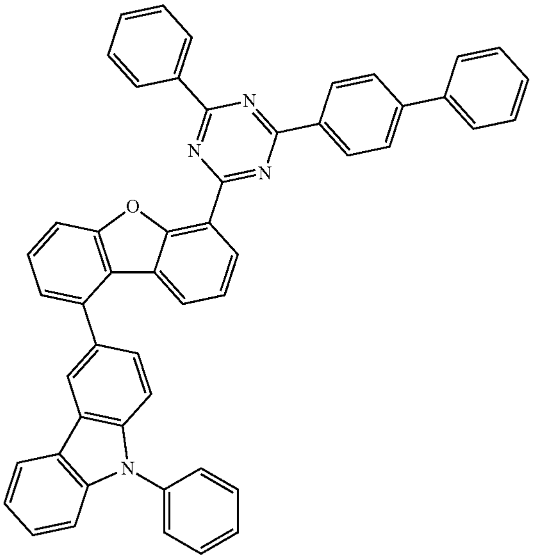
-continued
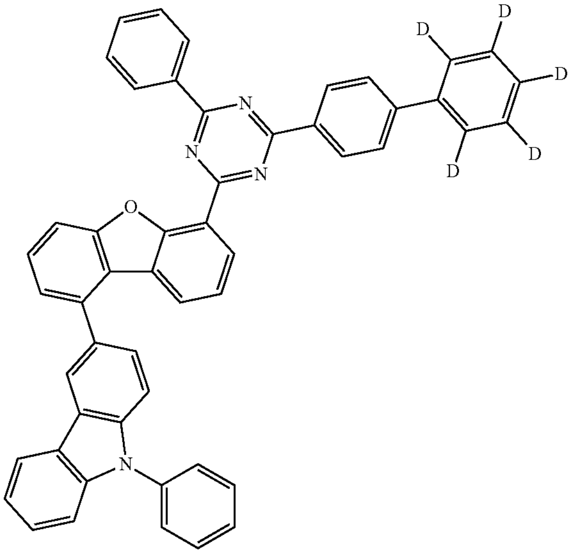
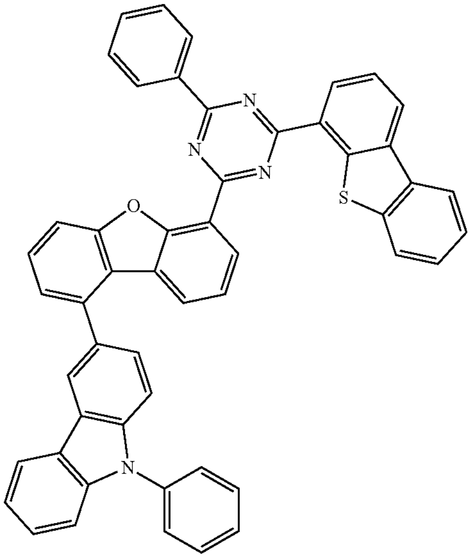
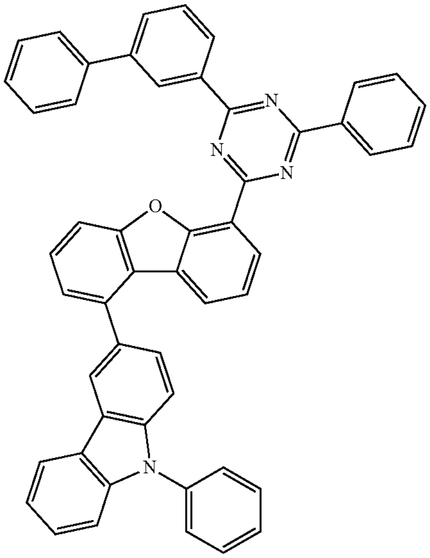

-continued
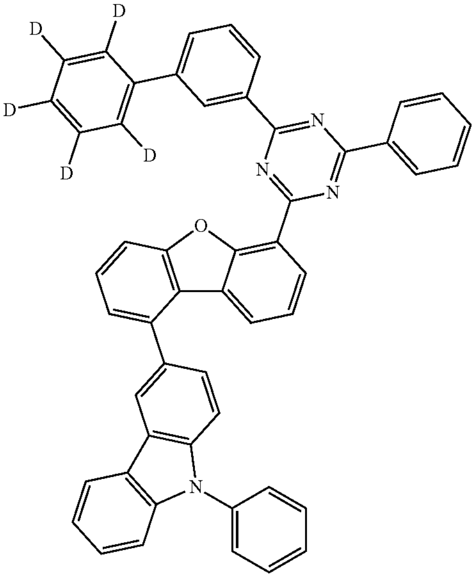
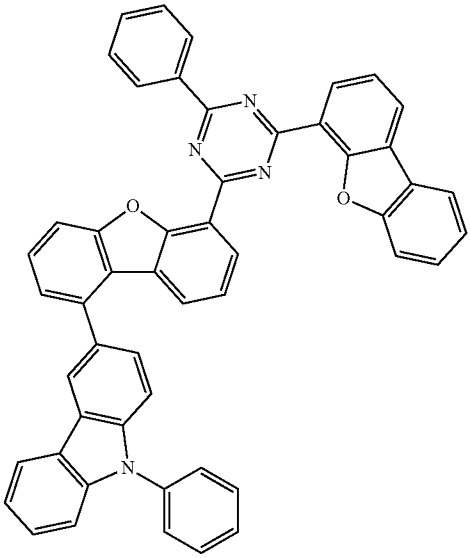
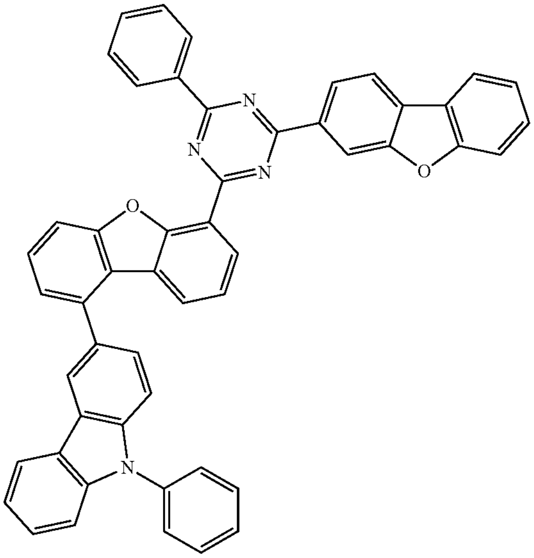
-continued
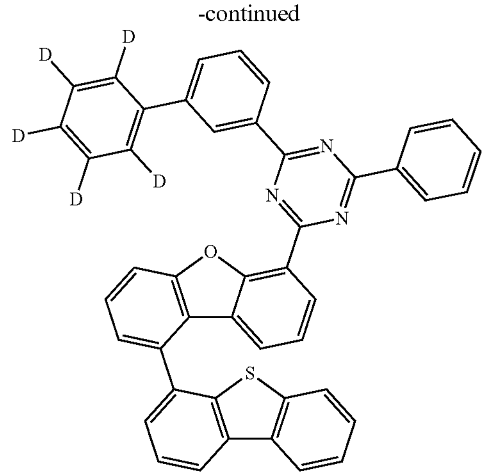
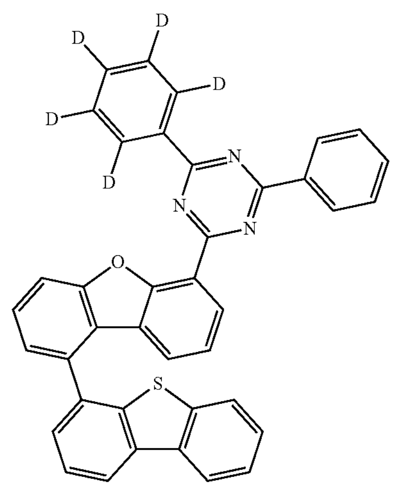
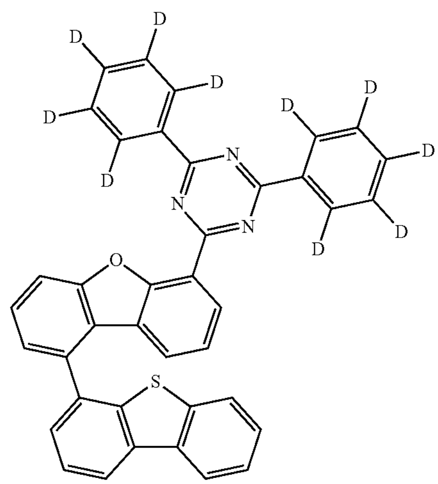

-continued
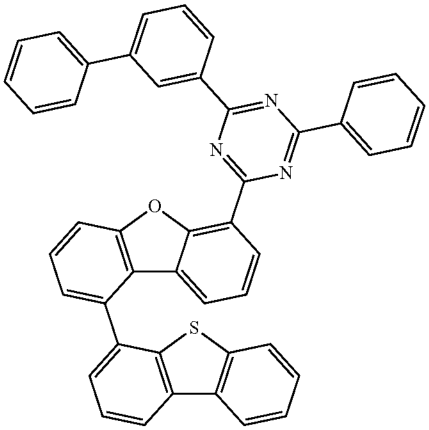
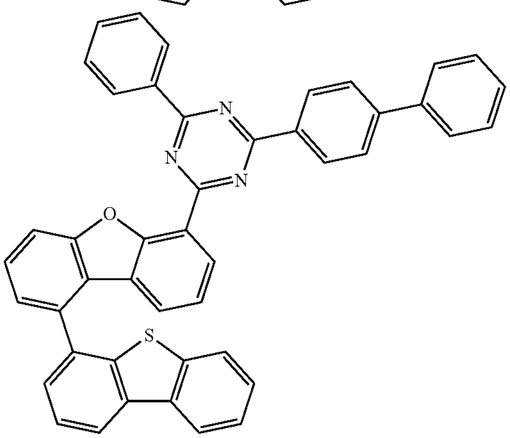
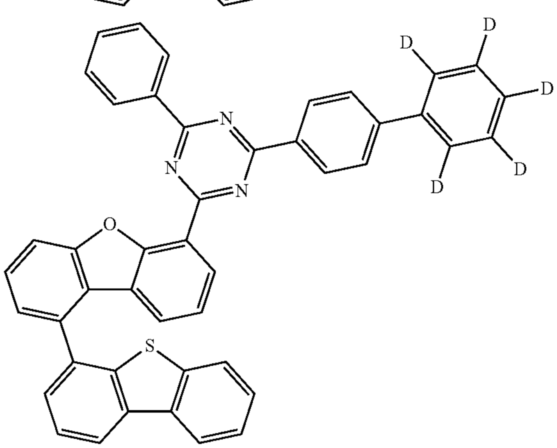
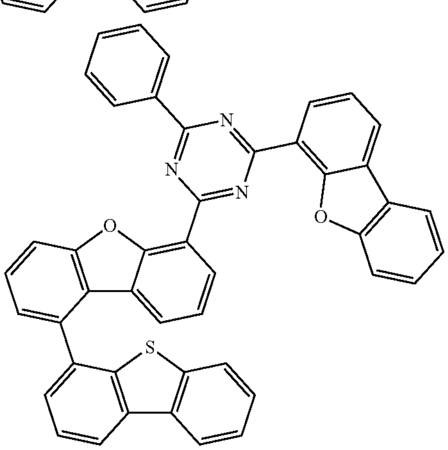
-continued
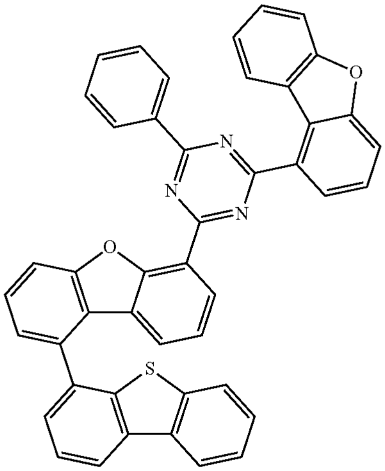
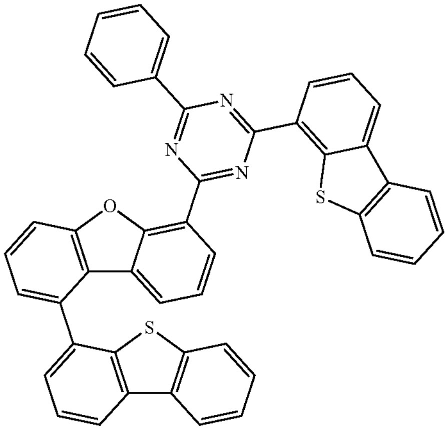
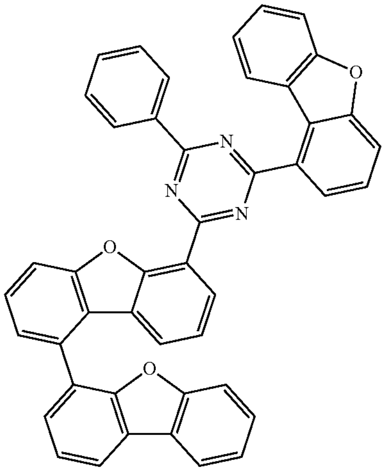

-continued
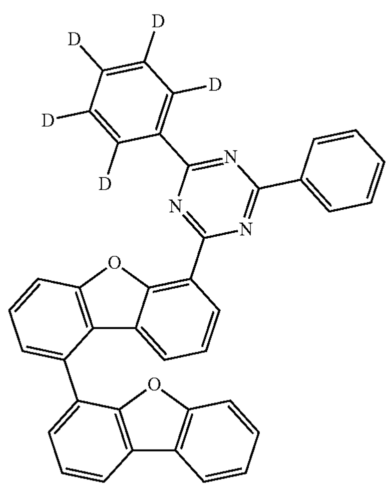
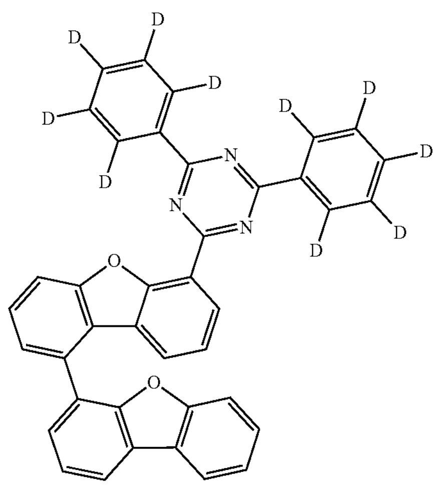
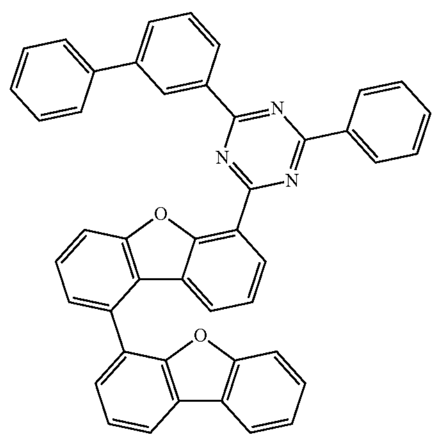
-continued
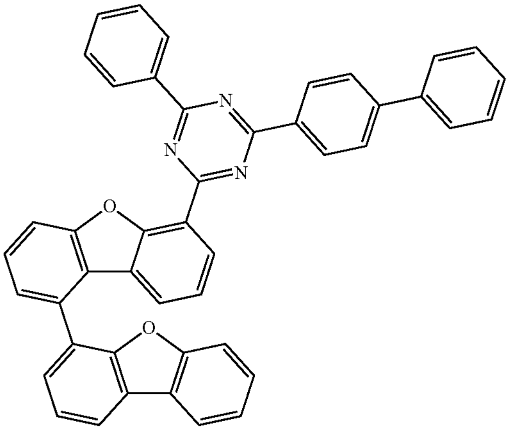
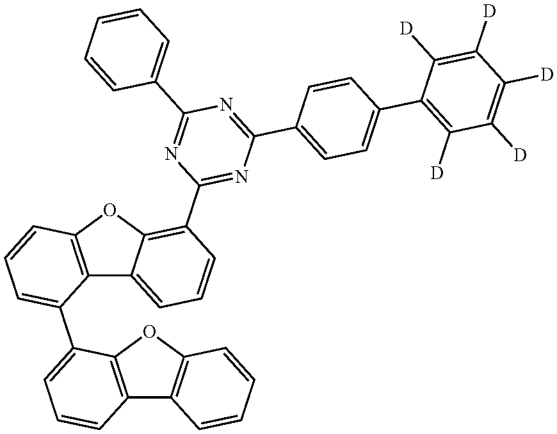
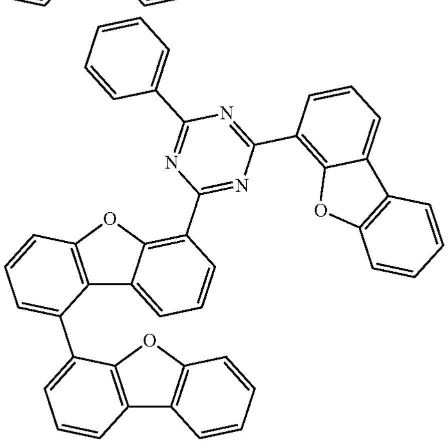
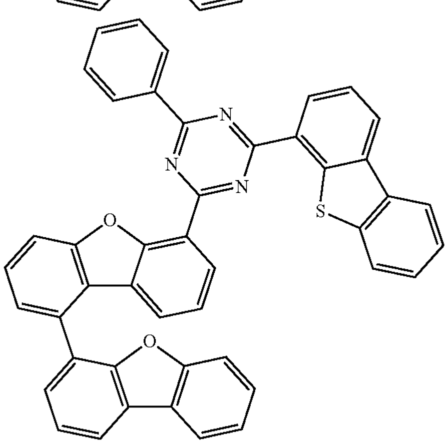

-continued
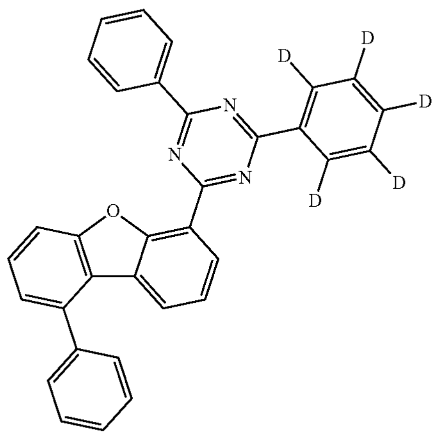
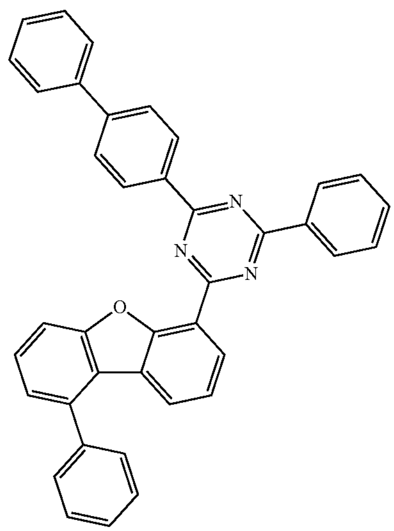
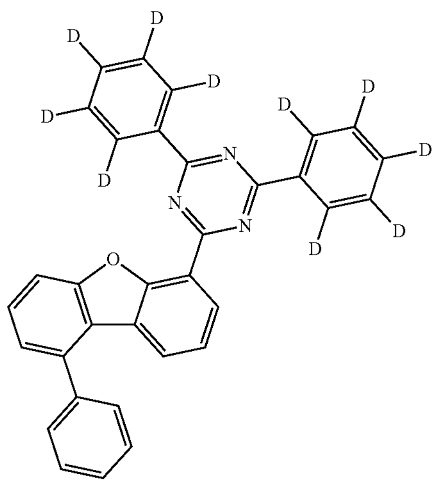
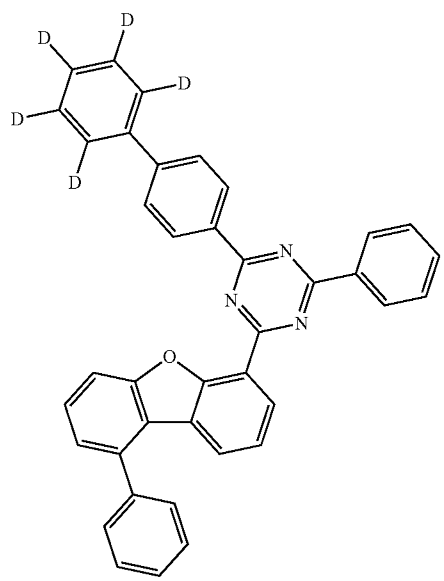
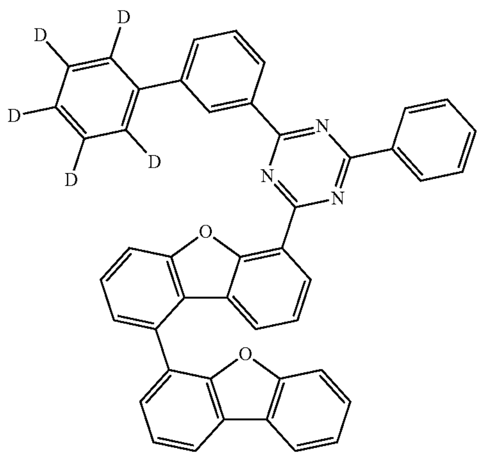
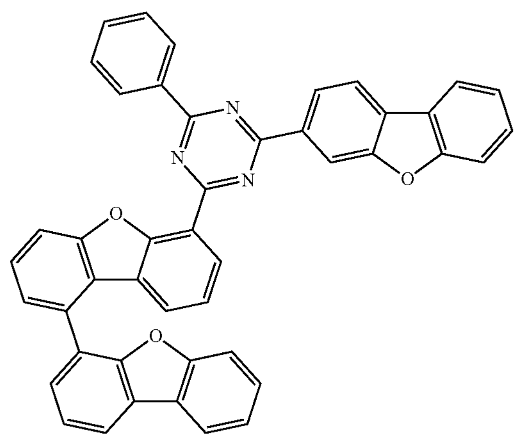
-continued -continued
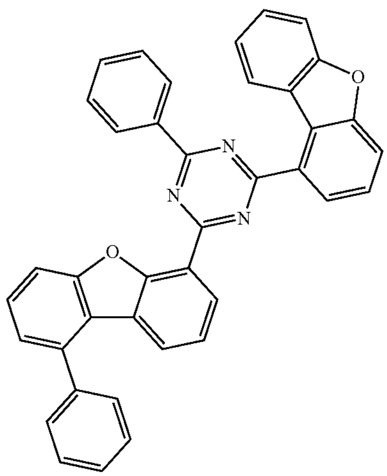
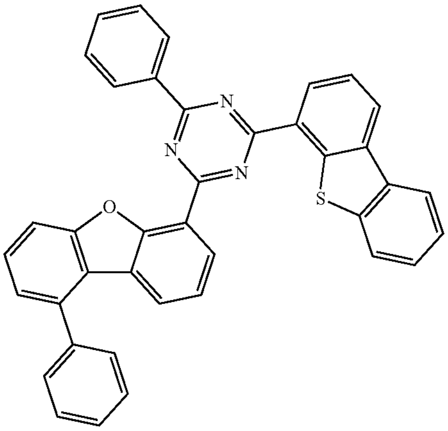
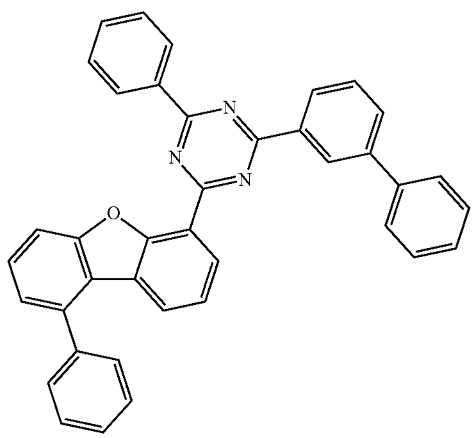
-continued
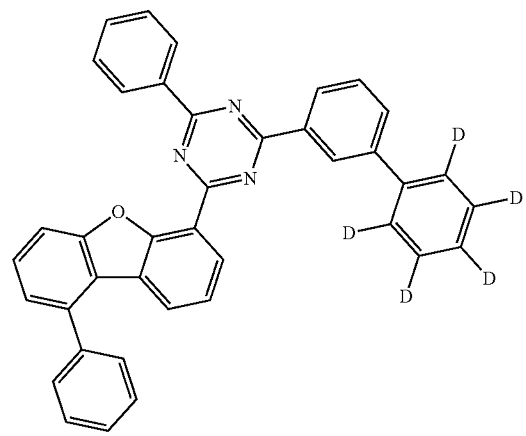
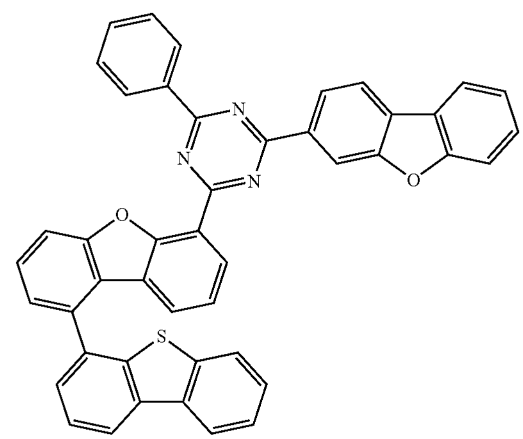
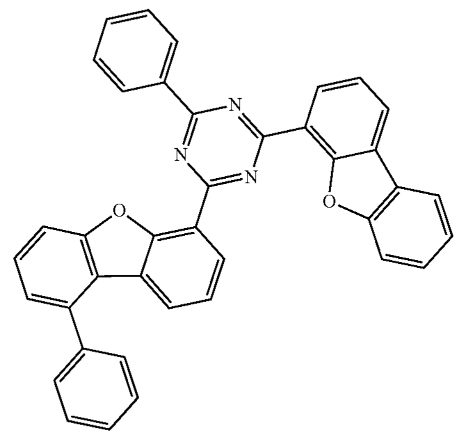

-continued
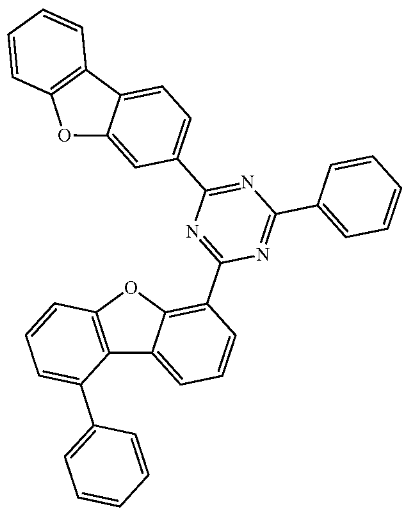
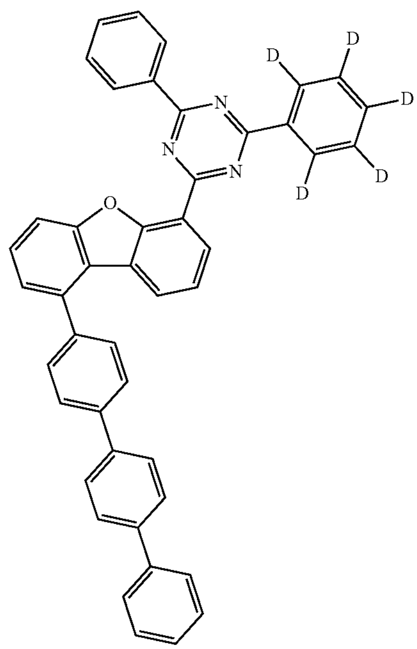
-continued
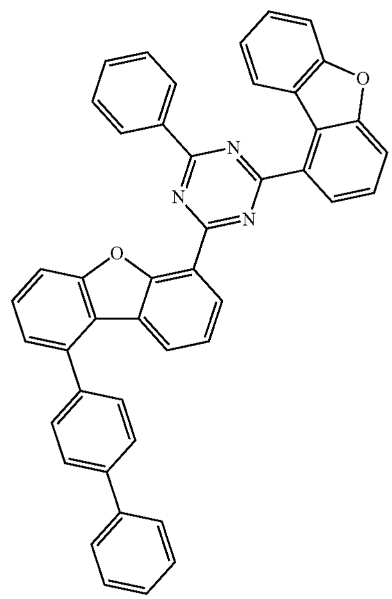
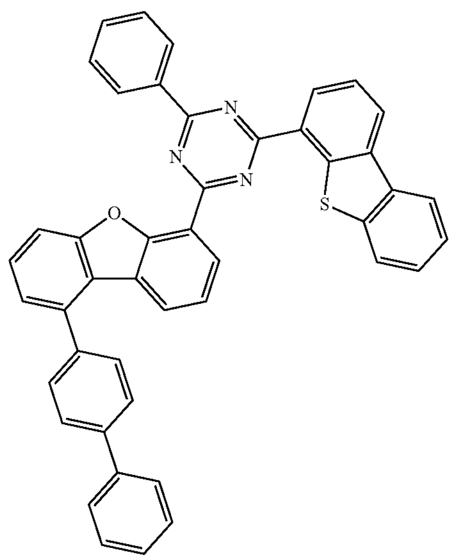

-continued
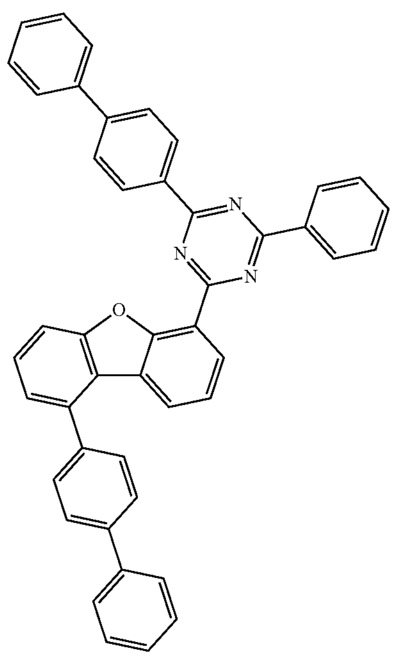
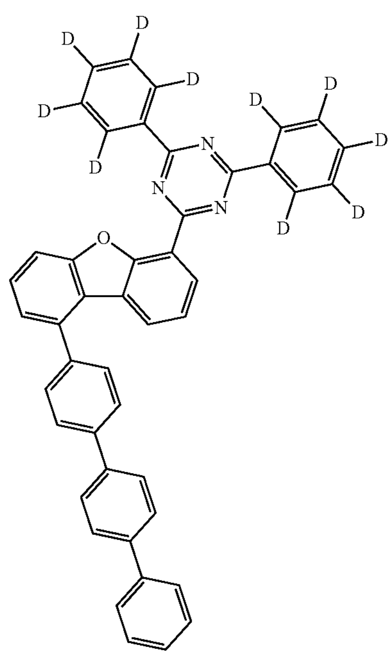
-continued
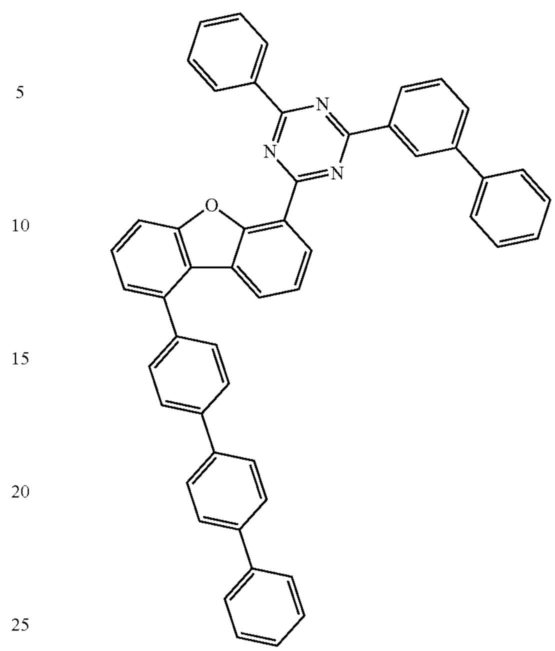
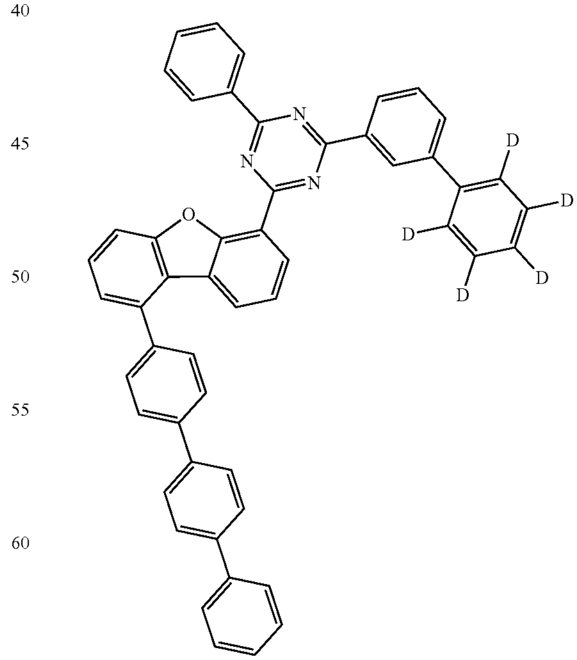

-continued
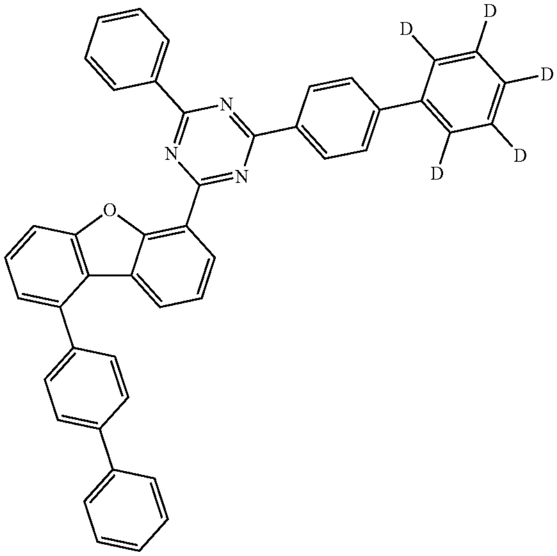
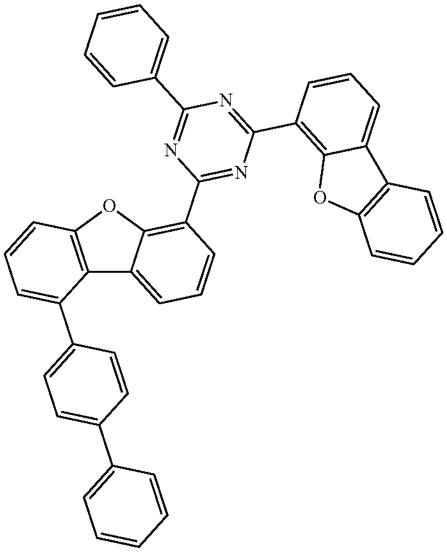
-continued
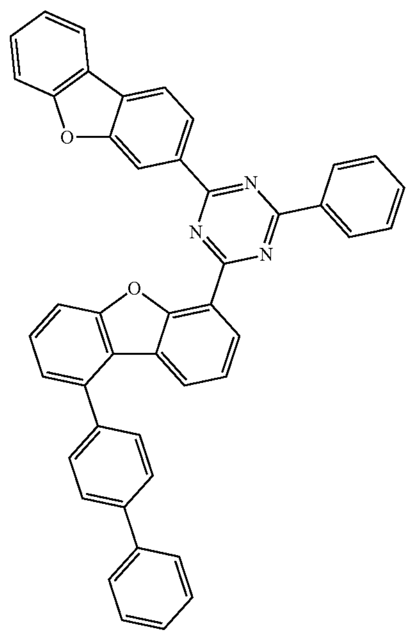
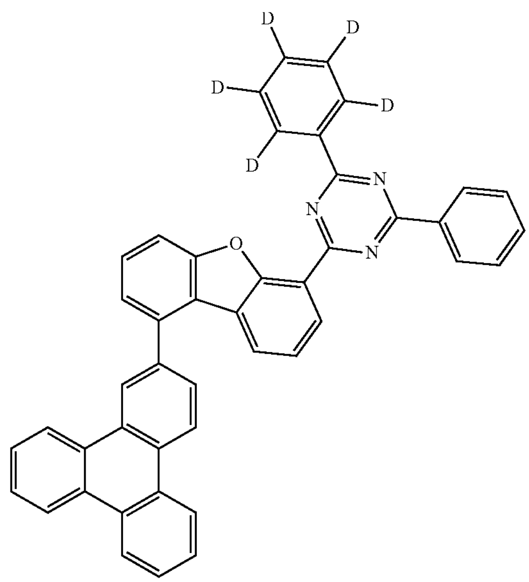

-continued
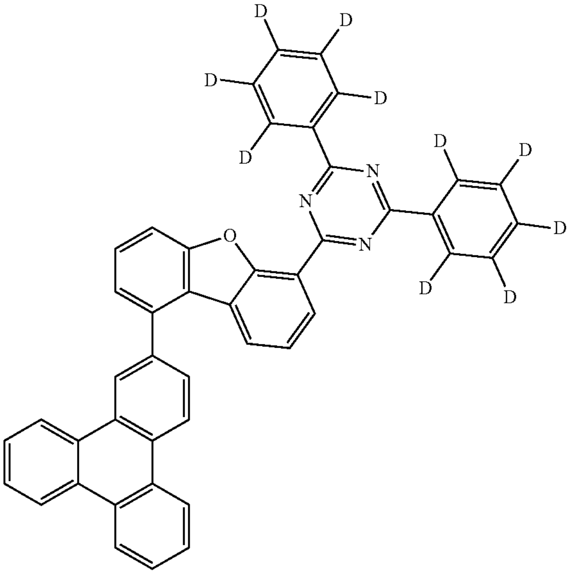
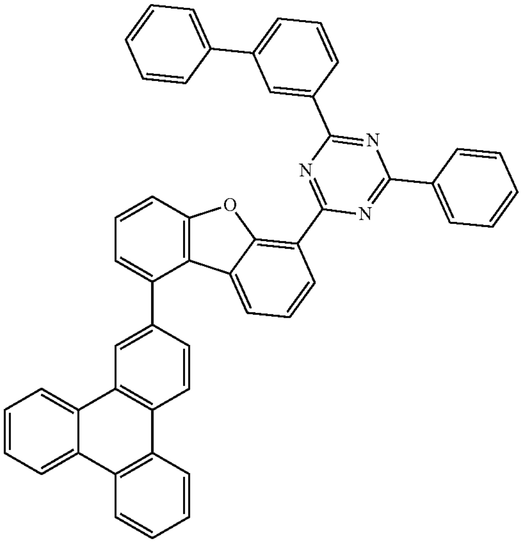
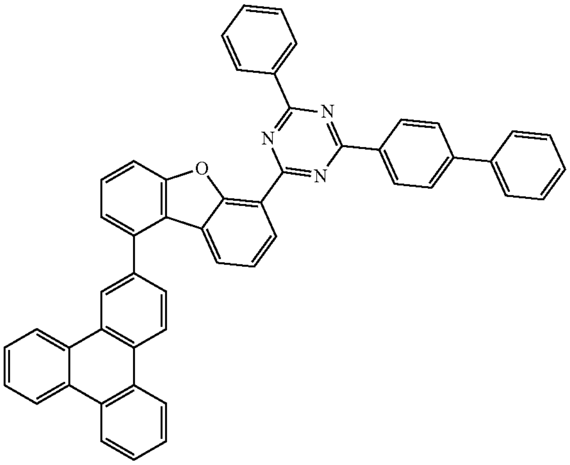
-continued
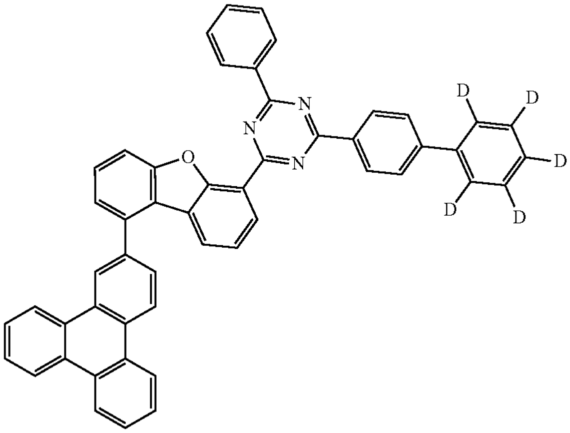
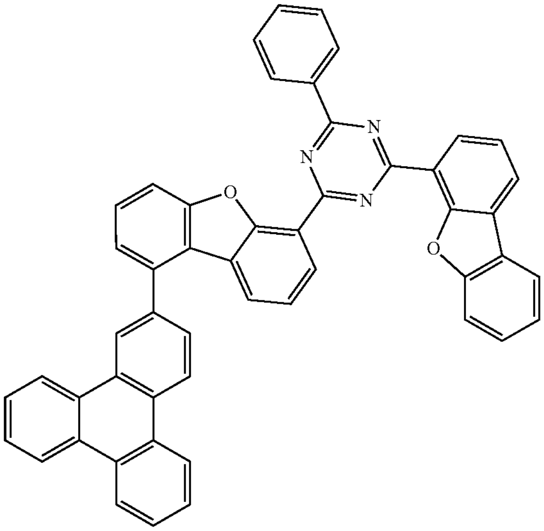
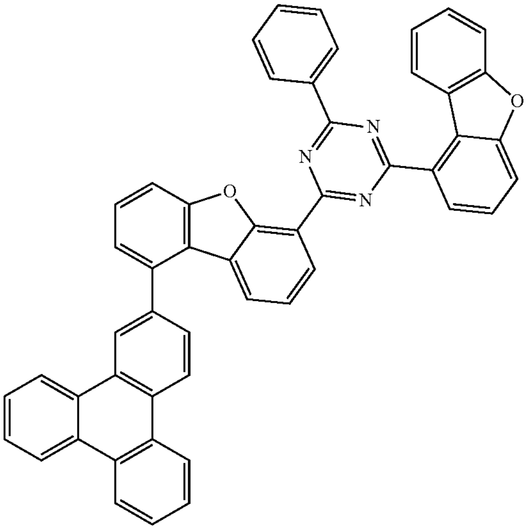

-continued
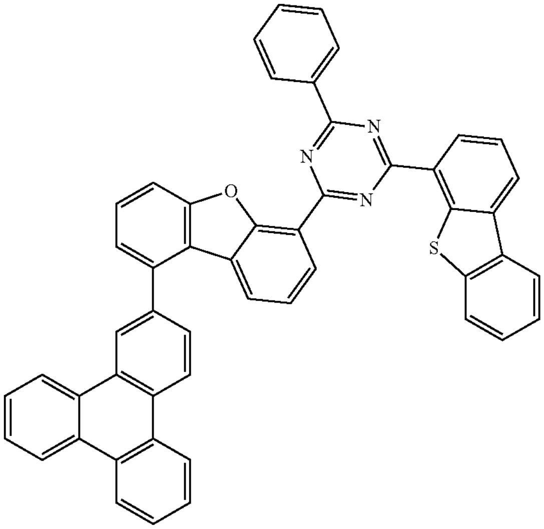
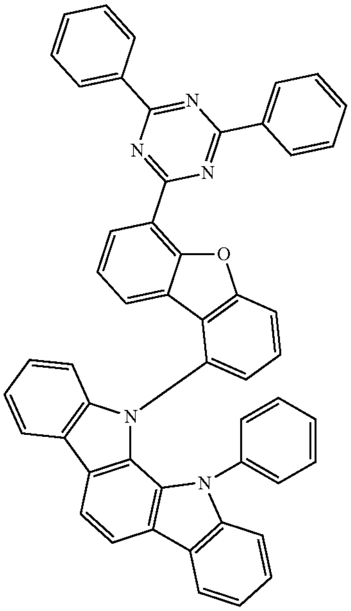
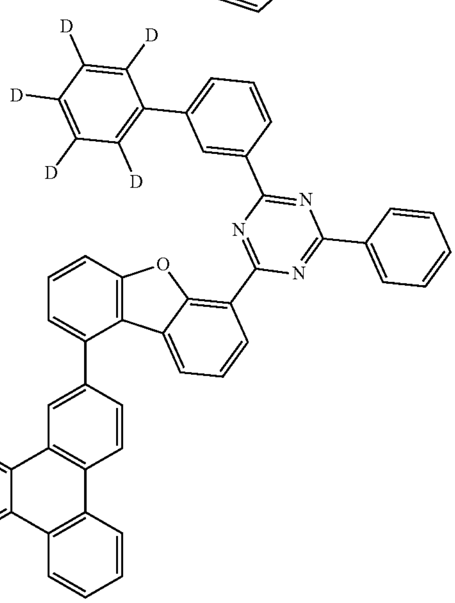
-continued
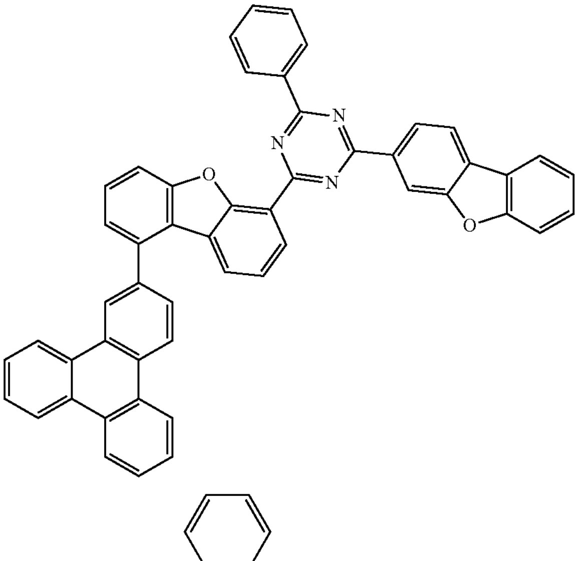
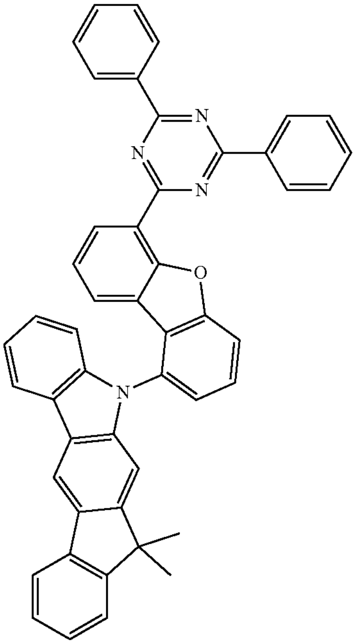
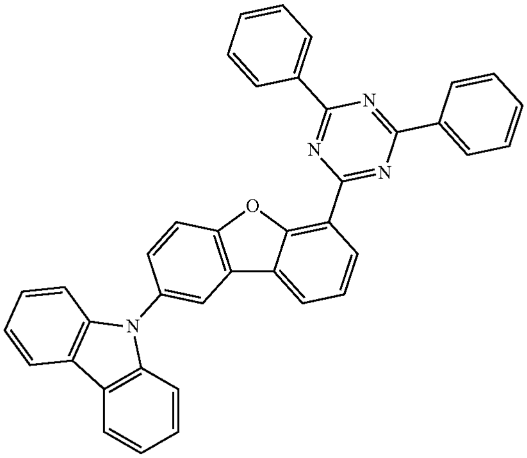

-continued
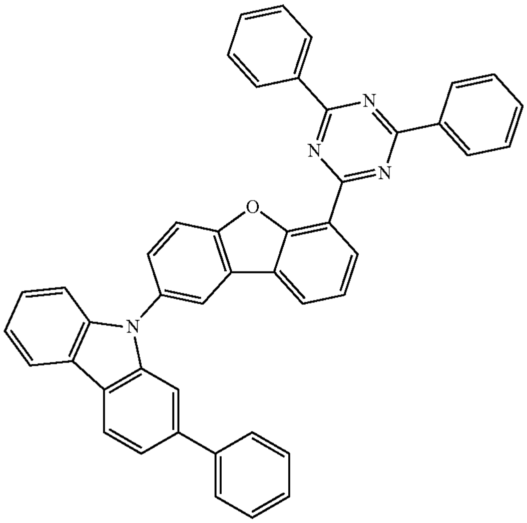
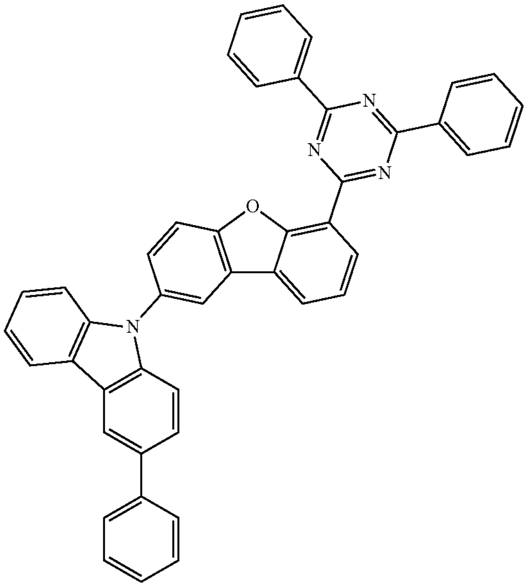
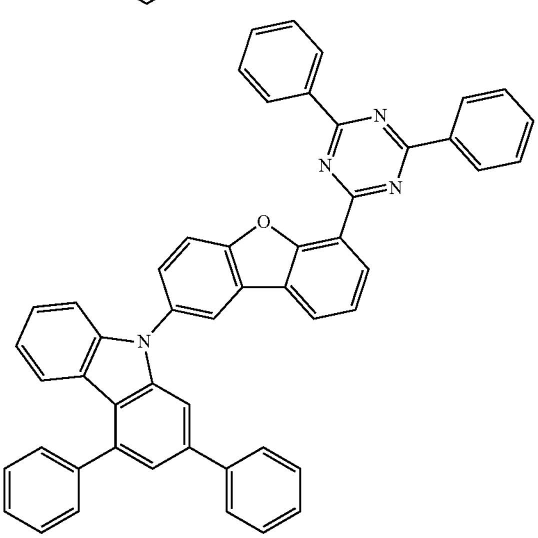
-continued
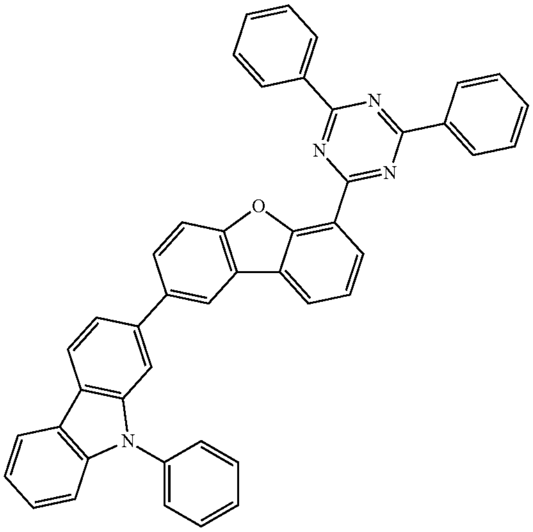
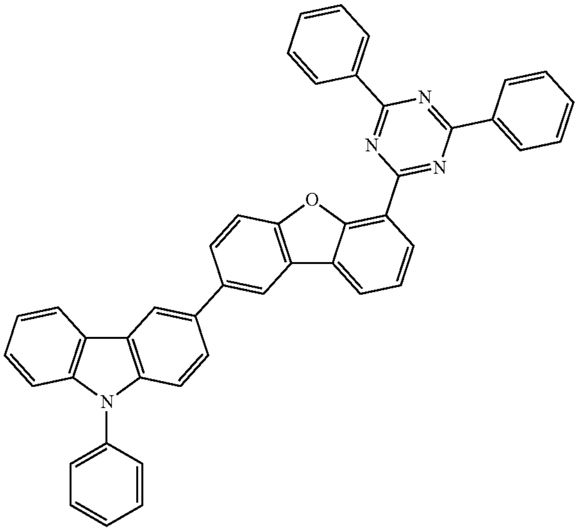
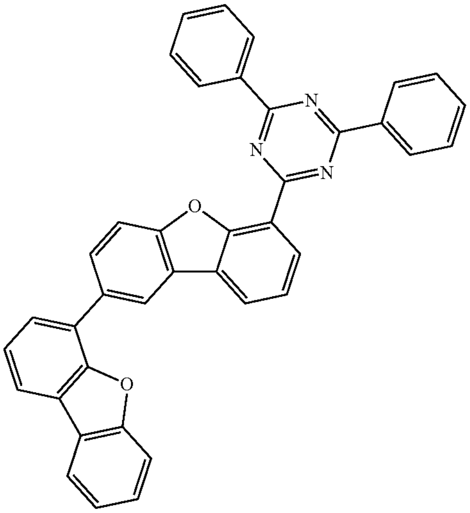

-continued
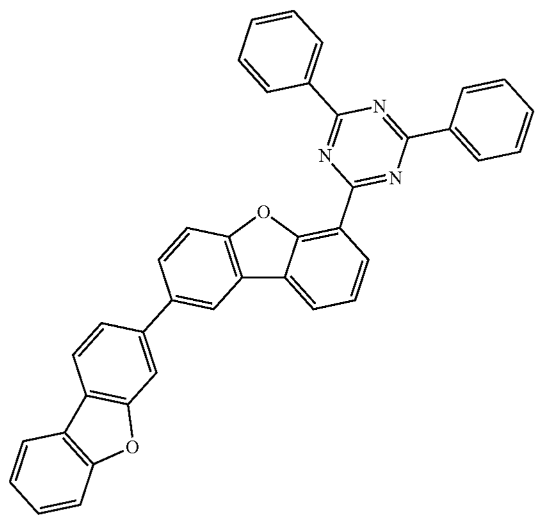
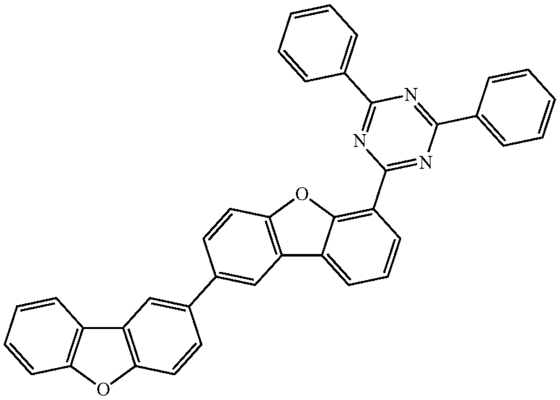
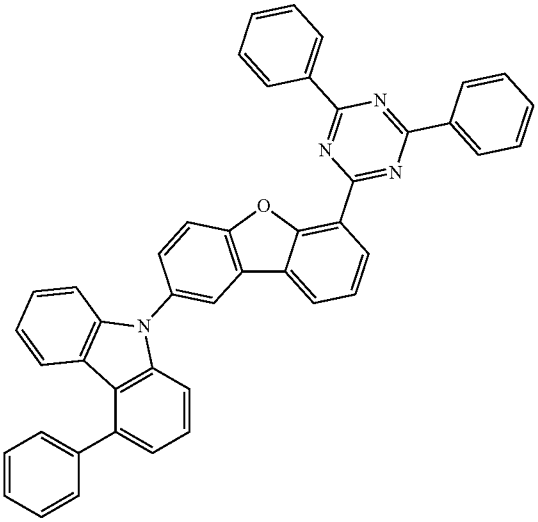
-continued
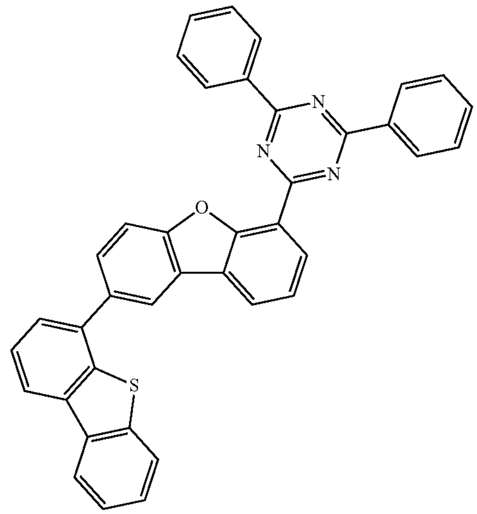
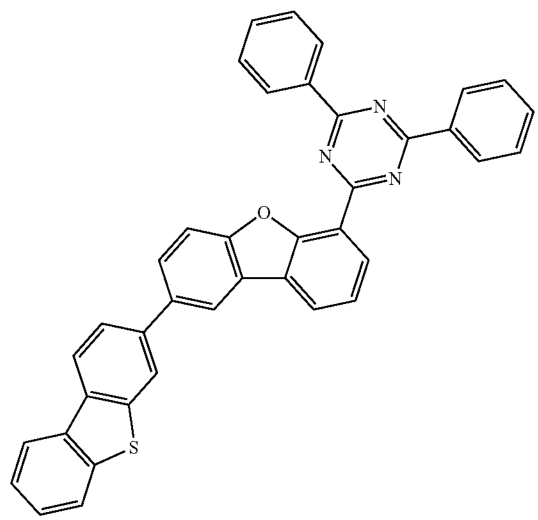
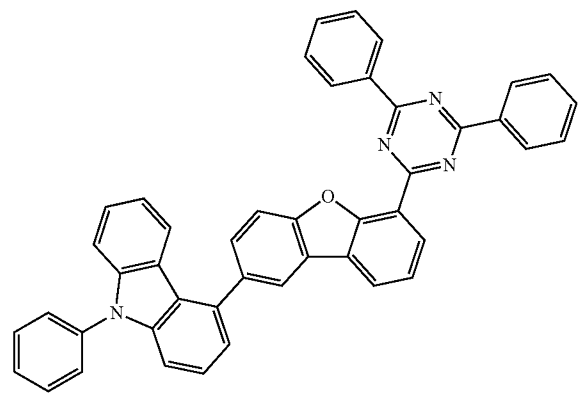

-continued
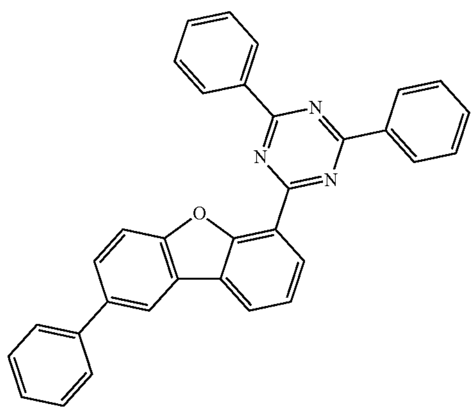
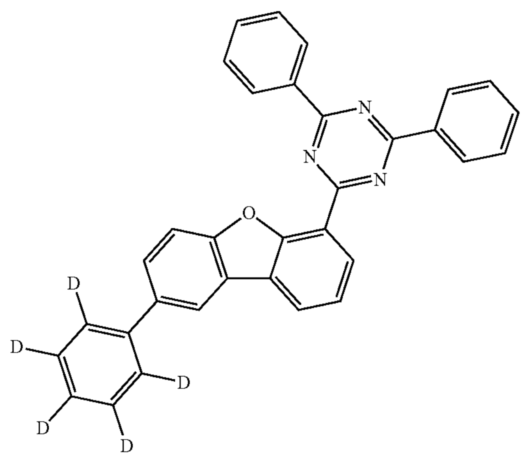
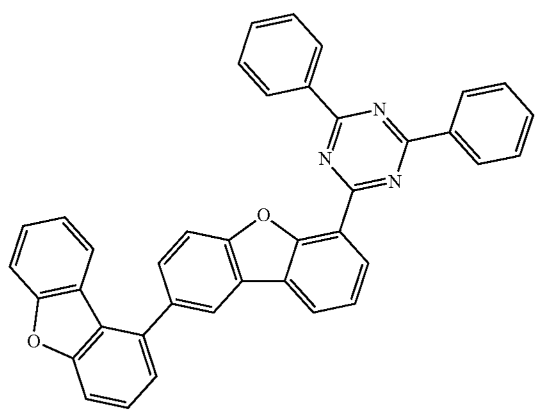
-continued
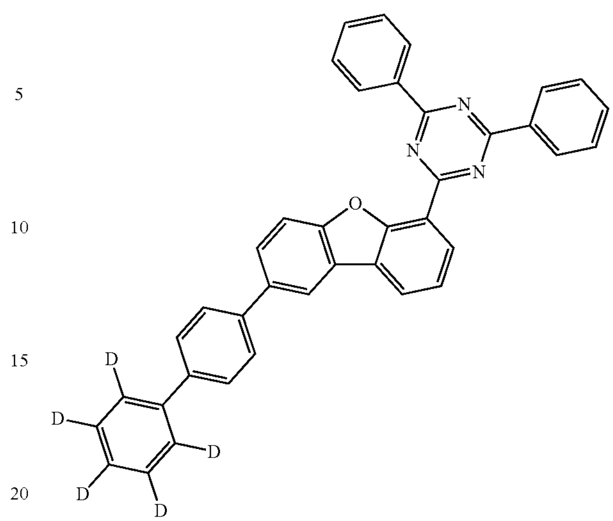
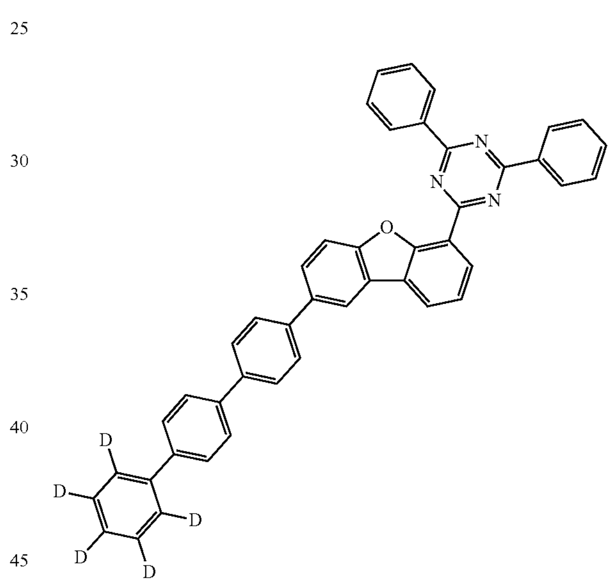
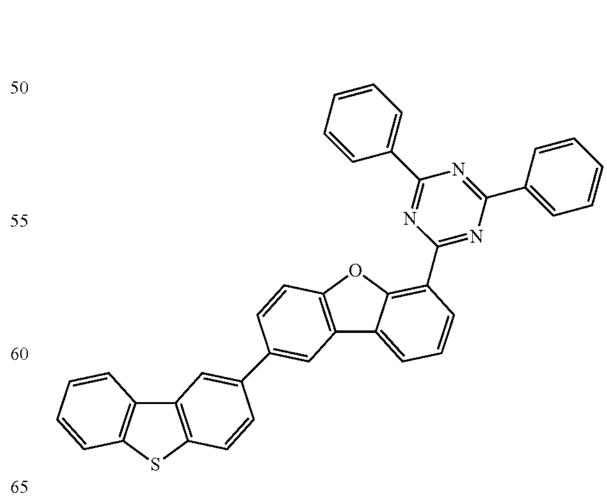

-continued
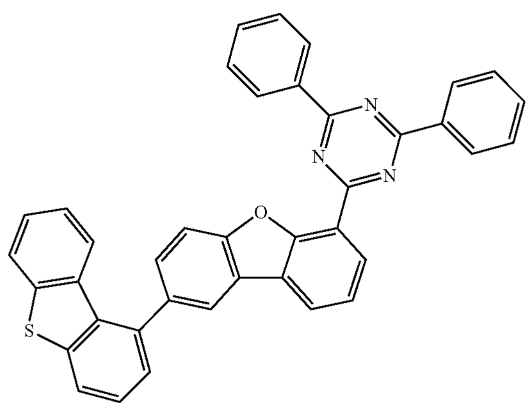
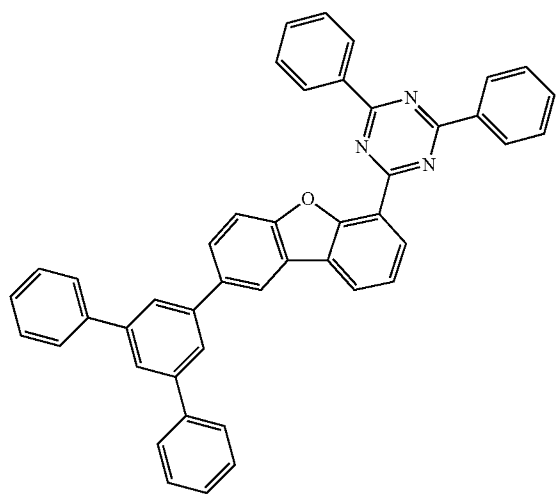
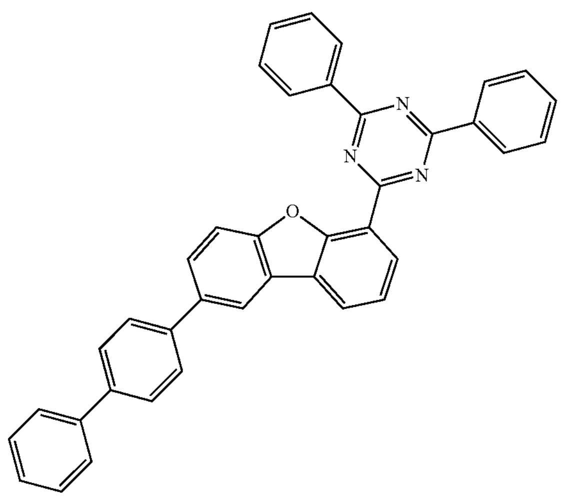
-continued
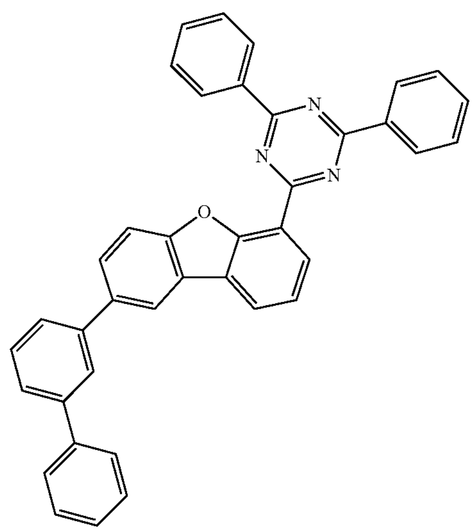
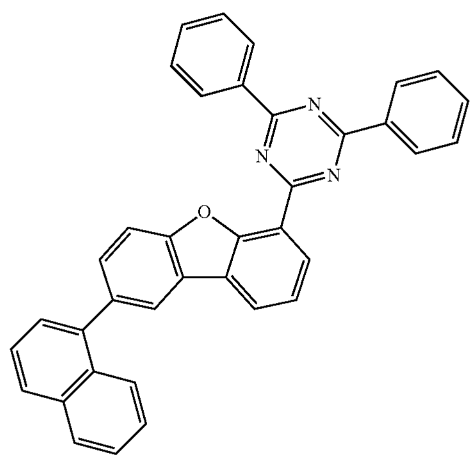
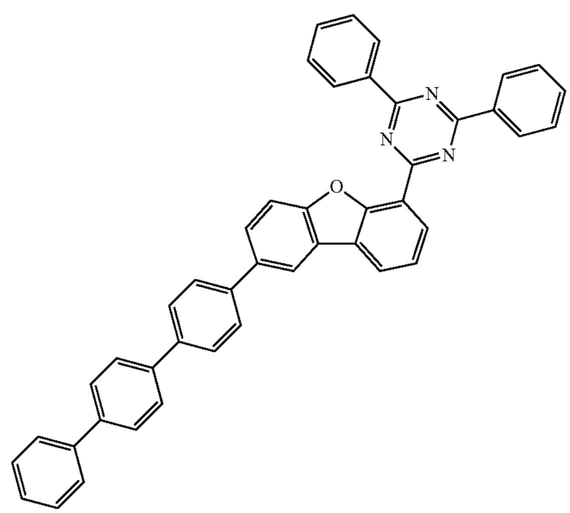

-continued
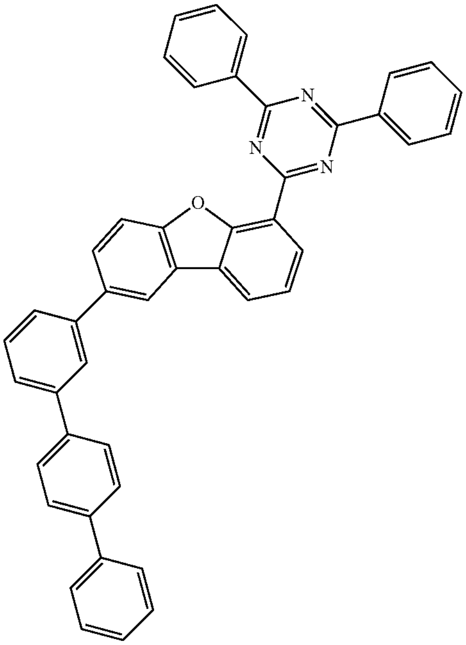
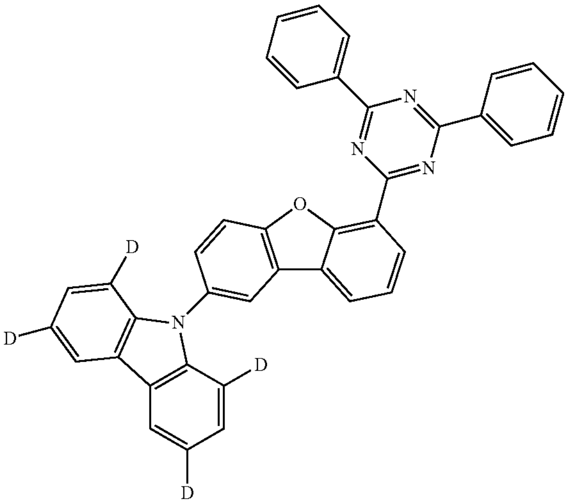
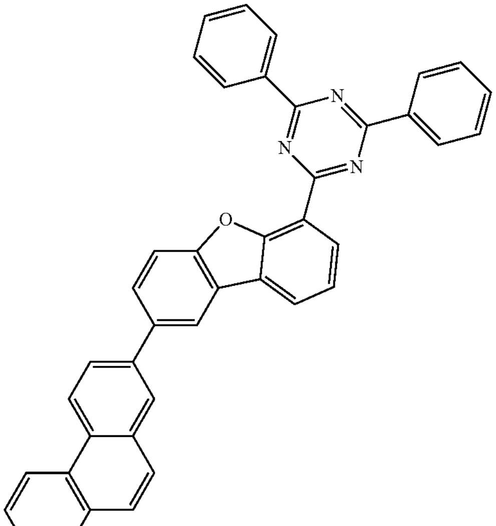
-continued
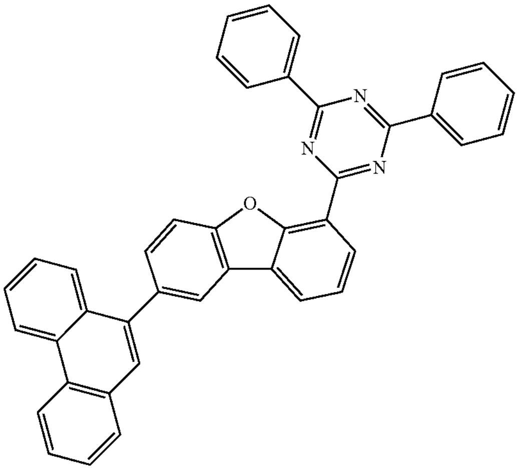
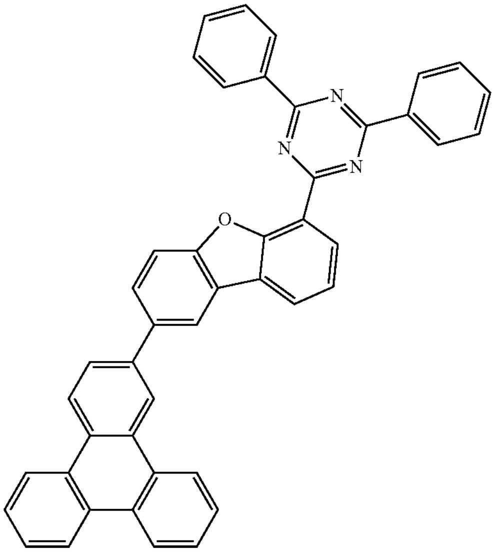
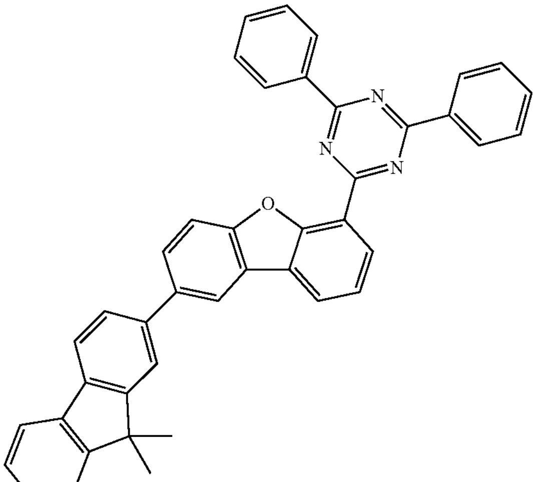

-continued
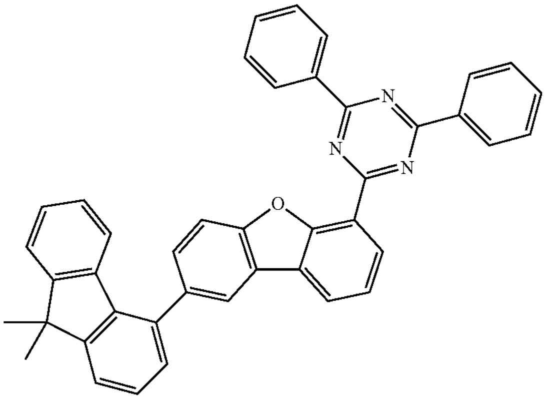
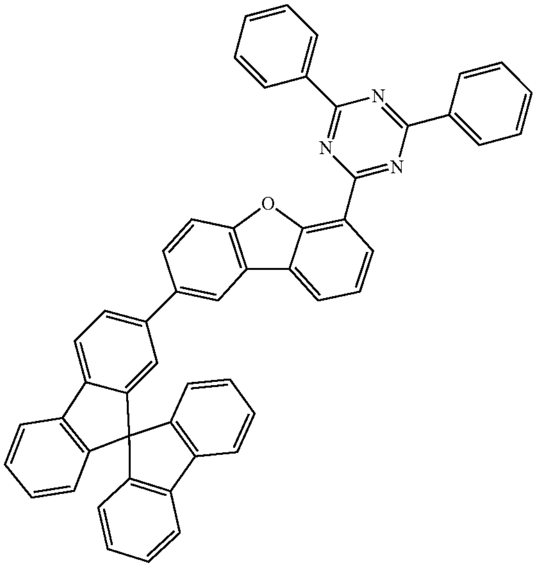
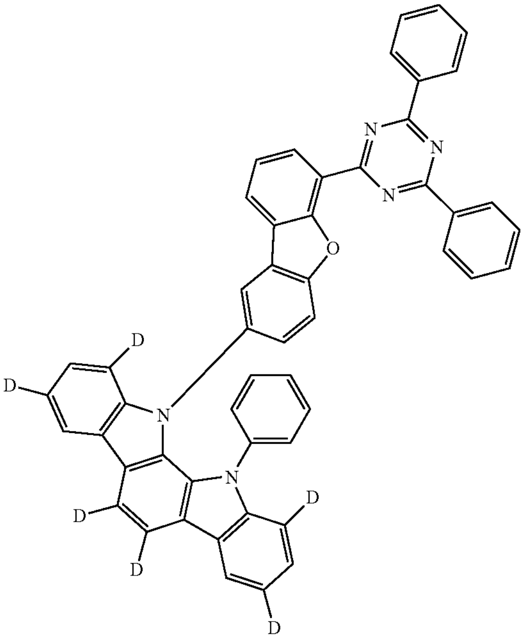
-continued
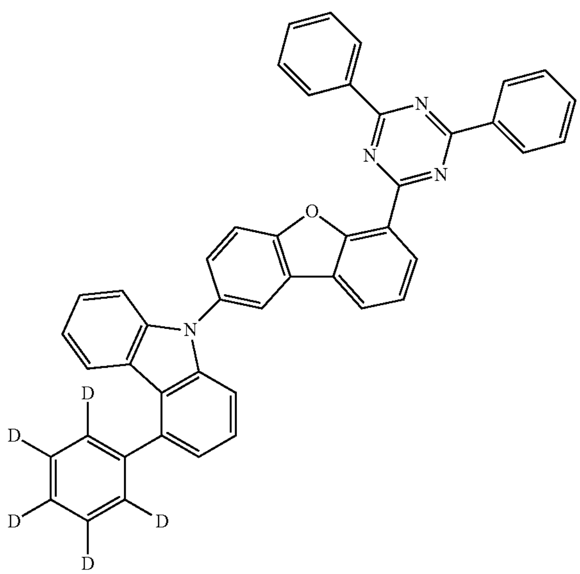
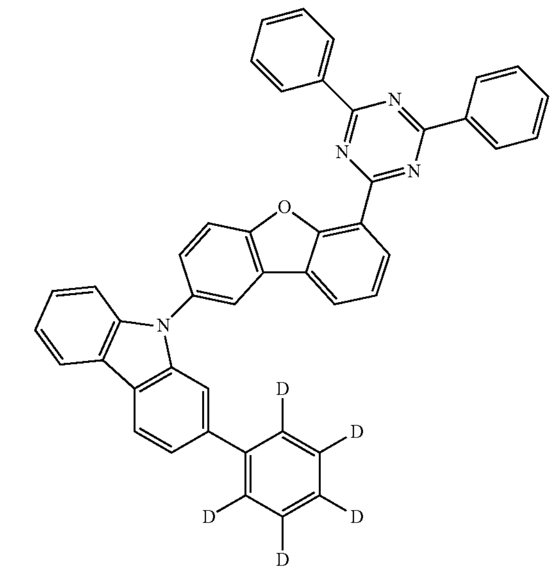
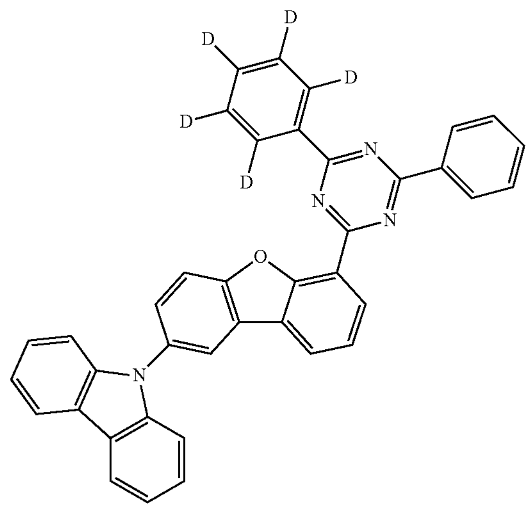

-continued
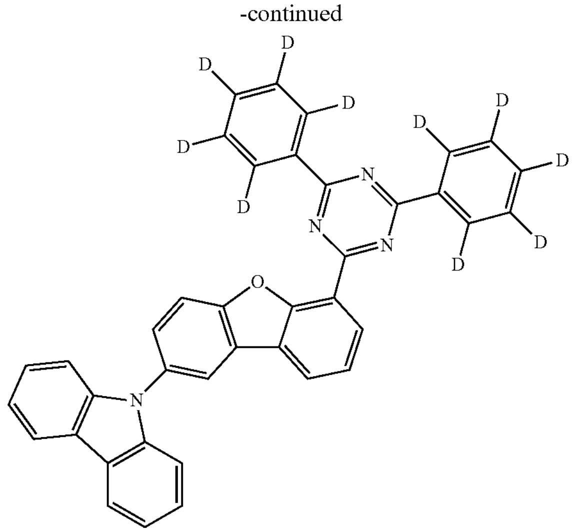
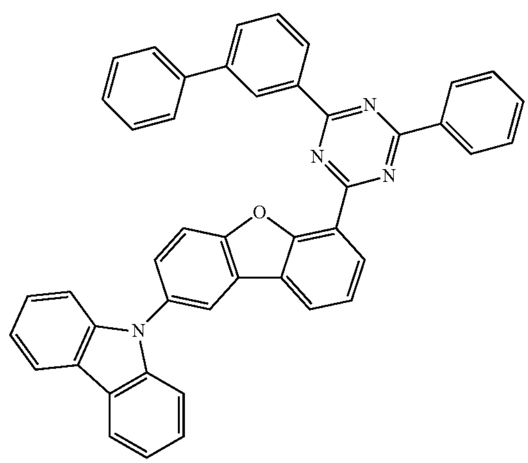
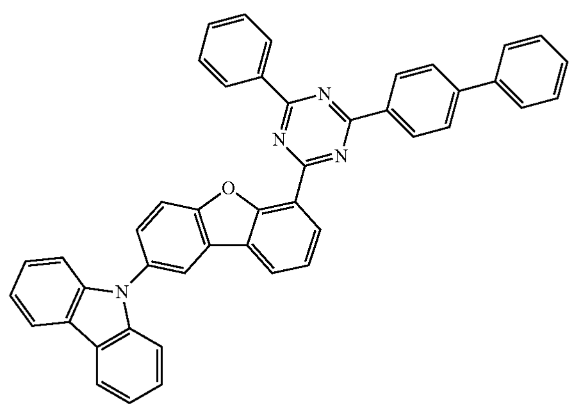
-continued
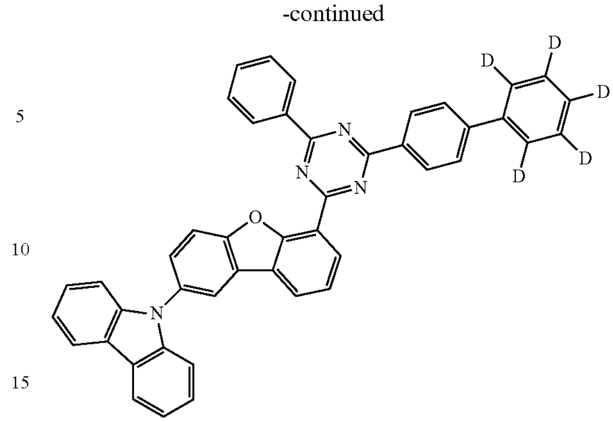
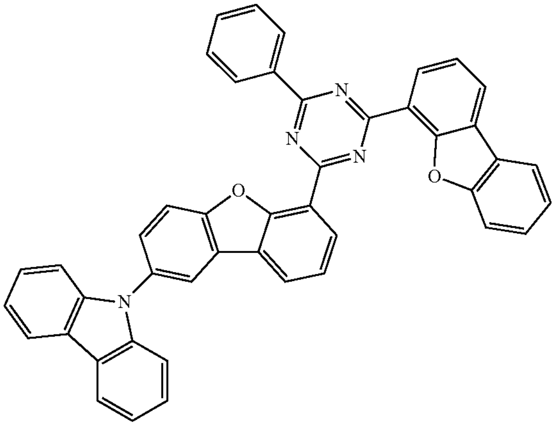
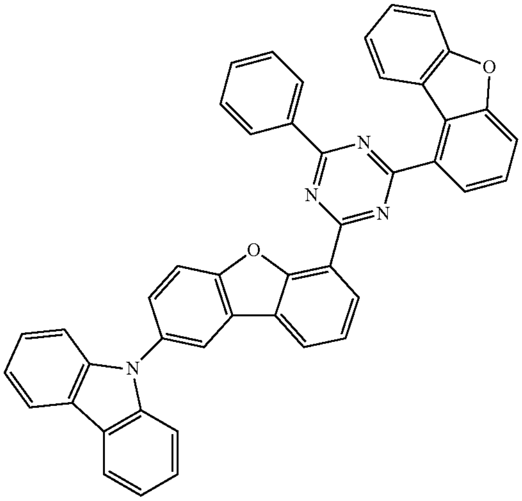

-continued
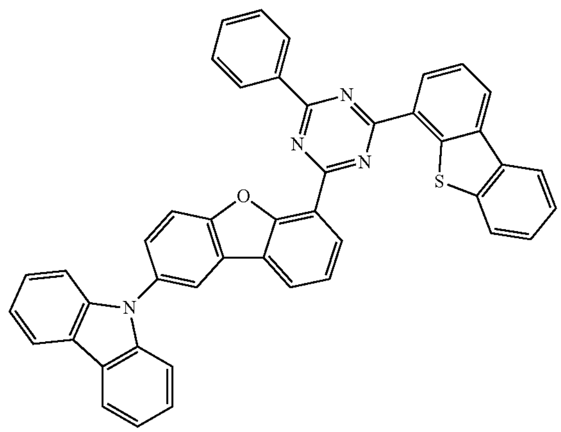
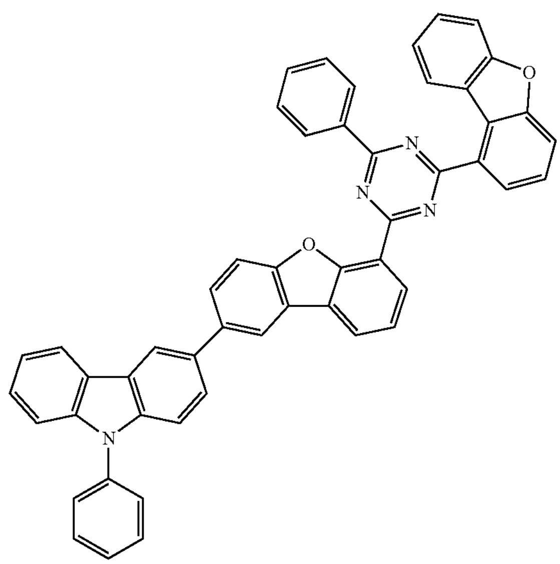
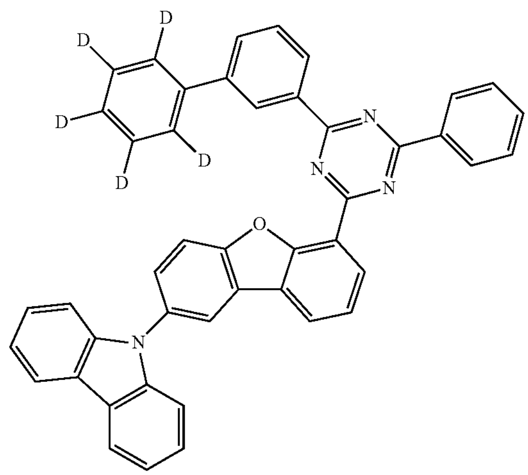
-continued
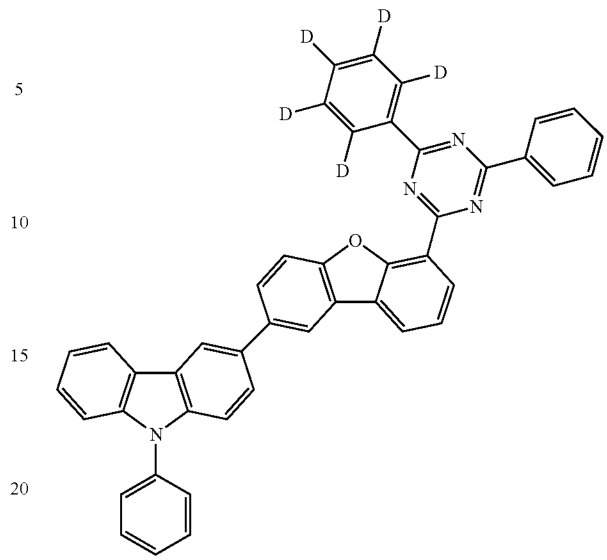
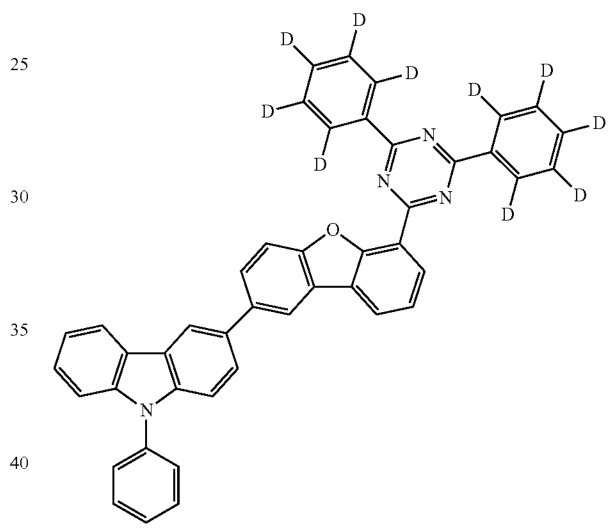
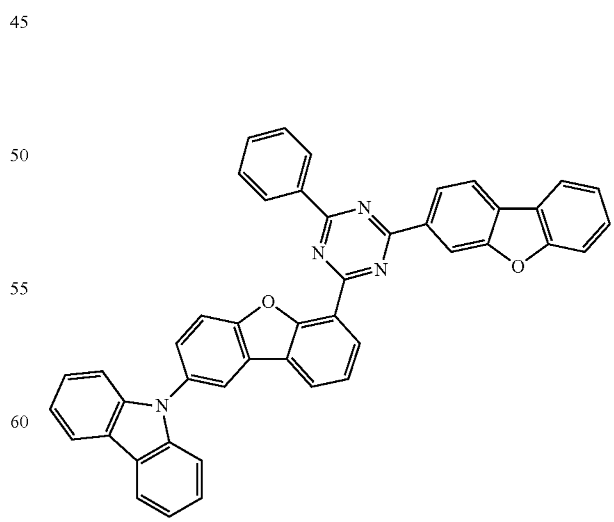

-continued
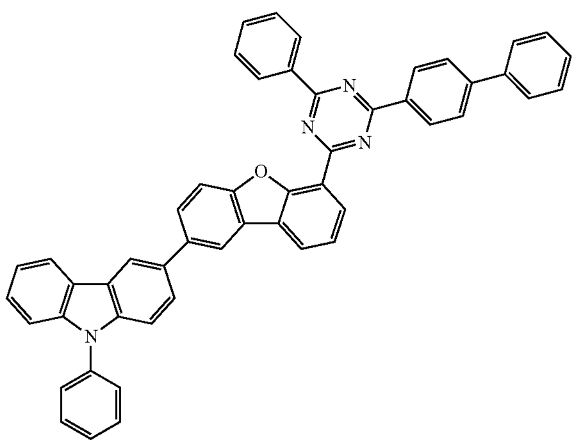
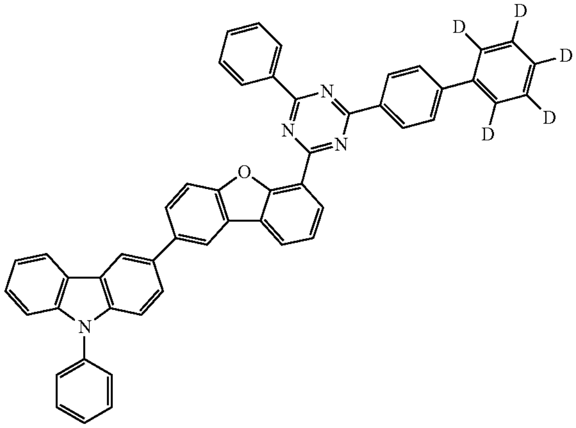
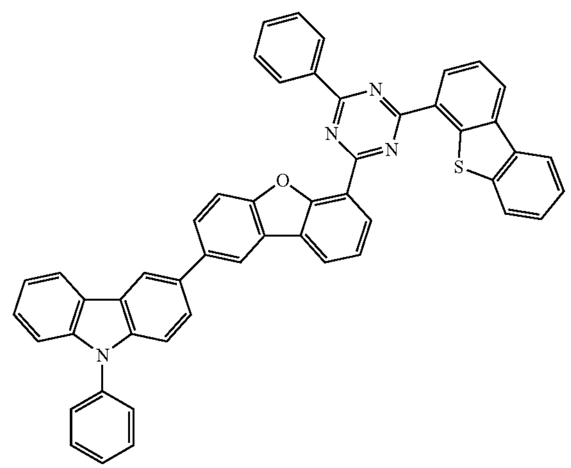
-continued
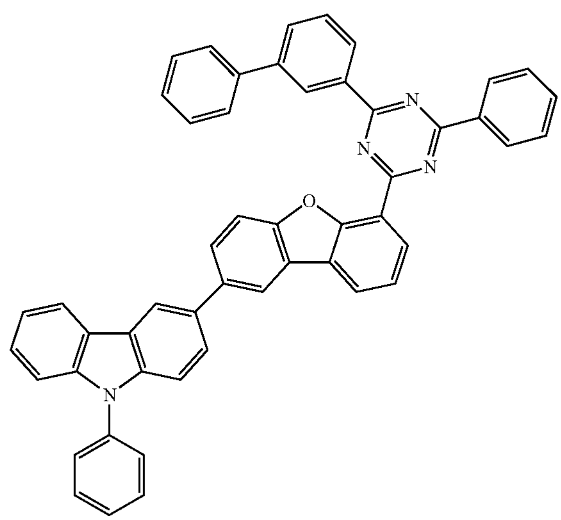
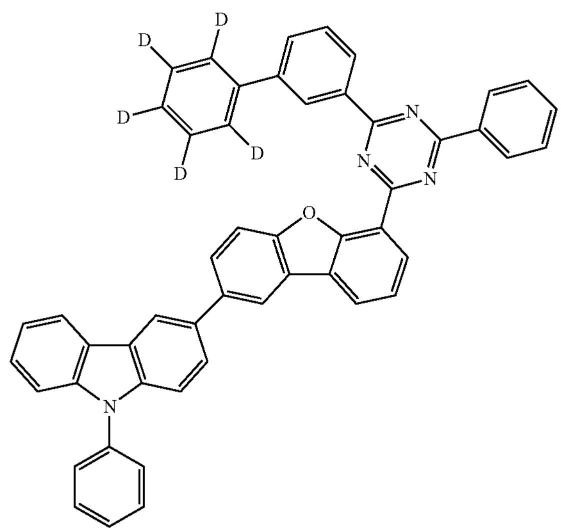
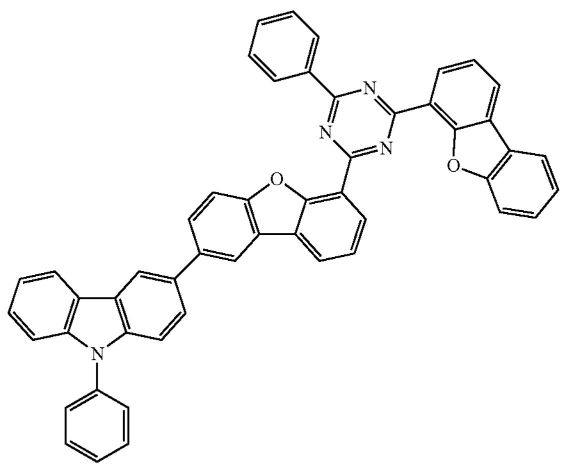

-continued
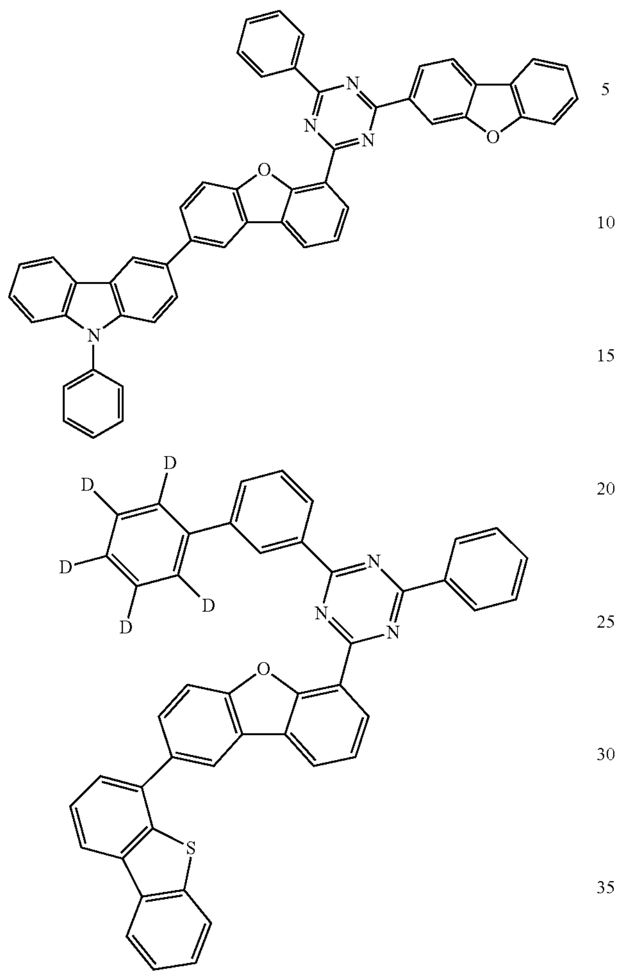
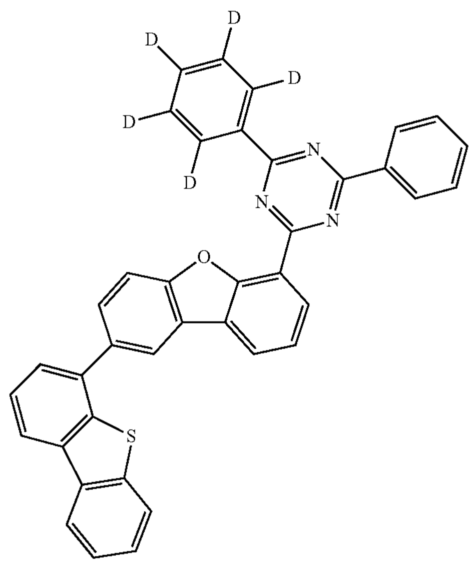
-continued
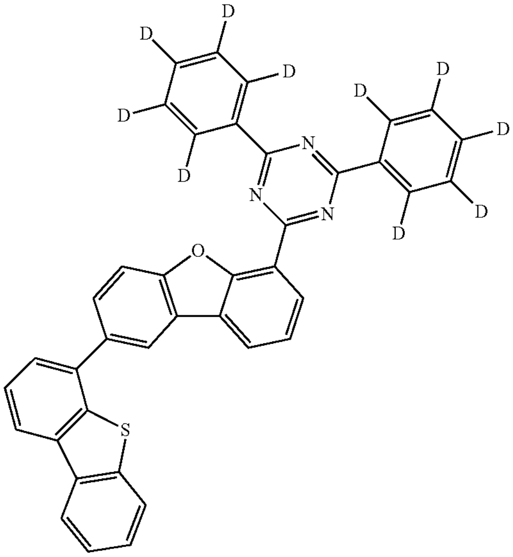
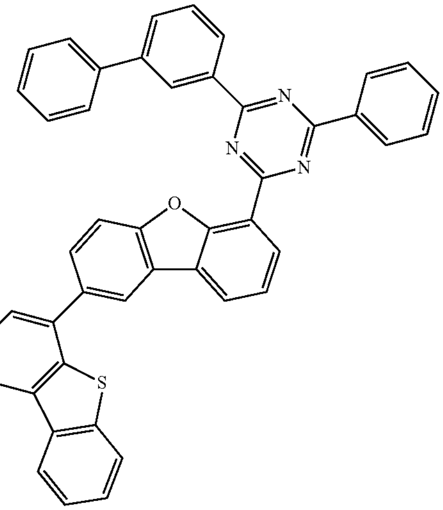
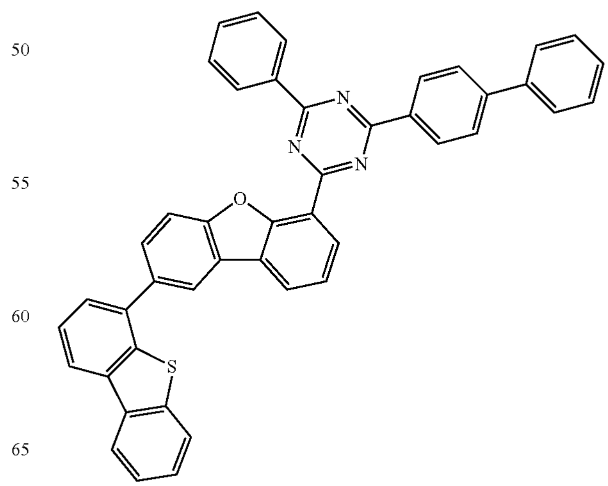

-continued
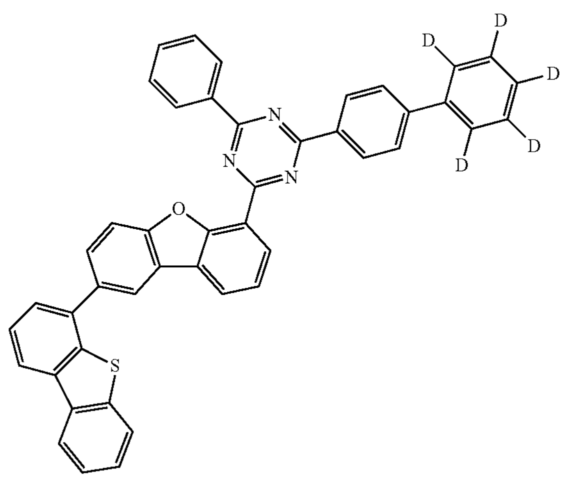
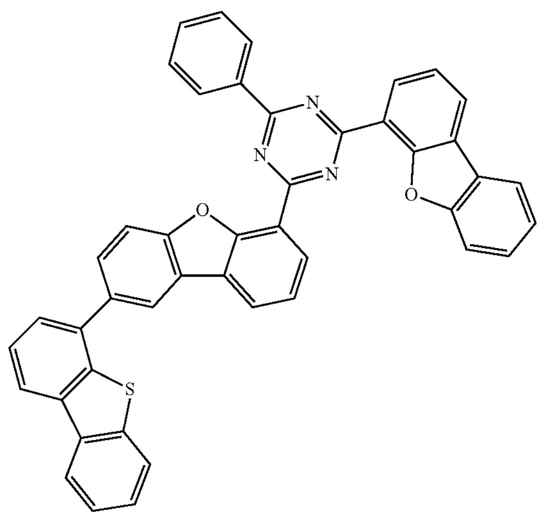
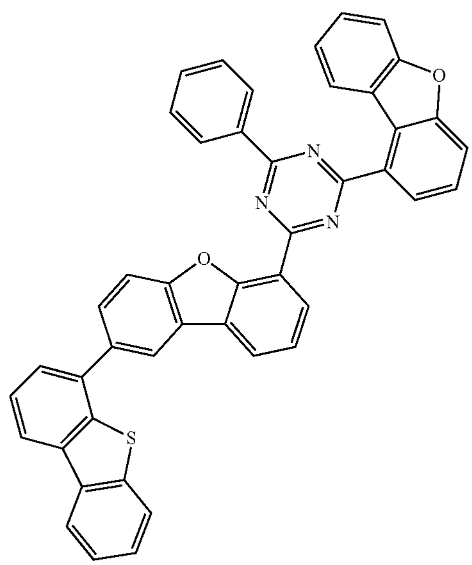
-continued
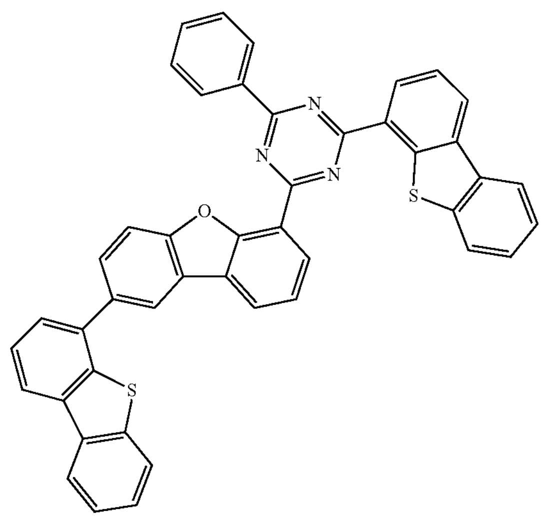
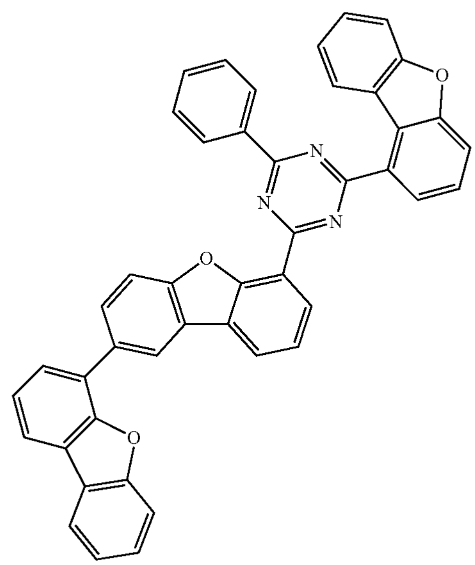
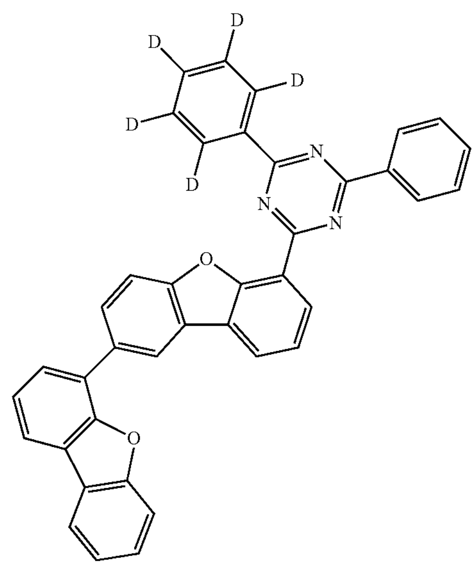

-continued
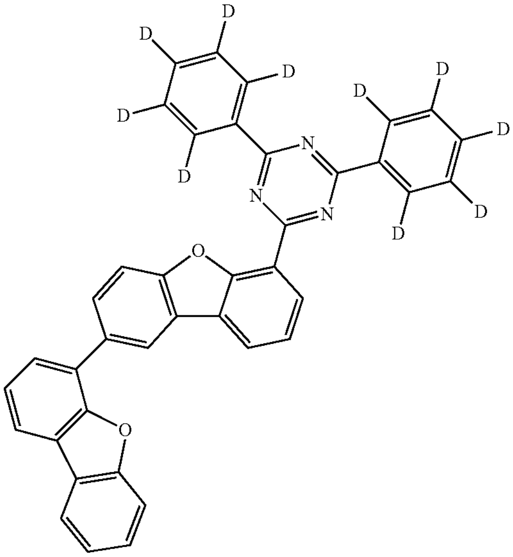
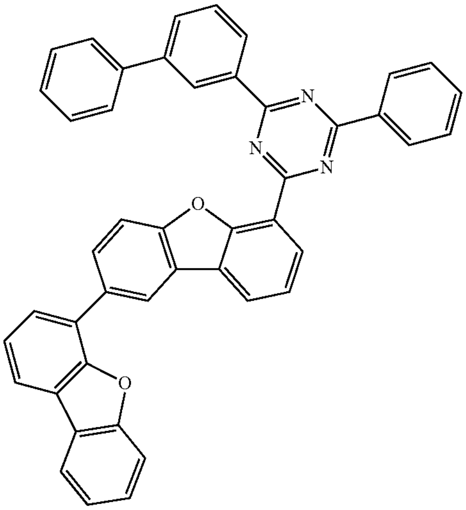
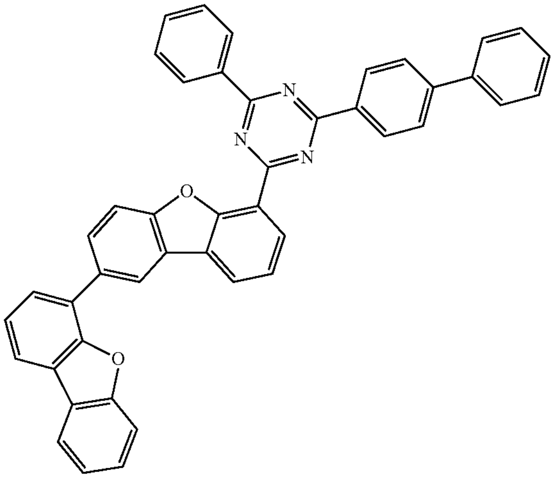
-continued
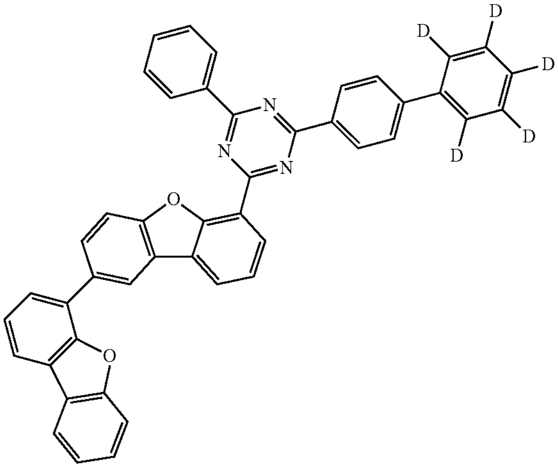
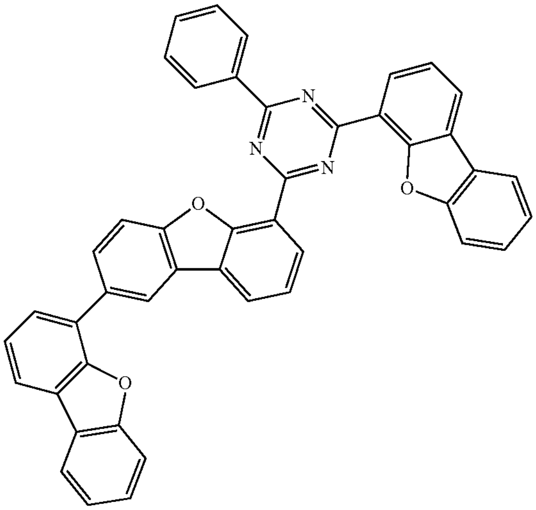
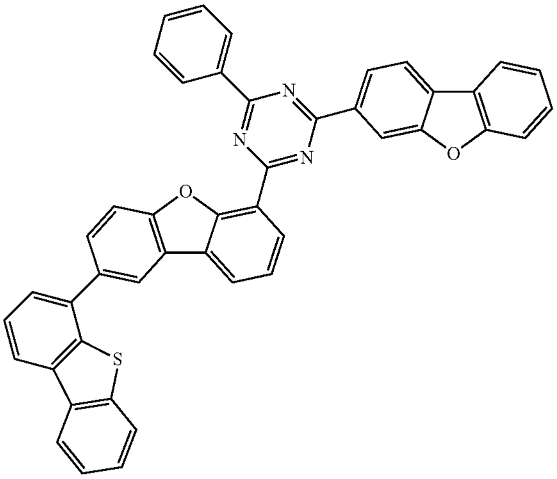

-continued
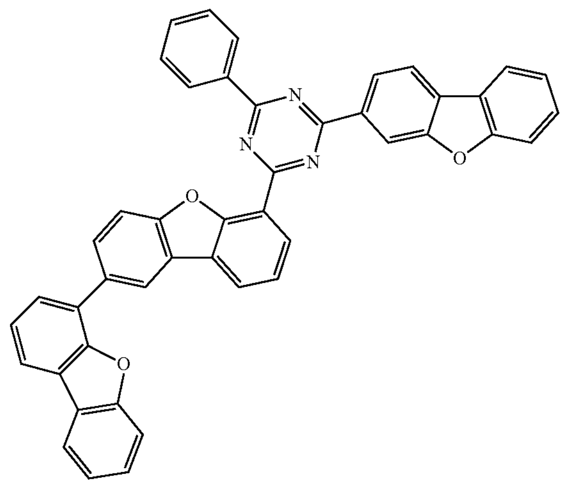
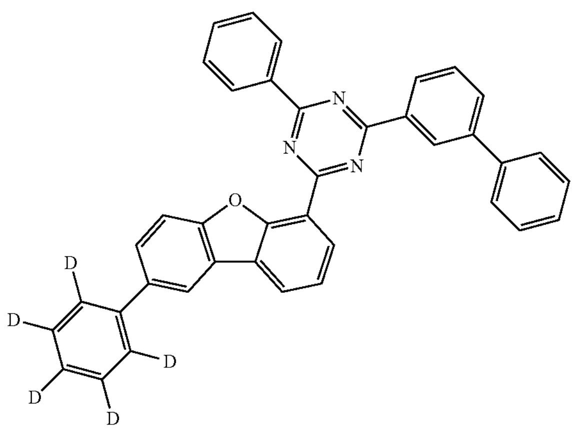
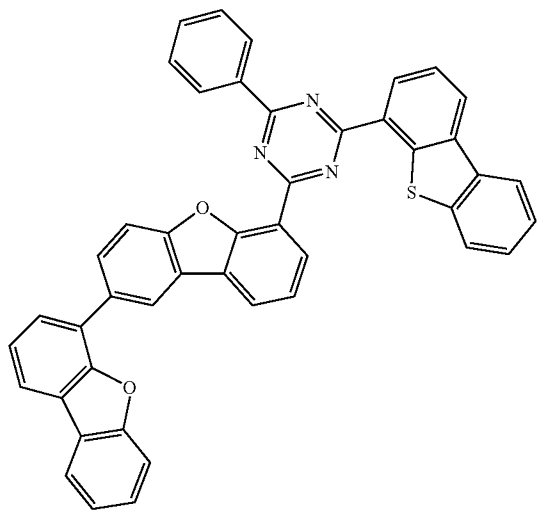
-continued
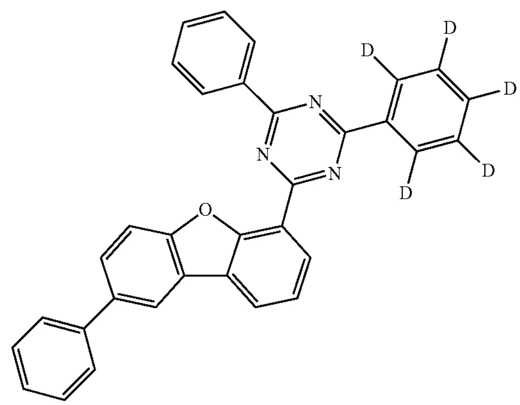
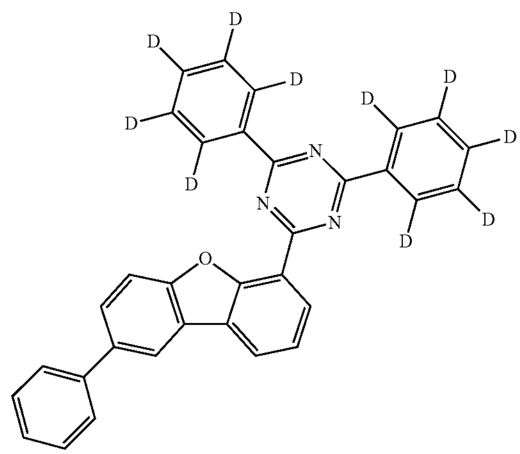
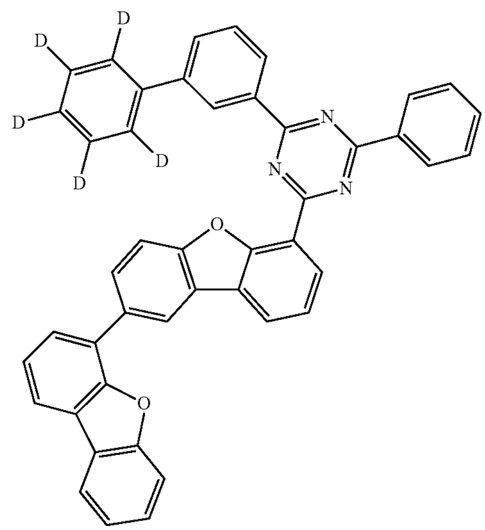

-continued
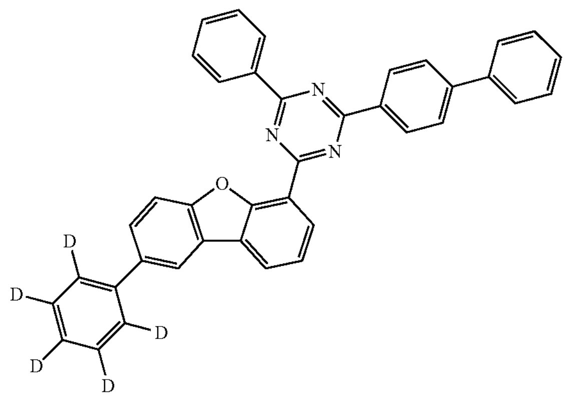
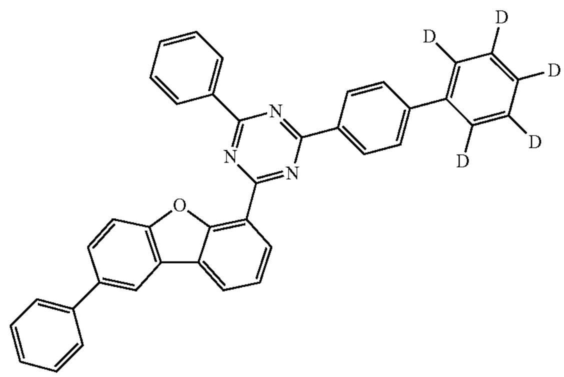
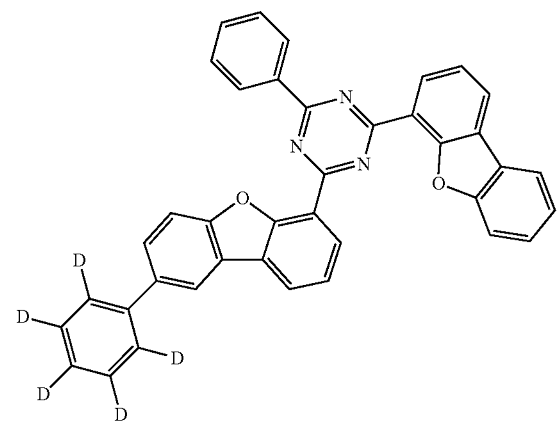
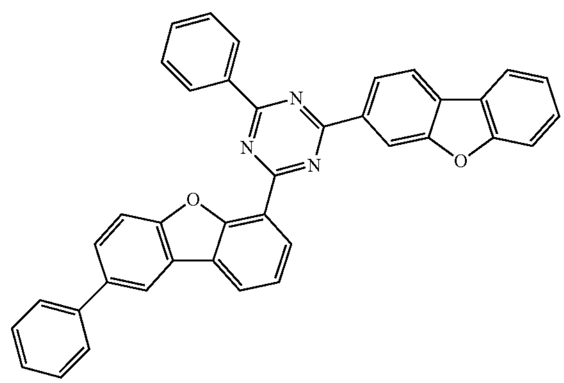
-continued
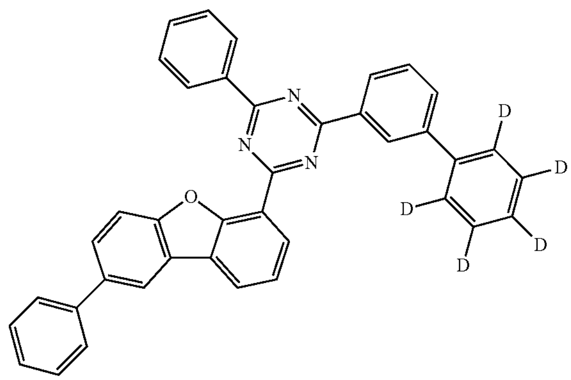
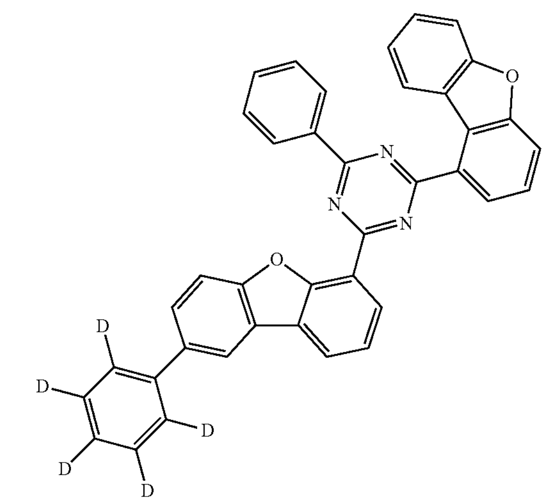
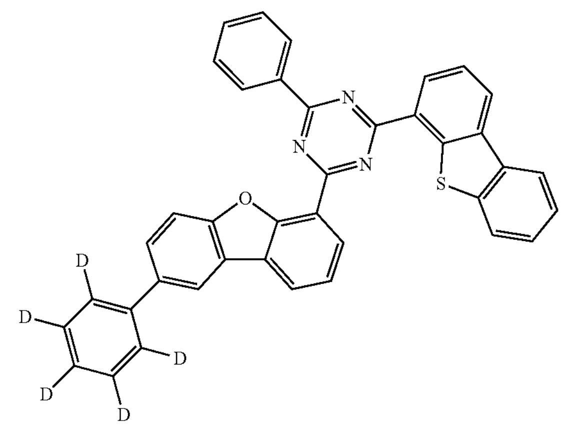

-continued
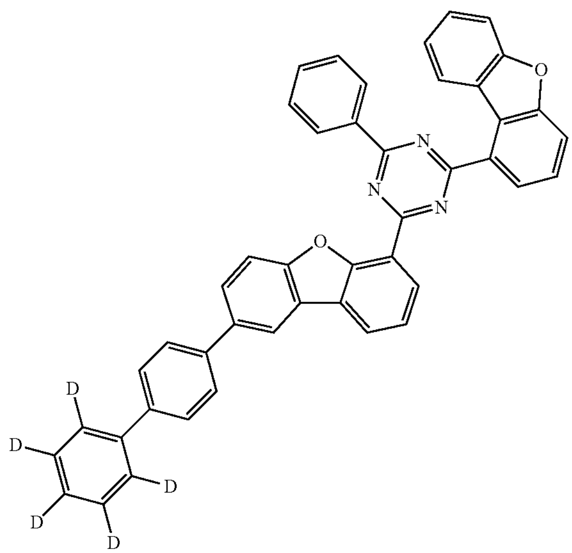
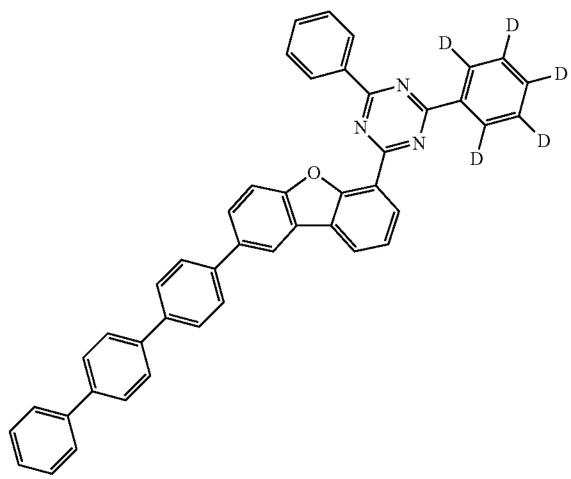
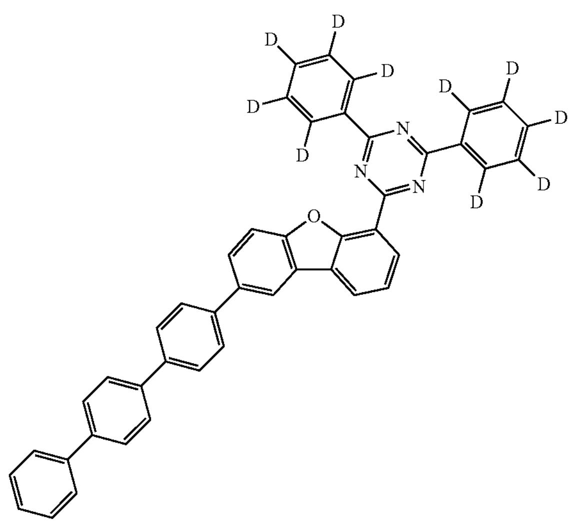
-continued
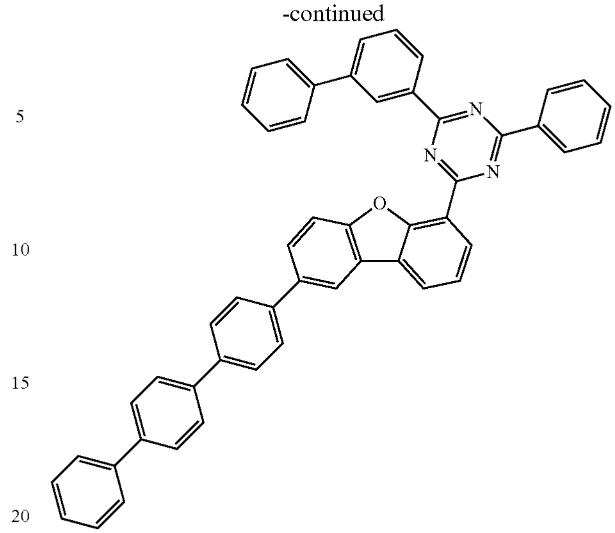
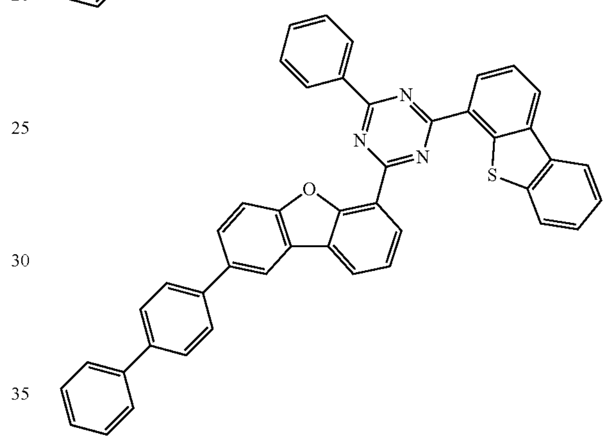
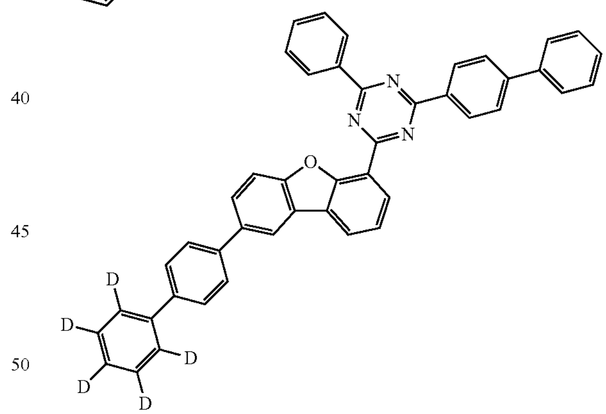
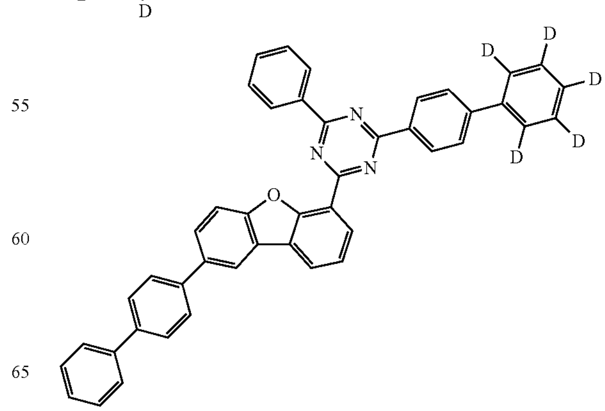

-continued
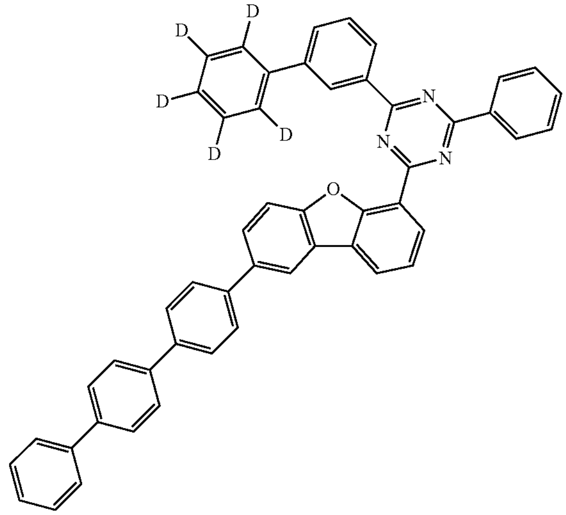
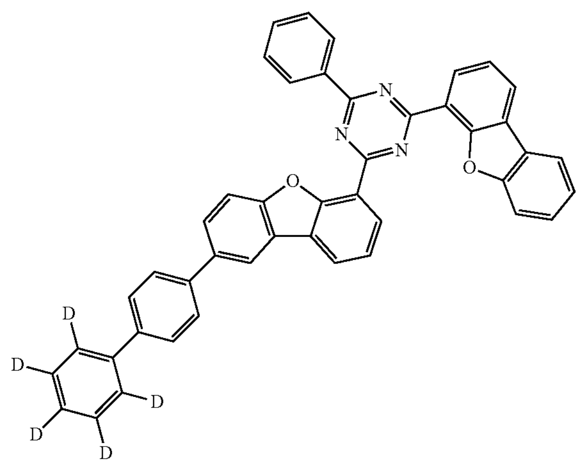
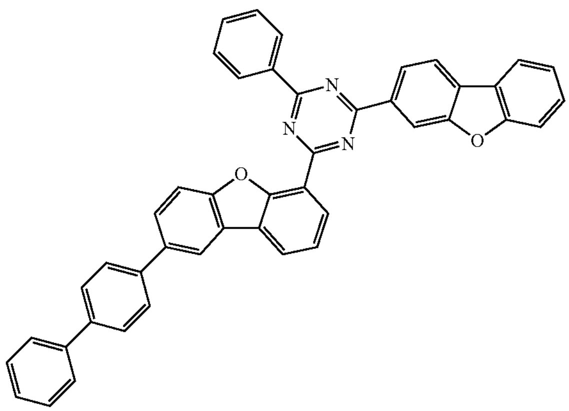
-continued
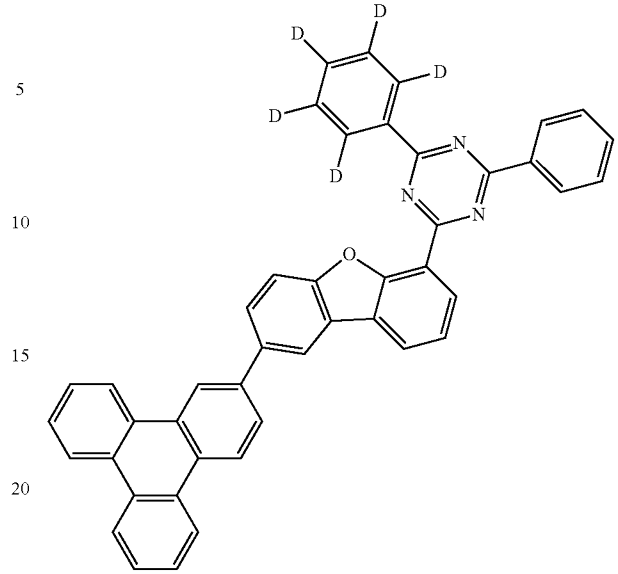
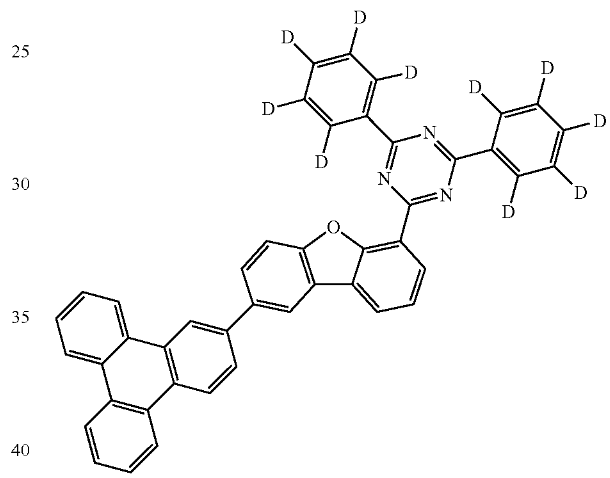
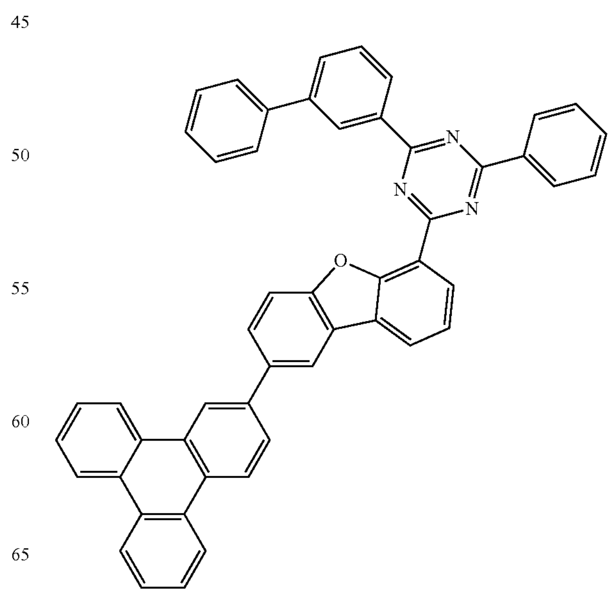

-continued
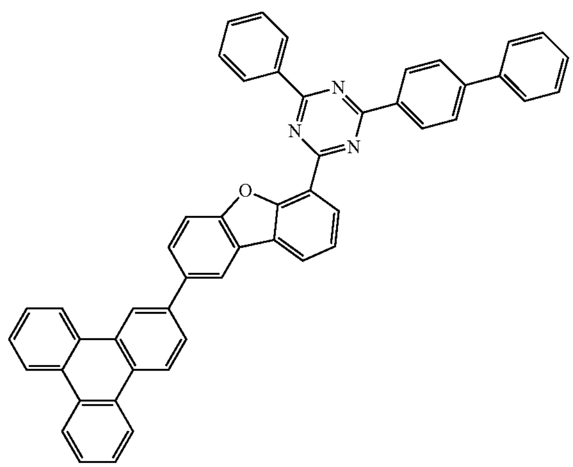
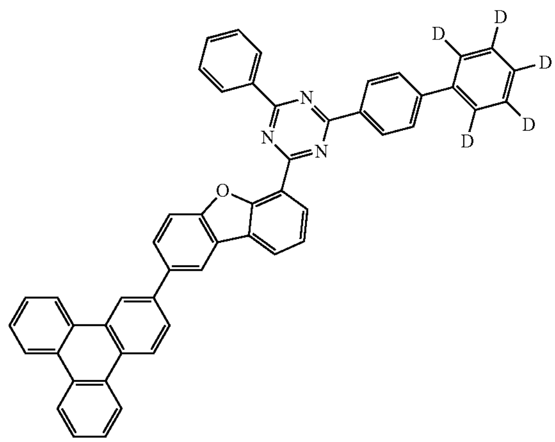
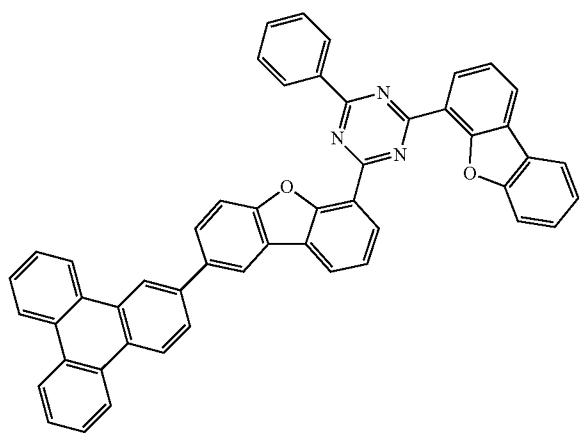
-continued
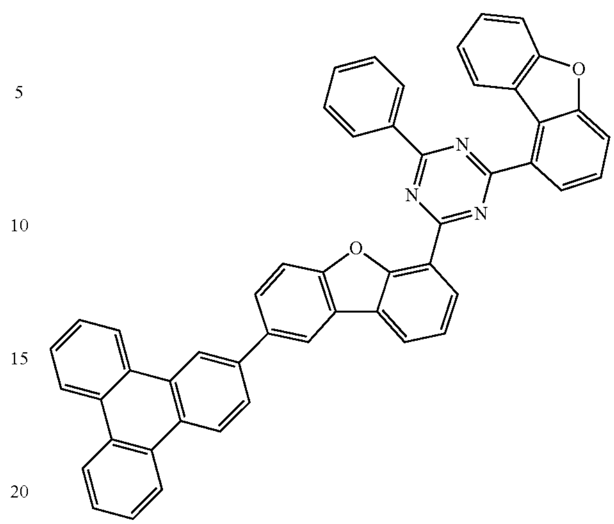
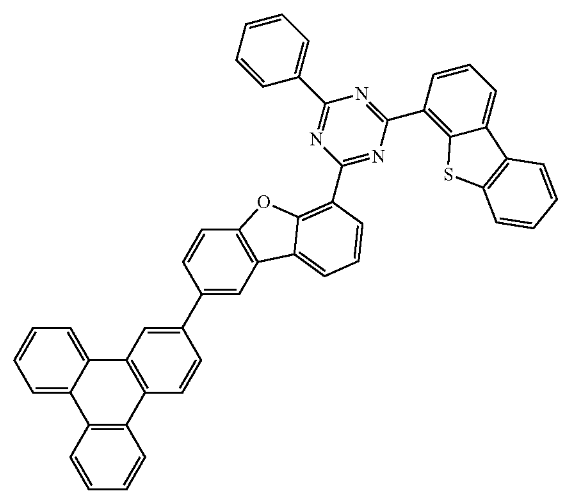
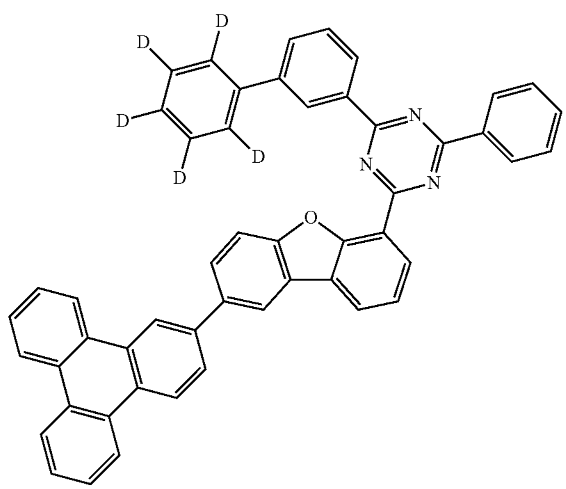

-continued
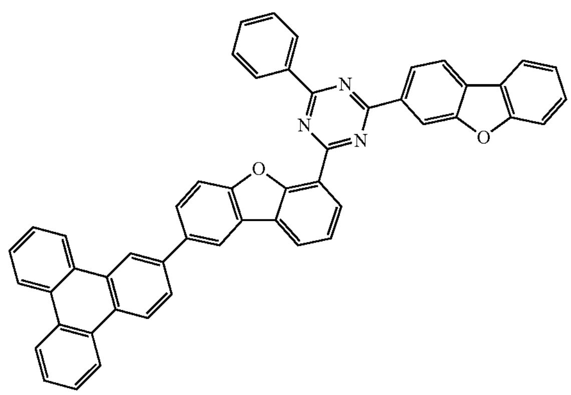
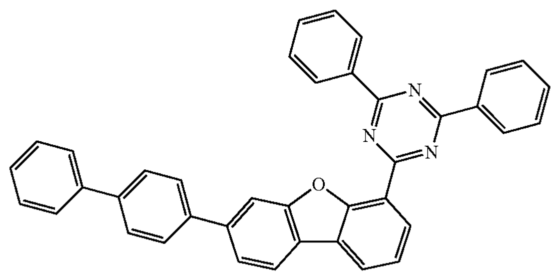
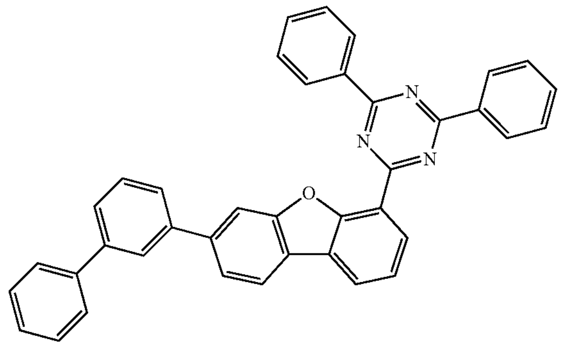
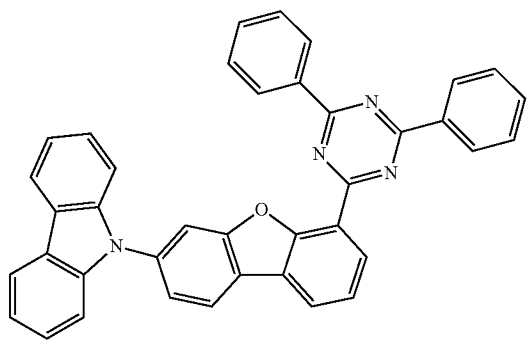
-continued
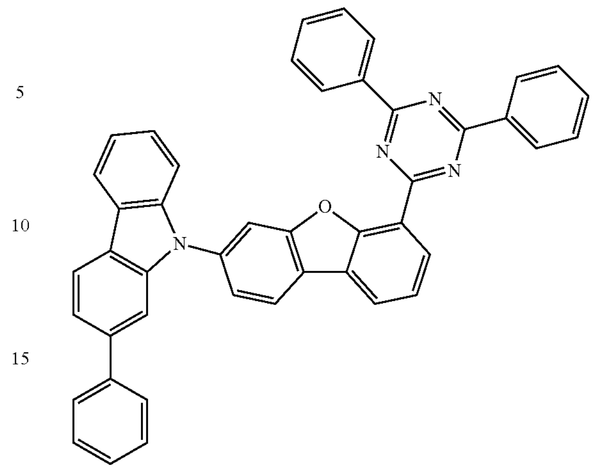
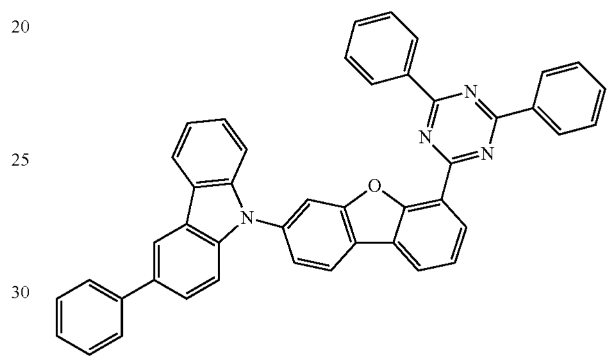
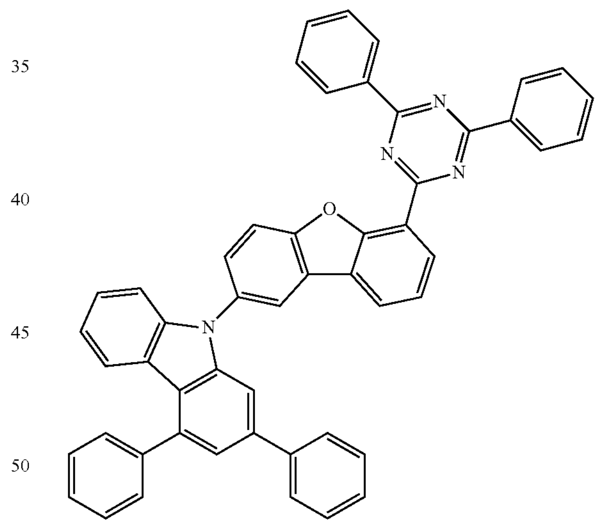
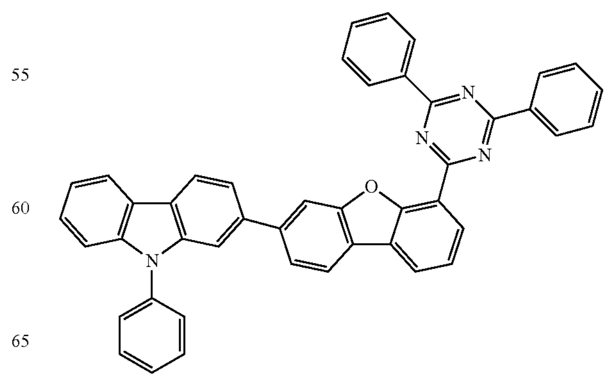

-continued
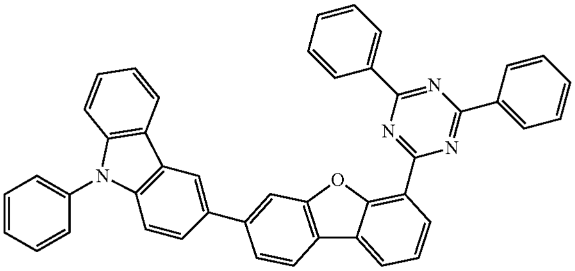
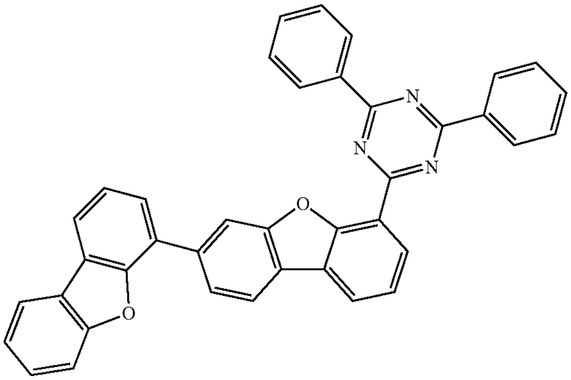
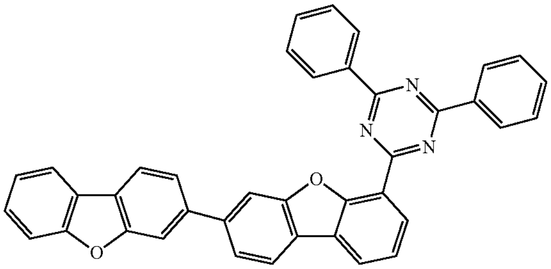
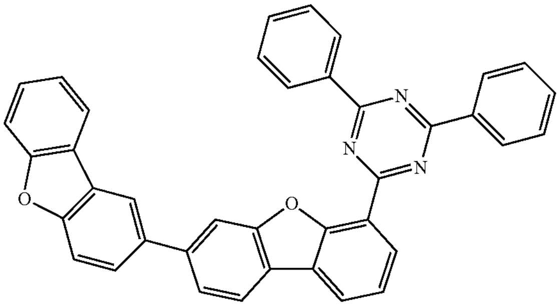
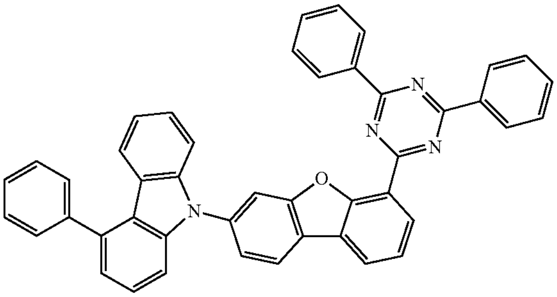
-continued
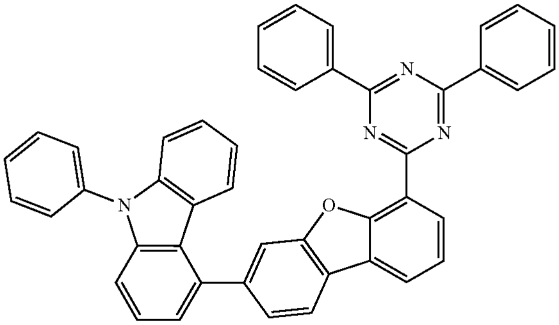
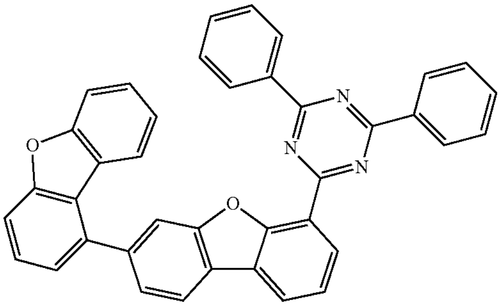
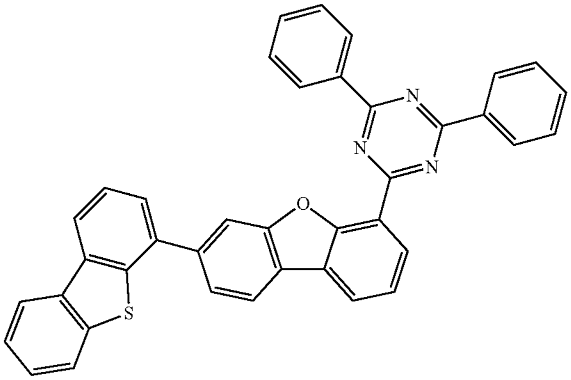
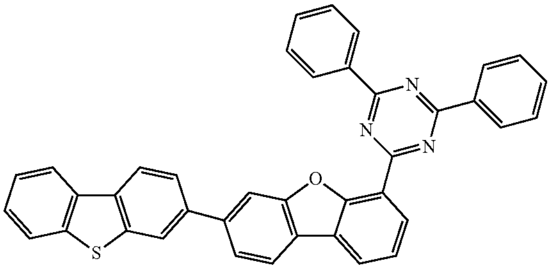
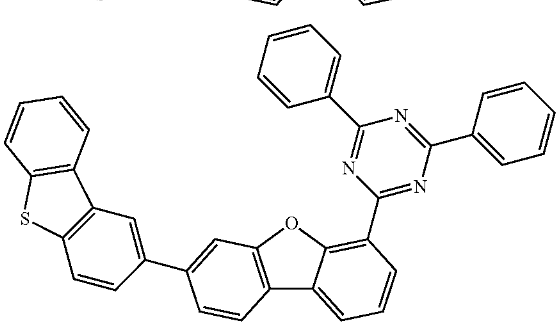

-continued
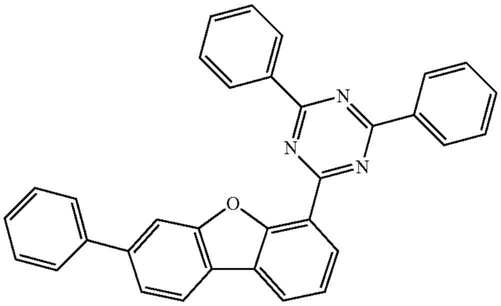
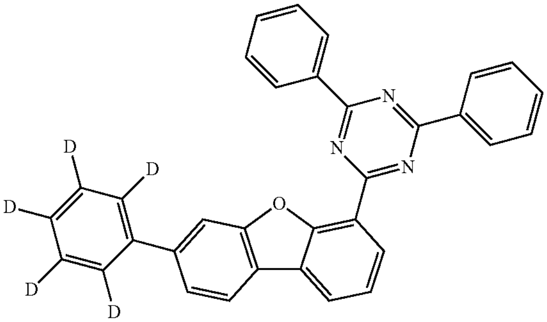
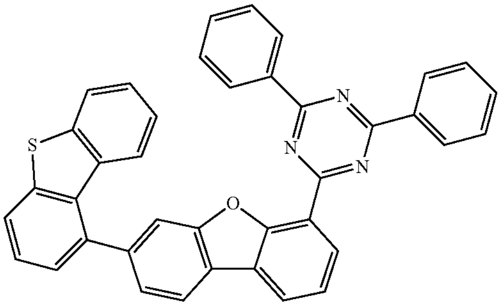
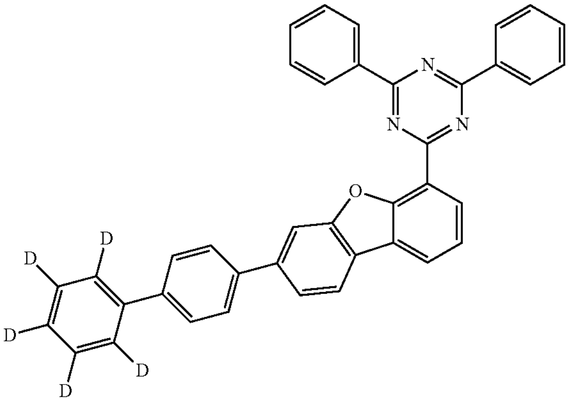
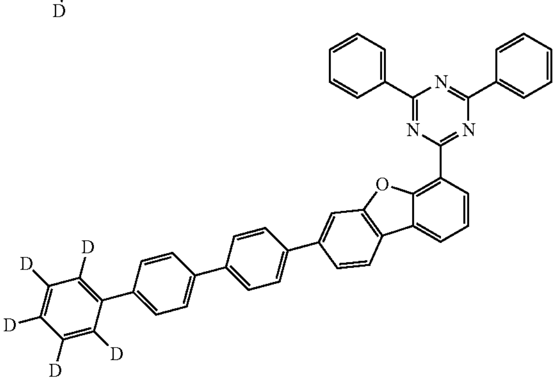
-continued
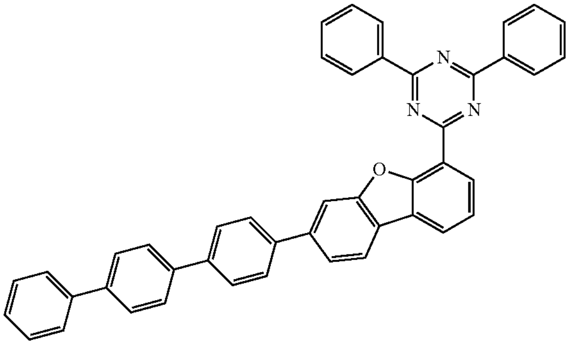
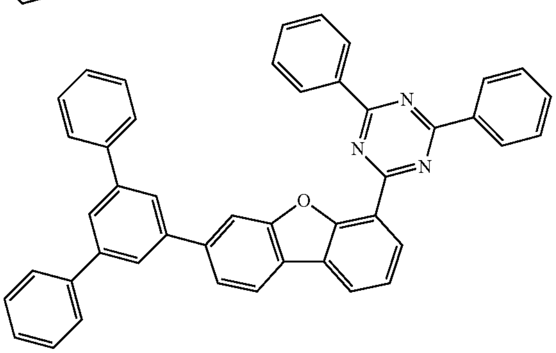
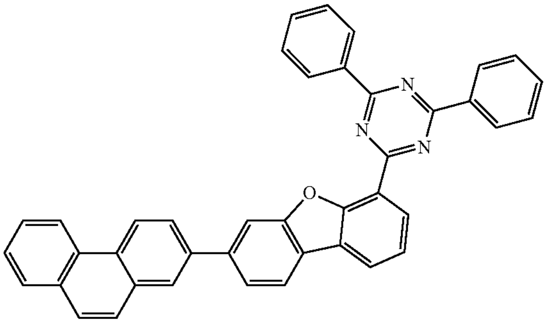
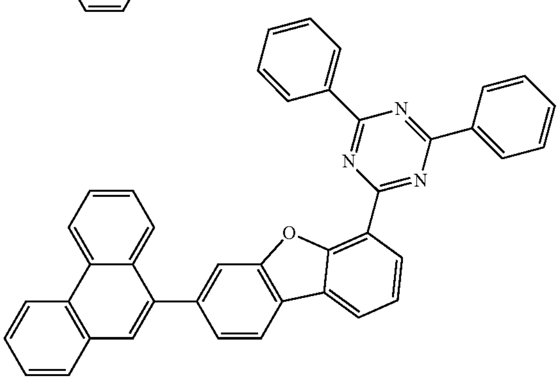
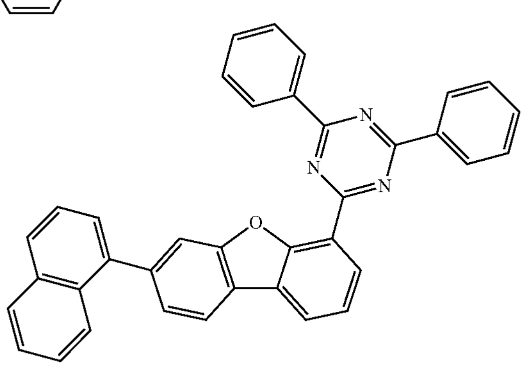

-continued
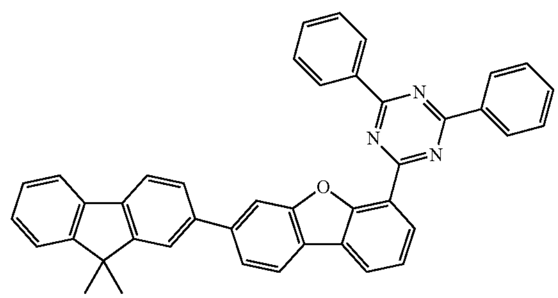
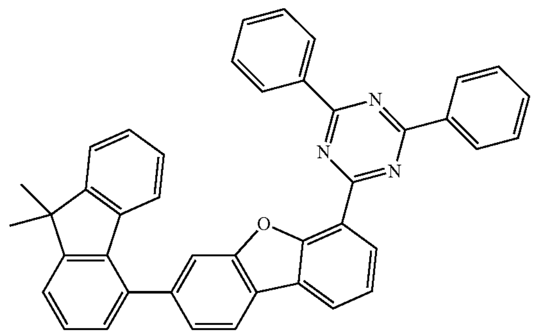
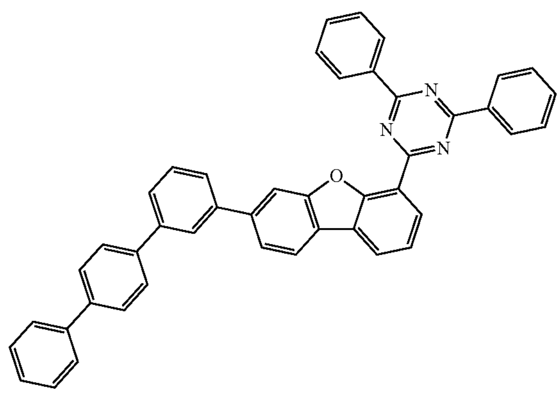
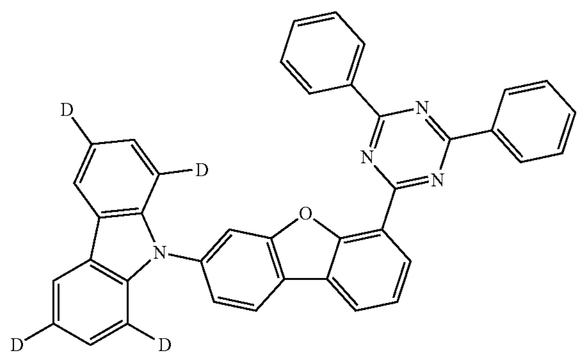
-continued
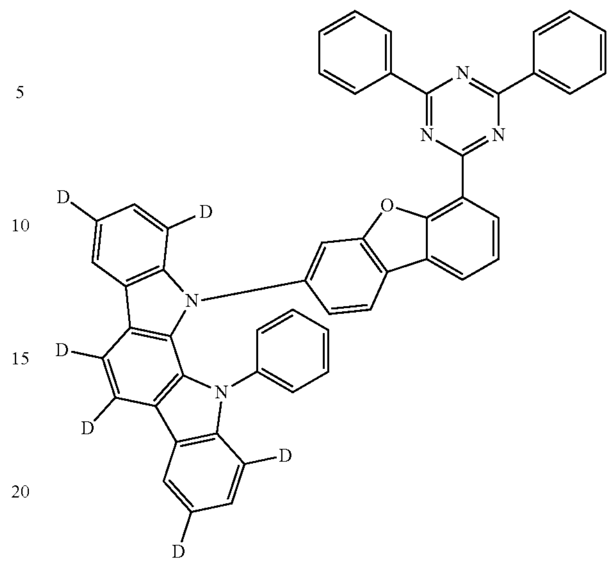
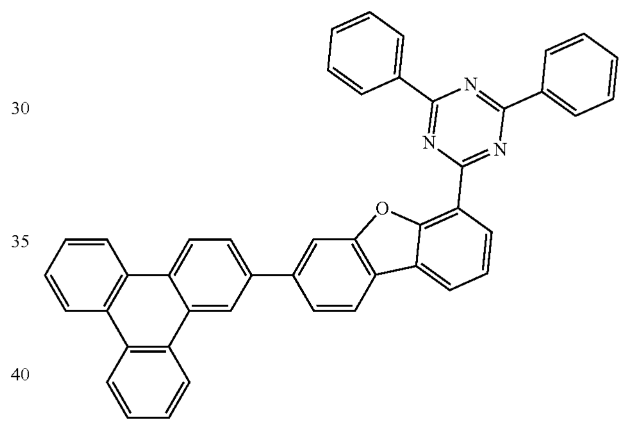
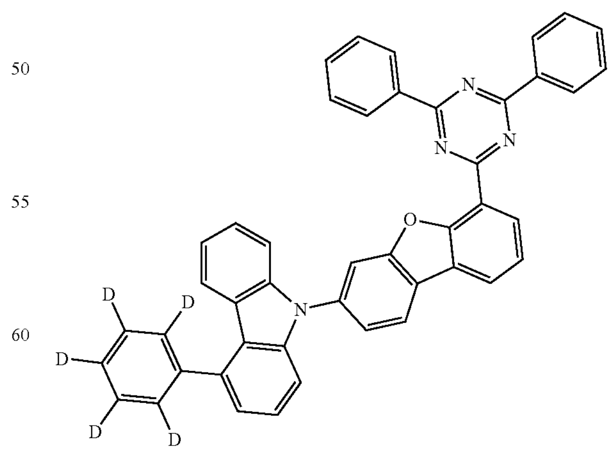

-continued
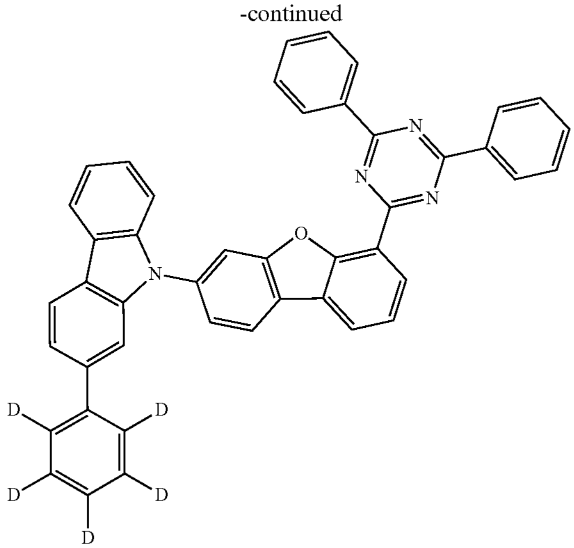
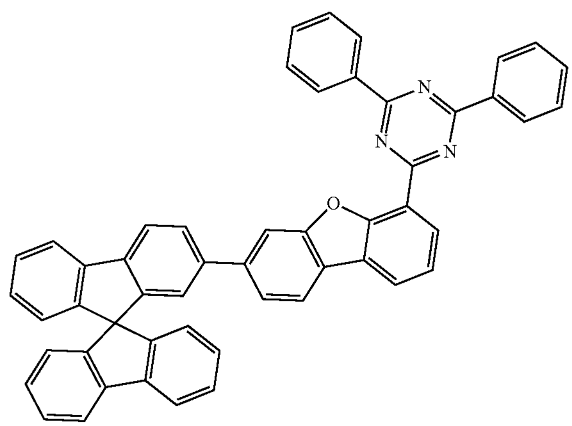
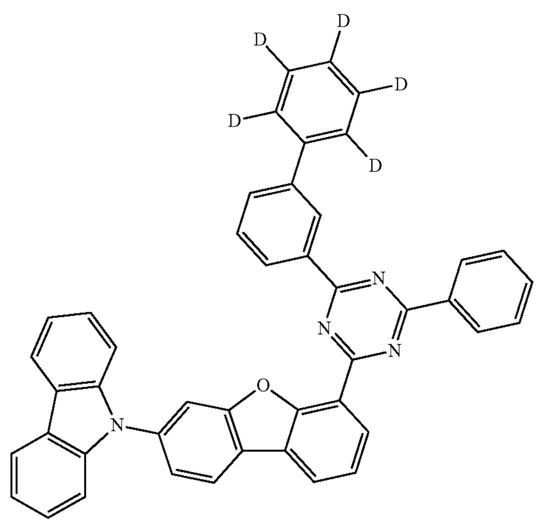
-continued
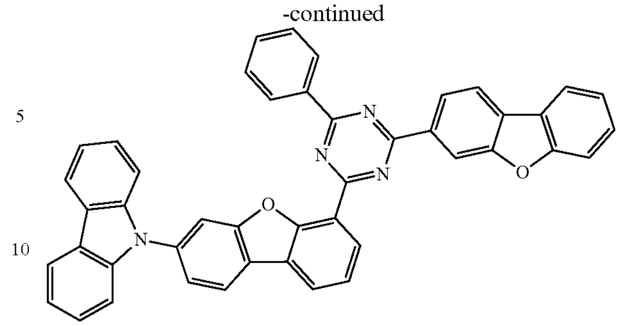
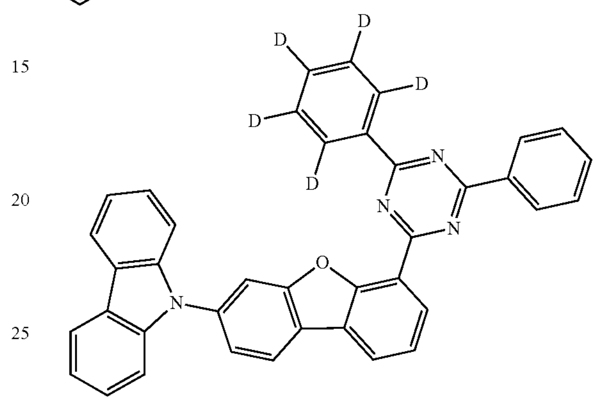
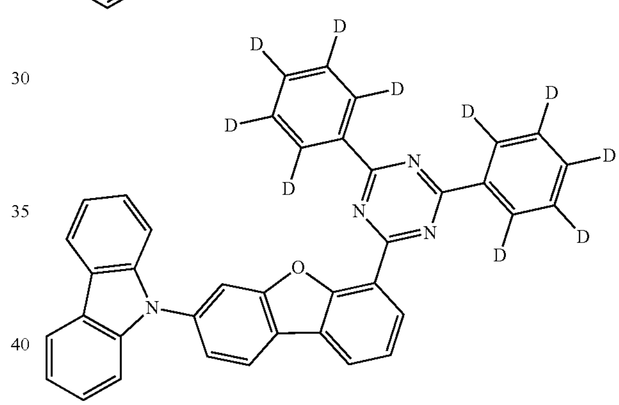
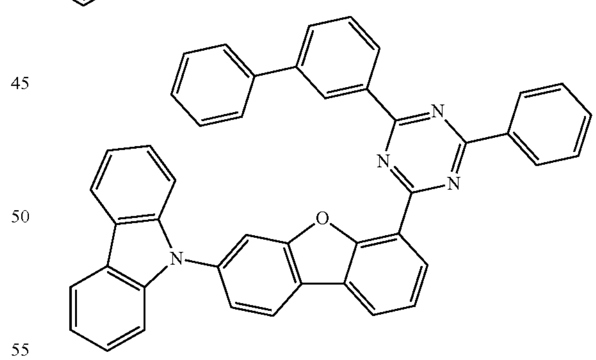
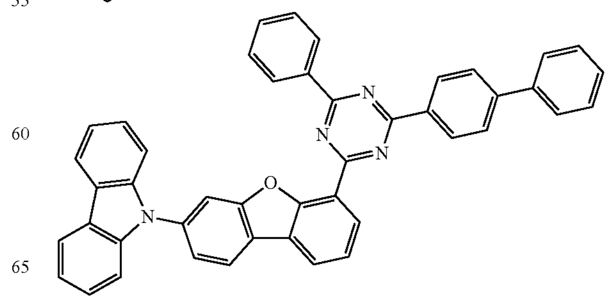

-continued
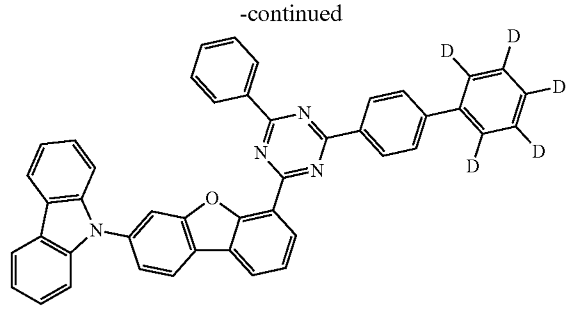
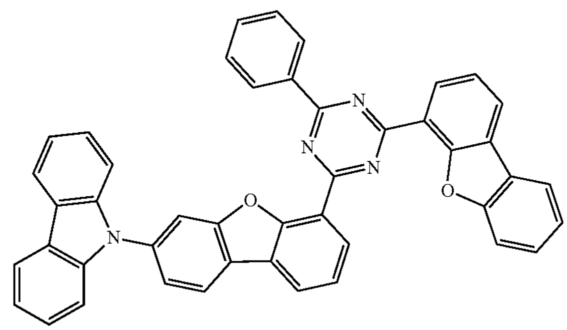
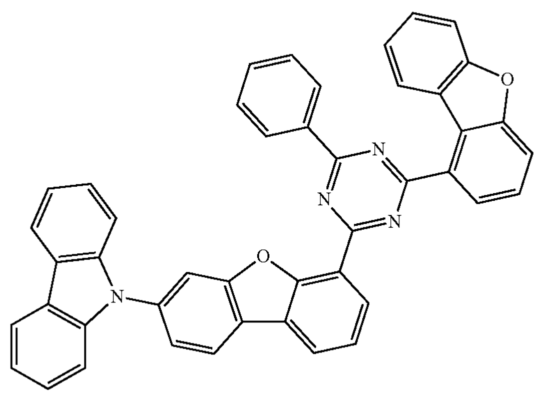
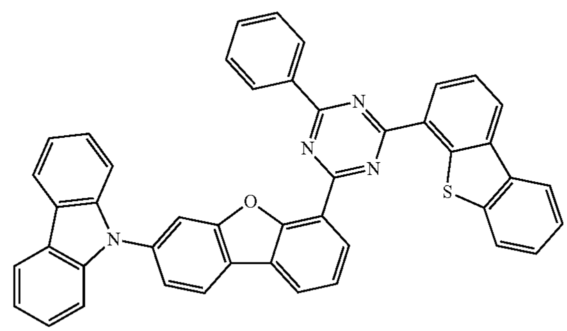
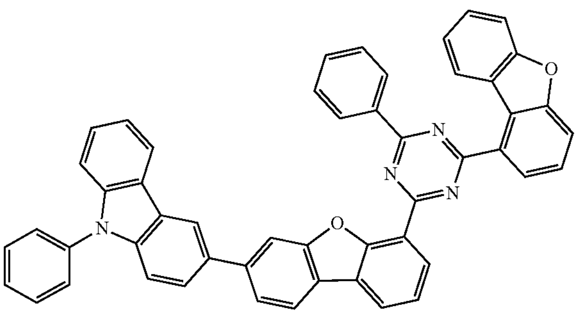
-continued
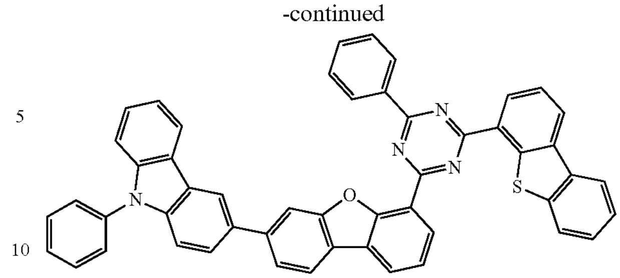
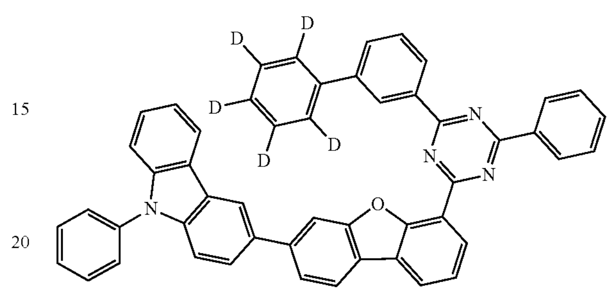
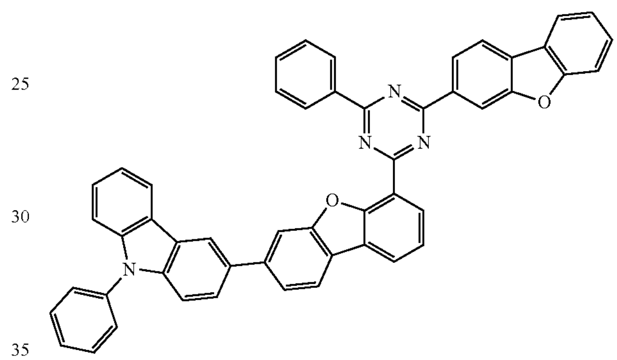
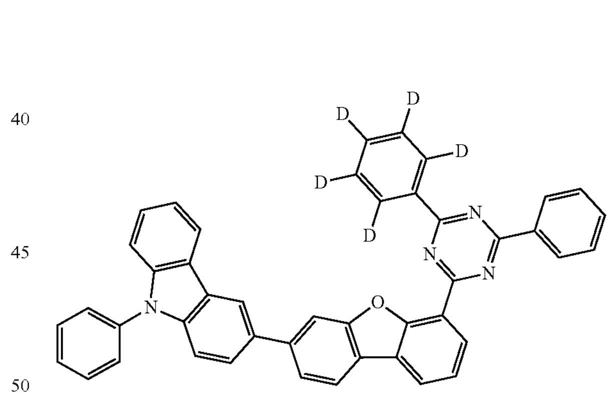
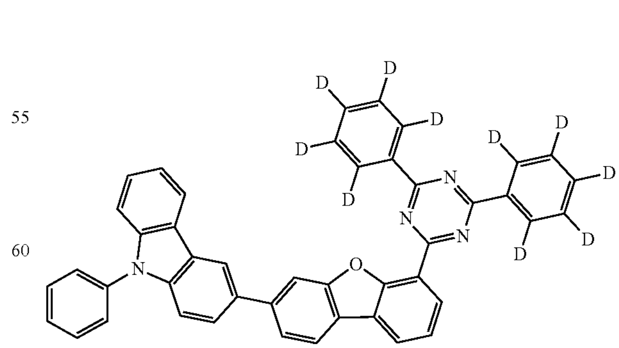

-continued
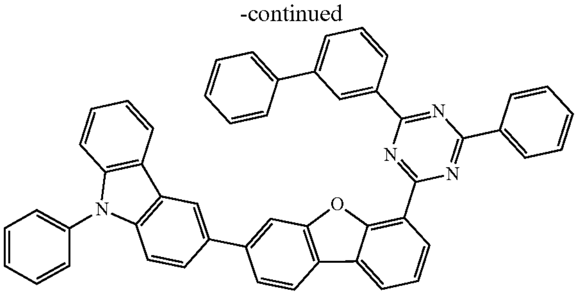
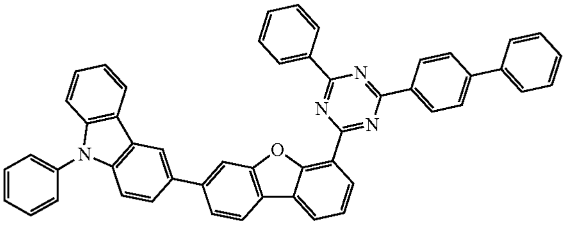
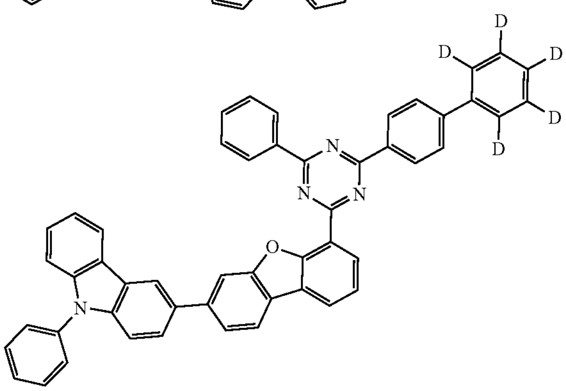
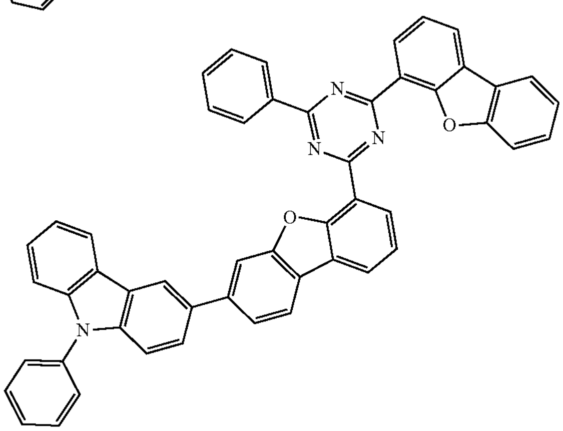
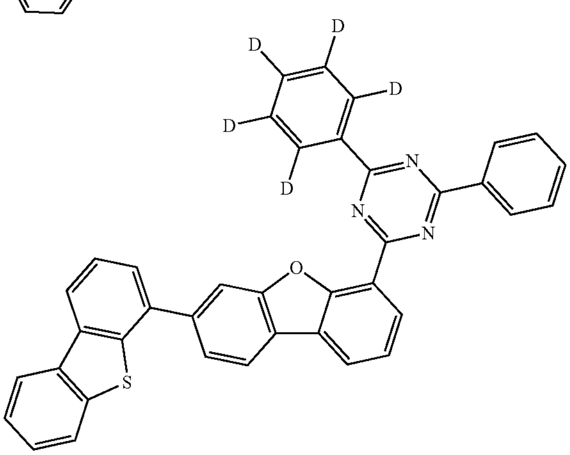
-continued
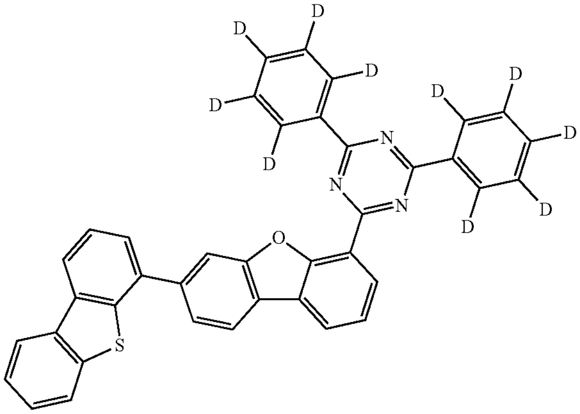
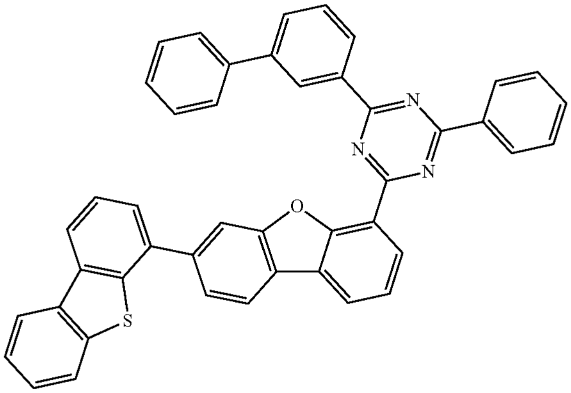
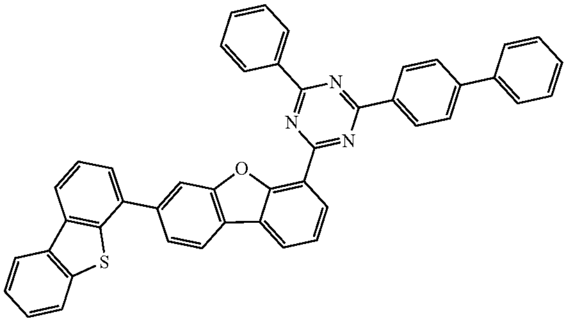
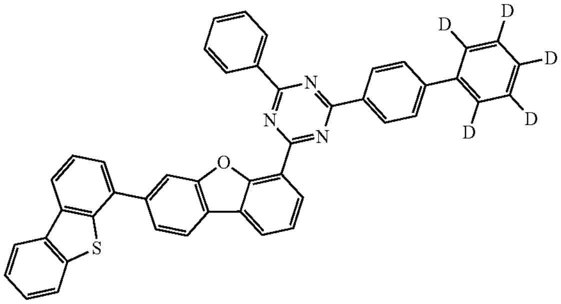

-continued
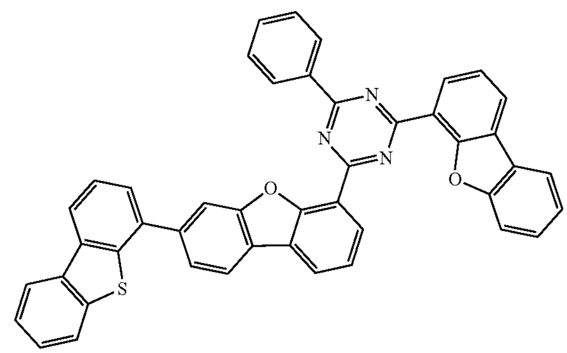
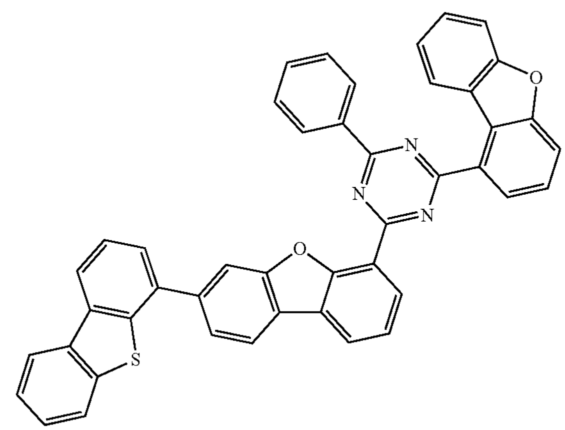
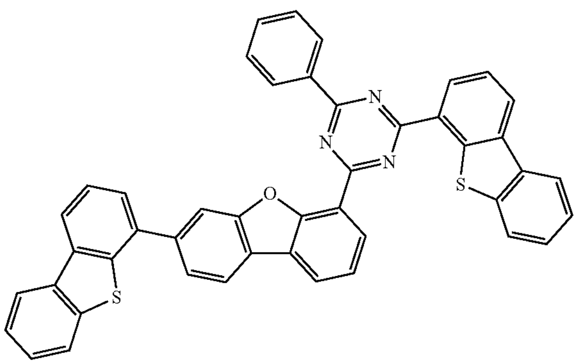
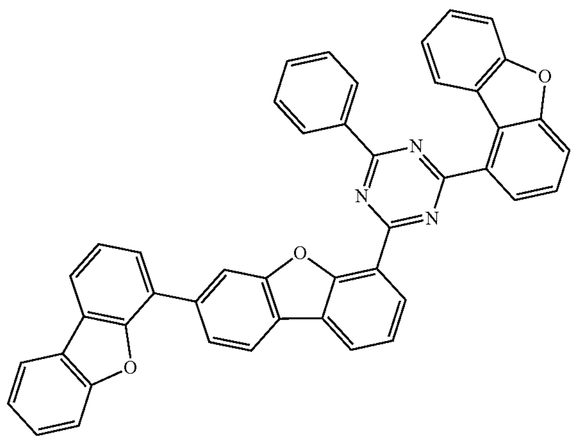
-continued
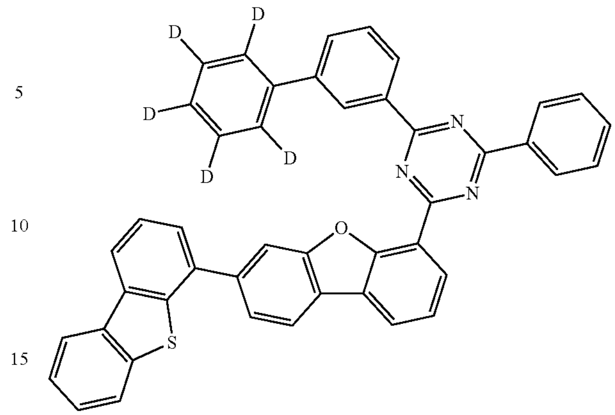
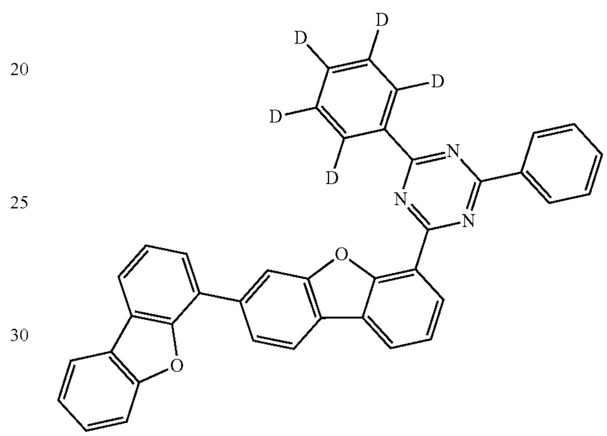
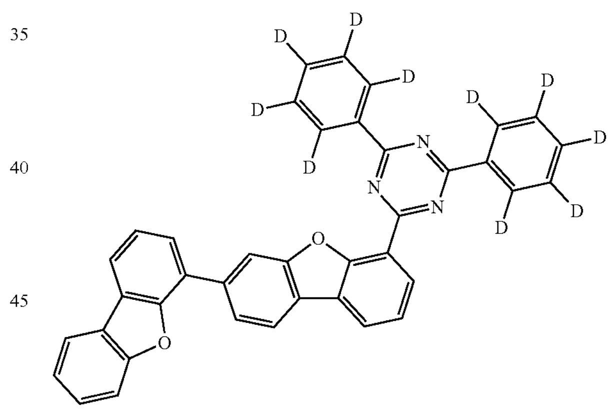
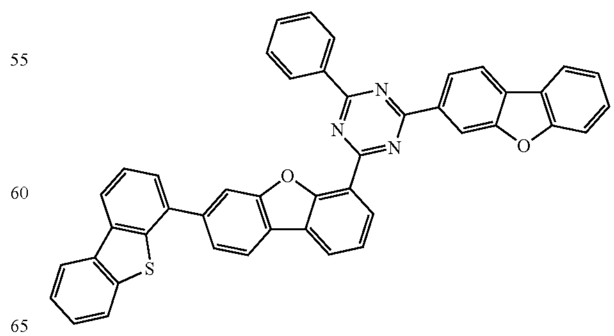

-continued
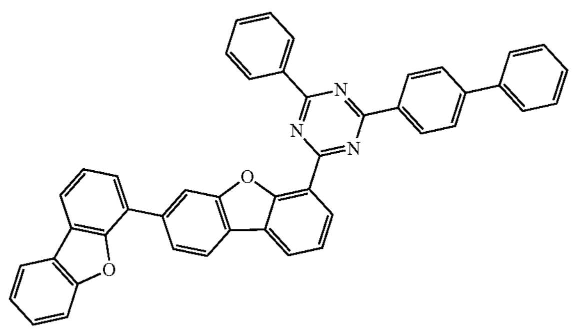
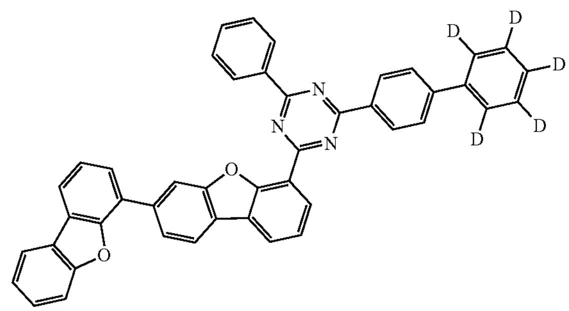
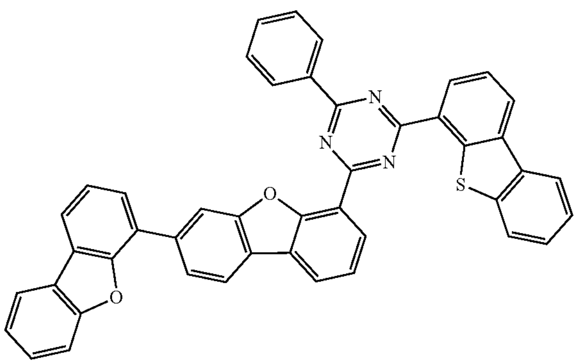
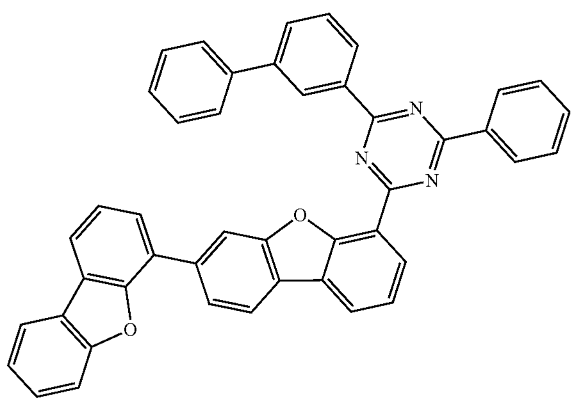
-continued
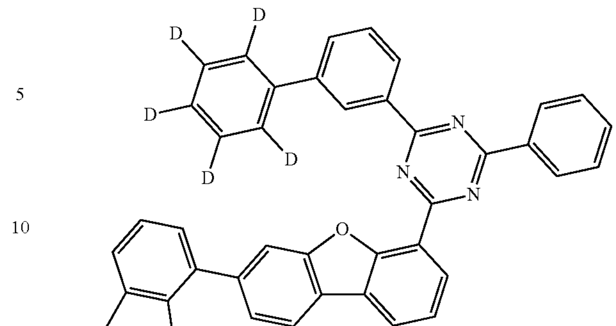
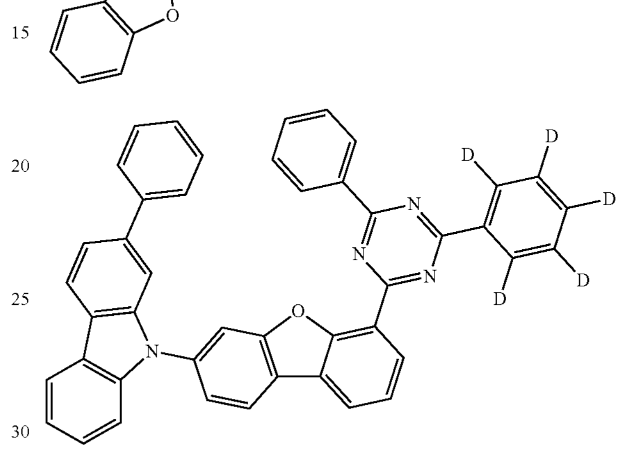
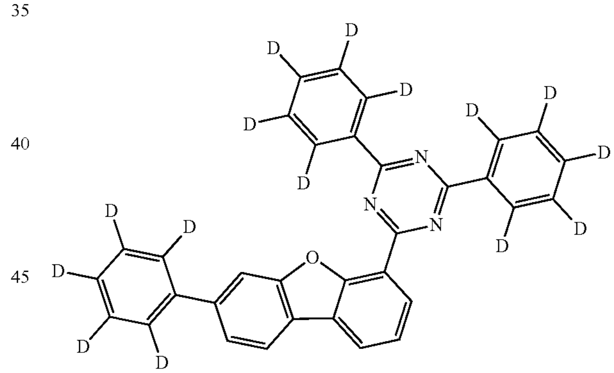
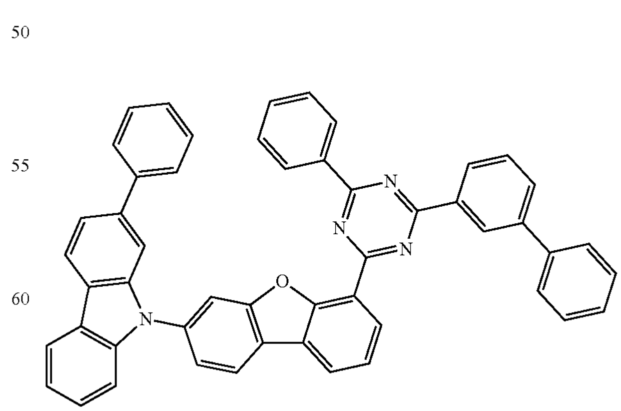

-continued
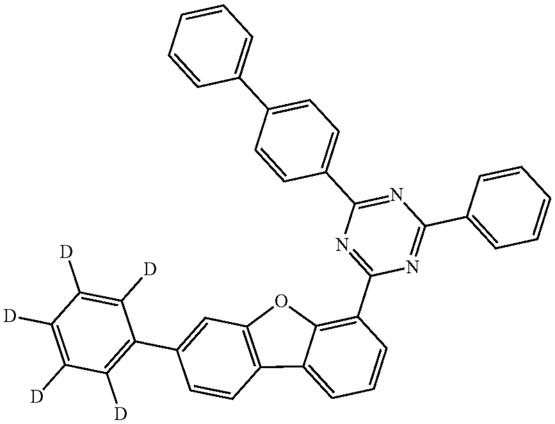
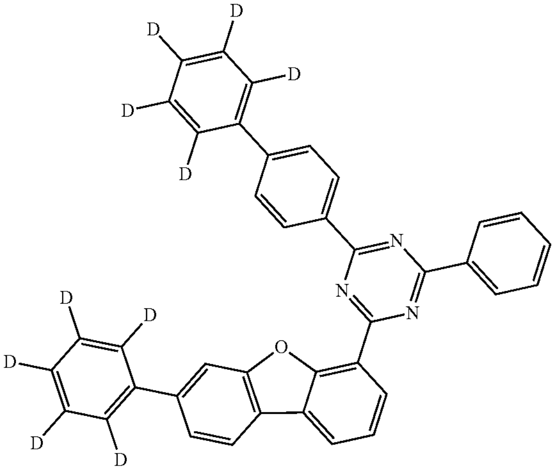
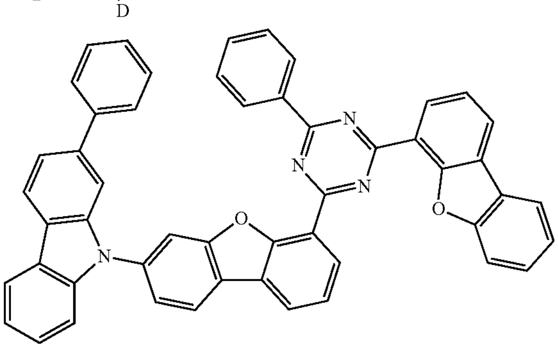
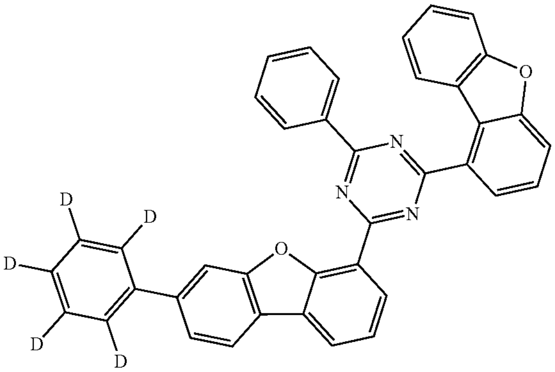
-continued
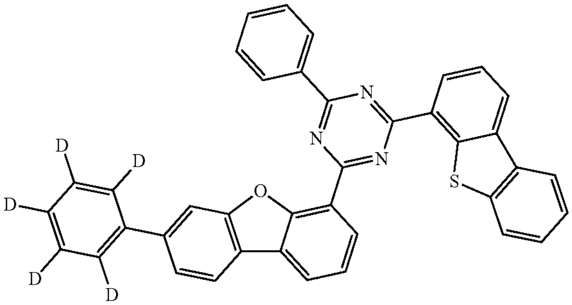
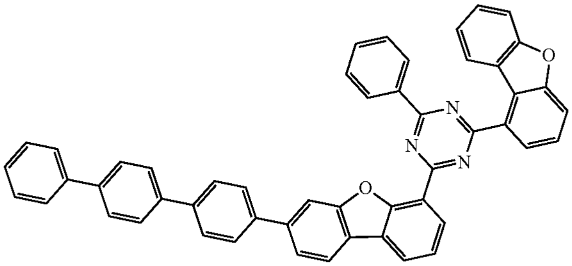
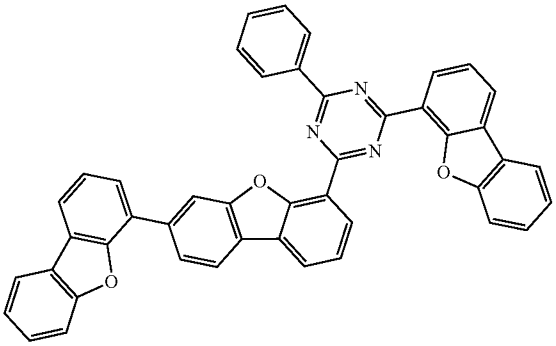
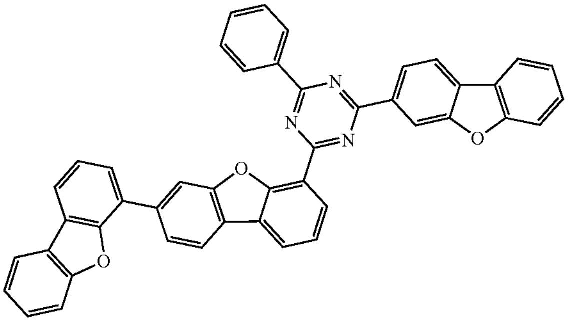
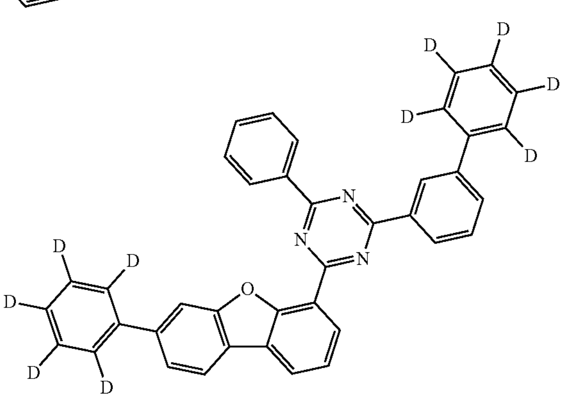

-continued
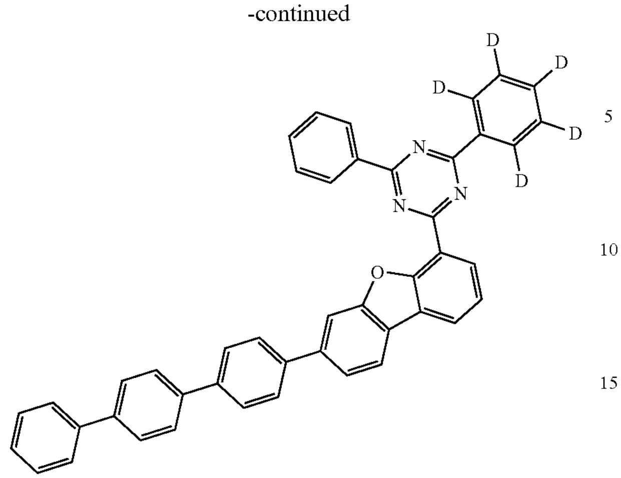
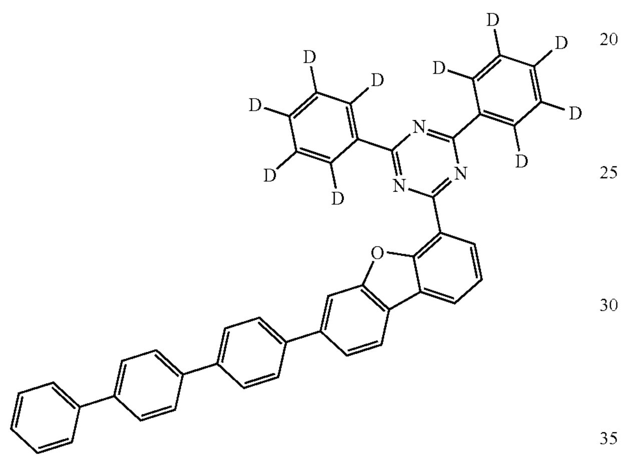
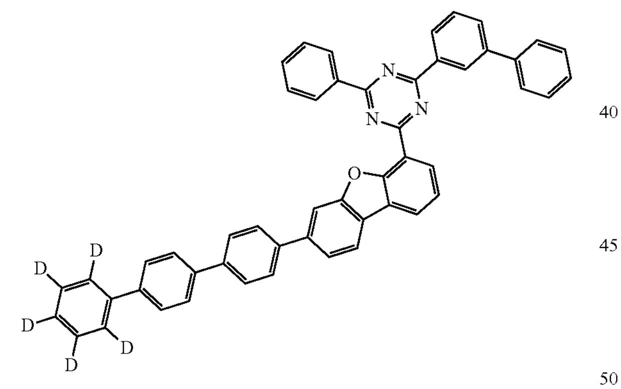
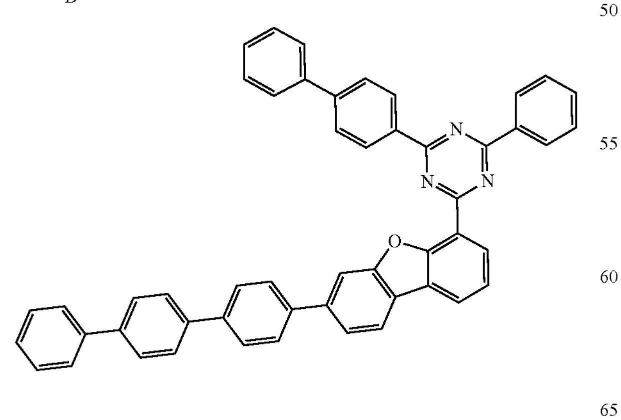
-continued
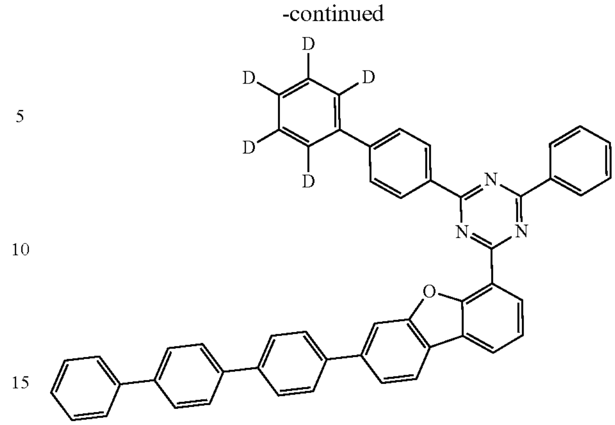
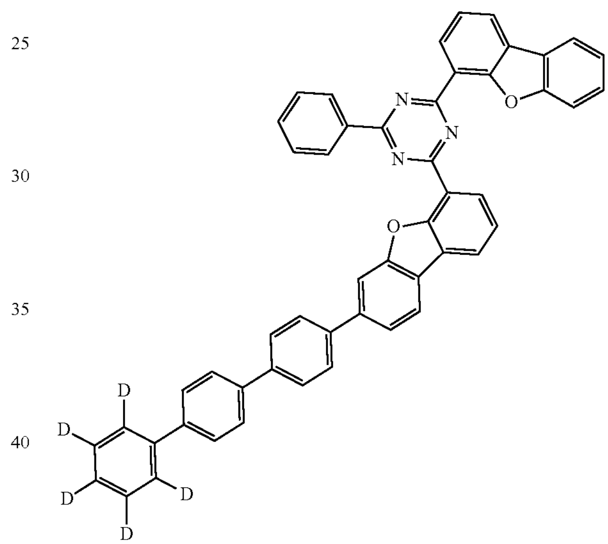
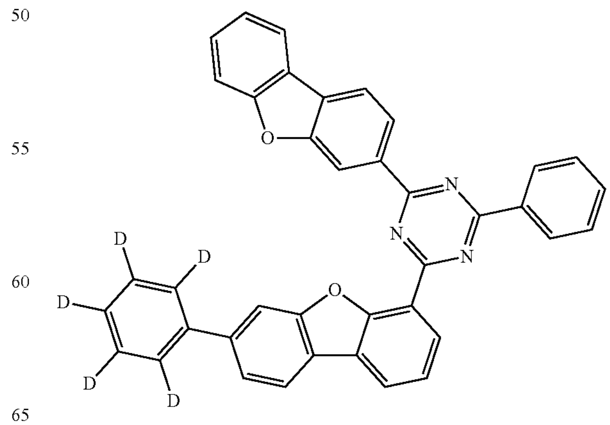

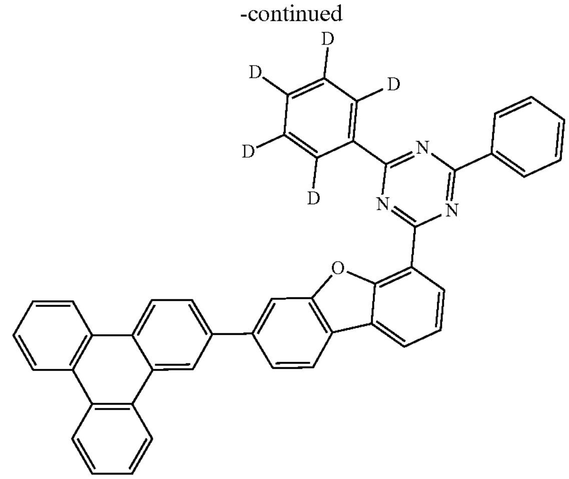
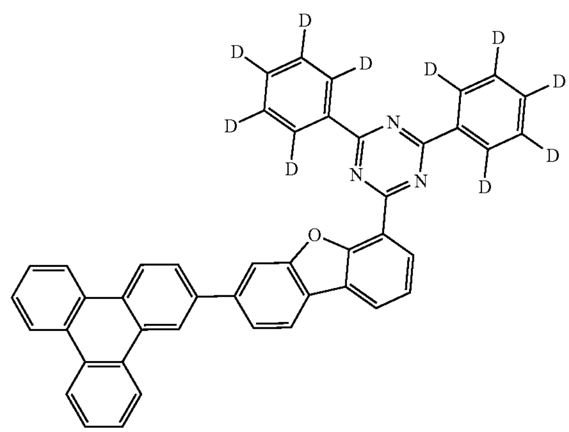
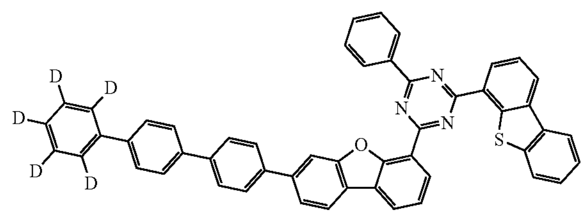
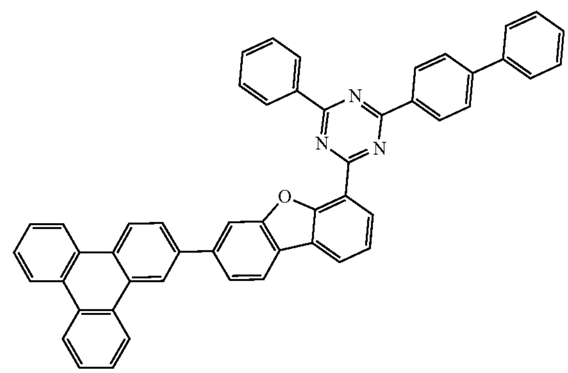
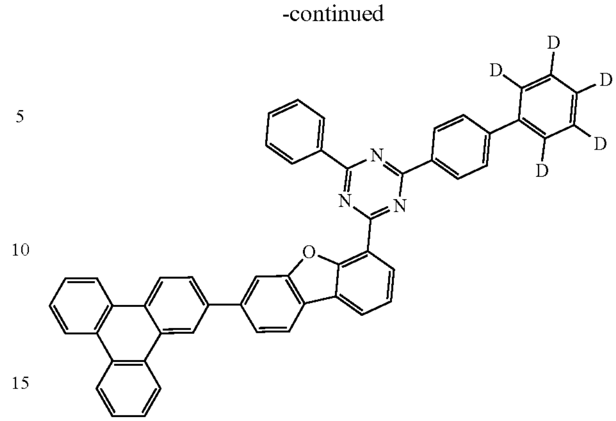
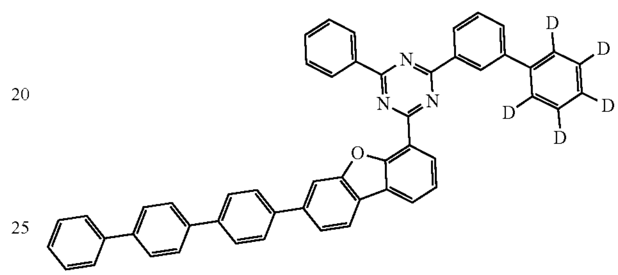
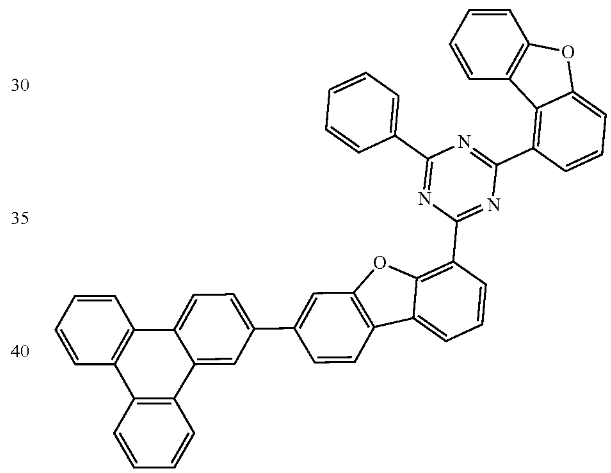
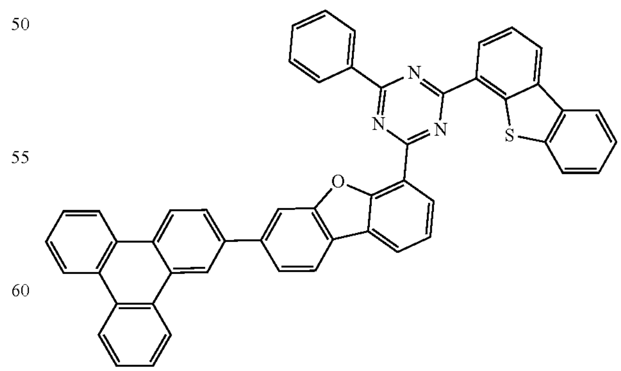

-continued
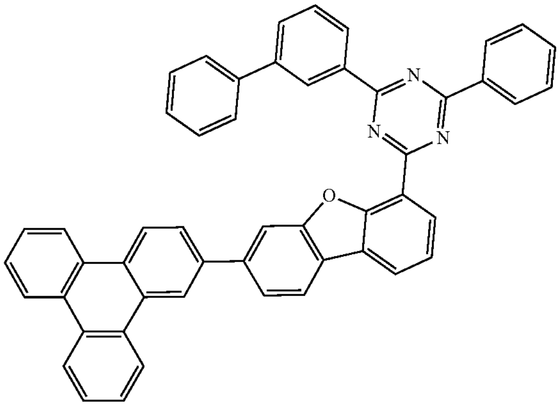
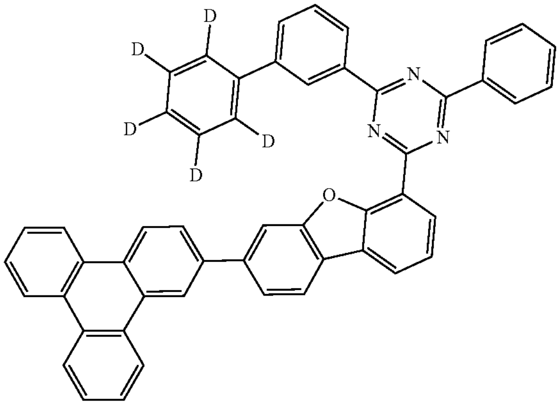
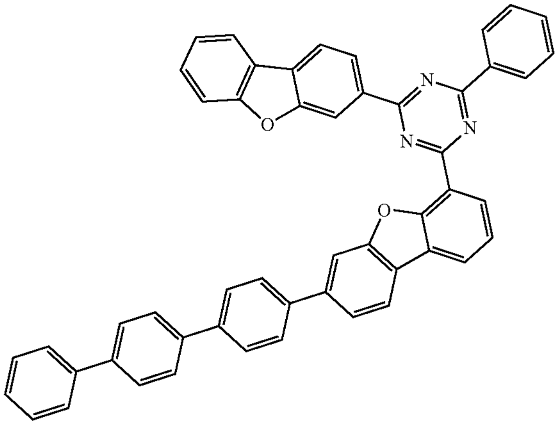
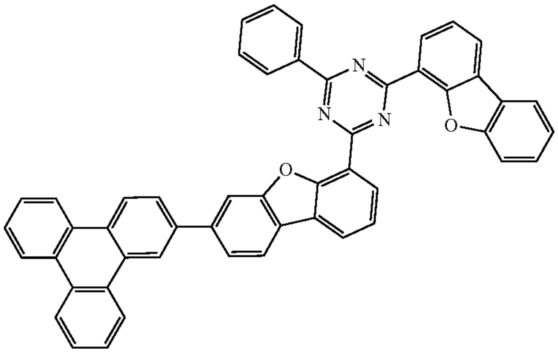
-continued
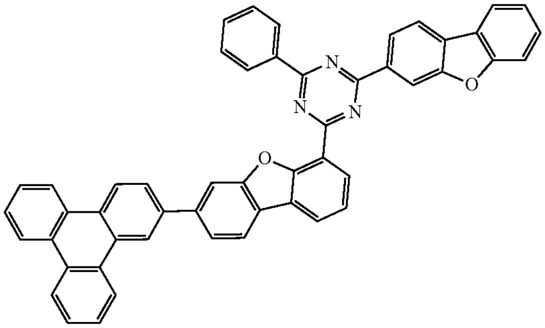
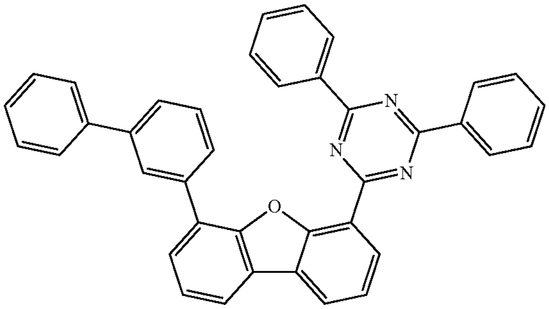
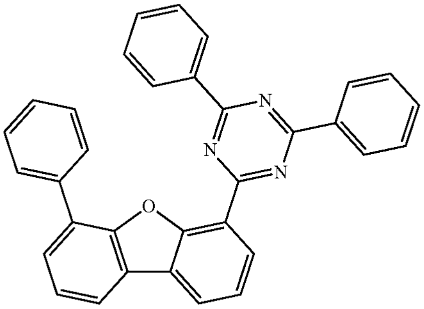
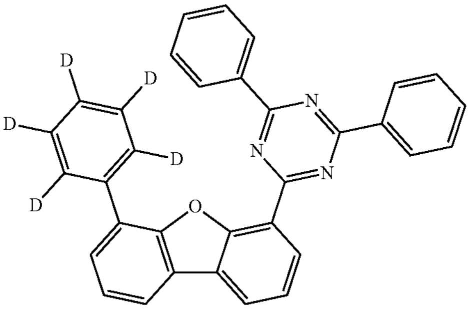
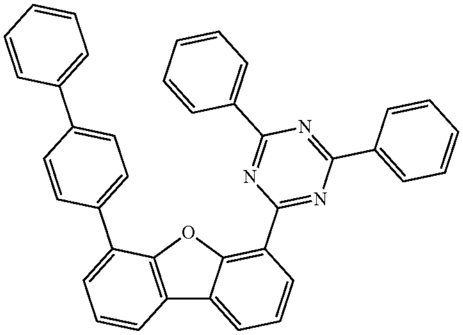

-continued
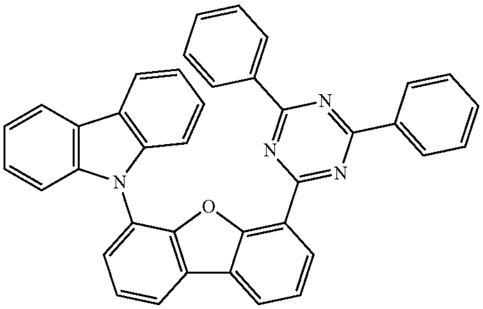
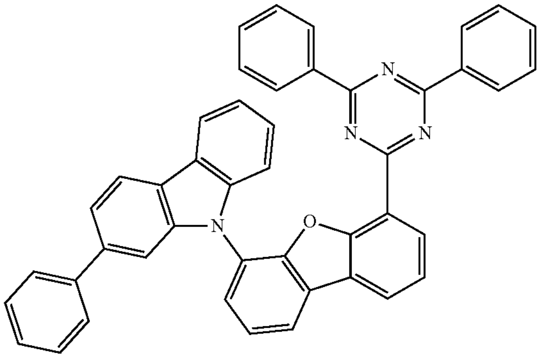
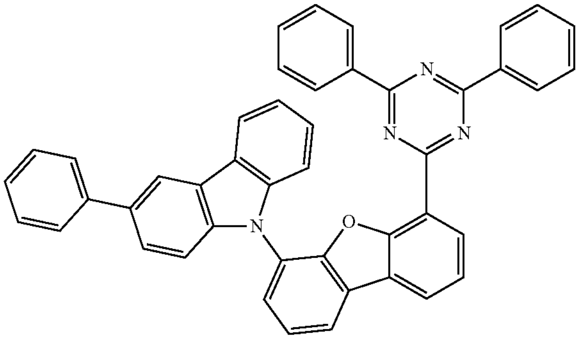
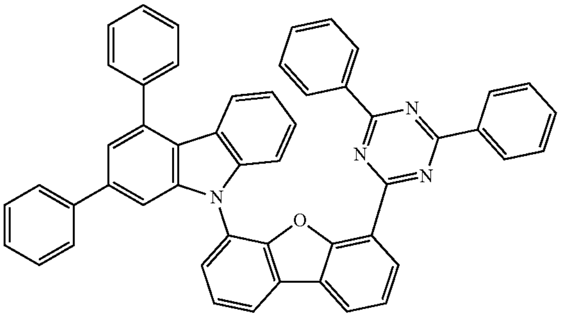
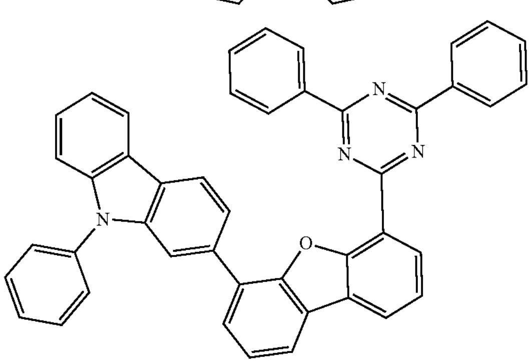
-continued
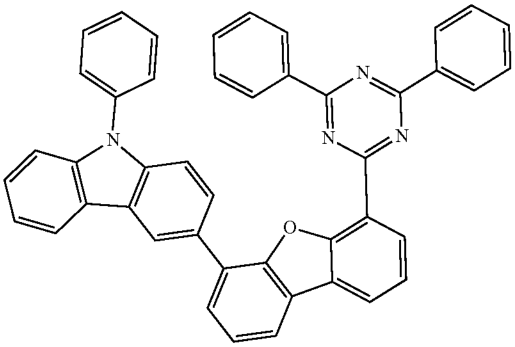
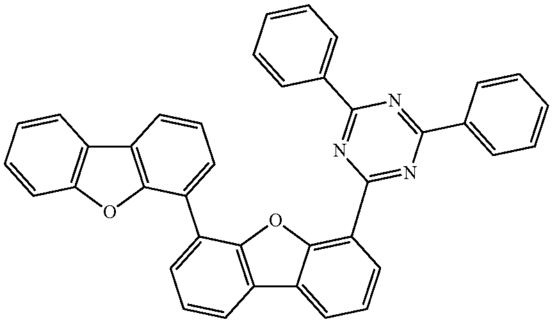
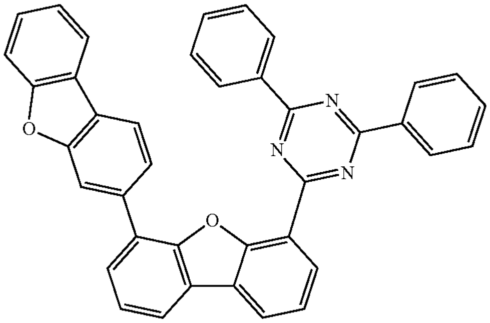
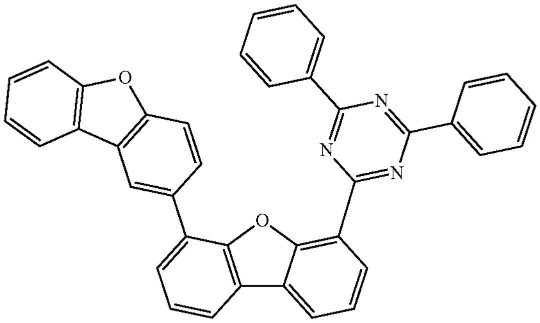
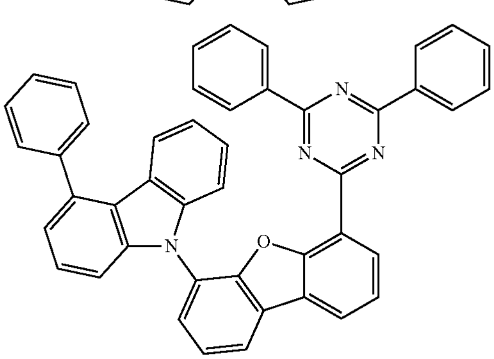

-continued
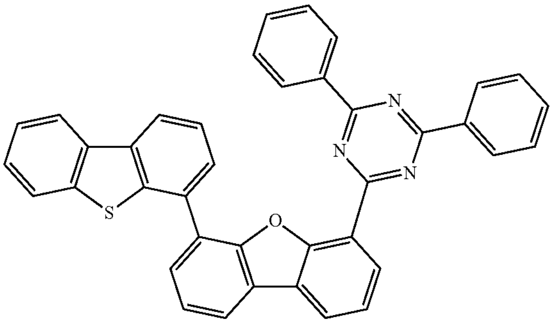
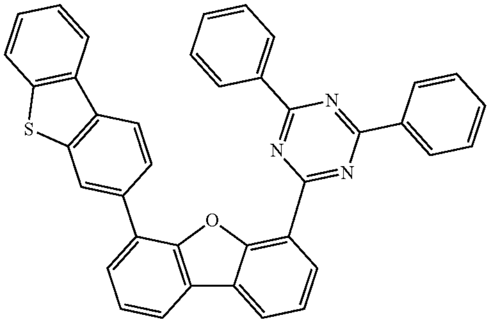
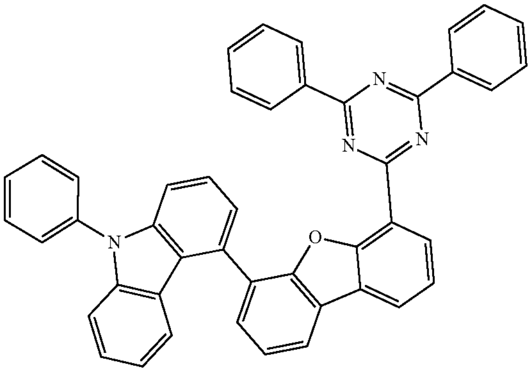
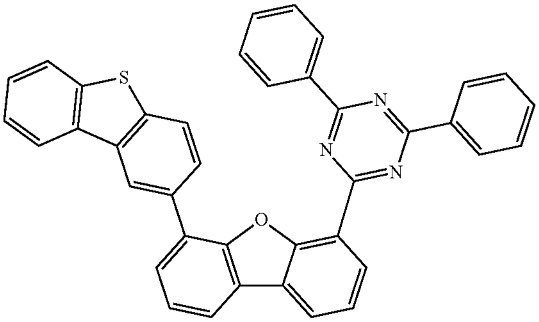
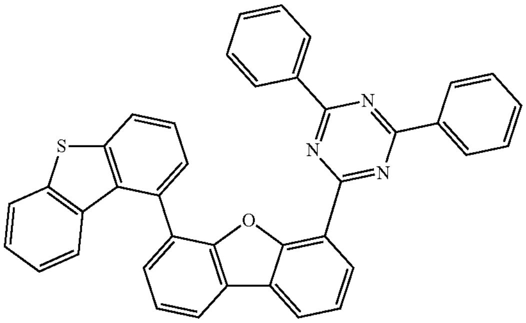
-continued
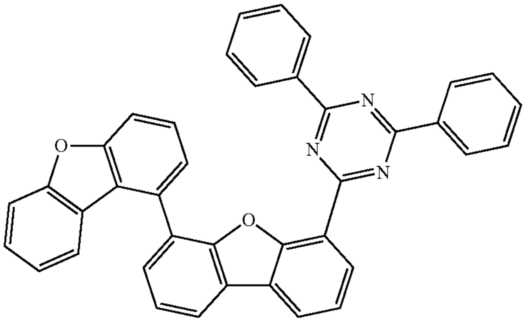
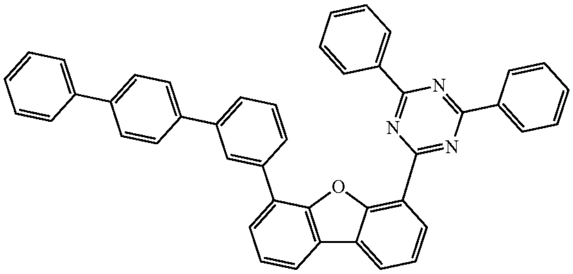
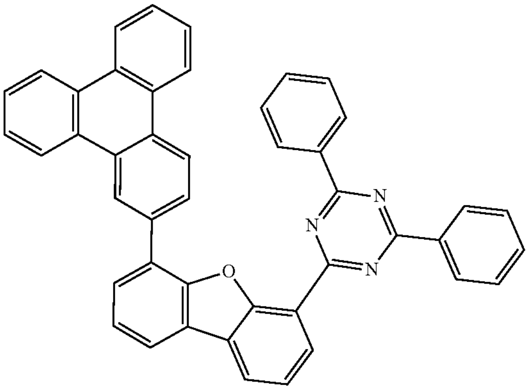
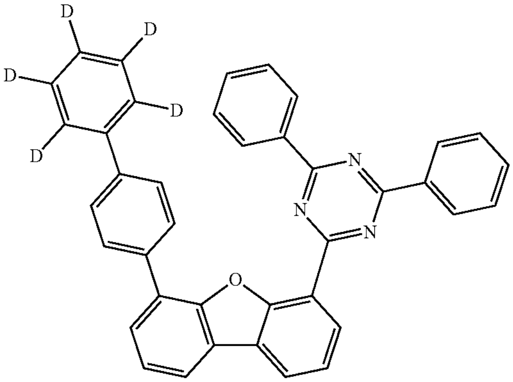

-continued
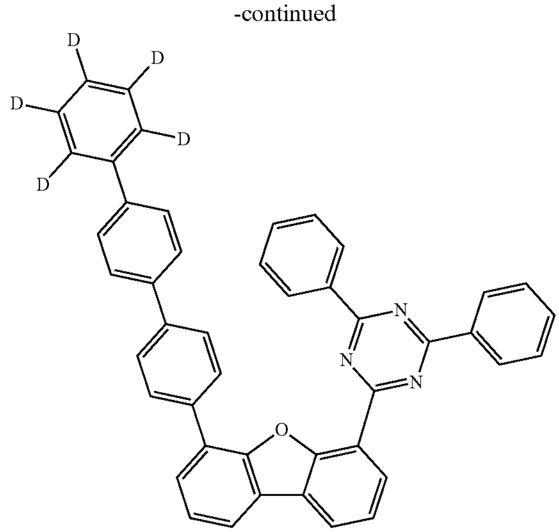
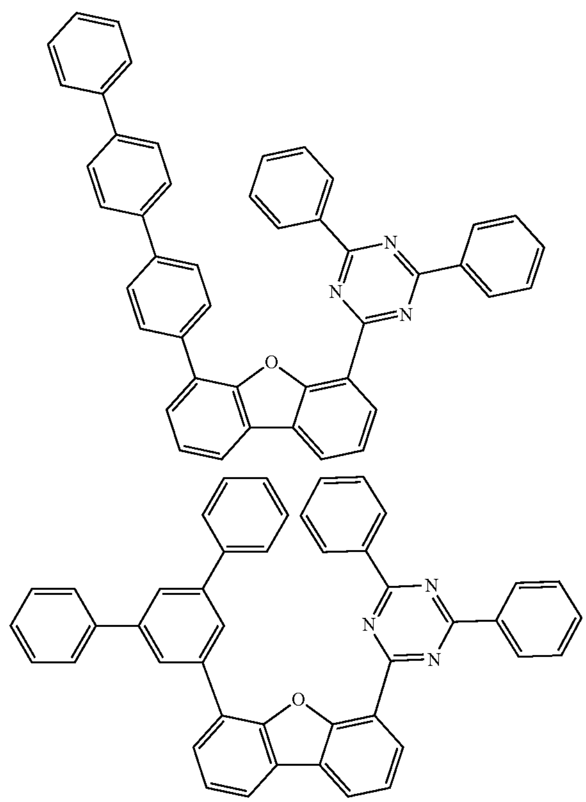
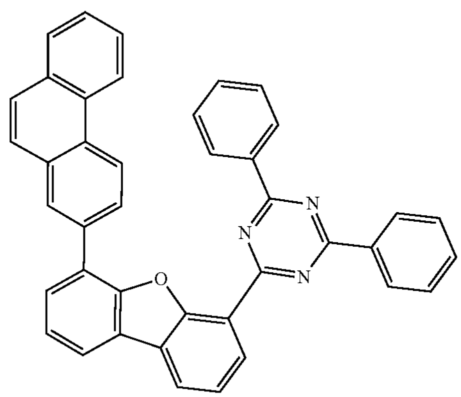
-continued
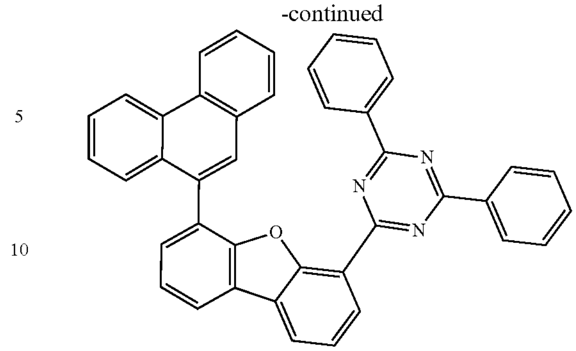
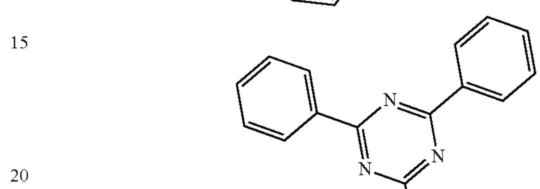
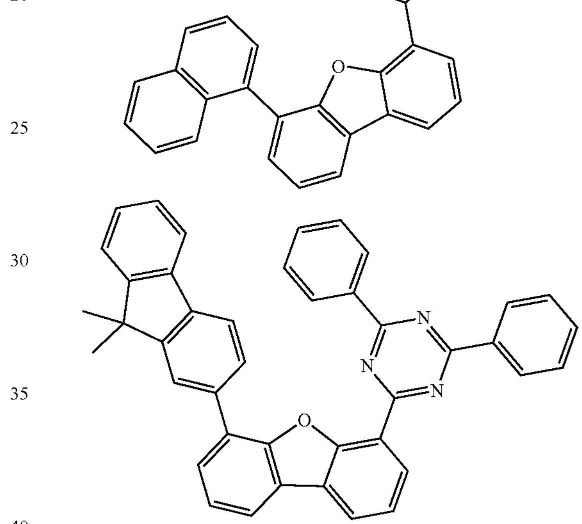
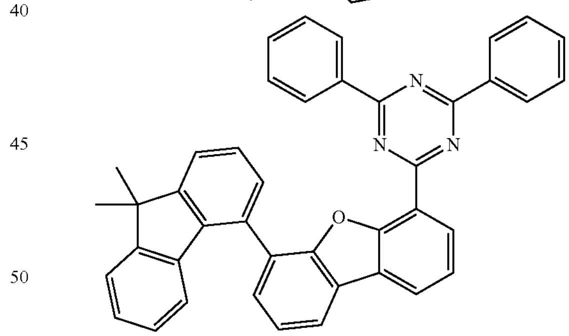
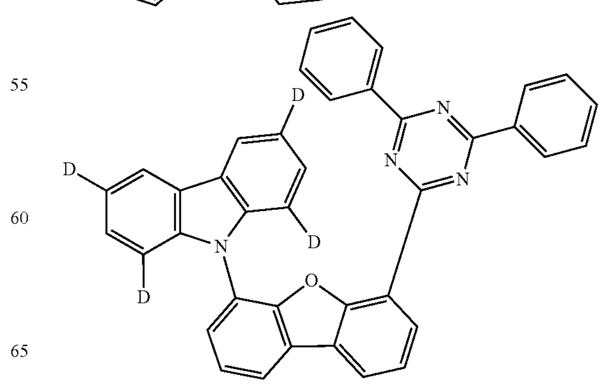

-continued
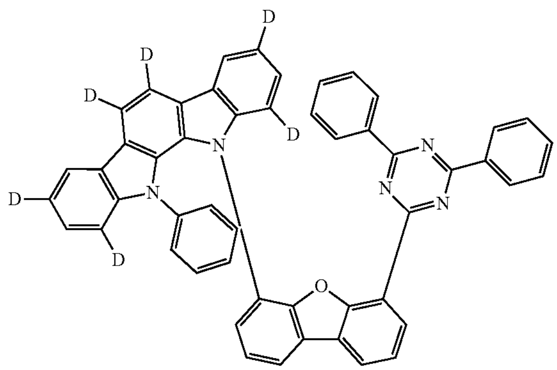
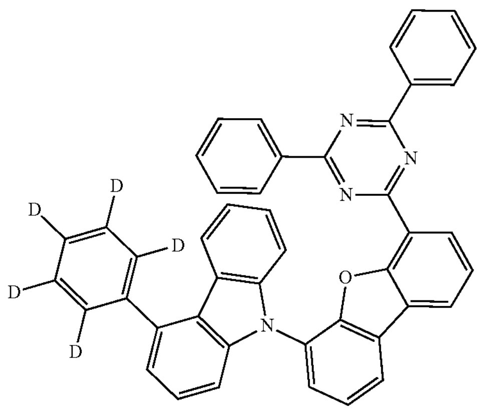
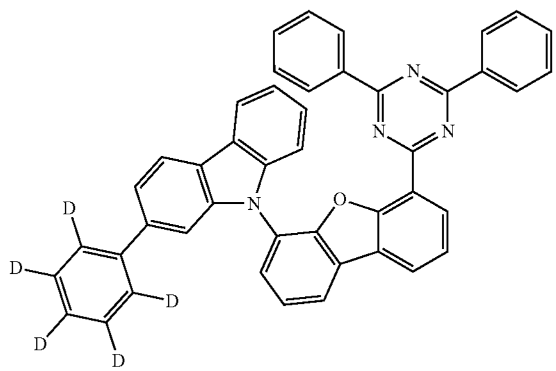
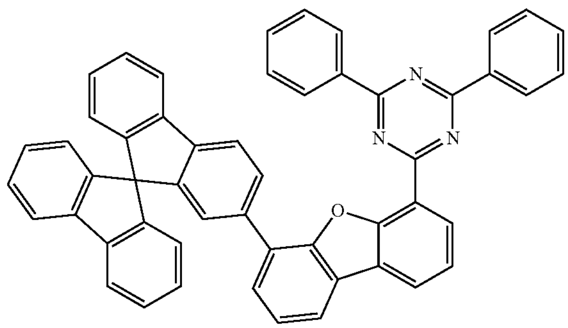
-continued
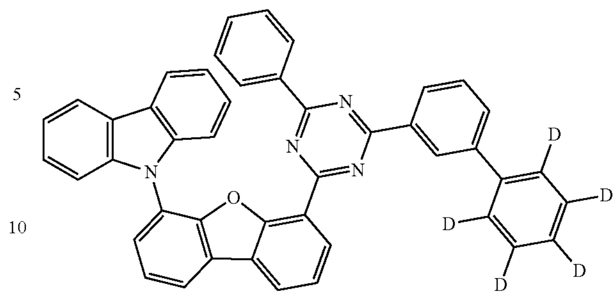
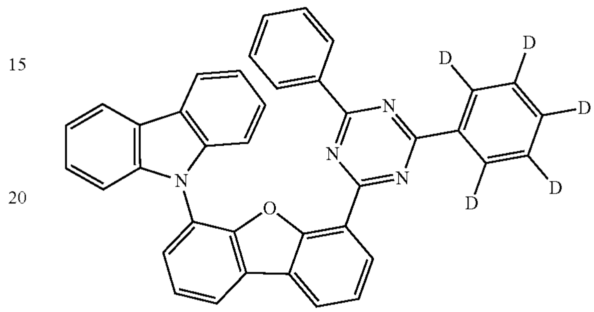
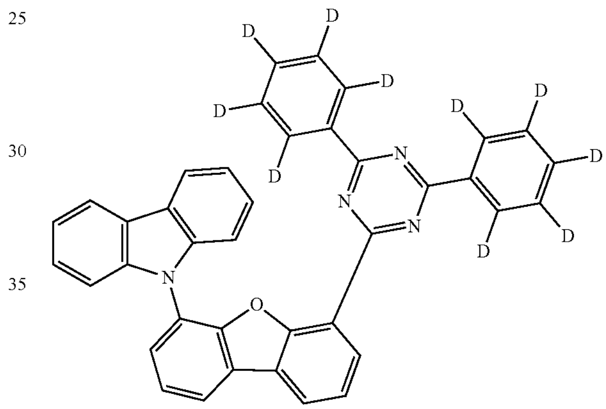
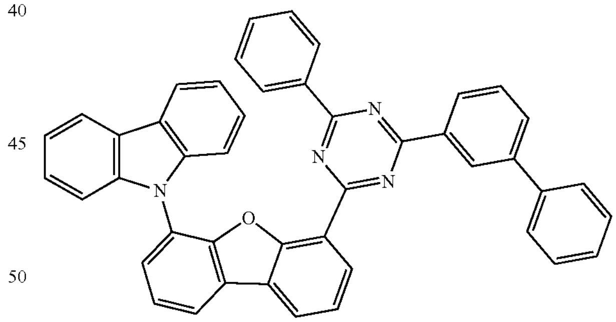
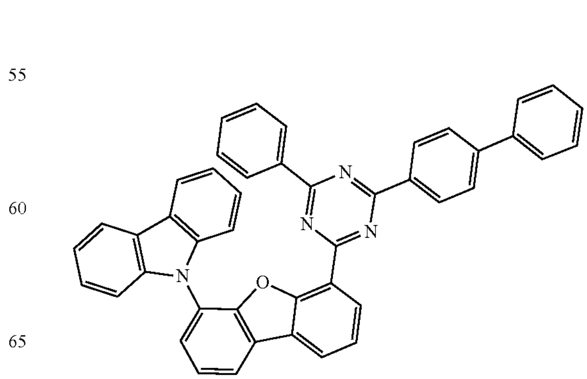

-continued
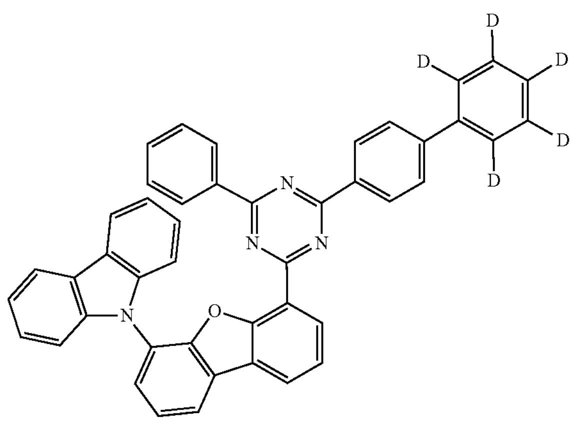
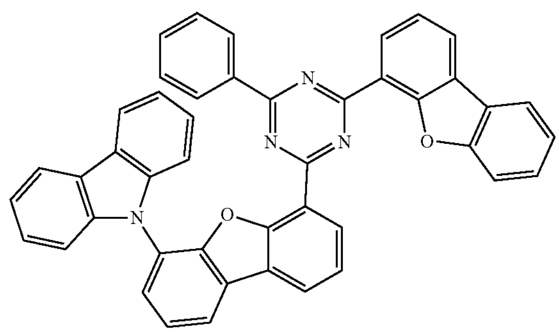
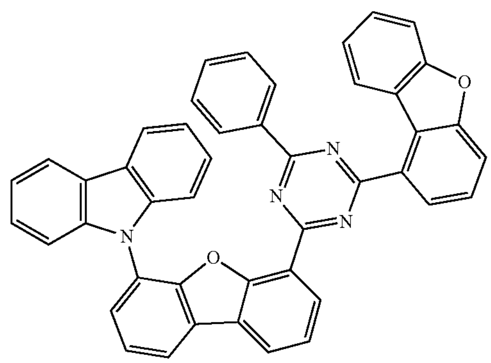
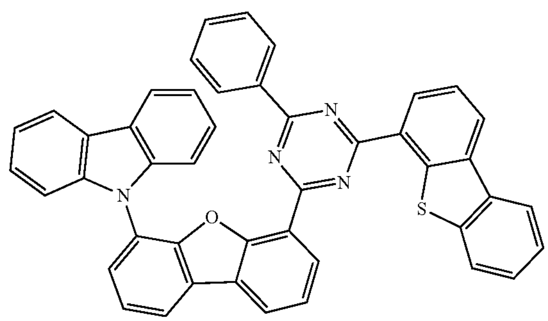
-continued
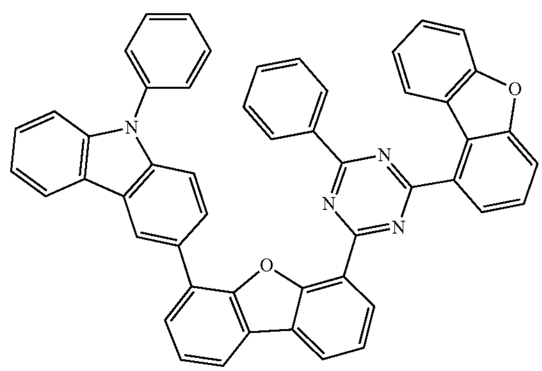
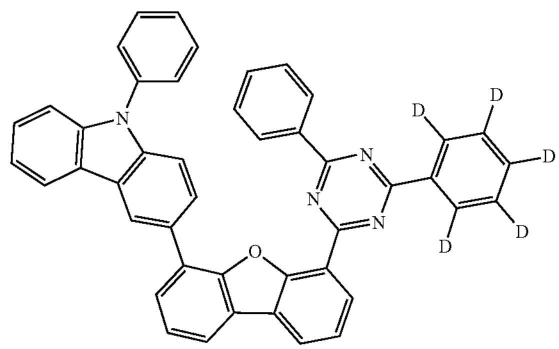
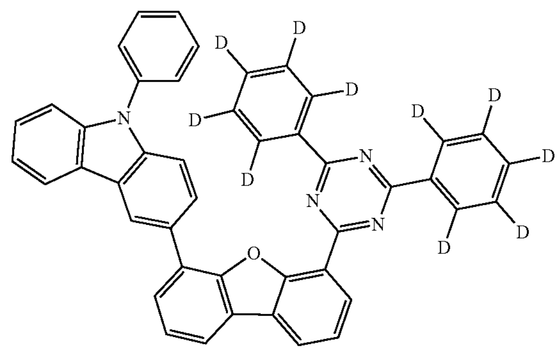
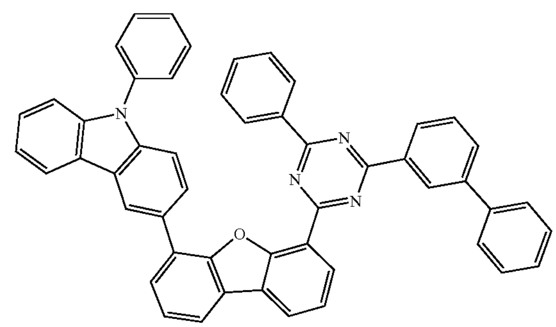
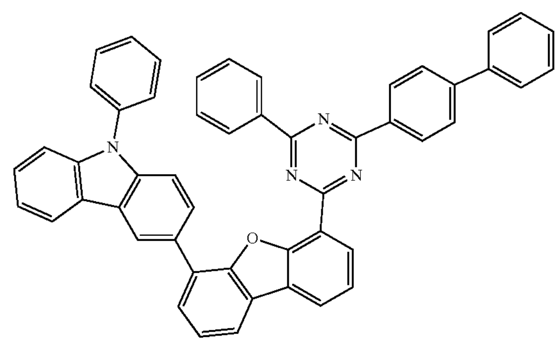

-continued
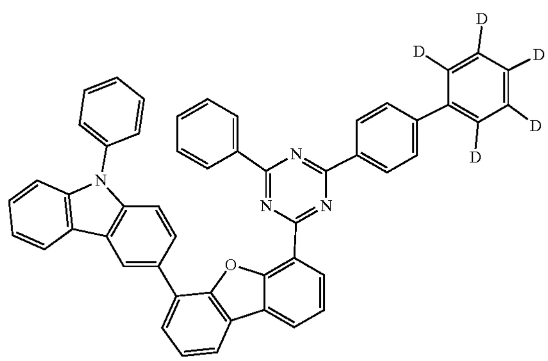
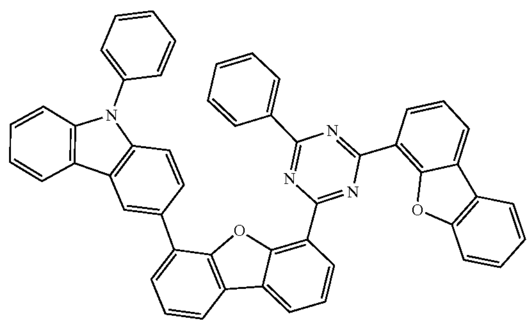
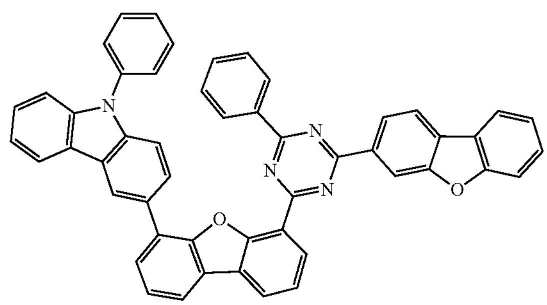
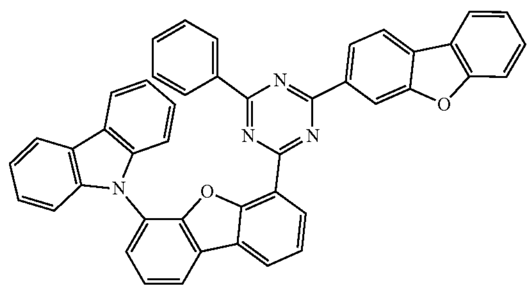
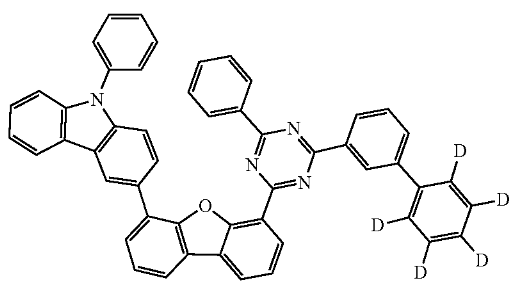
-continued
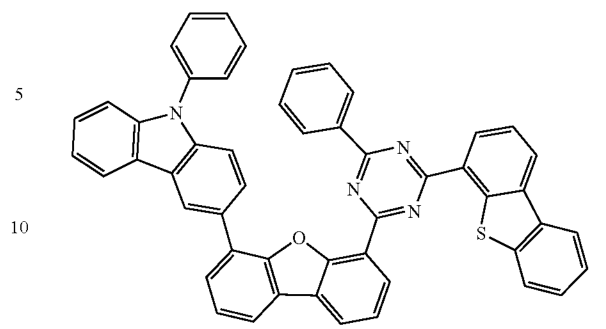
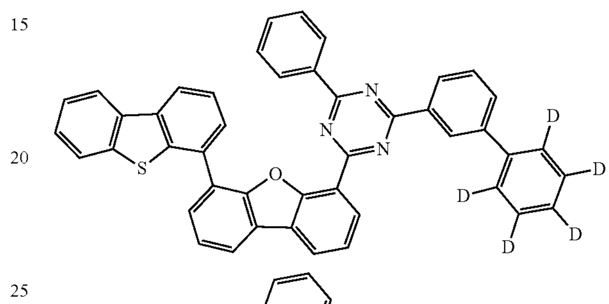
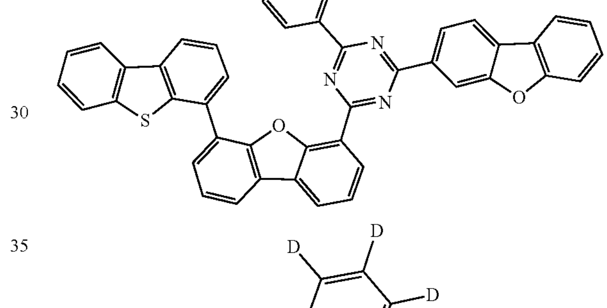
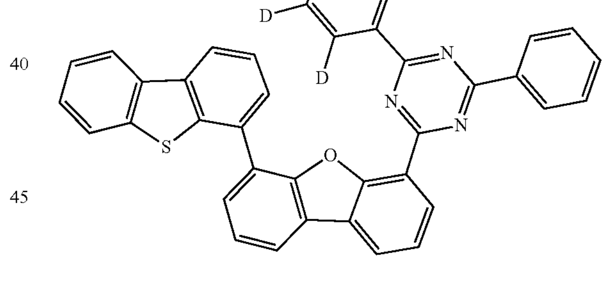
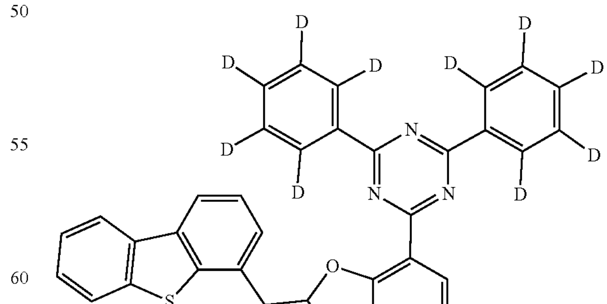

-continued
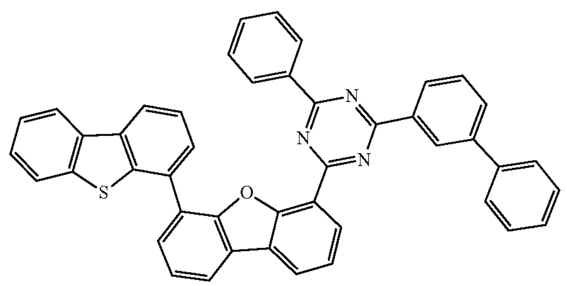
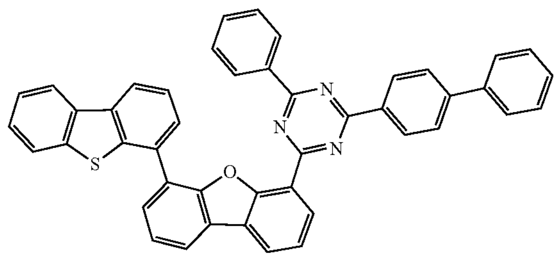
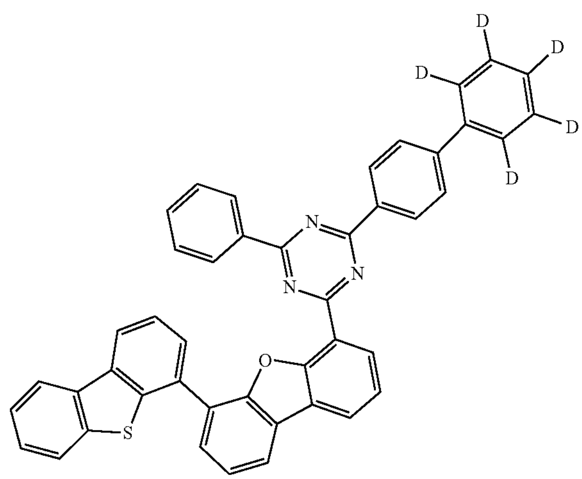
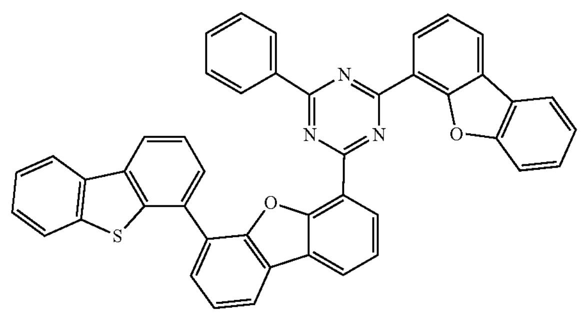
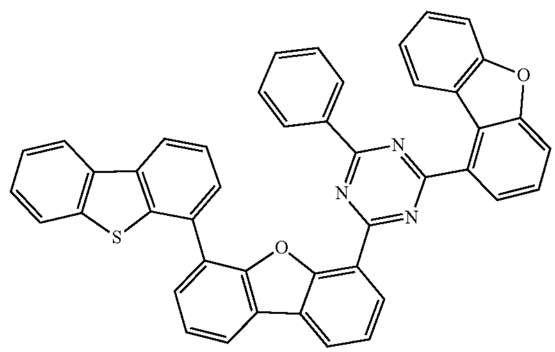
-continued
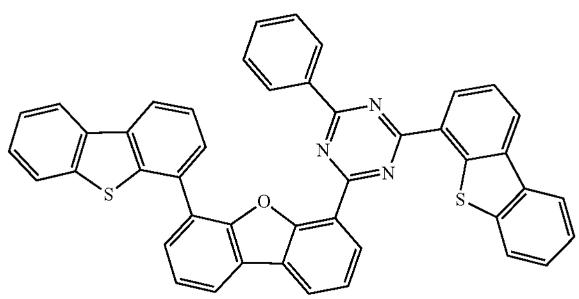
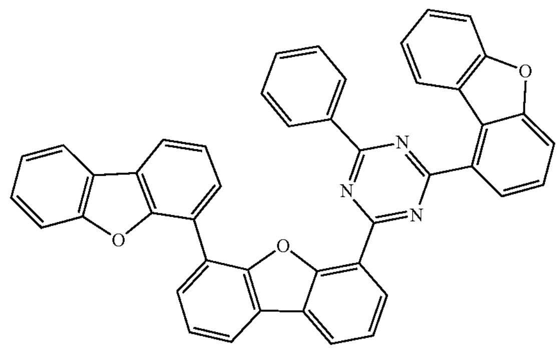
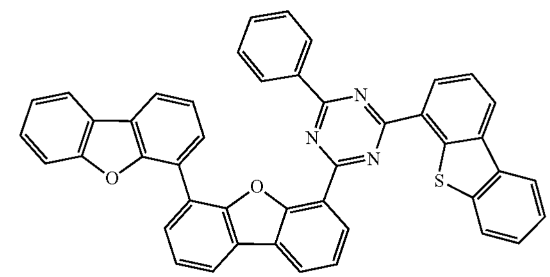
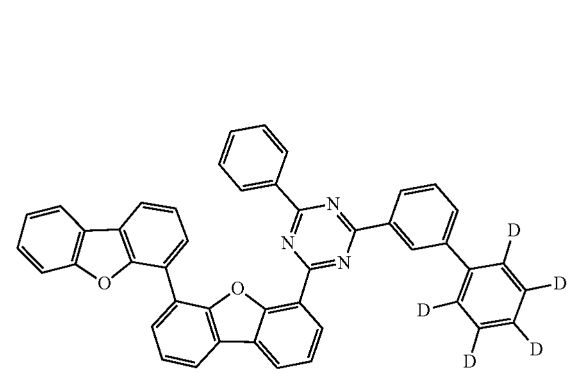
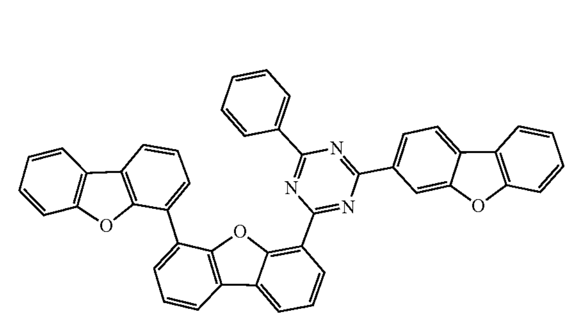

-continued
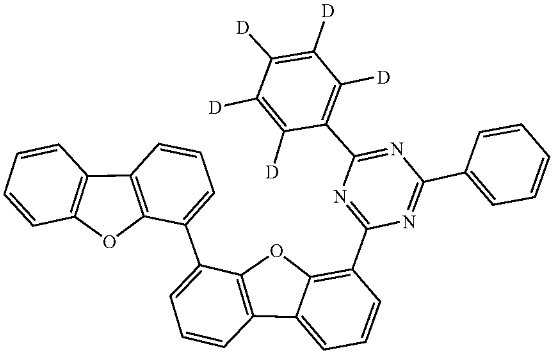
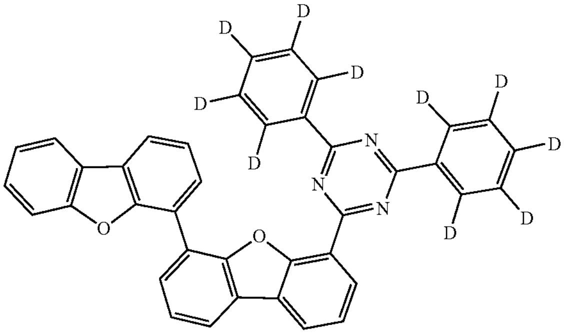
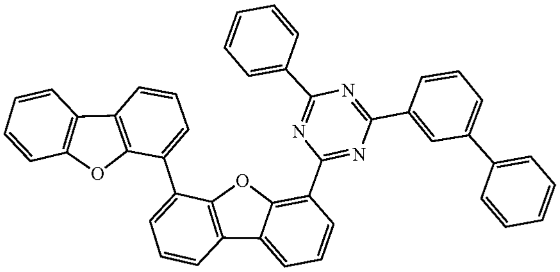
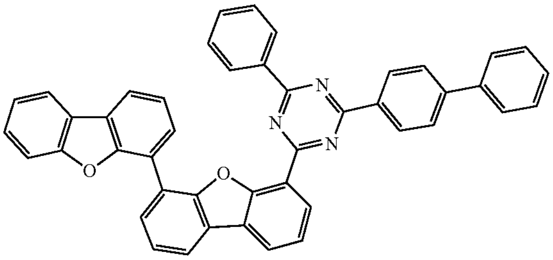
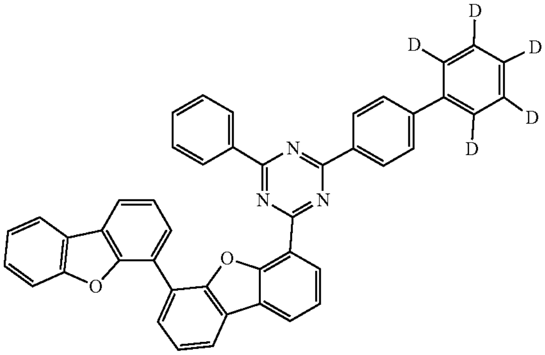
-continued
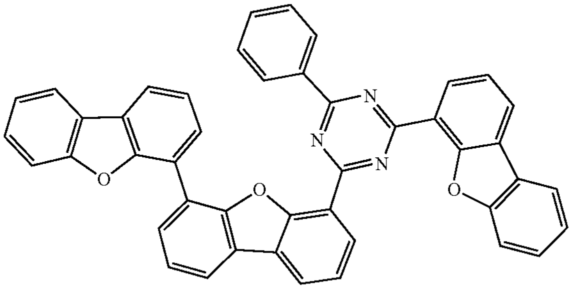
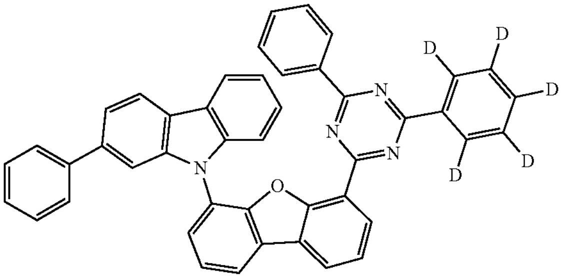
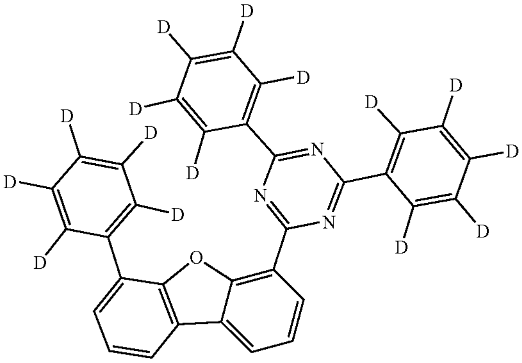
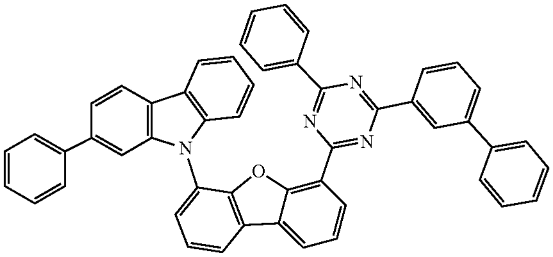
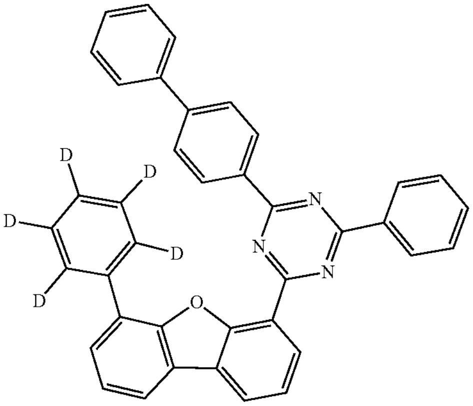

-continued
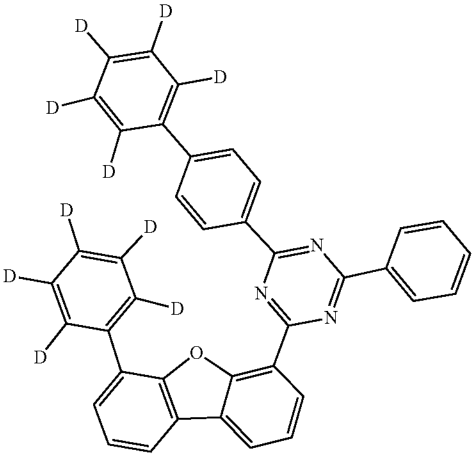
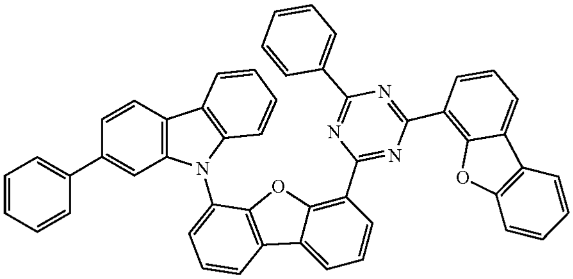
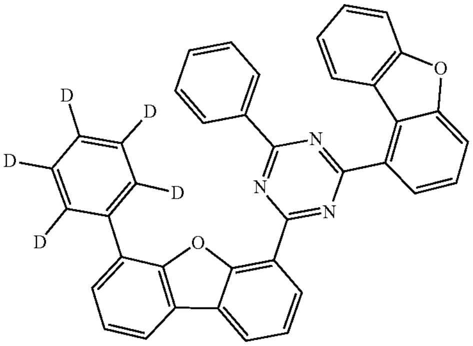
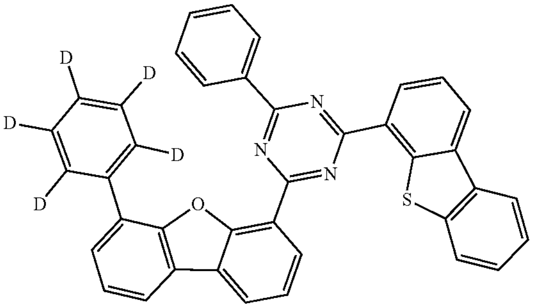
-continued
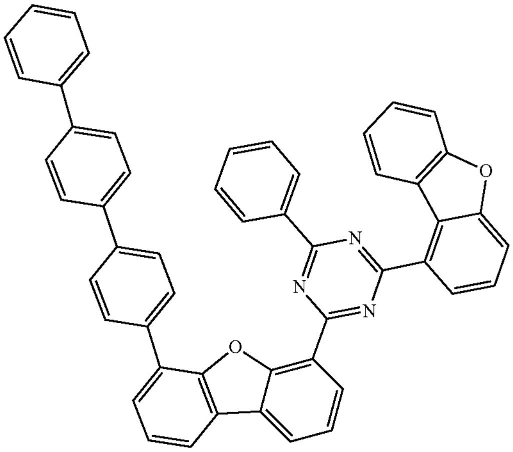
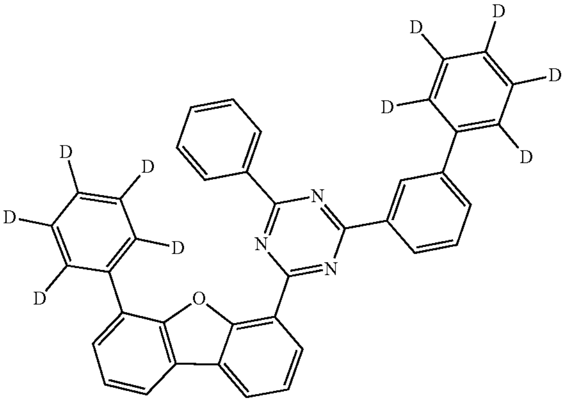
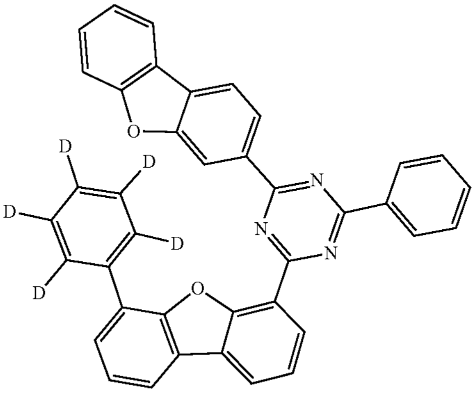
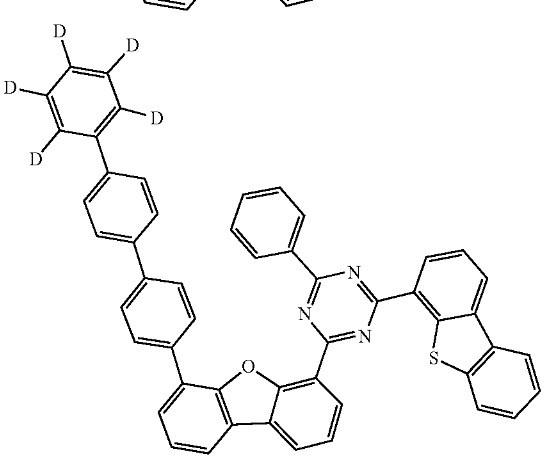

-continued
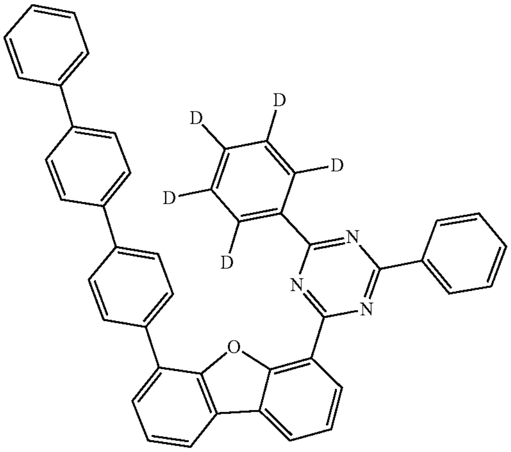
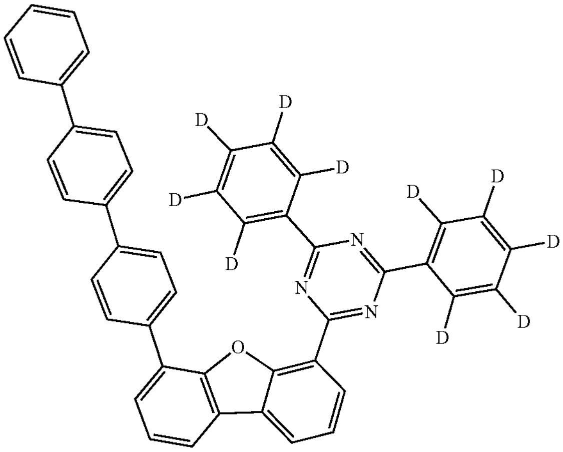
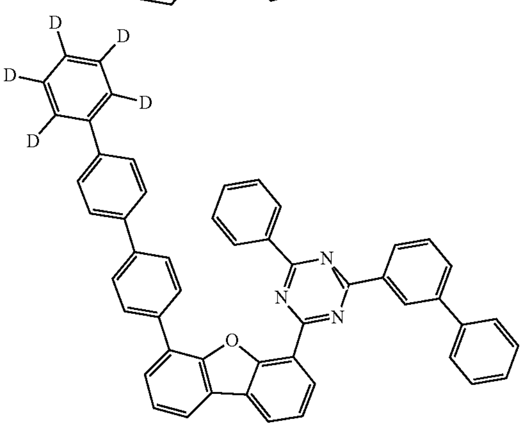
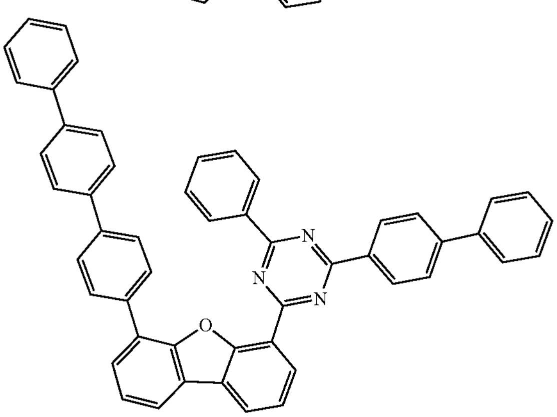
-continued
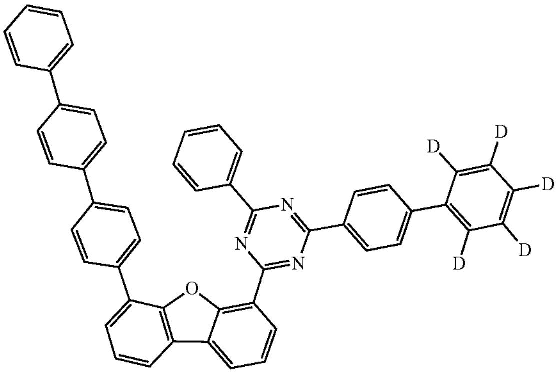
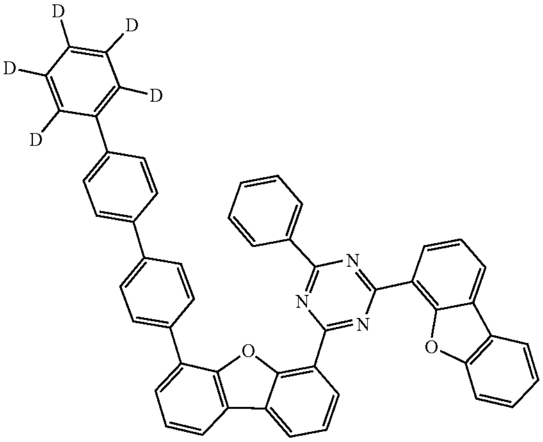
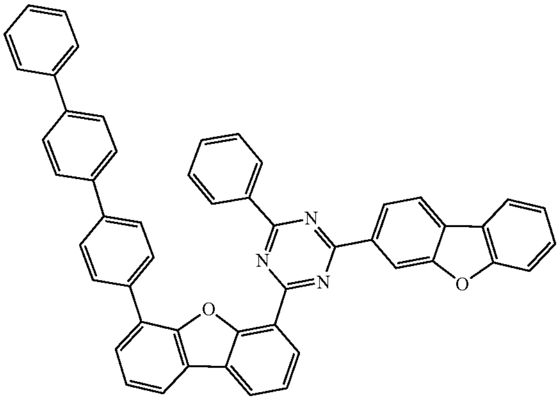
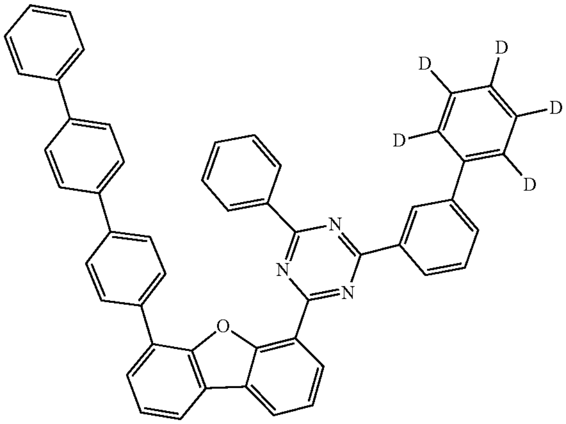

-continued
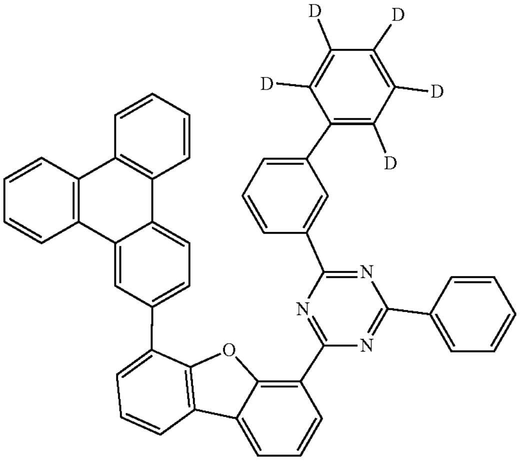
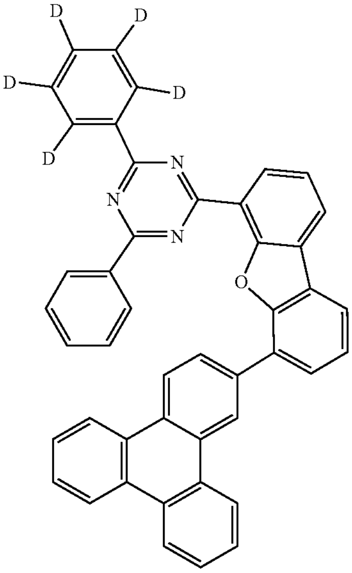
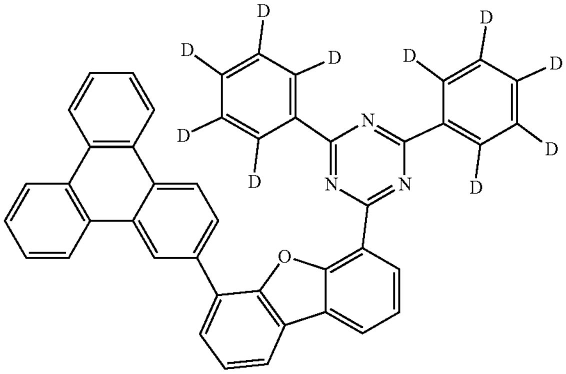
-continued
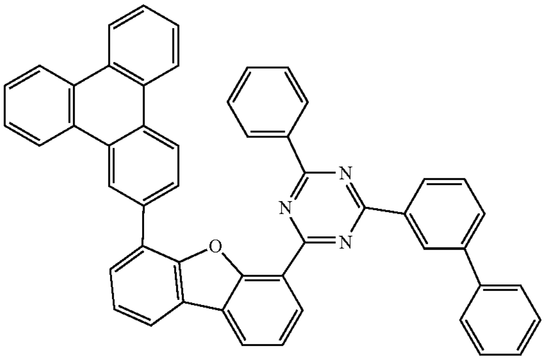
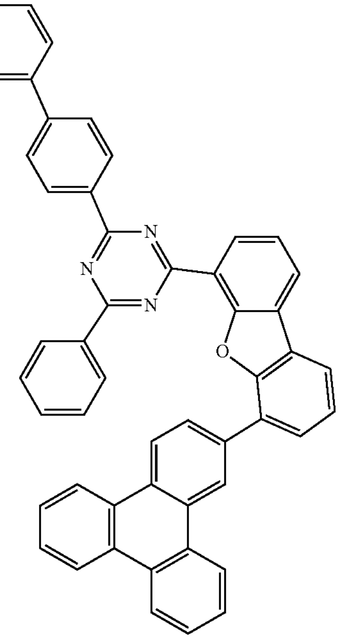
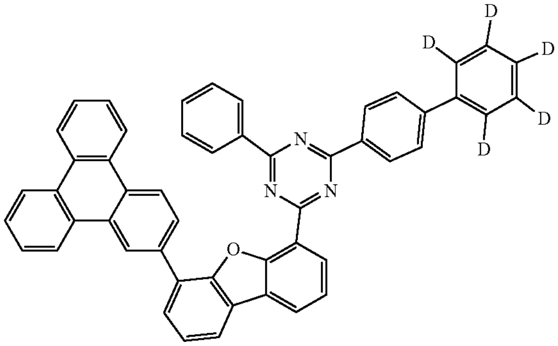
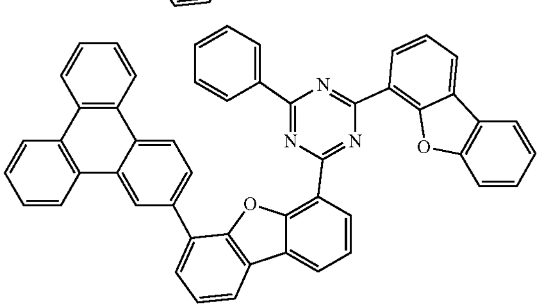

-continued
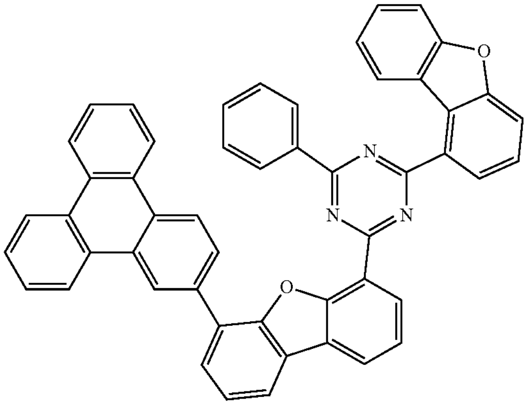
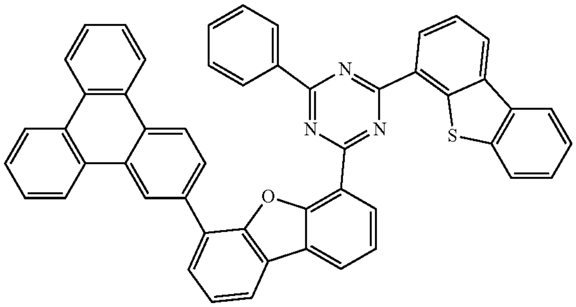
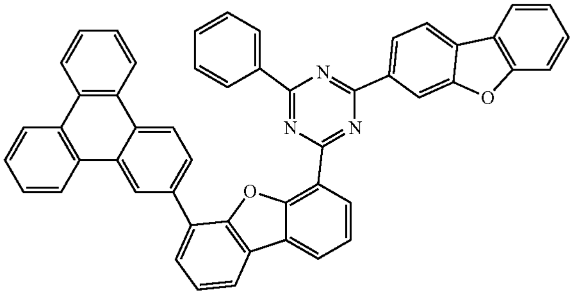
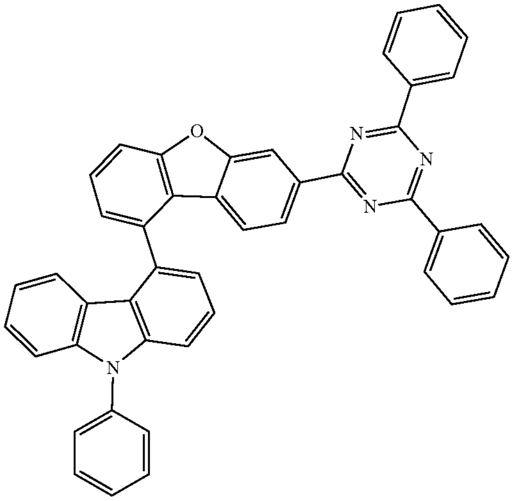
-continued
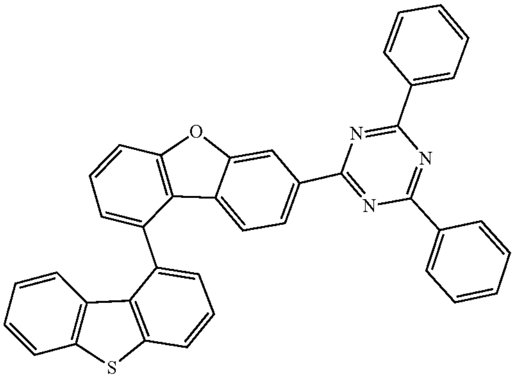
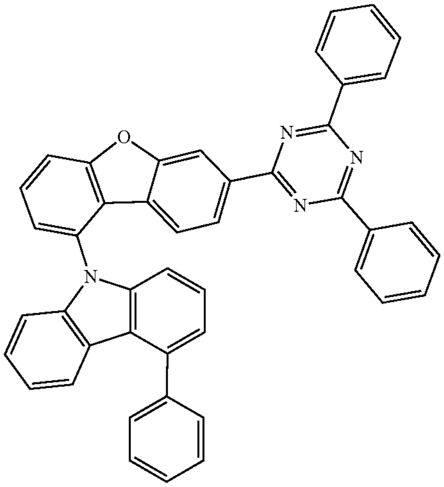
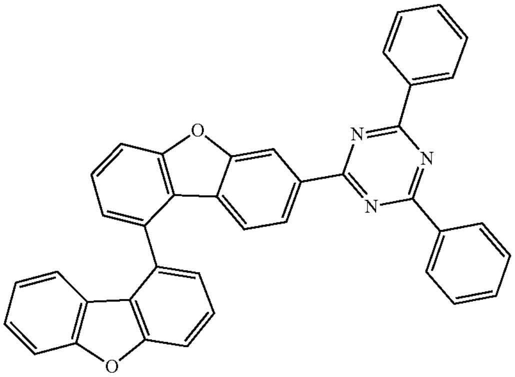
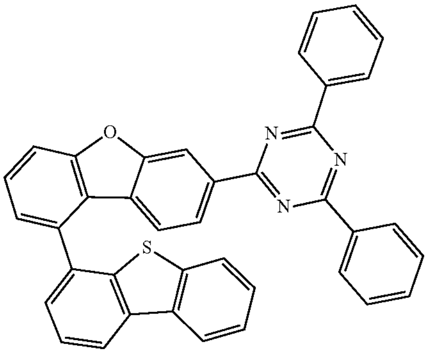

-continued
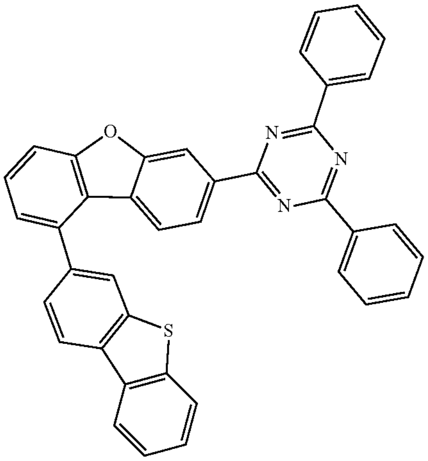
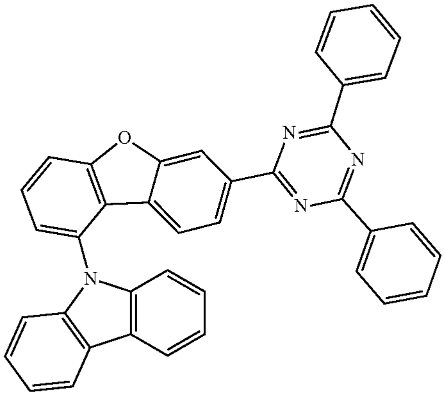
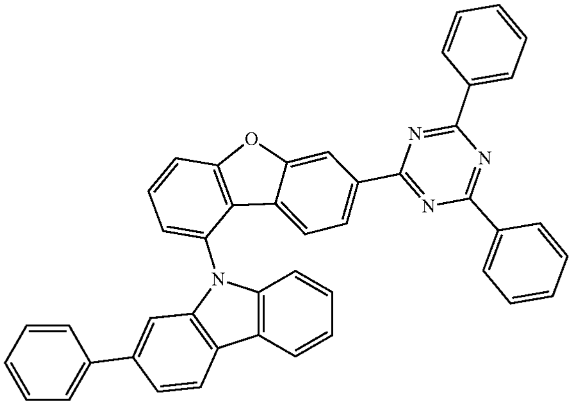
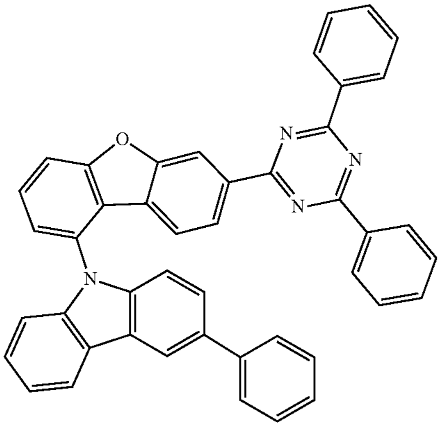
-continued
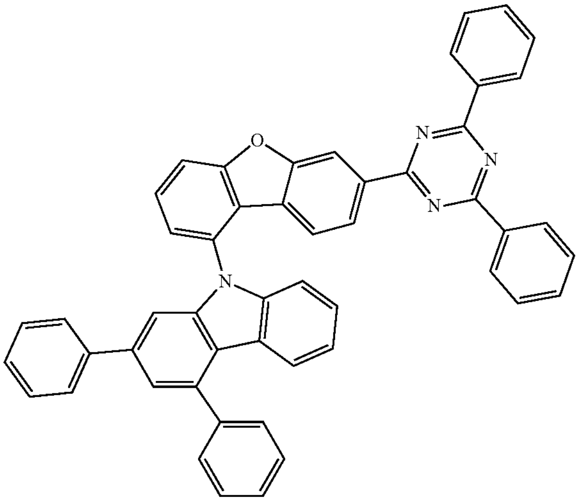
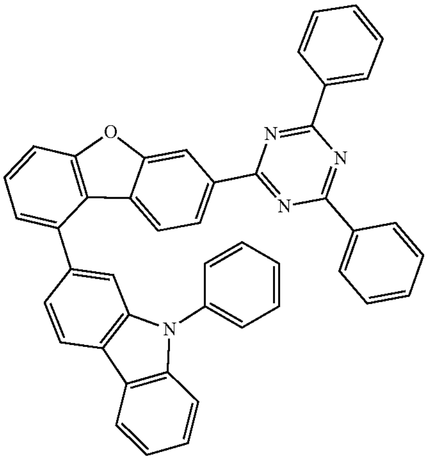
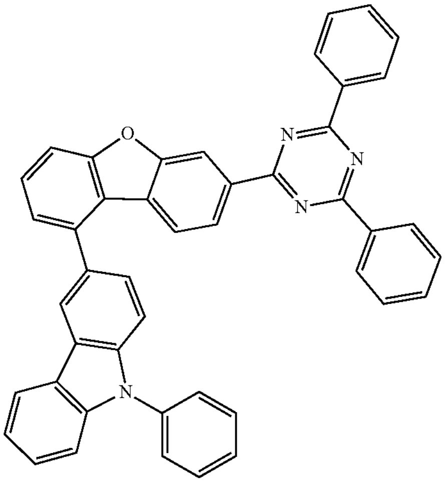

-continued
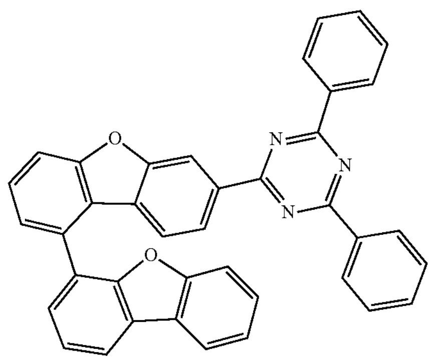
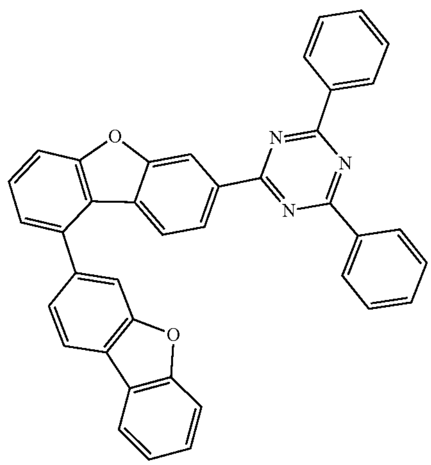
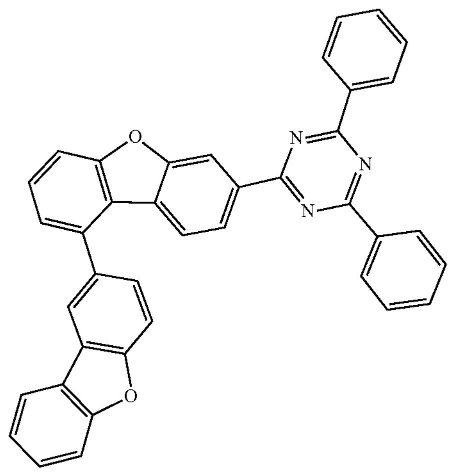
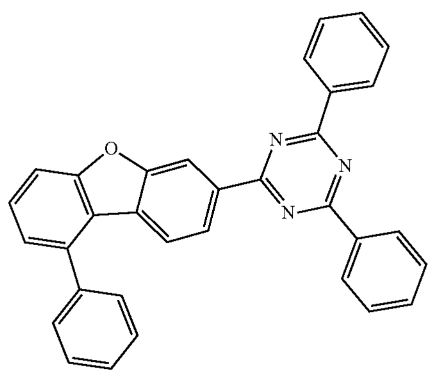
-continued
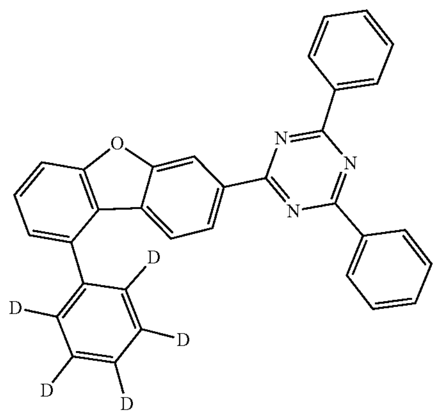
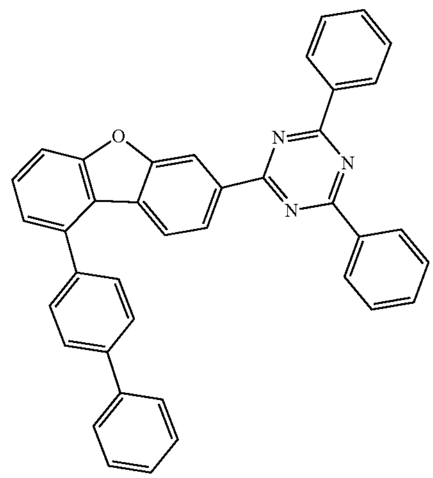
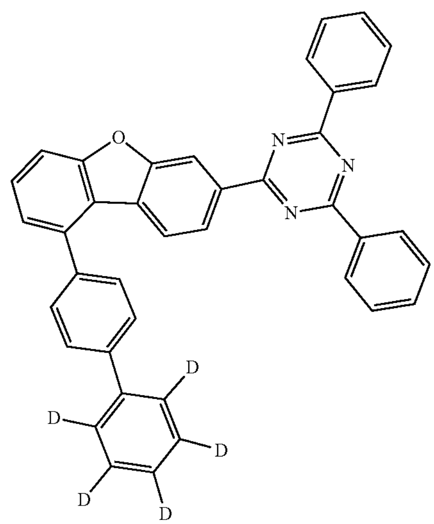

-continued
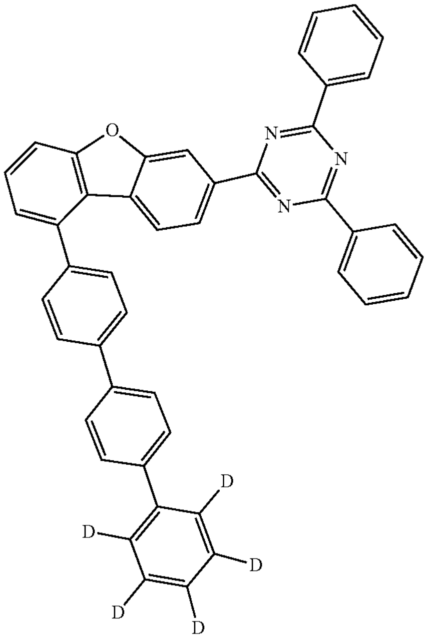
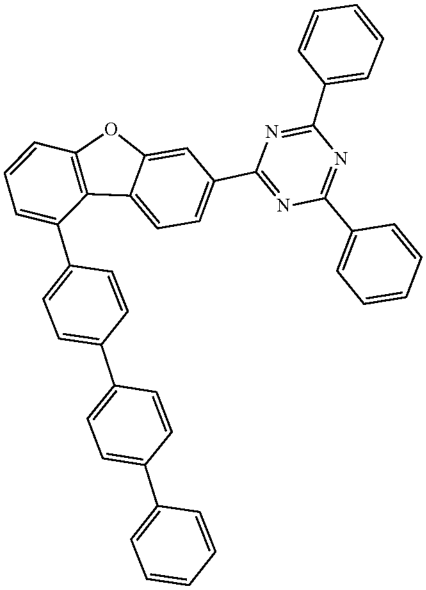
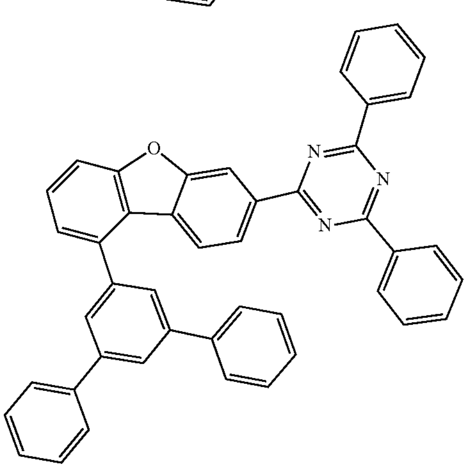
-continued
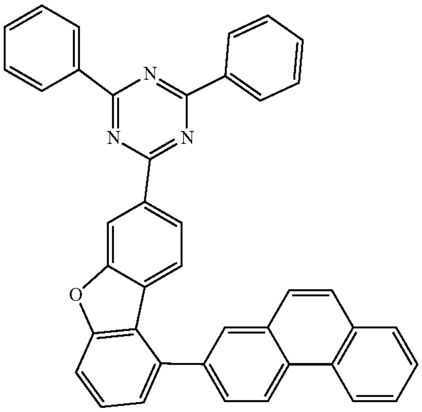
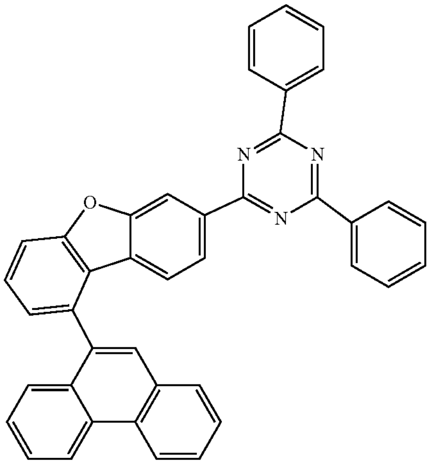
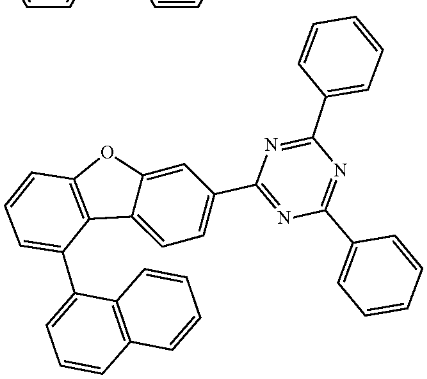
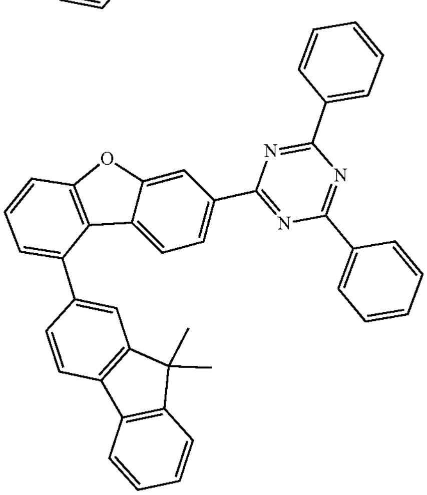

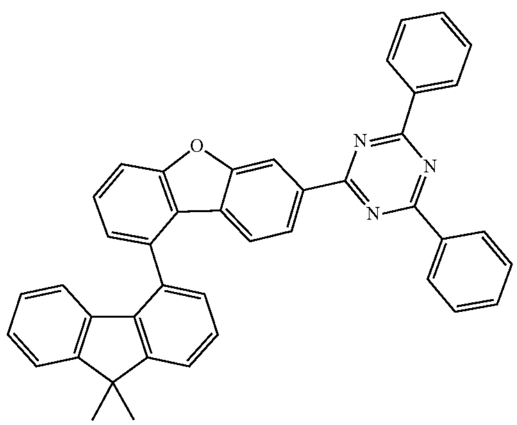
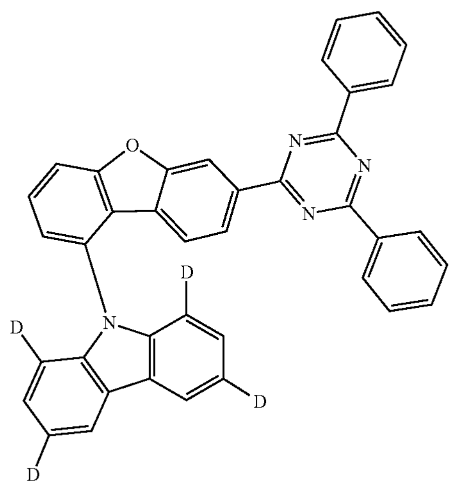
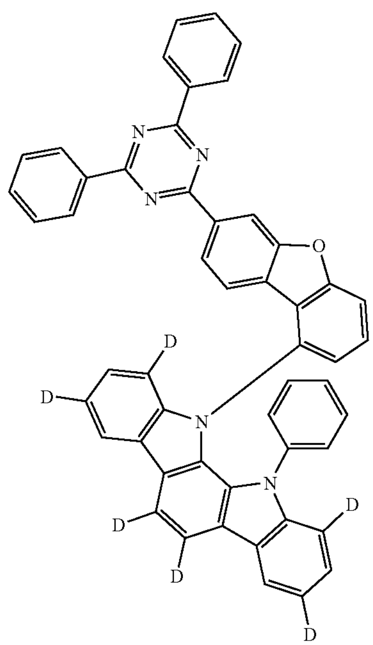
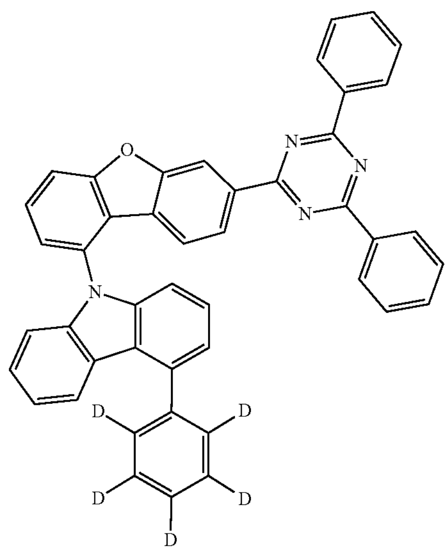
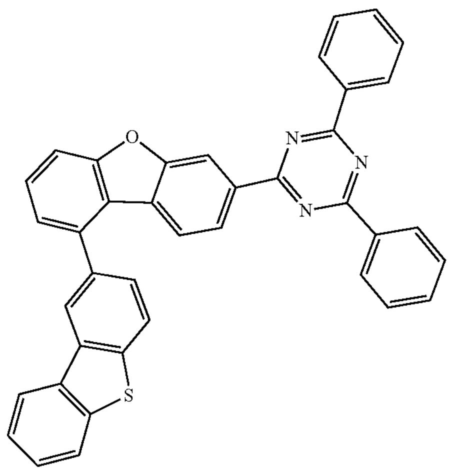
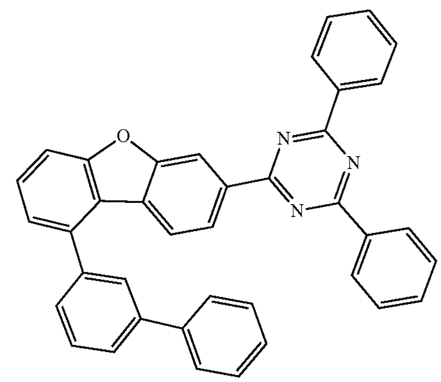

-continued
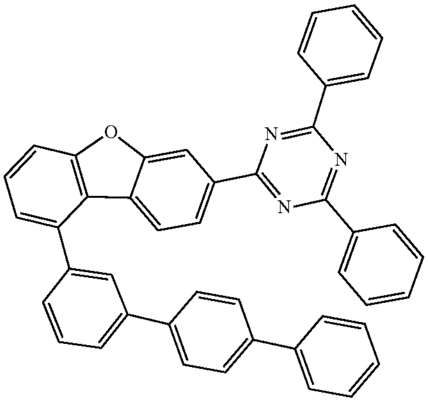
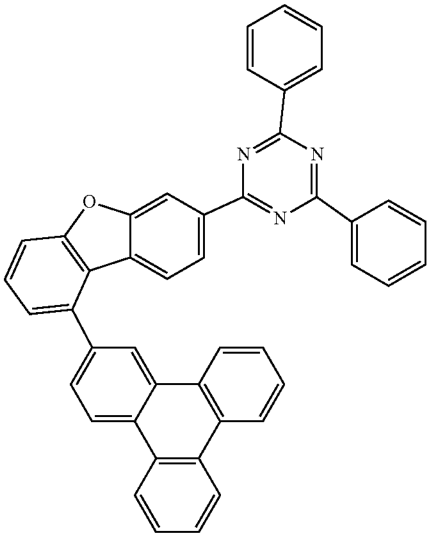
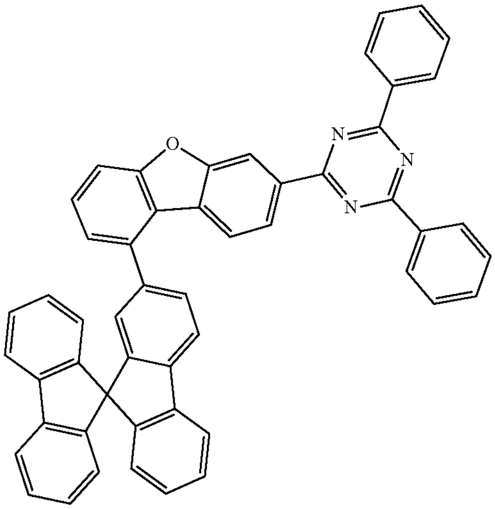
-continued
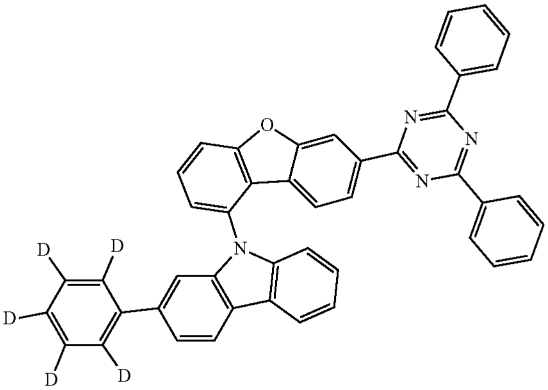
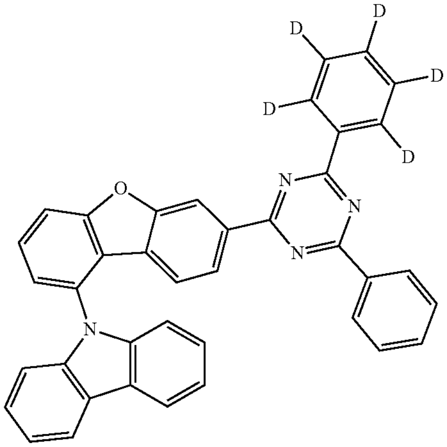
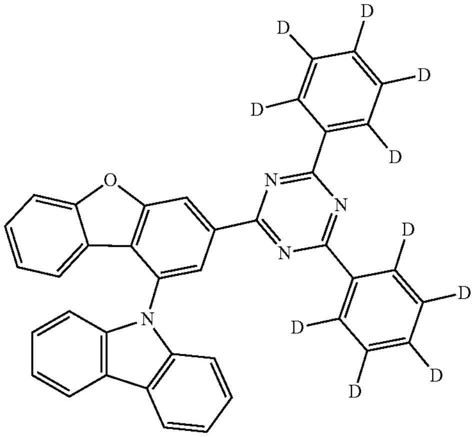

-continued
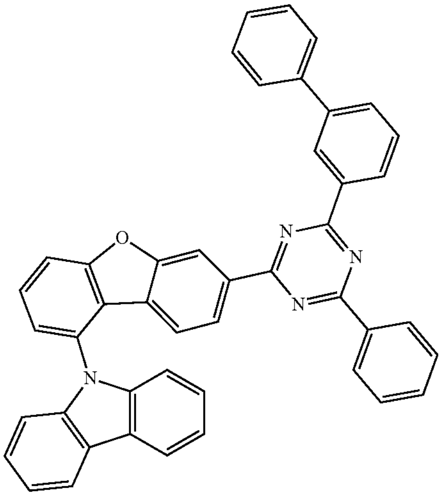
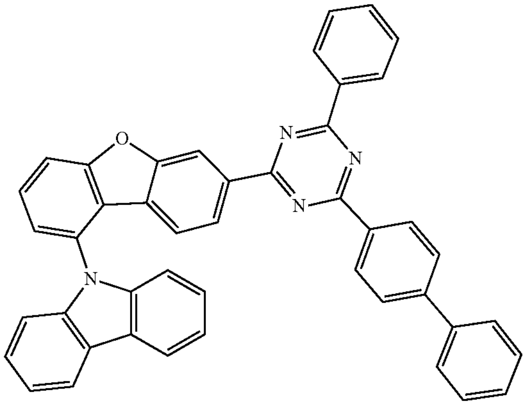
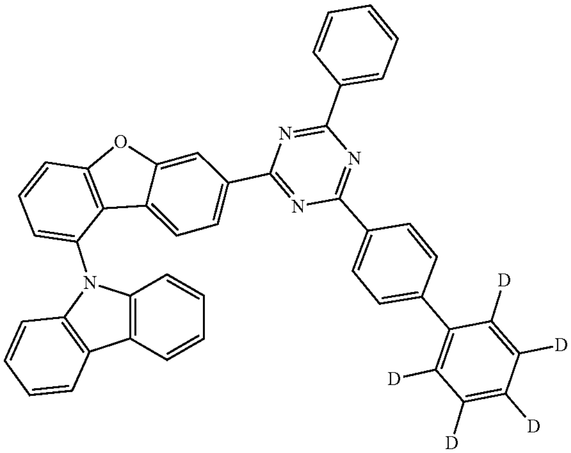
-continued
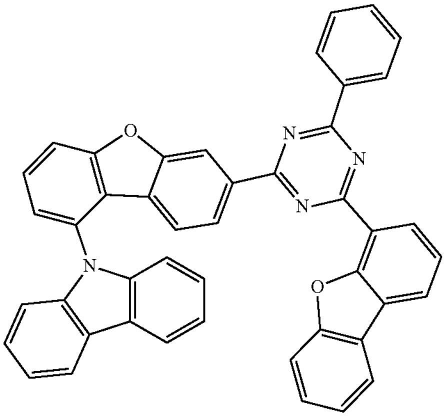
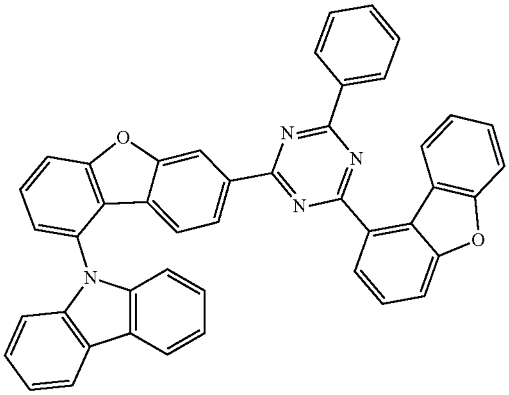
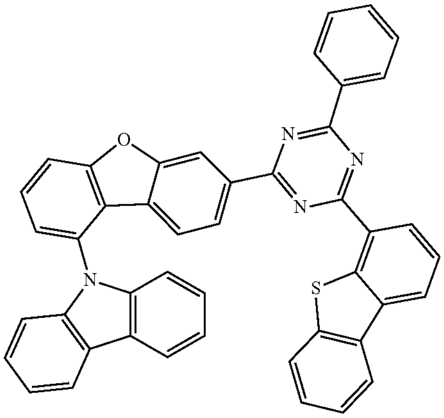
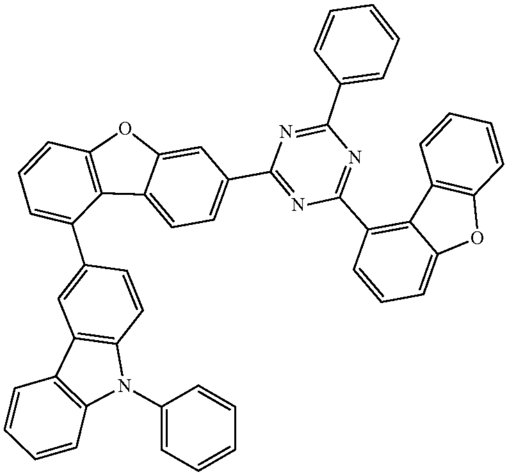

-continued
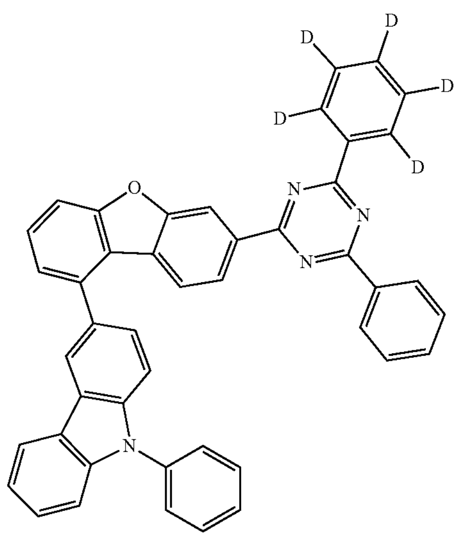
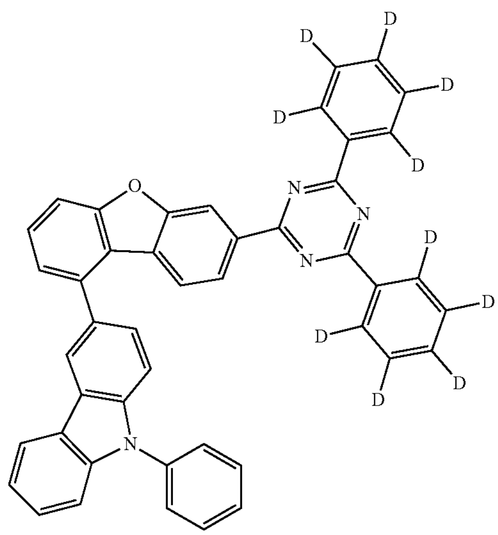
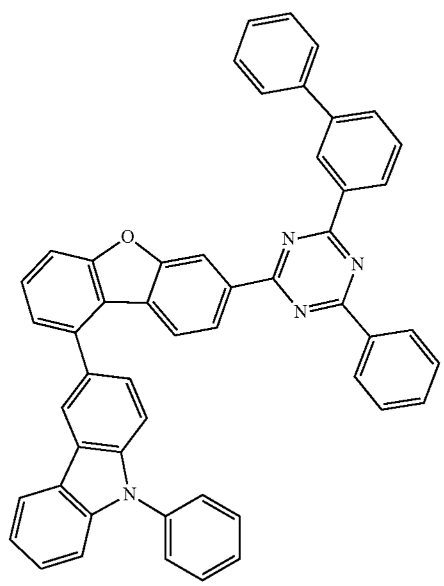
-continued
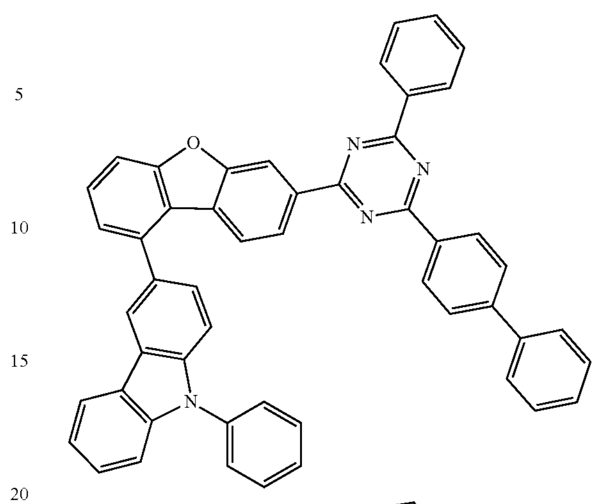
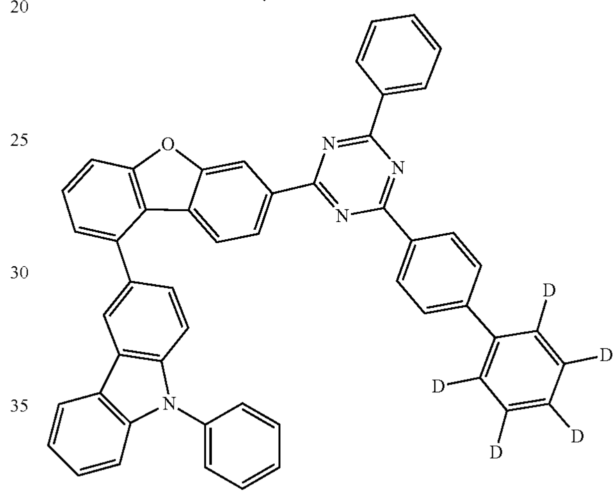
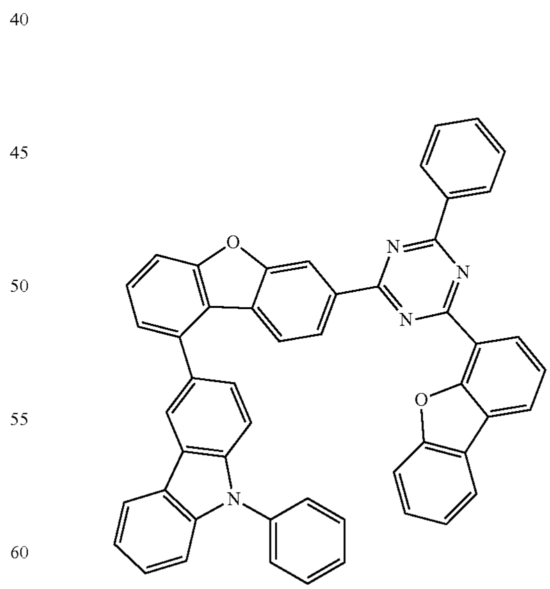

-continued
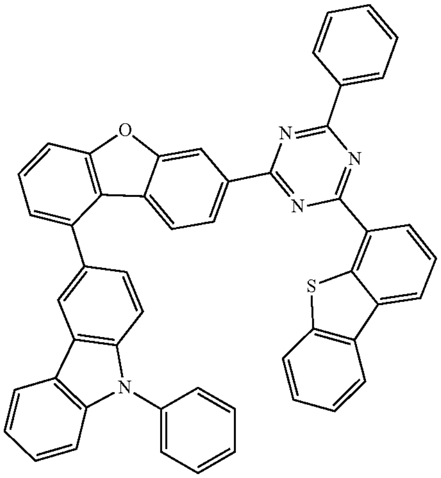
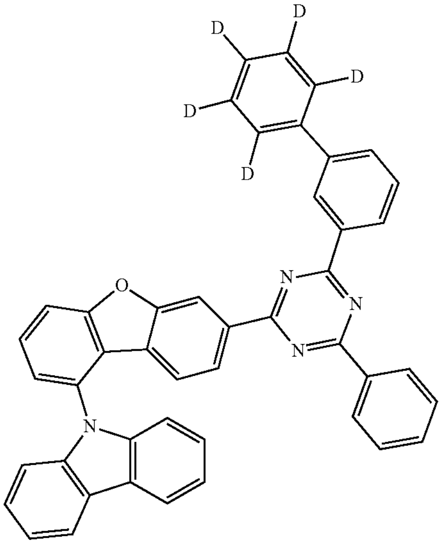
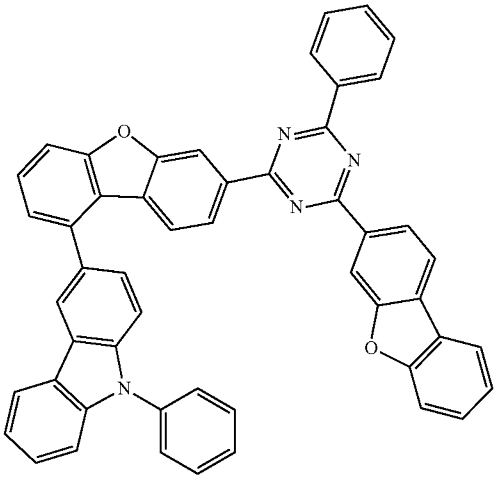
-continued
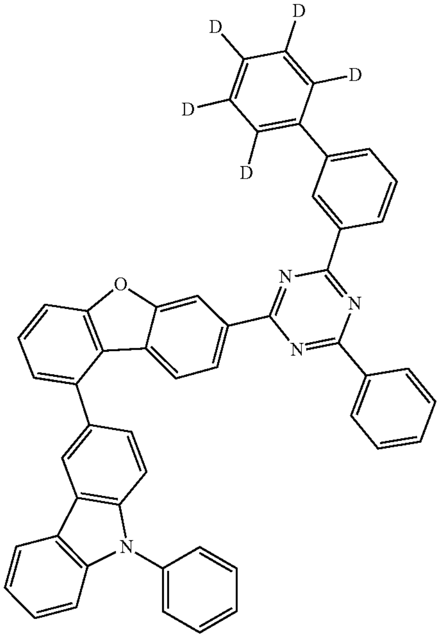
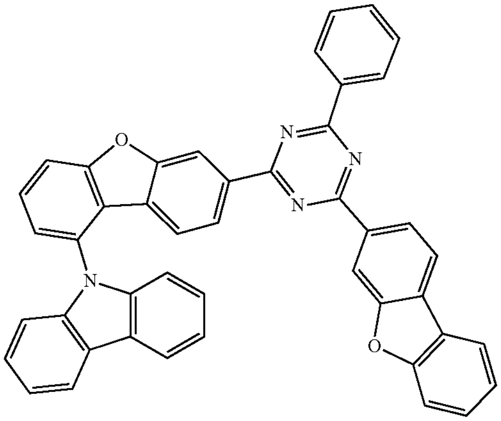
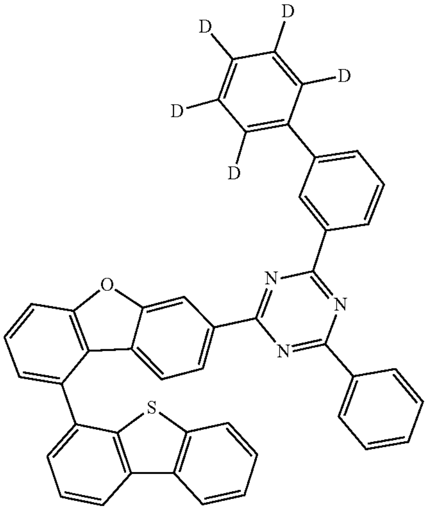

-continued
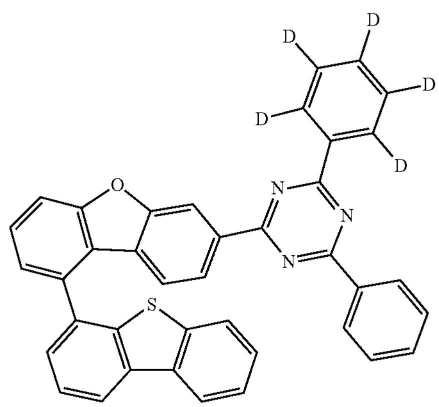
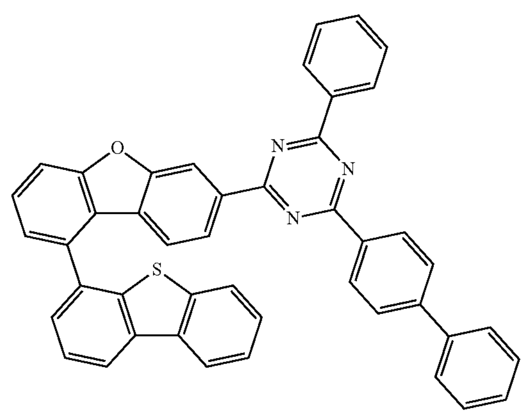
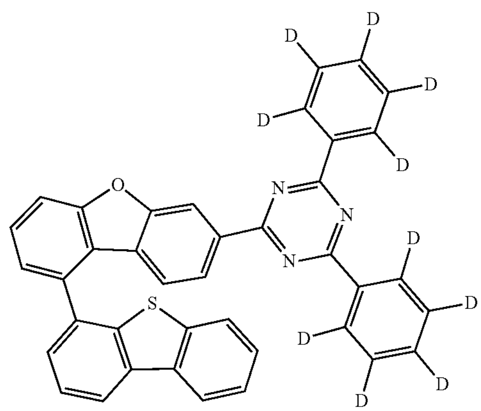
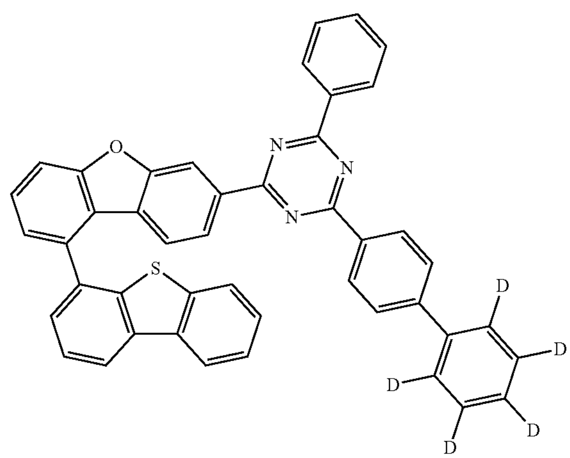
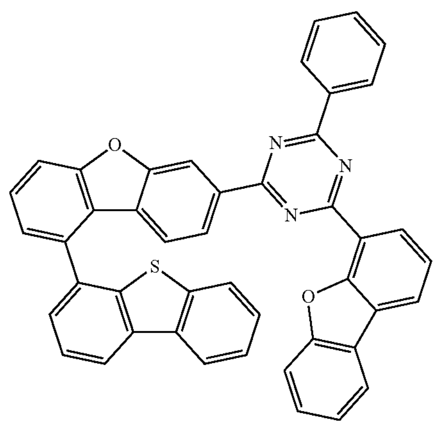
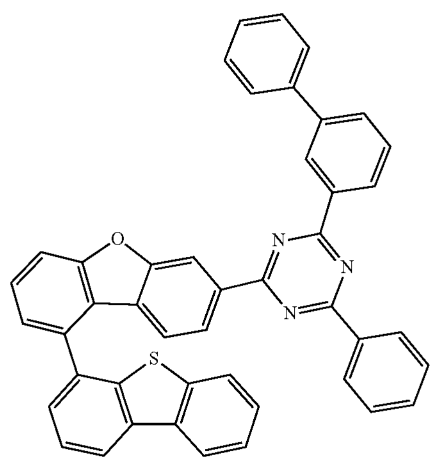
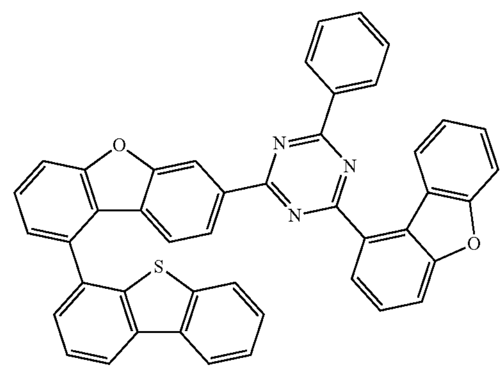

-continued
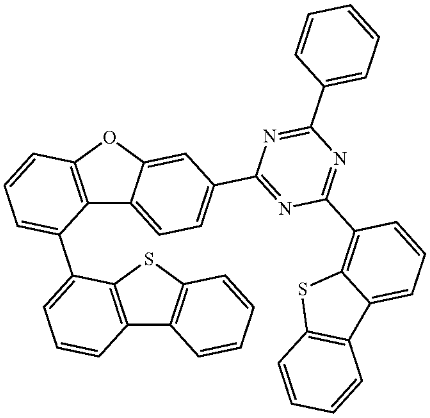
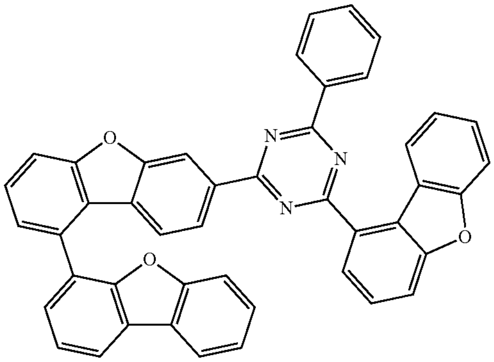
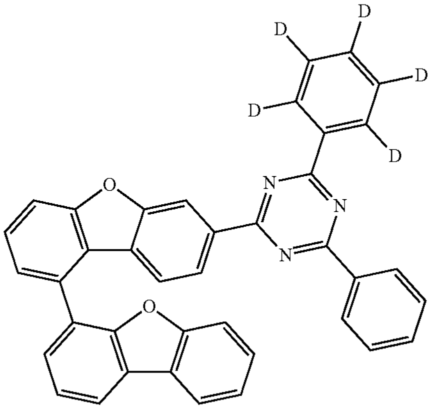
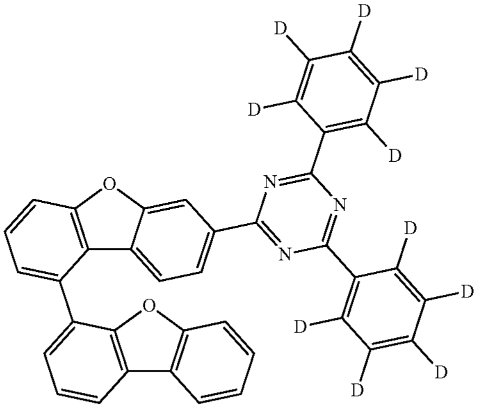
-continued
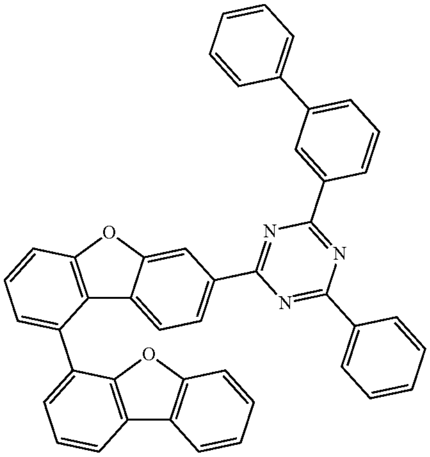
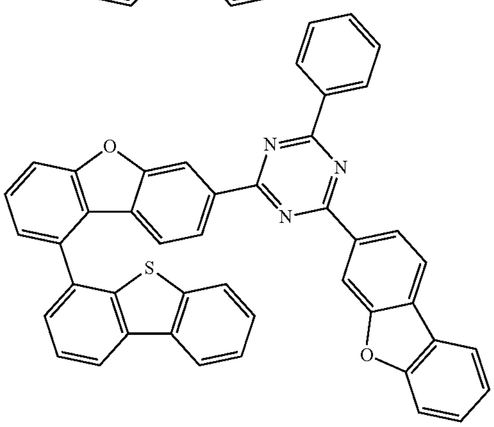
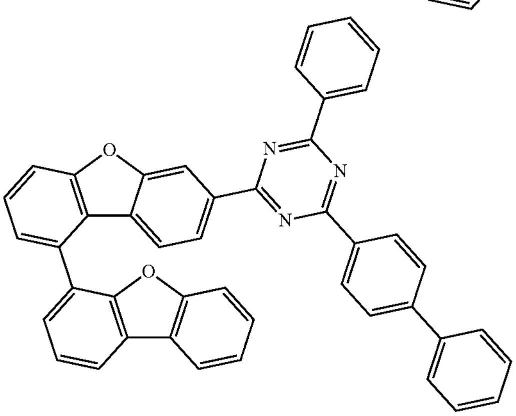
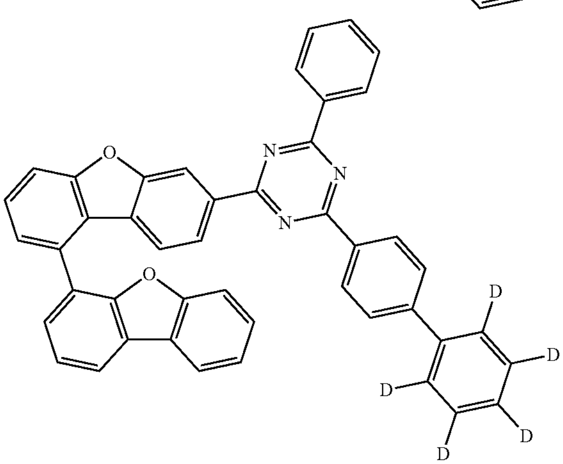

-continued
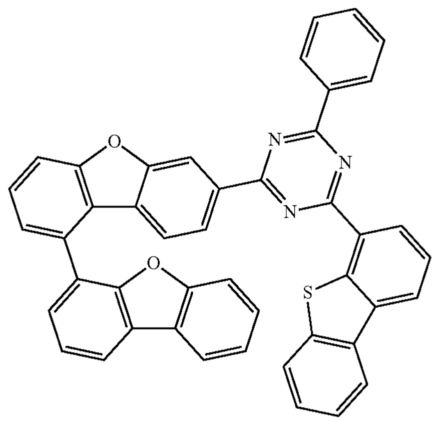
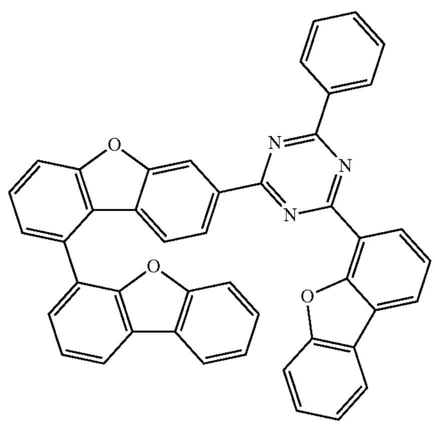
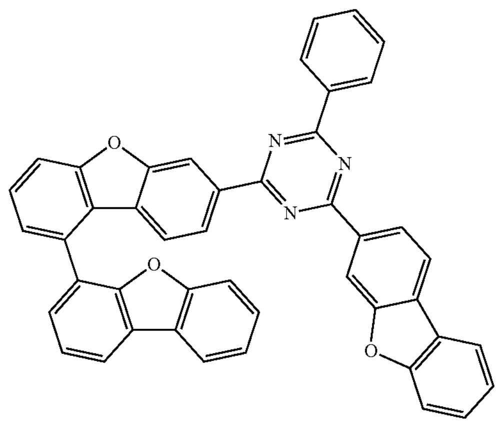
-continued
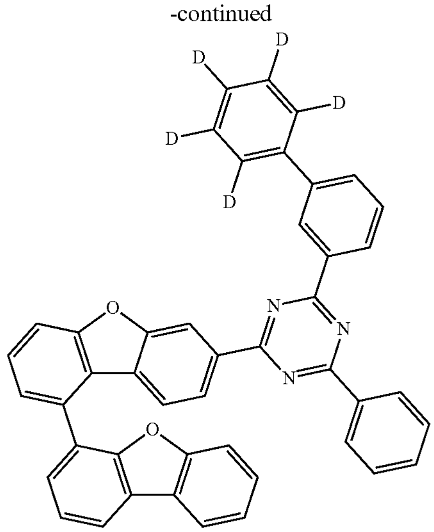
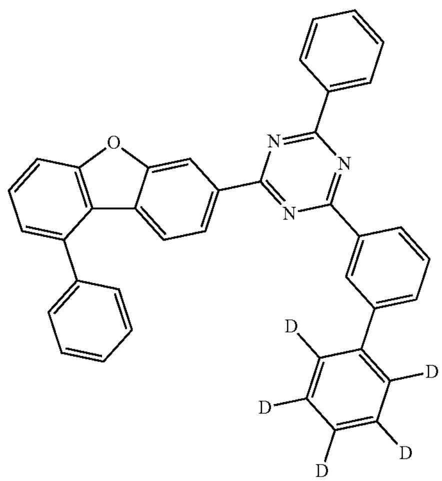
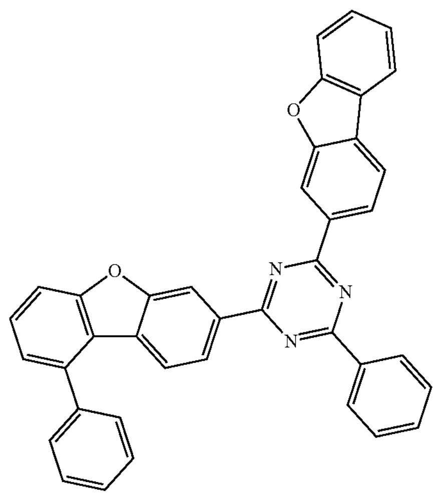

-continued
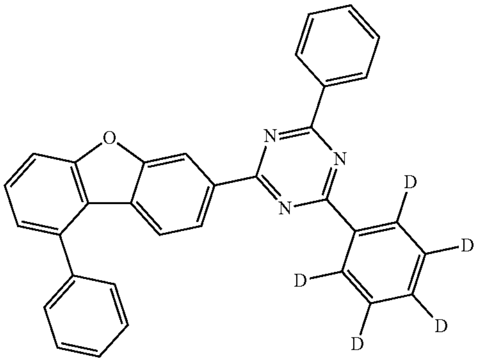
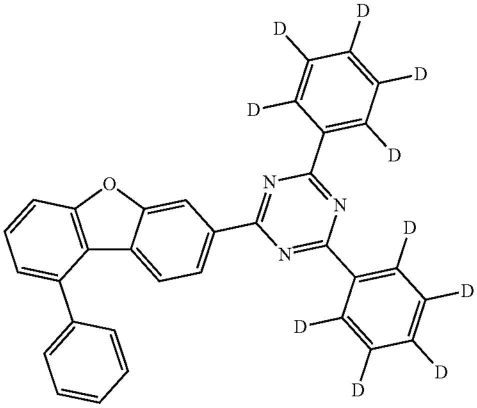
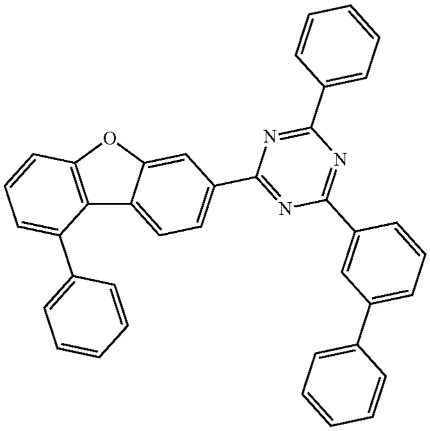
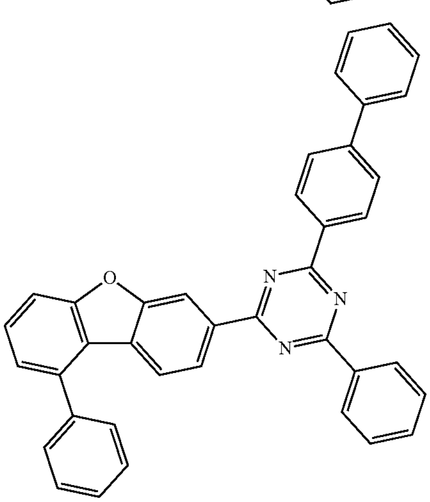
-continued
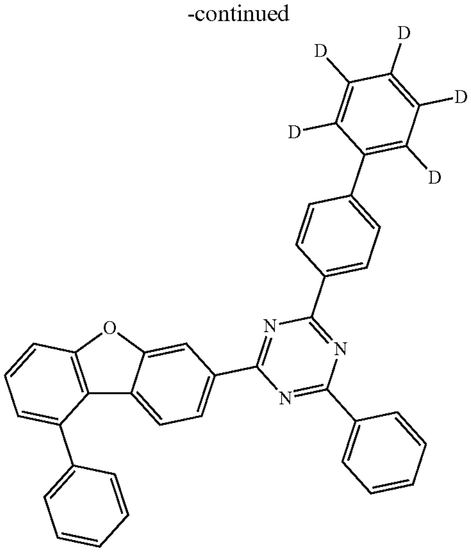
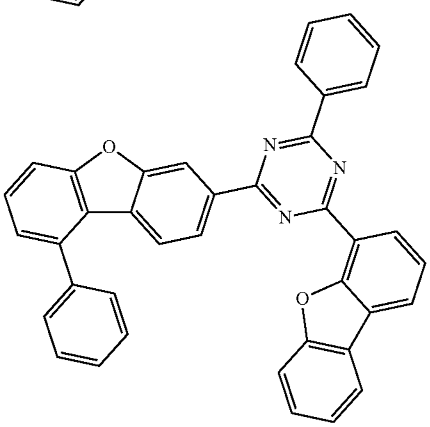
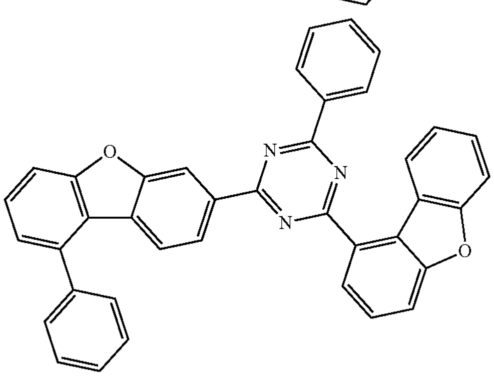
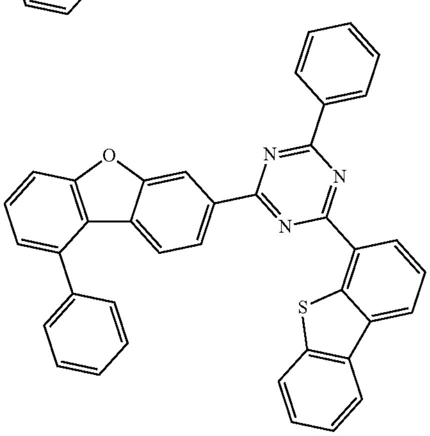

-continued
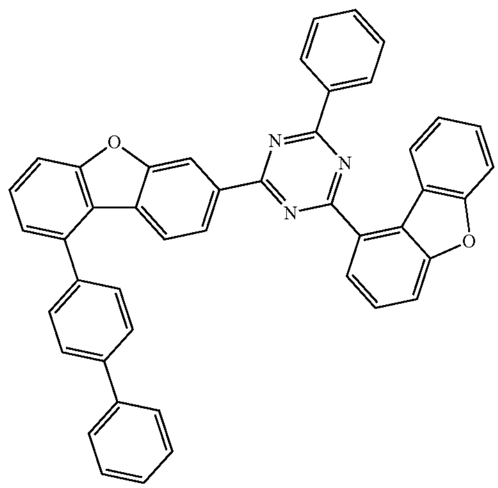
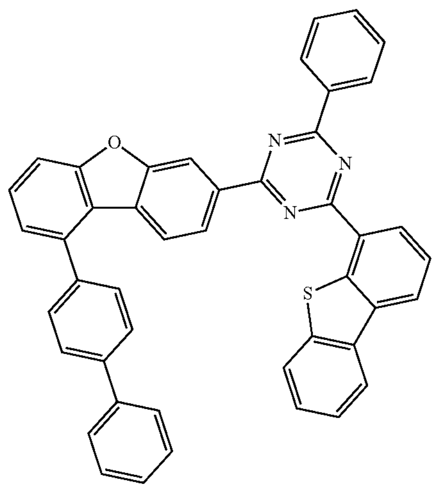
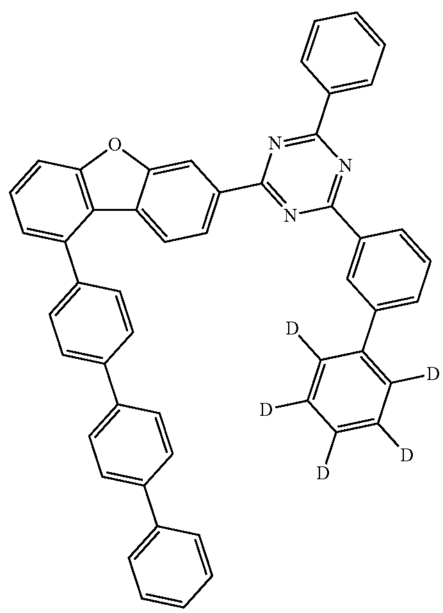
-continued
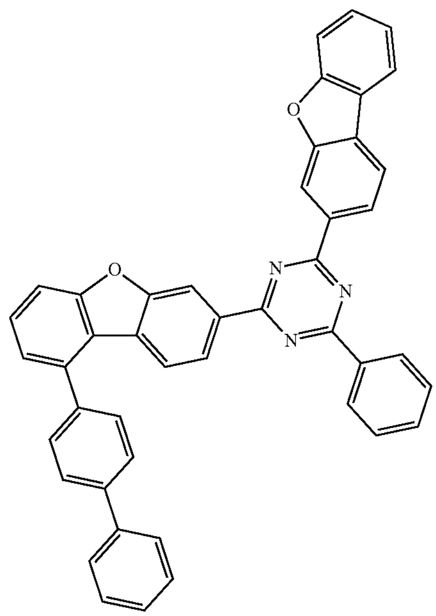
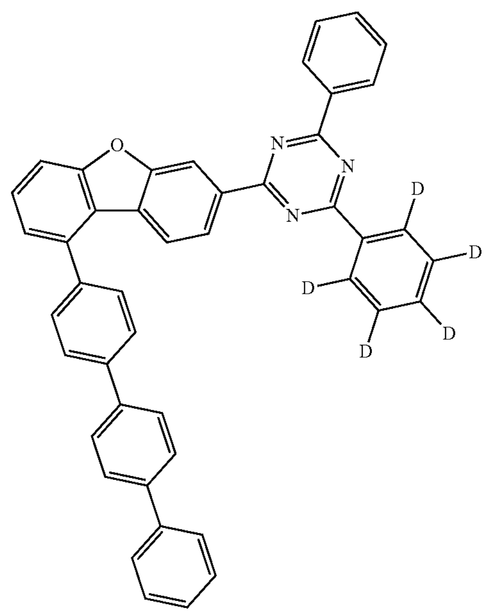

-continued
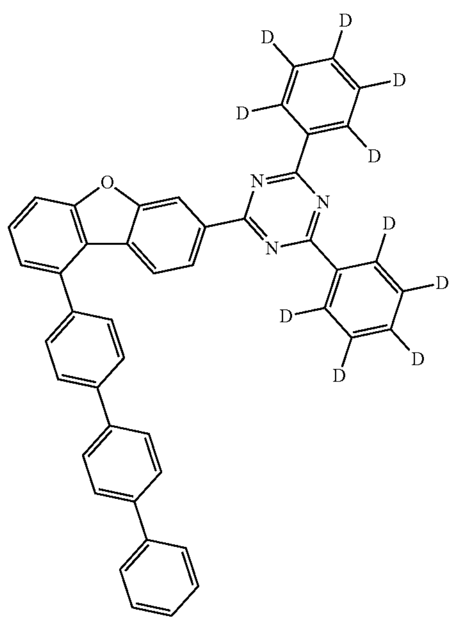
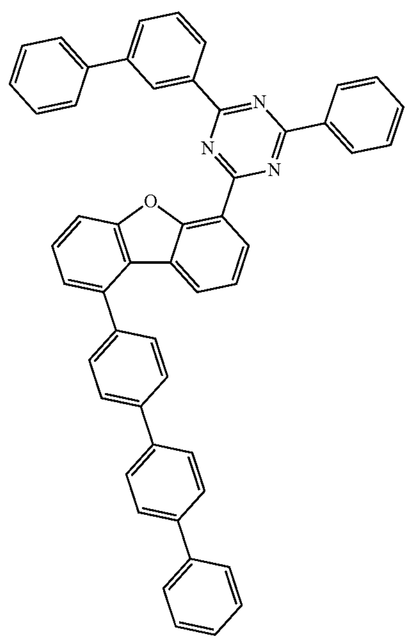
-continued
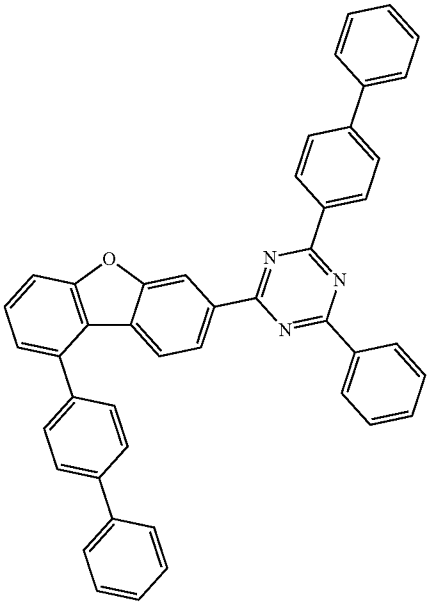
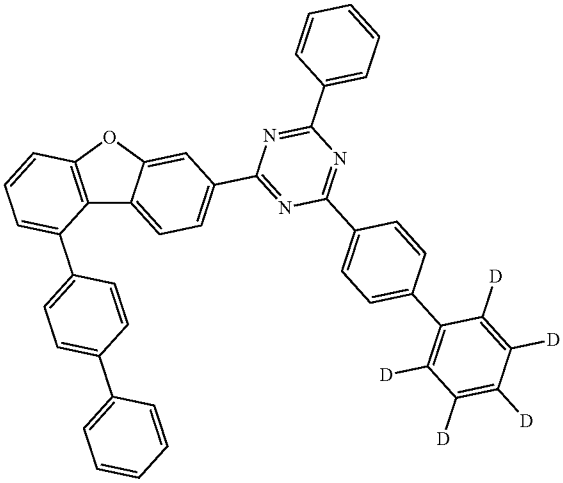
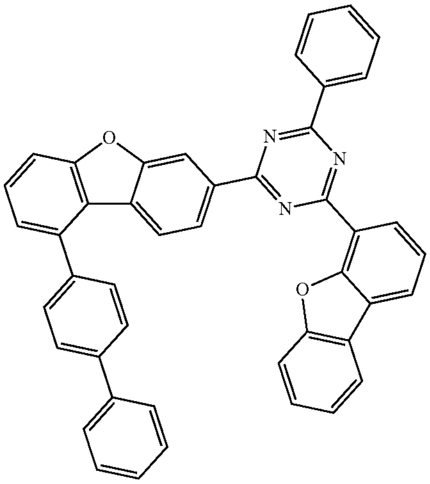

-continued
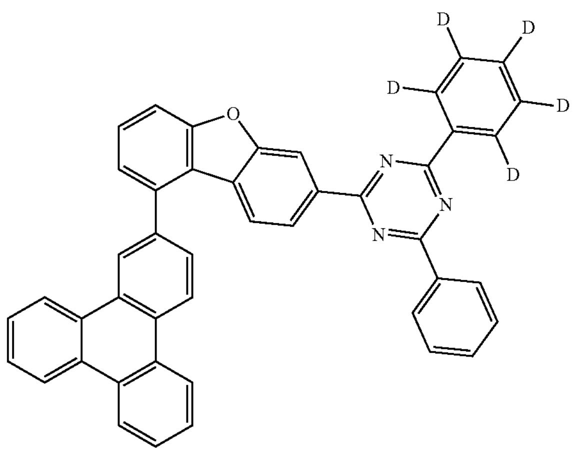
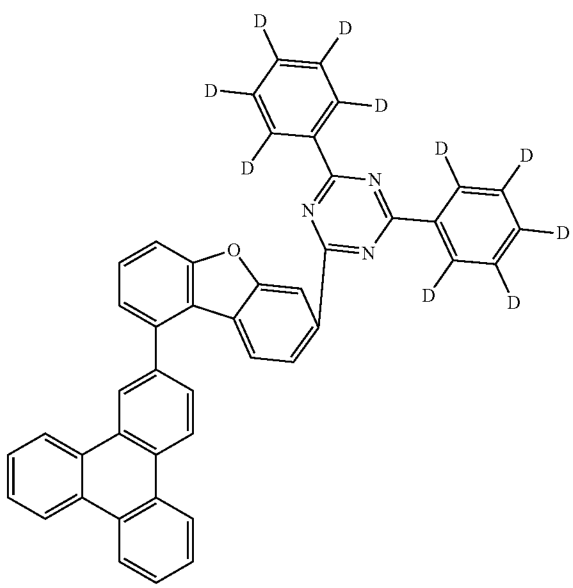
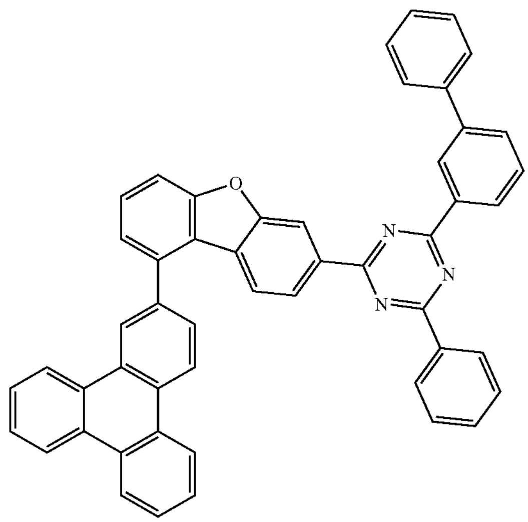
-continued
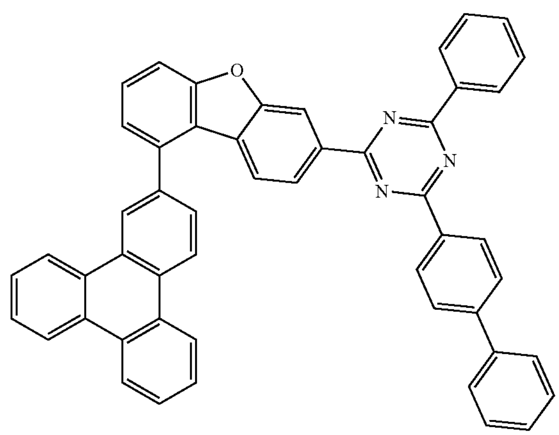
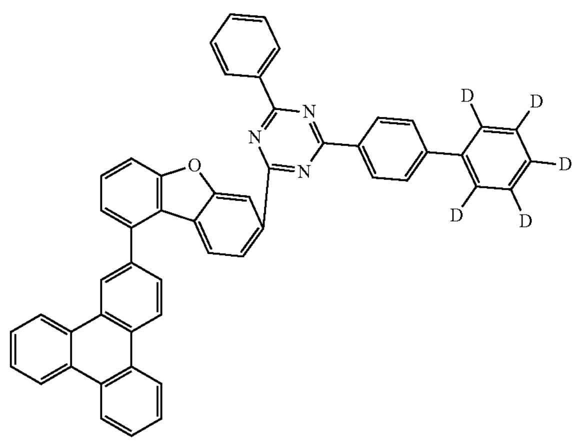
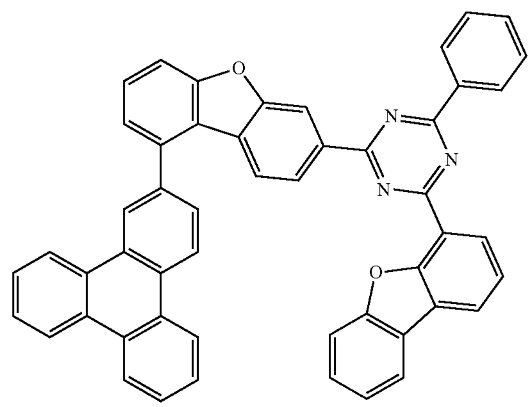
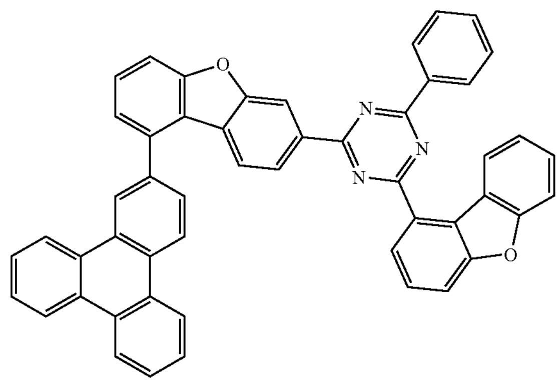

-continued
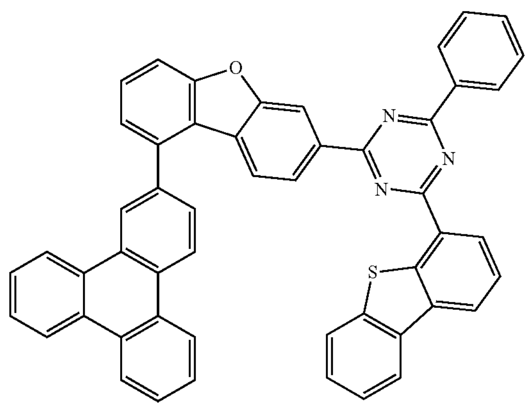
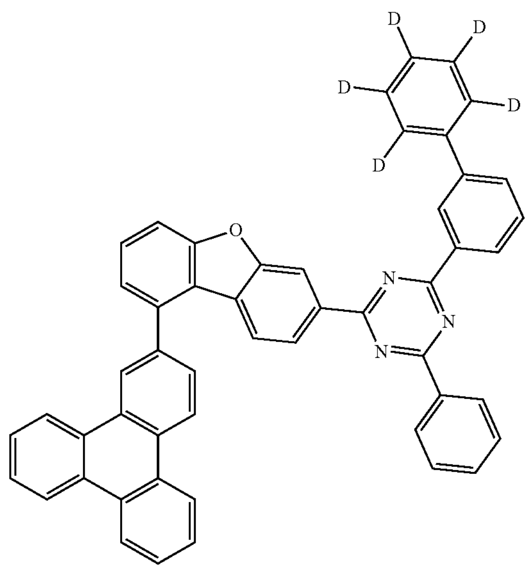
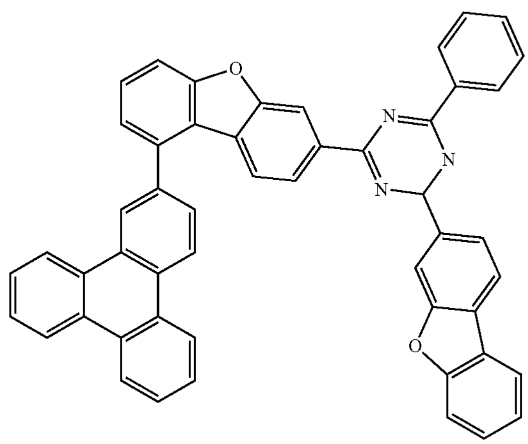
-continued
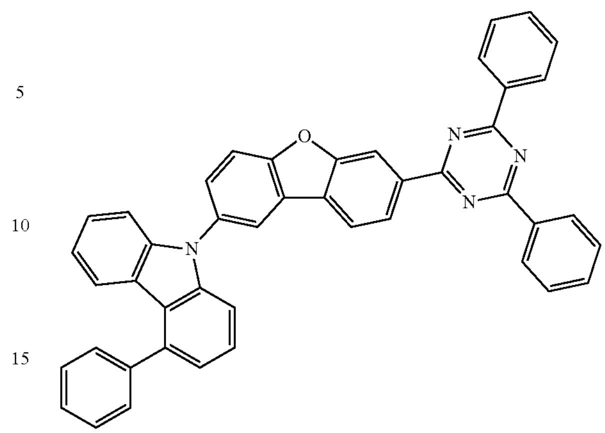
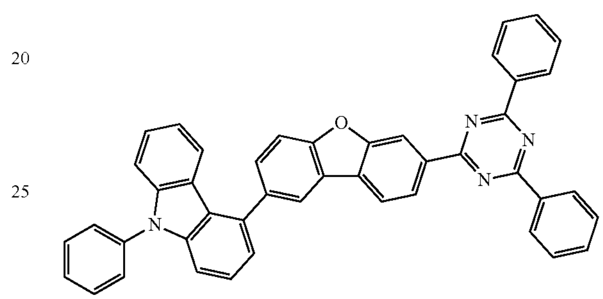
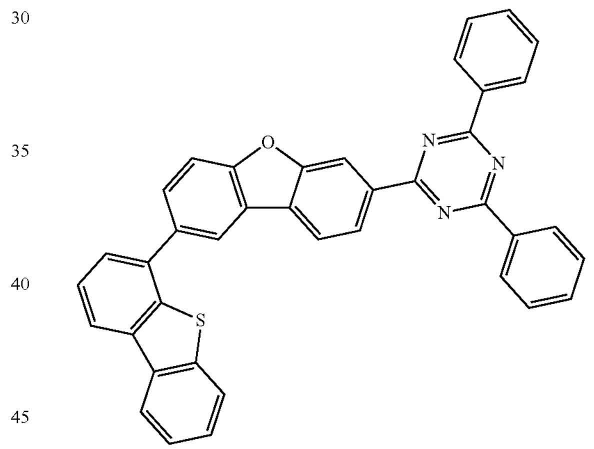
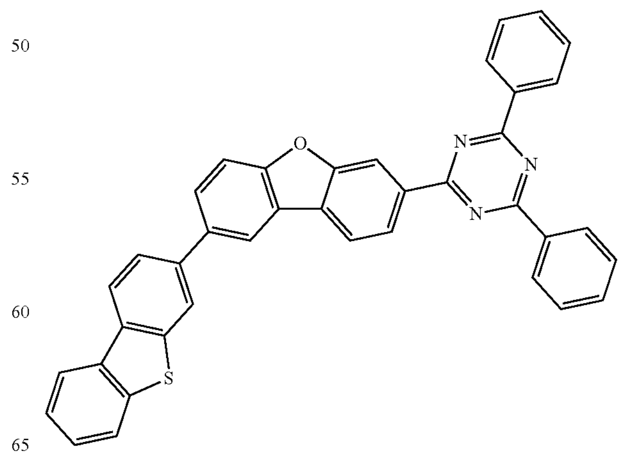

-continued
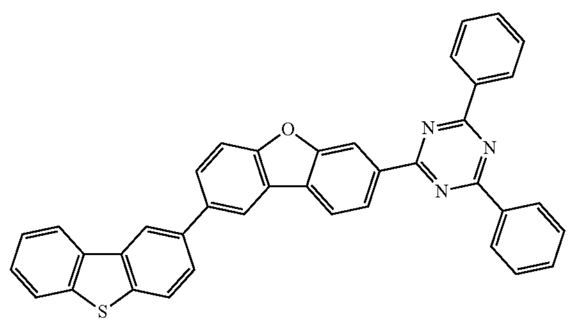
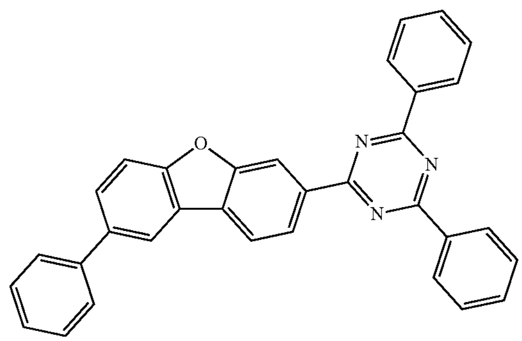
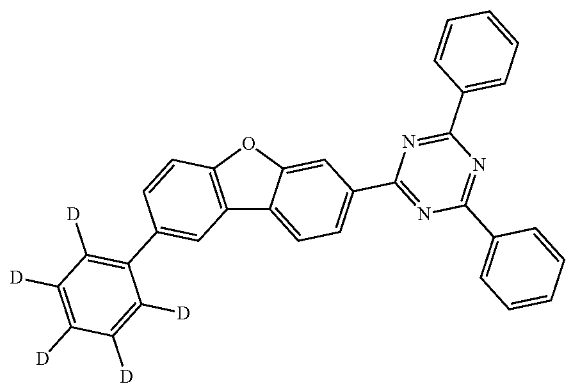
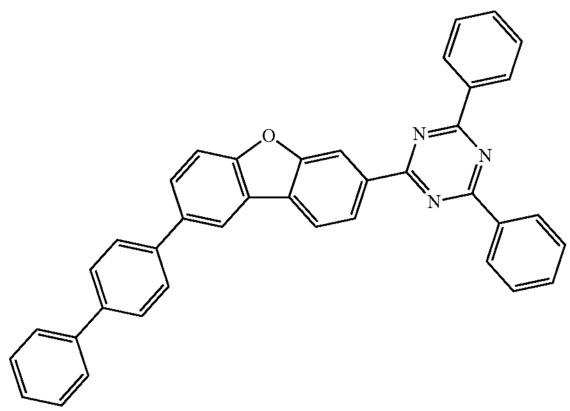
-continued
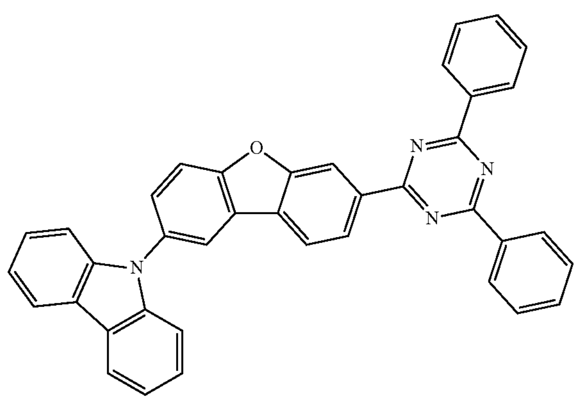
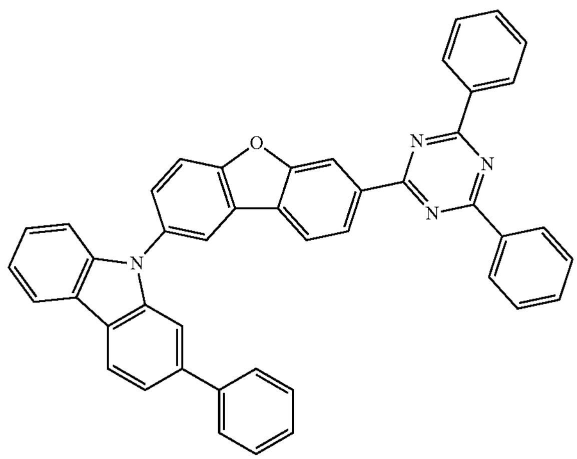
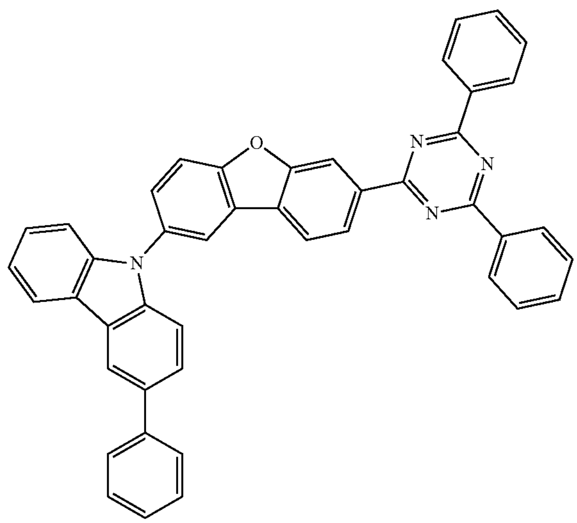

-continued
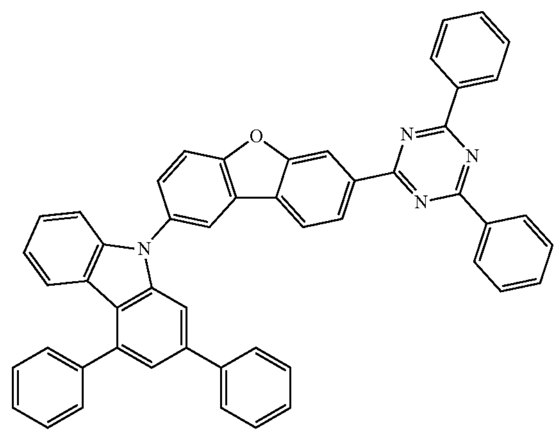
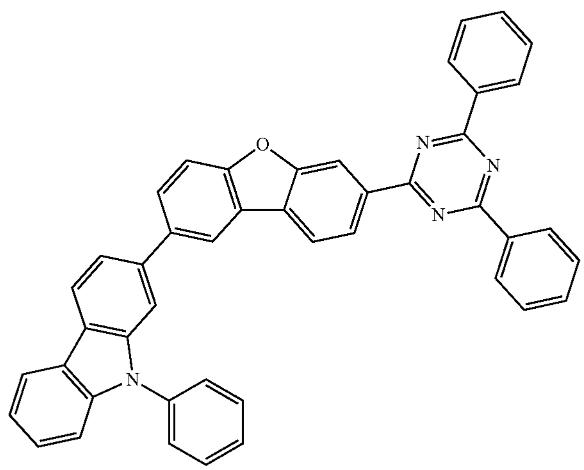
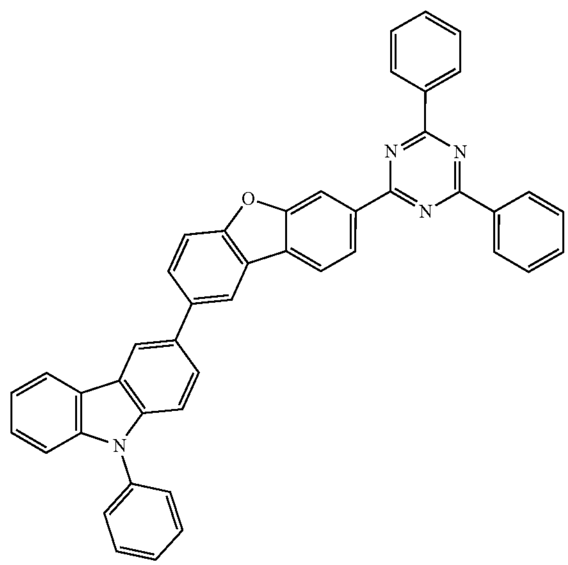
-continued
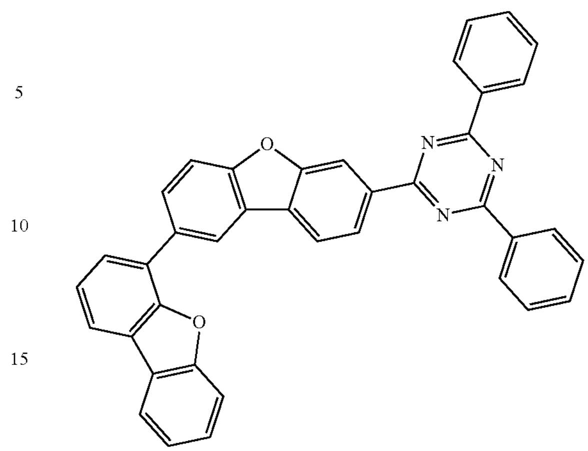
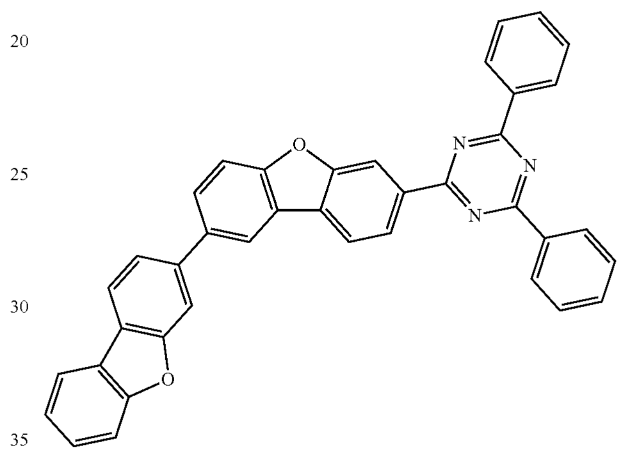
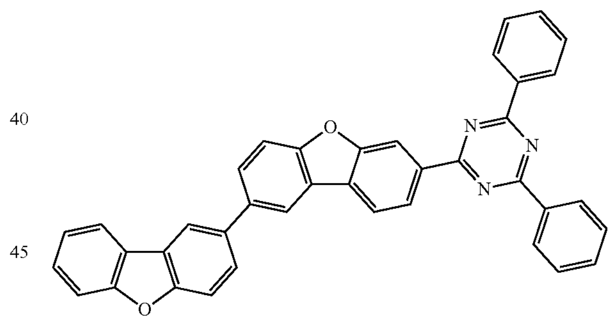
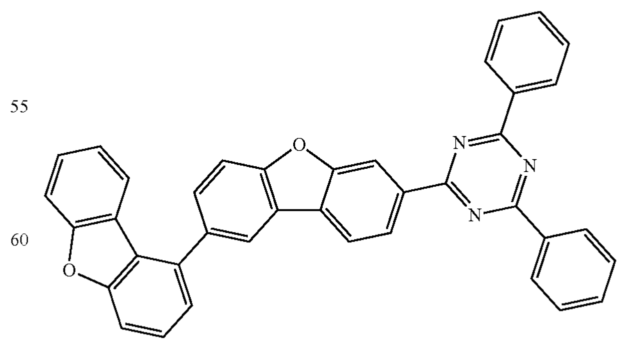

-continued
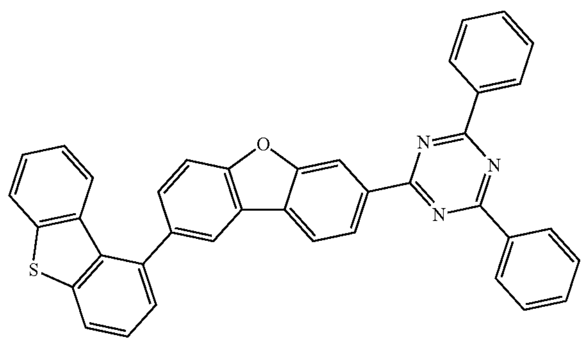
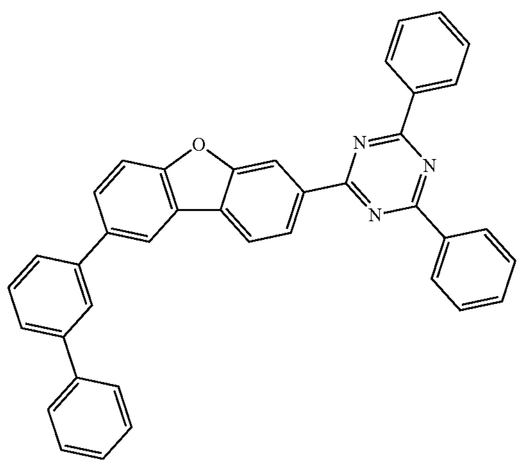
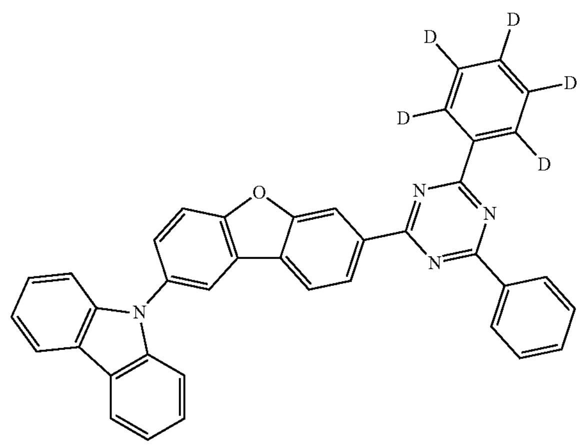
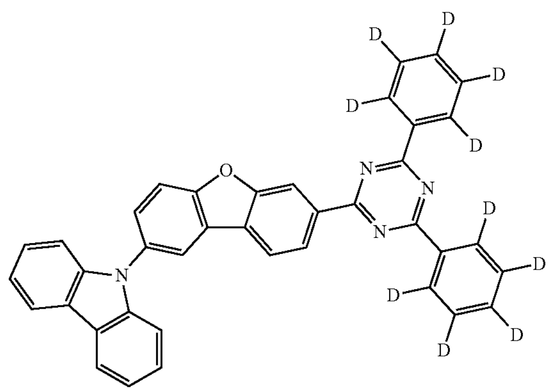
-continued
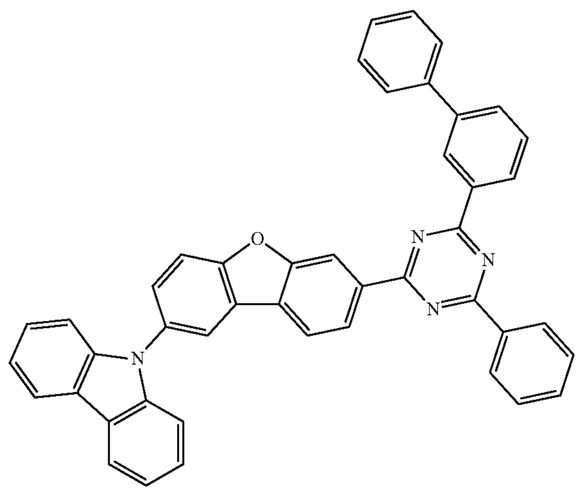
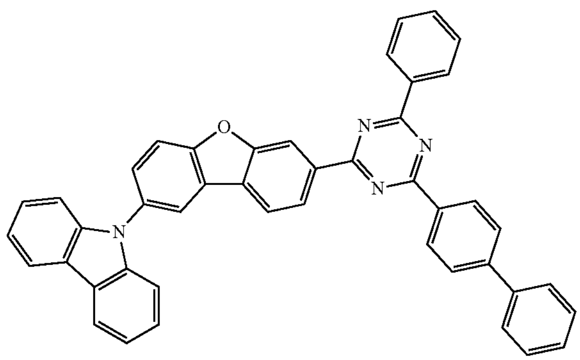
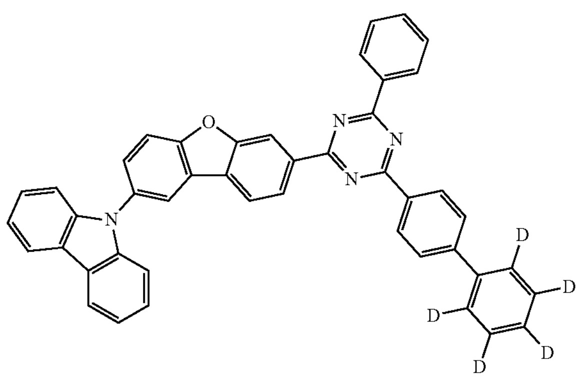
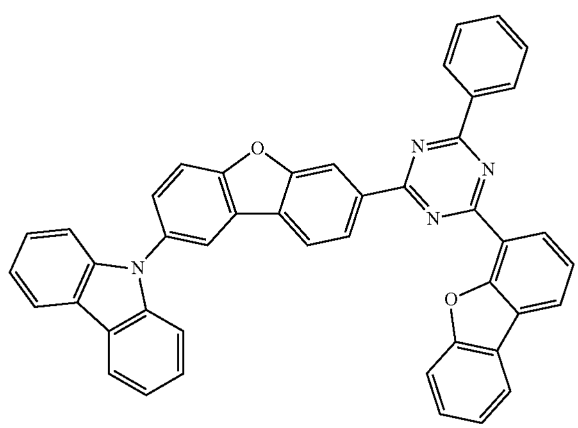

-continued
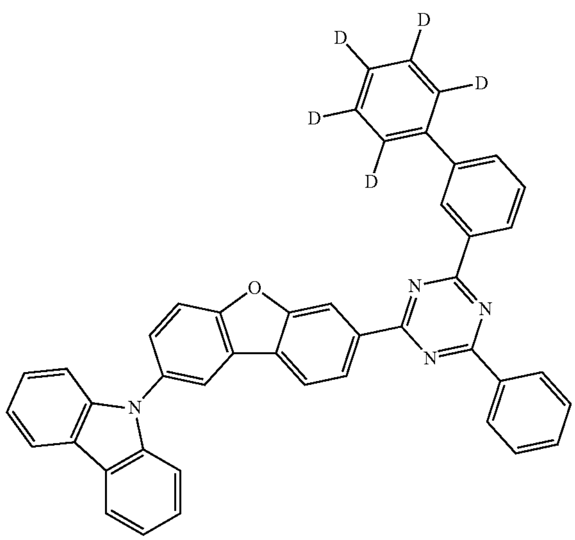
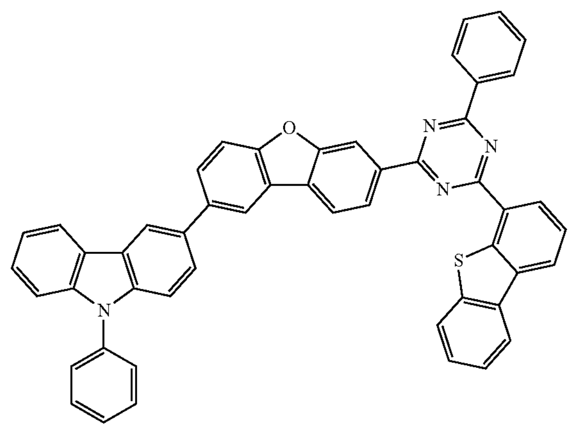
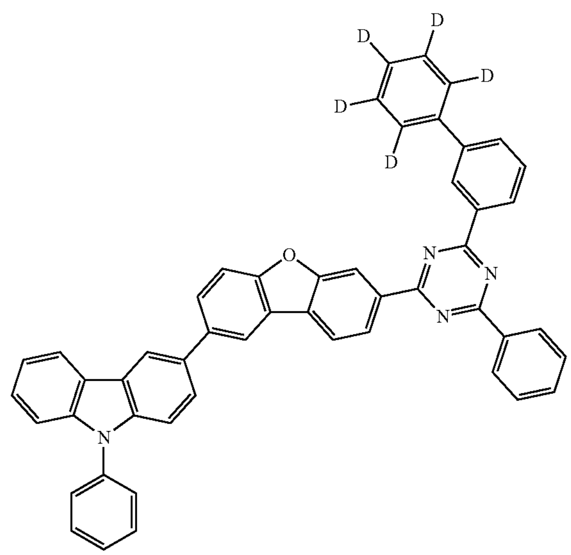
-continued
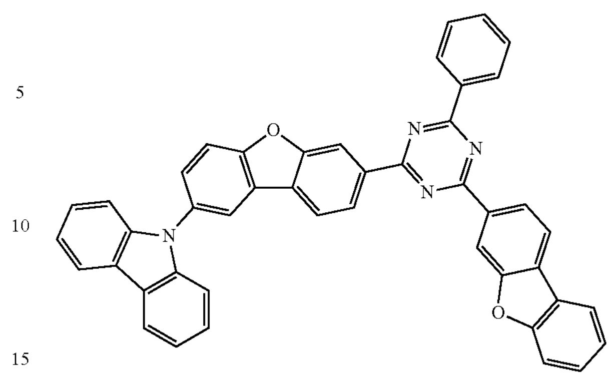
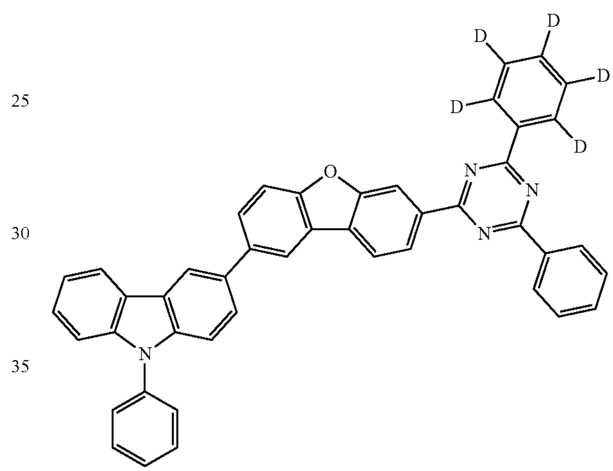
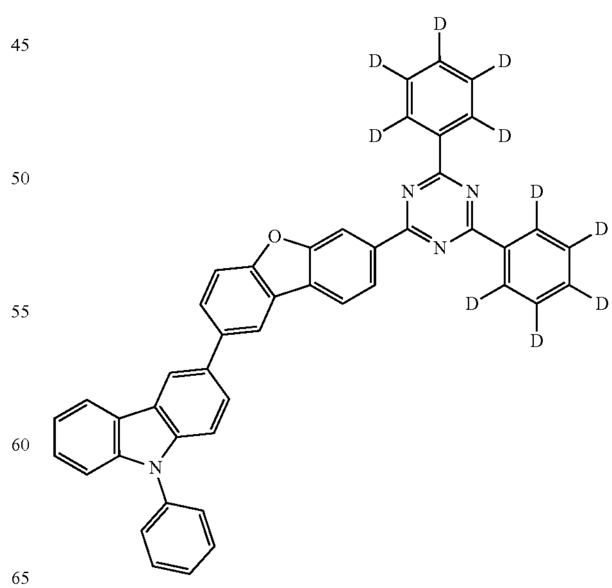

-continued
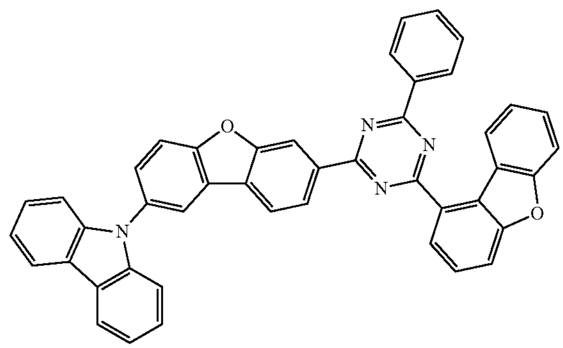
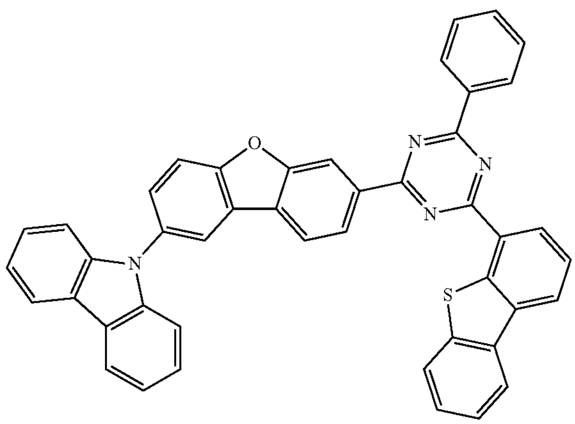
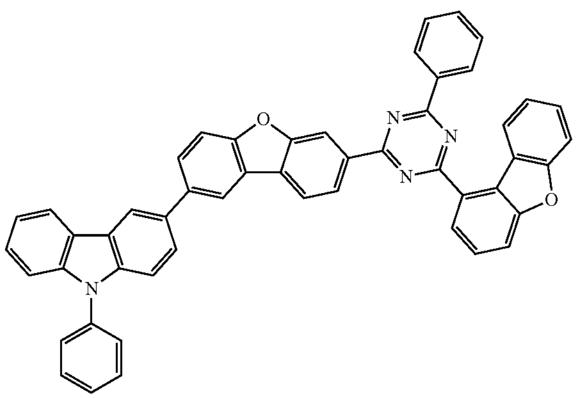
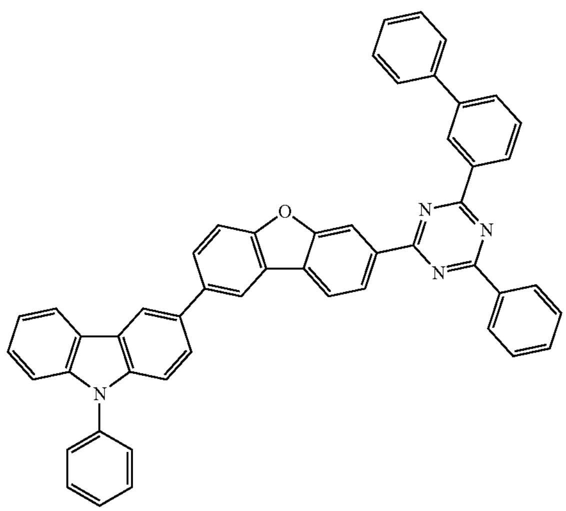
-continued
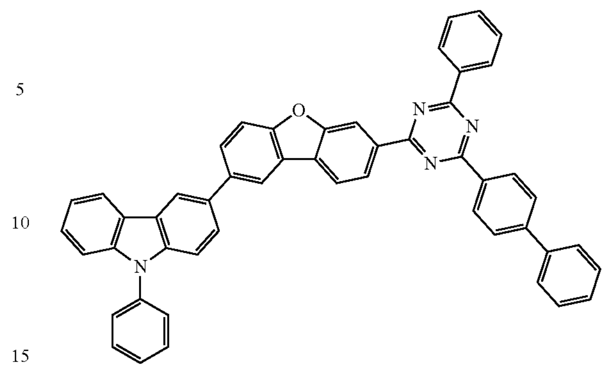
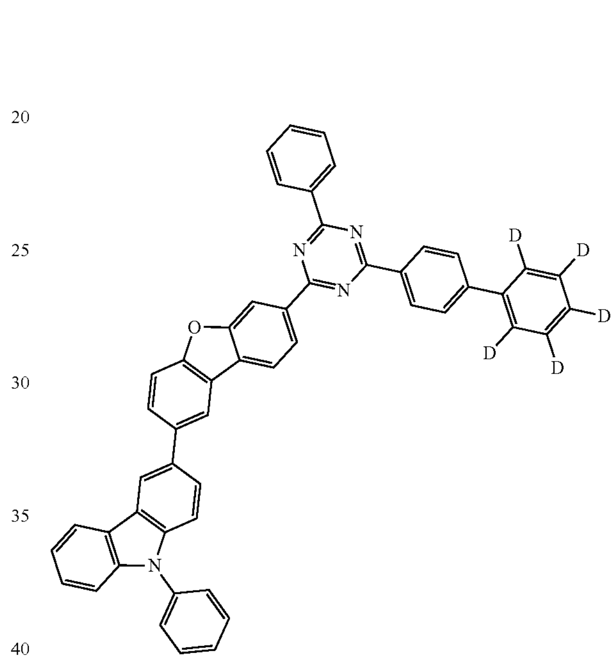
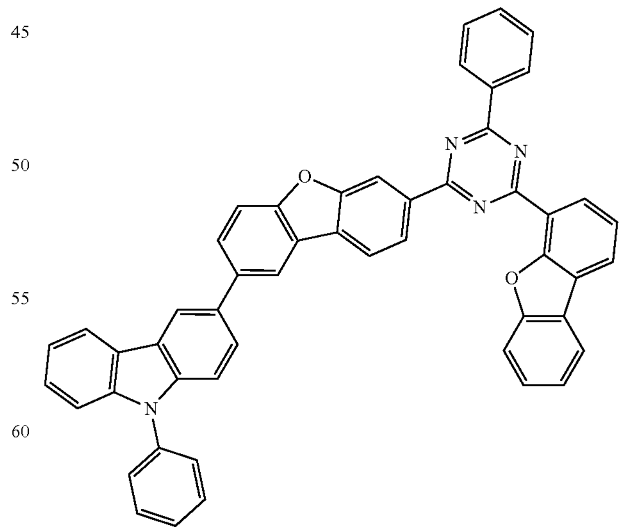

-continued
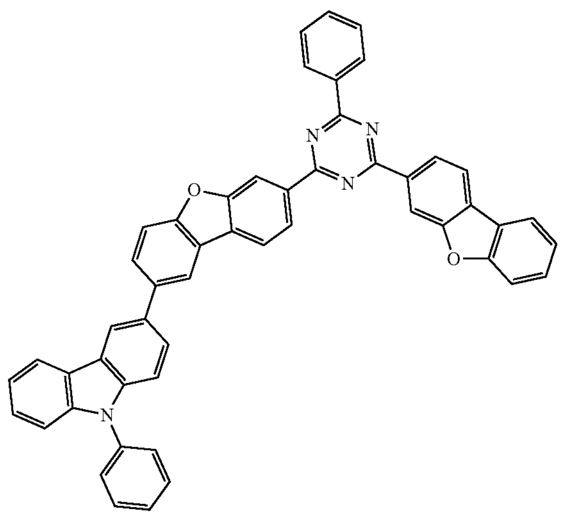
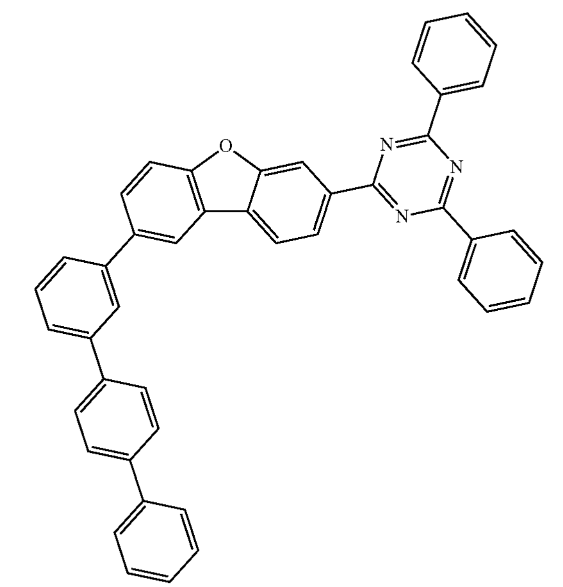
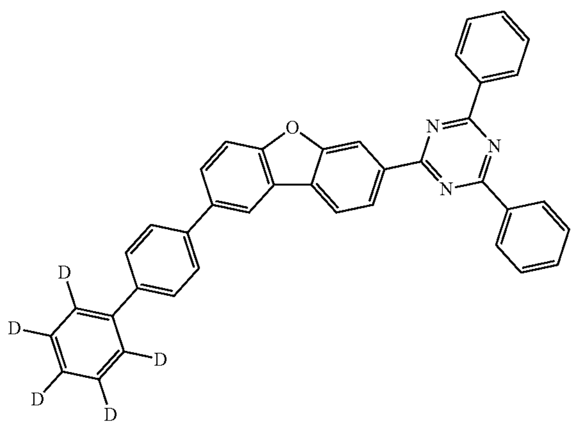
-continued
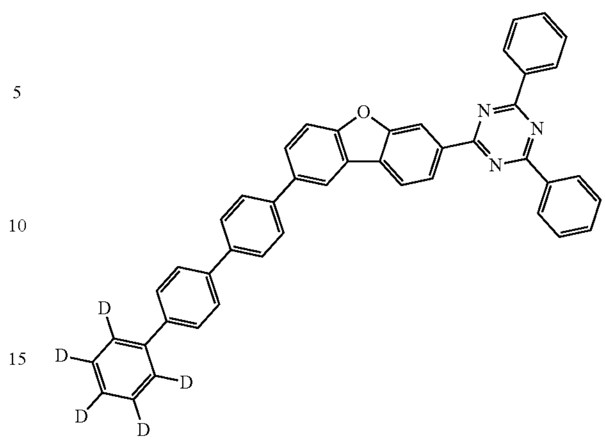
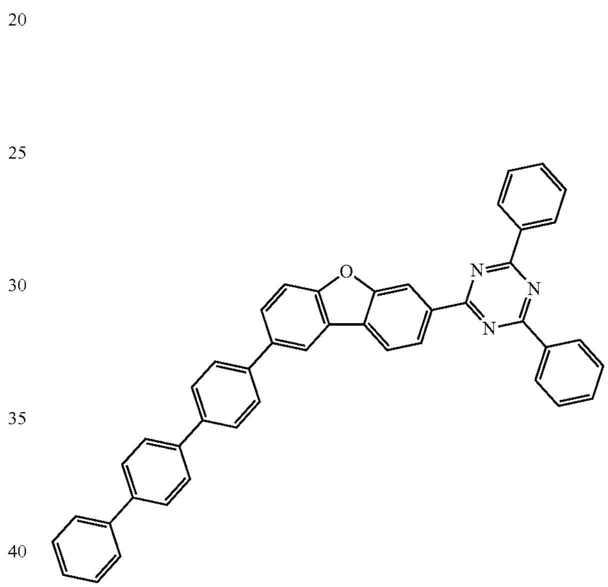
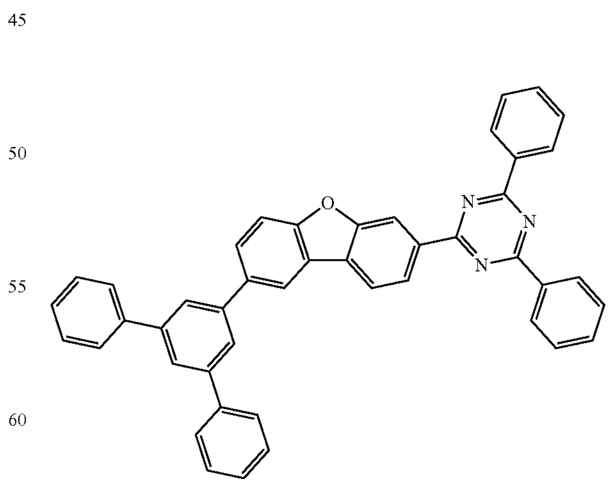

-continued
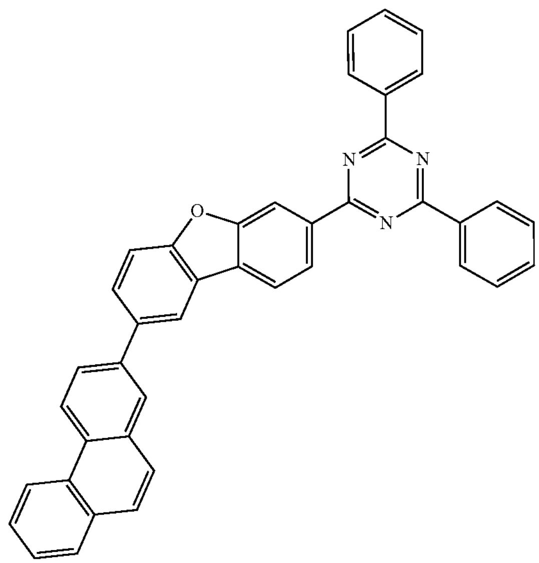
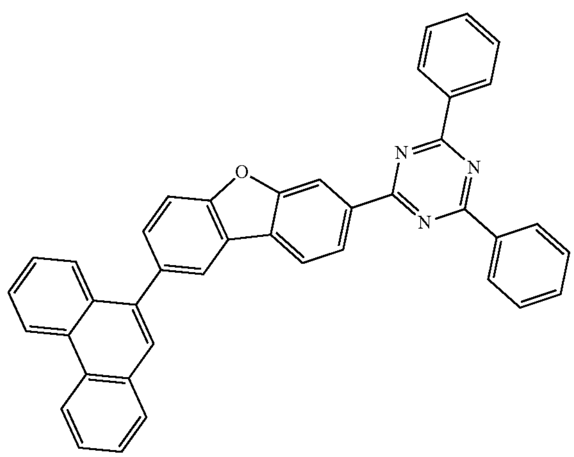
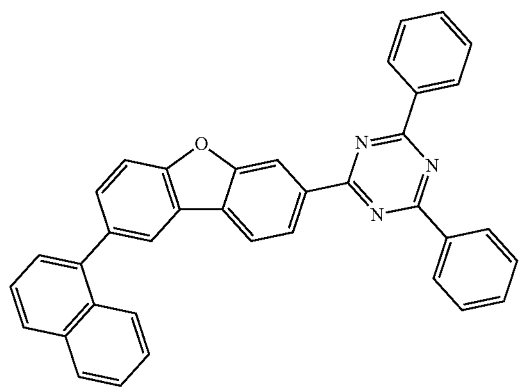
-continued
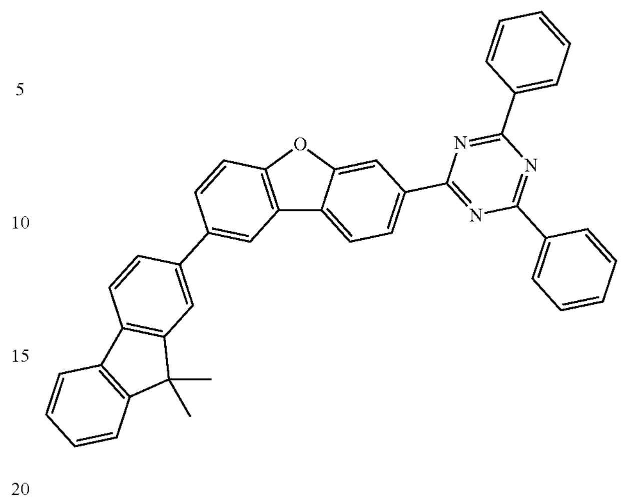
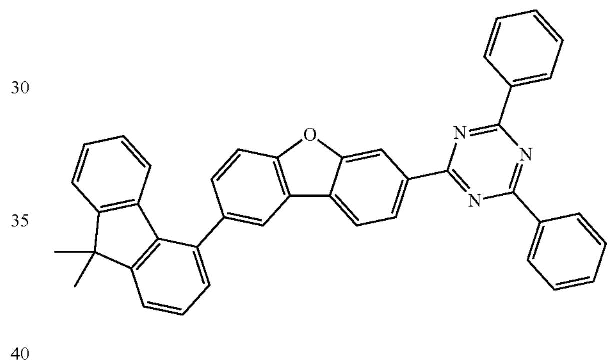
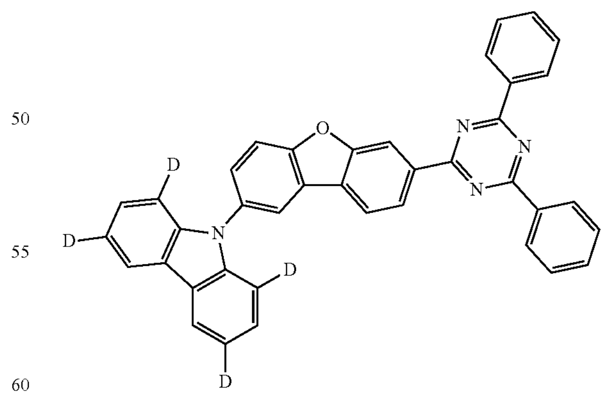

-continued
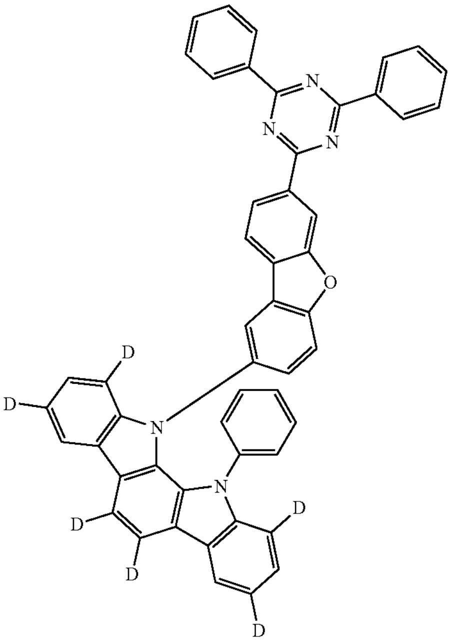
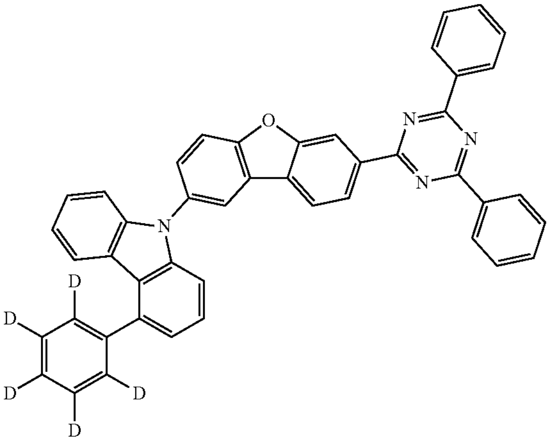
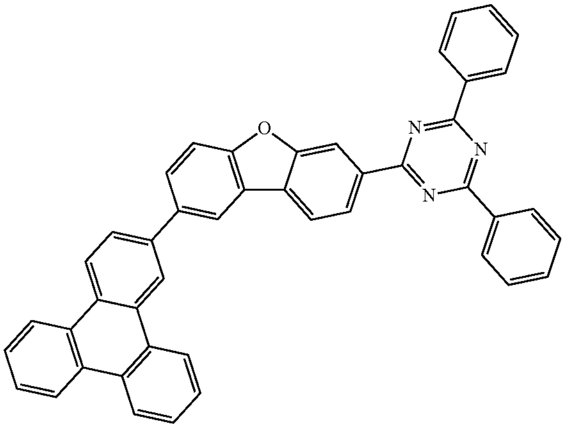
-continued
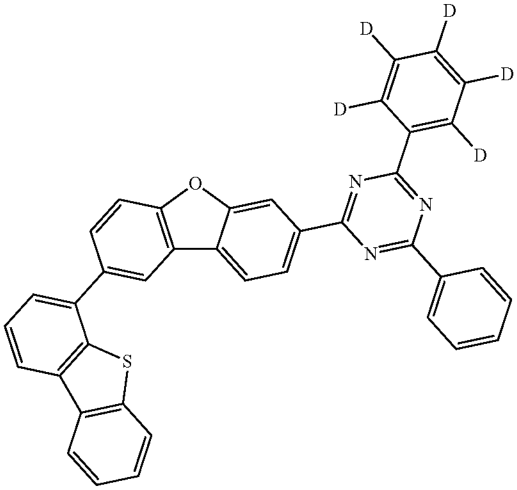
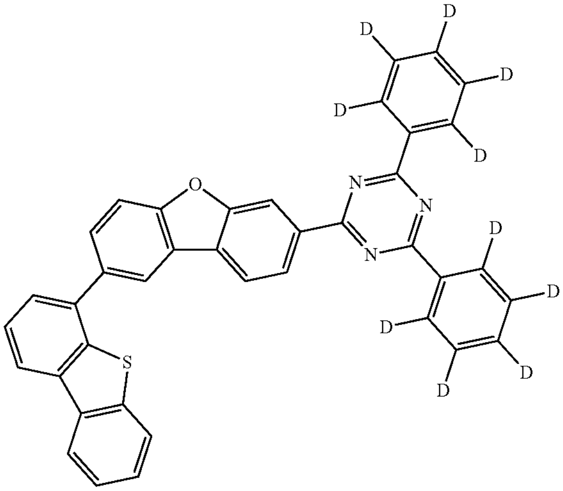
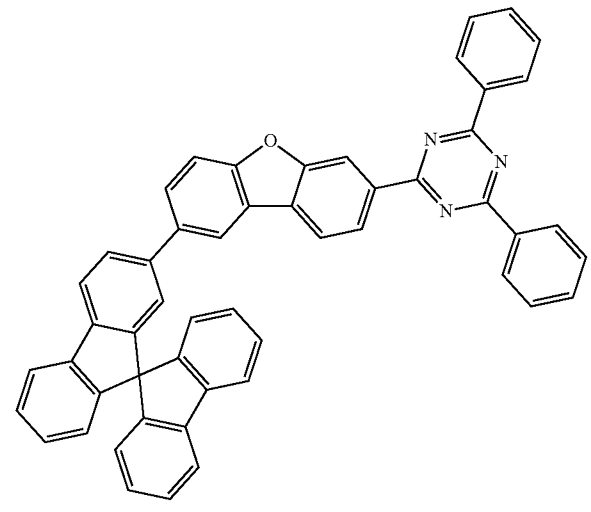

-continued
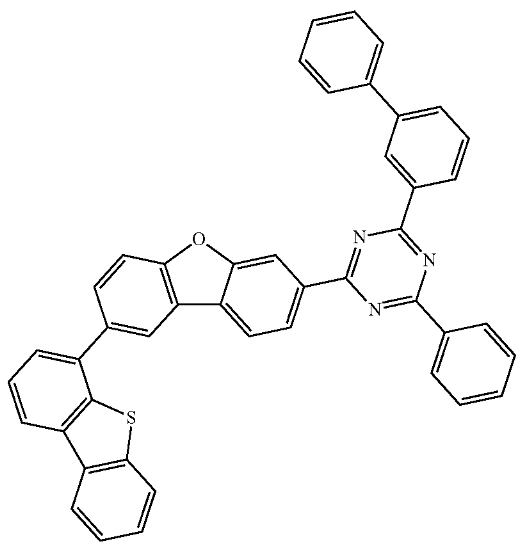
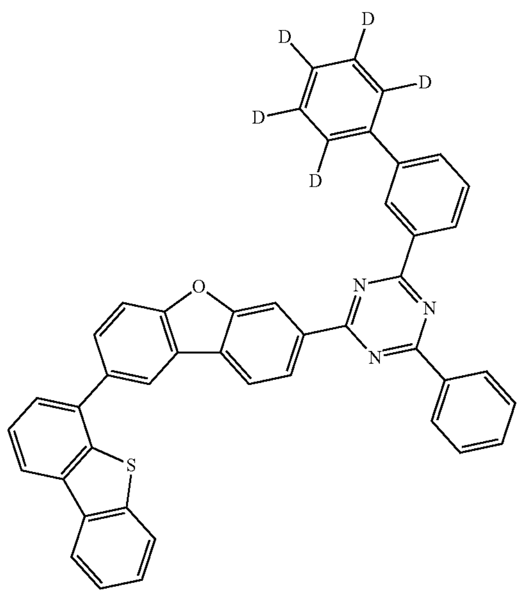
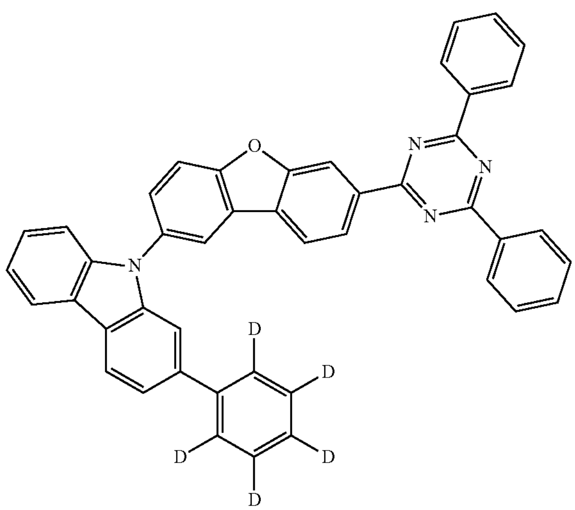
-continued
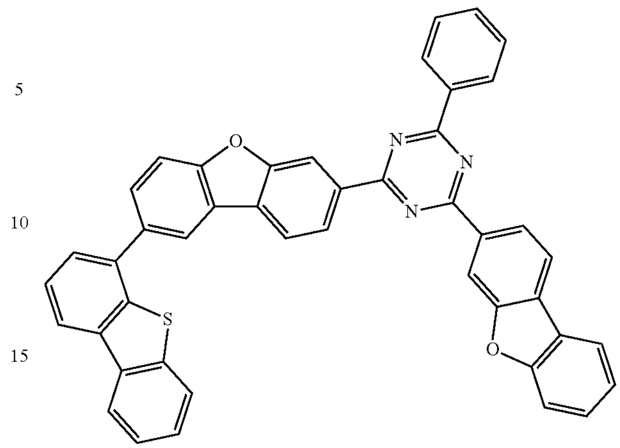
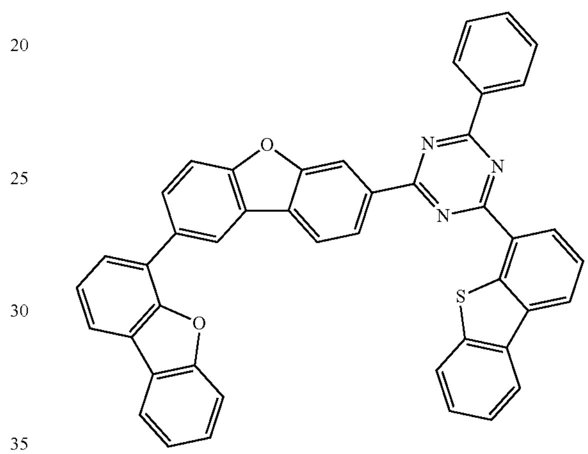
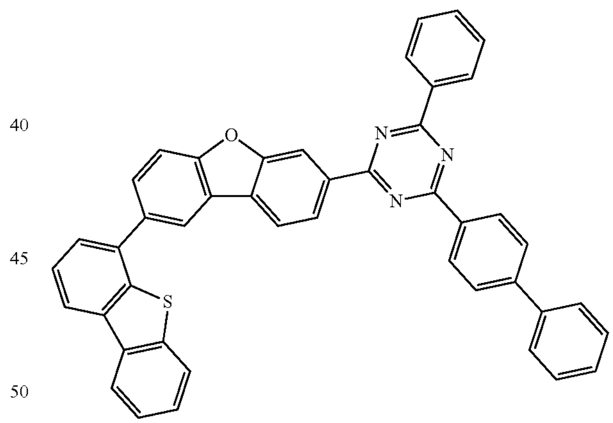
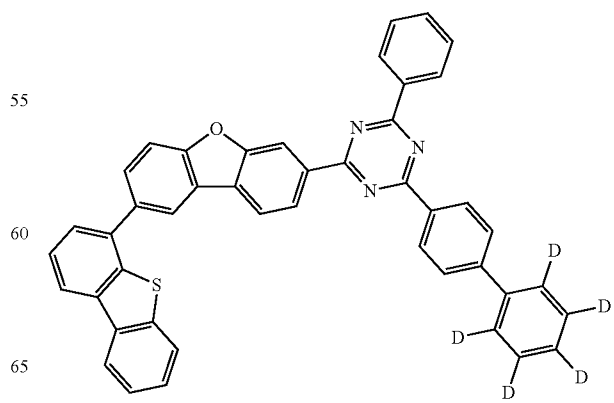

-continued
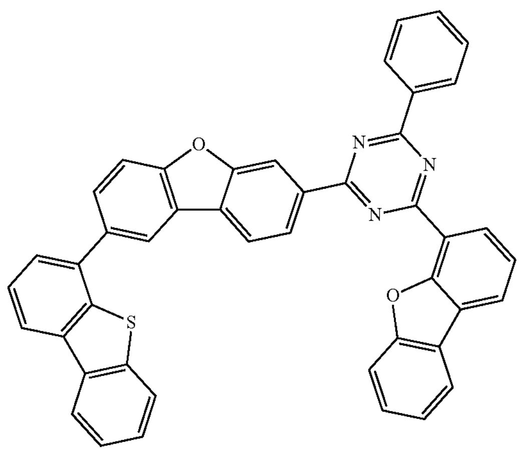
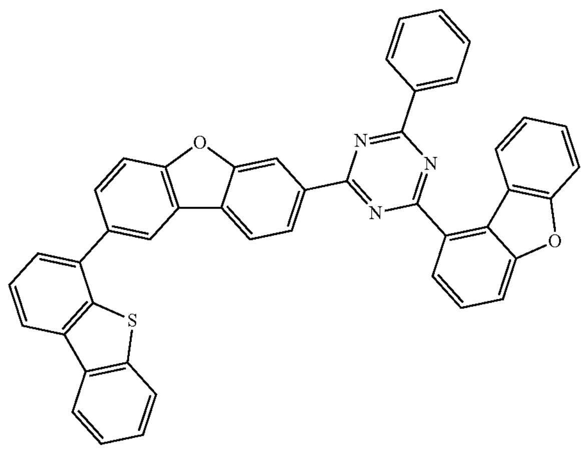
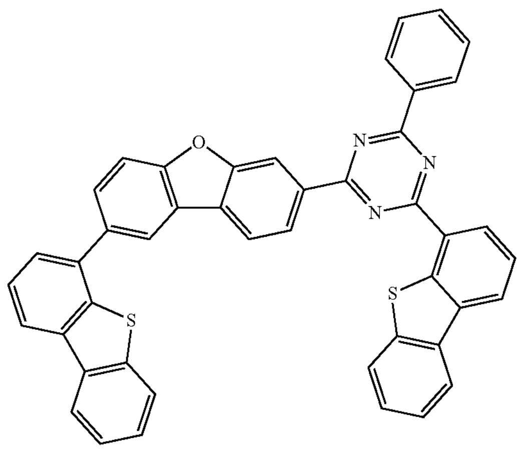
-continued
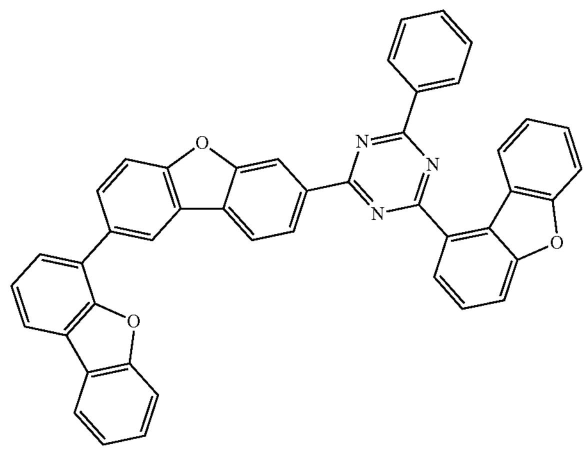
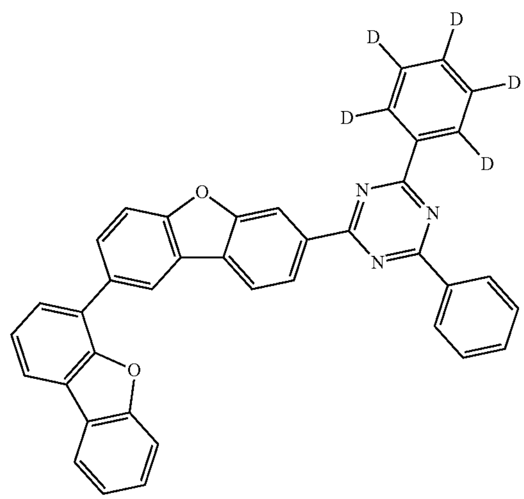
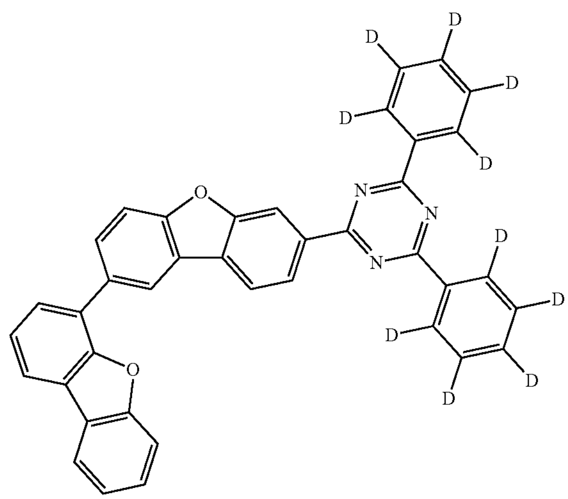

-continued
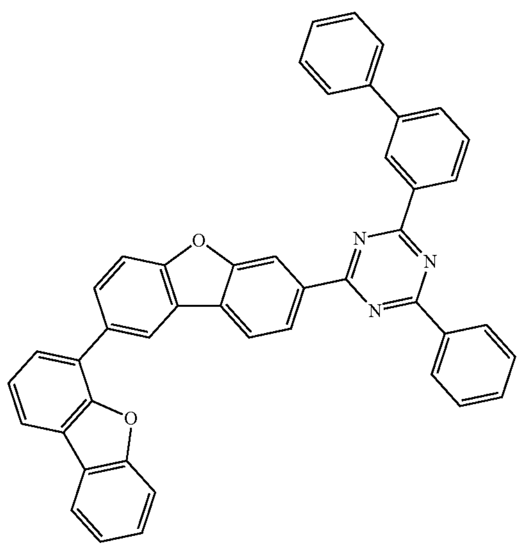 [SMILES: c1ccc(-c2cccc(-c3nc(-c4ccccc4)nc(-c4ccc5c(c4)oc4ccc(-c6cccc7c6oc6ccccc67)cc45)n3)c2)cc1]
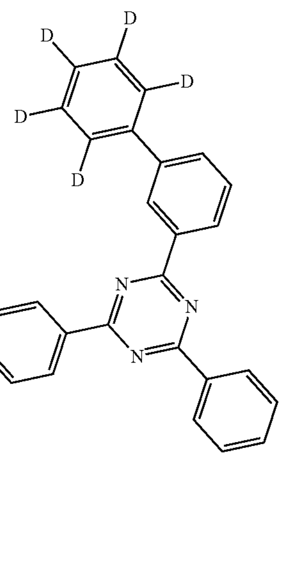
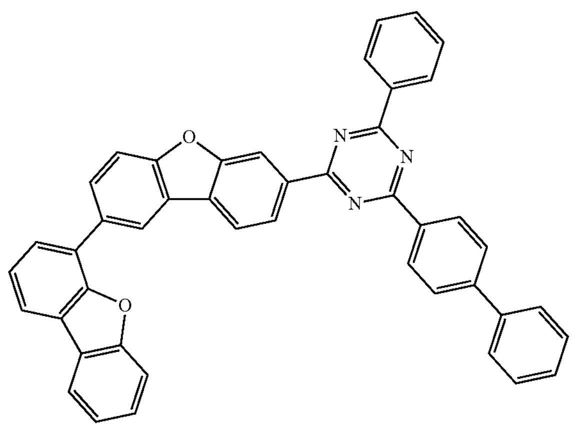
-continued
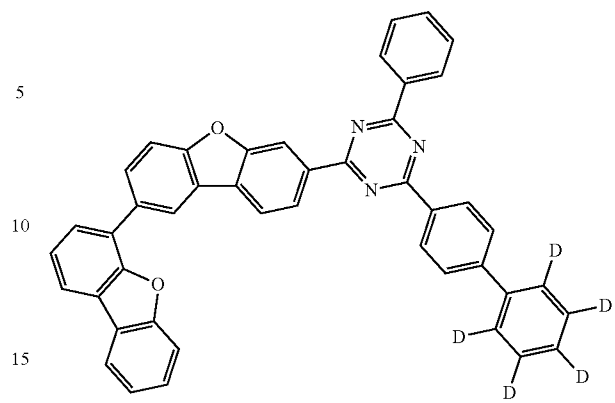
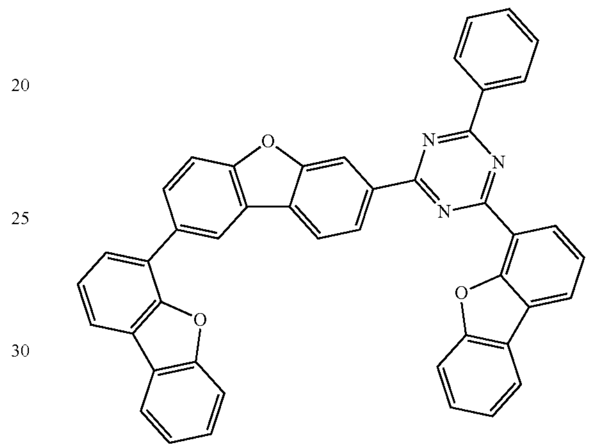
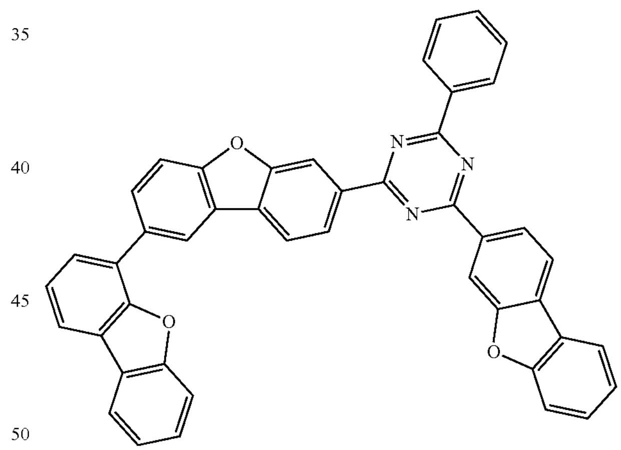
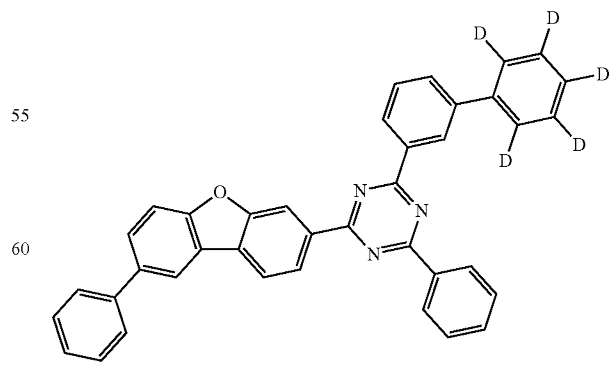

-continued
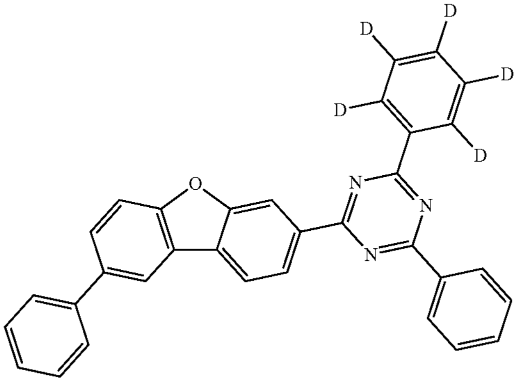
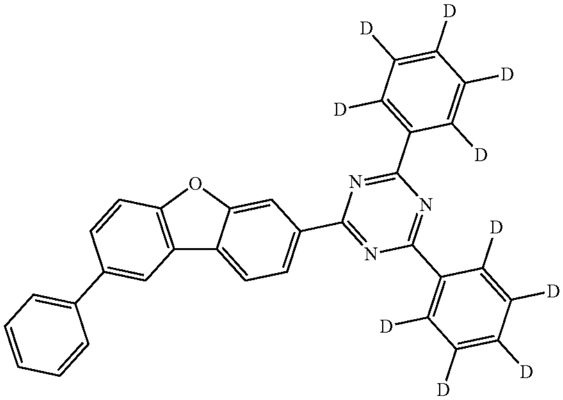
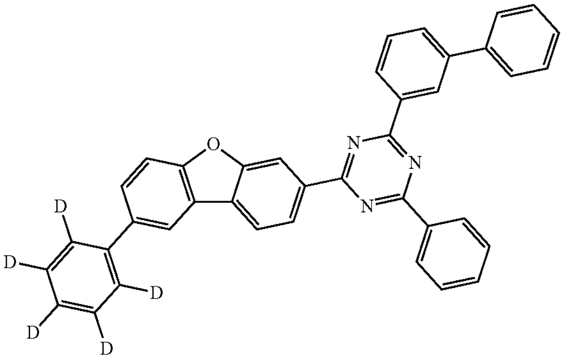
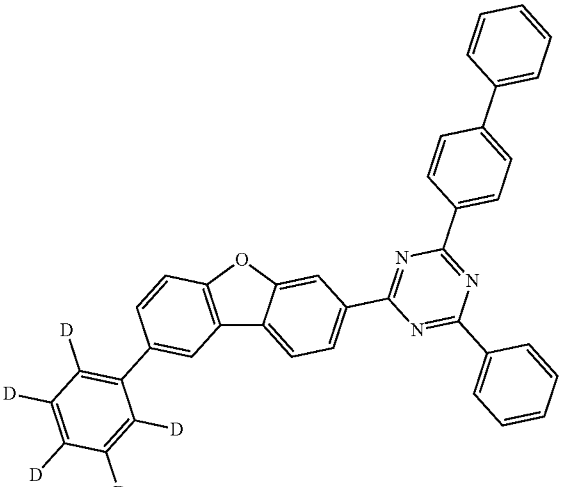
-continued
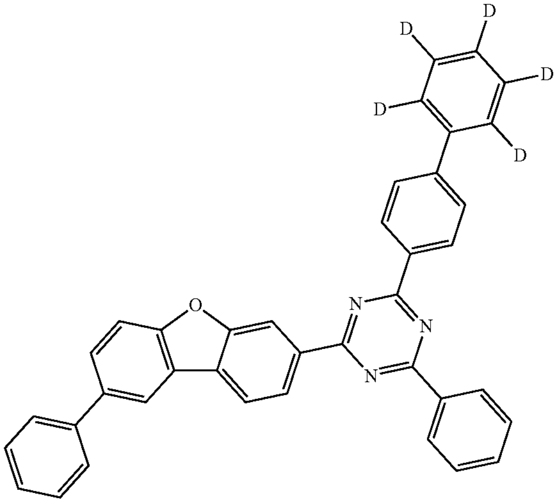
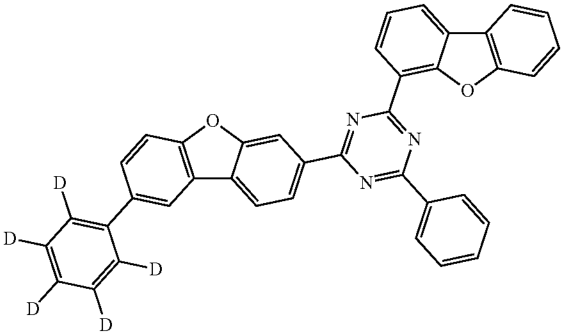
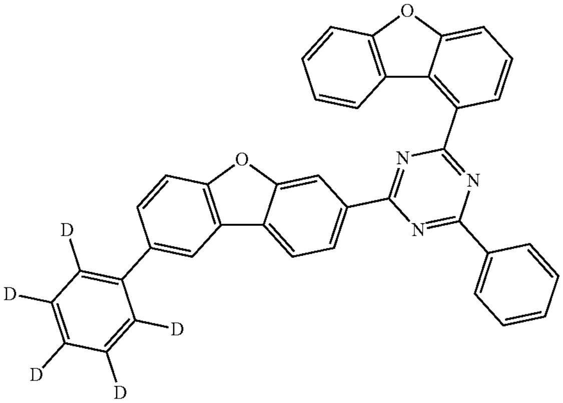
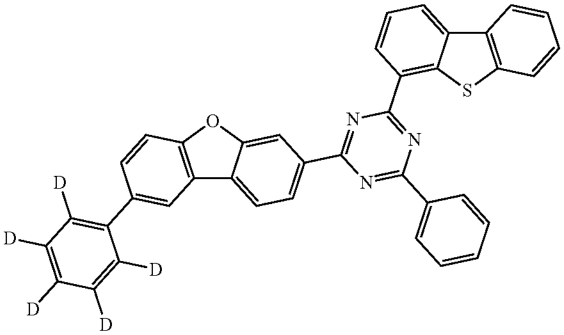

-continued
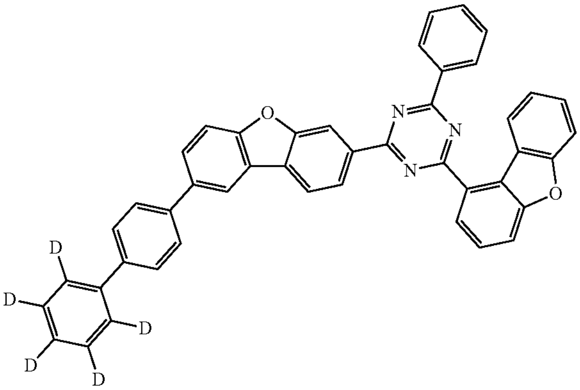
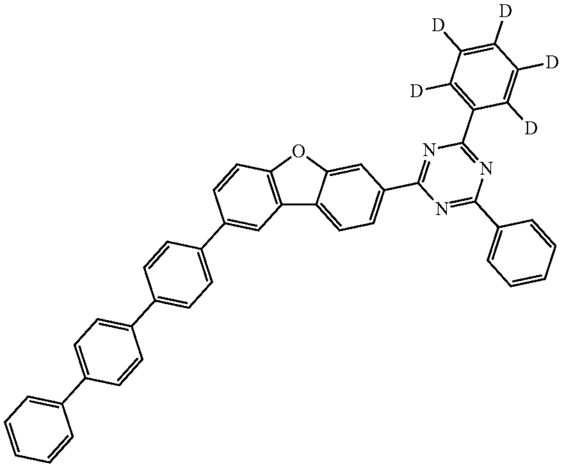
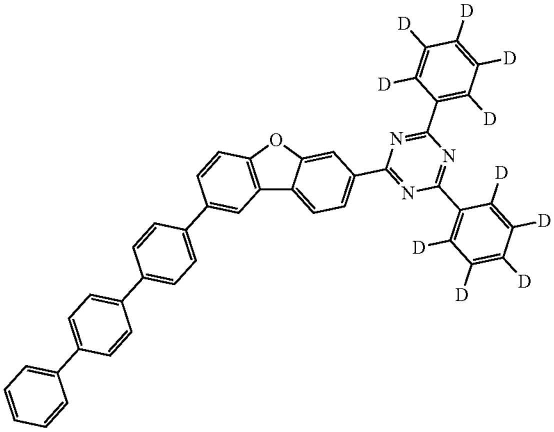
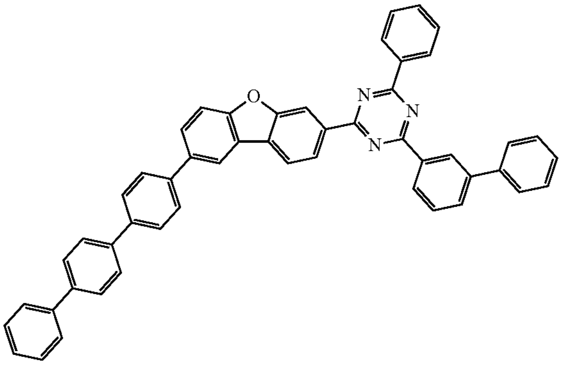
-continued
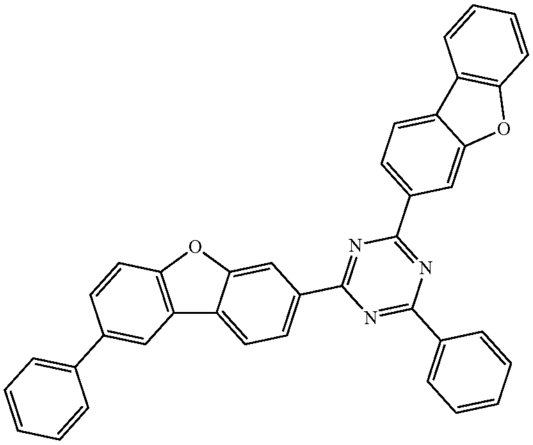
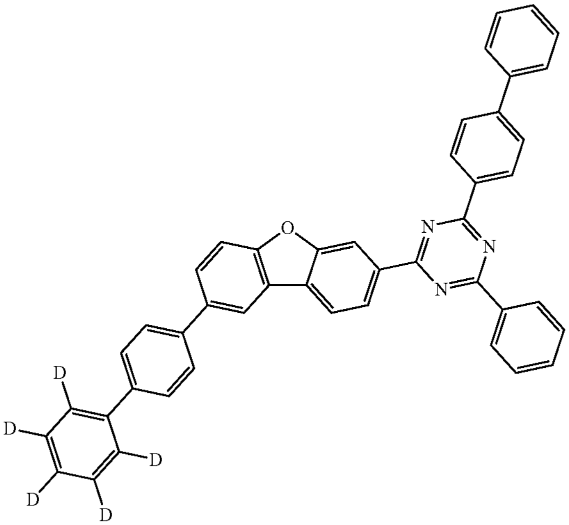
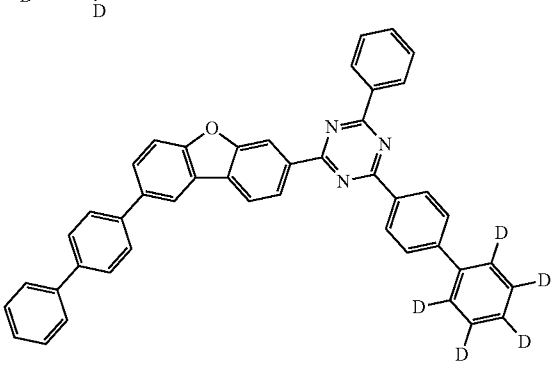
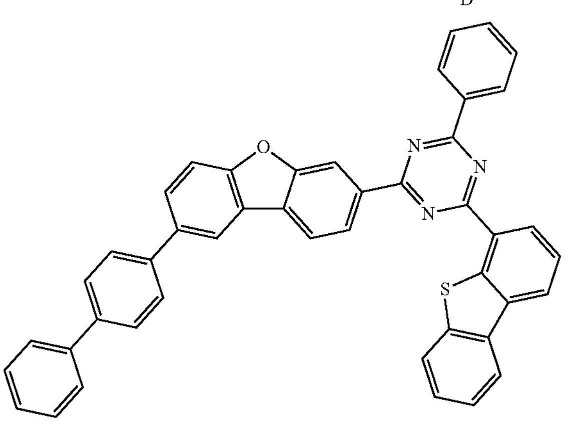

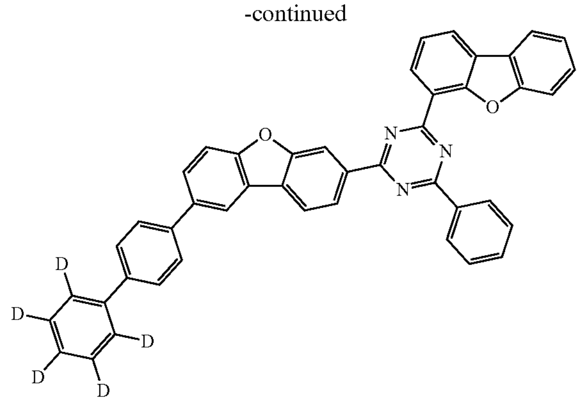
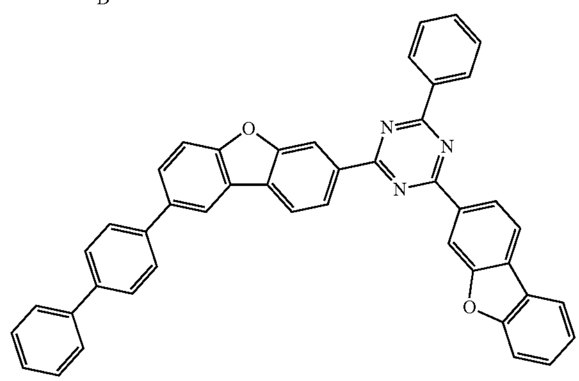
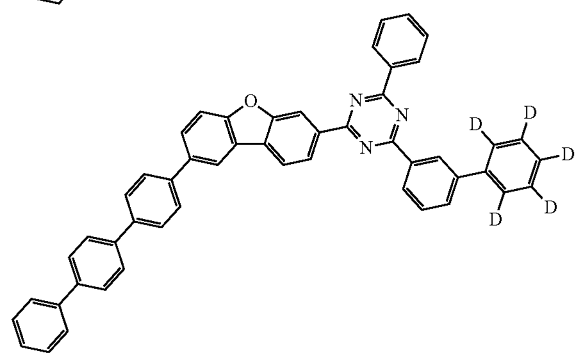
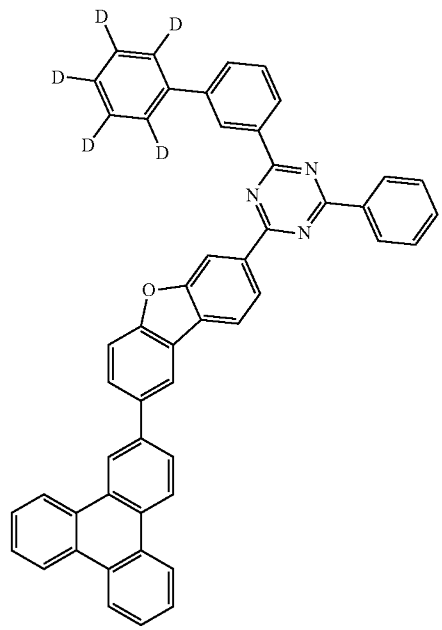
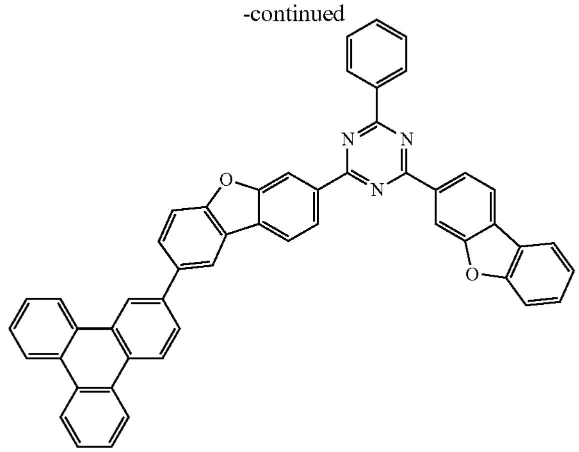
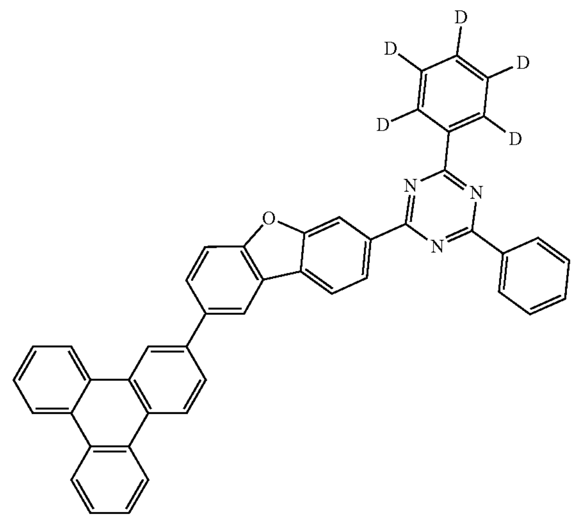
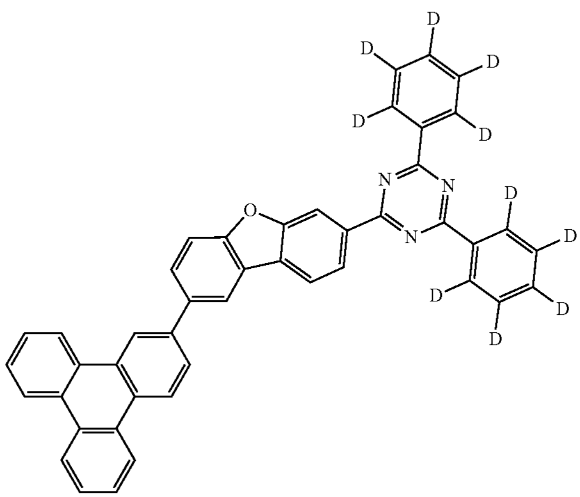

-continued
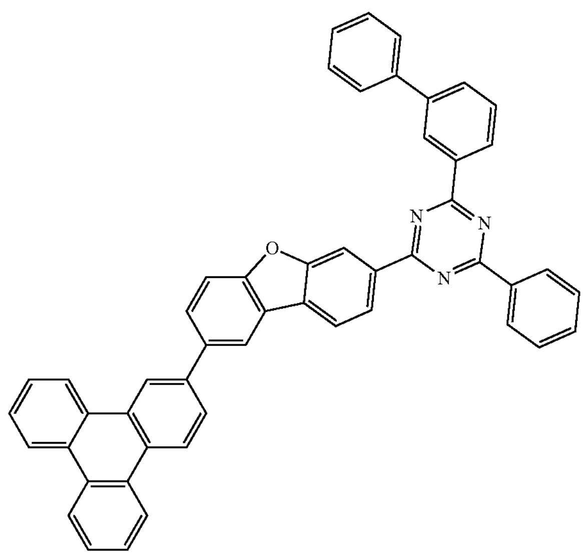
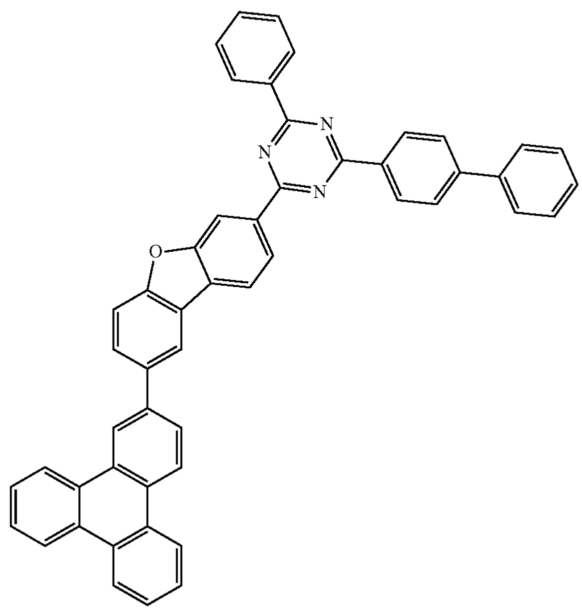
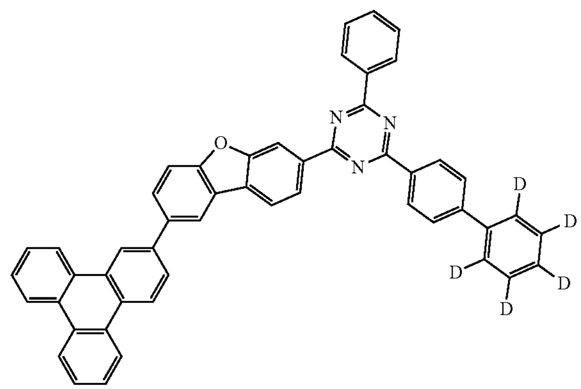
-continued
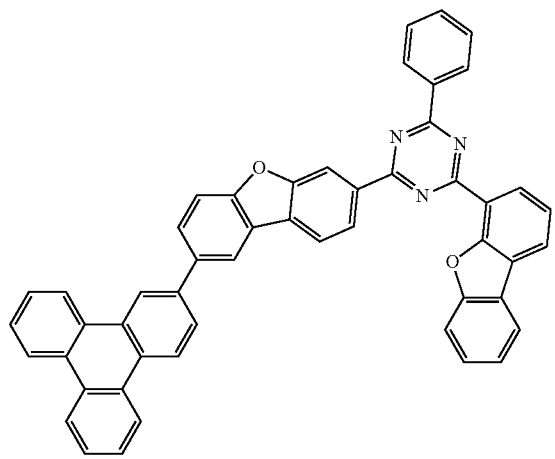
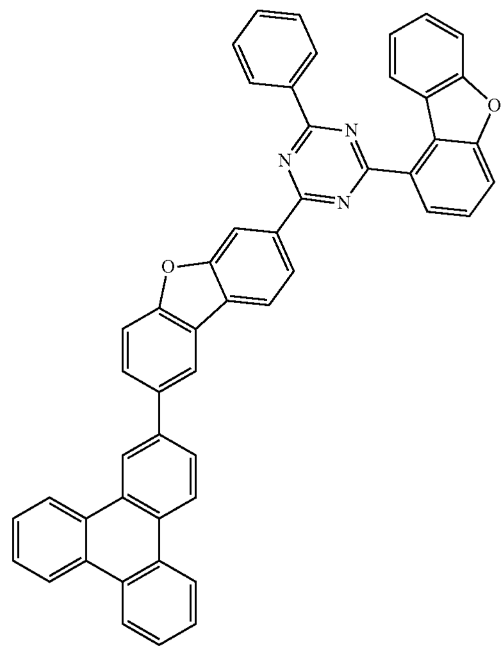

-continued
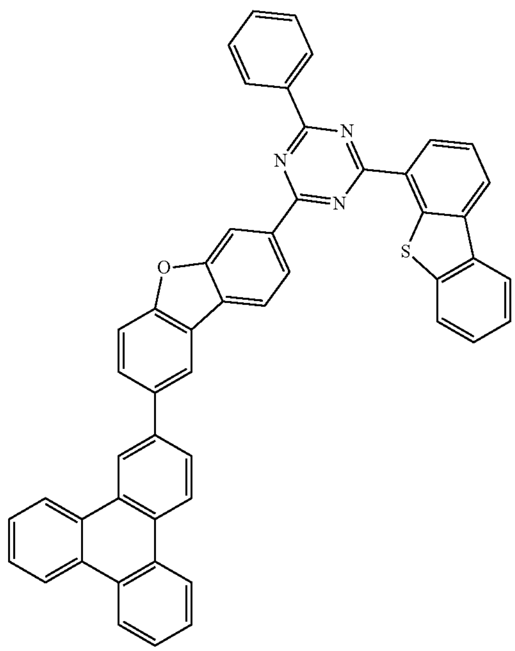
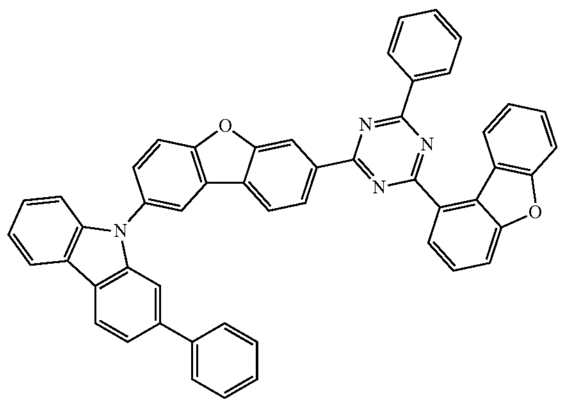
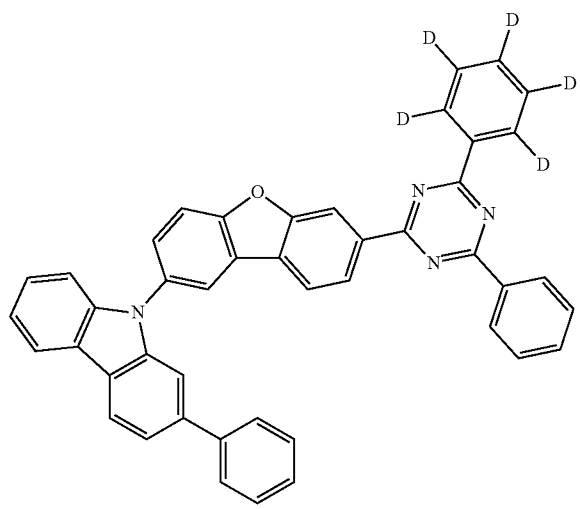
-continued
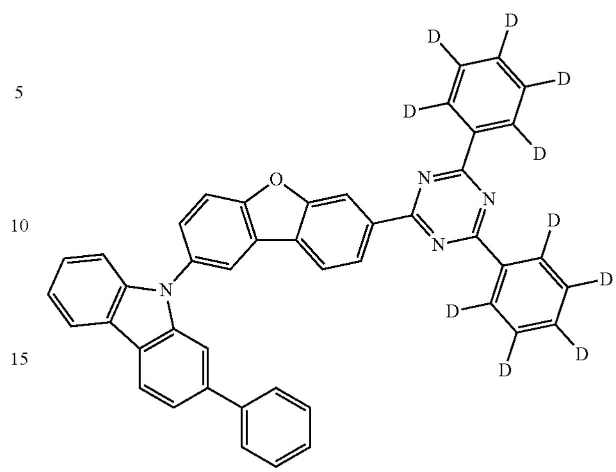
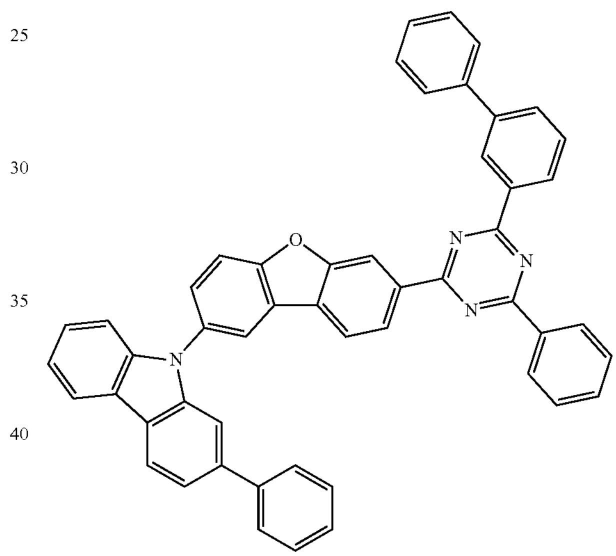
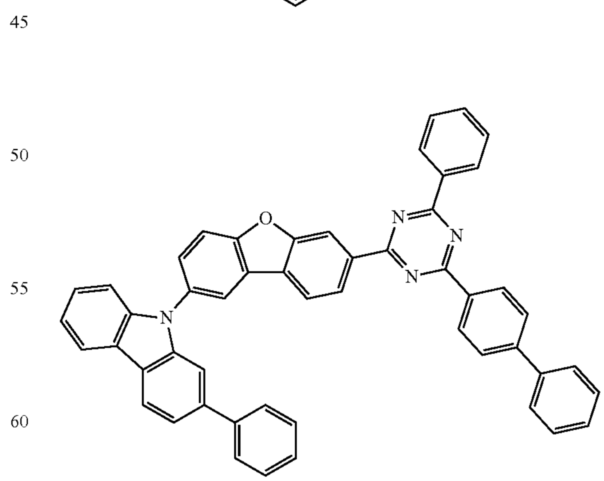

-continued
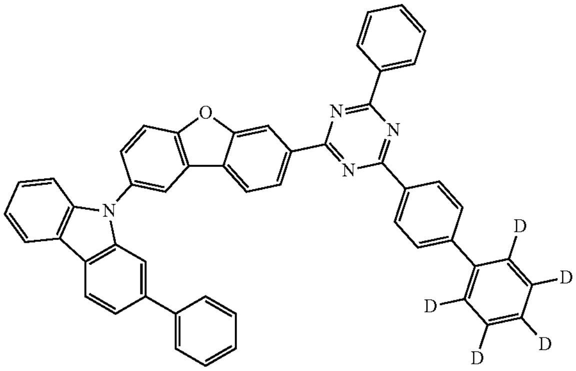
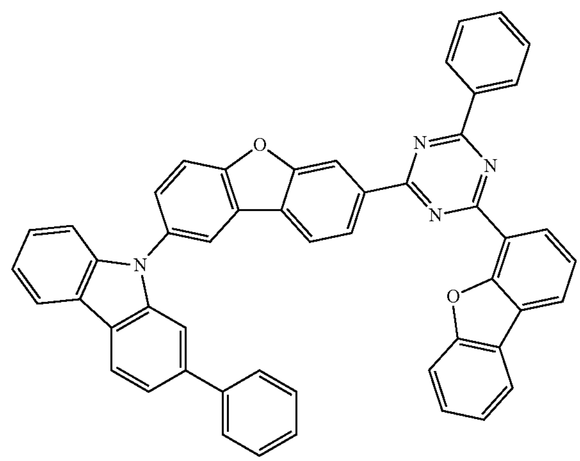
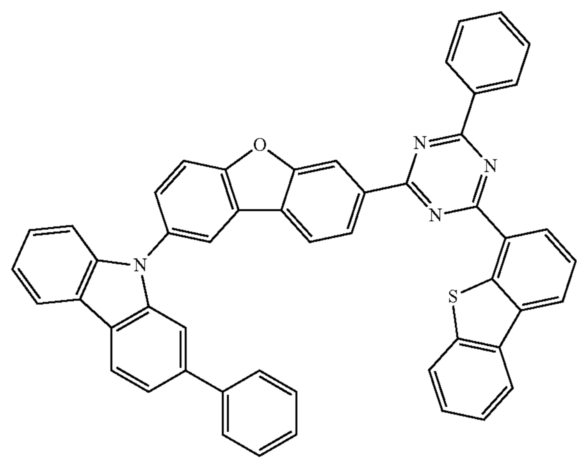
-continued
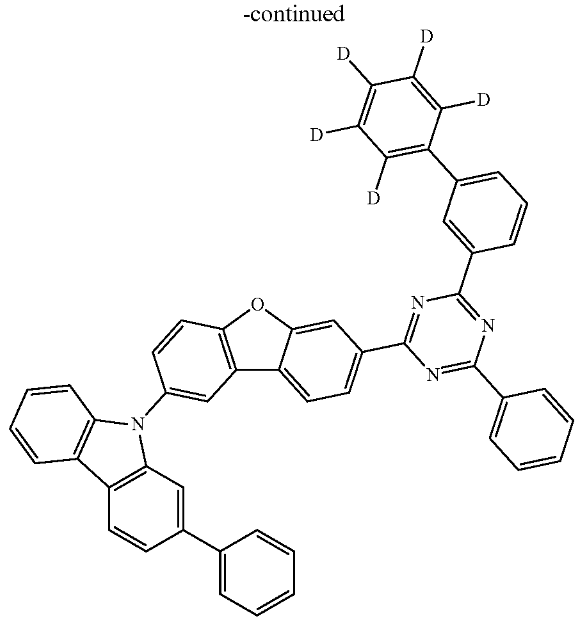
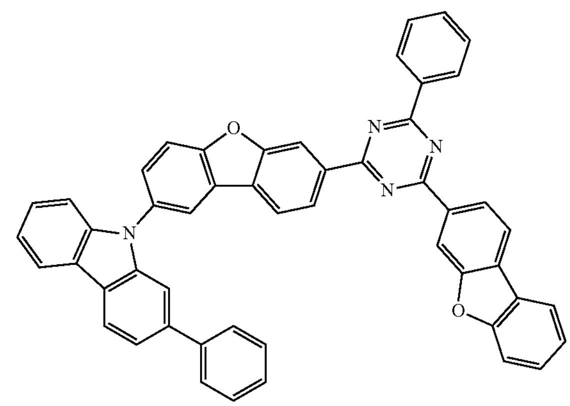
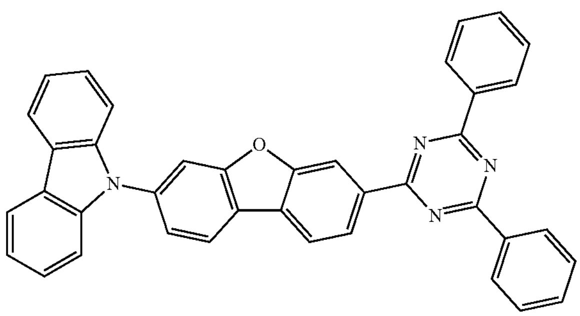
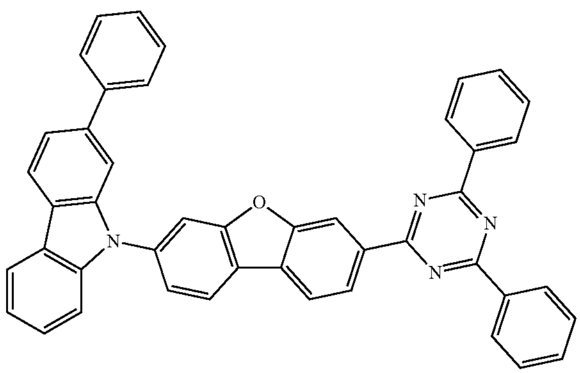

-continued
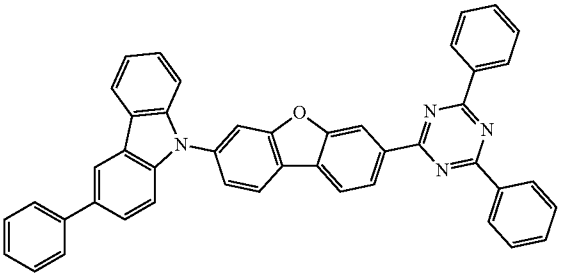
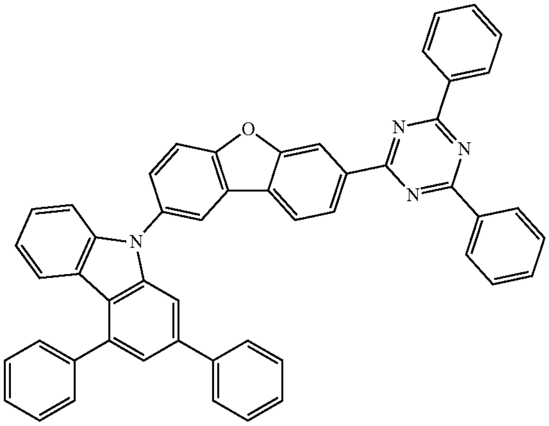
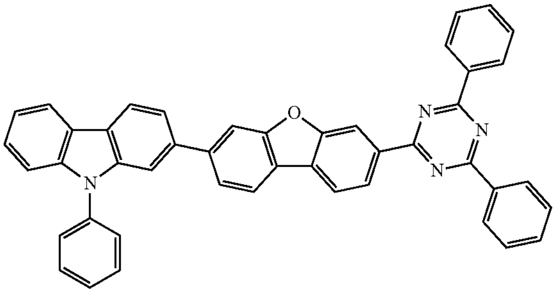
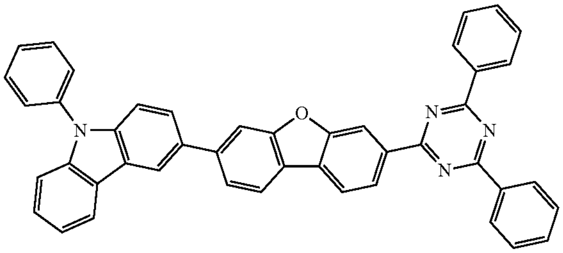
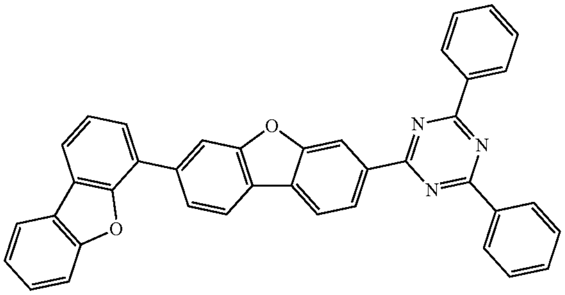
-continued
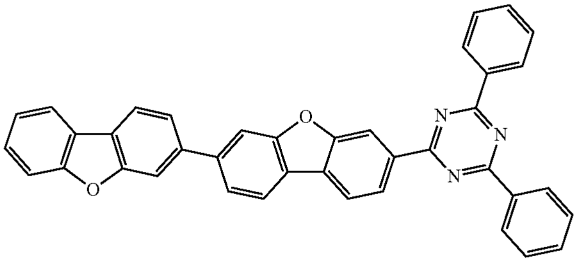
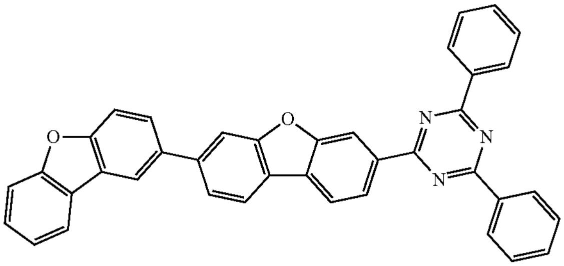
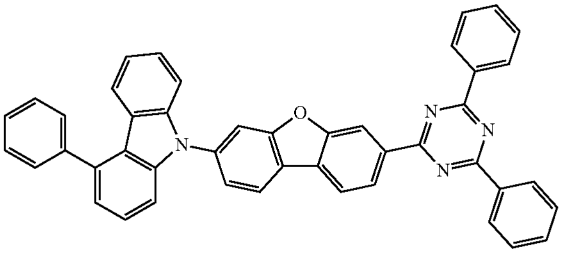
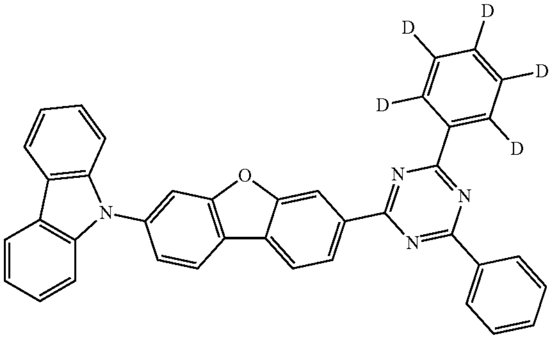
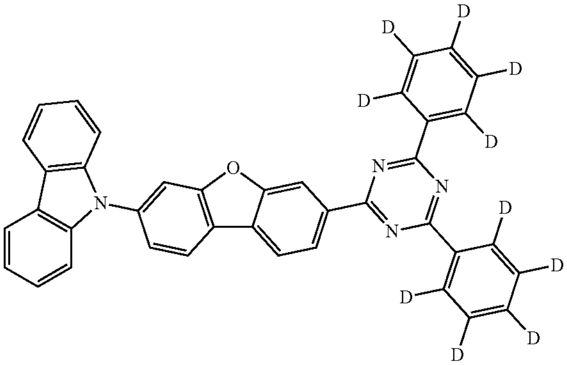

-continued
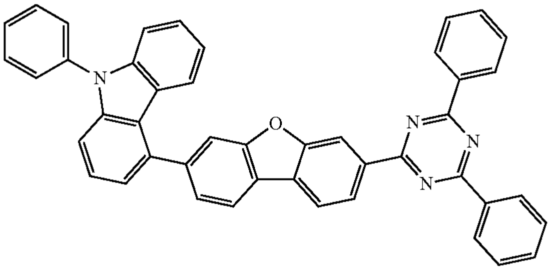
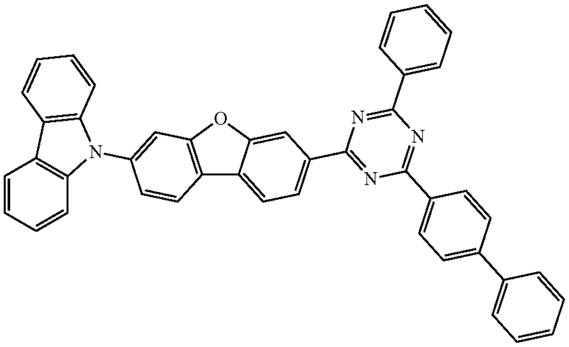
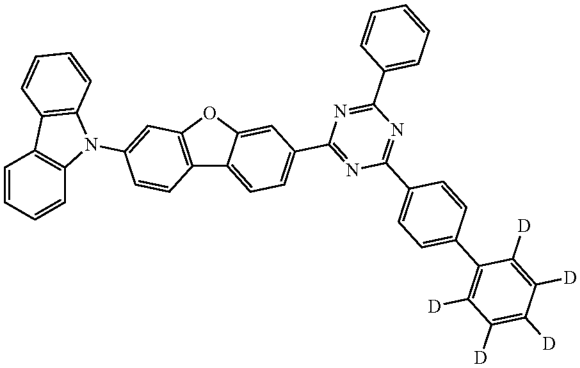
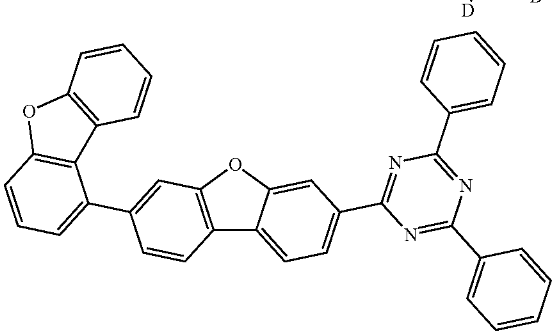
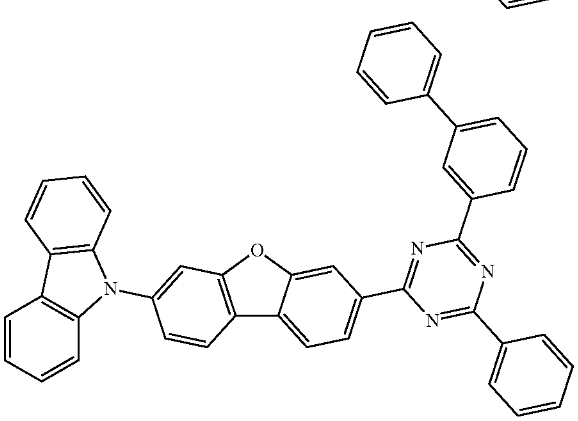
-continued
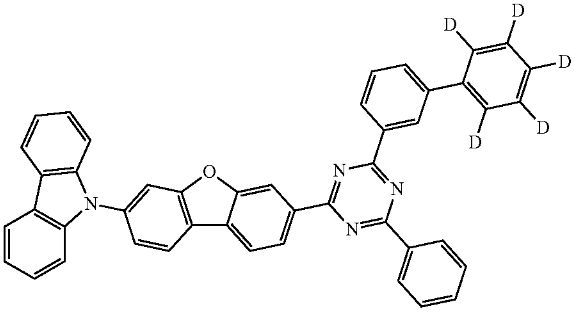
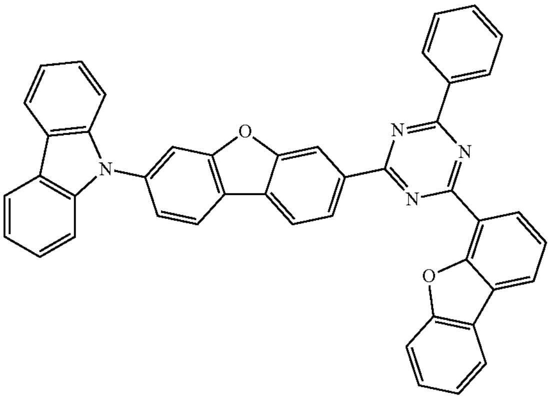 [SMILES: c1ccc(-c2nc(-c3ccc4c(c3)sc3cc(-n5c6ccccc6c6ccccc65)ccc34)nc(-c3cccc4c3oc3ccccc34)n2)cc1]
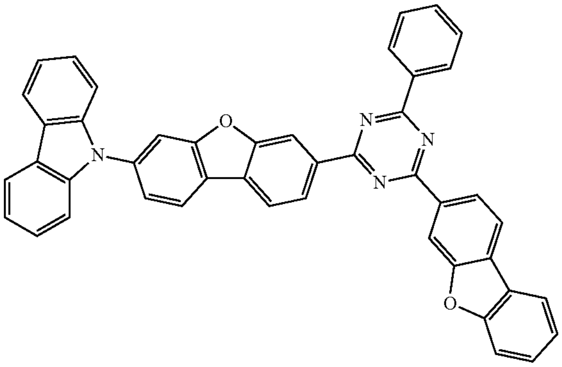
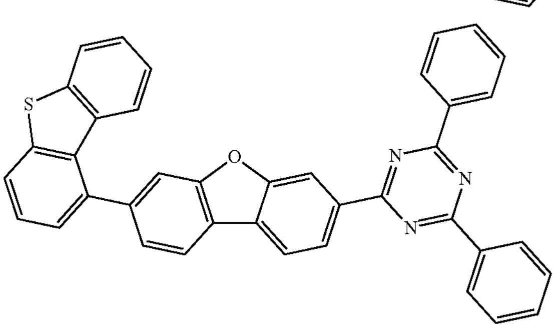
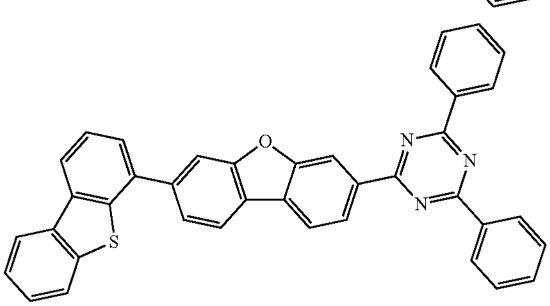

-continued
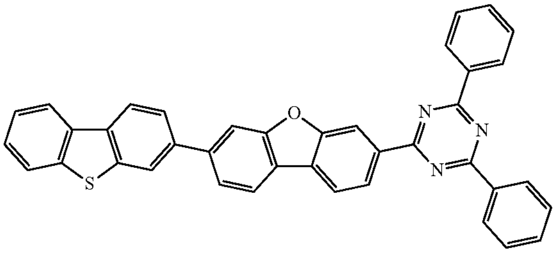
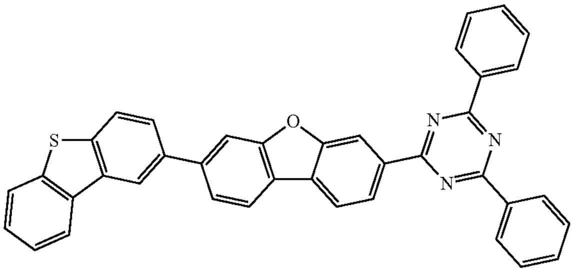
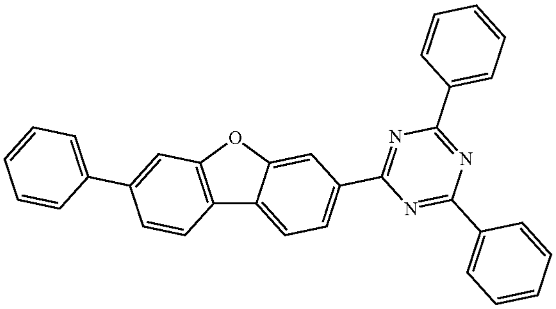
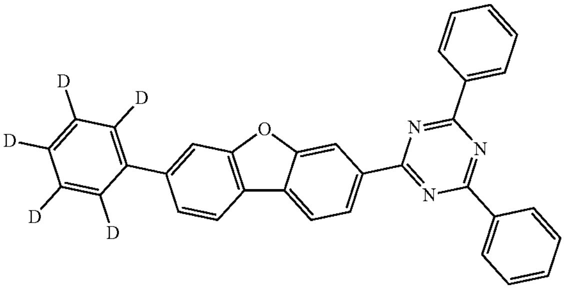
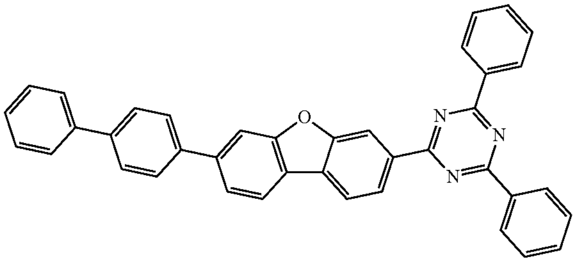
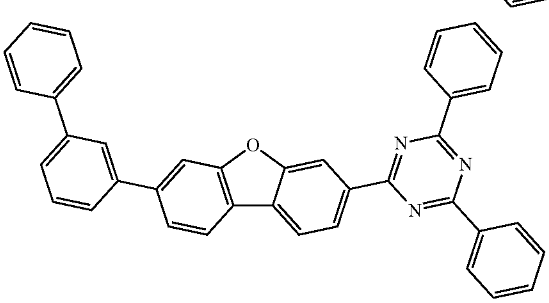
-continued
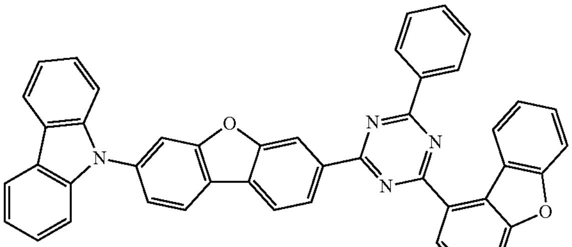
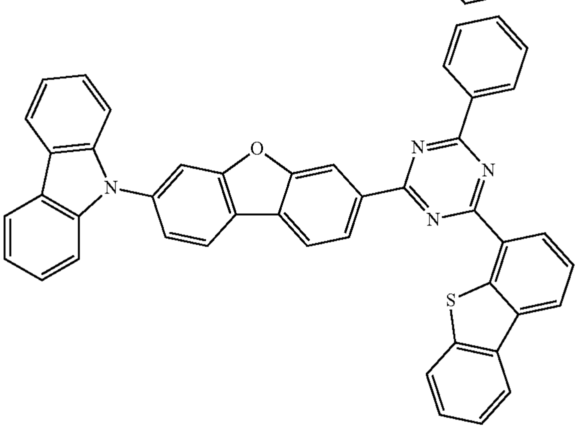
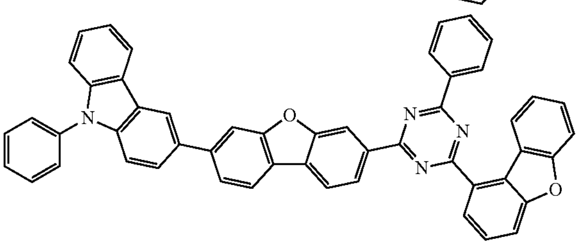
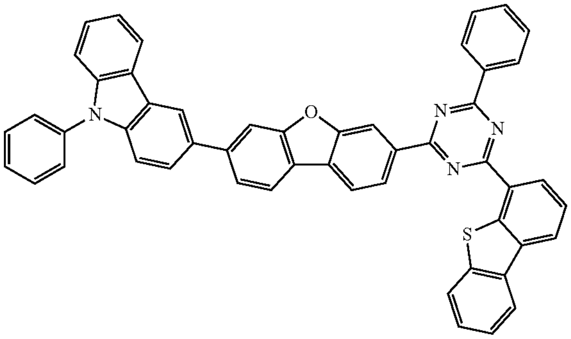
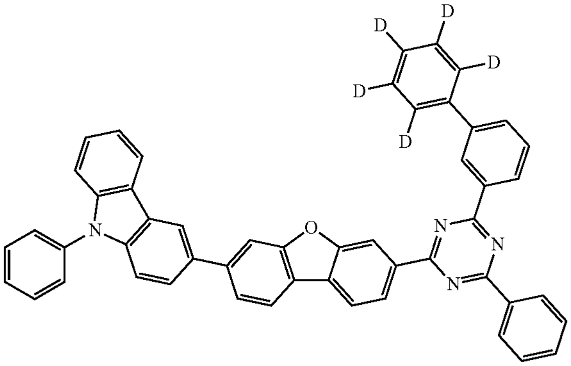

-continued
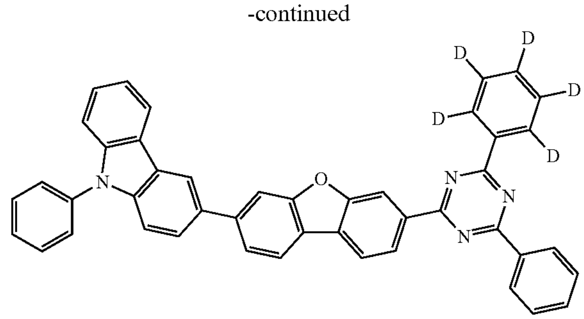
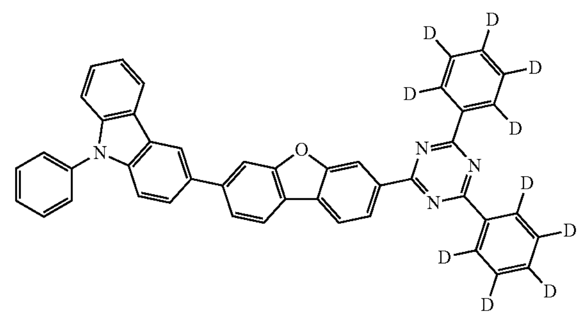
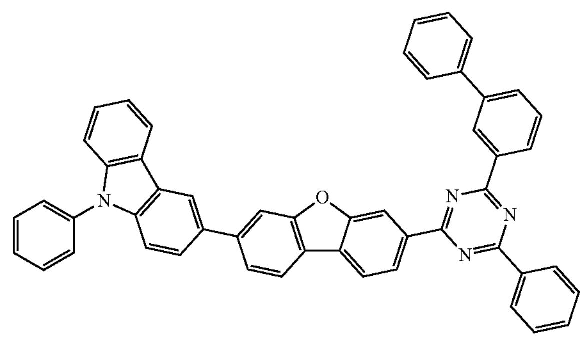
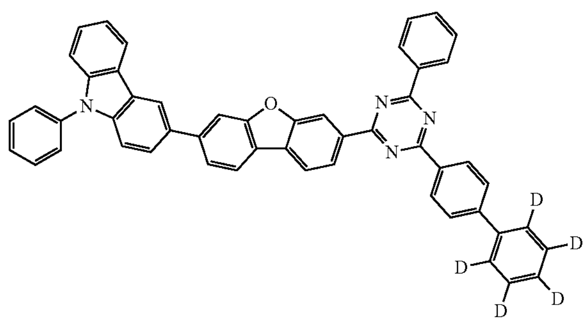
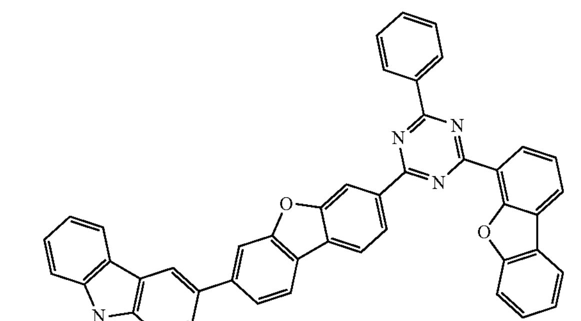
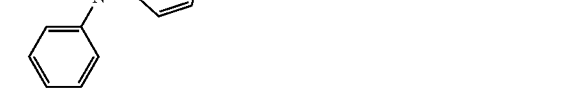
-continued
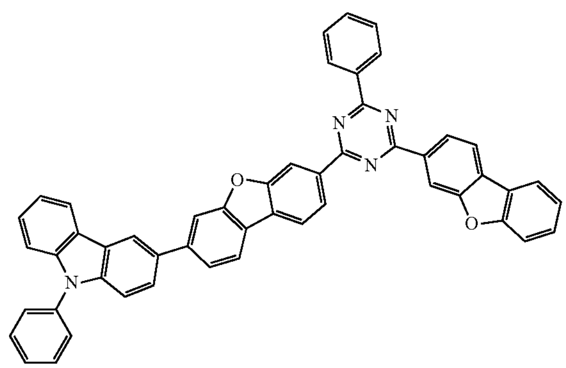
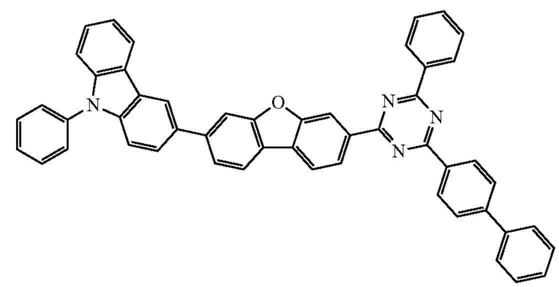
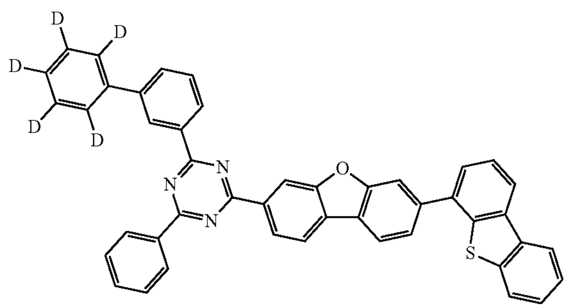
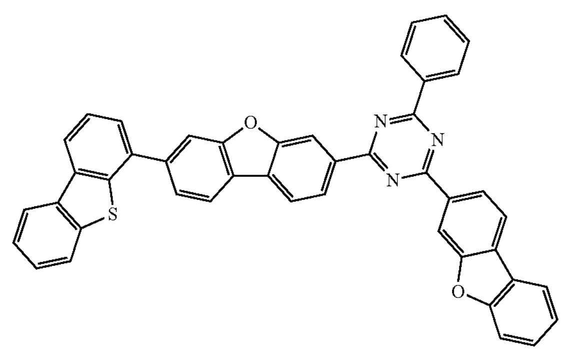
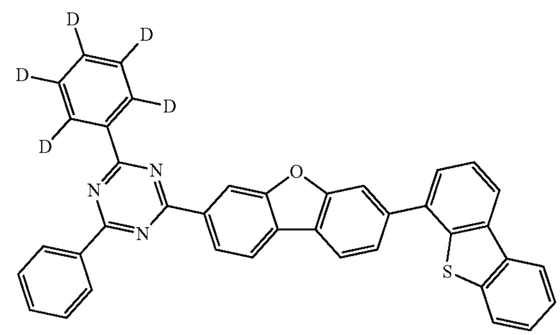
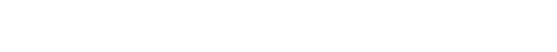

-continued
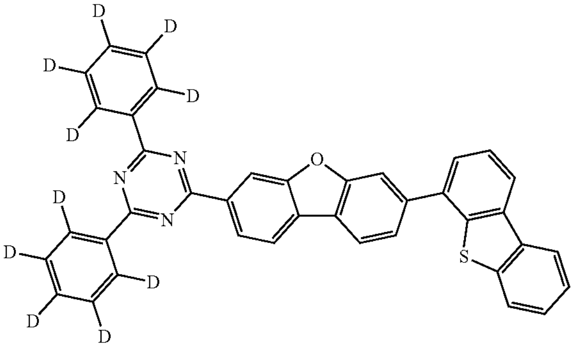
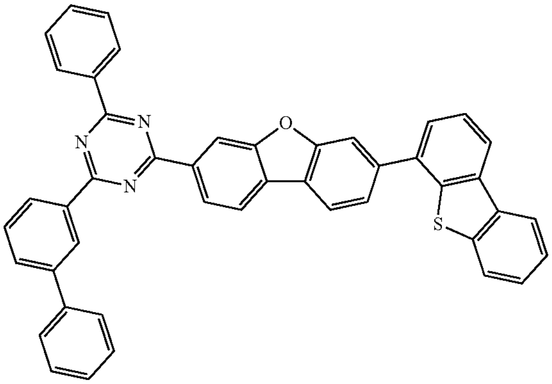
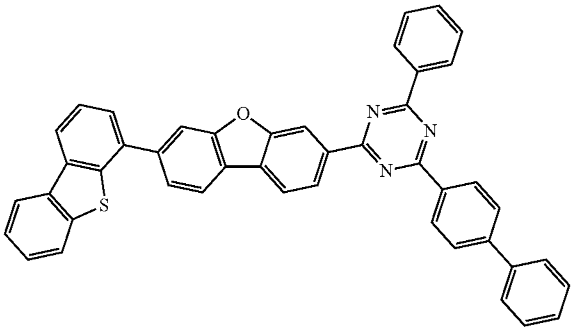
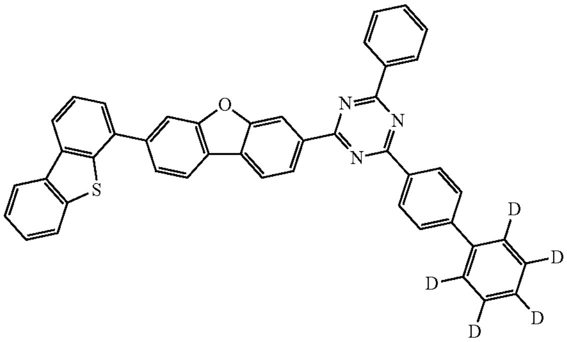
-continued
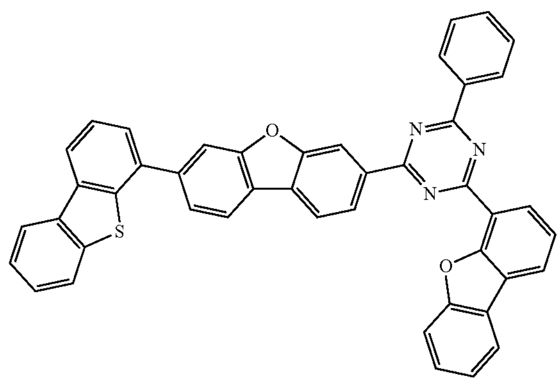
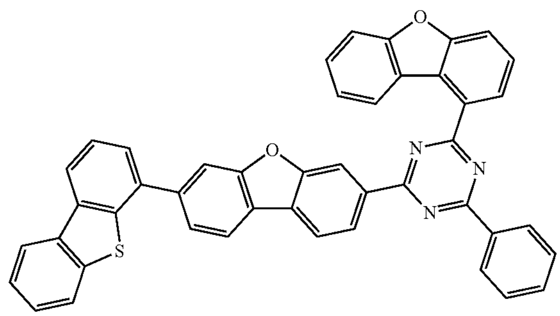
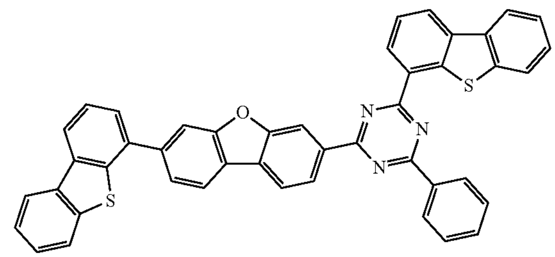
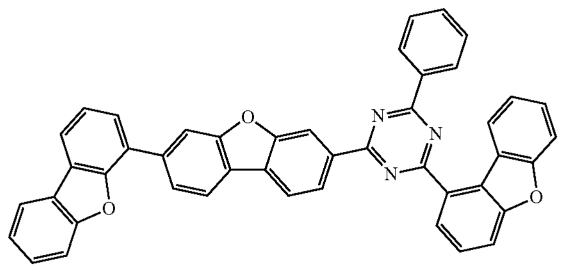
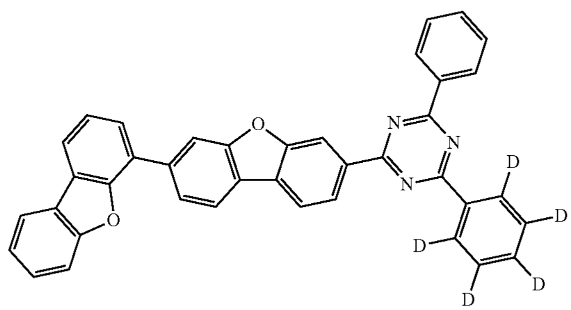

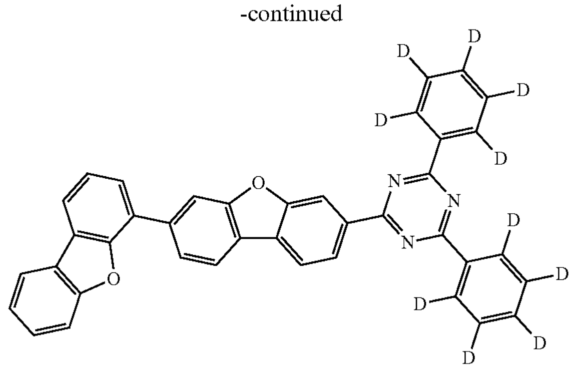
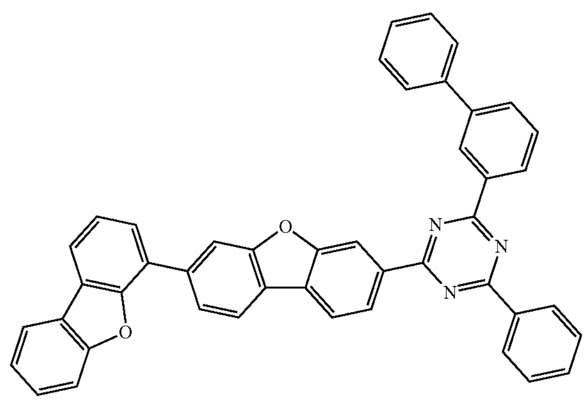
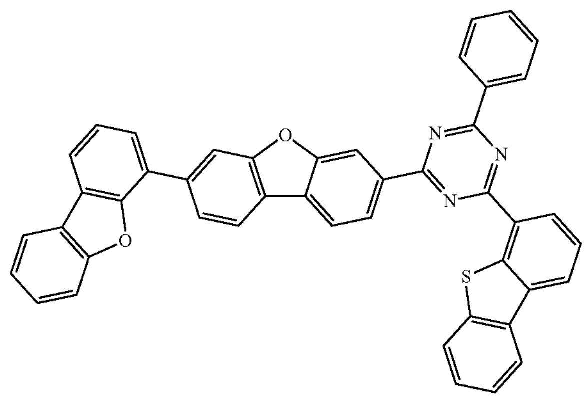
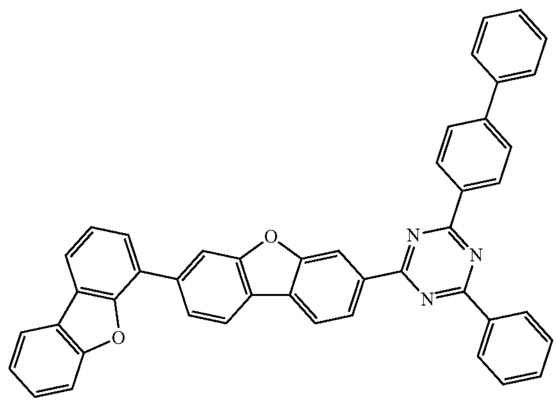
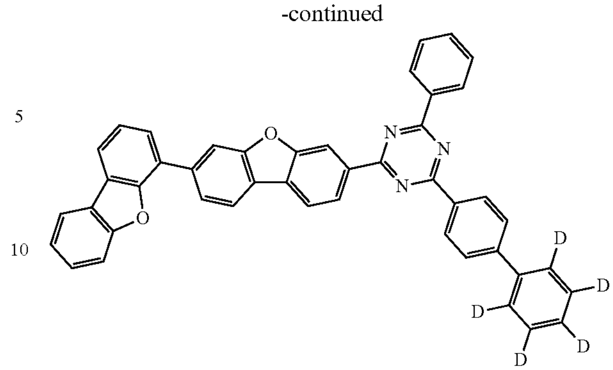
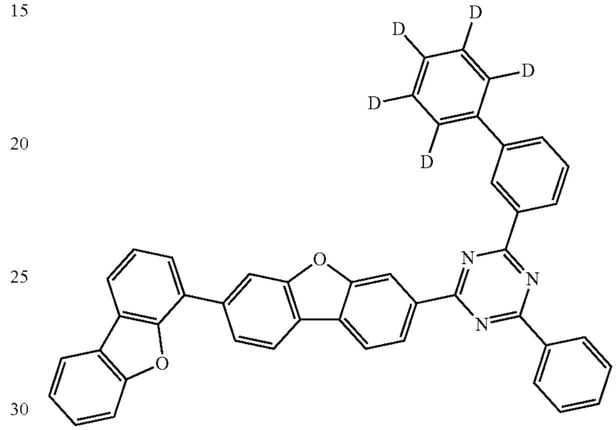
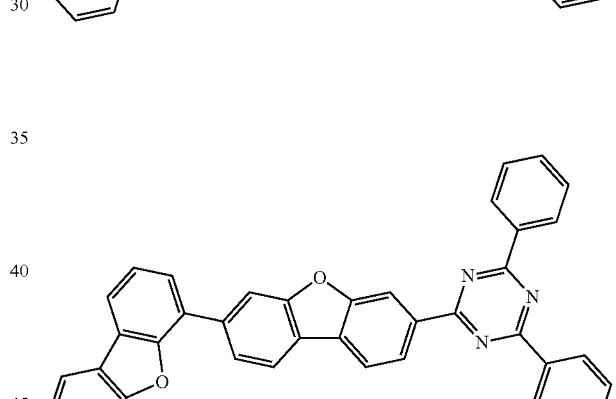
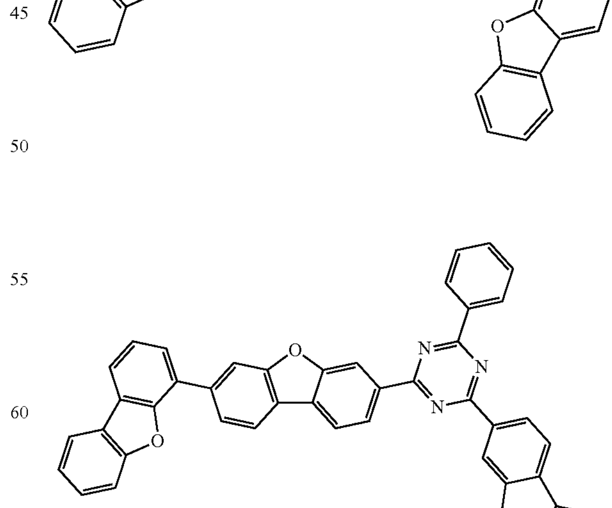

-continued
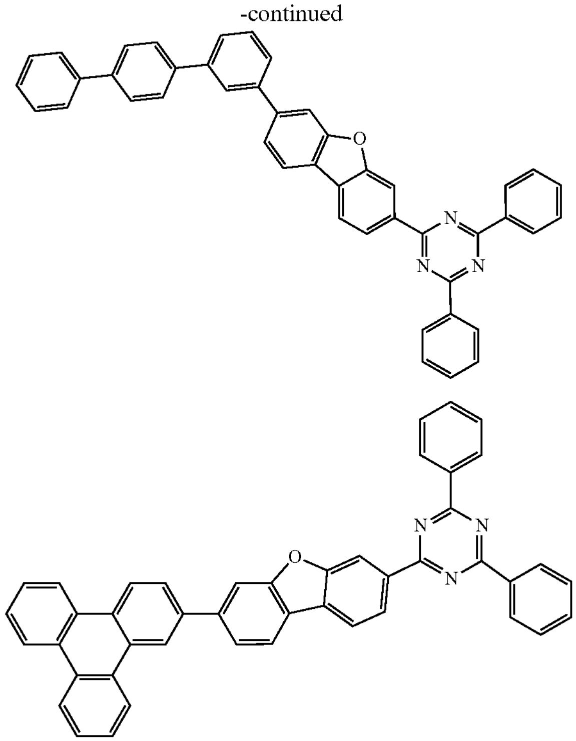
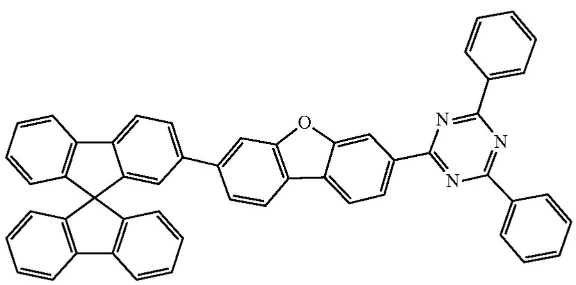
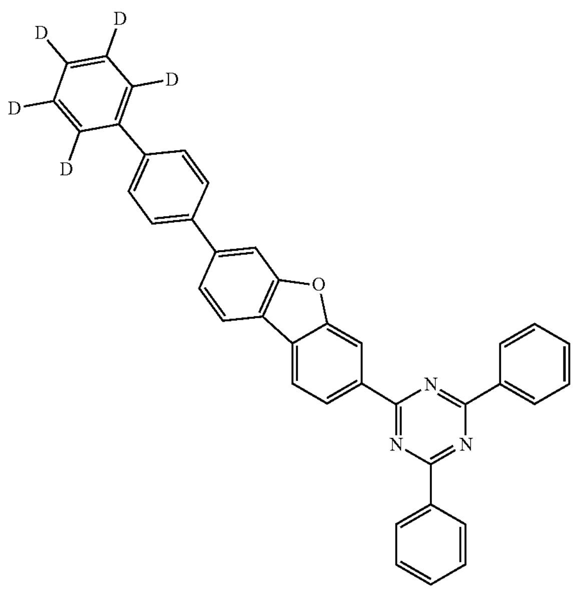
-continued
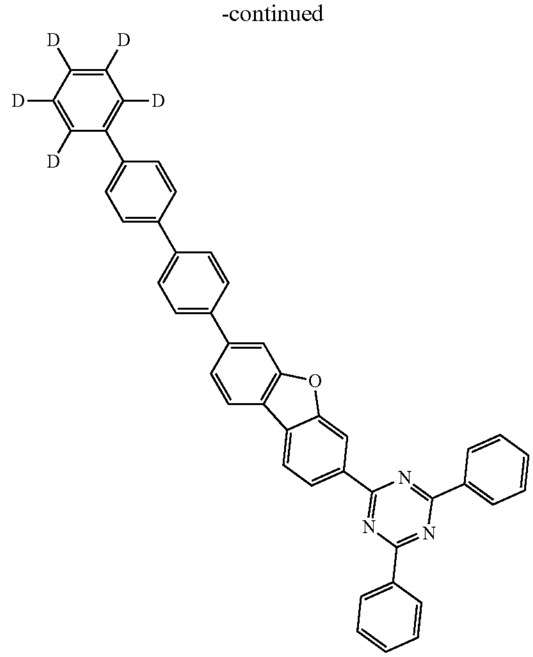
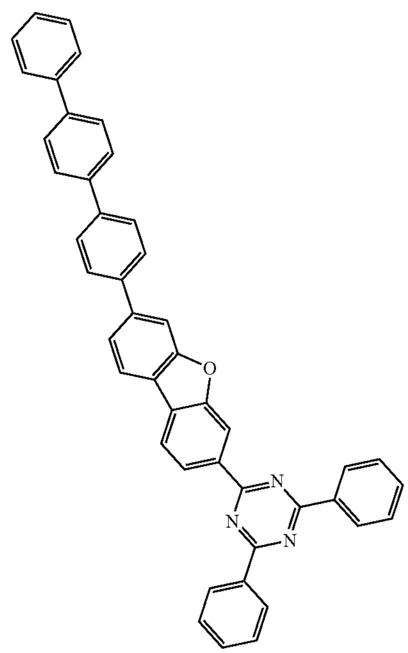

-continued
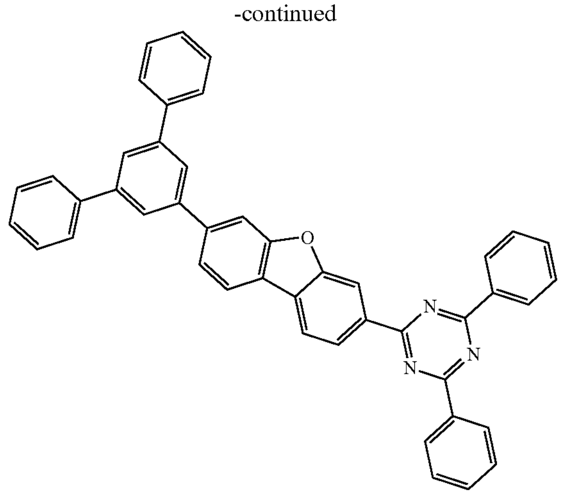
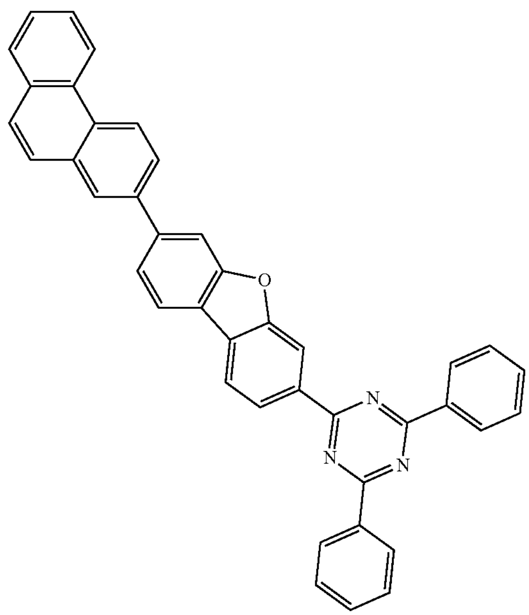
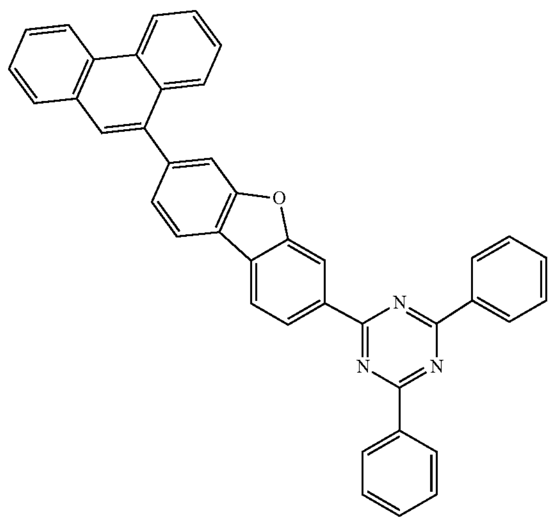
-continued
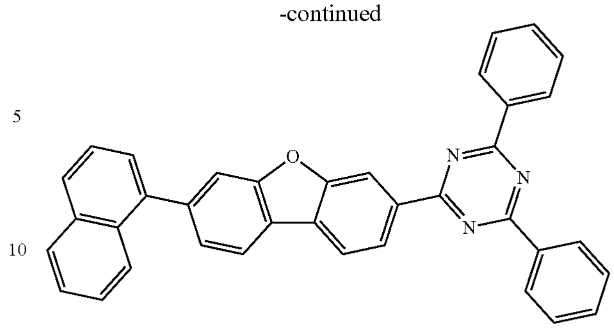
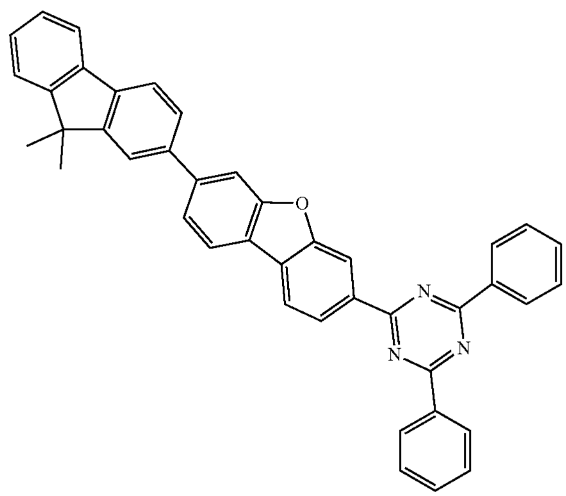
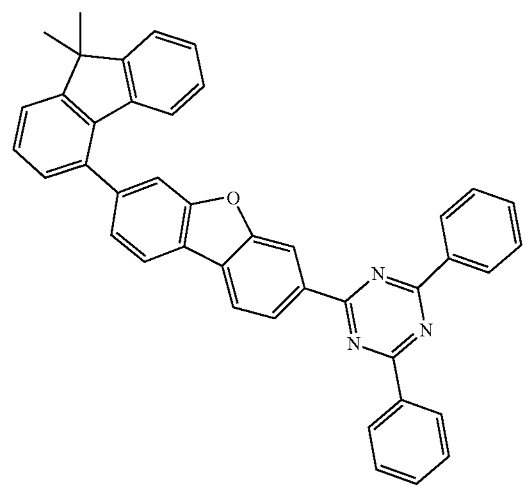

-continued
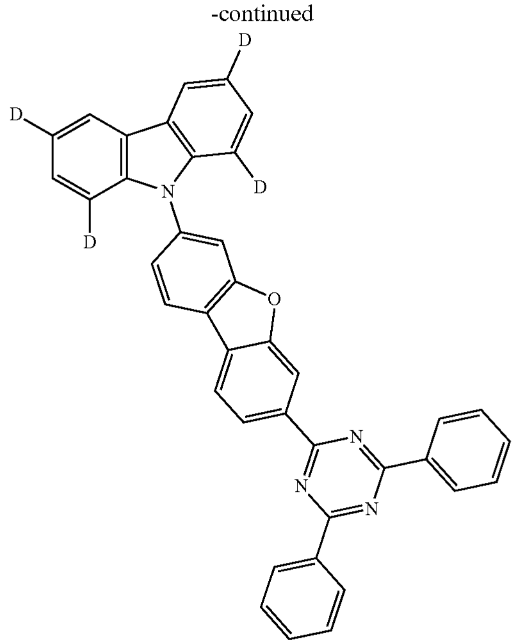
-continued
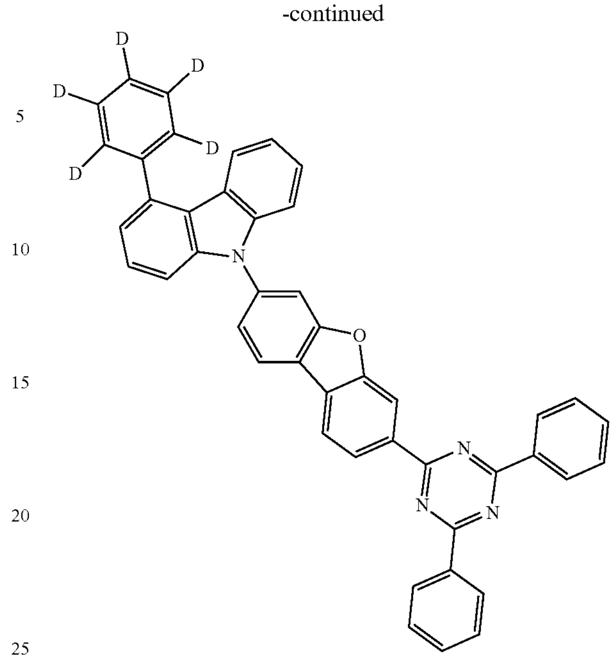
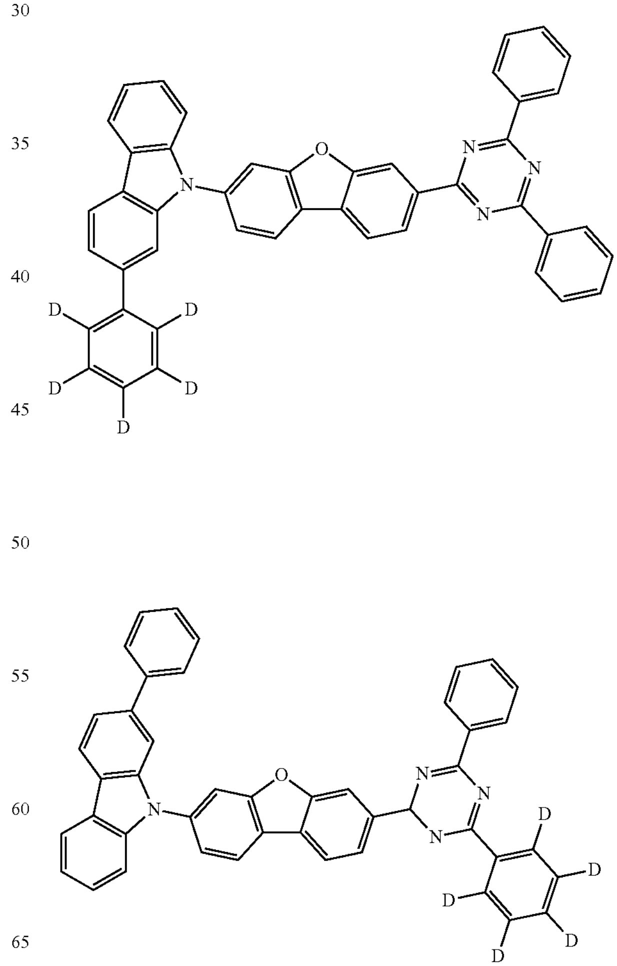
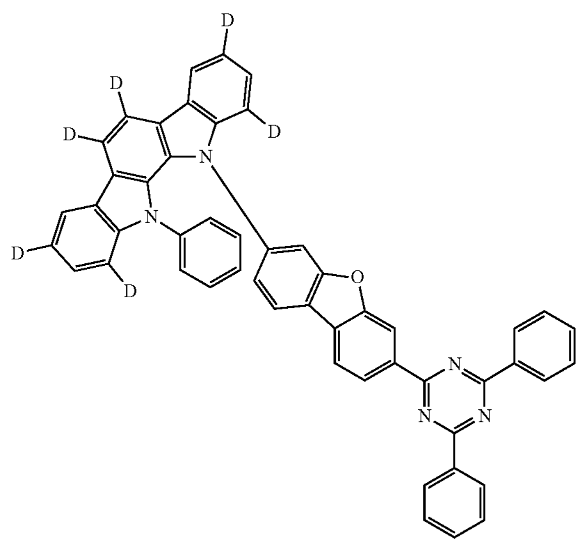

-continued
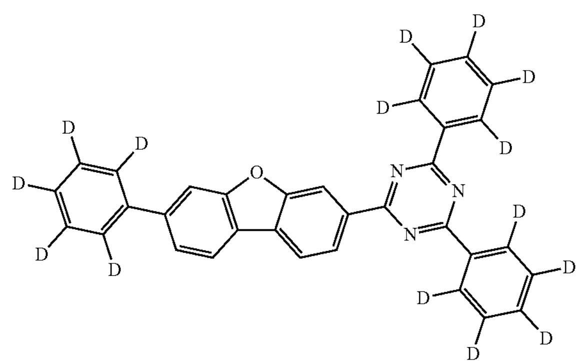
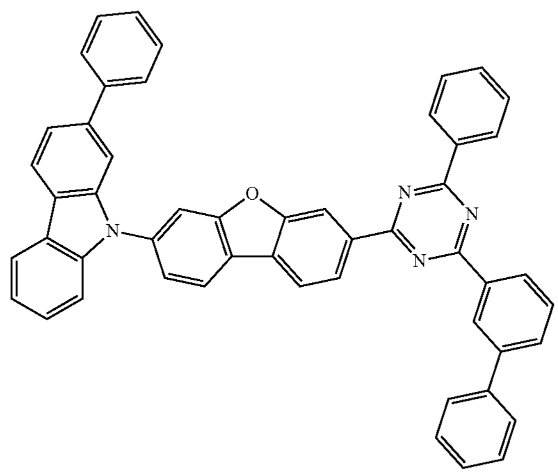
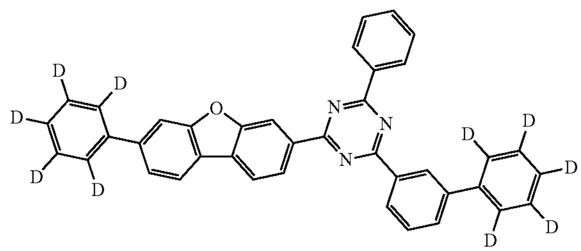
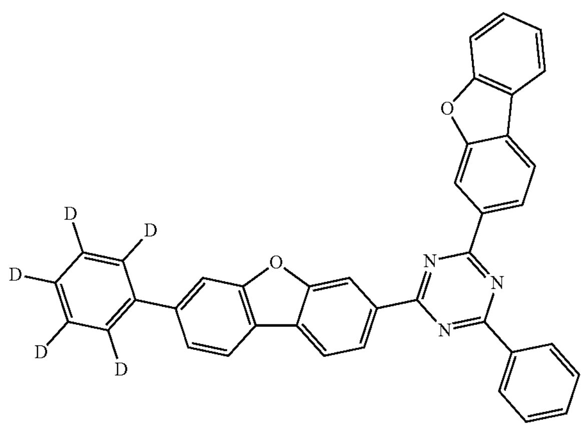
-continued
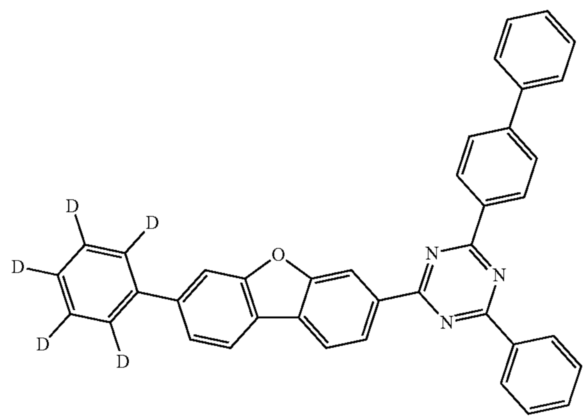
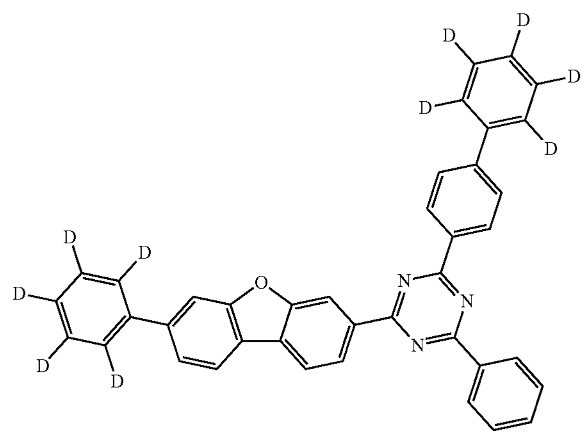
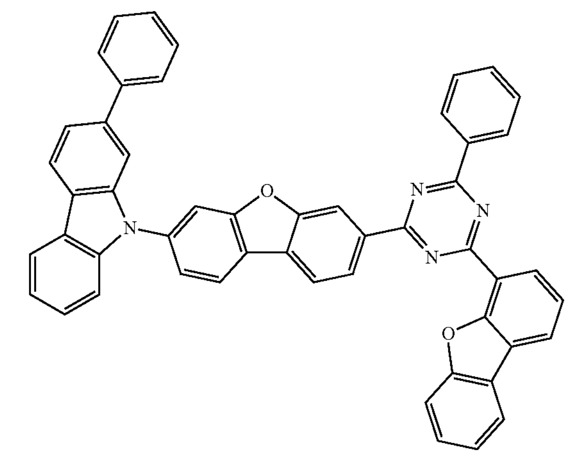
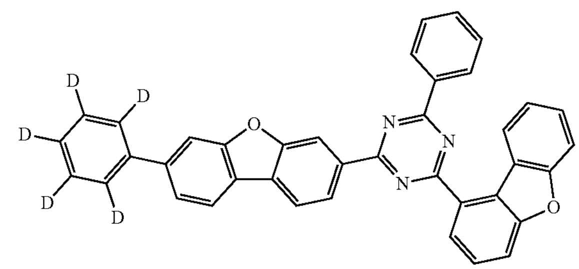

-continued
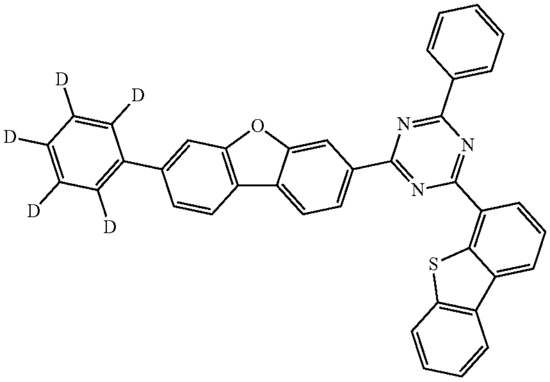
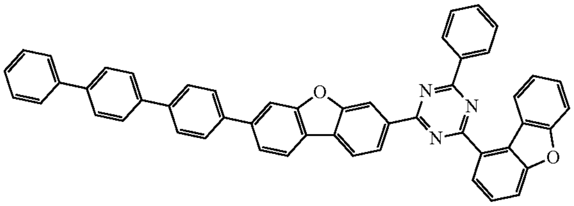
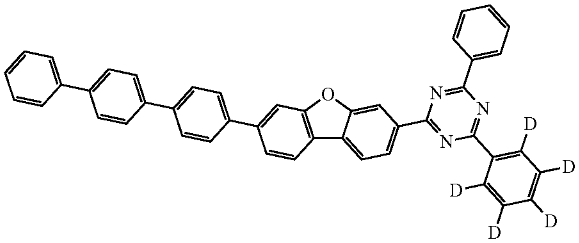
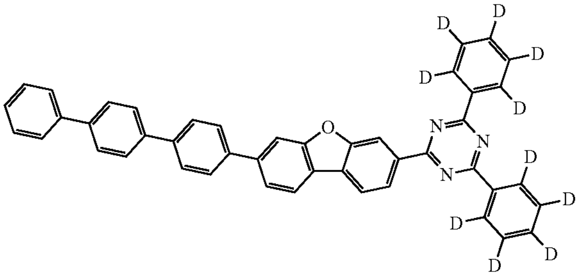
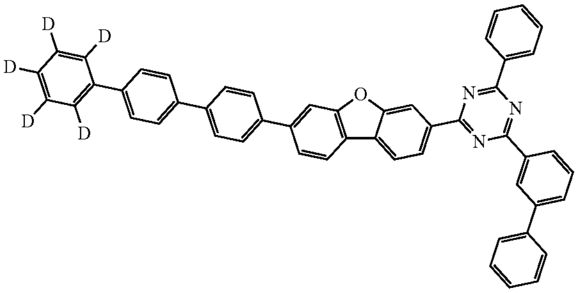
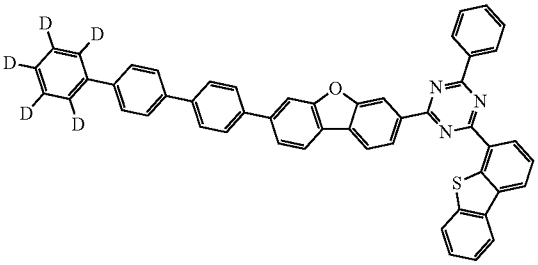
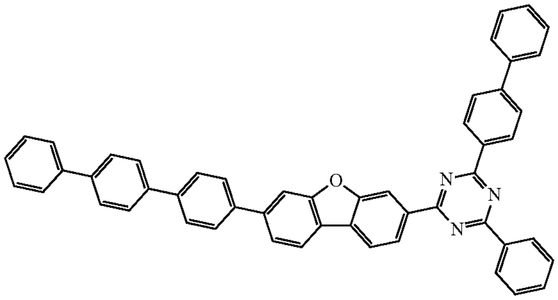
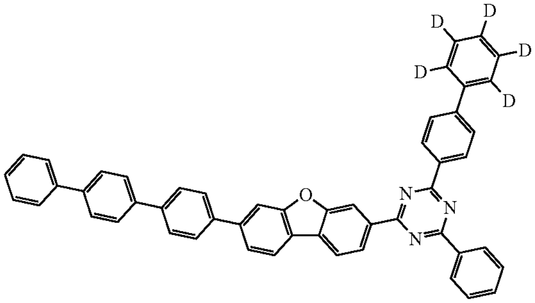
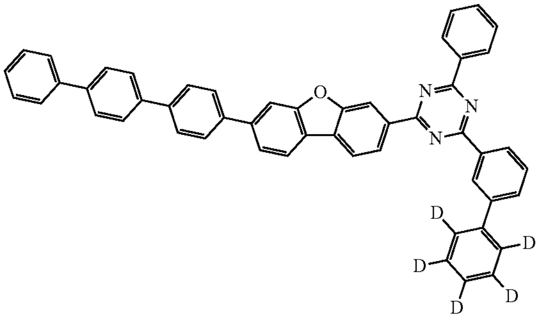
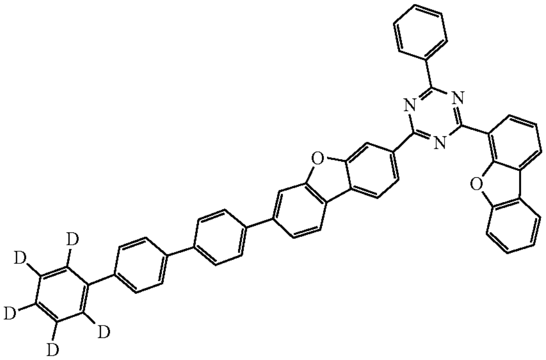

-continued
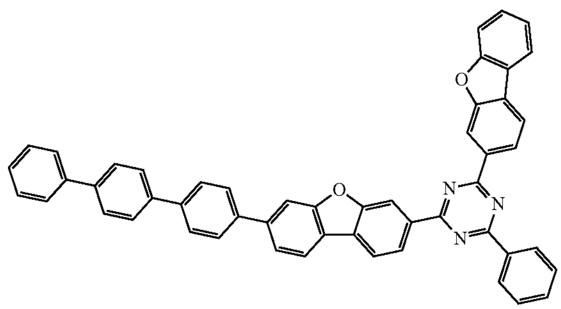
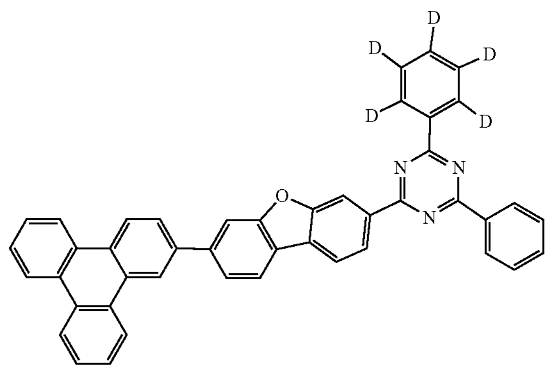
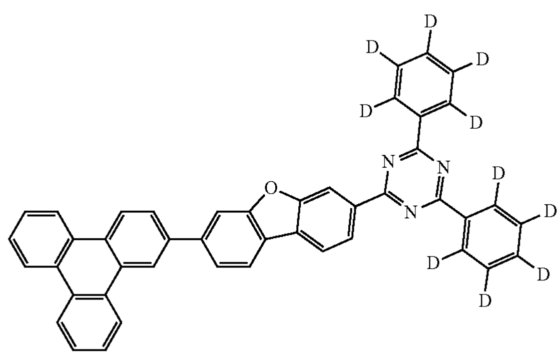
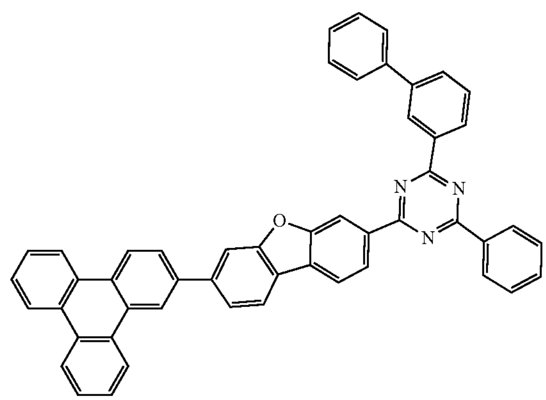
-continued
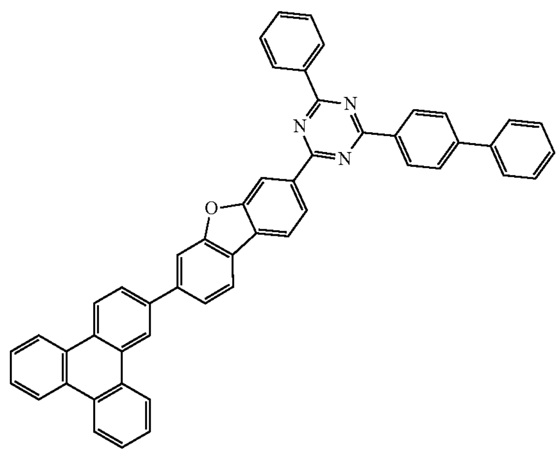
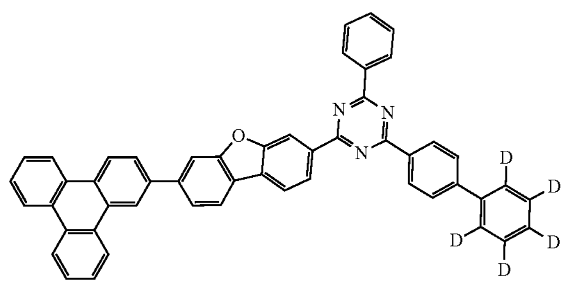
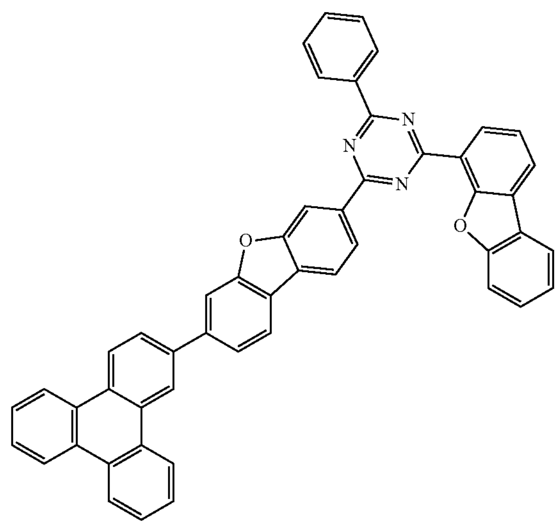
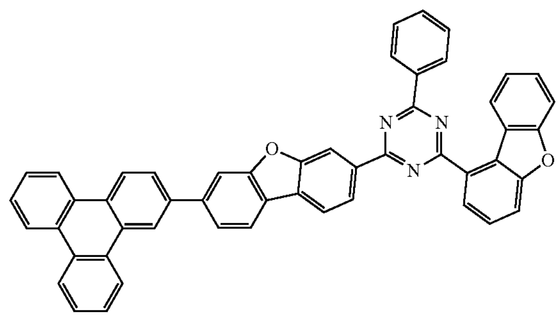

-continued
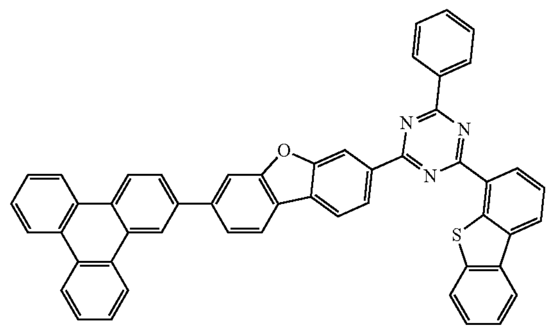
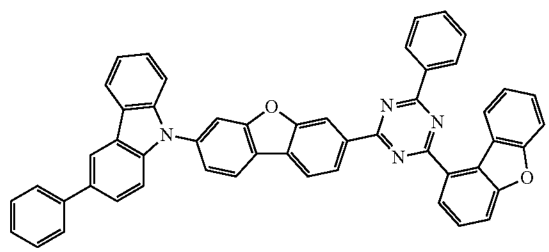
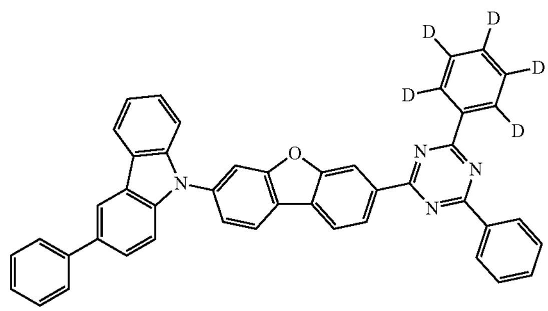
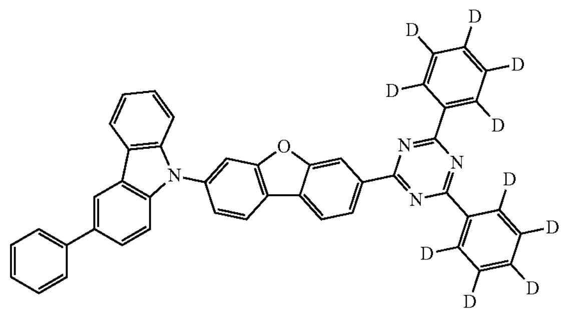
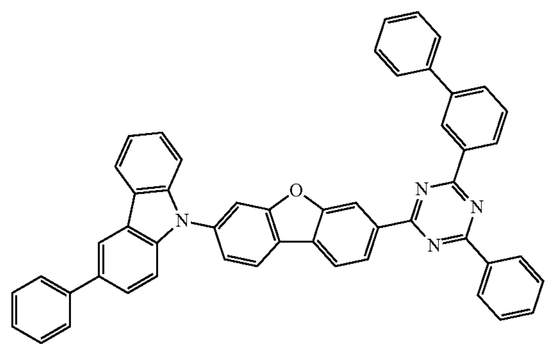
-continued
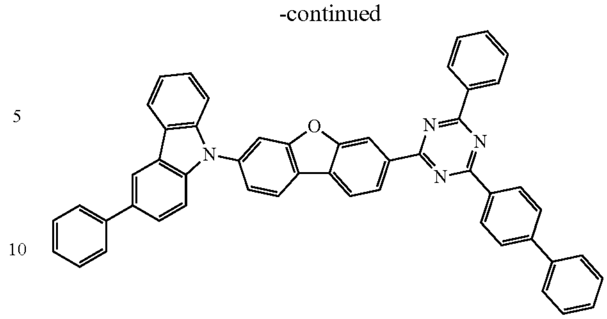
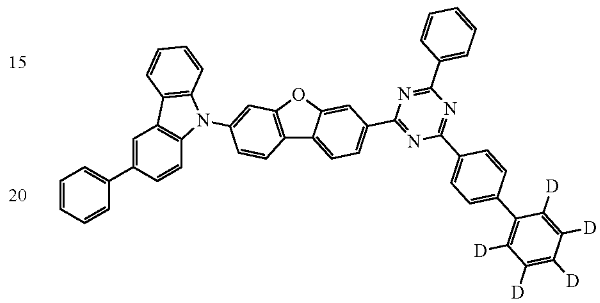
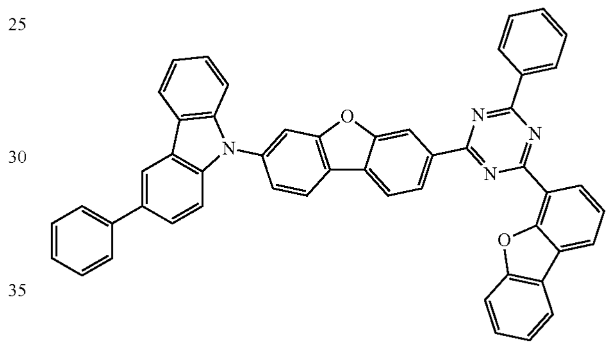
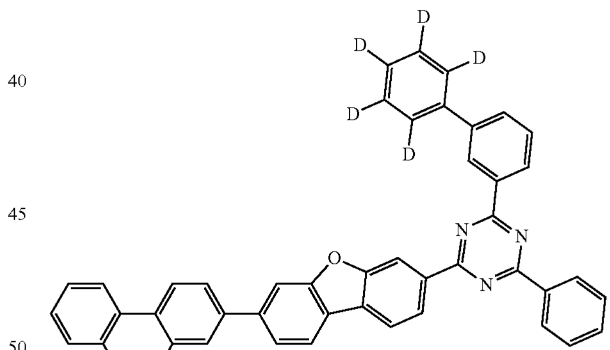
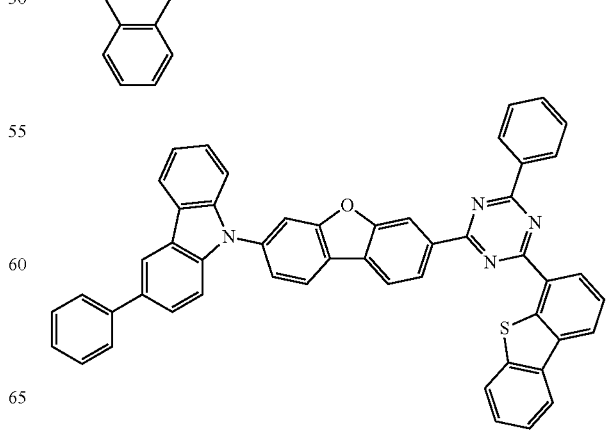

-continued
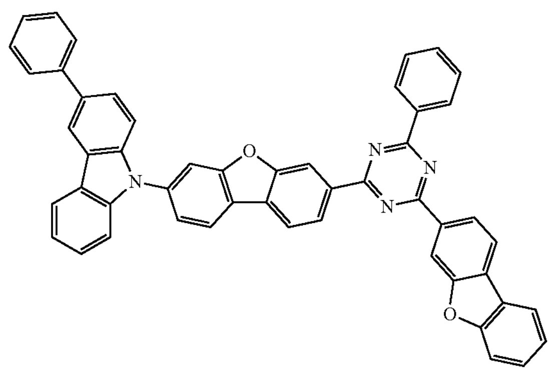
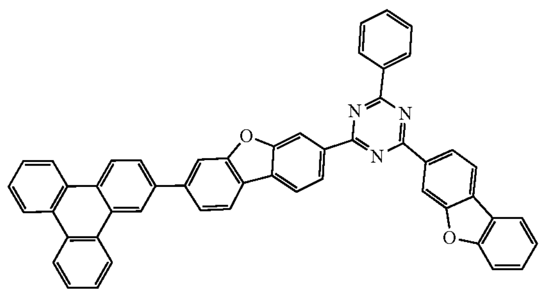
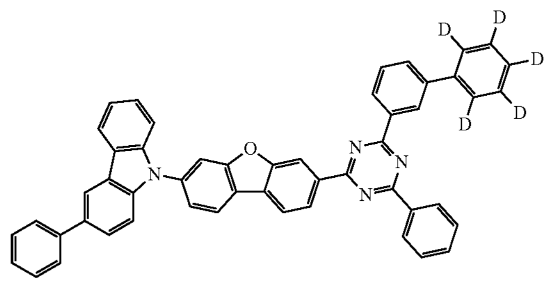
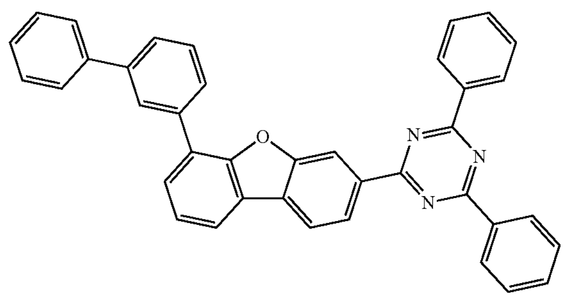
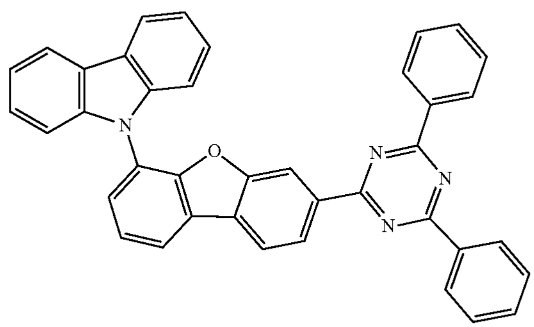
-continued
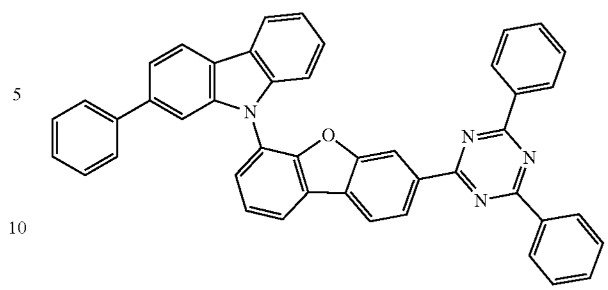
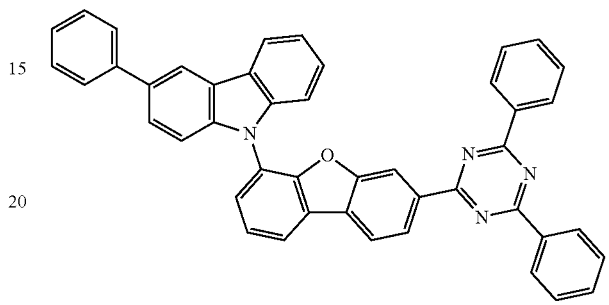
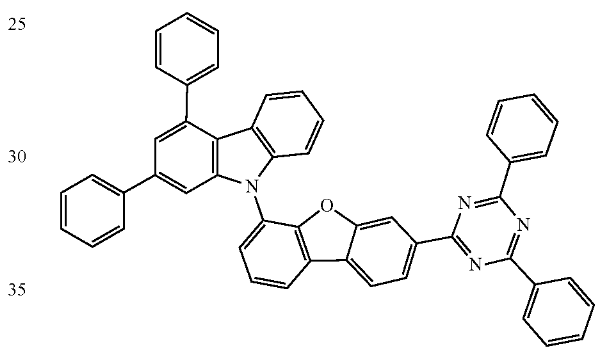
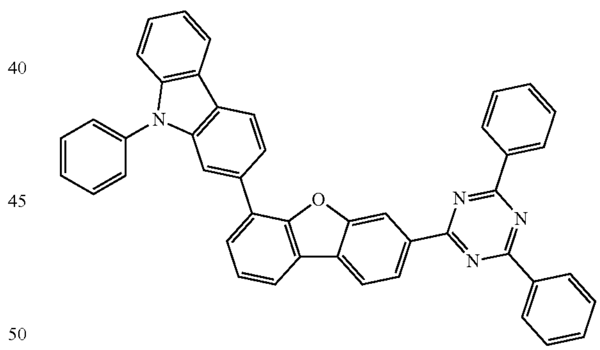
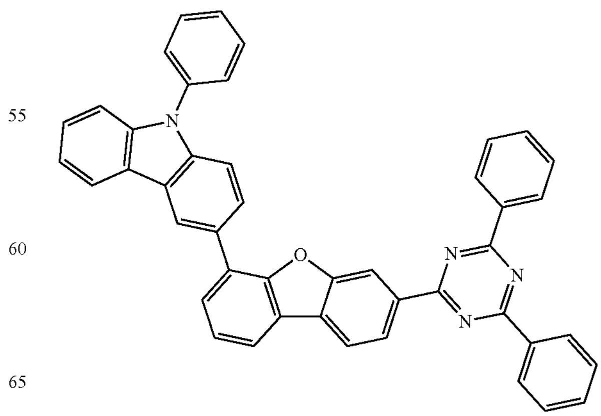

-continued
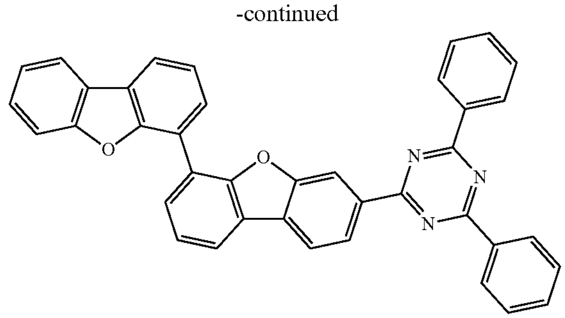
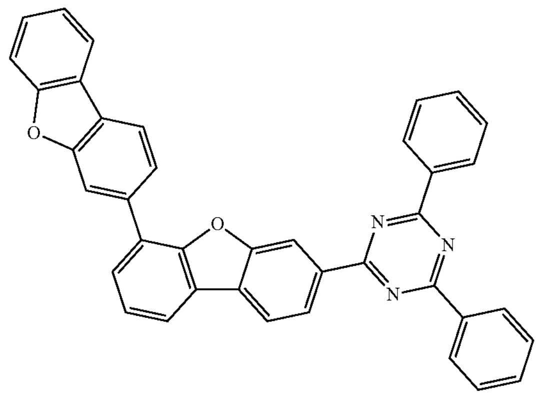
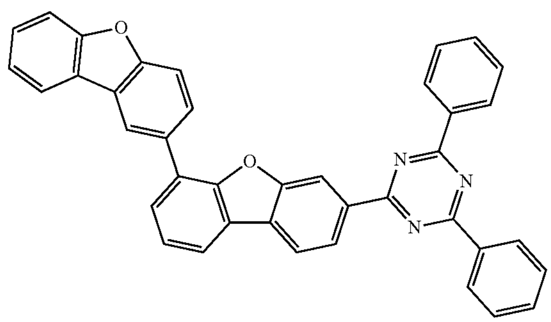
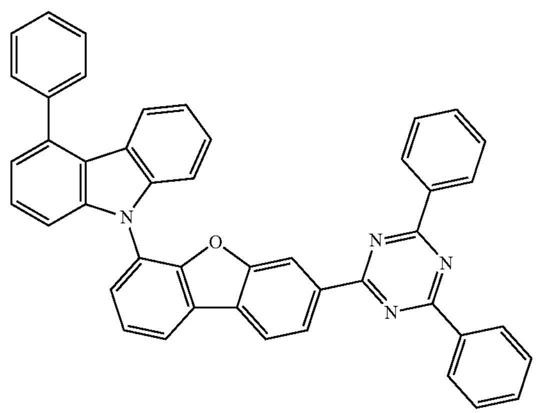
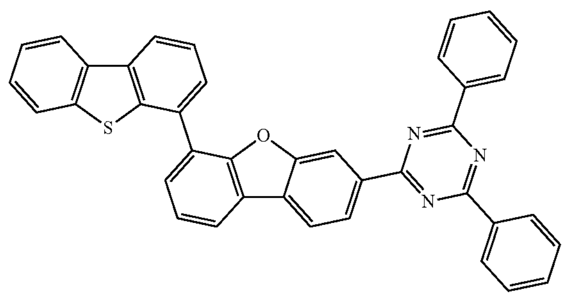
-continued
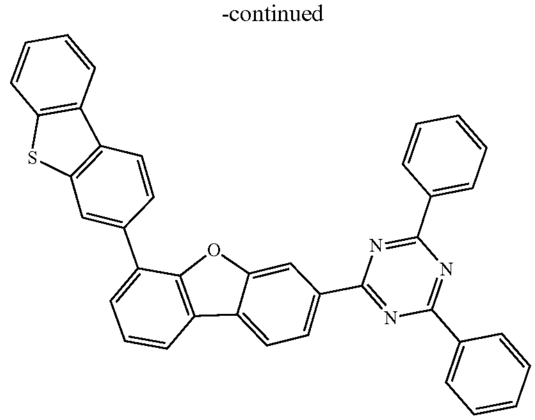
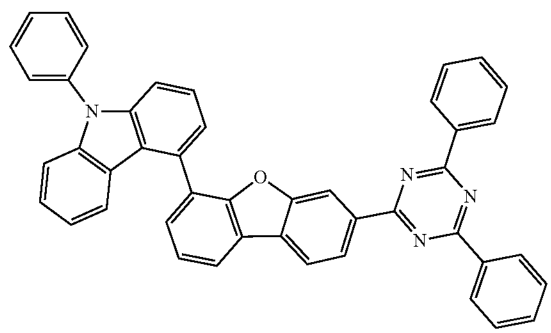
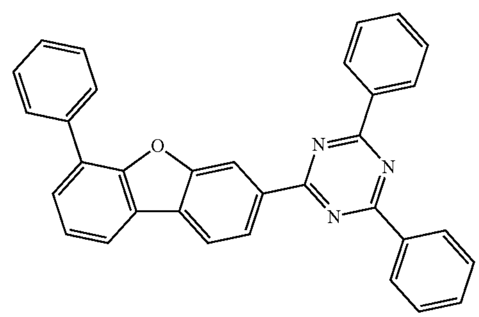
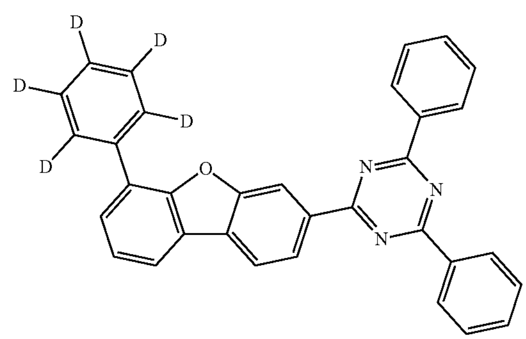
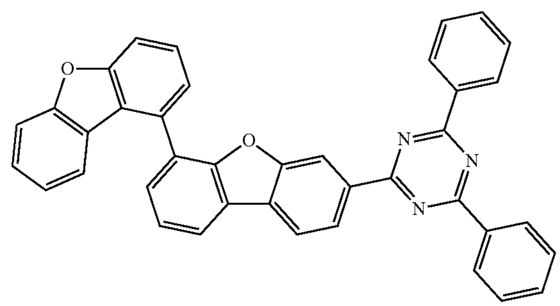

-continued
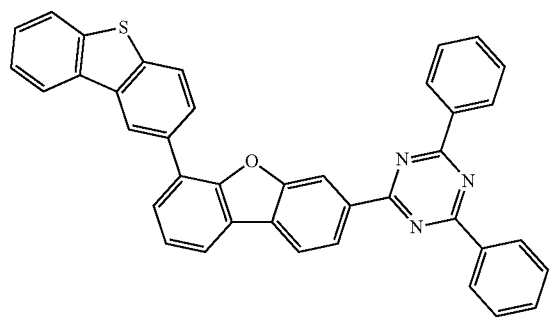
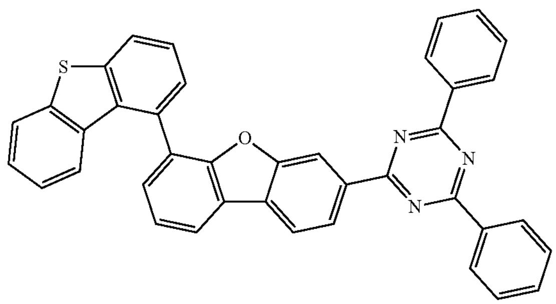
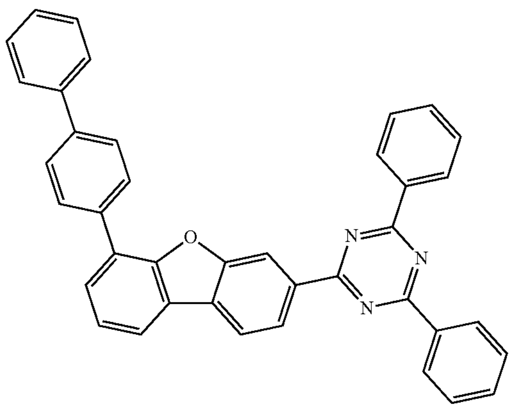
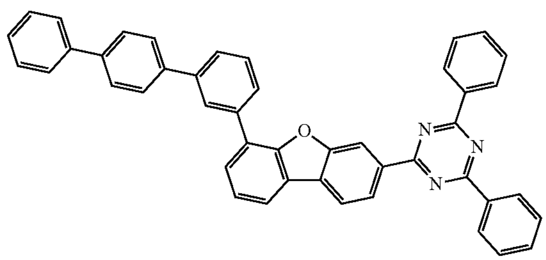
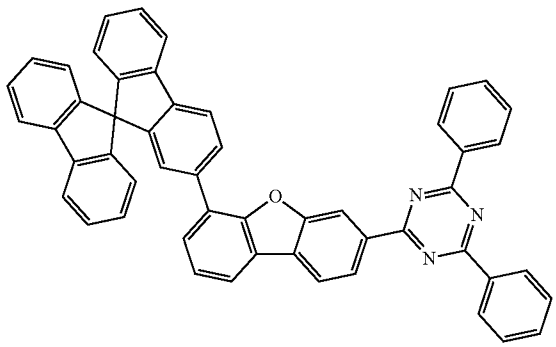
-continued
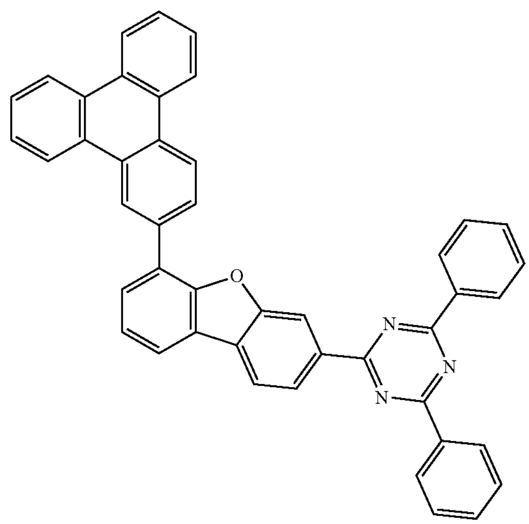
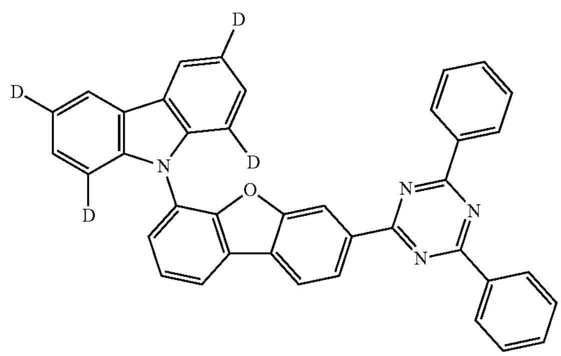
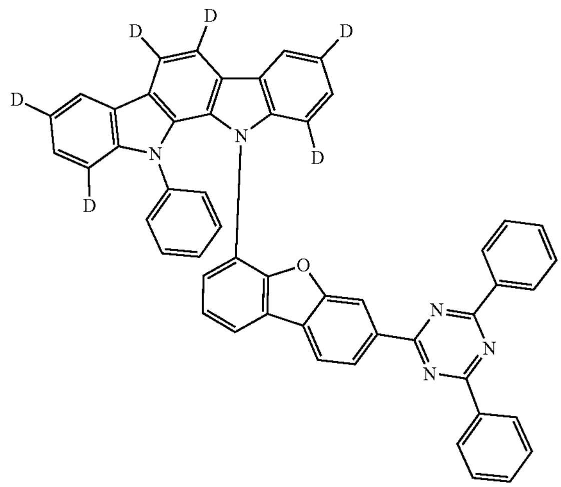

-continued
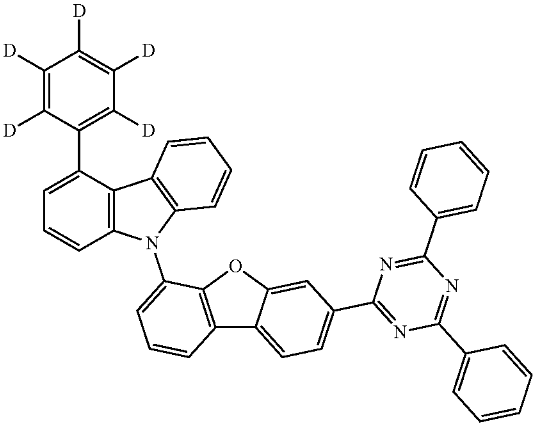
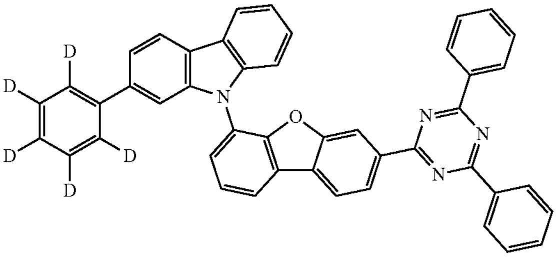
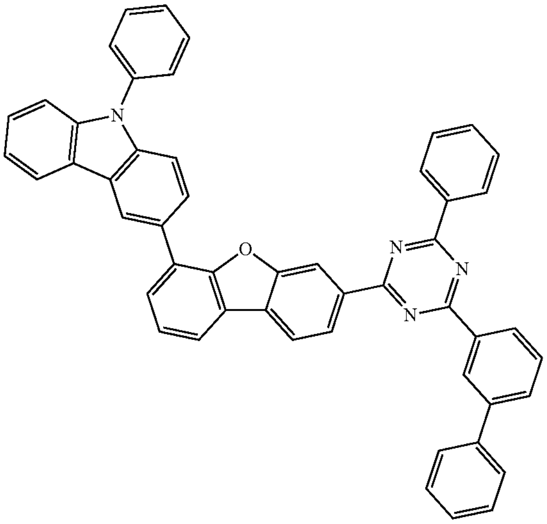
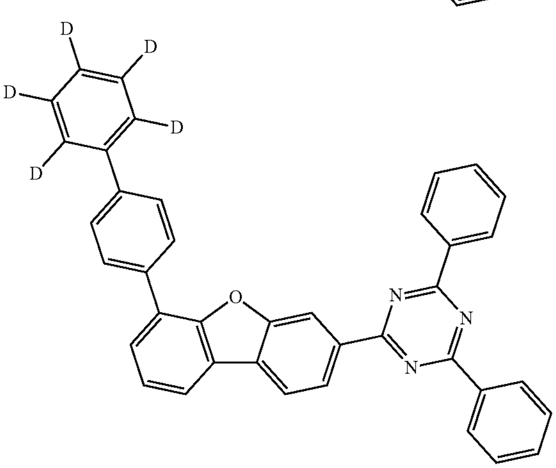
-continued
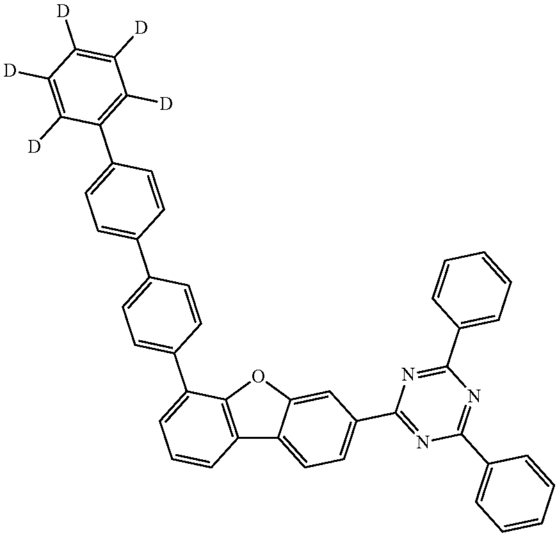
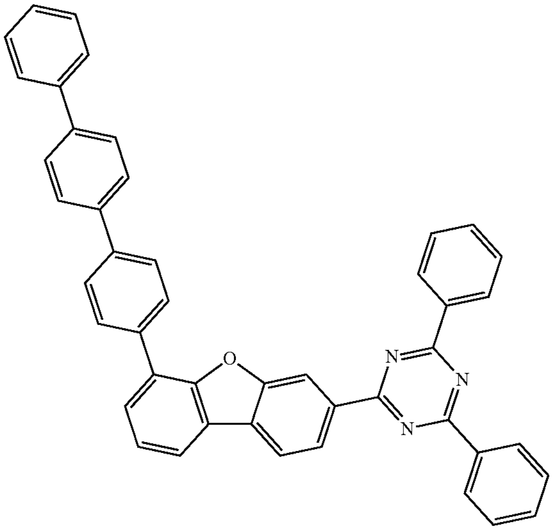
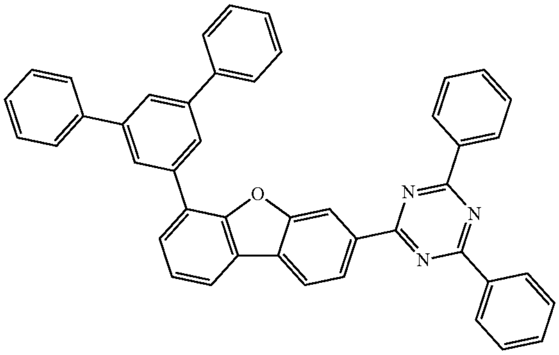

-continued
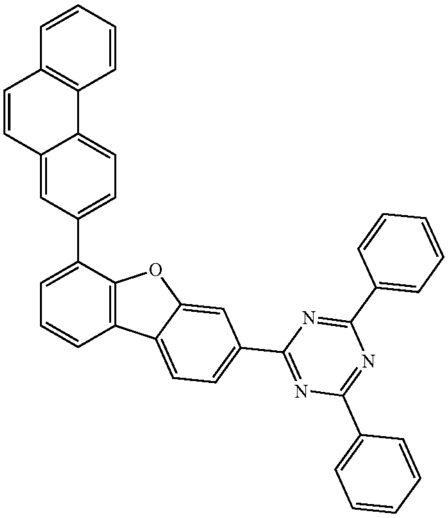
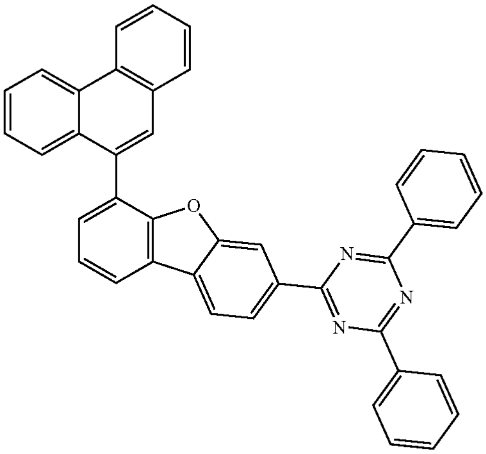
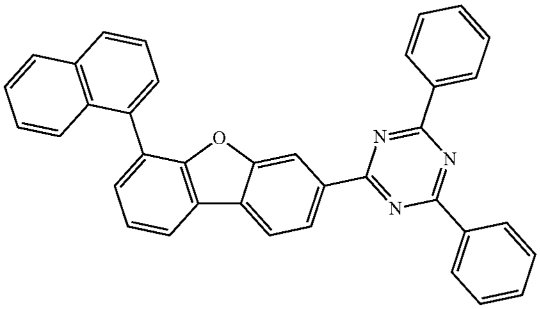
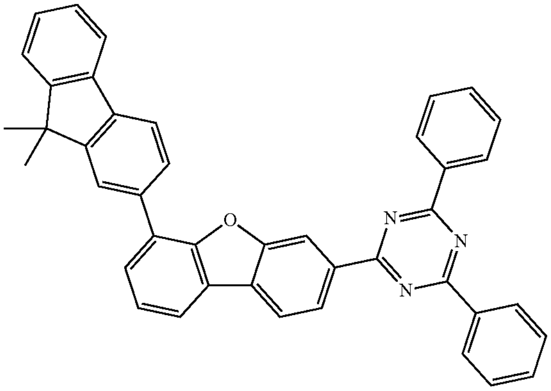
-continued
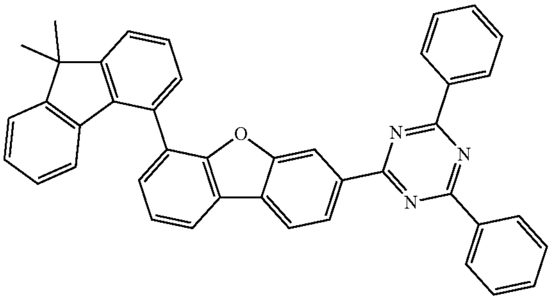
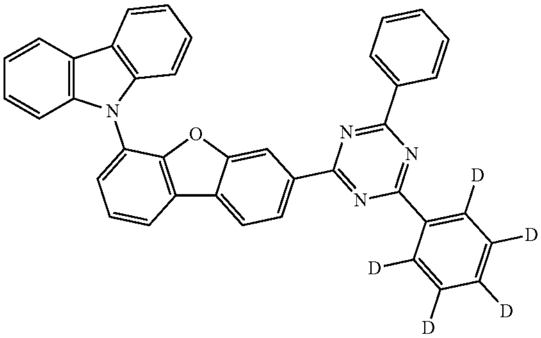
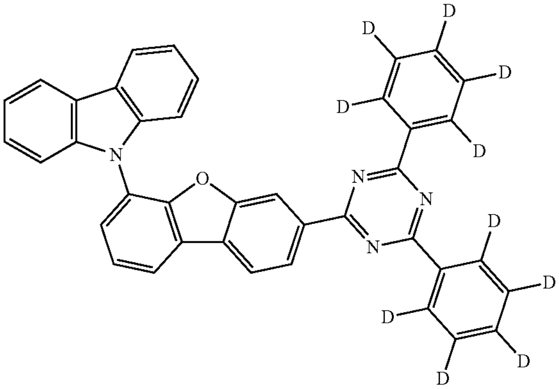
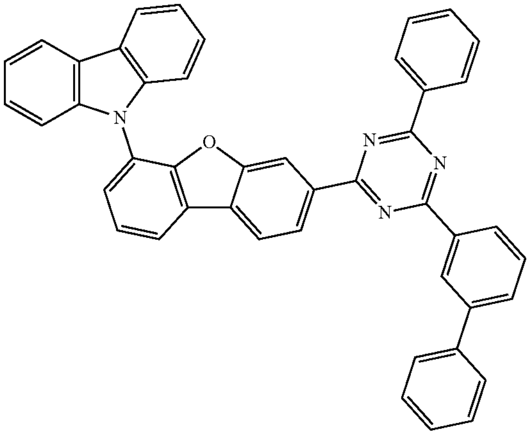

-continued
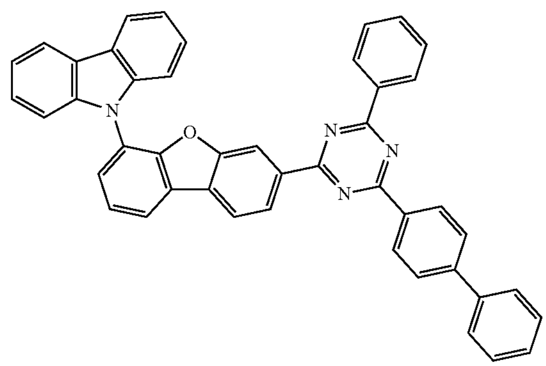
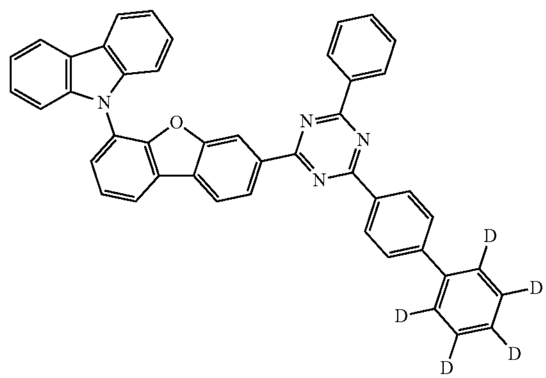
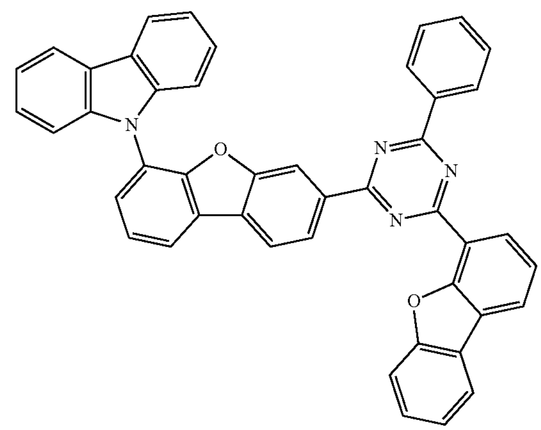 [SMILES: c1ccc(-c2nc(-c3ccc4c(c3)sc3c(-n5c6ccccc6c6ccccc65)cccc34)nc(-c3cccc4c3oc3ccccc34)n2)cc1]
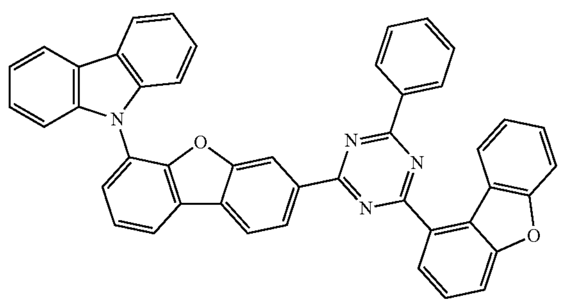
-continued
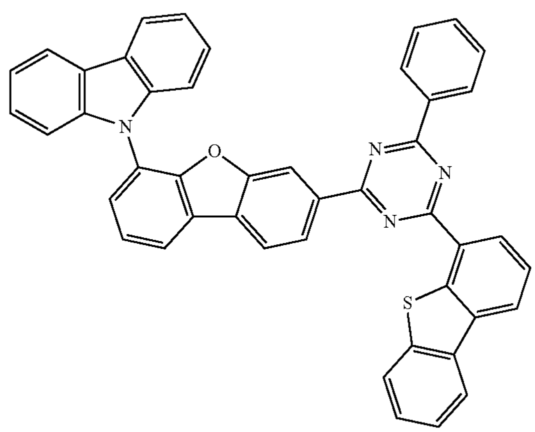
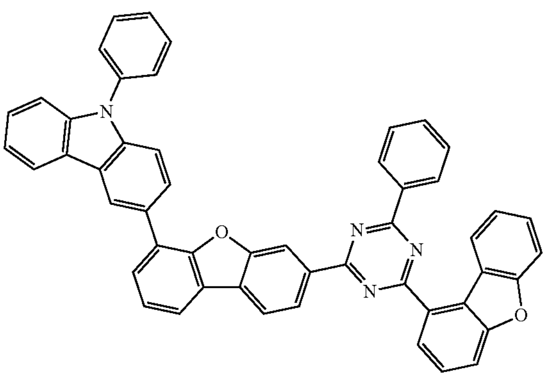
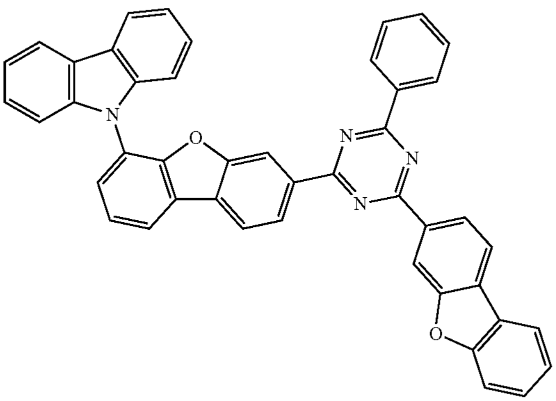
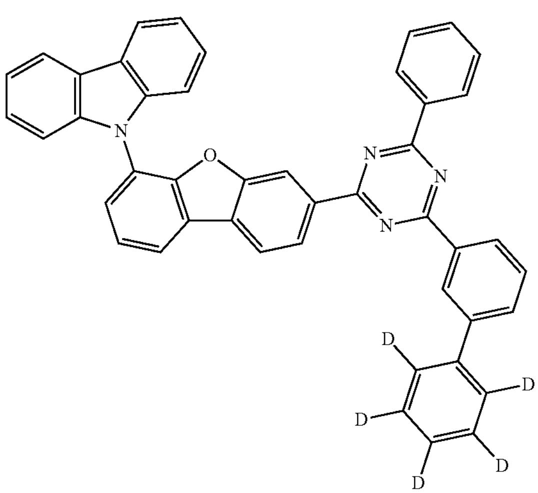

-continued
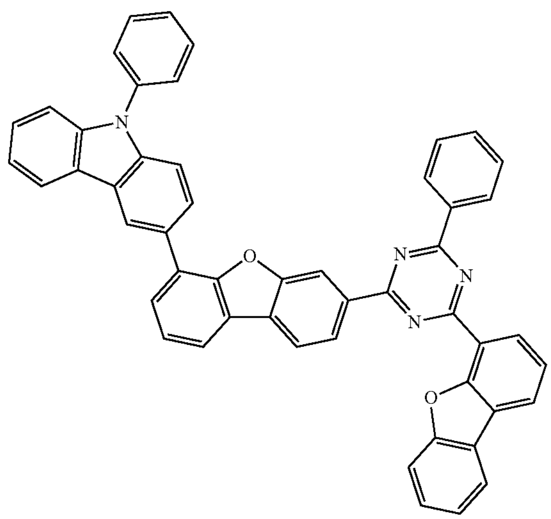
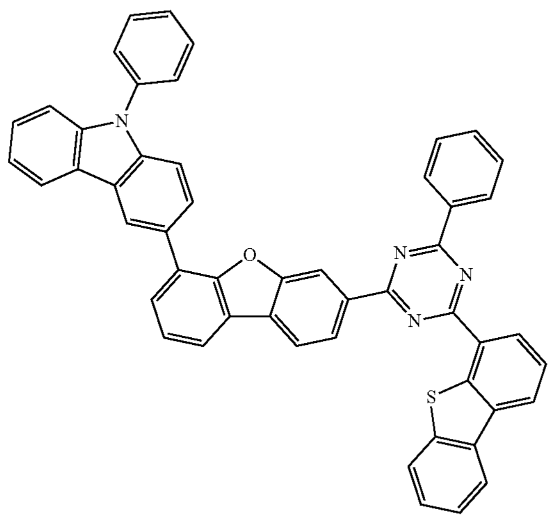
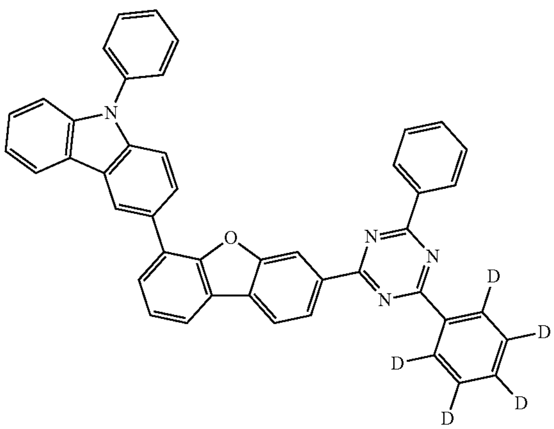
-continued
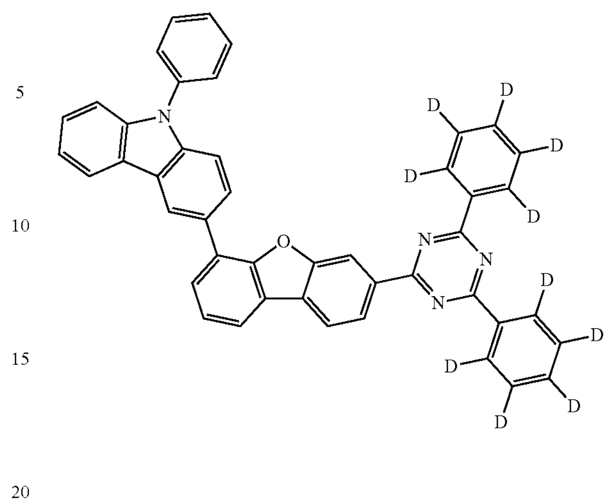
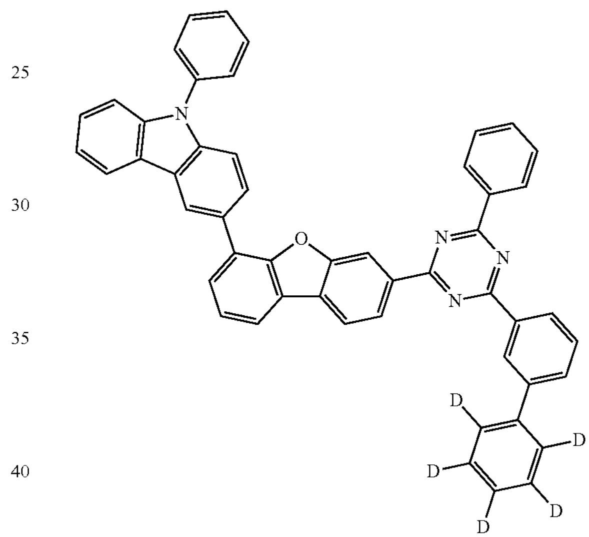
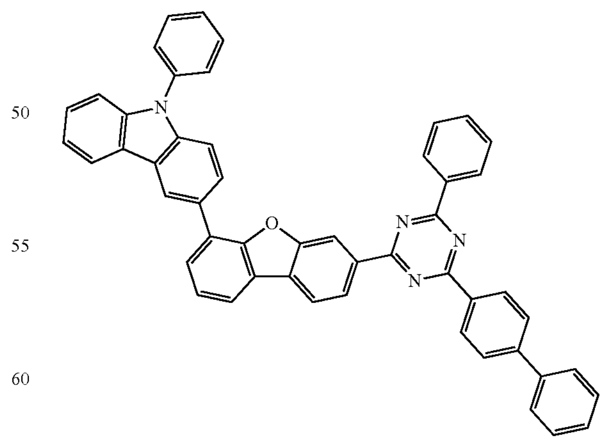

-continued
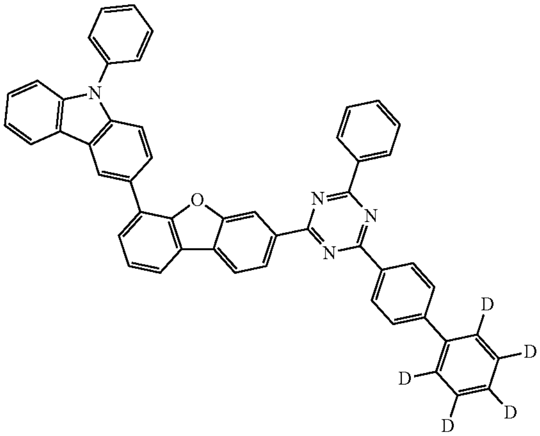
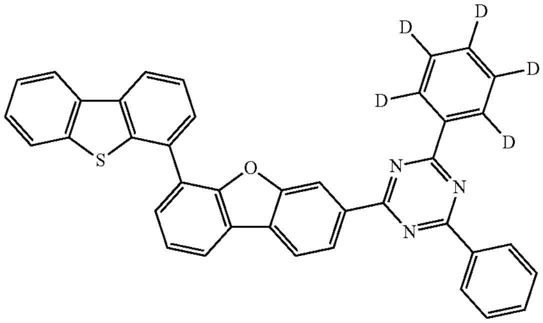
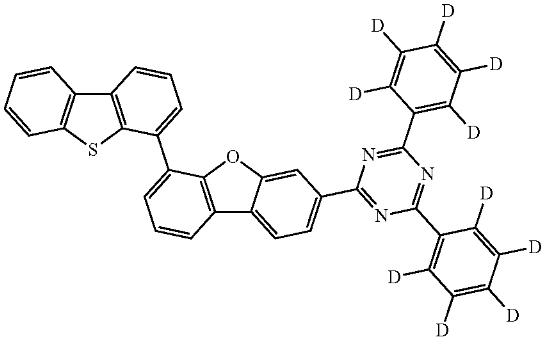
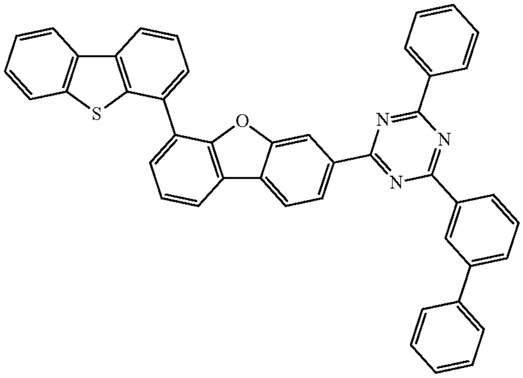
-continued
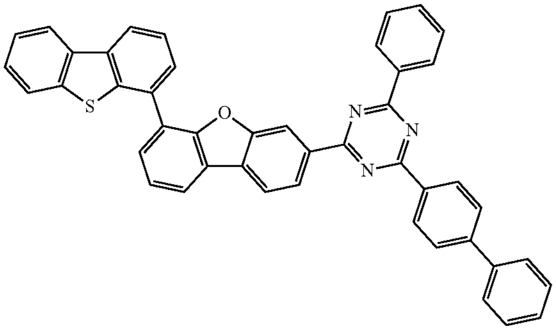
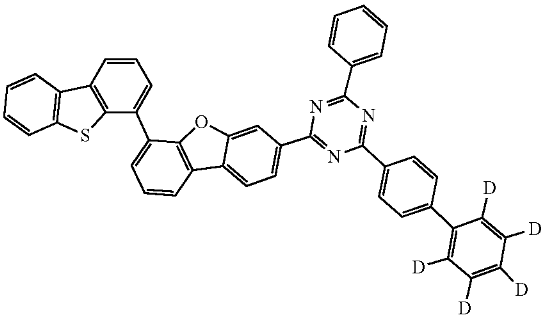
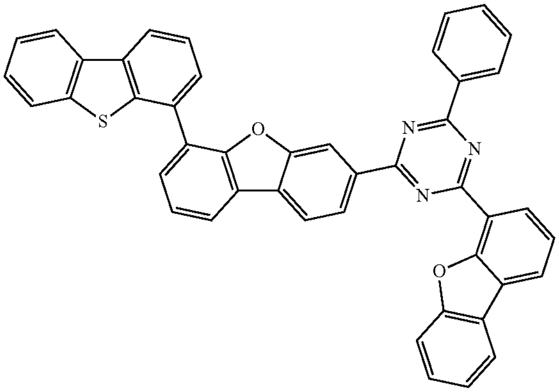
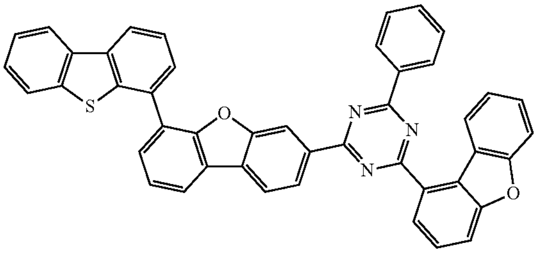
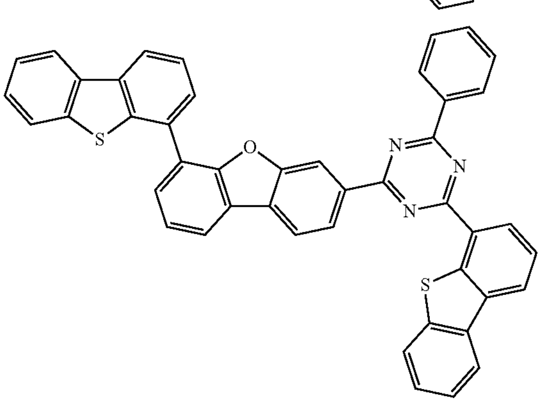

-continued
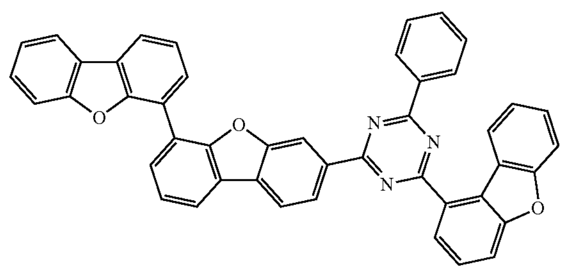
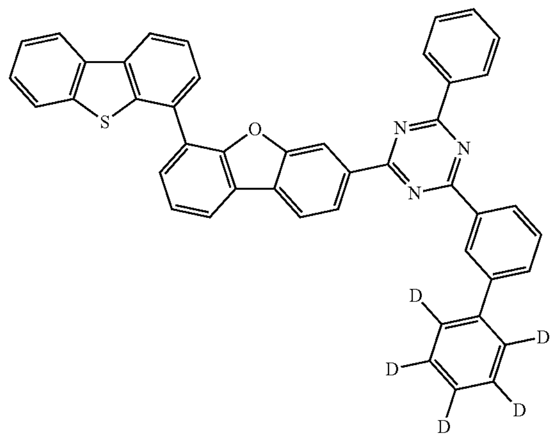
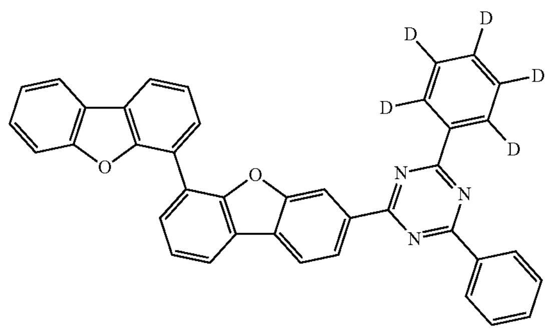
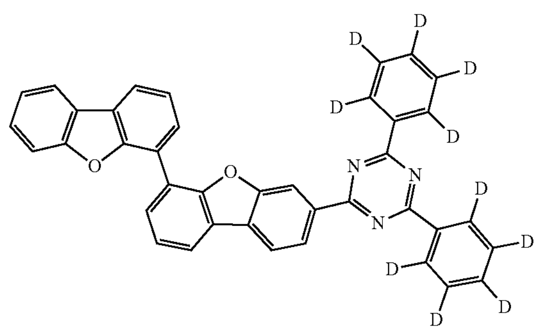
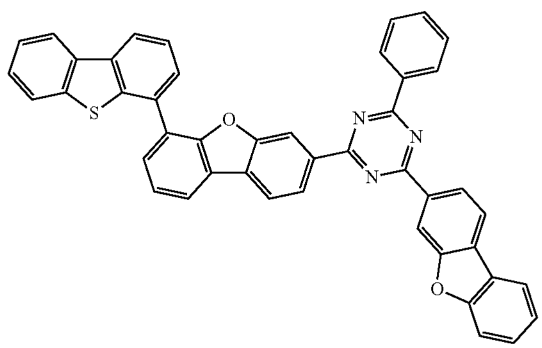
-continued
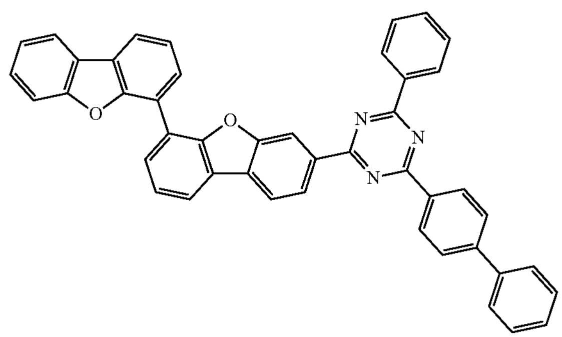
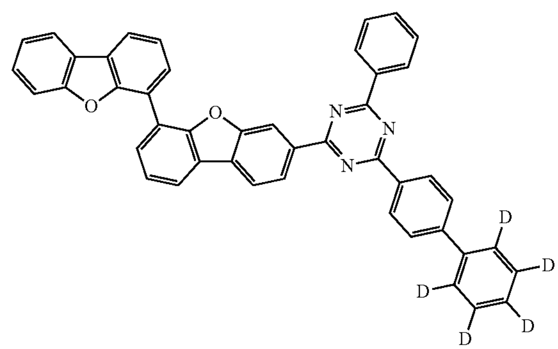
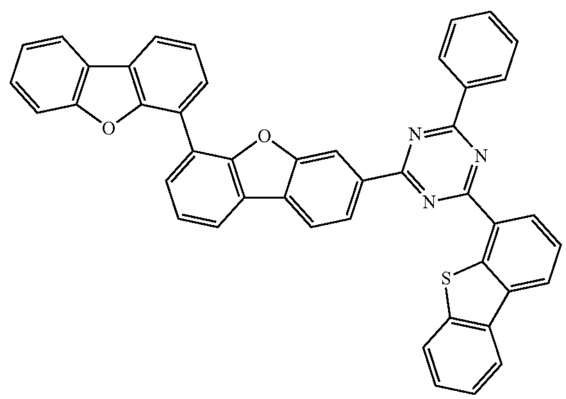
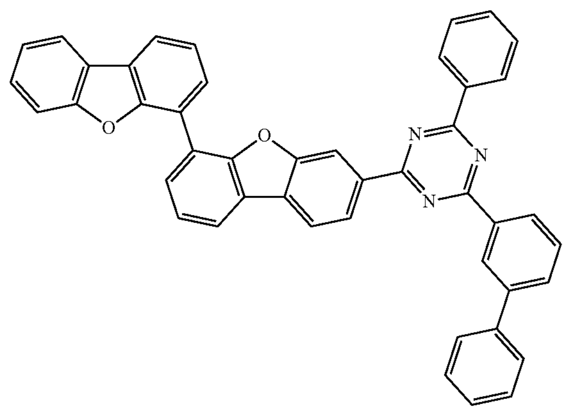

-continued
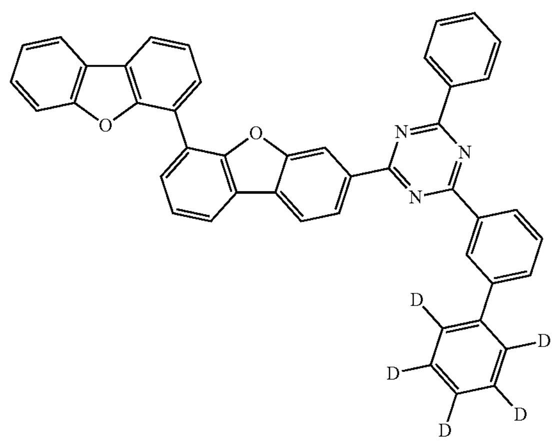
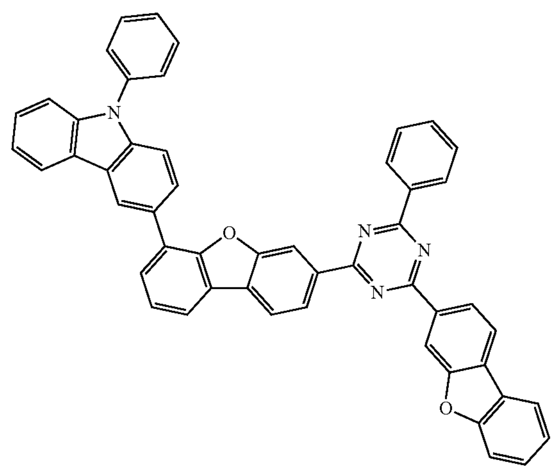
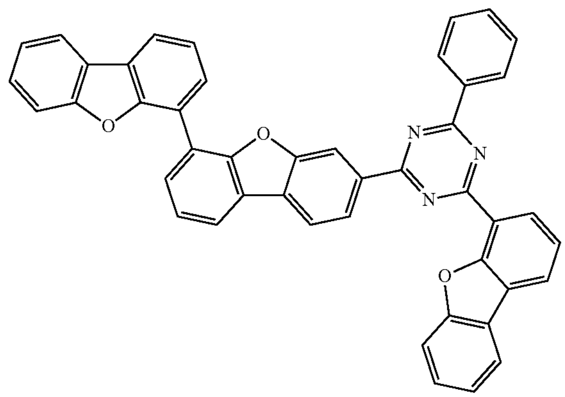
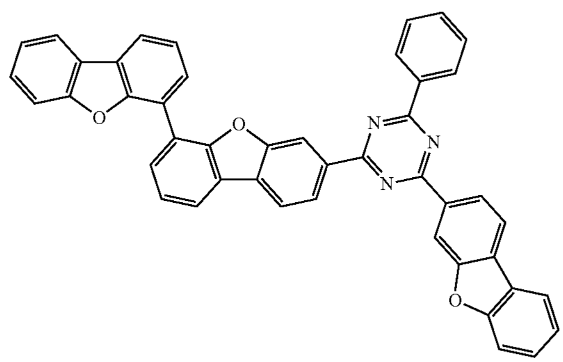
-continued
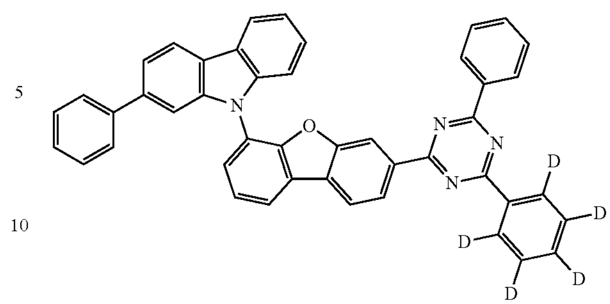
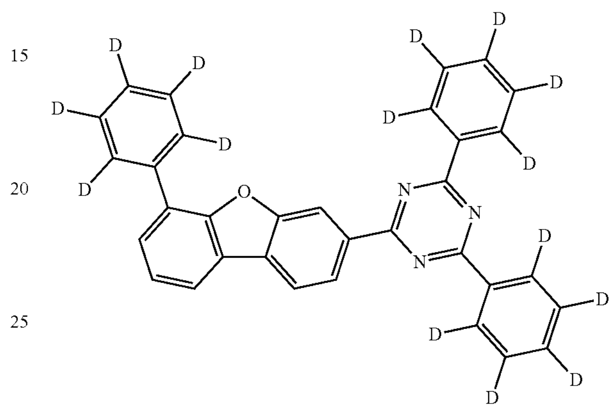
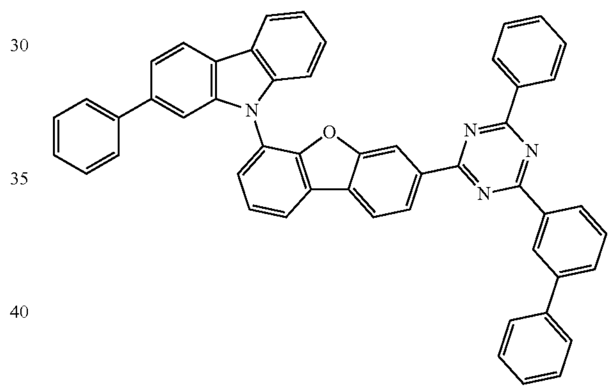
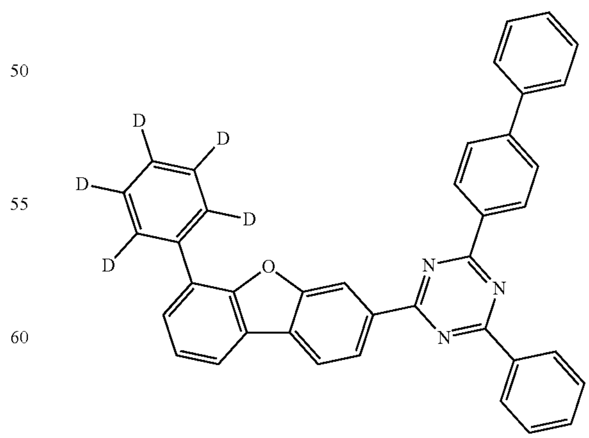

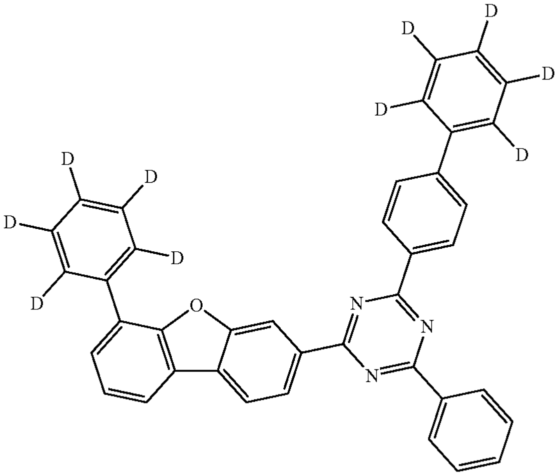
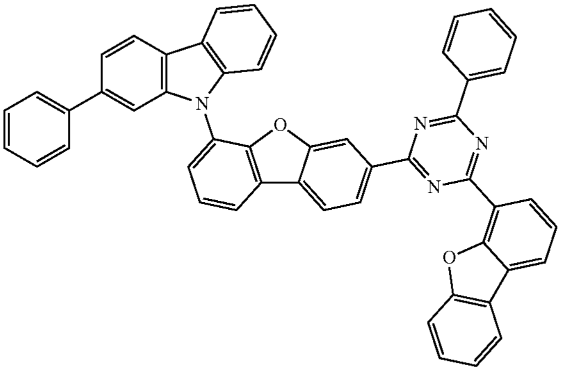
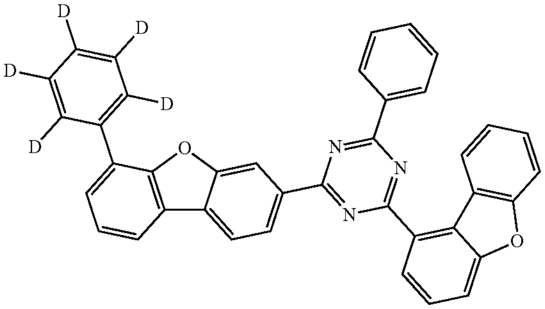
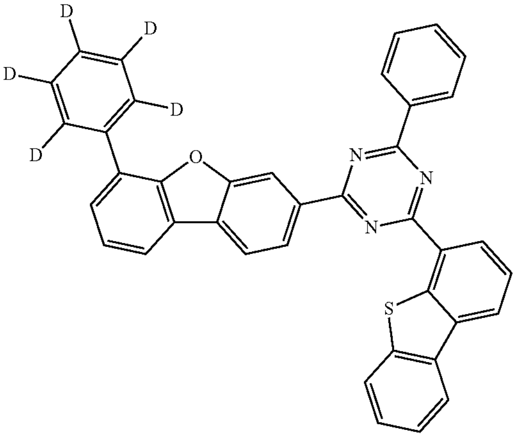
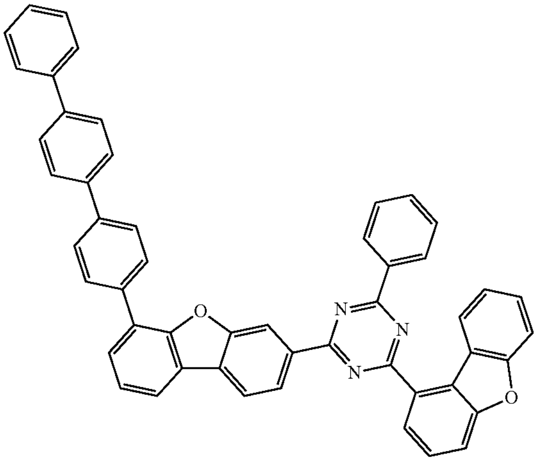
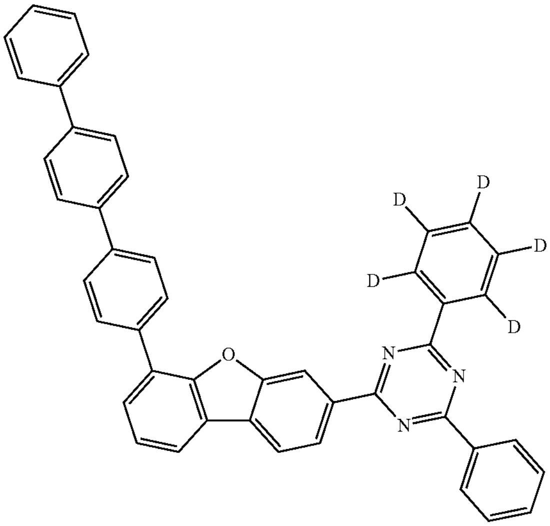
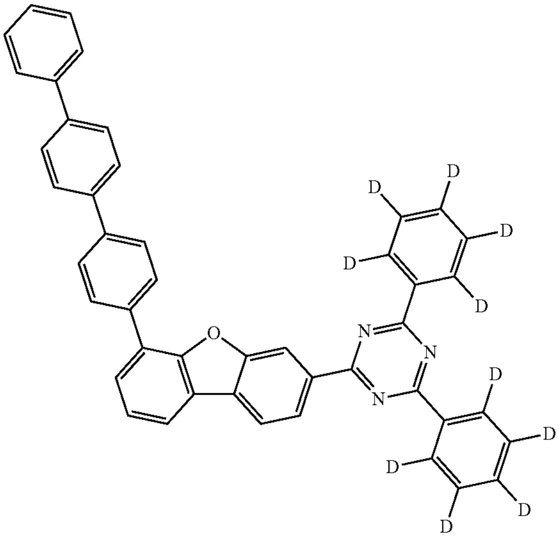

-continued
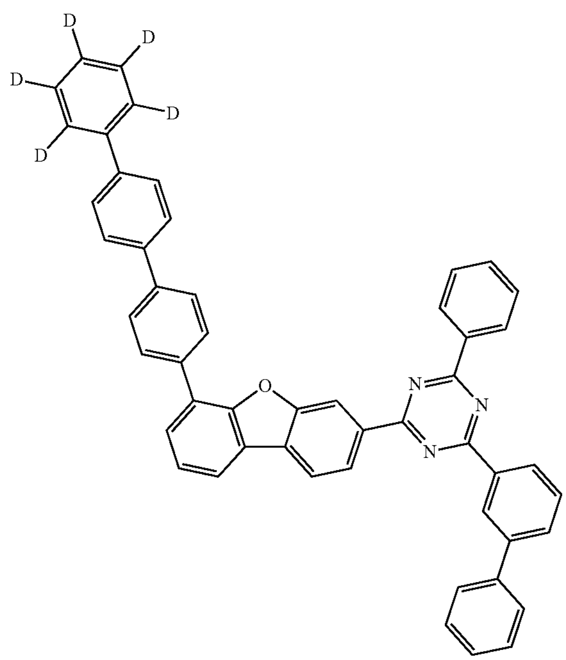
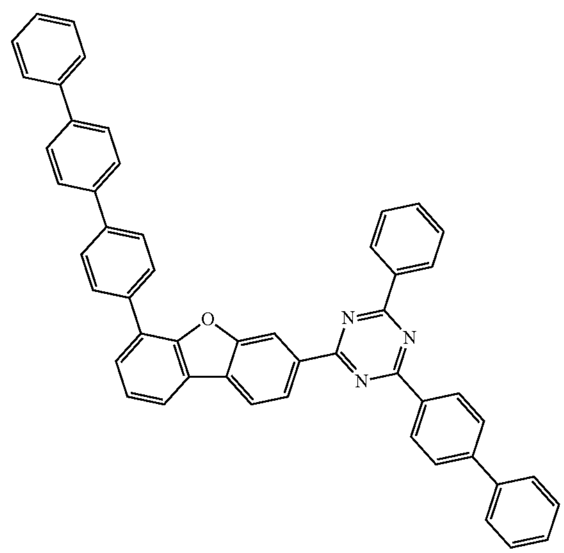
-continued
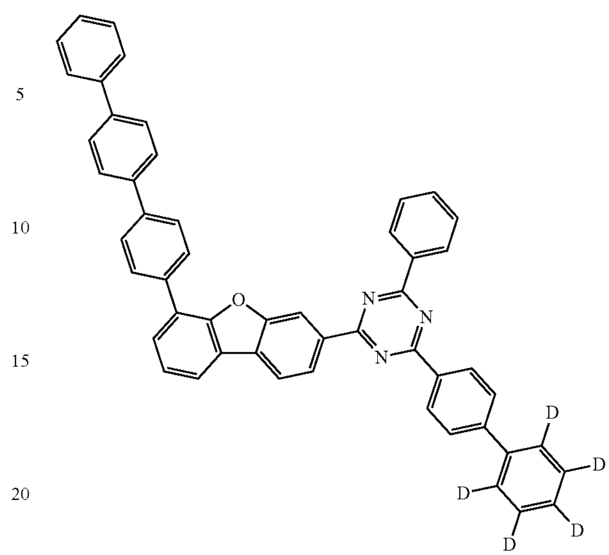
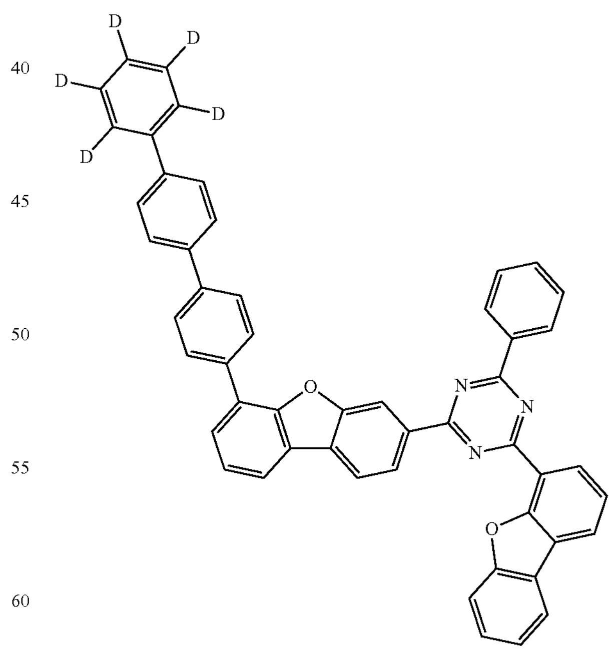

-continued
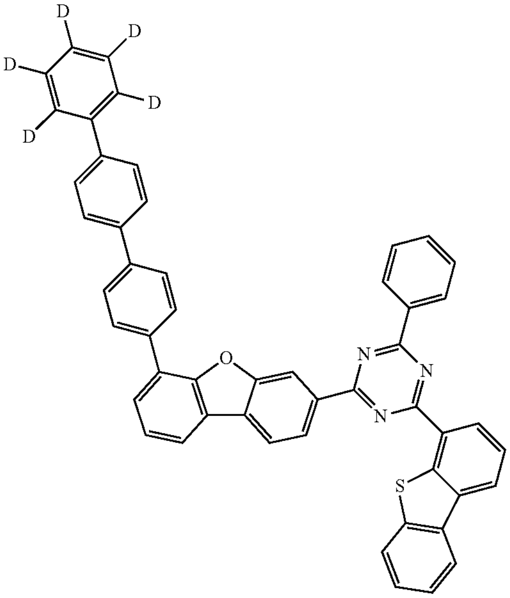
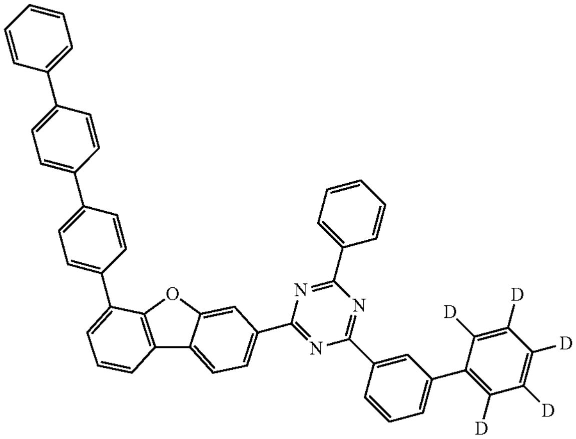
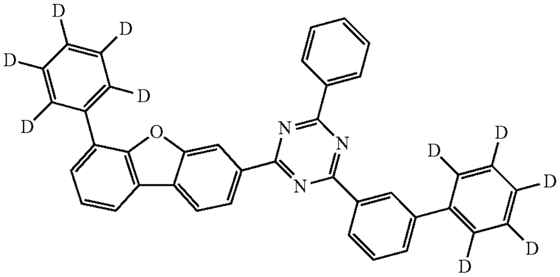
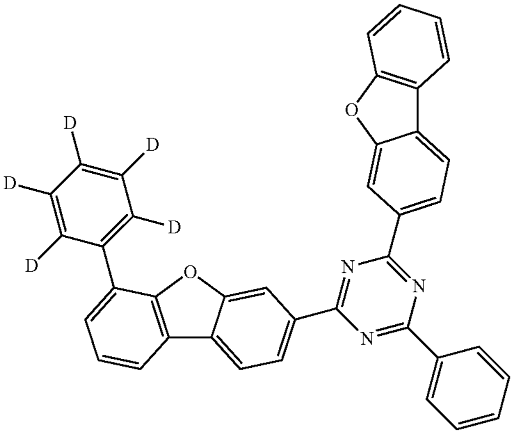
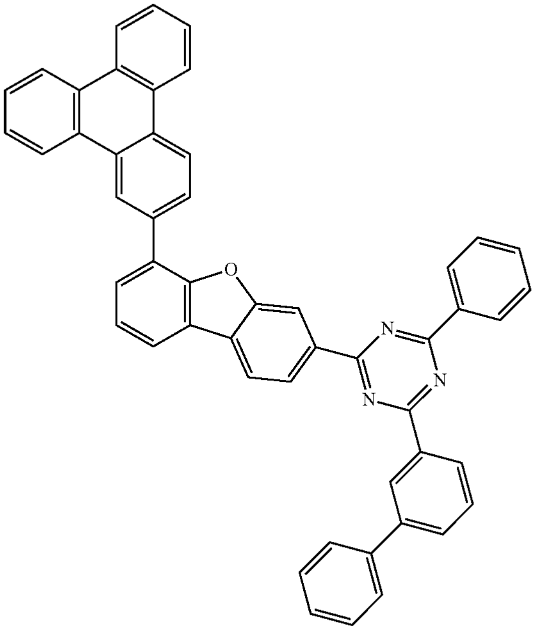
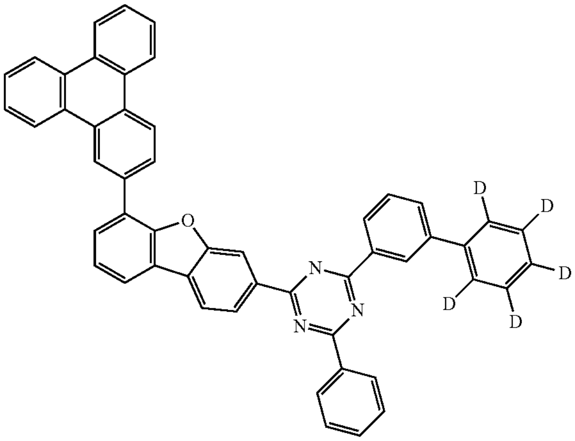

-continued
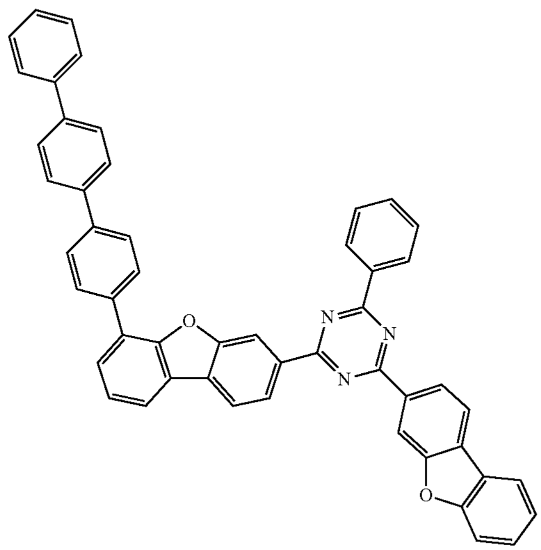
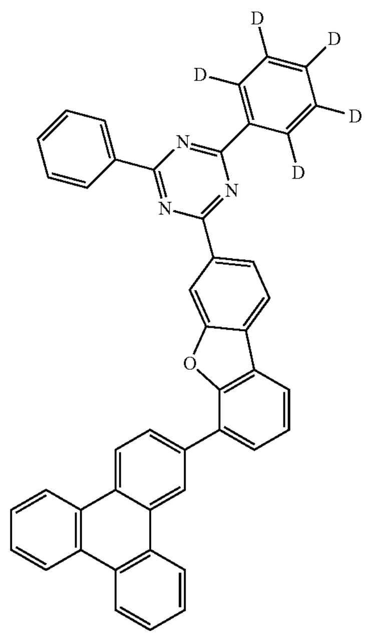
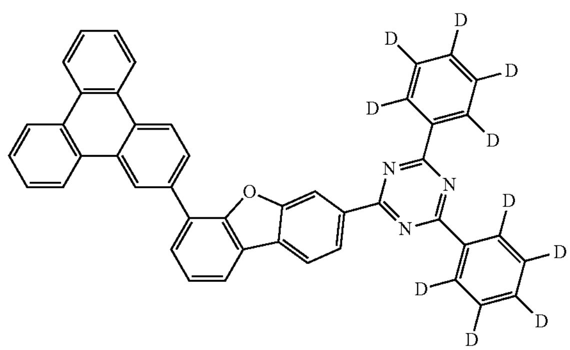
-continued
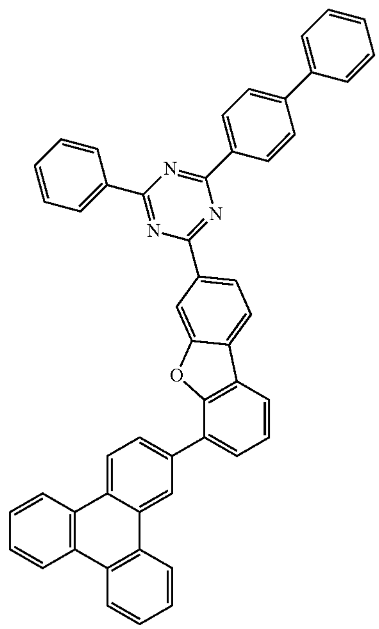
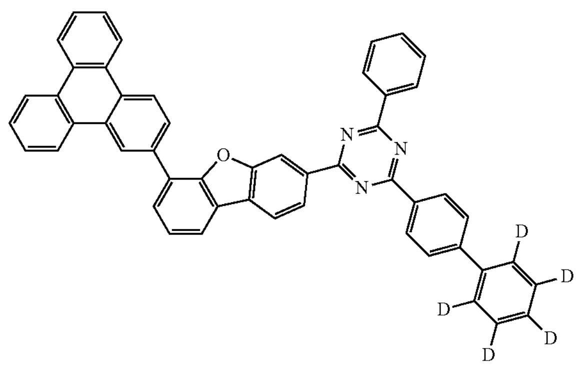
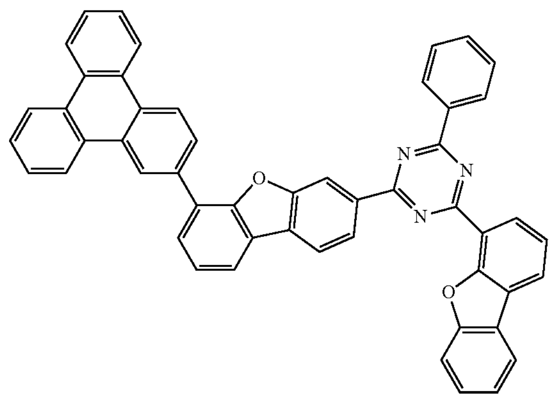
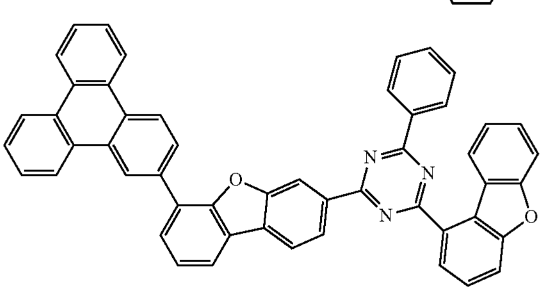

-continued
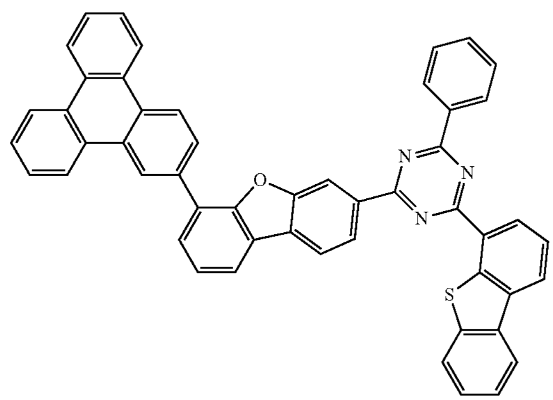
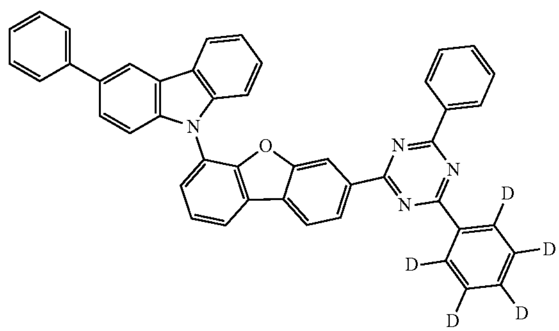
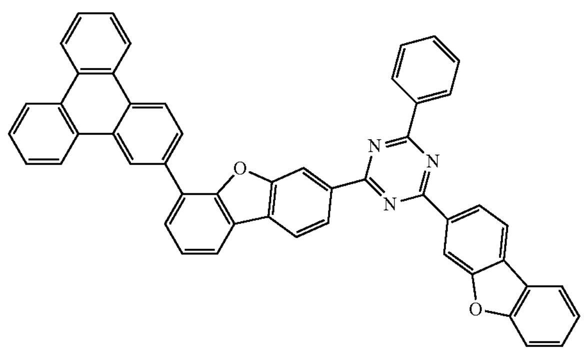
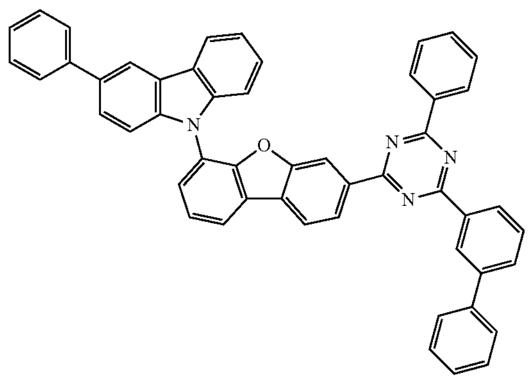
-continued
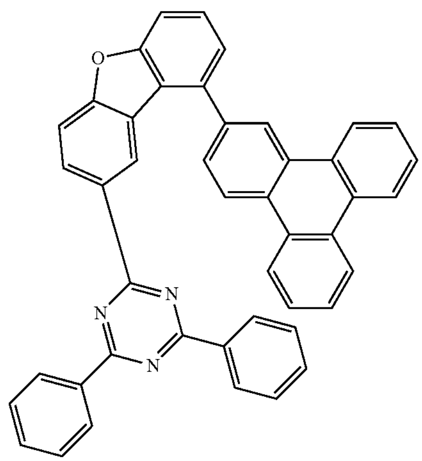
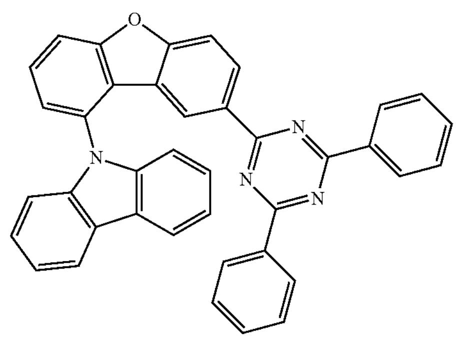
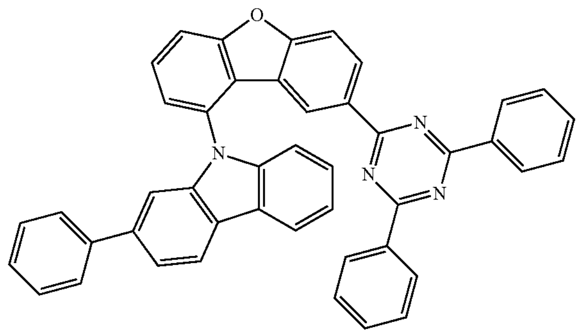
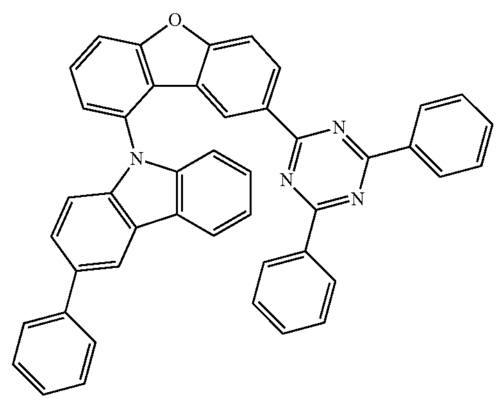

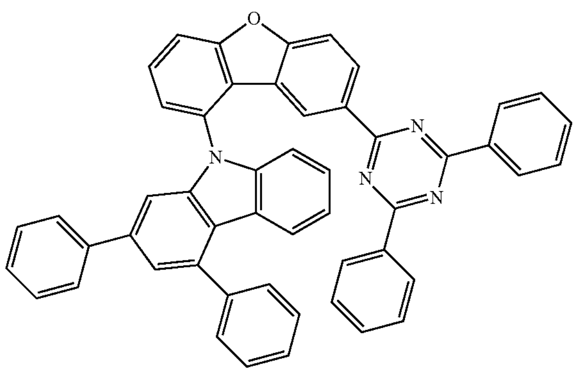
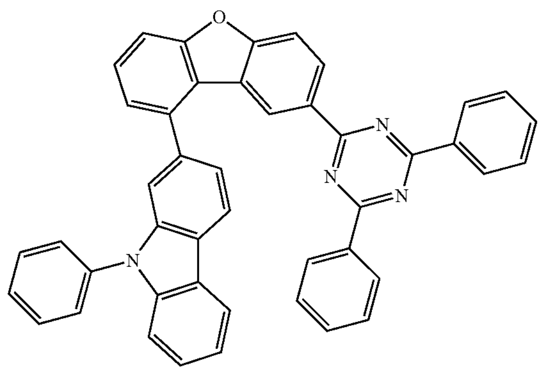
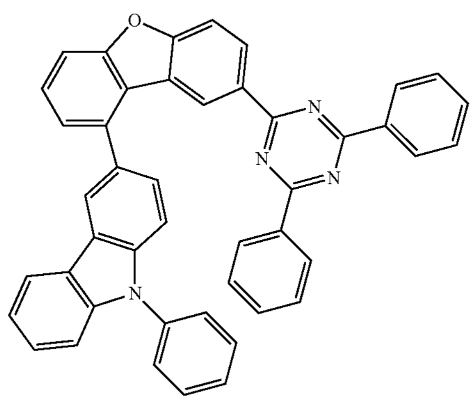
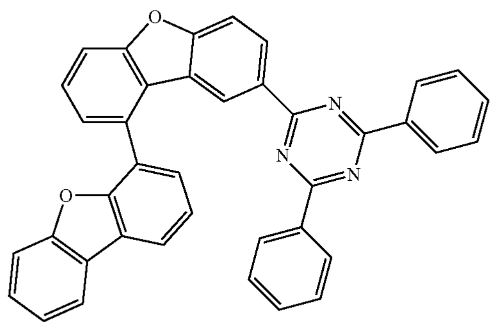
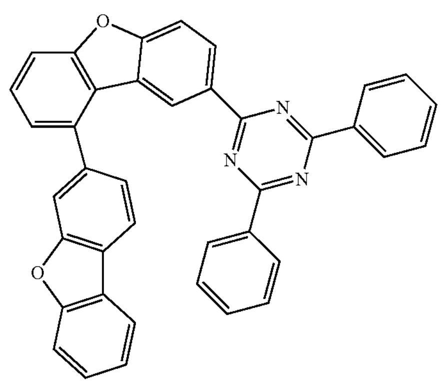
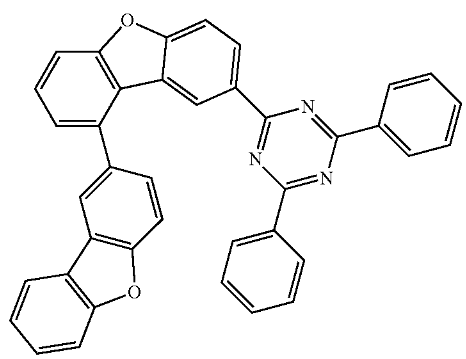
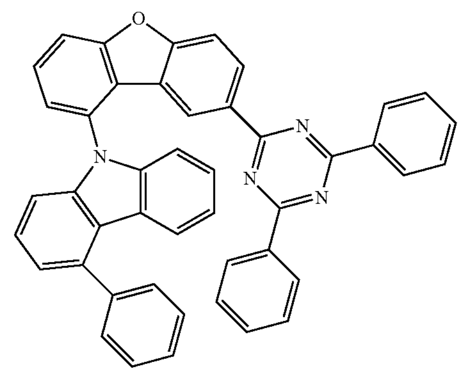
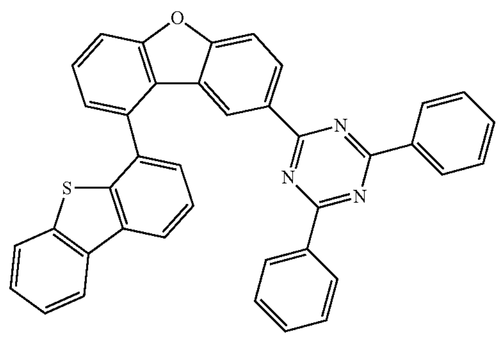

-continued
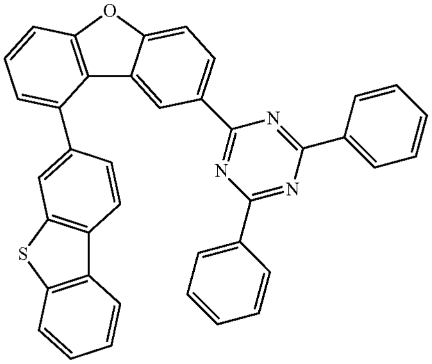
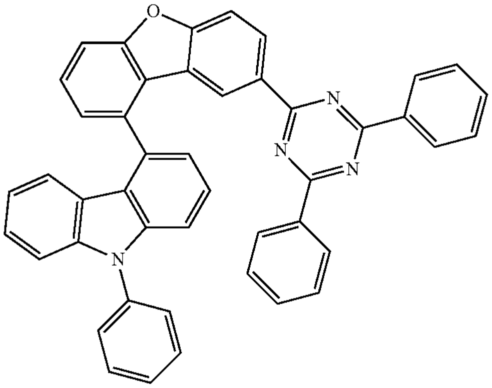
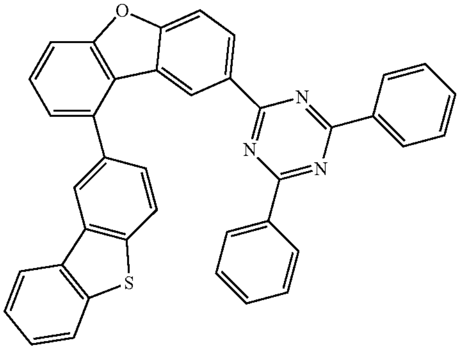
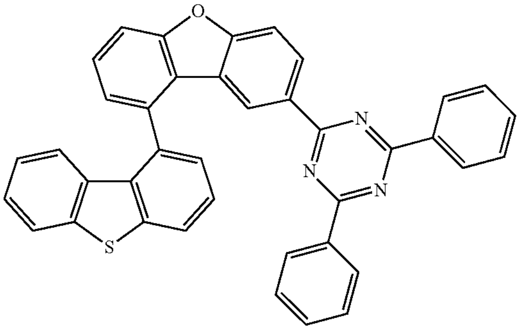
-continued
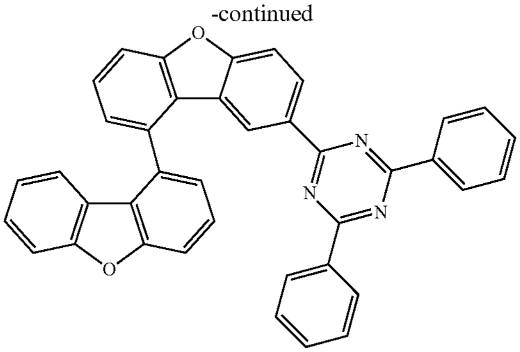
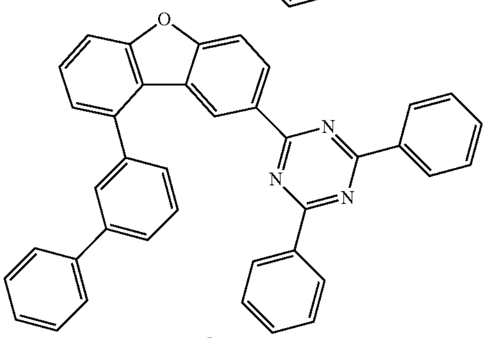
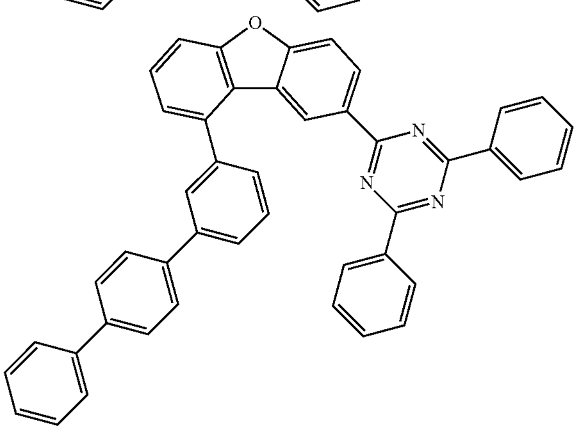
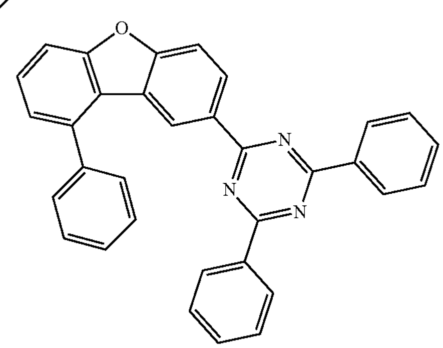
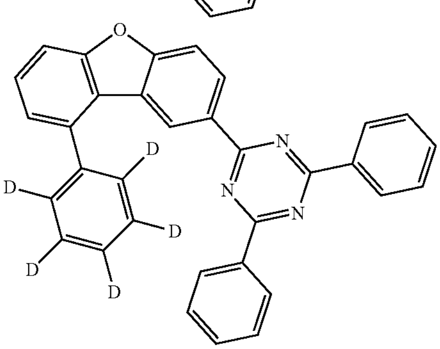

-continued
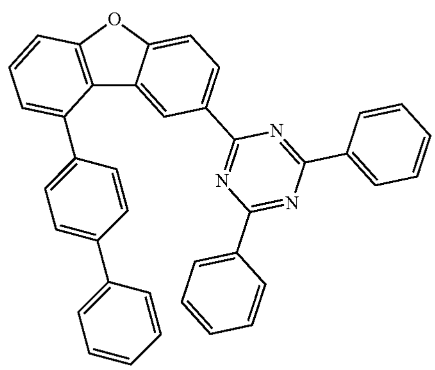
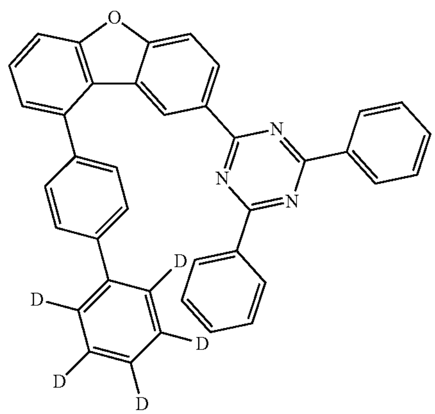
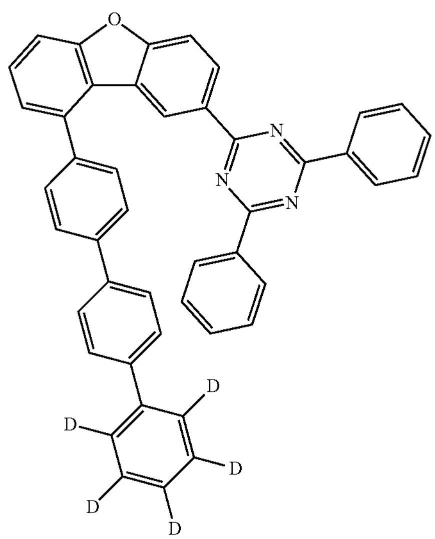
-continued
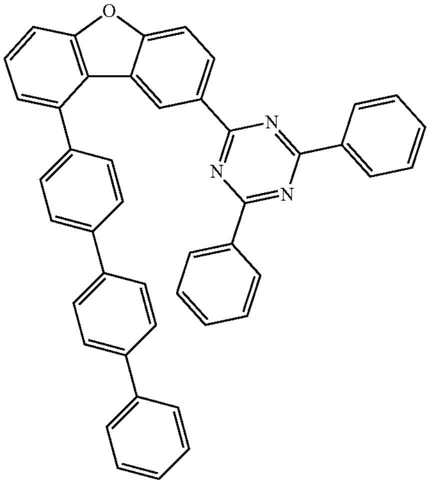
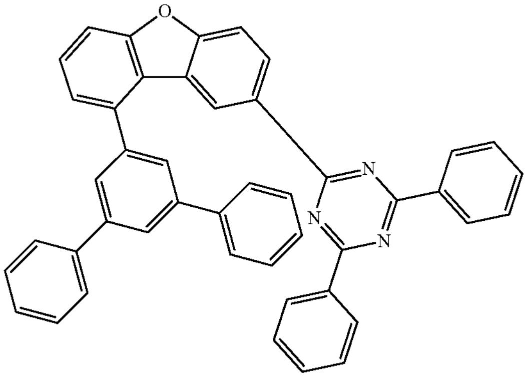
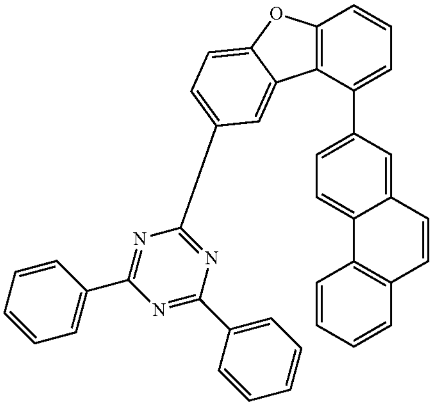
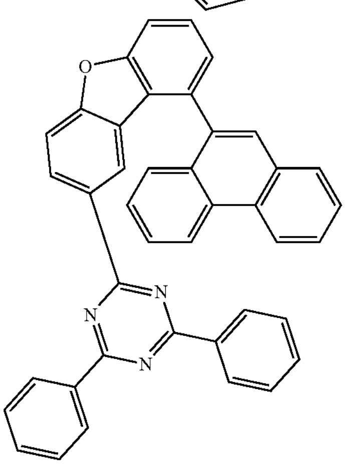

-continued
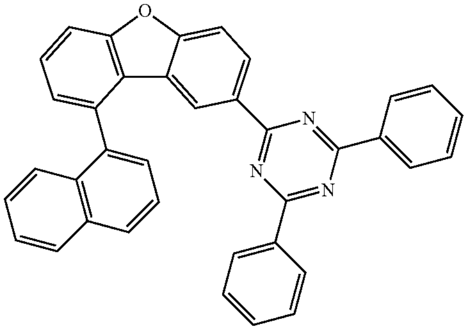
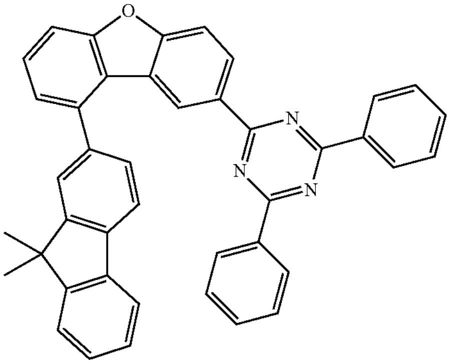
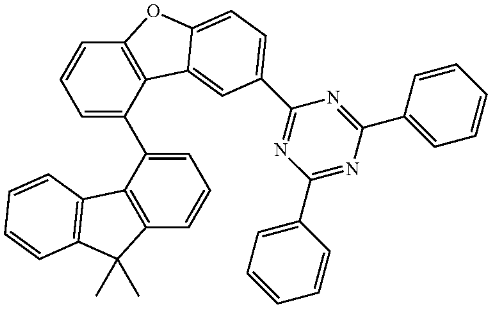
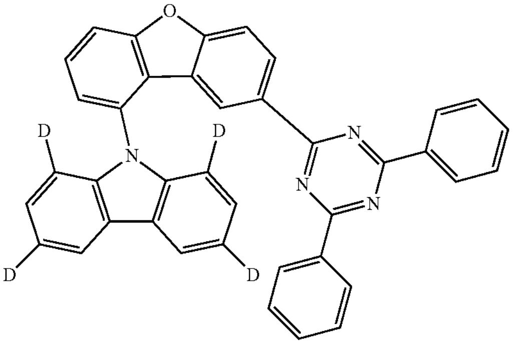
-continued
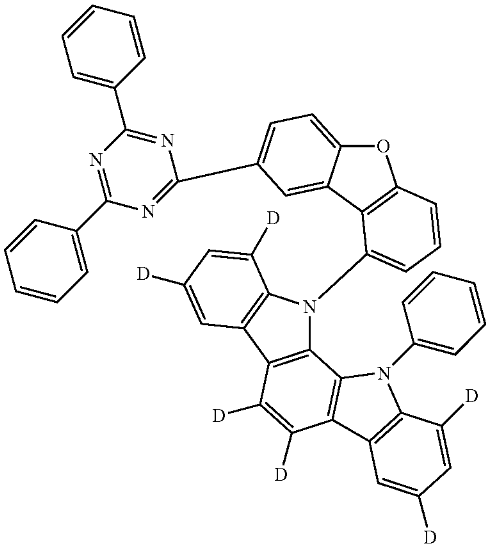
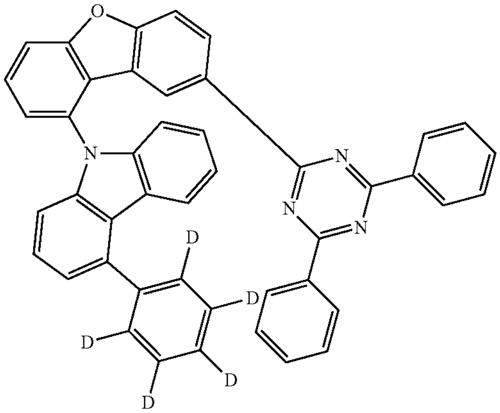
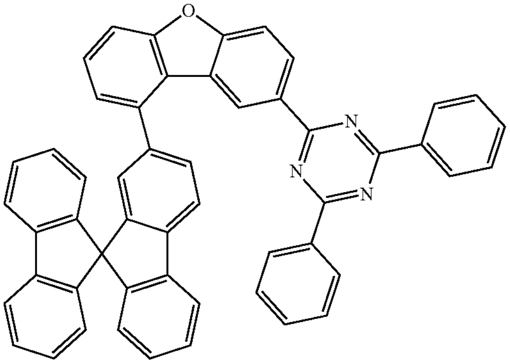
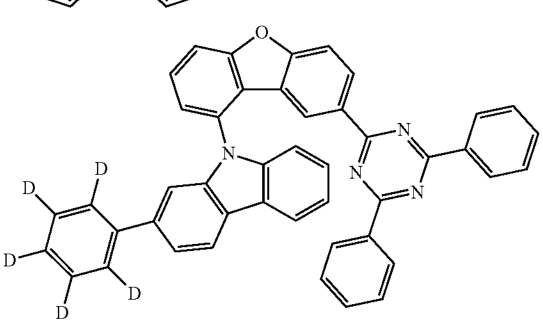

-continued
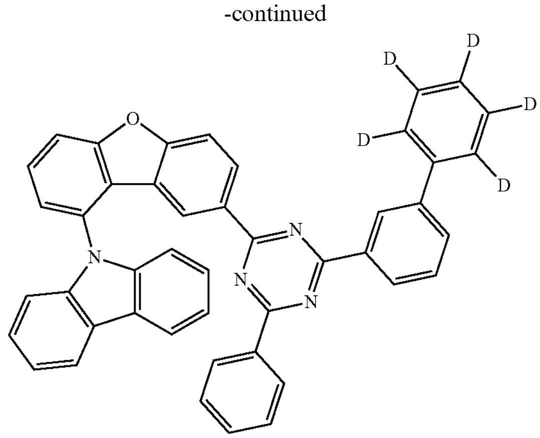
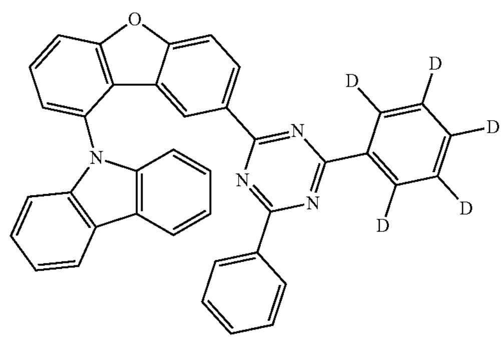
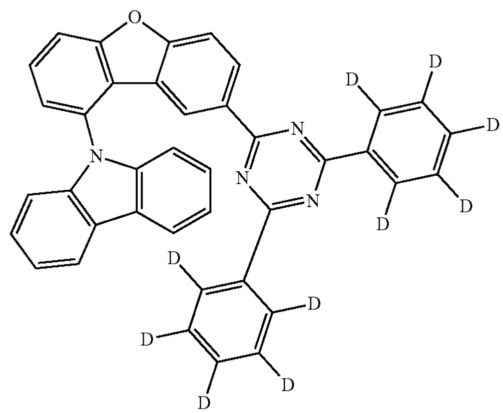
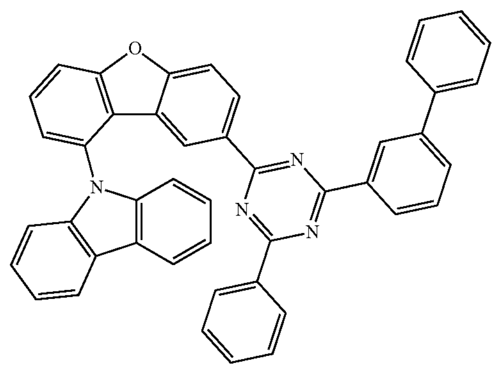
-continued
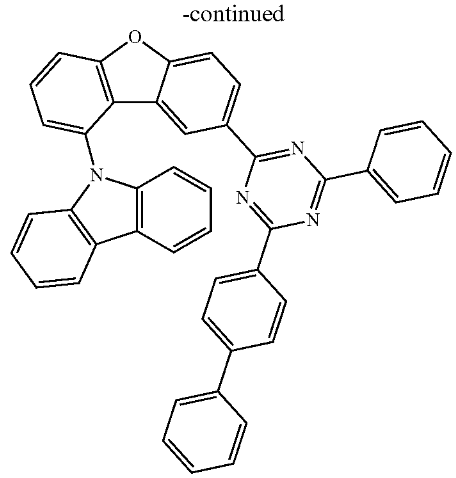
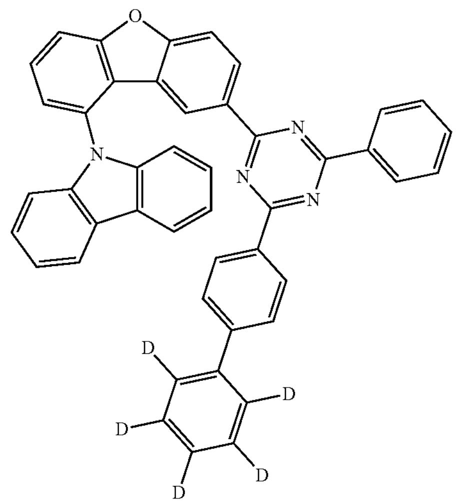
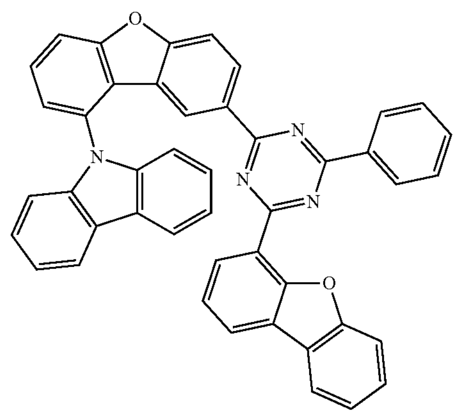
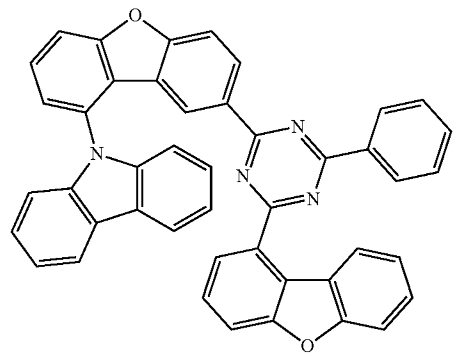

-continued
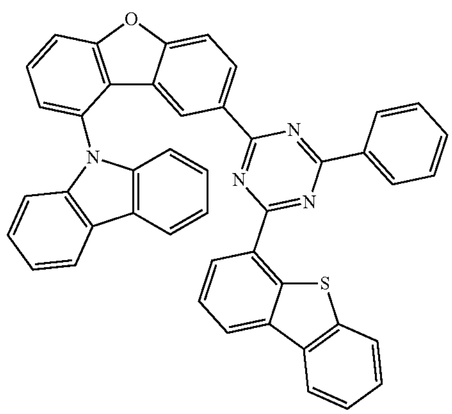
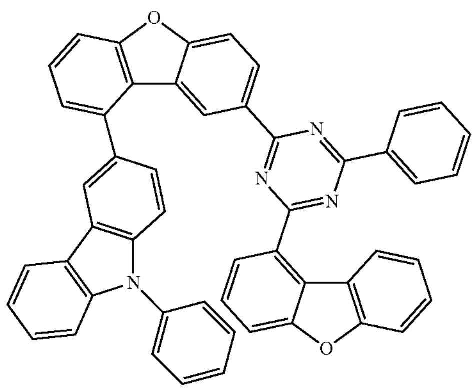
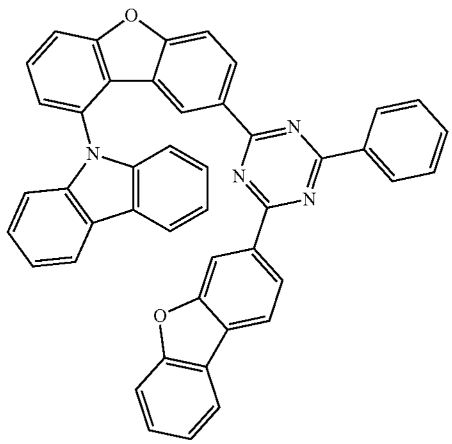
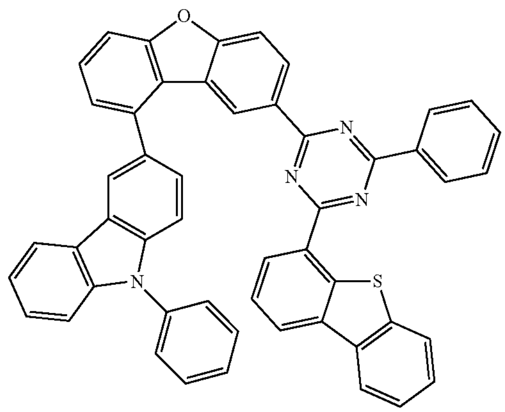
-continued
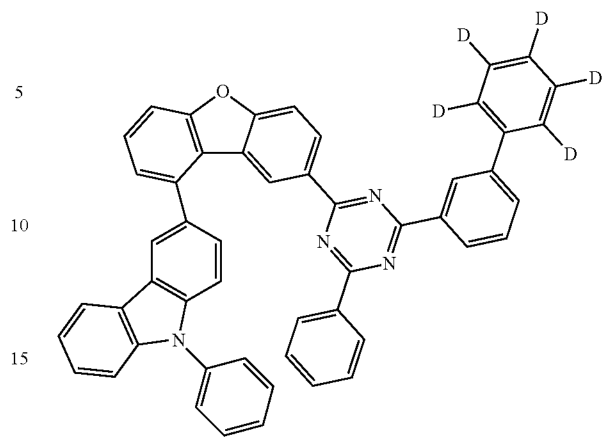
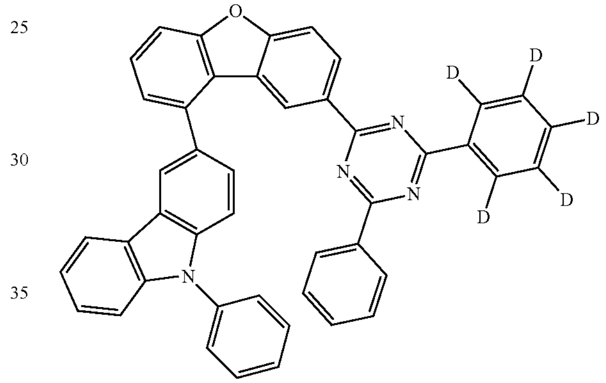
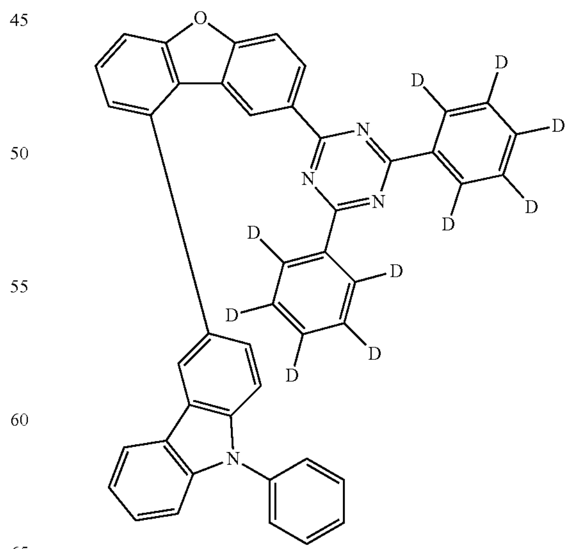

-continued
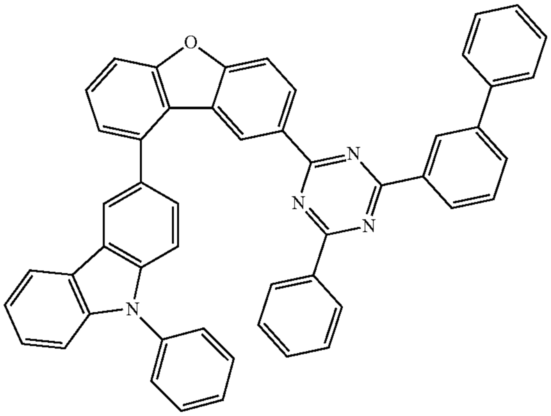
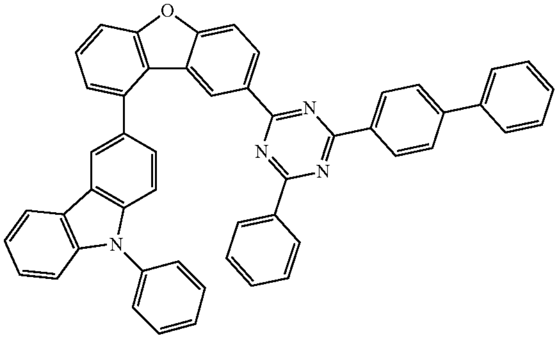
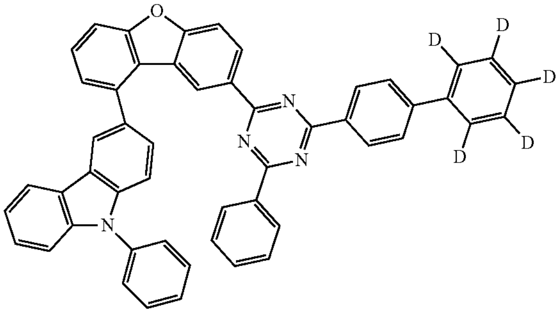
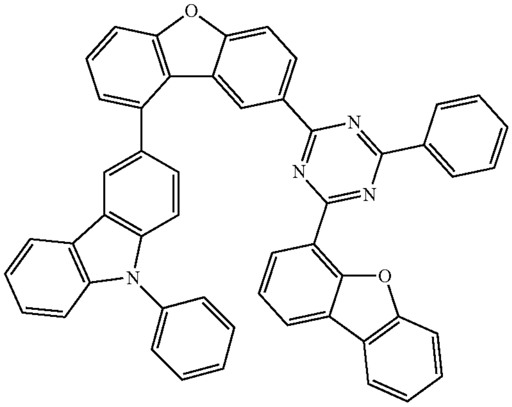
-continued
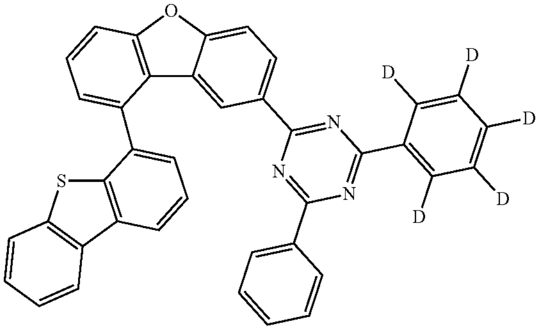
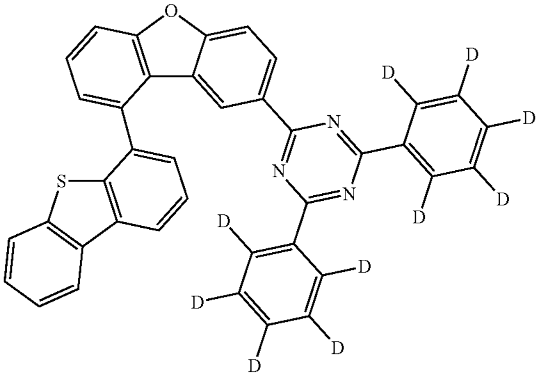
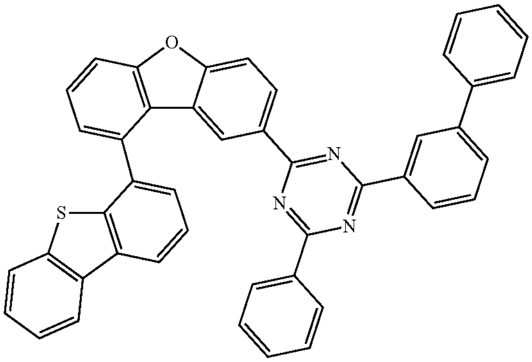
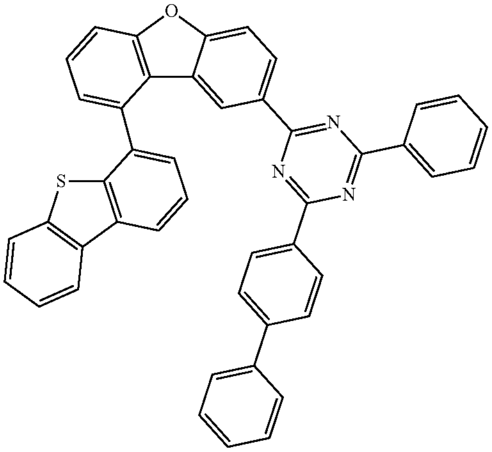

-continued
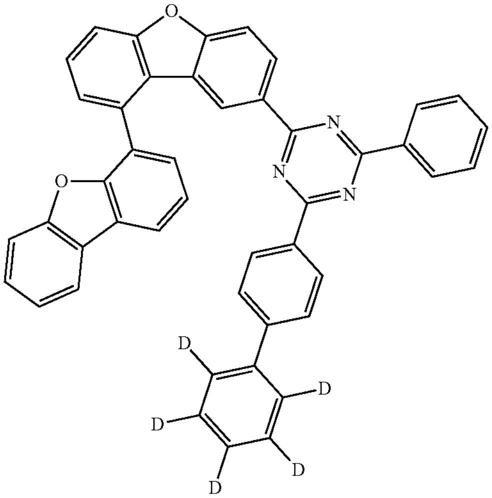
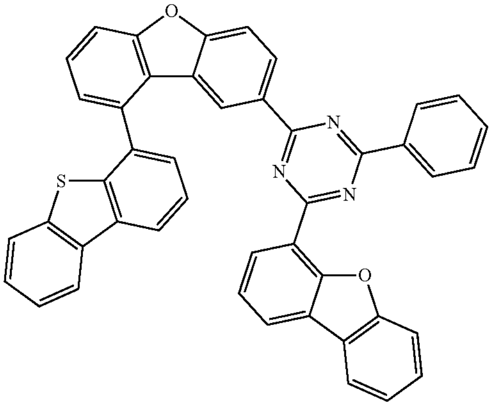
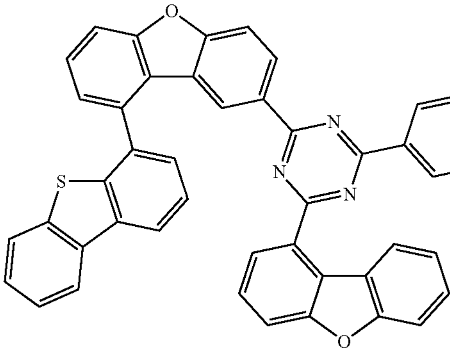
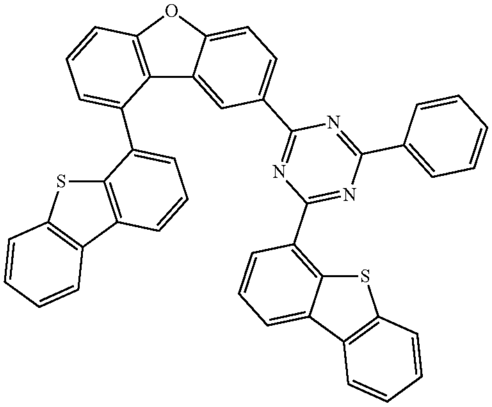
-continued
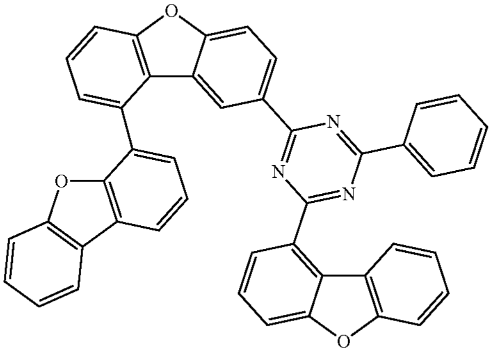
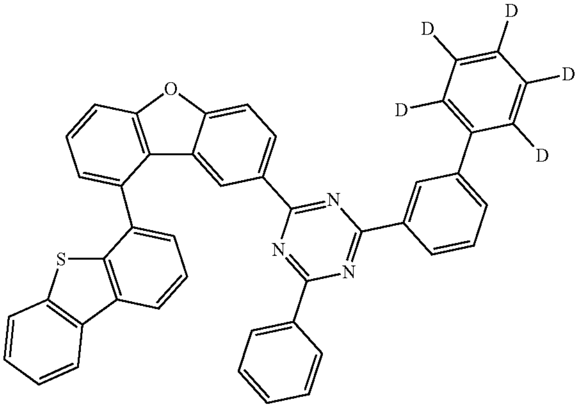
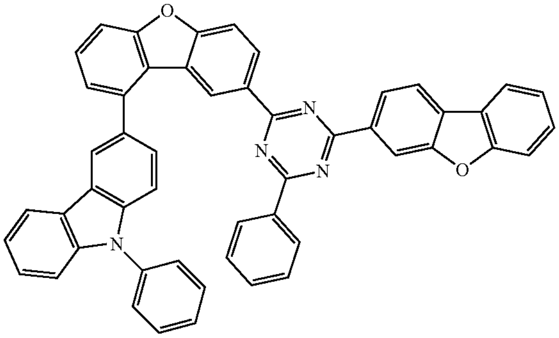
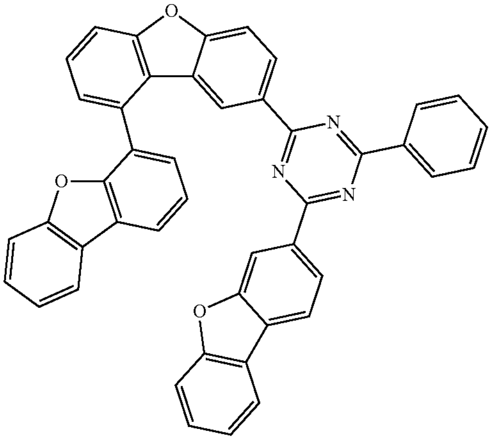

-continued
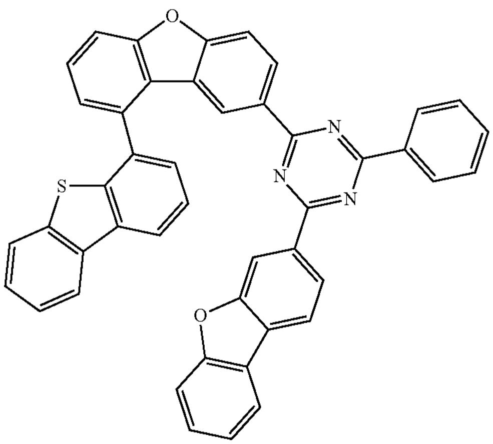
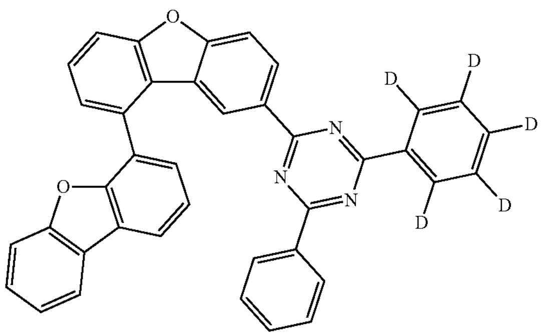
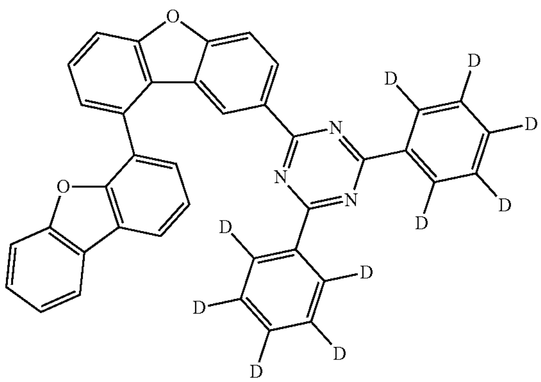
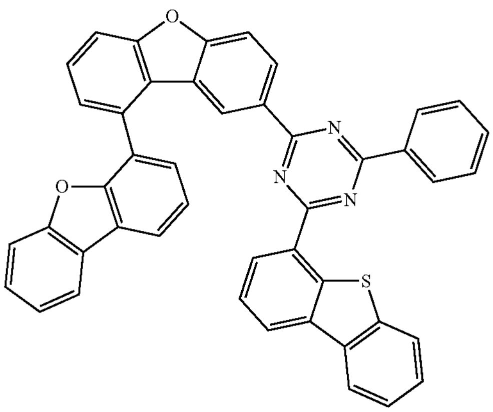
-continued
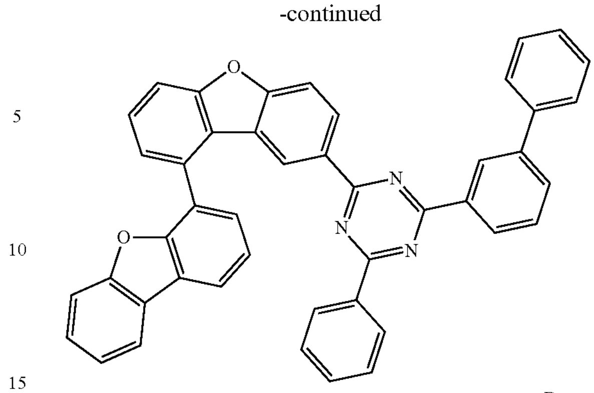
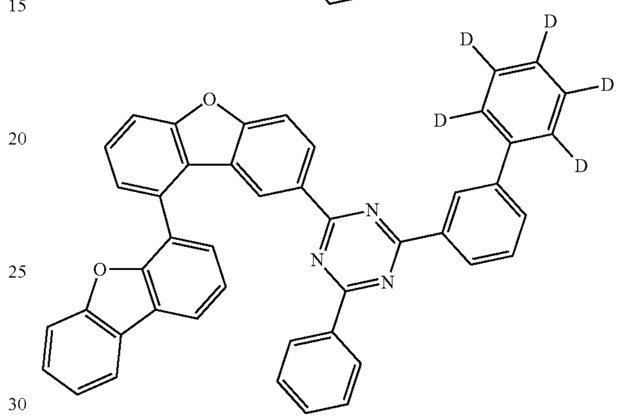
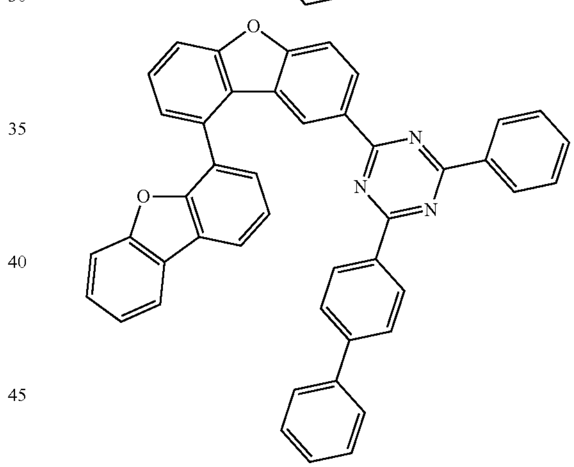
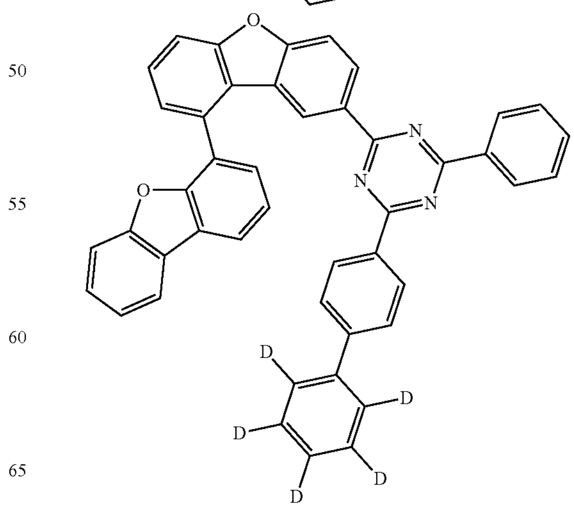

-continued
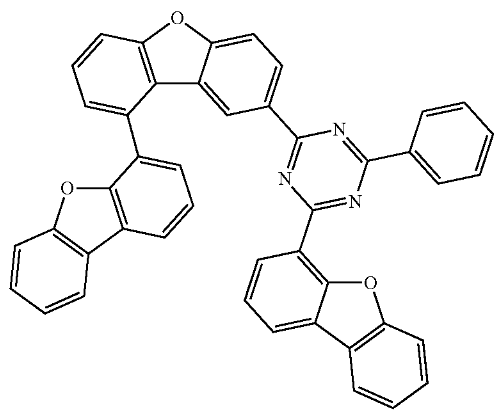
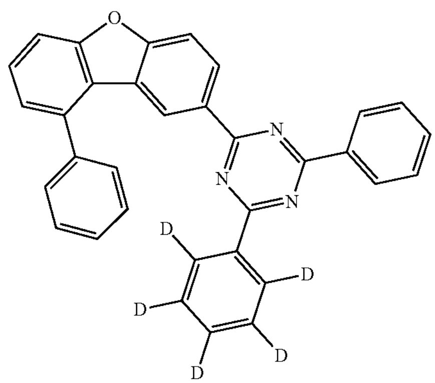
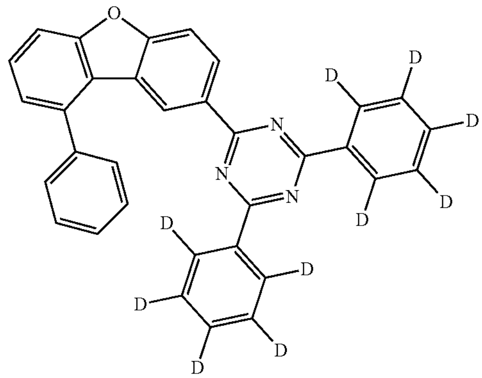
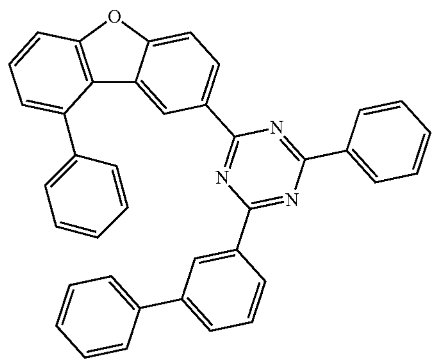
-continued
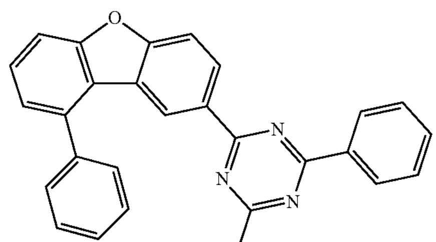
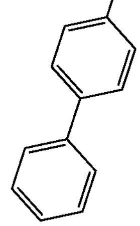
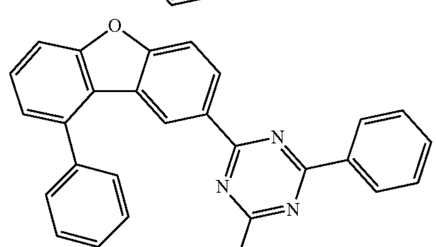
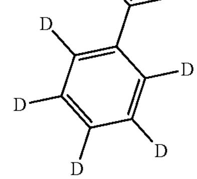
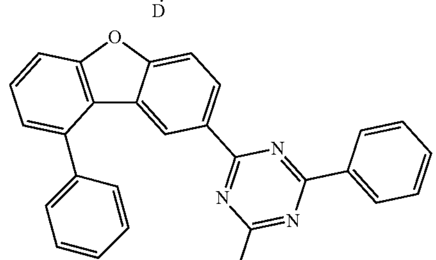
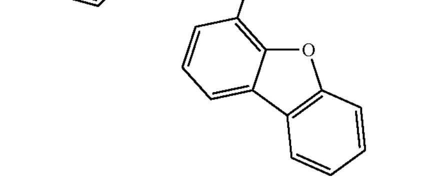
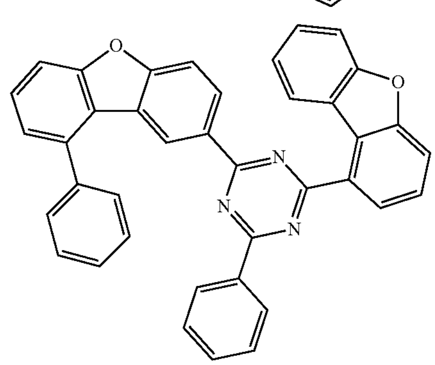

-continued
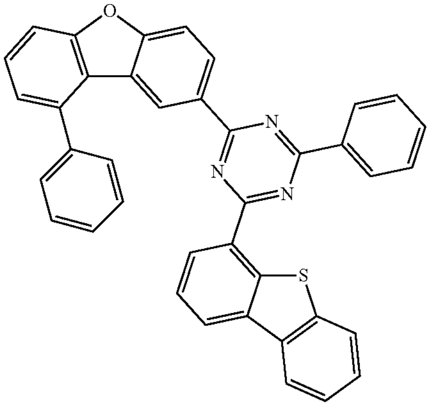
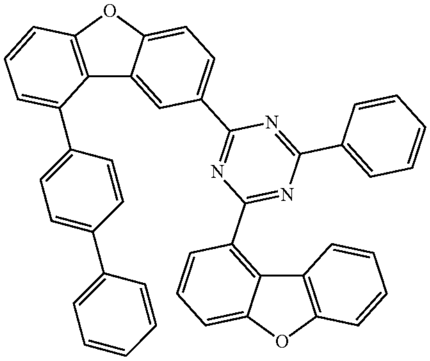
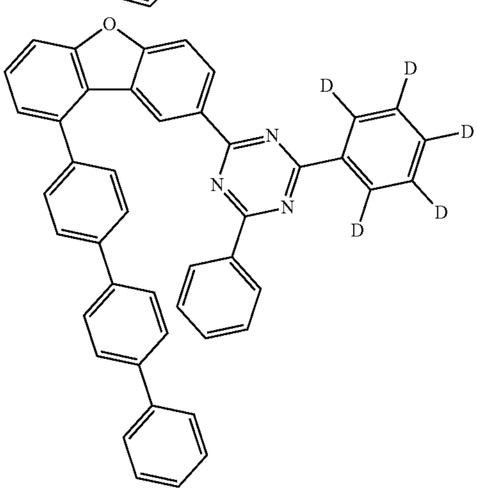
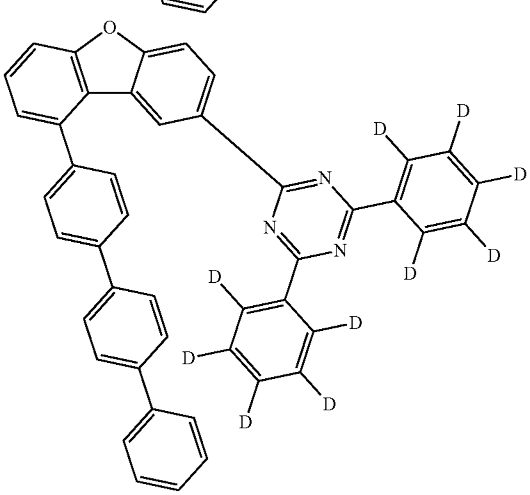
-continued
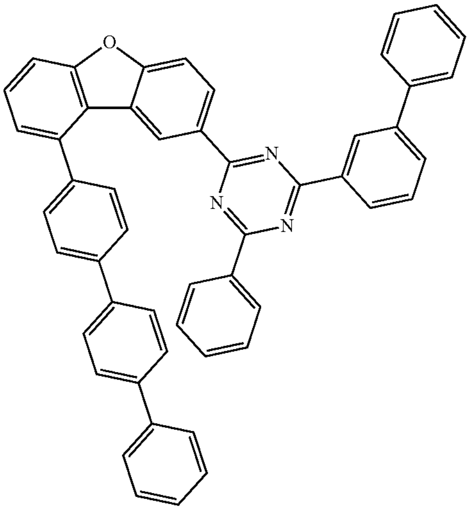
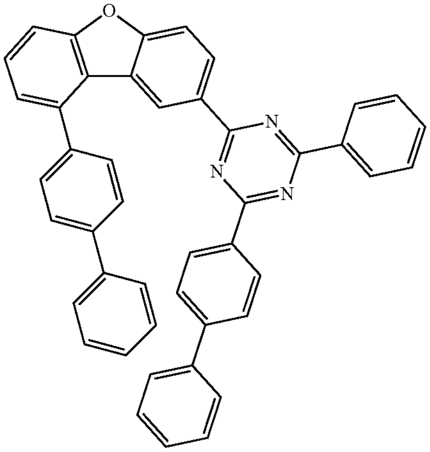
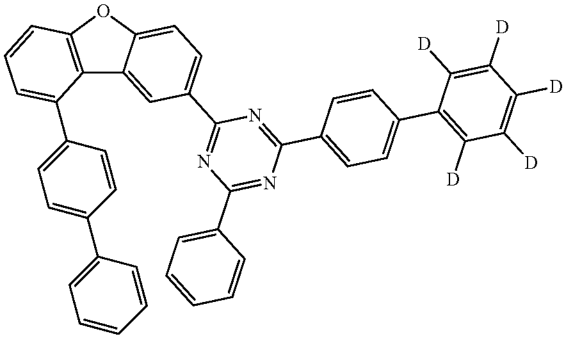
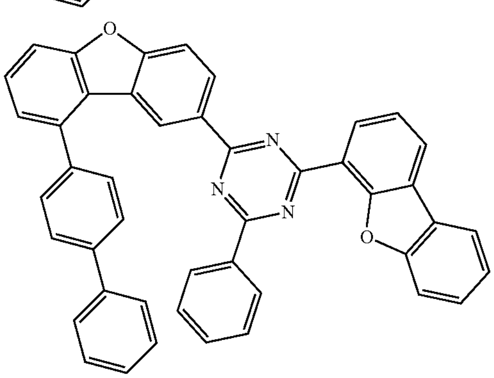

-continued
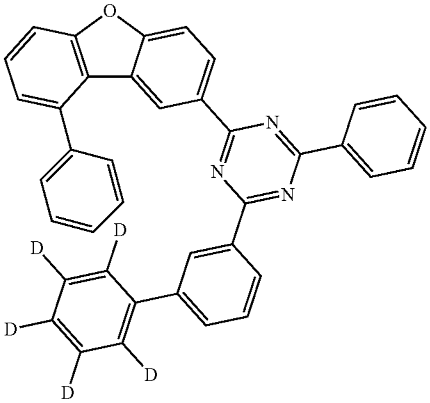
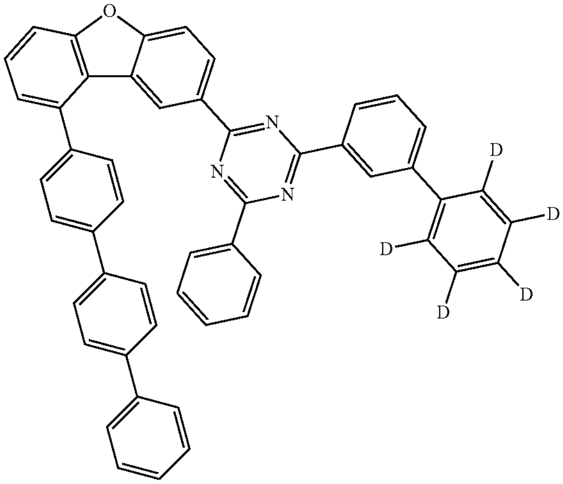
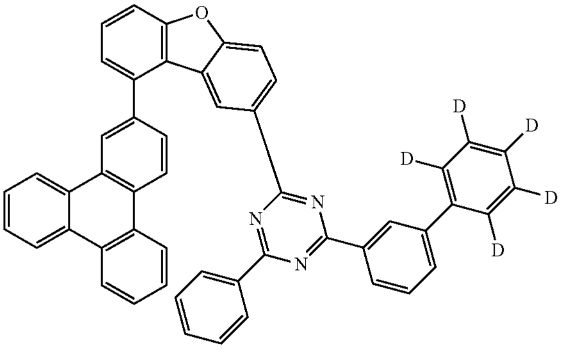
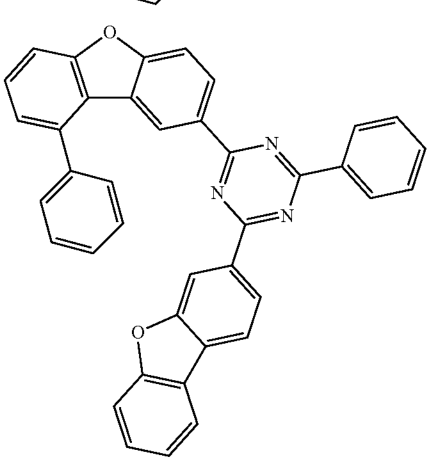
-continued
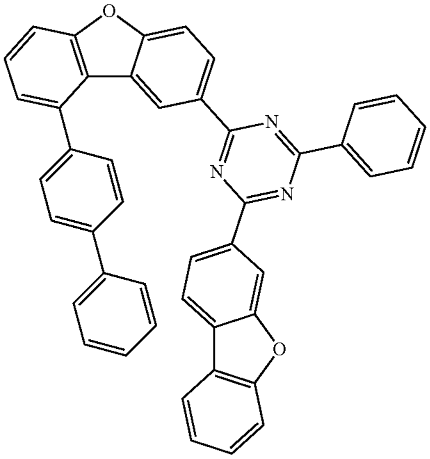
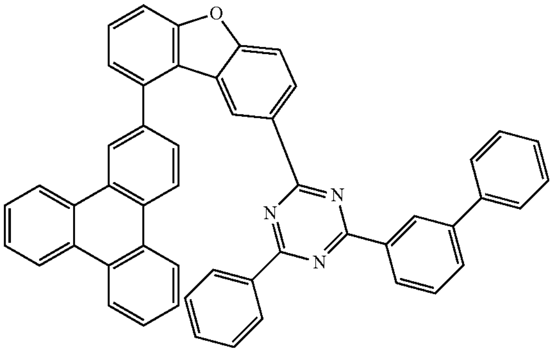
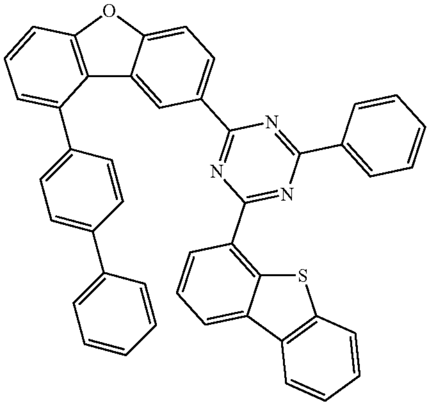
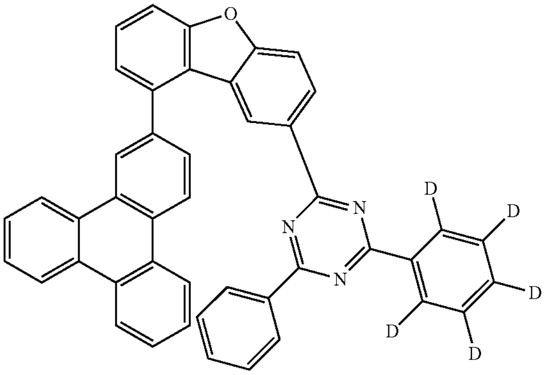

-continued
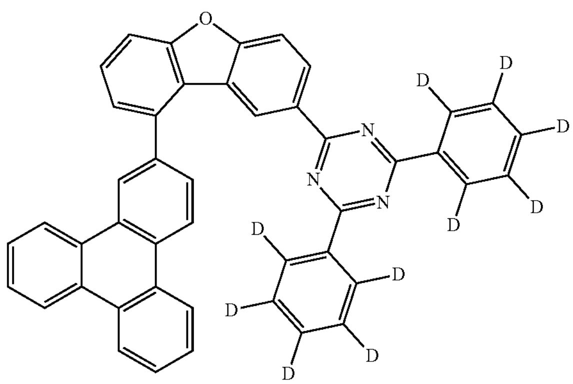
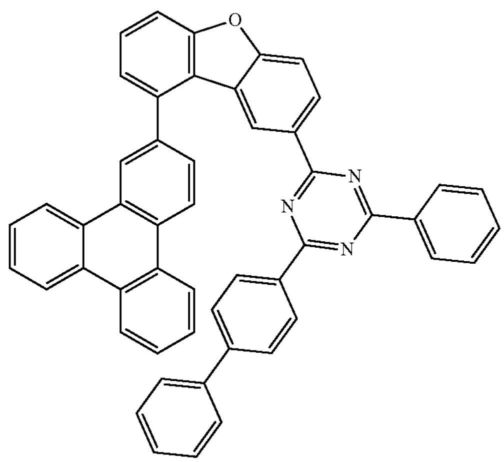
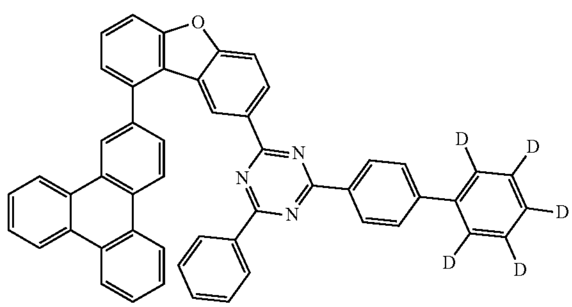
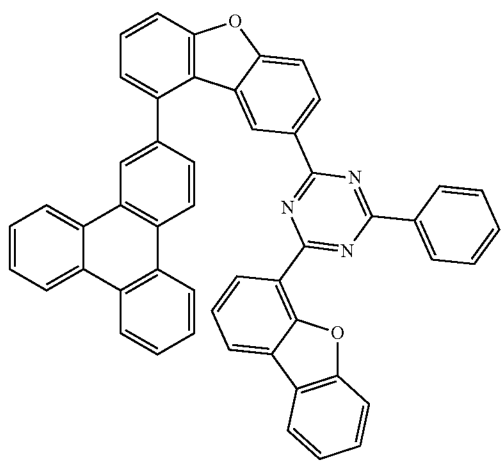
-continued
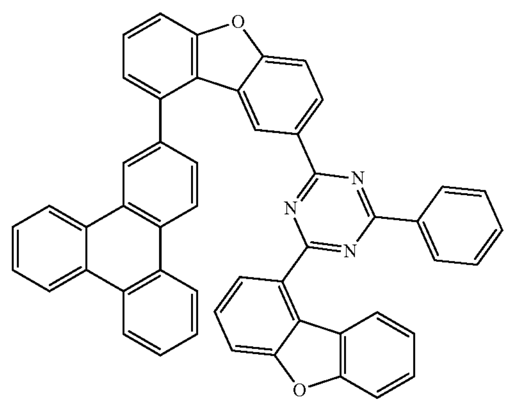
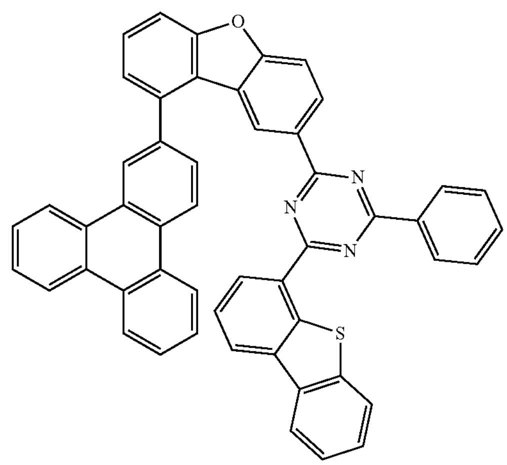
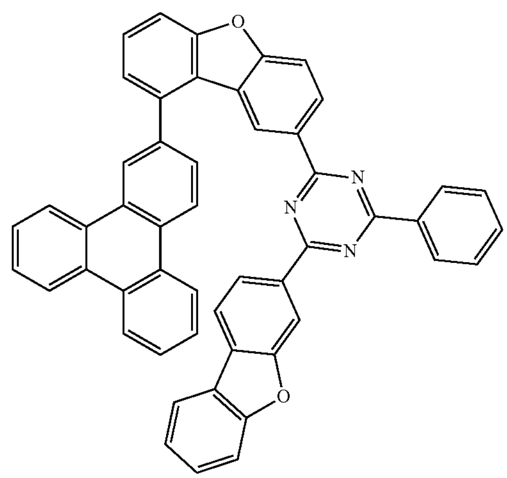
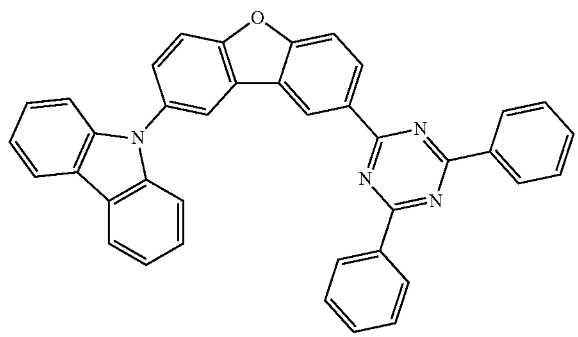

-continued
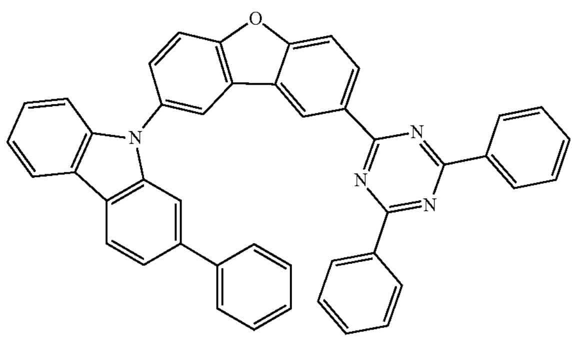
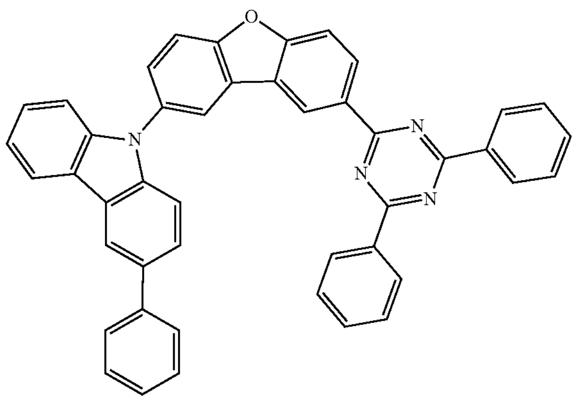
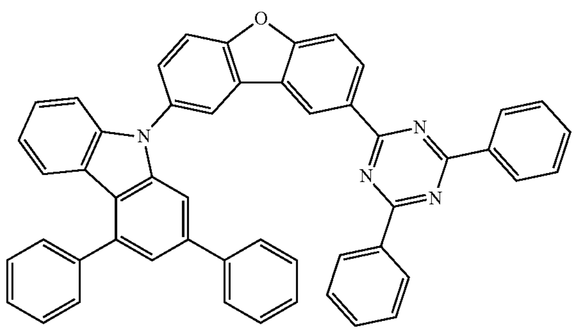
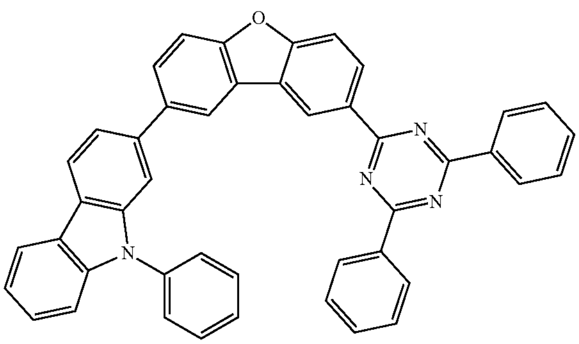
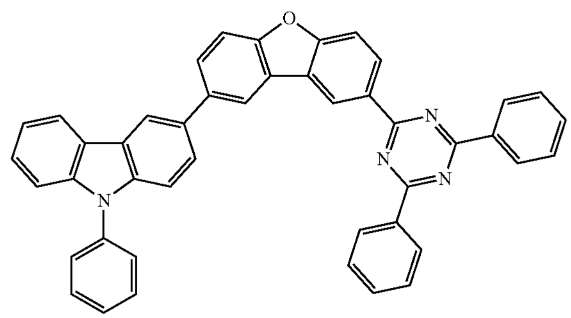
-continued
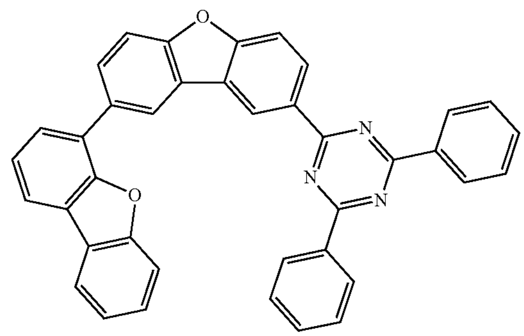
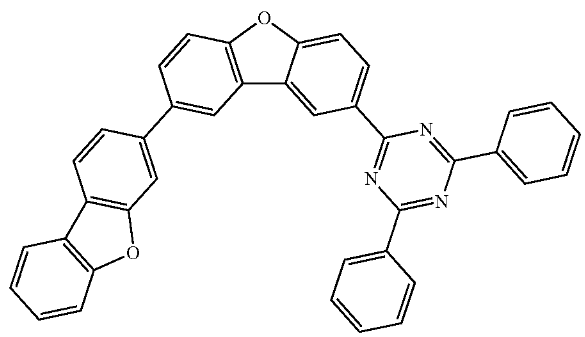
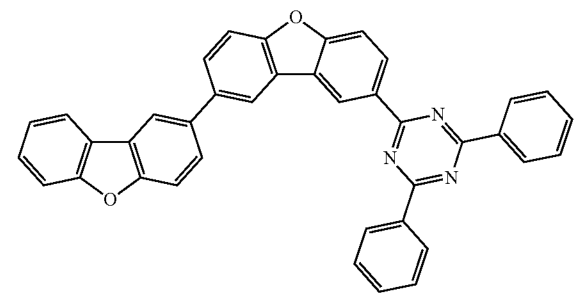
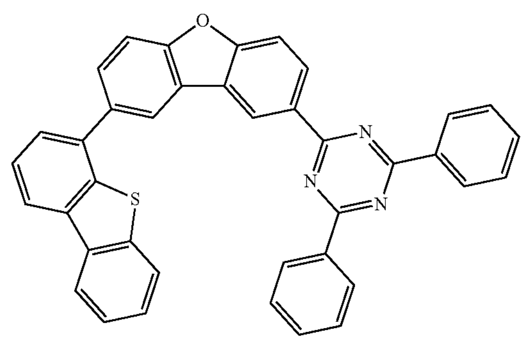
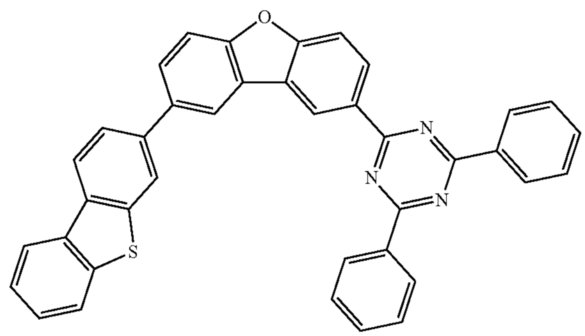

-continued
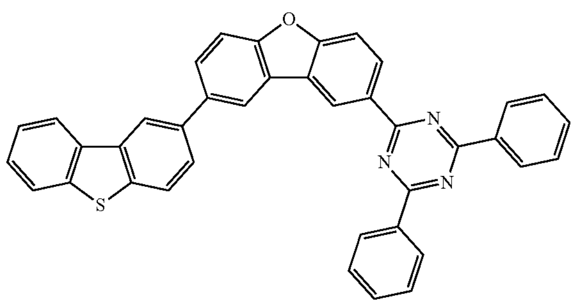
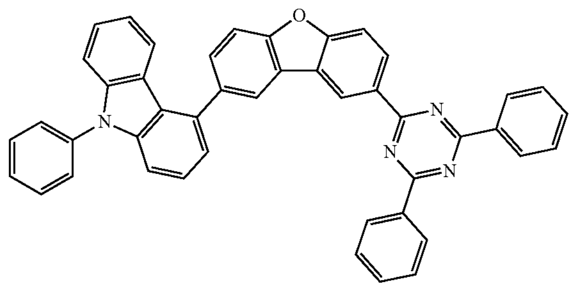
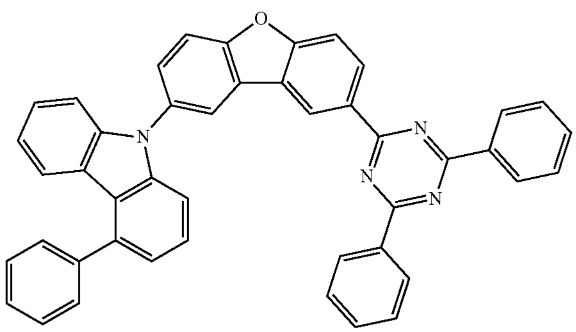
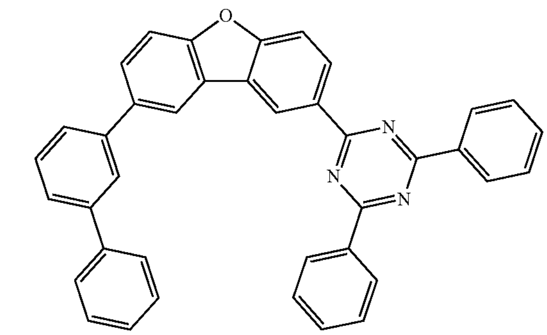
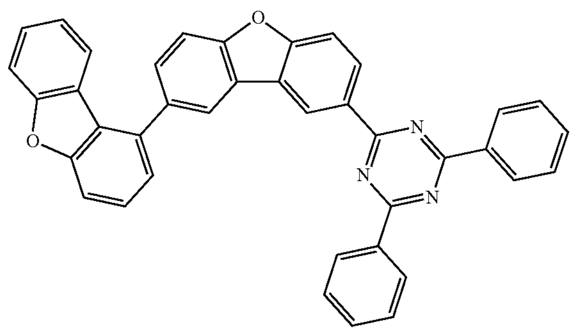
-continued
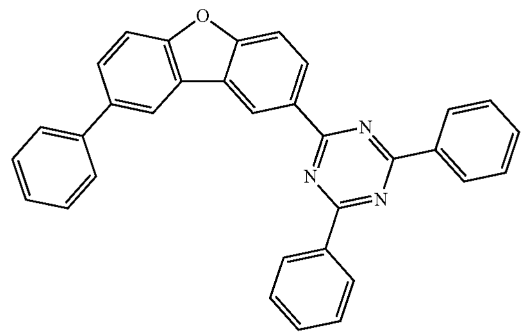
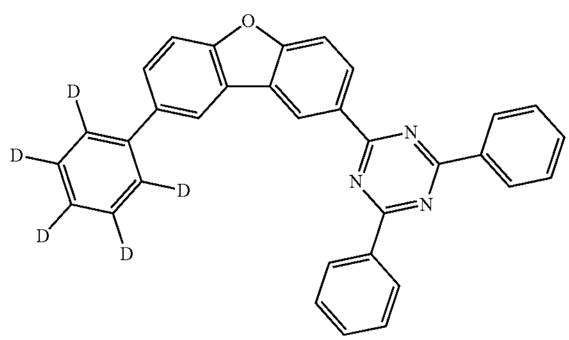
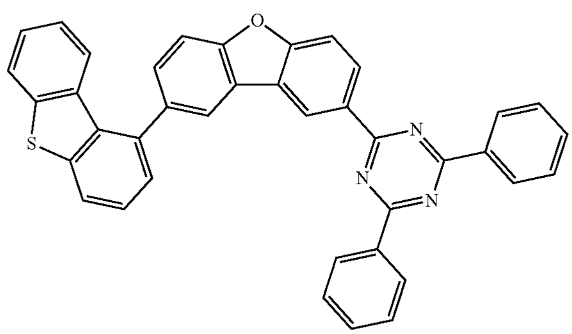
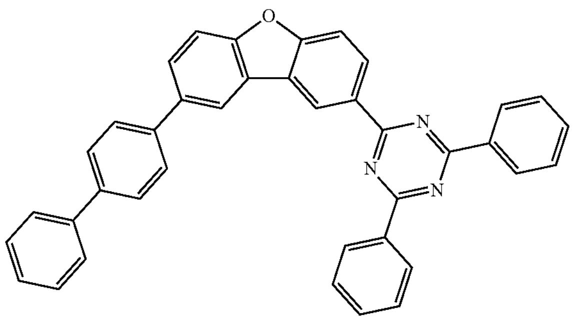

-continued
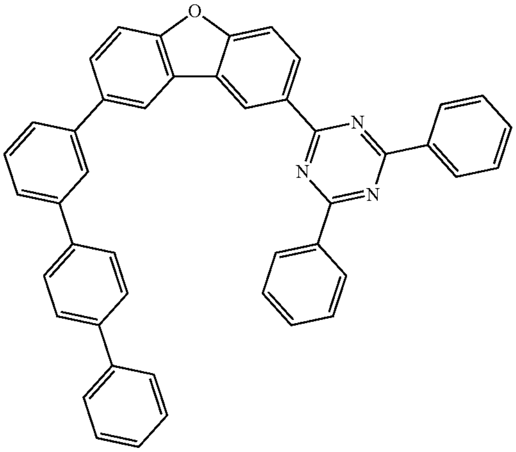
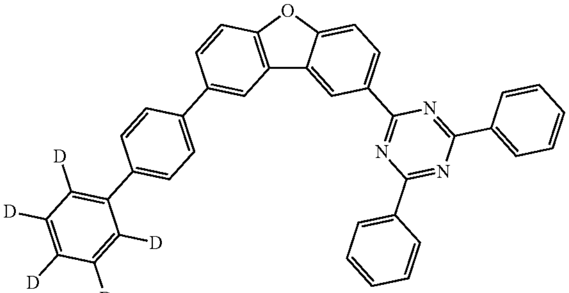
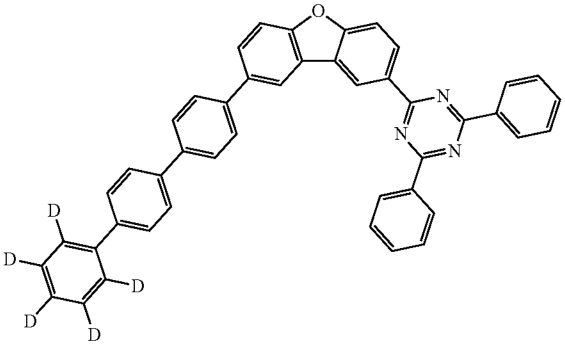
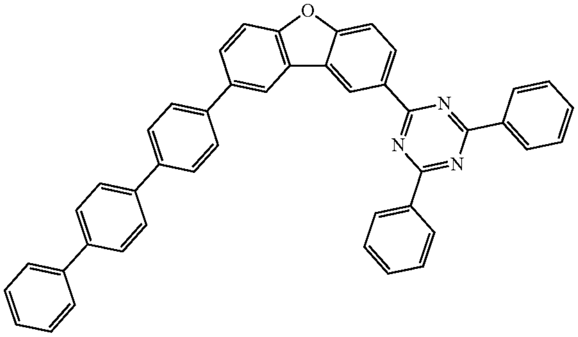
-continued
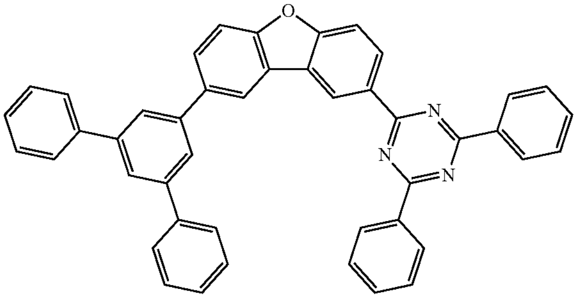
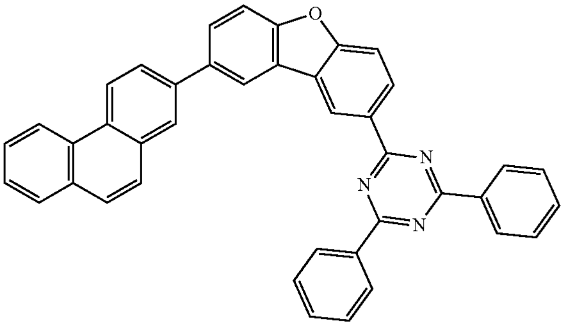
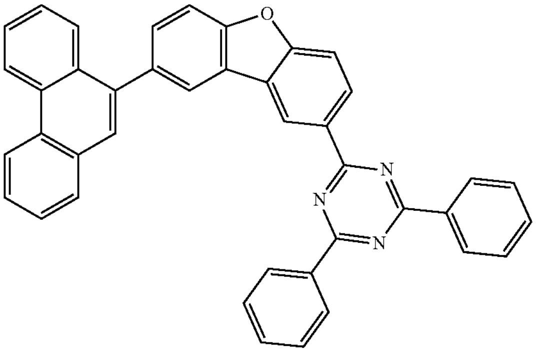
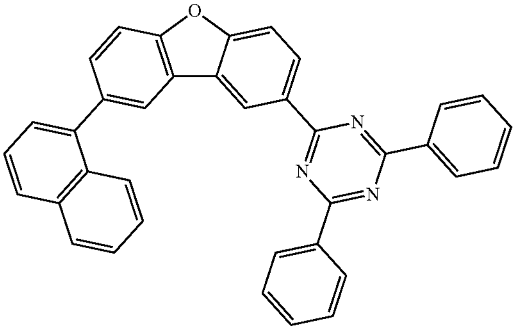
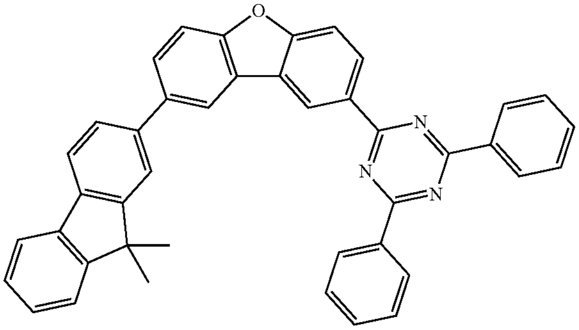

-continued
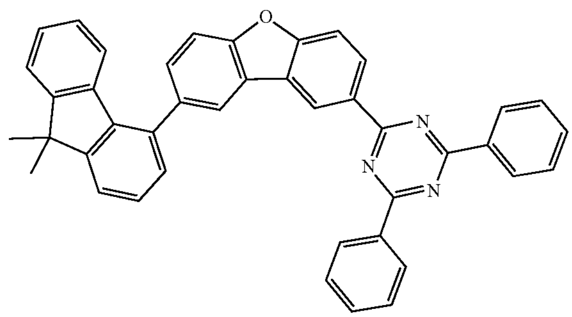
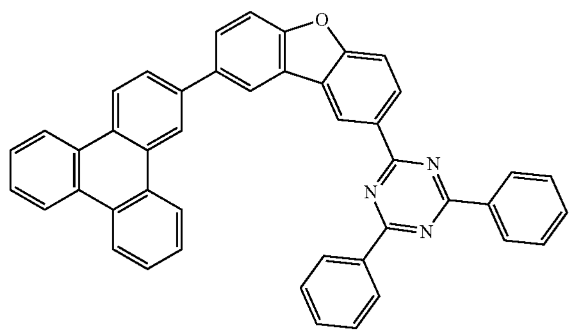
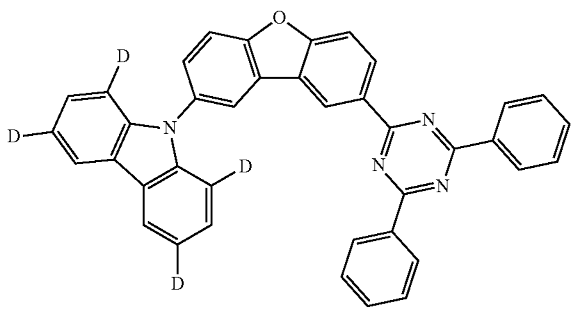
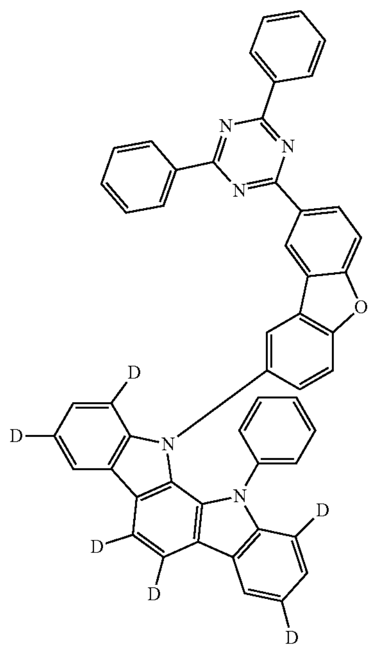
-continued
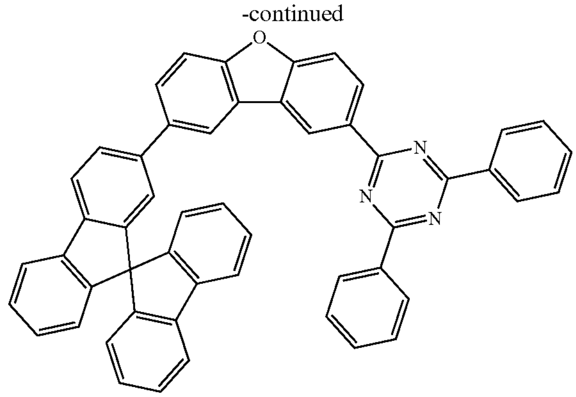
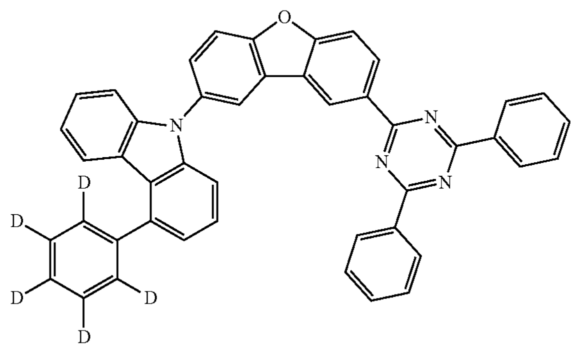
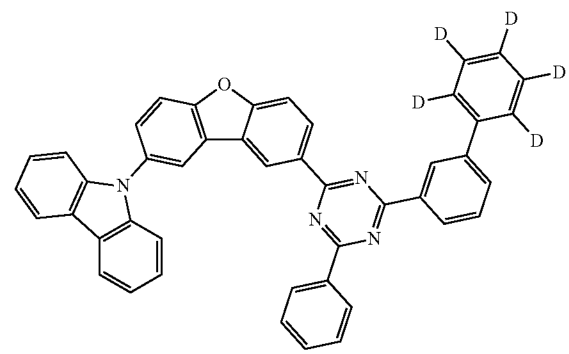
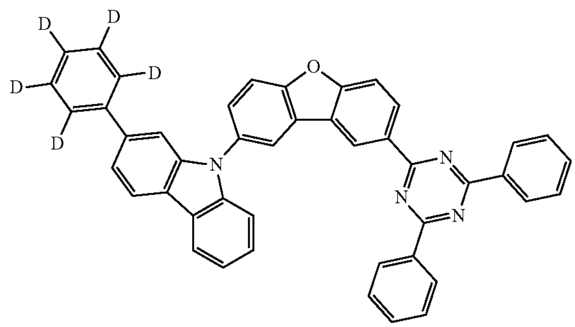
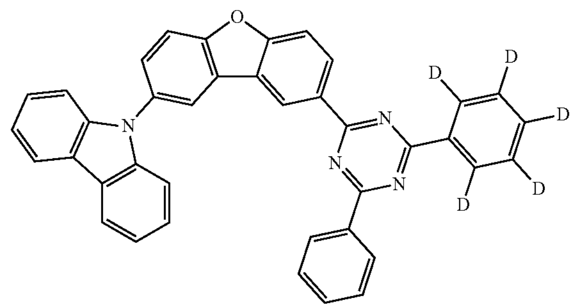

-continued
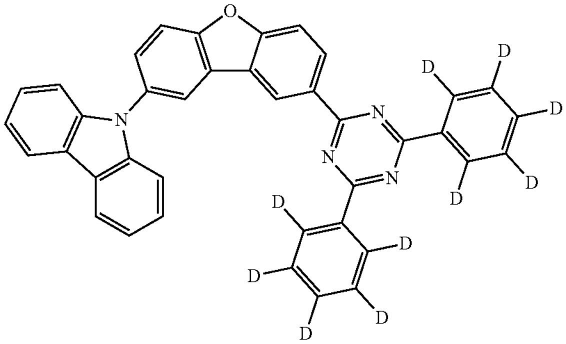
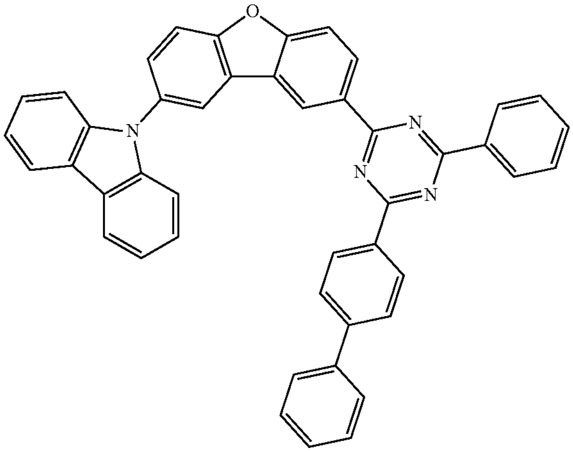
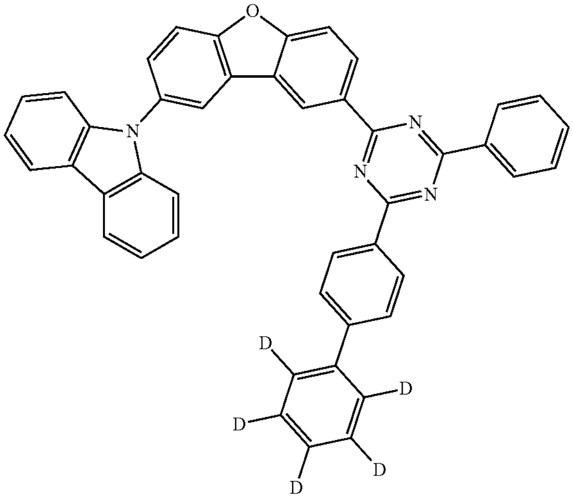
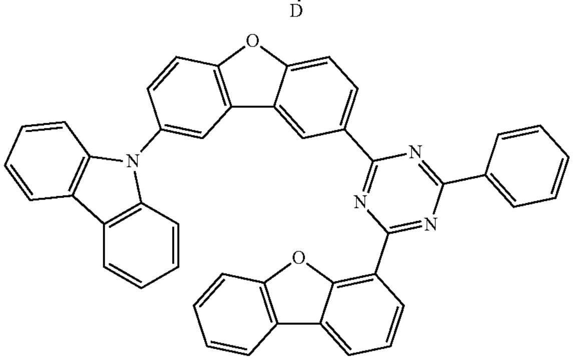
-continued
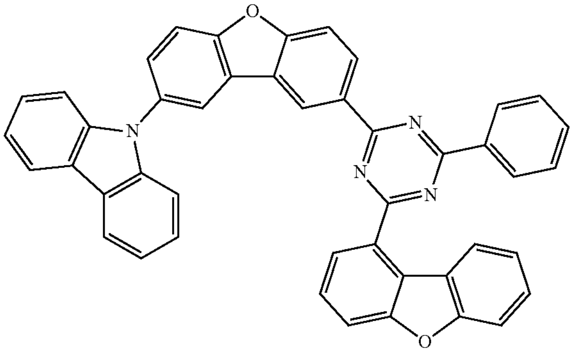
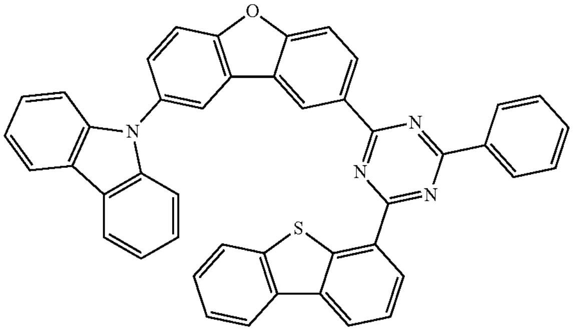
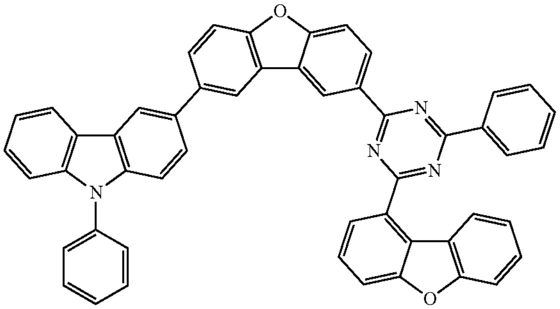
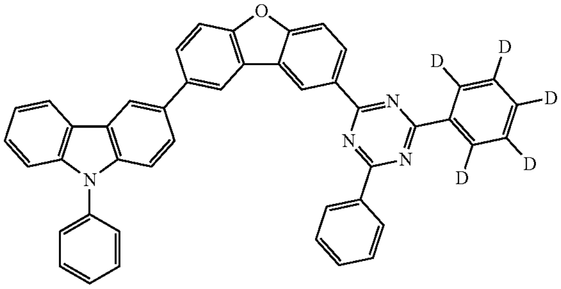
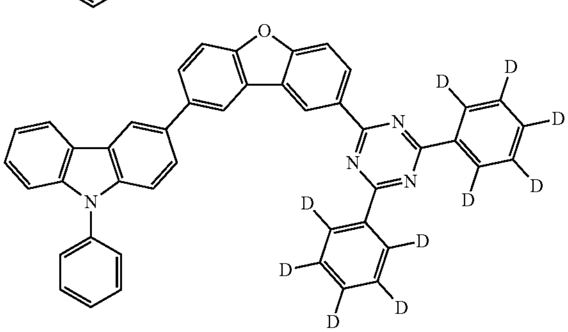

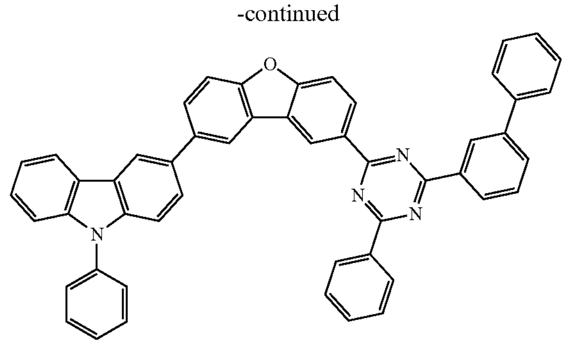
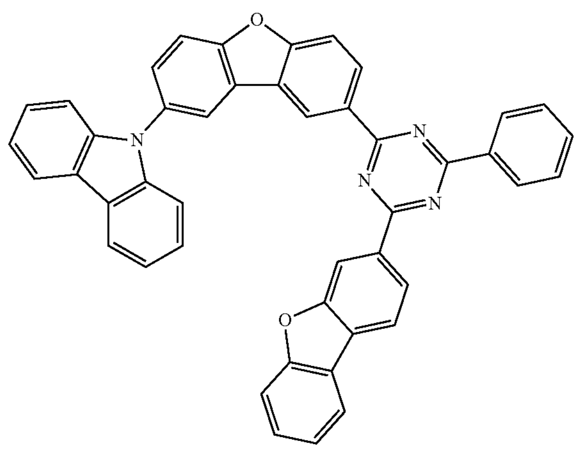
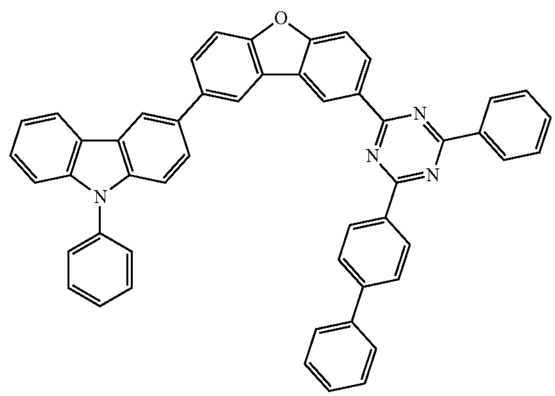
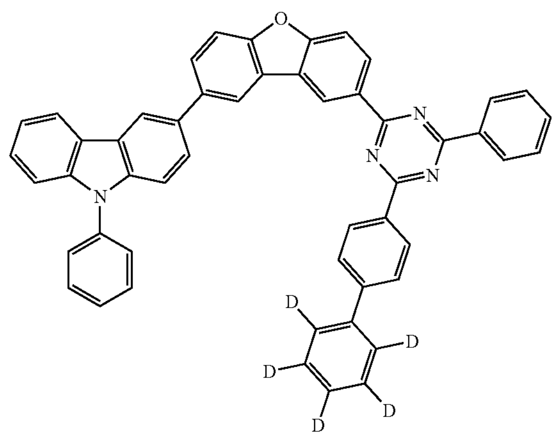
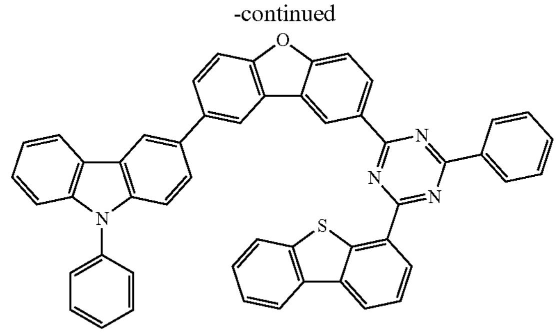
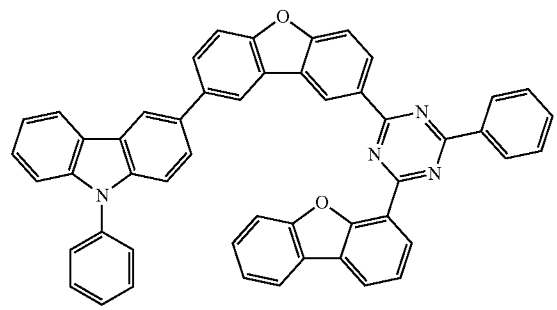
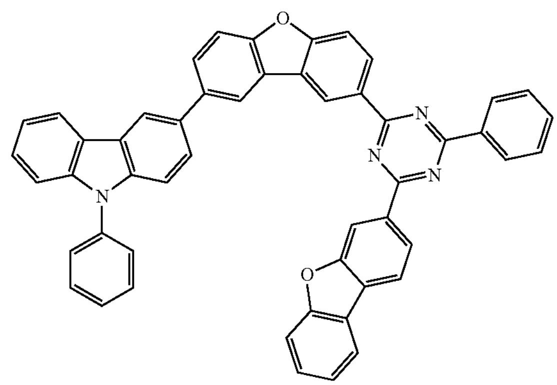
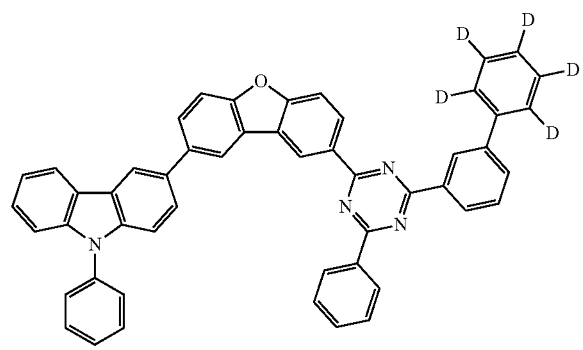
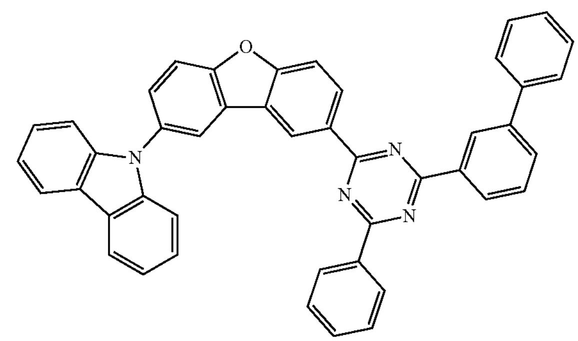

-continued
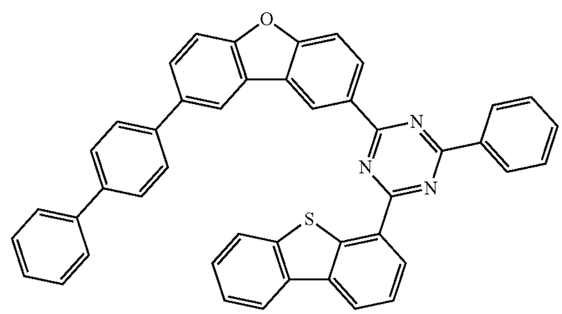
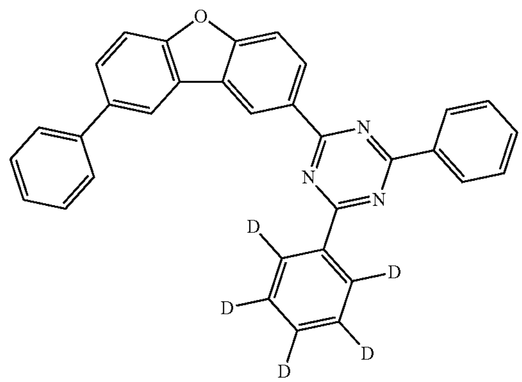
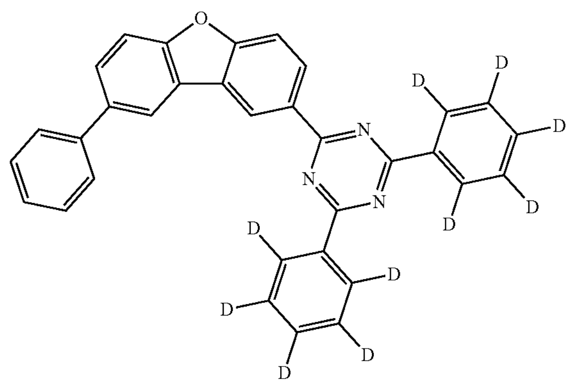
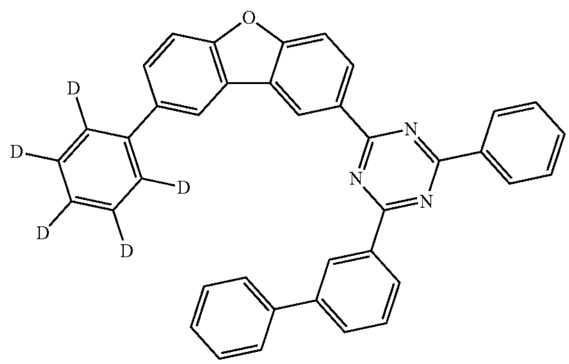
-continued
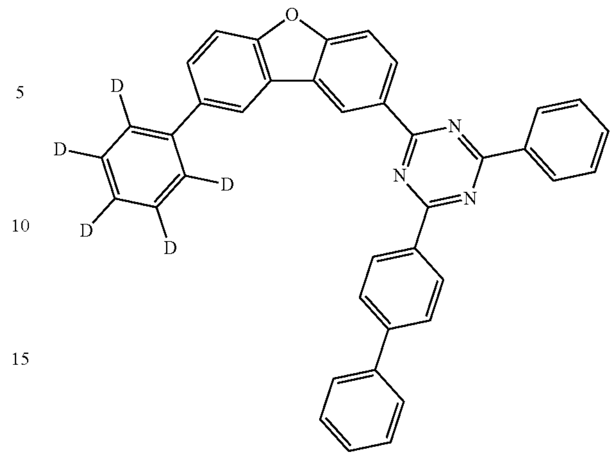
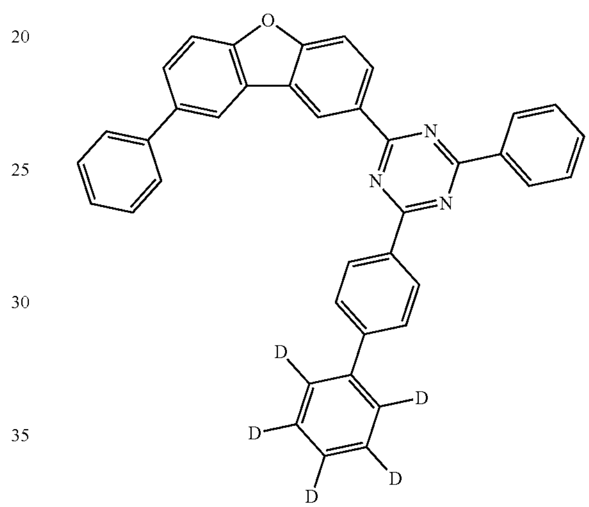
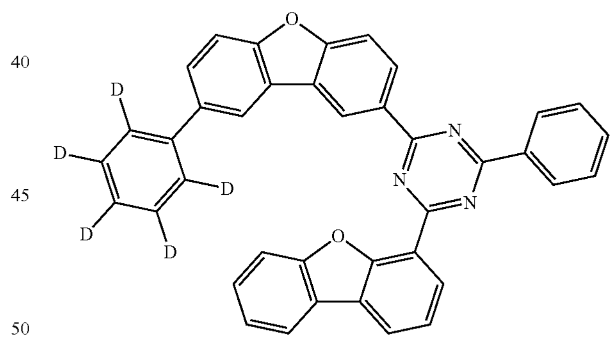
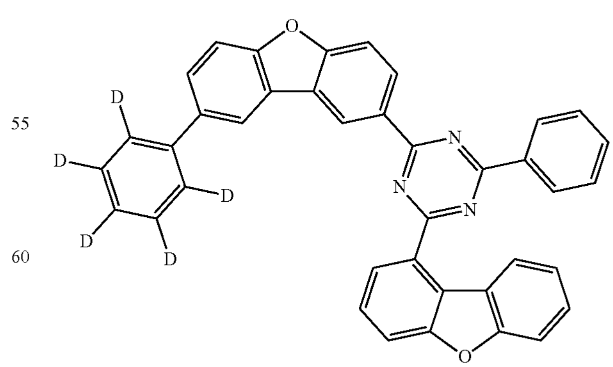

-continued
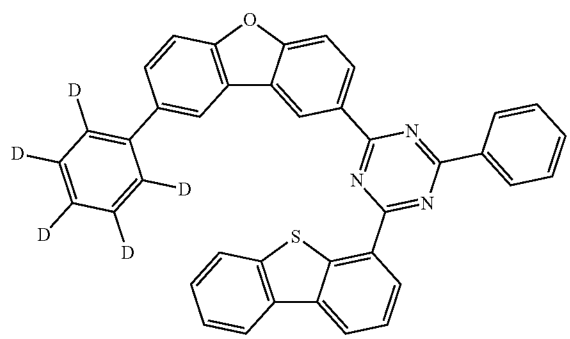
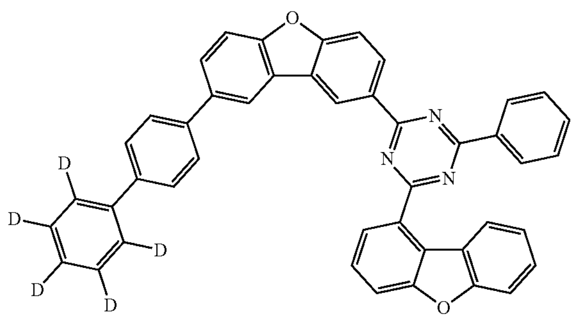
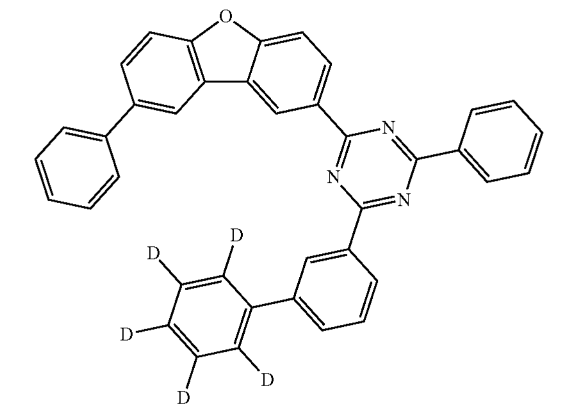
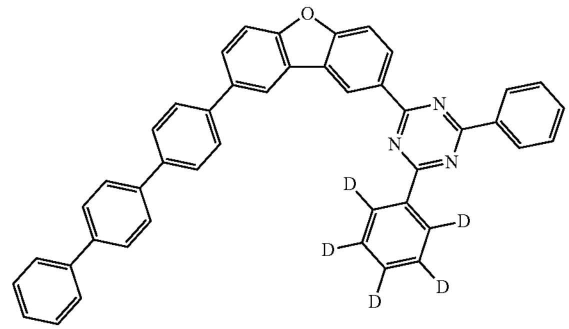
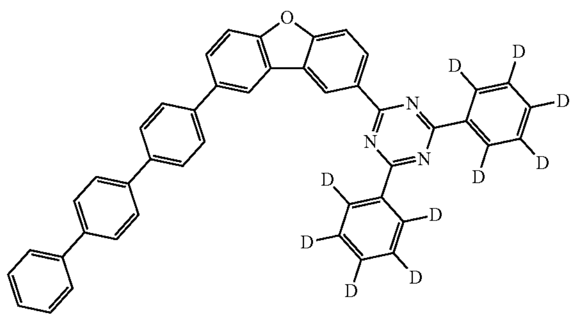
-continued
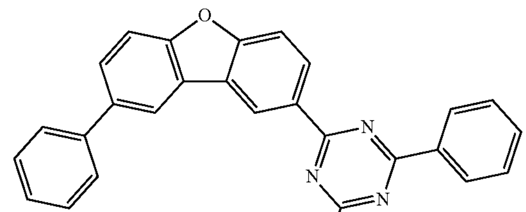
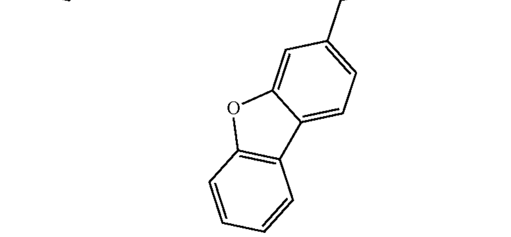
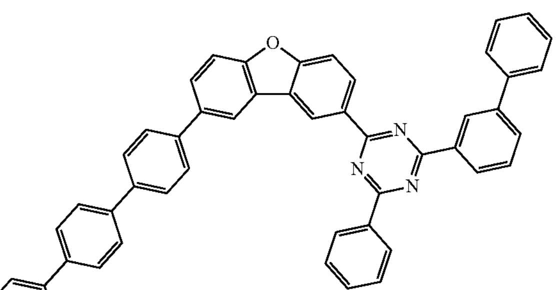
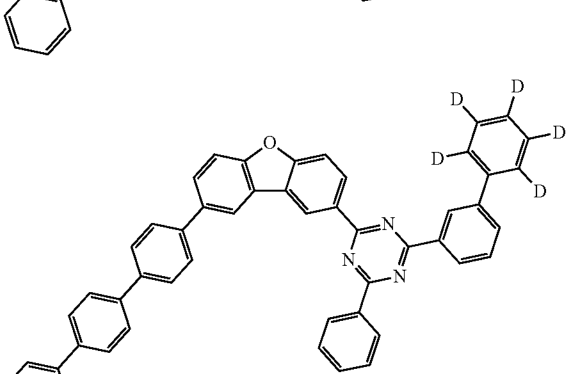
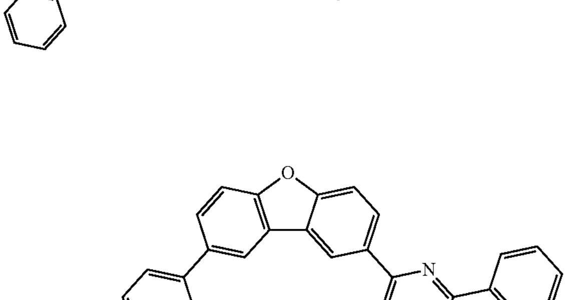
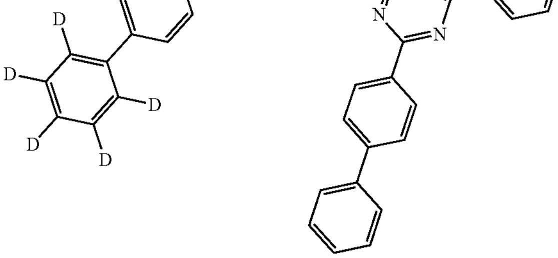

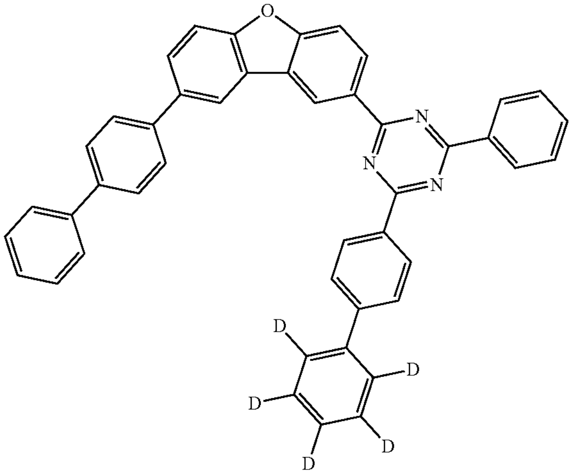
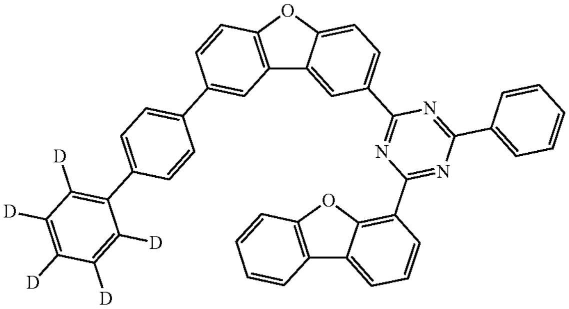
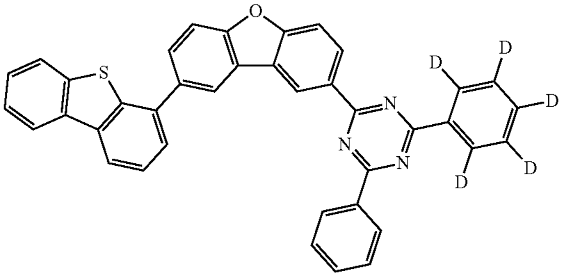
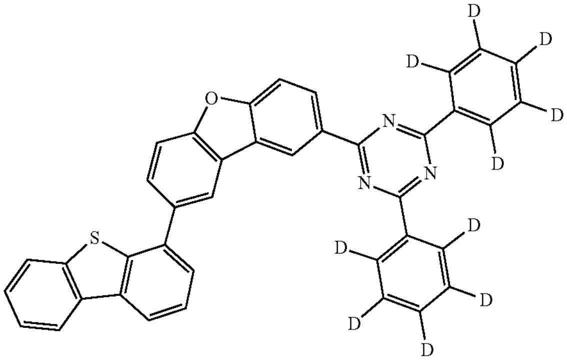
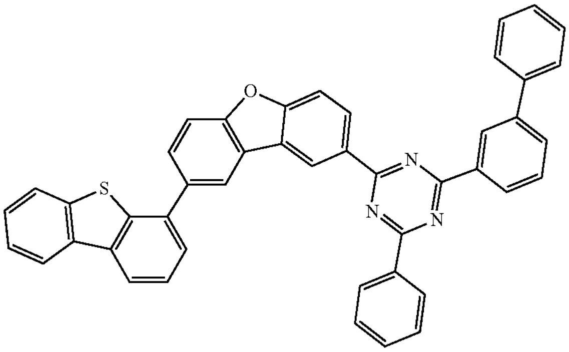
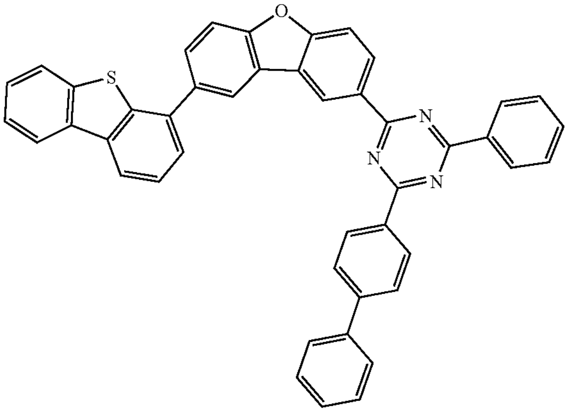
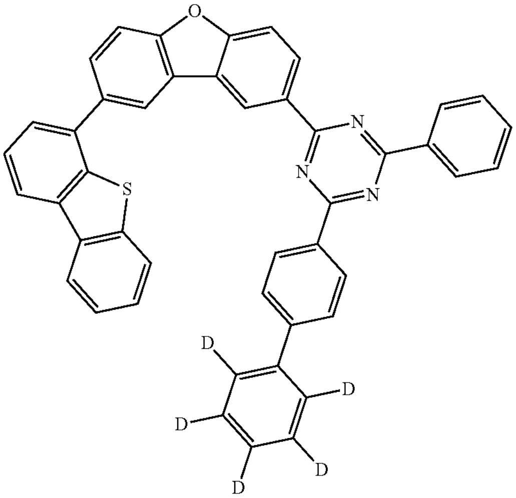
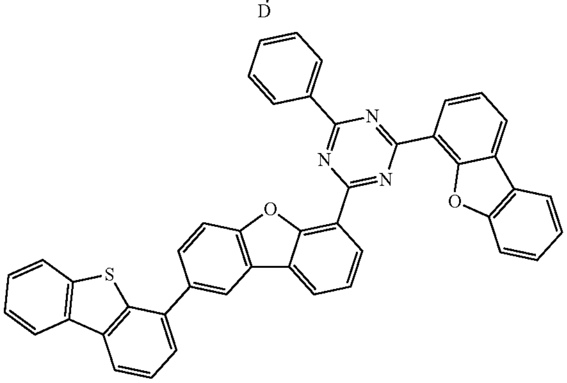

-continued
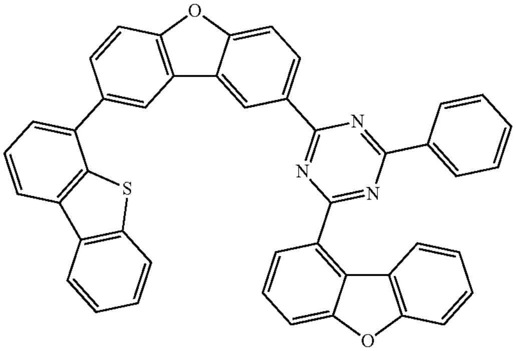
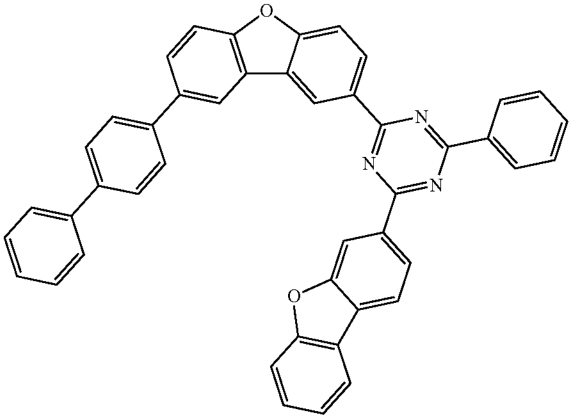
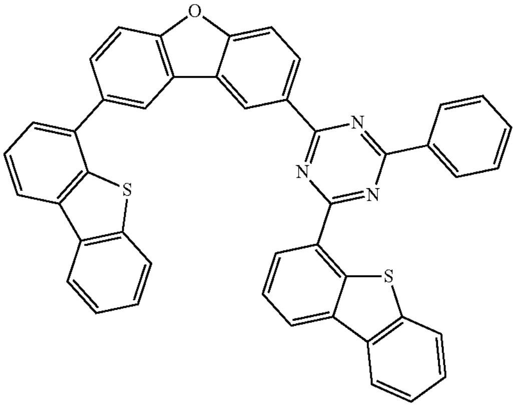
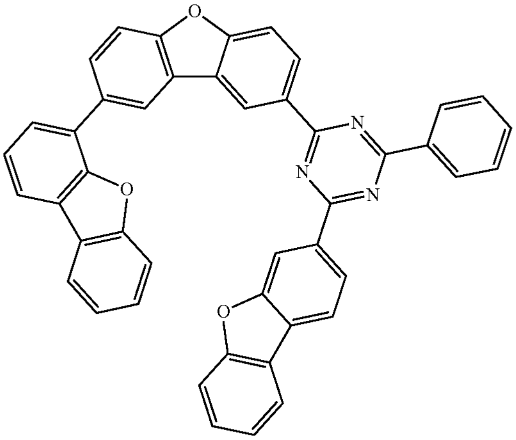
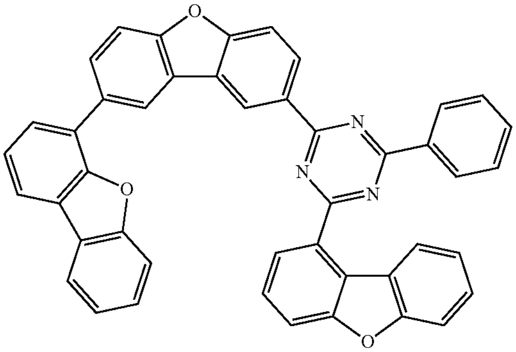
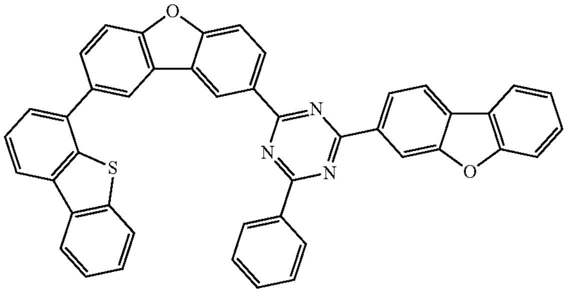
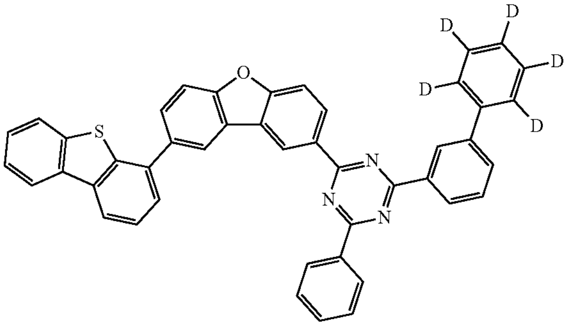
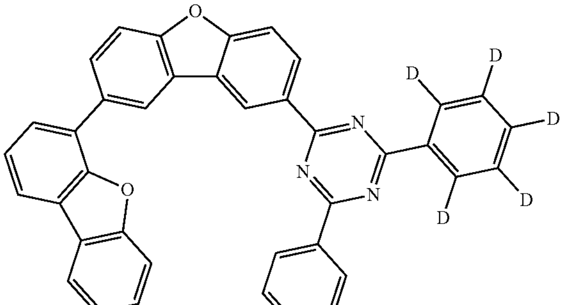

-continued
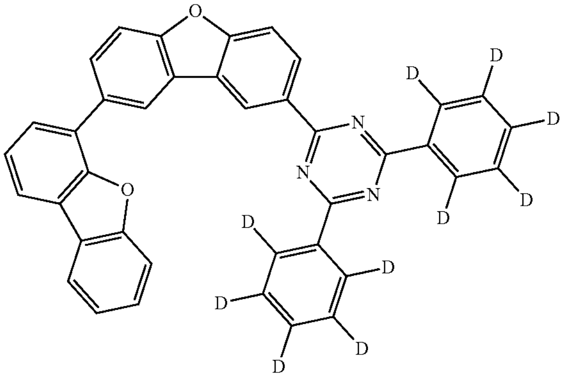
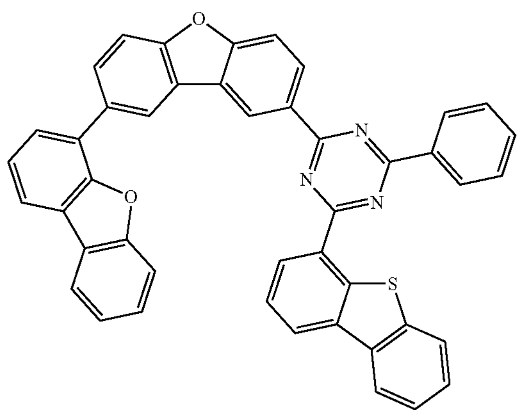
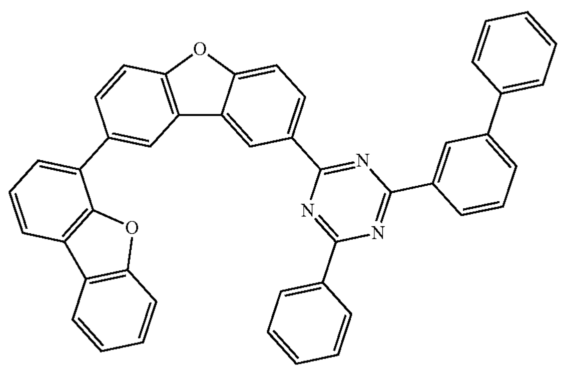
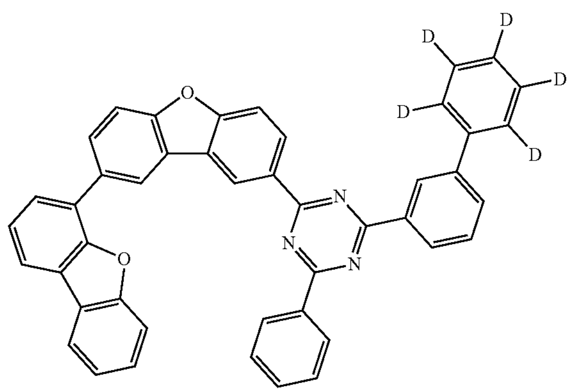
-continued
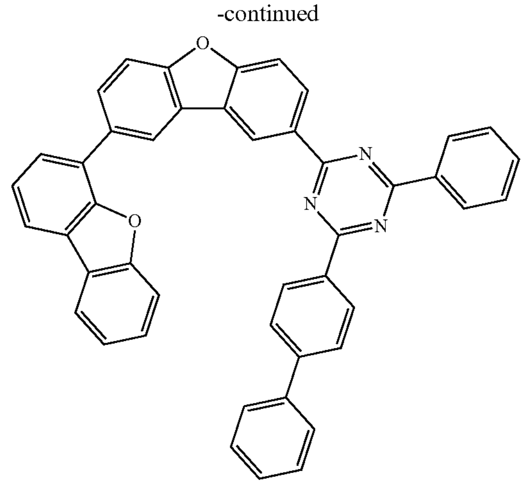
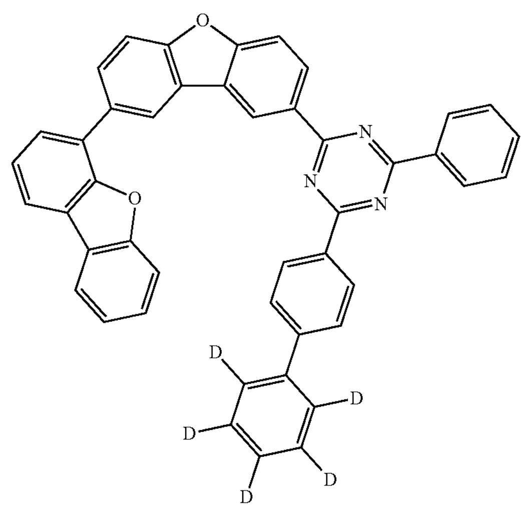
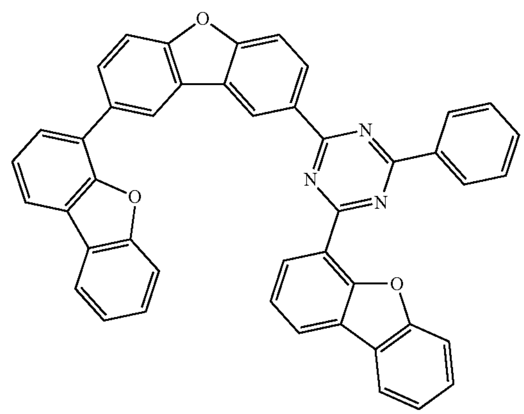
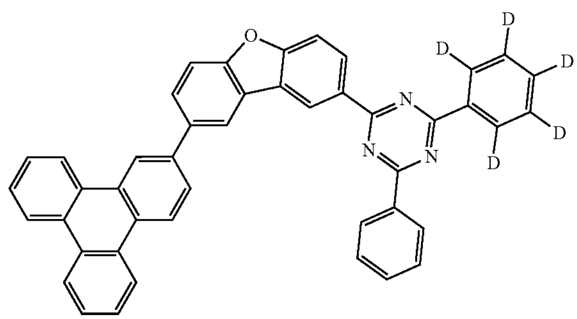

-continued
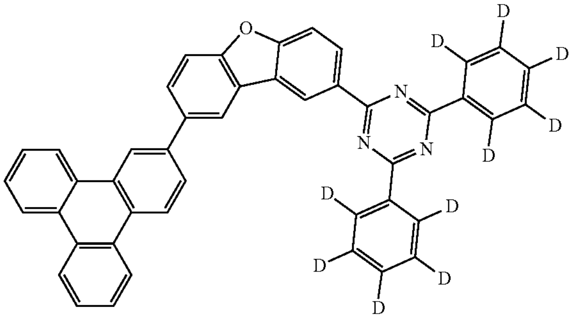
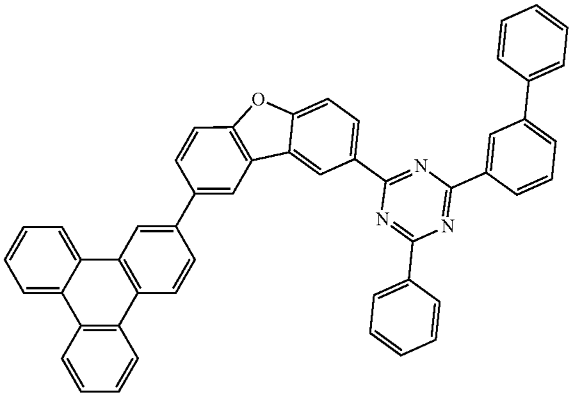
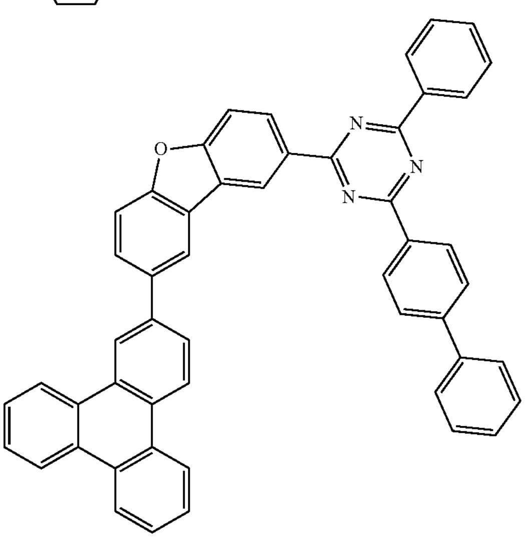
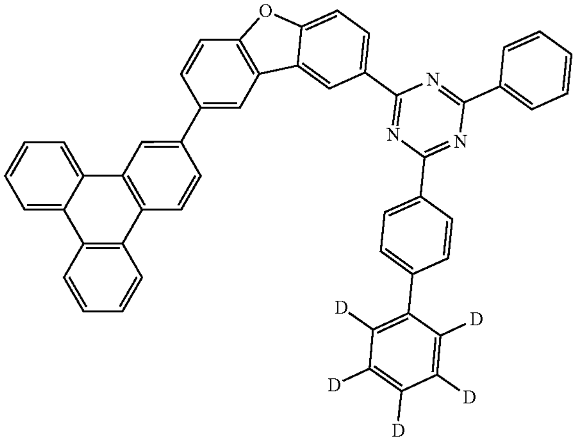
-continued
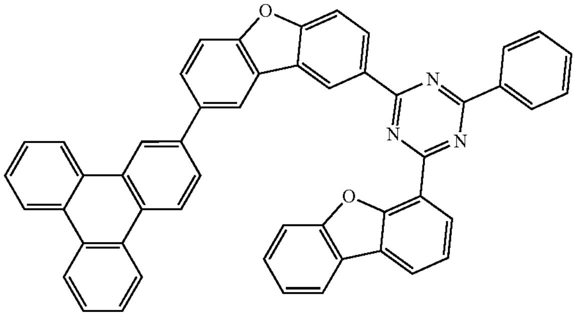
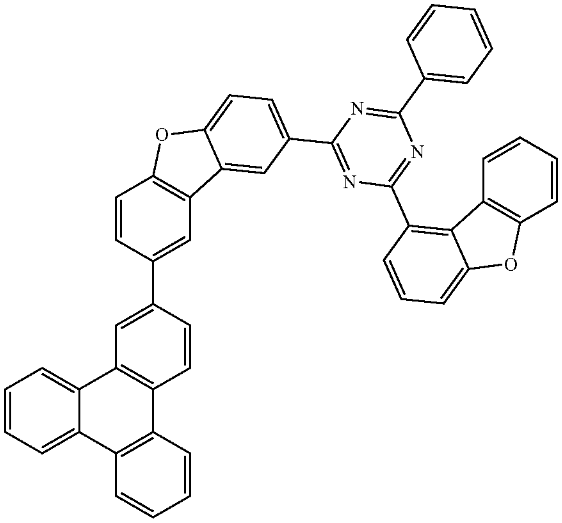
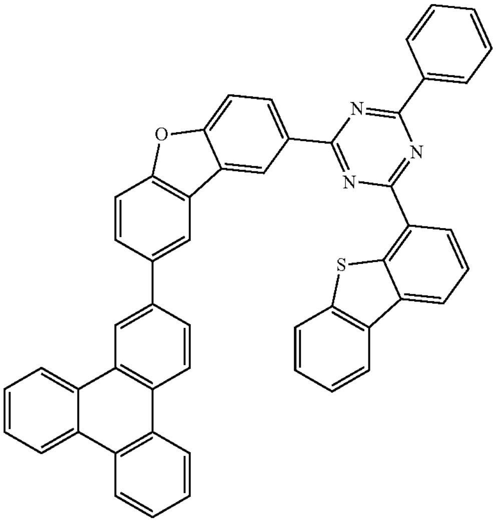
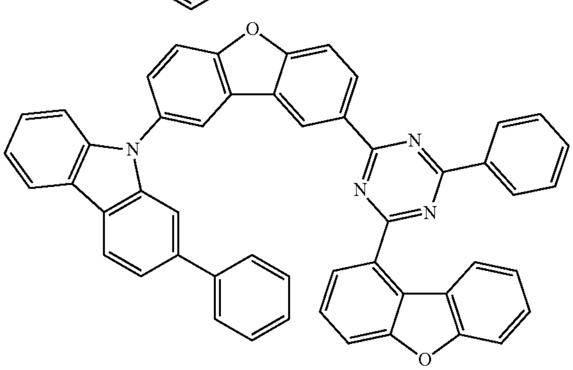

-continued
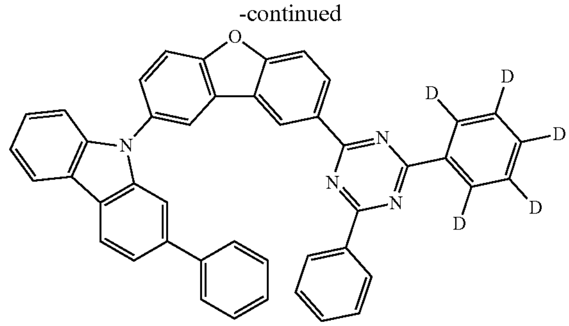
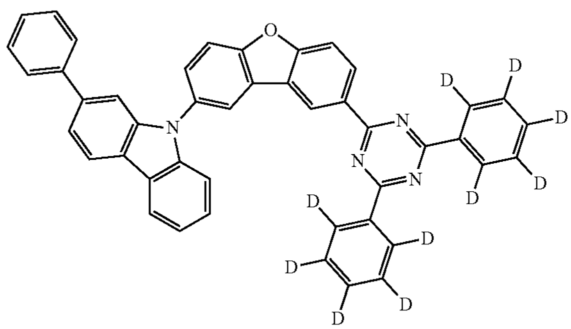
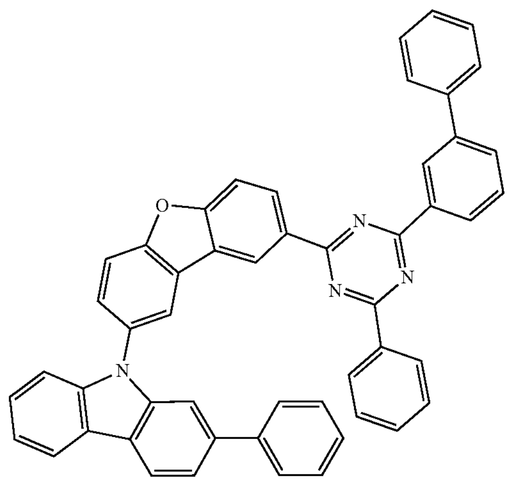
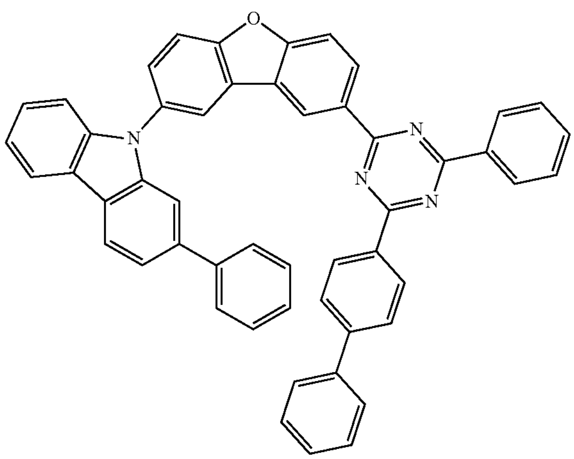
-continued
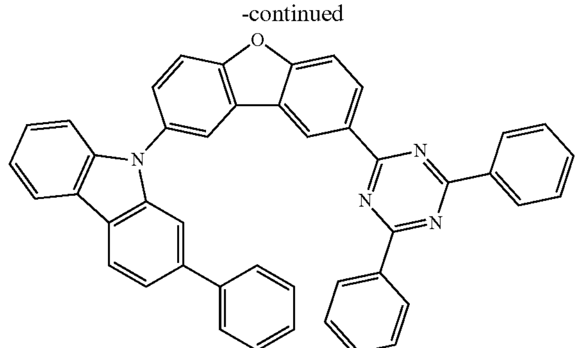
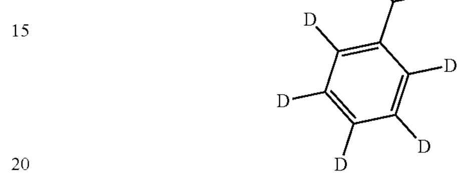
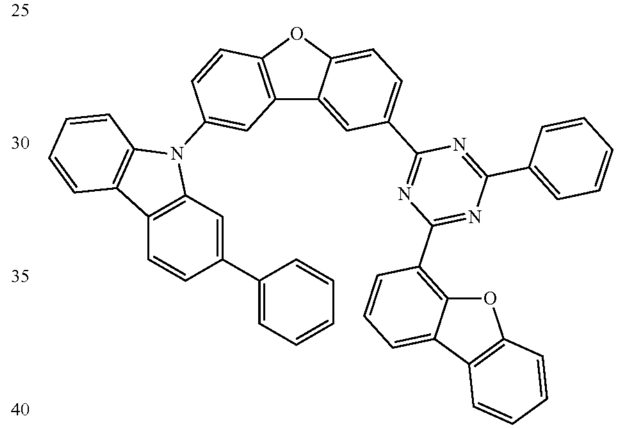
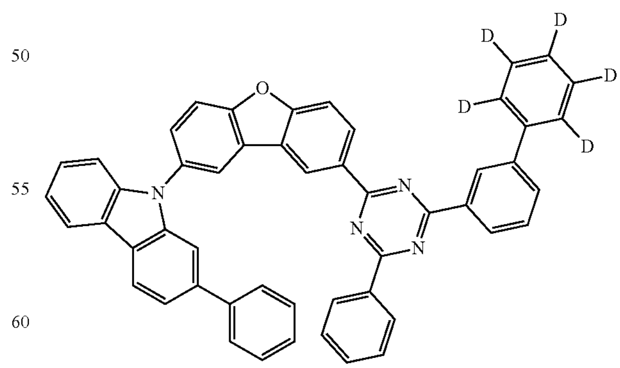

-continued
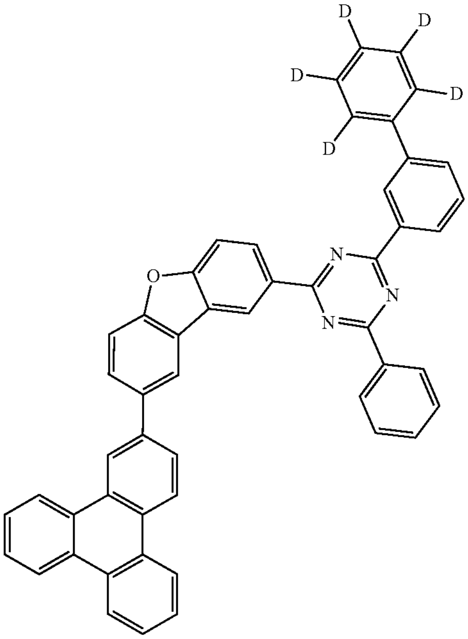
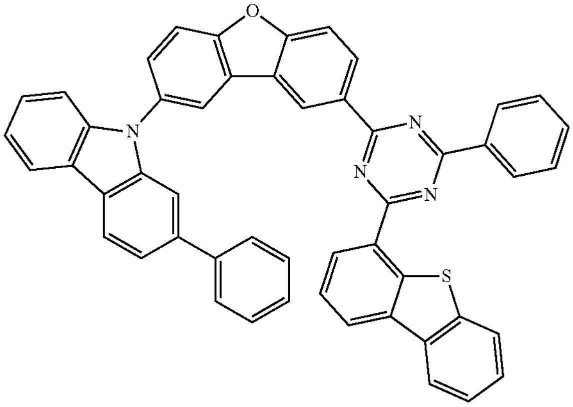
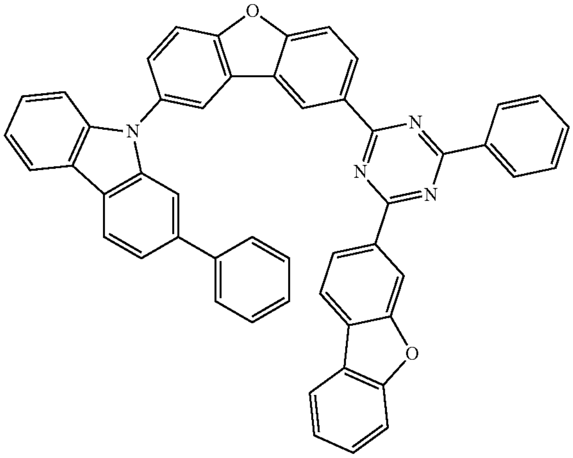
-continued
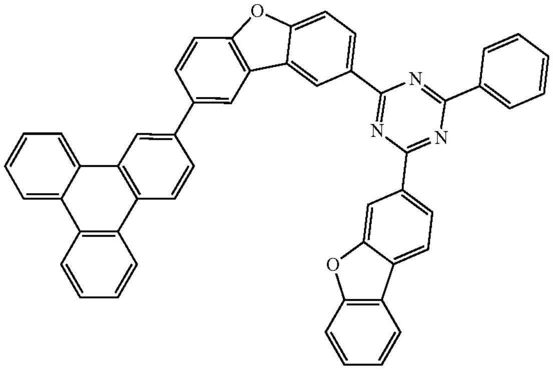
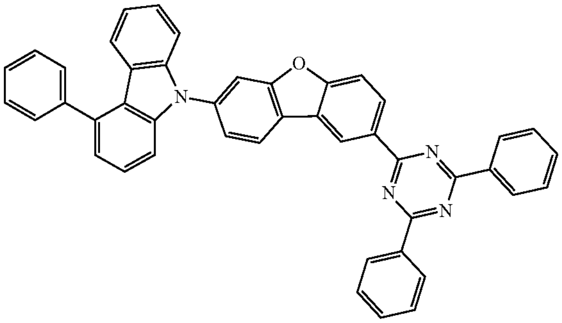
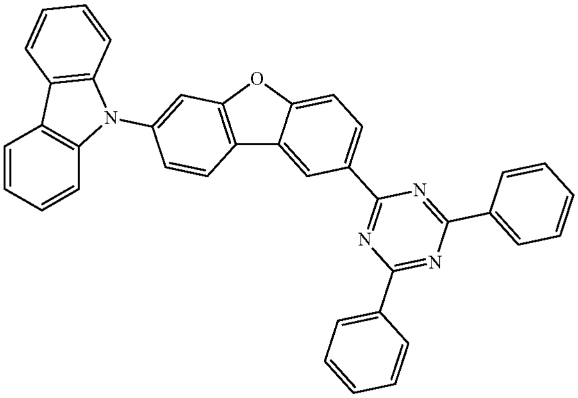
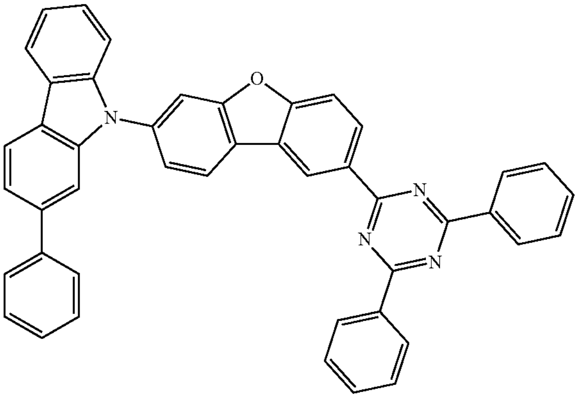

-continued
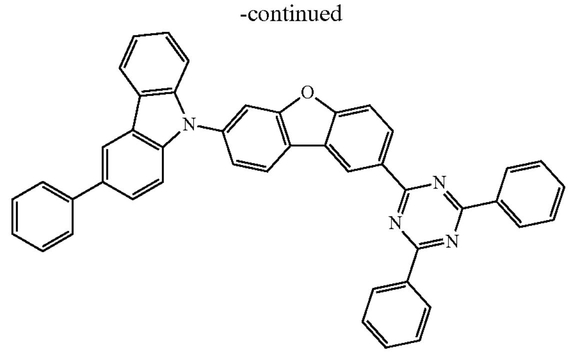
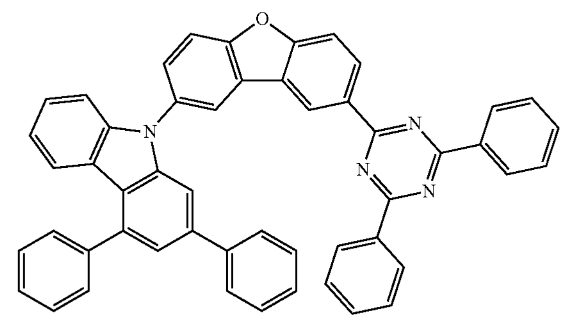
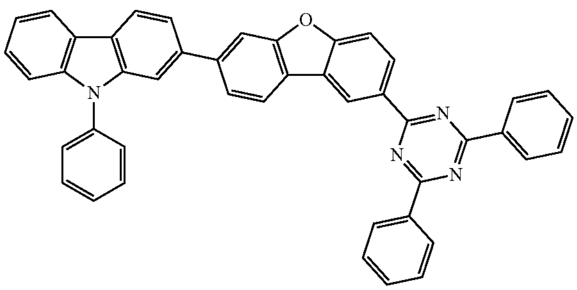
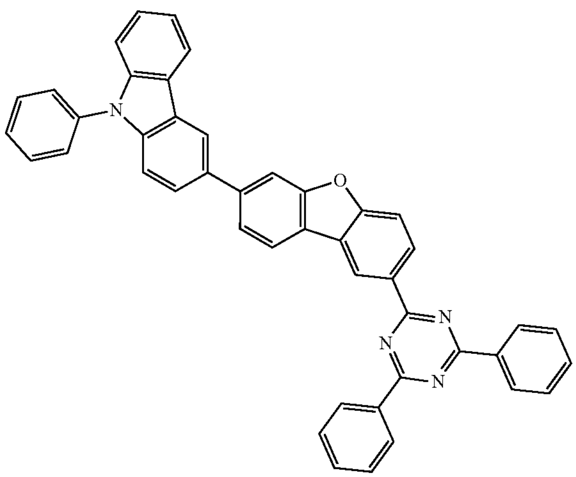
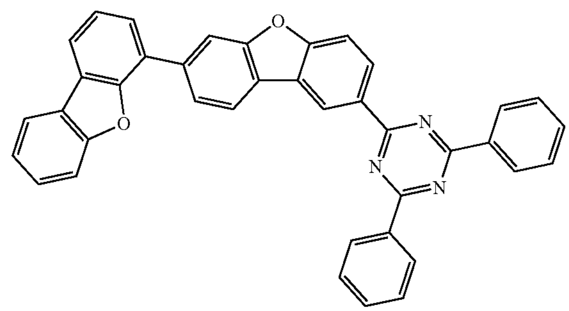
-continued
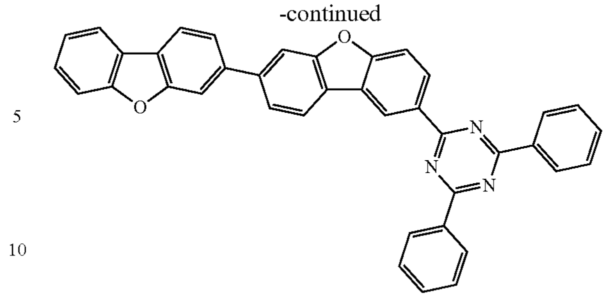
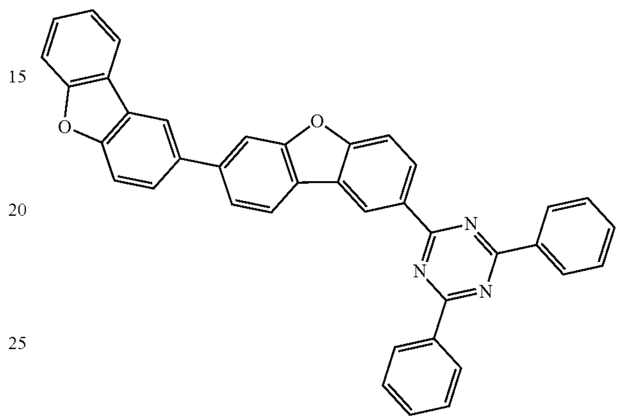
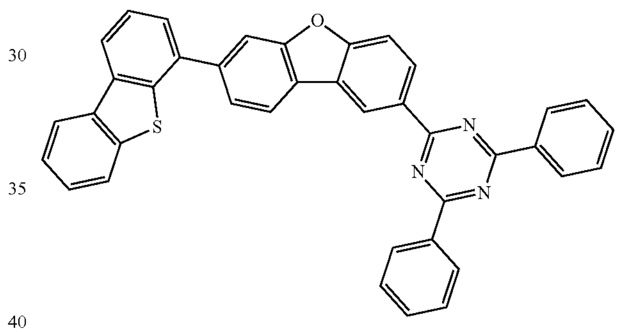
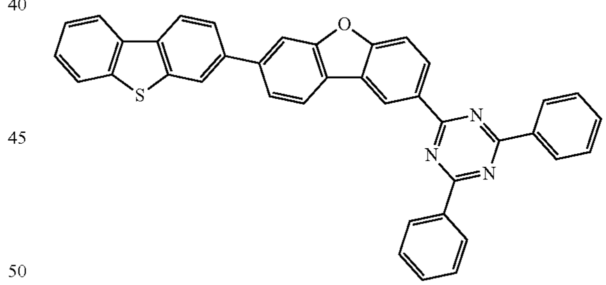
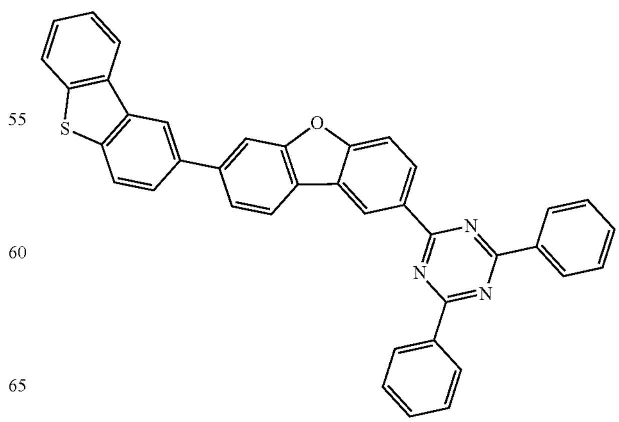

-continued
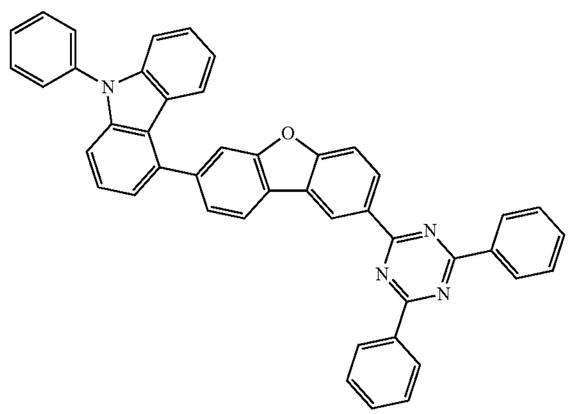
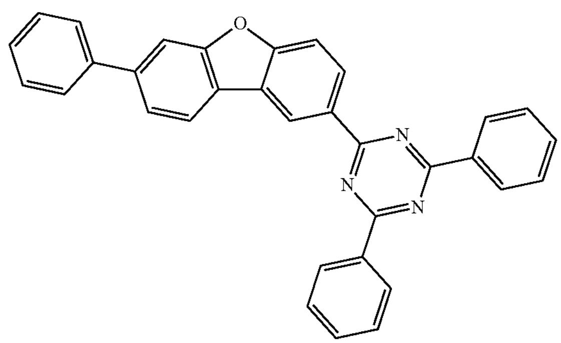
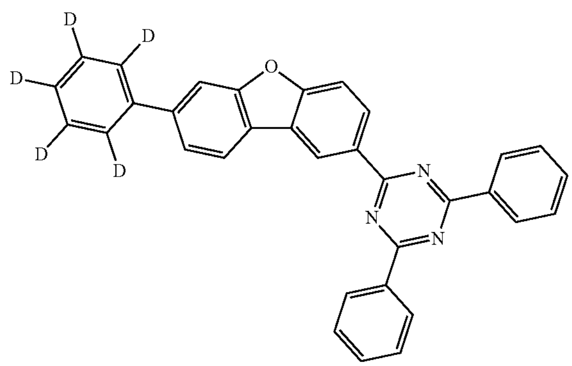
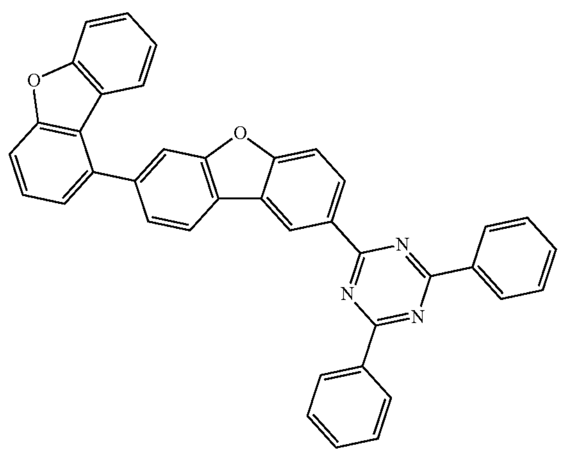
-continued
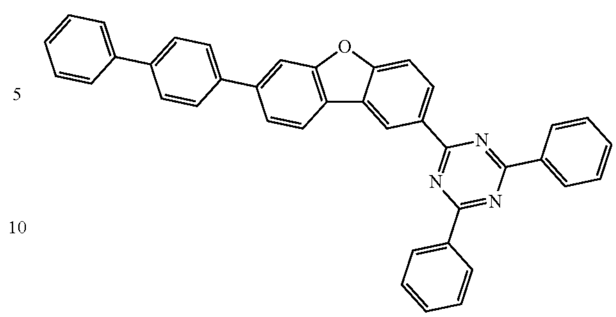
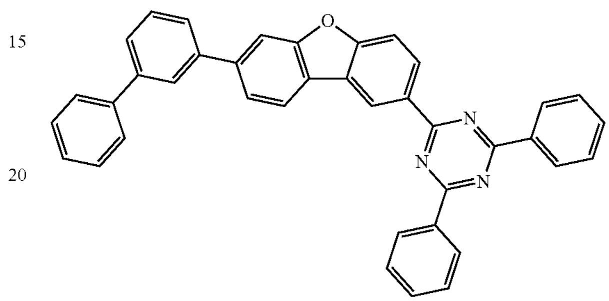
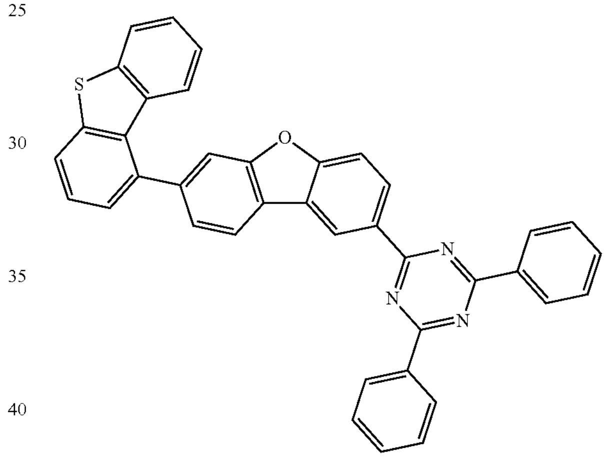
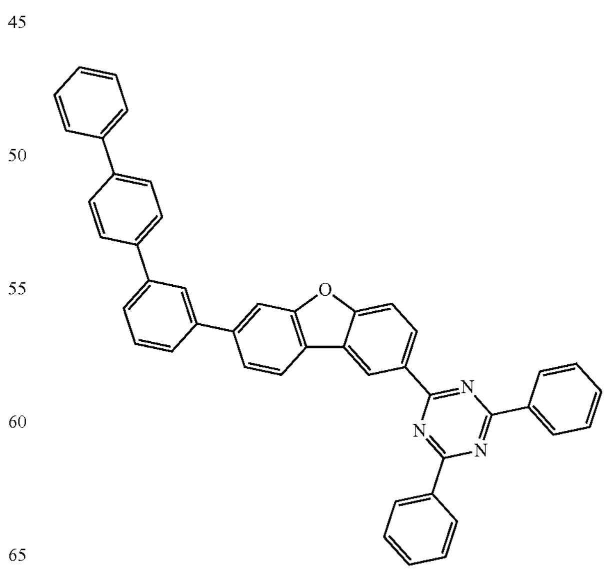

-continued
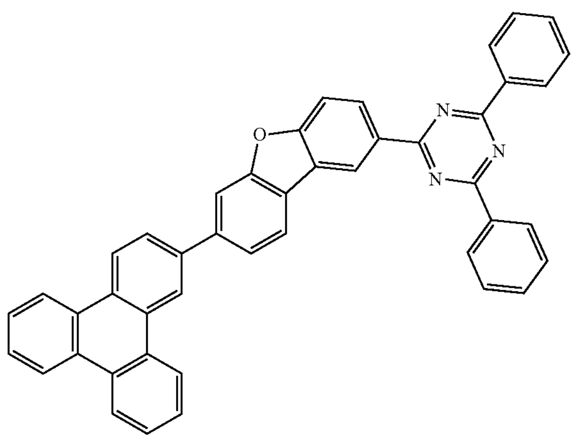
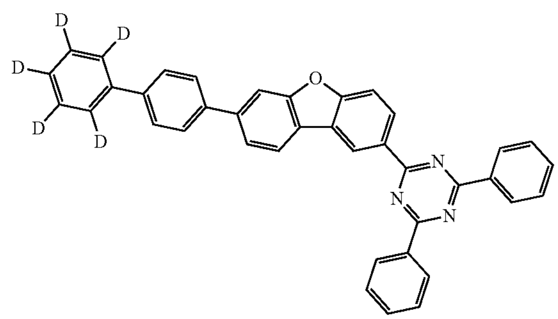
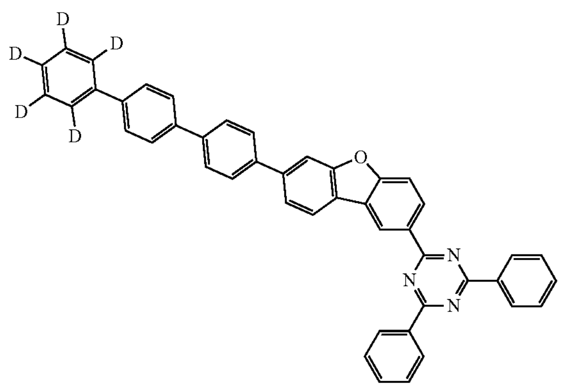
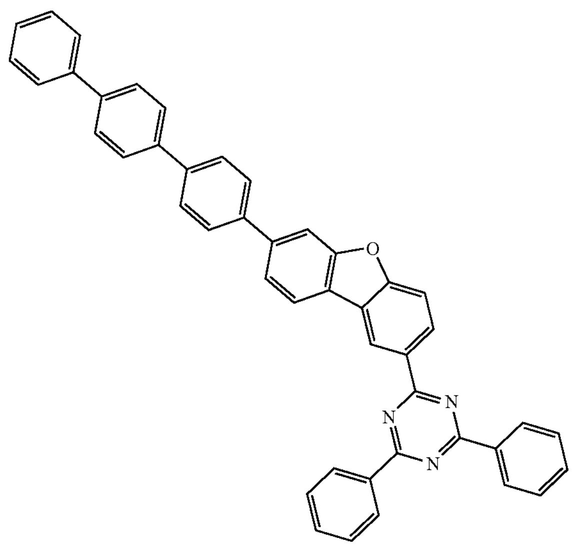
-continued
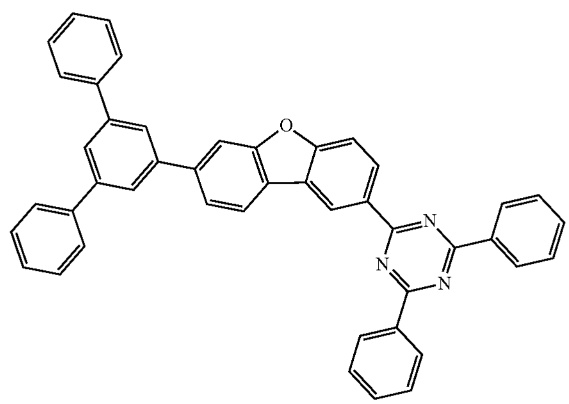
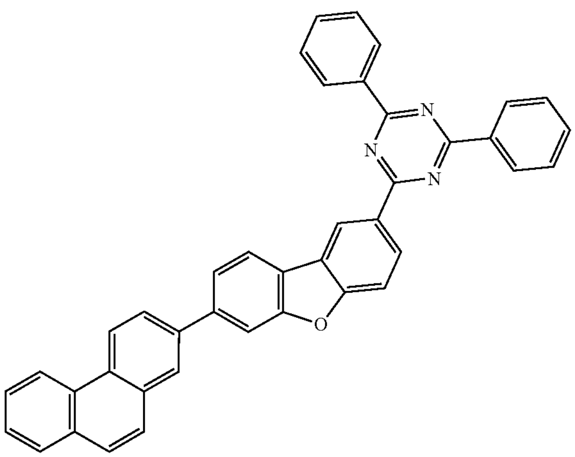
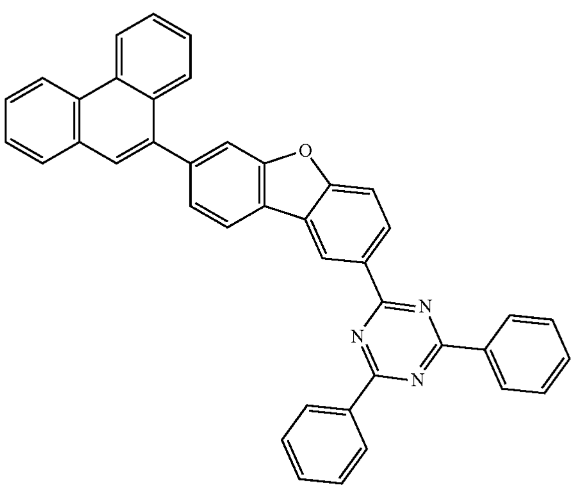
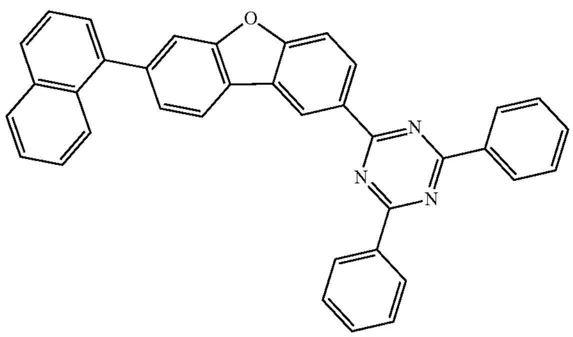

-continued
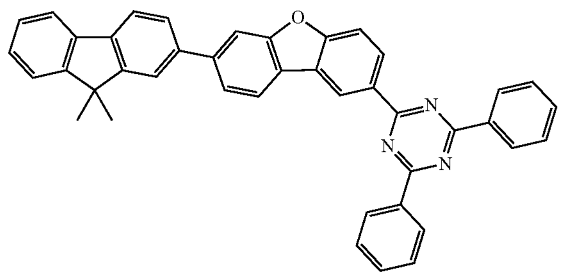
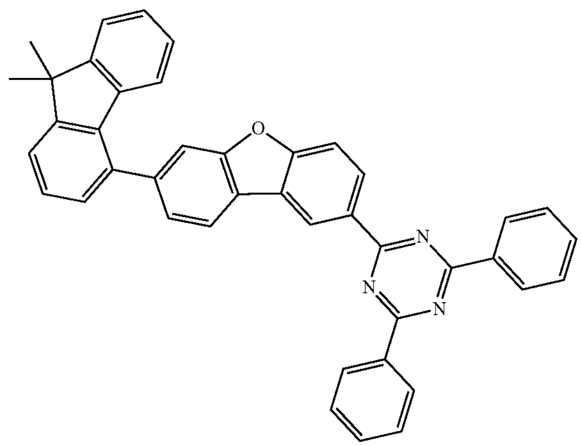
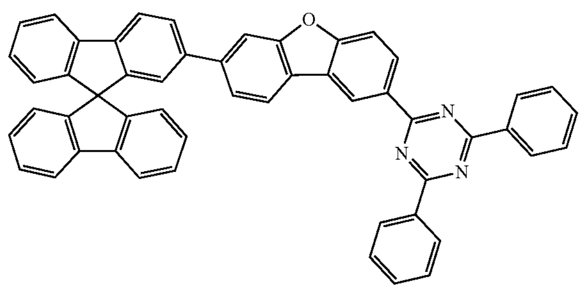
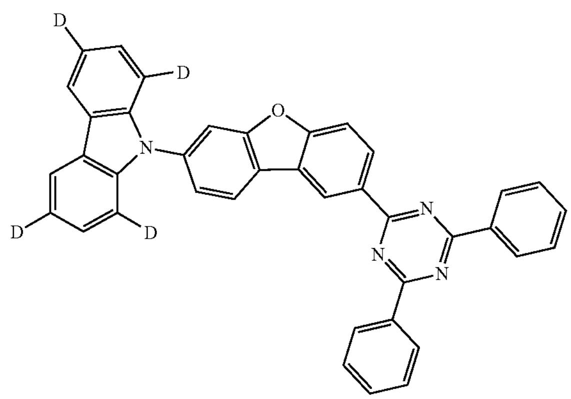
-continued
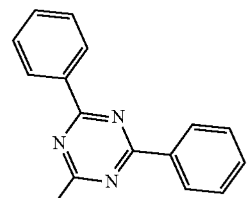
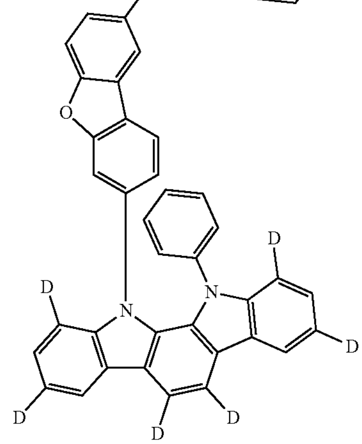
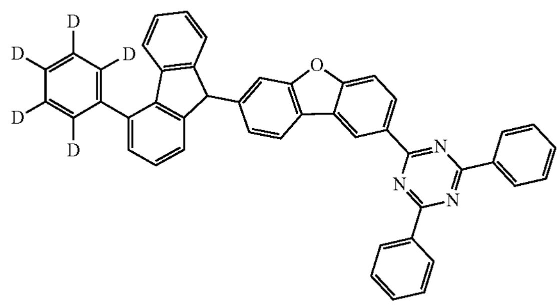
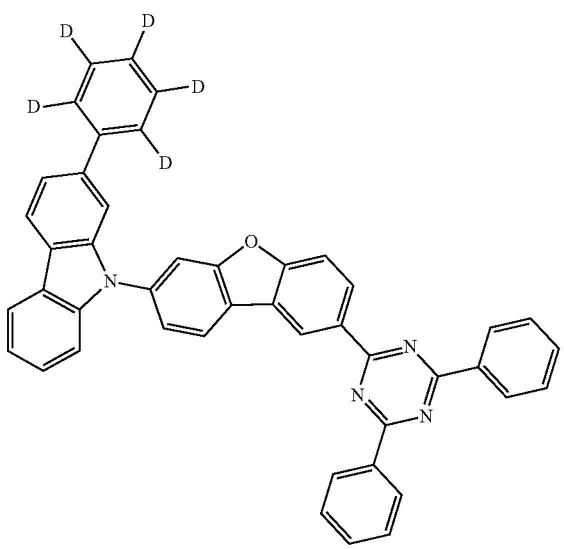

-continued
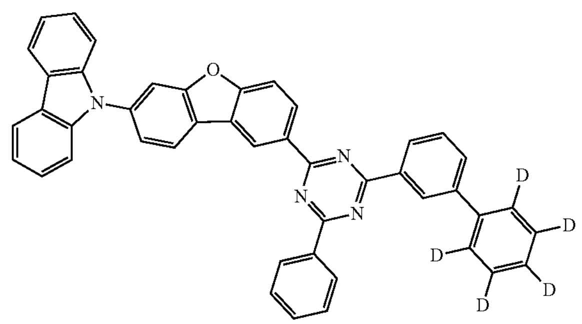
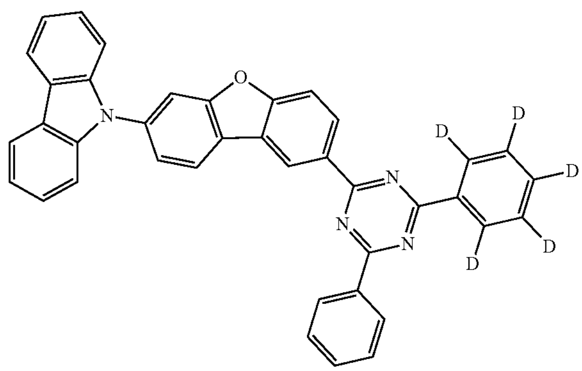
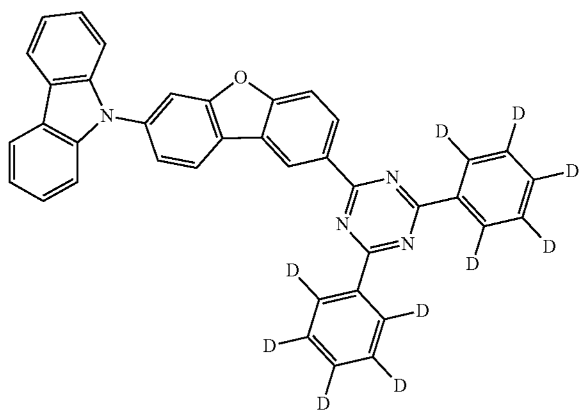
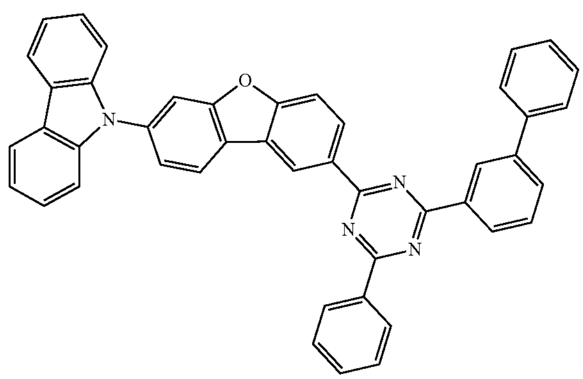
-continued
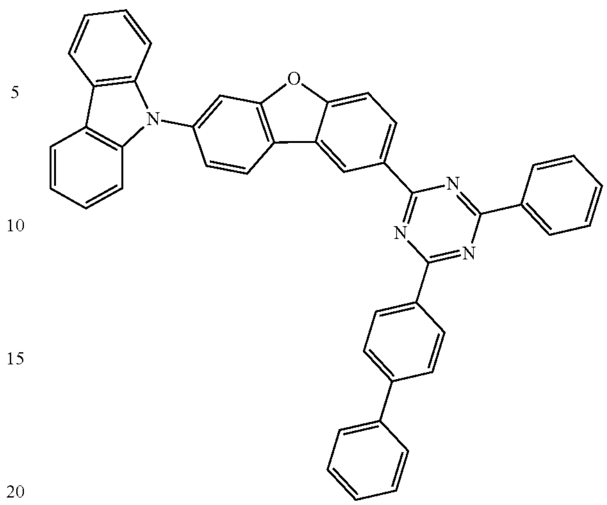
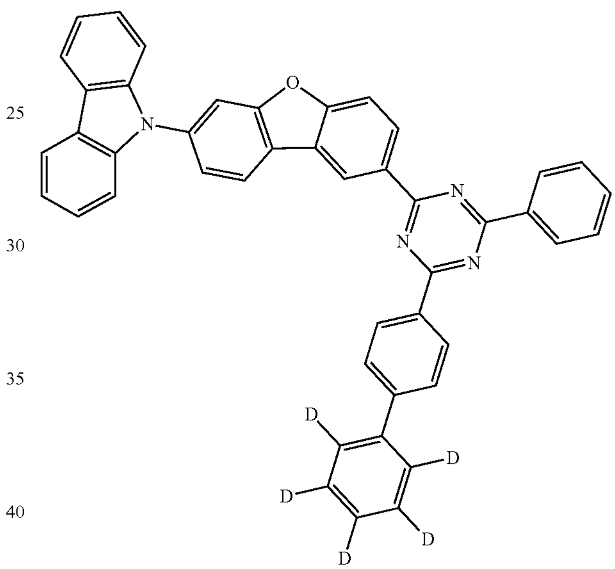
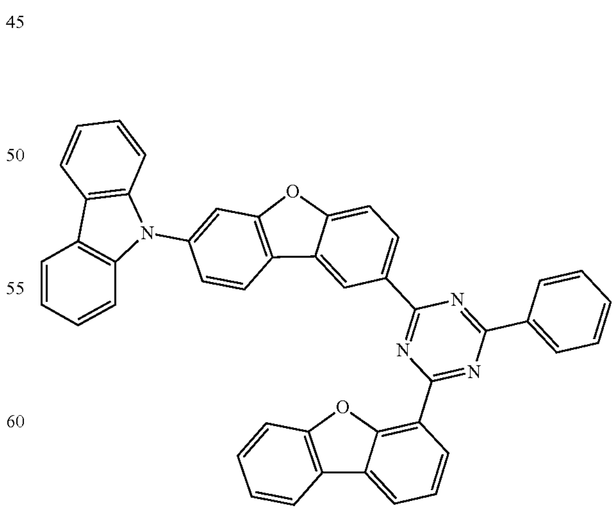

-continued
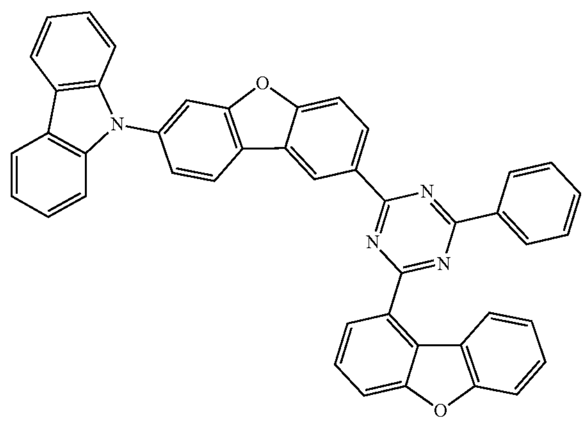
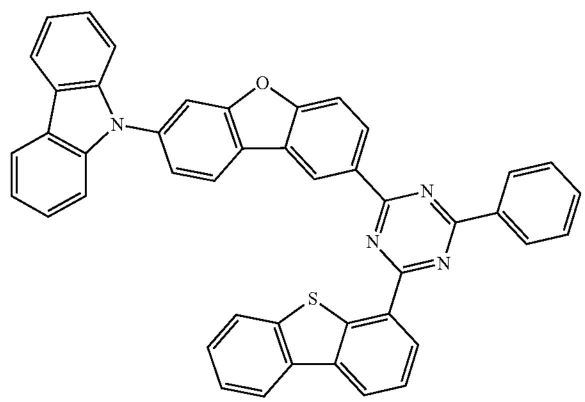
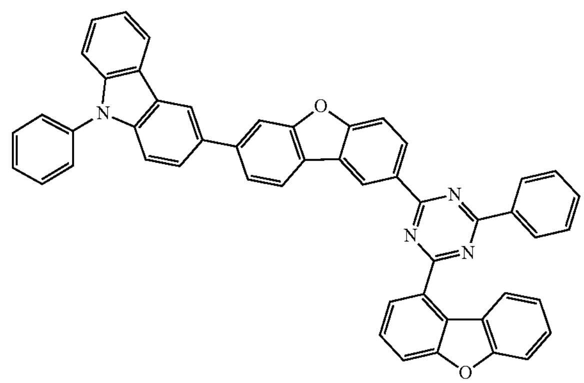
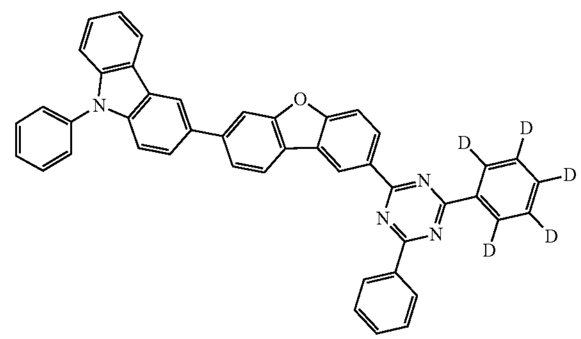
-continued
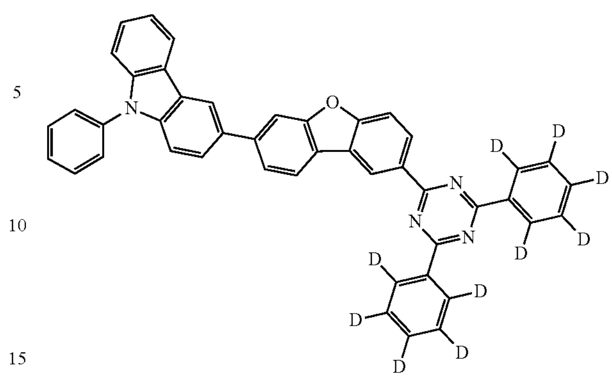
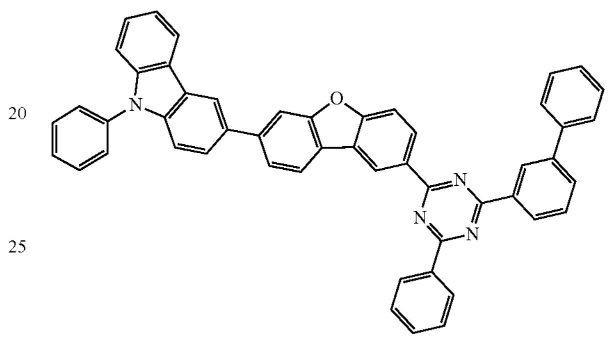
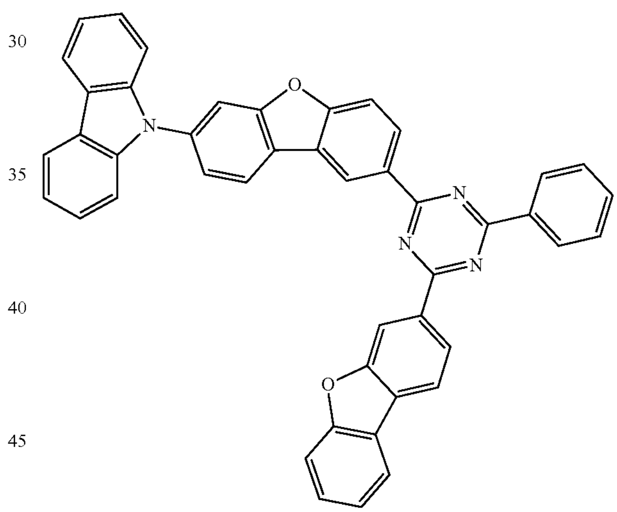
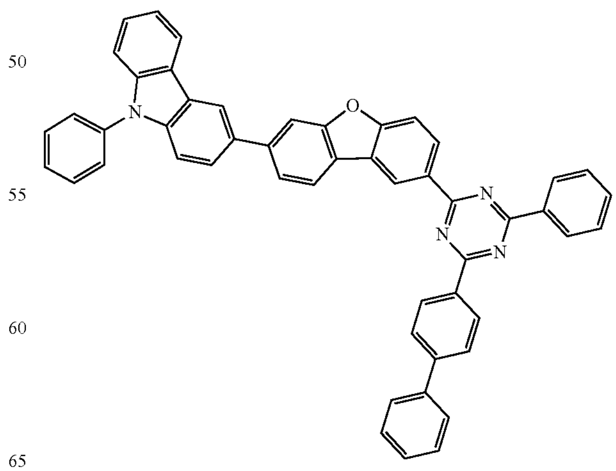

-continued
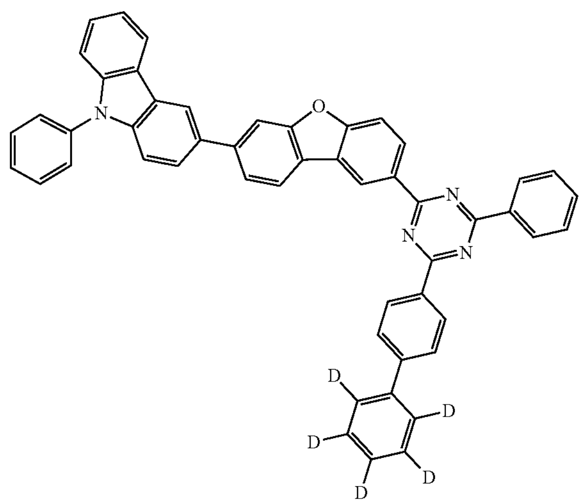
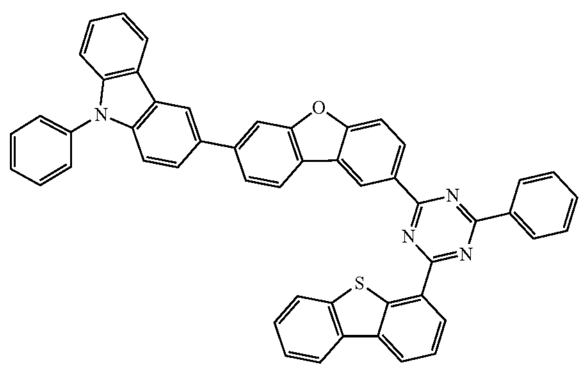
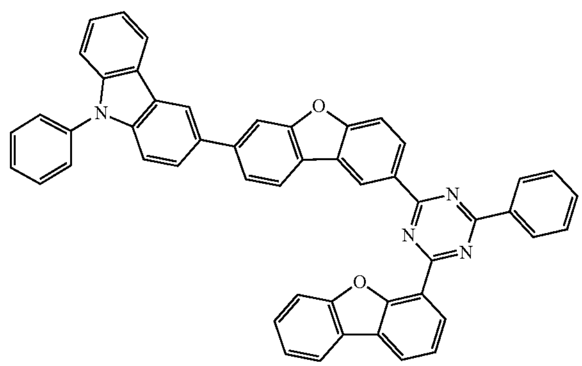
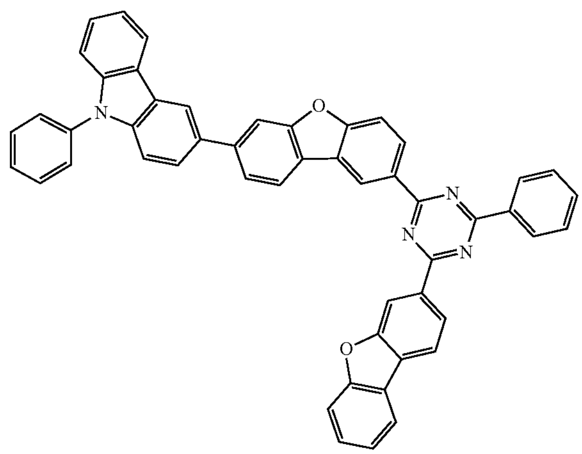
-continued
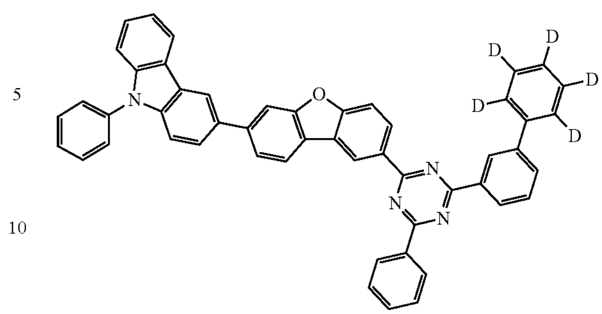
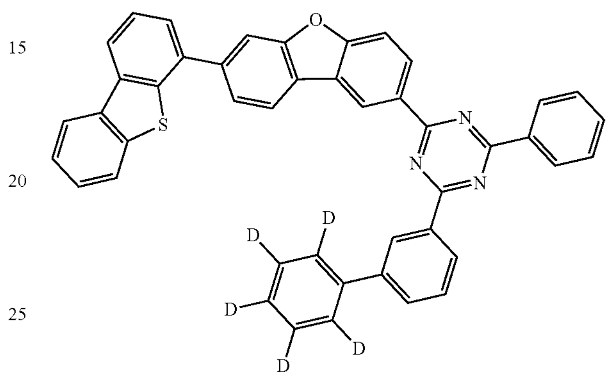
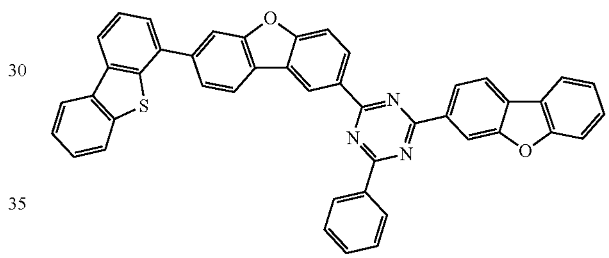
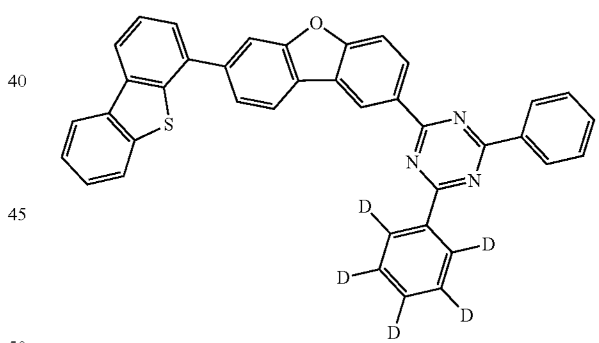
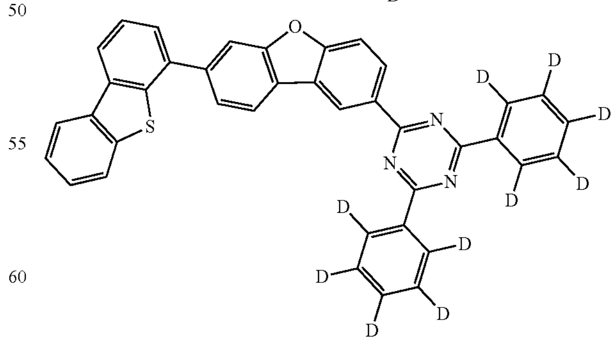

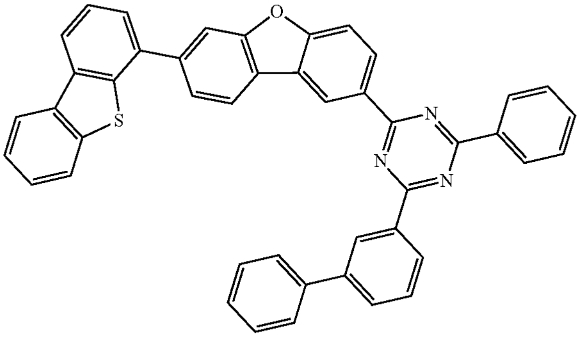
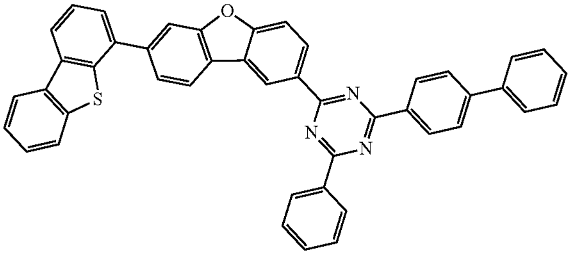
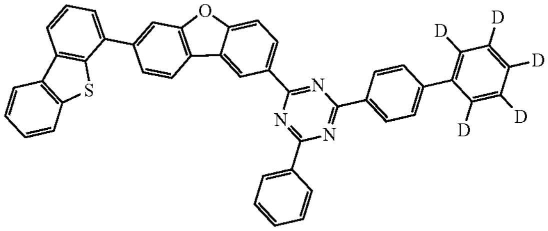
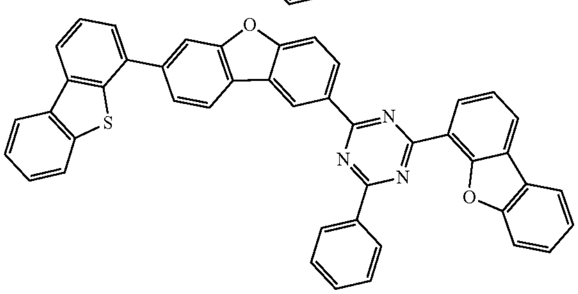
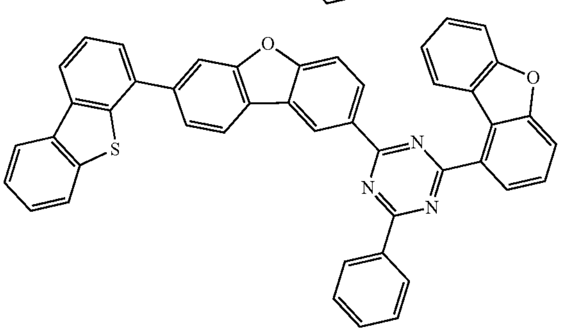
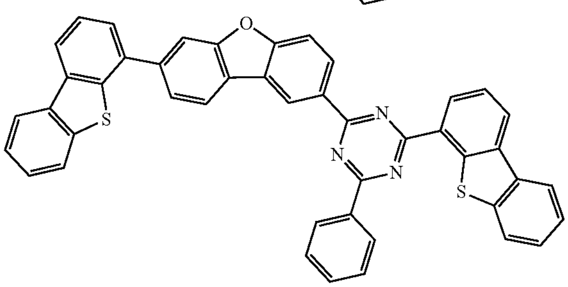
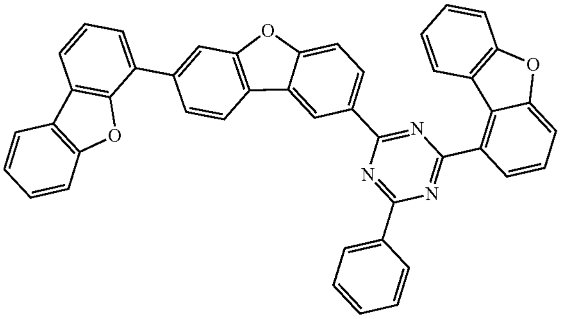
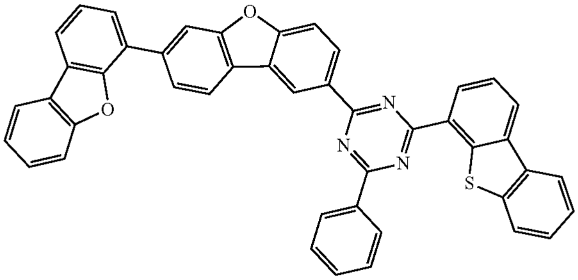
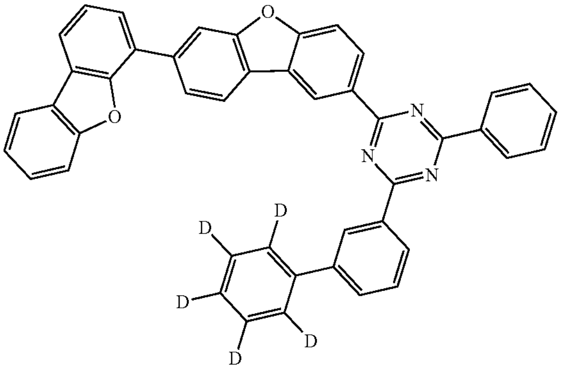
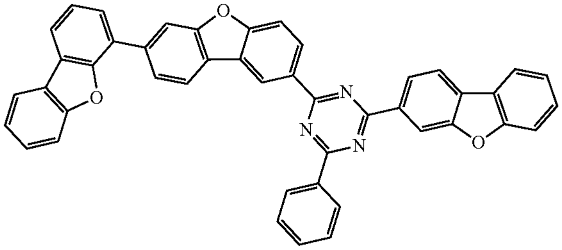
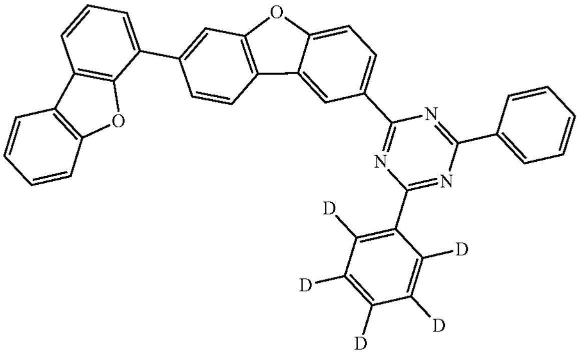

-continued
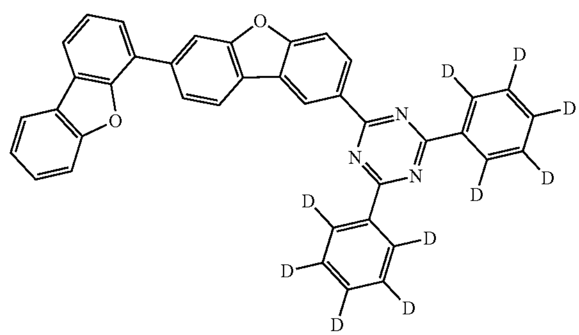
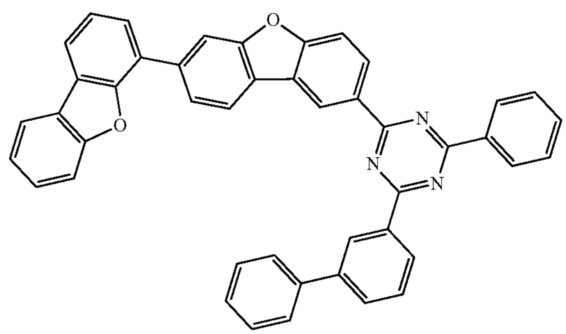
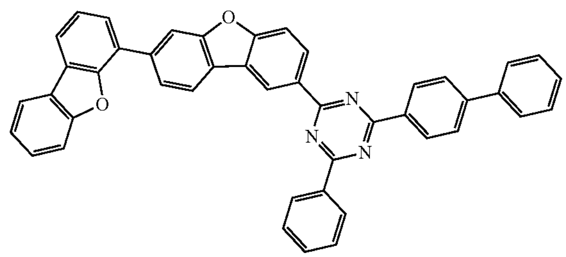
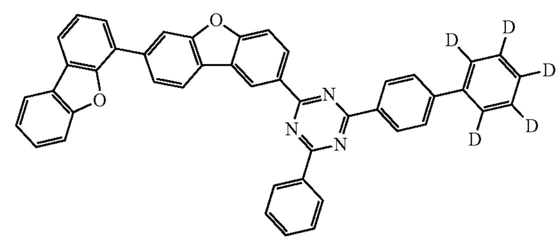
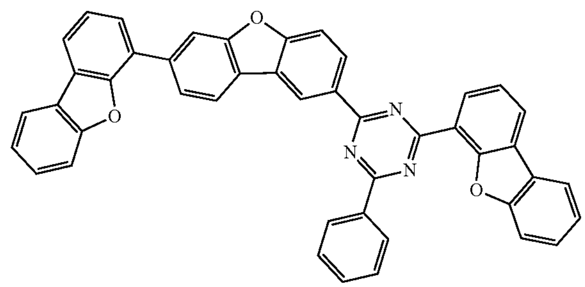
-continued
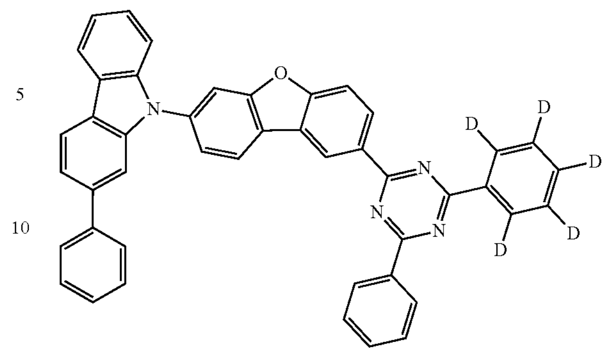
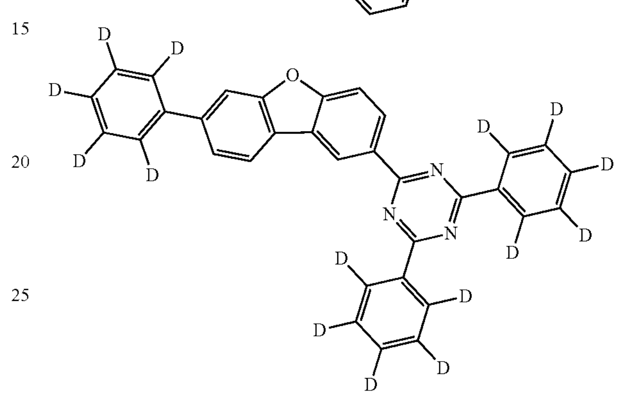
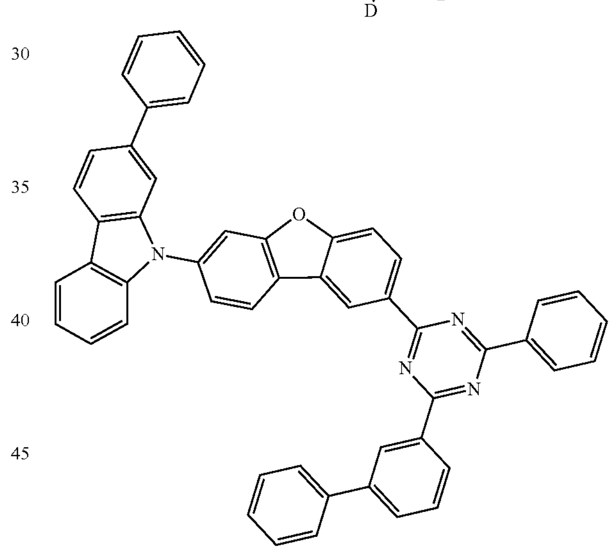
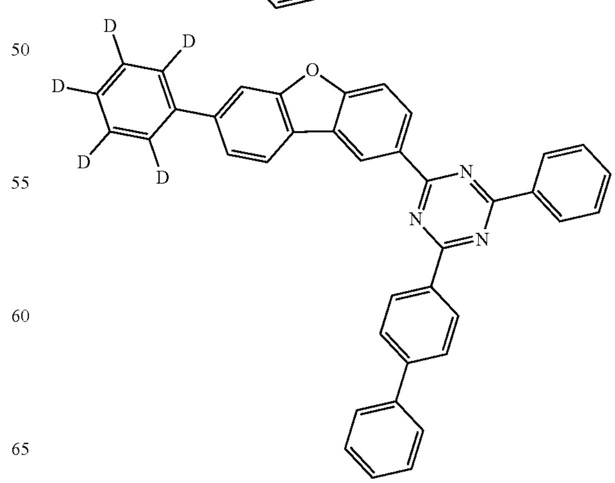

-continued
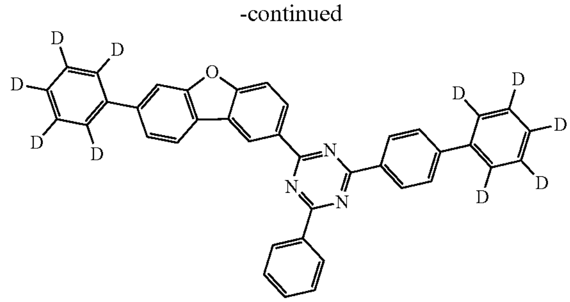
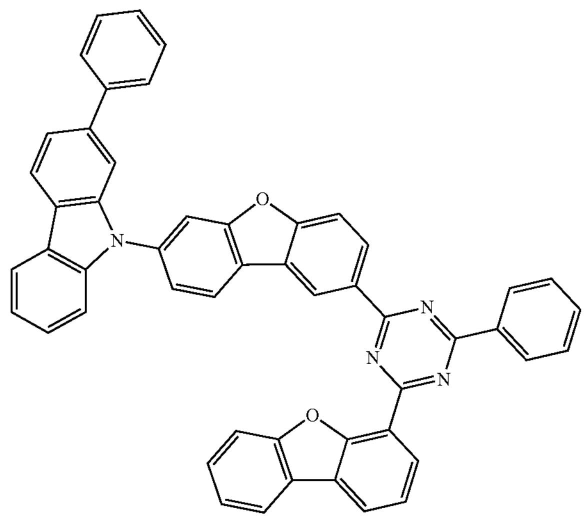
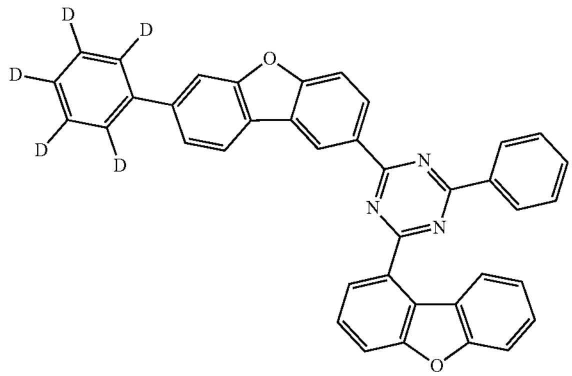
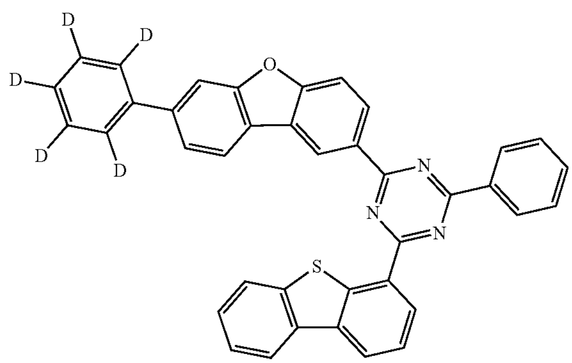
-continued
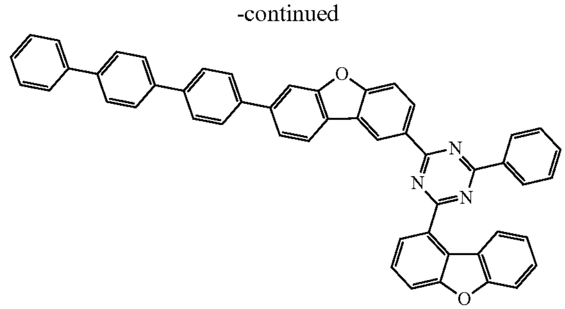
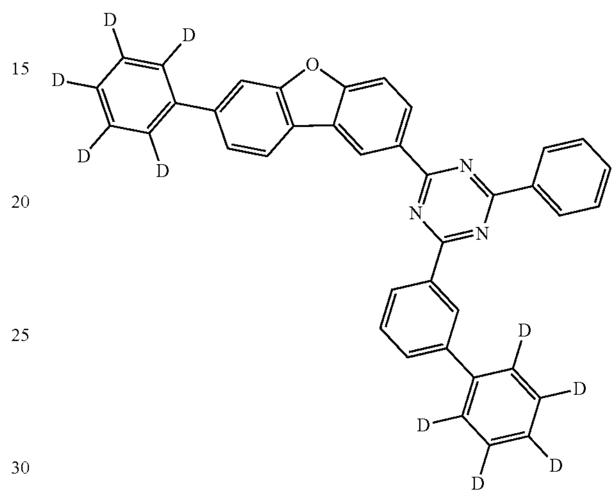
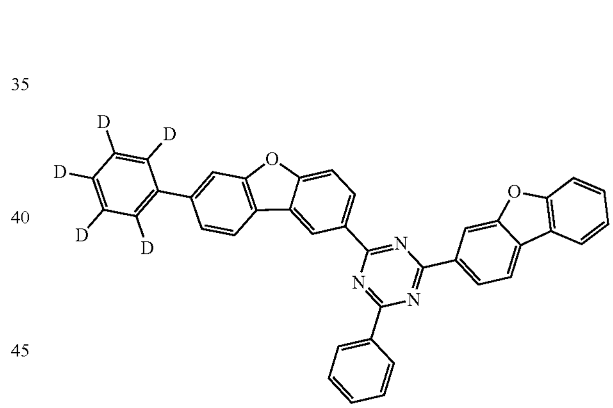
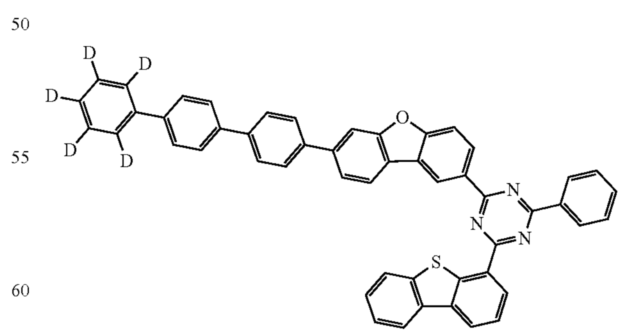

-continued
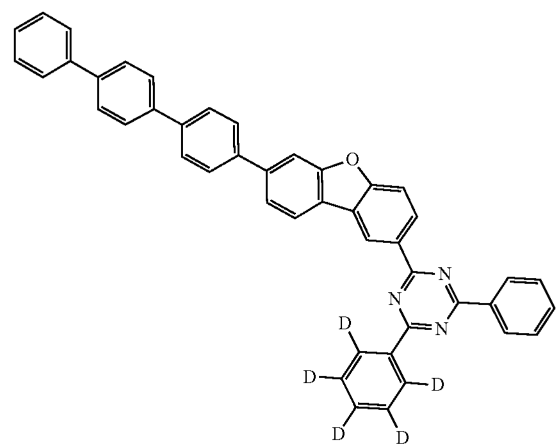
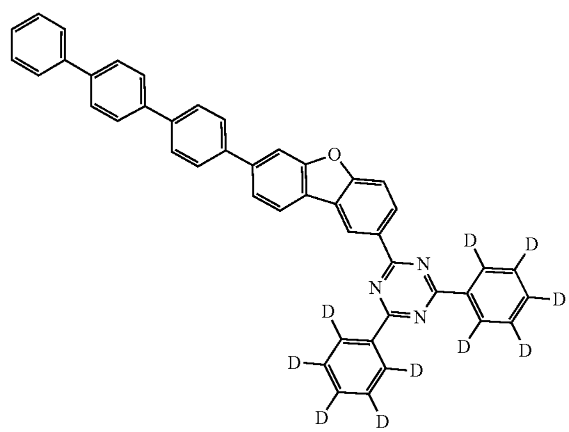
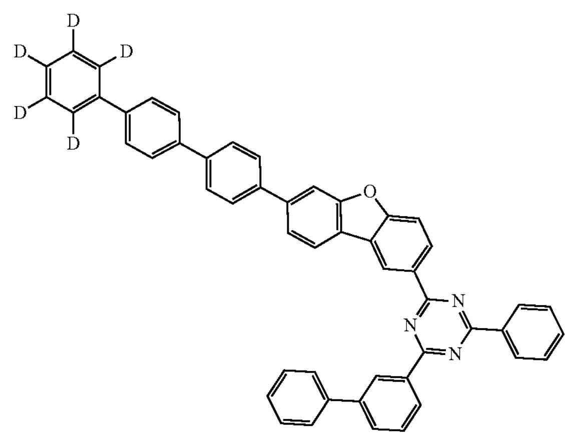
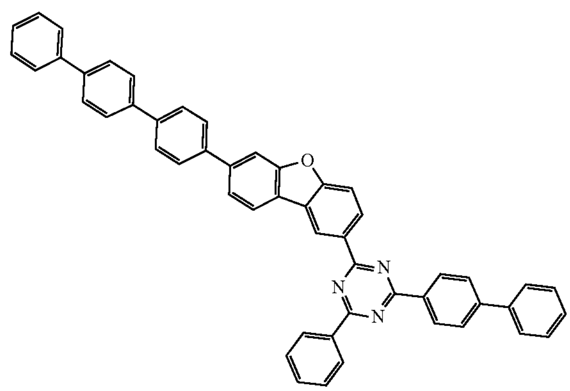
-continued
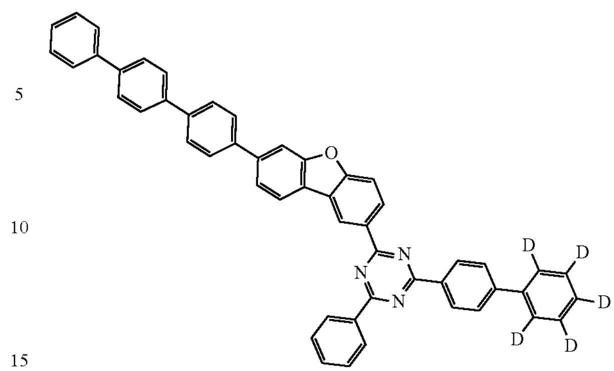
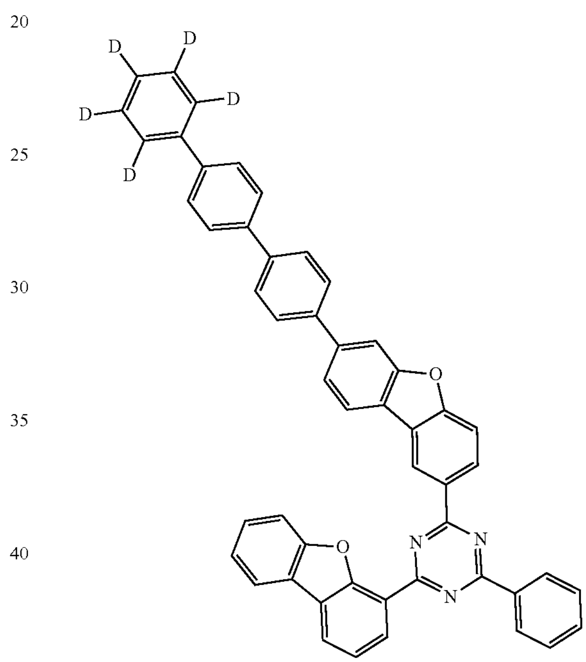
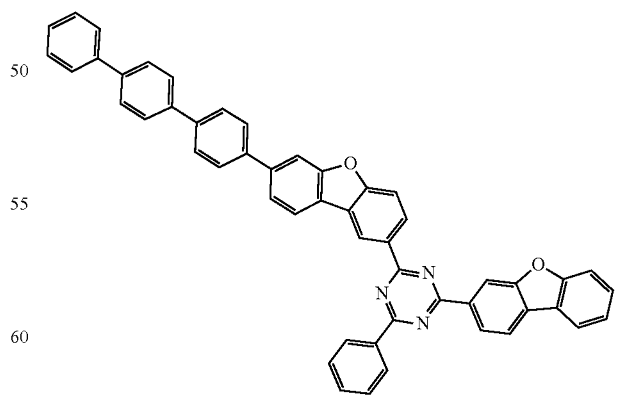

-continued
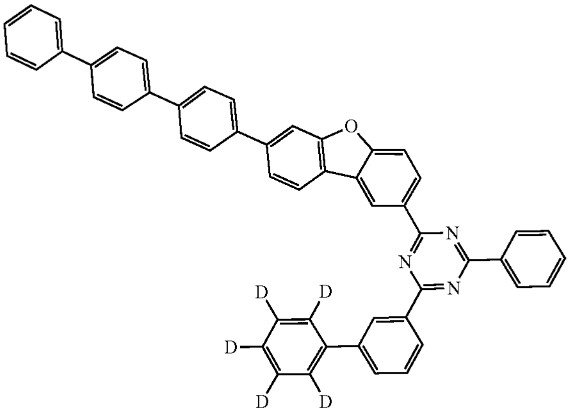
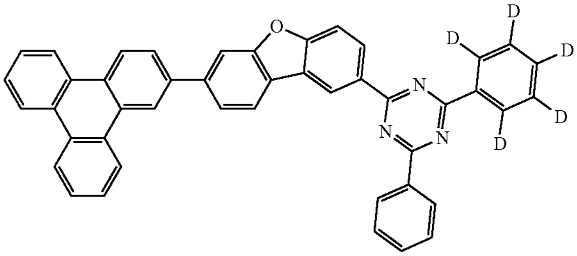
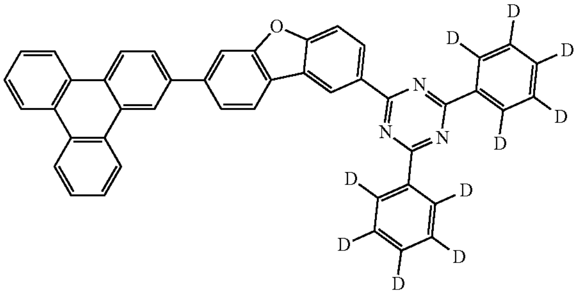
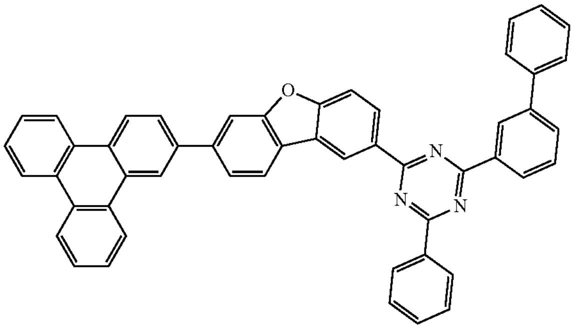
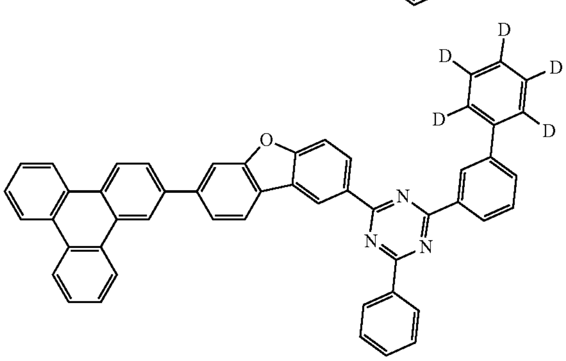
-continued
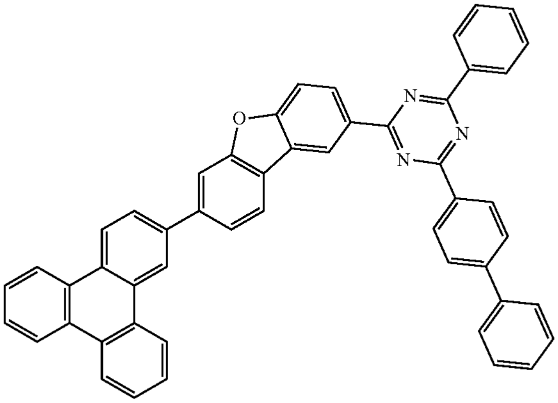
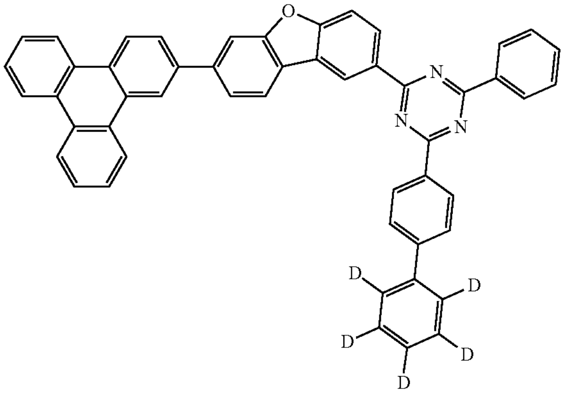
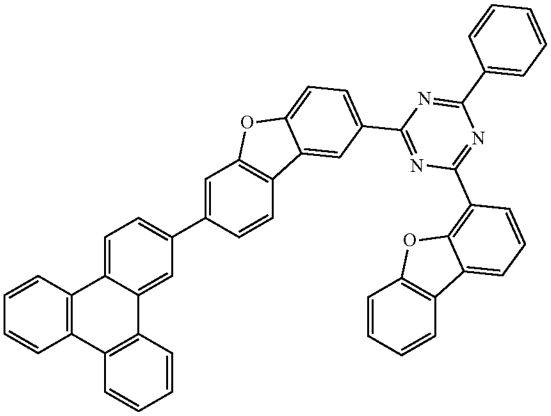
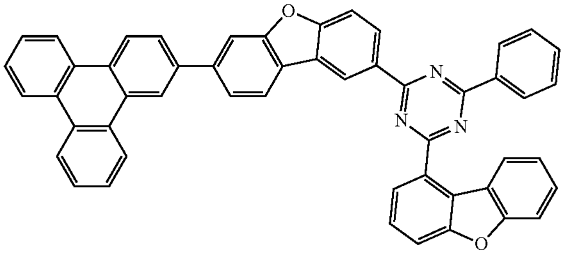

-continued
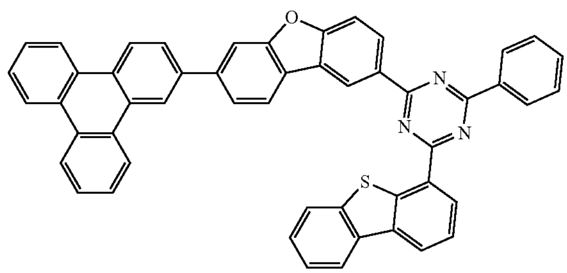
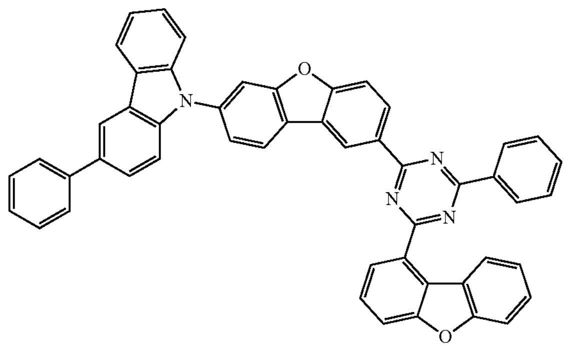
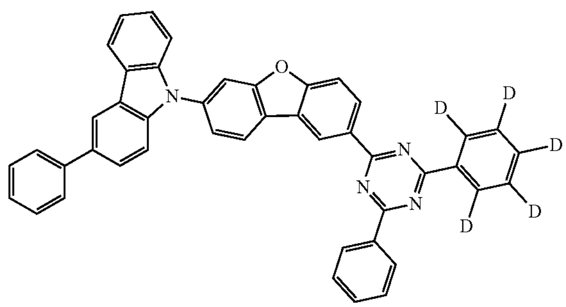
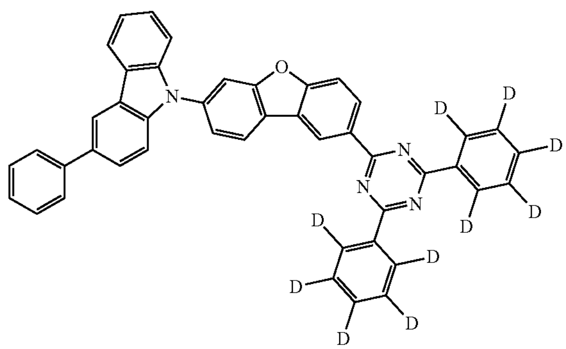
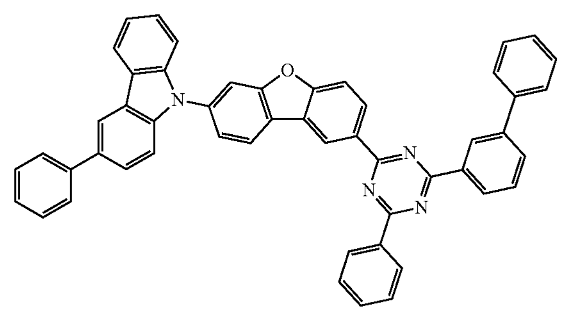
-continued
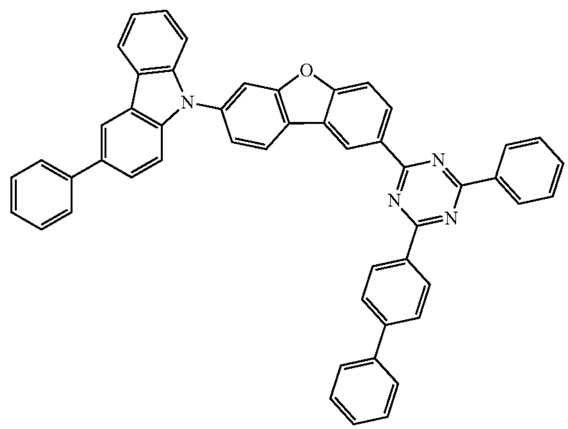
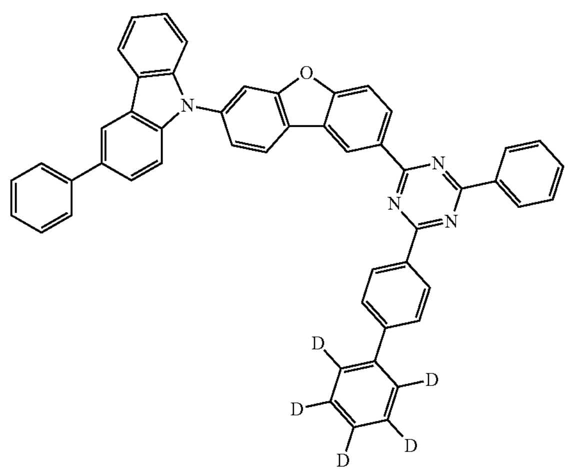
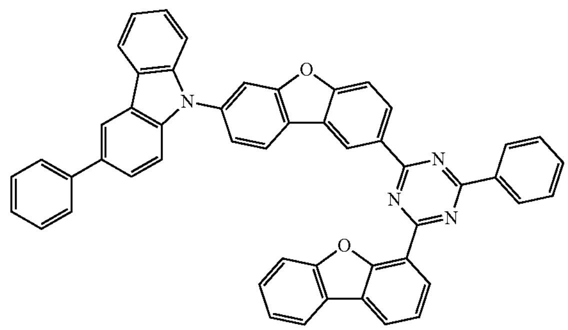
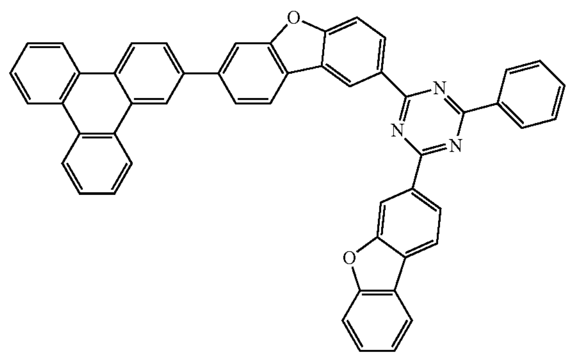

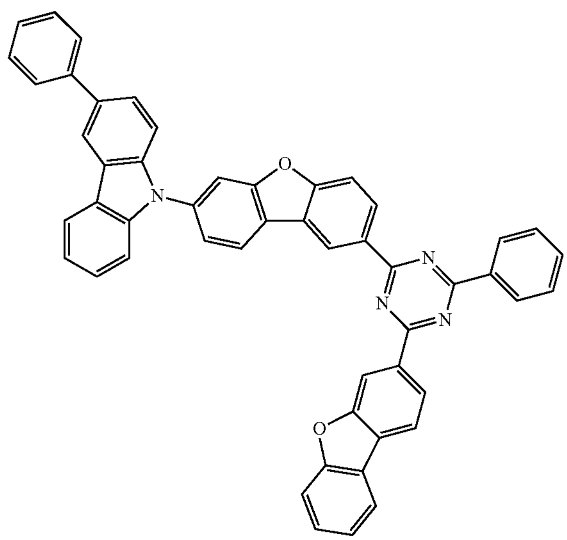
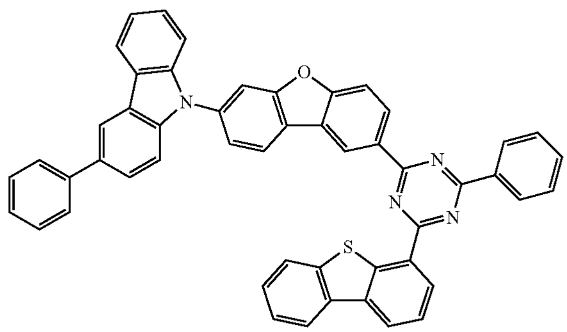
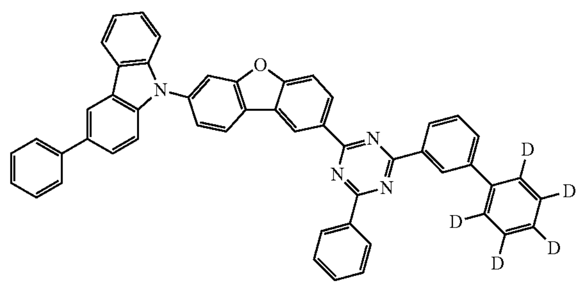
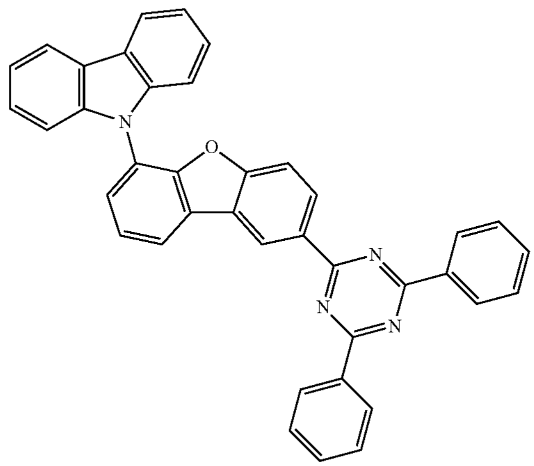
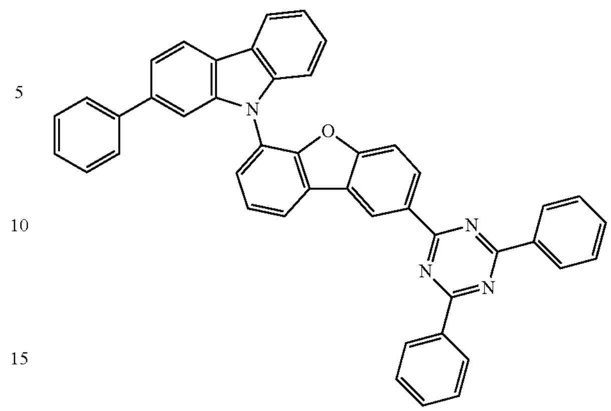
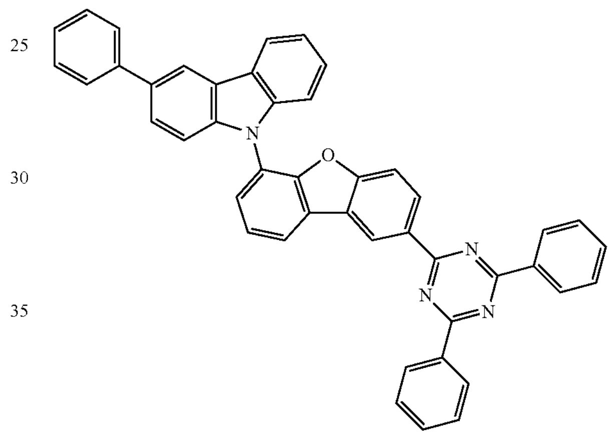
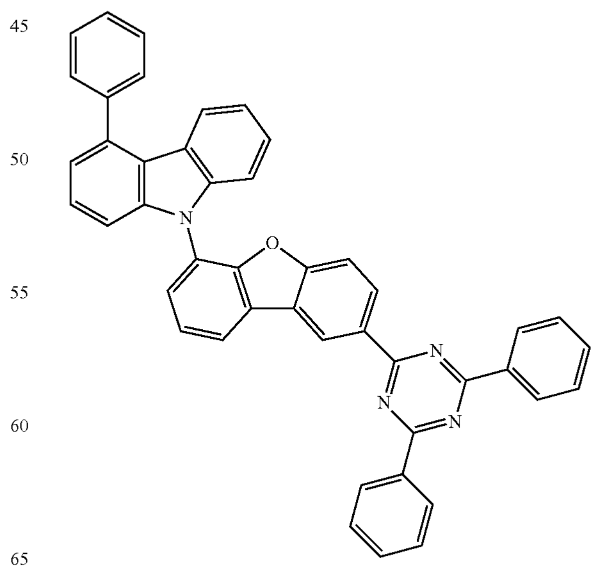

-continued
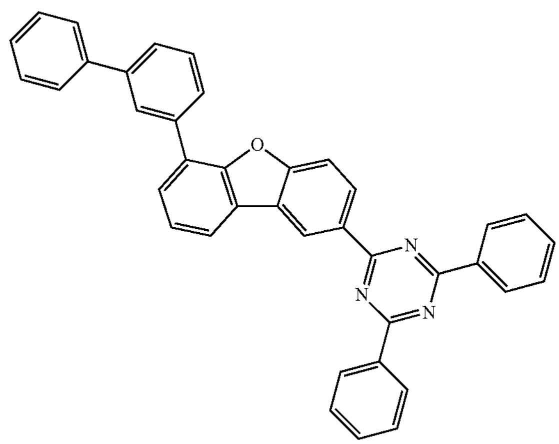
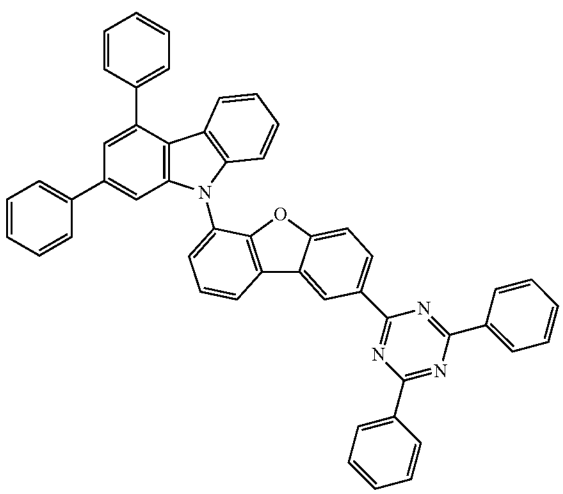
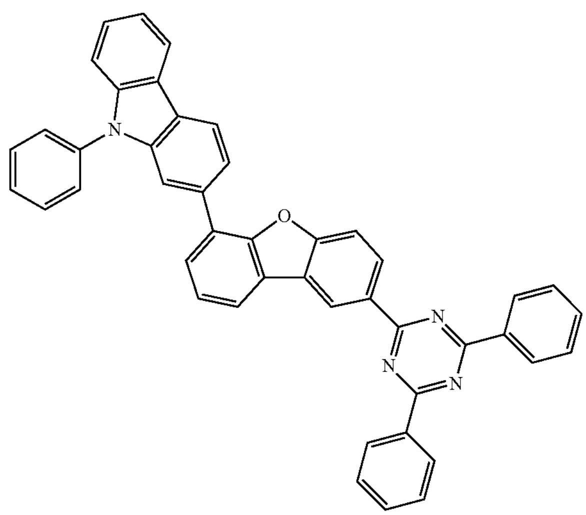
-continued
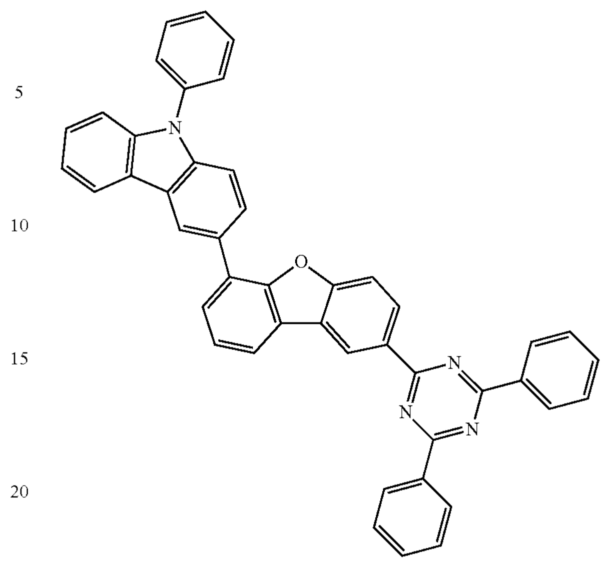
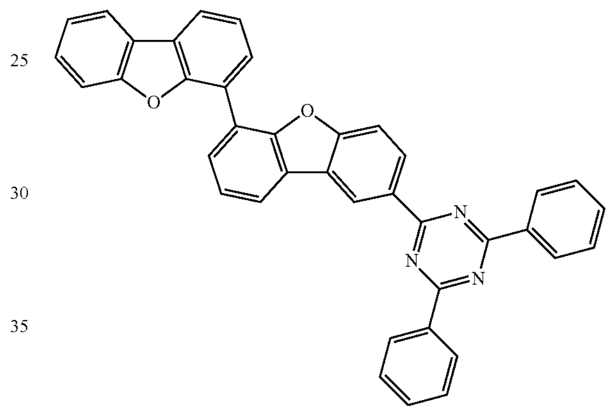
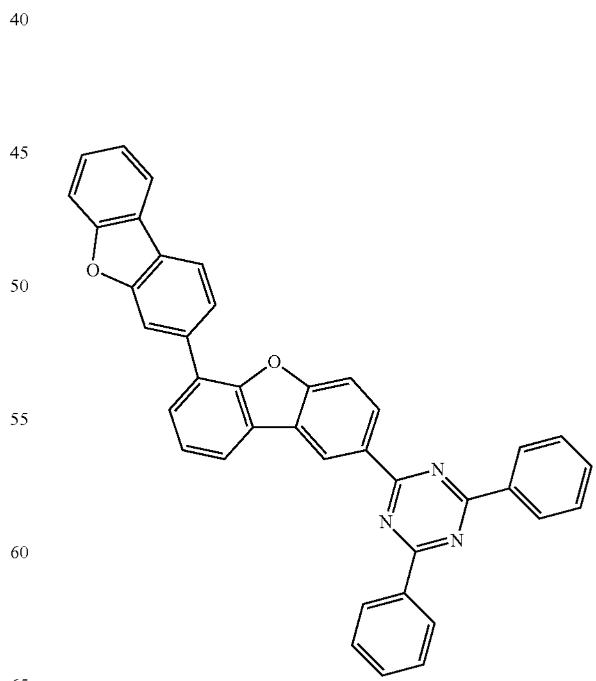

-continued
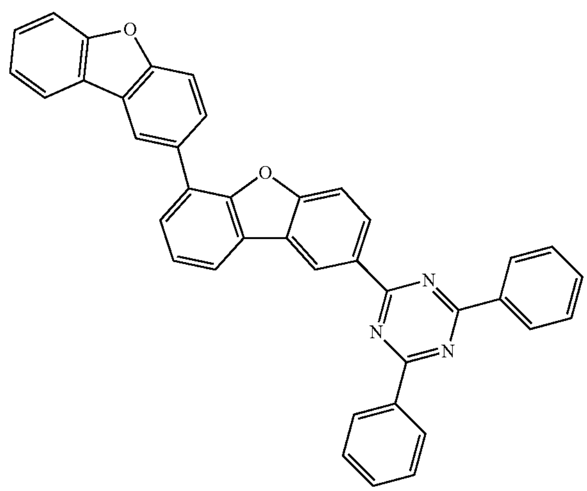
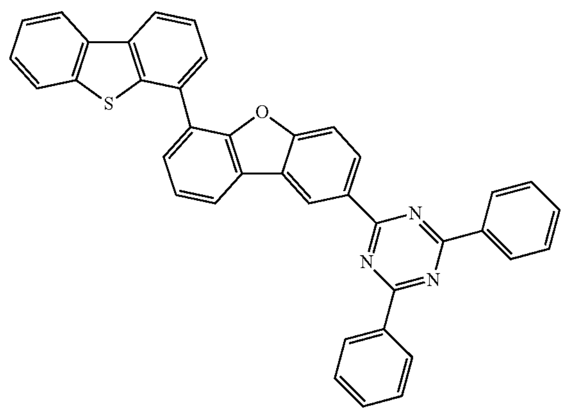
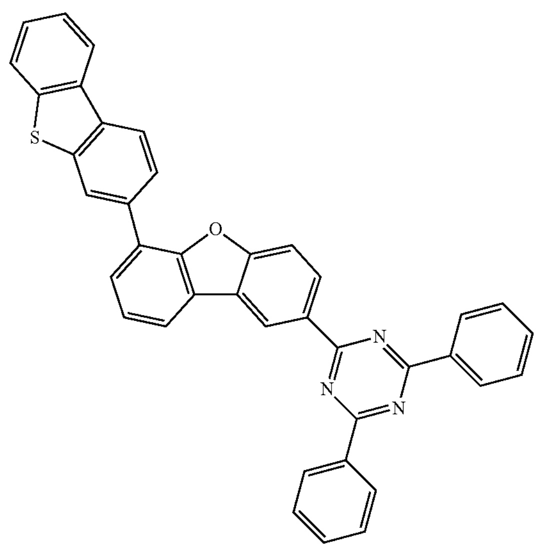
-continued
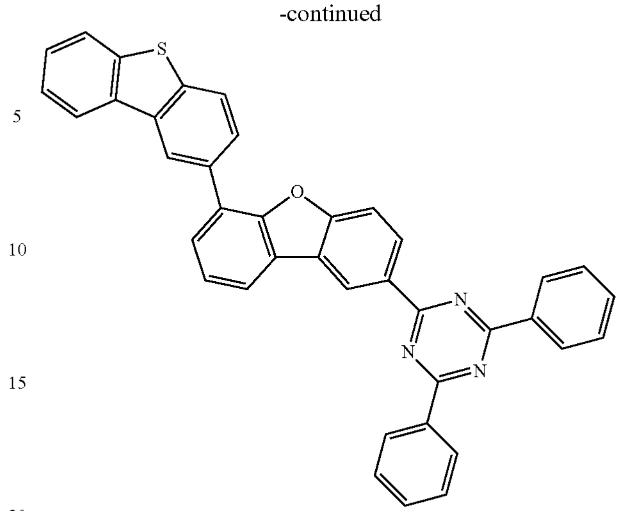
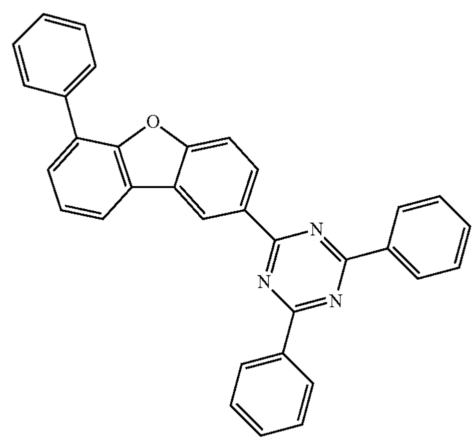
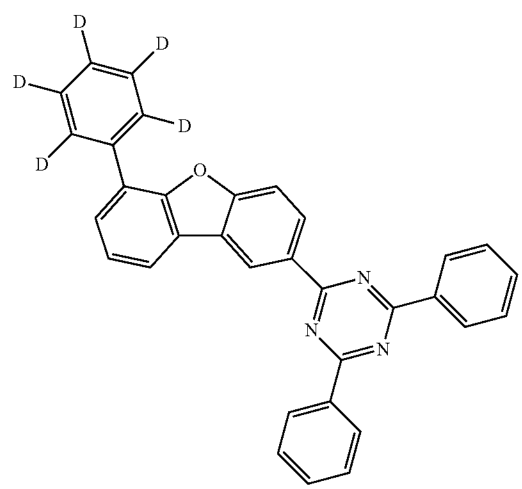

-continued
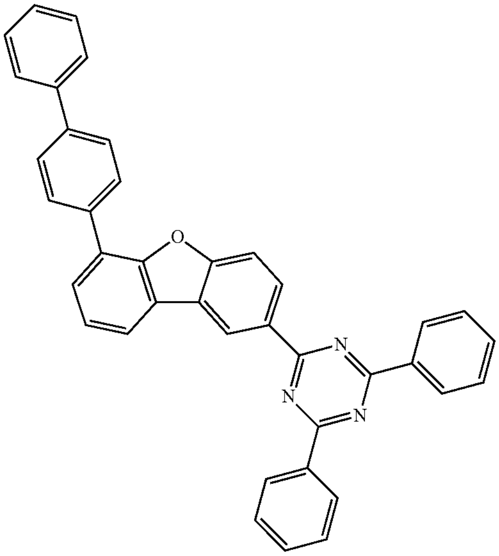
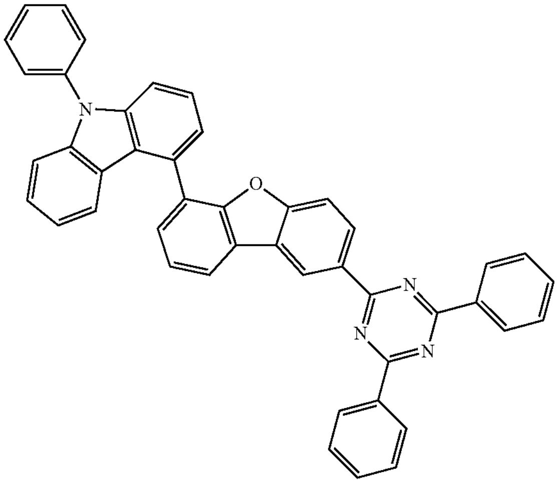
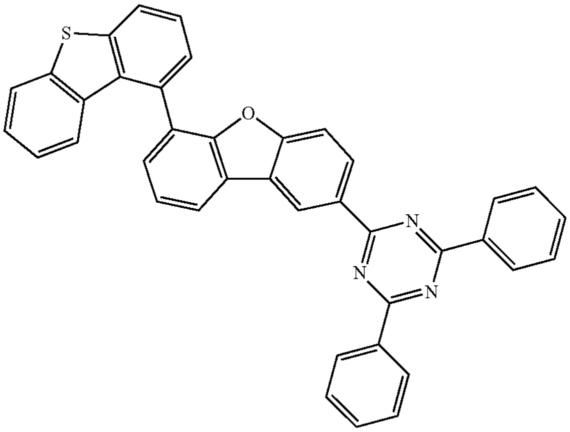
-continued
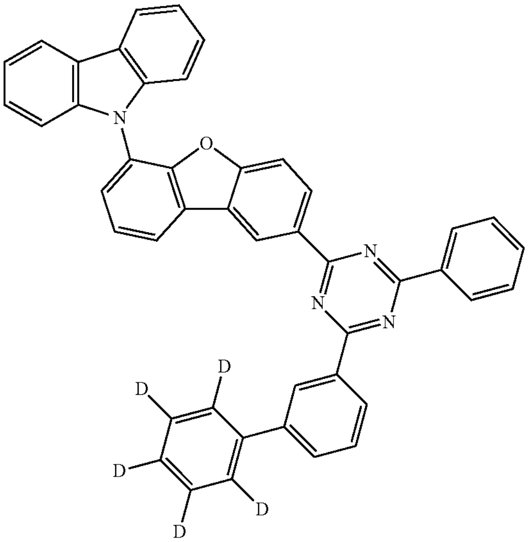
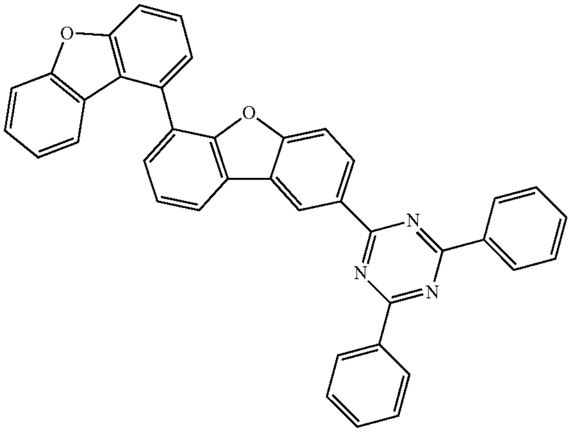
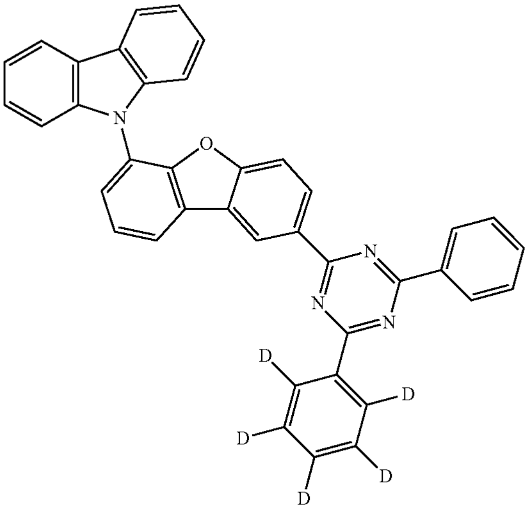

-continued
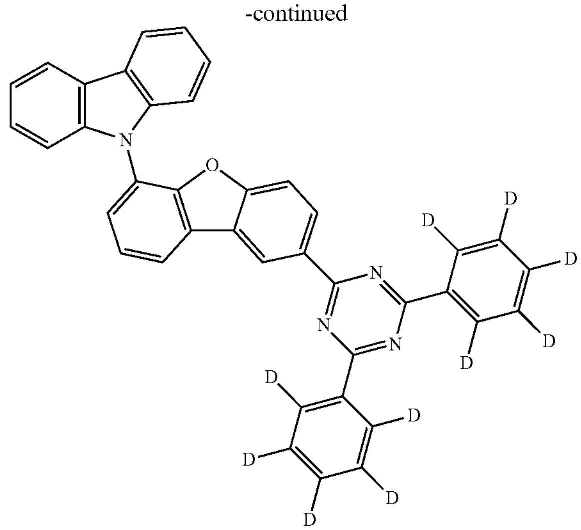
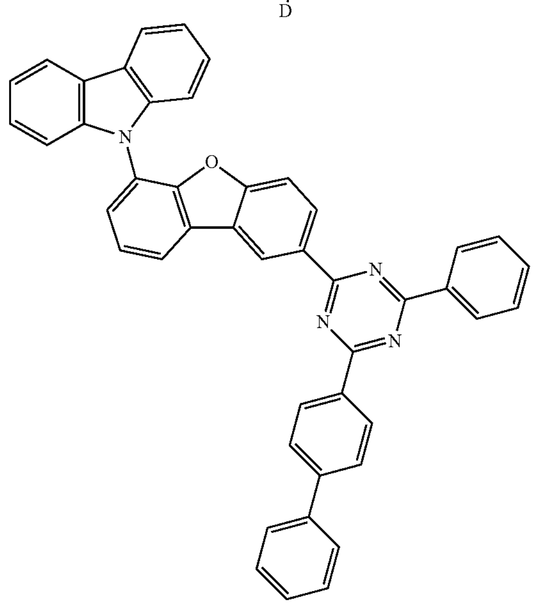
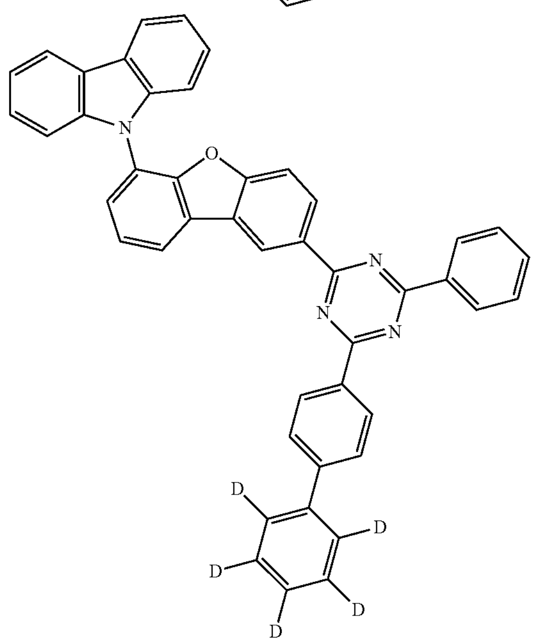
-continued
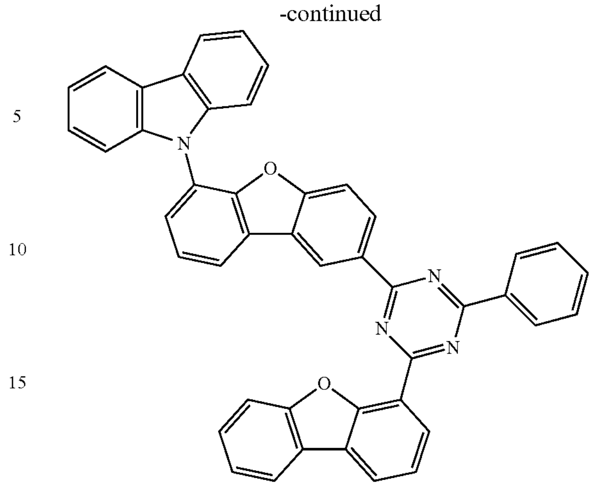
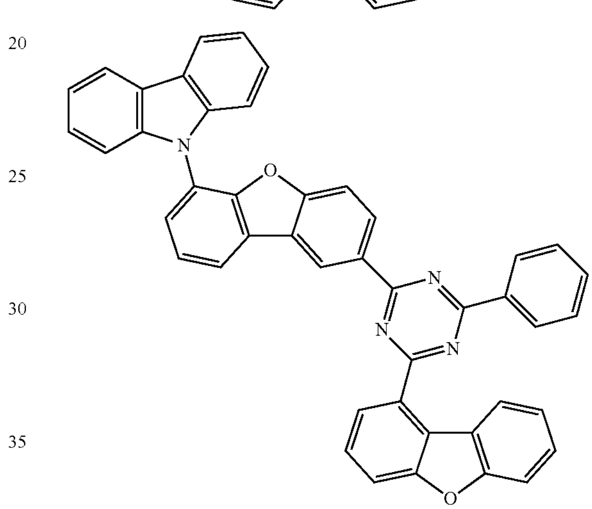
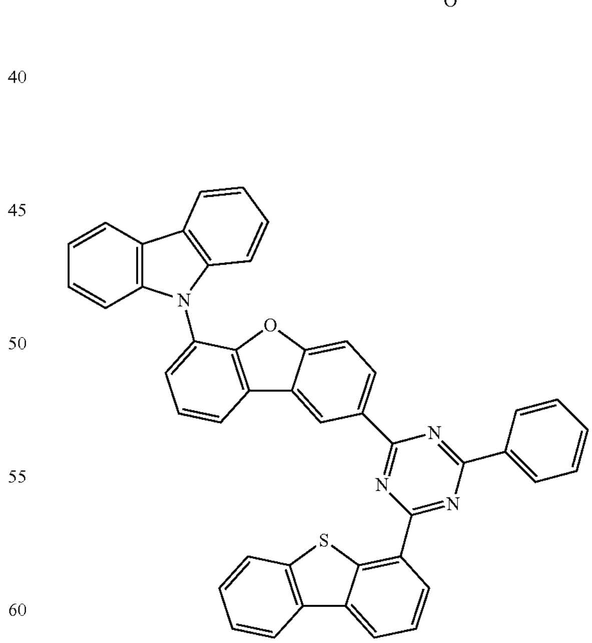

-continued
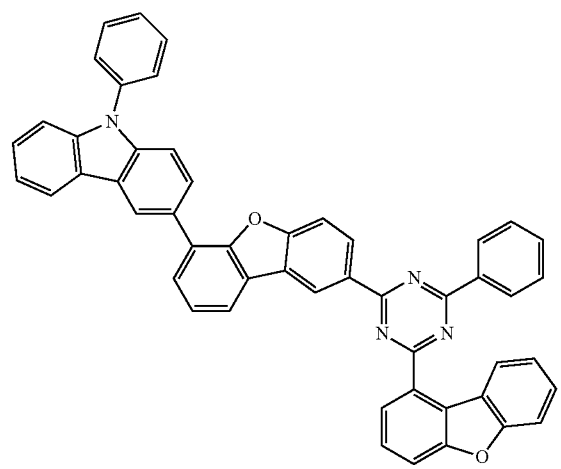
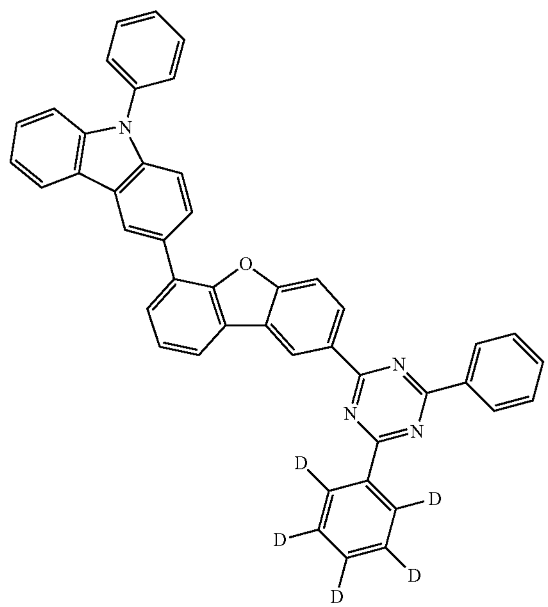
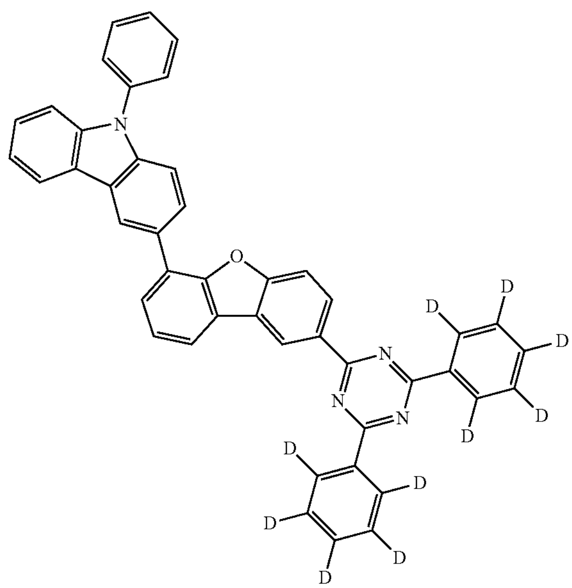
-continued
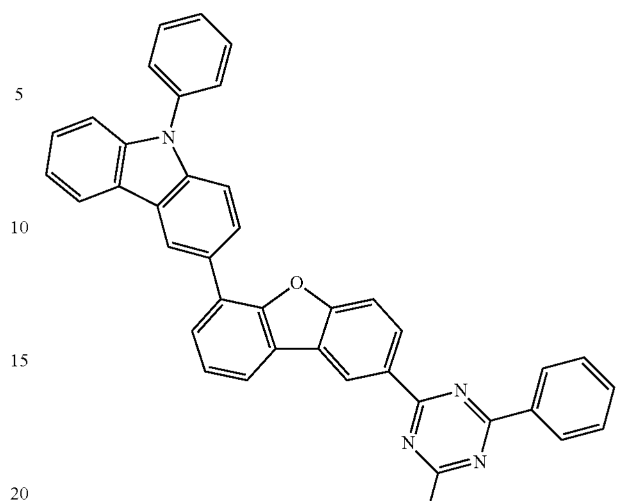
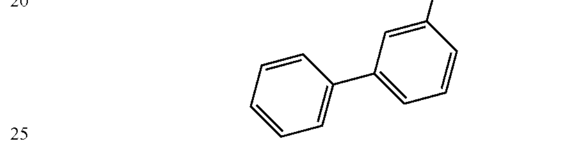
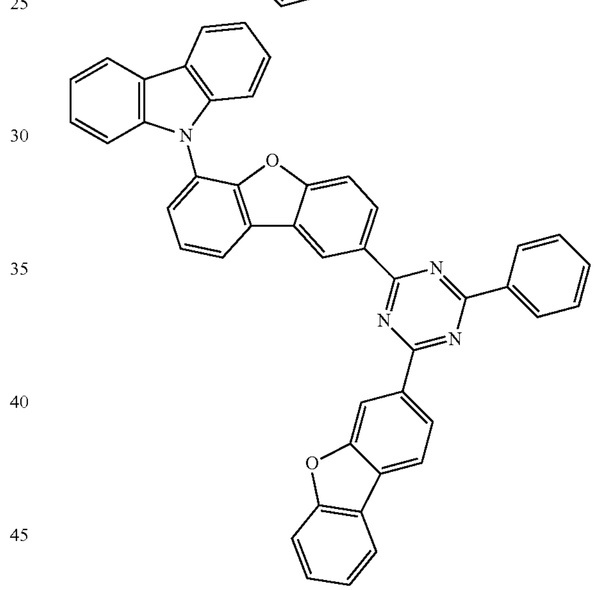
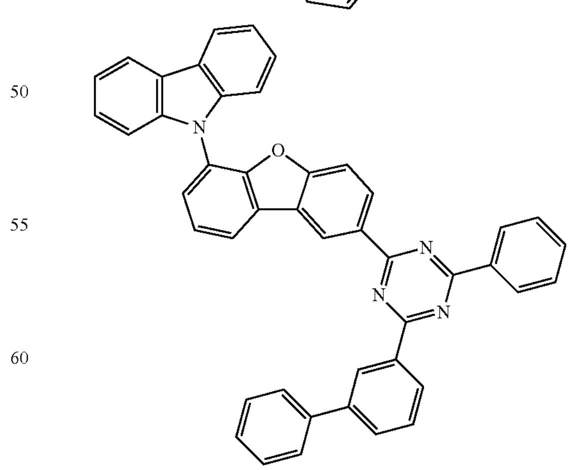

-continued
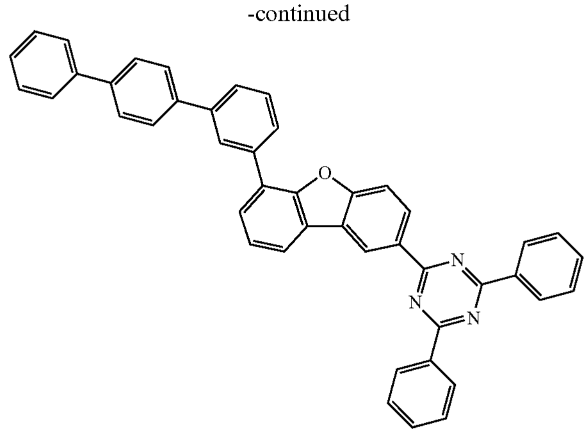
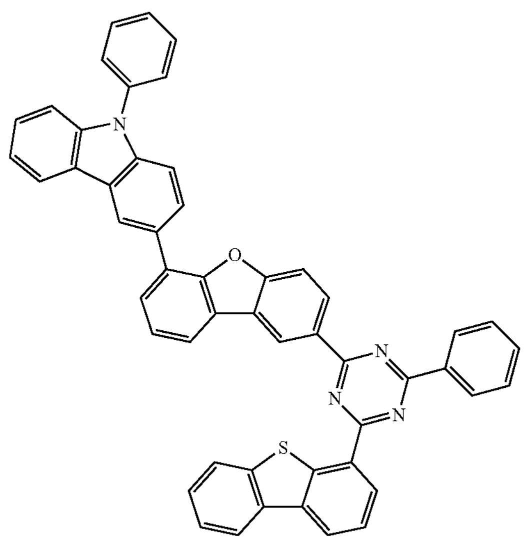
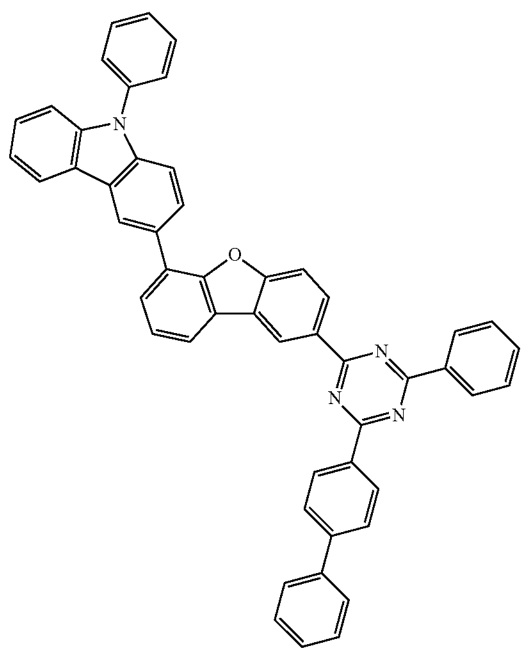
-continued
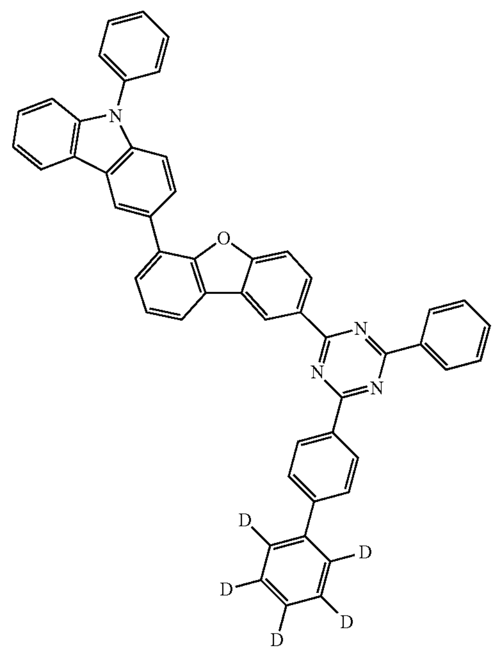
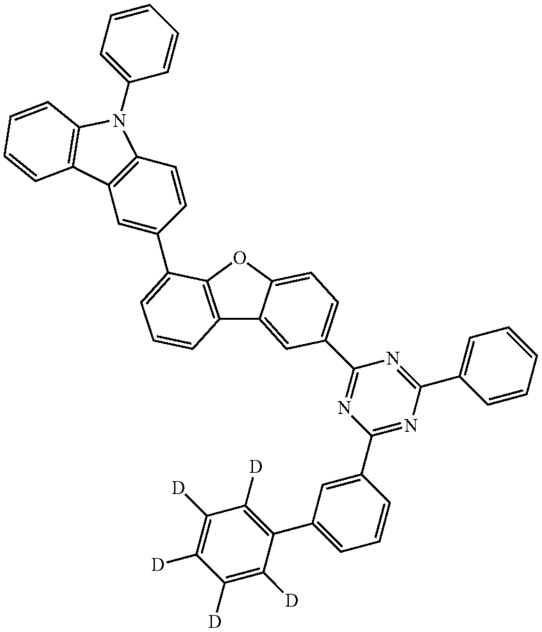

-continued
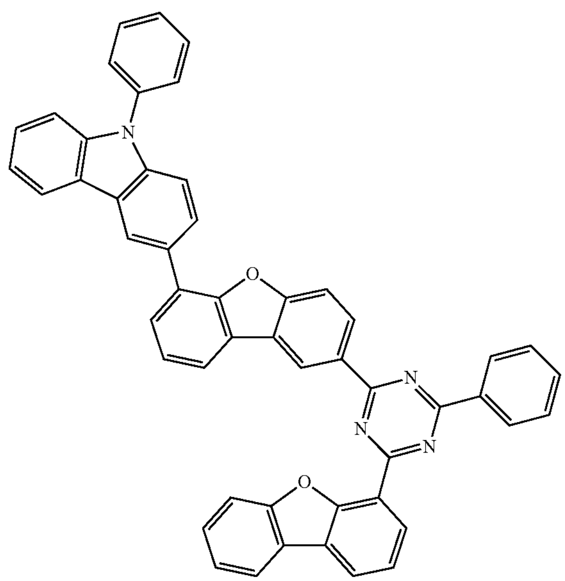
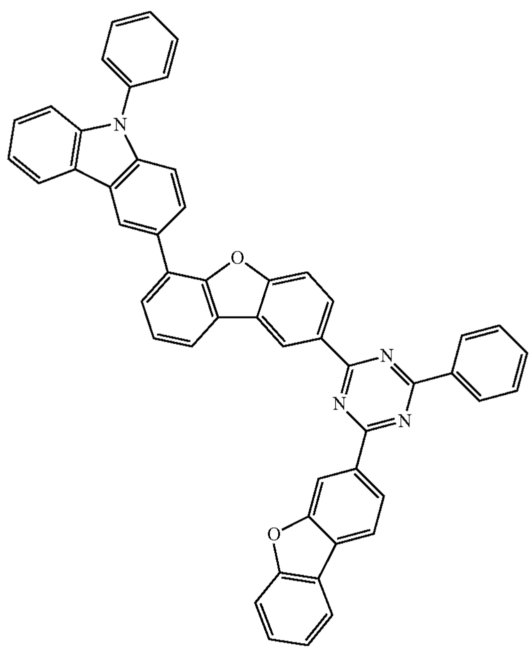
-continued
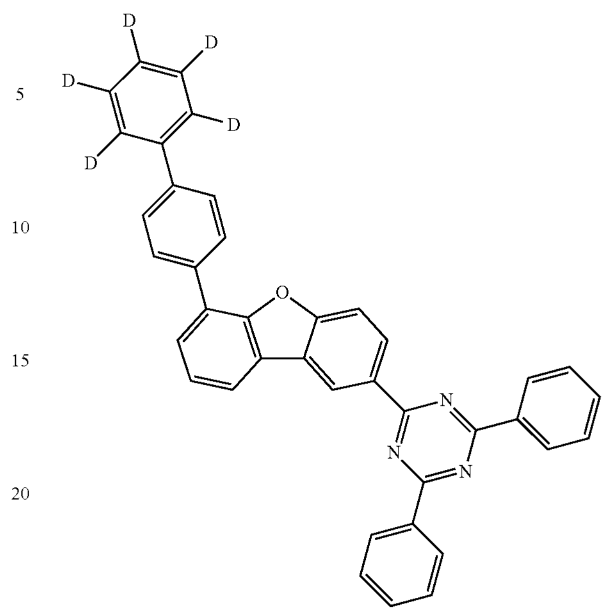
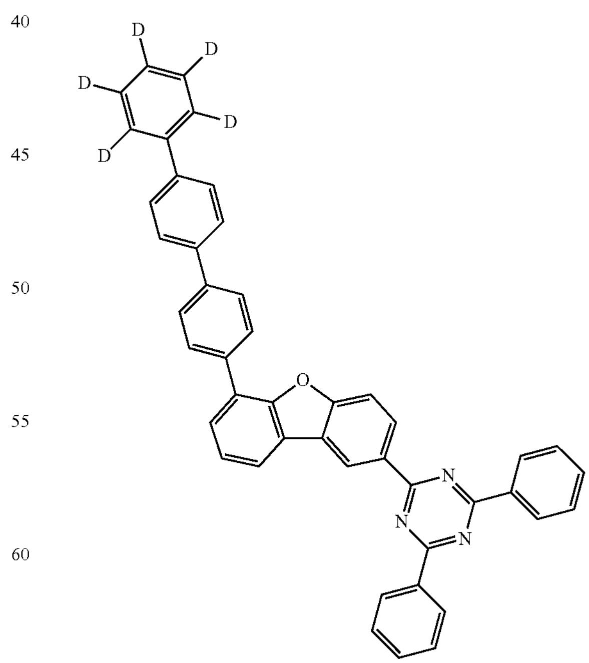

-continued
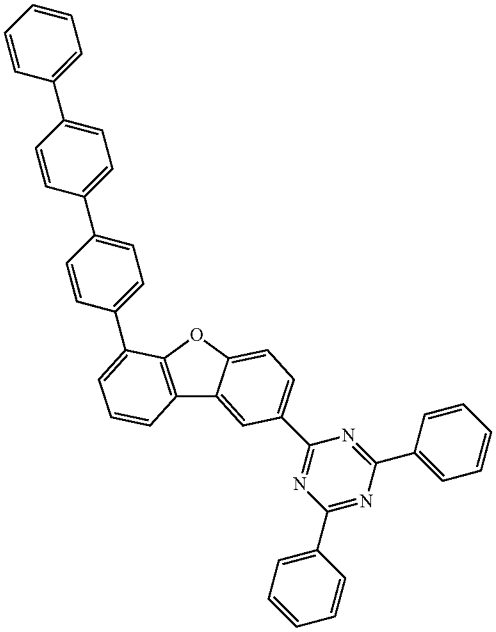
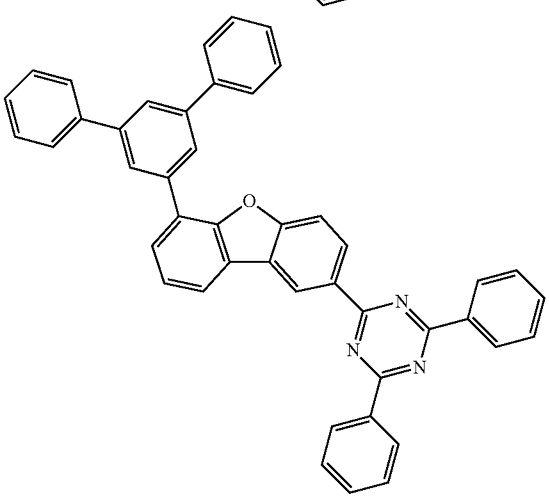
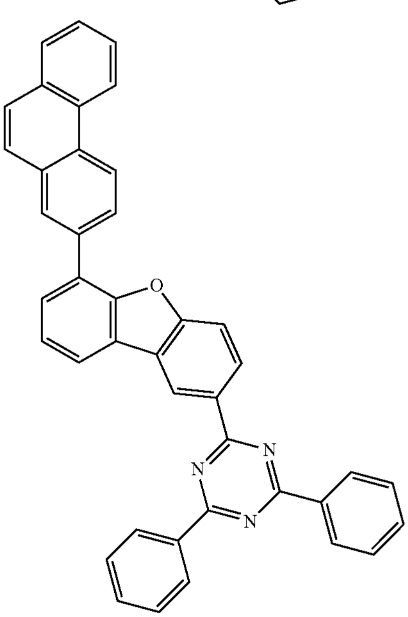
-continued
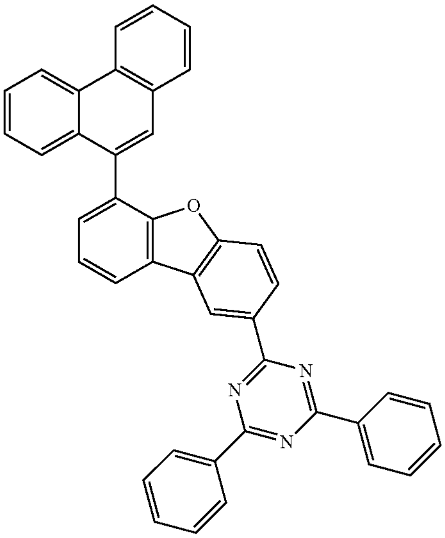
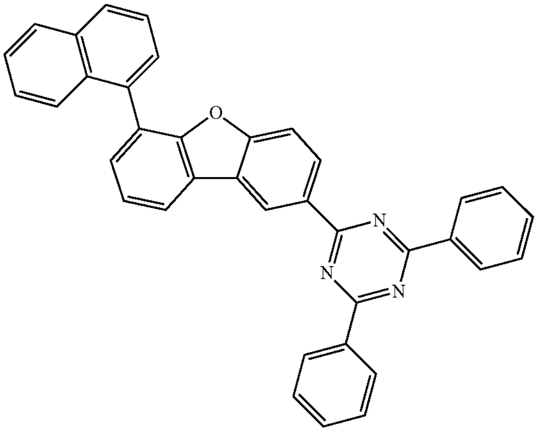
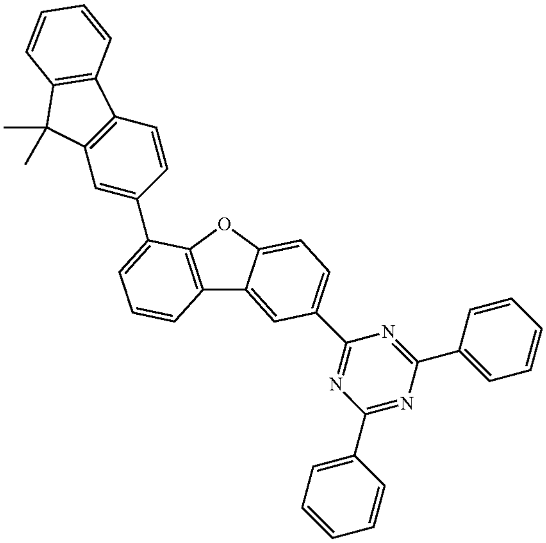

-continued
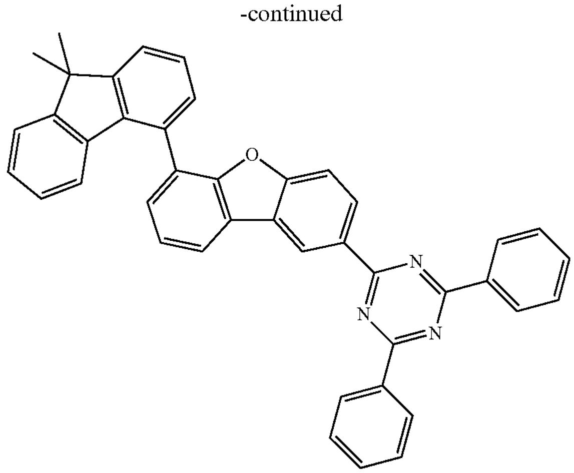
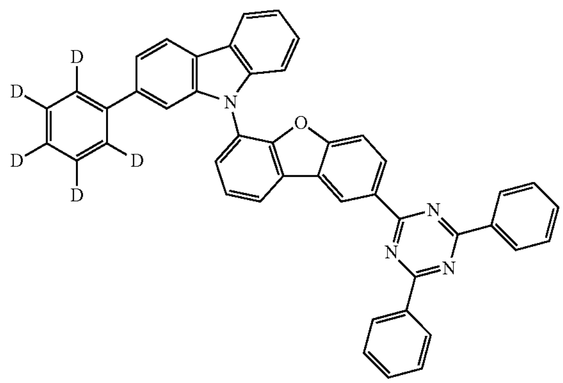
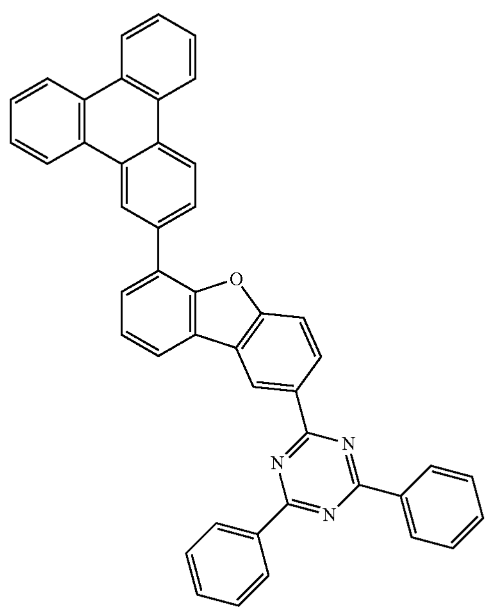
-continued
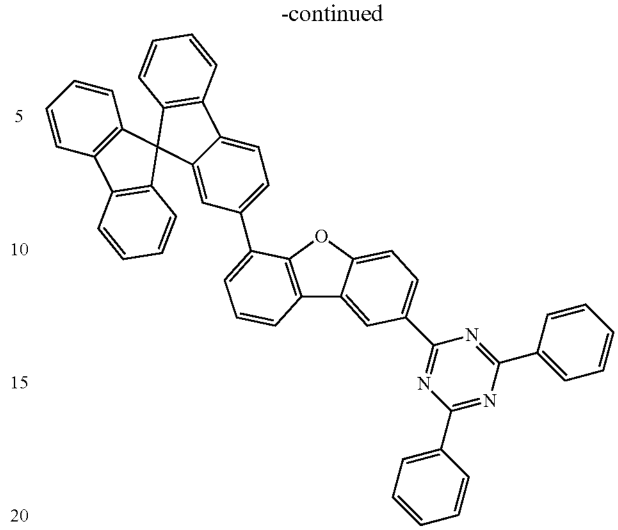
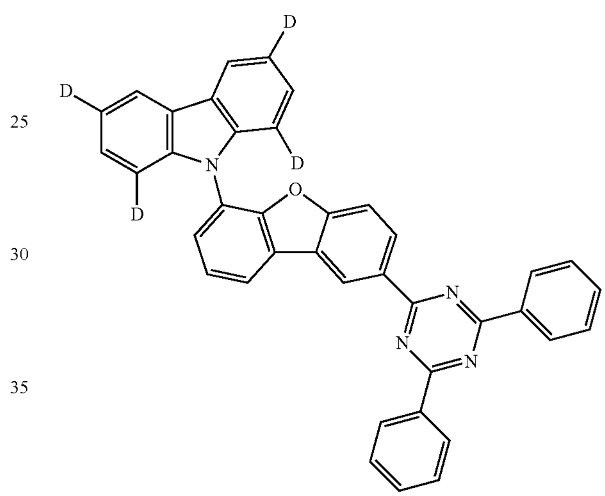
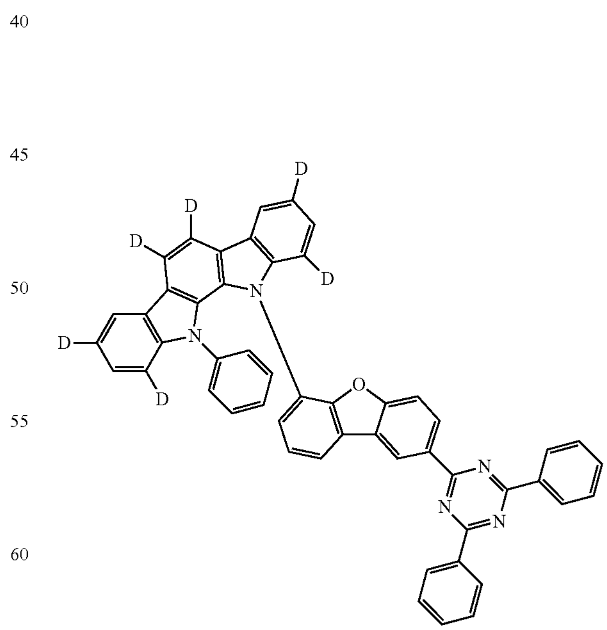

-continued
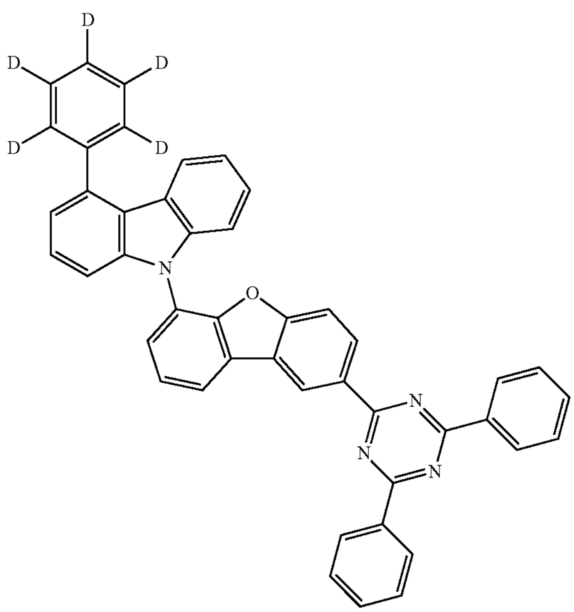
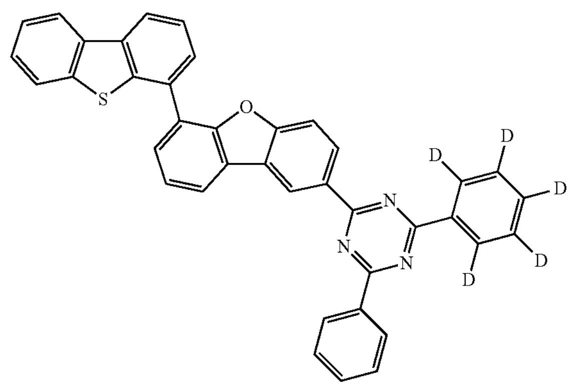
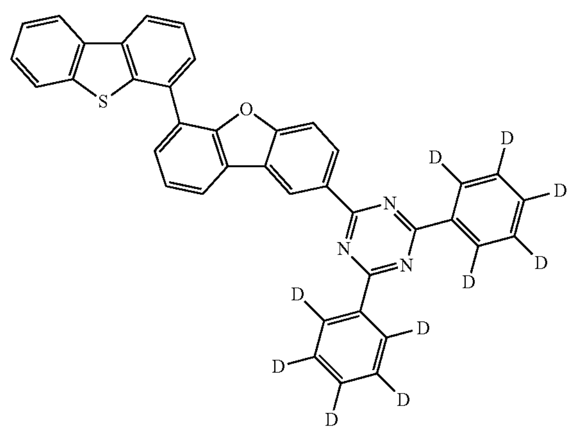
-continued
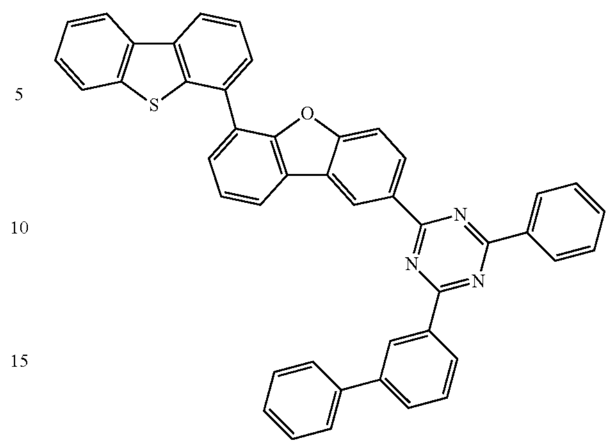
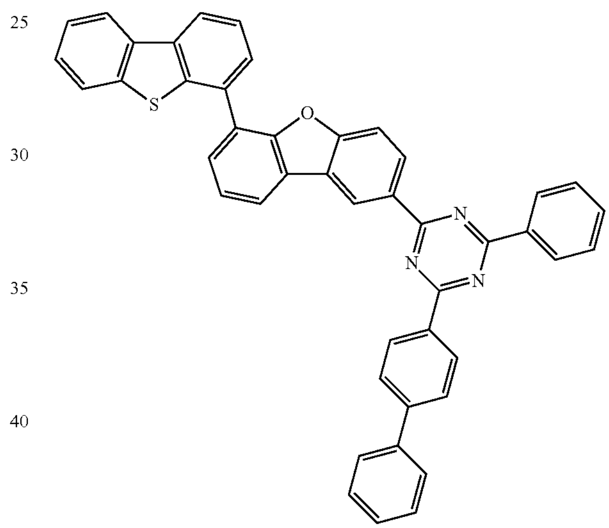
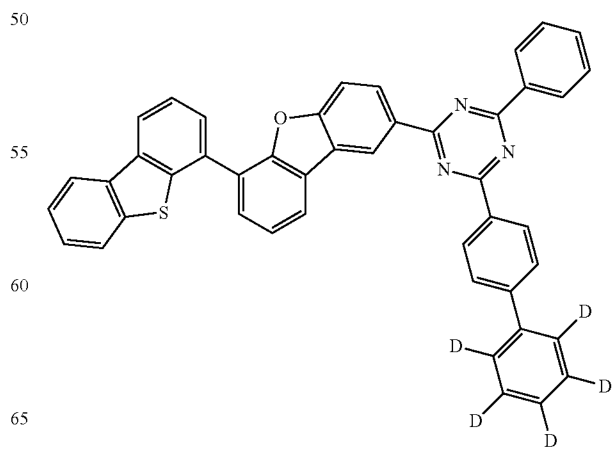

-continued
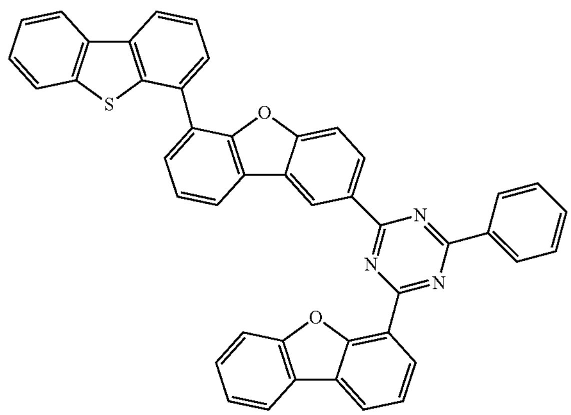
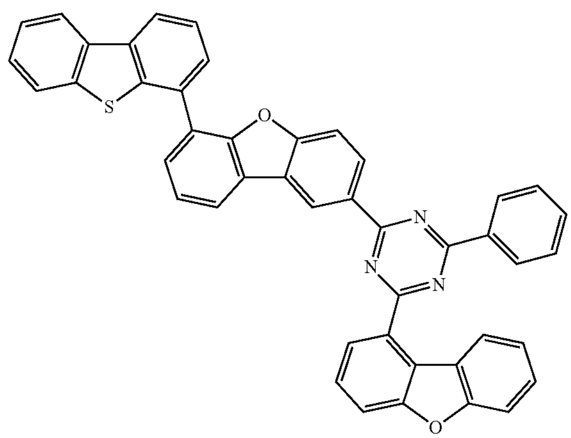
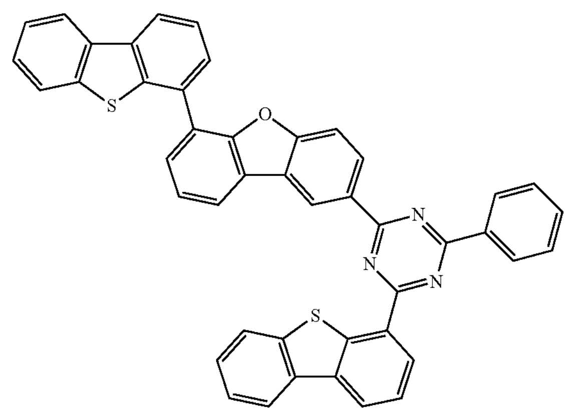
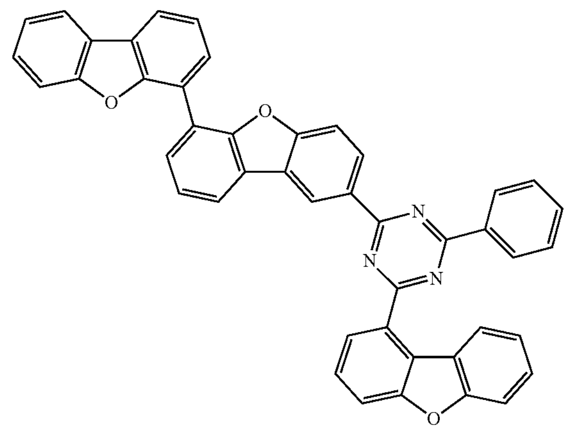
-continued
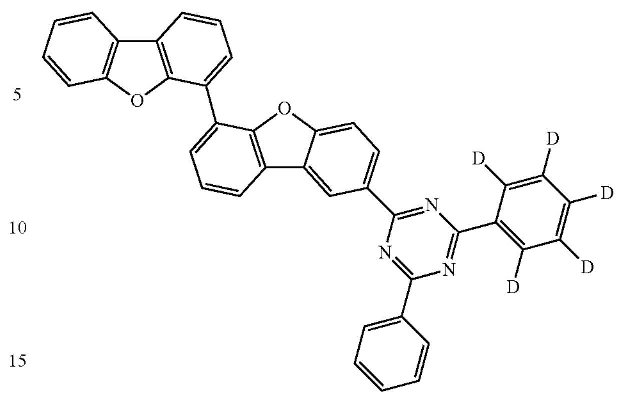
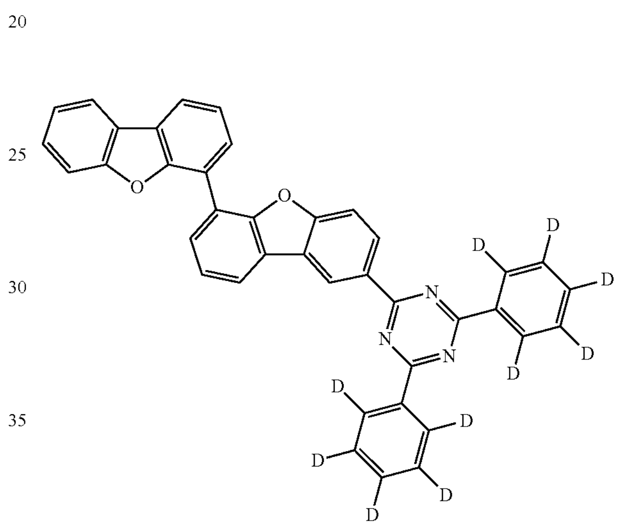
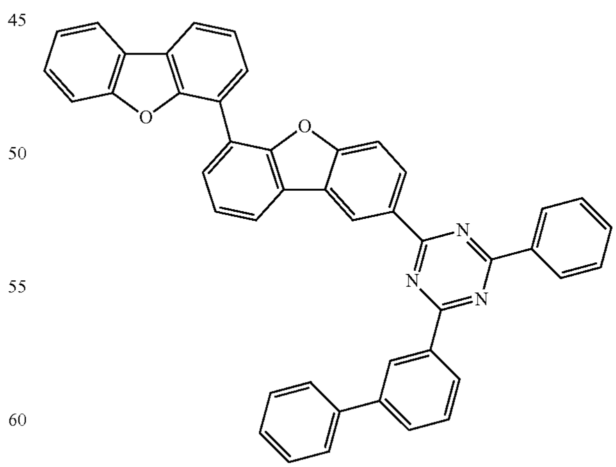

-continued
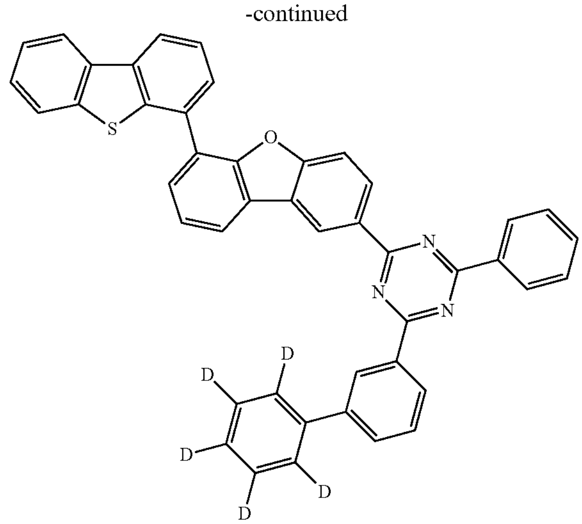
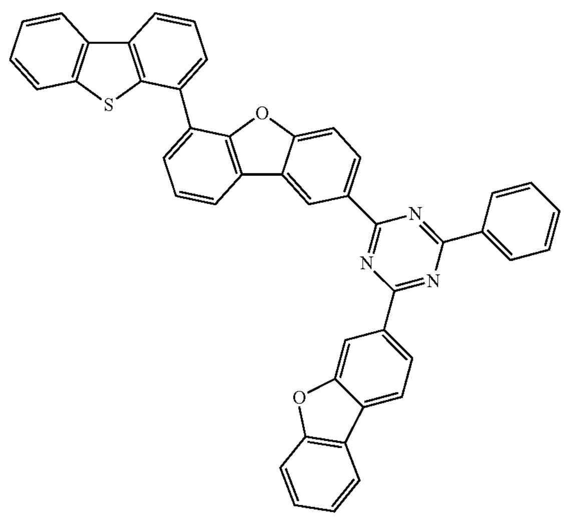
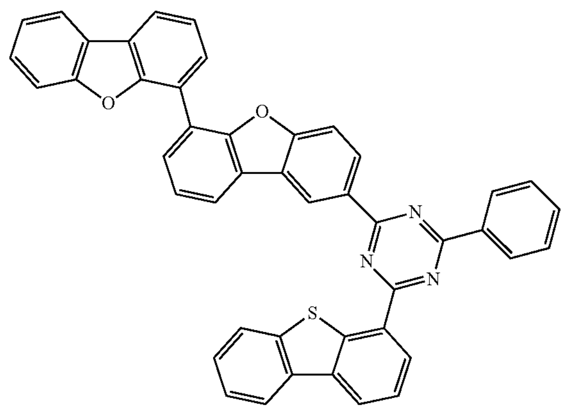
-continued
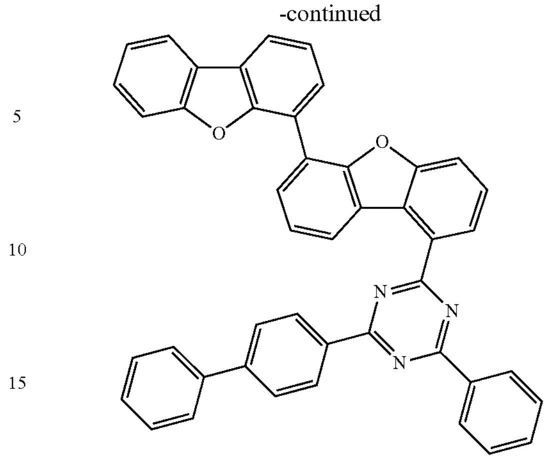
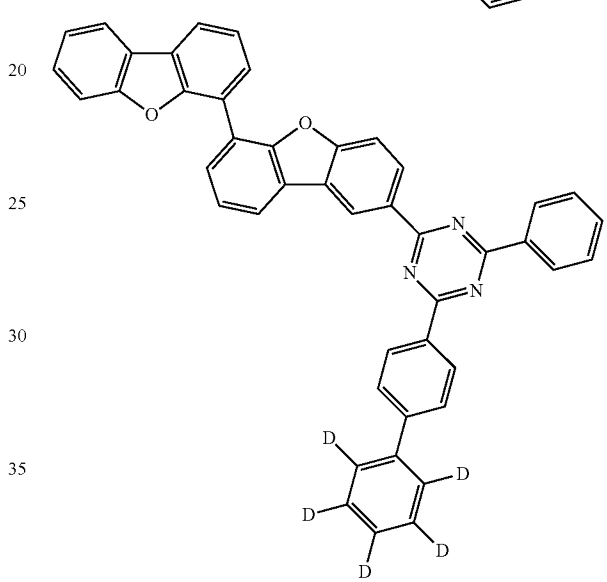
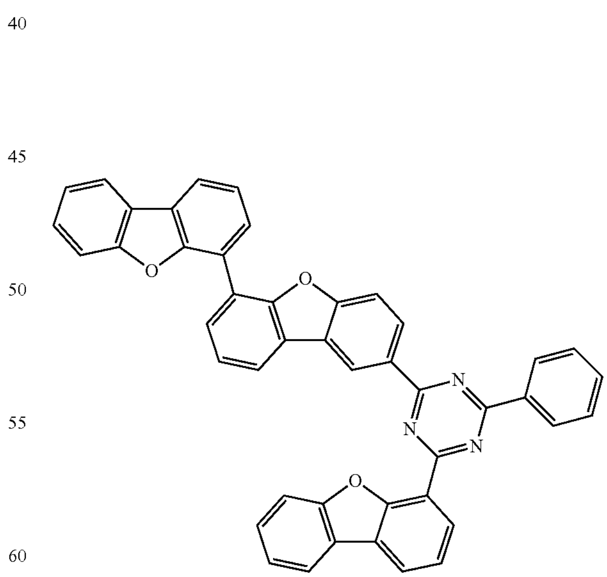

-continued
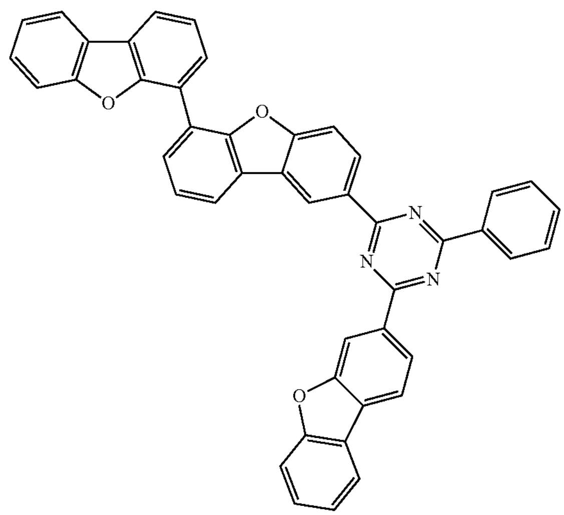
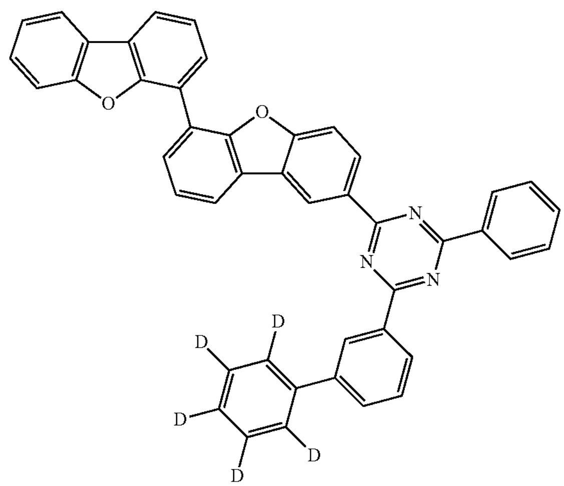
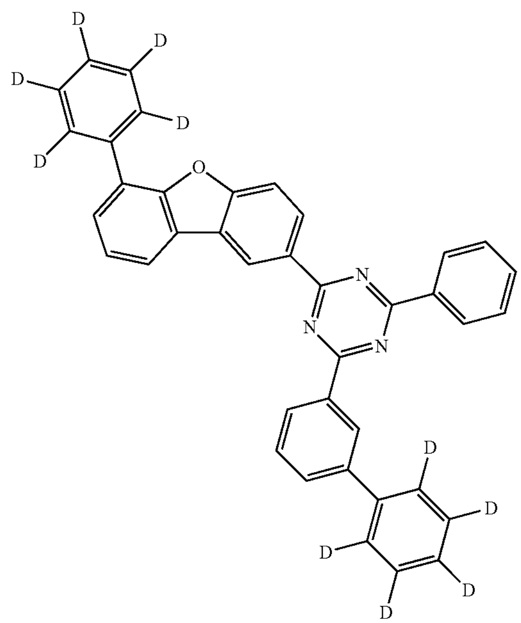
-continued
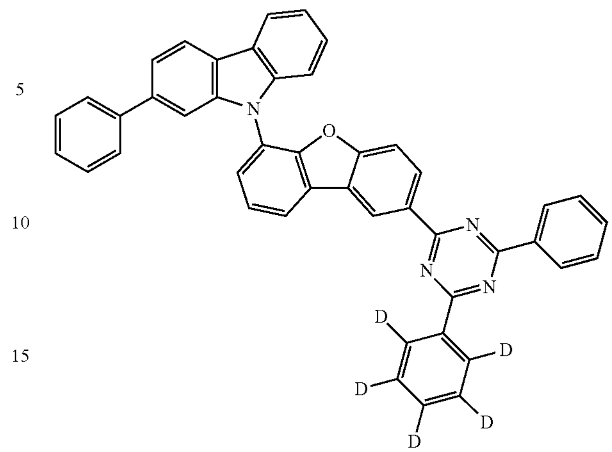
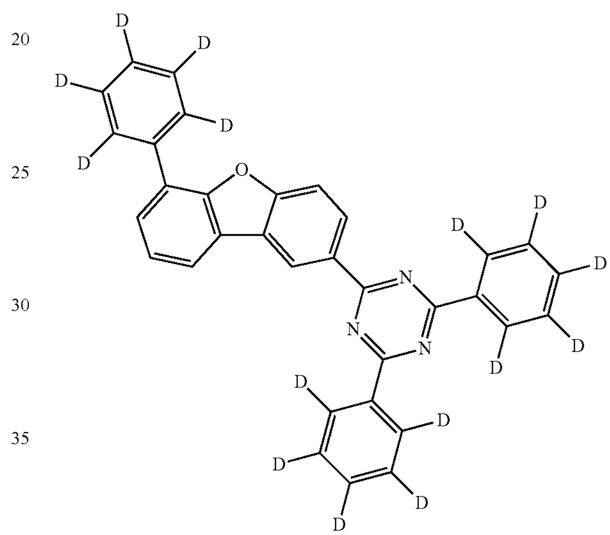
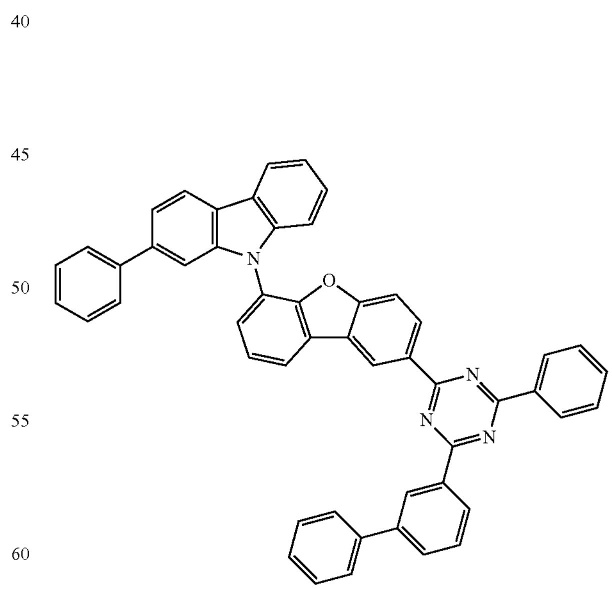

-continued
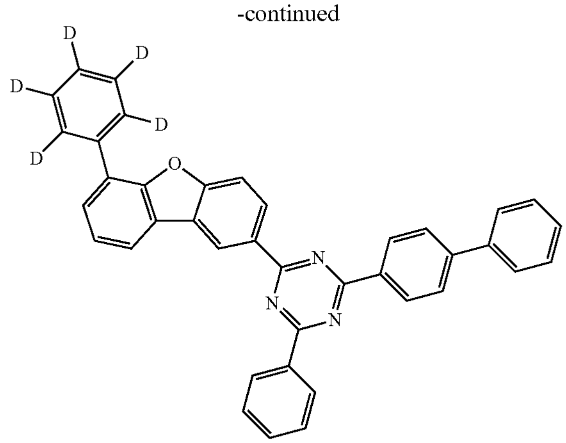
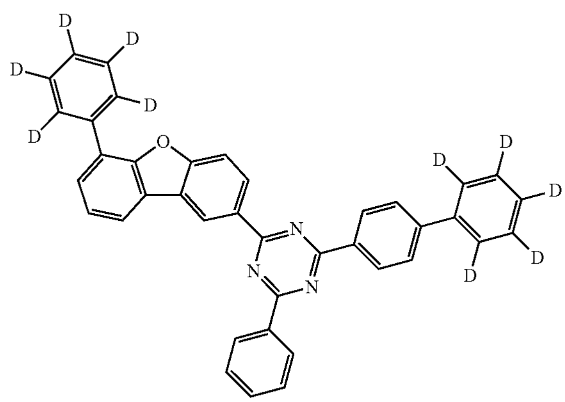
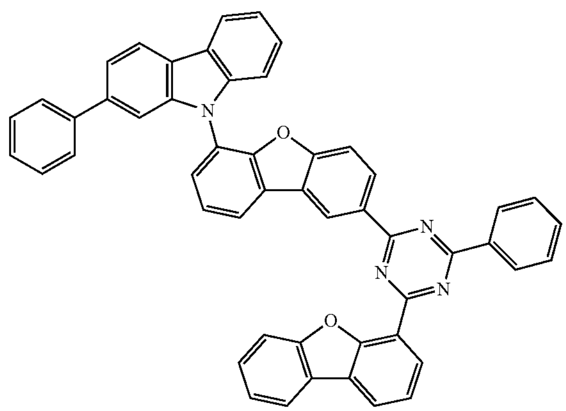
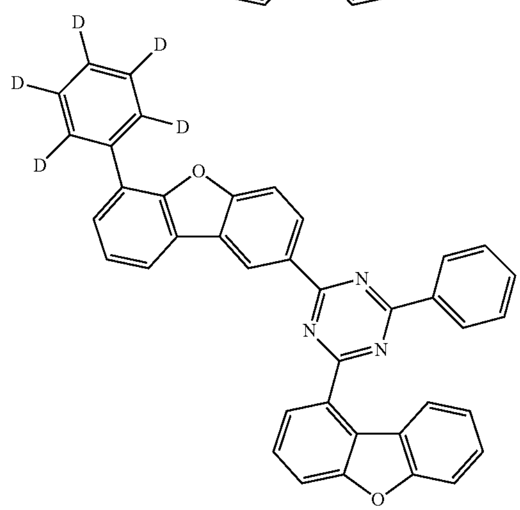
-continued
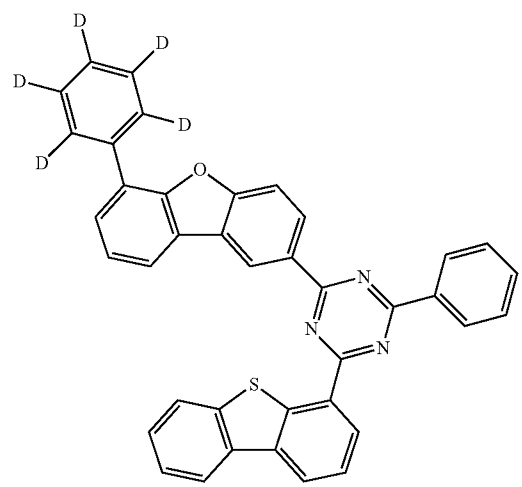
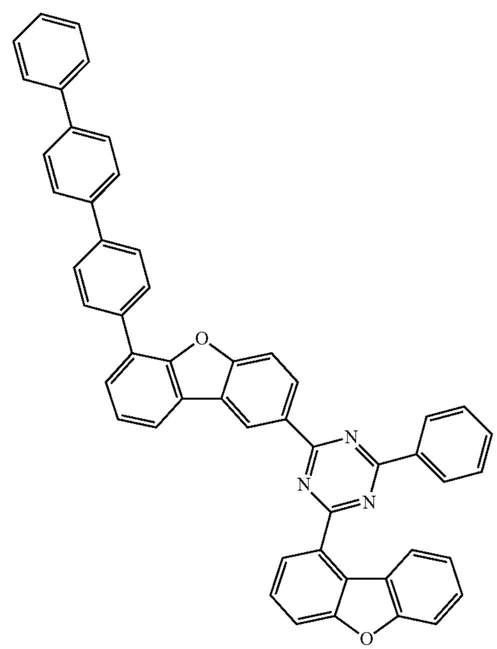
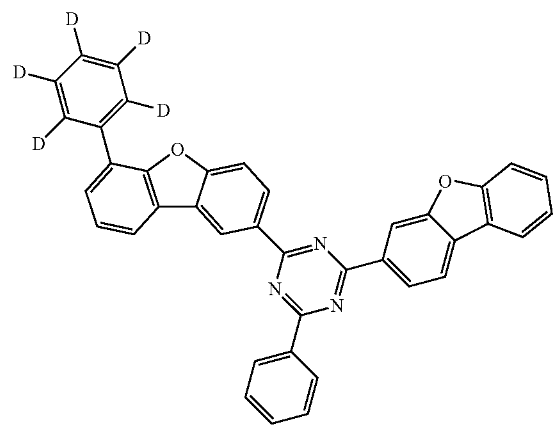

-continued
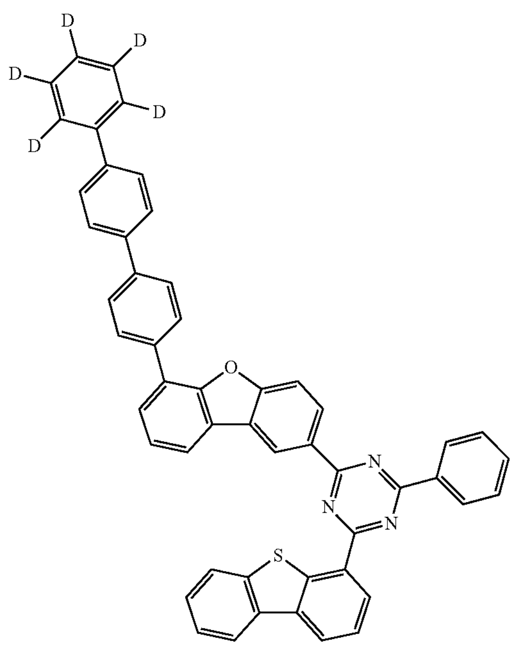
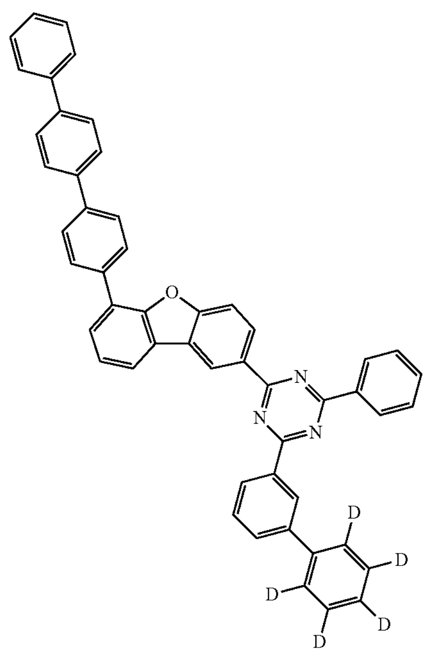
-continued
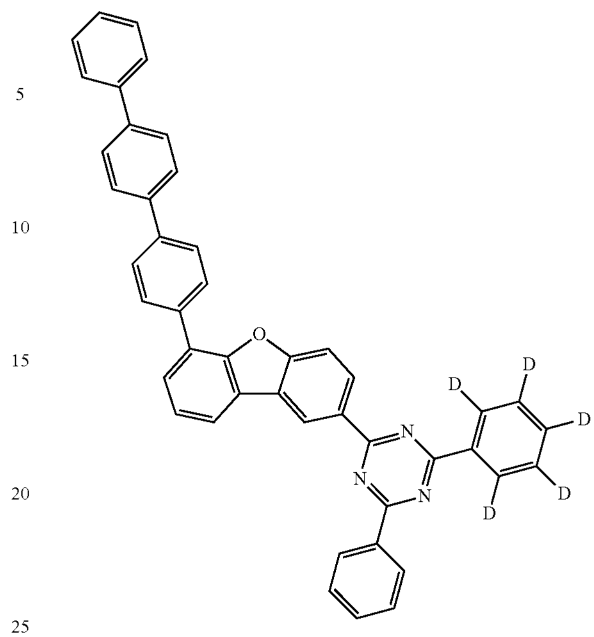
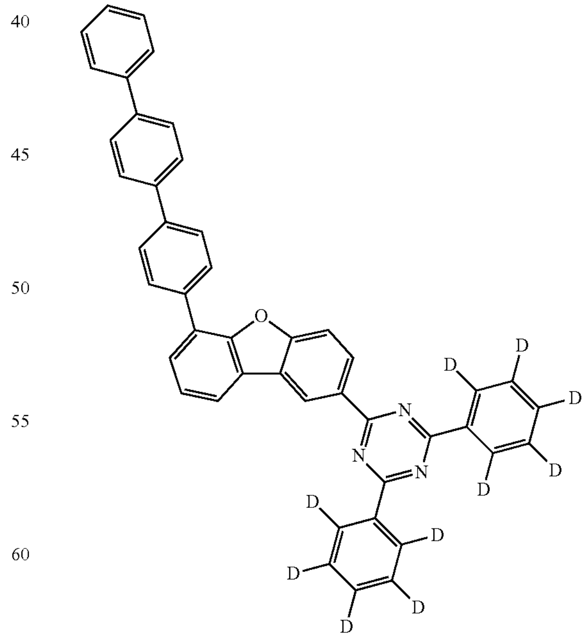

-continued
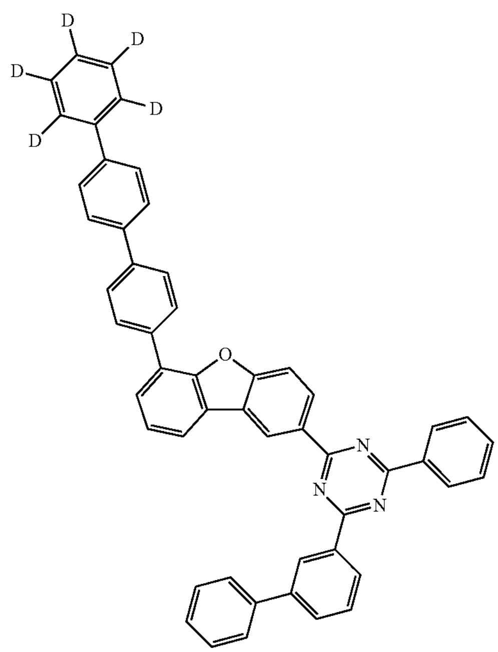
-continued
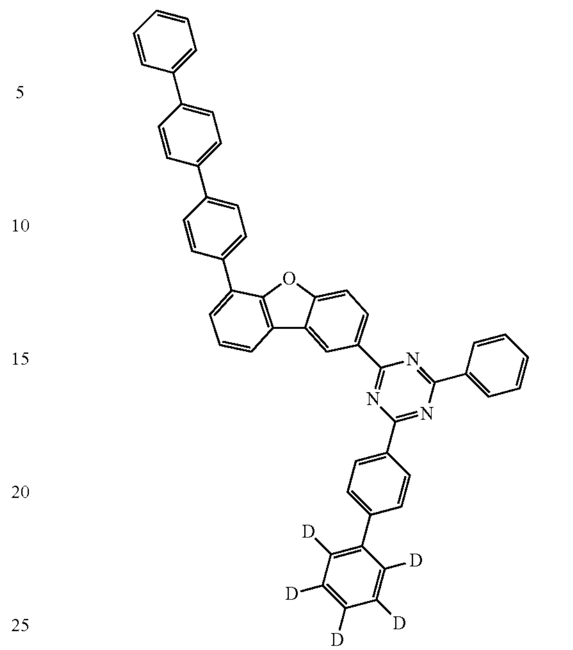
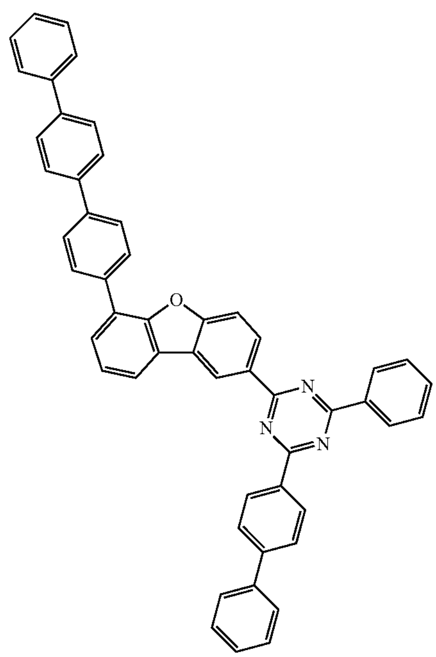
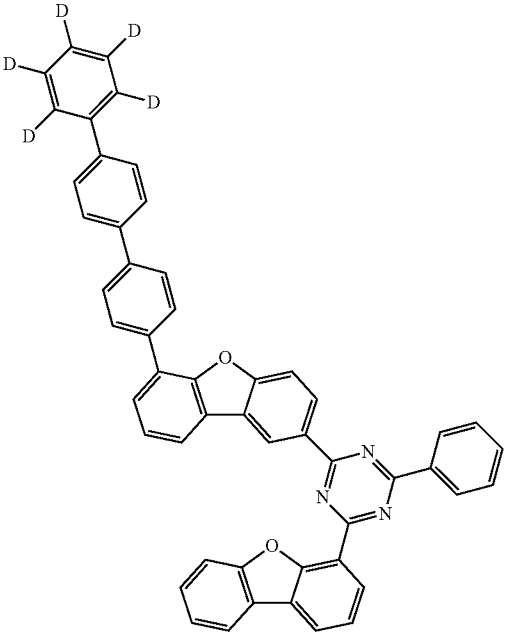

-continued
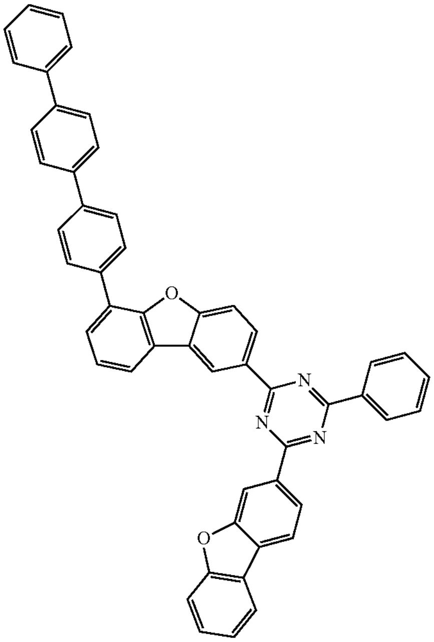
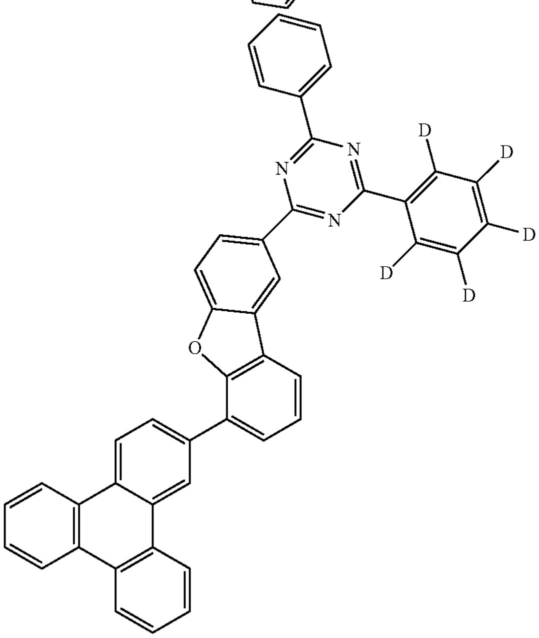
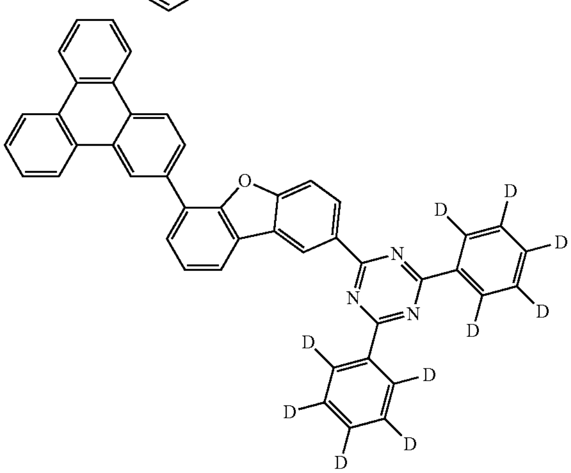
-continued
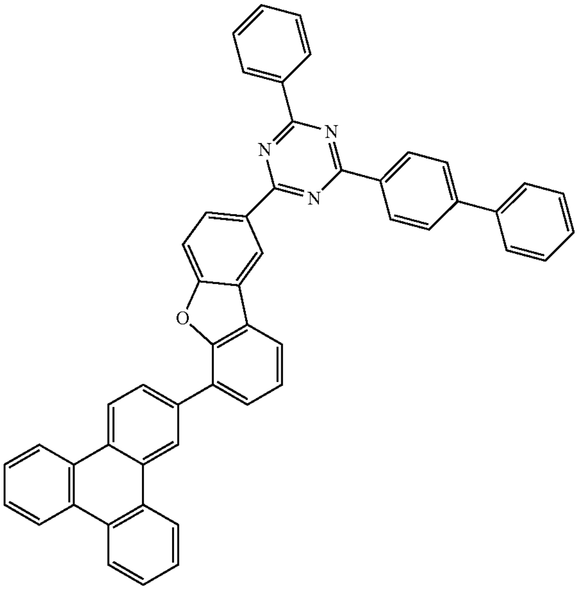
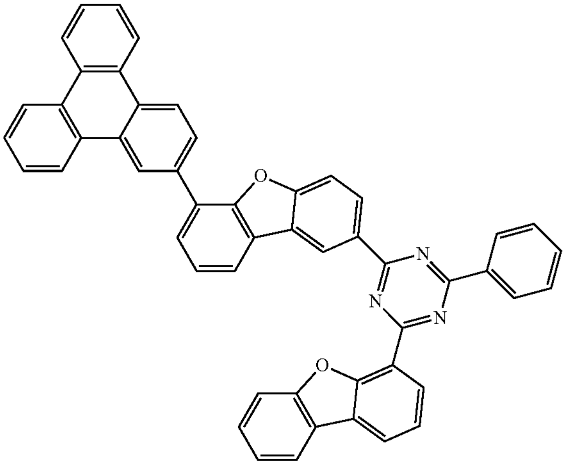
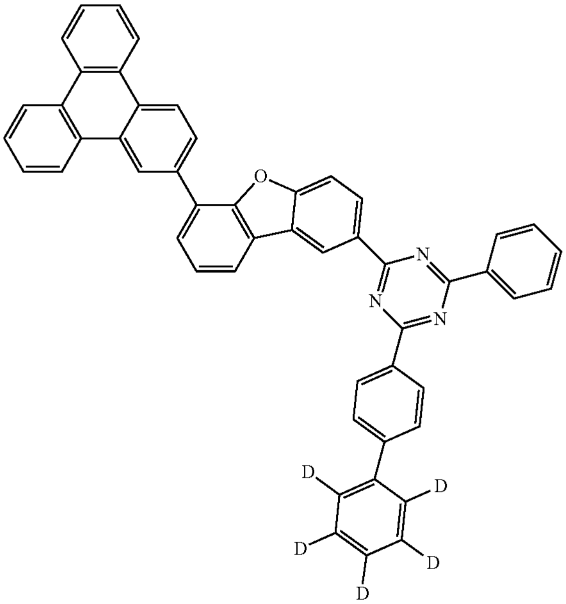

-continued
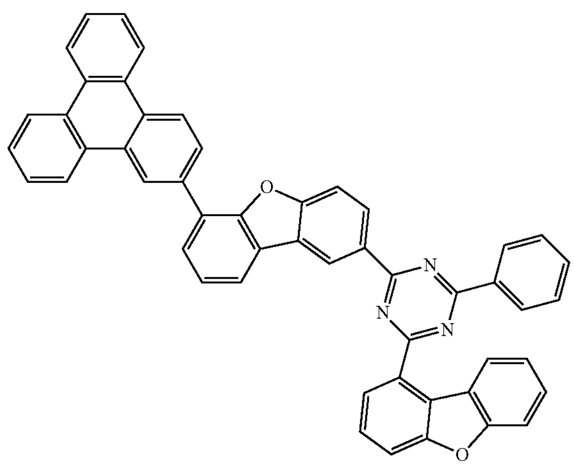
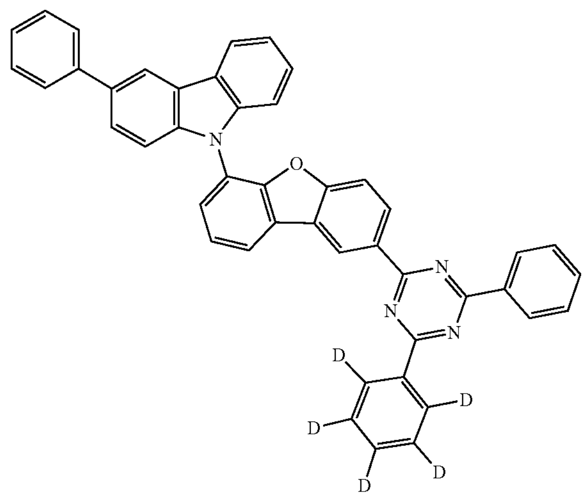
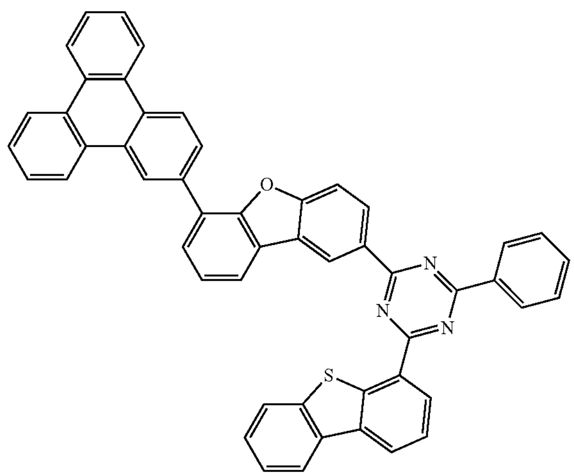
-continued
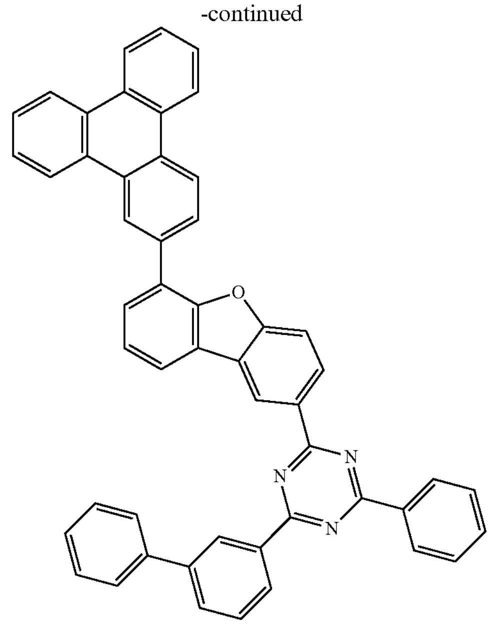
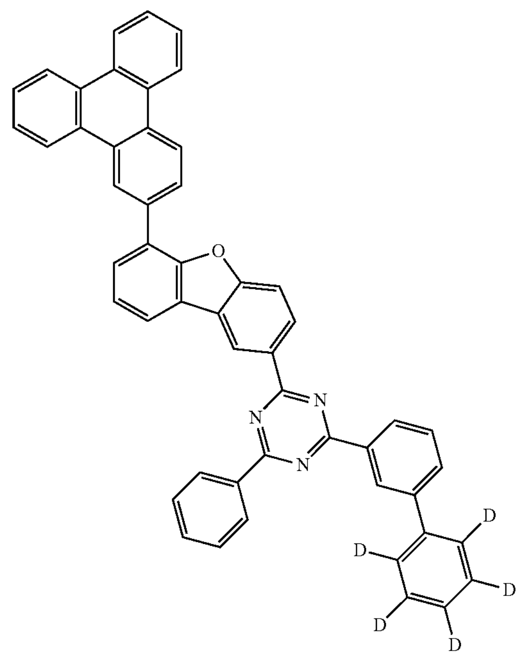
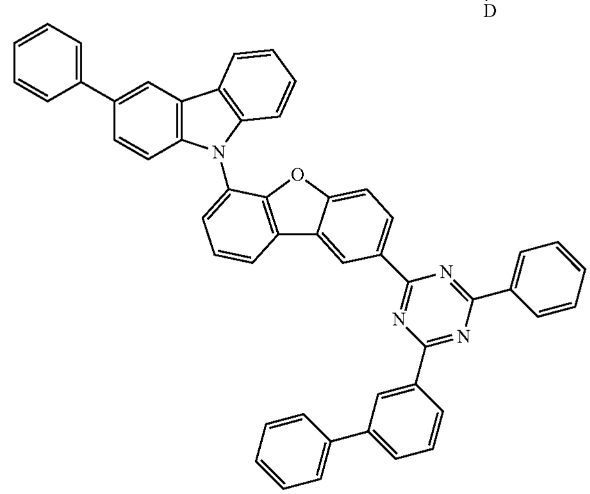

-continued
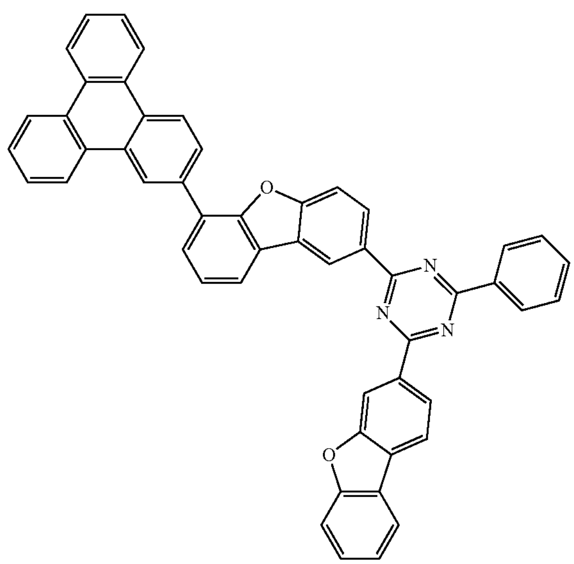
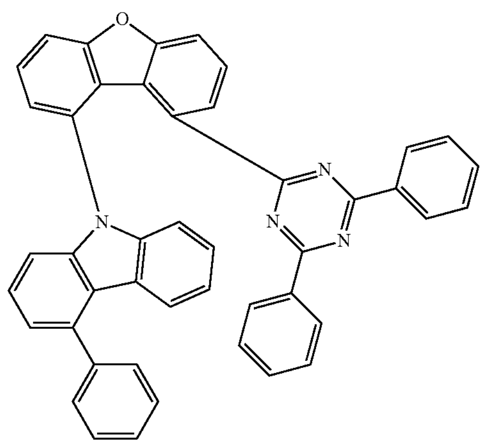
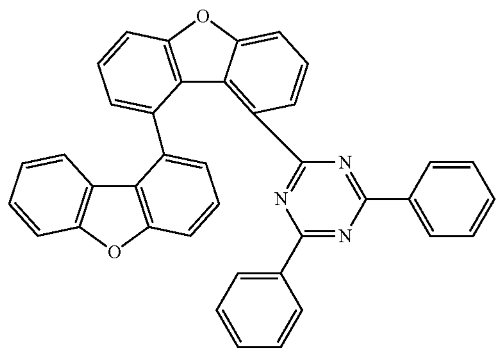
-continued
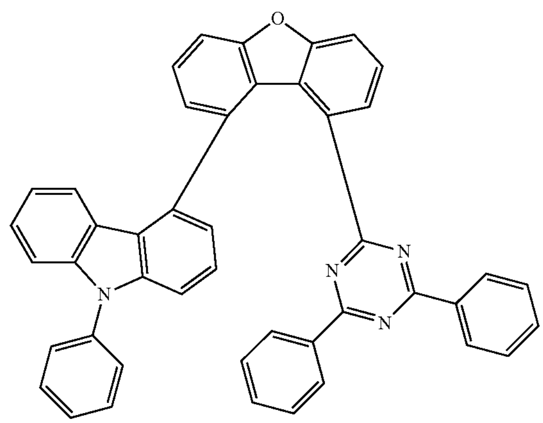
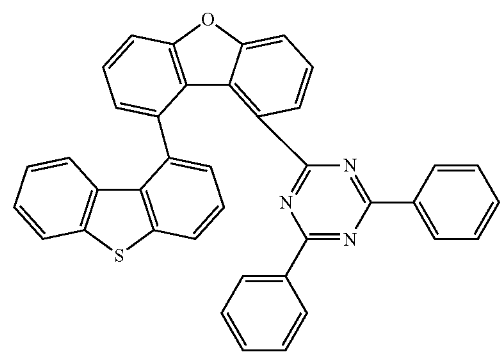
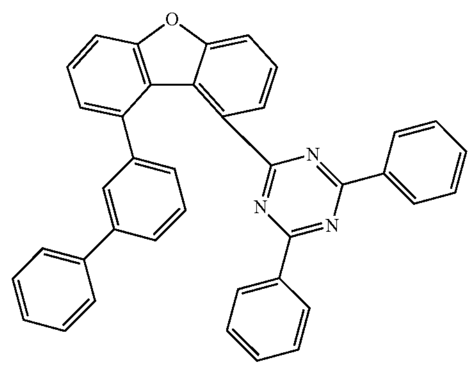
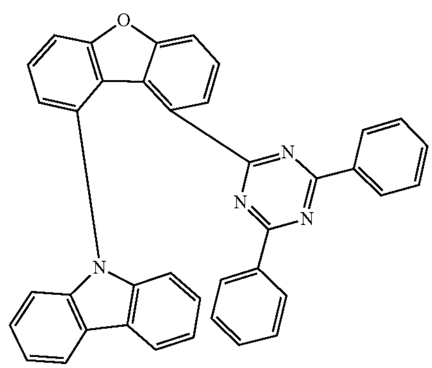

-continued
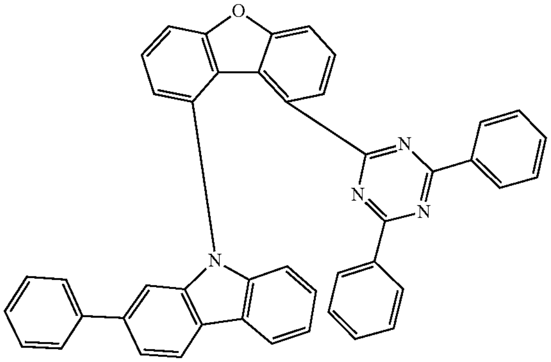
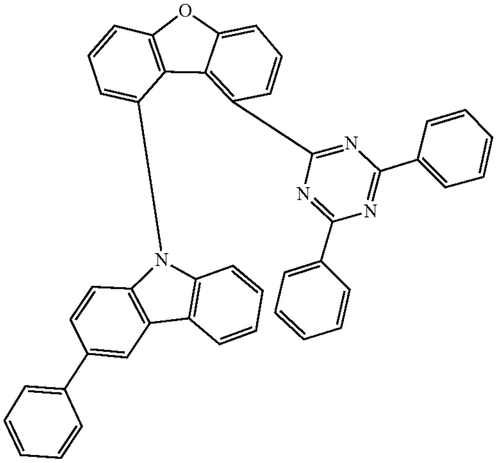
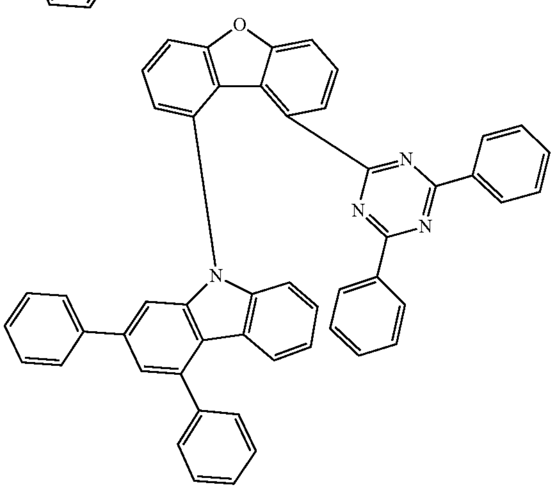
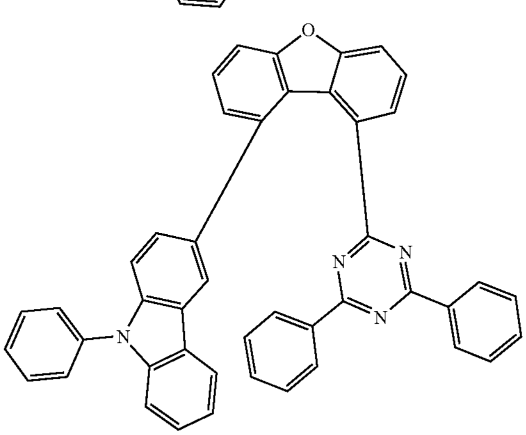
-continued
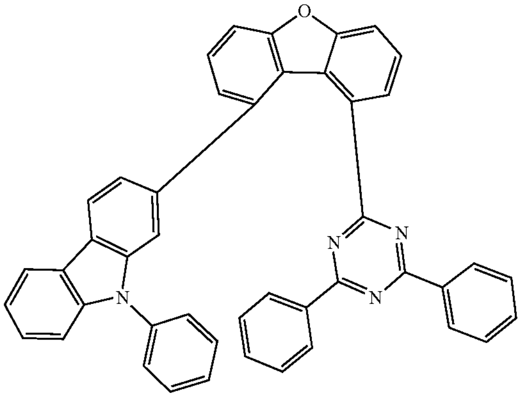
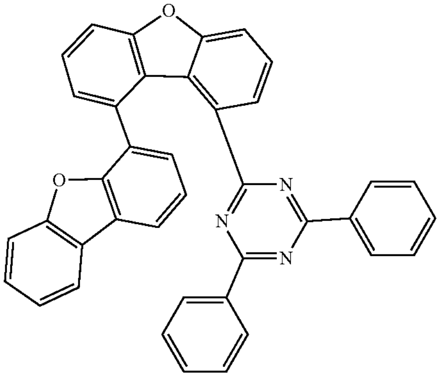
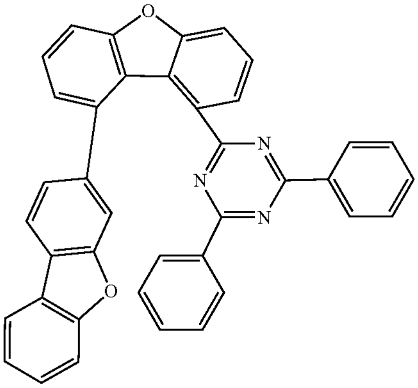
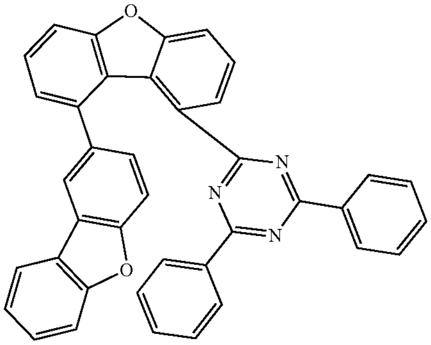

-continued
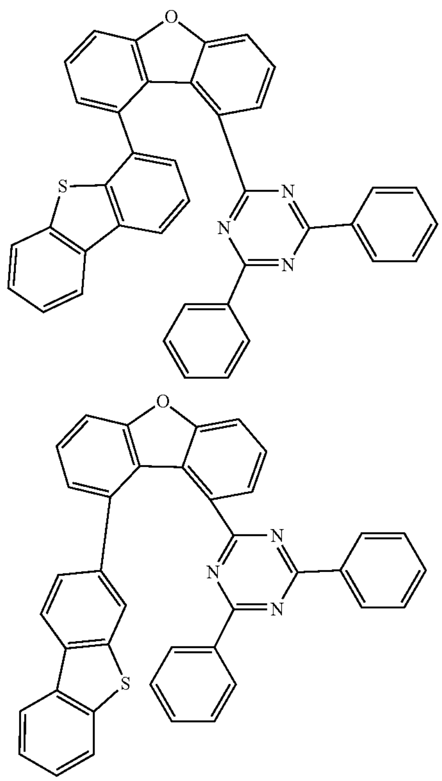
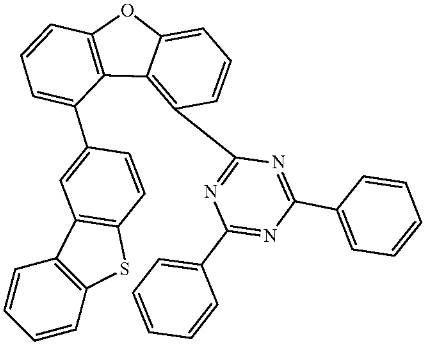
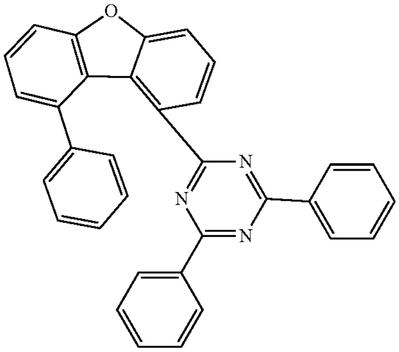
-continued
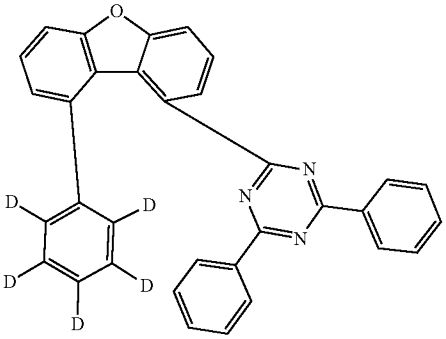
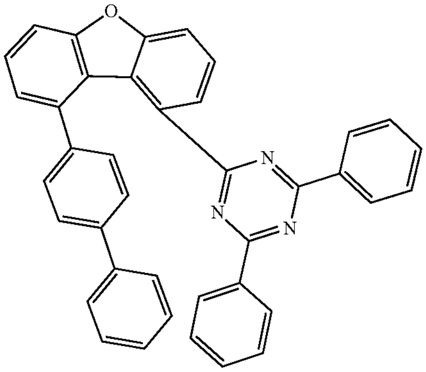
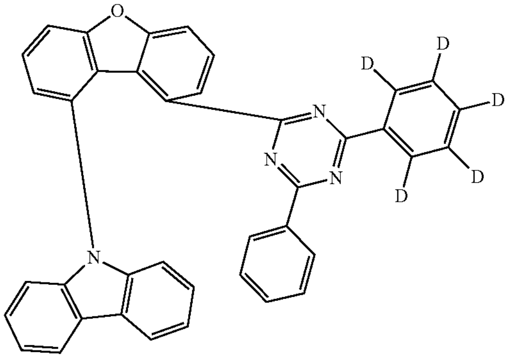
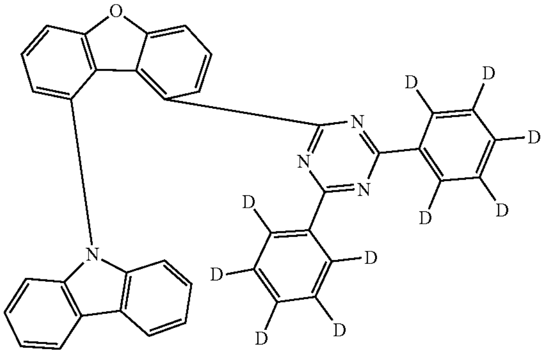

-continued
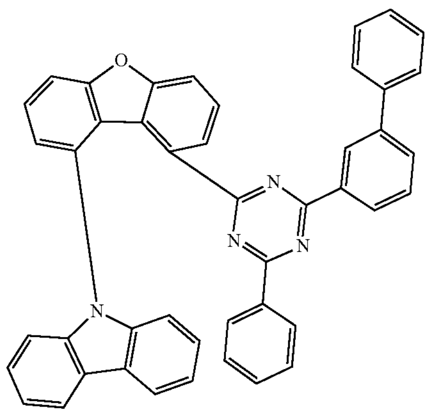
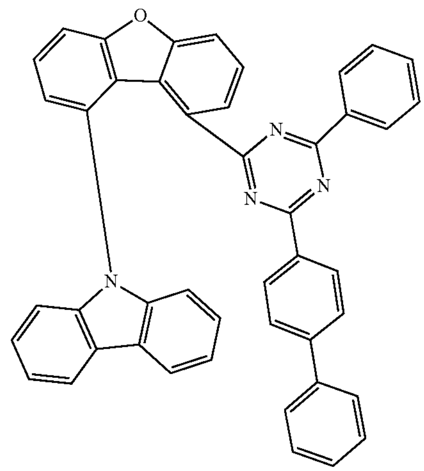
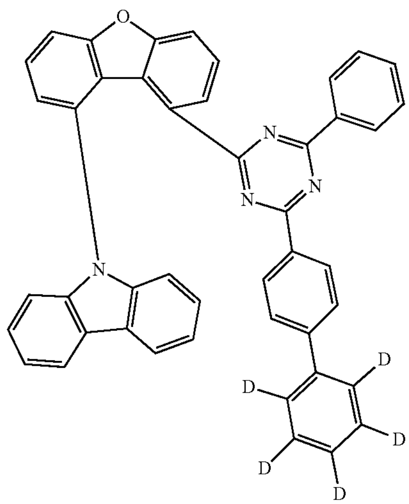
-continued
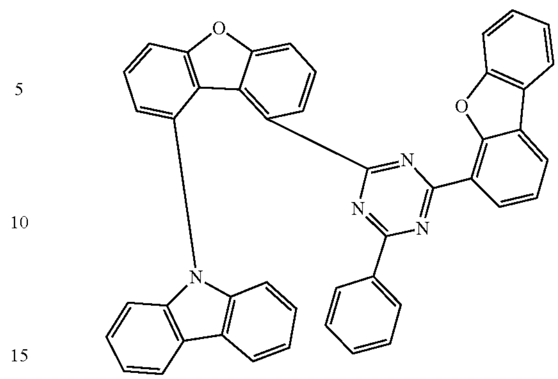
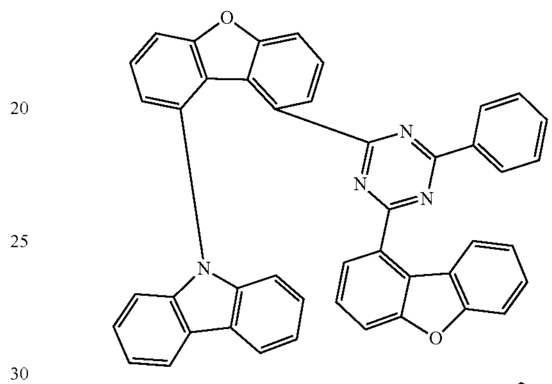
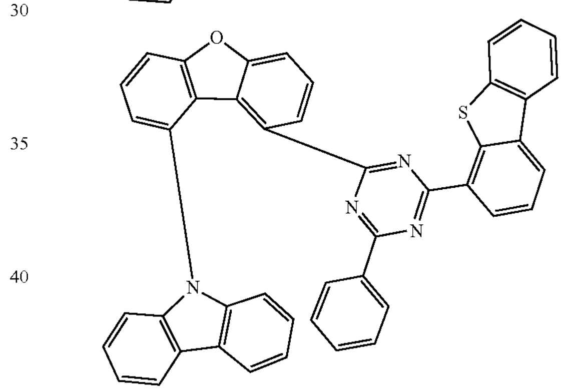
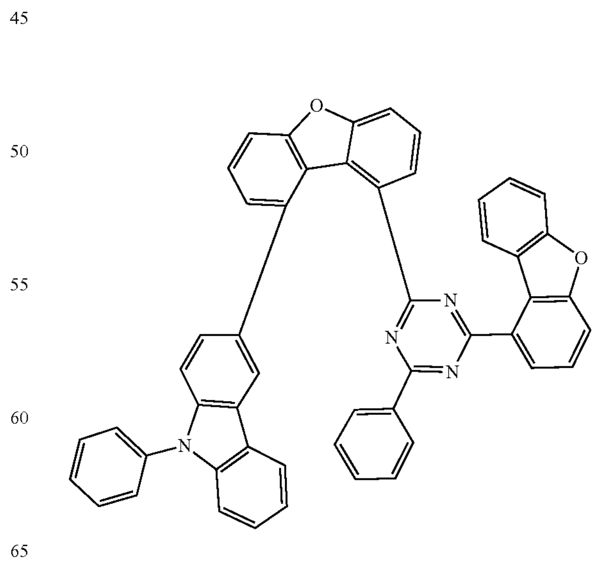

-continued
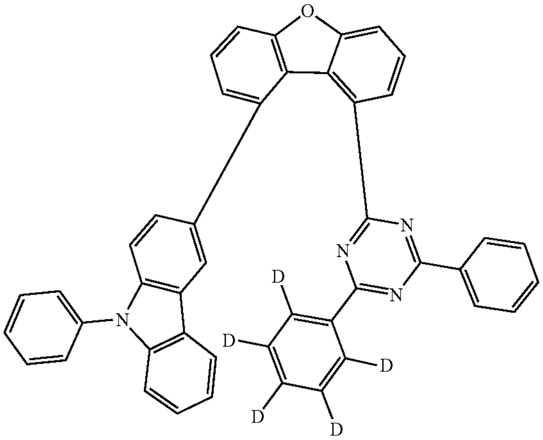
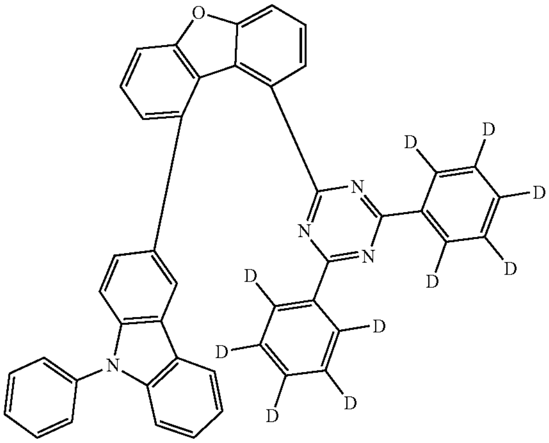
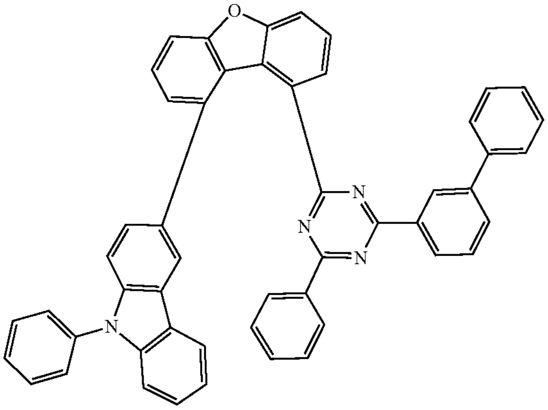
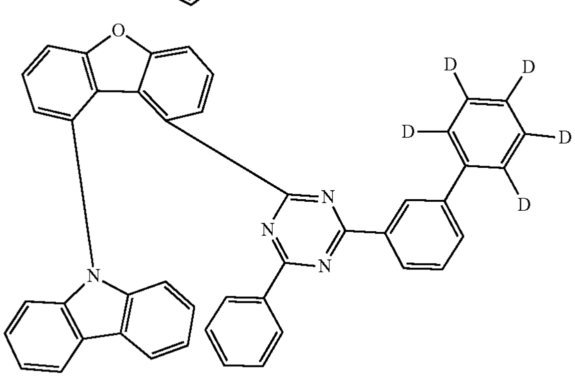
-continued
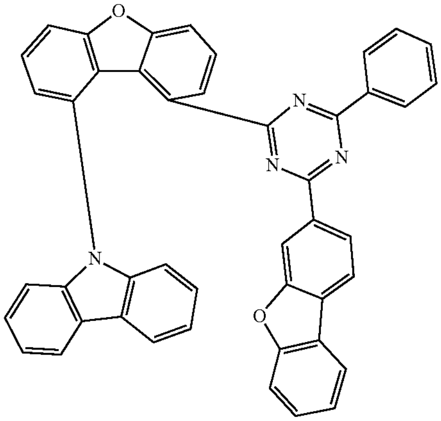
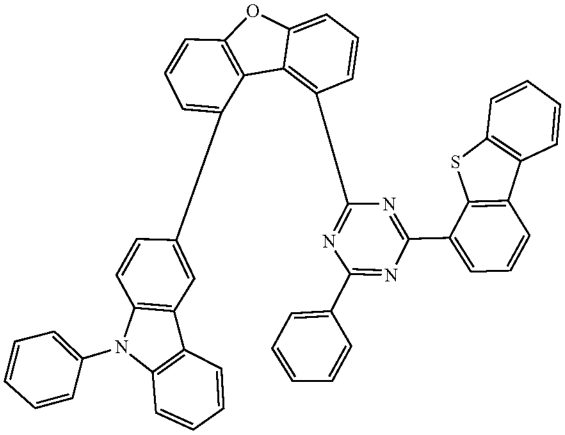
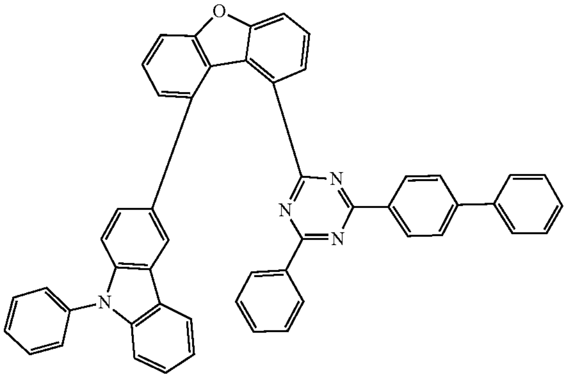
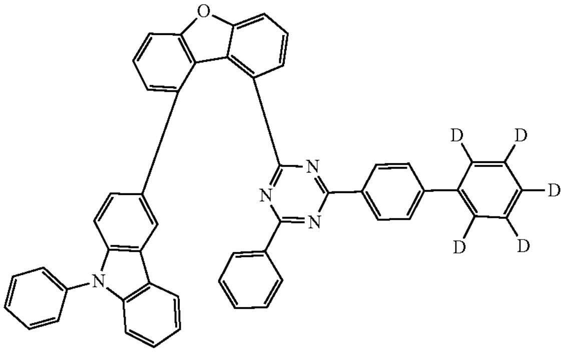

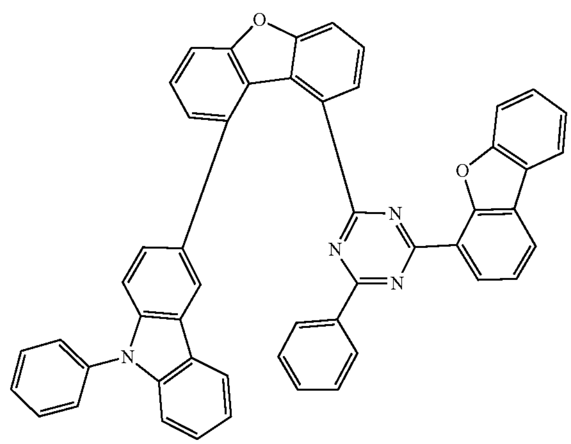
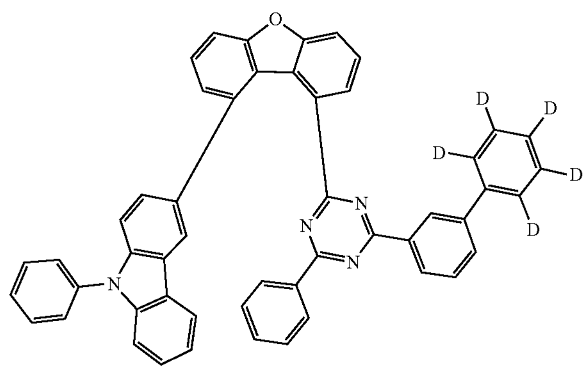
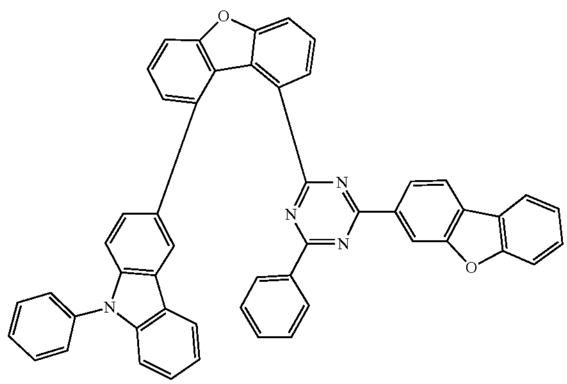
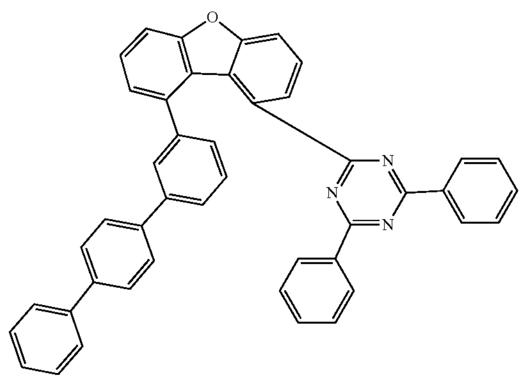
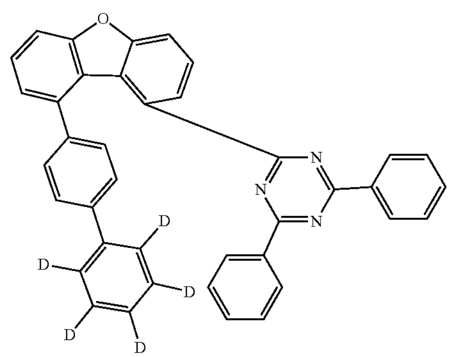
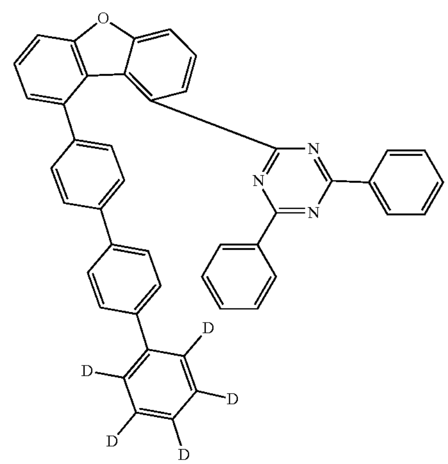
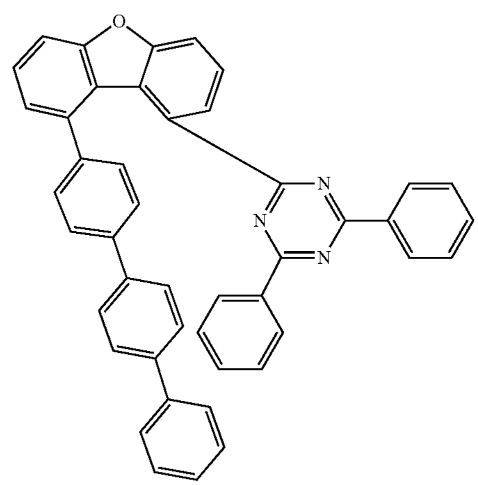
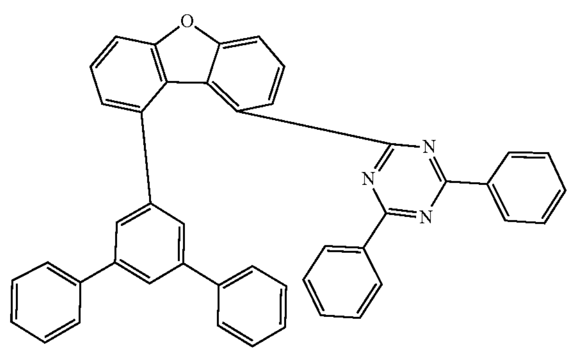

-continued
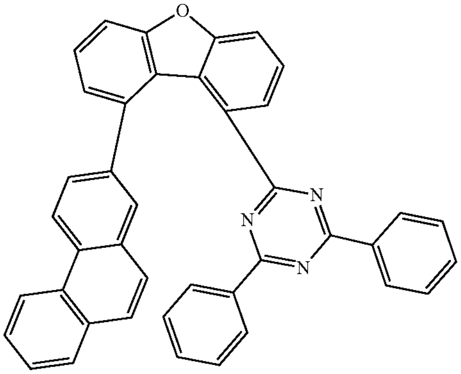
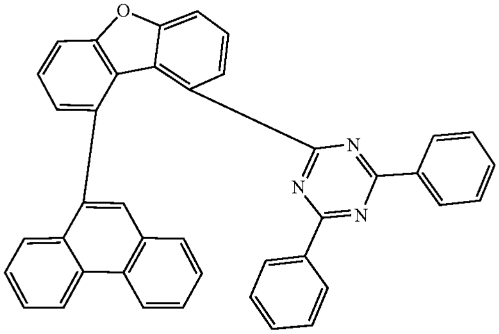
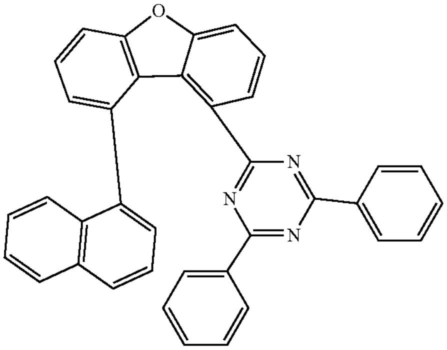
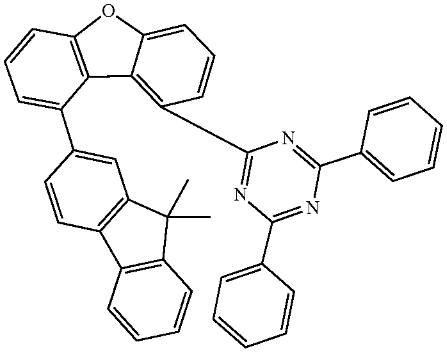
-continued
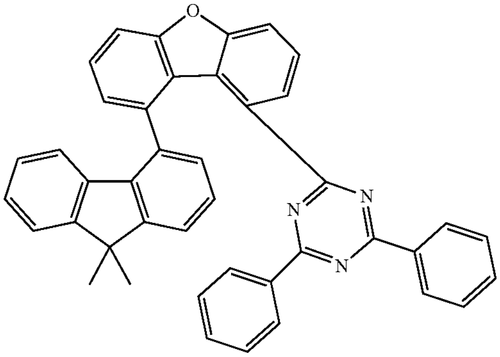
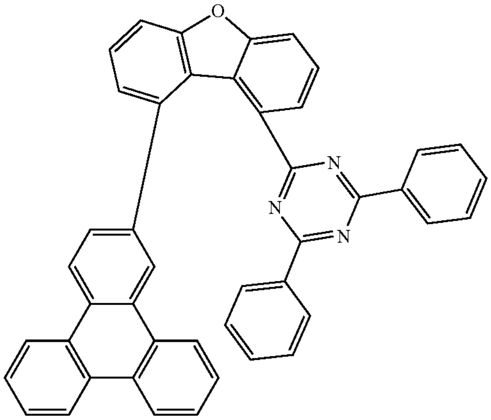
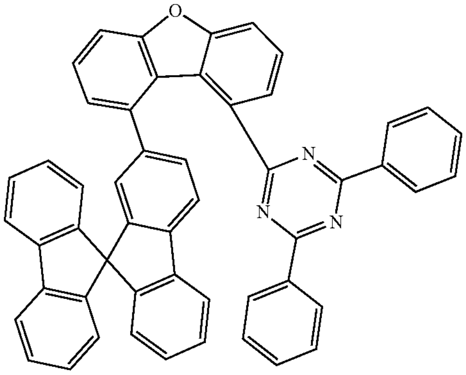
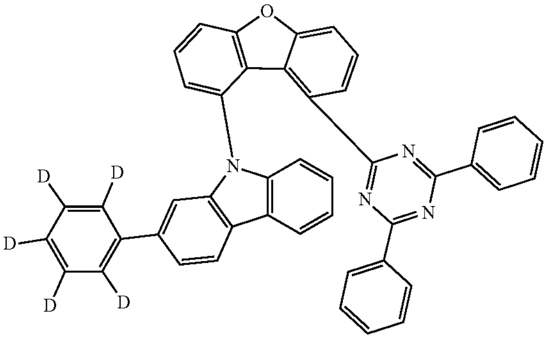

-continued
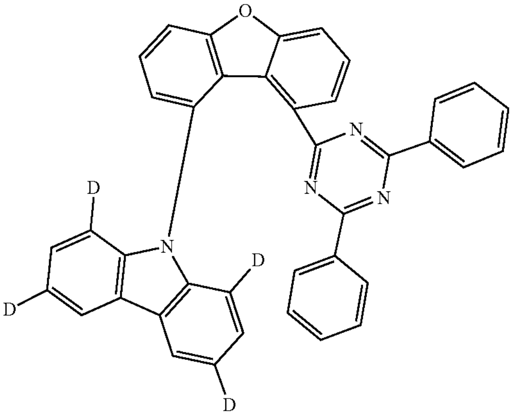
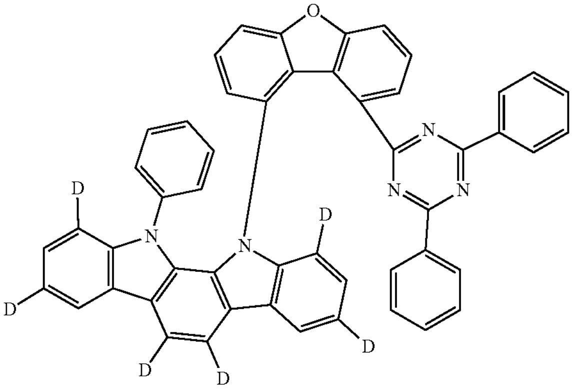
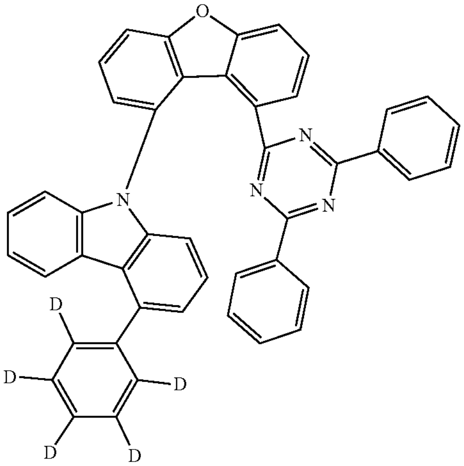
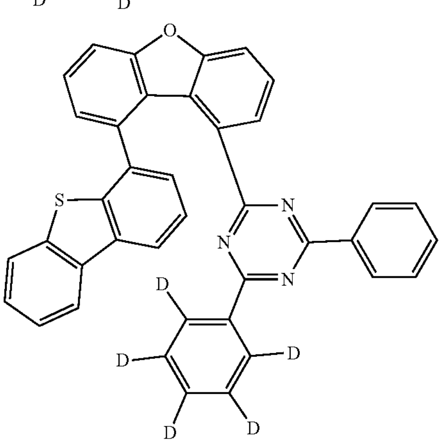
-continued
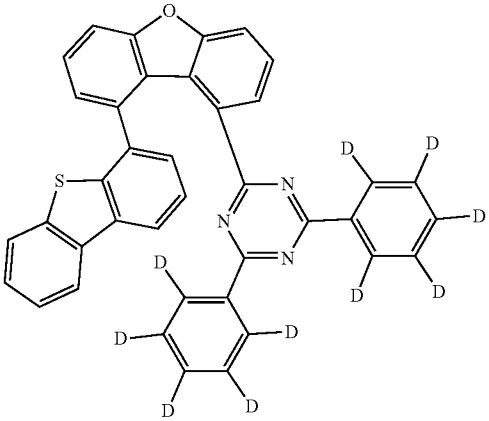
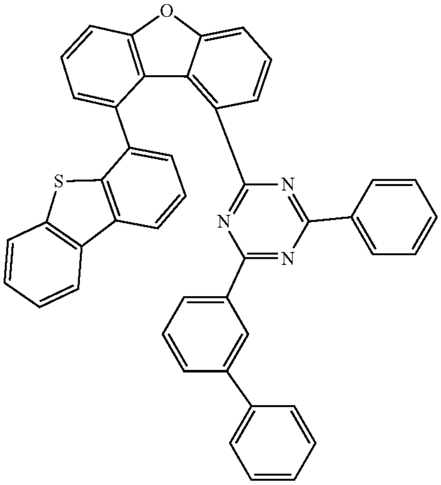
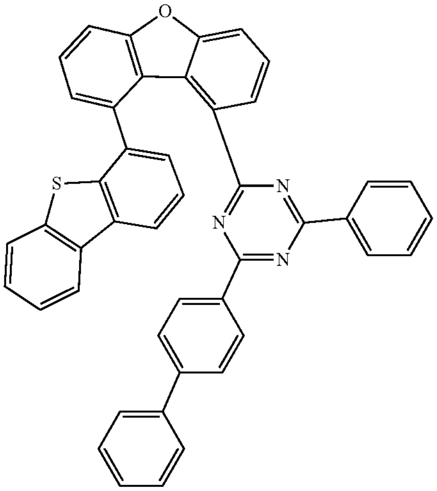

-continued
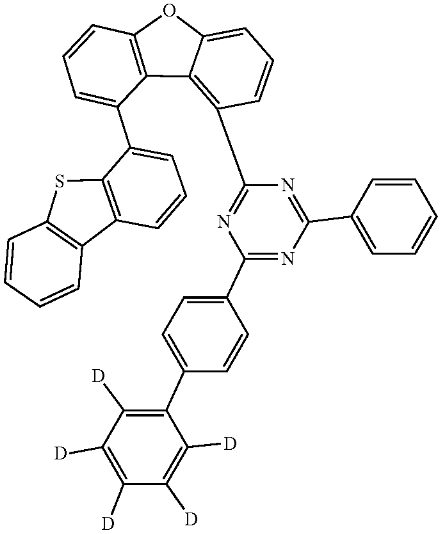
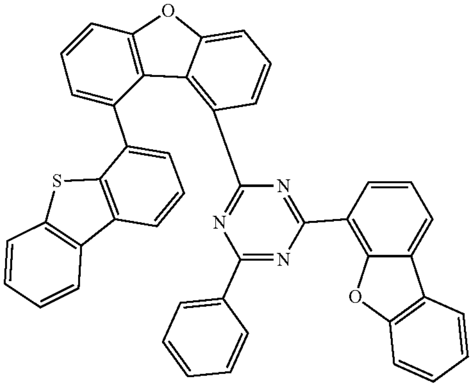
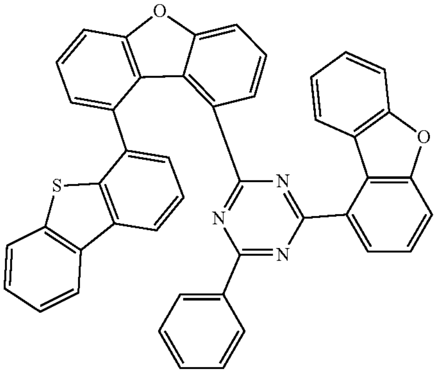
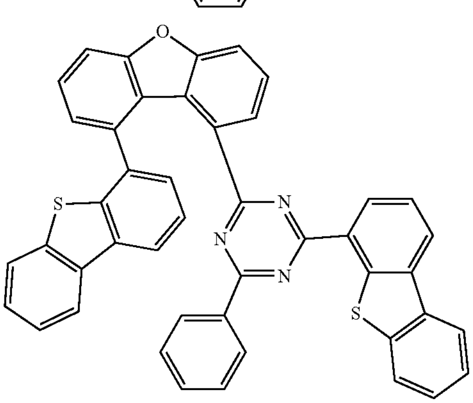
-continued
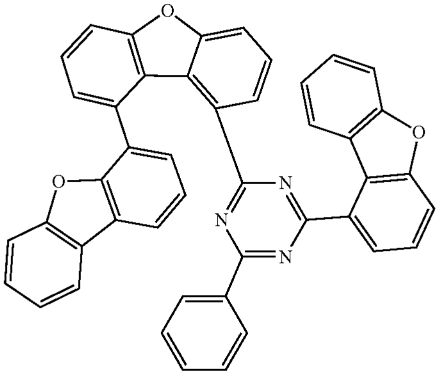
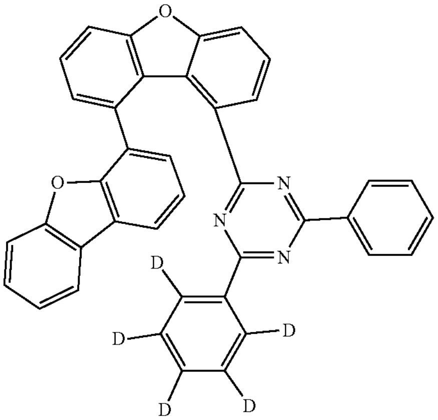
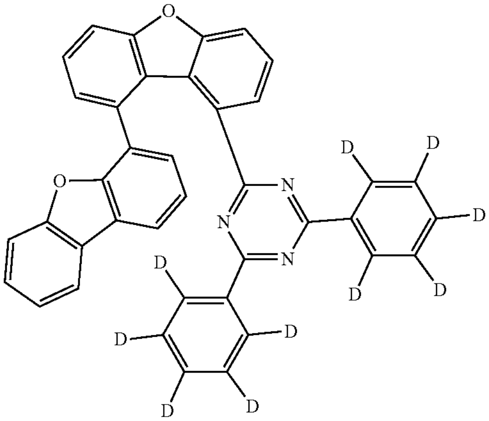
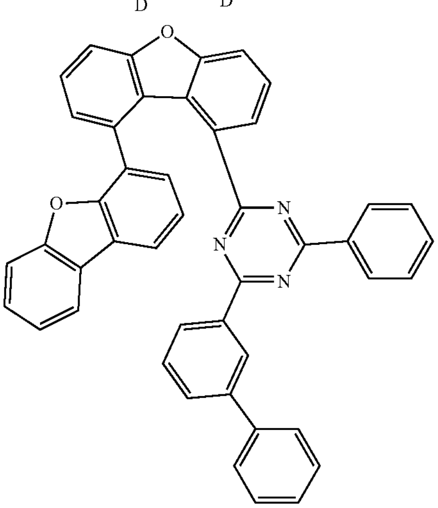

-continued
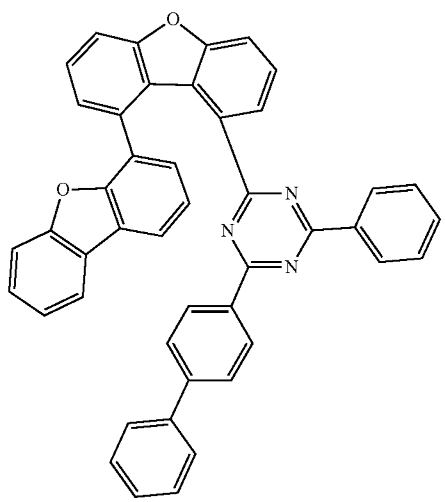
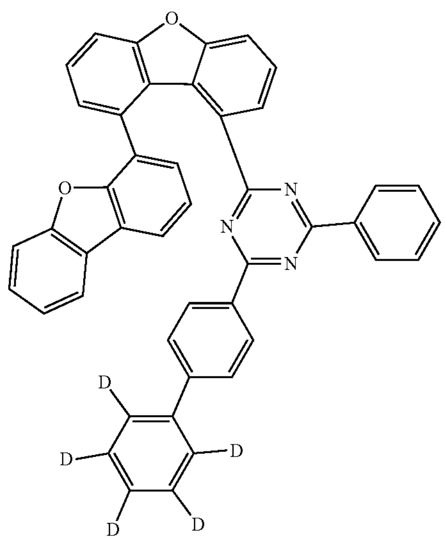
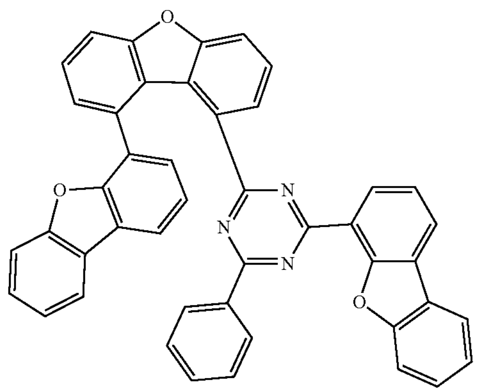
-continued
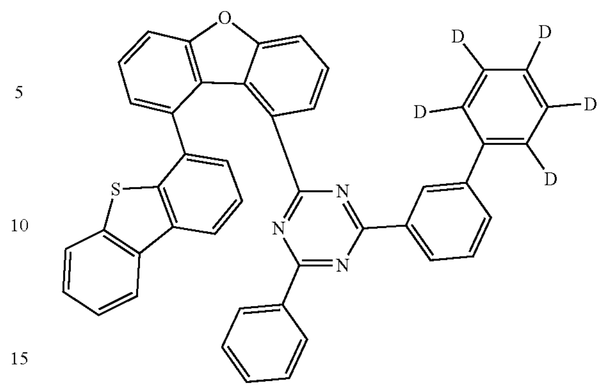
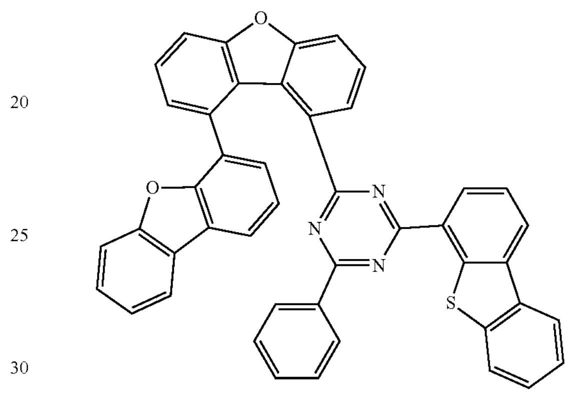
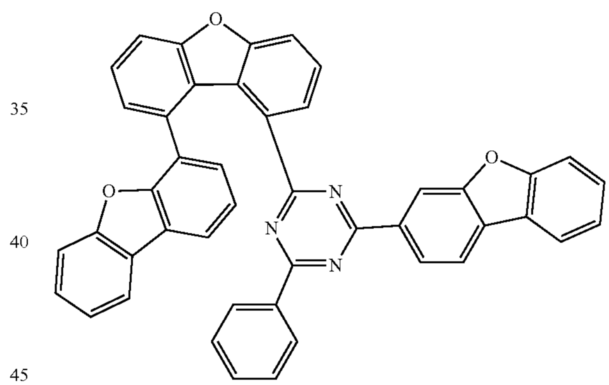
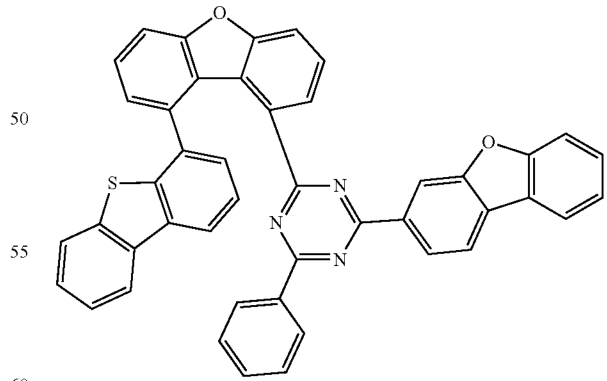

-continued
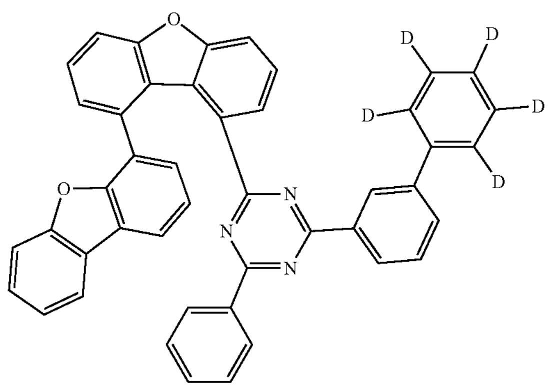
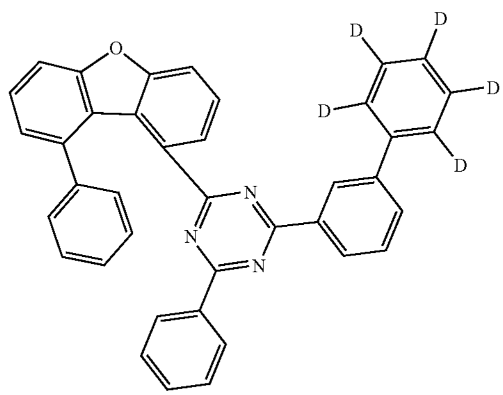
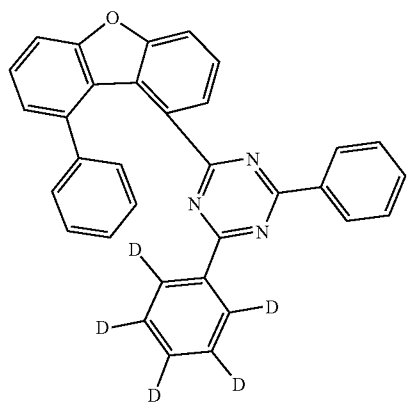
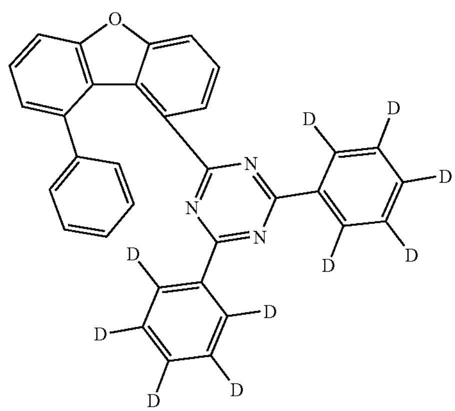
-continued
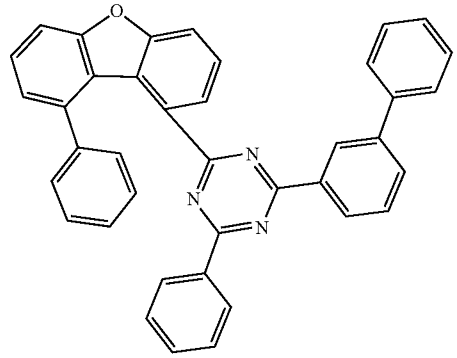
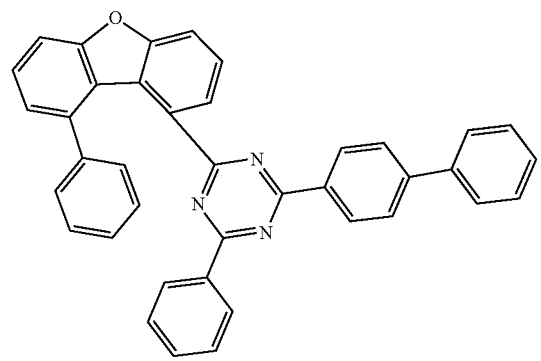
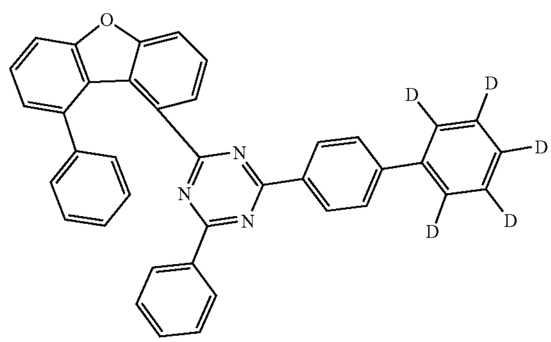
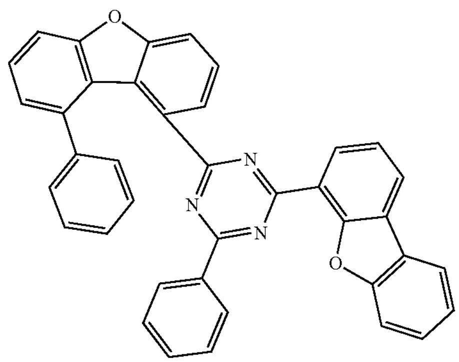

-continued
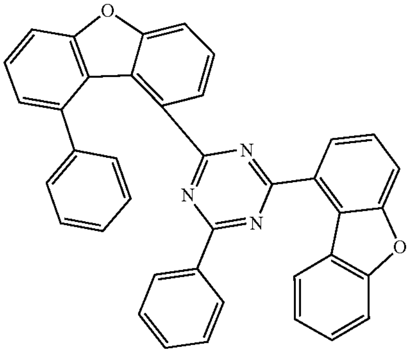
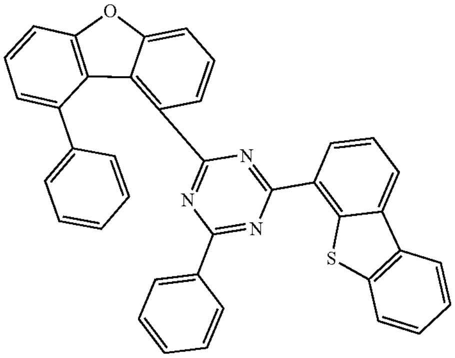
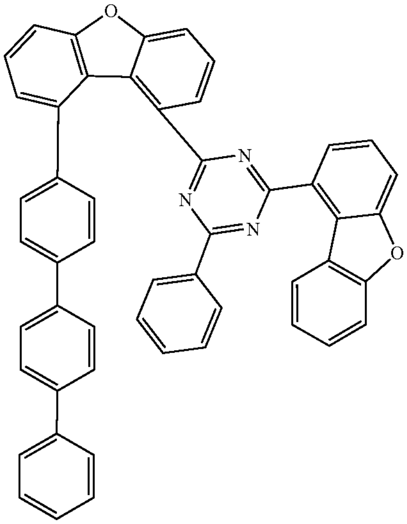
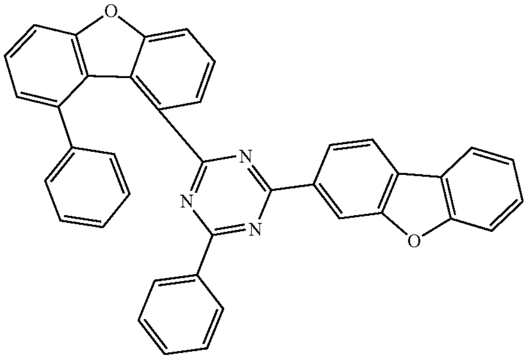
-continued
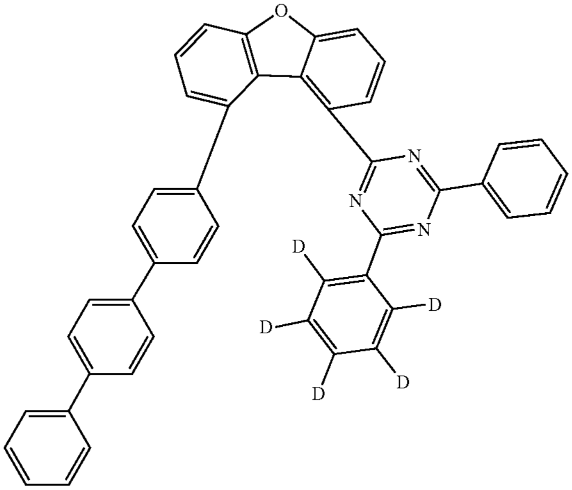
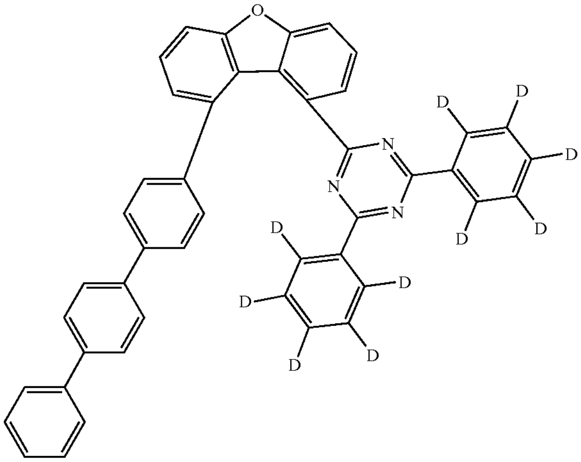
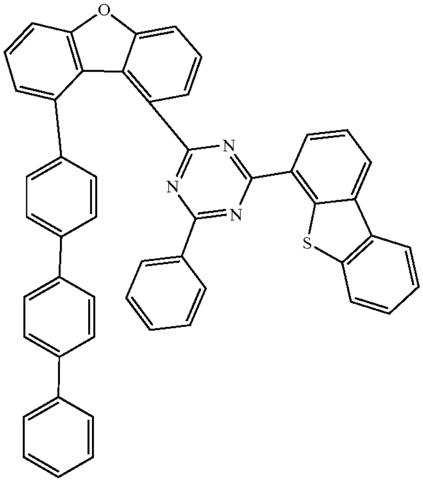

-continued
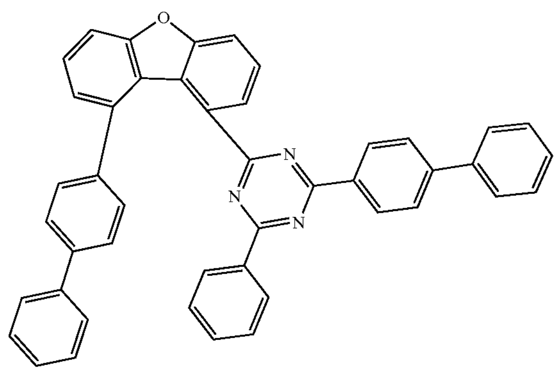
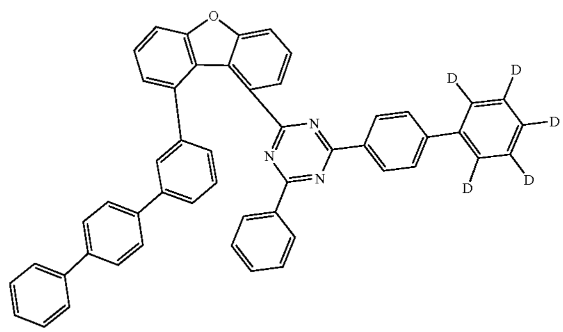
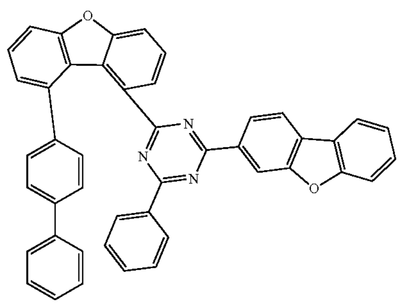
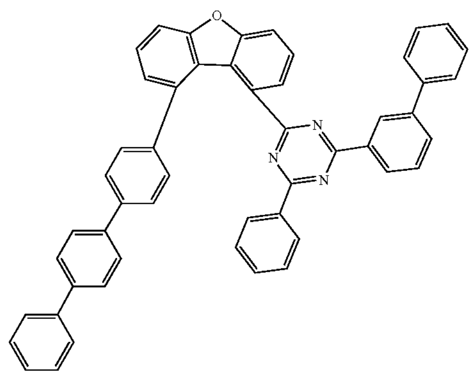
-continued
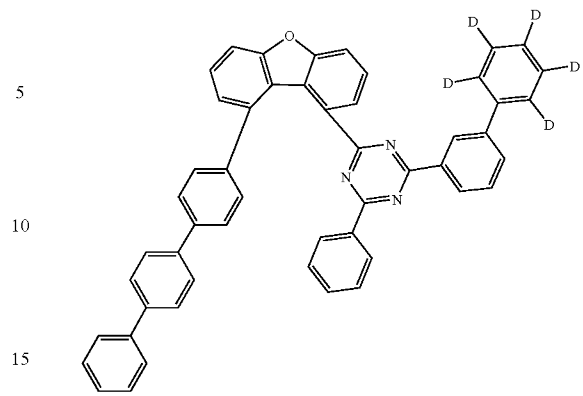
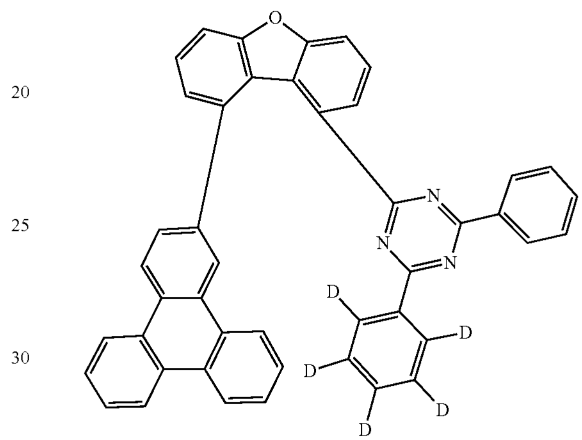
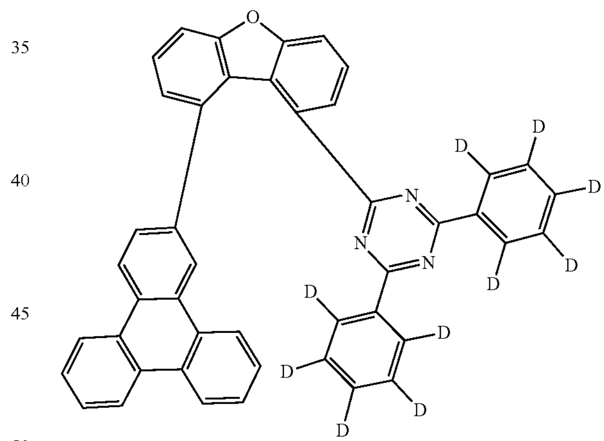
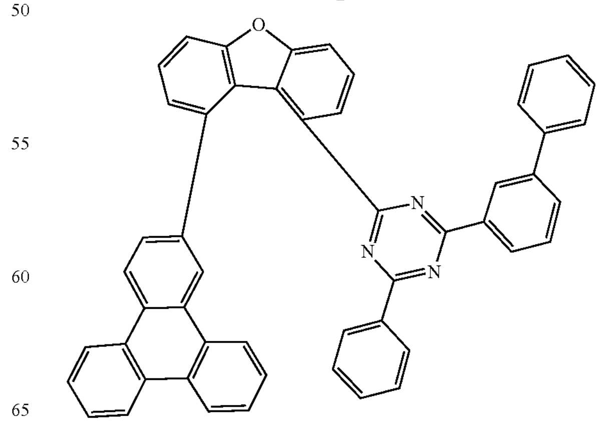

-continued
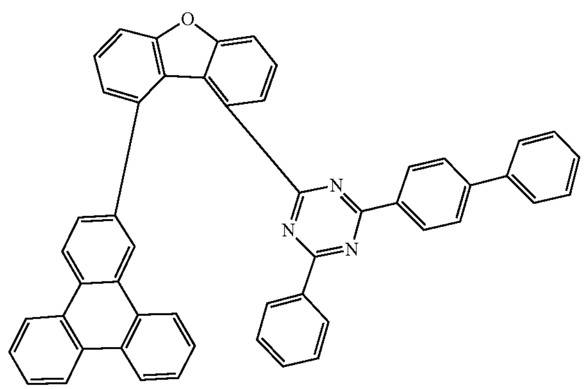
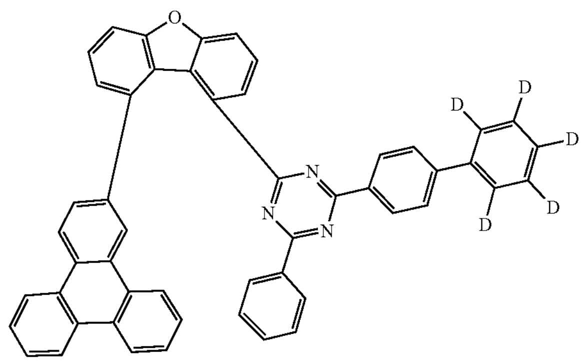
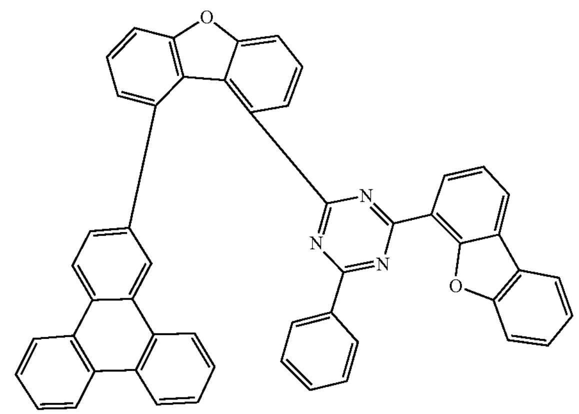
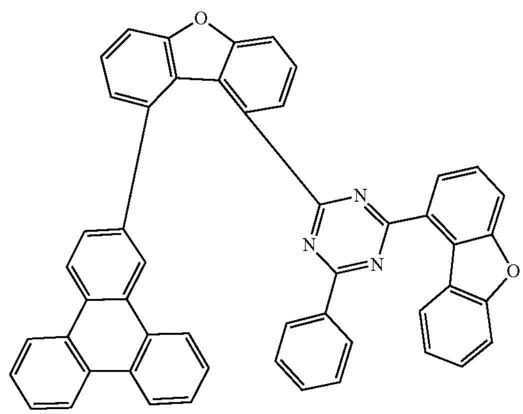
-continued
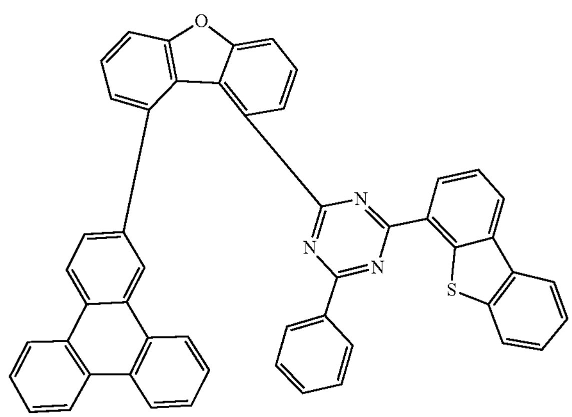
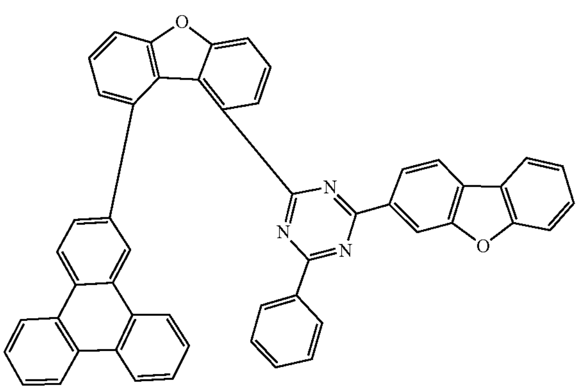
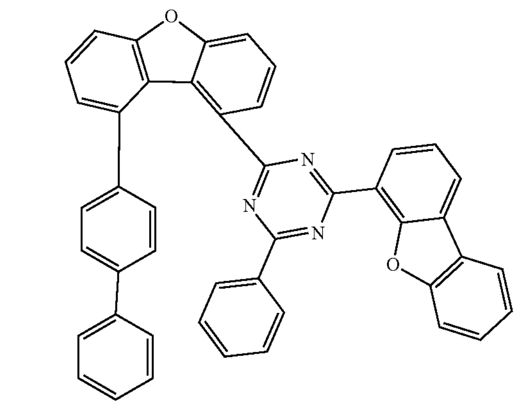
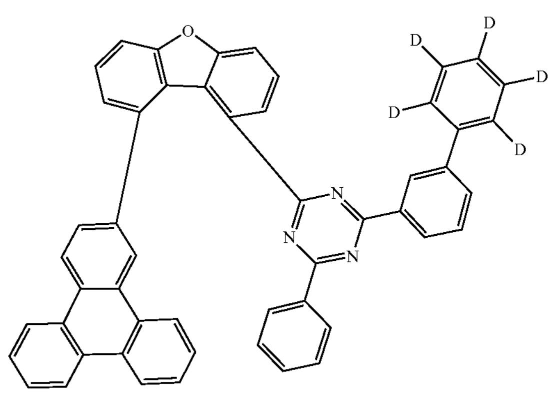

-continued
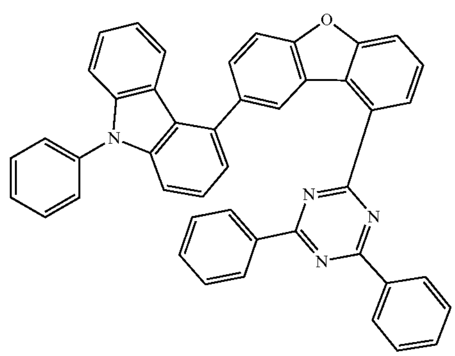
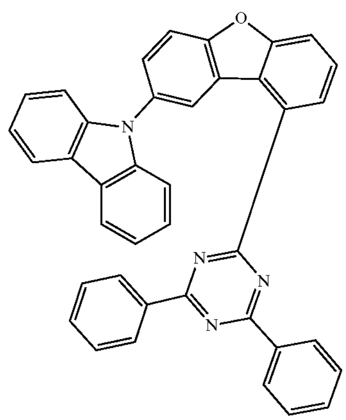
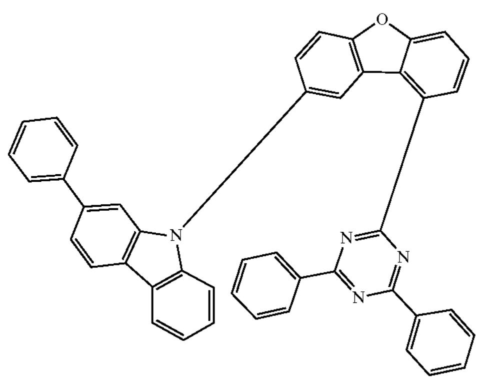
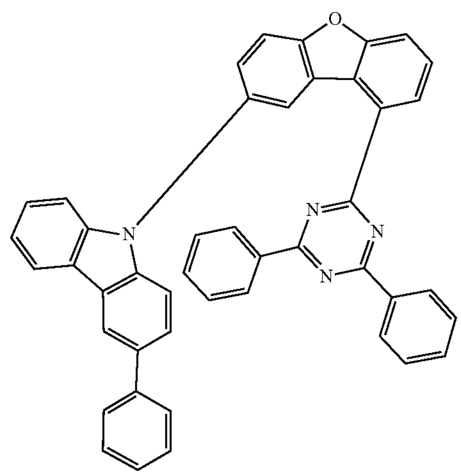
-continued
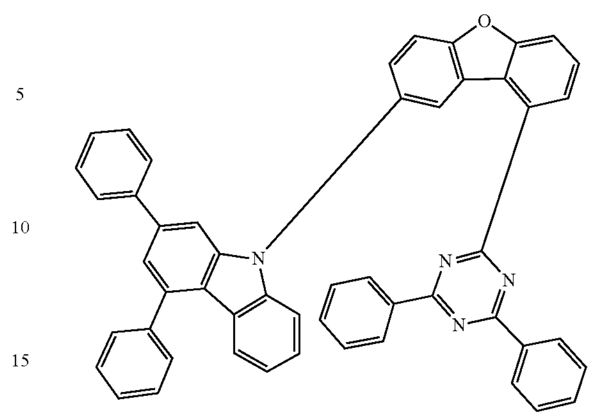
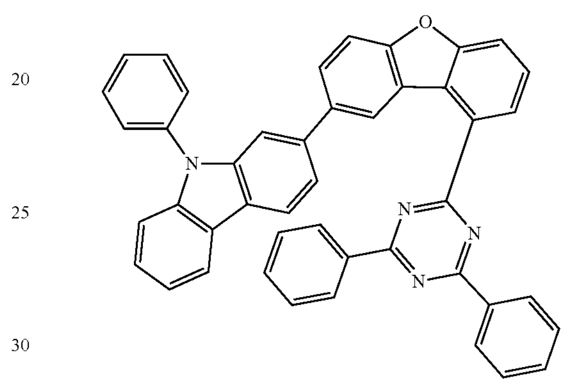
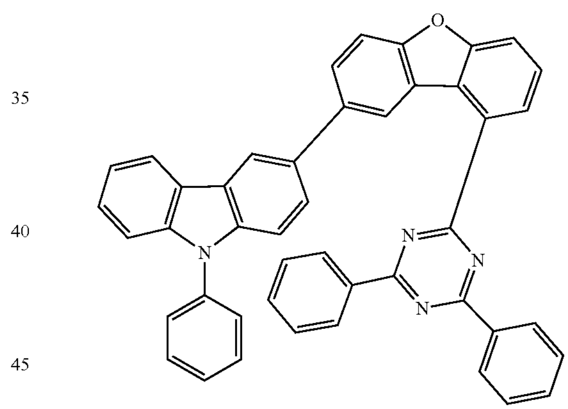
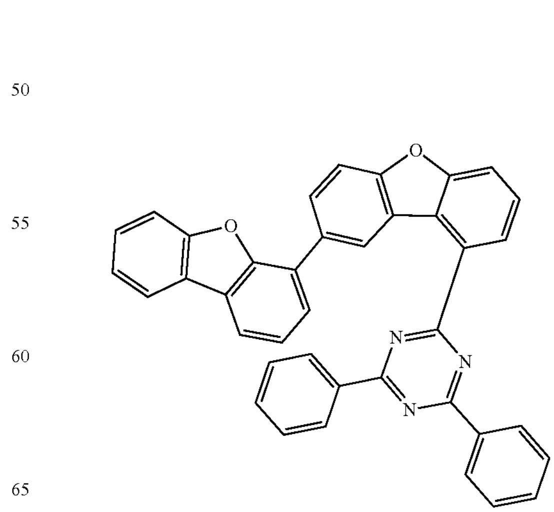

-continued
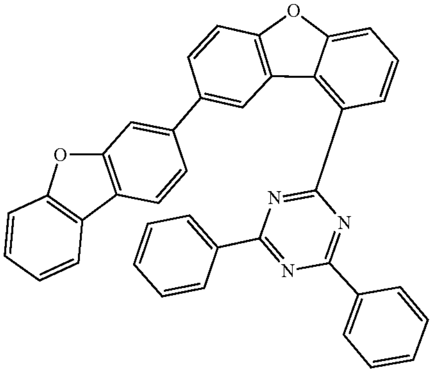
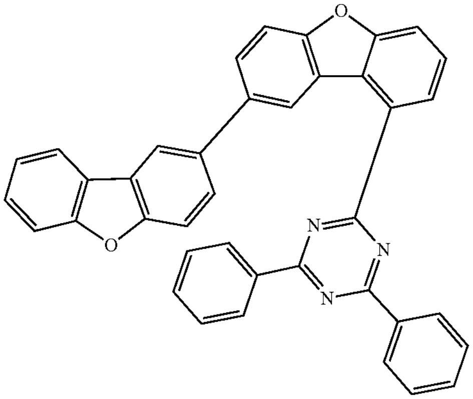
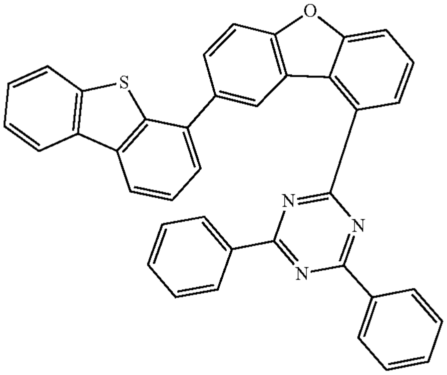
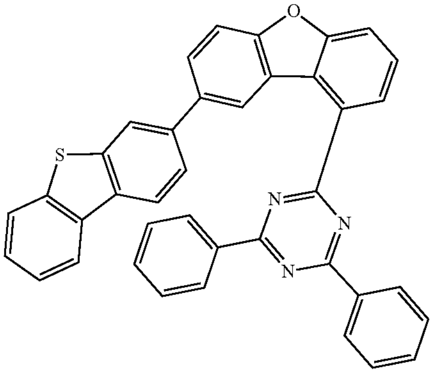
-continued
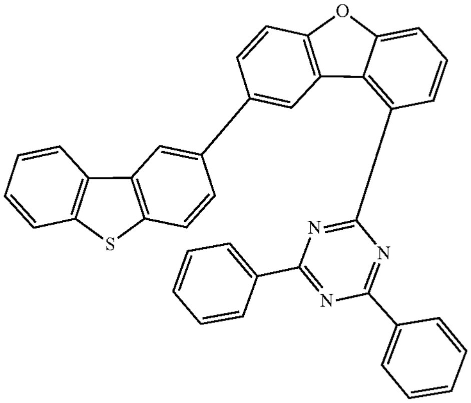
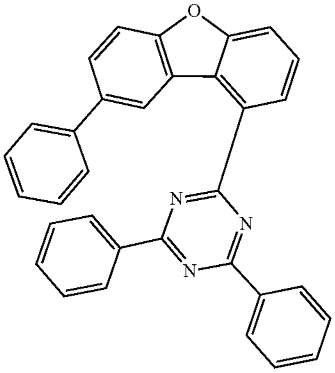
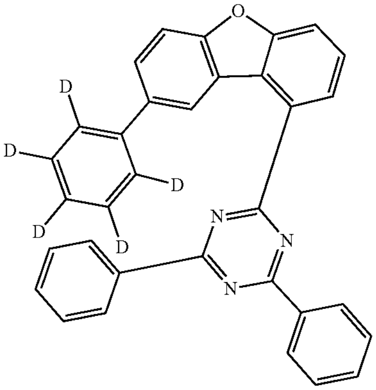
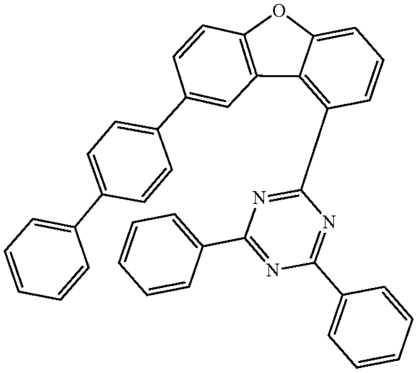

-continued
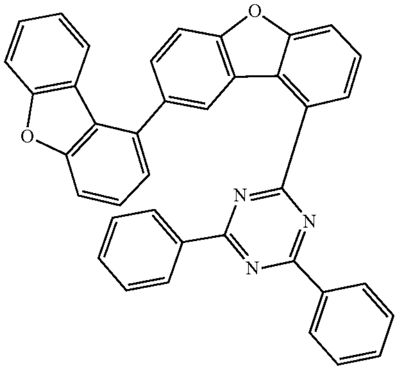
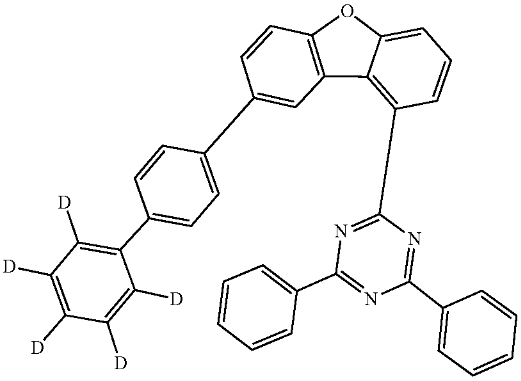
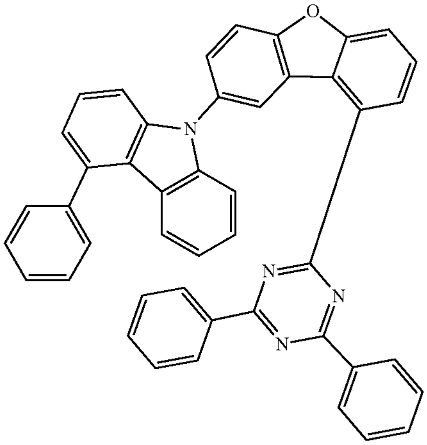
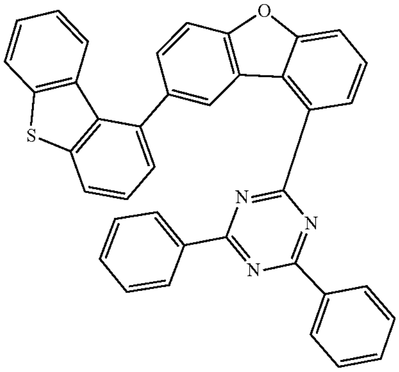
-continued
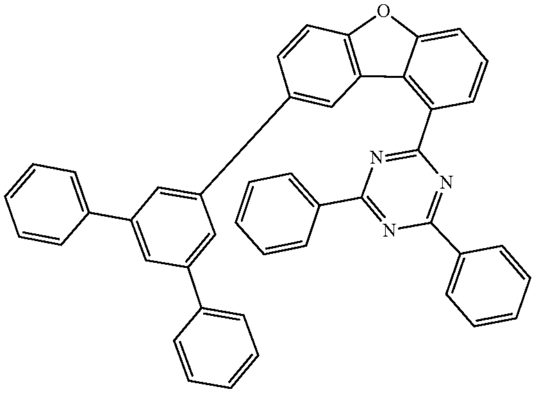
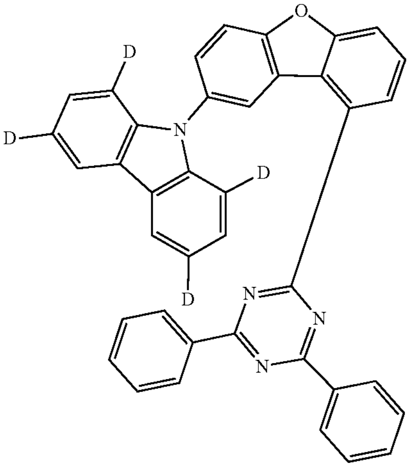
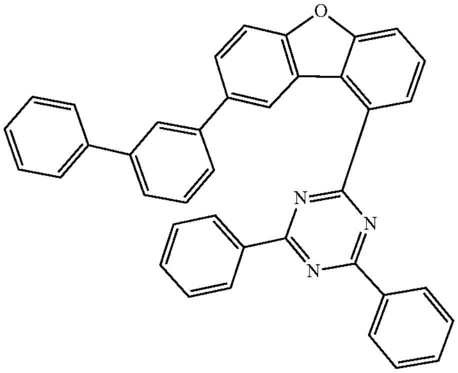
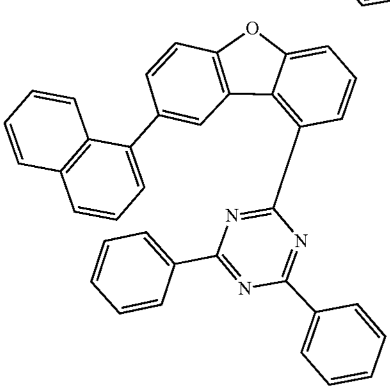

-continued
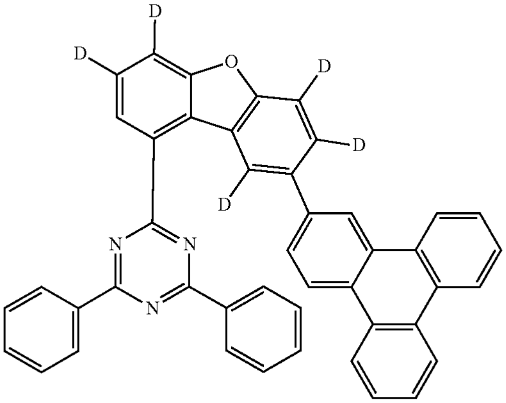
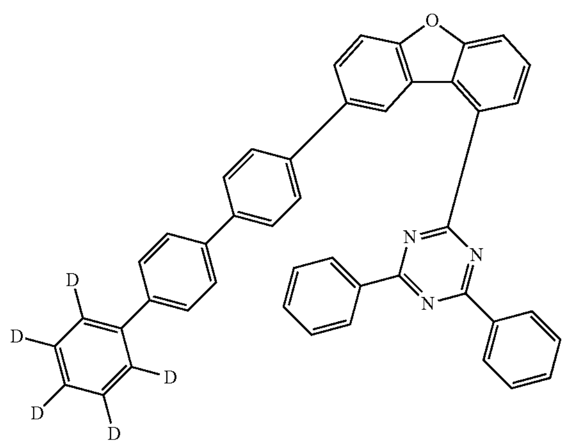
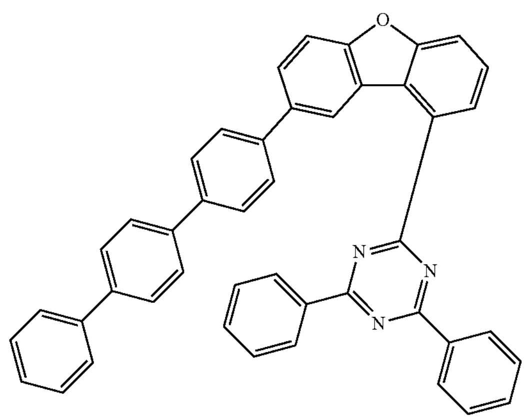
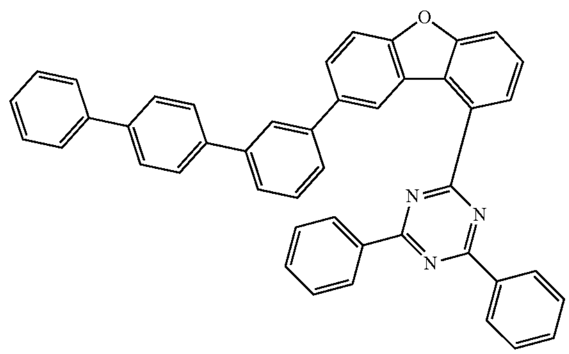
-continued
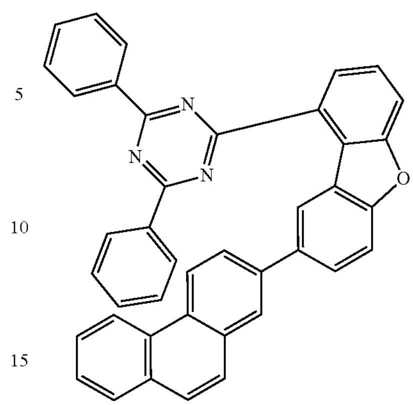
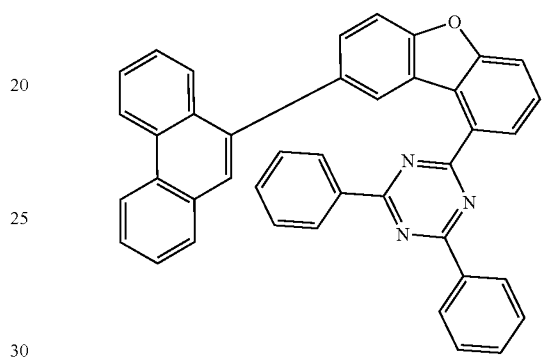
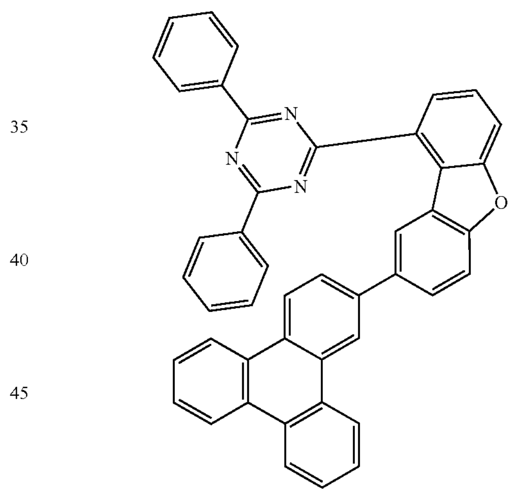
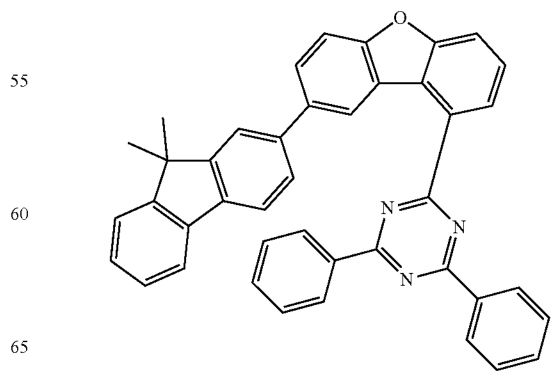

-continued
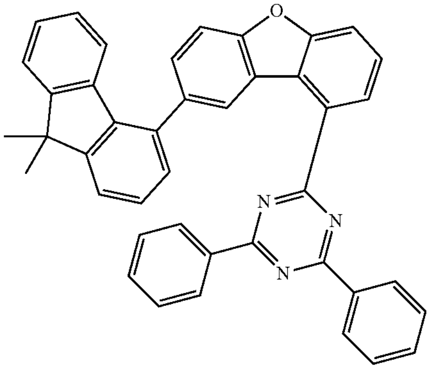
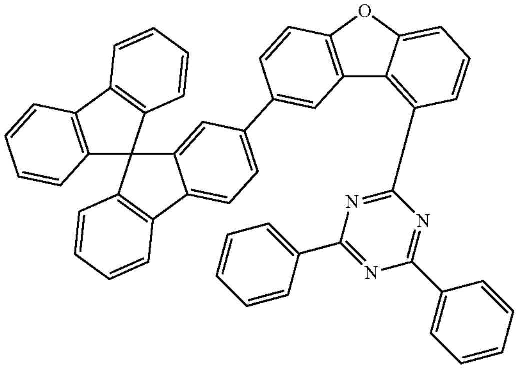
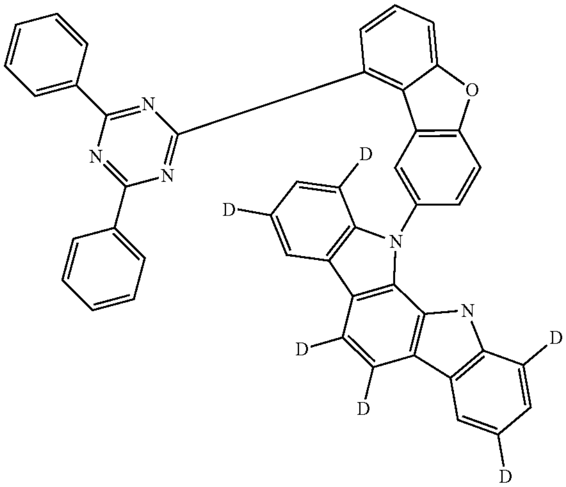
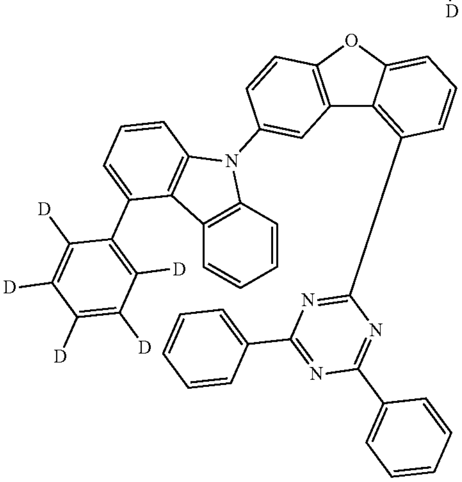
-continued
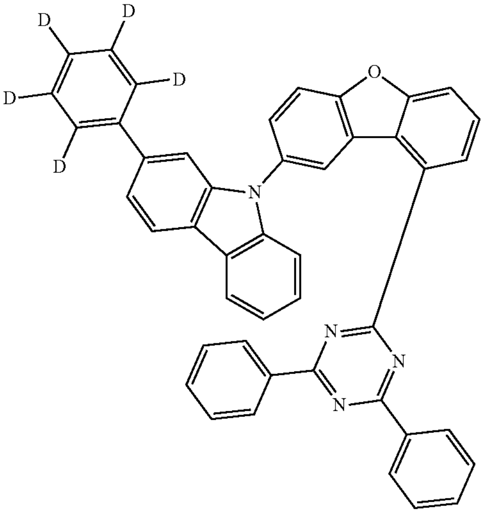
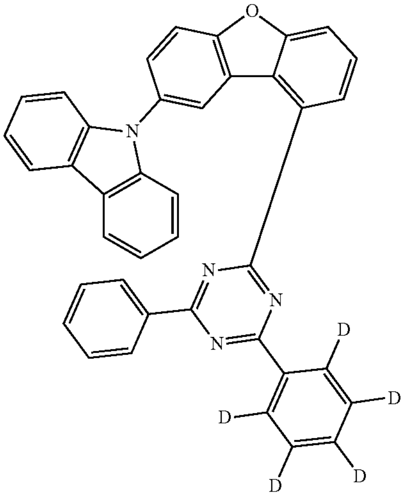
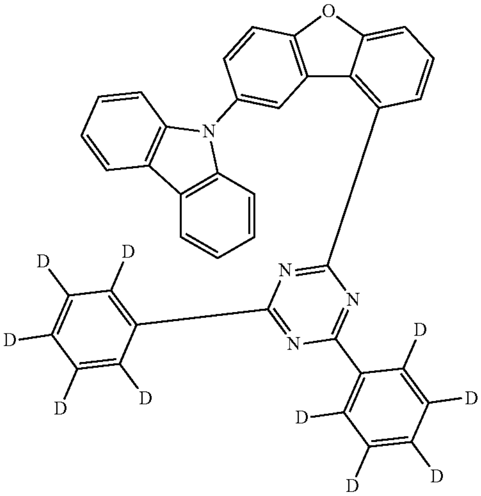

-continued
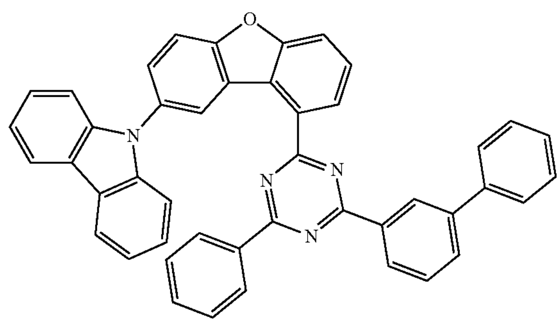
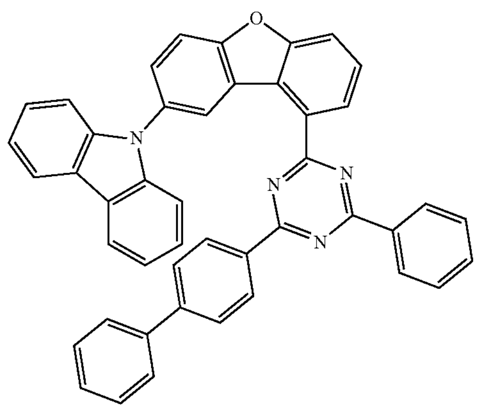
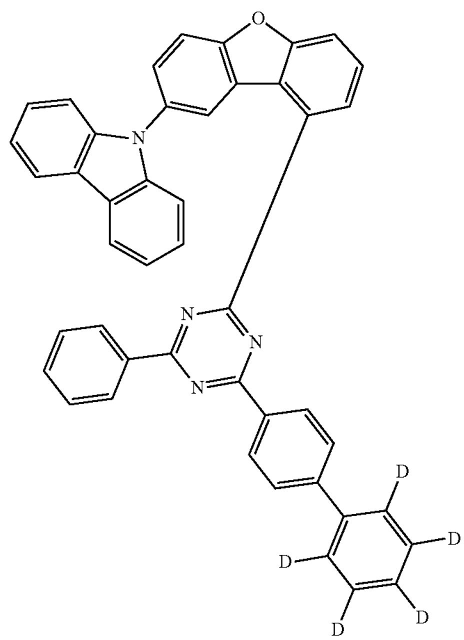
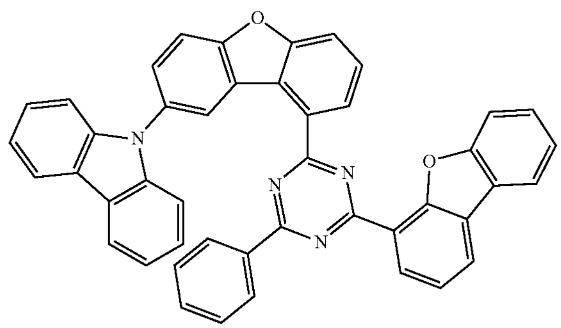
-continued
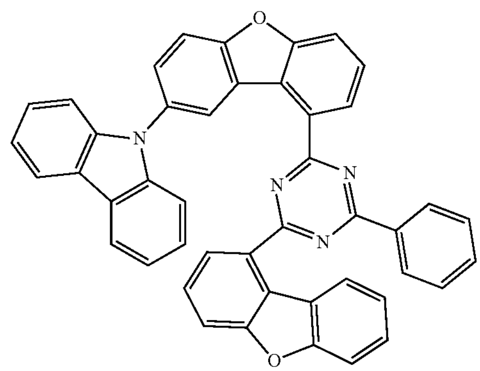
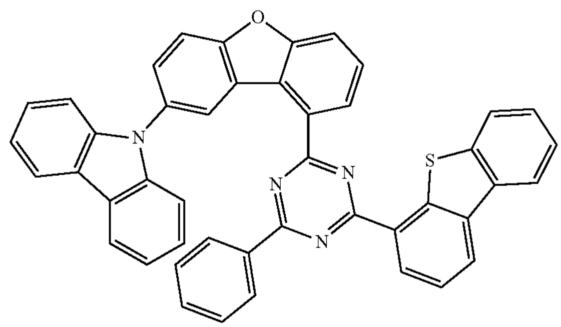
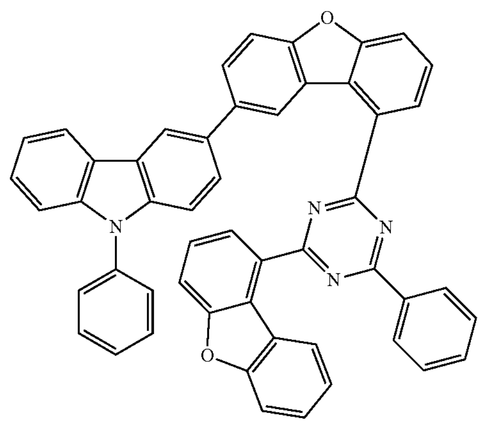
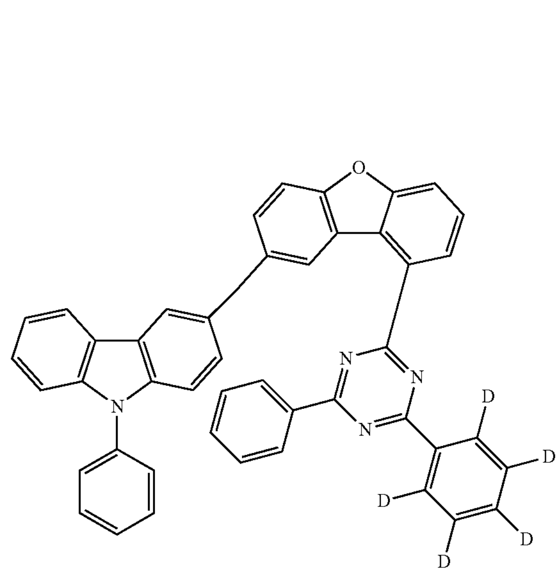

-continued
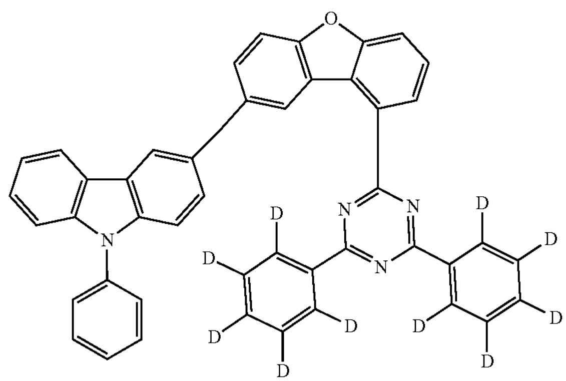
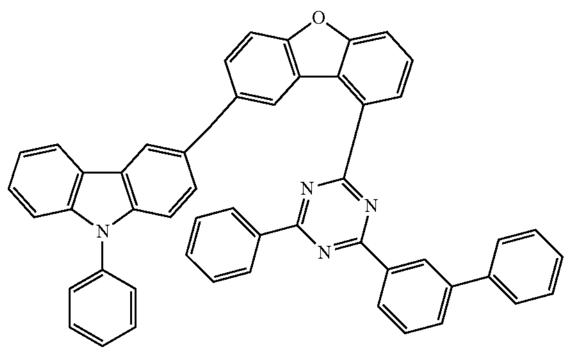
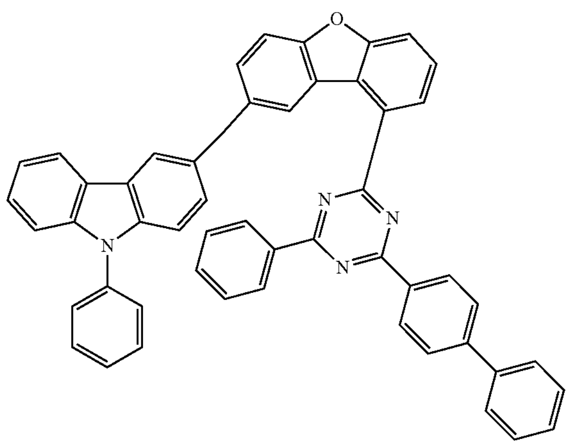
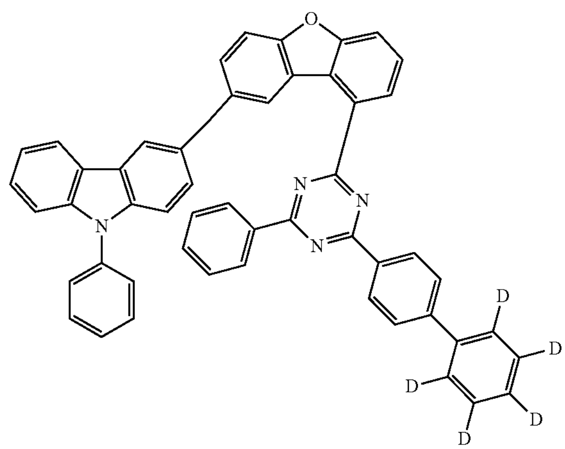
-continued
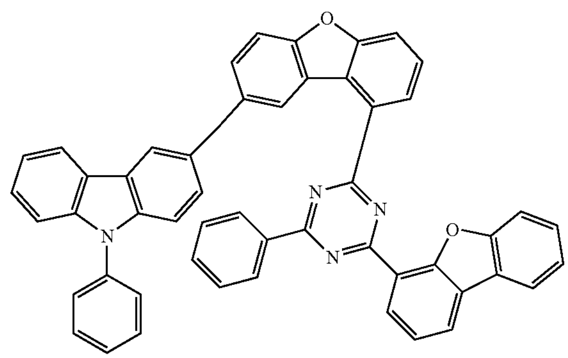
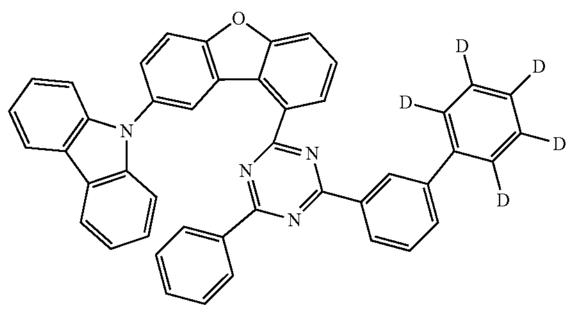
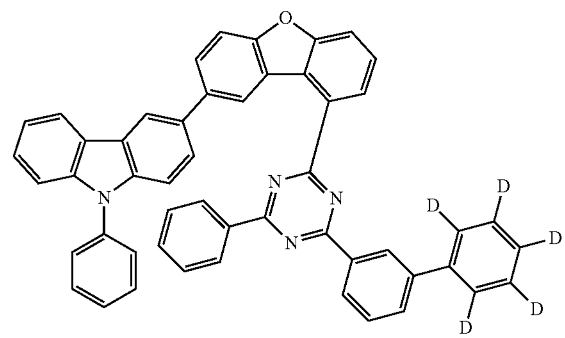
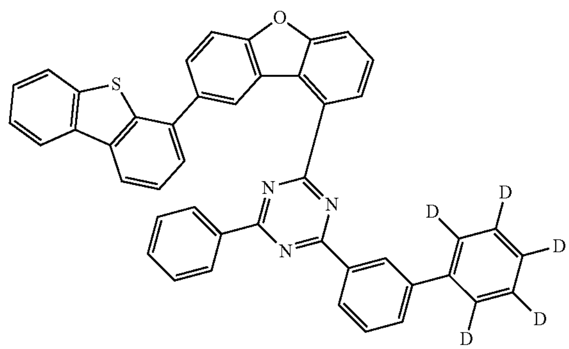
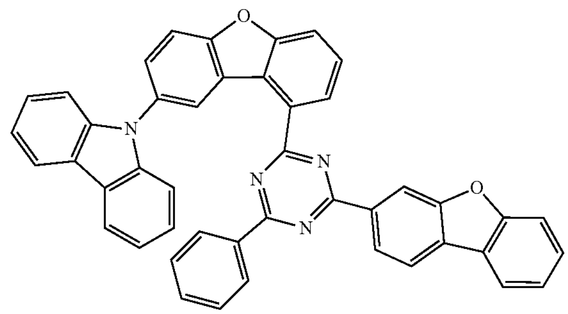

-continued
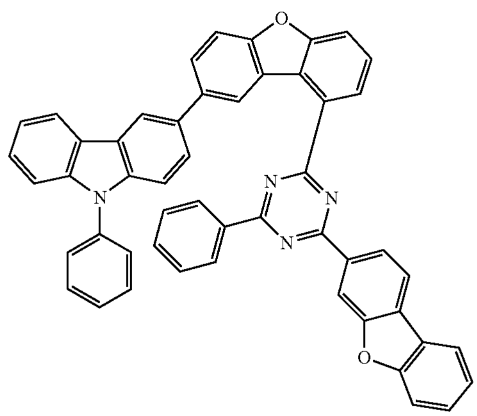
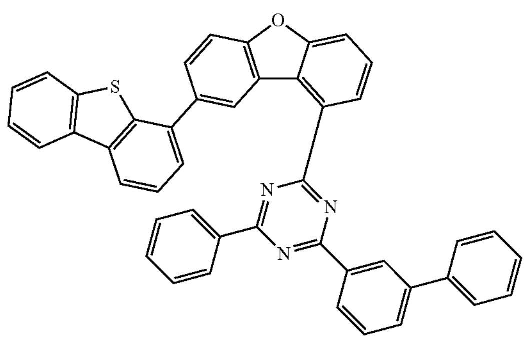
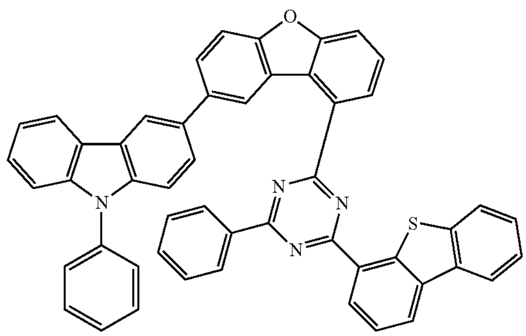
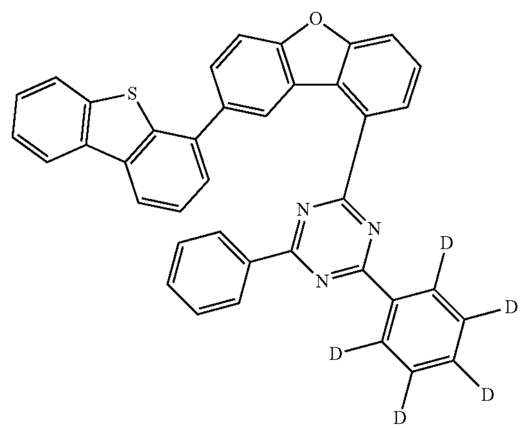
-continued
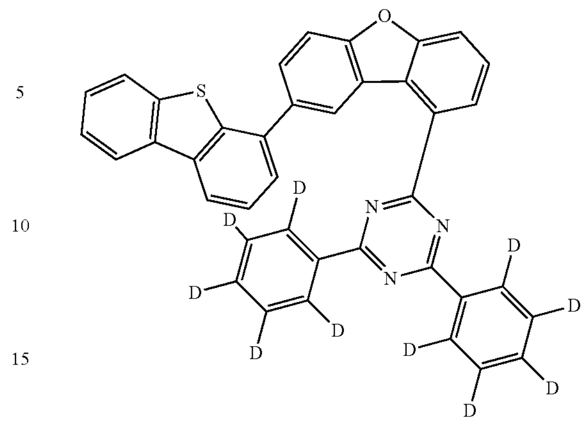
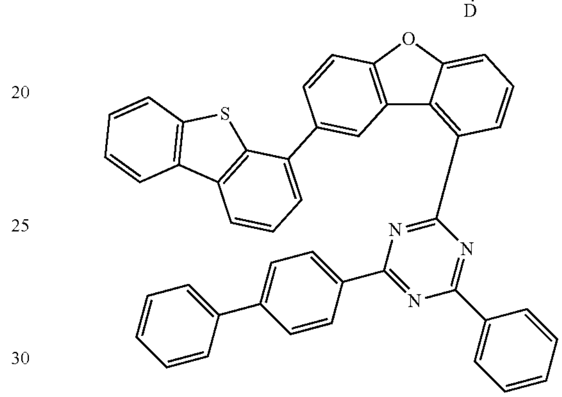
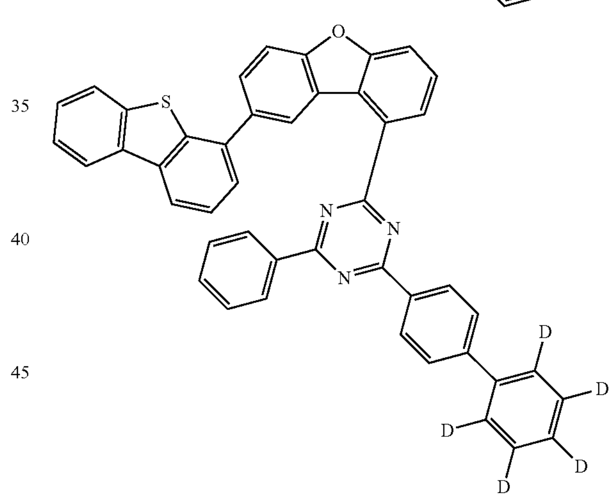
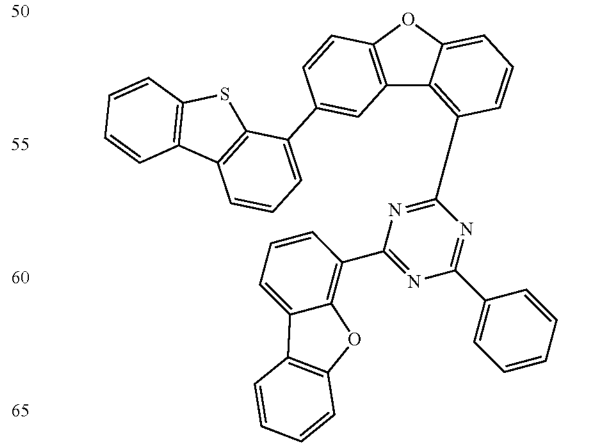

-continued
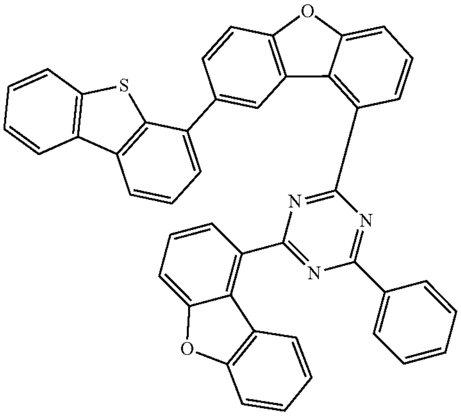
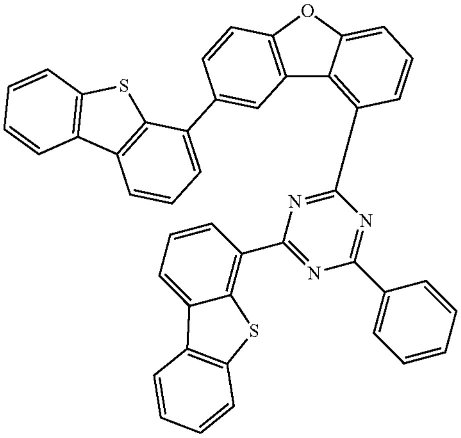
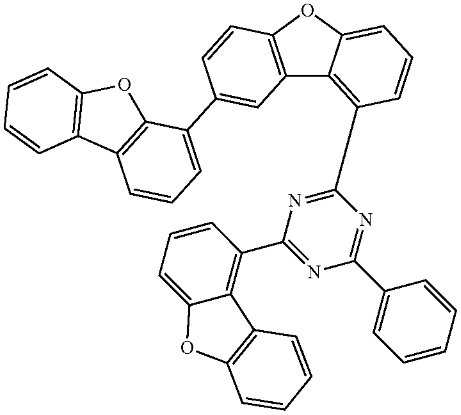
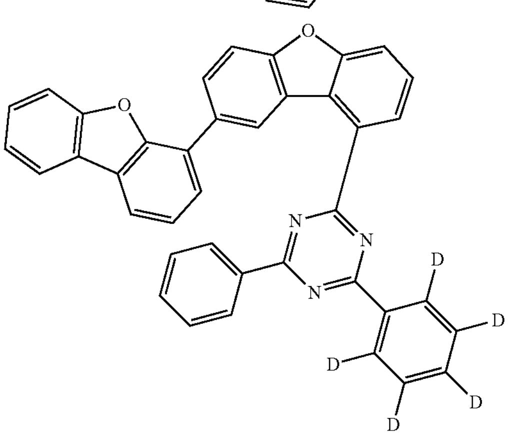
-continued
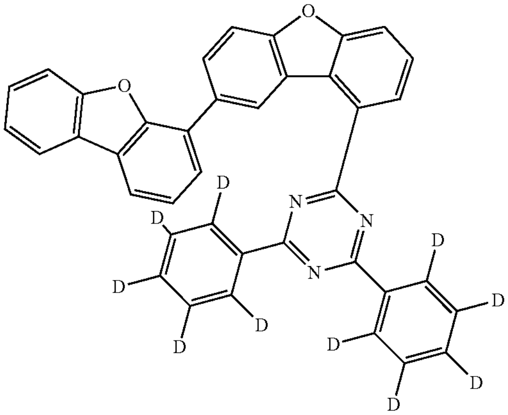
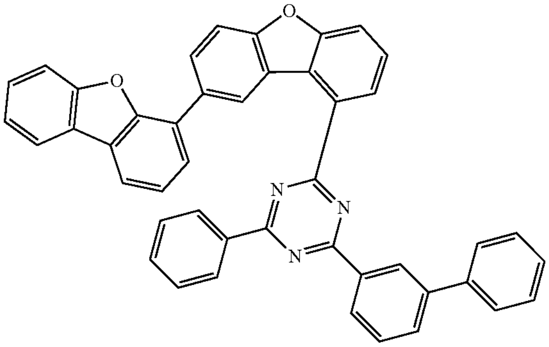
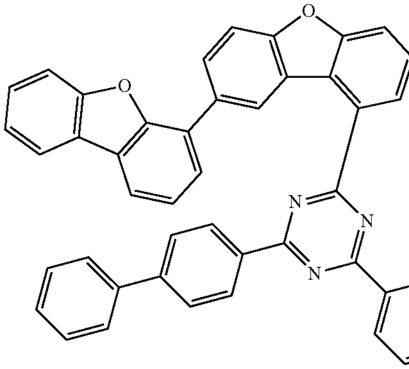
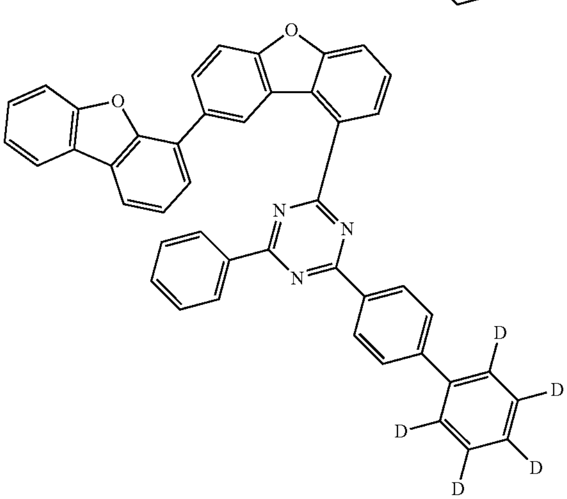

-continued
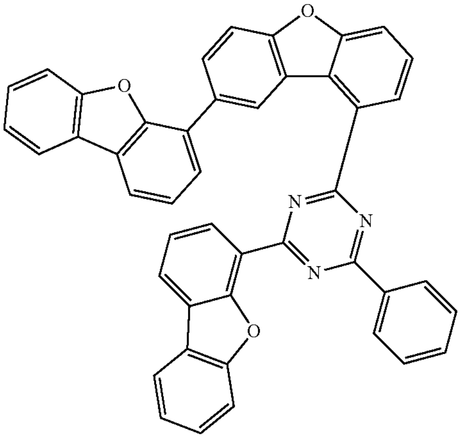
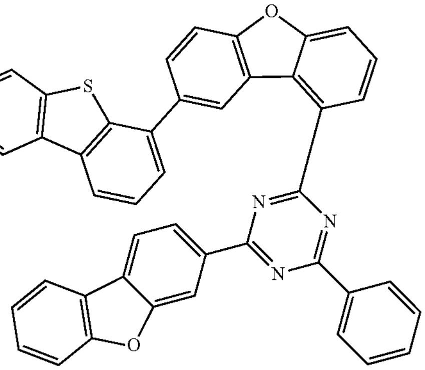
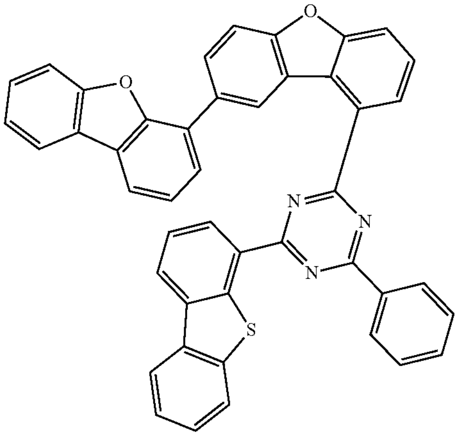
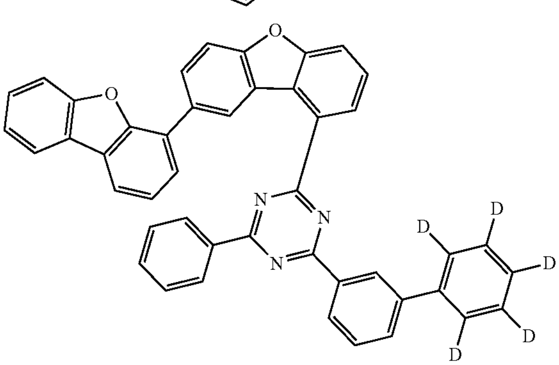
-continued
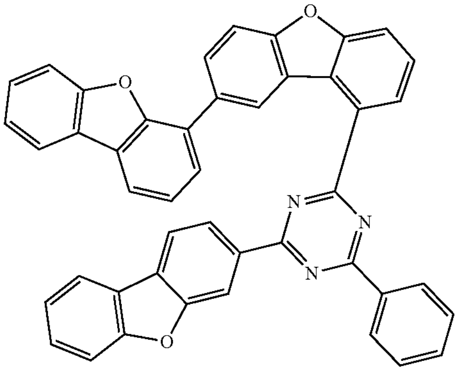
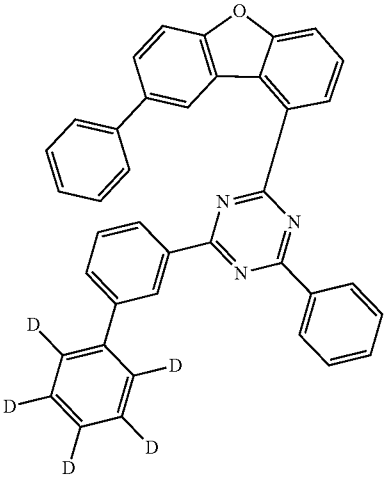
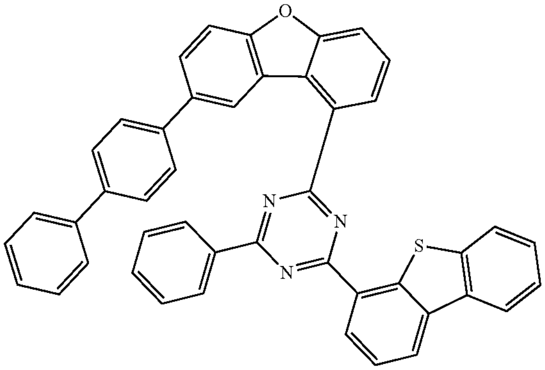
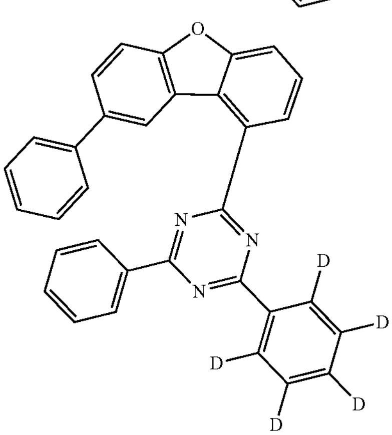

-continued
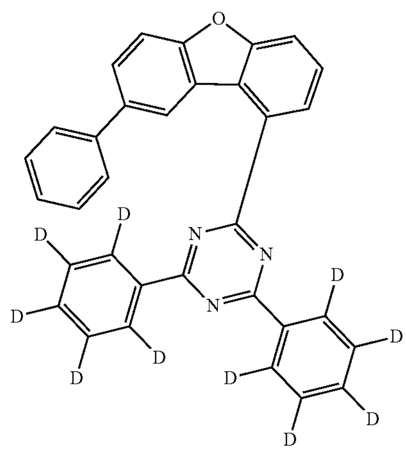
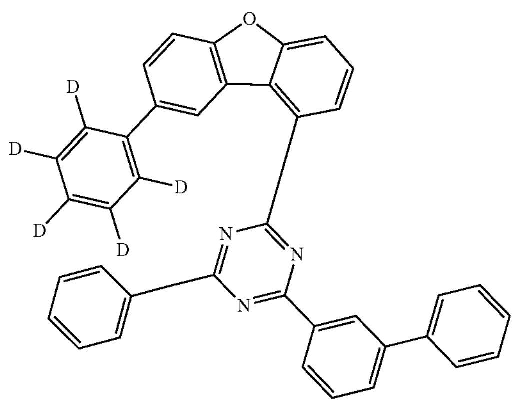
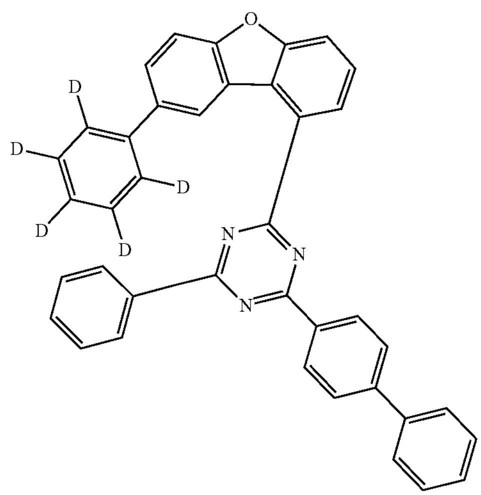
-continued
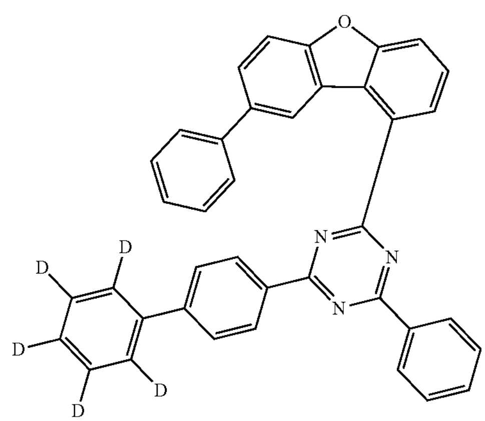
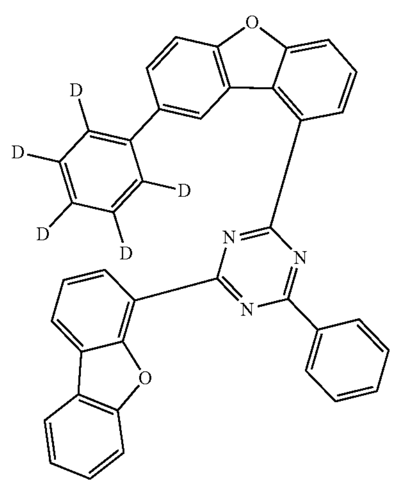
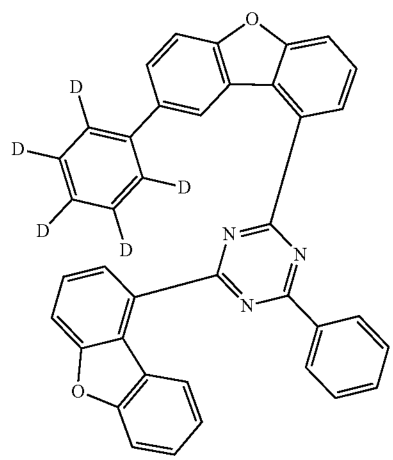

-continued
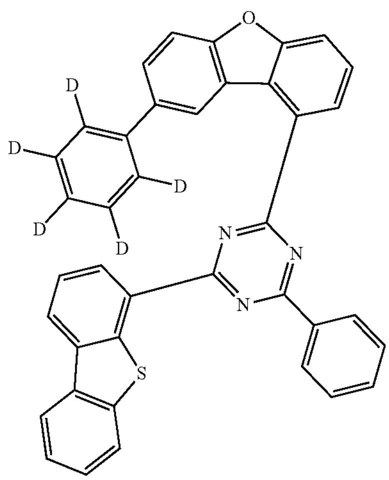
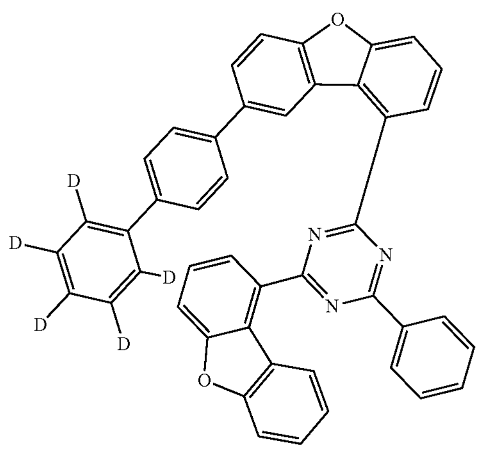
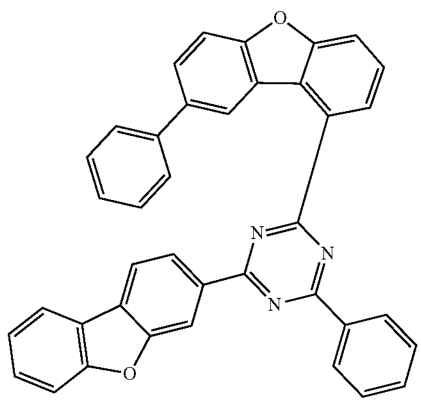
-continued
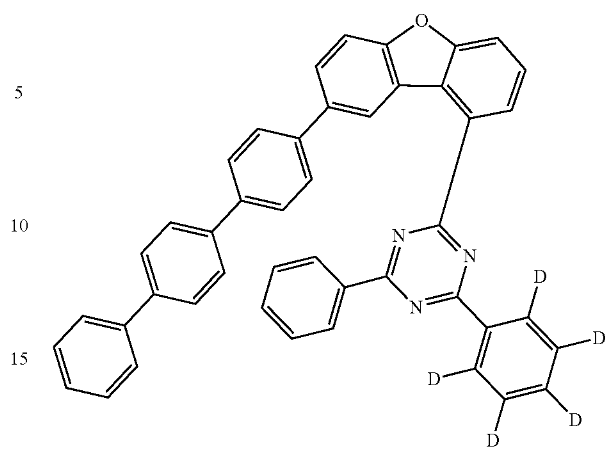
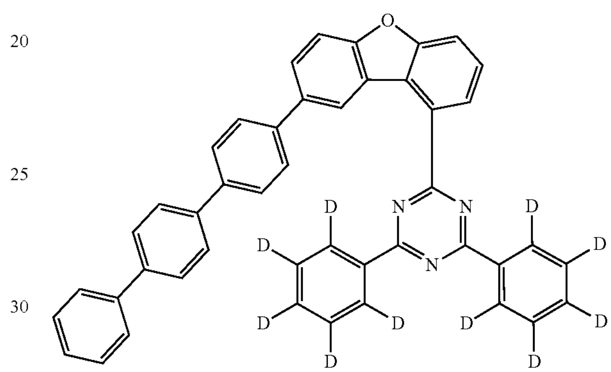
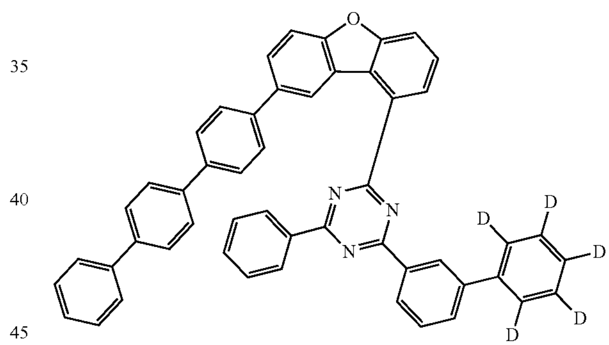
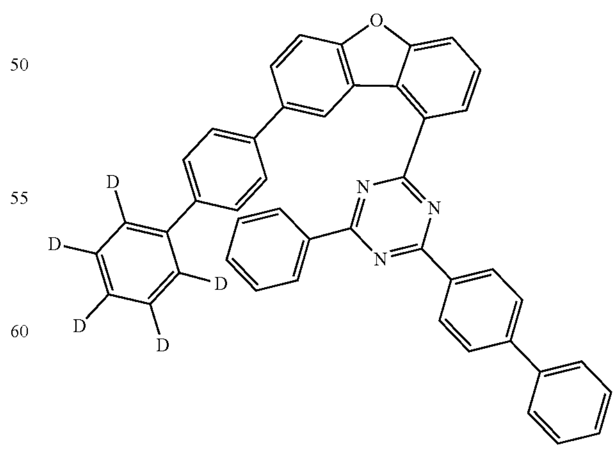

-continued
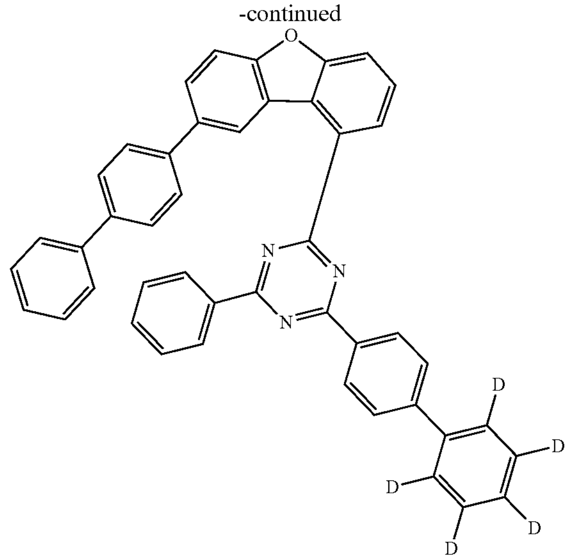
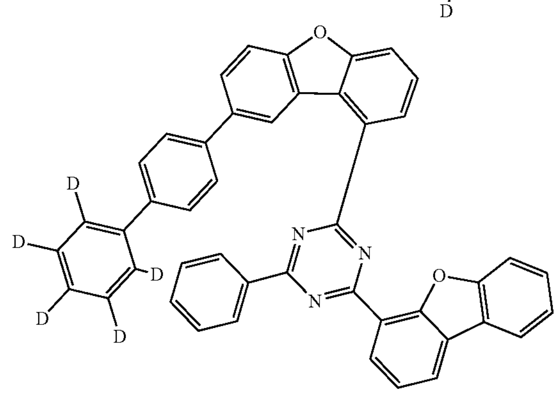
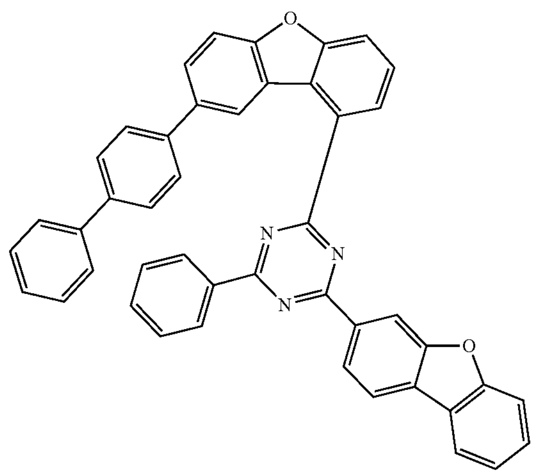
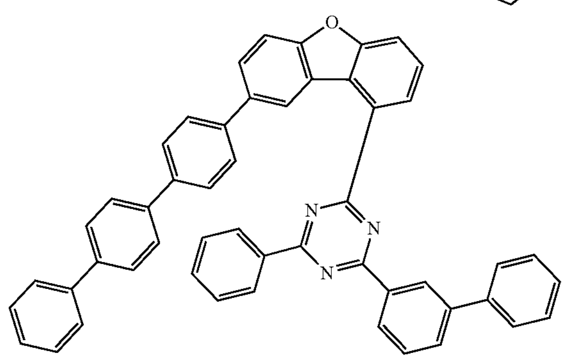
-continued
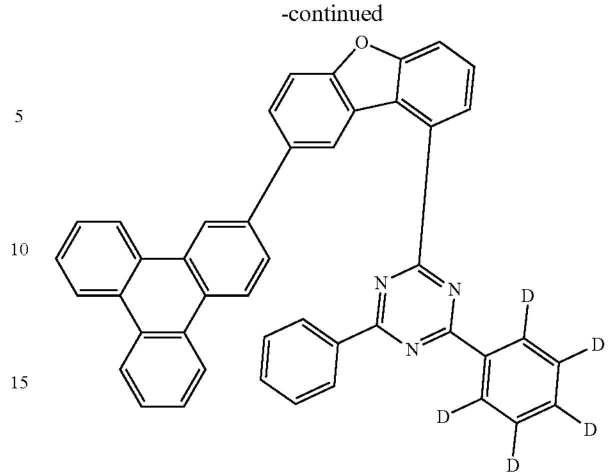
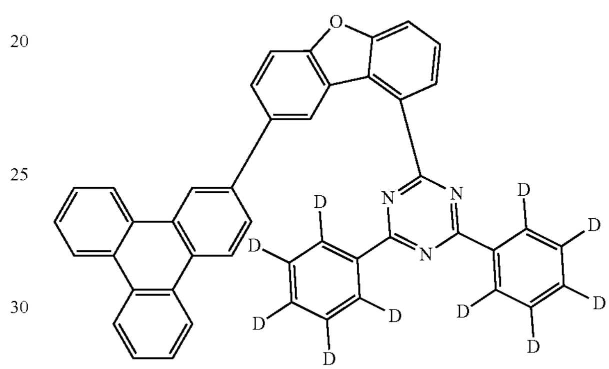
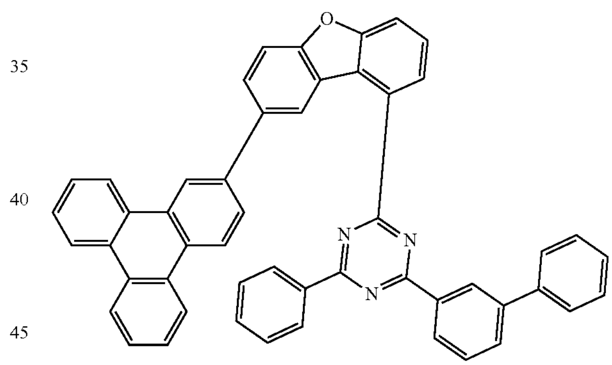
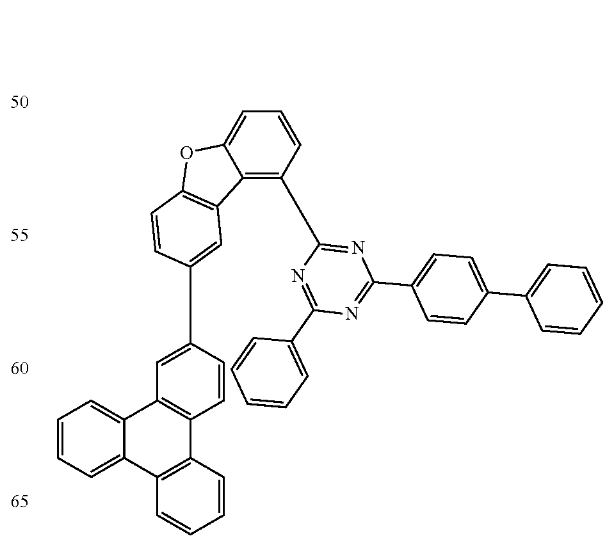

-continued
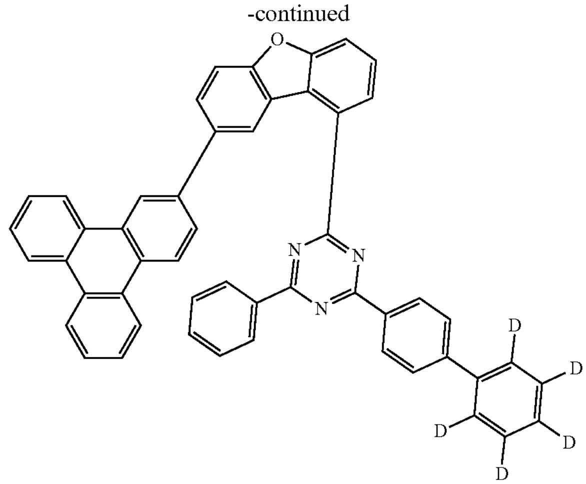
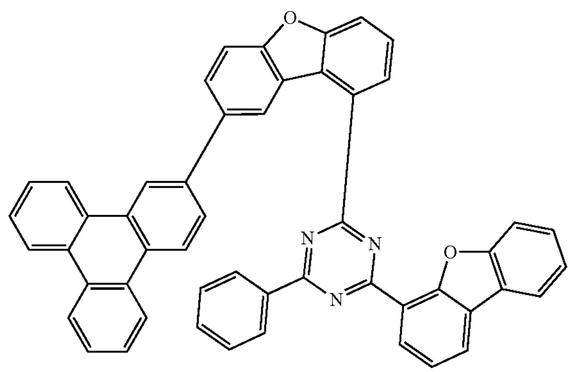
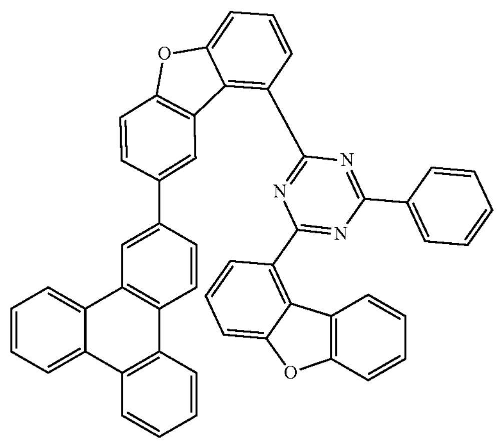
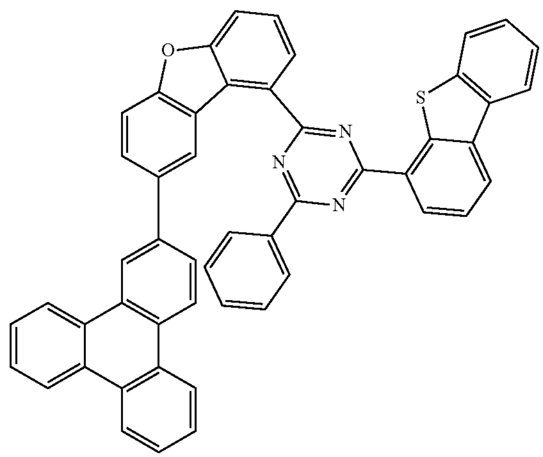
-continued
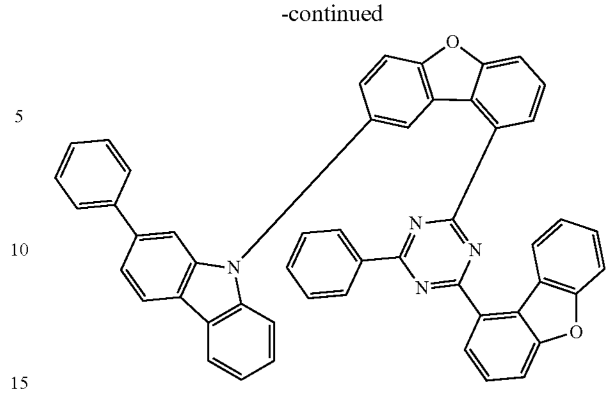
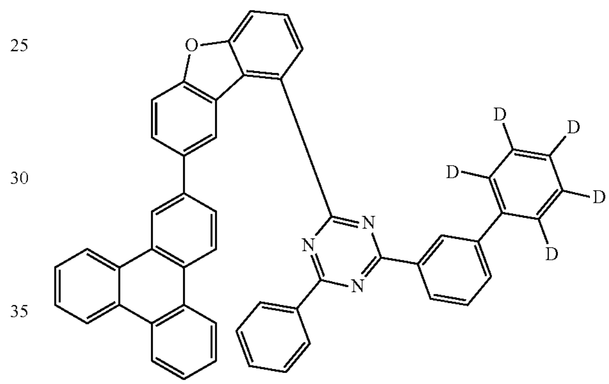
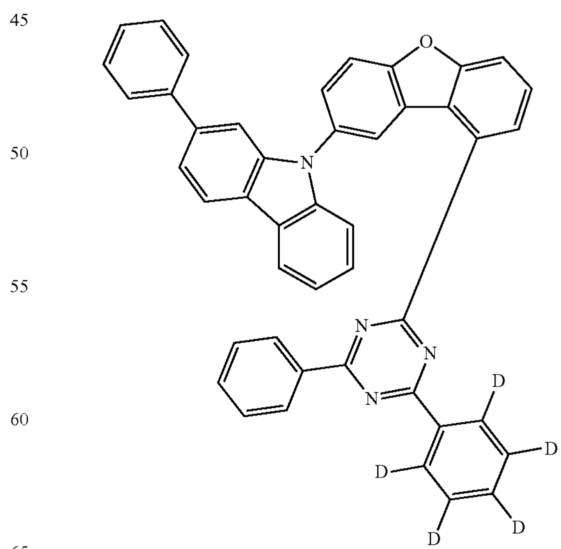

-continued
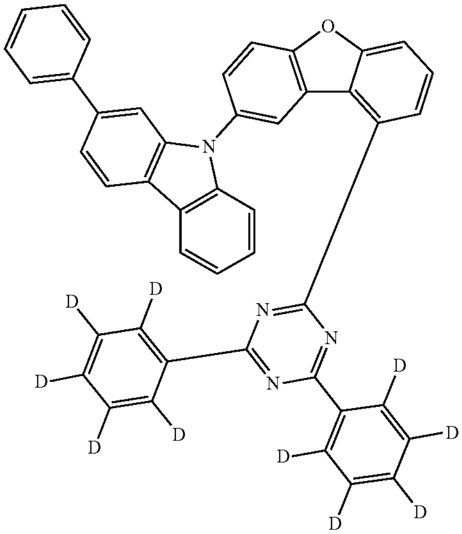
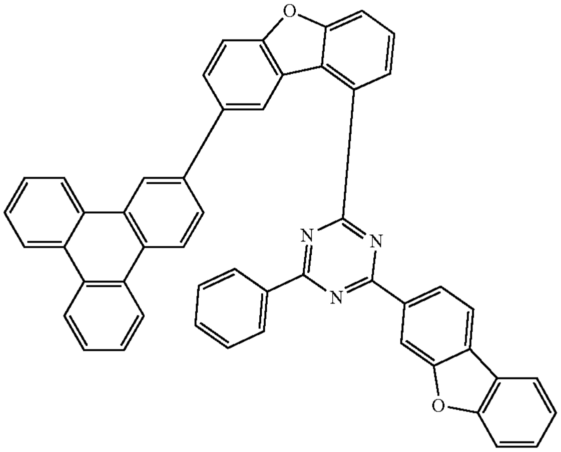
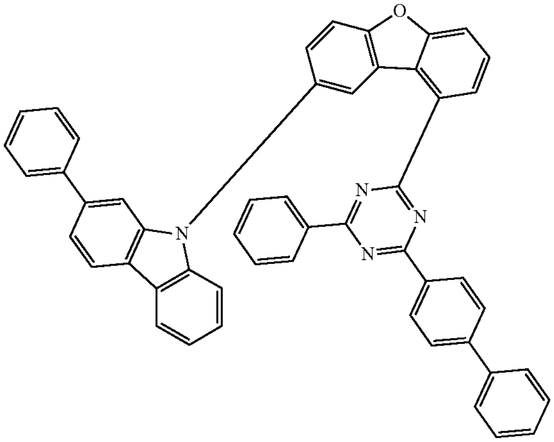
-continued
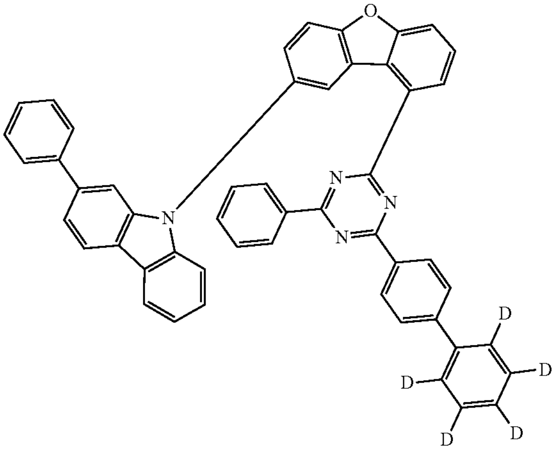
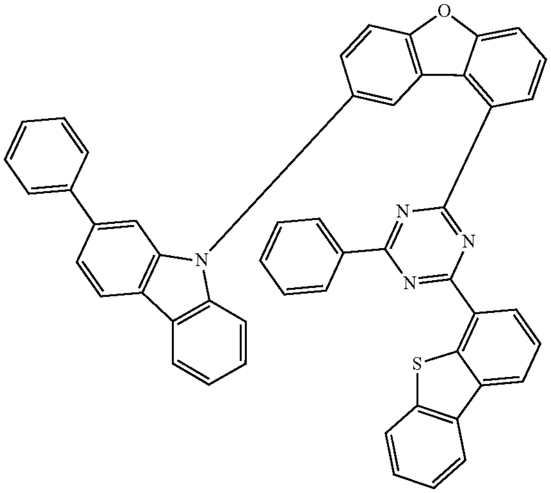
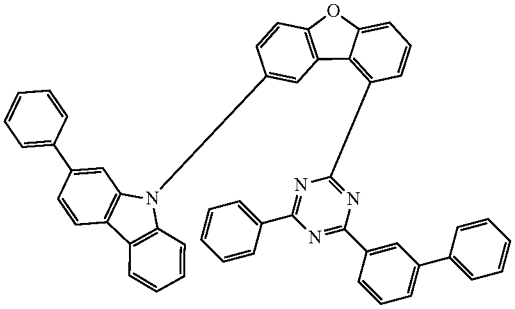
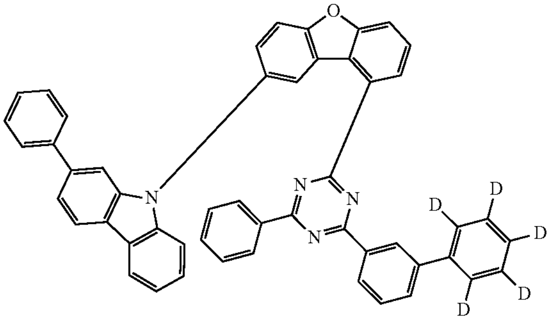

-continued
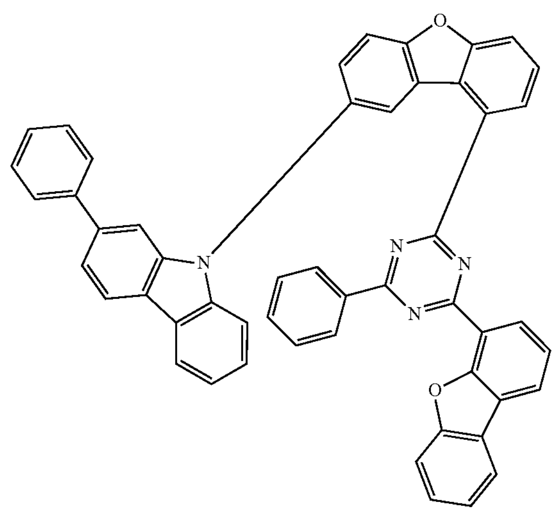
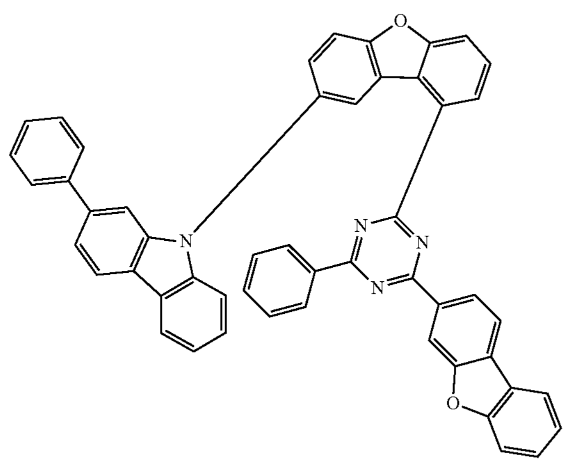
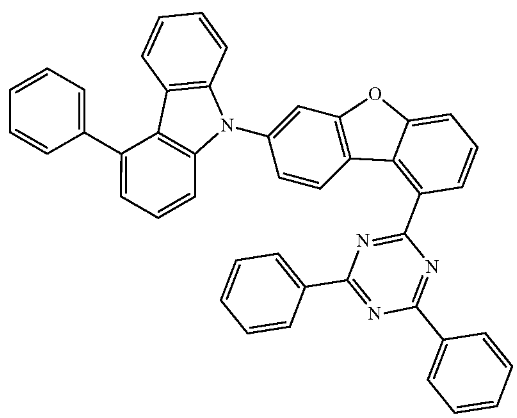
-continued
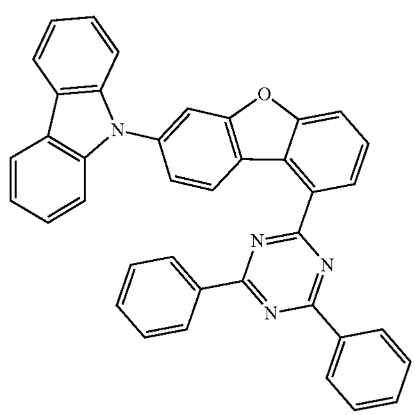
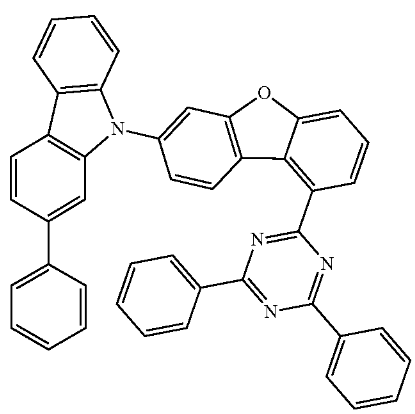
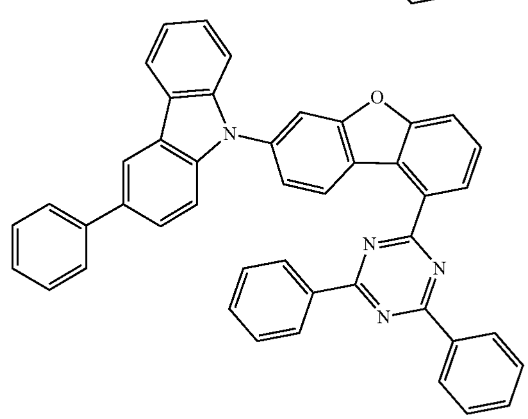
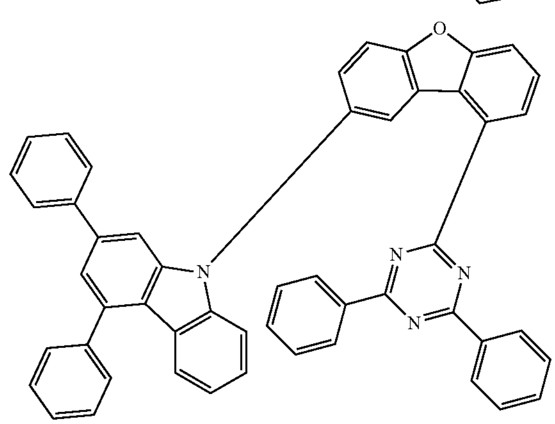

-continued
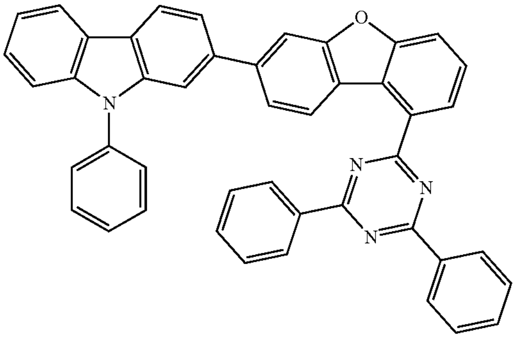
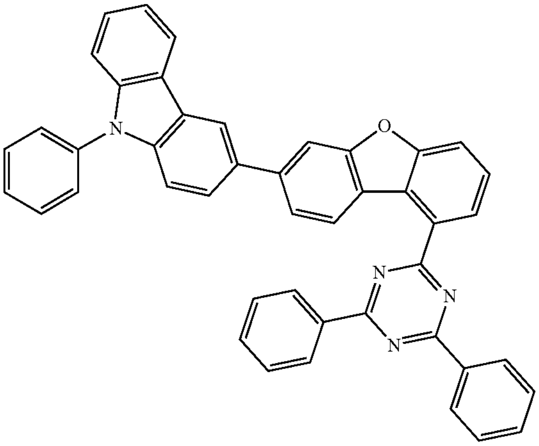
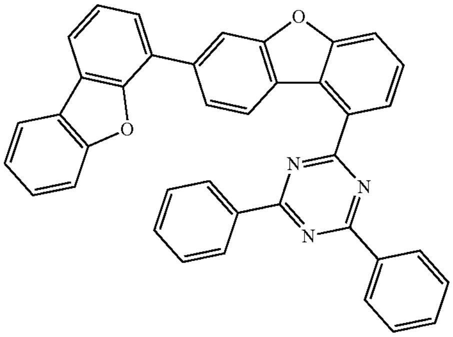
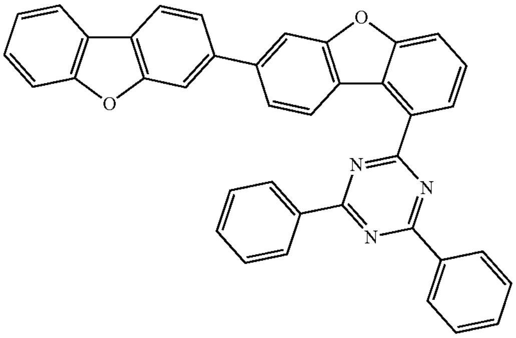
-continued
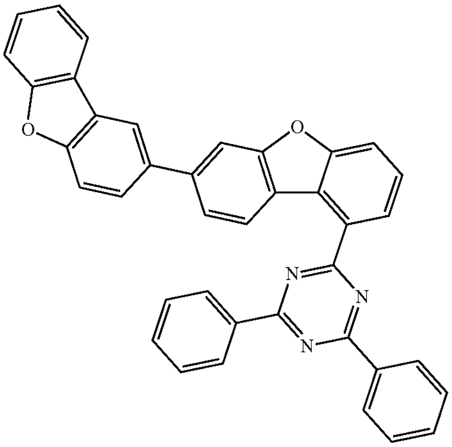
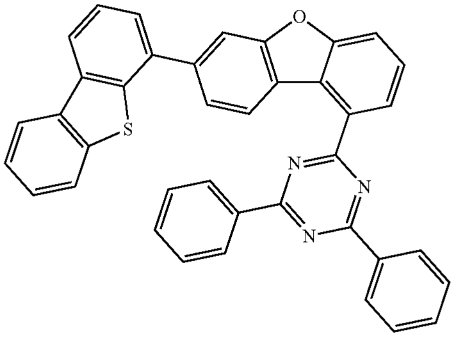
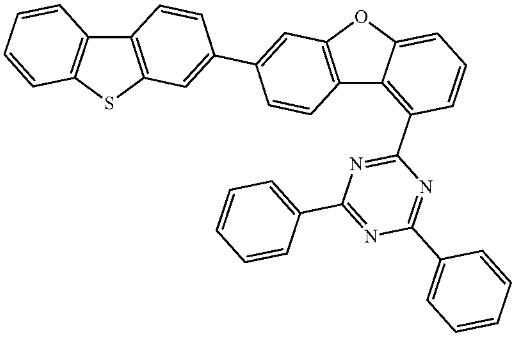
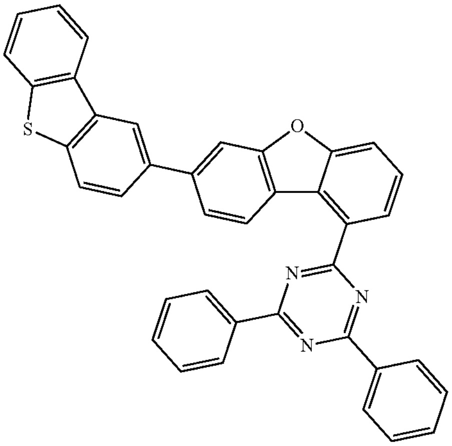

-continued
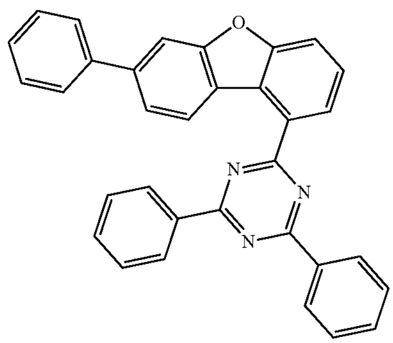
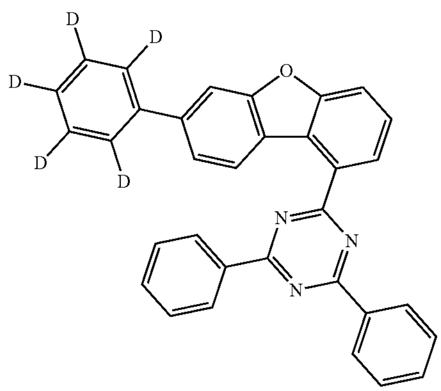
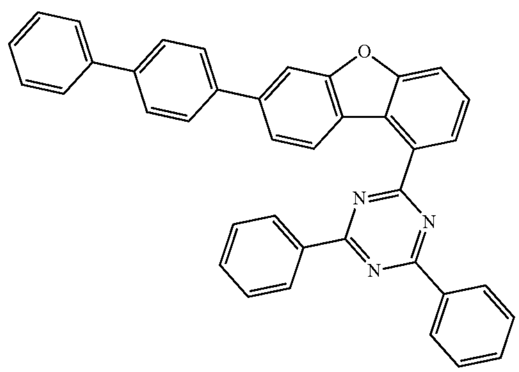
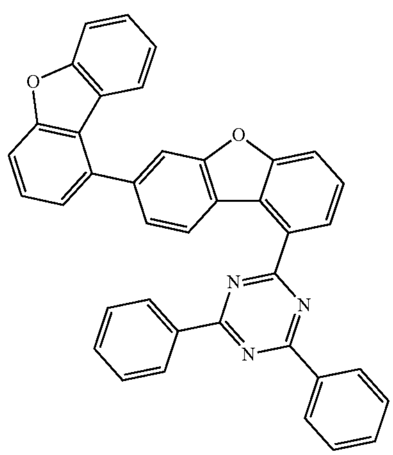
-continued
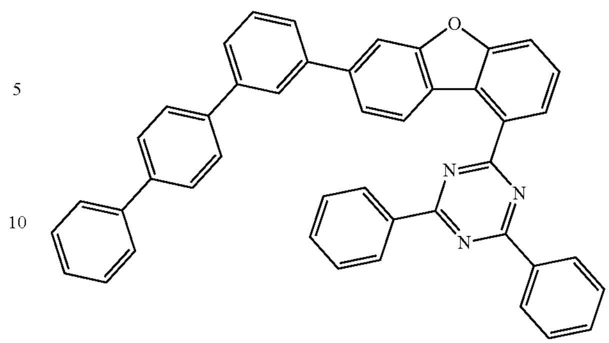
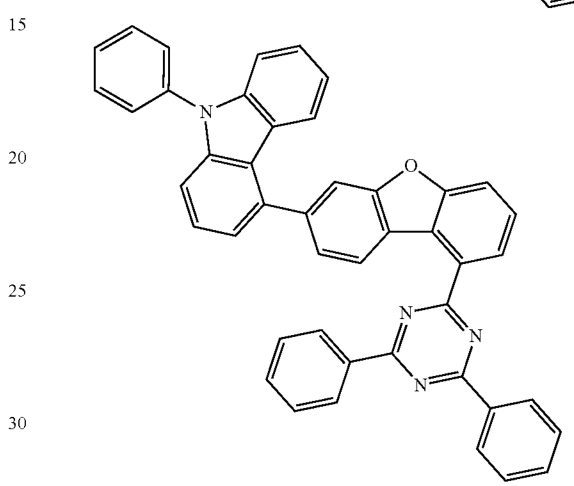
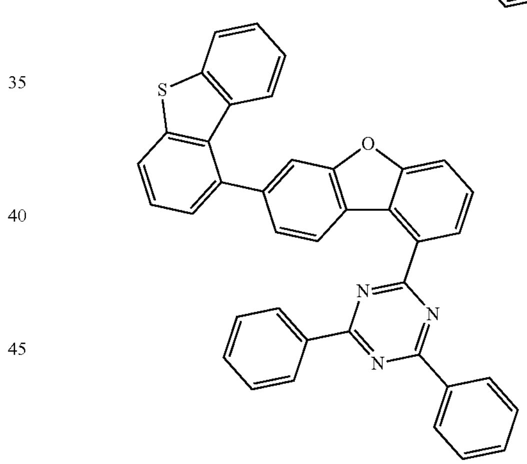
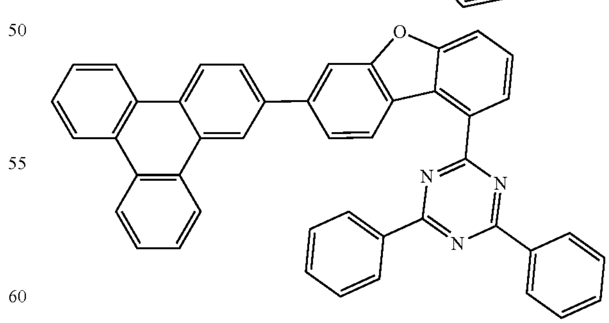

-continued
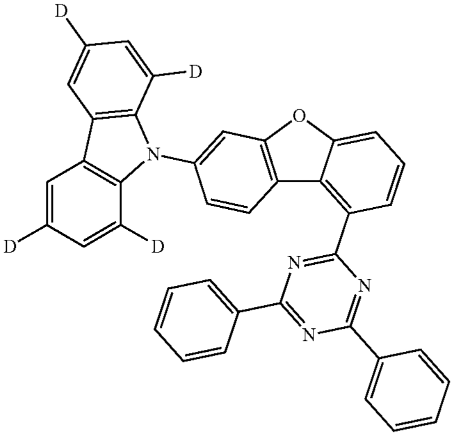
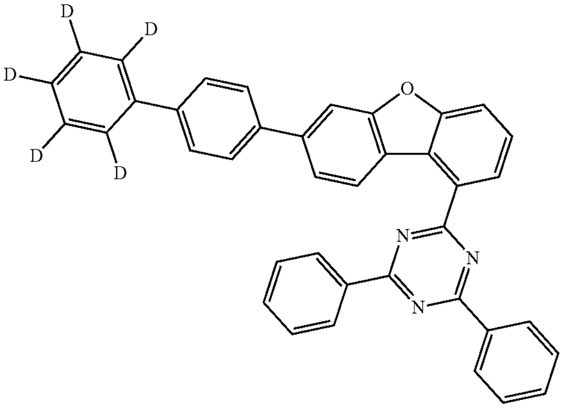
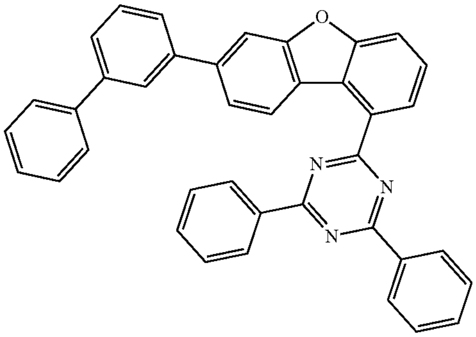
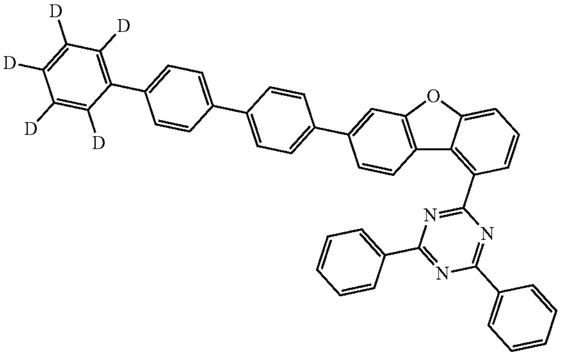
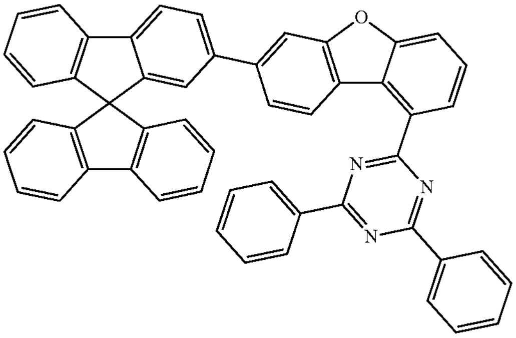
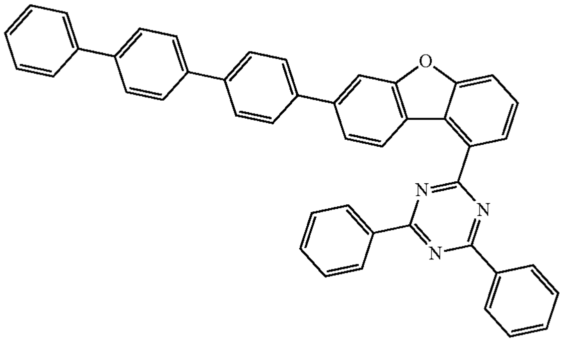
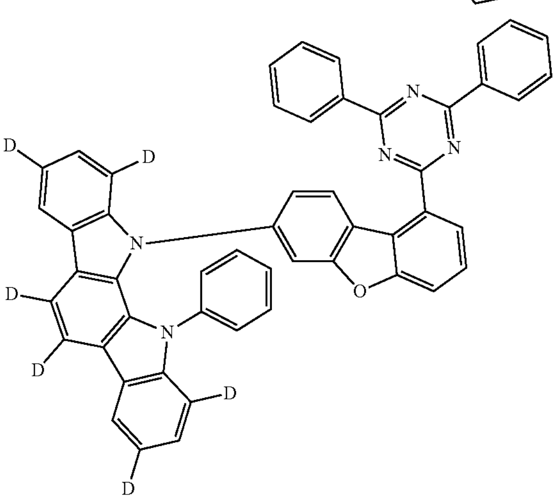
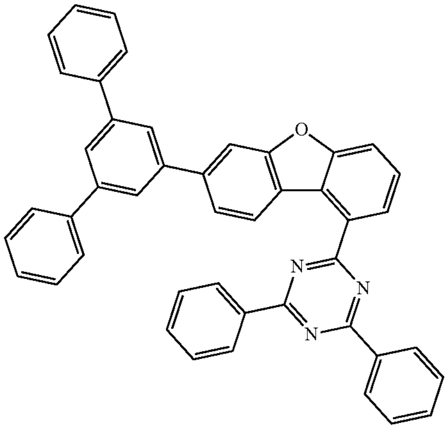

-continued
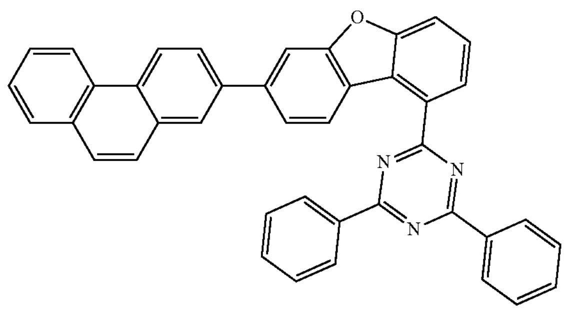
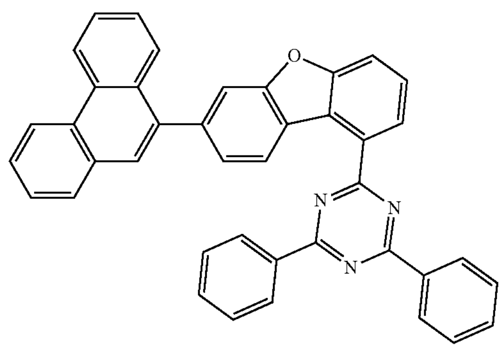
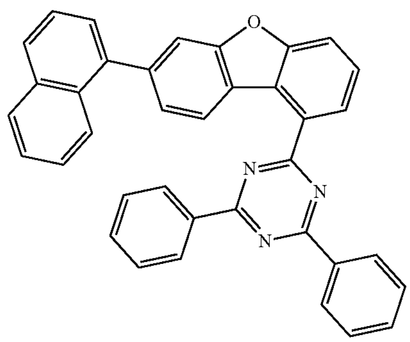
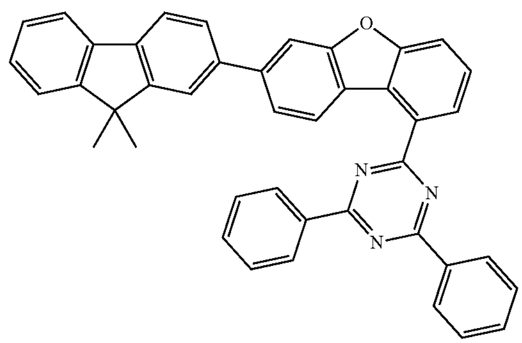
-continued
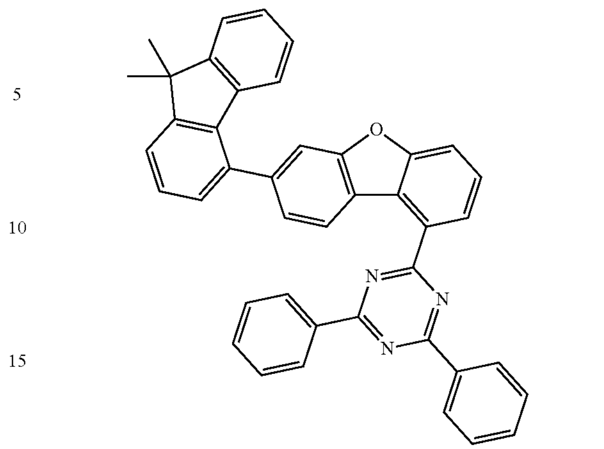
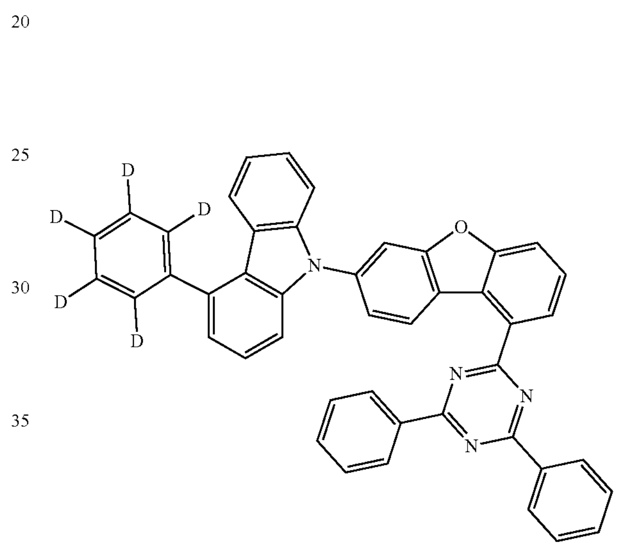
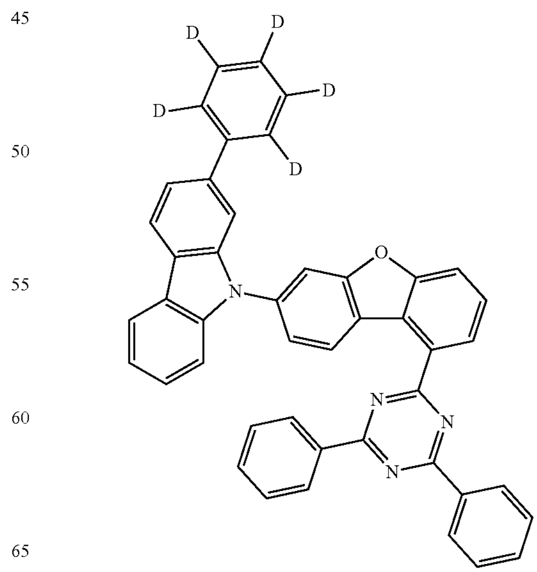

-continued
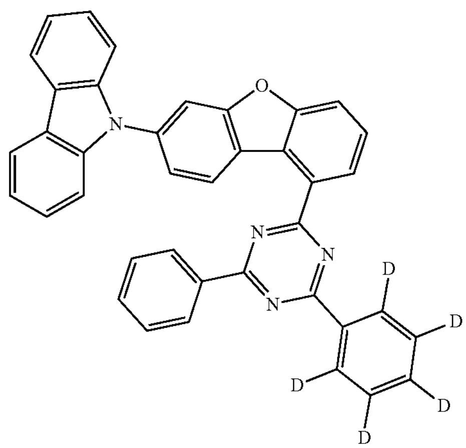
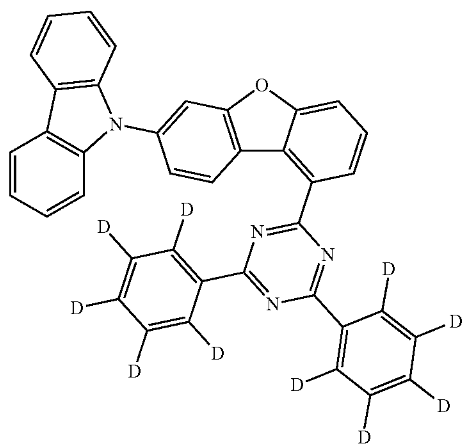
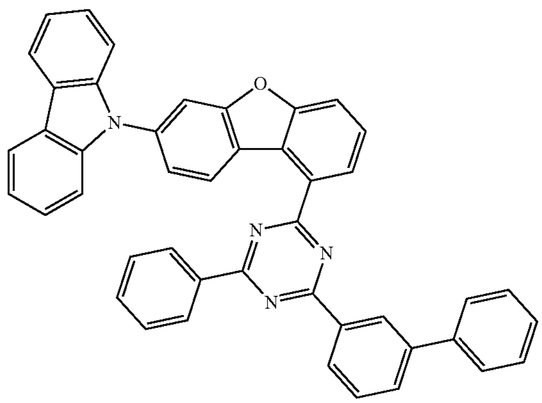
-continued
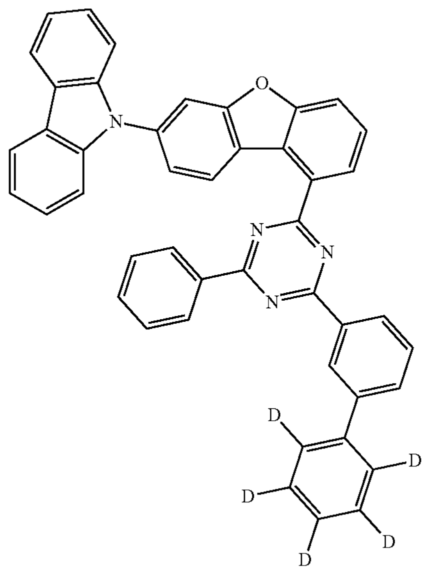
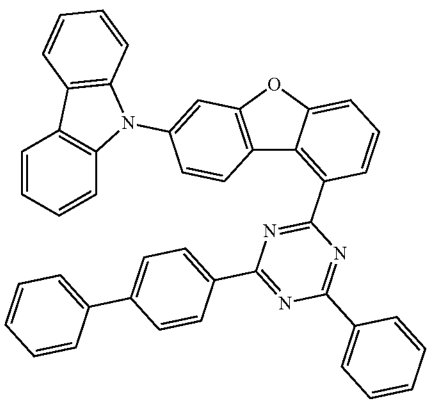
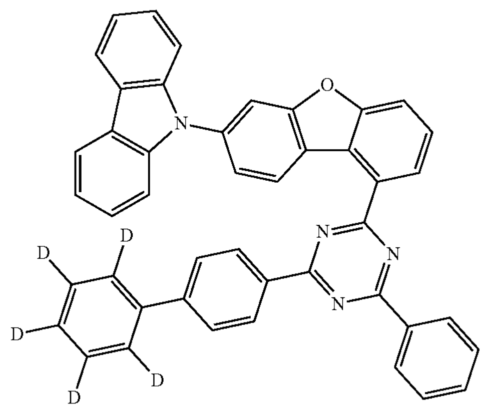

-continued
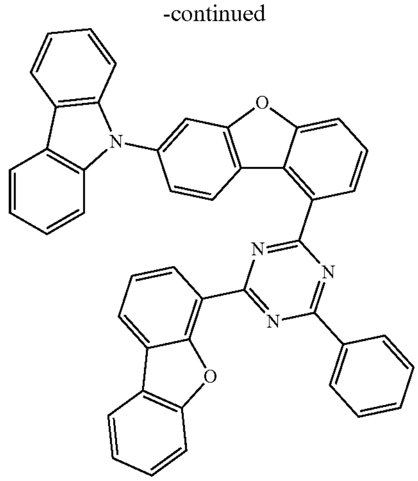
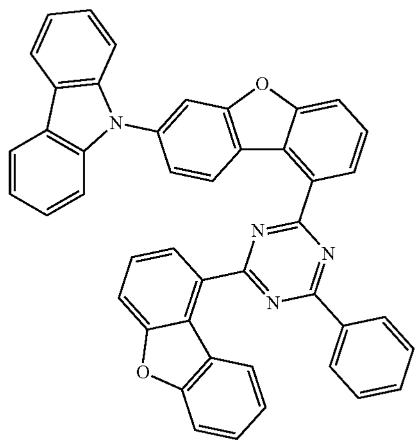
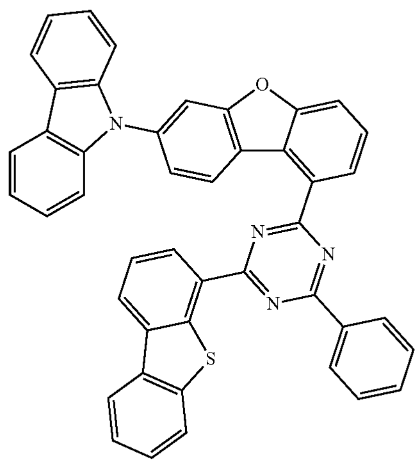
-continued
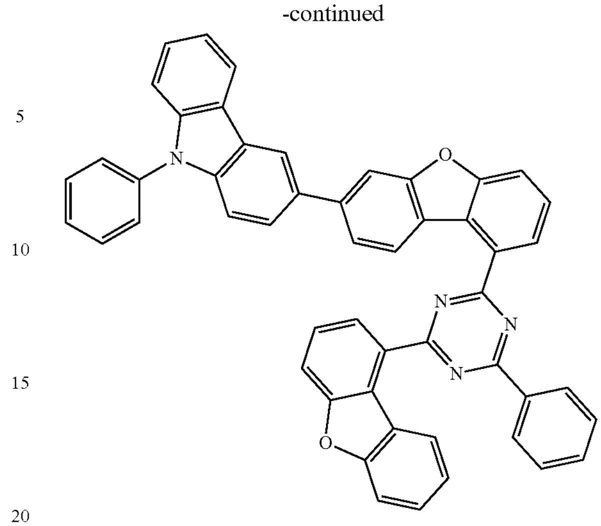
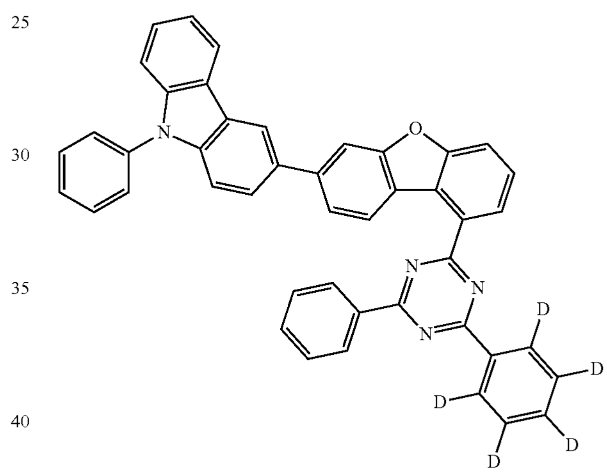
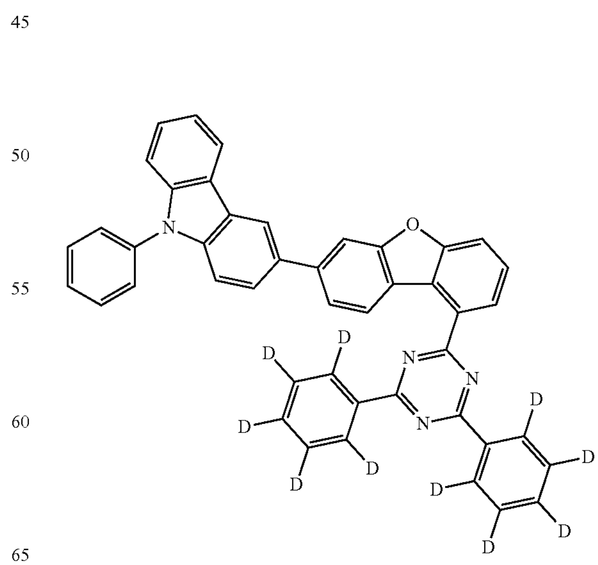

-continued
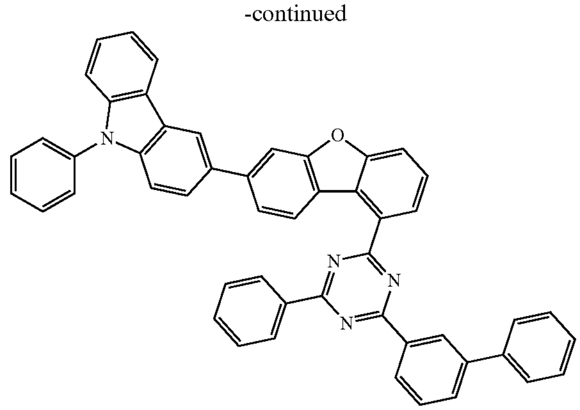
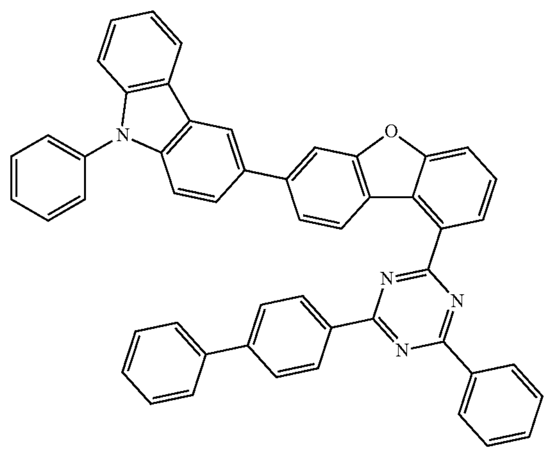
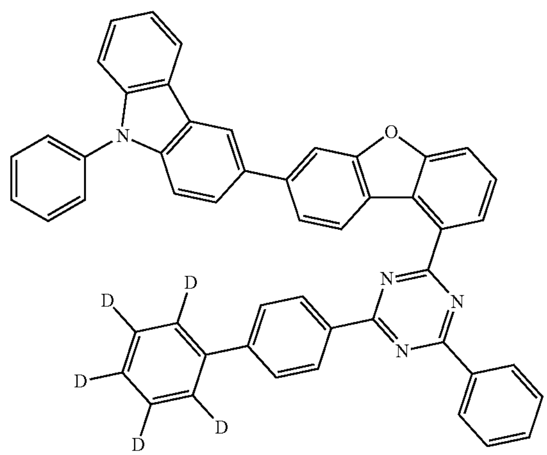
-continued
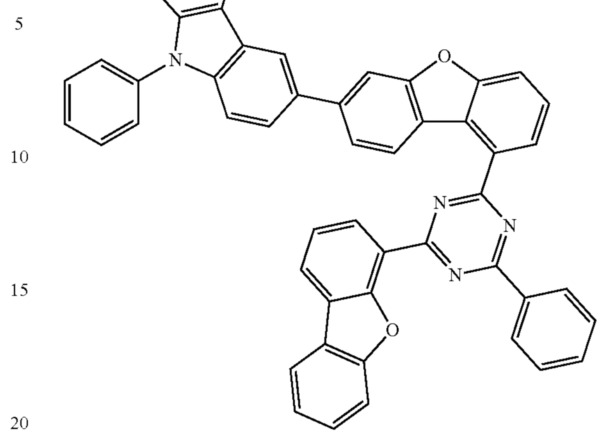
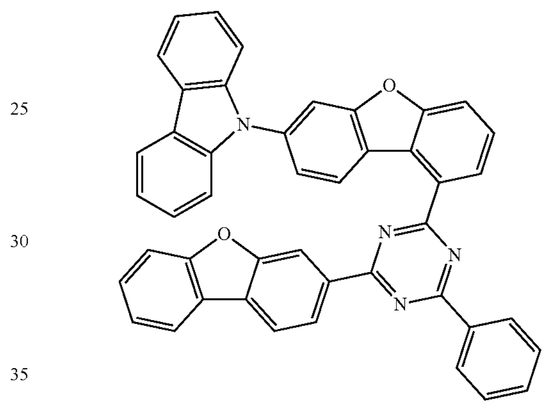
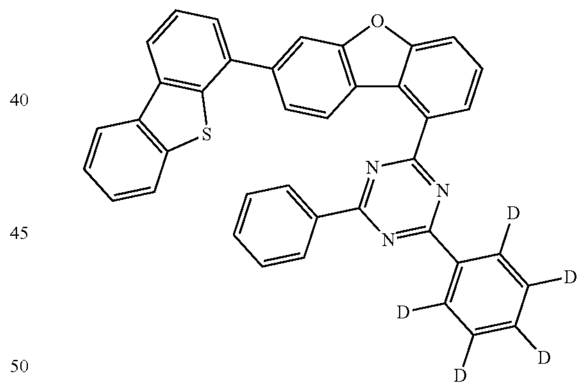
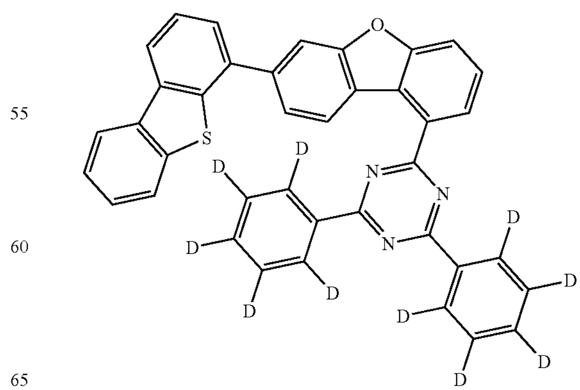

-continued
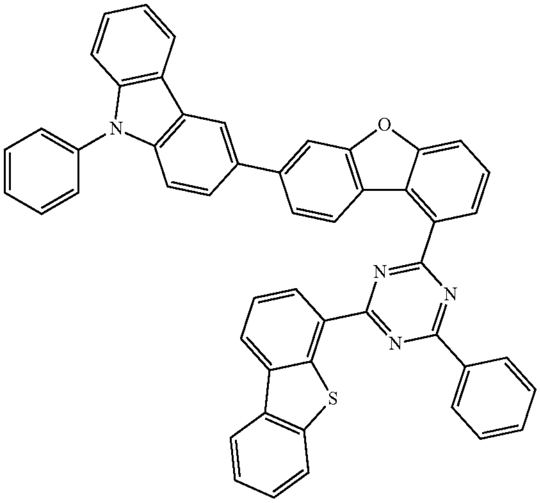
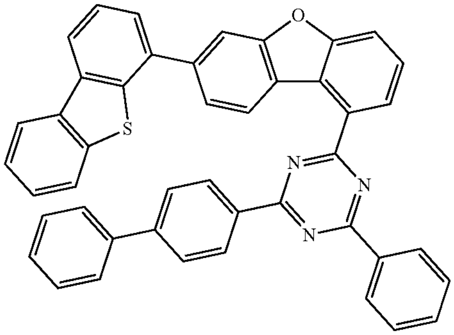
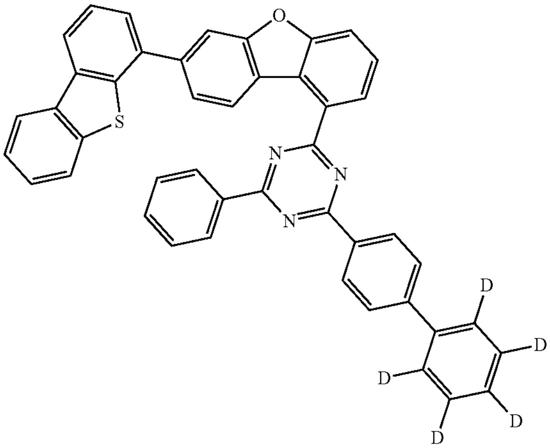
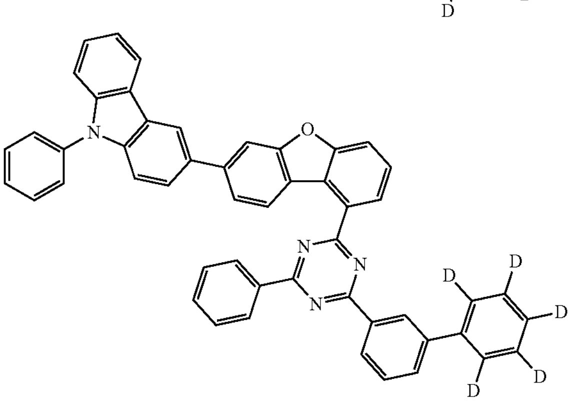
-continued
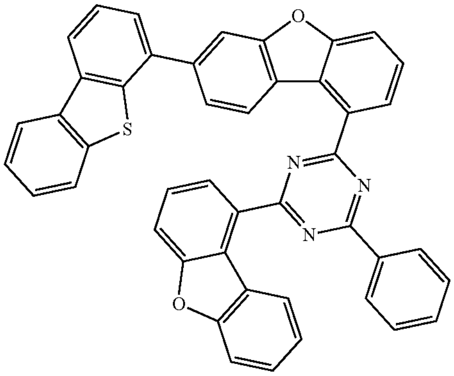
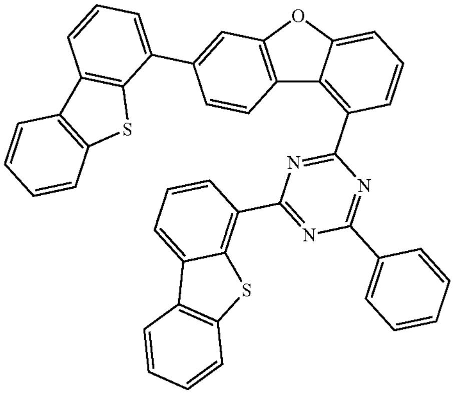
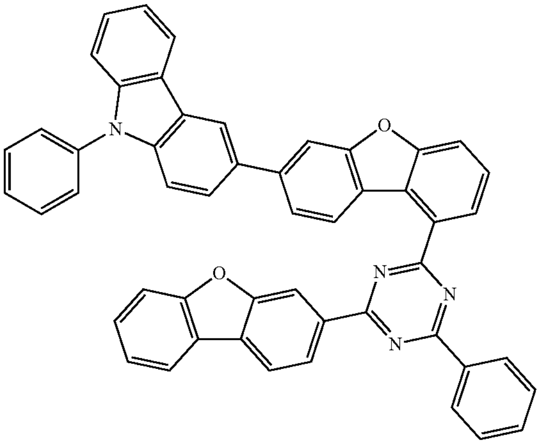
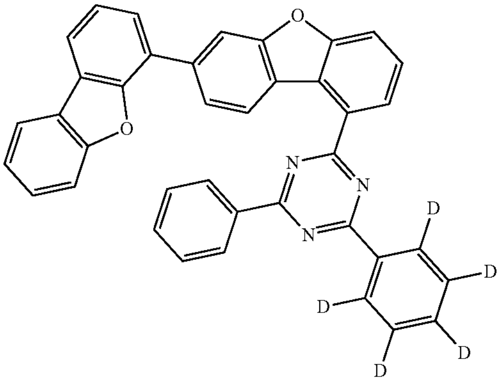

-continued
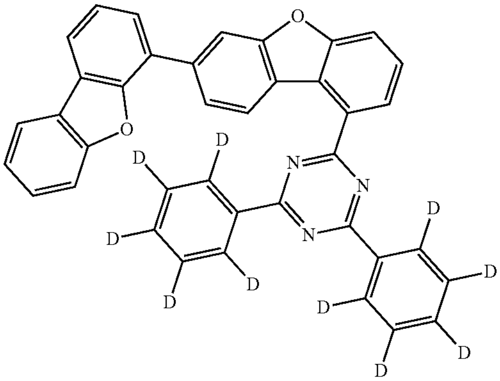
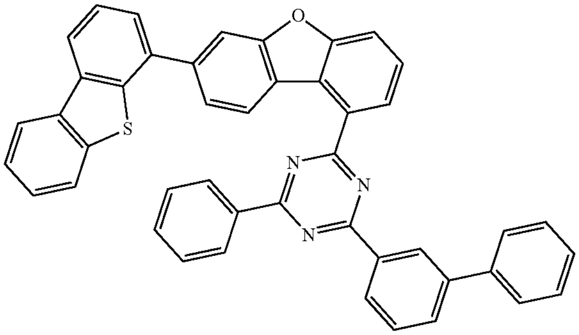
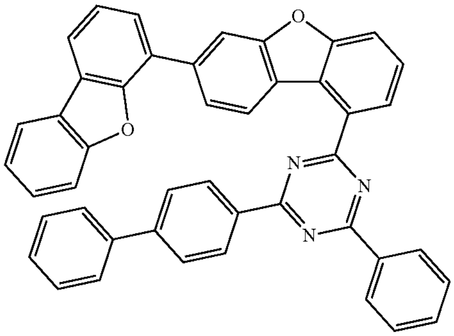
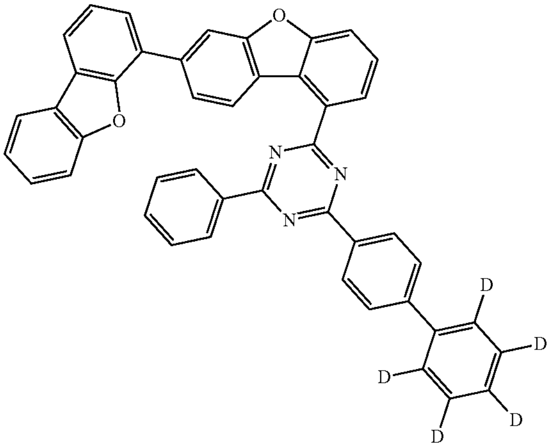
-continued
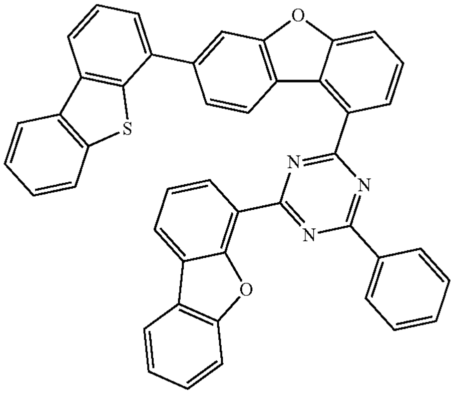
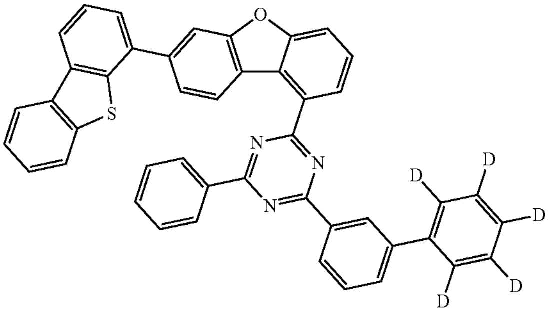
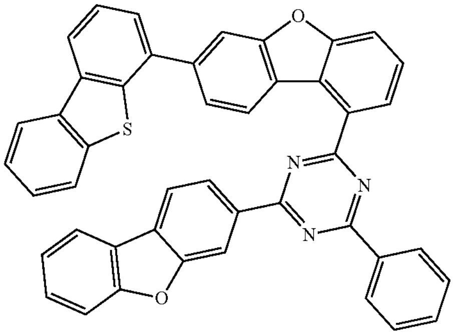
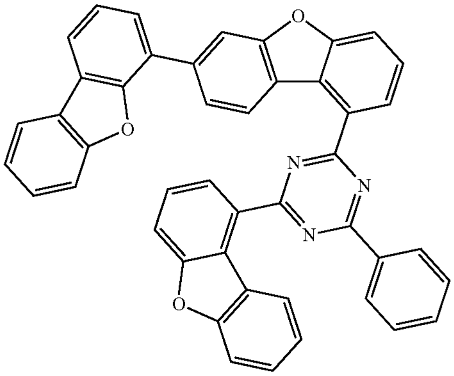

-continued
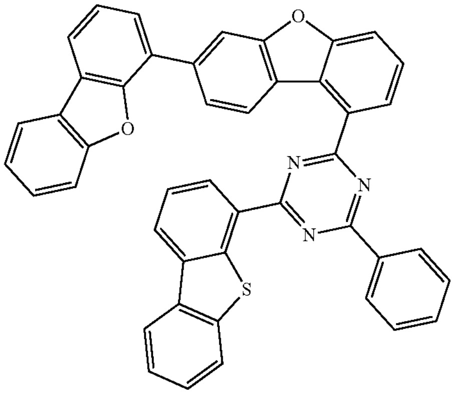
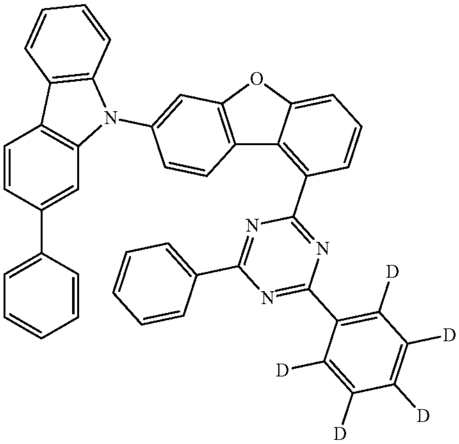
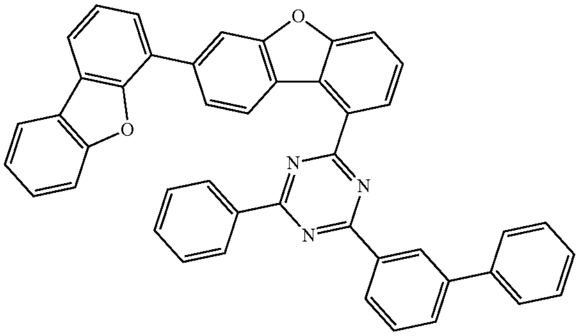
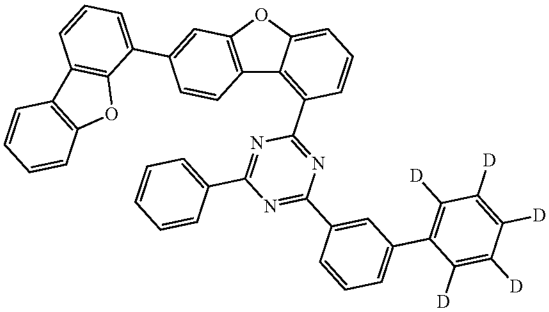
-continued
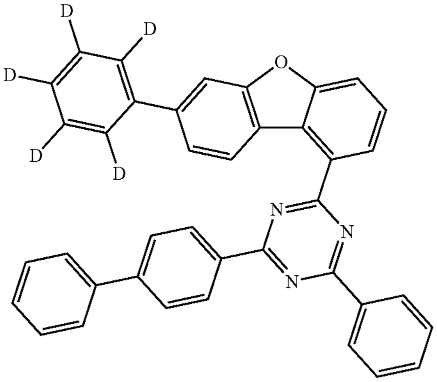
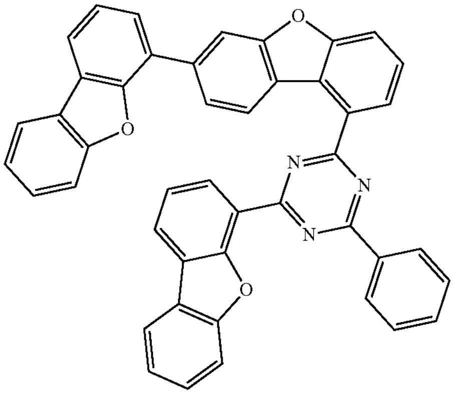
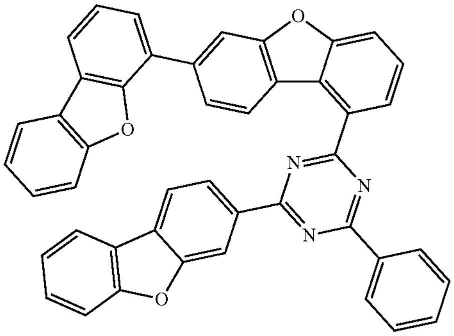
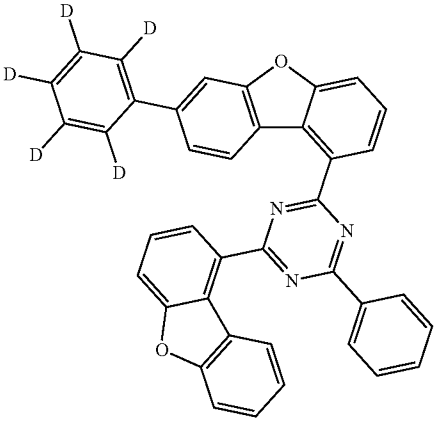

-continued
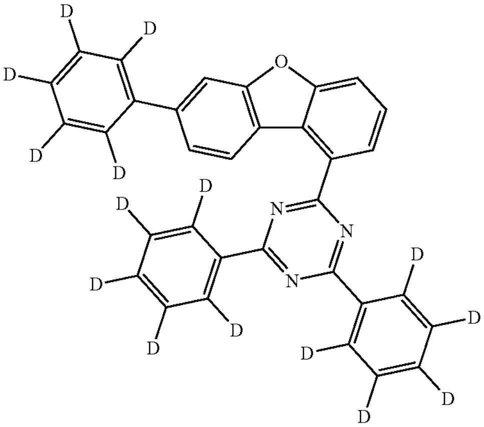
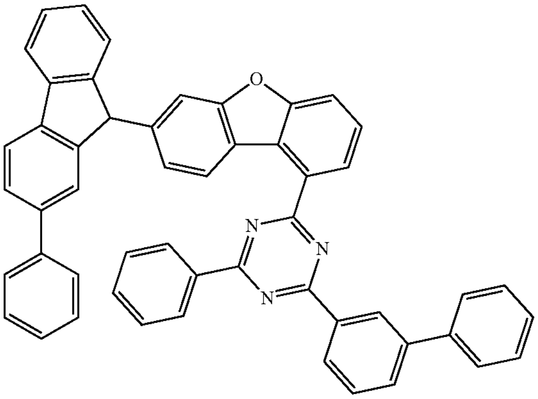
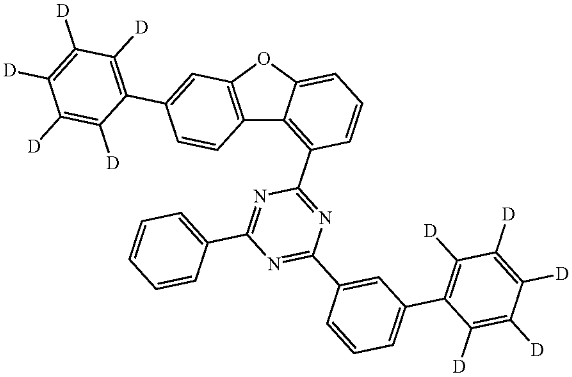
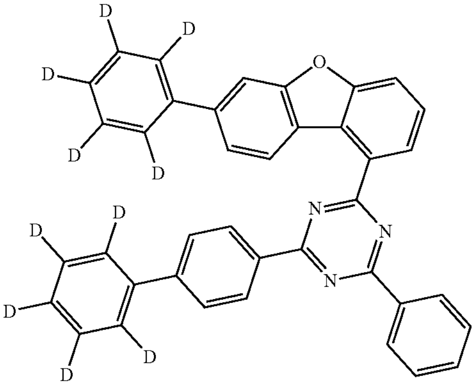
-continued
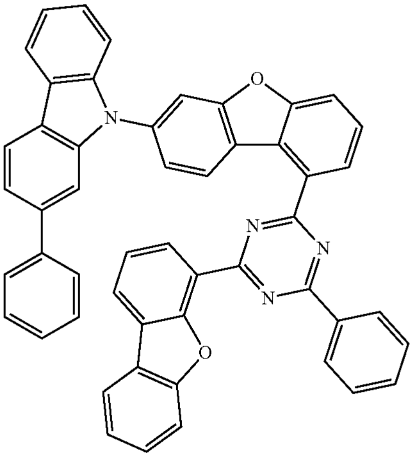
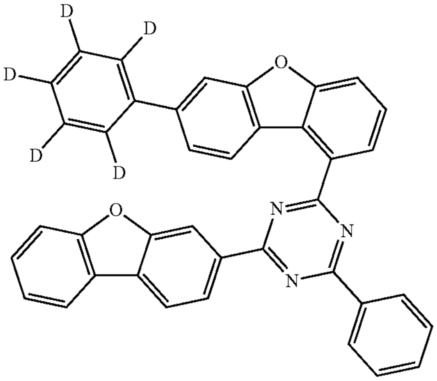
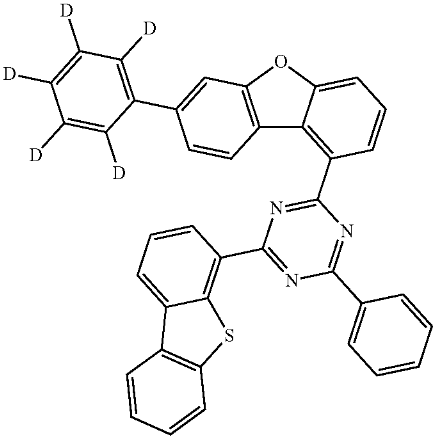
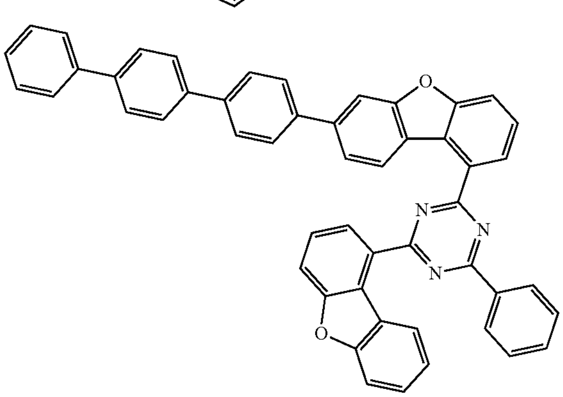

-continued
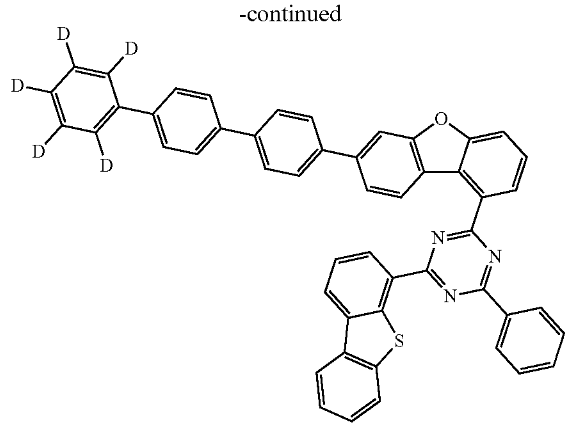
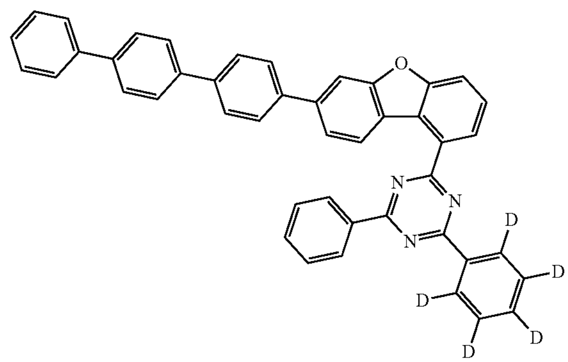
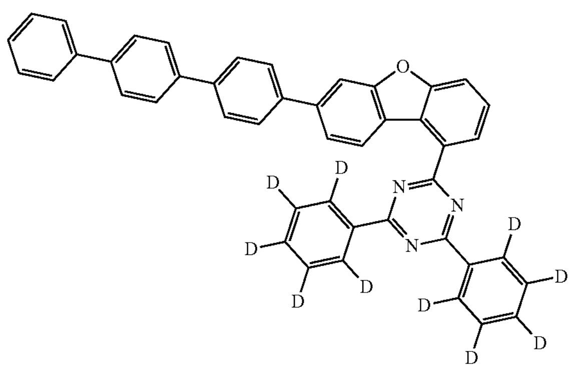
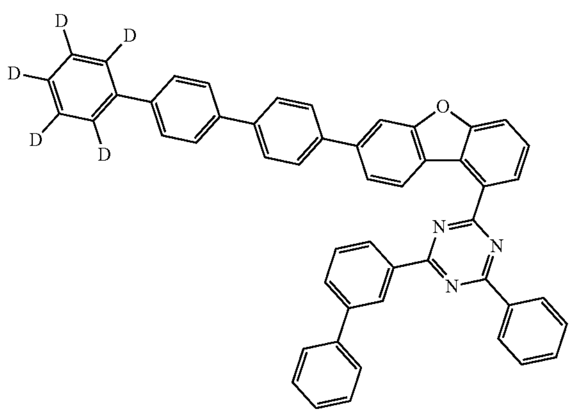
-continued
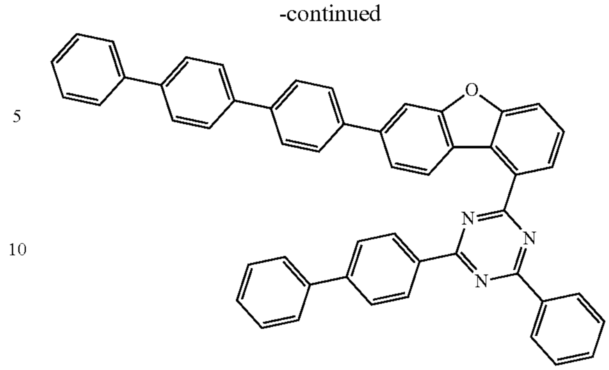
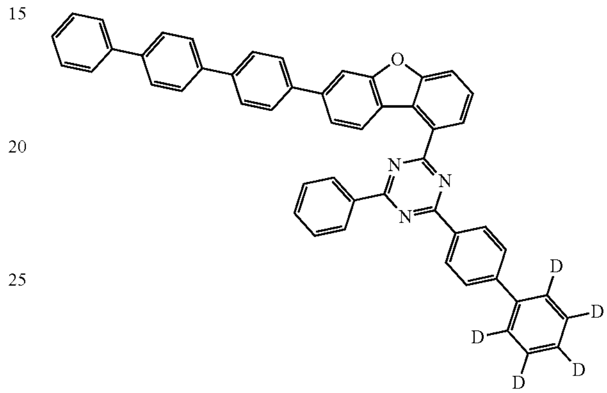
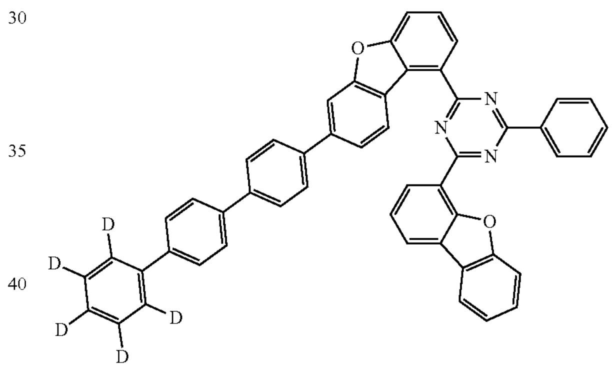
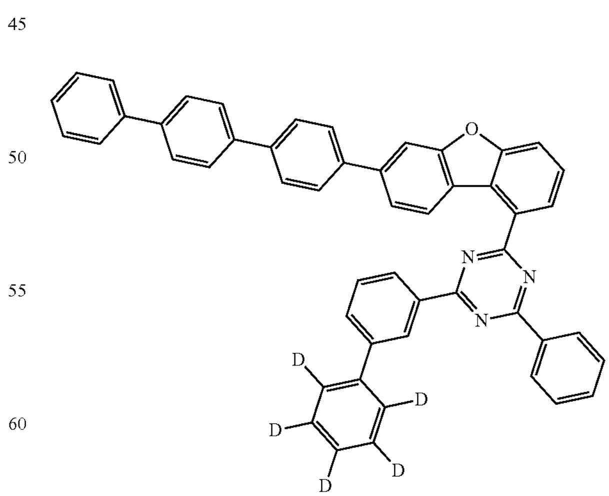

-continued
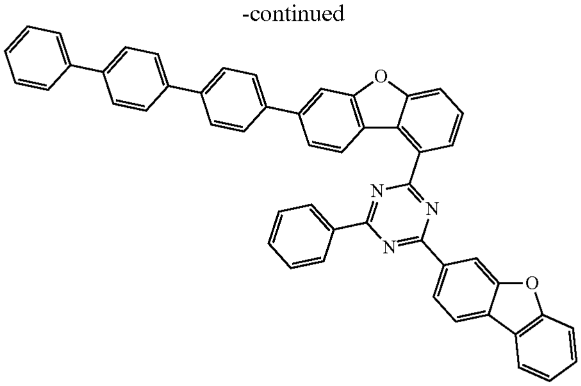
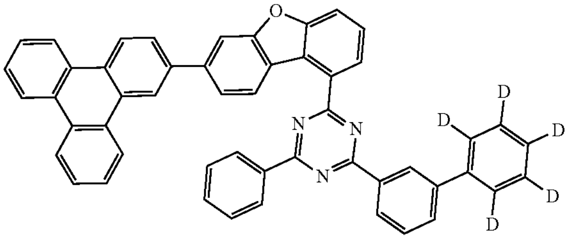
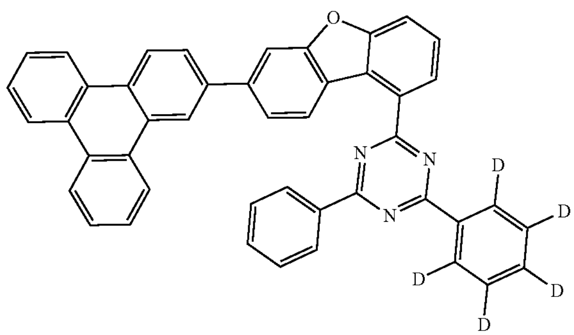
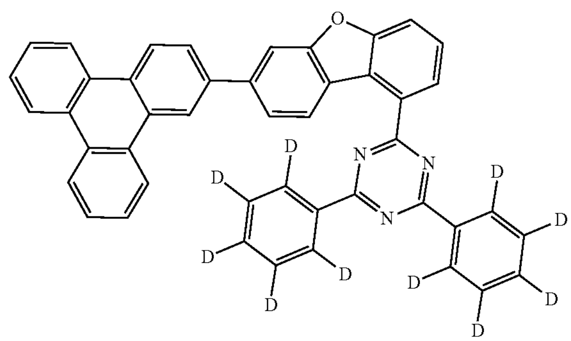
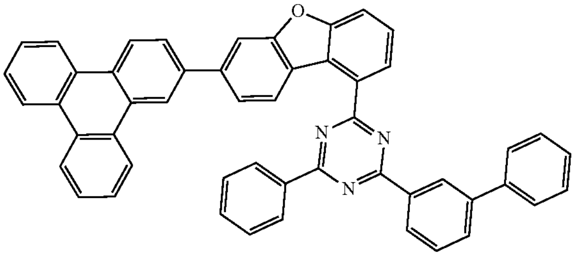
-continued
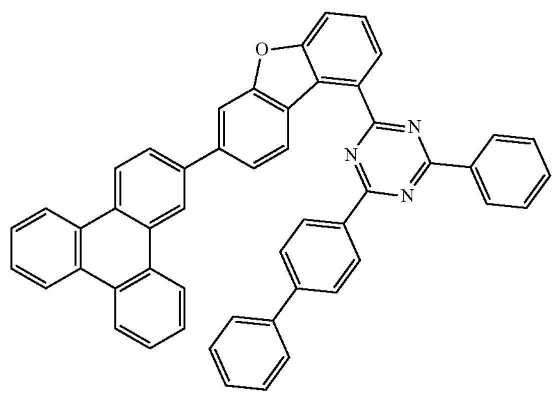
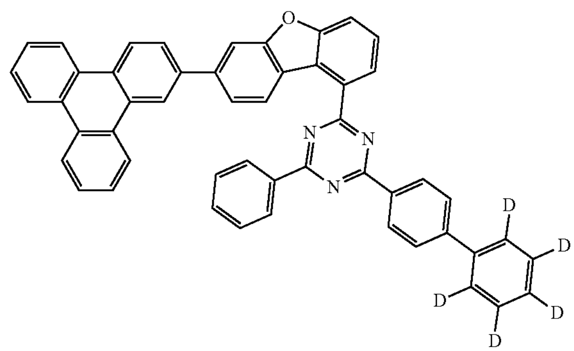
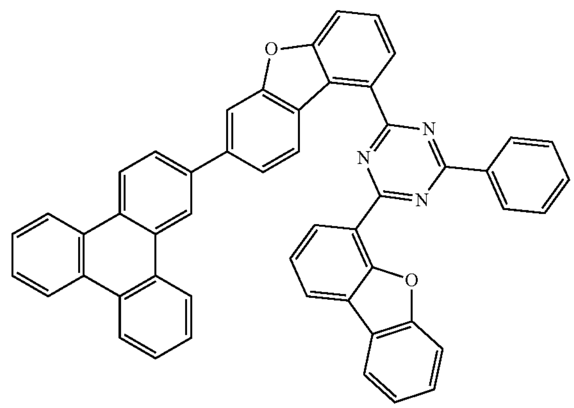
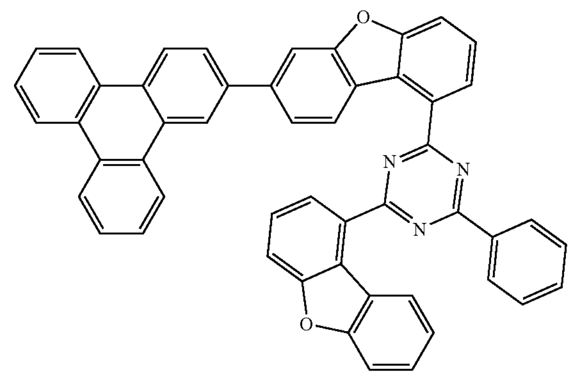

-continued
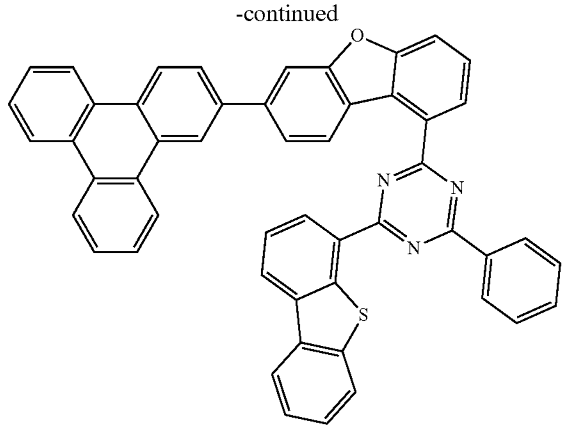
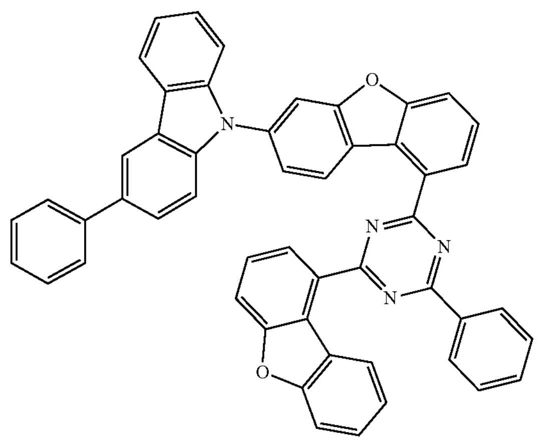
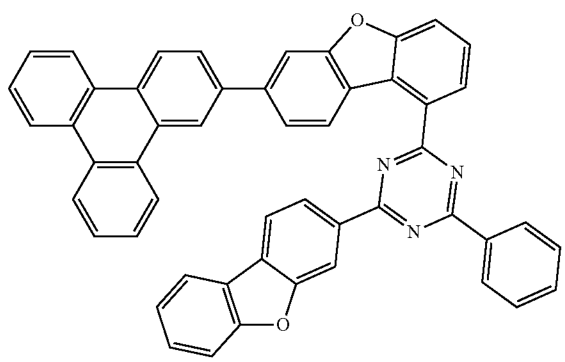
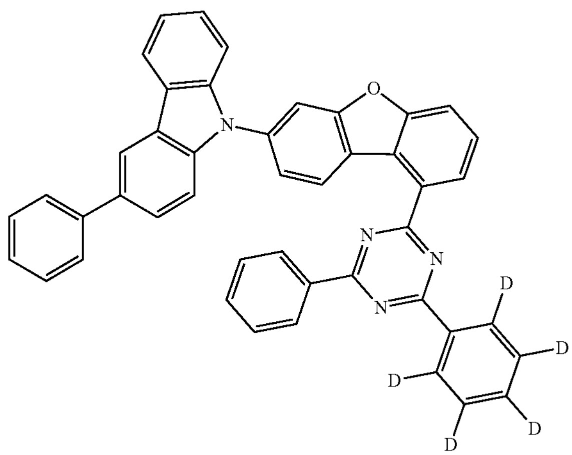
-continued
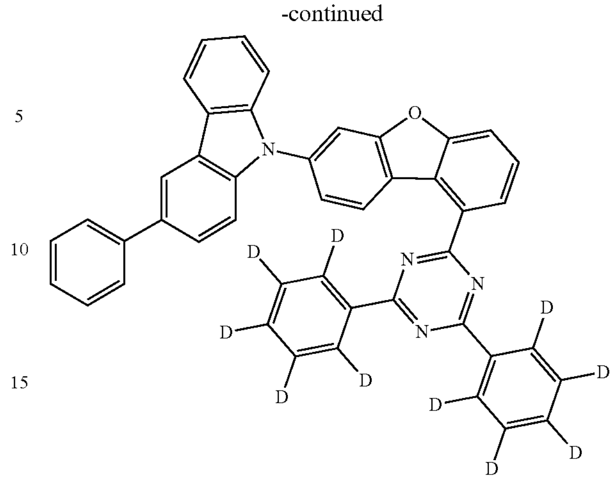
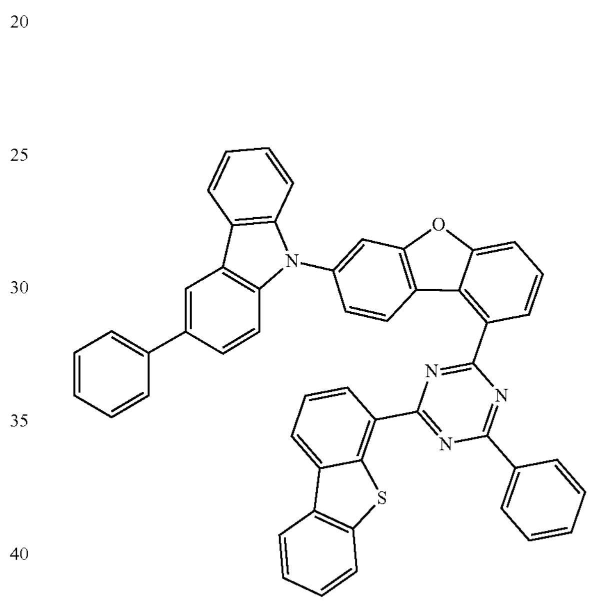
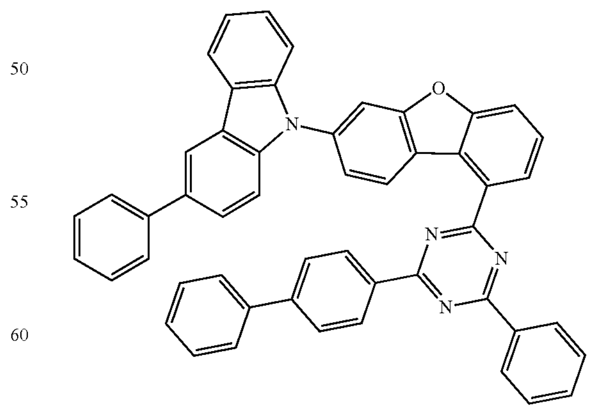

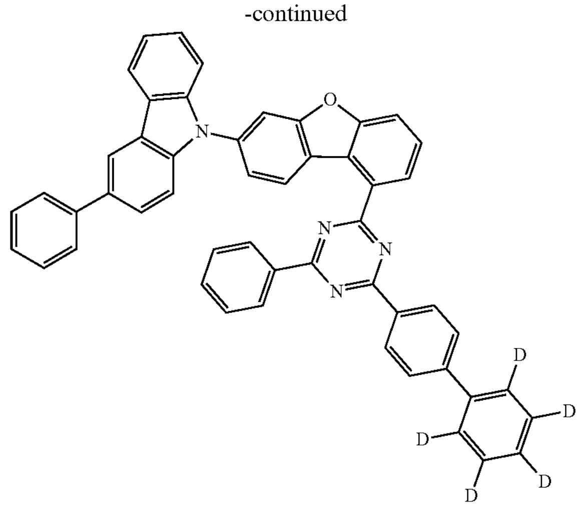
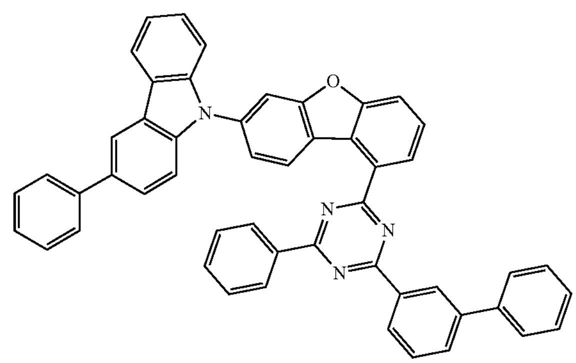
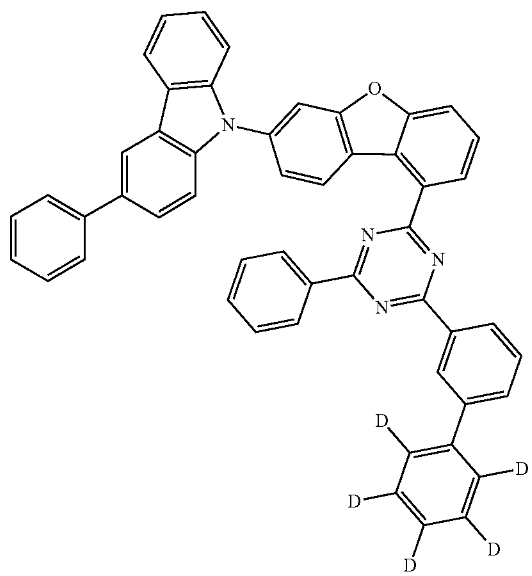
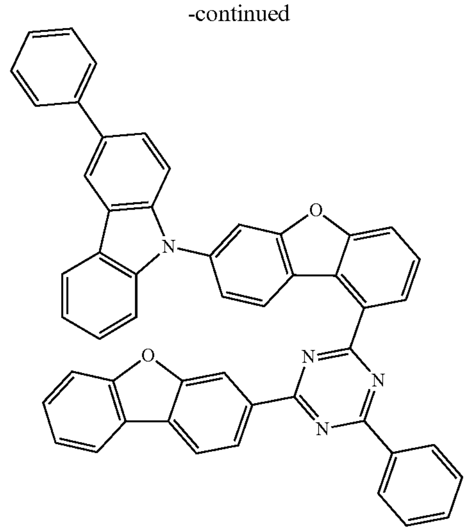
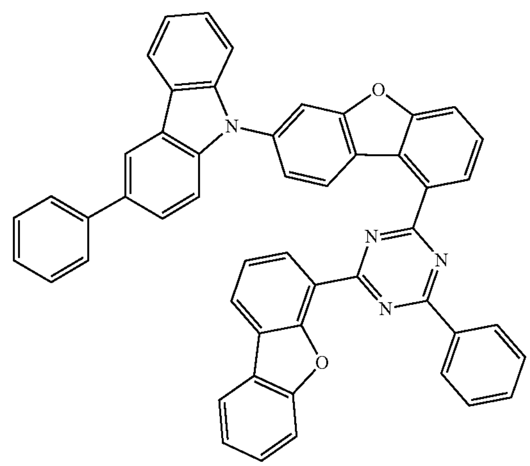
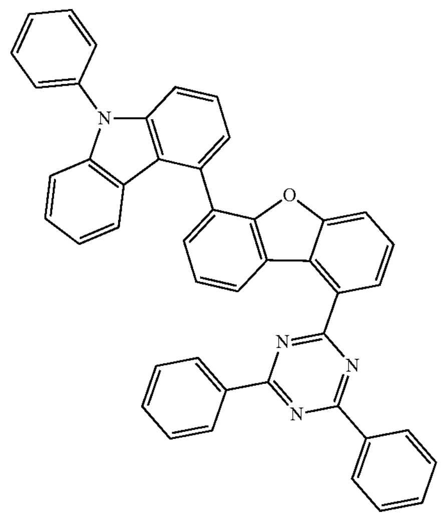

-continued
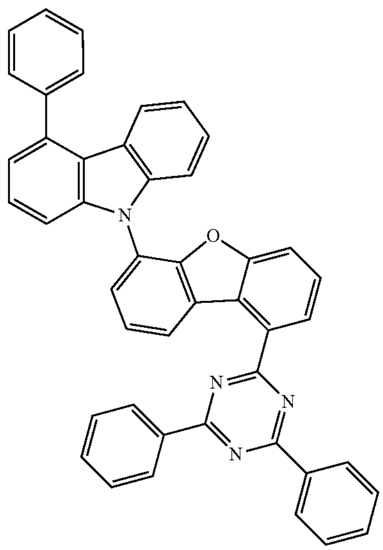
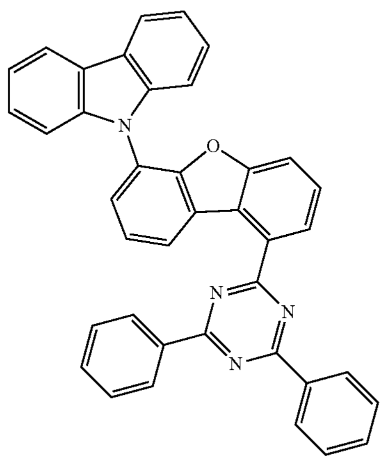
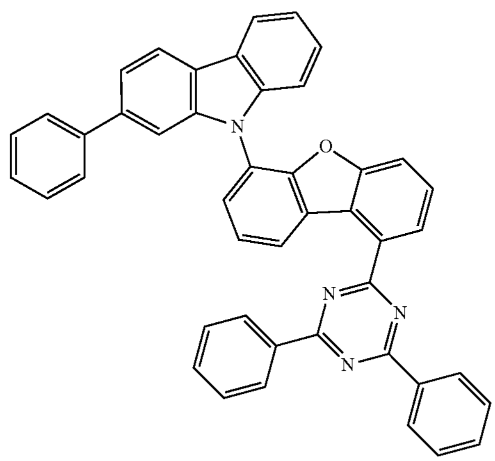
-continued
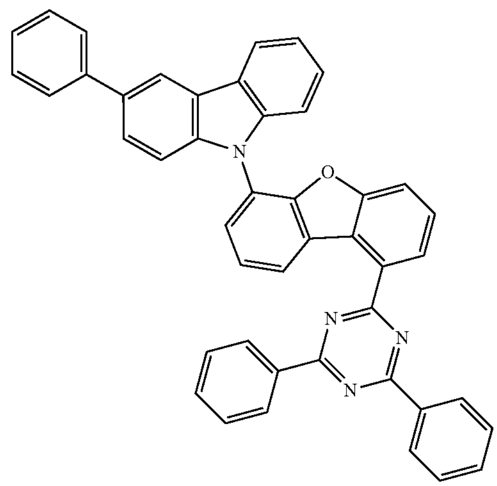
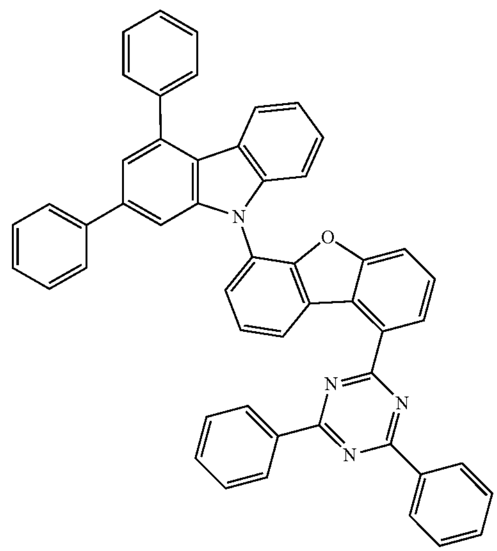
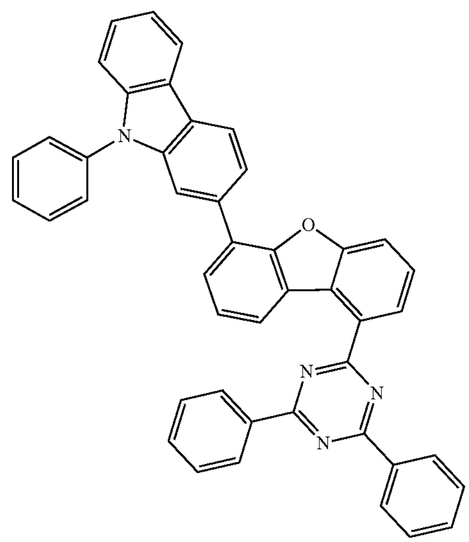

-continued
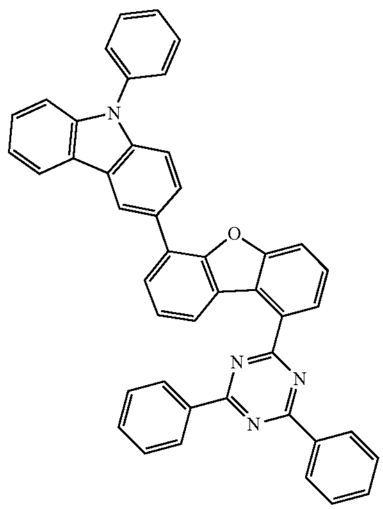
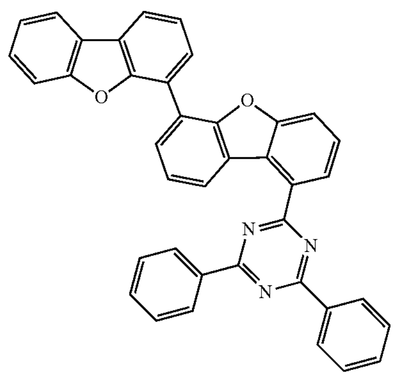
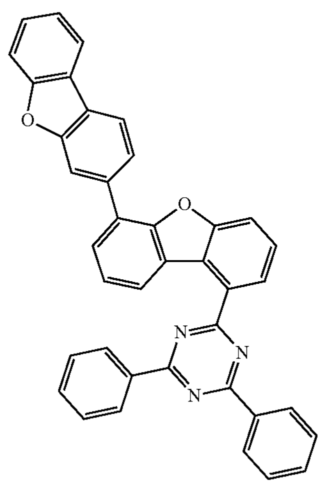
-continued
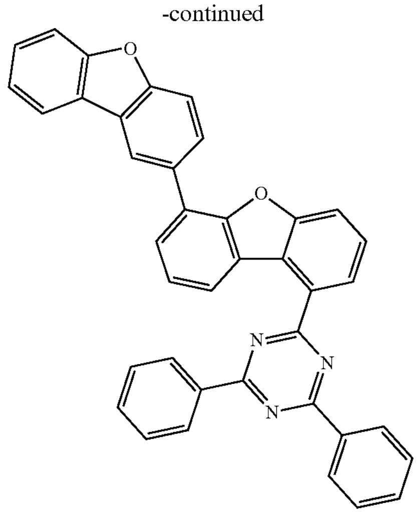
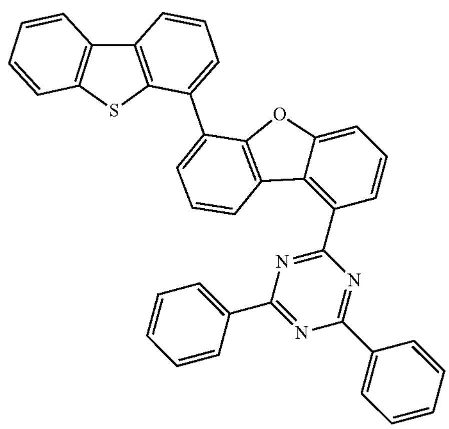
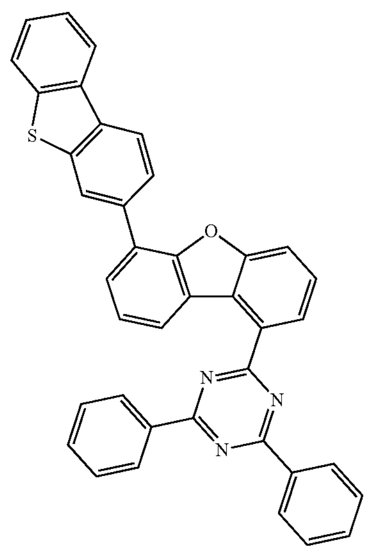

-continued
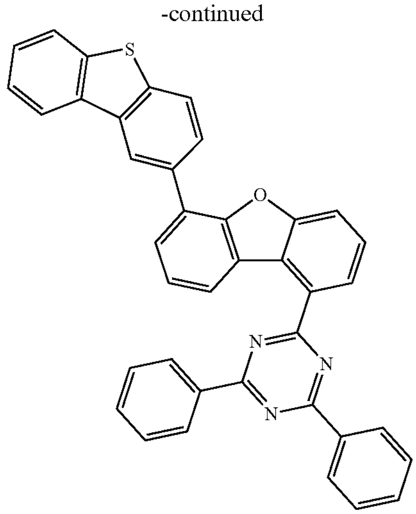
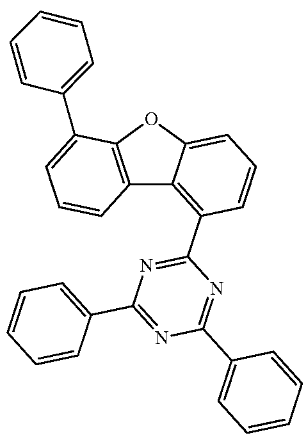
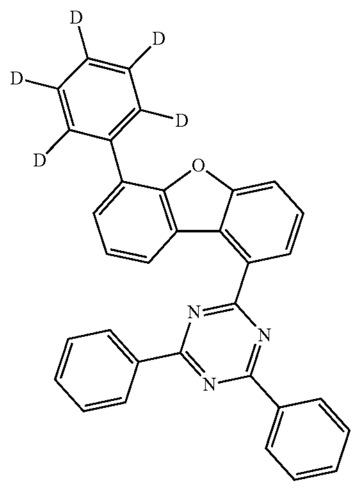
-continued
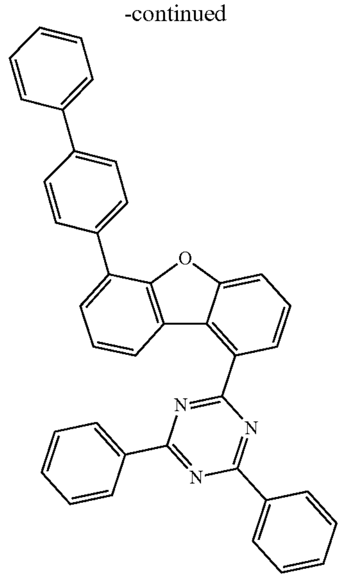
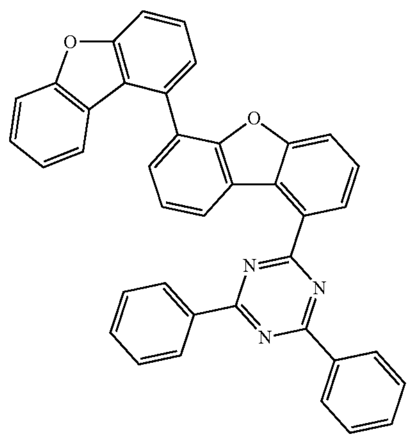
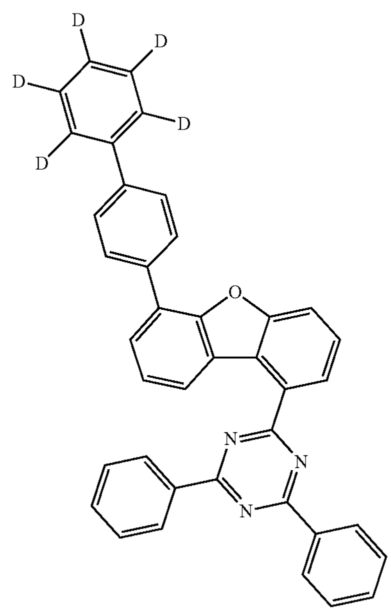

-continued
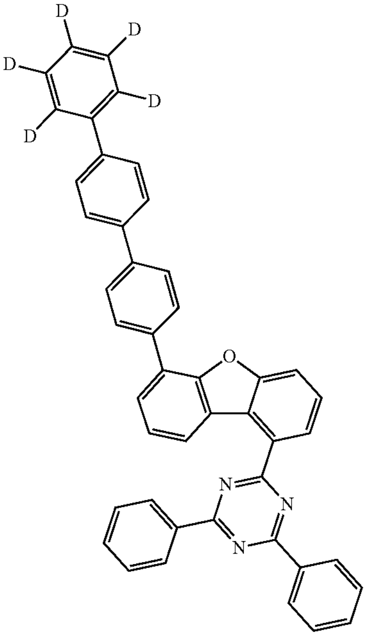
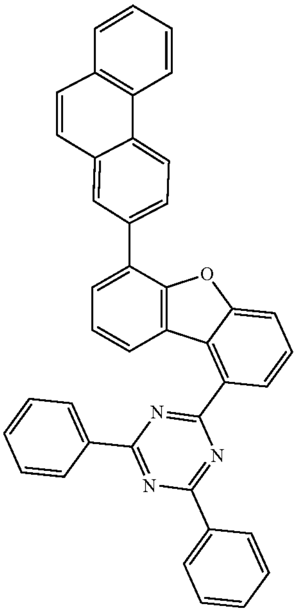
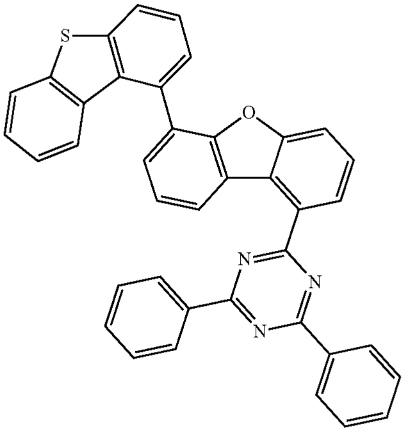
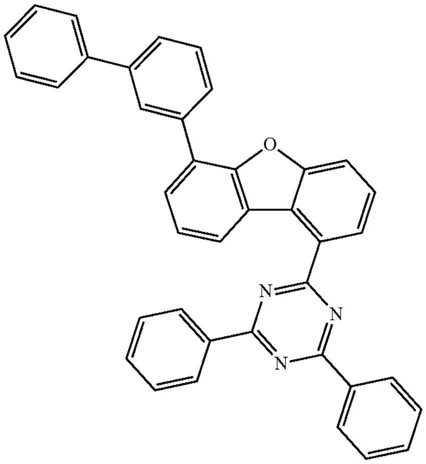
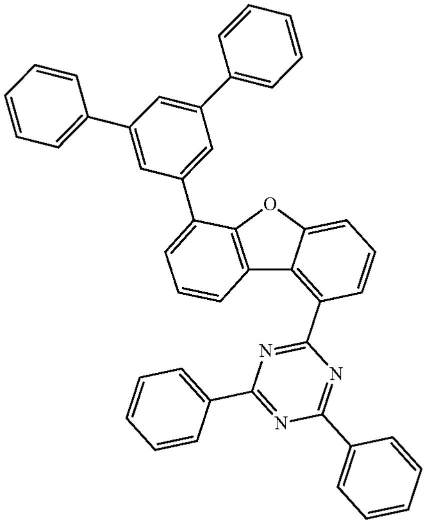
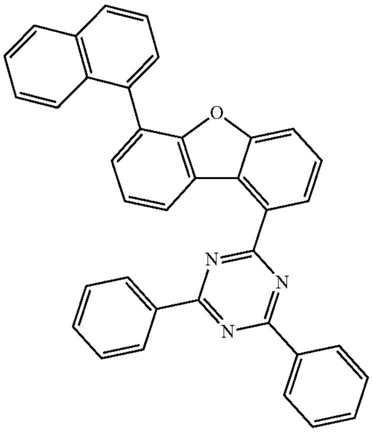

-continued
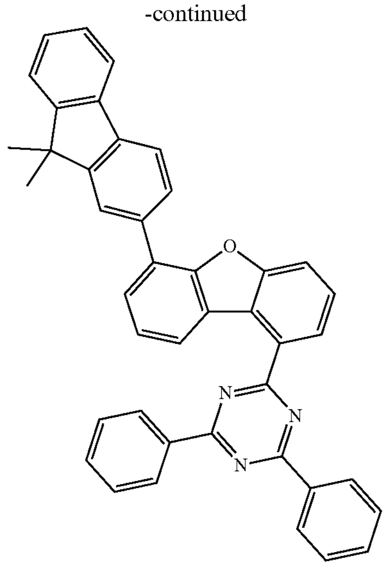
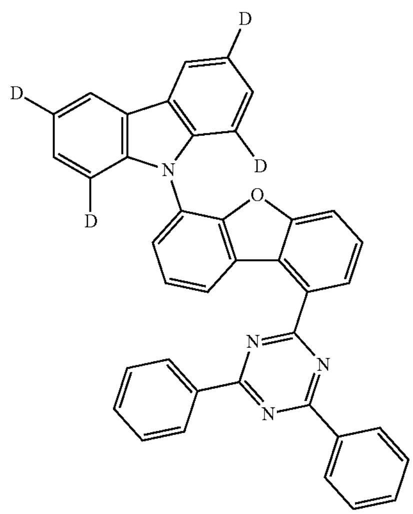
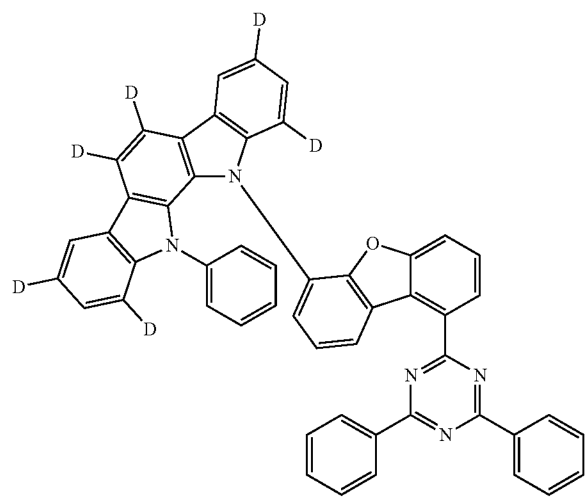
-continued
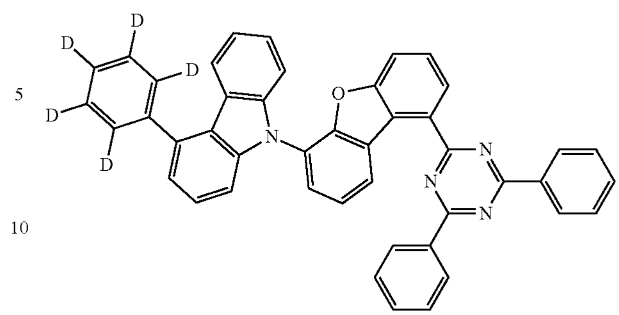
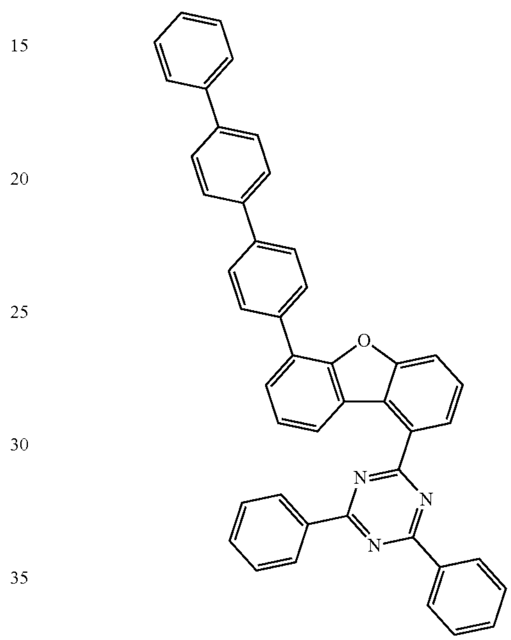
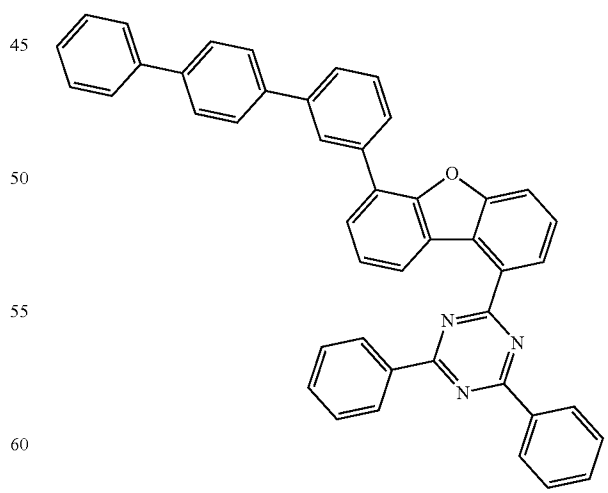

-continued
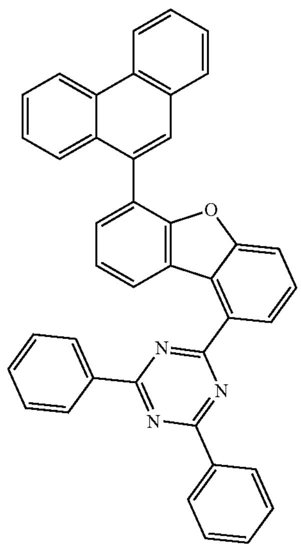
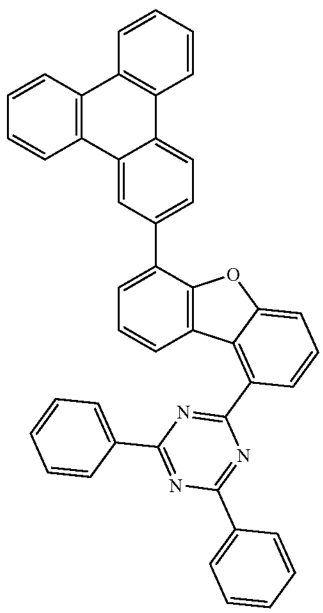
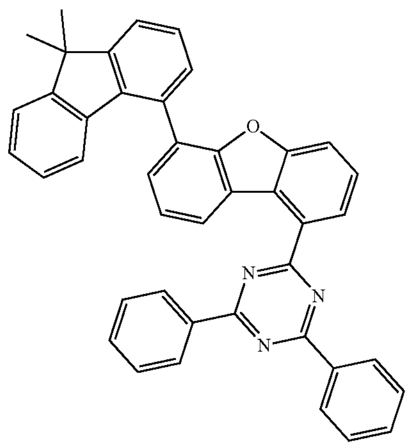
-continued
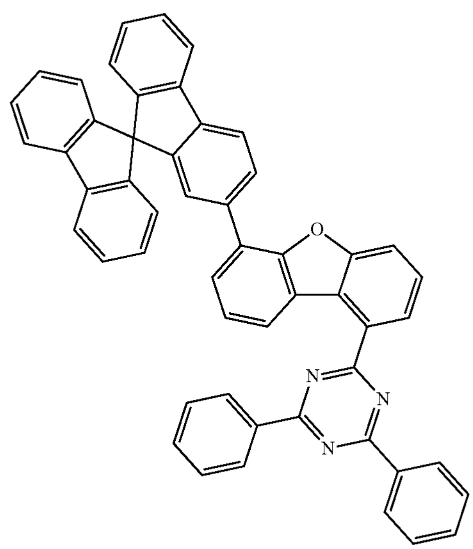
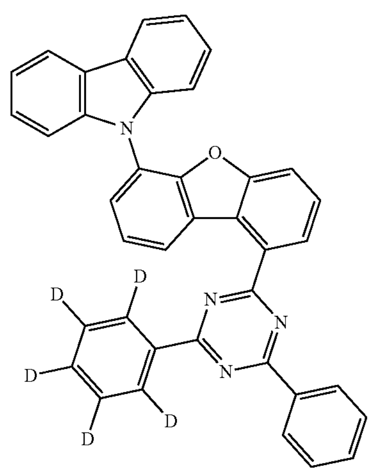
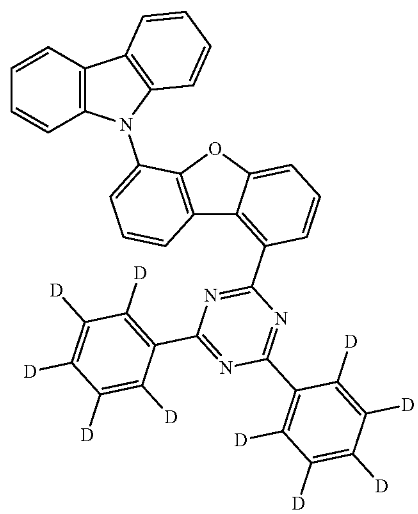

-continued
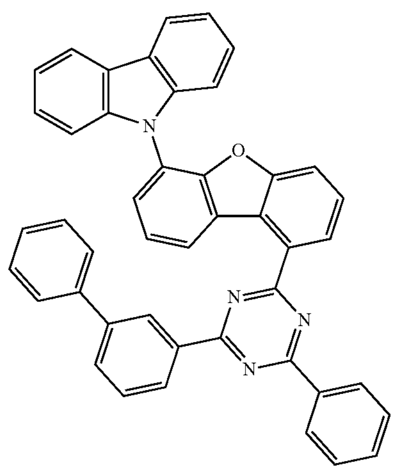
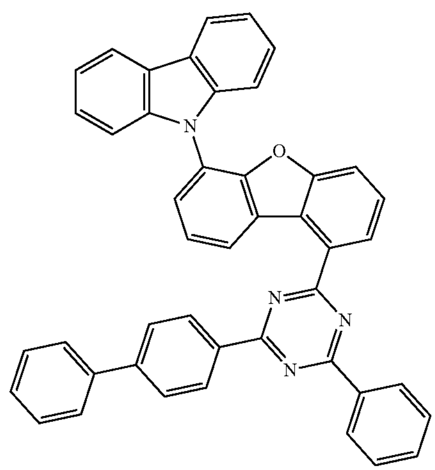
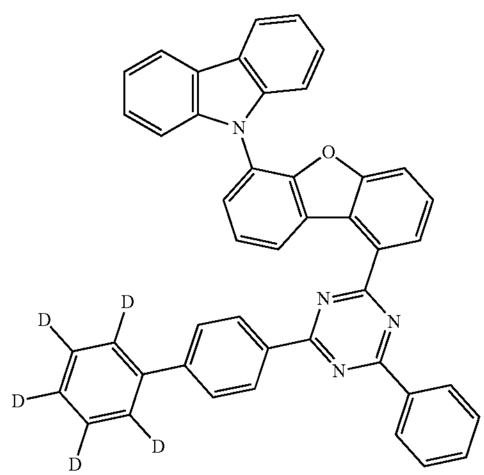
-continued
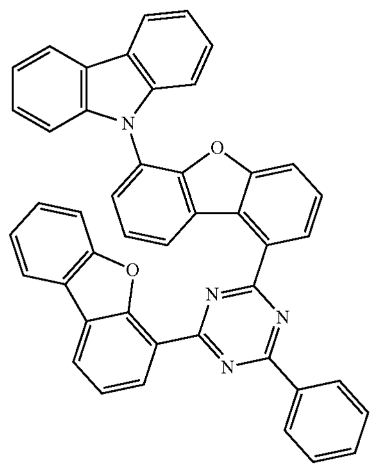
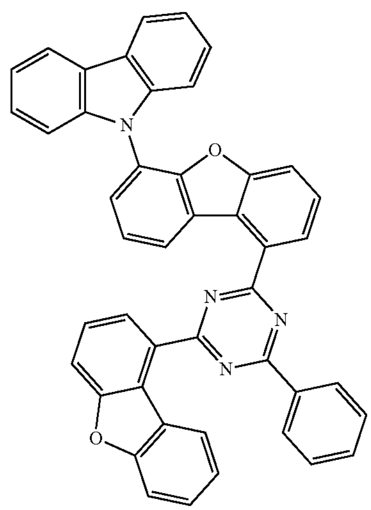
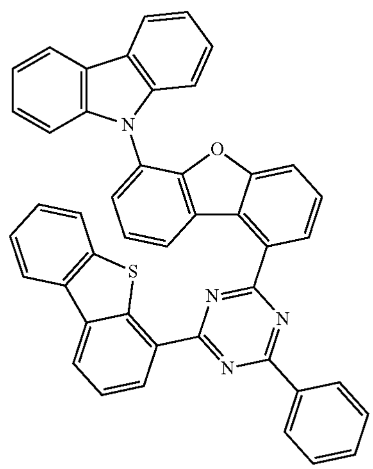

-continued
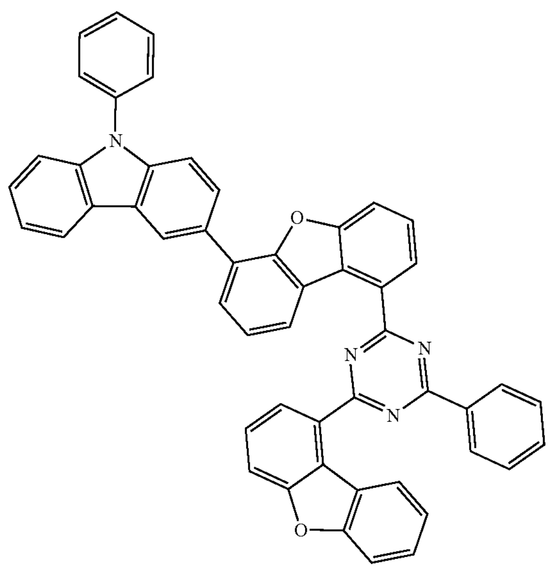
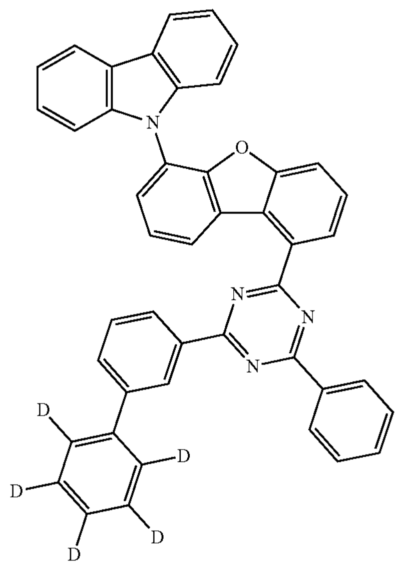
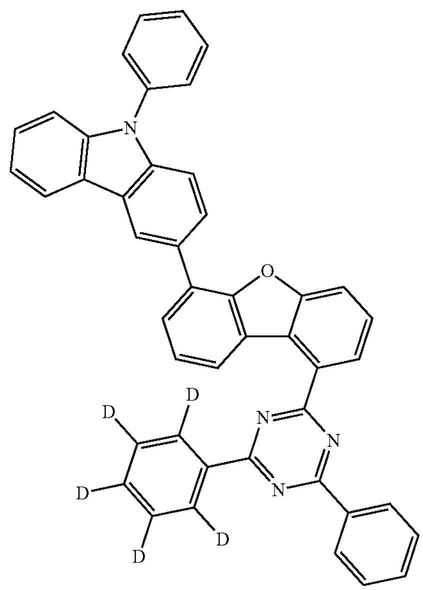
-continued
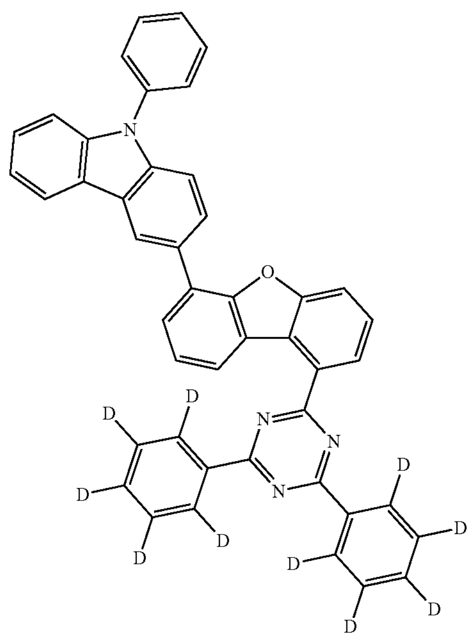
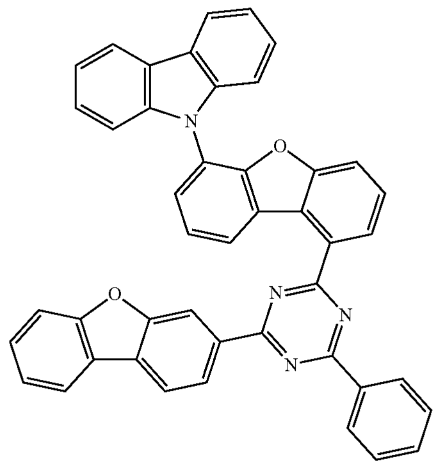
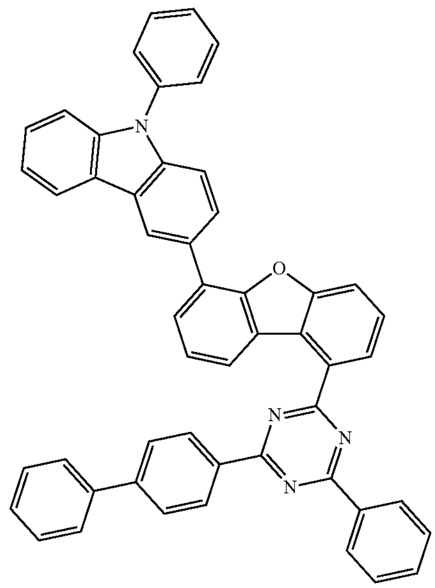

-continued
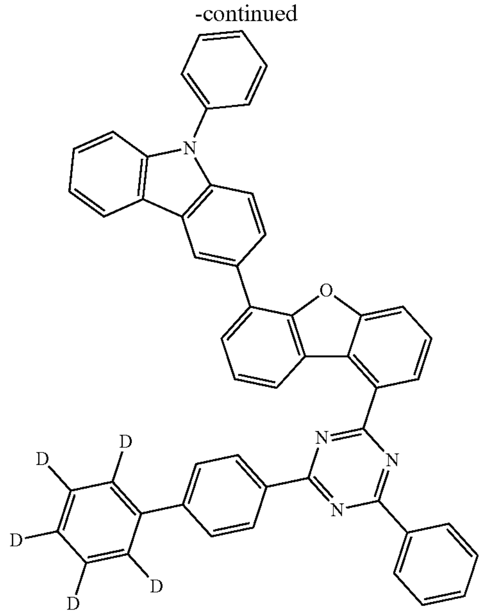
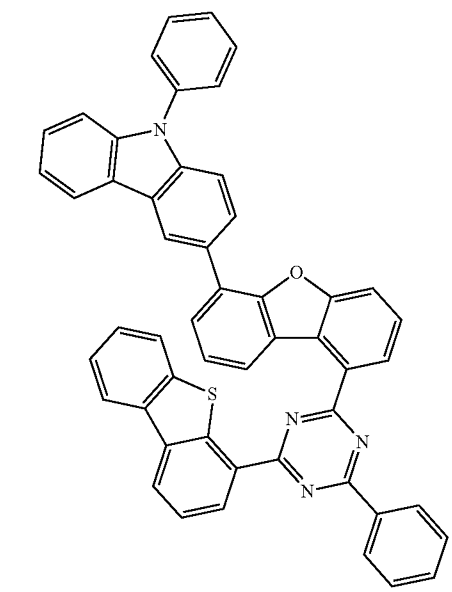
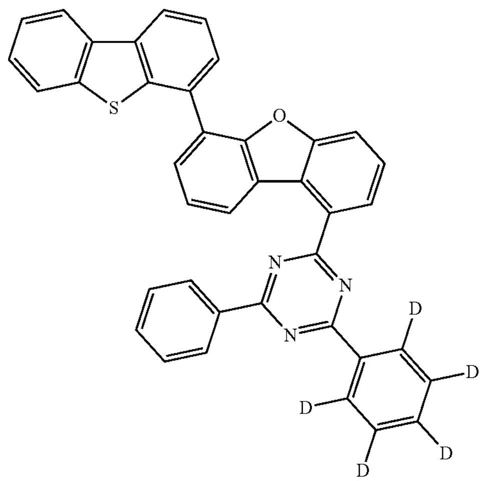
-continued
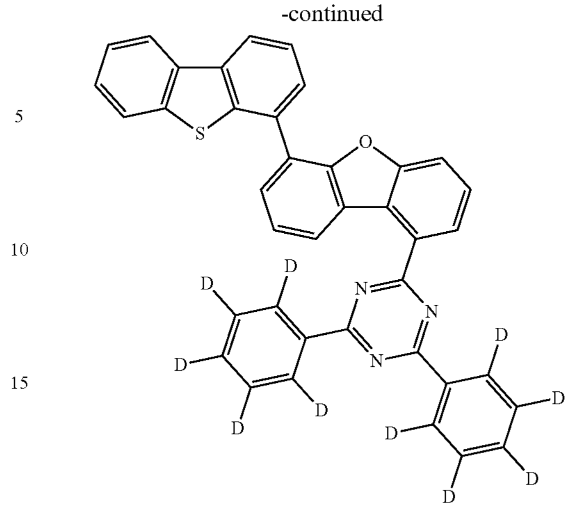
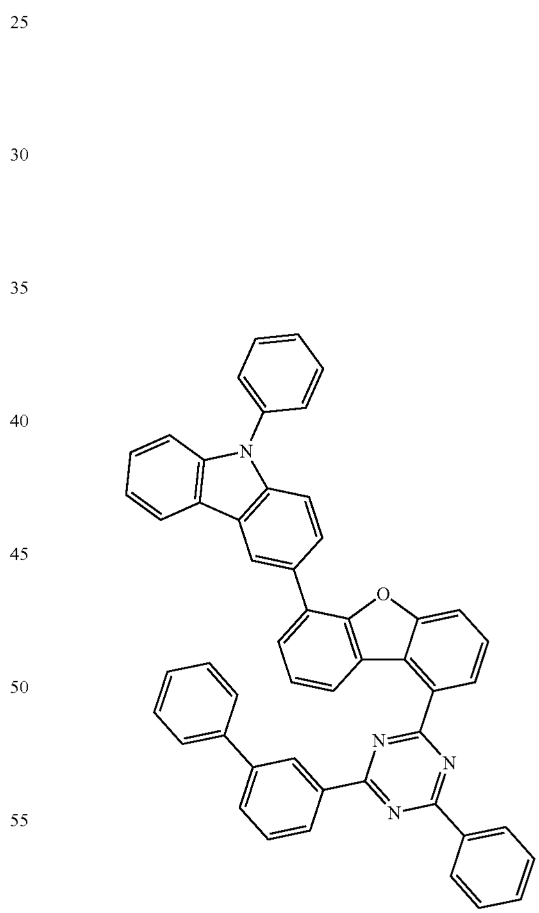

-continued
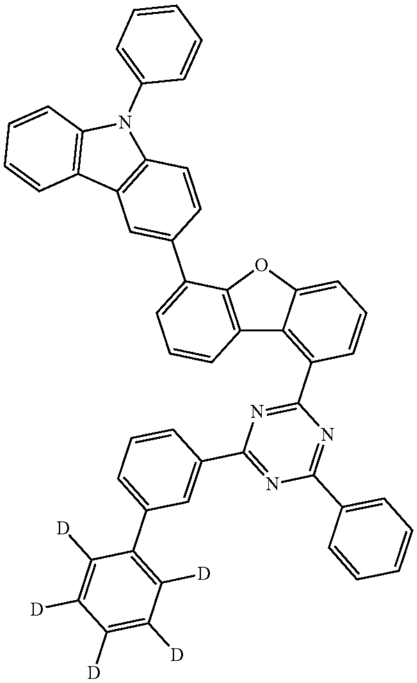
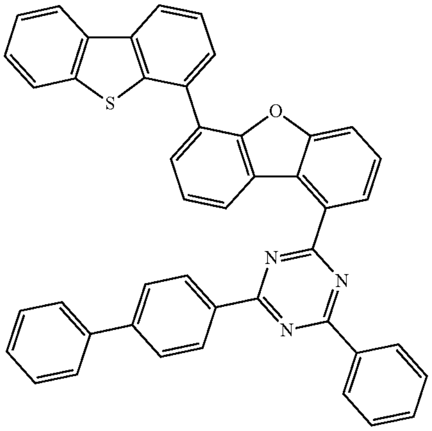
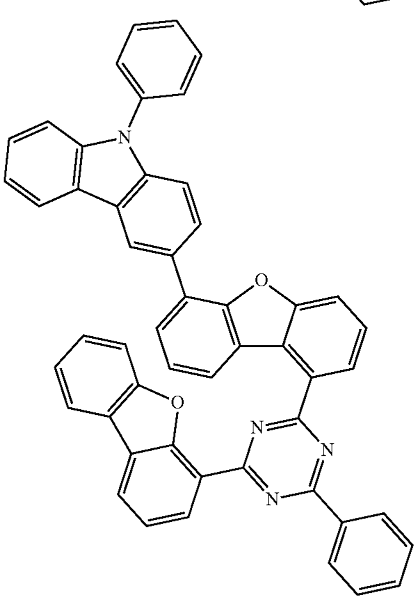
-continued
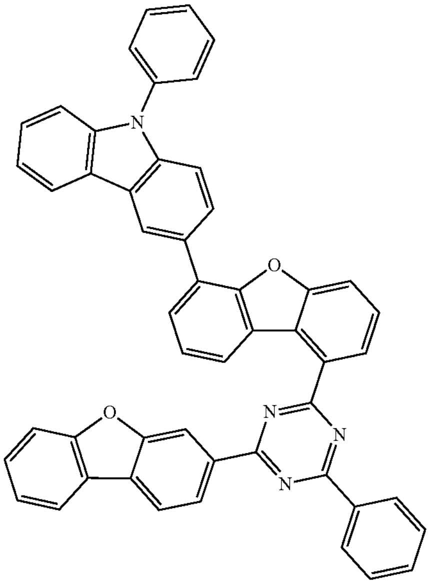
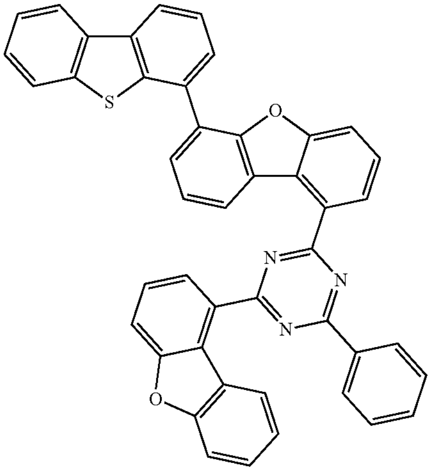
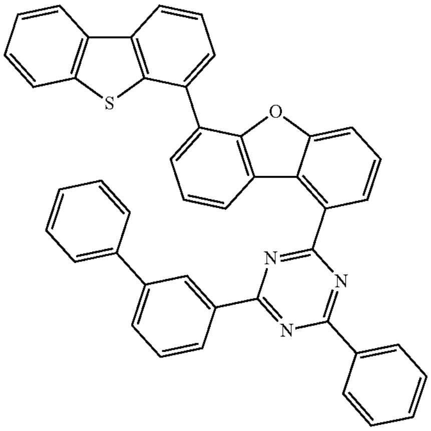

-continued
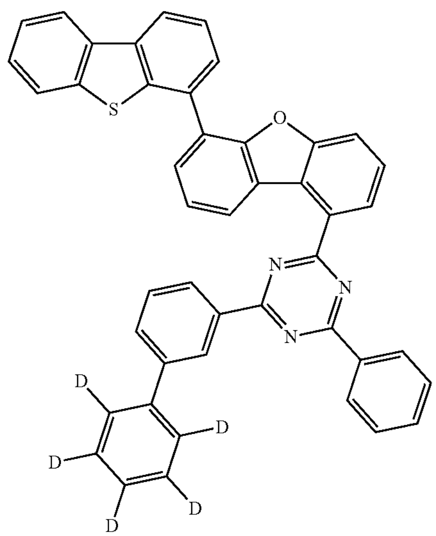
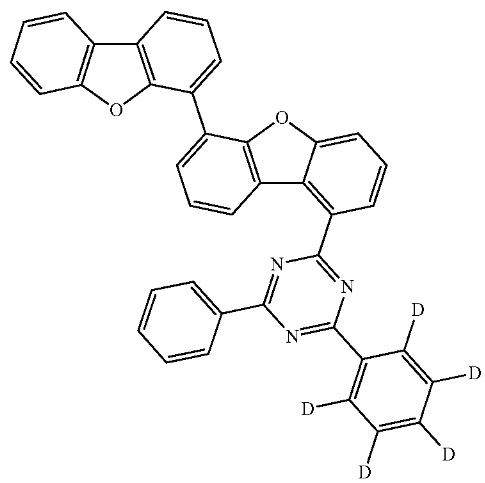
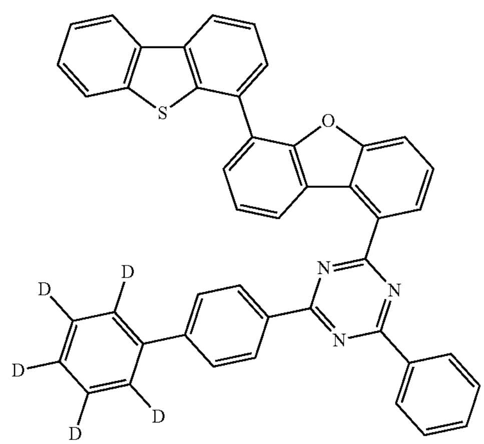
-continued
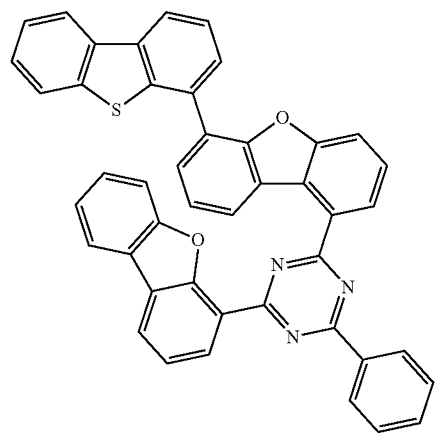
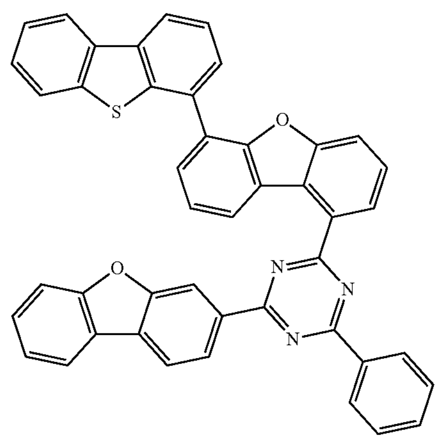
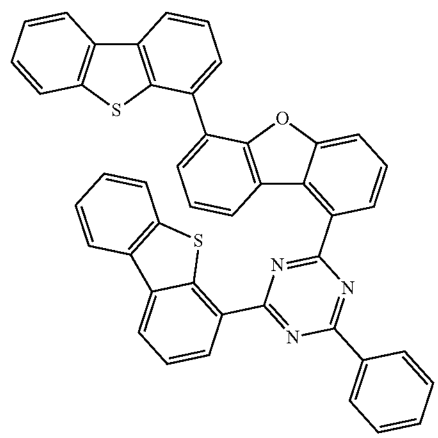

-continued
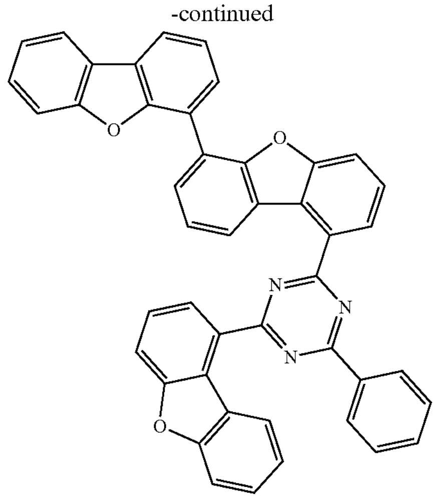
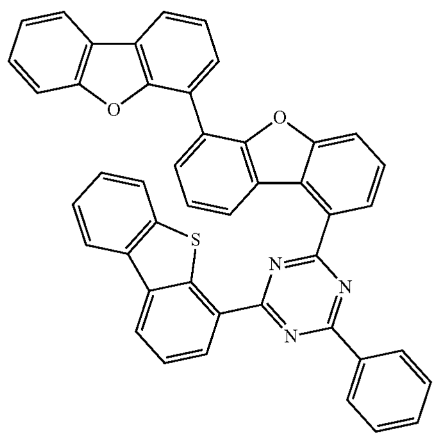
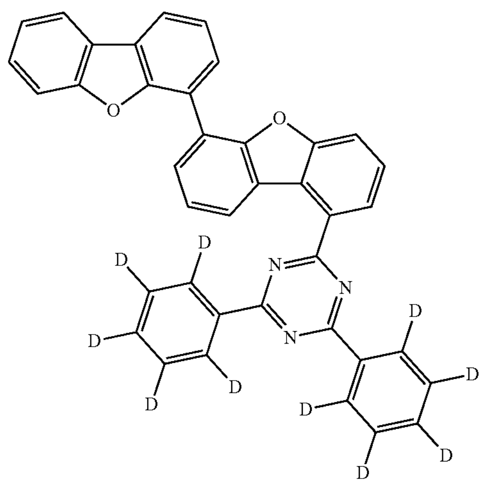
-continued
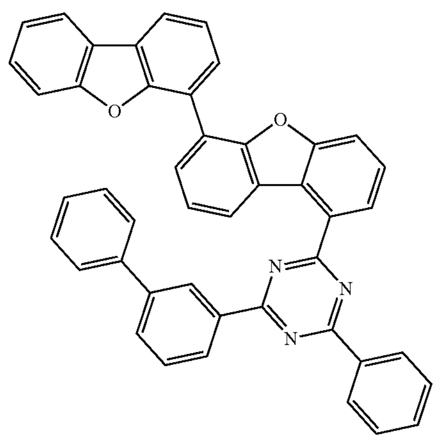
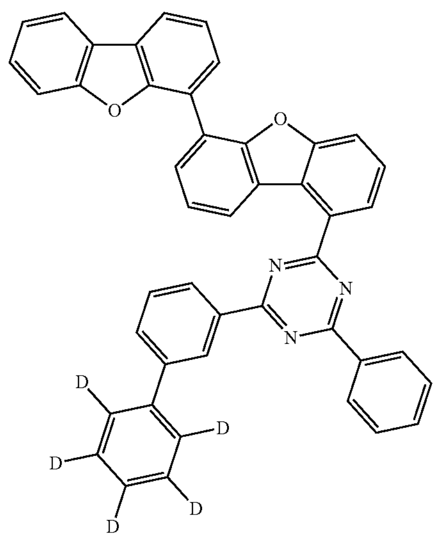
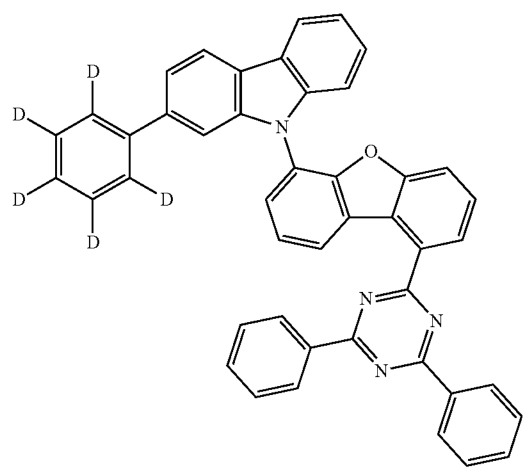

-continued
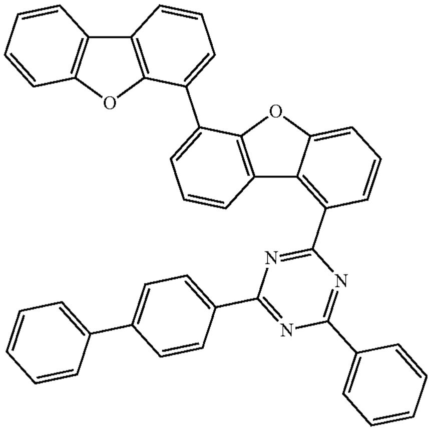
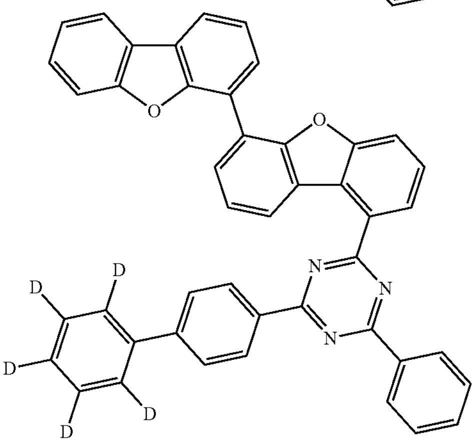
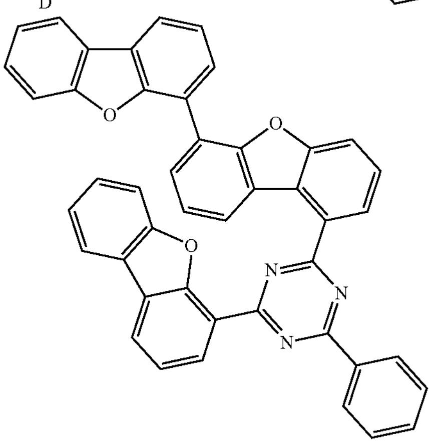
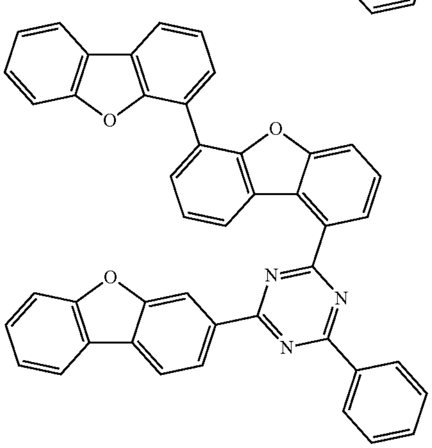
-continued
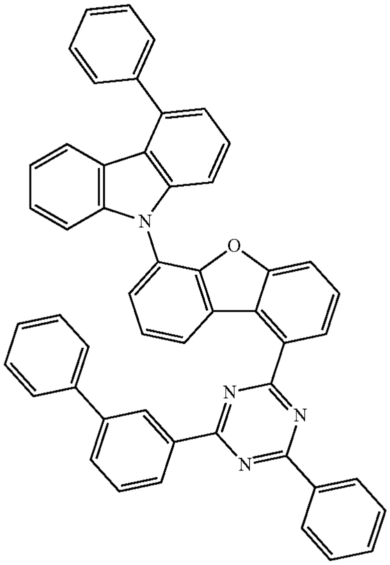
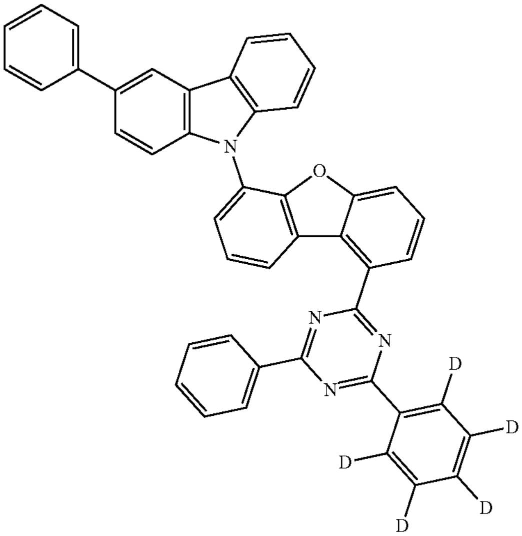
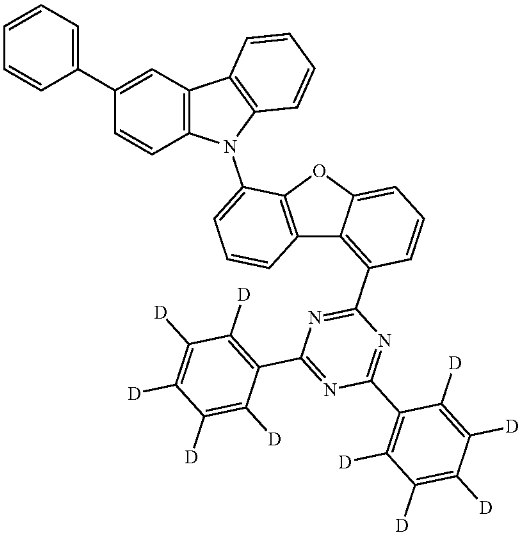

-continued
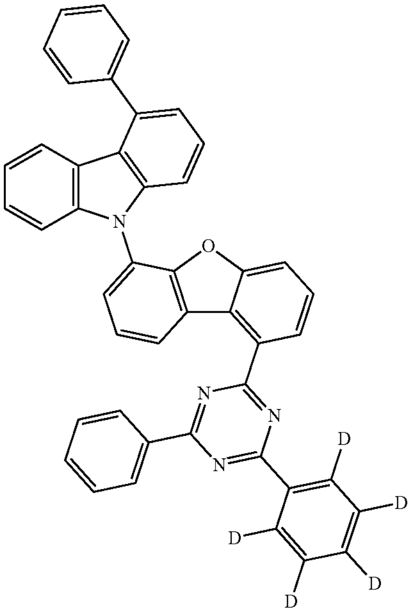
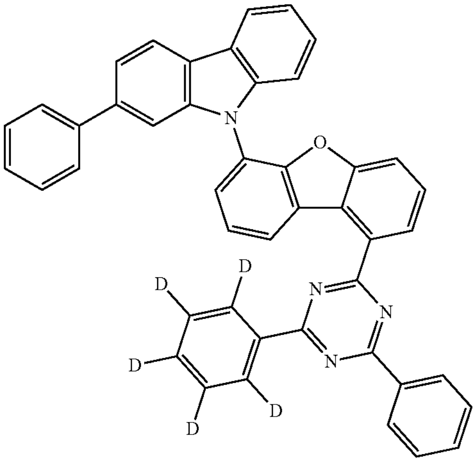
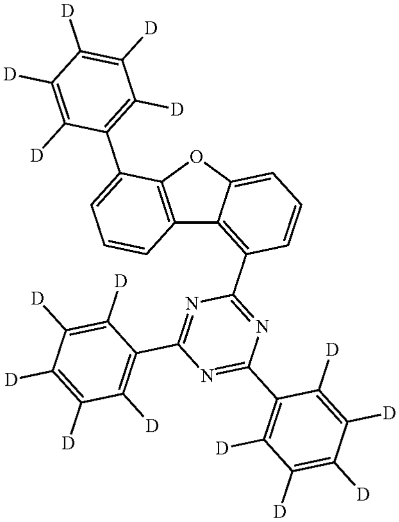
-continued
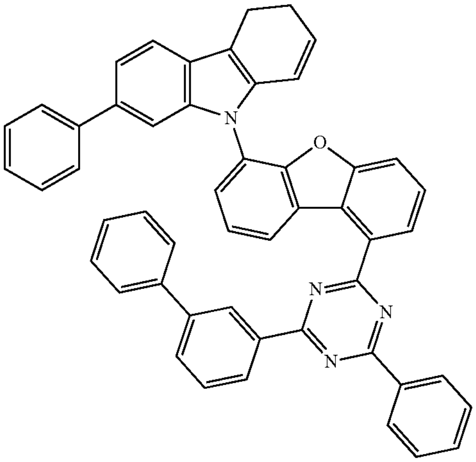
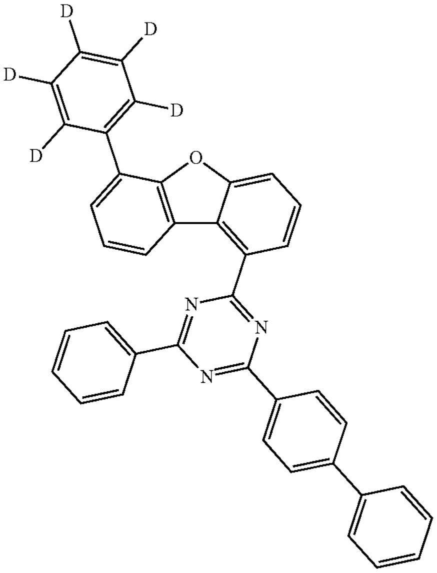
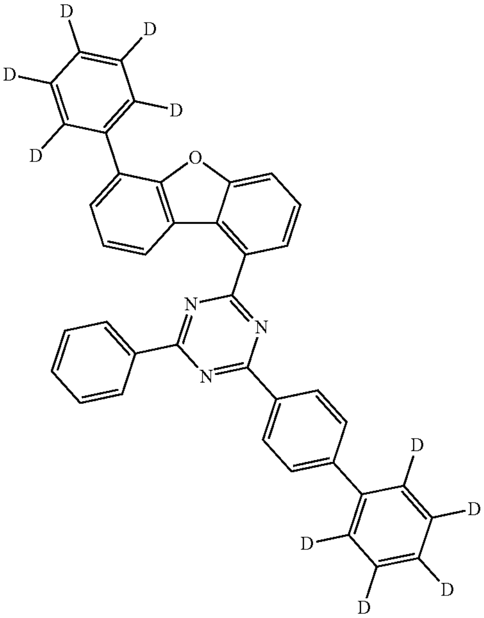

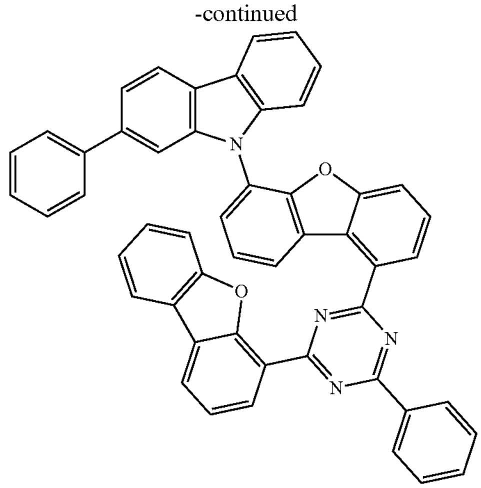
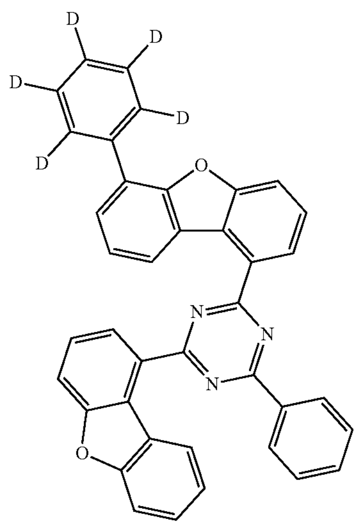
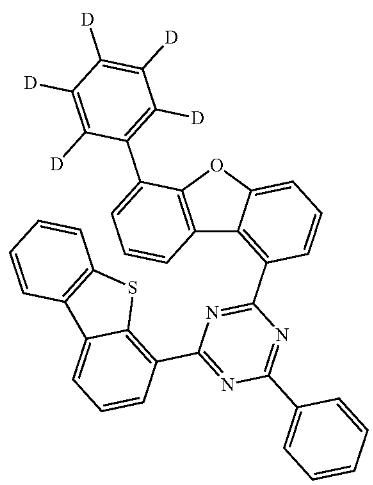
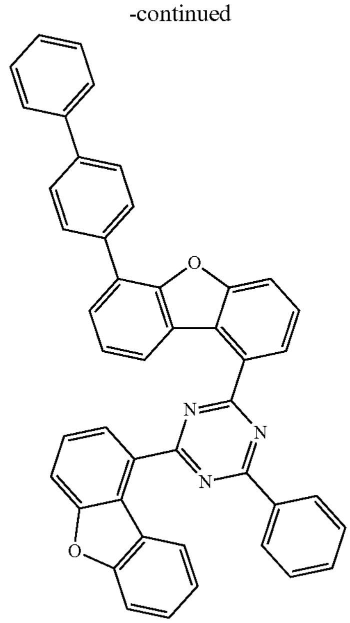
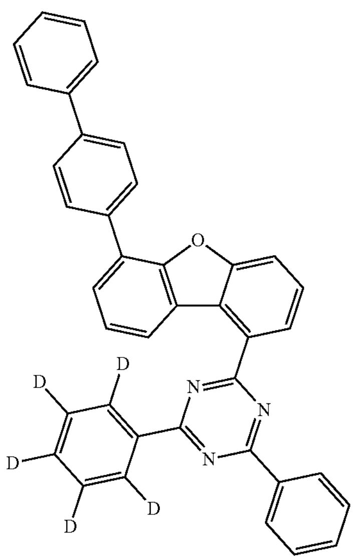

-continued
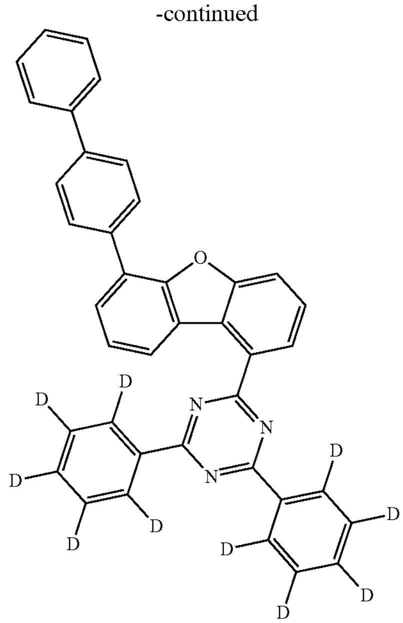
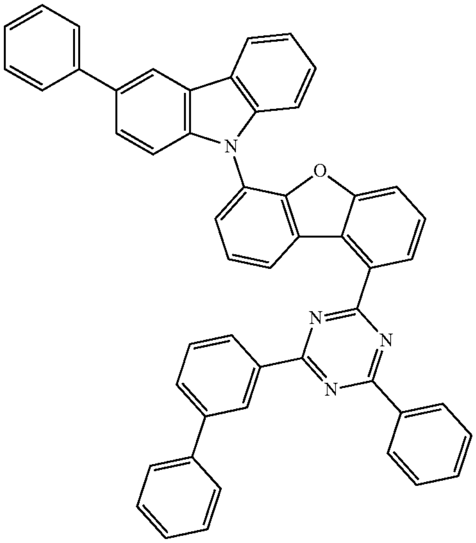
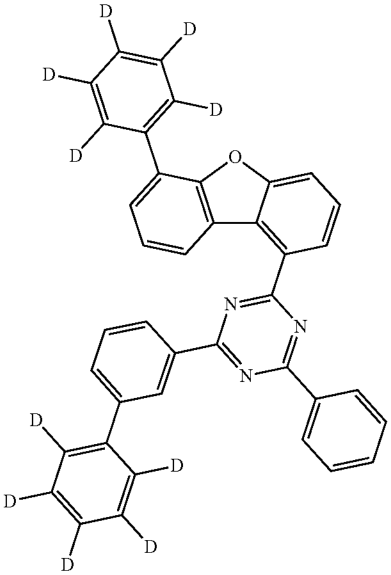
-continued
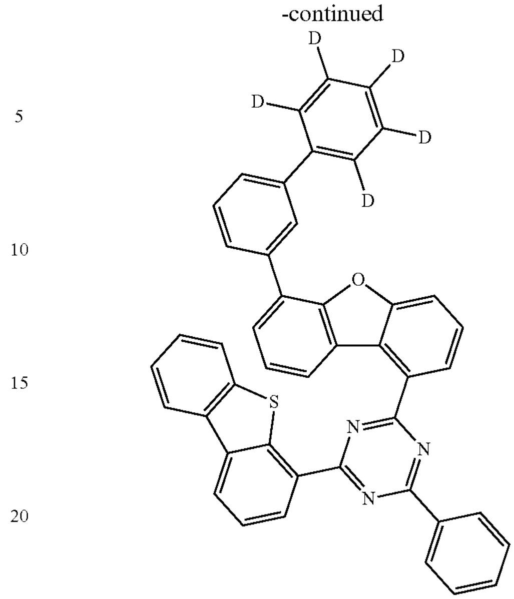
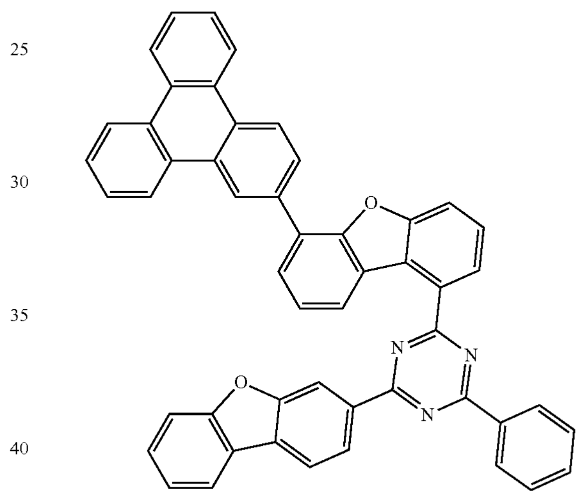
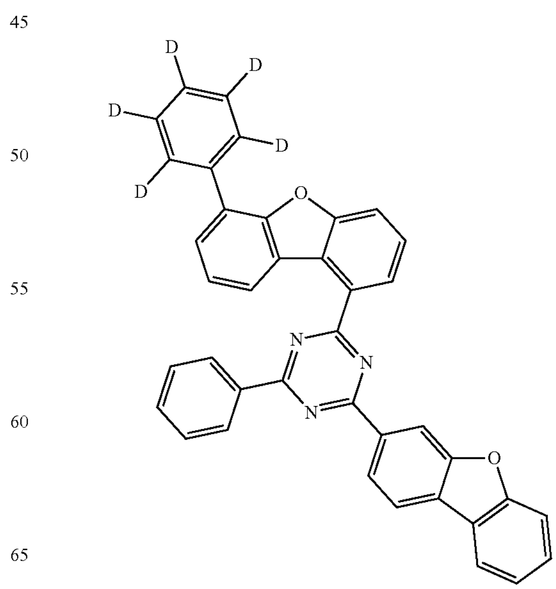

-continued
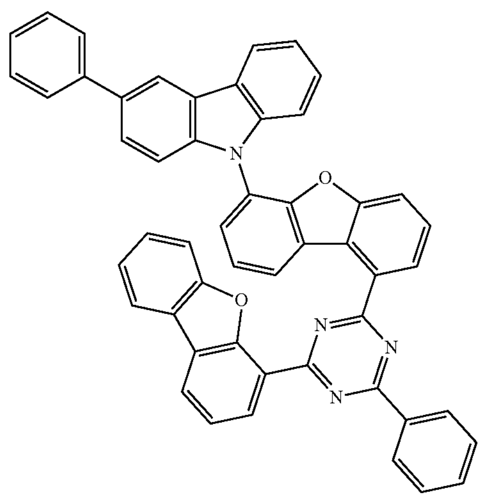
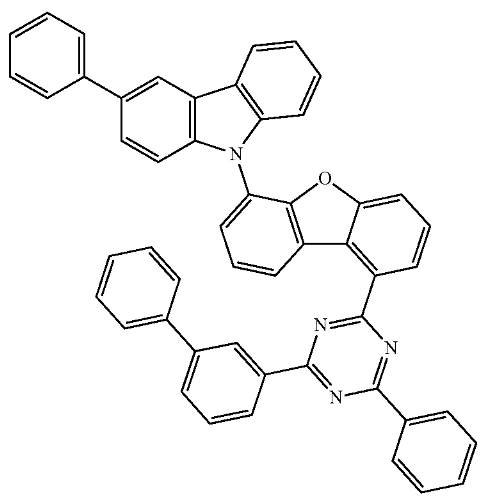
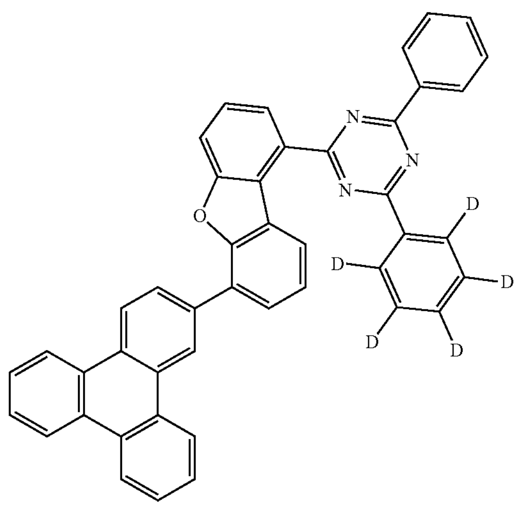
-continued
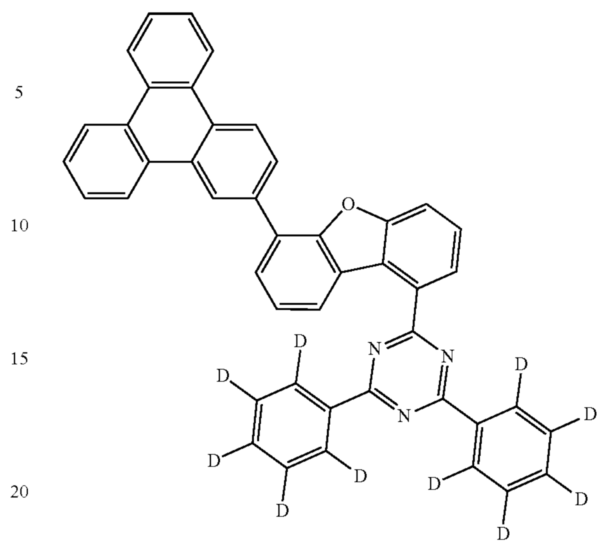
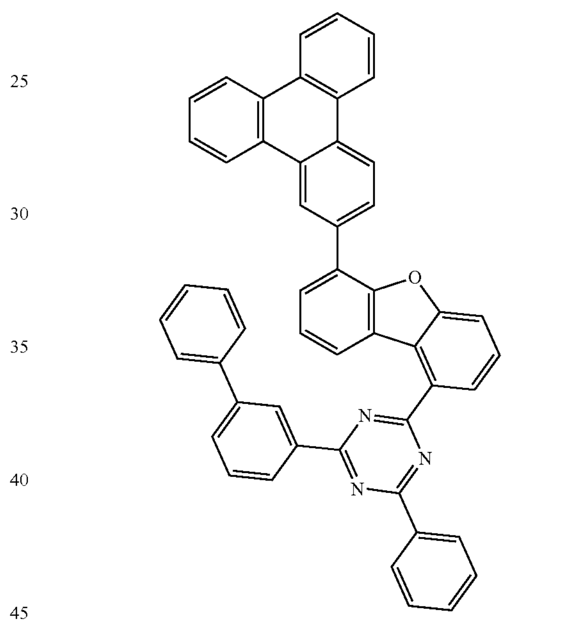
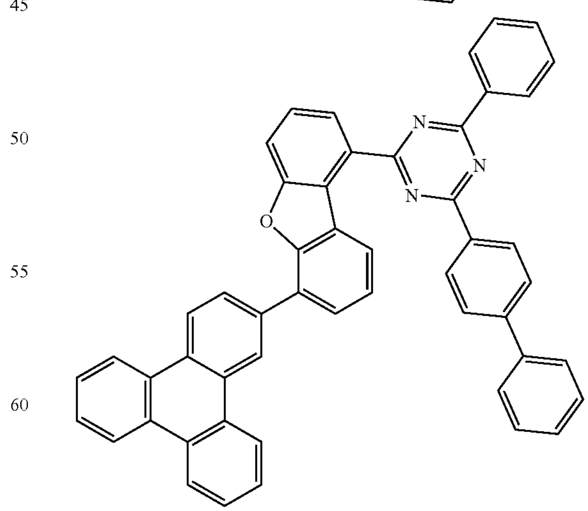

-continued
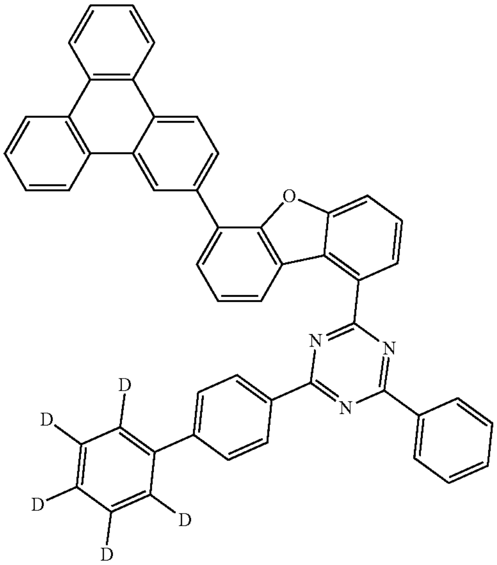
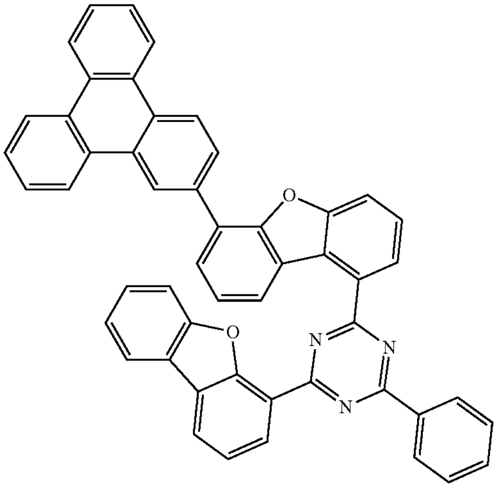
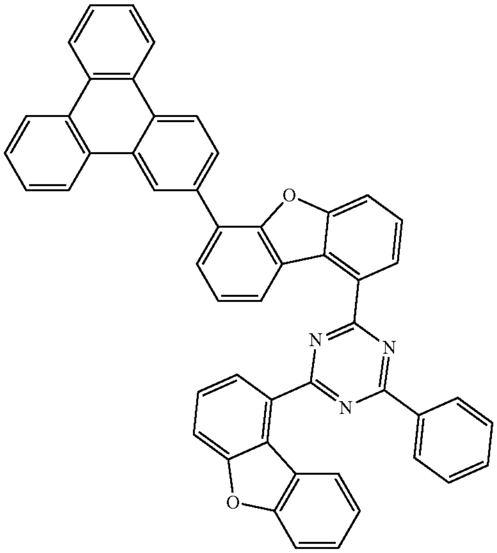
-continued
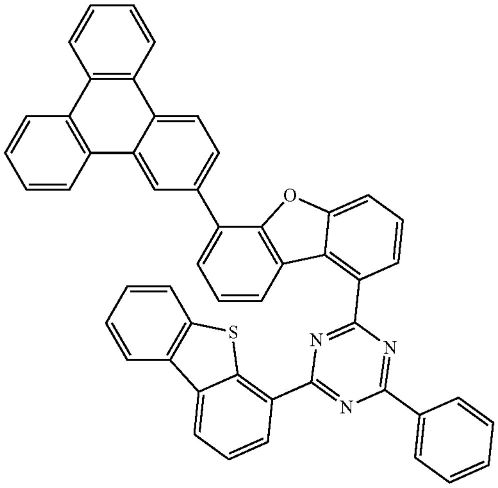
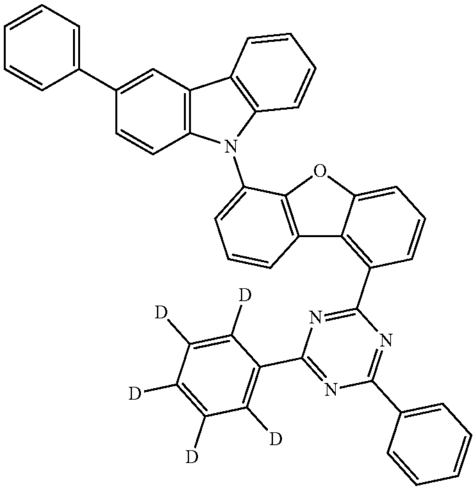
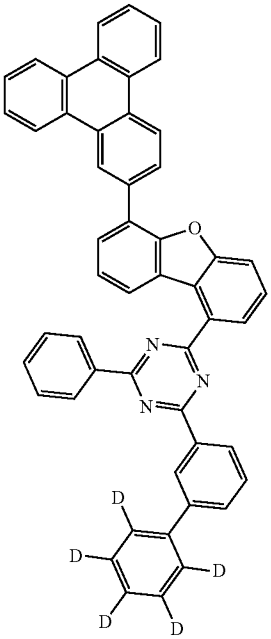

-continued
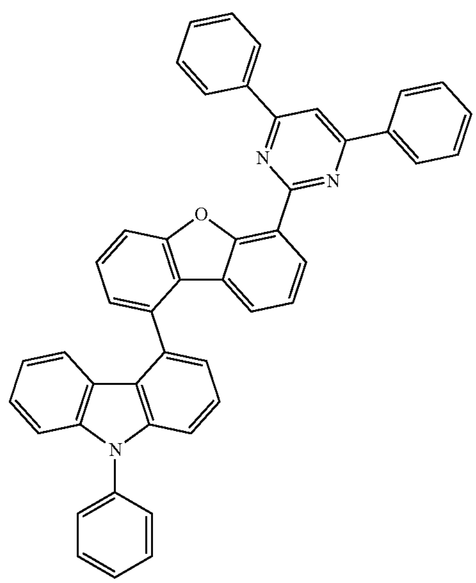
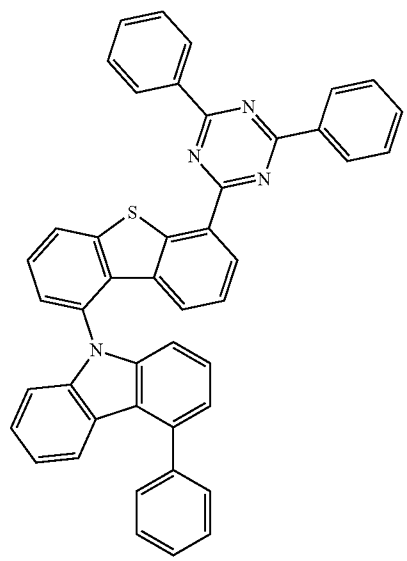
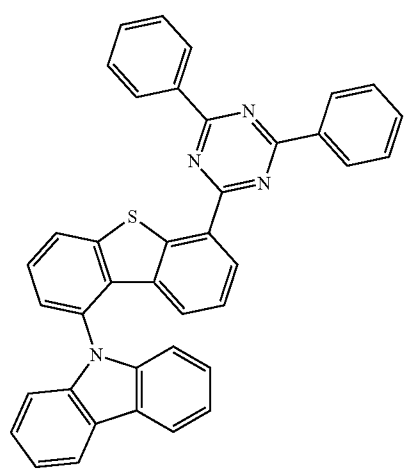
-continued
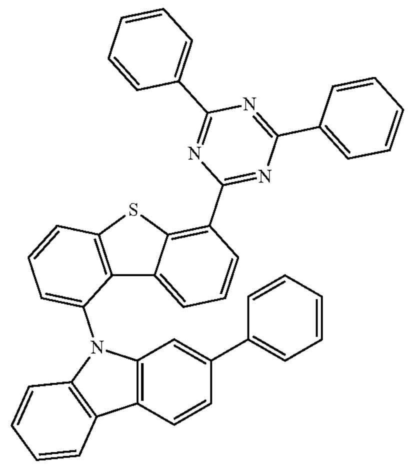
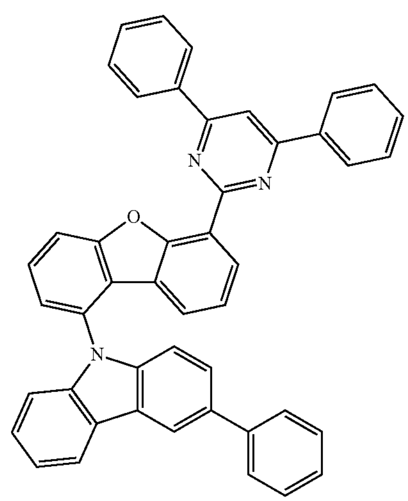
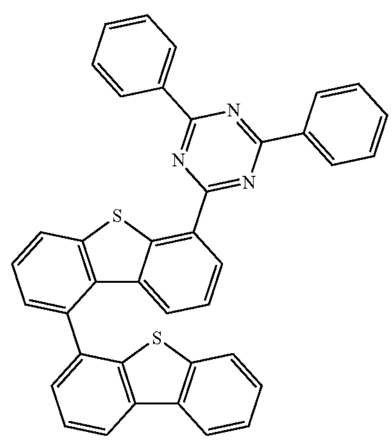

-continued
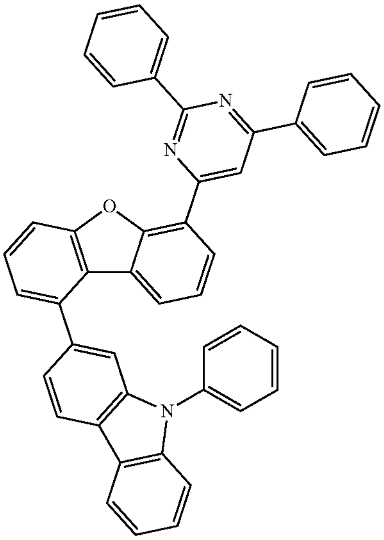
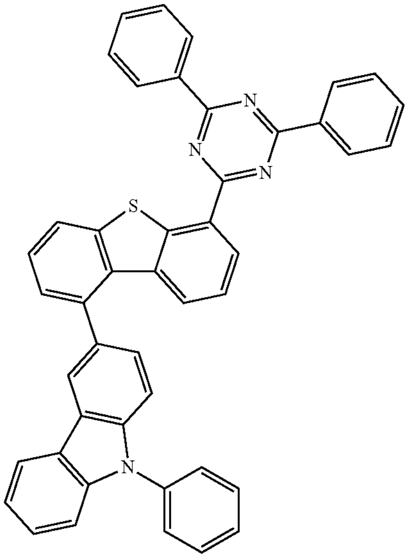
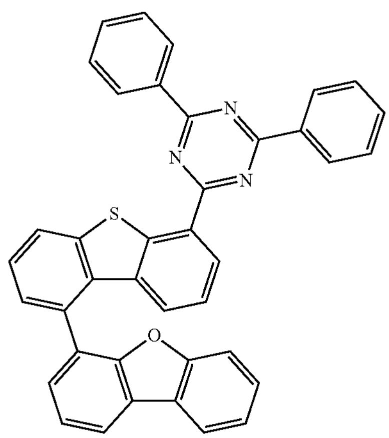
-continued
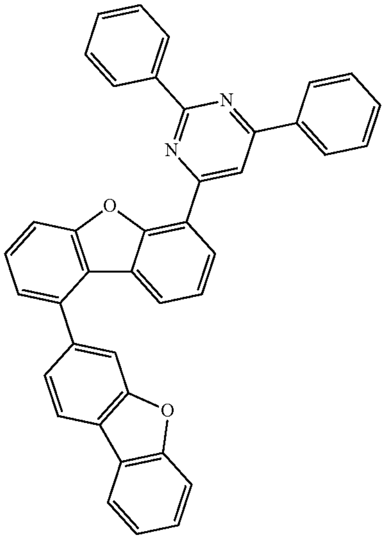
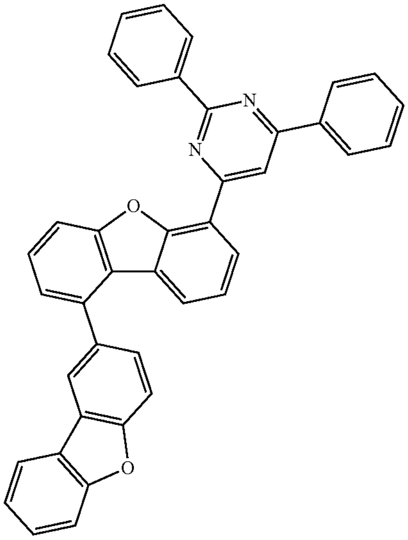
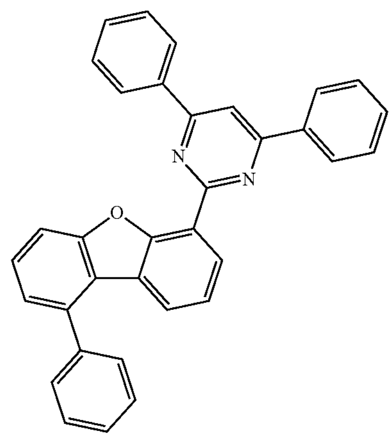

-continued
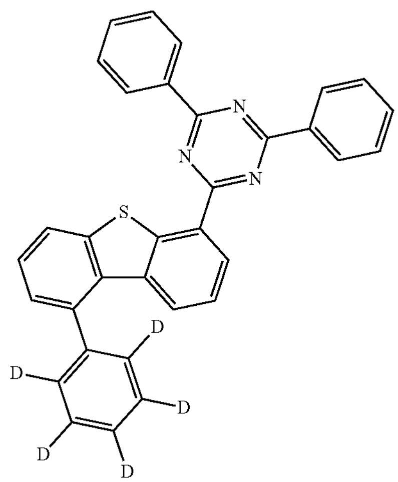
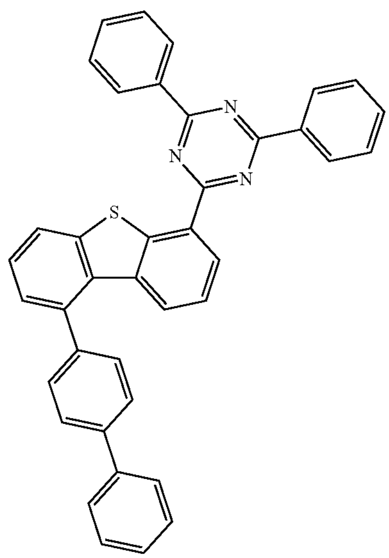
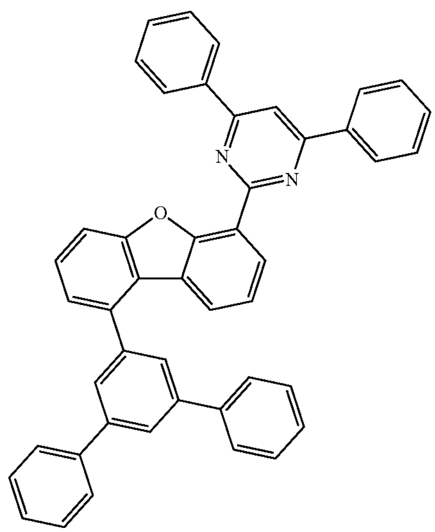
-continued
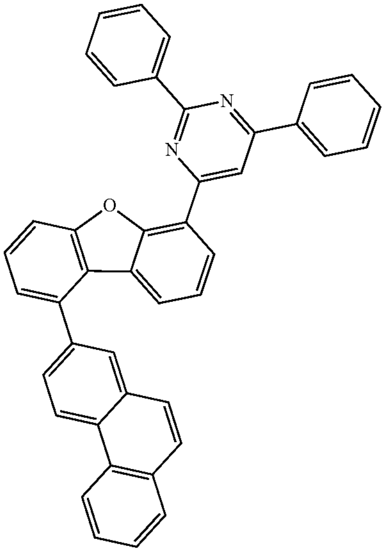
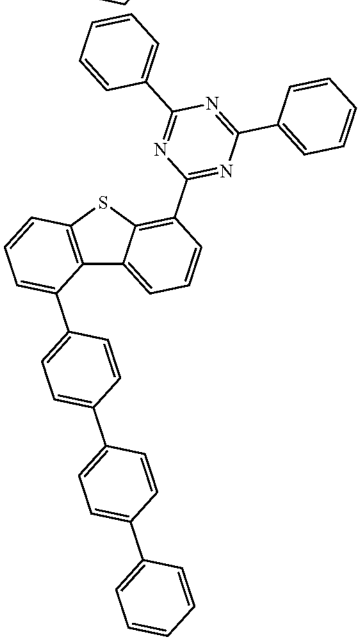
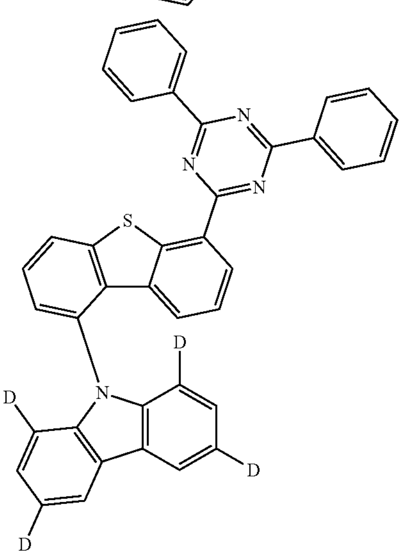

-continued
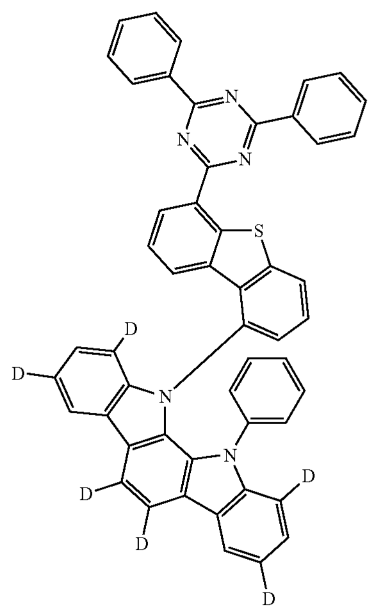
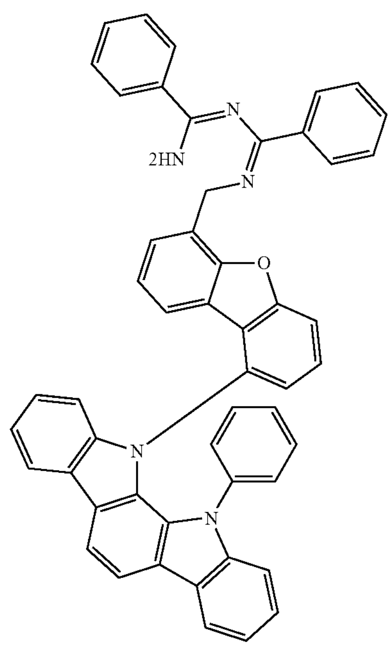
-continued
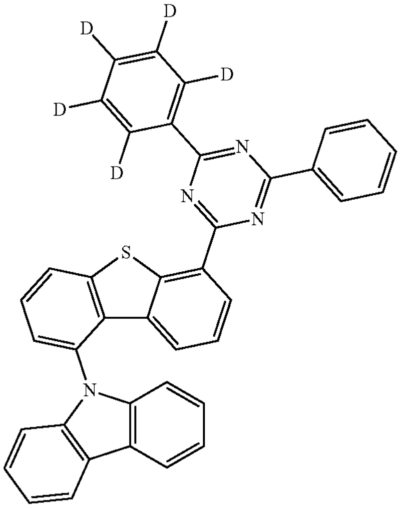
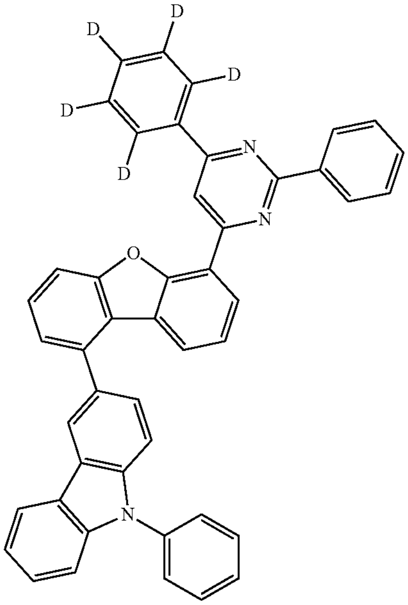
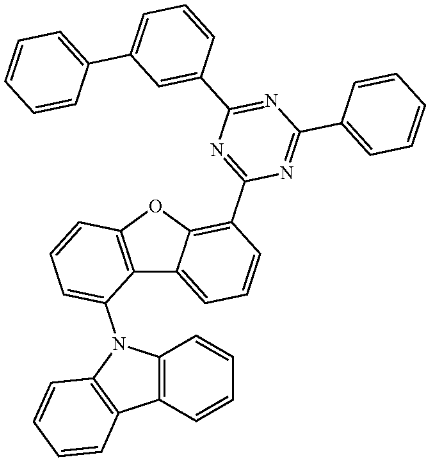

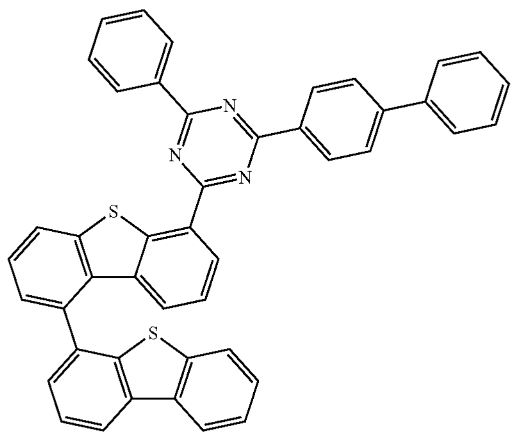
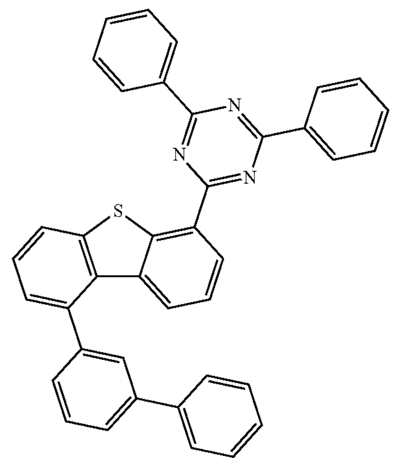
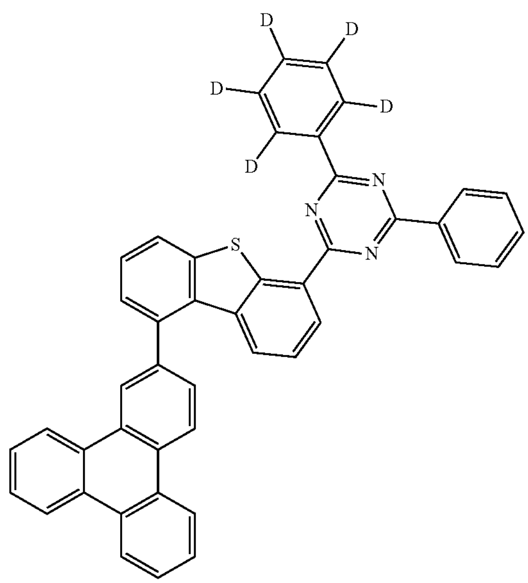
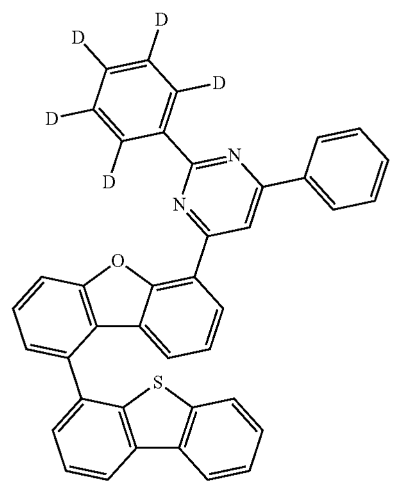
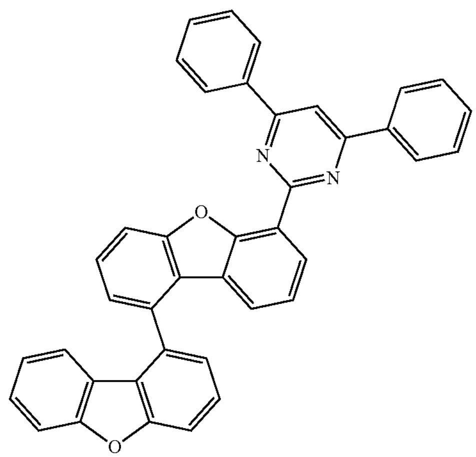
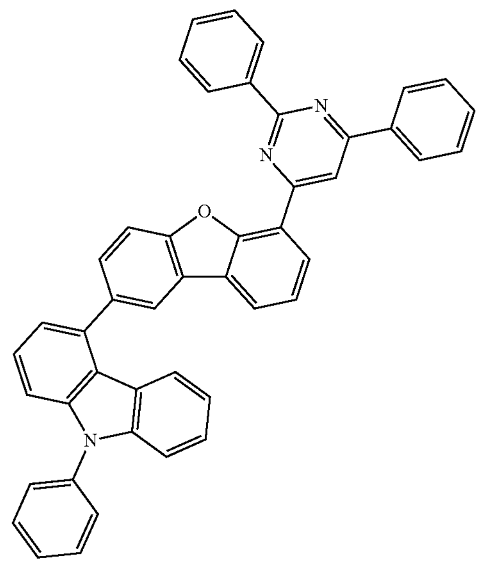

-continued
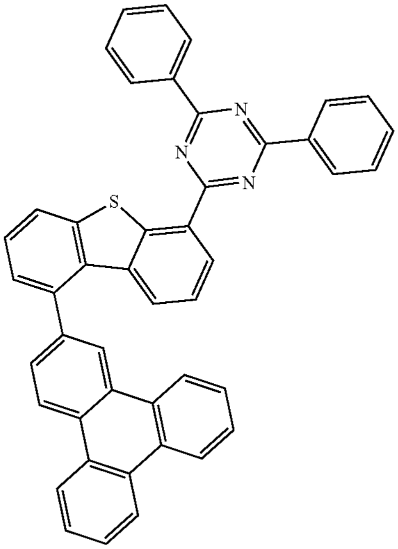
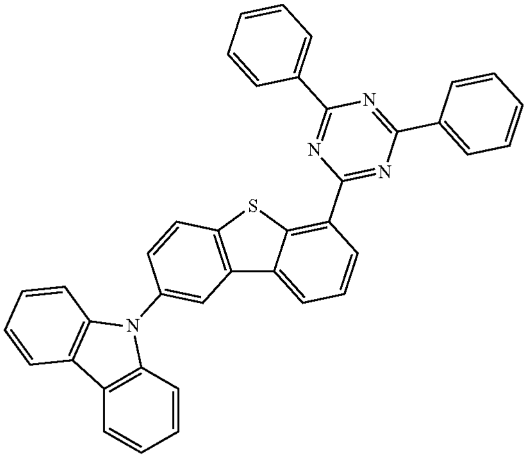
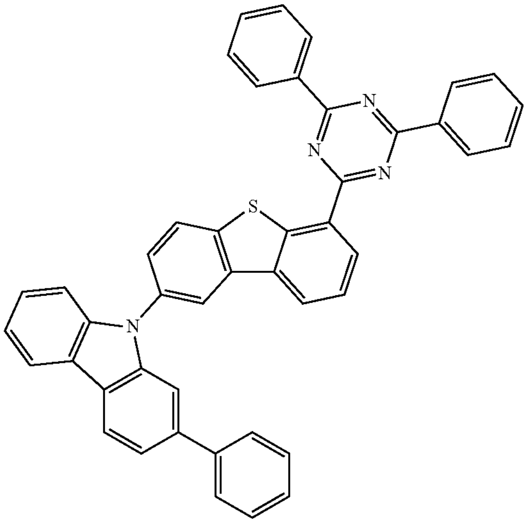
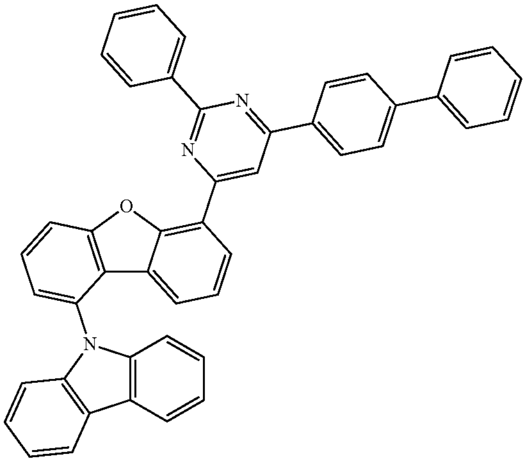
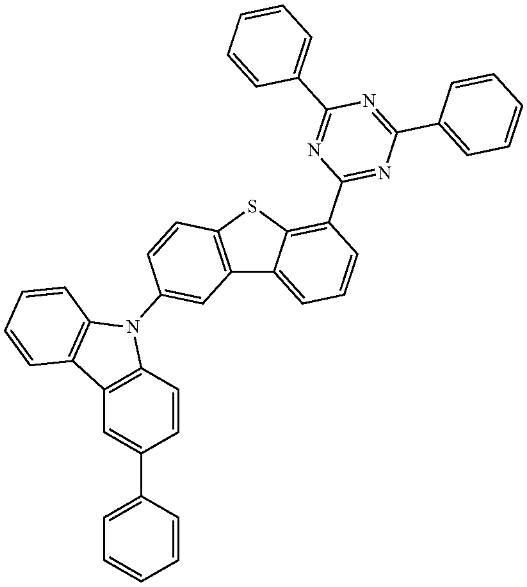
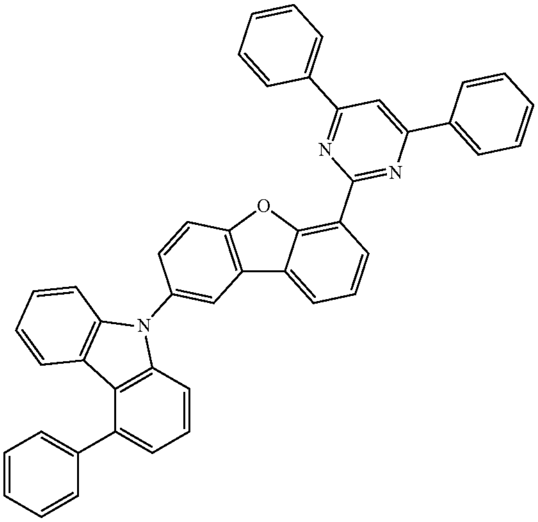

-continued
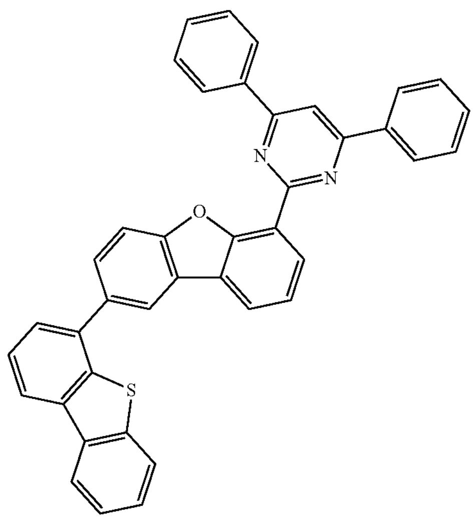
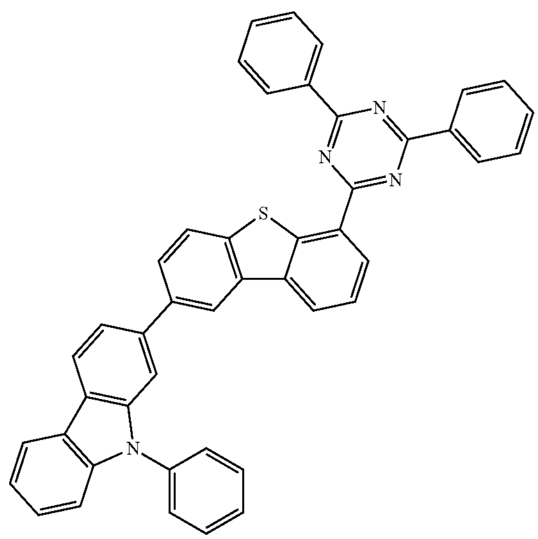
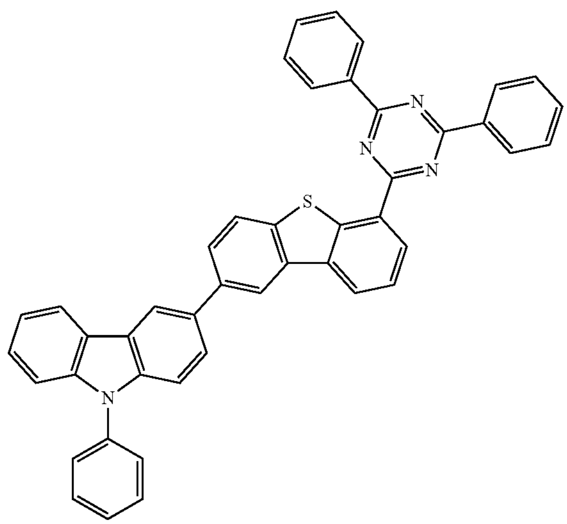
-continued
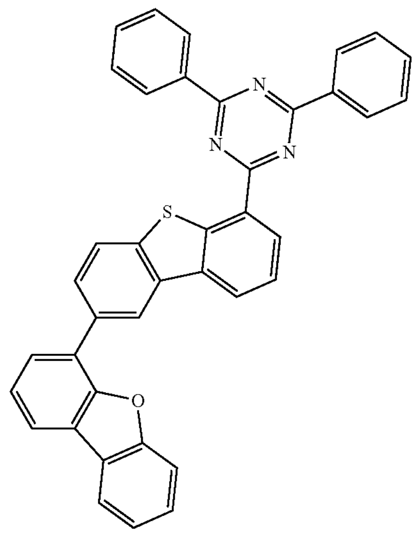
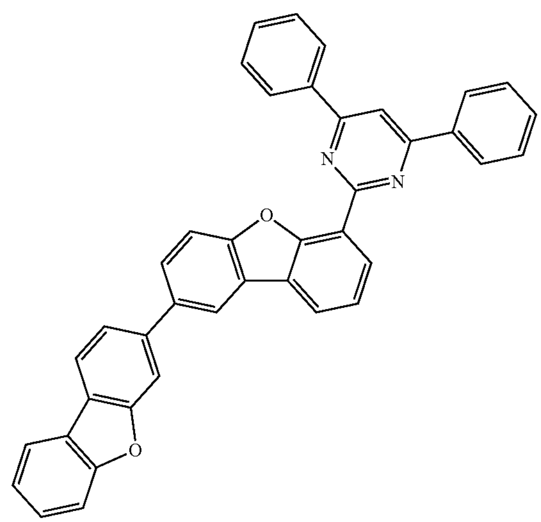
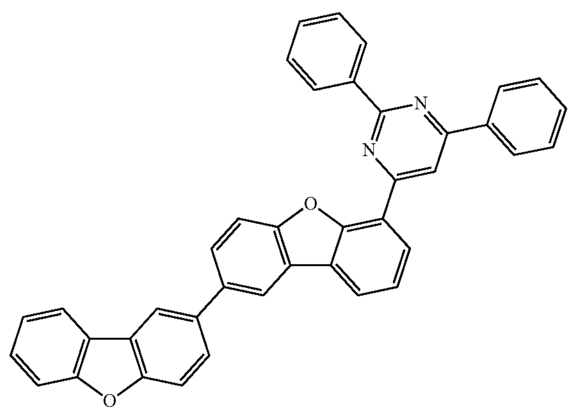

-continued
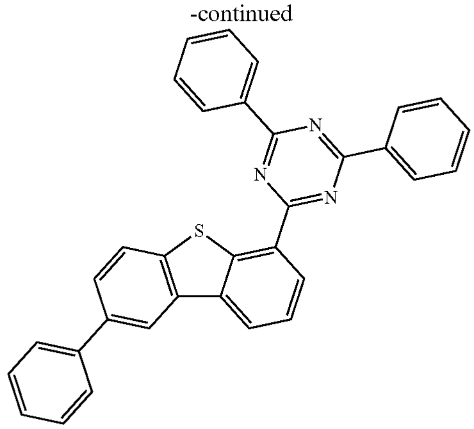
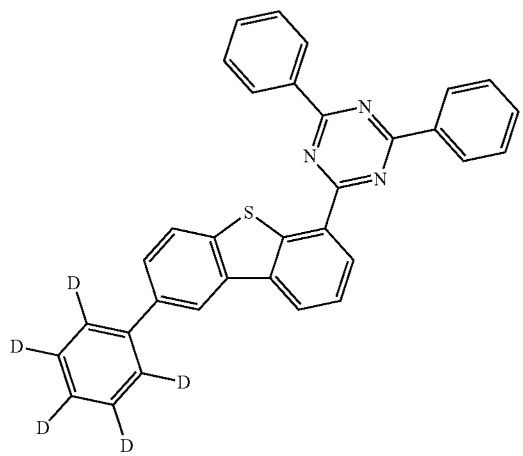
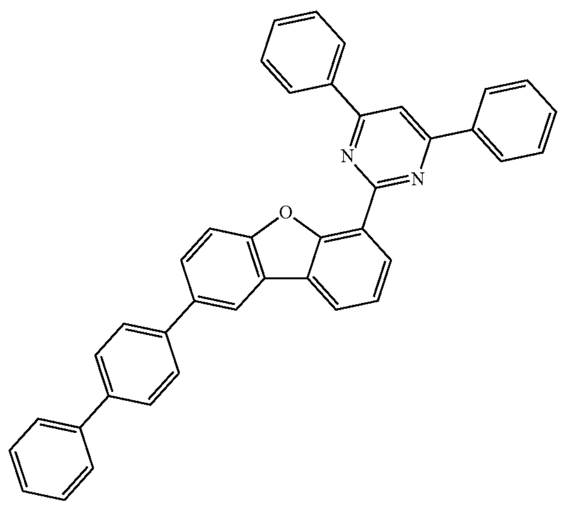
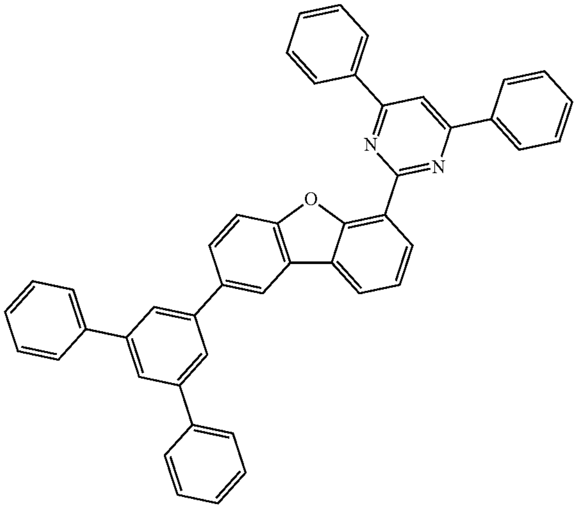
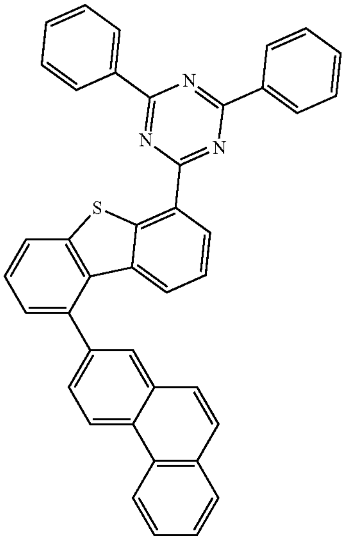
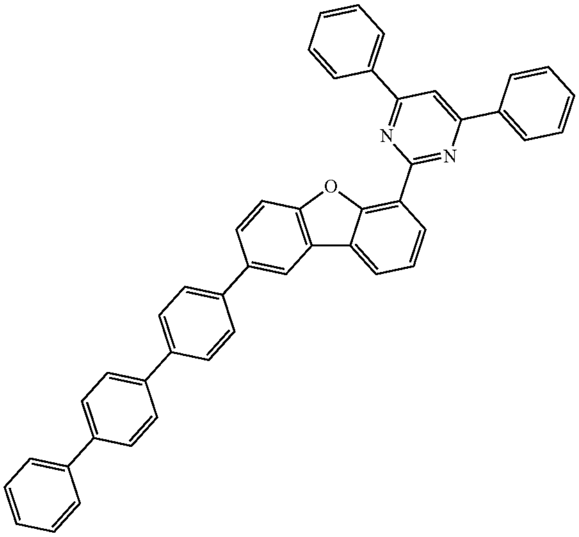

-continued
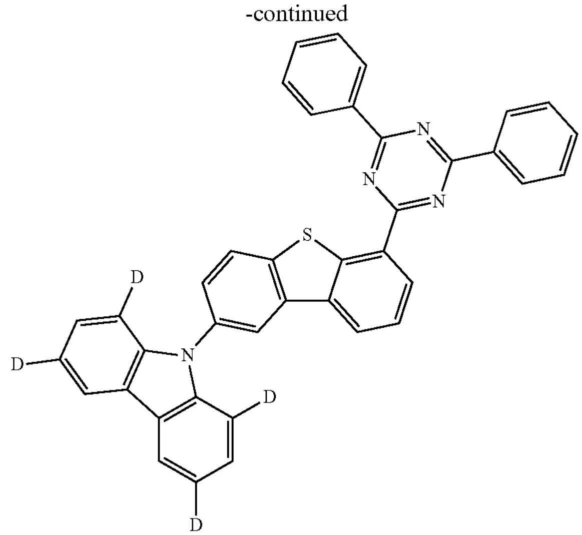
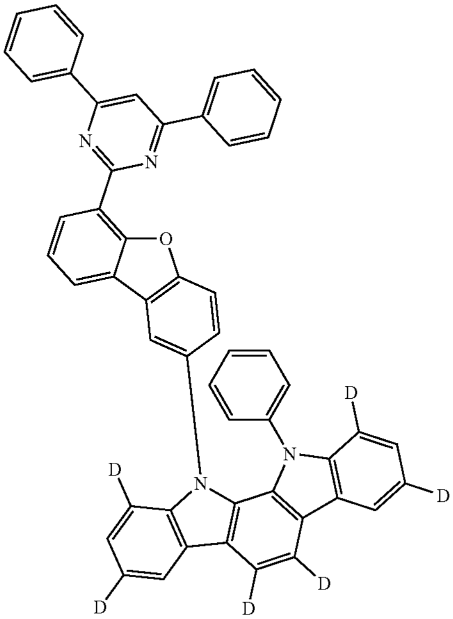
-continued
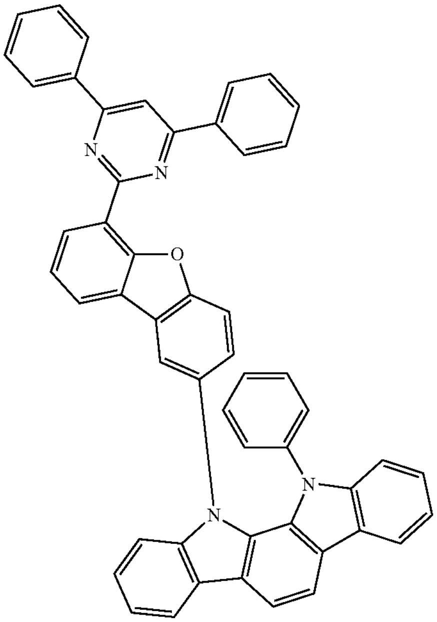
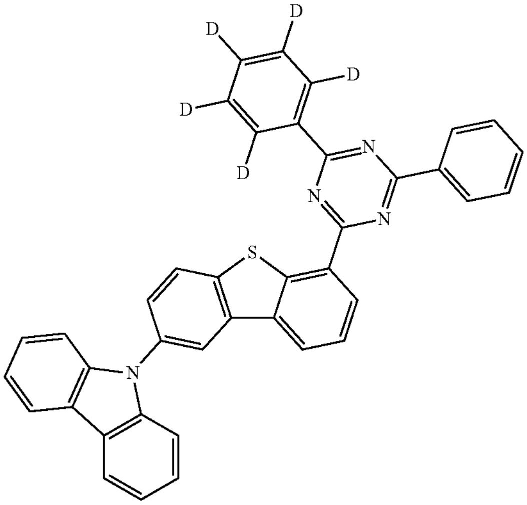
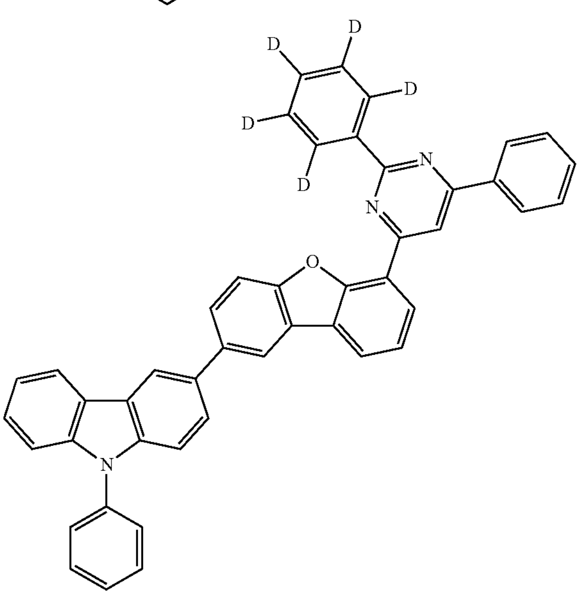

-continued
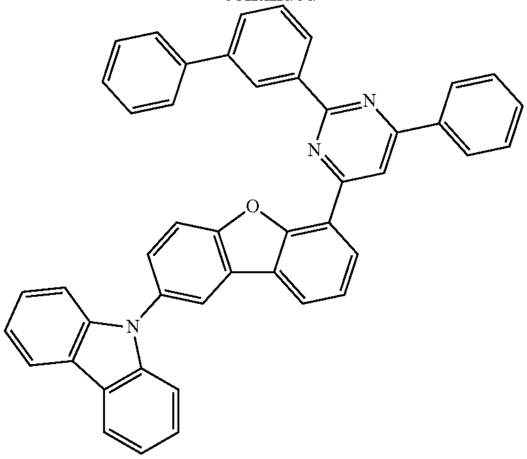
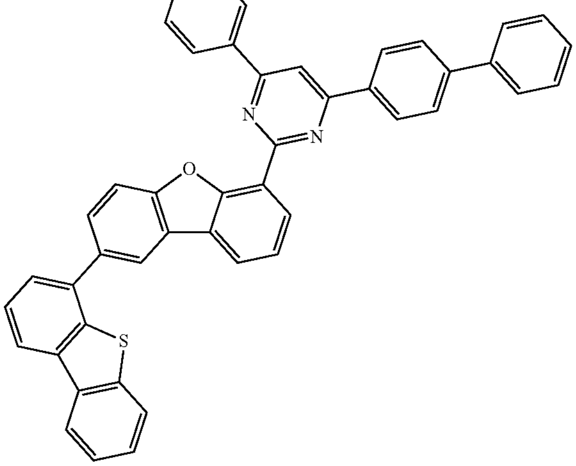
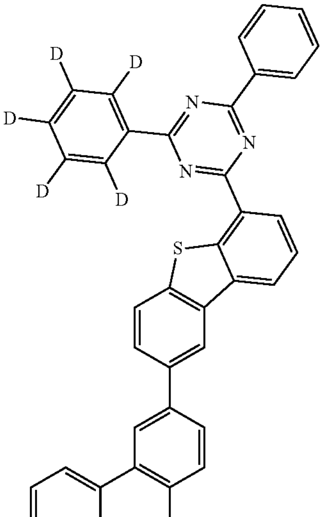
-continued
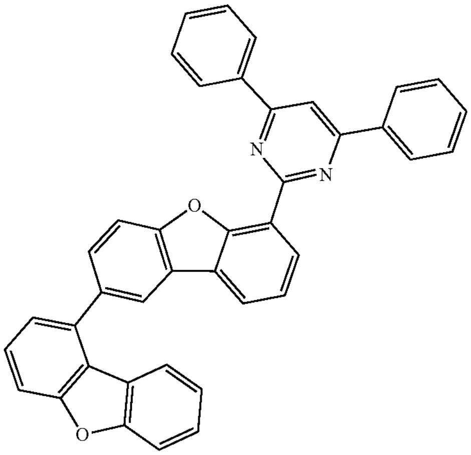
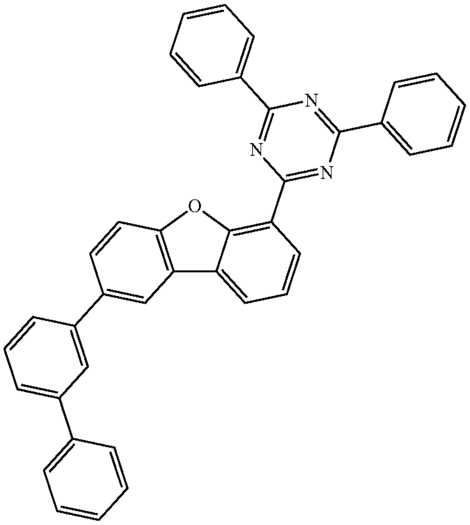
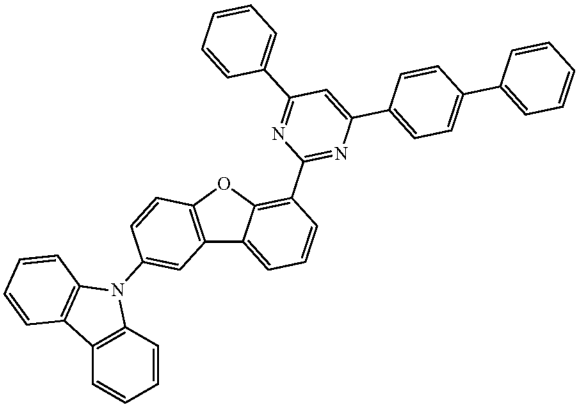

-continued
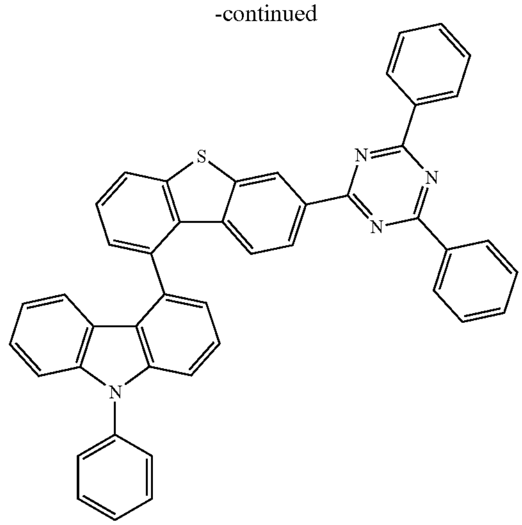
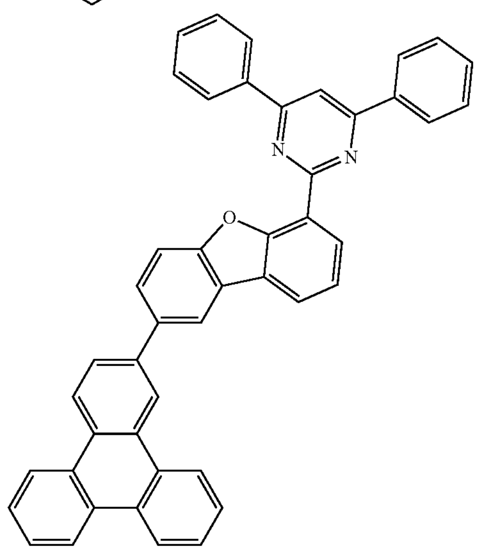
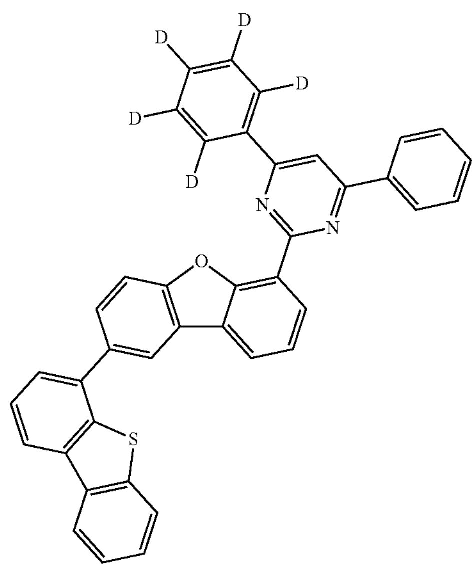
-continued
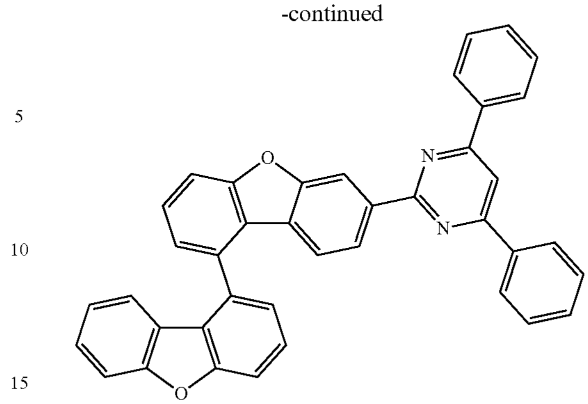
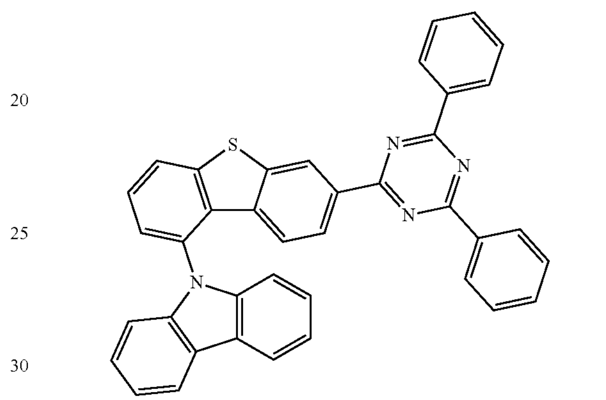
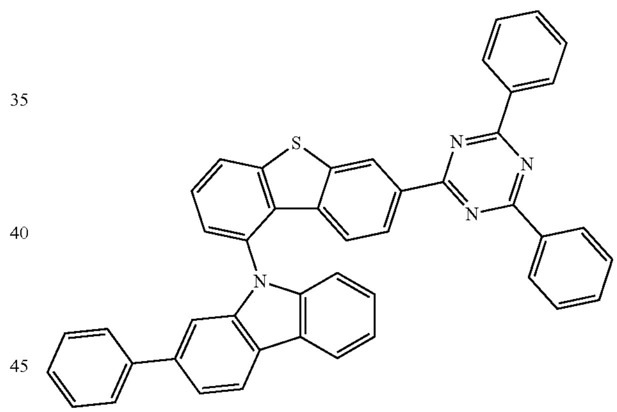
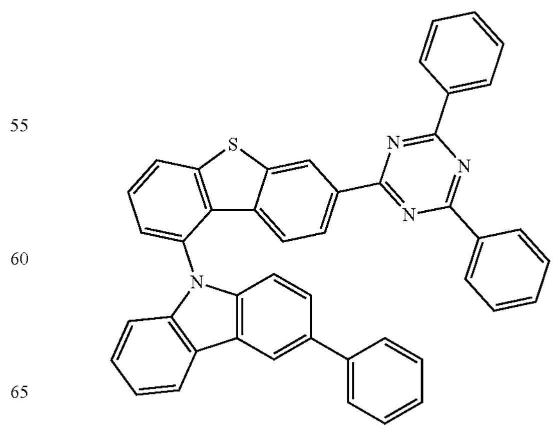

-continued
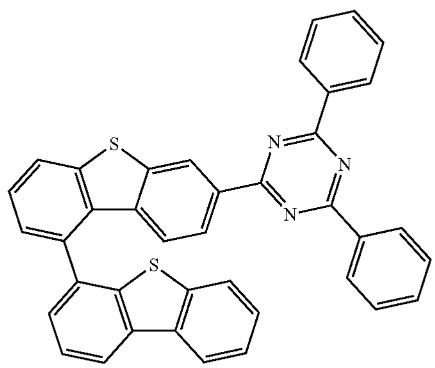
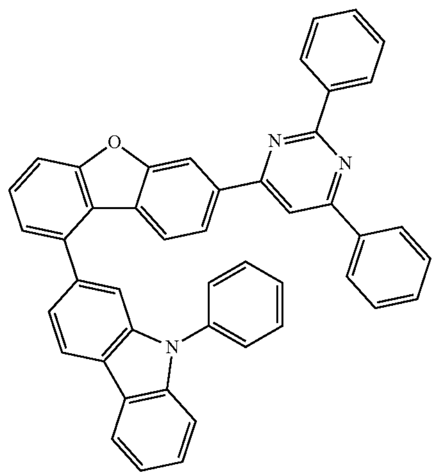
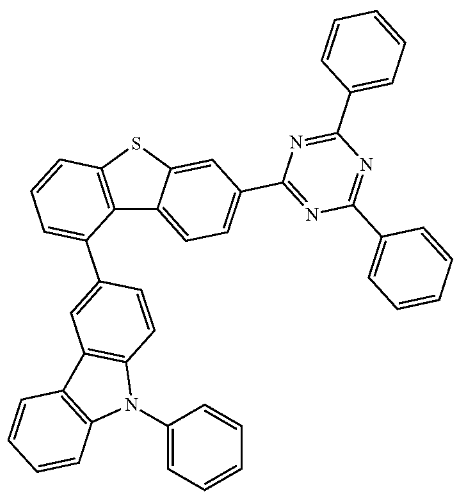
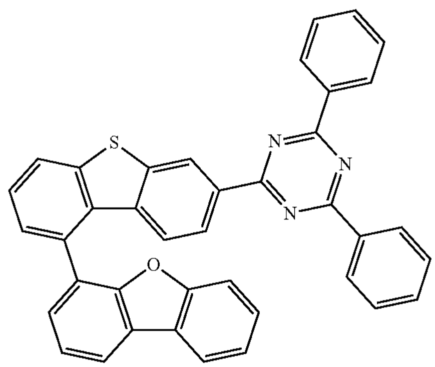
-continued
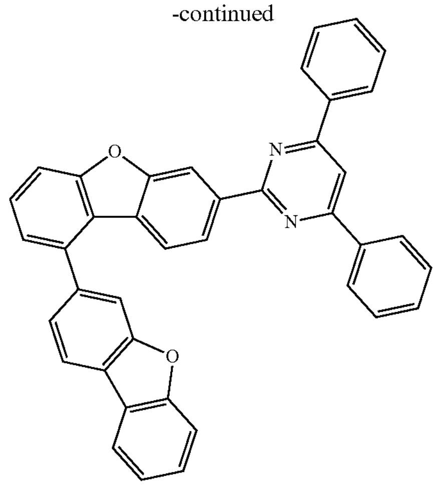
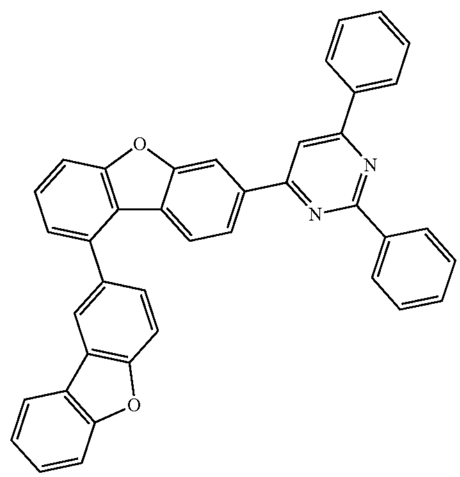
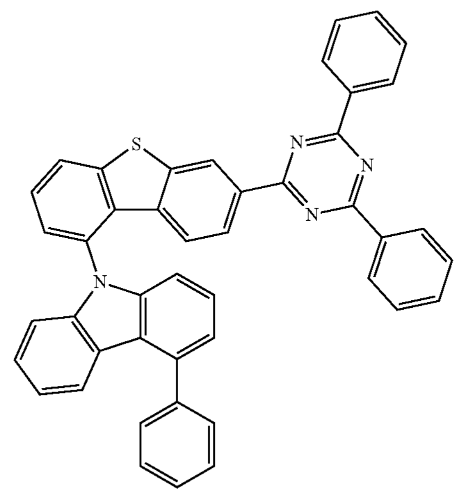

-continued
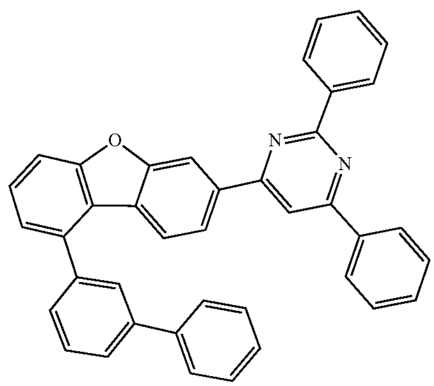
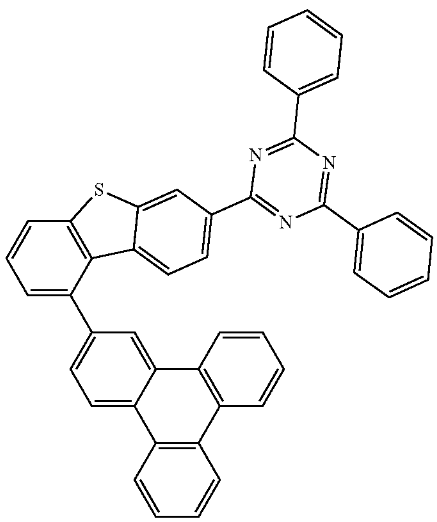
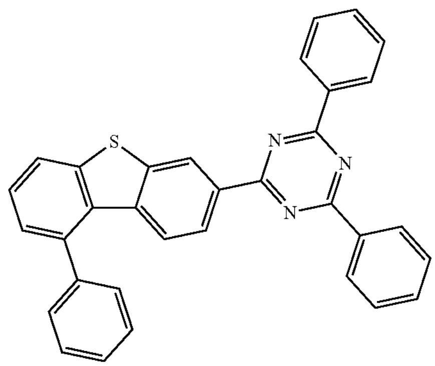
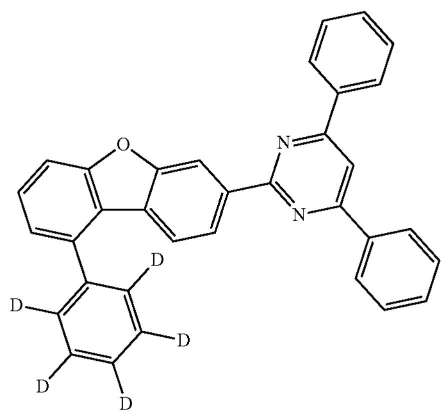
-continued
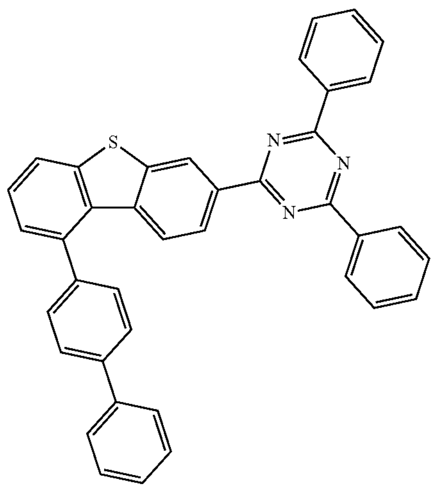
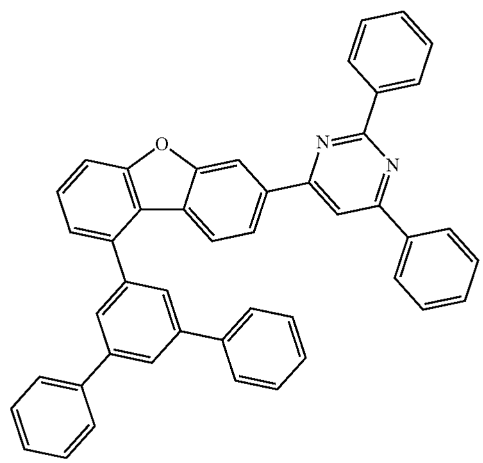
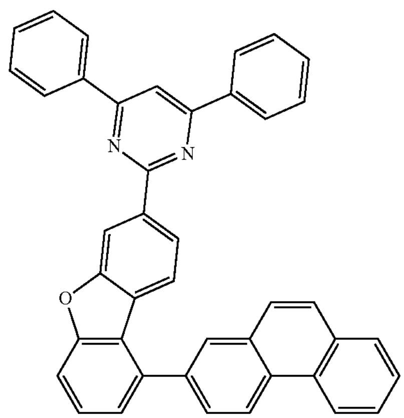

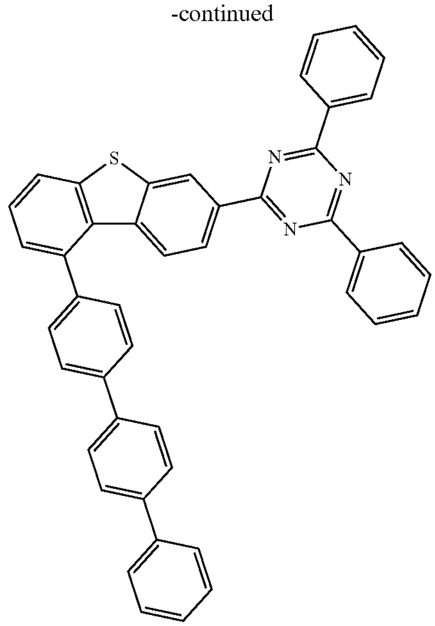
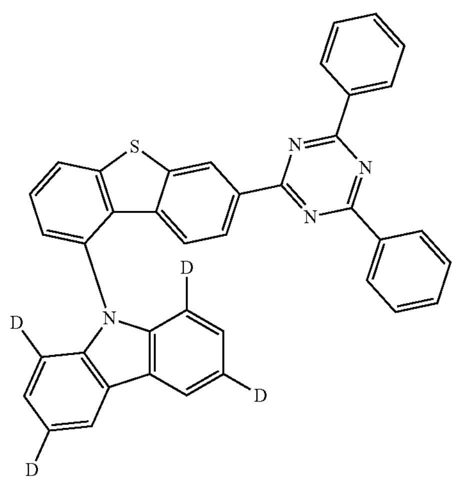
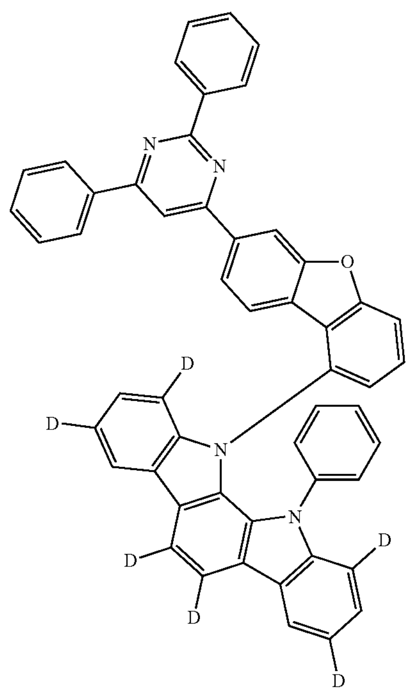
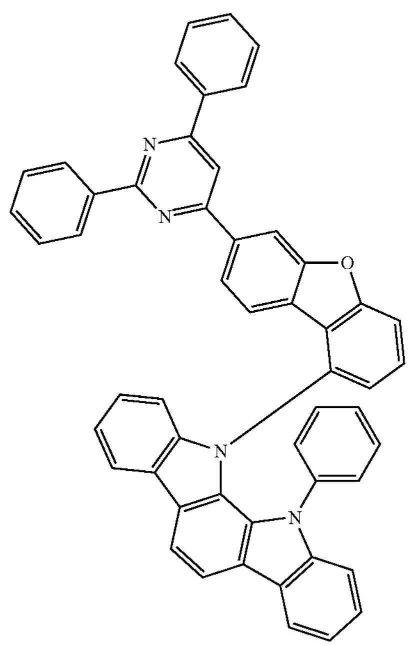

-continued
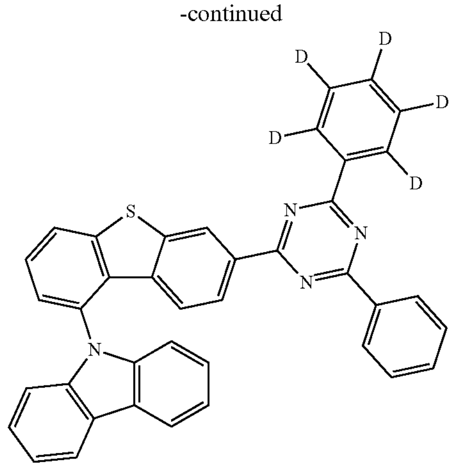
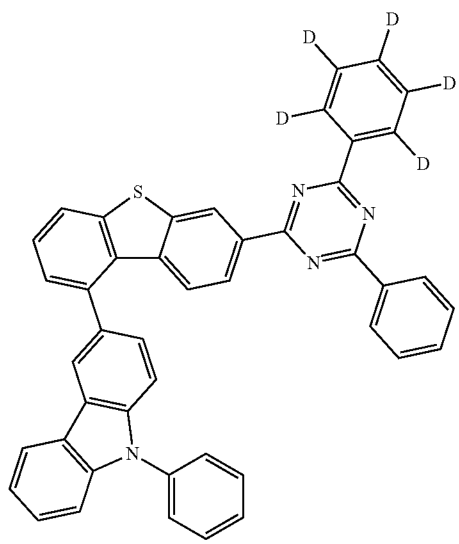
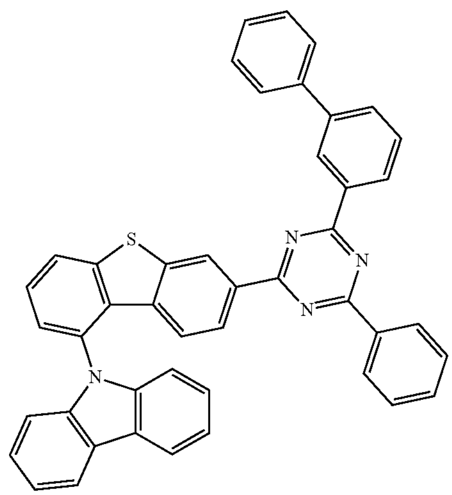
-continued
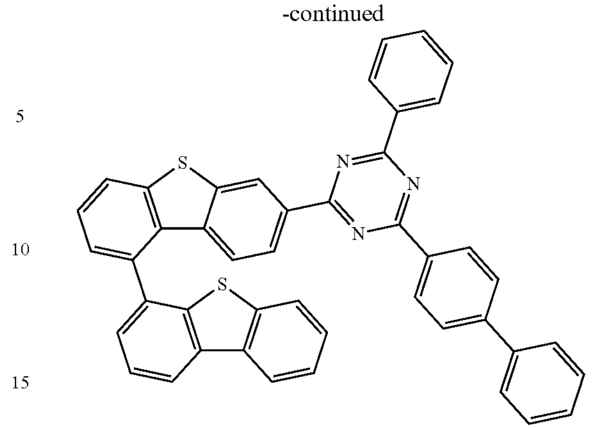
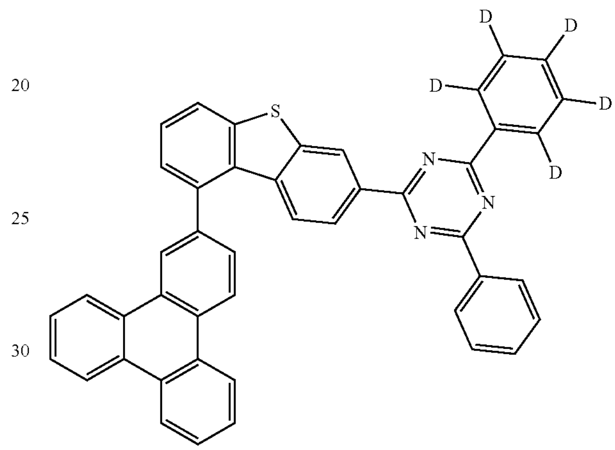
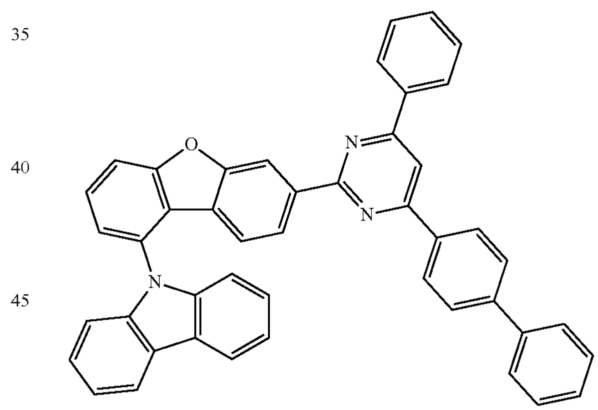
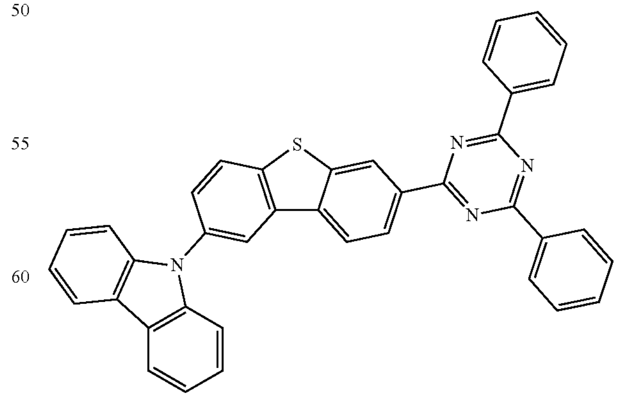

-continued
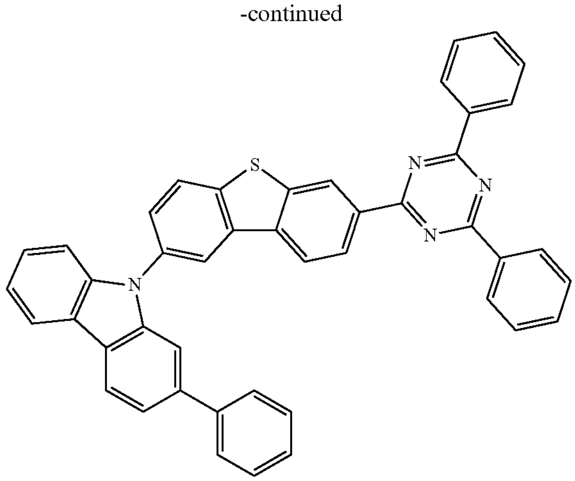
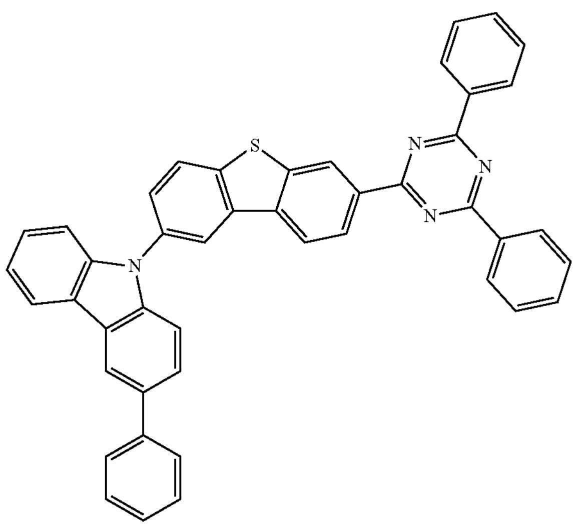
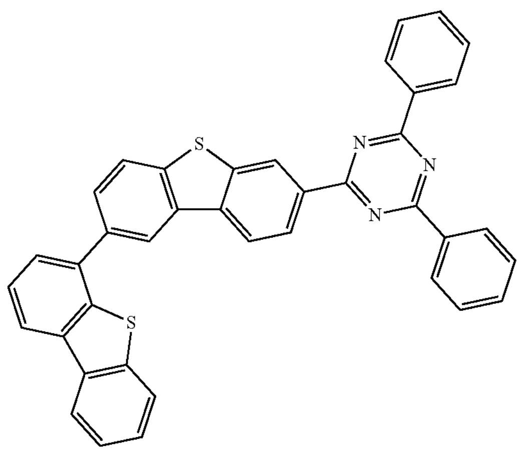
-continued
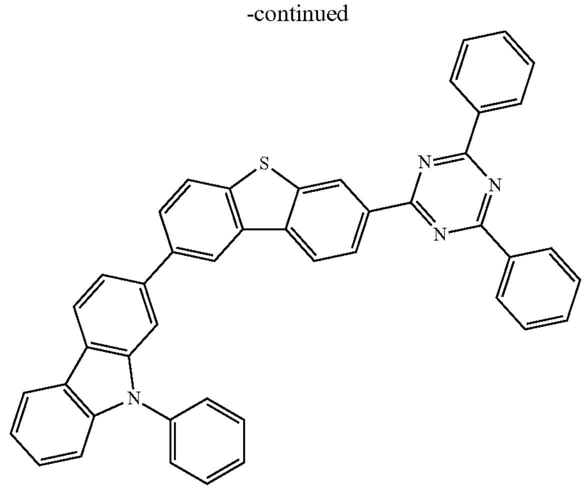
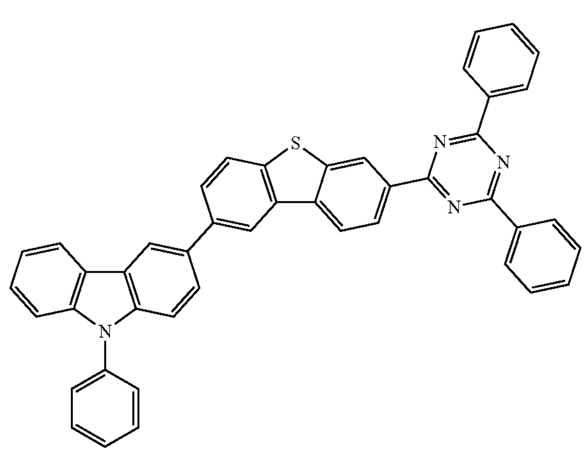
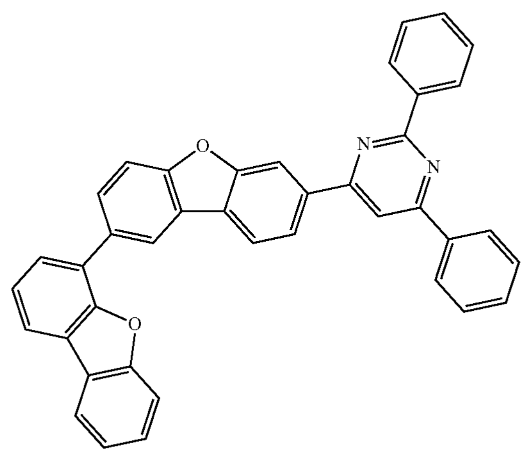

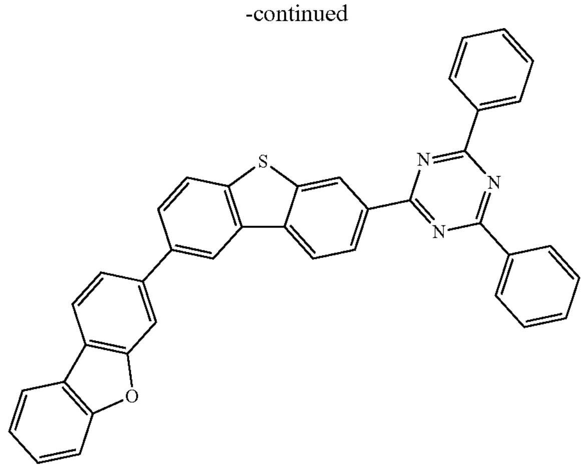
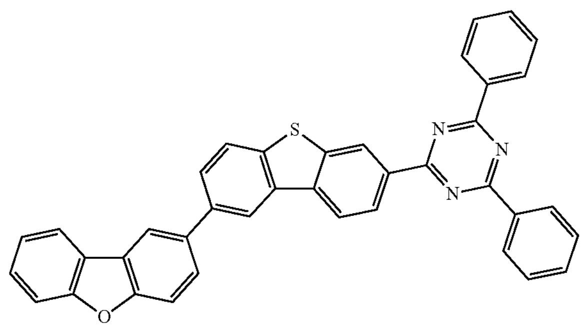
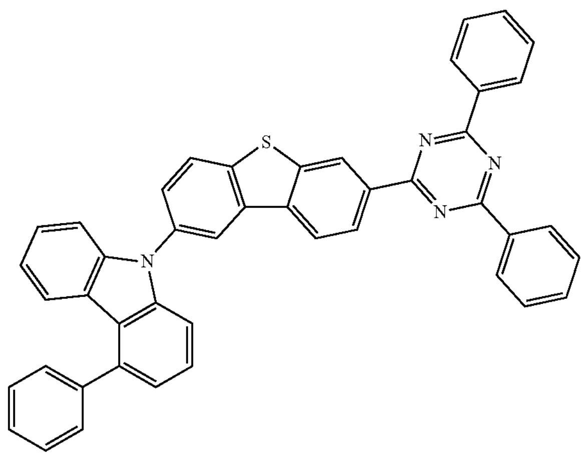
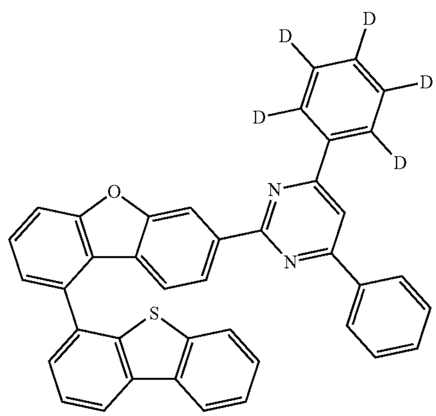
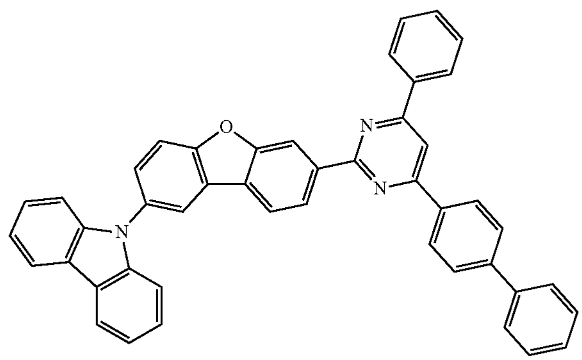
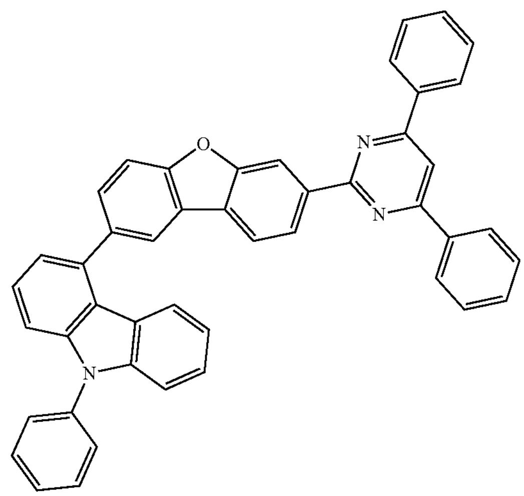
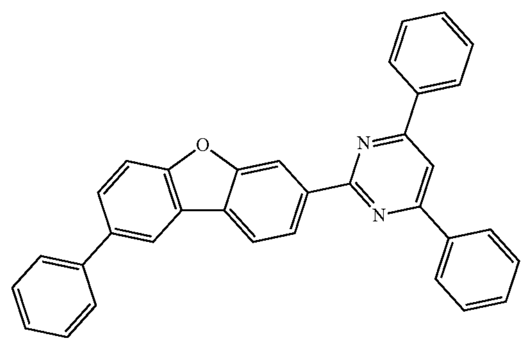
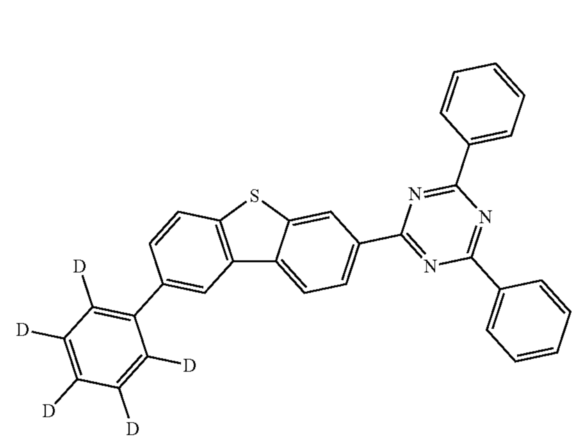

-continued
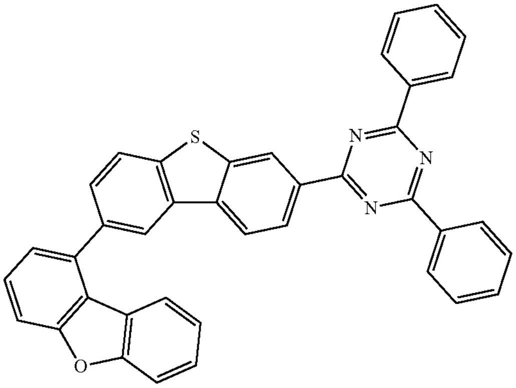
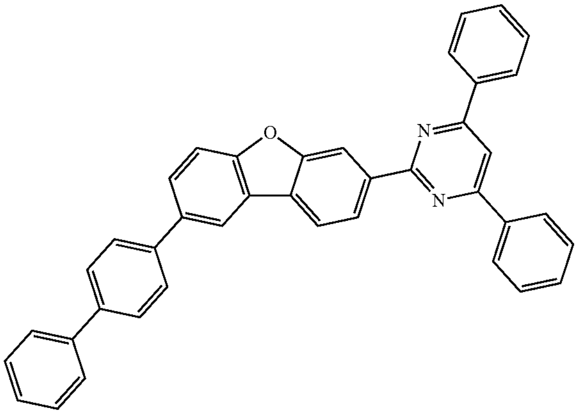
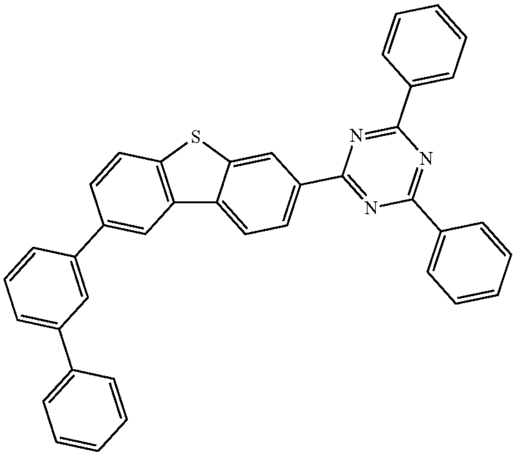
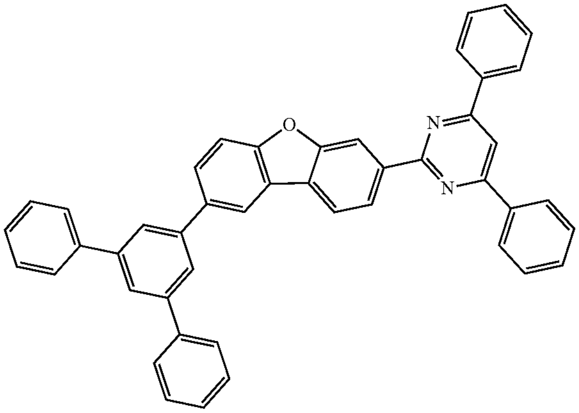
-continued
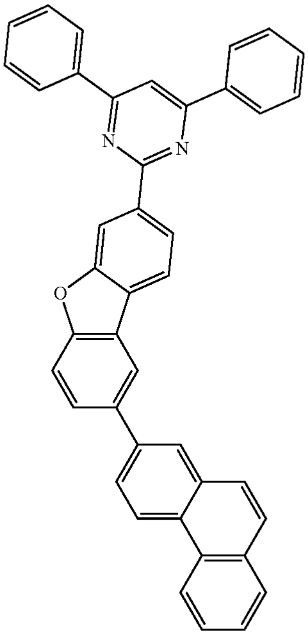
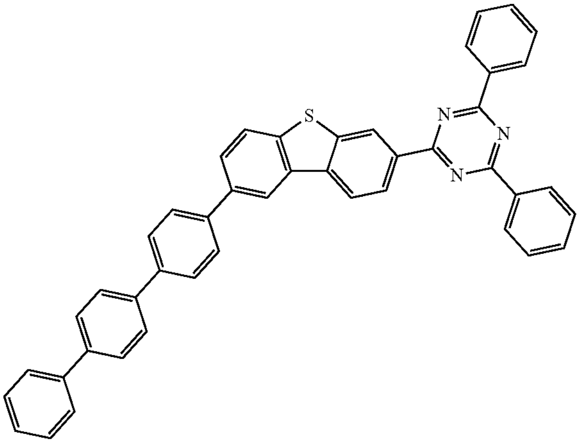
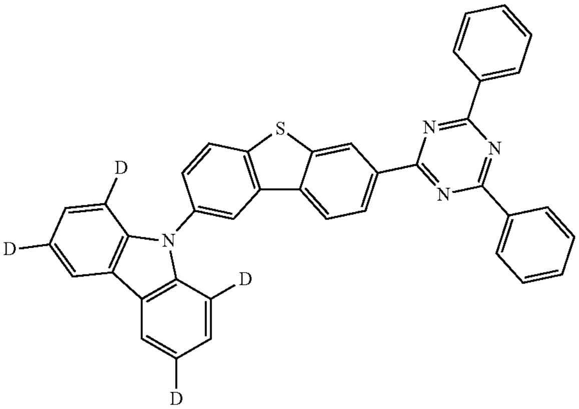

-continued
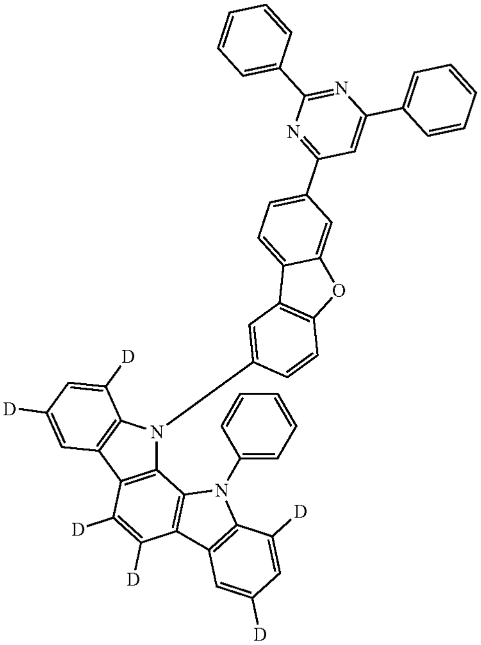
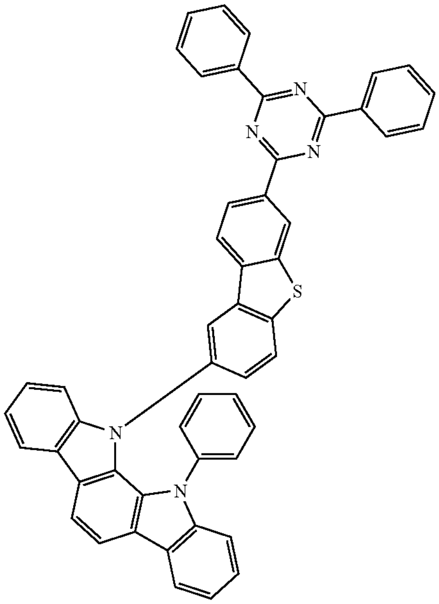
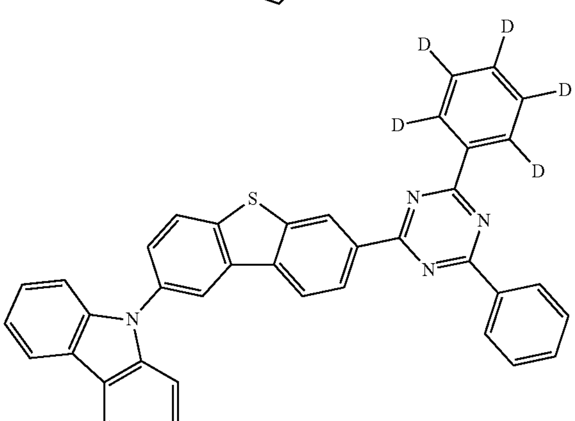
-continued
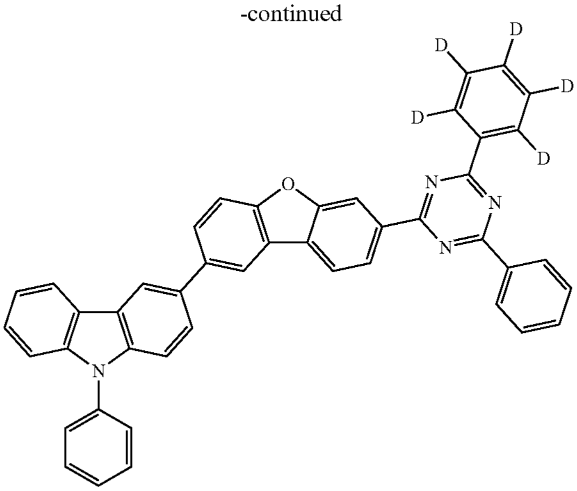
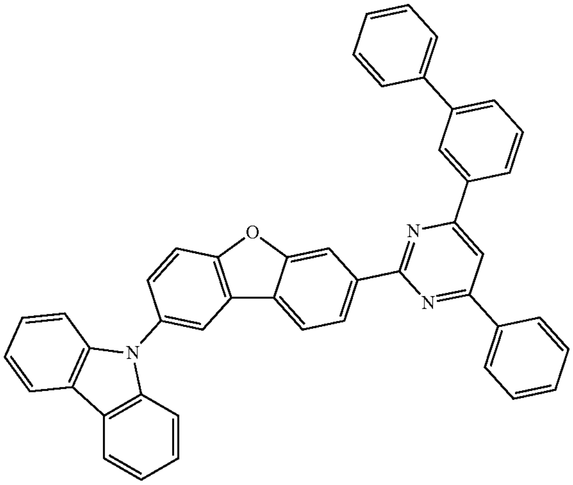
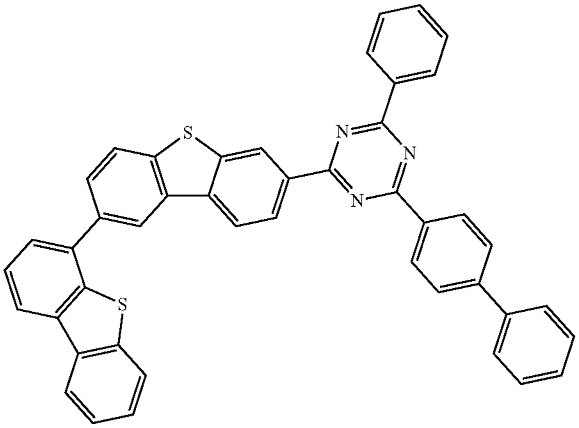

-continued
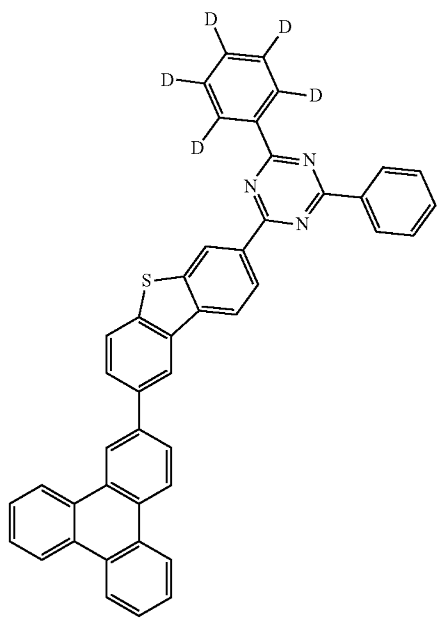
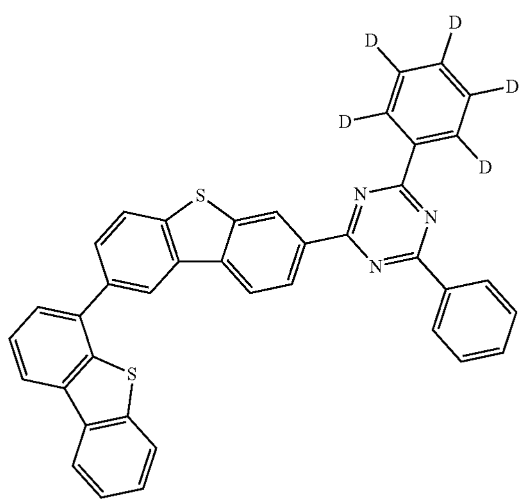
-continued
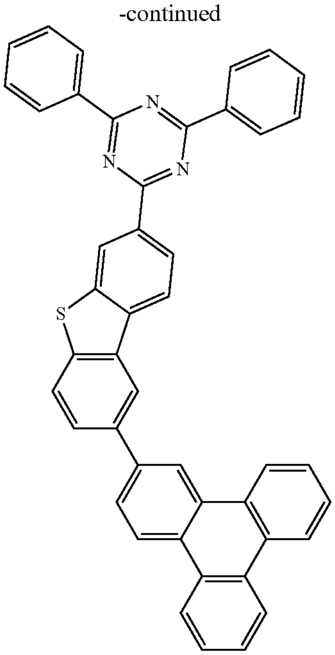
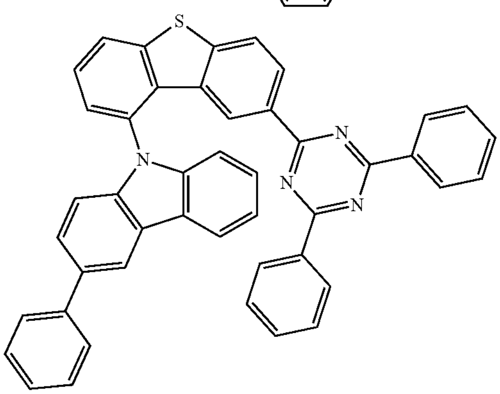
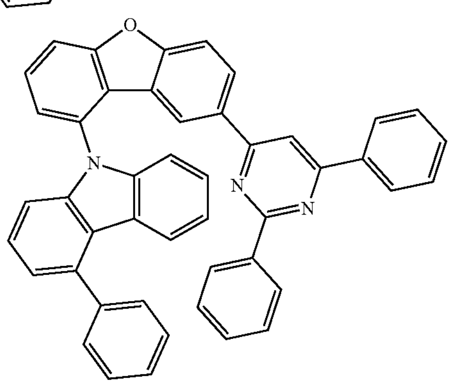
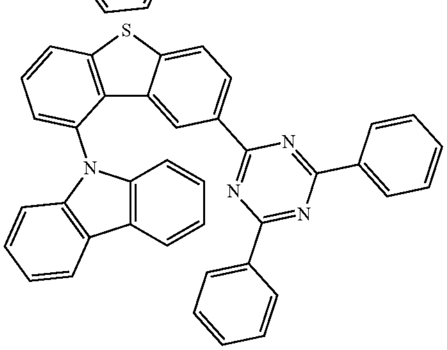

-continued
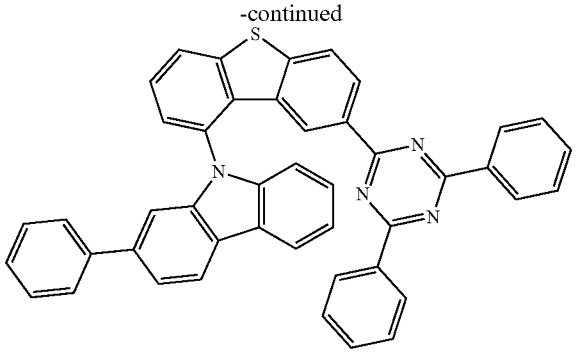
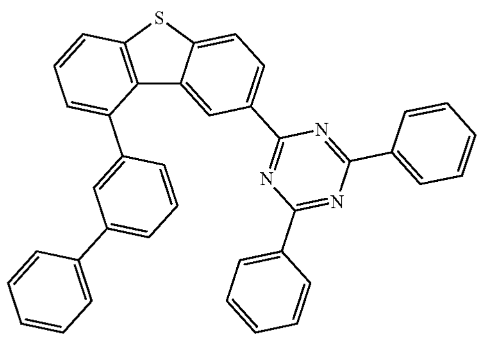
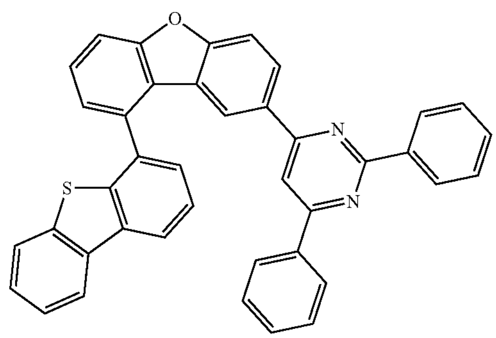
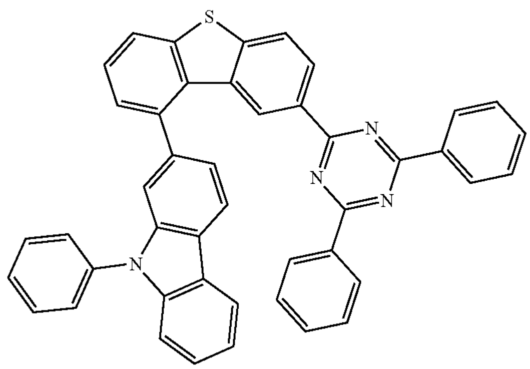
-continued
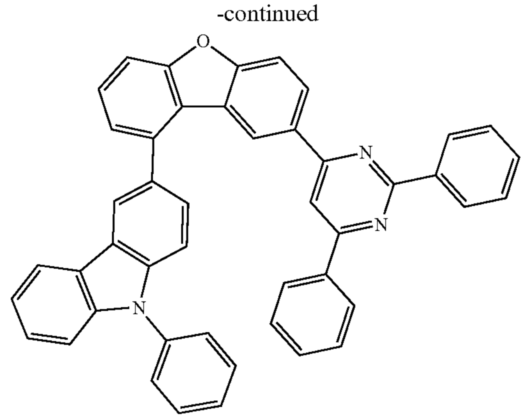
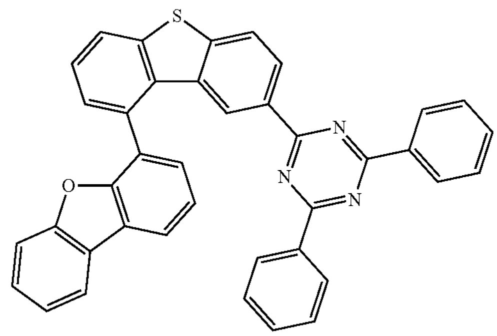
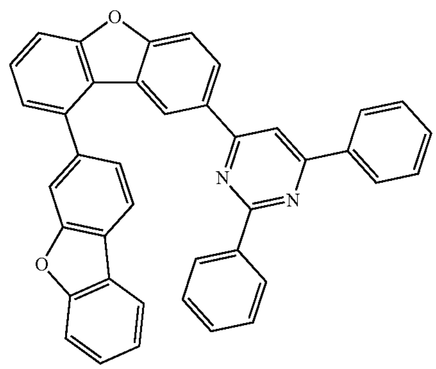
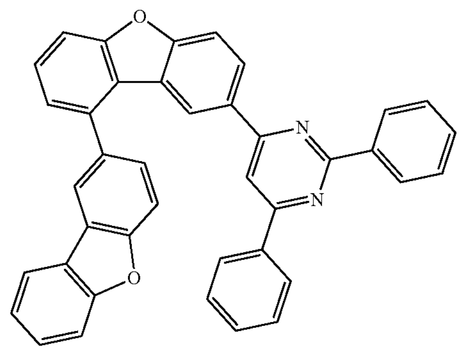

-continued
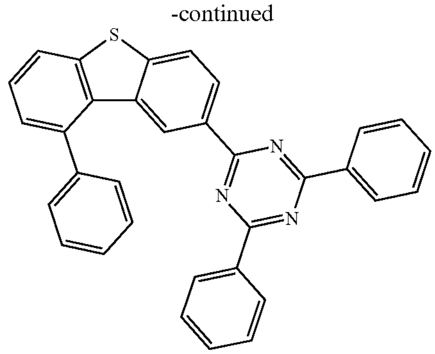
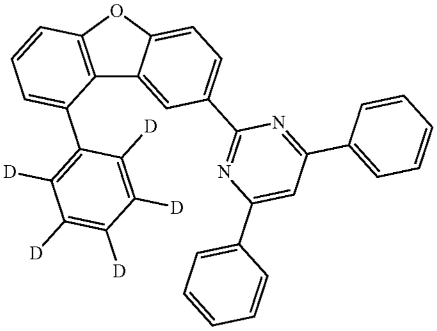
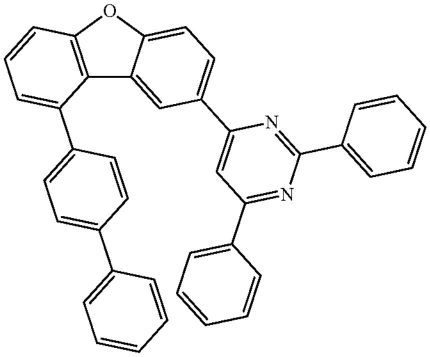
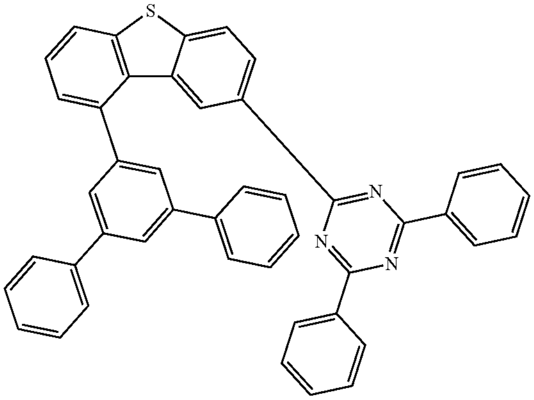
-continued
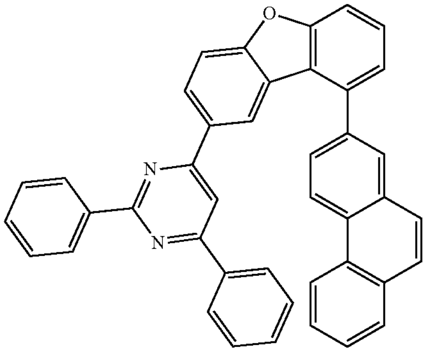
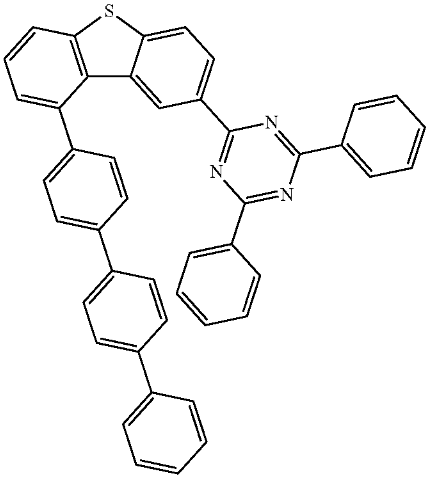
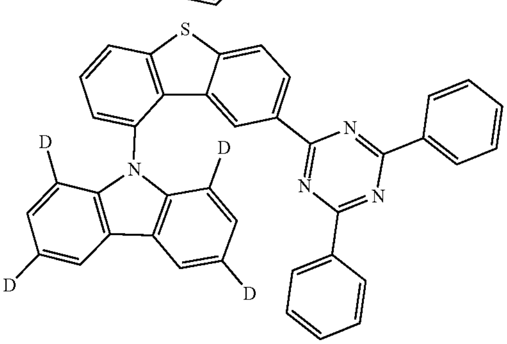
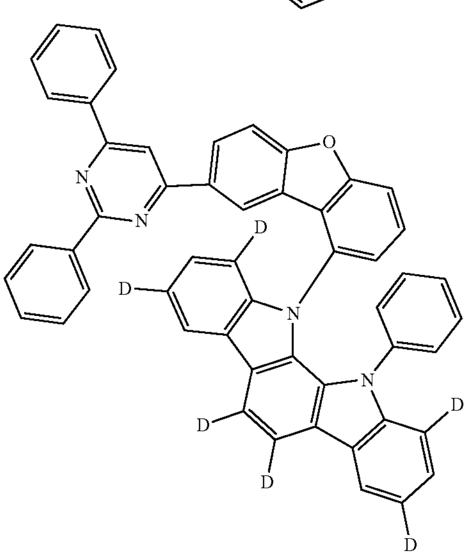

-continued
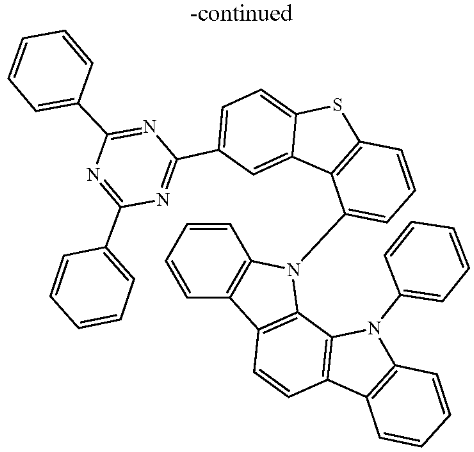
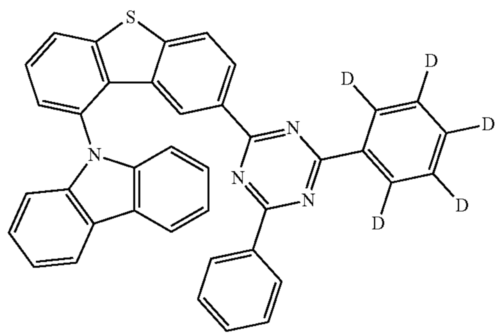
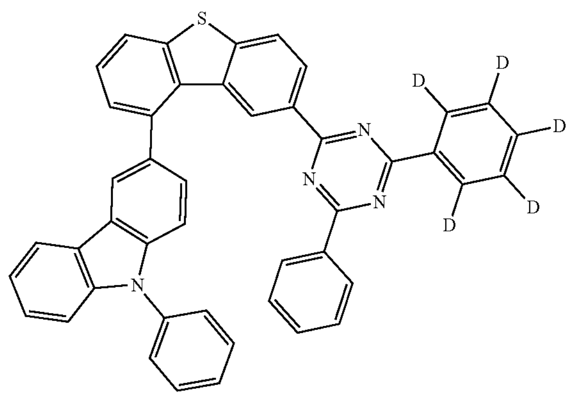
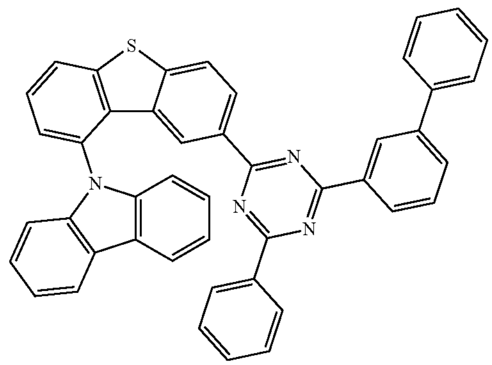
-continued
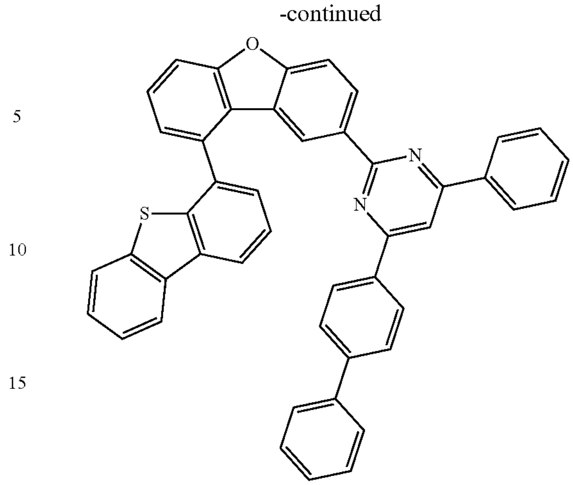
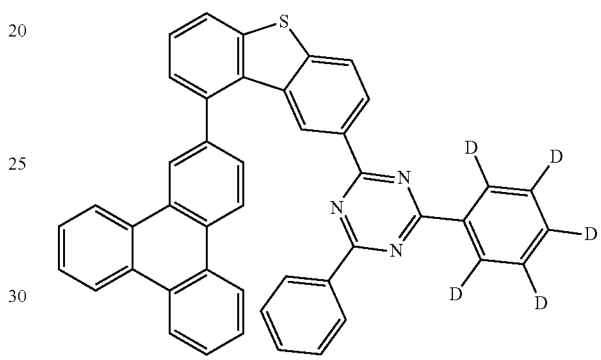
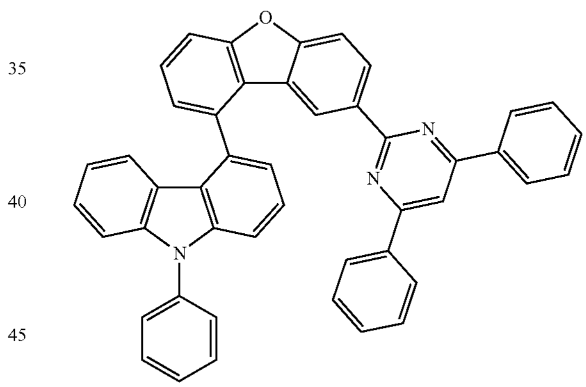
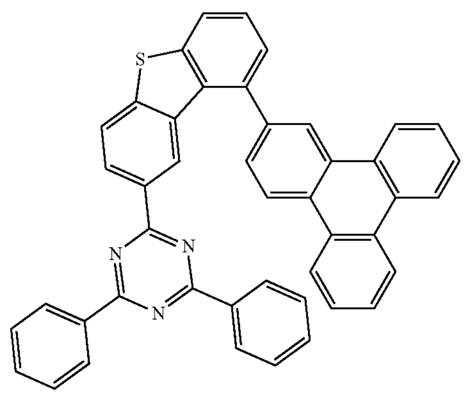

-continued
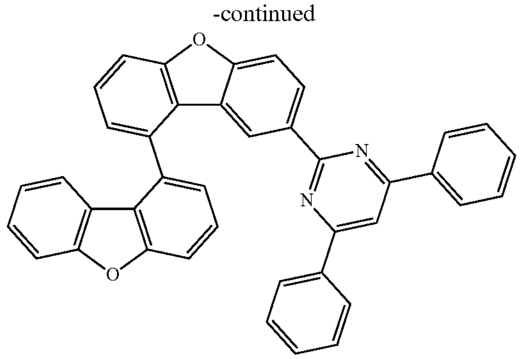
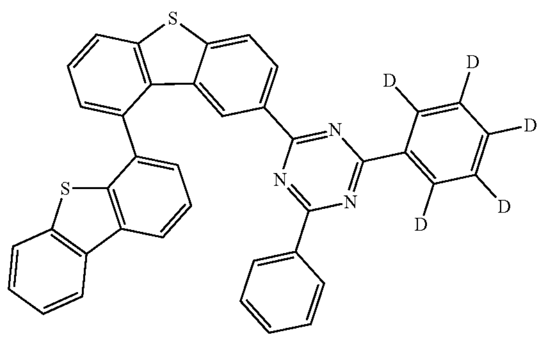
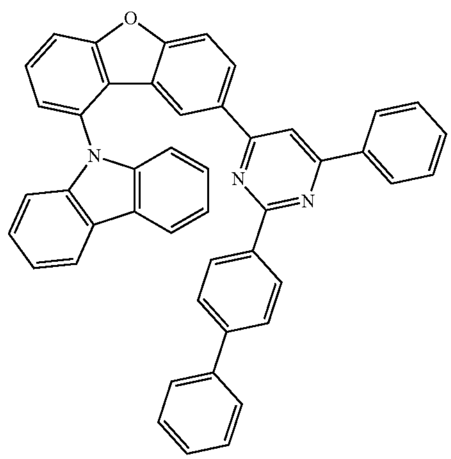
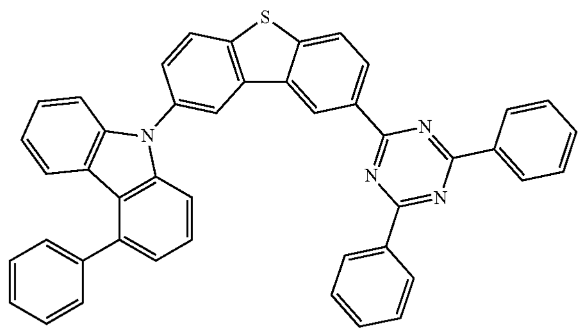
-continued
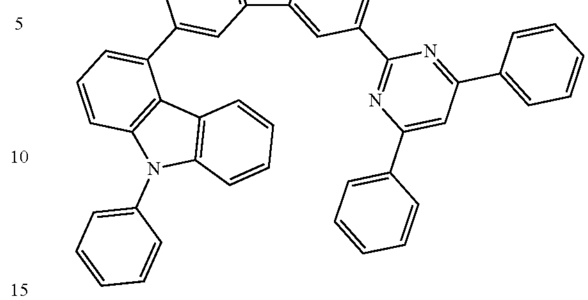
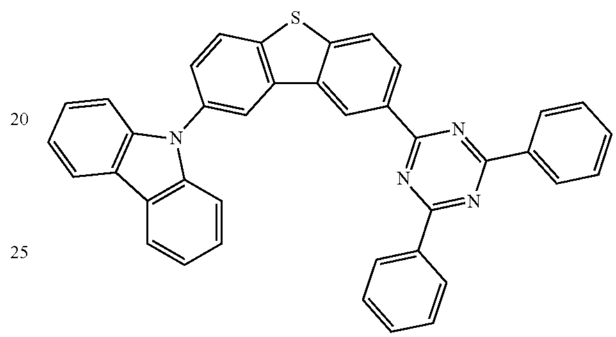
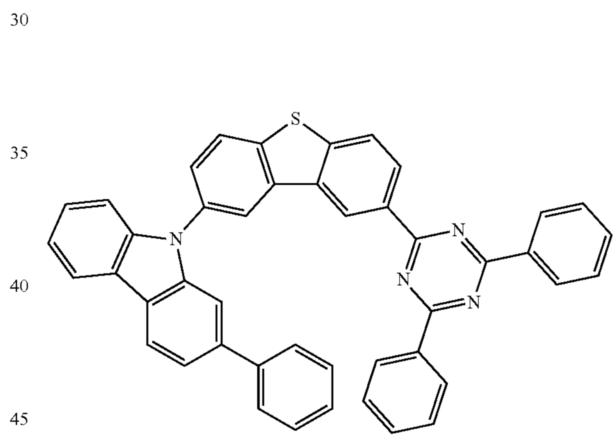
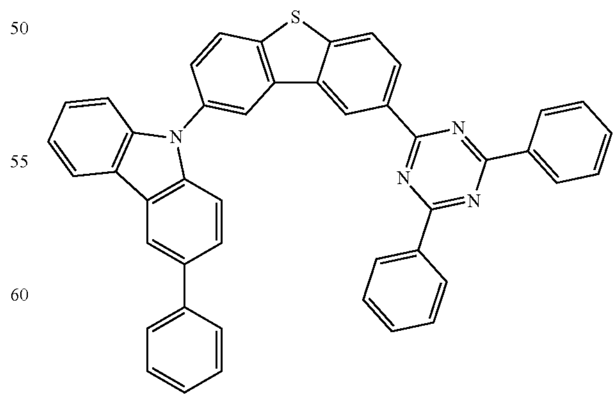

-continued
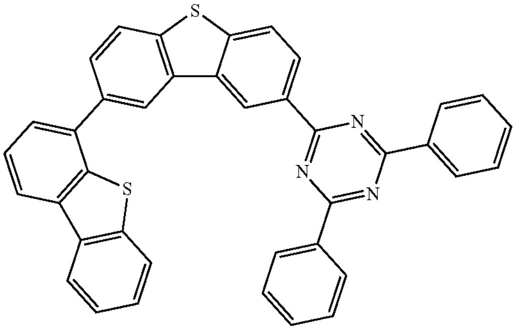
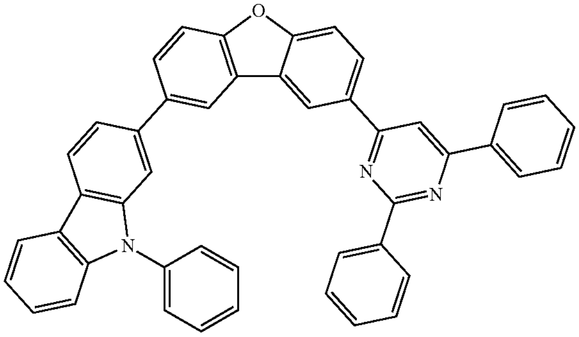
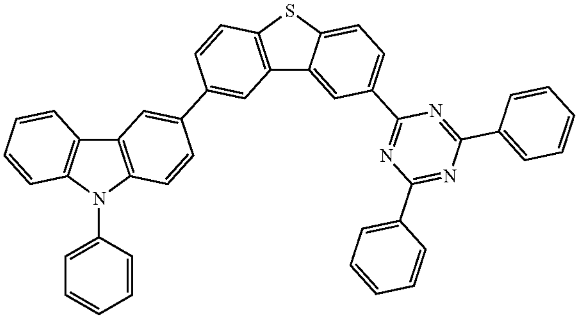
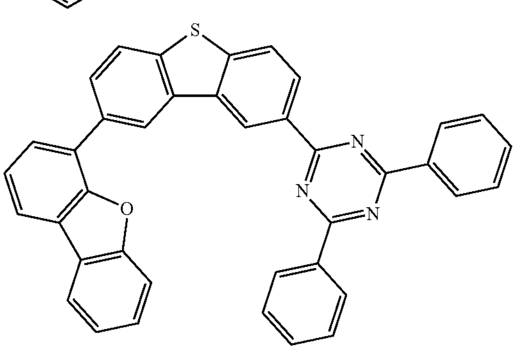
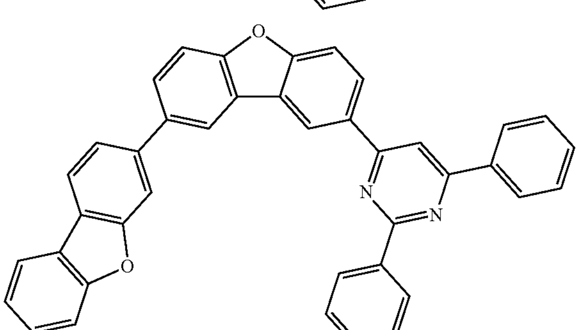
-continued
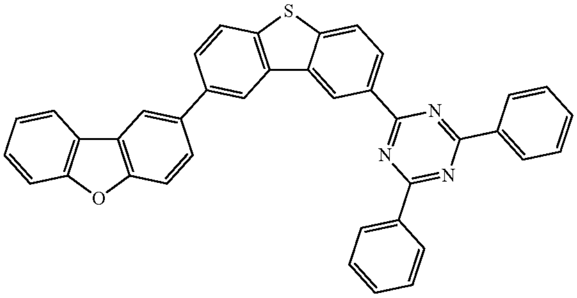
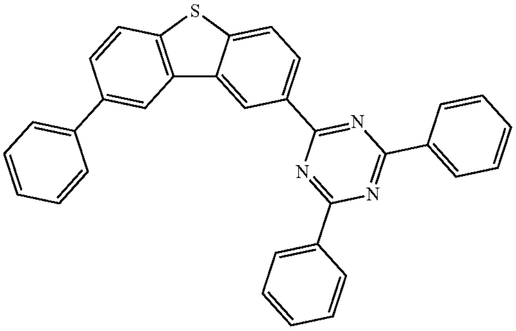
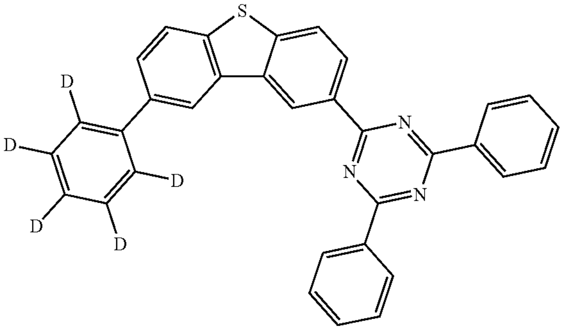
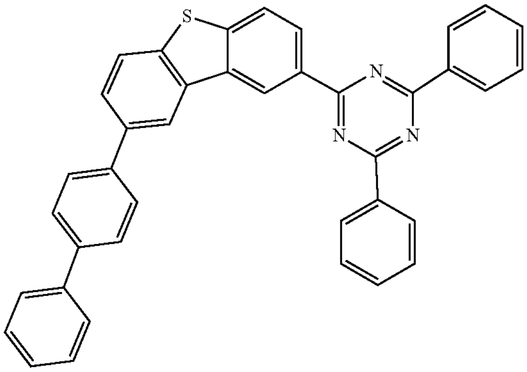
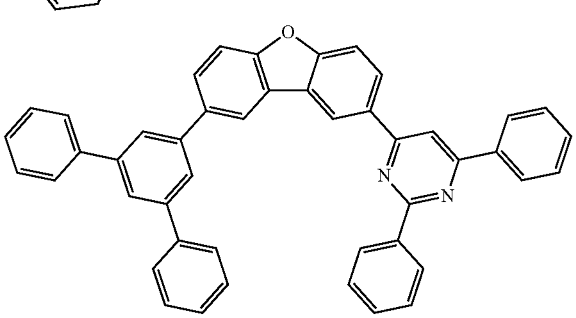

-continued
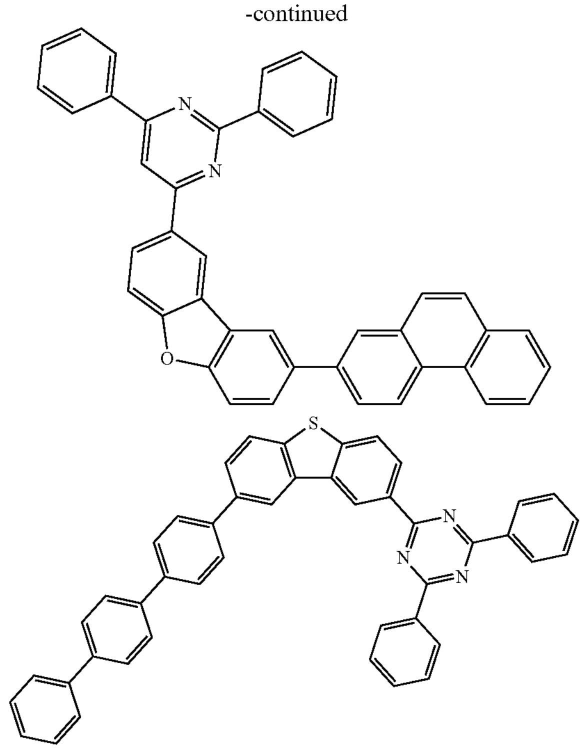
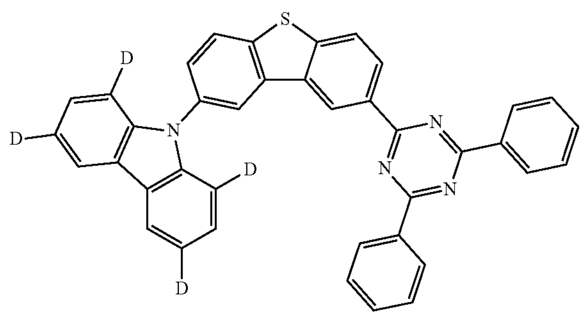
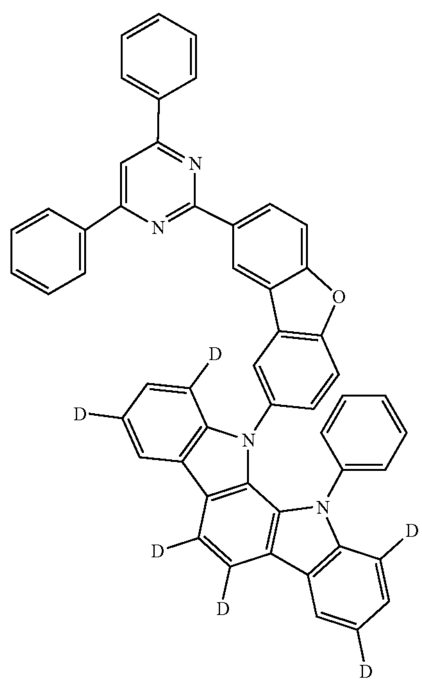
-continued
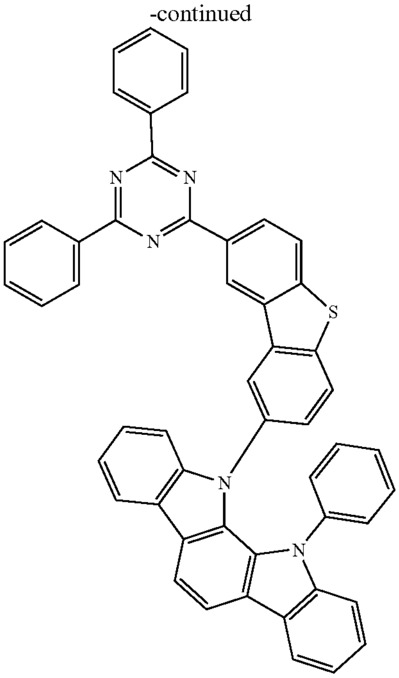
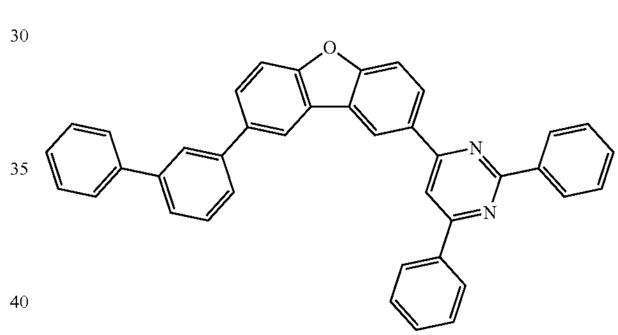
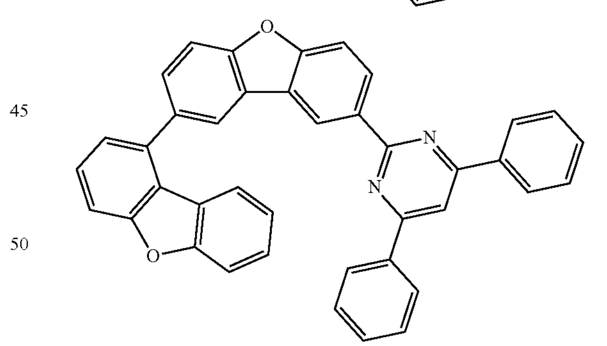
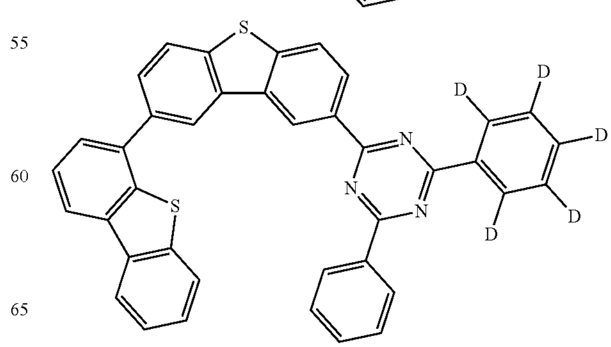

-continued
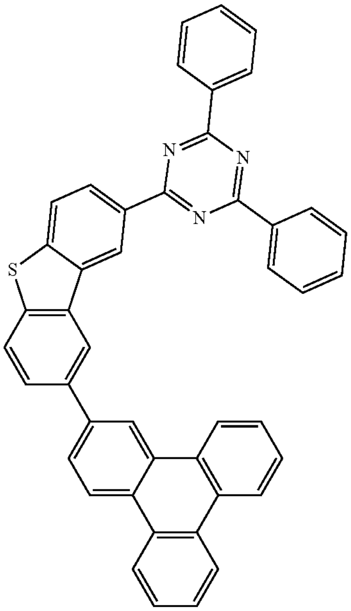
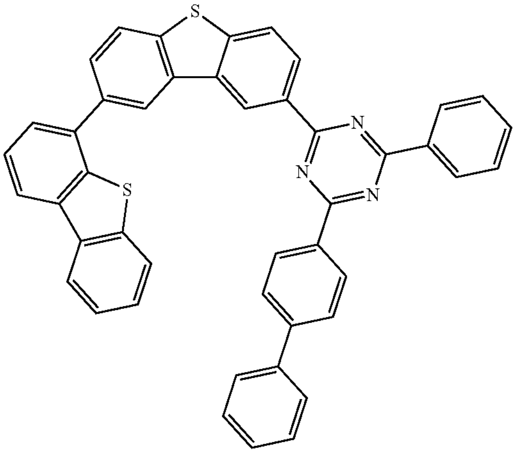
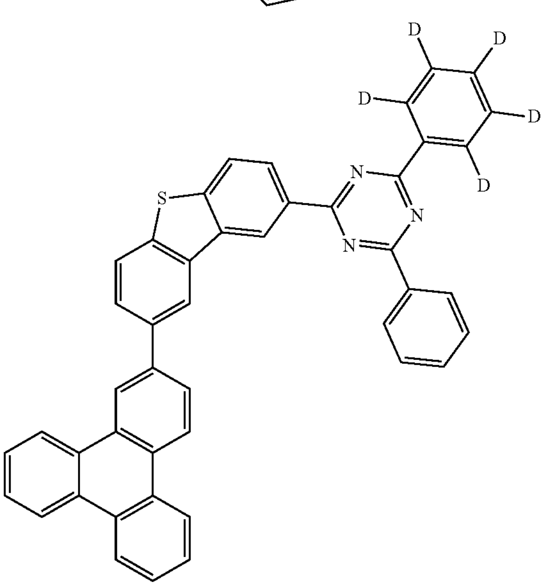
-continued
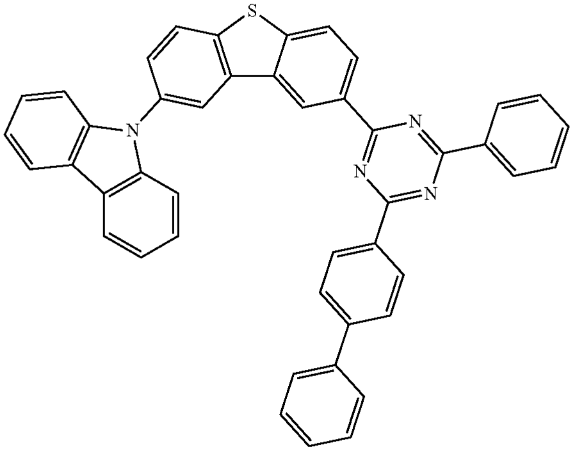
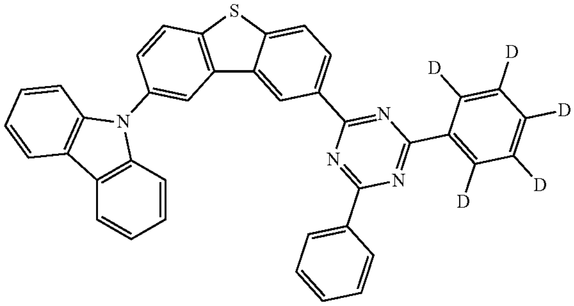
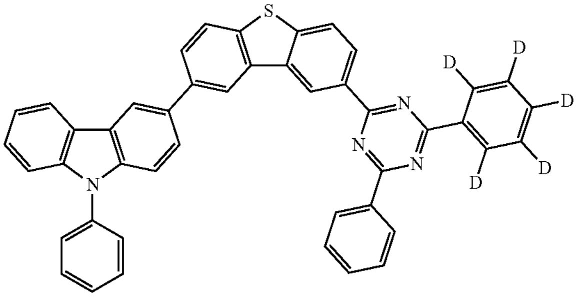
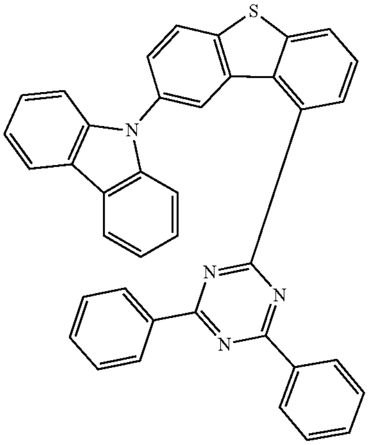

-continued
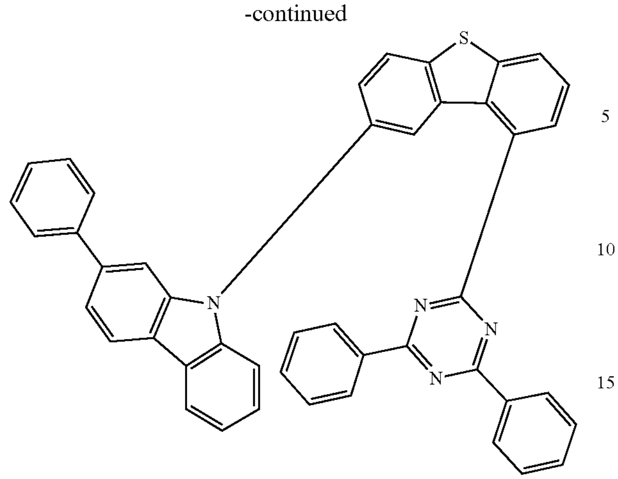
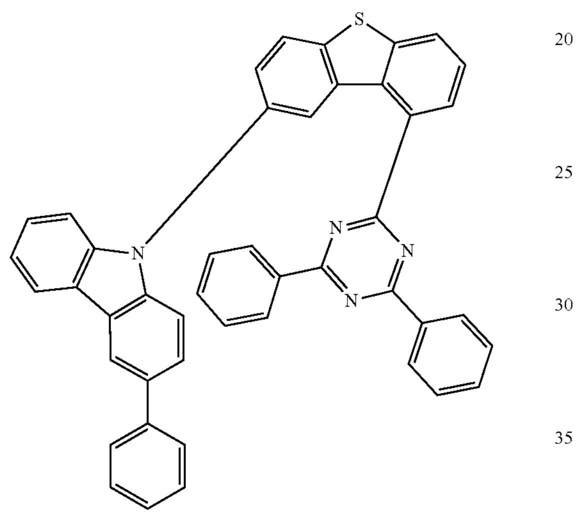
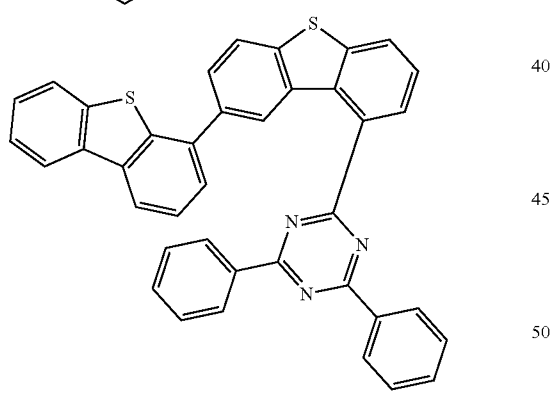
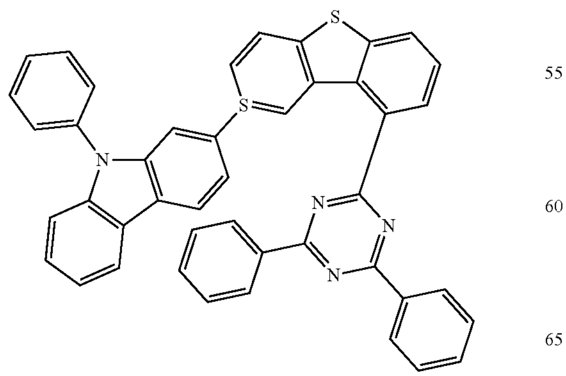
-continued
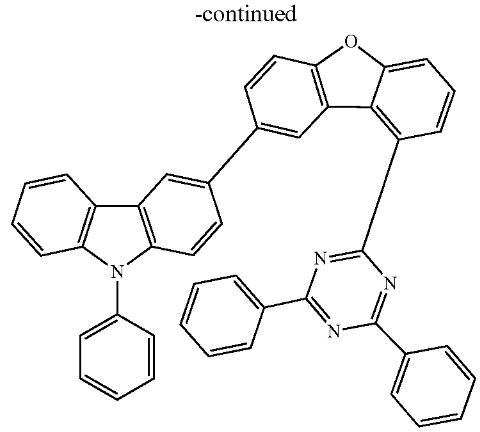
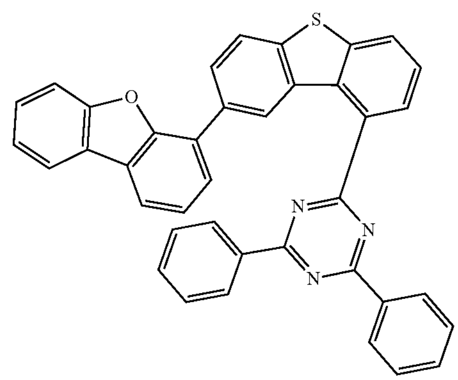
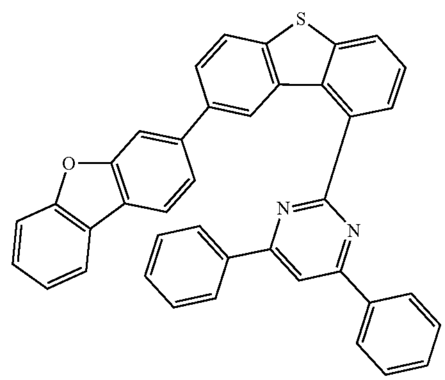
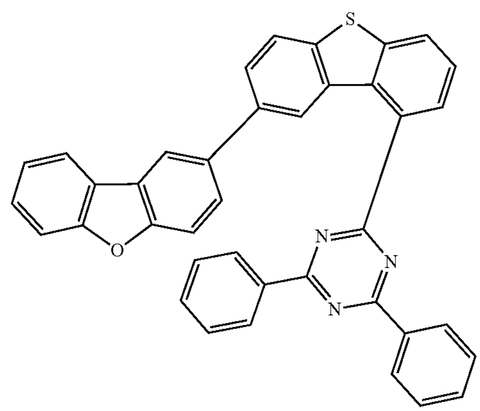

-continued
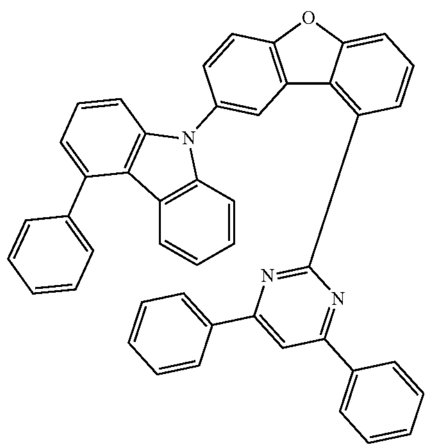
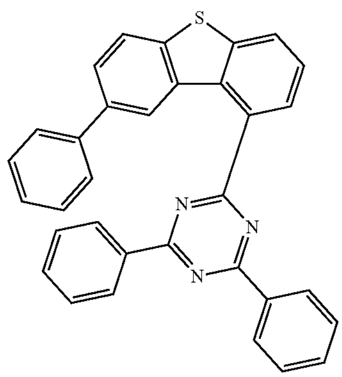
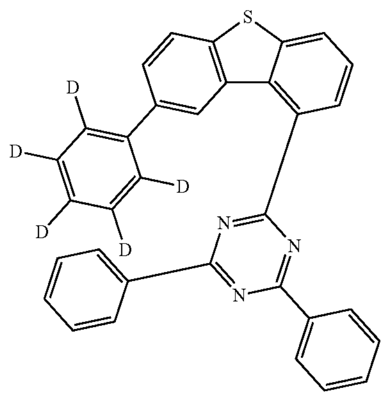
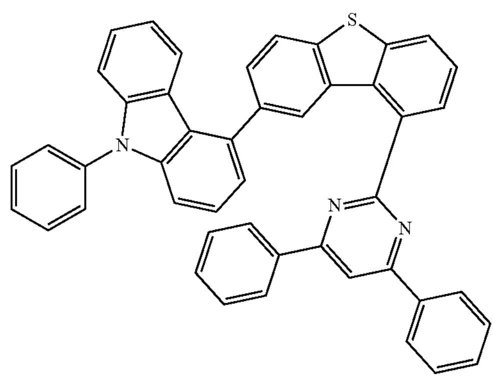
-continued
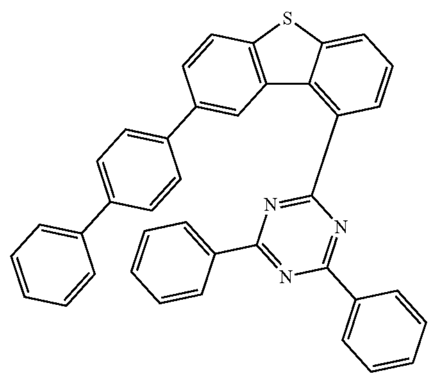
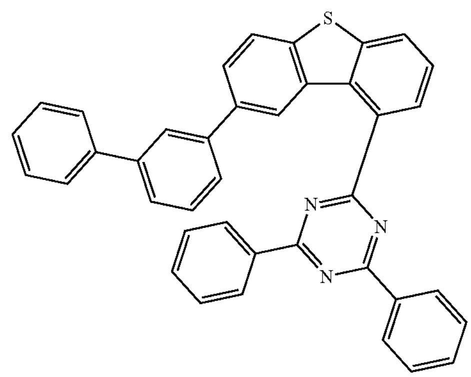
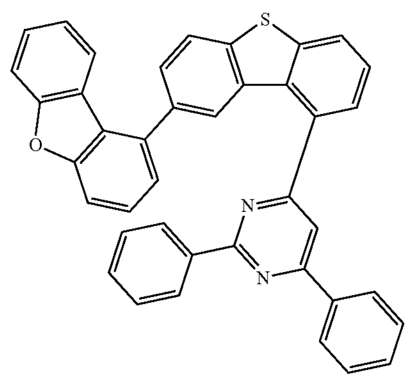
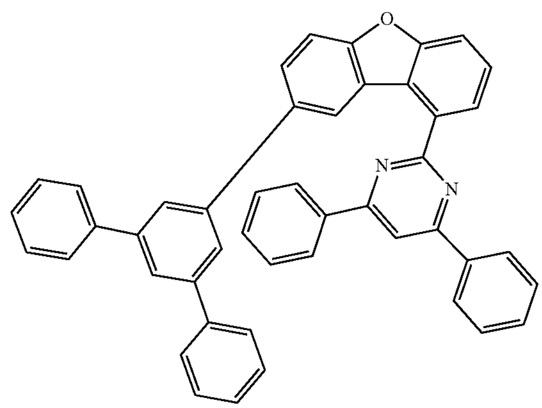

-continued
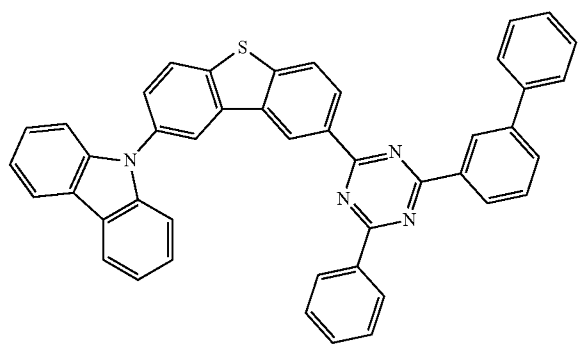
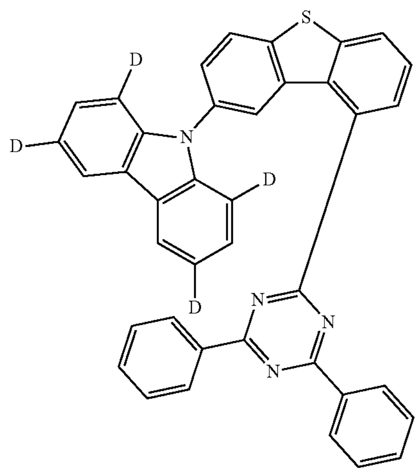
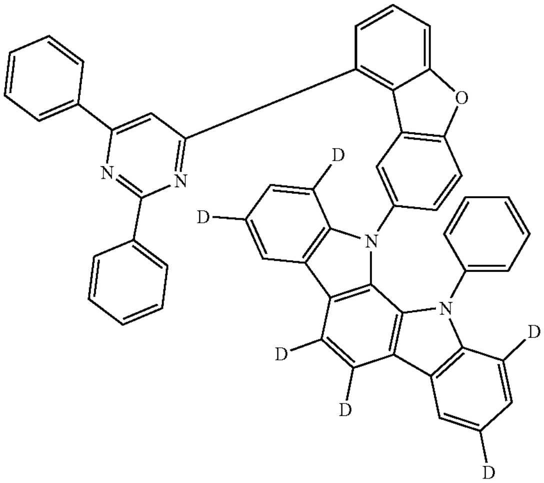
-continued
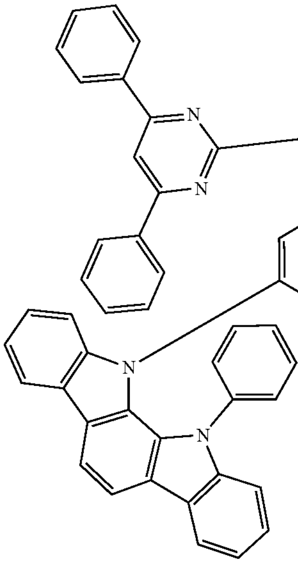
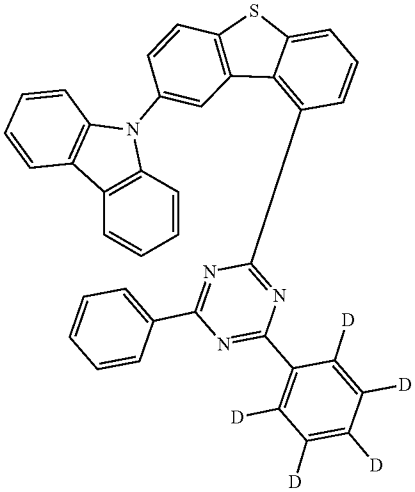
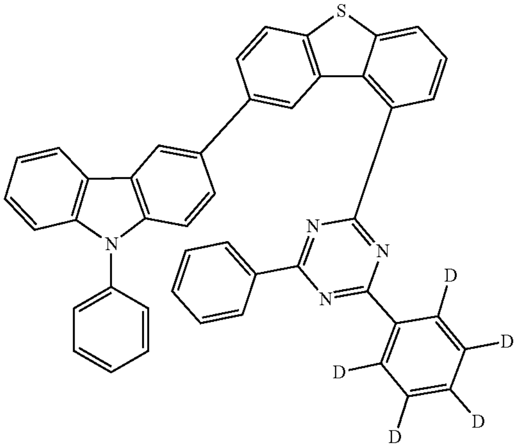

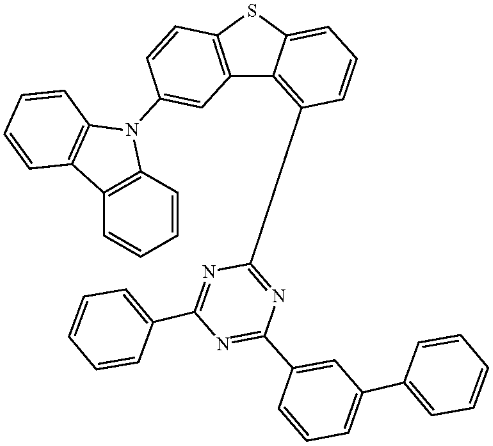
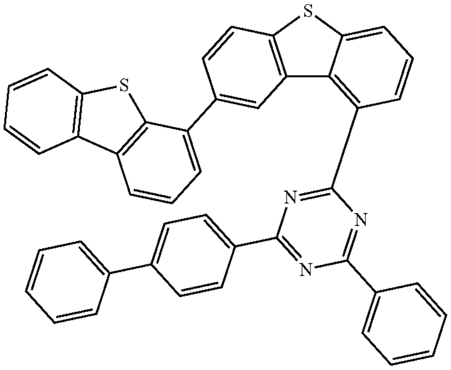
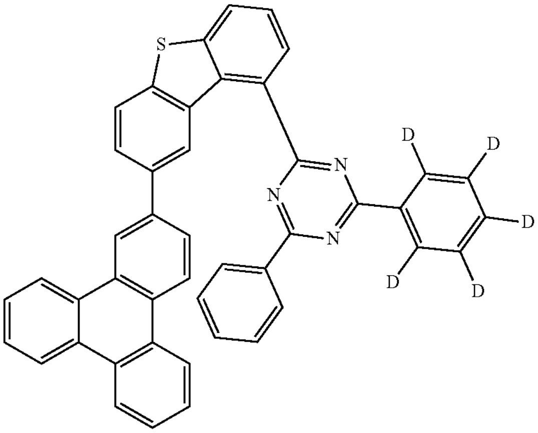
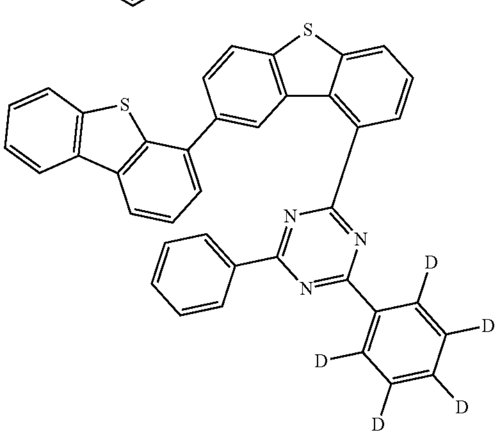
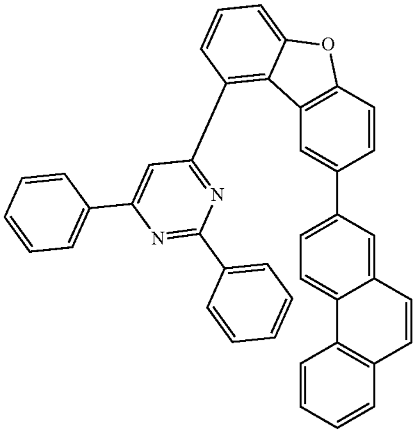
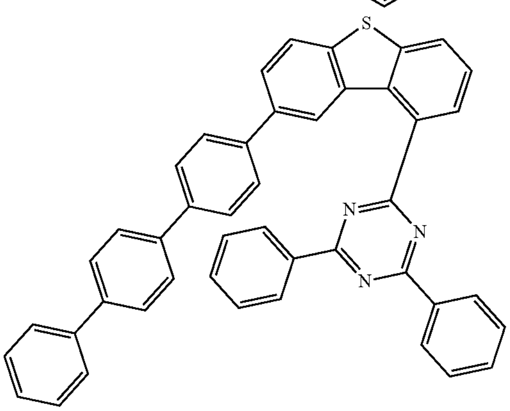
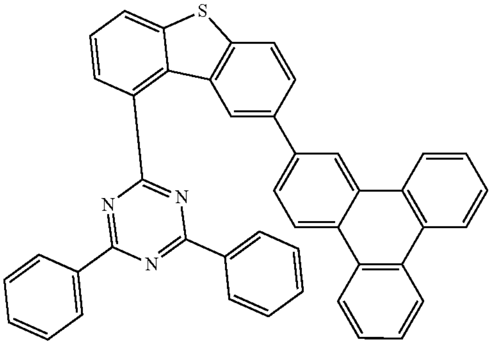
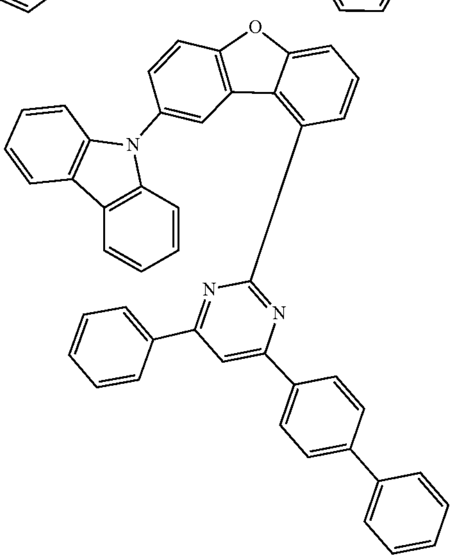

-continued
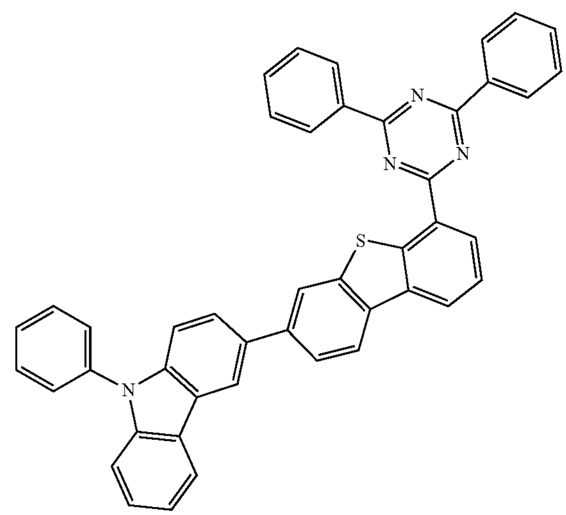
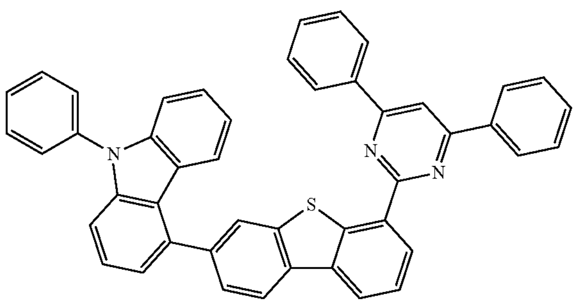
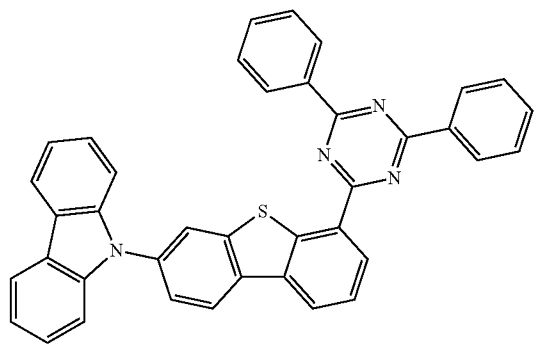
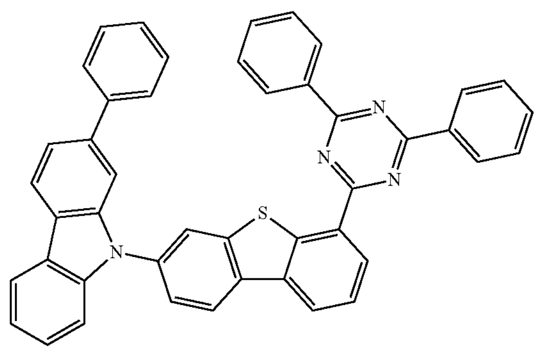
-continued
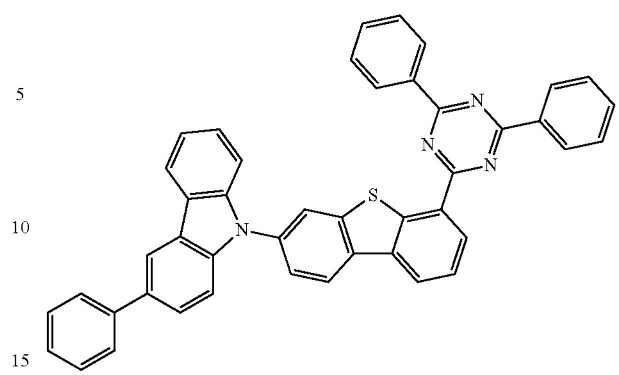
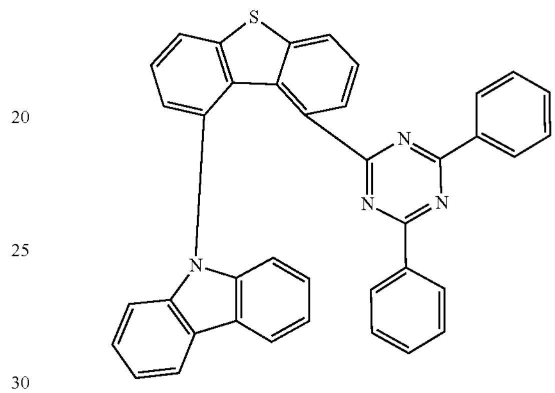
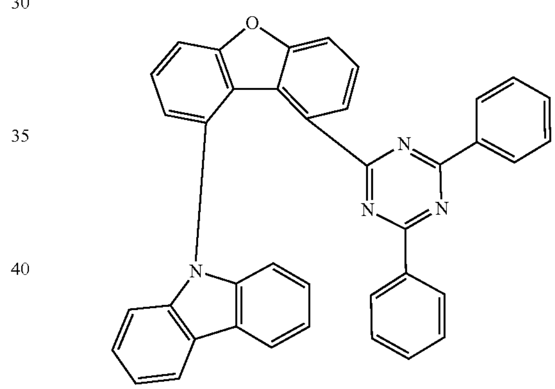
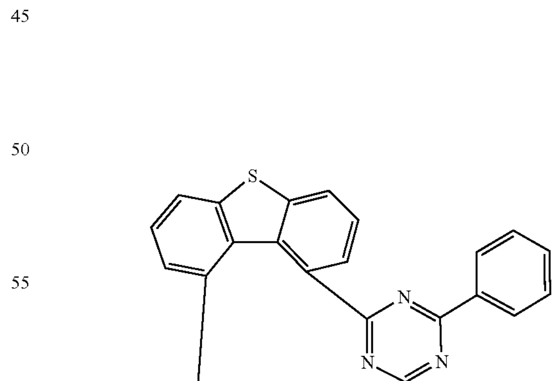
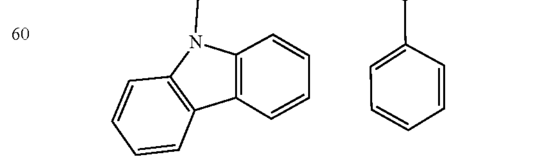

-continued
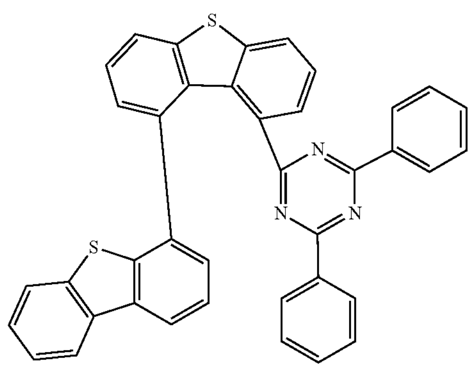
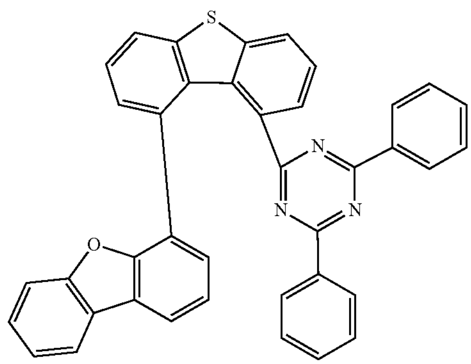
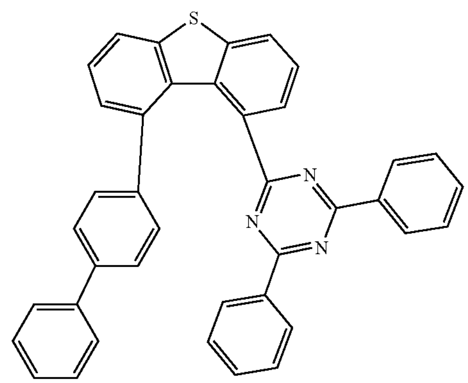
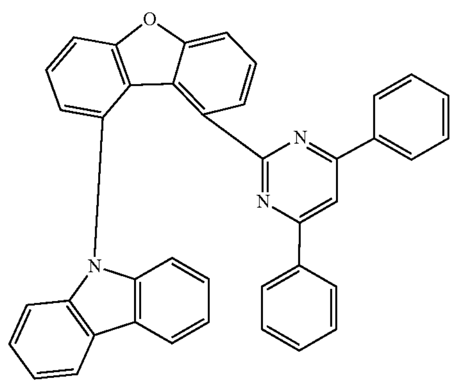
-continued
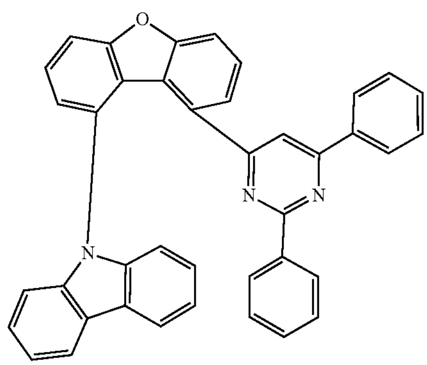
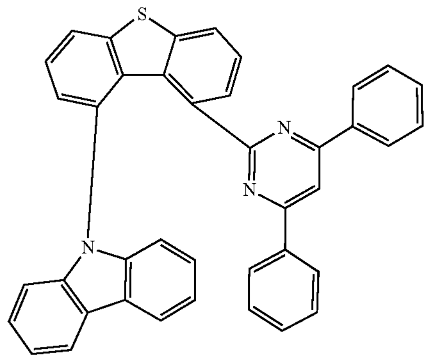
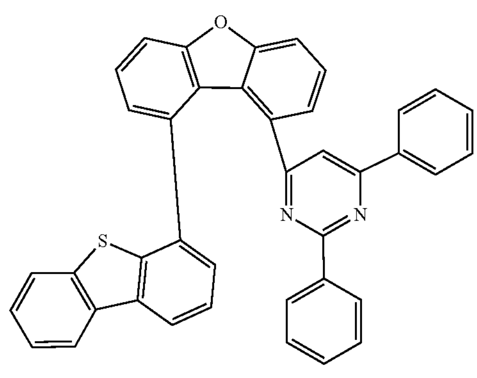
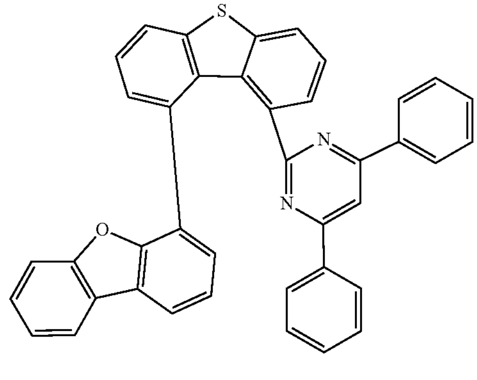

-continued
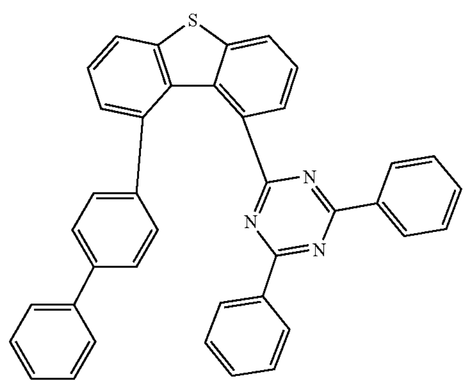
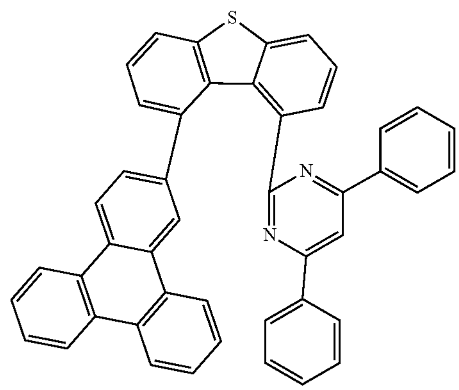
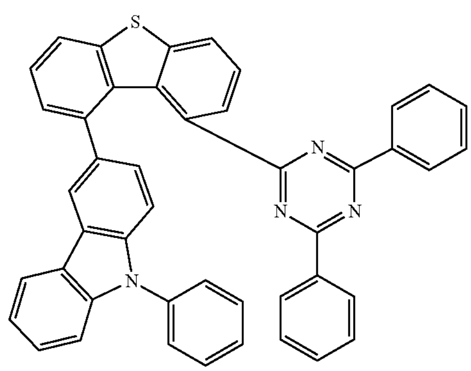
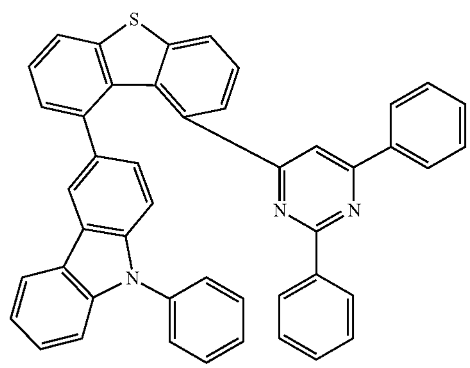
-continued
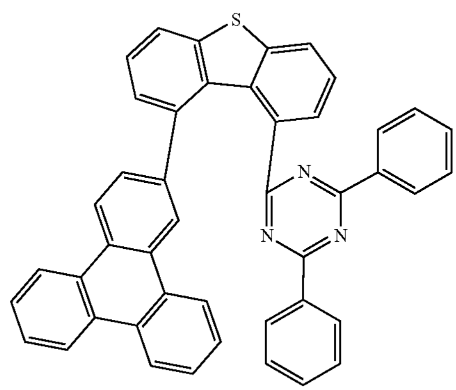
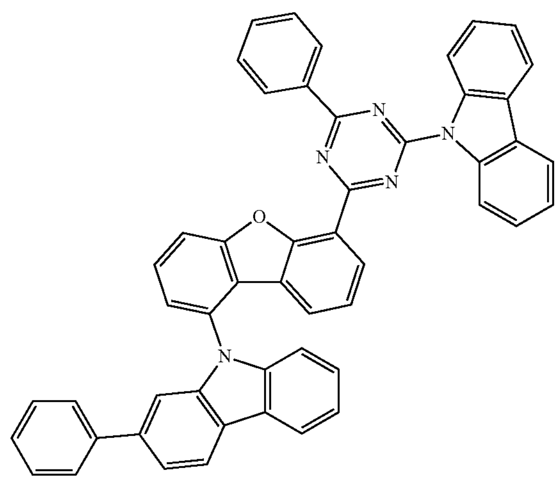
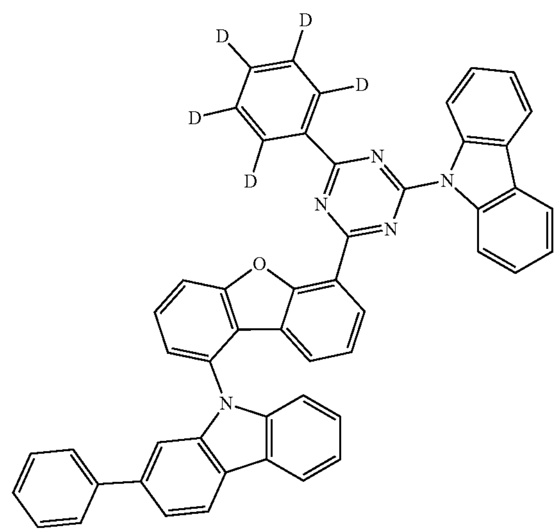

-continued
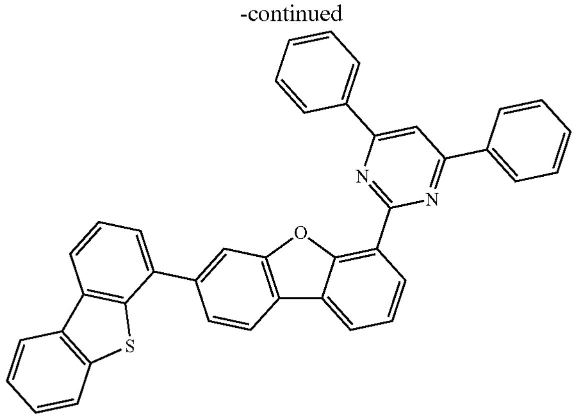
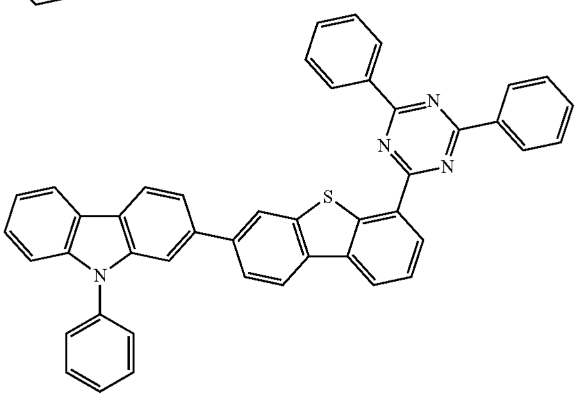
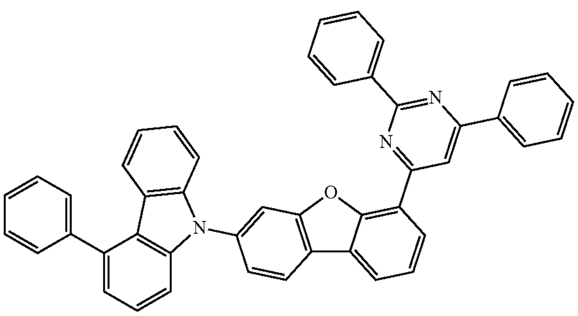
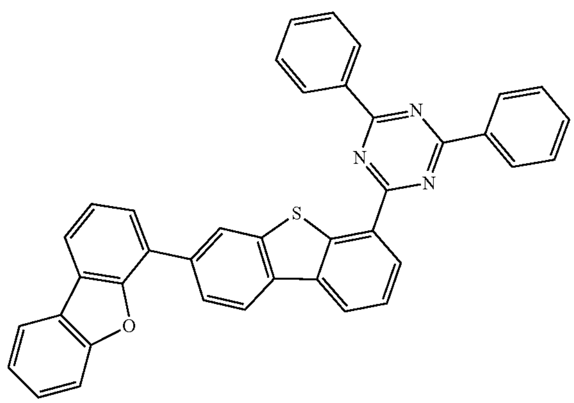
-continued
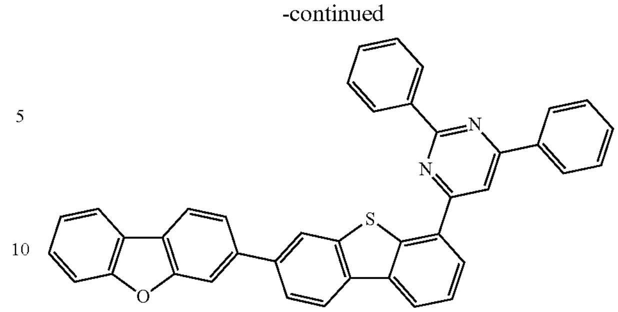
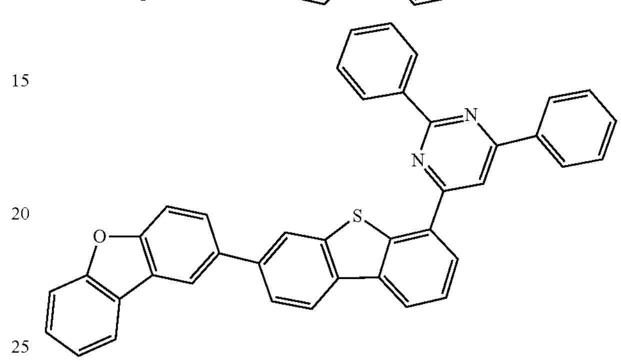
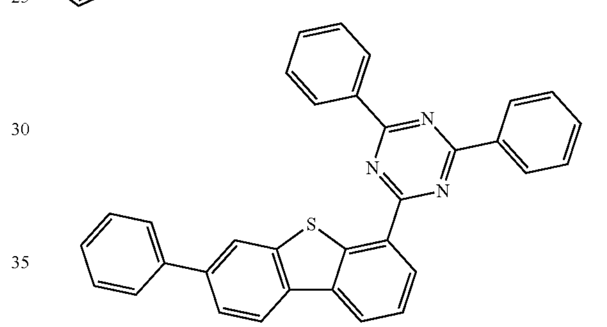
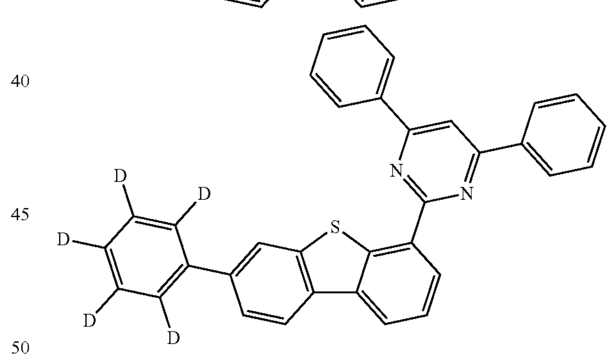
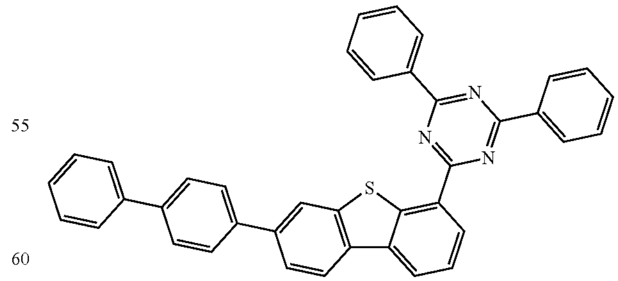
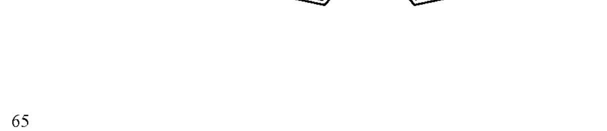

-continued
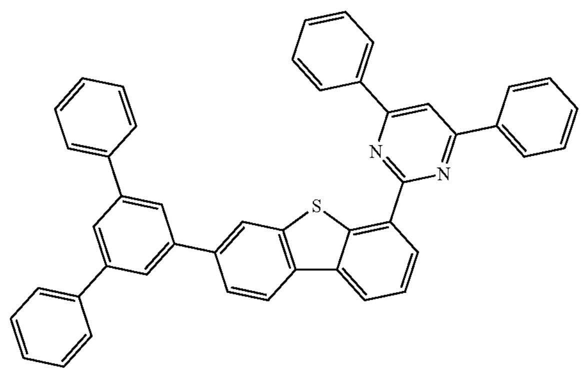
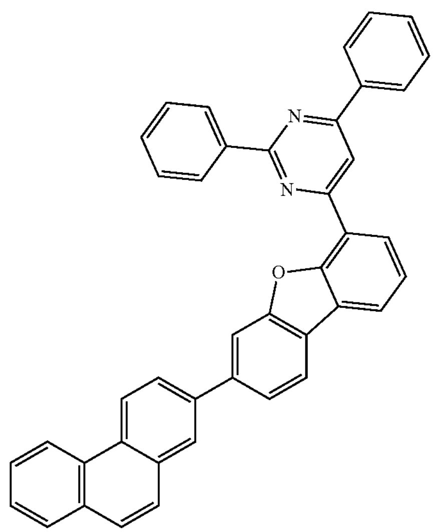
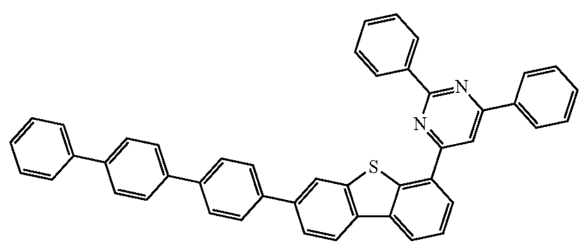
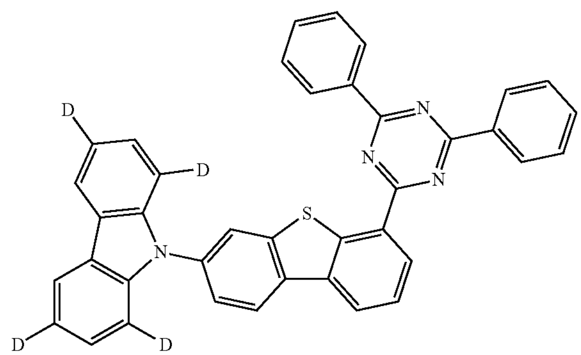
-continued
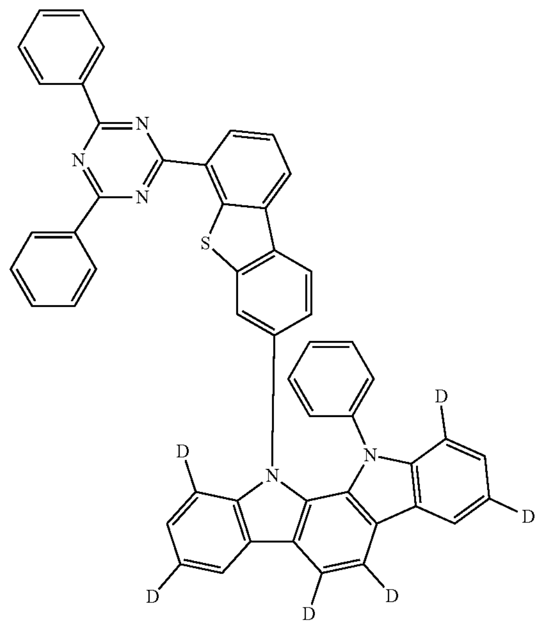
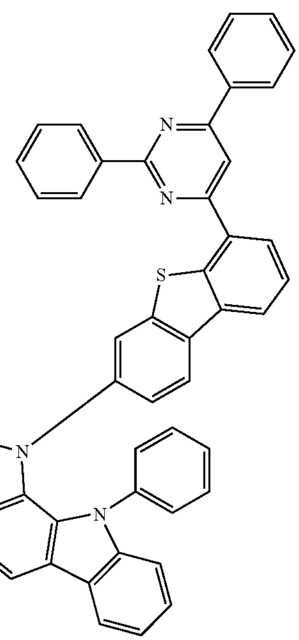
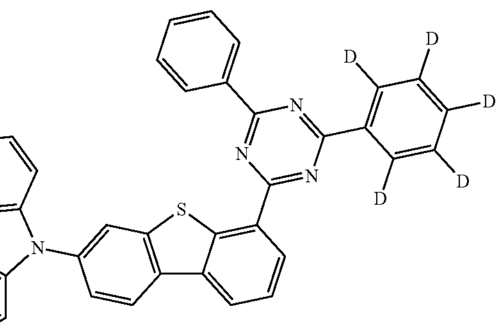

-continued
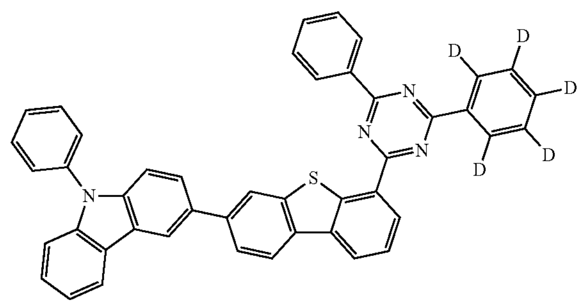
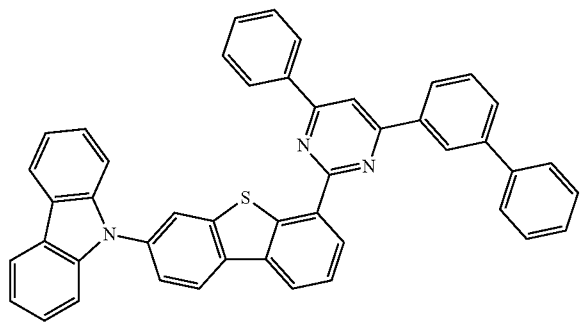
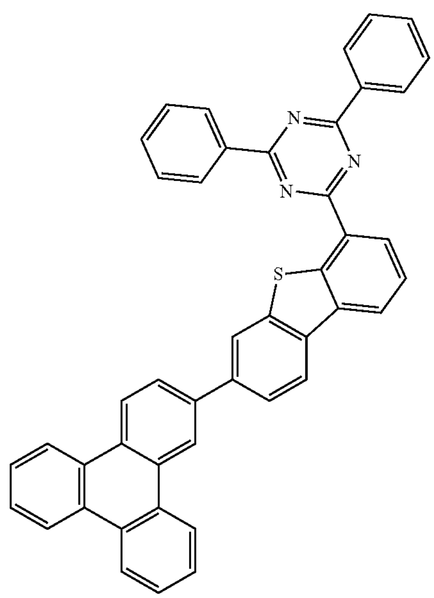
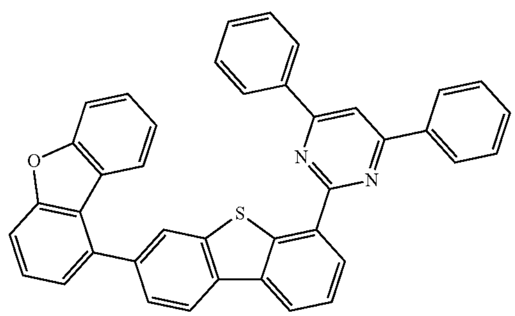
-continued
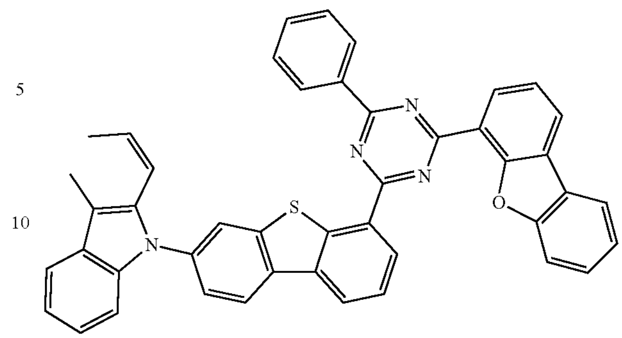
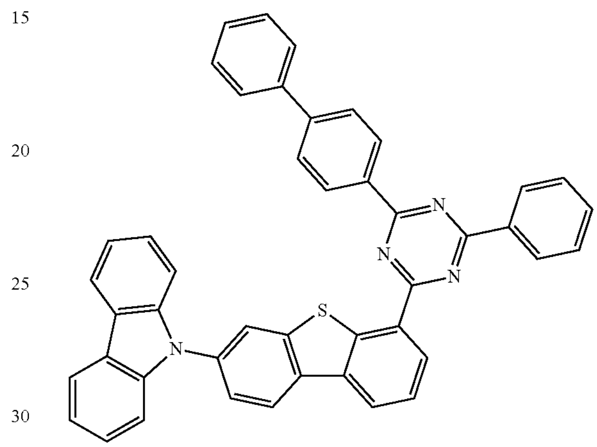
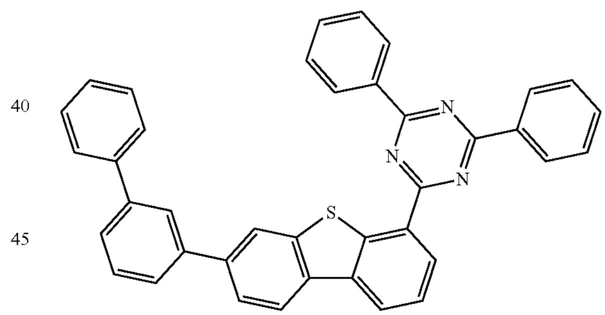
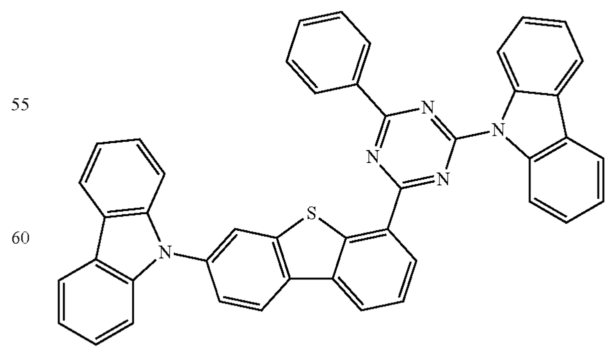

-continued
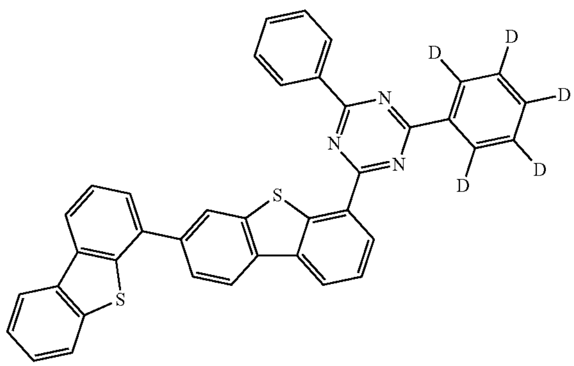
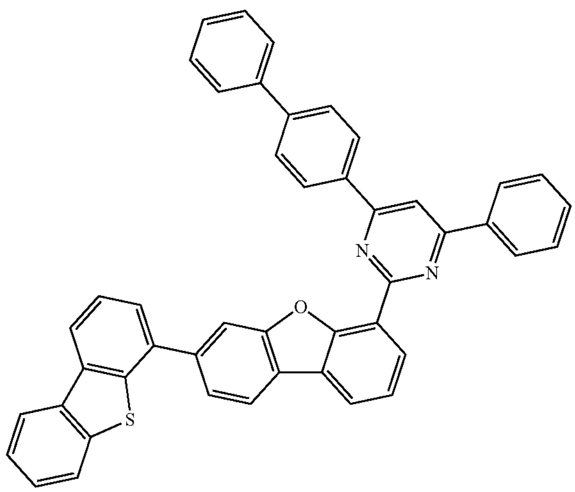
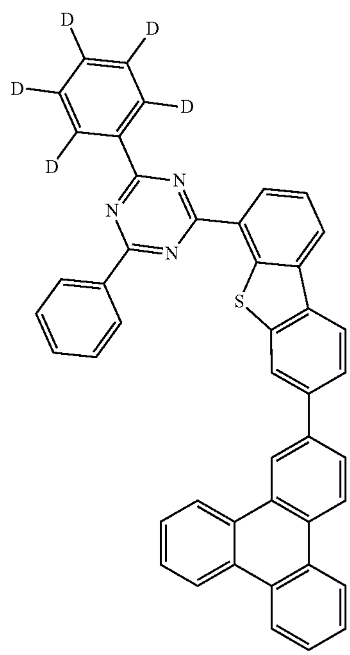
-continued
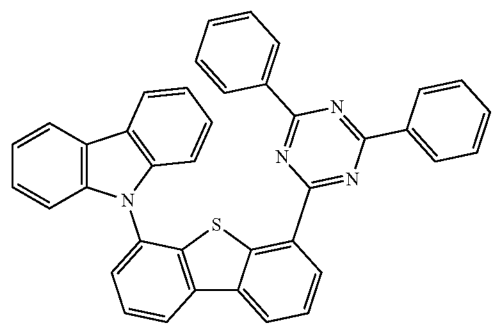
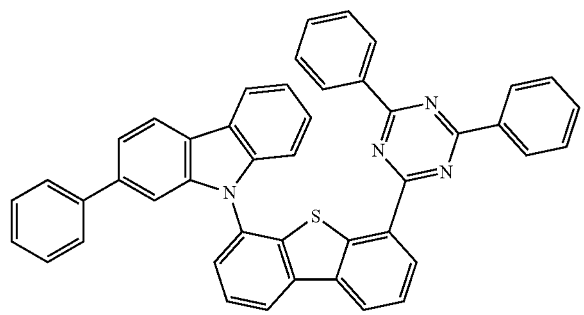
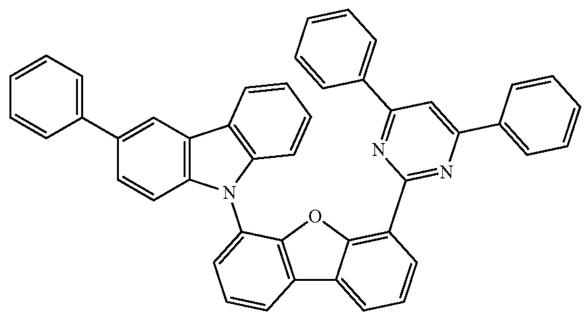
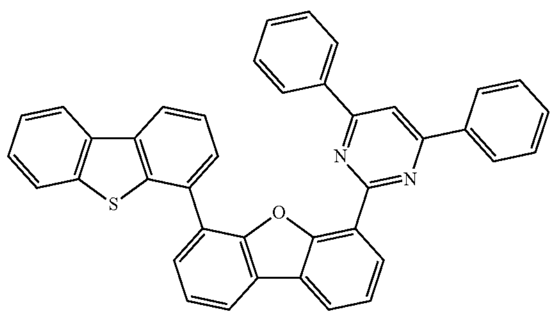
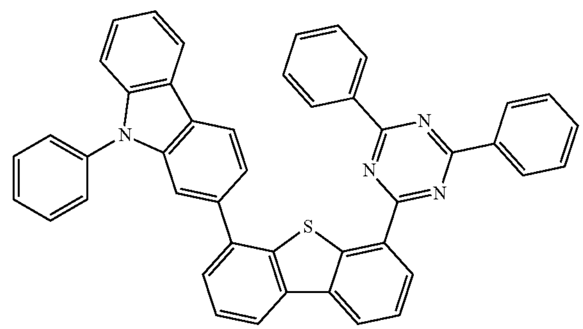

-continued
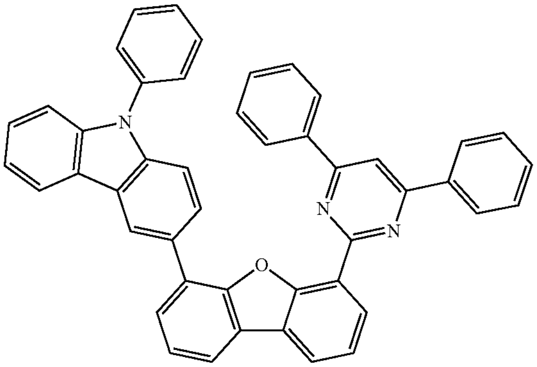
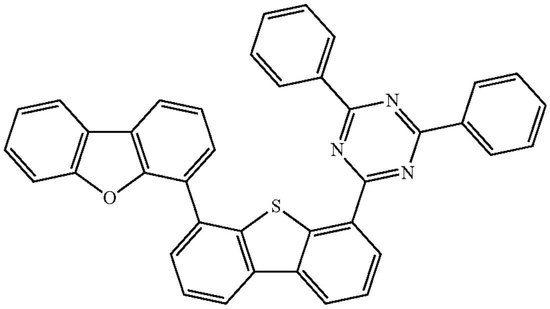
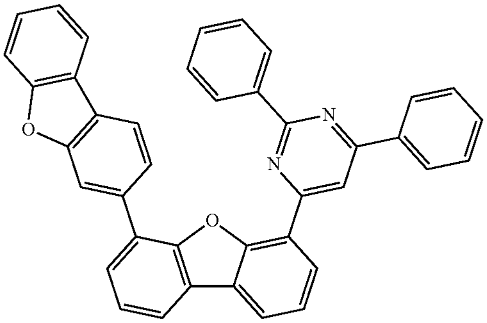
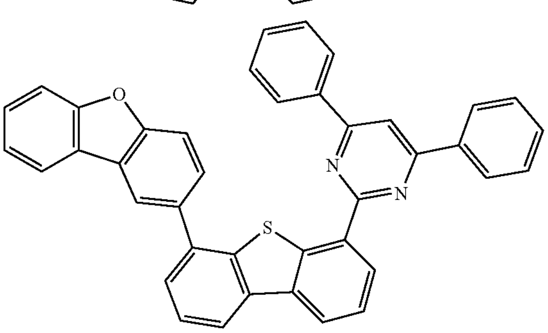
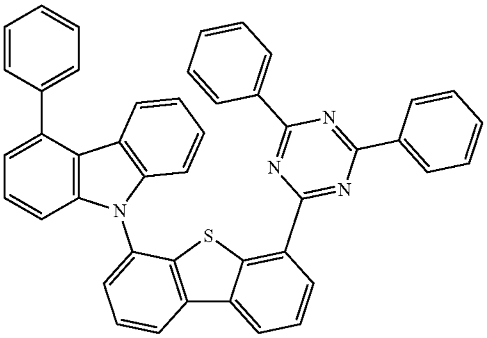
-continued
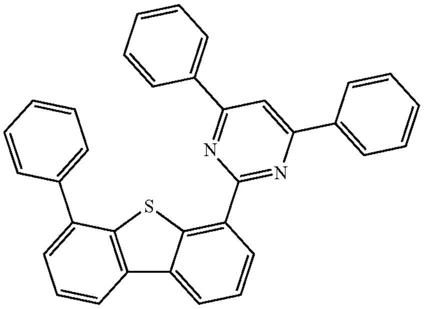
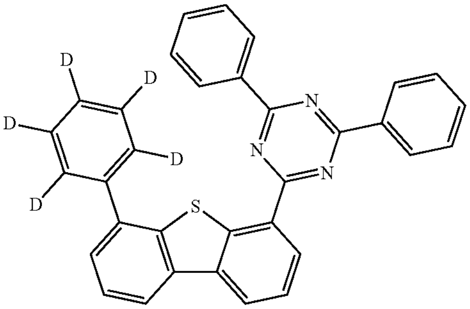
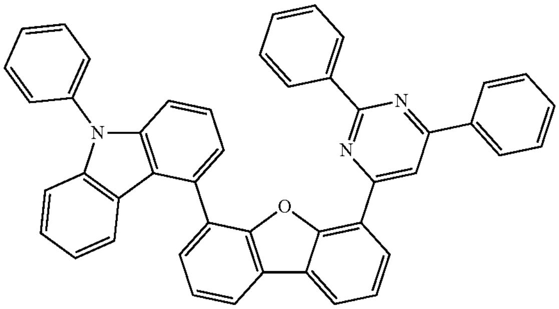
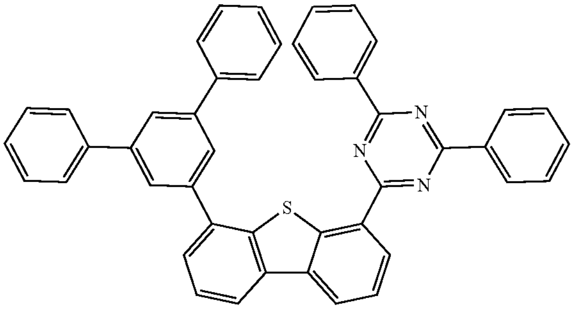
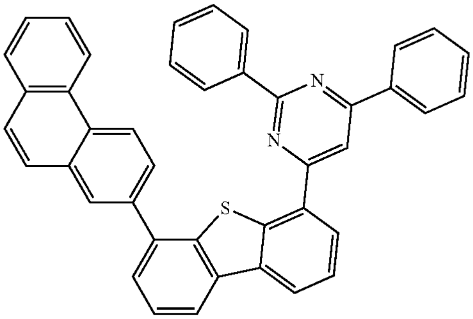

-continued
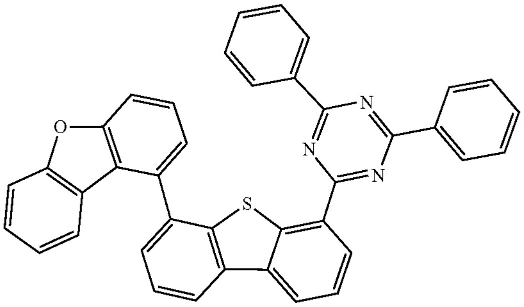
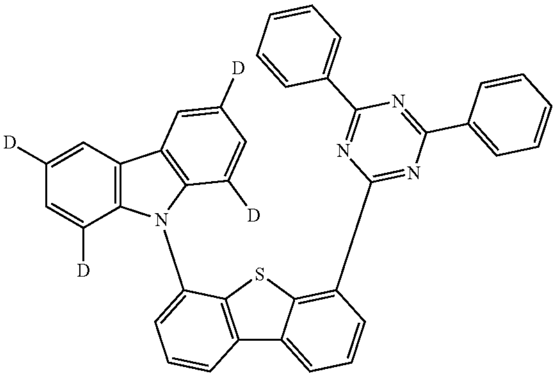
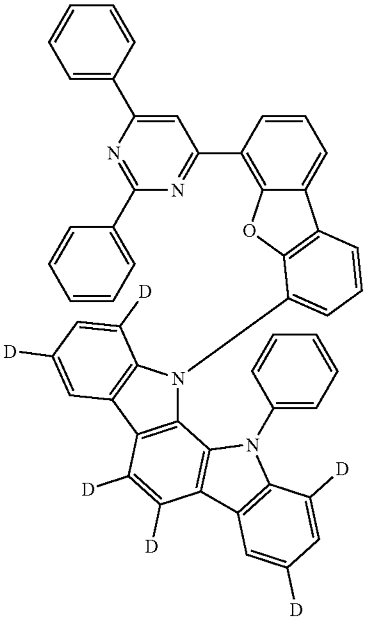
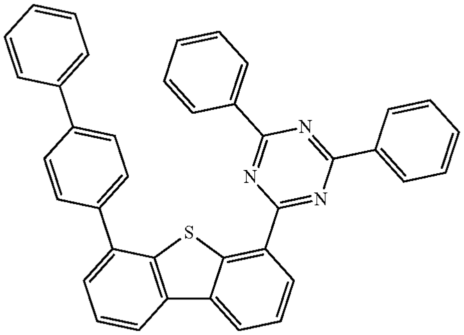
-continued
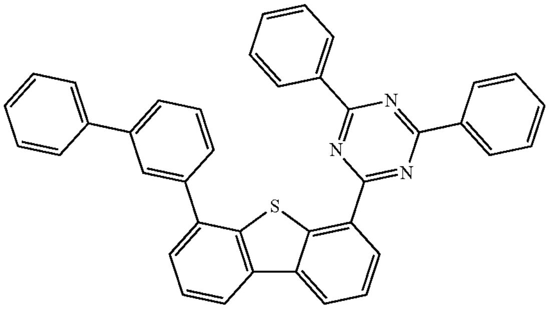
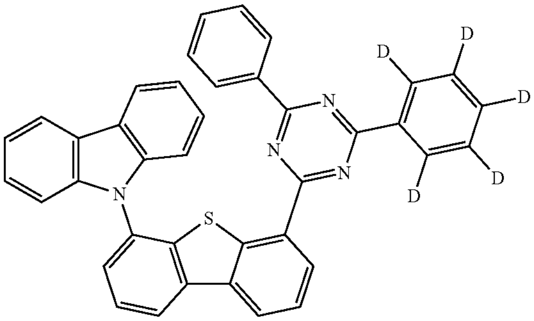
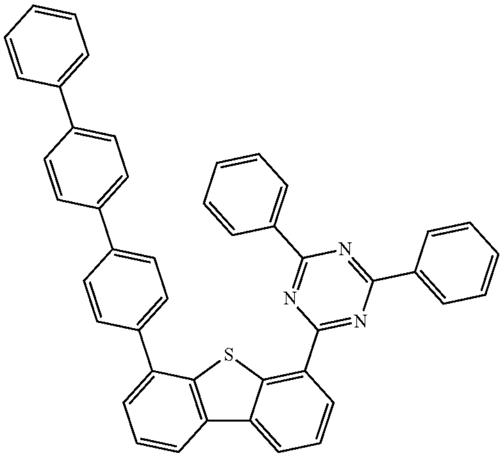
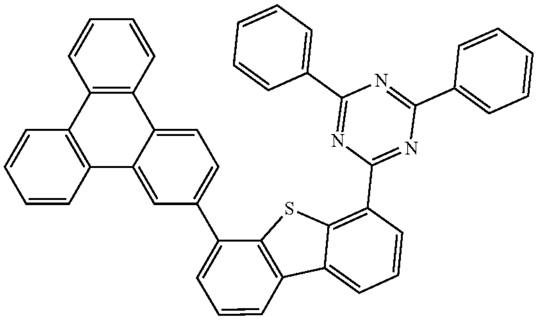

-continued
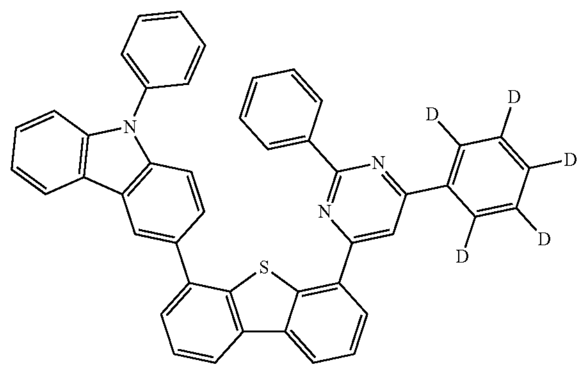
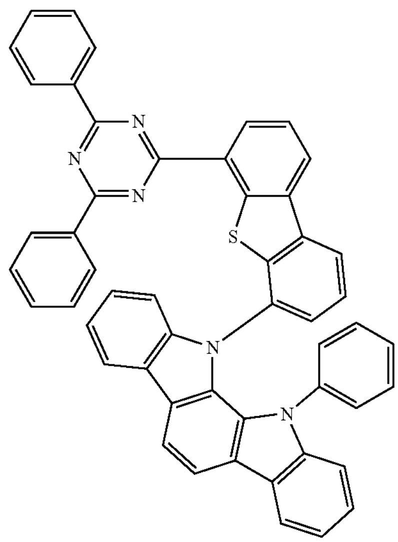
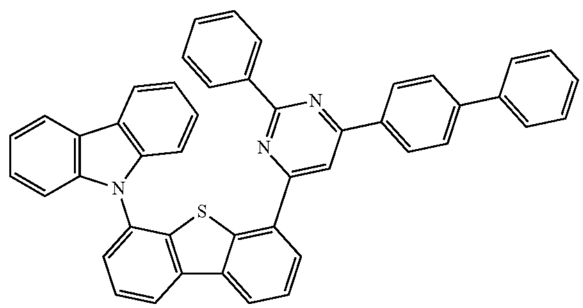
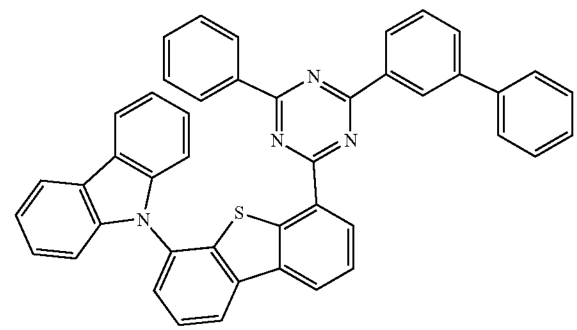
-continued
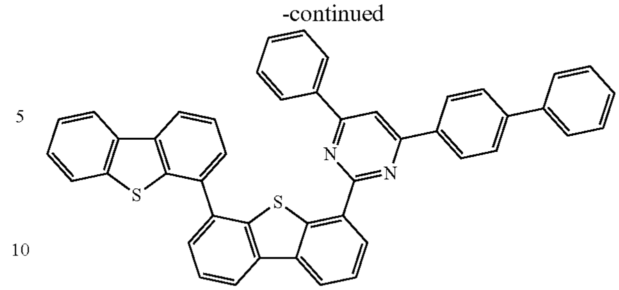
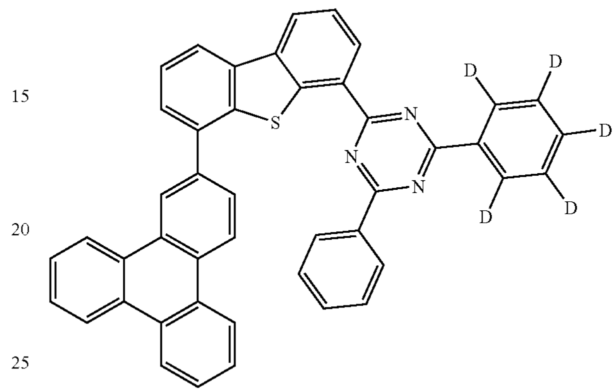
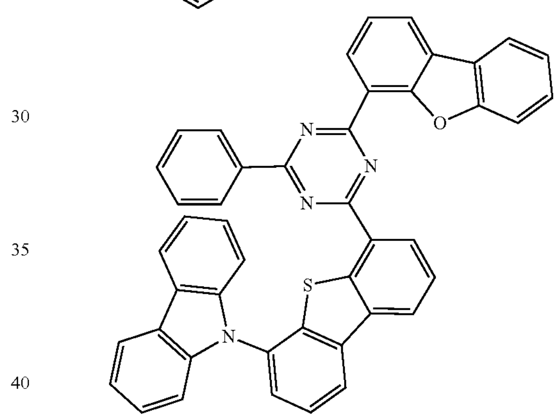
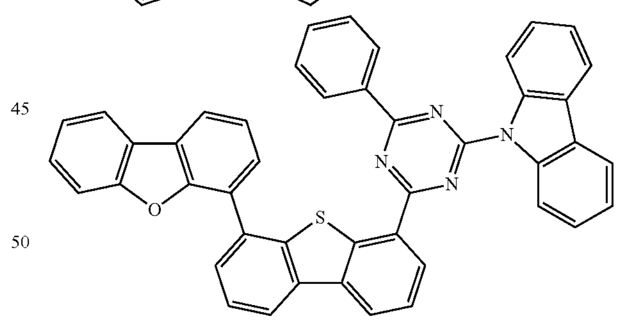
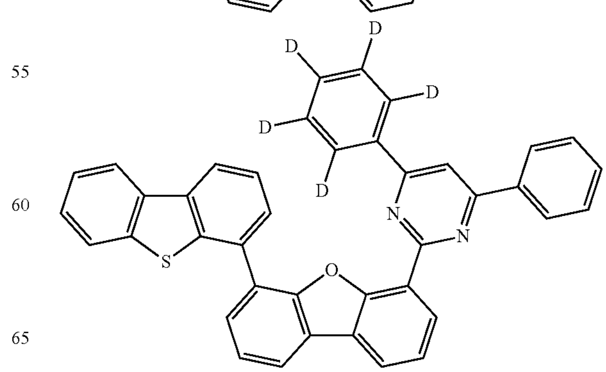

-continued
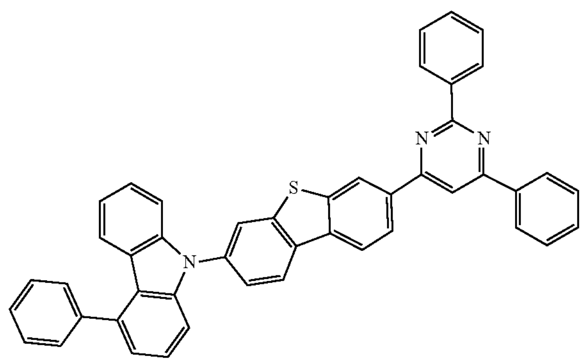
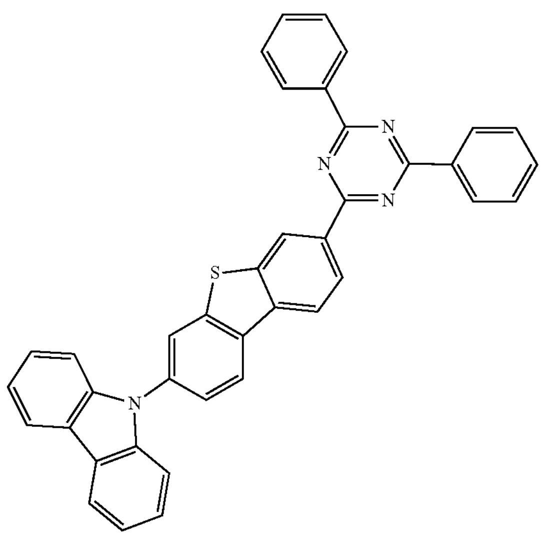
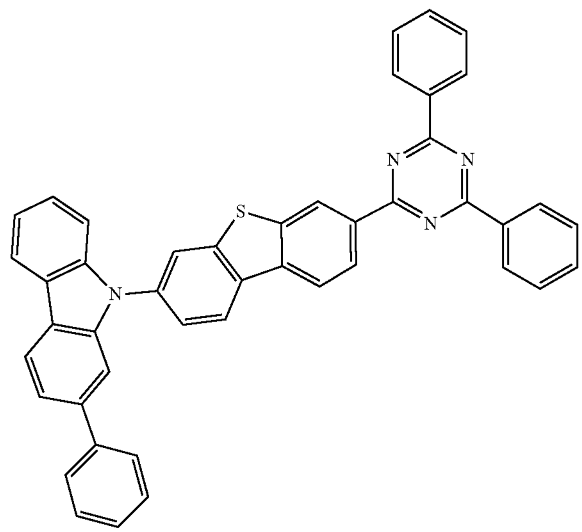
-continued
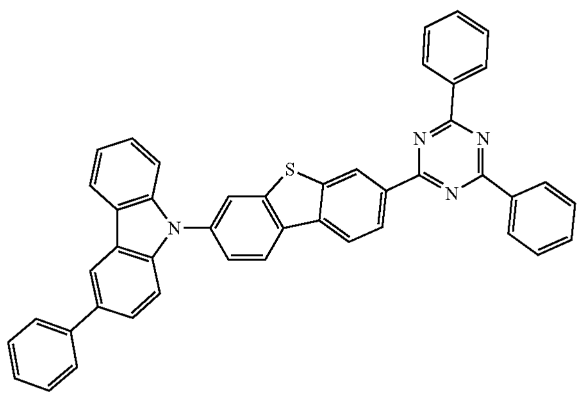
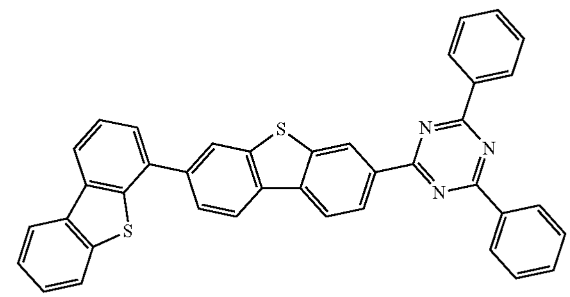
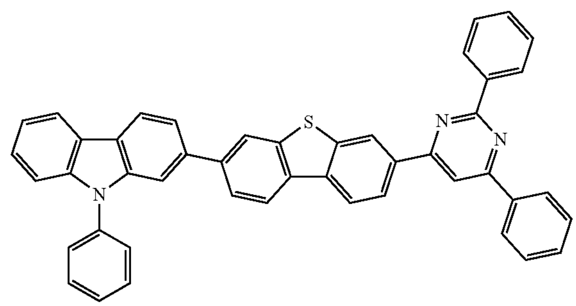
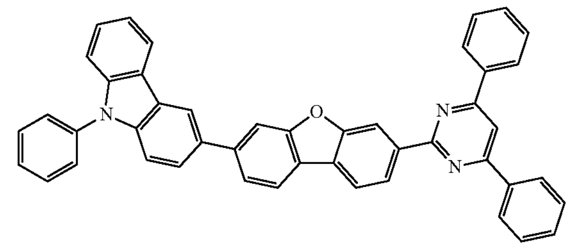
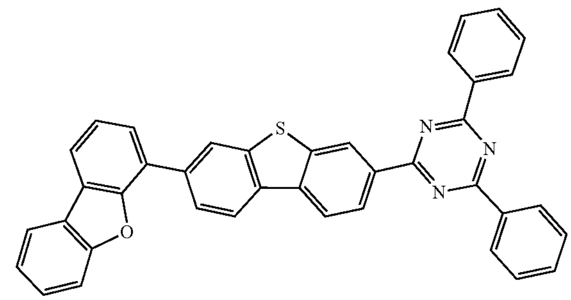

-continued
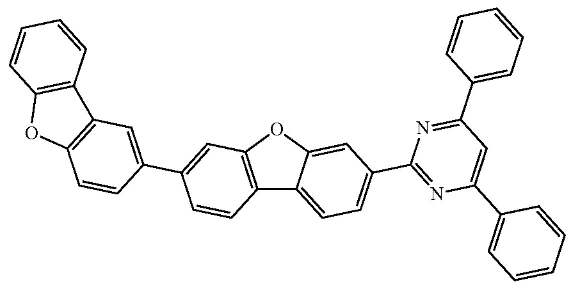
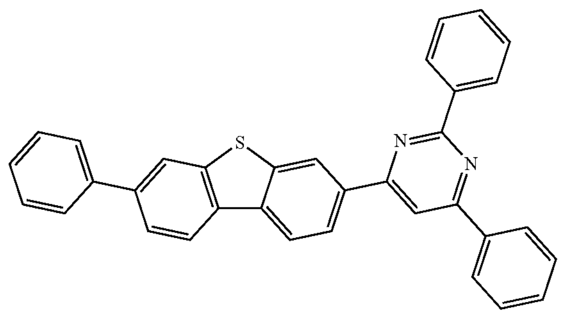
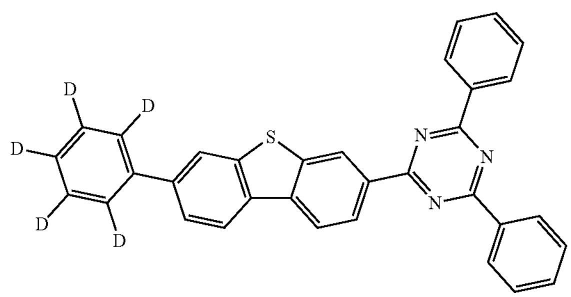
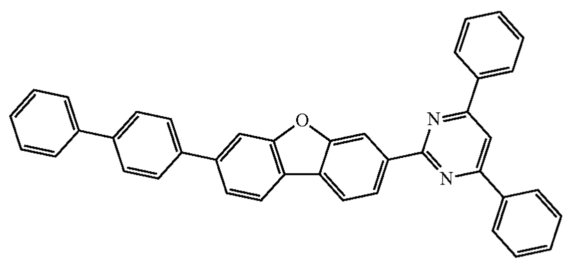
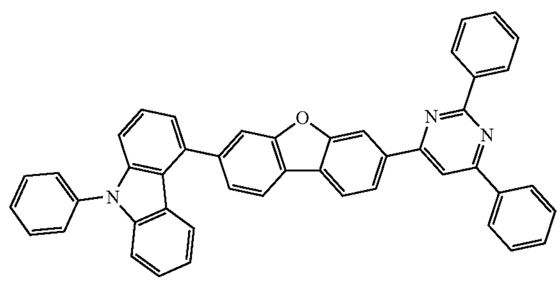
-continued
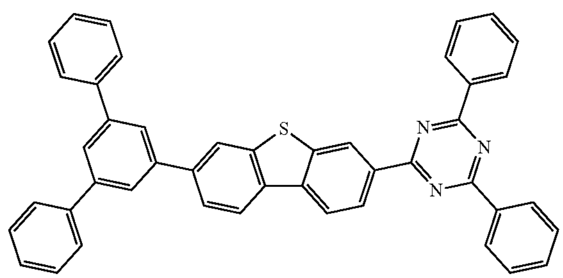
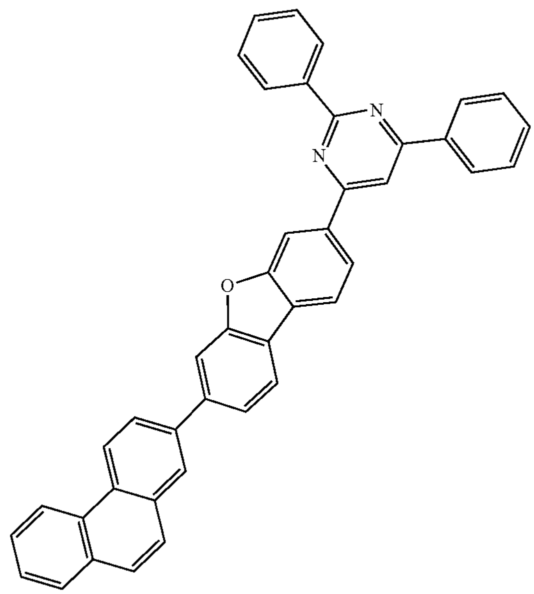
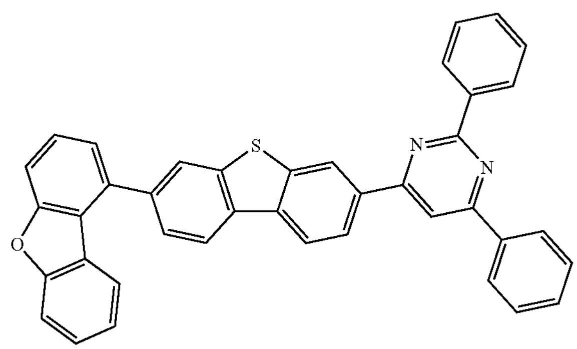
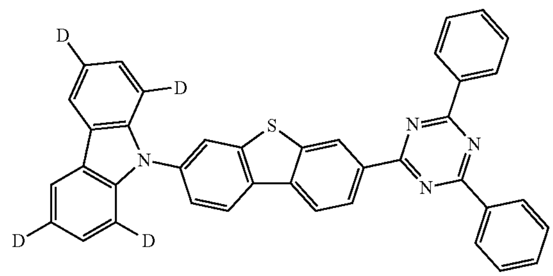

-continued
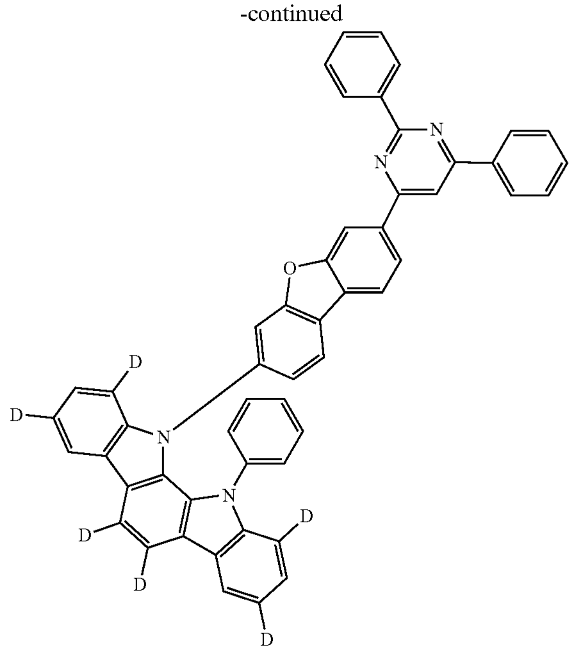
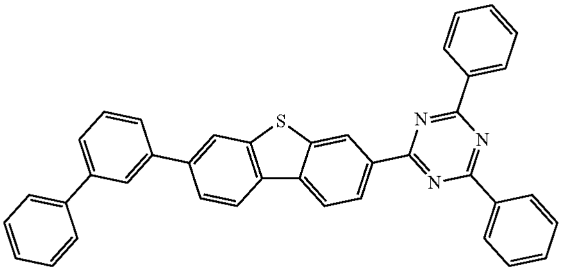
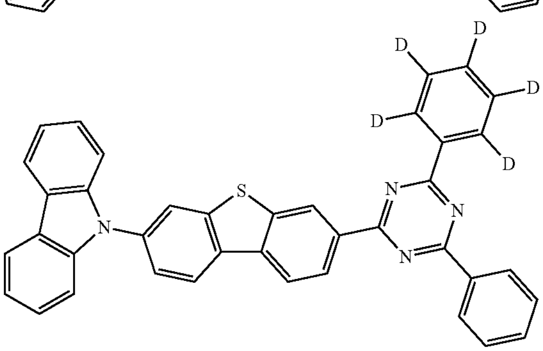
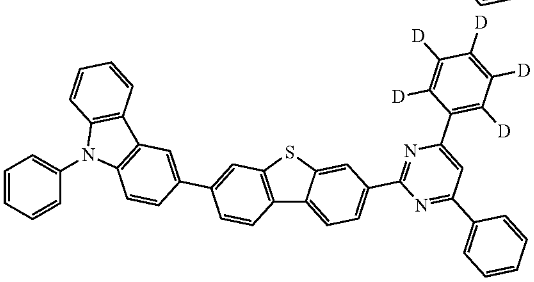
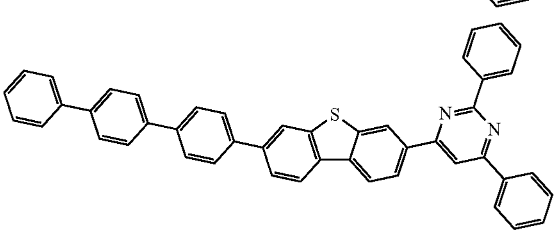
-continued
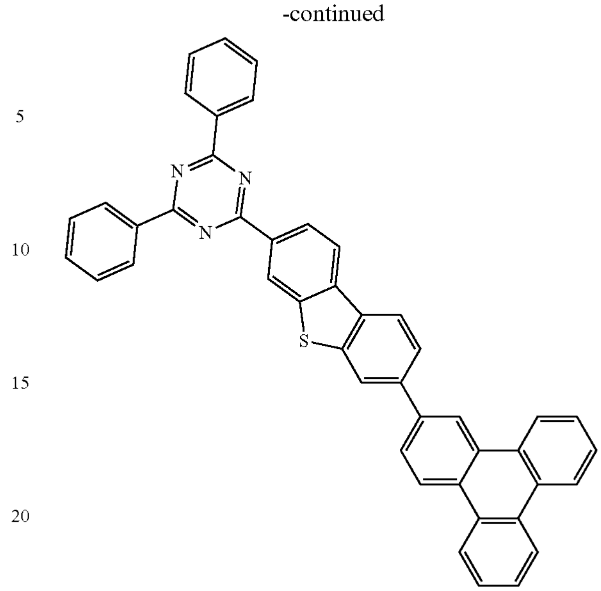
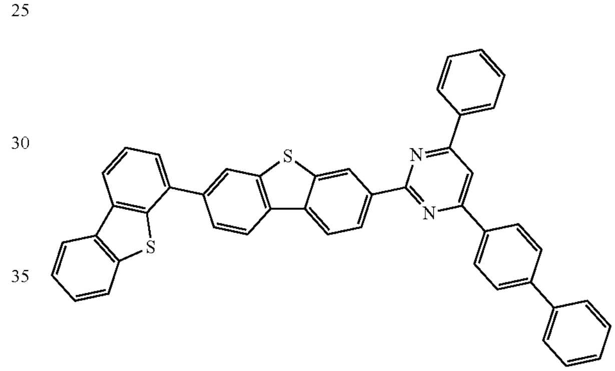
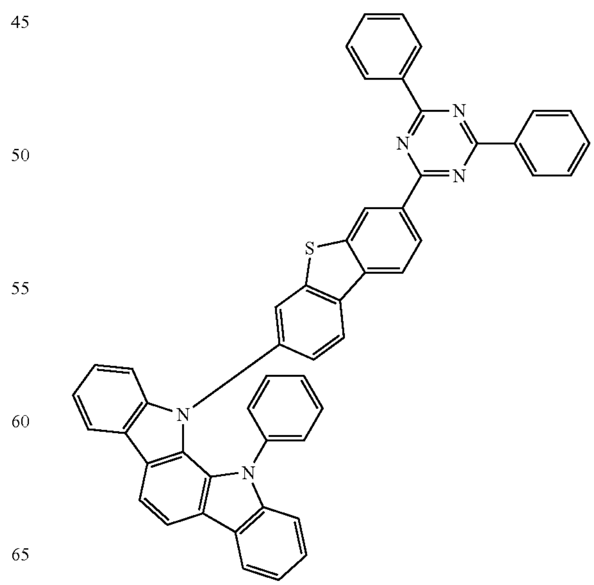

-continued
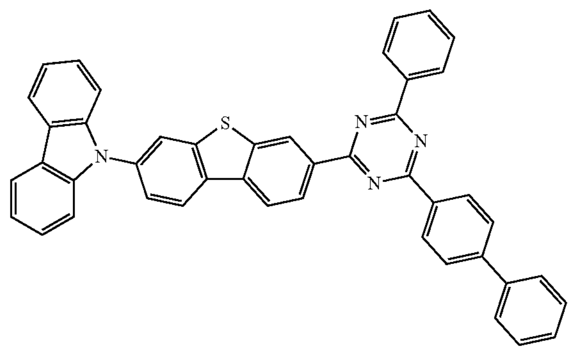
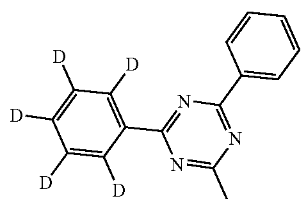
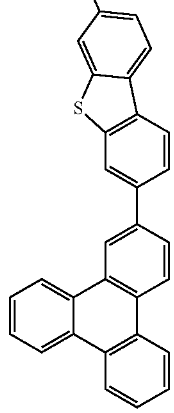
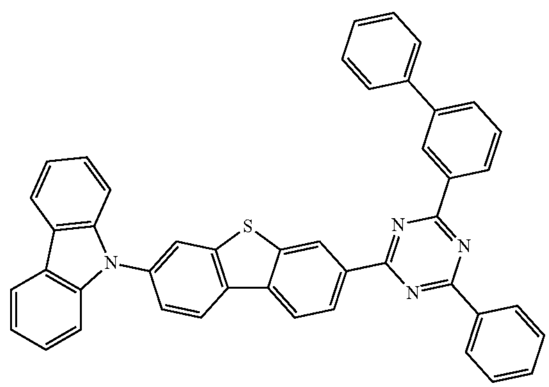
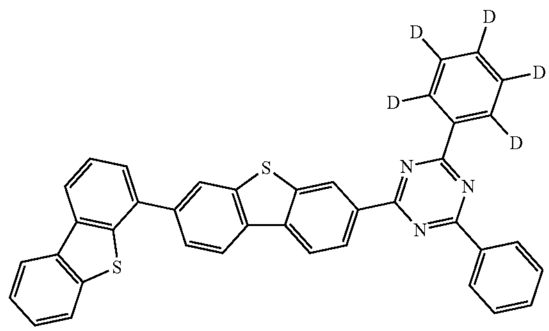
-continued
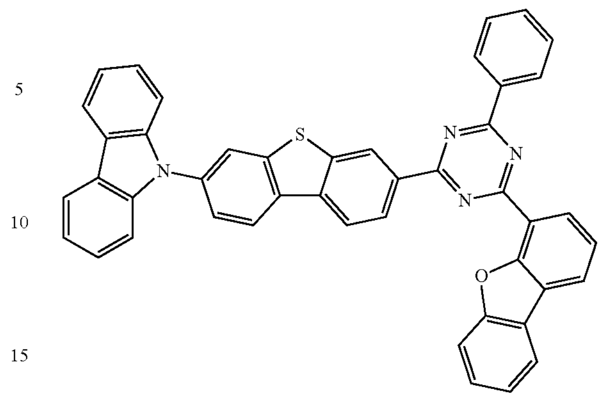
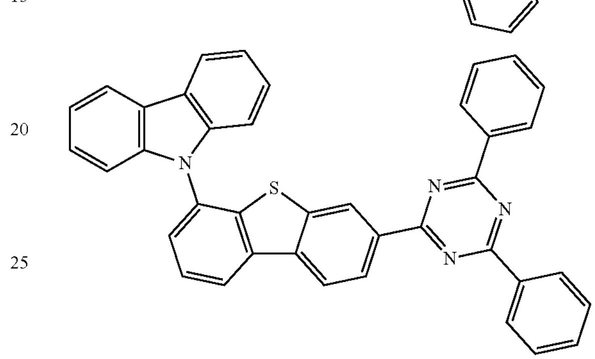
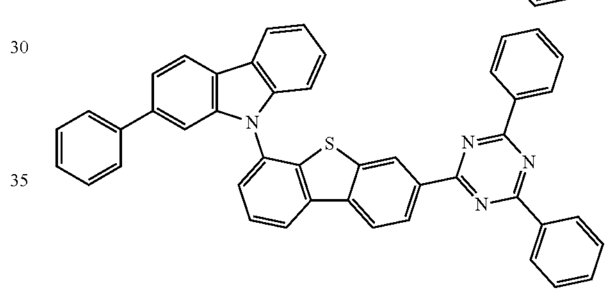
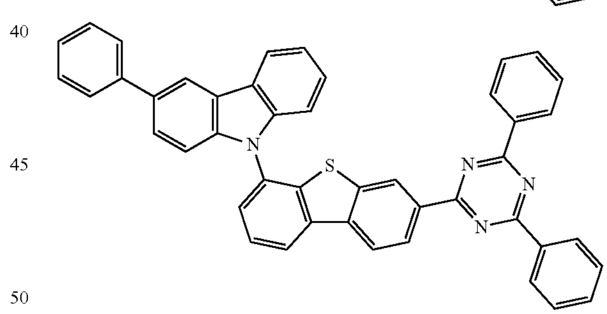
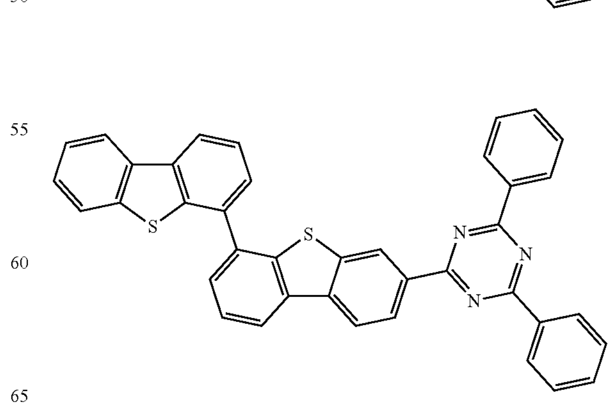

-continued
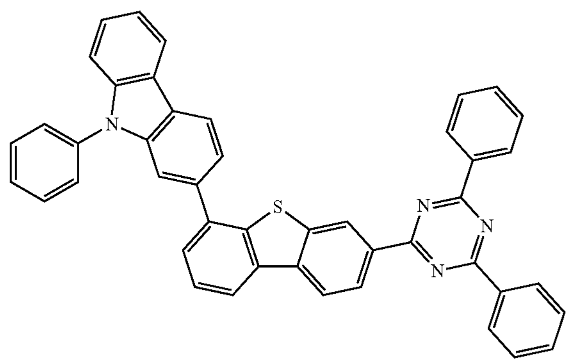
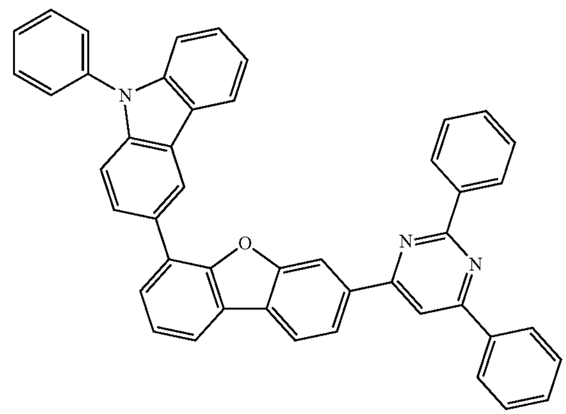
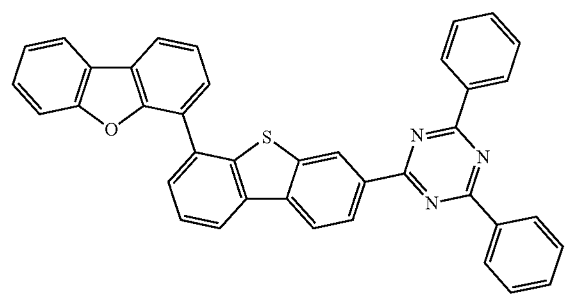
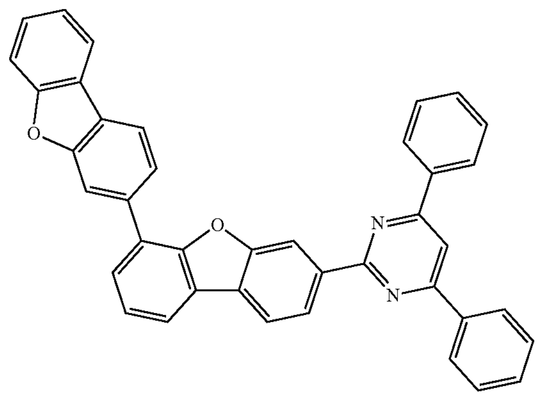
-continued
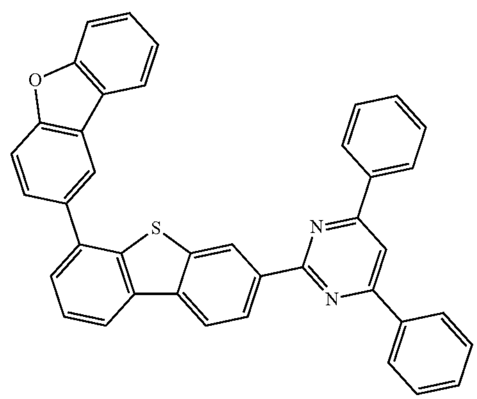
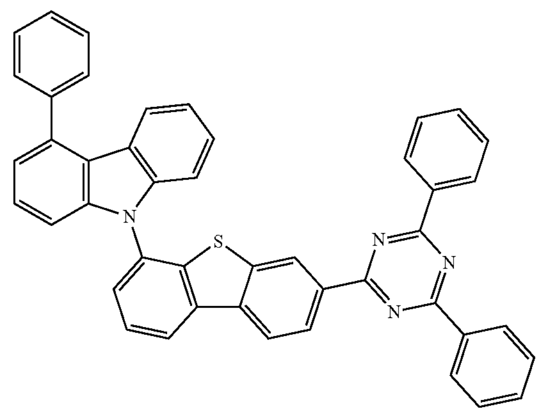
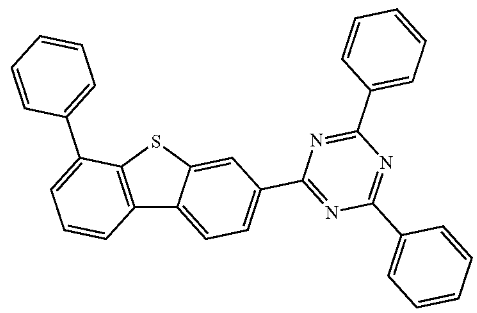
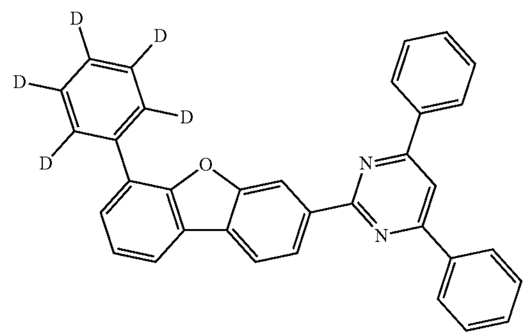

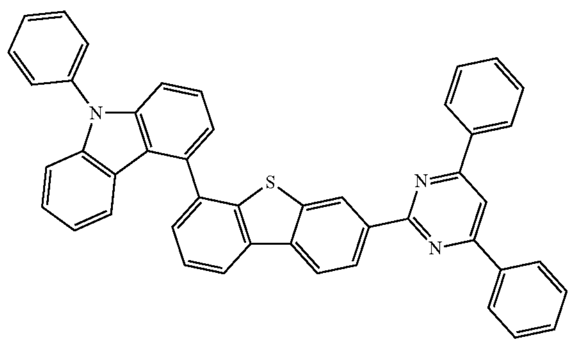
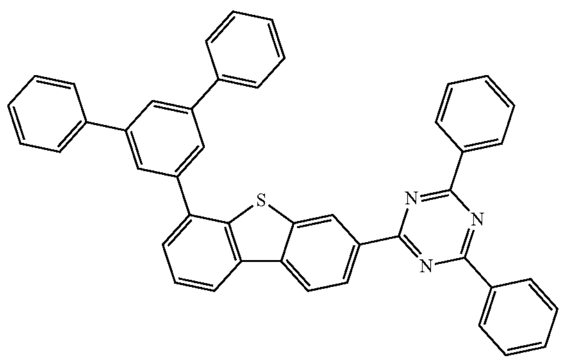
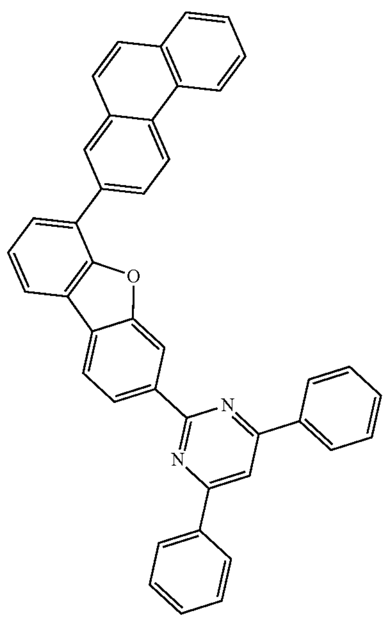
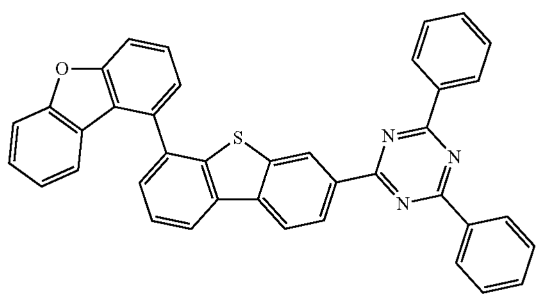
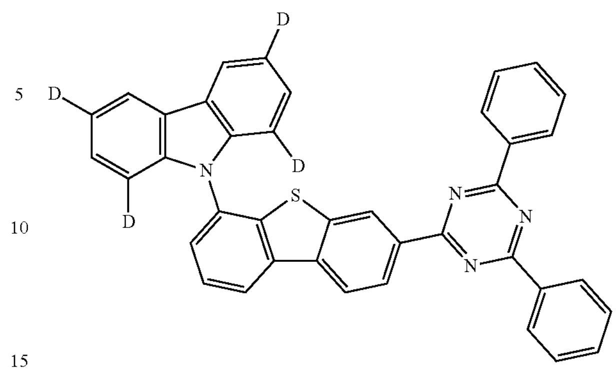
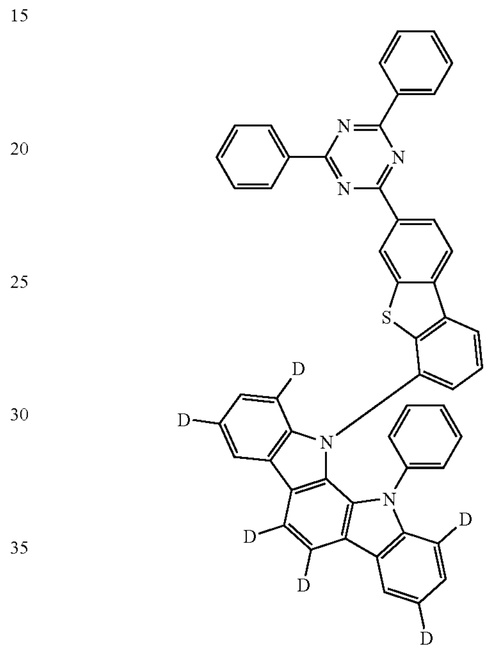
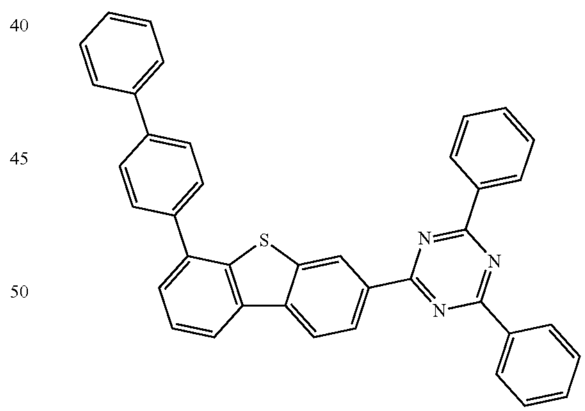
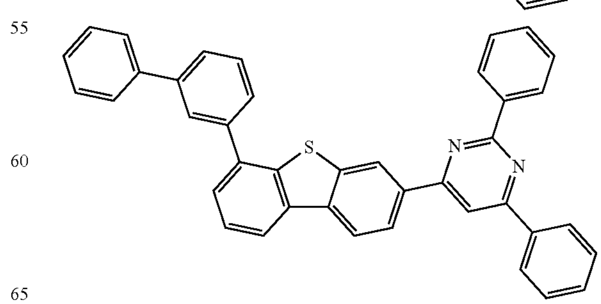

-continued
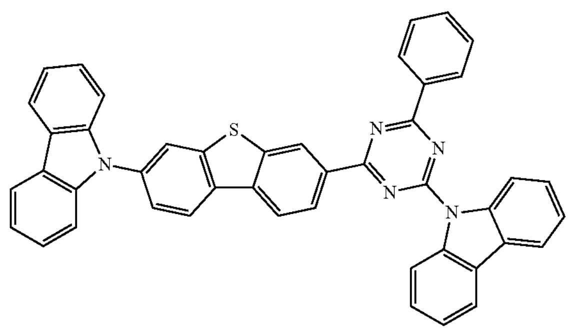
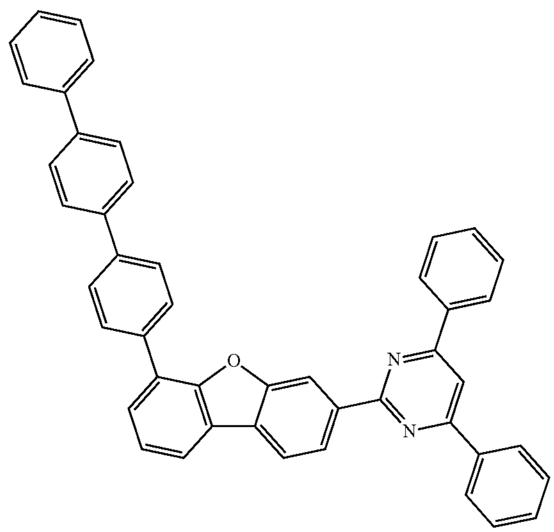
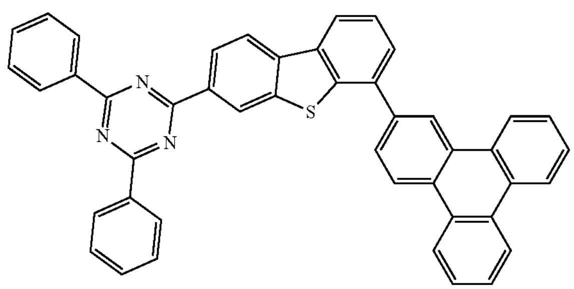
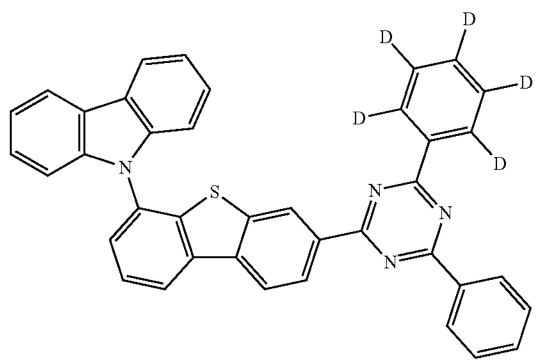
-continued
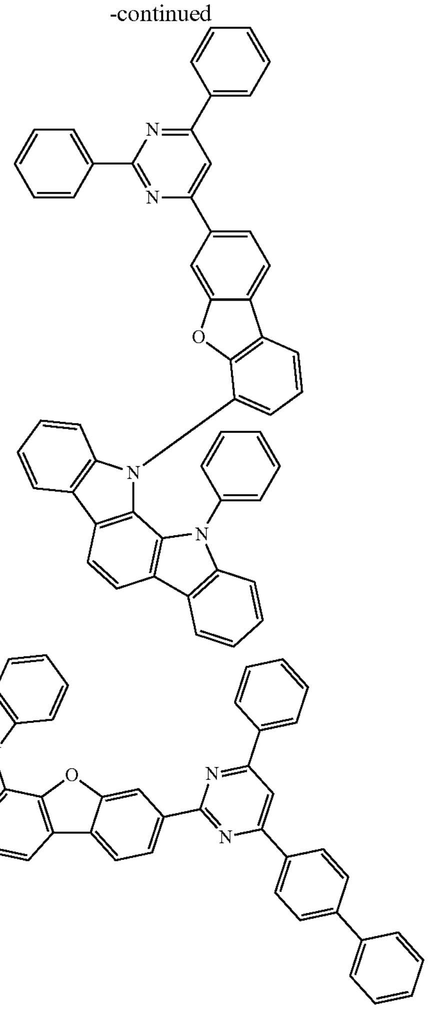
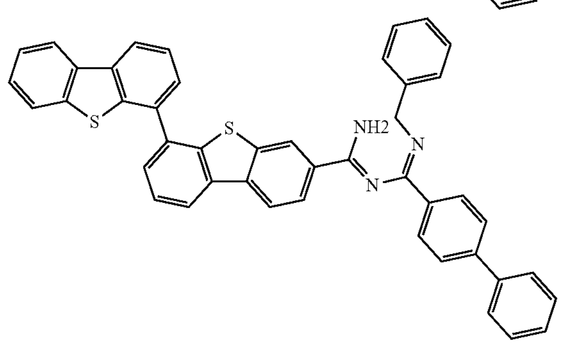
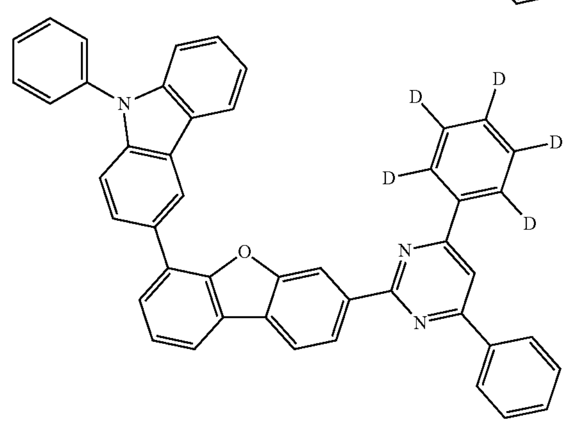

-continued
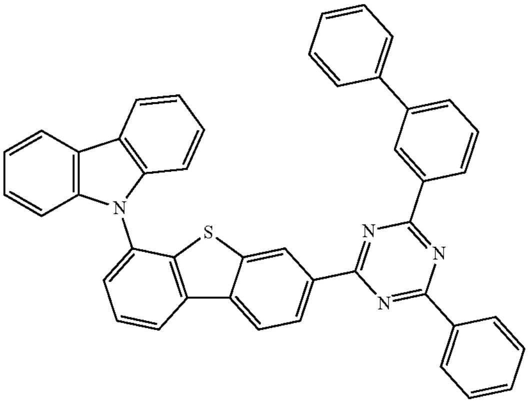
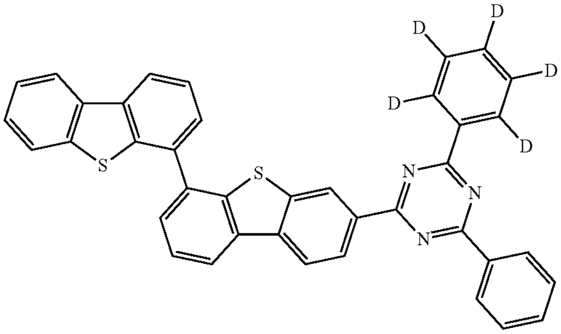
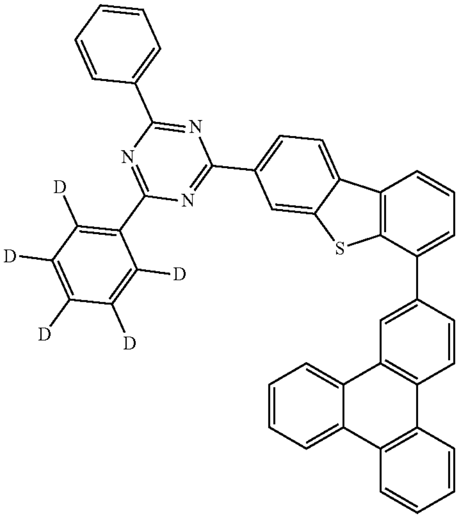
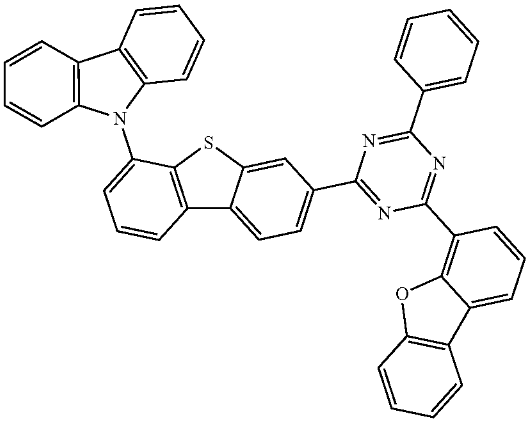
-continued
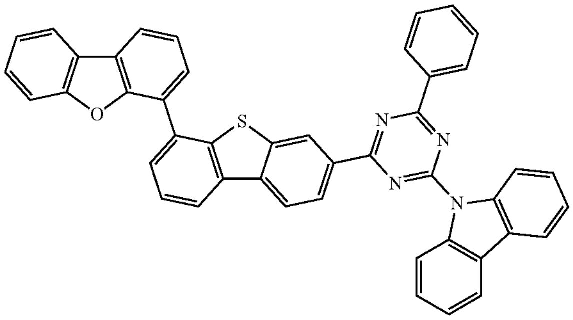
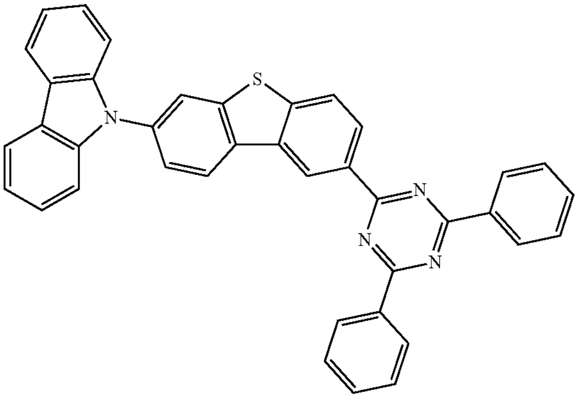
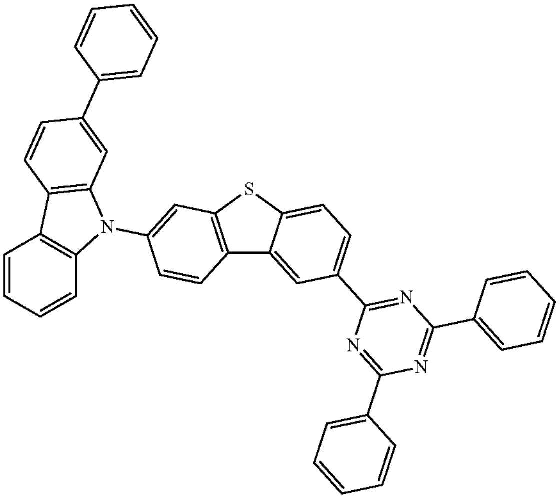
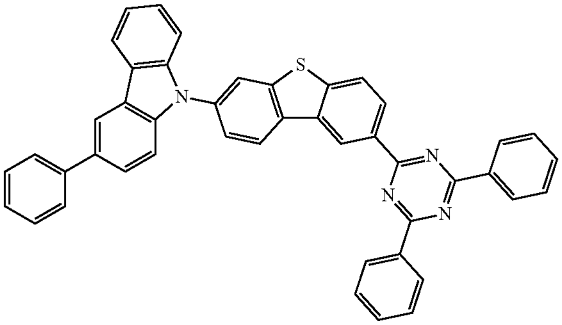

-continued
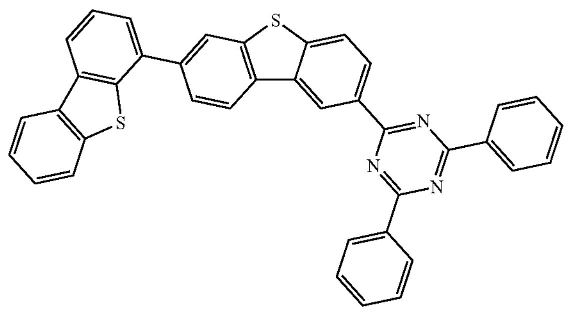
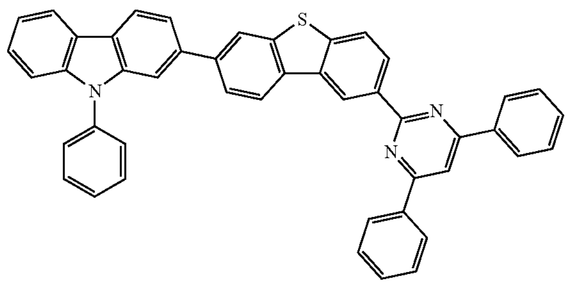
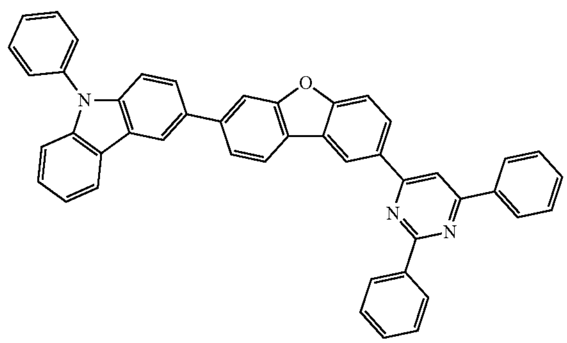
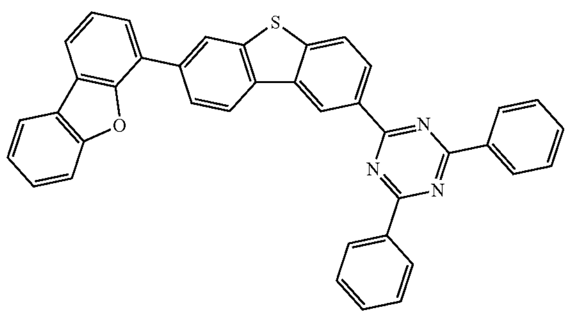
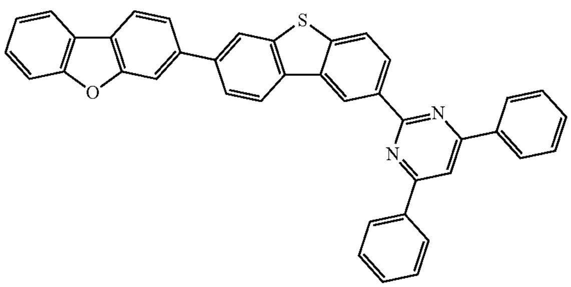
-continued
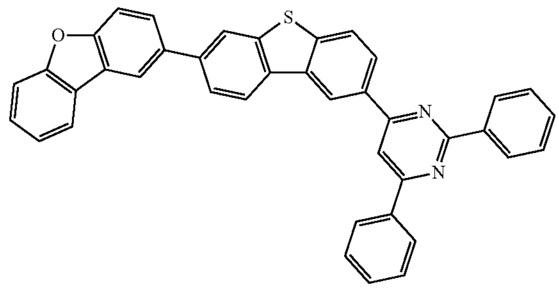
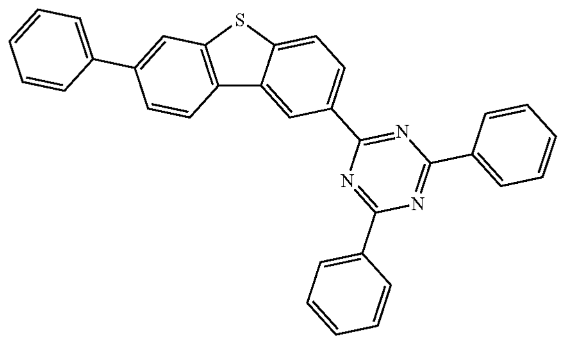
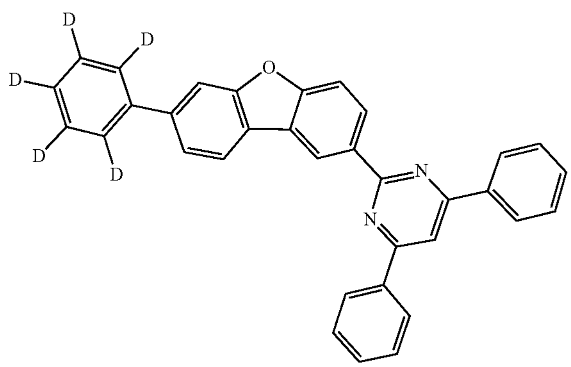
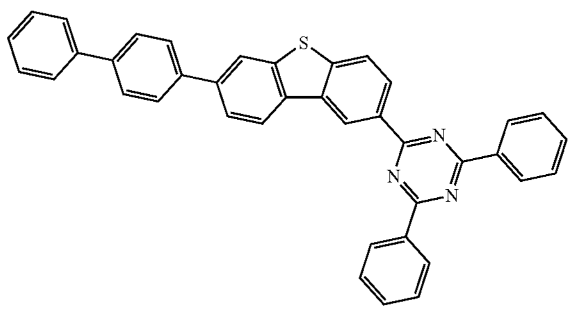
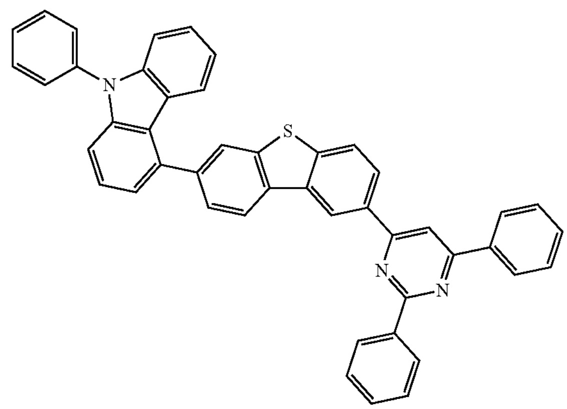

-continued
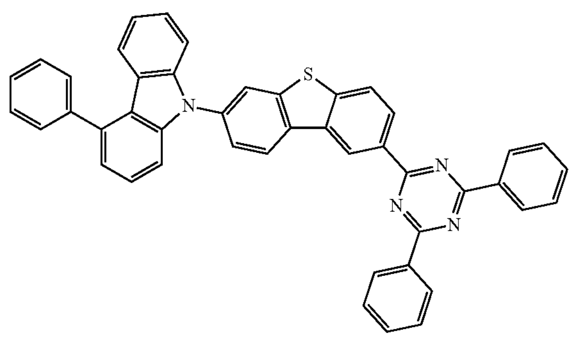
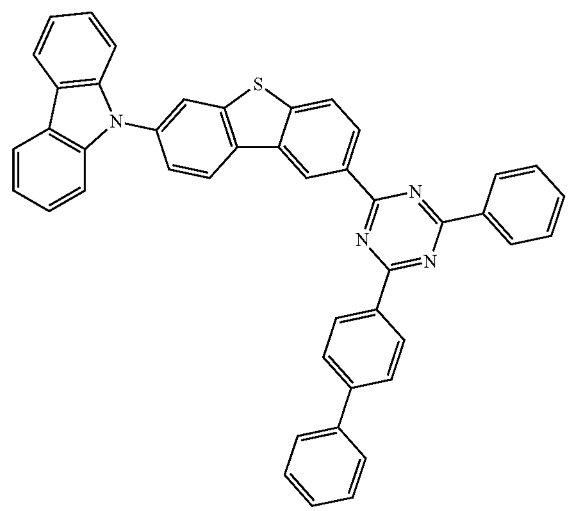
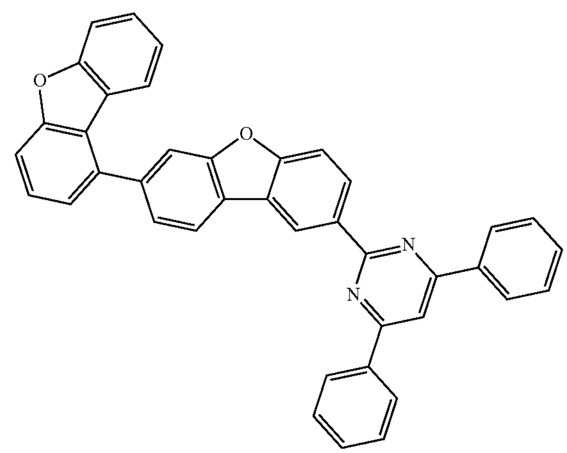
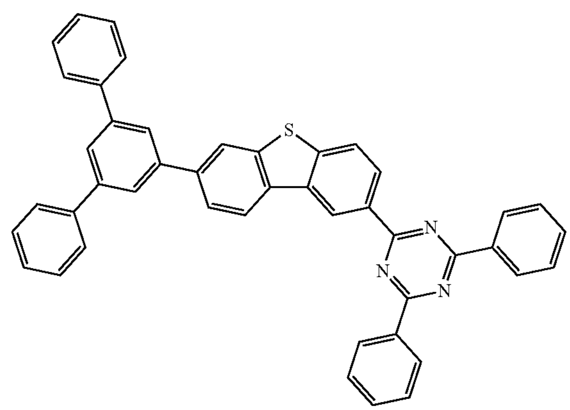
-continued
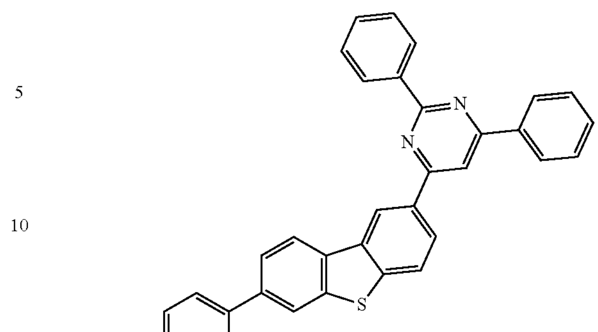
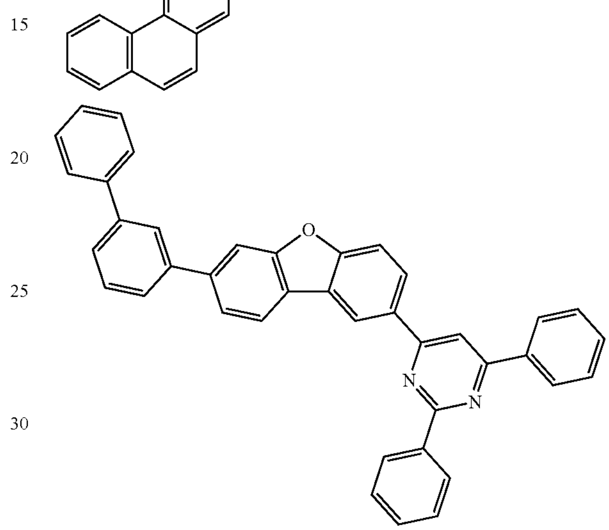
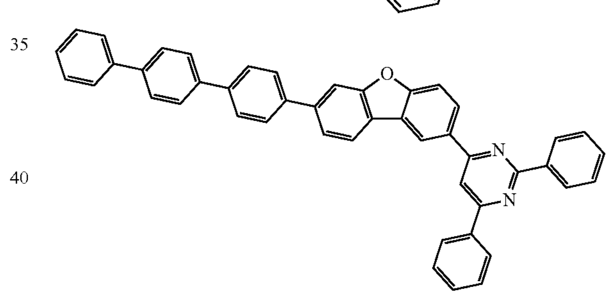
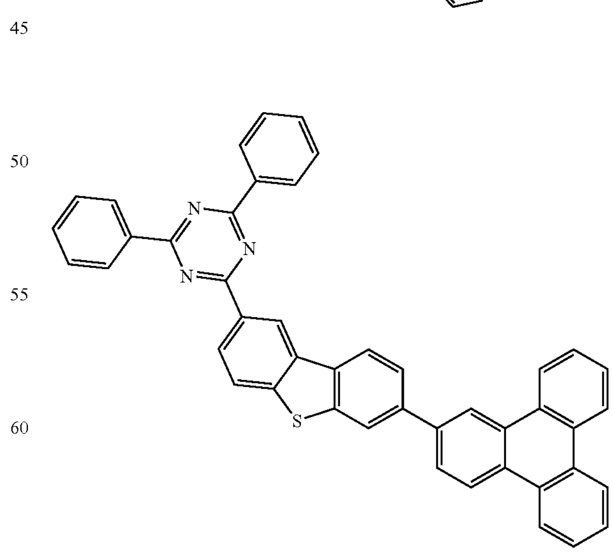

-continued
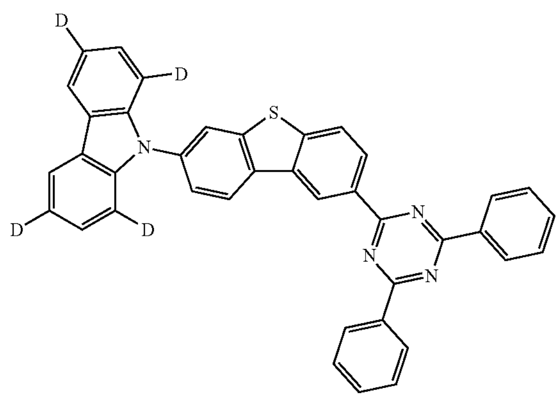
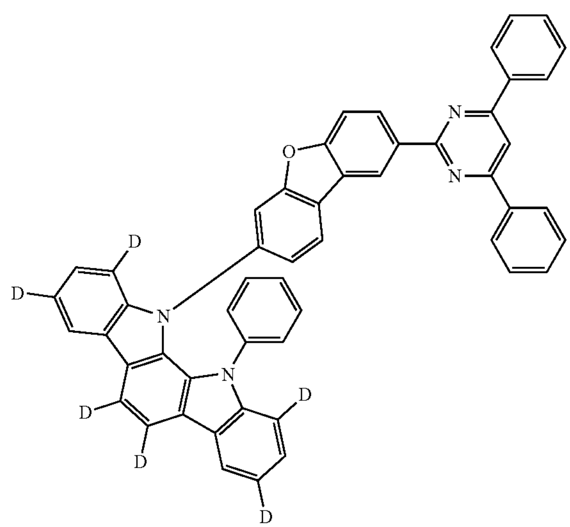
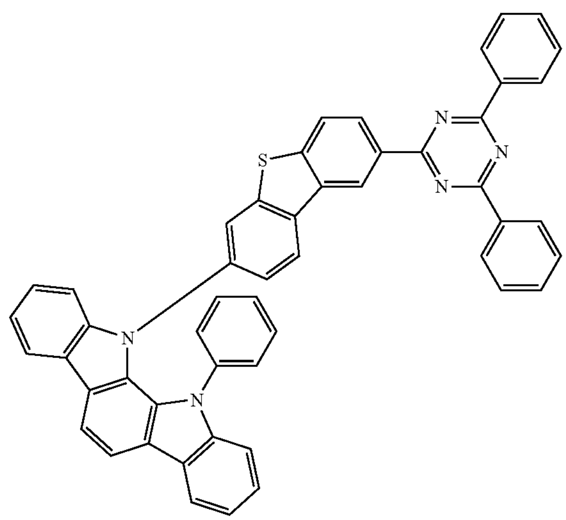
-continued
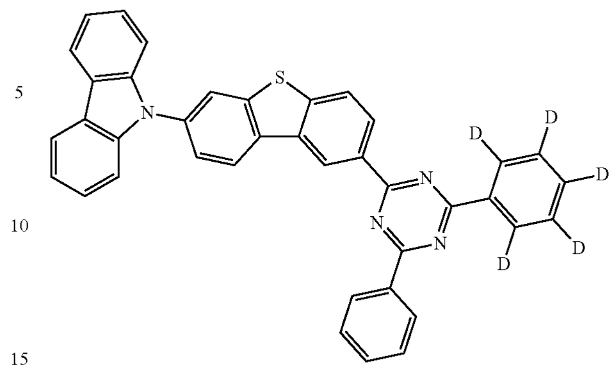
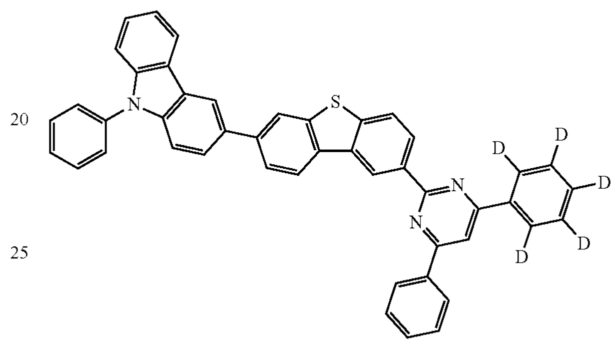
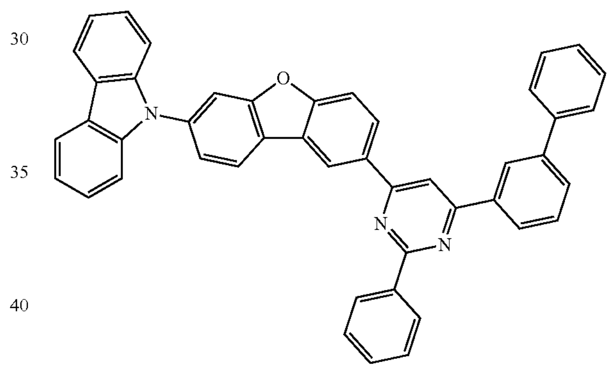
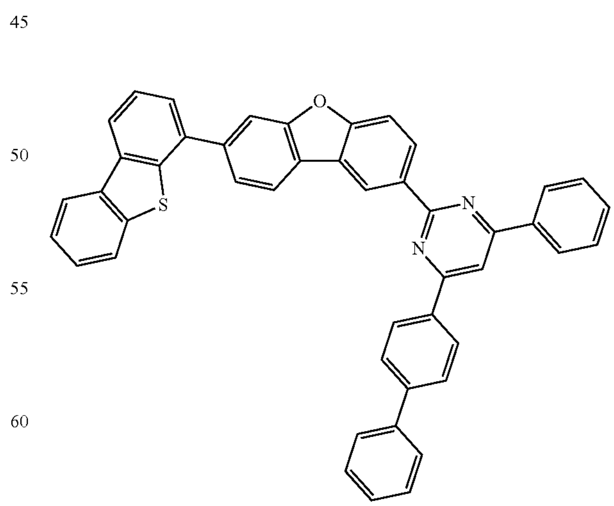

-continued
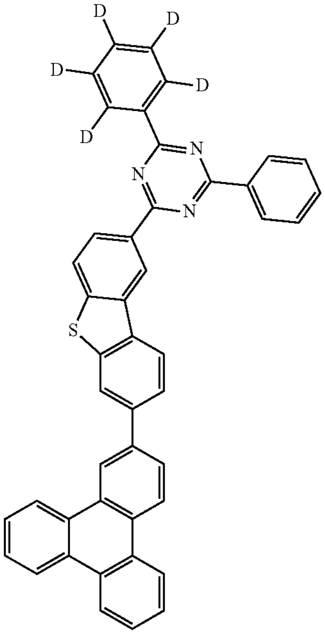
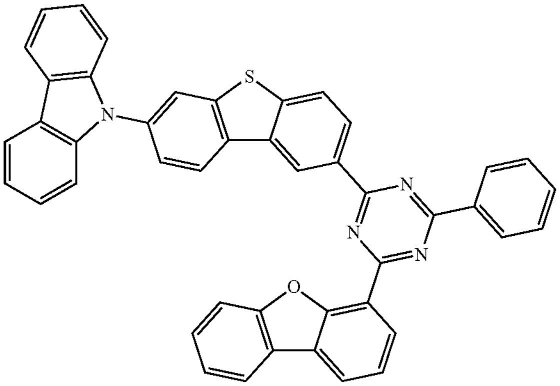 [SMILES: c1ccc(-c2nc(-c3ccc4sc5cc(-n6c7ccccc7c7ccccc76)ccc5c4c3)nc(-c3cccc4c3oc3ccccc34)n2)cc1]
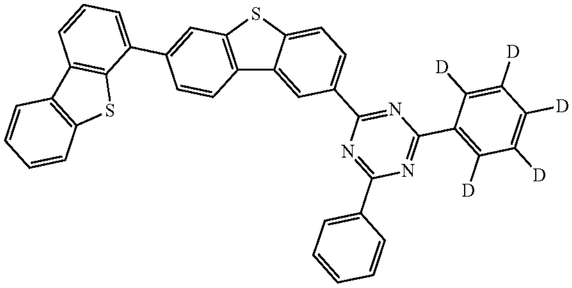
-continued
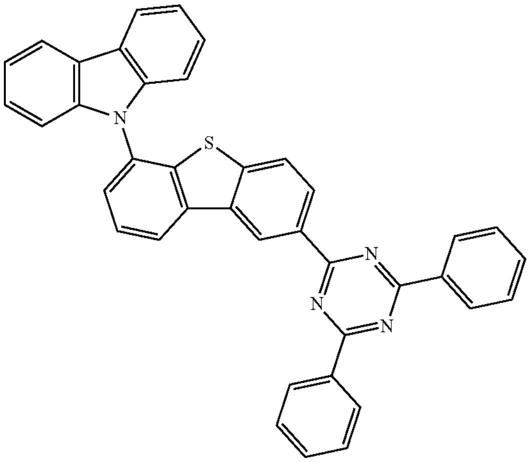
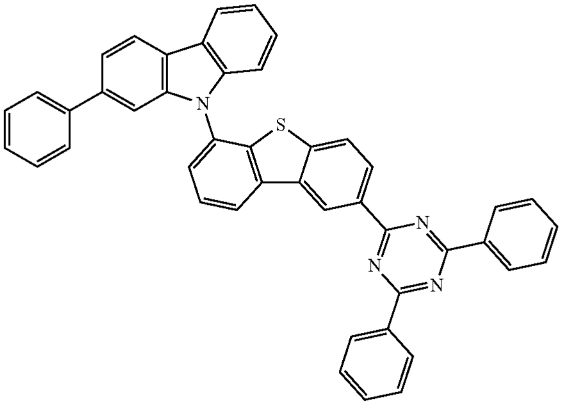
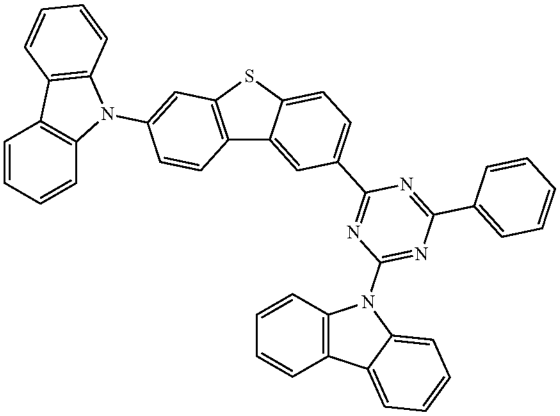
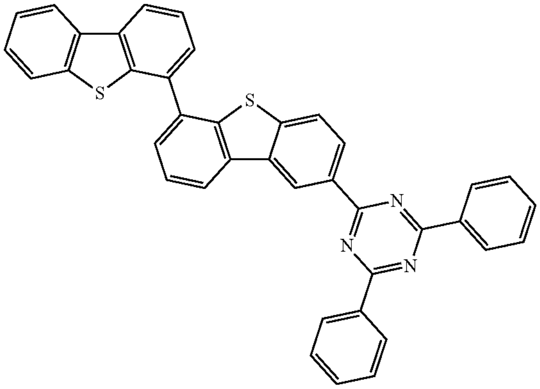

-continued
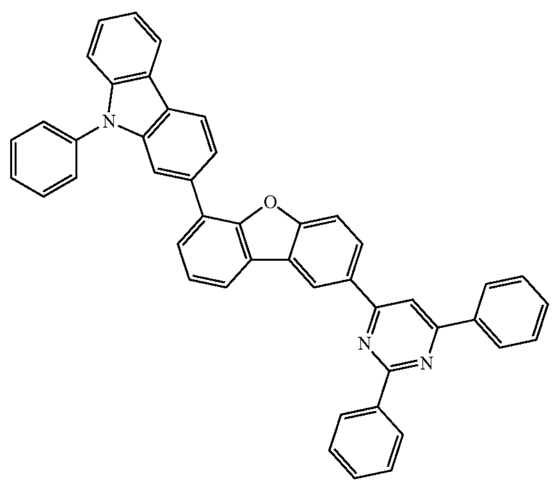
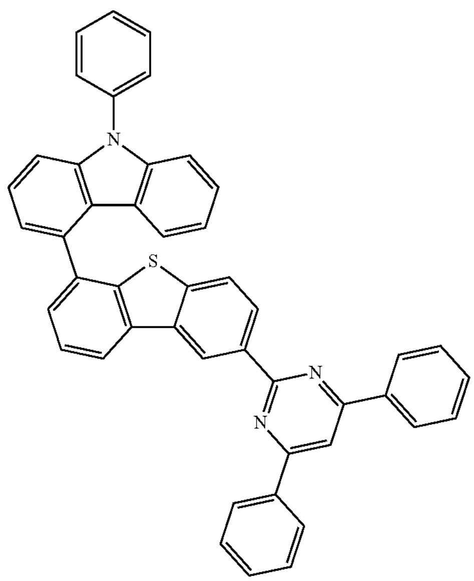
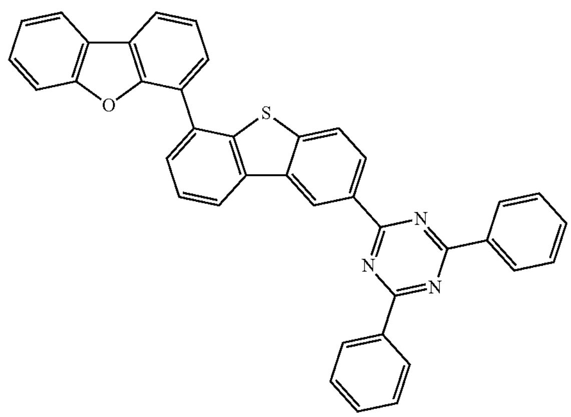
-continued
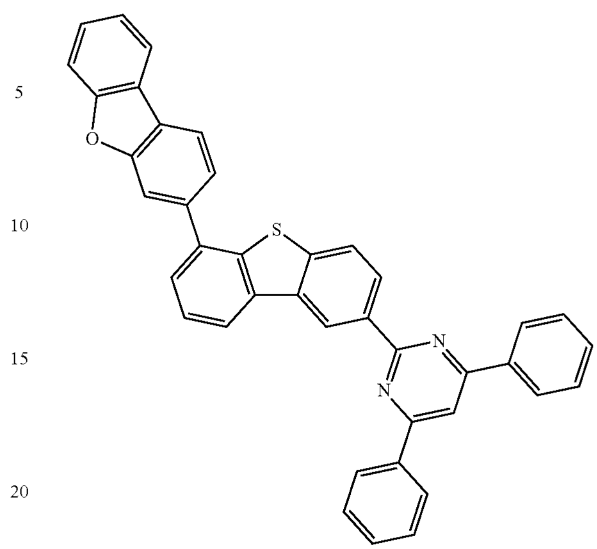
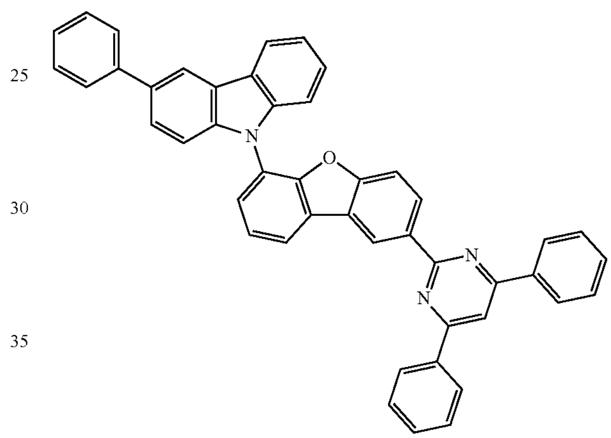
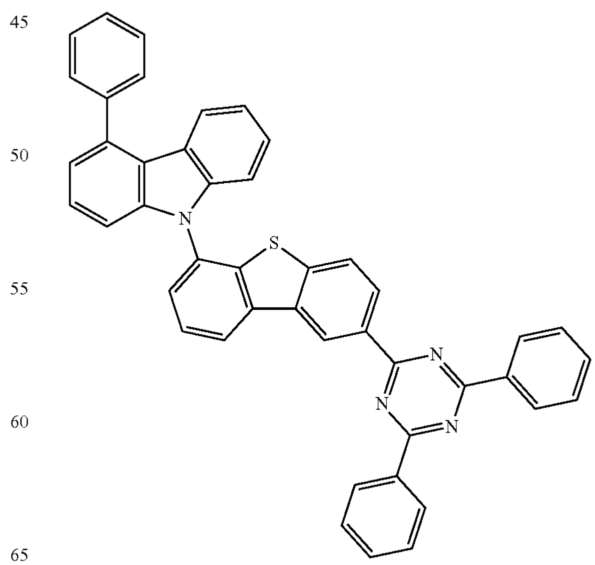

-continued
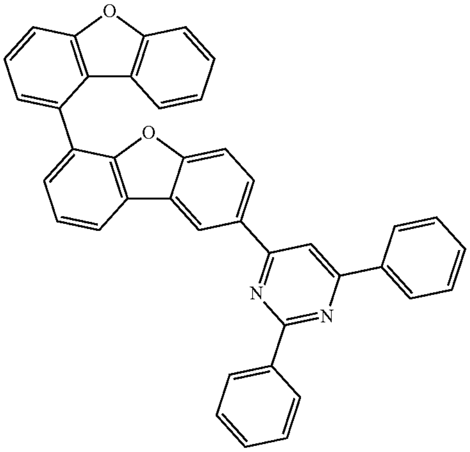
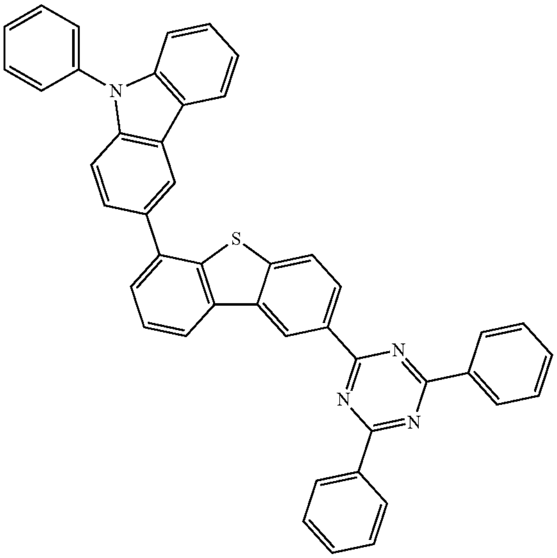
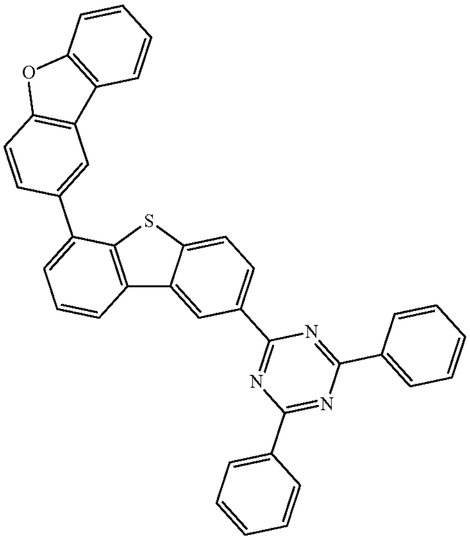
-continued
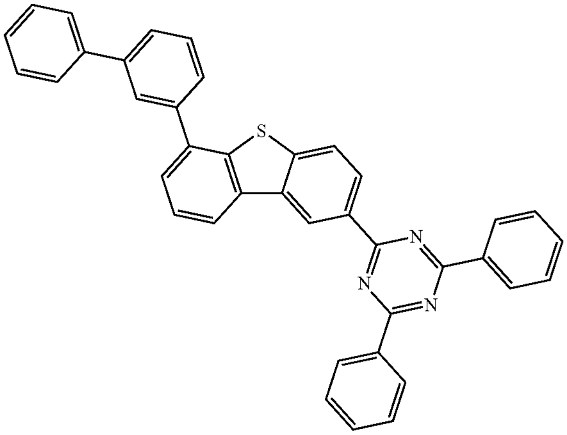
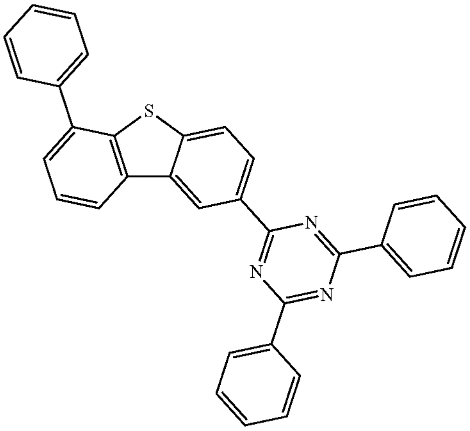
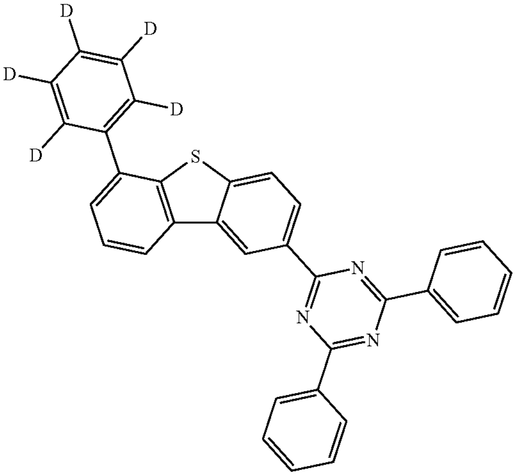

-continued
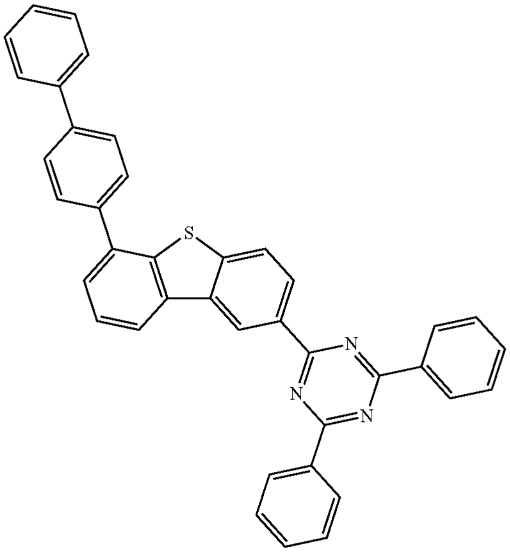
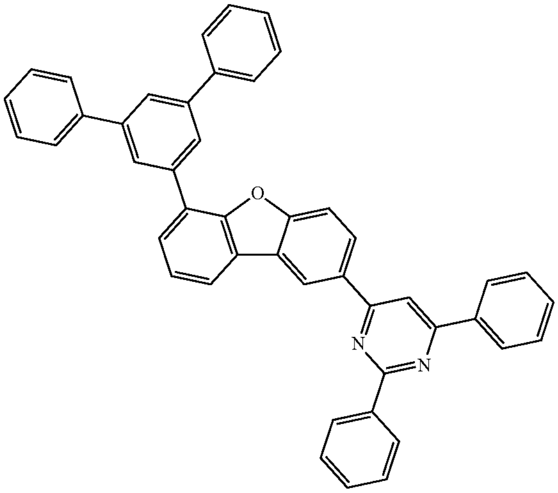
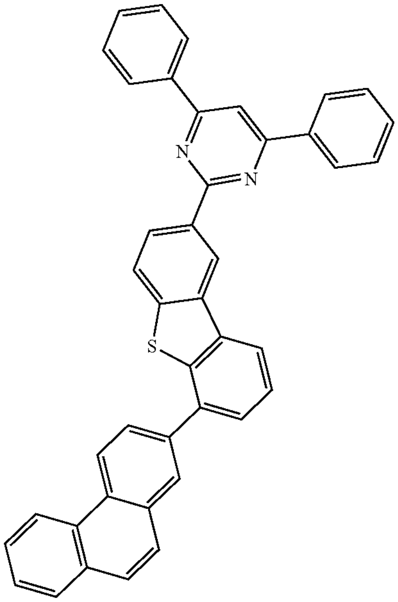
-continued
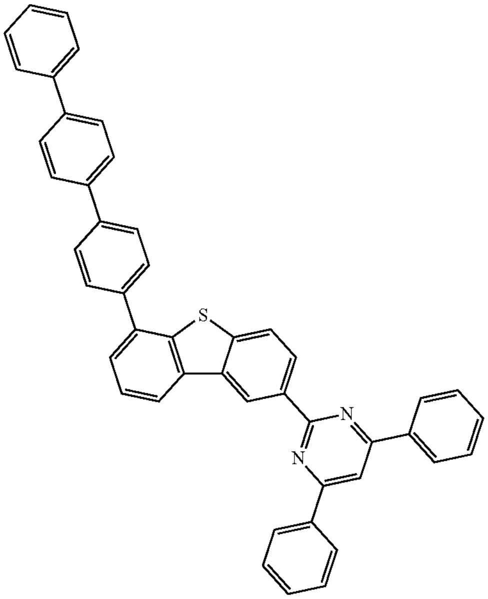
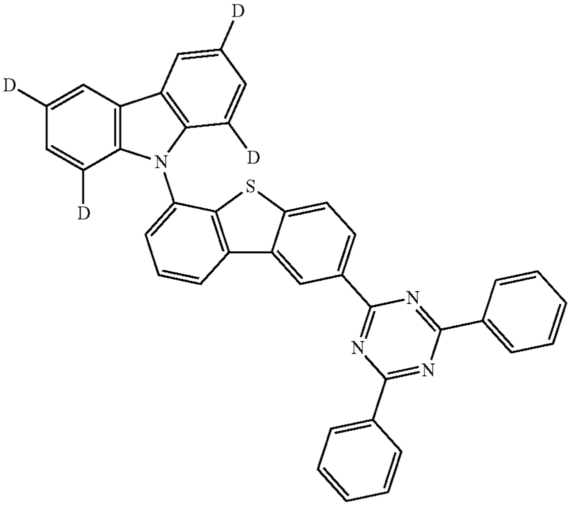

-continued
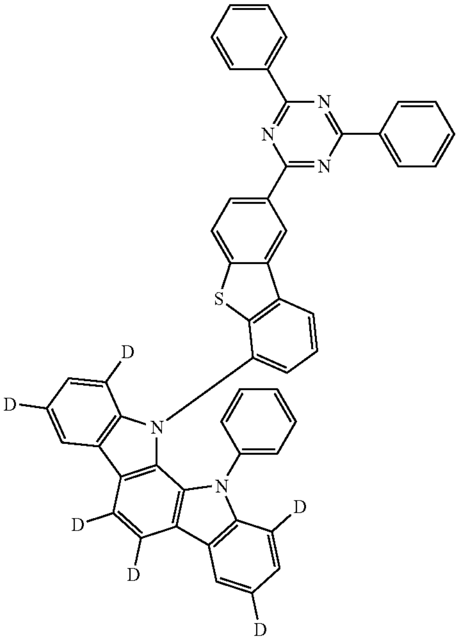
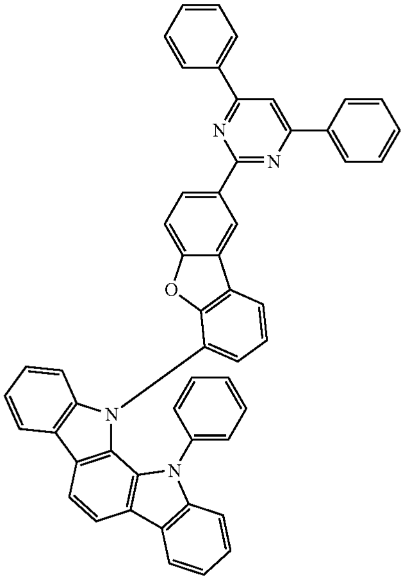
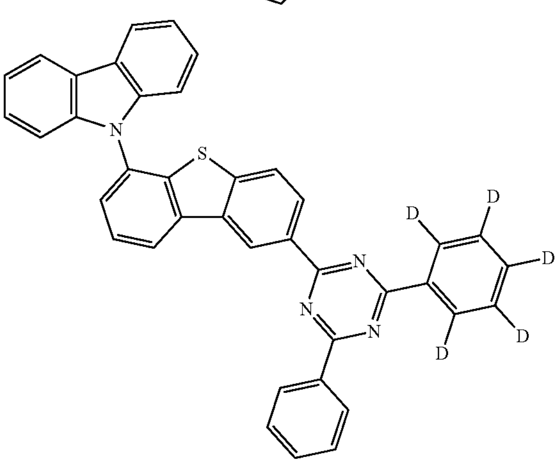
-continued
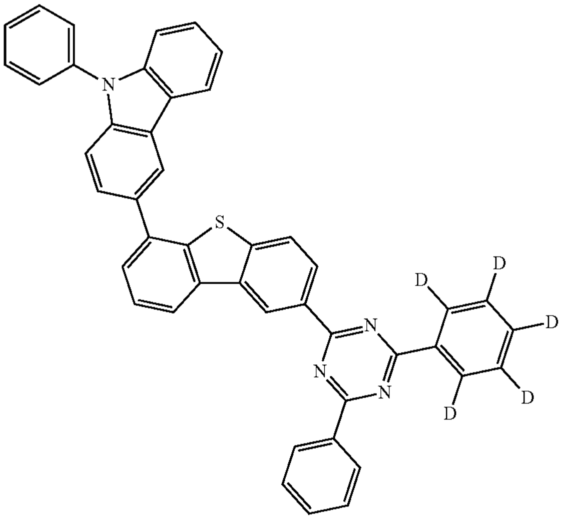
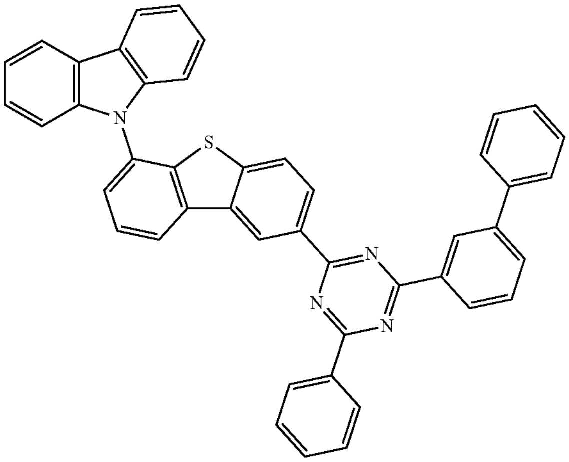 [SMILES: c1ccc(-c2cccc(-c3nc(-c4ccccc4)nc(-c4ccc5sc6c(-n7c8ccccc8c8ccccc87)cccc6c5c4)n3)c2)cc1]
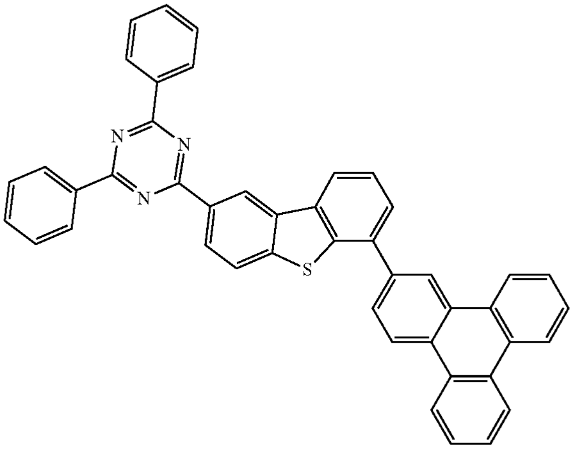

-continued
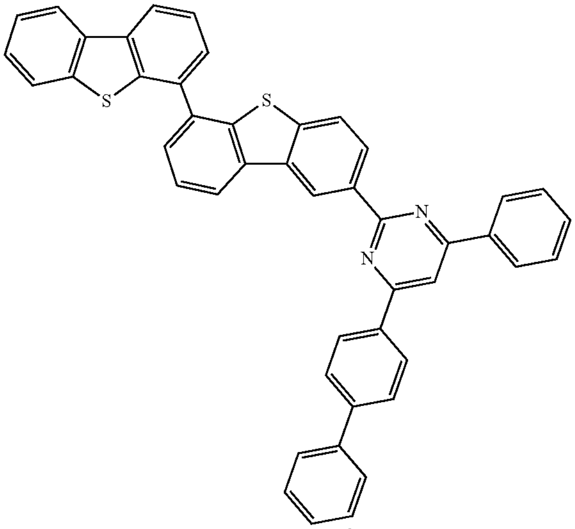
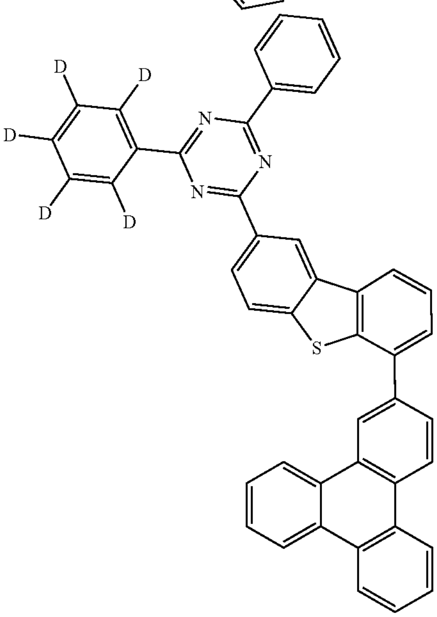
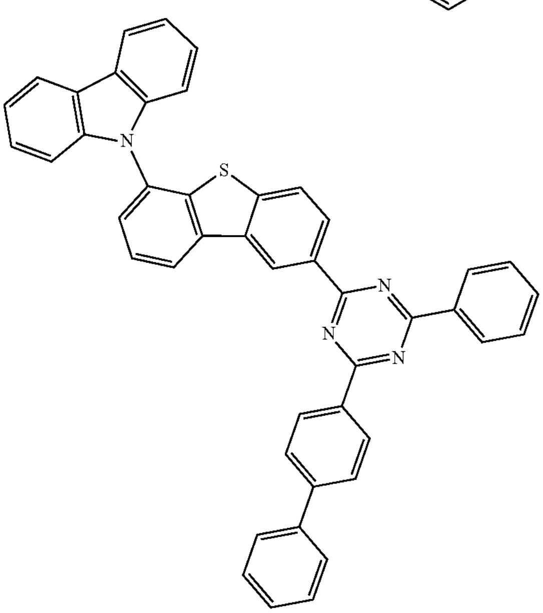
-continued
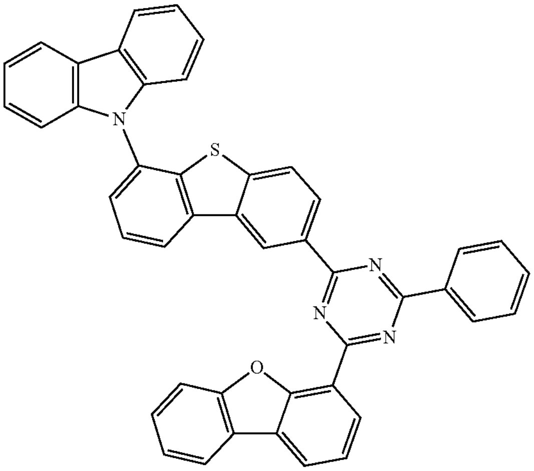
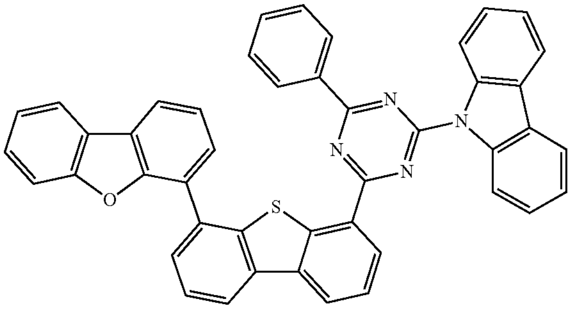
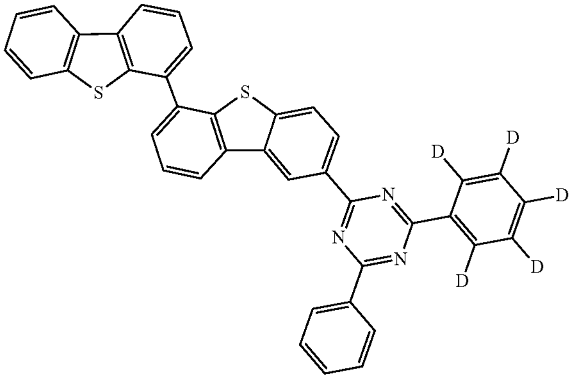
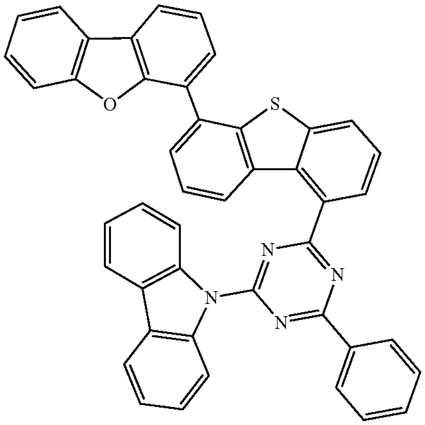

-continued
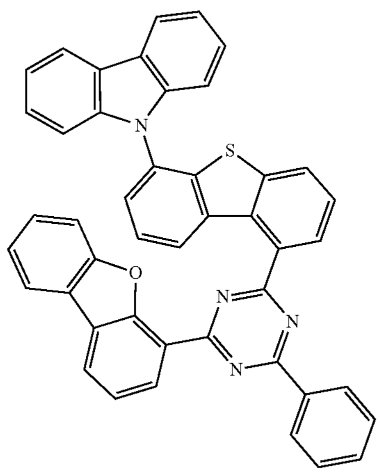
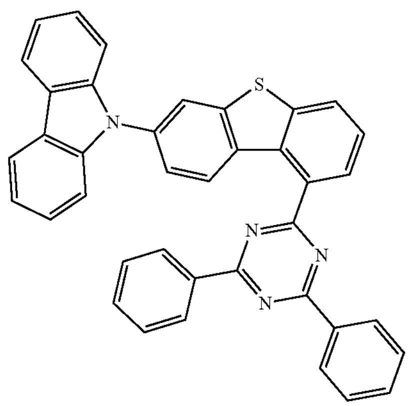
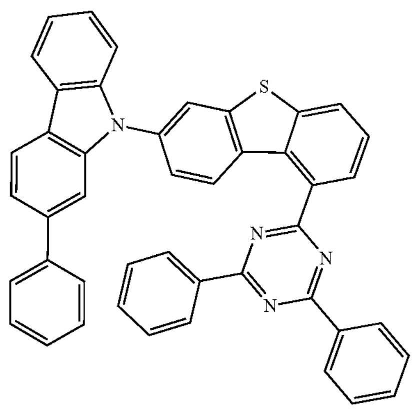
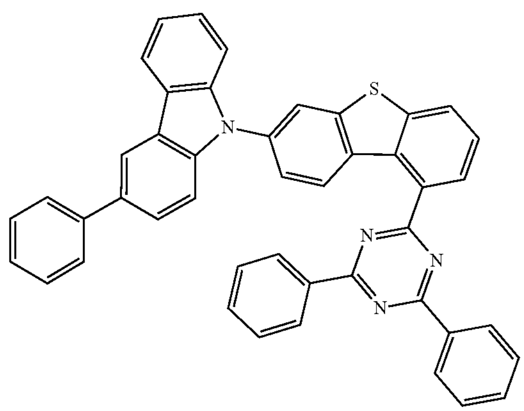
-continued
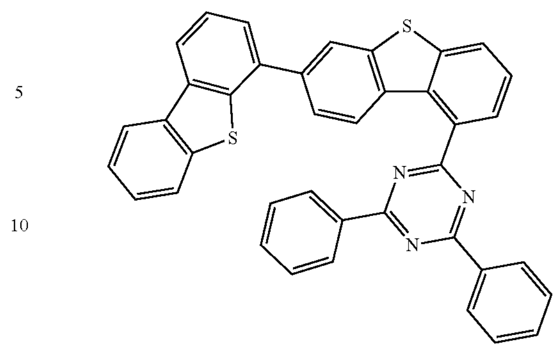
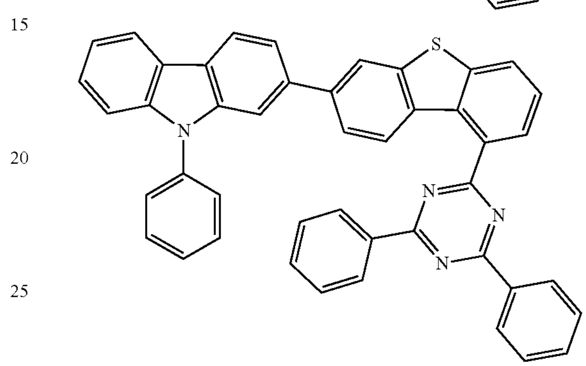
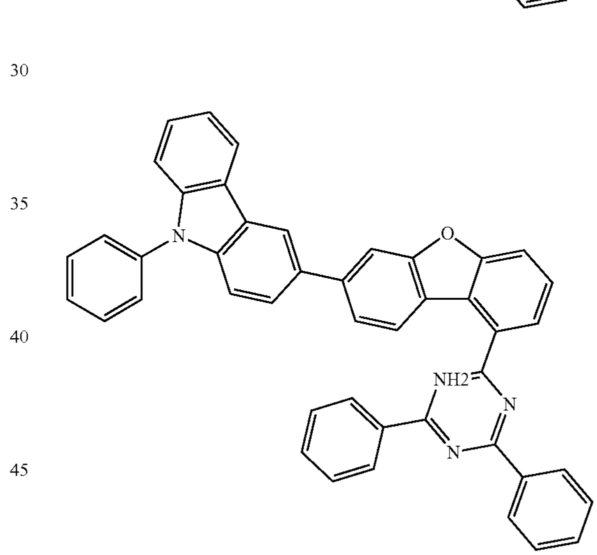
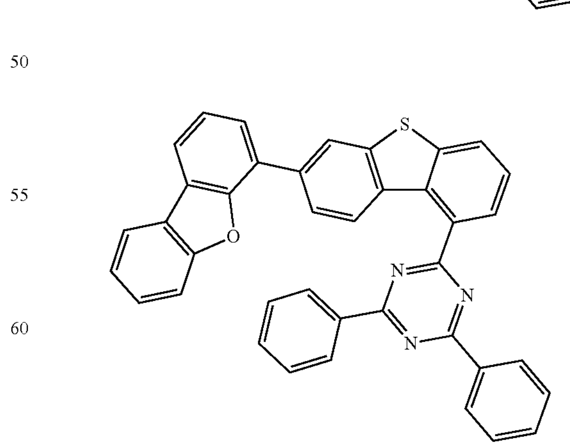

-continued
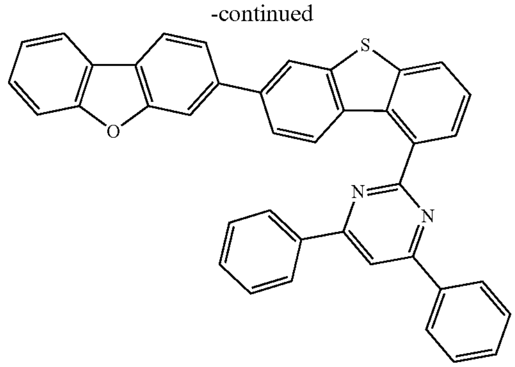
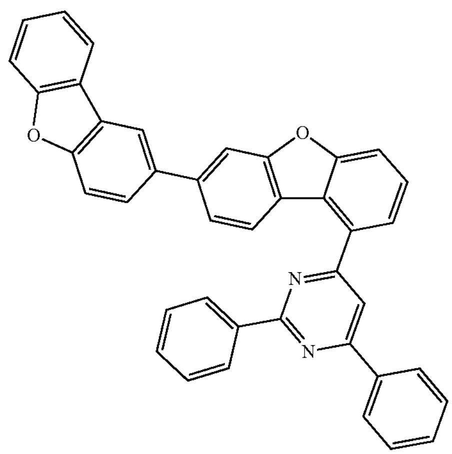
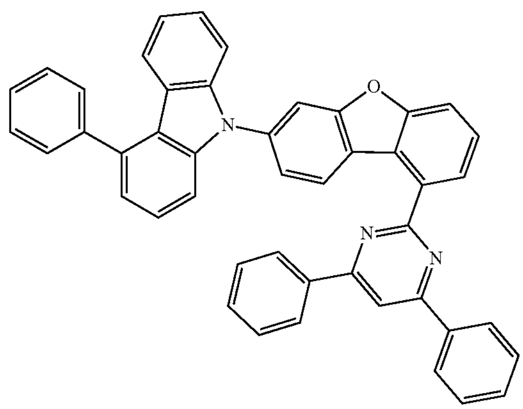
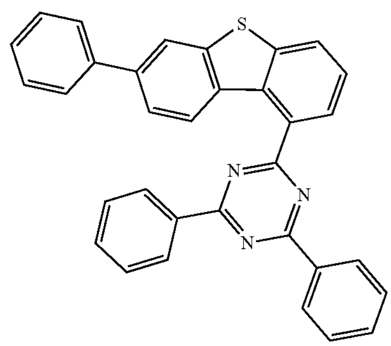
-continued
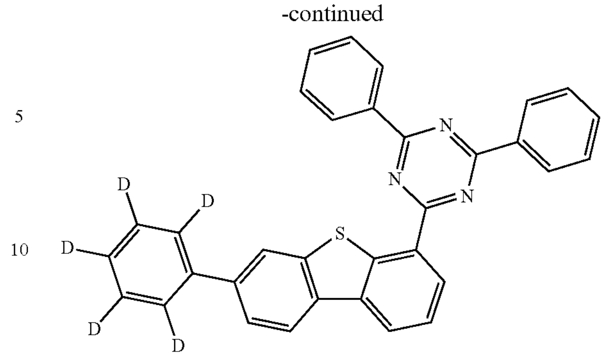
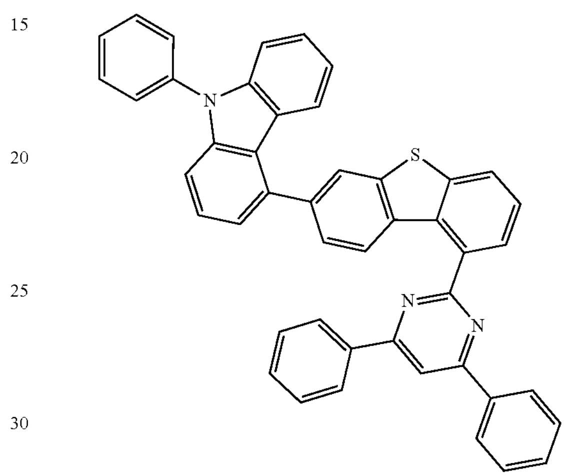
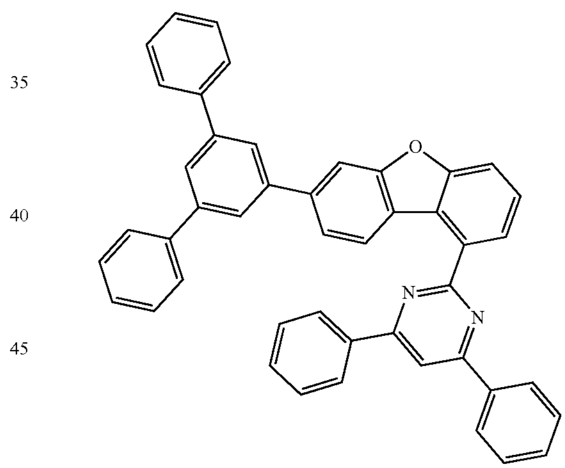
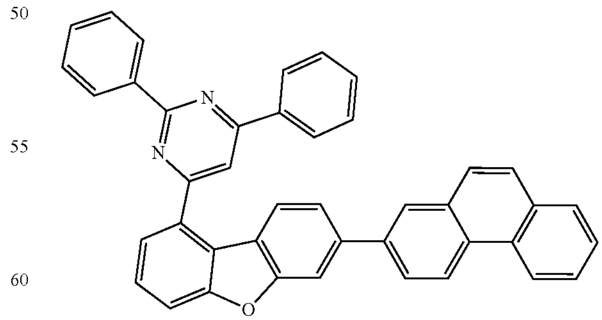

-continued
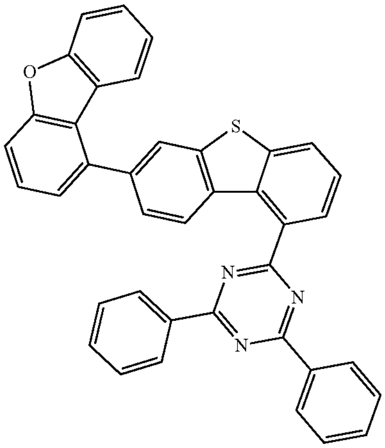
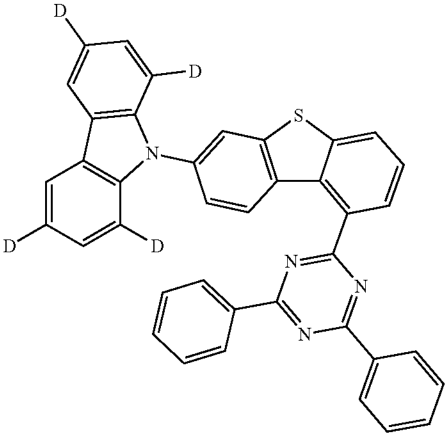
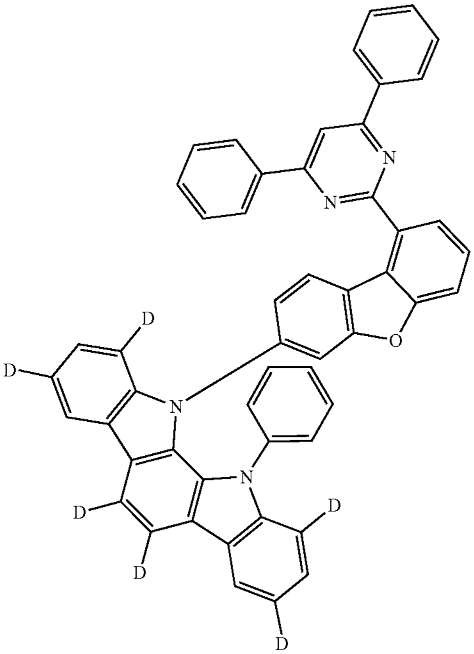
-continued
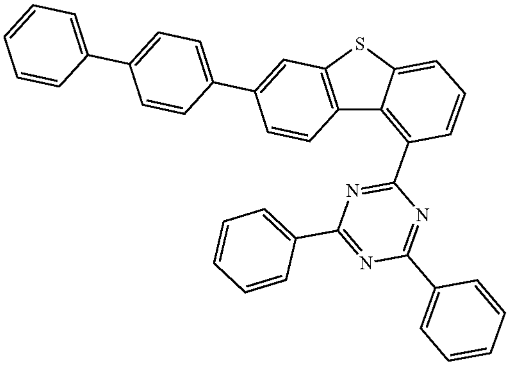
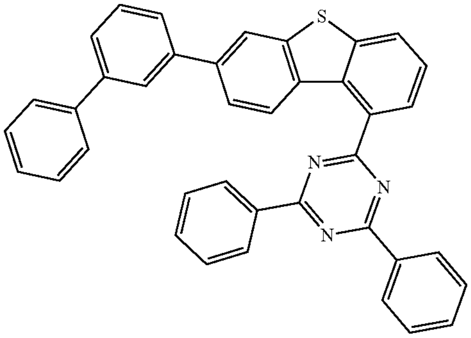
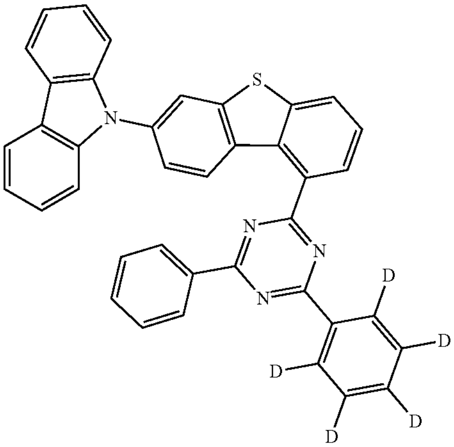
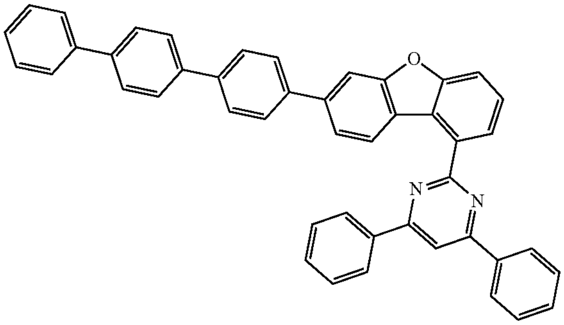

-continued
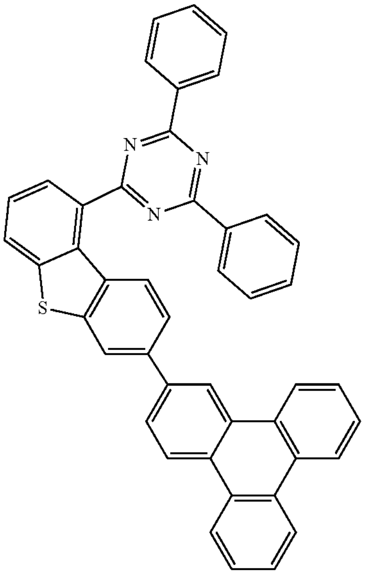
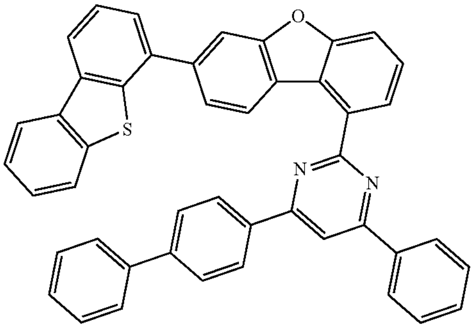
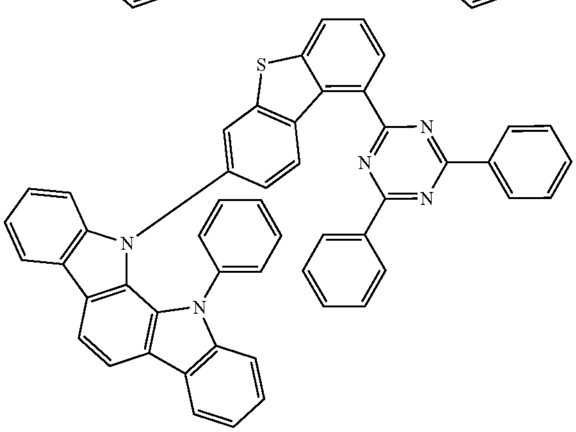
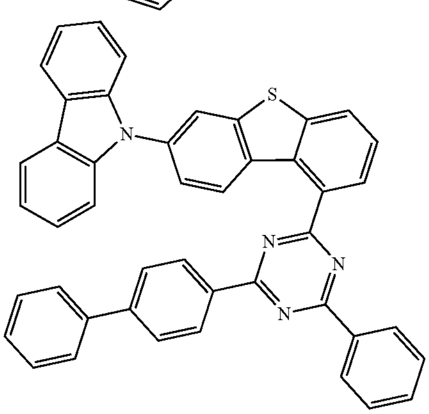
-continued
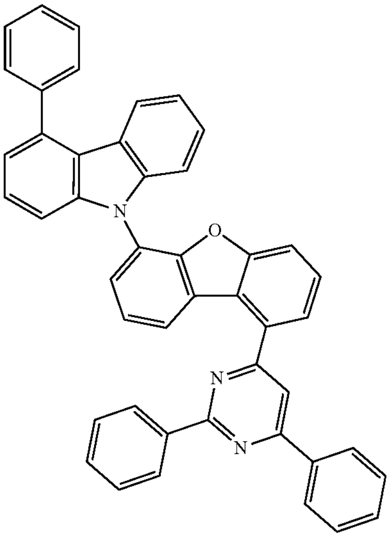
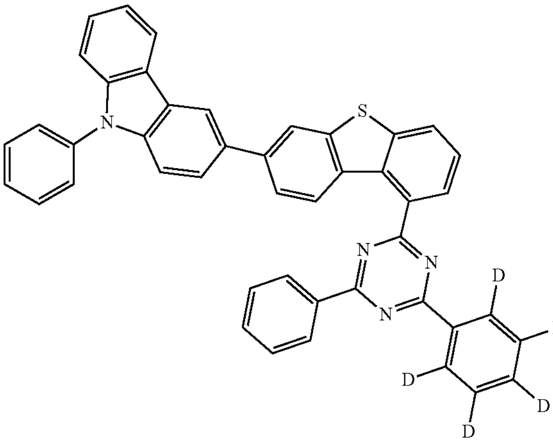
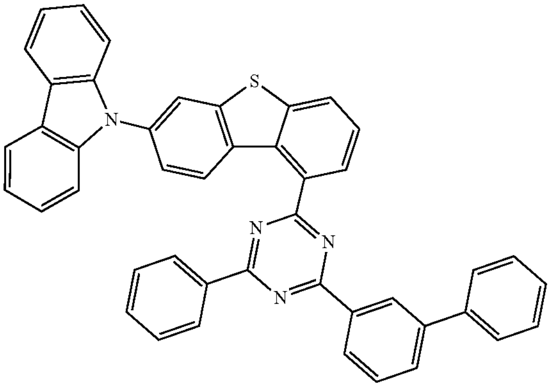

-continued
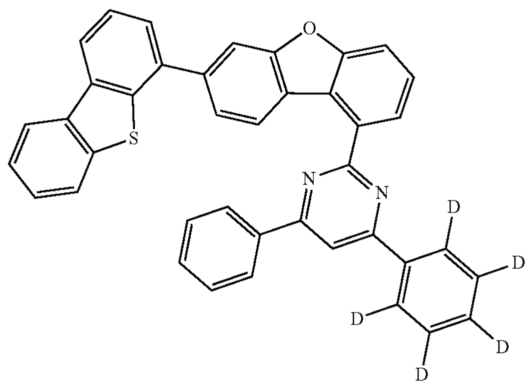
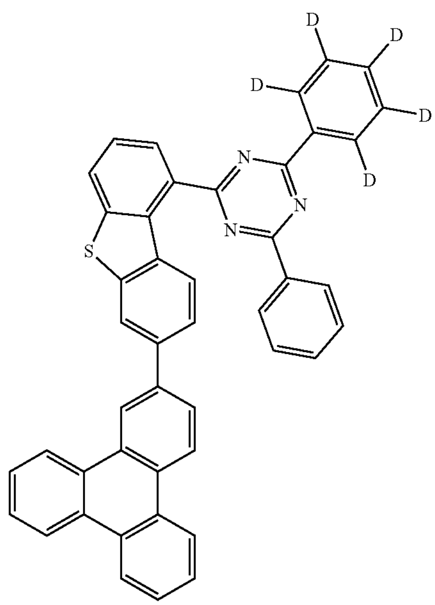
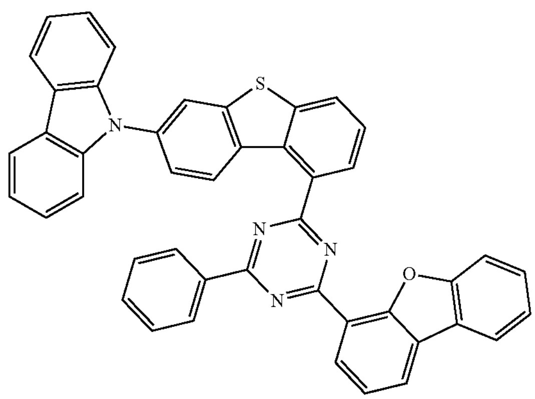
-continued
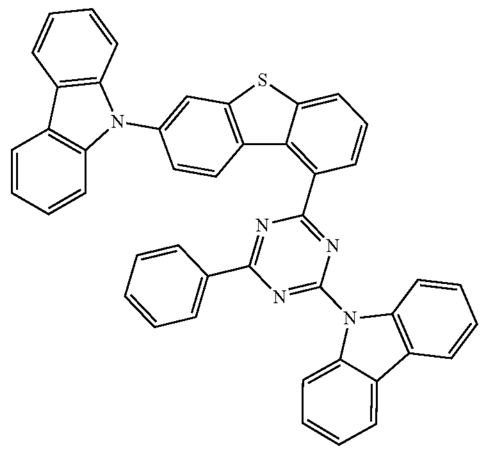
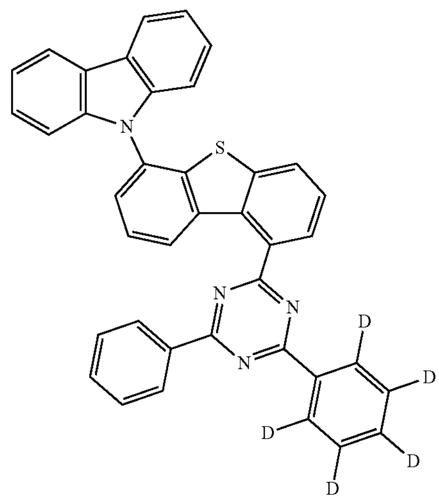
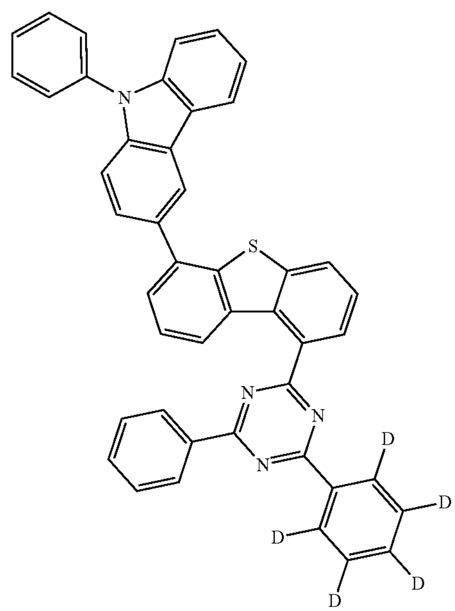

-continued
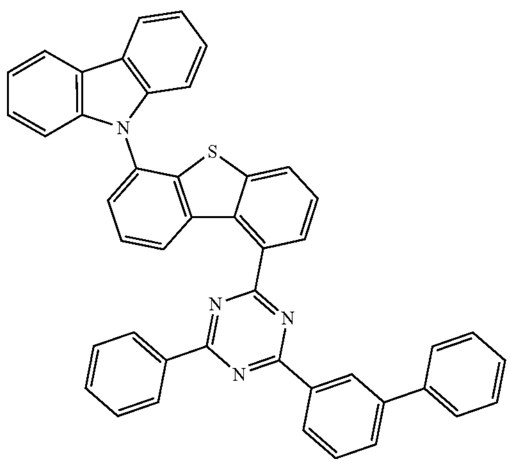
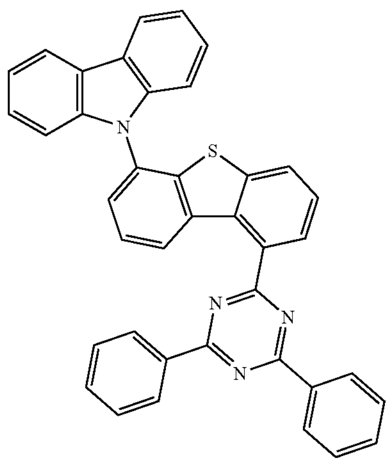
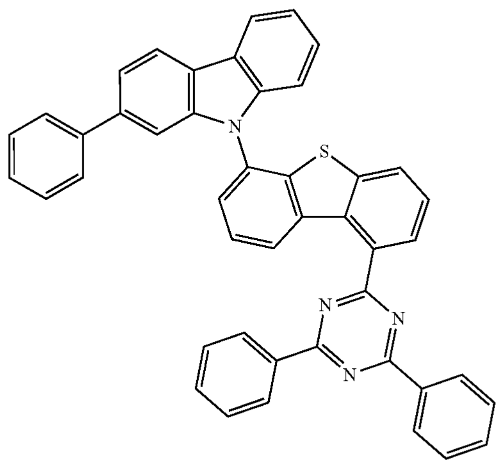
-continued
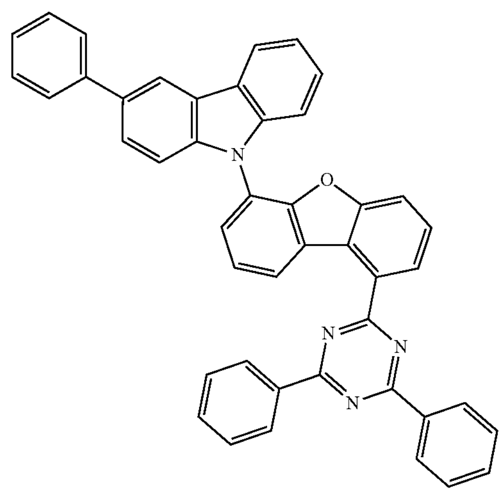
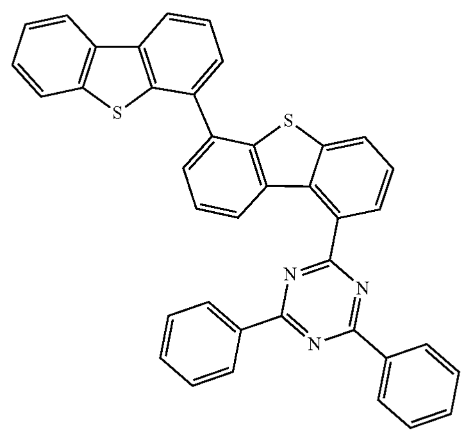
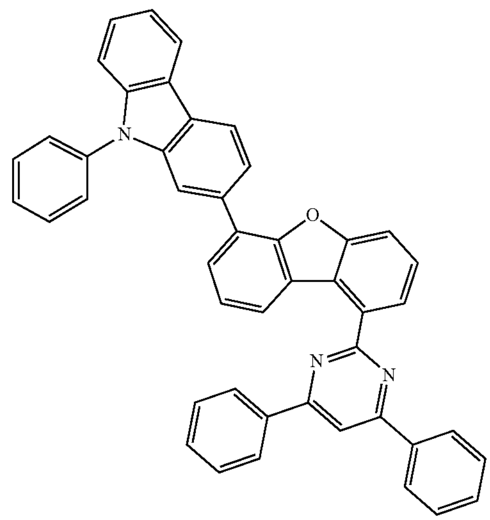

-continued
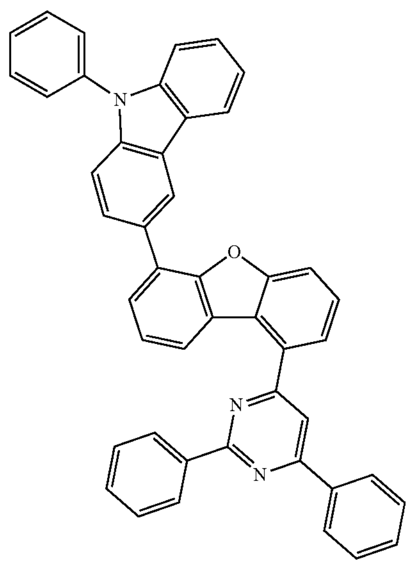
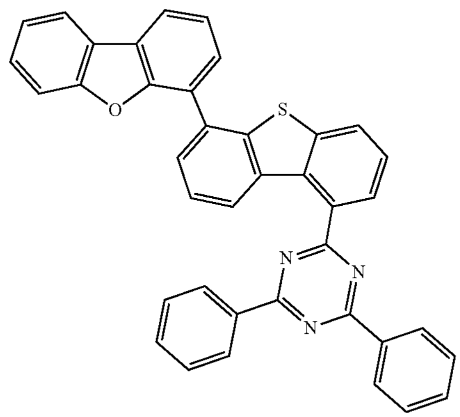
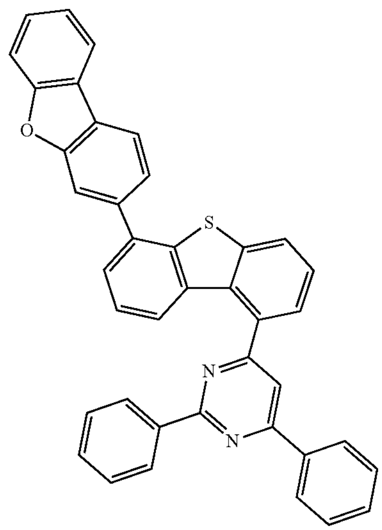
-continued
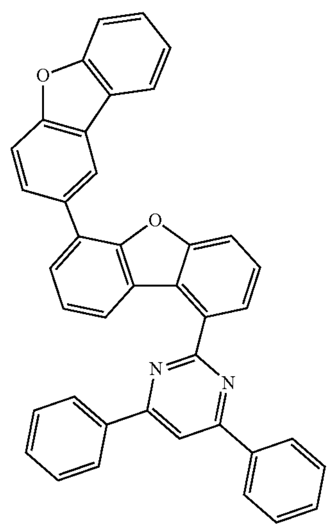
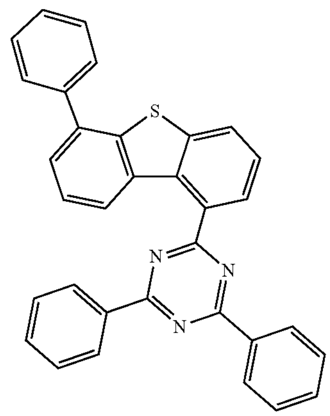
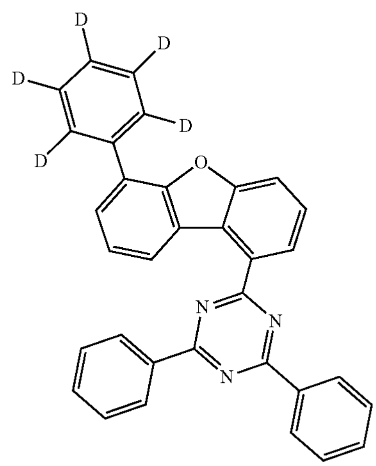

-continued
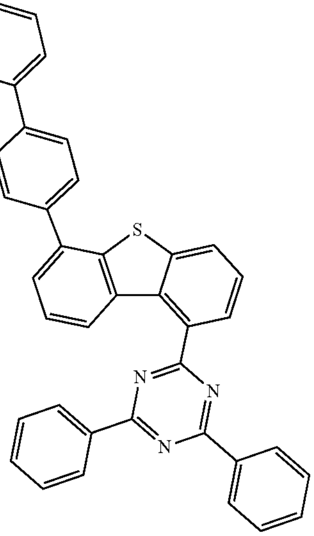
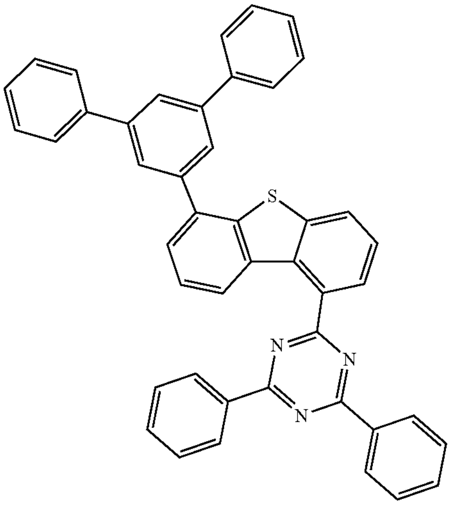
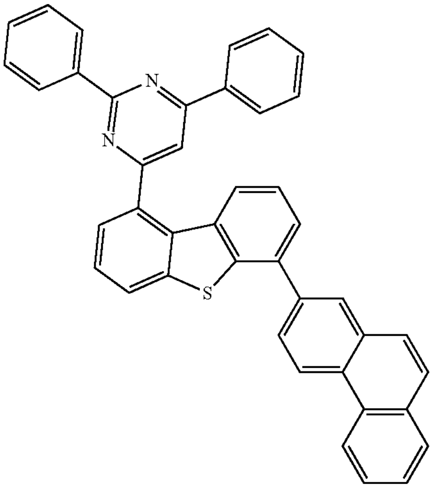
-continued
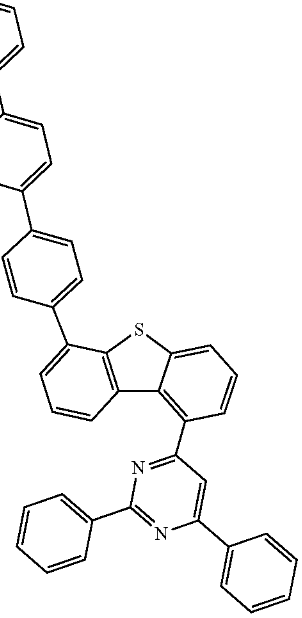
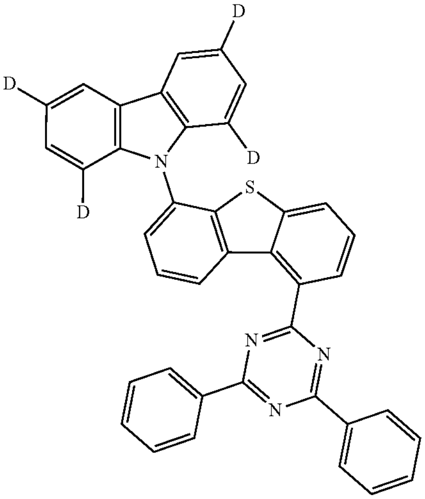

-continued
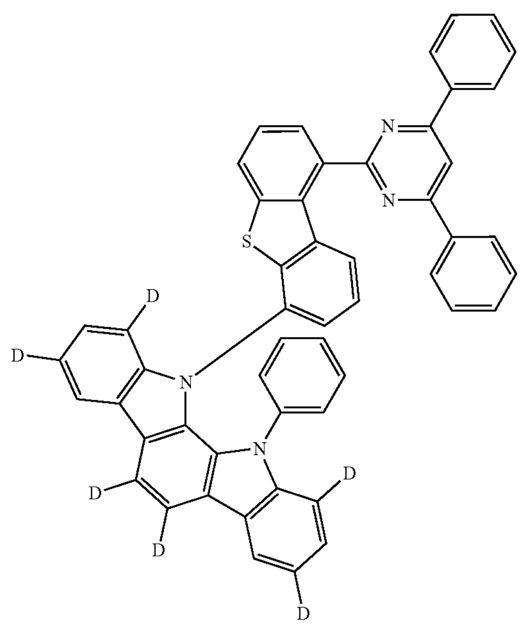
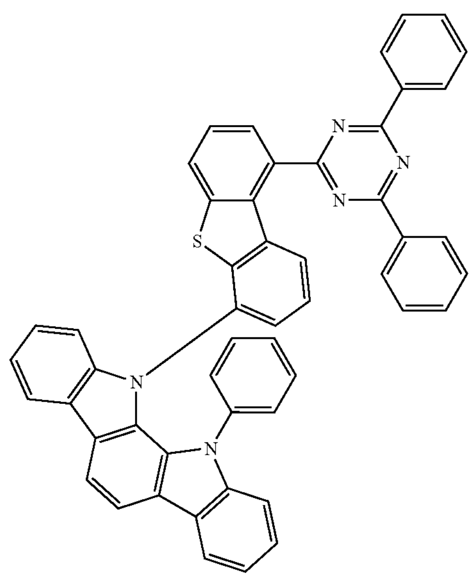
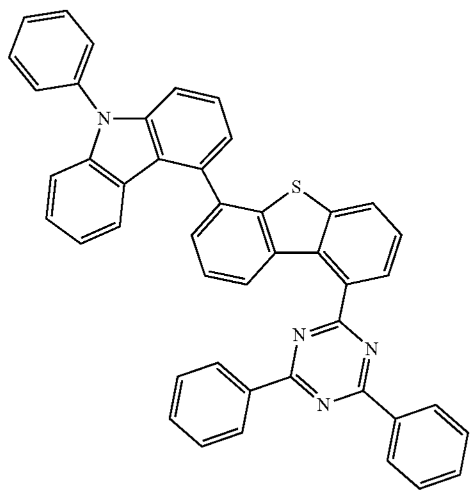
-continued
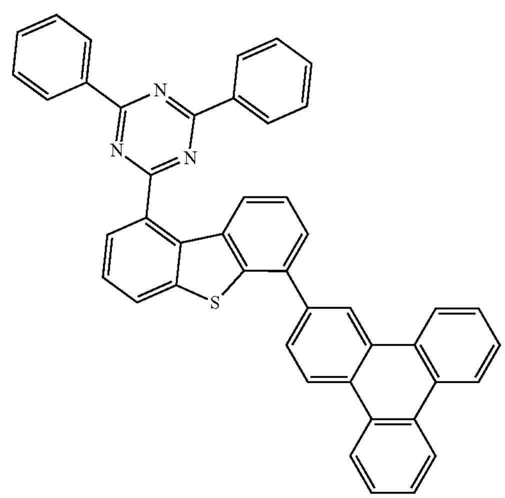
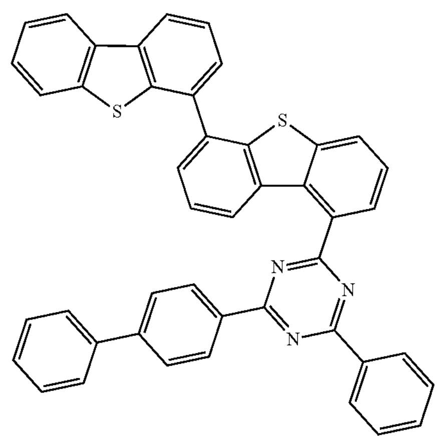
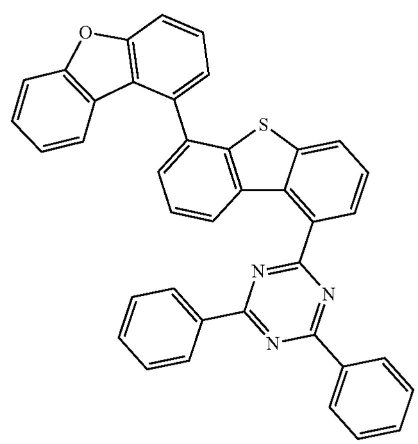

-continued
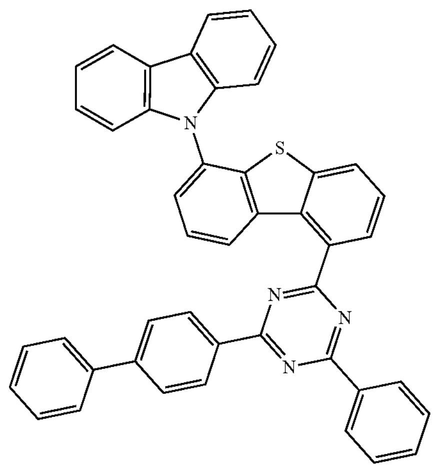
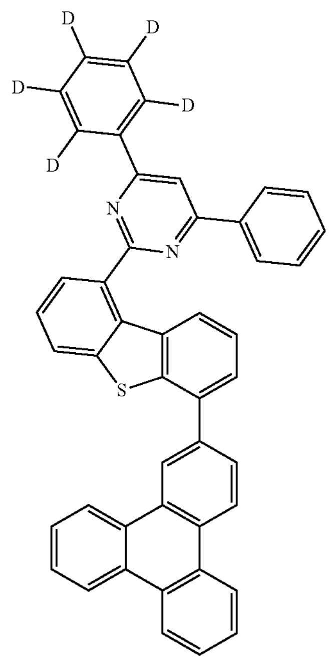
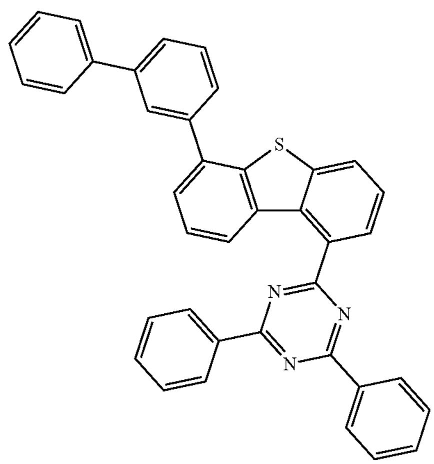
-continued
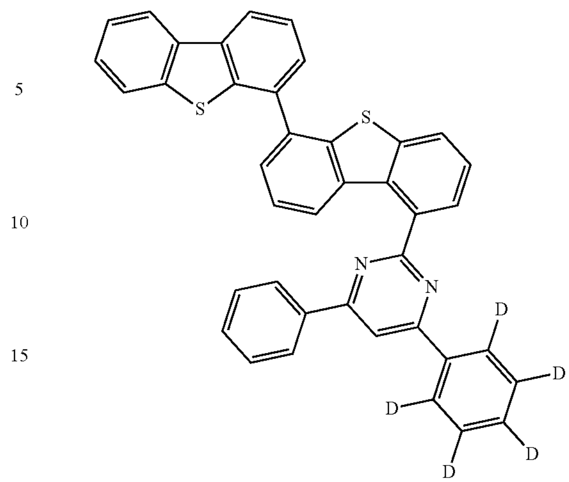
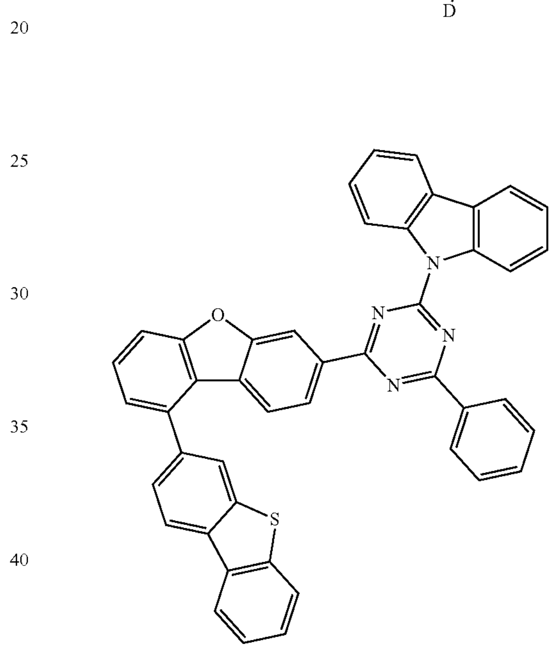
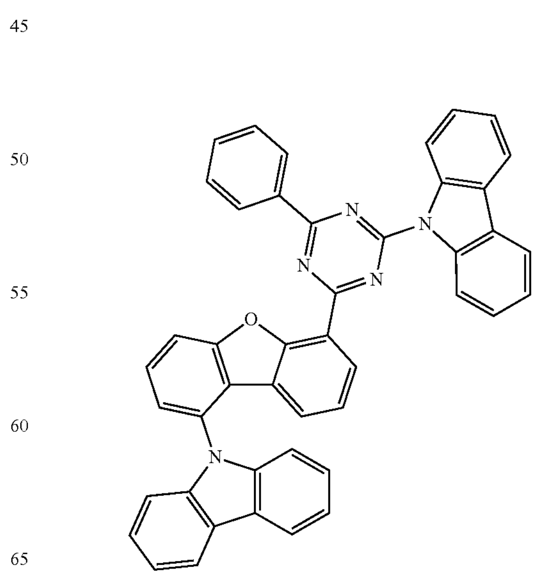

-continued
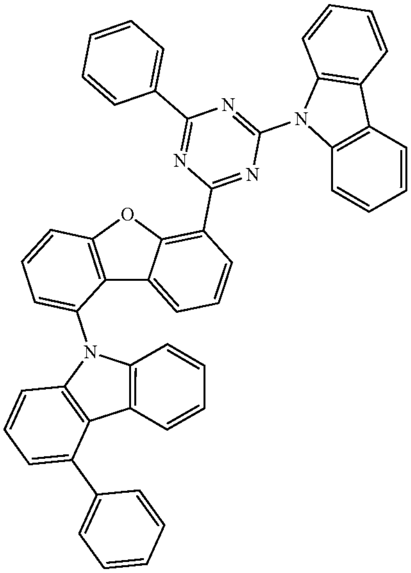
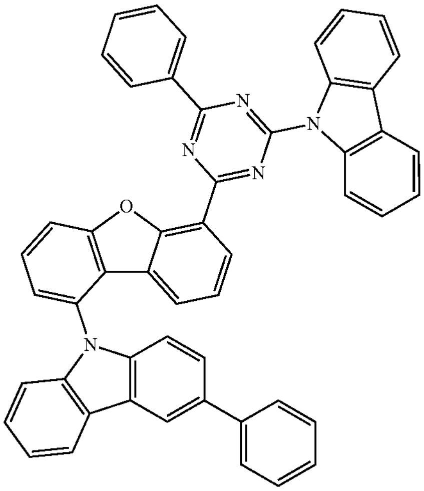
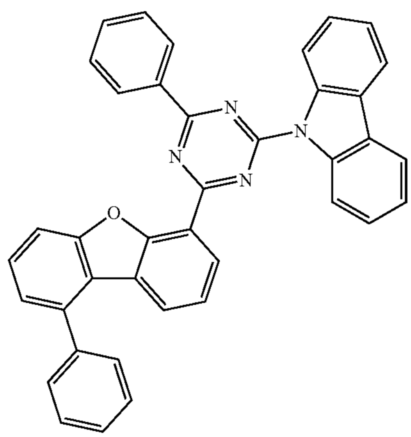
-continued
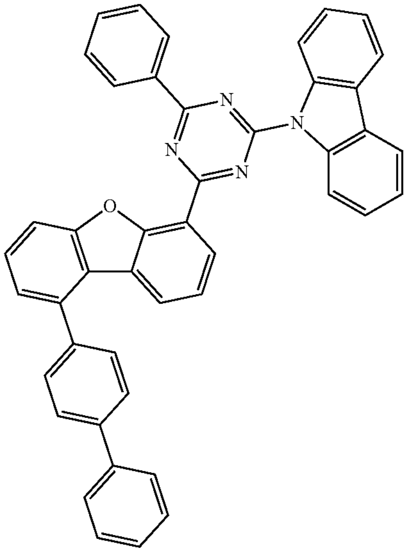
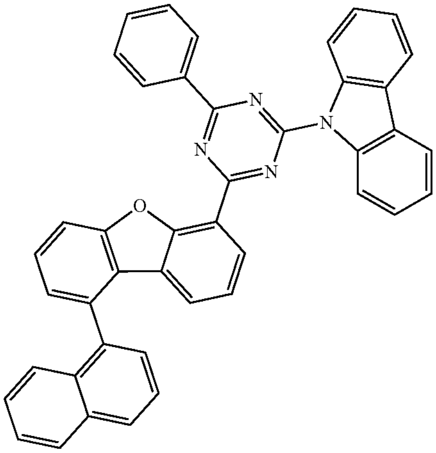
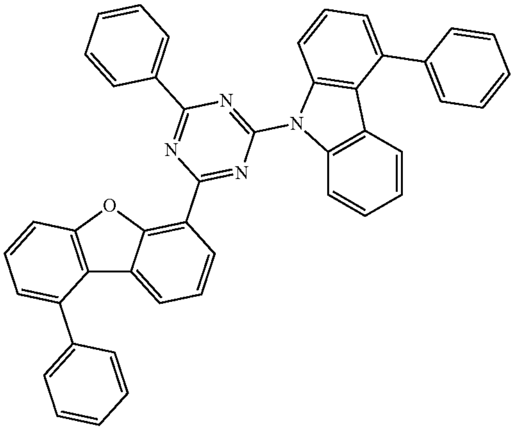

-continued
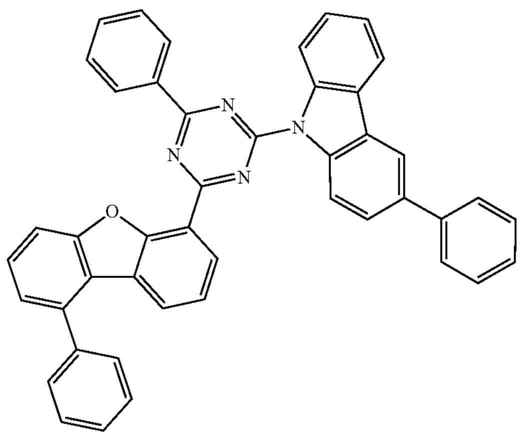
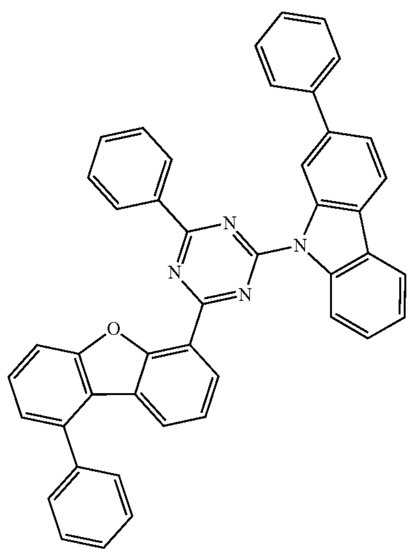
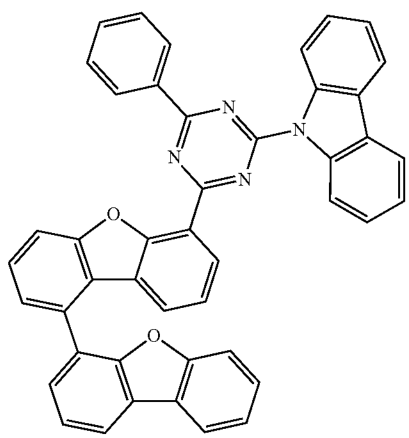
-continued
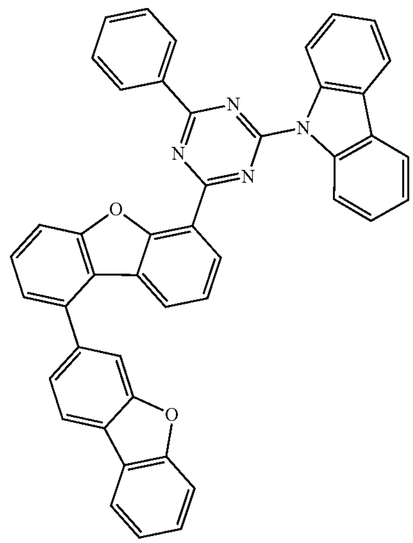
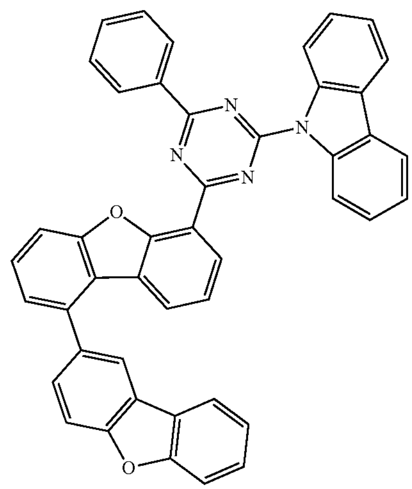
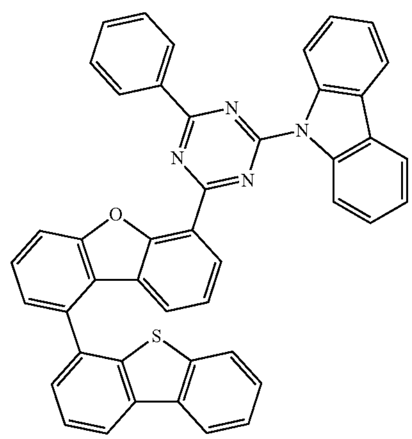

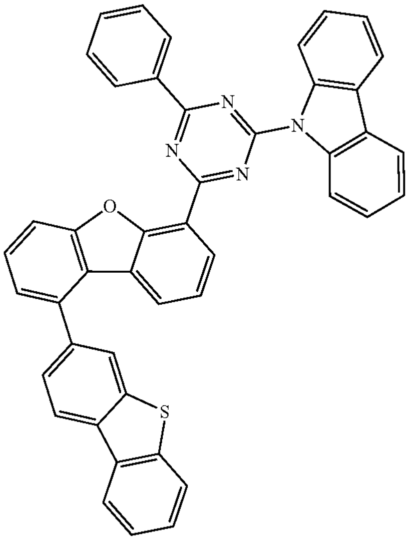
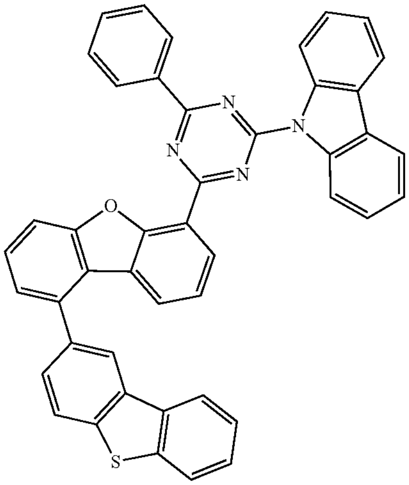
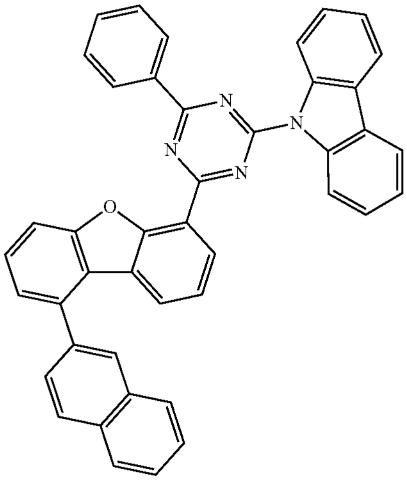
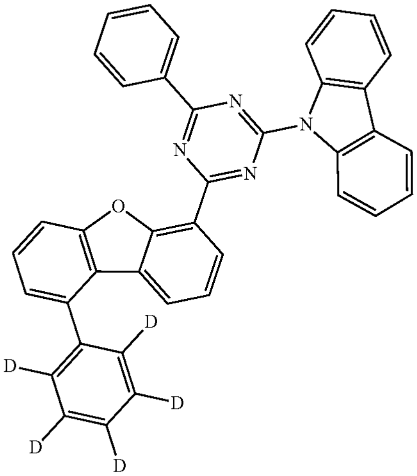
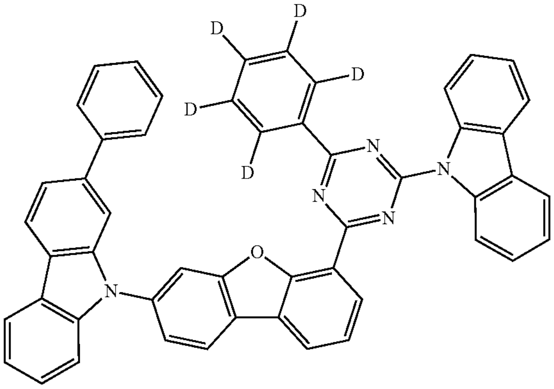
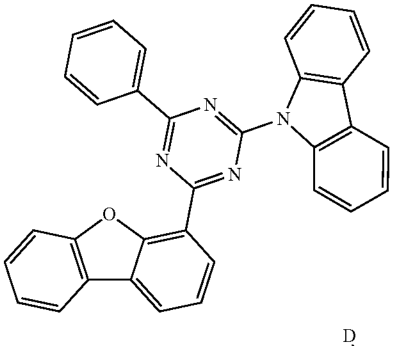
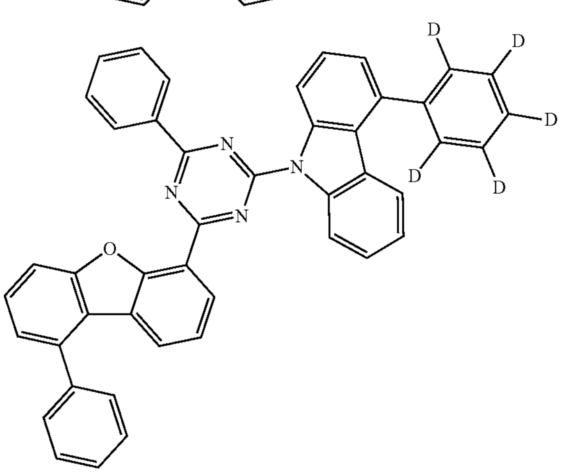

-continued
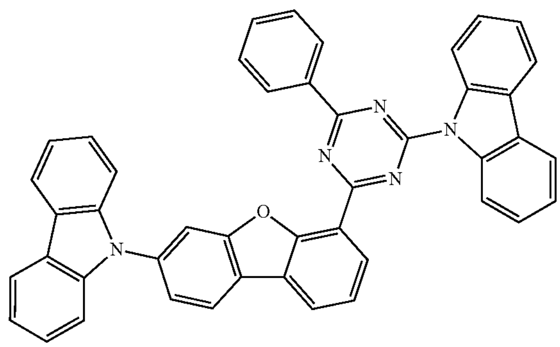
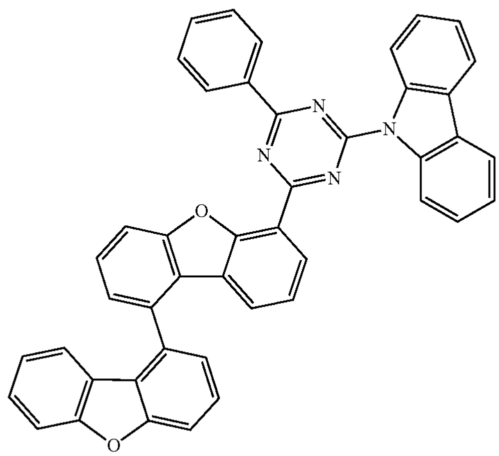
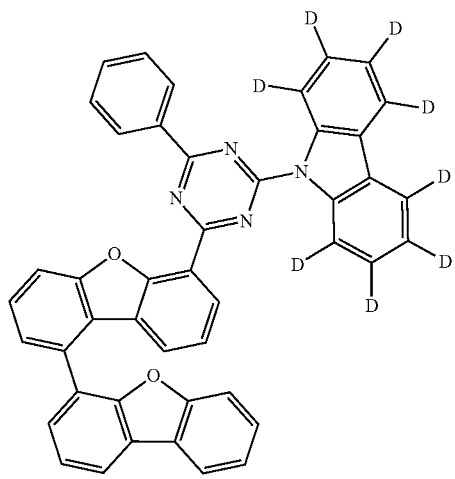
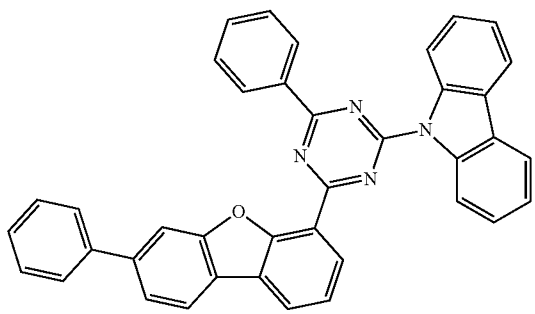
-continued
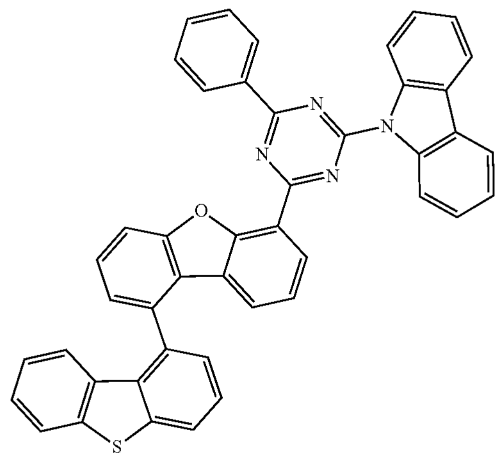
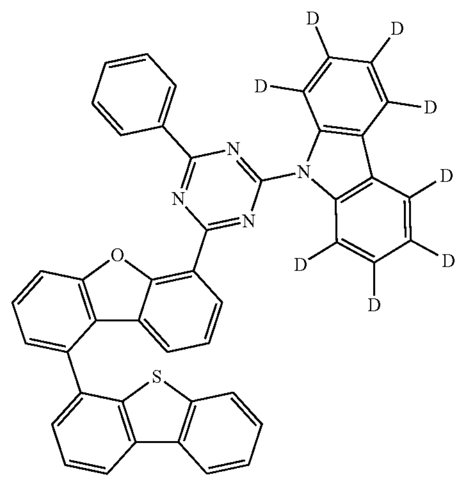
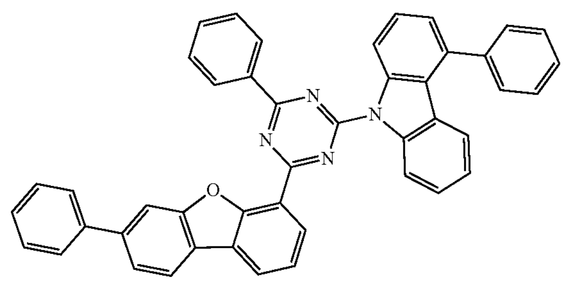
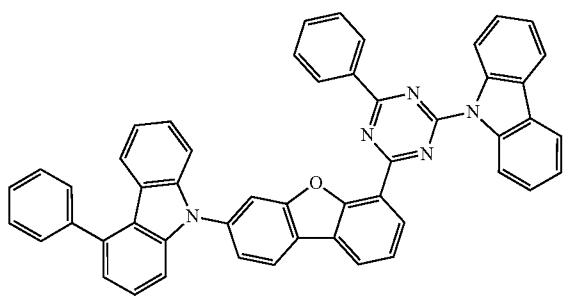

-continued
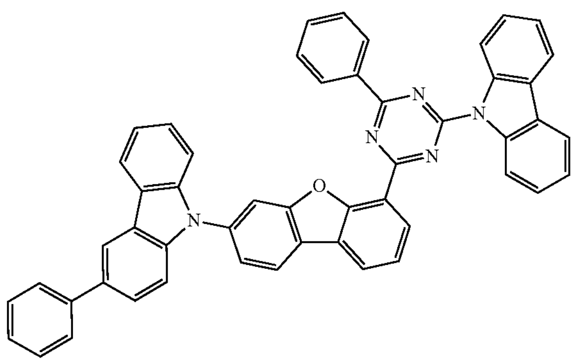
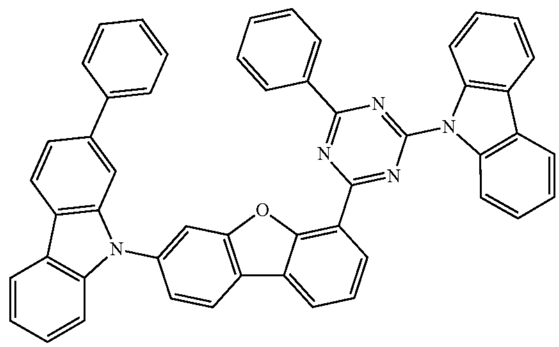
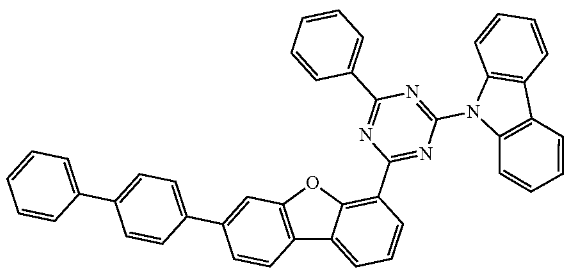
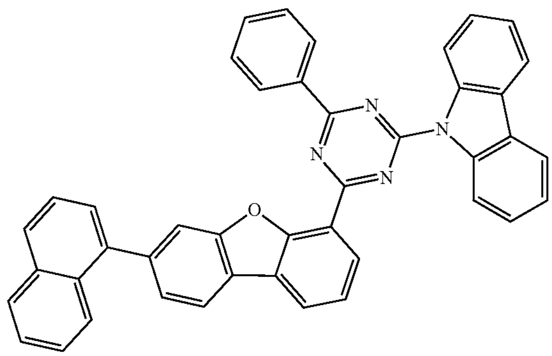
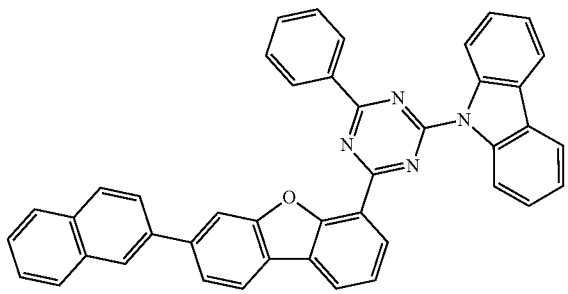
-continued
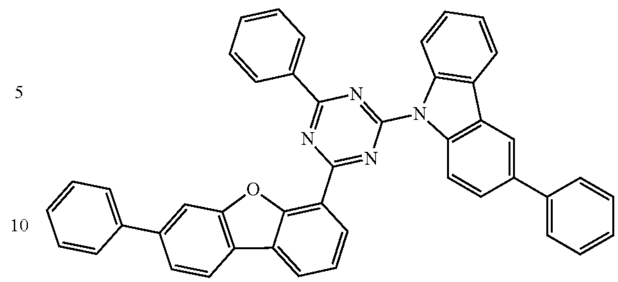
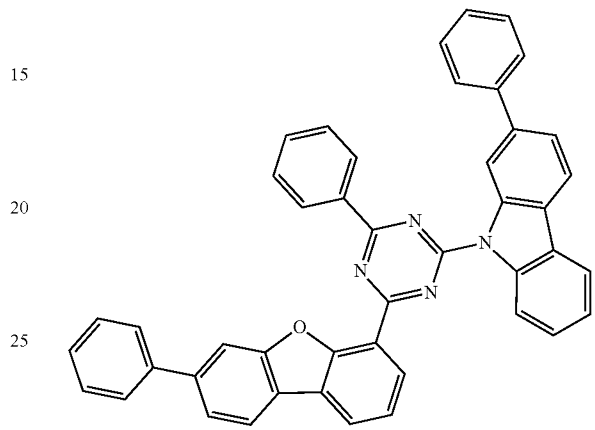
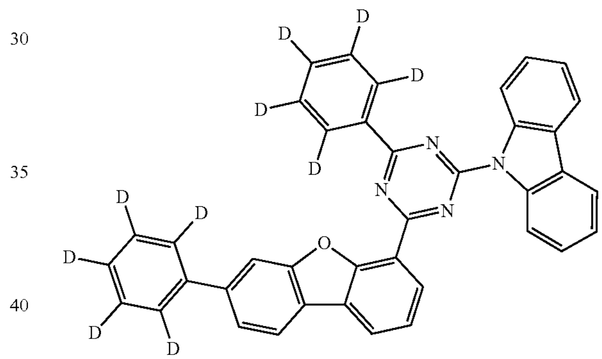
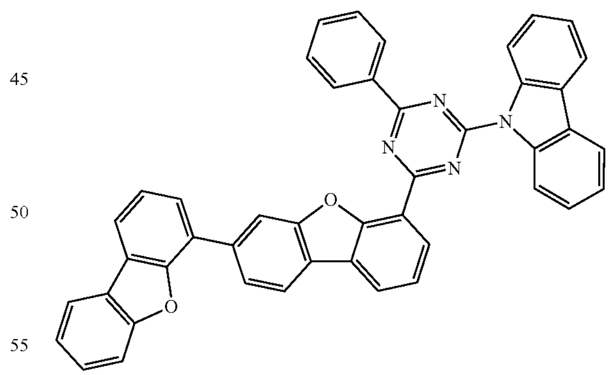
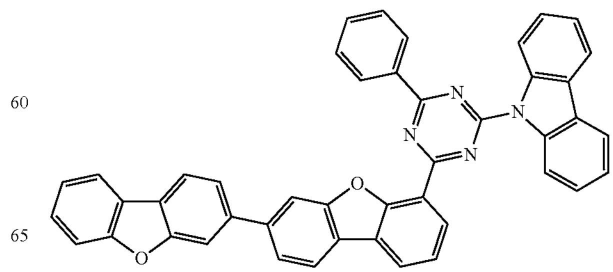

-continued
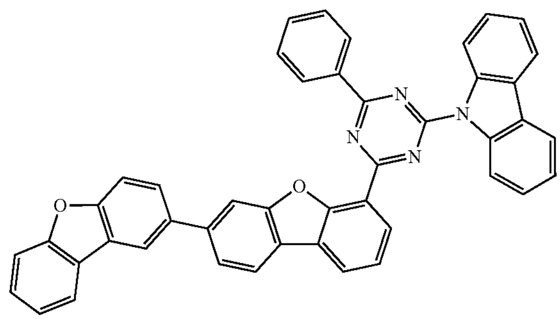
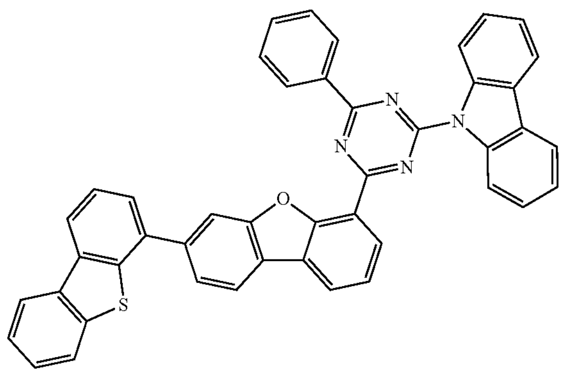
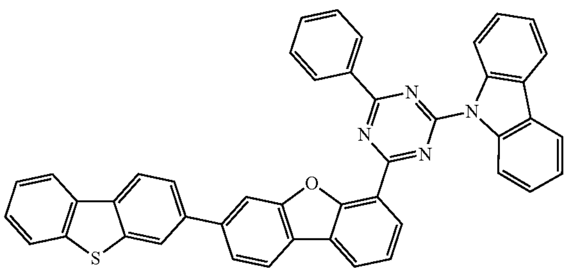
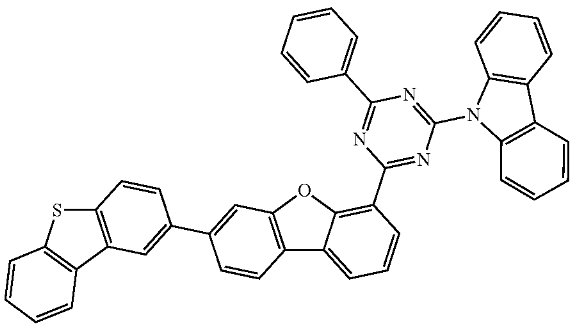
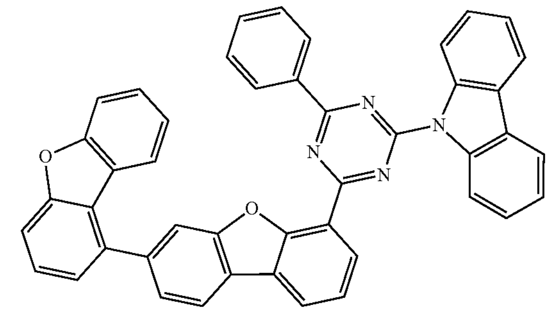
-continued
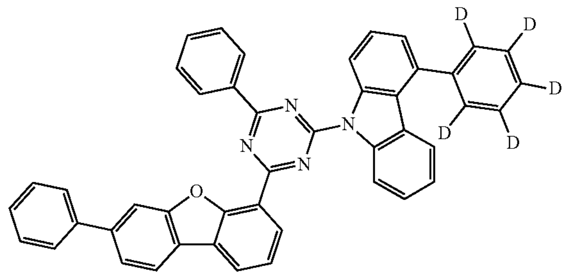
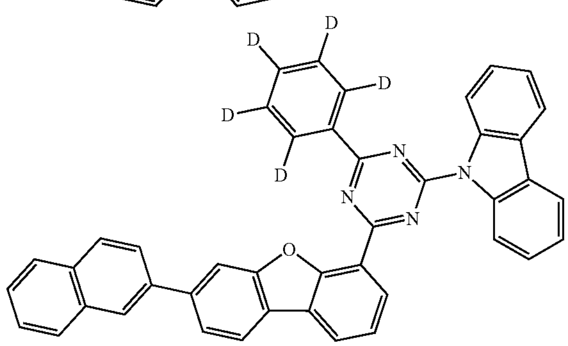
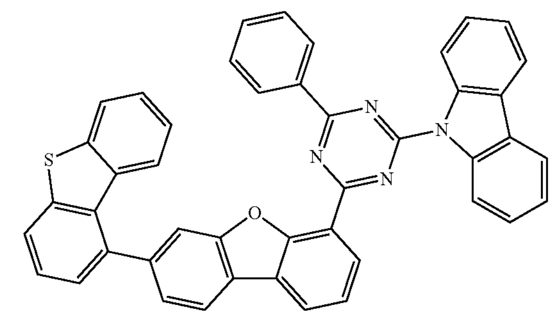
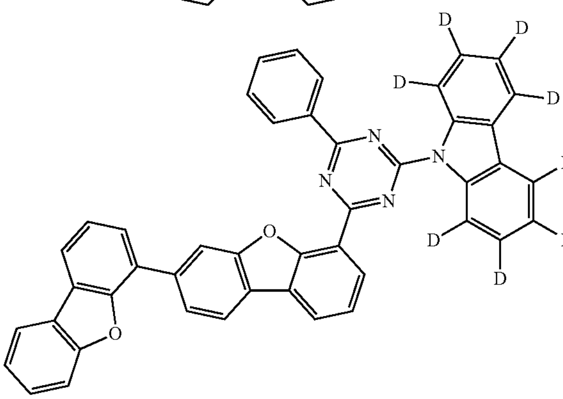
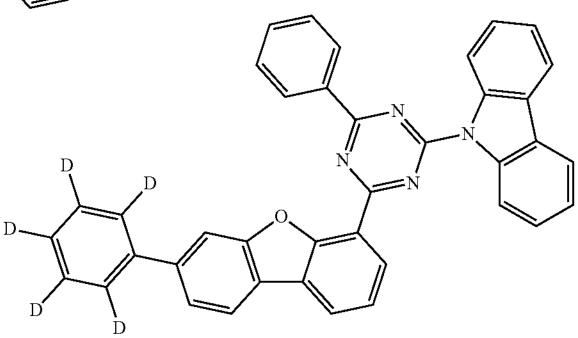

-continued
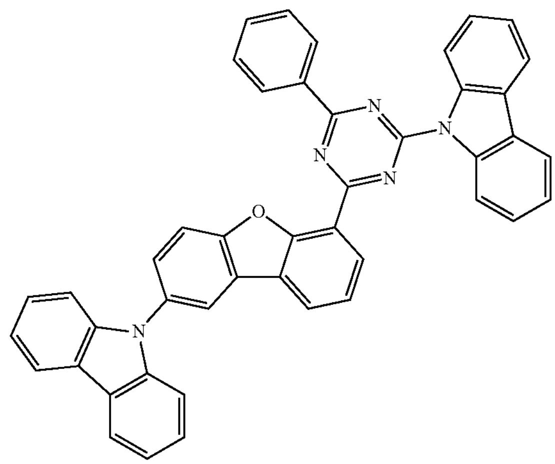
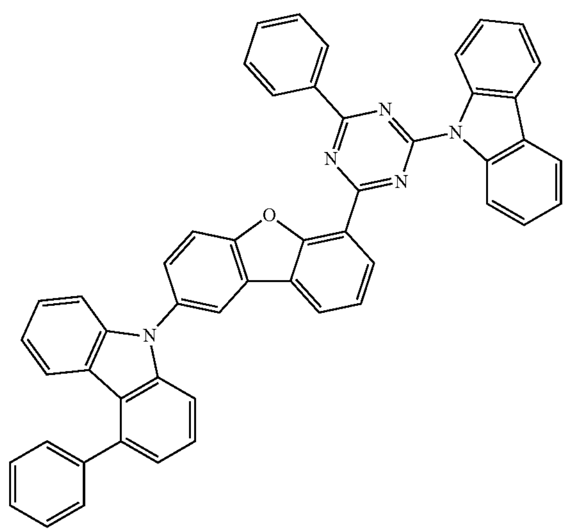
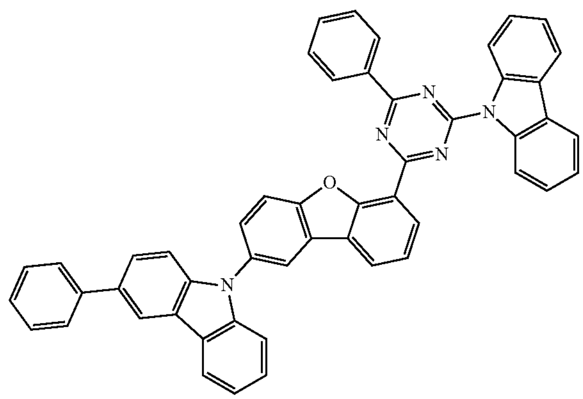
-continued
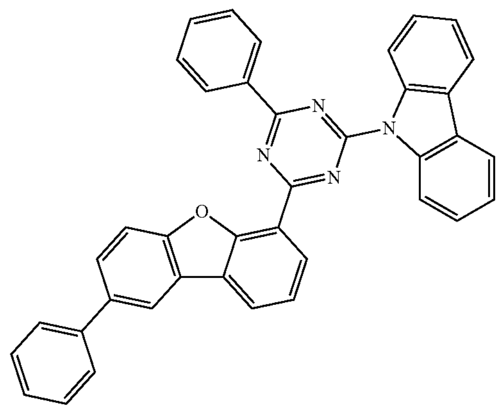
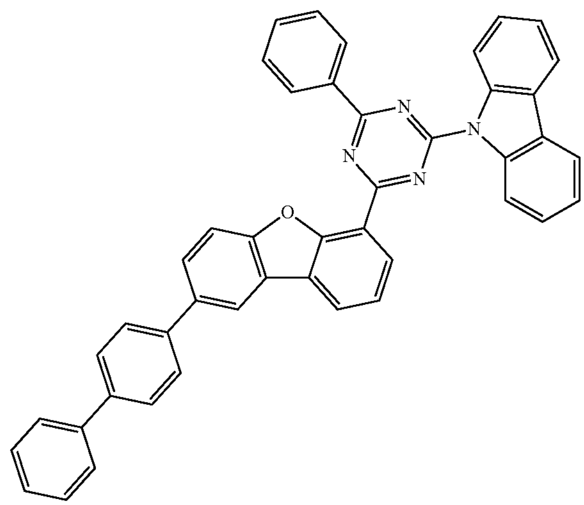
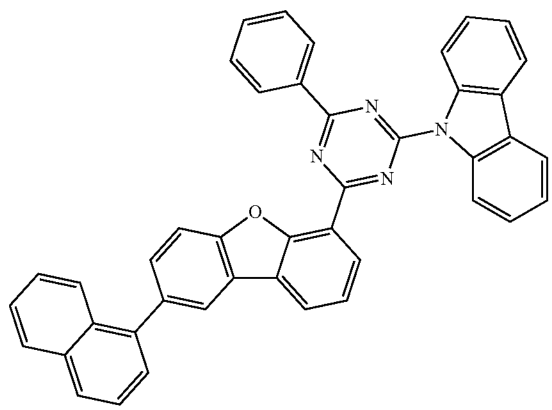
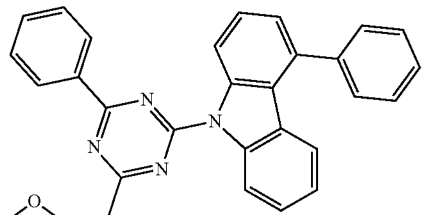
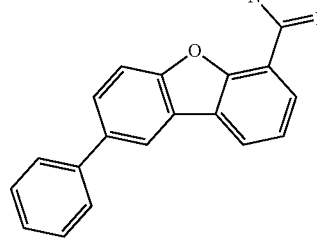

-continued
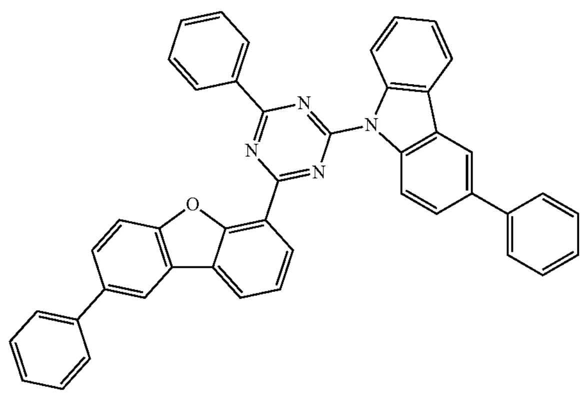
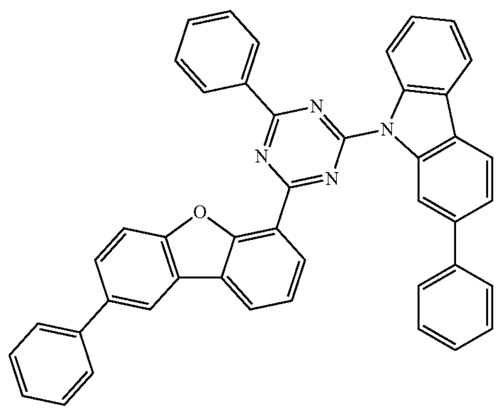
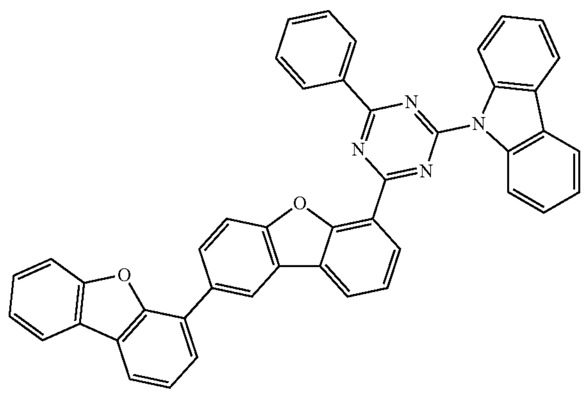
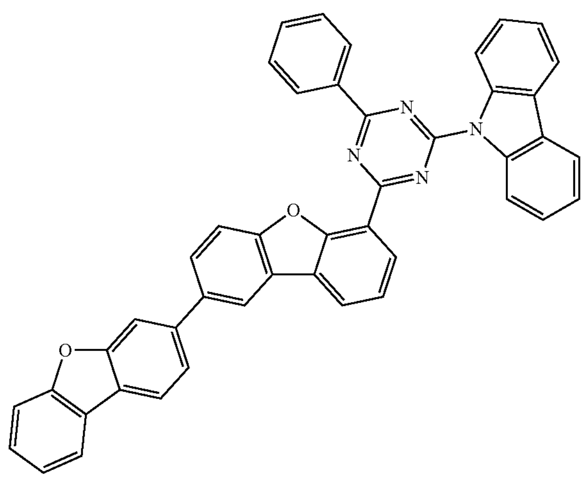
-continued
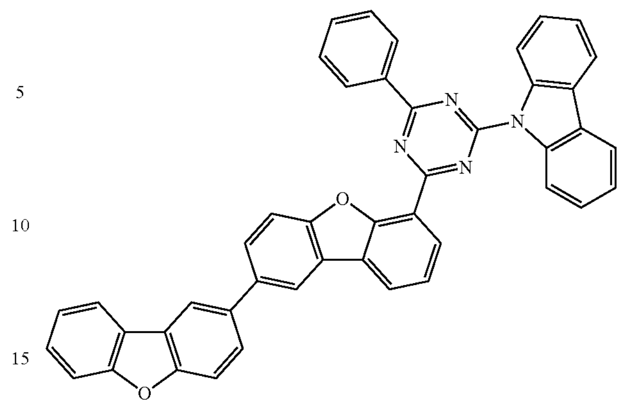
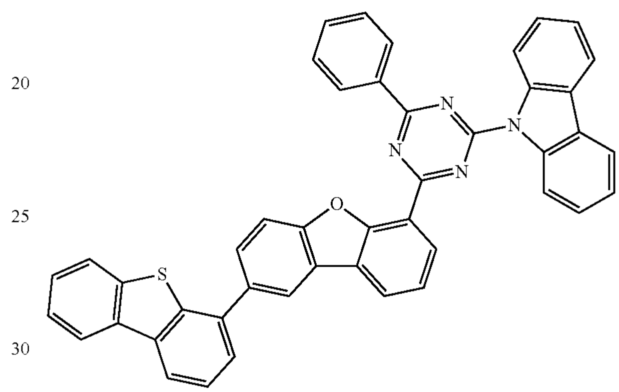
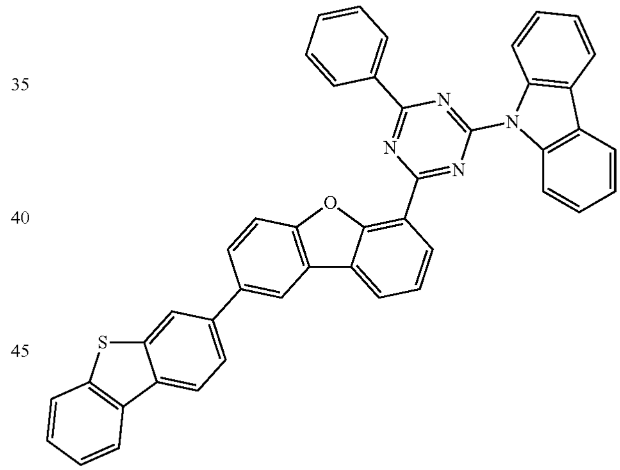
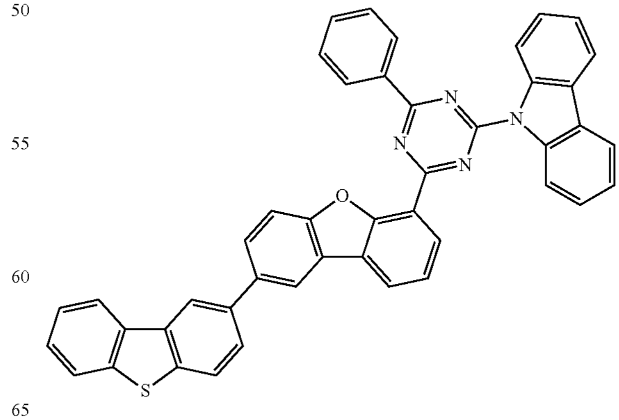

-continued
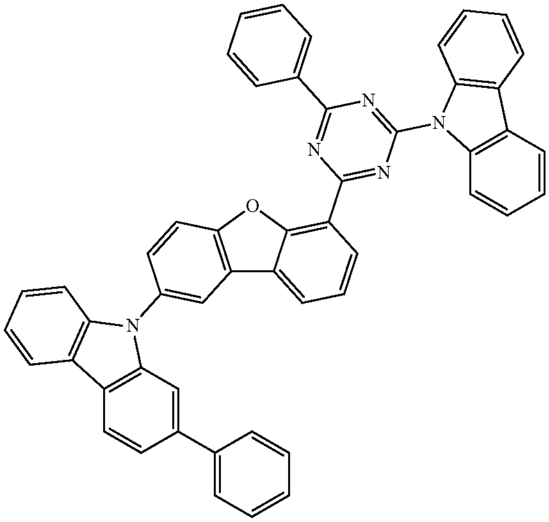
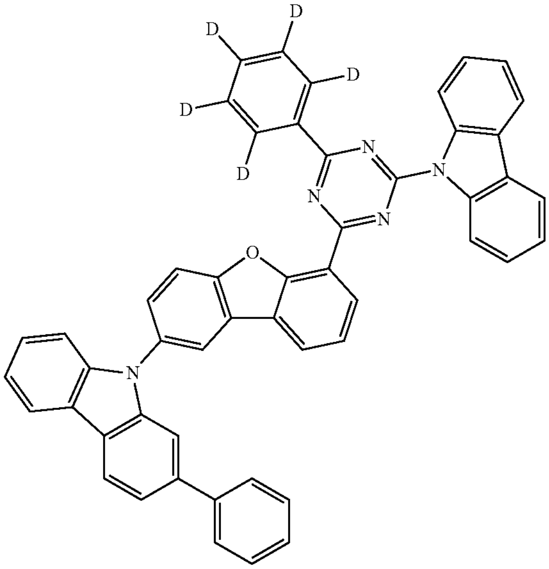
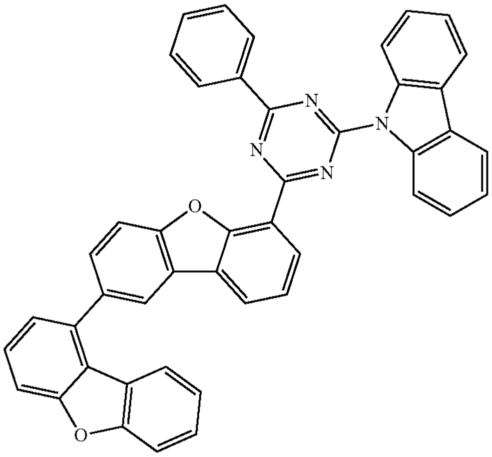
-continued
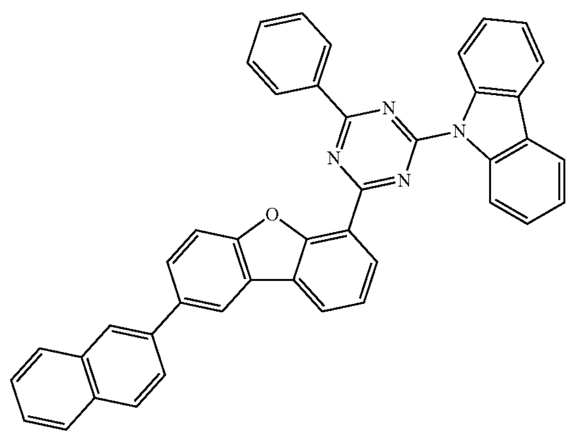
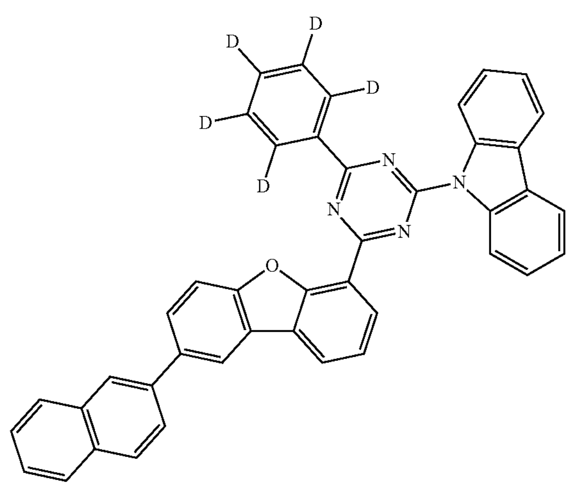
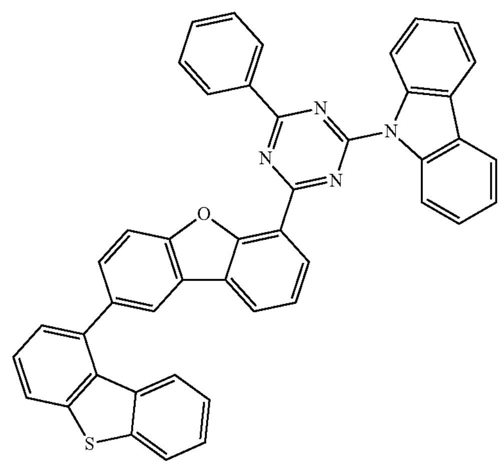

-continued
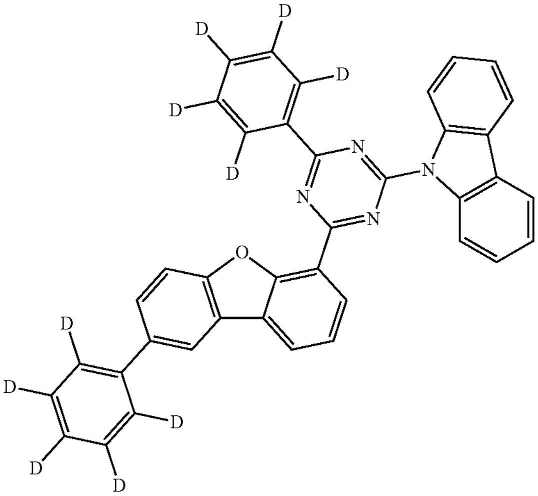
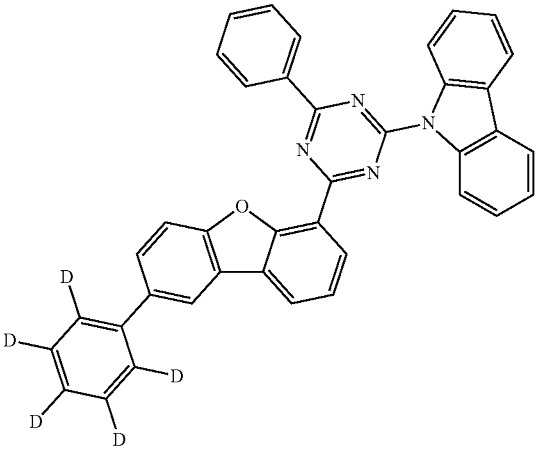
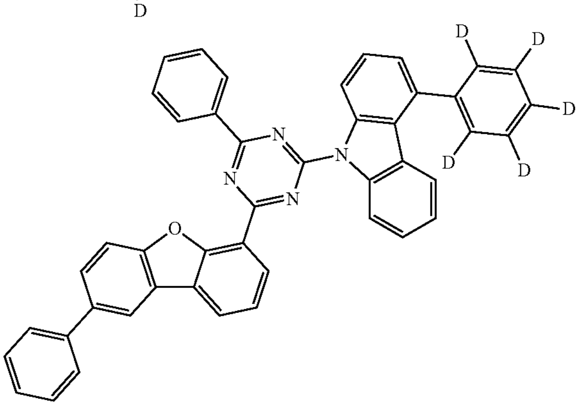
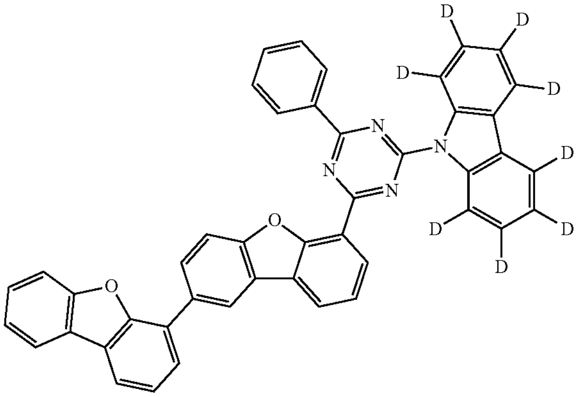
-continued
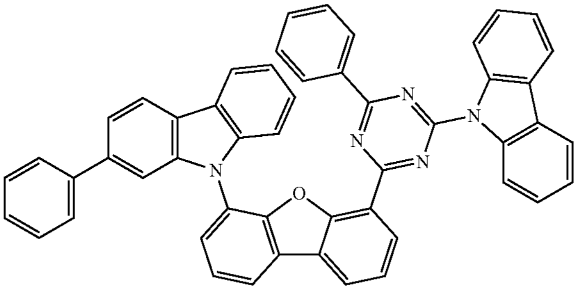
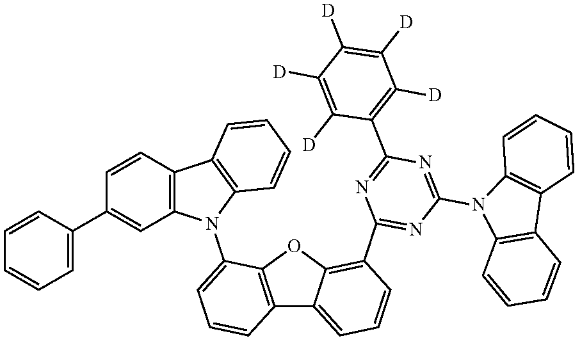
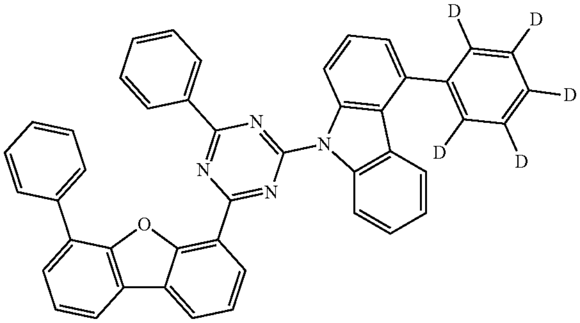
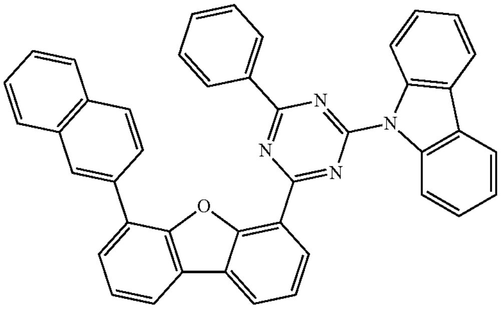
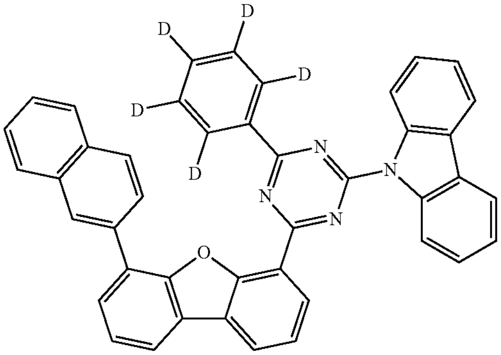

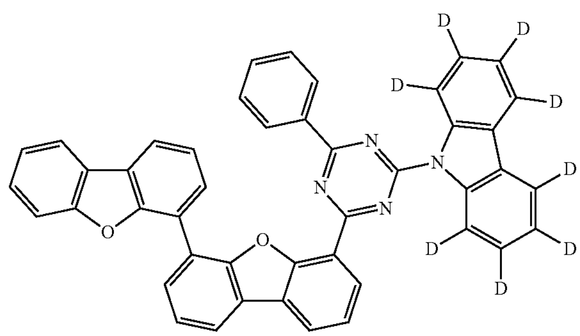
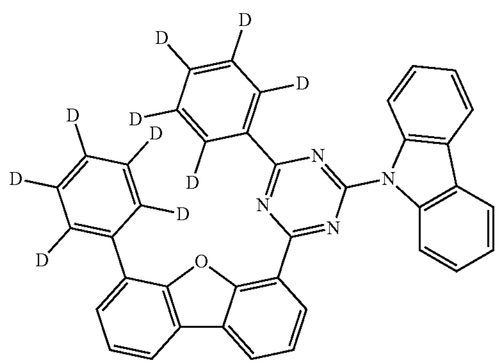
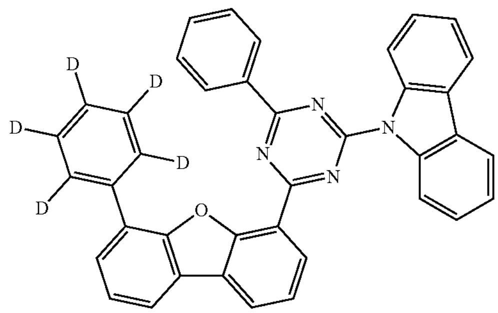
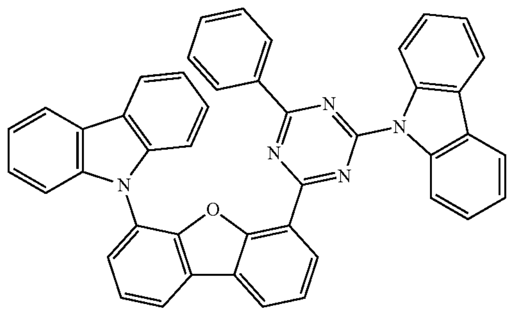
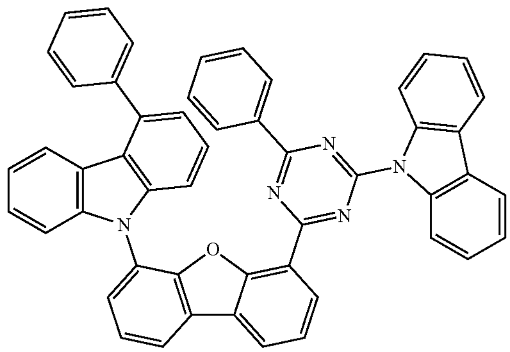
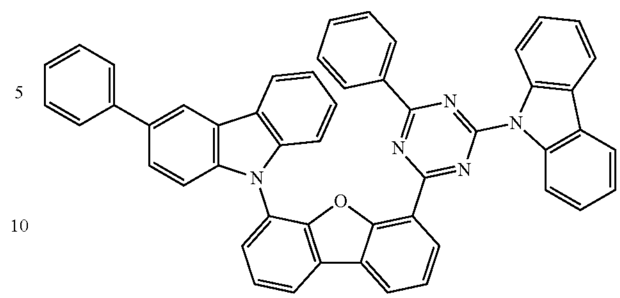
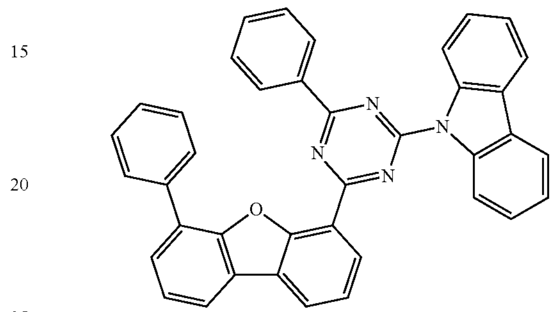
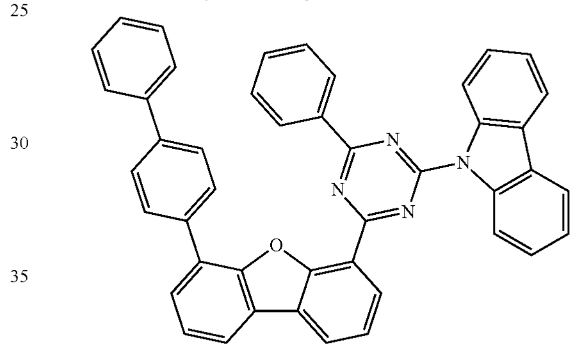
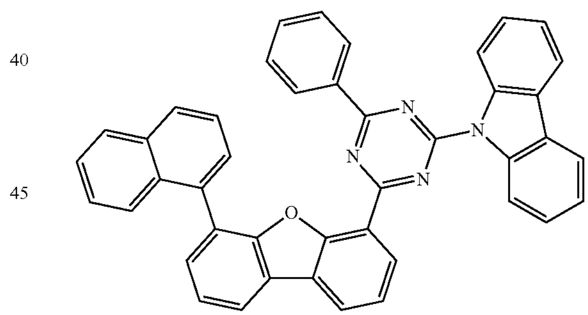
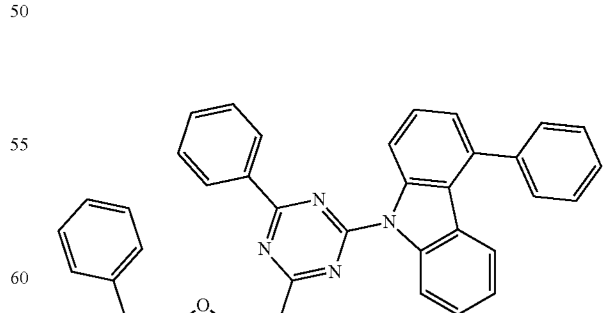
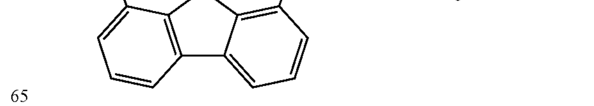

-continued
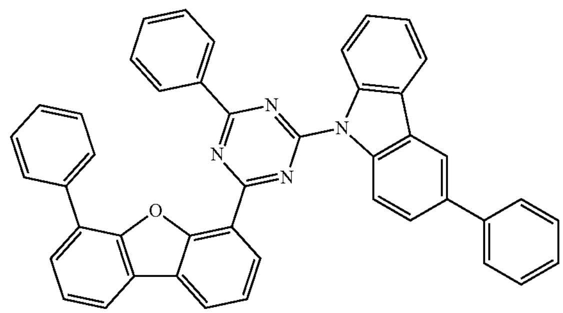
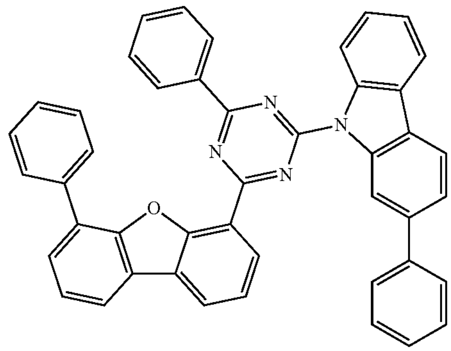
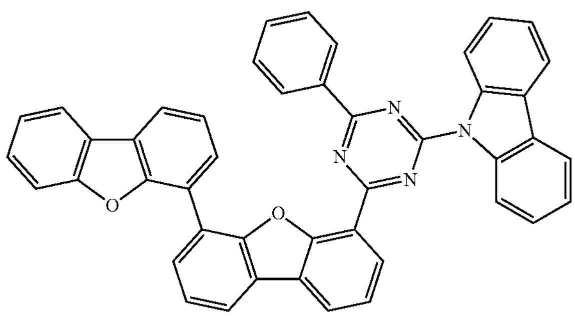
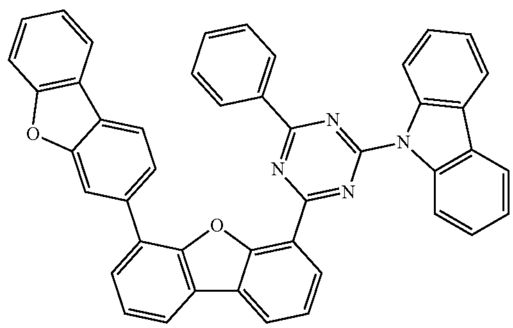
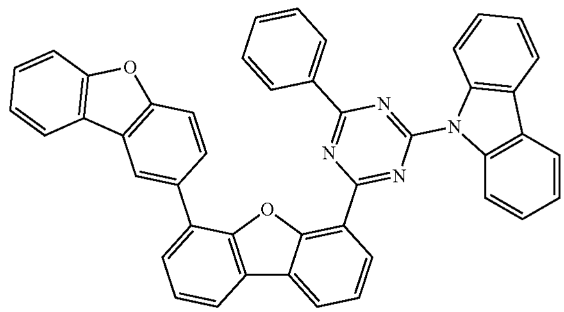
-continued
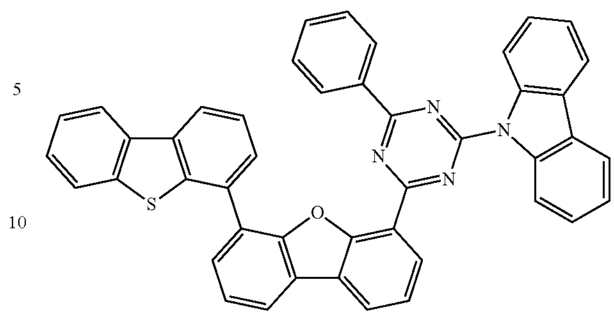
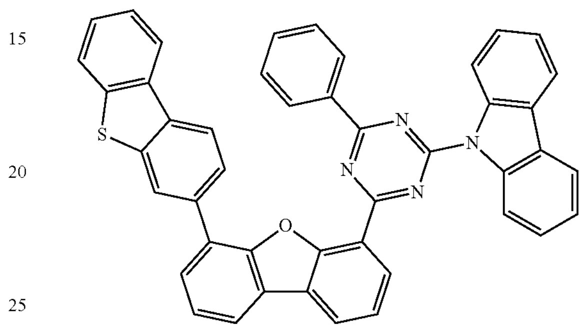
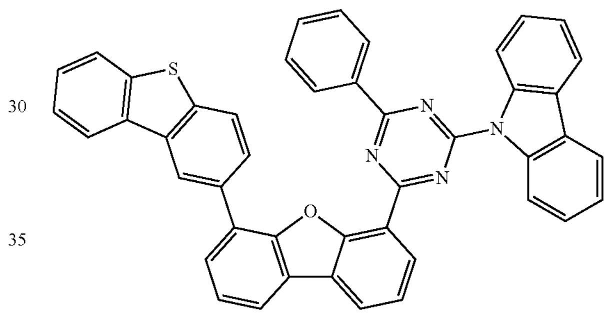
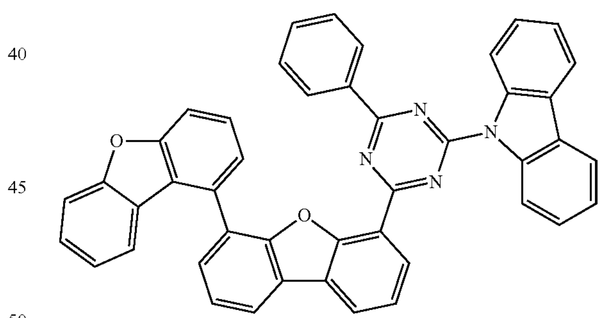
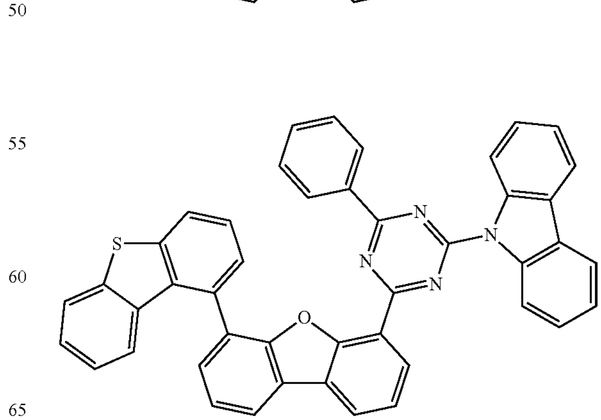

-continued
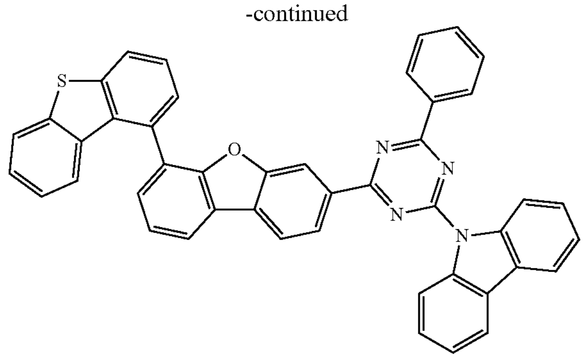
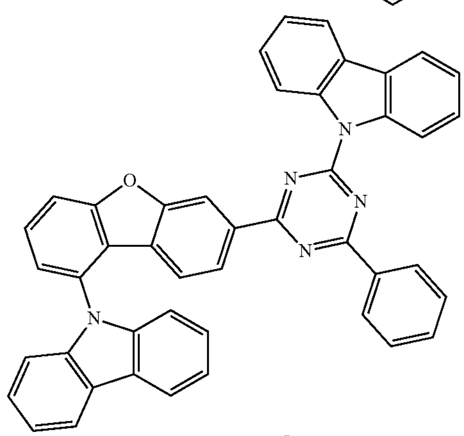
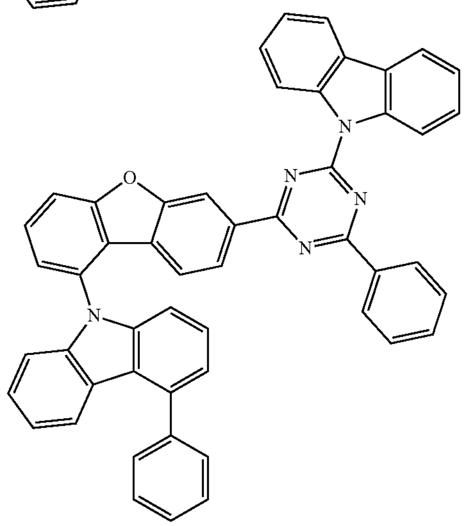
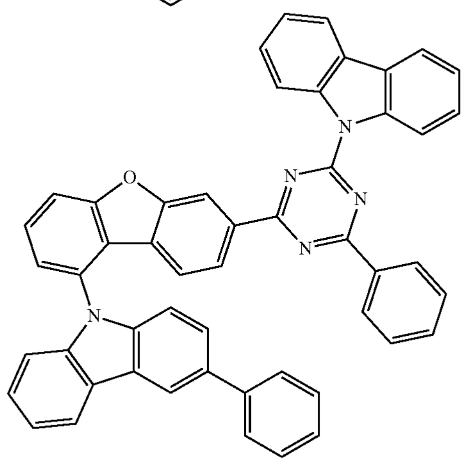
-continued
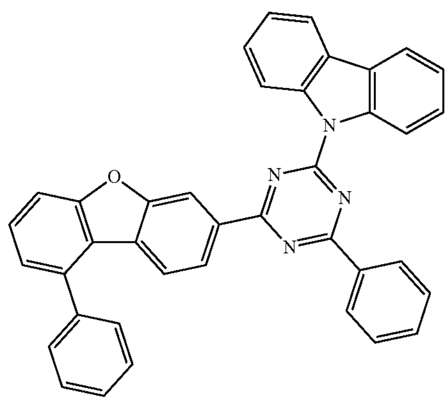
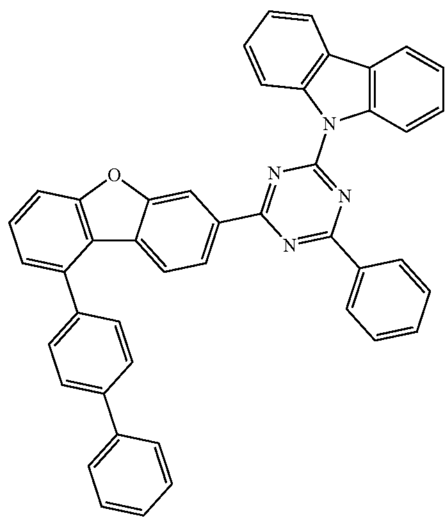
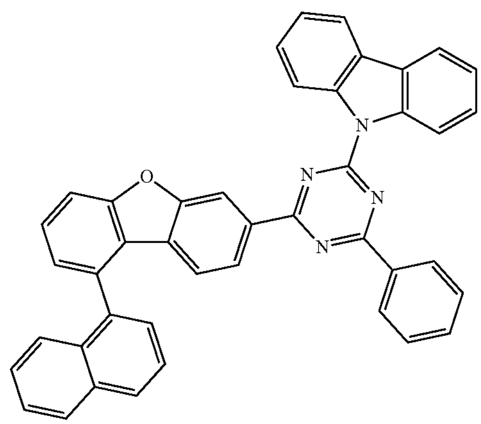

-continued
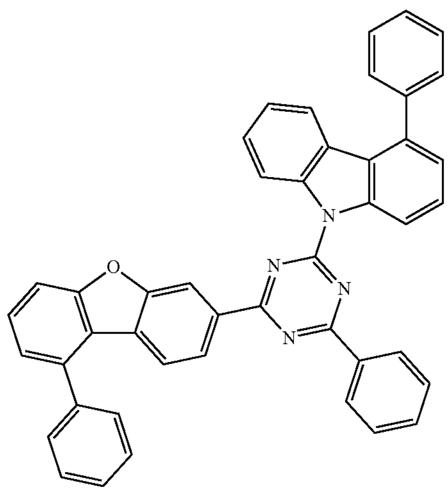
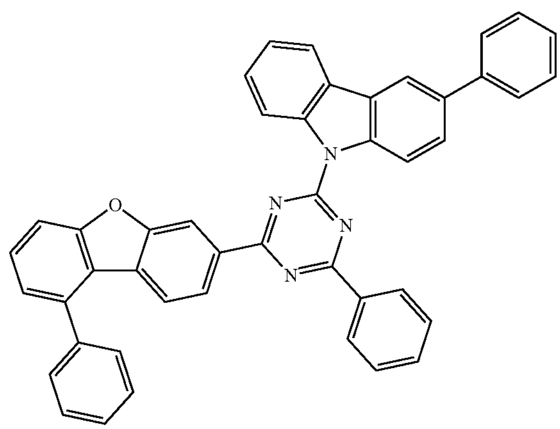
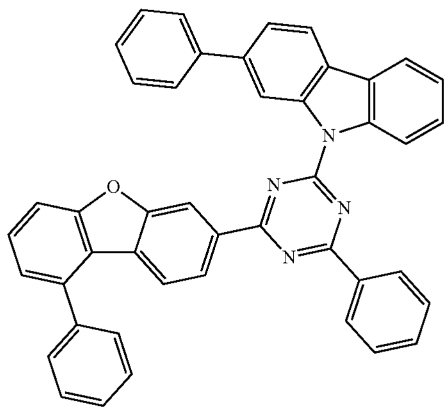
-continued
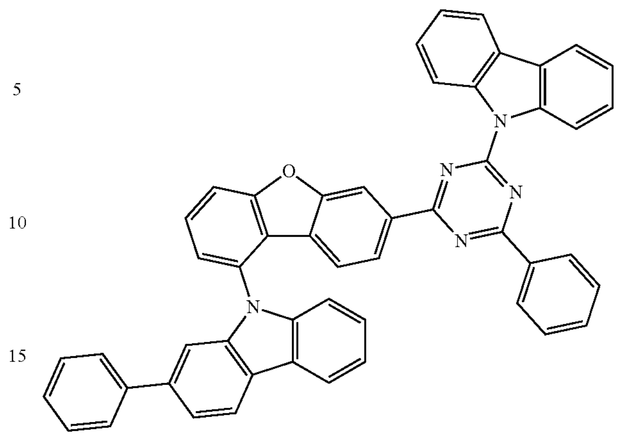
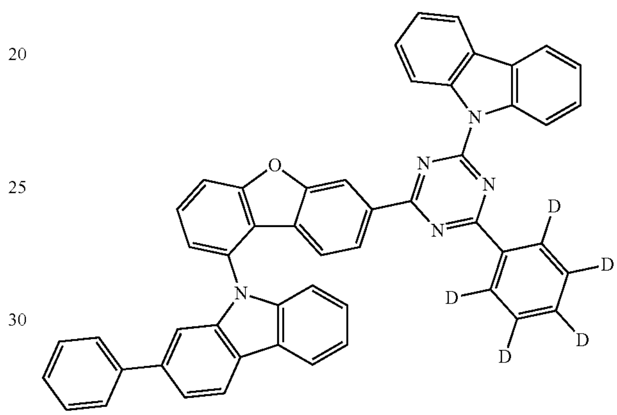
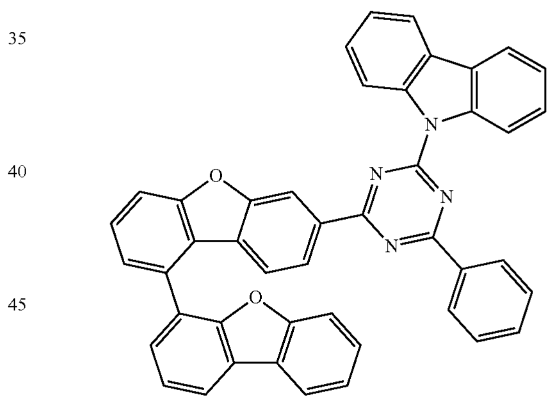
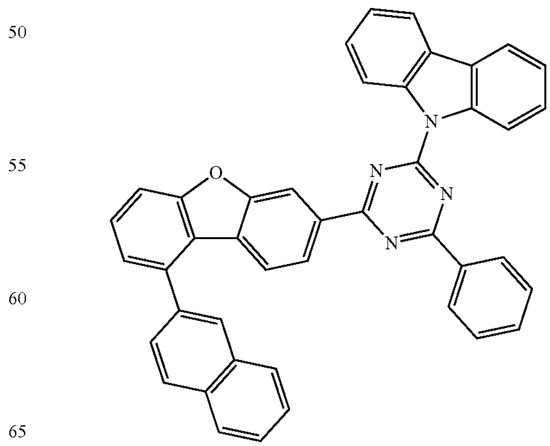

-continued
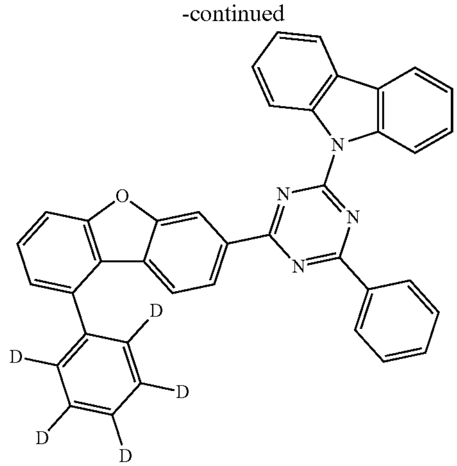
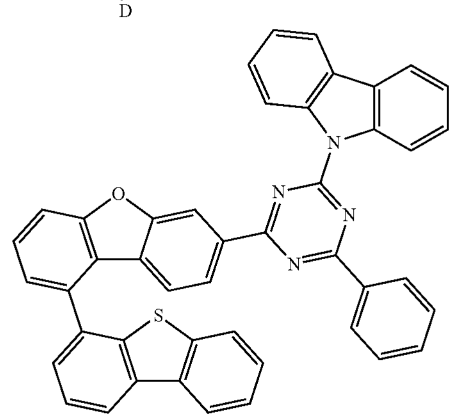
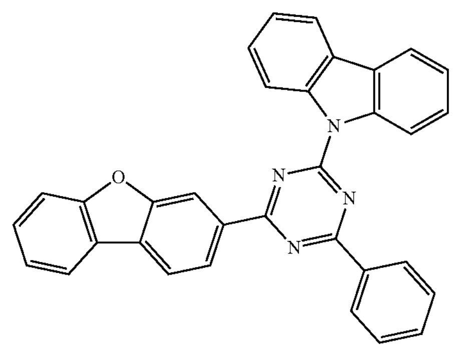
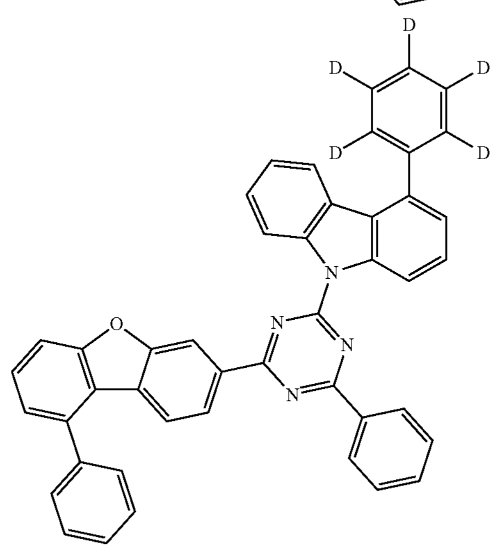
-continued
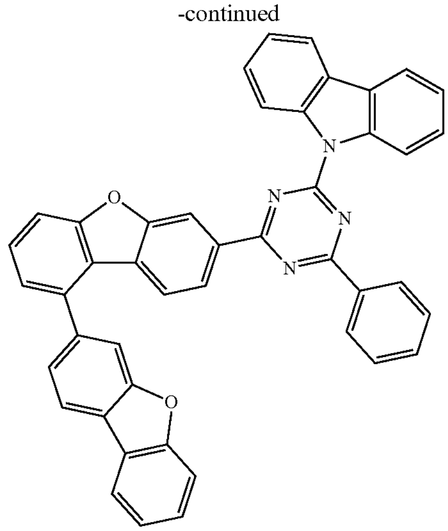
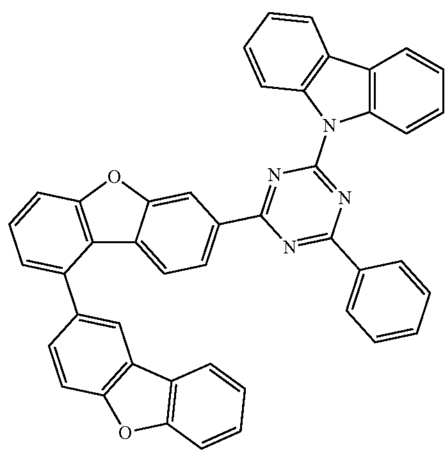
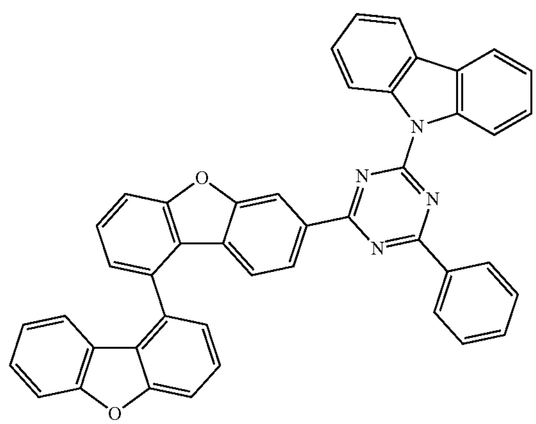

-continued
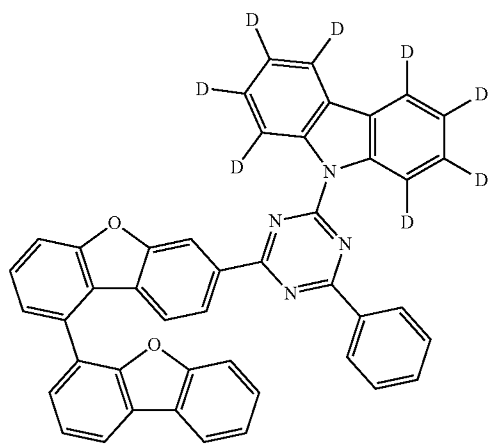
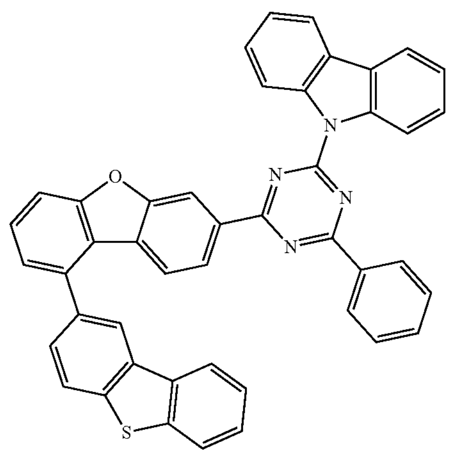
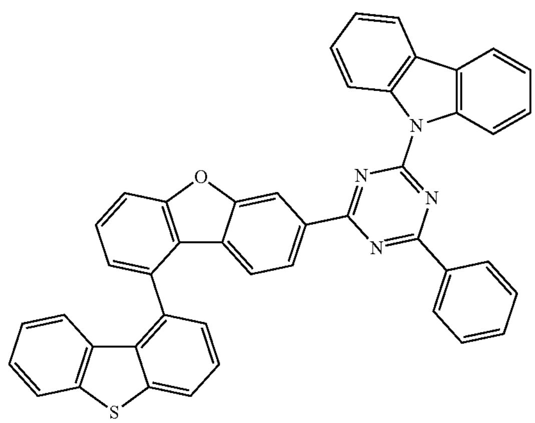
-continued
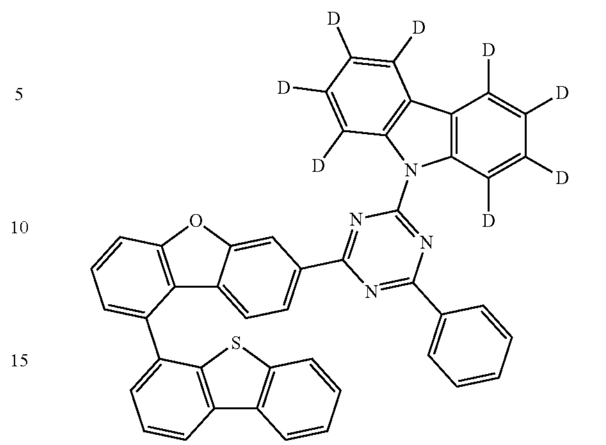
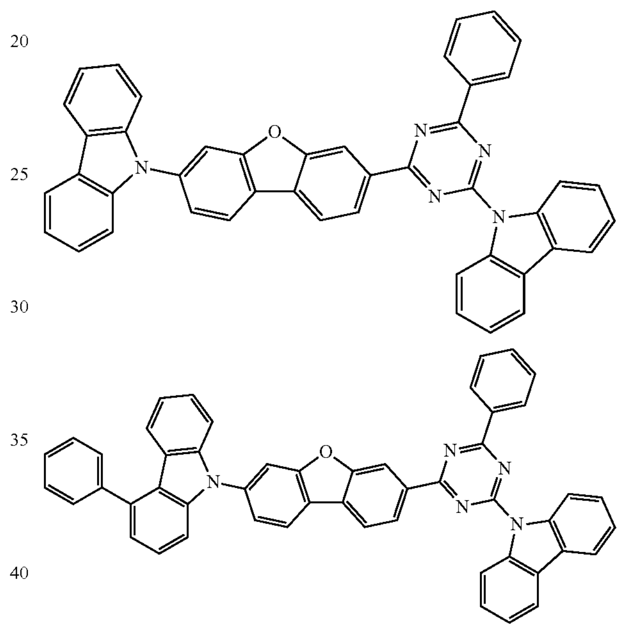
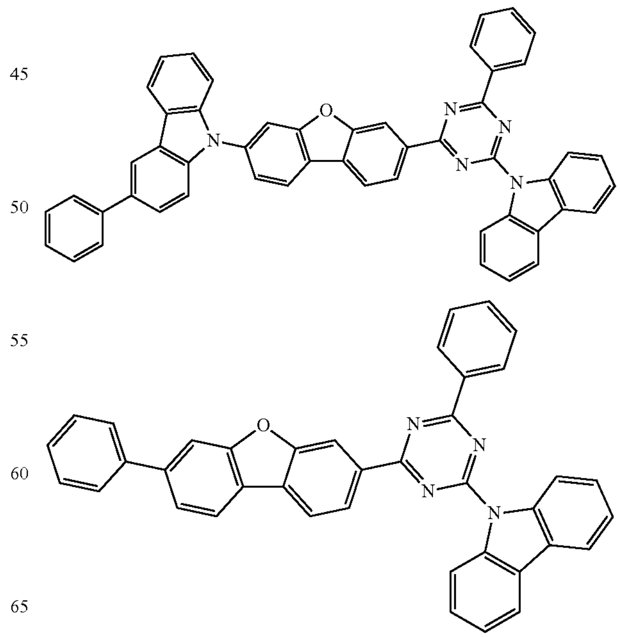

-continued
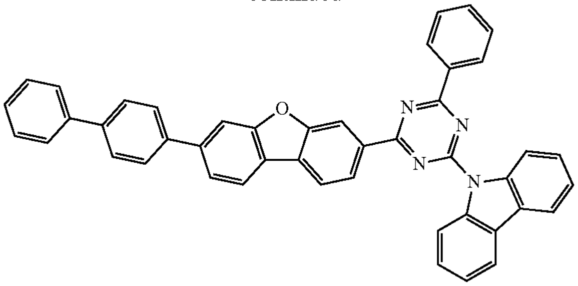
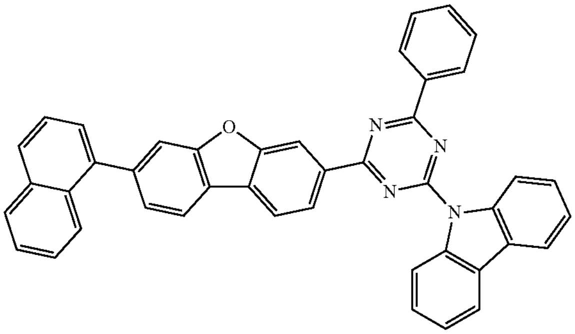
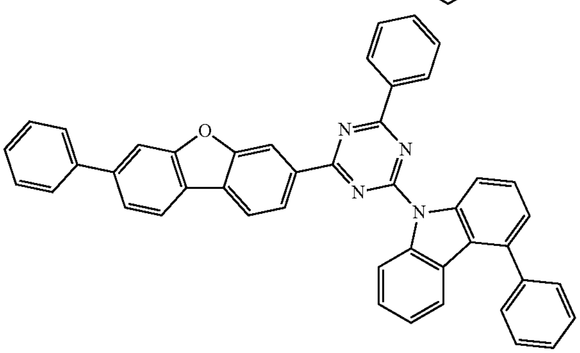
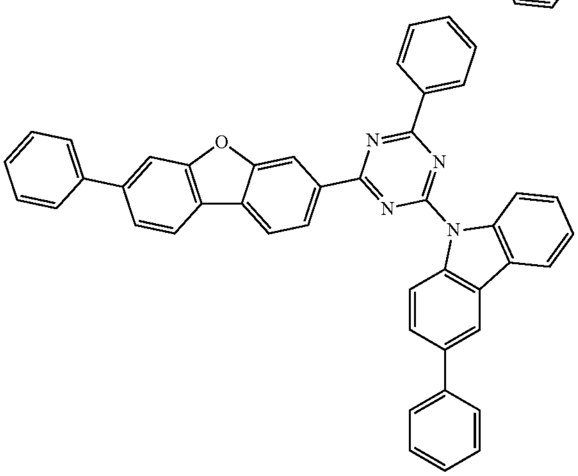
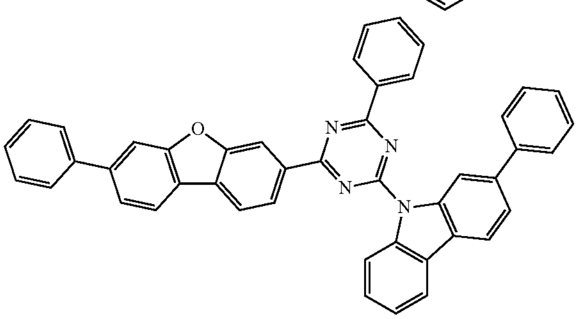
-continued
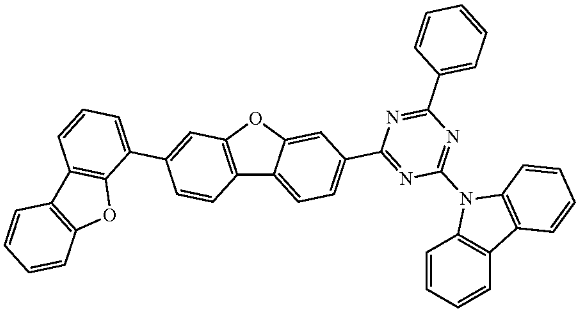
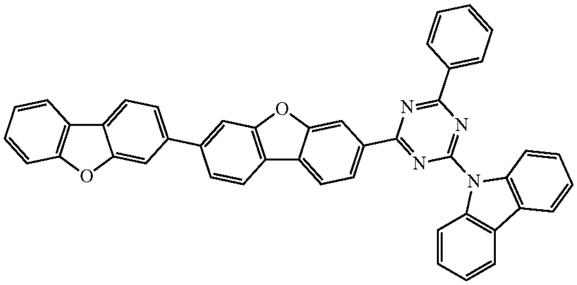
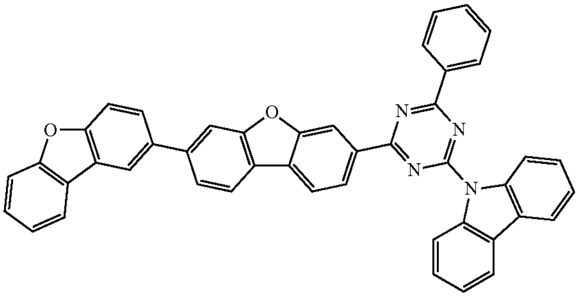
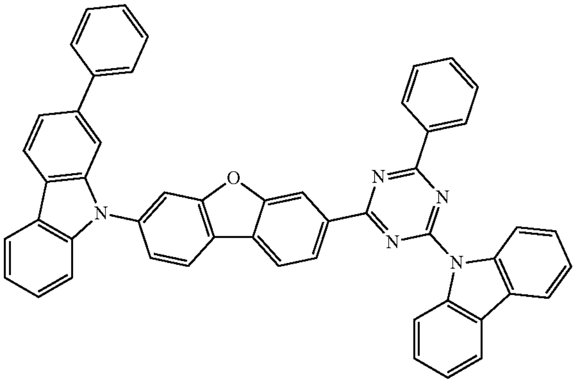
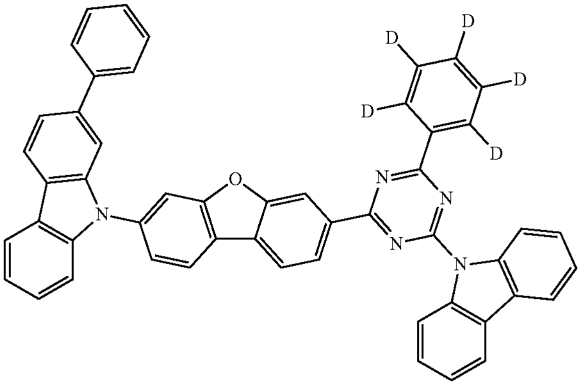

-continued
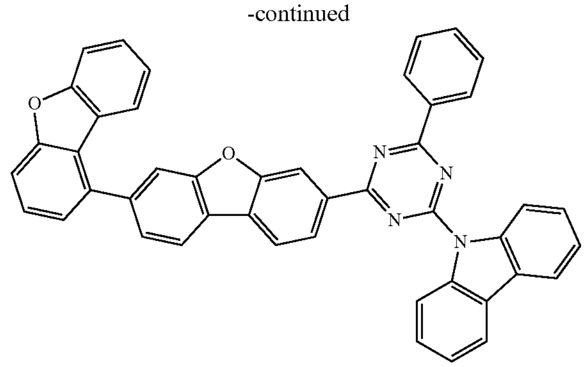
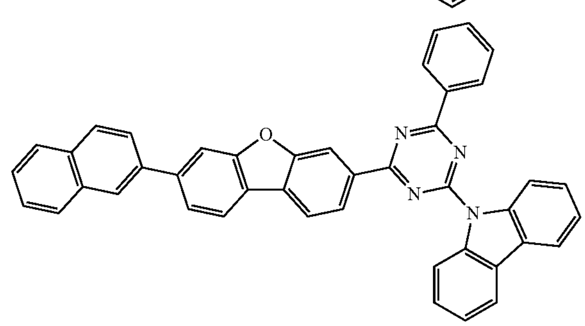
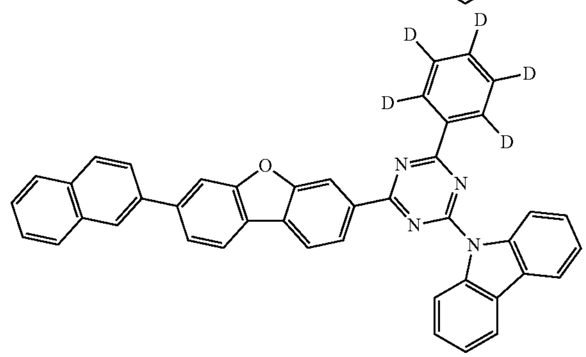
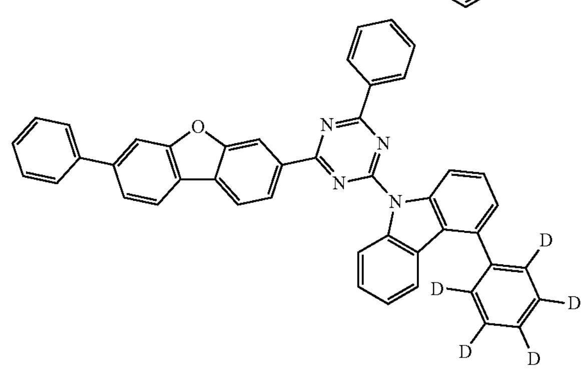
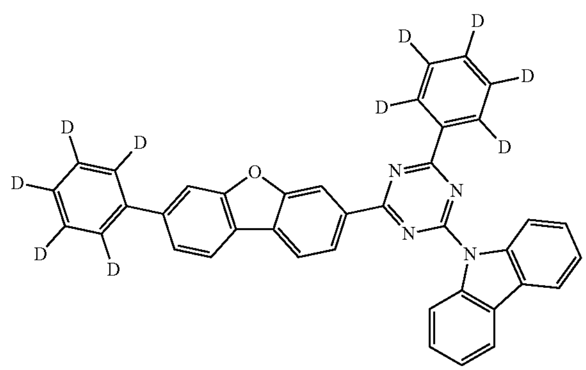
-continued
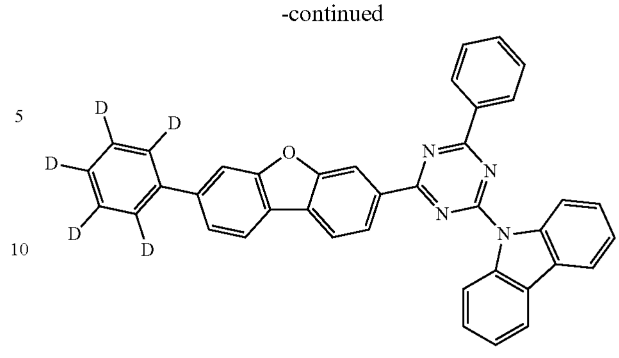
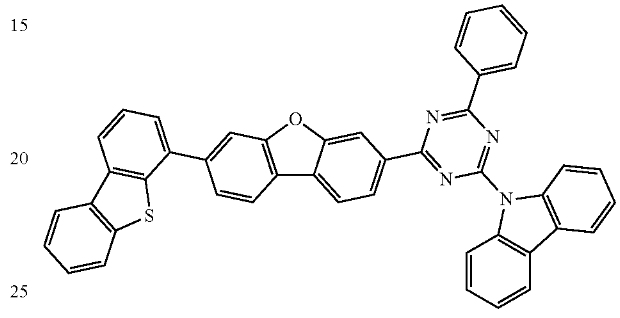
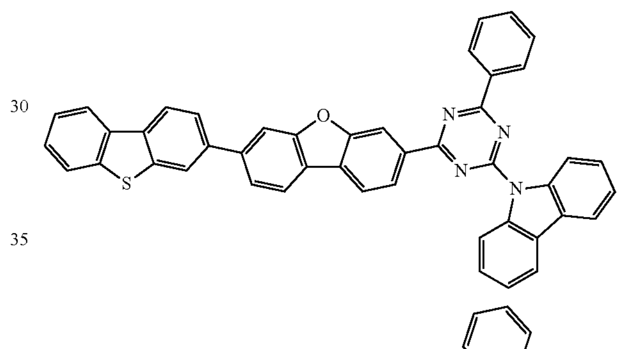
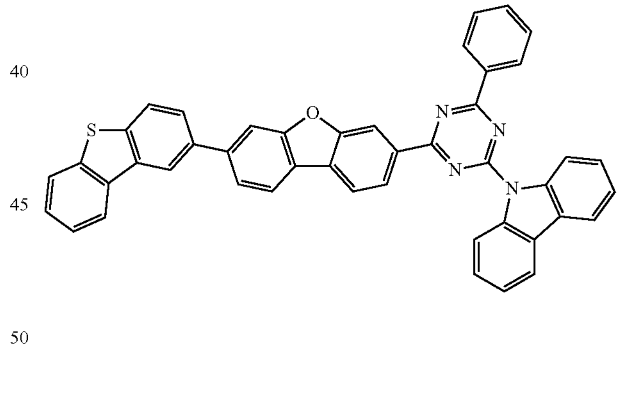
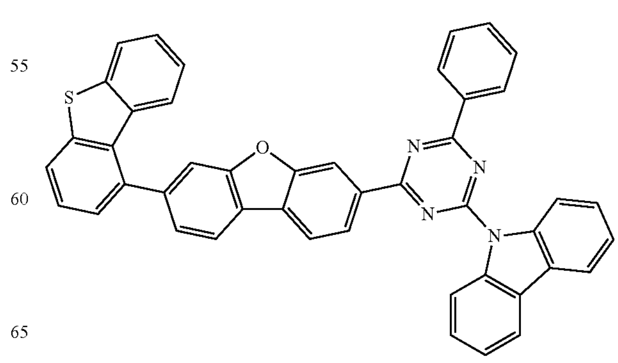

-continued
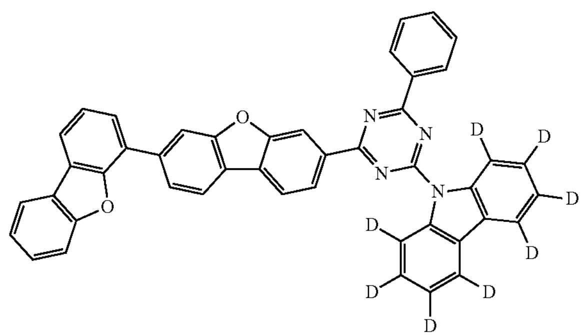
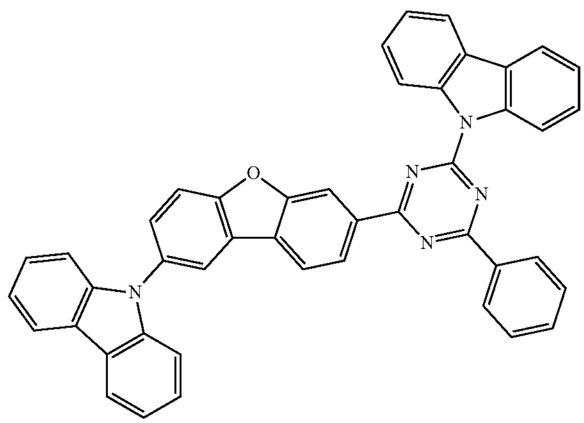
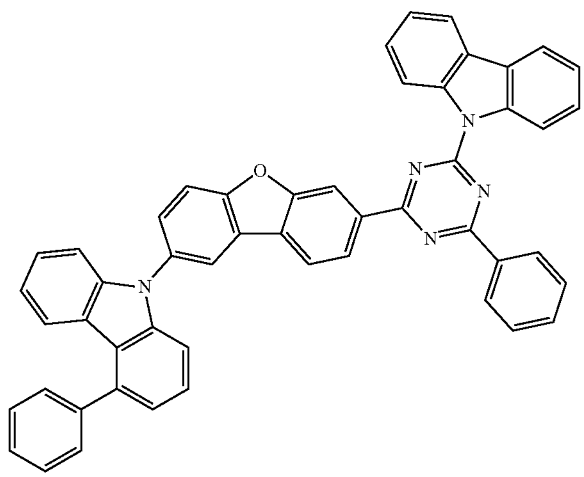
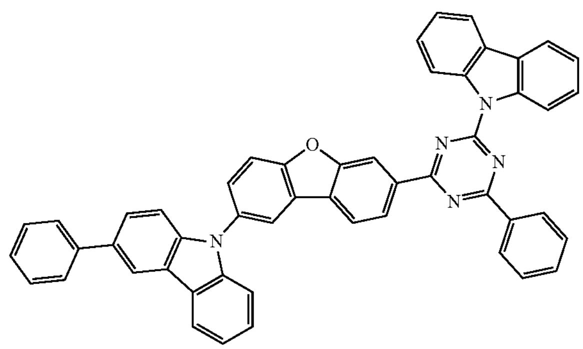
-continued
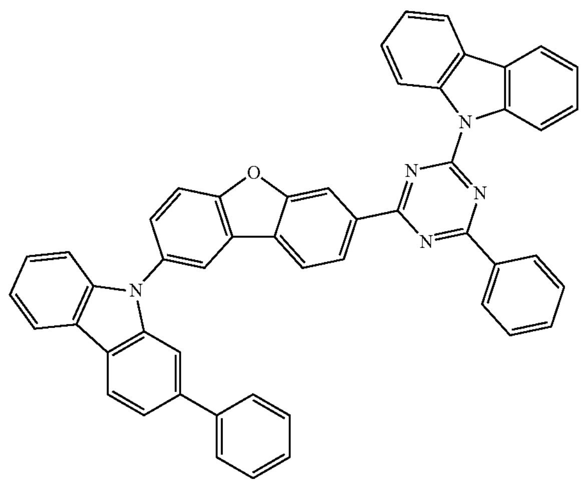
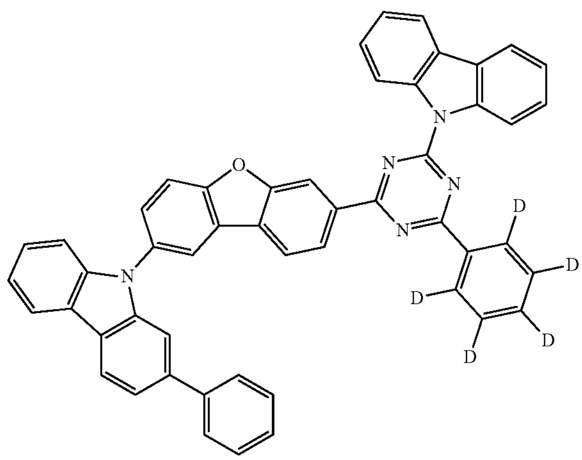
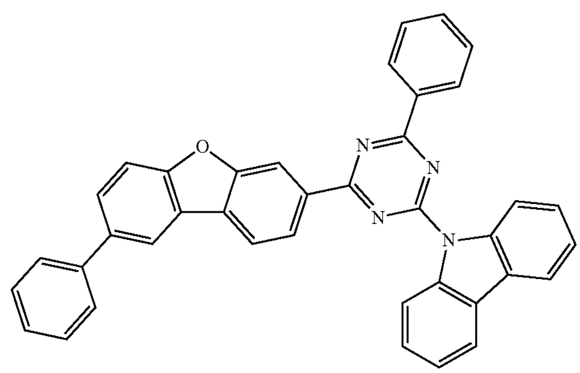
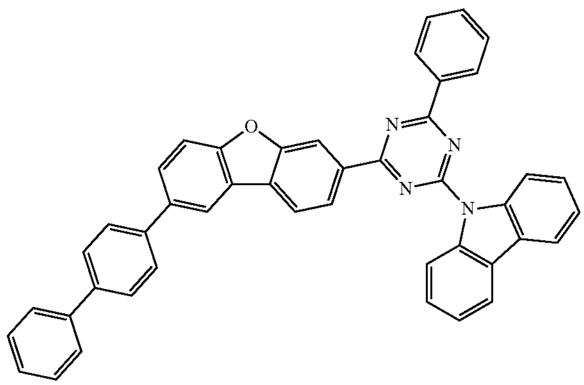

-continued
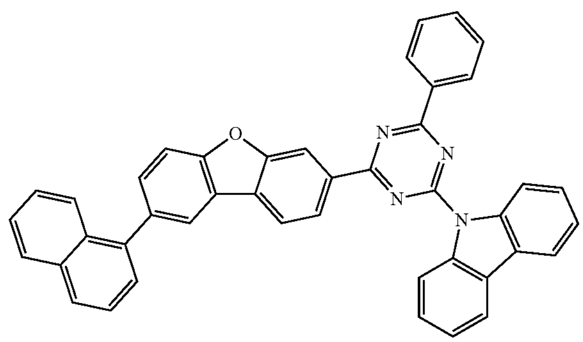
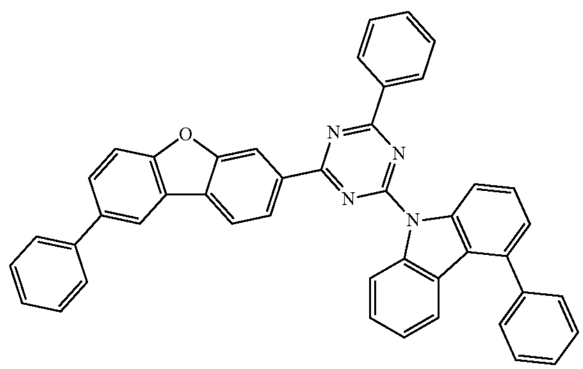
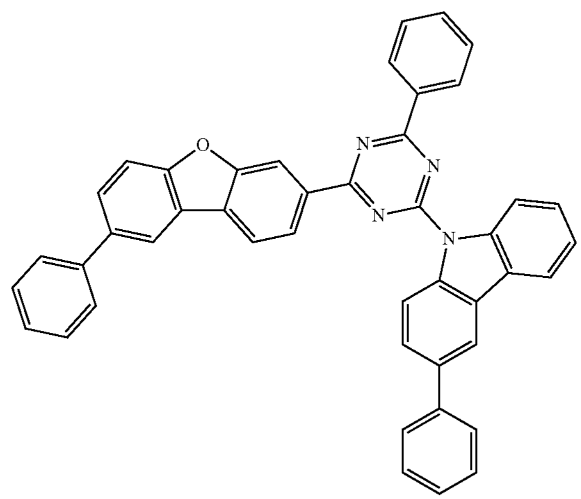
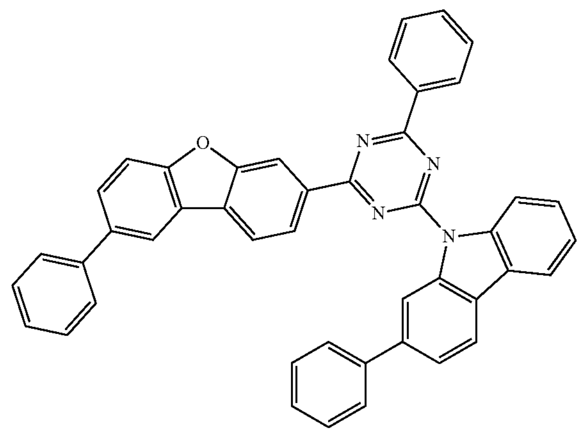
-continued
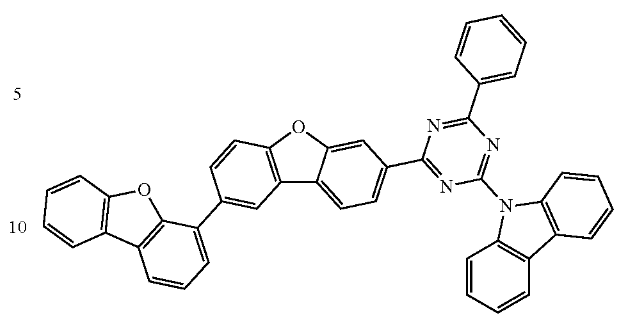
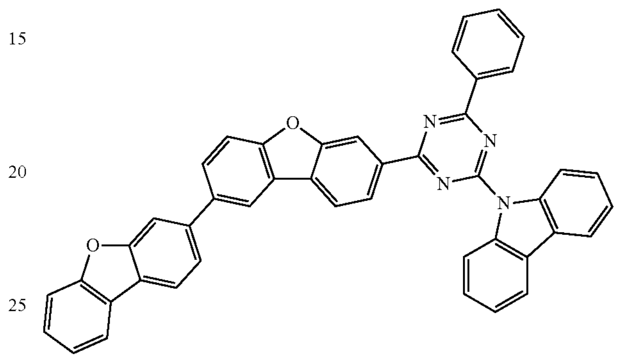
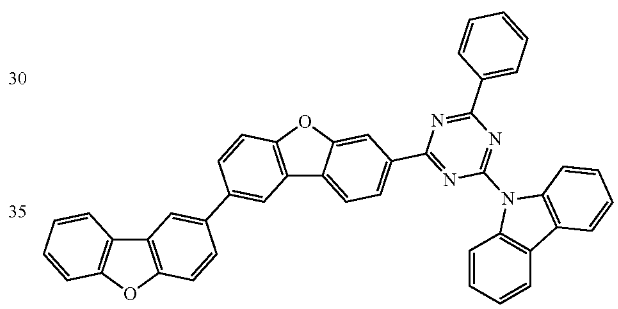
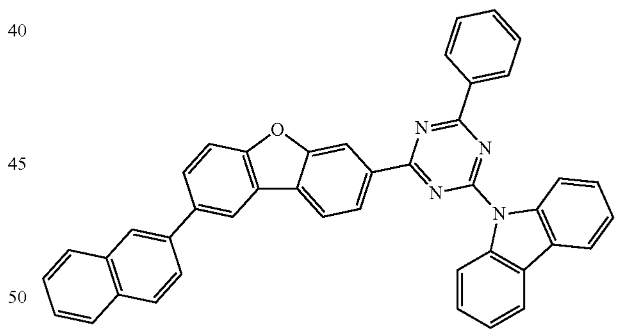
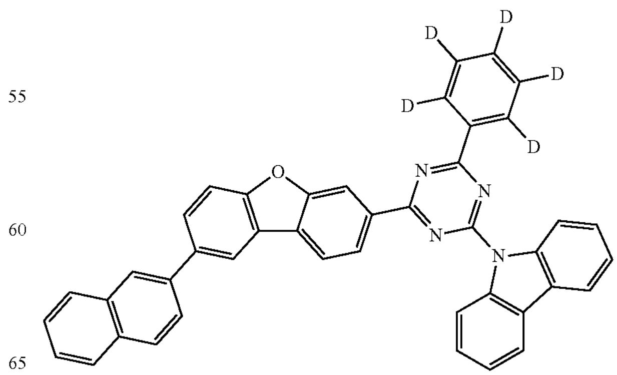

-continued
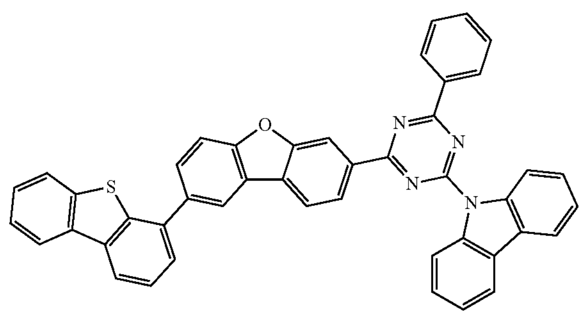
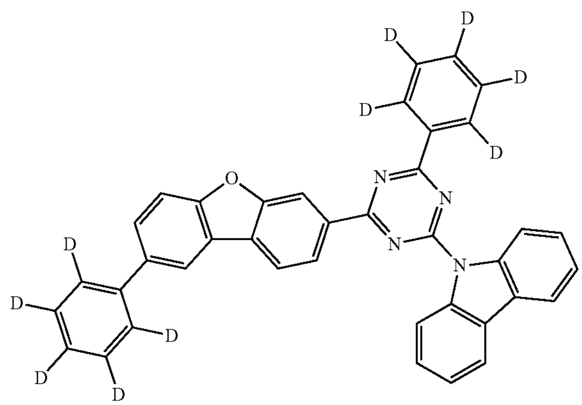
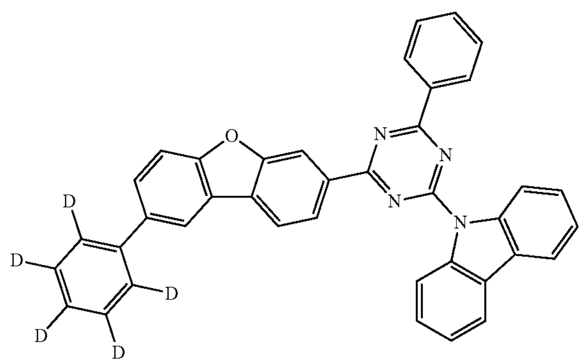
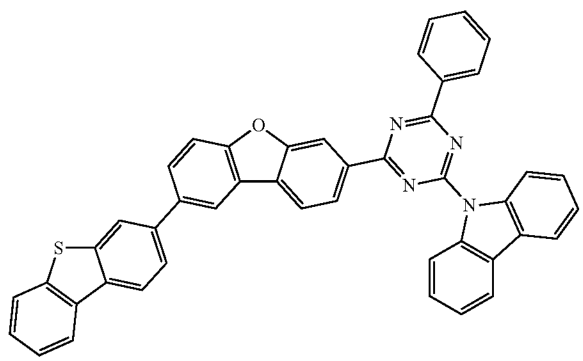
-continued
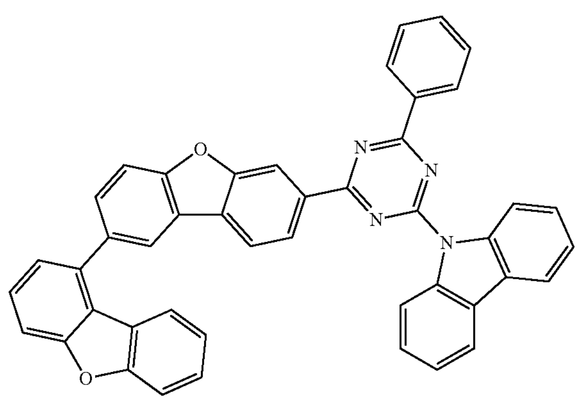
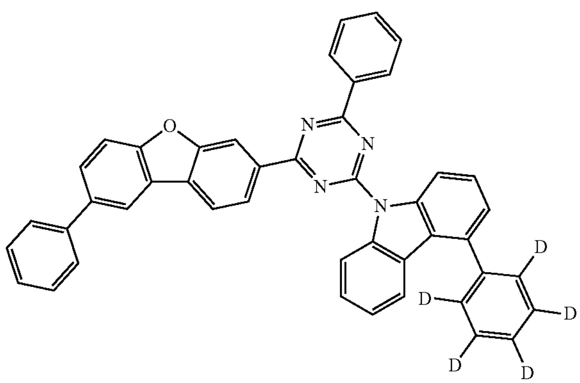
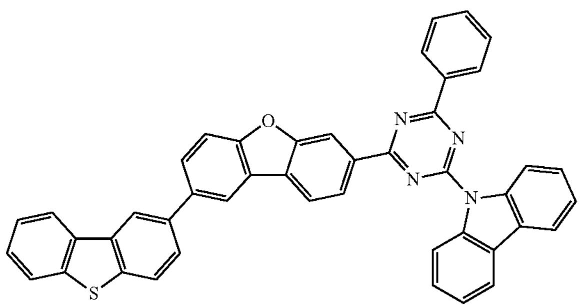
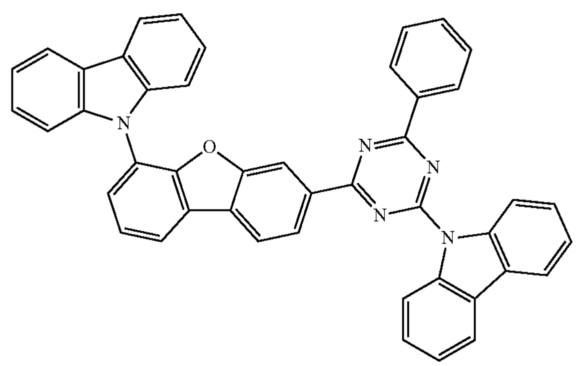

-continued
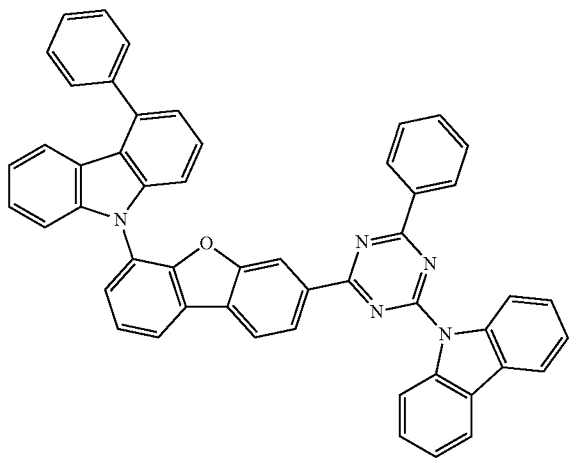
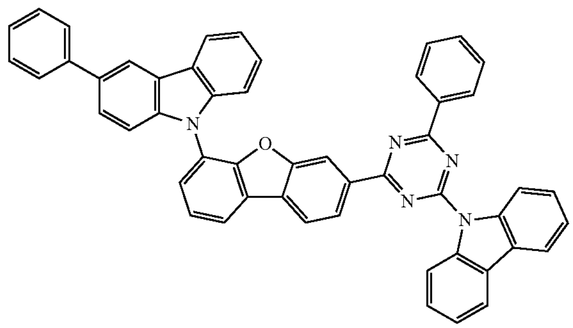
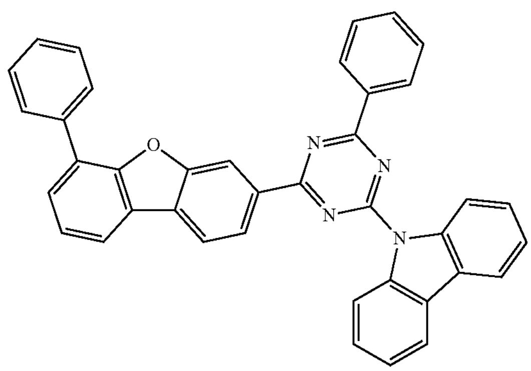
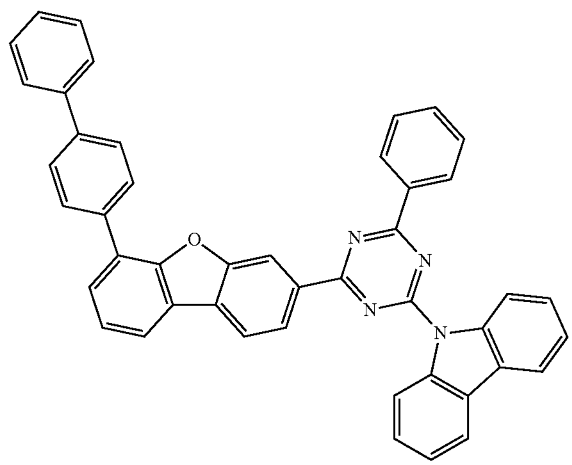
-continued
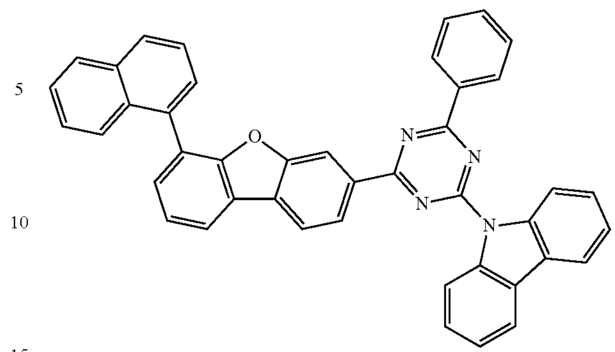
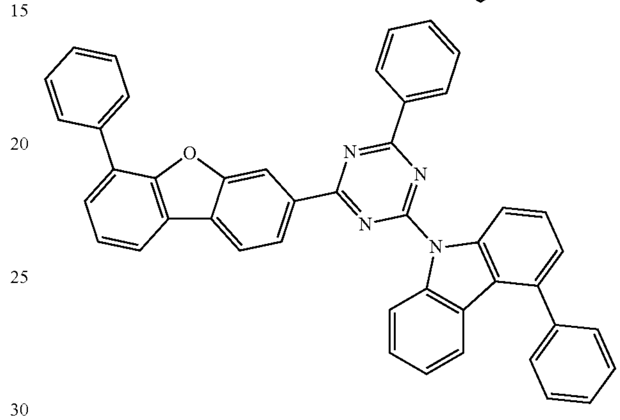
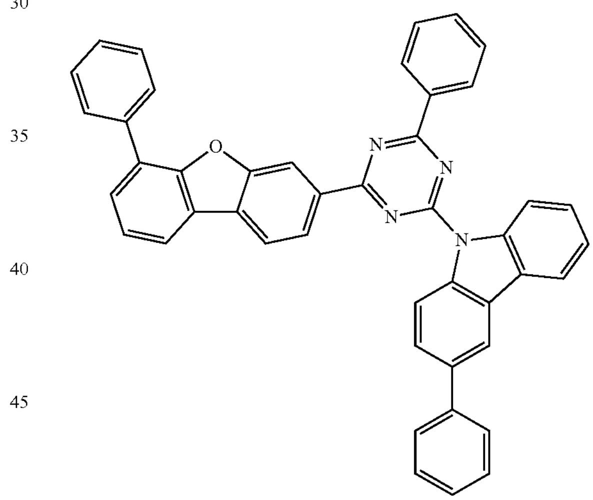
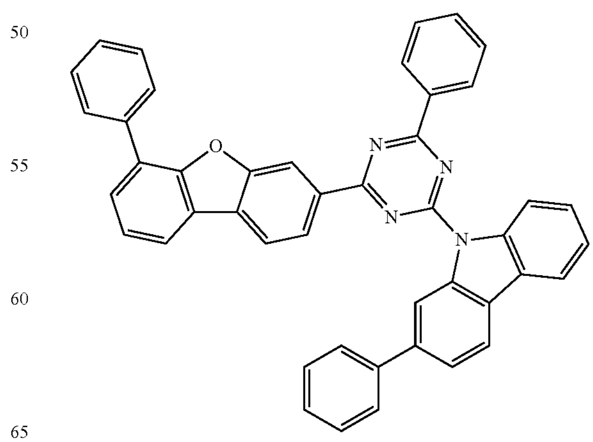

-continued
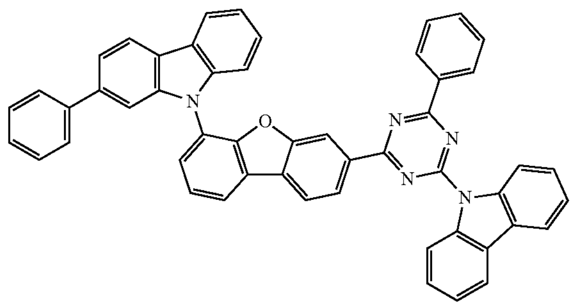
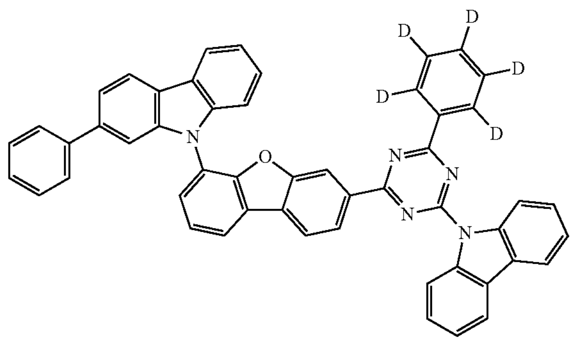
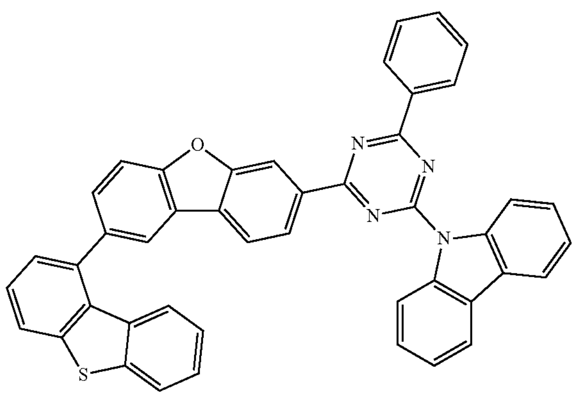
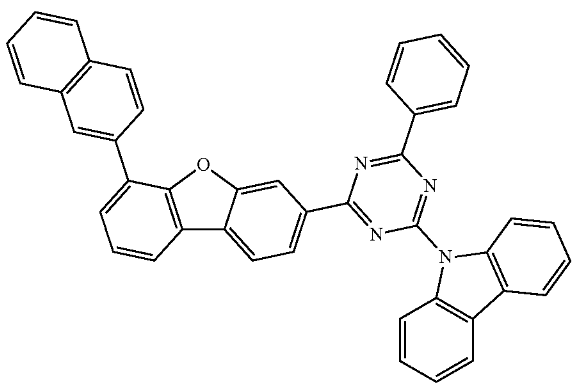
-continued
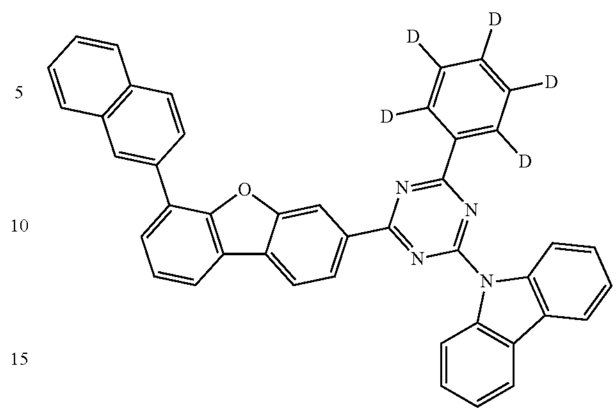
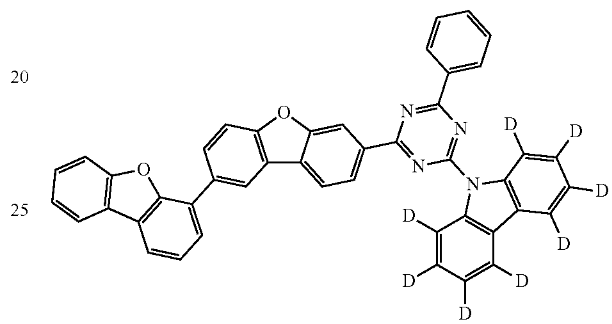
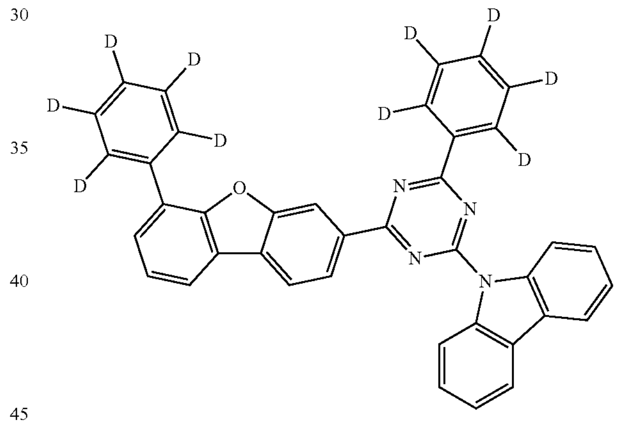
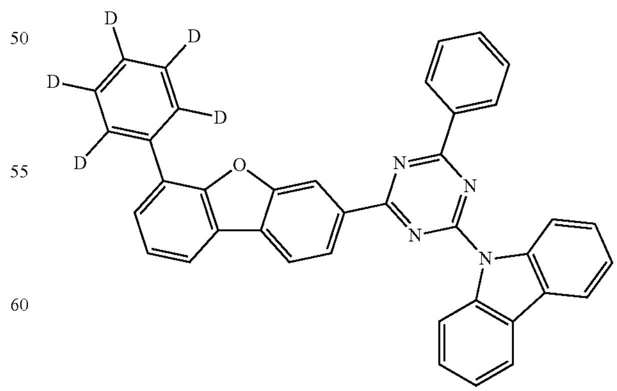

-continued
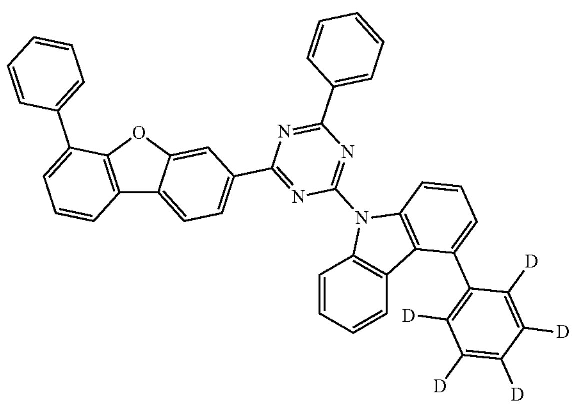
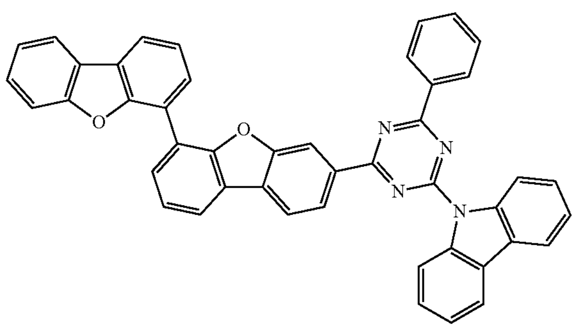
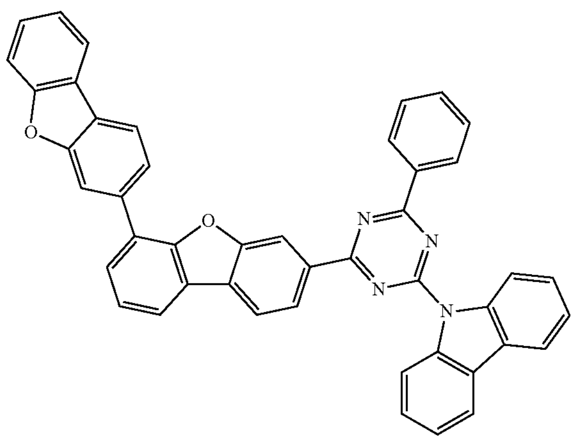
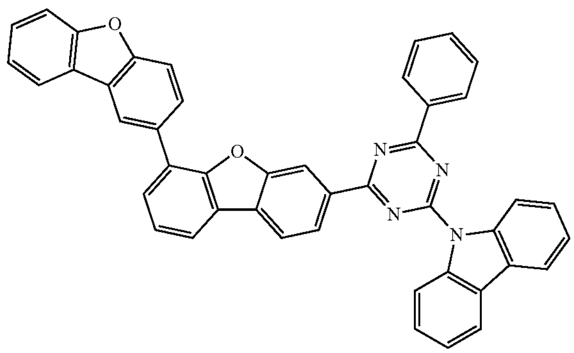
-continued
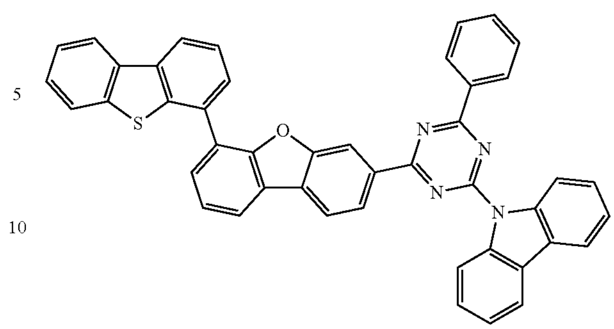
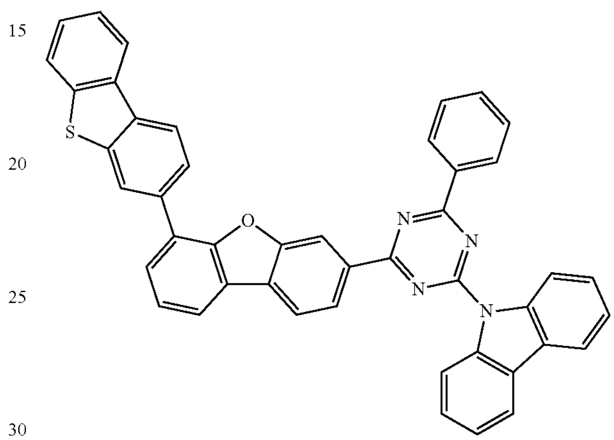
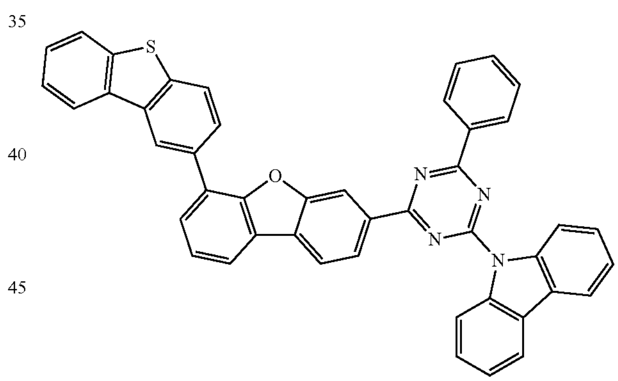
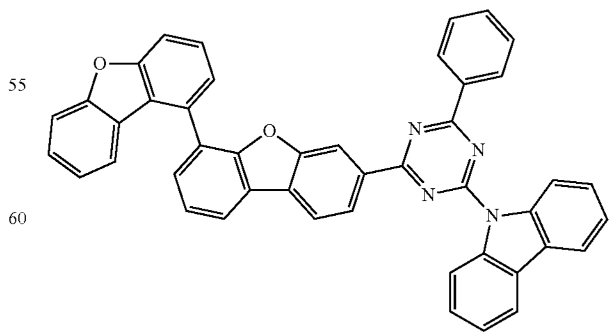

-continued
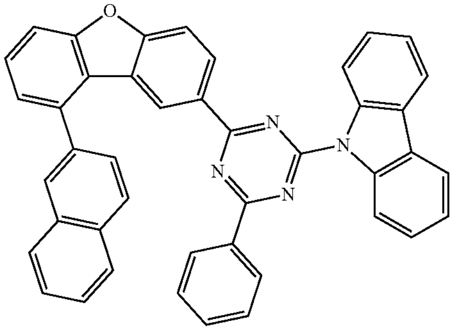
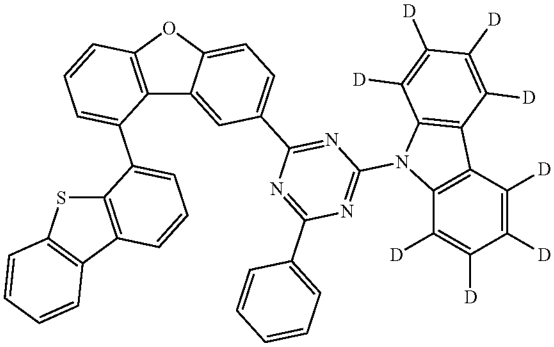
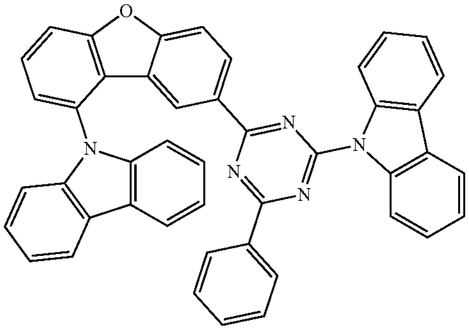
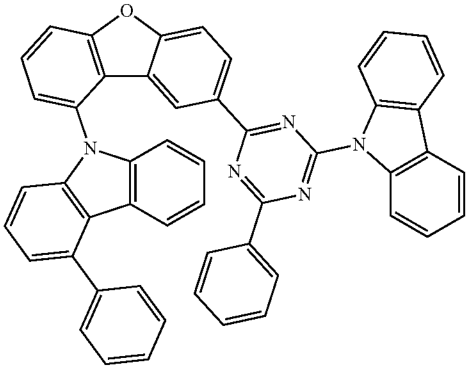
-continued
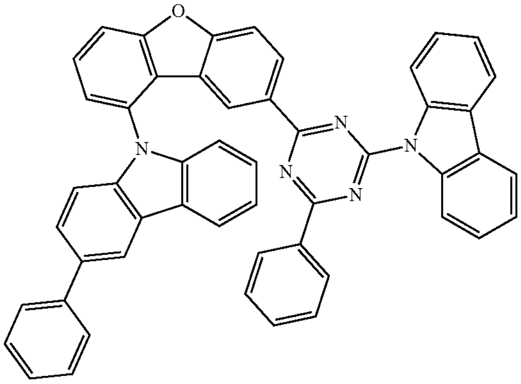
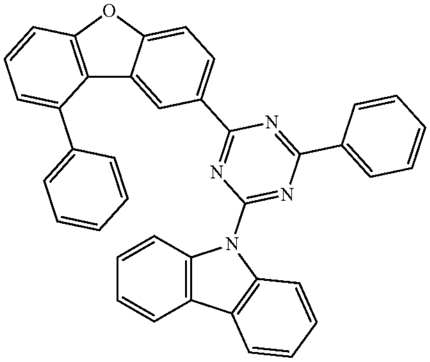
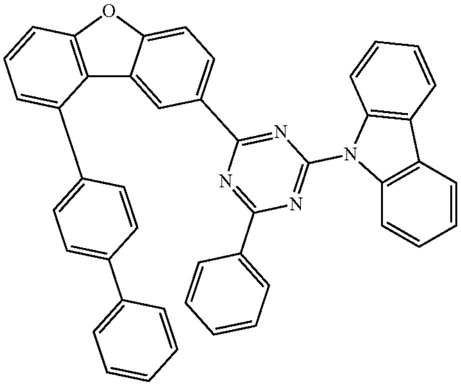
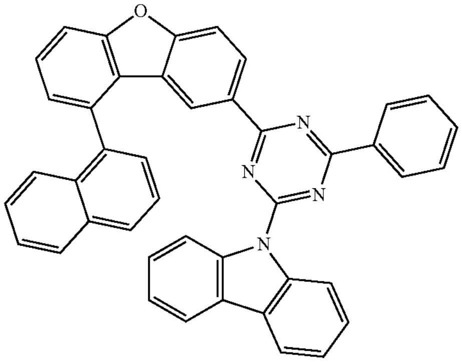

-continued
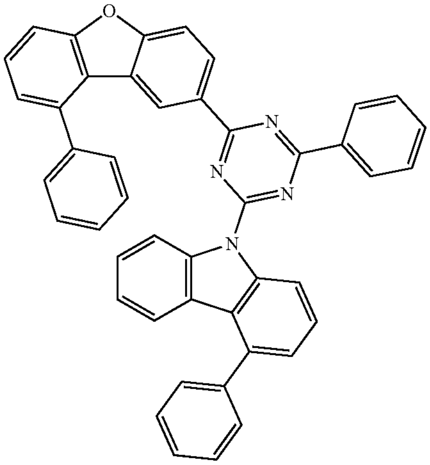
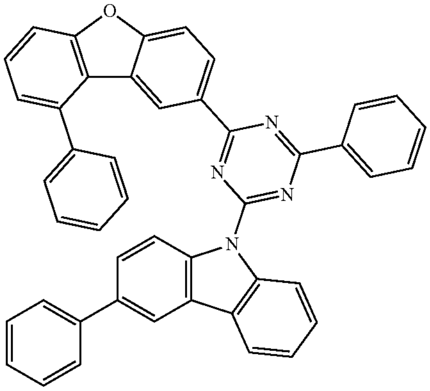
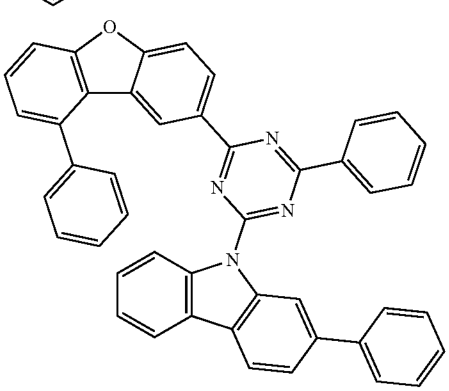
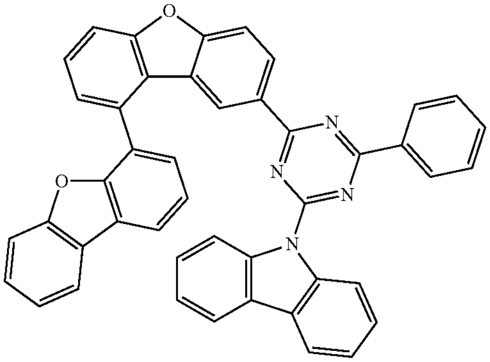
-continued
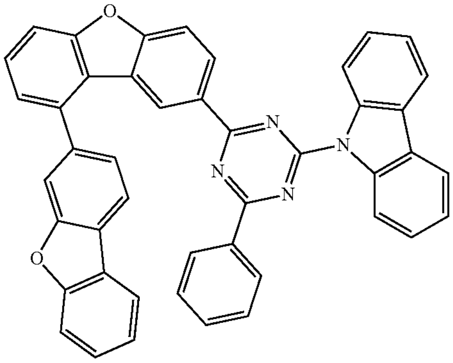
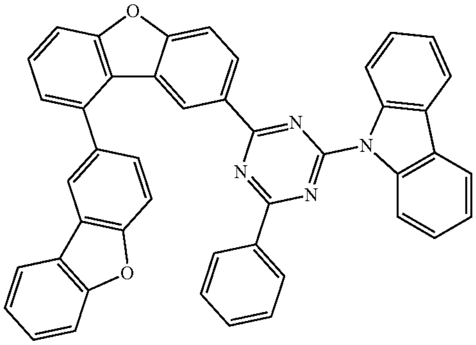
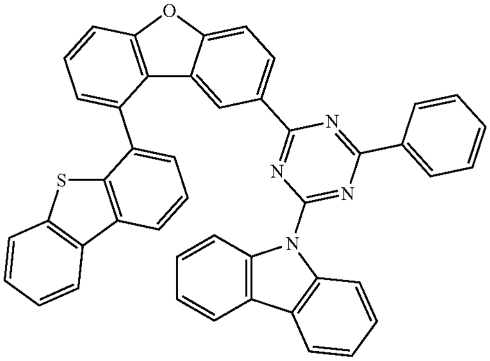
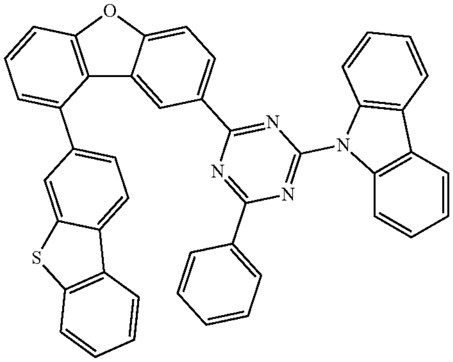

-continued
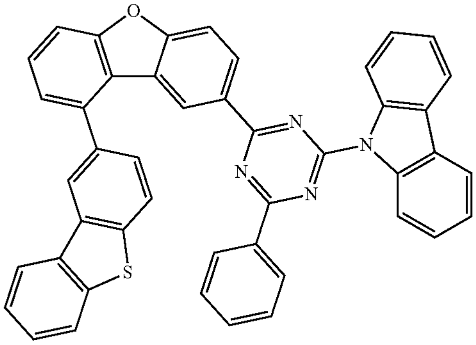
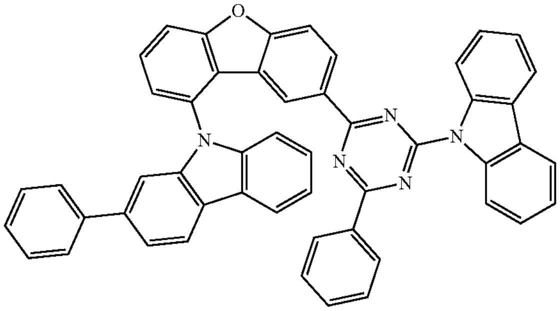
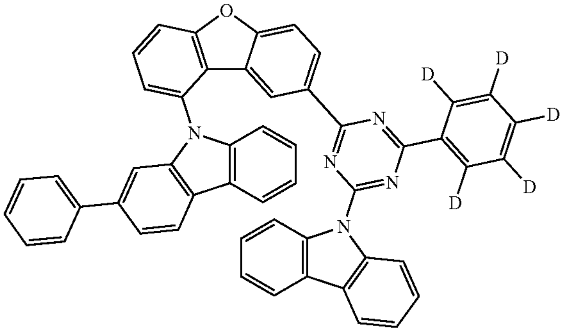
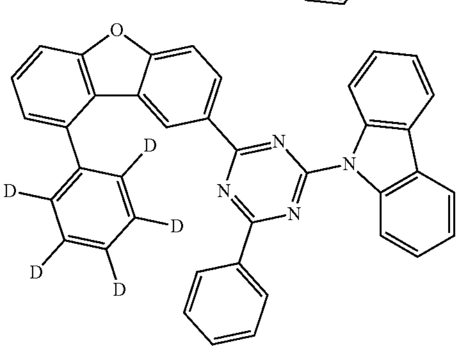
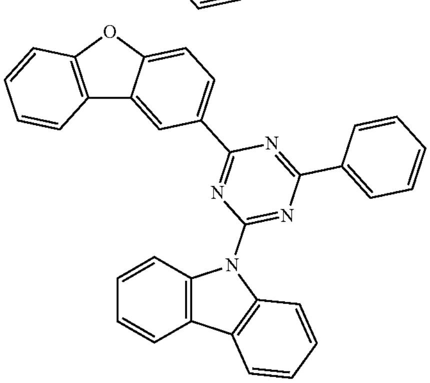
-continued
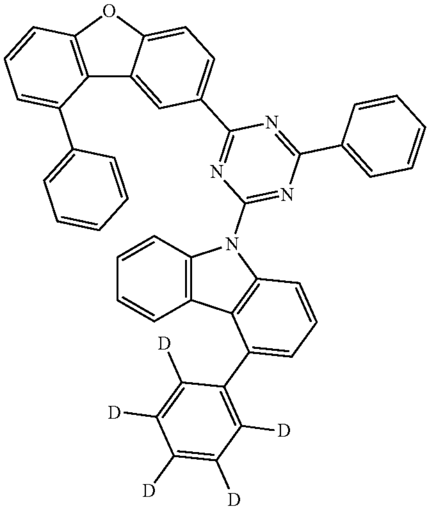
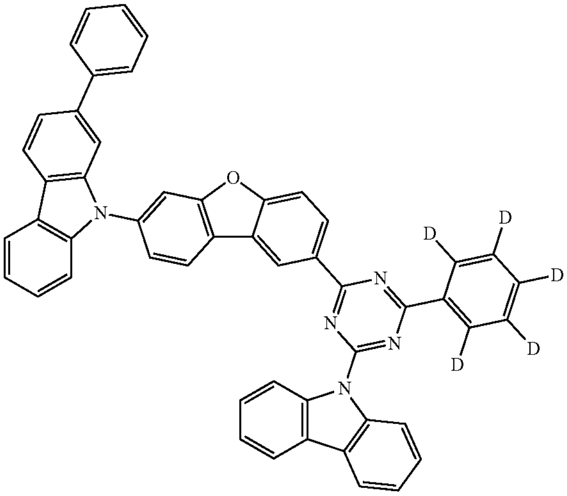
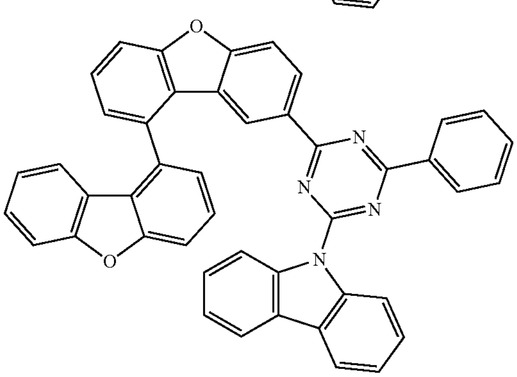
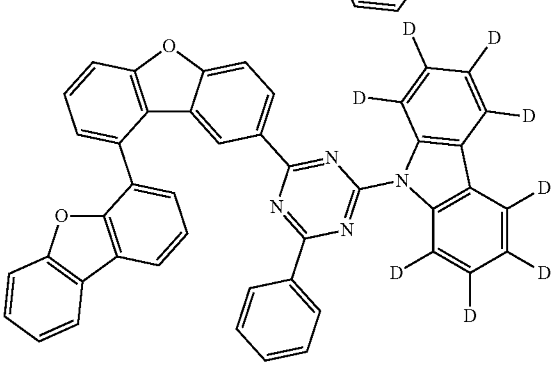

-continued
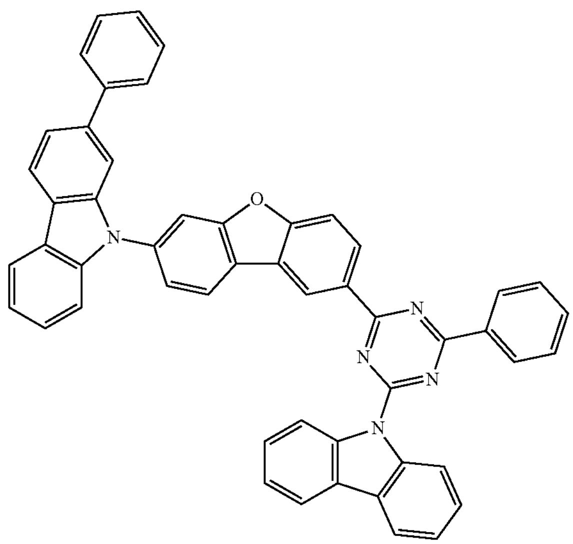
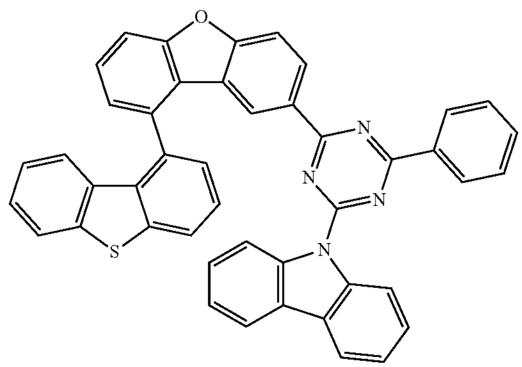
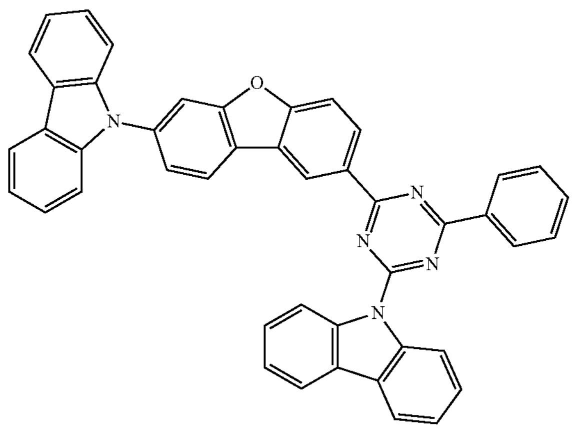
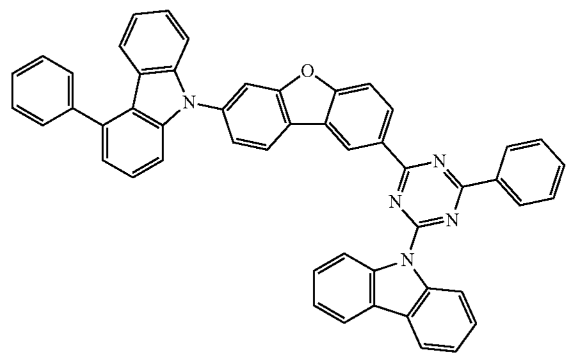
-continued
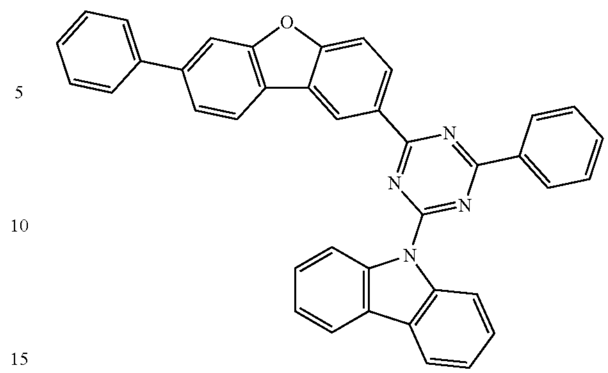
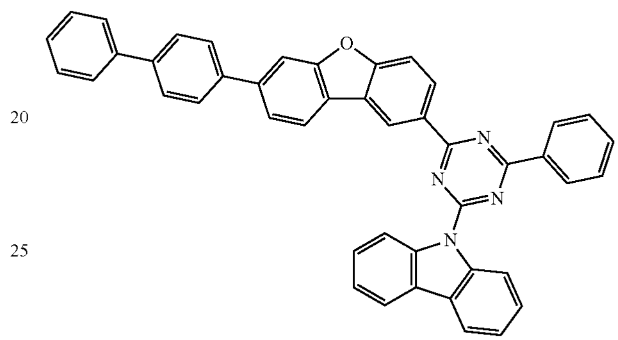
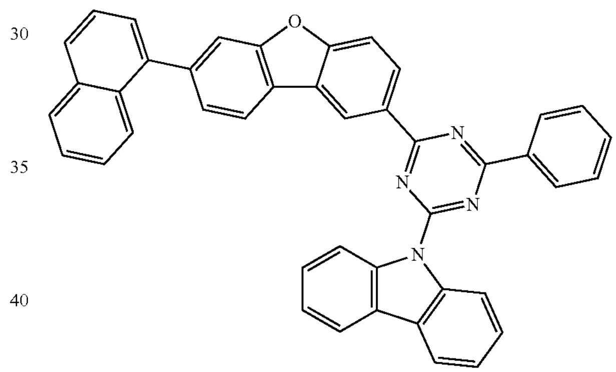
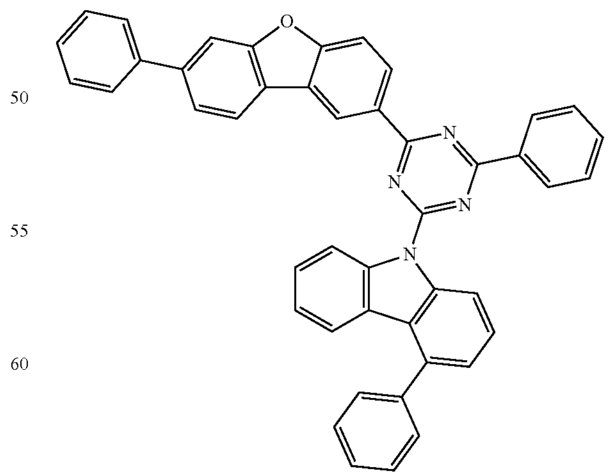

-continued
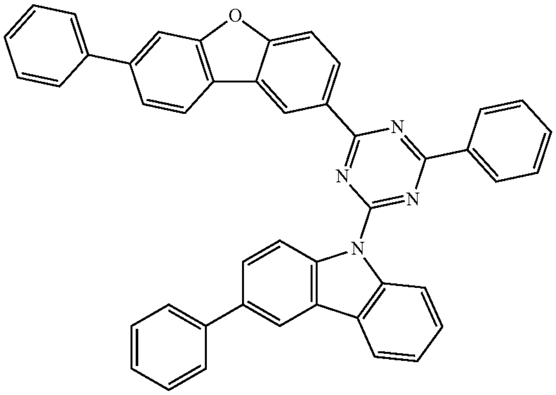
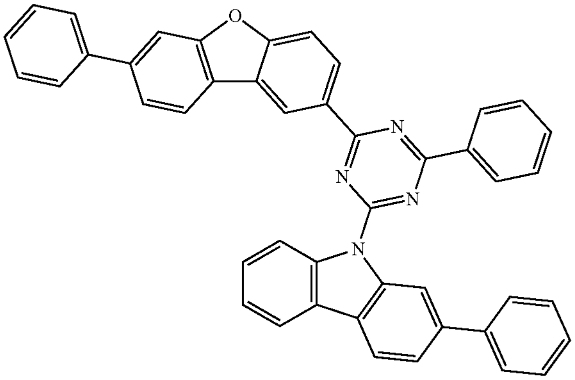
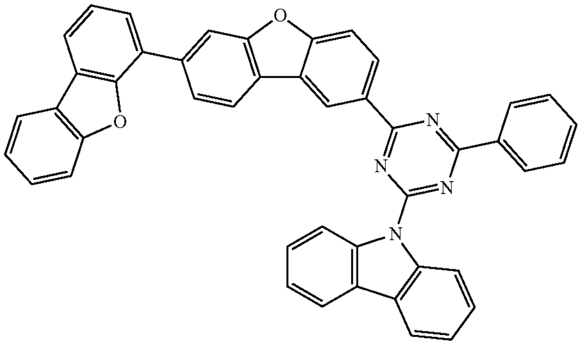
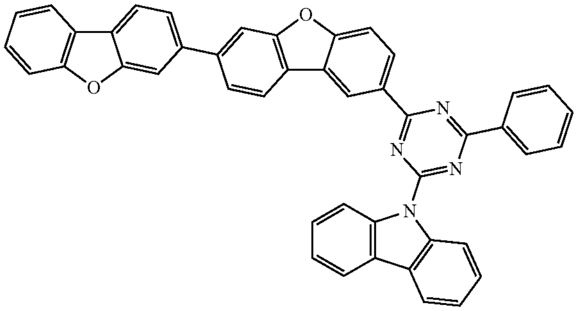
-continued
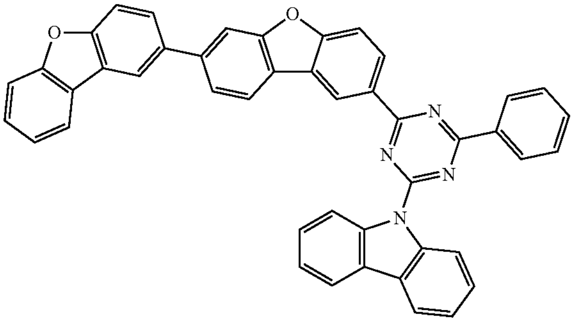
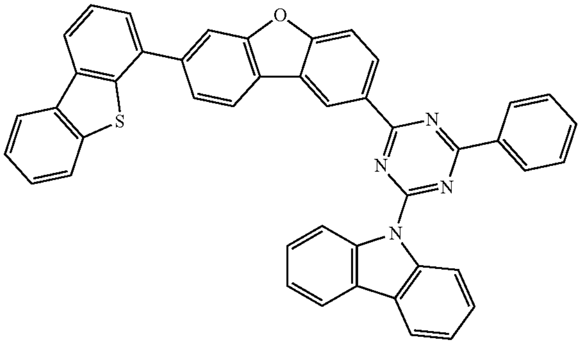
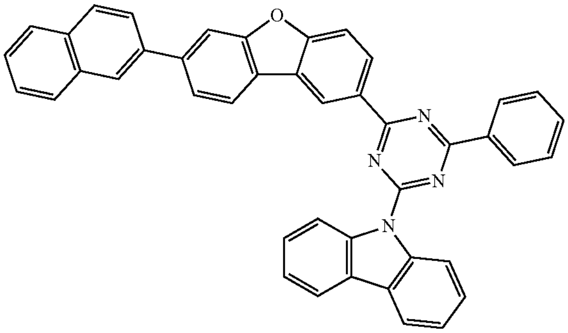
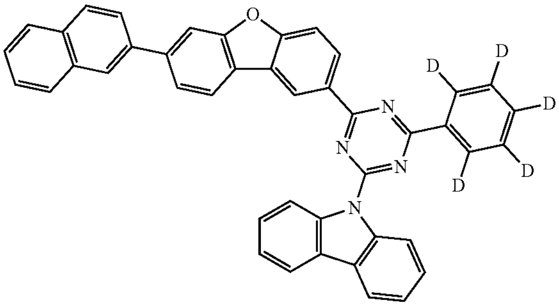
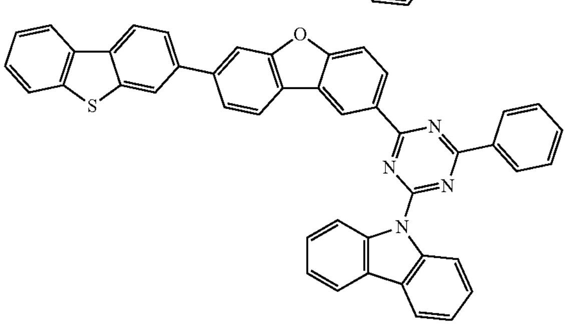

-continued
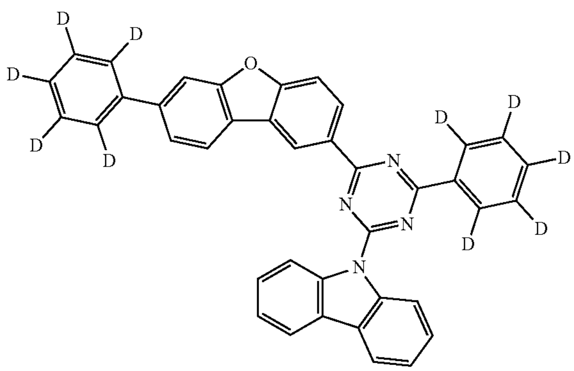
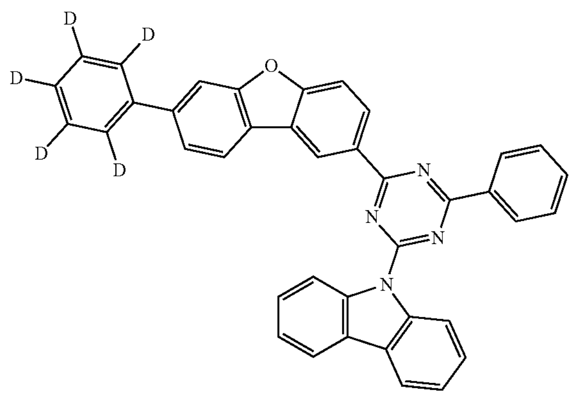
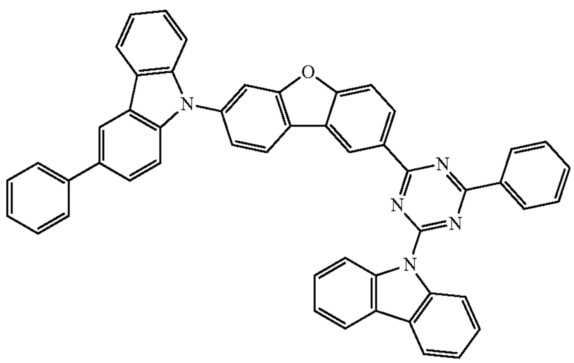
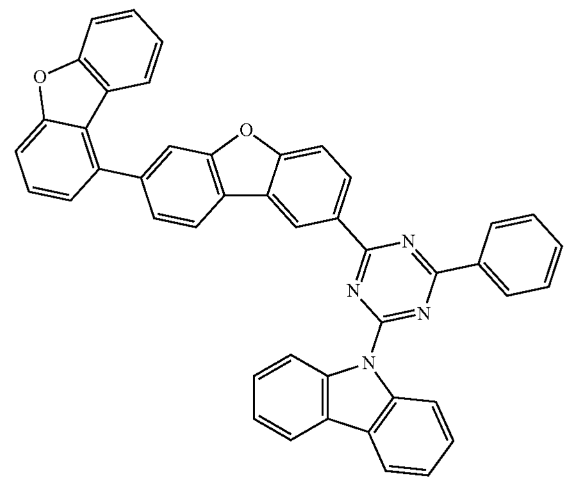
-continued
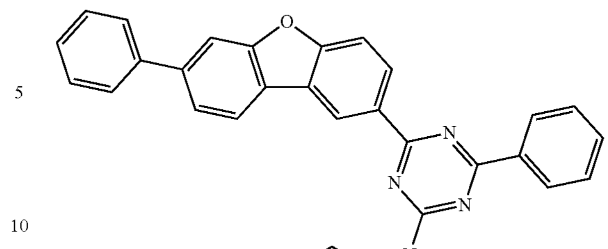
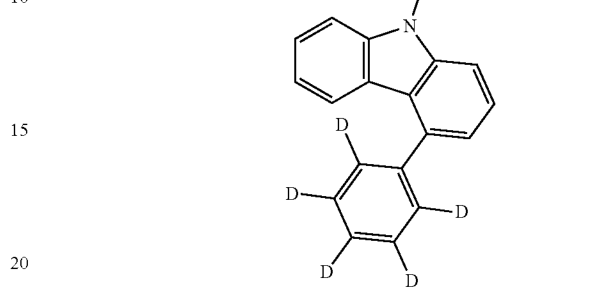
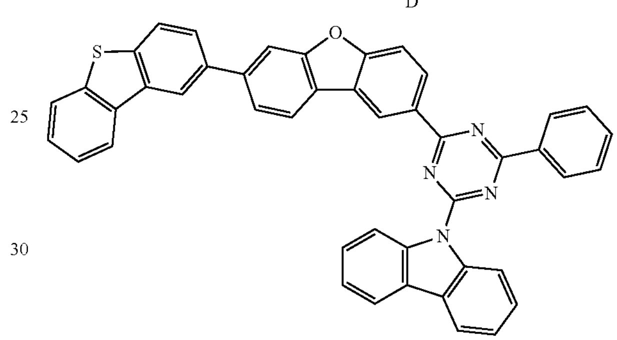
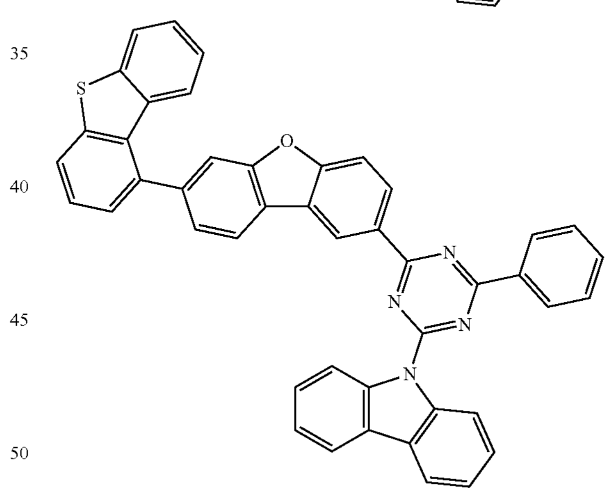
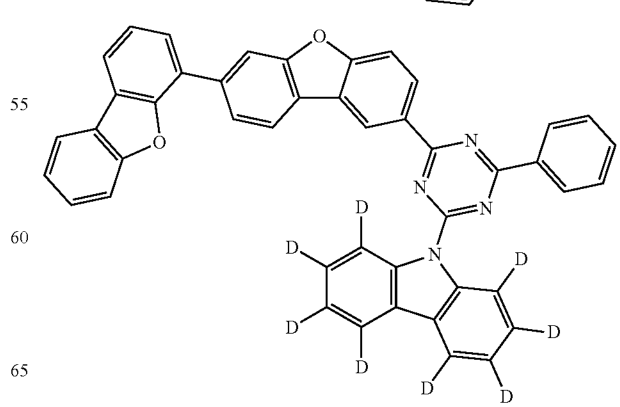

-continued
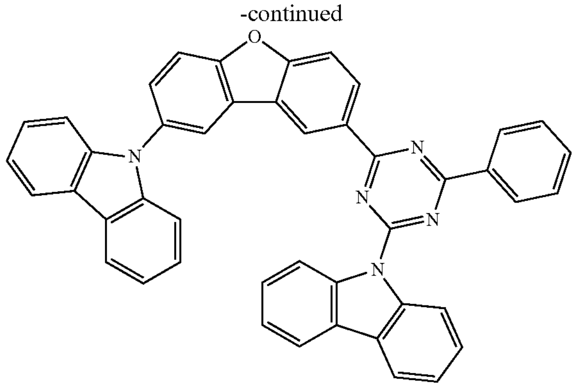
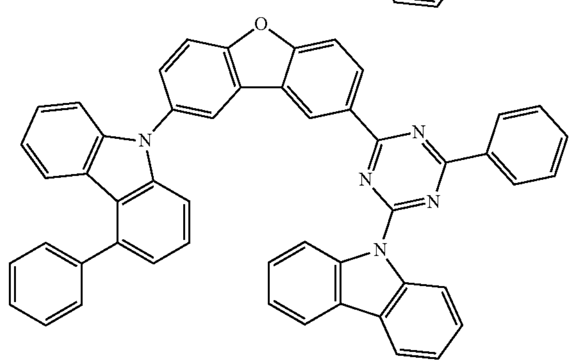
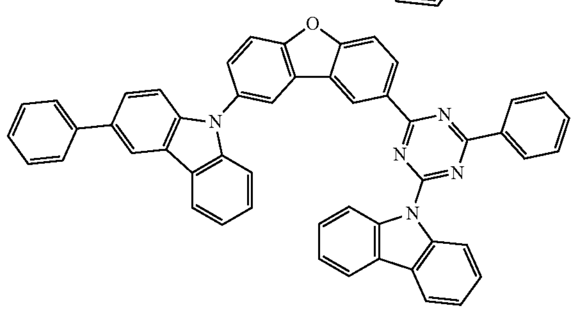
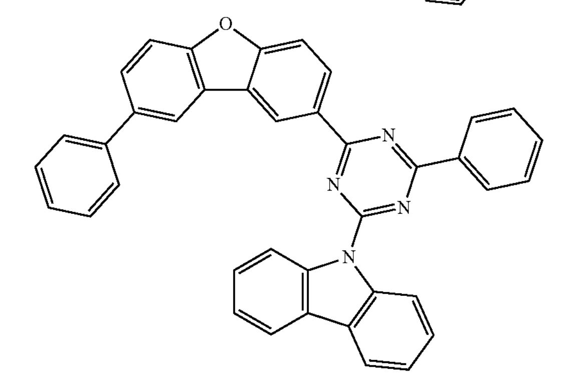
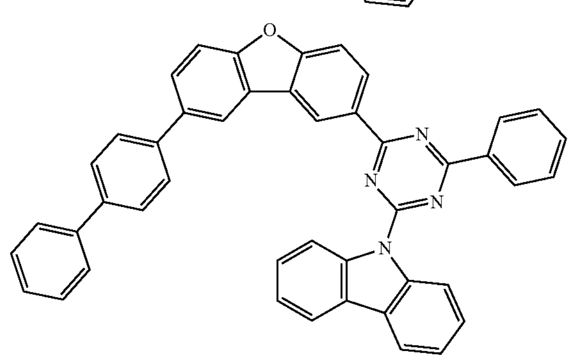
-continued
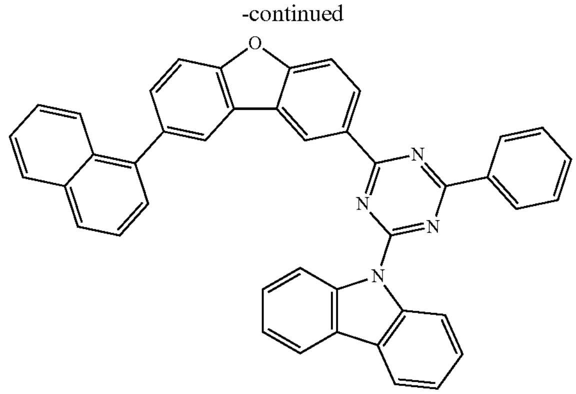
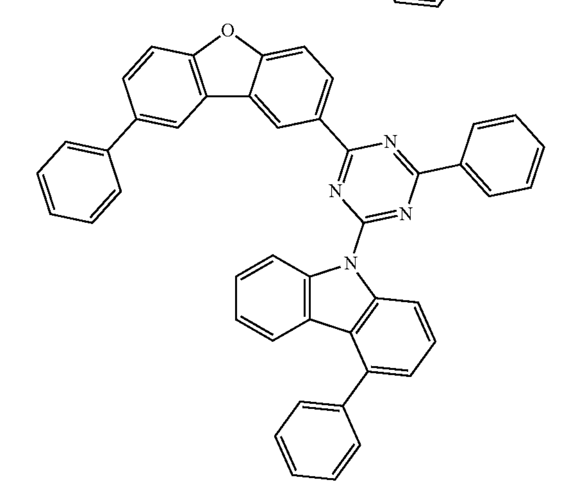
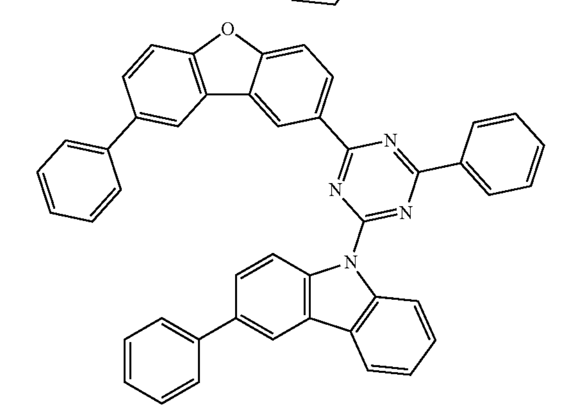
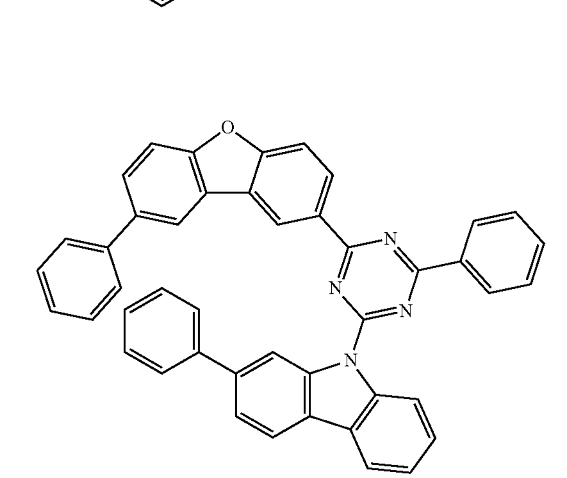

-continued
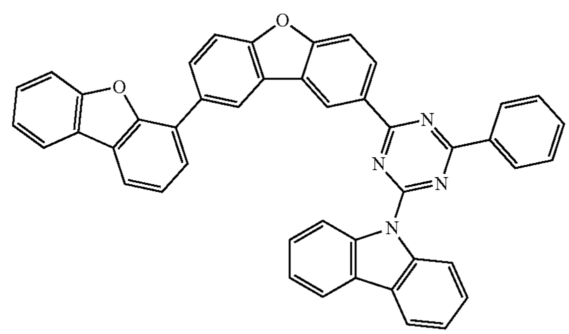
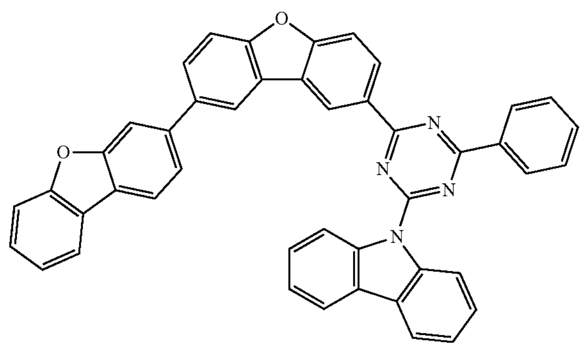
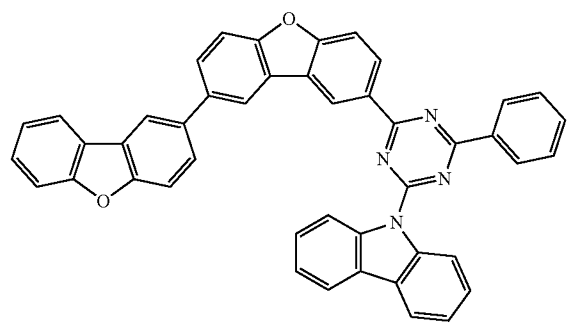
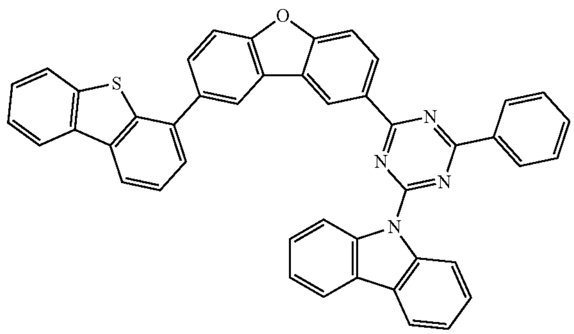
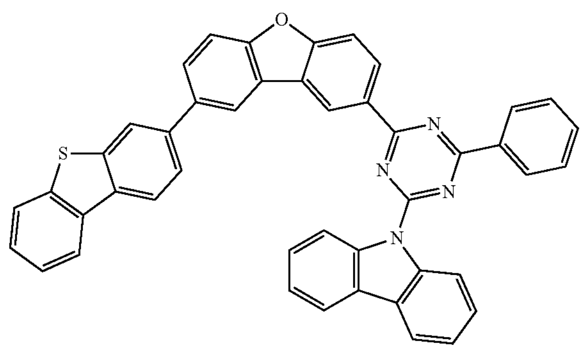
-continued
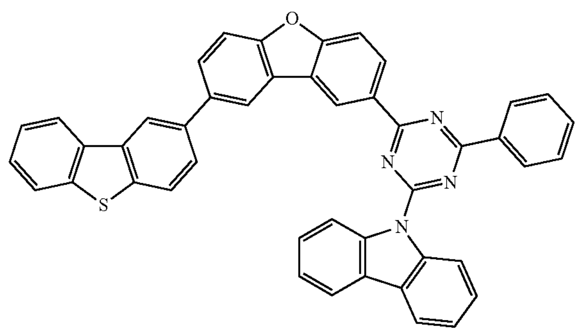
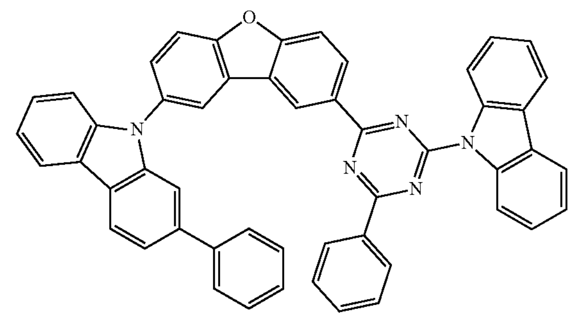
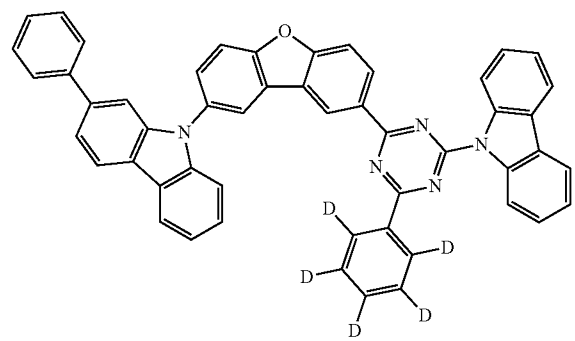
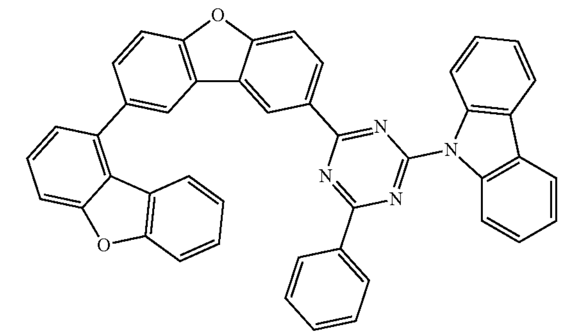
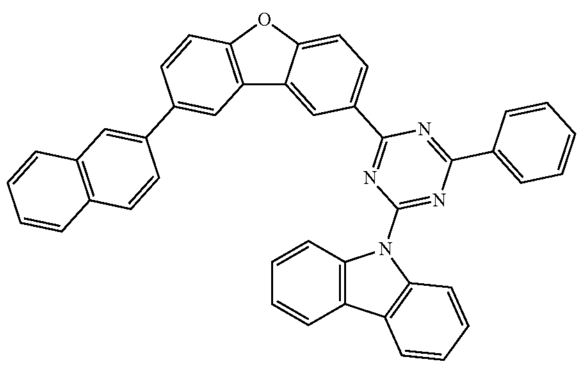

-continued
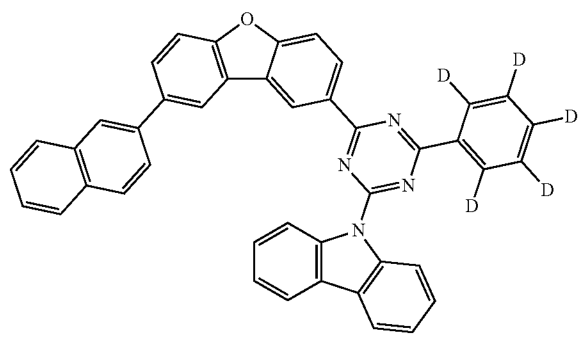
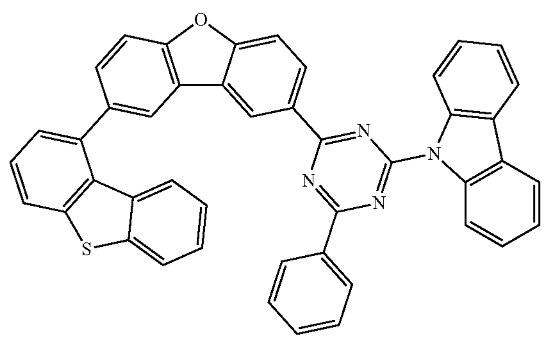
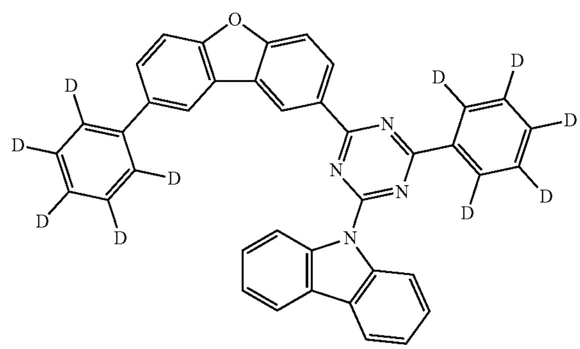
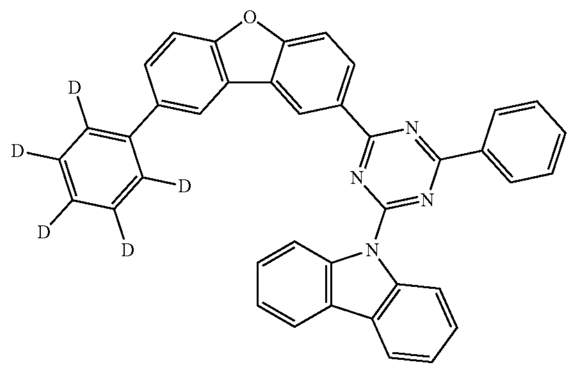
-continued
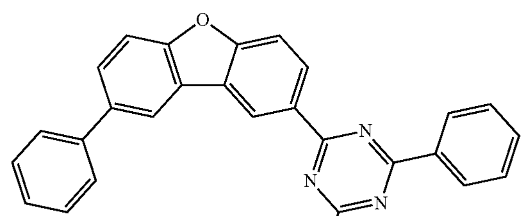
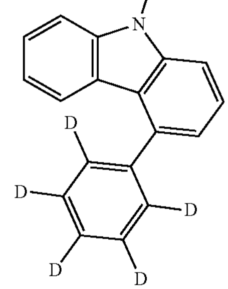
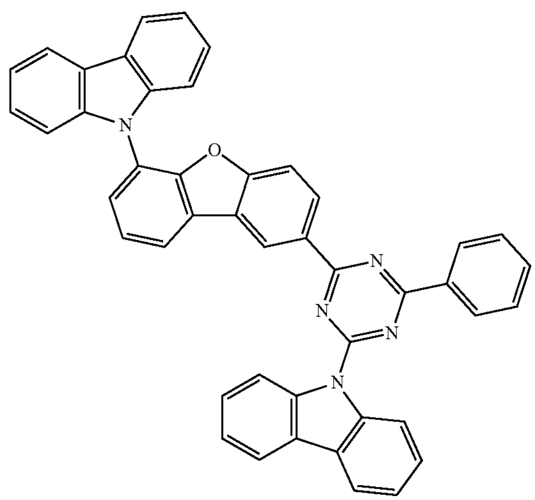
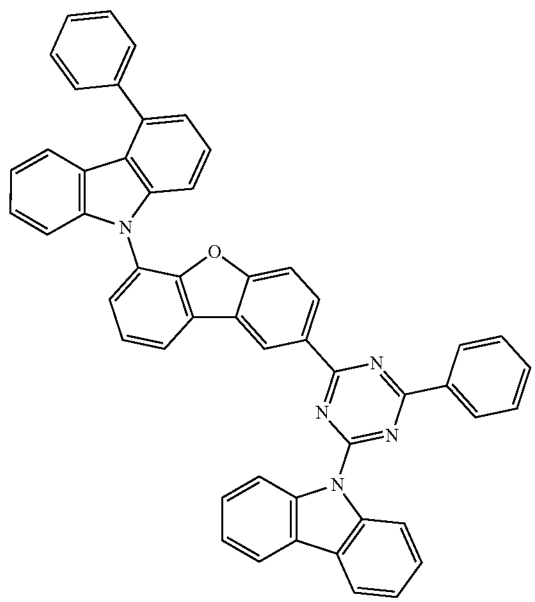

-continued
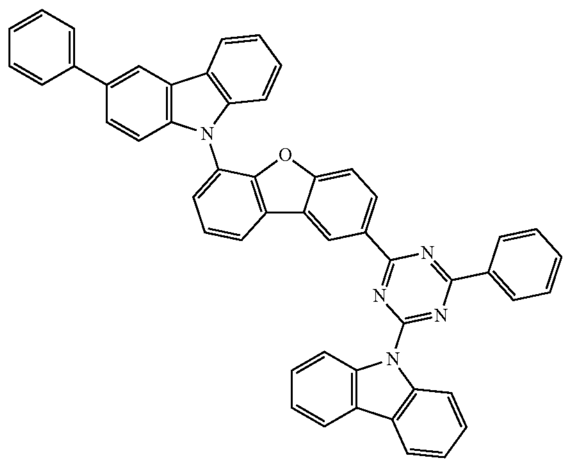
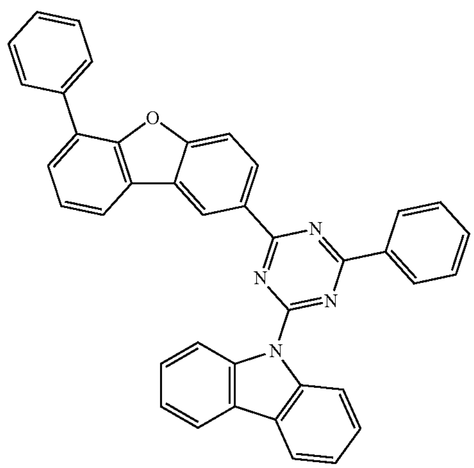
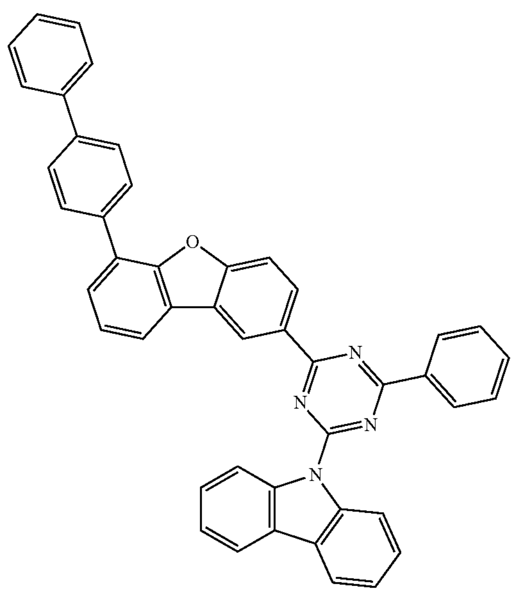
-continued
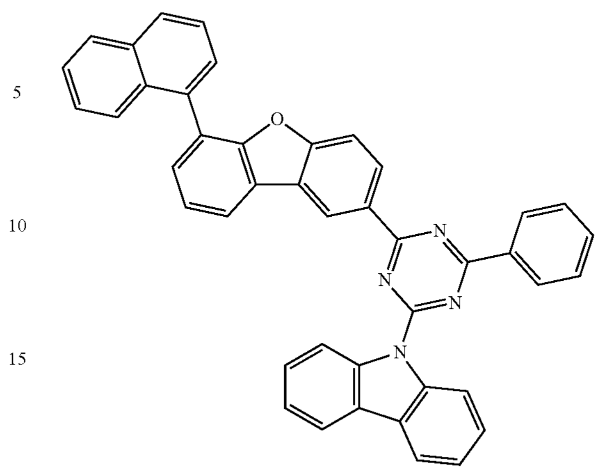
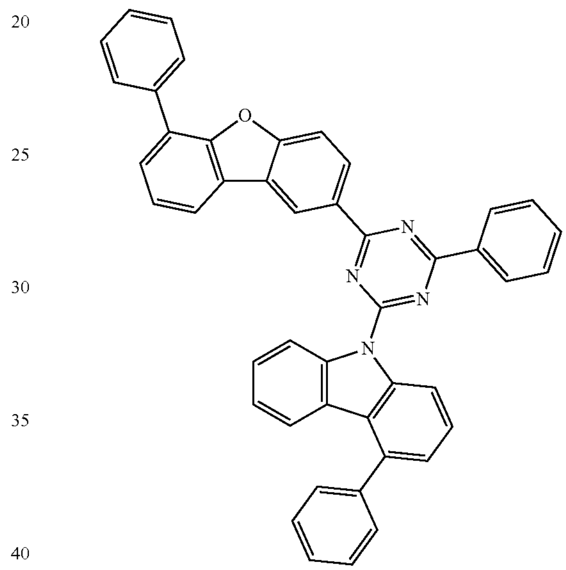
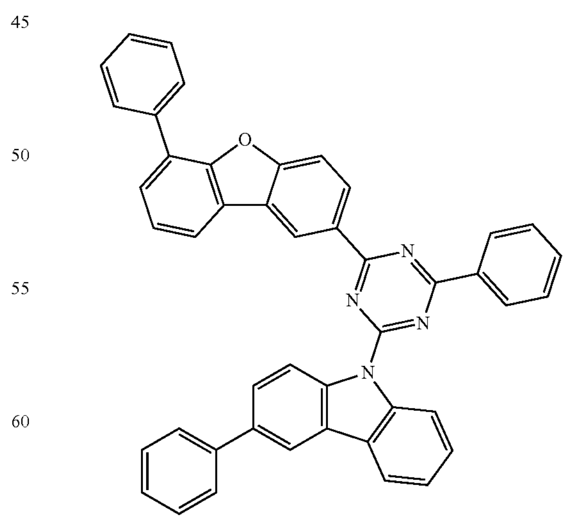

-continued
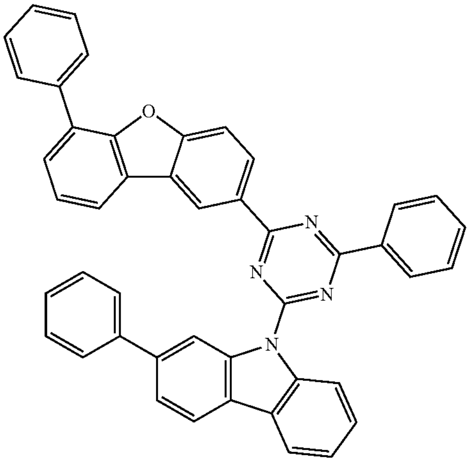
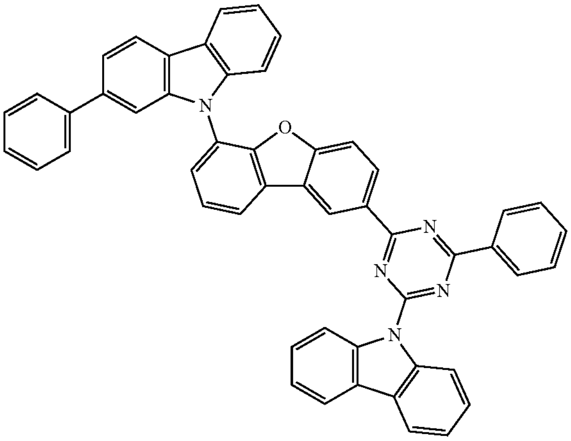
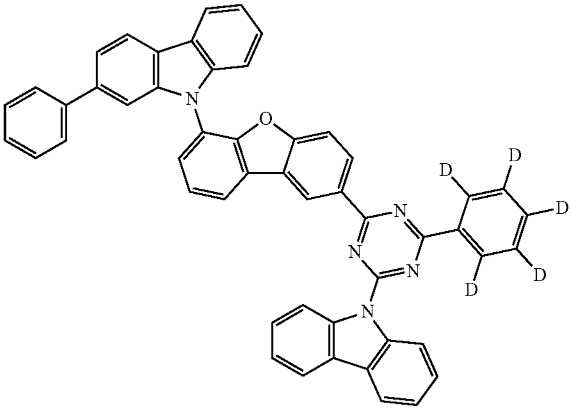
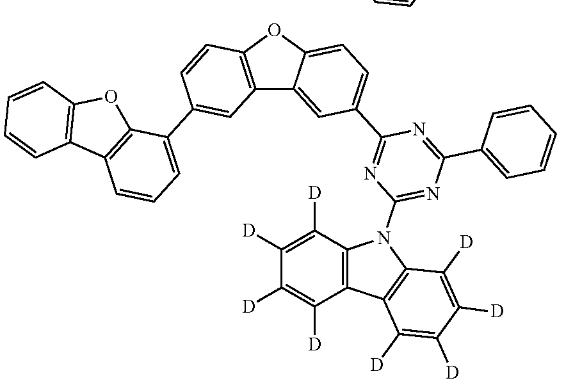
-continued
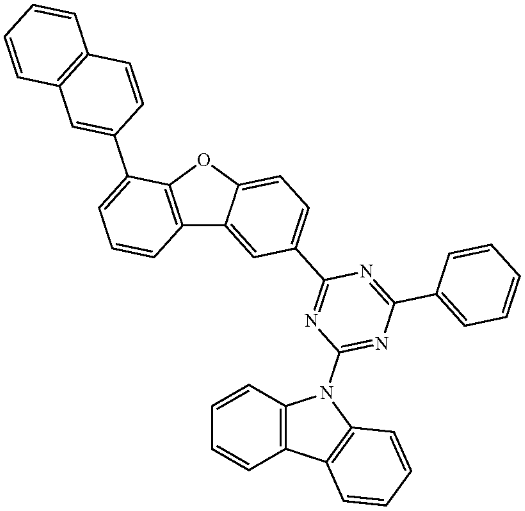
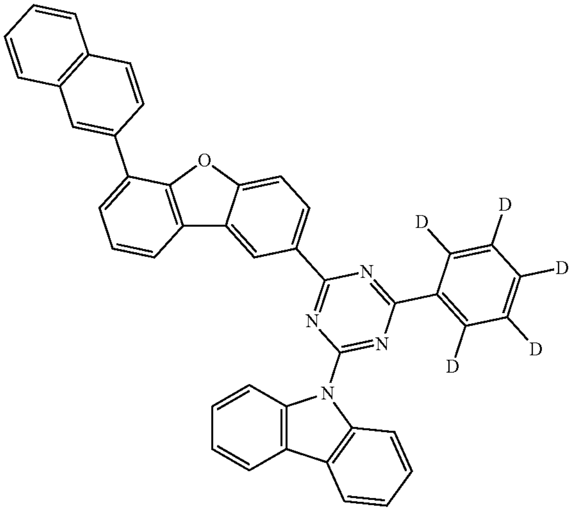
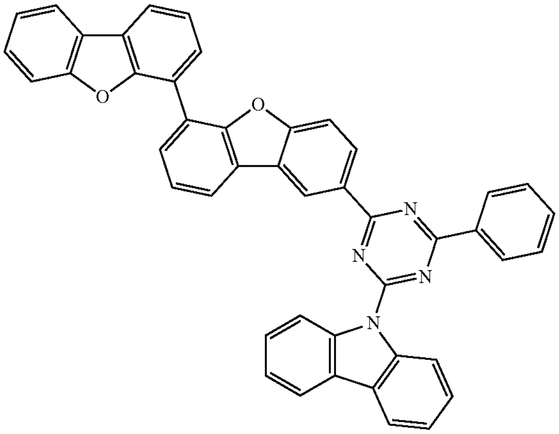

-continued
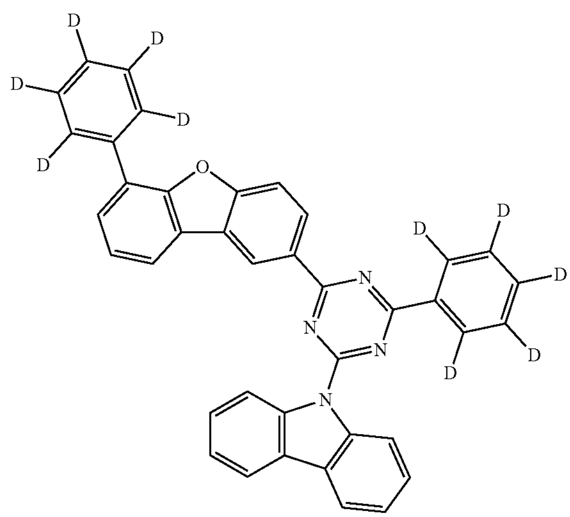
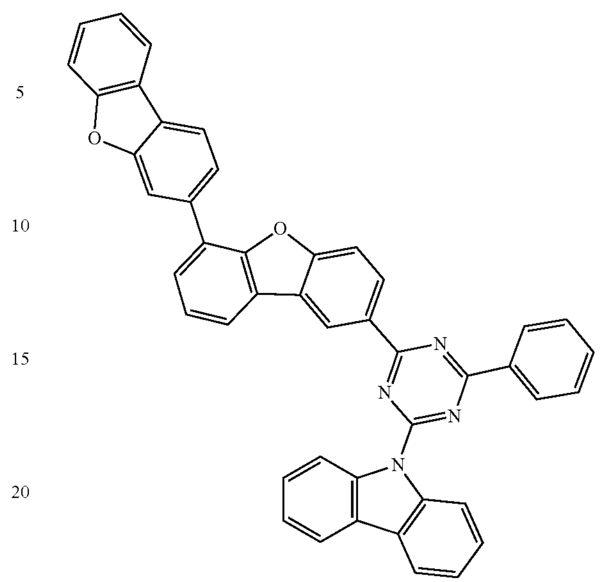
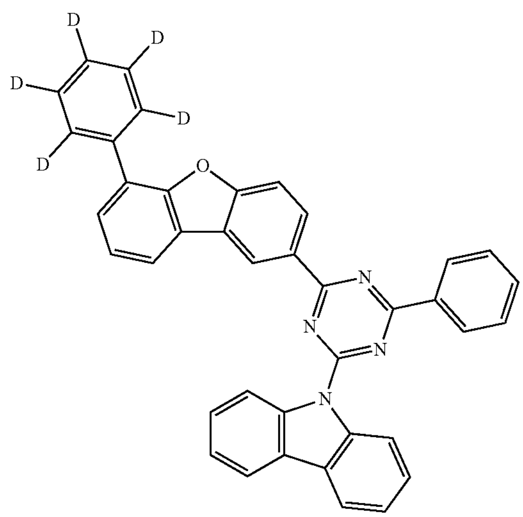
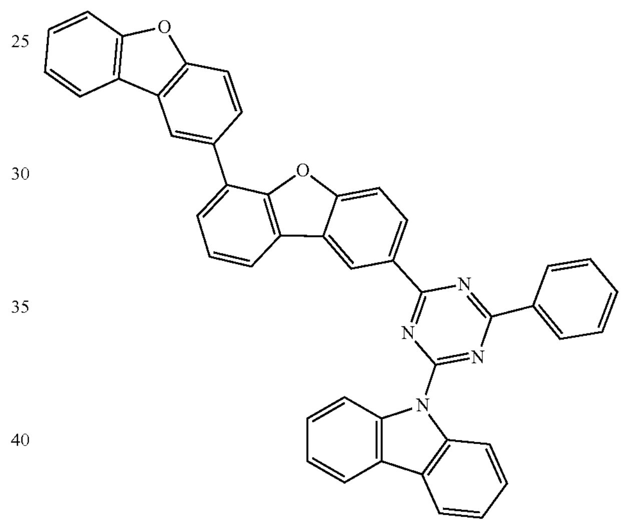
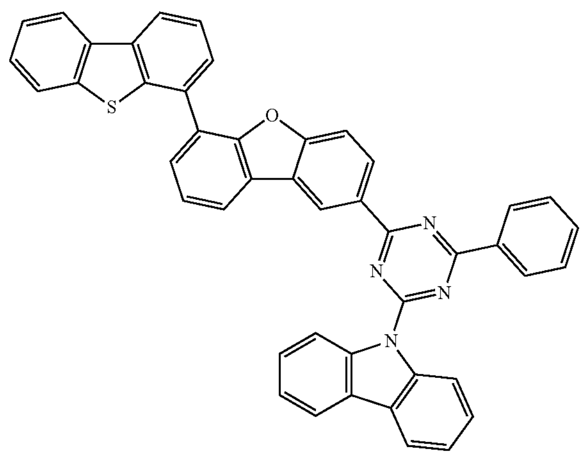
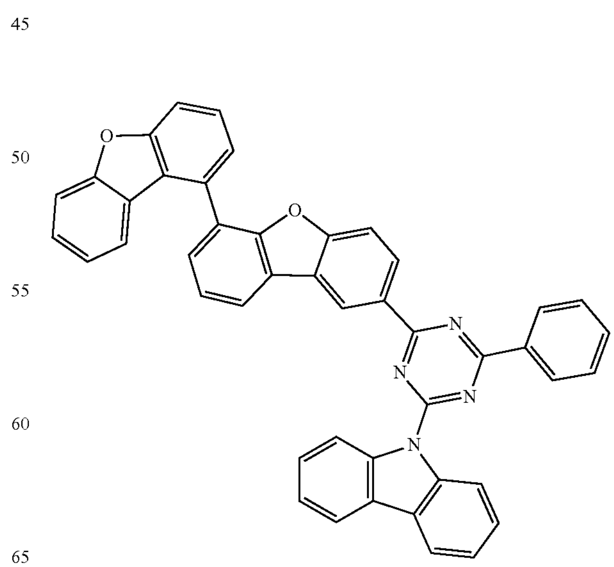

-continued
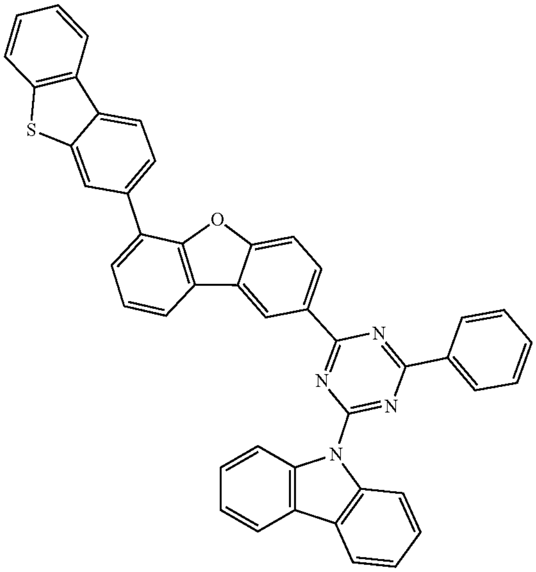
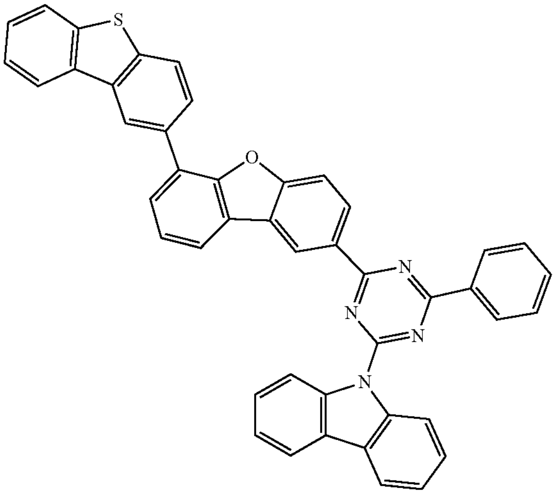
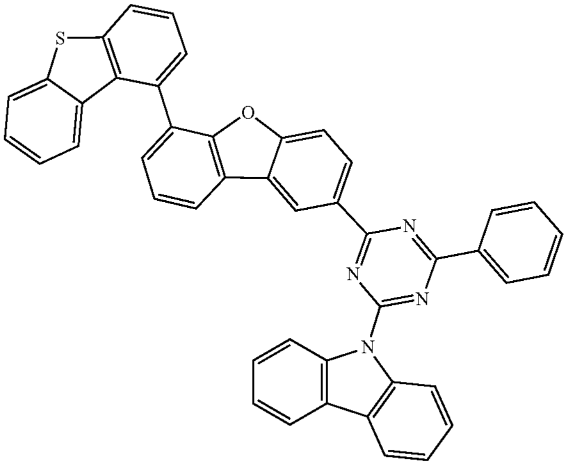
-continued
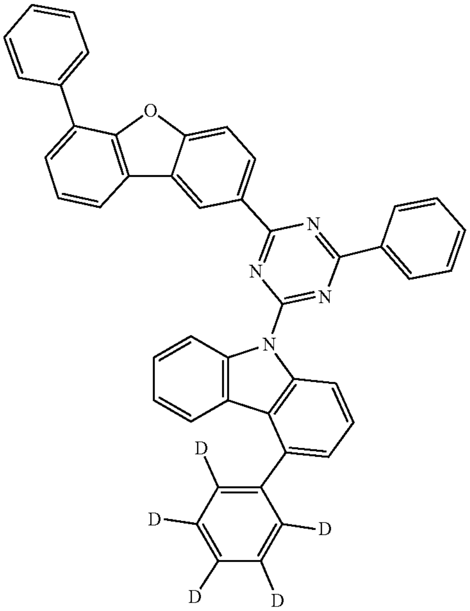
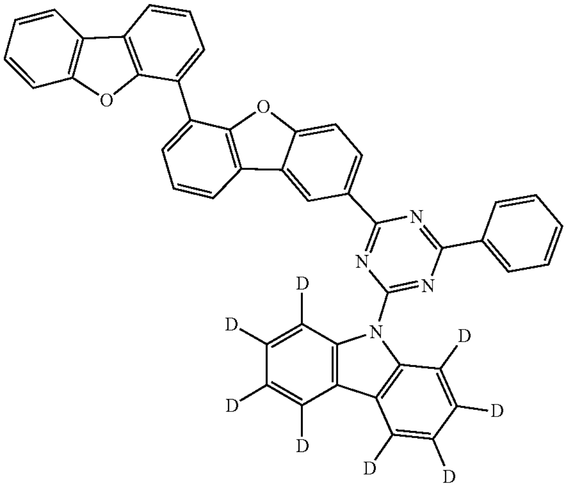
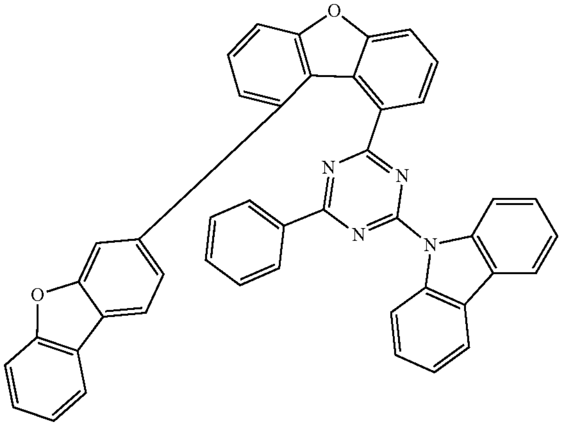

-continued
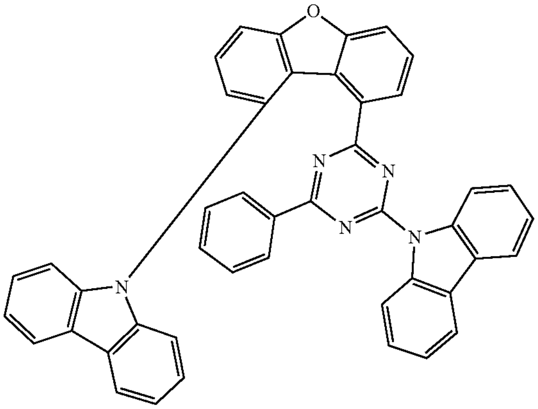
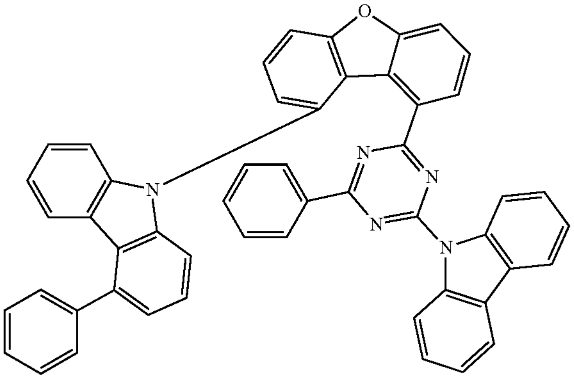
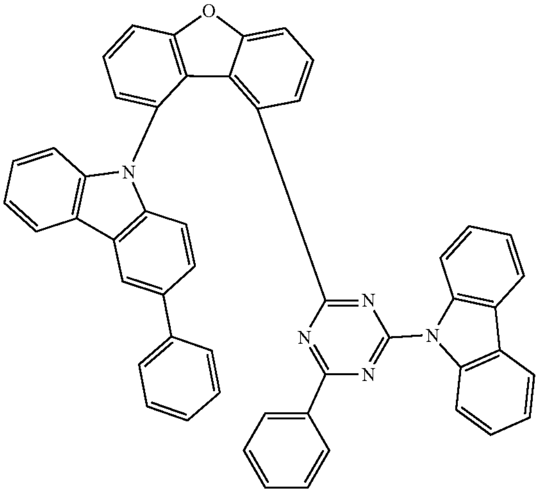
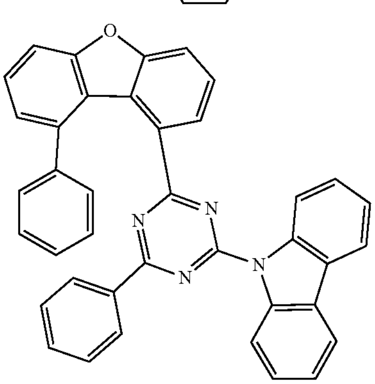
-continued
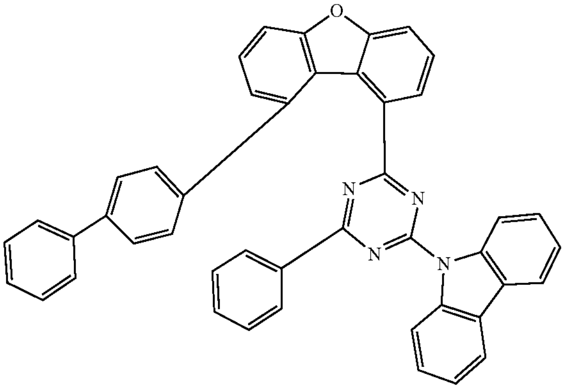
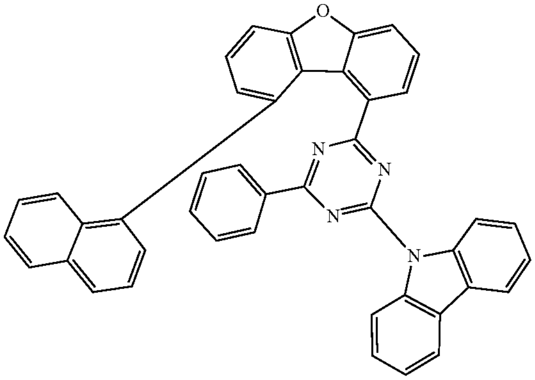
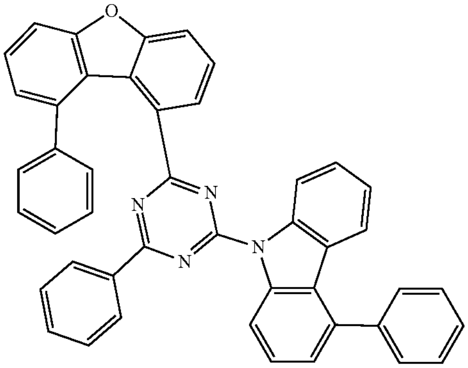
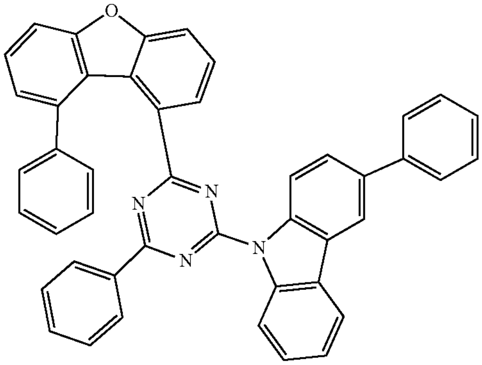

-continued
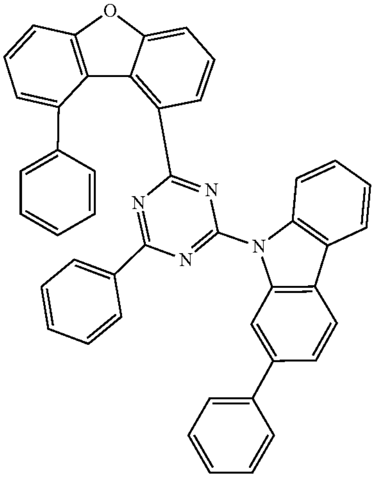
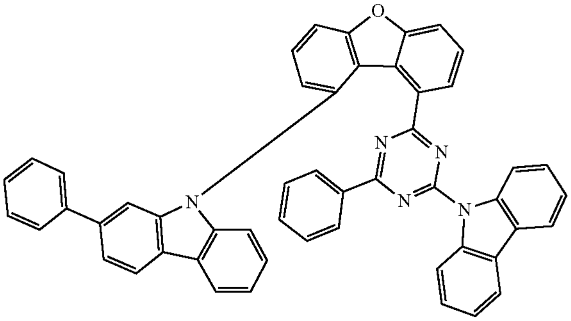
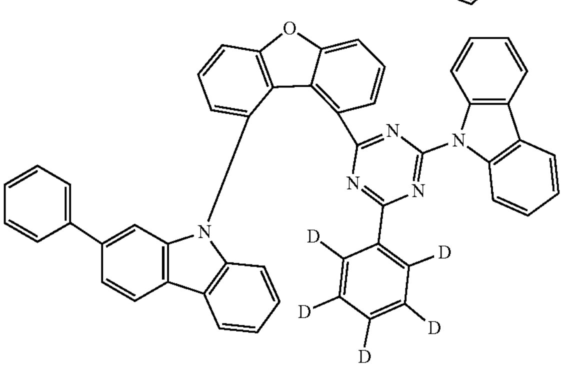
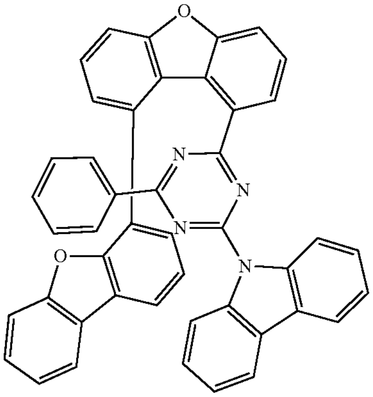
-continued
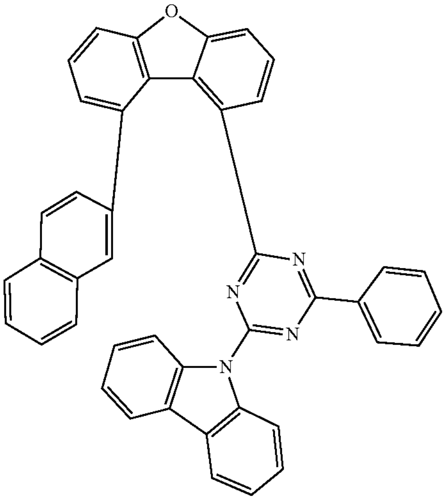
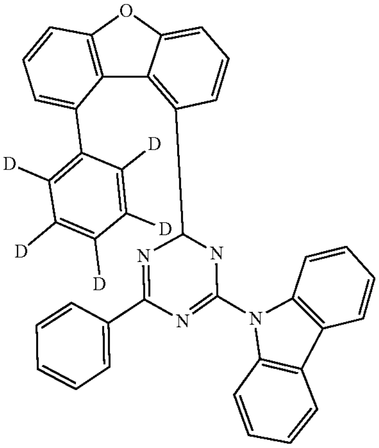
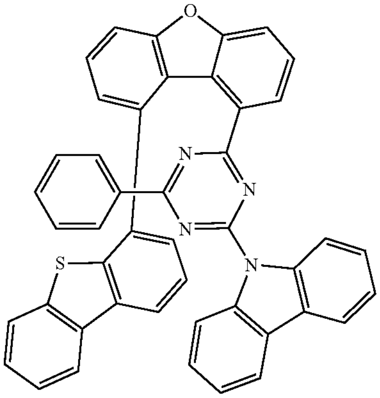
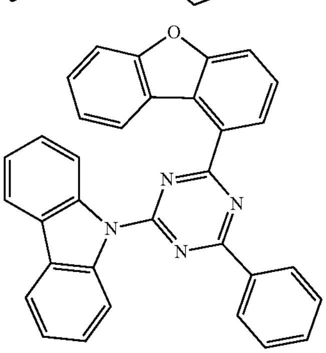

-continued
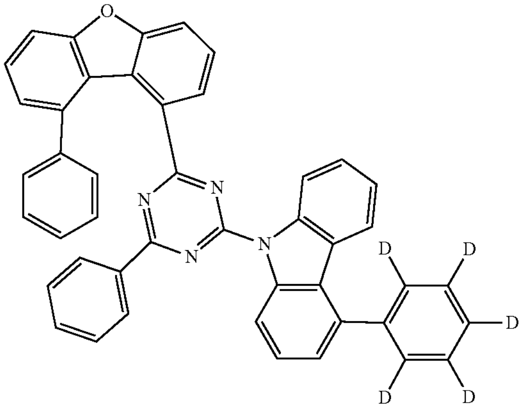
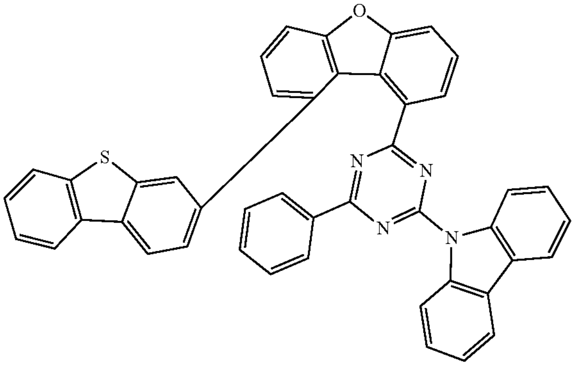
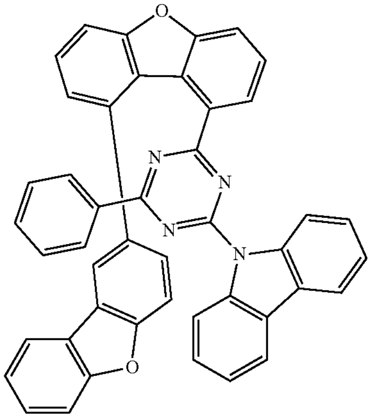
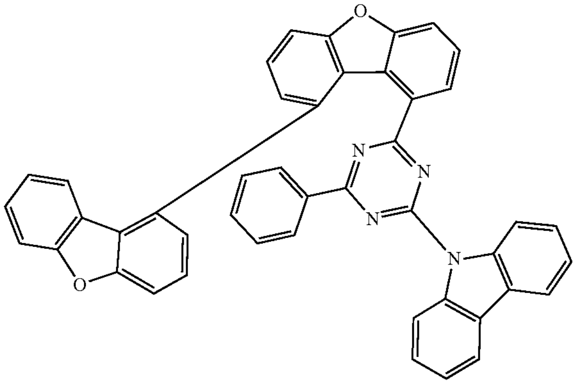
-continued
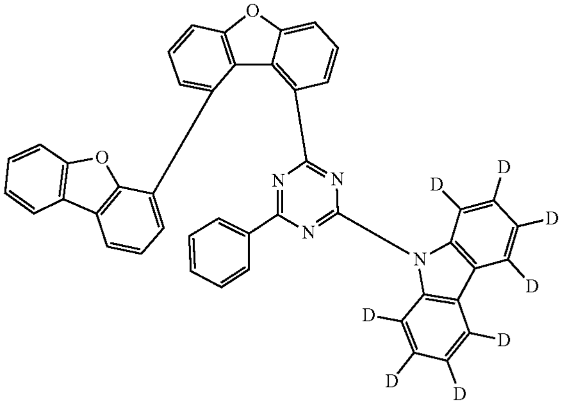
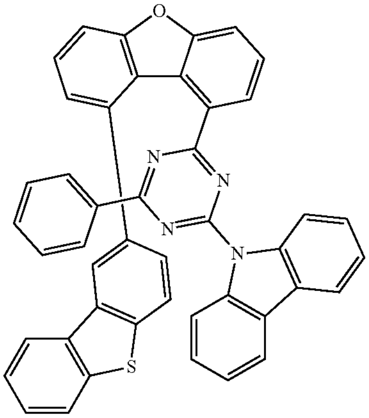
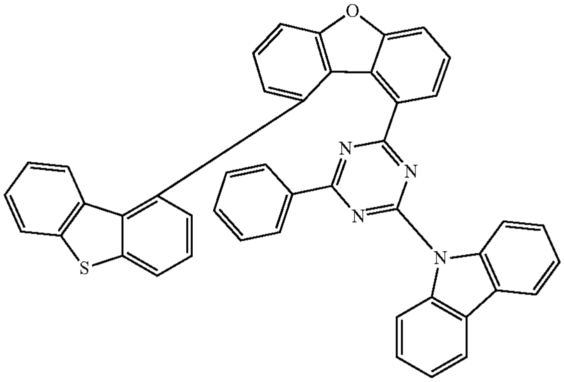
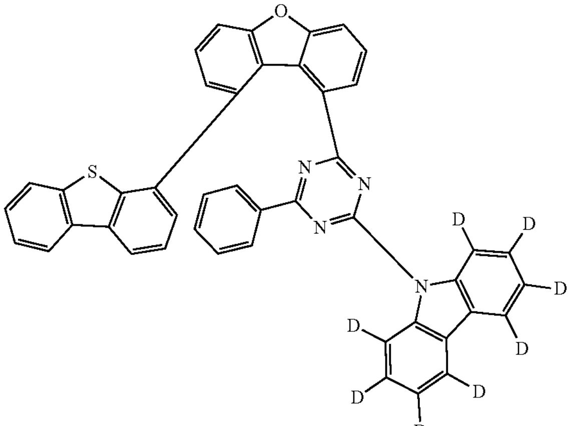

-continued
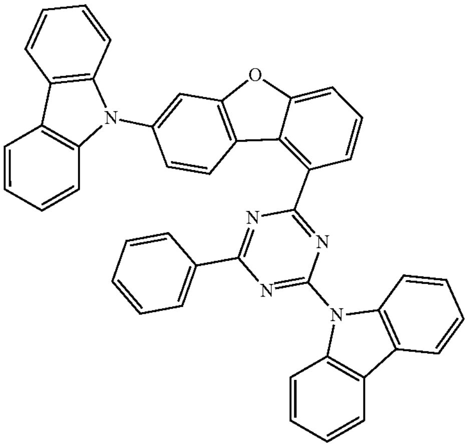
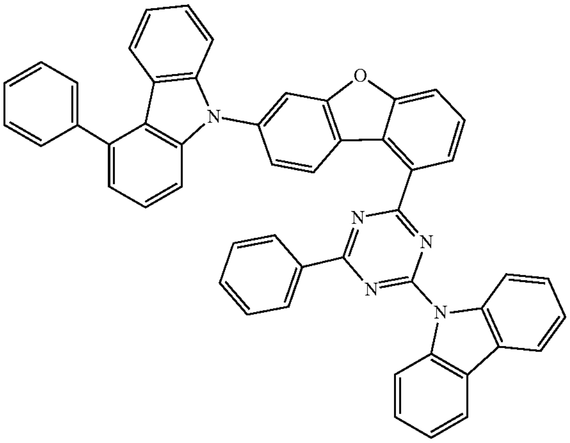
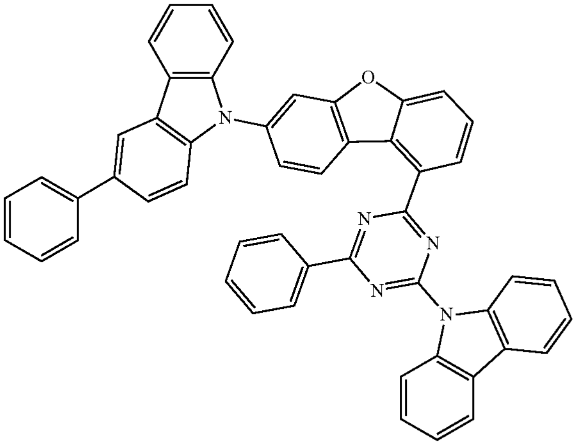
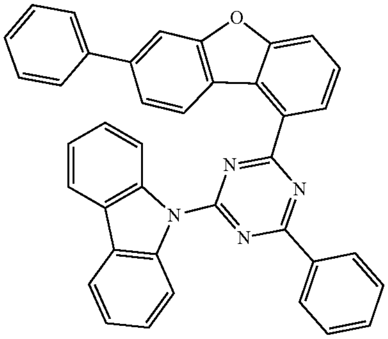
-continued
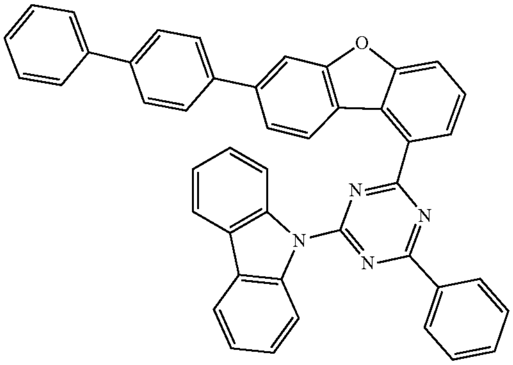
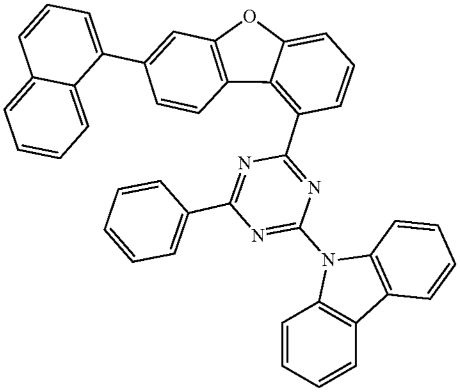
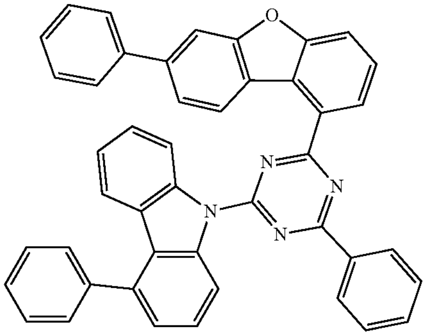
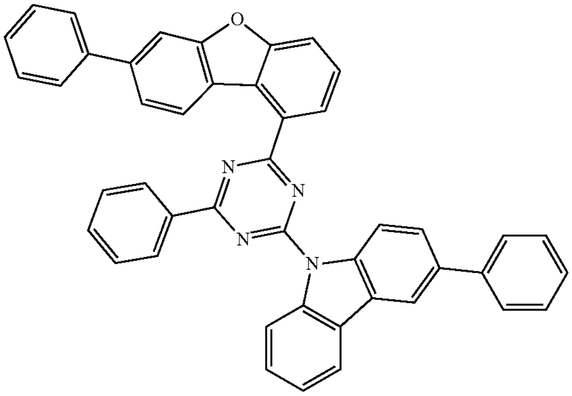

-continued
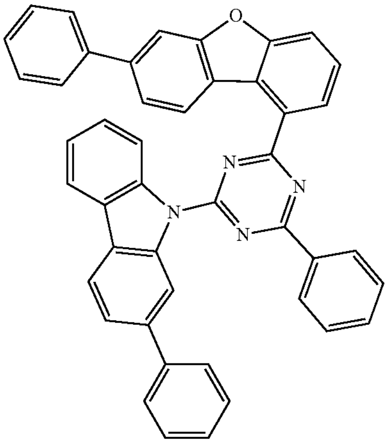
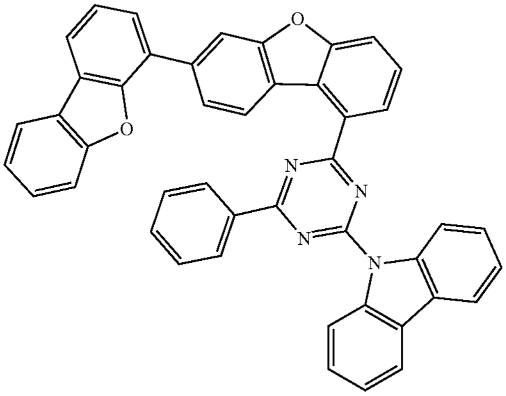
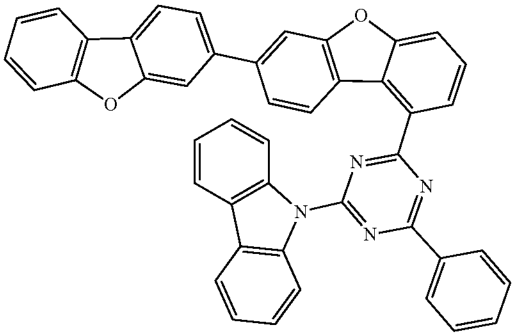
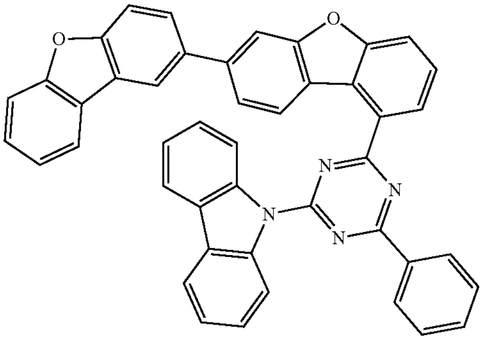
-continued
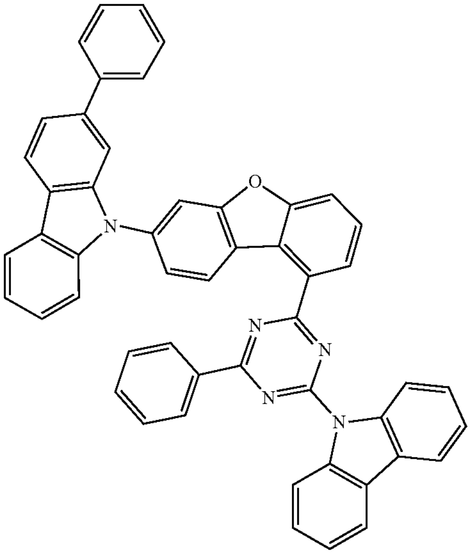
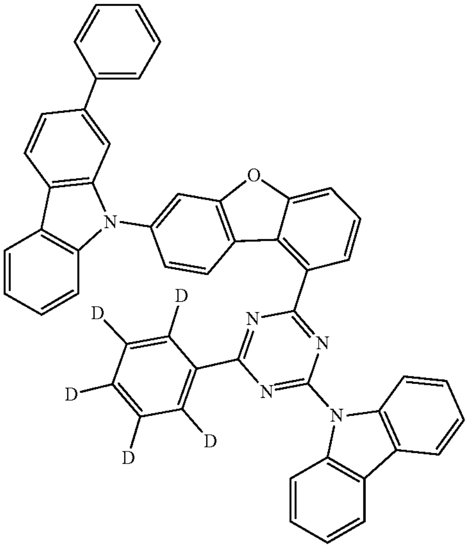
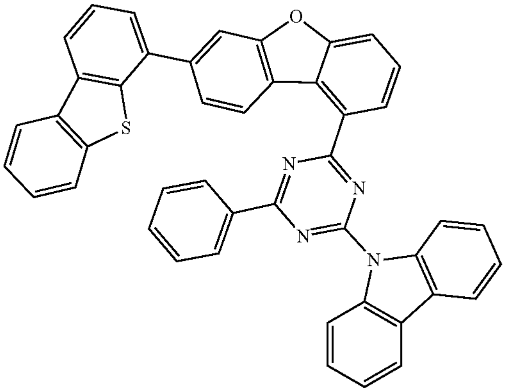

-continued
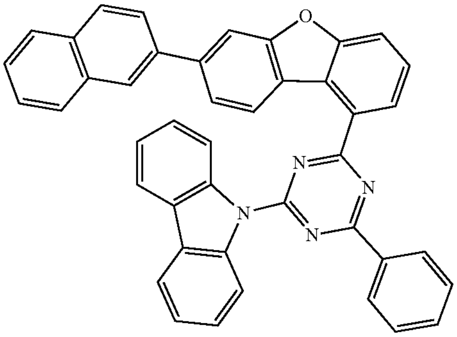
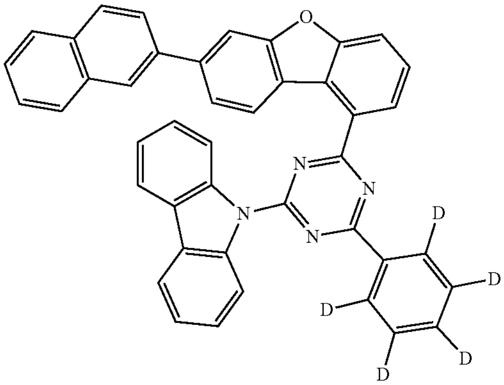
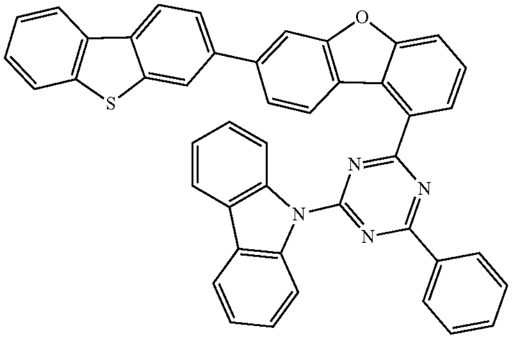
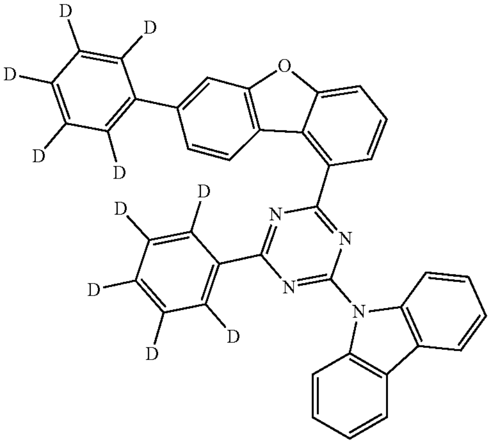
-continued
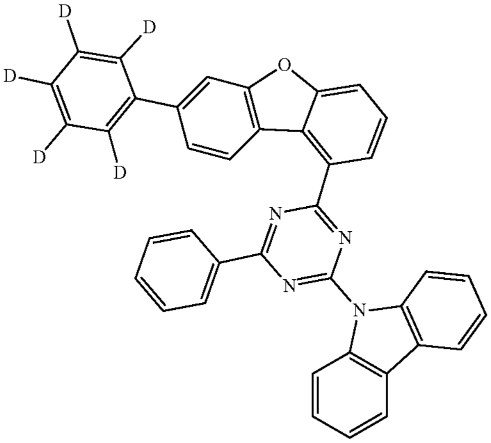
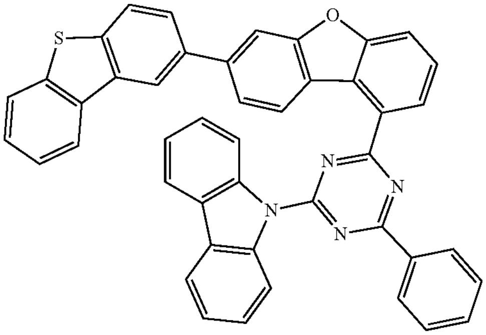
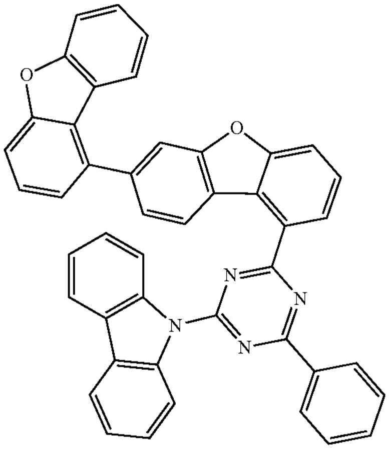
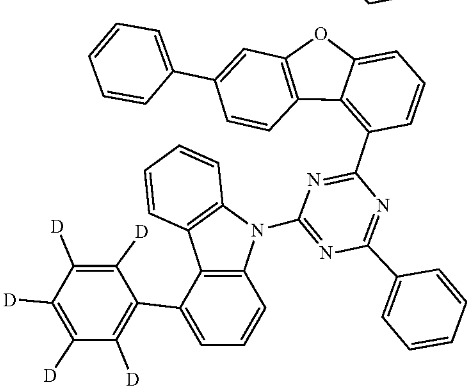

-continued
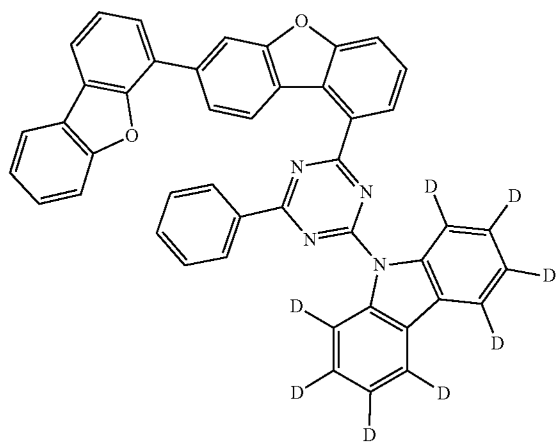
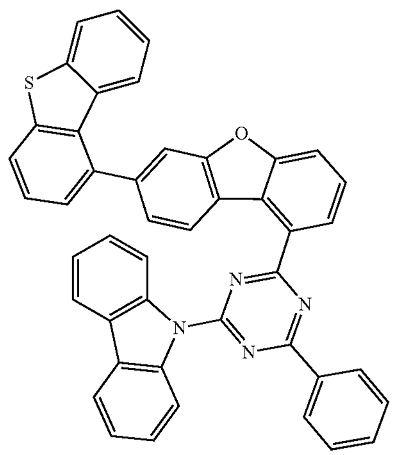
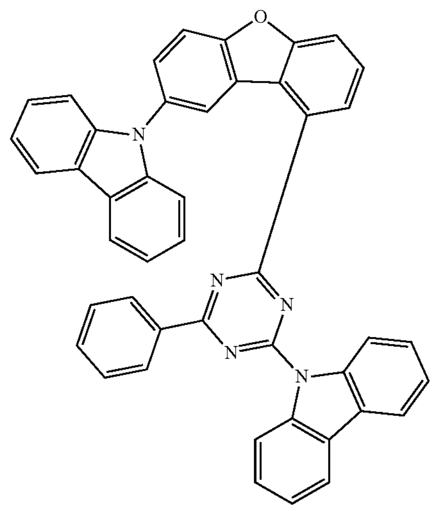
-continued
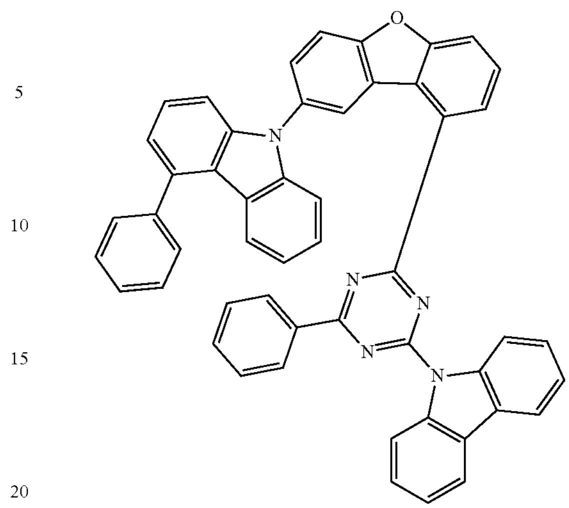
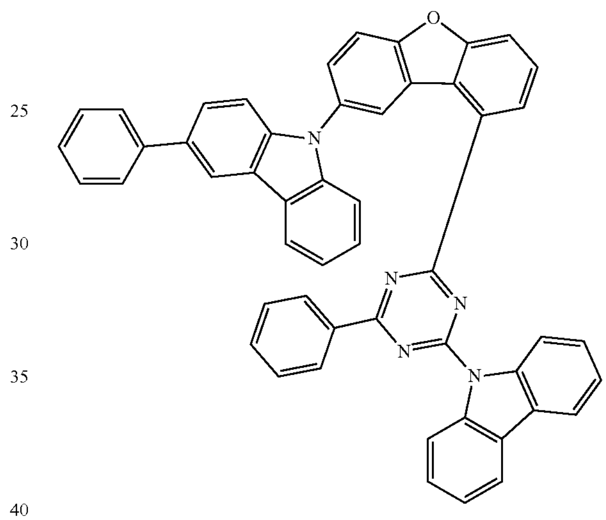
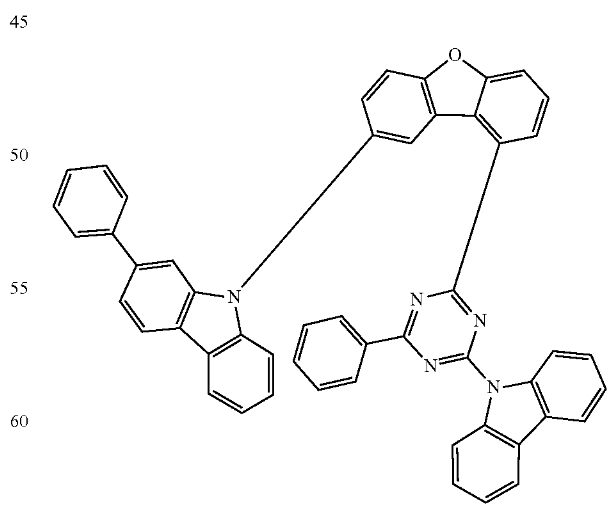

-continued
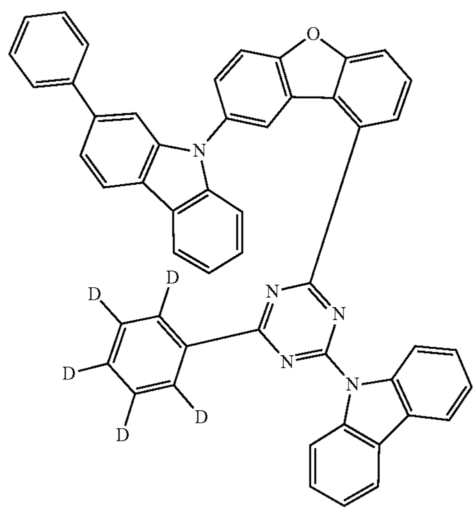
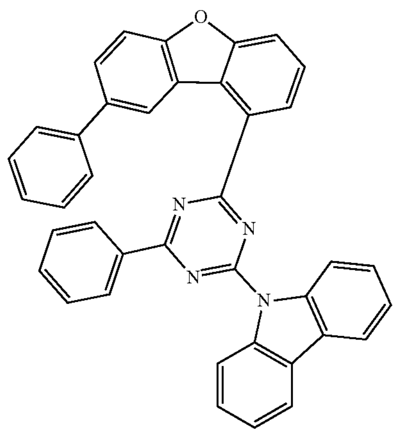
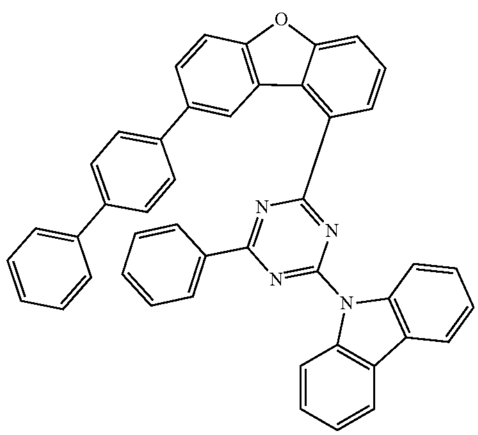
-continued
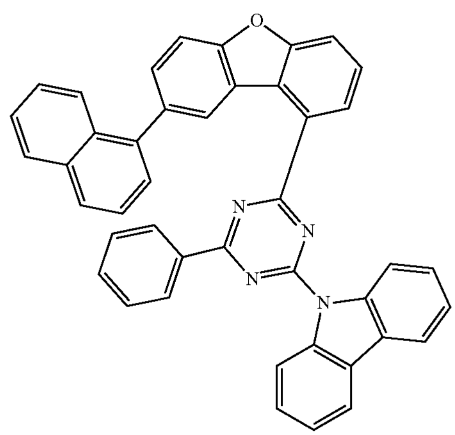
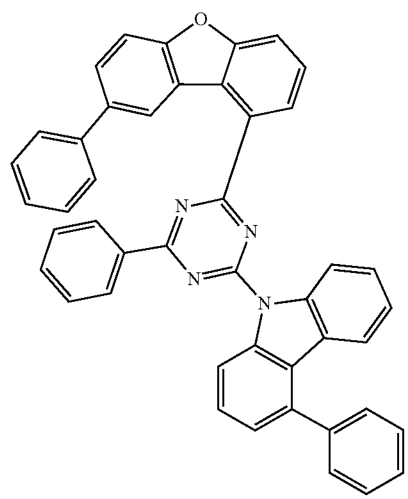
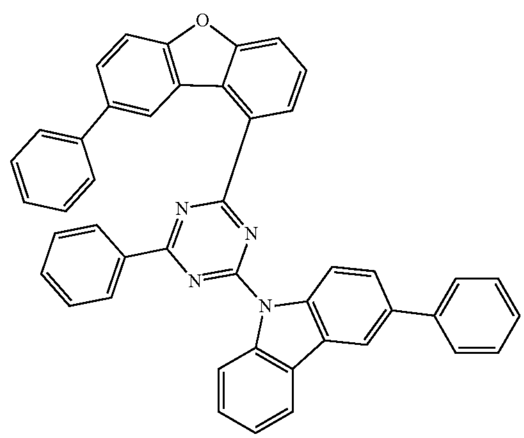

-continued
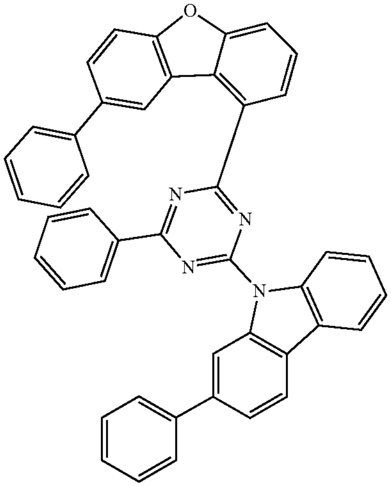
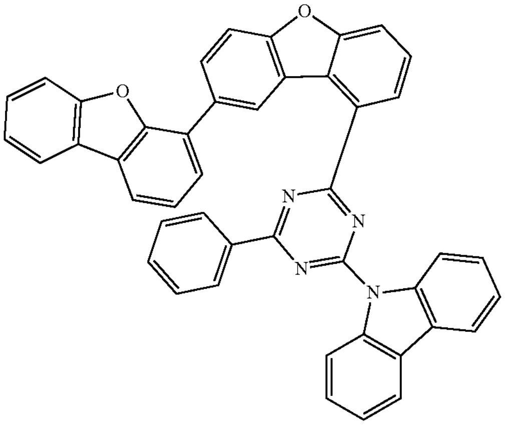
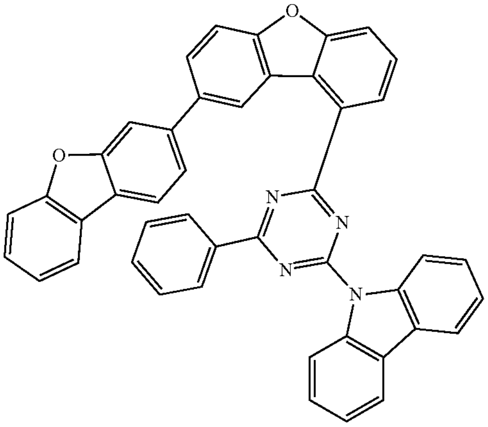
-continued
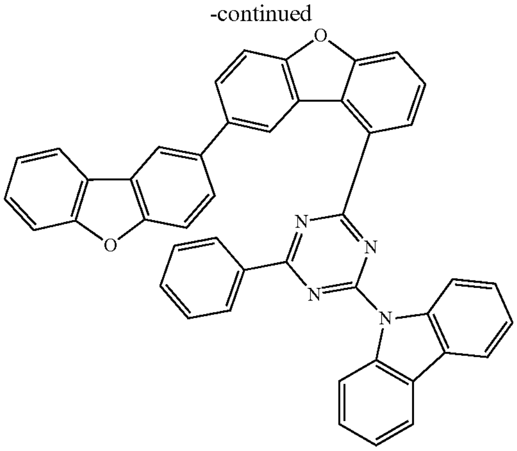
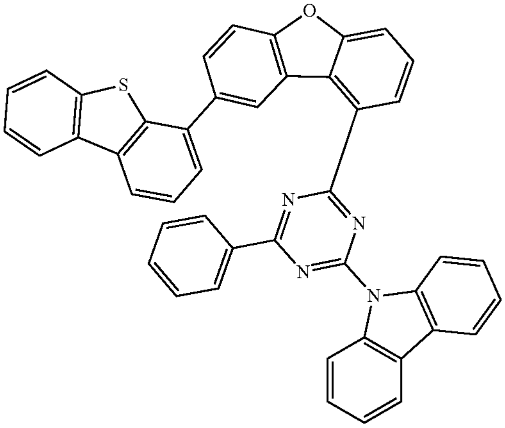
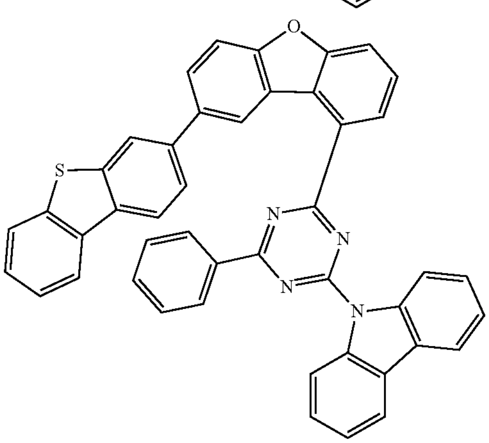
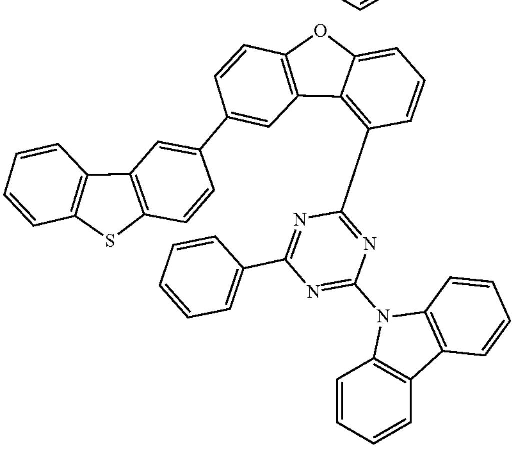

-continued
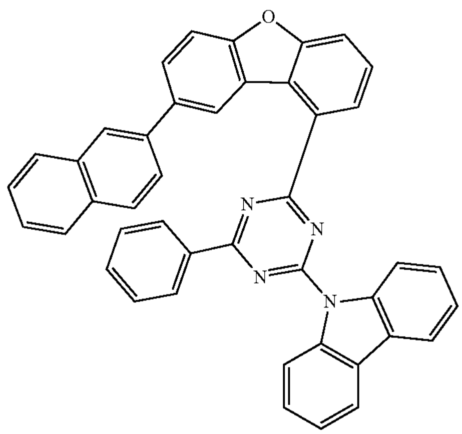
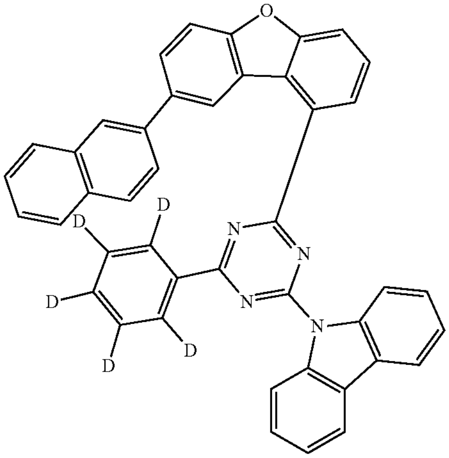
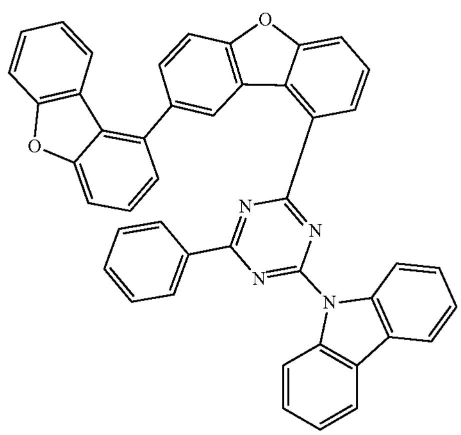
-continued
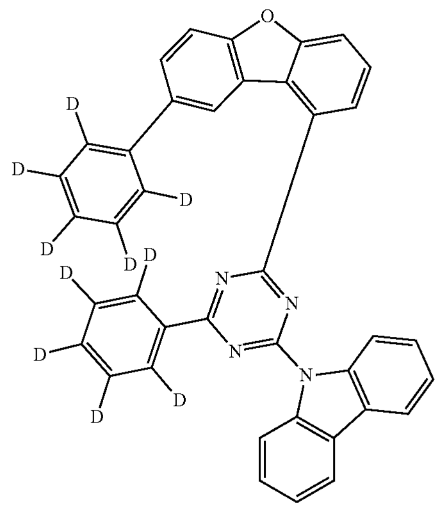
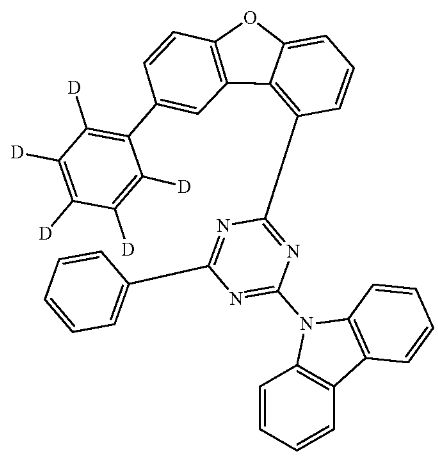
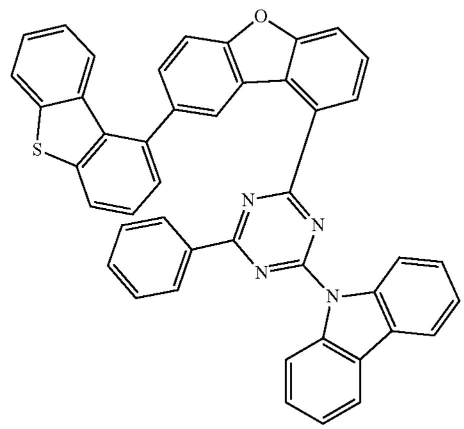

-continued
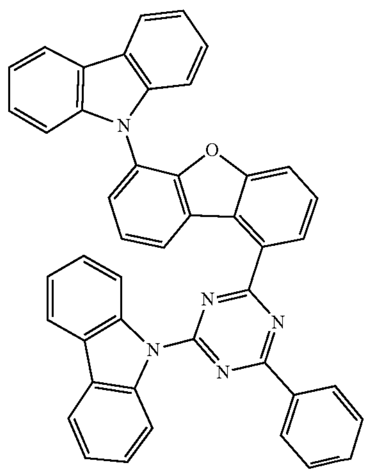
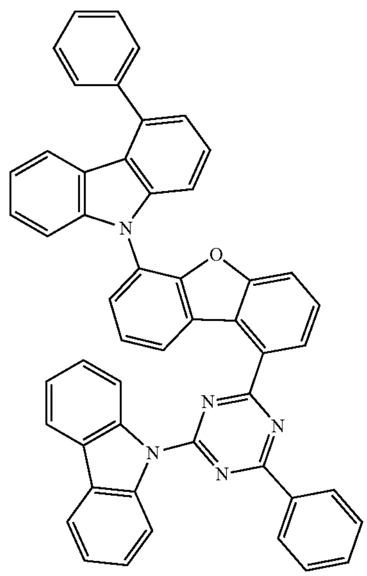
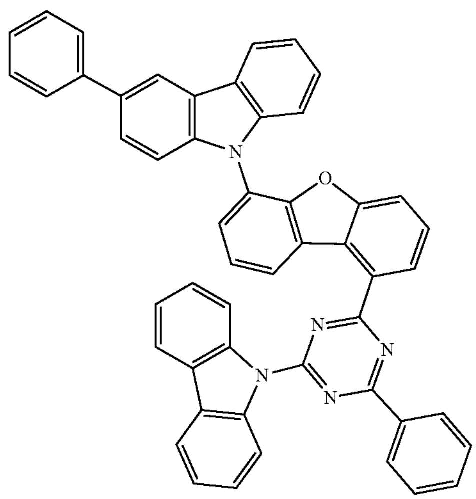
-continued
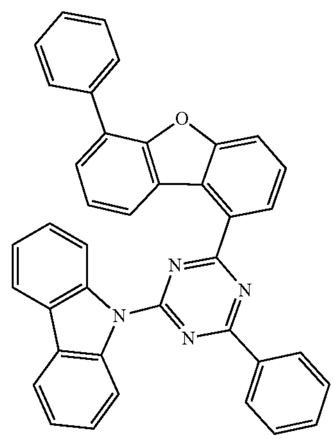
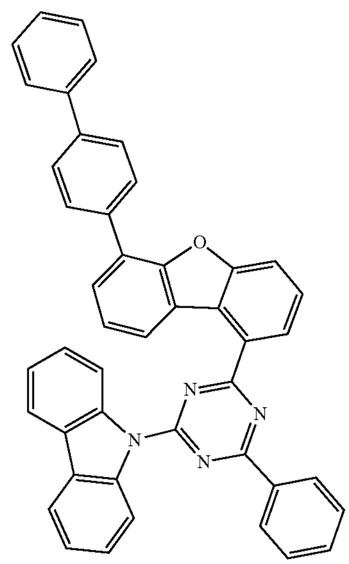
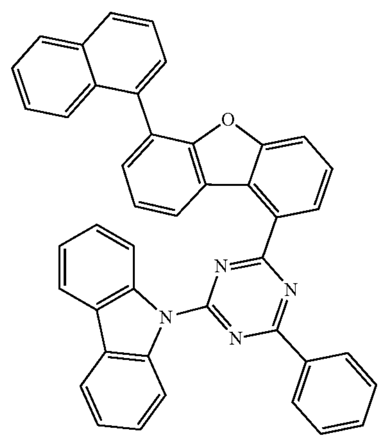

-continued
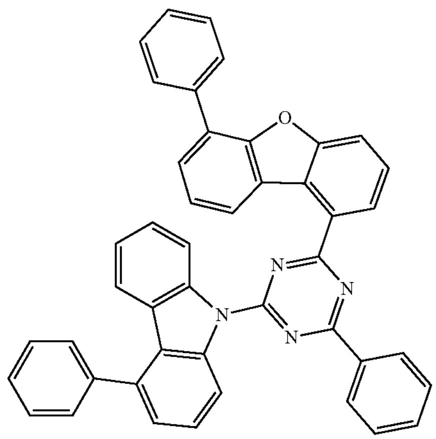
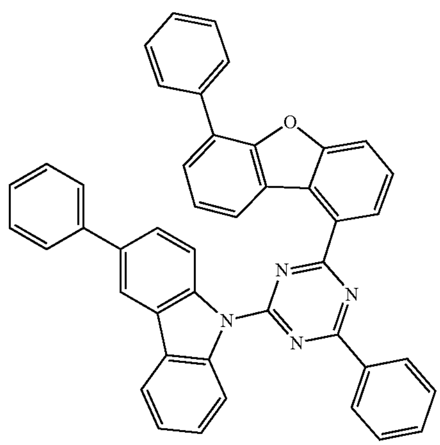
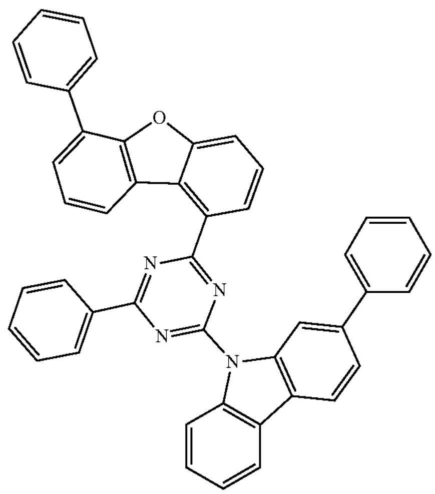
-continued
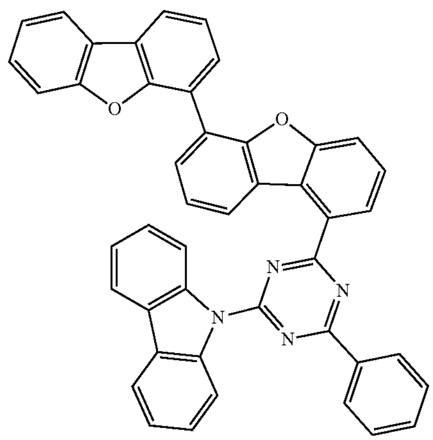
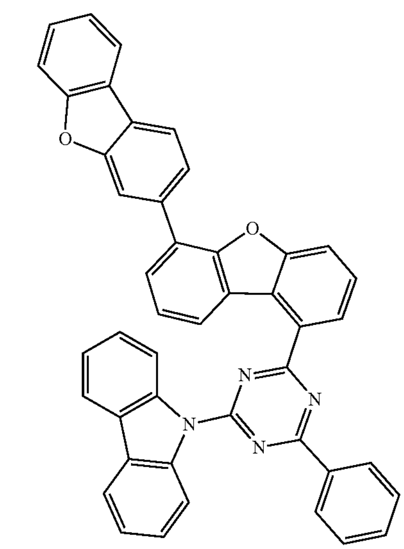
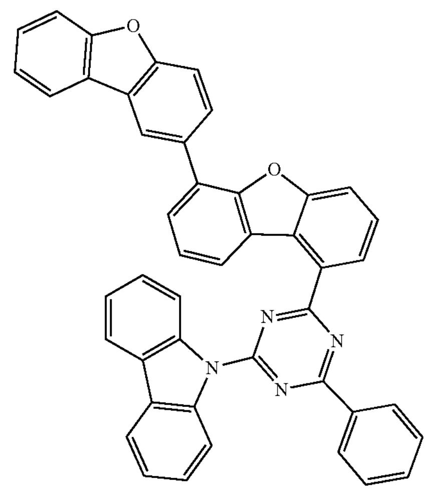

-continued
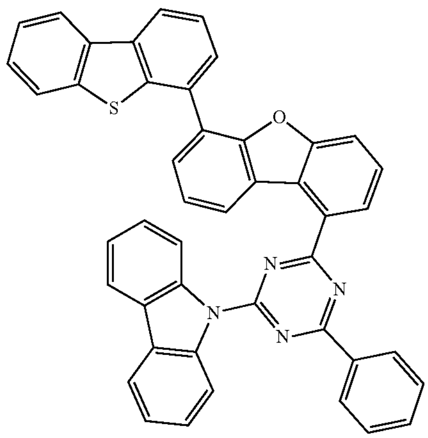
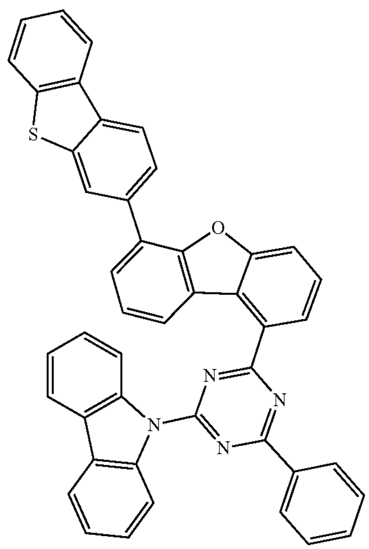
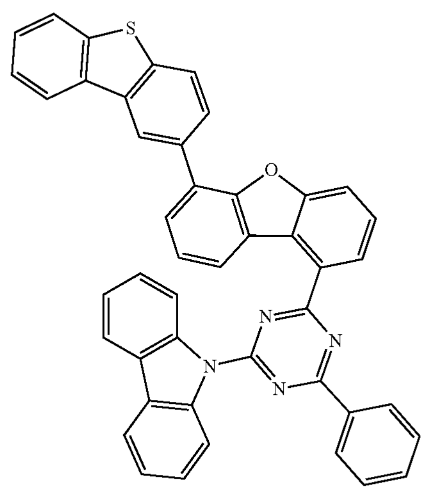
-continued
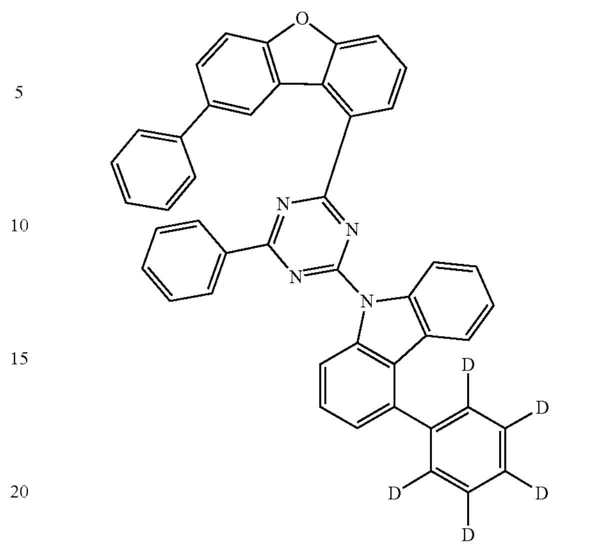
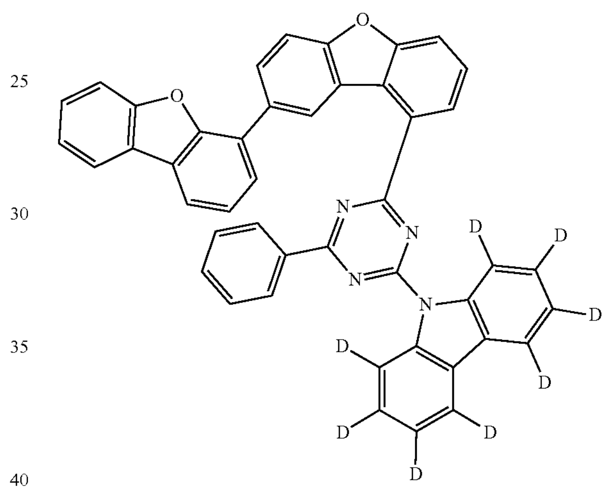
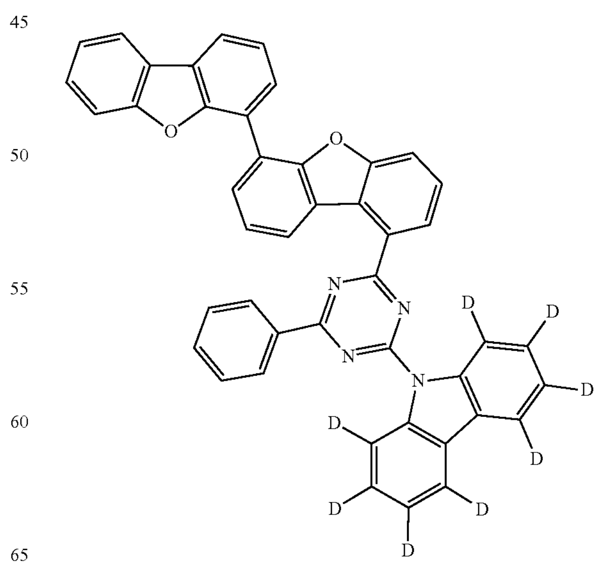

-continued
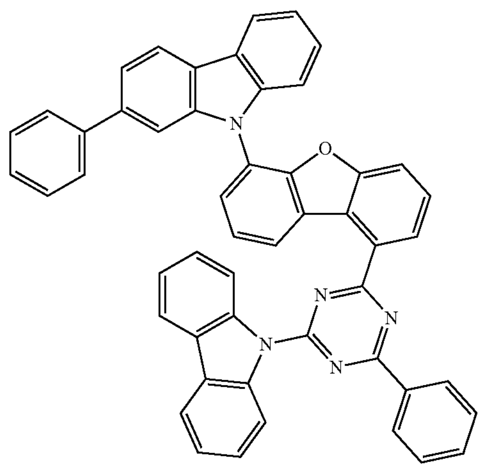
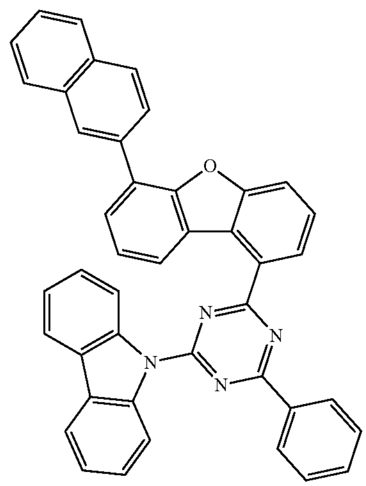
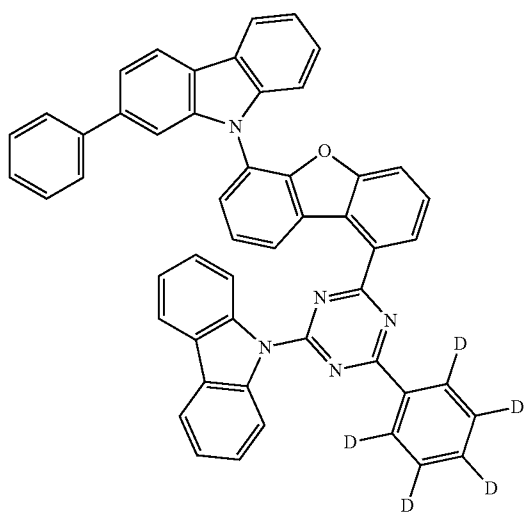
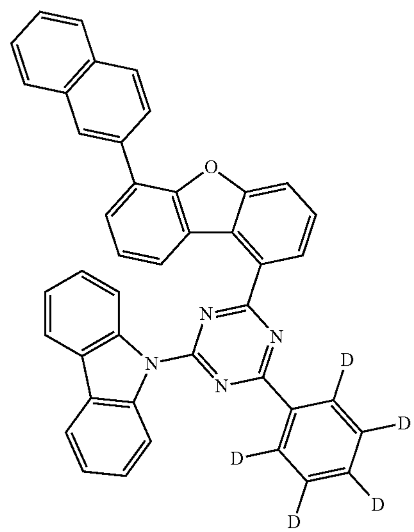
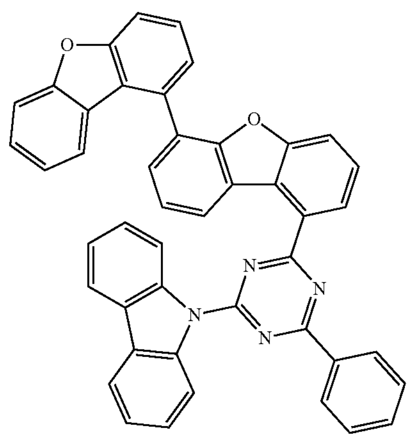
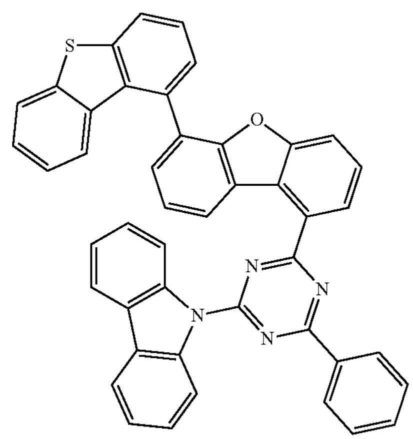

-continued
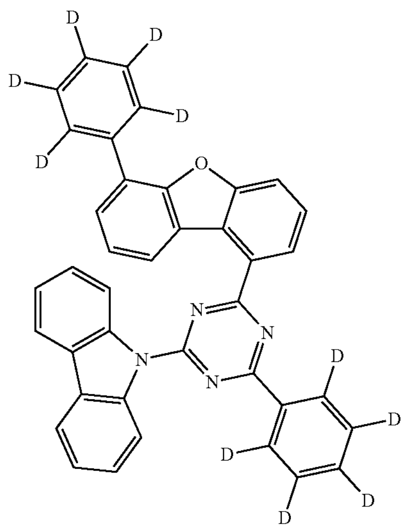
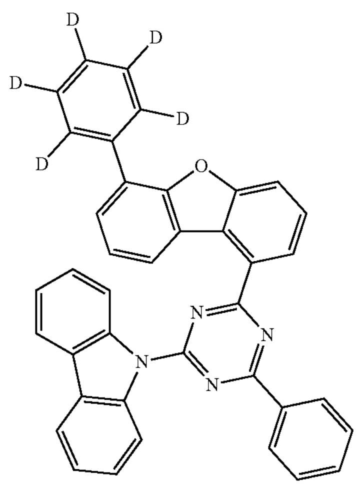
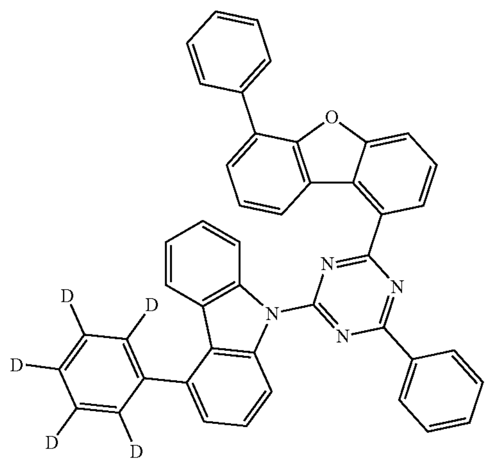
-continued
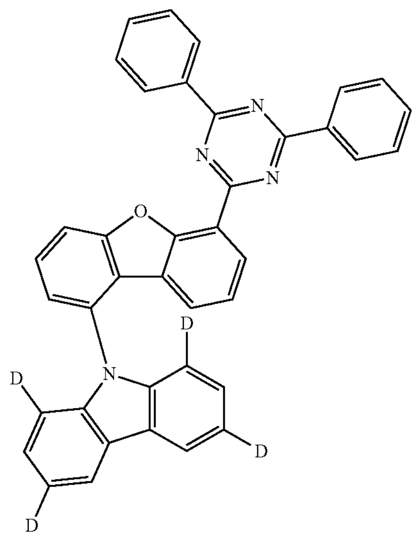
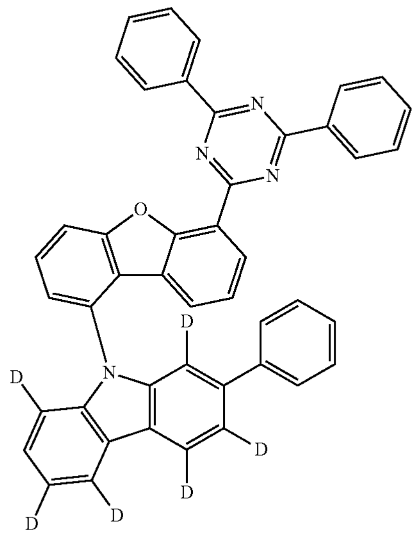
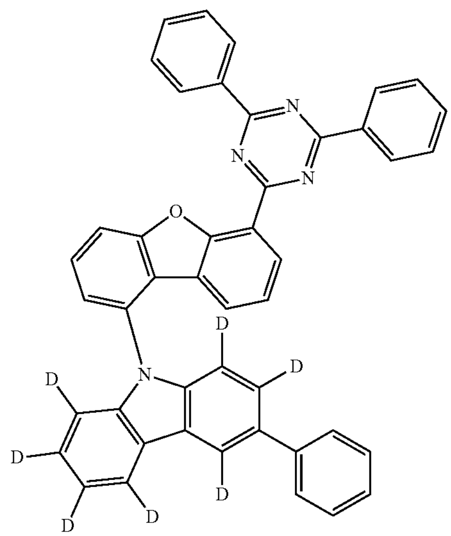

-continued
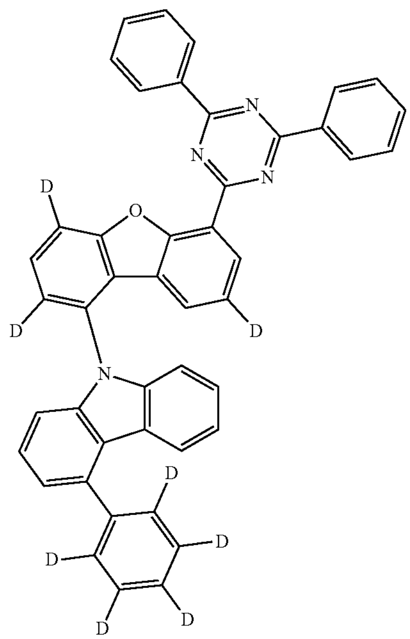
-continued
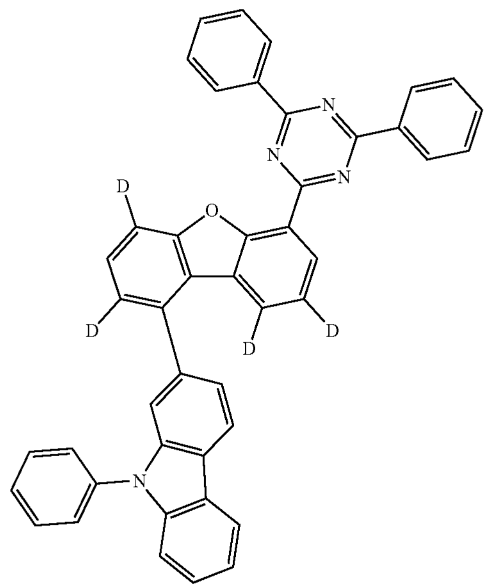
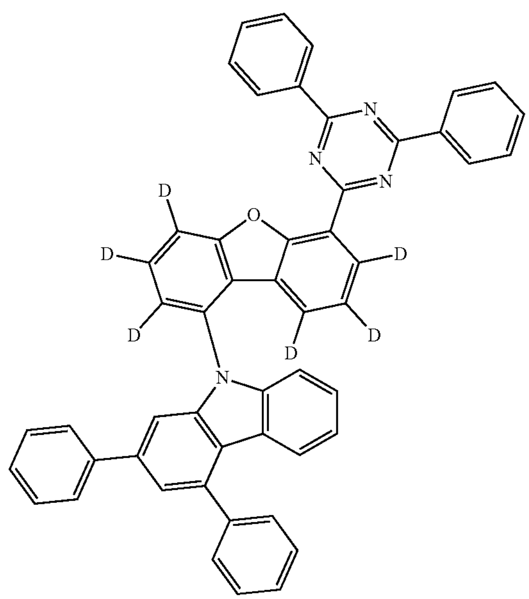
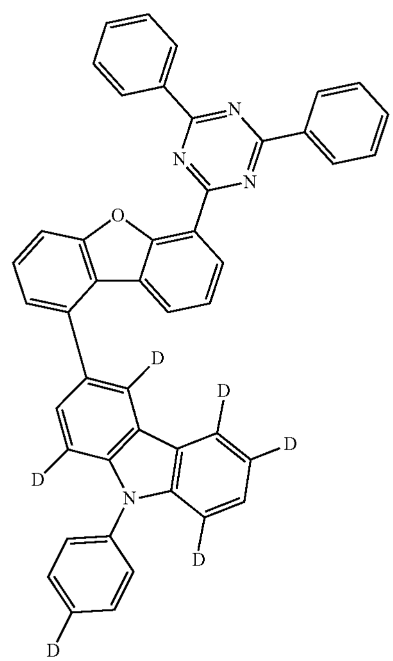

-continued
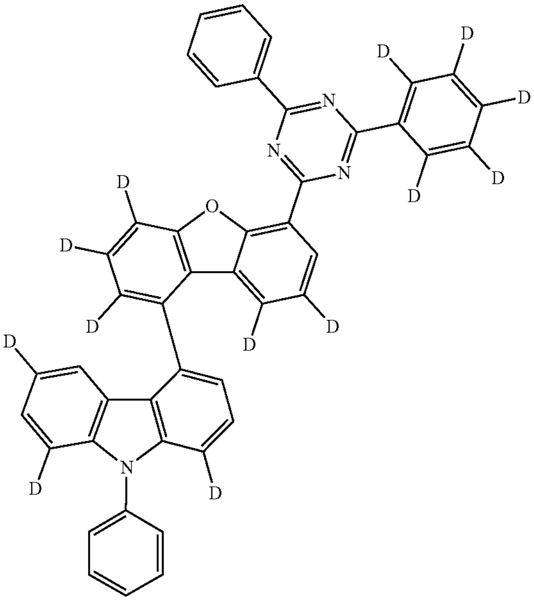
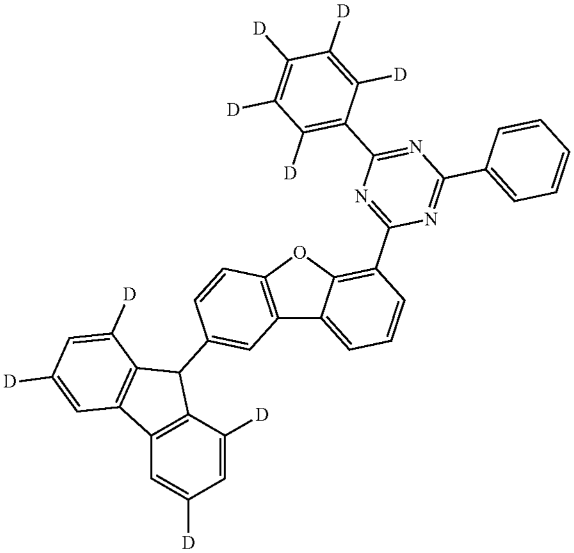
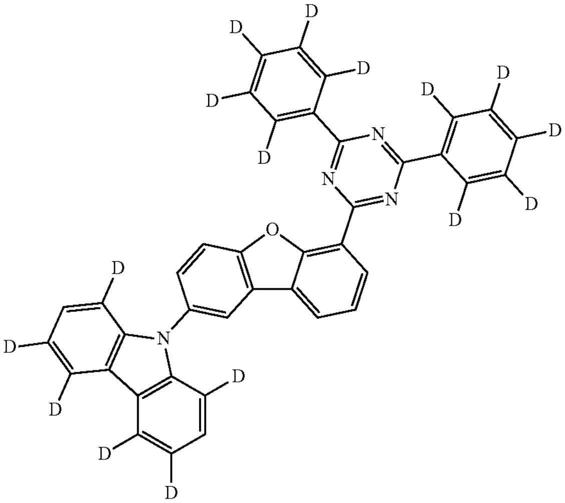
-continued
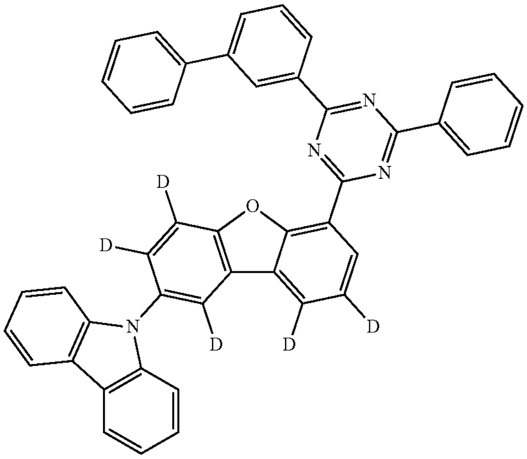
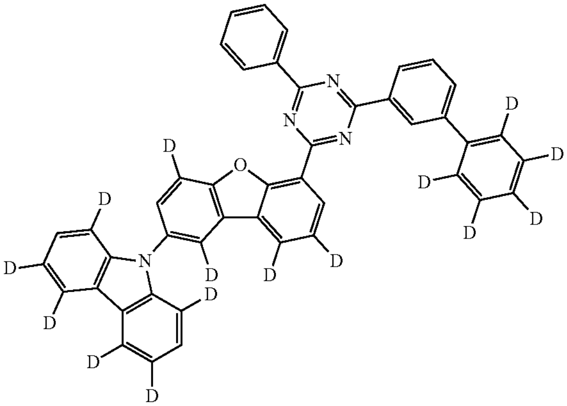
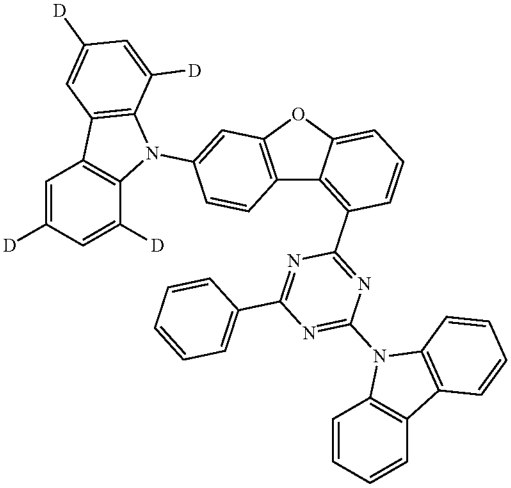

-continued
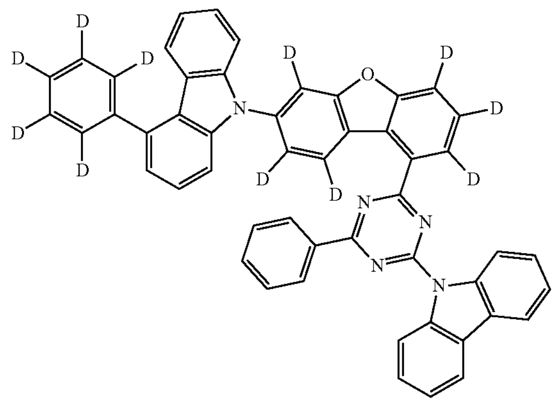
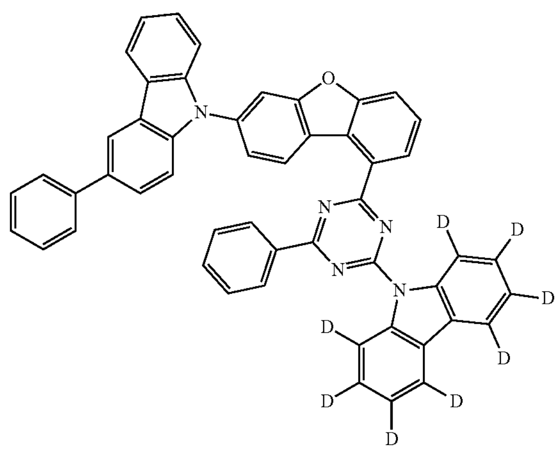
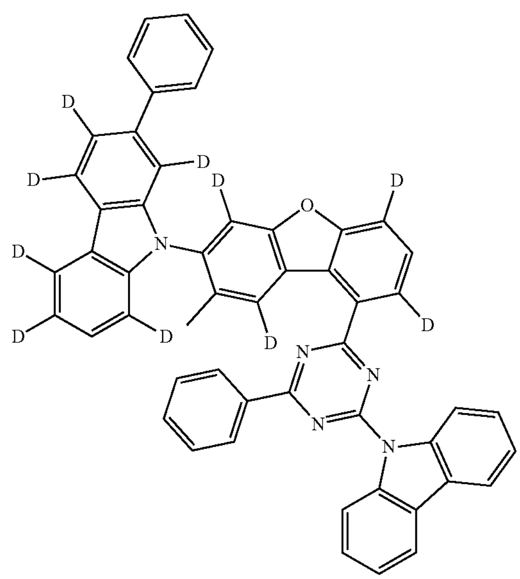
-continued
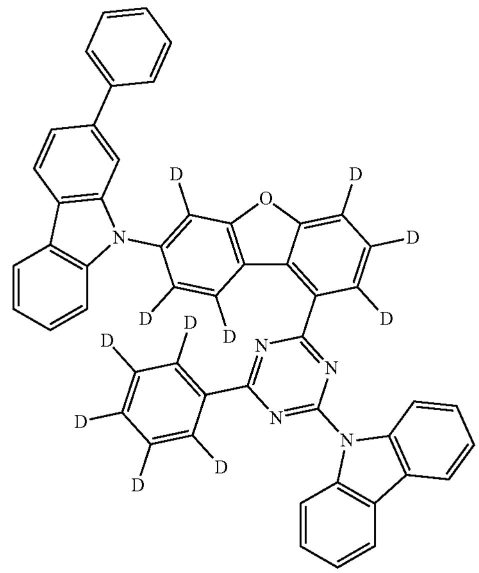
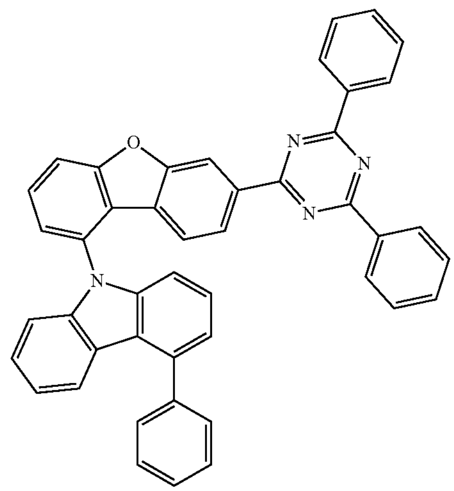
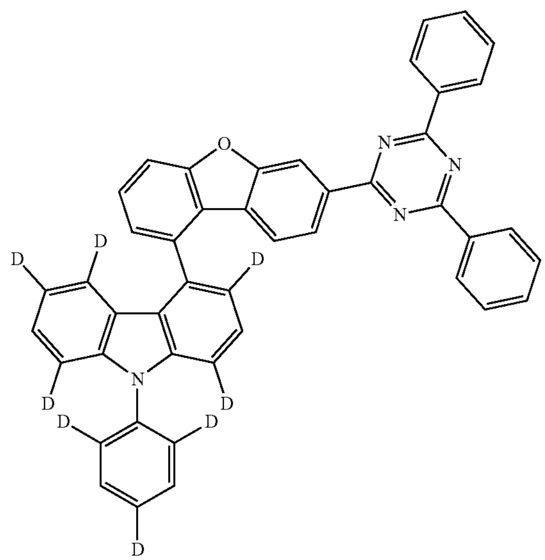

-continued

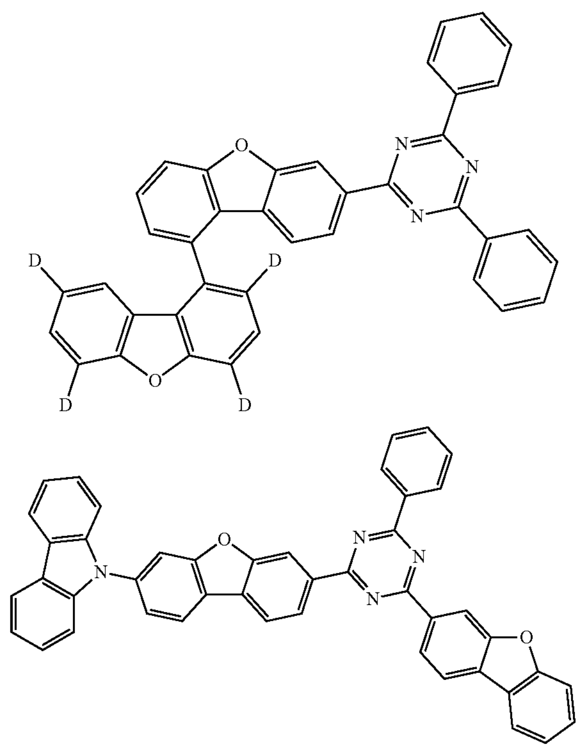

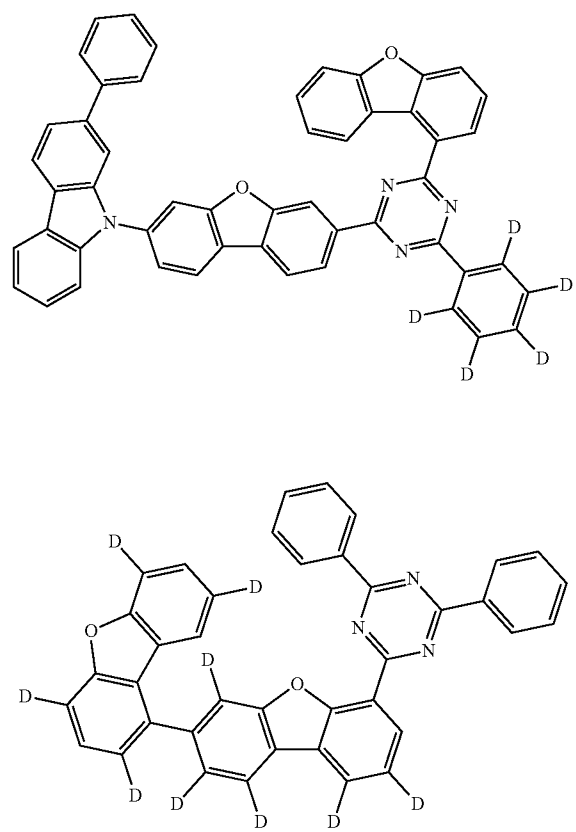

-continued

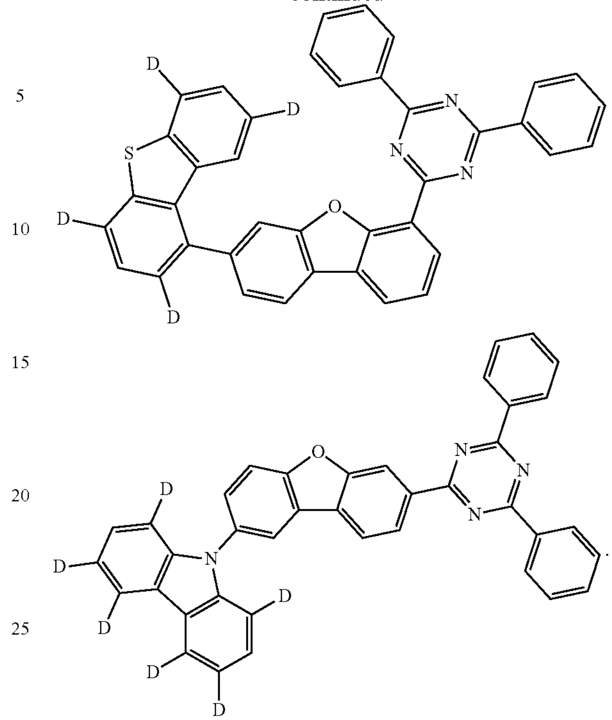

In addition, the present disclosure provides a method for preparing the compound of Chemical Formula 1 as shown in the following Reaction Scheme 1.

[Reaction Scheme 1]

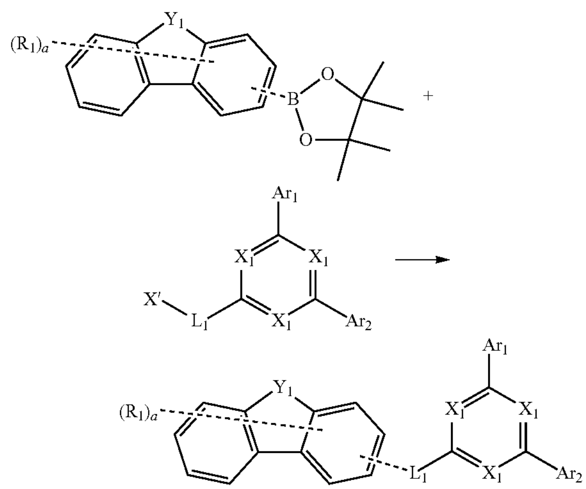

wherein in Reaction Scheme 1, the definition of the remaining substituents except for X' are the same as defined above, and X is halogen, more preferably fluoro, chloro or bromo.

The above reaction is a Suzuki coupling reaction which is preferably carried out in the presence of a palladium catalyst and a base, and a reactive group for the Suzuki coupling reaction can be modified as known in the art. The above preparation method can be further embodied in Preparation Examples described hereinafter.

Meanwhile, the Chemical Formula 2 can be the following Chemical Formula 2-1.

[Chemical Formula 2-1]

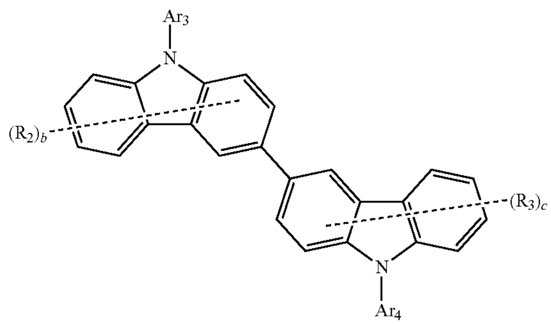

wherein in Chemical Formula 2-1, $Ar_3$, $Ar_4$, $R_3$, $R_4$, b and c are as defined in claim 1.

$Ar_3$ and $Ar_4$ can be each independently a substituted or unsubstituted $C_{6-30}$ aryl, or a substituted or unsubstituted $C_{2-30}$ heteroaryl containing any one or more selected from the group consisting of N, O and S. Specifically, $Ar_3$ and $Ar_4$ can be each independently phenyl, biphenylyl, terphenylyl, naphthyl, dimethylfluorenyl, dibenzofuranyl, or dibenzothiophenyl.

$R_2$ and $R_3$ can be each independently hydrogen, deuterium, a substituted or unsubstituted $C_{6-30}$ aryl, or a substituted or unsubstituted $C_{2-30}$ heteroaryl containing any one or more selected from the group consisting of N, O and S. Specifically, $R_2$ and $R_3$ can be each independently hydrogen or phenyl. For example, one of $R_2$ and $R_3$ is phenyl and the rest is hydrogen, or both $R_2$ and $R_3$ can be hydrogen.

b and c can be each independently an integer of 1 to 7, and for example, each can be 1.

Representative examples of the compound of Chemical Formula 2 are as follows:

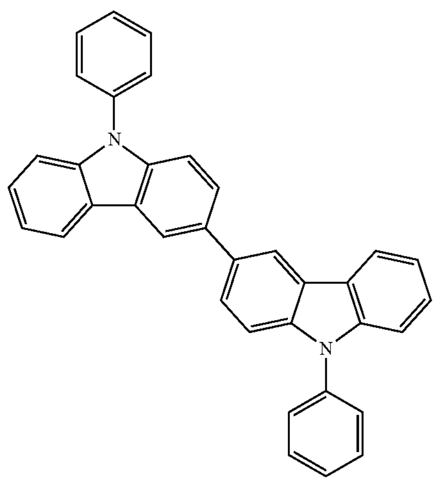

-continued

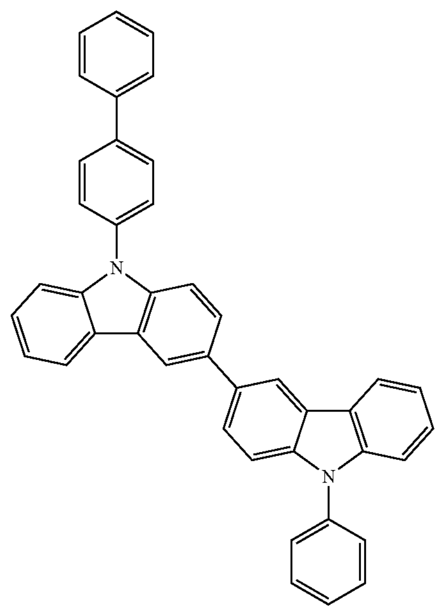

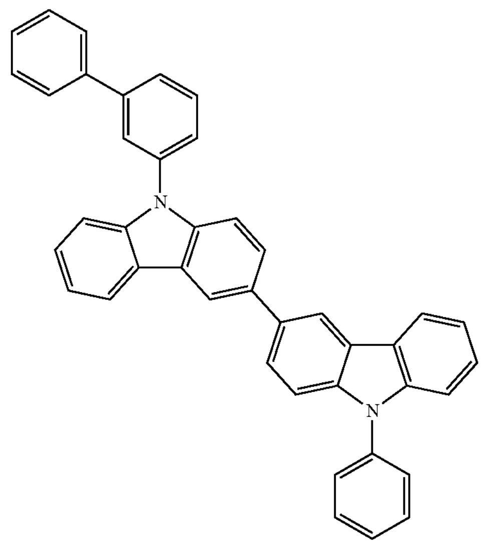

-continued
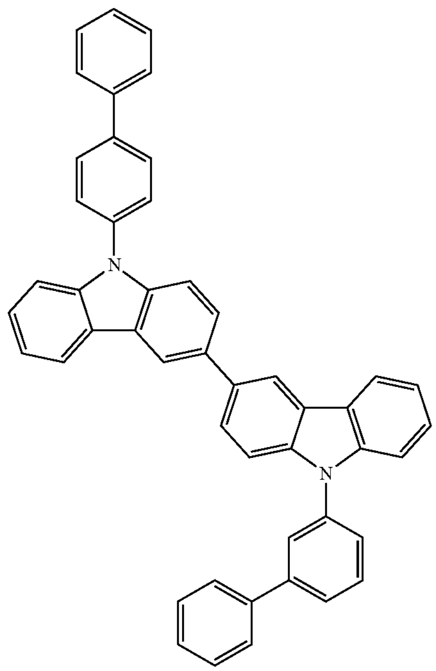
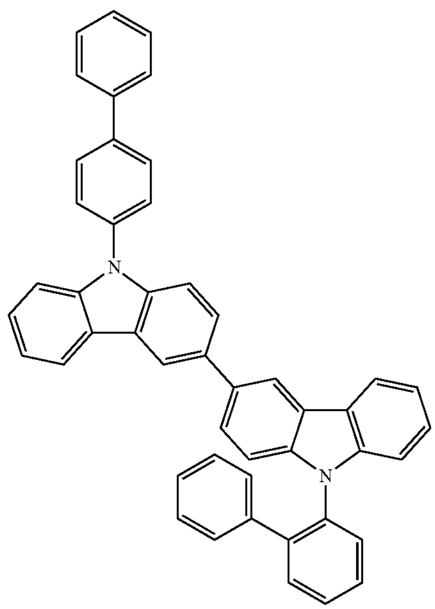
-continued
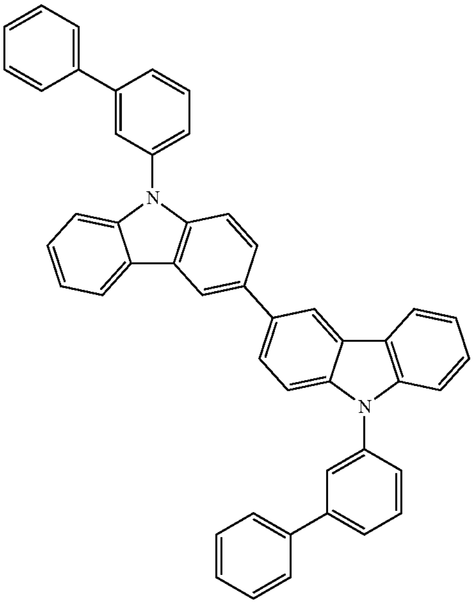
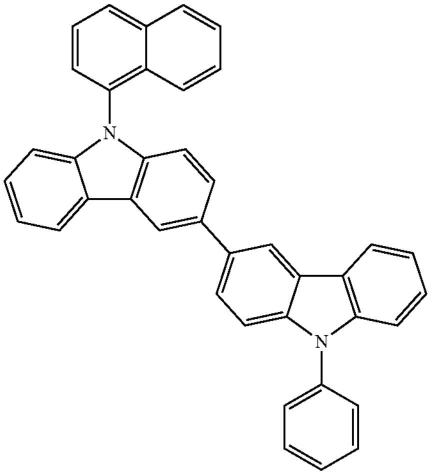
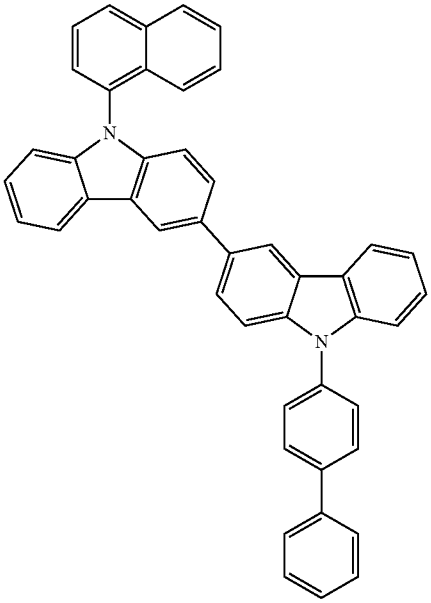

-continued
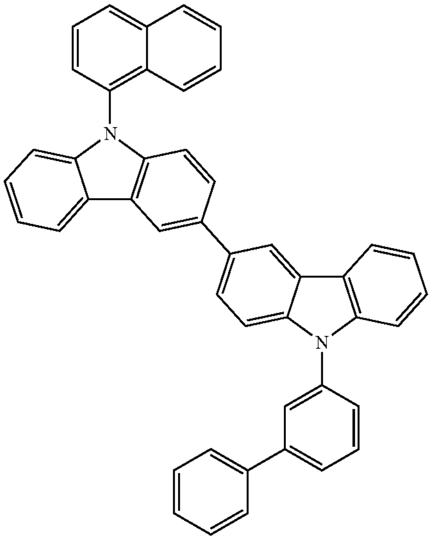
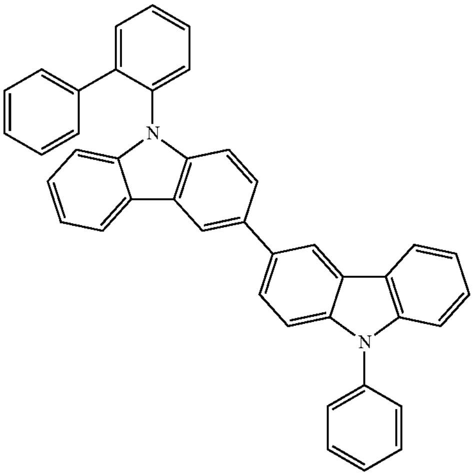
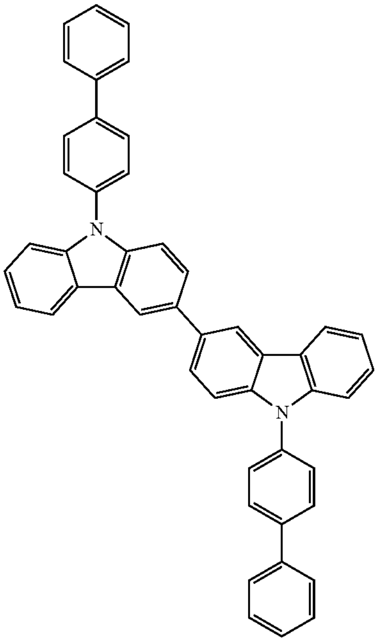
-continued
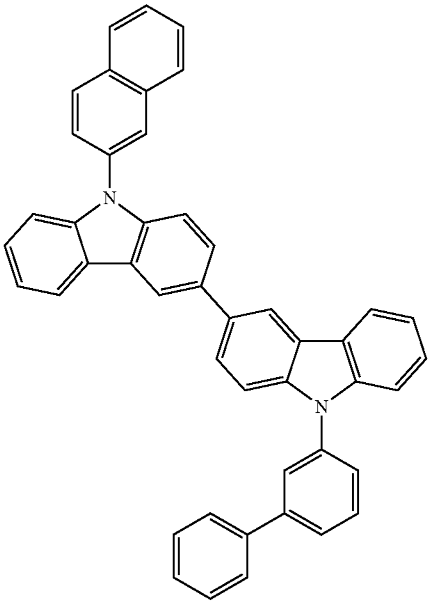
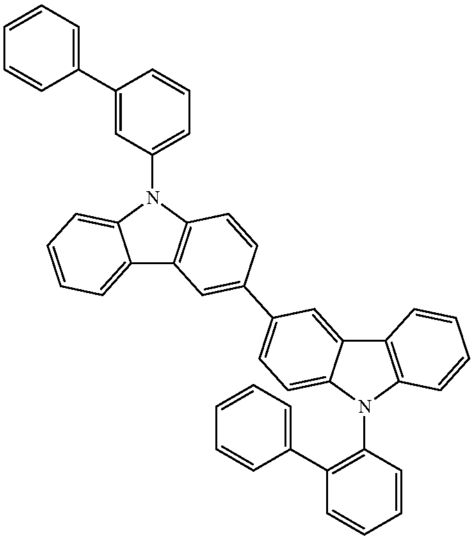
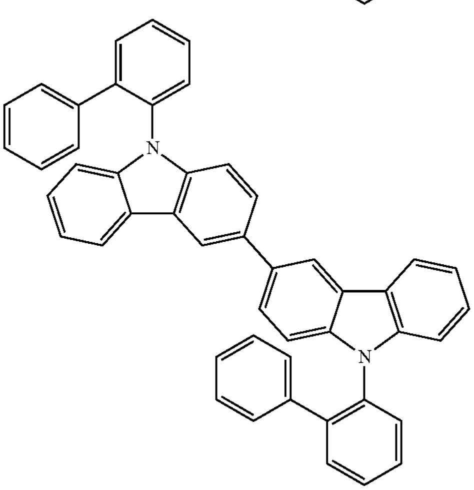

-continued
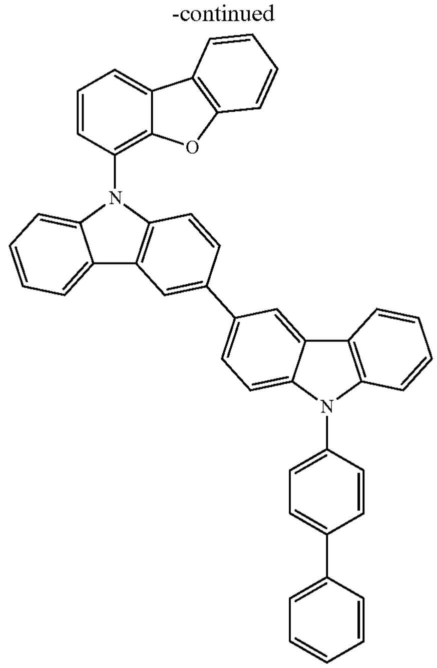
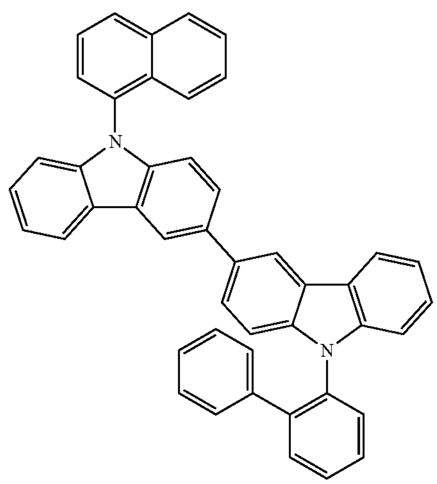
-continued
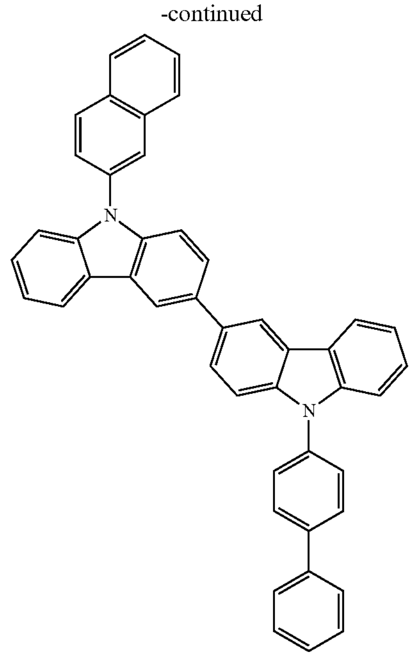
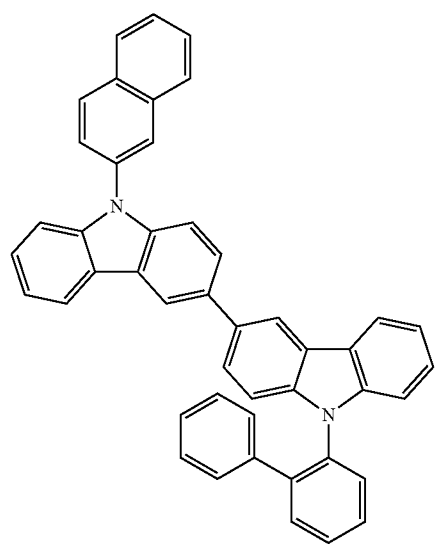
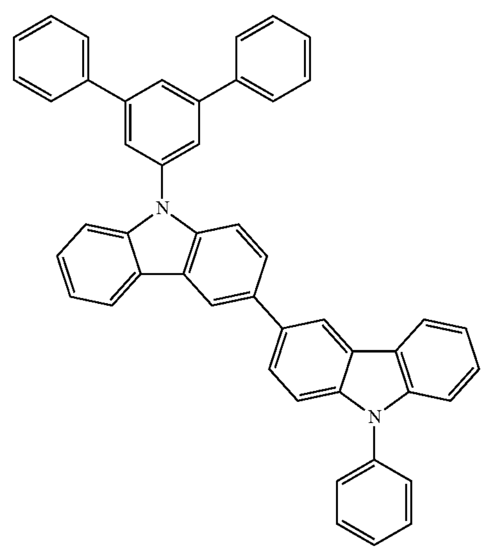

-continued
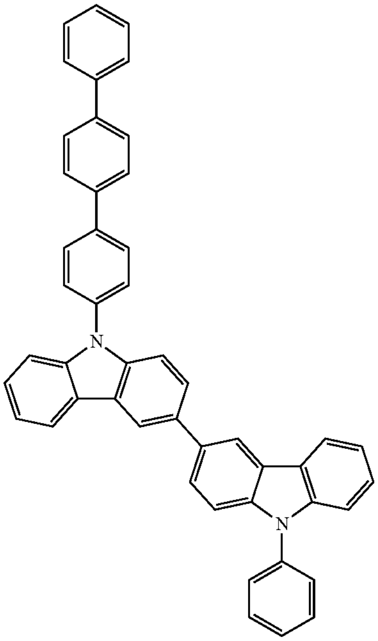
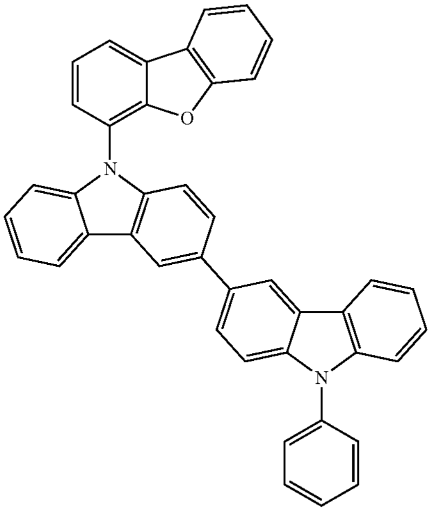
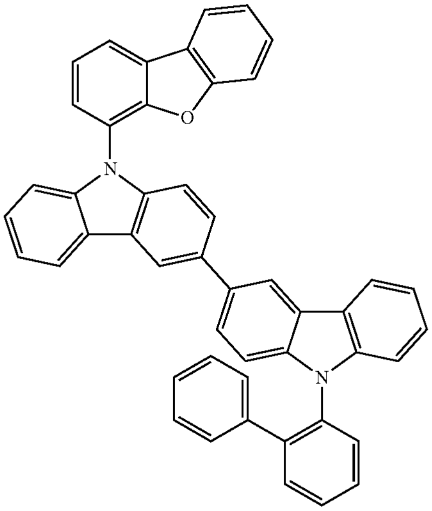
-continued
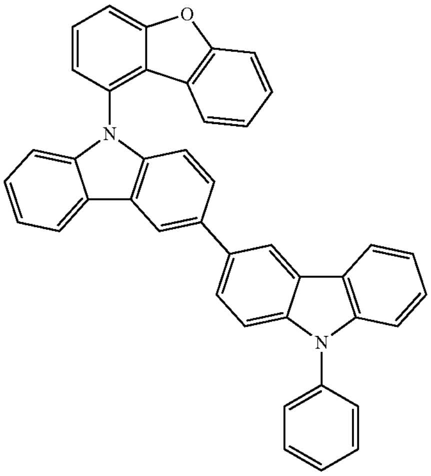
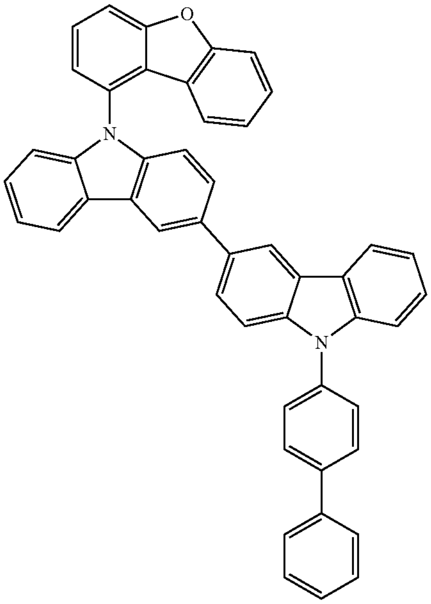
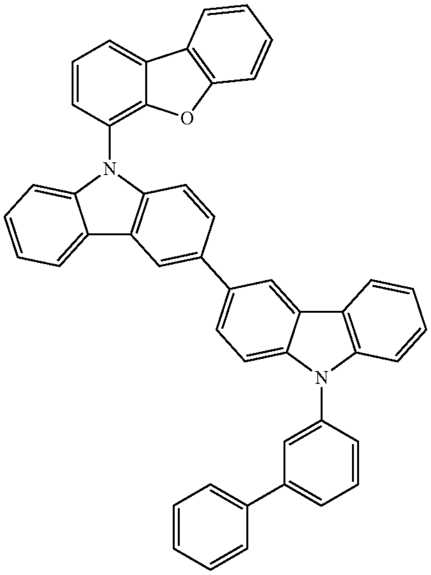

-continued
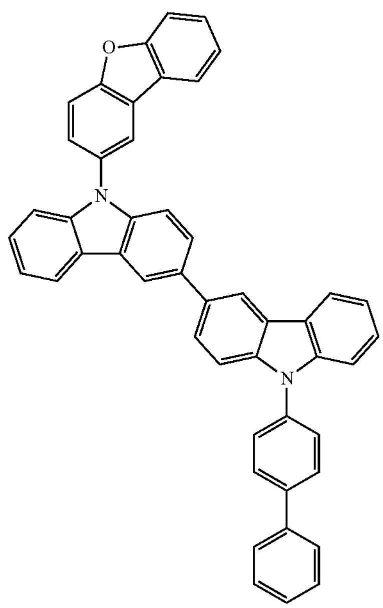
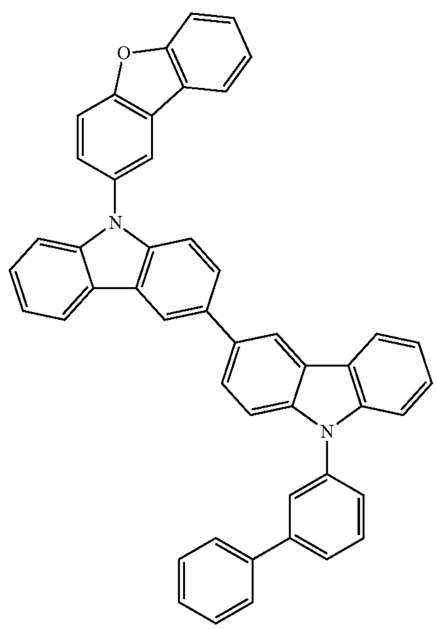
-continued
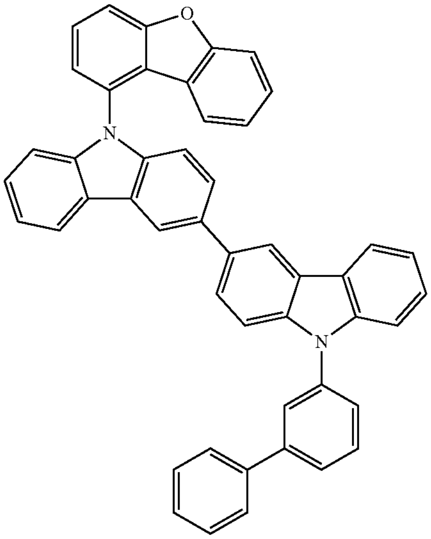
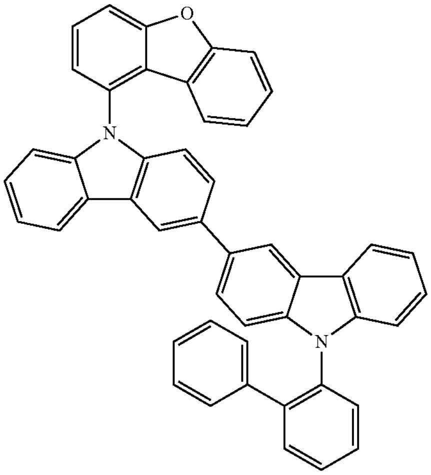
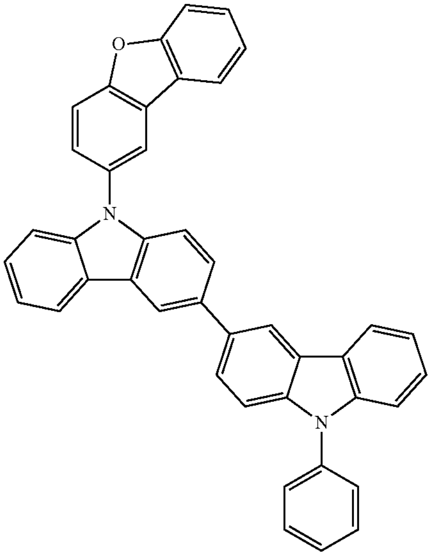

-continued
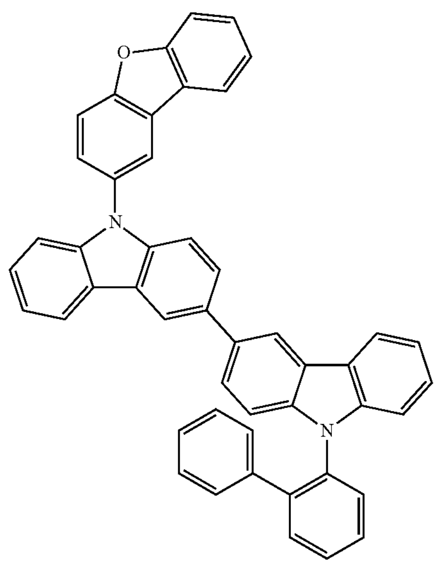
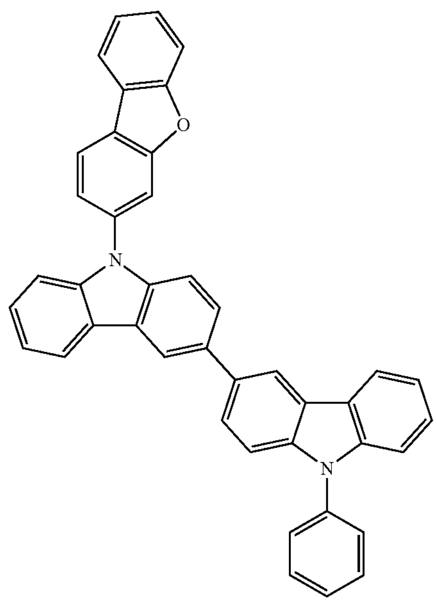
-continued
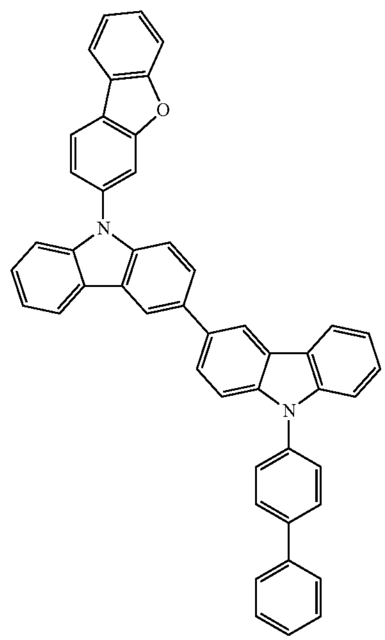
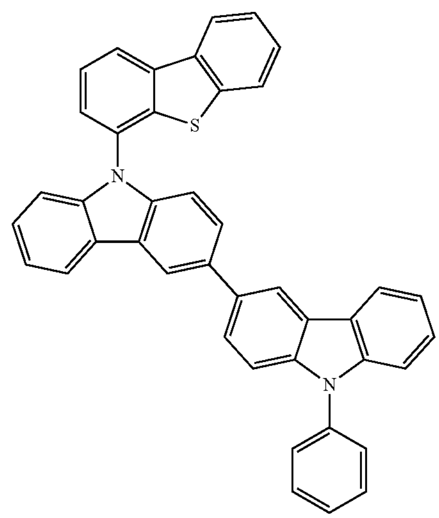

-continued
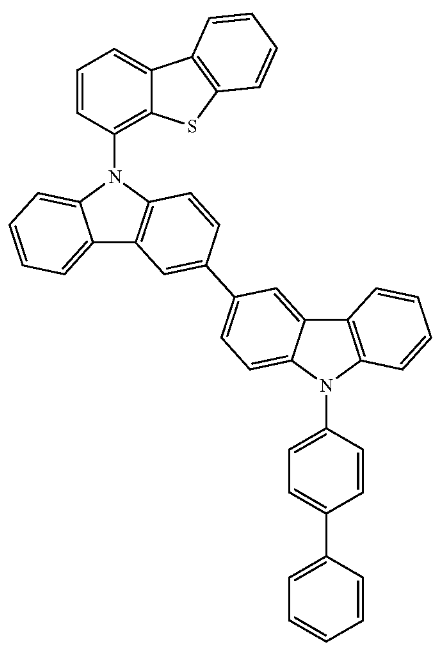
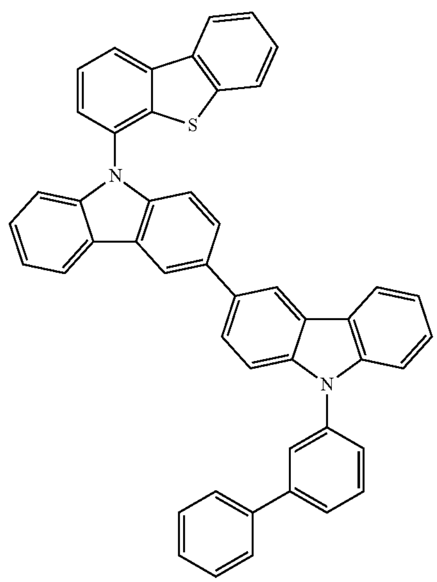
-continued
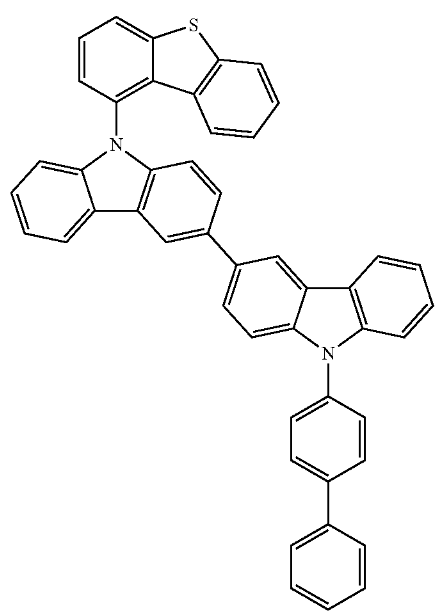
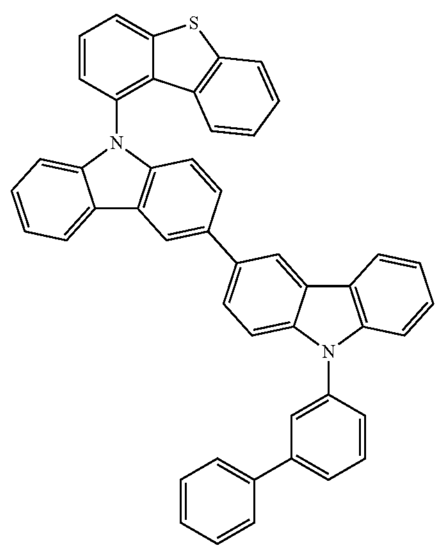
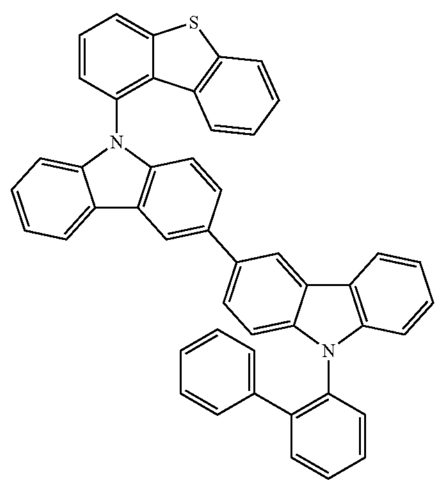

-continued
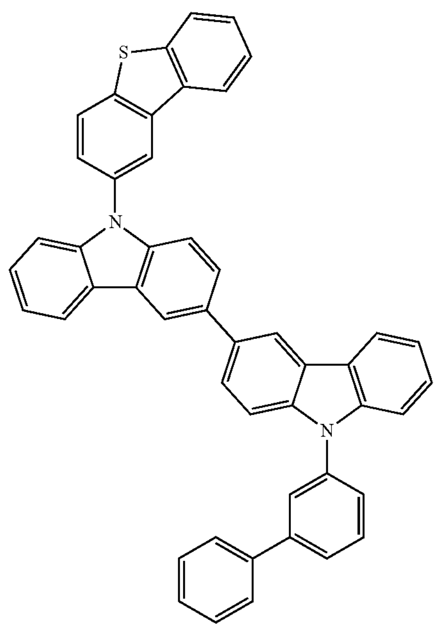
-continued
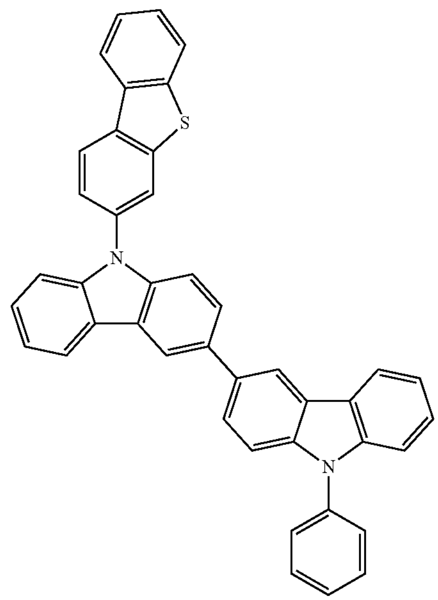
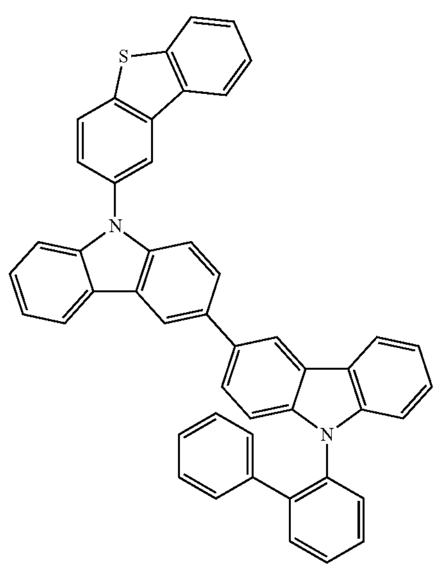
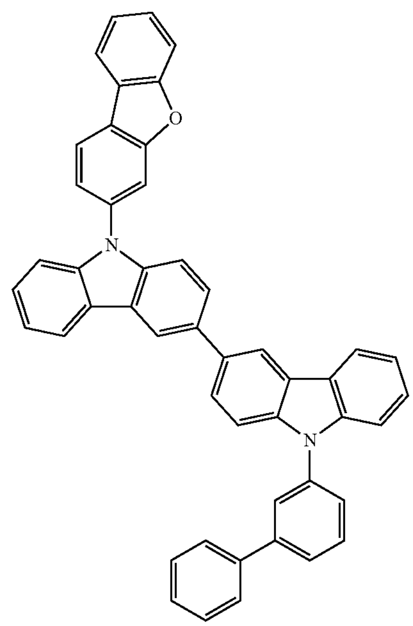

-continued
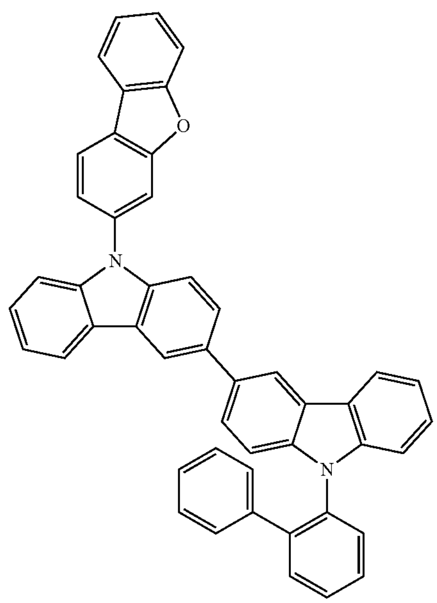
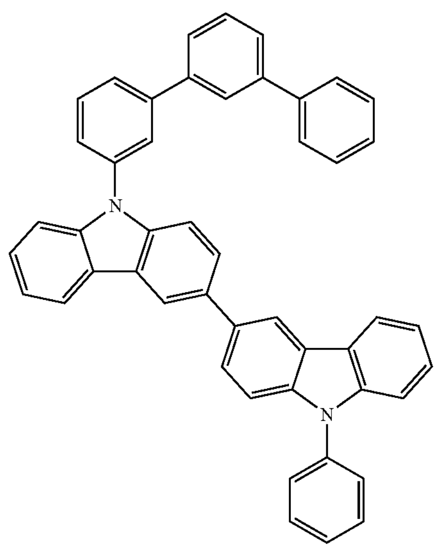
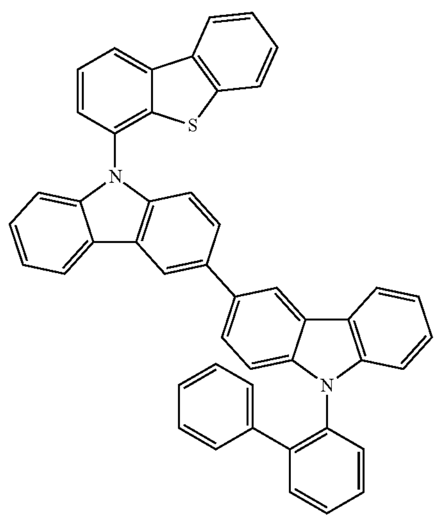
-continued
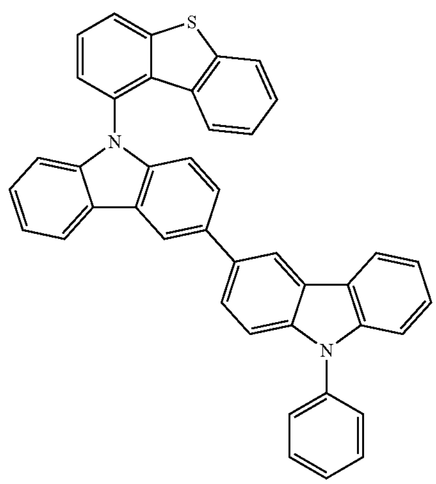
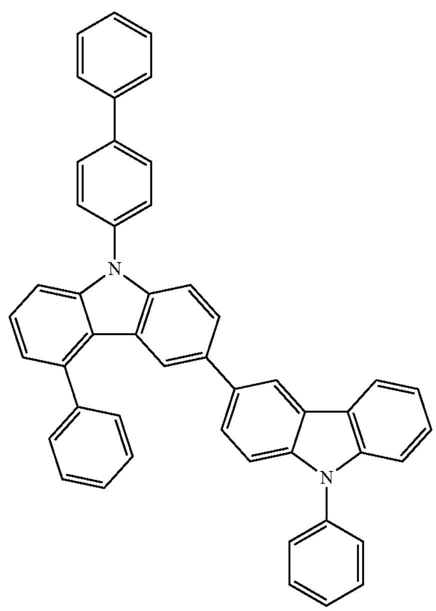
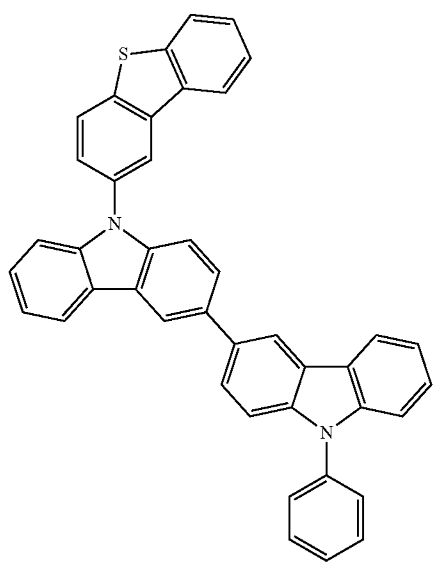

-continued
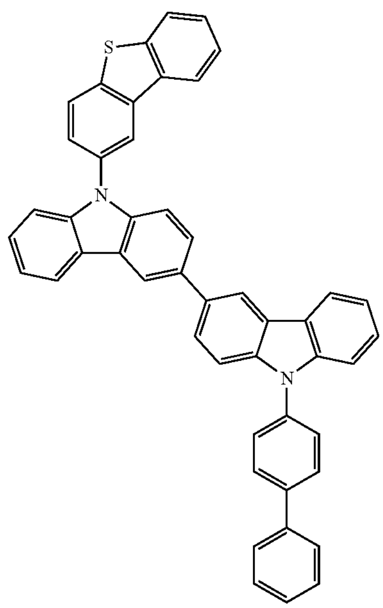
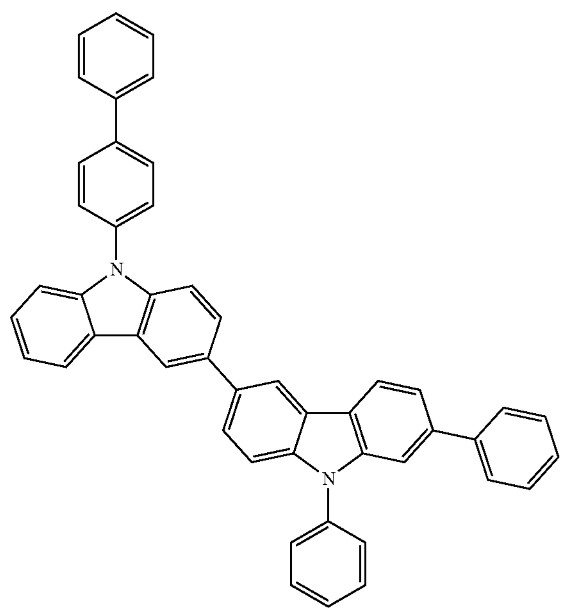
-continued
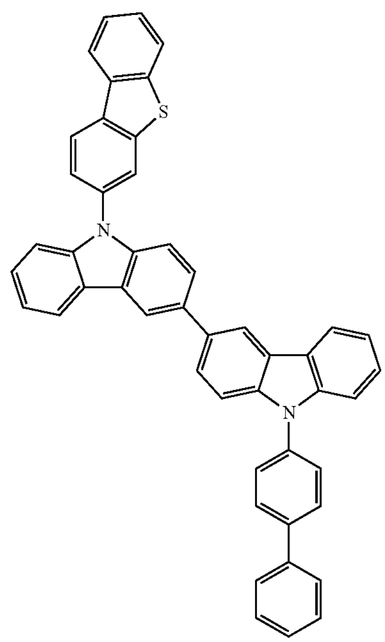
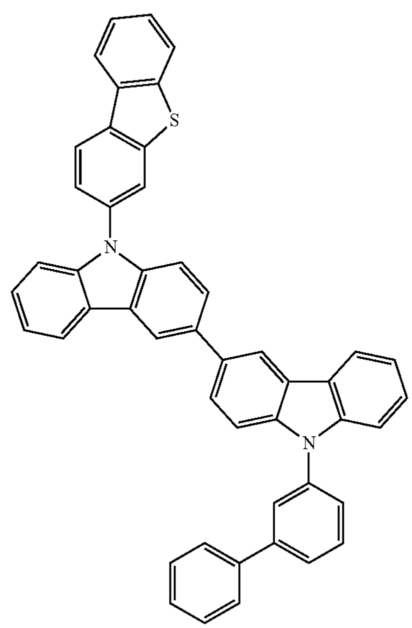

-continued
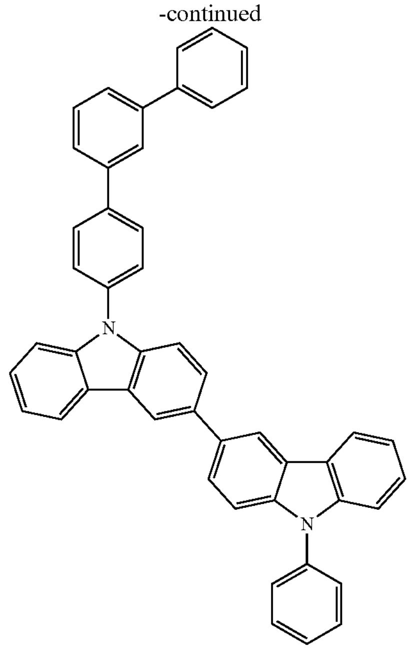
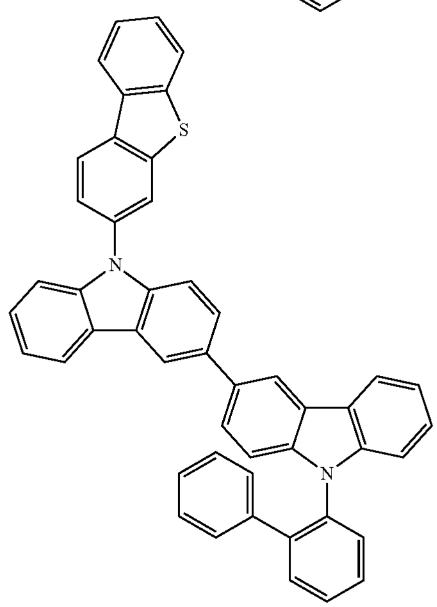
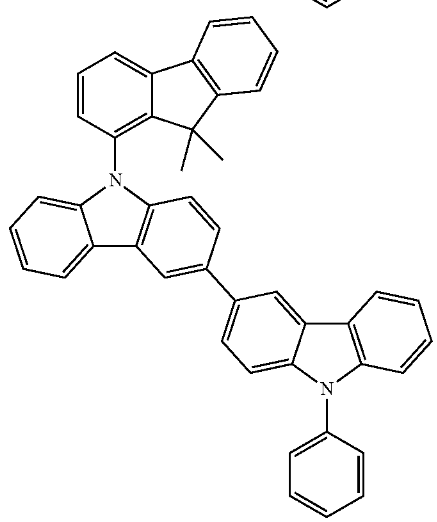
-continued
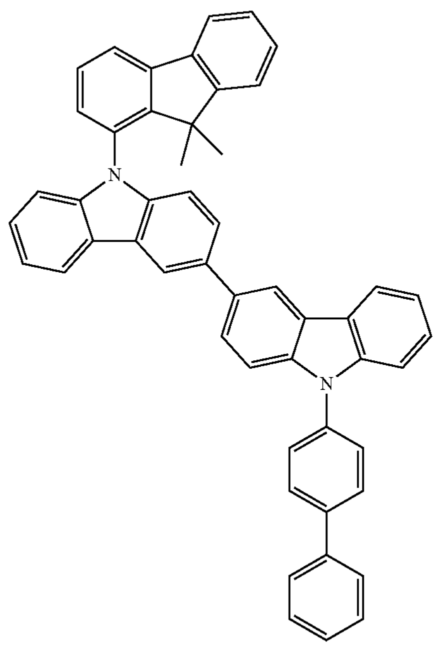
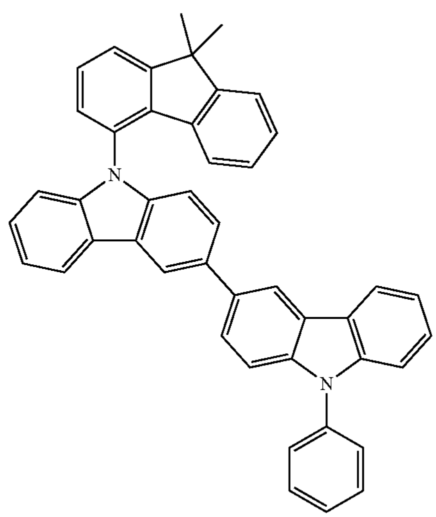

-continued
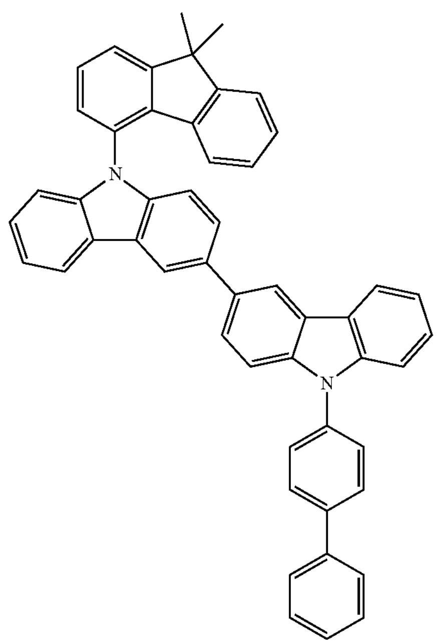
-continued
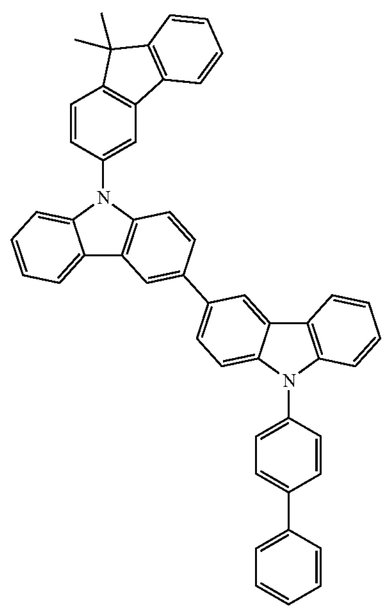
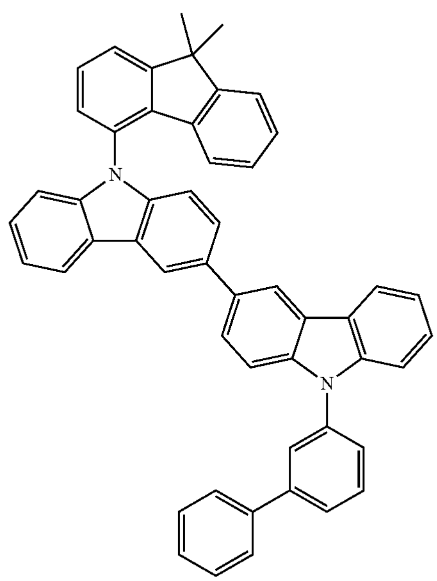
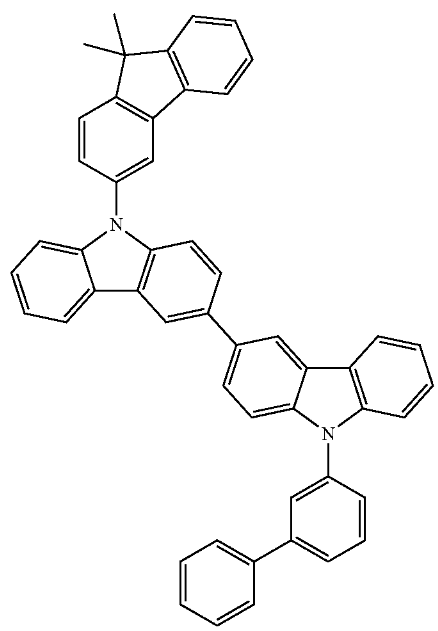

-continued
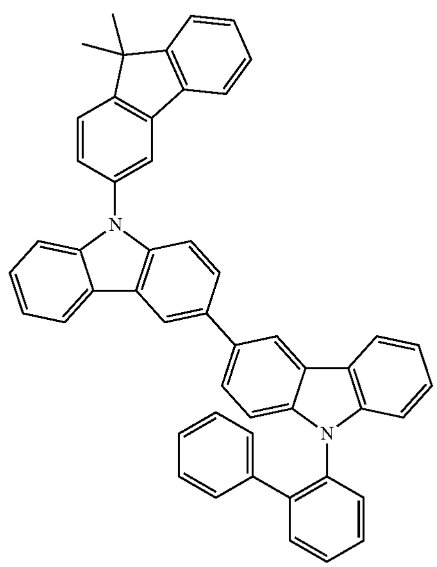
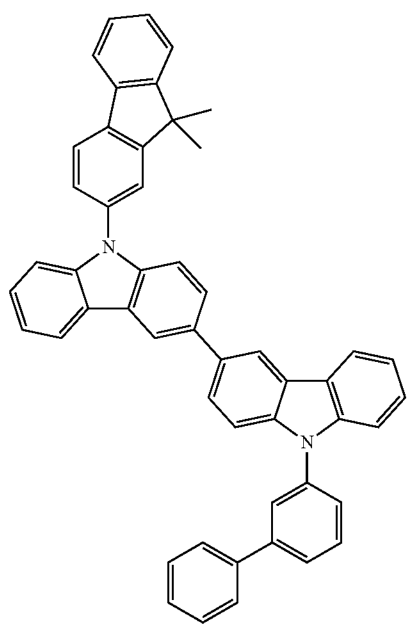
-continued
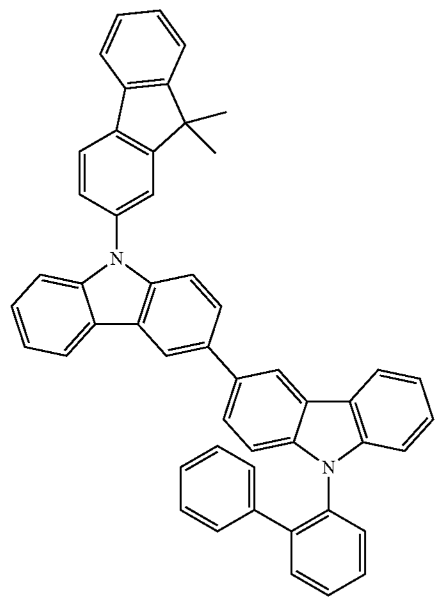
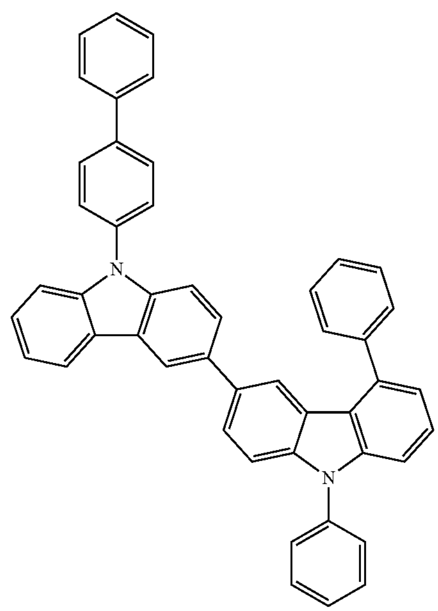

-continued
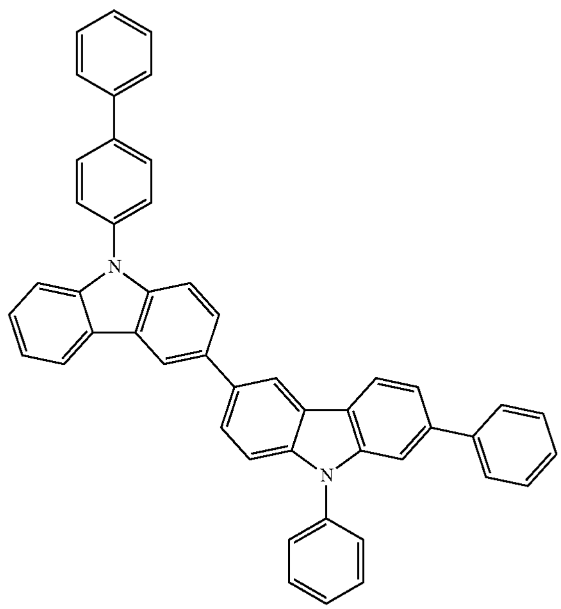
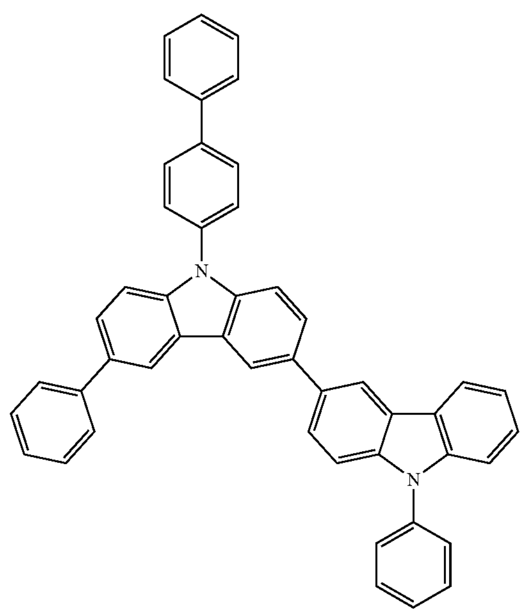
-continued
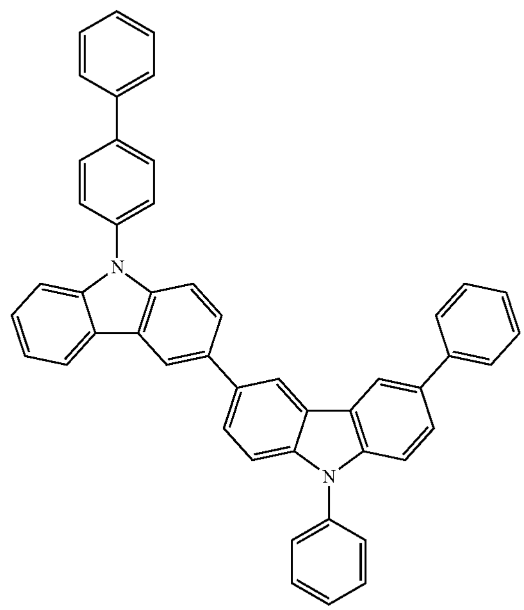
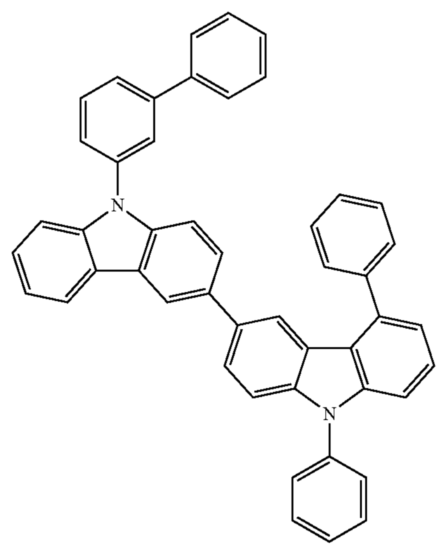
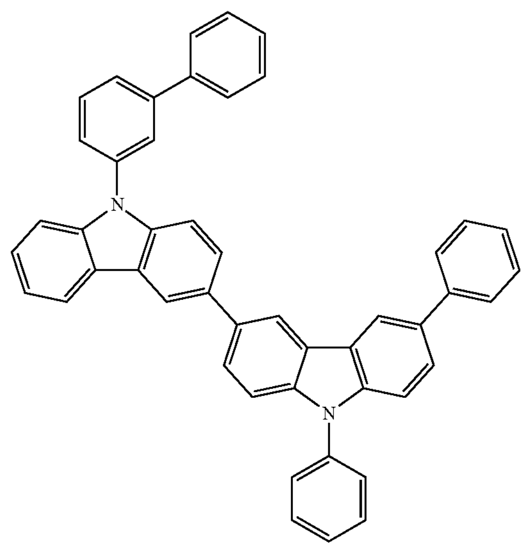

-continued
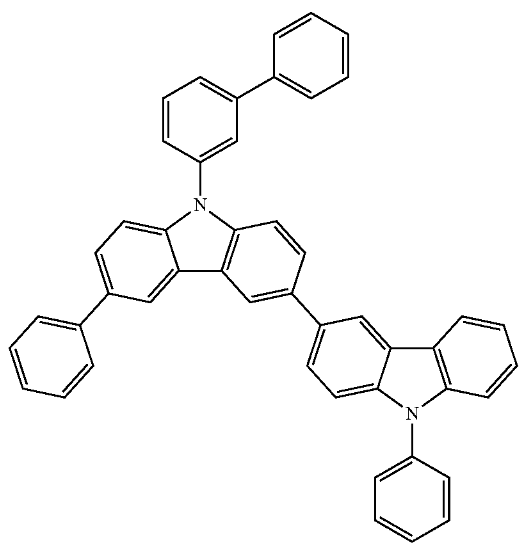
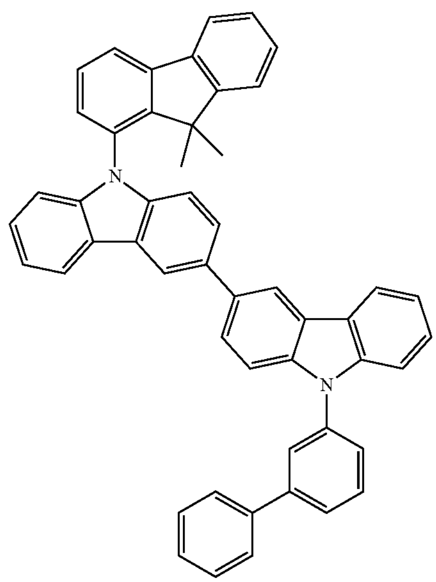
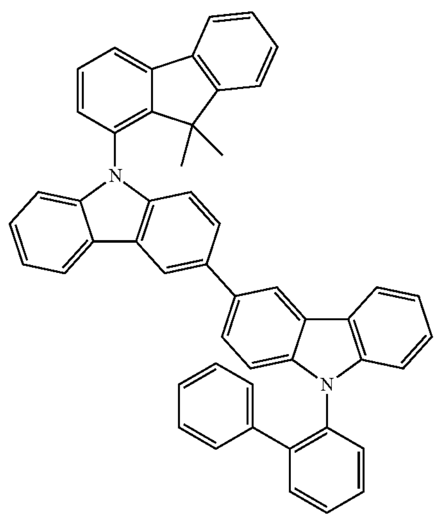
-continued
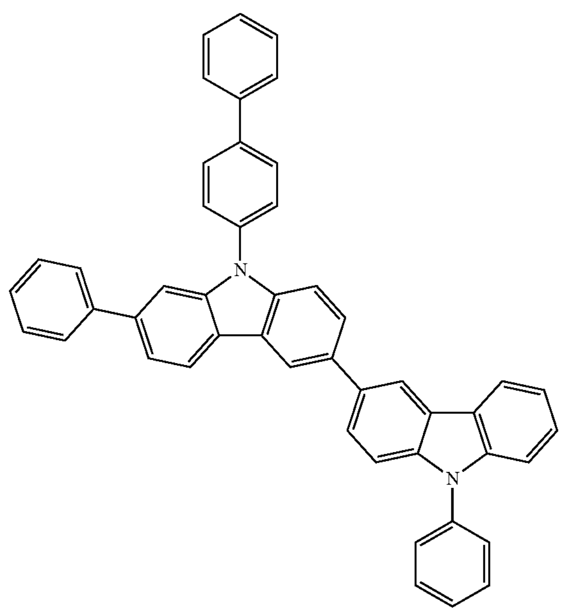
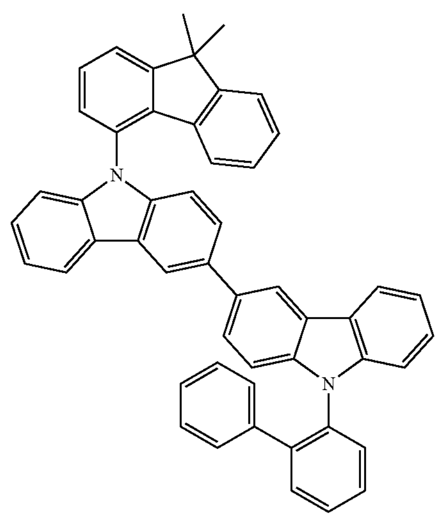
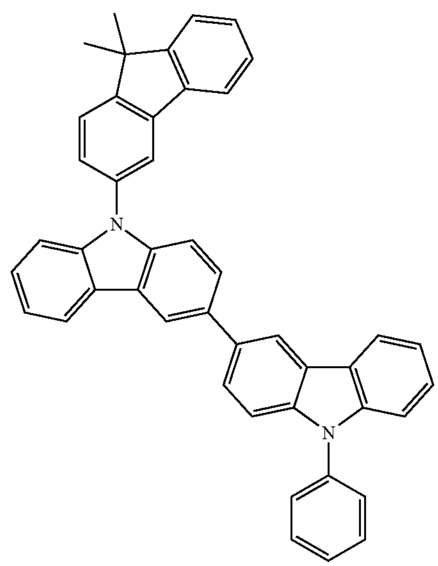

-continued
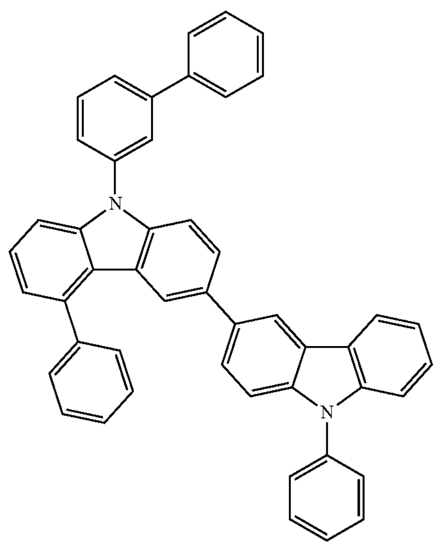
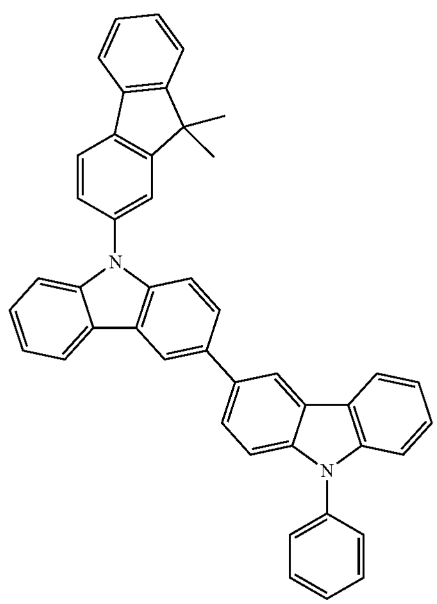
-continued
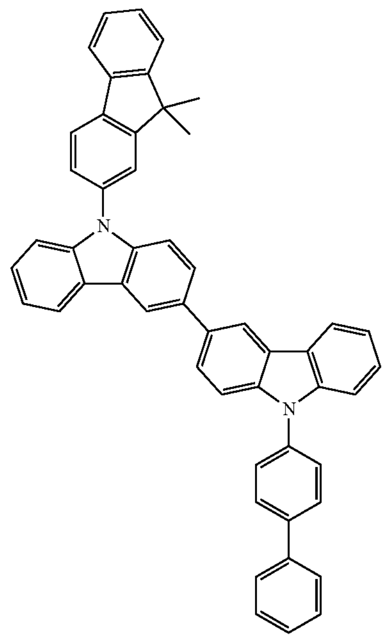
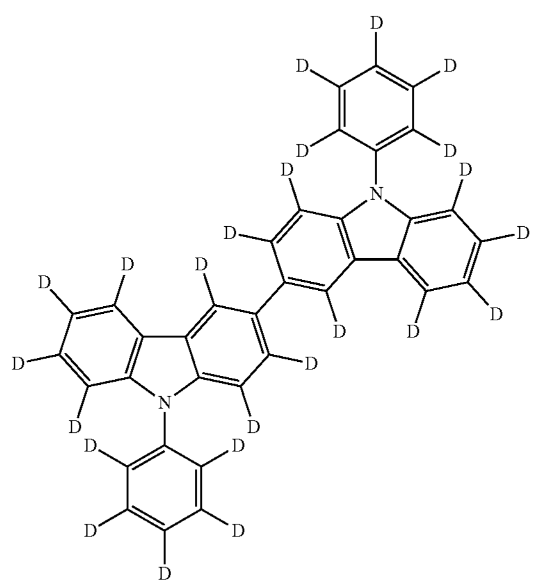

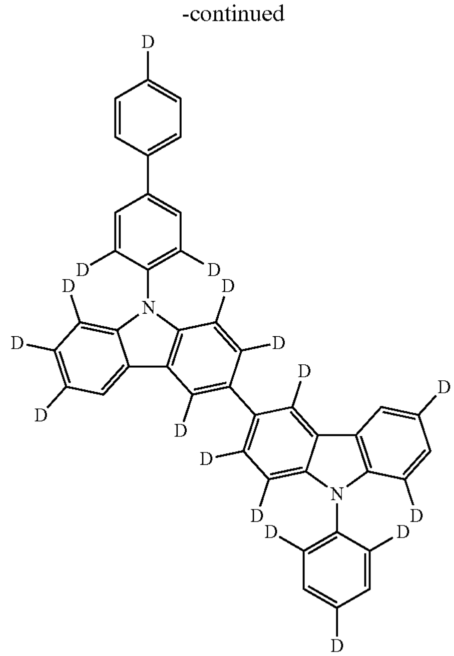
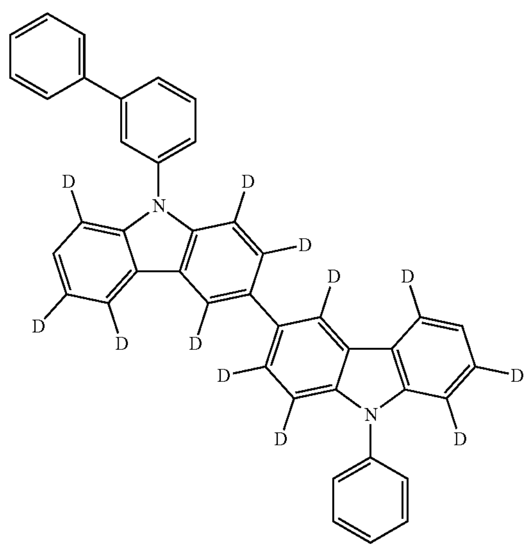
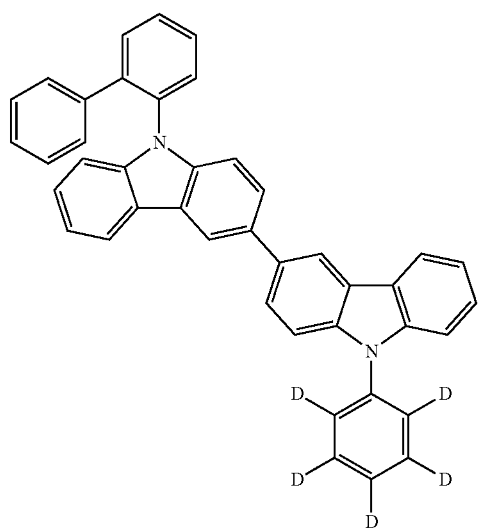
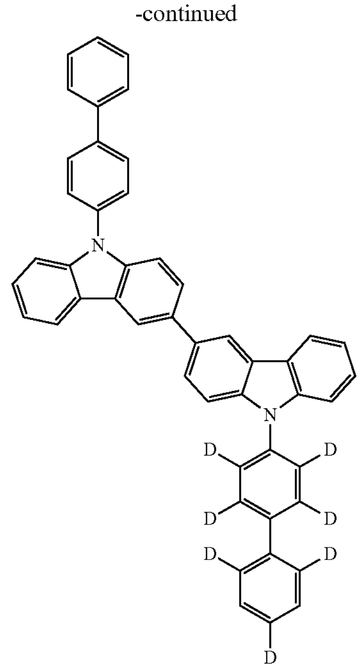
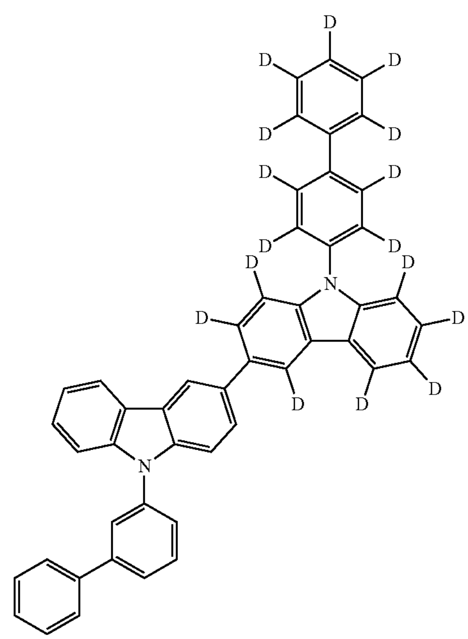

-continued
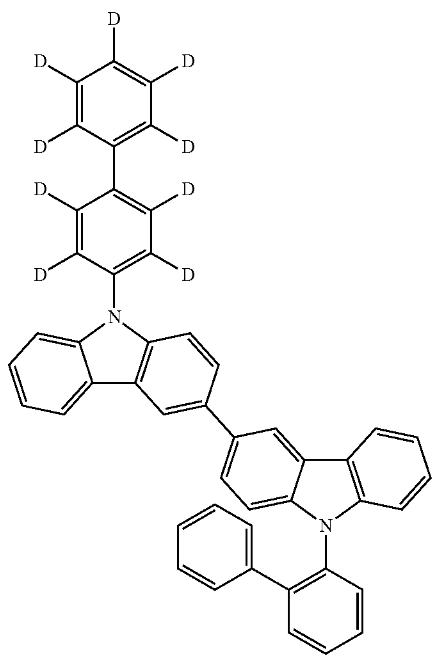
-continued
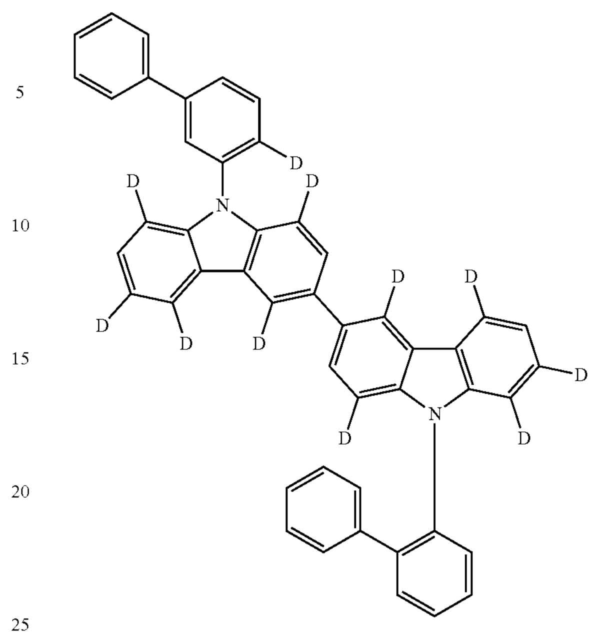
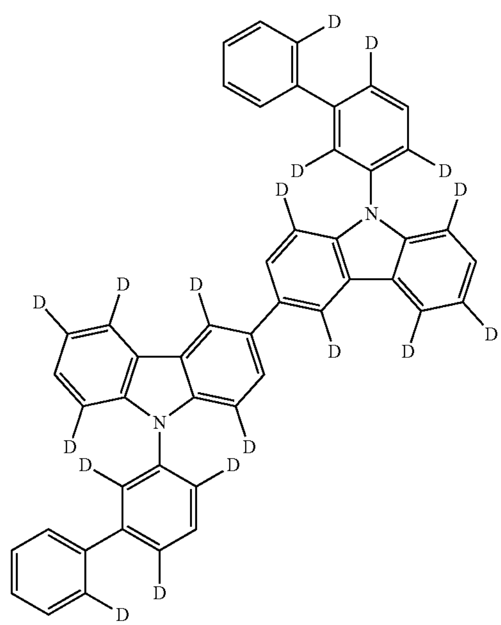
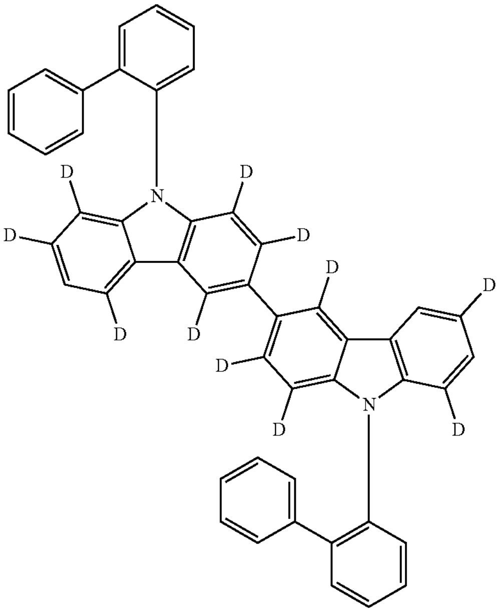

-continued
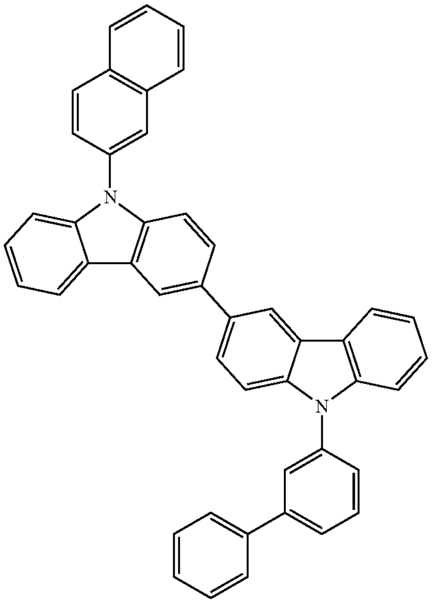
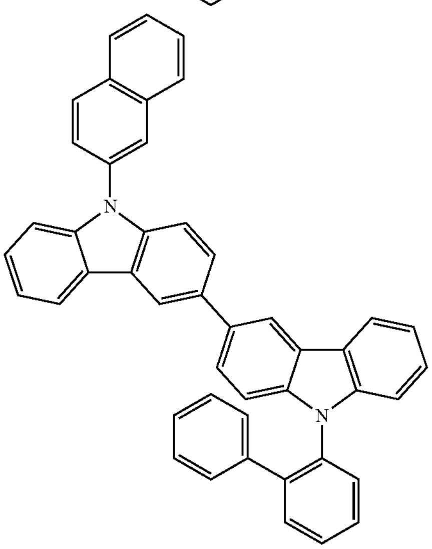
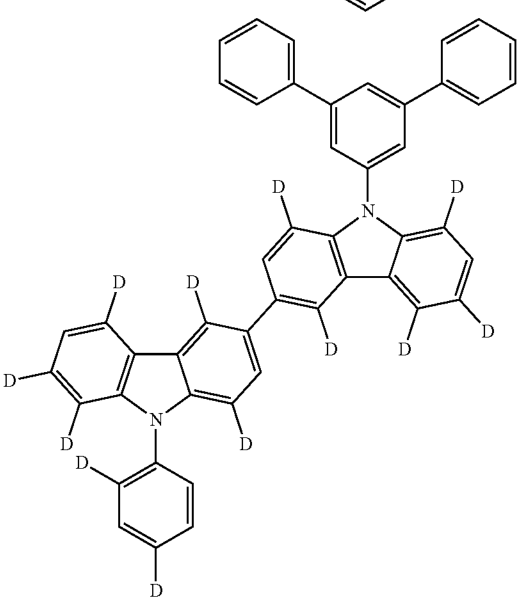
-continued
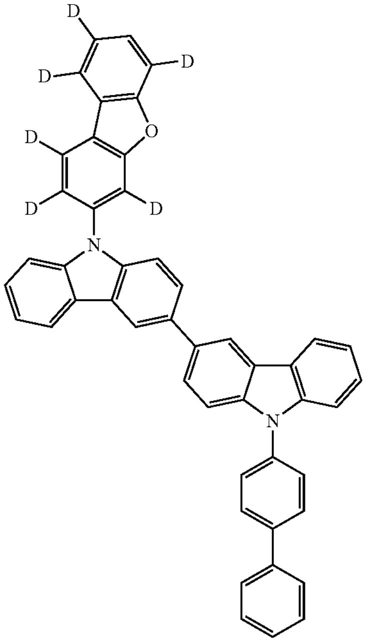
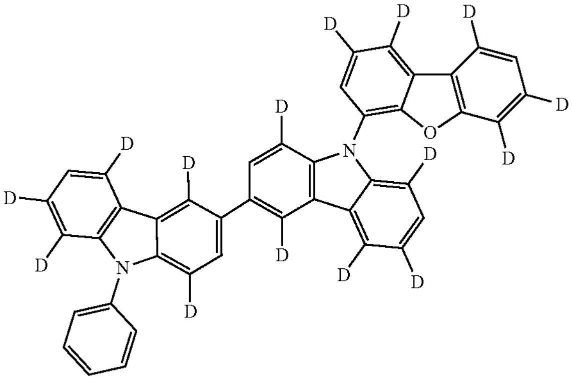
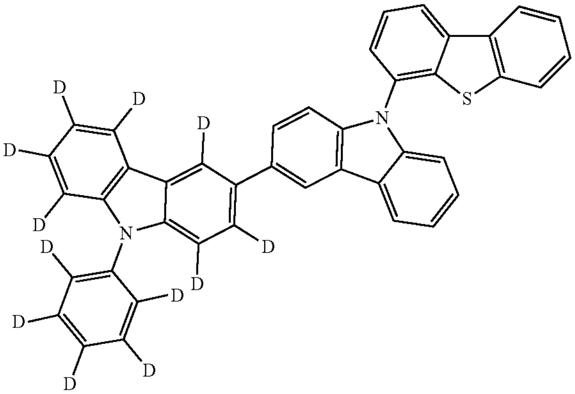

-continued

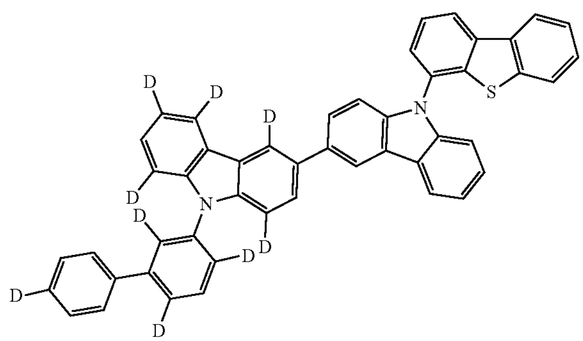

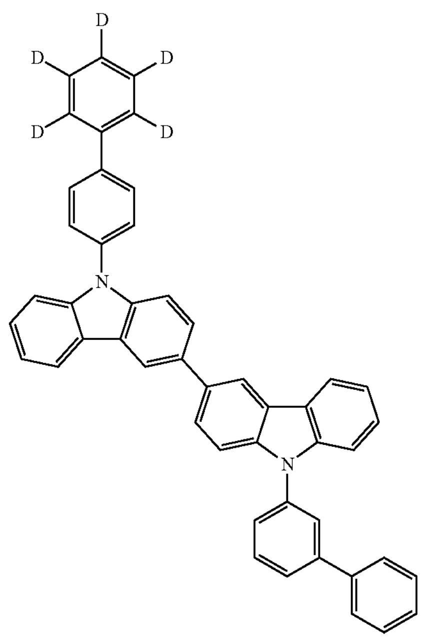

Further, the present disclosure provides a method for preparing the compound of Chemical Formula 2 as shown in the following Reaction Scheme 2.

[Reaction Scheme 2]

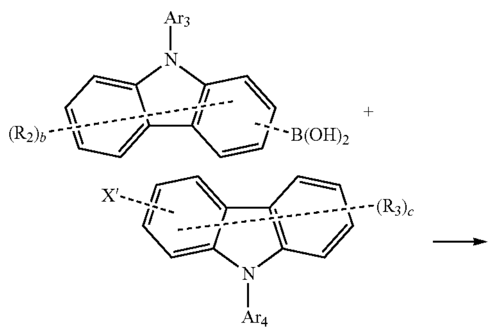

-continued

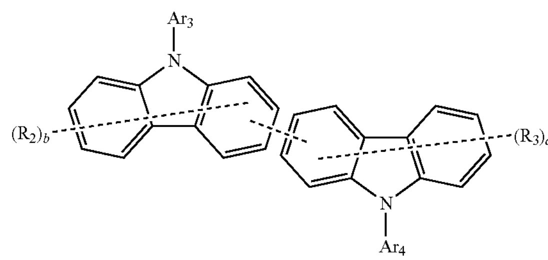

wherein in Reaction Scheme 2, the definition of the remaining substituents except for X' are the same as defined above, and X' is halogen, more preferably fluoro, chloro or bromo.

The above reaction is a Suzuki coupling reaction which is preferably carried out in the presence of a palladium catalyst and a base, and a reactive group for the Suzuki coupling reaction can be modified as known in the art. The above preparation method can be further embodied in Preparation Examples described hereinafter.

In Chemical Formula 3, B is a benzene ring fused with two adjacent pentagonal rings, and C is the following Chemical Formula 4-1 or 4-2:

[Chemical Formula 4-1]

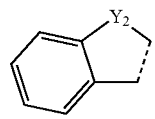

[Chemical Formula 4-2]

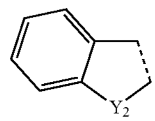

wherein in Chemical Formulas 4-1 and 4-2, the dotted line is a bond that is fused with B.

Depending on the fused form of B and C, the Chemical Formula 3 can be any one of the following Chemical Formulas 3-1 to 3-6:

[Chemical Formula 3-1]

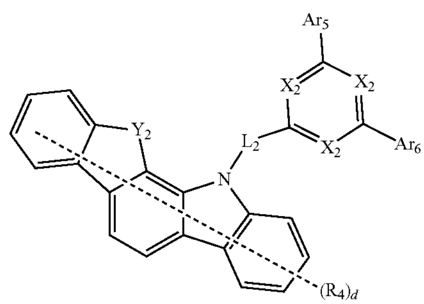

-continued

[Chemical Formula 3-2]

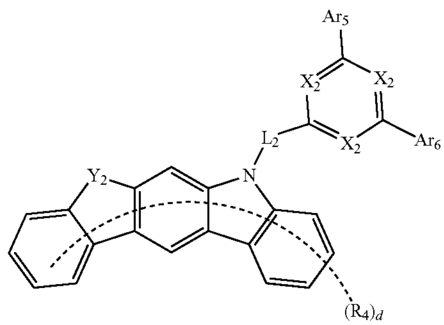

[Chemical Formula 3-3]

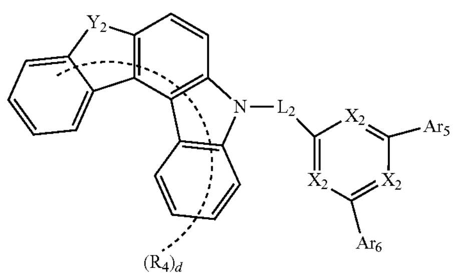

[Chemical Formula 3-4]

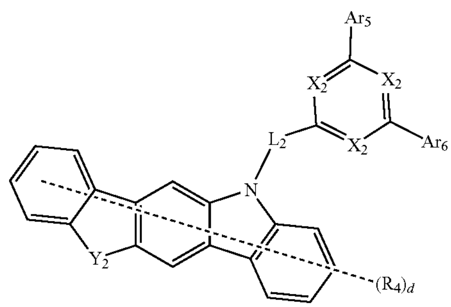

[Chemical Formula 3-5]

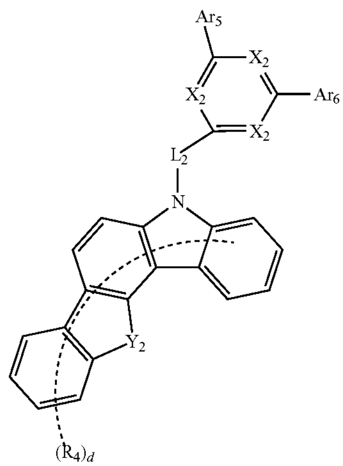

-continued

[Chemical Formula 3-6]

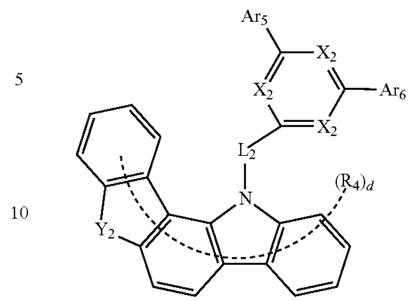

wherein in Chemical Formulas 3-1 to 3-6, $X_2$, $L_2$, $Ar_5$, $Ar_6$, $R_4$, $Y_2$ and d are as defined above.

$X_1$ to $X_3$ are each independently CH or N, provided that at least one of $X_1$ to $X_3$ is N.

$L_2$ can be a direct bond, a substituted or unsubstituted $C_{6-30}$ arylene, or a substituted or unsubstituted $C_{2-30}$ heteroarylene containing any one or more selected from the group consisting of N, O and S. Specifically, $L_2$ is a direct bond or phenylene, provided that when $L_2$ is phenylene, it is unsubstituted or substituted with at least one deuterium.

$Ar_5$ and $Ar_6$ can be each independently a substituted or unsubstituted $C_{6-30}$ aryl or a substituted or unsubstituted $C_{2-30}$ heteroaryl containing any one or more selected from the group consisting of N, O and S. Specifically, $Ar_5$ and Are can be each independently phenyl, biphenylyl, (phenyl) biphenylyl, triphenylenyl, dimethylfluorenyl, dibenzofuranyl, dibenzothiophenyl, carbazol-9-yl, or 9-phenyl-9H-carbazolyl with the $Ar_5$ and $Ar_6$ being each independently unsubstituted or substituted with at least one deuterium.

$Y_2$ can be $C(CH_3)_2$, $C(C_6C_5)_2$, O, S, or $NAr_7$, wherein $Ar_7$ is a substituted or unsubstituted $C_{6-30}$ aryl, or a substituted or unsubstituted $C_{2-30}$ heteroaryl containing any one or more selected from the group consisting of N, O and S. Specifically, $Ar_7$ is dibenzofuranyl, or dibenzothiophenyl, with the $Ar_7$ being unsubstituted or substituted with at least one deuterium.

$R_4$ can be hydrogen, deuterium, a substituted or unsubstituted $C_{6-30}$ aryl, or a substituted or unsubstituted $C_{2-30}$ heteroaryl containing any one or more selected from the group consisting of N, O and S. Specifically, $R_4$ can be hydrogen or deuterium.

d is an integer of 1 to 10.

Representative examples of the compound of Chemical Formula 3 are as follows:

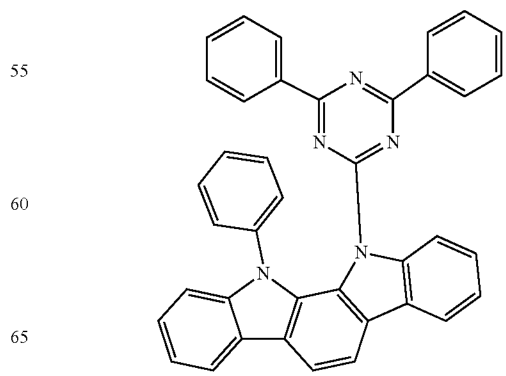

-continued
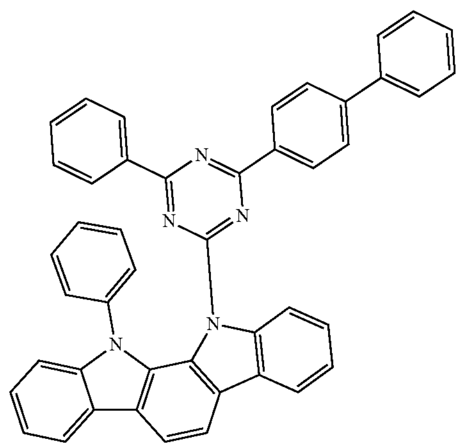
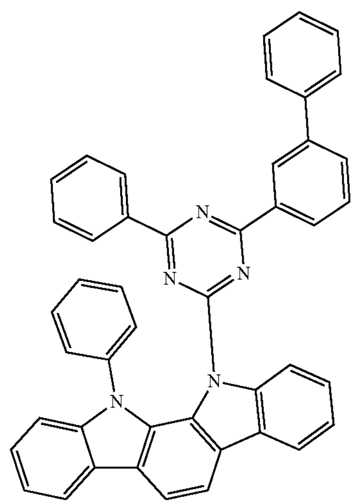
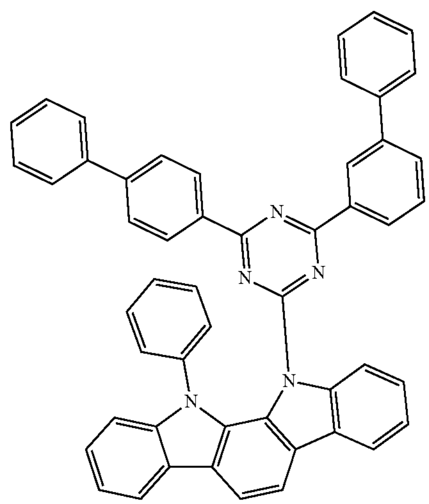
-continued
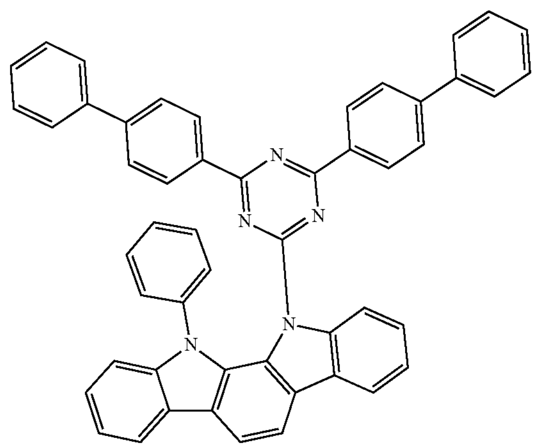
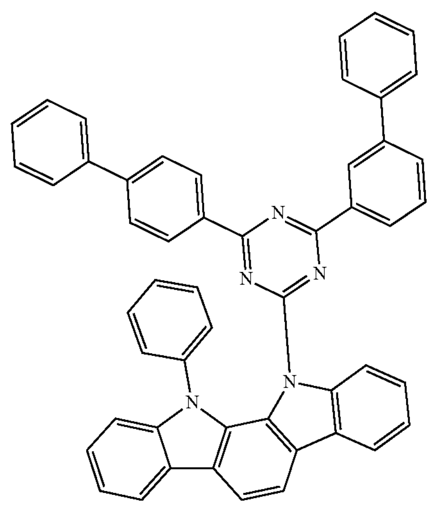
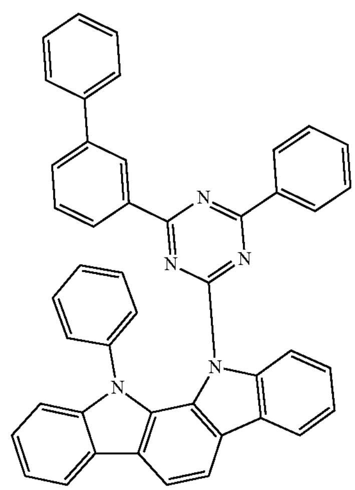

-continued
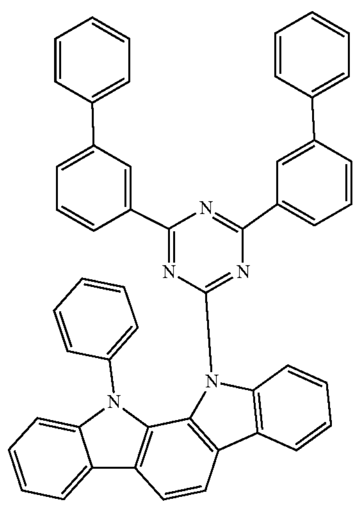
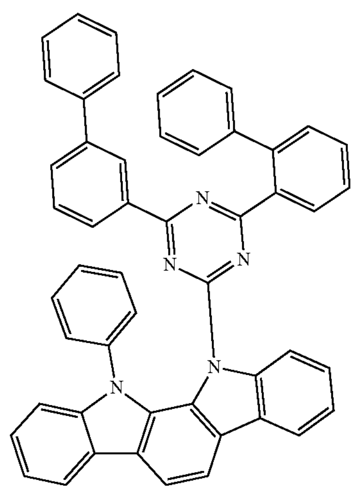
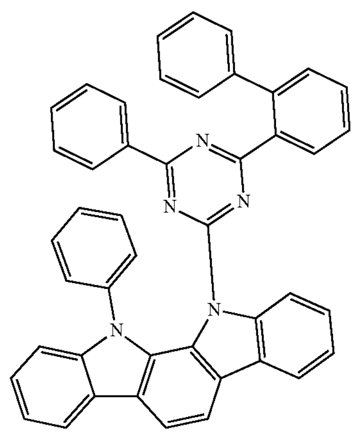
-continued
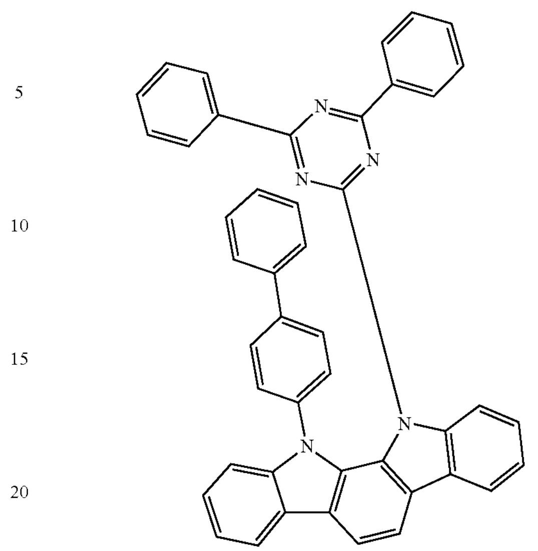
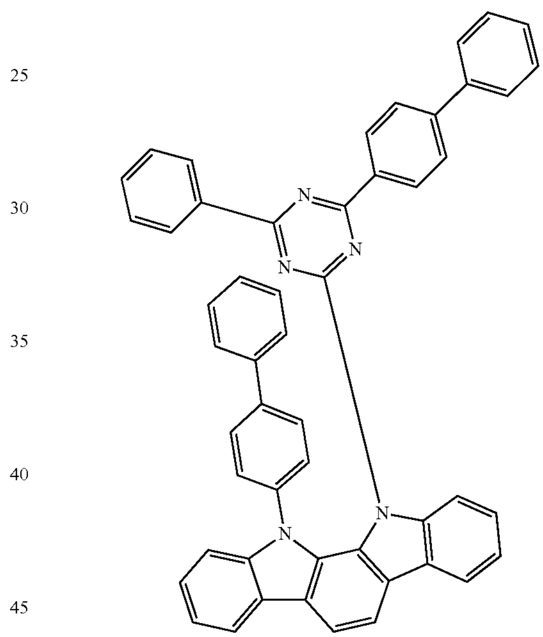
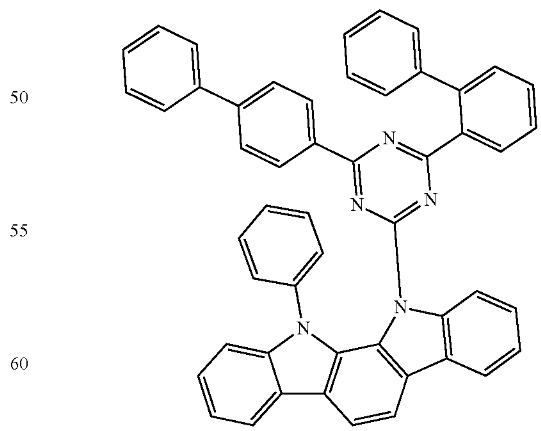

-continued
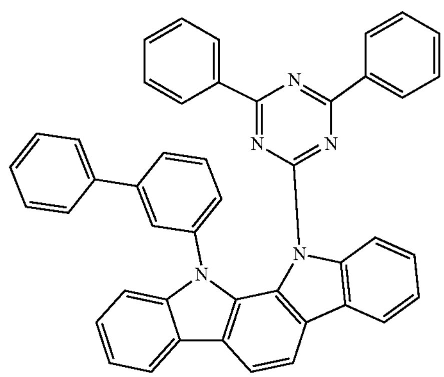
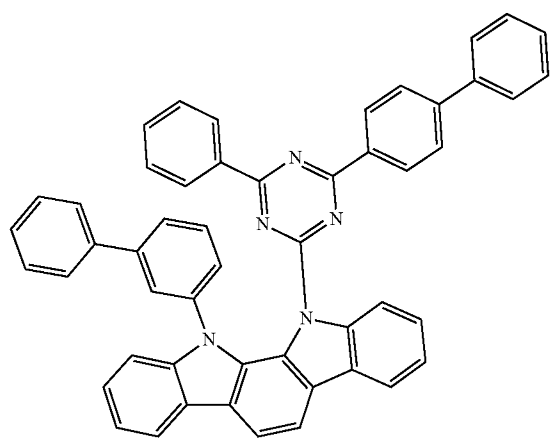
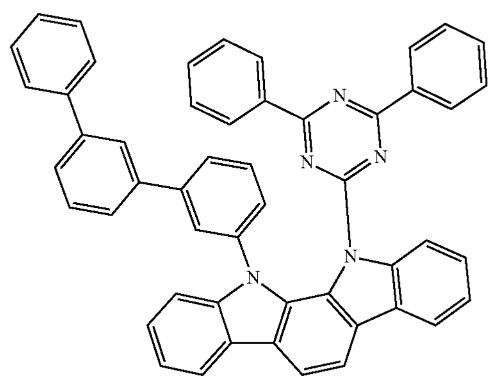
-continued
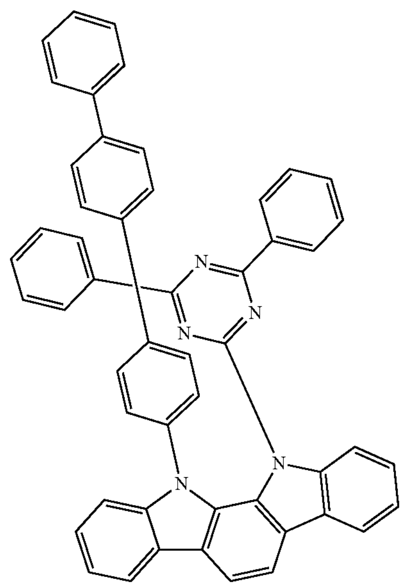
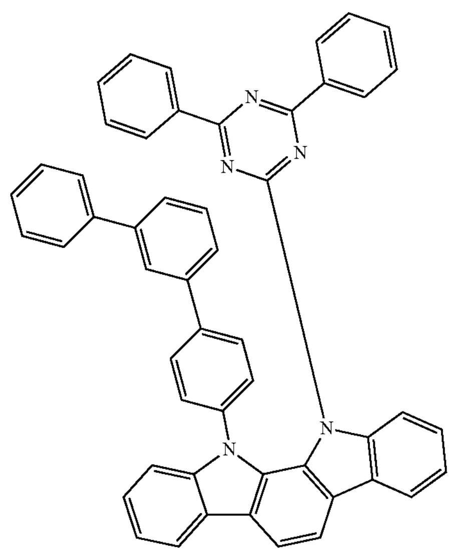

-continued
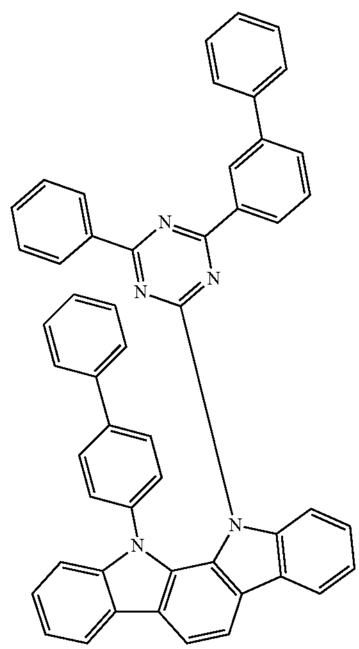
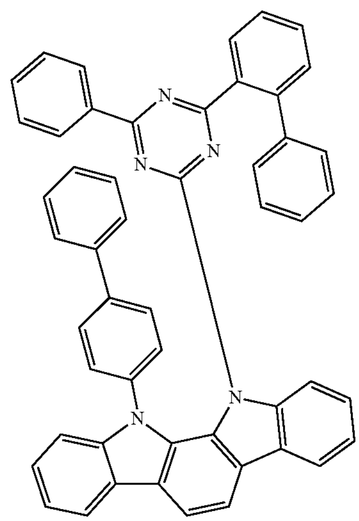
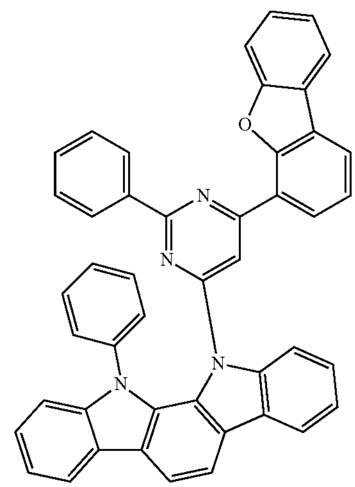
-continued
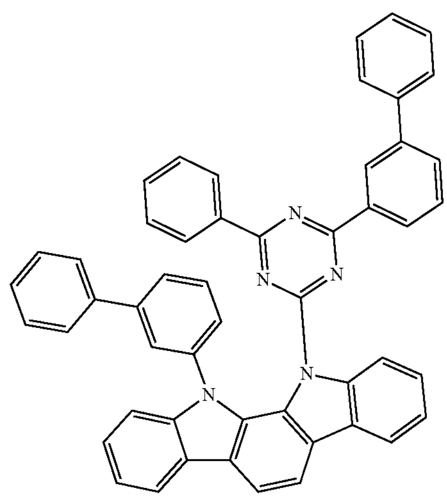
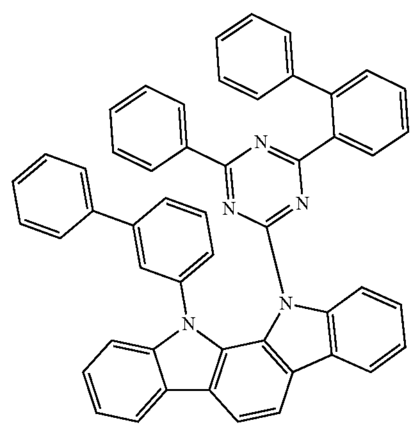
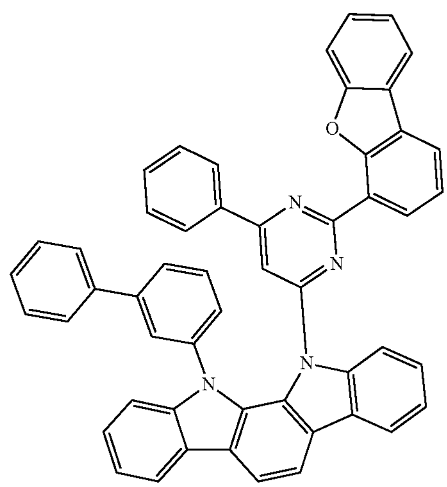

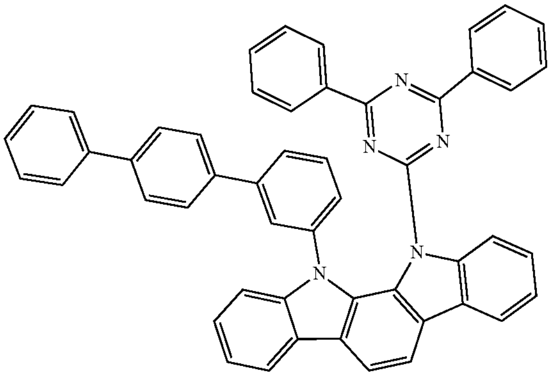
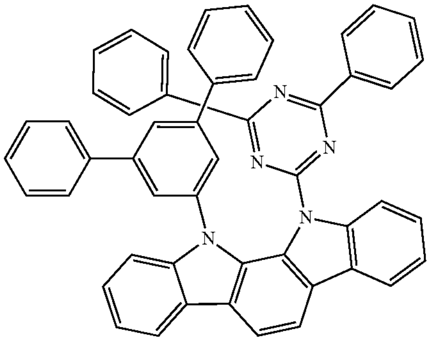
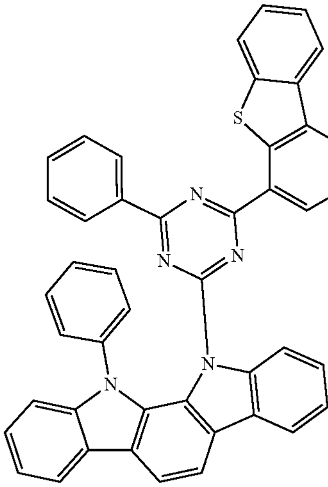
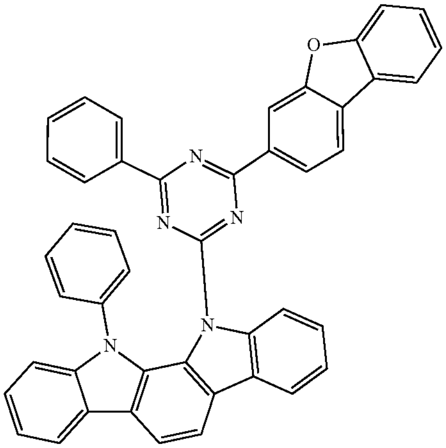
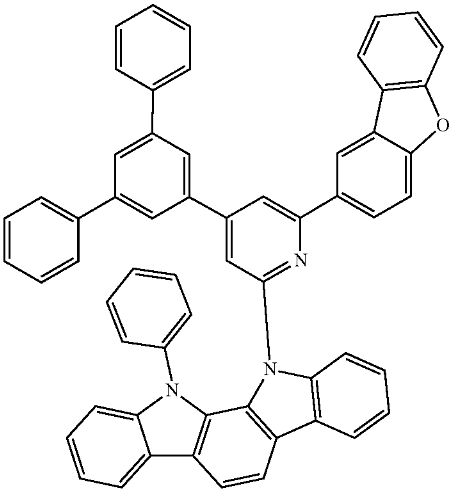
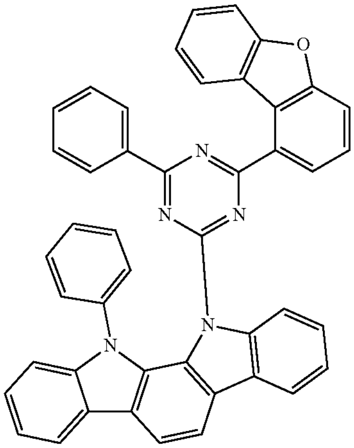
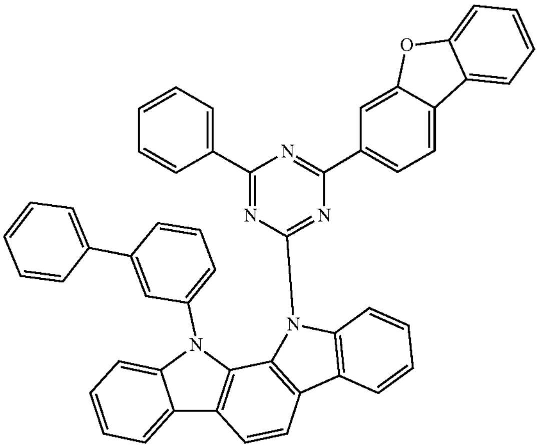

-continued
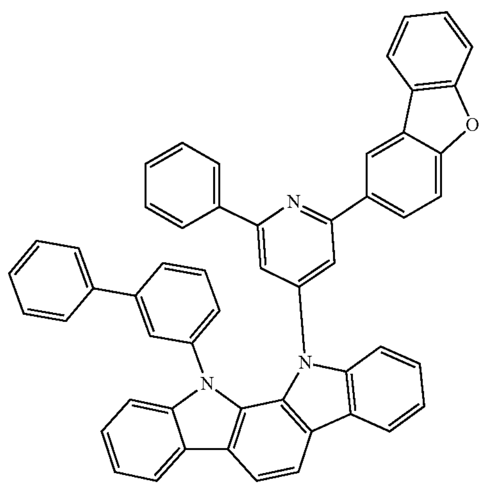
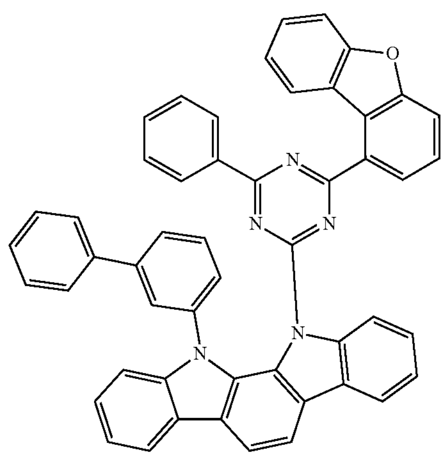
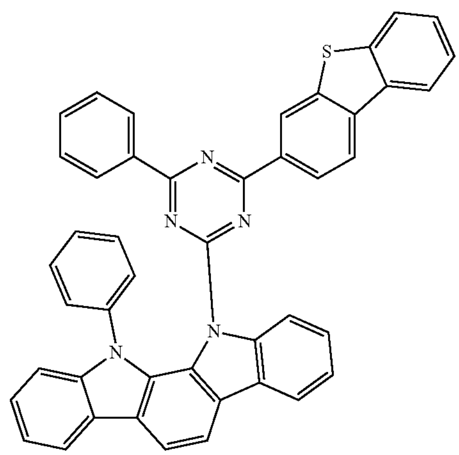
-continued
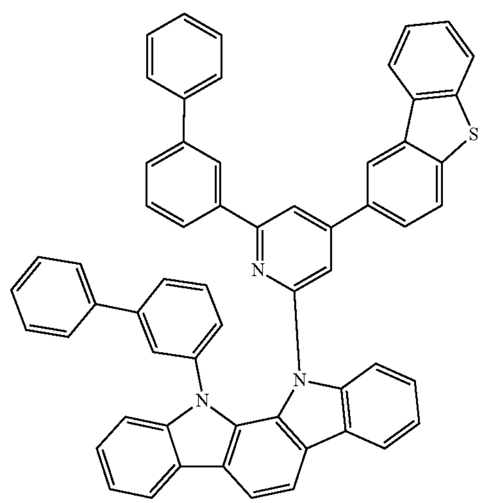
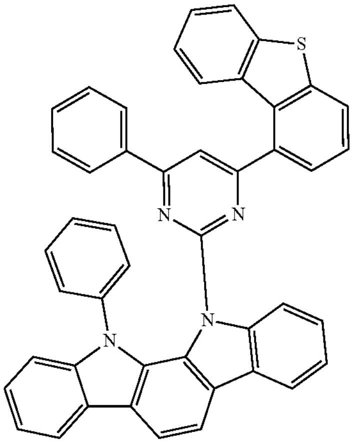
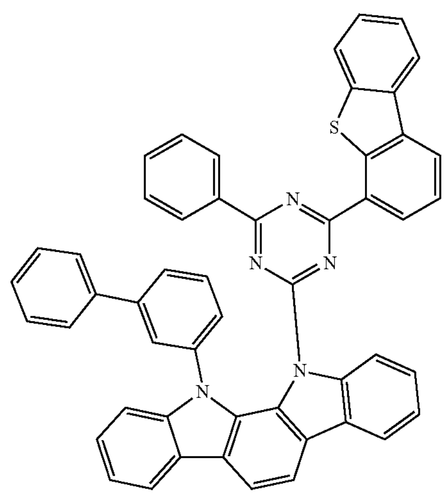

-continued
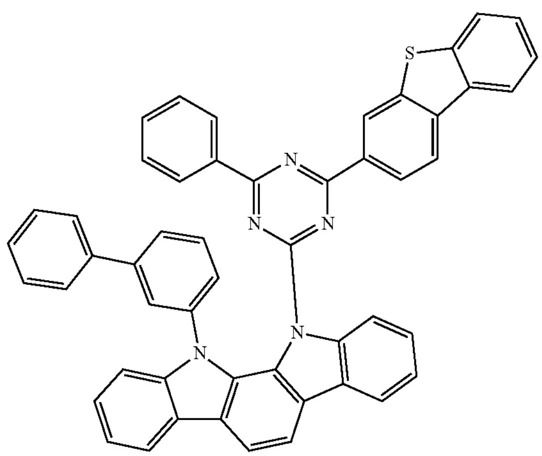
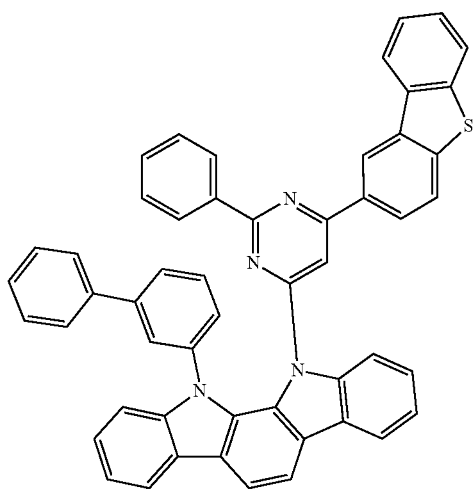
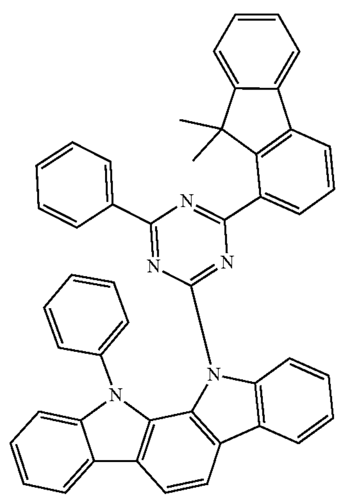
-continued
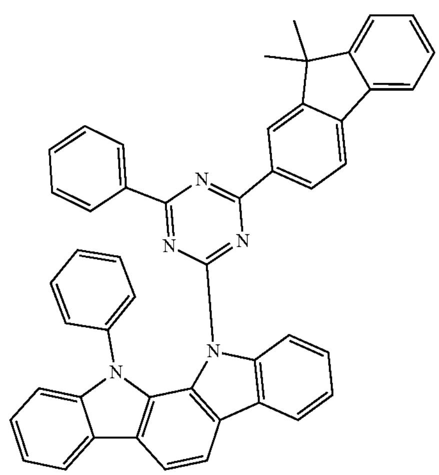
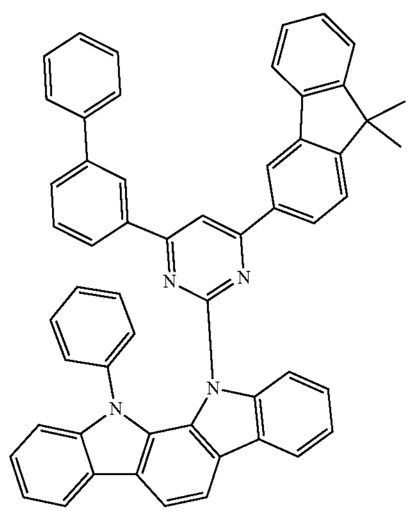
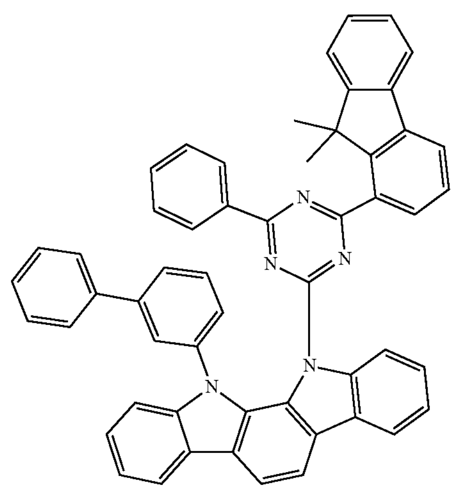

-continued
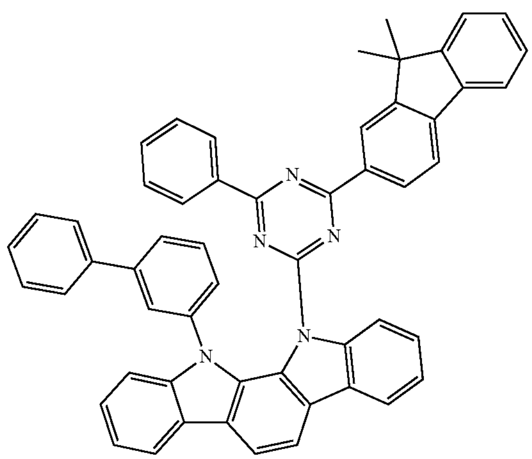
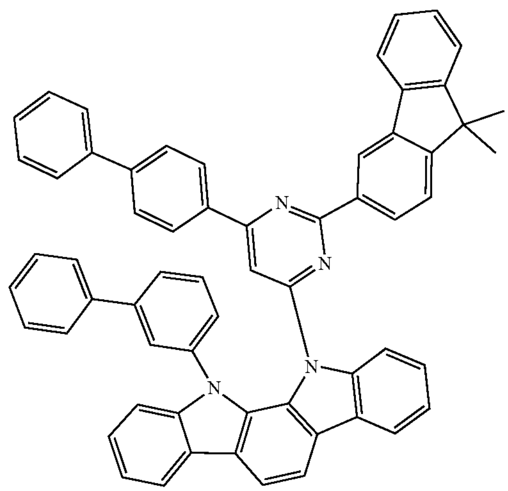
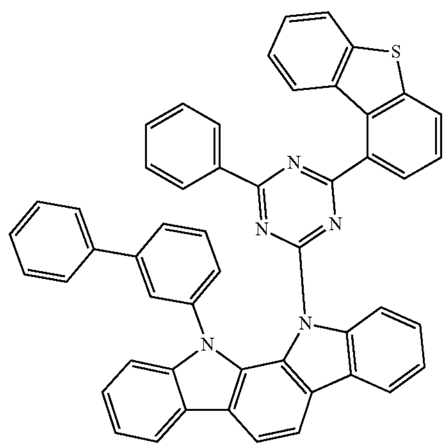
-continued
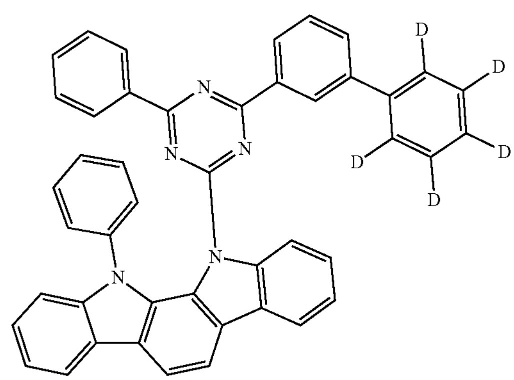
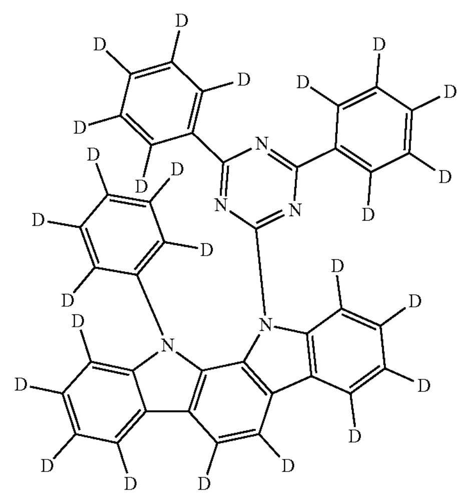
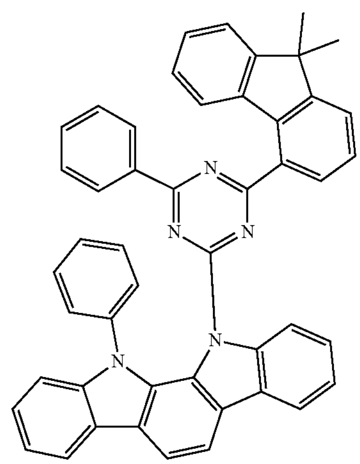

-continued
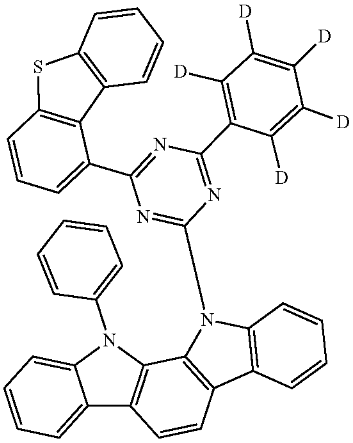
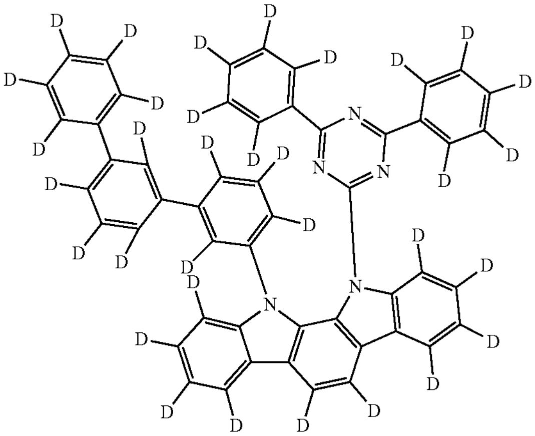
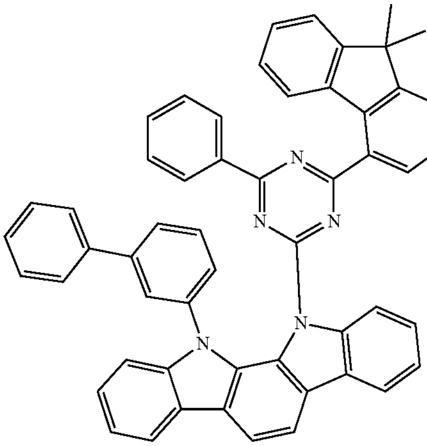
-continued
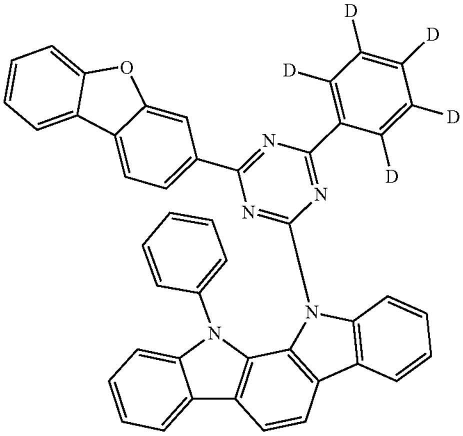
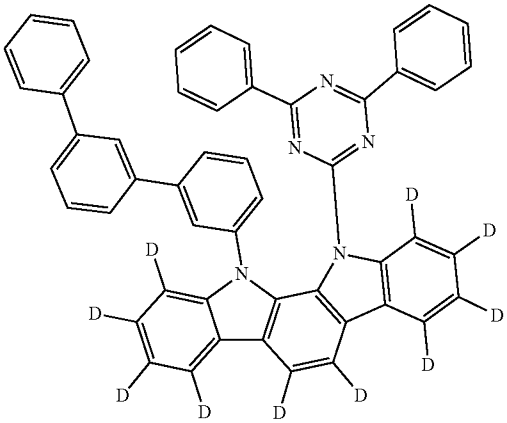
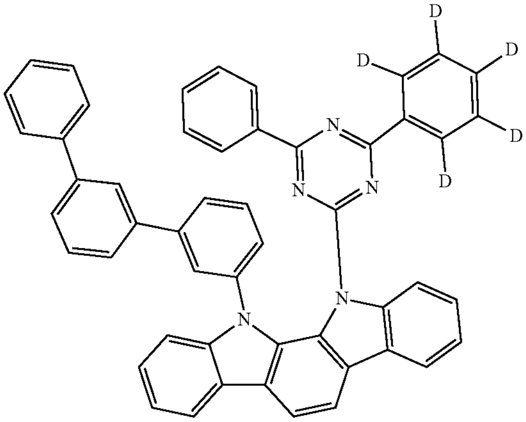
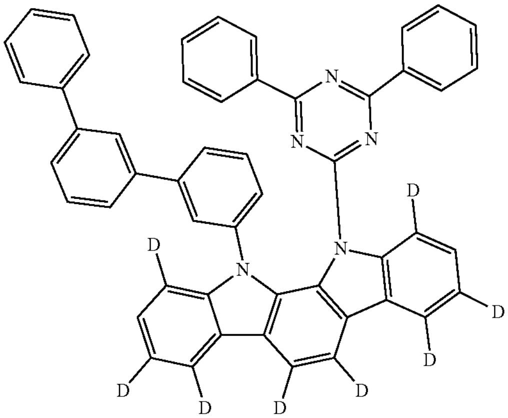

-continued
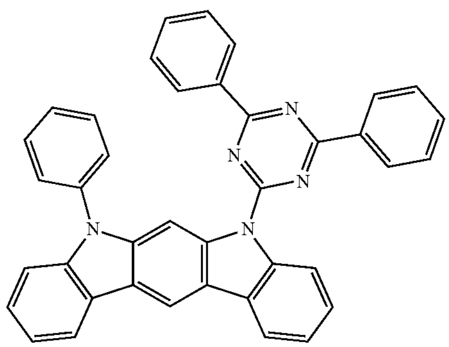
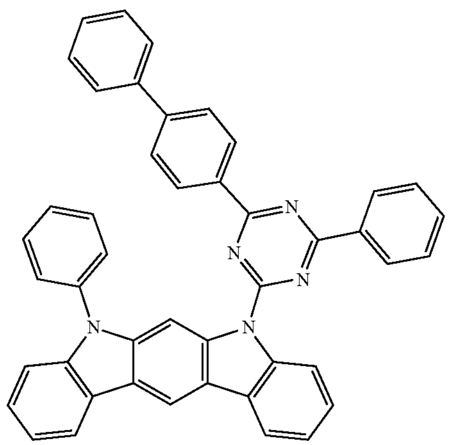
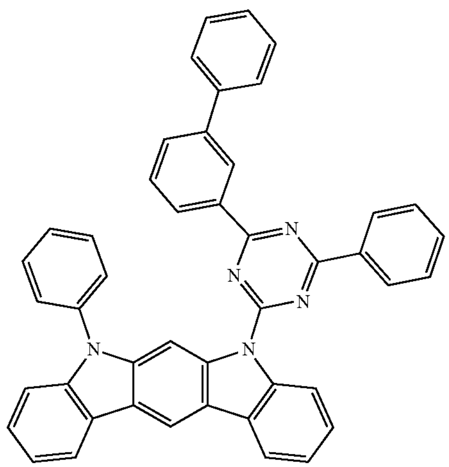
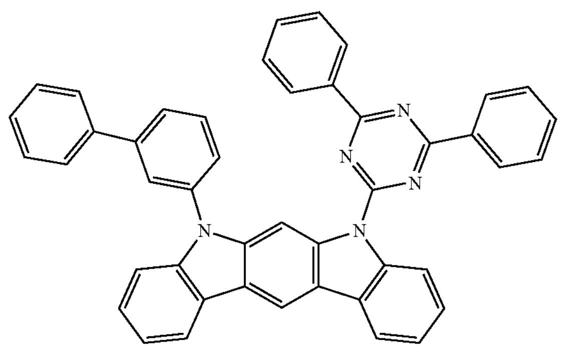
-continued
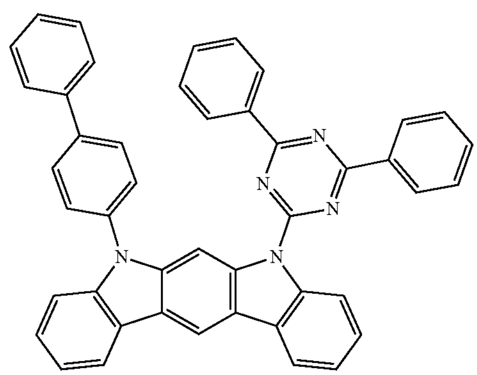
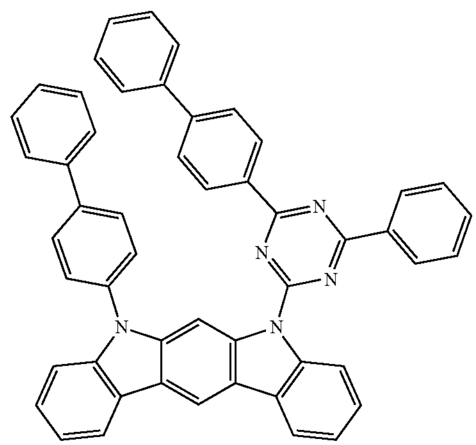
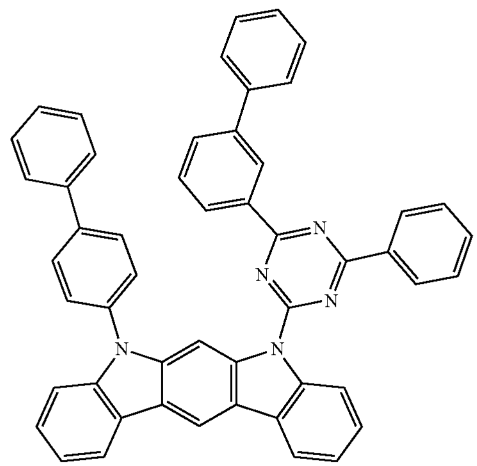
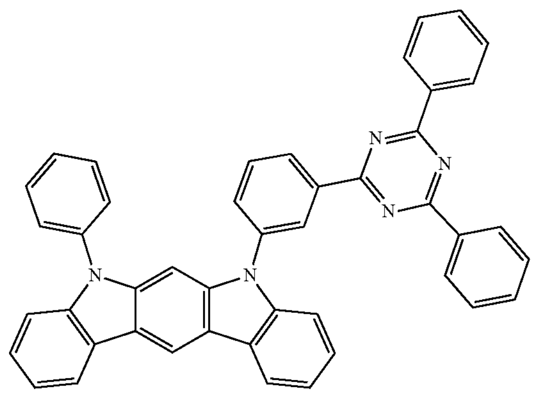

-continued
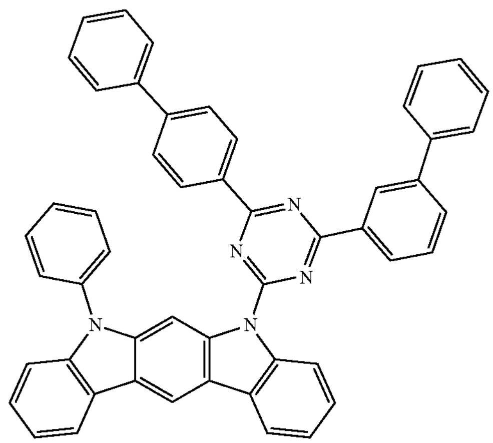
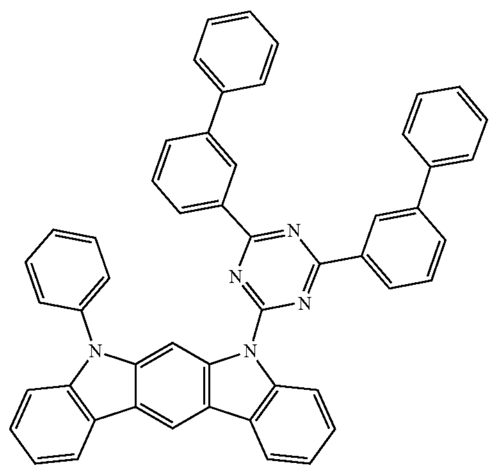
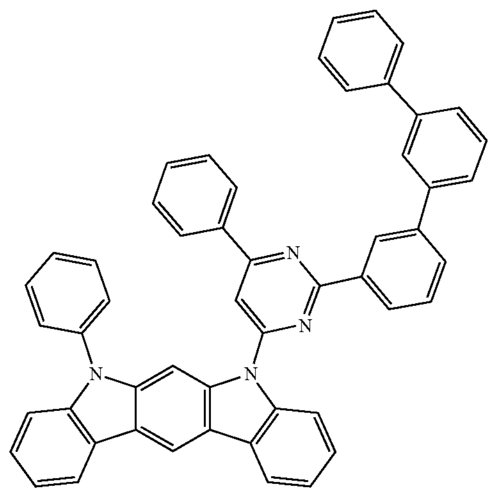
-continued
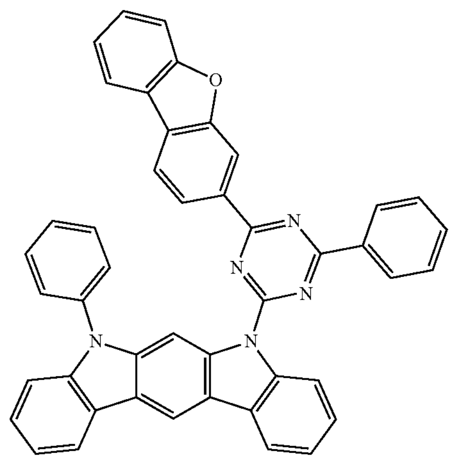
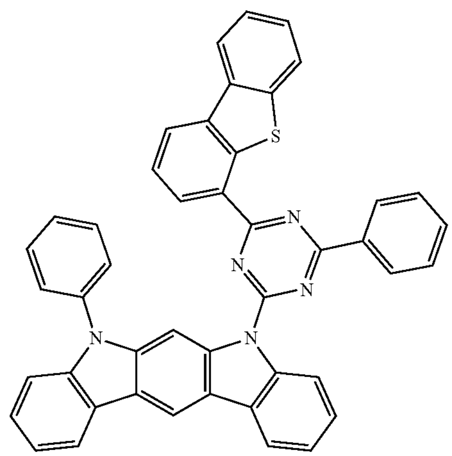
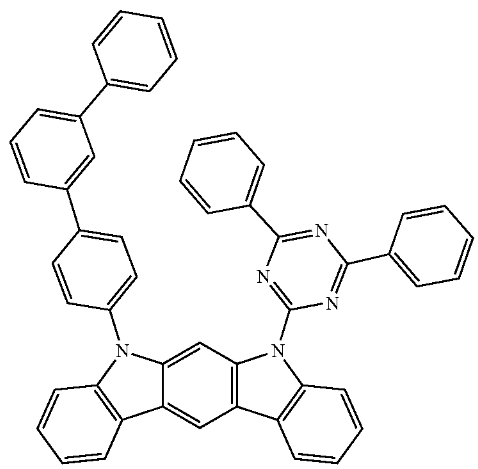

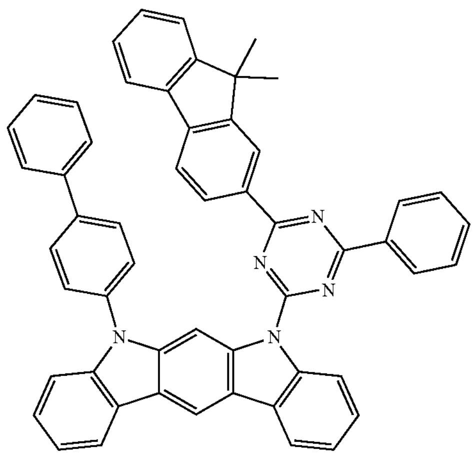
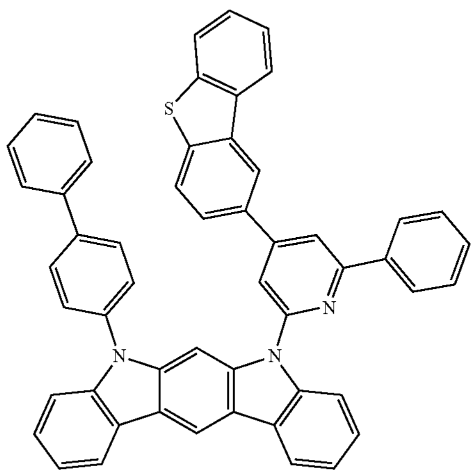
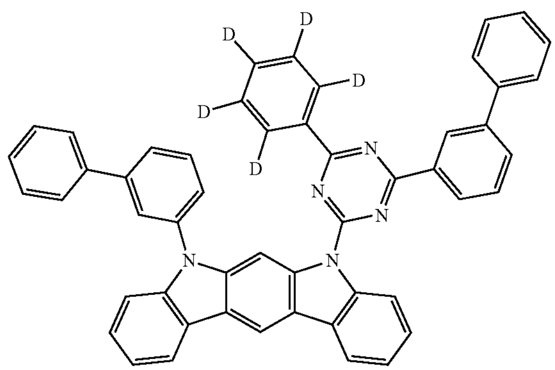
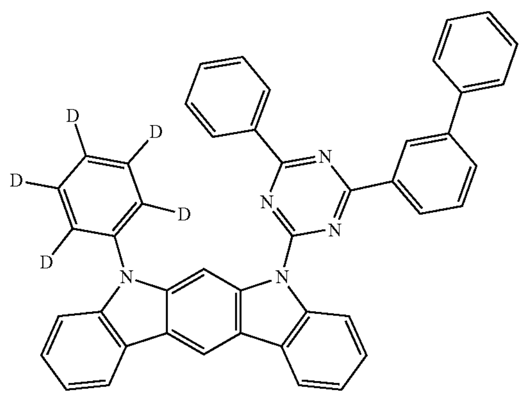
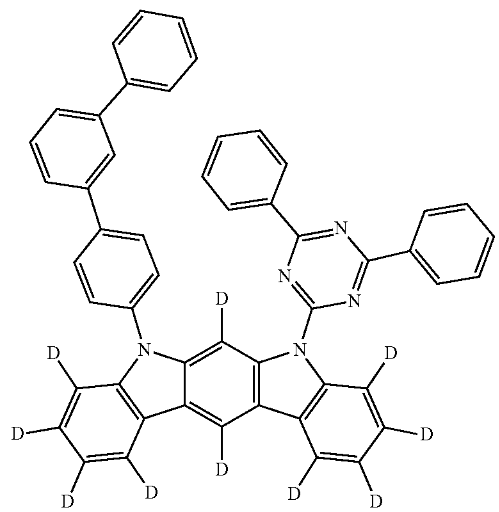
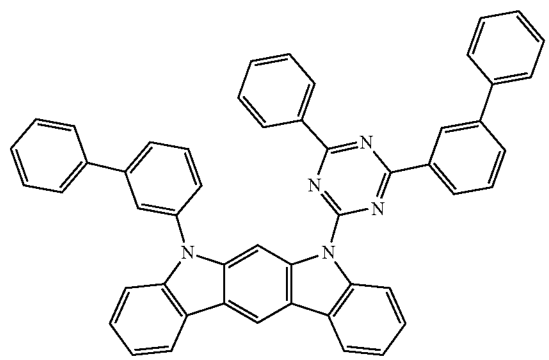
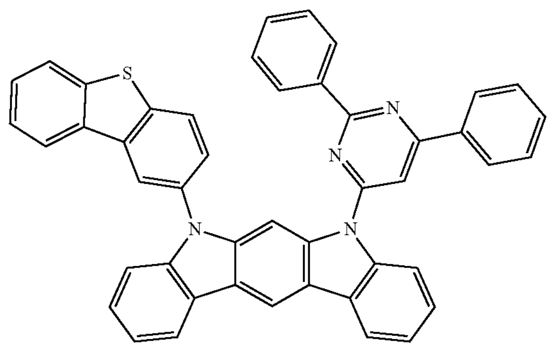
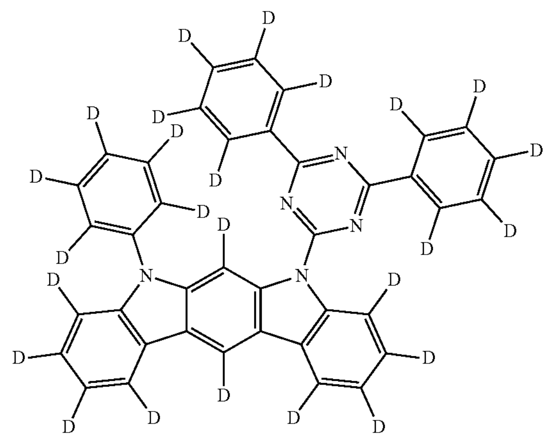

-continued
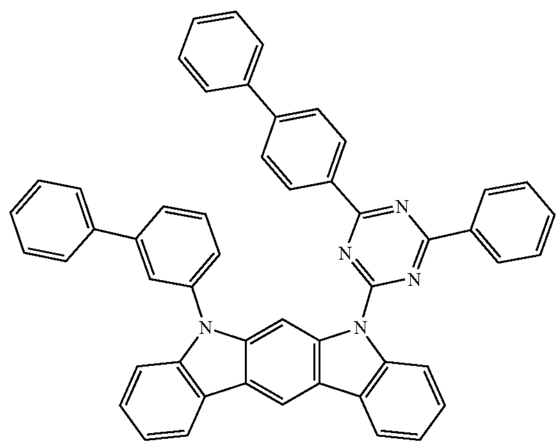
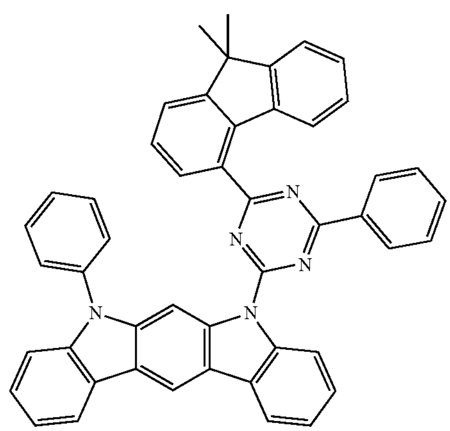
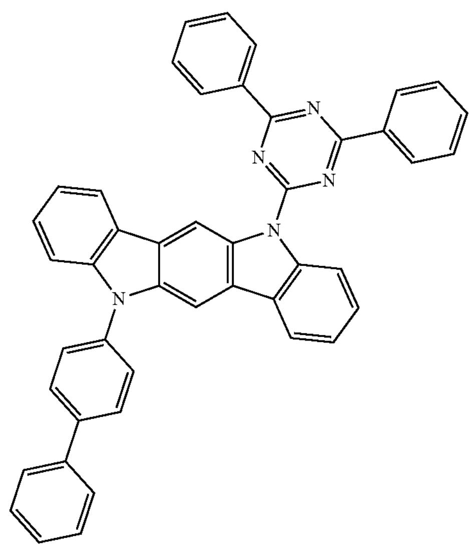
-continued
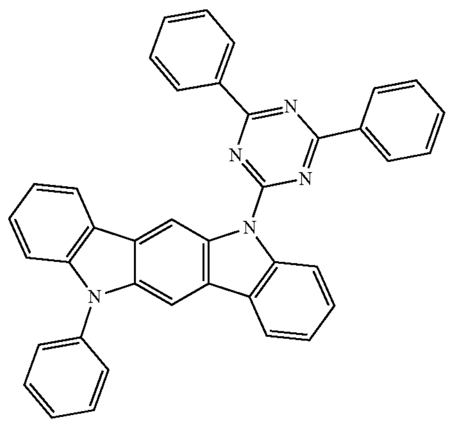
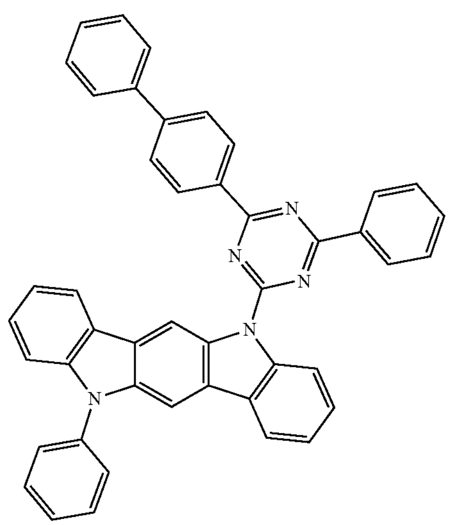
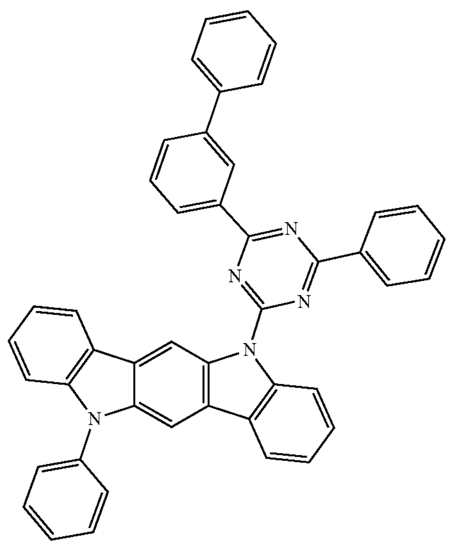

-continued
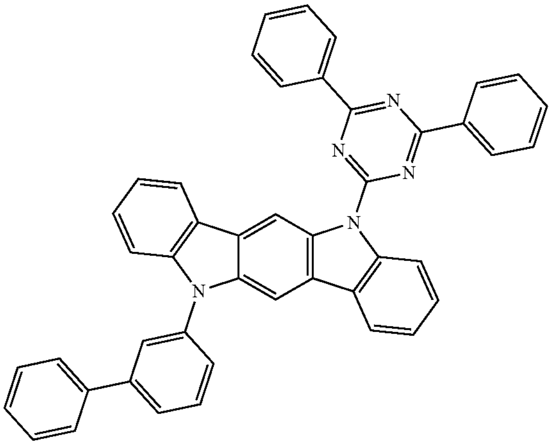
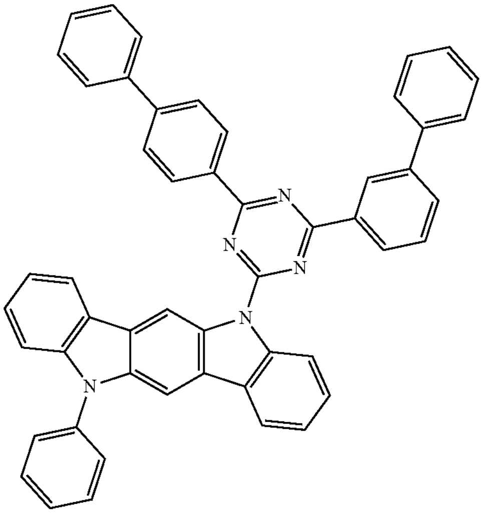
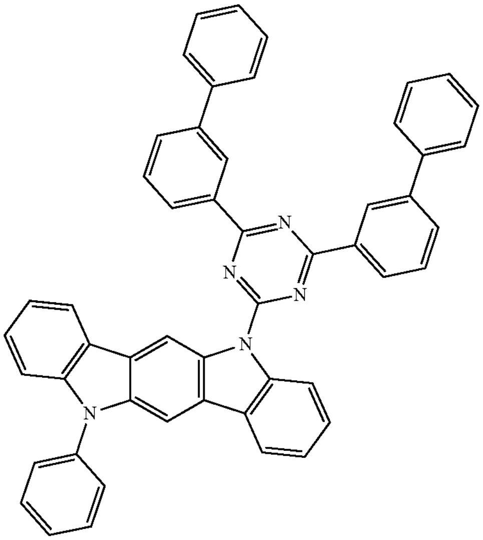
-continued
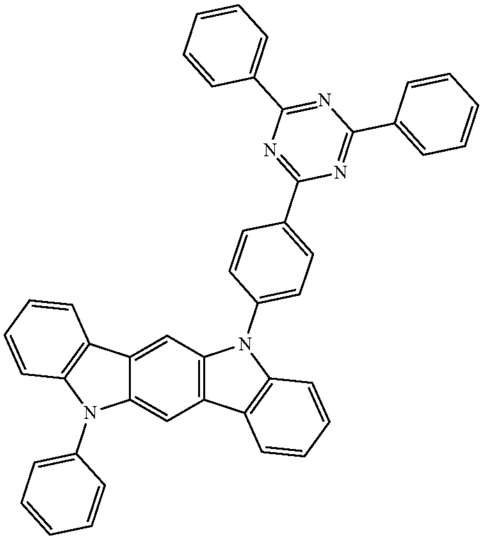
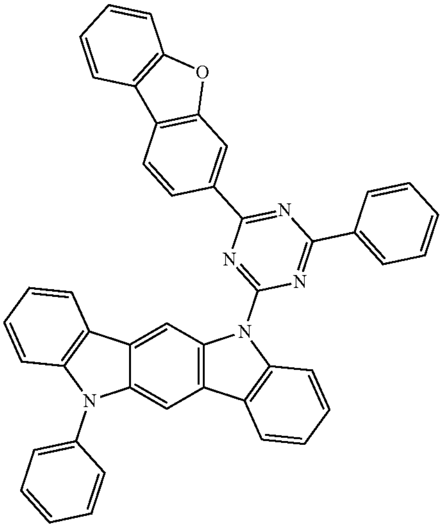
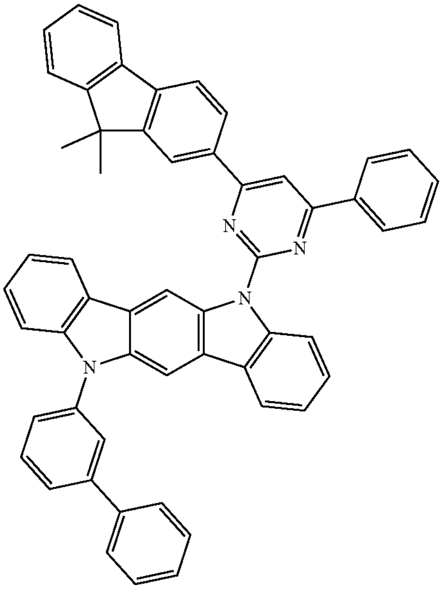

-continued
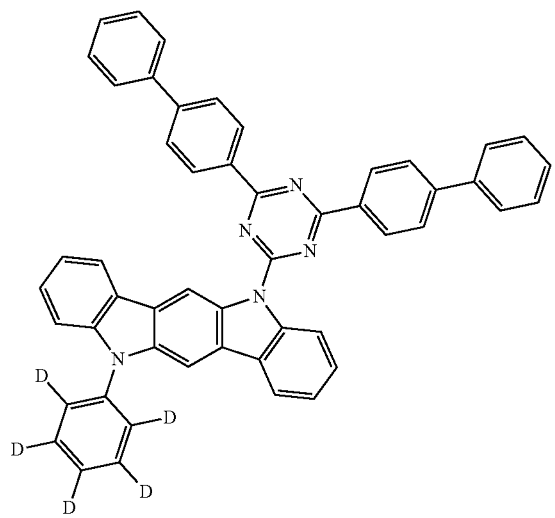
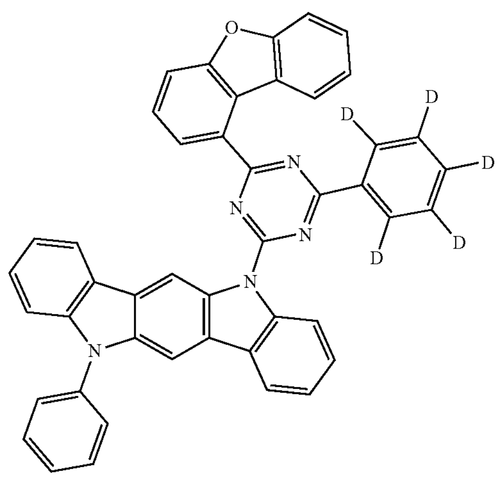
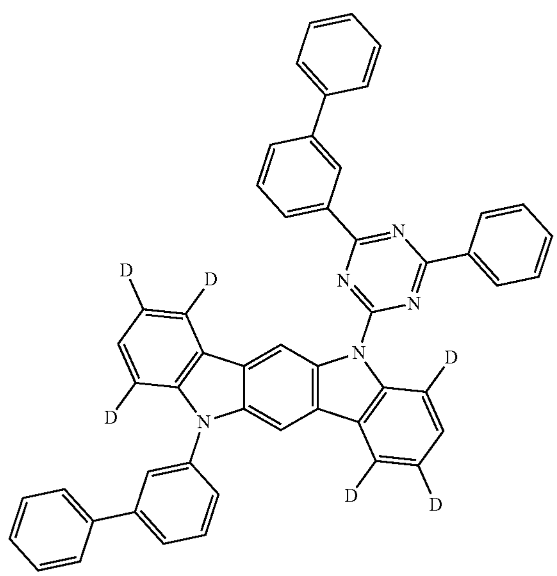
-continued
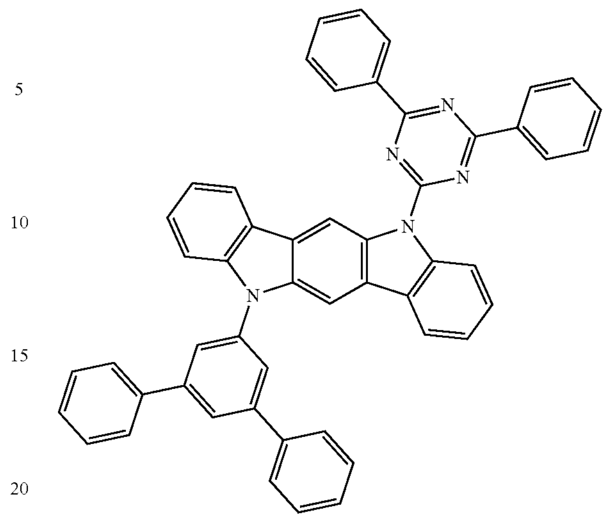
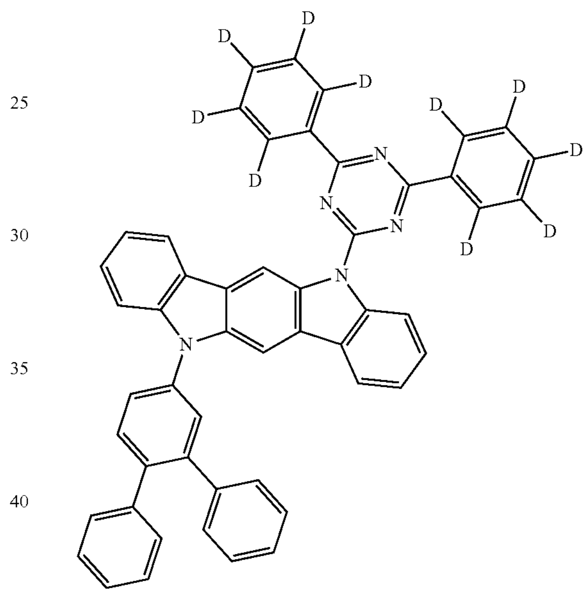
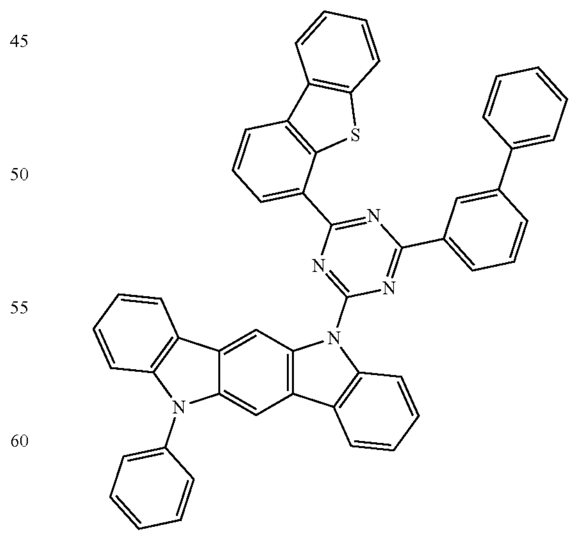

-continued
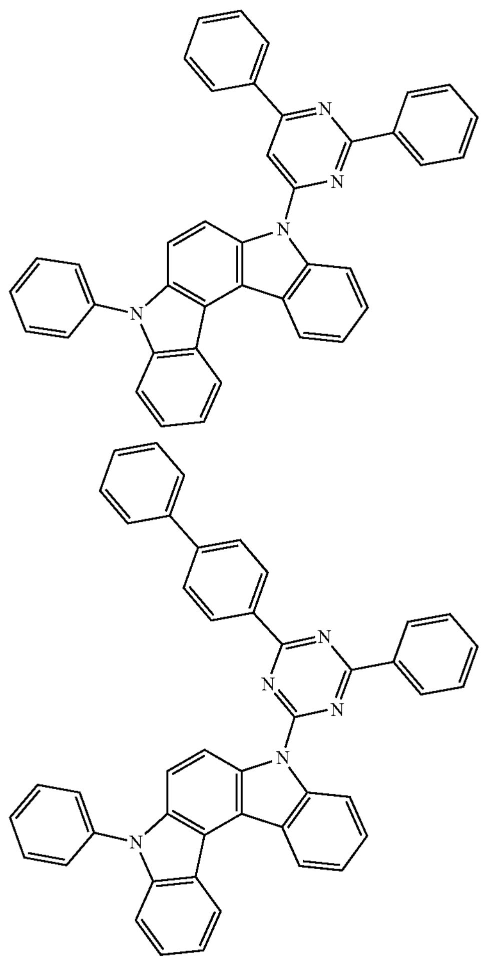
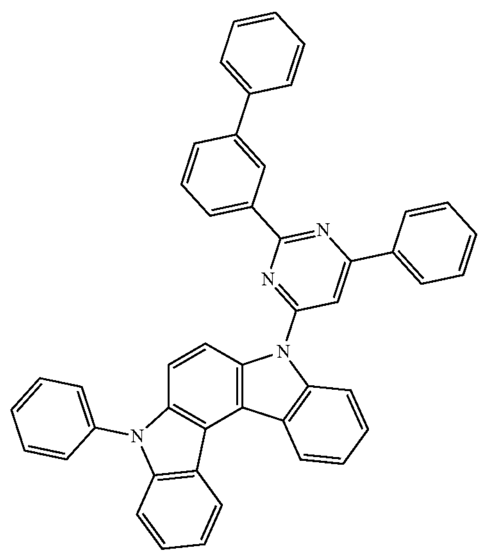
-continued
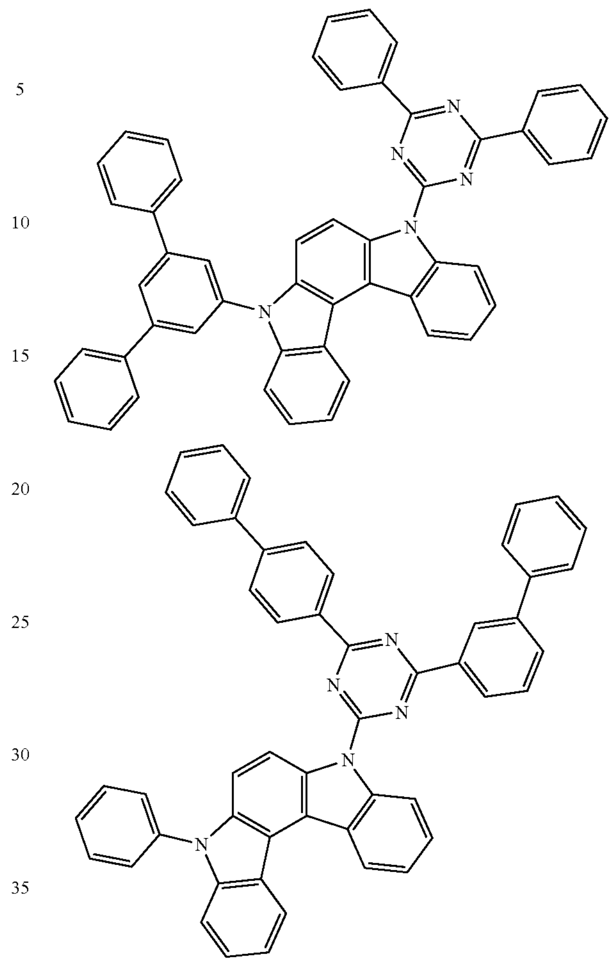
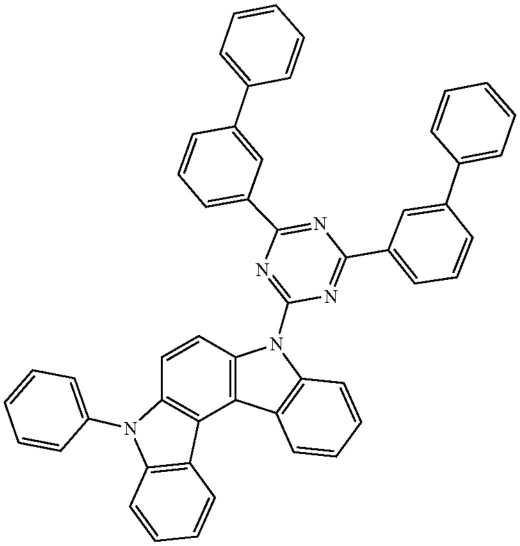

-continued
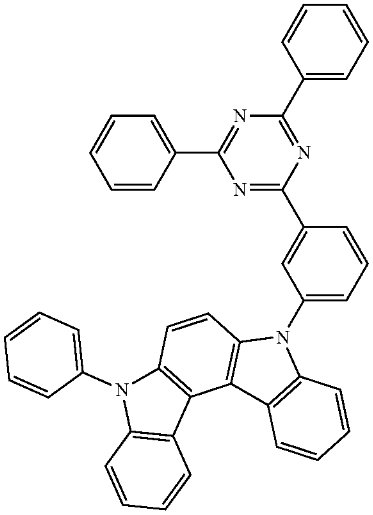
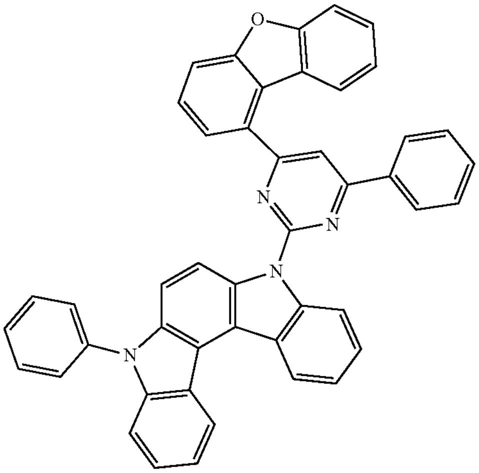
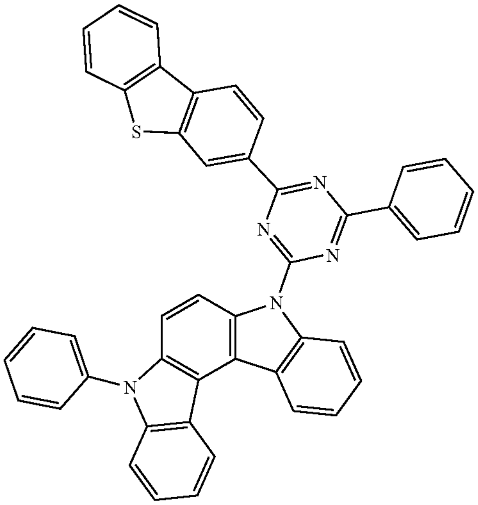
-continued
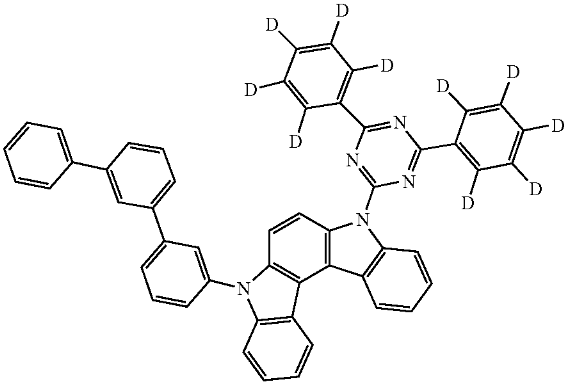
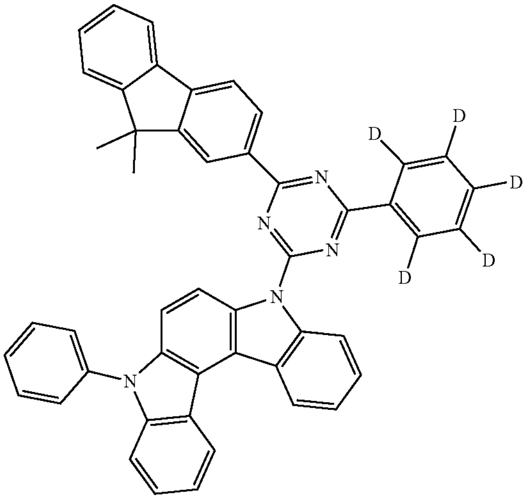
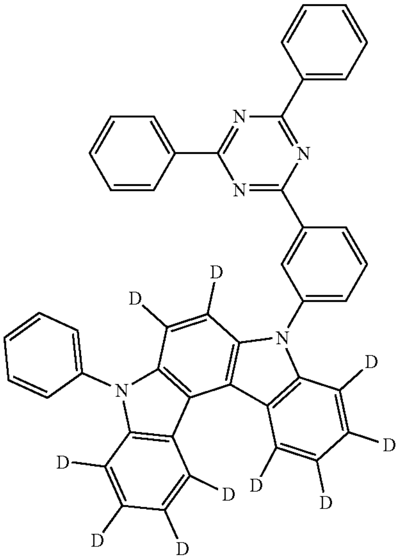

-continued
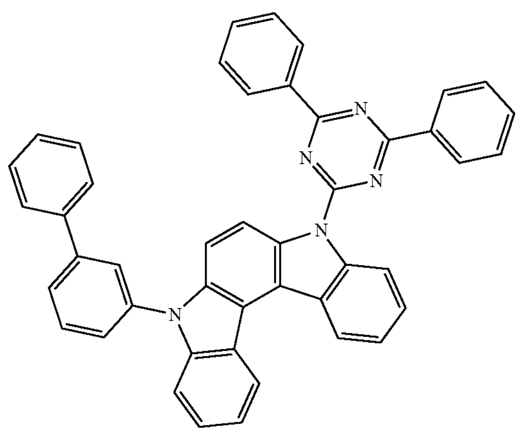
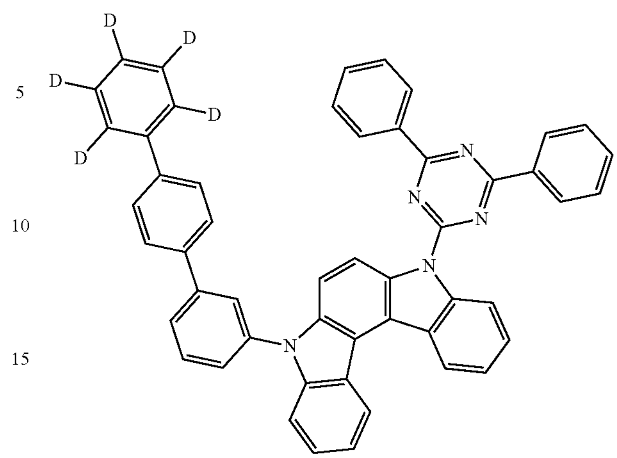
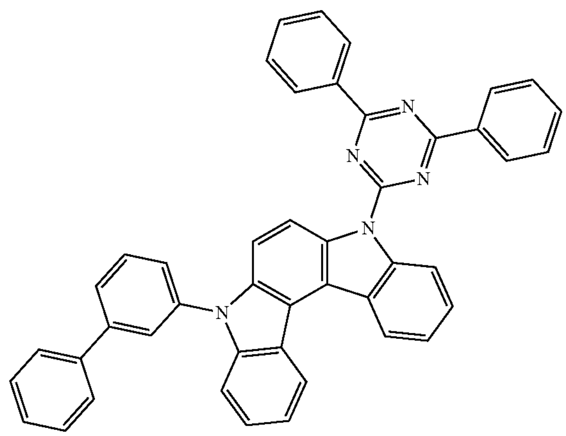
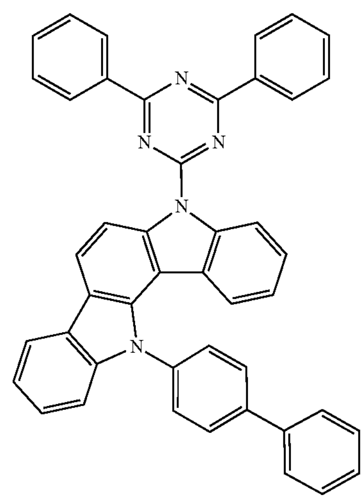
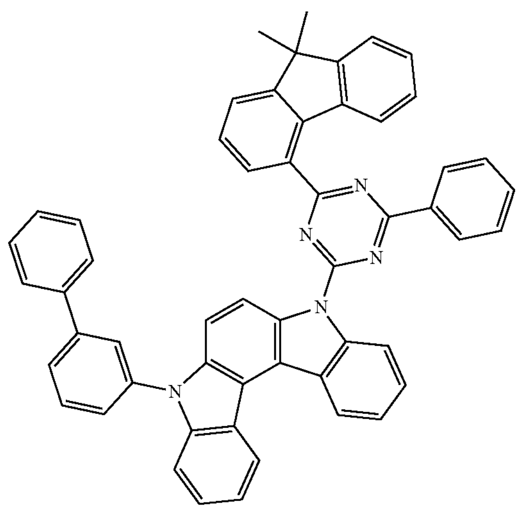
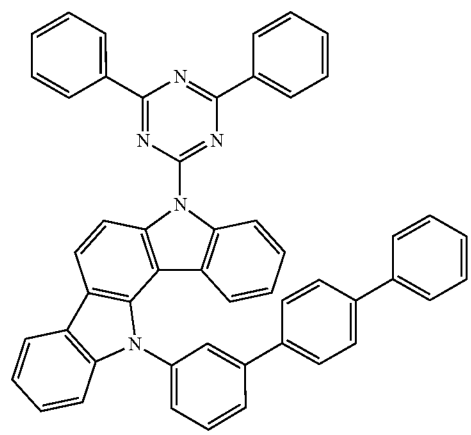

-continued
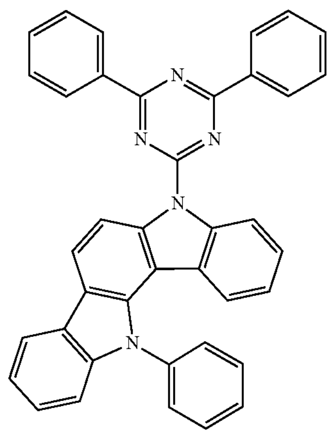
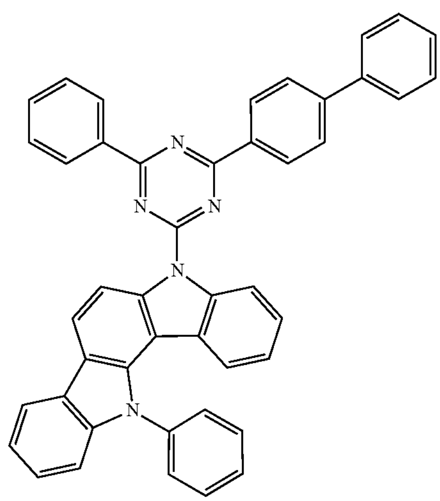
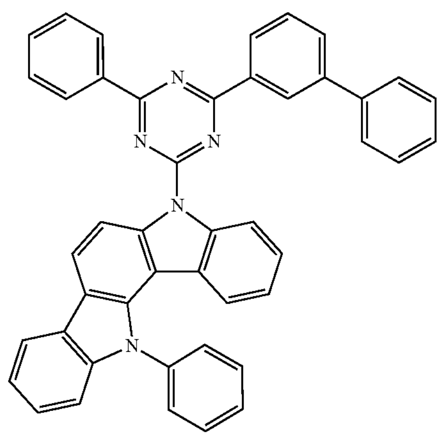
-continued
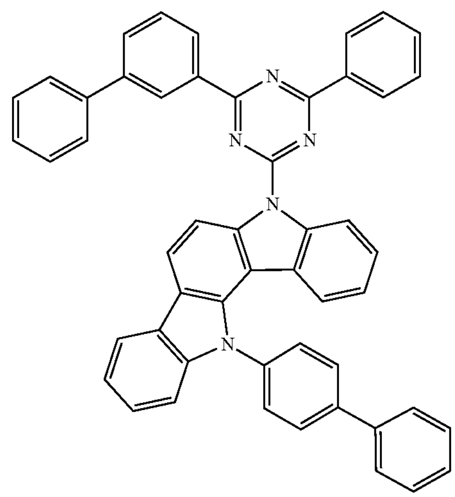
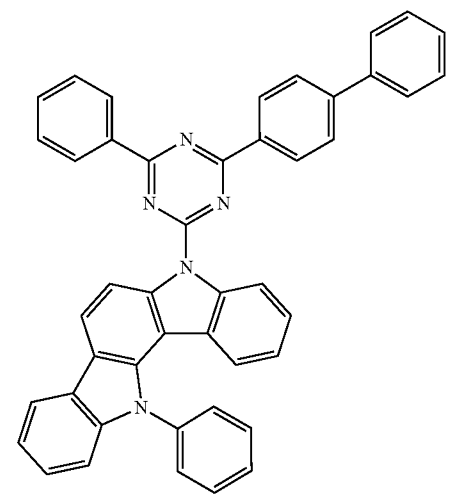
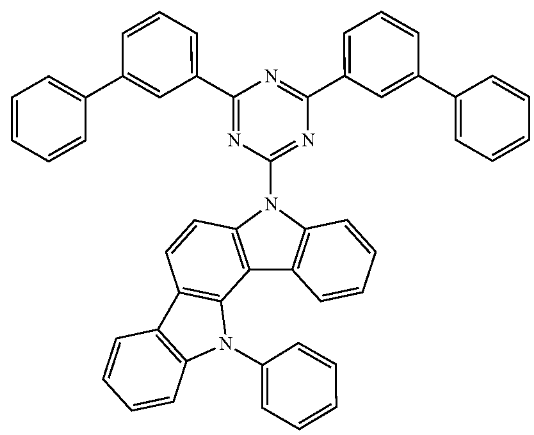

-continued
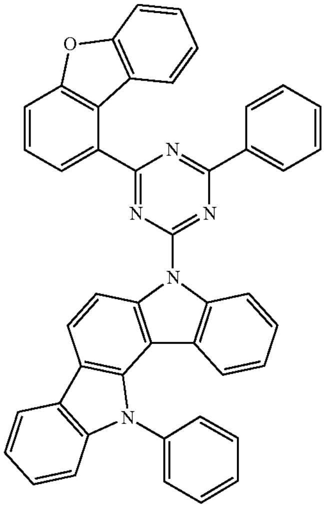
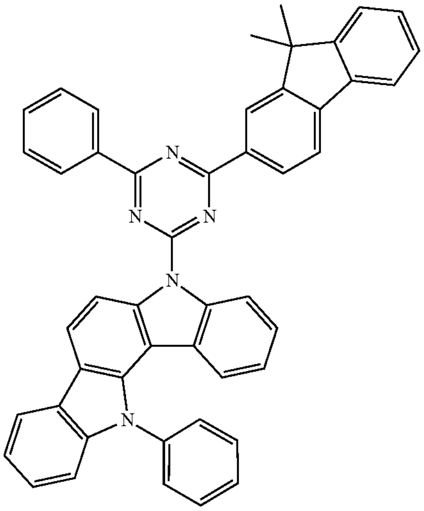
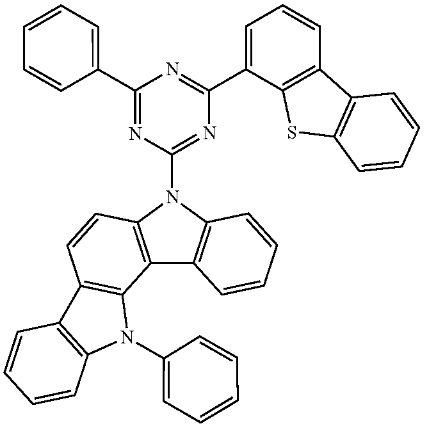
-continued
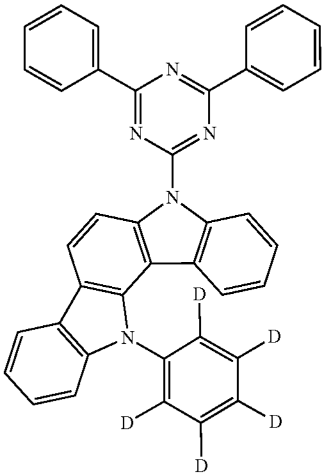
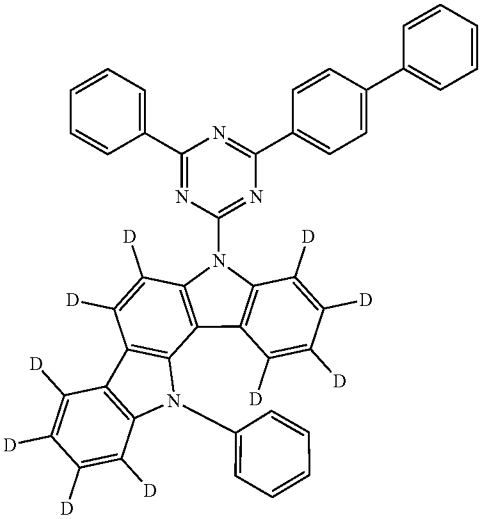
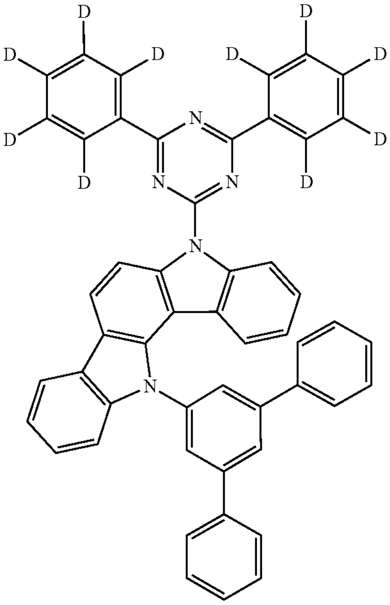

-continued
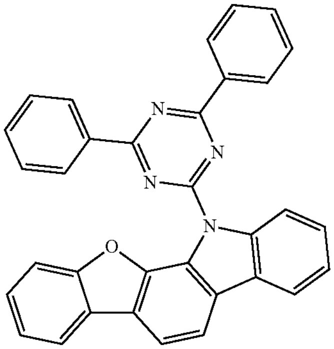
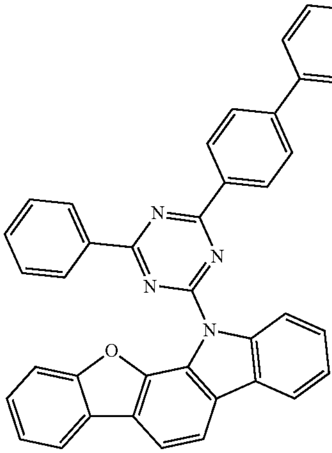
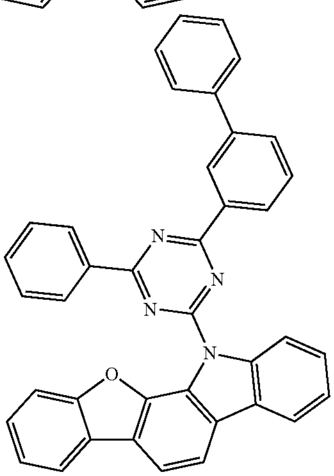
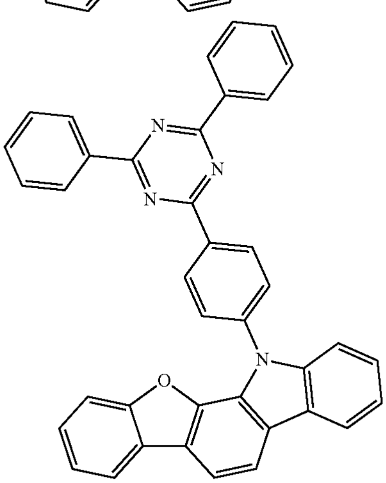
-continued
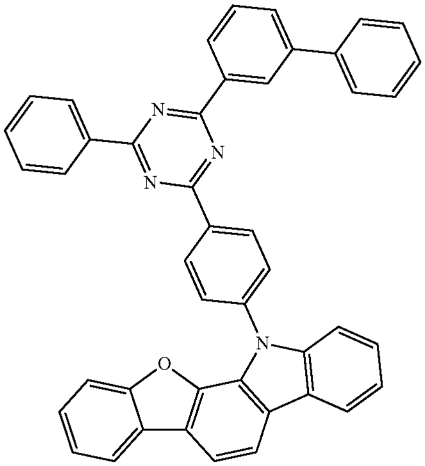
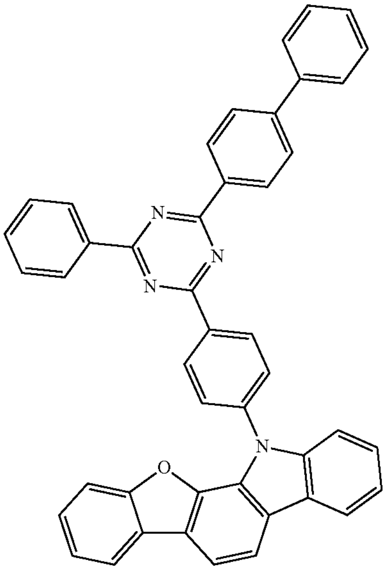
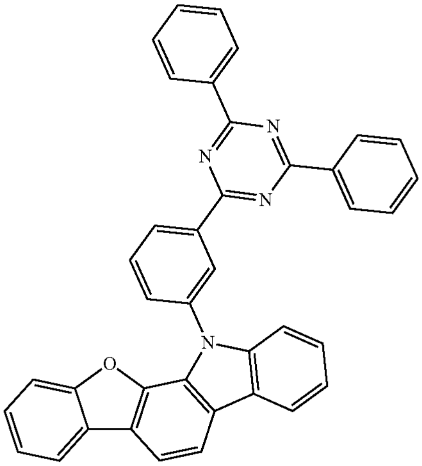

-continued
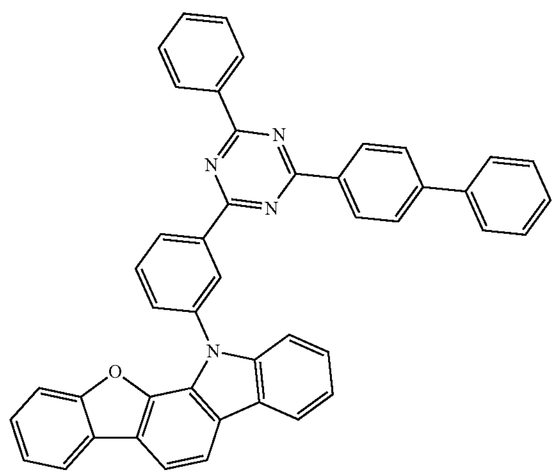
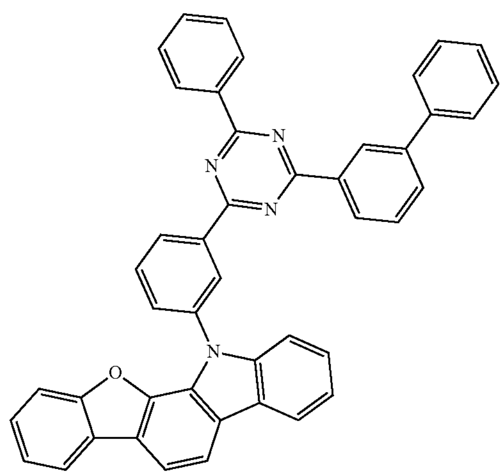
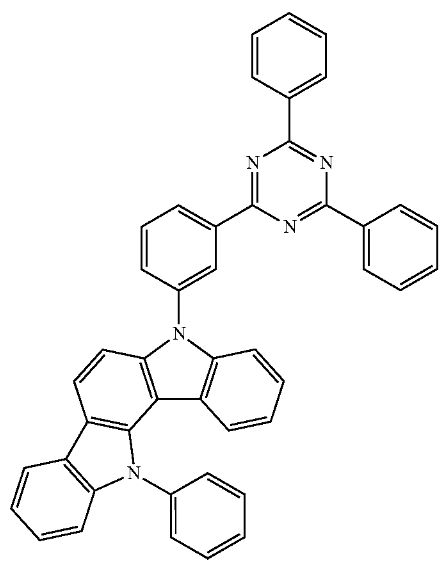
-continued
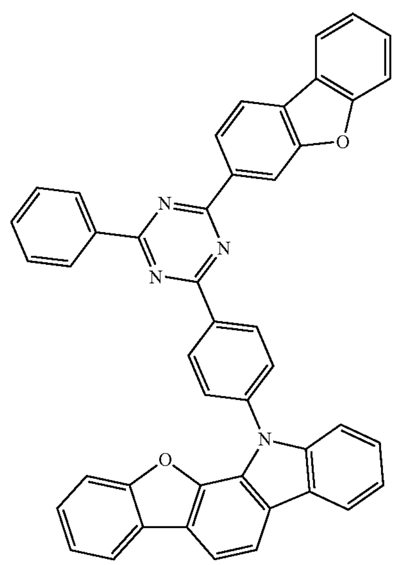
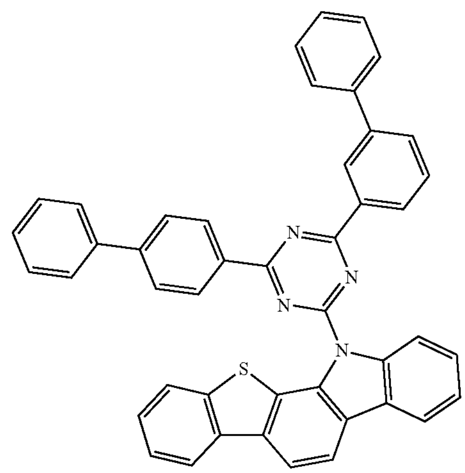
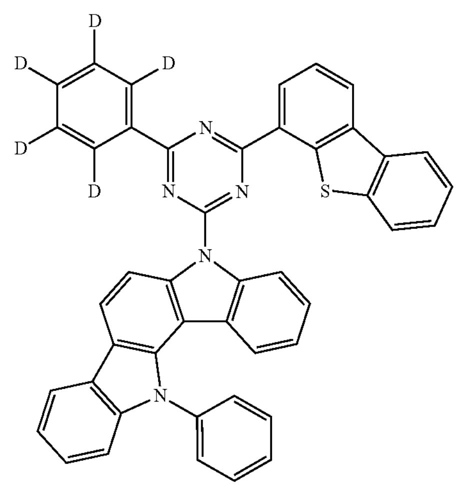

-continued
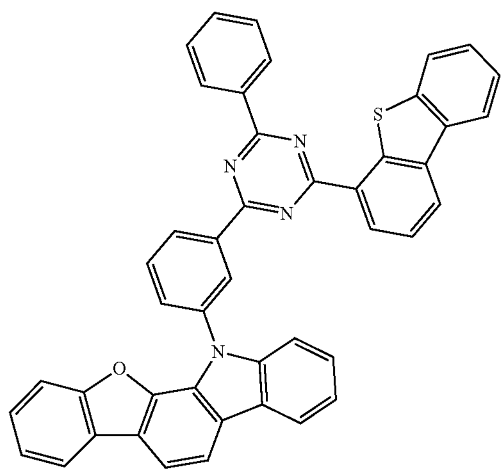
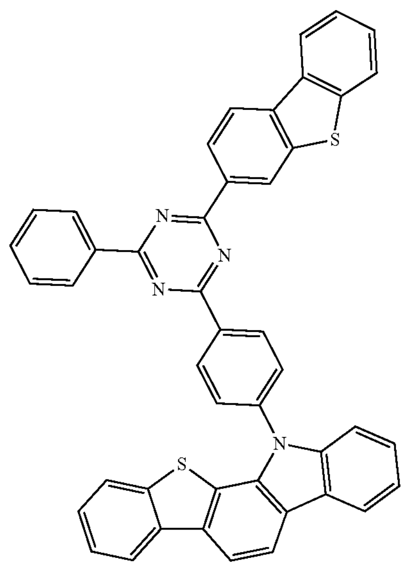
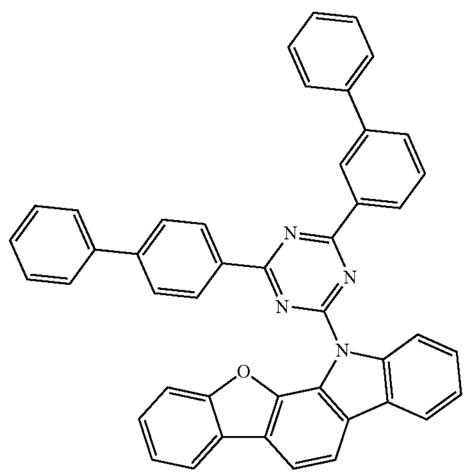
-continued
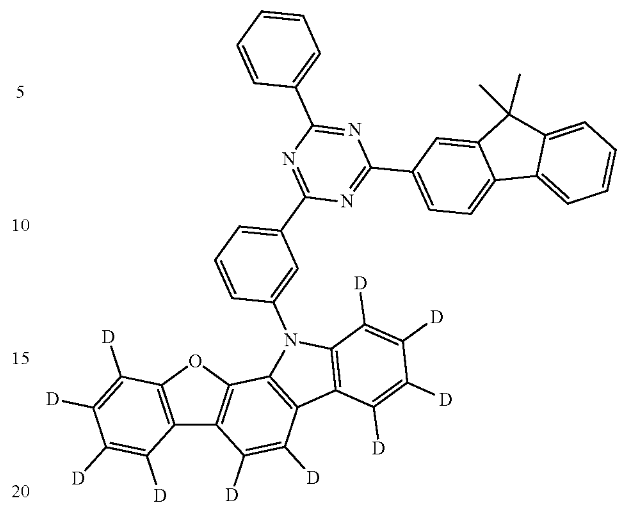
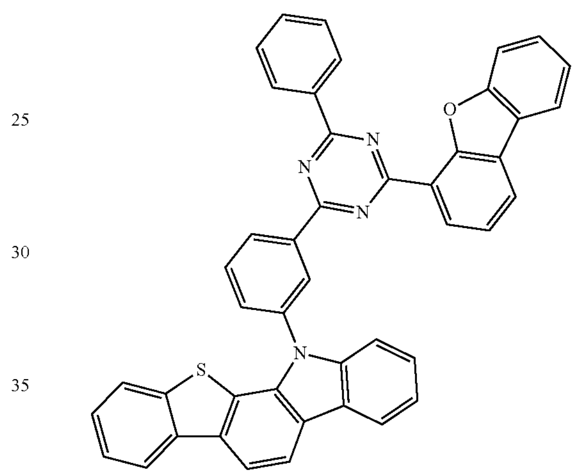
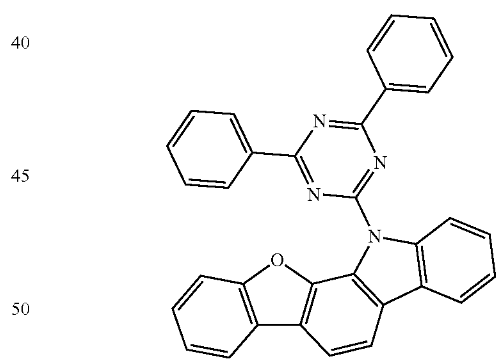
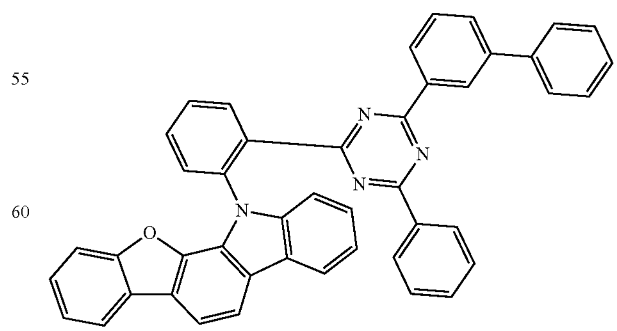

-continued
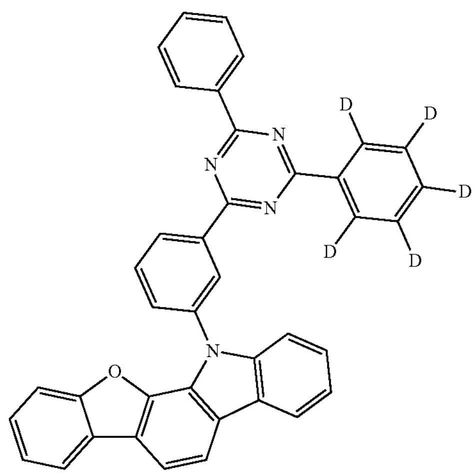
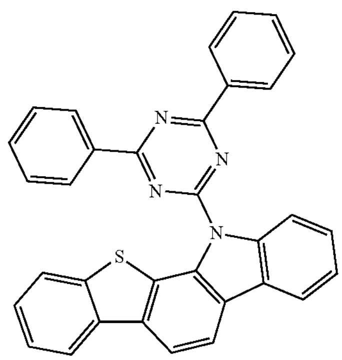
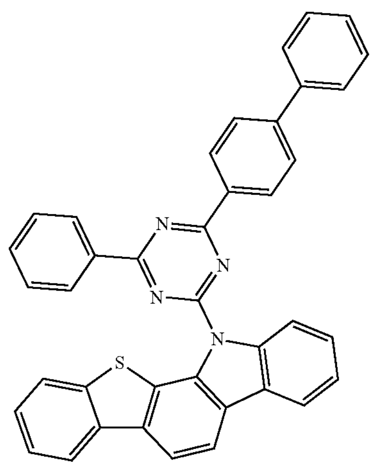
-continued
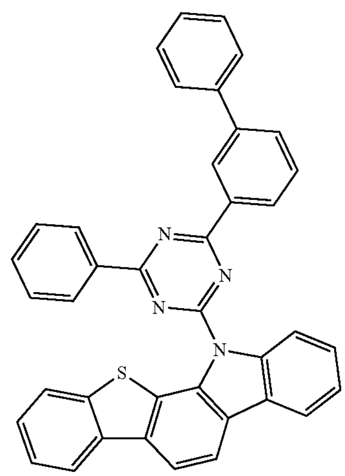
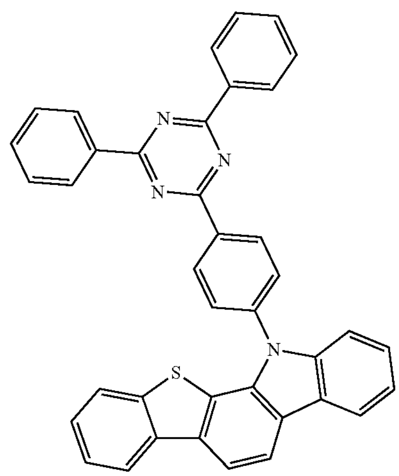
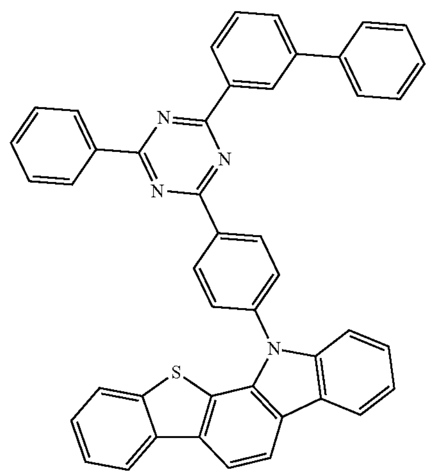

-continued
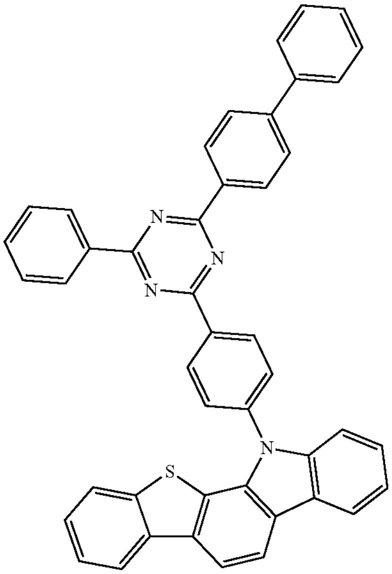
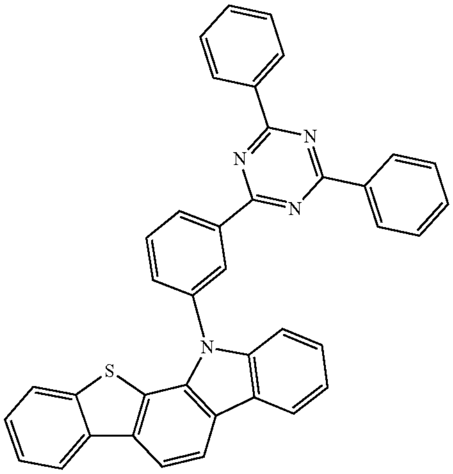
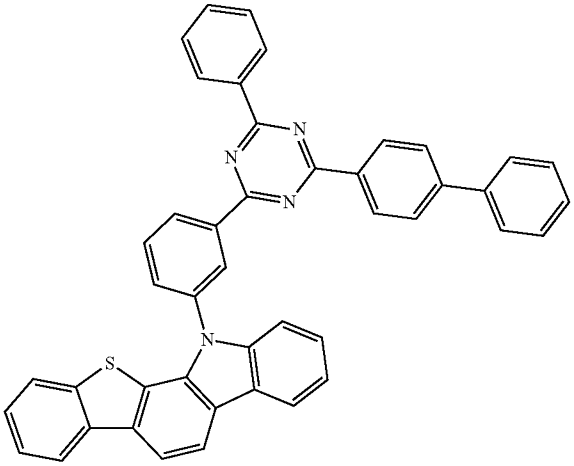
-continued
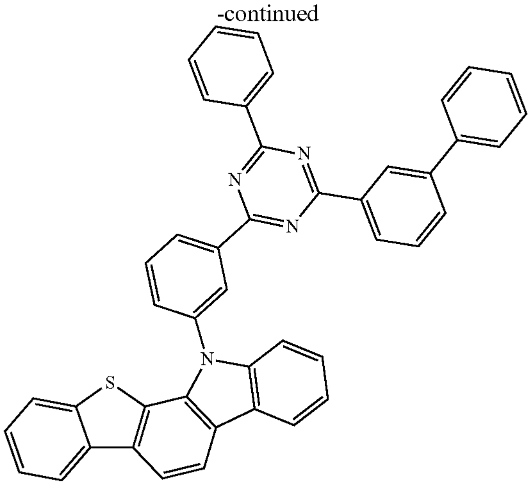
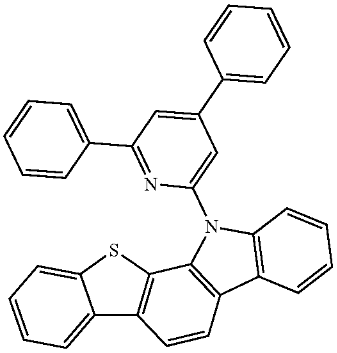
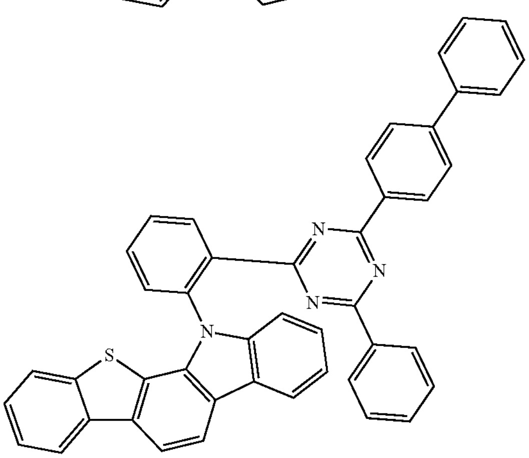
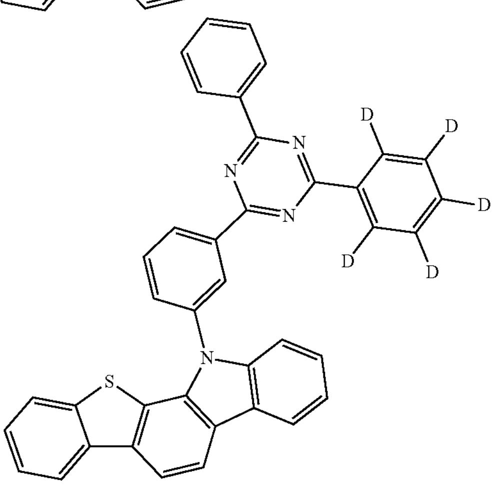

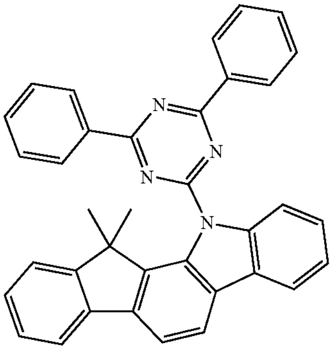
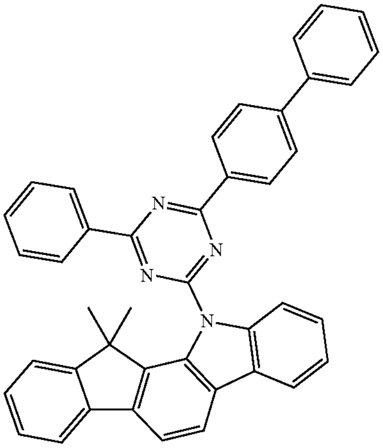
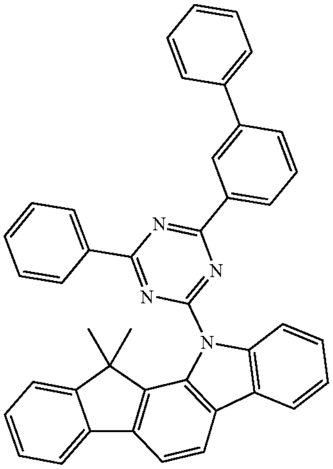
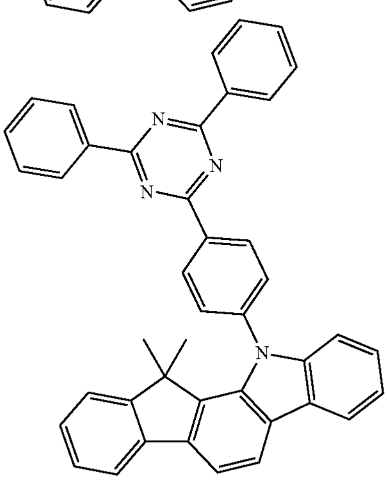
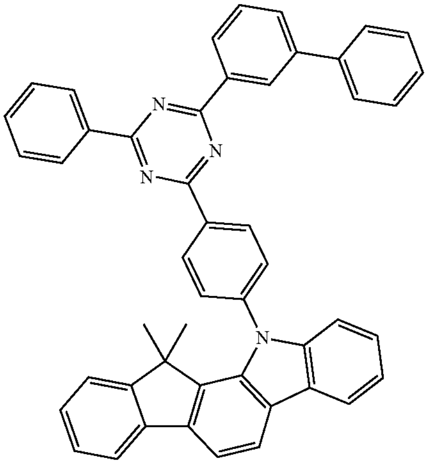
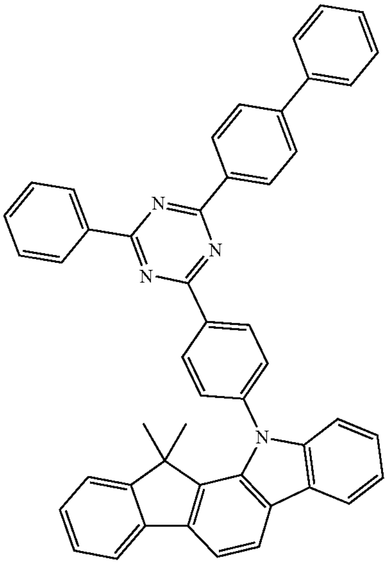
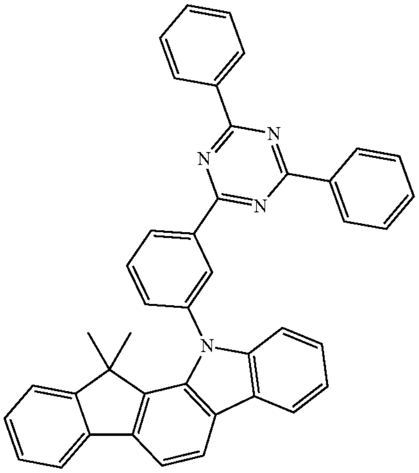

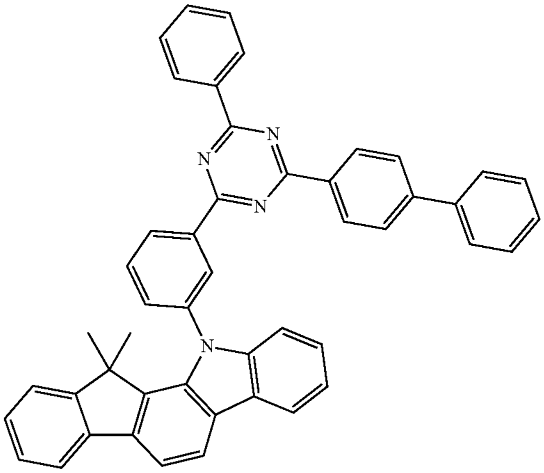
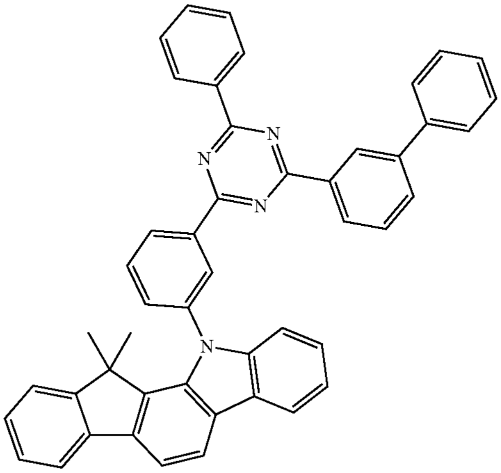
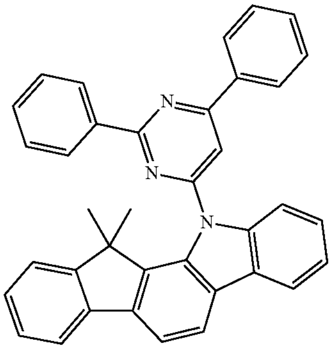
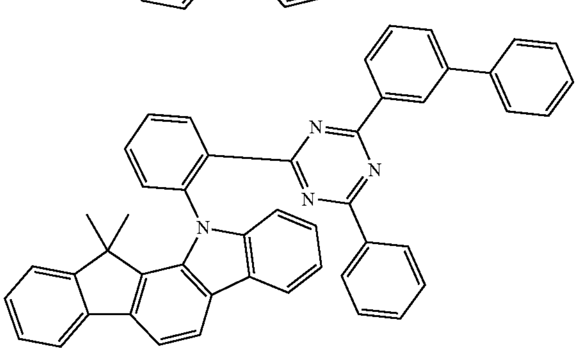
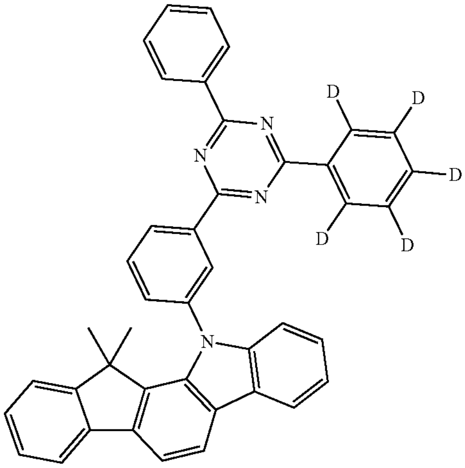
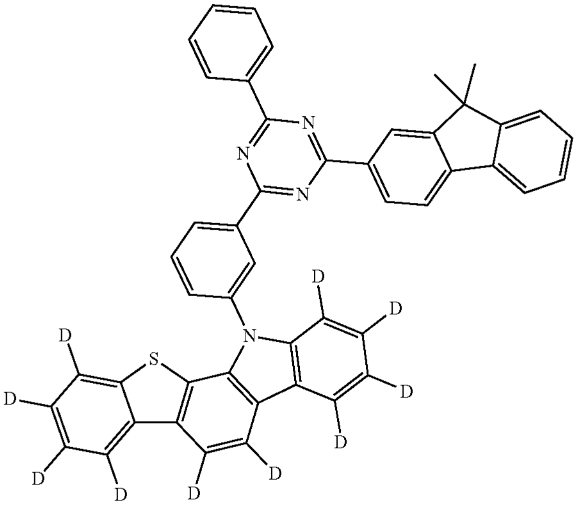
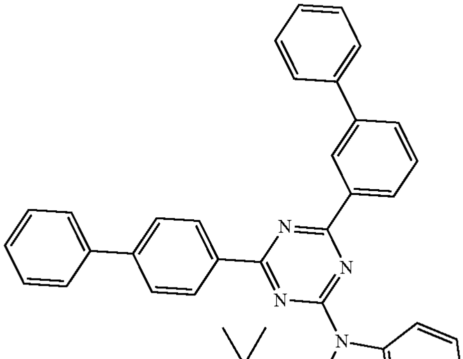

-continued
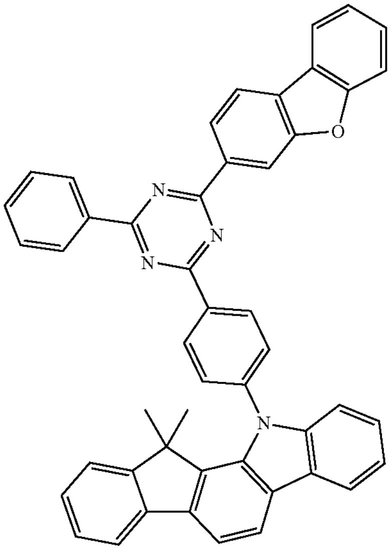
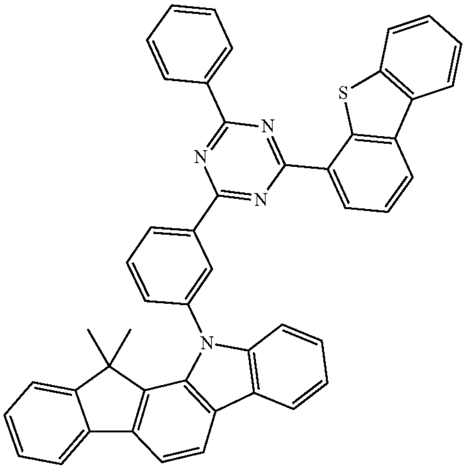
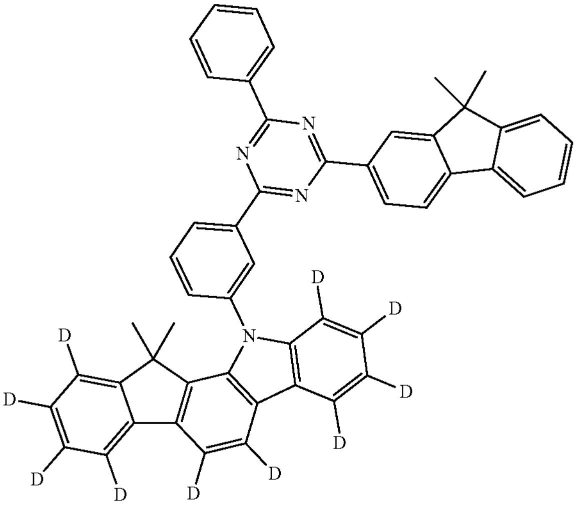
-continued
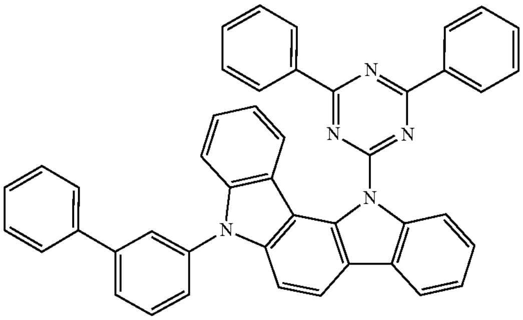
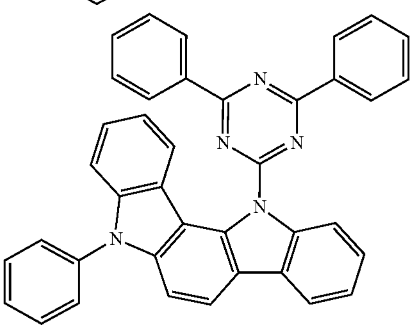
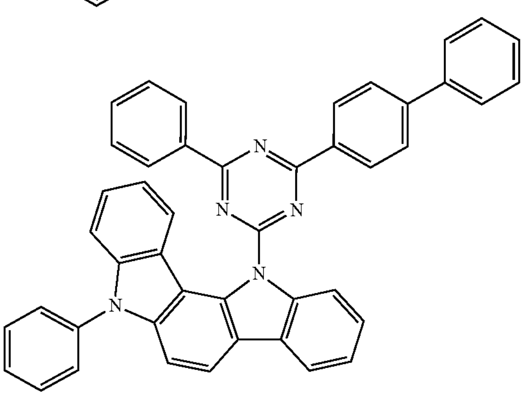
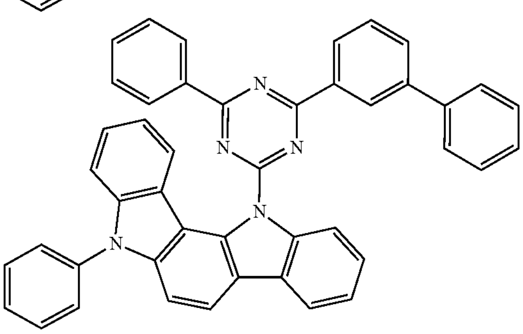
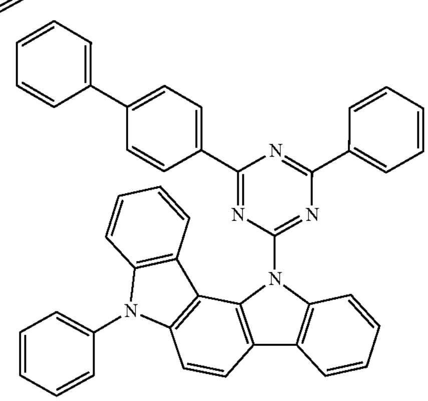

-continued
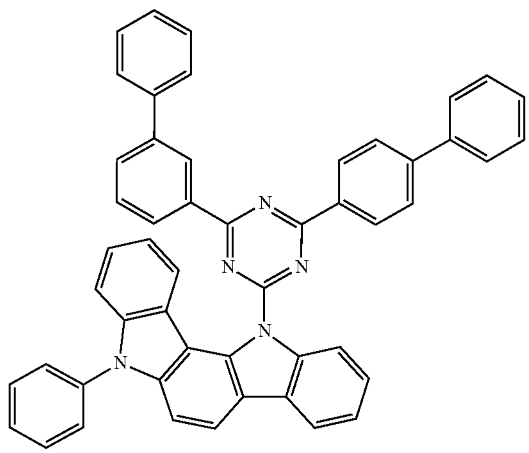
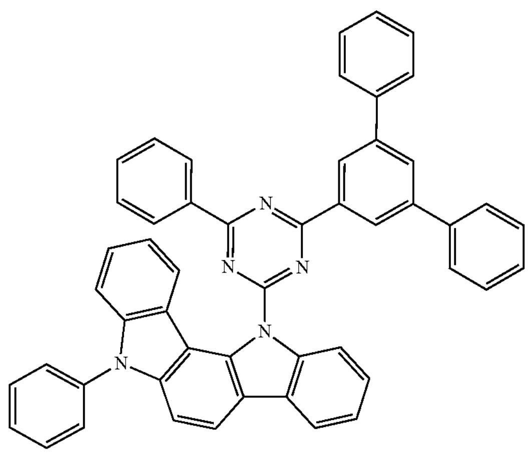
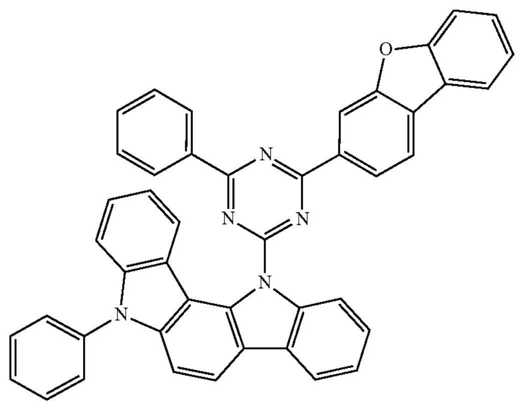
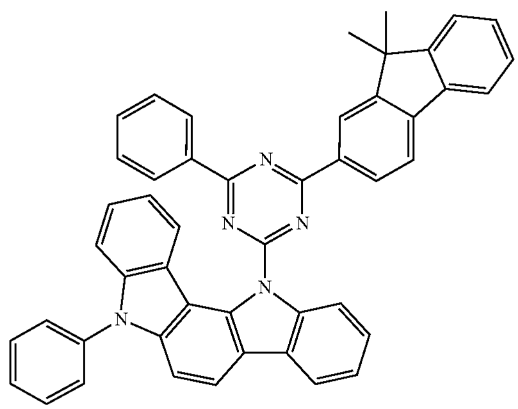
-continued
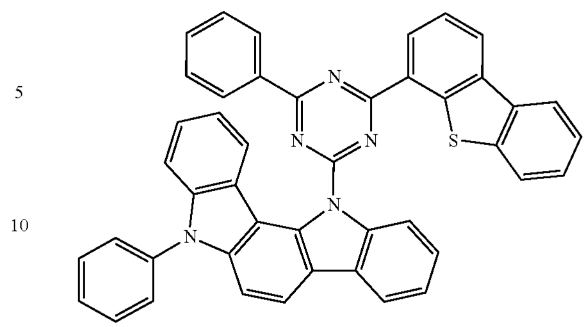
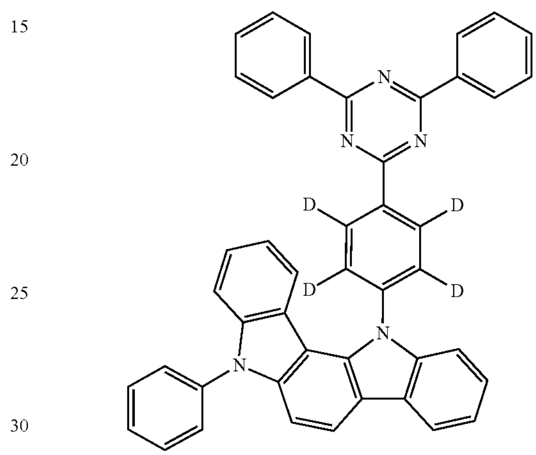
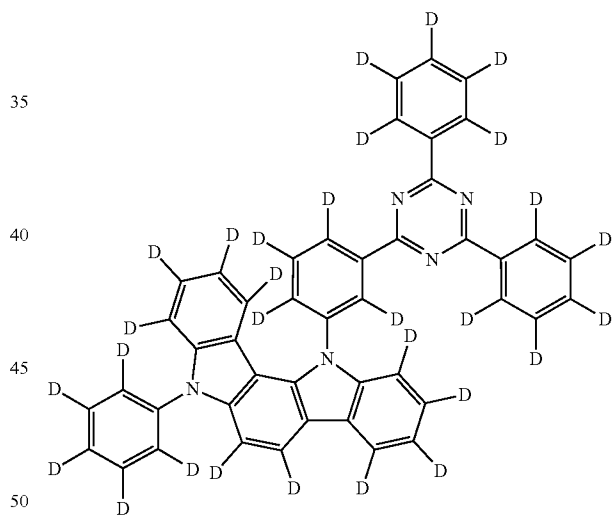
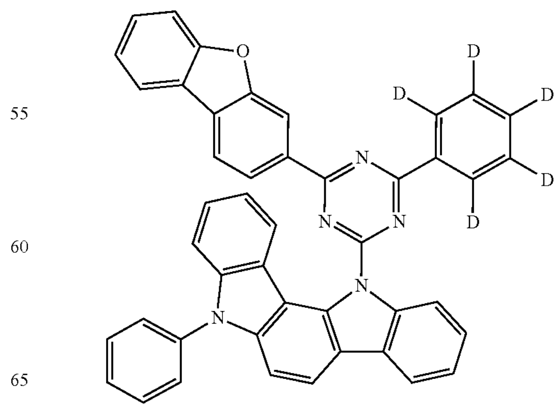

-continued
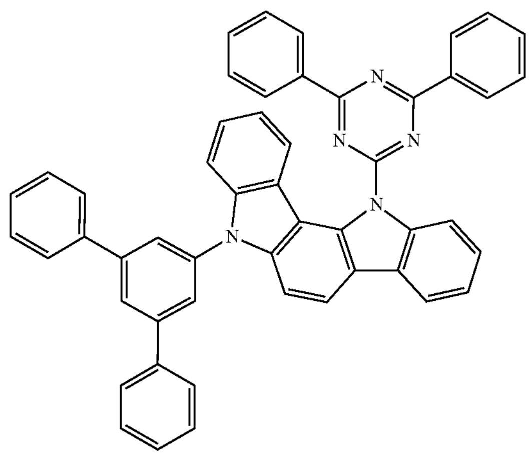
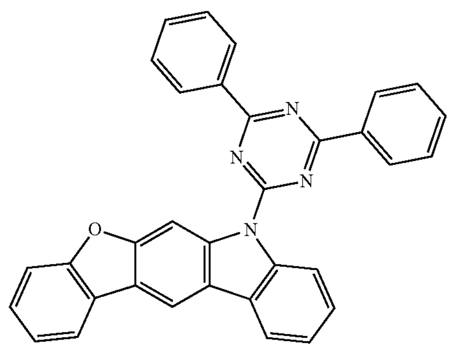
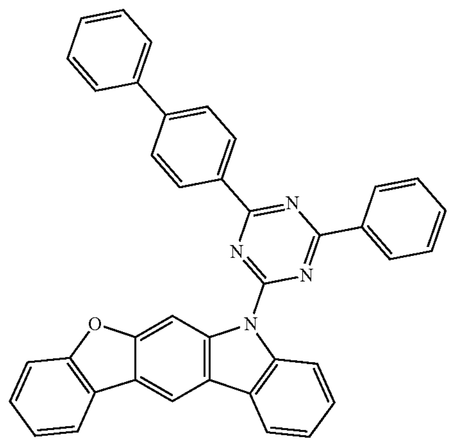
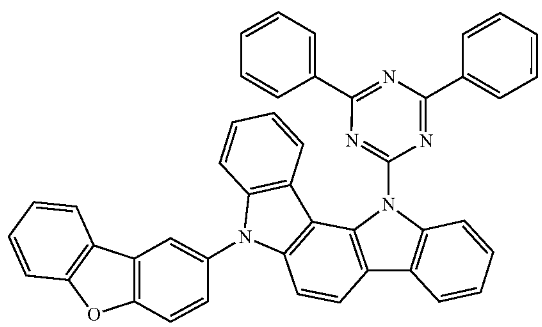
-continued
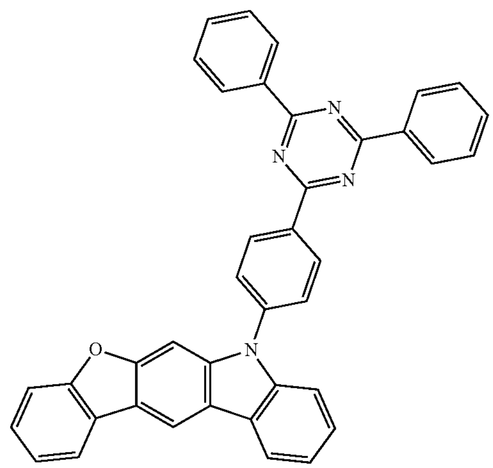
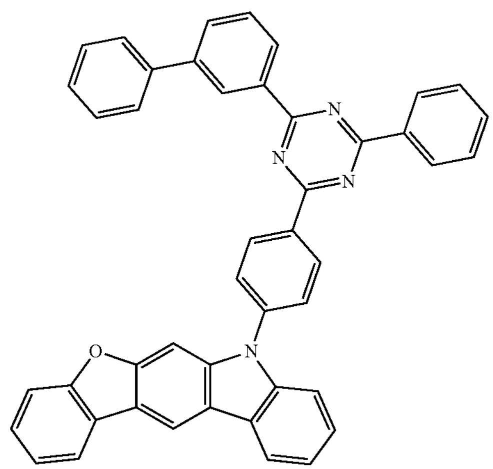
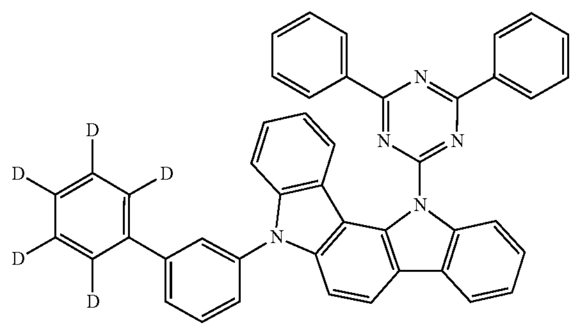
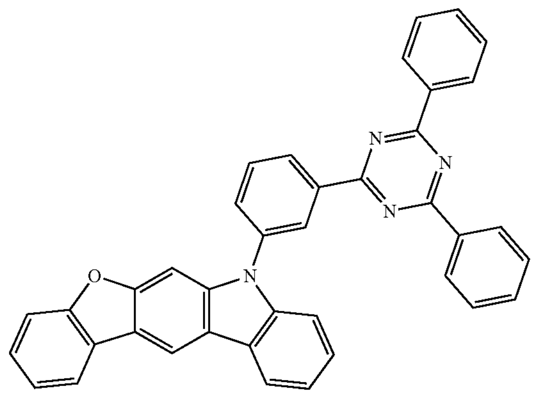

-continued
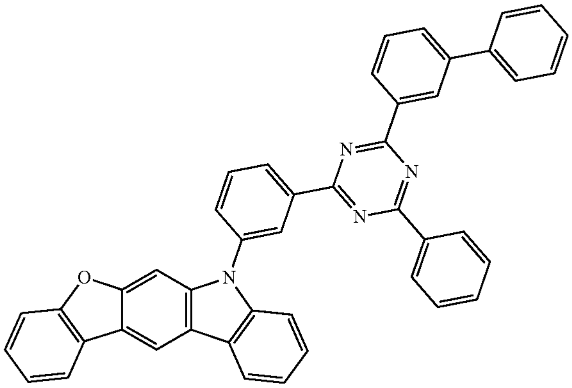
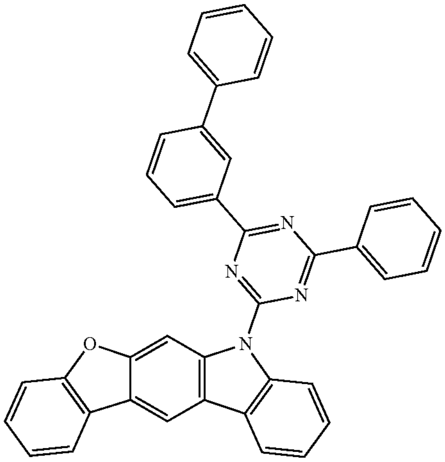
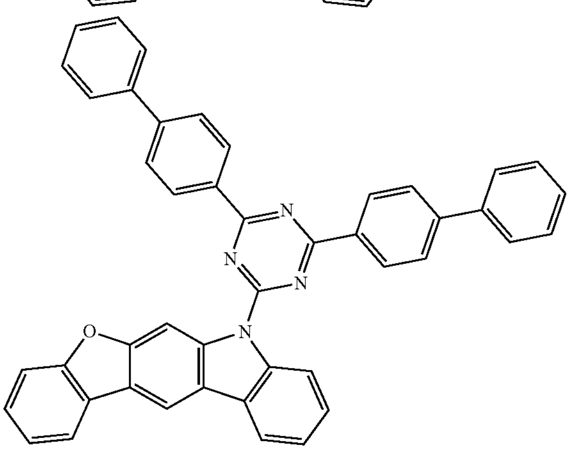
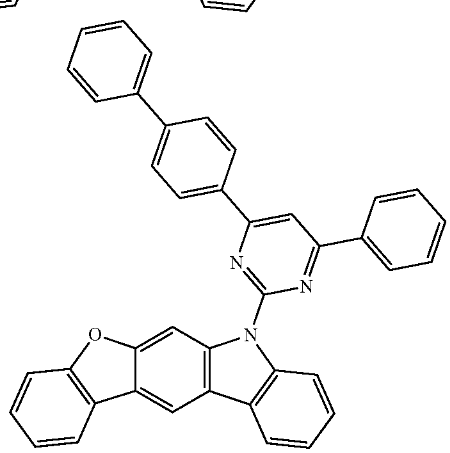
-continued
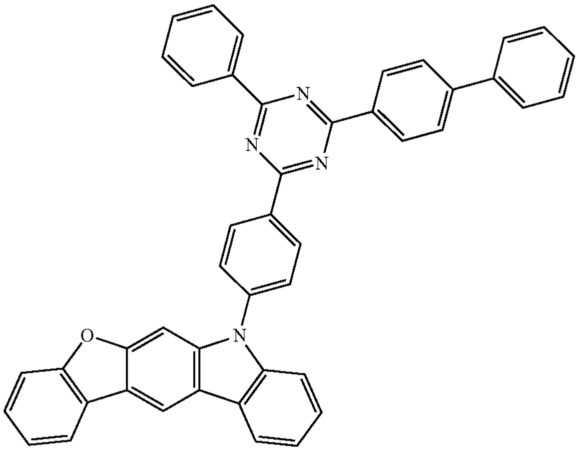
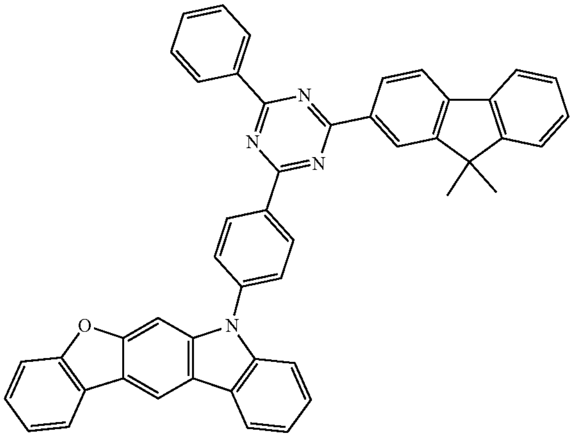
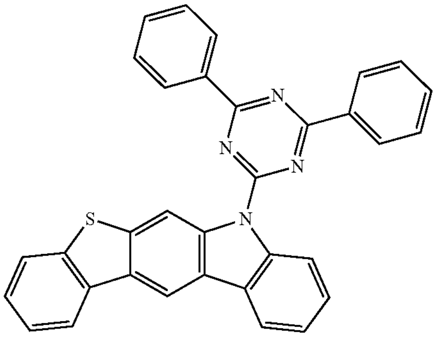

-continued
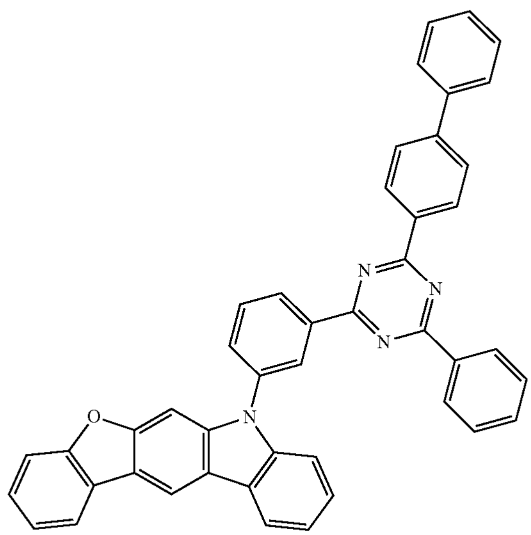
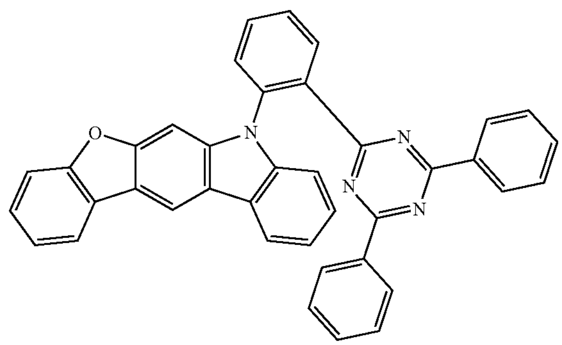
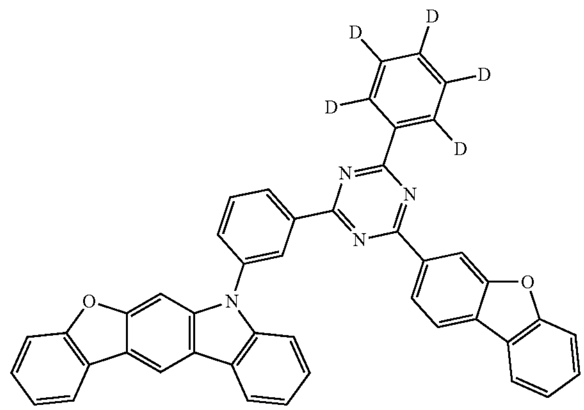
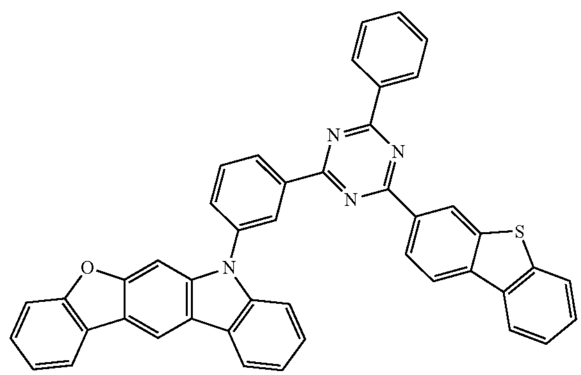
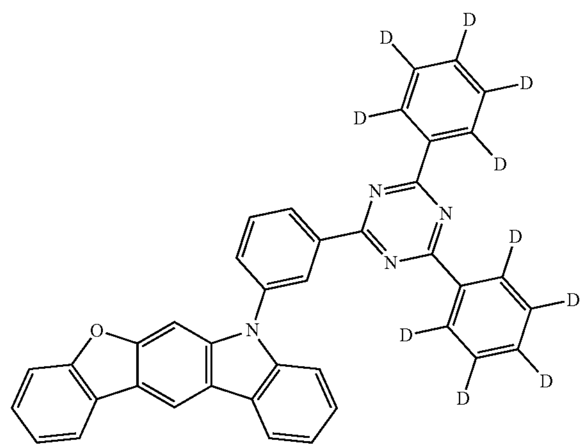
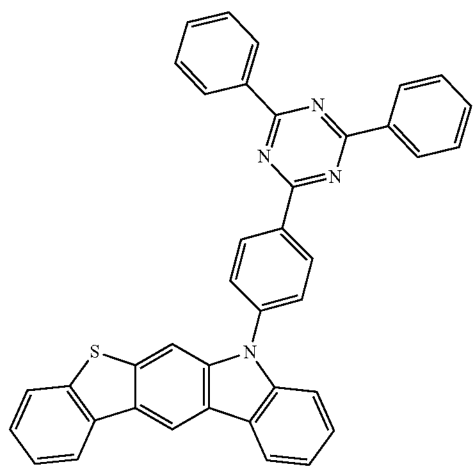
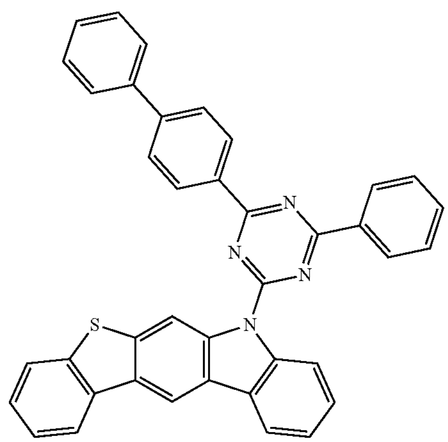

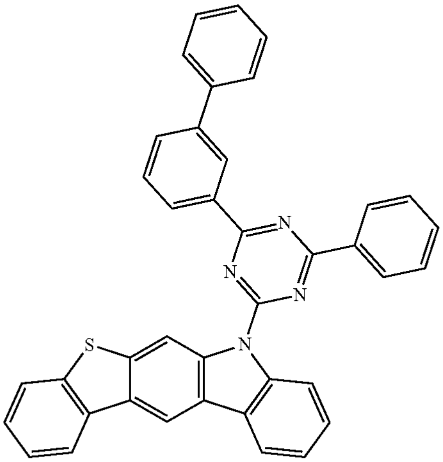
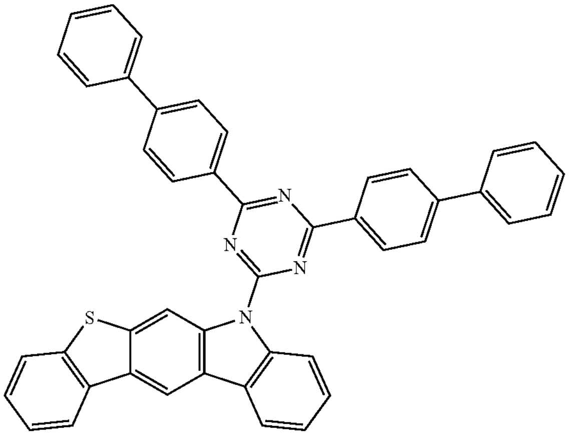
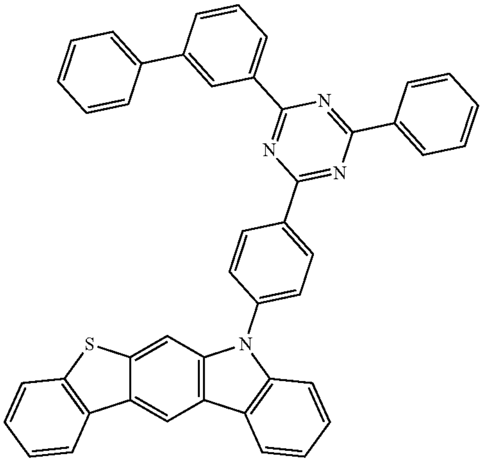
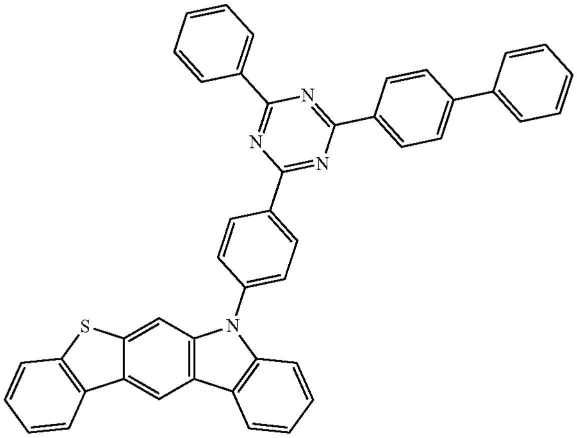
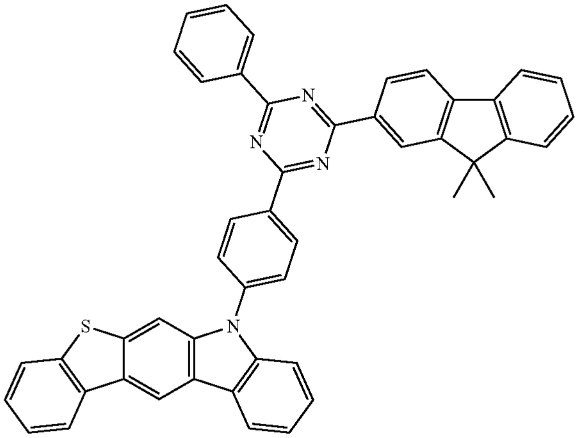
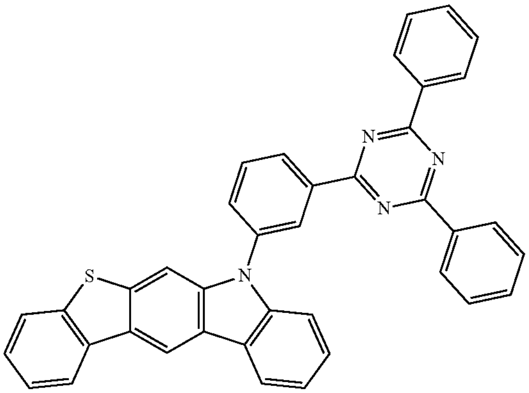
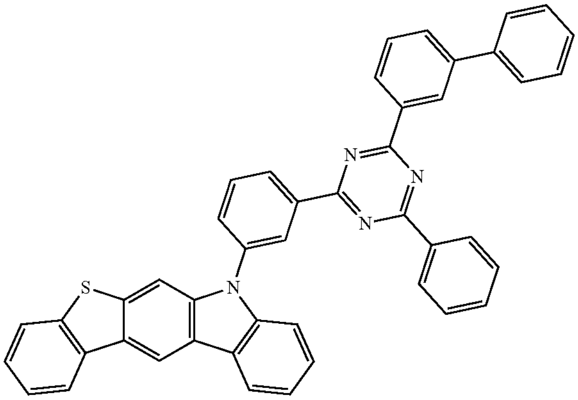

-continued
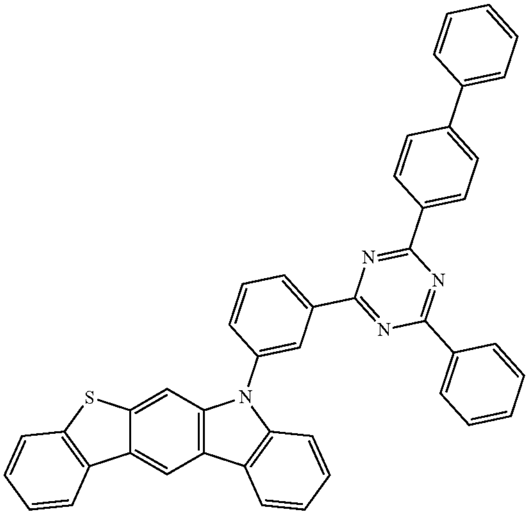
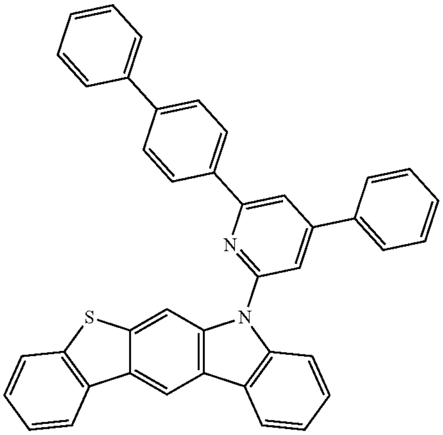
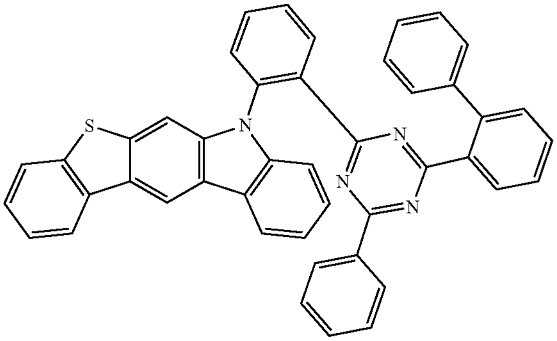
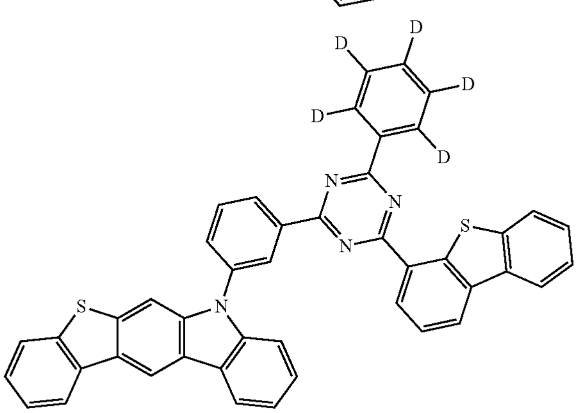
-continued
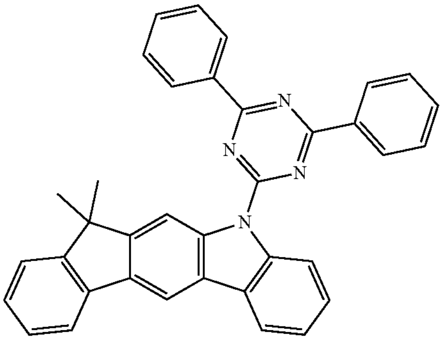
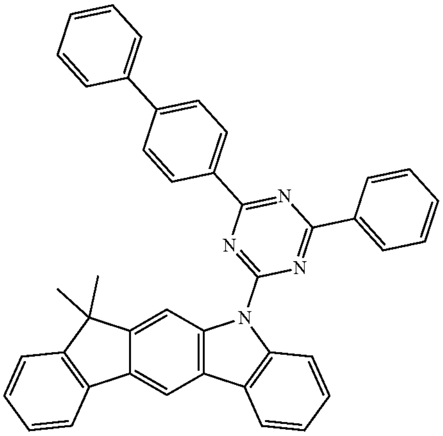
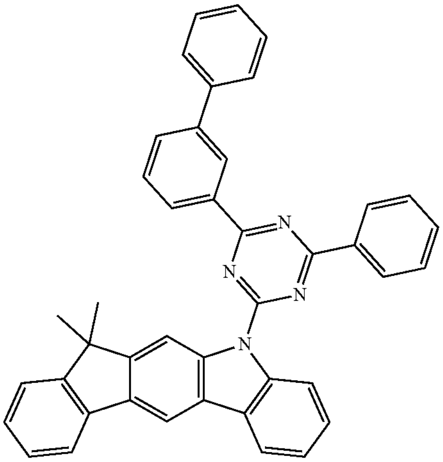
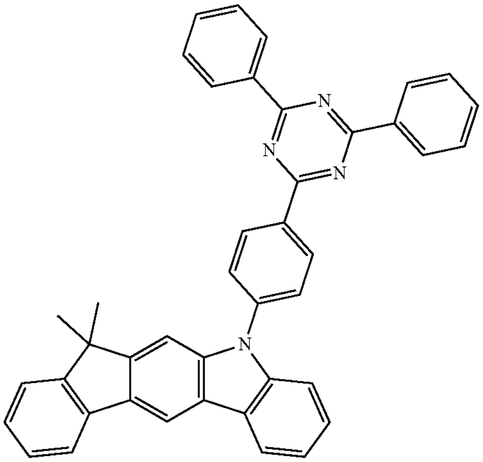

-continued
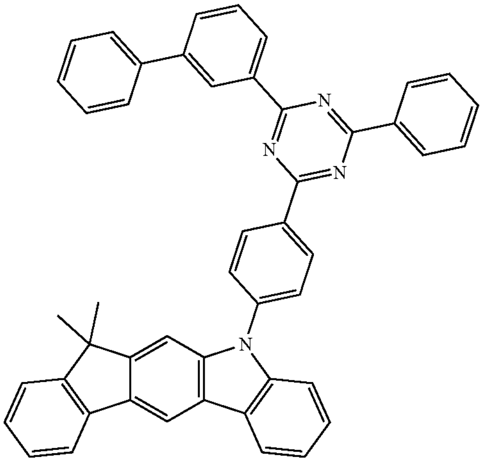
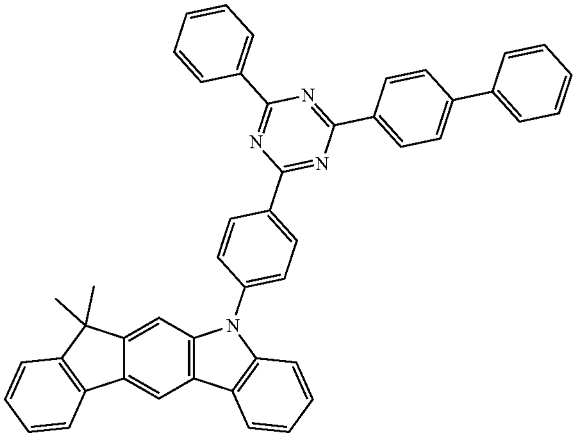
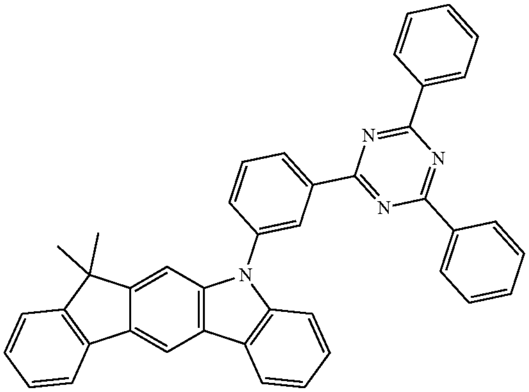
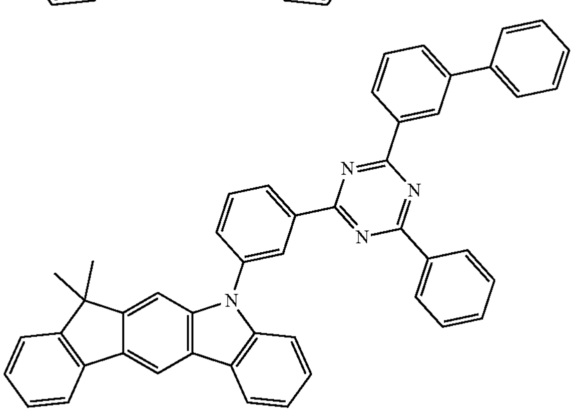
-continued
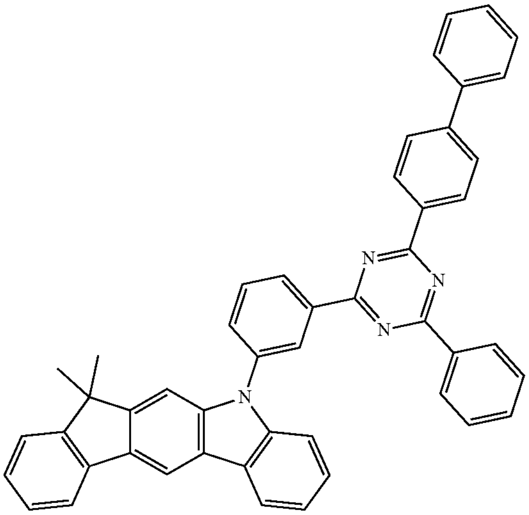
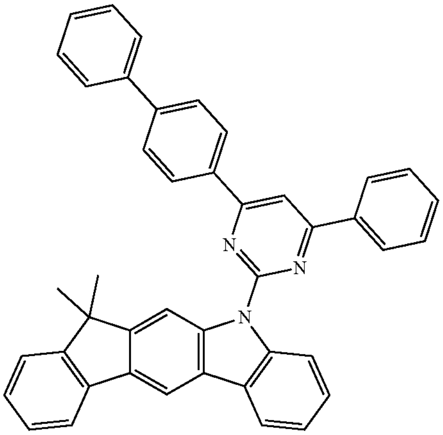
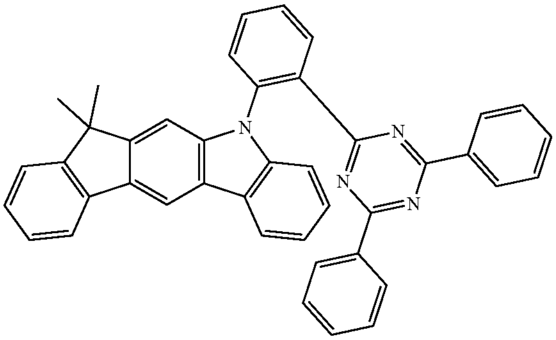
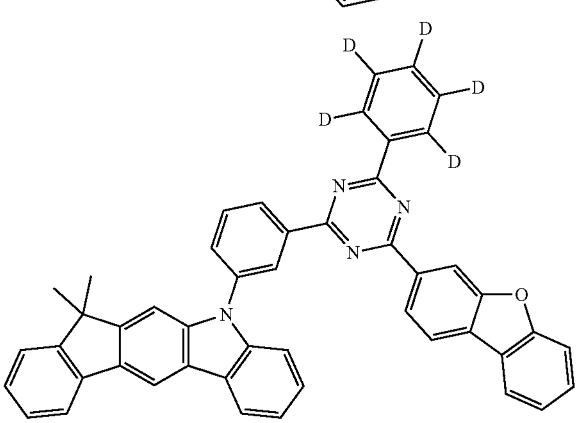

-continued
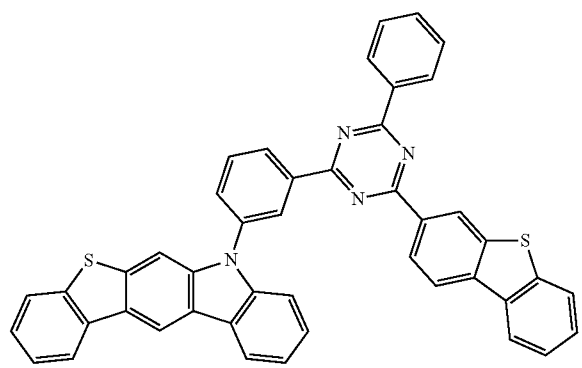
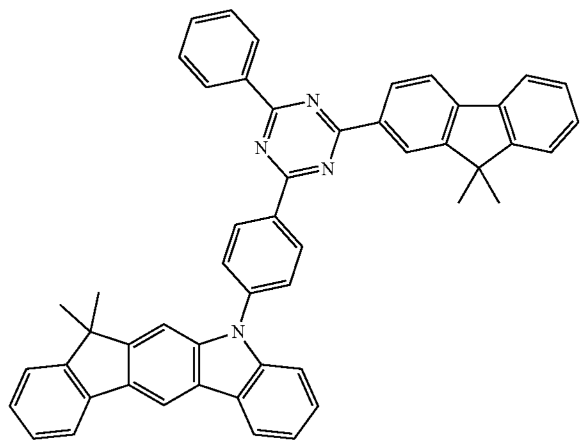
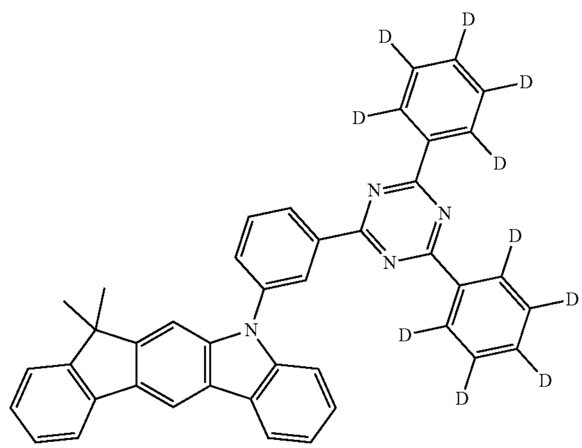
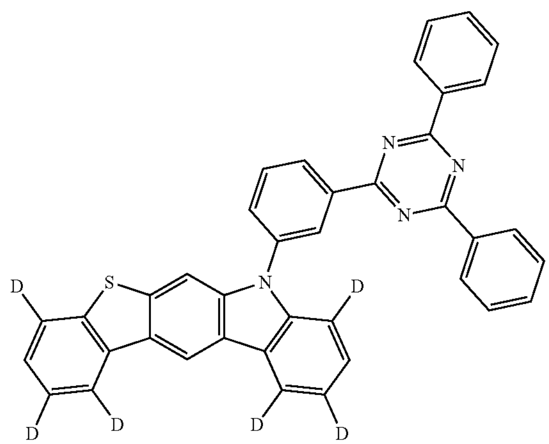
-continued
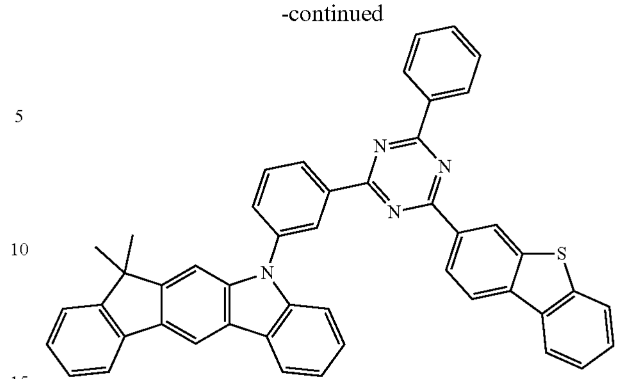
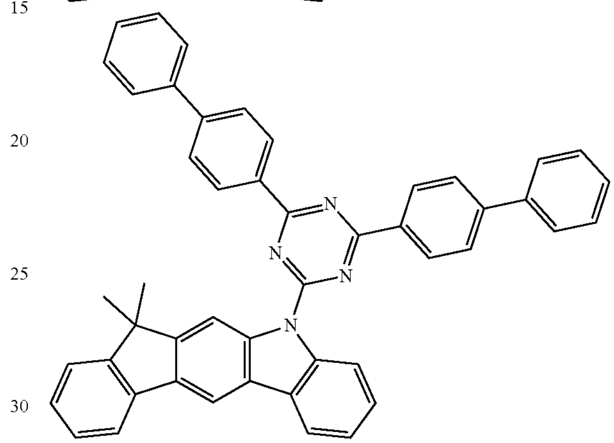
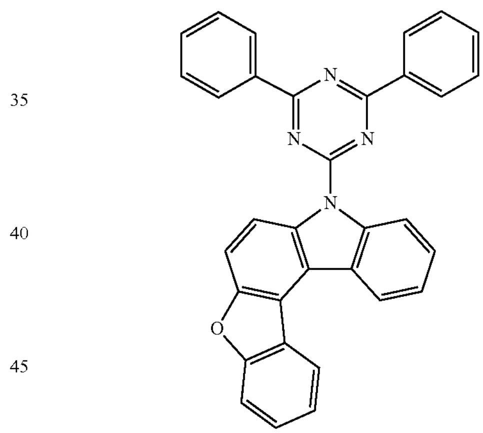
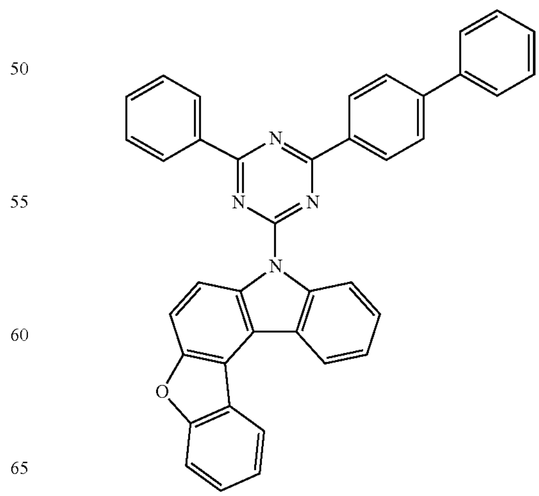

-continued
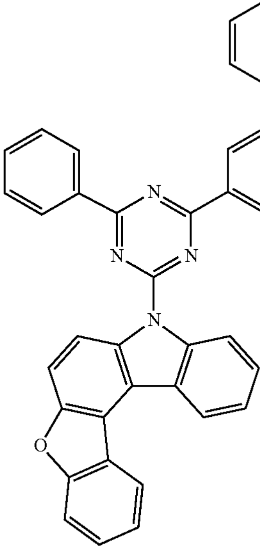
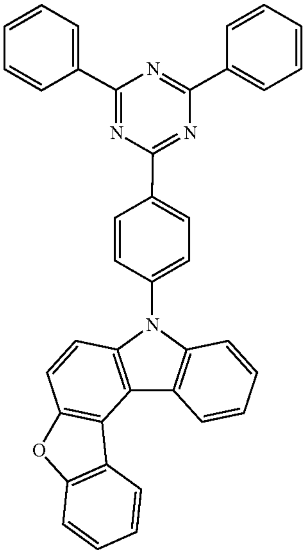
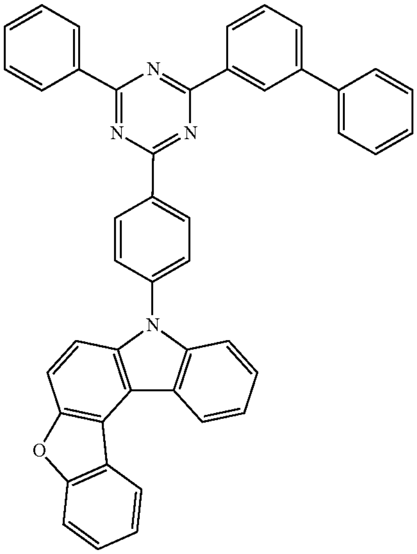
-continued
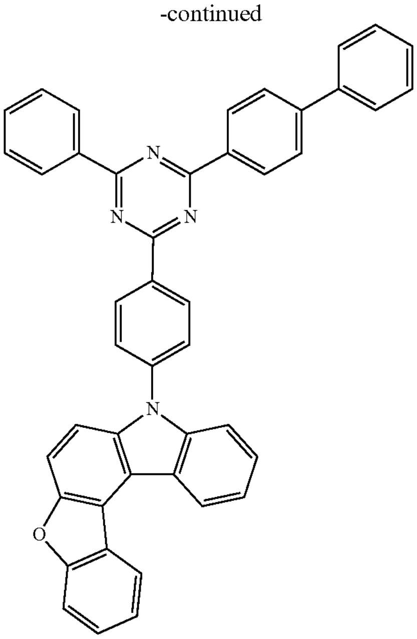
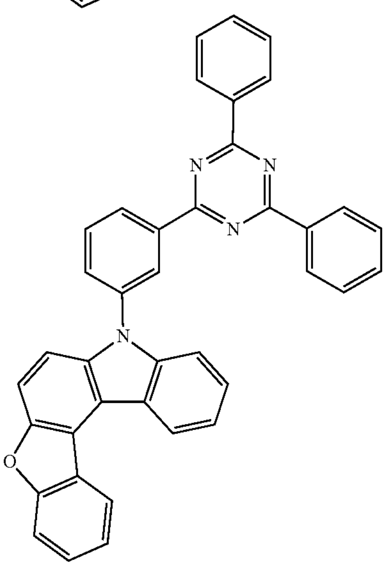
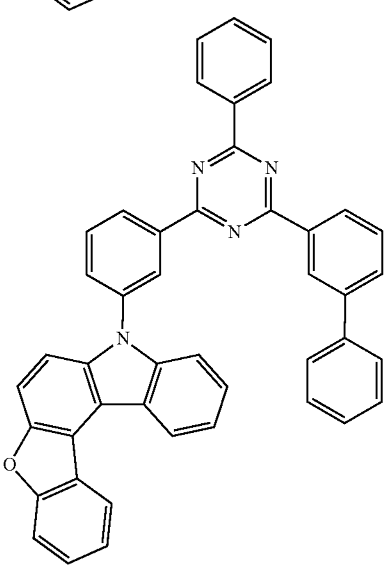

-continued
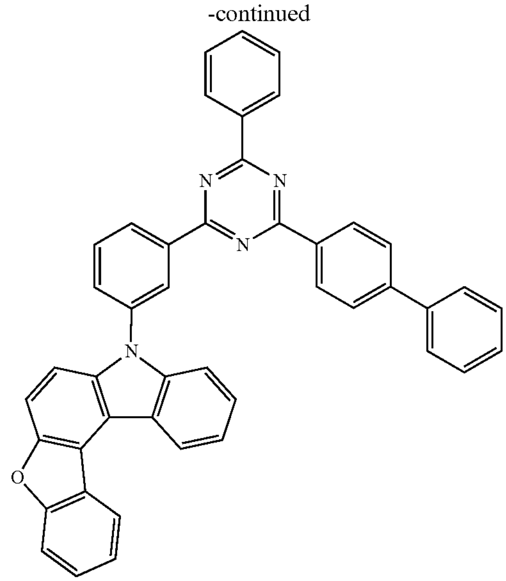
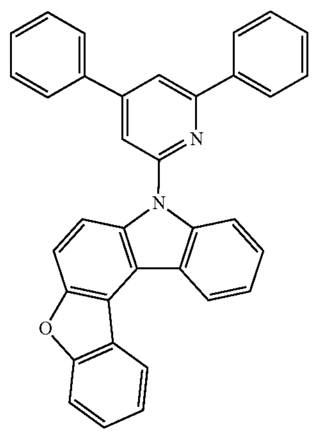
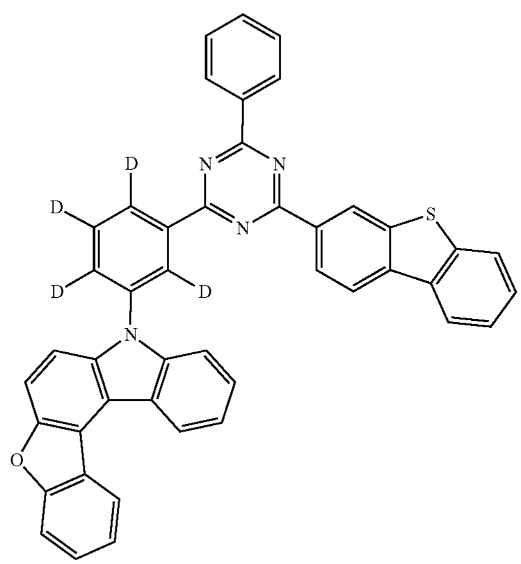
-continued
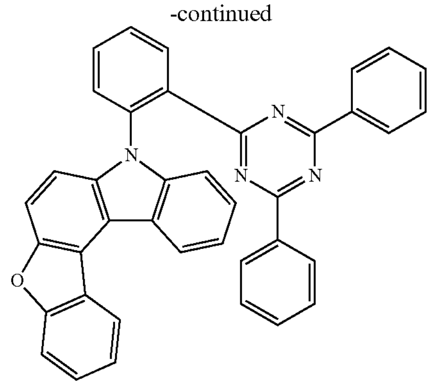
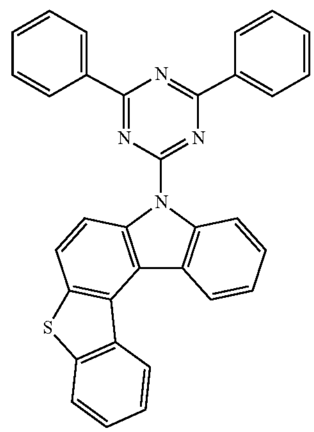
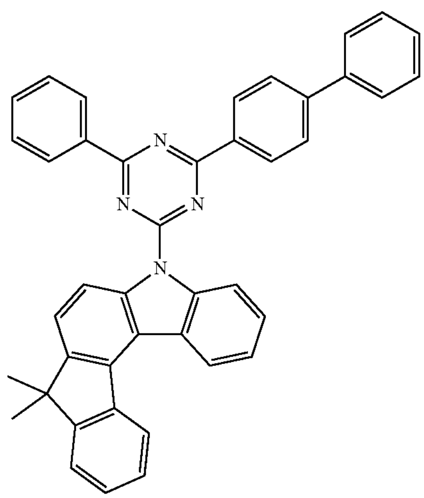

-continued
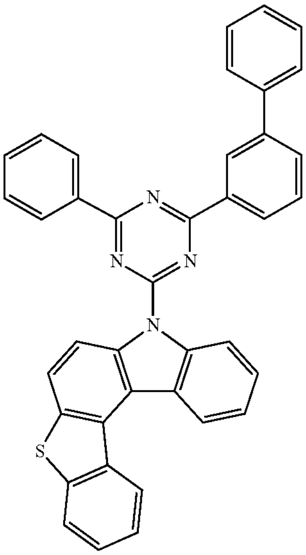
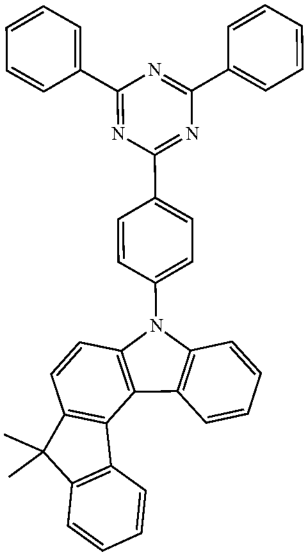
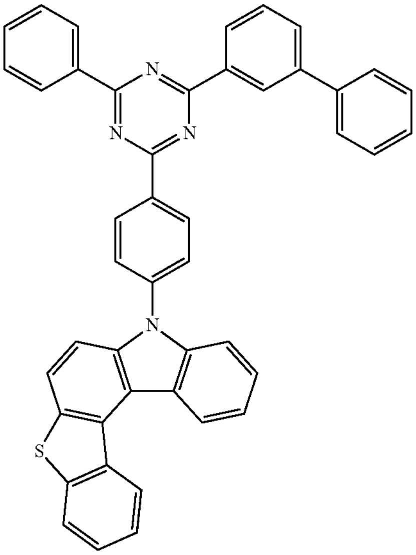
-continued
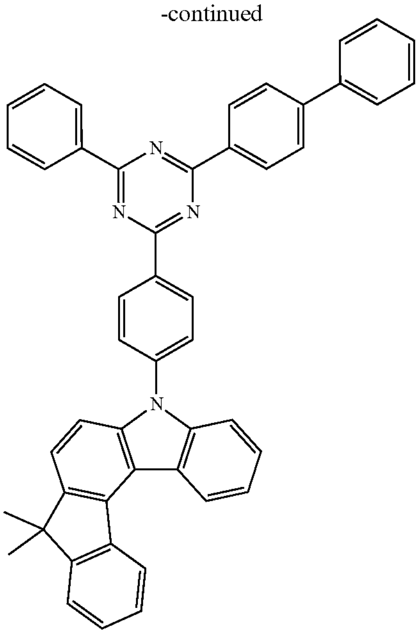
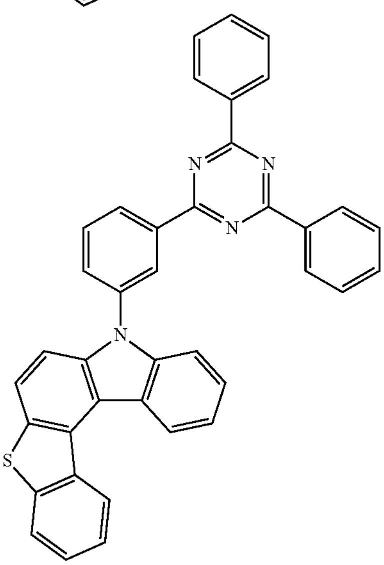
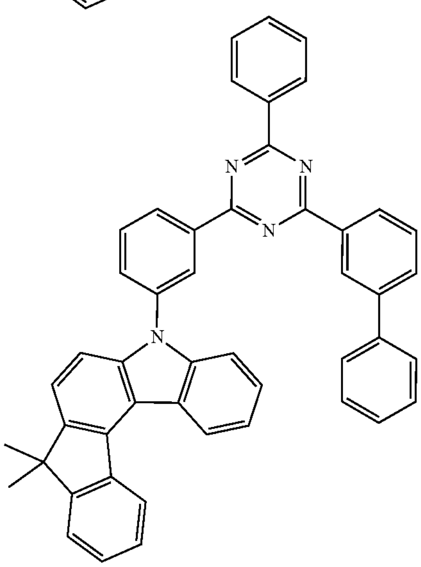

-continued
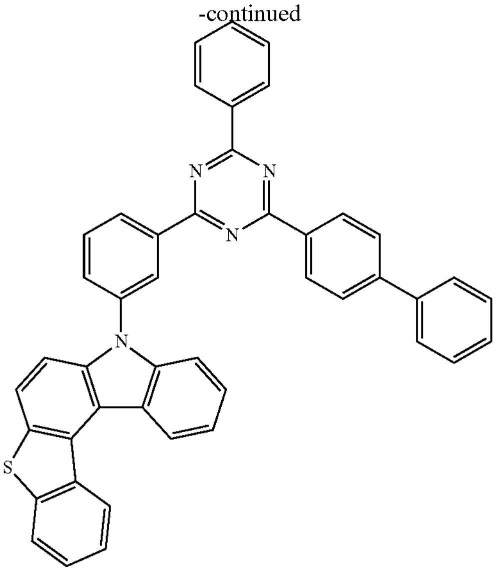
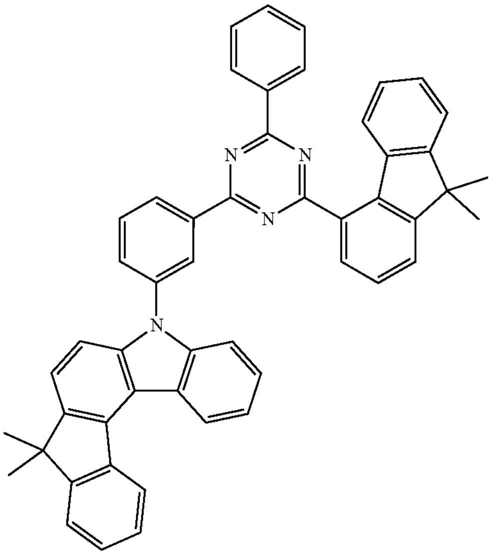
-continued
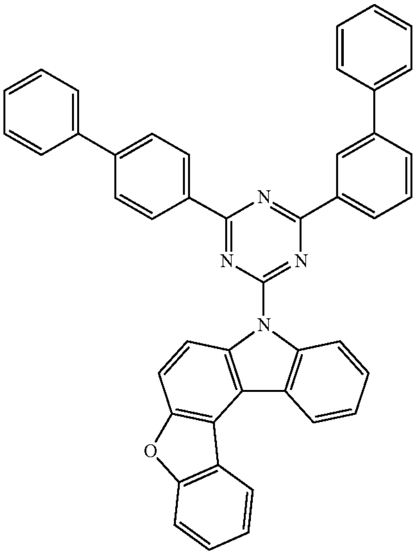
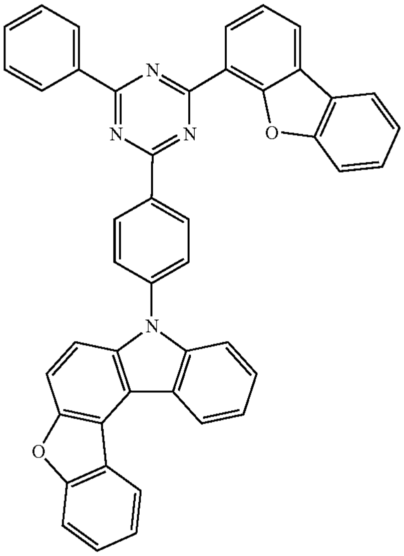
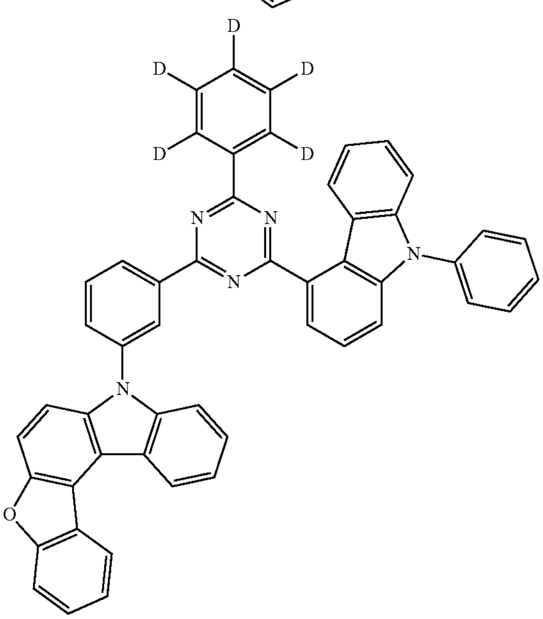
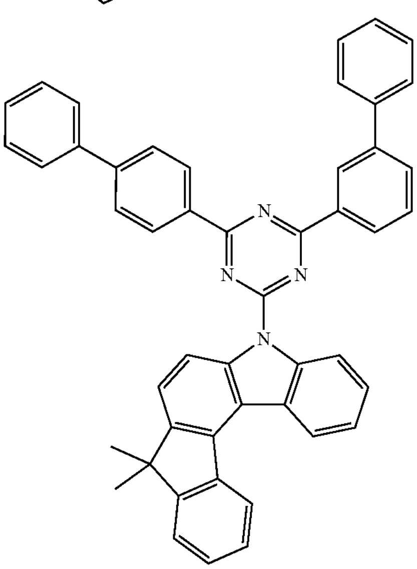

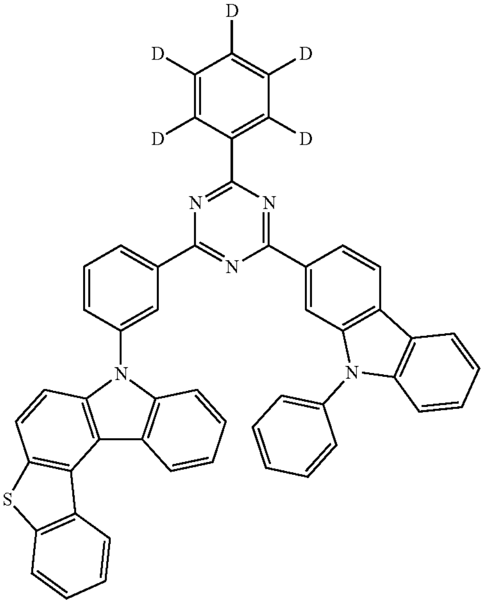
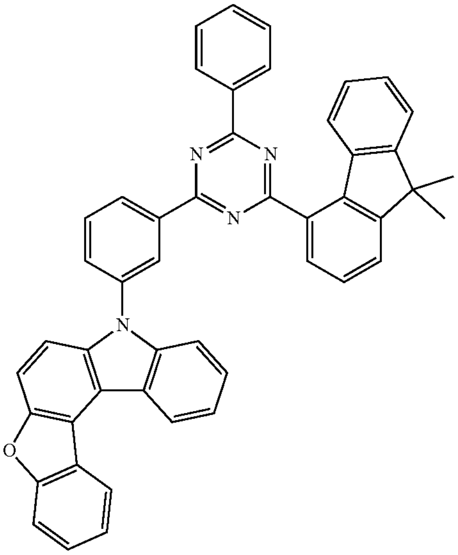
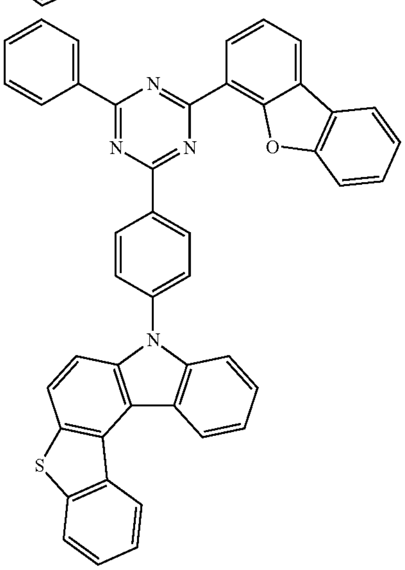
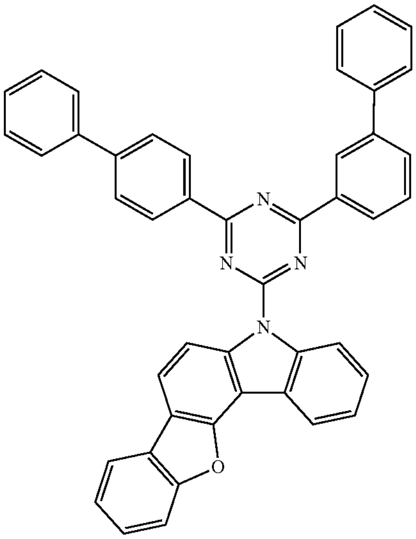
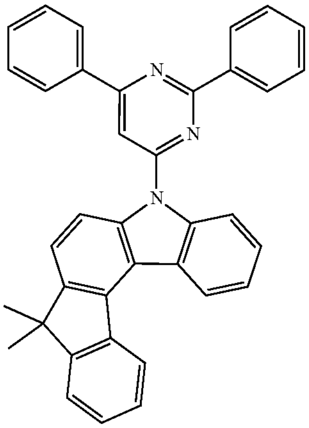
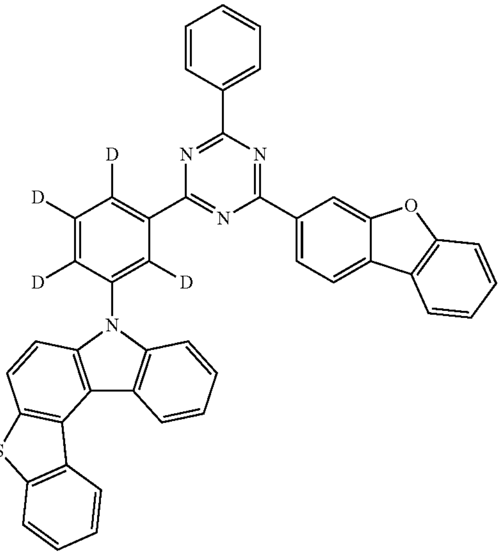

-continued
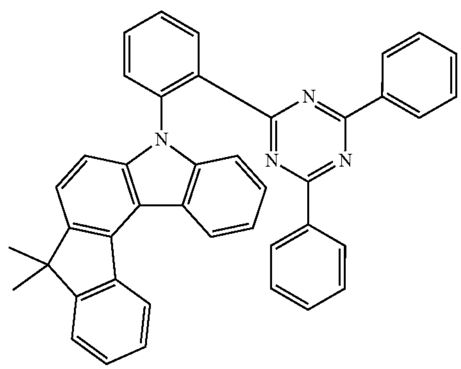
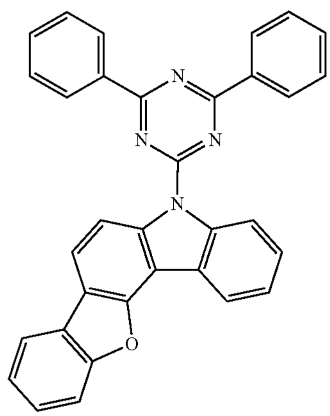
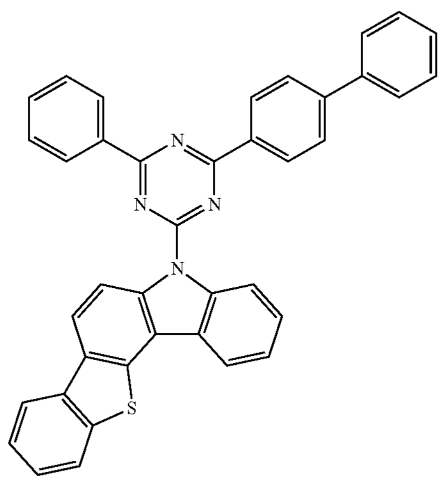
-continued
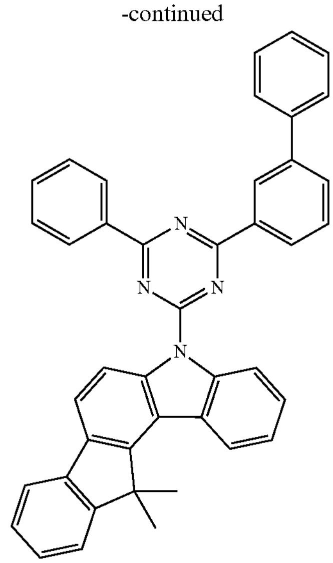
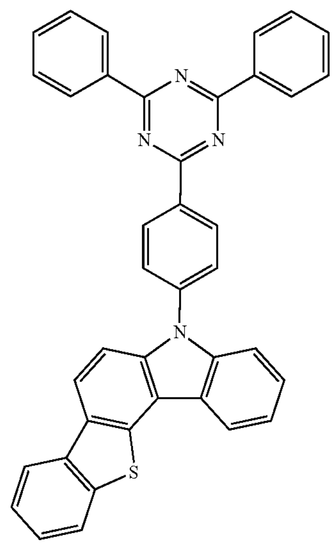
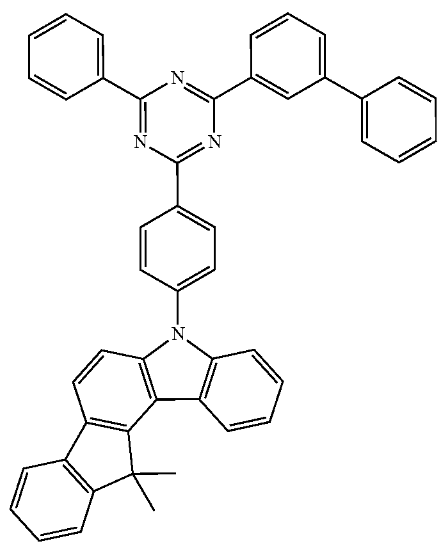

-continued
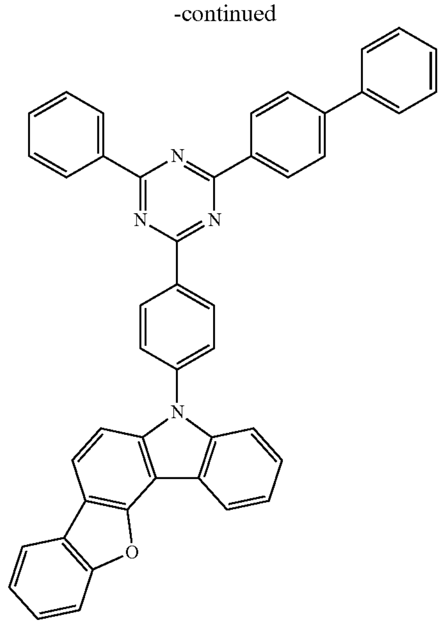
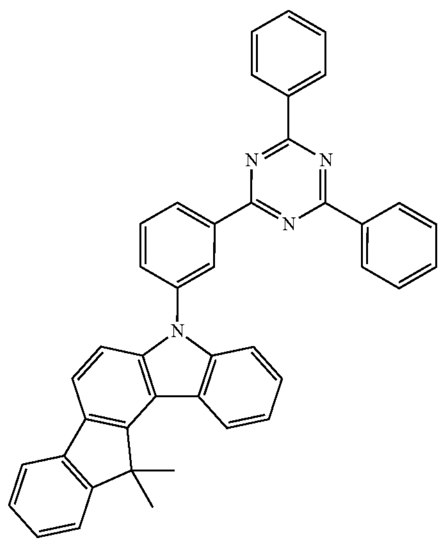
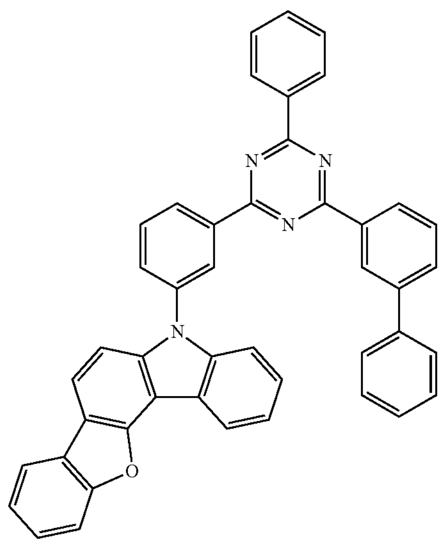
-continued
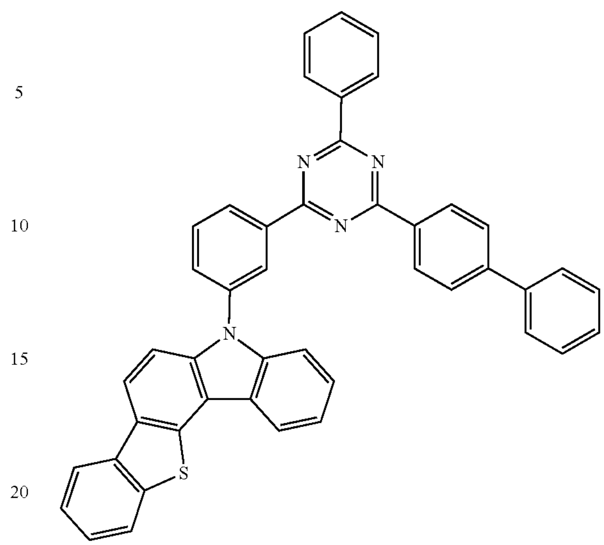
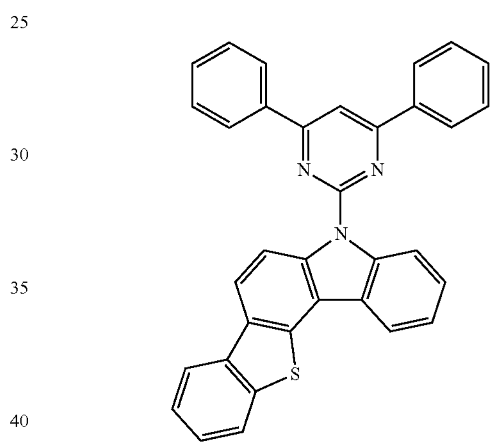
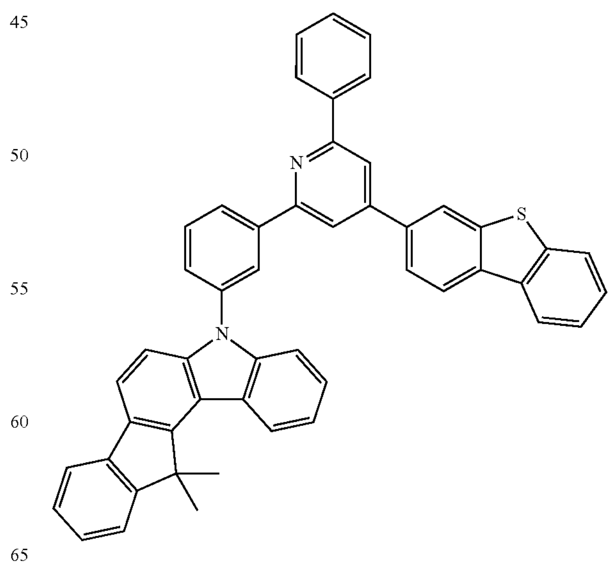

-continued
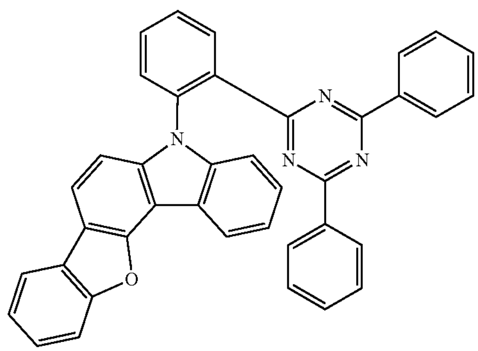
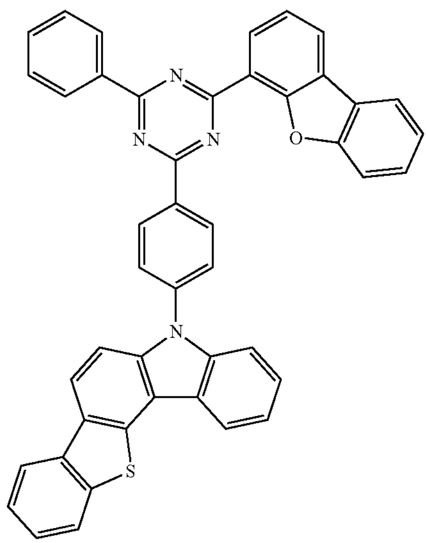
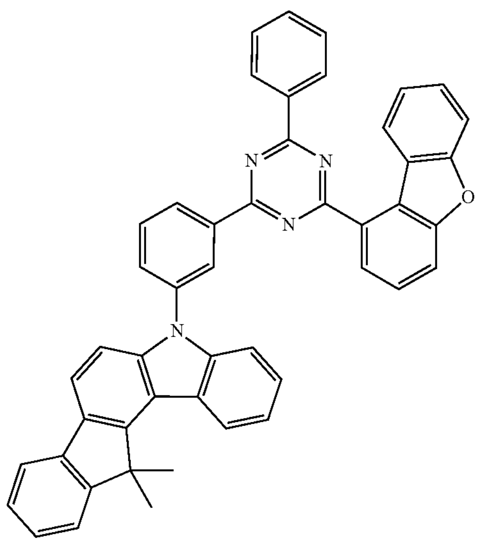
-continued
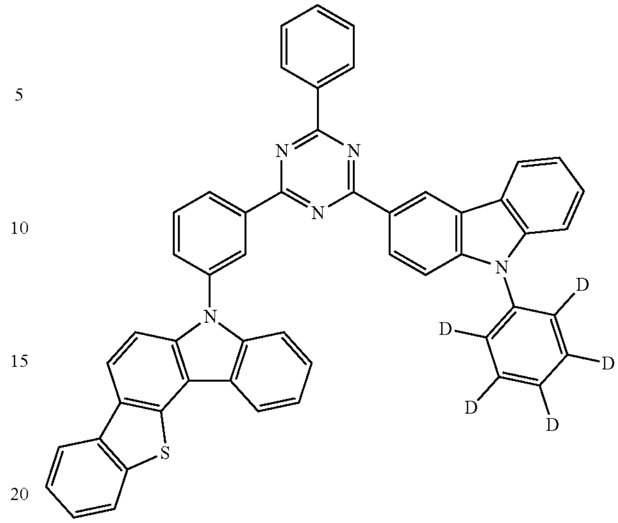
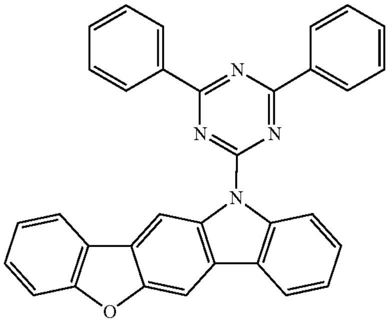
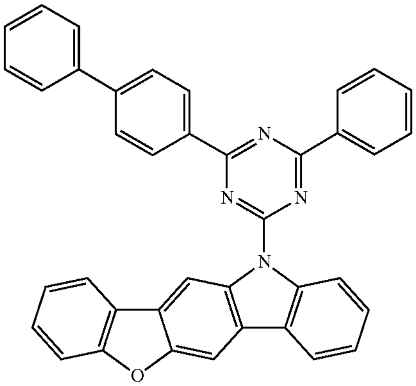
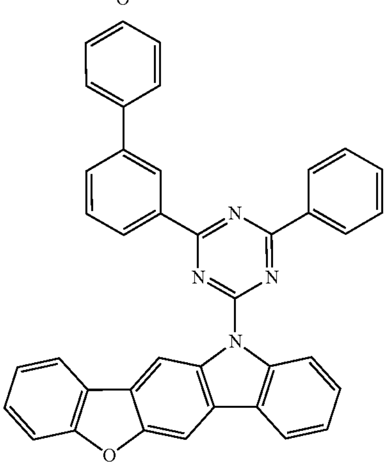

-continued
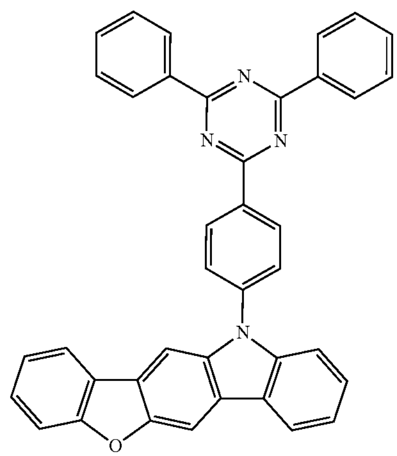
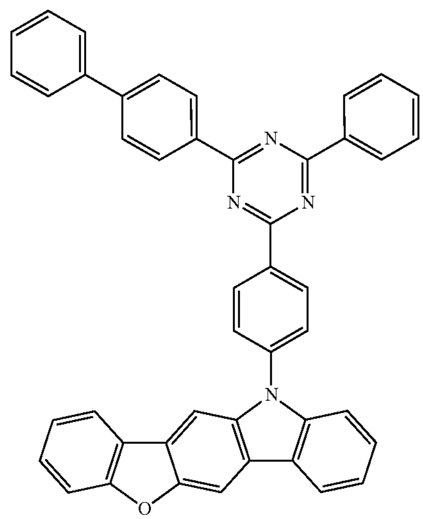
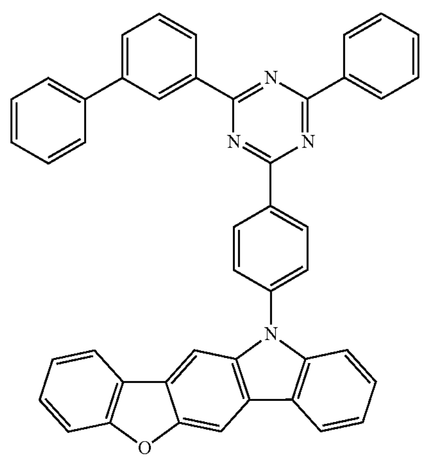
-continued
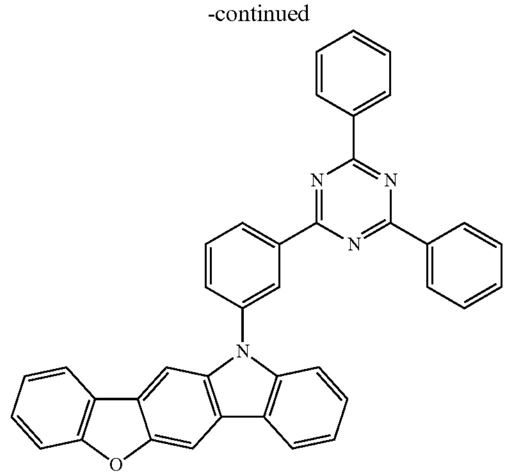
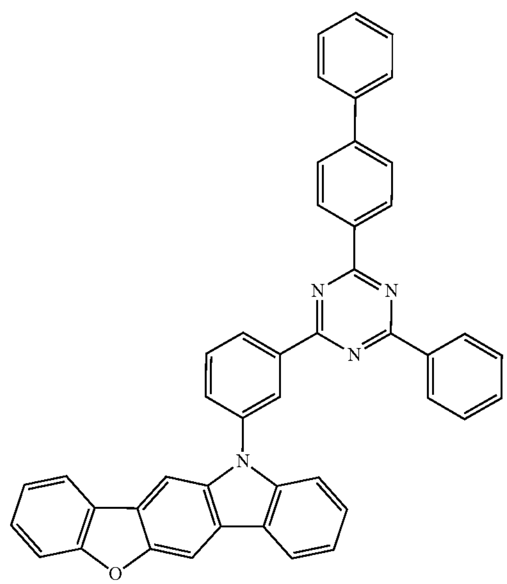
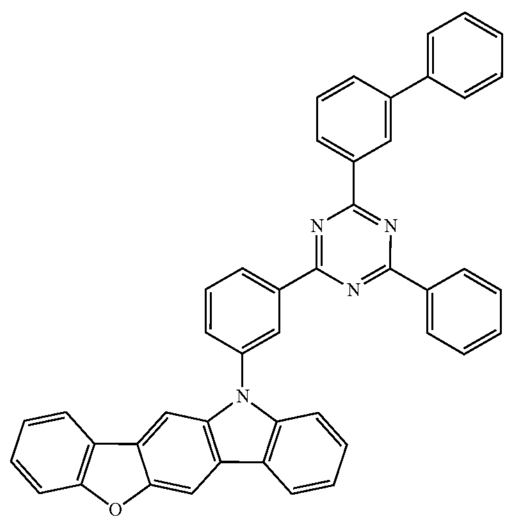

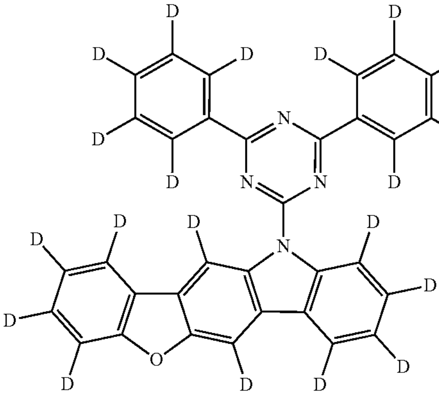
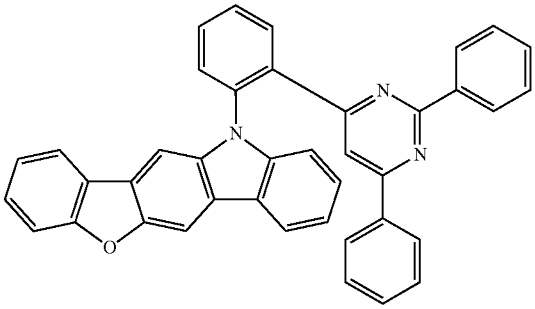
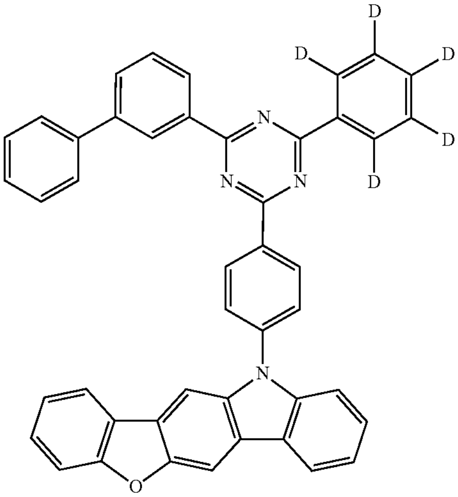
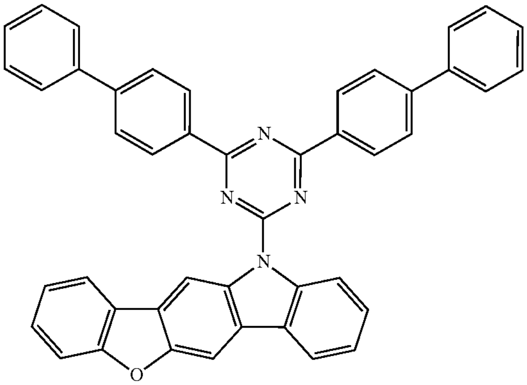
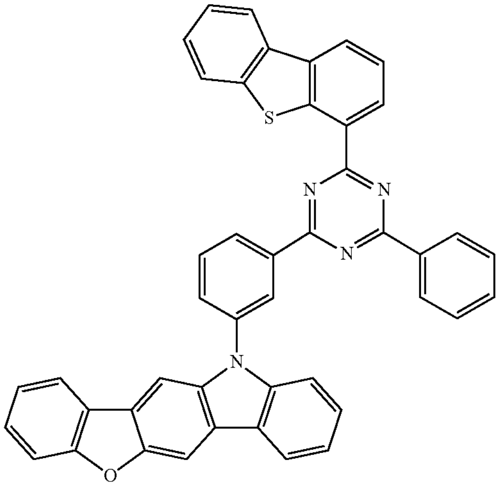
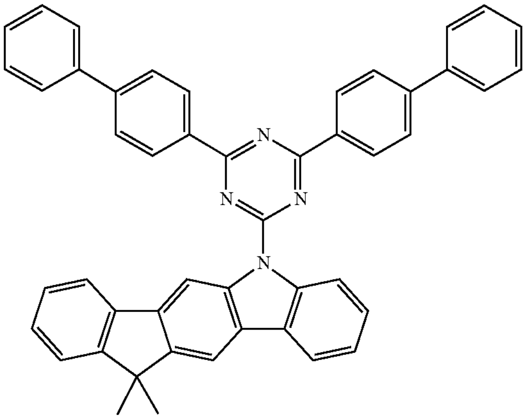
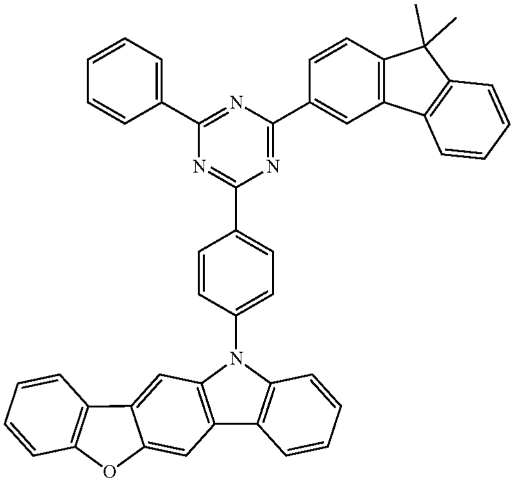

-continued
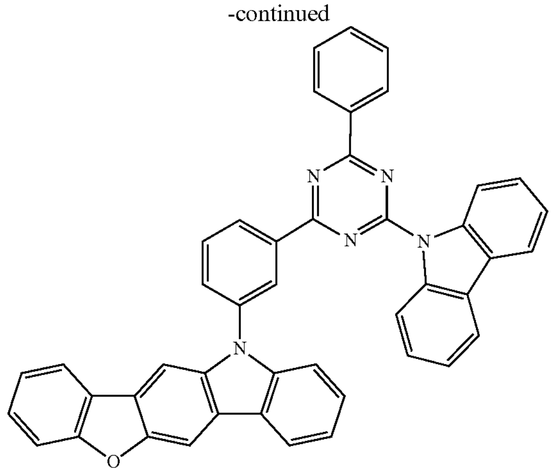
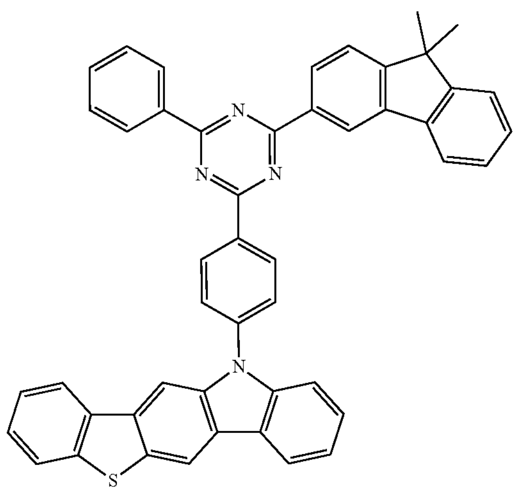
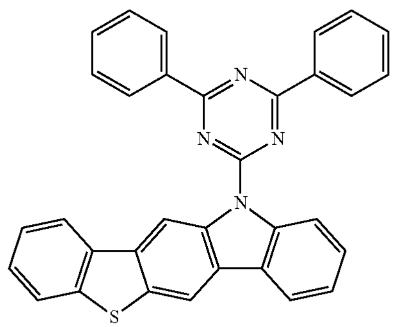
-continued
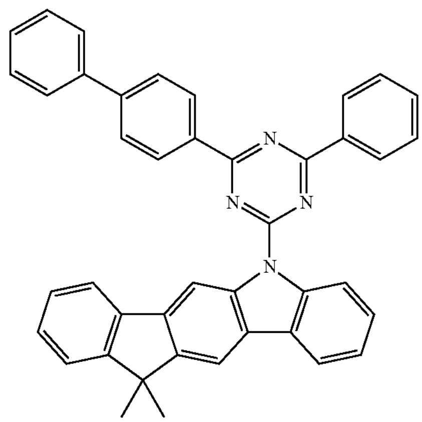
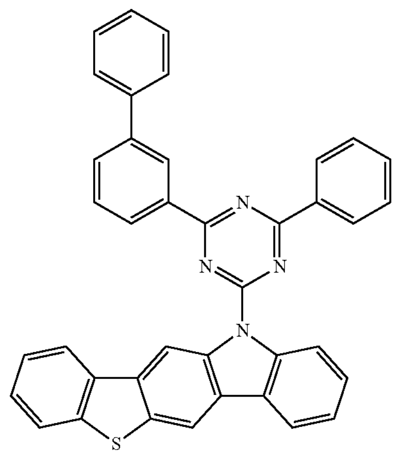
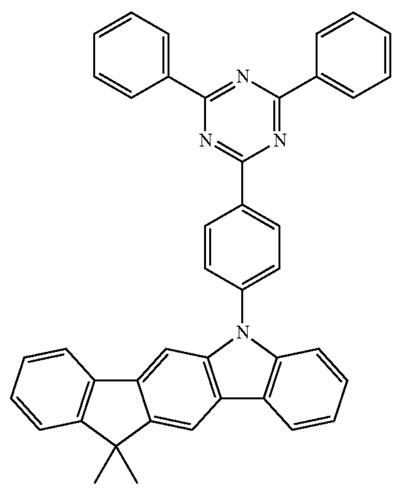

-continued
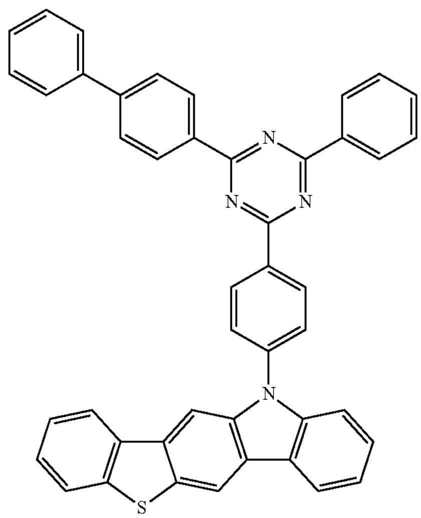
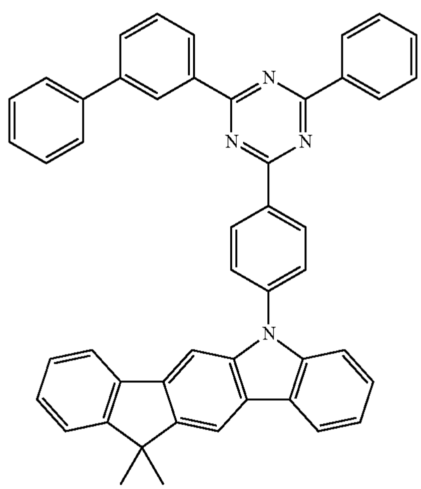
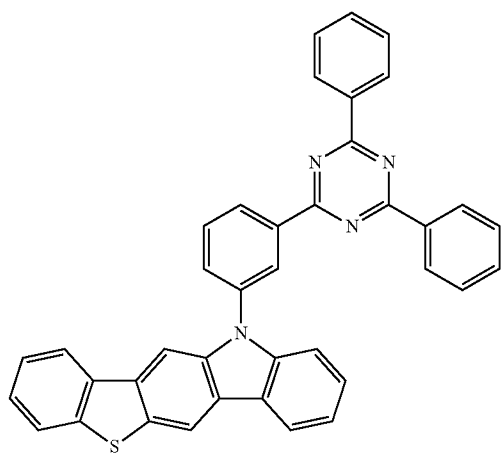
-continued
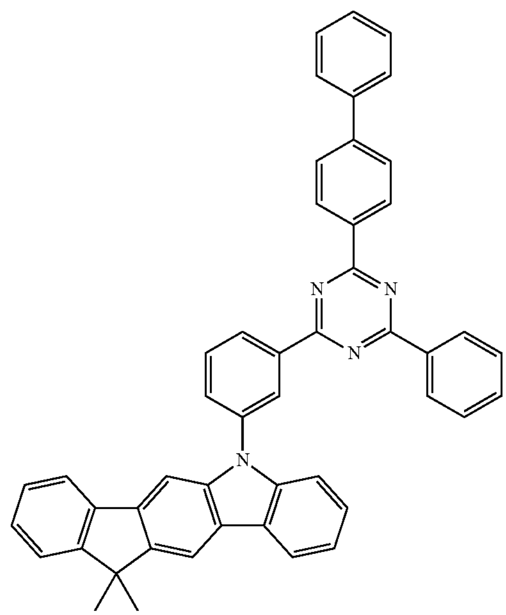
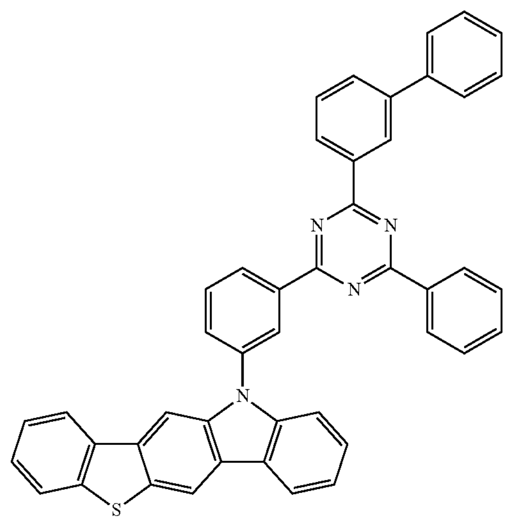
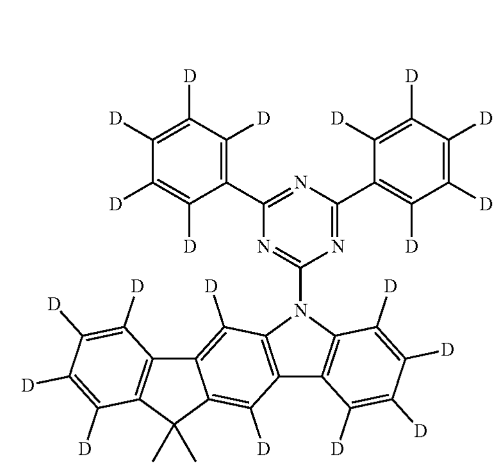

-continued
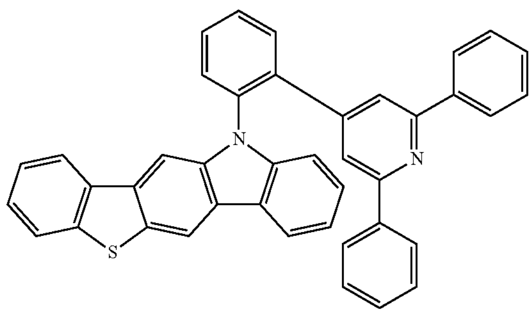
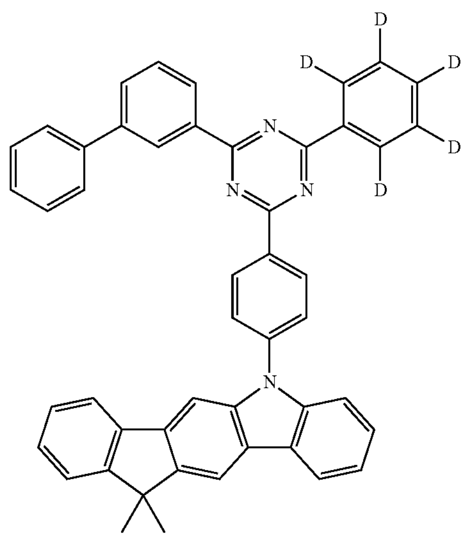
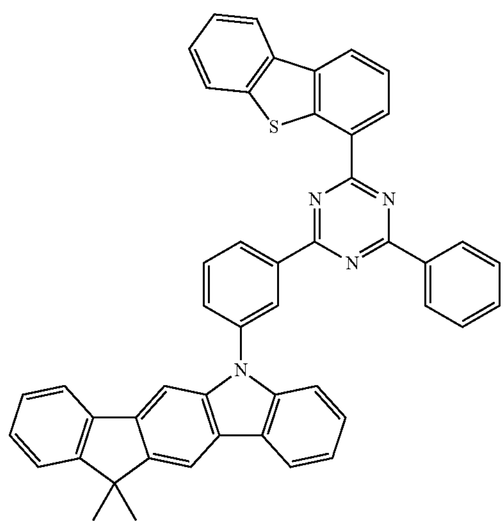
-continued
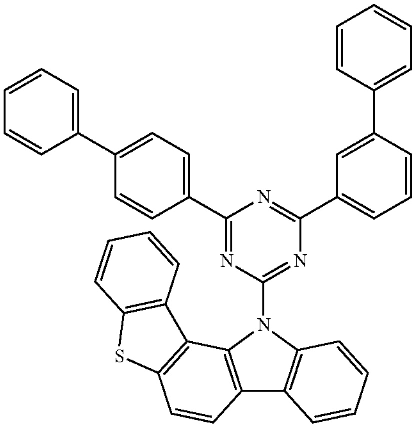
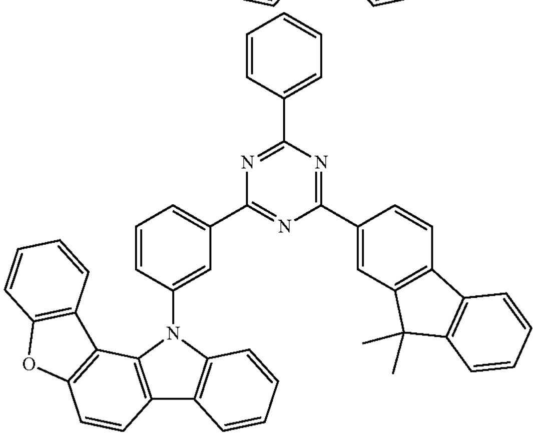
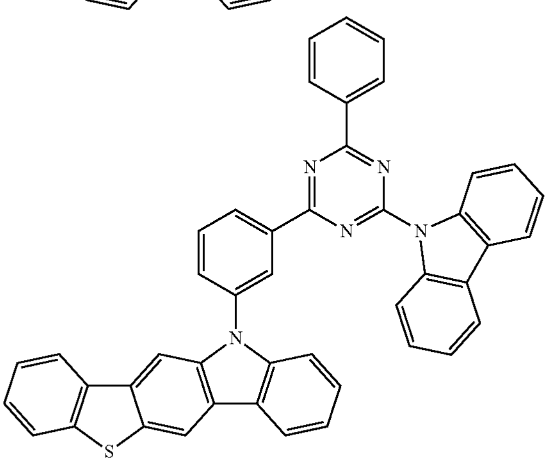
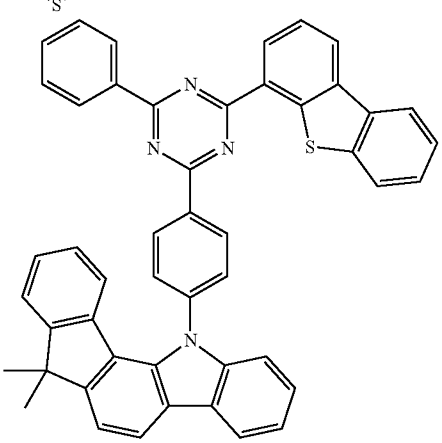

-continued
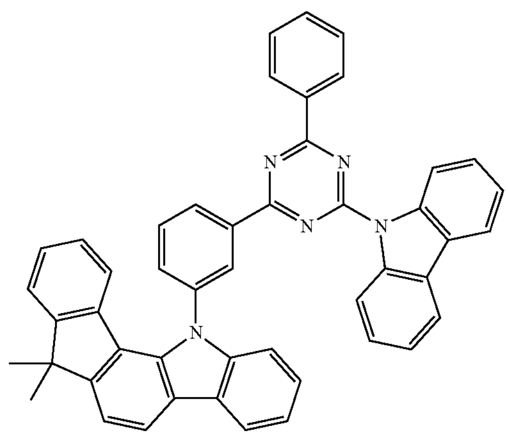
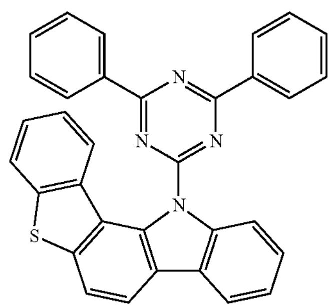
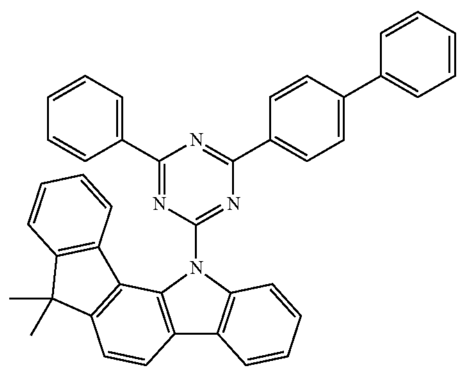
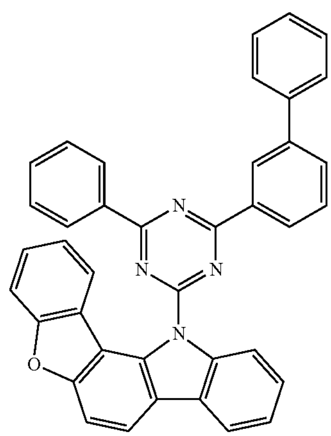
-continued
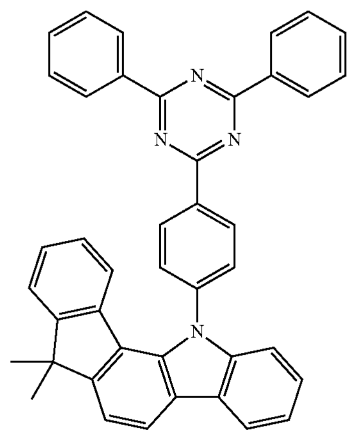
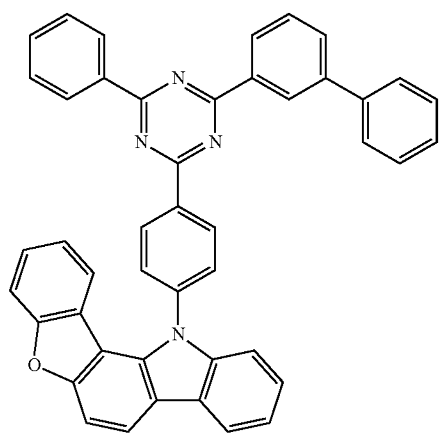
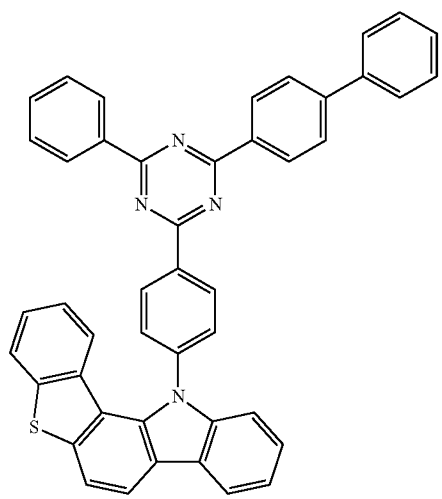

-continued
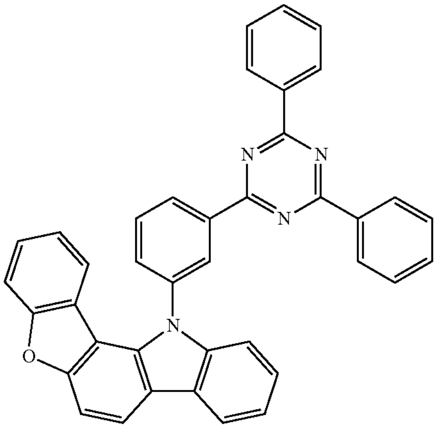
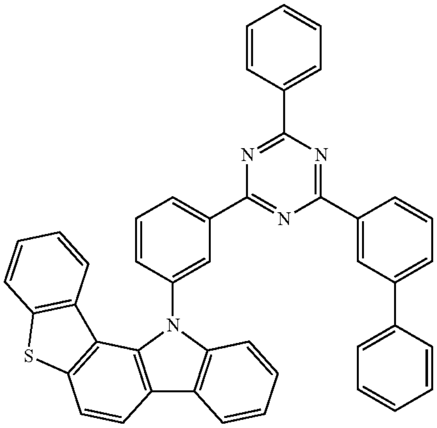
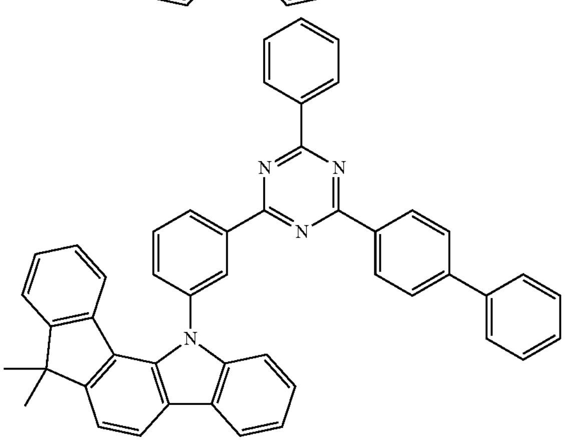
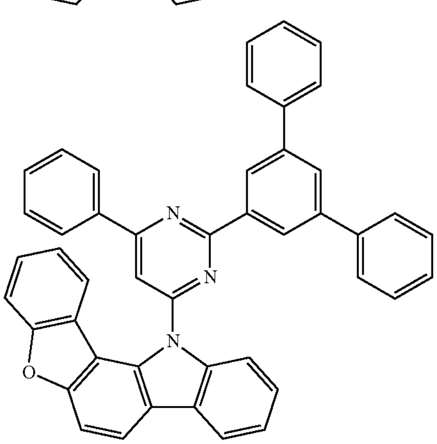
-continued
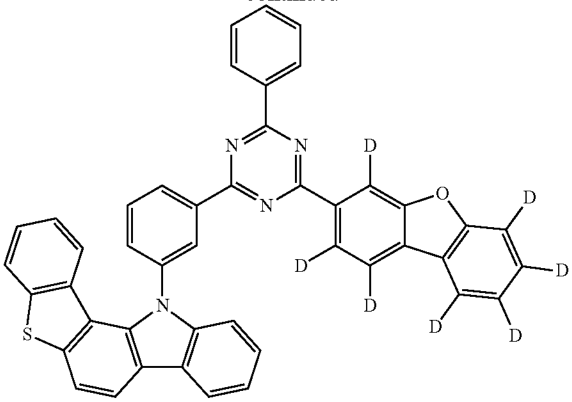
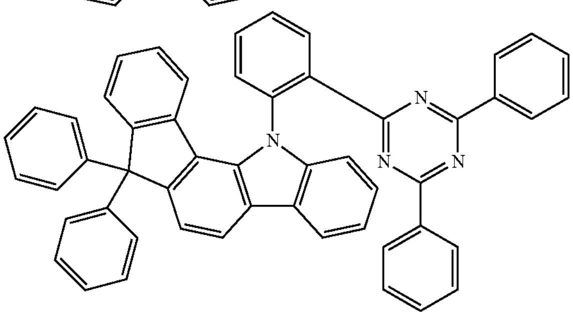
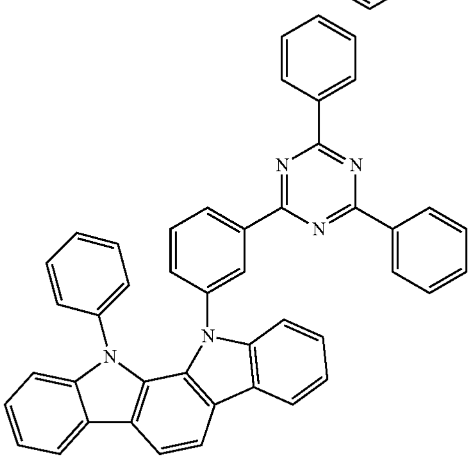
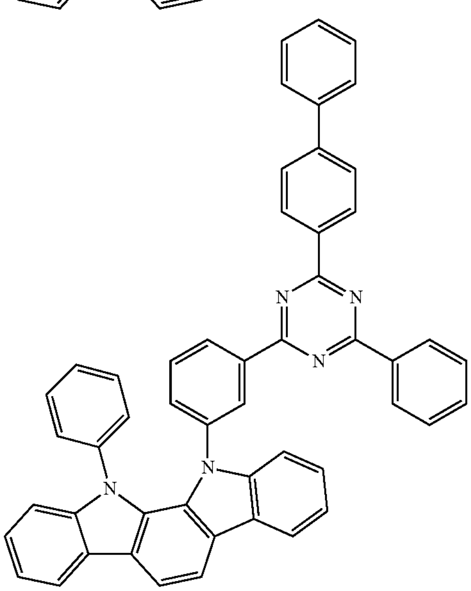

-continued
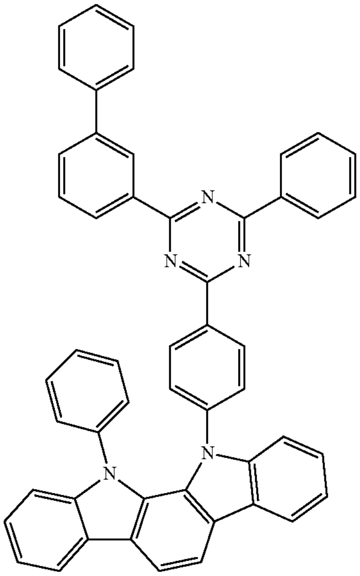
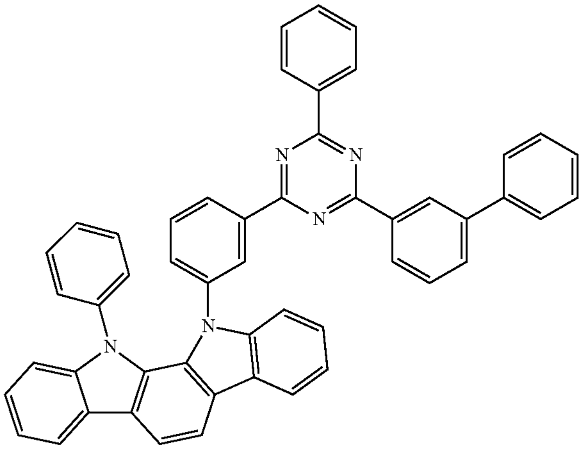
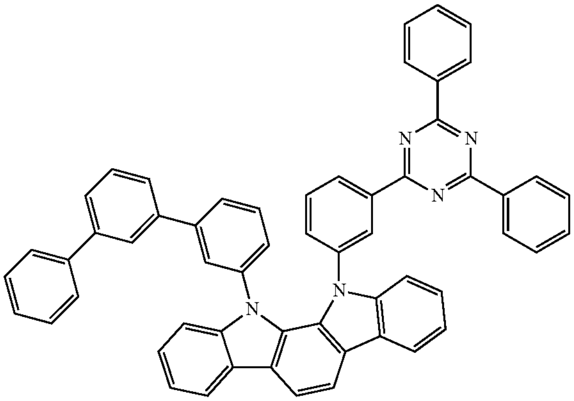
-continued
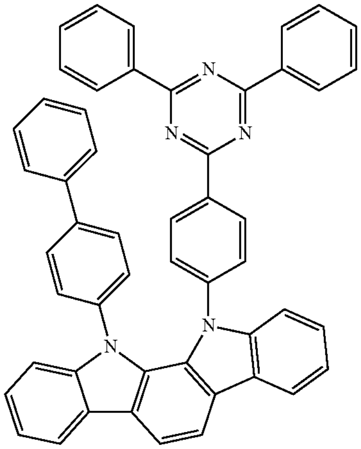
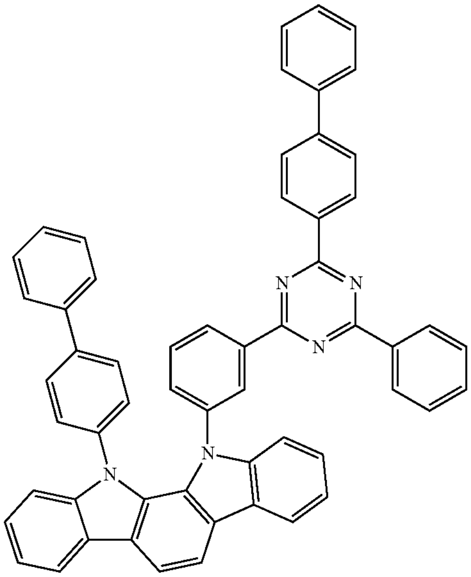
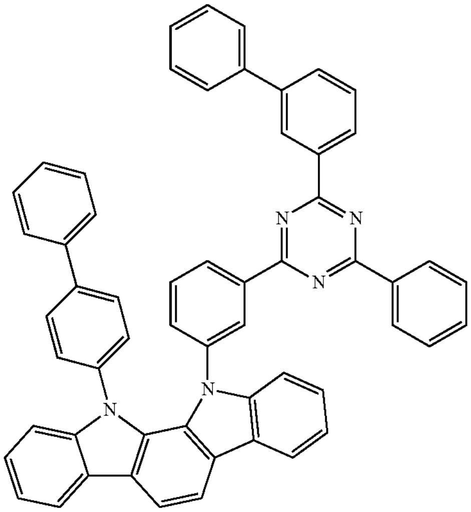

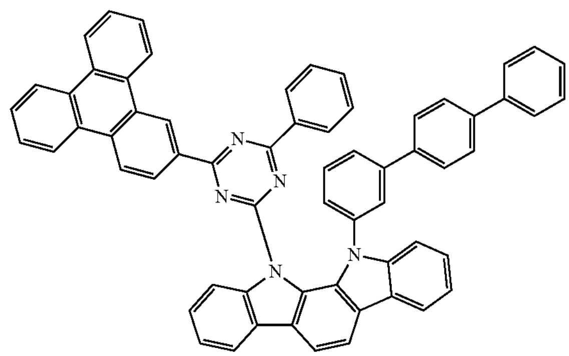
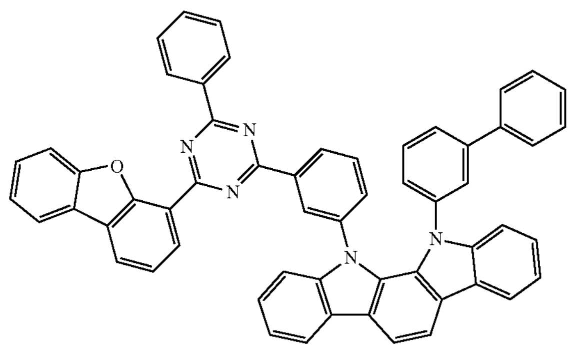
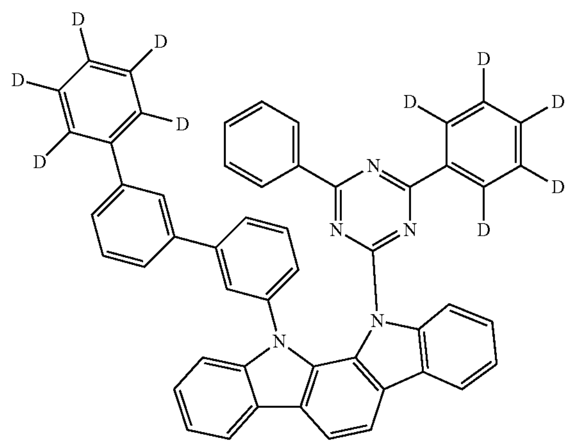
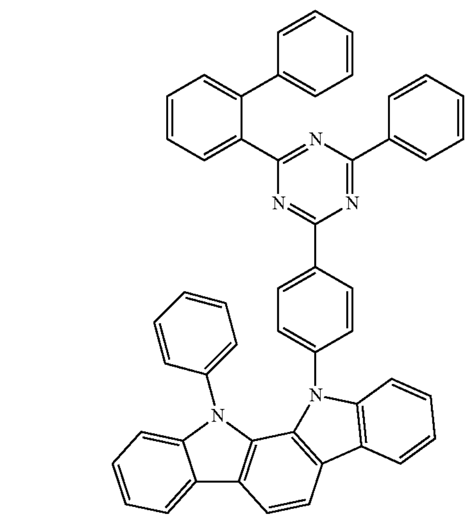
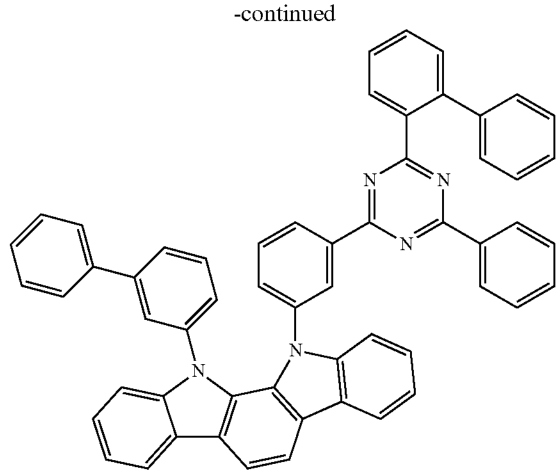
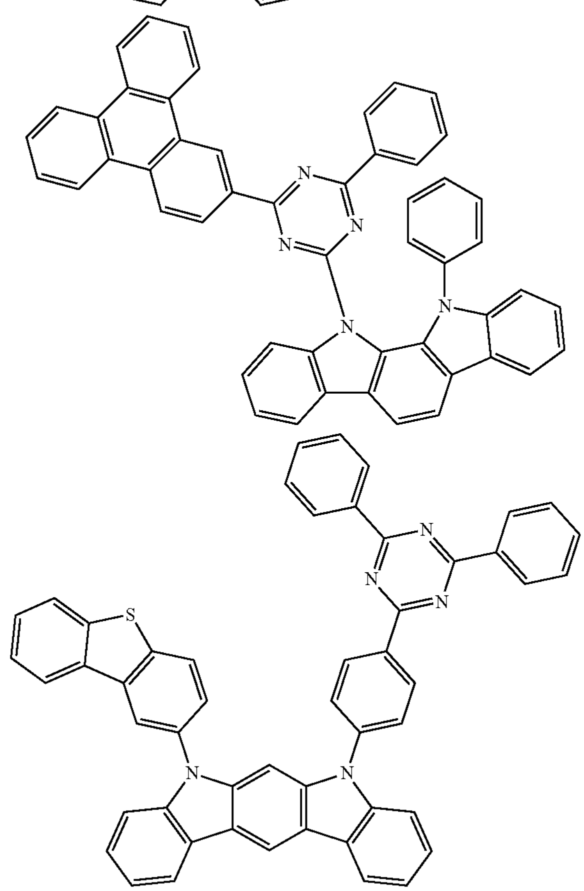
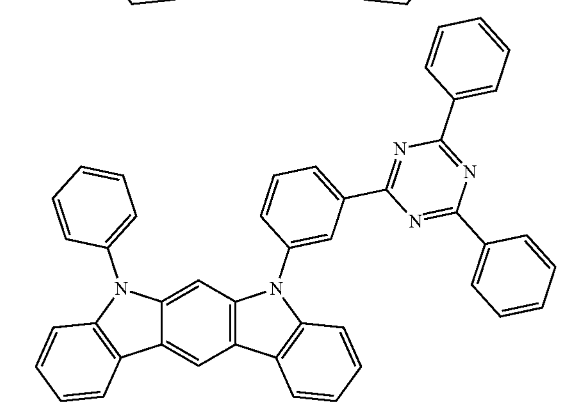

-continued
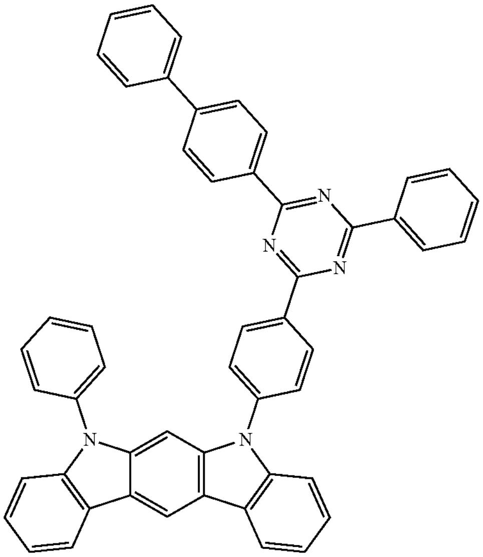
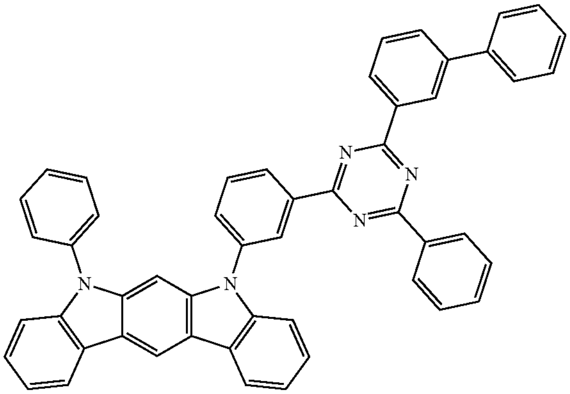
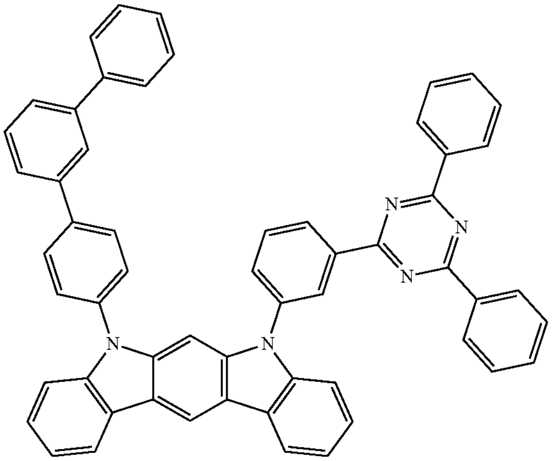
-continued
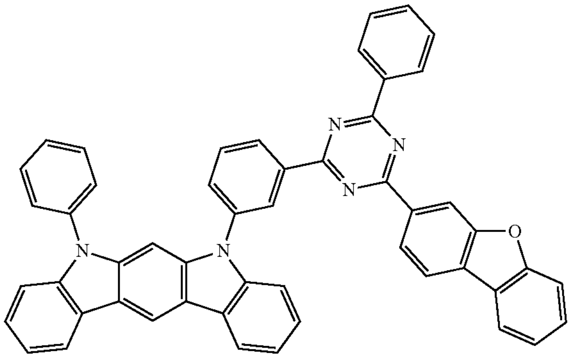
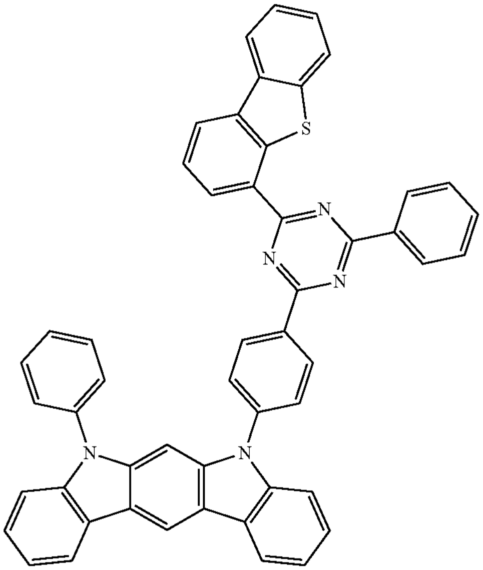
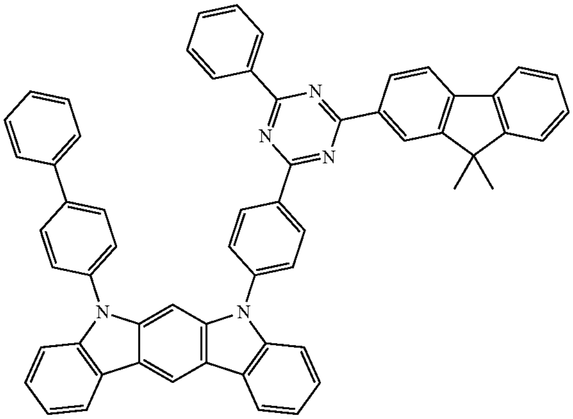

-continued
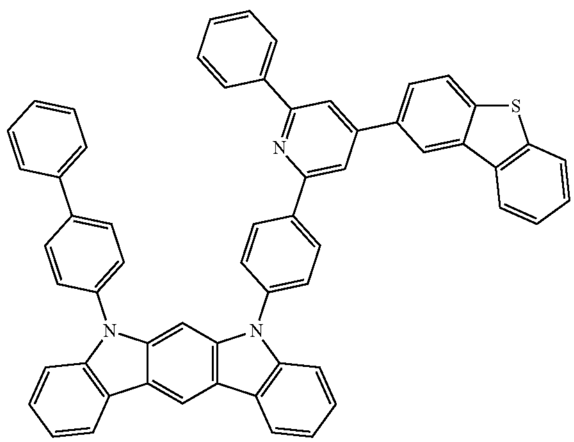
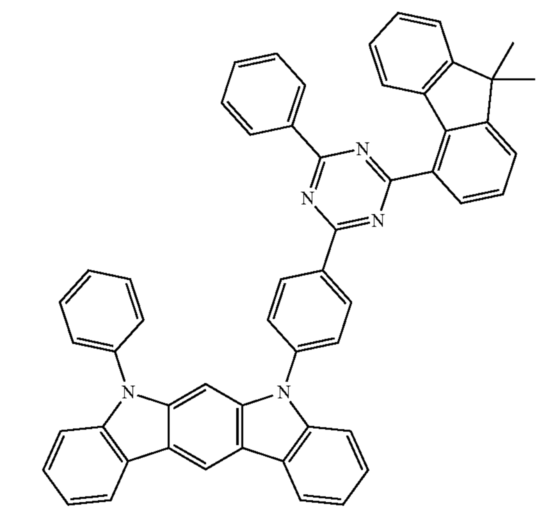
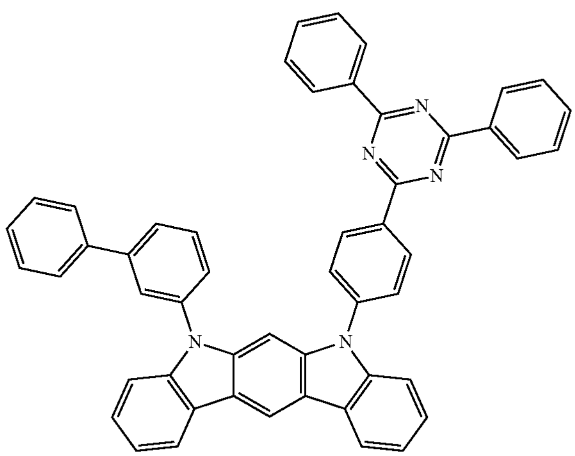
-continued
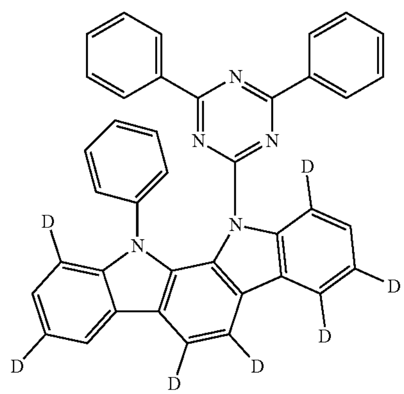
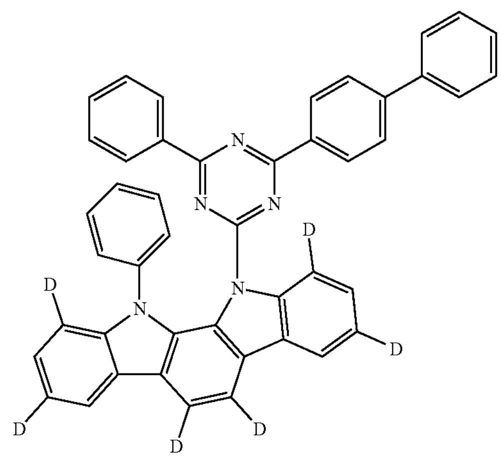
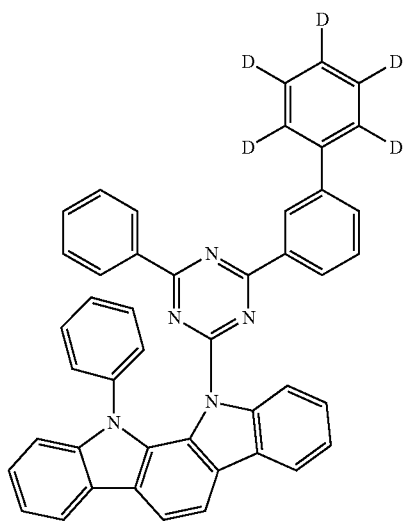

-continued
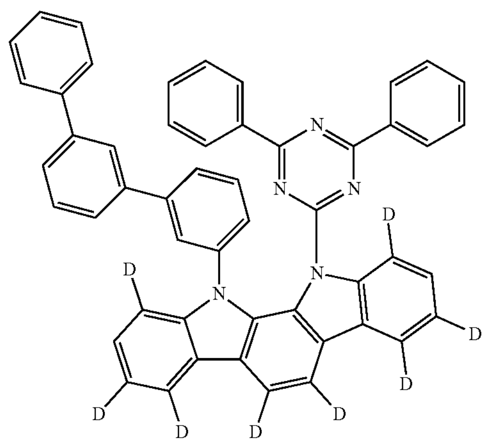
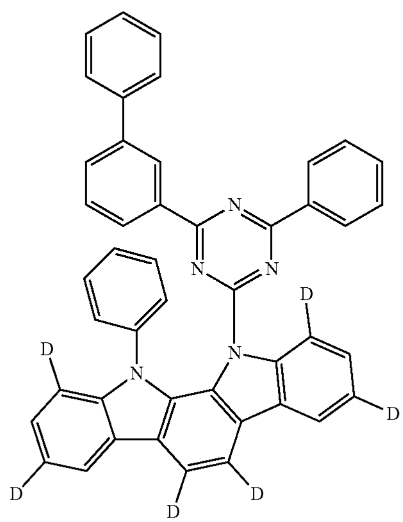
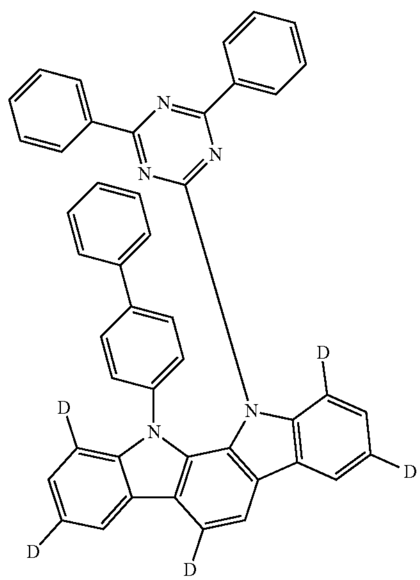
-continued
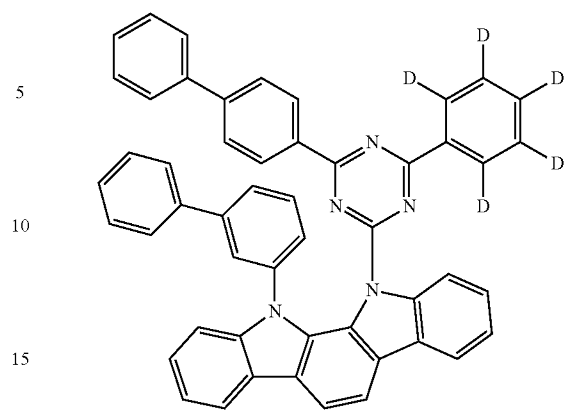
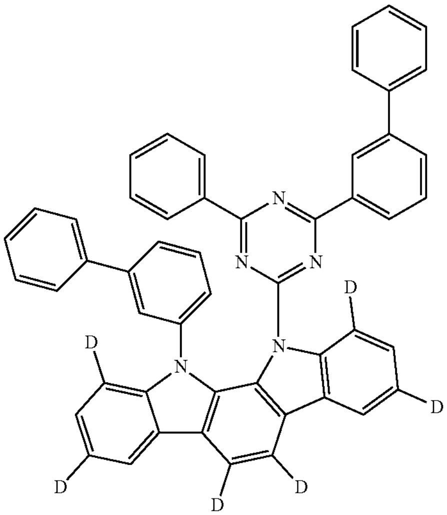
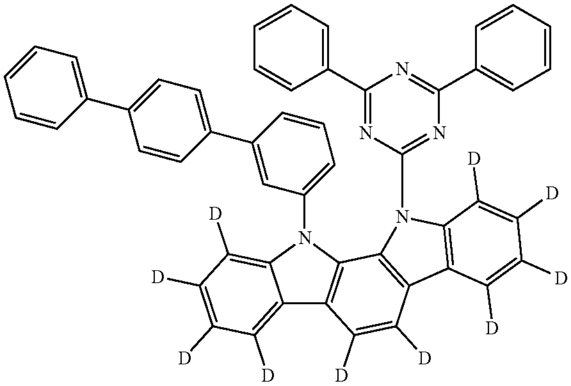

-continued
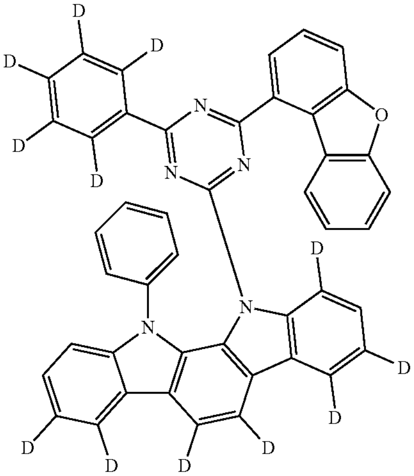
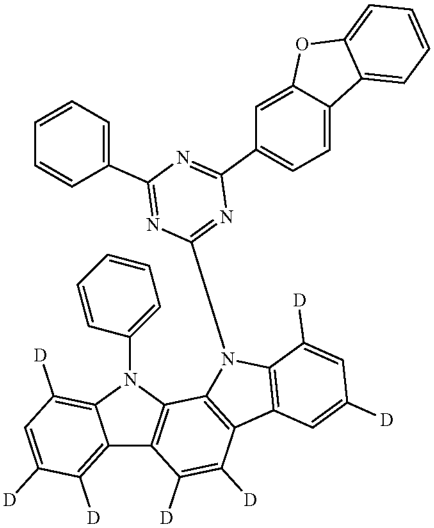
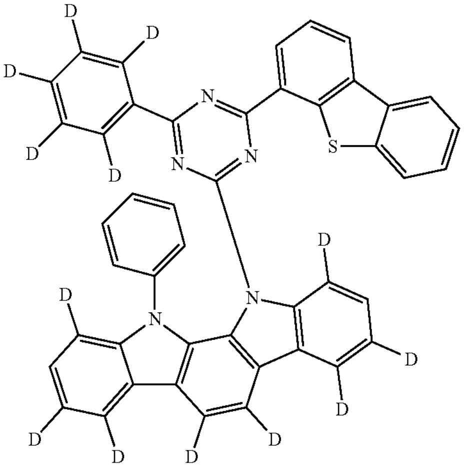
-continued
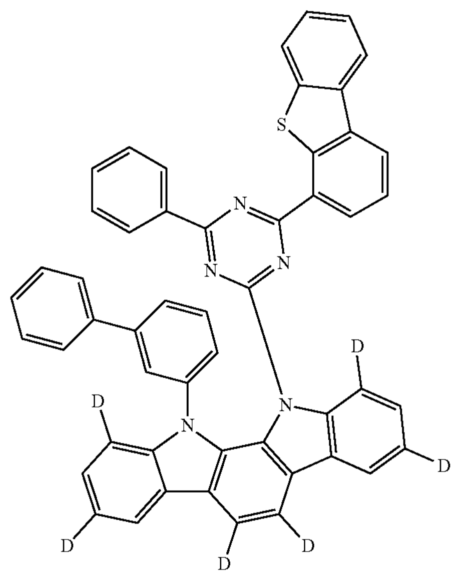
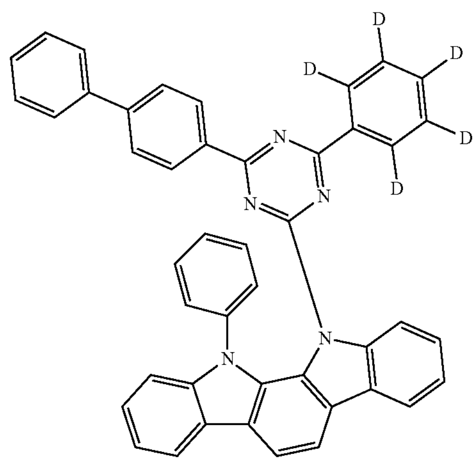
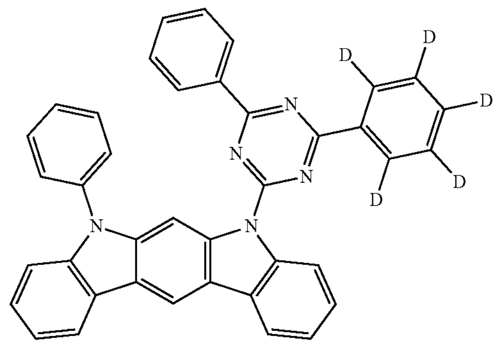

-continued
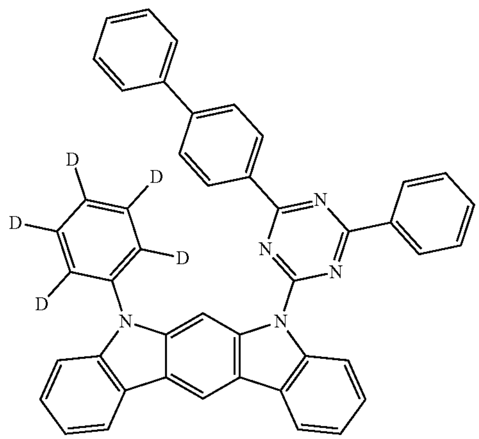
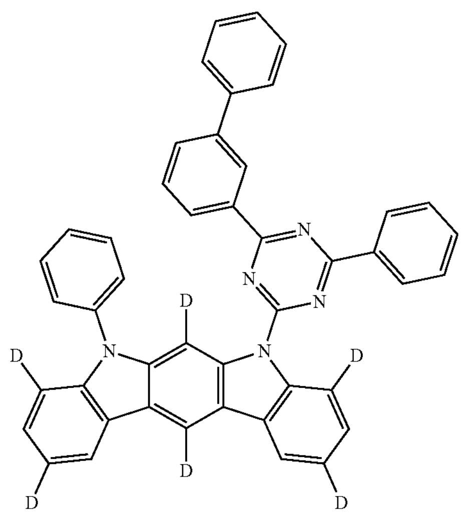
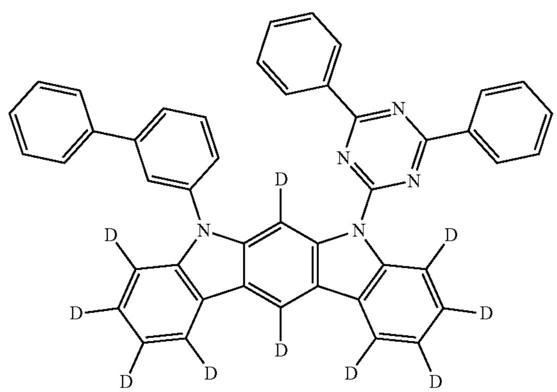
-continued
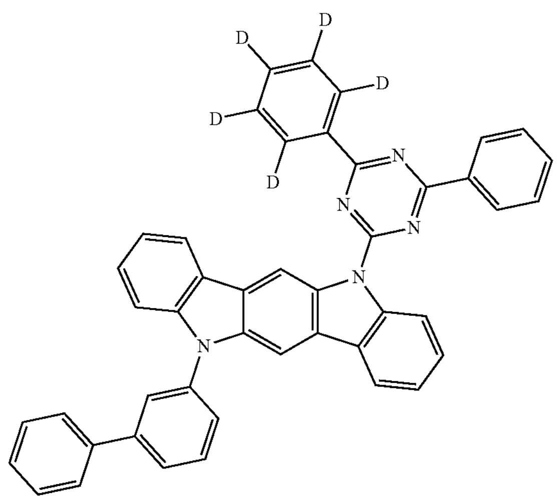
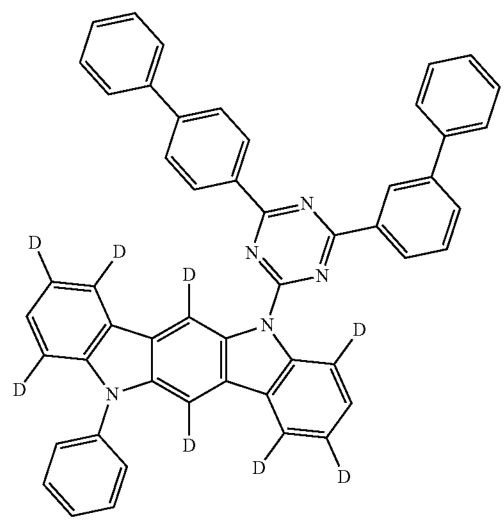
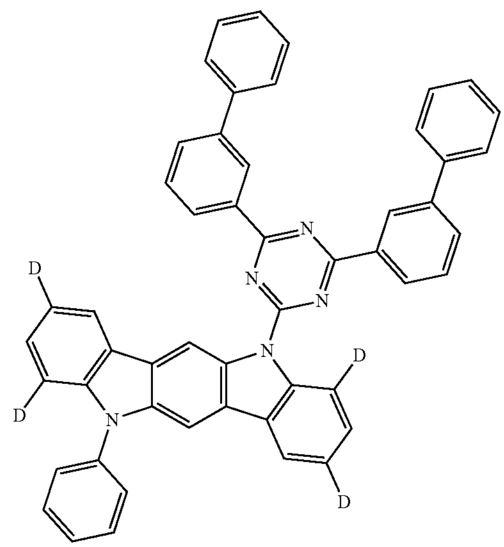

-continued
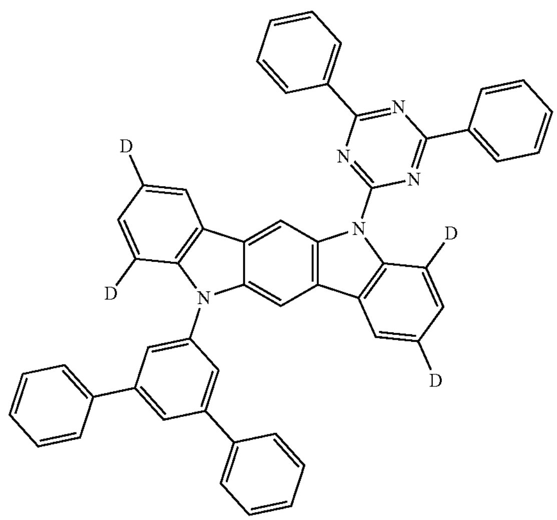
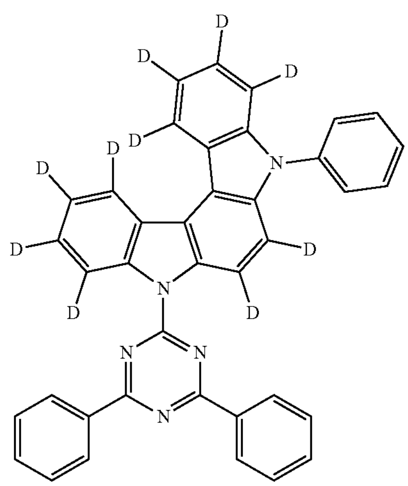
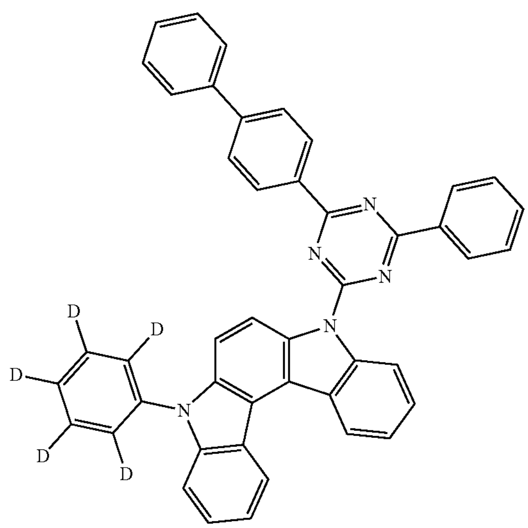
-continued
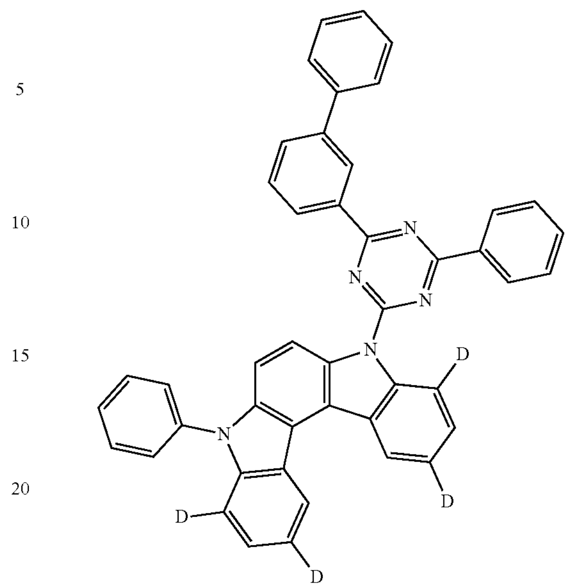
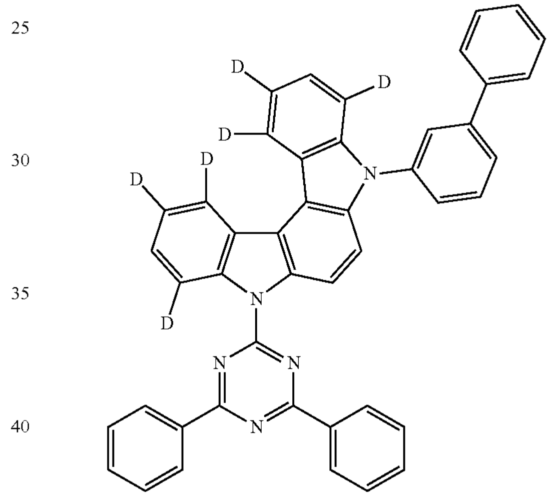
Further, the present disclosure provides a method for preparing the compound of Chemical Formula 3 as shown in the following Reaction Scheme 3.
[Reaction Scheme 3]
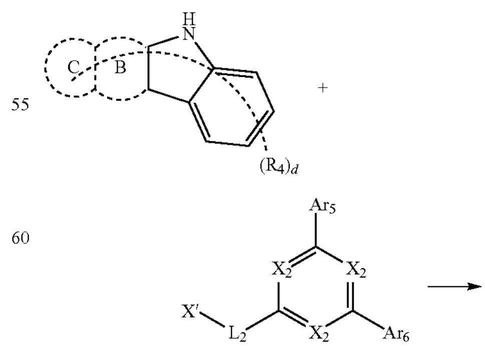

-continued

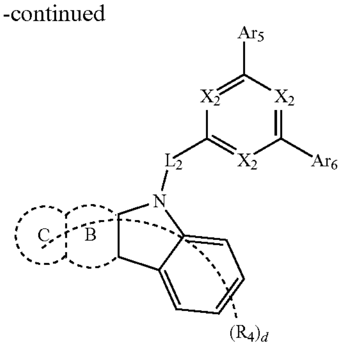

wherein in Reaction Scheme 3, the definition of the remaining substituents except for X' are the same as defined above, and X' is halogen, more preferably fluoro, chloro or bromo.

The above reaction is an amine substitution reaction which is preferably carried out in the presence of a palladium catalyst and a base, and a reactive group for the amine substitution reaction can be modified as known in the art. The above preparation method can be further embodied in Preparation Examples described hereinafter.

The dopant material is not particularly limited as long as it is a material used for the organic light emitting device. As an example, an aromatic amine derivative, such as a styrylamine compound, a boron complex, a fluoranthene compound, a metal complex, and the like can be mentioned. Specific examples of the aromatic amine derivatives include substituted or unsubstituted fused aromatic ring derivatives having an arylamino group, examples thereof include pyrene, anthracene, chrysene, and periflanthene having the arylamino group, and the like. The styrylamine compound is a compound where at least one arylvinyl group is substituted in substituted or unsubstituted arylamine, wherein one or two or more substituent groups selected from the group consisting of an aryl group, a silyl group, an alkyl group, a cycloalkyl group and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto Hole Transport Layer The organic light emitting device according to the present disclosure can include a hole transport layer between the electron inhibition layer and the anode.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer.

The hole transport material can include an arylamine-based organic material, a conductive polymer, a block copolymer in which a conjugate portion and a non-conjugate portion are present together, and the like, but are not limited thereto.

Electron Inhibition Layer

The organic light emitting device according to the present disclosure includes an electron inhibition layer between the anode and the light emitting layer. Preferably, the electron inhibition layer is included in contact with the anode side of the light emitting layer.

The electron inhibition layer includes an electron blocking layer and serves to suppress the electrons injected from the cathode from being transmitted toward the anode without being recombined in the light emitting layer.

The electron inhibition layer includes an electron blocking layer, and examples of the electron blocking layer include an arylamine-based organic material, or the like, but is not limited thereto.

Hole Injection Layer

The organic light emitting device according to the present disclosure can further include a hole injection layer between the anode and the hole transport layer, if necessary.

The hole injection layer is a layer injecting holes from an electrode, and the hole injection material is preferably a compound which has a capability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer.

Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

Electron Transport Layer

The organic light emitting device according to the present disclosure can include an electron transport layer between the light emitting layer and the cathode.

The electron transport layer is a layer that receives electrons from a cathode and an electron injection layer formed on the cathode and transports the electrons to the light emitting layer, and that suppress the transfer of holes from the light emitting layer, and an electron transport material is suitably a material which can receive electrons well from a cathode and transfer the electrons to a light emitting layer, and has a large mobility for electrons.

Specific examples of the electron transport material include: an Al complex of 8-hydroxyquinoline; a complex including $Alq_3$; an organic radical compound; a hydroxyflavone-metal complex, and the like, but are not limited thereto. The electron transport layer can be used with any desired cathode material, as used according to a conventional technique. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

Electron Injection Layer

The organic light emitting device according to the present disclosure can further include an electron injection layer between the electron transport layer and the cathode, if necessary.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples of the materials that can be used as the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

Organic Light Emitting Device

The structure of the organic light emitting device according to the present disclosure is illustrated in FIG. 1. FIG. 1 shows an example of an organic light emitting device comprising a substrate 1, an anode 2, an electron inhibition layer 3, a light emitting layer 4, and a cathode 5. In addition, the structure of the organic light emitting device including the hole transport layer 6 and the electron transport layer 7 is illustrated in FIG. 2.

The organic light emitting device according to the present disclosure can be manufactured by sequentially stacking the above-described structures. In this case, the organic light emitting device can be manufactured by depositing a metal, metal oxides having conductivity, or an alloy thereof on the substrate by using a PVD (physical vapor deposition) method such as a sputtering method or an e-beam evaporation method to form the anode, forming the respective layers described above thereon, and then depositing a material that can be used as the cathode thereon. In addition to such a method, the organic light emitting device can be manufactured by sequentially depositing from the cathode material to the anode material on a substrate in the reverse order of the above-mentioned configuration (WO 2003/012890). Further, the light emitting layer can be formed by subjecting hosts and dopants to a vacuum deposition method and a solution coating method. Herein, the solution coating method means a spin coating, a dip coating, a doctor blading, an inkjet printing, a screen printing, a spray method, a roll coating, or the like, but is not limited thereto.

On the other hand, the organic light emitting device according to the present disclosure can be a front side emission type, a back side emission type, or a double side emission type according to the used material.

The preparation of the organic light emitting device according to the present disclosure will be described in detail in the following examples. However, these examples are presented for illustrative purposes only, and are not intended to limit the scope of the present disclosure.

Preparation Example 1

Preparation Example 1-1: Preparation of Compound 1-1

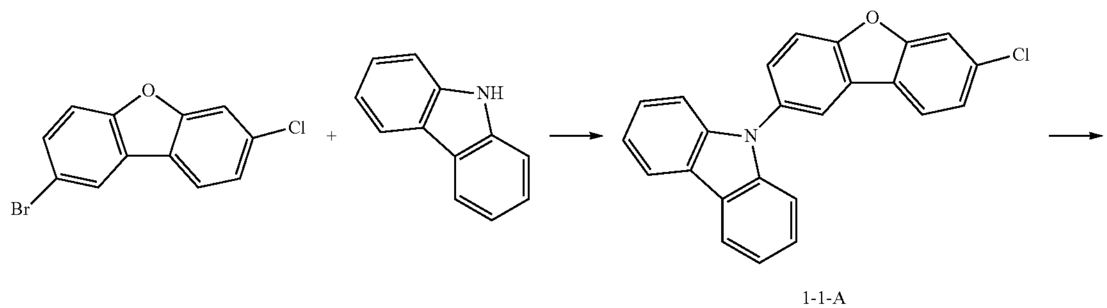

1-1-A

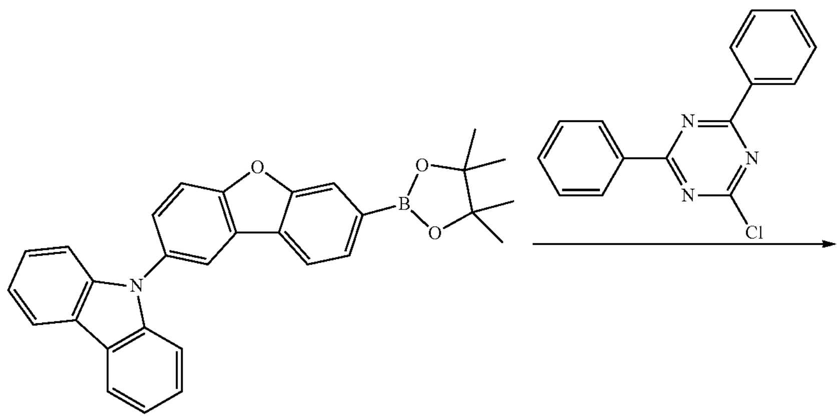

1-1-B

-continued

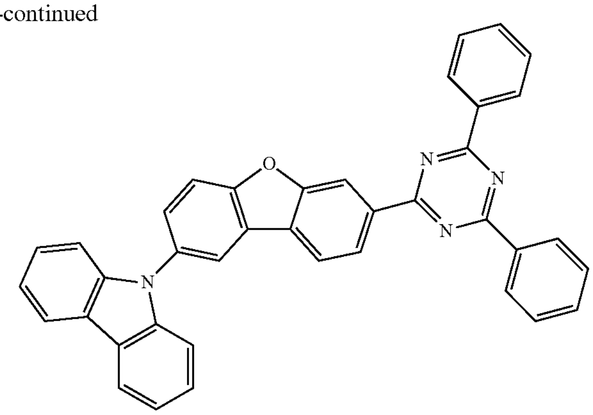

1-1

Step 1) Preparation of Compound 1-1-A

2-Bromo-7-chlorodibenzo[b,d]furan (20 g, 71 mmol) and 9H-carbazole (11.9 g, 71 mmol) were added to xylene (400 ml) under a nitrogen atmosphere, and the mixture was stirred and refluxed. Then, $K_3PO_4$ (20.5 g, 213.1 mmol) was added thereto, and the mixture was sufficiently stirred and then bis(tri-tert-butylphosphine)palladium(0) (1.1 g, 2.1 mmol) was added. After the reaction for 3 hours, the reaction mixture was cooled to room temperature, and the organic layer was filtered to remove salts, and then the filtered organic layer was distilled. This was again added to and dissolved in chloroform (261 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethanol to prepare a beige solid Compound 1-1-A (17.8 g, yield: 68%).

MS: $[M+H]^+$=368.8

Step 2) Preparation of Compound 1-1-B

Compound 1-1-A (30 g, 81.6 mmol) and bis(pinacolato) diboron (20.7 g, 81.6 mmol) were added to dioxane (600 ml) under a nitrogen atmosphere, and the mixture was stirred and refluxed. Then, potassium acetate (24 g, 244.7 mmol) was added thereto, and the mixture was sufficiently stirred and then bis(dibenzylideneacetone)palladium(0) (1.4 g, 2.4 mmol) and tricyclohexylphosphine (1.4 g, 4.9 mmol) were added. After the reaction for 5 hours, the reaction mixture was cooled to room temperature, and the organic layer was filtered to remove salts, and then the filtered organic layer was distilled. This was again added to and dissolved in chloroform (375 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethanol to prepare a white solid Compound 1-1-B (19.5 g, yield: 52%).

MS: $[M+H]^+$=460.4

Step 3) Preparation of Compound 1-1

Compound 1-1-B (20 g, 43.5 mmol) and 2-chloro-4,6-diphenyl-1,3,5-triazine (11.7 g, 43.5 mmol) were added to THF (400 ml) under a nitrogen atmosphere, and the mixture was stirred and refluxed. Then, potassium carbonate (18.1 g, 130.6 mmol) was dissolved in water (54 ml), added thereto, and the mixture was sufficiently stirred and then bis(tri-tert-butylphosphine)palladium(0) (0.7 g, 1.3 mmol) was added. After the reaction for 5 hours, the reaction mixture was cooled to room temperature, and the organic layer and the aqueous layer were separated and then the organic layer was distilled. This was again added to and dissolved in chloroform (1229 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethyl acetate to prepare a fluorescent solid Compound 1-1 (17.5 g, yield: 71%).

MS: $[M+H]^+$=565.7

Preparation Example 1-2: Preparation of Compound 1-2

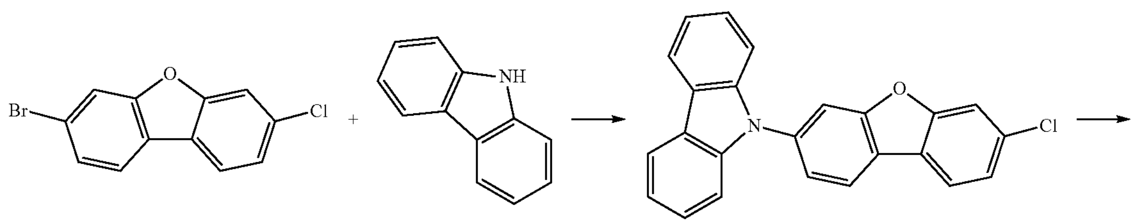

1-2-A

-continued

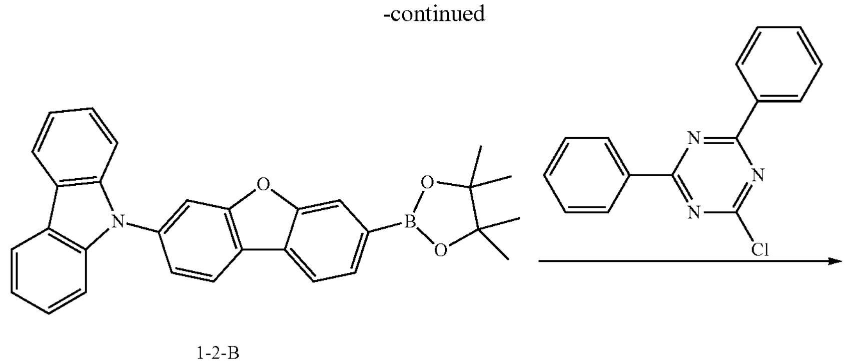

1-2-B

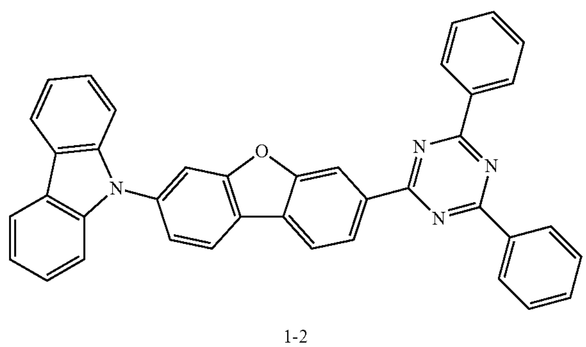

1-2

Compound 1-2 (16.7 g, yield: 68%) was prepared in the same manner as in the Preparation of Compound 1-1, except that 3-bromo-7-chlorodibenzo[b,d]furan was used instead of 2-bromo-7-chlorodibenzo[b,d]furan.

MS: $[M+H]^+$=565.7

Preparation Example 1-3: Preparation of Compound 1-3

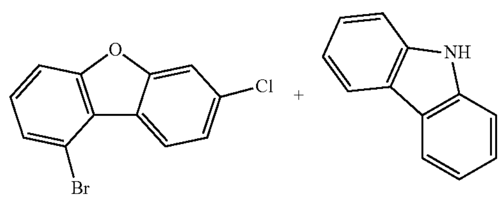

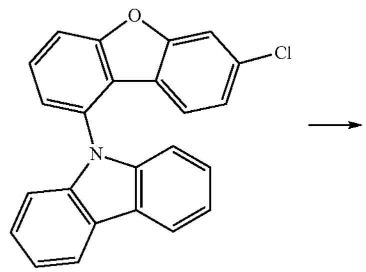

1-3-A

-continued

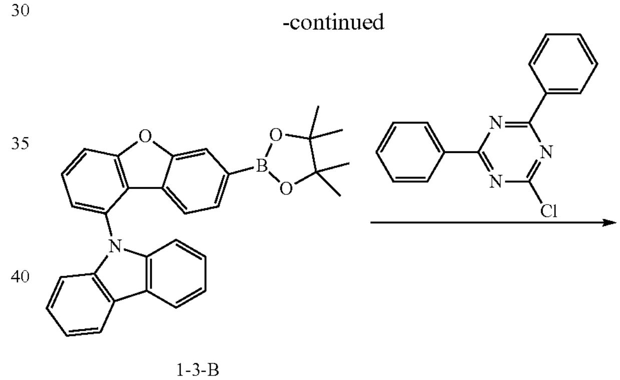

1-3-B

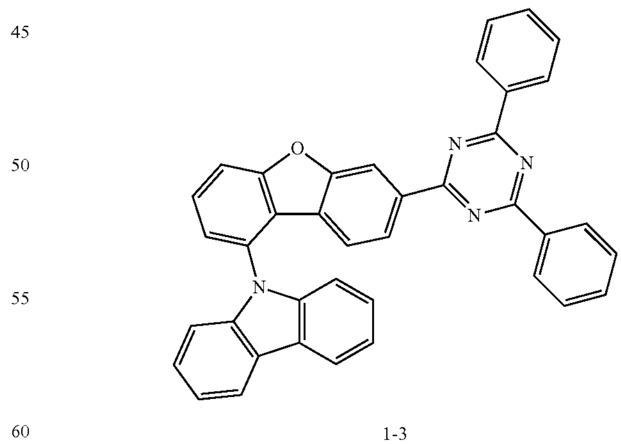

1-3

Compound 1-3 (12.8 g, yield: 52%) was prepared in the same manner as in the Preparation of Compound 1-1, except that 1-bromo-7-chlorodibenzo[b,d]furan was used instead of 2-bromo-7-chlorodibenzo[b,d]furan.

MS: $[M+H]^+$=565.7

Preparation Example 1-4: Preparation of Compound 1-4

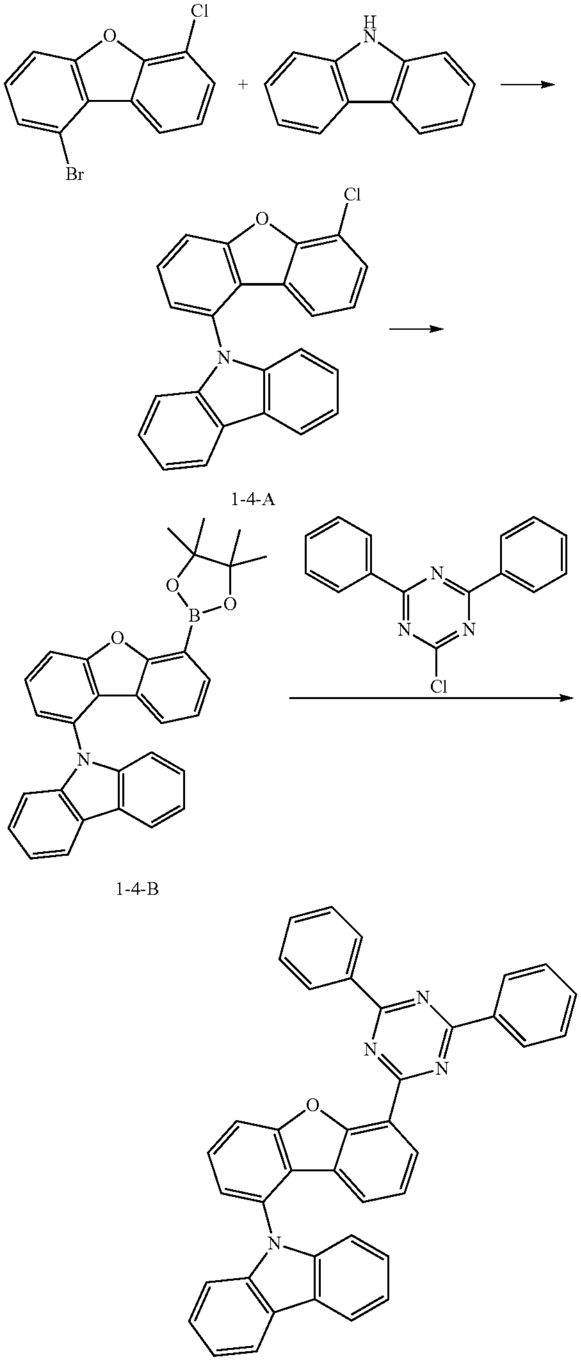

1-4-A 1-4-B 1-4

Compound 1-4 (17.9 g, yield: 73%) was prepared in the same manner as in the Preparation of Compound 1-1, except that 1-bromo-6-chlorodibenzo[b,d]furan was used instead of 2-bromo-7-chlorodibenzo[b,d]furan.

MS: $[M+H]^+$=565.7

Preparation Example 1-5: Preparation of Compound 1-5

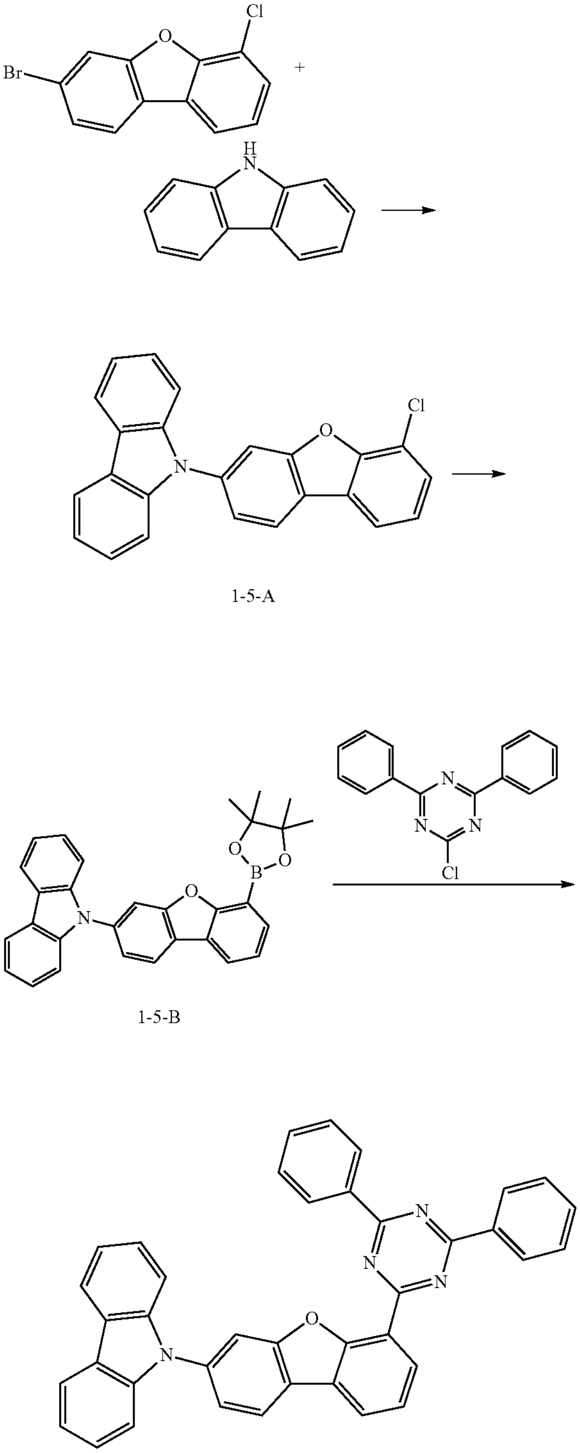

1-5-A 1-5-B 1-5

Compound 1-5 (13.8 g, yield: 56%) was prepared in the same manner as in the Preparation of Compound 1-1, except that 3-bromo-6-chlorodibenzo[b,d]furan was used instead of 2-bromo-7-chlorodibenzo[b,d]furan.

MS: $[M+H]^+$=565.7

Preparation Example 1-6: Preparation of Compound 1-6
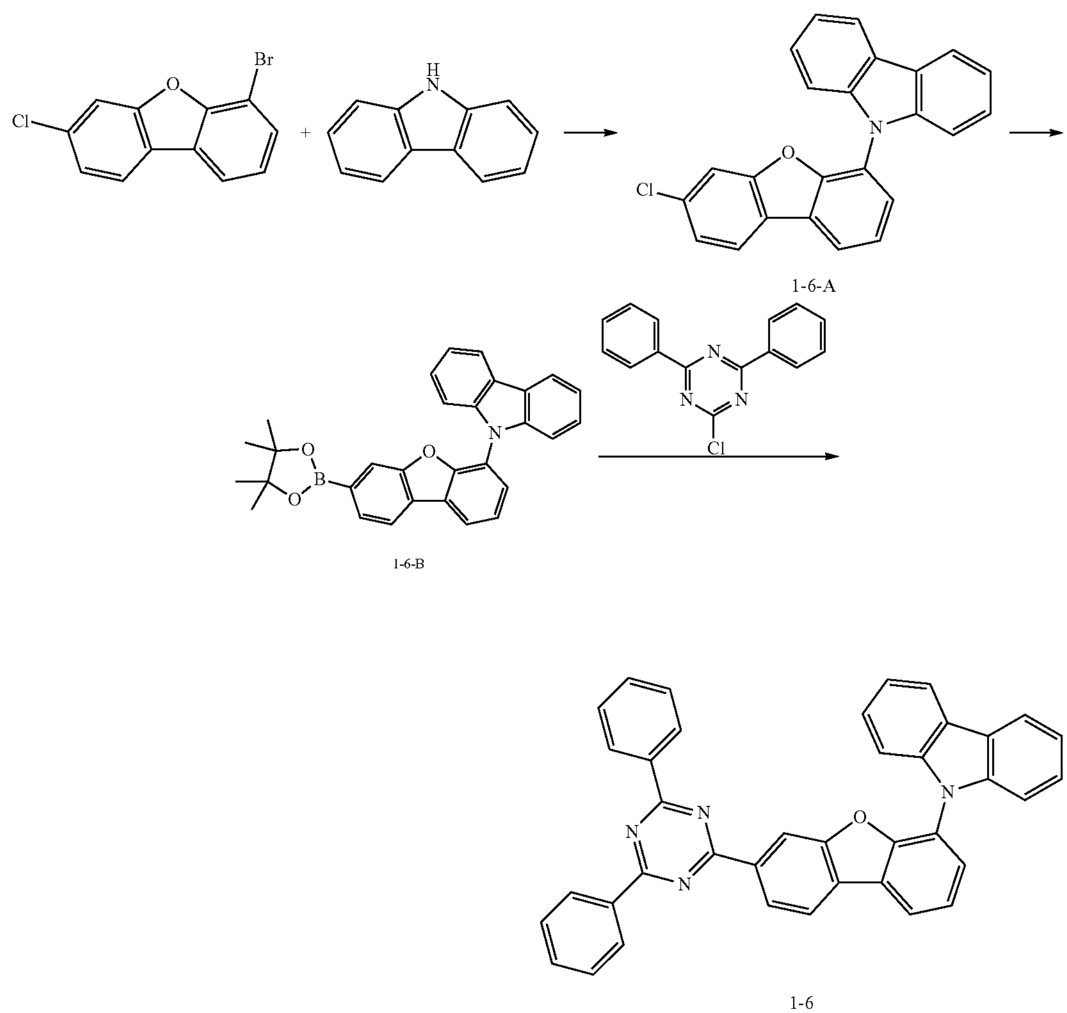
1-6-A
1-6-B
1-6
Compound 1-6 (15.7 g, yield: 64%) was prepared in the same manner as in the Preparation of Compound 1-1, except that 6-bromo-3-chlorodibenzo[b,d]furan was used instead of 2-bromo-7-chlorodibenzo[b,d]furan.
MS: $[M+H]^+=565.7$
Preparation Example 1-7: Preparation of Compound 1-7
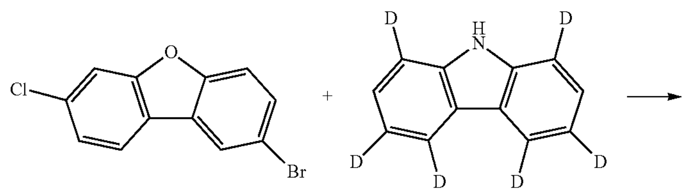

-continued
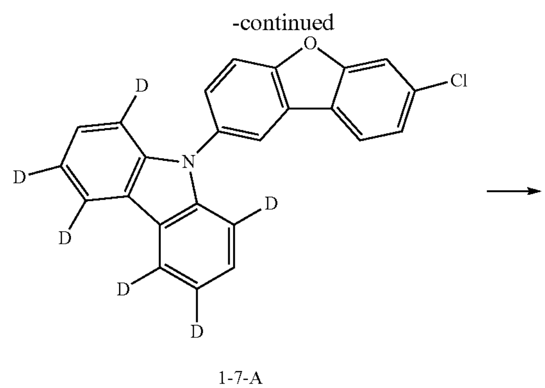
1-7-A
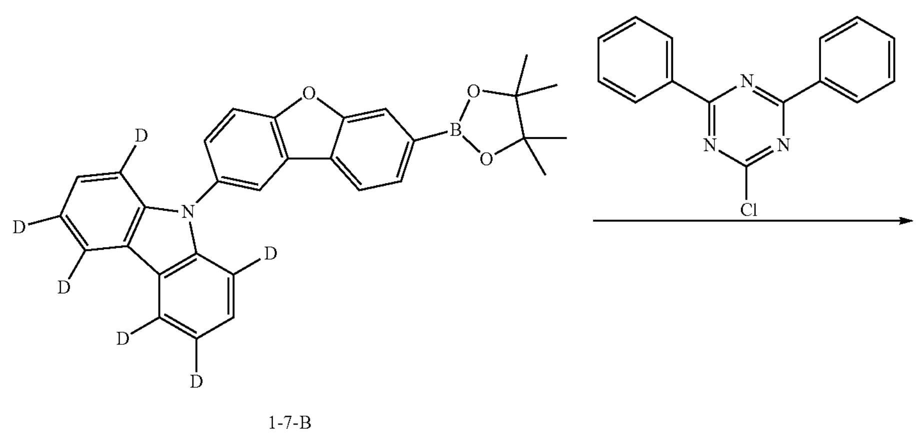
1-7-B
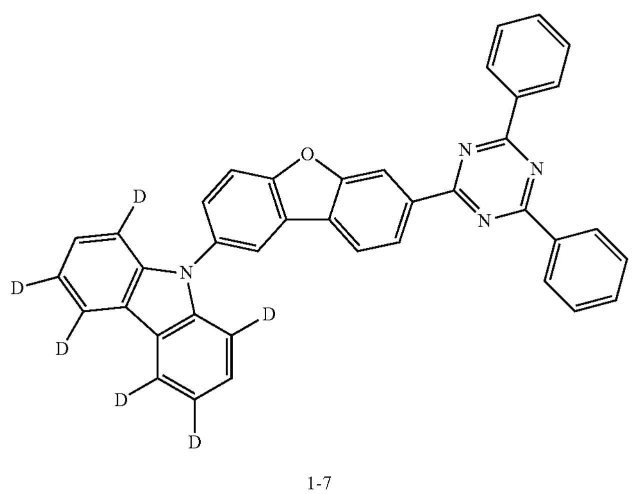
1-7
Compound 1-7 (16.4 g, yield: 66%) was prepared in the same manner as in the Preparation of Compound 1-1, except that 9H-carbazole-1,3,4,5,6,8-d6 was used instead of 9H-carbazole.
MS: $[M+H]^+$=571.7

Preparation Example 1-8: Preparation of Compound 1-8

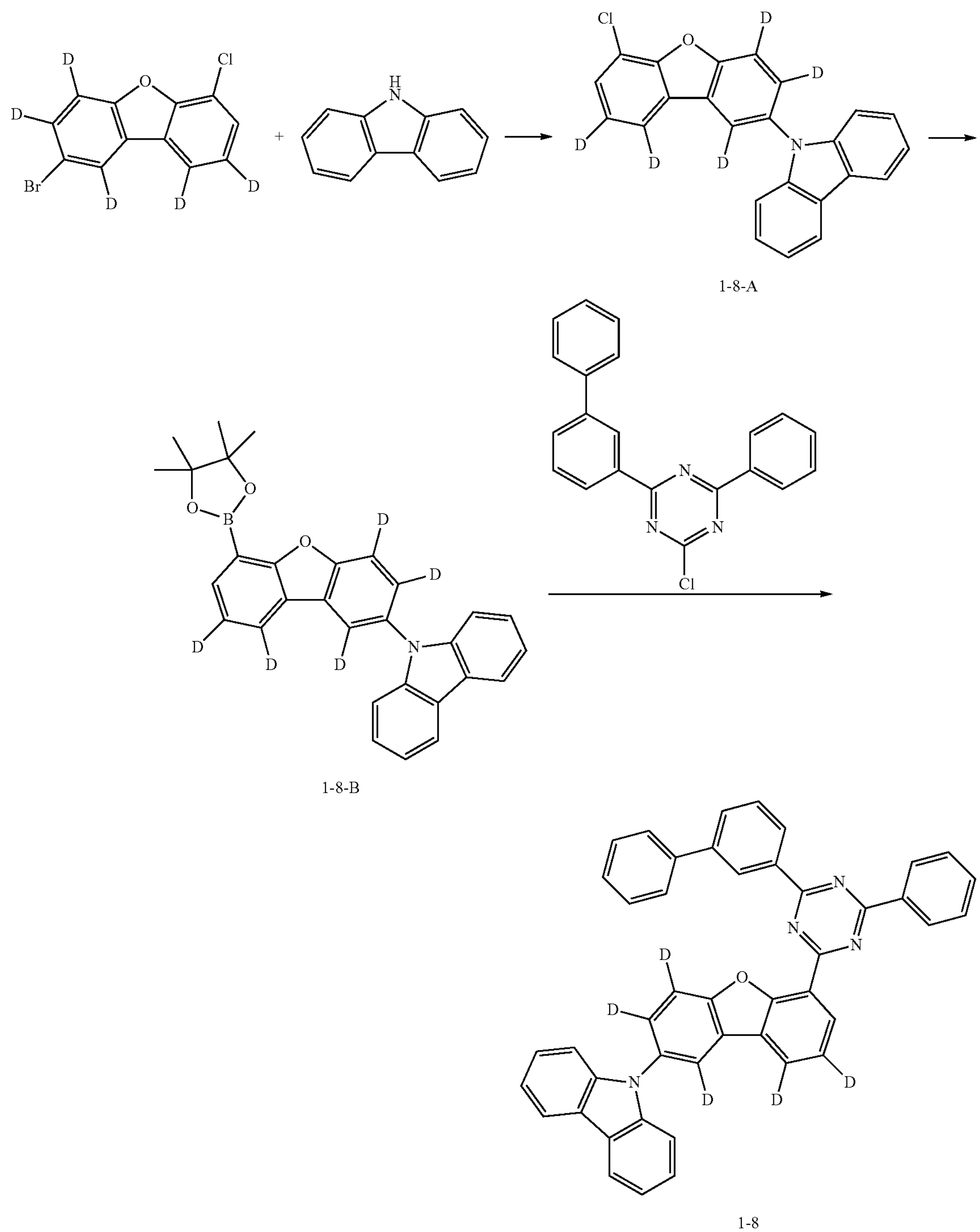

1-8-A 1-8-B 1-8

Compound 1-8 (16.9 g, yield: 60%) was prepared in the same manner as in the Preparation of Compound 1-1, except that in step 1 of the Preparation of Compound 1-1, 2-bromo-6-chlorodibenzo[b,d]furan-1,3,4,8,9-d5 was used instead of 2-bromo-7-chlorodibenzo[b,d]furan, and in step 3, 2-([1,1'-biphenyl]-3-yl)-4-chloro-6-phenyl-1,3,5-triazine was used instead of 2-chloro-4,6-diphenyl-1,3,5-triazine.

MS: $[M+H]^+$=646.8

Preparation Example 1-9: Preparation of Compound 1-9

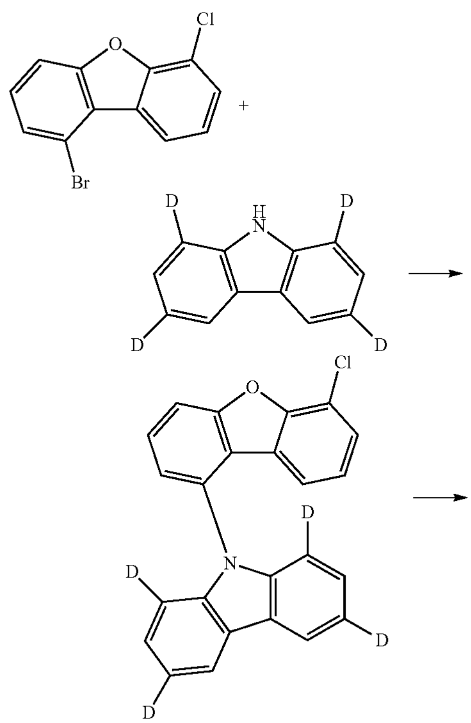

1-9-A

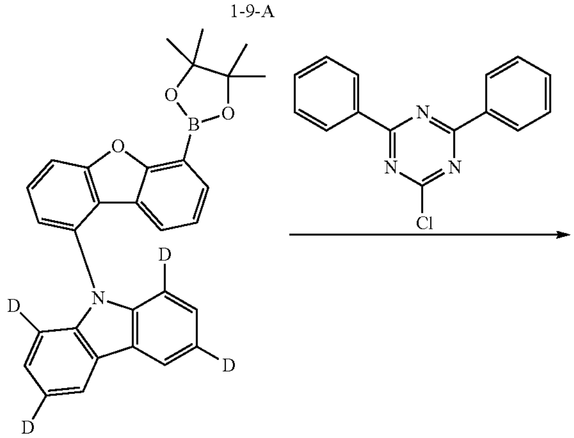

1-9-B

-continued

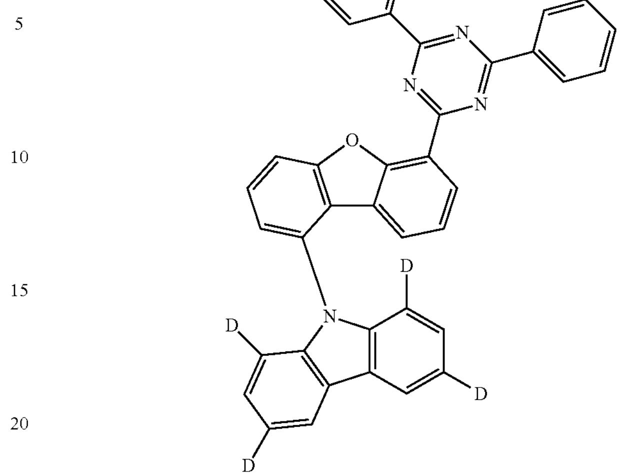

1-9

Compound 1-9 (19.3 g, yield: 78%) was prepared in the same manner as in the Preparation of Compound 1-1, except that in step 1 of the Preparation of Compound 1-1, 1-bromo-6-chlorodibenzo[b,d]furan was used instead of 2-bromo-7-chlorodibenzo[b,d]furan, and 9H-carbazole-1,3,6,8-d4 was used instead of 9H-carbazole.

MS: $[M+H]^+$=569.7

Preparation Example 1-10: Preparation of Compound 1-10

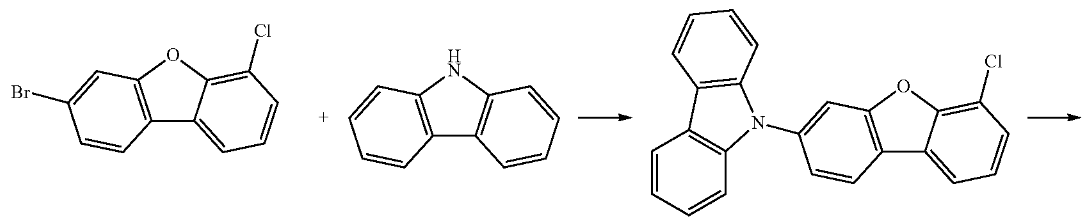

1-10-A

-continued

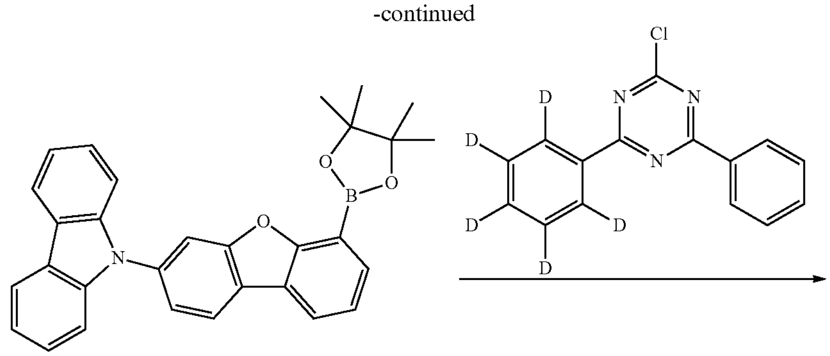

1-10-B

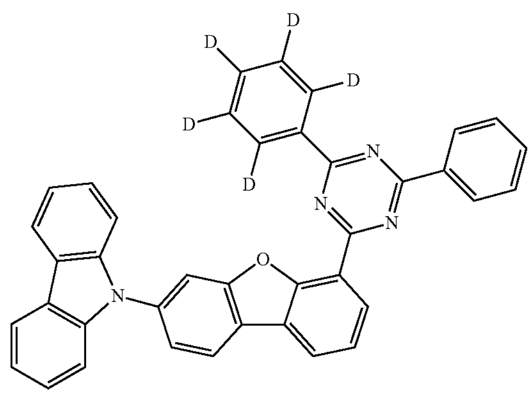

1-10

Compound 1-10 (18.6 g, yield: 75%) was prepared in the same manner as in the Preparation of Compound 1-1, except that in step 1 of the Preparation of Compound 1-1, 3-bromo-6-chlorodibenzo[b,d]furan was used instead of 2-bromo-7-chlorodibenzo[b,d]furan, and in step 3, 2-chloro-4-phenyl-6-(phenyl-d5)-1,3,5-triazine was used instead of 2-chloro-4,6-diphenyl-1,3,5-triazine.

MS: $[M+H]^+$=570.7

Preparation Example 1-11: Preparation of Compound 1-11

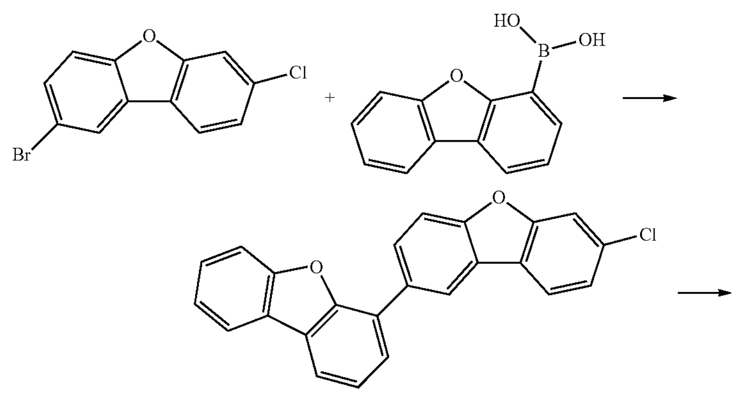

1-11-A

-continued

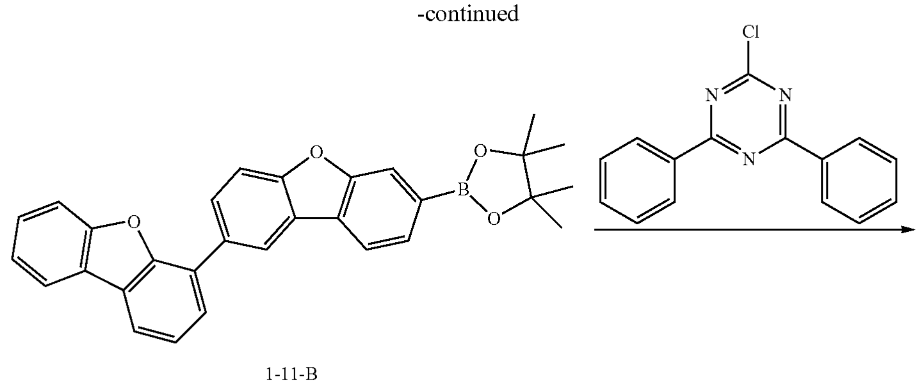

1-11-B

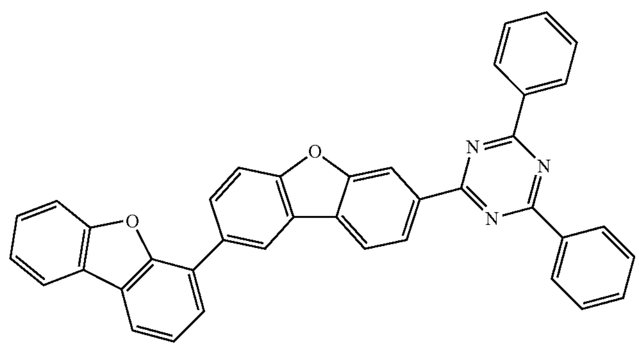

1-11

Step 1) Preparation of Compound 1-11-A

2-Bromo-7-chlorodibenzo[b,d]furan (20 g, 71 mmol) and dibenzo[b,d]-furan-4-ylboronic acid (15.1 g, 71 mmol) were added to THF (400 ml) under a nitrogen atmosphere, and the mixture was stirred and refluxed. Then, potassium carbonate (29.5 g, 213.1 mmol) was dissolved in water (88 ml), added thereto, and the mixture was sufficiently stirred and then tetrakis(triphenylphosphine)palladium(0) (1.1 g, 2.1 mmol) was added. After the reaction for 4 hours, the reaction mixture was cooled to room temperature, and the organic layer and the aqueous layer were separated and then the organic layer was distilled. This was again added to and dissolved in chloroform (1310 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethanol to prepare a white solid Compound 1-11-A (14.1 g, yield: 54%).

MS: $[M+H]^+$=369.8

Step 2) Preparation of Compound 1-11-B

Compound 1-11-A (30 g, 81.3 mmol) and bis(pinacolato) diboron (20.7 g, 81.3 mmol) were added to dioxane (600 ml) under a nitrogen atmosphere, and the mixture was stirred and refluxed. Then, potassium acetate (24 g, 244 mmol) was added thereto, and the mixture was sufficiently stirred and then bis(dibenzylideneacetone)palladium(0) (1.4 g, 2.4 mmol) and tricyclohexylphosphine (1.4 g, 4.9 mmol) were added. After the reaction for 8 hours, the reaction mixture was cooled to room temperature, and the organic layer was filtered to remove to remove salts, and then the filtered organic layer was distilled. This was again added to and dissolved in chloroform (374 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethanol to prepare a beige solid Compound 1-11-B (26.6 g, yield: 71%).

MS: $[M+H]^+$=461.3

Step 3) Preparation of Compound 1-11

Compound 1-11-B (20 g, 43.4 mmol) and 2-chloro-4,6-diphenyl-1,3,5-triazine (11.6 g, 43.4 mmol) were added to THF (400 ml) under a nitrogen atmosphere, and the mixture was stirred and refluxed. Then, potassium carbonate (18 g, 130.3 mmol) was dissolved in water (54 ml), added thereto, and the mixture was sufficiently stirred and then bis(tri-tert-butylphosphine)palladium(0) (0.7 g, 1.3 mmol) was added. After the reaction for 5 hours, the reaction mixture was cooled to room temperature, and the organic layer and the aqueous layer were separated and then the organic layer was distilled. This was again added to and dissolved in chloroform (1229 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethyl acetate to prepare a white solid Compound 1-11 (17 g, yield: 69%).

MS: $[M+H]^+$=566.6

Preparation Example 1-12: Preparation of Compound 1-12

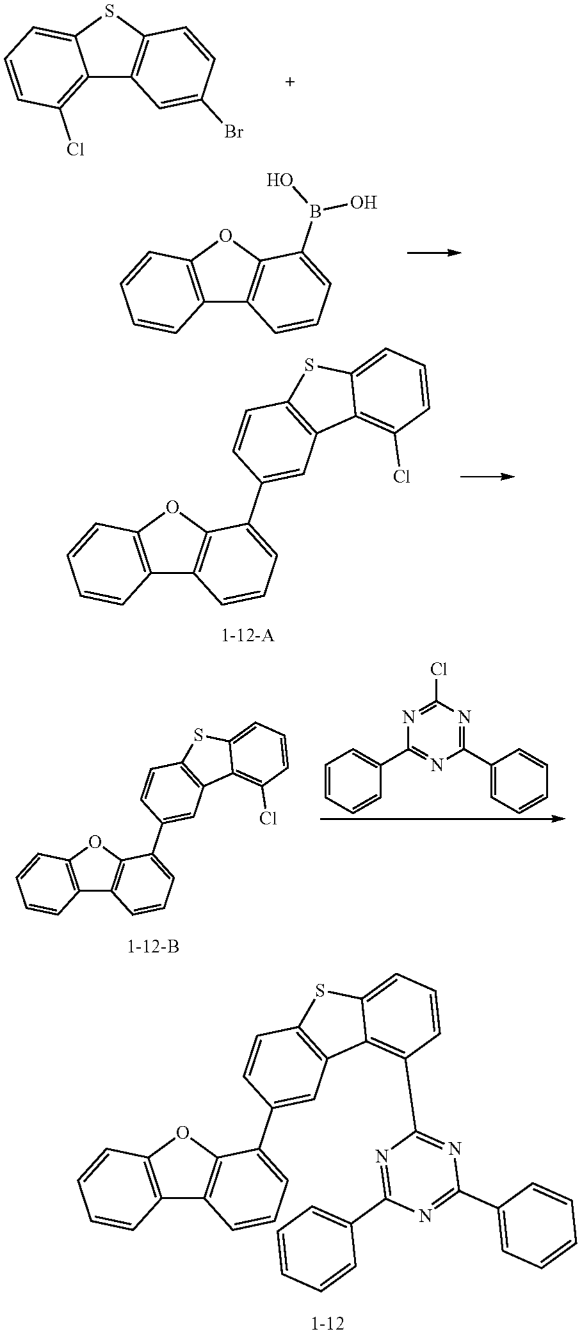

Compound 1-12 (16.9 g, yield: 67%) was prepared in the same manner as in the Preparation of Compound 1-11, except that in step 1 of the Preparation of Compound 1-11, 8-bromo-1-chlorodibenzo[b,d]thiophene was used instead of 2-bromo-7-chlorodibenzo[b,d]furan.

MS: $[M+H]^+$=582.7

Preparation Example 1-13: Preparation of Compound 1-13

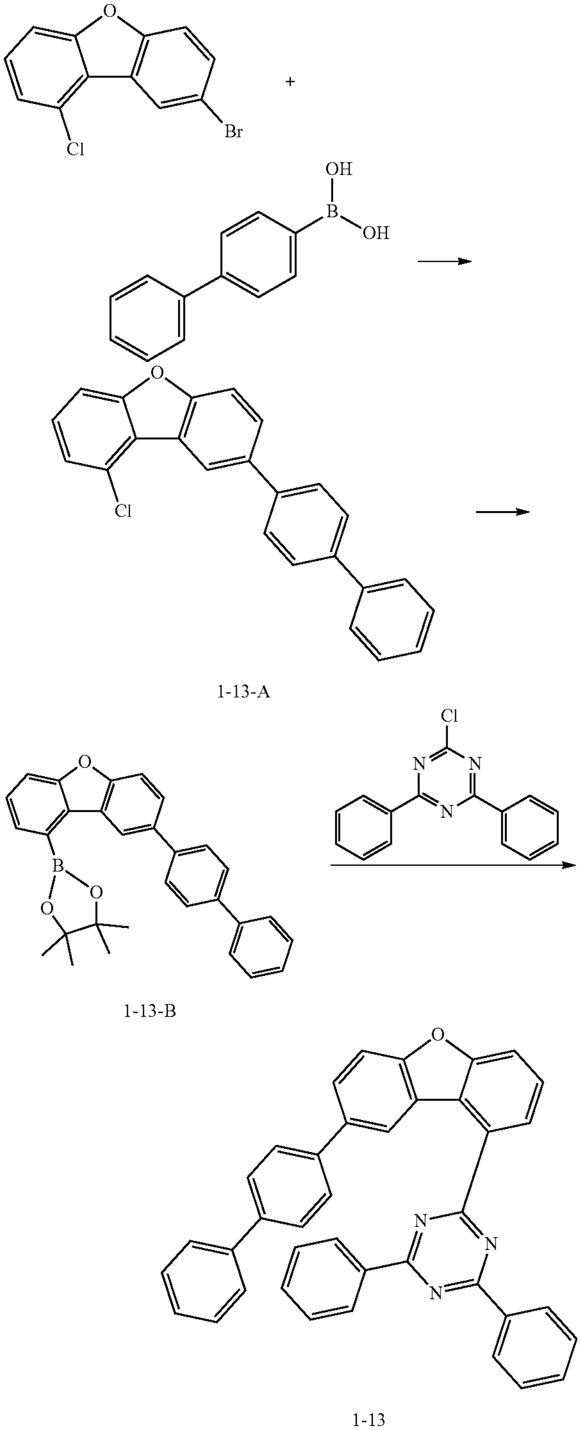

Compound 1-13 (12.9 g, yield: 54%) was prepared in the same manner as in the Preparation of Compound 1-11, except that in step 1 of the Preparation of Compound 1-11, 8-bromo-1-chlorodibenzo[b,d]thiophene was used instead of 2-bromo-7-chlorodibenzo[b,d]furan, and [1,1'-biphenyl]-4-ylboronic acid was used instead of dibenzo[b,d]furan-4-ylboronic acid.

MS: $[M+H]^+$=552.7

Preparation Example 2

Preparation Example 2-1: Preparation of Compound 2-1

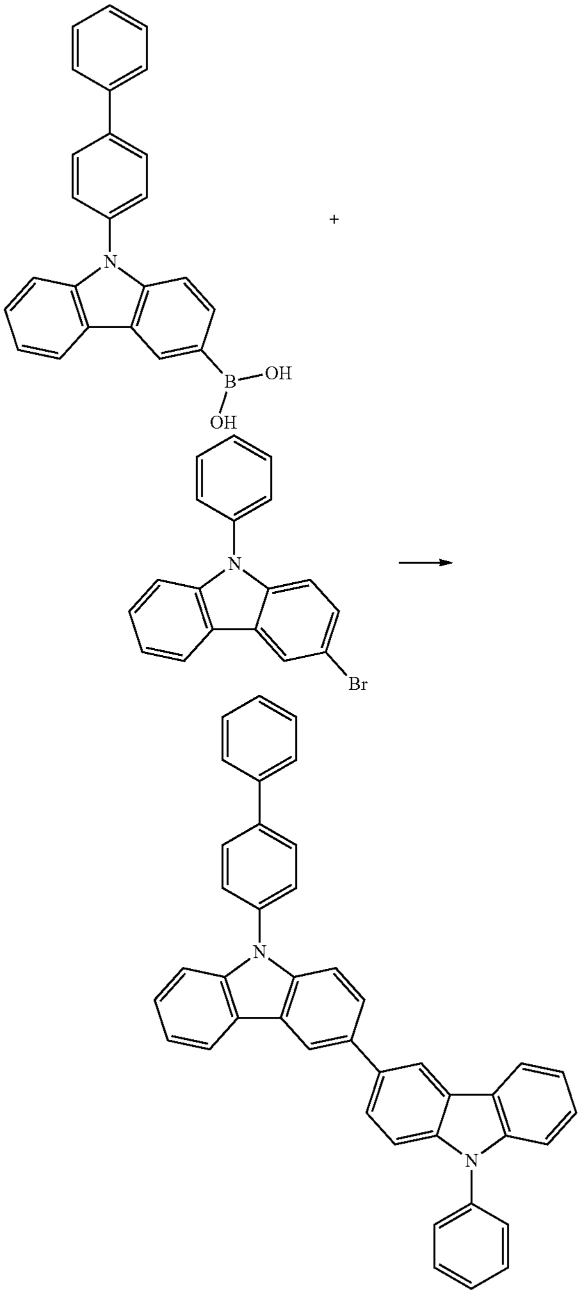

2-1

(9-([1,1'-biphenyl]-4-yl)-9H-carbazol-3-yl)boronic acid (15 g, 41.3 mmol) and 3-bromo-9-phenyl-9H-carbazole (13.3 g, 41.3 mmol) were added to THF (300 ml) under a nitrogen atmosphere, and the mixture was stirred and refluxed. Then, potassium carbonate (17.1 g, 123.9 mmol) was dissolved in water (51 ml), added thereto, and the mixture was sufficiently stirred and then bis(tri-tert-butylphosphine)palladium(0) (0.6 g, 1.2 mmol) was added. After the reaction for 3 hours, the reaction mixture was cooled to room temperature, and the organic layer and the aqueous layer were separated and then the organic layer was distilled. This was again added to and dissolved in chloroform (1158 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethyl acetate to prepare a white solid Compound 2-1 (16.2 g, yield: 70%).

MS: $[M+H]^+$=561.7

Preparation Example 2-2: Preparation of Compound 2-2

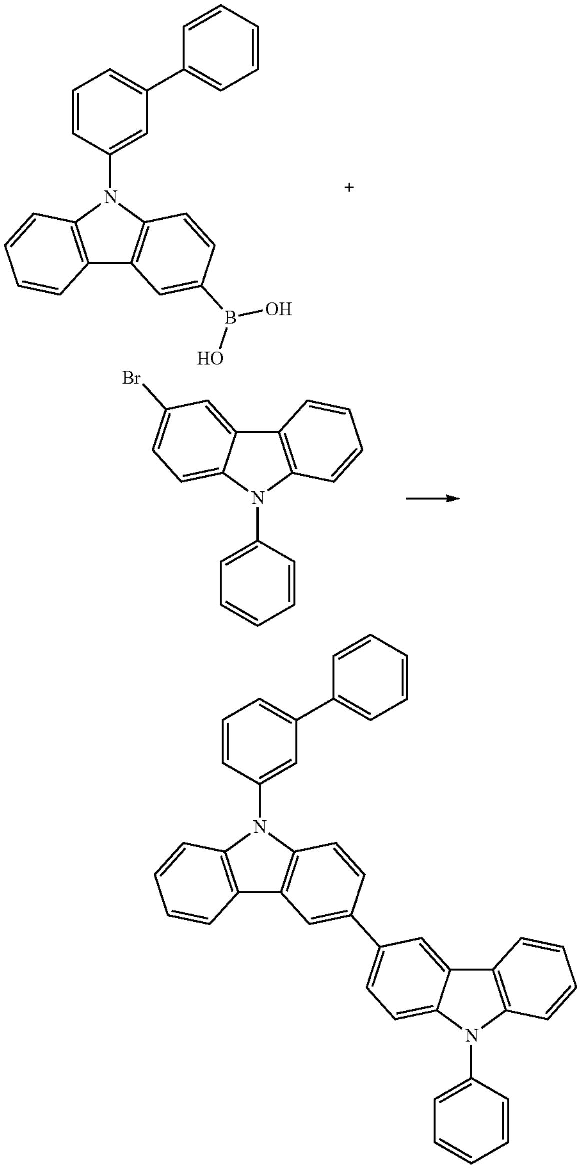

2-2

(9-([1,1'-Biphenyl]-3-yl)-9H-carbazol-3-yl)boronic acid (15 g, 41.3 mmol) and 3-bromo-9-phenyl-9H-carbazole (13.3 g, 41.3 mmol) were added to THF (300 ml) under a nitrogen atmosphere, and the mixture was stirred and refluxed. Then, potassium carbonate (17.1 g, 123.9 mmol) was dissolved in water (51 ml), added thereto, and the mixture was sufficiently stirred and then bis(tri-tert-butylphosphine)palladium(0) (0.6 g, 1.2 mmol) was added. After the reaction for 3 hours, the reaction mixture was cooled to room temperature, and the organic layer and the aqueous layer were separated and then the organic layer was distilled. This was again added to and dissolved in chloroform (1158 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethyl acetate to prepare a white solid Compound 2-2 (18.1 g, yield: 78%).

MS: $[M+H]^+$=561.7

Preparation Example 2-3: Preparation of Compound 2-3

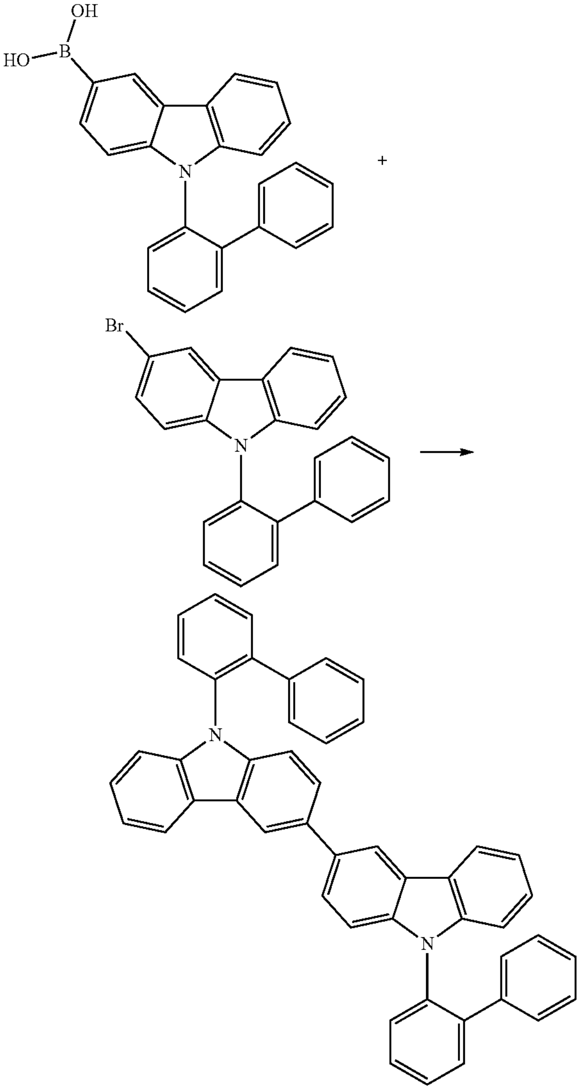

2-3

(9-([1,1'-Biphenyl]-2-yl)-9H-carbazol-3-y)boronic acid (15 g, 41.3 mmol) and 9-([1,1'-biphenyl]-2-yl)-3-bromo-9H-carbazole (16.4 g, 41.3 mmol) were added to THF (300 ml) under a nitrogen atmosphere, and the mixture was stirred and refluxed. Then, potassium carbonate (17.1 g, 123.9 mmol) was dissolved in water (51 ml), added thereto, and the mixture was sufficiently stirred and then bis(tri-tert-butylphosphine)palladium(0) (0.6 g, 1.2 mmol) was added. After the reaction for 4 hours, the reaction mixture was cooled to room temperature, and the organic layer and the aqueous layer were separated and then the organic layer was distilled. This was again added to and dissolved in chloroform (1315 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethyl acetate to prepare a white solid Compound 2-3 (15.3 g, yield: 58%).

MS: $[M+H]^+$=637.8

Preparation Example 2-4: Preparation of Compound 2-4

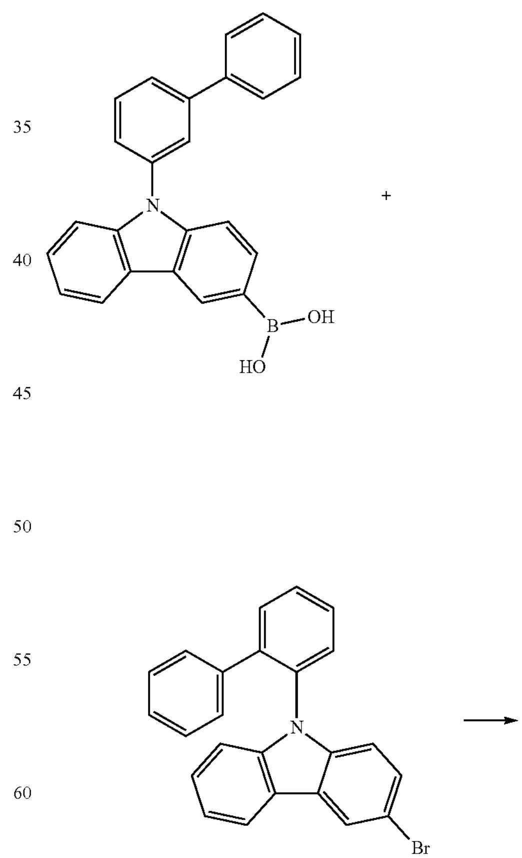

-continued

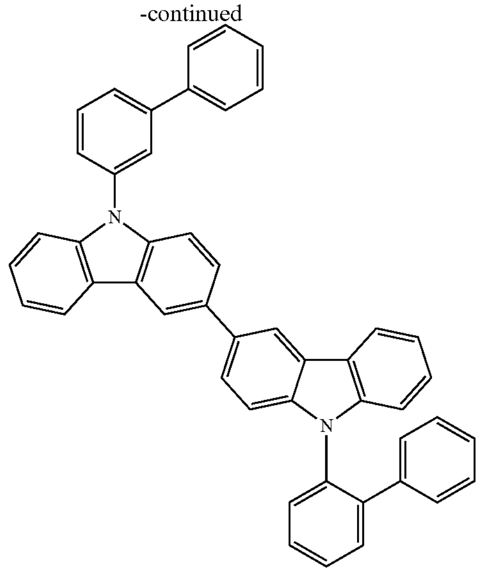

2-4

A white solid compound 2-4 (17.1 g, yield: 65%) was prepared in the same manner as in the Preparation of Compound 2-1, except that (9-([1,1'-biphenyl]-3-yl)-9H-carbazol-3-yl)boronic acid was used instead of (9-([1,1'-biphenyl]-4-yl)-9H-carbazol-3-yl)boronic acid, and 9-([1,1'-biphenyl]-2-yl)-3-bromo-9H-carbazole was used instead of 3-bromo-9-phenyl-9H-carbazole.

MS: $[M+H]^+=637.8$

Preparation Example 2-5: Preparation of Compound 2-5

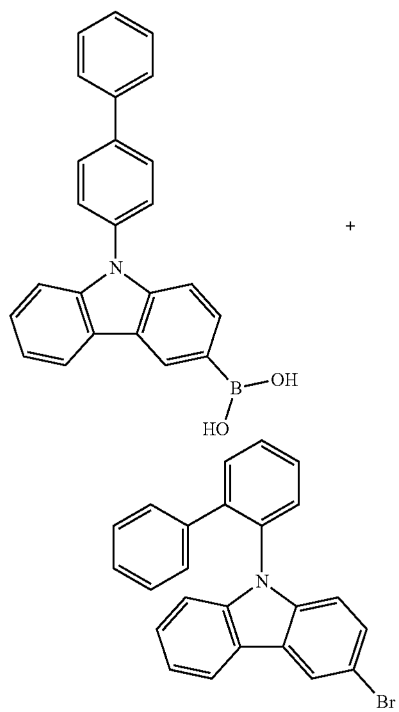

-continued

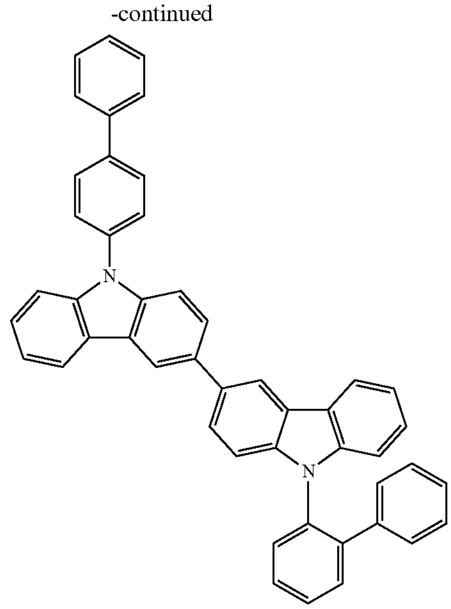

2-5

A white solid Compound 2-5 (16 g, yield: 61%) was prepared in the same manner as in the Preparation of Compound 2-1, except that 9-([1,1'-biphenyl]-2-yl)-3-bromo-9H-carbazole was used instead of 3-bromo-9-phenyl-9H-carbazole.

MS: $[M+H]^+=637.8$

Preparation Example 2-6: Preparation of Compound 2-6

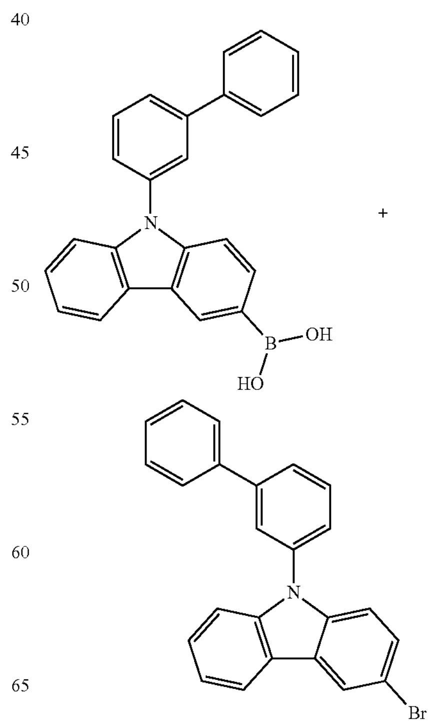

-continued

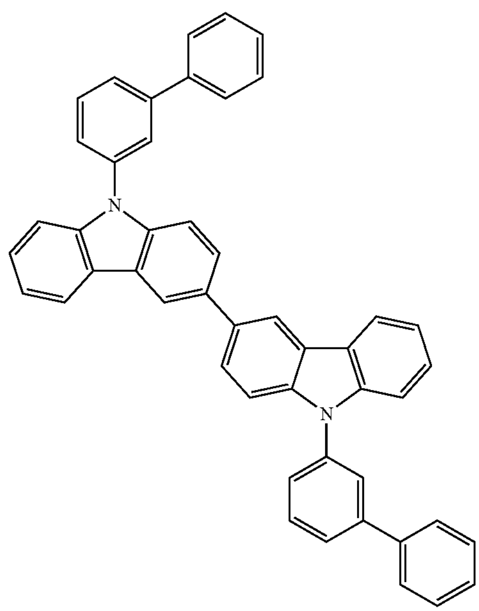

2-6

A white solid Compound 2-6 (15.3 g, yield: 58%) was prepared in the same manner as in the Preparation of Compound 2-1, except that (9-([1,1'-biphenyl]-3-yl)-9H-carbazol-3-yl)boronic acid was used instead of (9-([1,1'-biphenyl]-4-yl)-9H-carbazol-3-yl)boronic acid, and 9-([1,1'-biphenyl]-3-yl)-3-bromo-9H-carbazole was used instead of 3-bromo-9-phenyl-9H-carbazole.

MS: $[M+H]^+$=637.8

Preparation Example 2-7: Preparation of Compound 2-7

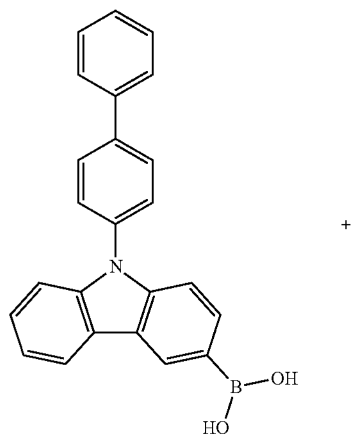

+

-continued

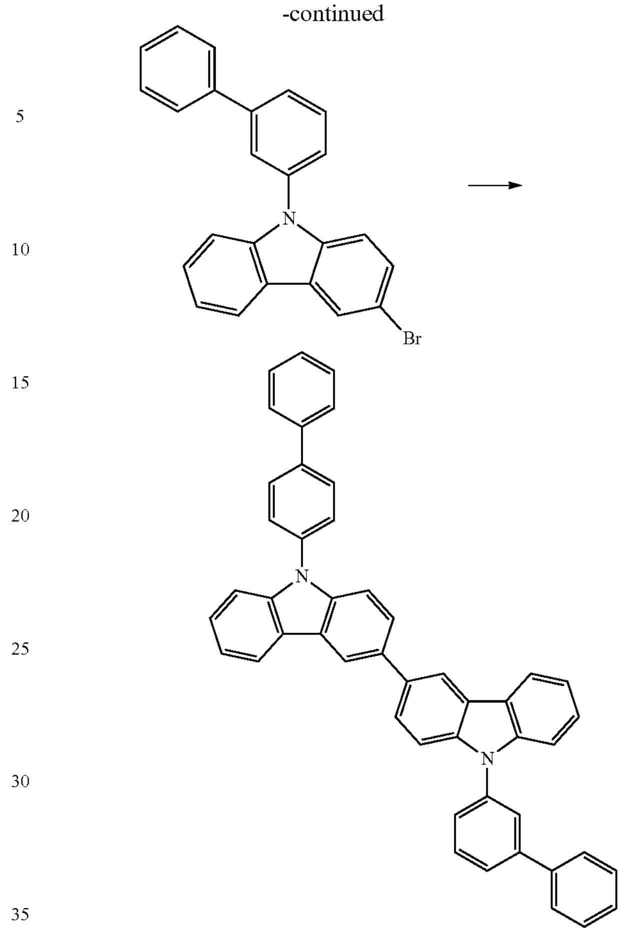

2-7

A white solid Compound 2-7 (17.5 g, yield: 50%) was prepared in the same manner as in the Preparation of Compound 2-1, except that 9-([1,1'-biphenyl]-3-yl)-3-bromo-9H-carbazole was used instead of 3-bromo-9-phenyl-9H-carbazole.

MS: $[M+H]^+$=637.8

Preparation Example 2-8: Preparation of Compound 2-8

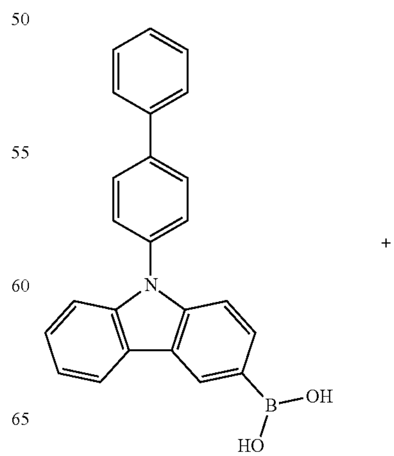

+

-continued

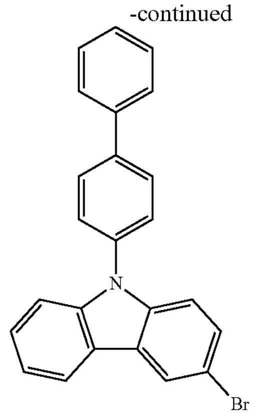

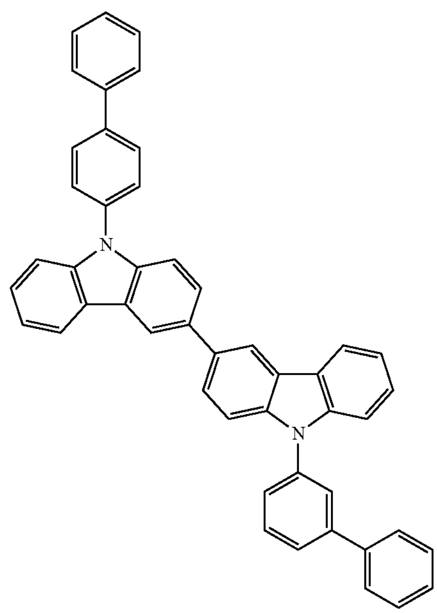

2-8

A white solid Compound 2-8 (24.2 g, yield: 69%) was prepared in the same manner as in the Preparation of Compound 2-1, except that 9-([1,1'-biphenyl]-4-yl)-3-bromo-9H-carbazole was used instead of 3-bromo-9-phenyl-9H-carbazole.

MS: $[M+H]^+$=637.8

Preparation Example 2-9: Preparation of Compound 2-9

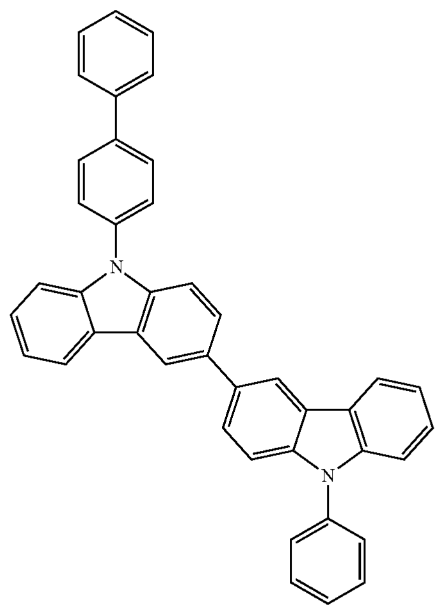

2-1

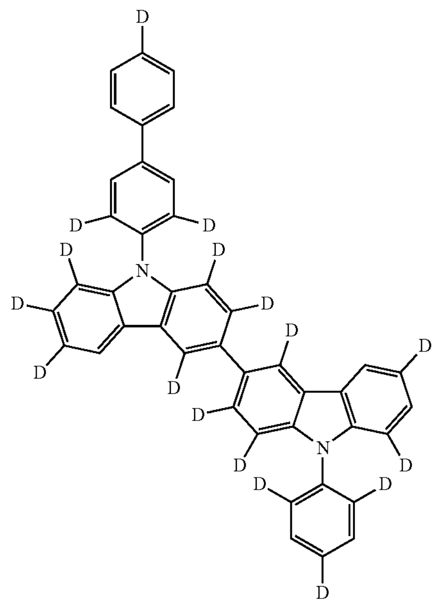

2-9

Compound 2-1 (20 g, 31.41 mmol) was added to benzene-D6 (200 ml) under a nitrogen atmosphere, and the mixture was stirred. Then, triflic acid (3.4 g, 22.65 mmol) was added thereto, and the mixture was heated and stirred. After the reaction for 4 hours, the reaction mixture was cooled to room temperature, ethanol was added thereto and the resulting solid was filtered. The solid was added to and dissolved in chloroform (886 ml), washed twice with water, and the organic layer was separated, anhydrous magnesium sulfate was added thereto, stirred, and then filtered, and the filtrate was distilled under reduced pressure. The concentrated compound was purified through a silica column using chloroform and ethyl acetate to prepare a white solid Compound 2-9 (13.2 g, yield: 64%).

MS: $[M+H]^+$=578.8

Preparation Example 2-10: Preparation of Compound 2-10

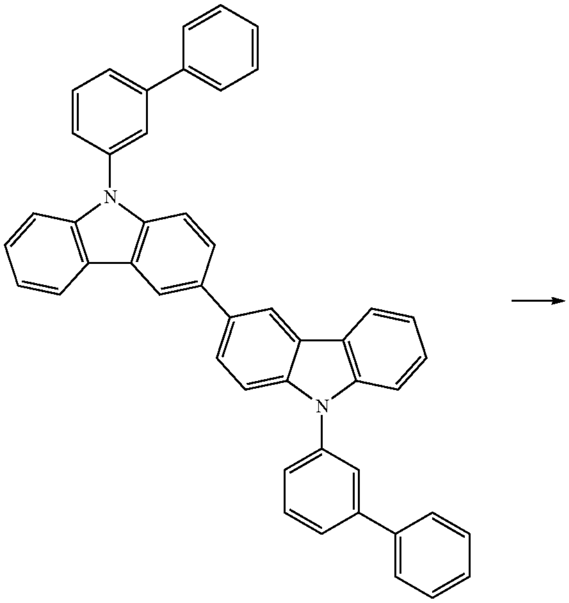

2-6

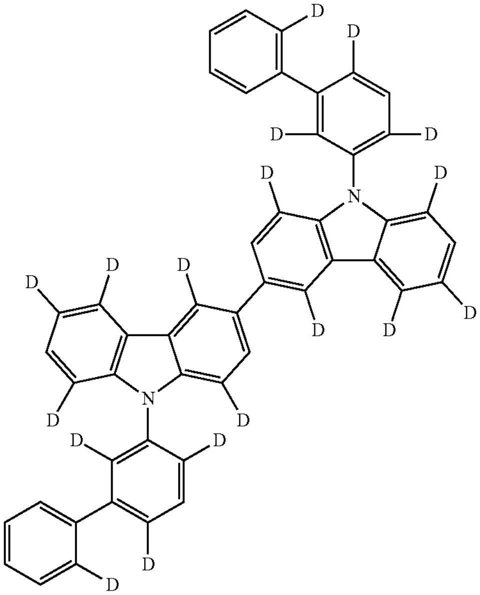

2-10

A white solid Compound 2-10 (12.6 g, yield: 61%) was prepared in the same manner as in the Preparation of Compound 2-9, except that Compound 2-6 was used instead of Compound 2-1.

MS: $[M+H]^+$=655.9

Preparation Example 2-11: Preparation of Compound 2-11

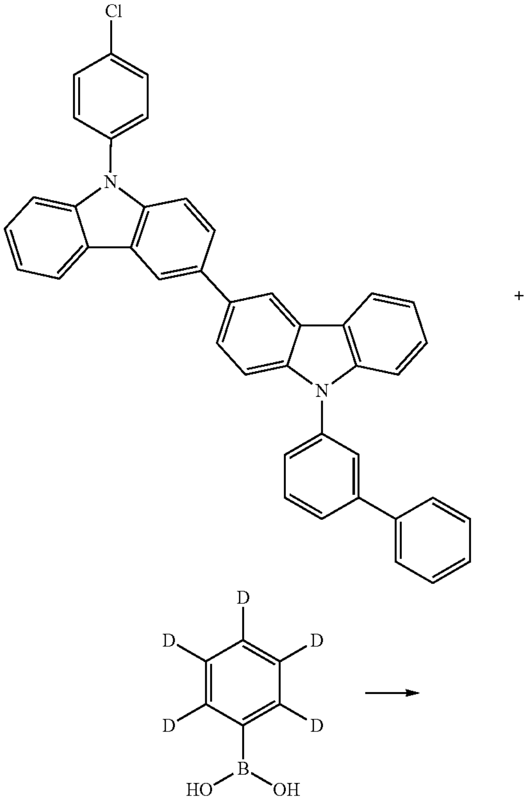

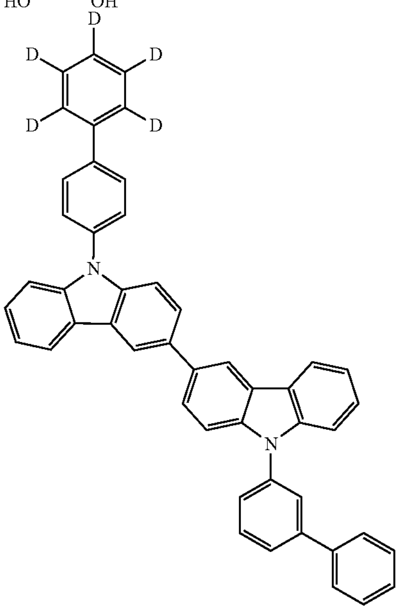

2-11

9-([1,1'-Biphenyl]-3-yl)-9'-(4-chlorophenyl)-9H,9'H-3,3'-bicarbazole (15 g, 25.2 mmol) and (phenyl-d5)boronic acid (3.2 g, 25.2 mmol) were added to dioxane (300 ml) under a nitrogen atmosphere, and the mixture was stirred and refluxed. Then, $K_3PO_4$ (16.1 g, 75.6 mmol) was dissolved in water (16 ml), added thereto, and the mixture was sufficiently stirred, and bis(dibenzylideneacetone)palladium(0) (0.4 g, 0.8 mmol) and tricyclohexylphosphine (0.4 g, 1.5 mmol) were added. After the reaction for 9 hours, the reaction mixture was cooled to room temperature, and then the resulting solid was filtered. The solid was added to and dissolved in dichlorobenzene (485 ml), washed twice with water, and the organic layer was separated, anhydrous magnesium sulfate was added thereto, stirred, and then filtered, and the filtrate was distilled under reduced pressure. The concentrated compound was recrystallized using dichlorobenzene and ethyl acetate to prepare a white solid Compound 2-11 (9.9 g, yield: 61%).

MS: $[M+H]^+$=642.8

Preparation Example 3

Preparation Example 3-1: Preparation of Compound 3-1

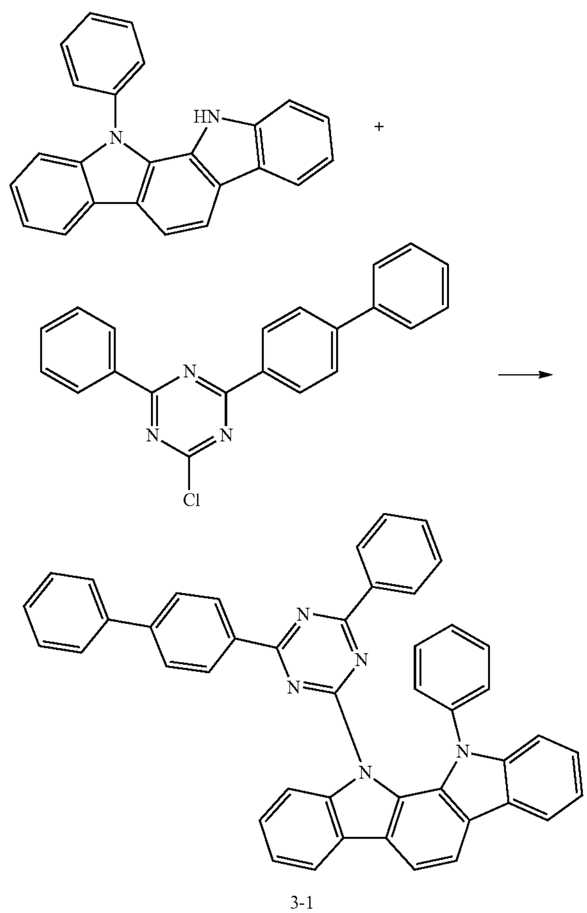

3-1

11-Phenyl-11,12-dihydroindolo[2,3-a]carbazole (20.7 g, 60.2 mmol) and 2-([1,1'-biphenyl]-4-yl)-4-chloro-6-phenyl-1,3,5-triazine (20.7 g, 60.2 mmol) were added to DMF (400 ml) under a nitrogen atmosphere, and the mixture was stirred and refluxed. Then, sodium tertbutoxide (17.4 g, 180.5 mmol) was added thereto, heated and stirred. After the reaction for 3 hours, the reaction mixture was cooled to room temperature, and then the resulting solid was filtered. The solid was added to and dissolved in chloroform (1155 ml), washed twice with water, and the organic layer was separated, anhydrous magnesium sulfate was added thereto, stirred, and then filtered, and the filtrate was distilled under reduced pressure. The concentrated compound was purified through a silica column using chloroform and ethyl acetate to prepare a yellow solid Compound 3-1 (23.1 g, yield: 60%).

MS: $[M+H]^+$=640.8

Preparation Example 3-2: Preparation of Compound 3-2

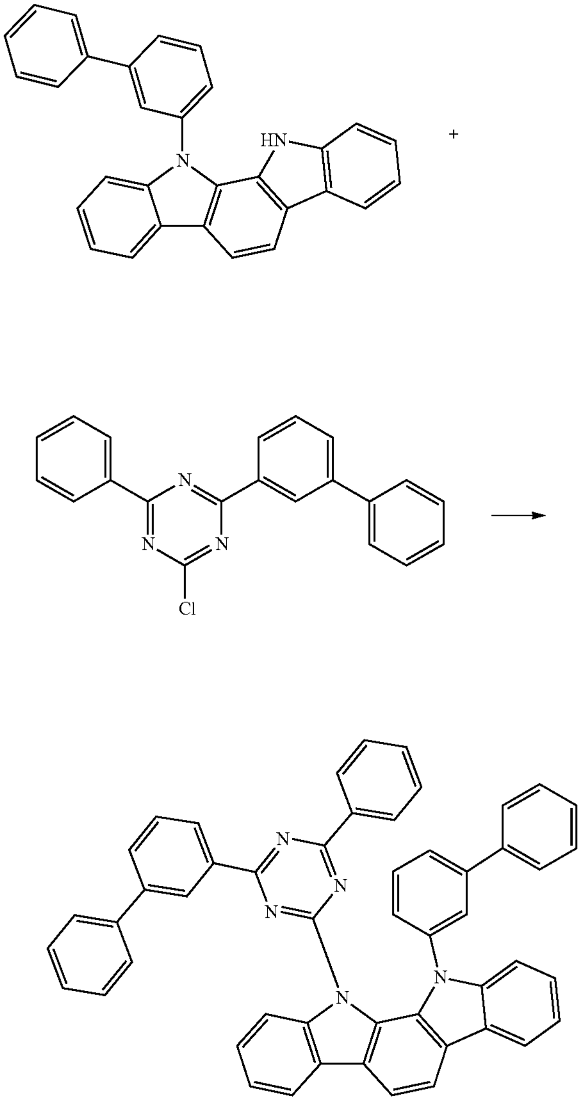

3-2

Compound 3-2 (19.3 g, yield: 55%) was prepared in the same manner as in the Preparation of Compound 3-1, except that 11-([1,1'-biphenyl]-3-yl)-11,12-dihydroindolo[2,3-a]carbazole was used instead of 11-phenyl-11,12-dihydroindolo[2,3-a]carbazole, and [2-([1,1'-biphenyl]-3-yl)-4-chloro-6-phenyl-1,3,5-triazine was used instead of 2-([1,1'-biphenyl]-4-yl)-4-chloro-6-phenyl-1,3,5-triazine.

MS: $[M+H]^+$=716.9

Preparation Example 3-3: Preparation of Compound 3-3

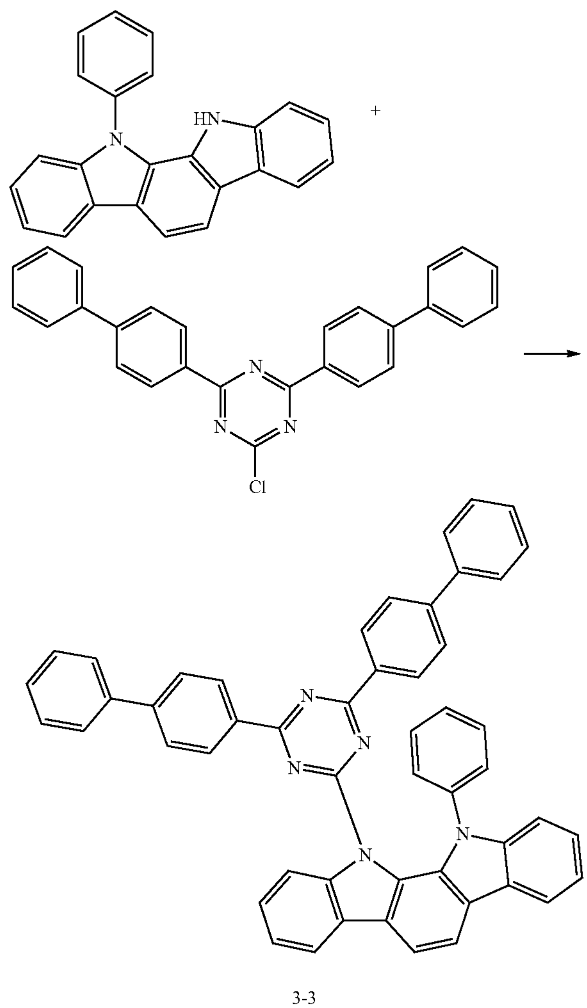

3-3

Compound 3-3 (22.4 g, yield: 52%) was prepared in the same manner as in the Preparation of Compound 3-1, except that 2,4-di([1,1'-biphenyl]-4-yl)-6-chloro-1,3,5-triazine was used instead of 2-([1,1'-biphenyl]-4-yl)-4-chloro-6-phenyl-1,3,5-triazine.

MS: $[M+H]^+$=716.9

Preparation Example 3-4: Preparation of Compound 3-4

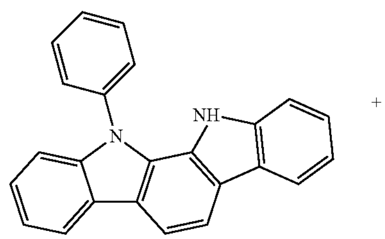

-continued

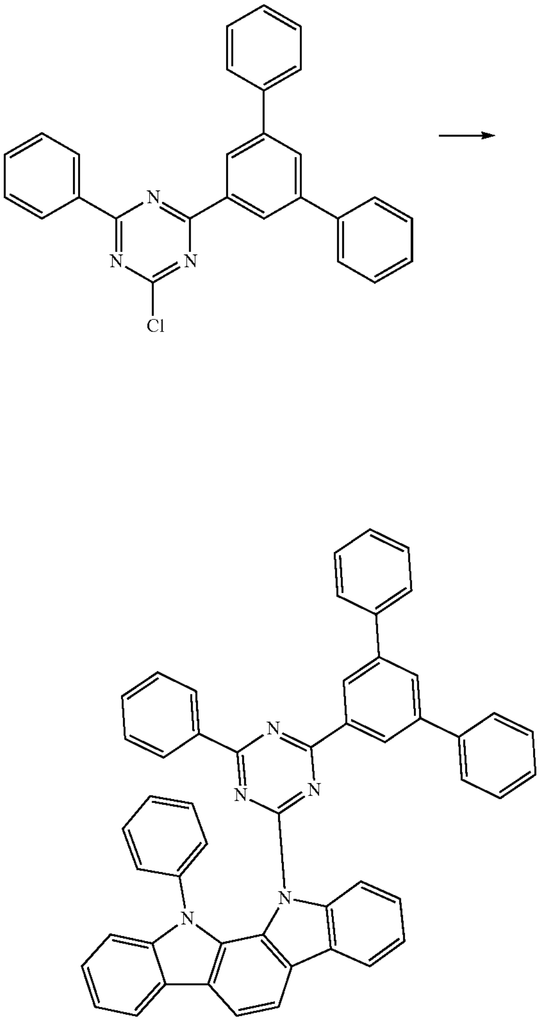

3-4

Compound 3-4 (28.4 g, yield: 66%) was prepared in the same manner as in the Preparation of Compound 3-1, except that 2-([1,1':3',1''-terphenyl]-5'-yl)-4-chloro-6-phenyl-1,3,5-triazine was used instead of 2-([1,1'-biphenyl]-4-yl)-4-chloro-6-phenyl-1,3,5-triazine.

MS: $[M+H]^+$=716.9

Preparation Example 3-5: Preparation of Compound 3-5

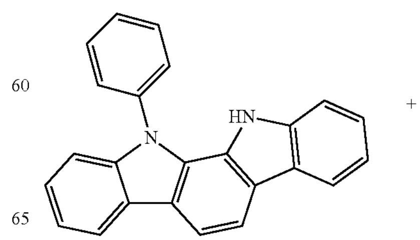

-continued

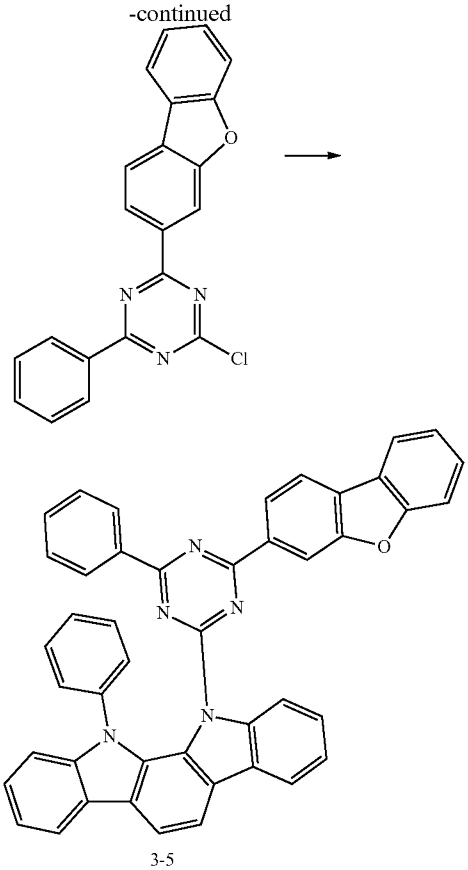

3-5

Compound 3-5 (24.4 g, yield: 62%) was prepared in the same manner as in the Preparation of Compound 3-1, except that 2-chloro-4-(dibenzo[b,d]furan-3-yl)-6-phenyl-1,3,5-triazine was used instead of 2-([1,1'-biphenyl]-4-yl)-4-chloro-6-phenyl-1,3,5-triazine.

MS: $[M+H]^+$=654.8

Preparation Example 3-6: Preparation of Compound 3-6

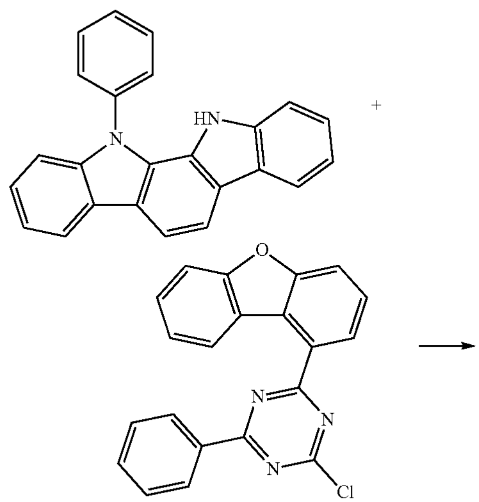

-continued

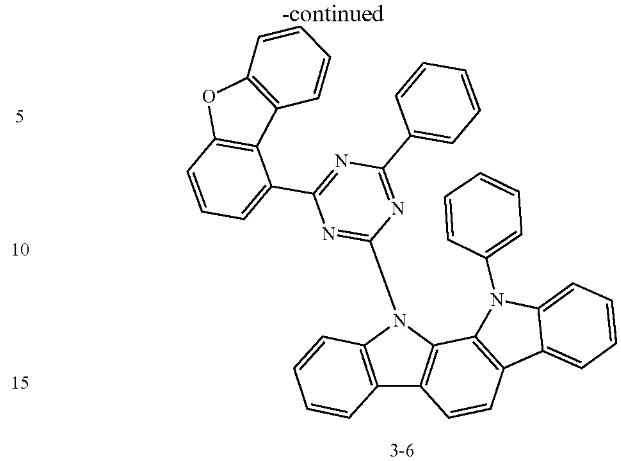

3-6

Compound 3-6 (23.2 g, yield: 59%) was prepared in the same manner as in the Preparation of Compound 3-1, except that 2-chloro-4-(dibenzo[b,d]furan-1-yl)-6-phenyl-1,3,5-triazine was used instead of 2-([1,1'-biphenyl]-4-yl)-4-chloro-6-phenyl-1,3,5-triazine.

MS: $[M+H]^+$=654.8

Preparation Example 3-7: Preparation of Compound 3-7

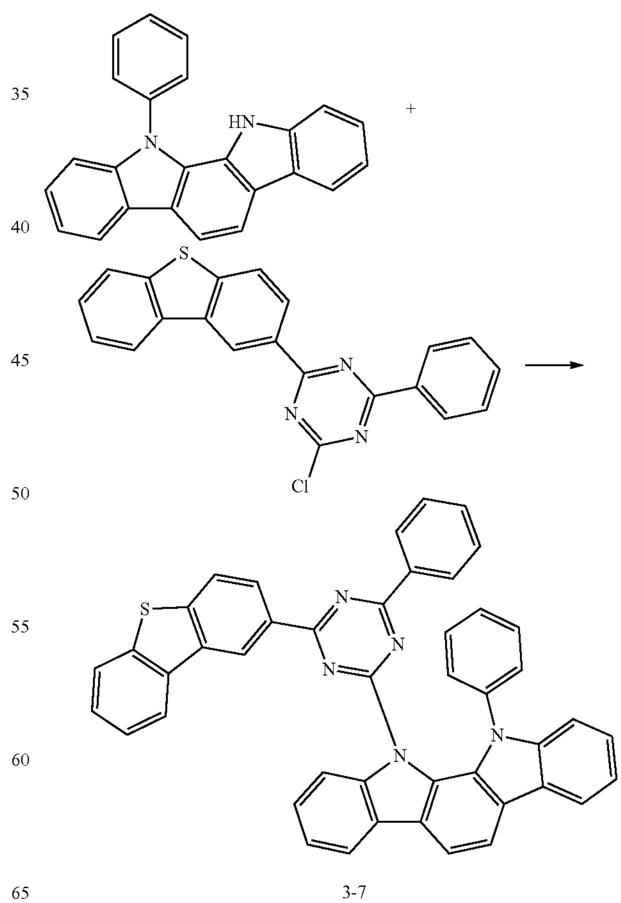

3-7

Compound 3-7 (25 g, yield: 62%) was prepared in the same manner as in the Preparation of Compound 3-1, except that 2-chloro-4-(dibenzo[b,d]thiophen-2-yl)-6-phenyl-1,3,5-triazine was used instead of 2-([1,1'-biphenyl]-4-yl)-4-chloro-6-phenyl-1,3,5-triazine.

MS: $[M+H]^+$=670.8

Preparation Example 3-8: Preparation of Compound 3-8

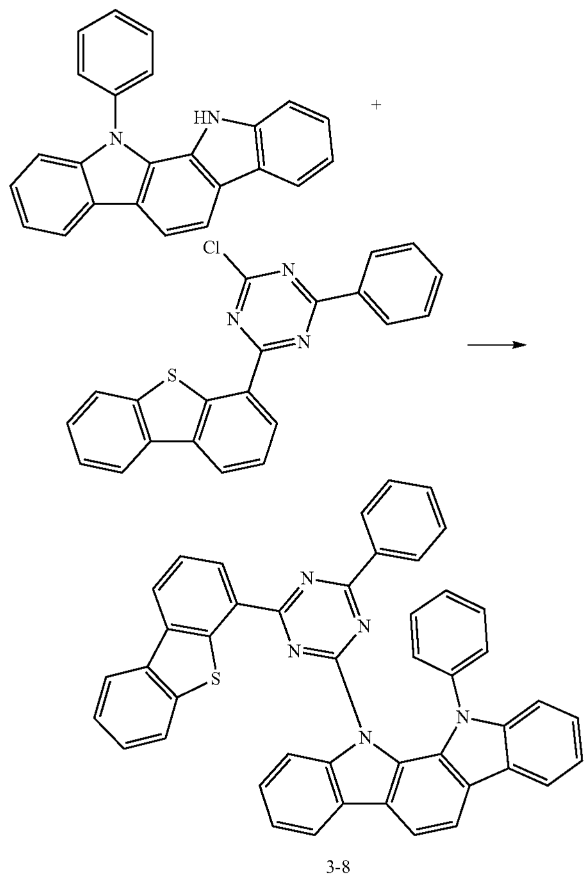

3-8

Compound 3-8 (22.6 g, yield: 56%) was prepared in the same manner as in the Preparation of Compound 3-1, except that 2-chloro-4-(dibenzo[b,d]thiophen-4-yl)-6-phenyl-1,3,5-triazine was used instead of 2-([1,1'-biphenyl]-4-yl)-4-chloro-6-phenyl-1,3,5-triazine.

MS: $[M+H]^+$=670.8

Preparation Example 3-9: Preparation of Compound 3-9

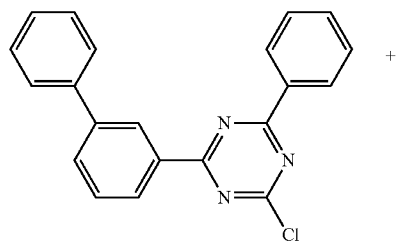

-continued

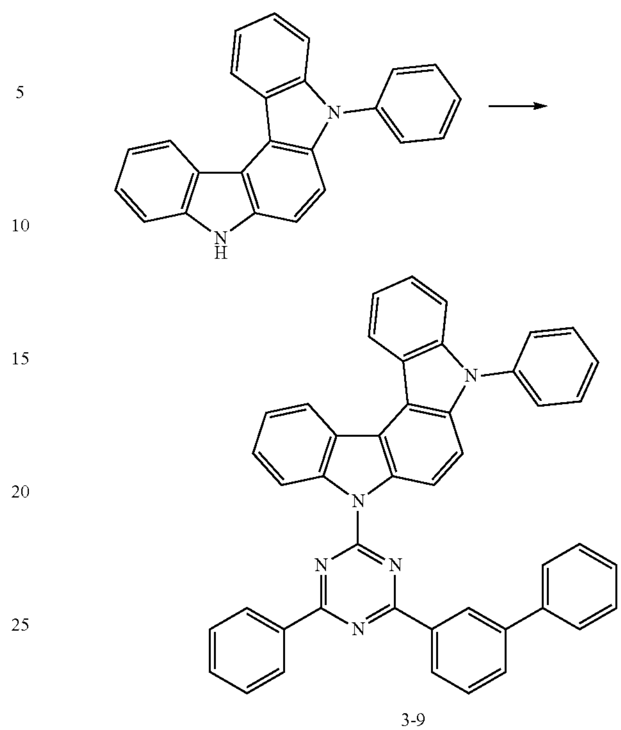

3-9

Compound 3-9 (28.5 g, yield: 74%) was prepared in the same manner as in the Preparation of Compound 3-1, except that 5-phenyl-5,8-dihydroindolo[2,3-c]carbazole was used instead of 11-phenyl-11,12-dihydroindolo[2,3-a]carbazole, and 2-([1,1'-biphenyl]-3-yl)-4-chloro-6-phenyl-1,3,5-triazine was used instead of 2-([1,1'-biphenyl]-4-yl)-4-chloro-6-phenyl-1,3,5-triazine.

MS: $[M+H]^+$=640.8

Preparation Example 3-10: Preparation of Compound 3-10

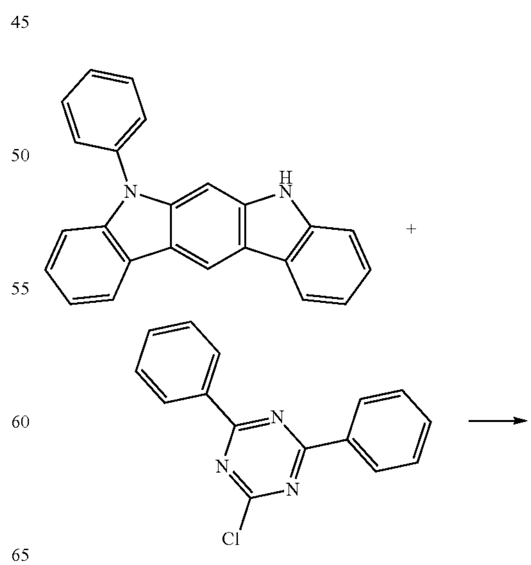

-continued

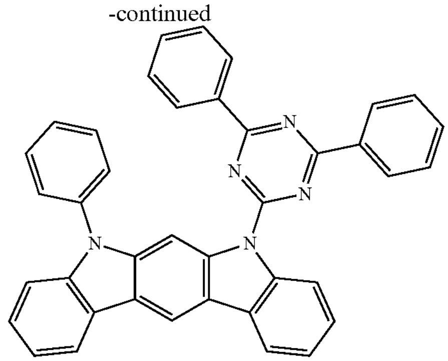

3-10

Compound 3-10 (20 g, yield 59%) was prepared in the same manner as in the Preparation of Compound 3-1, except that 5-phenyl-5,7-dihydroindolo[2,3-b]carbazole was used instead of 11-phenyl-11,12-dihydroindolo[2,3-a]carbazole, and 2-chloro-4,6-diphenyl-1,3,5-triazine was used instead of 2-([1,1'-biphenyl]-4-yl)-4-chloro-6-phenyl-1,3,5-triazine.

MS: $[M+H]^+$=564.7

Preparation Example 3-11: Preparation of Compound 3-11

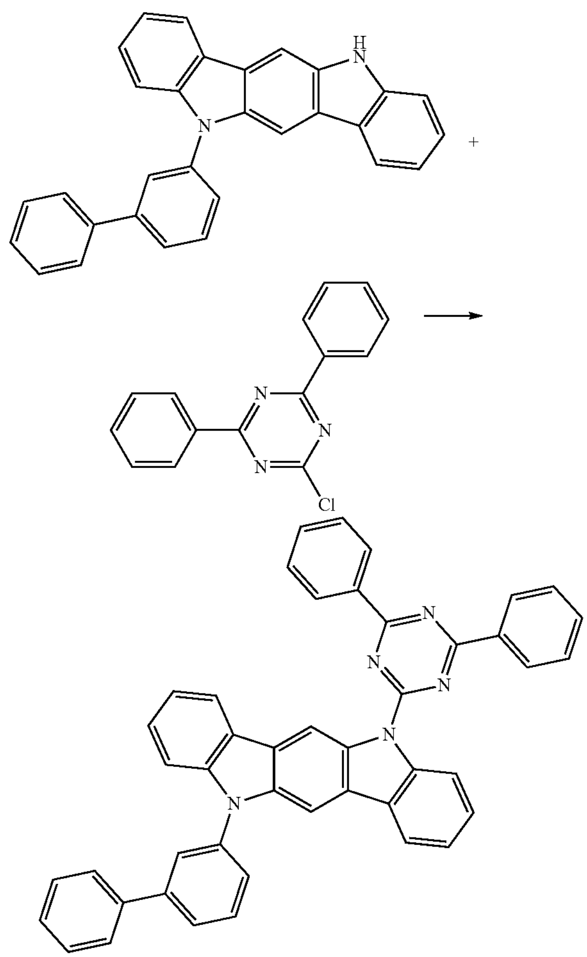

3-11

Compound 3-11 (23.5 g, yield: 61%) was prepared in the same manner as in the Preparation of Compound 3-1, except that 5-([1,1'-biphenyl]-3-yl)-5,11-dihydroindolo[3,2-b]carbazole was used instead of 11-phenyl-11,12-dihydroindolo[2,3-a]carbazole, and 2-chloro-4,6-diphenyl-1,3,5-triazine was used instead of 2-([1,1'-biphenyl]-4-yl)-4-chloro-6-phenyl-1,3,5-triazine.

MS: $[M+H]^+$=640.8

Preparation Example 3-12: Preparation of Compound 3-12

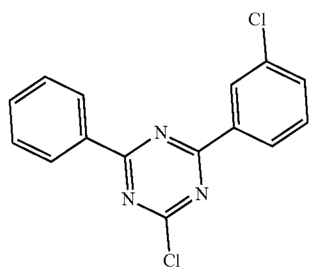

+

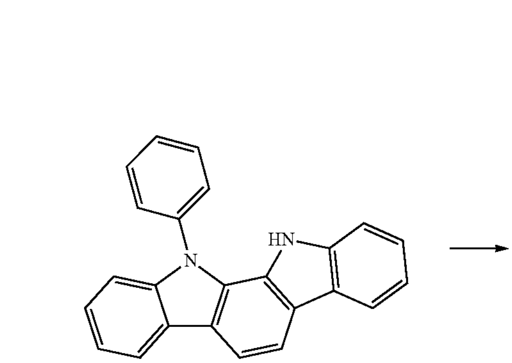

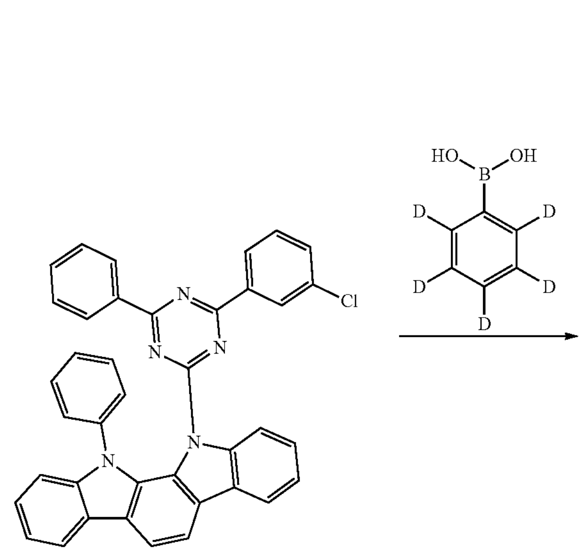

3-12-A

-continued

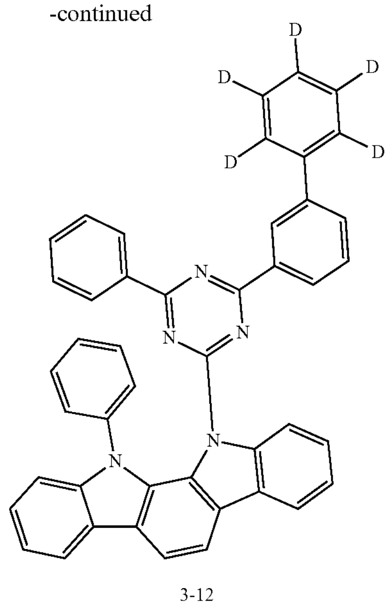

3-12

Step 1) Preparation of compound 3-12-A 11-phenyl-11,12-dihydroindolo[2,3-a]carbazole (20 g, 60.2 mmol) and 2-chloro-4-(3-chlorophenyl)-6-phenyl-1,3,5-triazine (18.2 g, 60.2 mmol) were added to dirmethylacetamide (200 ml) under a nitrogen atmosphere, and the mixture was stirred and refluxed. Then, $K_3P04$ (383 g, 180.5 mmol) was added thereto, heated and stirred. After the reaction for 3 hours, the reaction mixture was cooled to room temperature, and then the resulting solid was filtered. The solid was added to and dissolved in chloroform (1080 ml), washed twice with water, and the organic layer was separated, anhydrous magnesium sulfate was added thereto, stirred, and then filtered, and the filtrate was distilled under reduced pressure. The concentrated compound was purified through a silica column using chloroform and ethyl acetate to prepare a yellow solid Compound 3-12-A (21.2 g, yield: 59%).

MS: $[M+H]^+$=599.1

Step 2) Preparation of compound 3-12

Compound 3-12-A (15 g, 25.1 mmol) and (phenyl-d5) boronic acid (3.2 g, 25.1 mmol) were added to dioxane (300 ml) under a nitrogen atmosphere, and the mixture was stirred and refluxed. Then, $K_3P04$ (16 g, 75.2 mmol) was dissolved in water (16 ml), added thereto, and the mixture was sufficiently stirred, and then bis(dibenzylideneacetone)palladium(0) (0.4 g, 0.8 mmol) and tricyclohexylphosphine (0.4 g, 1.5 mmol) were added. After the reaction for 6 hours, the reaction mixture was cooled to room temperature, and then the resulting solid was filtered. The solid was added to and dissolved in chloroform (1080 ml), washed twice with water, and the organic layer was separated, anhydrous magnesium sulfate was added thereto, stirred, and then filtered, and the filtrate was distilled under reduced pressure. The concentrated compound was purified through a silica column using dichlorobenzene and ethyl acetate to prepare a yellow solid Compound 3-12 (10.5 g, yield: 65%).

MS: $[M+H]^+$=645.8

Preparation Example 3-13: Preparation of Compound 3-13

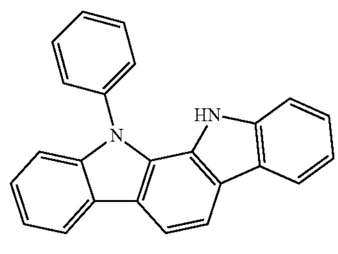

+

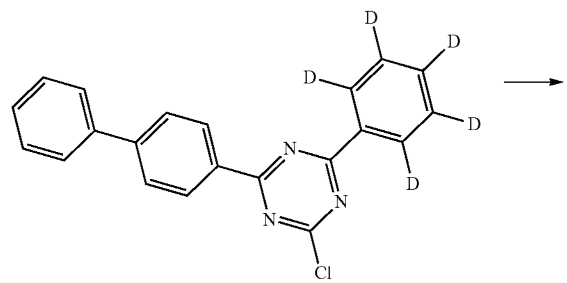

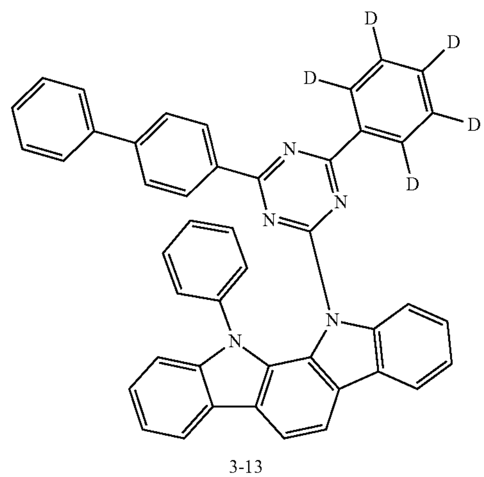

3-13

Compound 3-13 (9.5 g, yield: 59%) was prepared in the same manner as in the Preparation of Compound 3-1, except that 2-([1,1'-biphenyl]-4-yl)-4-chloro-6-(phenyl-d5)-1,3,5-triazine was used instead of 2-([1,1'-biphenyl]-4-yl)-4-chloro-6-phenyl-1,3,5-triazine.

MS: $[M+H]^+$=645.8

Preparation Example 3-14: Preparation of Compound 3-14

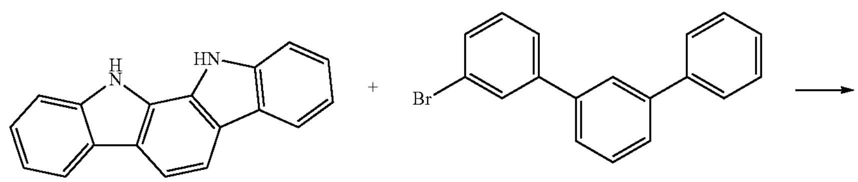

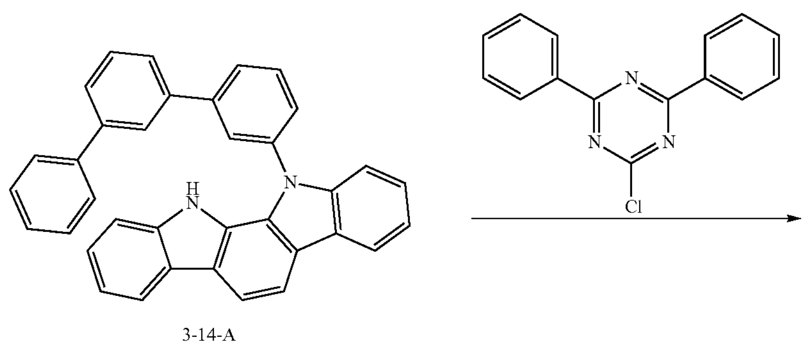

3-14-A

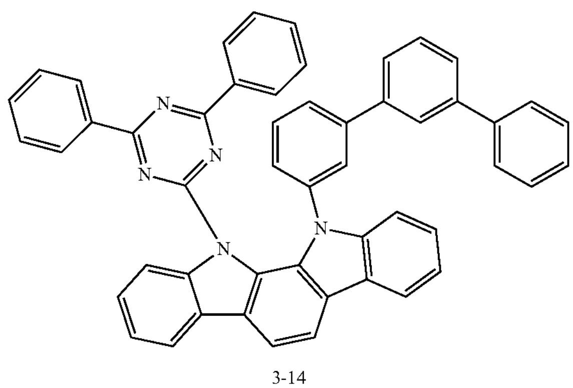

3-14

Step 1) Preparation of Compound 3-14-A 11,12-dihydroindolo[2,3-a]carbazole (20 g, 78 mmol) and 3-bromo-1,1':3,1"-terphenyl (24.1 g, 78 mmol) were added to xylene (400 ml) under a nitrogen atmosphere, and the mixture was stirred and refluxed. Then, $K_3PO_4$ (22.5 g, 234.1 mmol) was added thereto, and the mixture was sufficiently stirred and then bis(tri-tert-butylphosphine)palladium(0) (1.2 g, 2.3 mmol) was added. After the reaction for 3 hours, the reaction mixture was cooled to room temperature, and the organic layer was filtered to remove salts, and then the filtered organic layer was distilled. This was again added to and dissolved in chloroform (378 ml), washed twice with water, and then the organic layer was separated, anhydrous magnesium sulfate was added thereto, stirred, and then filtered, and the filtrate was distilled under reduced pressure. The concentrated compound was recrystallized using chloroform and ethanol to prepare a beige solid Compound 3-14-A (25.3 g, yield: 67%).

MS: $[M+H]^+$=485.6

Step 2) Preparation of Compound 3-14

Compound 3-14-A (20 g, 41.3 mmol) and 2-chloro-4,6-diphenyl-1,3,5-triazine (11 g, 41.3 mmol) were added to dimethylacetamide (200 mi) under a nitrogen atmosphere, and the mixture was stirred and refluxed. Then, $K_3PO_4$ (26.3 g, 123.8 mmol) was added thereto, and the mixture was heated and stirred. After the reaction for 1 hour, the reaction mixture was cooled to room temperature, and the resulting solid was filtered. The solid was added to and dissolved in chloroform (886 ml), washed twice with water, and the organic layer was separated, anhydrous magnesium sulfate was added thereto, stirred, and then filtered, and the filtrate was distilled under reduced pressure. The concentrated compound was purified through a silica column using chloroform and ethyl acetate to prepare a yellow solid Compound 3-14 (15.1 g, yield: 51%).

MS: $[M+H]^+$=716.9

Preparation Example 3-15: Preparation of Compound 3-15

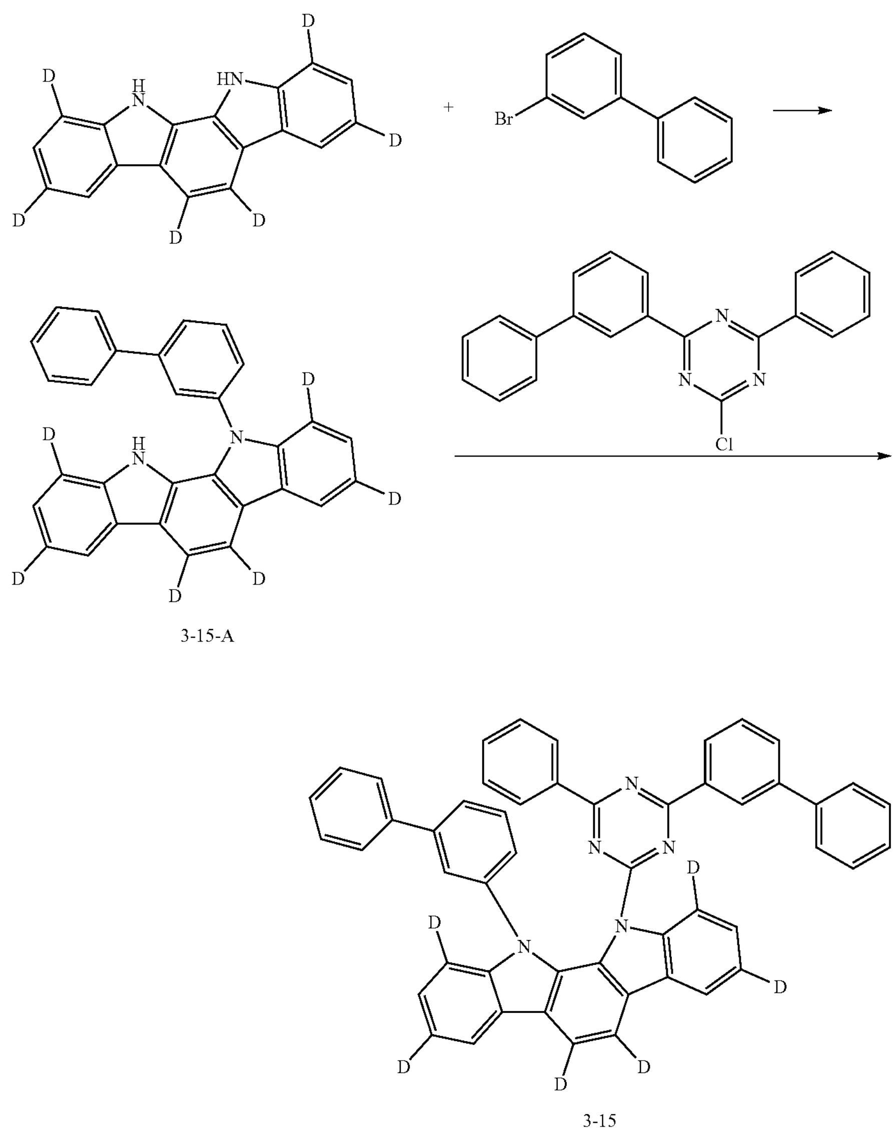

3-15-A 3-15

Step 1) Preparation of Compound 3-15-A

Compound 3-15-A (20.2 g, yield: 64%) was prepared in the same manner as in step 1 of the Preparation of Compound 3-14, except that 11,12-dihydroindolo[2,3-a]carbazole-1,3,5,6,8,10-d6 was used instead of 11,12-dihydroindolo[2,3-a]carbazole, and 3-bromo-1,1'-biphenyl was used instead of 3-bromo-1,1':3',1"-terphenyl.

MS: $[M+H]^+$=415.5

Step 2) Preparation of Compound 3-15

Compound 3-15 (29.7 g, yield: 54%) was prepared in the same manner as in the Preparation of Compound 3-1, except that 11-([1,1'-biphenyl]-3-yl)-11,12-dihydroindolo[2,3-a]carbazole-1,3,5,6,8,10-d6 was used instead of 11-phenyl-11,12-dihydroindolo[2,3-a]carbazole, and 2-([1,1'-biphenyl]-3-yl)-4-chloro-6-phenyl-1,3,5-triazine was used instead of 2-([1,1'-biphenyl]-4-yl)-4-chloro-6-phenyl-1,3,5-triazine.

MS: $[M+H]^+$=722.9

Preparation Example 3-16: Preparation of Compound 3-16

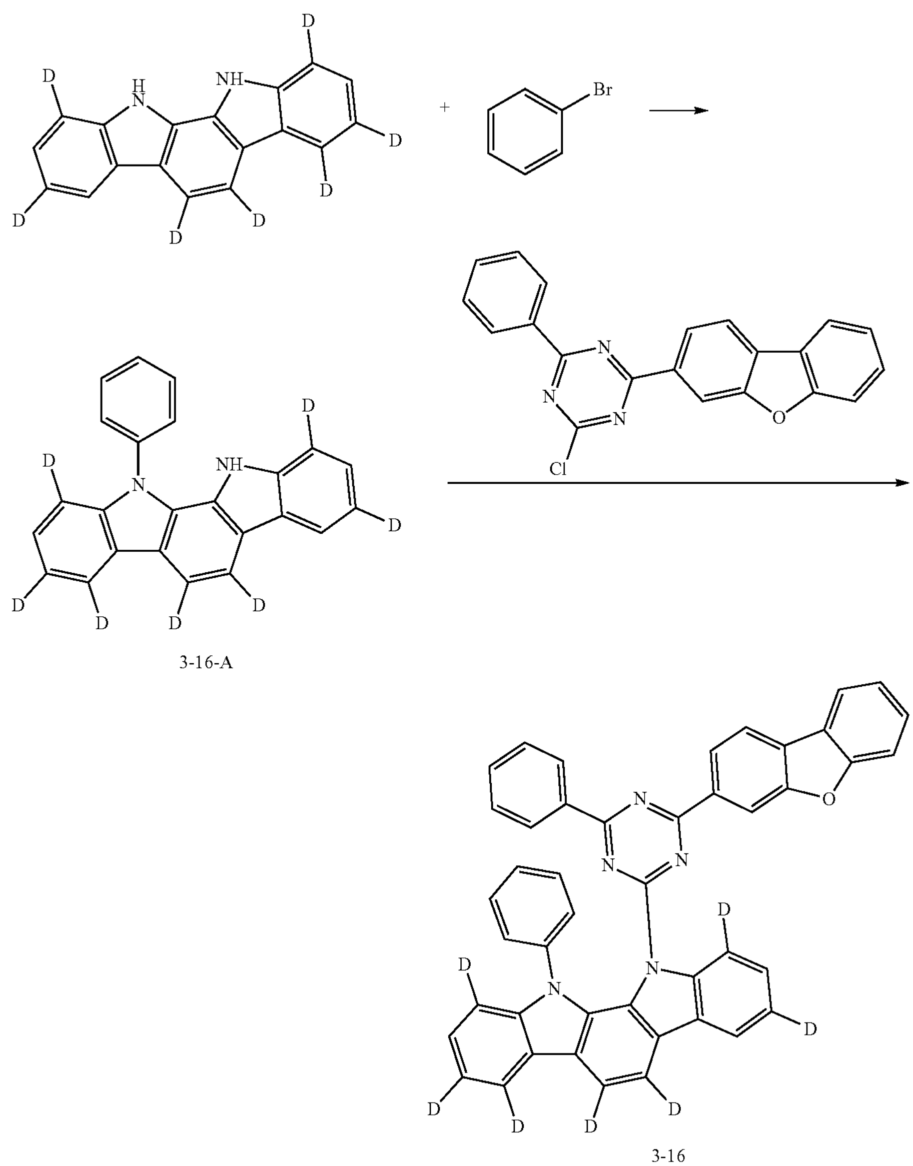

3-16-A 3-16

Step 1) Preparation of Compound 3-16-A

Compound 3-16-A (14 g, yield: 54%) was prepared in the same manner as in step 1 of the Preparation of Compound 3-14, except that 11,12-dihydroindolo[2,3-a]carbazole-1,3,5,6,7,8,10-d7 was used instead of 11,12-dihydroindolo[2,3-a]carbazole, and bromobenzene was used instead of 3-bromo-1,1':3',1"-terphenyl.

MS: $[M+H]^+$=340.5

Step 2) Preparation of Compound 3-16

Compound 3-16 (14.9 g, yield: 59%) was prepared in the same manner as in the Preparation of Compound 3-1, except that 11-phenyl-11,12-dihydroindolo[2,3-a]carbazole-1,3,5,6,7,8,10-d7 was used instead of 11-phenyl-11,12-dihydroindolo[2,3-a]carbazole, and 2-chloro-4-(dibenzo[b,d]furan-3-yl)-6-phenyl-1,3,5-triazine was used instead of 2-([1,1'-biphenyl]-4-yl)-4-chloro-6-phenyl-1,3,5-triazine.

MS: $[M+H]^+$=661.8

Examples

Example 1: Manufacture of Organic Light Emitting Device

A glass substrate on which a thin film of ITO (indium tin oxide) was coated in a thickness of 1,400 Å was put into distilled water containing a detergent dissolved therein and ultrasonically washed. In this case, the detergent used was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, the following compound HT-A and the following compound PD were thermally vacuum-deposited in a ratio of 95:5 to a thickness of 100 Å, and then only the following compound HT-A was deposited to a thickness of 1150 Å to form a hole transport layer. The following compound HT-B was thermally vacuum-deposited to a thickness of 450 Å on the hole transport layer to form an electron blocking layer. Then, 92 wt % of the host in which the compound 1-1 previously prepared as a first host, the compound 2-1 previously prepared as a second host, and the compound 3-1 previously prepared as a third host were mixed in a weight ratio of 30:35:35, and 8 wt % of the following compound GD were vacuum-deposited to a thickness of 350 Å on the electron blocking layer to form a light emitting layer. The following compound ET-A was vacuum-deposited to a thickness of 50 Å on the light emitting layer to form a hole blocking layer. The following compound ET-B and the following compound Liq were thermally vacuum-deposited in a ratio of 1:1 to a thickness of 300 Å on the hole blocking layer, and Yb (ytterbium) was vacuum-deposited to a thickness of 10 Å on the electron transport layer to form an electron injection layer. Magnesium and silver were deposited in a weight ratio of 1:4 to a thickness of 150 Å on the electron injection layer to form a cathode, thereby completing the manufacture of an organic light emitting device.

HT-A

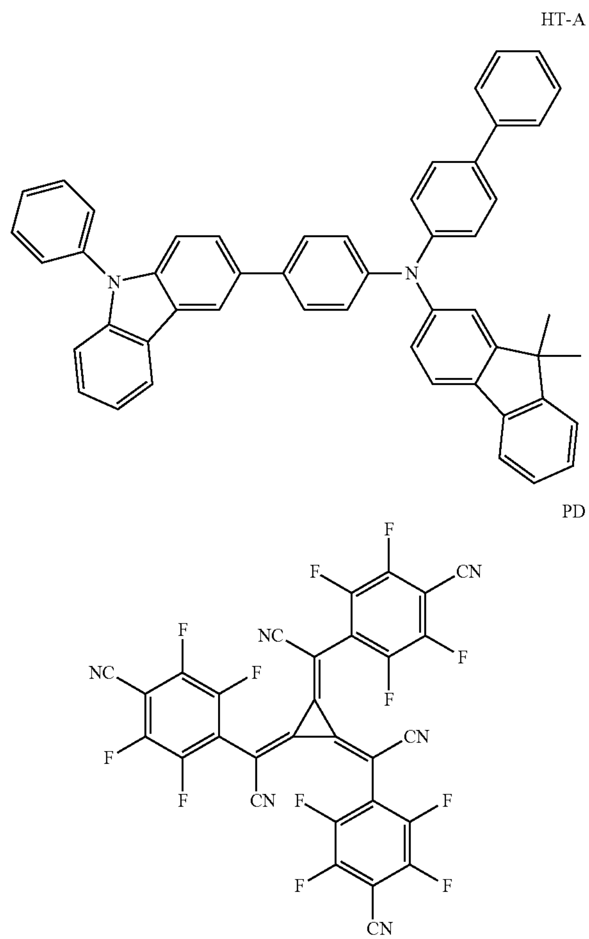

PD

-continued

HT-B

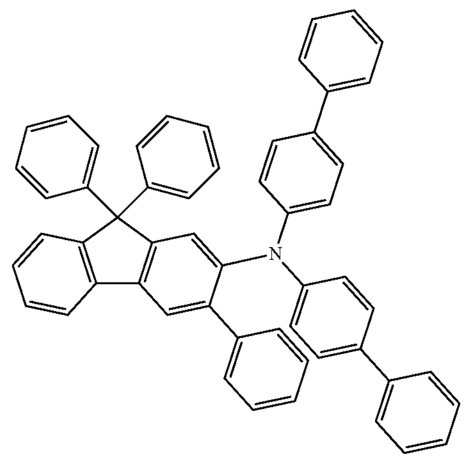

GD

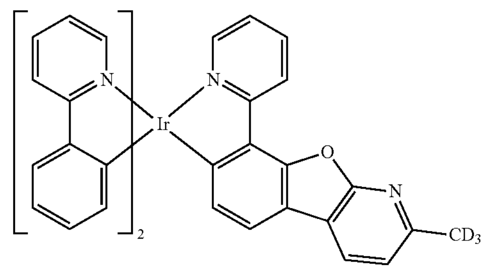

ET-A

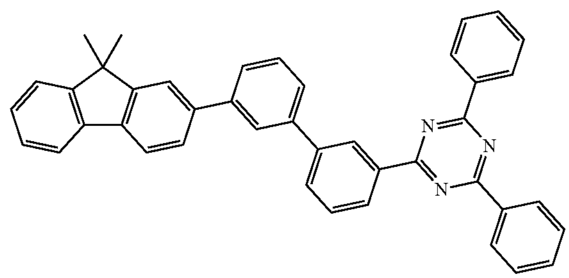

ET-B

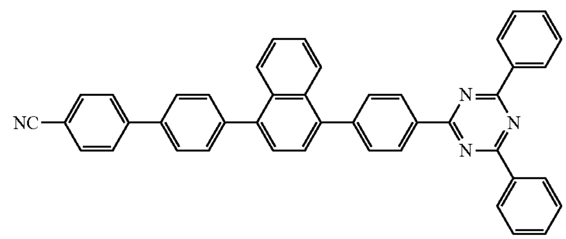

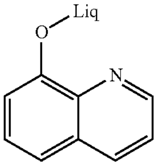

Liq

In the above-mentioned process, the vapor deposition rate of the organic material was maintained at 0.4 to 0.7 Å/sec, the deposition rate of ytterbium, magnesium and silver were maintained at 2 Å/sec, and the degree of vacuum during the deposition was maintained at $2\times10^{-7}$ to $5\times10^{-6}$ torr, thereby manufacturing an organic light emitting device.

Examples 2 to 18, and Comparative Examples 1 to 10

The organic light emitting devices were manufactured in the same manner as in Example 1, except that the host material was changed as shown in Table 1 below. At this time, the ratio means a weight ratio of the first host, the second host, and the third host. Further, the CE1, CE2, CE3 compounds shown in Table 1 are as follows, respectively.

CE1

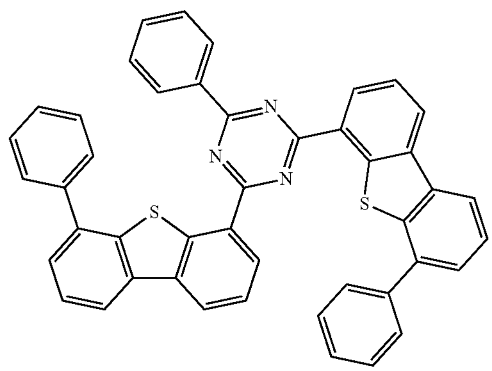

CE2

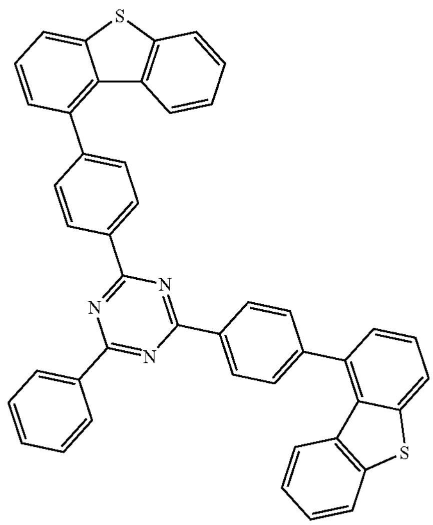

-continued

CE3

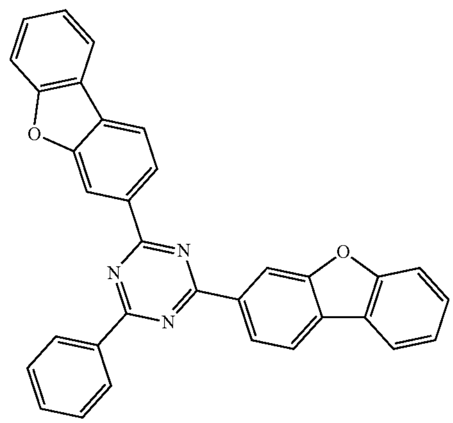

The organic light emitting devices prepared in Examples and Comparative Examples were heat-treated in an oven at 120° C. for 30 minutes, then taken out, and the voltage, efficiency, and lifetime (T95) were measured by applying a current, and the results are shown in Table 1 below. At this time, the driving voltage and luminous efficiency were measured by applying a current density of 10 $mA/cm^2$, and the lifetime (T95) means the time (hr) required for the luminance to be reduced to 95% of the initial luminance at a current density of 20 $mA/cm^2$.

TABLE 1

| | Host | | | | @10 $mA/cm^2$ | | @20 $mA/cm^2$ |
|---|---|---|---|---|---|---|---|
| | First host | Second host | Third host | Host ratio (weight ratio) | Voltage (V) | Efficiency (cd/A) | Lifetime (T95) (hr) |
| Ex. 1 | Com. 1-1 | Com. 2-1 | Com. 3-1 | 30:35:35 | 3.88 | 79.3 | 183 |
| Ex. 2 | Com. 1-9 | Com. 2-1 | Com. 3-12 | 30:35:35 | 4.61 | 75.1 | 213 |
| Ex. 3 | Com. 1-3 | Com. 2-2 | Com. 3-2 | 30:35:35 | 3.71 | 75.3 | 210 |
| Ex. 4 | Com. 1-3 | Com. 2-2 | Com. 3-15 | 30:35:35 | 3.70 | 75.3 | 235 |
| Ex. 5 | Com. 1-4 | Com. 2-3 | Com. 3-3 | 30:35:35 | 3.67 | 75.2 | 196 |
| Ex. 6 | Com. 1-5 | Com. 2-4 | Com. 3-4 | 30:35:35 | 3.62 | 70.7 | 208 |
| Ex. 7 | Com. 1-6 | Com. 2-4 | Com. 3-13 | 30:35:35 | 4.40 | 75.9 | 167 |
| Ex. 8 | Com. 1-7 | Com. 2-5 | Com. 3-5 | 30:35:35 | 3.68 | 79.5 | 172 |
| Ex. 9 | Com. 1-8 | Com. 2-6 | Com. 3-6 | 30:35:35 | 4.19 | 70.2 | 162 |
| Ex. 10 | Com. 1-9 | Com. 2-6 | Com. 3-14 | 30:35:35 | 4.08 | 73.1 | 224 |
| Ex. 11 | Com. 1-10 | Com. 2-7 | Com. 3-7 | 30:35:35 | 4.16 | 72.0 | 161 |
| Ex. 12 | Com. 1-11 | Com. 2-8 | Com. 3-8 | 30:35:35 | 4.03 | 74.7 | 162 |
| Ex. 13 | Com. 1-12 | Com. 2-9 | Com. 3-9 | 30:35:35 | 3.89 | 79.5 | 225 |
| Ex. 14 | Com. 1-1 | Com. 2-9 | Com. 3-1 | 30:35:35 | 3.68 | 72.6 | 234 |
| Ex. 15 | Com. 1-7 | Com. 2-9 | Com. 3-10 | 30:35:35 | 3.65 | 75.9 | 175 |

TABLE 1-continued

| | Host | | | | @10 mA/cm² | | @20 mA/cm² |
|---|---|---|---|---|---|---|---|
| | First host | Second host | Third host | Host ratio (weight ratio) | Voltage (V) | Efficiency (cd/A) | Lifetime (T95) (hr) |
| Ex. 16 | Com. 1-13 | Com. 2-10 | Com. 3-15 | 30:35:35 | 3.77 | 70.4 | 215 |
| Ex. 17 | Com. 1-2 | Com. 2-10 | Com. 3-16 | 30:35:35 | 3.81 | 73.5 | 239 |
| Ex. 18 | Com. 1-6 | Com. 2-11 | Com. 3-11 | 30:35:35 | 3.76 | 80.3 | 183 |
| Comparative Ex. 1 | — | Com. 2-1 | — | 0:100:0 | 7.01 | 8.9 | 16 |
| Comparative Ex. 2 | — | — | Com. 3-1 | 0:0:100 | 7.52 | 9.0 | 13 |
| Comparative Ex. 3 | Com. 1-1 | — | — | 100:0:0 | 7.21 | 14.1 | 21 |
| Comparative Ex. 4 | — | Com. 2-1 | Com. 3-1 | 0:50:50 | 4.41 | 56.3 | 116 |
| Comparative Ex. 5 | Com. 1-1 | Com. 2-1 | — | 30:70:0 | 4.23 | 66.7 | 103 |
| Comparative Ex. 6 | Com. 1-3 | — | Com. 3-5 | 30:0:70 | 7.31 | 23.5 | 34 |
| Comparative Ex. 7 | CE-1 | Com. 2-1 | — | 30:70:0 | 4.35 | 66.5 | 103 |
| Comparative Ex. 8 | CE-1 | Com. 2-2 | Com. 3-2 | 30:35:35 | 4.11 | 67.2 | 143 |
| Comparative Ex. 9 | CE-2 | Com. 2-3 | — | 30:70:0 | 4.85 | 60.3 | 85 |
| Comparative Ex. 10 | CE-3 | Com. 2-4 | — | 30:70:0 | 4.97 | 62.5 | 117 |

As shown in Table 1 above, it was confirmed that the organic light emitting devices of Examples 1 to 18 exhibit low driving voltage and improved efficiency and lifetime, as compared with the organic light emitting devices of Comparative Examples 1 to 10.

The compound of Chemical Formula 2 according to the present disclosure has excellent capability of transferring holes and serves as a P-type host. The compound of Chemical Formula 1 and the compound of Chemical Formula 3 according to the present disclosure serve as an N-type host. In general, when a P-type host and an N-type host are mixed and applied as a host of the light emitting layer, an exciplex is formed, whereby the characteristics of the device can be improved as compared with the case where only one of the P-type host and the N-type host is applied. As shown in Table 1 above, in the case of Examples 1 to 18 in which a P-type host and an N-type host are mixed and applied as a host of the light emitting layer, the driving voltage of the device is significantly lowered, and the efficiency and lifespan are significantly improved, as compared to Comparative Examples 1, 2, 3 and 6 to which only one of the P-type host and the N-type host is applied.

In particular, when the P-type host of Chemical Formula 2 according to the present disclosure is mixed with the N-type host of Chemical Formulas 1 and 3 according to the present disclosure (Chemical Formula 1+Chemical Formula 2+Chemical Formula 3), the characteristics of the device can be improved as compared with the case where only one type of N-type host mixed and used (Chemical Formula 2+Chemical Formula 1; or Chemical Formula 2+Chemical Formula 3). As shown in Table 1 above, the organic light emitting devices of Examples 1 to 18 have improved voltage, efficiency and lifetime characteristics, as compared with Comparative Examples 4, 5, 7, 9 and 10 in which only one type of N-type host is mixed and used.

| <Explanation of symbols> | |
|---|---|
| 1: substrate | 2: anode |
| 3: electron inhibition layer | 4: light emitting layer |

-continued

| <Explanation of symbols> | |
|---|---|
| 5: cathode | 6: hole transport layer |
| 7: electron transport layer | |

The invention claimed is:

1. An organic light emitting device comprising:

an anode, a cathode, a light emitting layer between the anode and the cathode, an electron inhibition layer between the anode and the light emitting layer, and a hole transport layer between the electron inhibition layer and the anode, wherein the light emitting layer comprises a compound of the following Chemical Formula 1, a compound of the following Chemical Formula 2, and a compound of the following Chemical Formula 3:

[Chemical Formula 1]

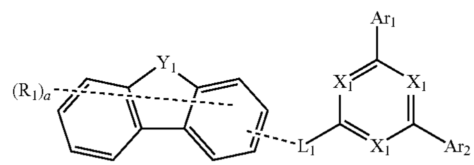

wherein in Chemical Formula 1:

$Y_1$ is O or S;

each $X_1$ is independently CH, or N, provided that at least one of $X_1$ is N;

$L_1$ is a direct bond, a substituted or unsubstituted $C_{6-60}$ arylene, or a substituted or unsubstituted $C_{2-60}$ heteroarylene containing any one or more selected from the group consisting of N, O and S;

$Ar_1$ and $Ar_2$ are each independently phenyl, biphenylyl, dibenzofuranyl, carbazol-9-yl, or (phenyl) carbazol-9-yl, wherein the $Ar_1$ and $Ar_2$ are each independently unsubstituted or substituted with at least one deuterium;

$R_1$ is hydrogen, deuterium, a substituted or unsubstituted $C_{6-60}$ alkyl, a substituted or unsubstituted $C_{6-60}$ aryl, or a substituted or unsubstituted $C_{2-60}$ heteroaryl containing any one or more selected from the group consisting of N, O and S; and a is an integer of 1 to 7;

[Chemical Formula 2]

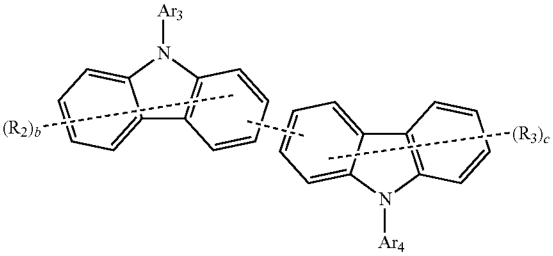

wherein in Chemical Formula 2:

$Ar_3$ and $Ar_4$ are each independently a substituted or unsubstituted $C_{6-60}$ aryl or a substituted or unsubstituted $C_{2-60}$ heteroaryl containing any one or more selected from the group consisting of N, O and S;

$R_2$ and $R_3$ are each independently hydrogen, deuterium, a substituted or unsubstituted $C_{6-60}$ aryl, or a substituted or unsubstituted $C_{2-60}$ heteroaryl containing any one or more selected from the group consisting of N, O and S; and b and c are each independently an integer of 1 to 7;

[Chemical Formula 3]

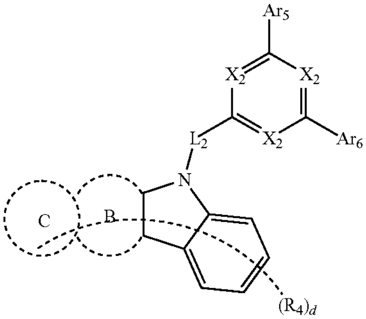

wherein in Chemical Formula 3;

B is a benzene ring fused with two adjacent pentagonal rings;

each $X_2$ is independently CH or N, provided that at least one of $X_2$ is N;

$L_2$ is a direct bond or phenylene, provided that when $L_2$ is phenylene, it is unsubstituted or substituted with at least one deuterium $Ar_5$ and $Ar_6$ are each independently a substituted or unsubstituted $C_{6-60}$ aryl or a substituted or unsubstituted $C_{2-60}$ heteroaryl containing any one or more selected from the group consisting of N, O and S; and C is the following Chemical Formula 4-1 or 4-2;

[Chemical Formula 4-1]

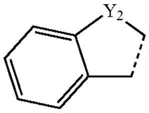

[Chemical Formula 4-2]

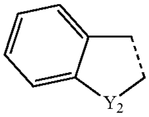

wherein in Chemical Formulas 4-1 and 4-2:

the dotted line is a bond that is fused with B;

$Y_2$ is CRR', $C(CH_3)_2$, O, S, or $NAr_7$, wherein R and R' are each independently a substituted or unsubstituted $C_{6-60}$ alkyl, or a substituted or unsubstituted $C_{6-60}$ aryl, and $Ar_7$ is a substituted or unsubstituted $C_{6-60}$ aryl, or a substituted or unsubstituted $C_{2-60}$ heteroaryl containing any one or more selected from the group consisting of N, O and S;

$R_4$ is hydrogen, deuterium, a substituted or unsubstituted $C_{6-60}$ aryl, or a substituted or unsubstituted $C_{2-60}$ heteroaryl containing any one or more selected from the group consisting of N, O and S; and d is an integer of 1 to 10.

2. The organic light emitting device according to claim 1, wherein:

the Chemical Formula 1 is any one of the following Chemical Formulas 1-1 to 1-4:

[Chemical Formula 1-1]

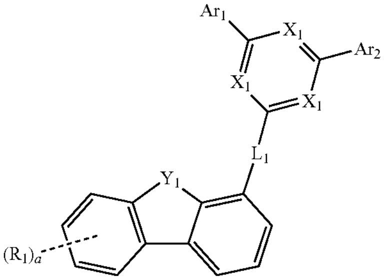

[Chemical Formula 1-2]

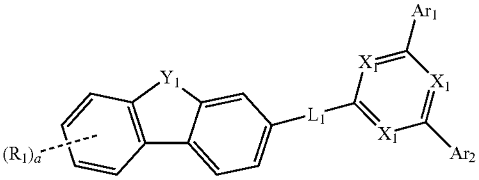

[Chemical Formula 1-3]

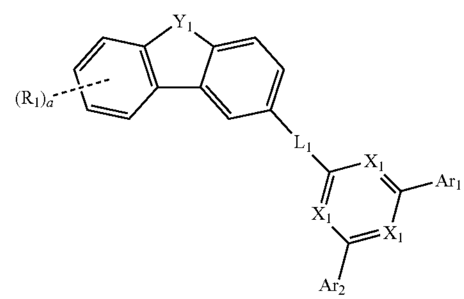

-continued

[Chemical Formula 1-4]

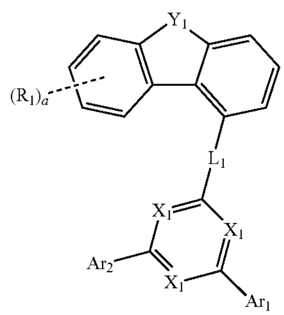

wherein in Chemical Formulas 1-1 to 1-4:

$Y_1$, $X_1$, $L_1$, $Ar_1$, $Ar_2$, $R_1$, and a are as defined in claim 1.

3. The organic light emitting device according to claim 1, wherein:

two or three of $X_1$ are N.

4. The organic light emitting device according to claim 1, wherein:

$L_1$ is a direct bond.

5. The organic light emitting device according to claim 1, wherein:

$R_1$ is phenyl, biphenylyl, (phenyl) biphenylyl, terphenylyl, naphthyl, phenanthrenyl, triphenylenyl, dimethylfluorenyl, spirobifluorenyl, dibenzofuranyl, dibenzothiophenyl, carbazol-9-yl, (phenyl) carbazol-9-yl, (diphenyl) carbazol-9-yl, 9-phenyl-9H-carbazolyl, 12-phenyl-11,12-dihydroindolo[2,3-a]carbazol-11-yl, or 1,1-dimethyl-1,3-dihydroindeno[2,1-b]carbazol-3-yl; and the $R_1$ is unsubstituted or substituted with at least one deuterium.

6. The organic light emitting device according to claim 1, wherein:

the compound of Chemical Formula 1 is any one compound selected from the group consisting of the following compounds:

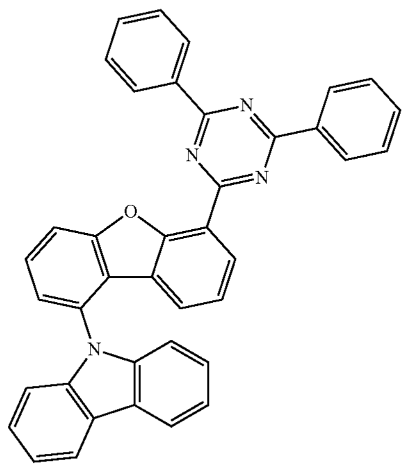

-continued

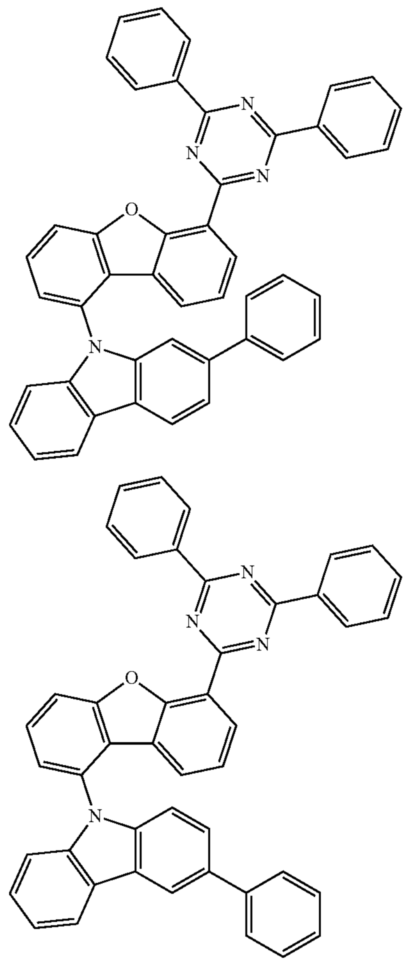

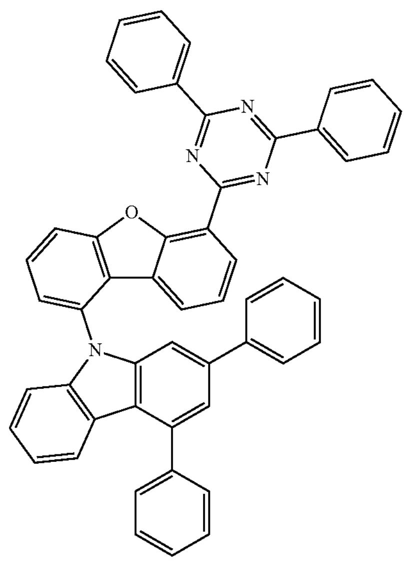

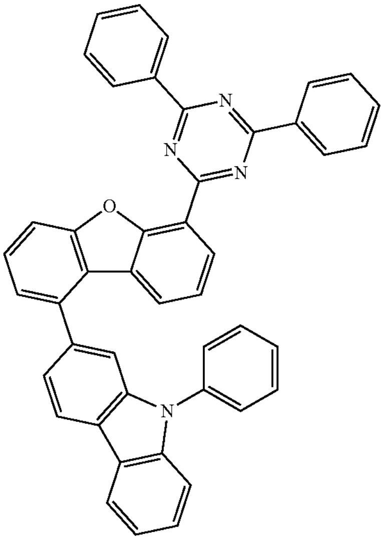
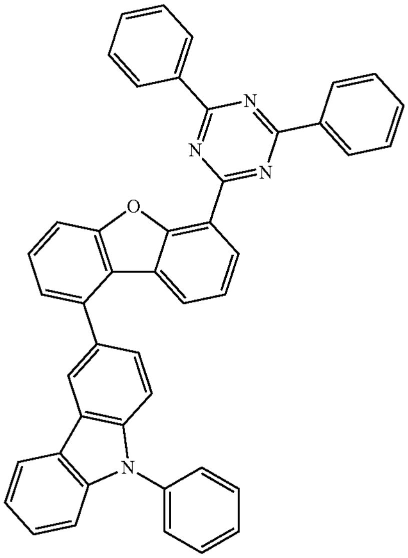
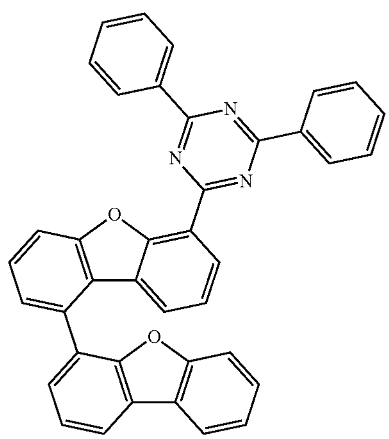
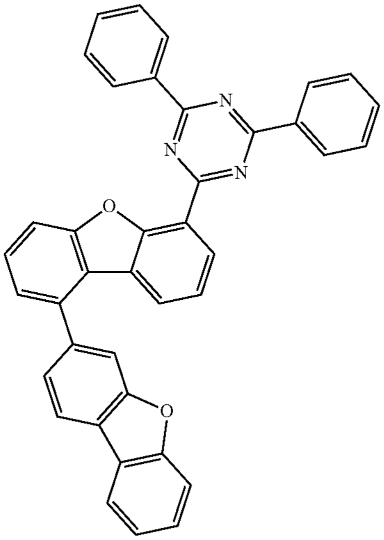
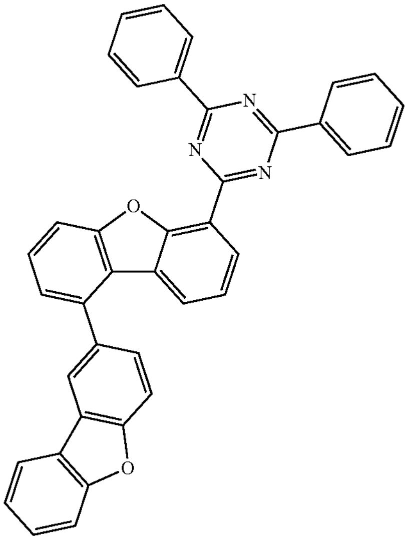
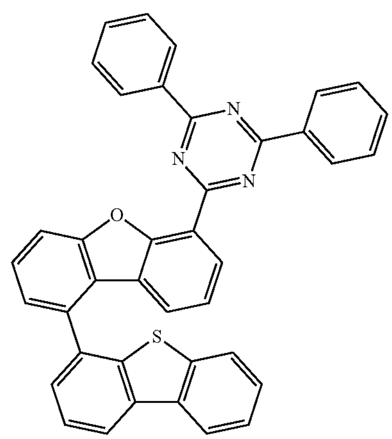

-continued
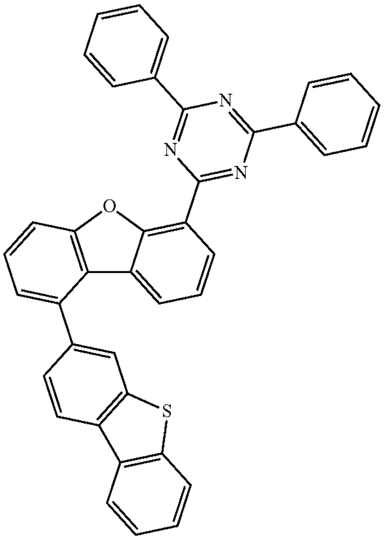
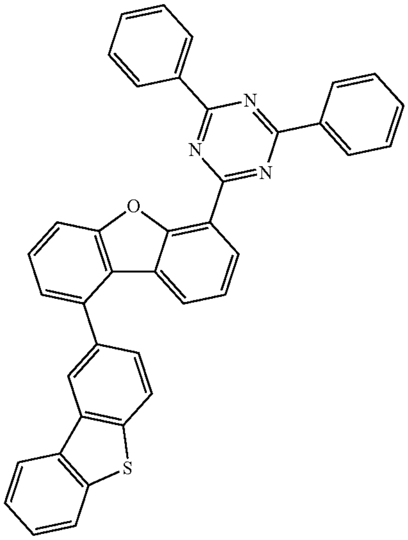
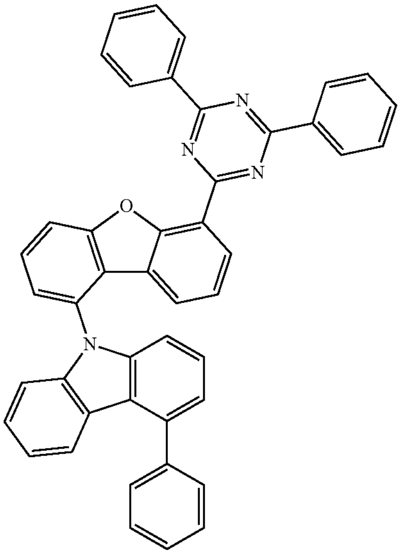
-continued
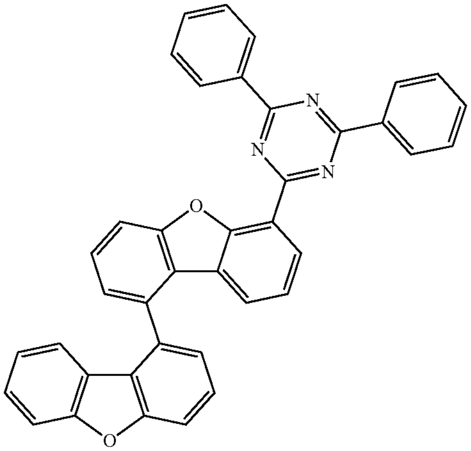
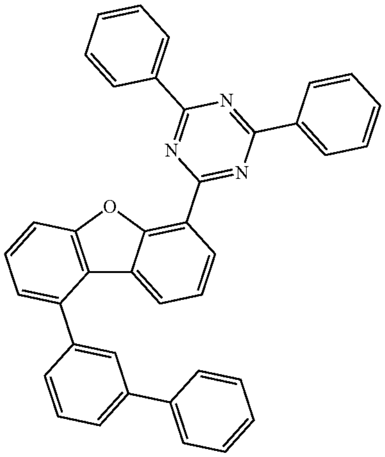
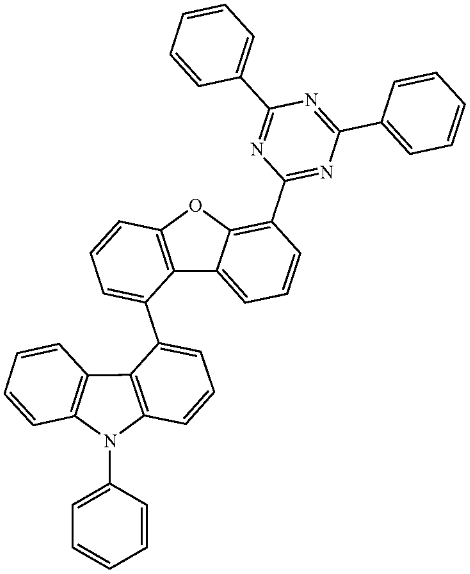

-continued
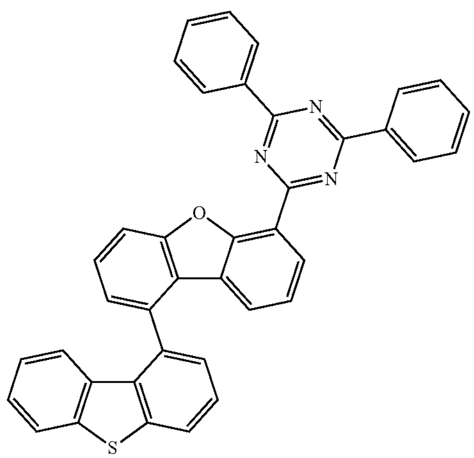
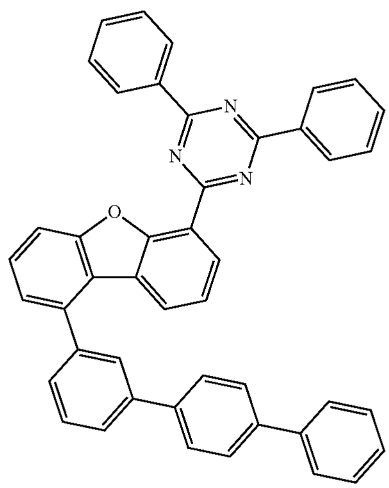
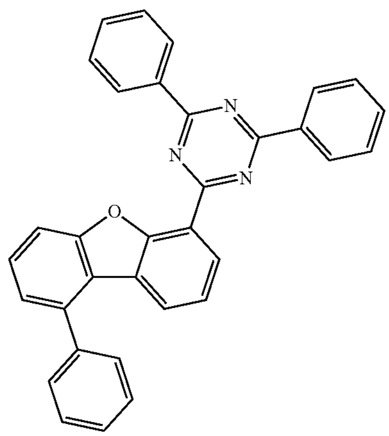
-continued
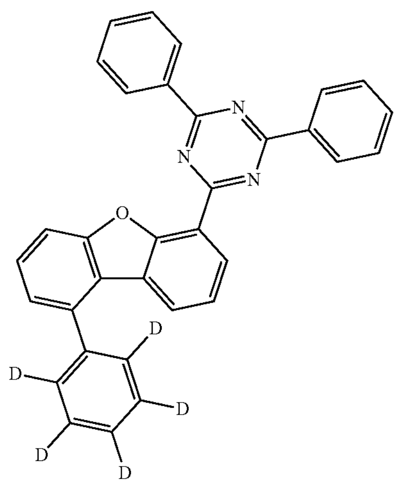
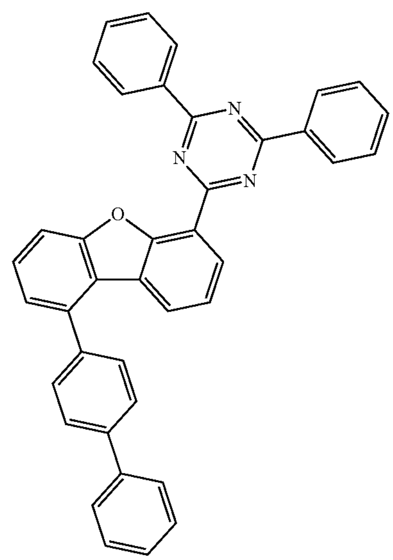
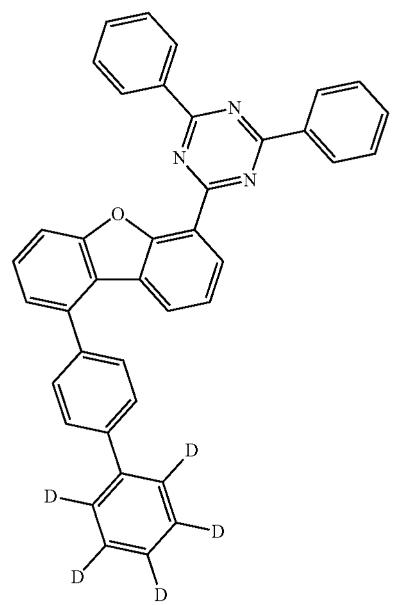

-continued
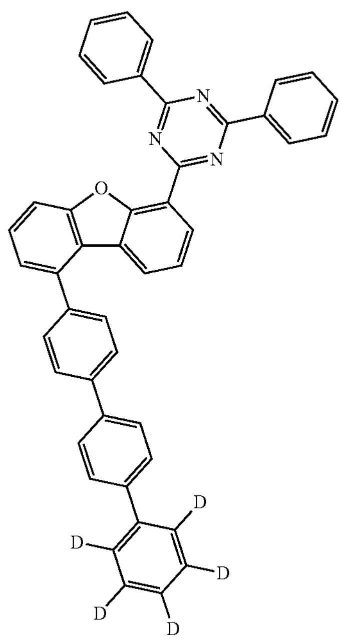
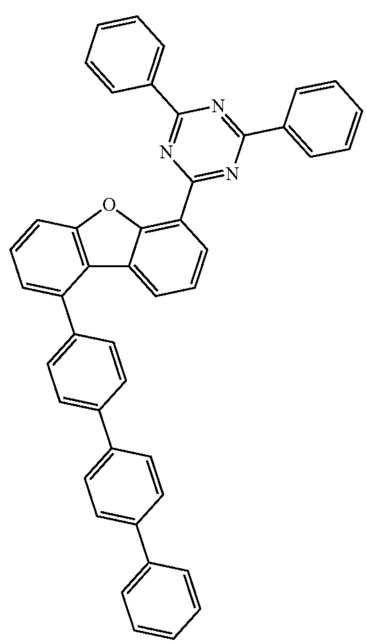
-continued
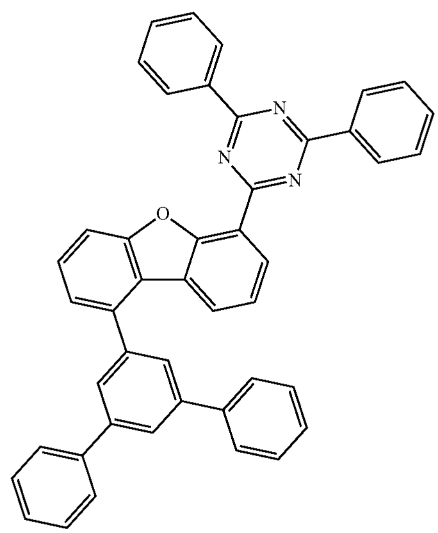
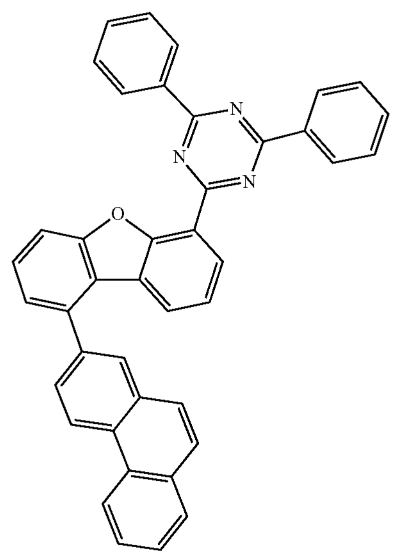
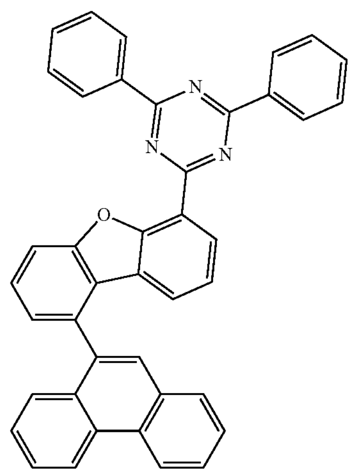

-continued
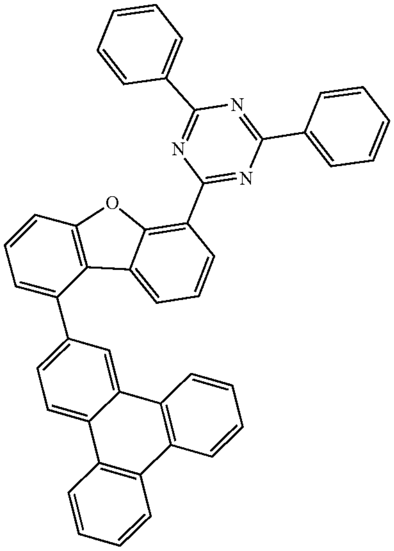
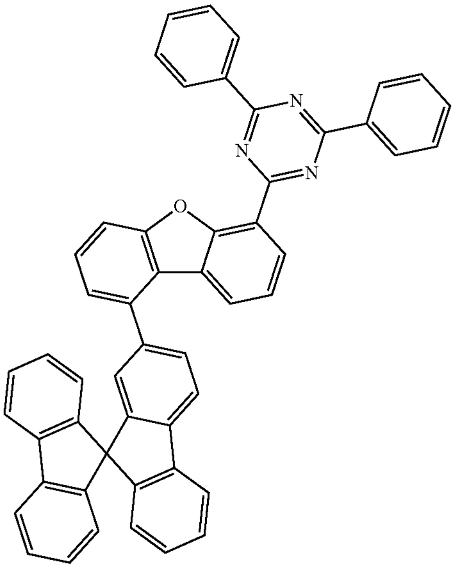
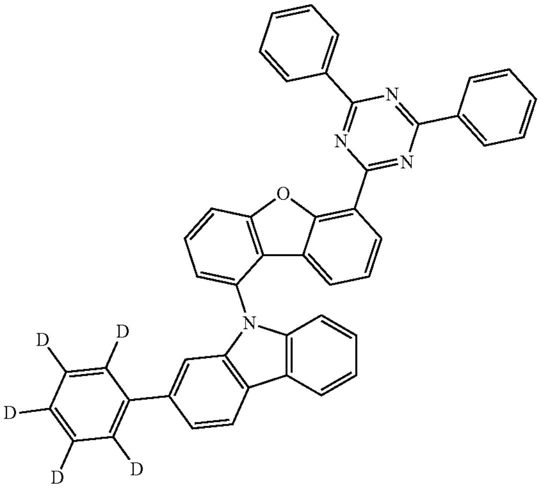
-continued
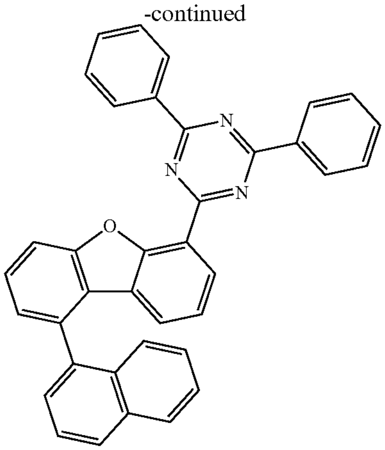
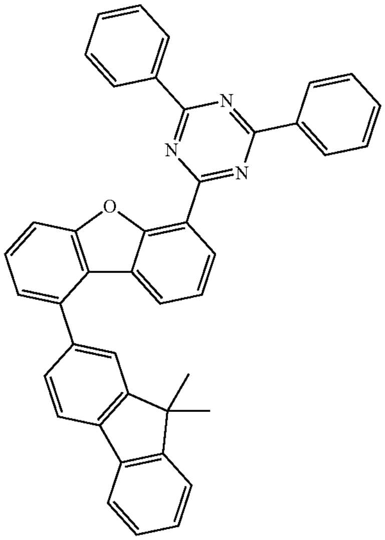
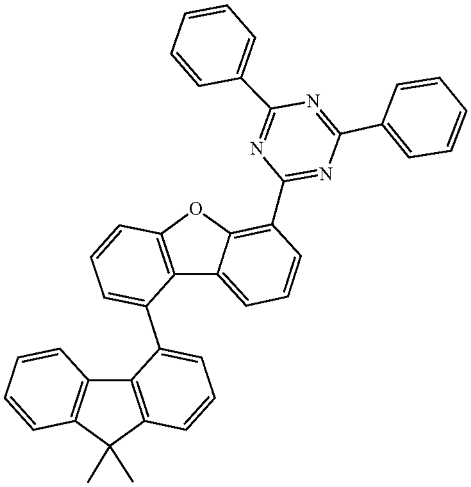

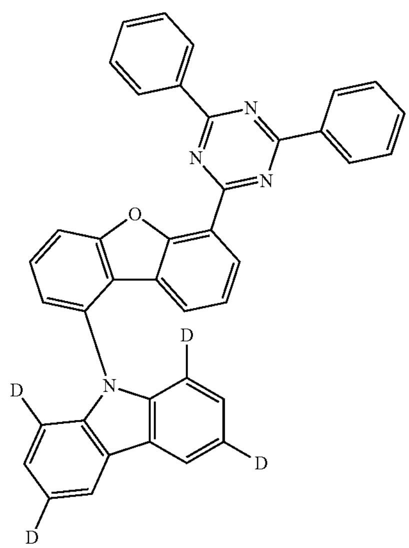
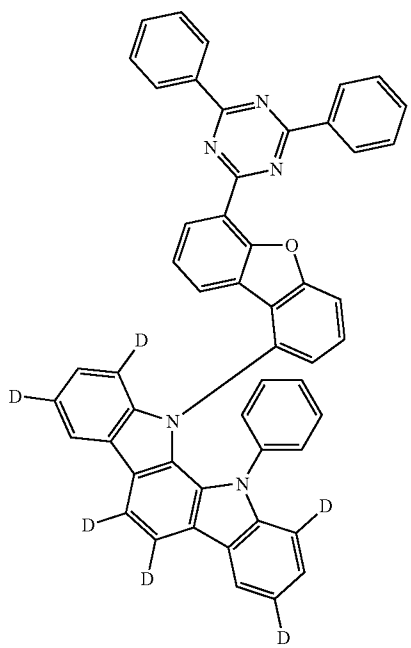
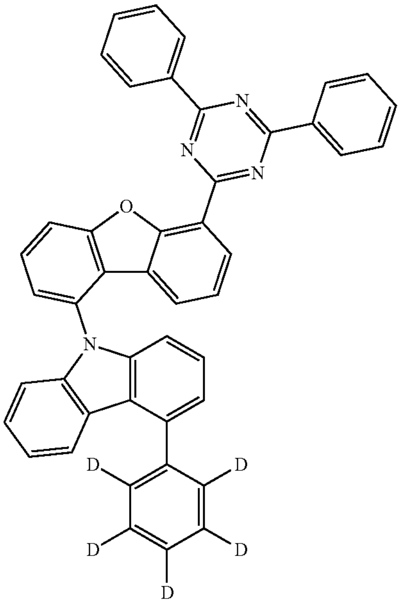
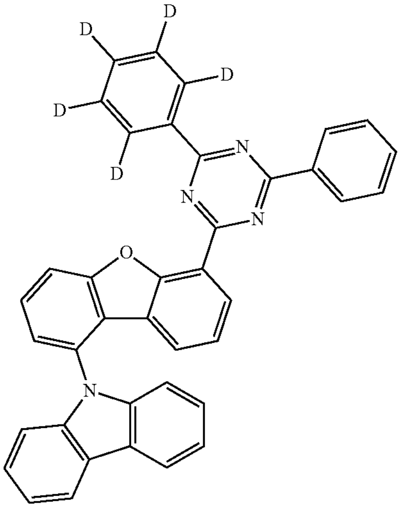
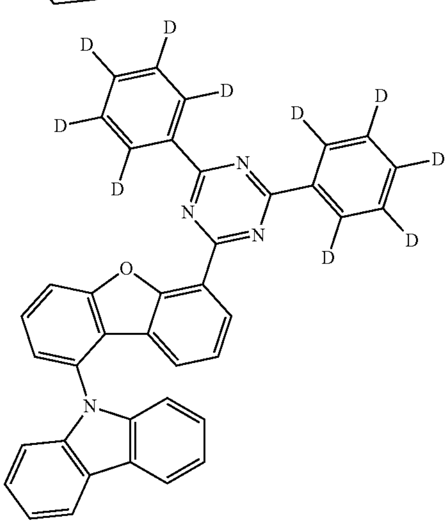

-continued
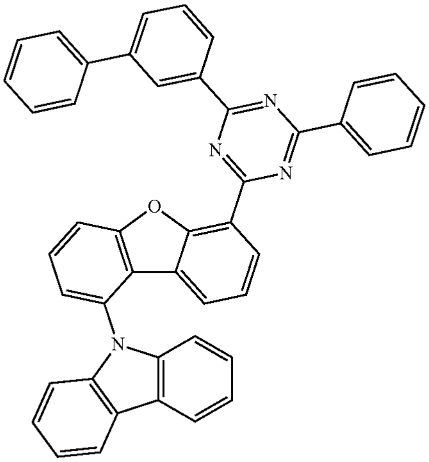
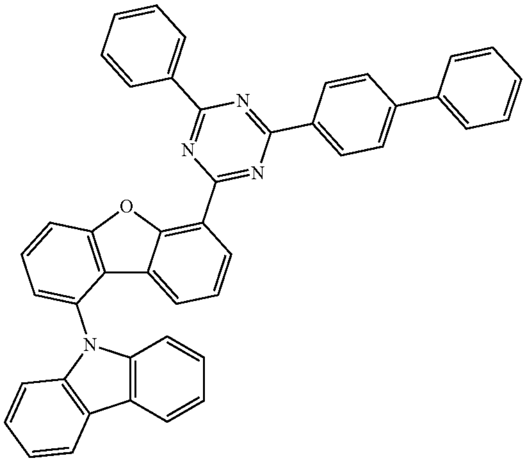
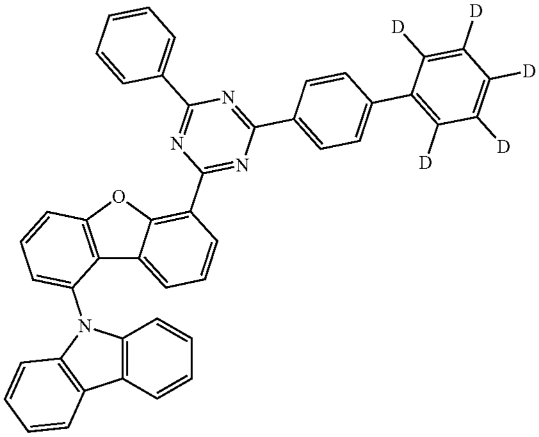
-continued
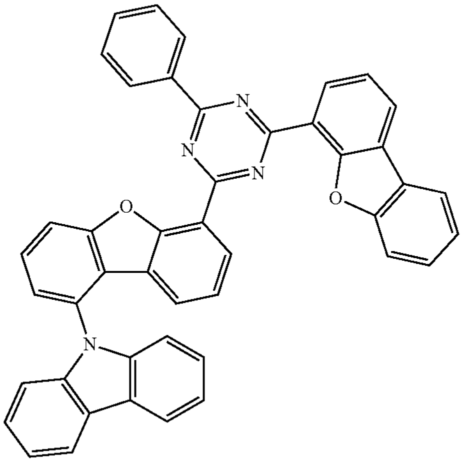
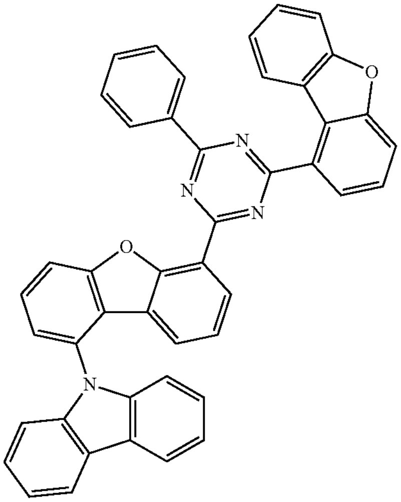
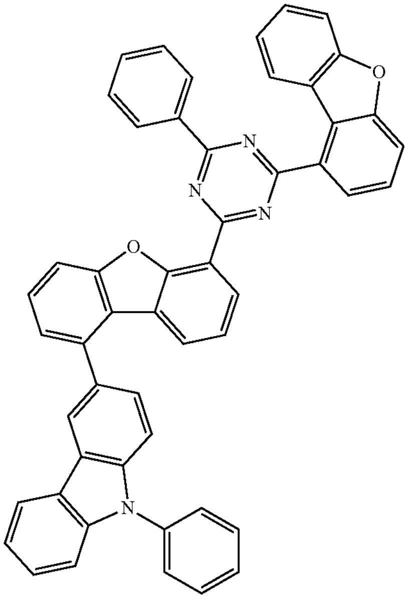

-continued
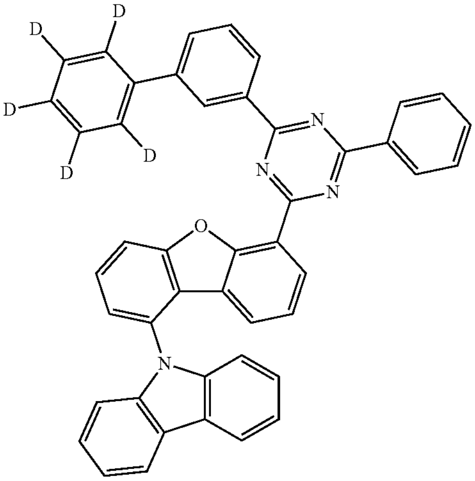
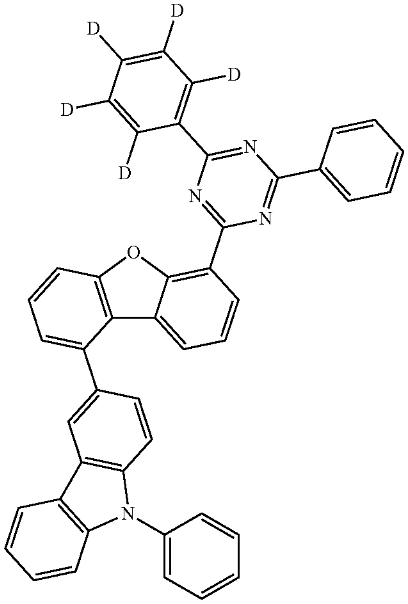
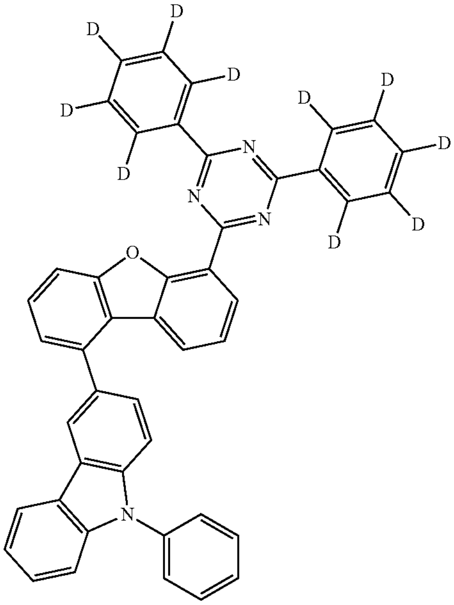
-continued
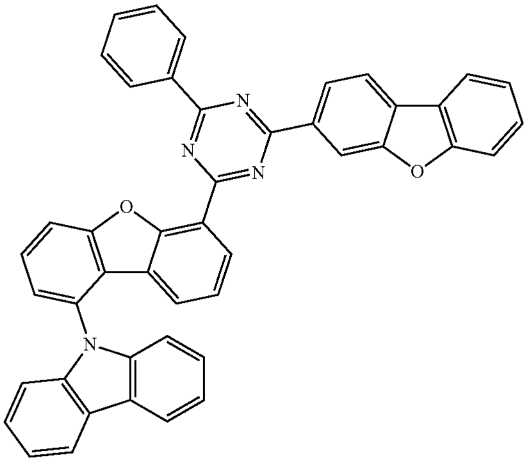
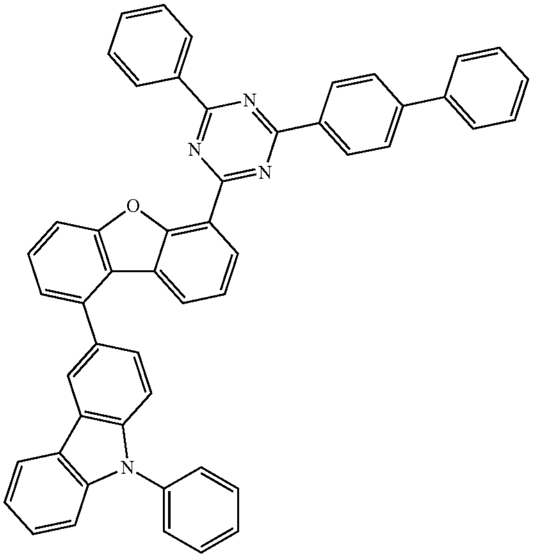
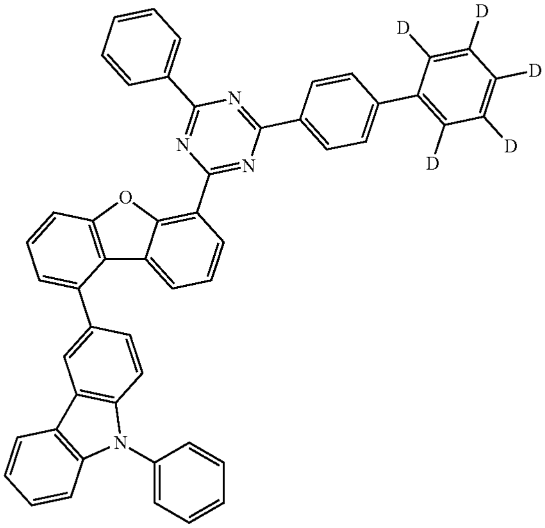

-continued
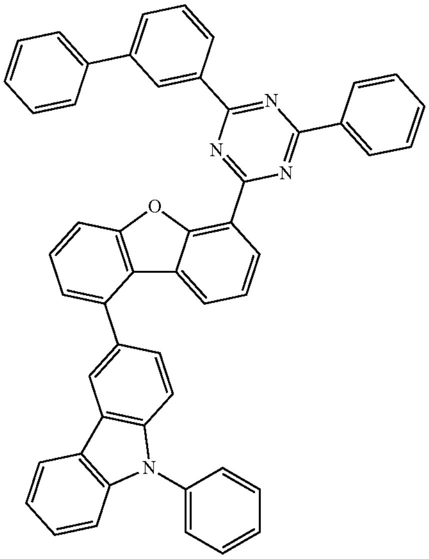
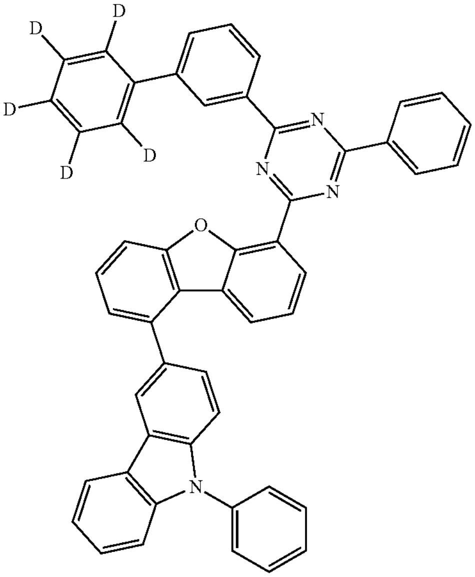
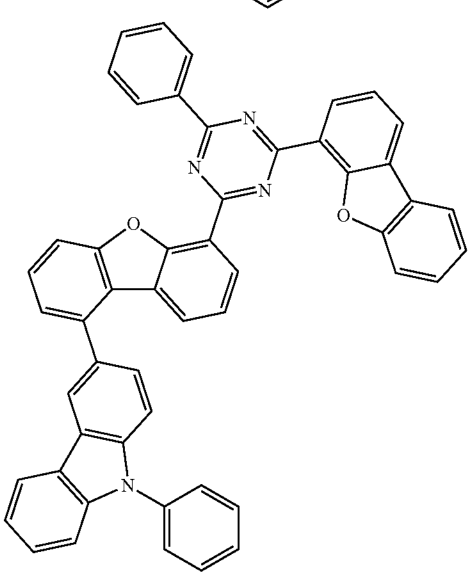
-continued
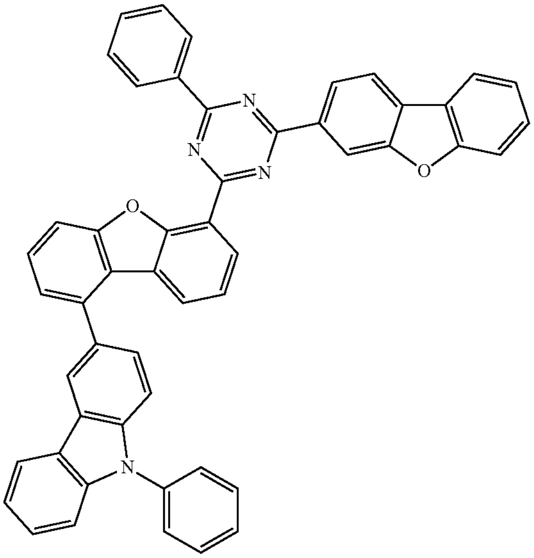
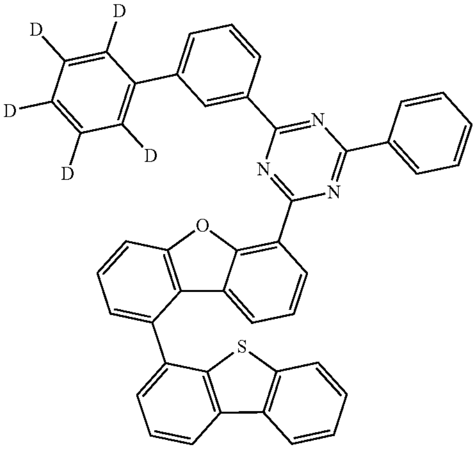
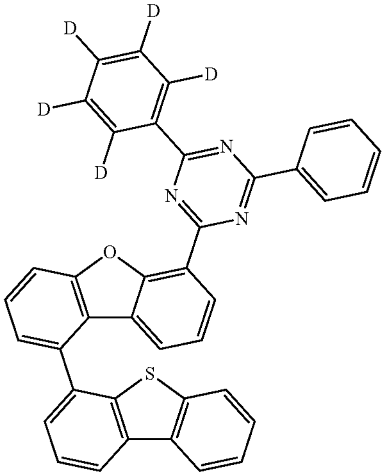

-continued
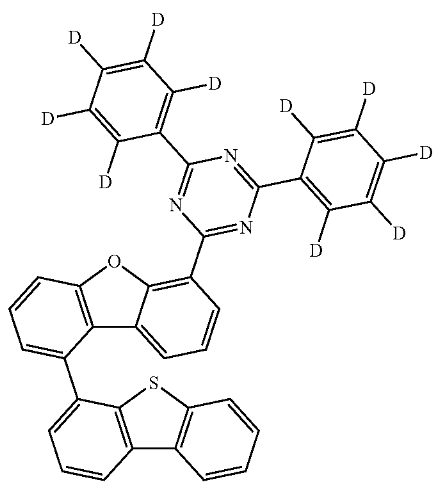
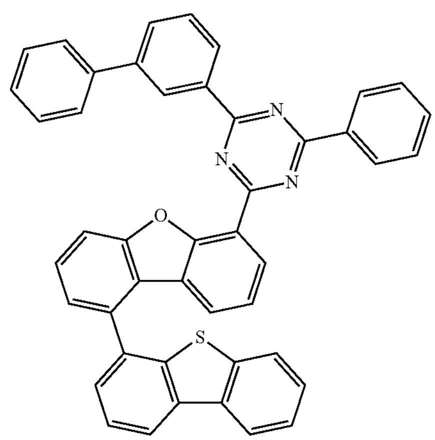
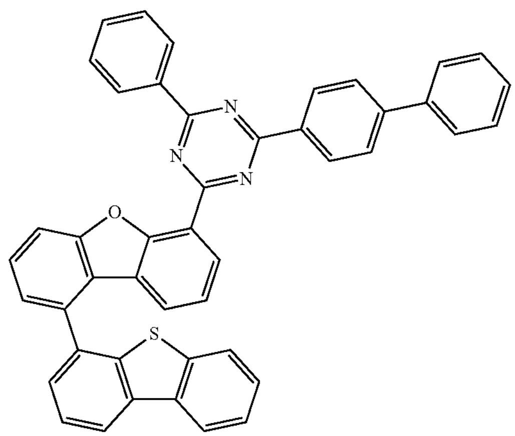
-continued
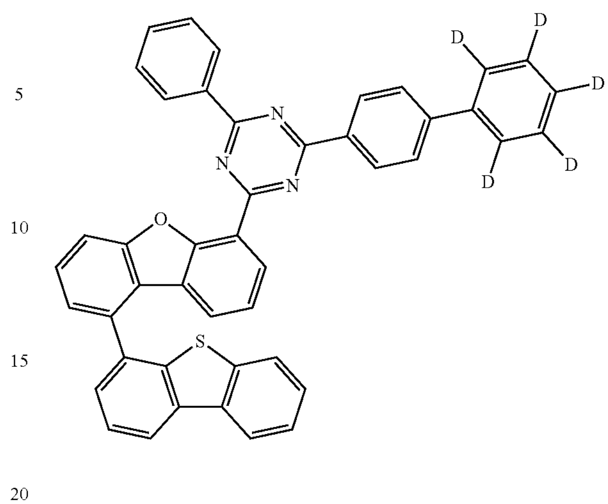
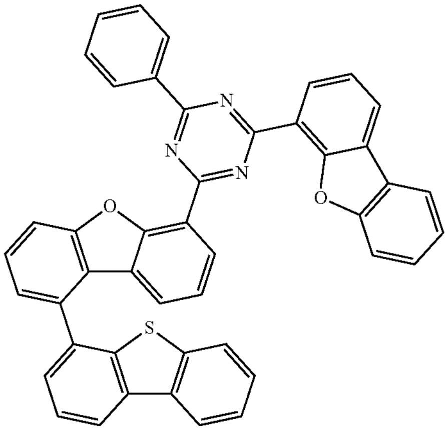
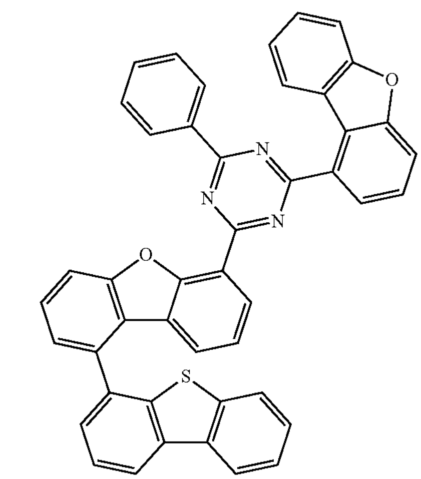

-continued
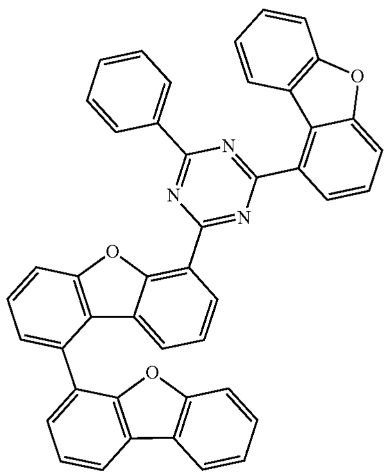
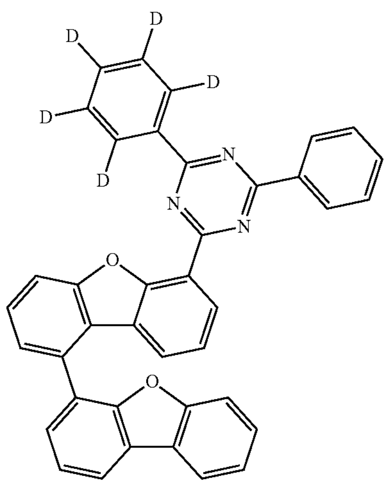
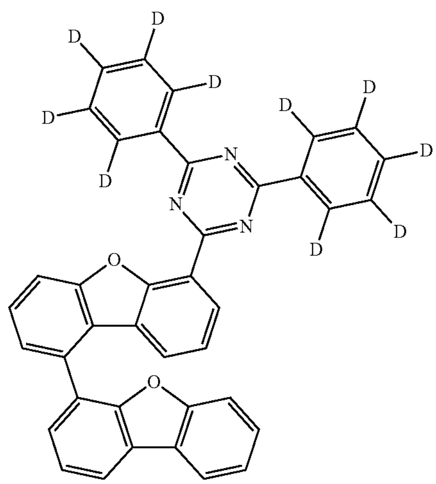
-continued
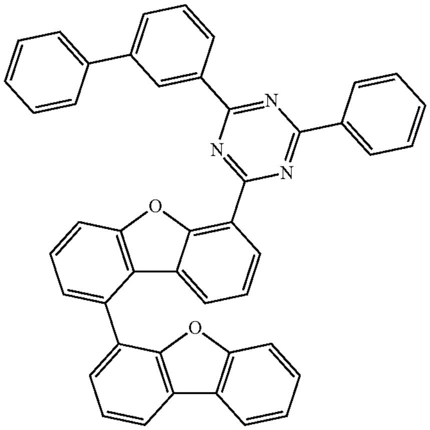
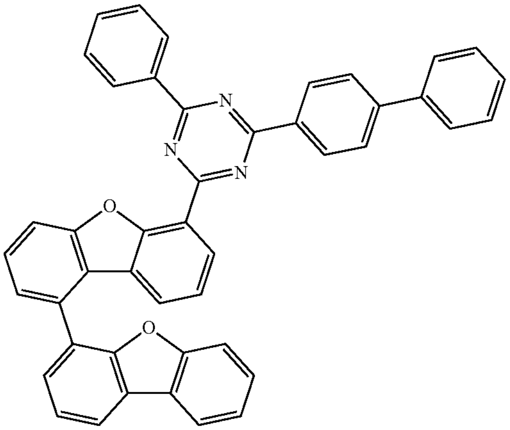
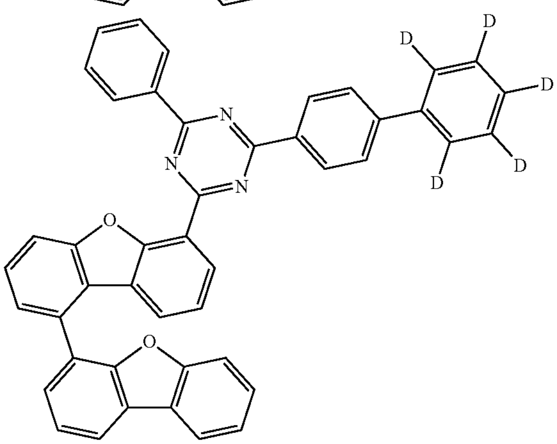
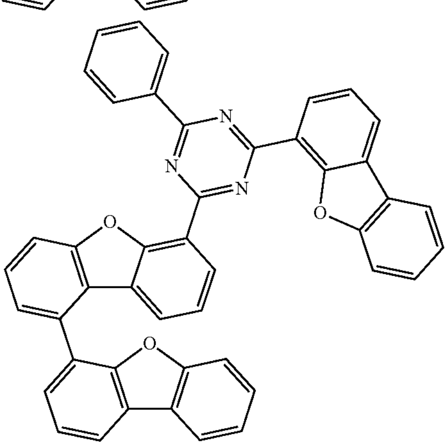

-continued
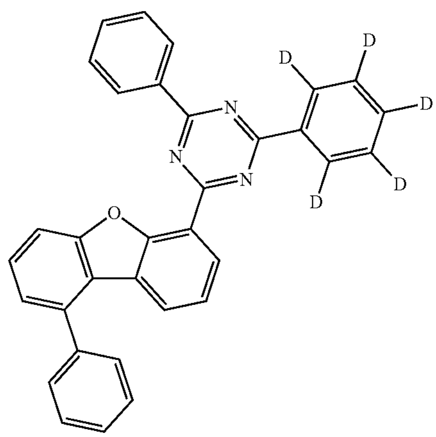
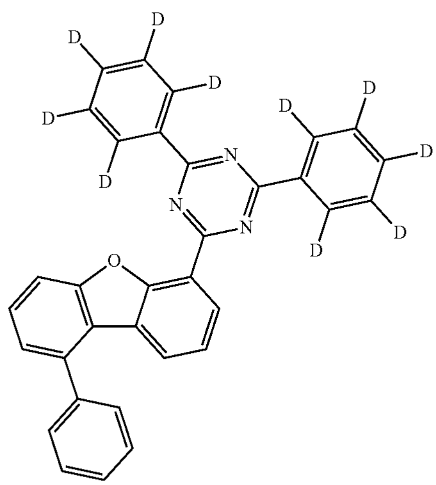
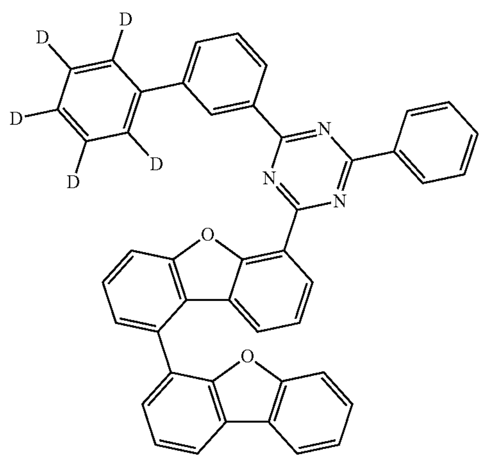
-continued
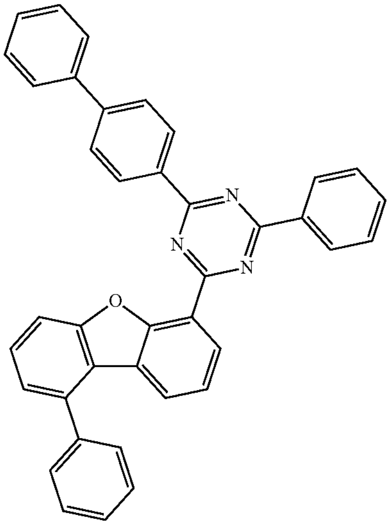
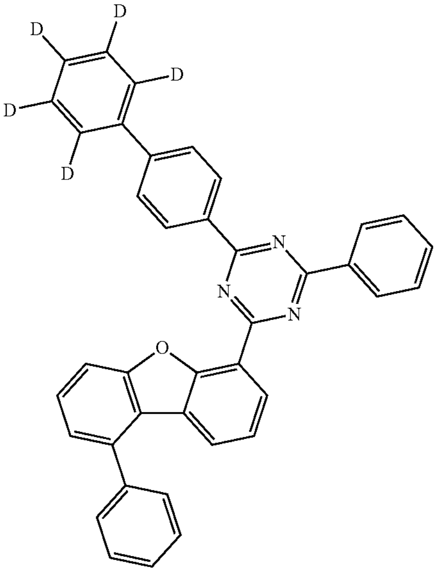
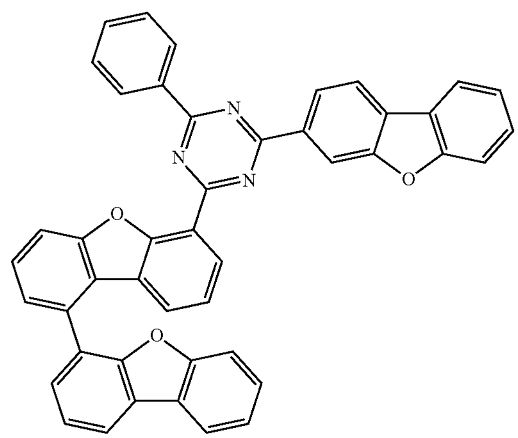

-continued
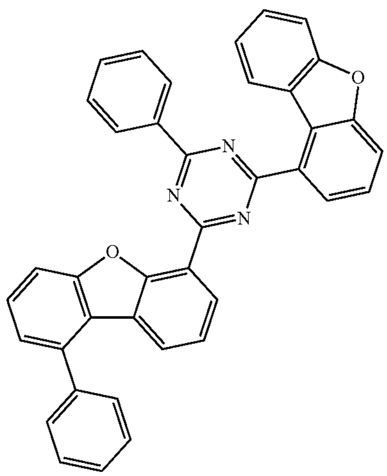
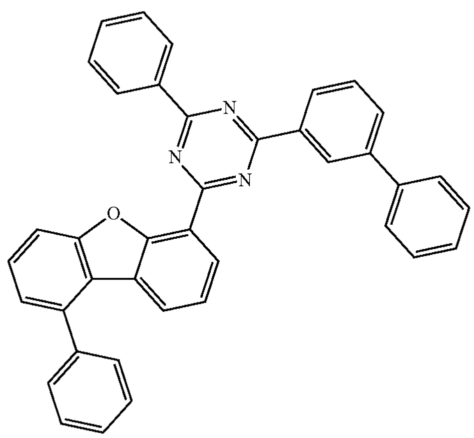
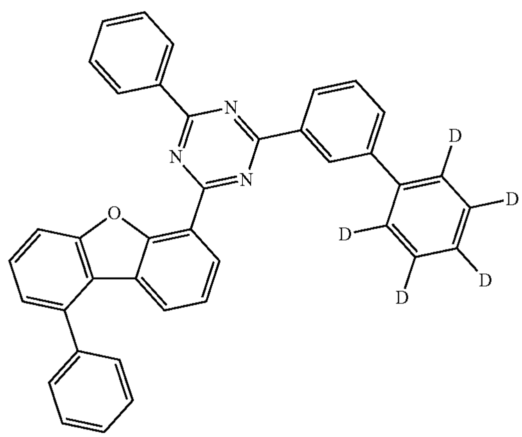
-continued
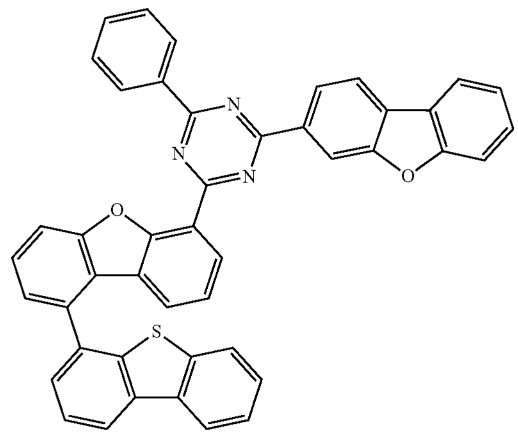
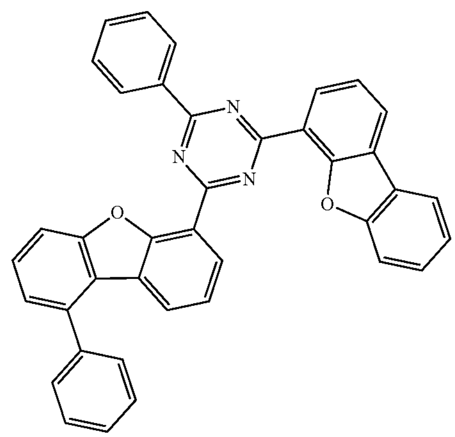
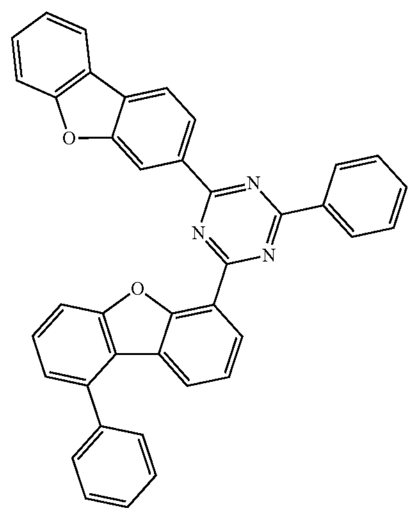

-continued
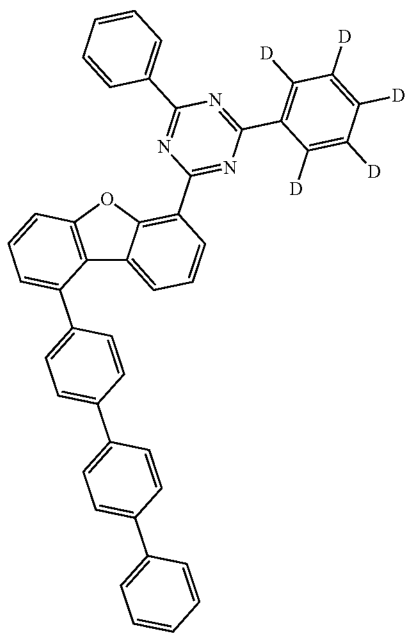
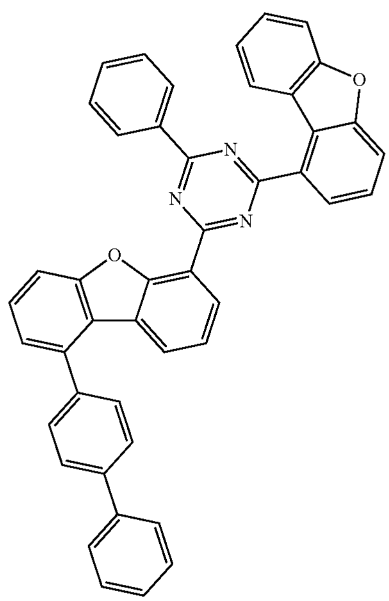
-continued
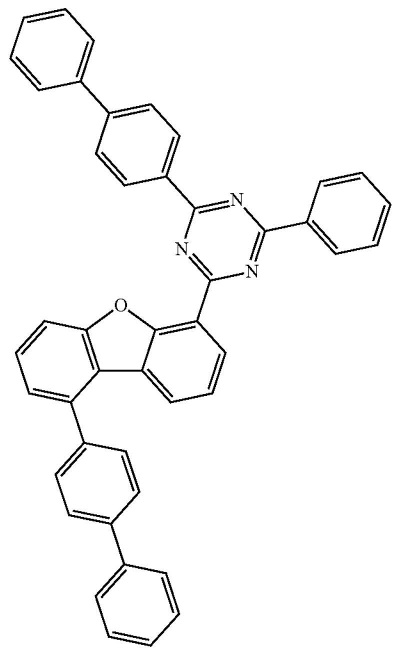
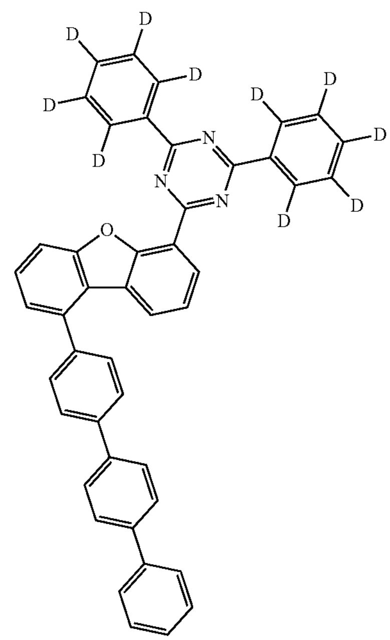

-continued
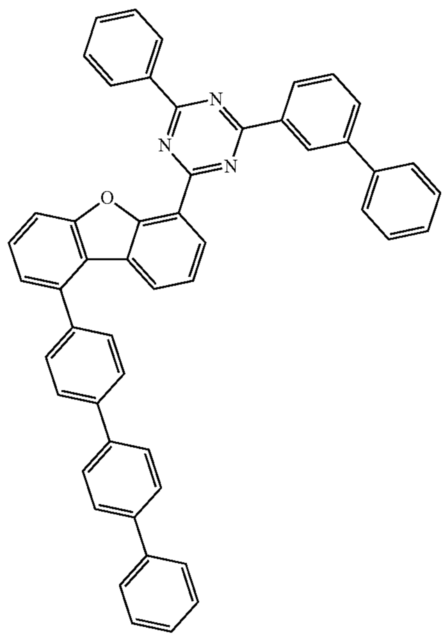
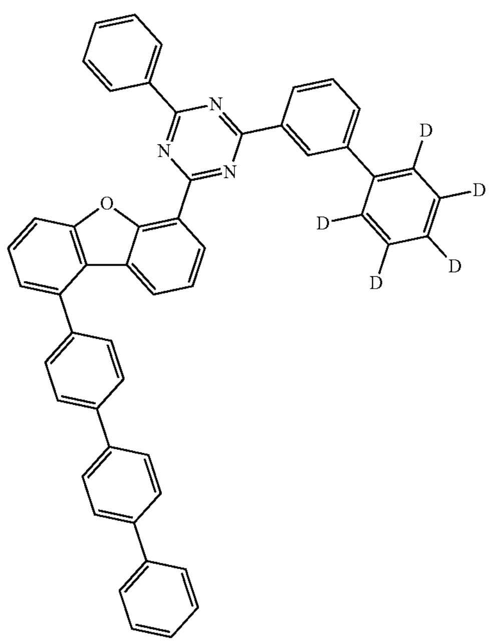
-continued
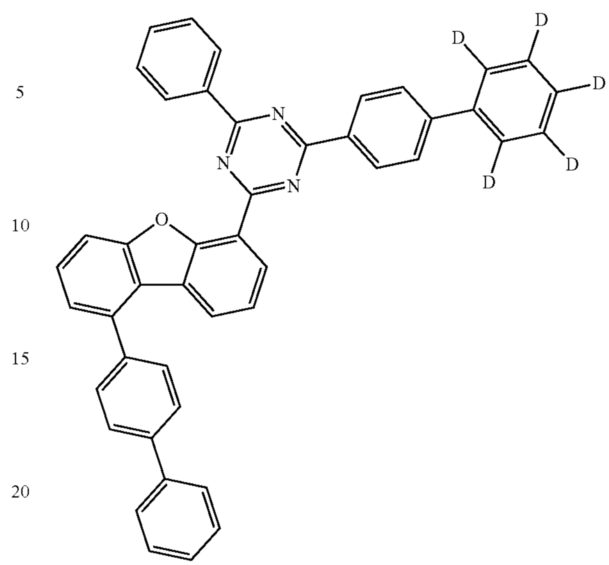
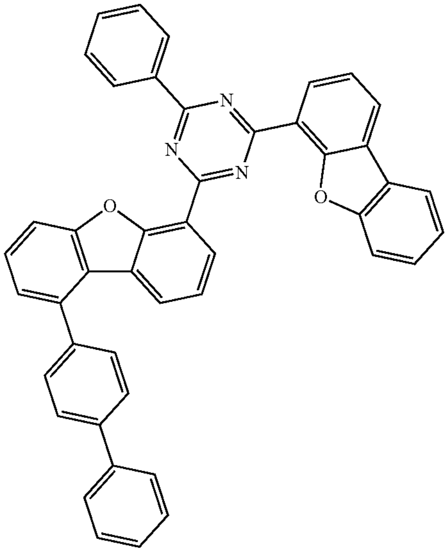

-continued
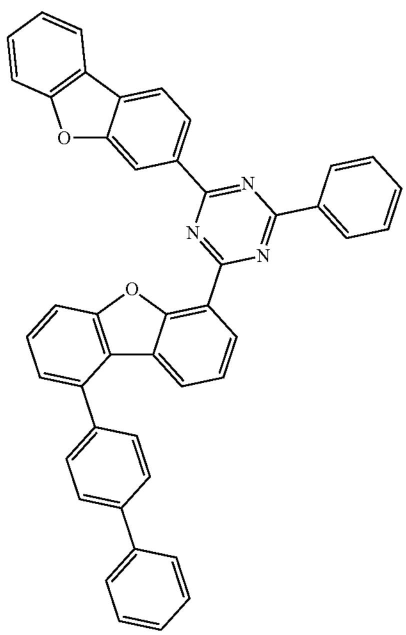
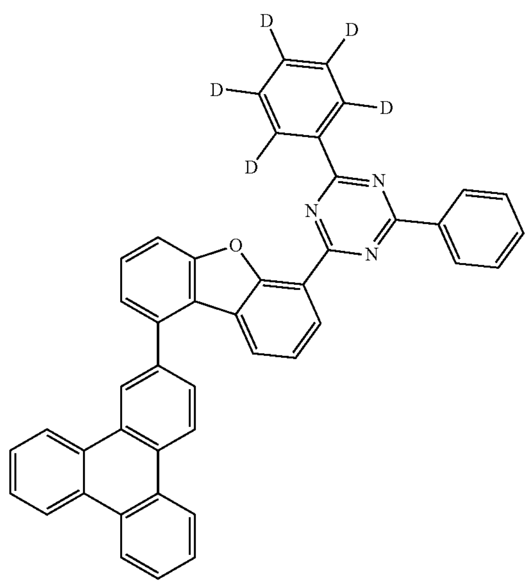
-continued
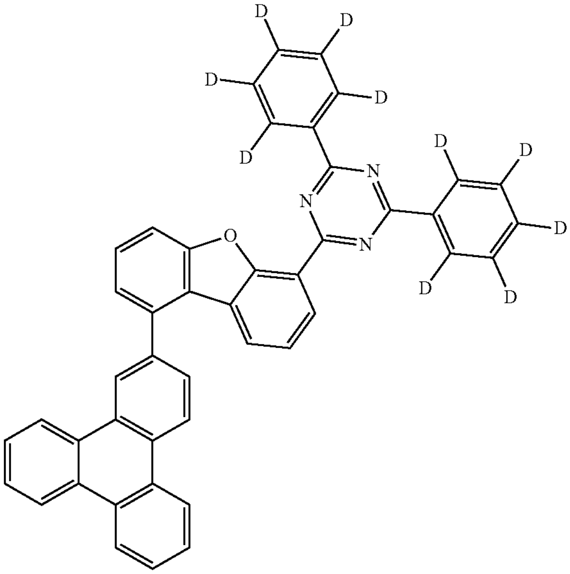
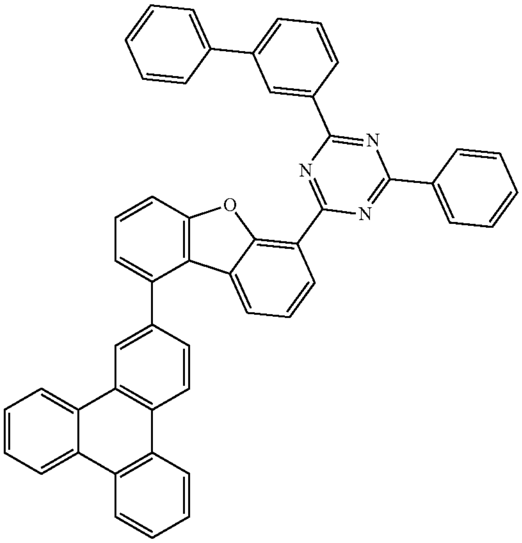
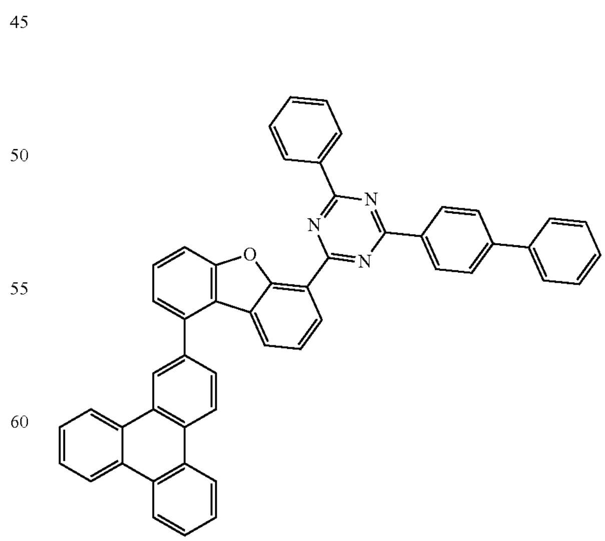

-continued
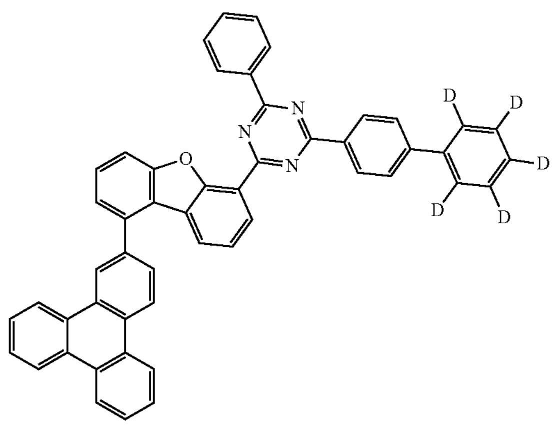
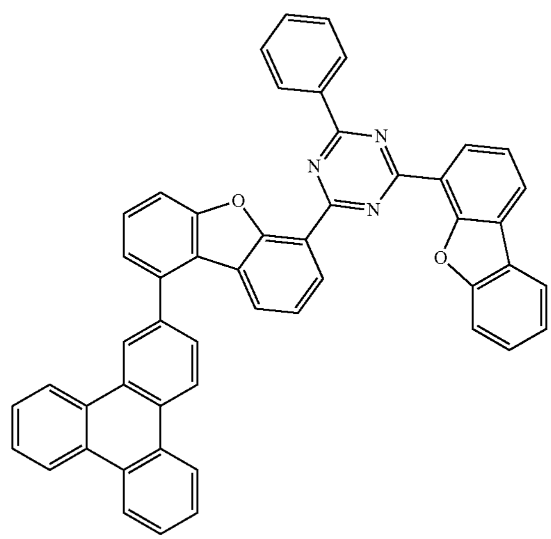
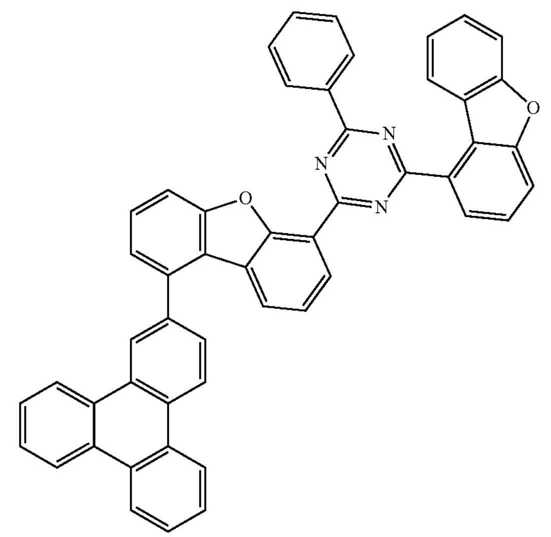
-continued
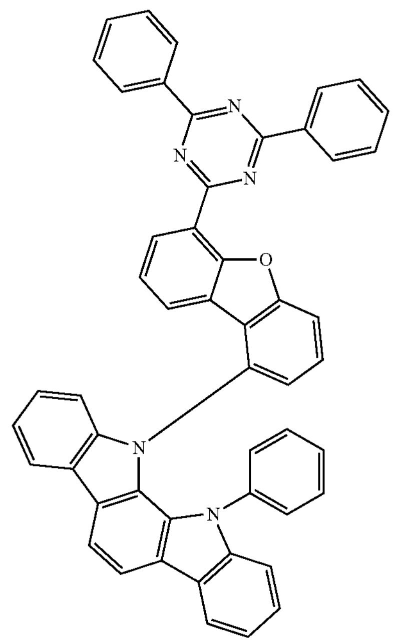
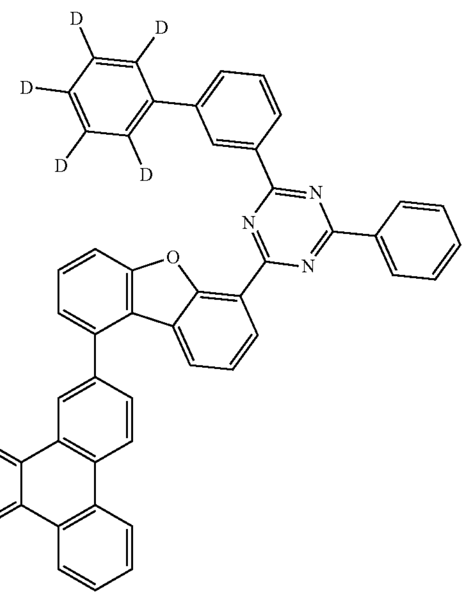
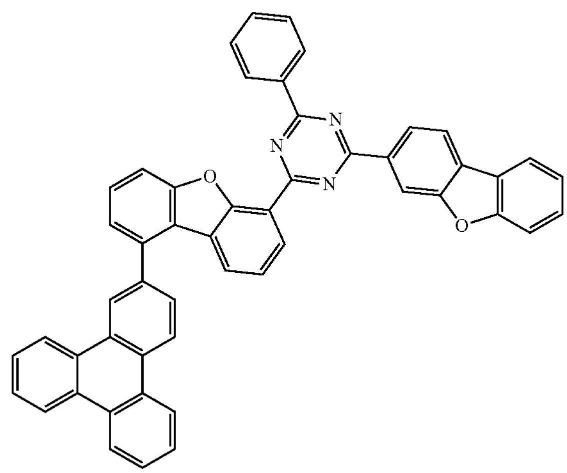

-continued
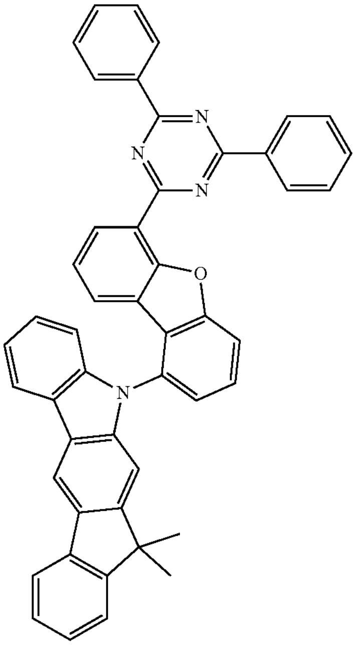
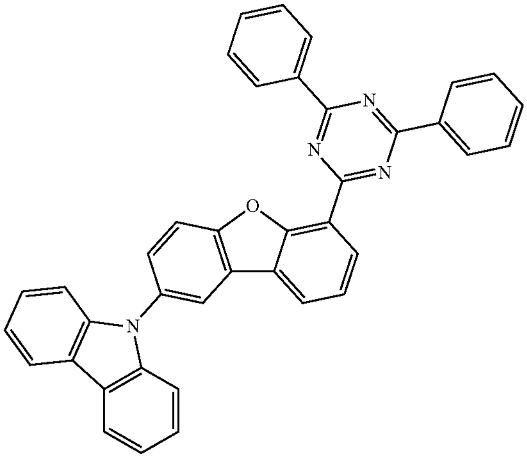
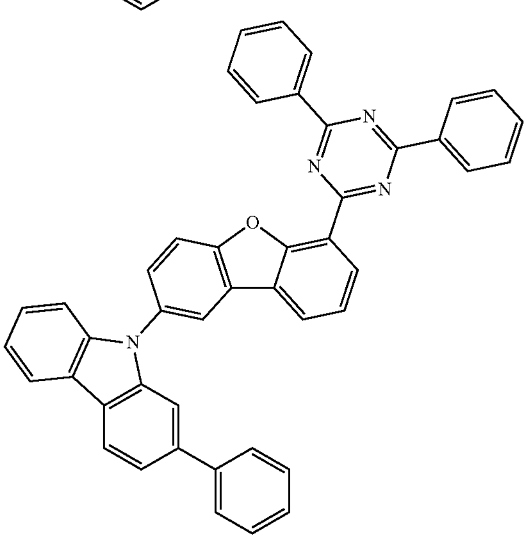
-continued
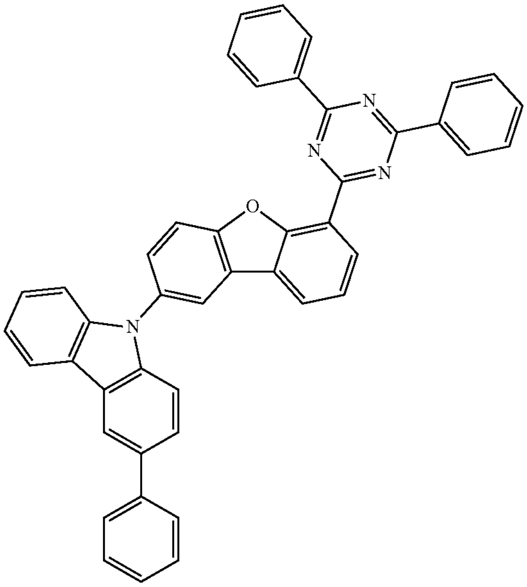
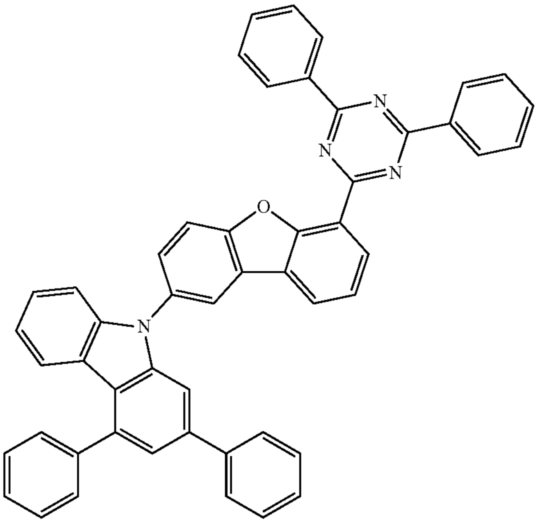
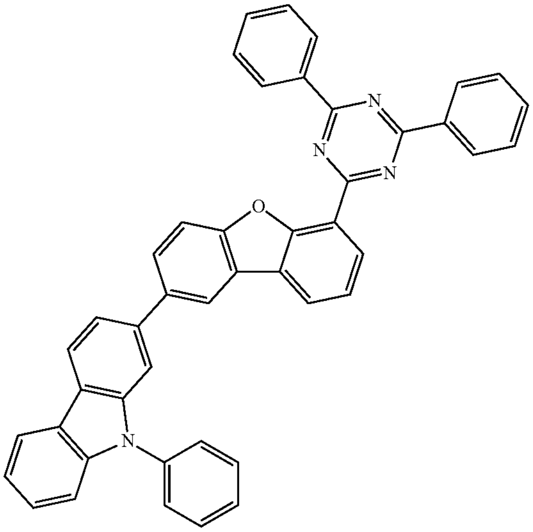

-continued
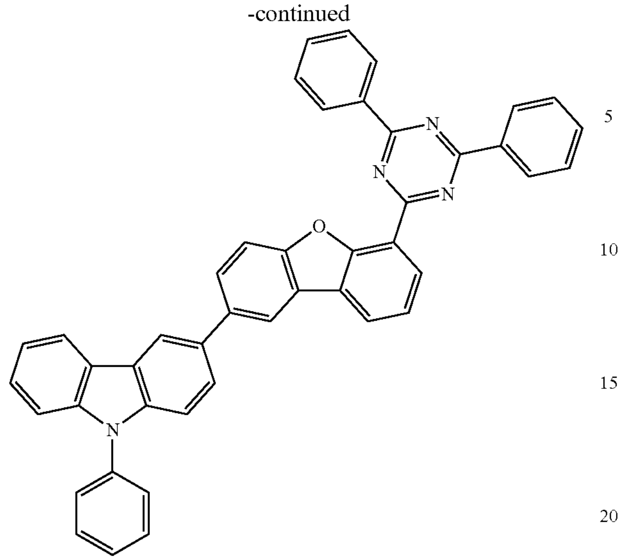
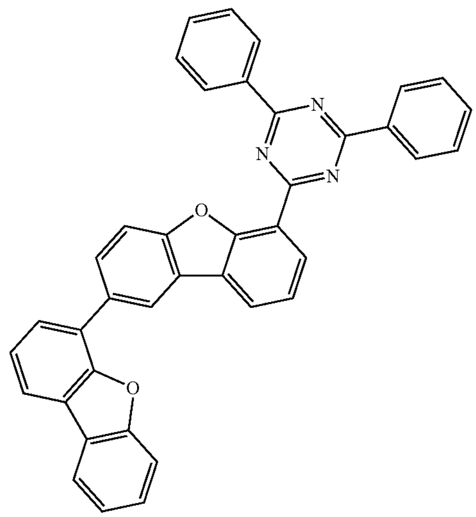
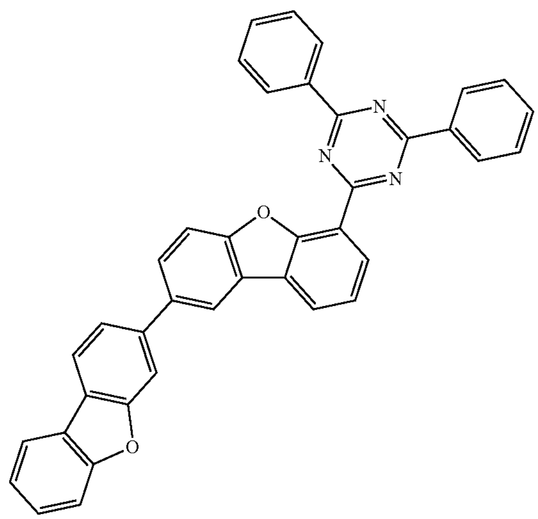
-continued
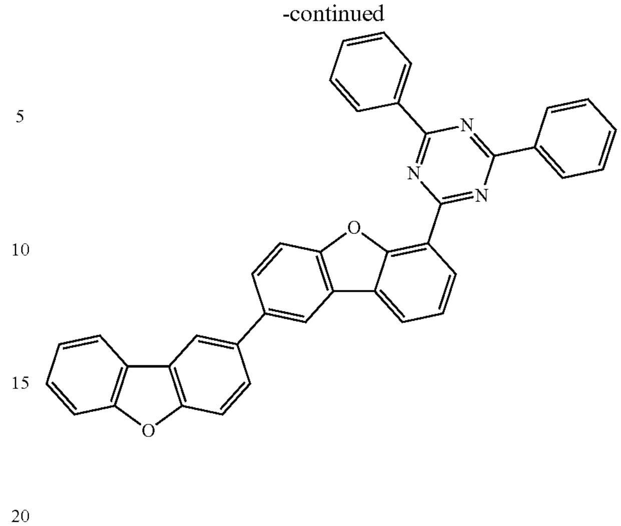
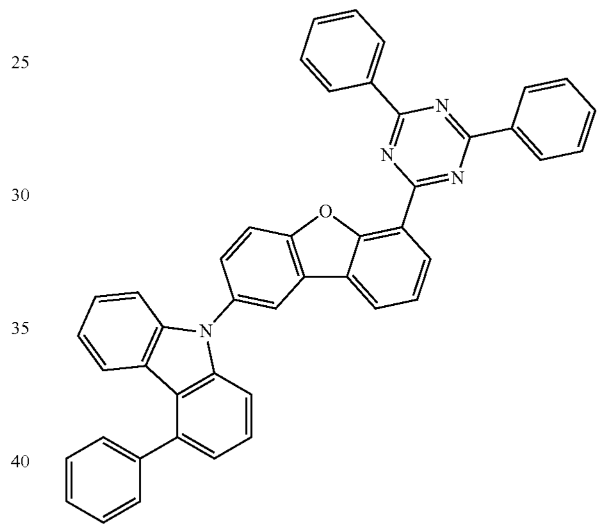
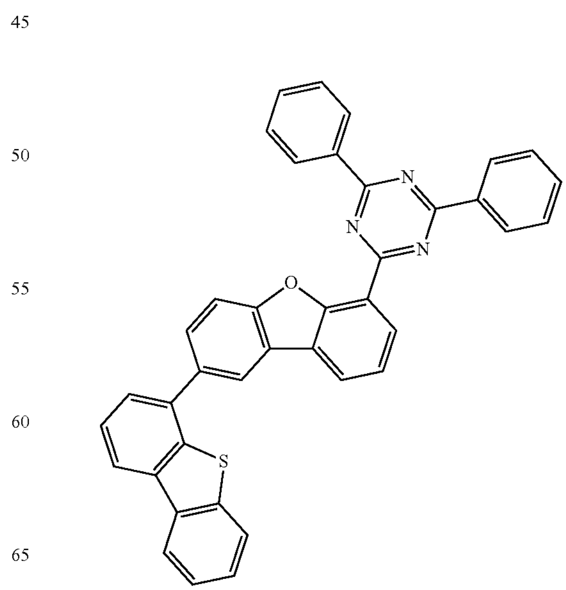

-continued
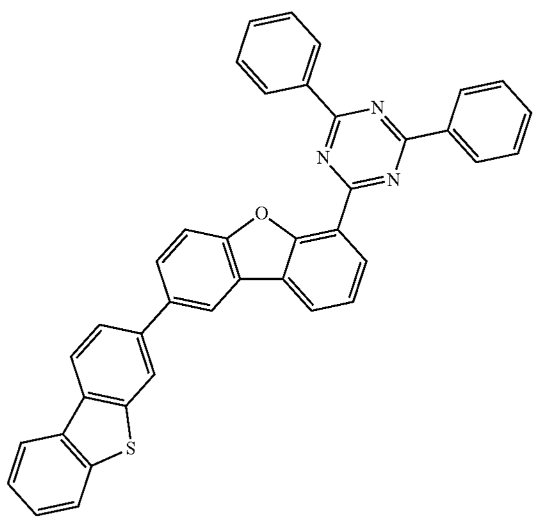
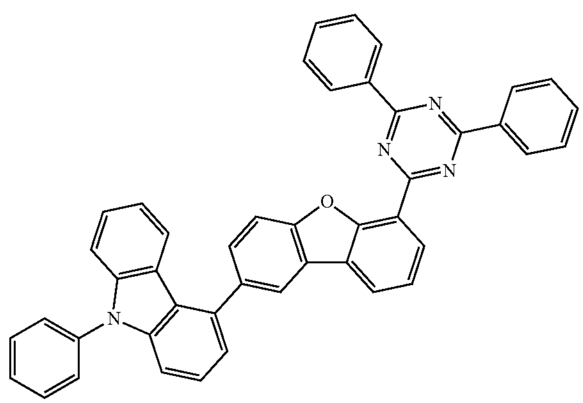
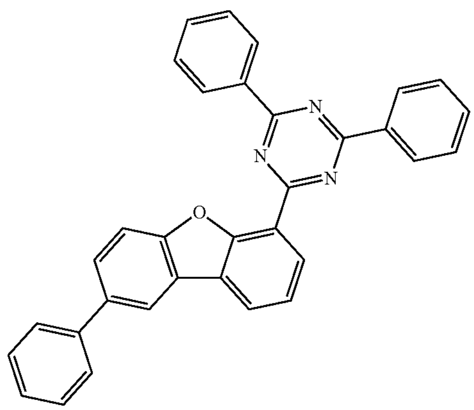
-continued
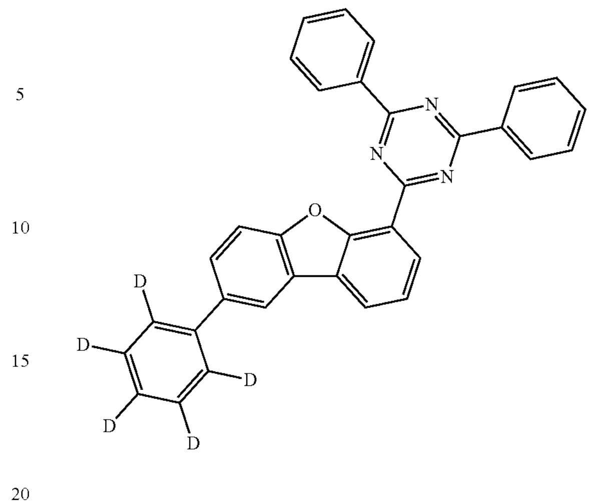
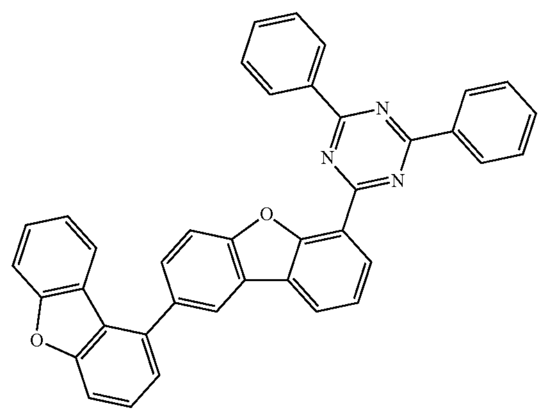
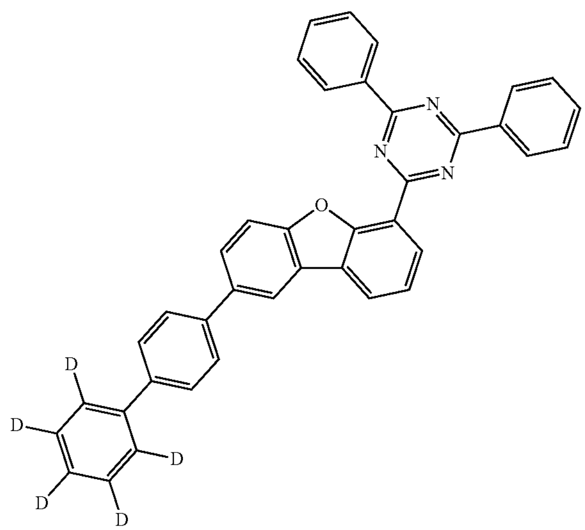

-continued
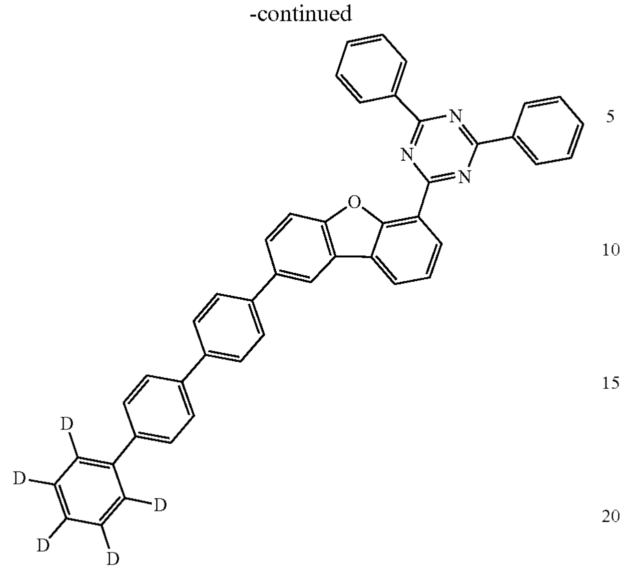
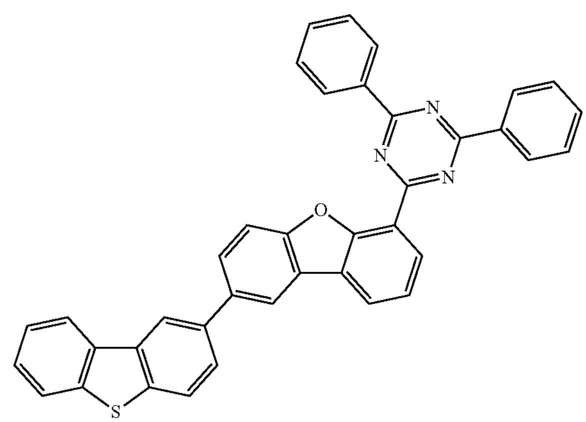
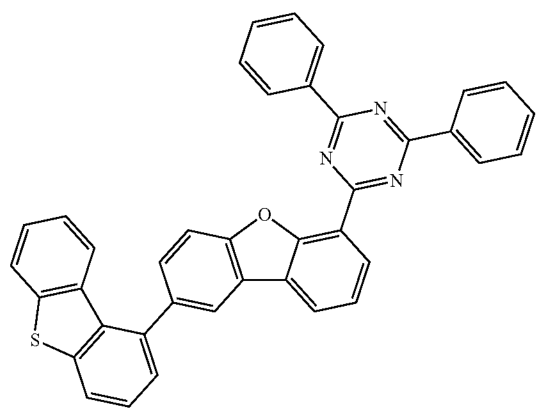
-continued
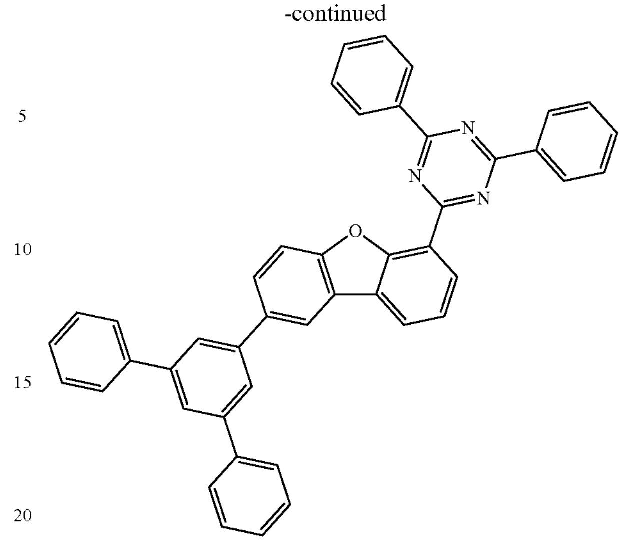
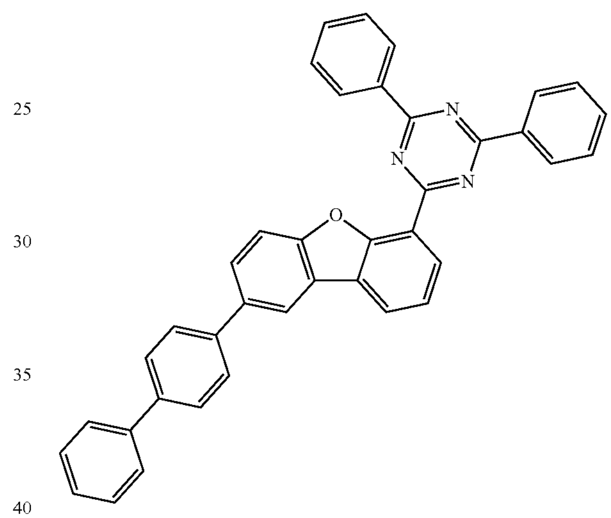
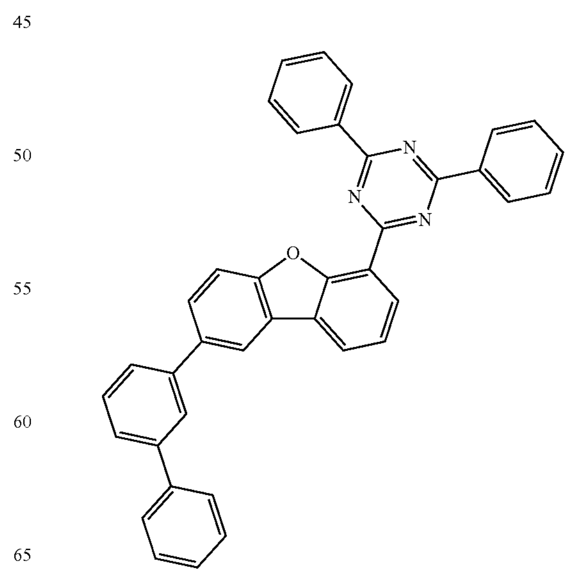

-continued
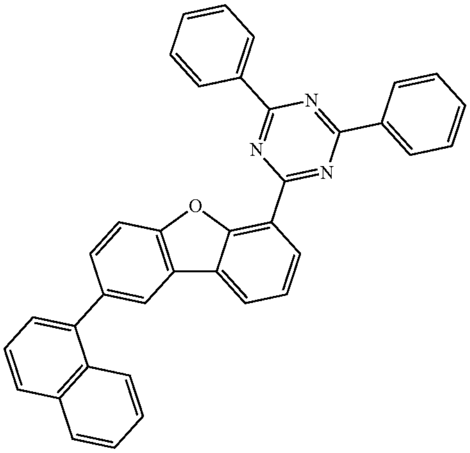
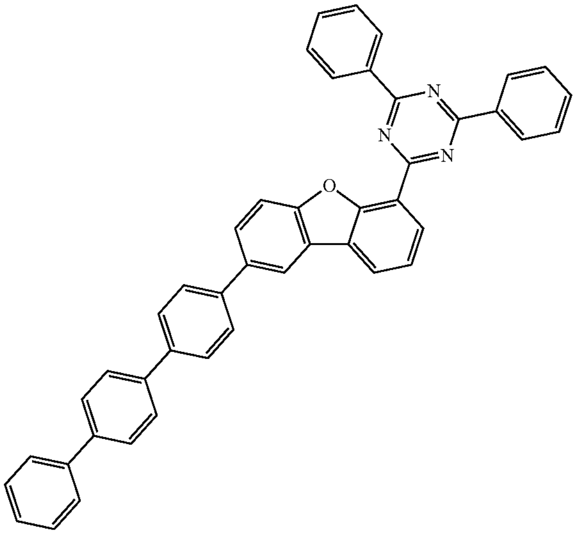
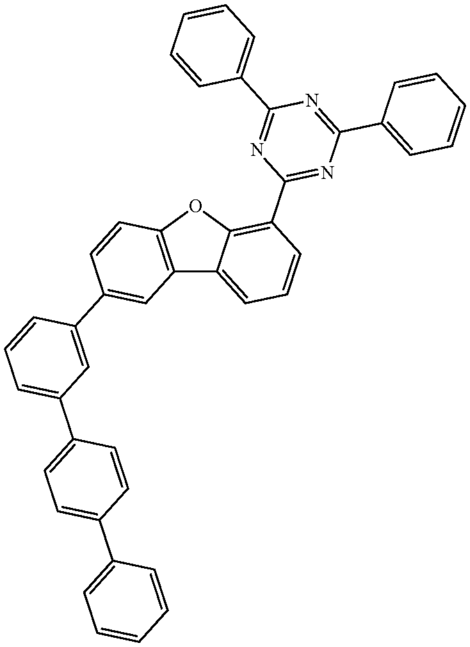
-continued
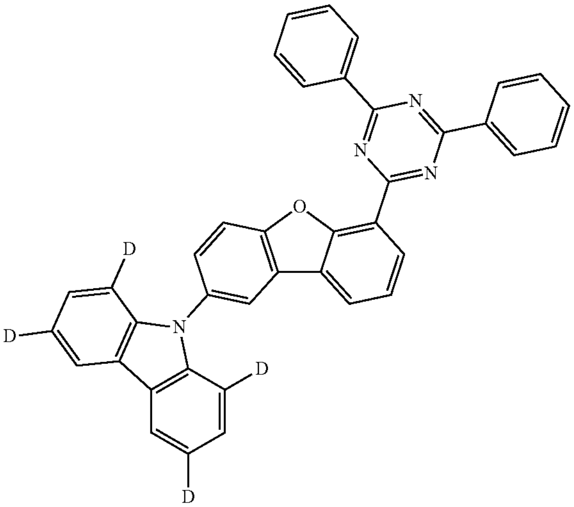
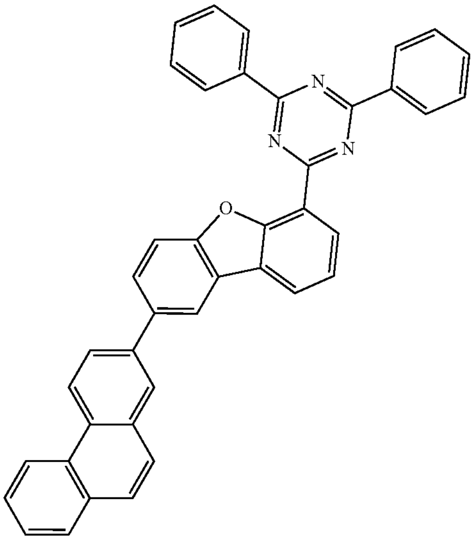
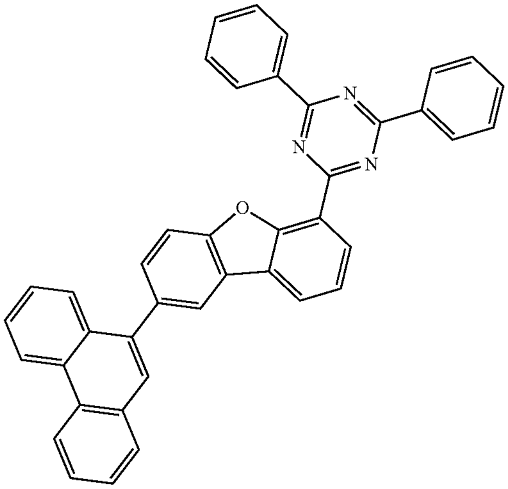

-continued
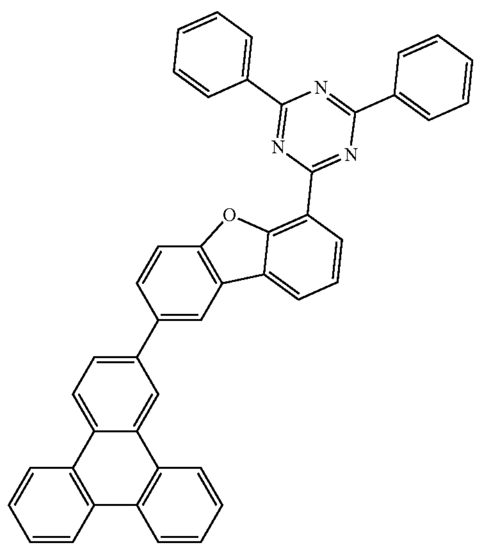
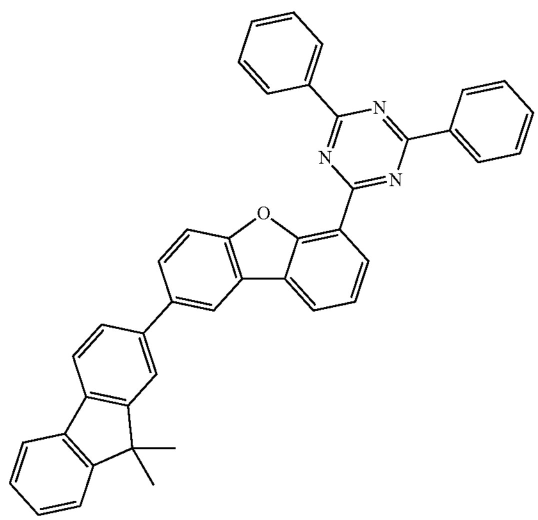
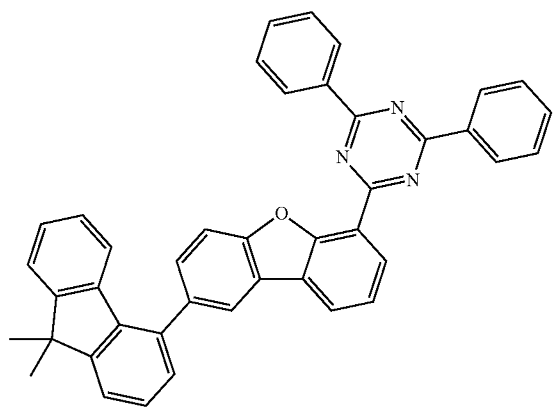
-continued
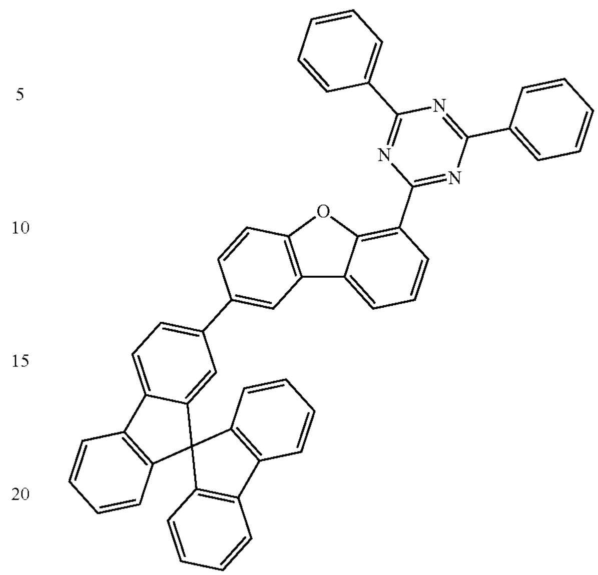
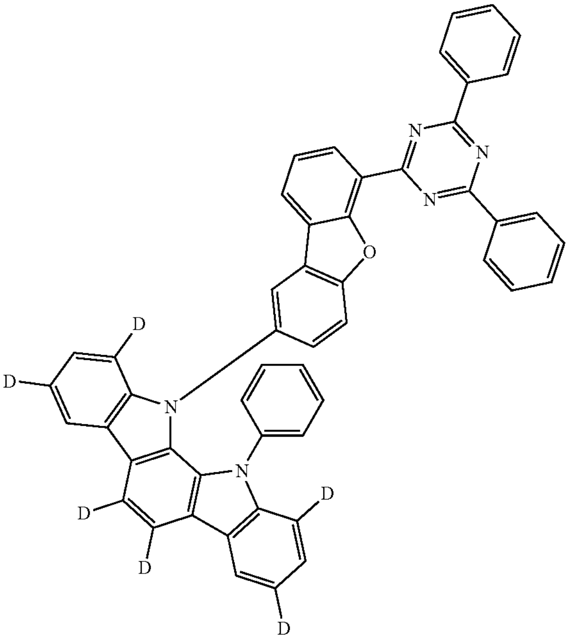

-continued
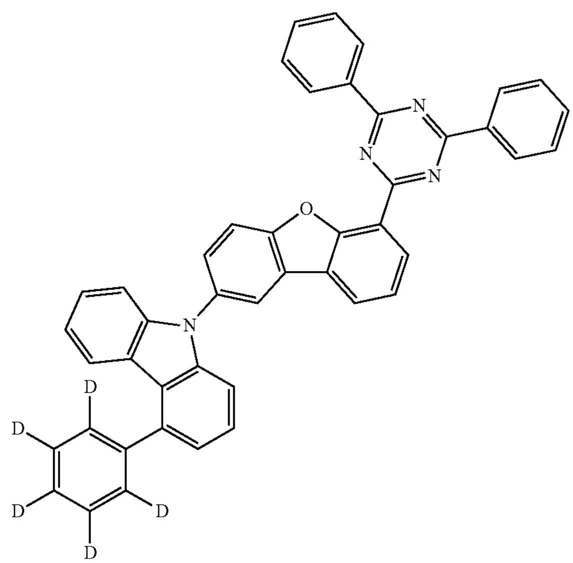
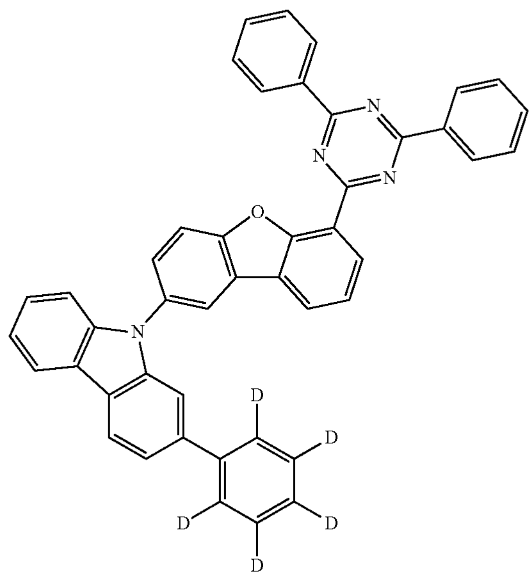
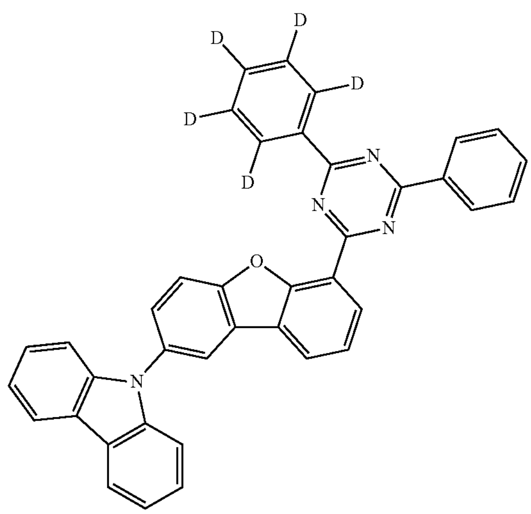
-continued
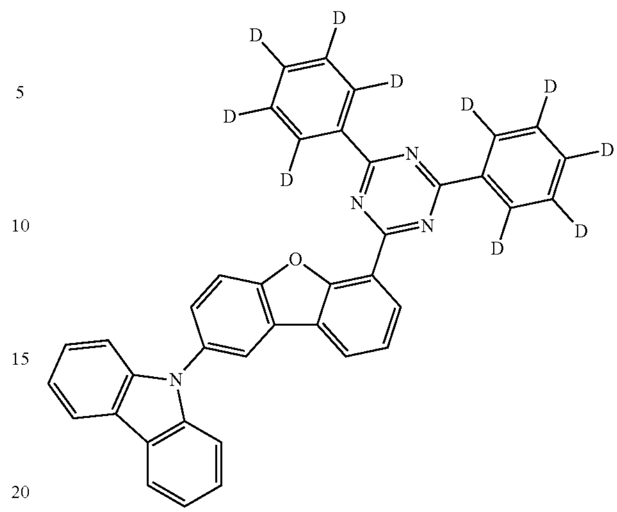
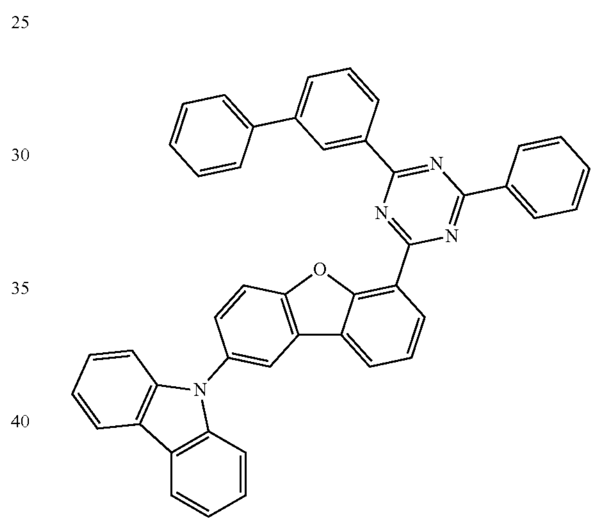
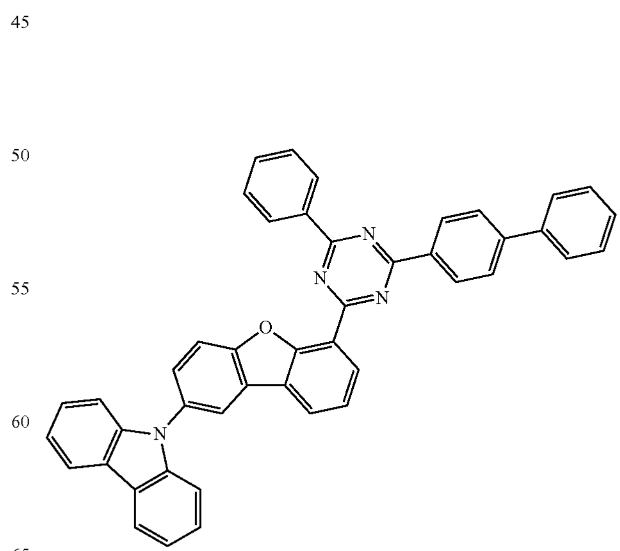

-continued
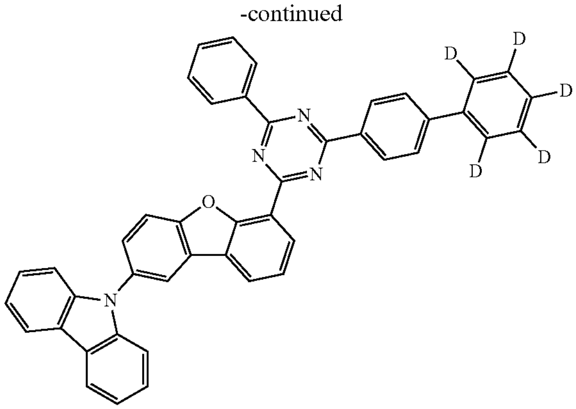
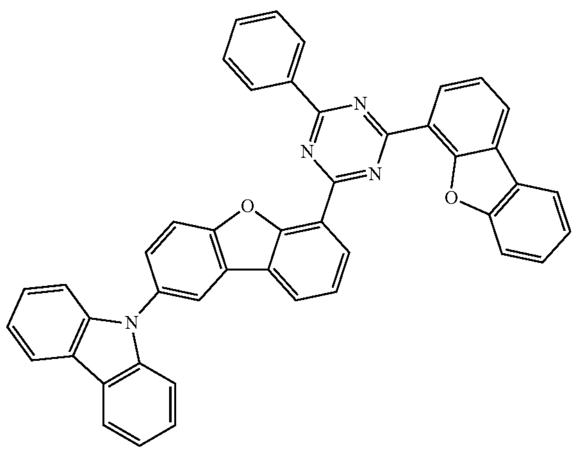
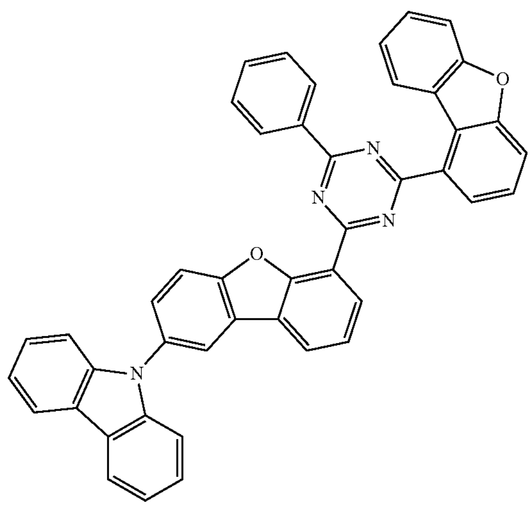
-continued
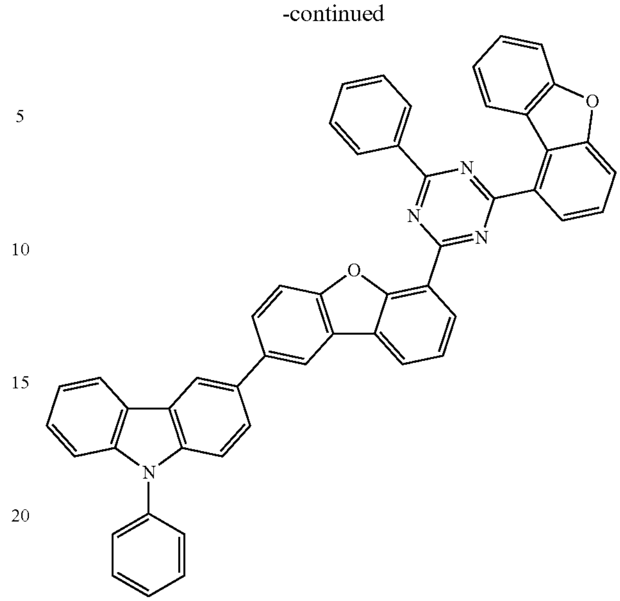
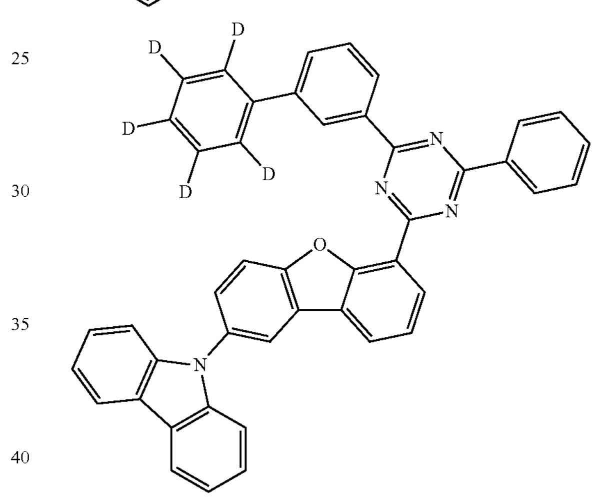
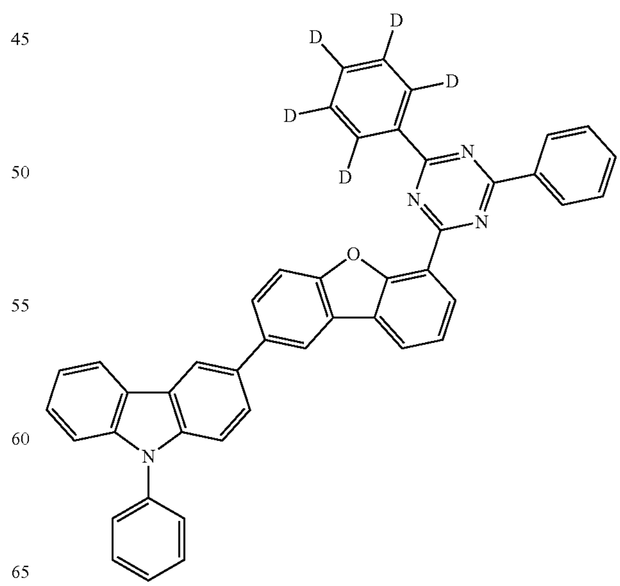

-continued
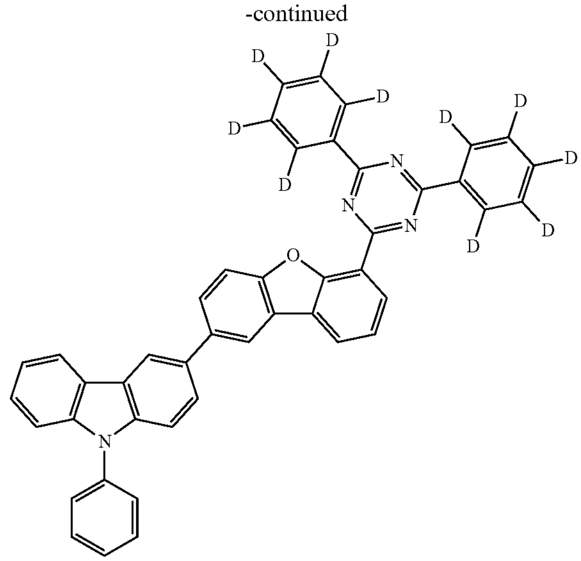
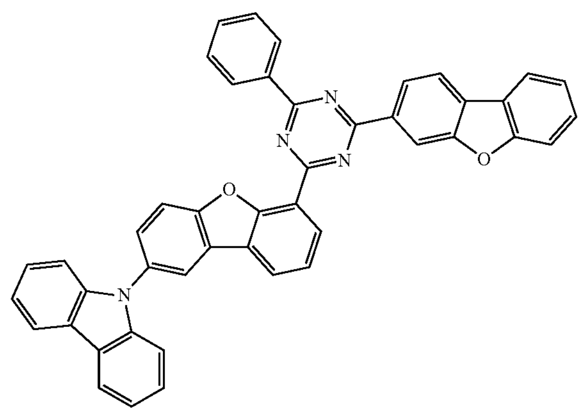
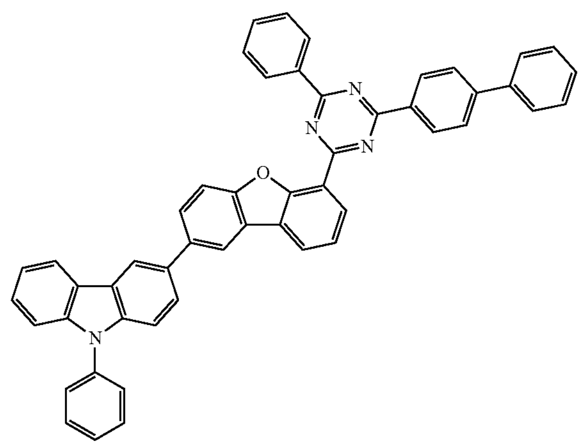
-continued
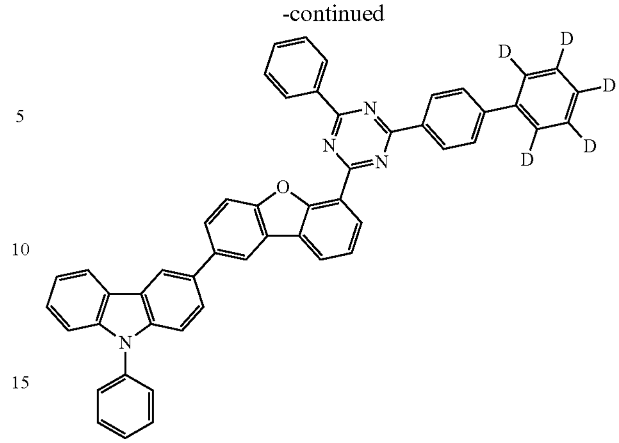
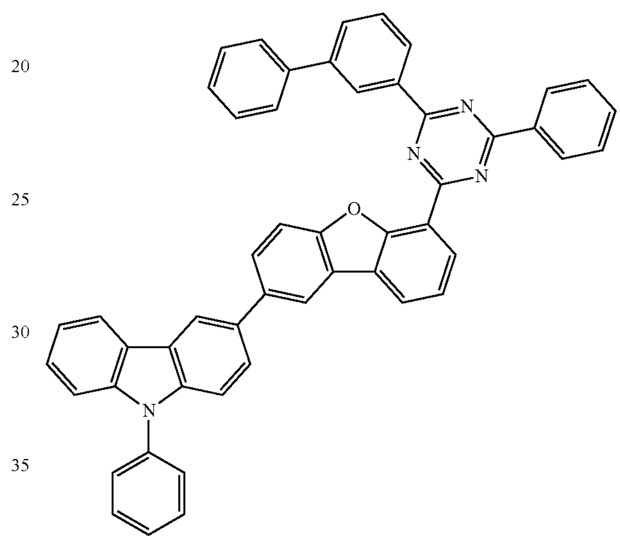
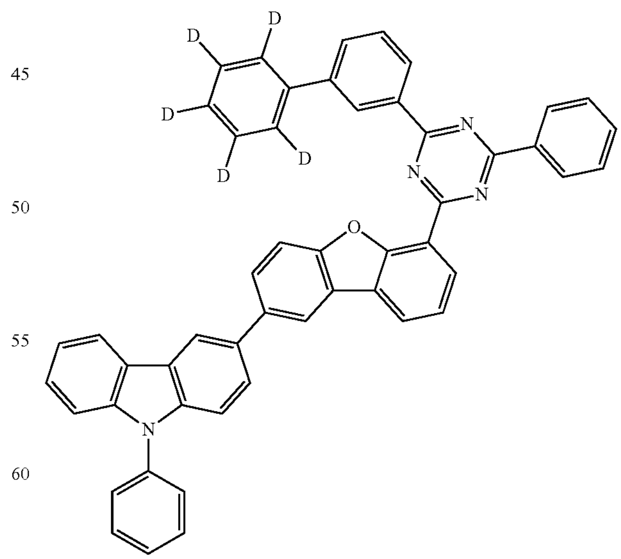

-continued
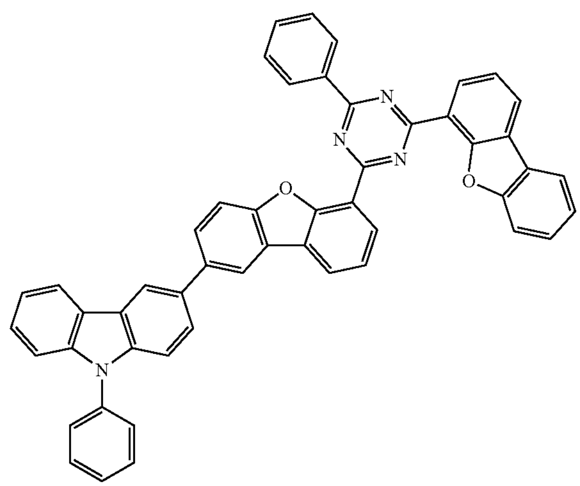
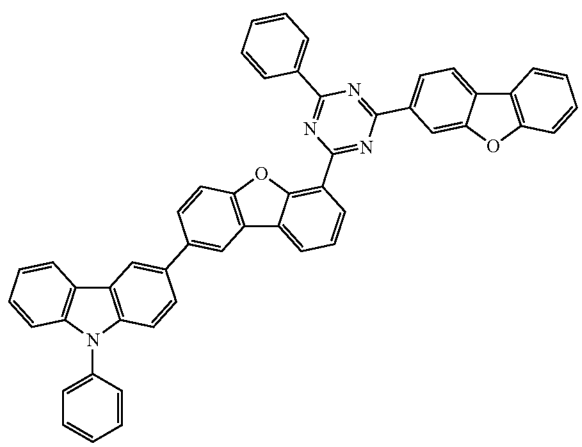
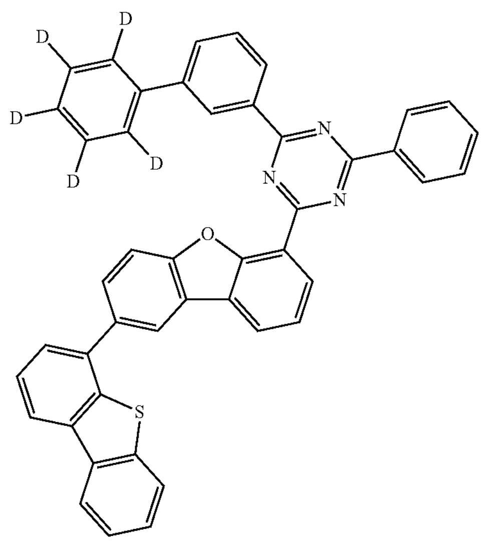
-continued
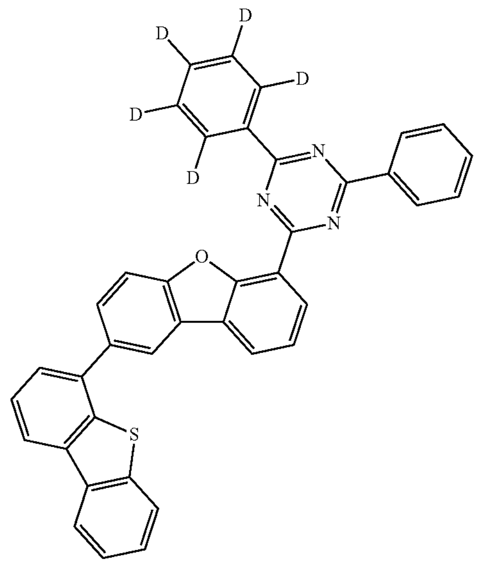
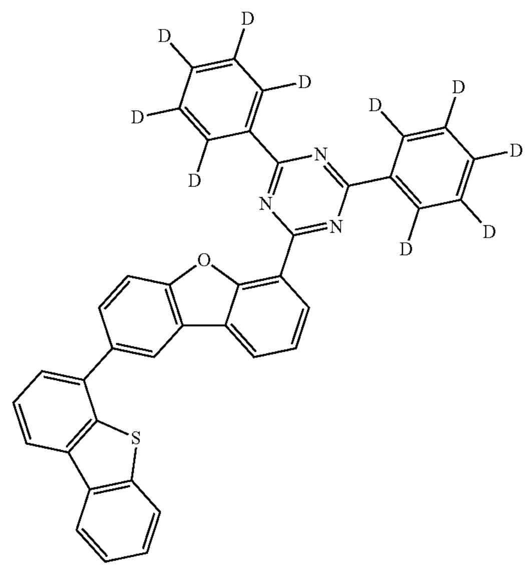
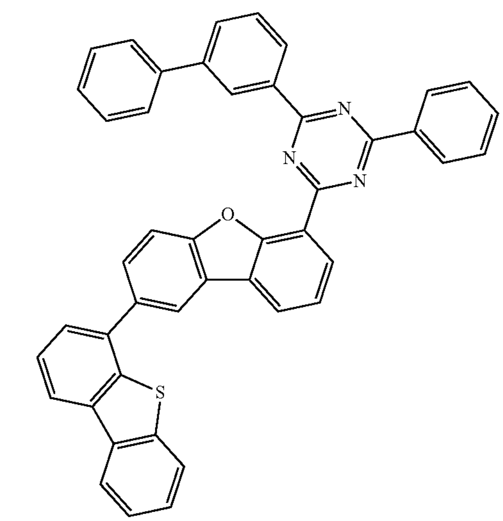

-continued
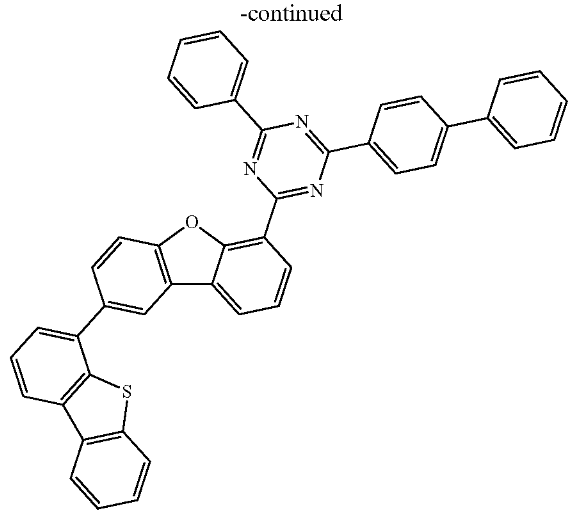
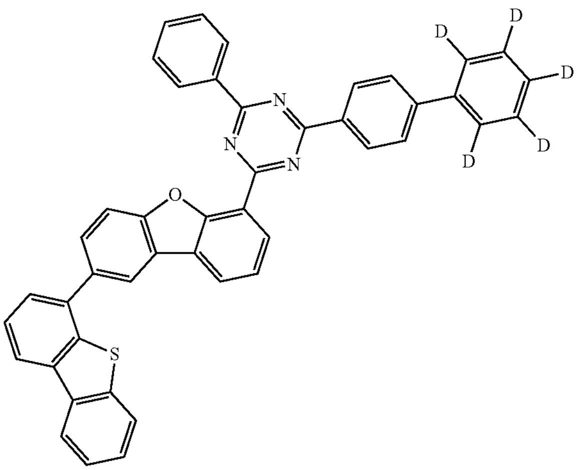
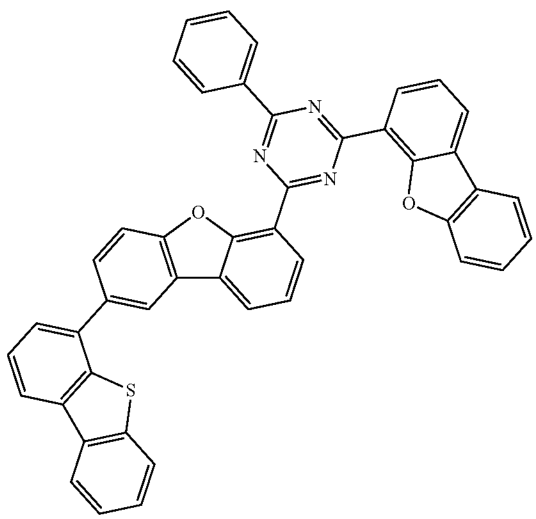
-continued
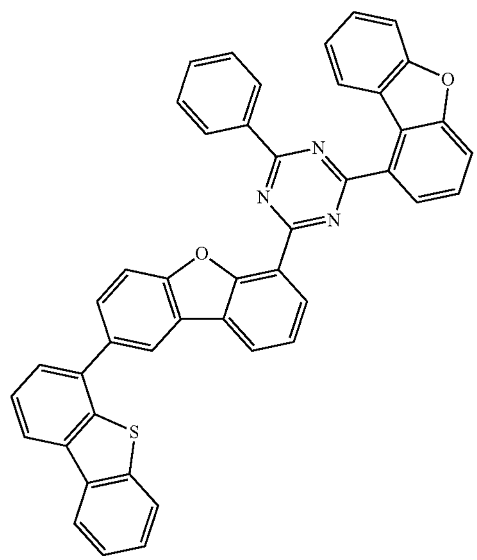
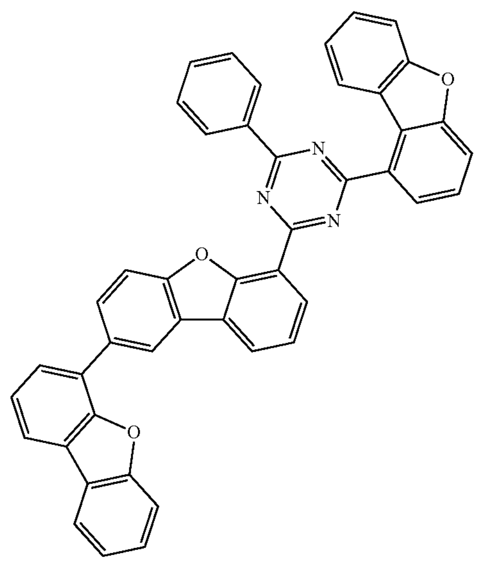
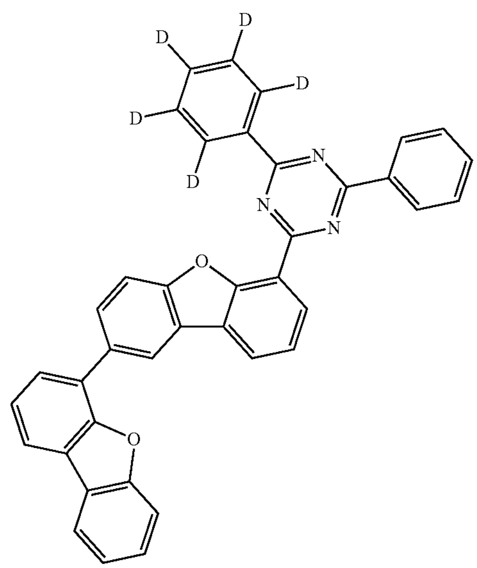

-continued
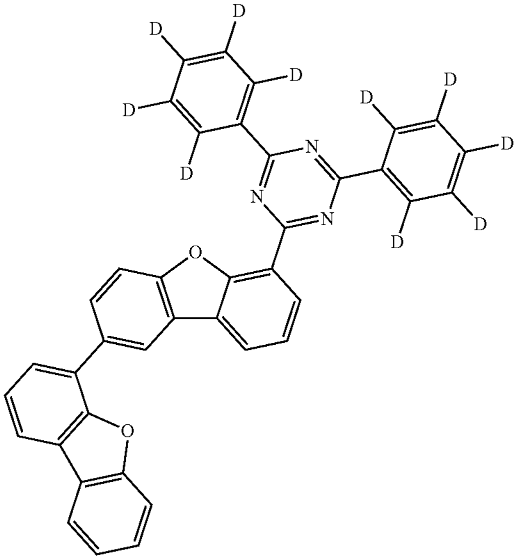
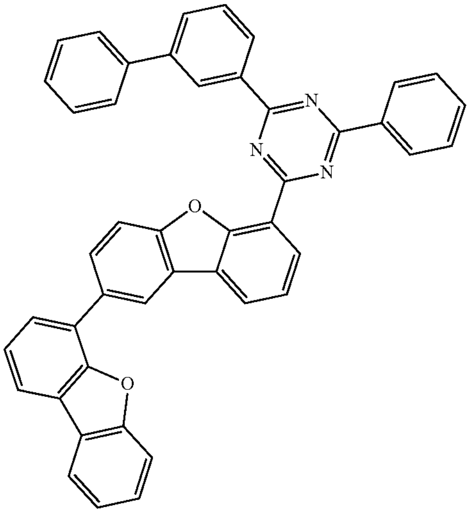
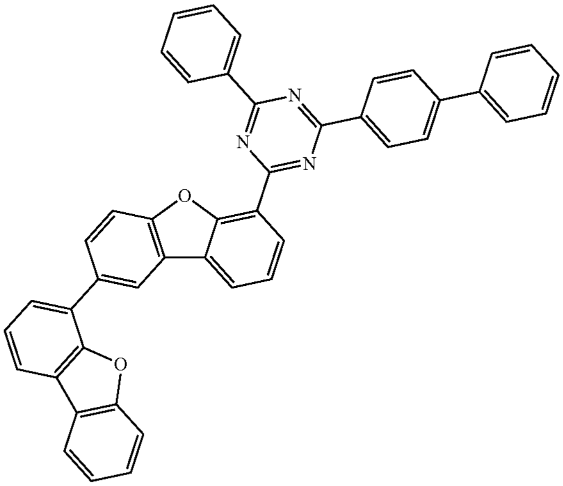
-continued
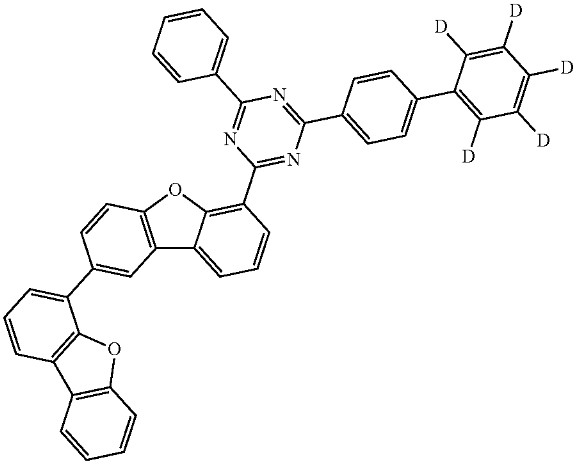
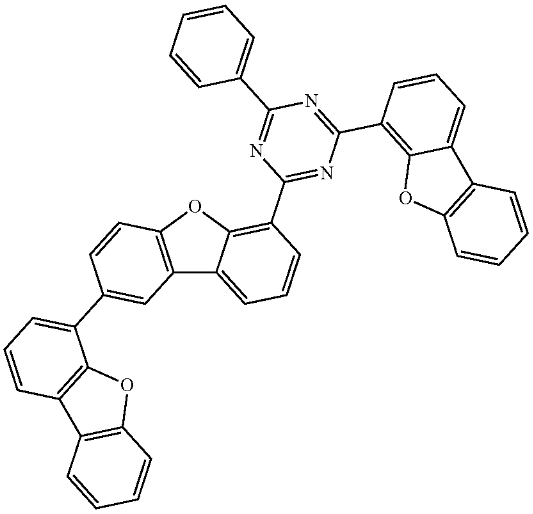
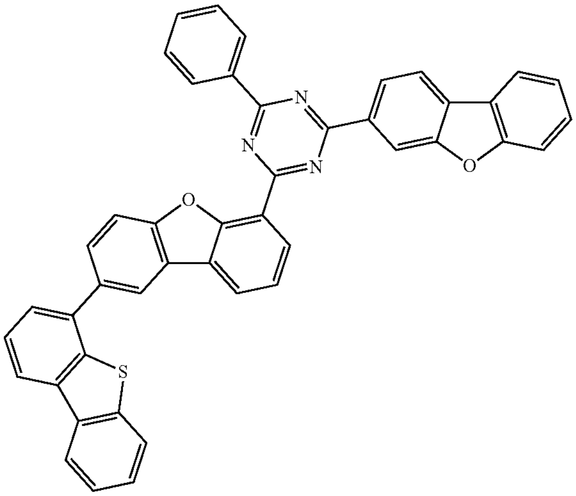

-continued
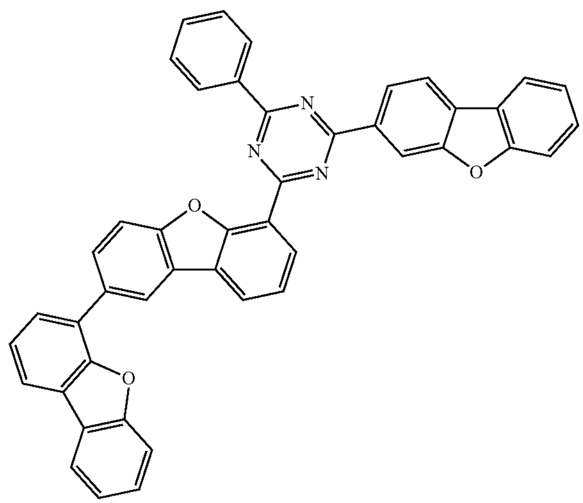
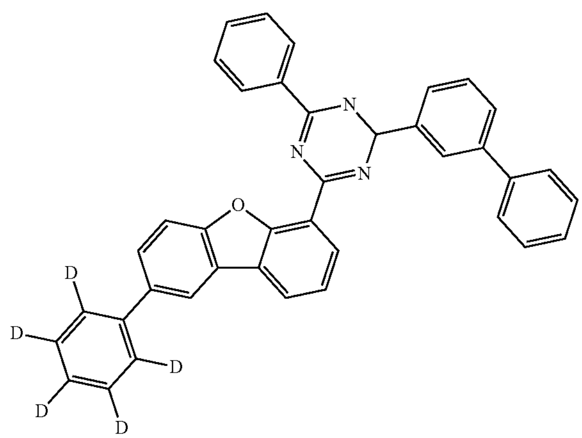
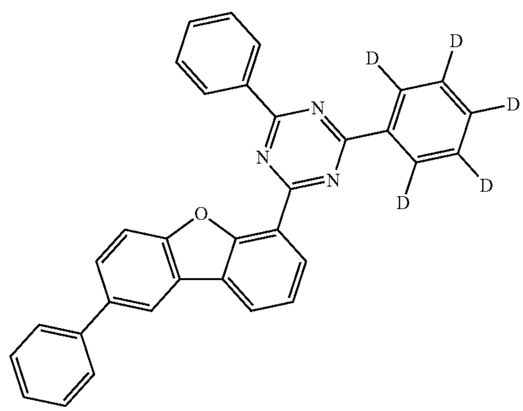
-continued
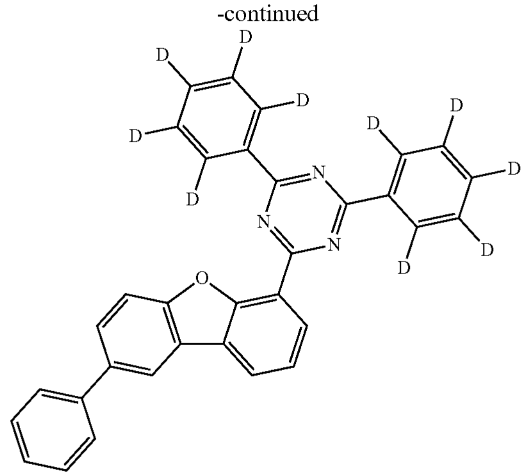
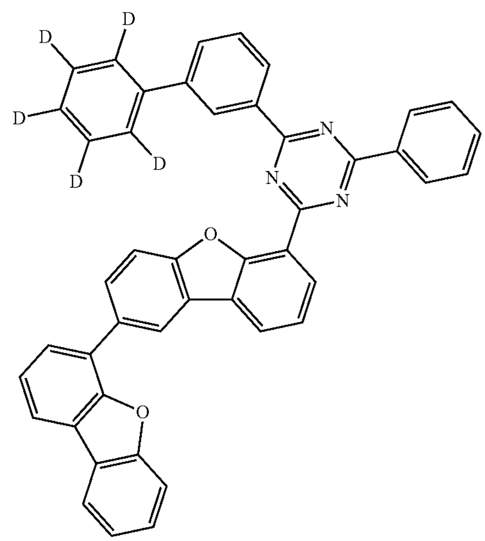
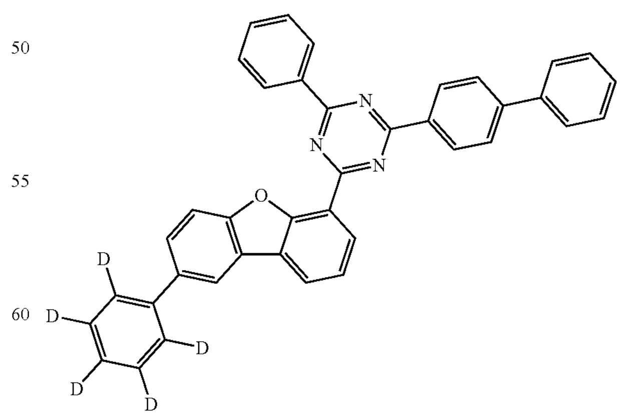

-continued
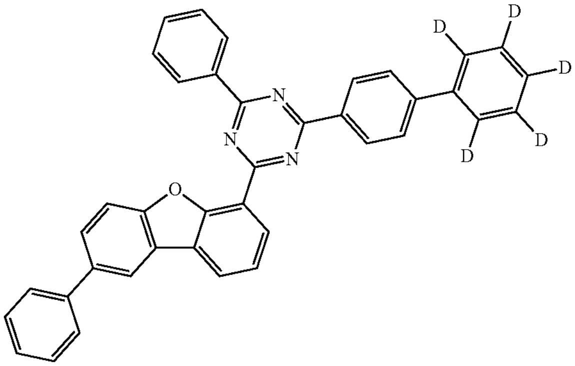
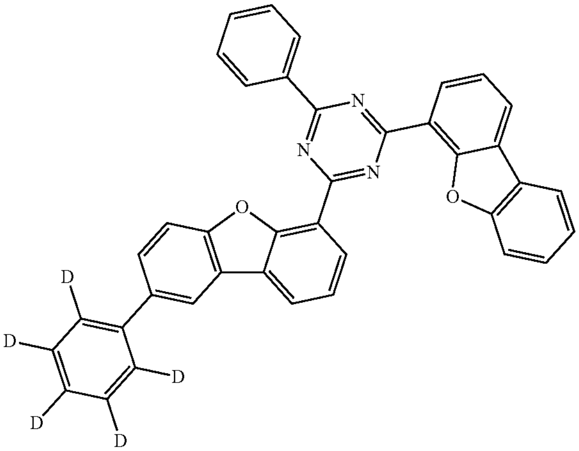
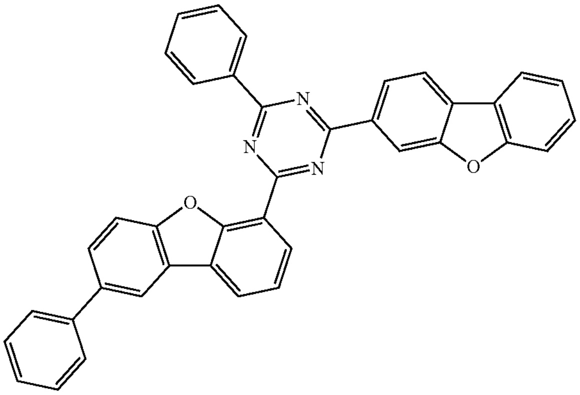
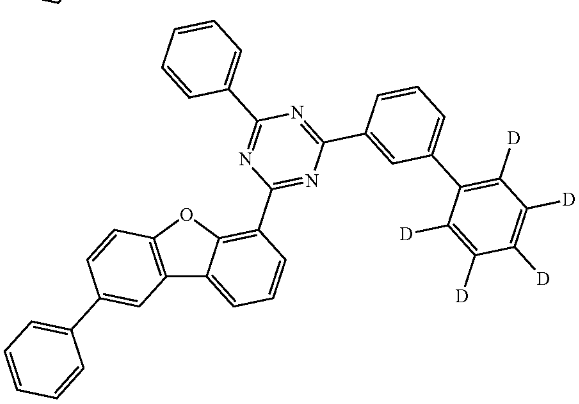
-continued
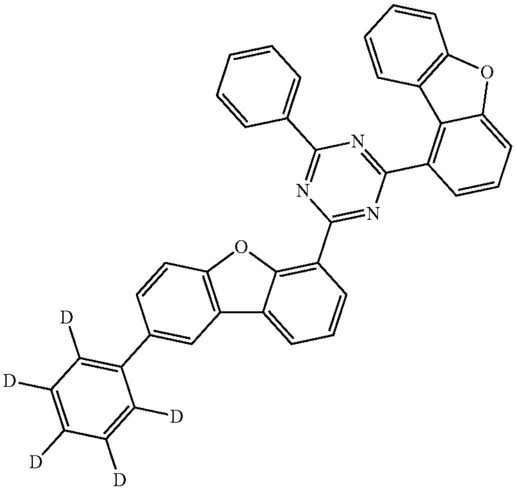
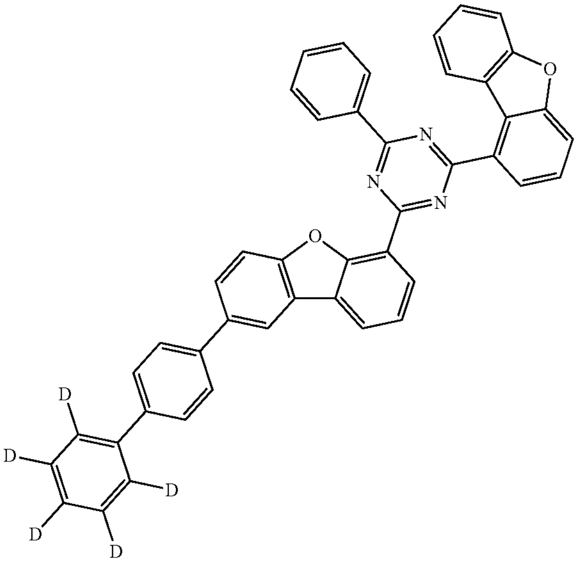
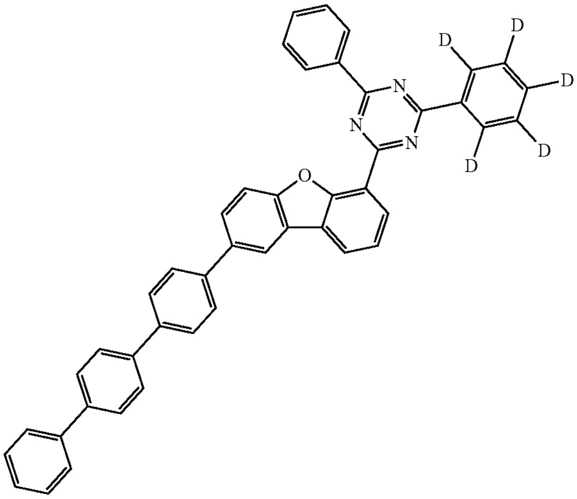

-continued
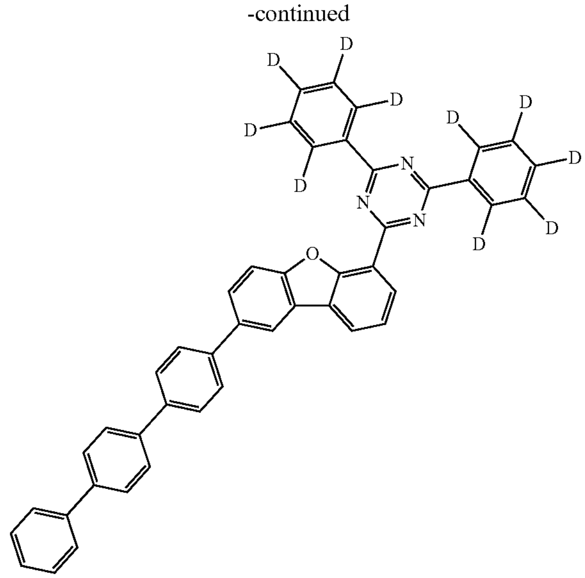
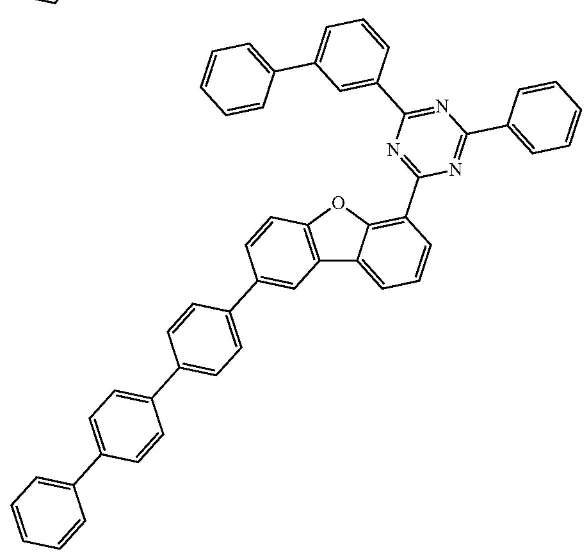
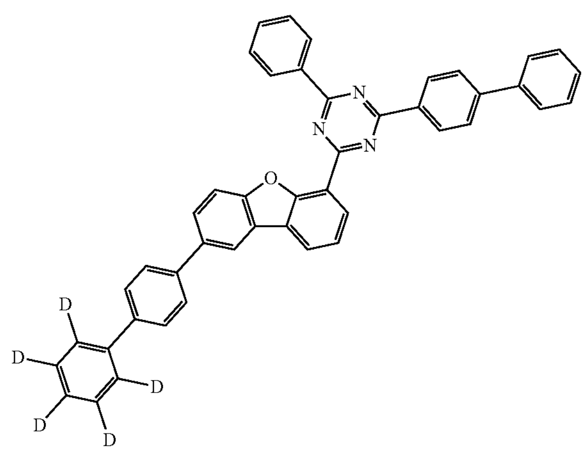
-continued
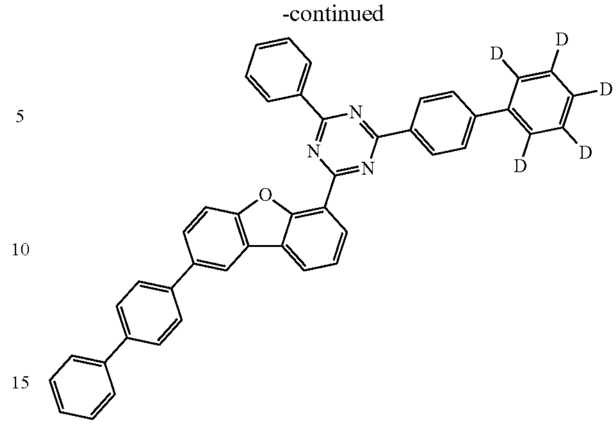
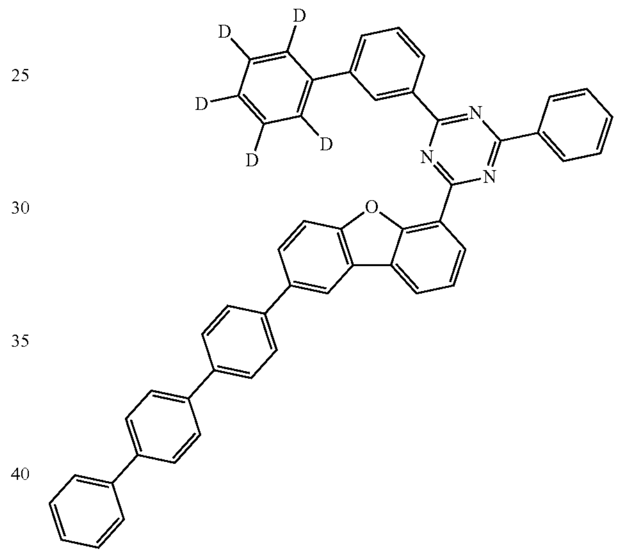
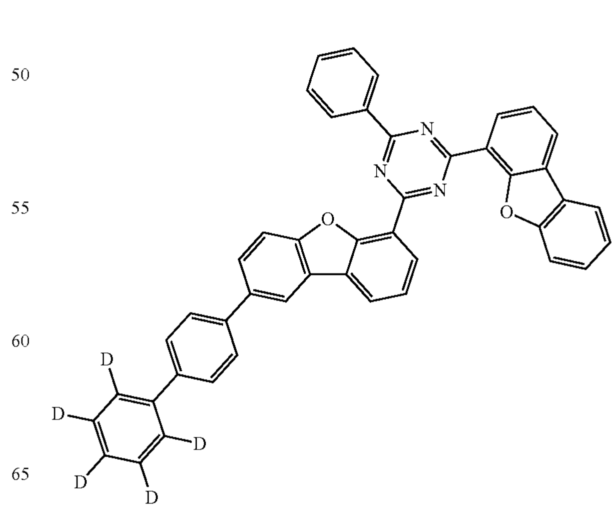

-continued
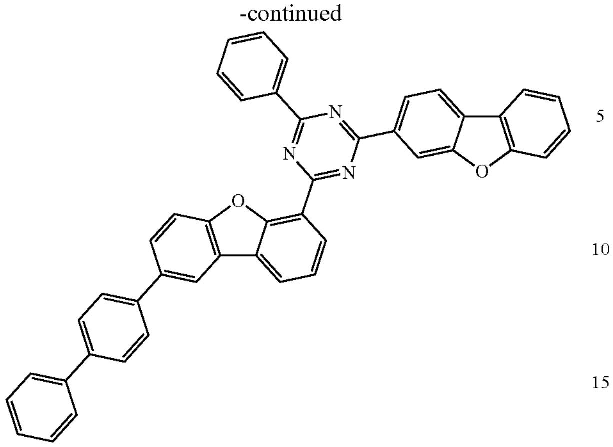
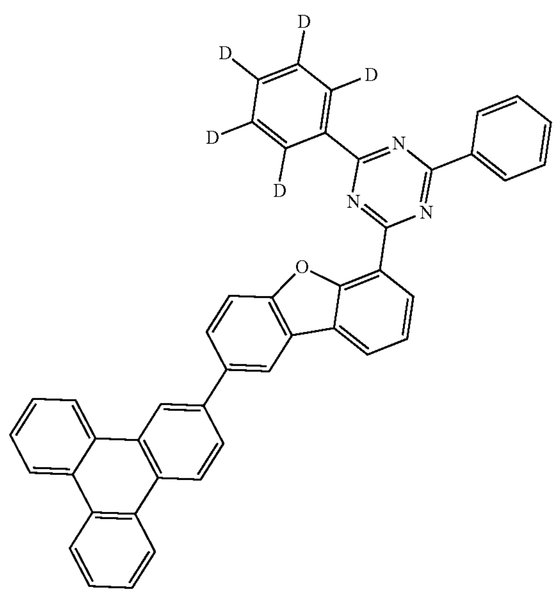
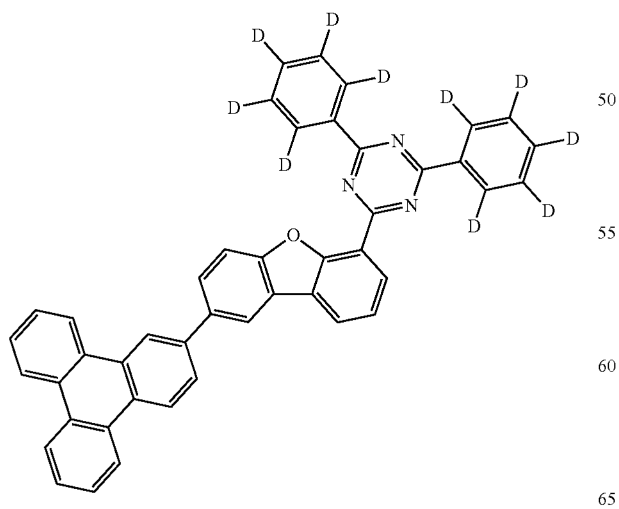
-continued
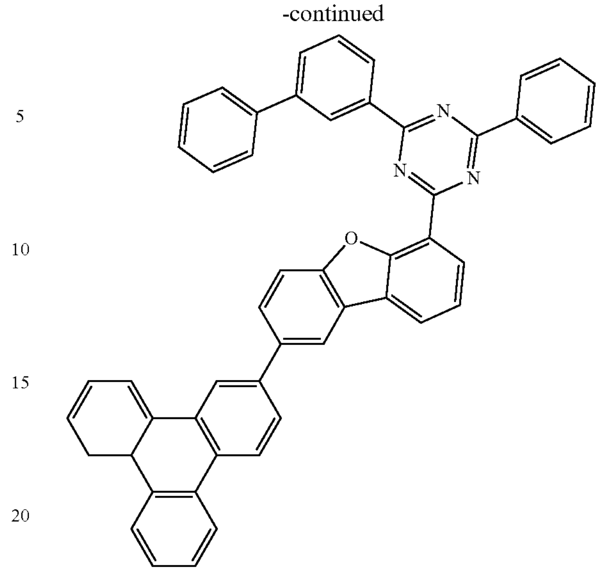
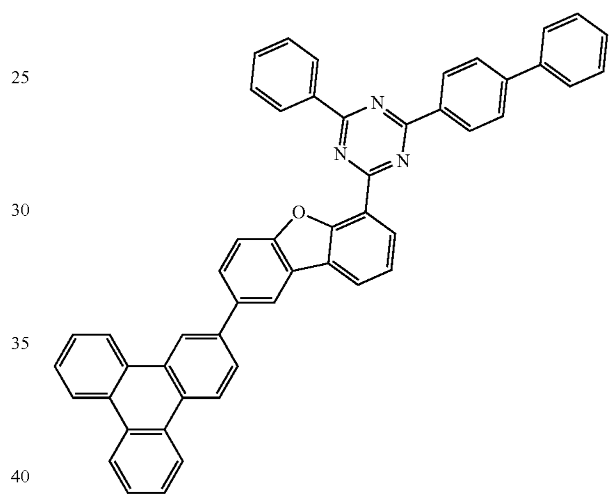
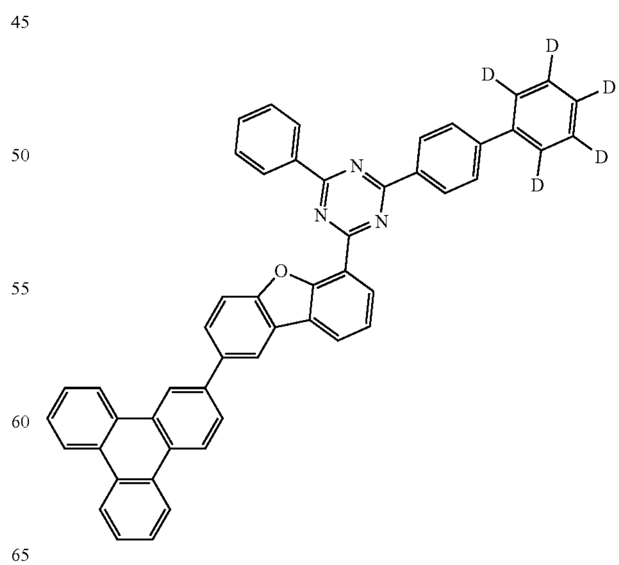

-continued
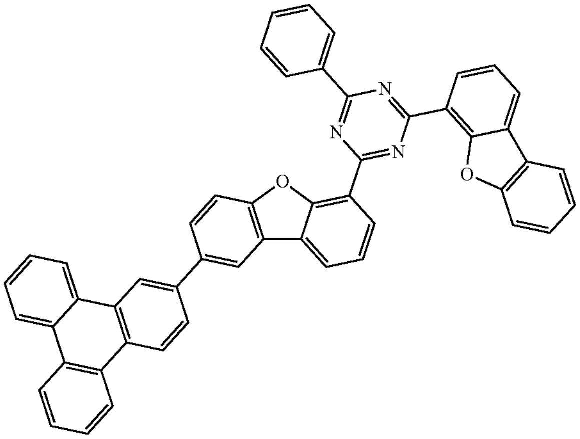
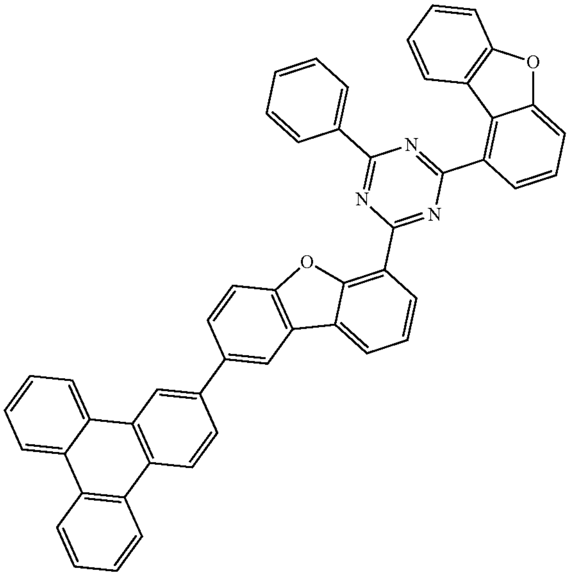
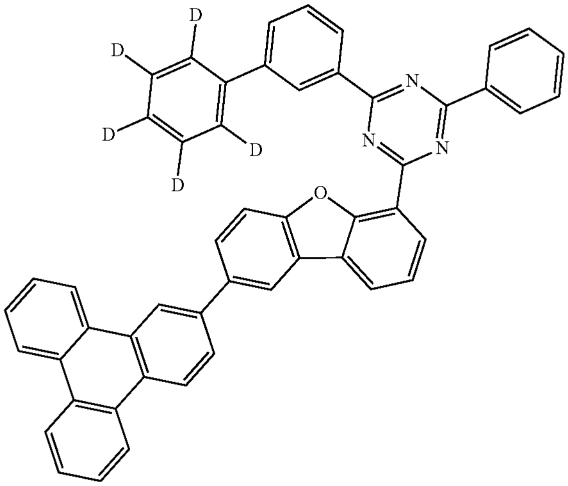
-continued
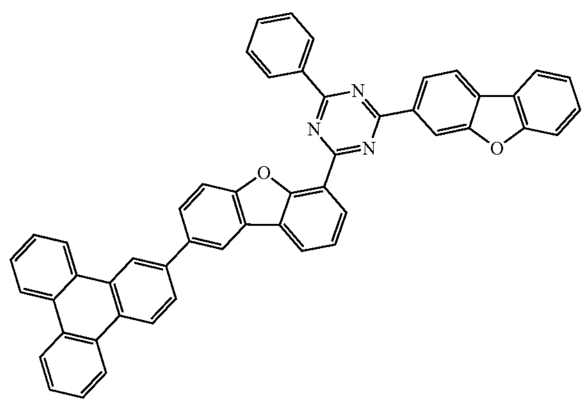
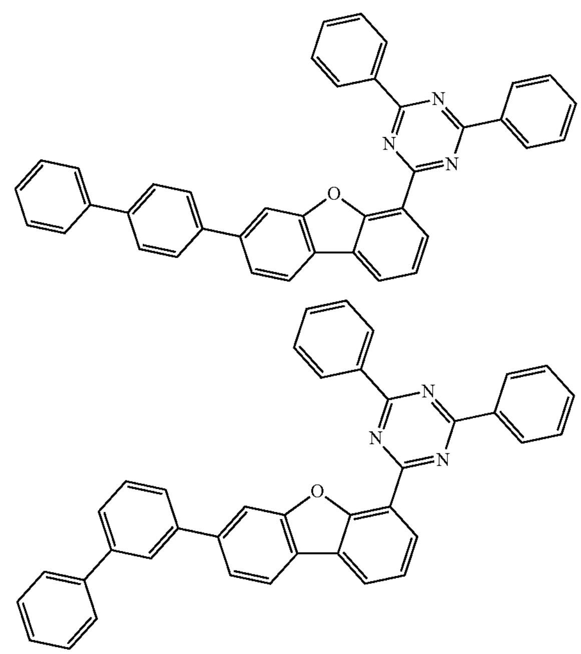
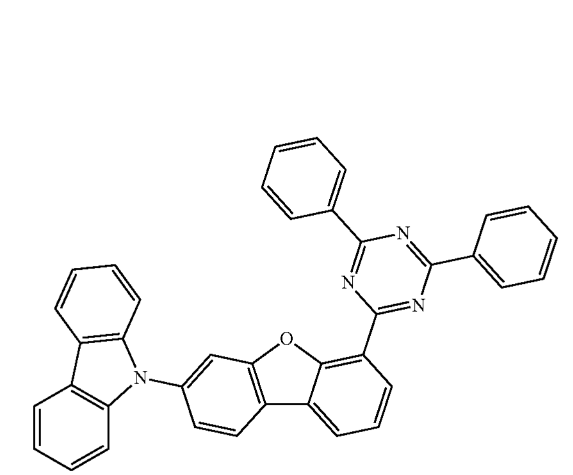

-continued
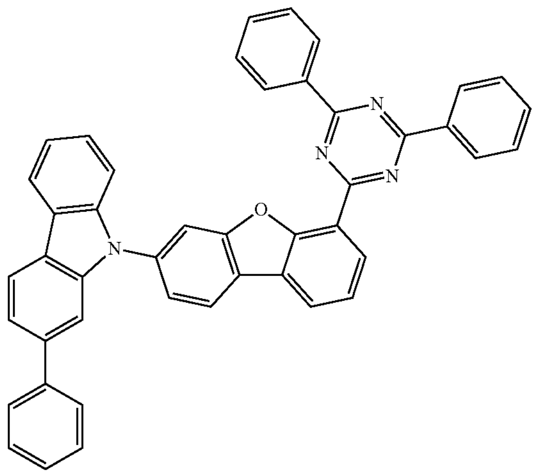
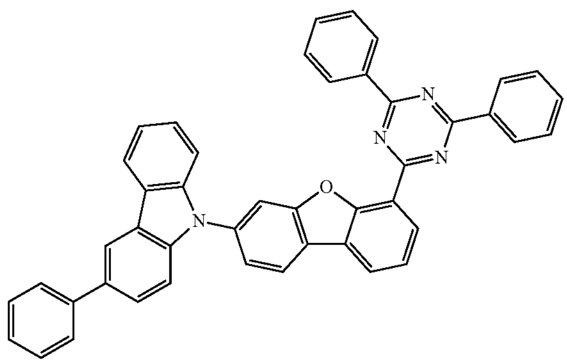
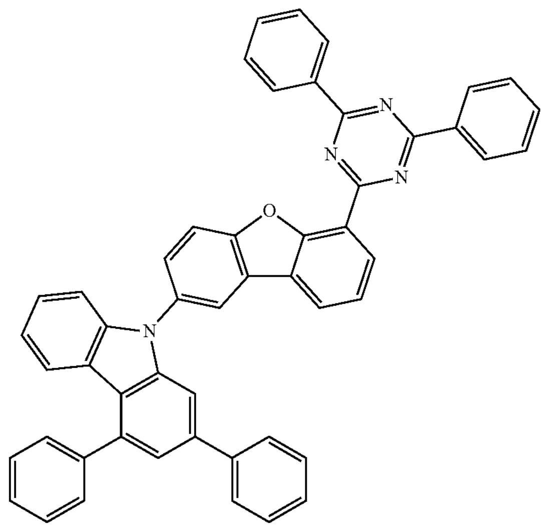
-continued
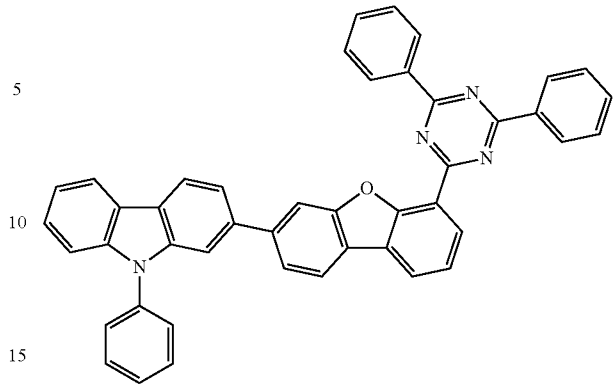
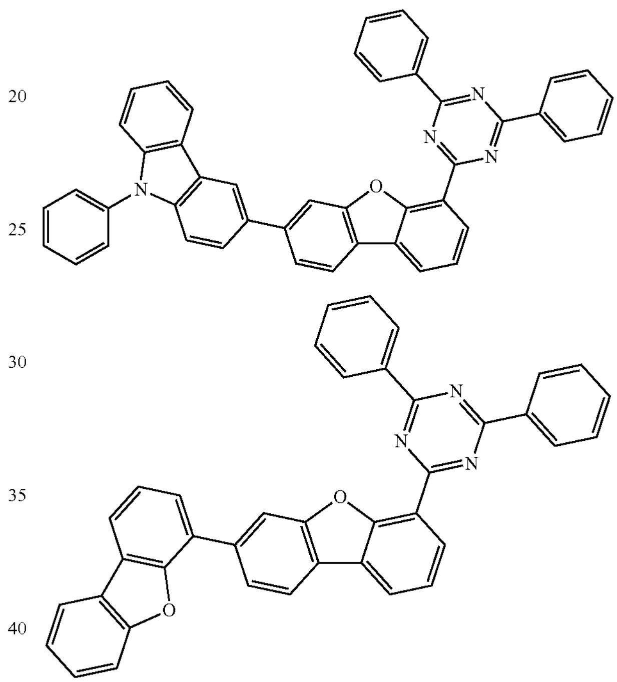
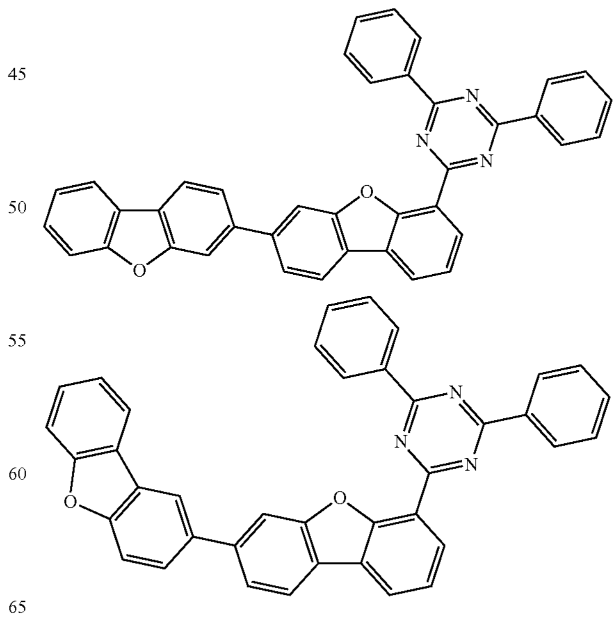

-continued
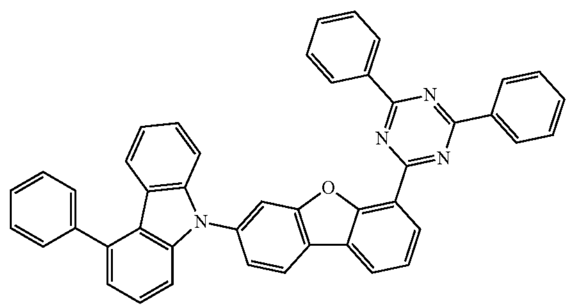
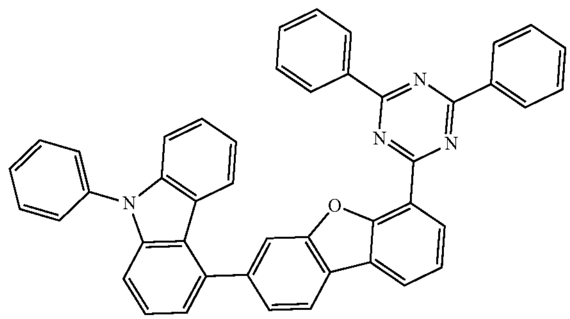
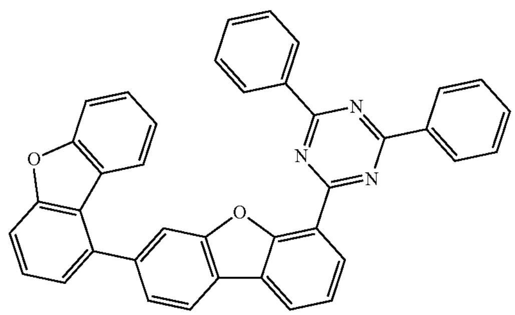
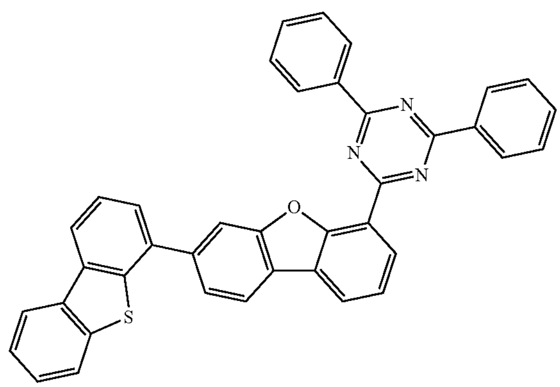
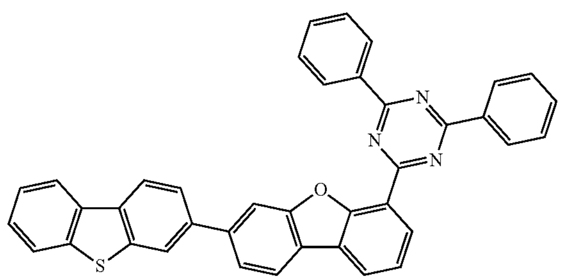
-continued
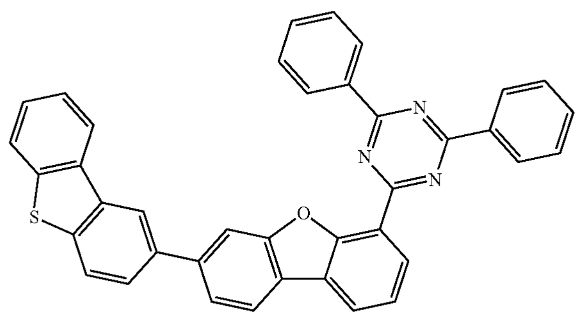
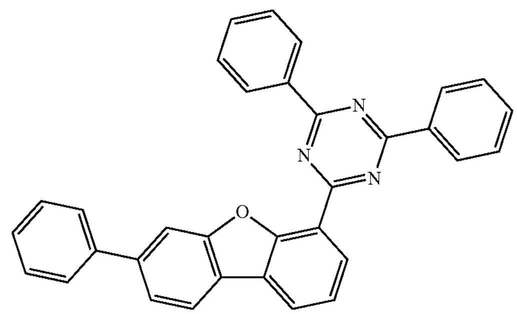
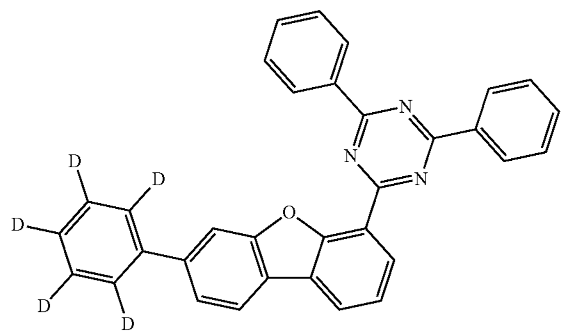
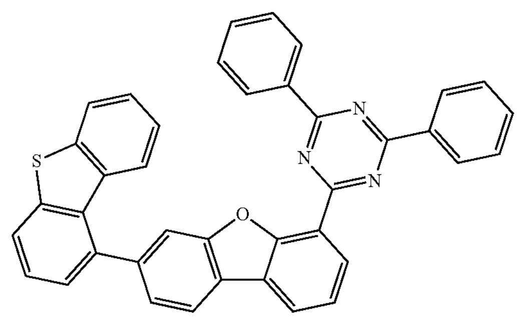
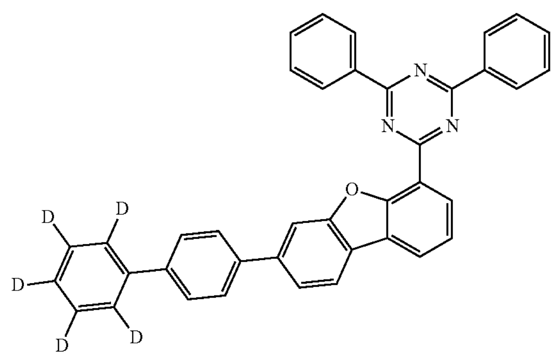

-continued
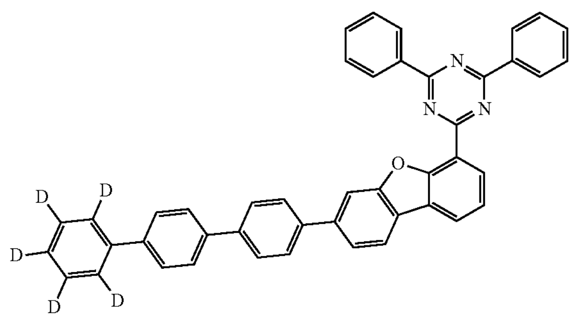
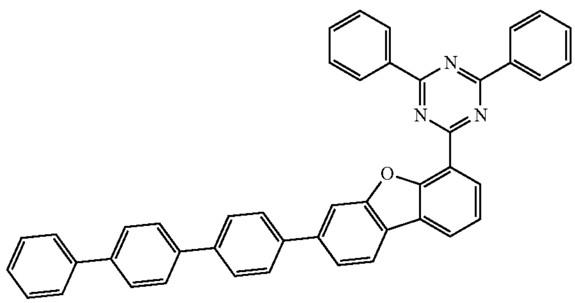
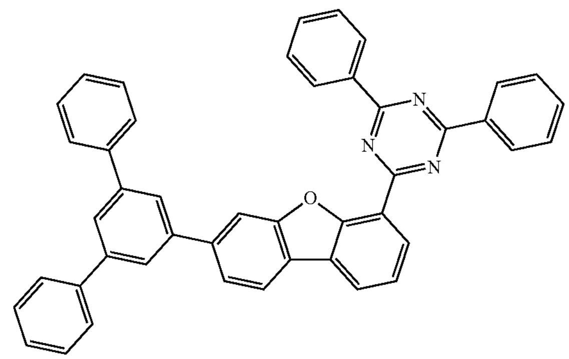
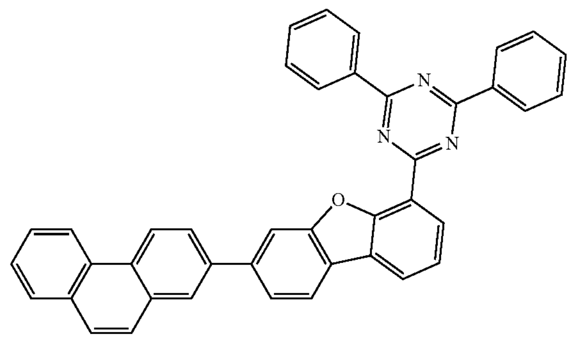
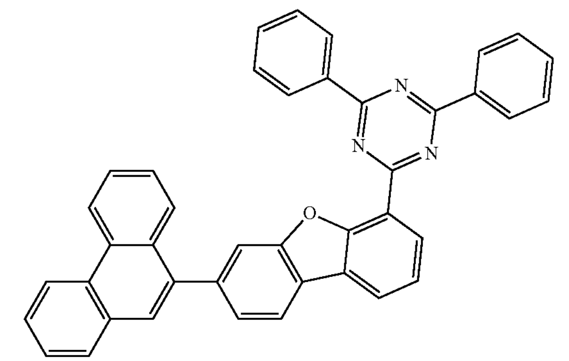
-continued
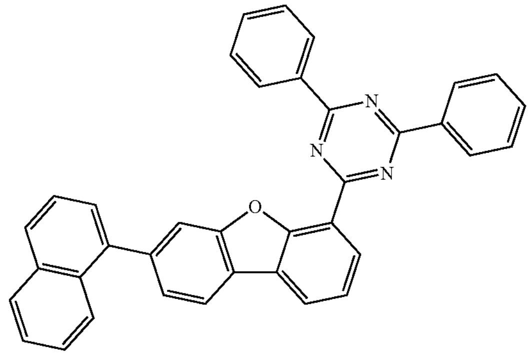
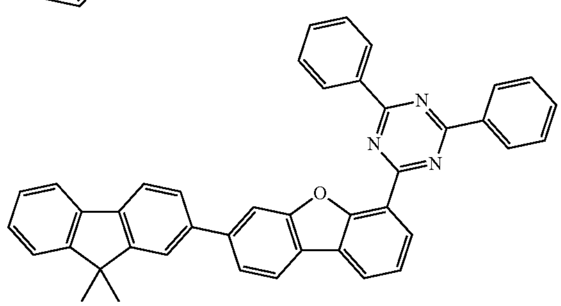
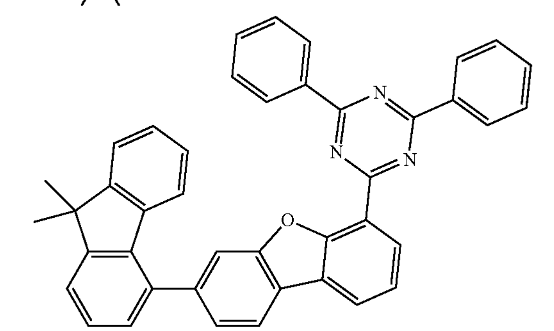
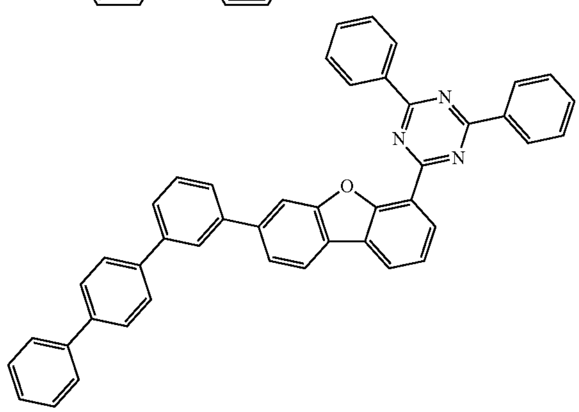
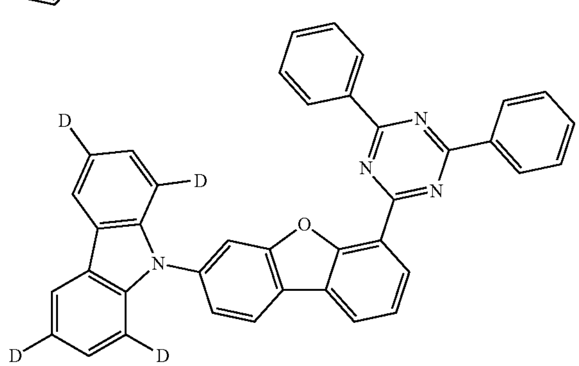

-continued
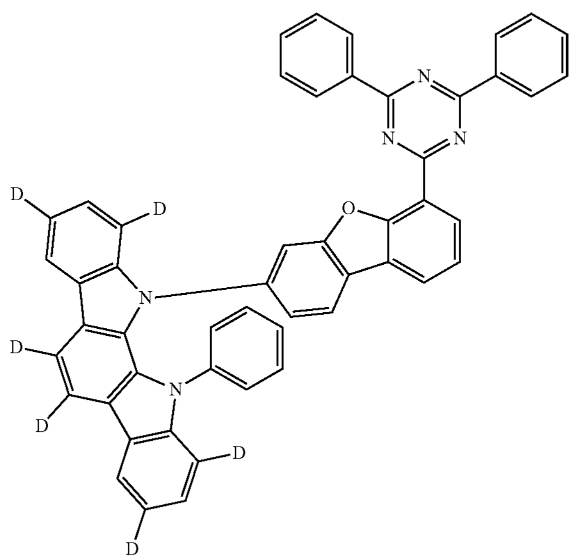
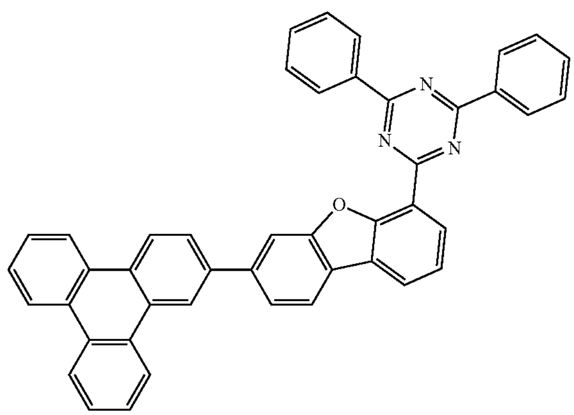
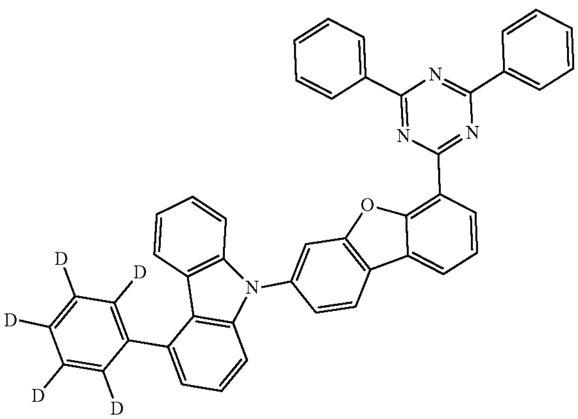
-continued
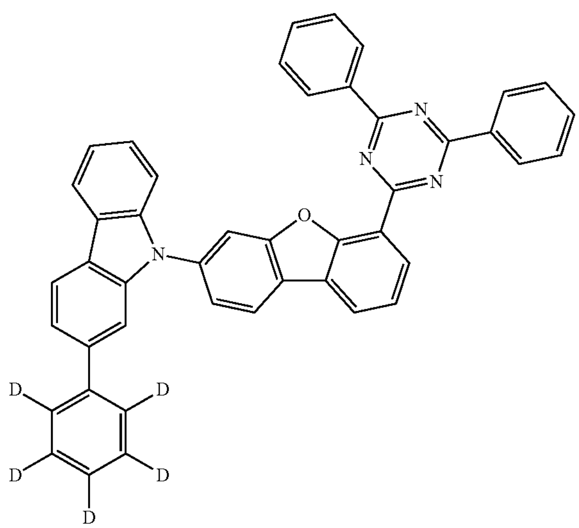
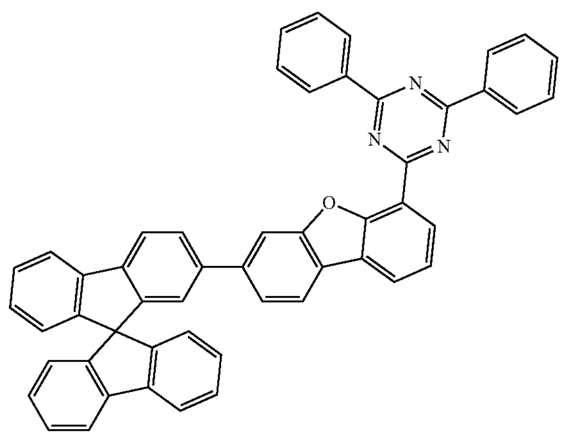
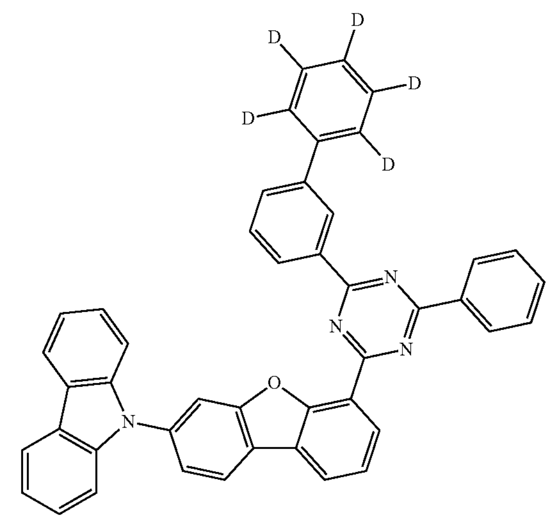

-continued
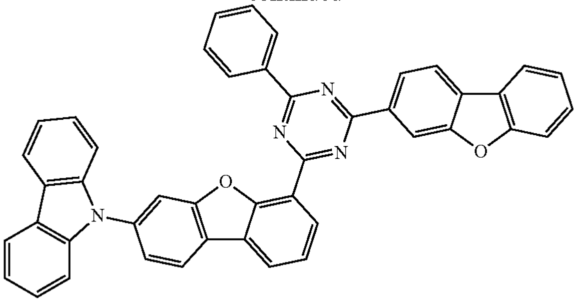
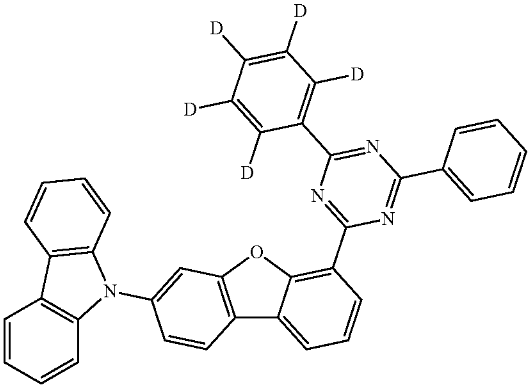
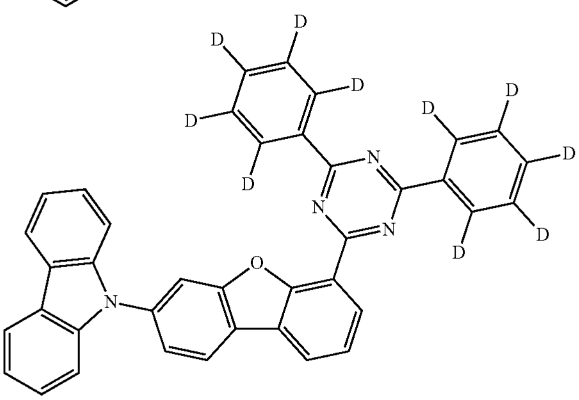
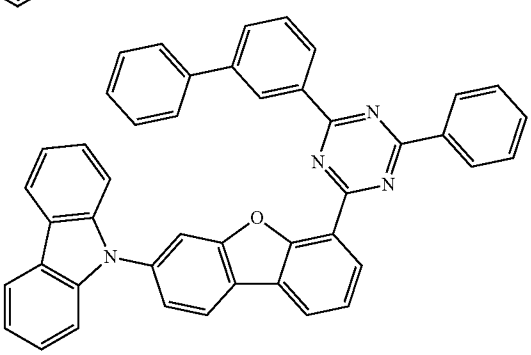
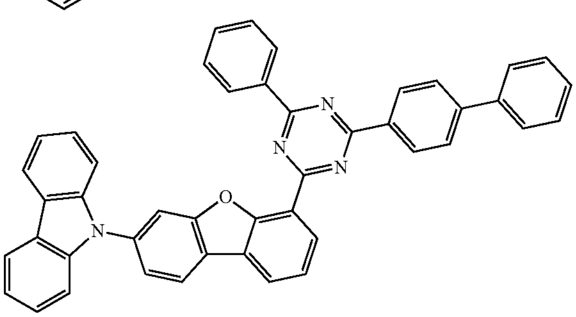
-continued
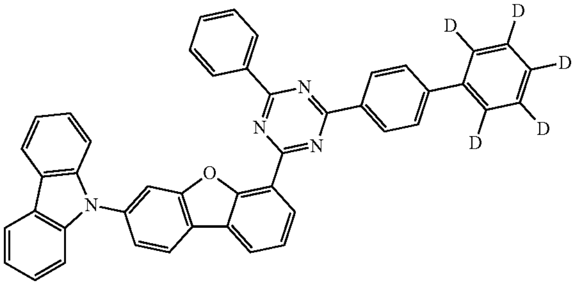
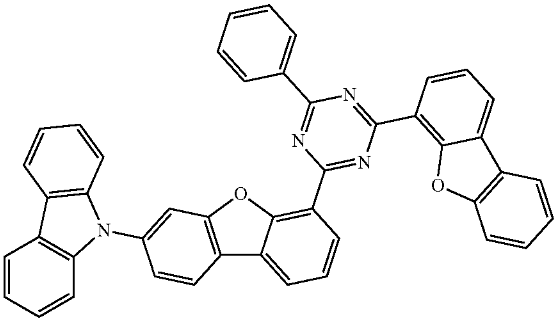
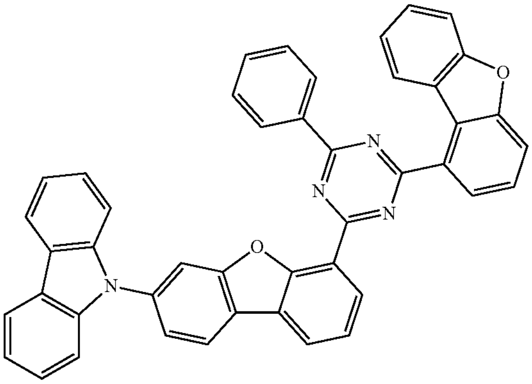
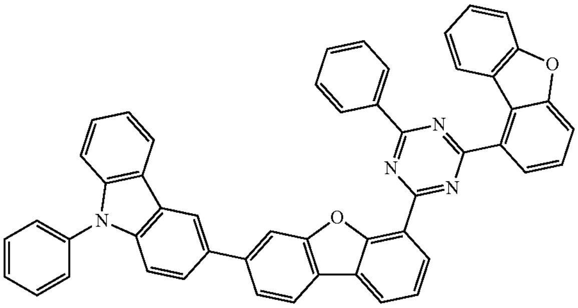
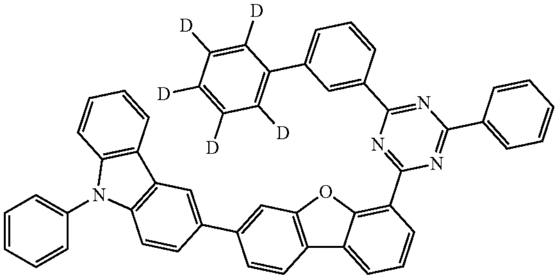

-continued
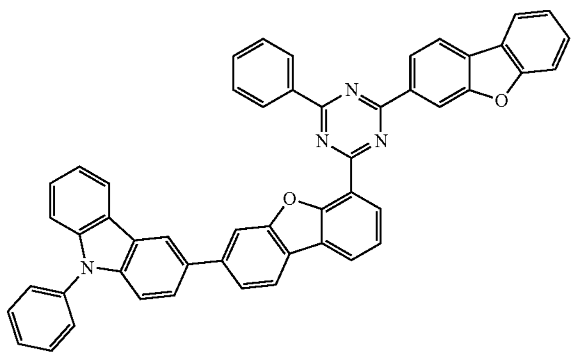
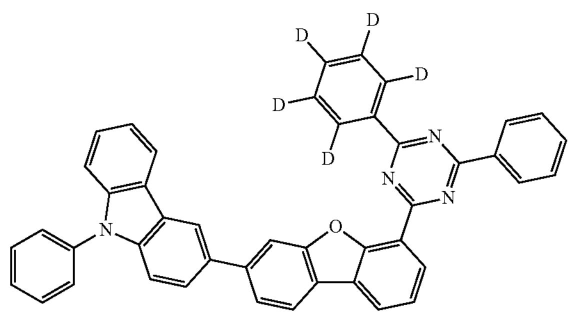
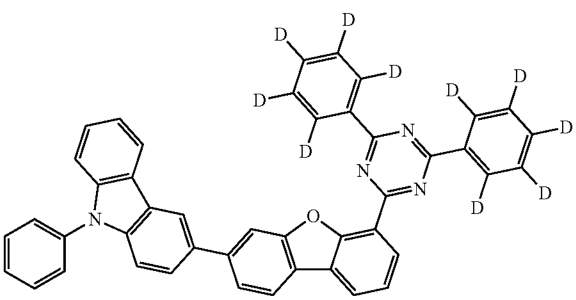
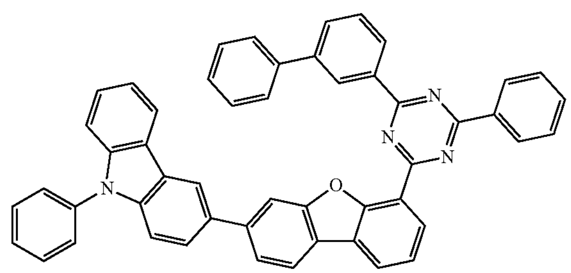
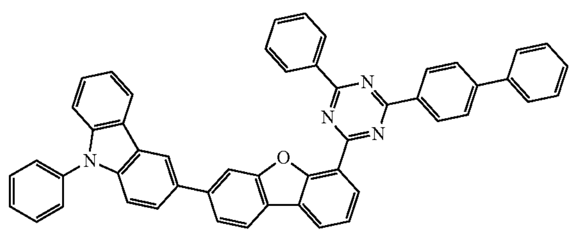
-continued
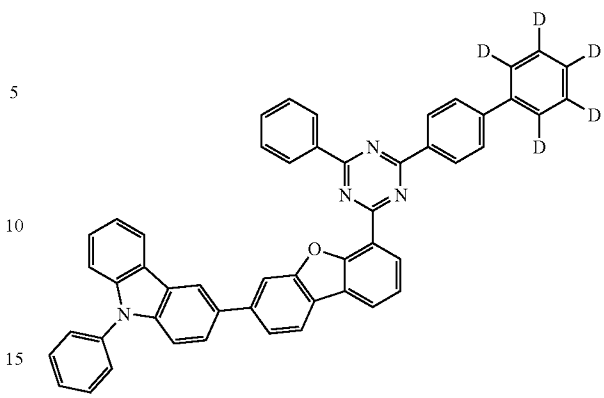
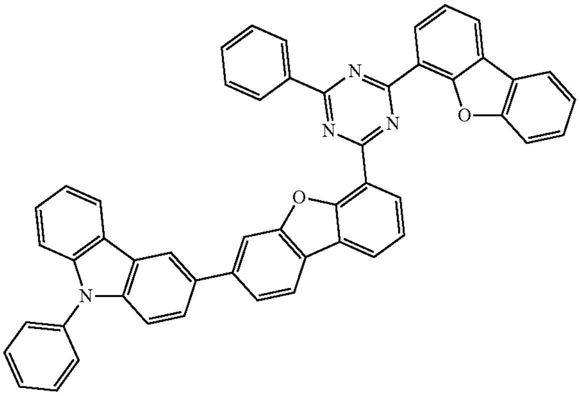
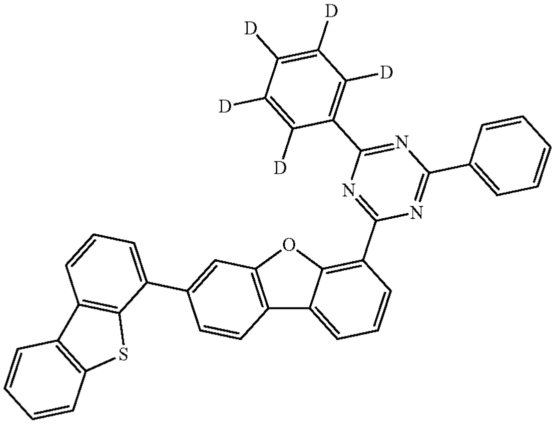
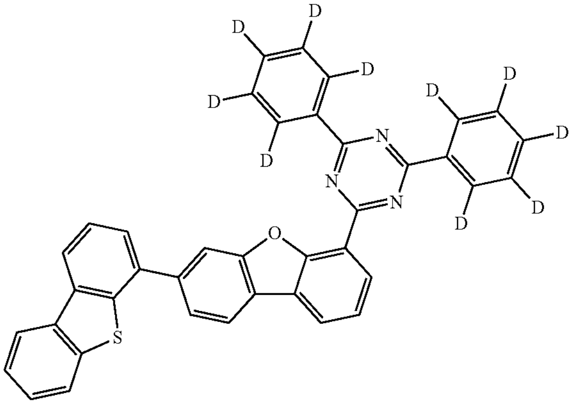

-continued
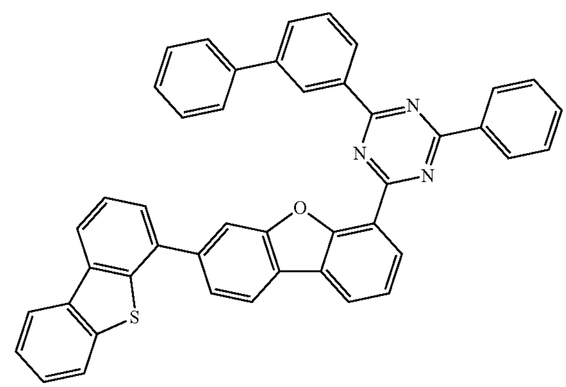
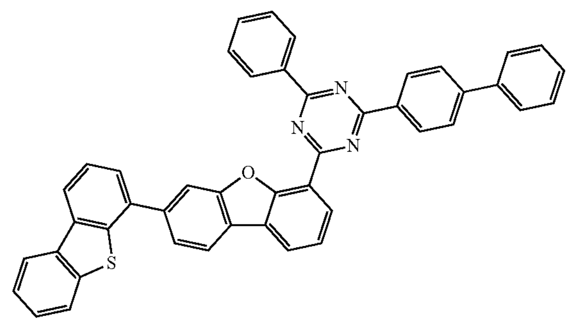
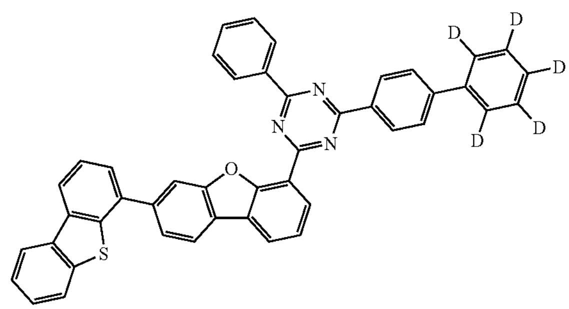
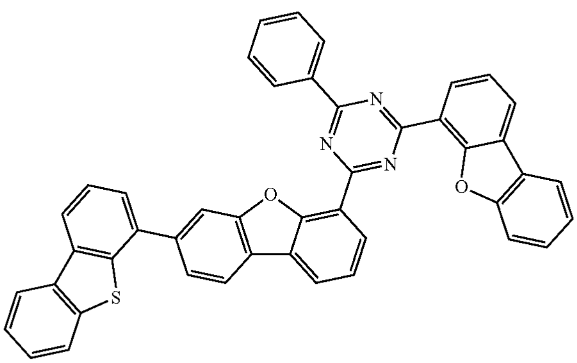
-continued
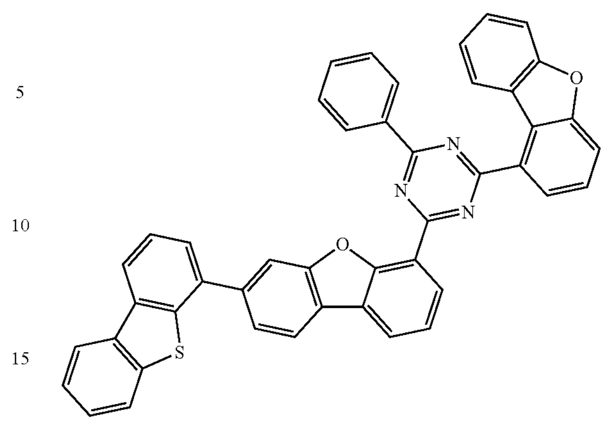
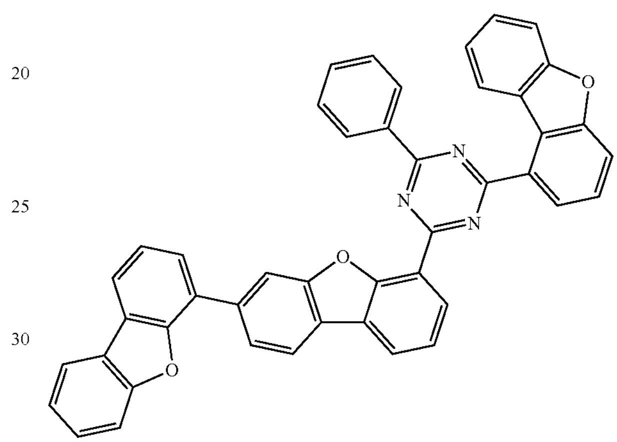
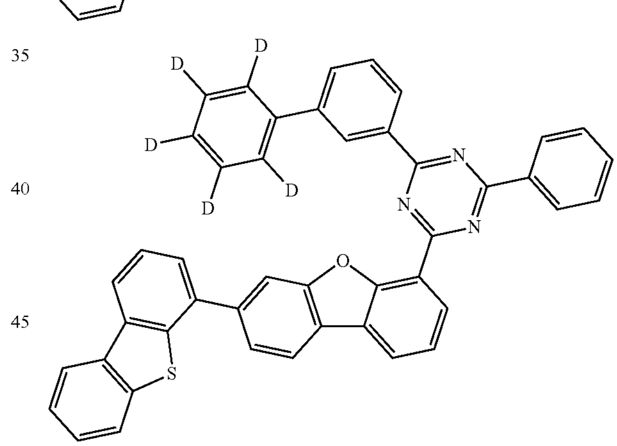
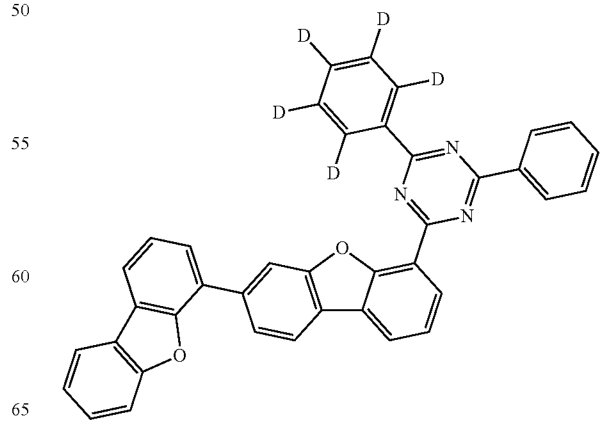

-continued
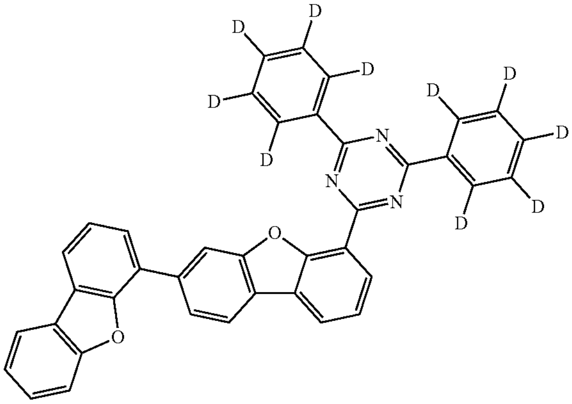
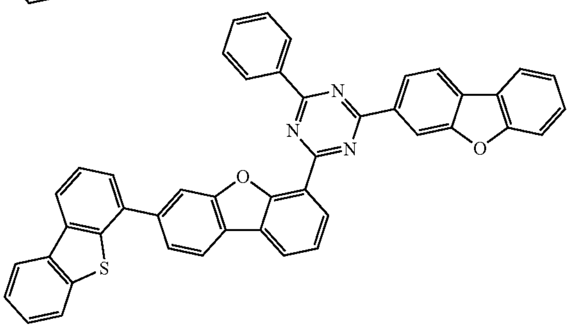
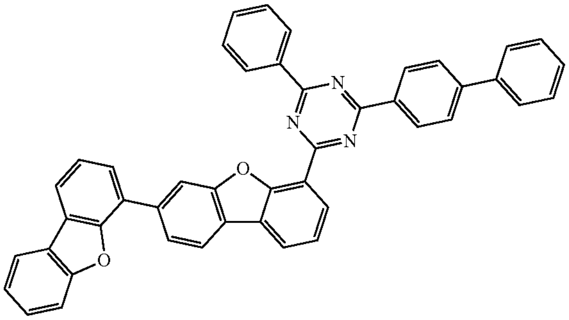
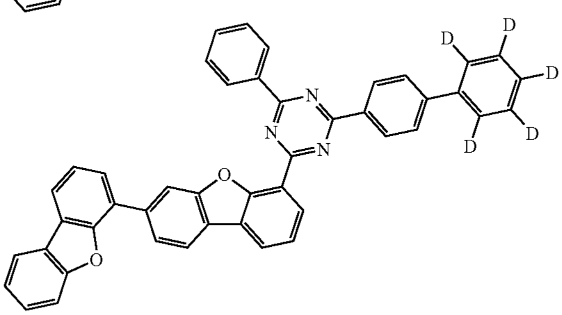
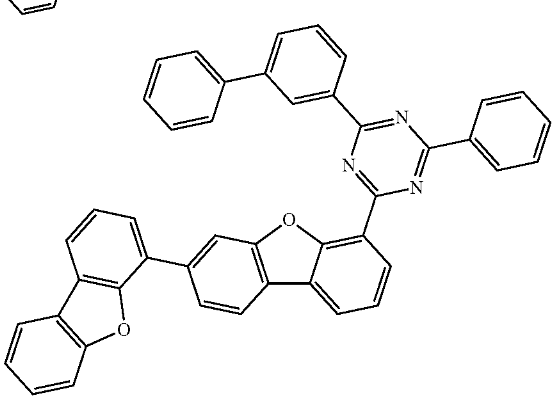
-continued
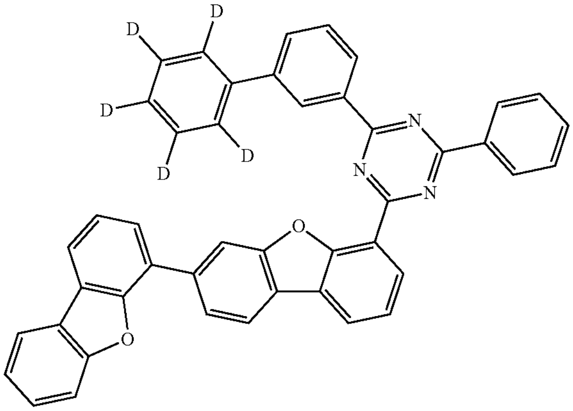
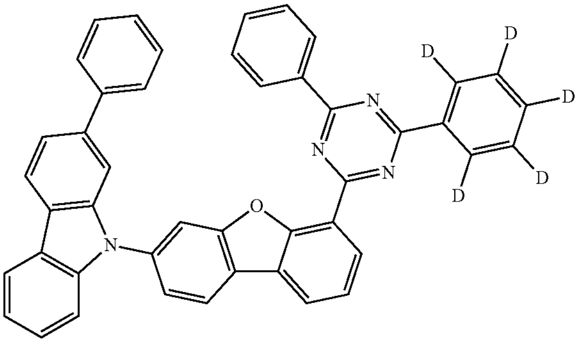
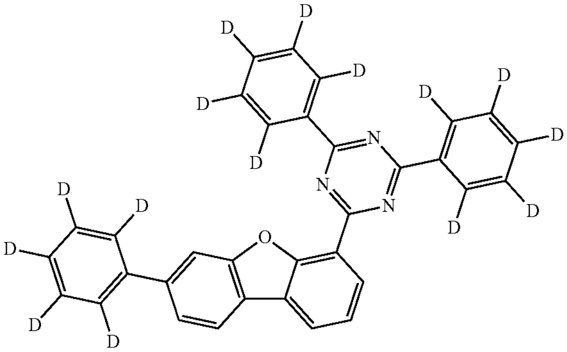
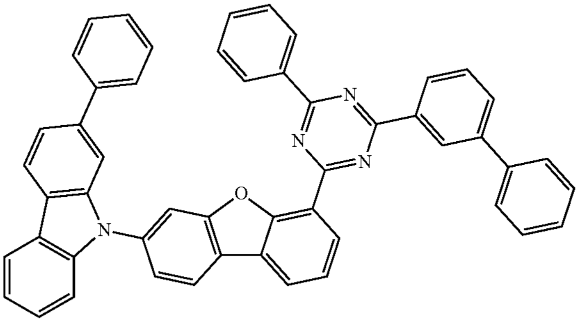

-continued
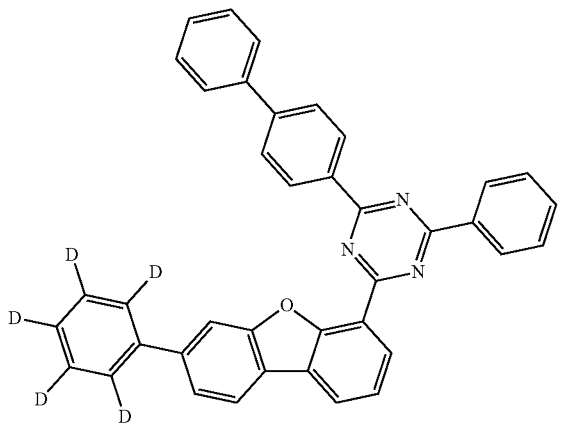
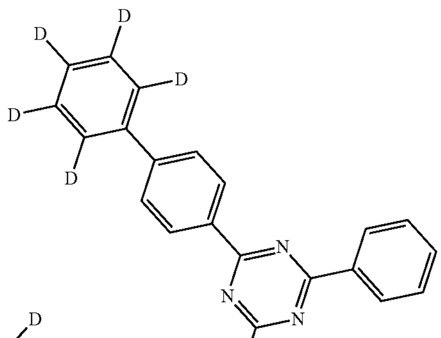
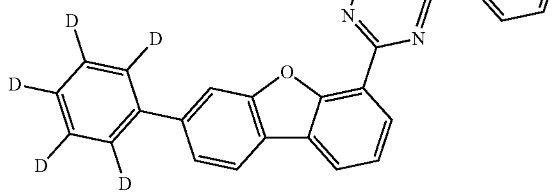
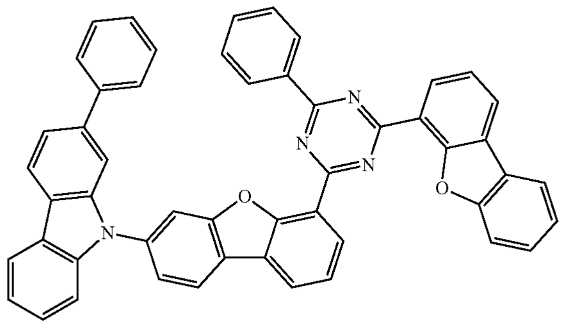
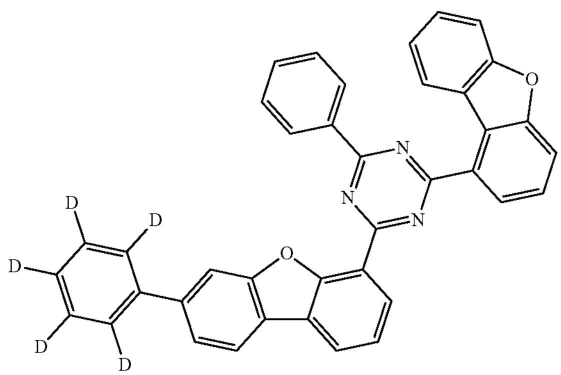
-continued
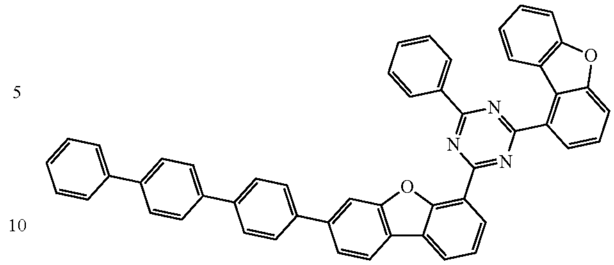
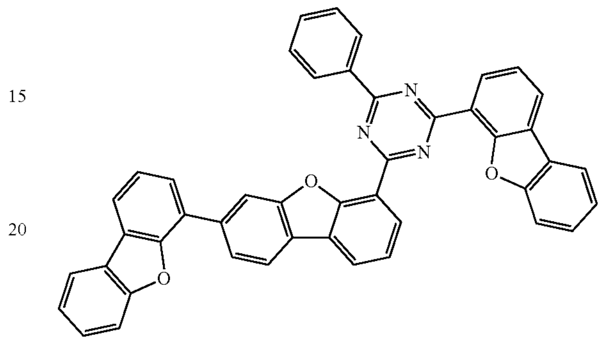
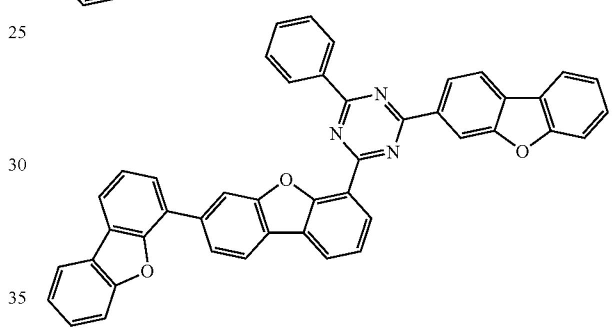
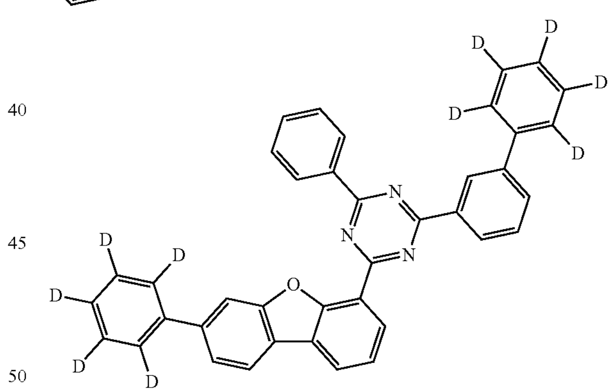
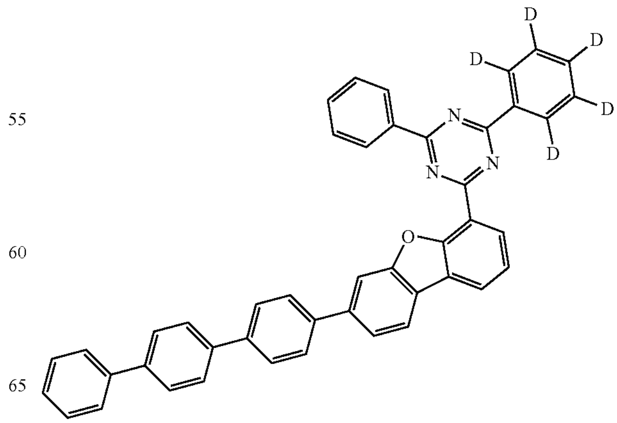

-continued
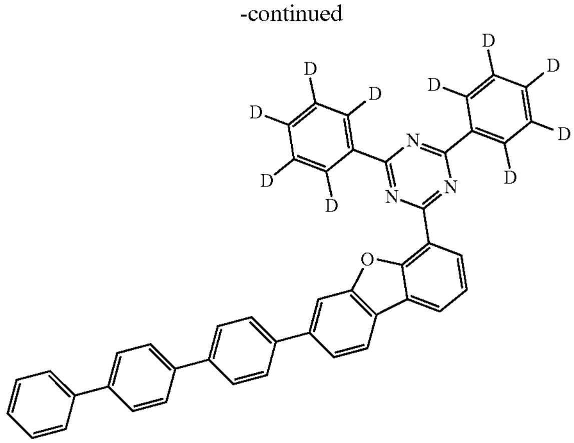
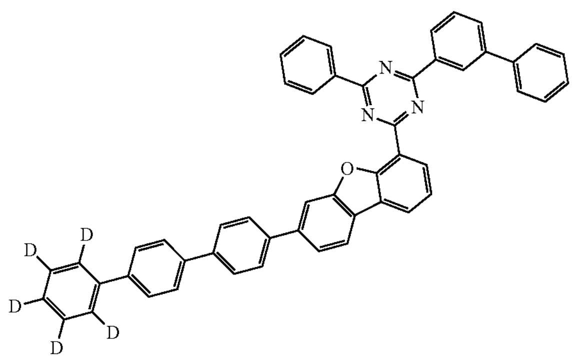
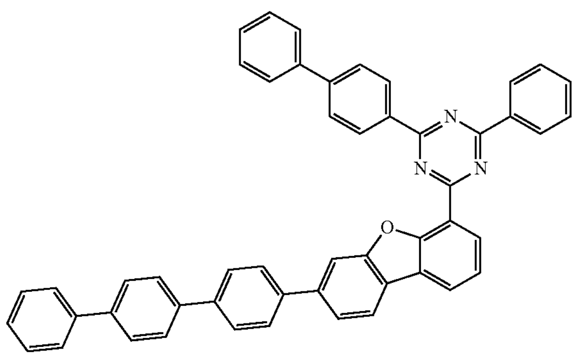
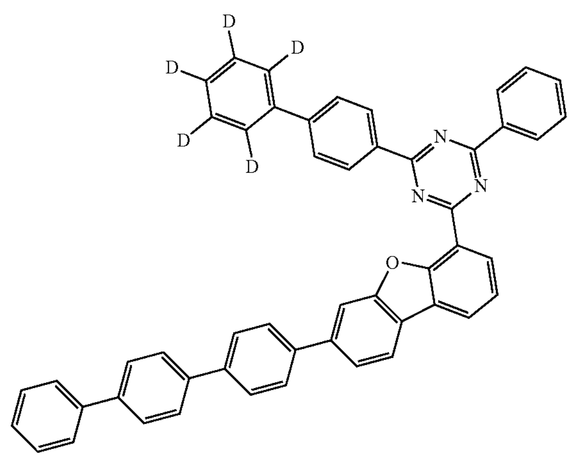
-continued
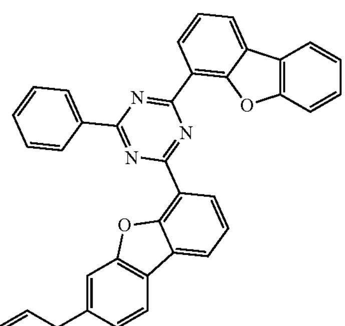
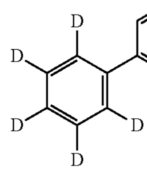
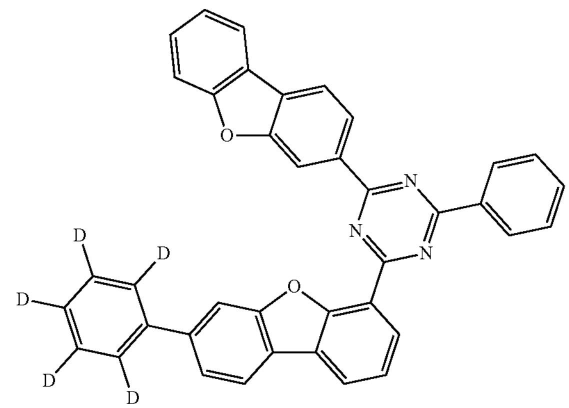
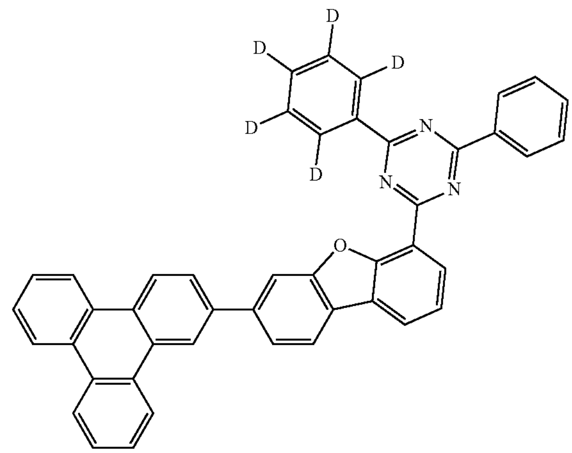

-continued
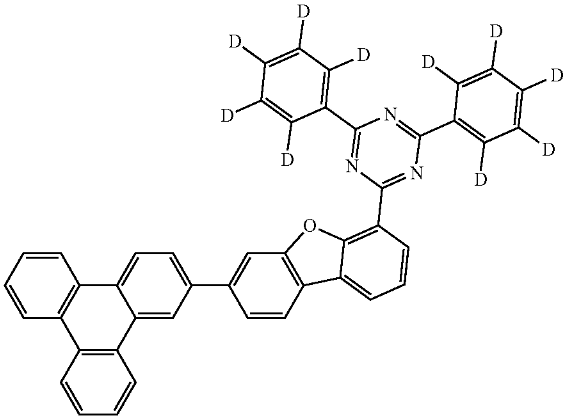
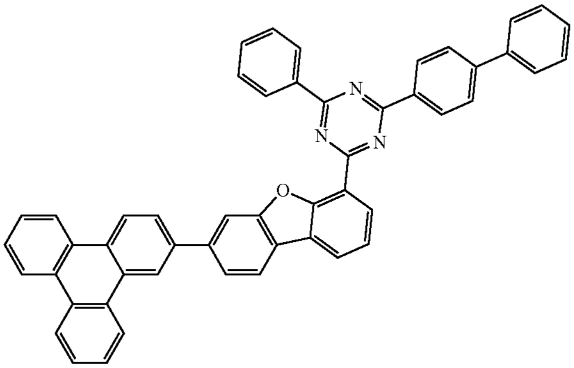
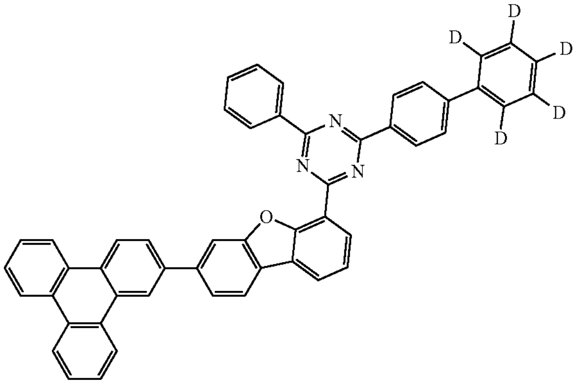
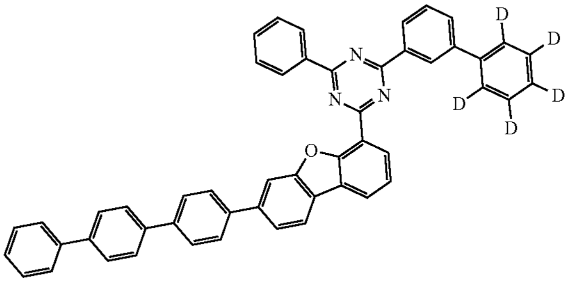
-continued
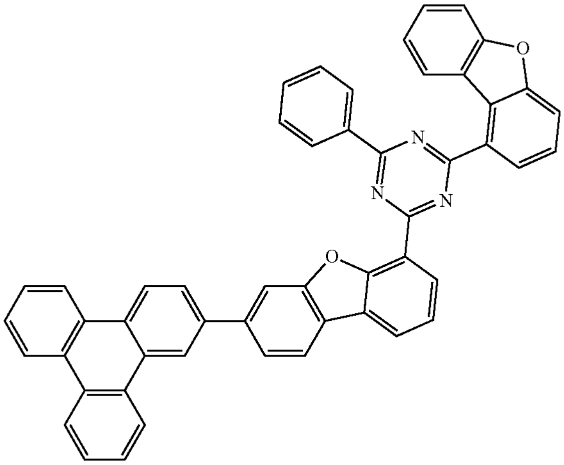
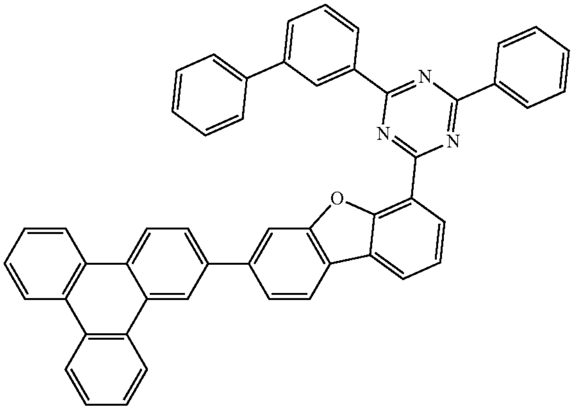
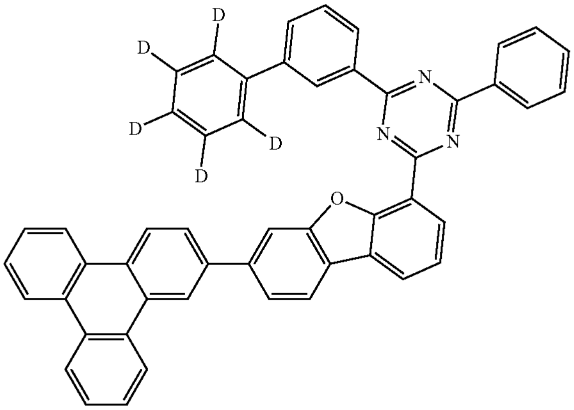
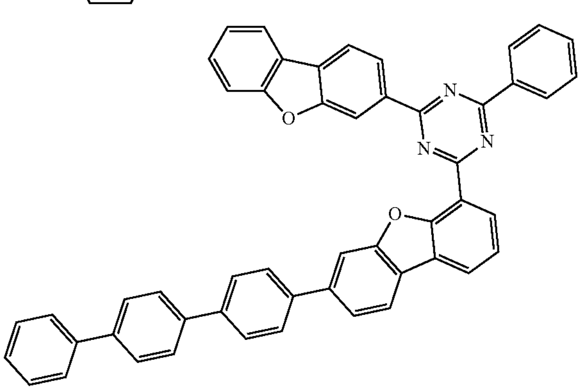

-continued
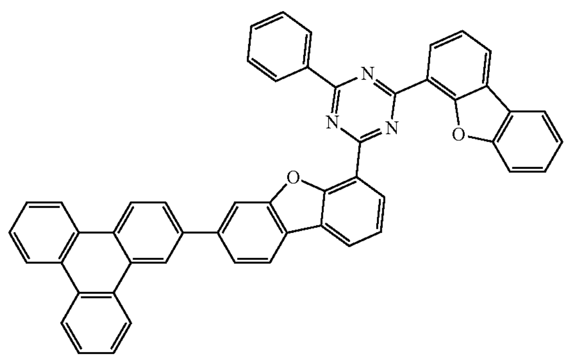
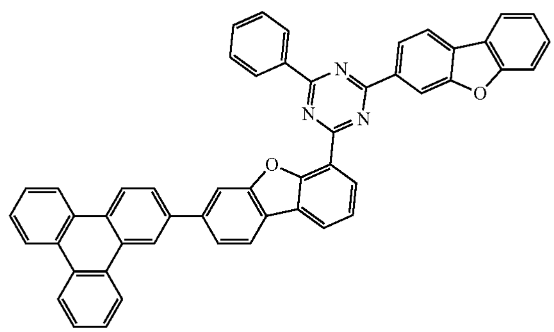
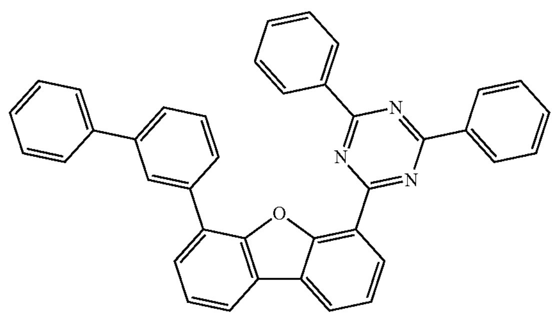
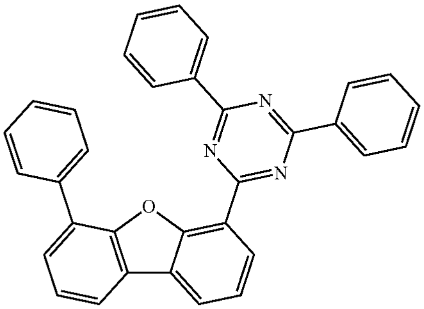
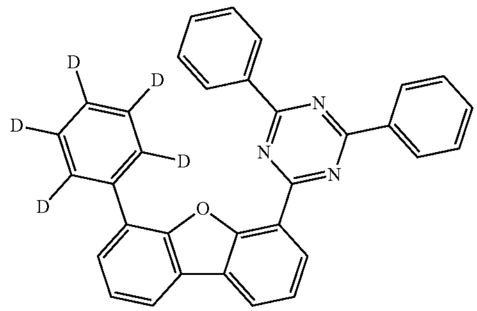
-continued
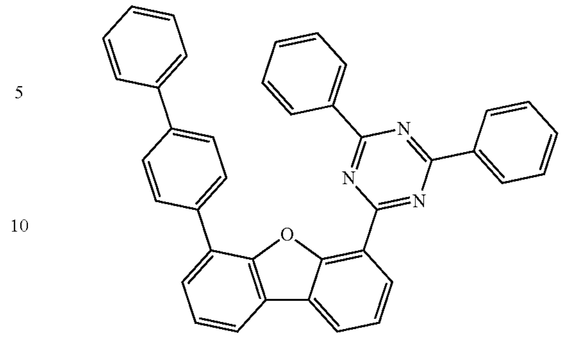
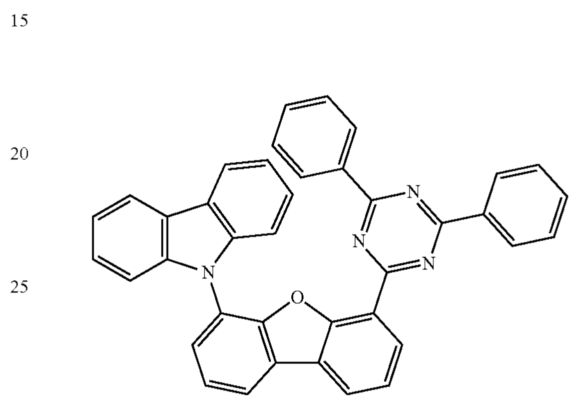
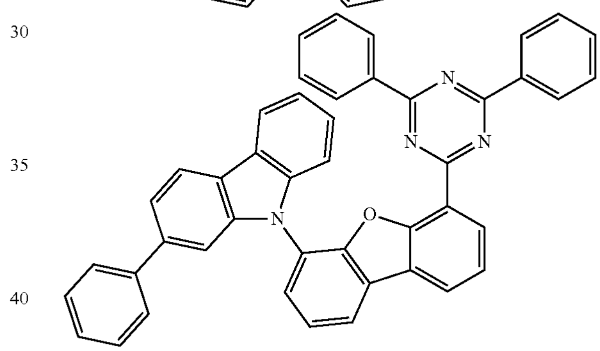
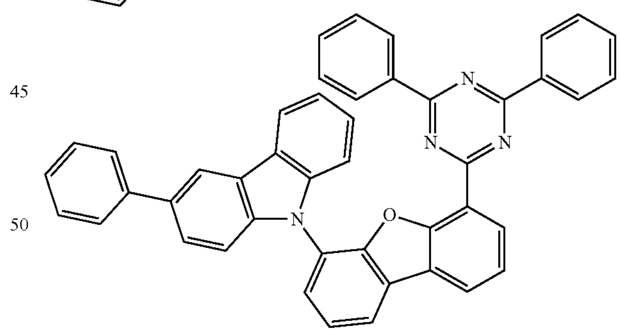
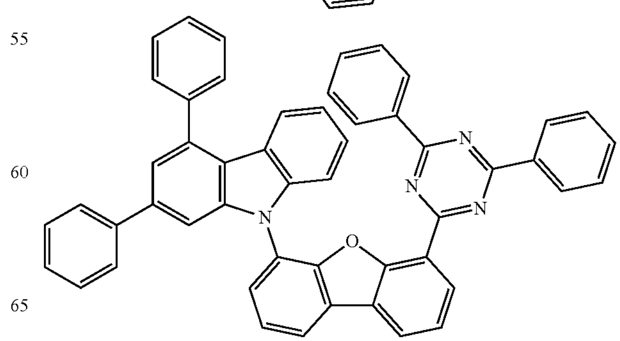

-continued
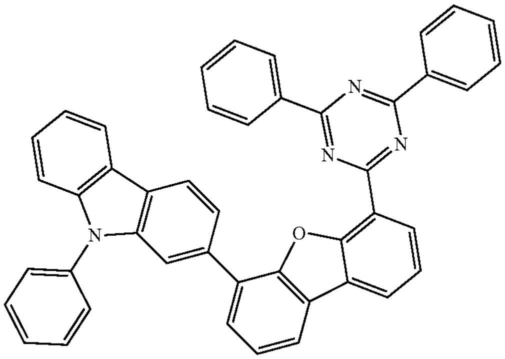
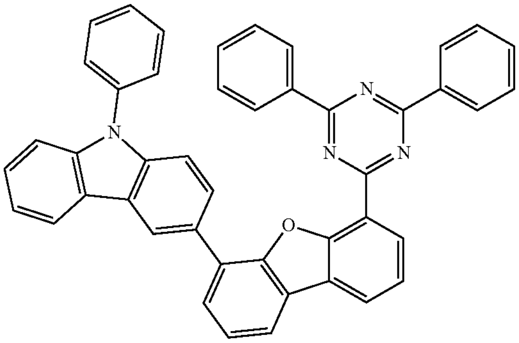
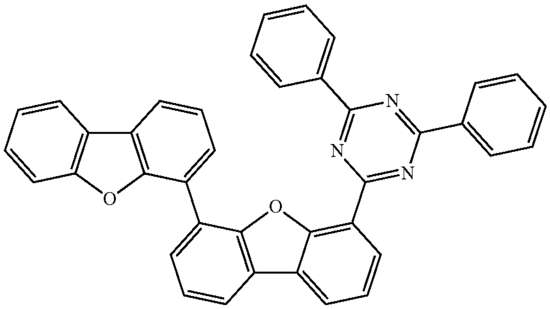
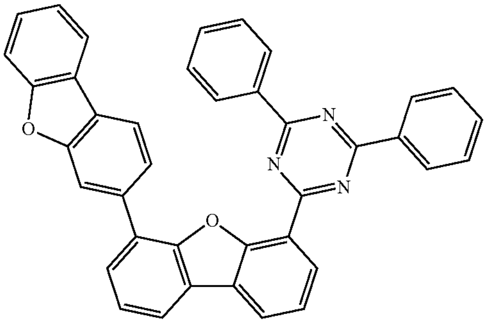
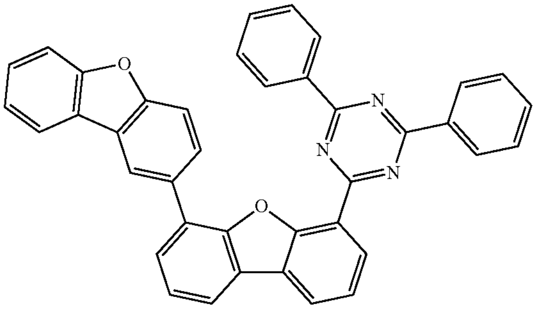
-continued
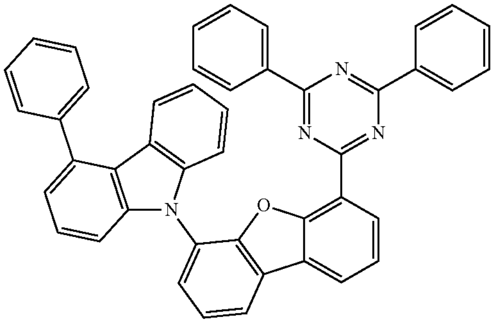
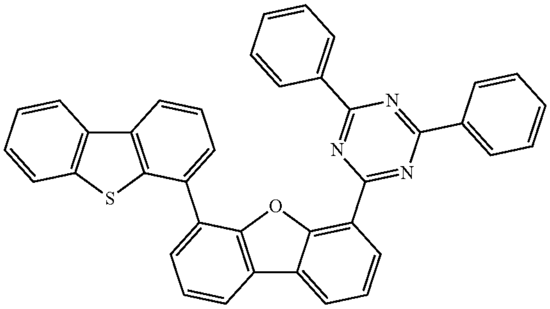
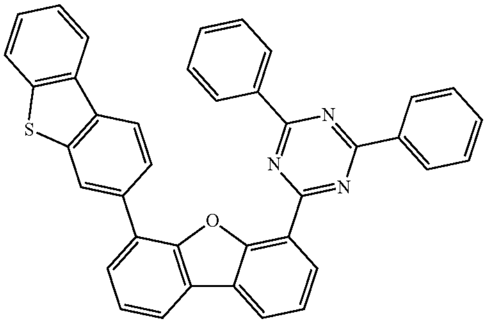
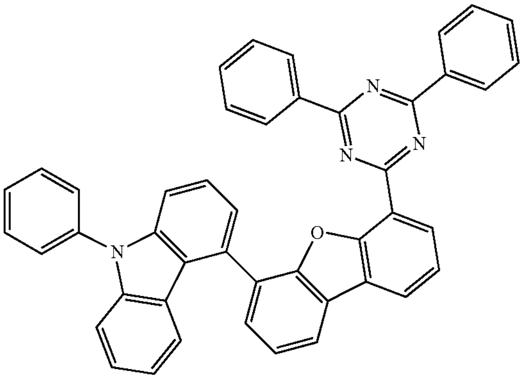
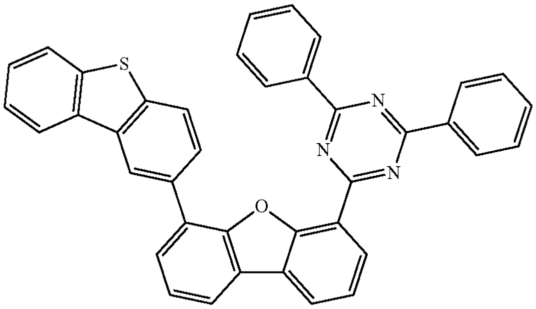

-continued
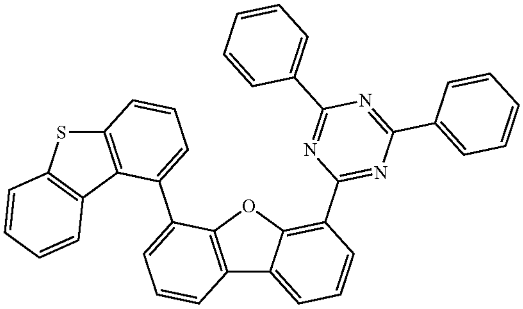
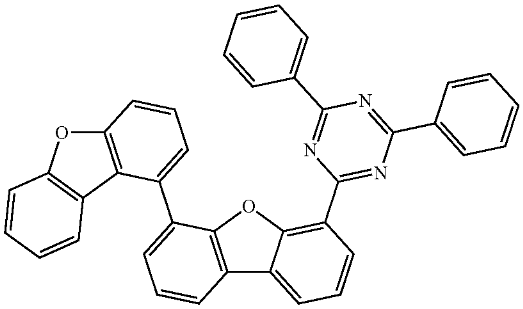
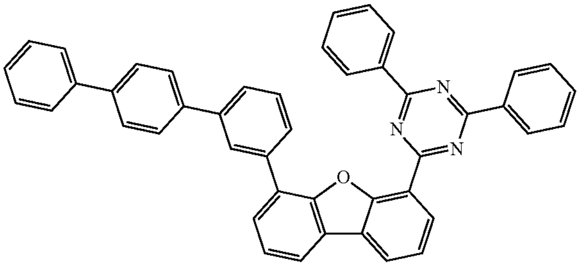
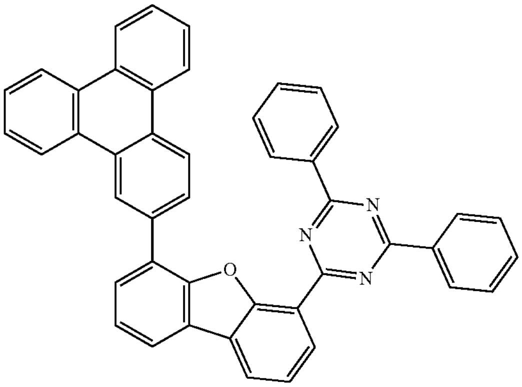
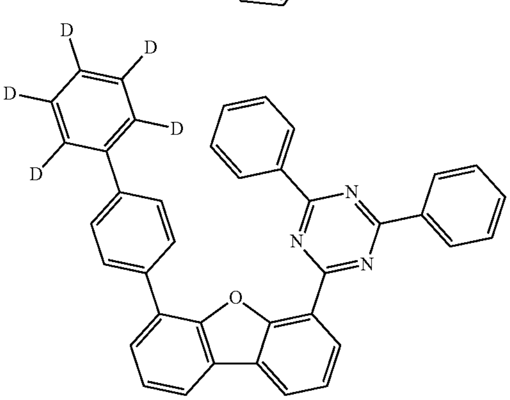
-continued
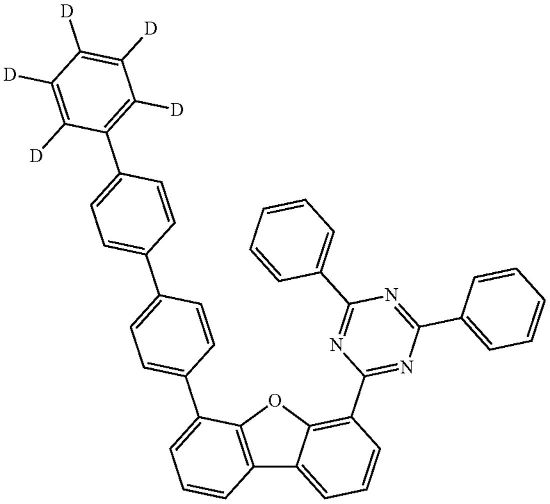
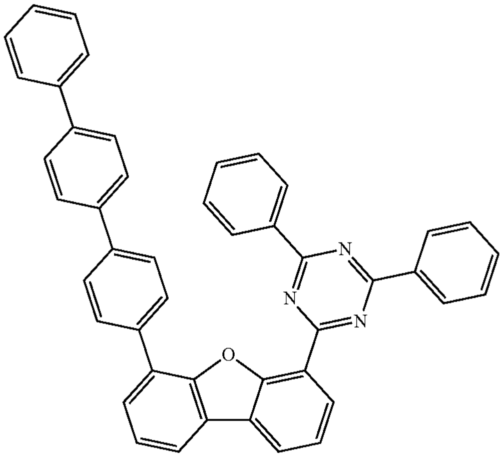
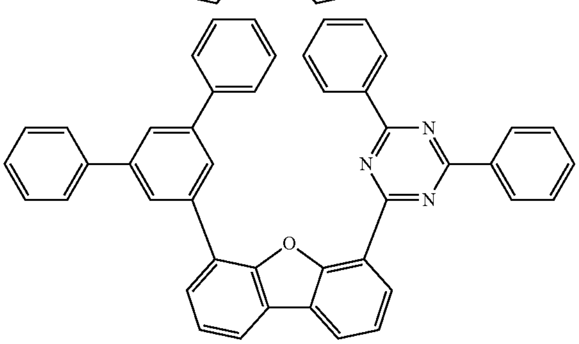
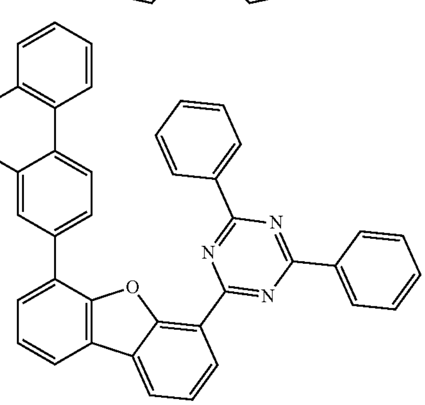

-continued
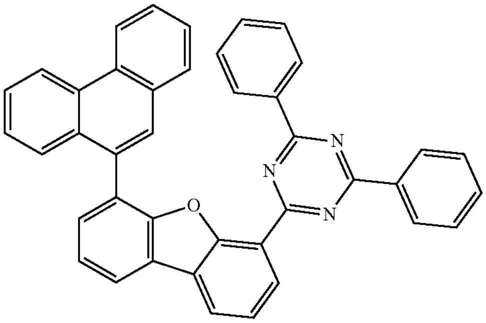
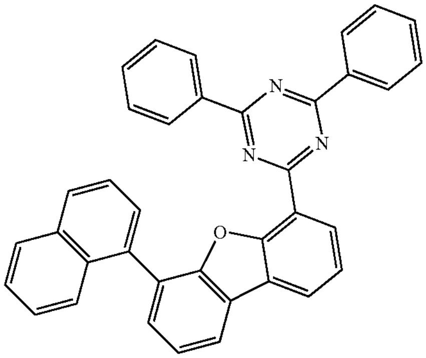
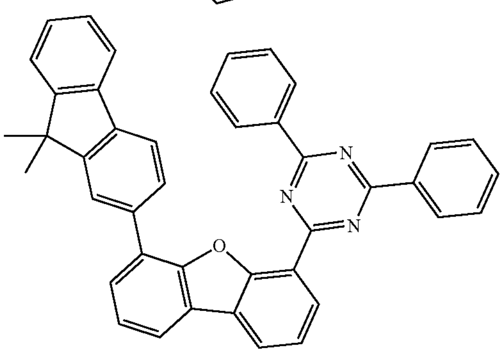
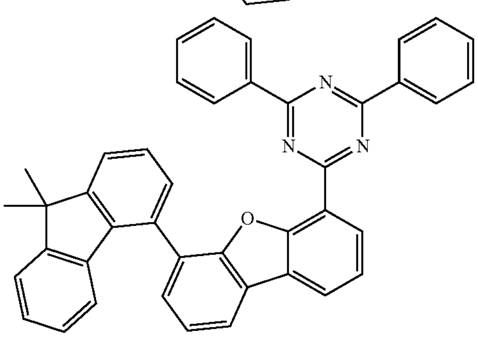
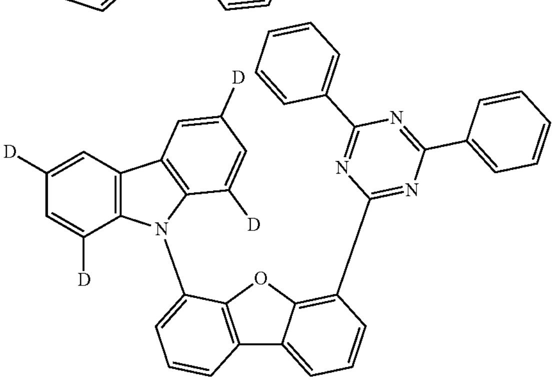
-continued
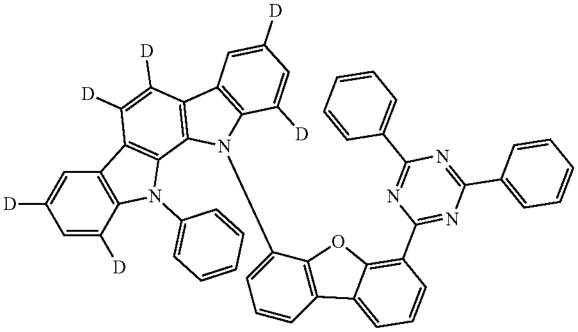
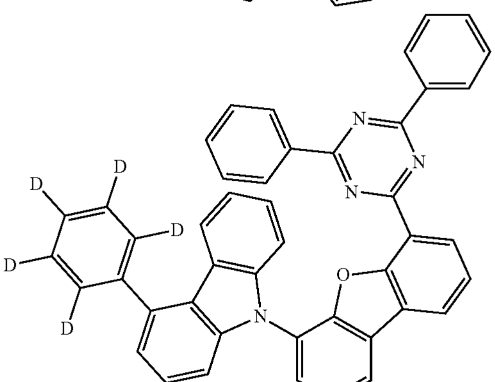
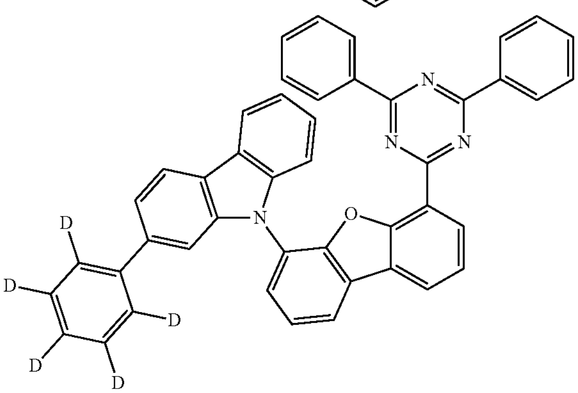
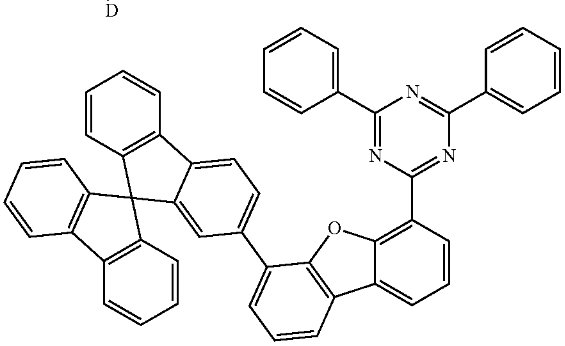
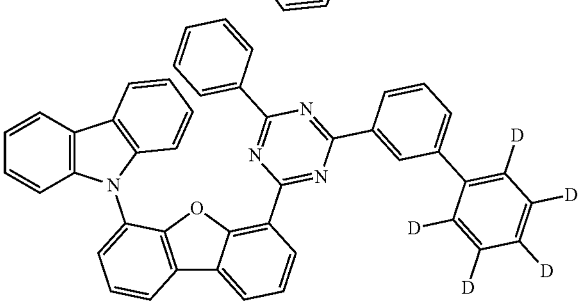

-continued
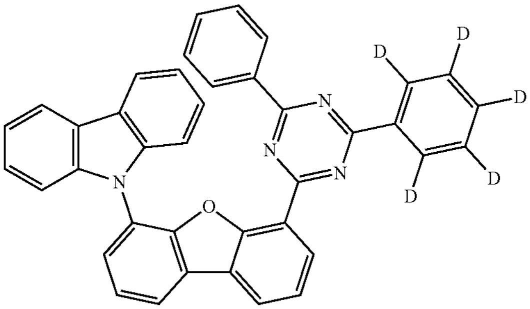
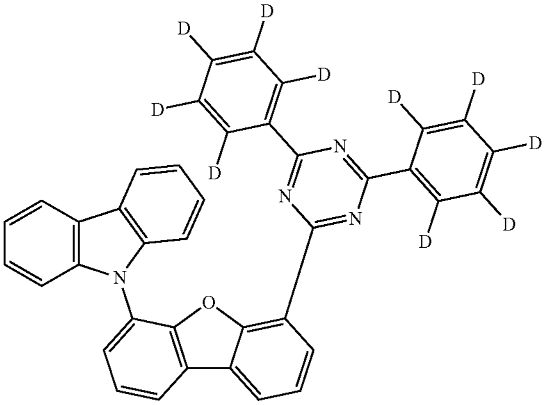
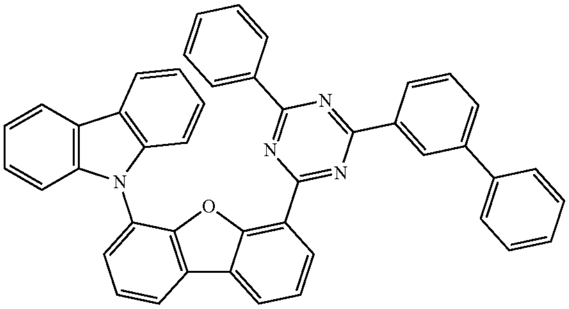
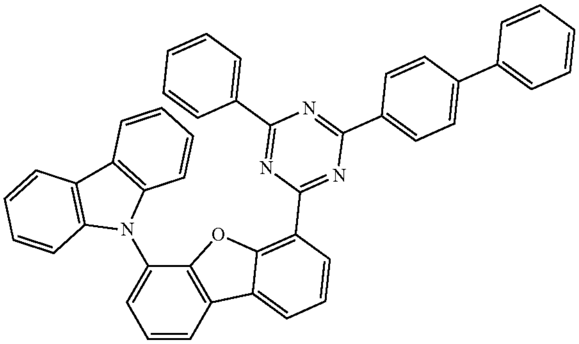
-continued
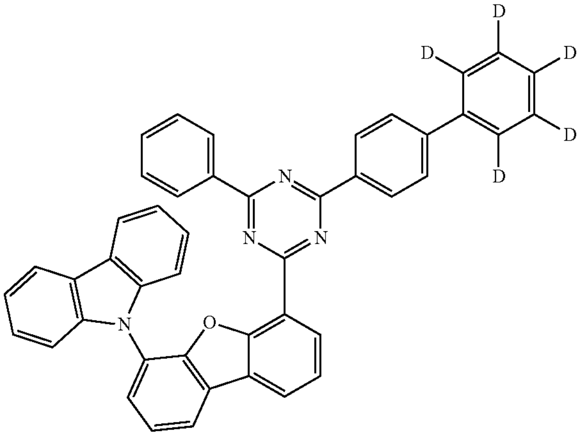
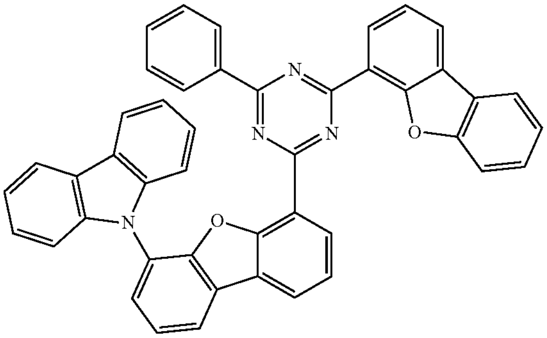
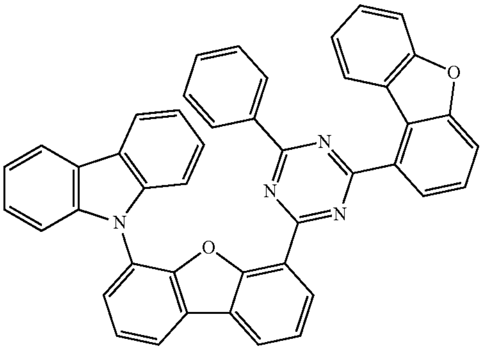
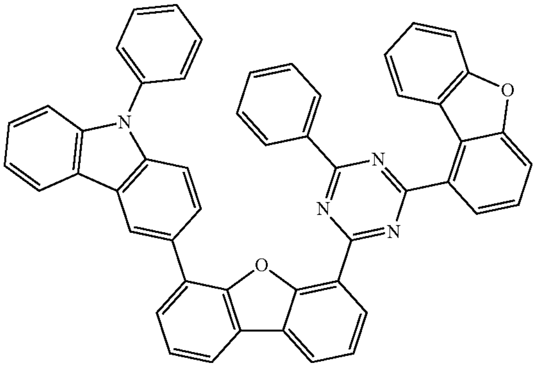

-continued
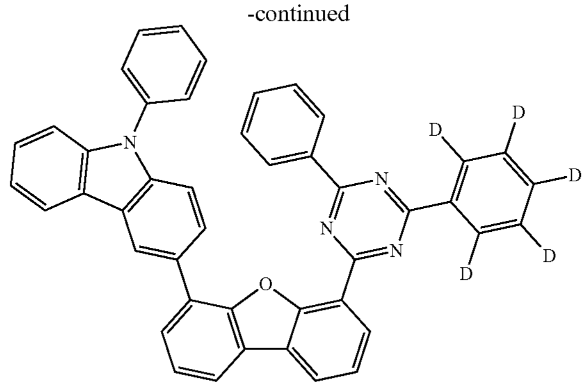
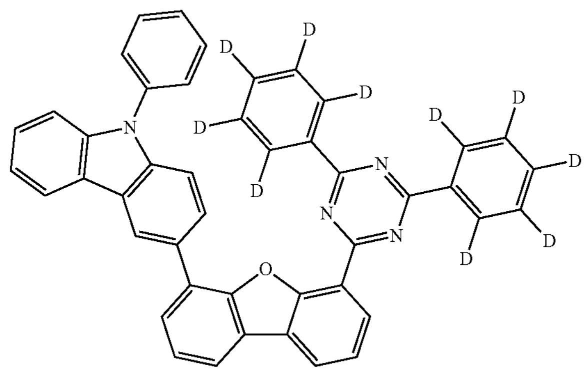
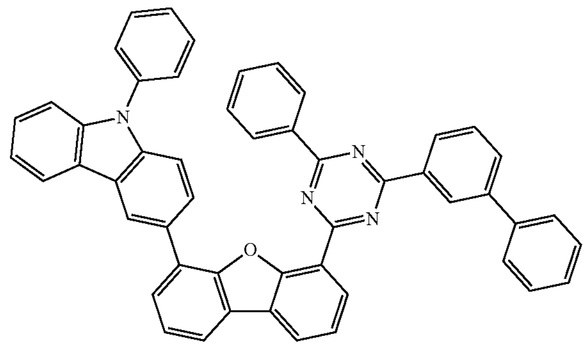
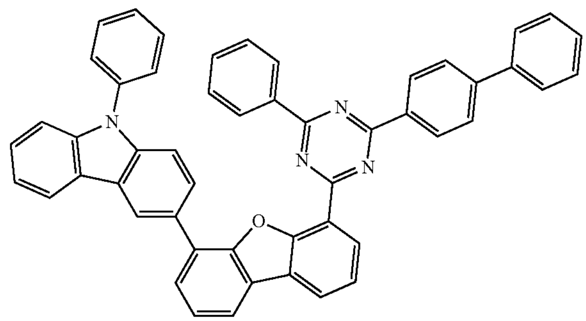
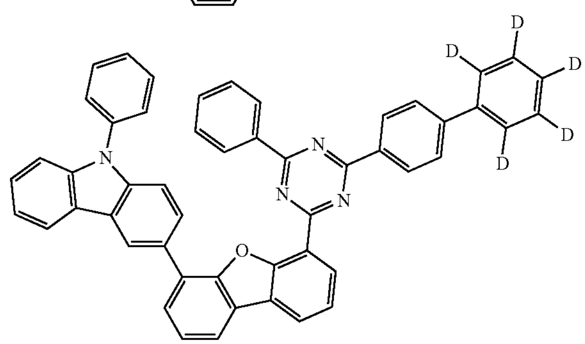
-continued
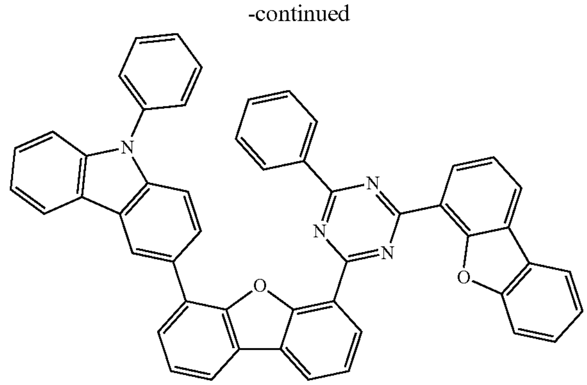
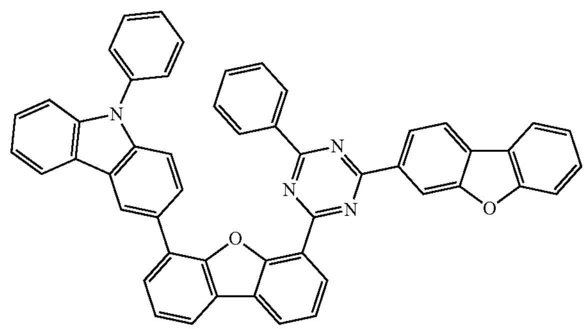
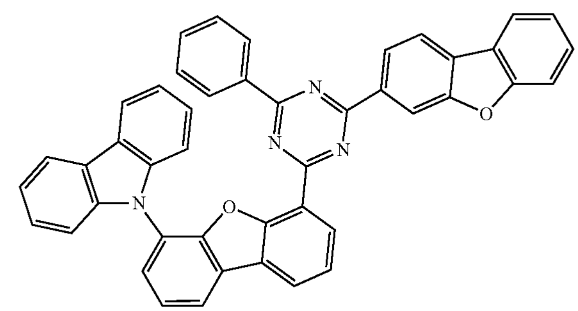
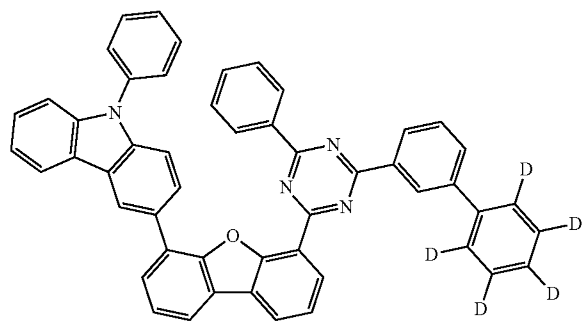
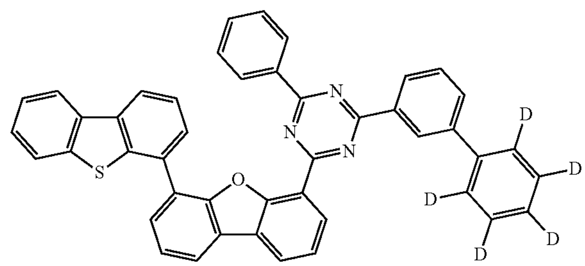

-continued
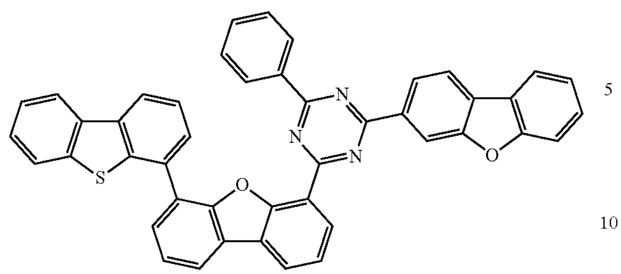
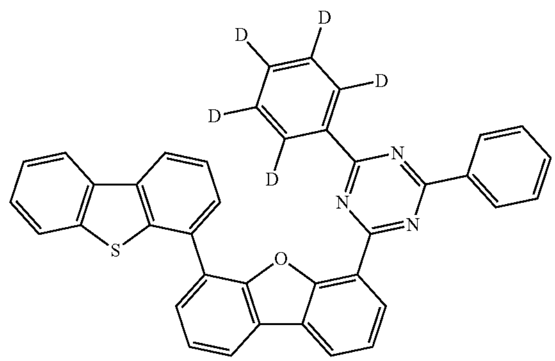
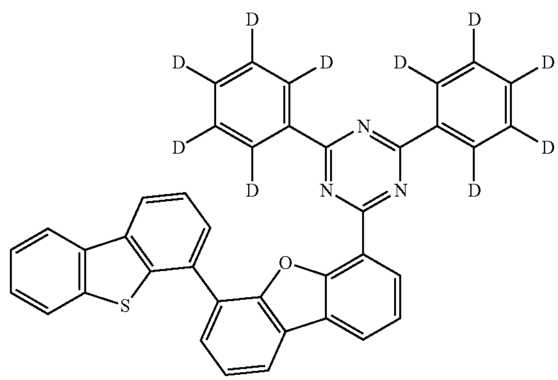
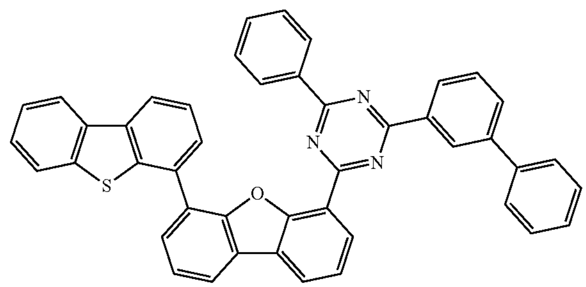
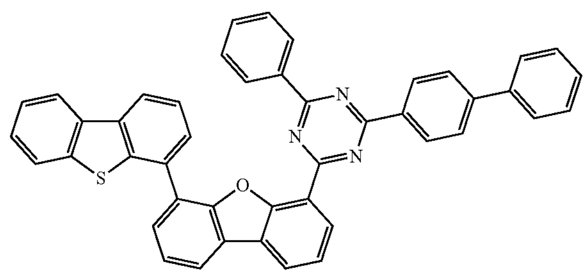
-continued
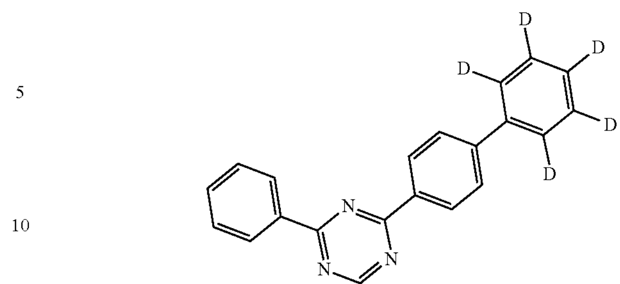
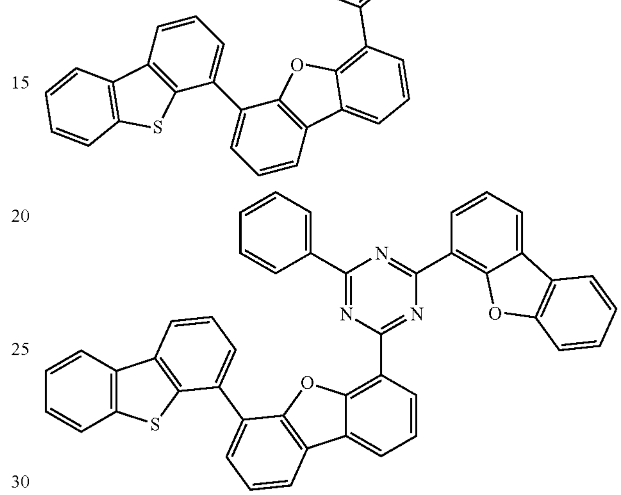
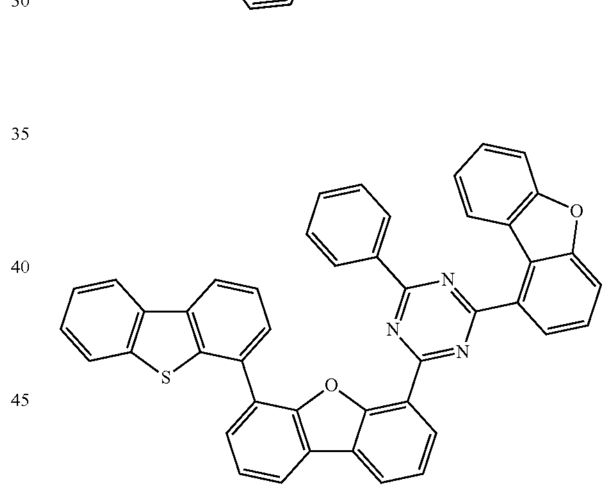
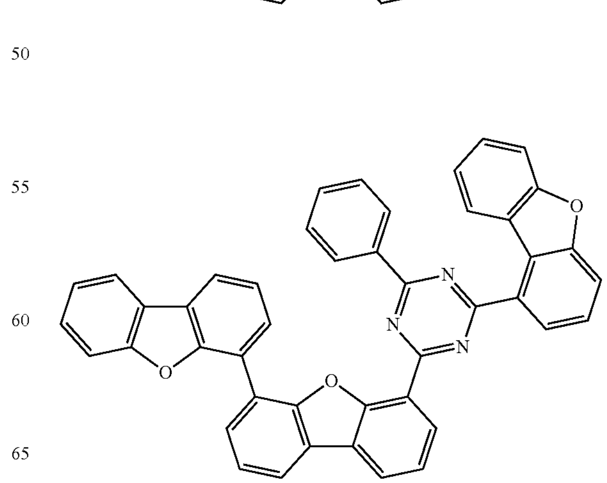

-continued
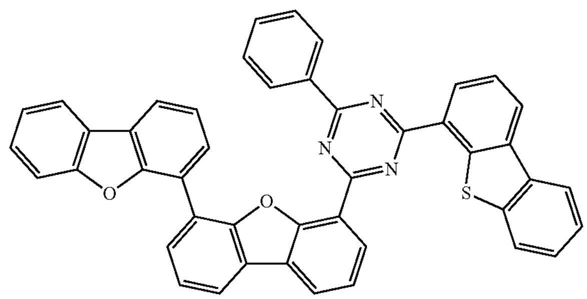
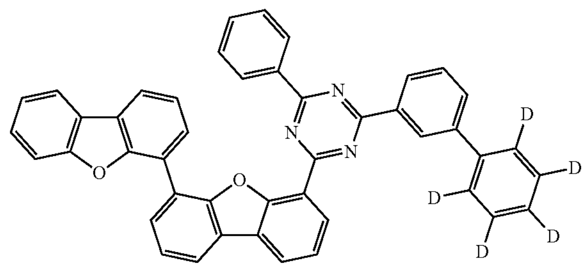
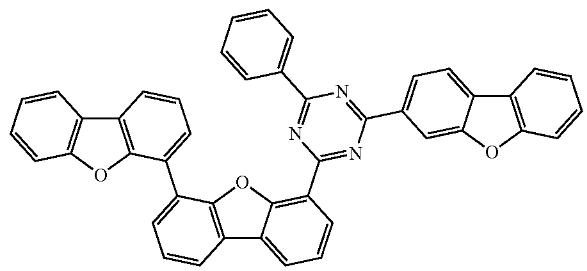
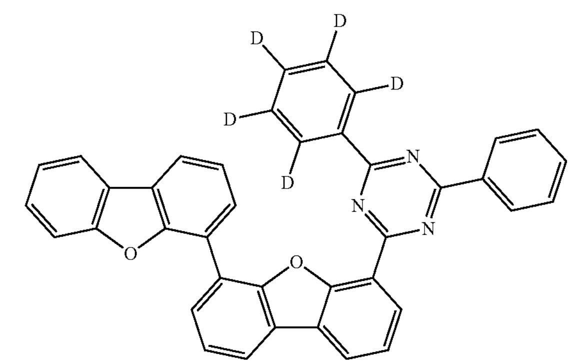
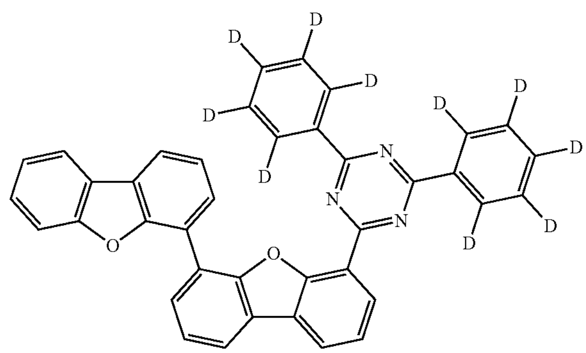
-continued
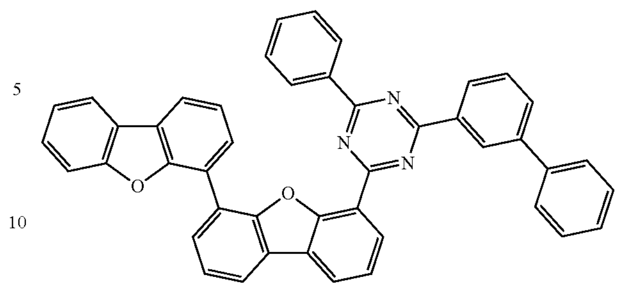
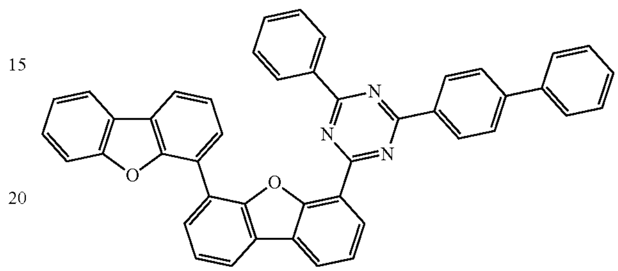
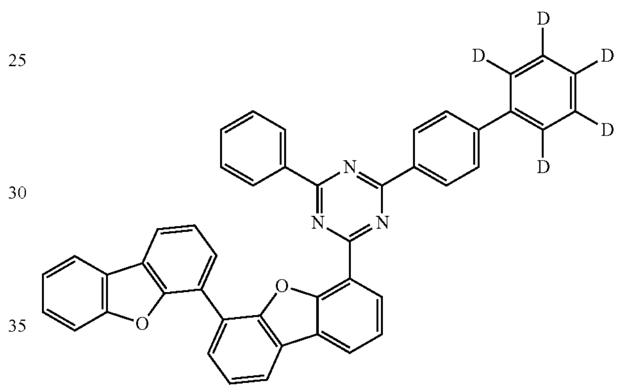
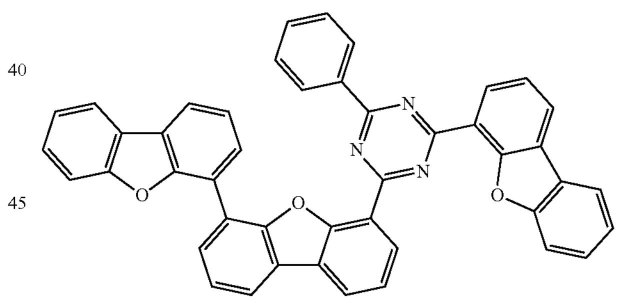
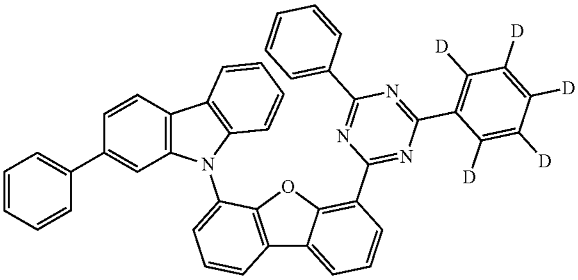

-continued
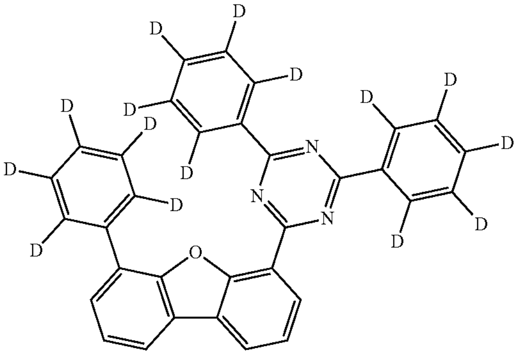
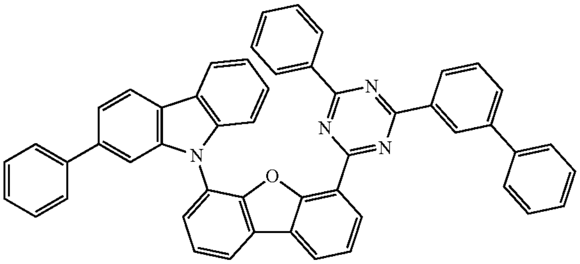
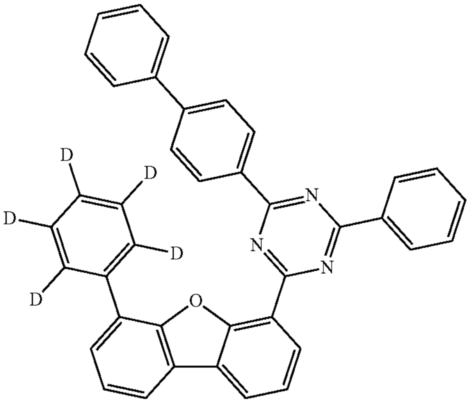
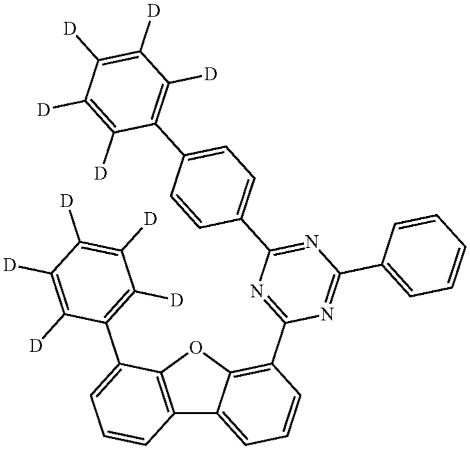
-continued
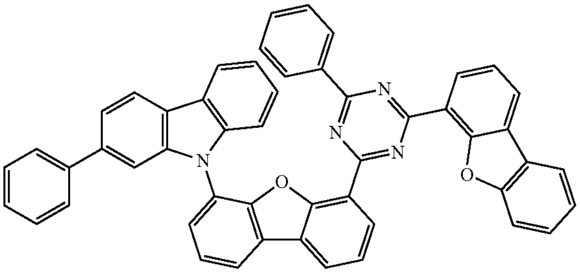
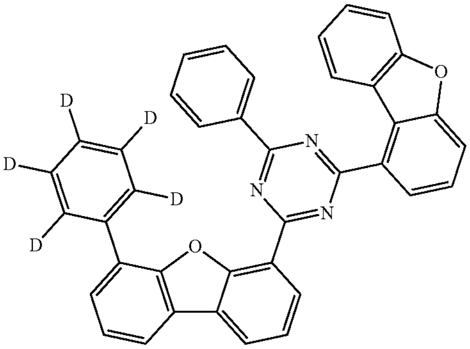
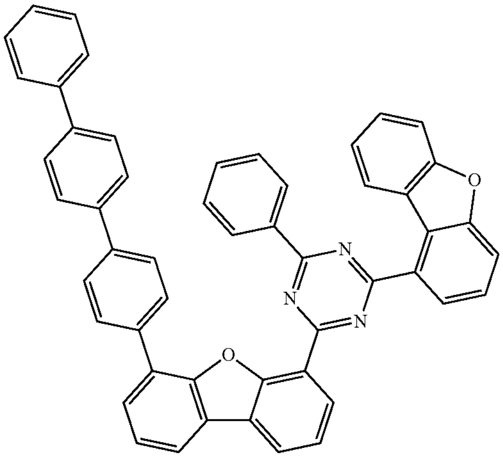
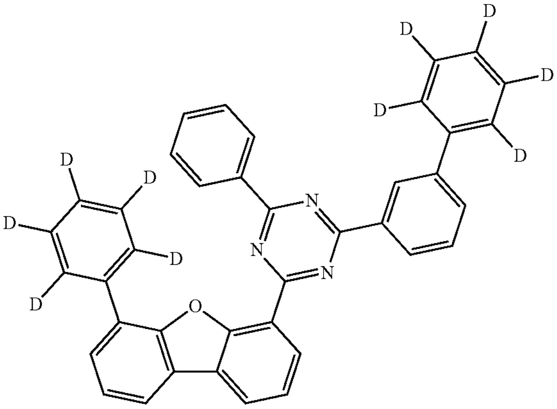

-continued
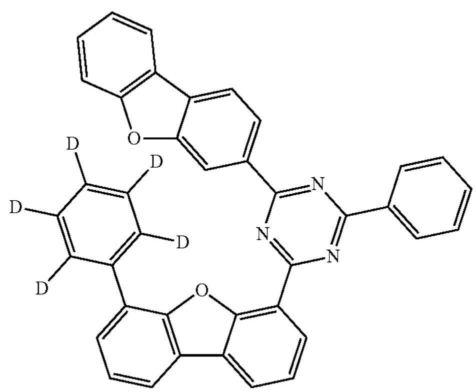
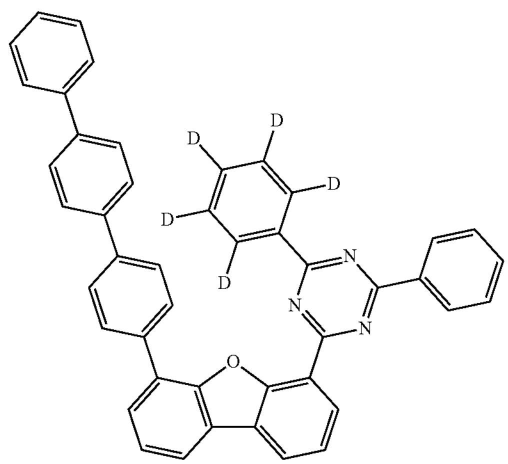
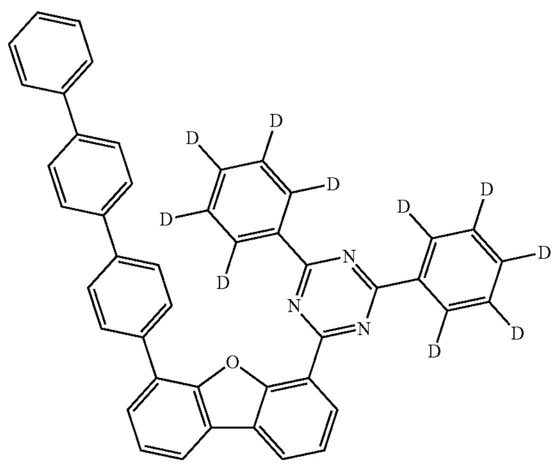
-continued
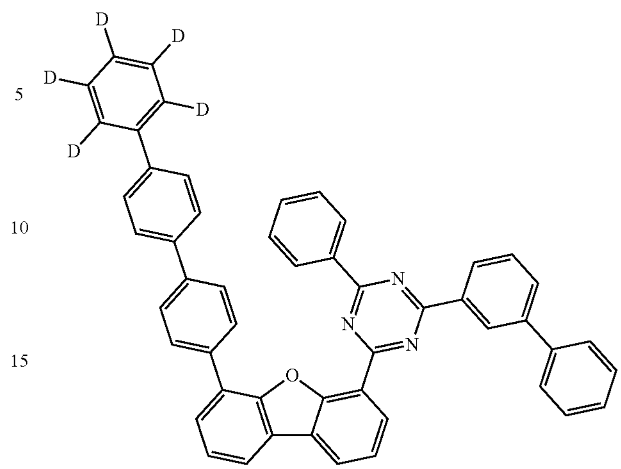
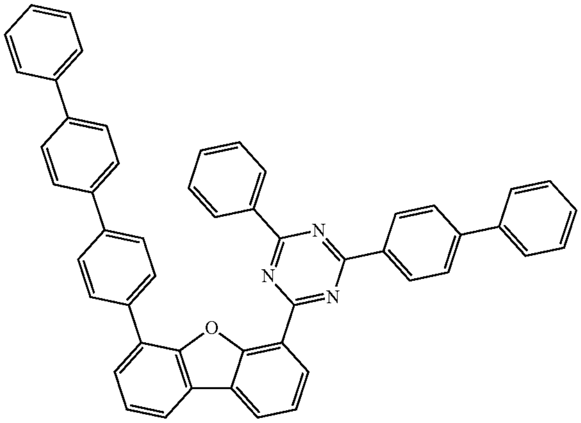
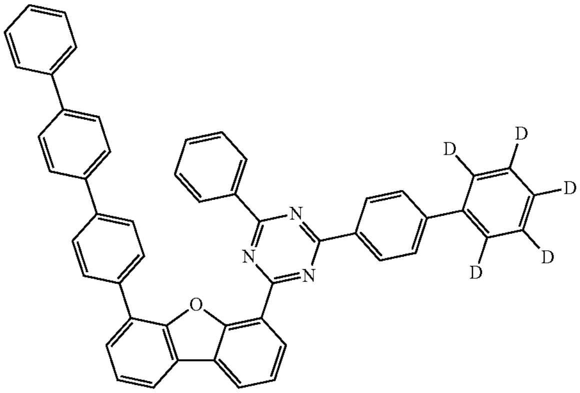

-continued
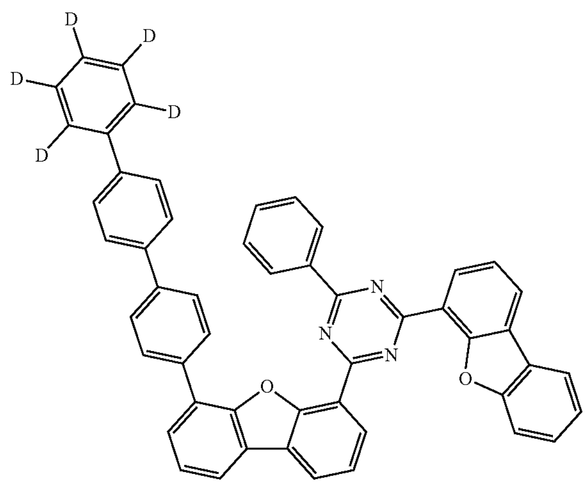
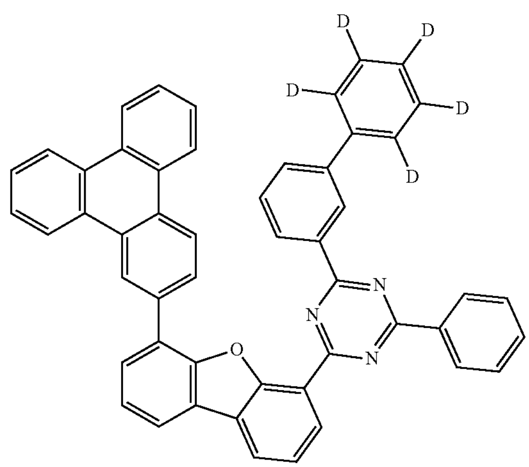
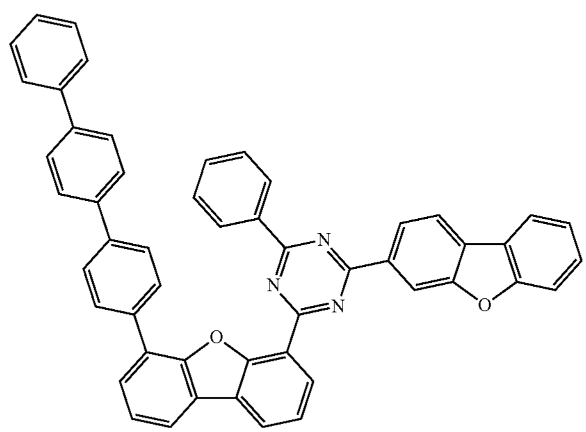
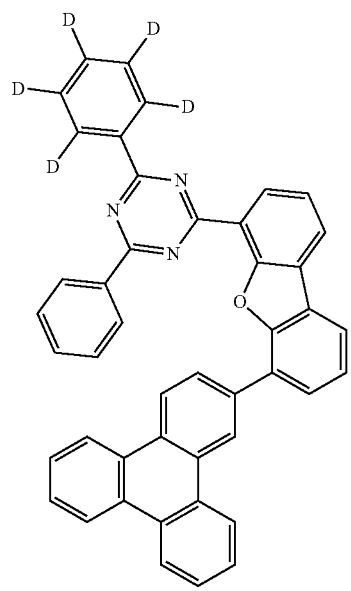
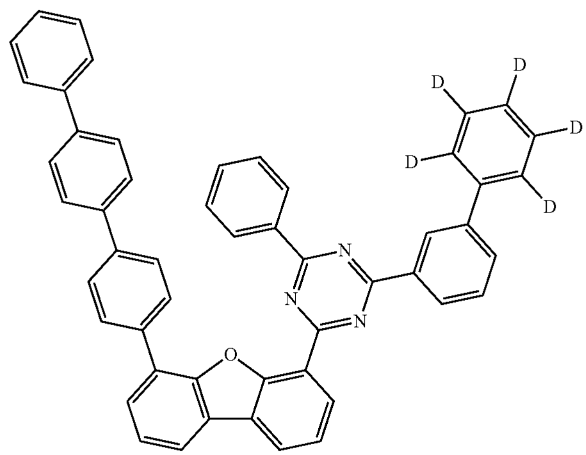
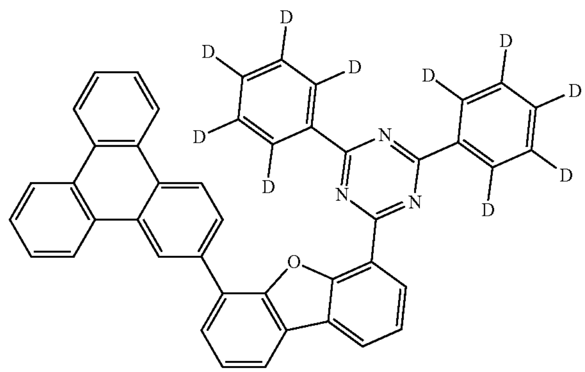
-continued -continued
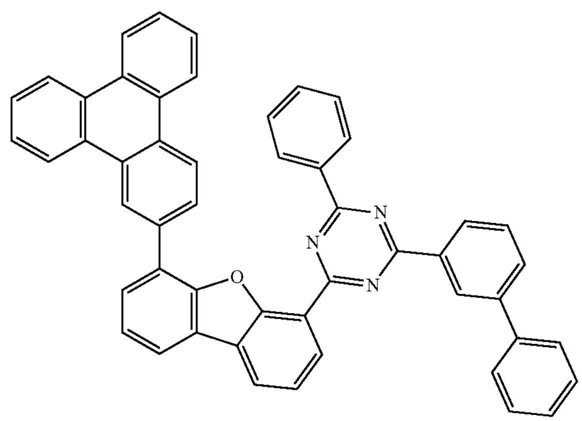
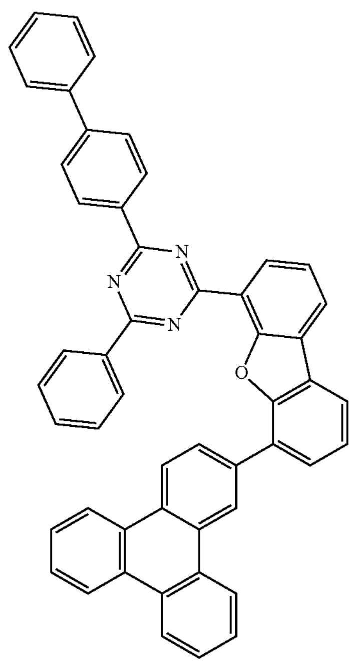
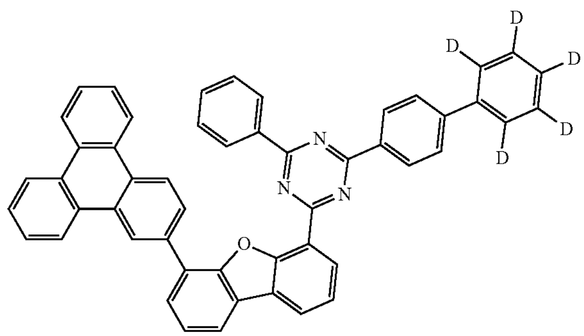
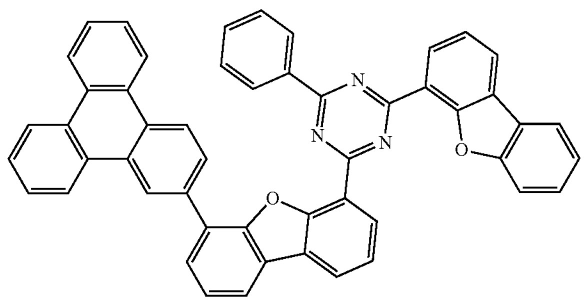
-continued
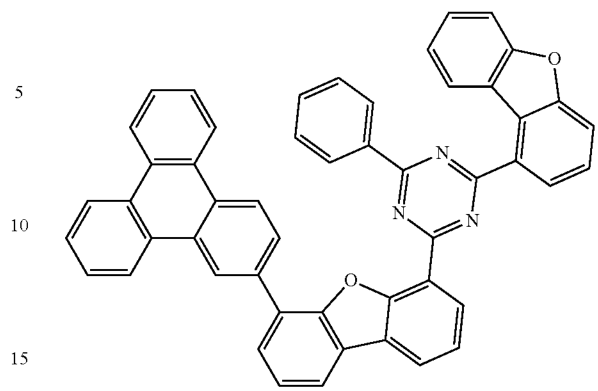
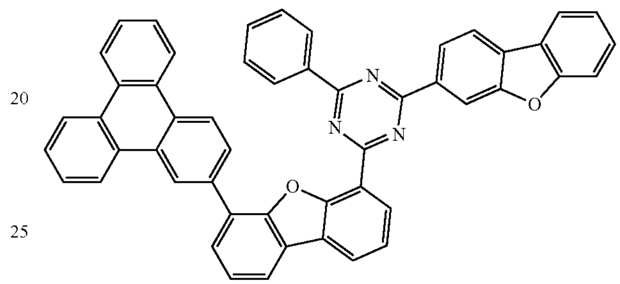
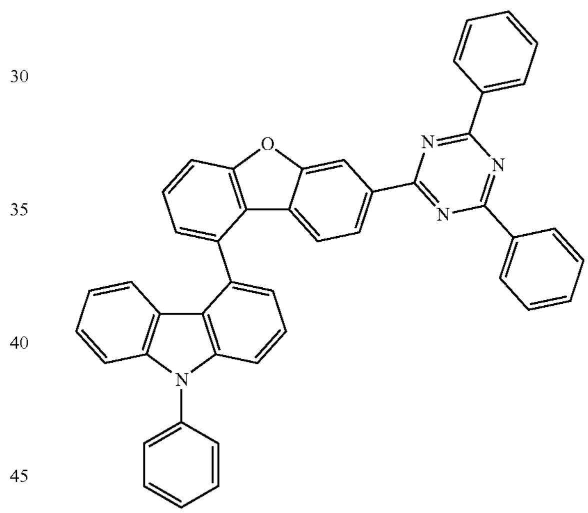
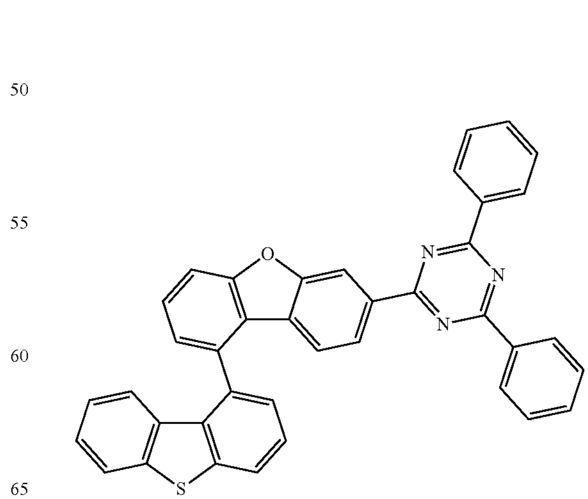

-continued
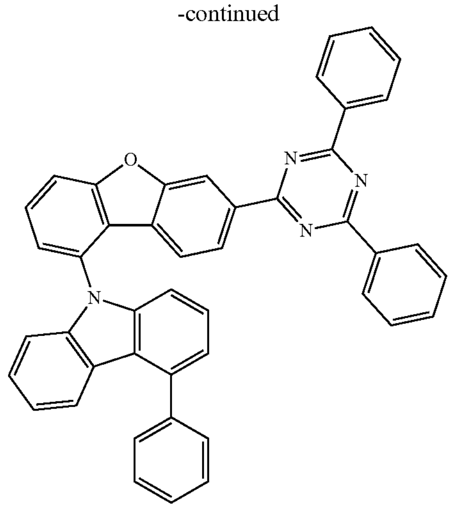
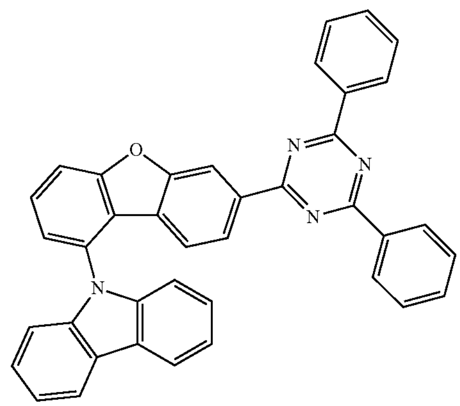
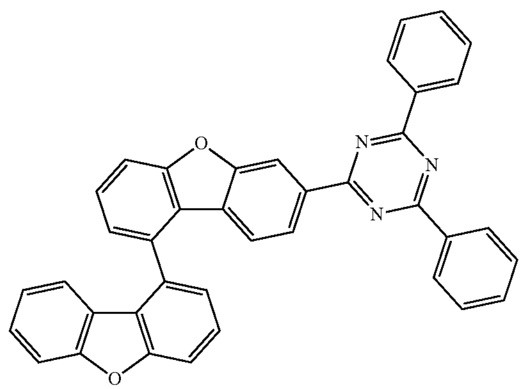
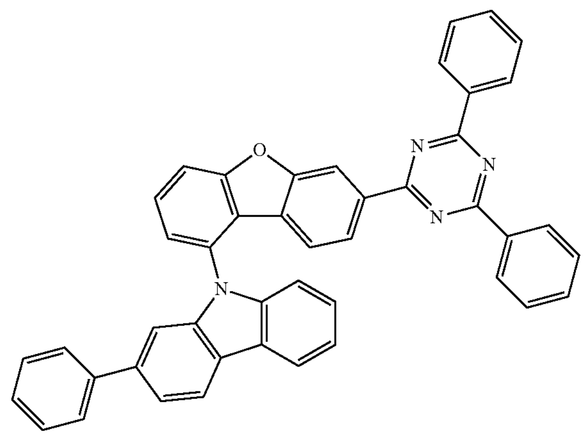
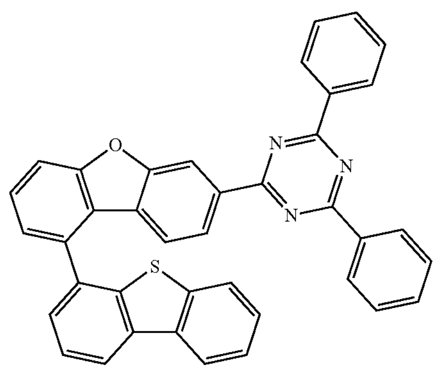
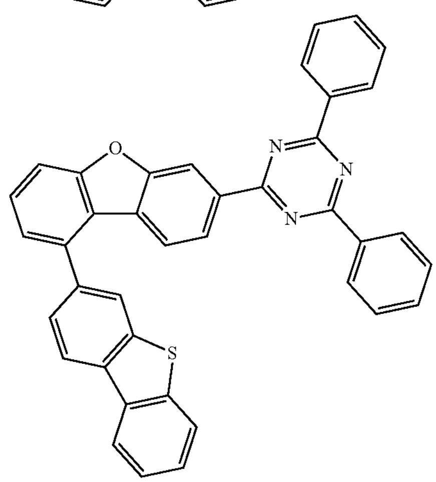
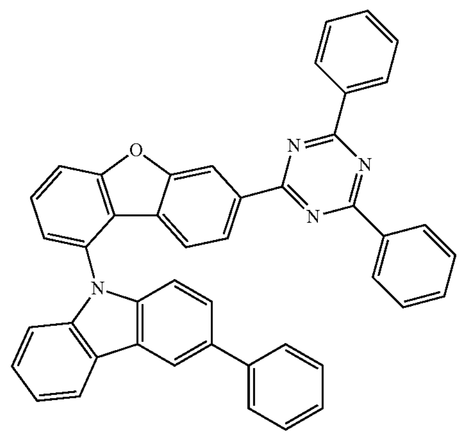

-continued
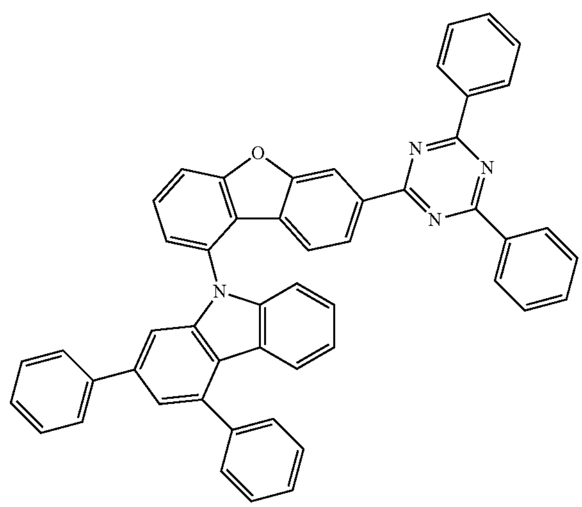
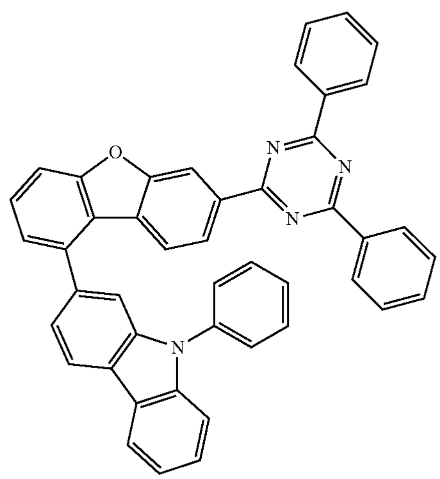
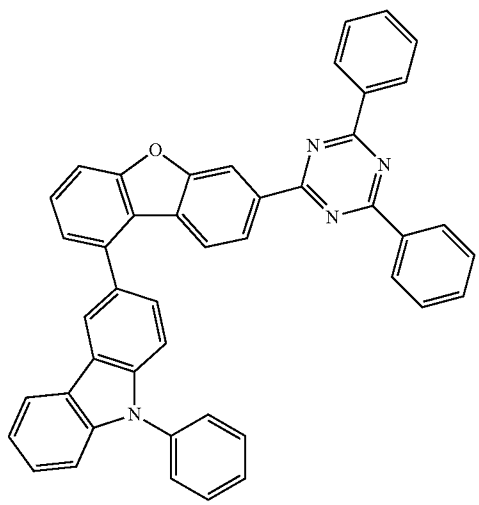
-continued
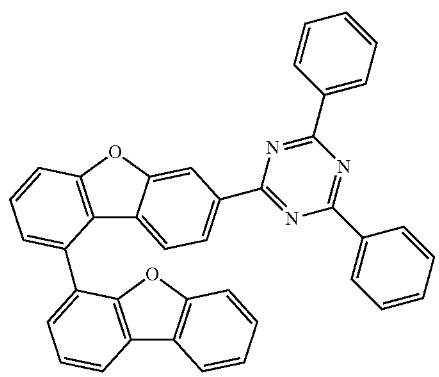
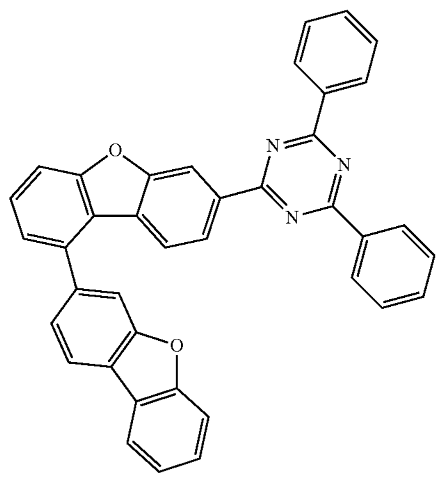
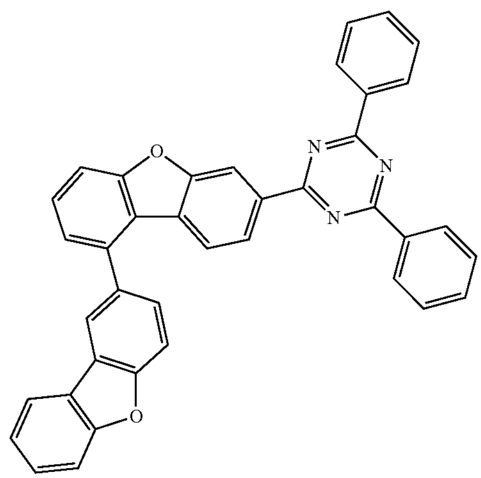
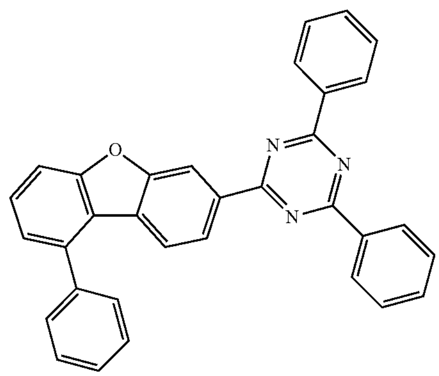

-continued
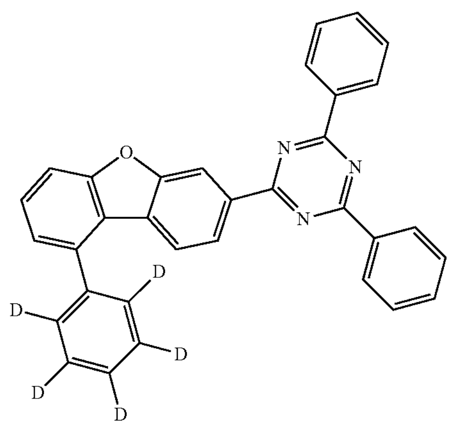
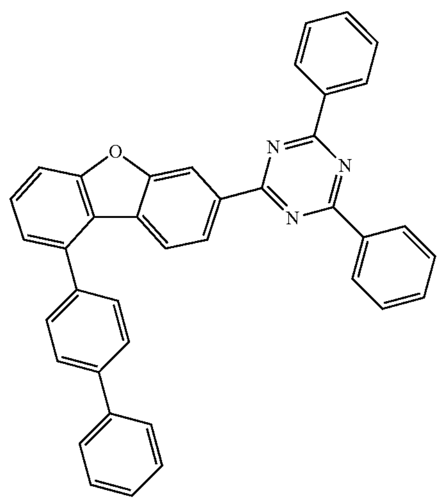
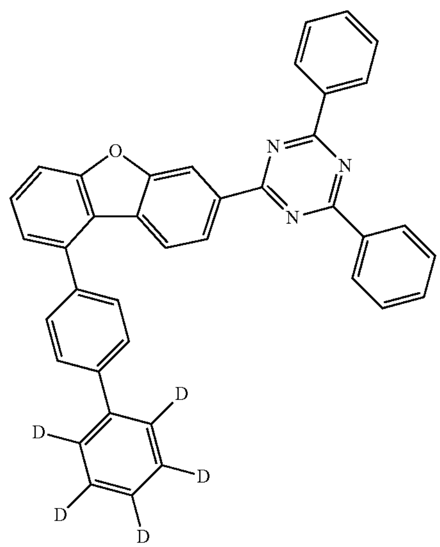
-continued
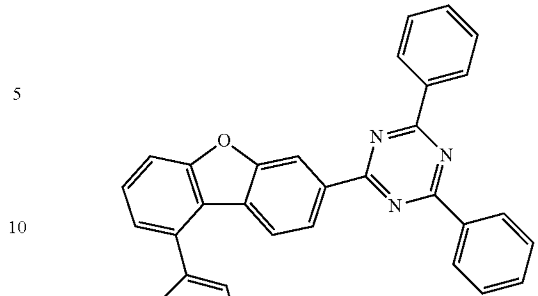
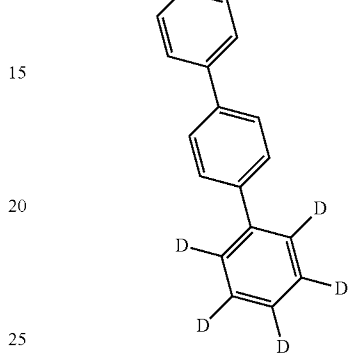
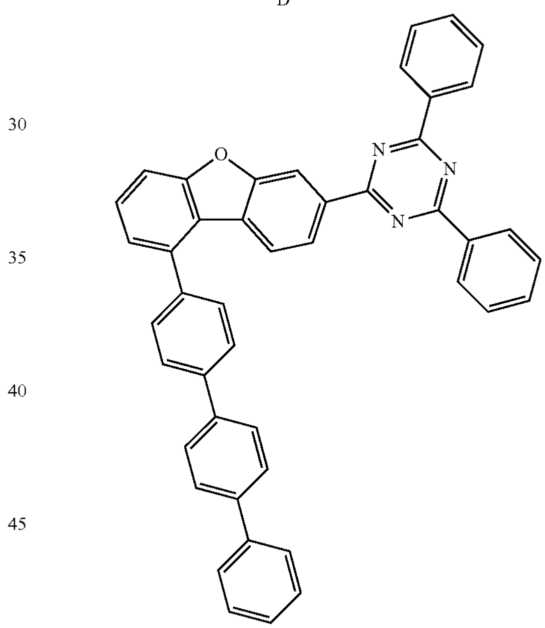
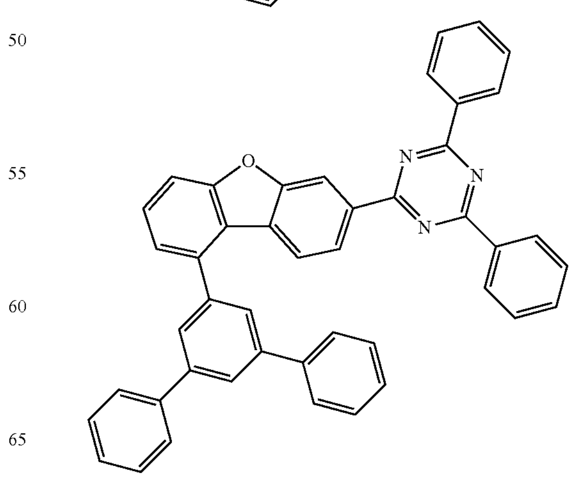

-continued
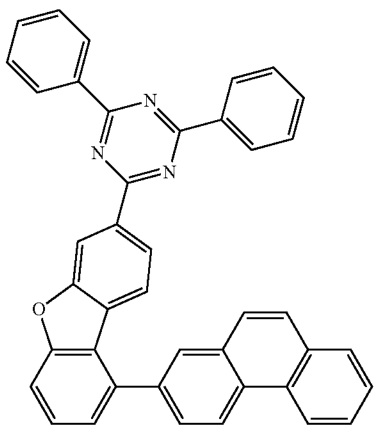
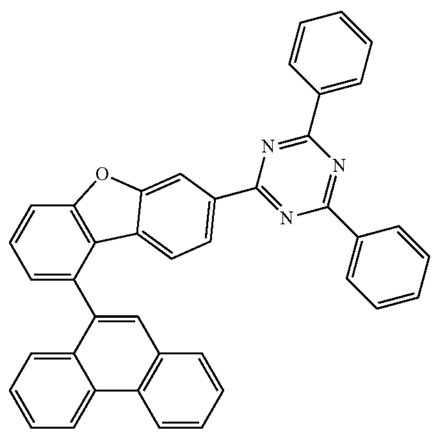
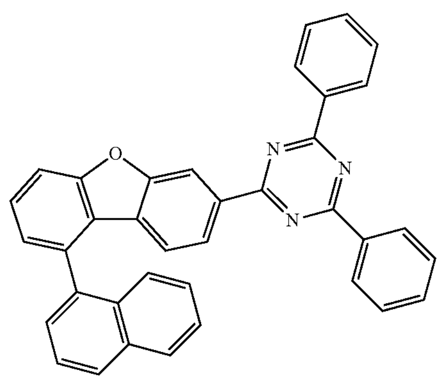
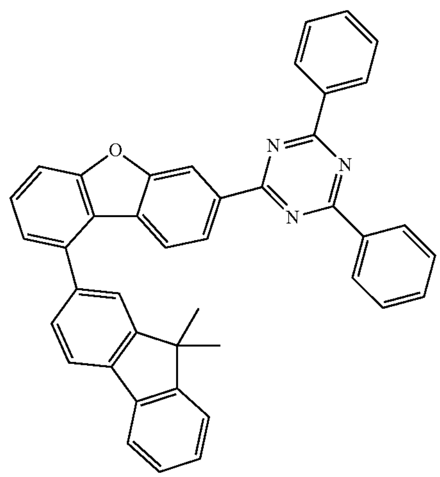
-continued
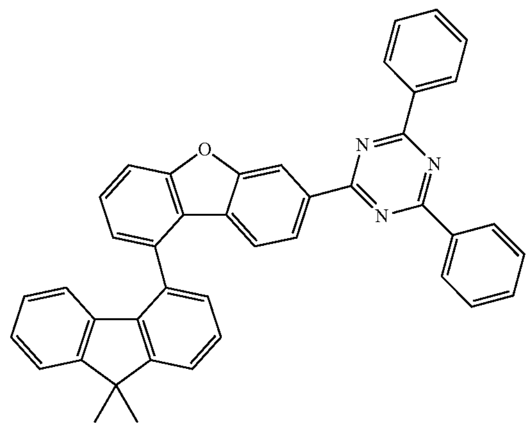
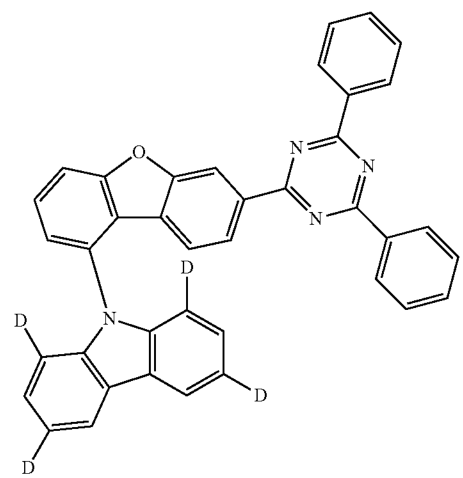
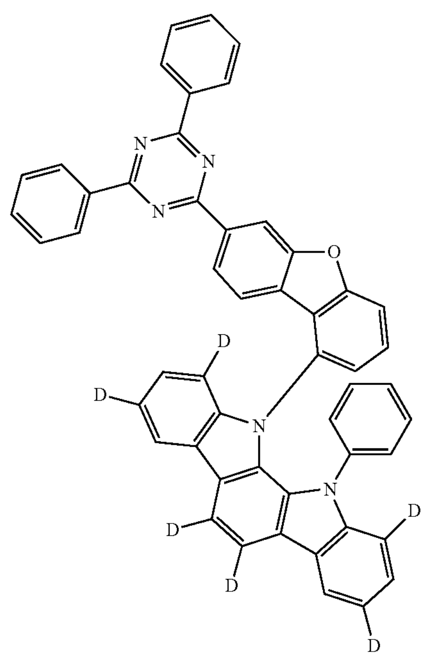

-continued
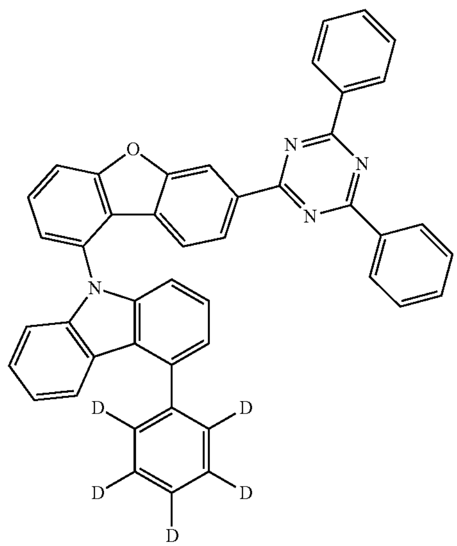
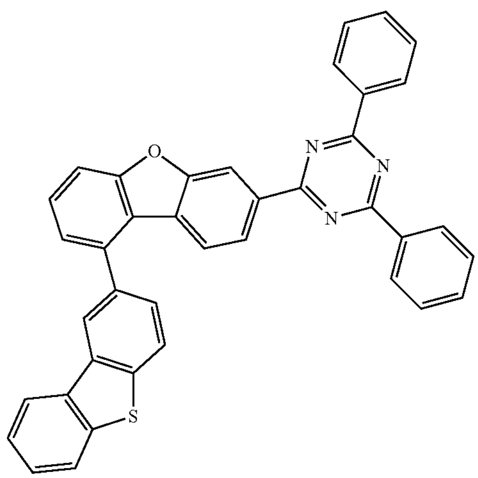
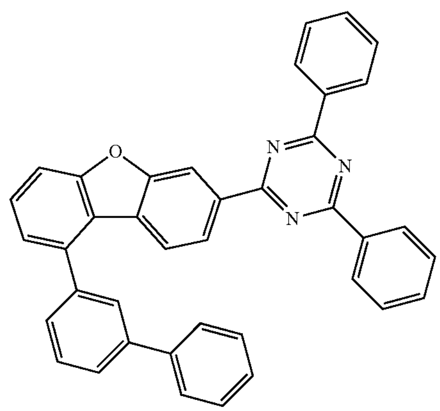
-continued
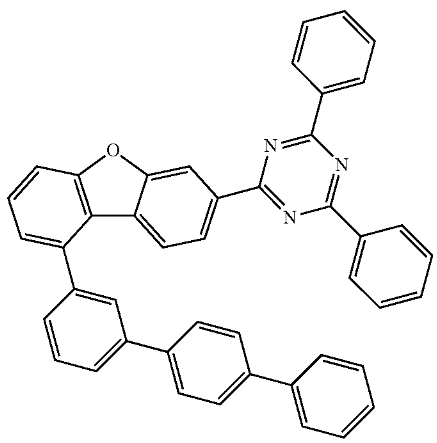
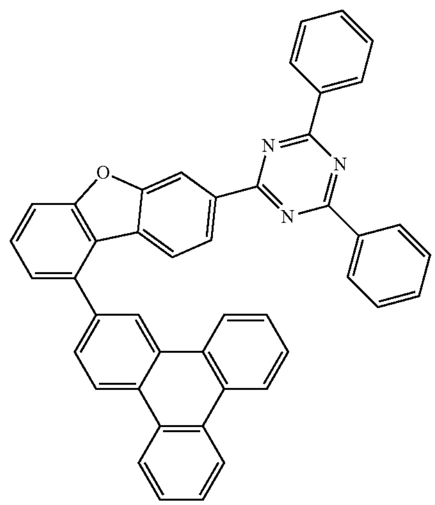
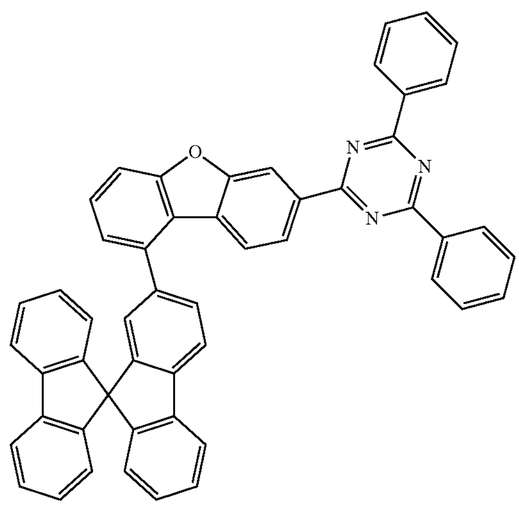

-continued
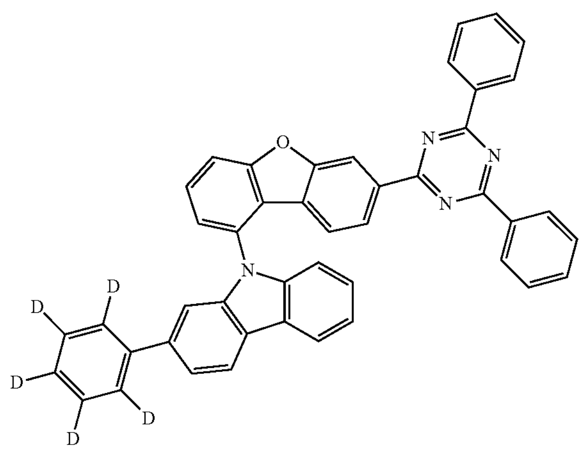
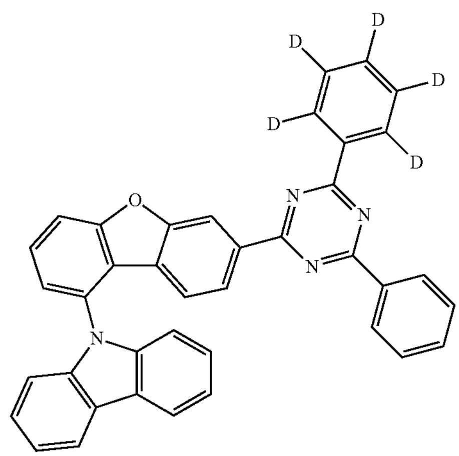
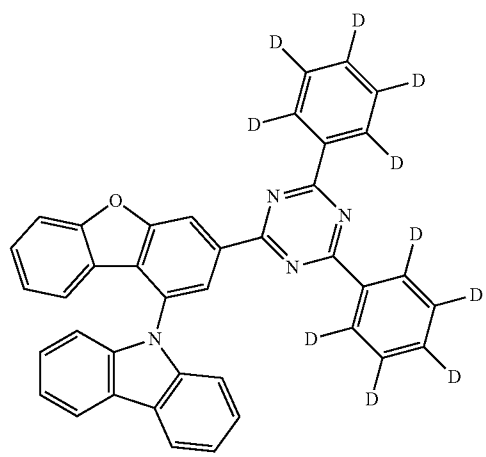
-continued
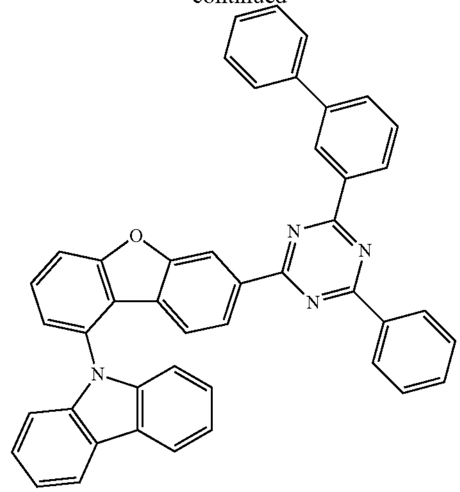
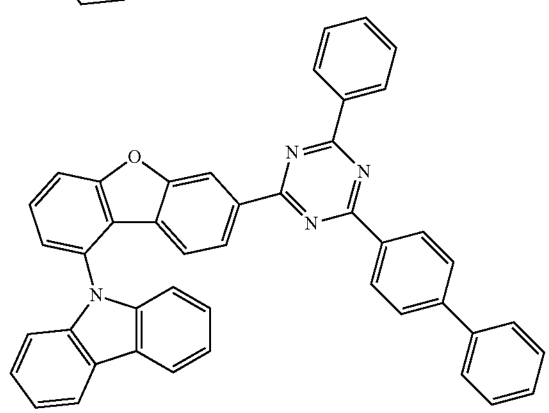
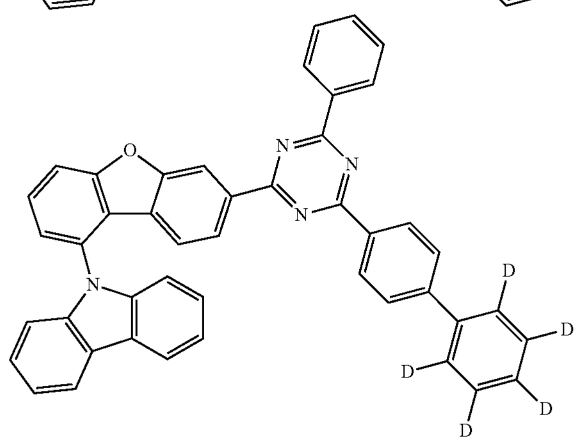
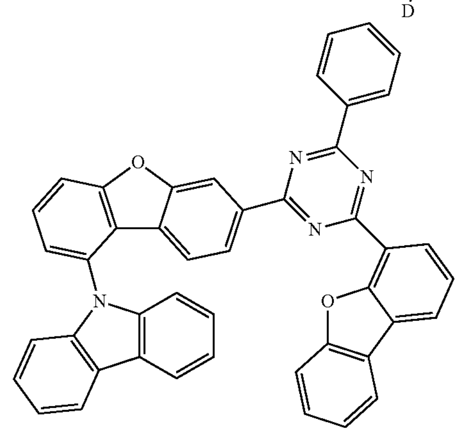

-continued
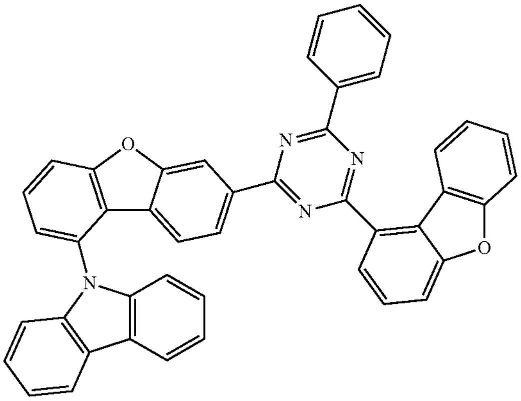
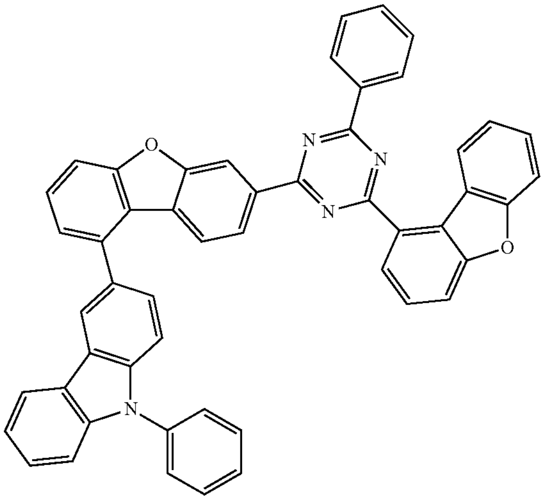
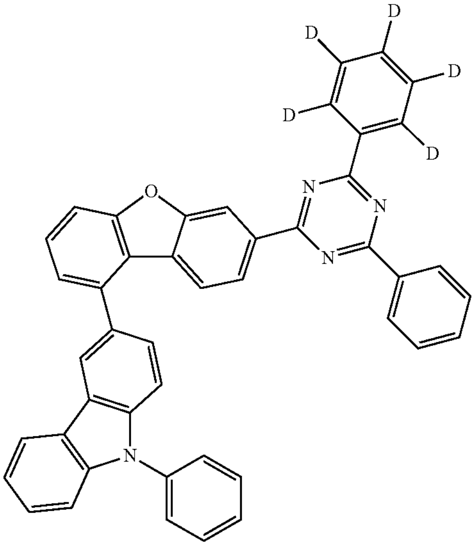
-continued
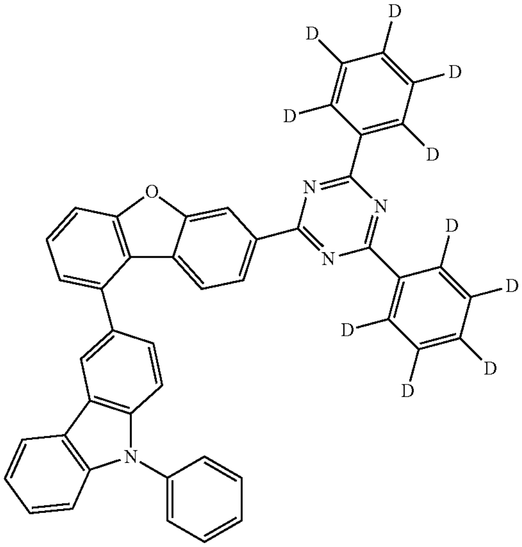
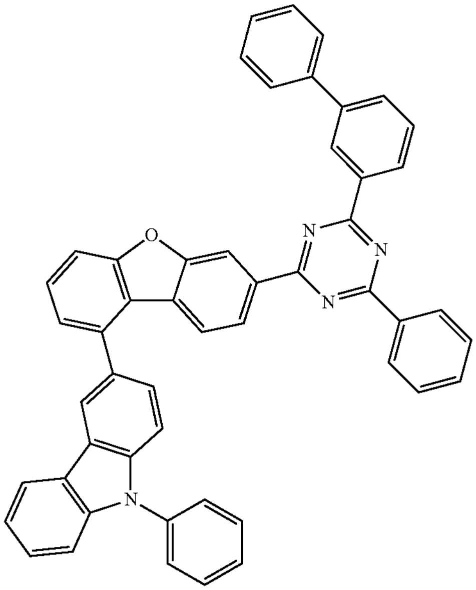
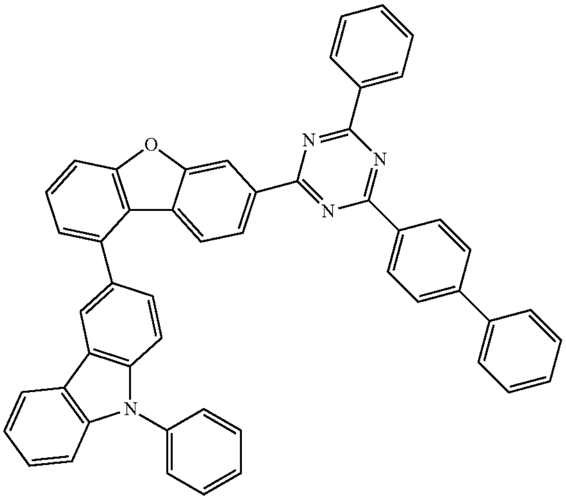

-continued
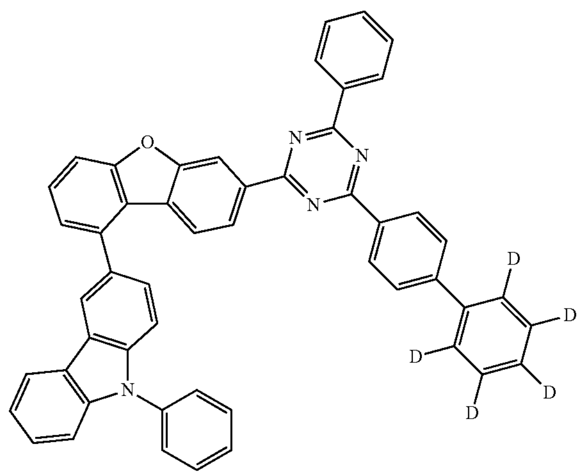
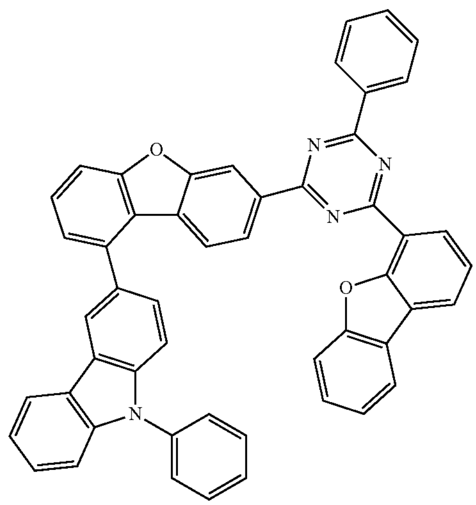
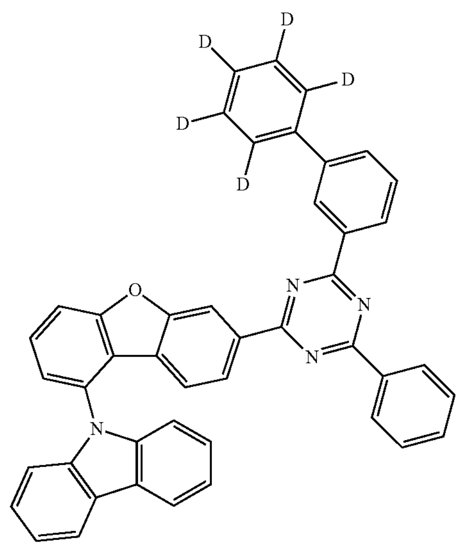
-continued
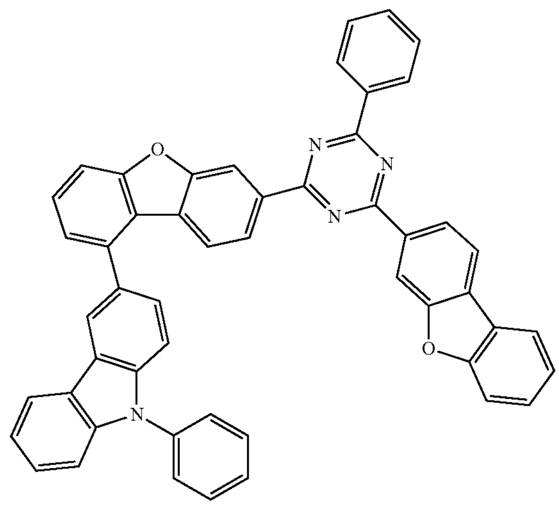
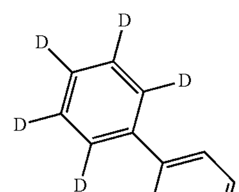
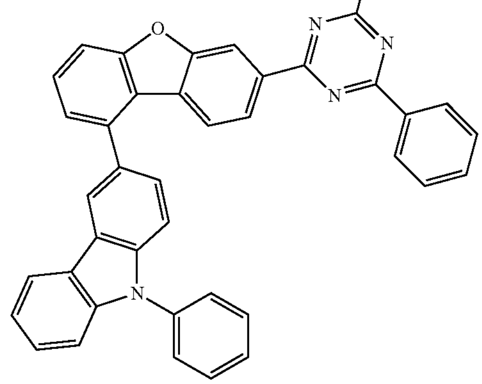
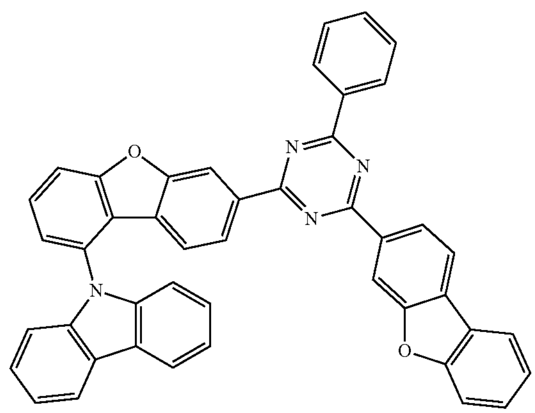

-continued
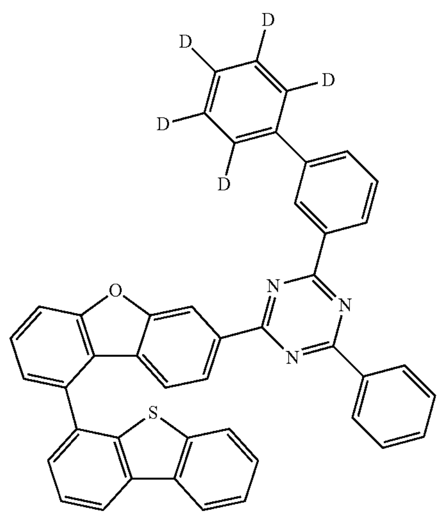
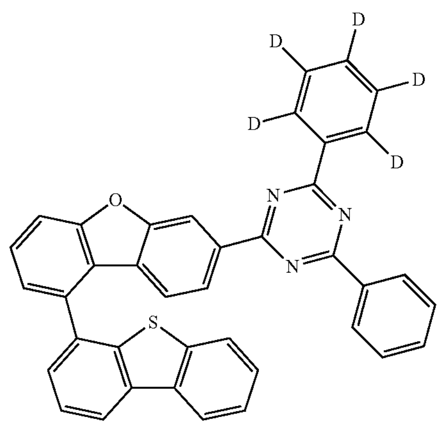
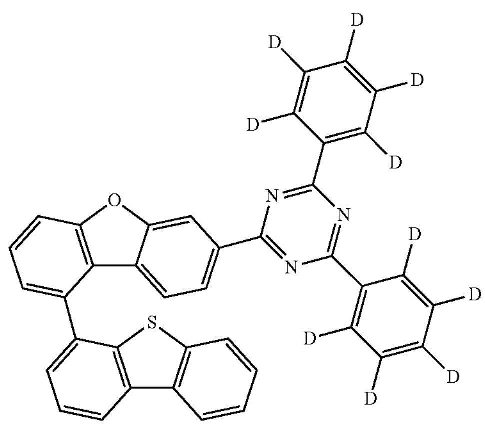
-continued
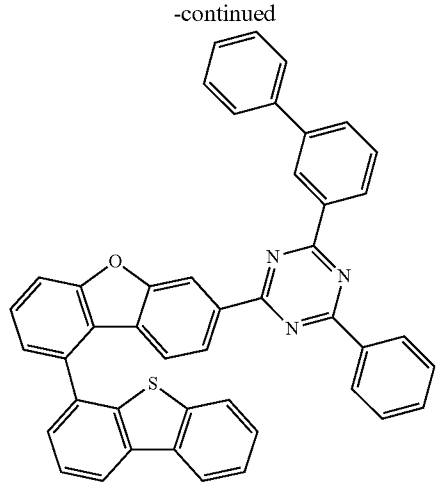
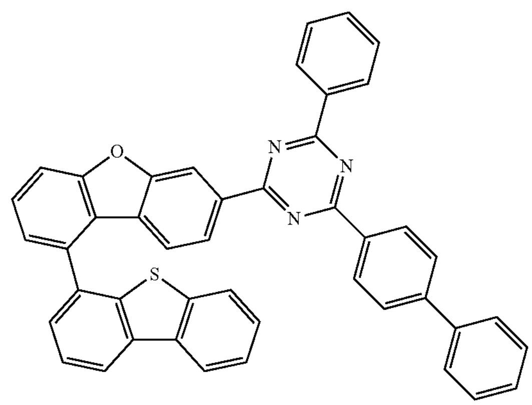
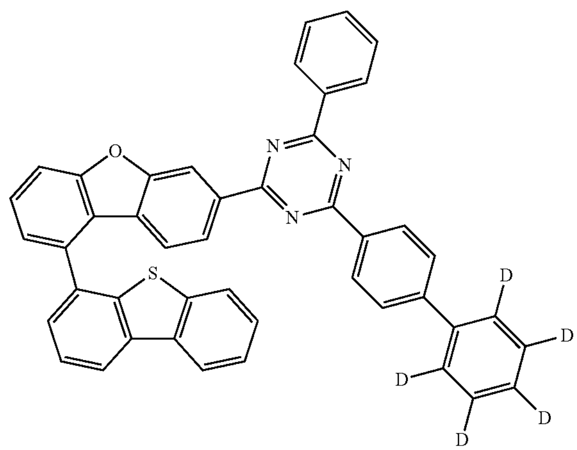
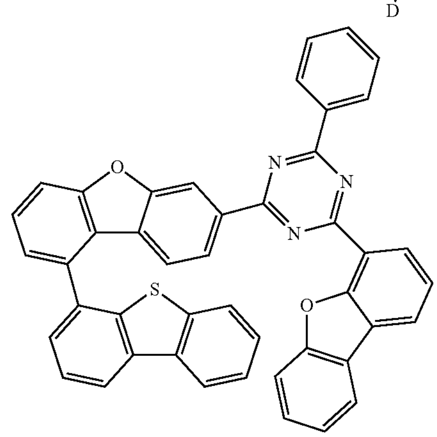

-continued
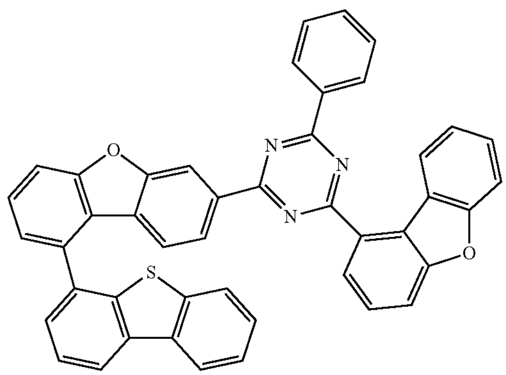
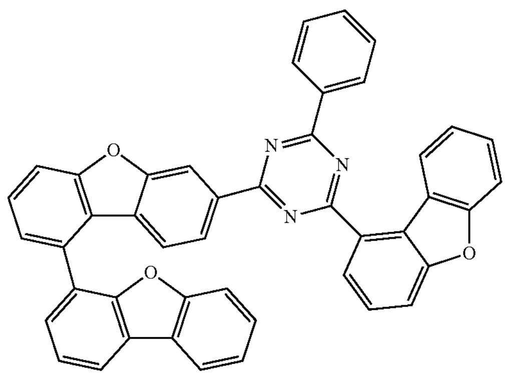
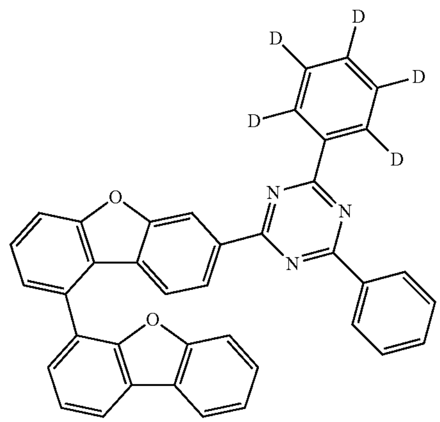
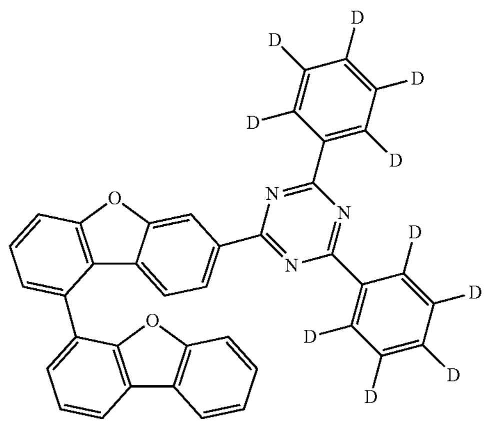
-continued
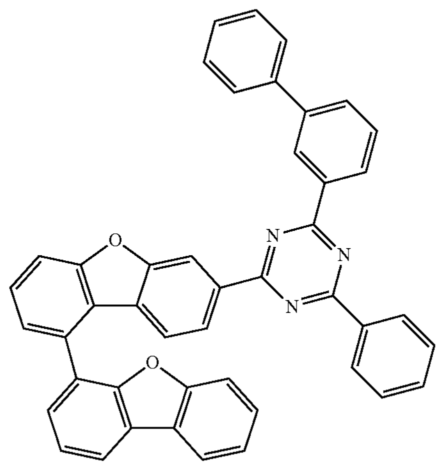
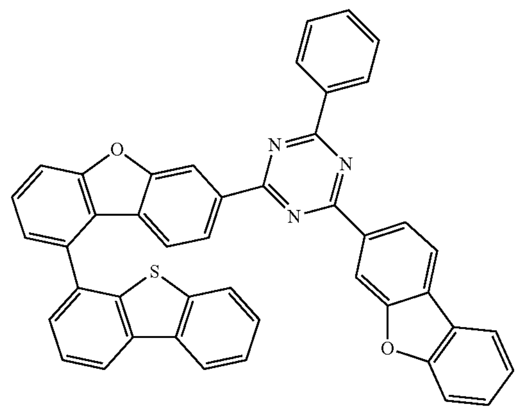
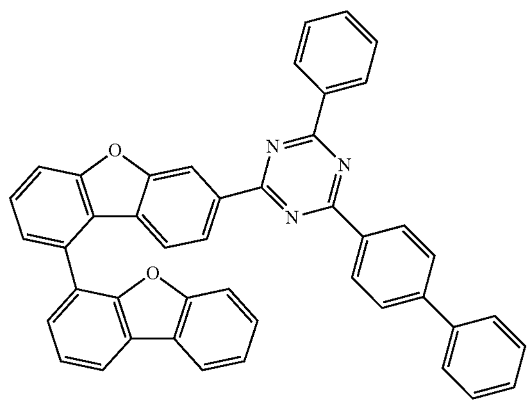
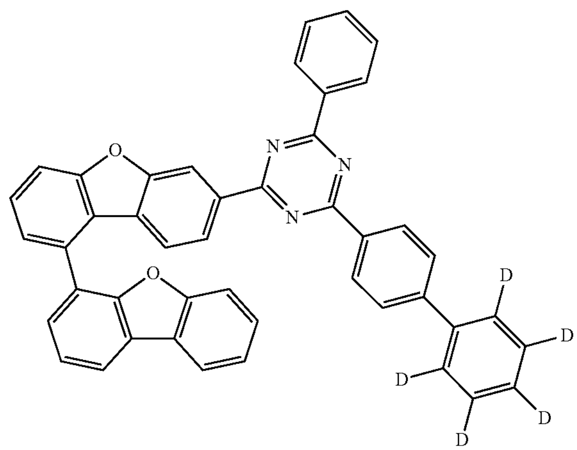

-continued
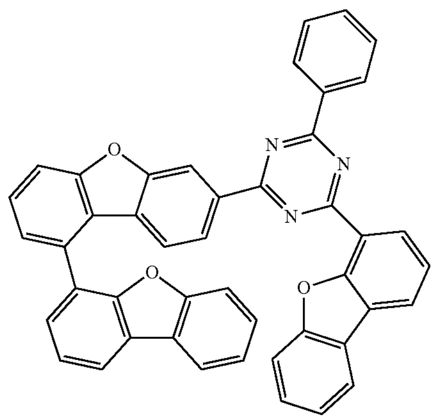
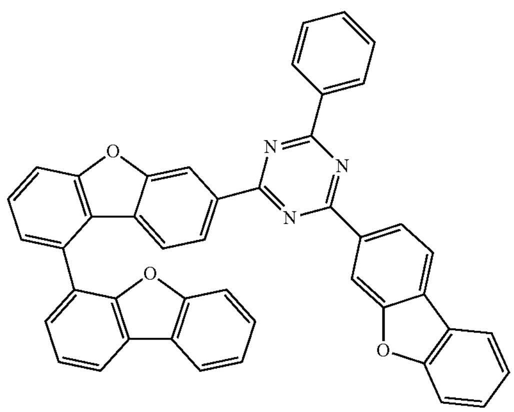
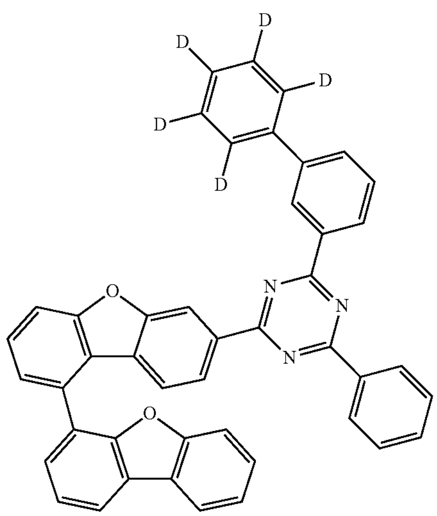
-continued
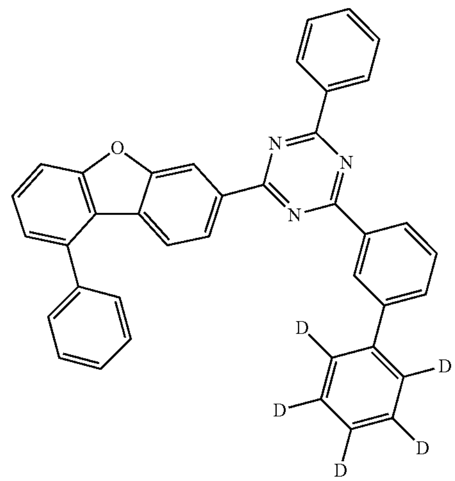
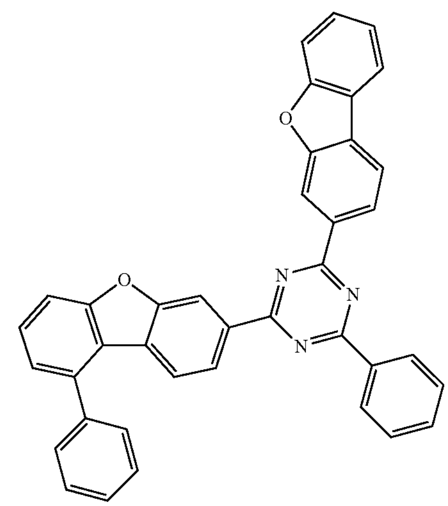
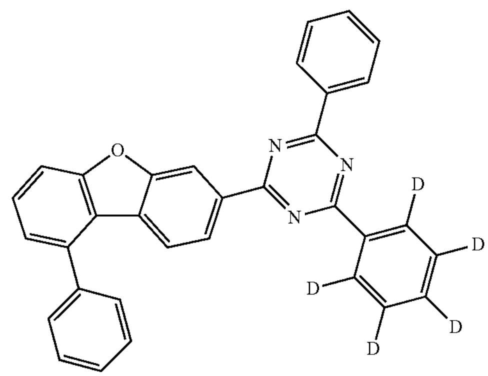

-continued
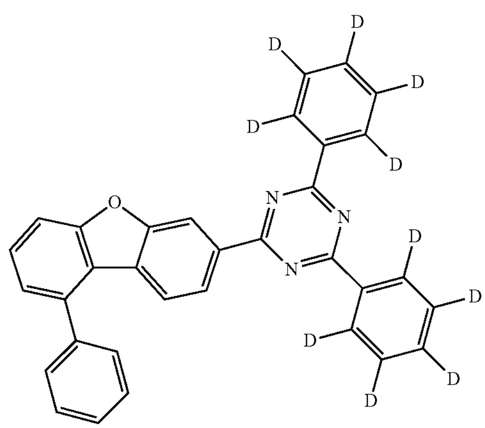
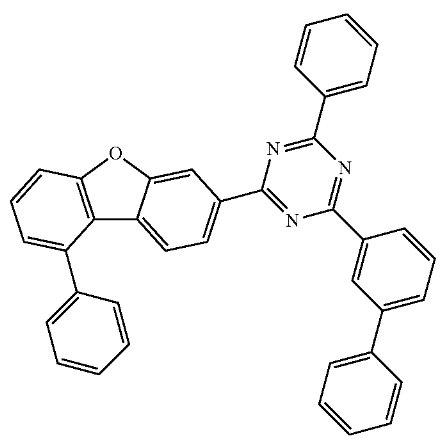
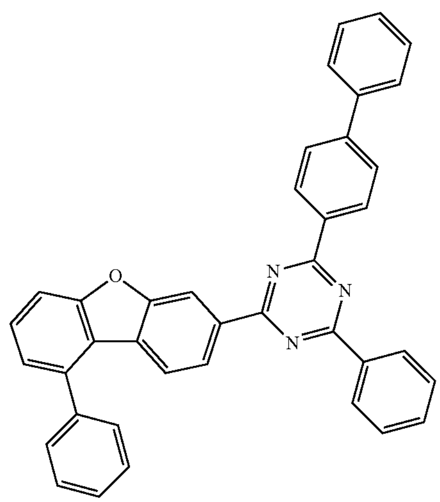
-continued
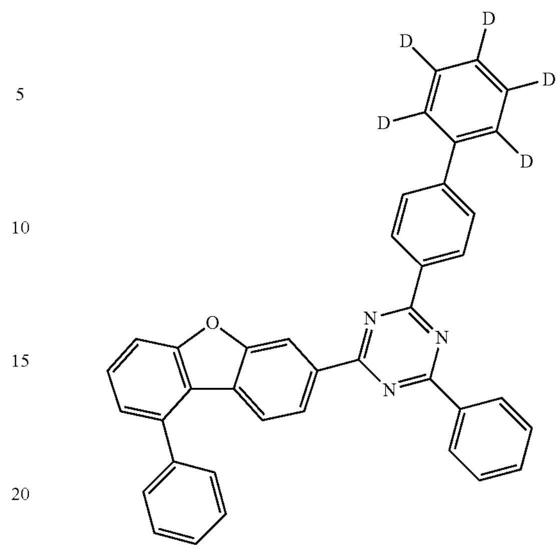
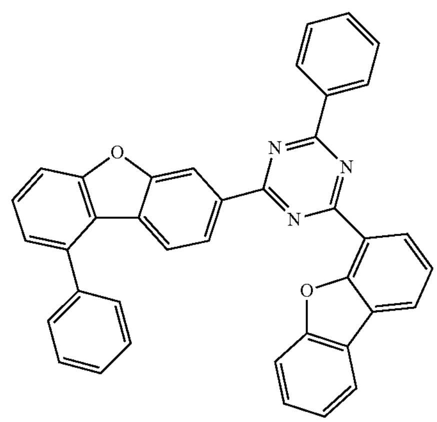
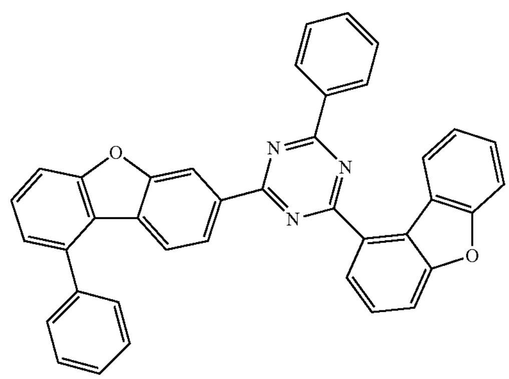

-continued
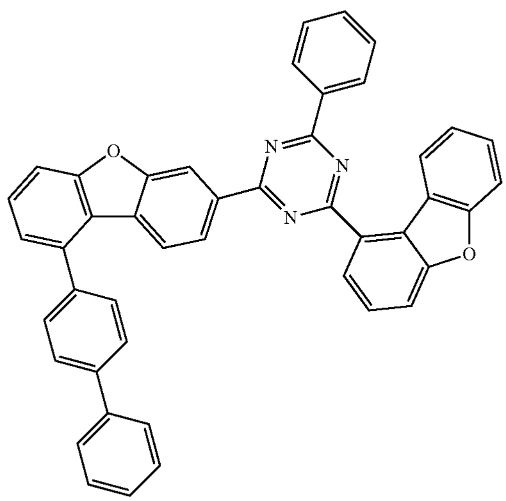
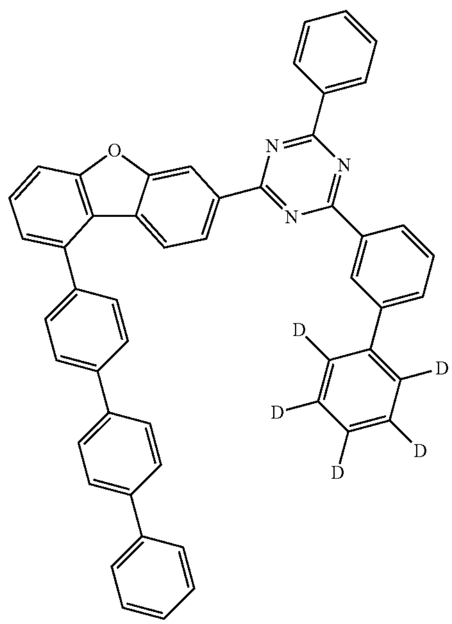
-continued
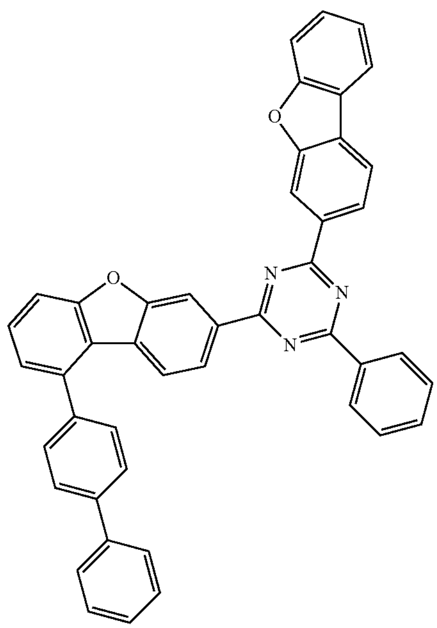
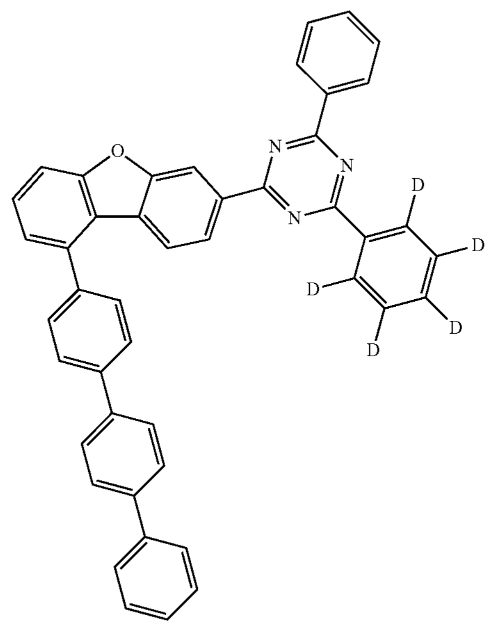

-continued
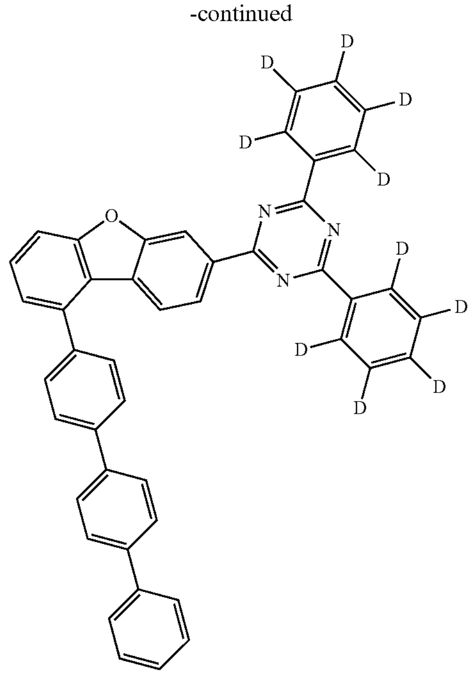
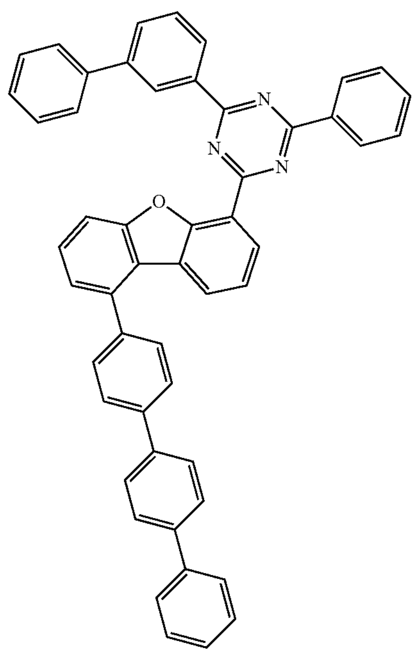
-continued
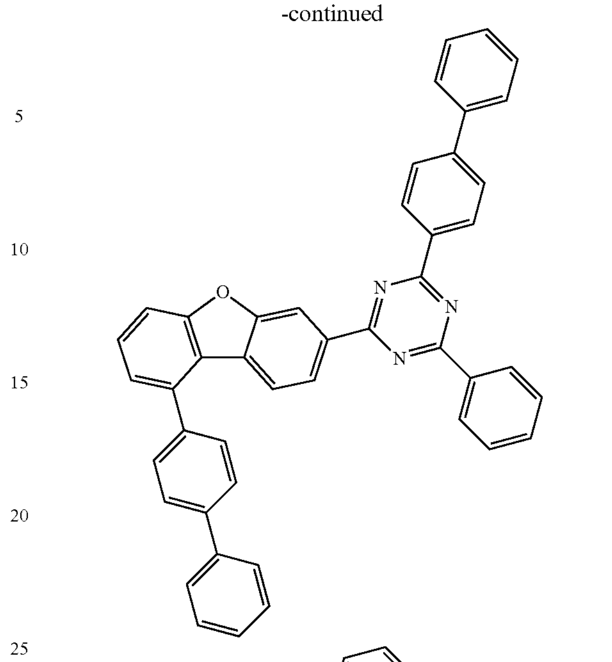
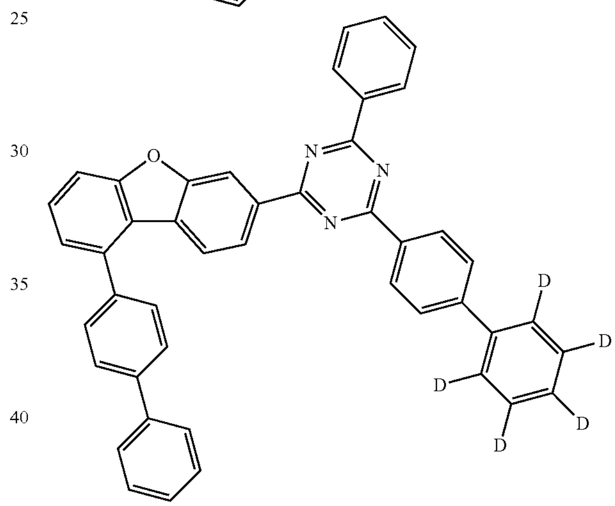
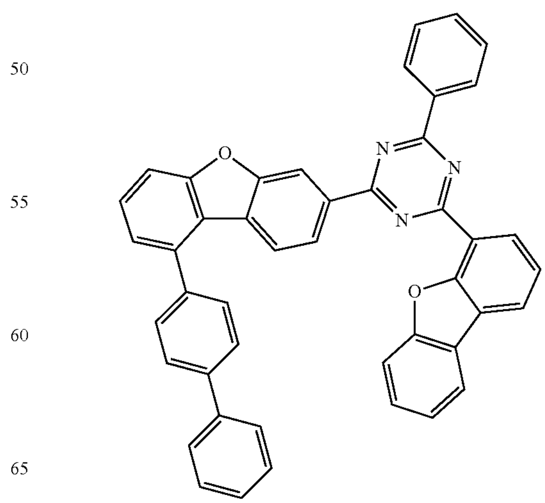

-continued
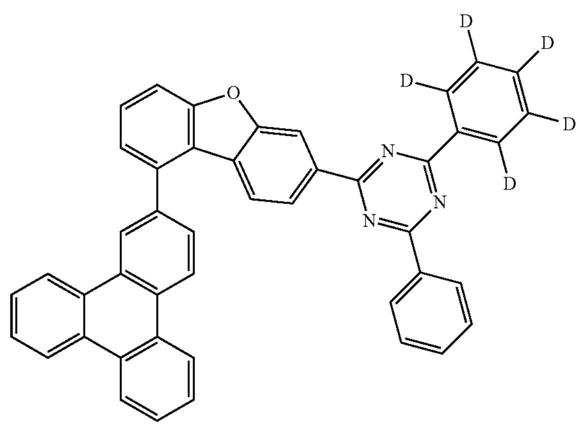
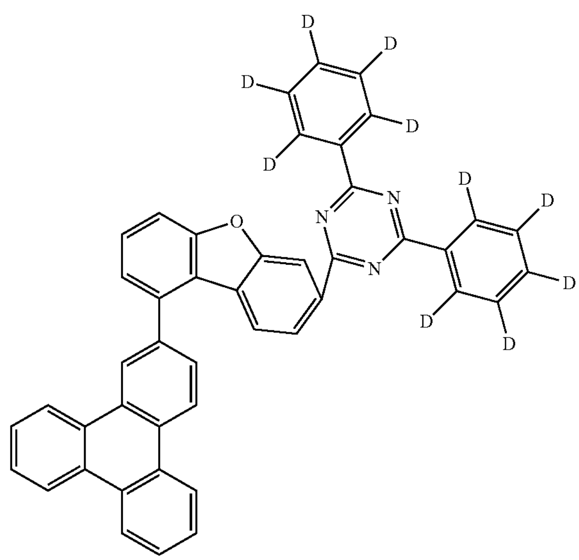
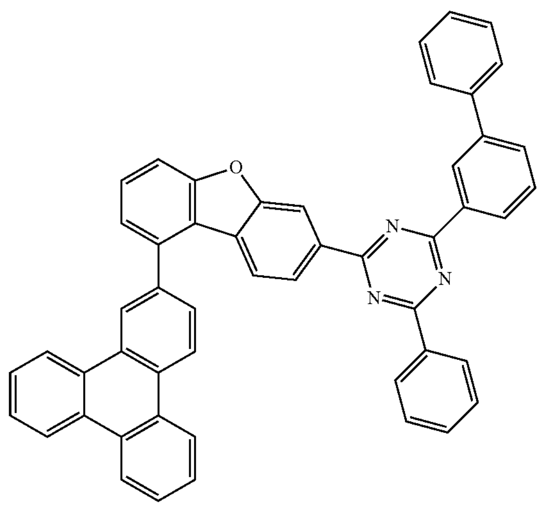
-continued
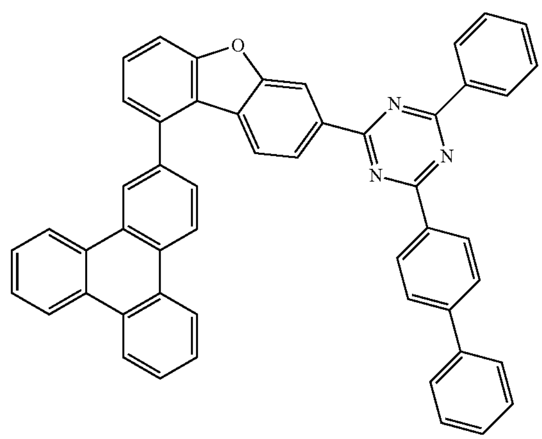
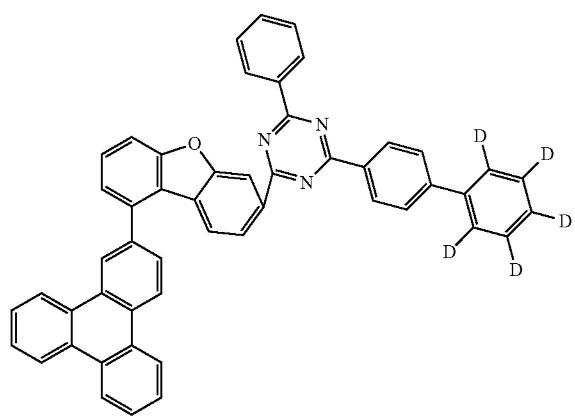
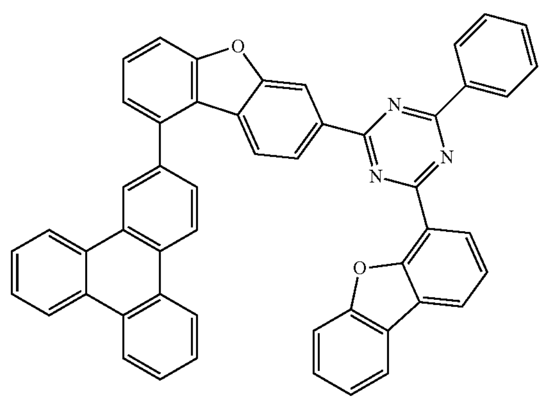

-continued
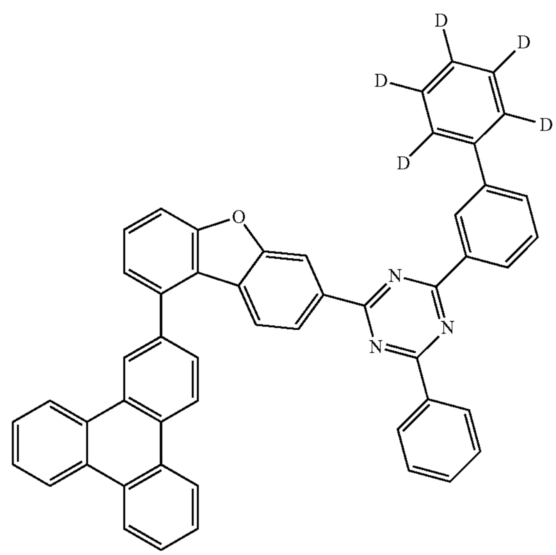
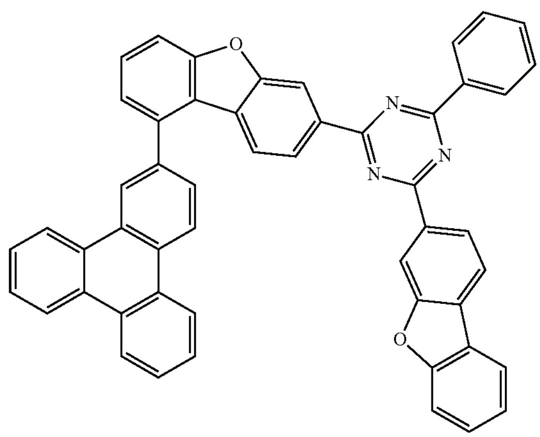
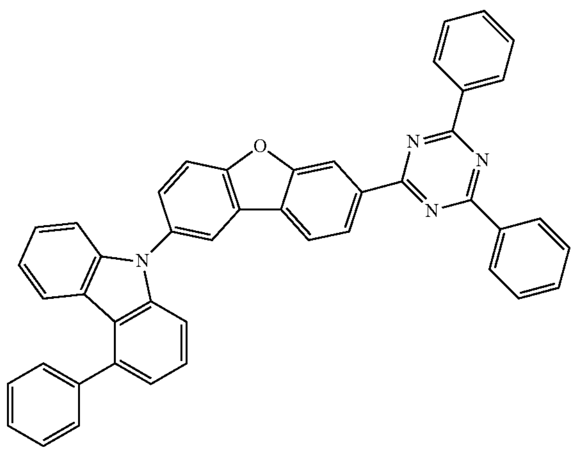
-continued
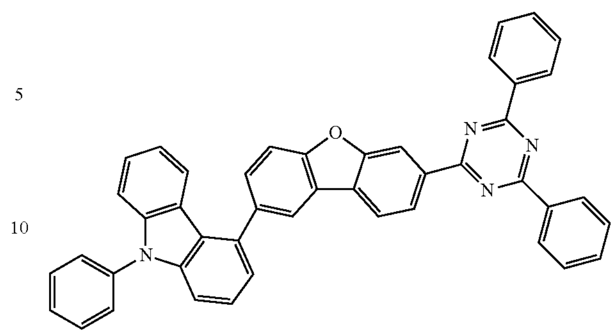
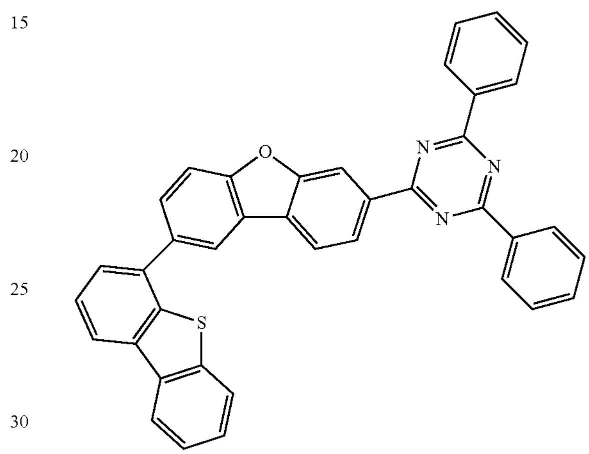
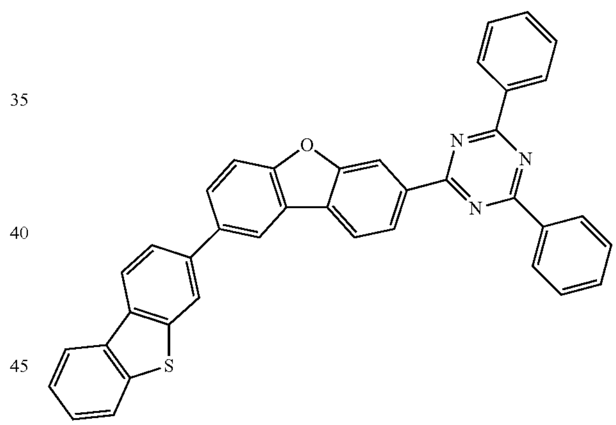
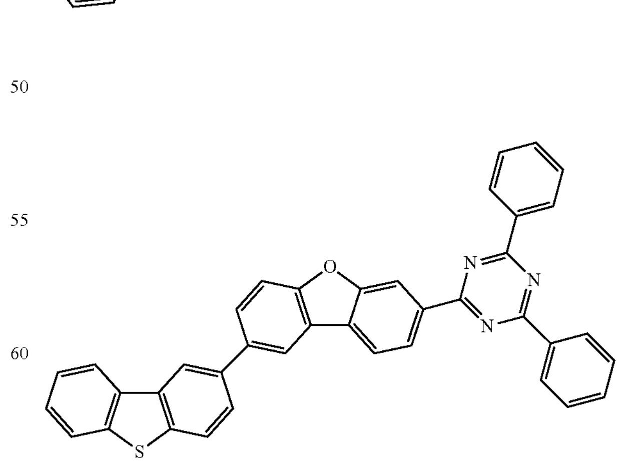

-continued
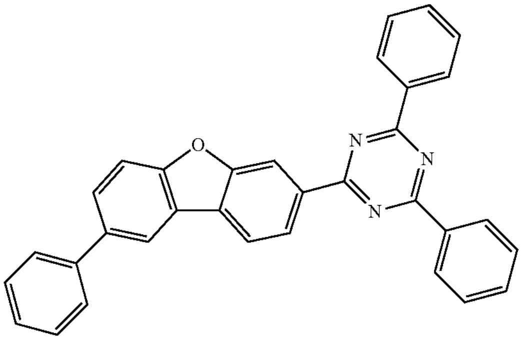
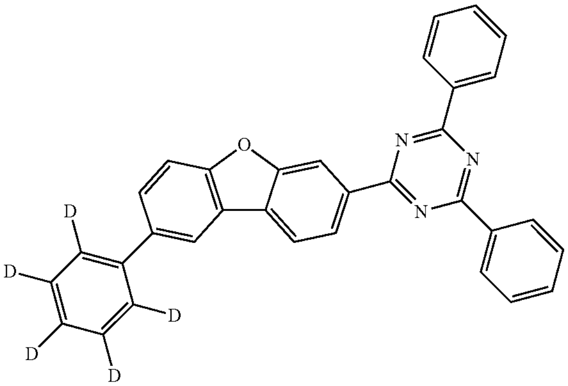
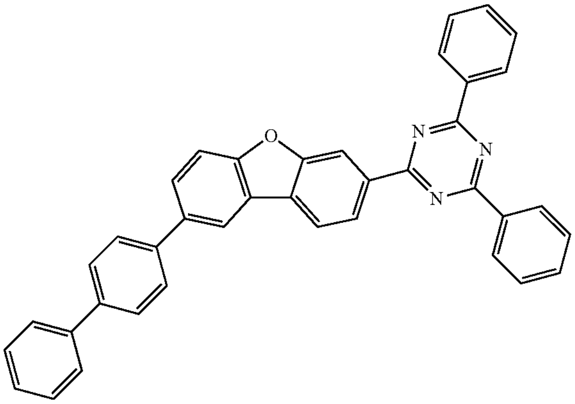
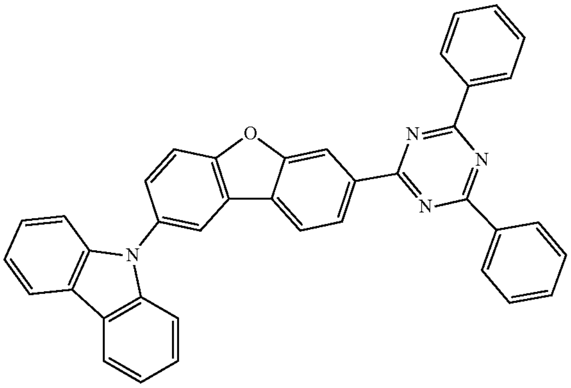
-continued
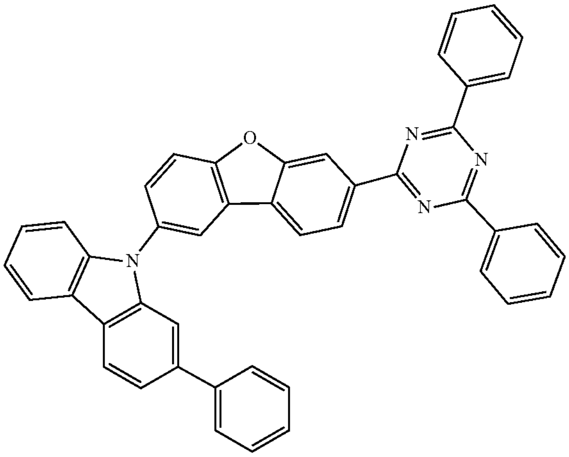
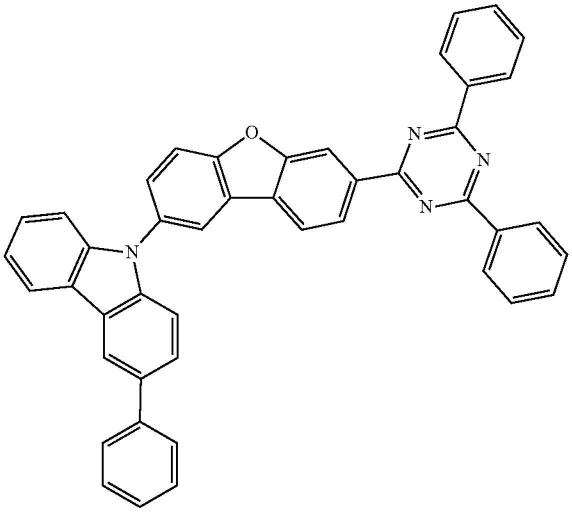
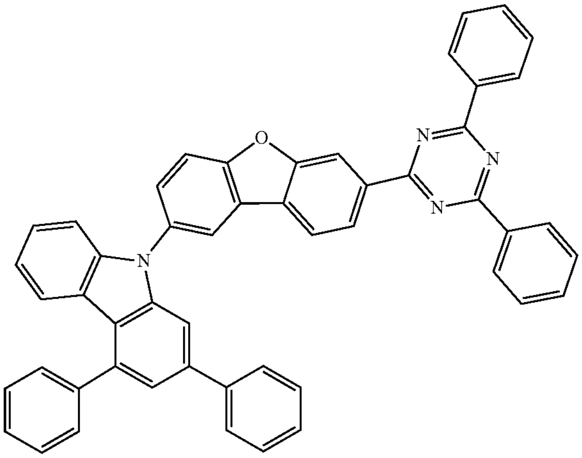

-continued
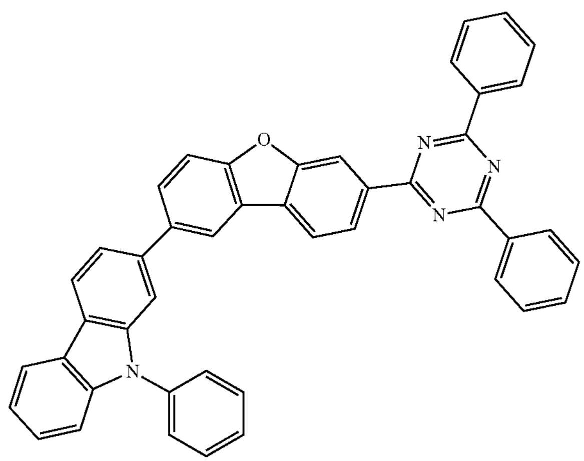
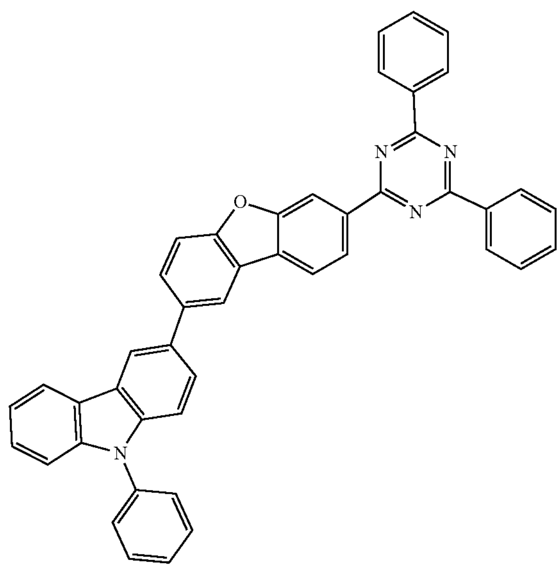
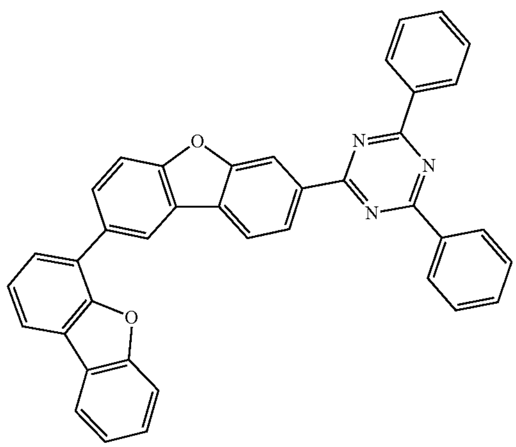
-continued
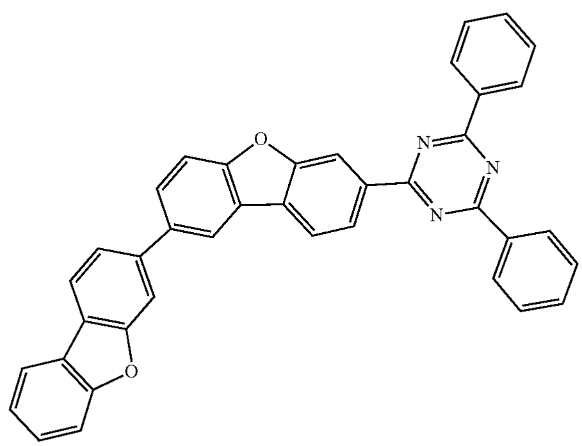
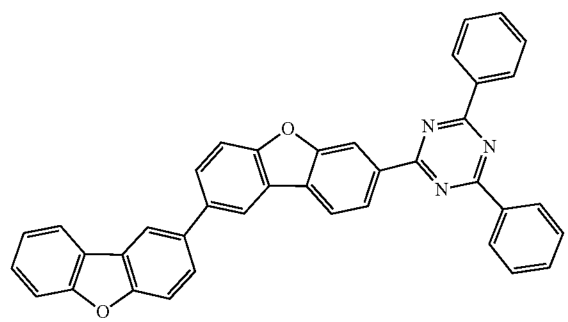
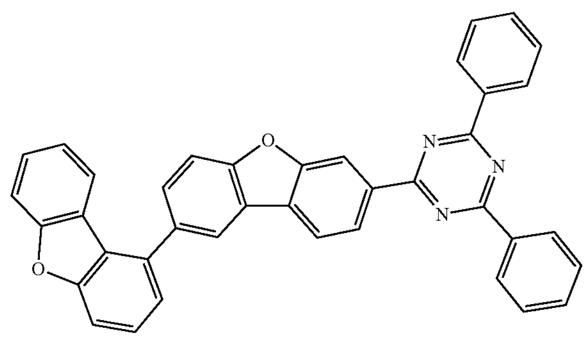
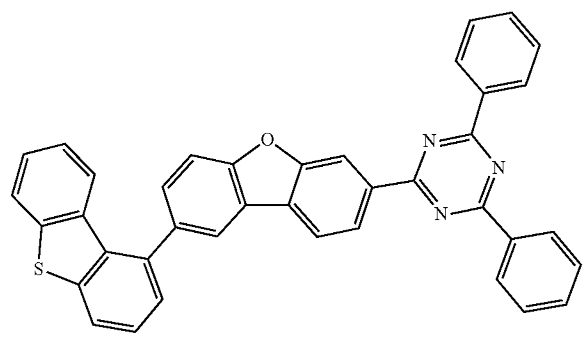

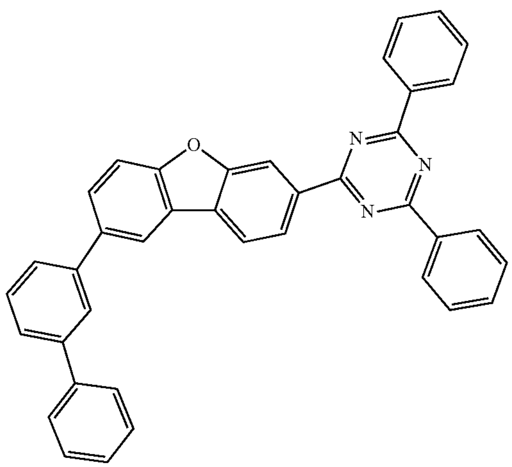
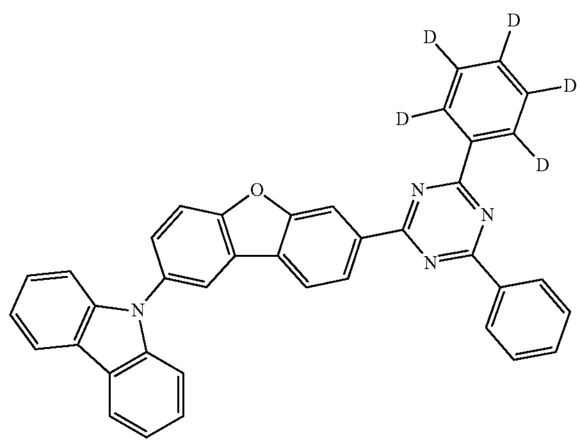
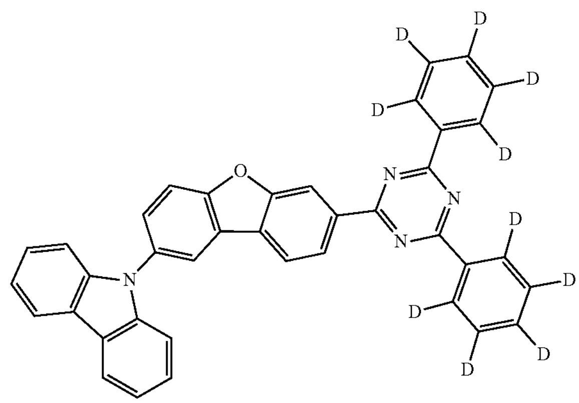
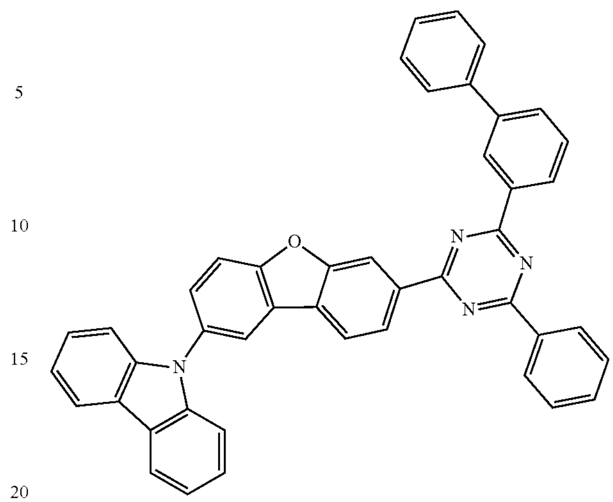
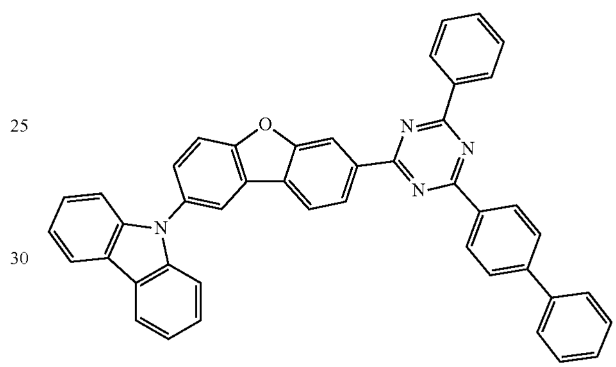
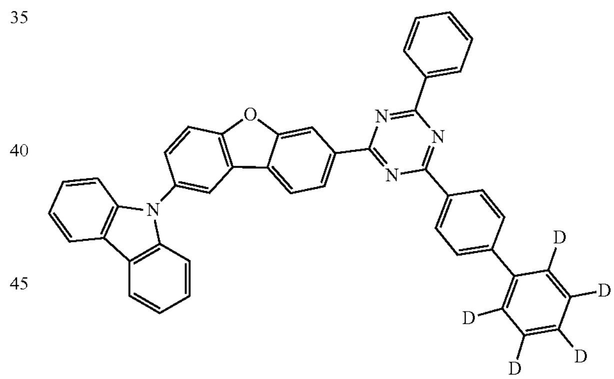
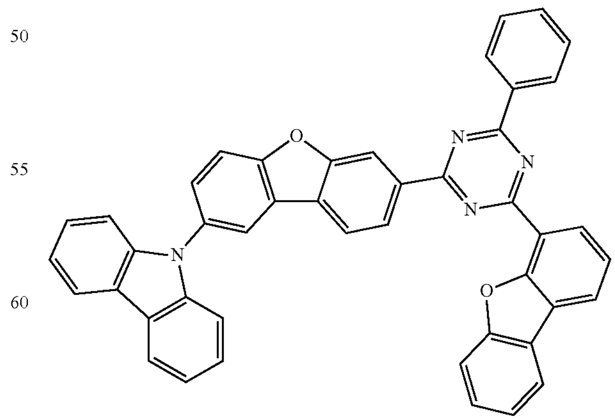

-continued
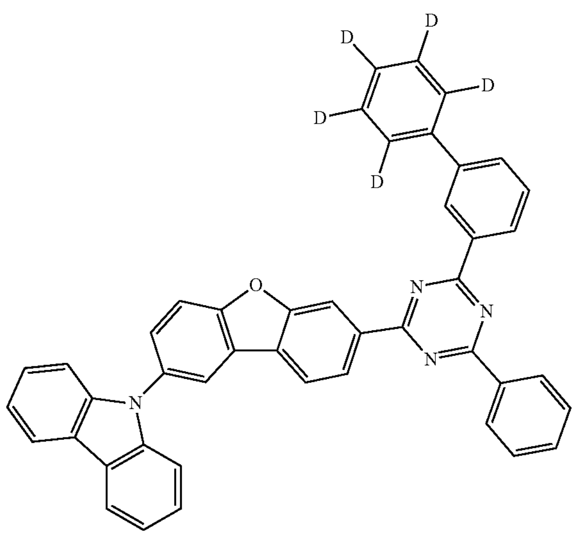
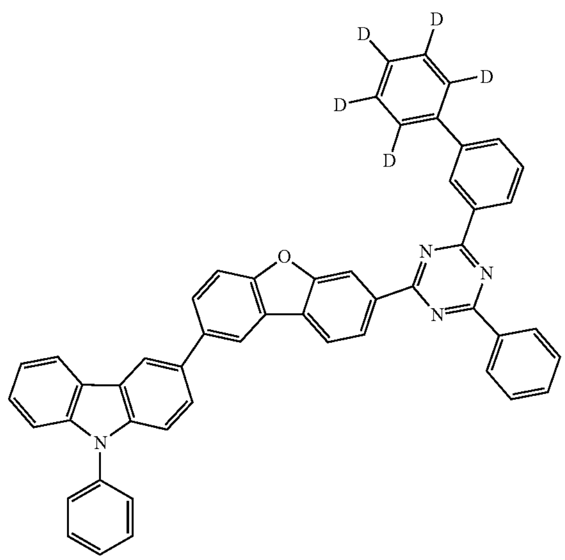
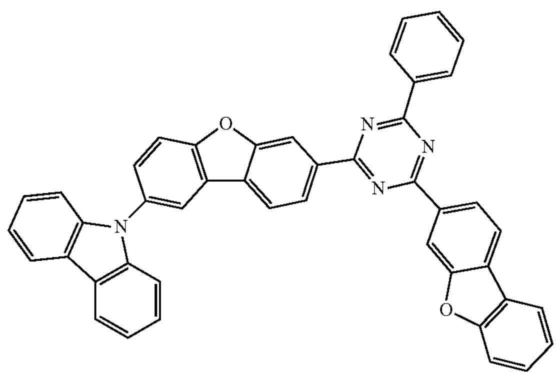
-continued
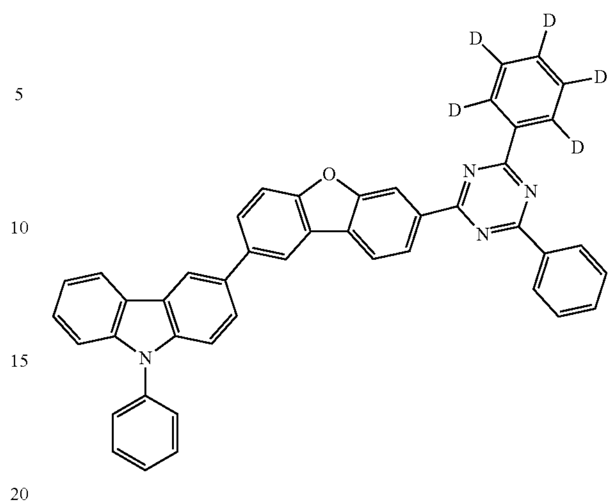
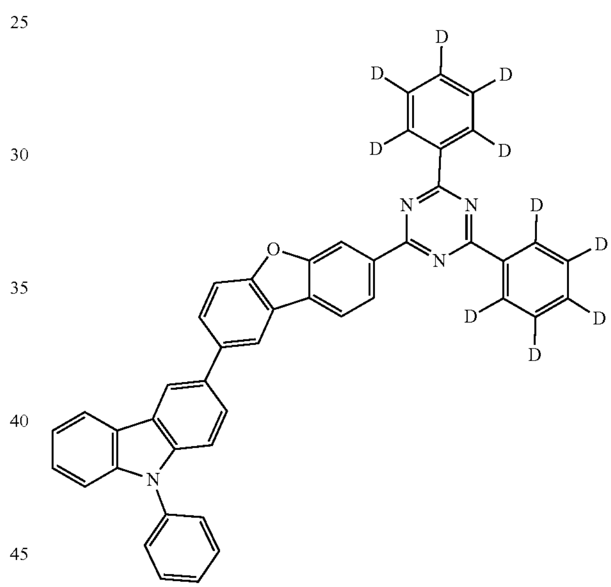
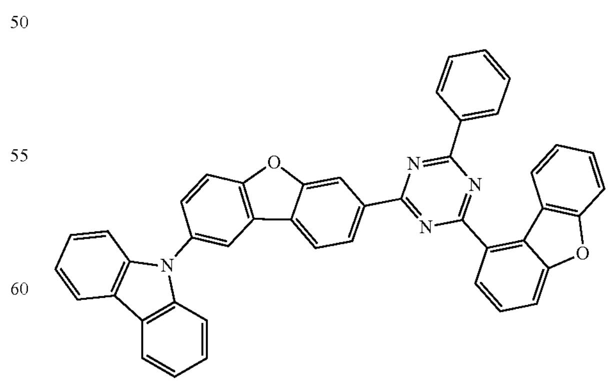

-continued
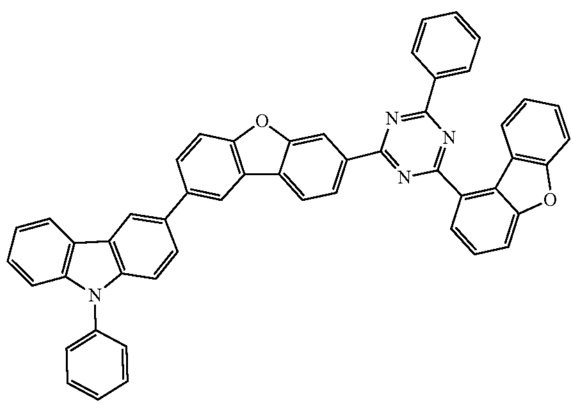
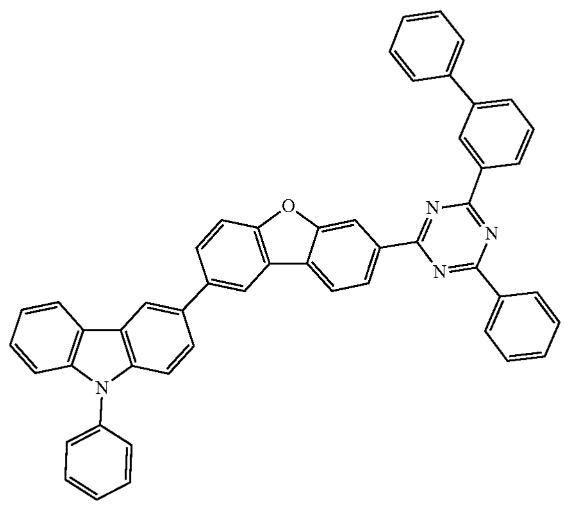
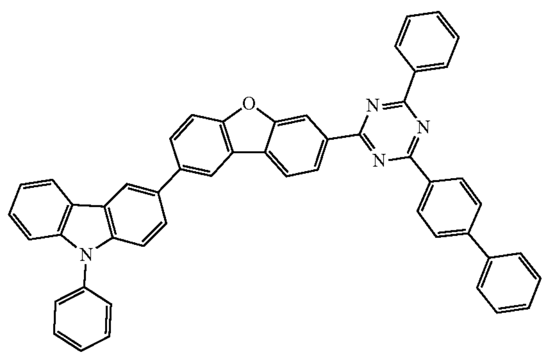
-continued
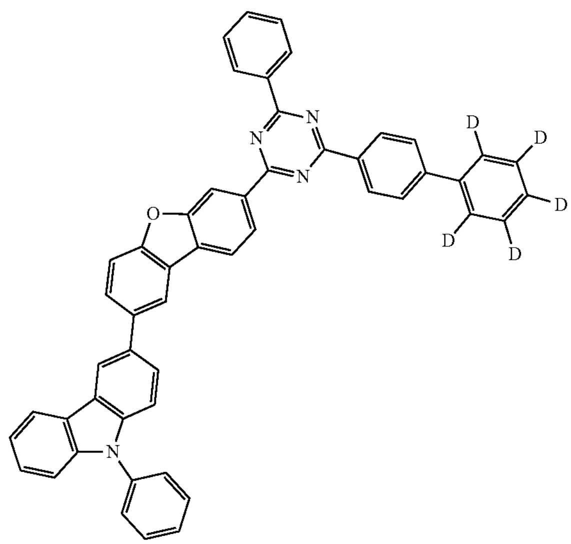
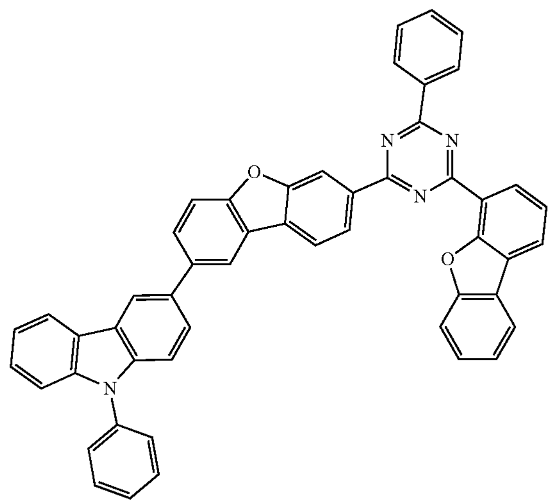
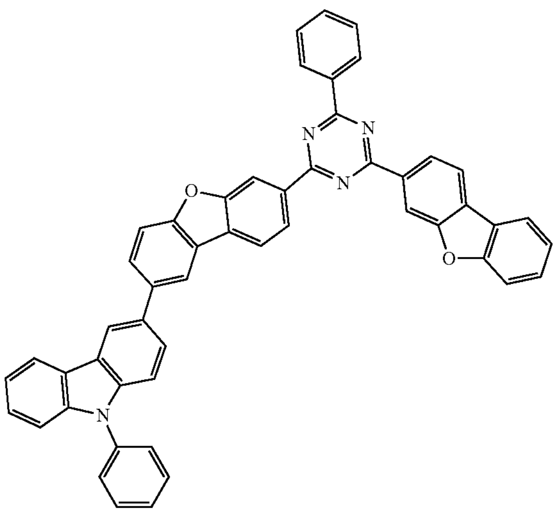

-continued
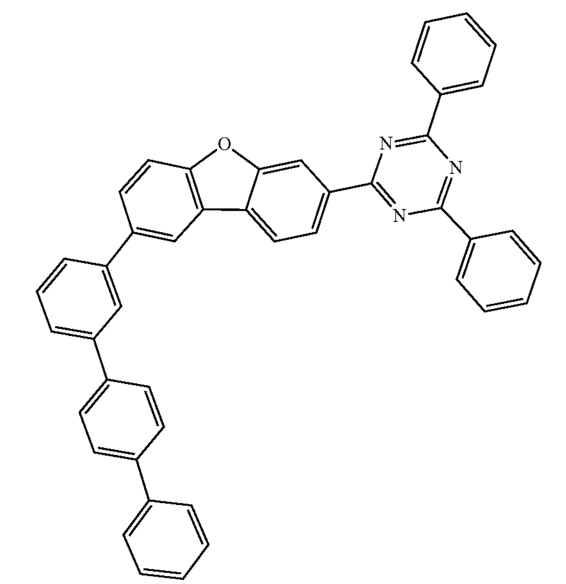
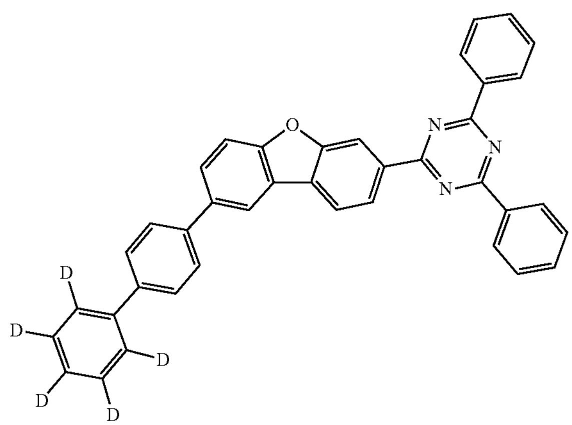
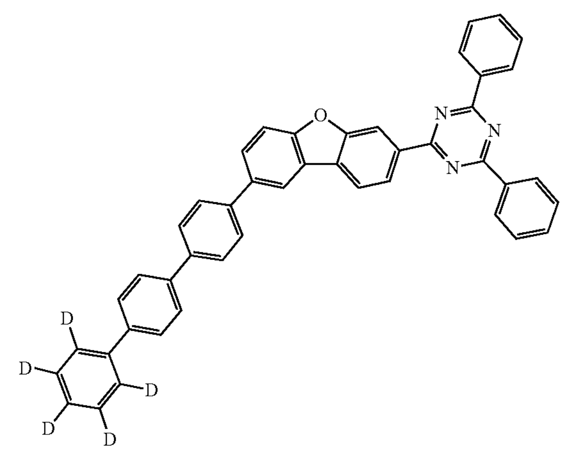
-continued
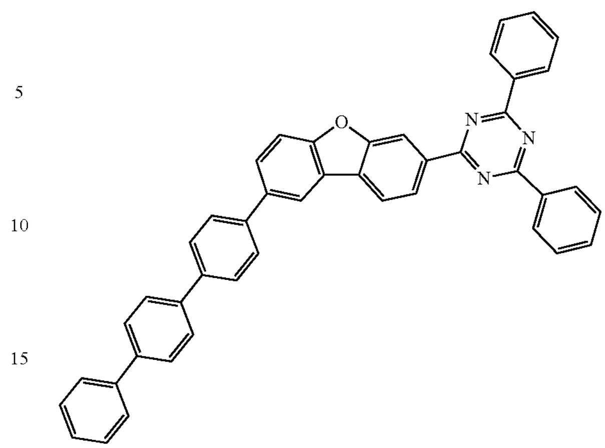
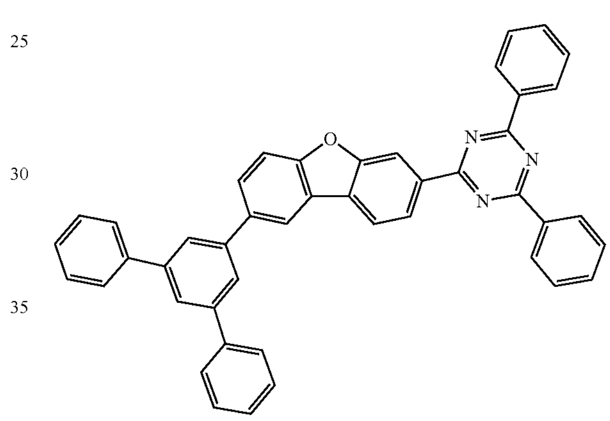
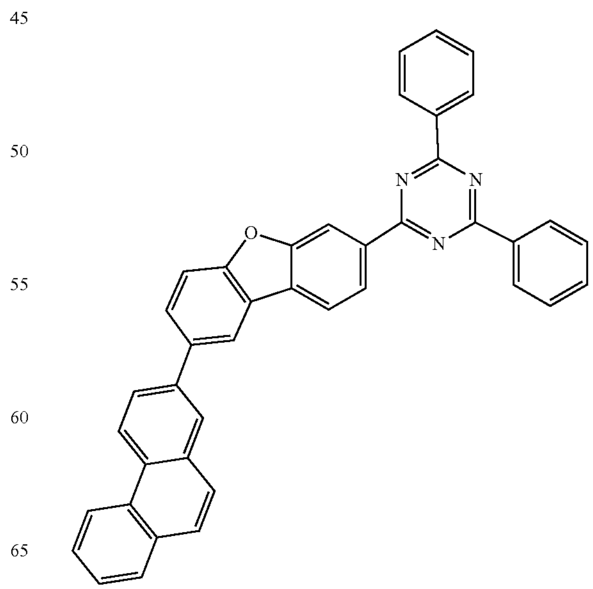

-continued
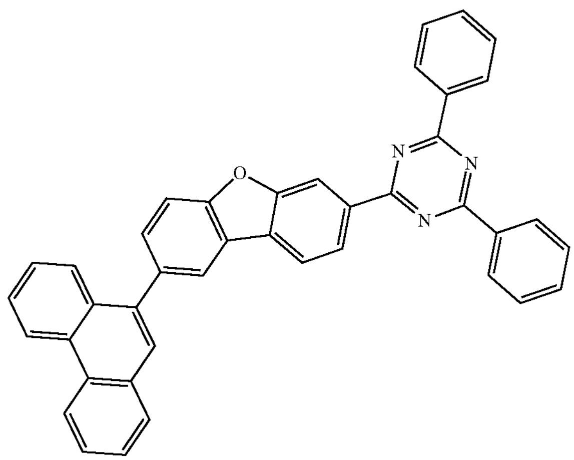
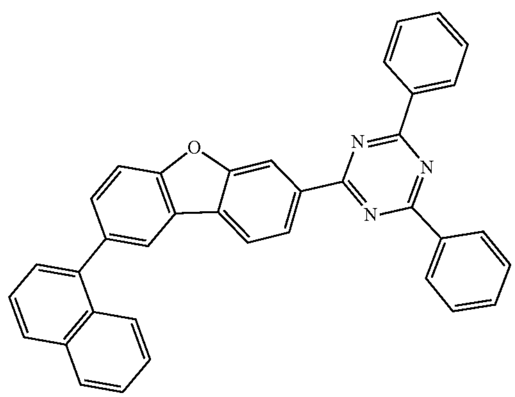
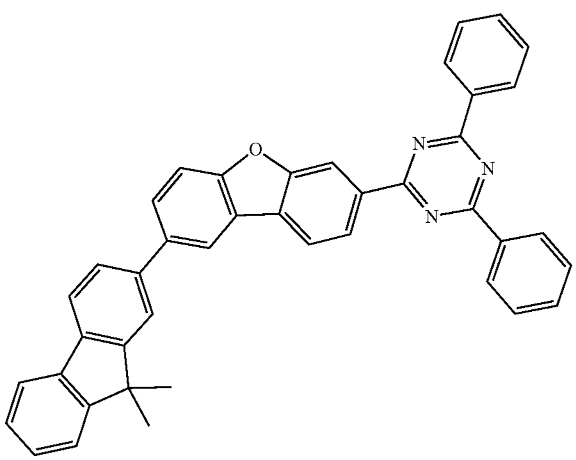
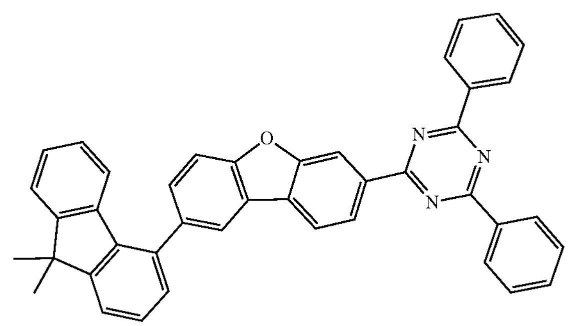
-continued
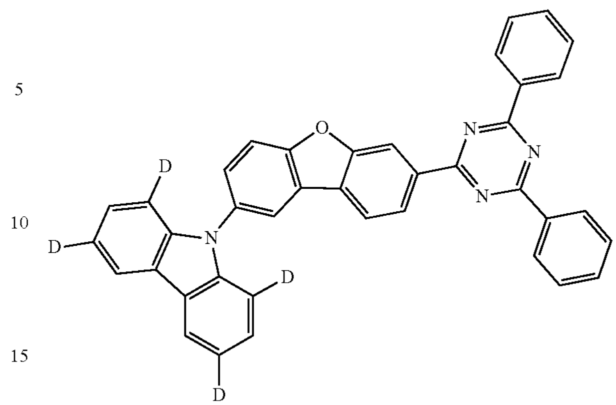
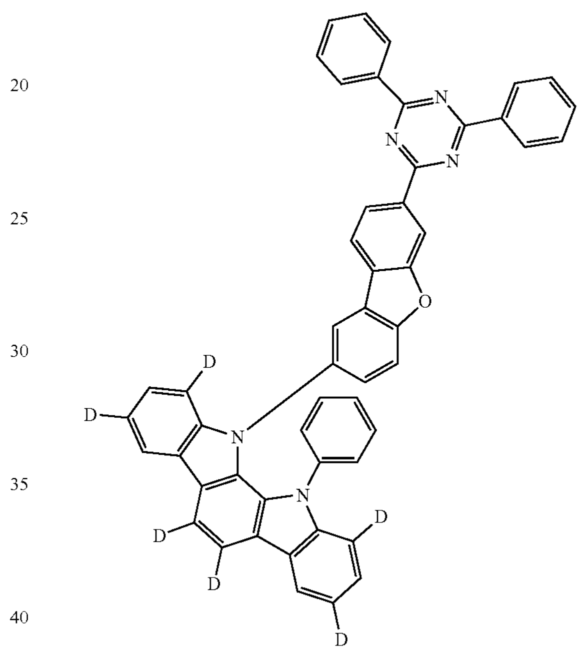
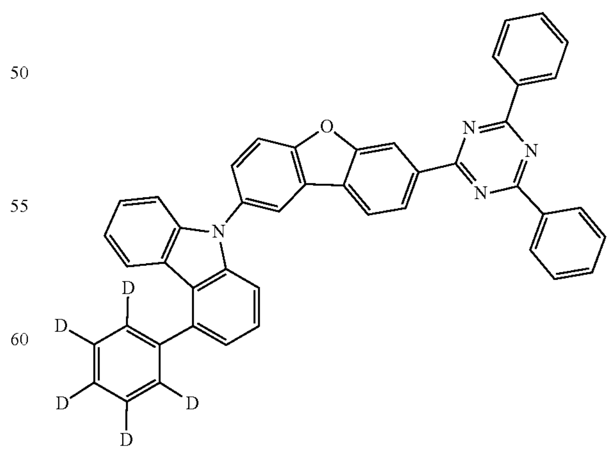

-continued
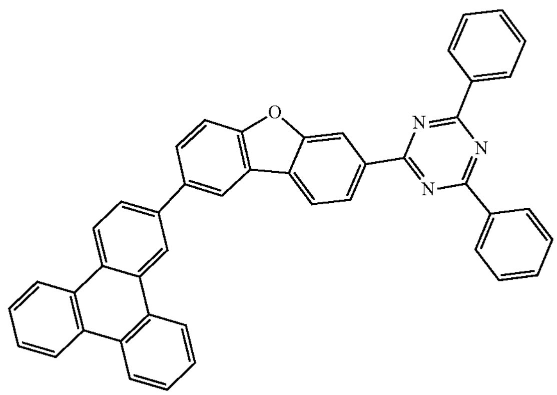
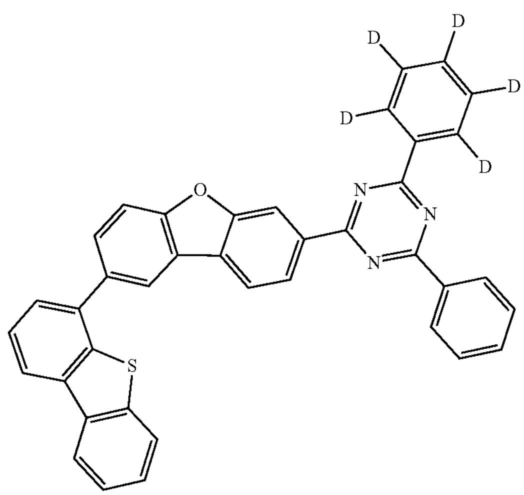
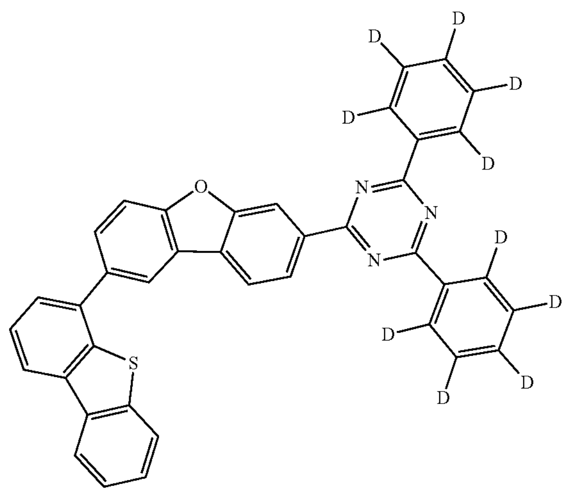
-continued
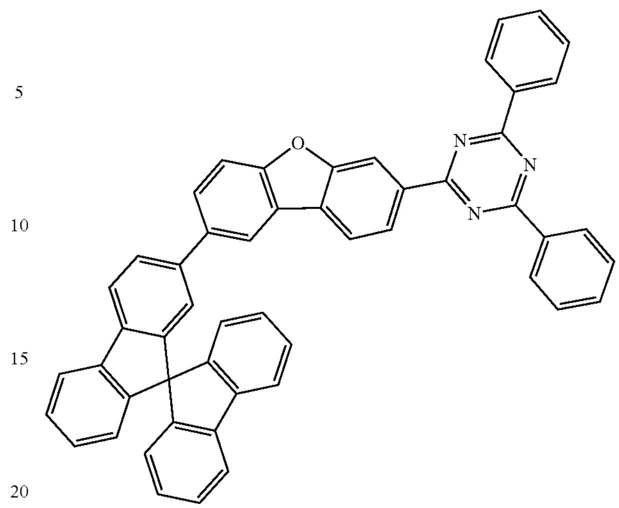
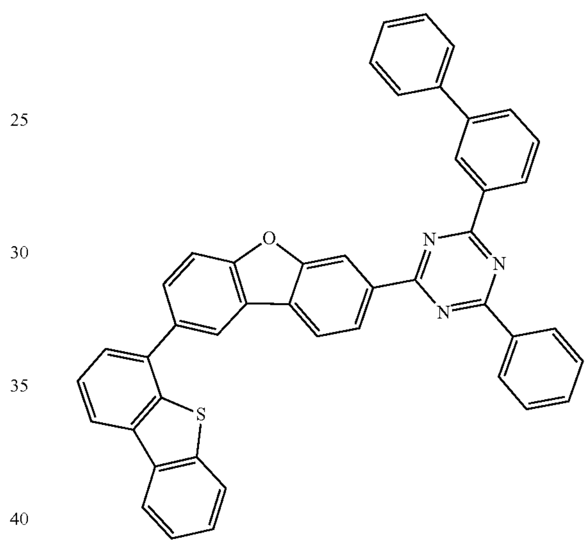
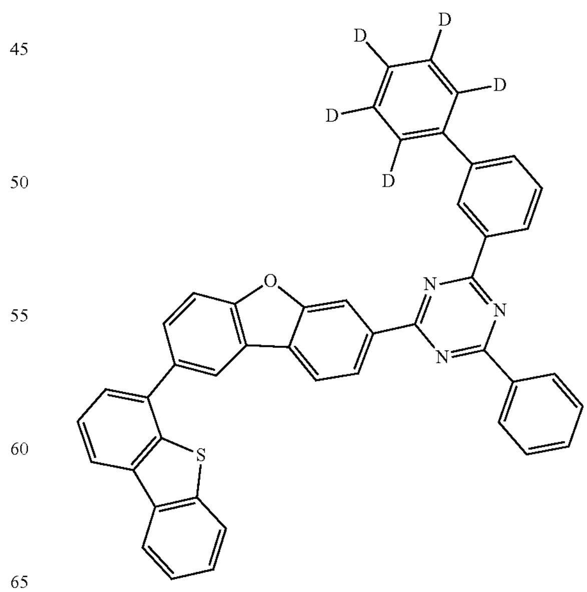

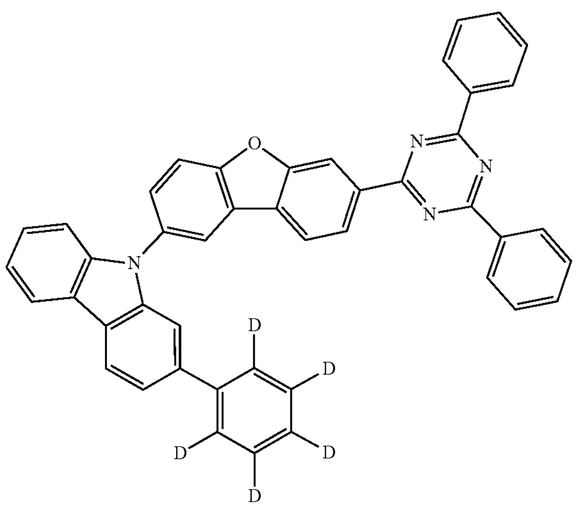
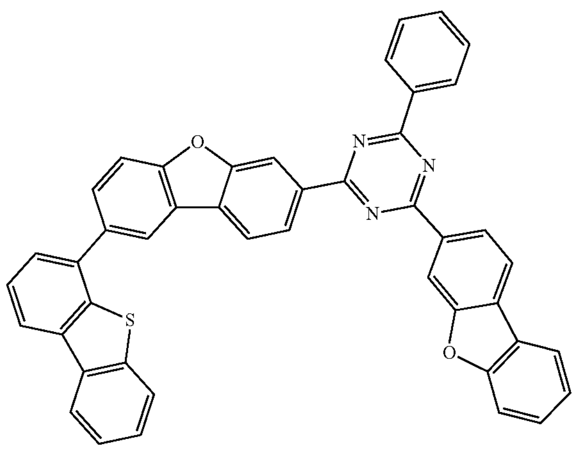
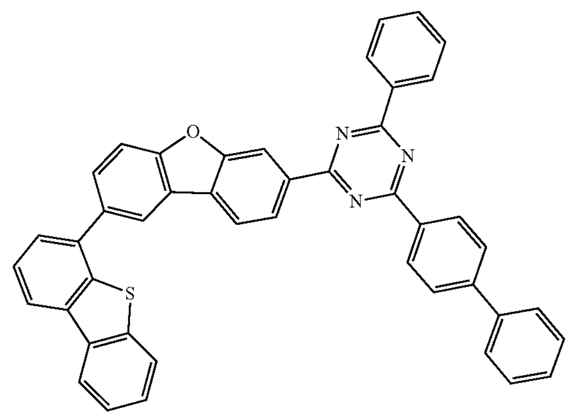
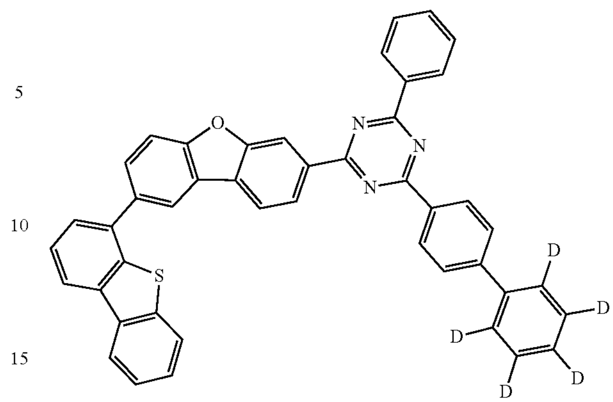
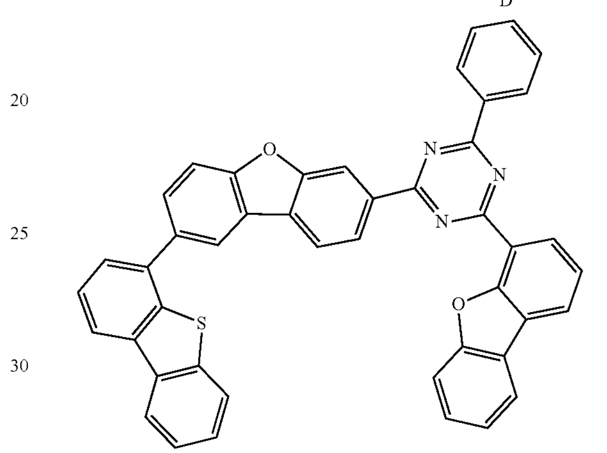
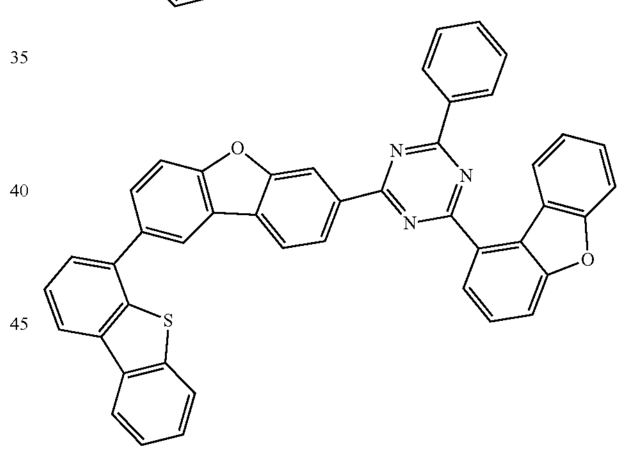
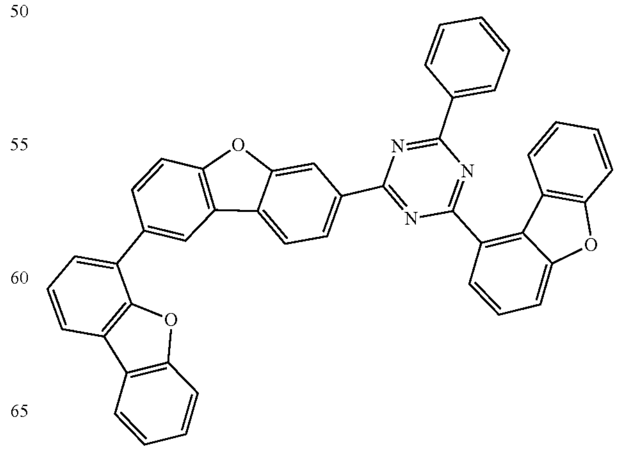

-continued
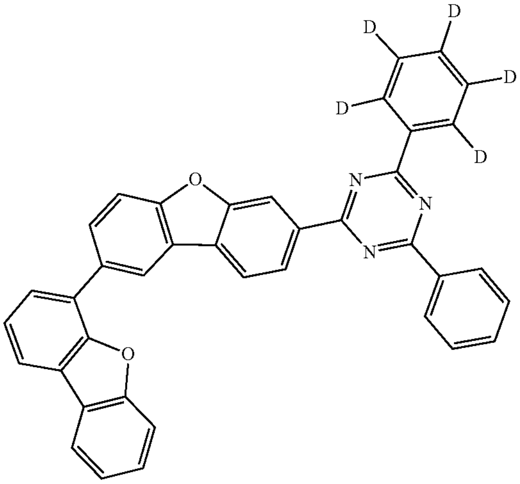
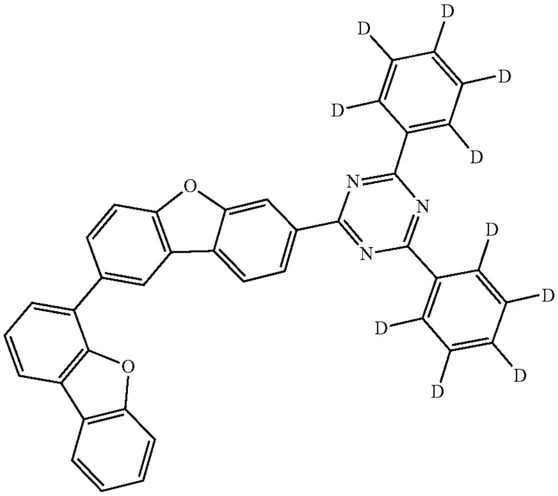
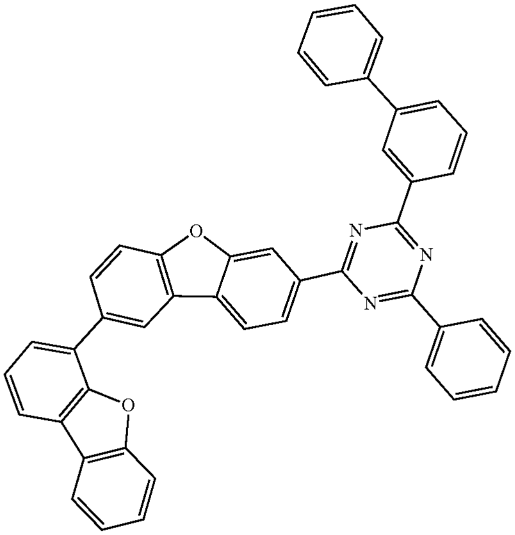
-continued
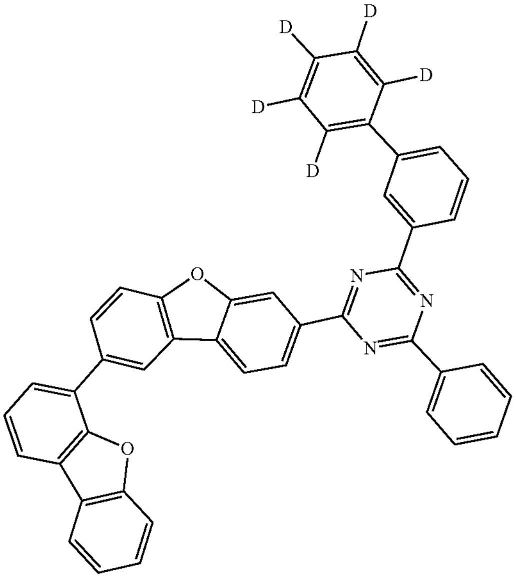
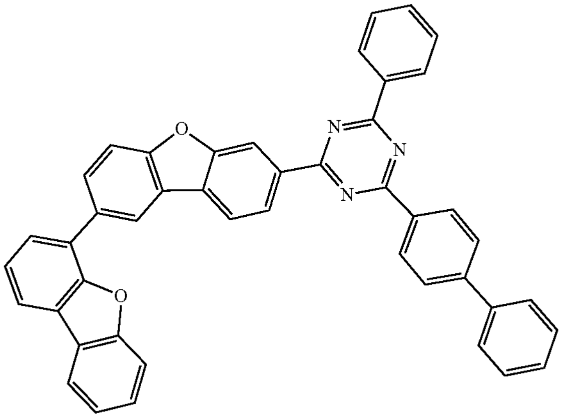
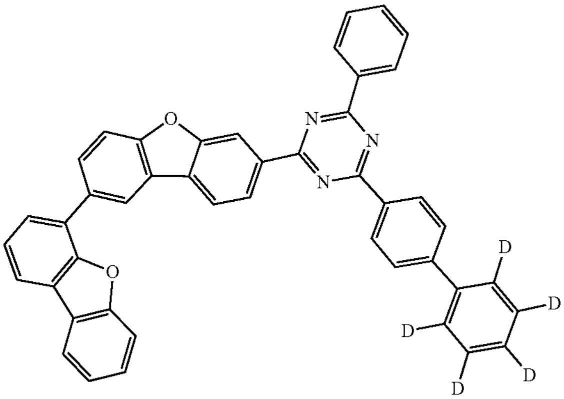

-continued
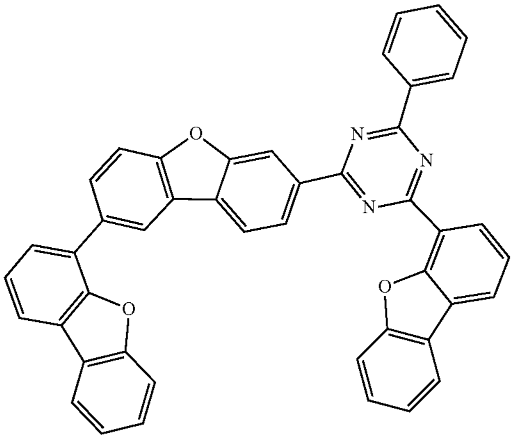
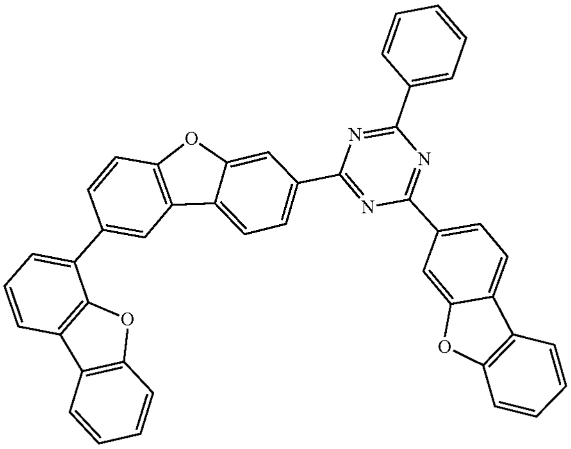
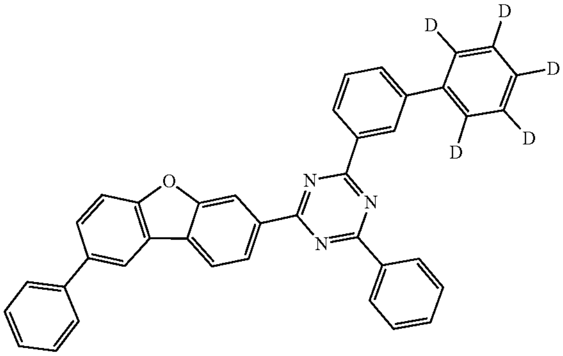
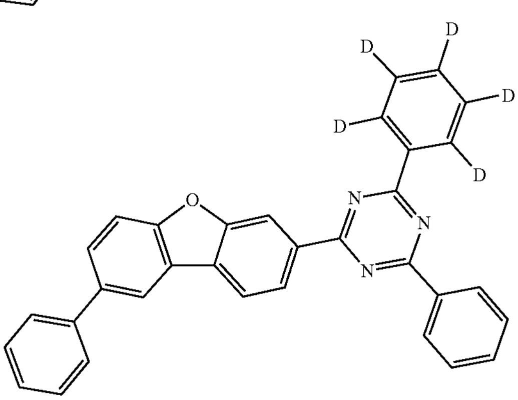
-continued
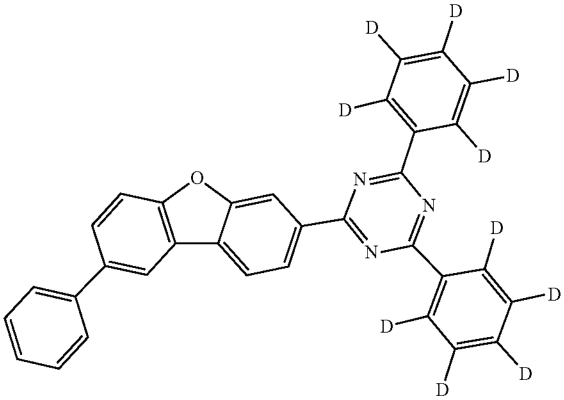
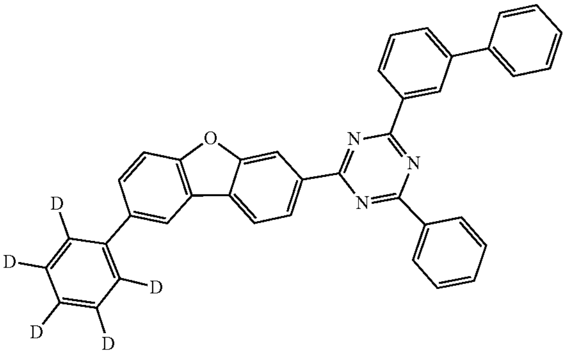
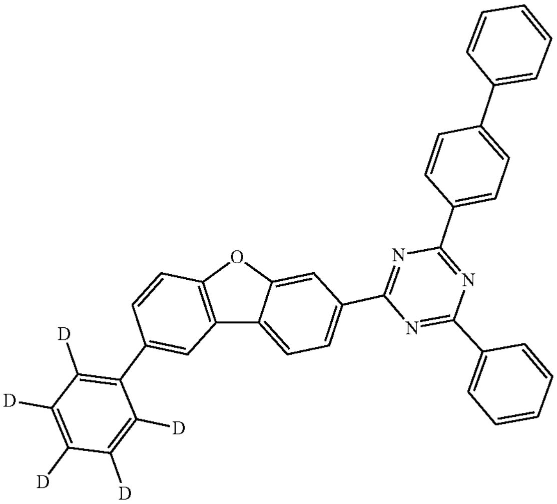

-continued
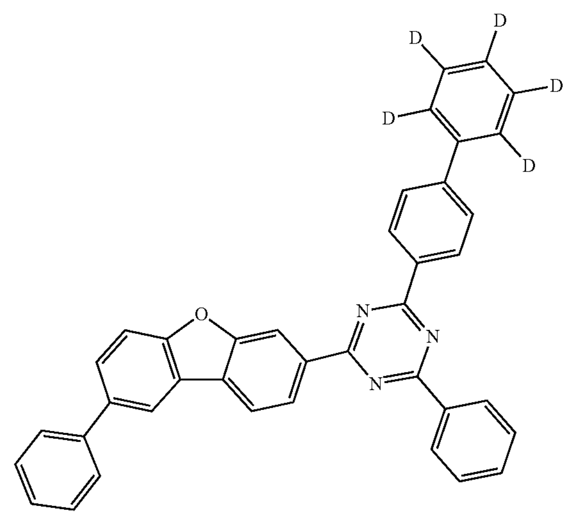
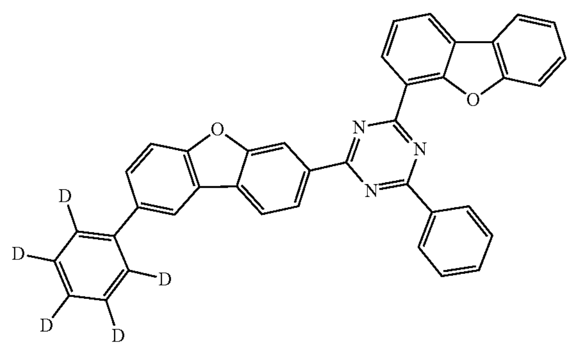
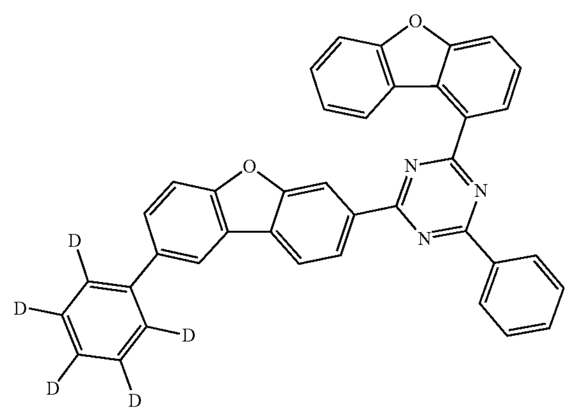
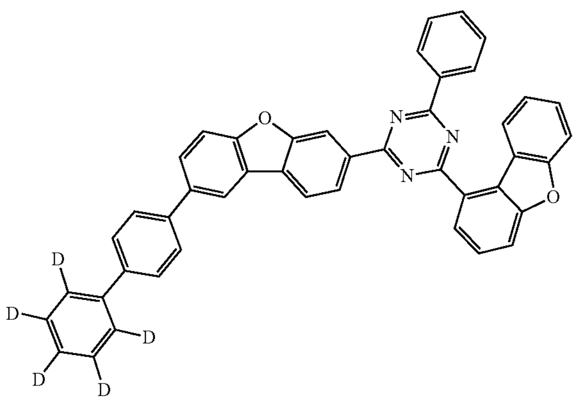
-continued
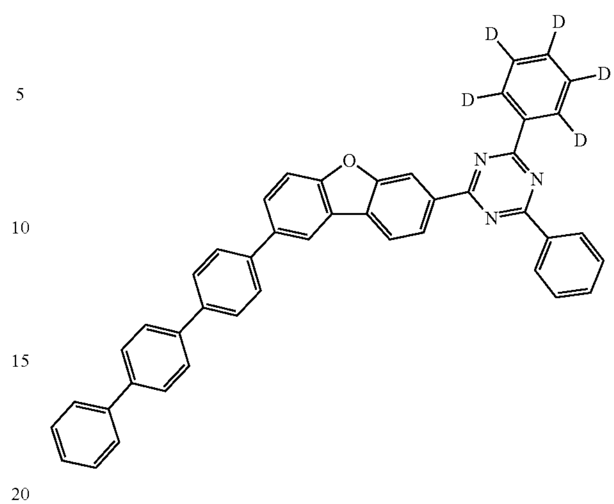
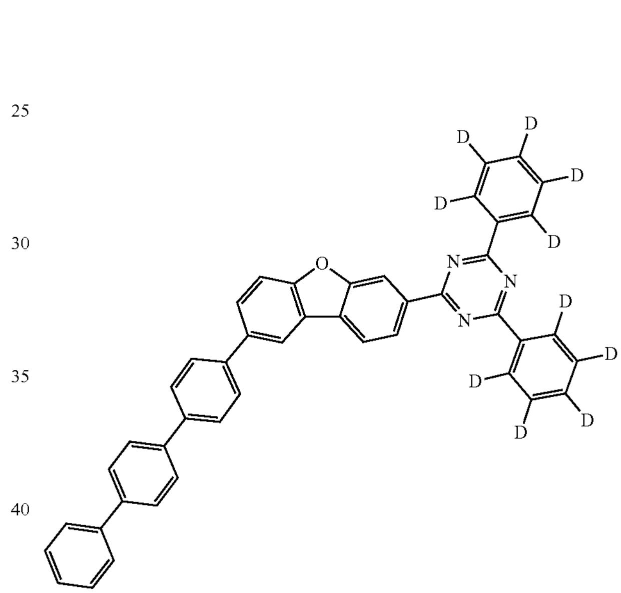
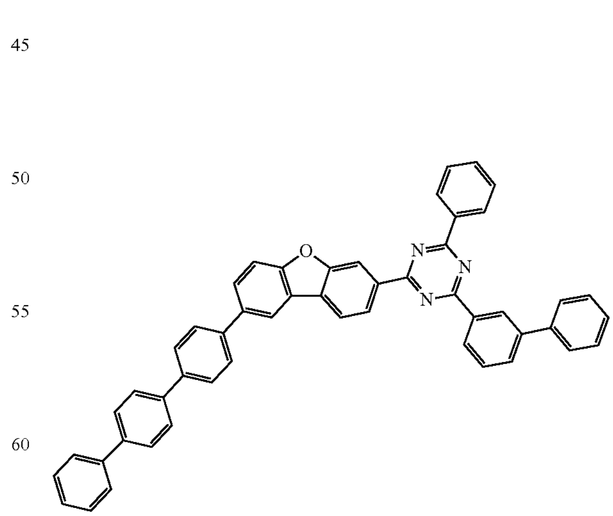

-continued
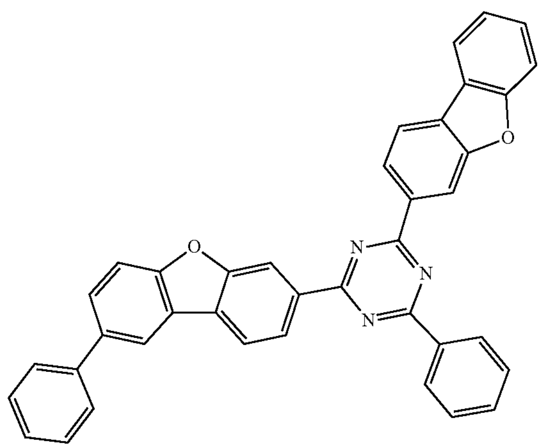
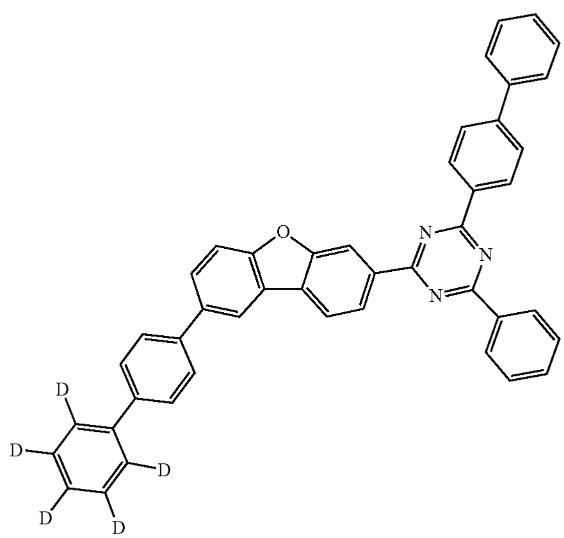
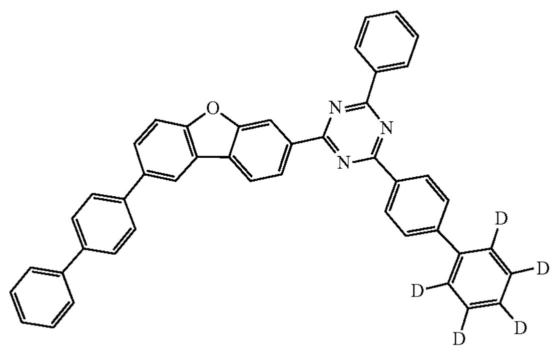
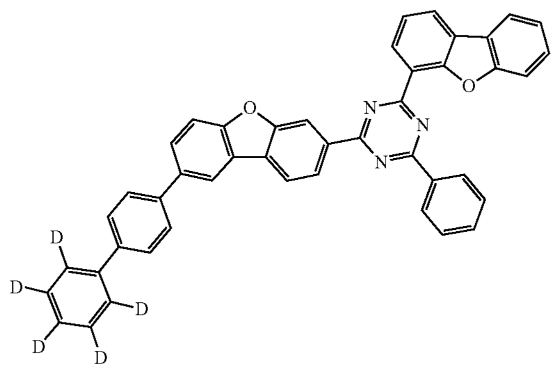
-continued
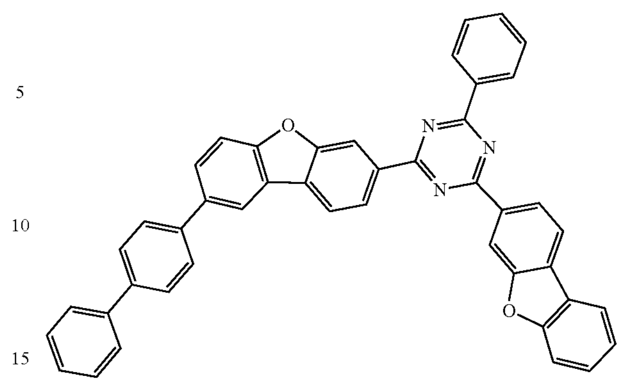
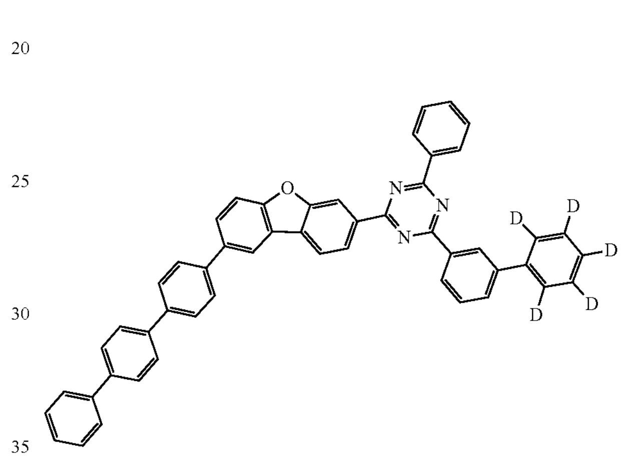
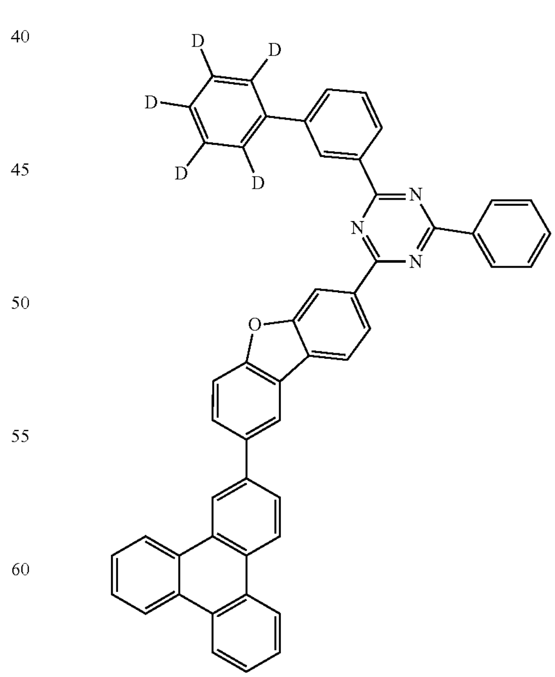

-continued
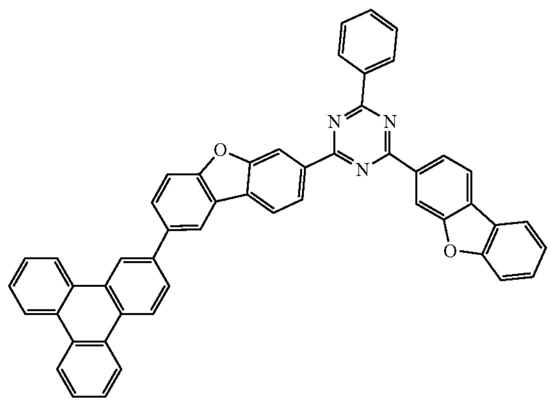
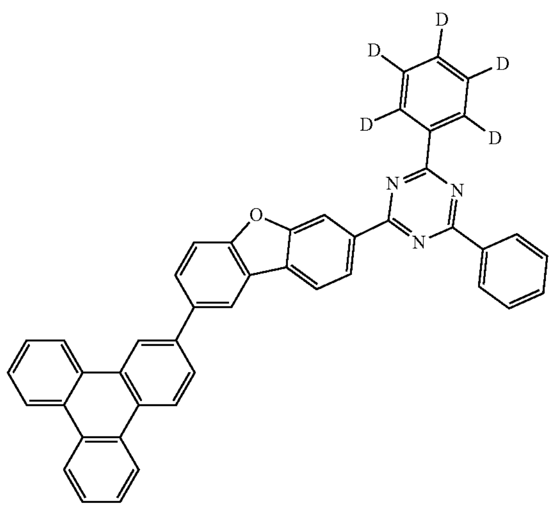
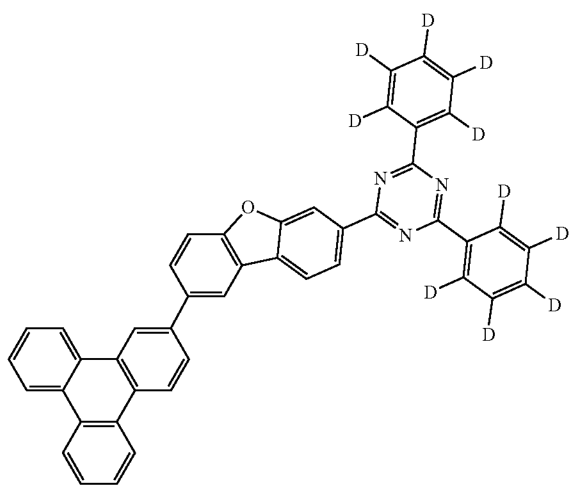
-continued
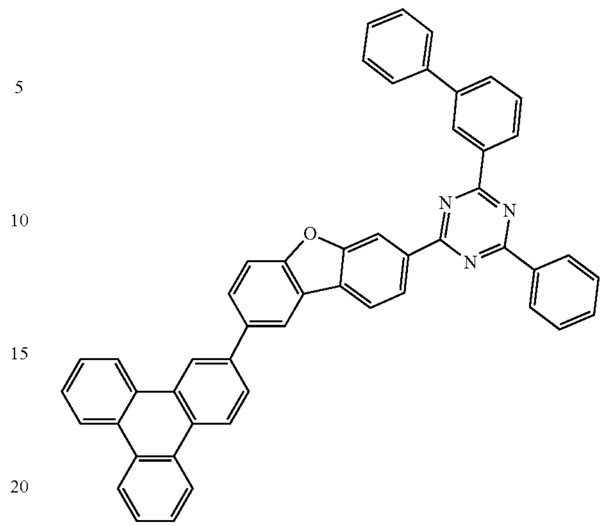
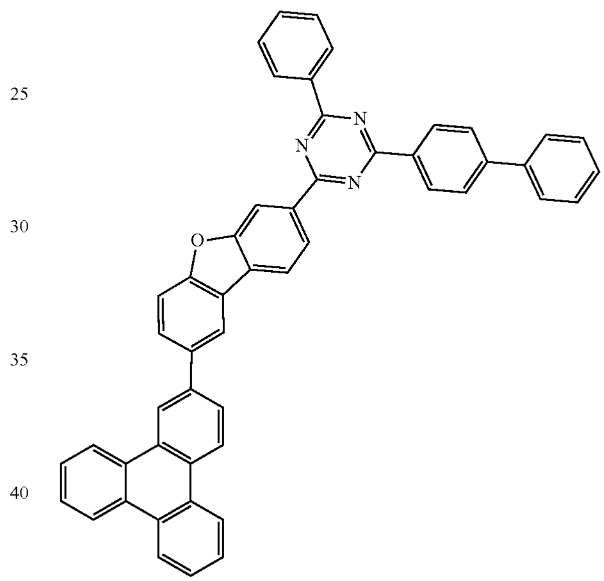
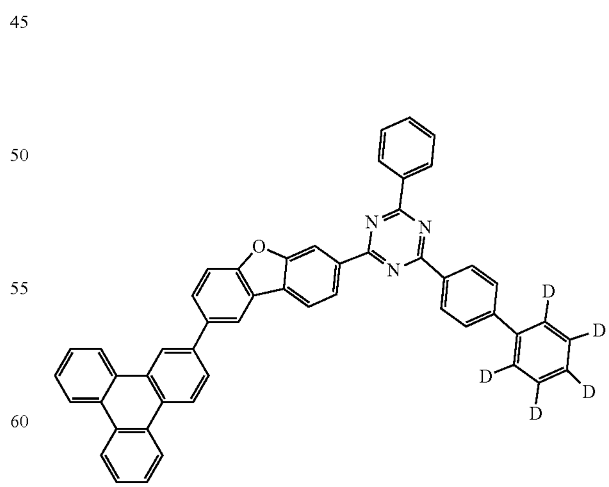

-continued
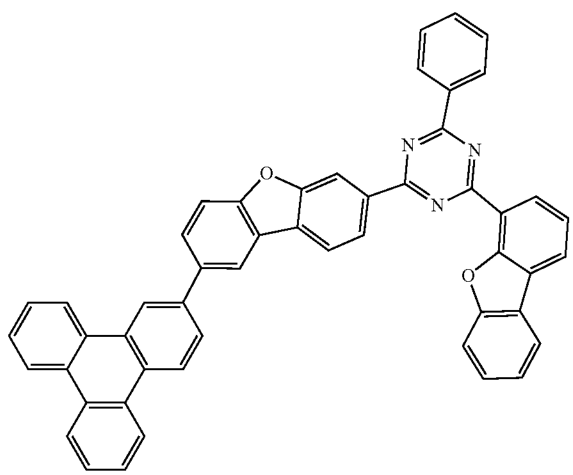
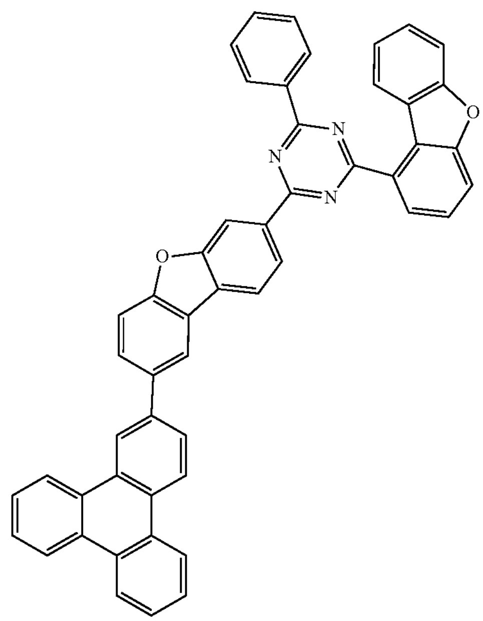
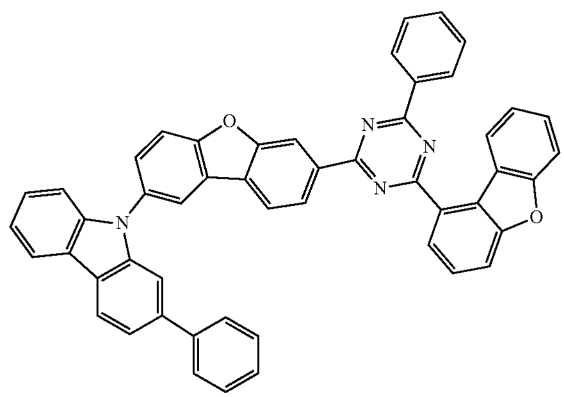
-continued
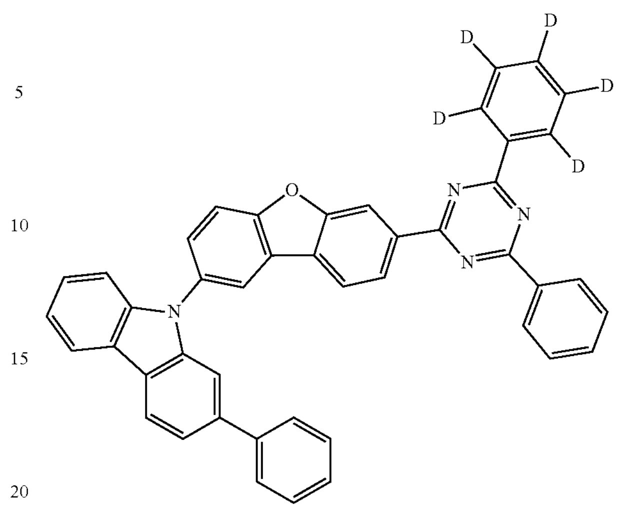
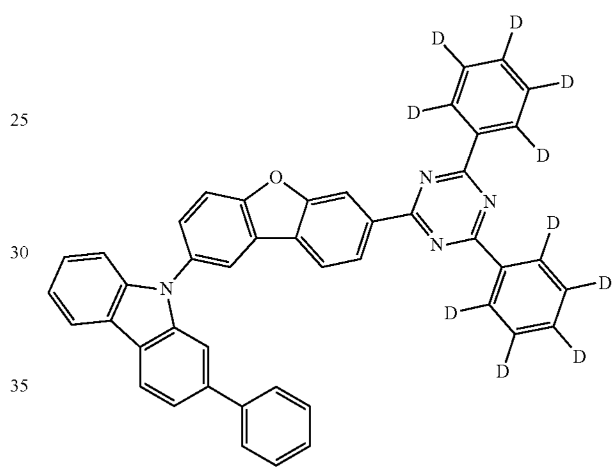
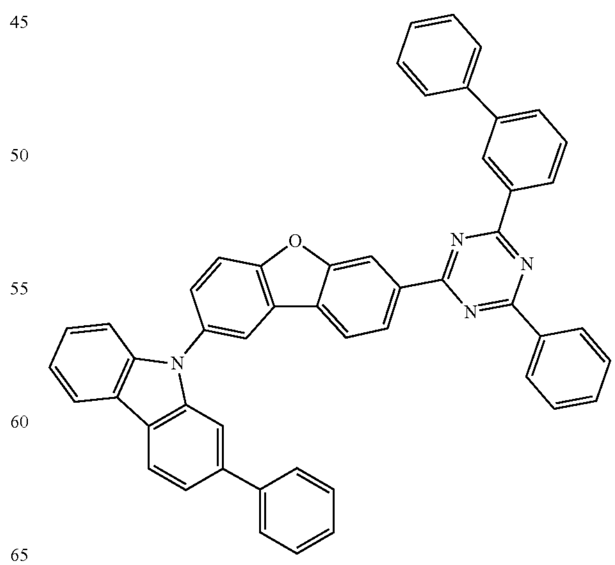

-continued
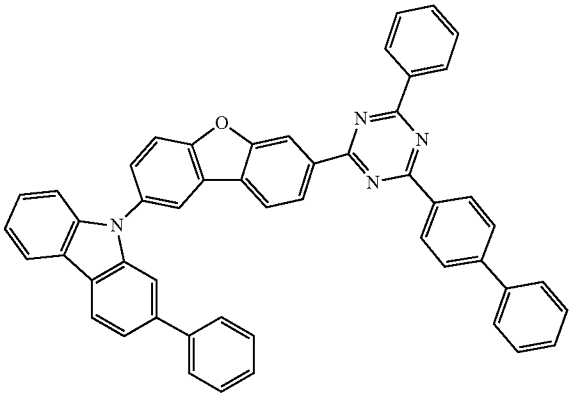
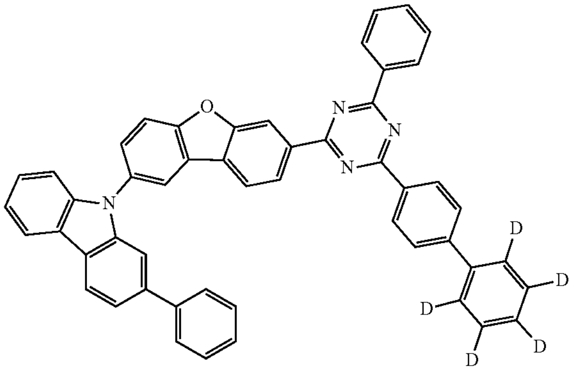
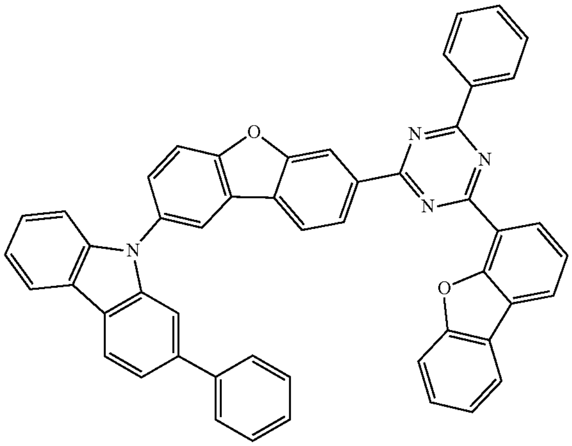
-continued
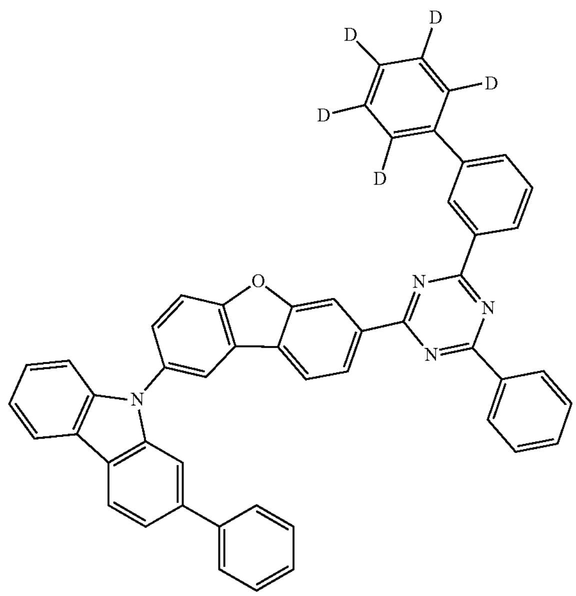
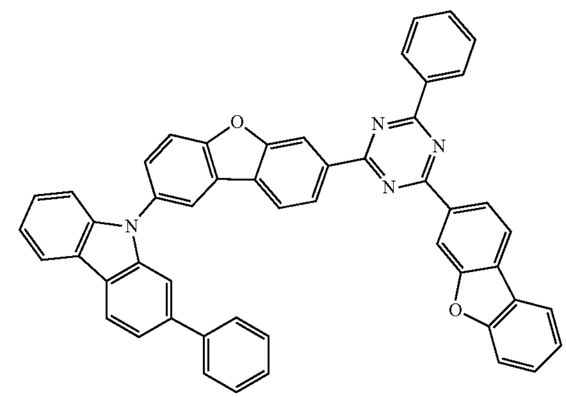
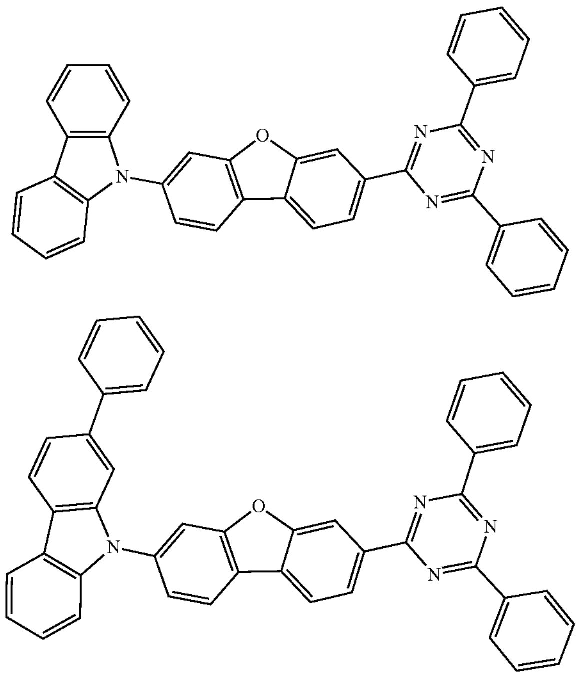

-continued
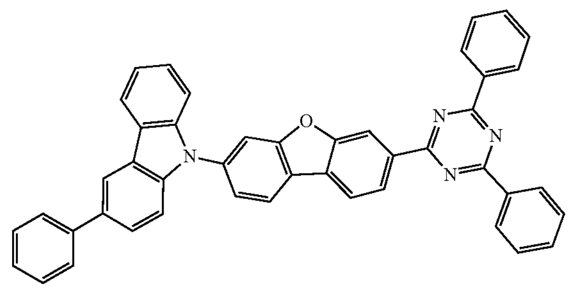
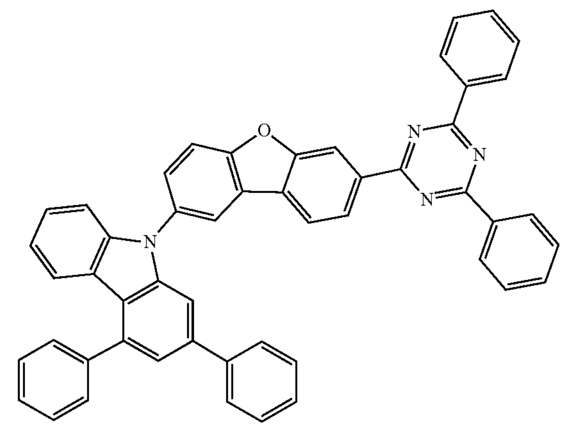
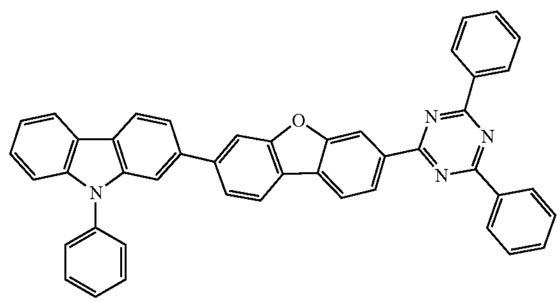
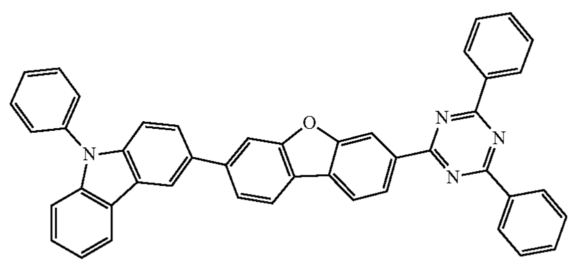
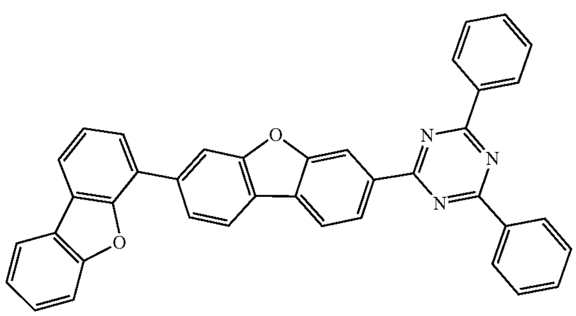
-continued
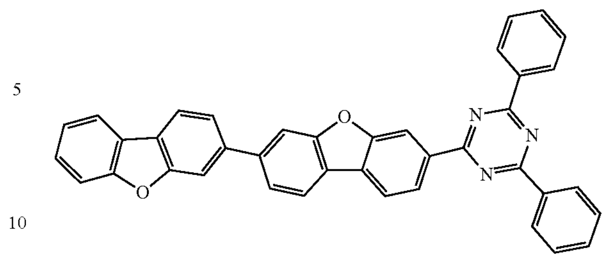
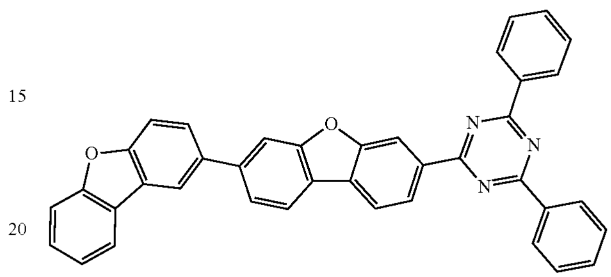
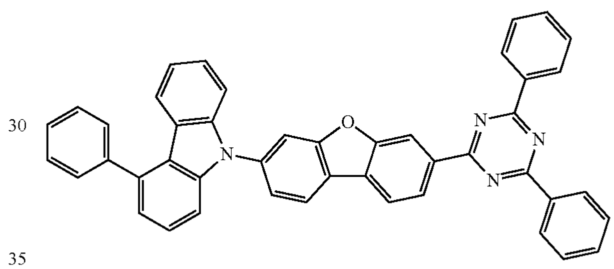
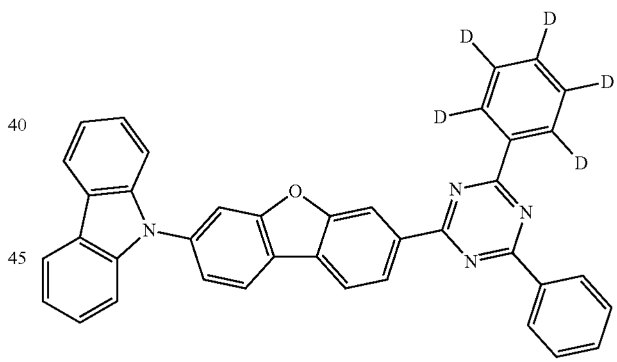
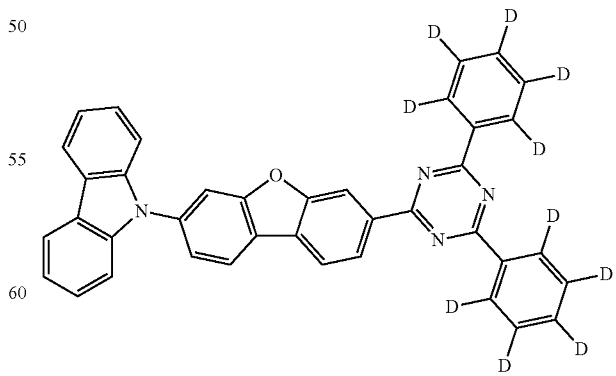

-continued
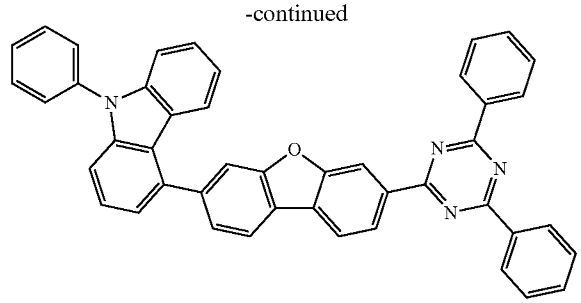
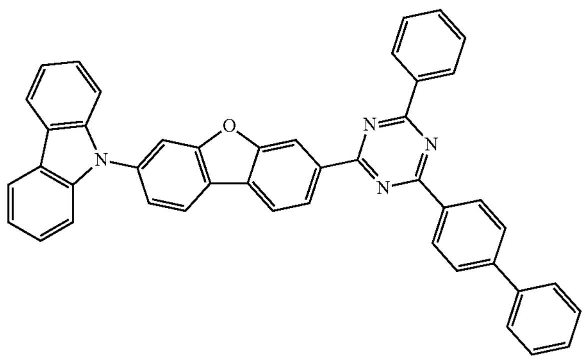
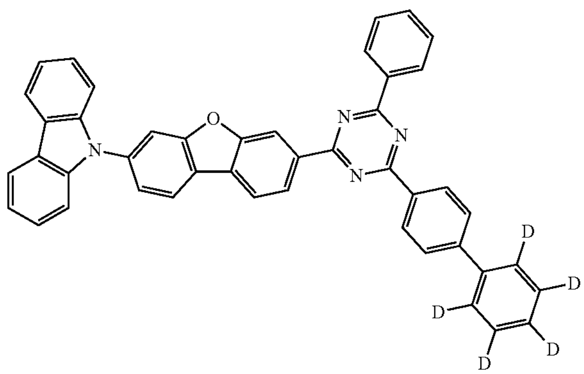
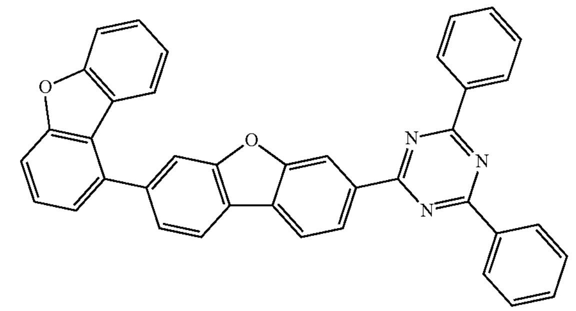
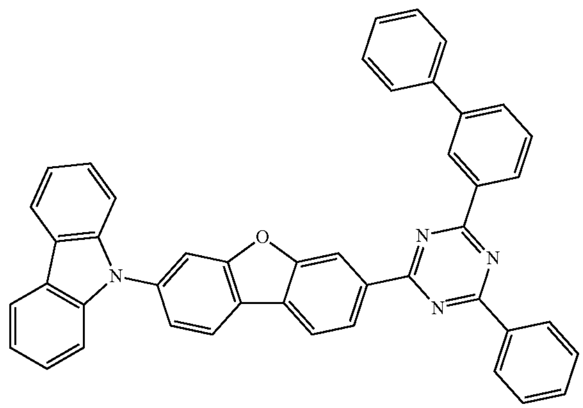
-continued
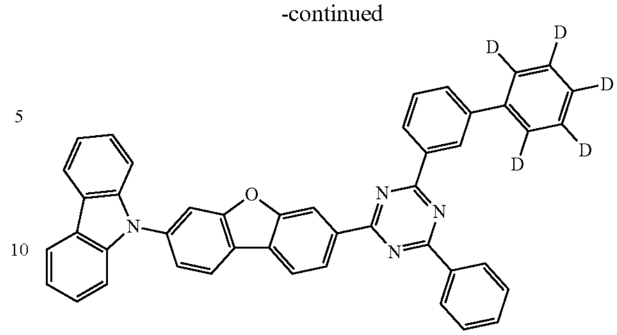
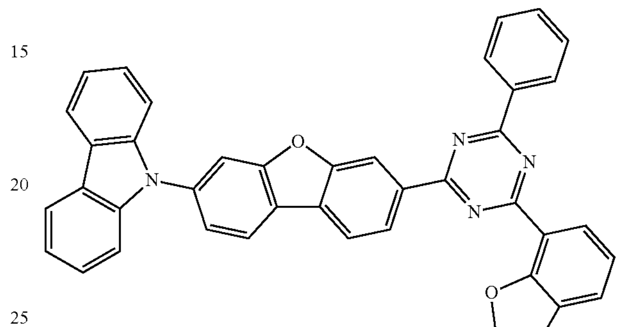
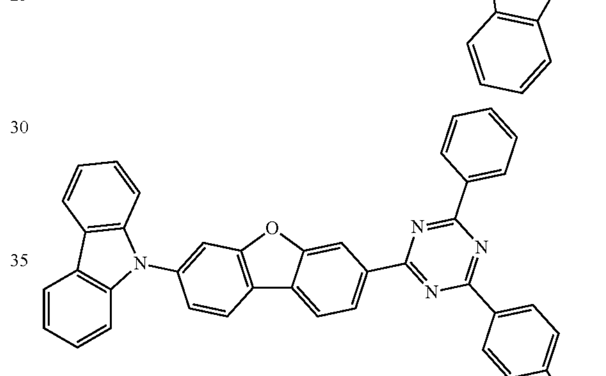
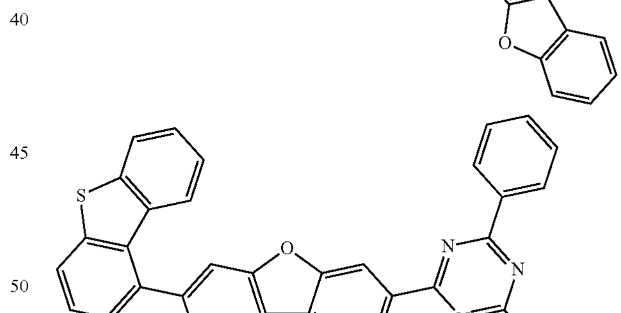
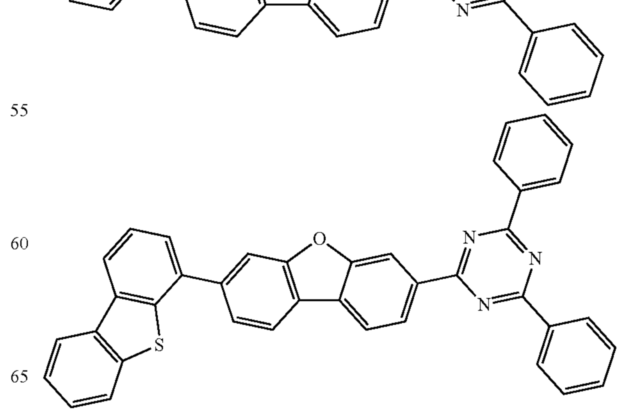

-continued
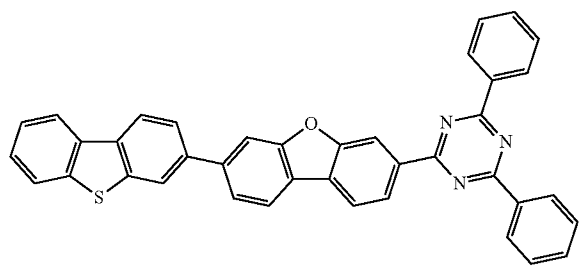
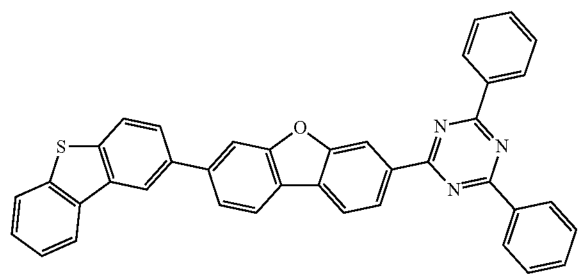
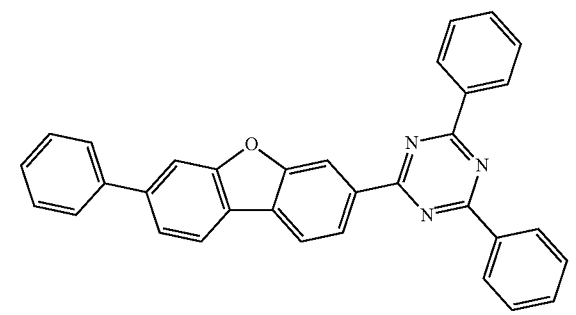
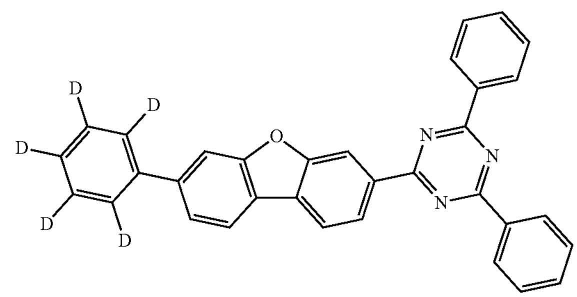
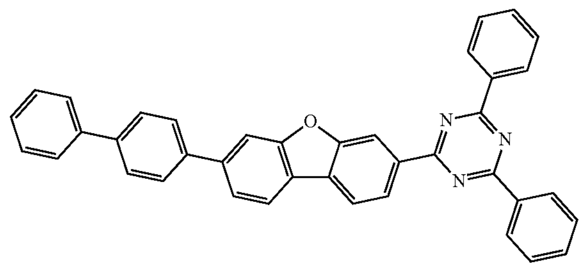
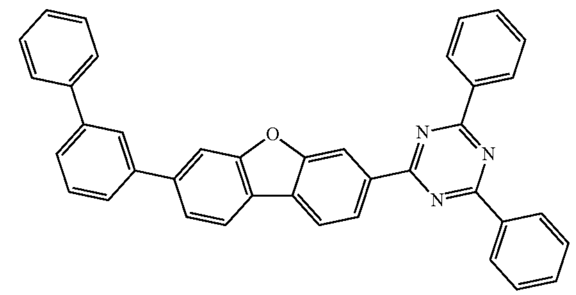
-continued
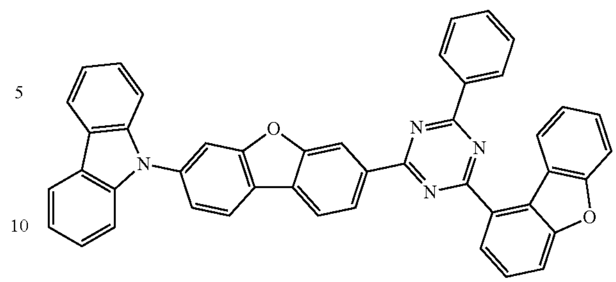
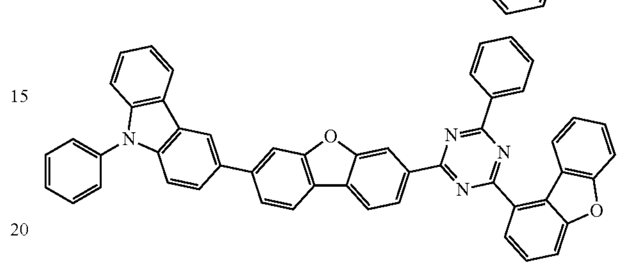
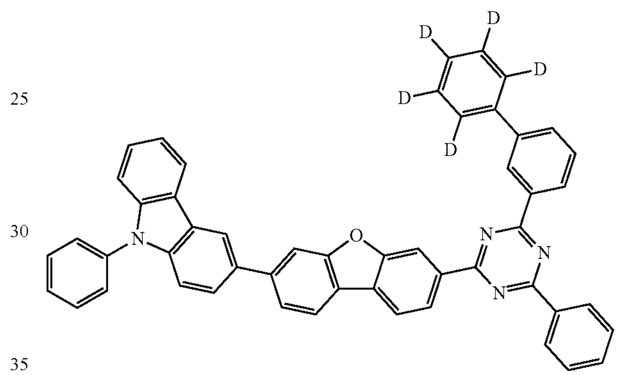
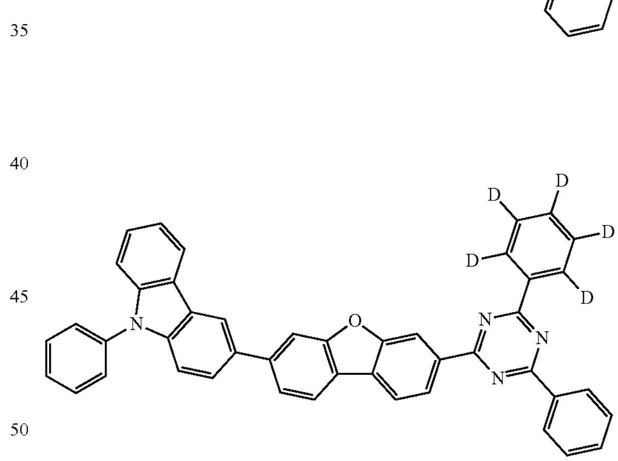
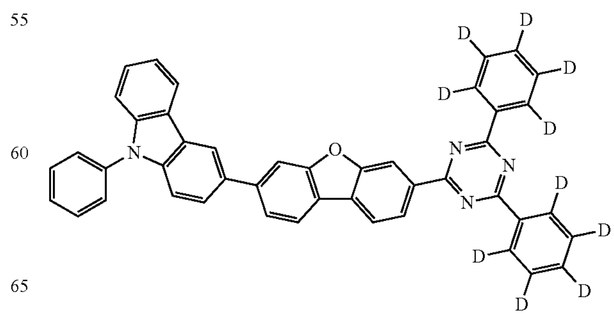

-continued
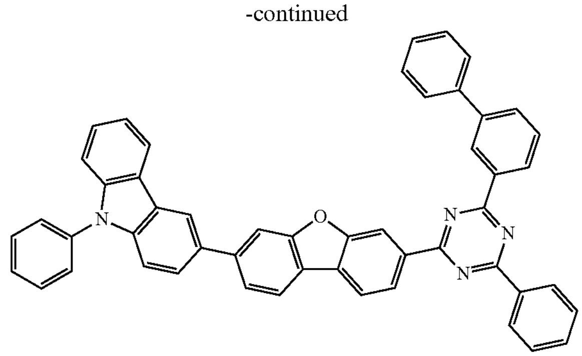
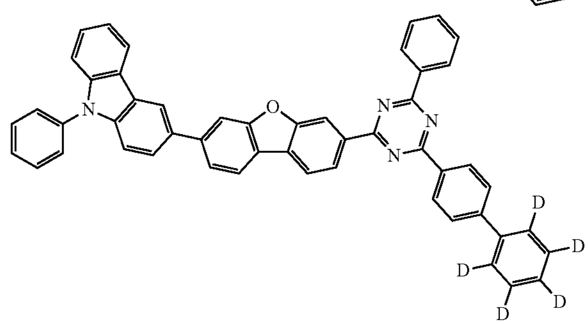
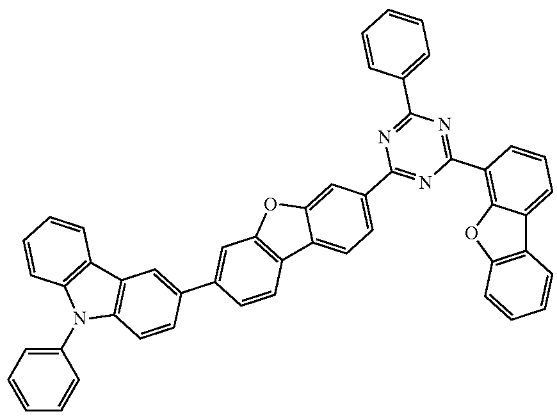
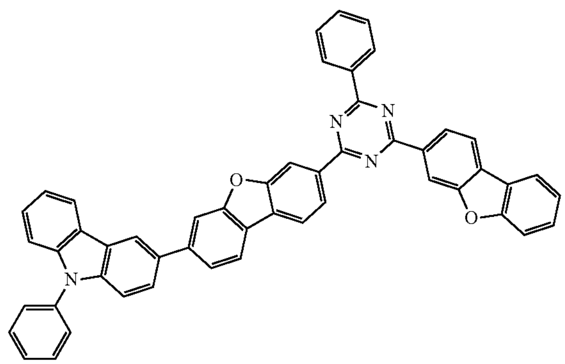
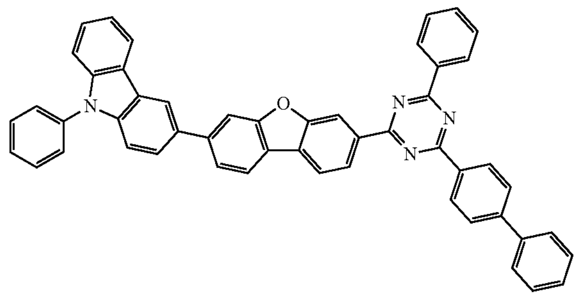
-continued
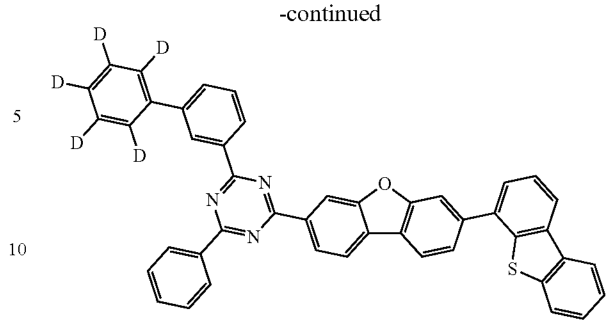
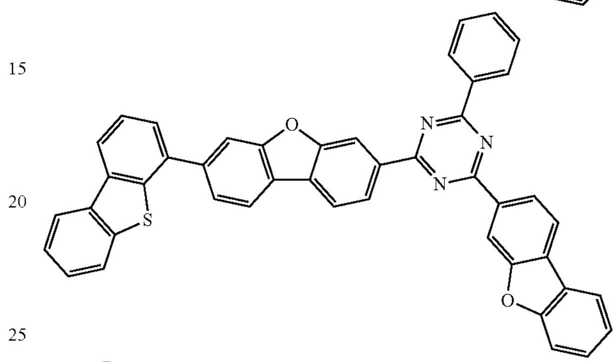
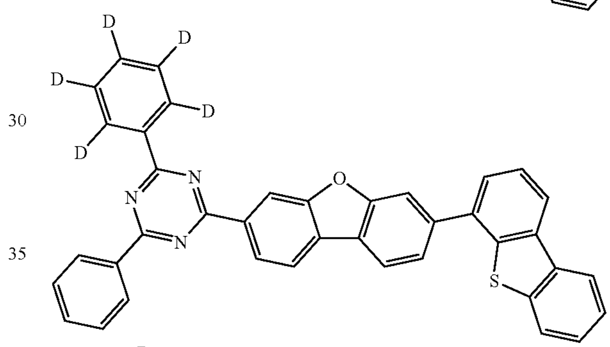
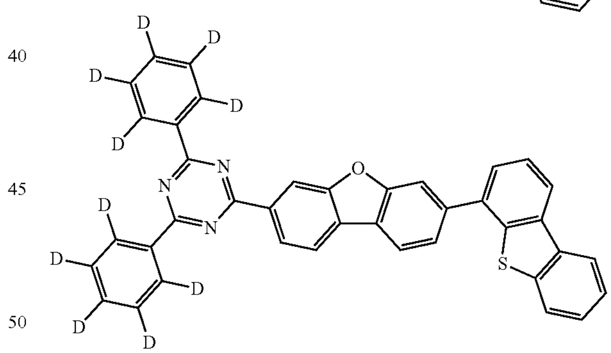
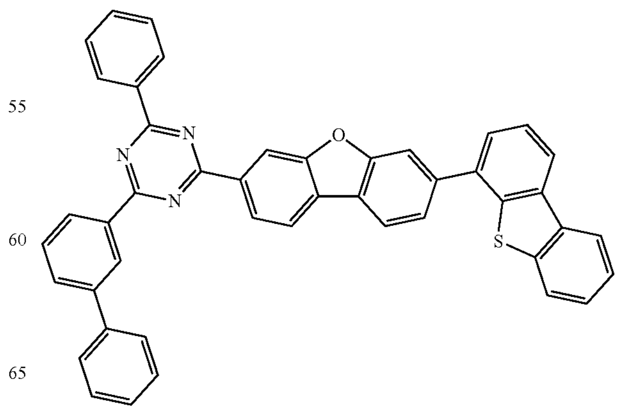

-continued
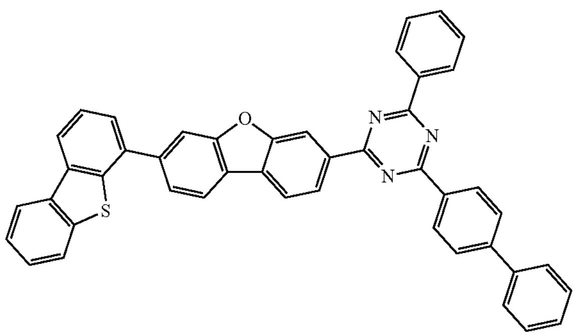
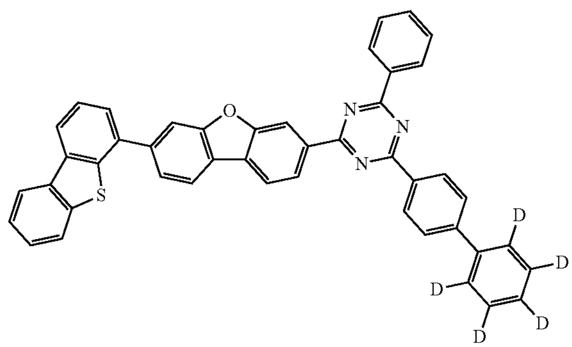
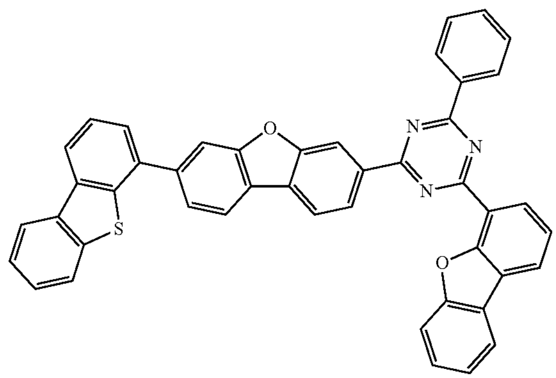
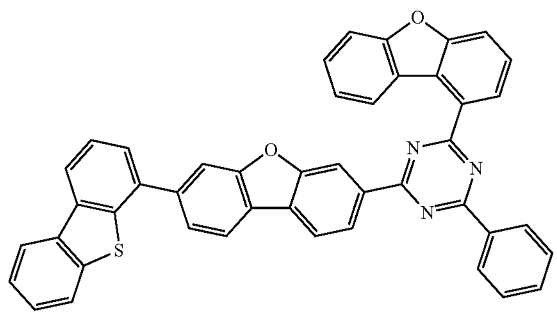
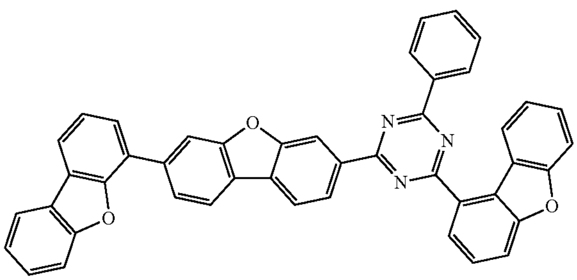
-continued
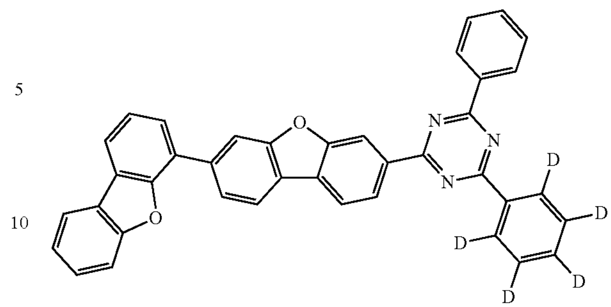
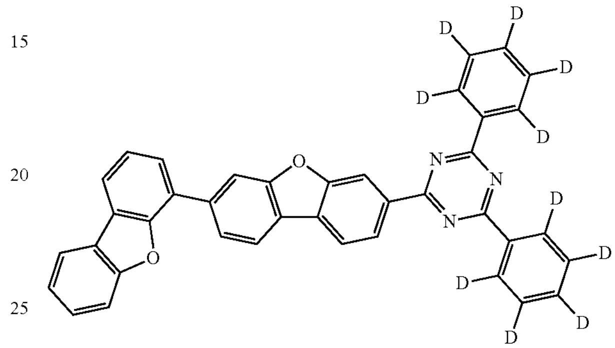
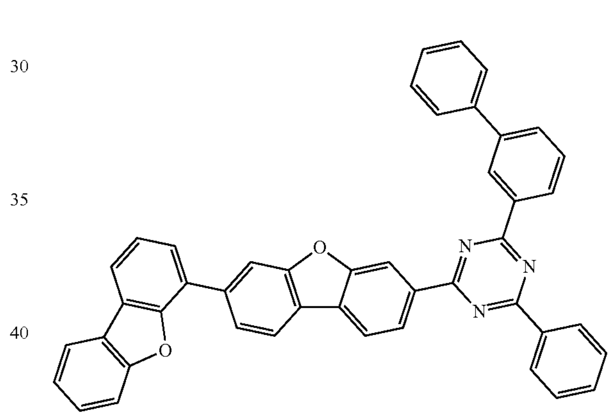
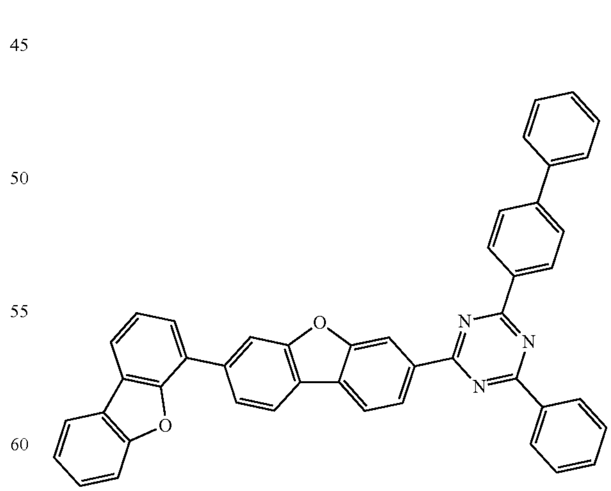

-continued
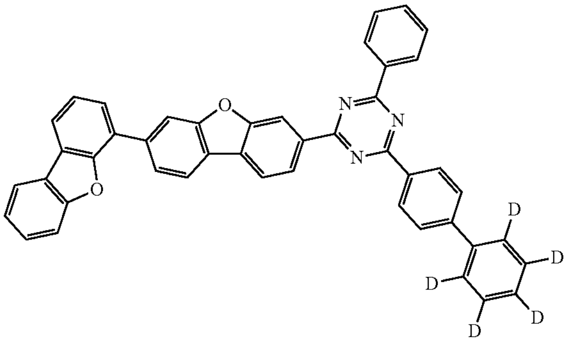 [SMILES: [2H]c1c([2H])c([2H])c(-c2ccc(-c3nc(-c4ccccc4)nc(-c4ccc5c(c4)oc4cc(-c6cccc7c6oc6ccccc67)ccc45)n3)cc2)c([2H])c1[2H]]
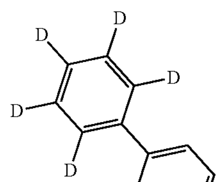
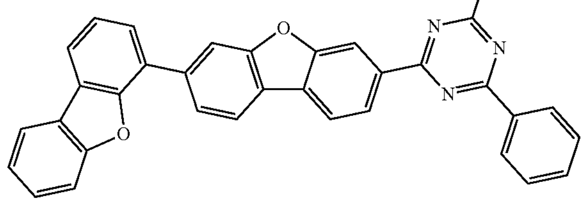
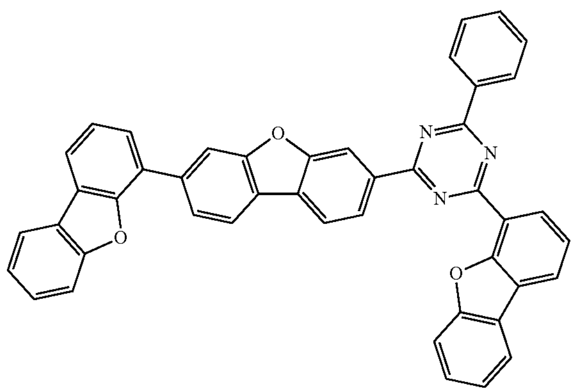
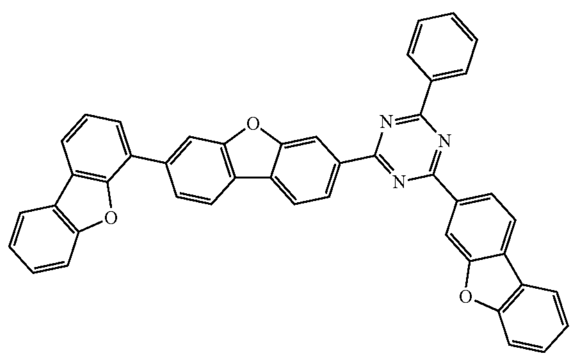
-continued
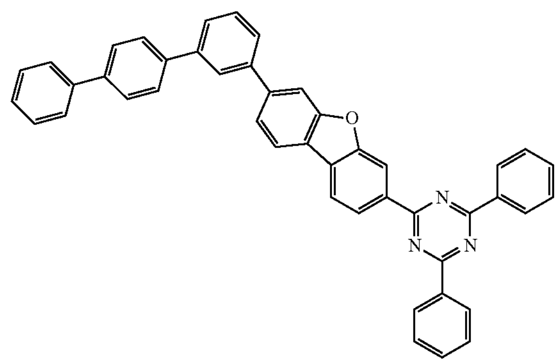
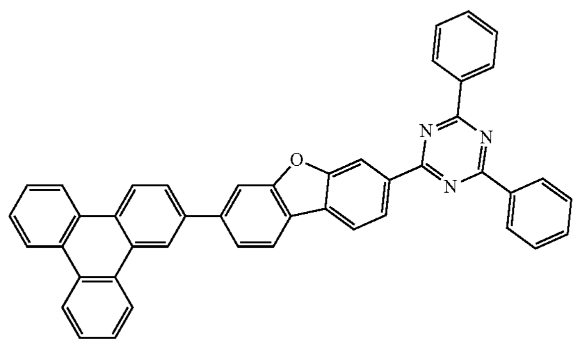
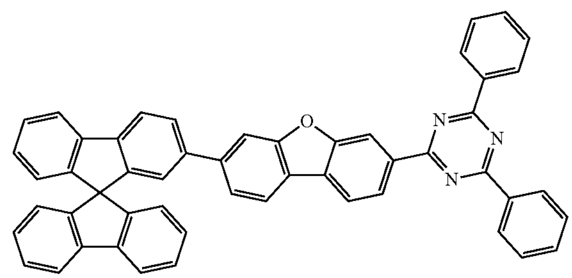
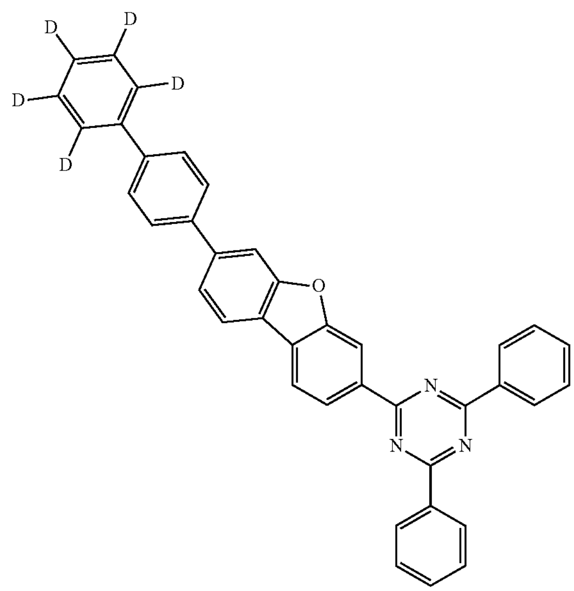

-continued
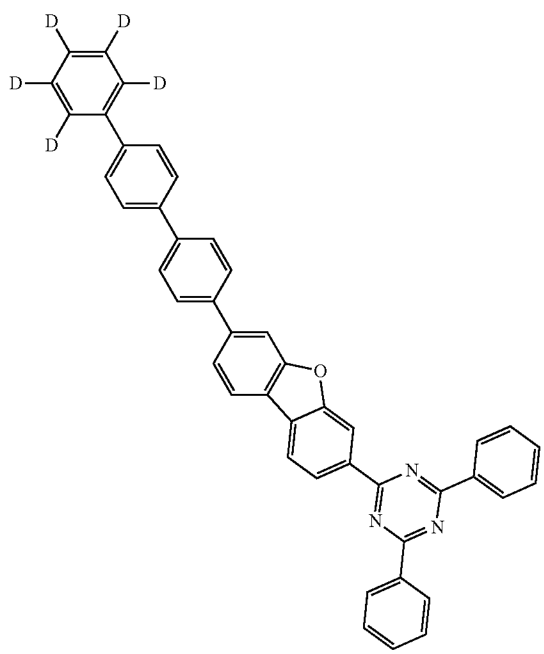
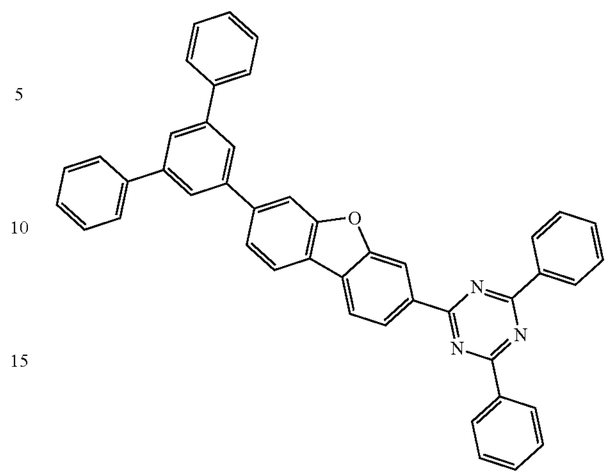
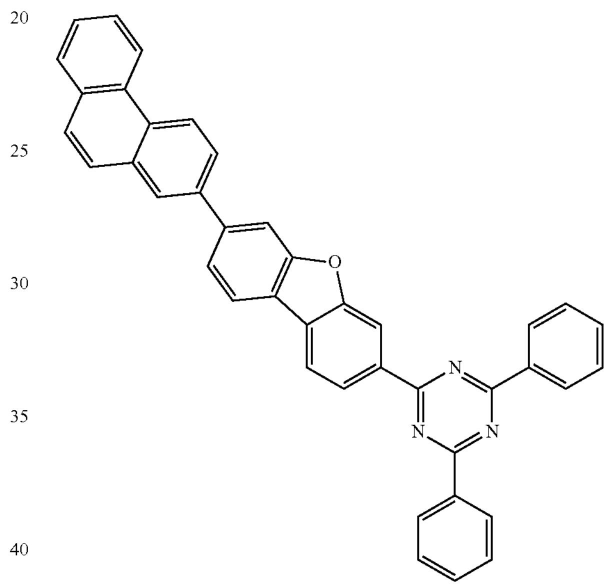
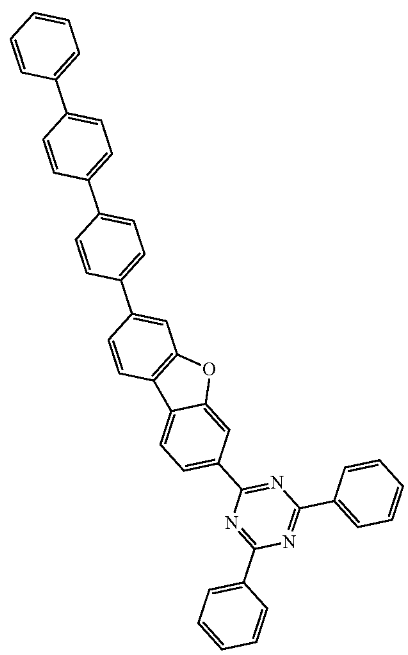
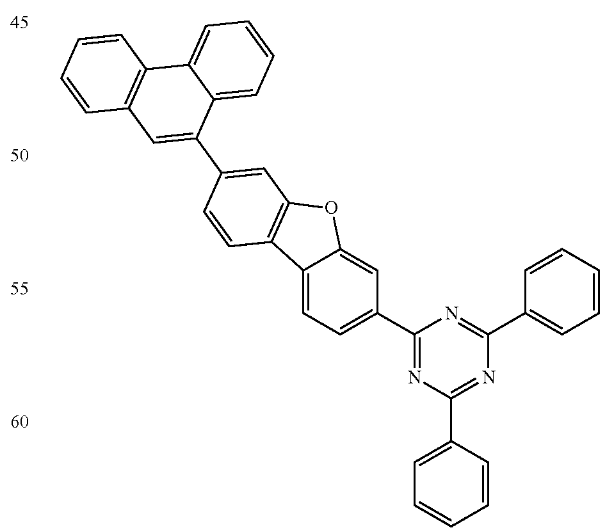

-continued
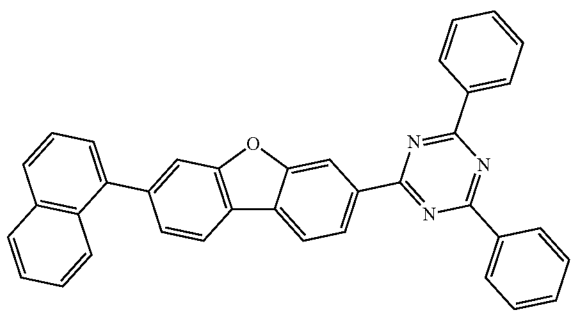
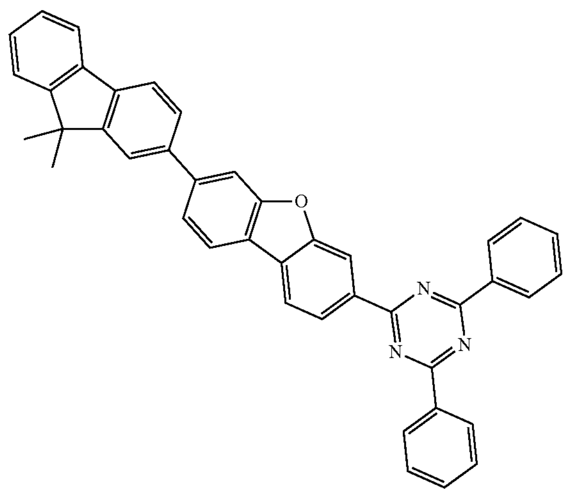
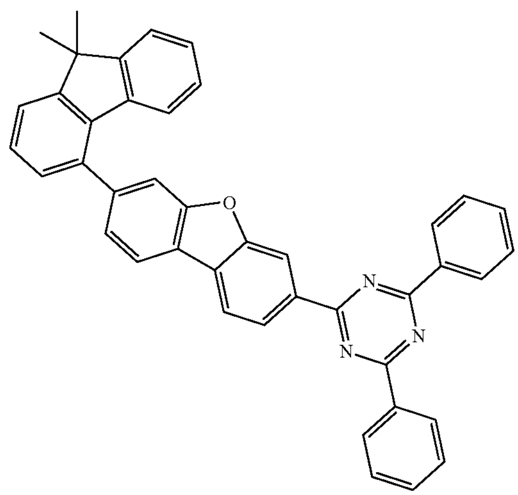
-continued
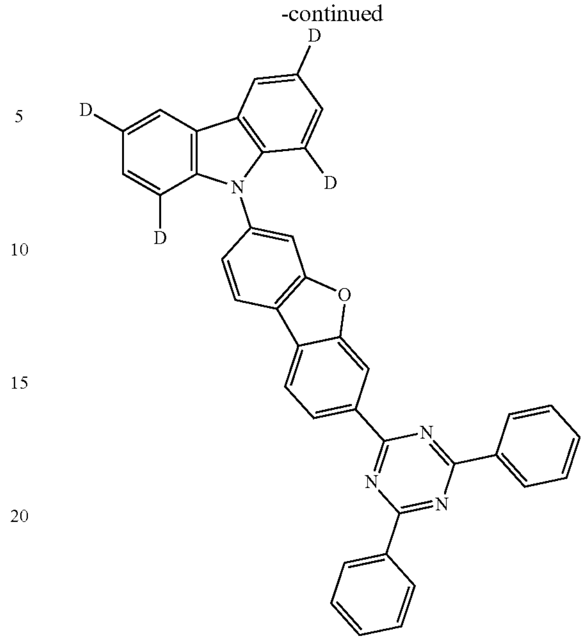
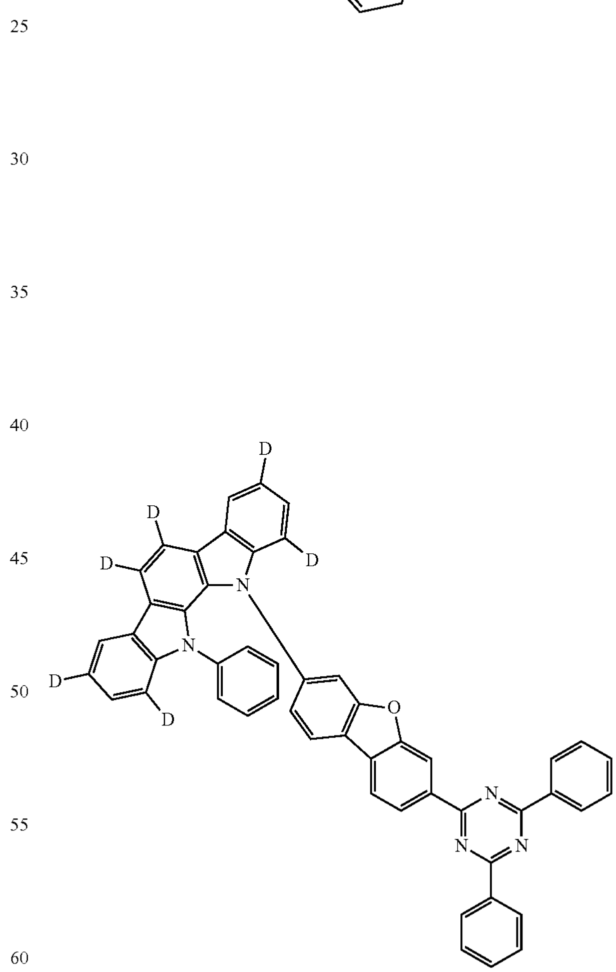

-continued
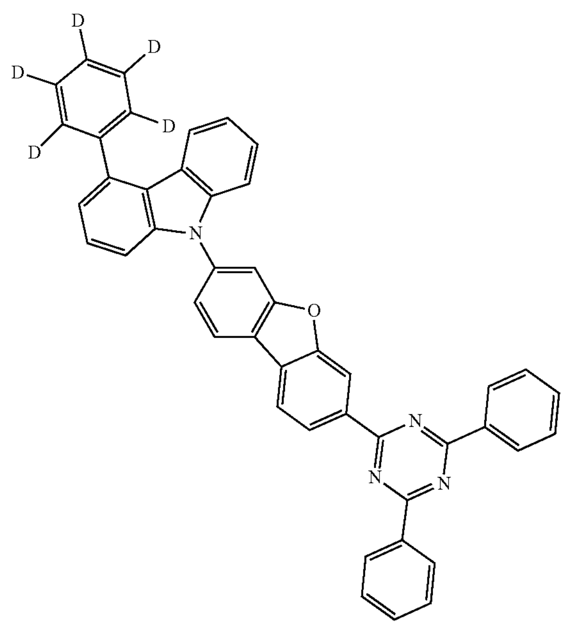
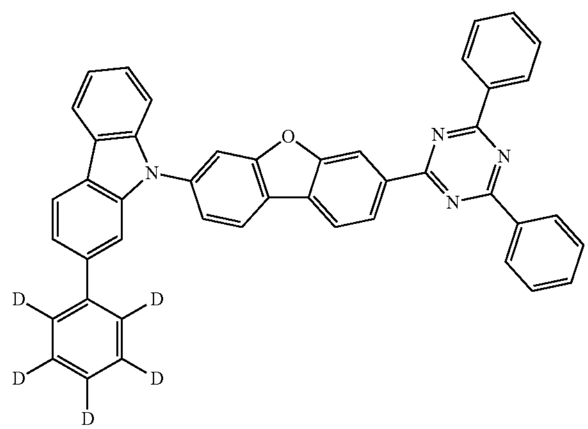
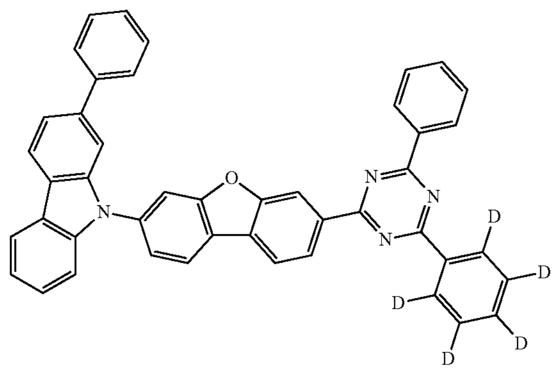
-continued
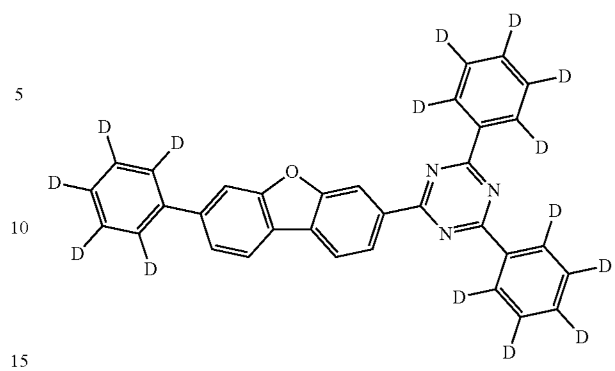
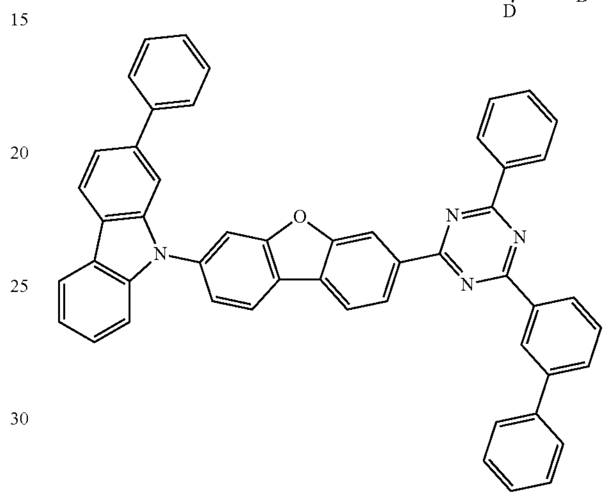
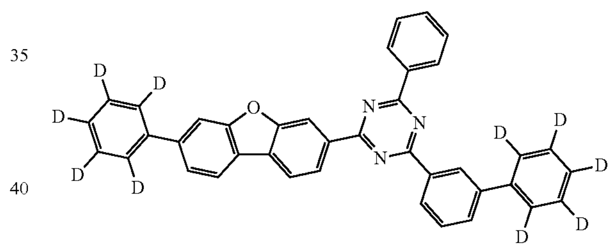
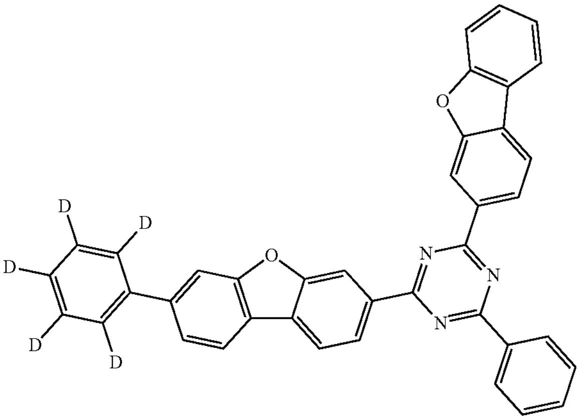

-continued
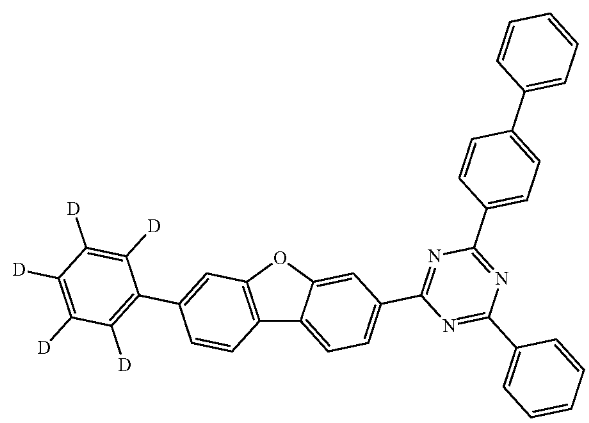
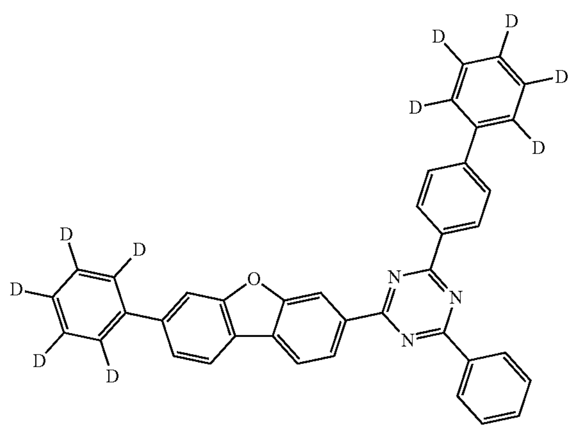
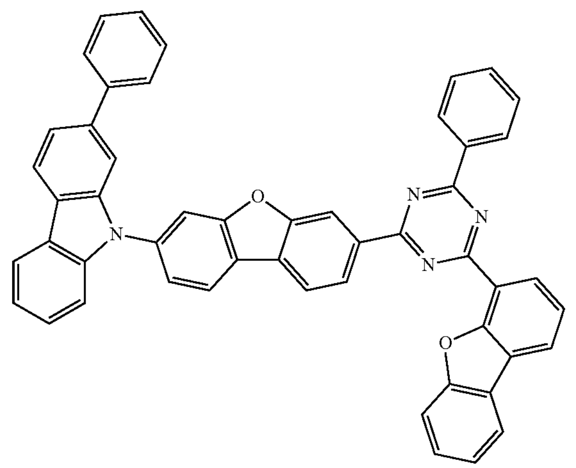
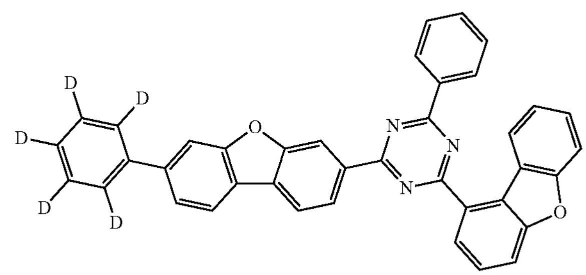
-continued
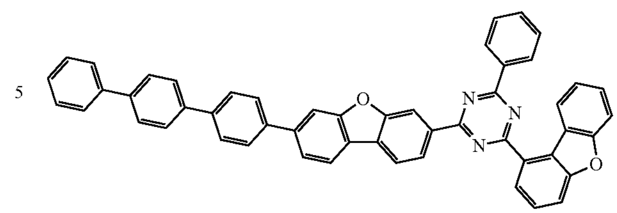
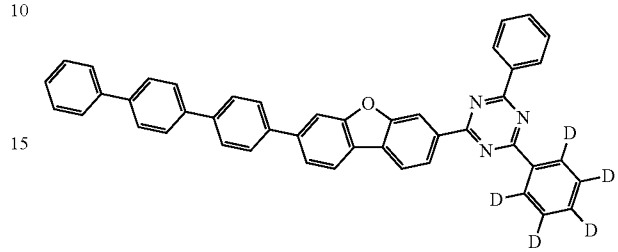
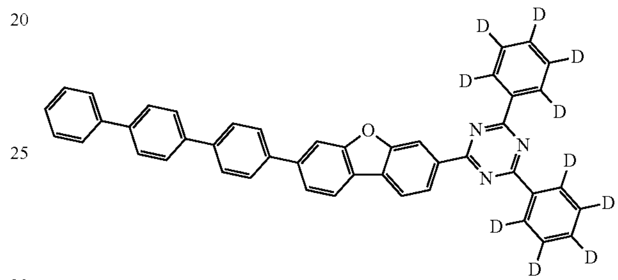
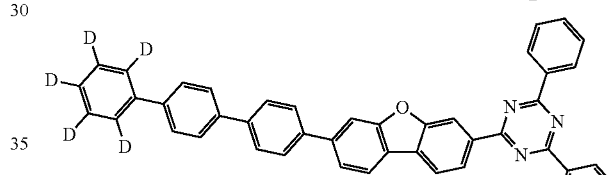
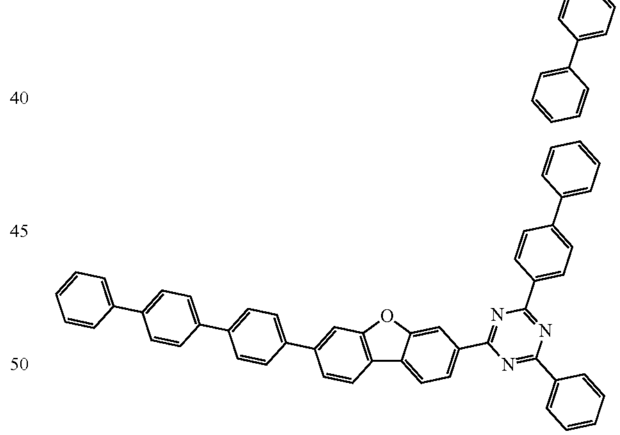
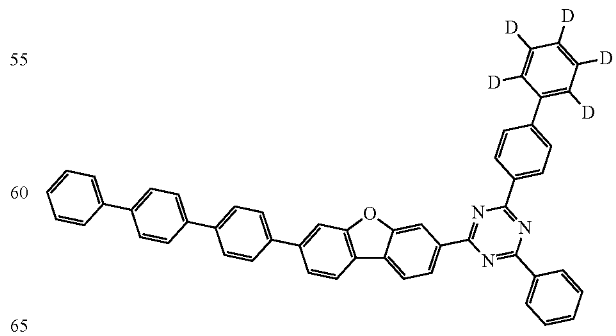

-continued
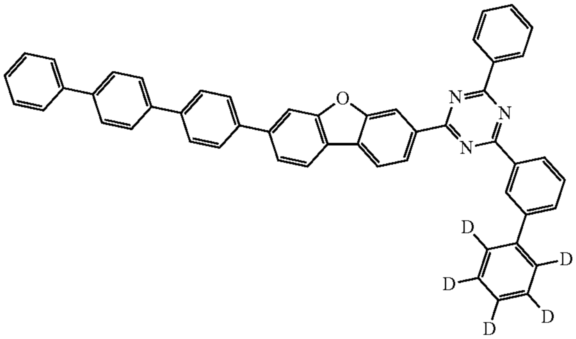
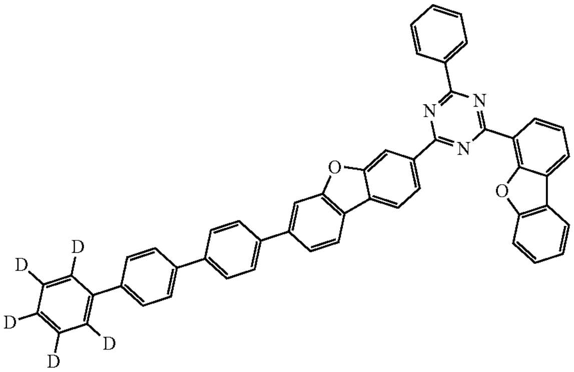
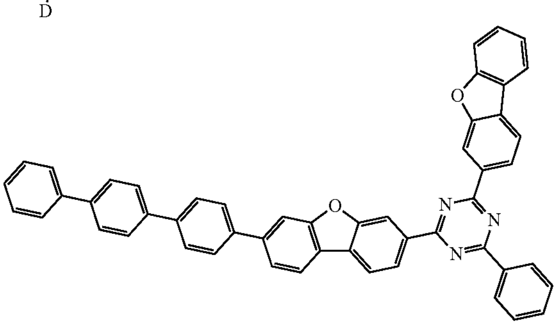
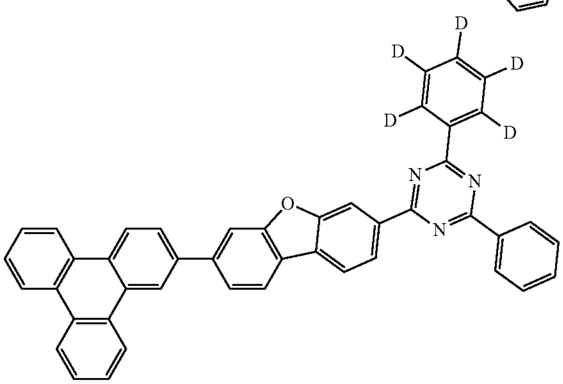
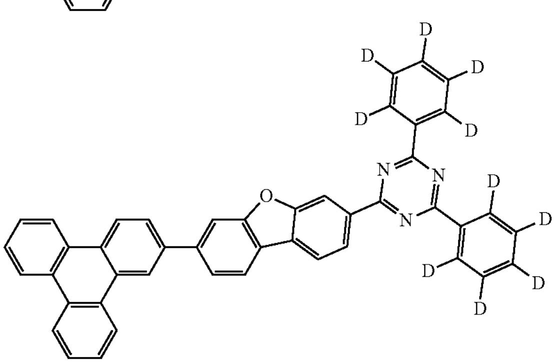
-continued
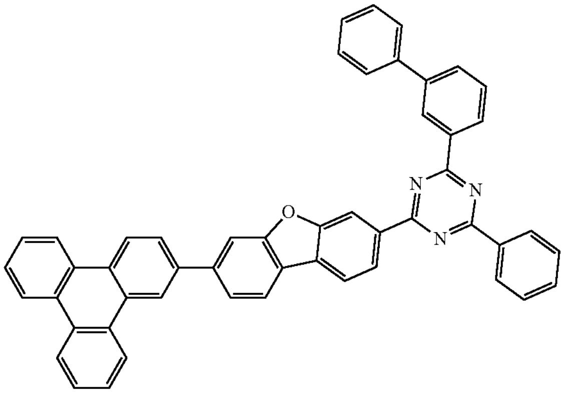
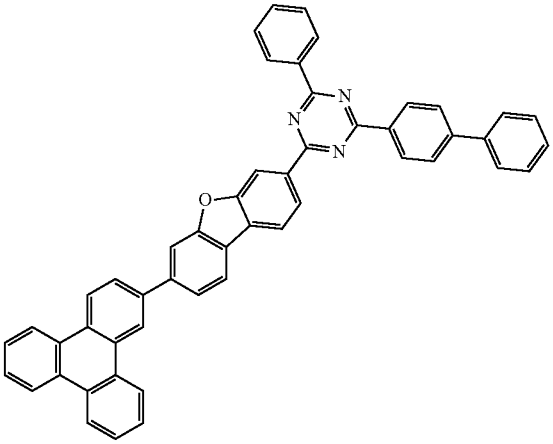
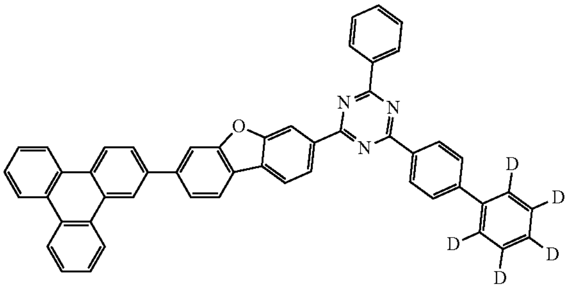
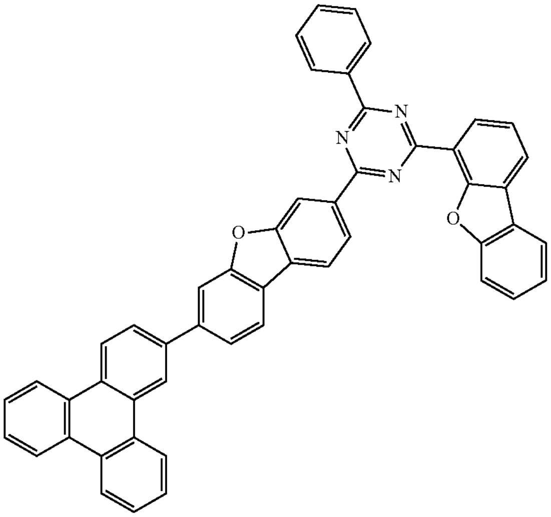

-continued
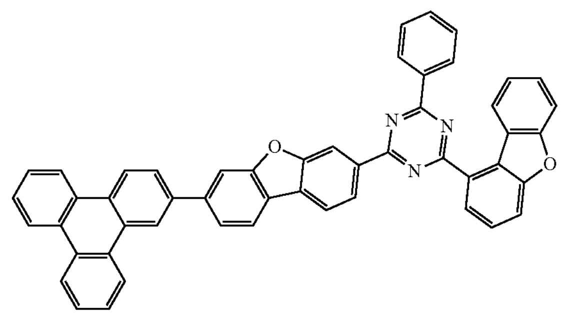
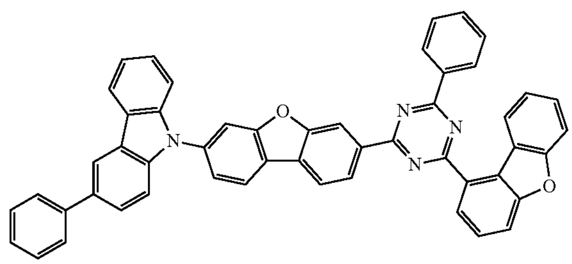
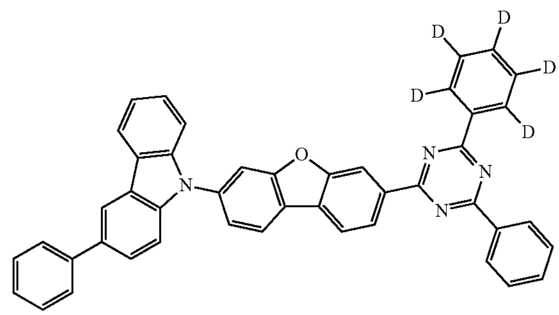
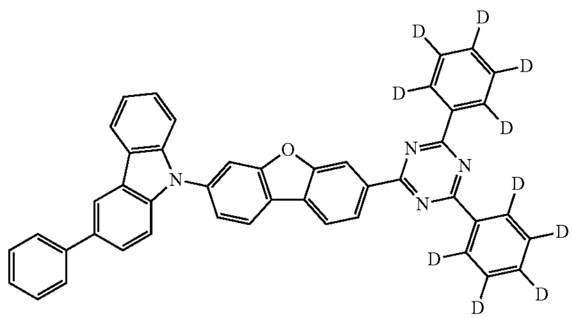
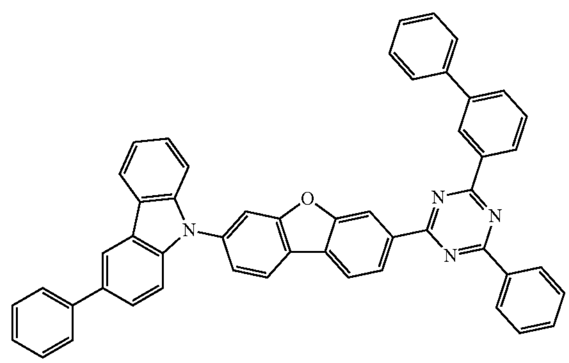
-continued
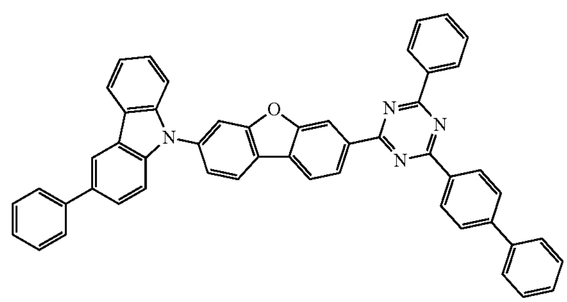
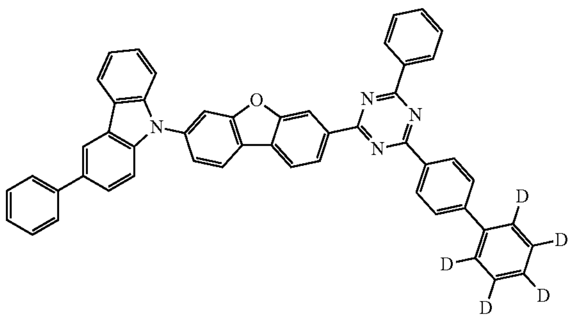
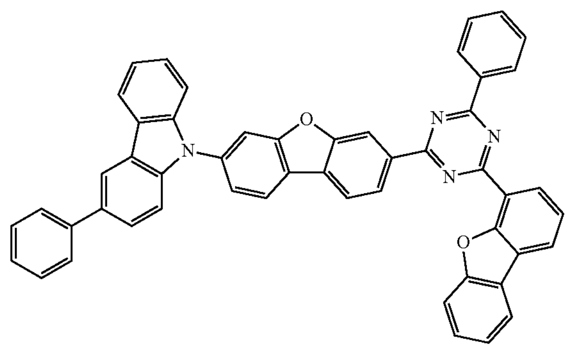
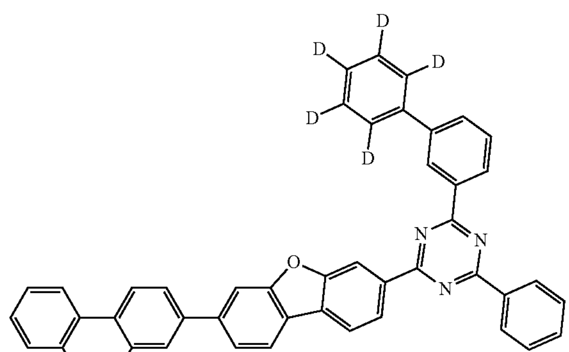

-continued
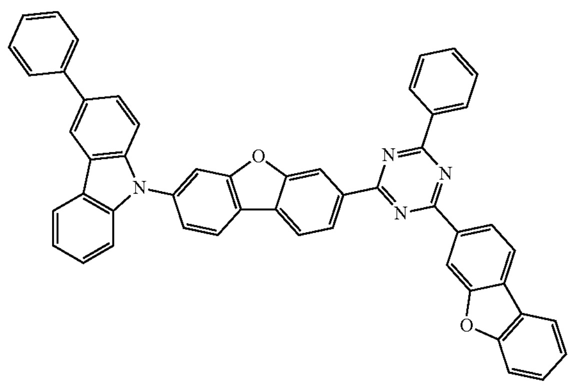 [SMILES: c1ccc(-c2ccc3c(c2)c2ccccc2n3-c2ccc3c(c2)oc2cc(-c4nc(-c5ccccc5)nc(-c5ccc6c(c5)oc5ccccc56)n4)ccc23)cc1]
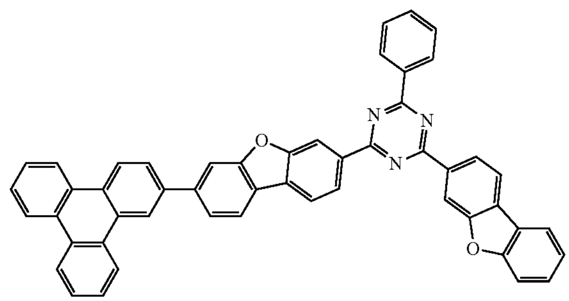
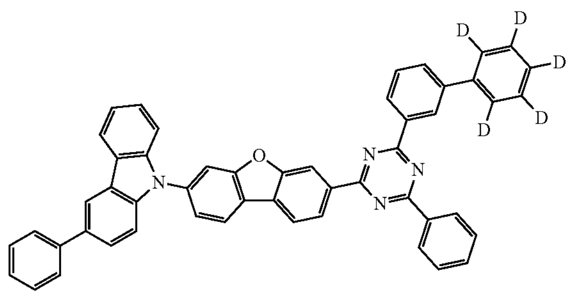
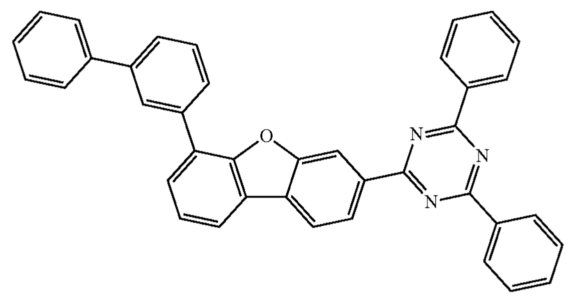
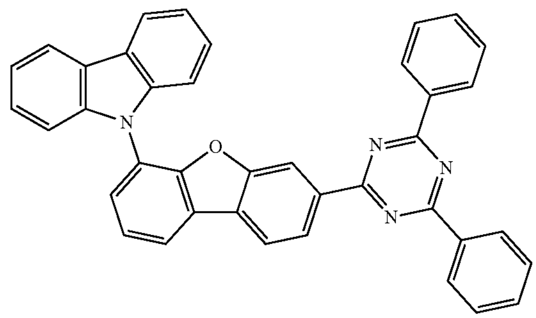
-continued
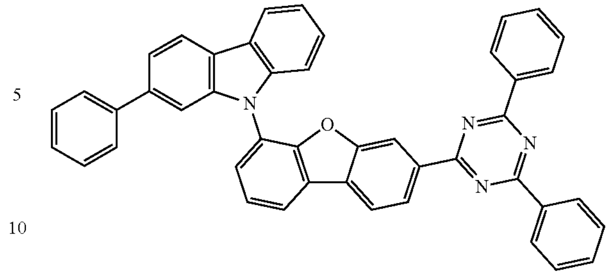
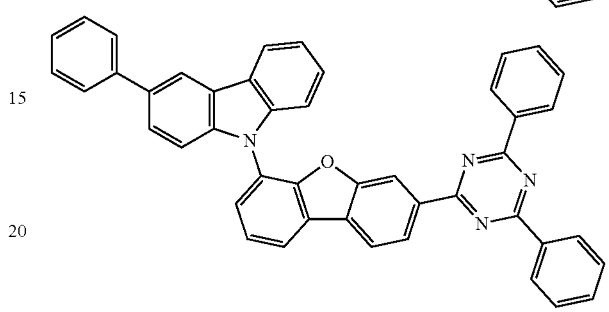
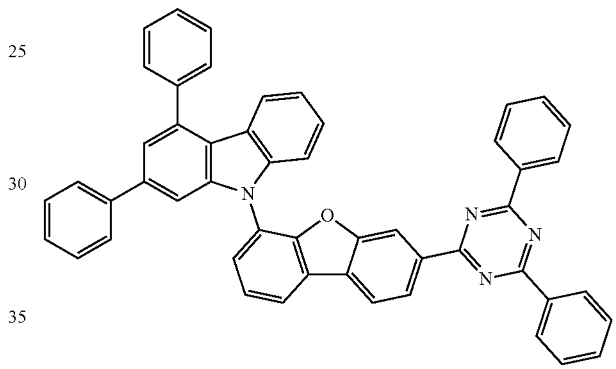
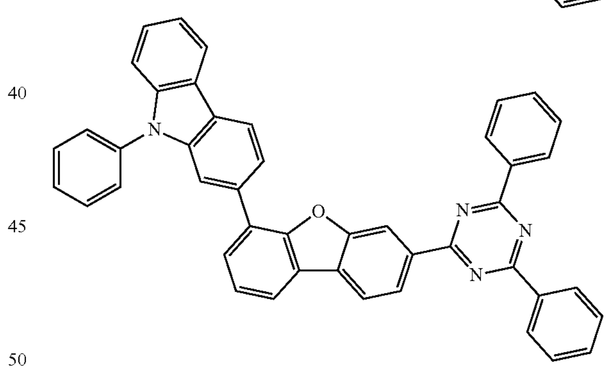
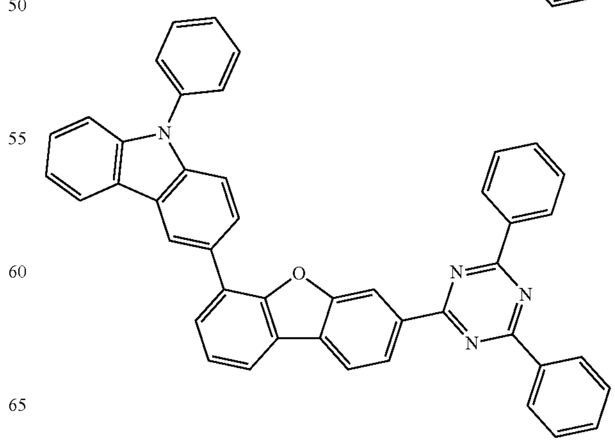

-continued
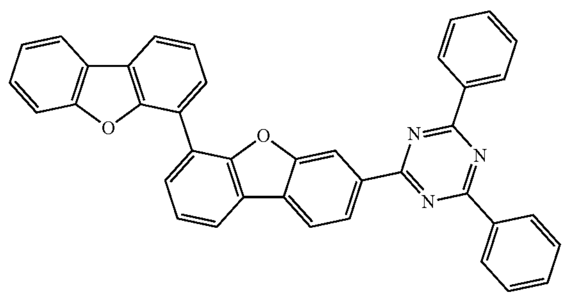
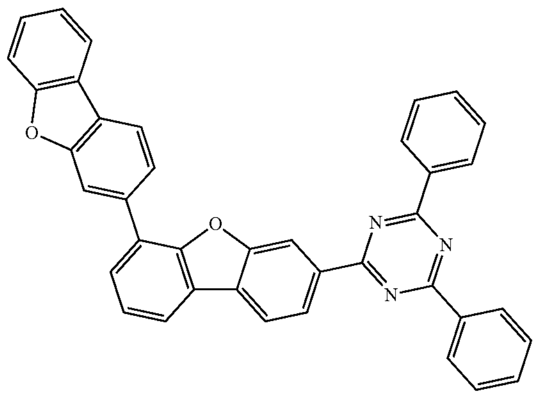
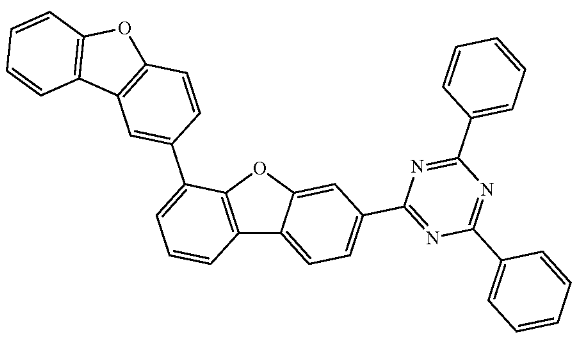
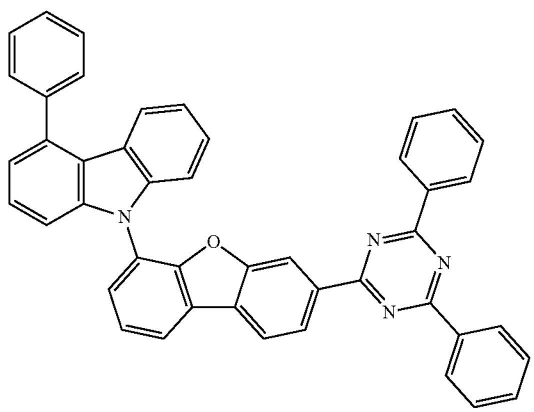
-continued
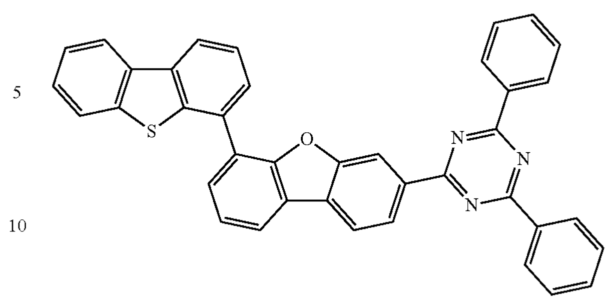
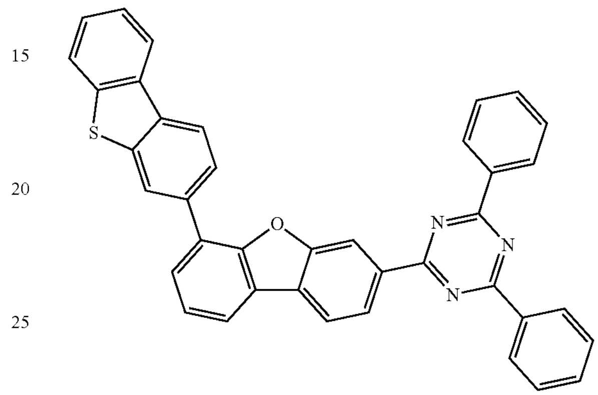
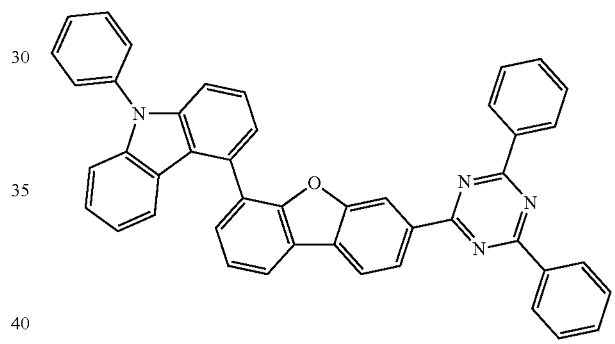
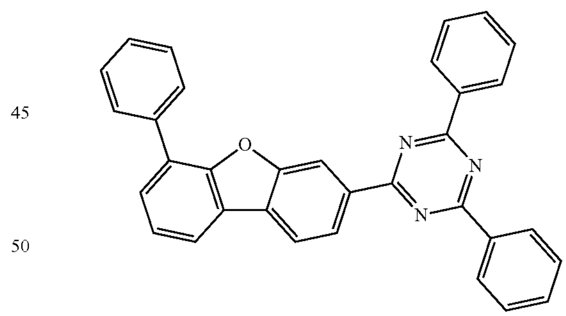
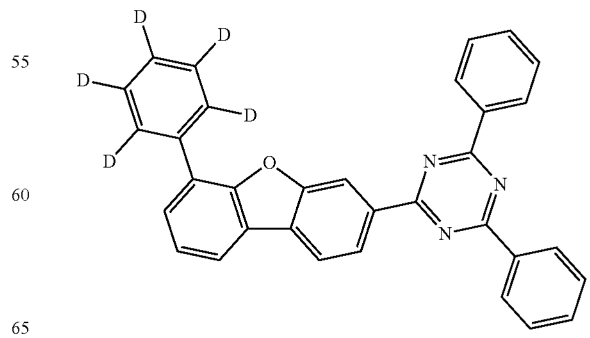

-continued
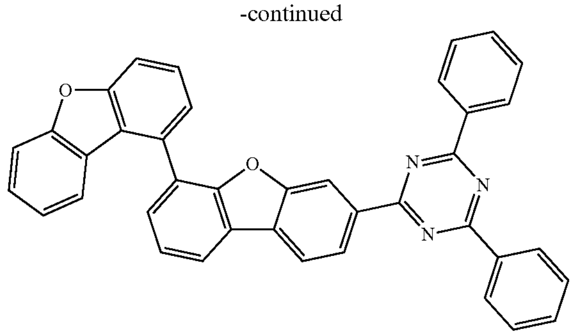
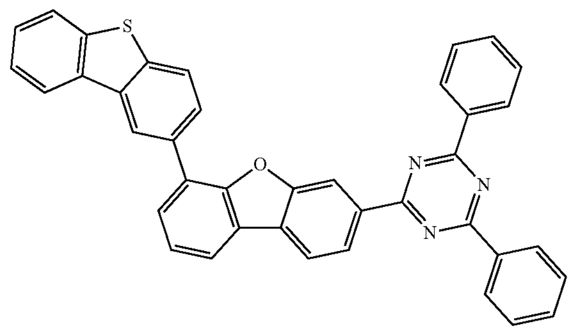
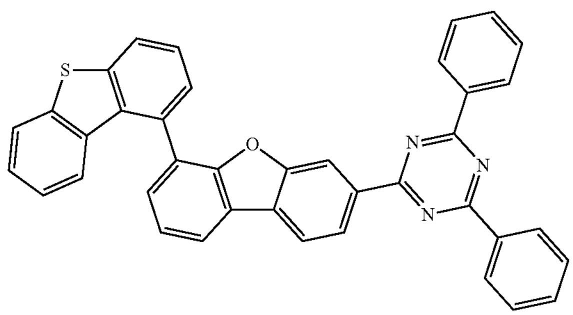
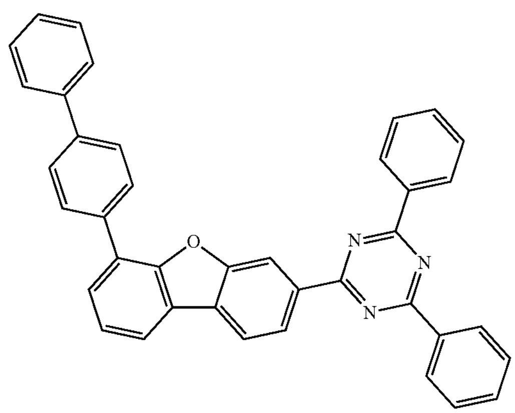
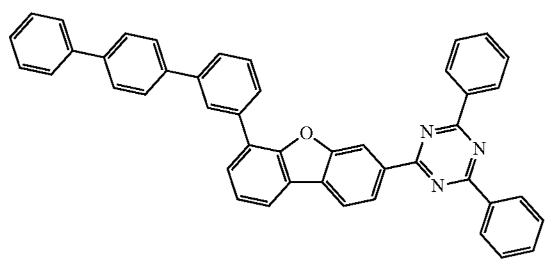
-continued
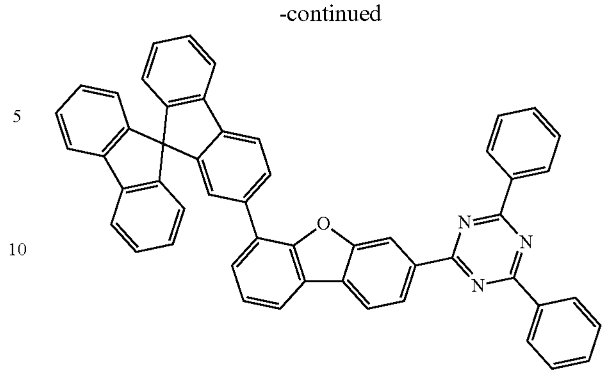
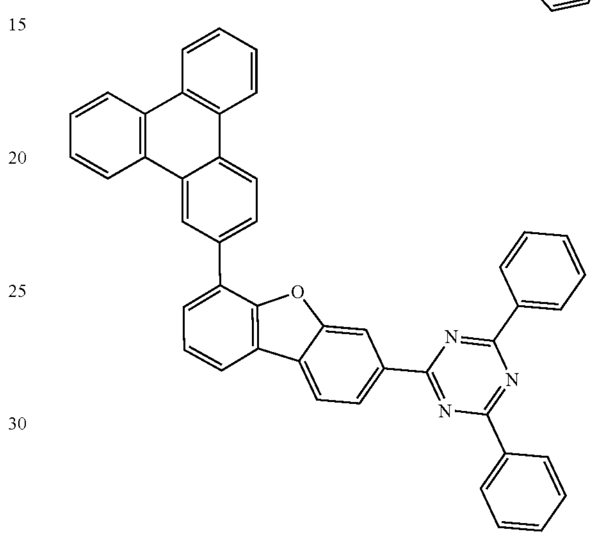
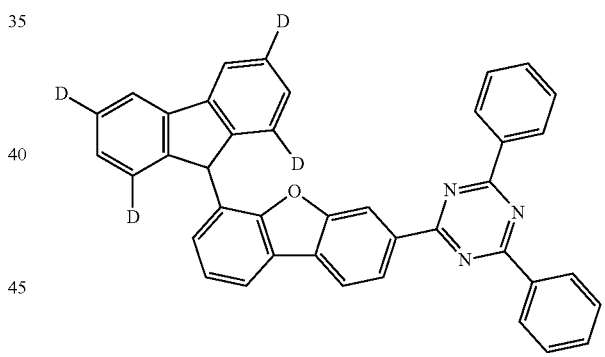
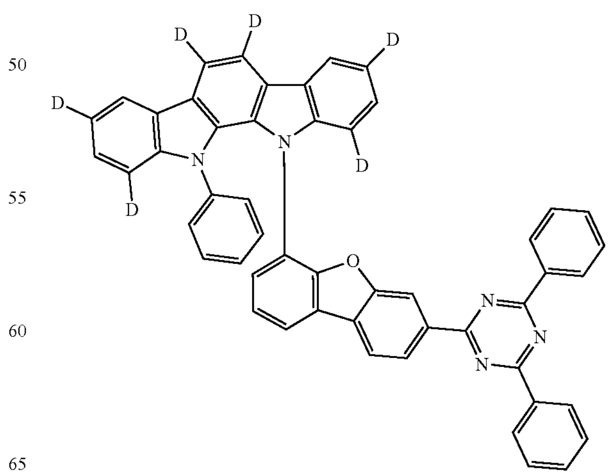

-continued
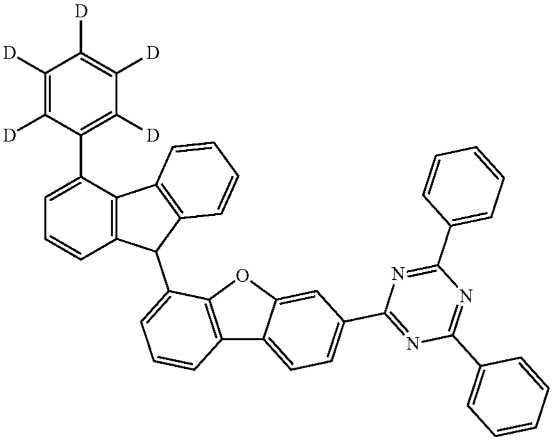
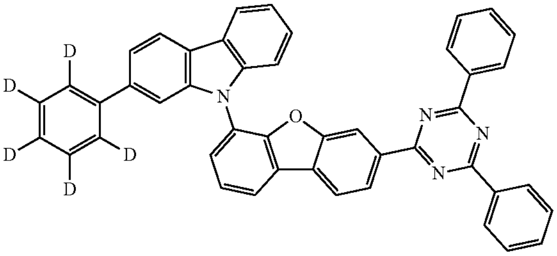
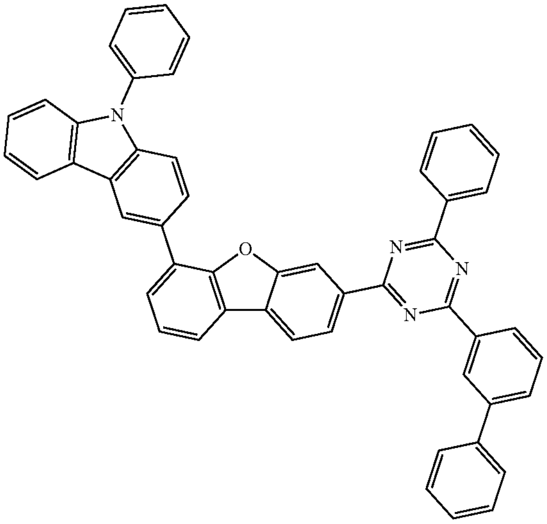
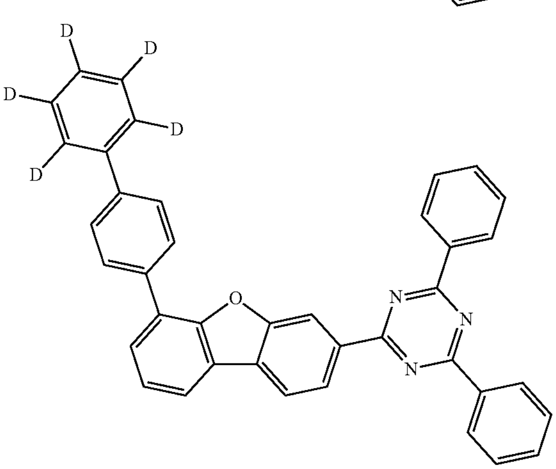
-continued
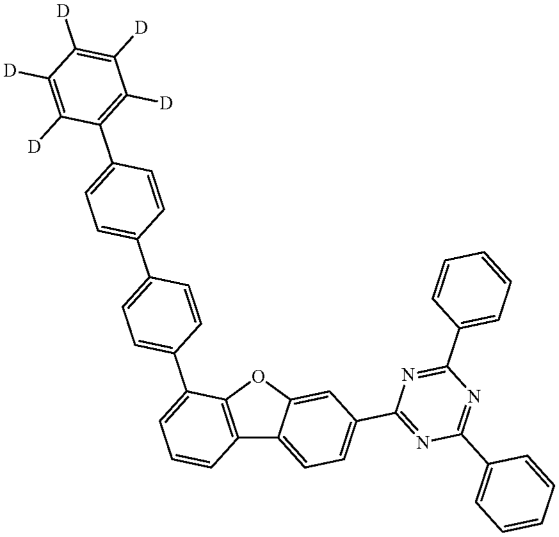
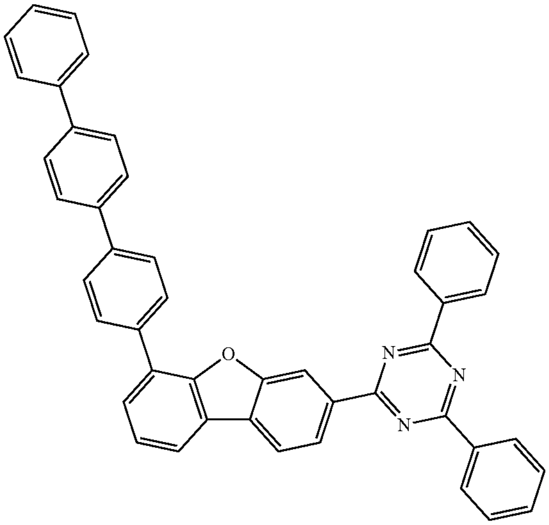
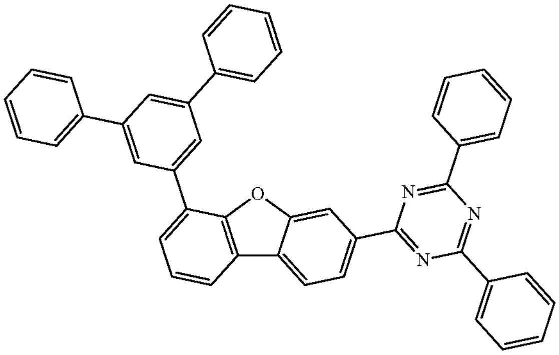

-continued
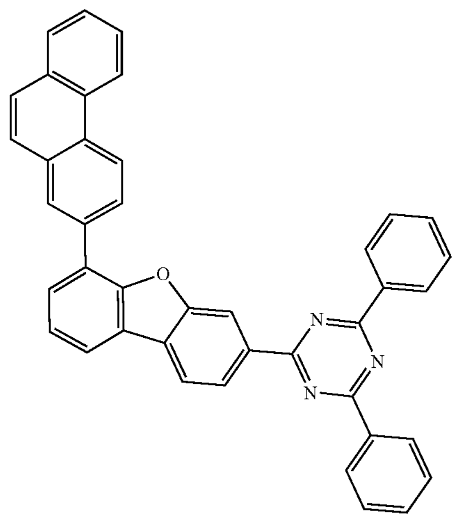
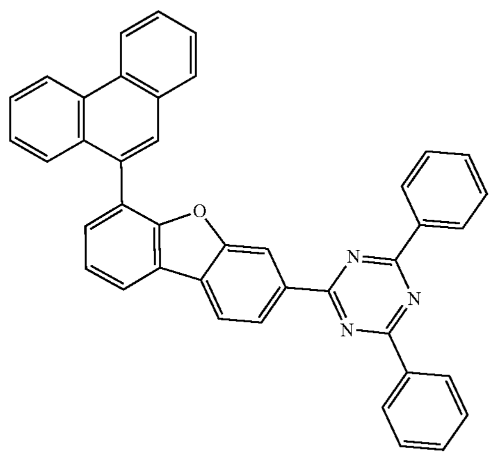
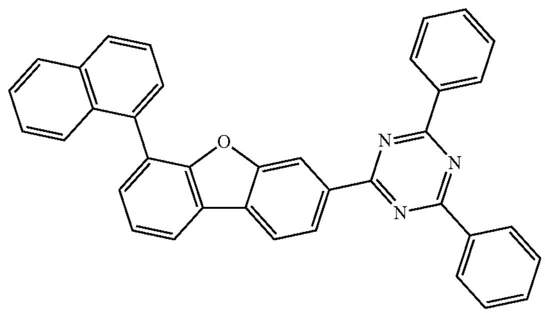
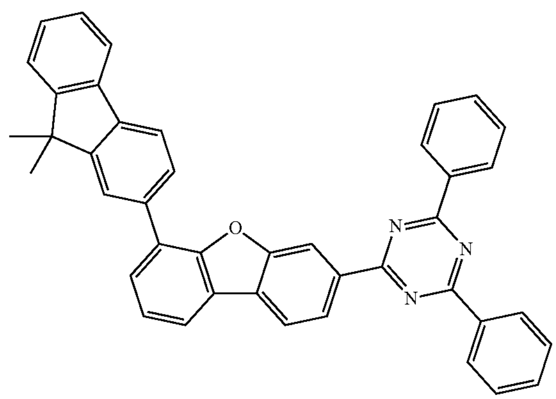
-continued
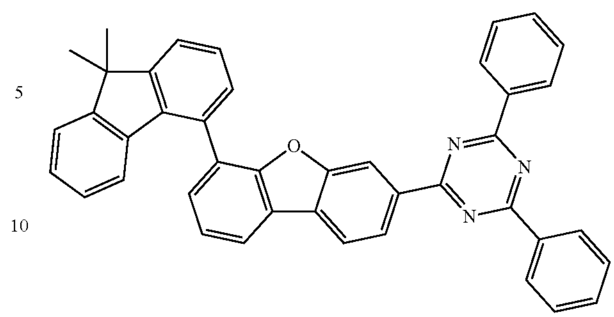
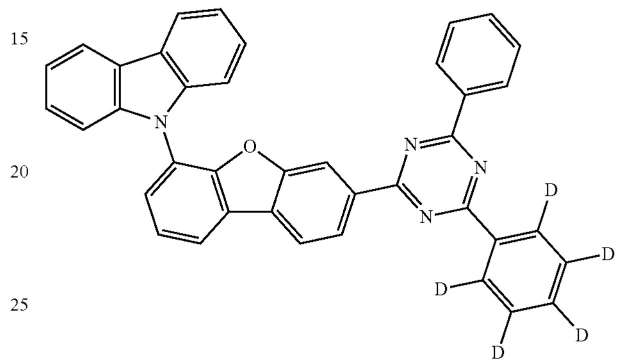
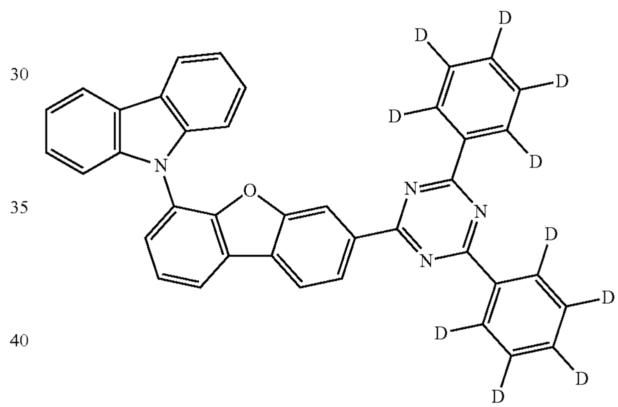
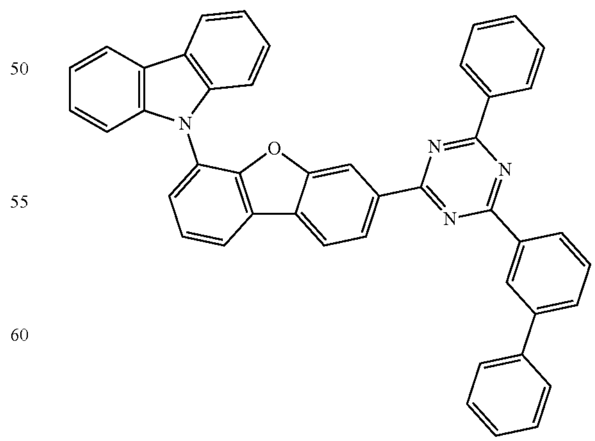

-continued
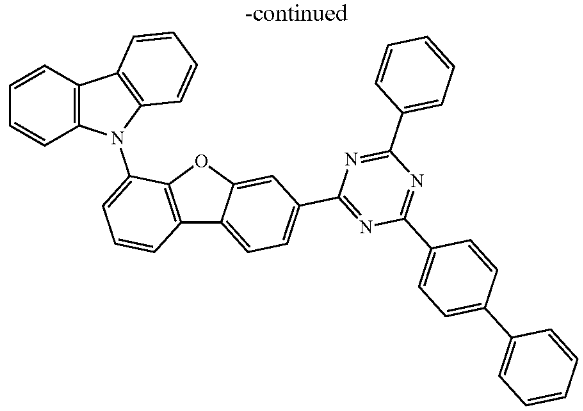
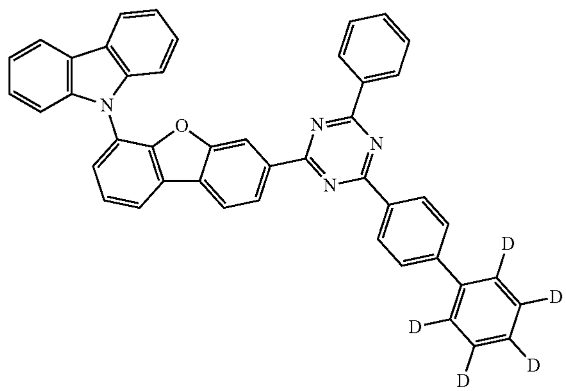
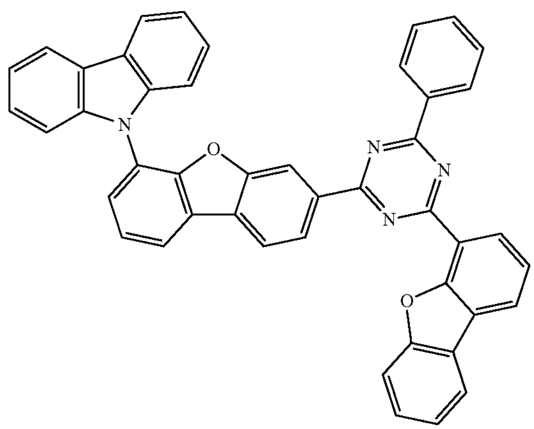
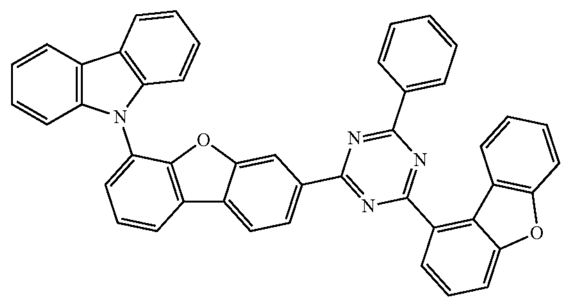
-continued
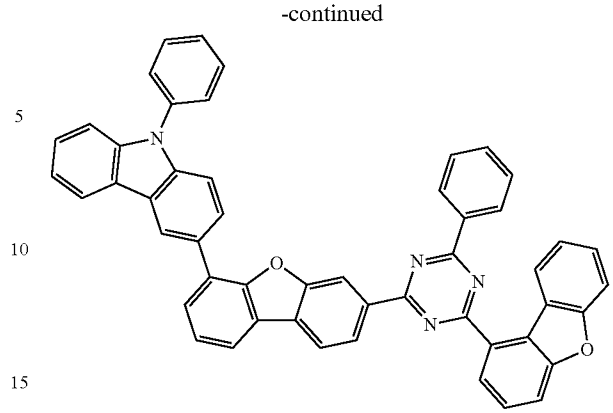
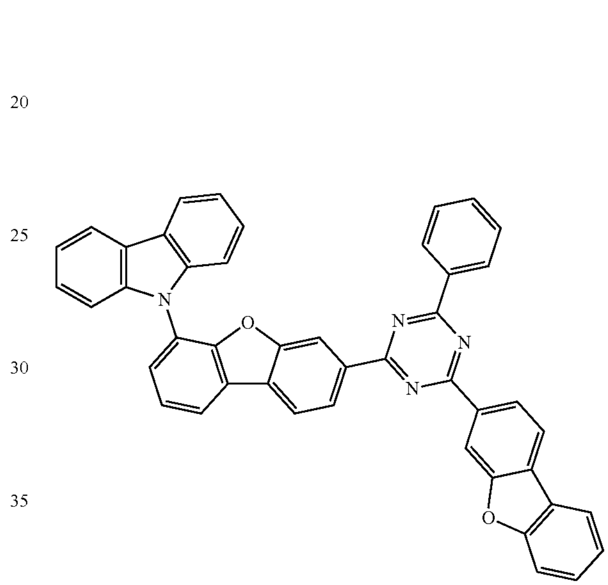
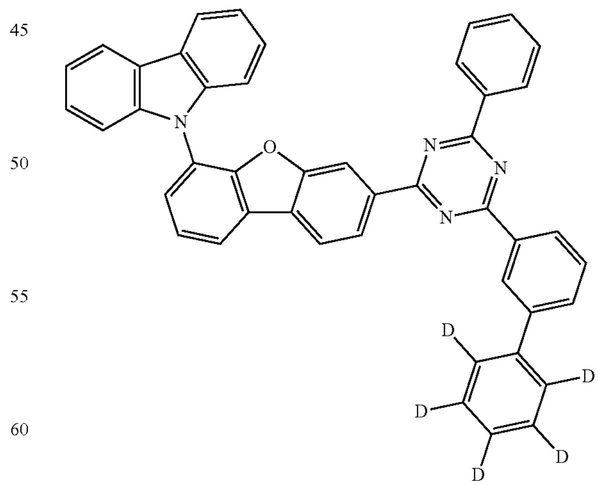

-continued
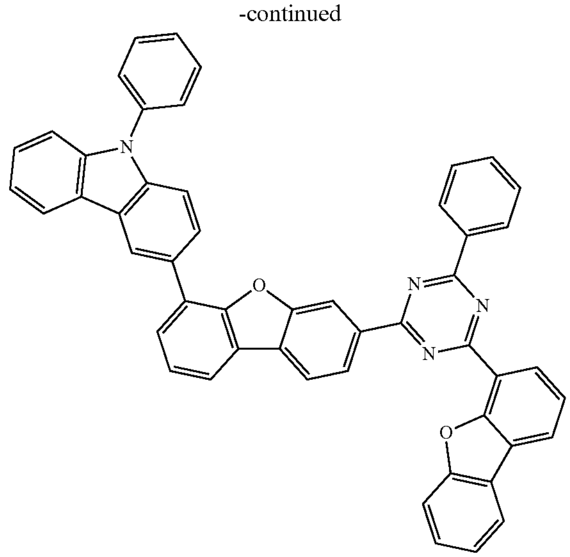
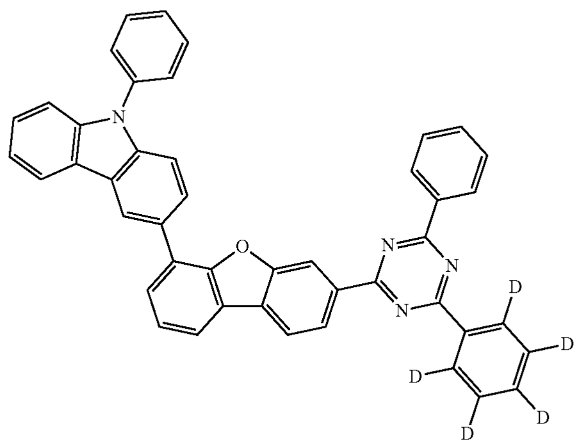
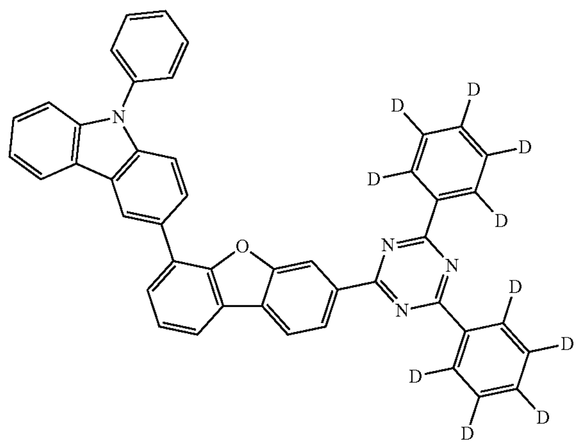
-continued
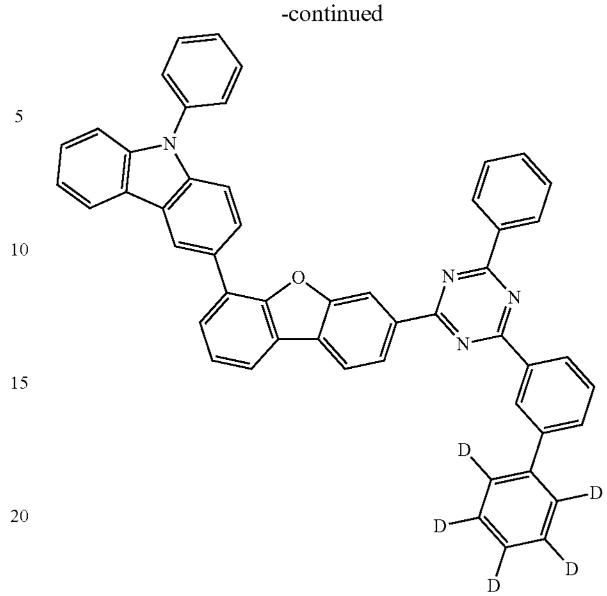
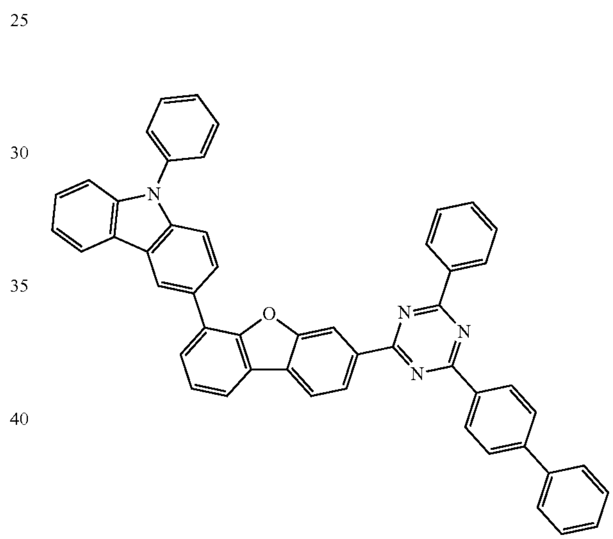
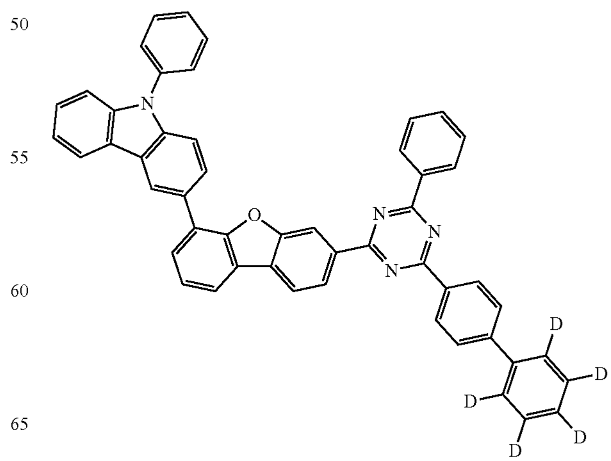

-continued
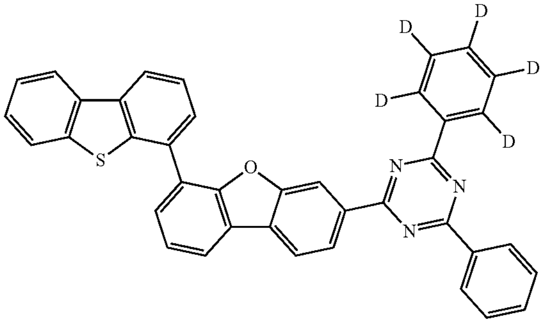
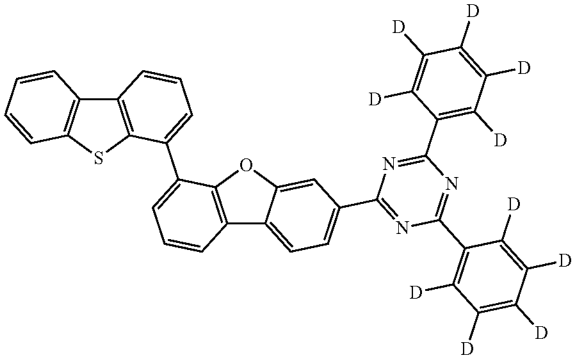
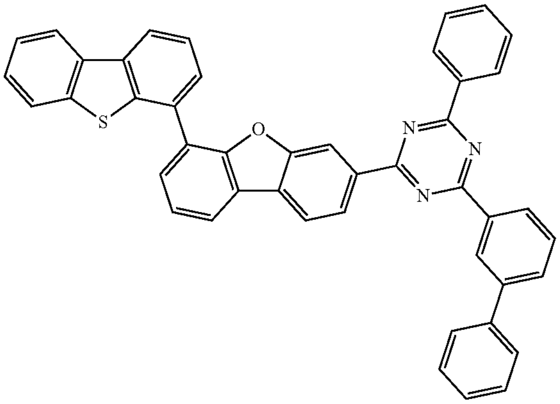
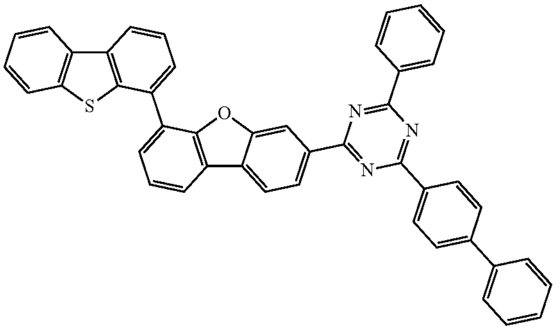
-continued
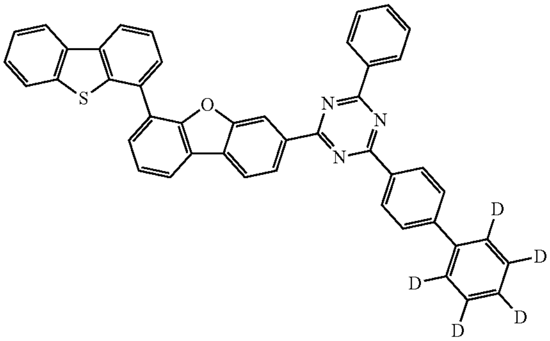
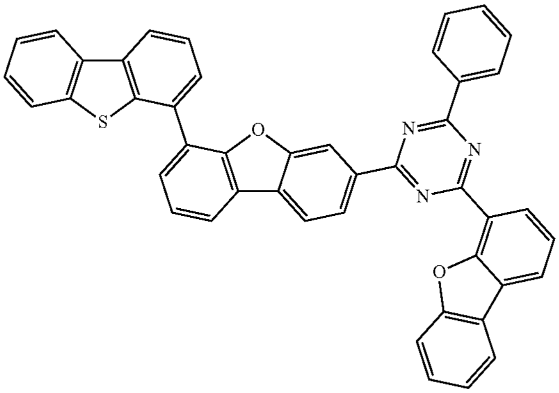
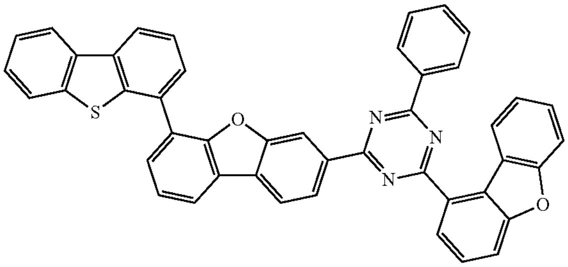
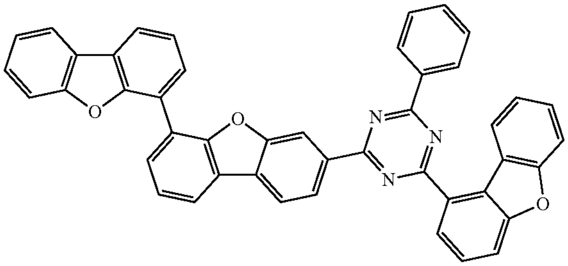
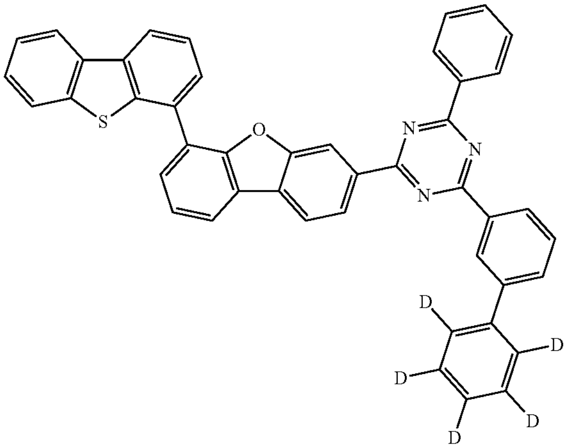

-continued
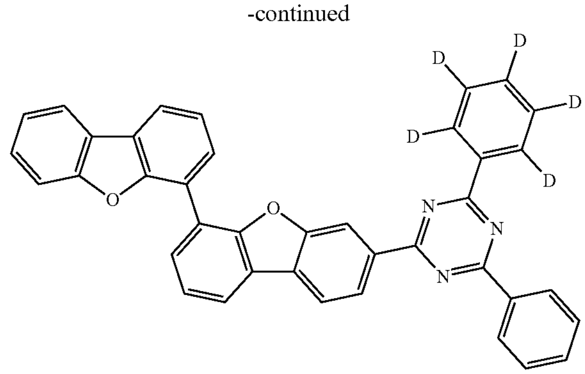
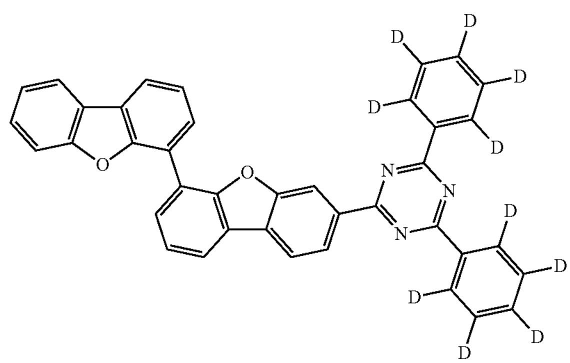
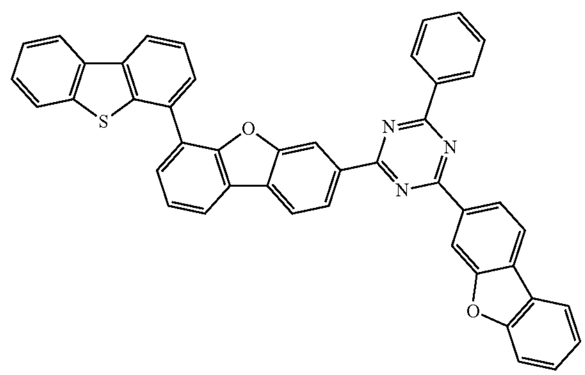
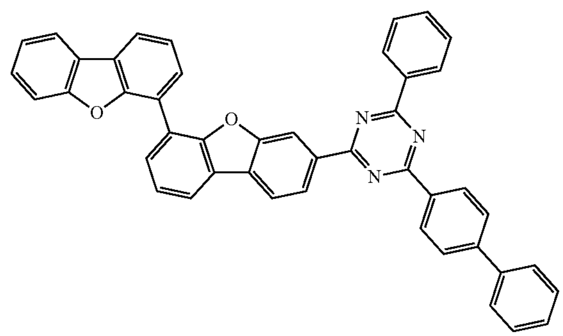
-continued
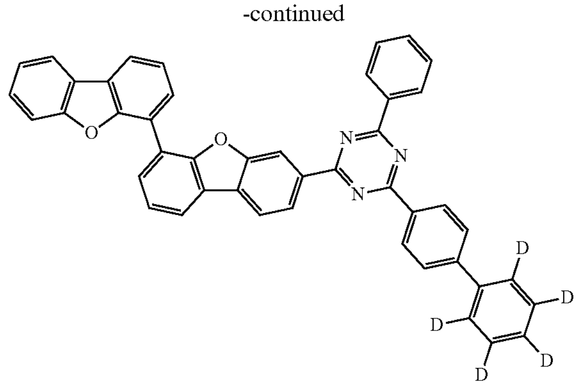
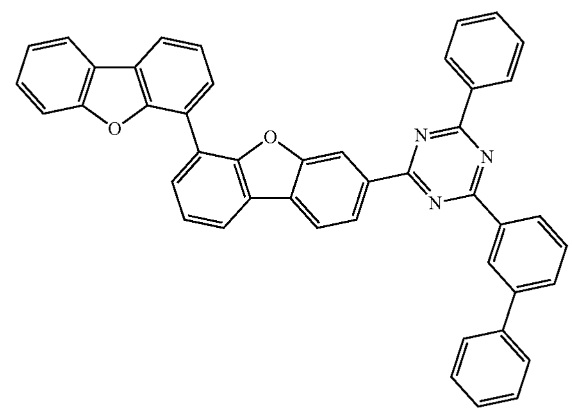
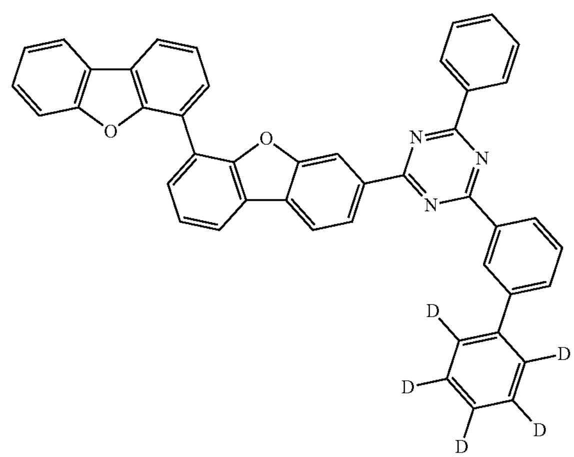
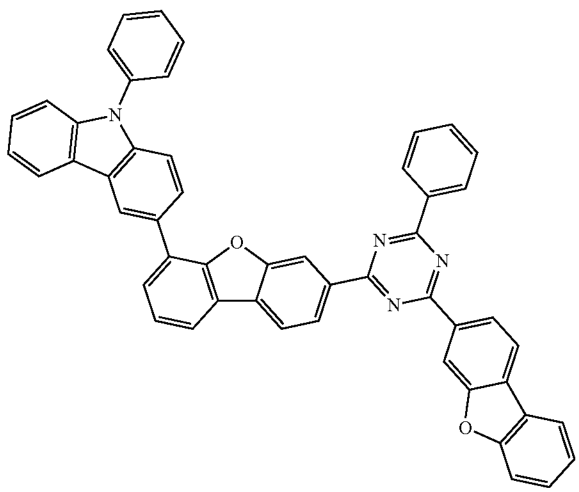

-continued
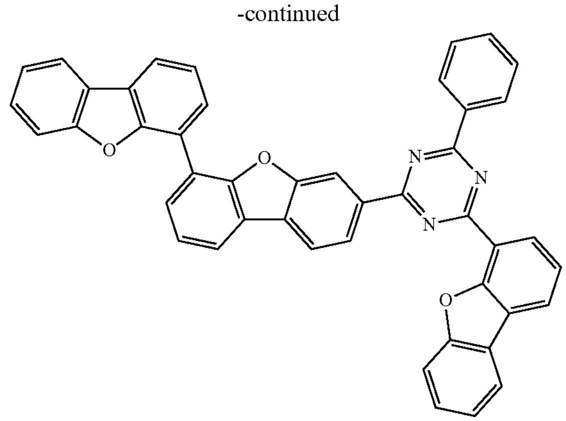
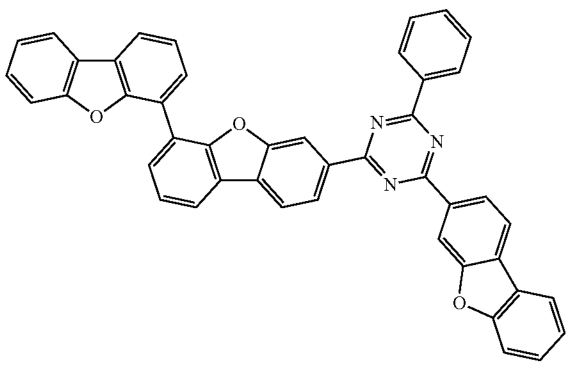
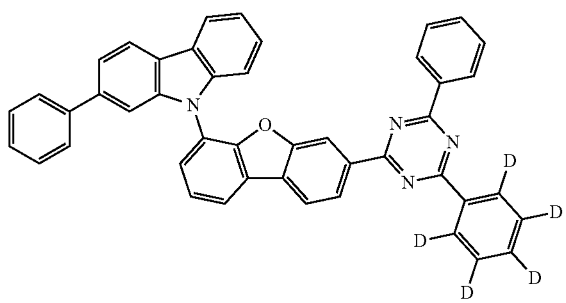
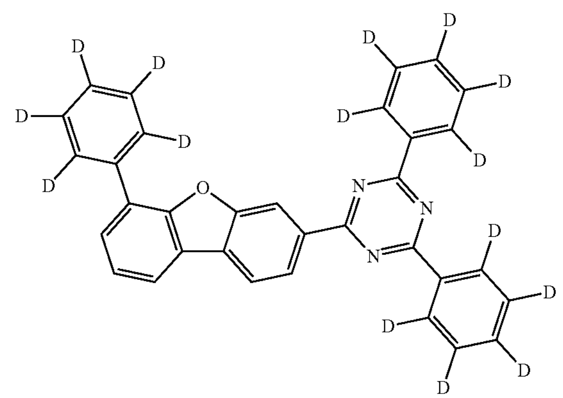
-continued
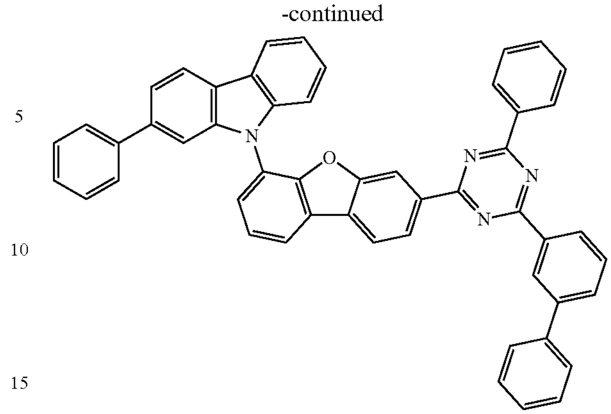
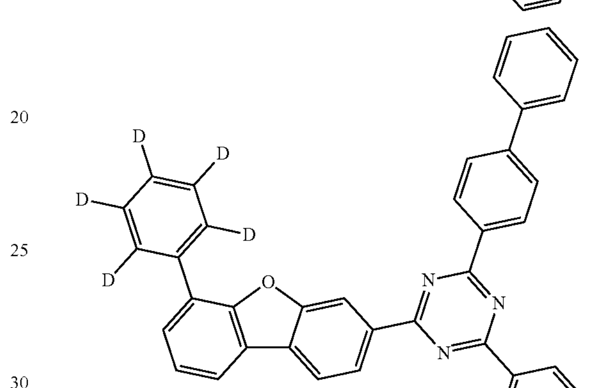
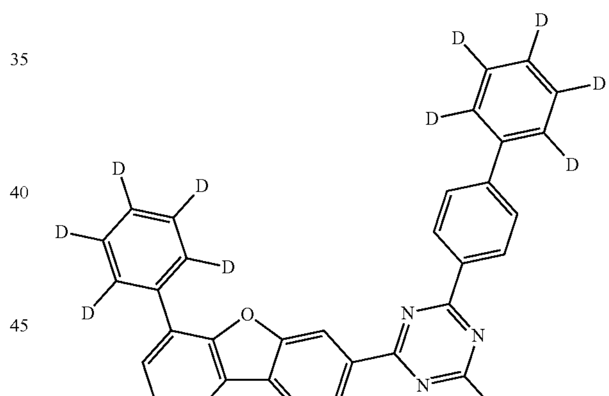
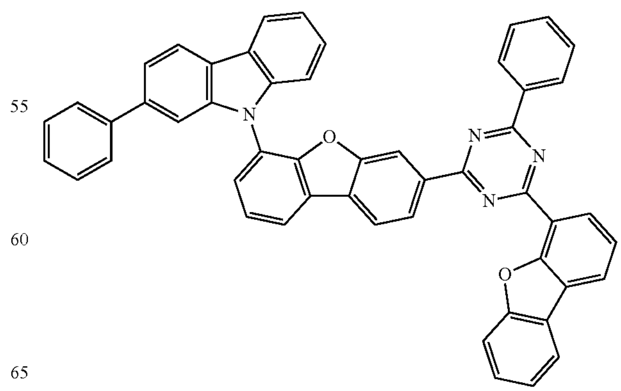

-continued
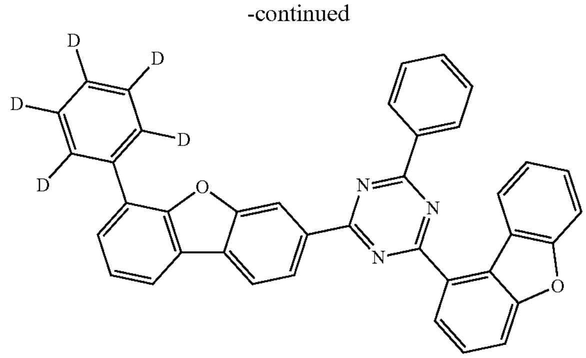
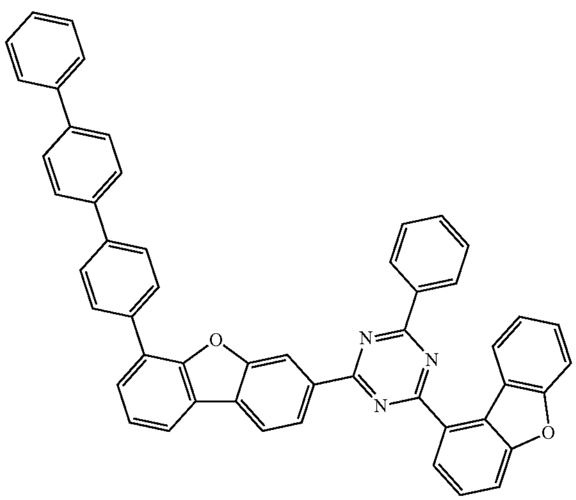
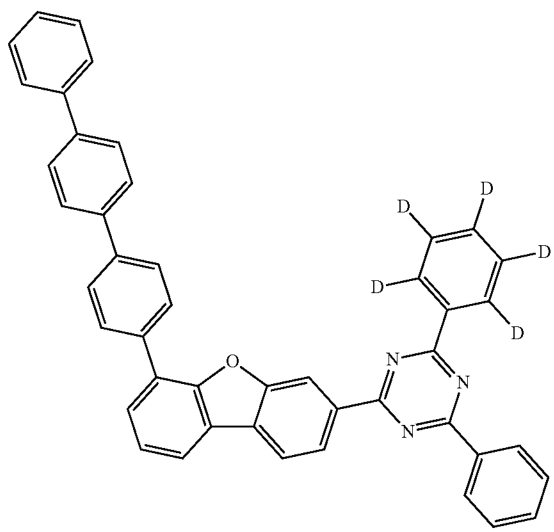
-continued
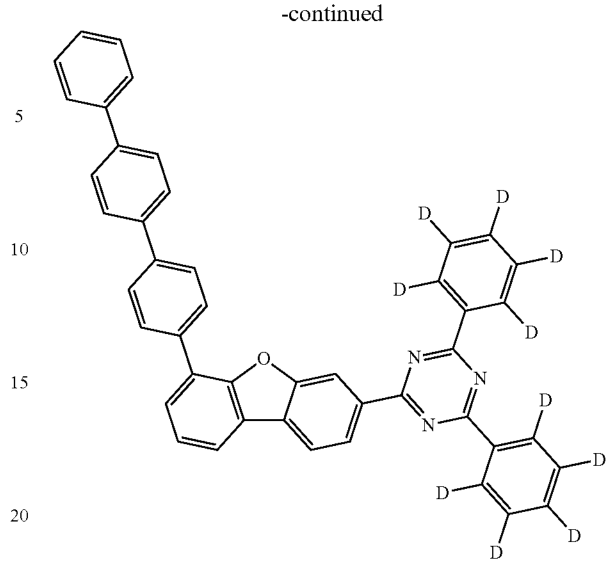
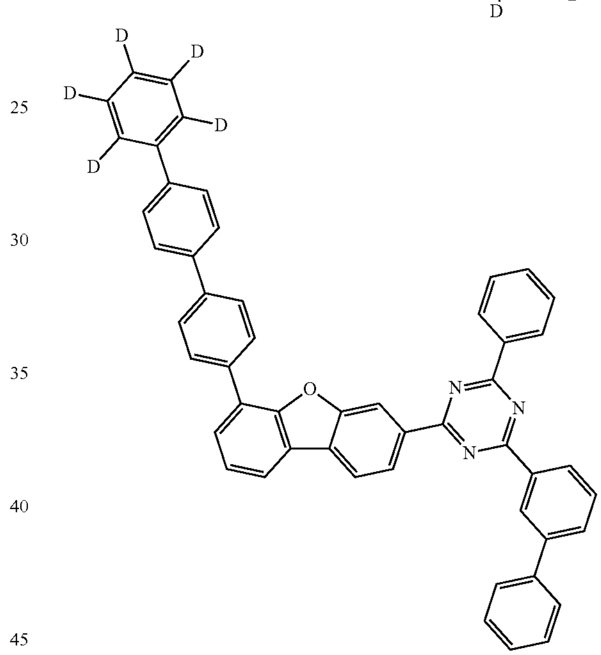
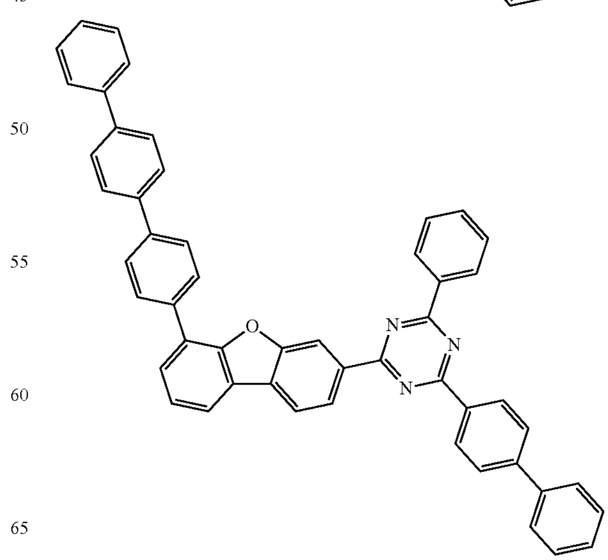

-continued
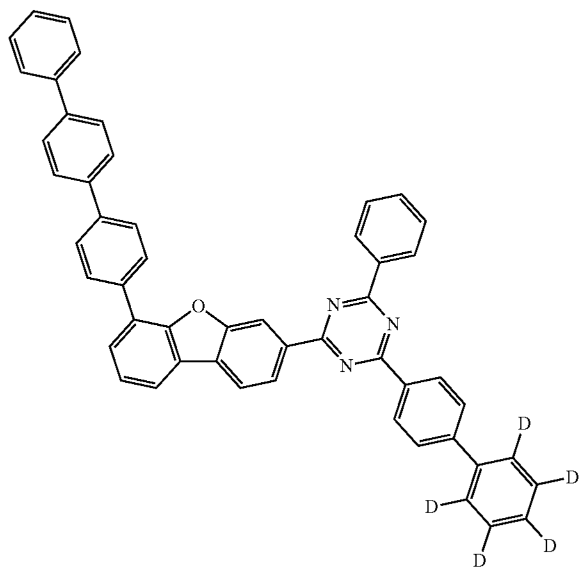
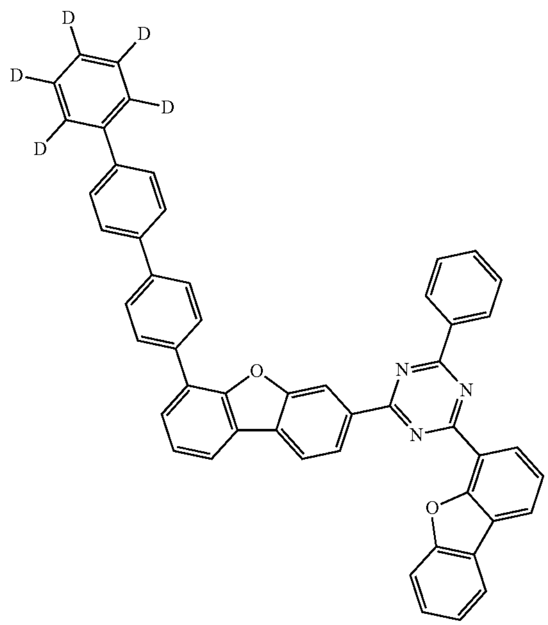
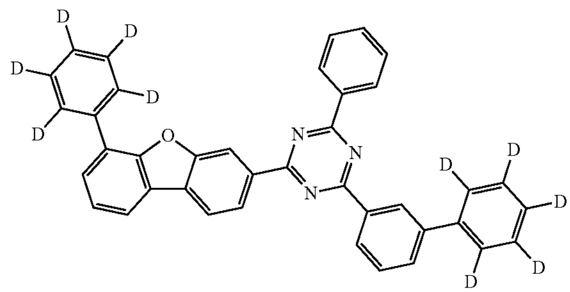 [SMILES: [2H]c1c([2H])c([2H])c(-c2cccc(-c3nc(-c4ccccc4)nc(-c4ccc5c(c4)oc4c(-c6c([2H])c([2H])c([2H])c([2H])c6[2H])cccc45)n3)c2)c([2H])c1[2H]]
-continued
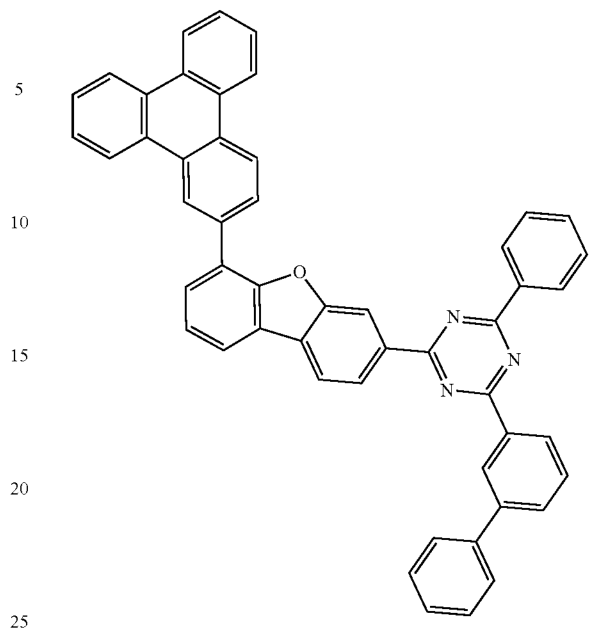
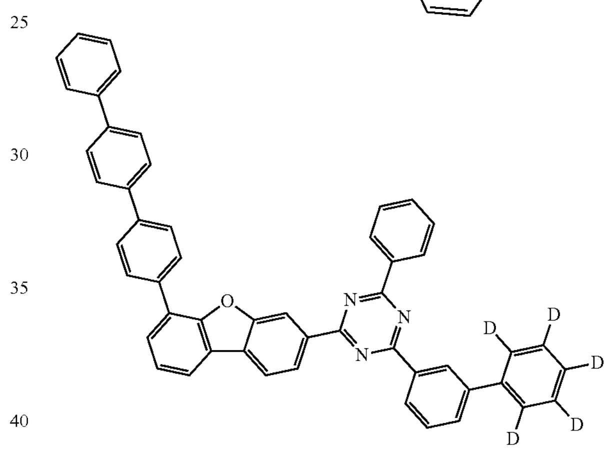
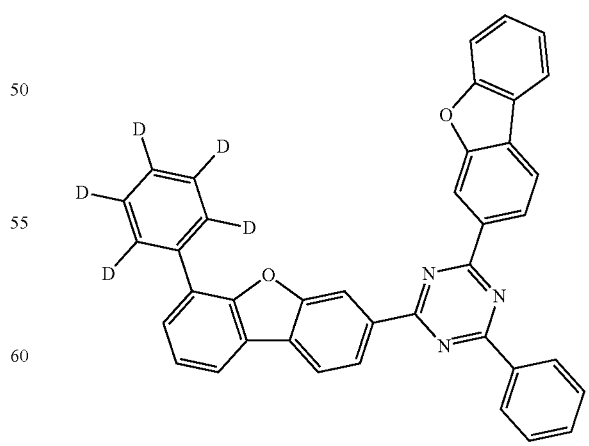

-continued
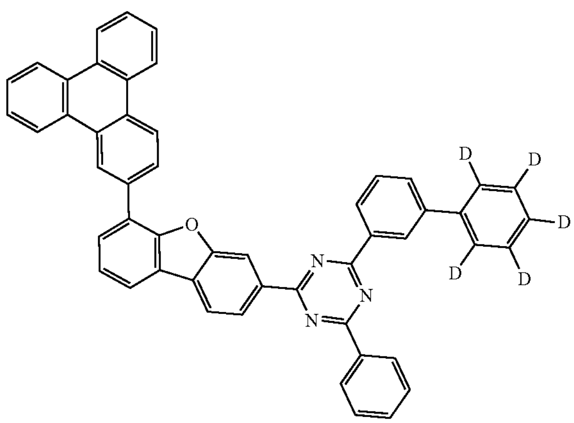
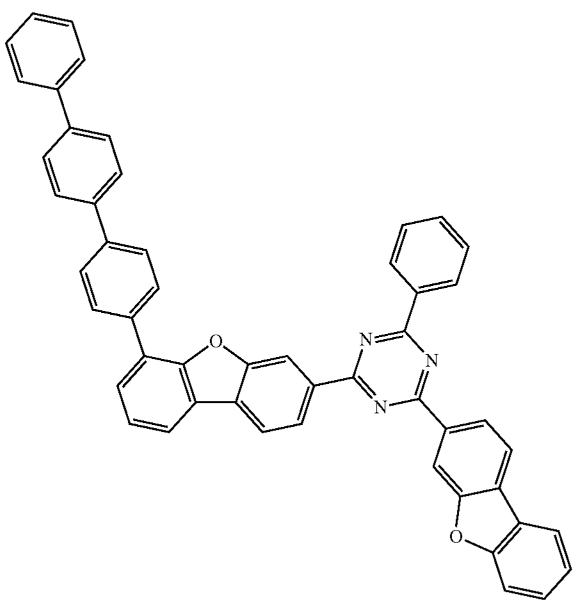
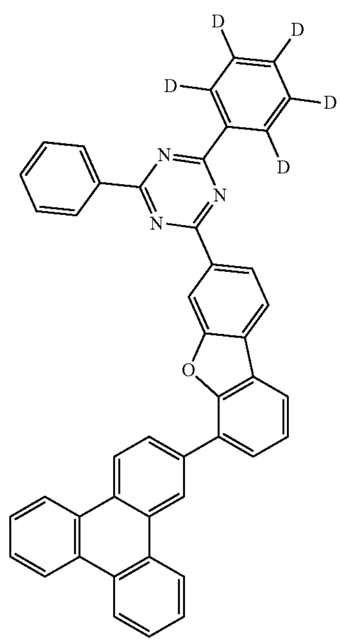
-continued
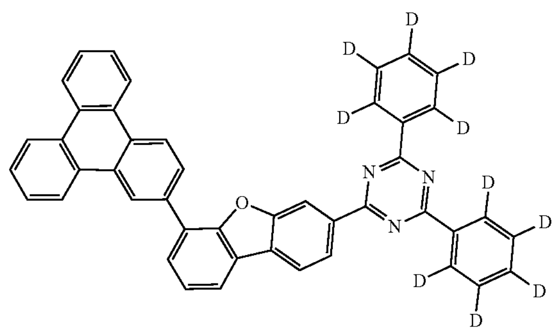
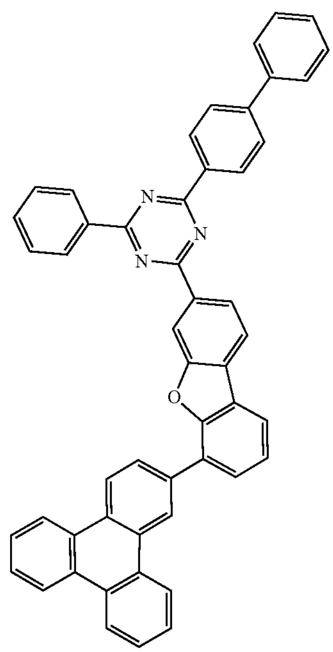
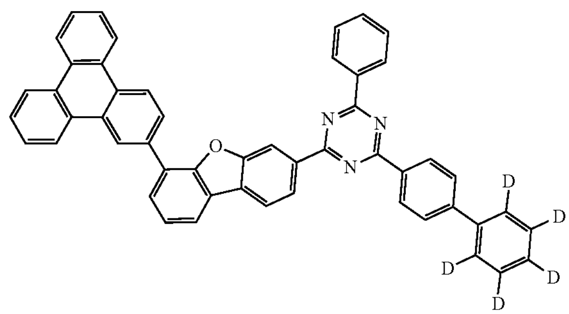
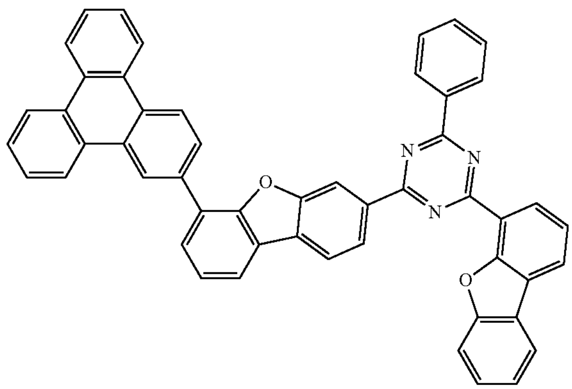

-continued
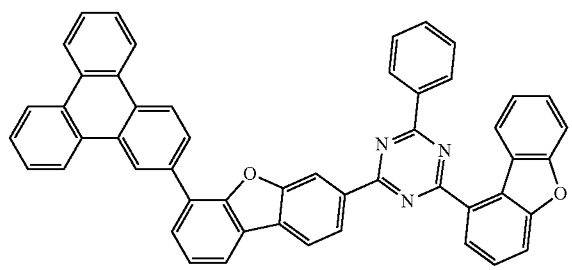
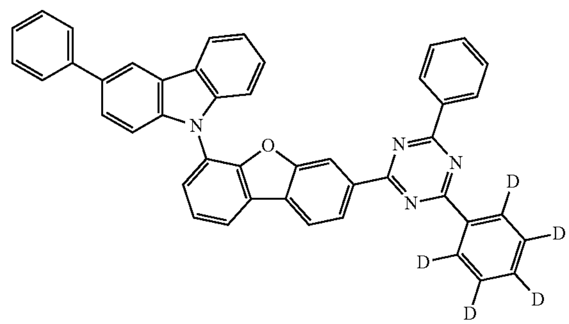
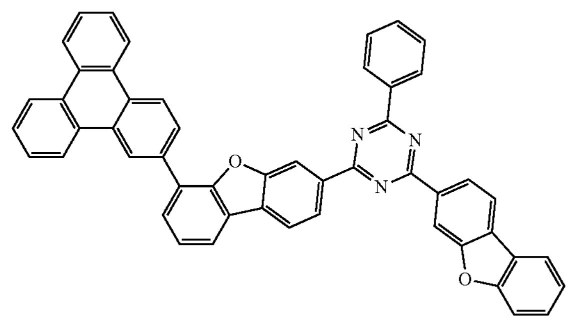
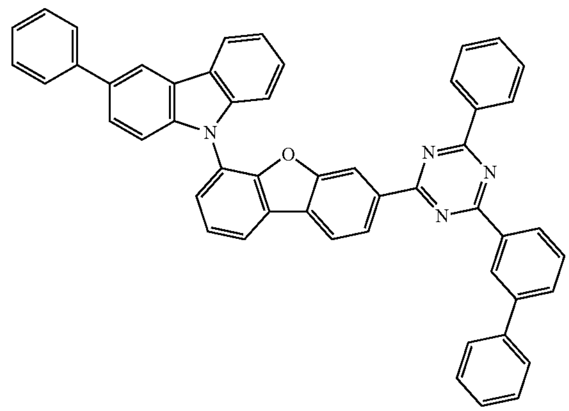
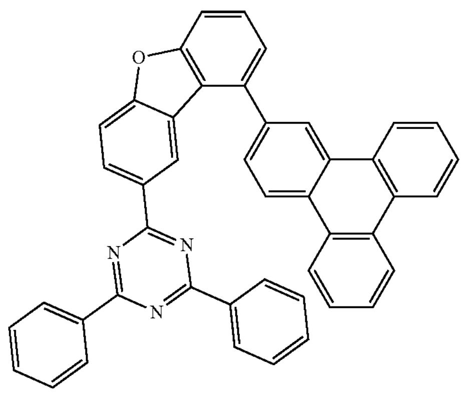
-continued
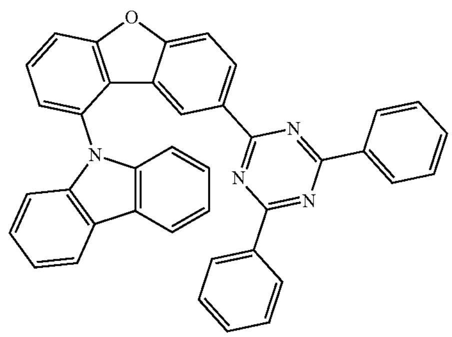
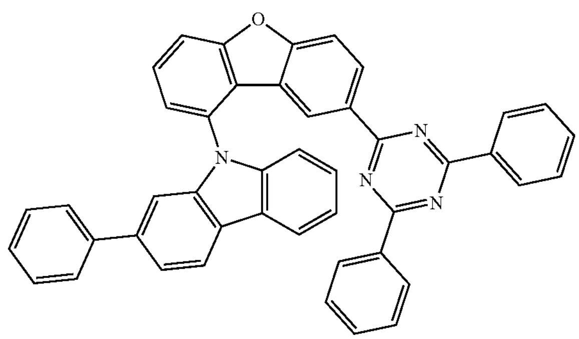
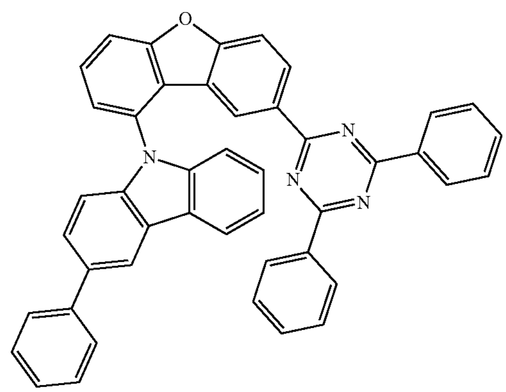
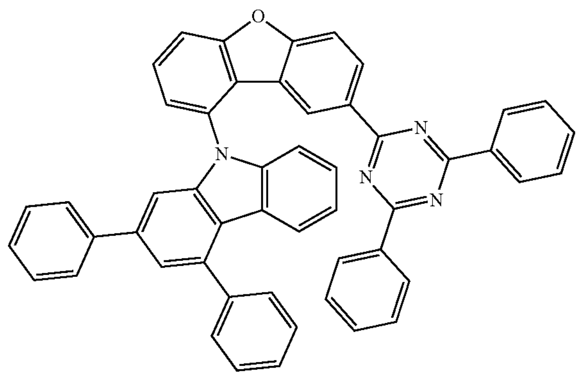

-continued
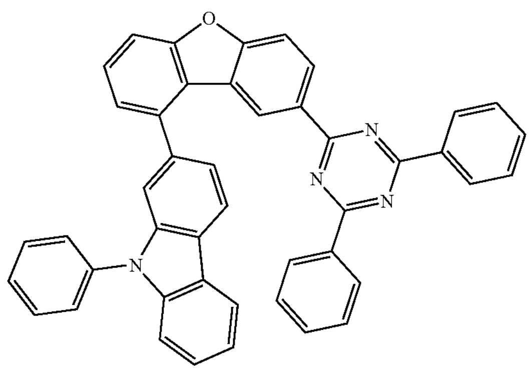
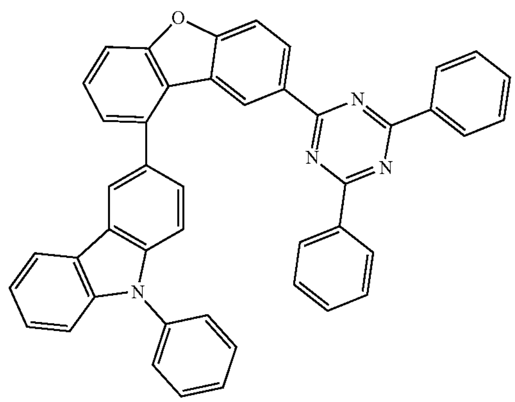
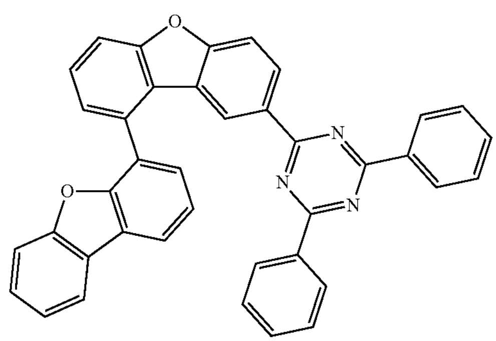
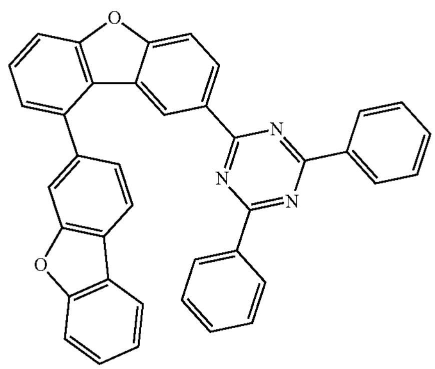
-continued
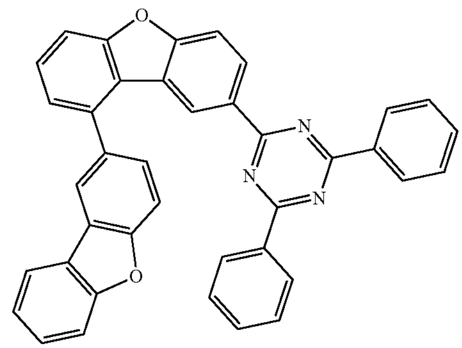
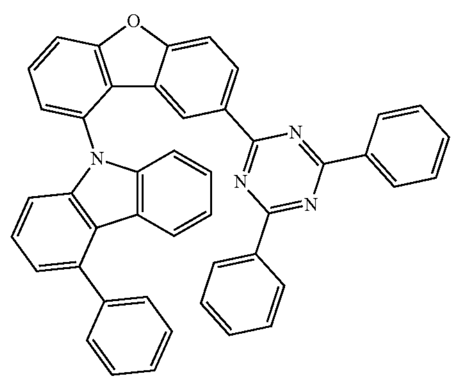
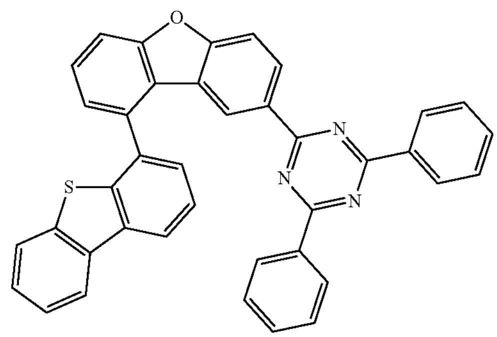
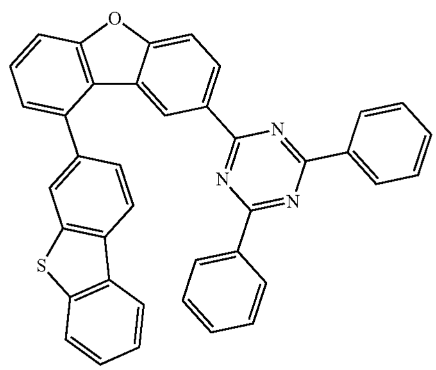

-continued
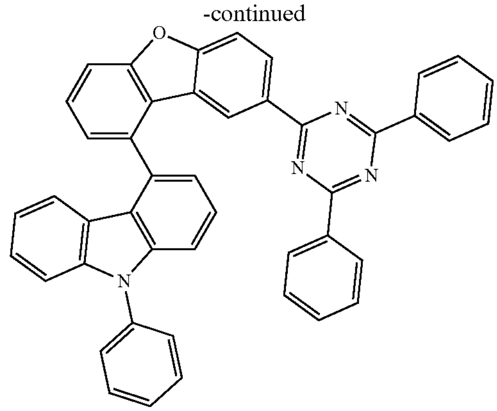
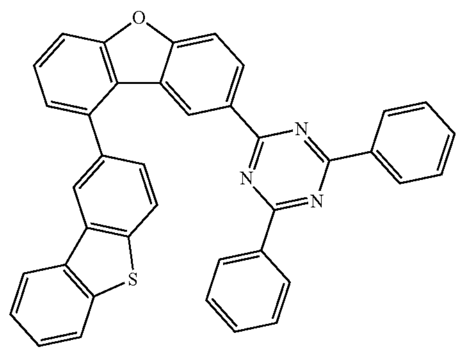
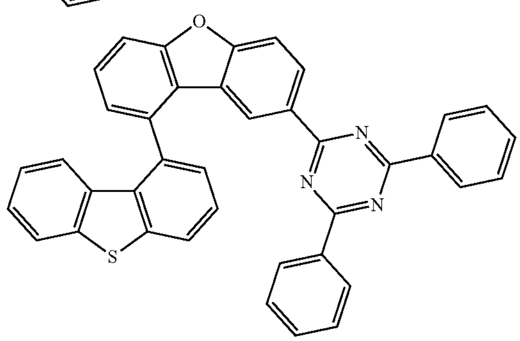
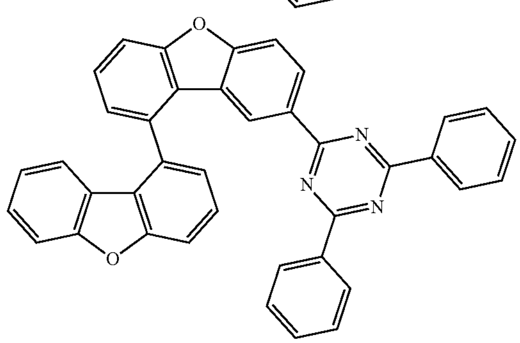
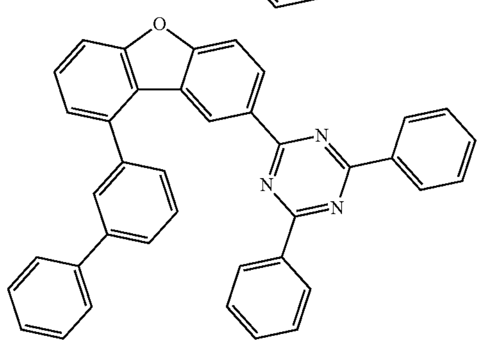
-continued
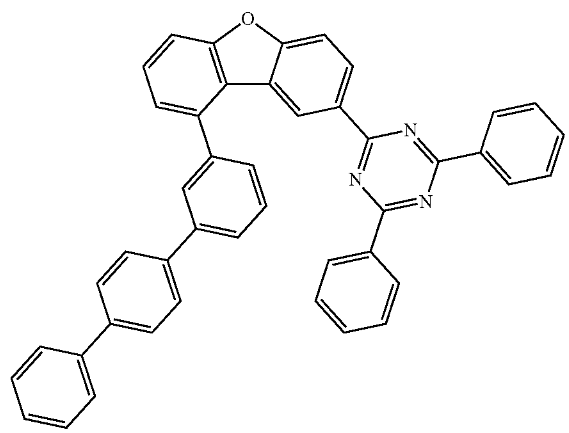
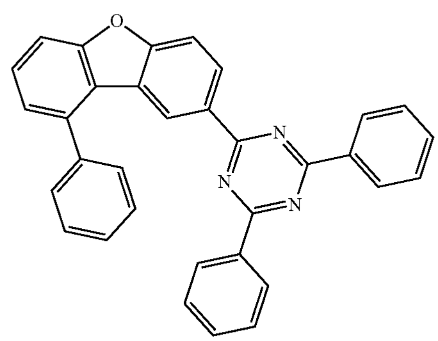
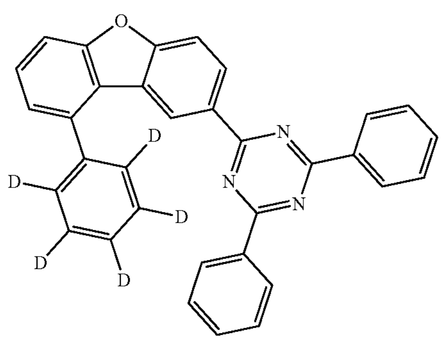
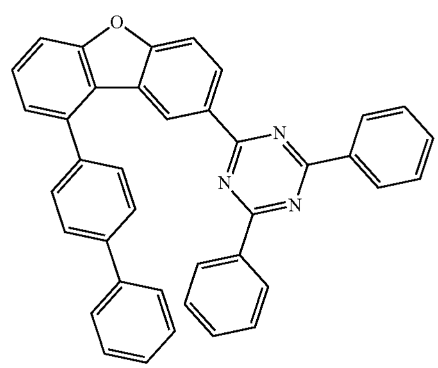

-continued
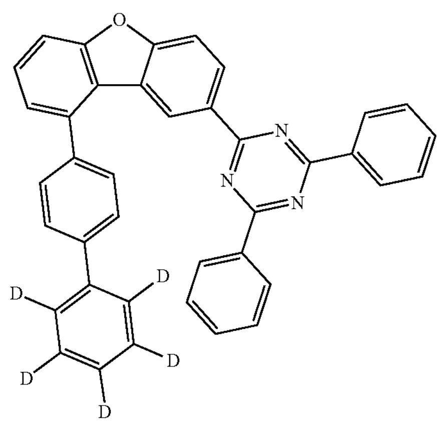
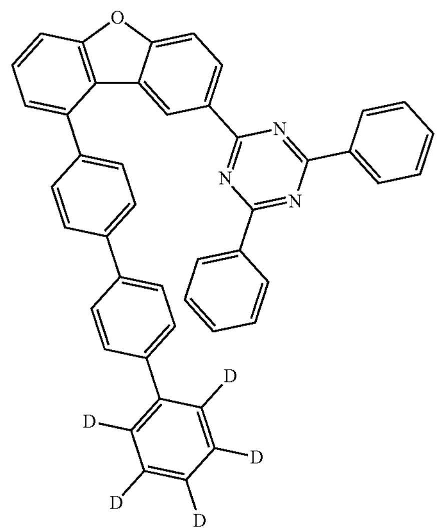
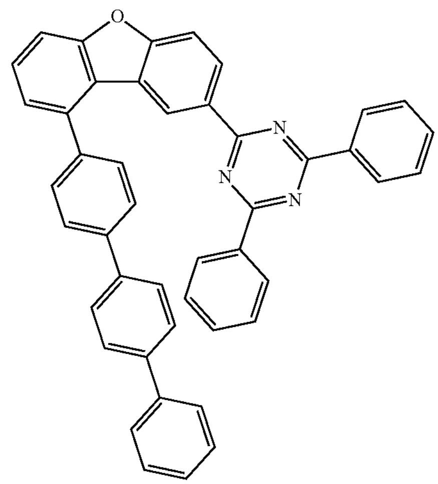
-continued
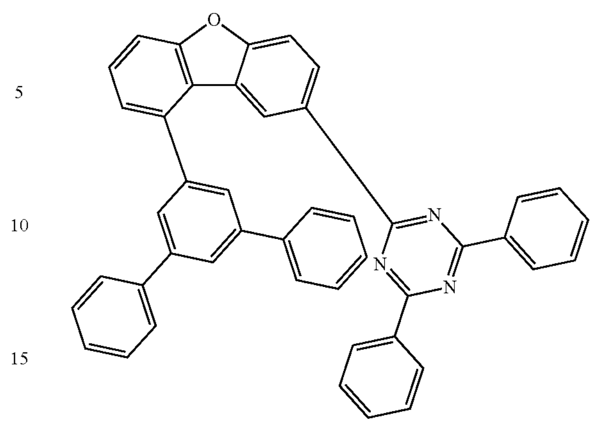
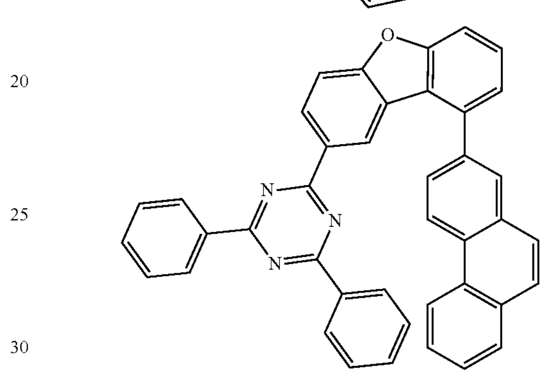
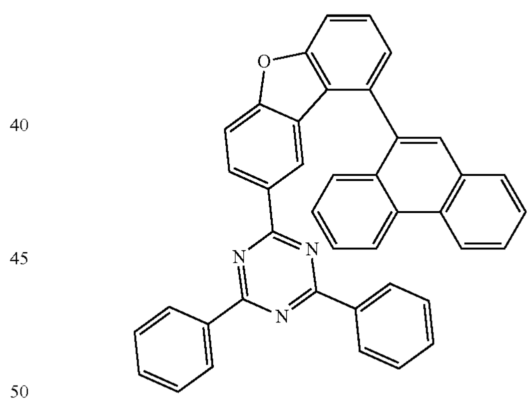
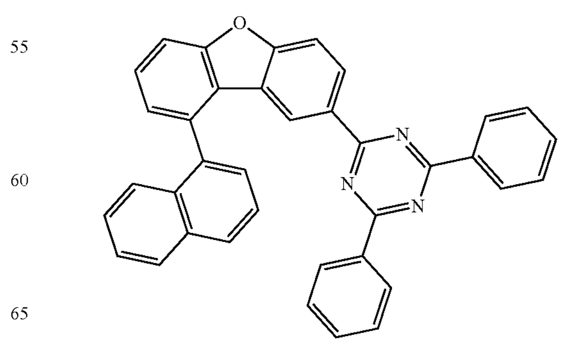

-continued
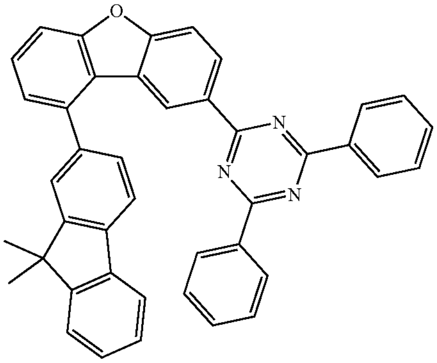
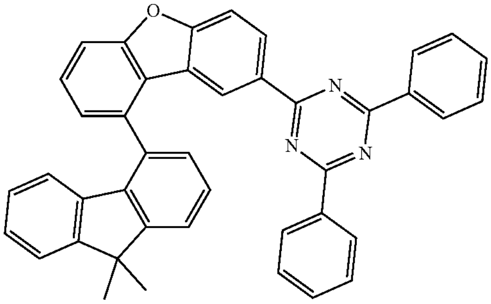
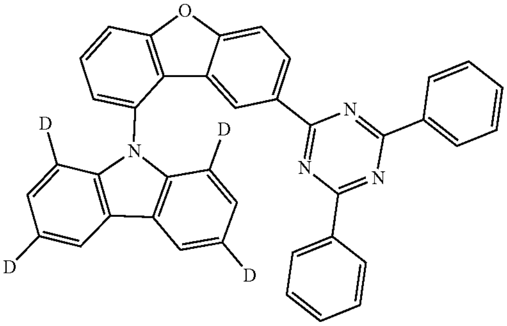
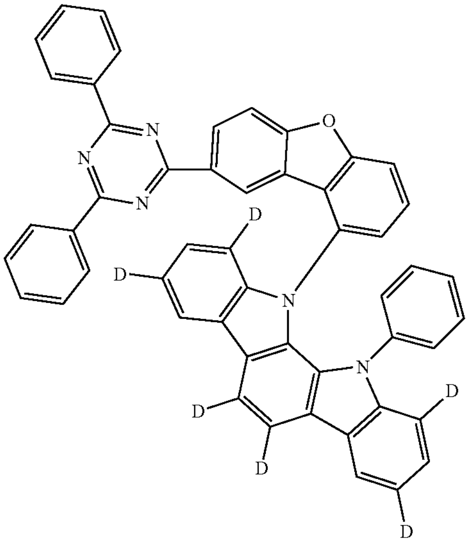
-continued
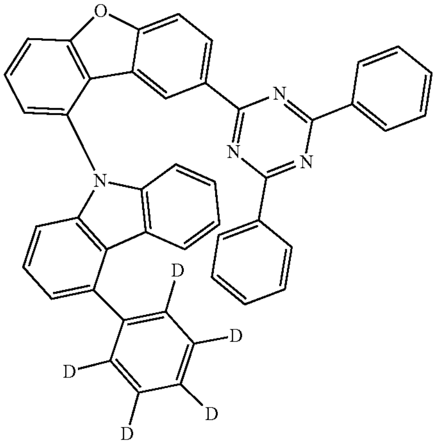
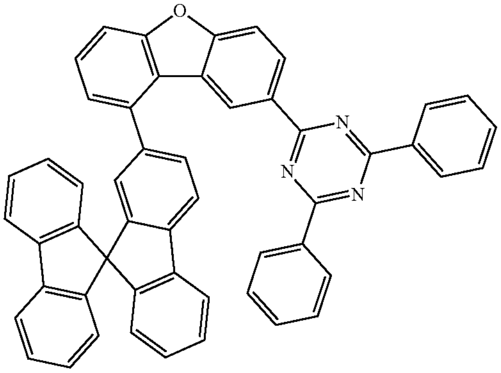
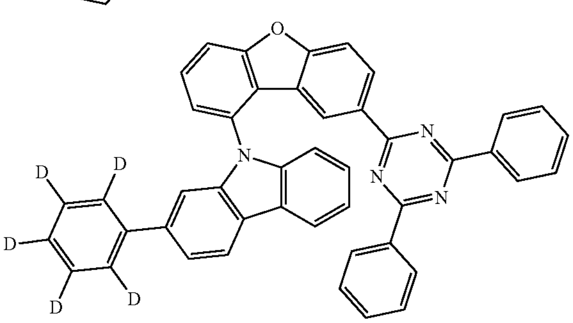
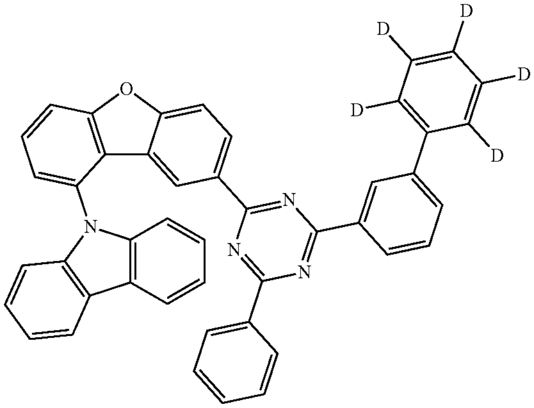

-continued
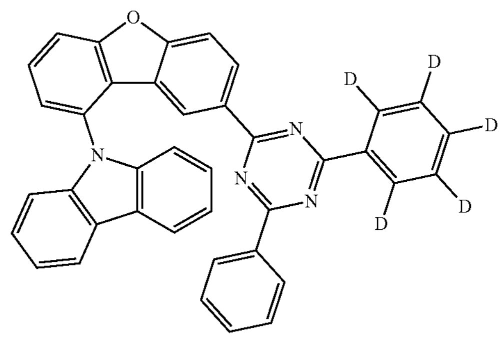
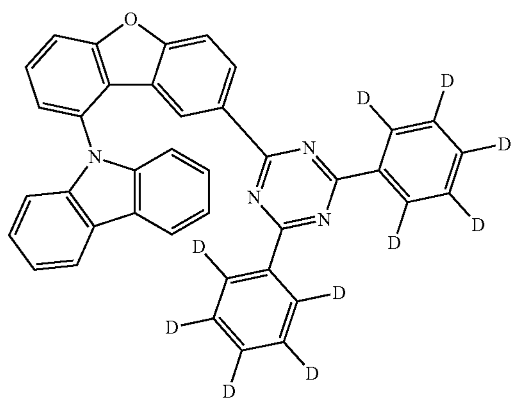
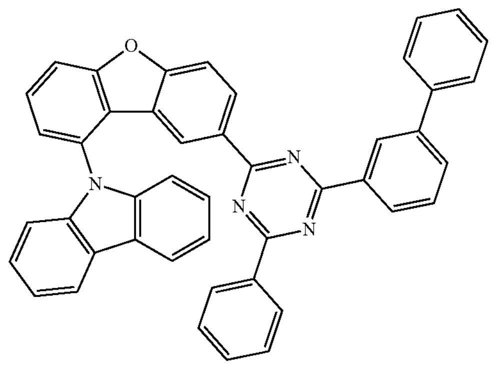
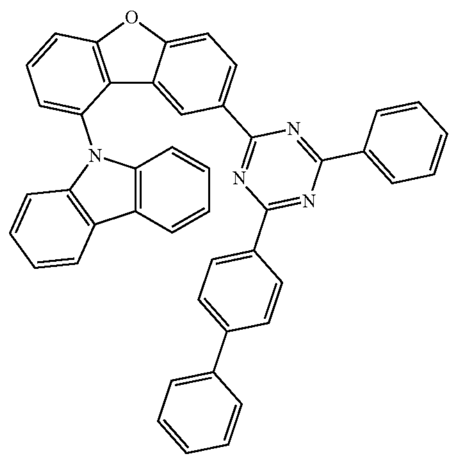
-continued
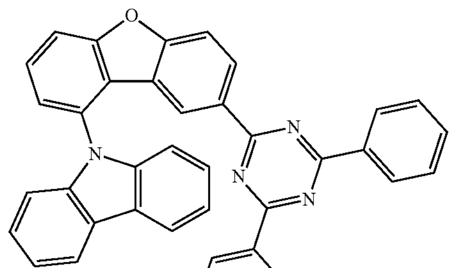
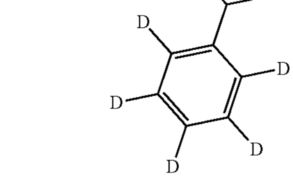
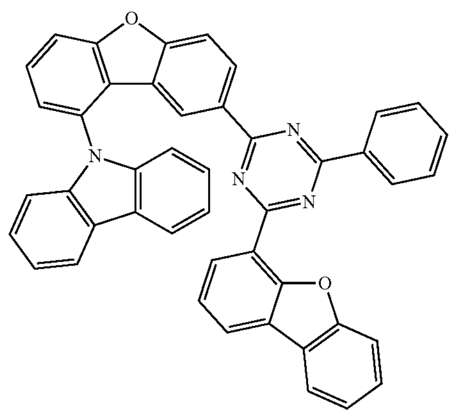
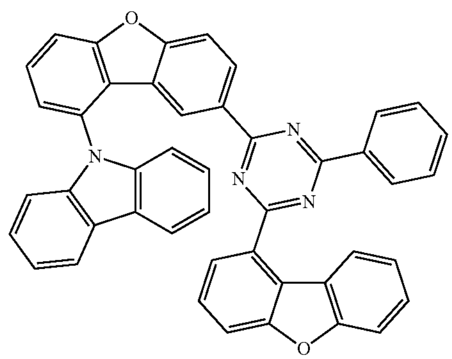
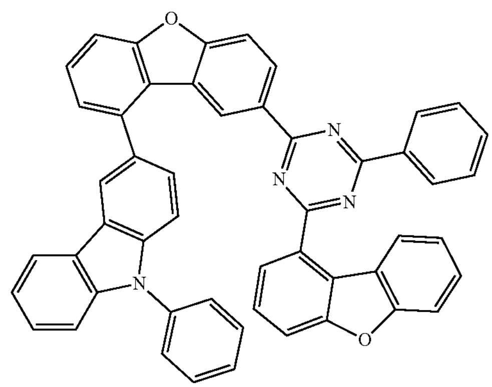

-continued
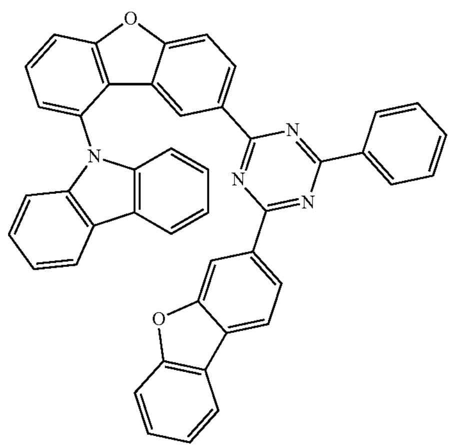
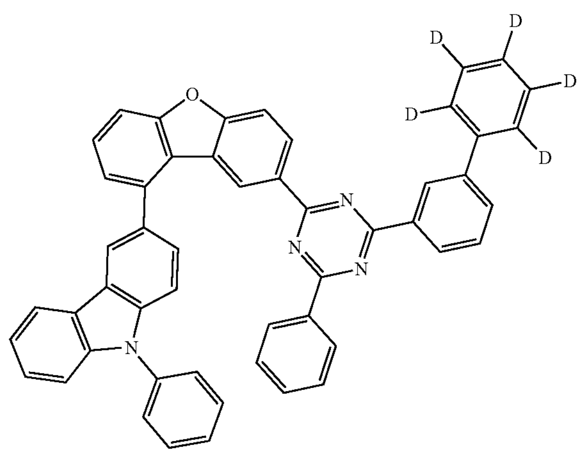
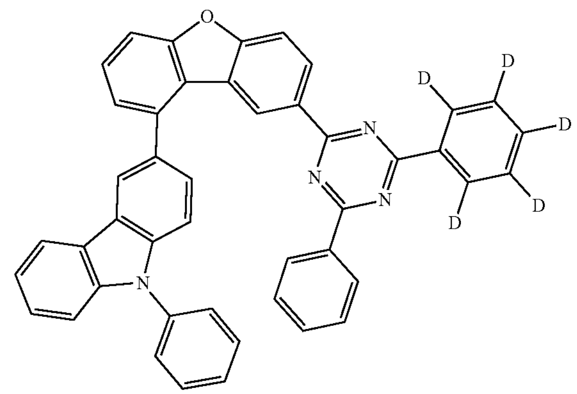
-continued
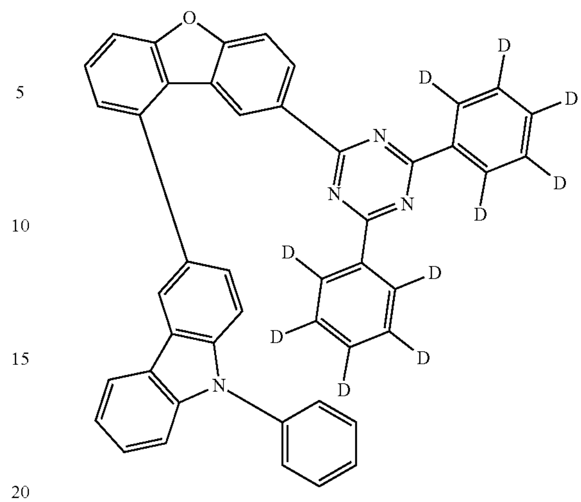
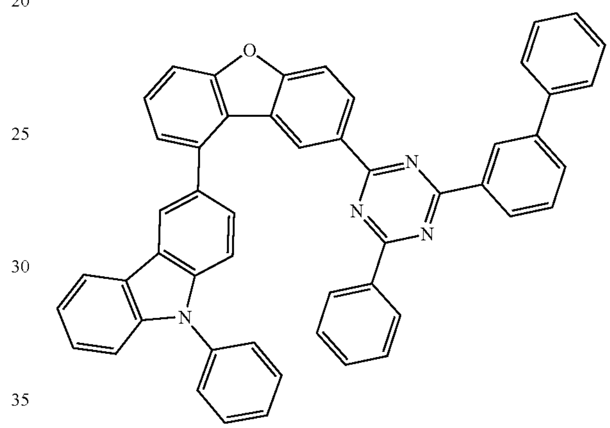
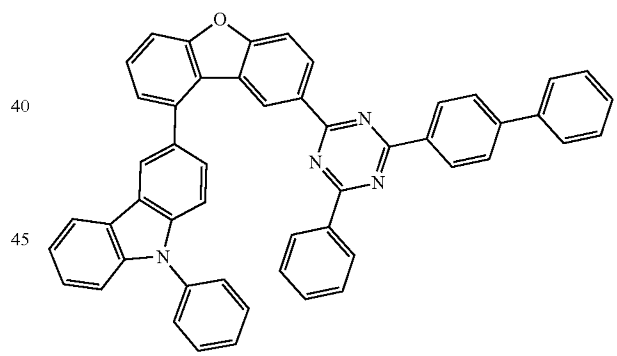
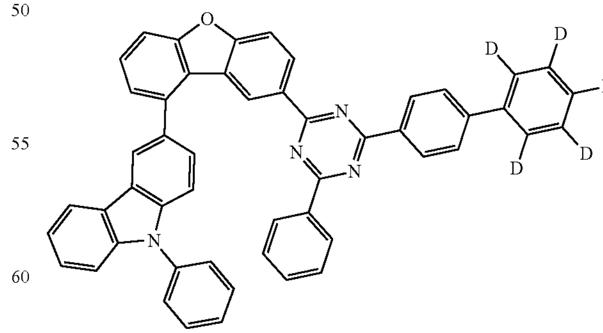

-continued
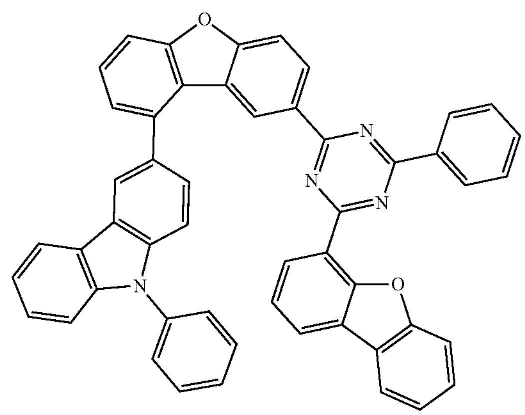
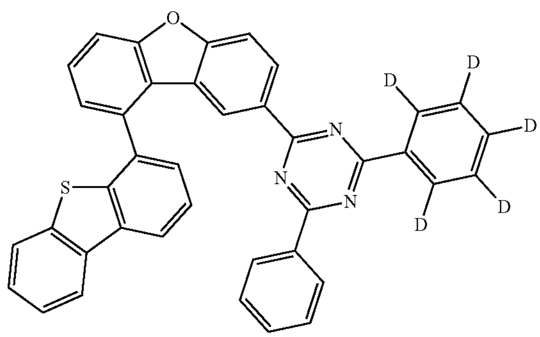
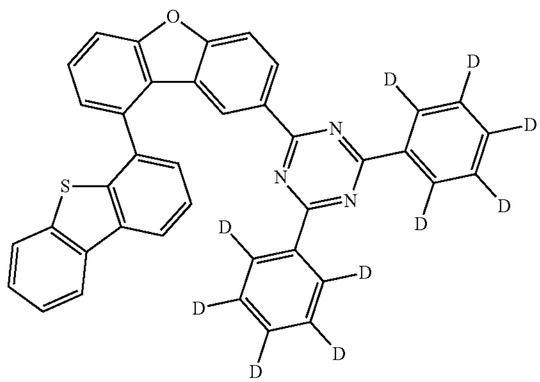
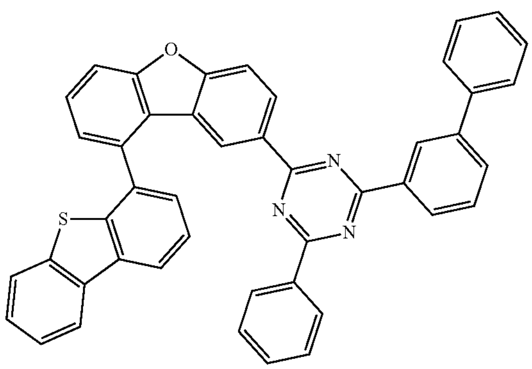
-continued
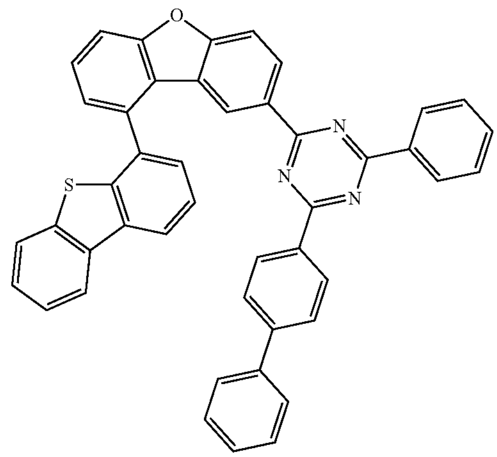
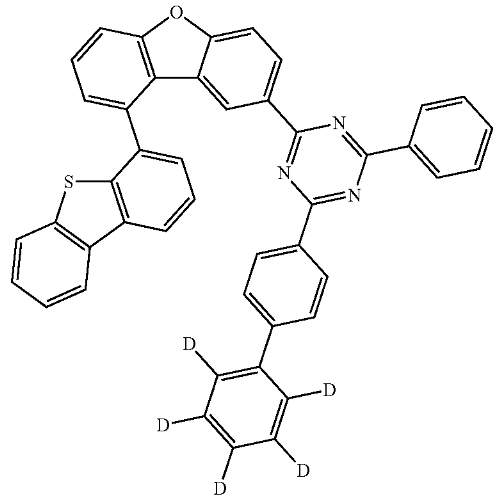
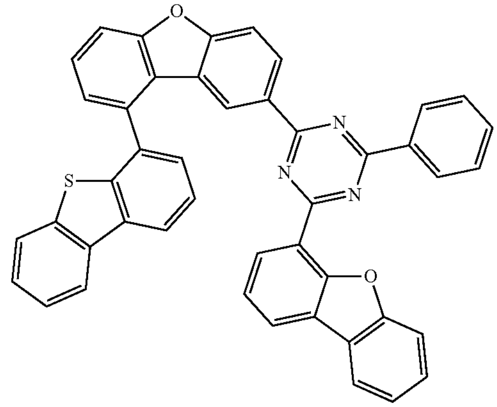
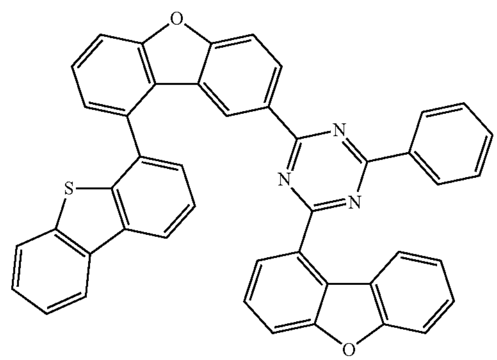

-continued
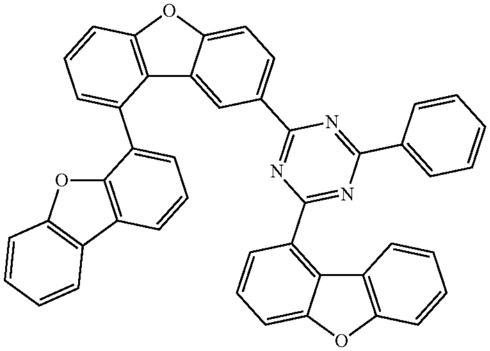
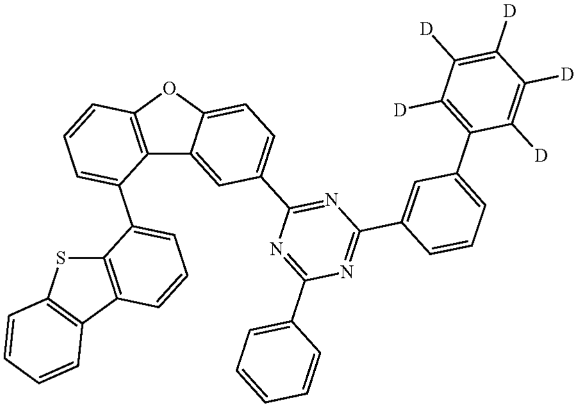
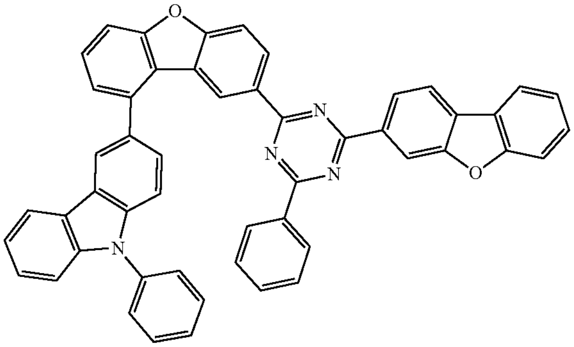
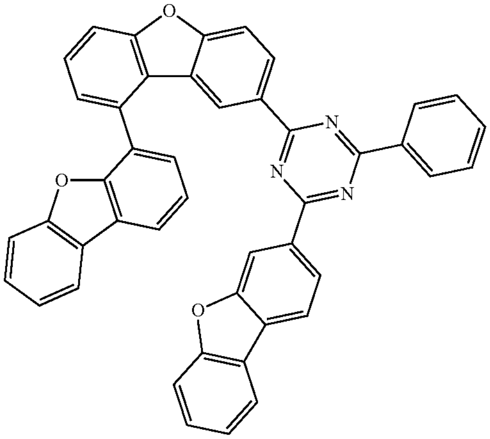
-continued
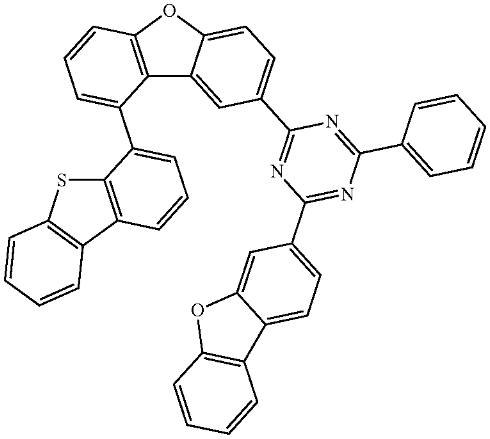
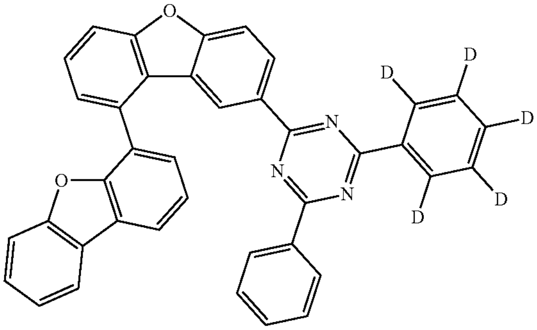
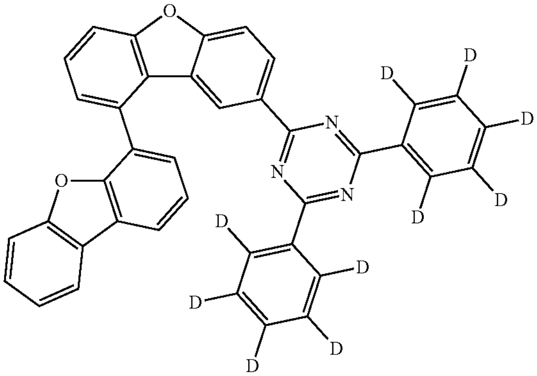
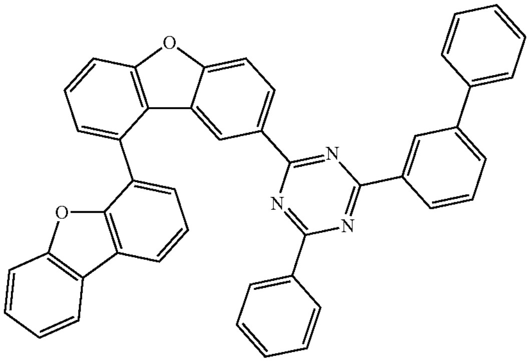

-continued
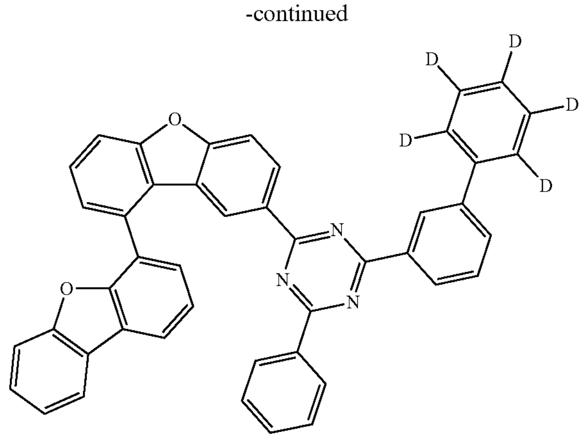
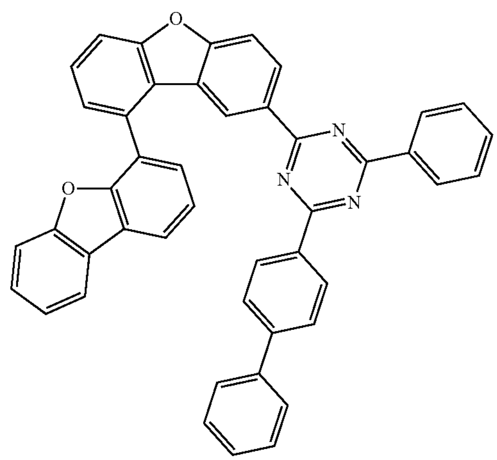
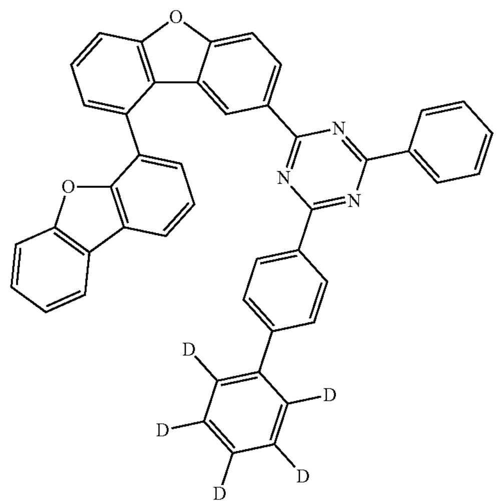
-continued
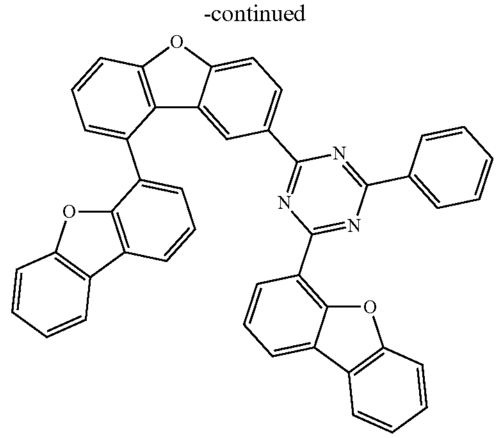
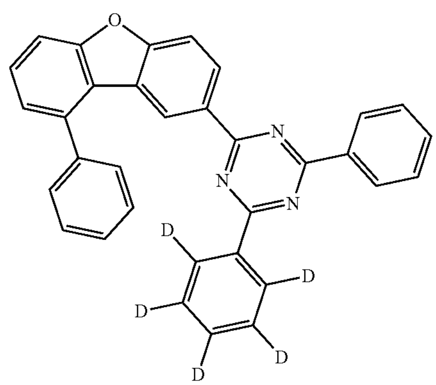
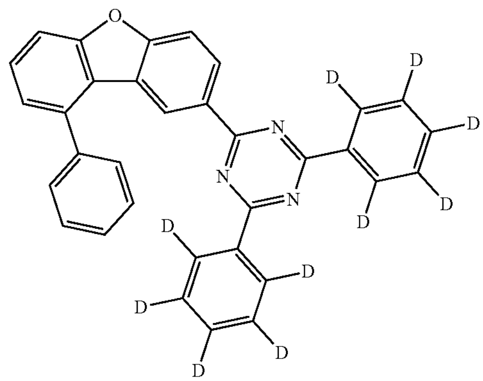
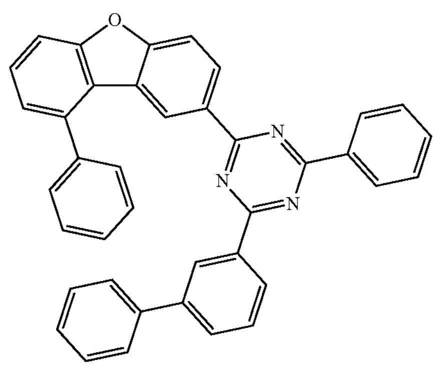

-continued
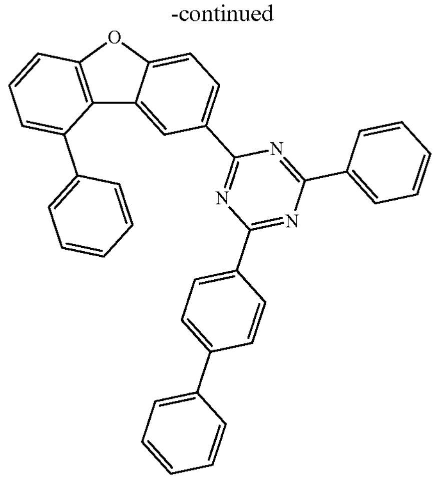
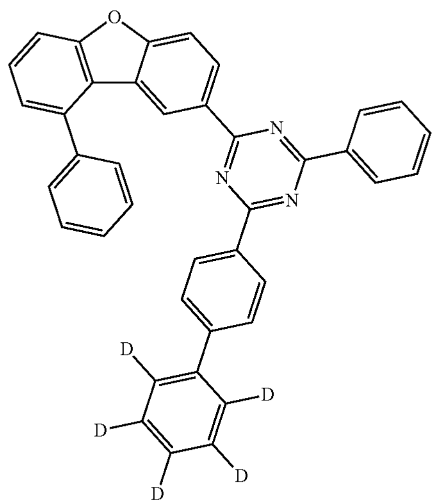
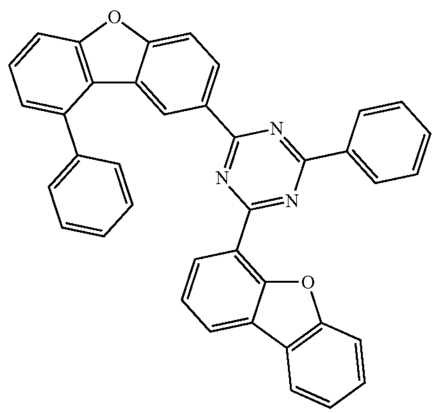
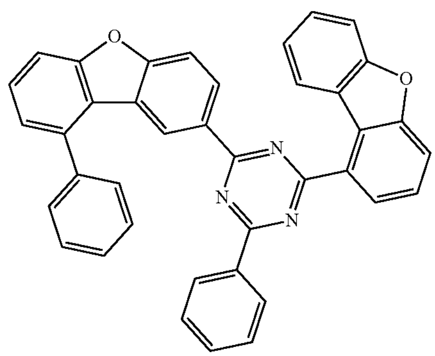
-continued
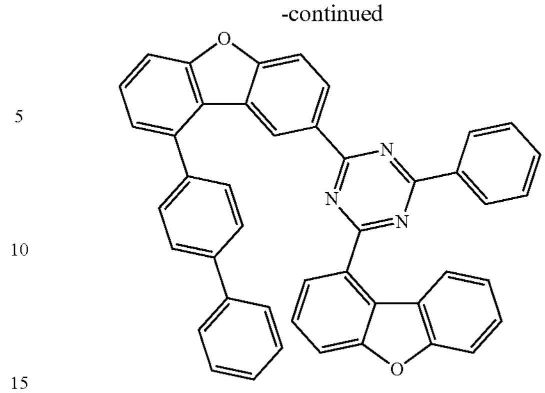
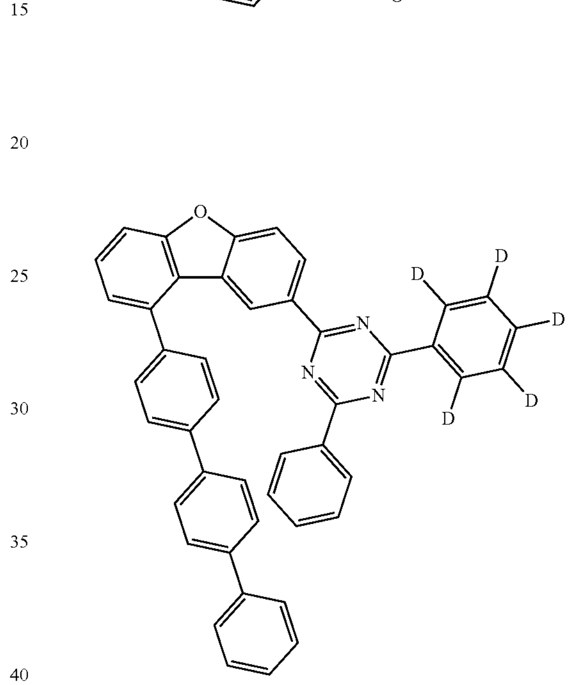
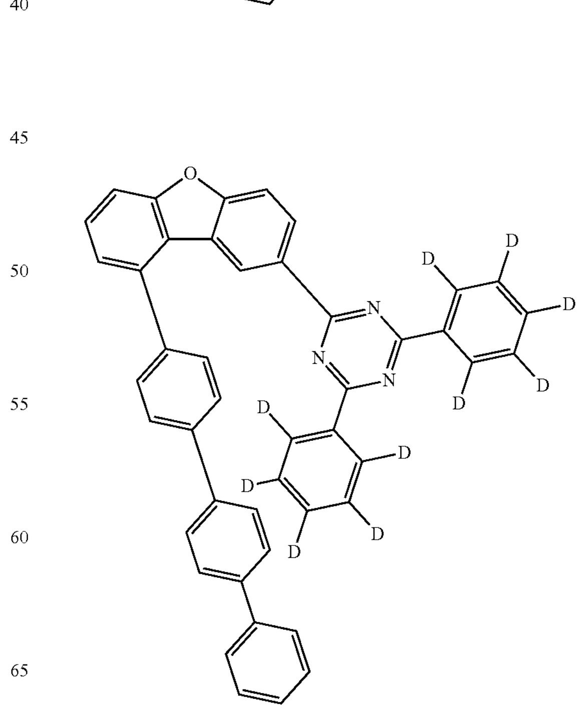

-continued
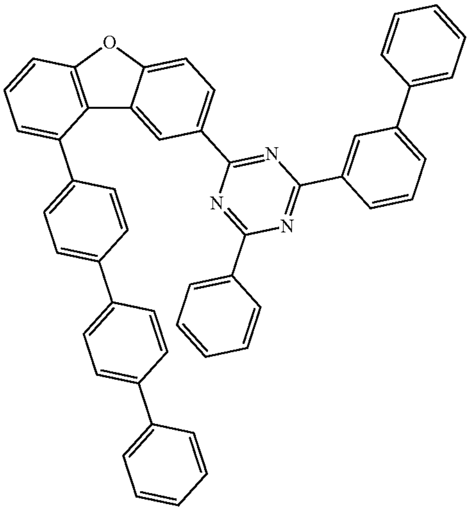
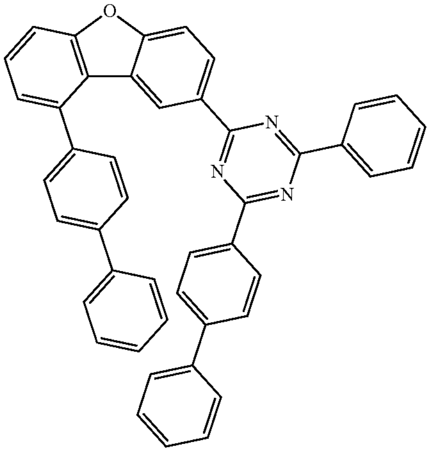
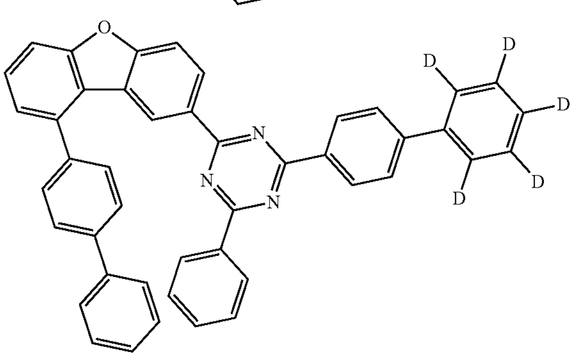
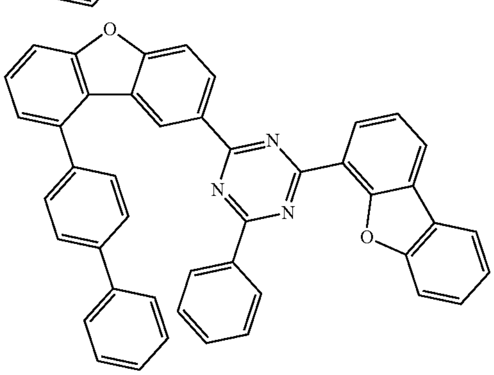
-continued
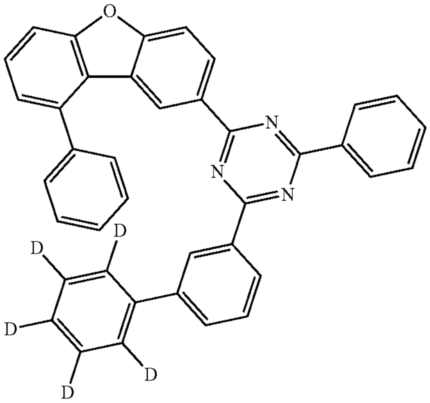
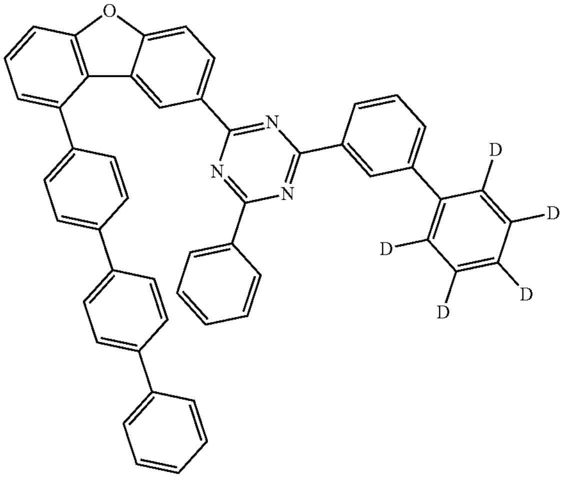
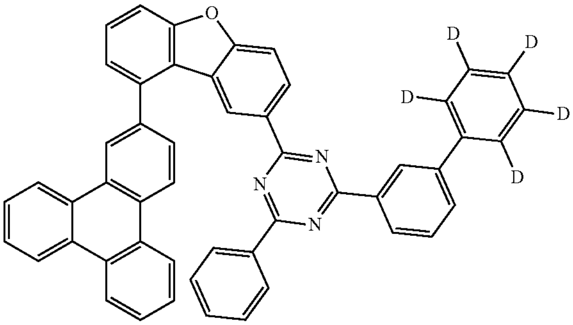
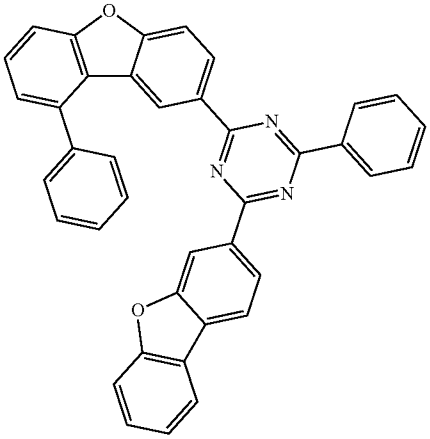

-continued
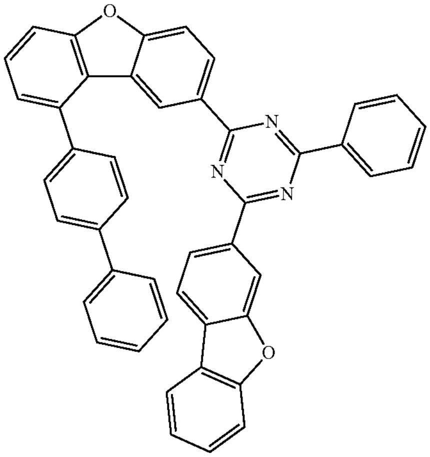
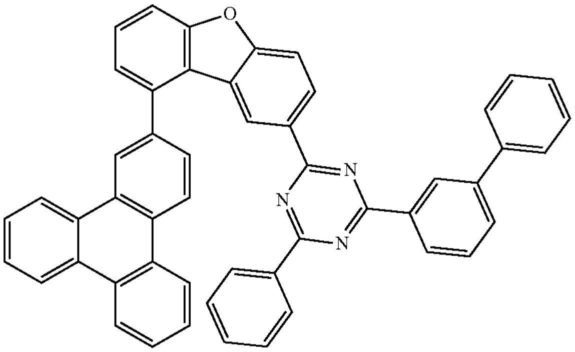
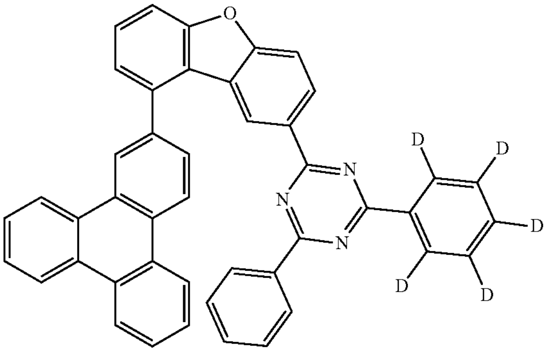
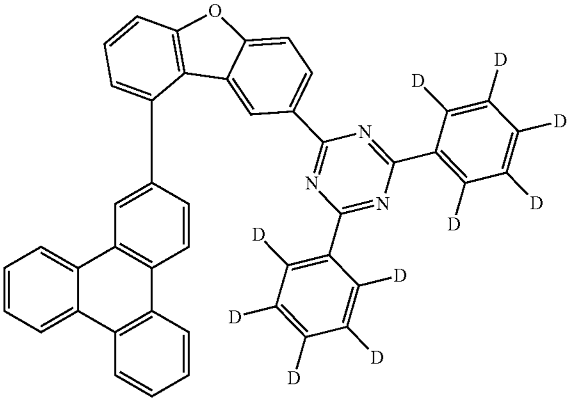
-continued
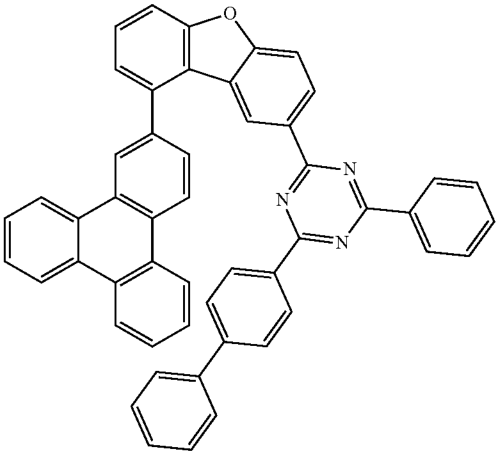
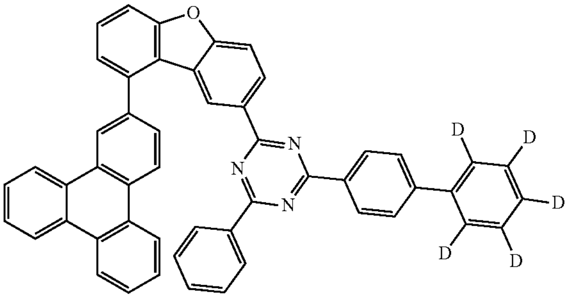
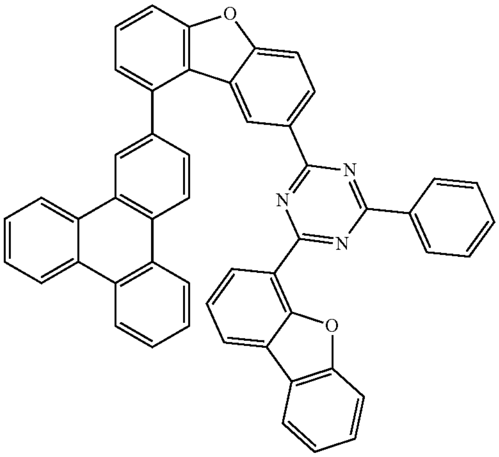
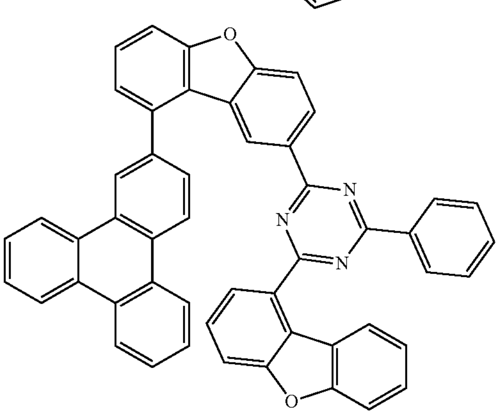

-continued
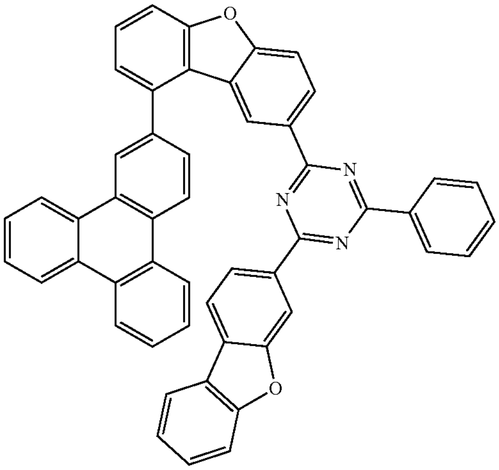
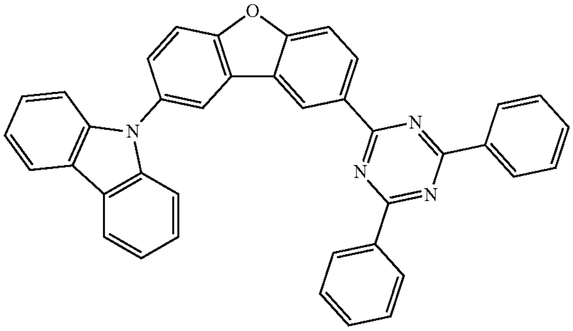
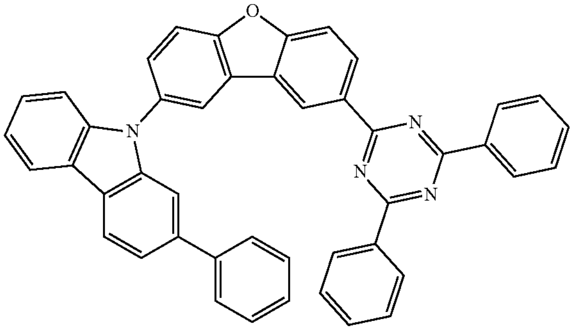
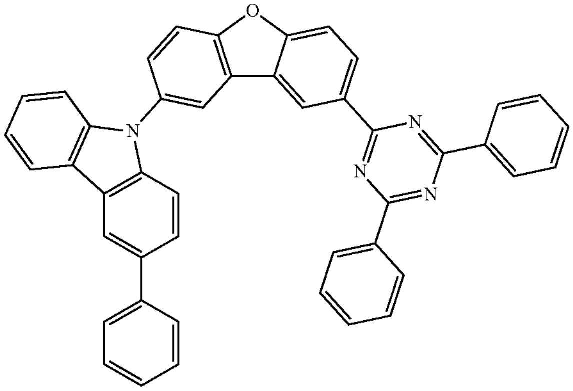
-continued
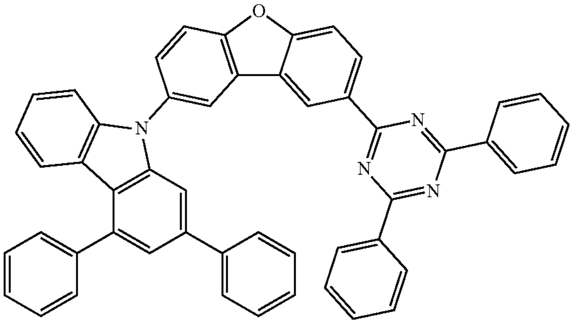
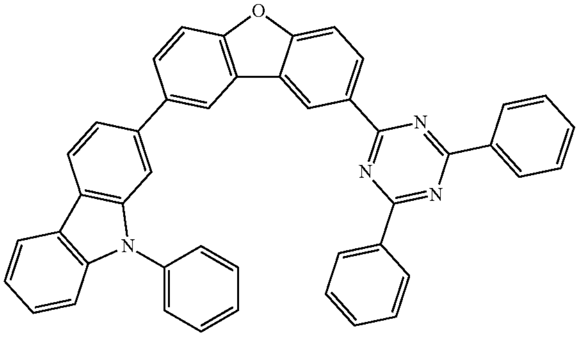
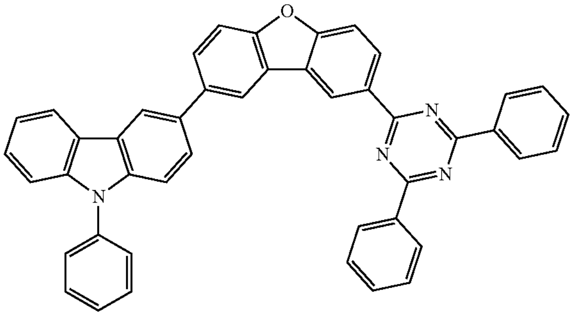
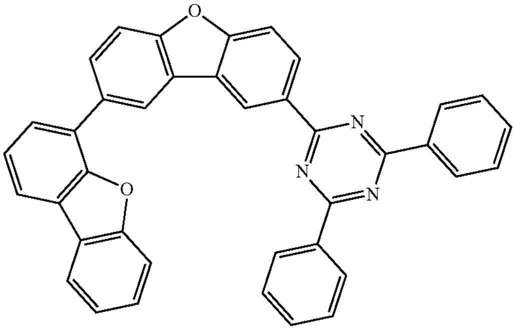
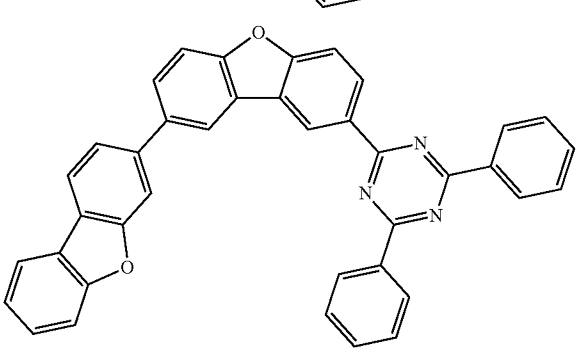

-continued
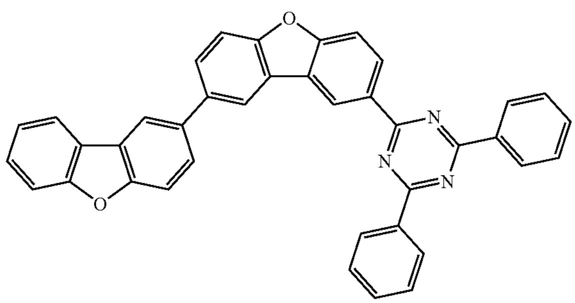
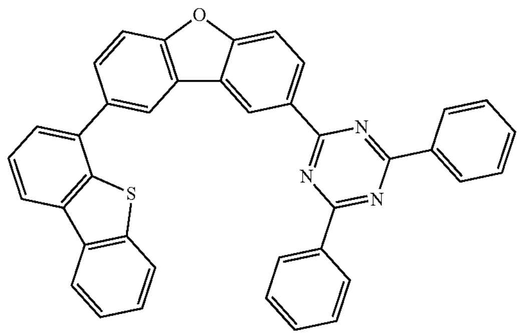
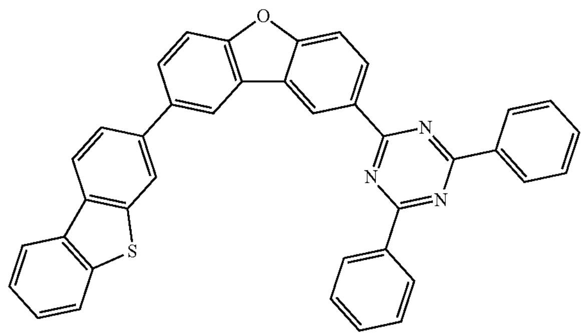
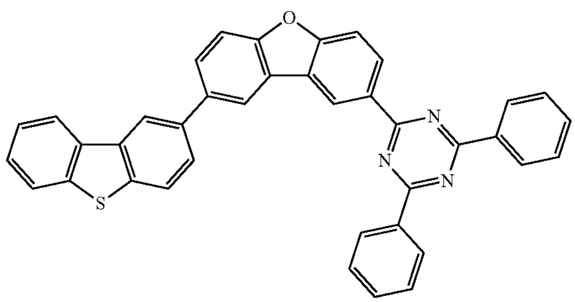
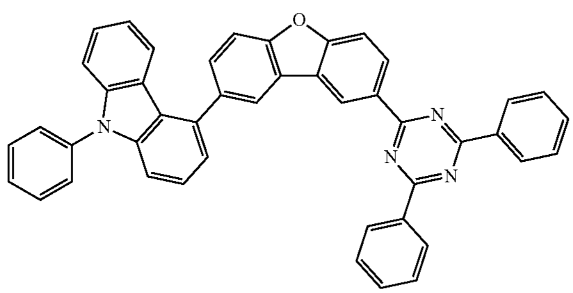
-continued
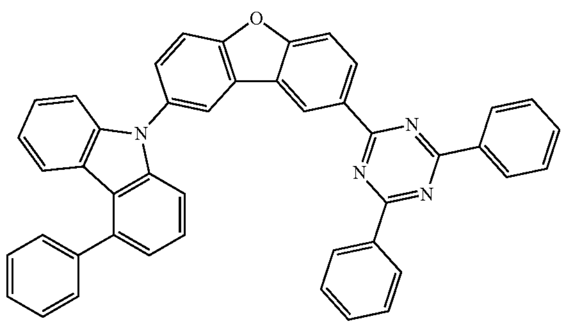
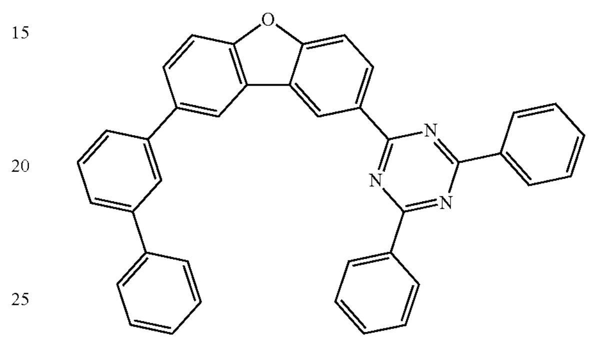
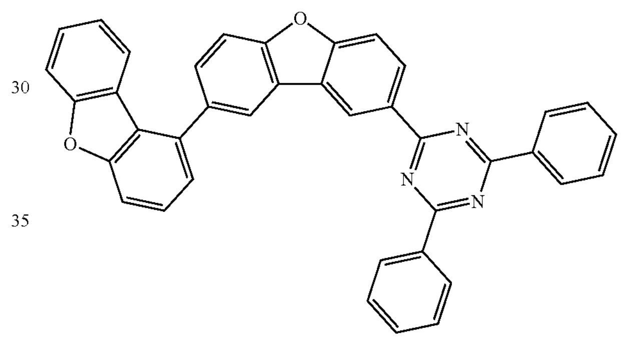
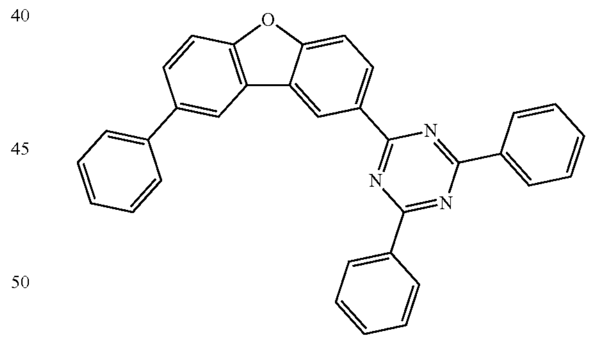
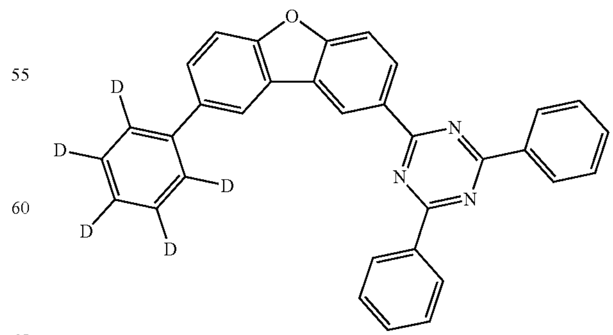

-continued
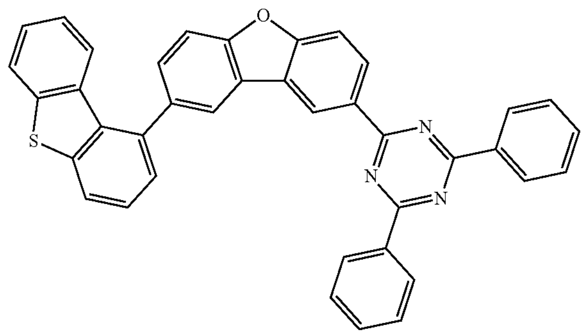
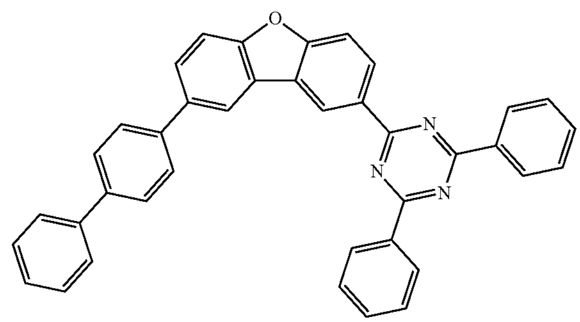
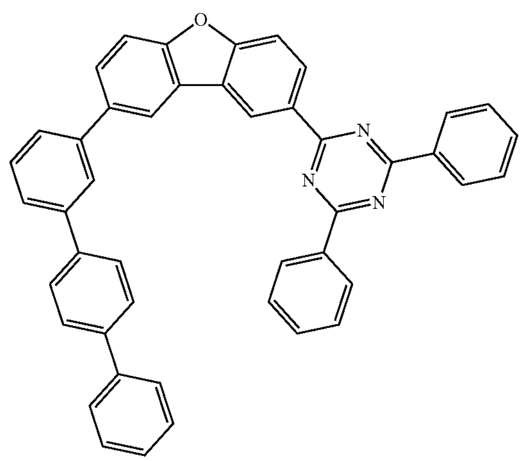 [SMILES: c1ccc(-c2ccc(-c3cccc(-c4ccc5oc6ccc(-c7nc(-c8ccccc8)nc(-c8ccccc8)n7)cc6c5c4)c3)cc2)cc1]
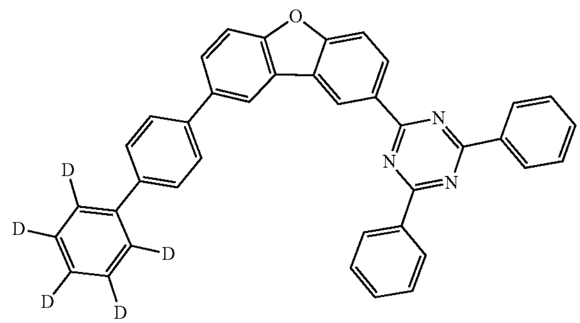
-continued
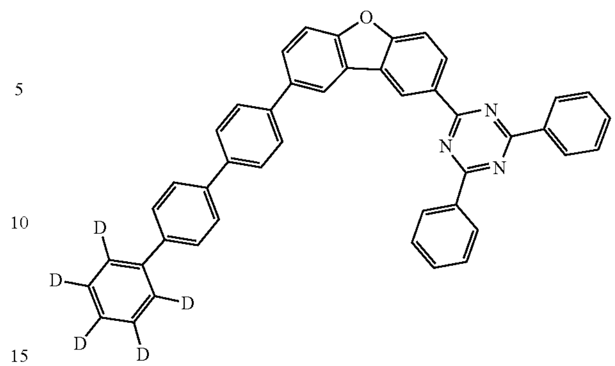
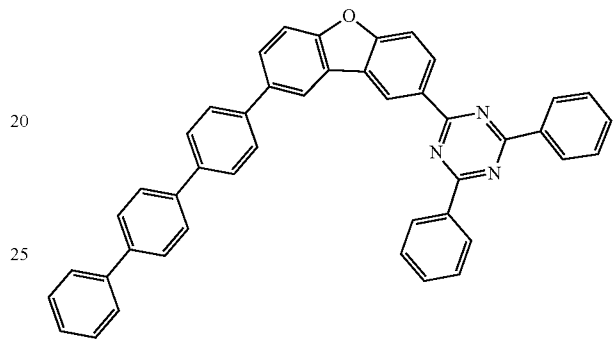
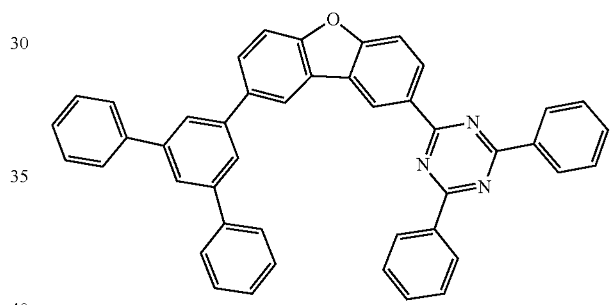
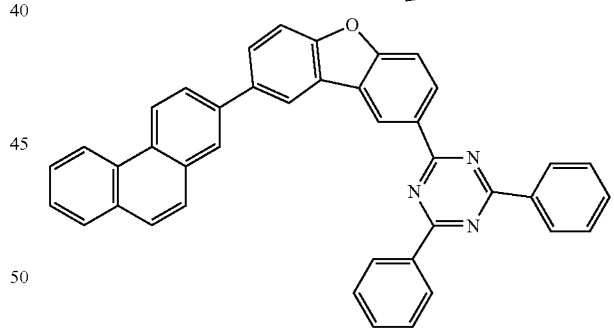
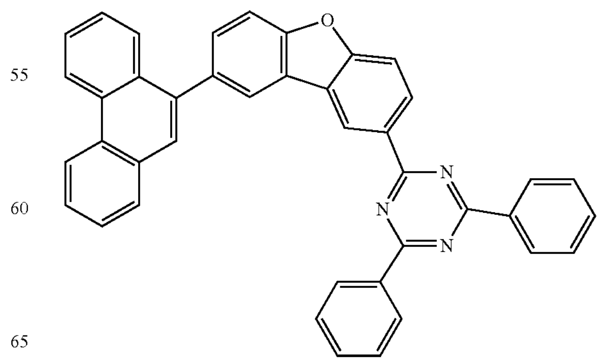

-continued
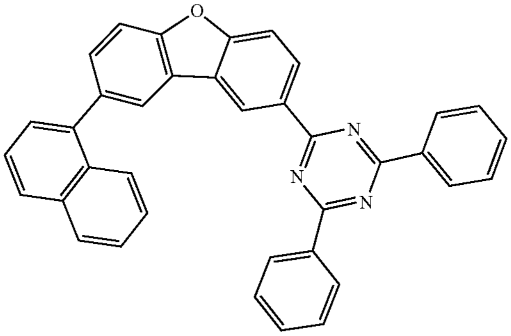
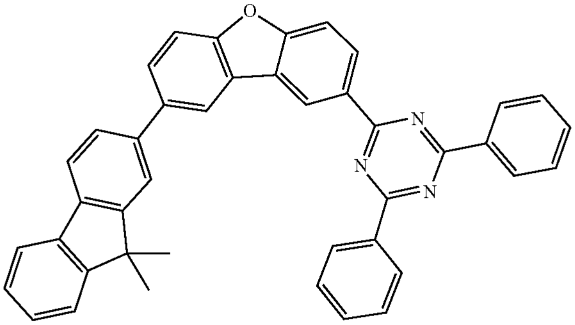
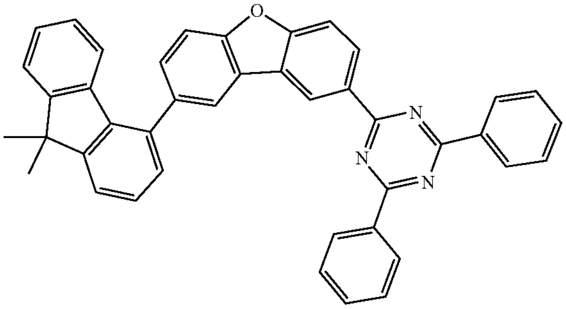
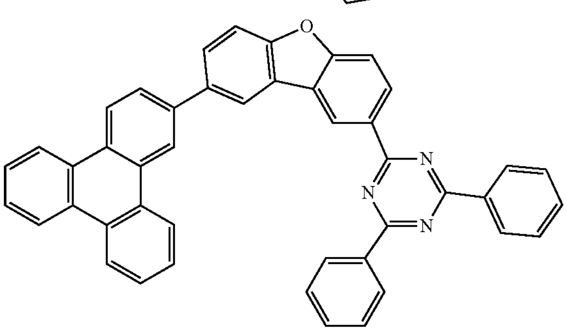
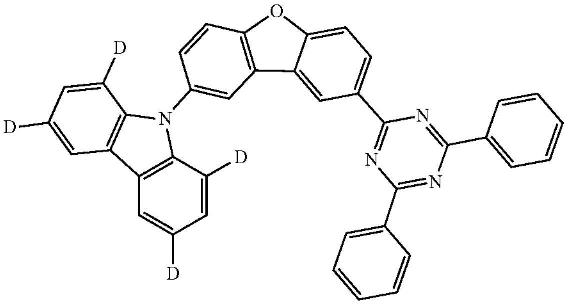
-continued
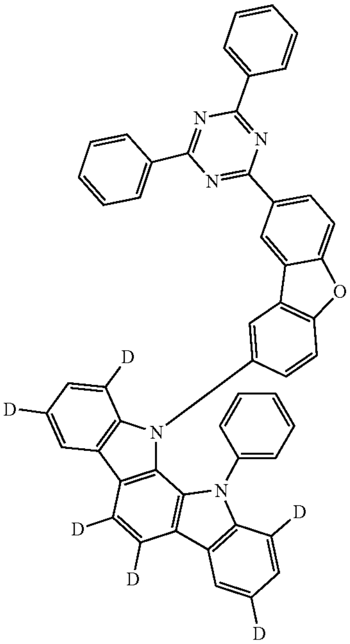
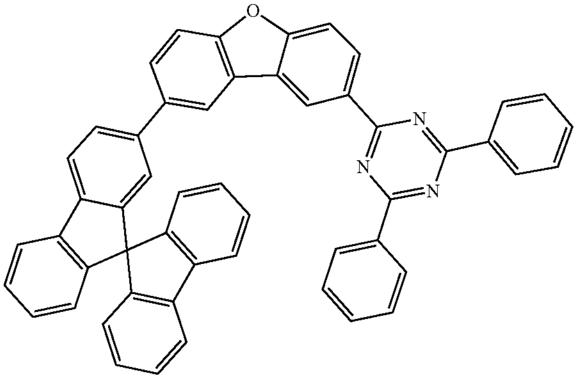
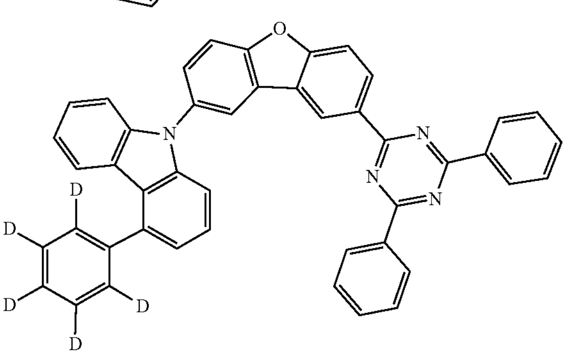
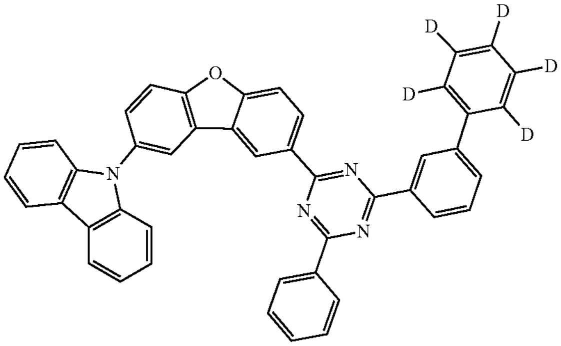

-continued
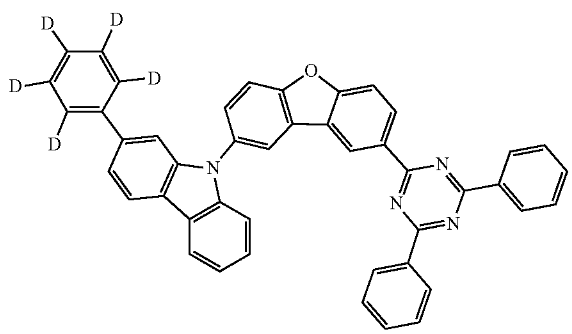
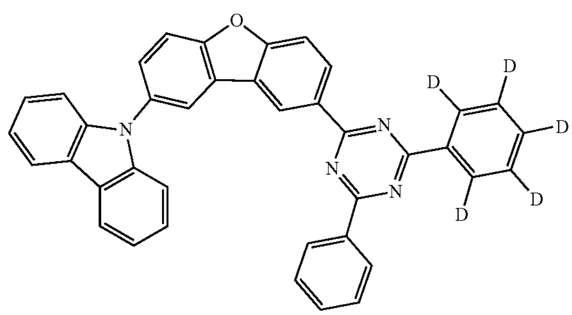
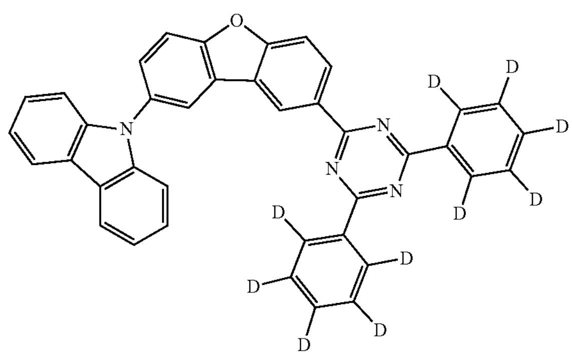
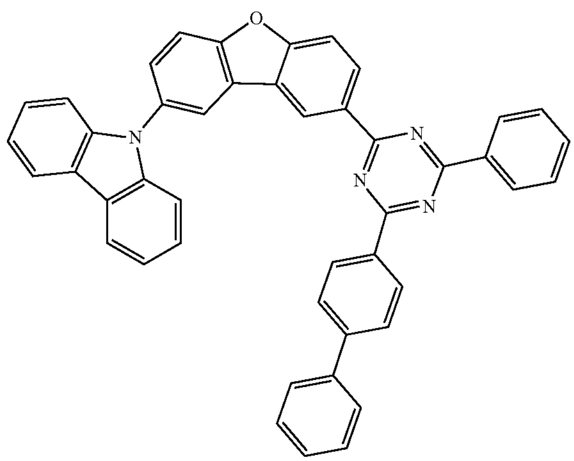
-continued
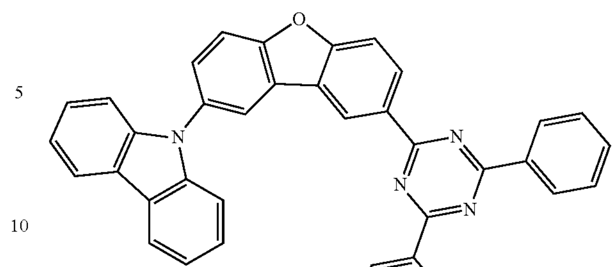
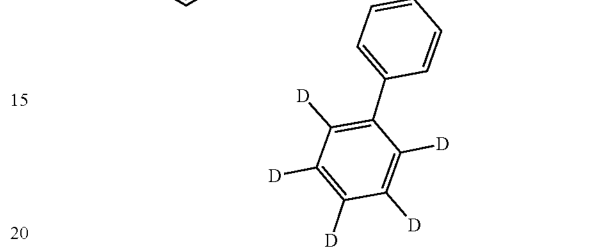
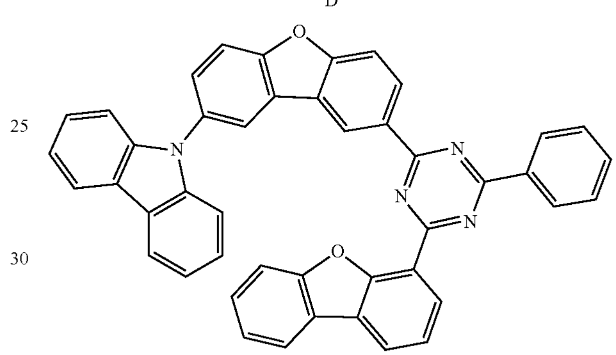
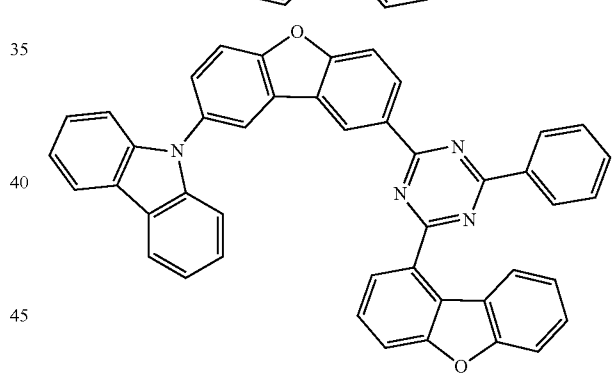
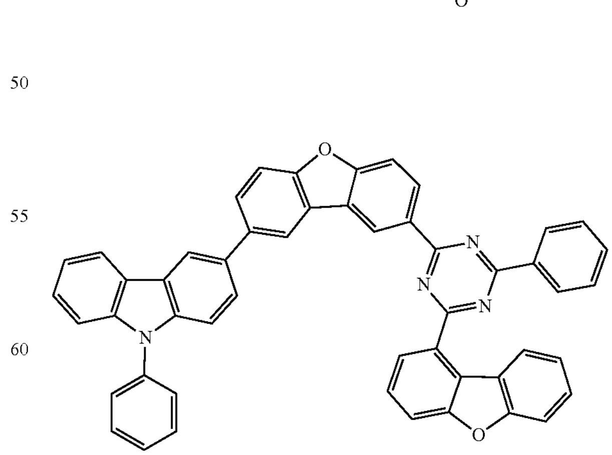

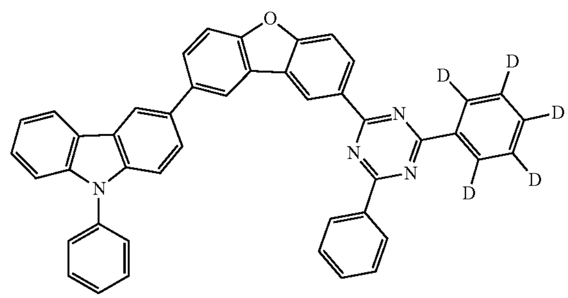
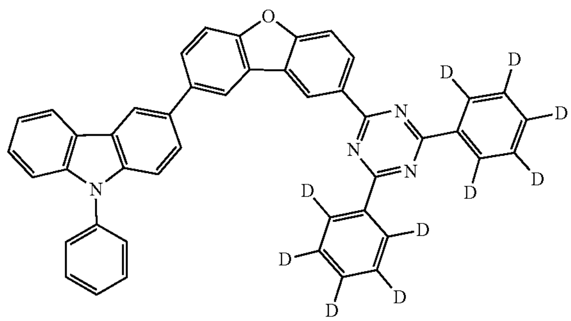
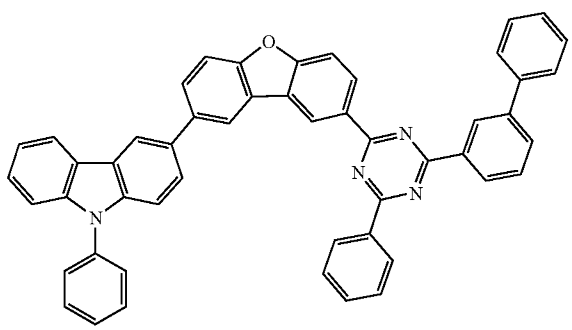
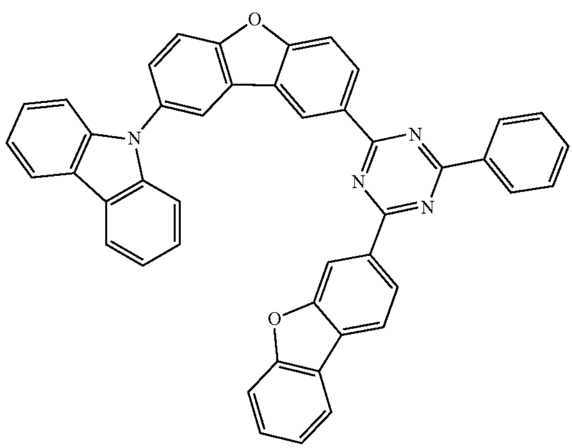
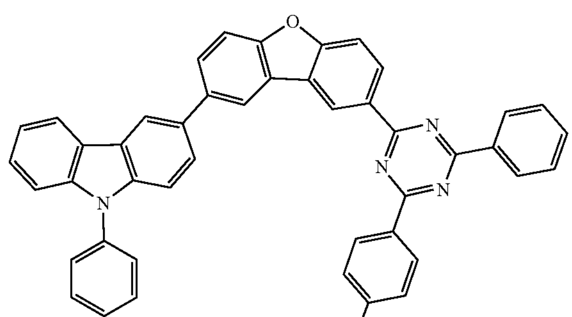
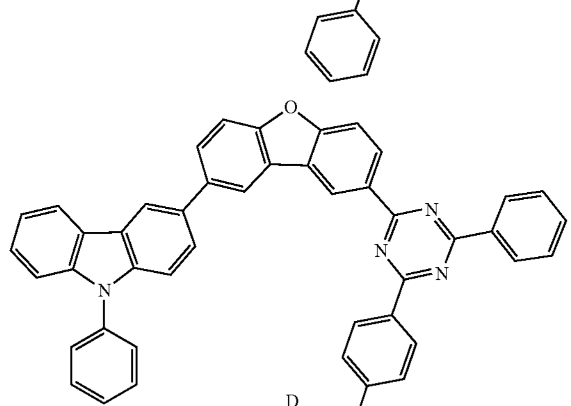
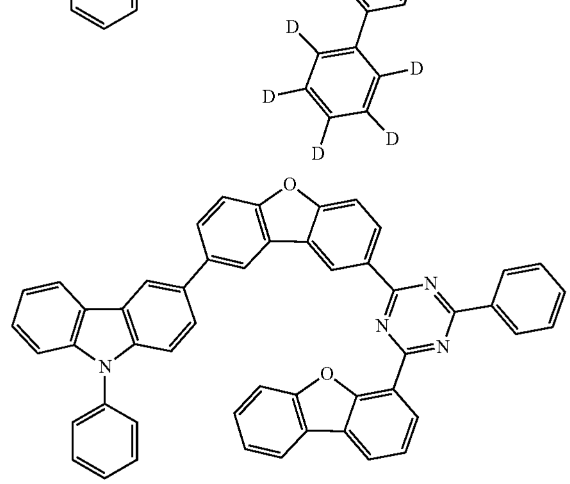
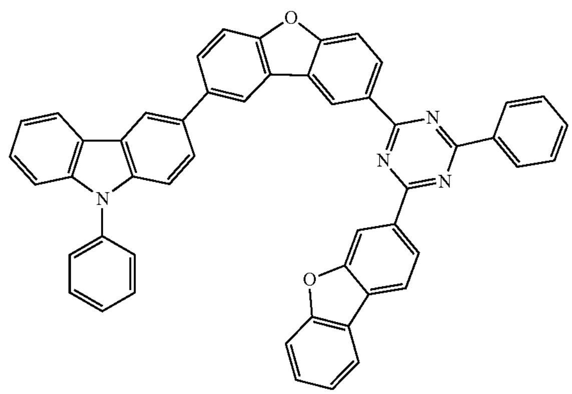

-continued
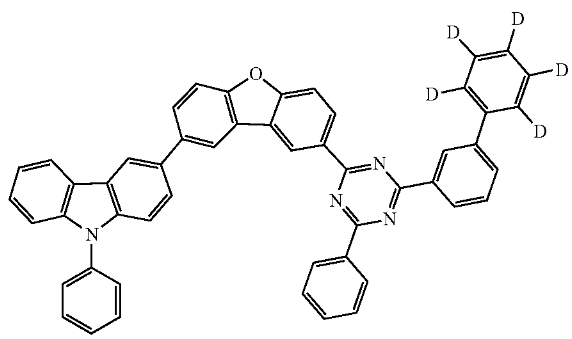
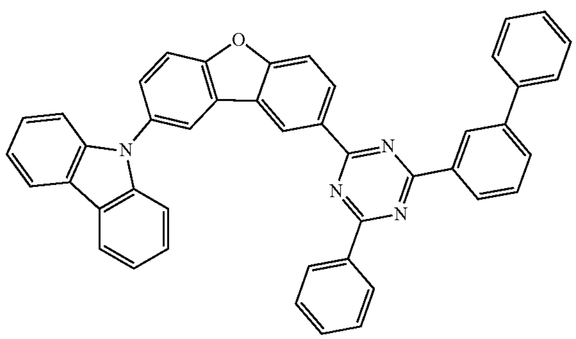
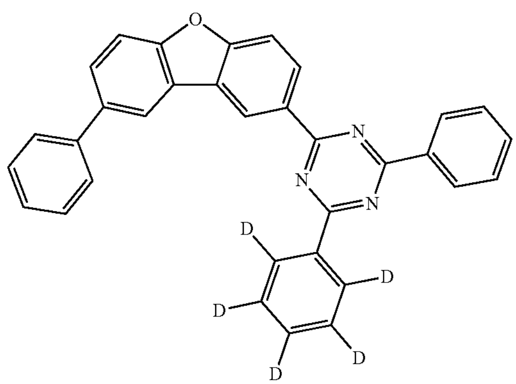
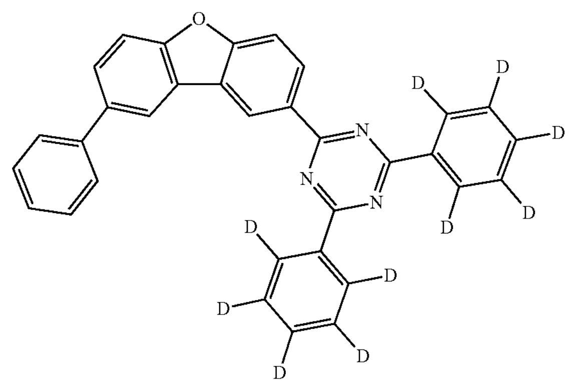
-continued
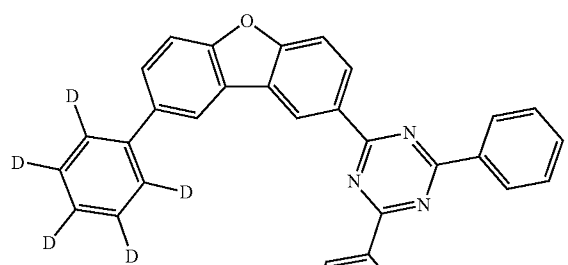
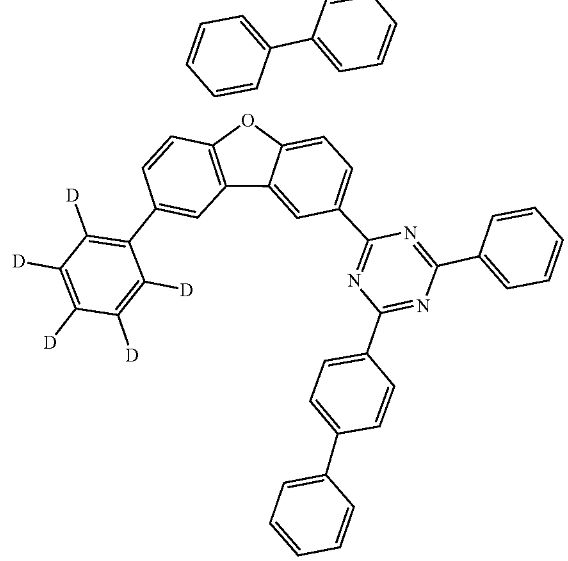
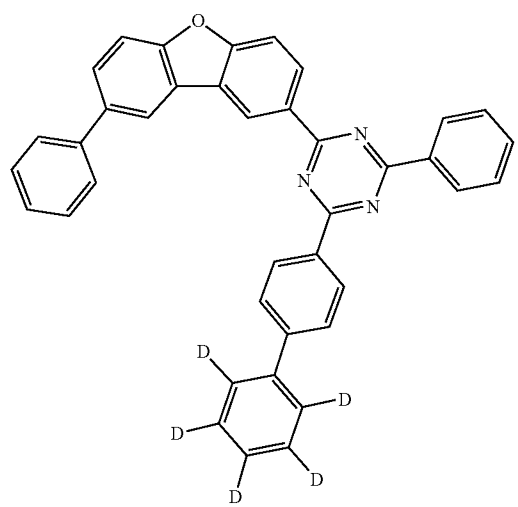
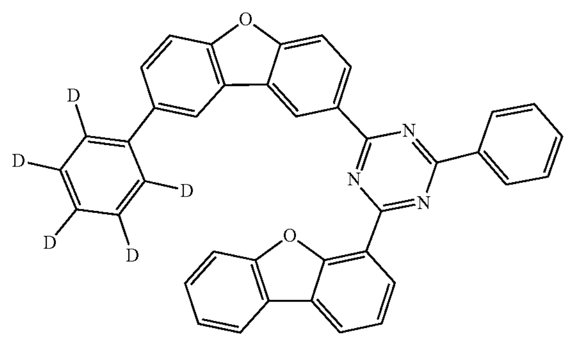

-continued
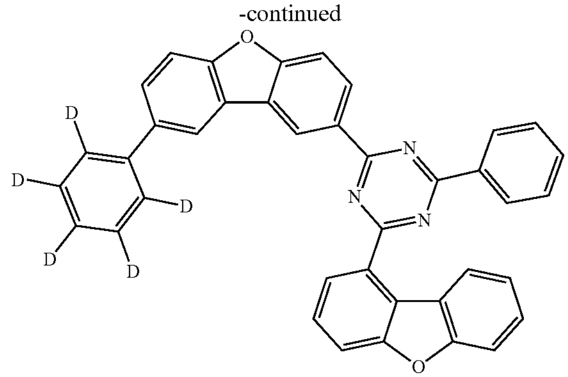
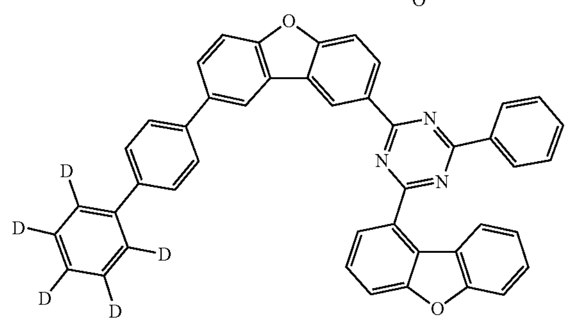
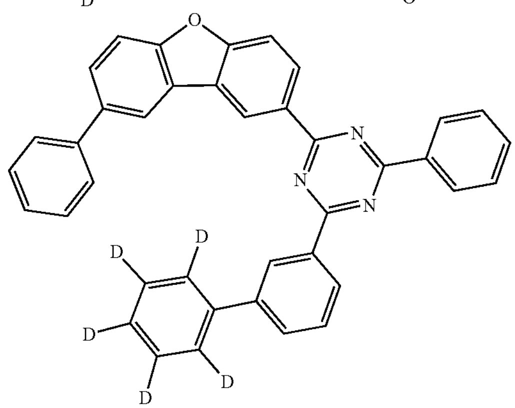
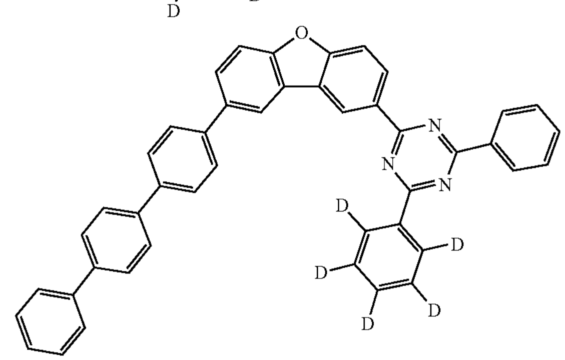
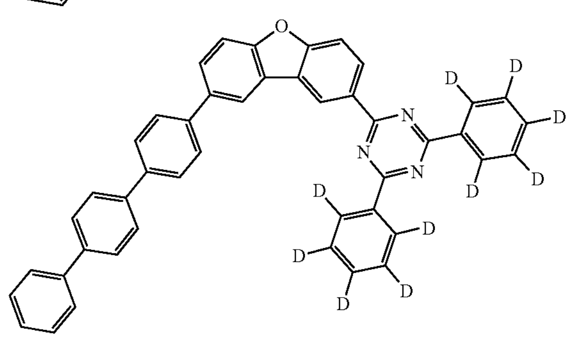
-continued
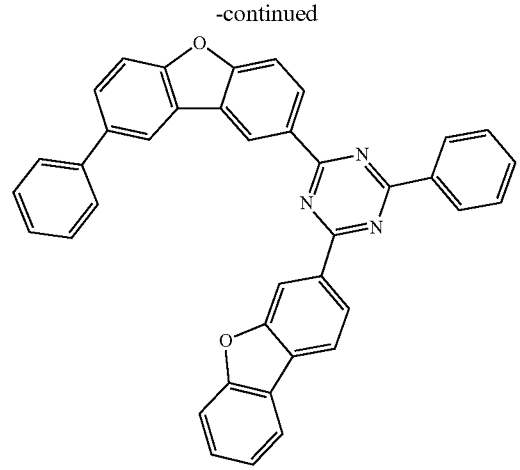
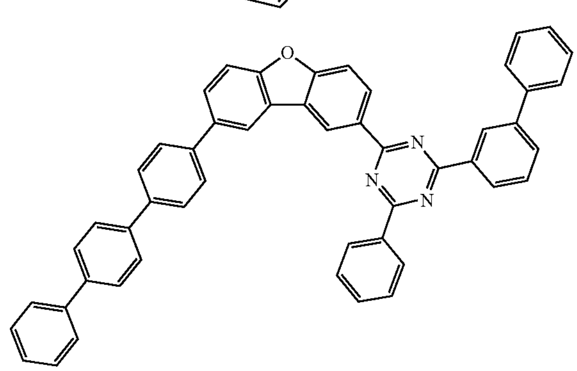
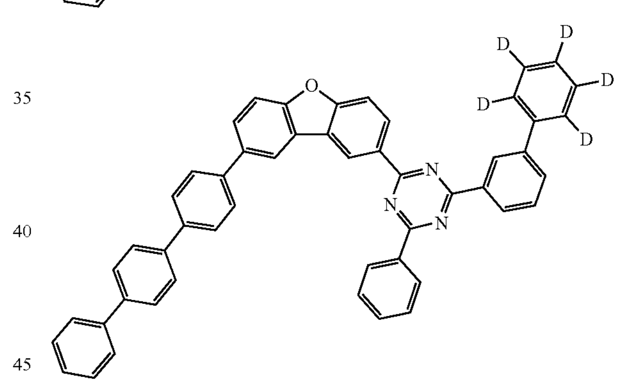
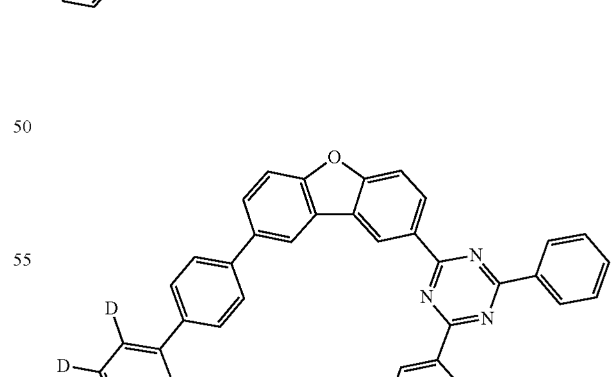
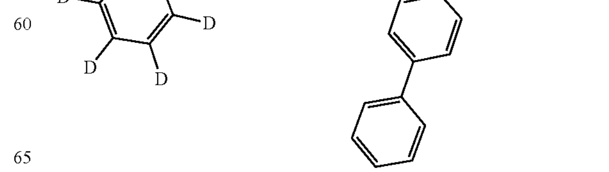

-continued
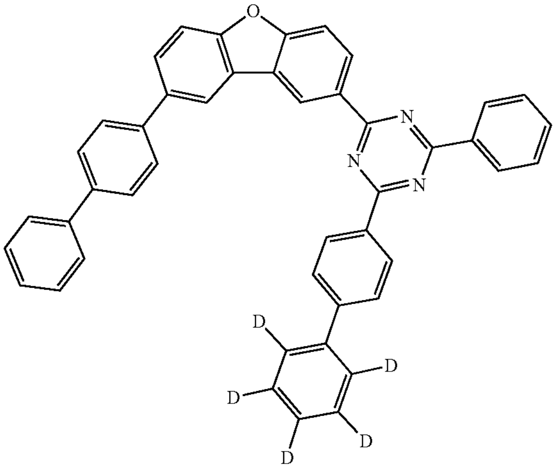
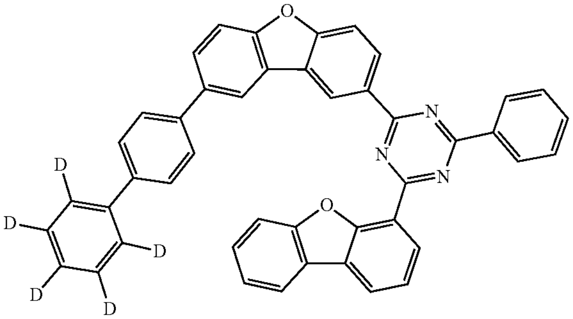
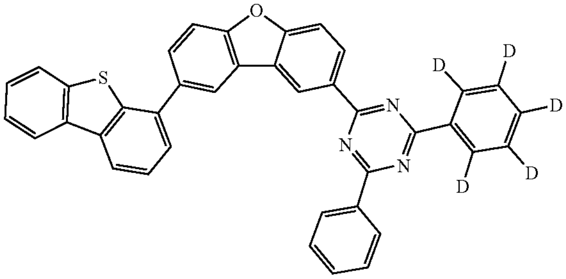
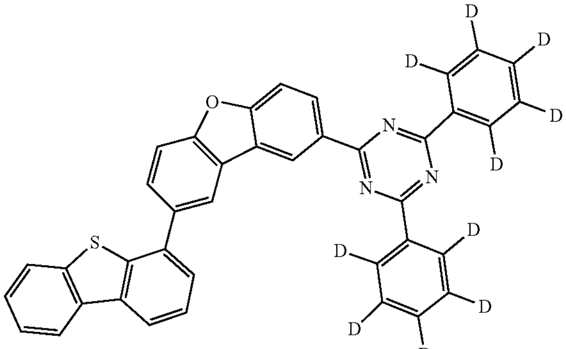
-continued
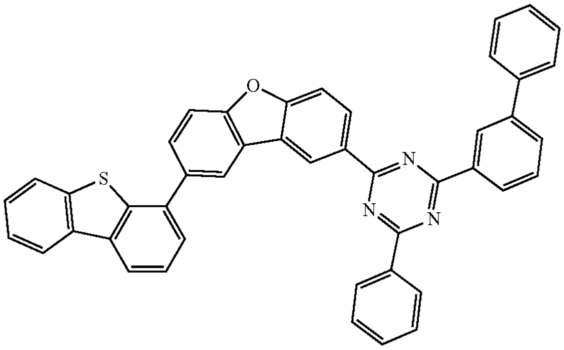
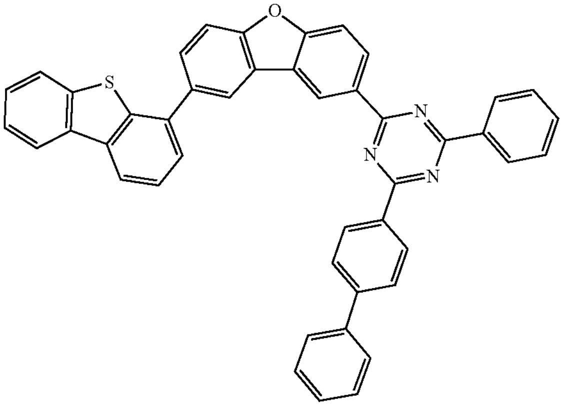
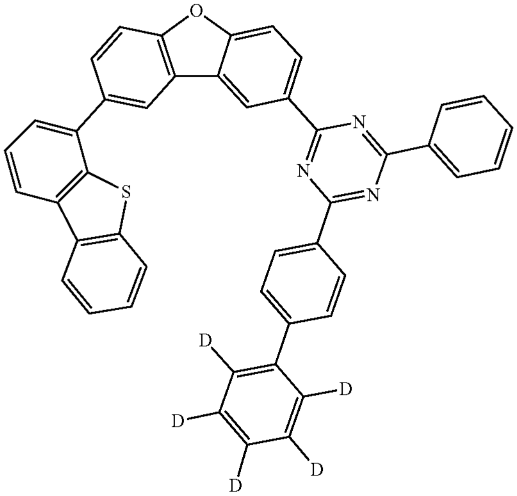
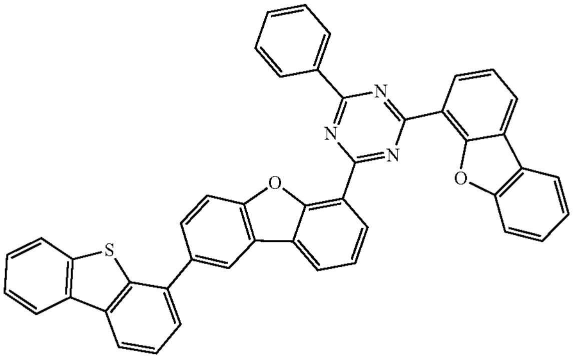

-continued
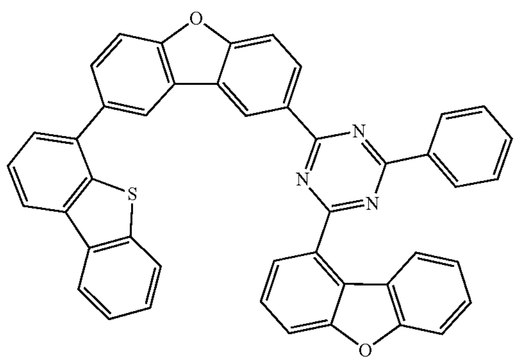
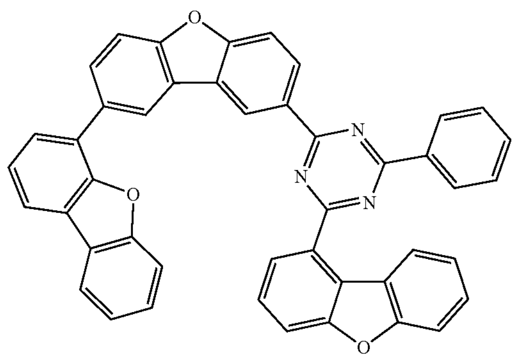
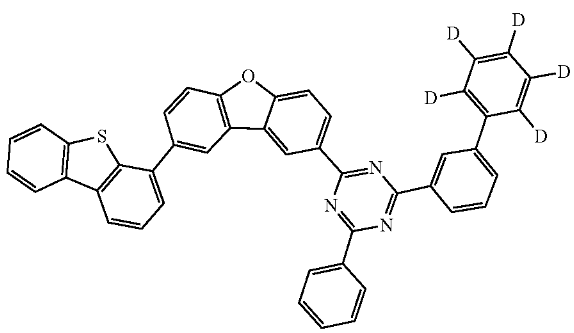
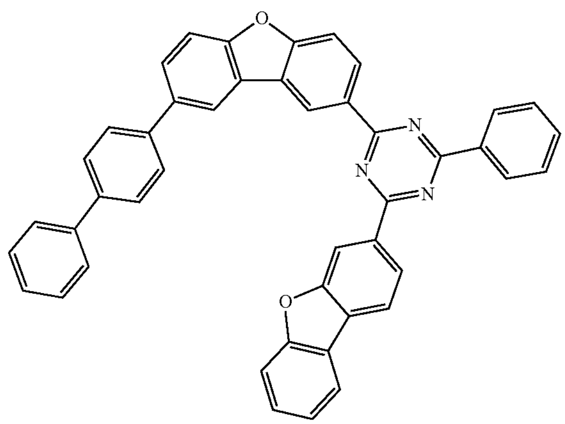
-continued
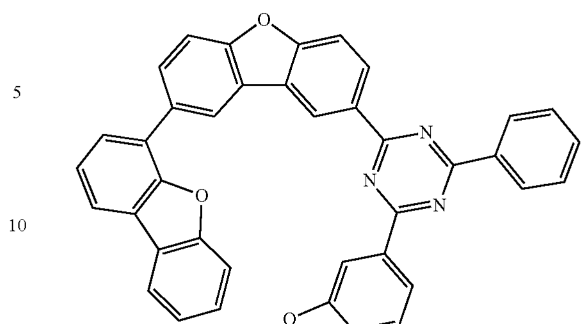
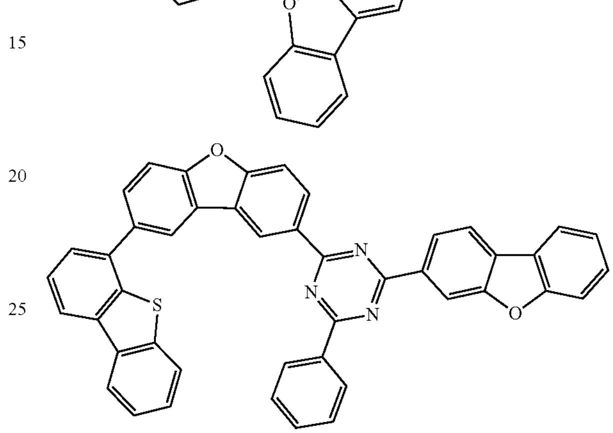
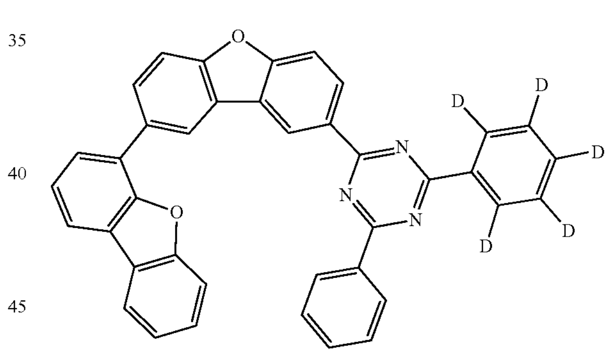
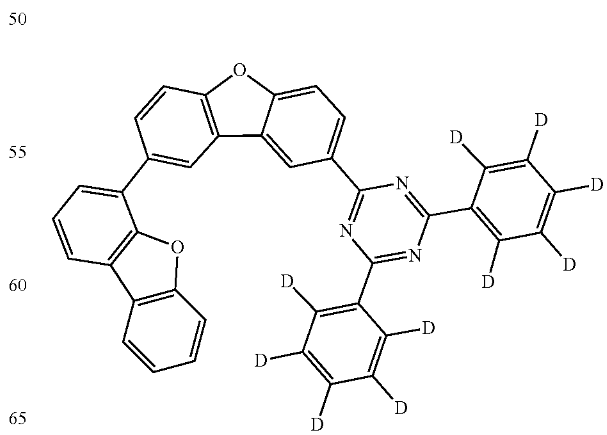

-continued
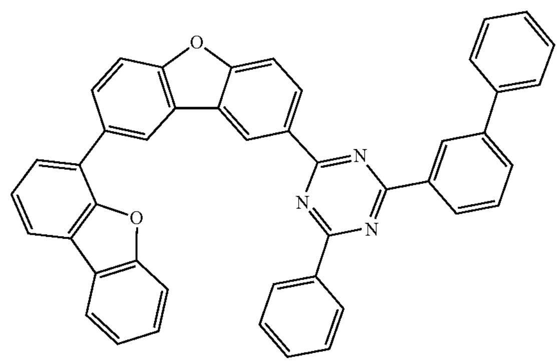
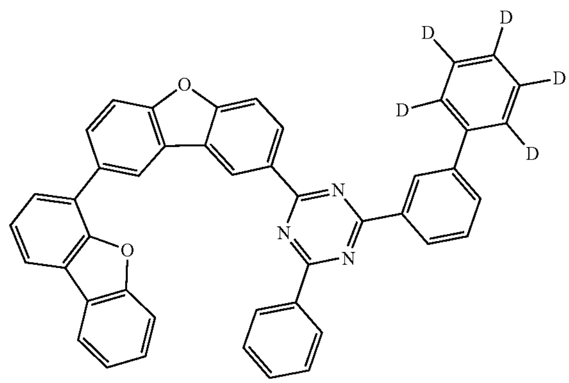
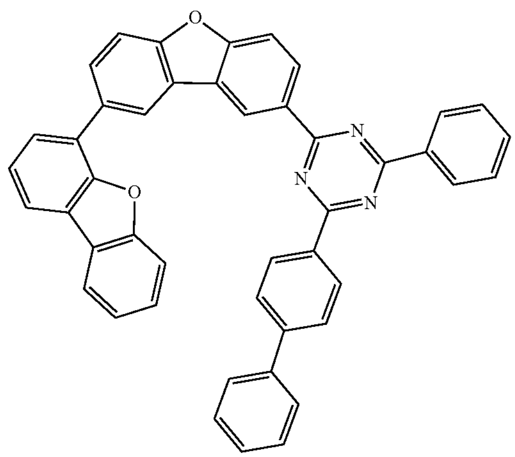
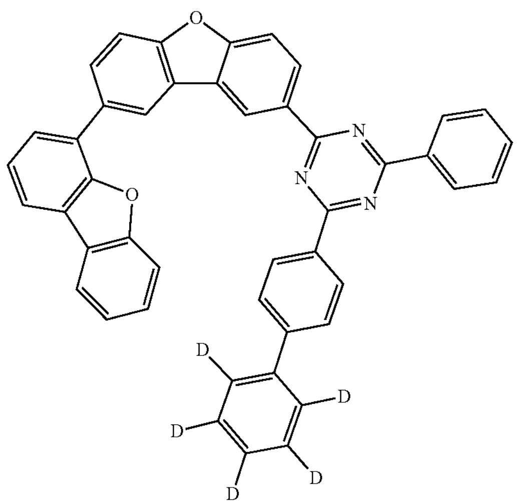
-continued
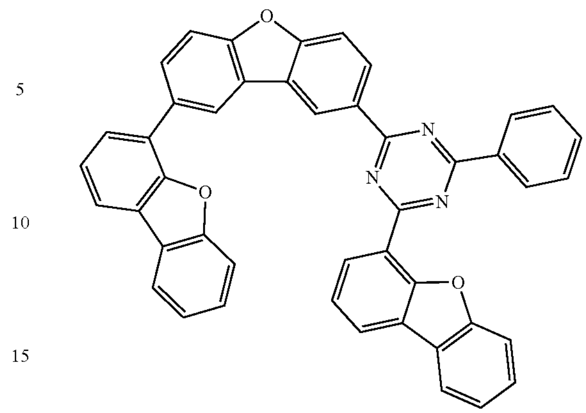
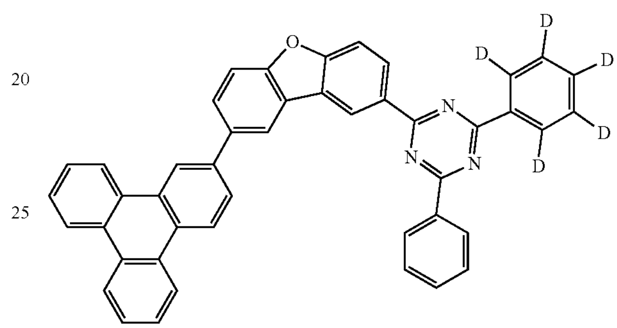
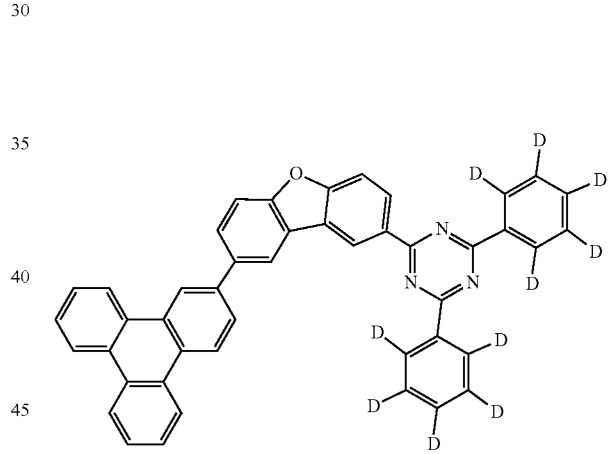
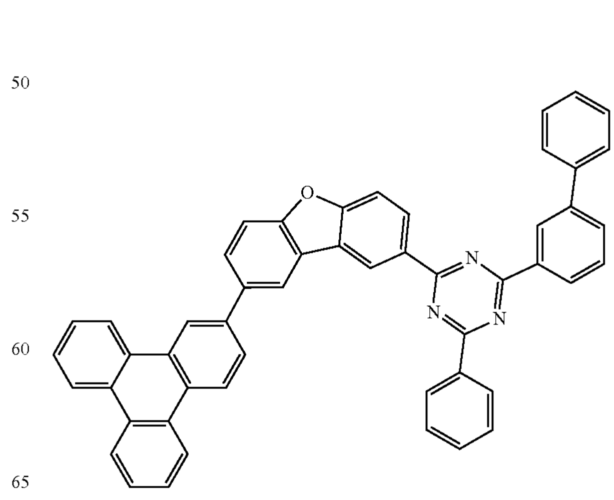

-continued
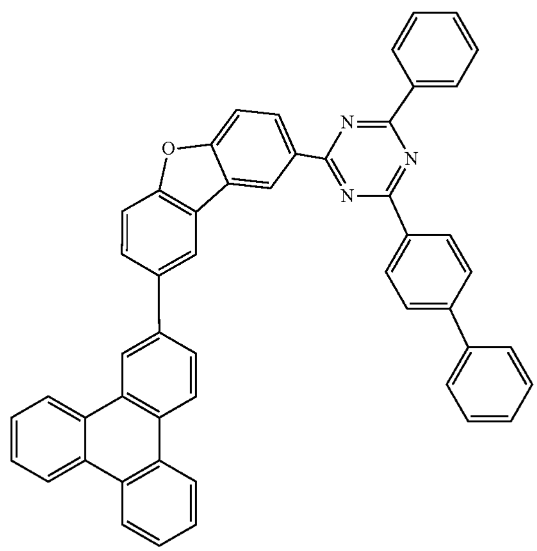
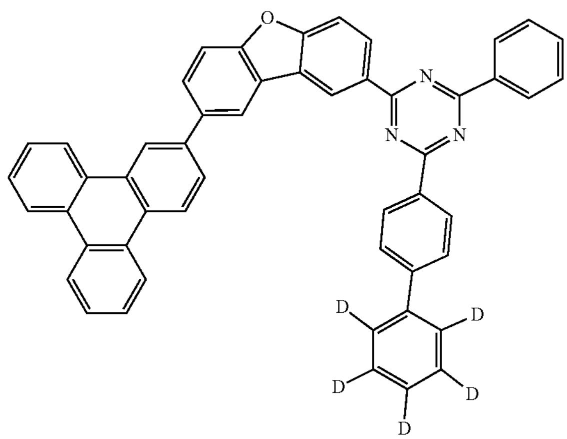
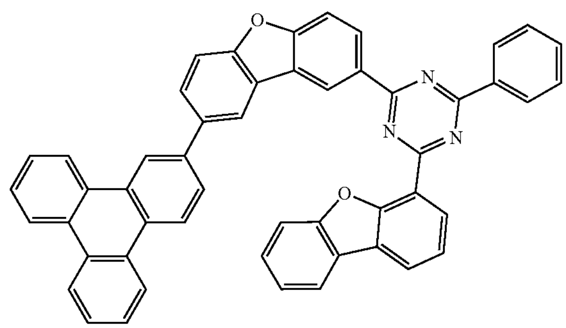
-continued
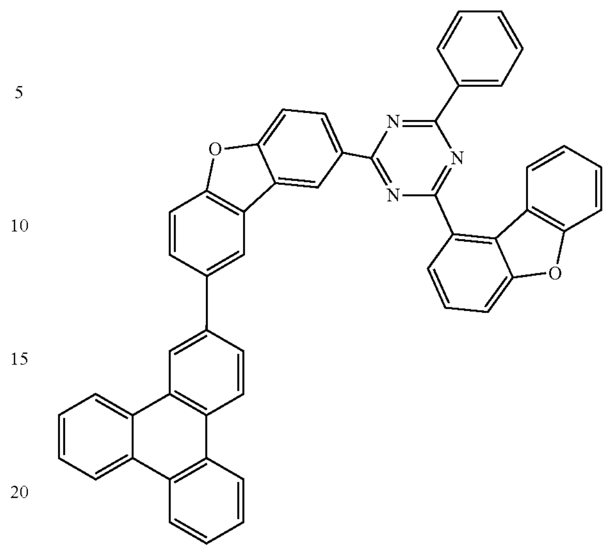
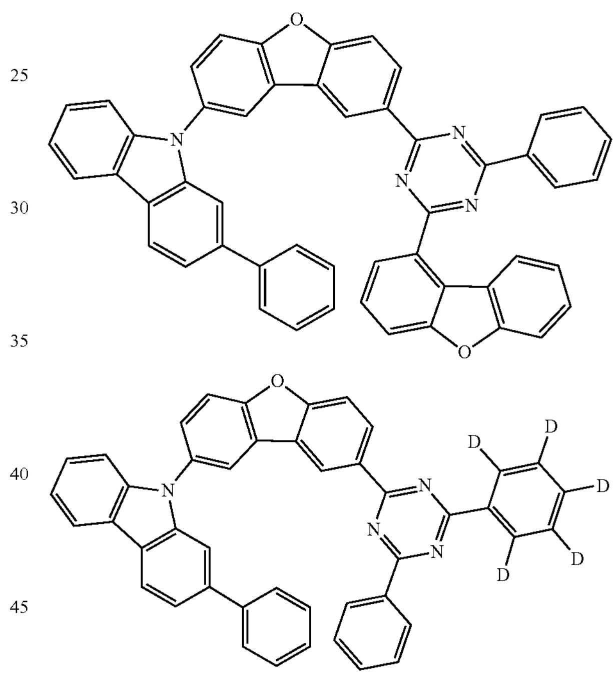
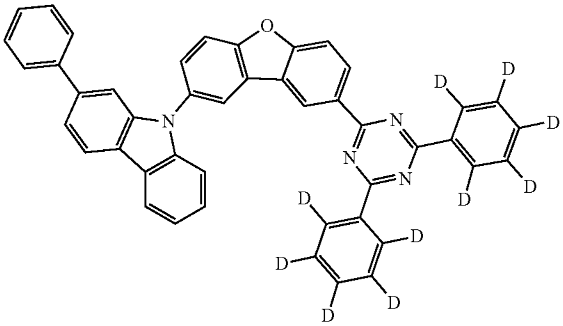

-continued
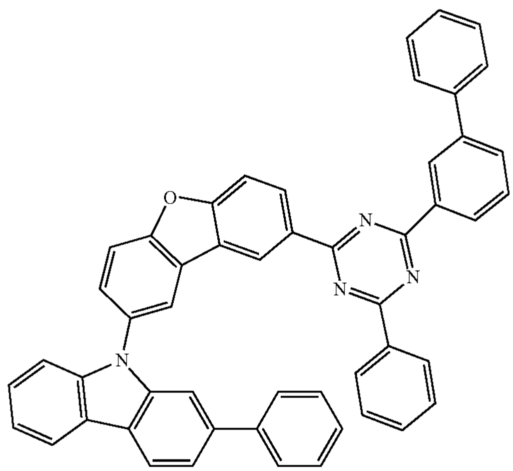
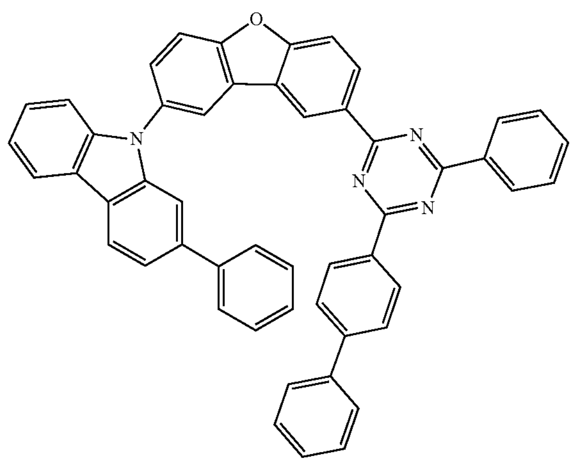
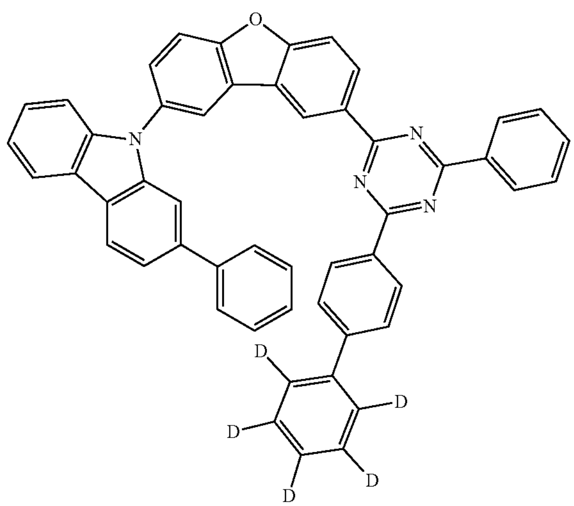
-continued
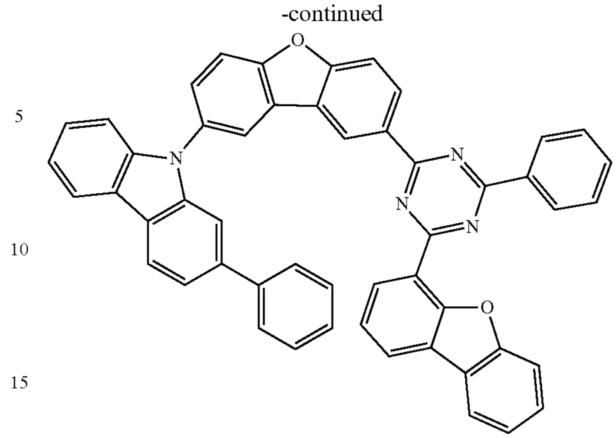
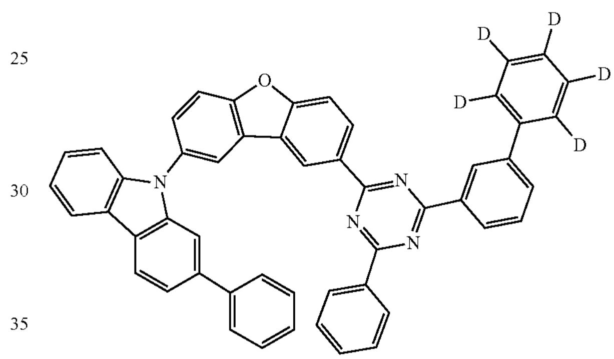
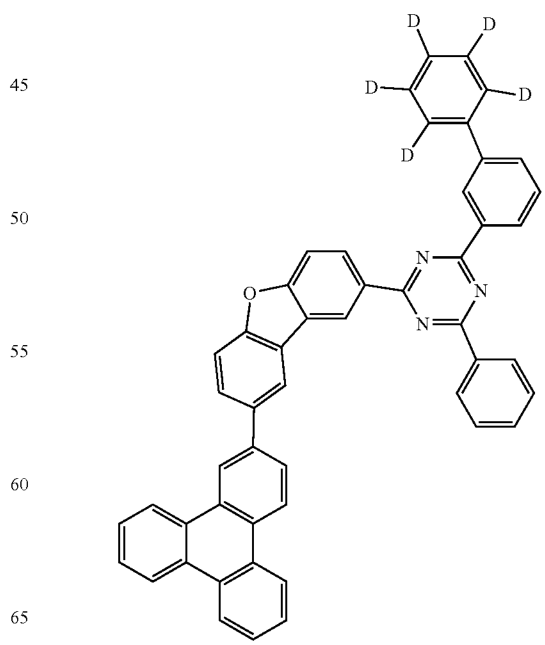

-continued
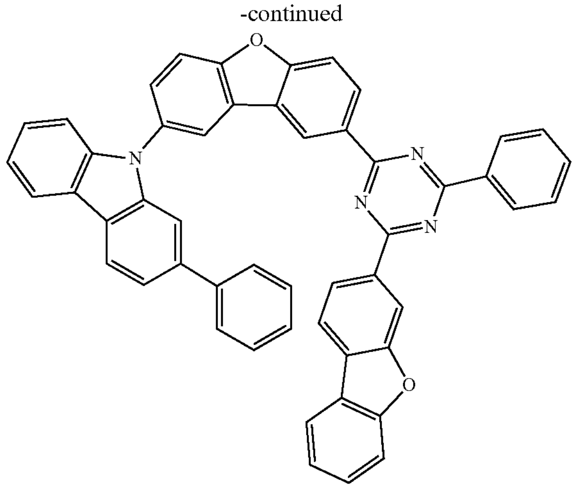
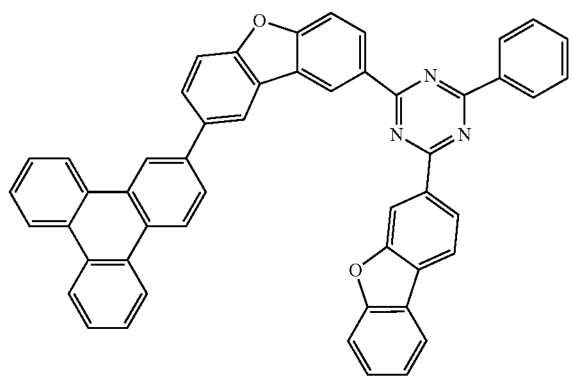
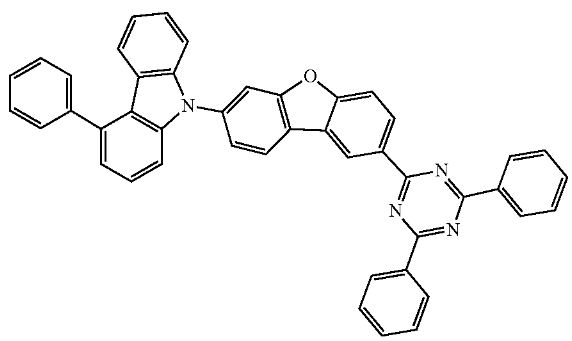
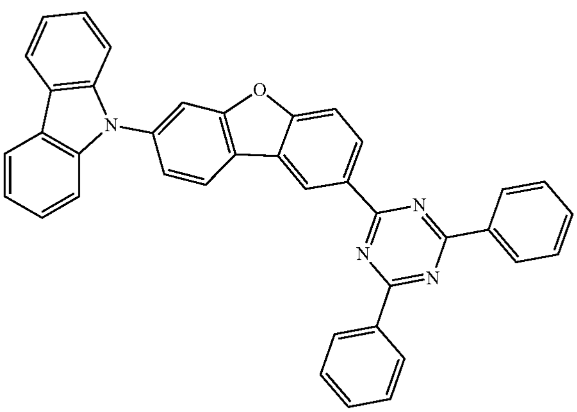
-continued
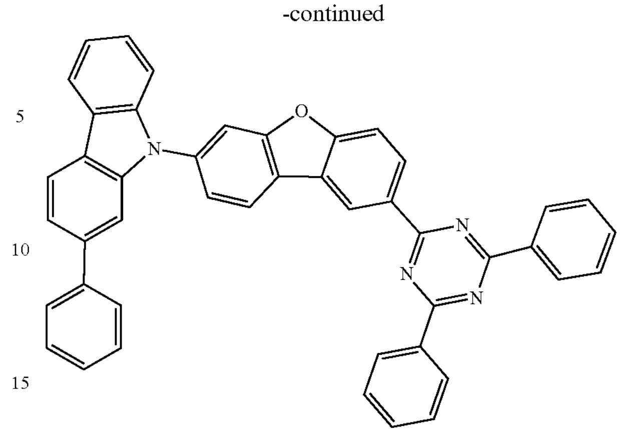
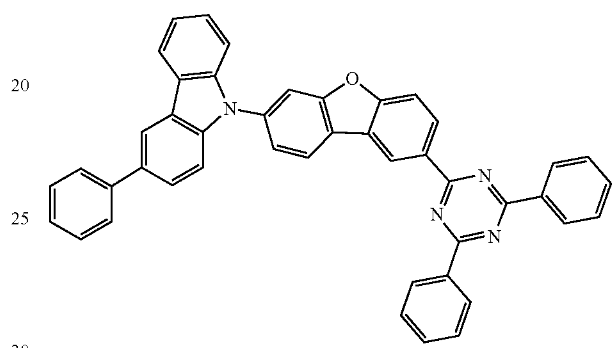
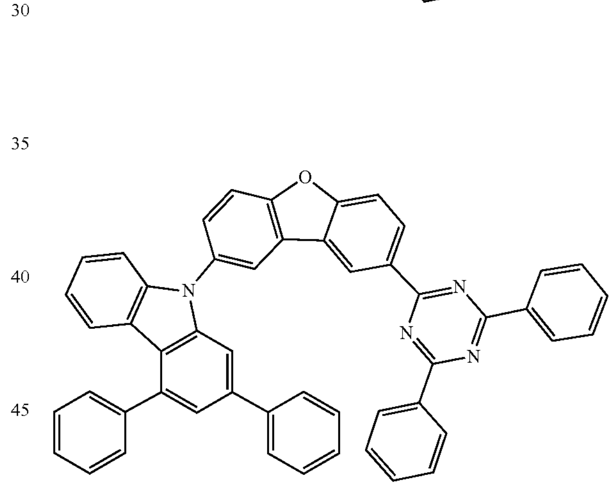
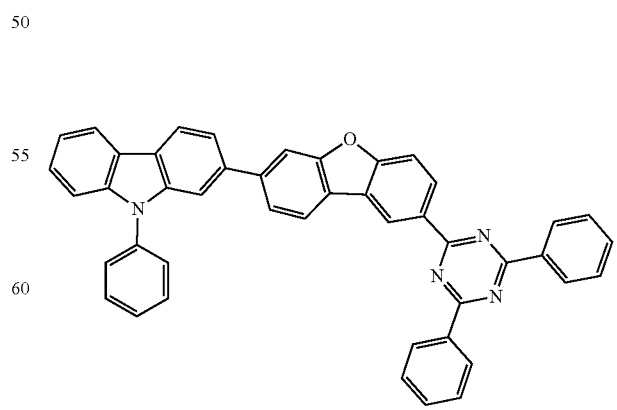

-continued
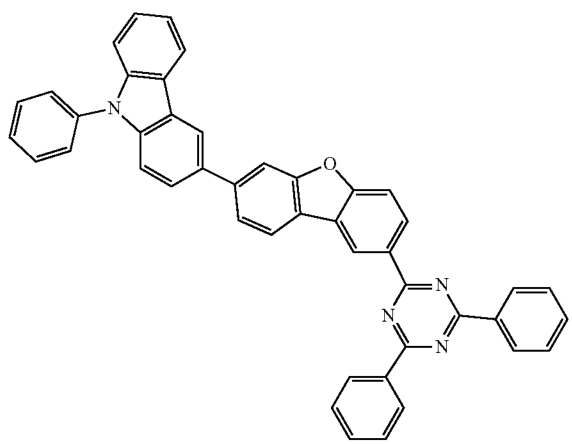
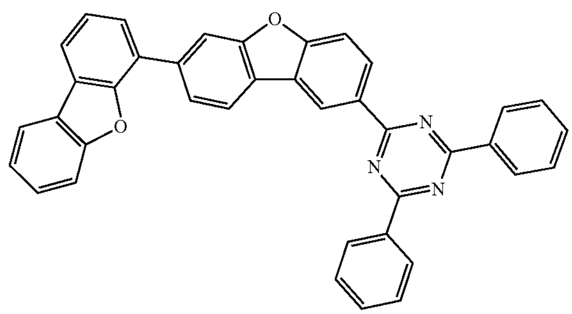
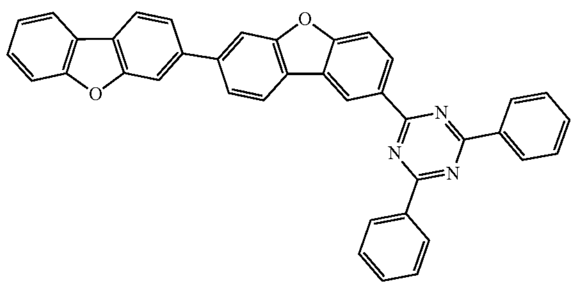
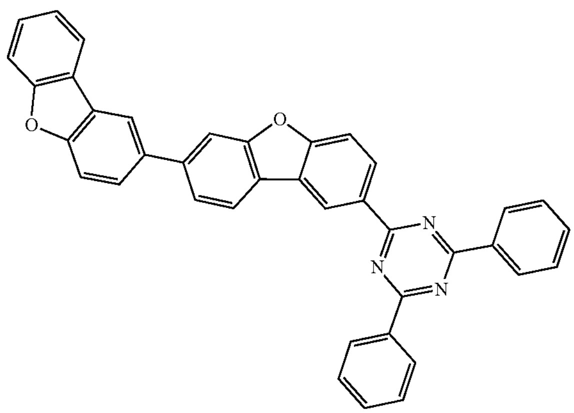
-continued
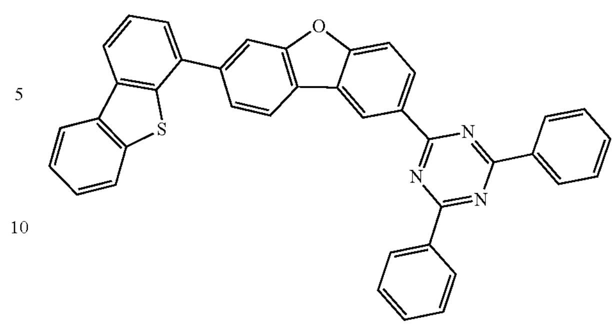
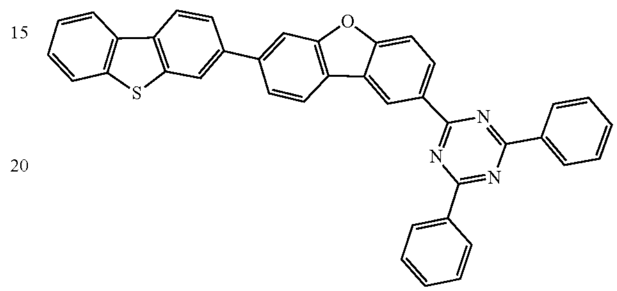
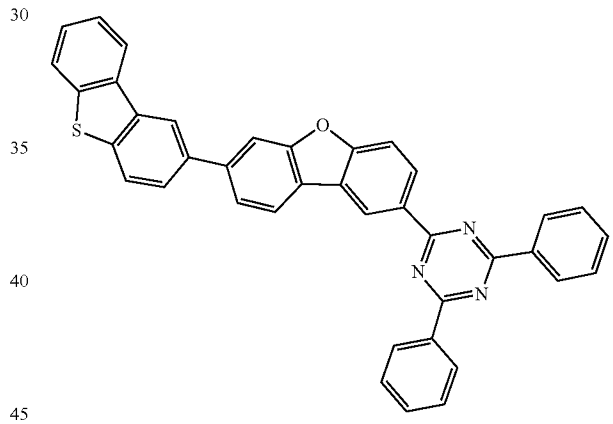
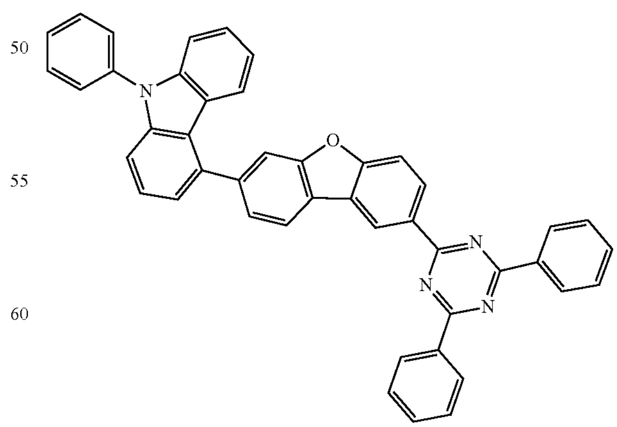

-continued
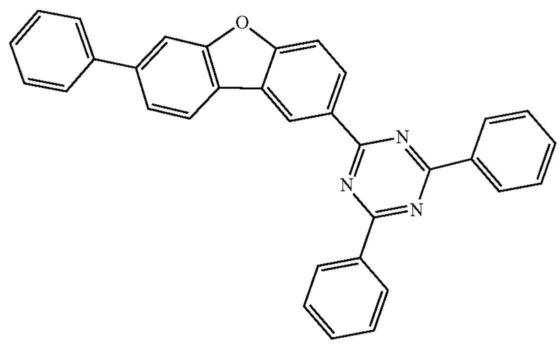
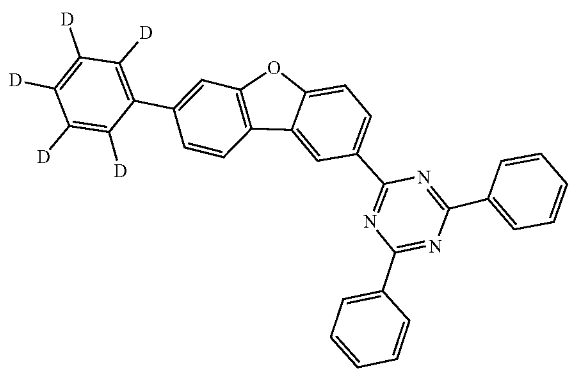
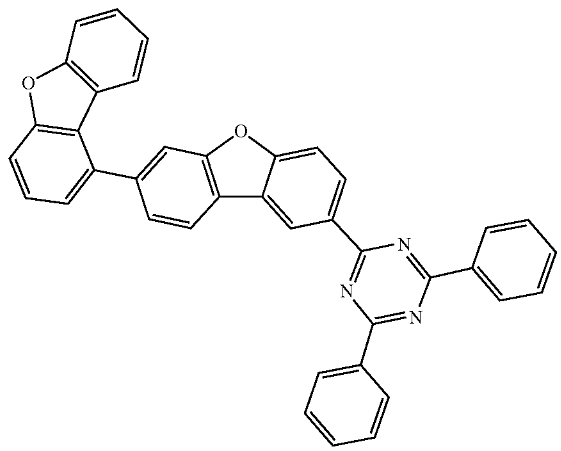
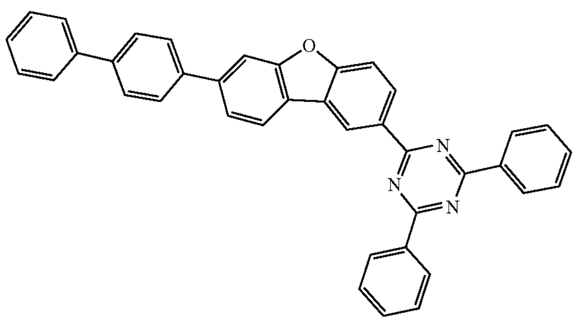
-continued
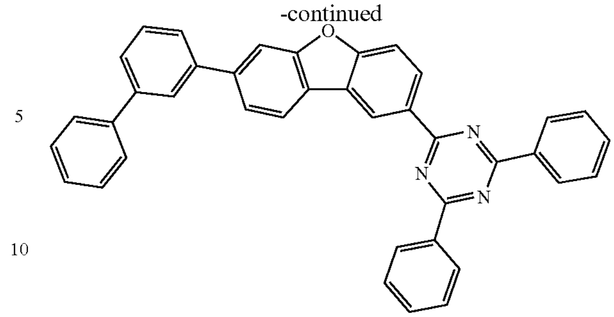
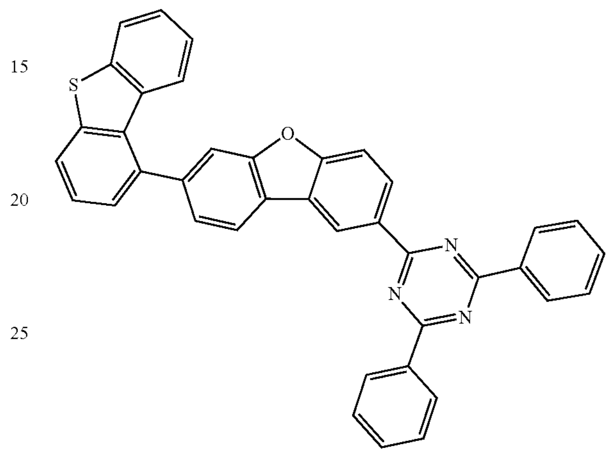
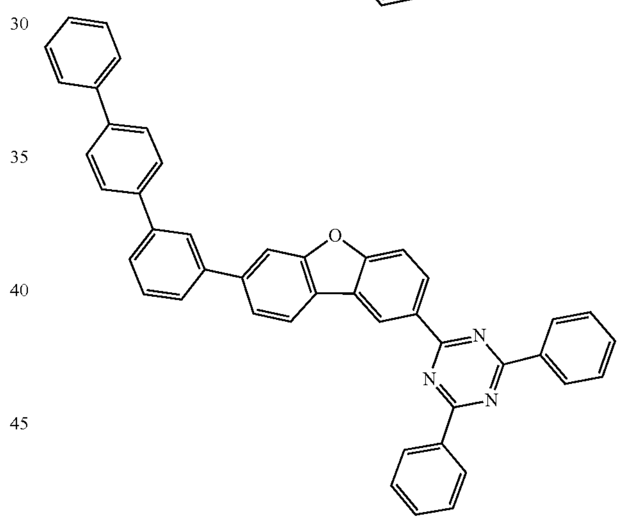
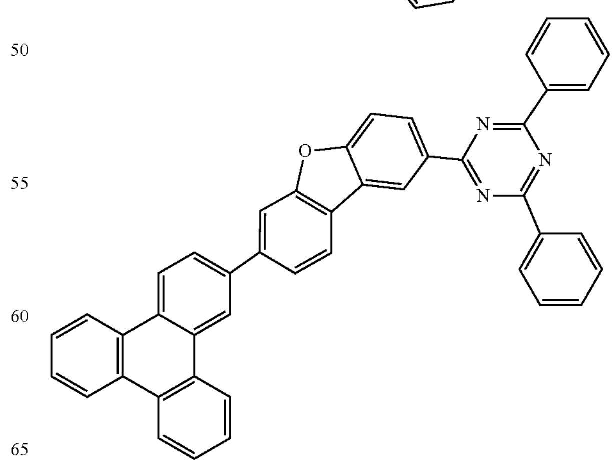

-continued
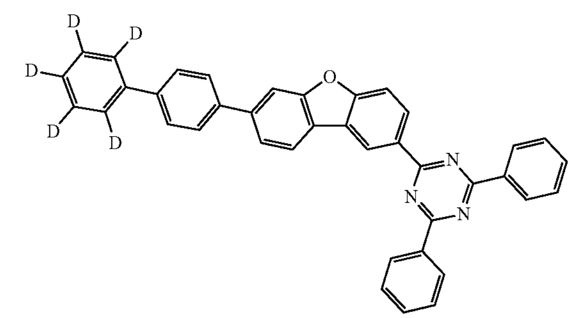
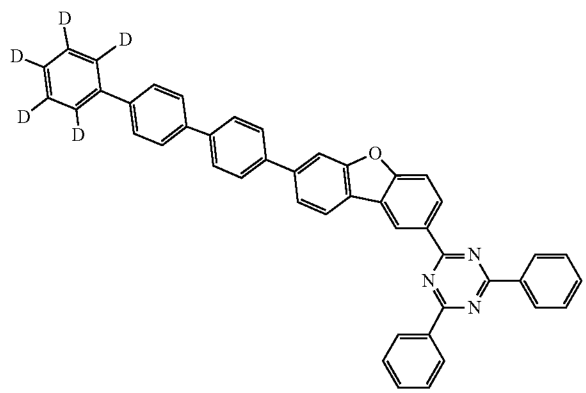
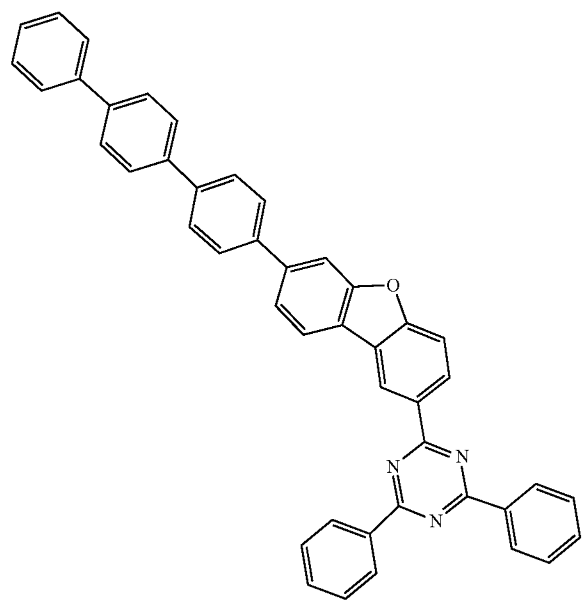
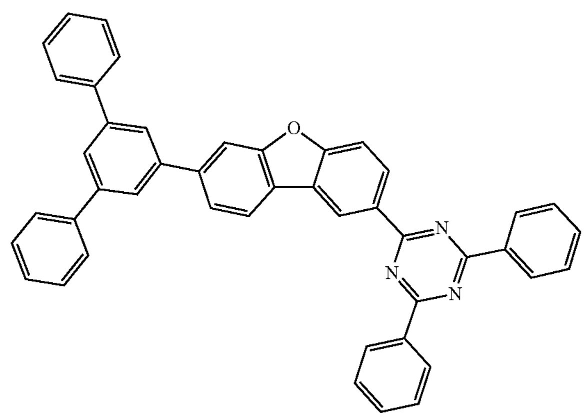
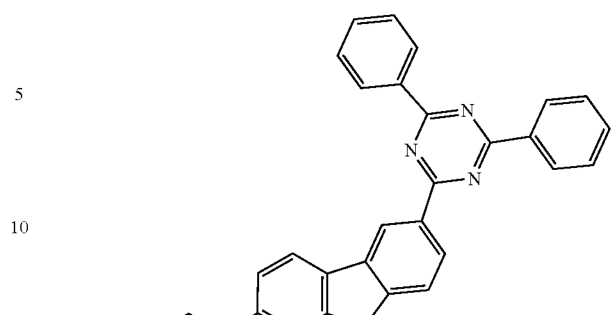
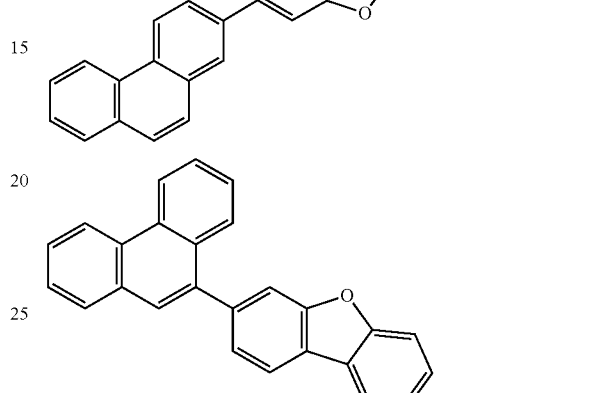
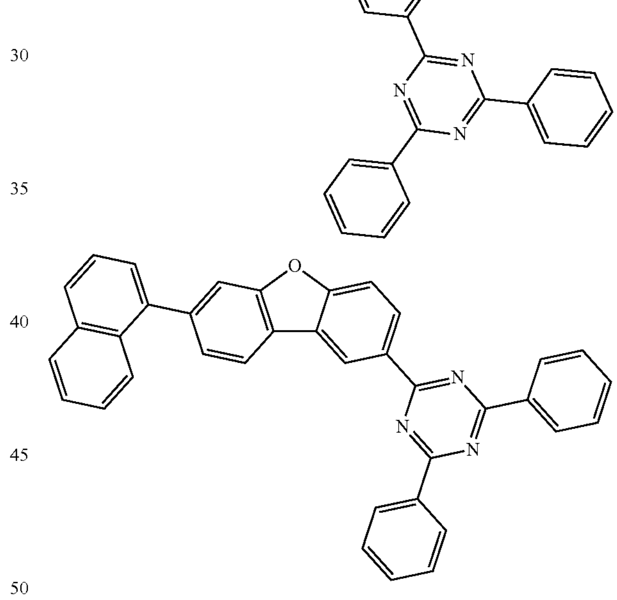
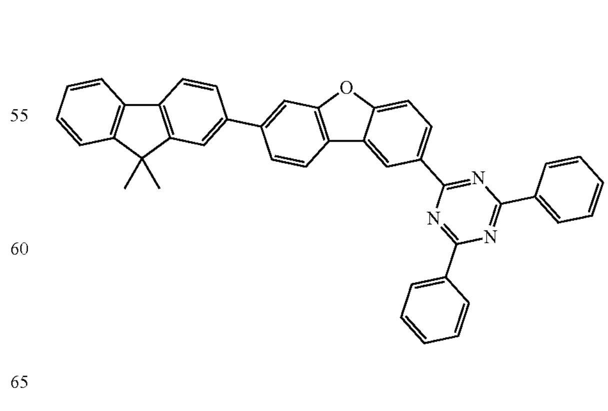

-continued
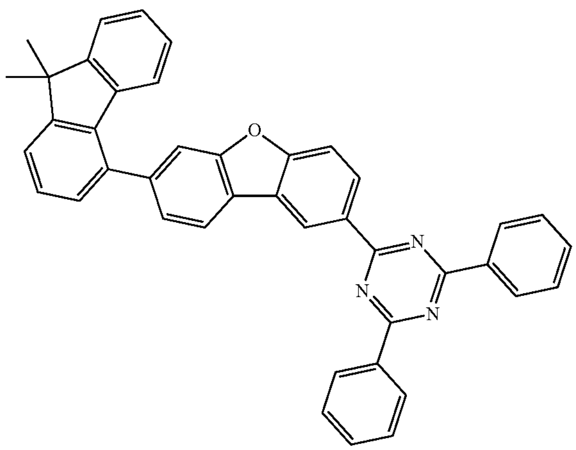
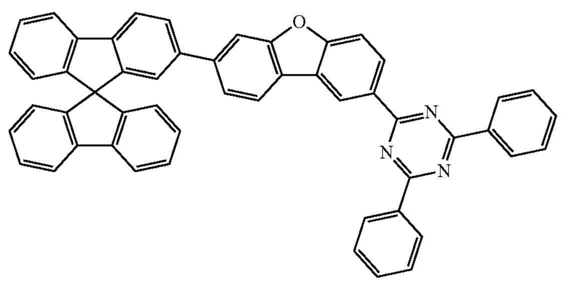
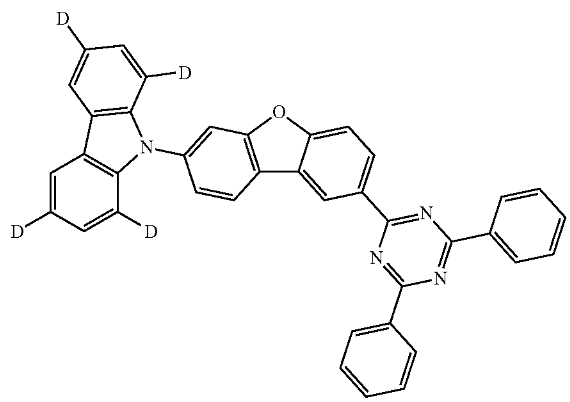
-continued
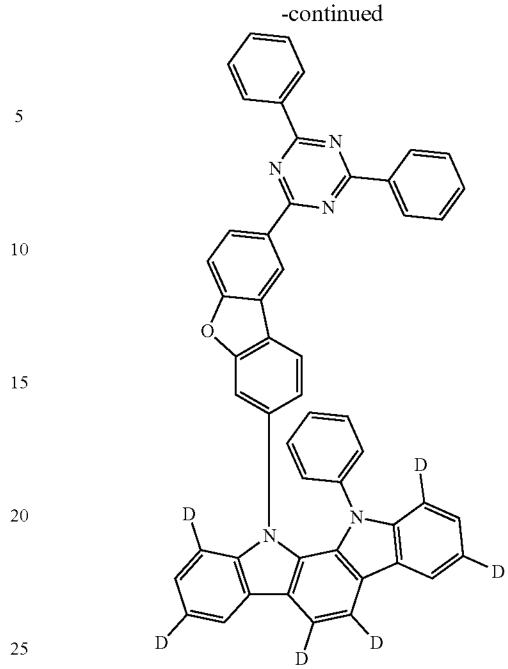
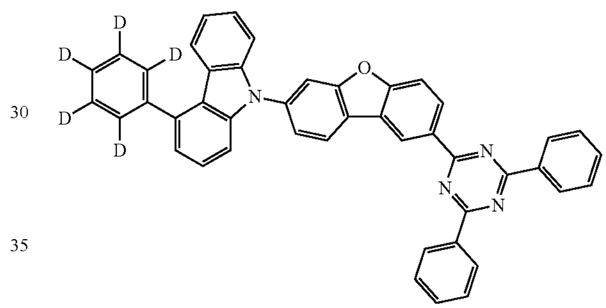
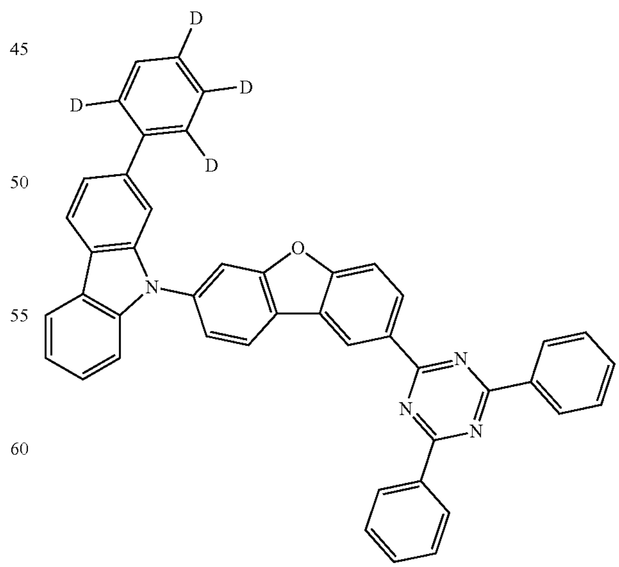

-continued
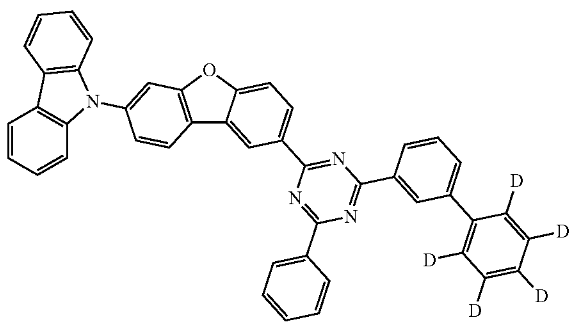
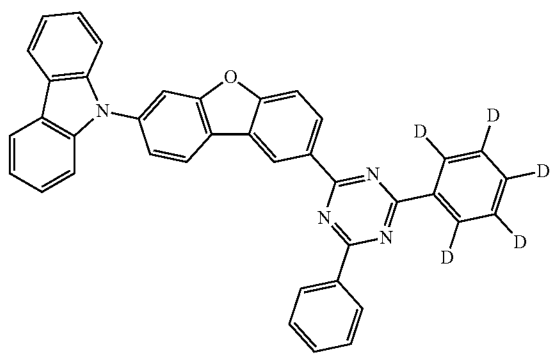
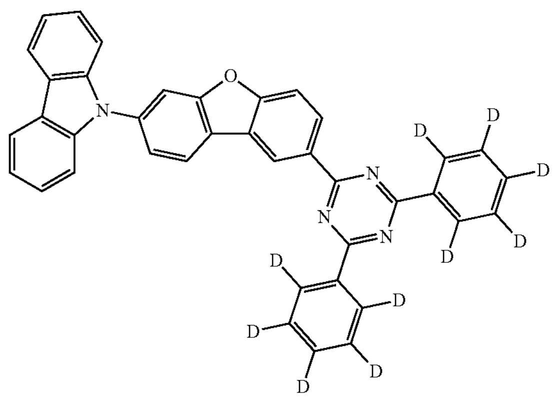
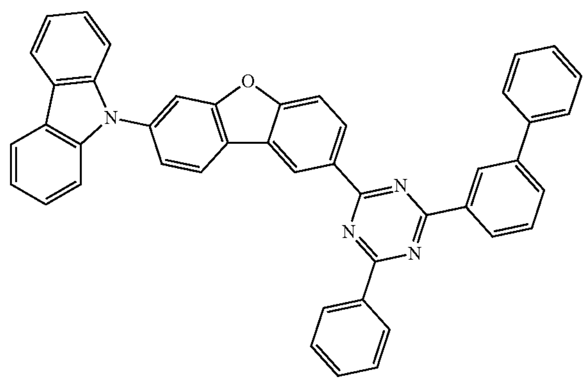
-continued
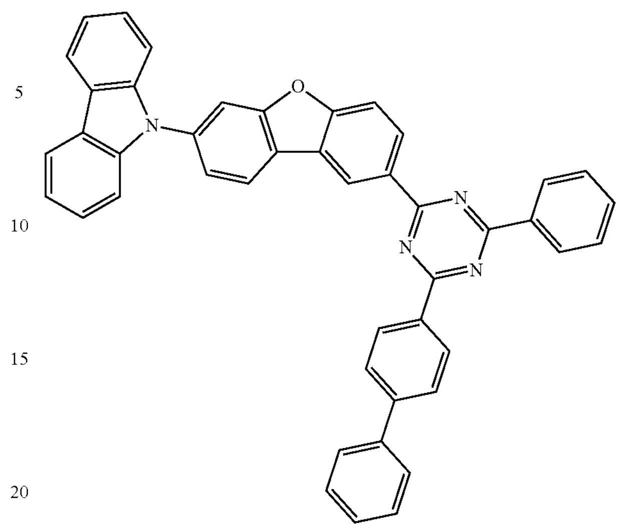
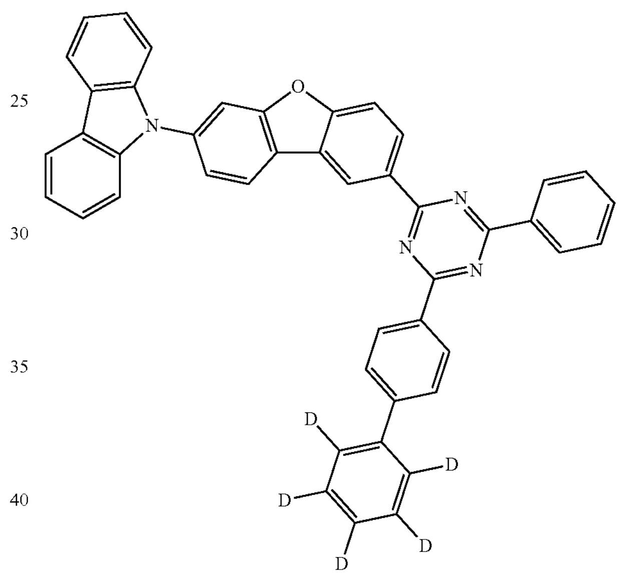
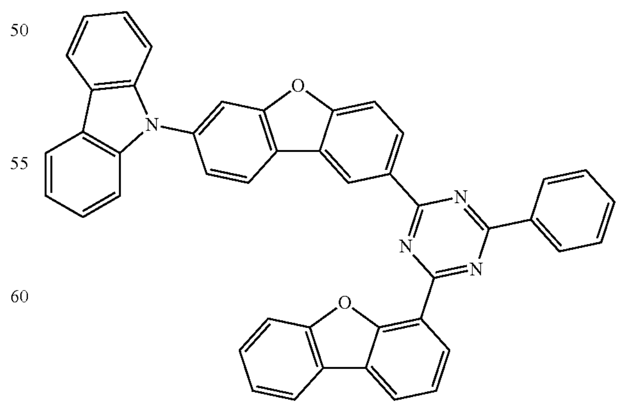

-continued
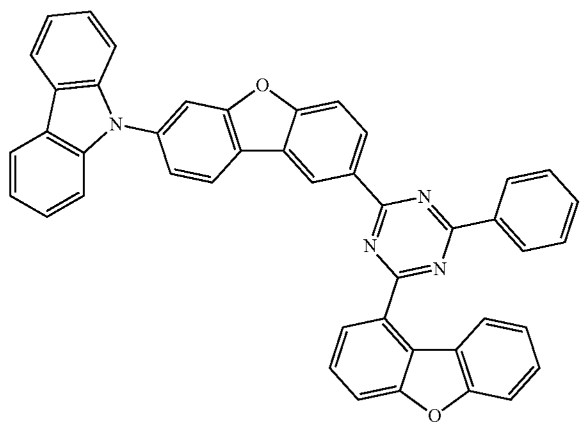
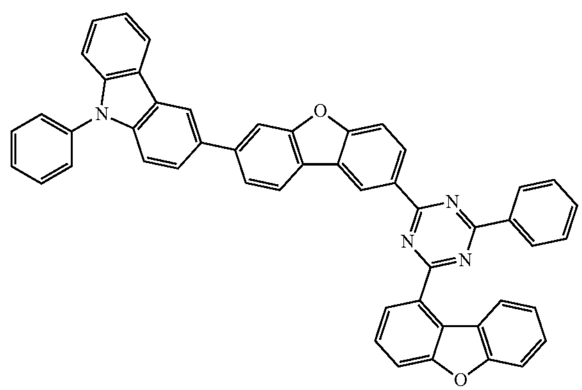
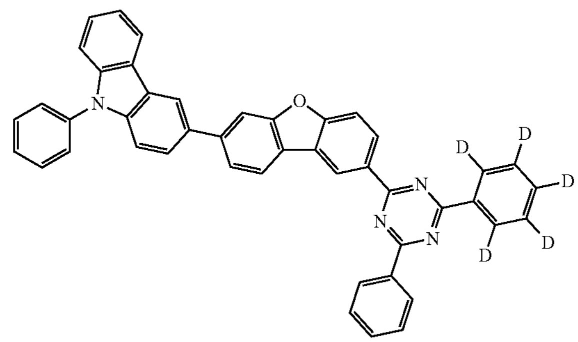
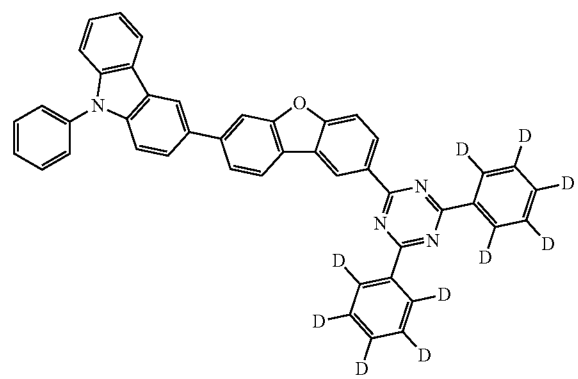
-continued
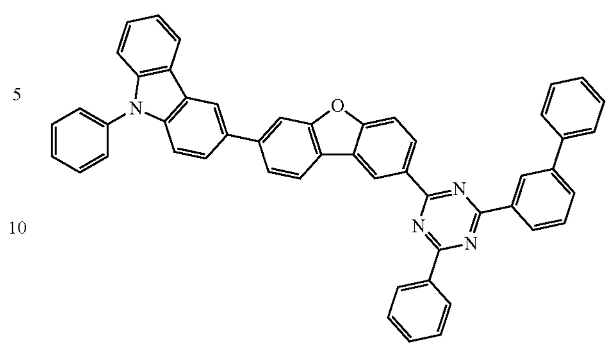
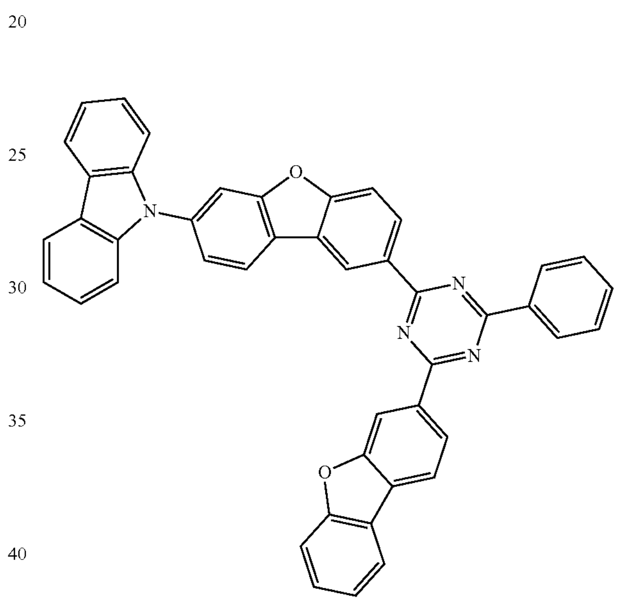
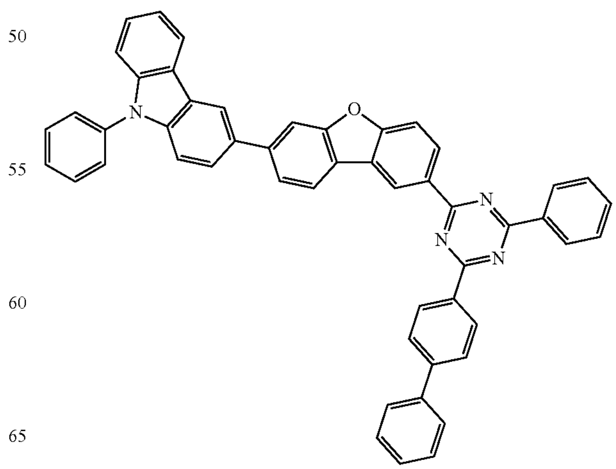

-continued
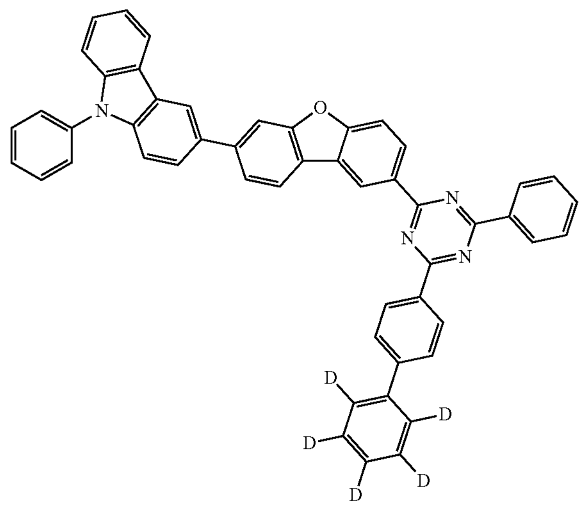
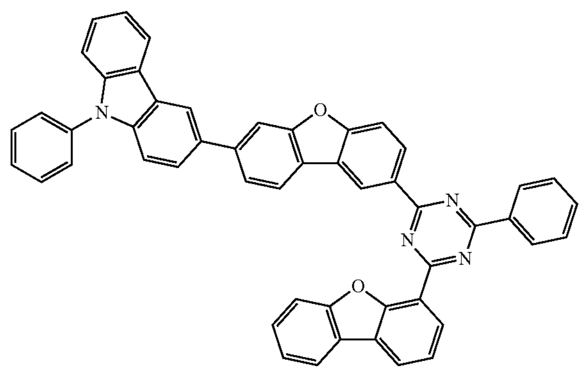
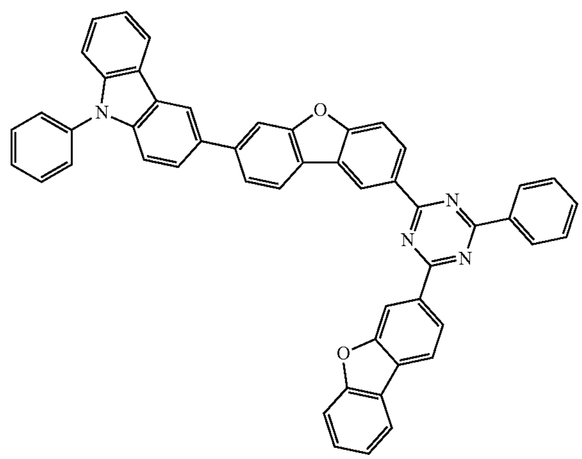
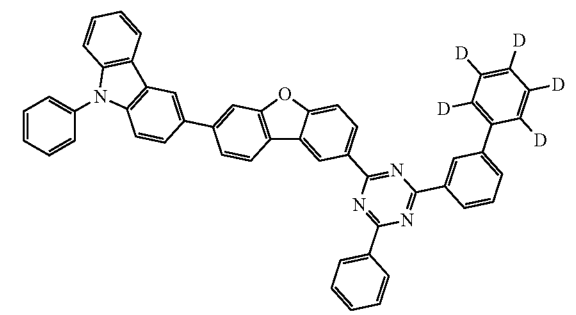
-continued
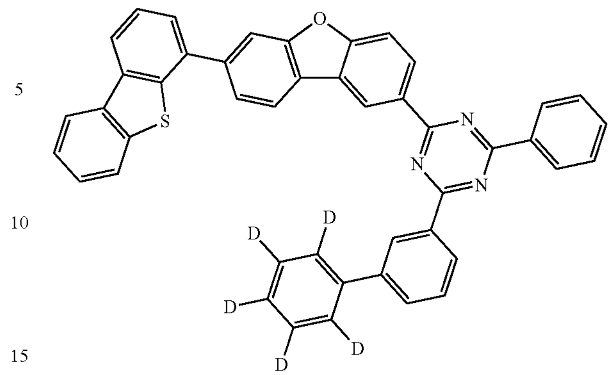
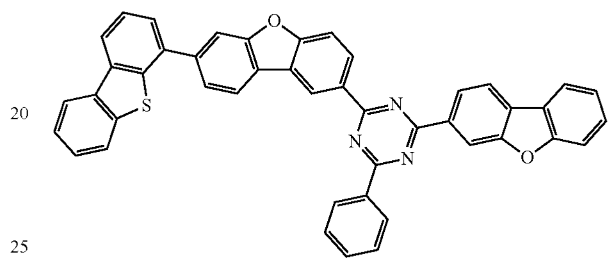
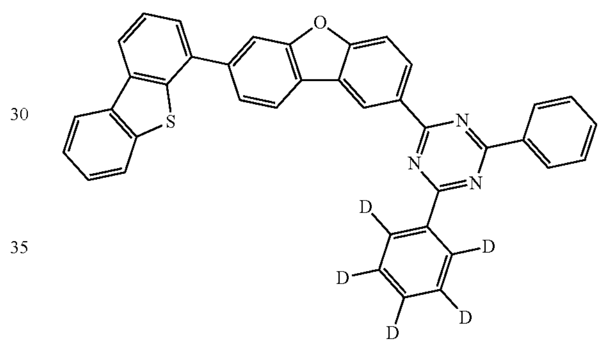
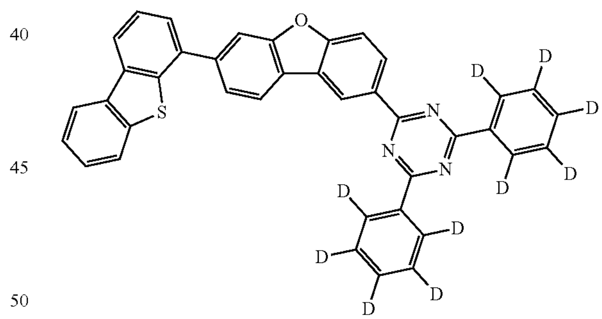
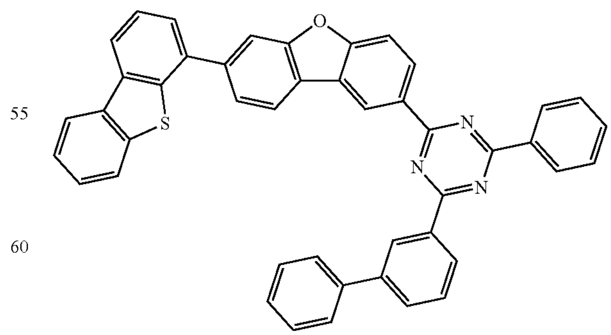

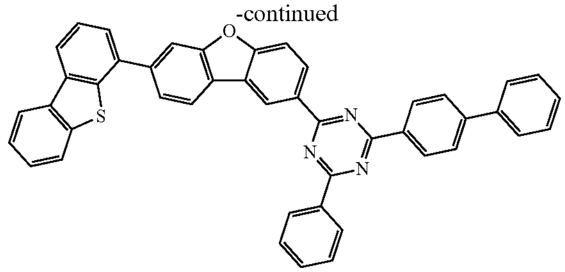
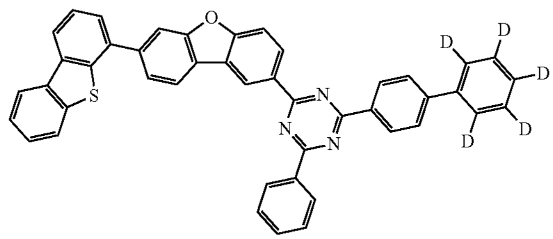
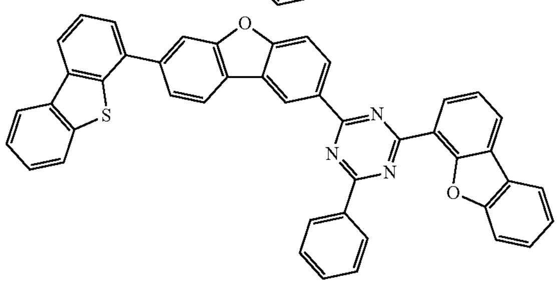
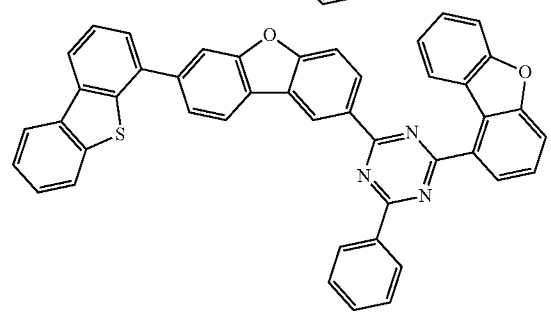
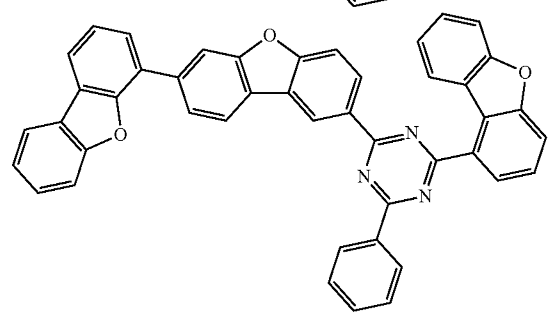
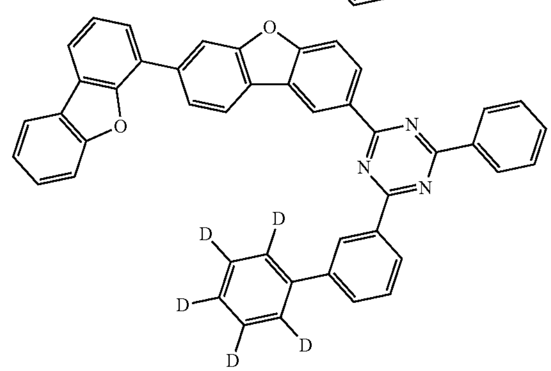
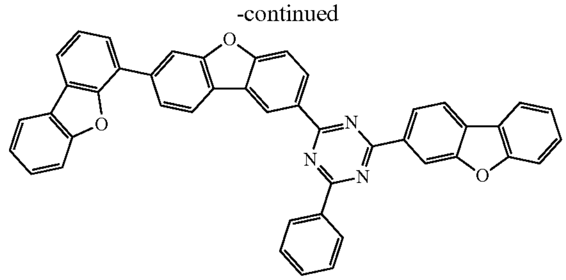
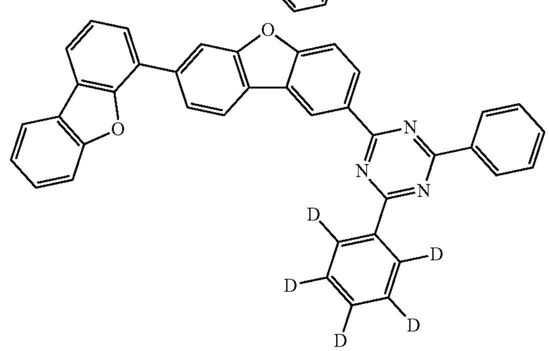
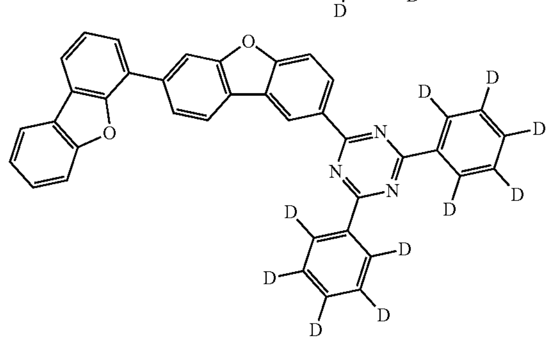
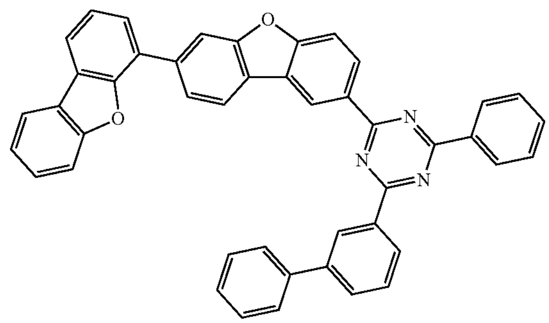
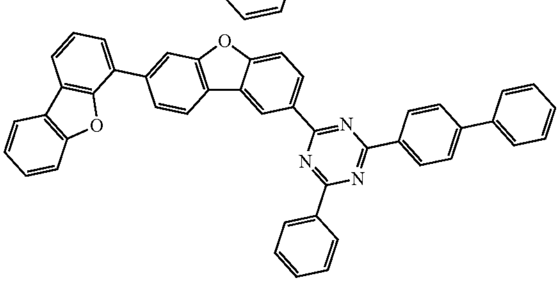
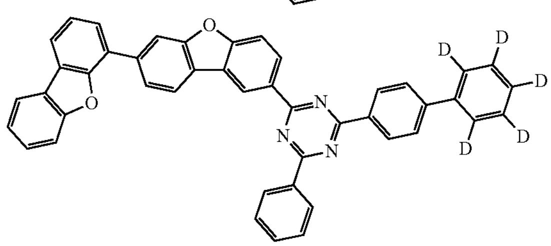

-continued
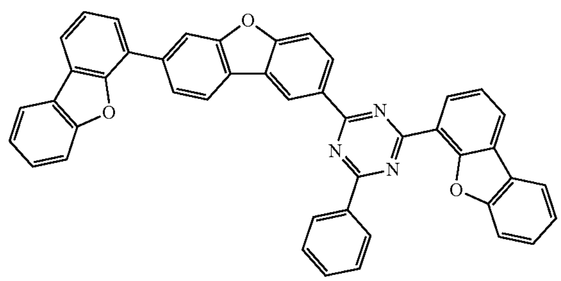
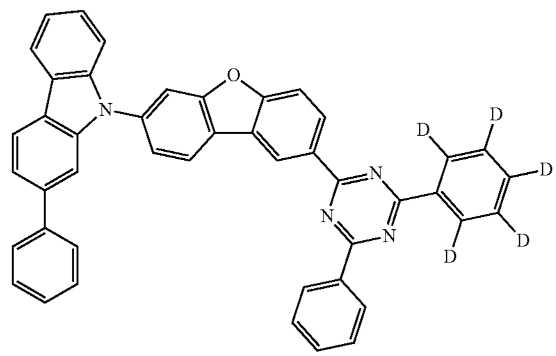
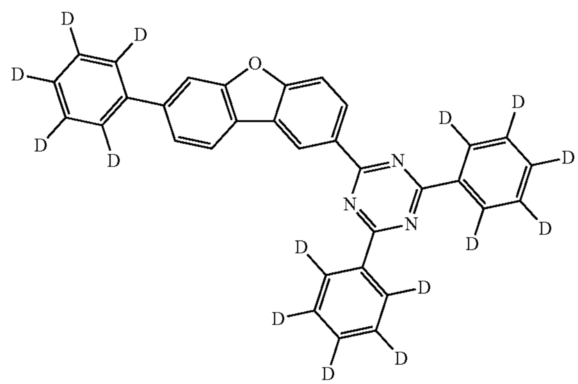
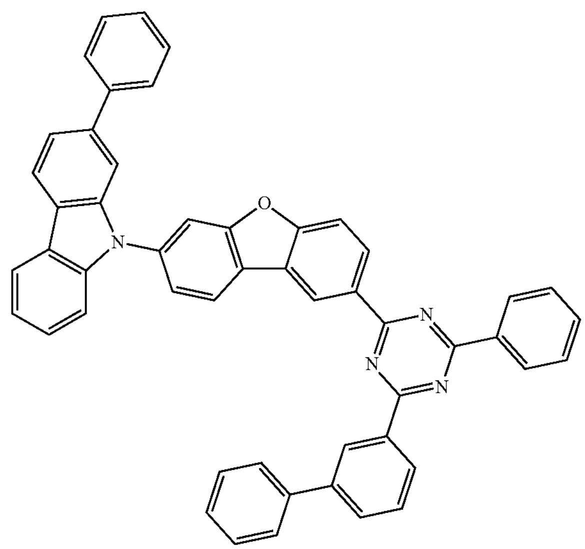
-continued
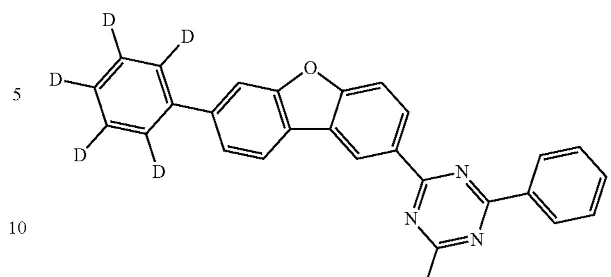
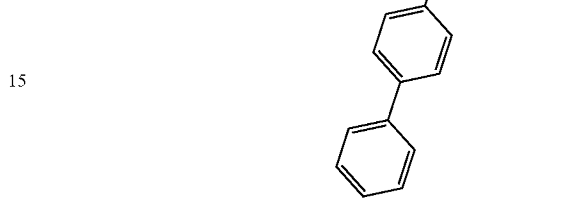
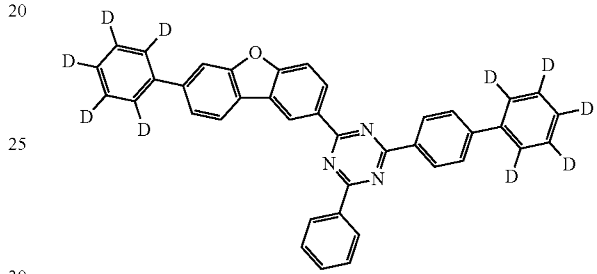
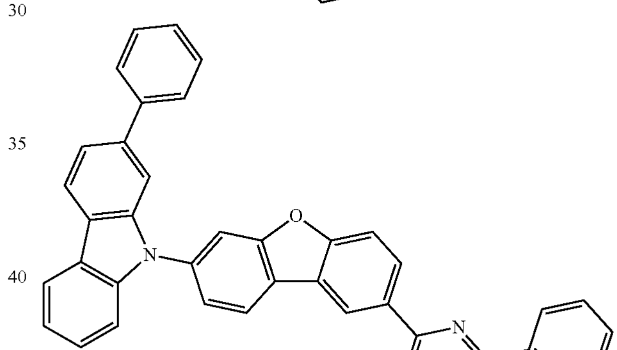
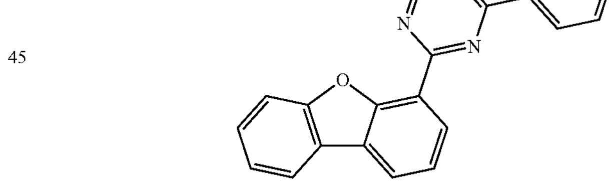
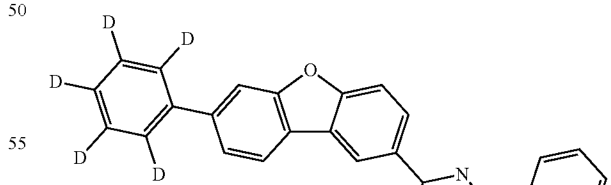
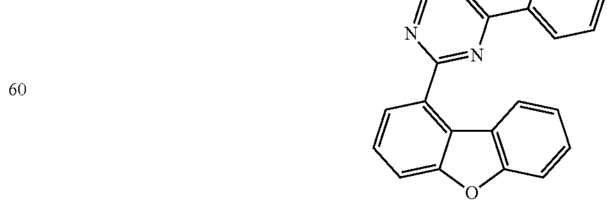

-continued
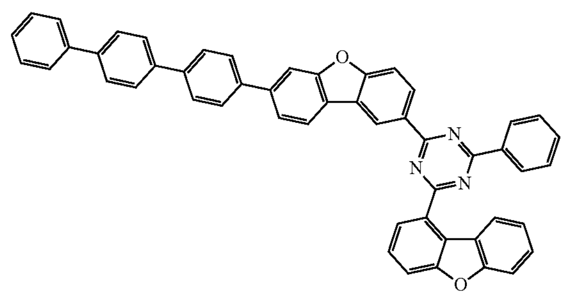
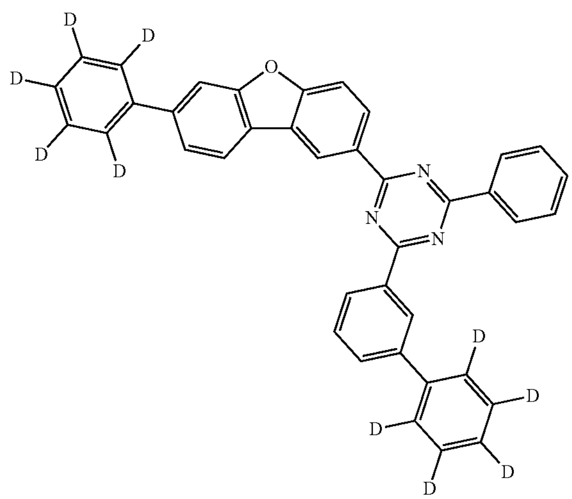
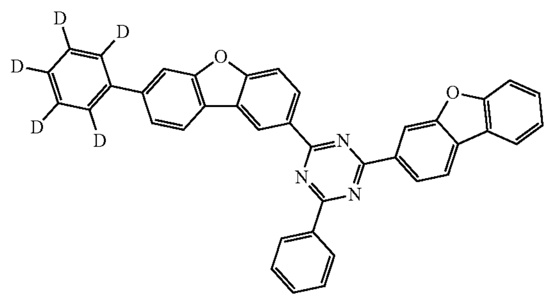
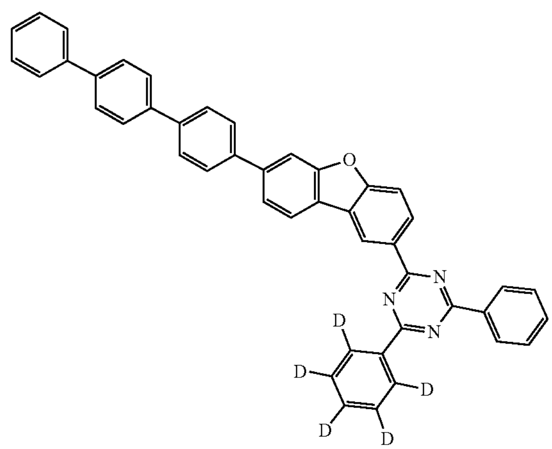
-continued
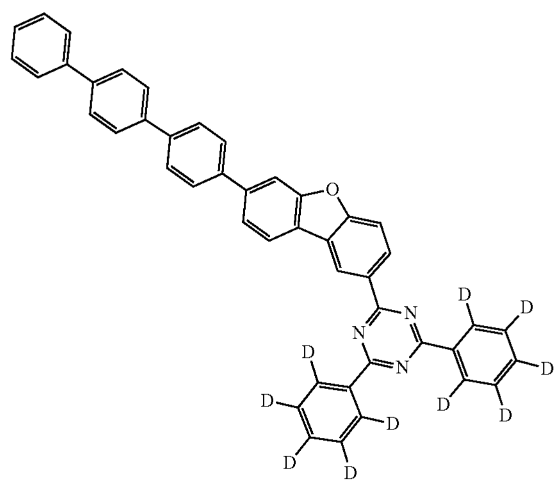
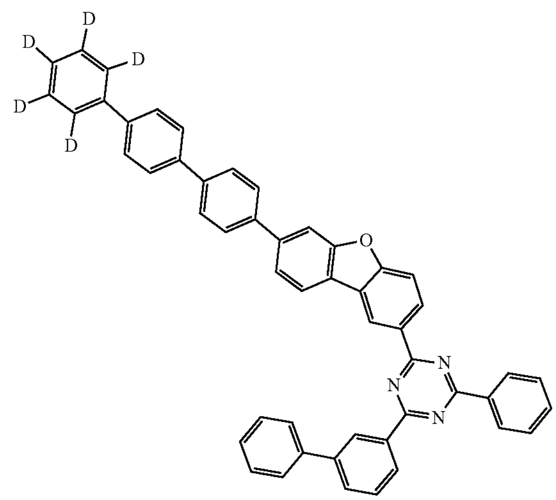
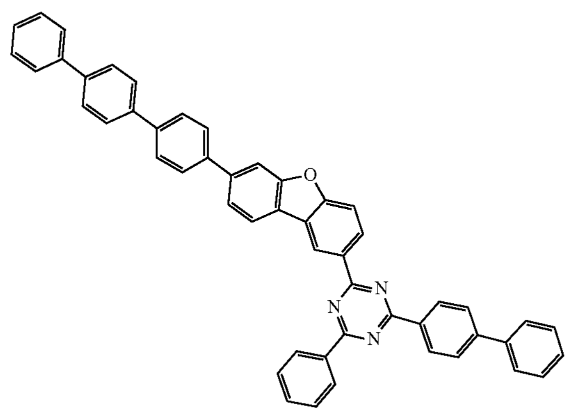

-continued
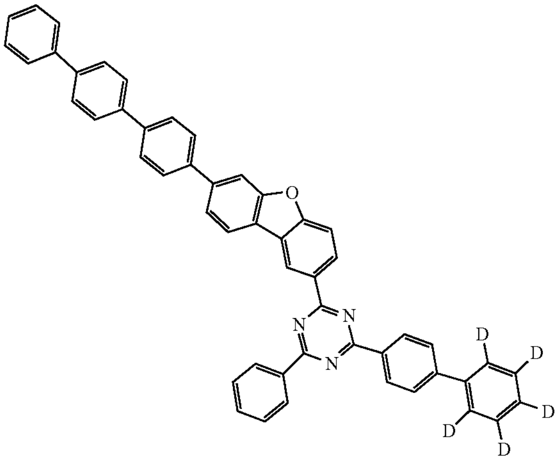
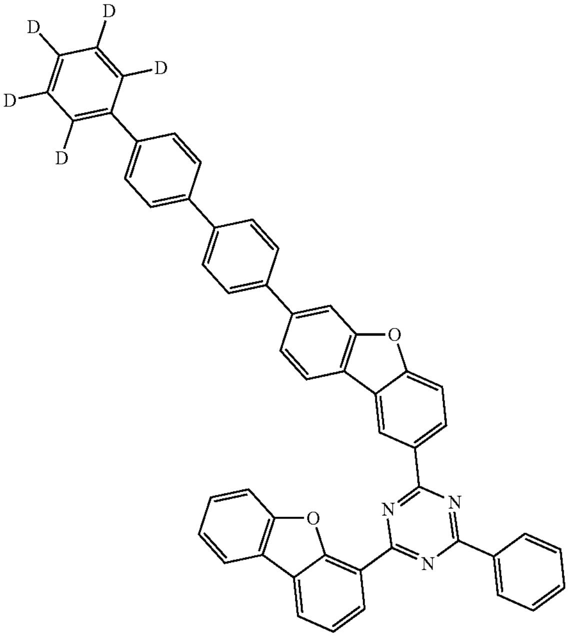
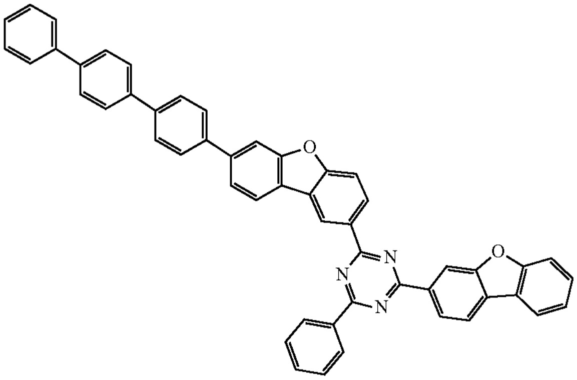
-continued
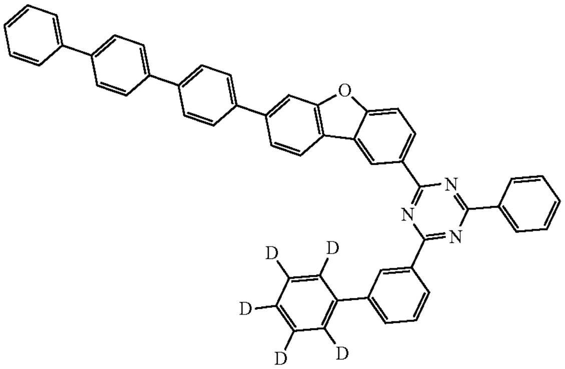
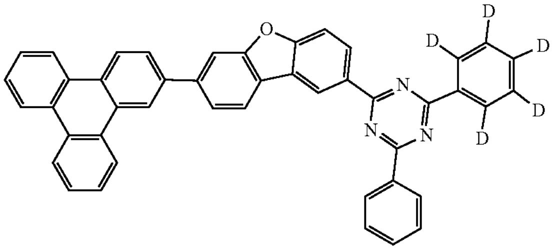
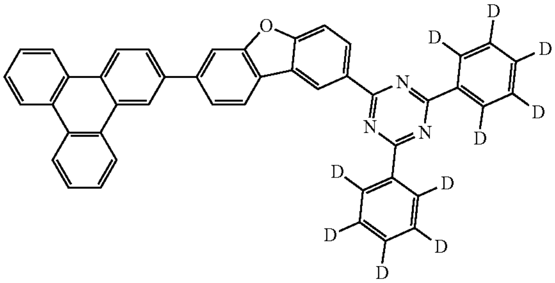
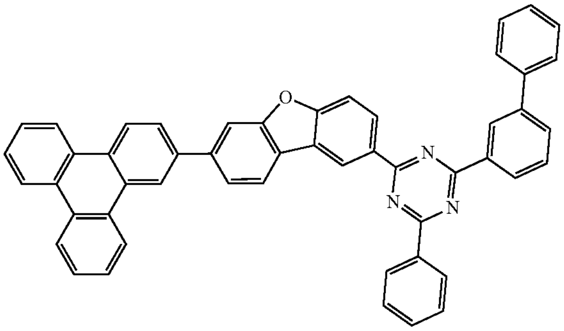
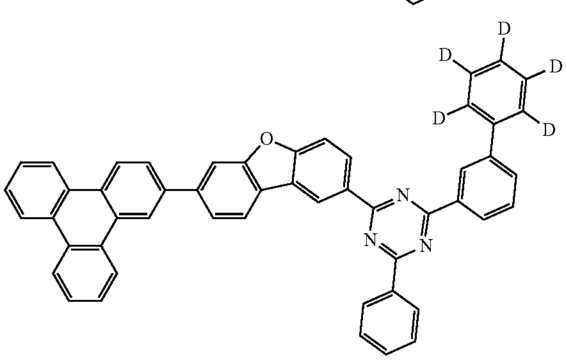

-continued
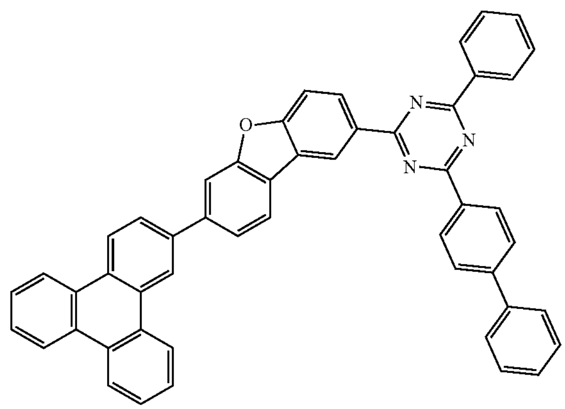
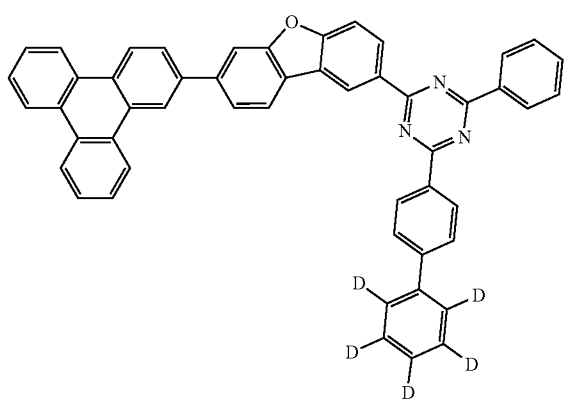
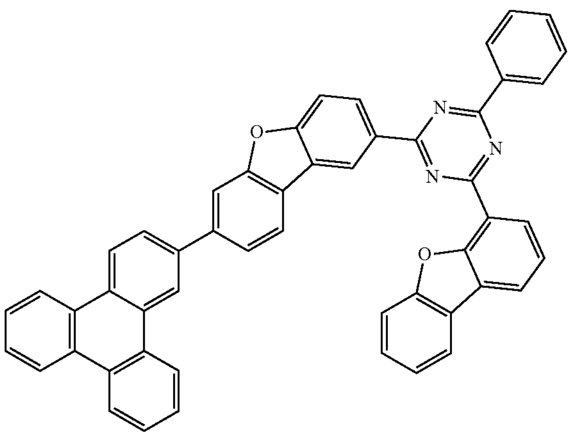
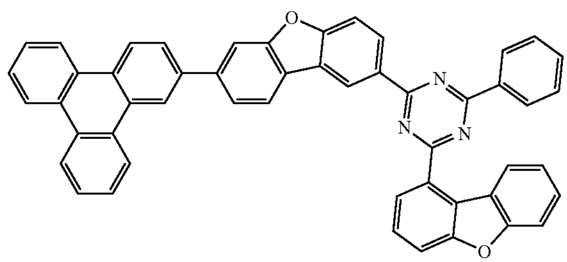
-continued
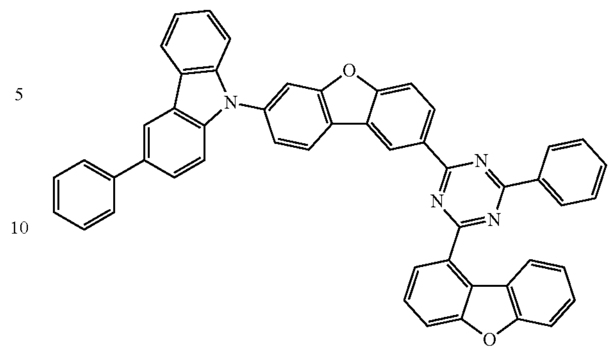
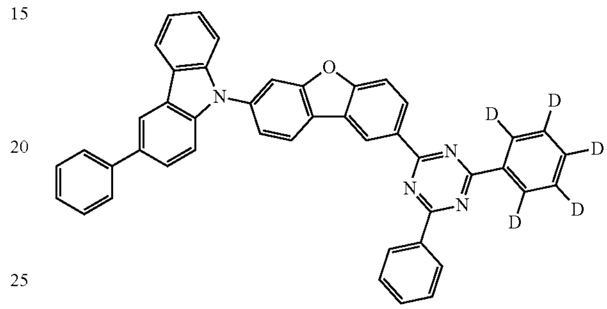
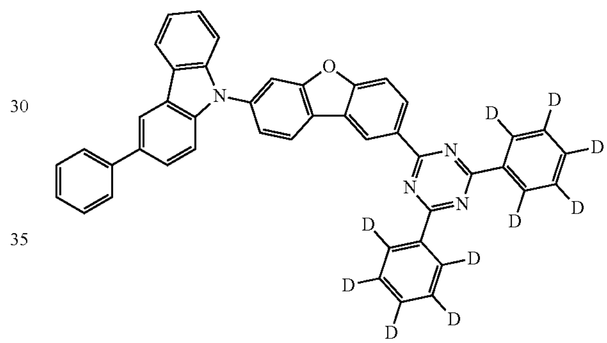
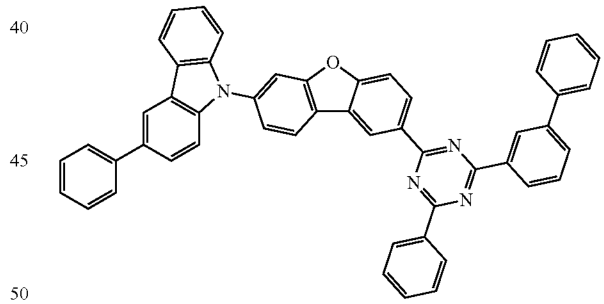
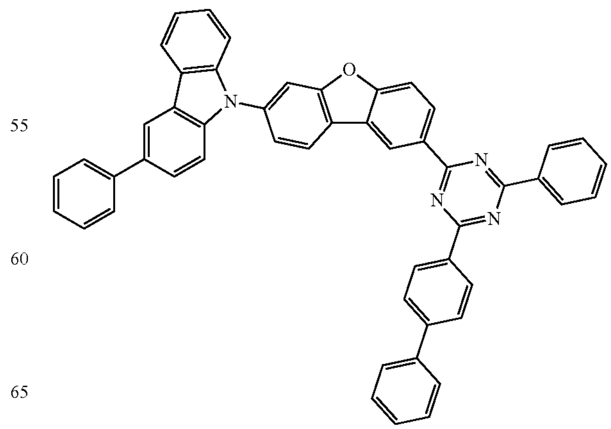

-continued
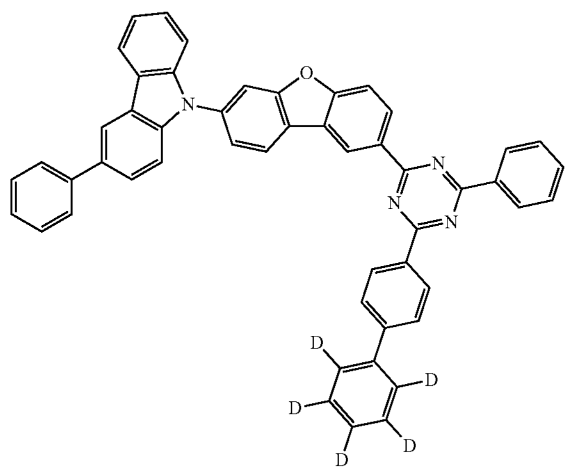
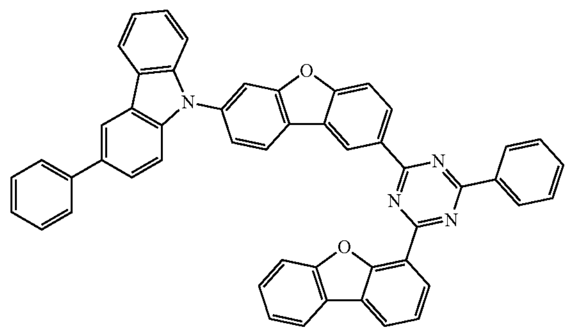
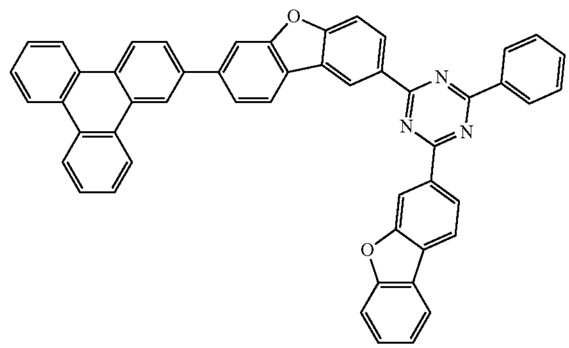
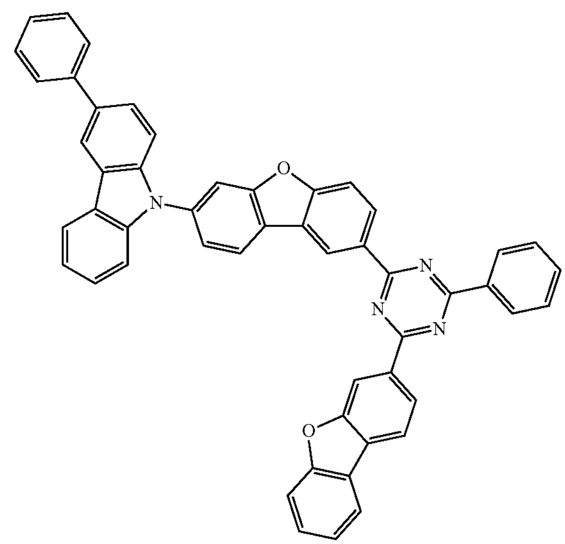
-continued
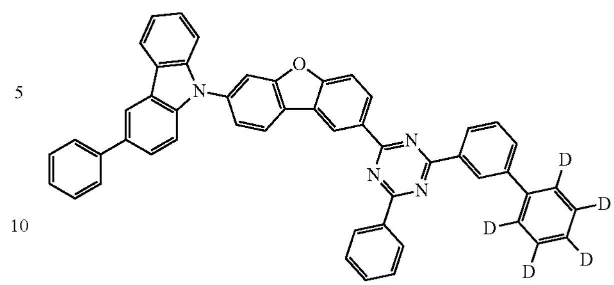
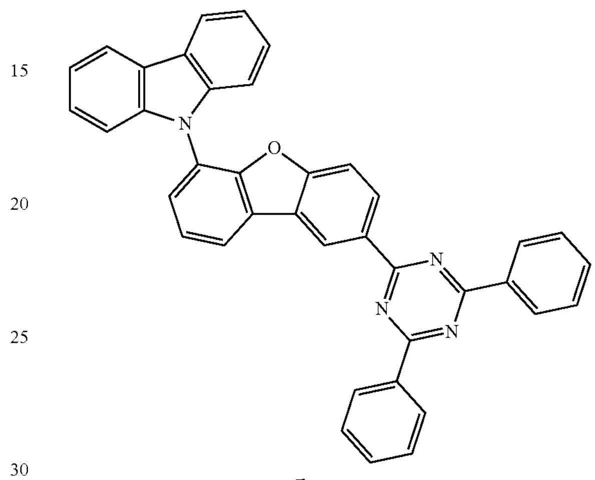
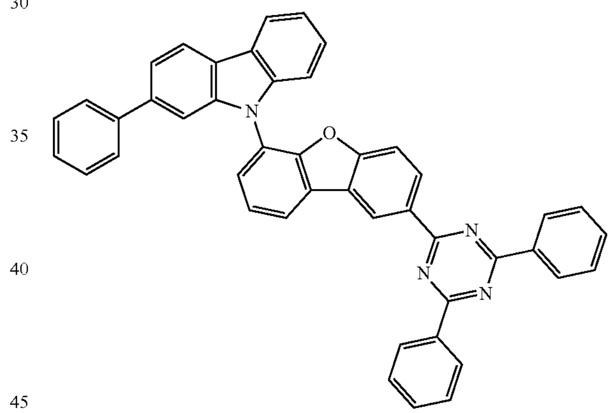
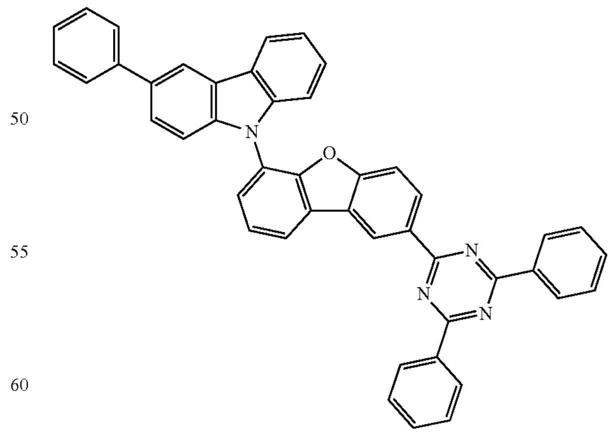

-continued
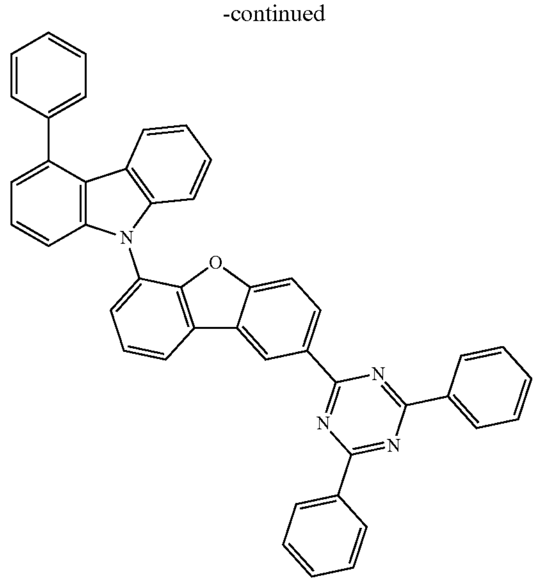
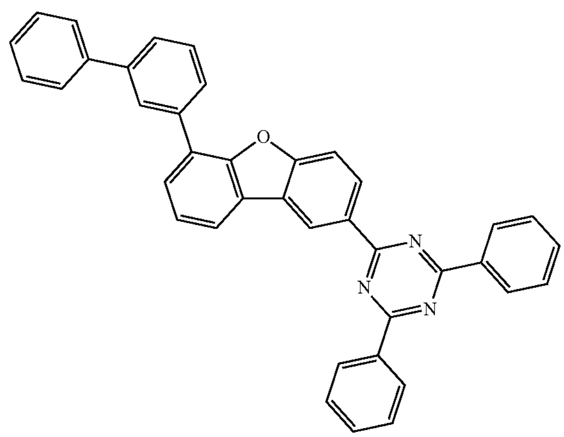
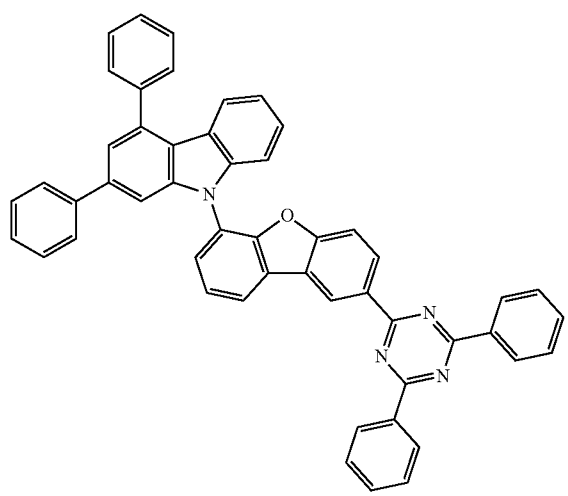
-continued
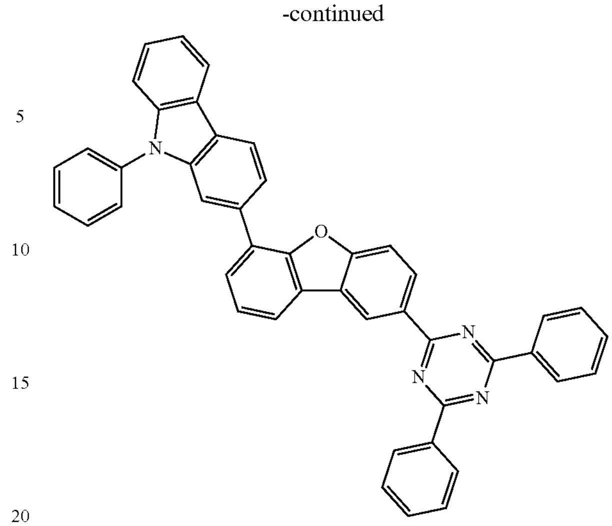
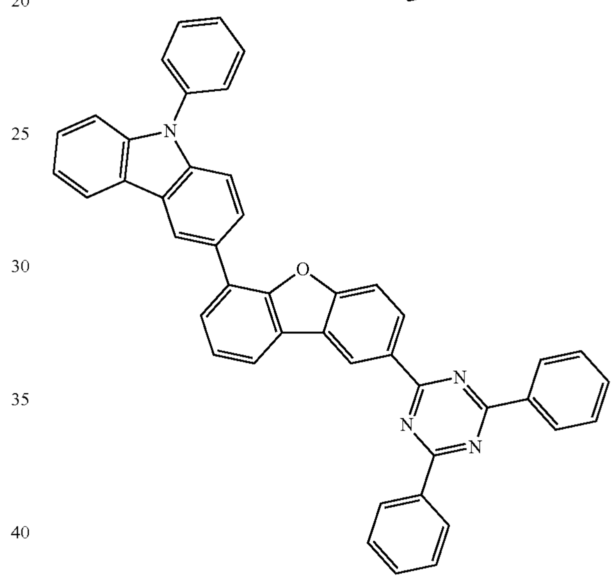
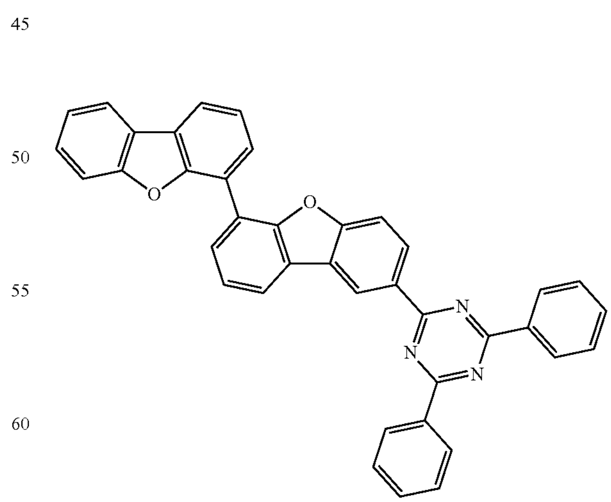

-continued
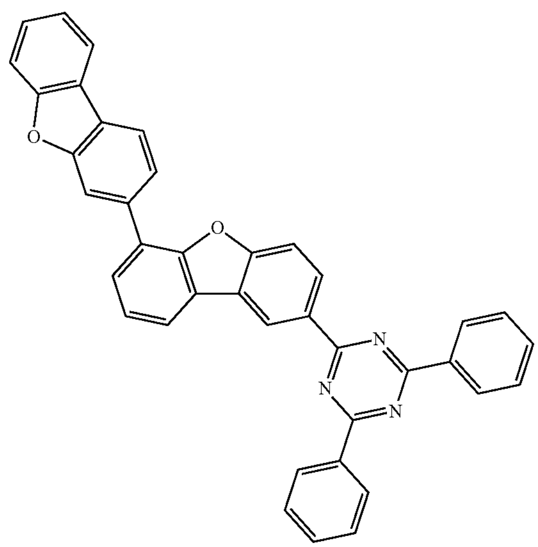
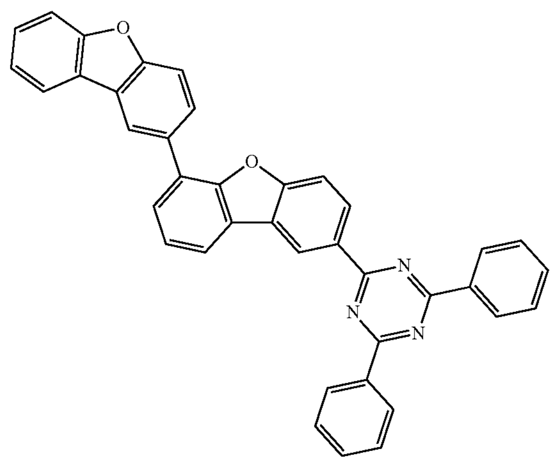
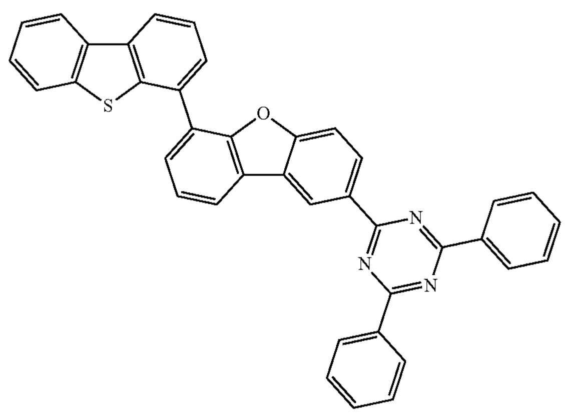
-continued
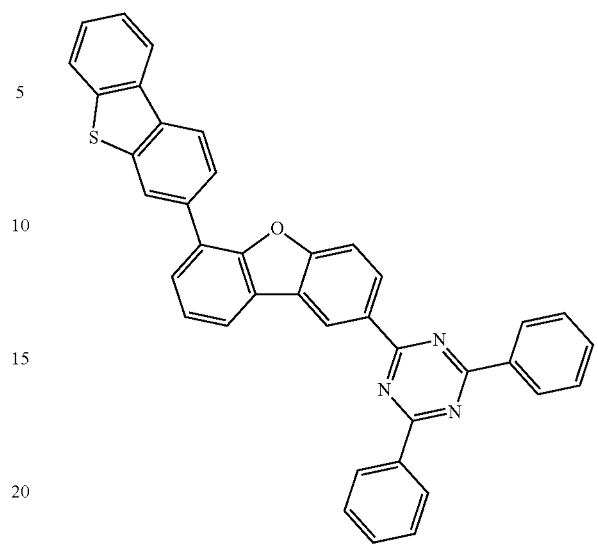
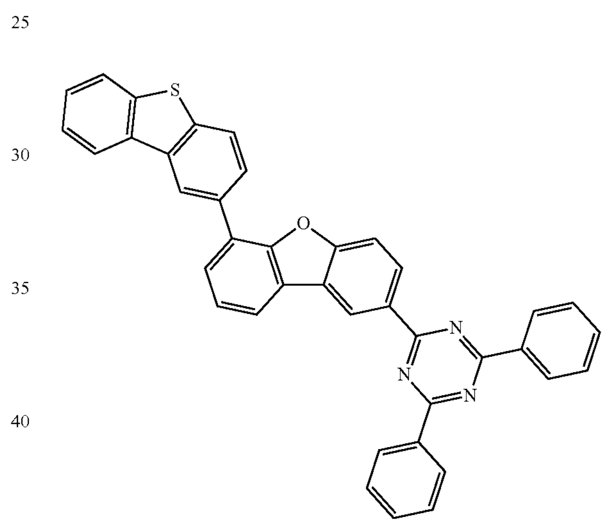
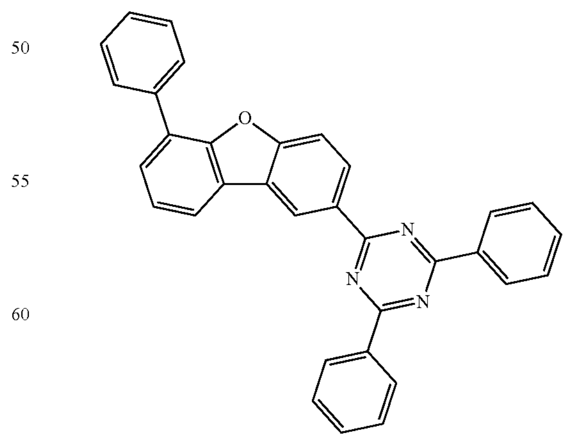

-continued
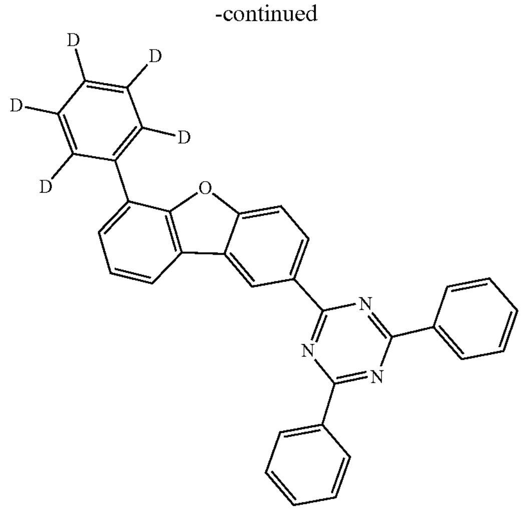
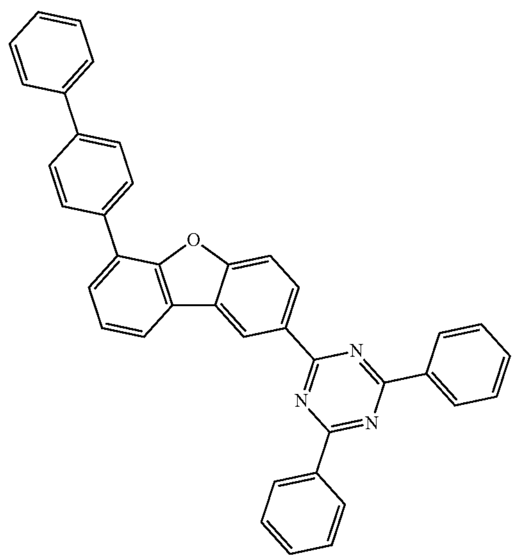
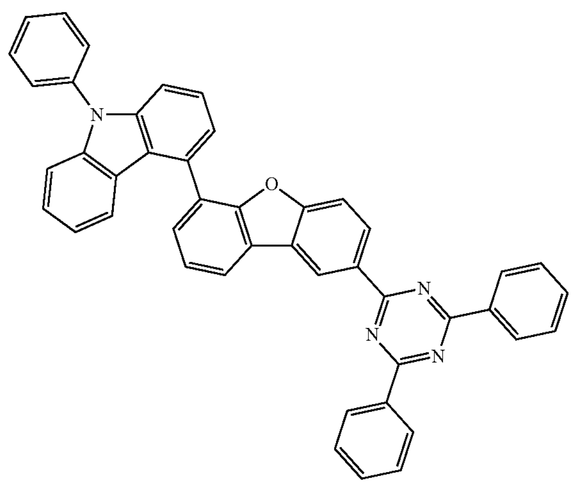
-continued
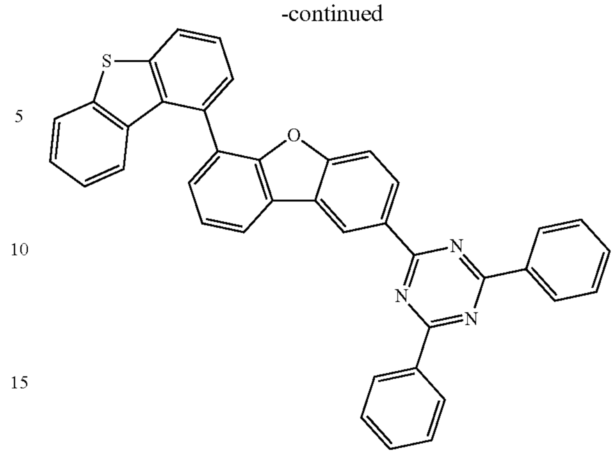
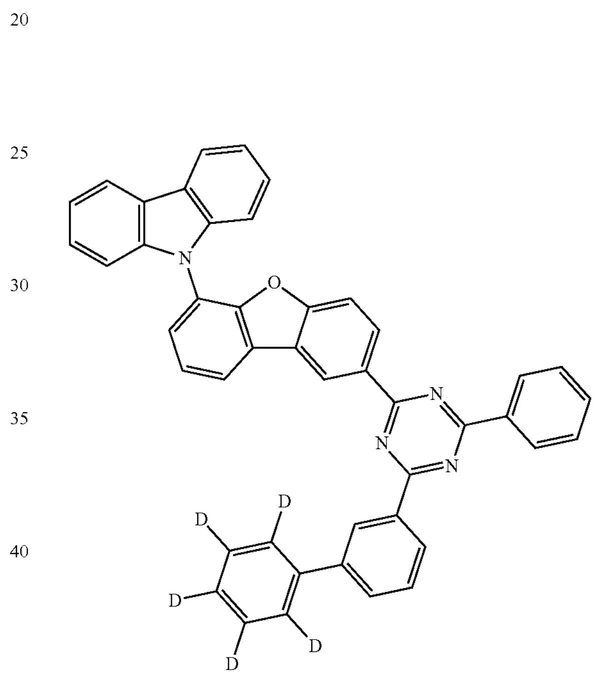
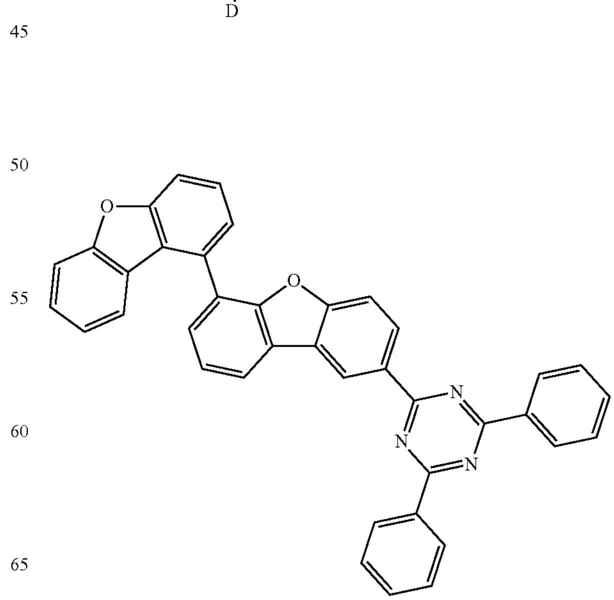

-continued
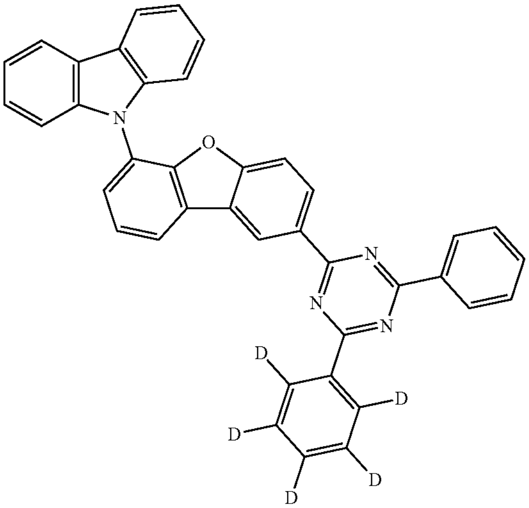
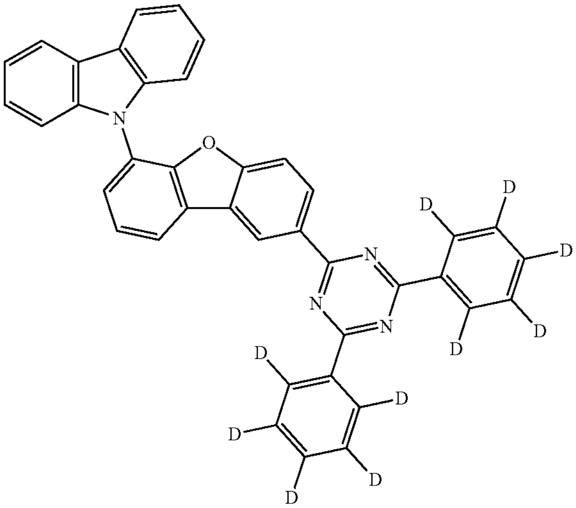
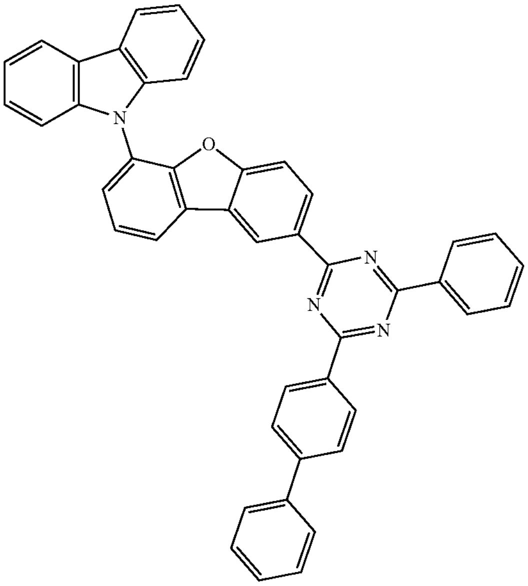
-continued
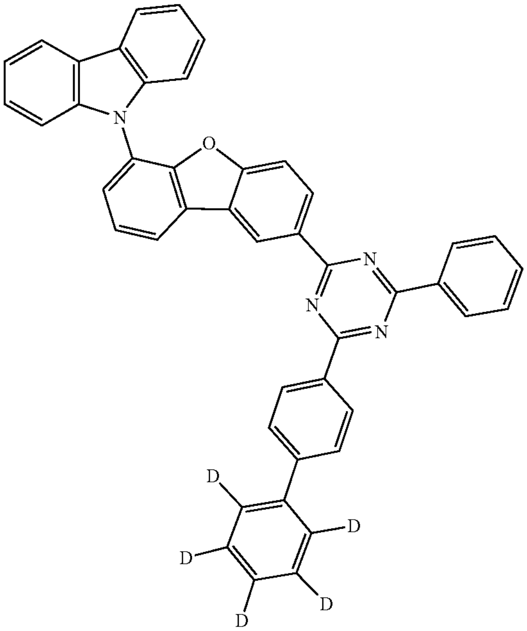
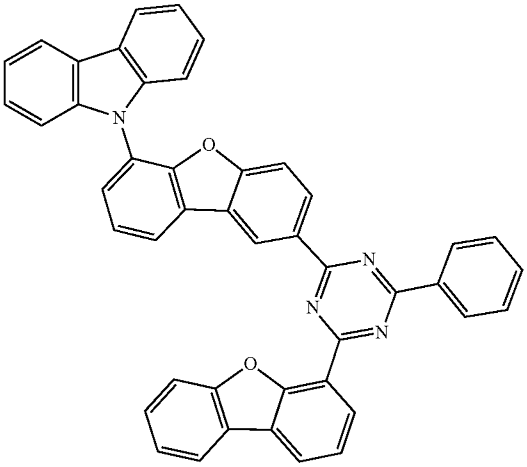
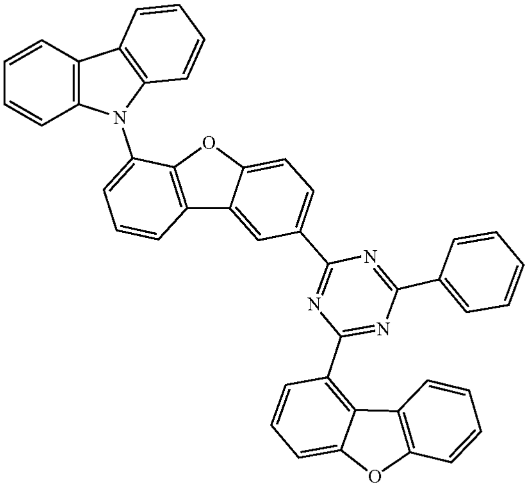

-continued
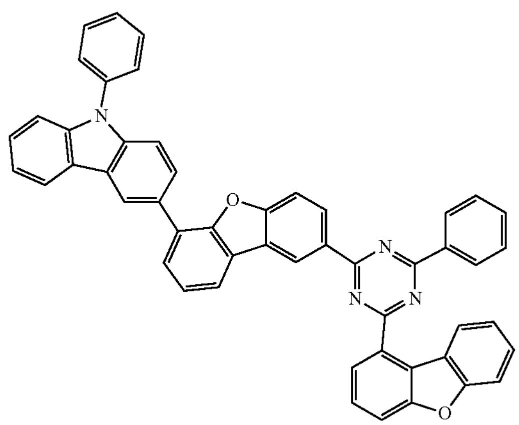
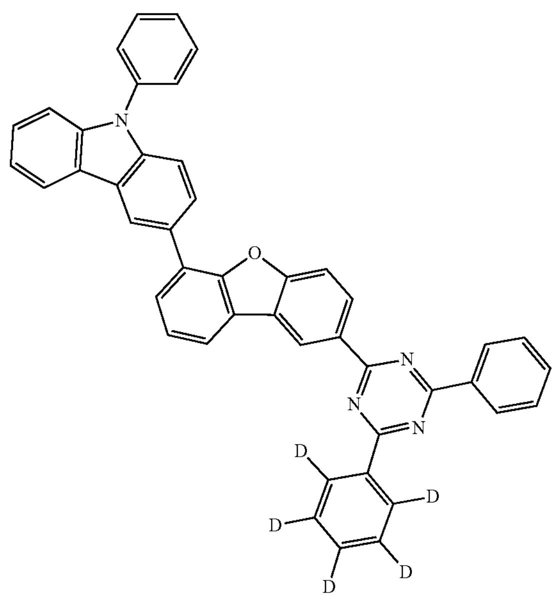
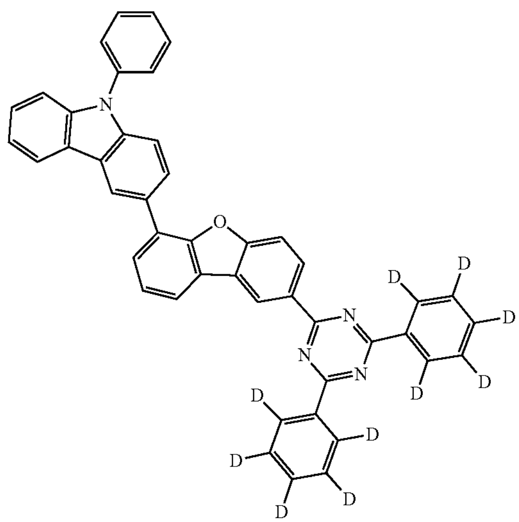
-continued
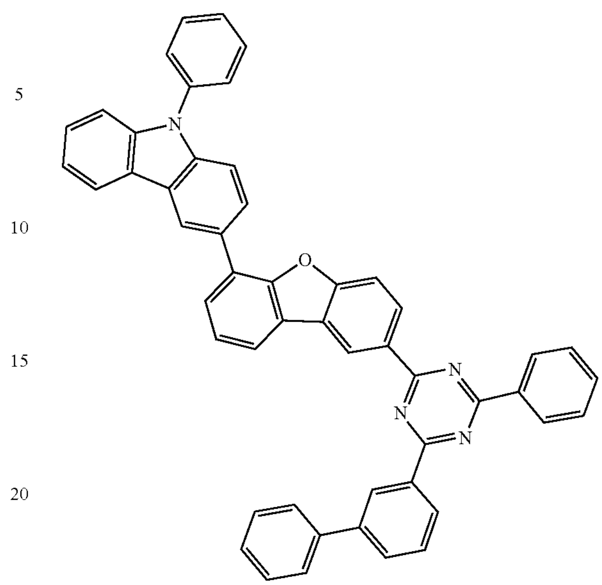
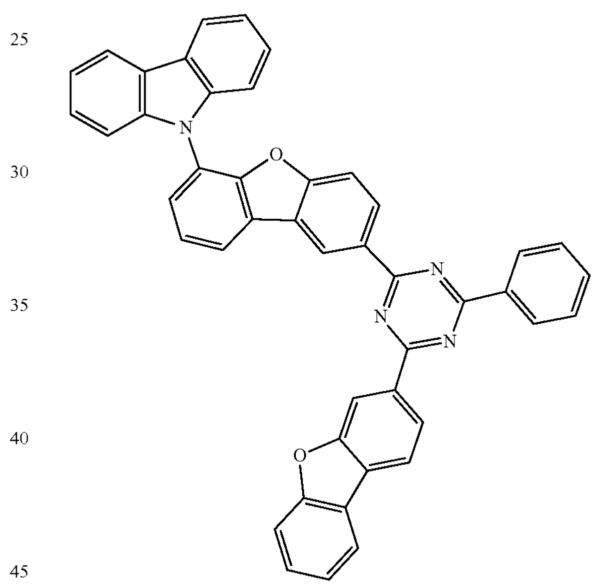
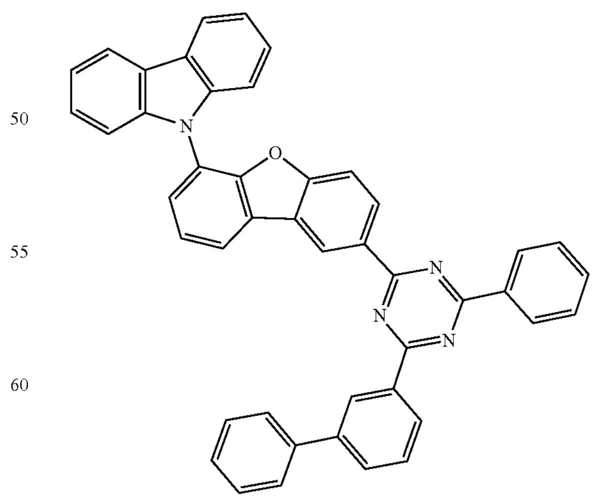

-continued
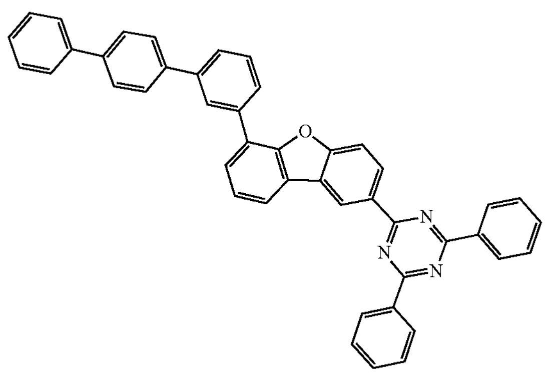
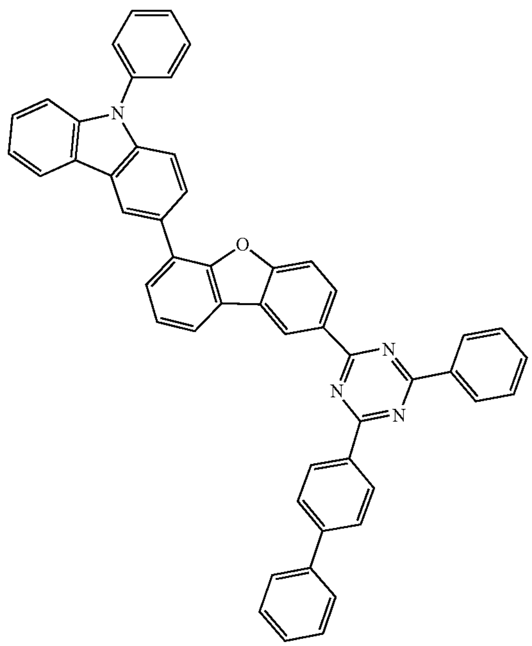 [SMILES: c1ccc(-c2ccc(-c3nc(-c4ccccc4)nc(-c4ccc5oc6c(-c7ccc8c(c7)c7ccccc7n8-c7ccccc7)cccc6c5c4)n3)cc2)cc1]
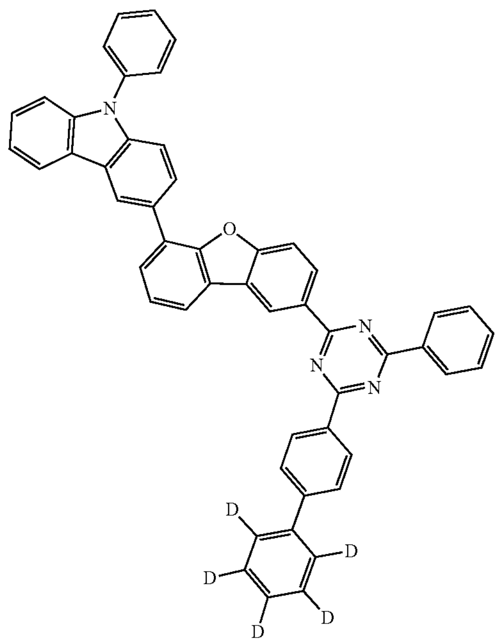
-continued
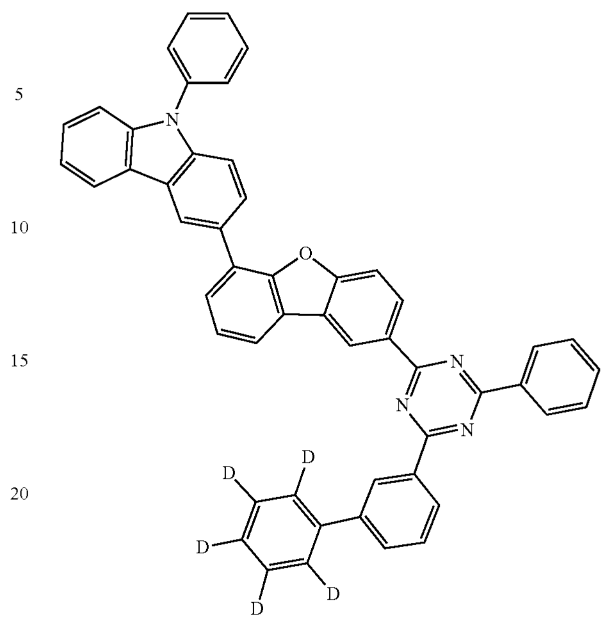
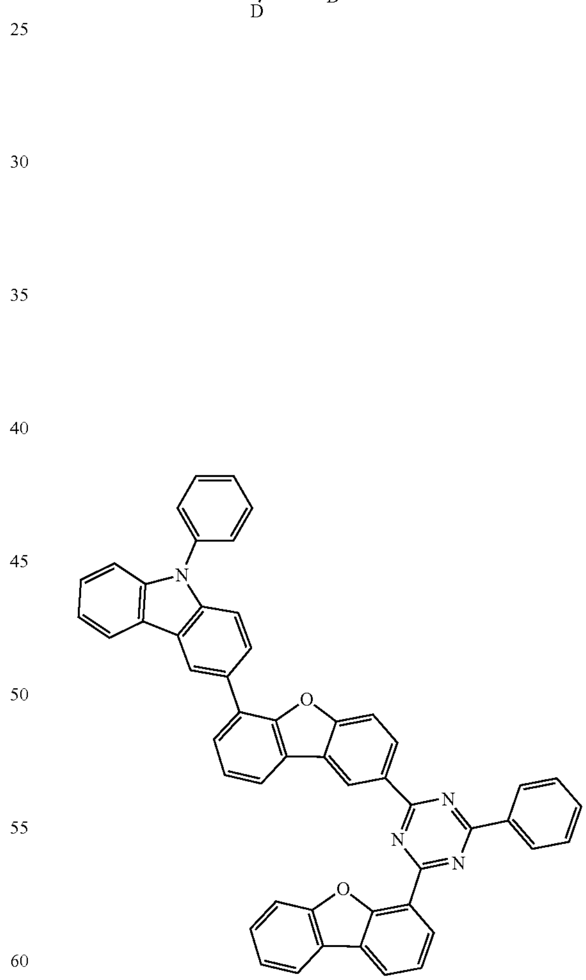

-continued
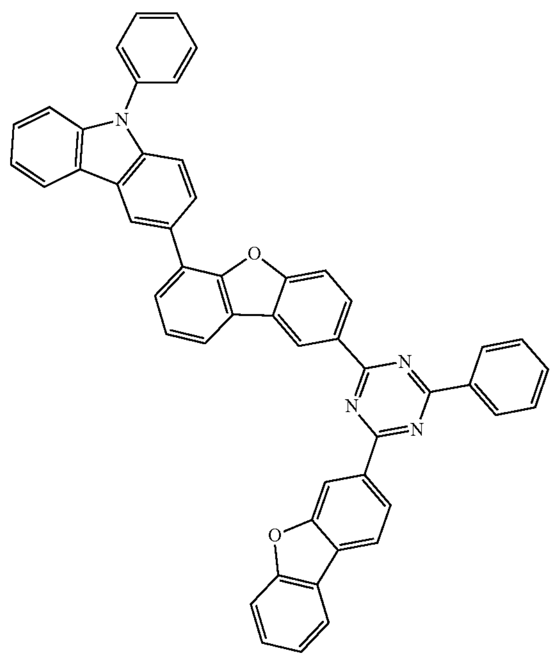
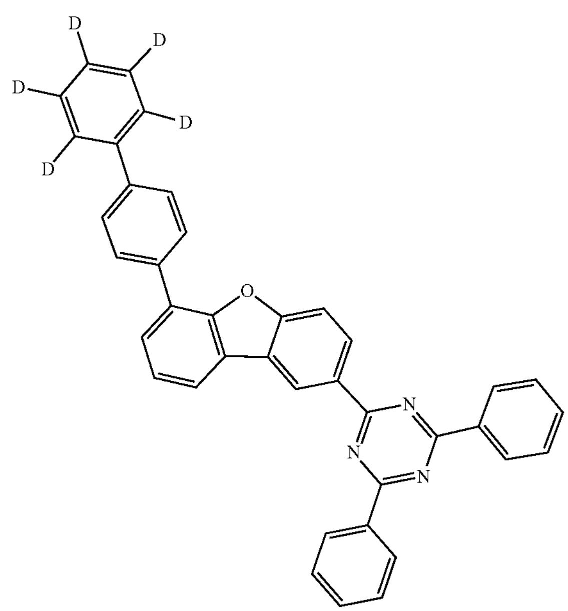
-continued
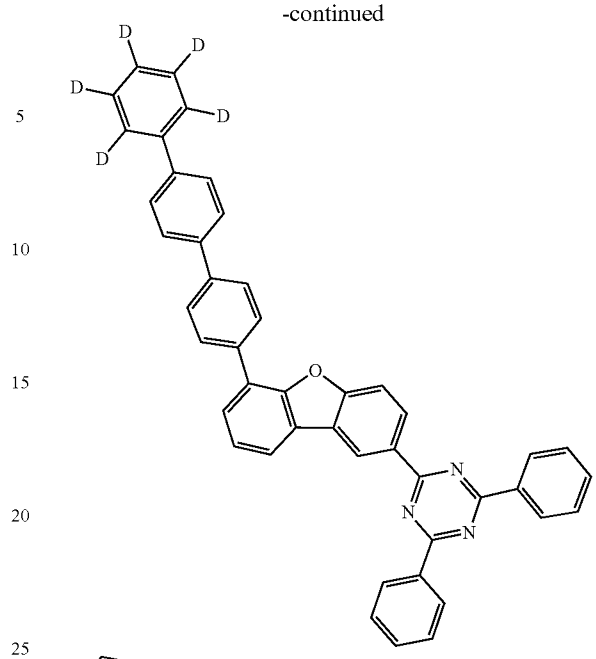
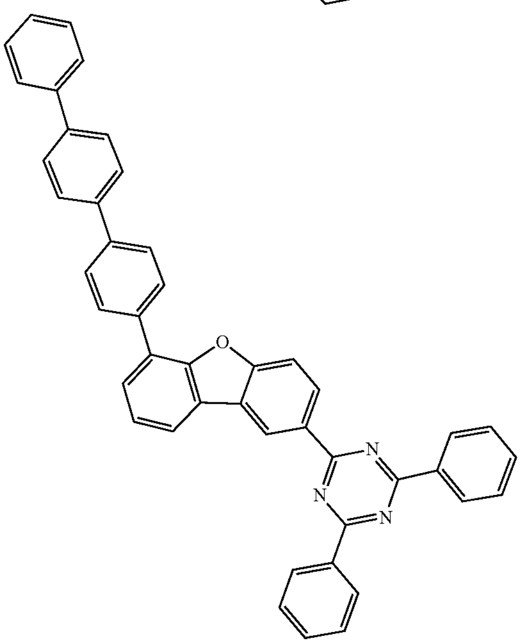
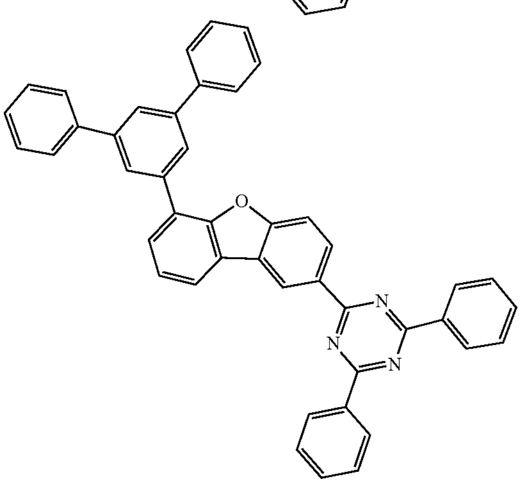

-continued
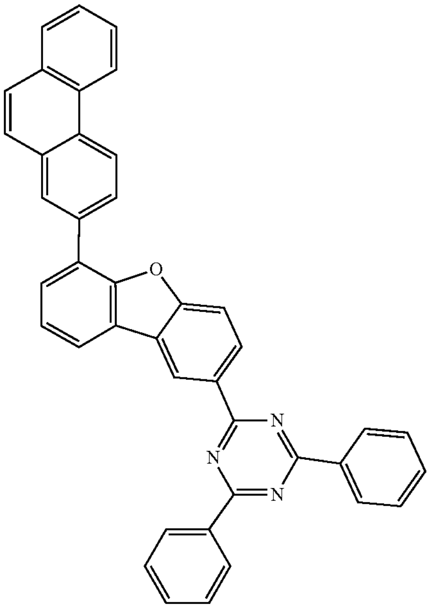
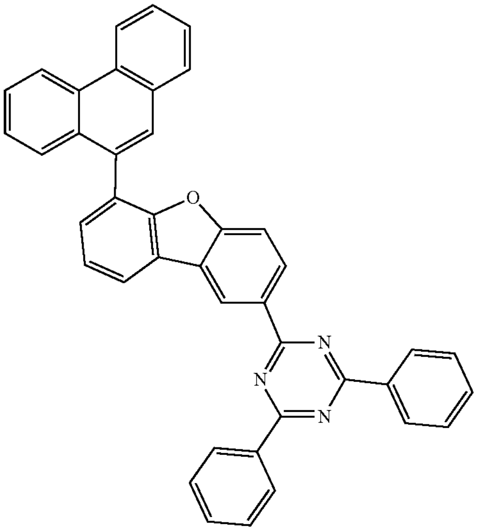
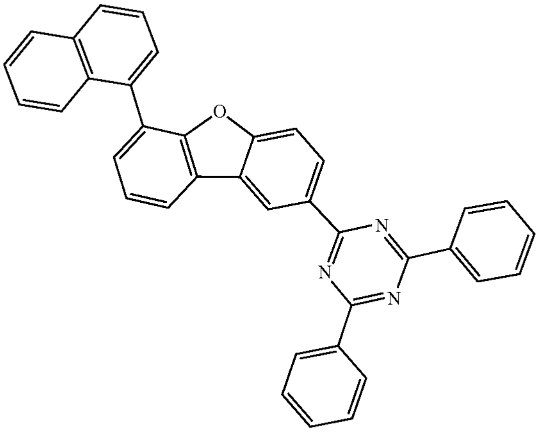
-continued
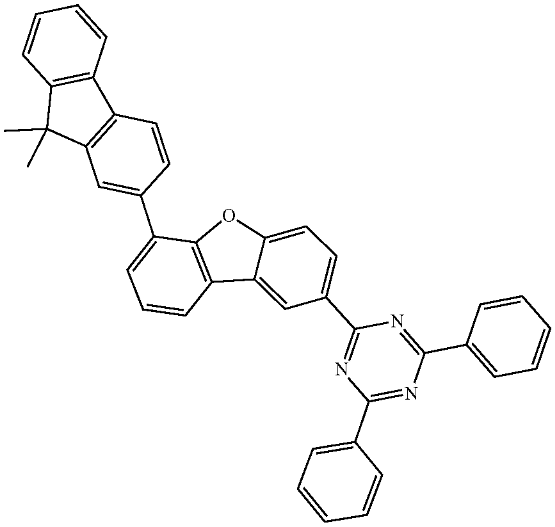
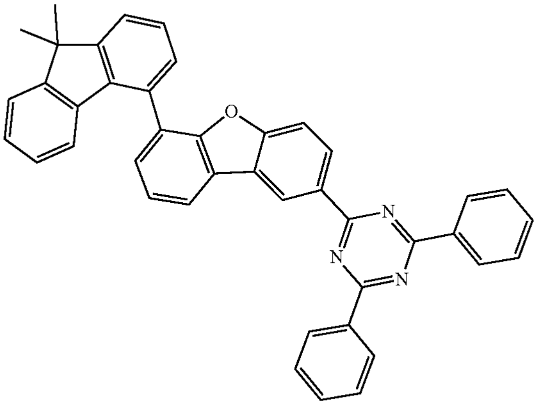
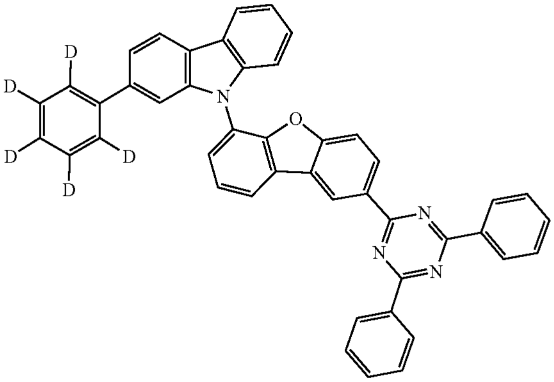

-continued
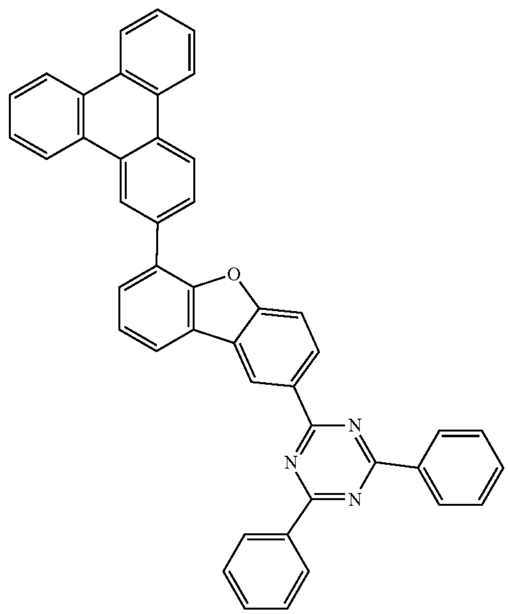
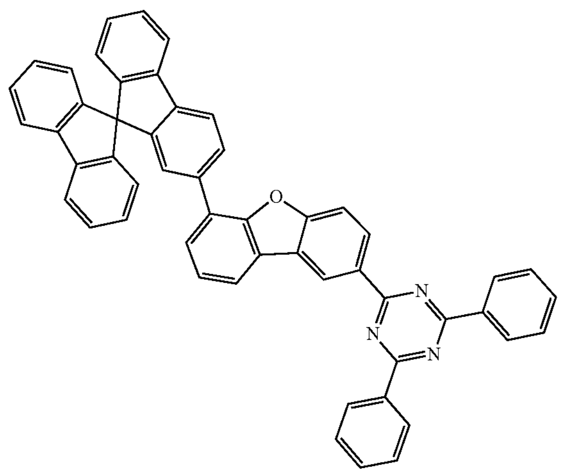
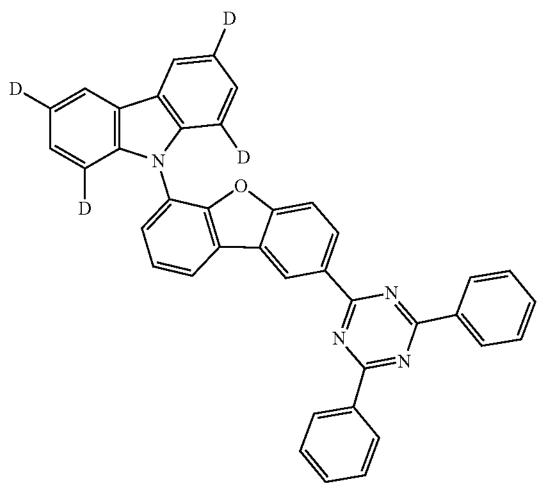
-continued
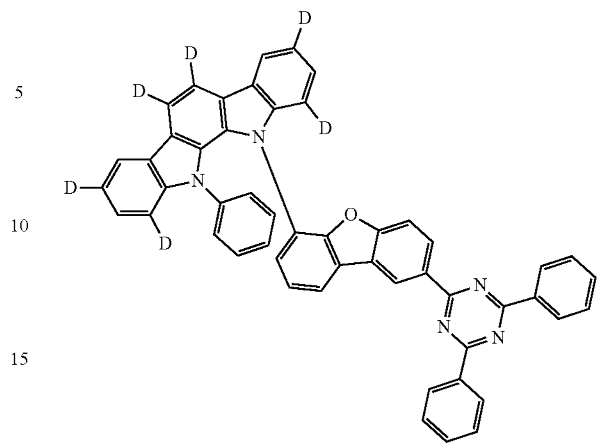
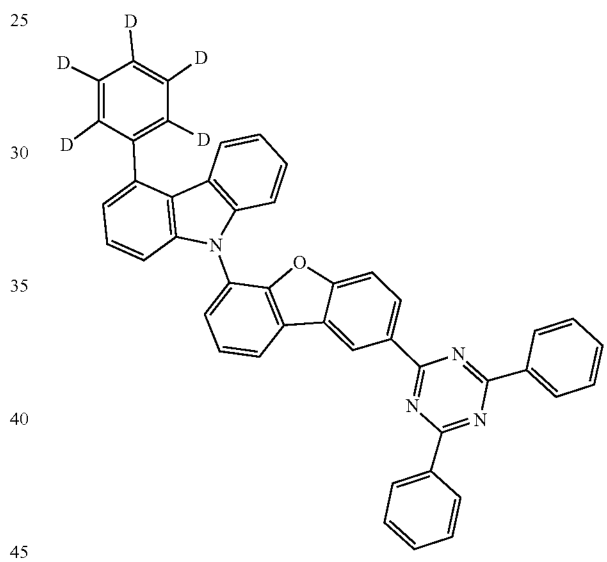
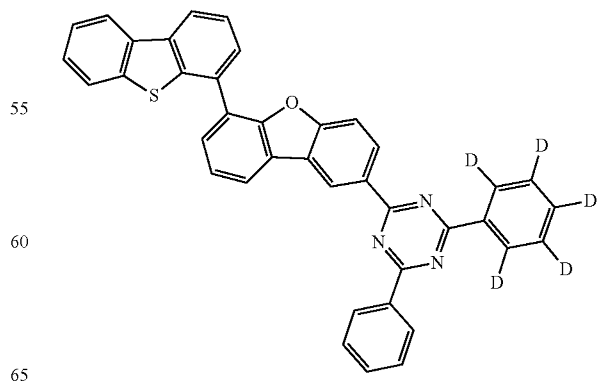

-continued
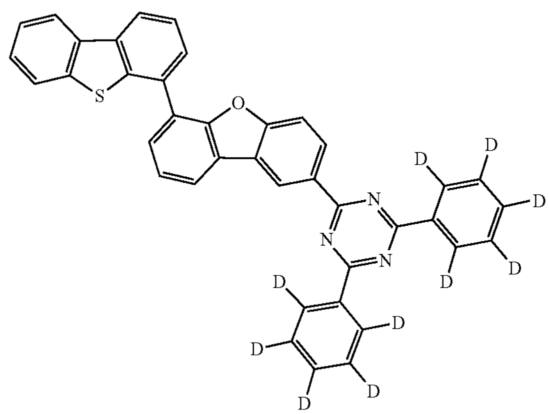
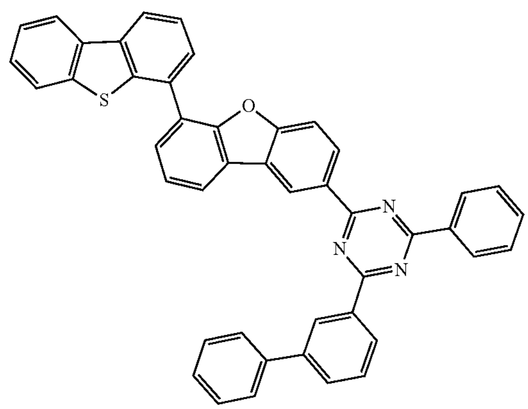
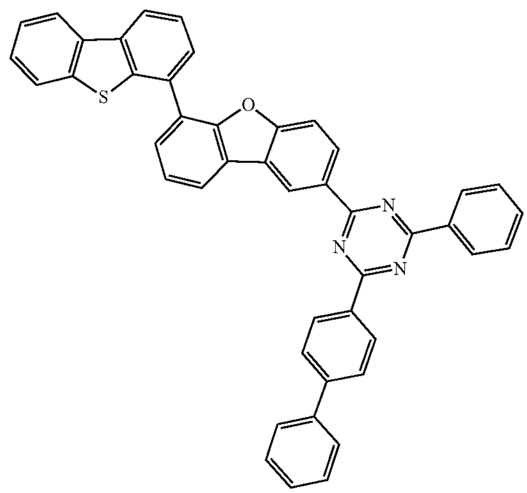
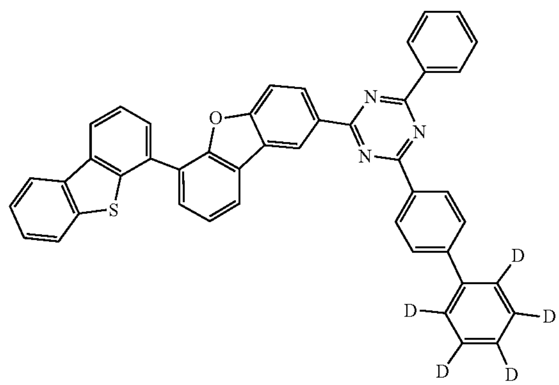
-continued
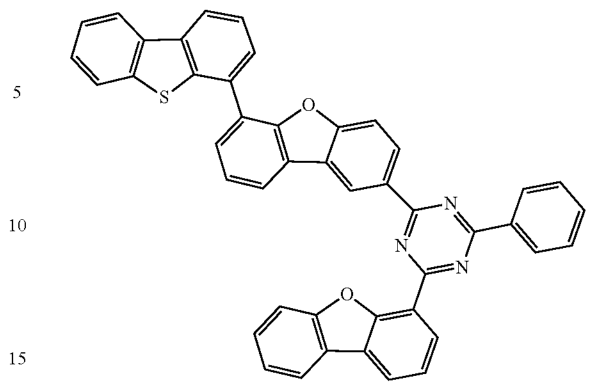
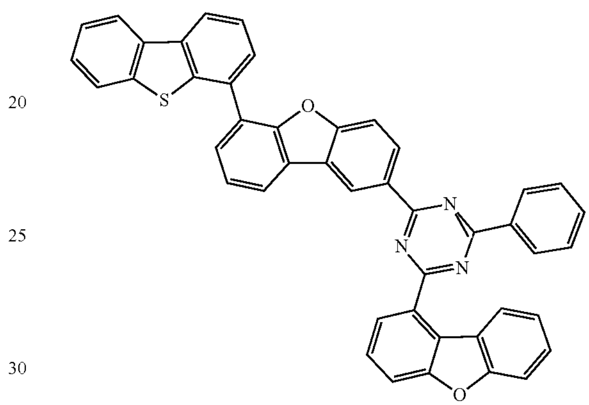
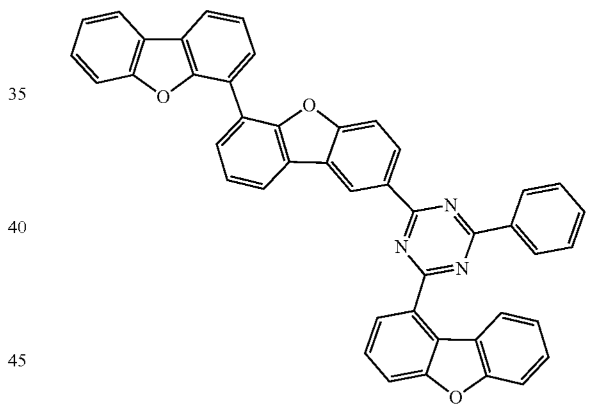
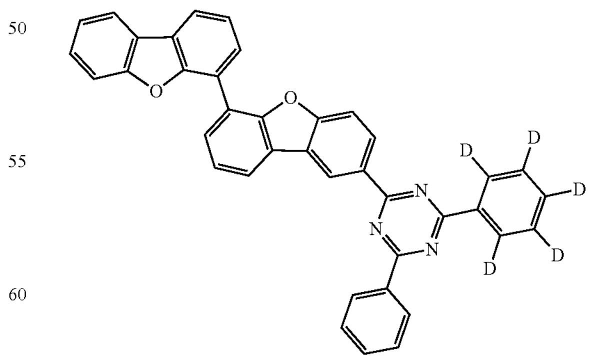

-continued
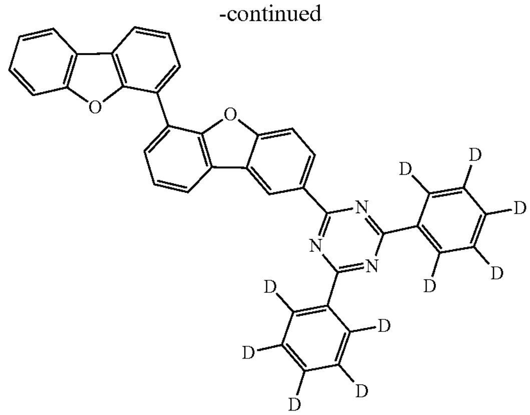
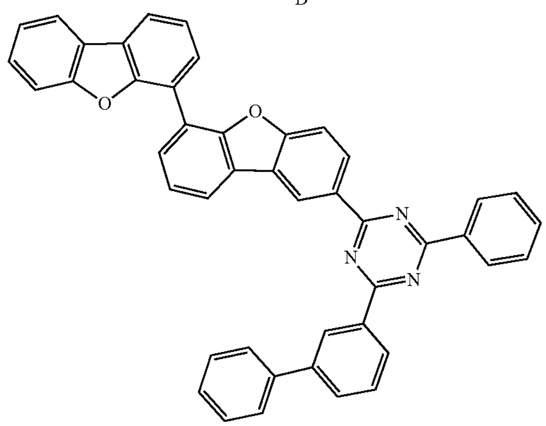
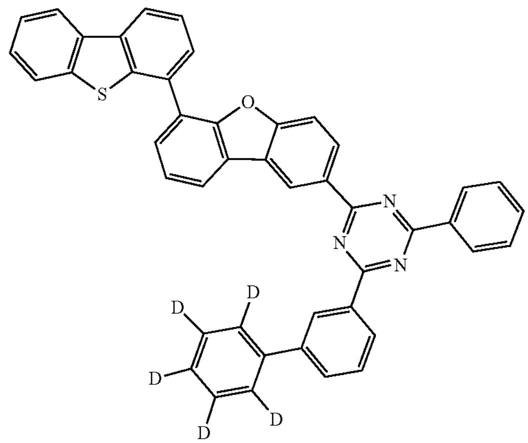
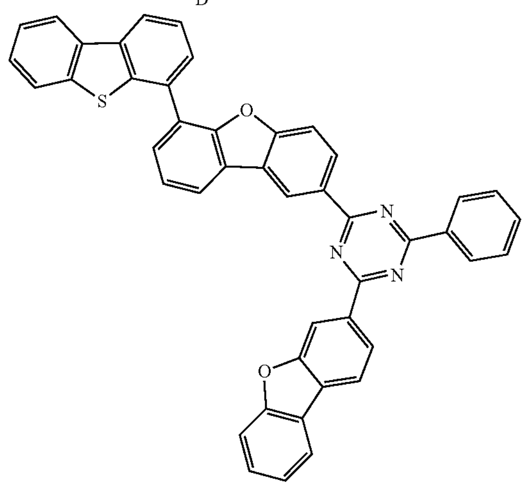
-continued
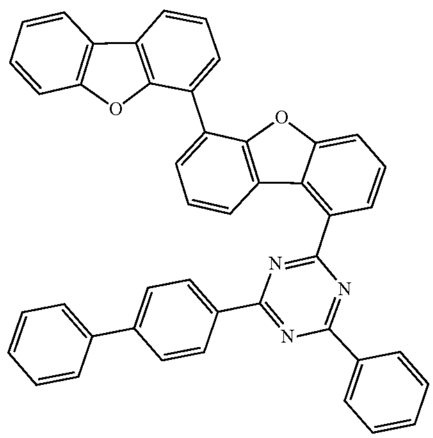
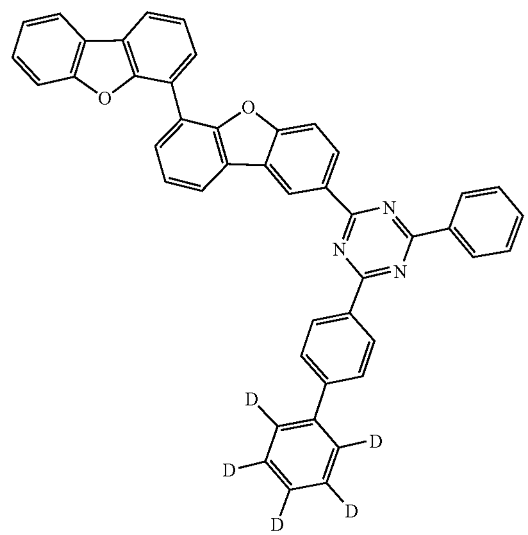
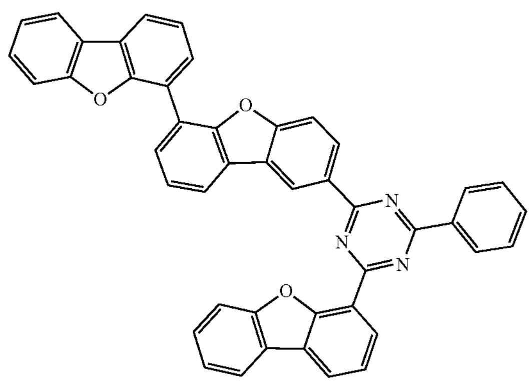

-continued
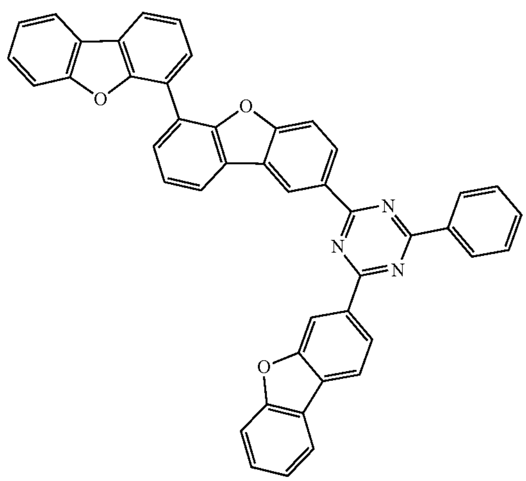
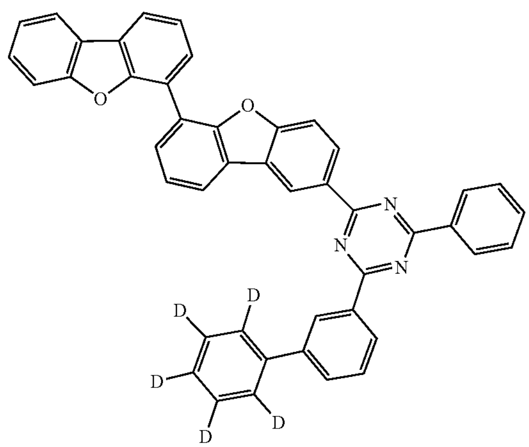
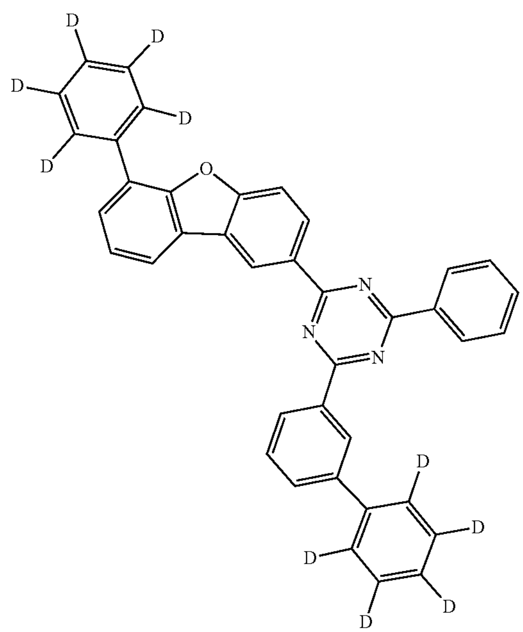
-continued
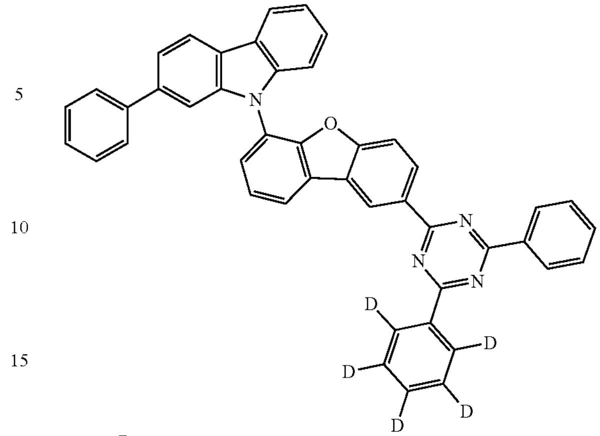
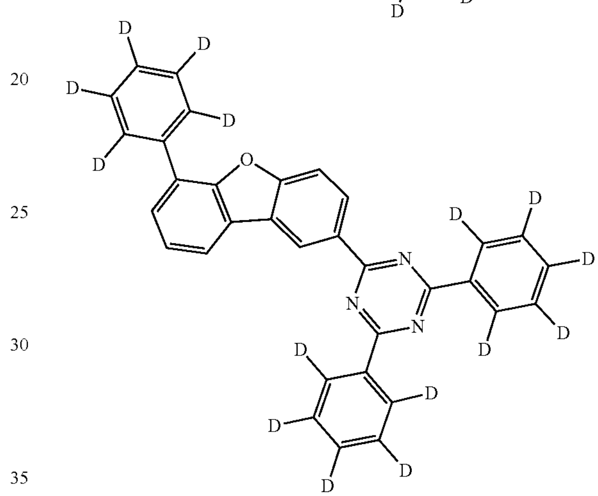
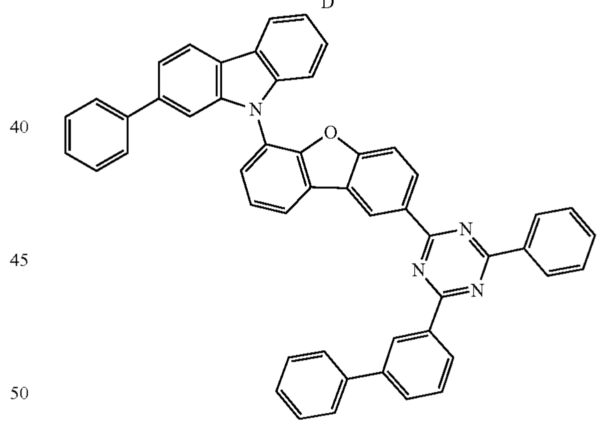
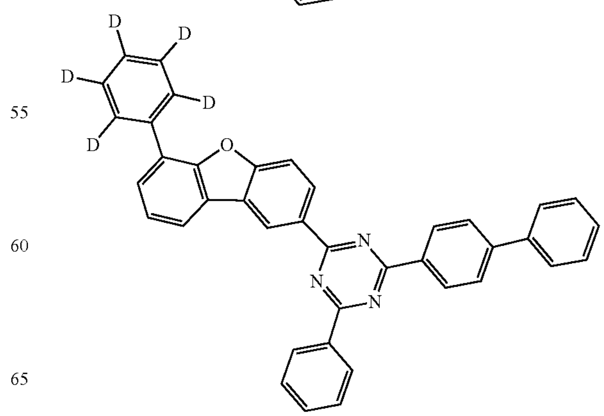

-continued
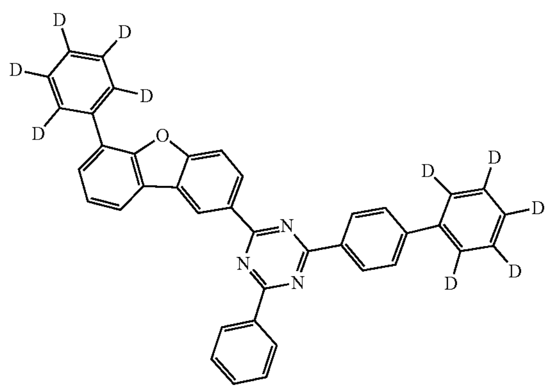
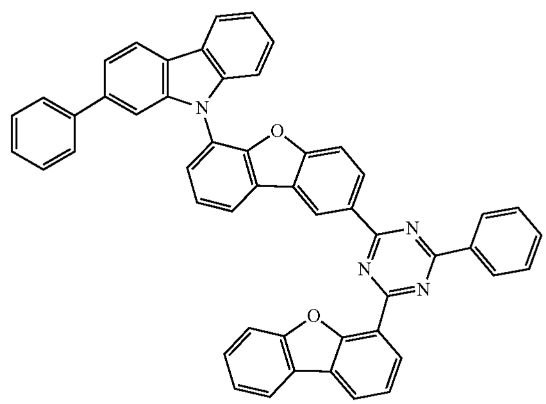
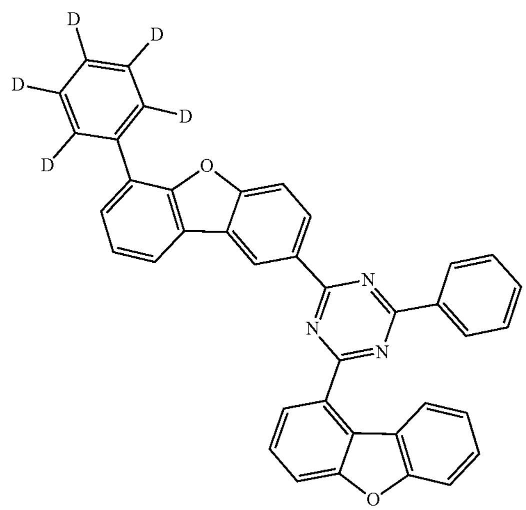
-continued
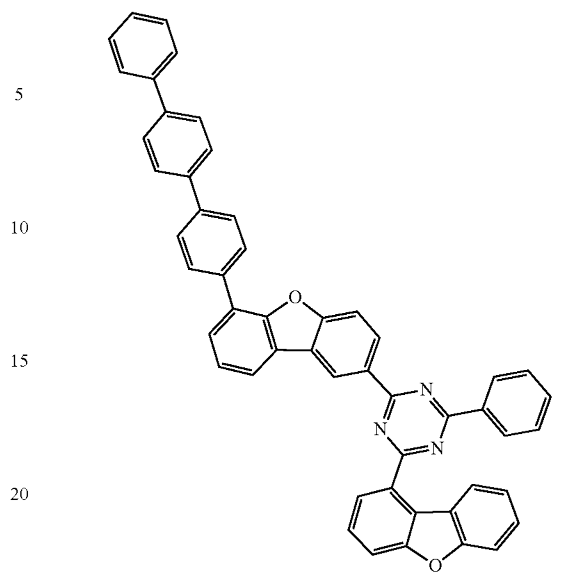
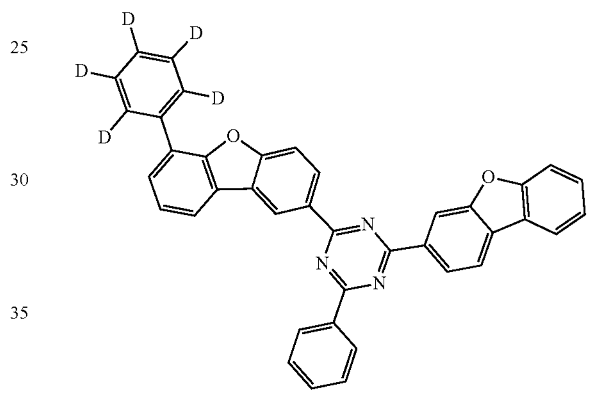
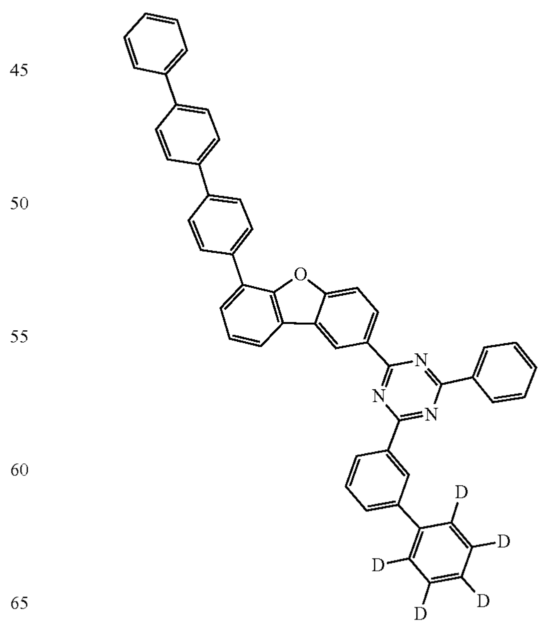

-continued
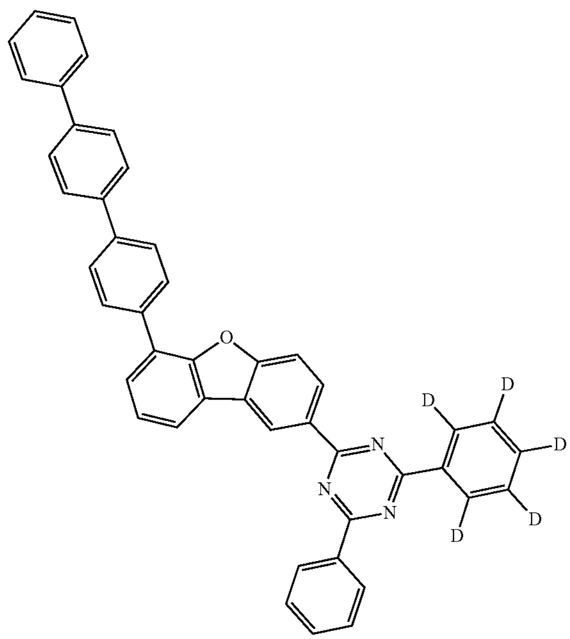
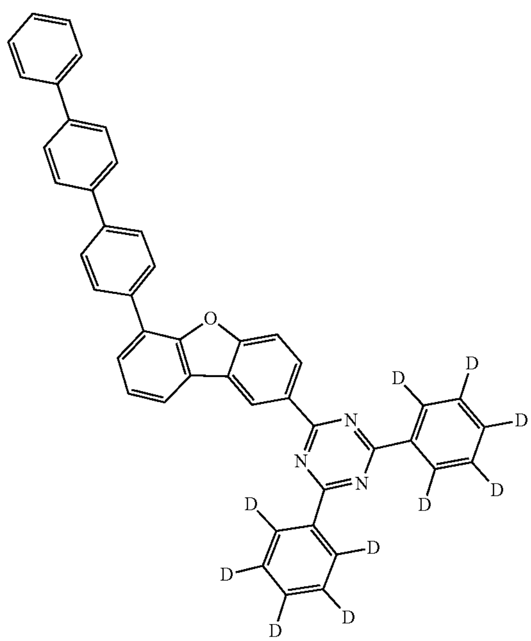
-continued
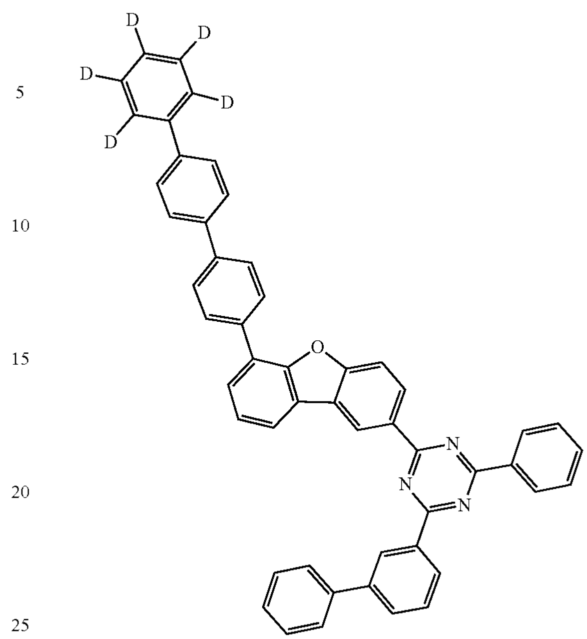
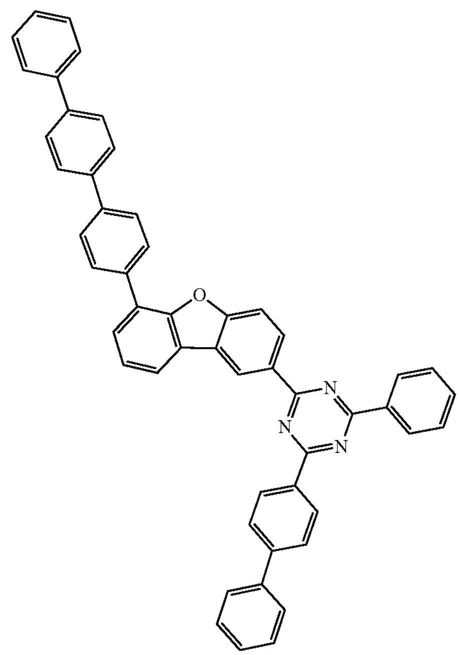

-continued
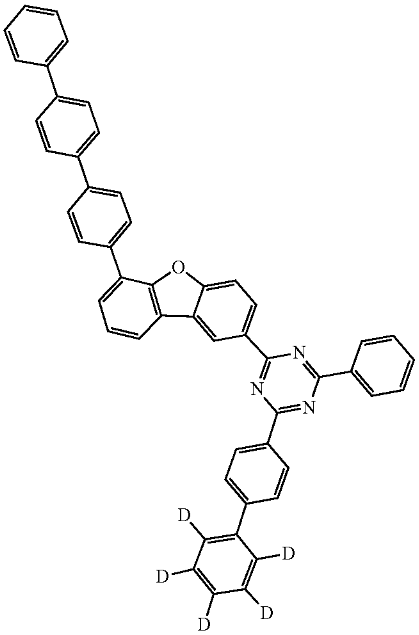
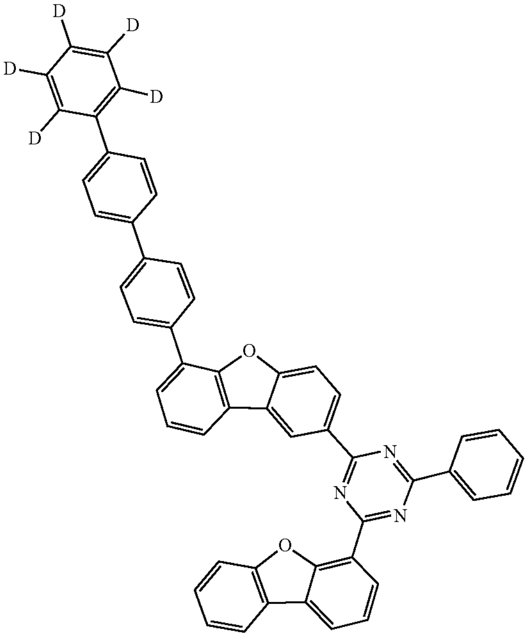
-continued
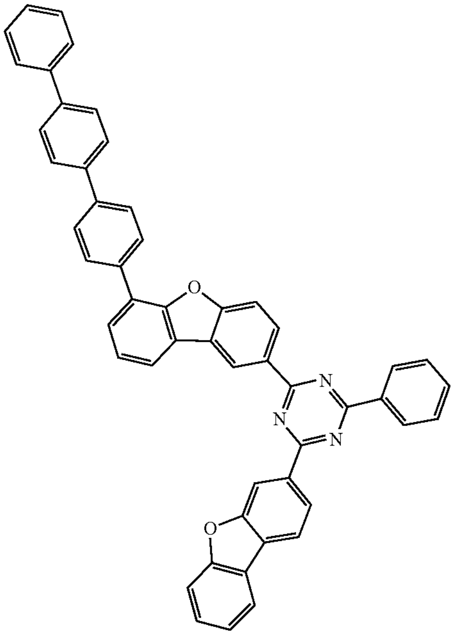
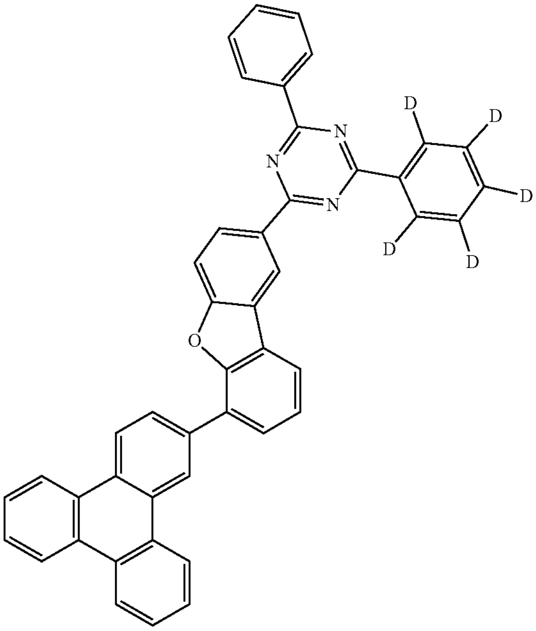
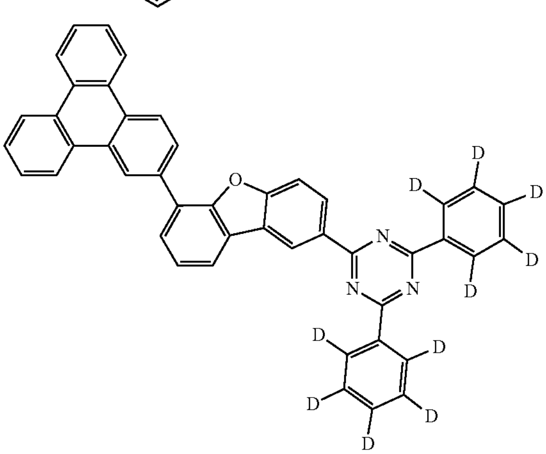

-continued
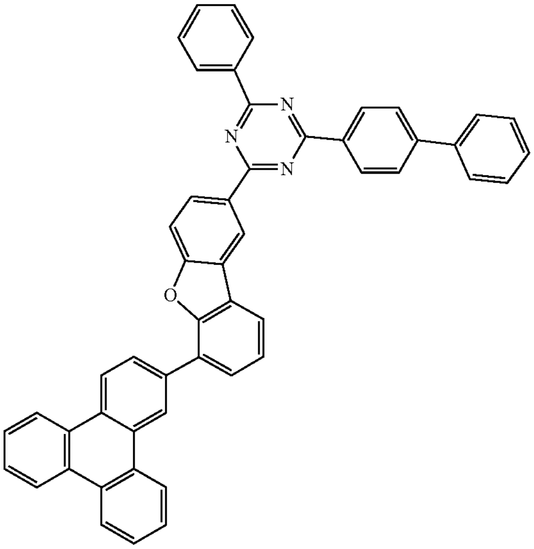
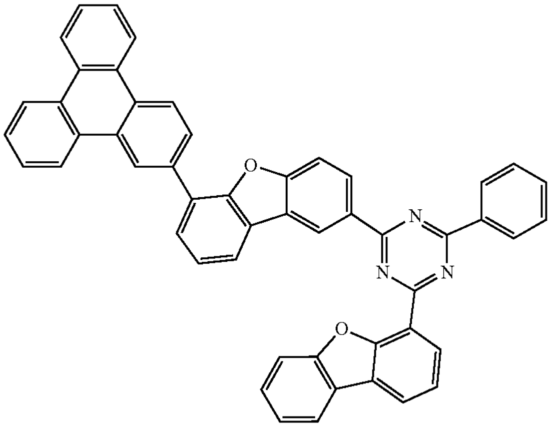
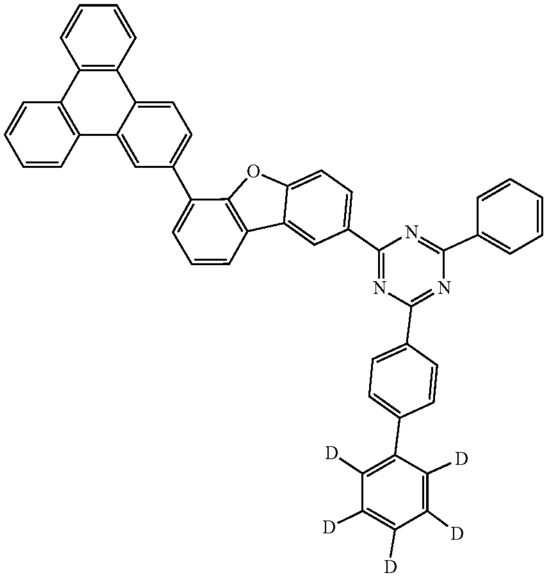
-continued
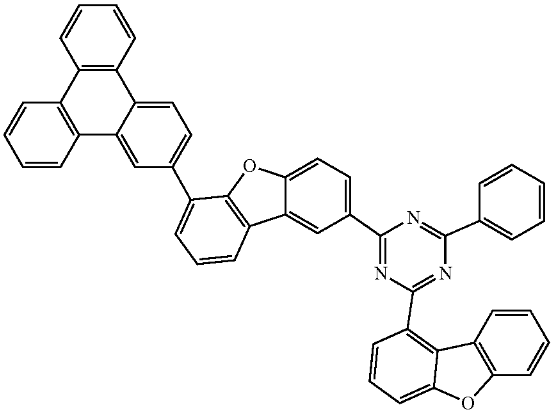
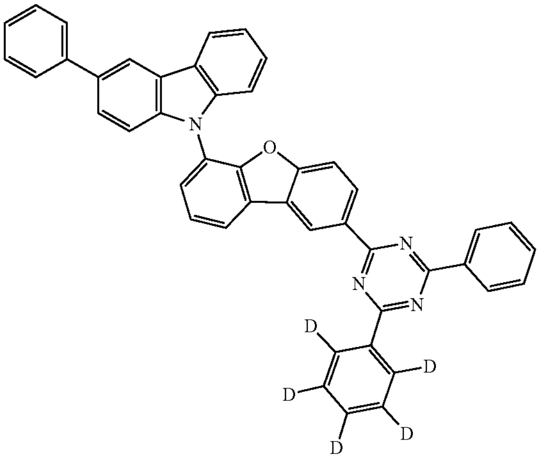
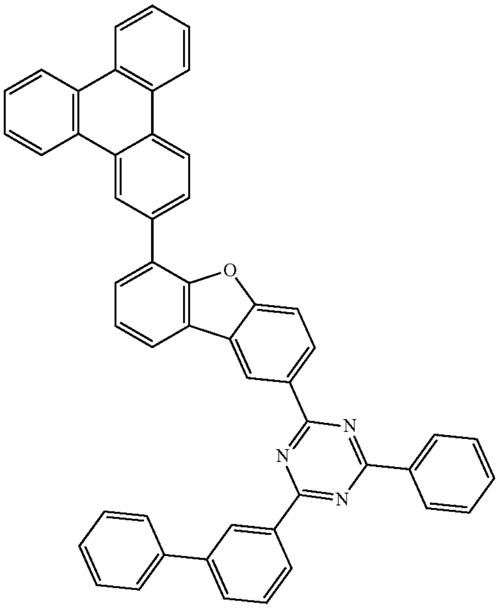

-continued
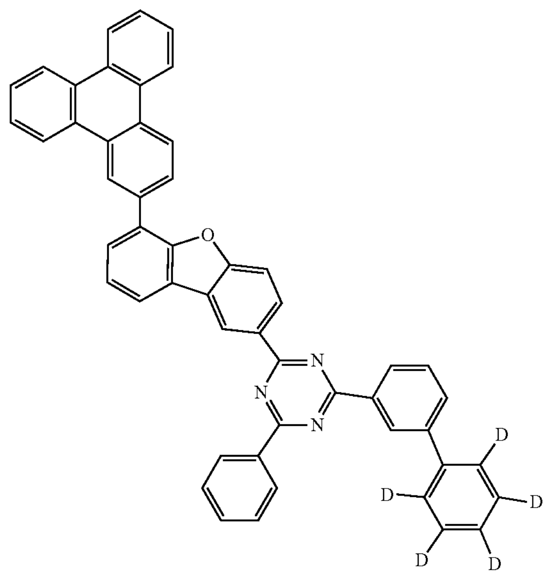
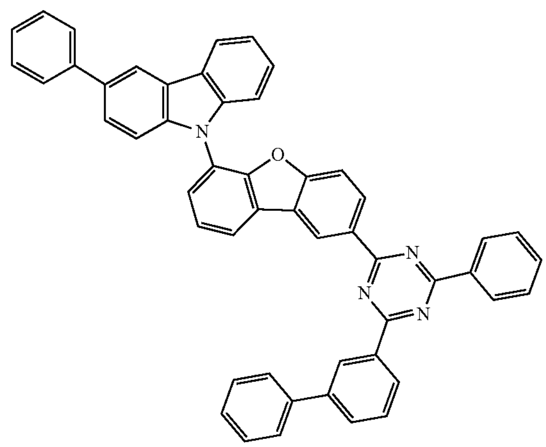
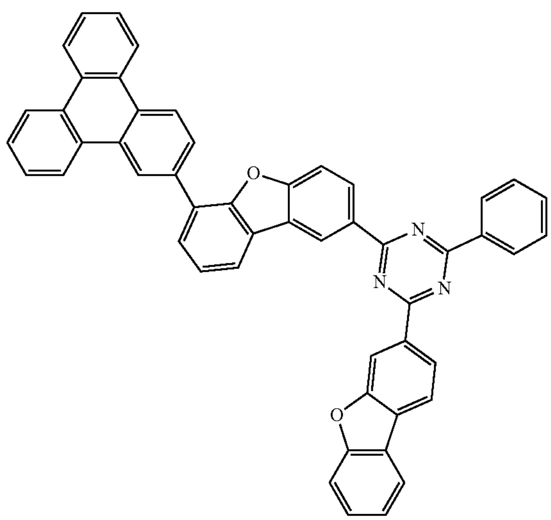
-continued
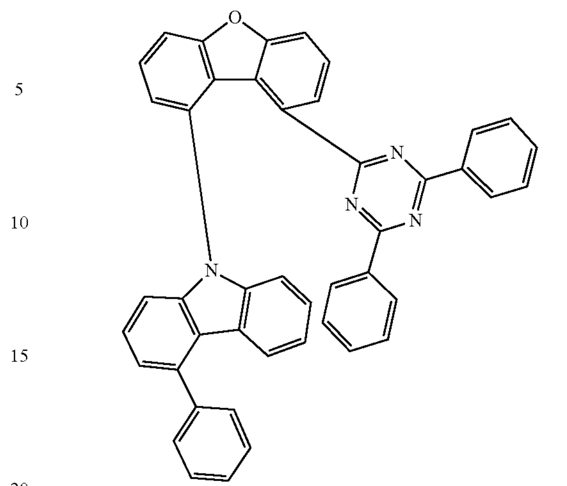
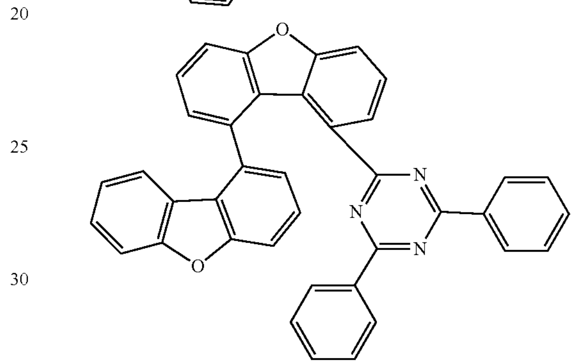
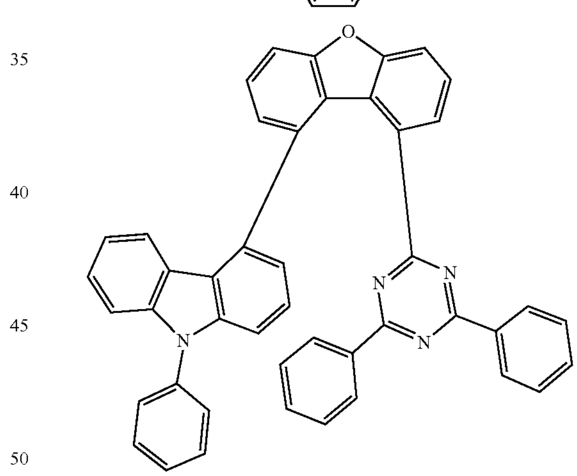
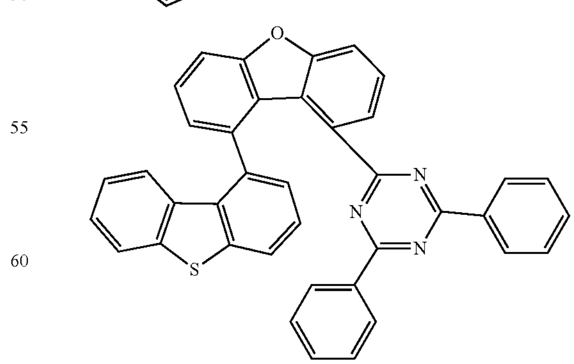

-continued
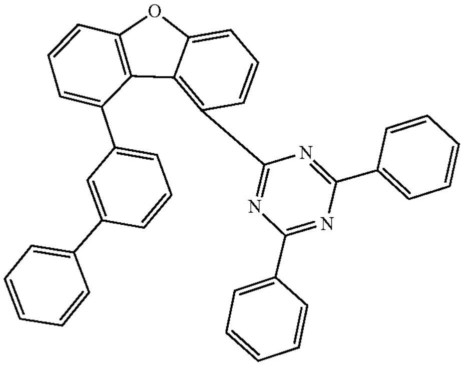
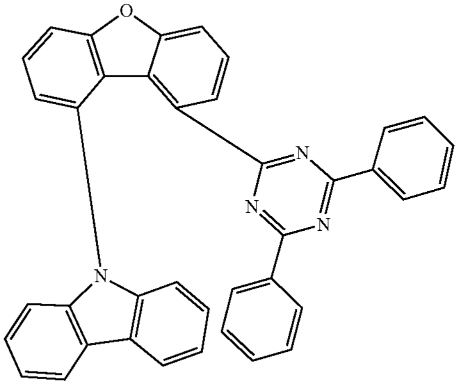
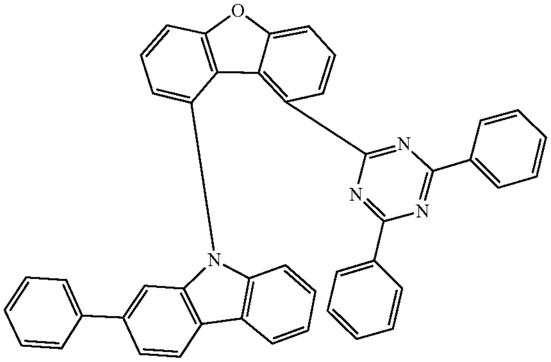
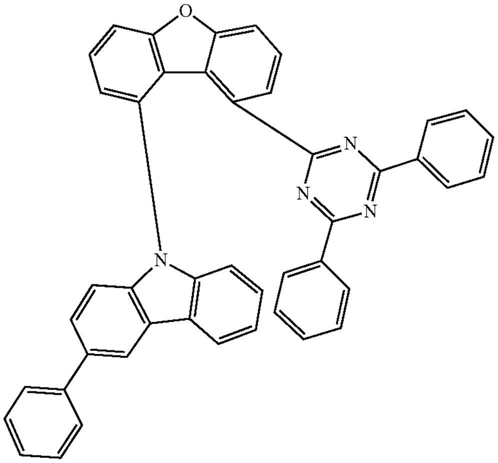
-continued
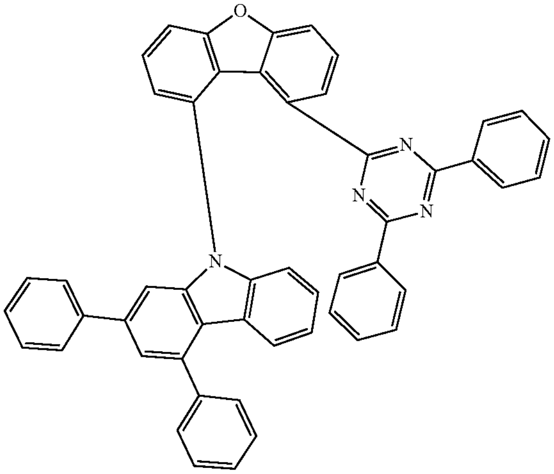
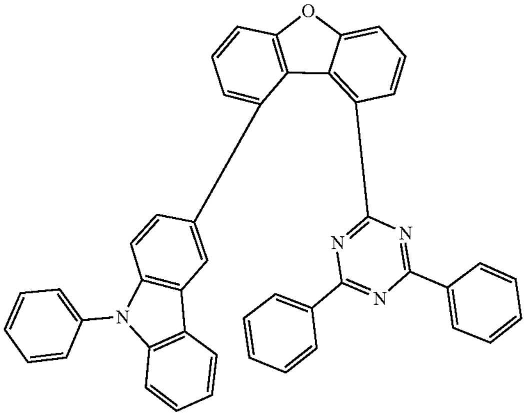
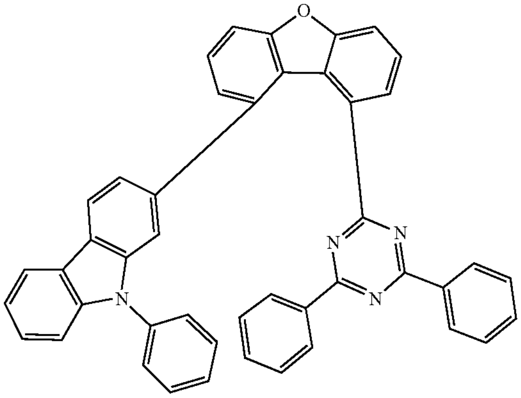
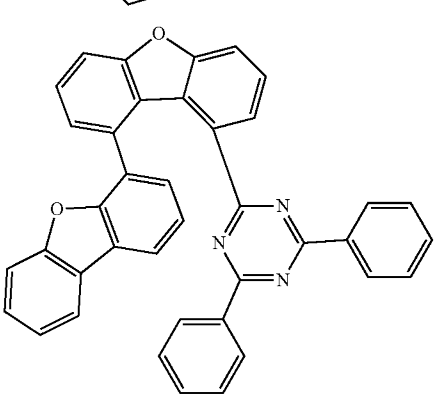

-continued
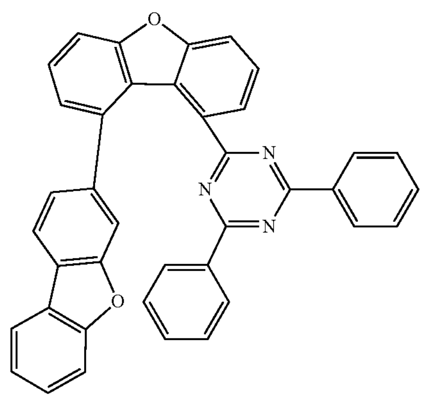
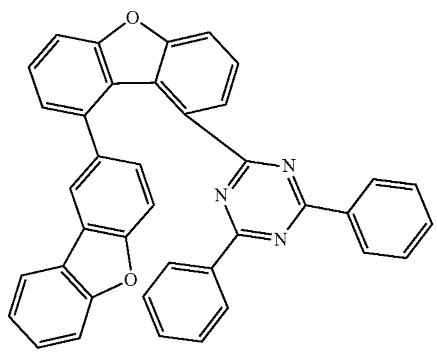
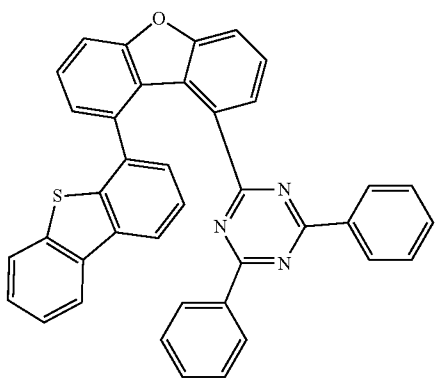
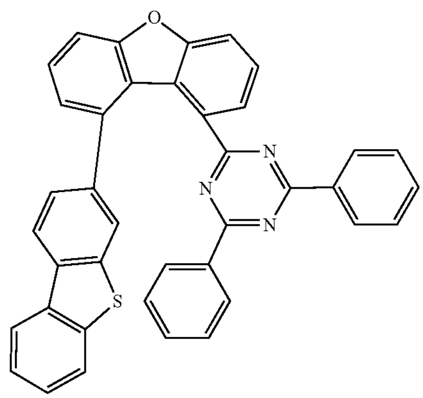
-continued
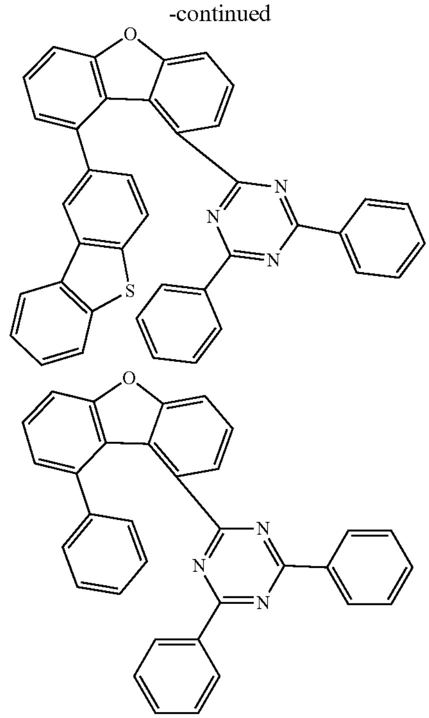
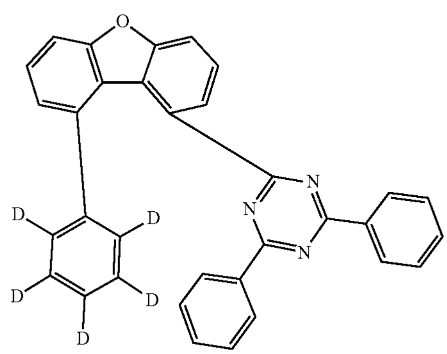
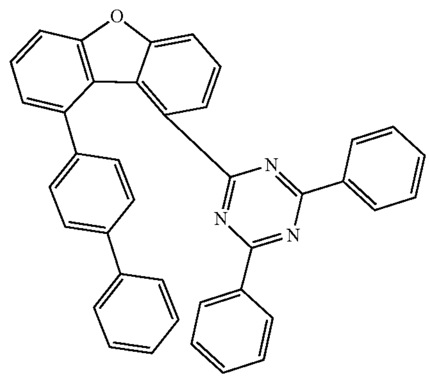

-continued
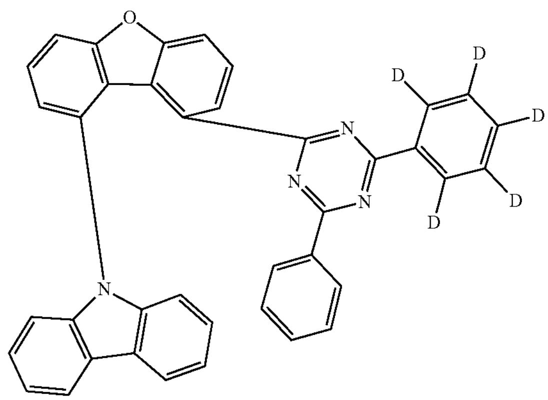
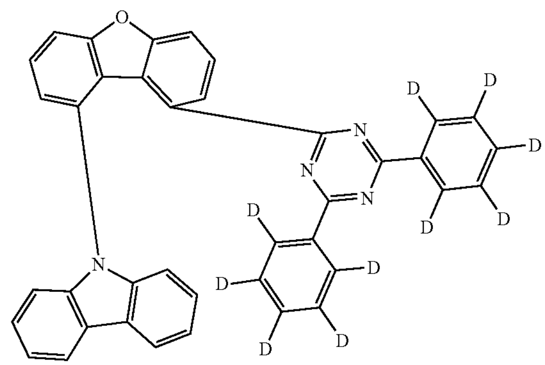
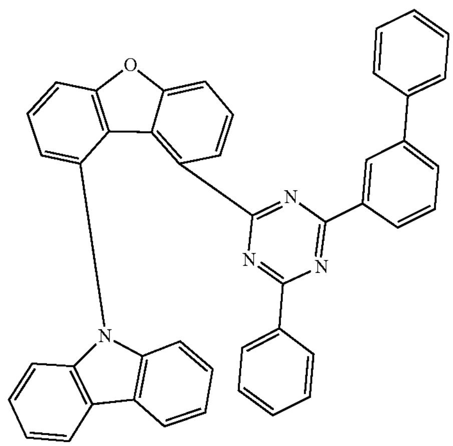
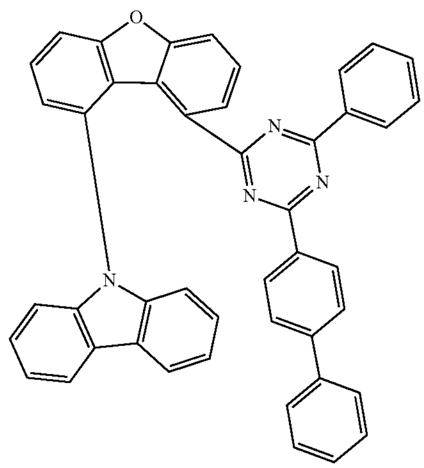
-continued
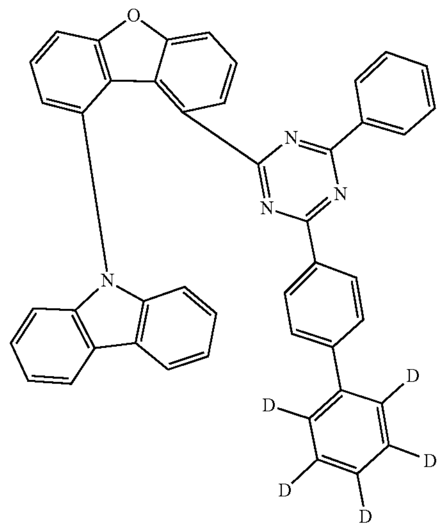
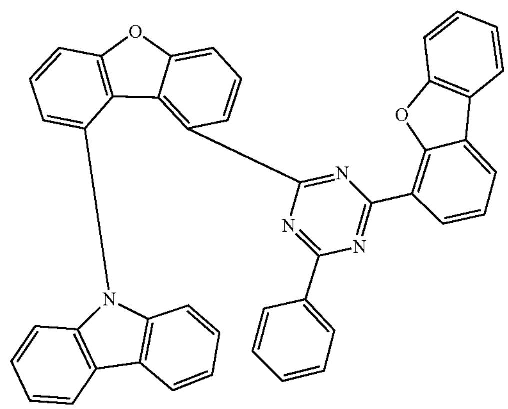
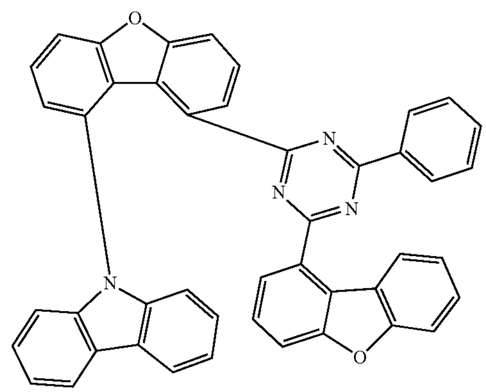

-continued
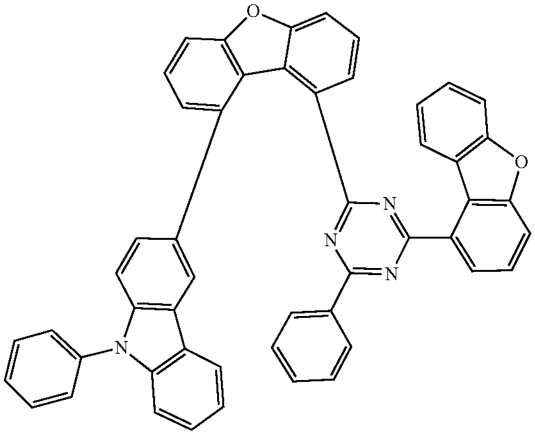
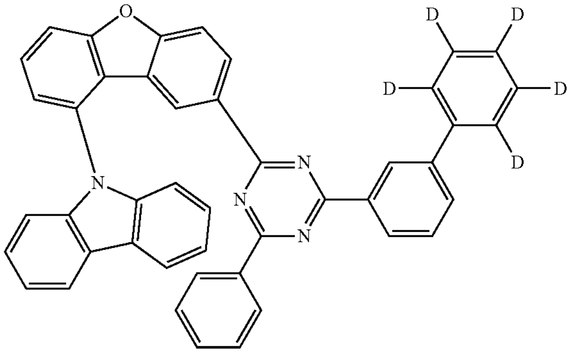
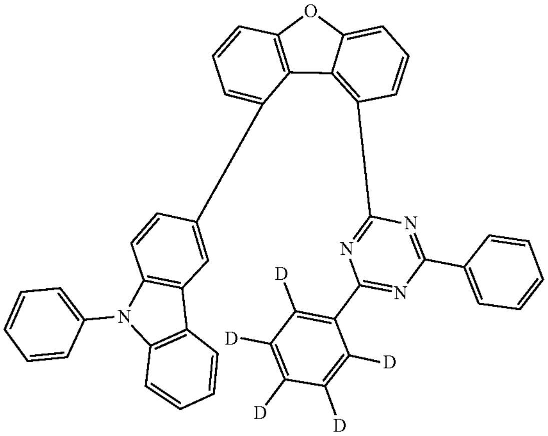
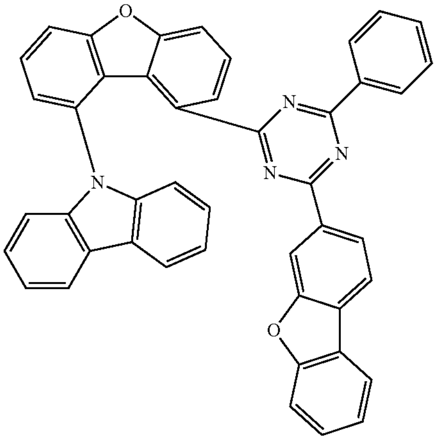
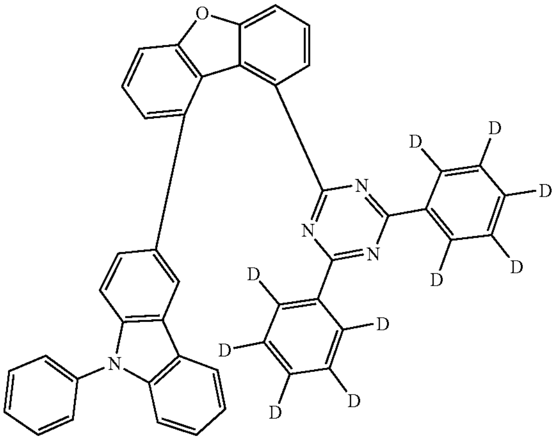
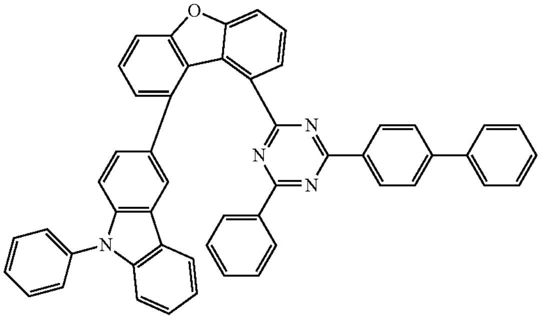
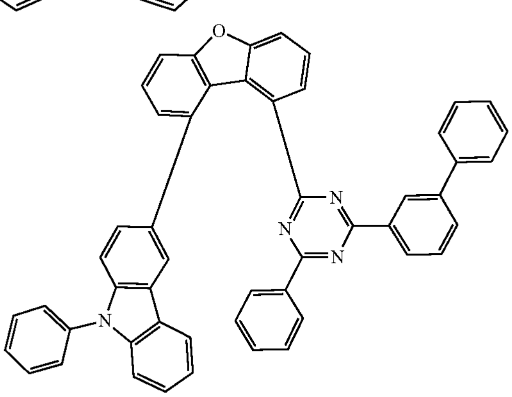
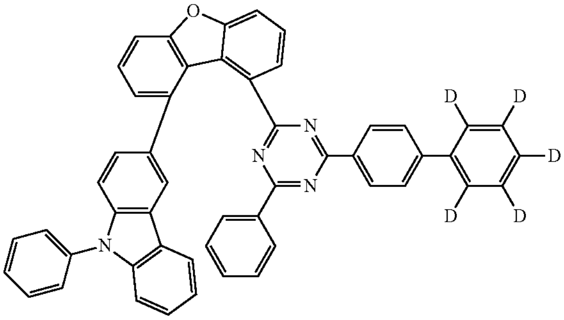

-continued
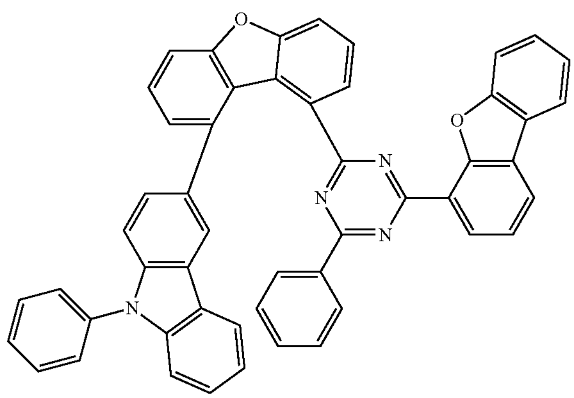
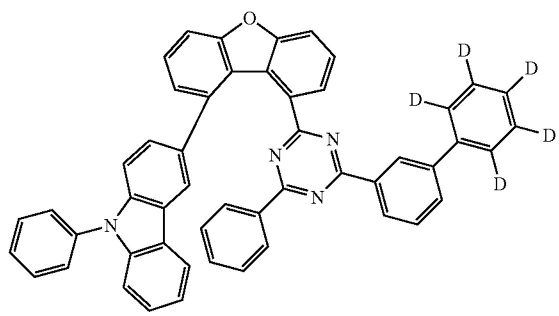
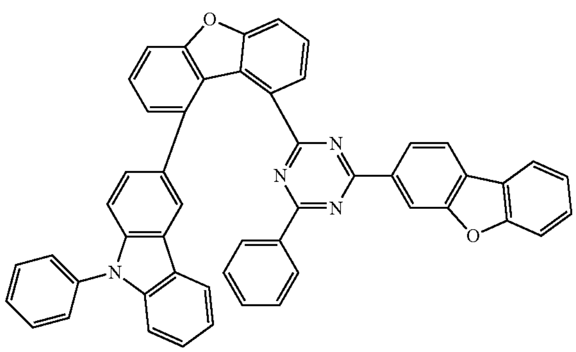
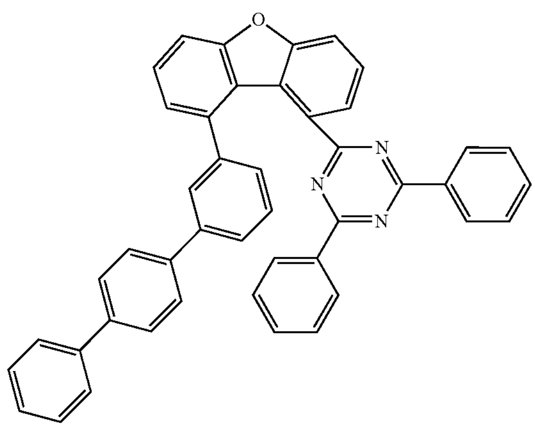
-continued
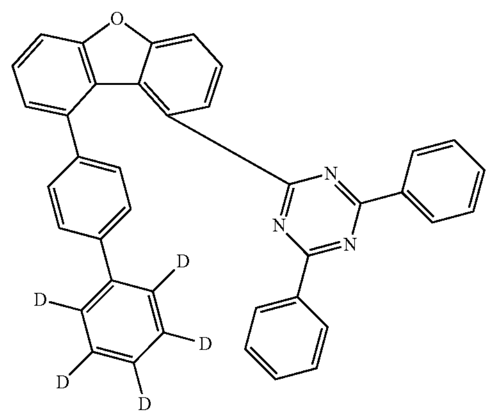
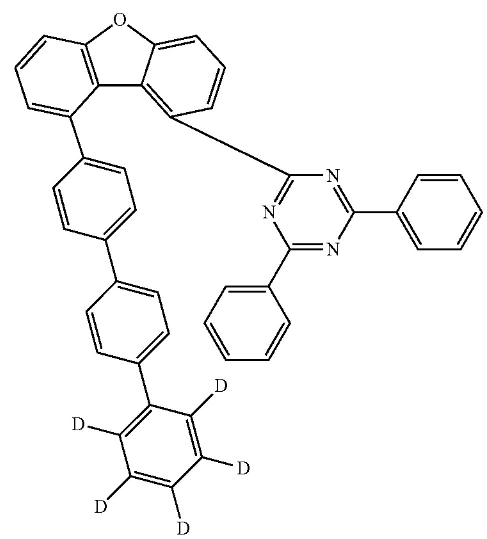
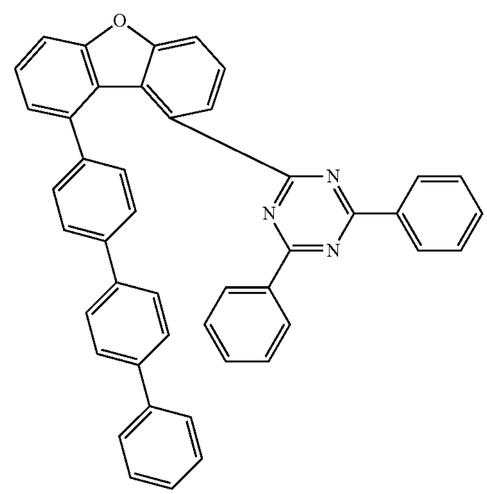

-continued
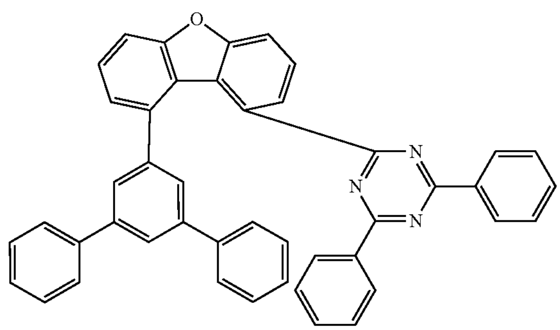
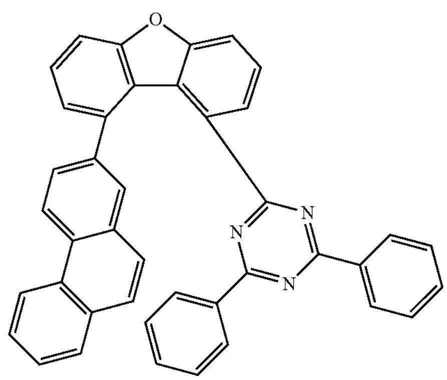
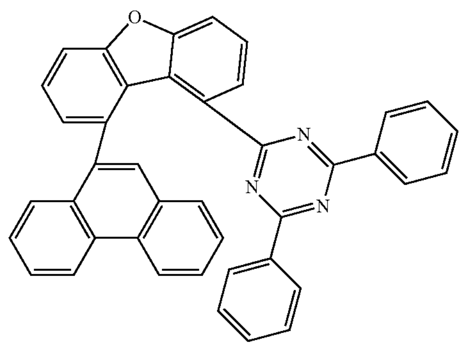
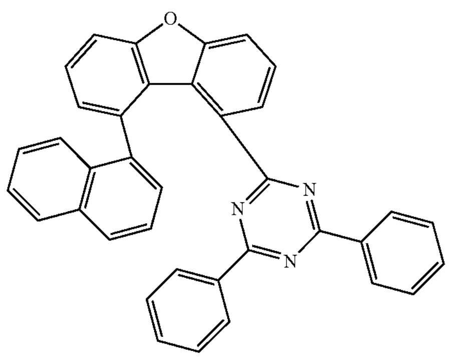
-continued
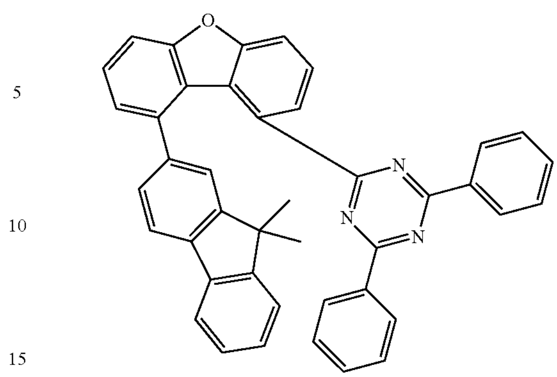
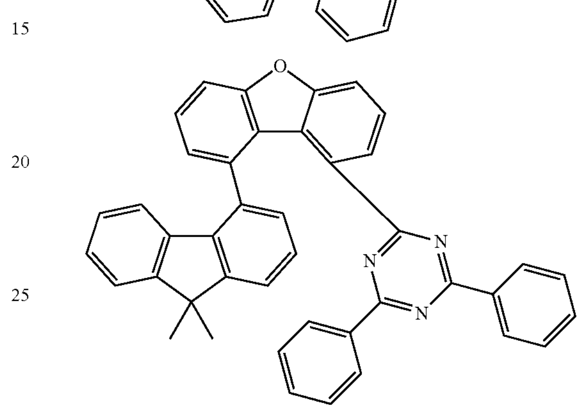
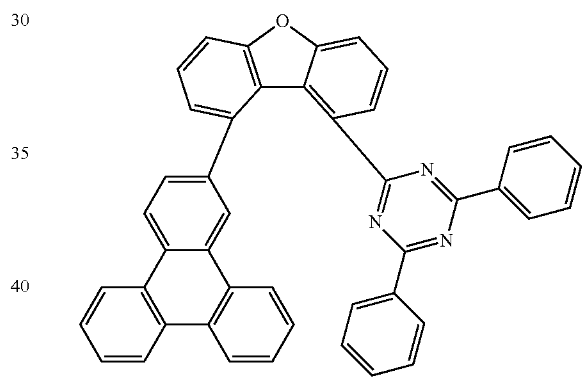
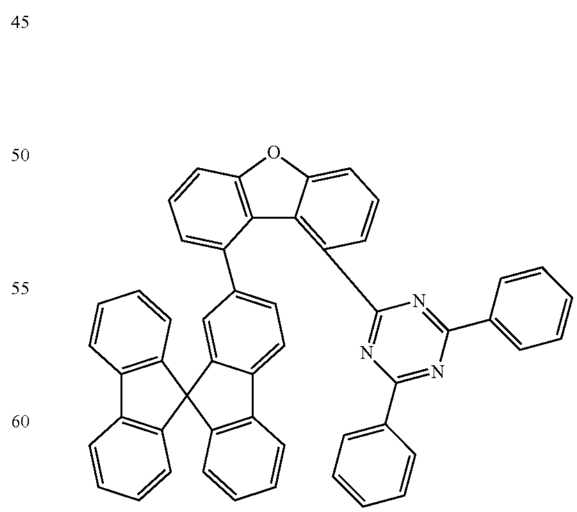

-continued
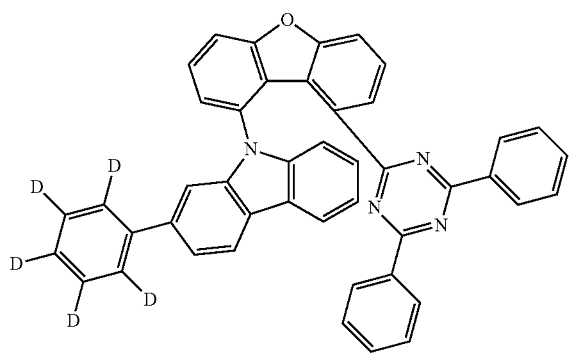
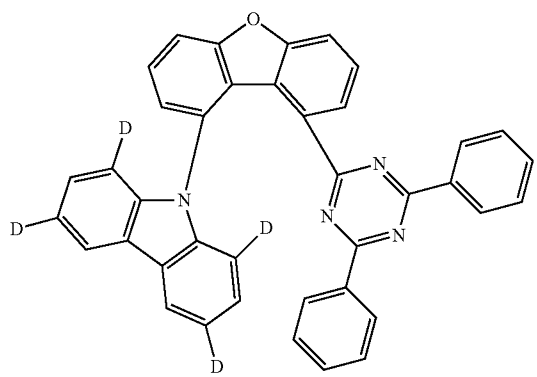
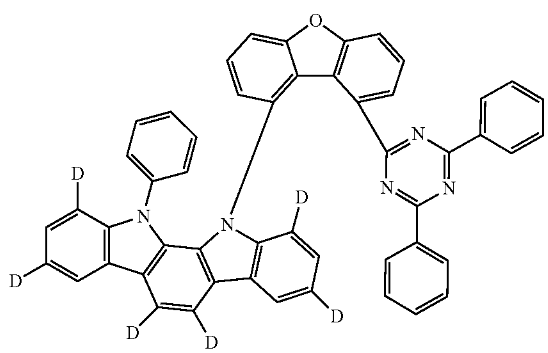
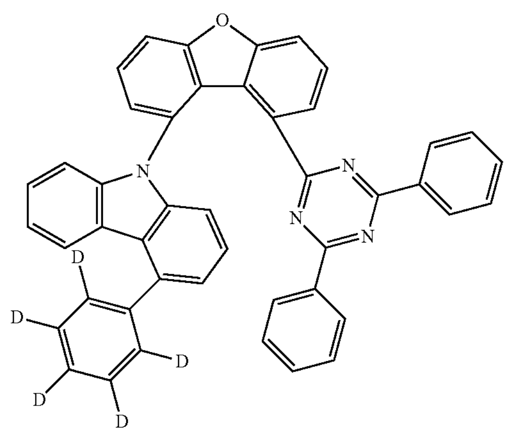
-continued
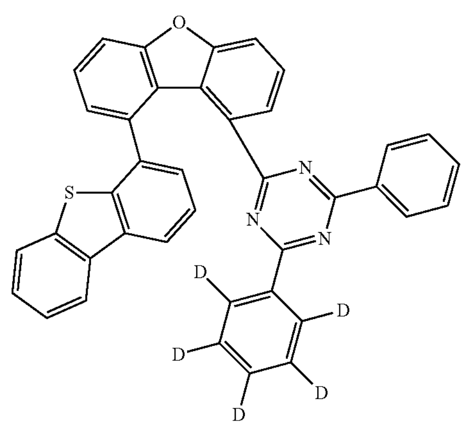
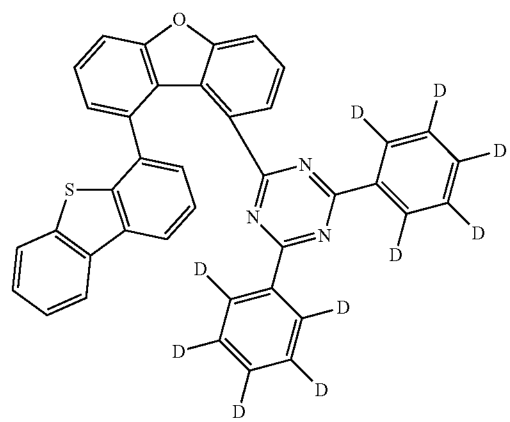
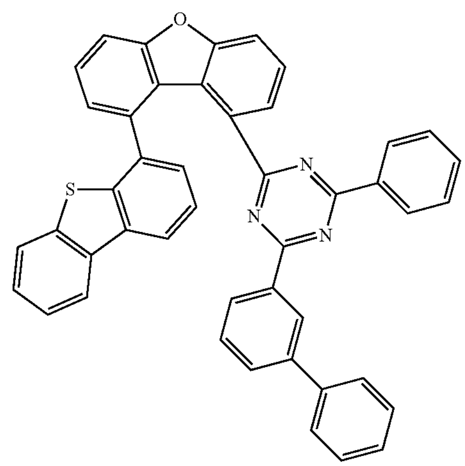

-continued
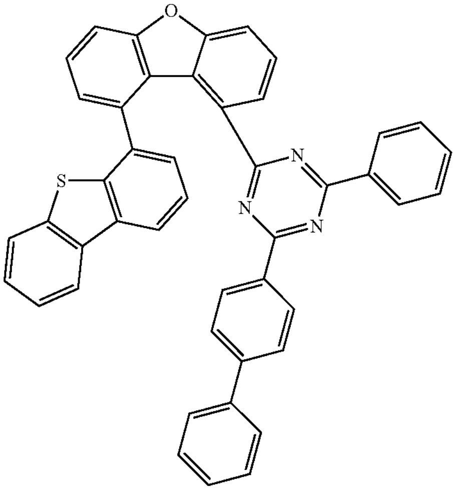
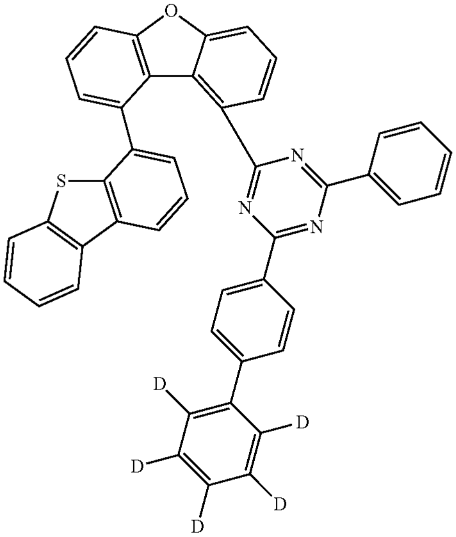
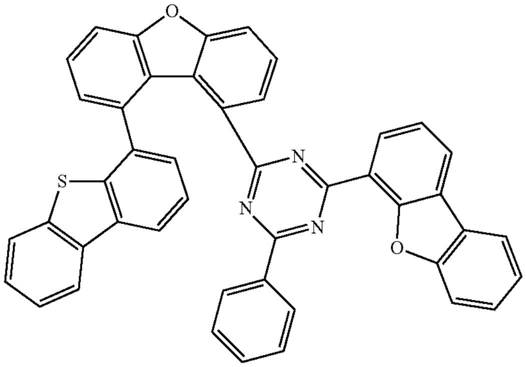
-continued
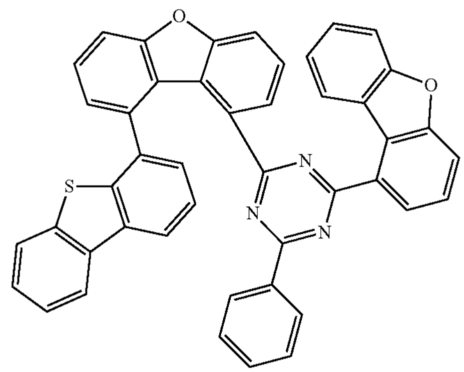
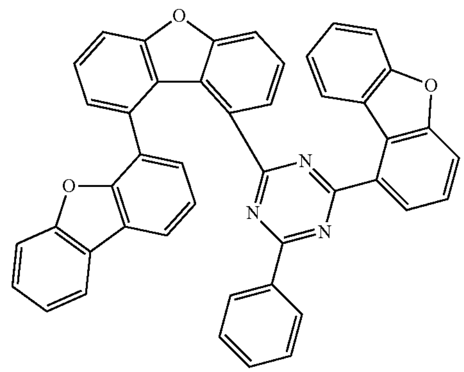
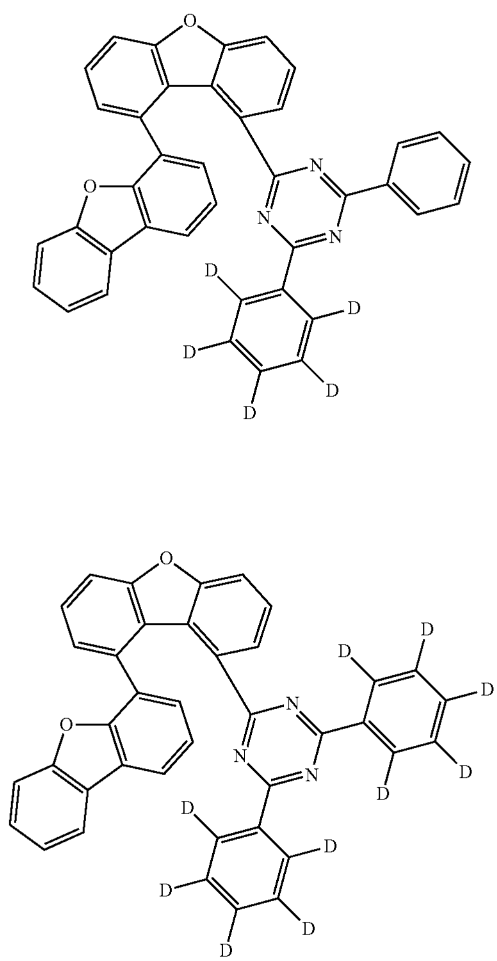

-continued
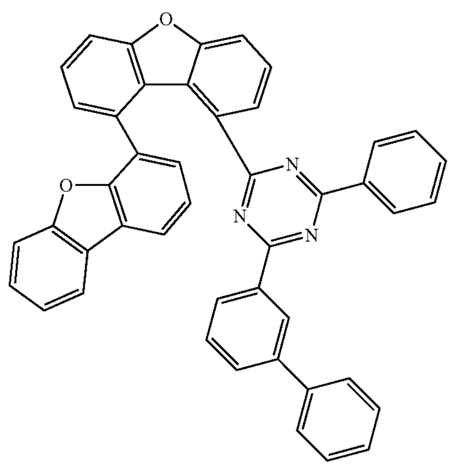
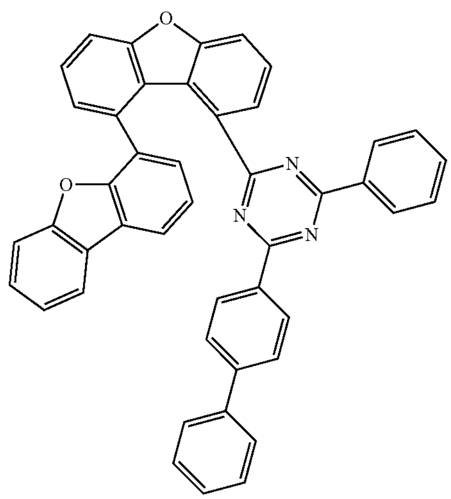
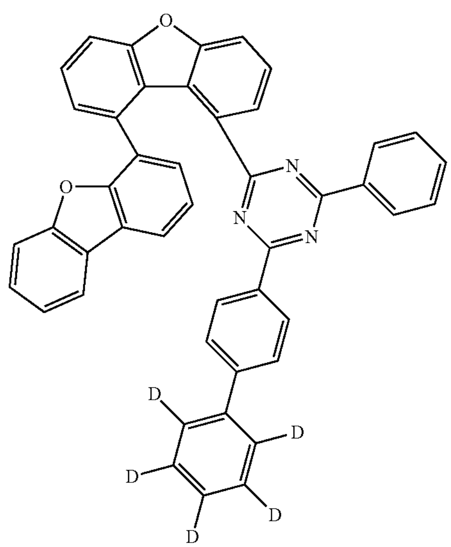
-continued
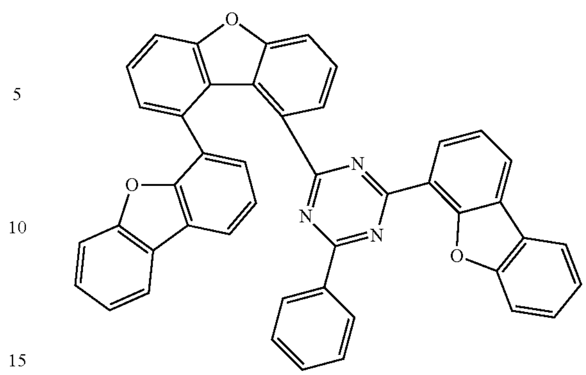
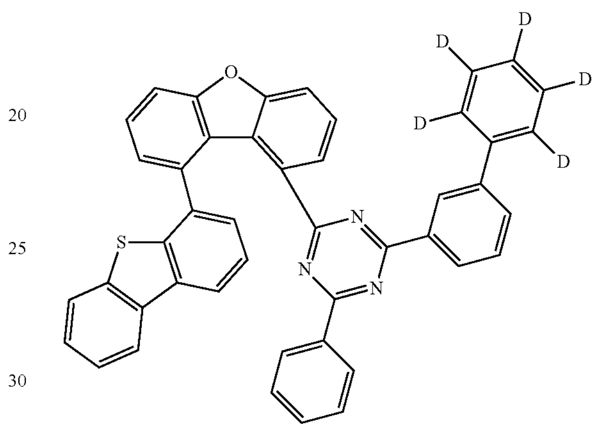
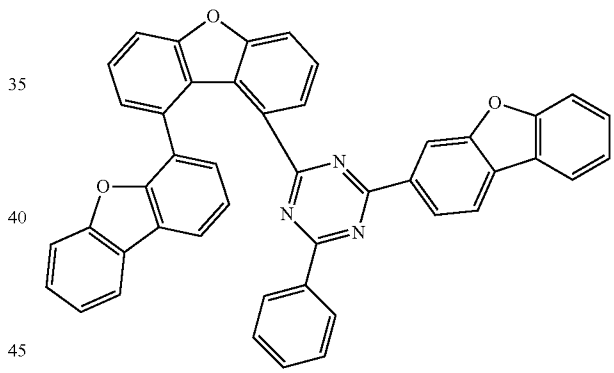
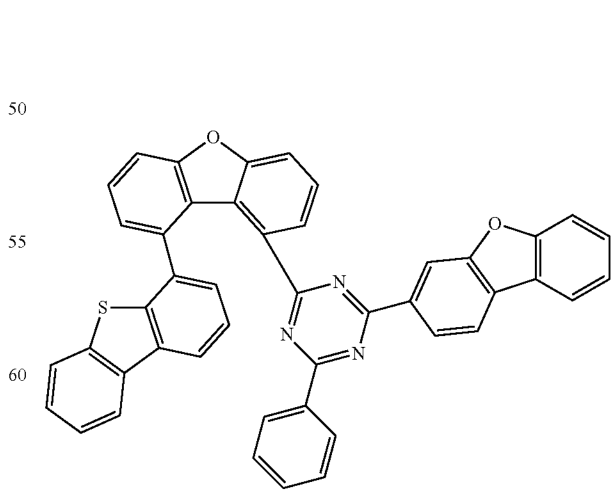

-continued
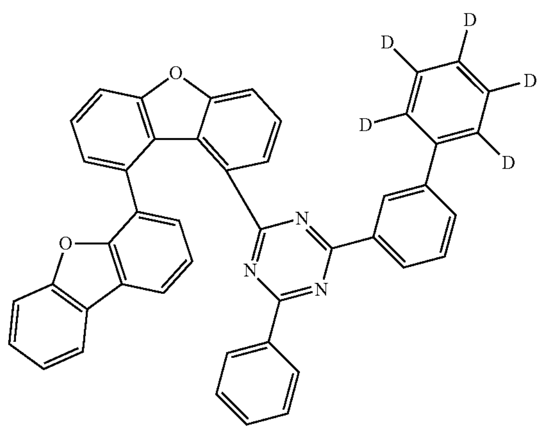
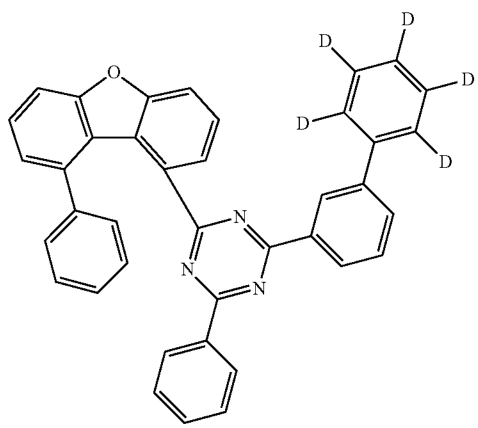
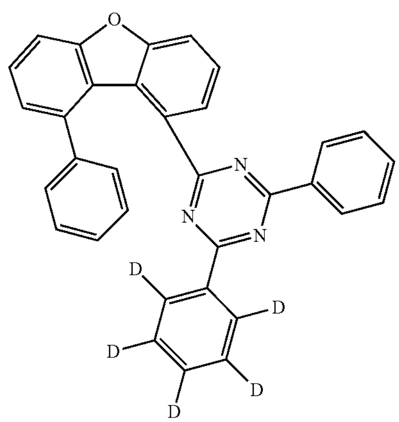
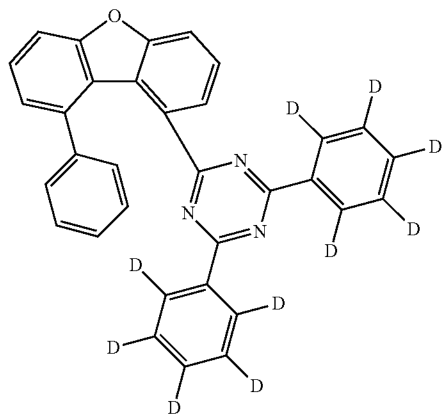
-continued
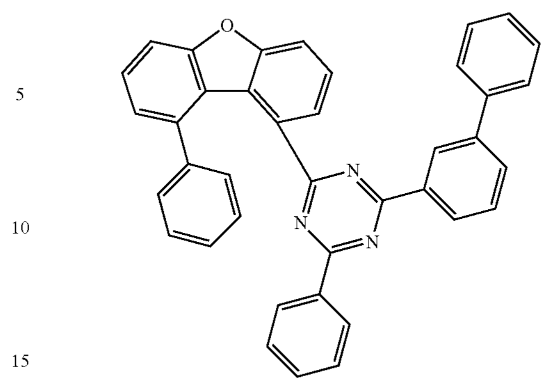
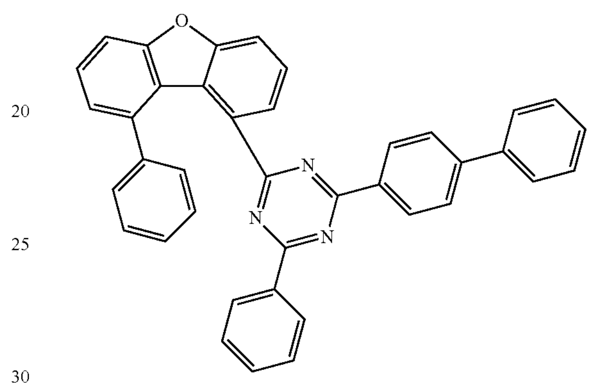
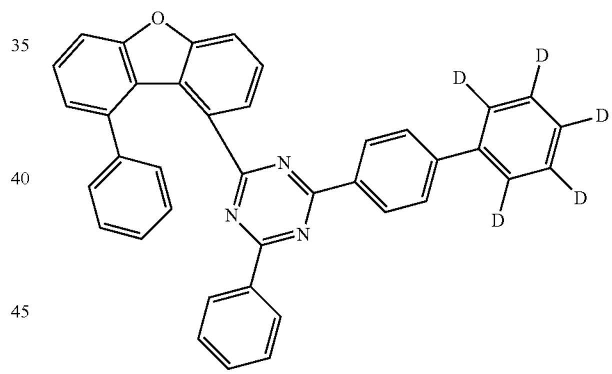
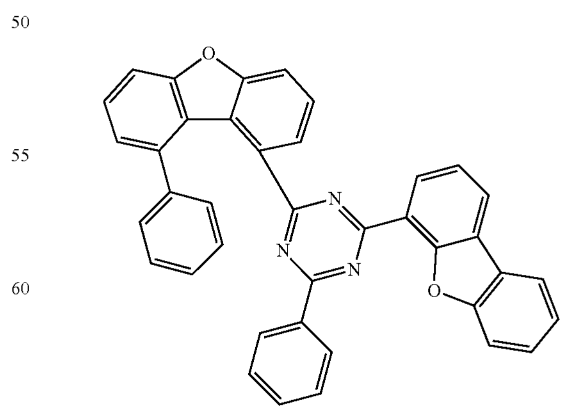

-continued
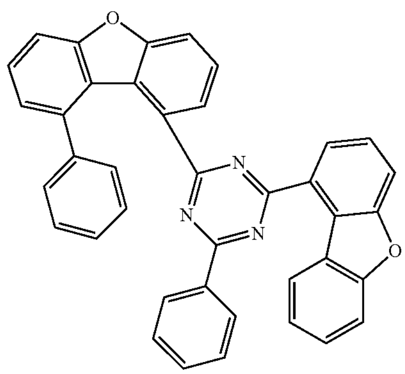
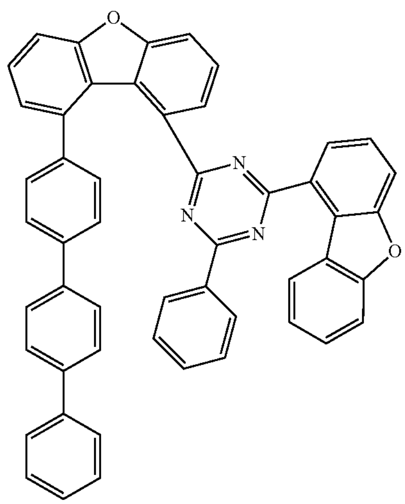
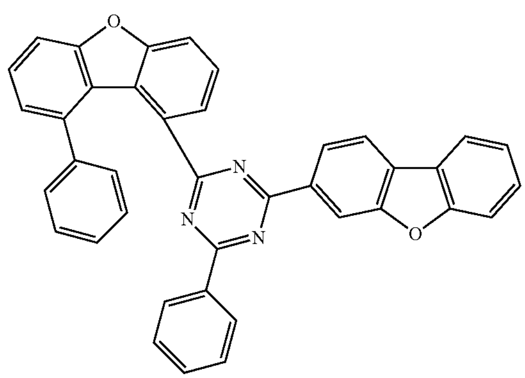
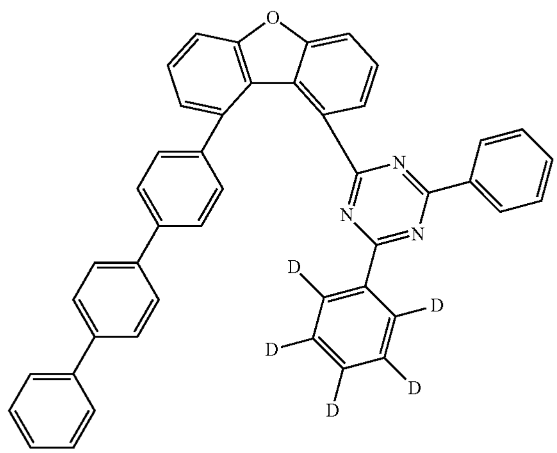
-continued
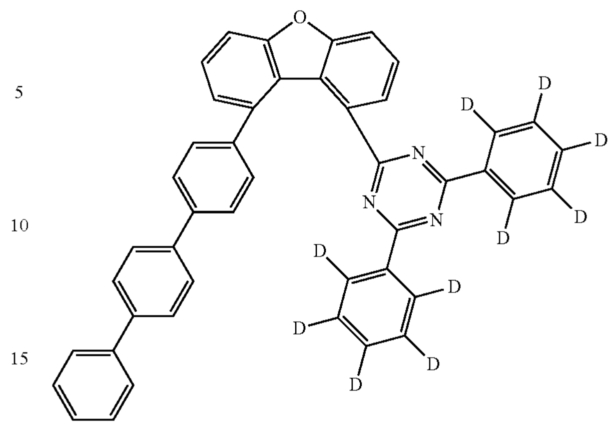
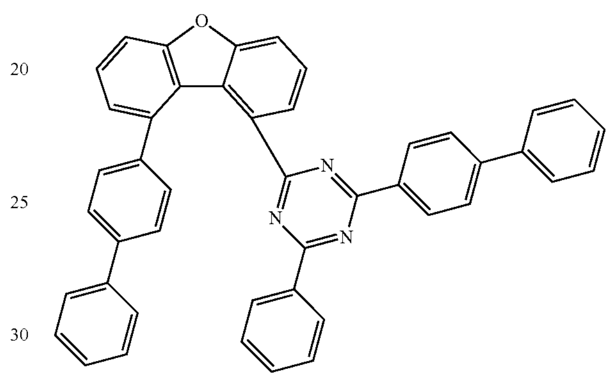
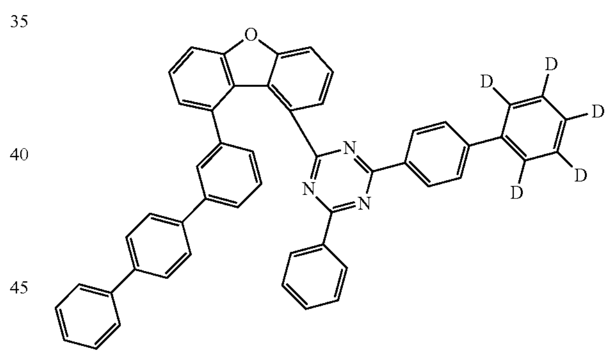
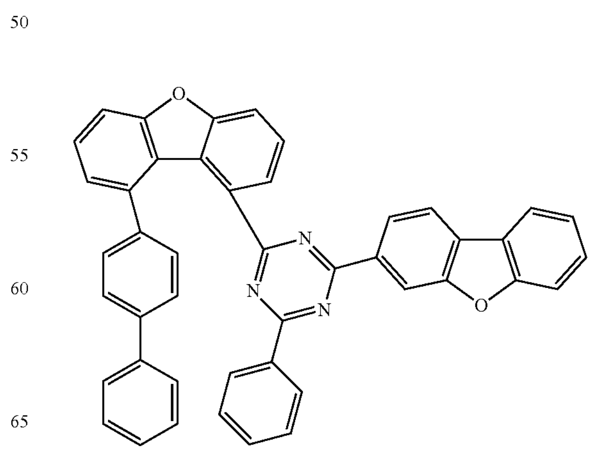

-continued
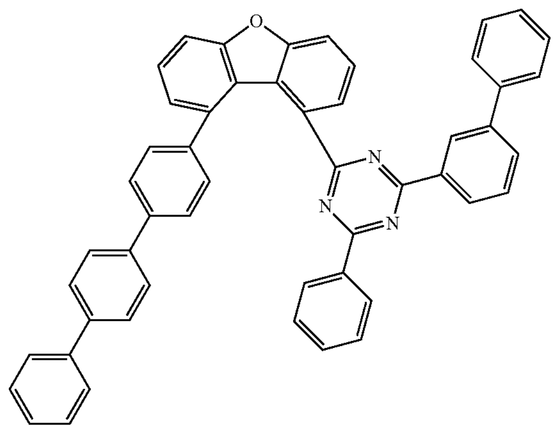
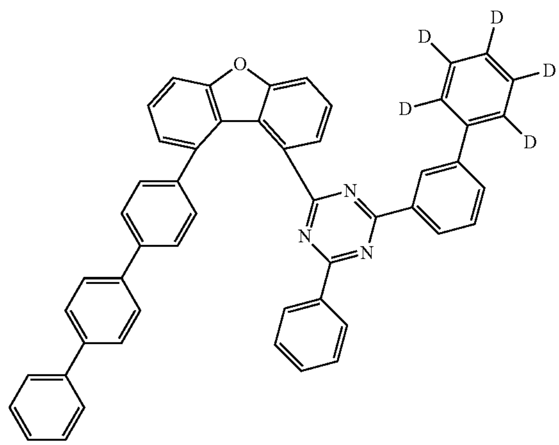
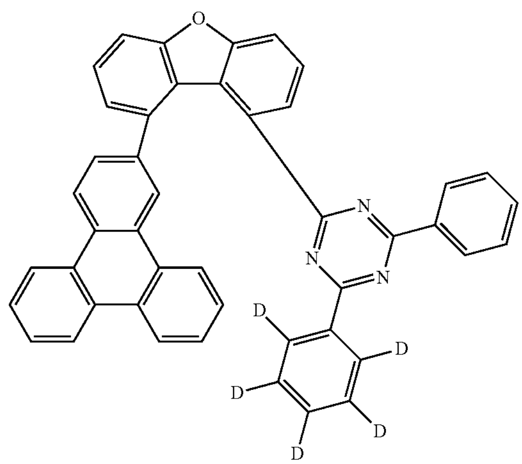
-continued
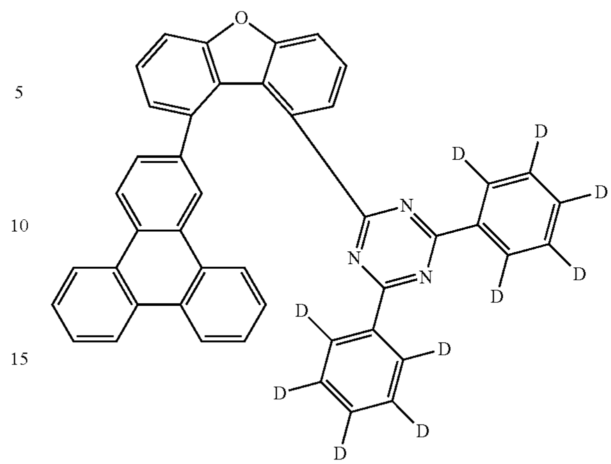
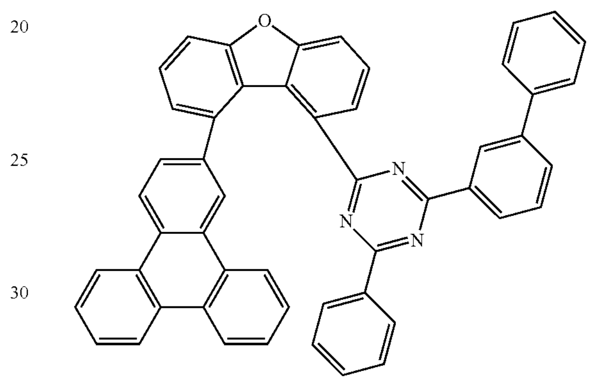
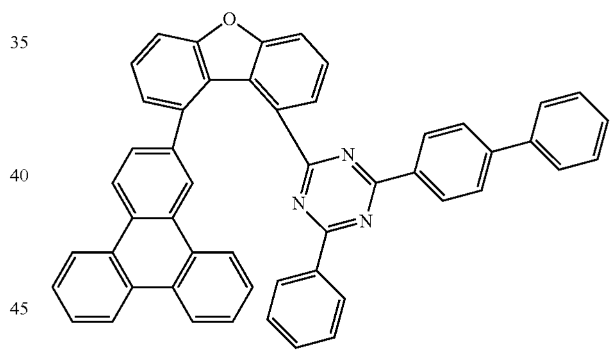
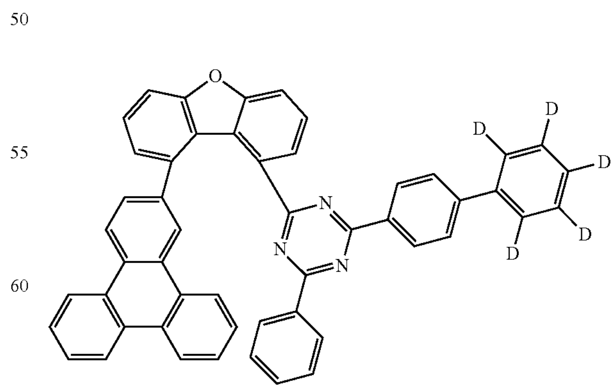

-continued
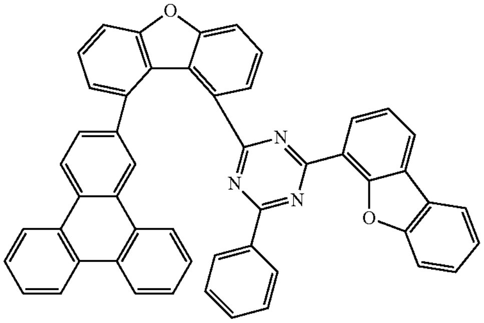
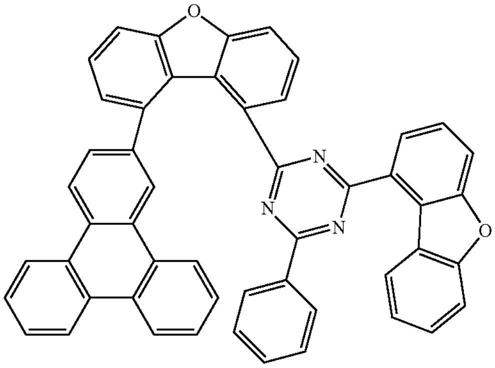
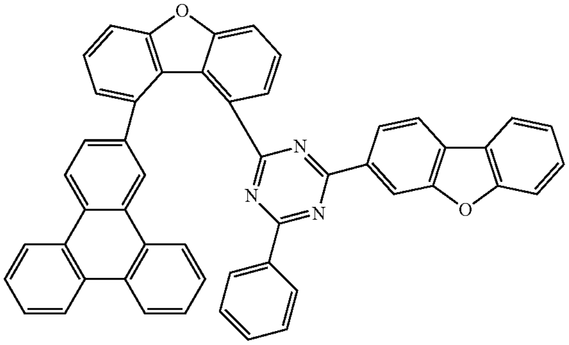
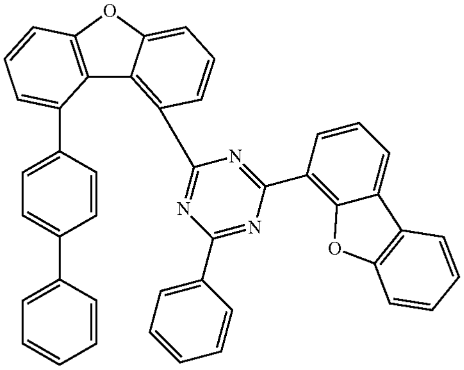
-continued
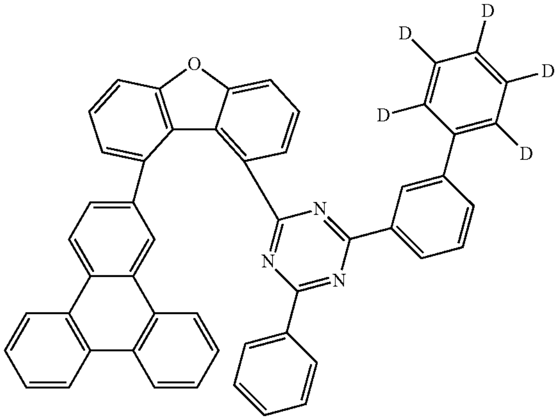
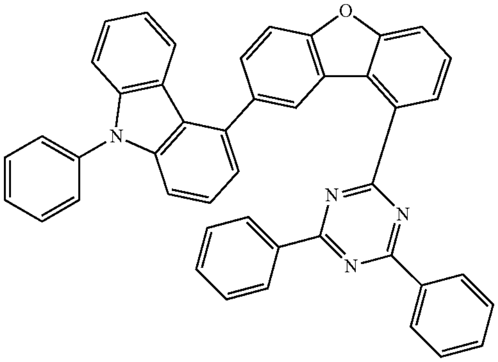
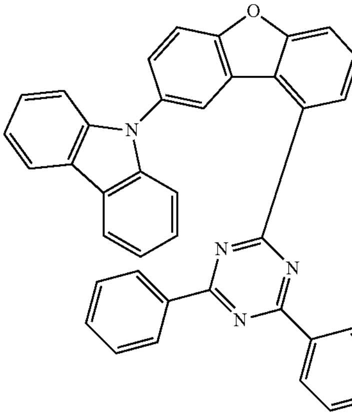
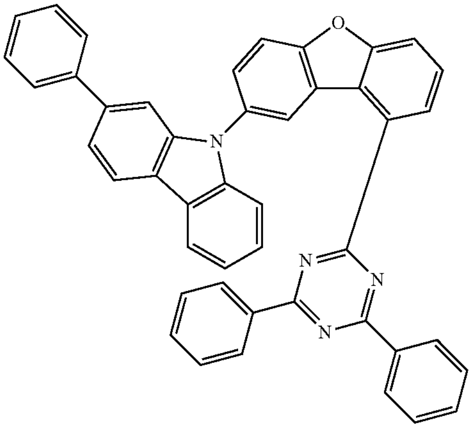

-continued
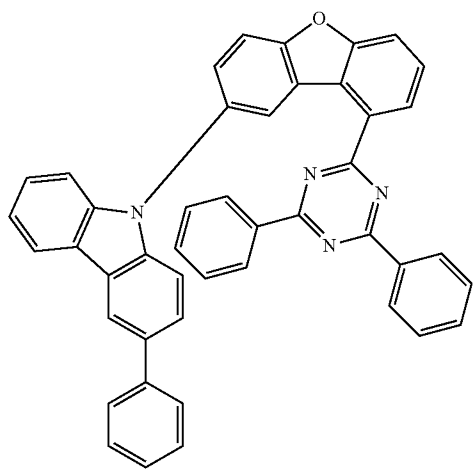
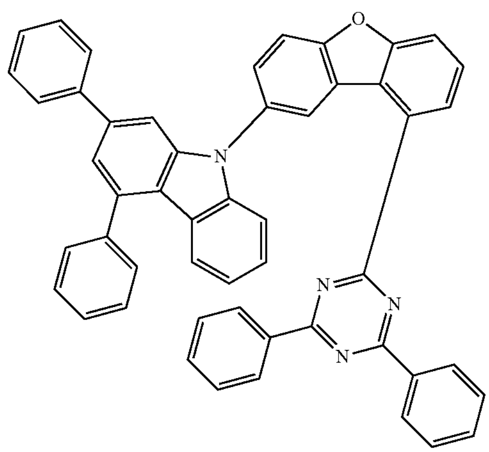
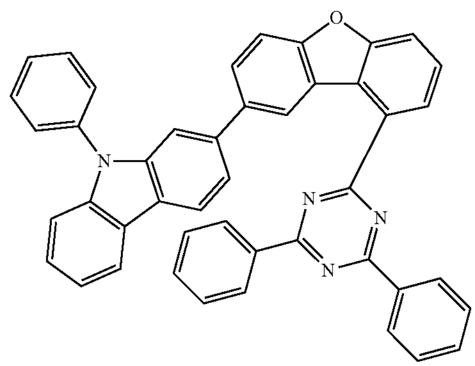
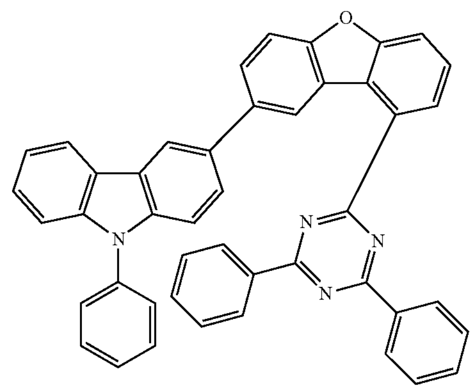
-continued
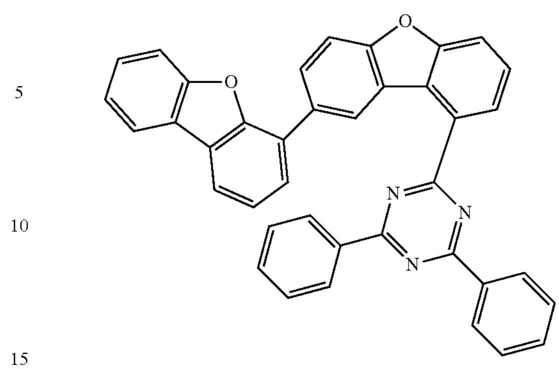
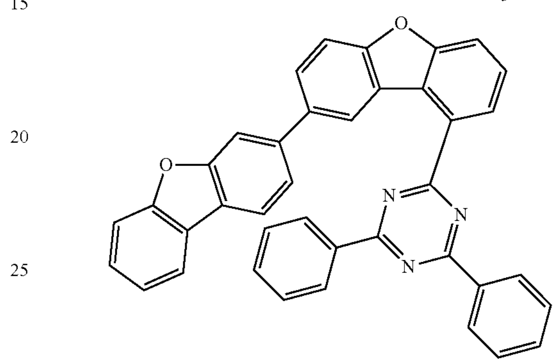
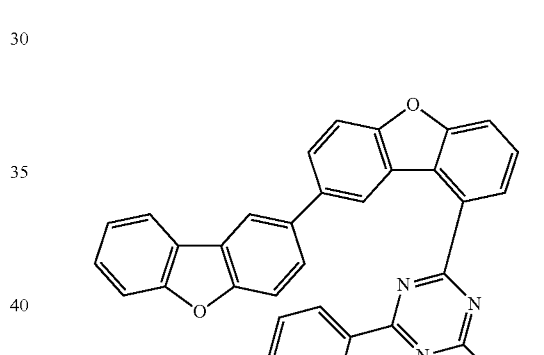
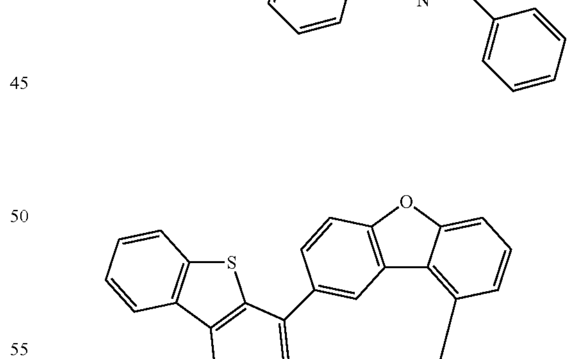
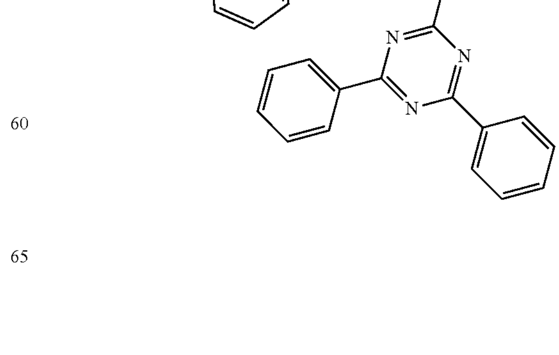

-continued
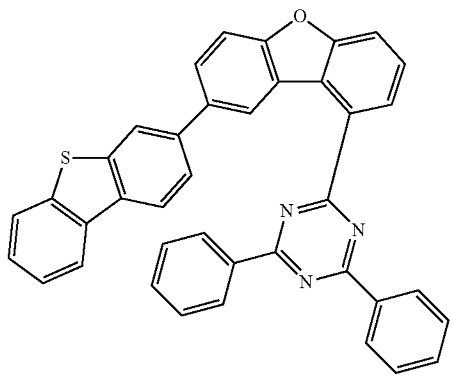
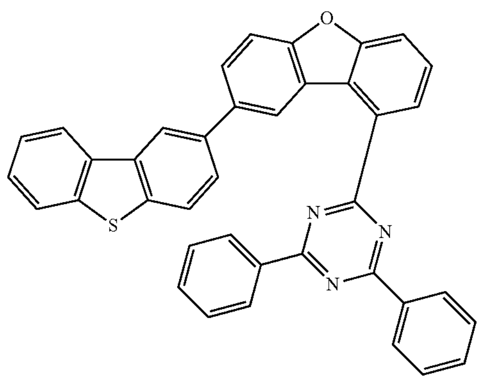
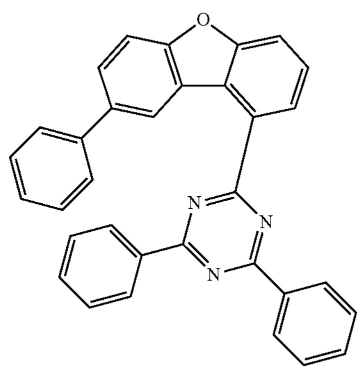
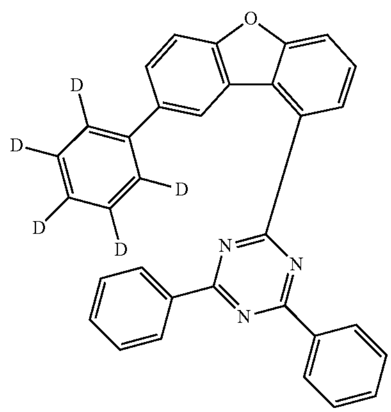
-continued
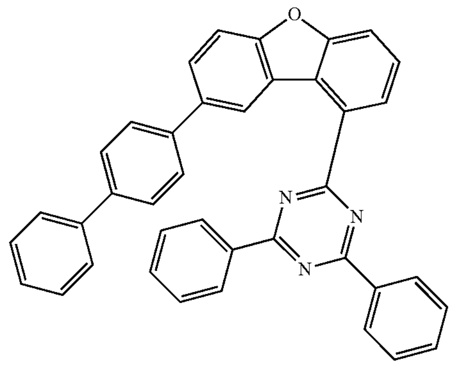
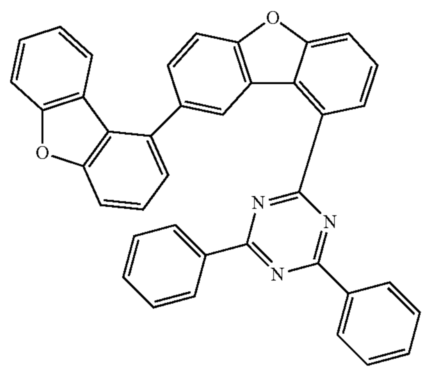
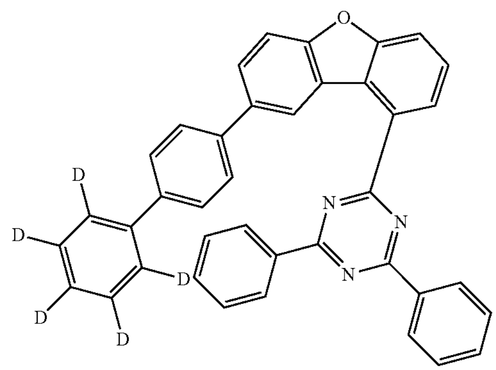
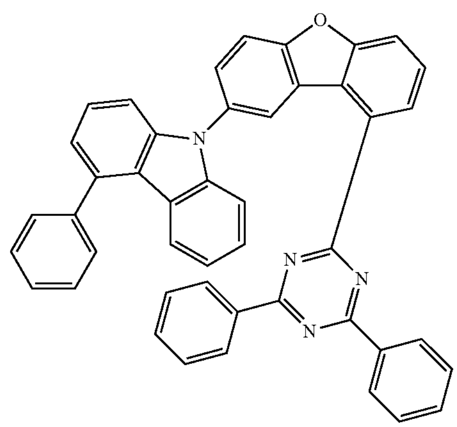

-continued
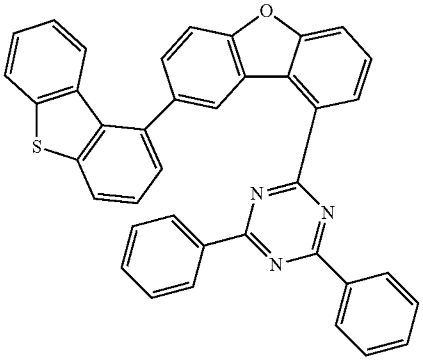
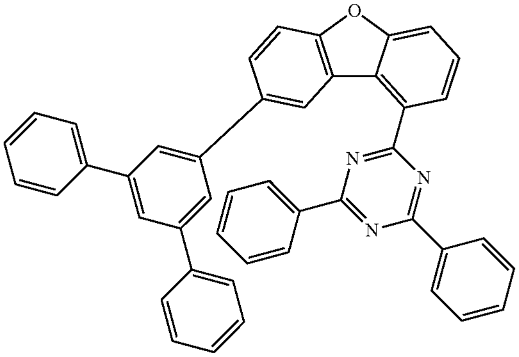
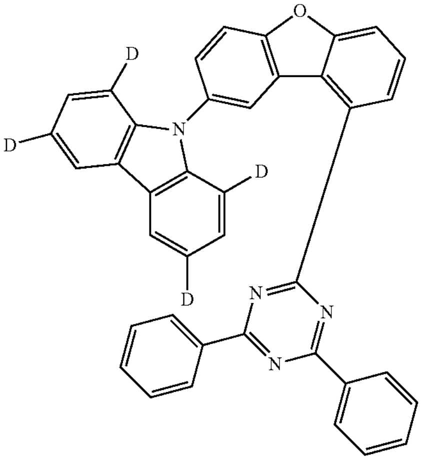
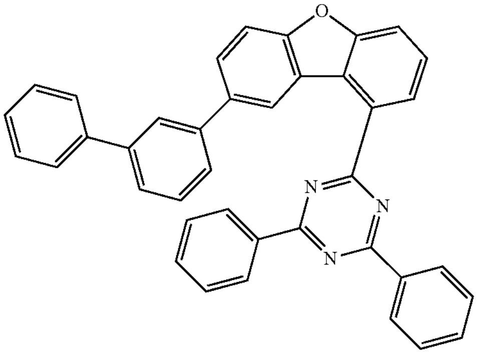
-continued
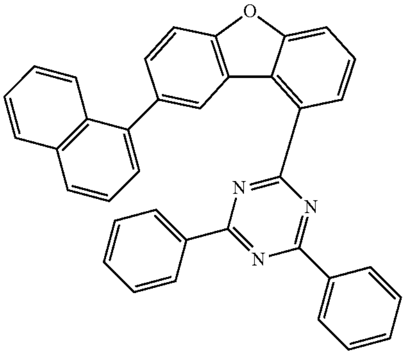
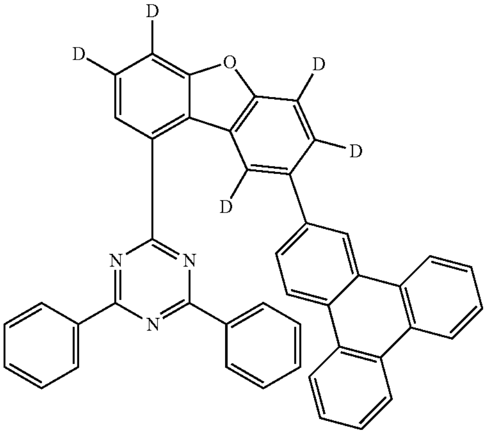
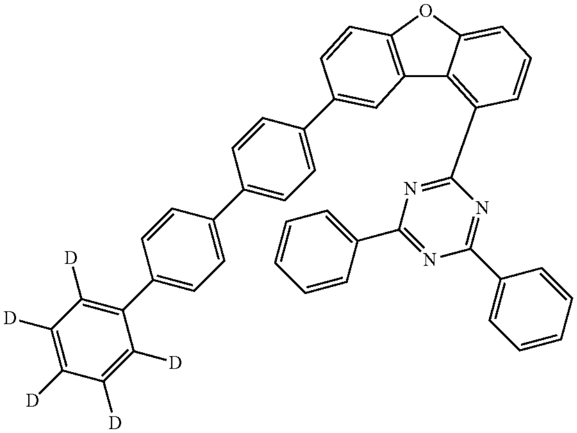
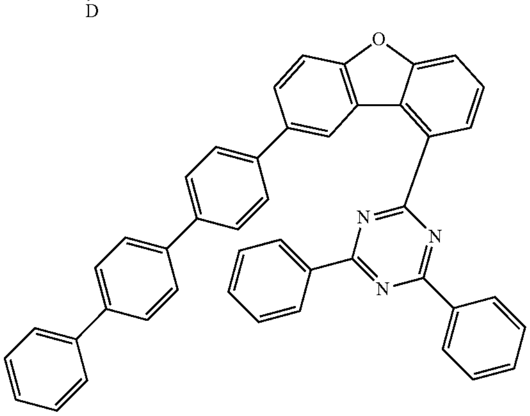

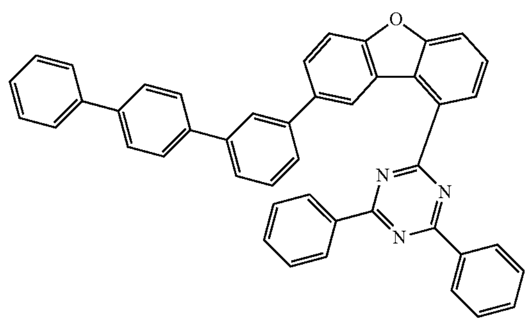
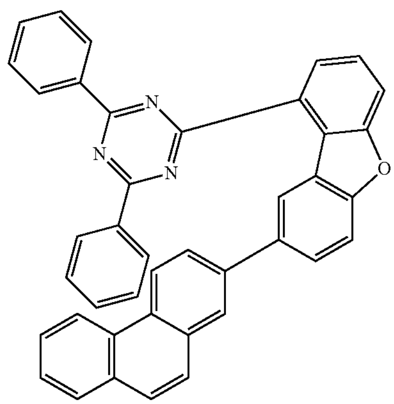
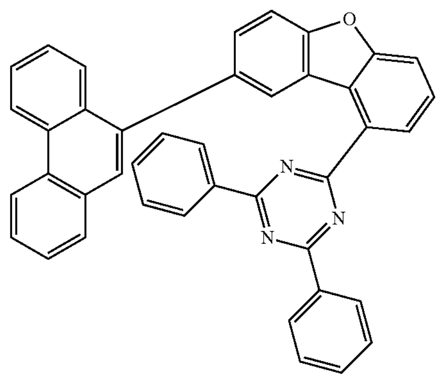
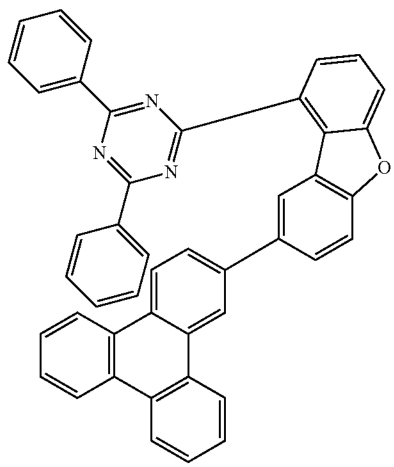
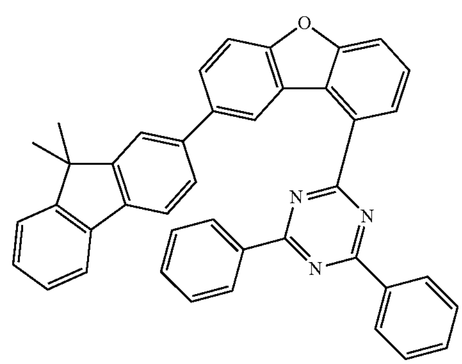
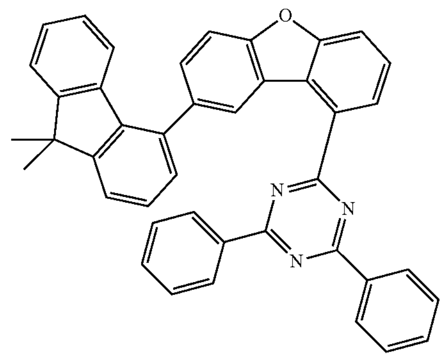
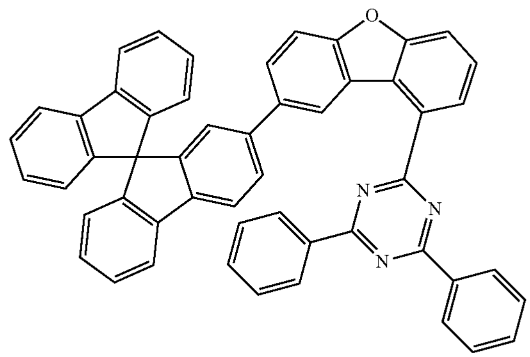
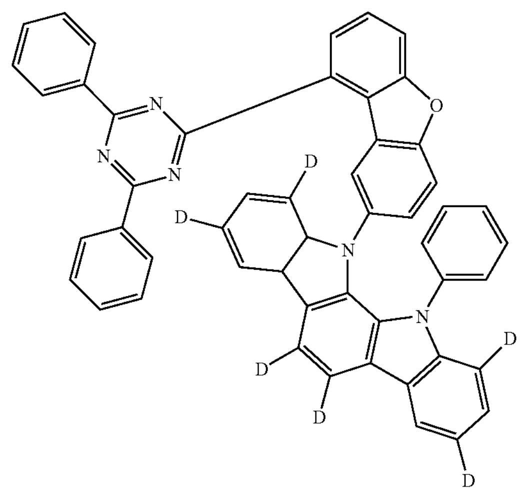

-continued
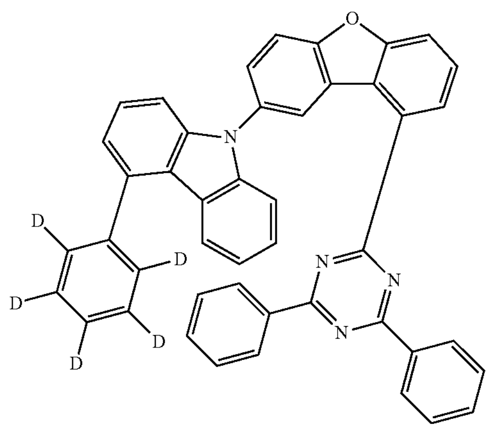
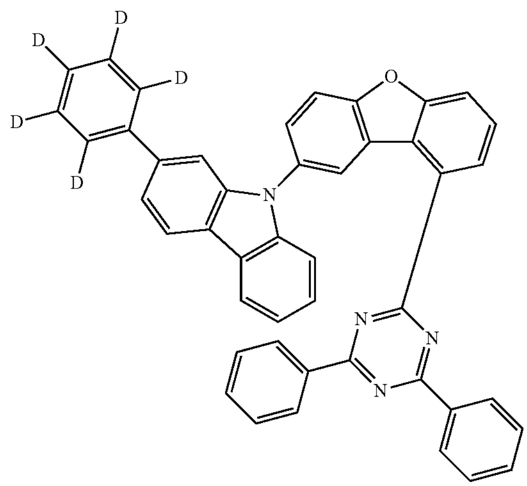
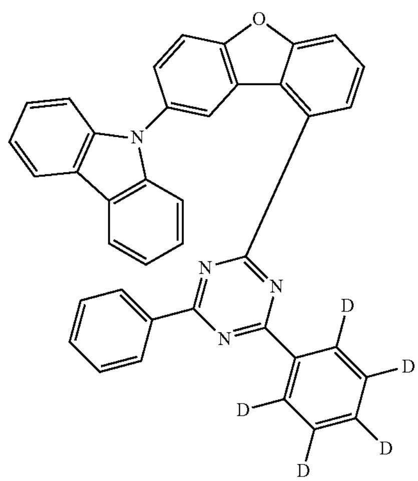
-continued
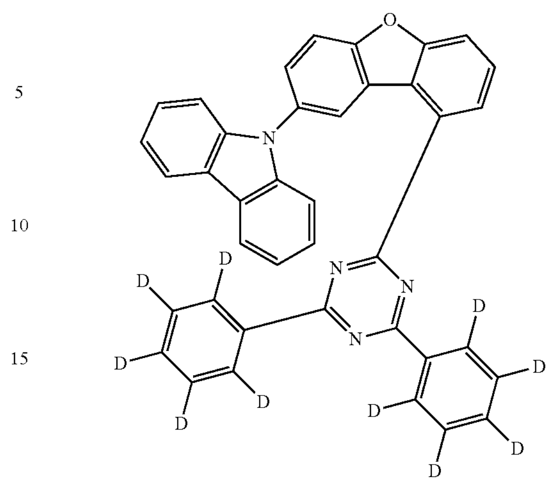
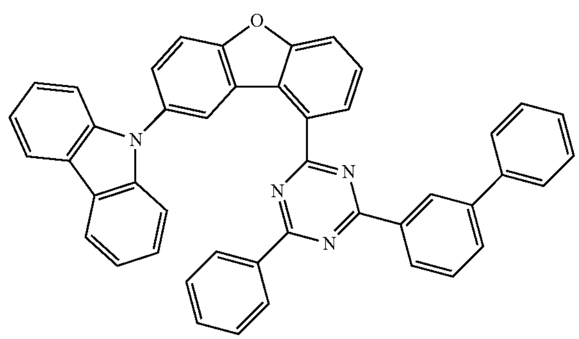
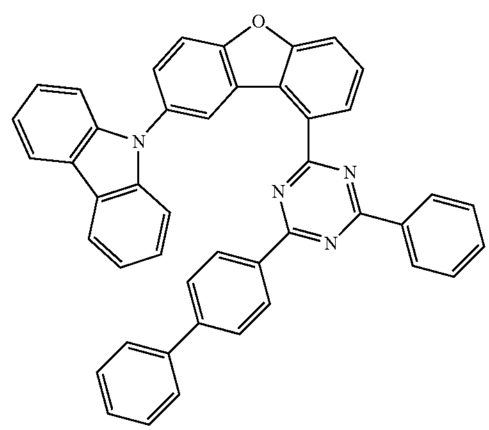

-continued
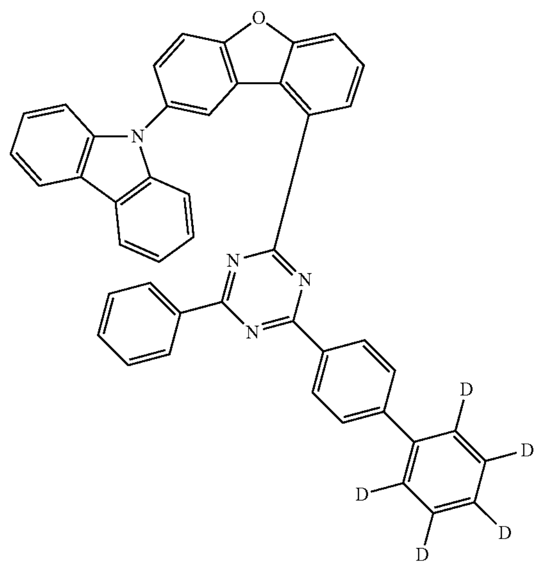
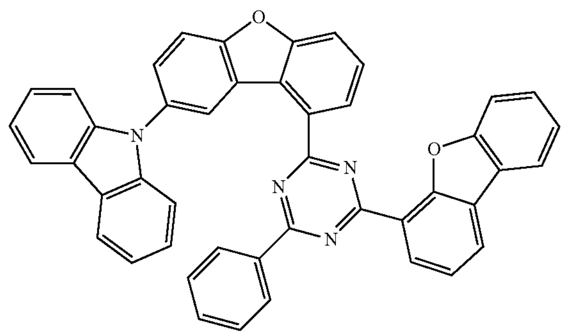
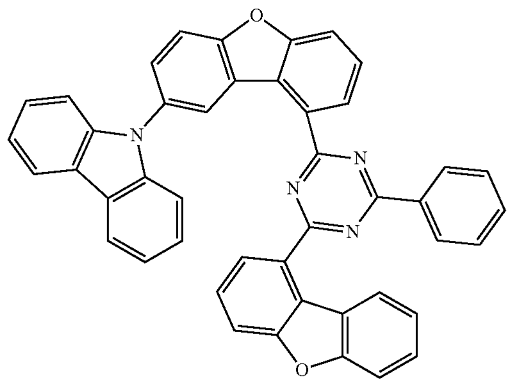
-continued
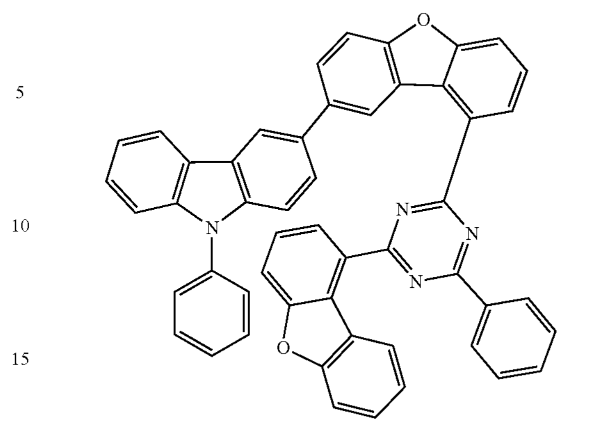
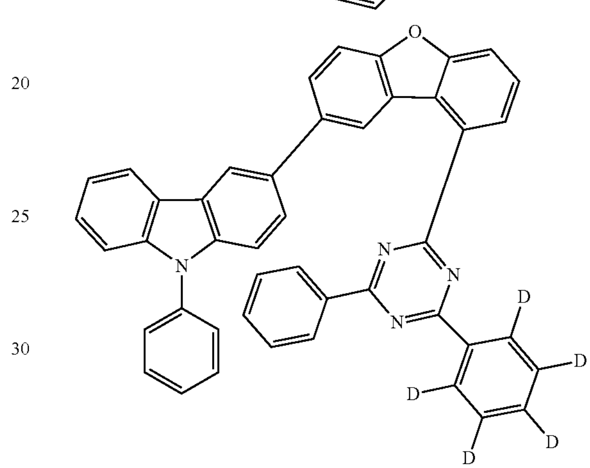
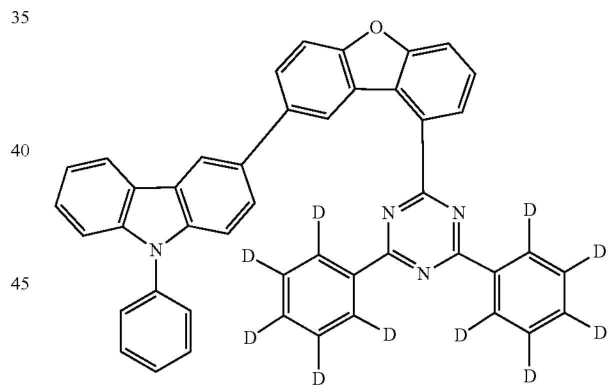
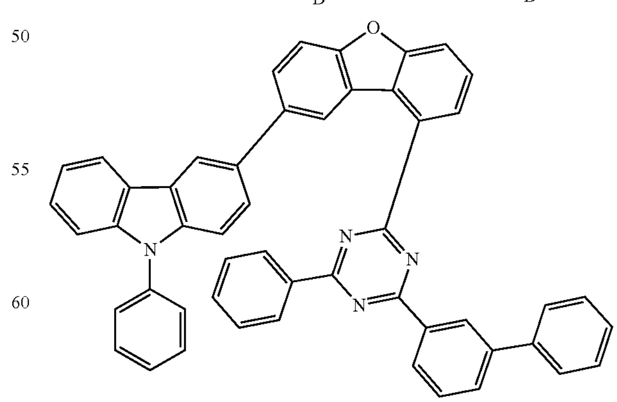

-continued
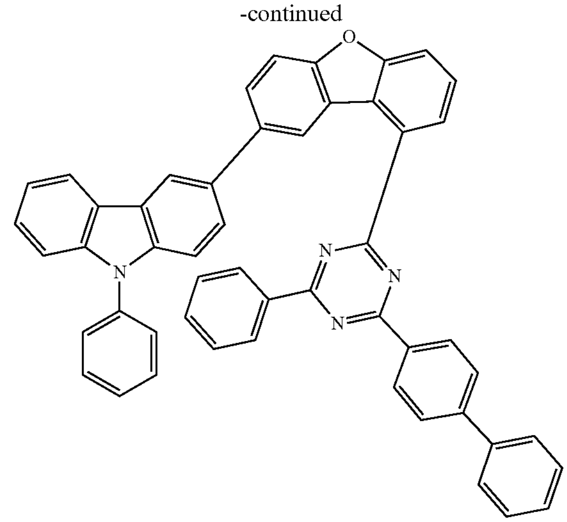
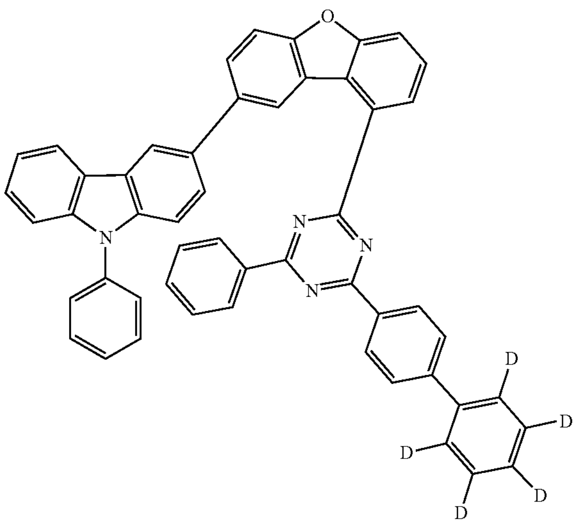
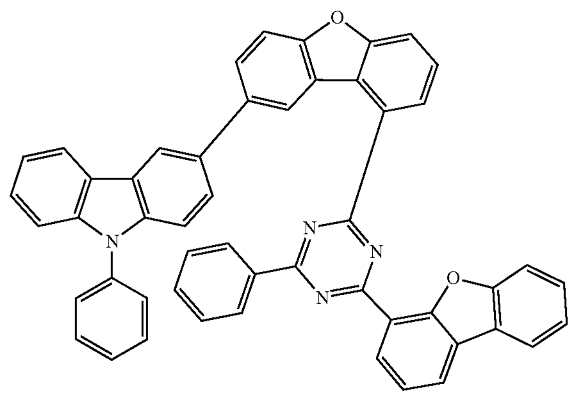
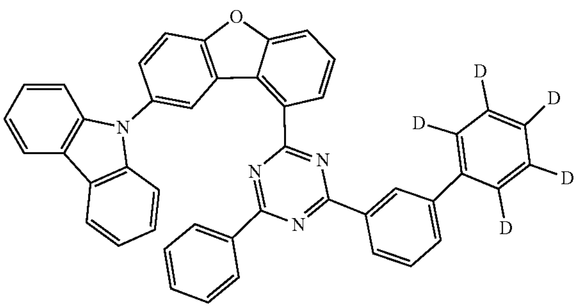
-continued
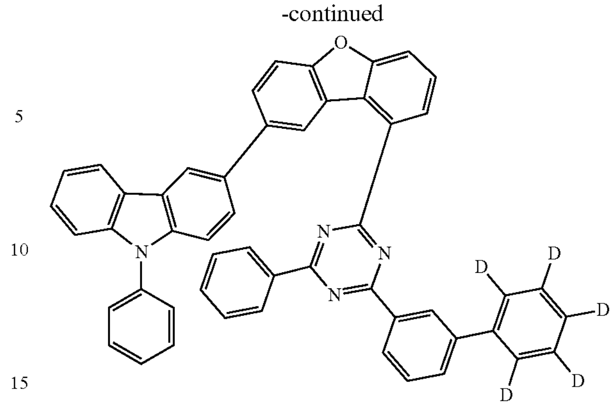
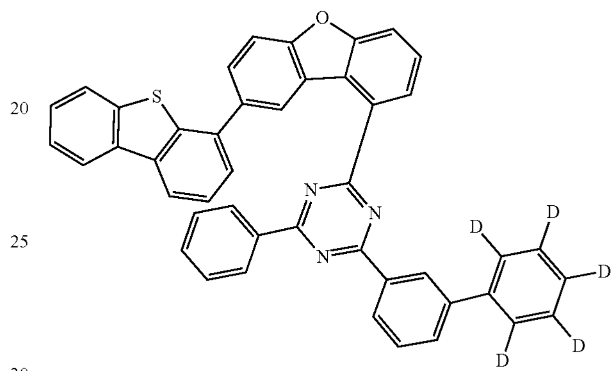
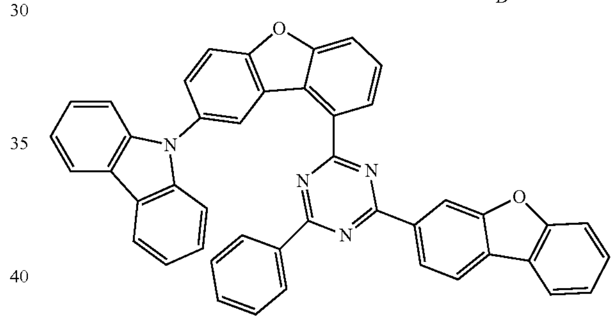
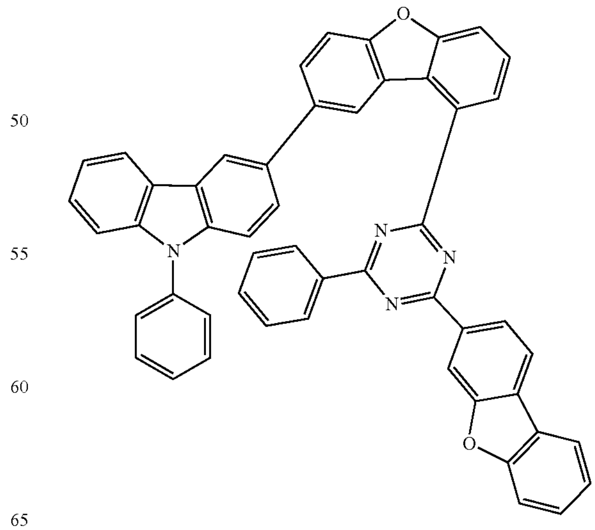

-continued
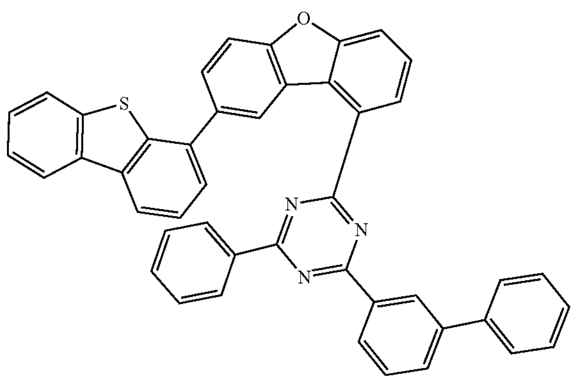
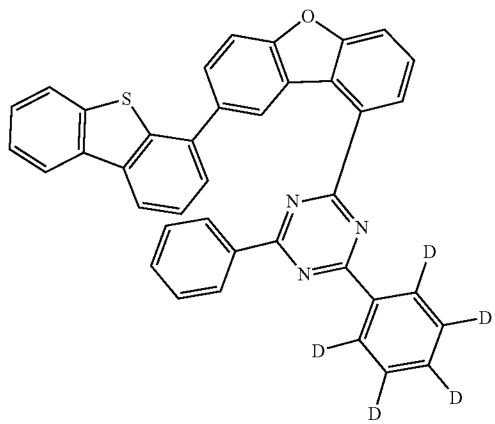
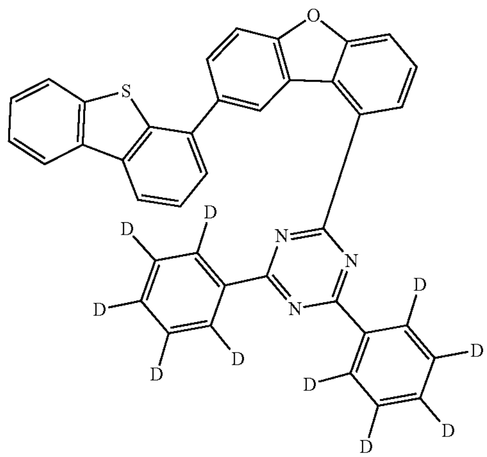
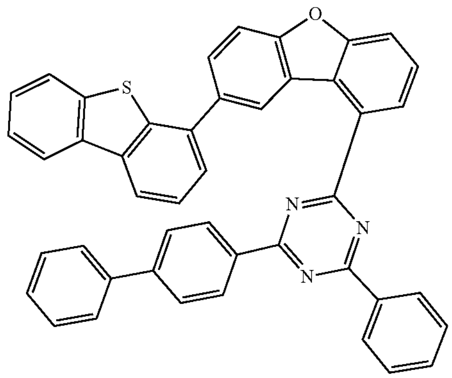
-continued
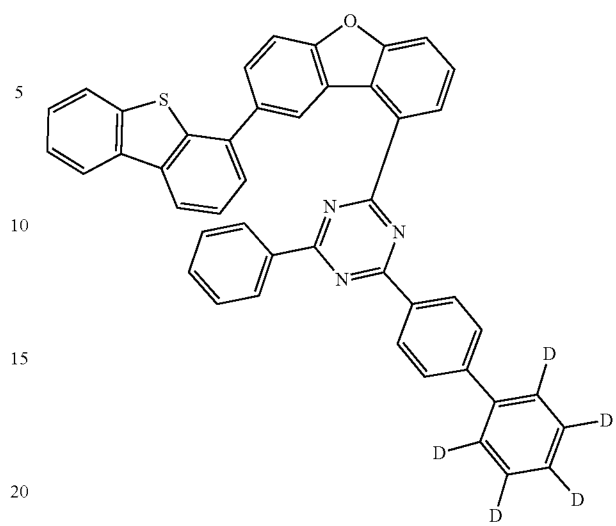
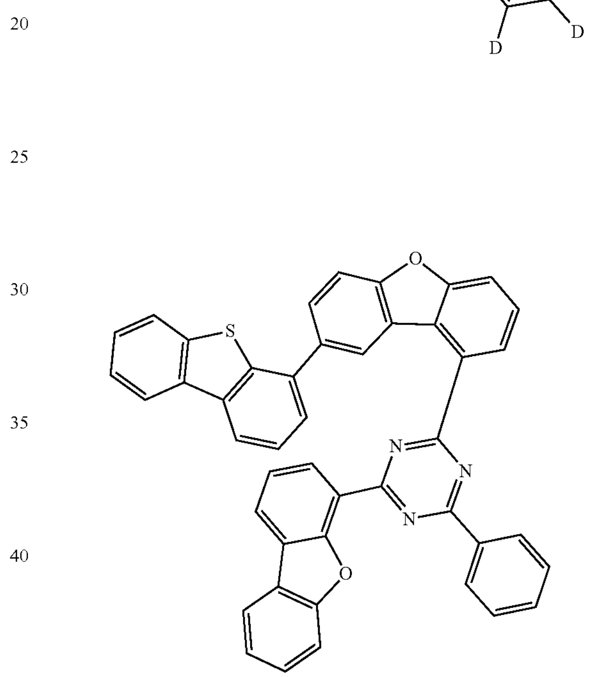
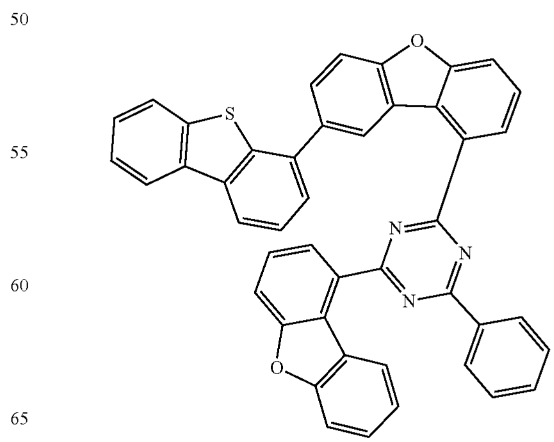

-continued
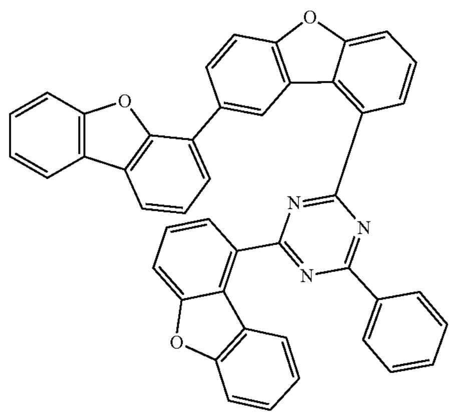
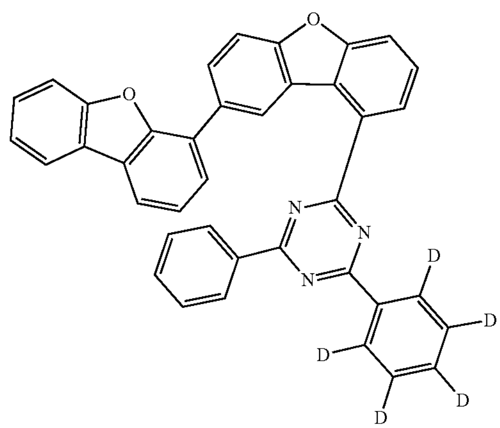
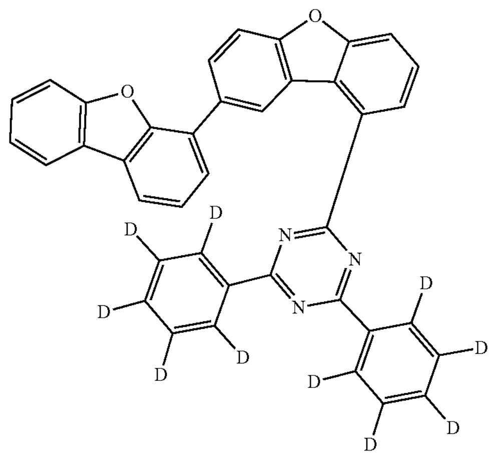
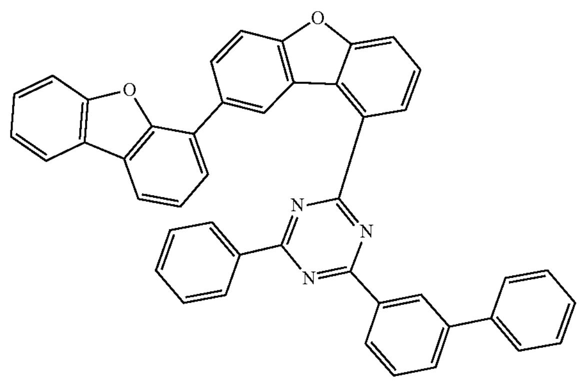
-continued
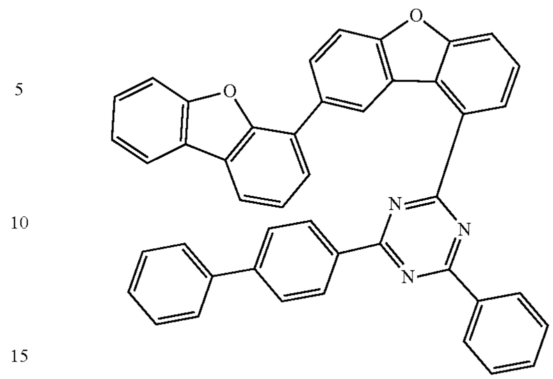
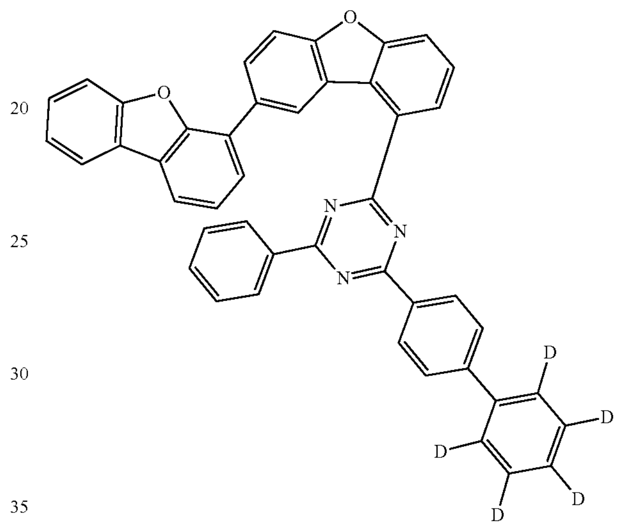
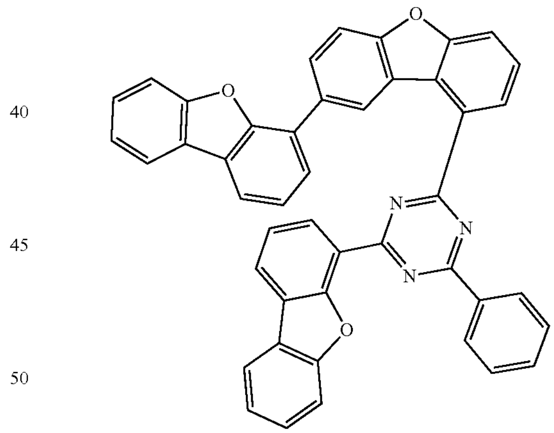
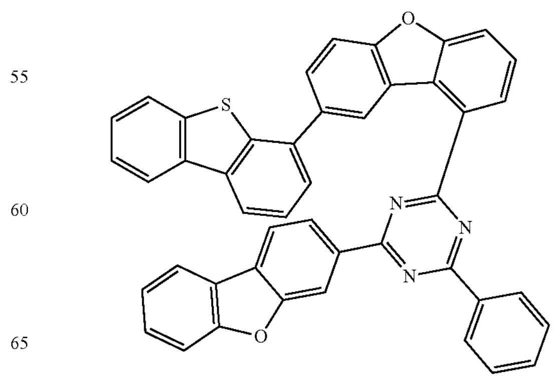

-continued
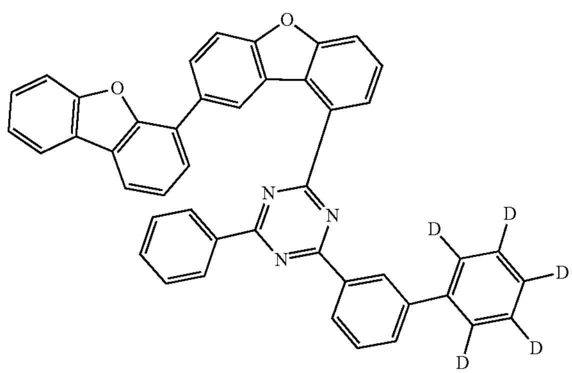
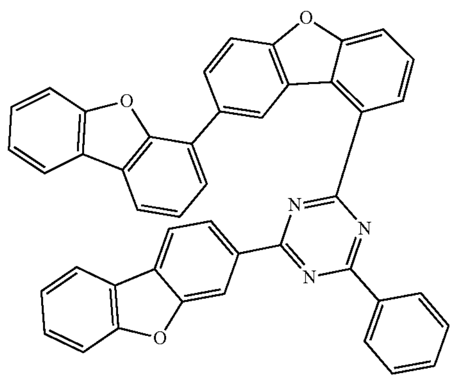
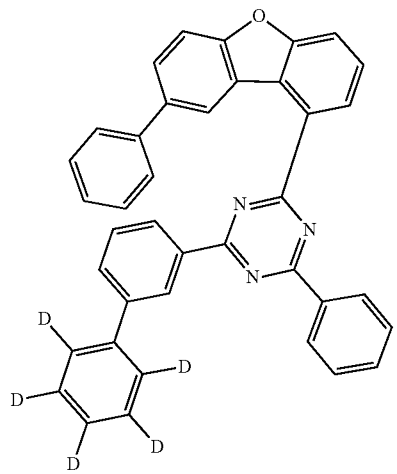
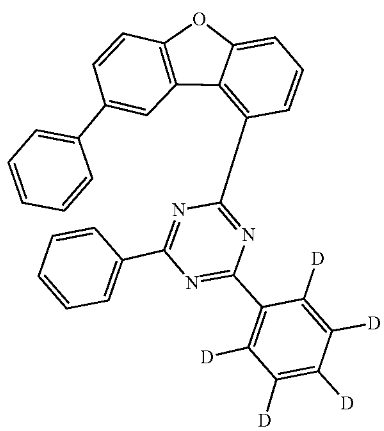
-continued
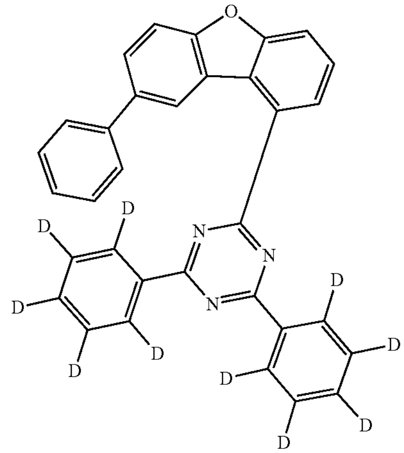
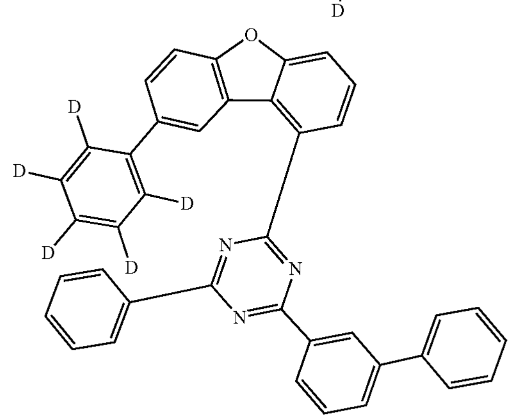
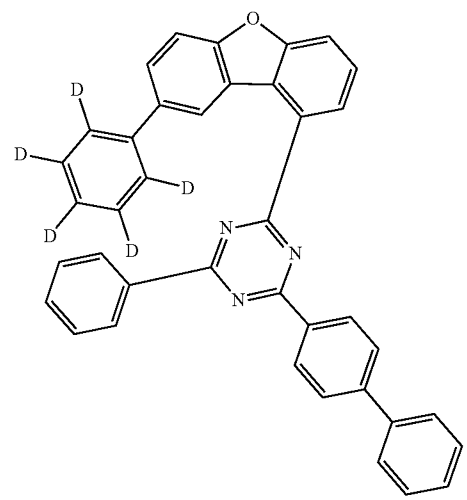
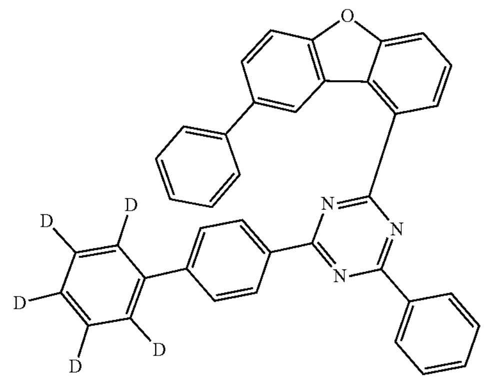

-continued
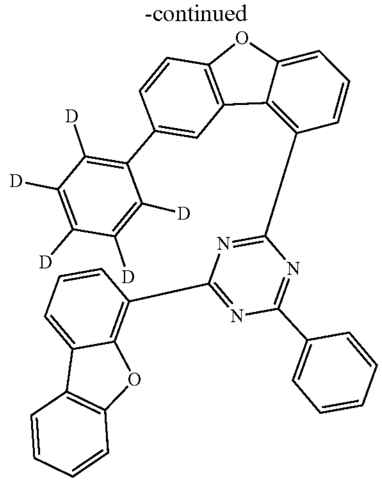
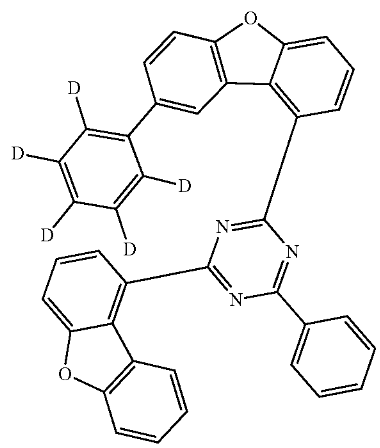
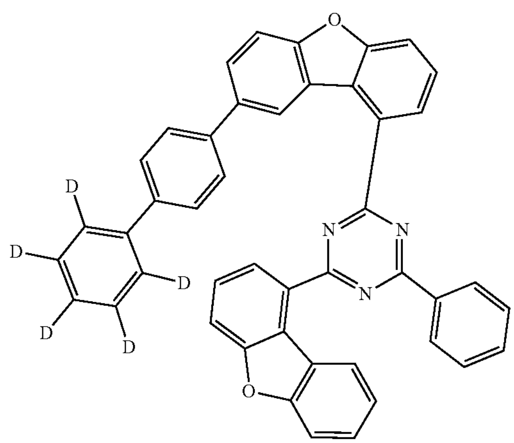
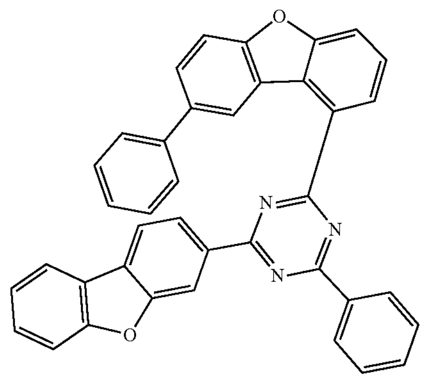
-continued
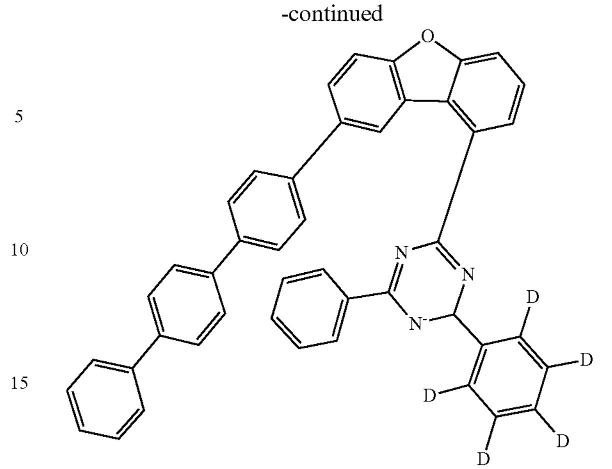
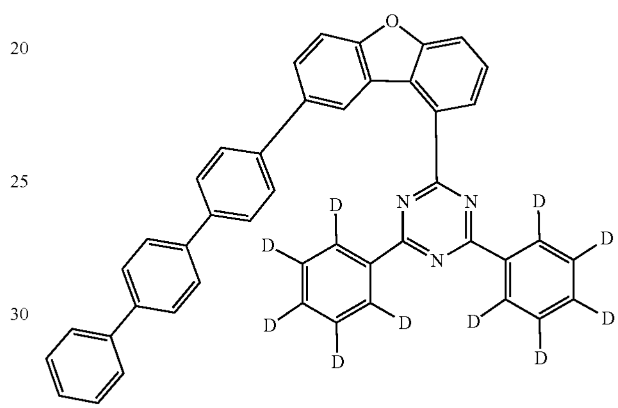
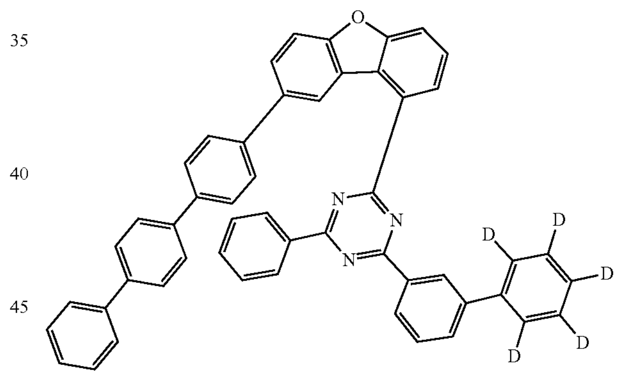
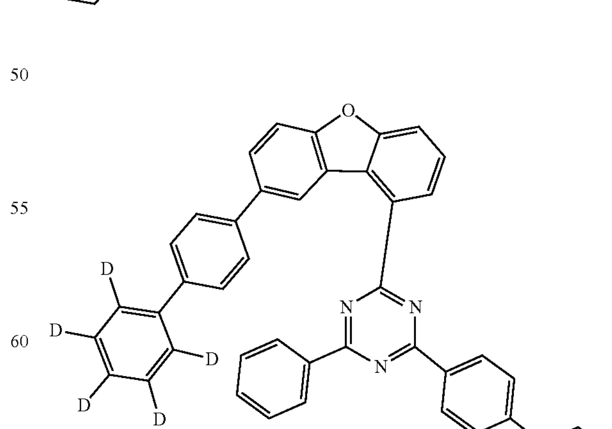
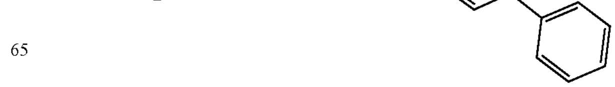

-continued
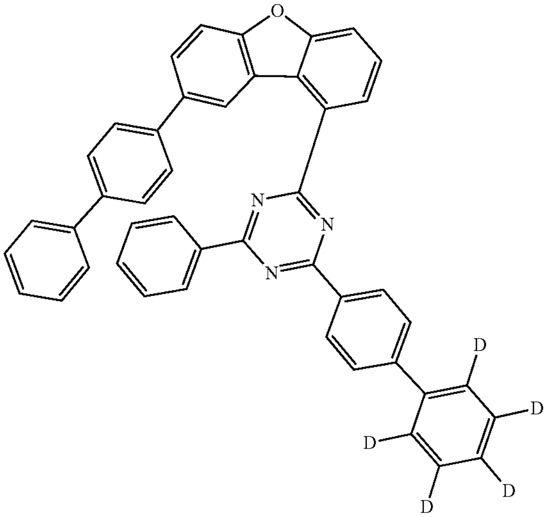
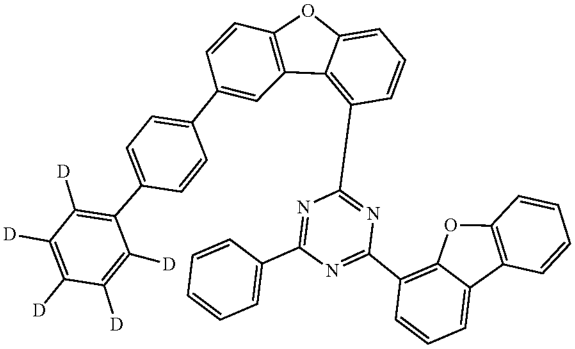
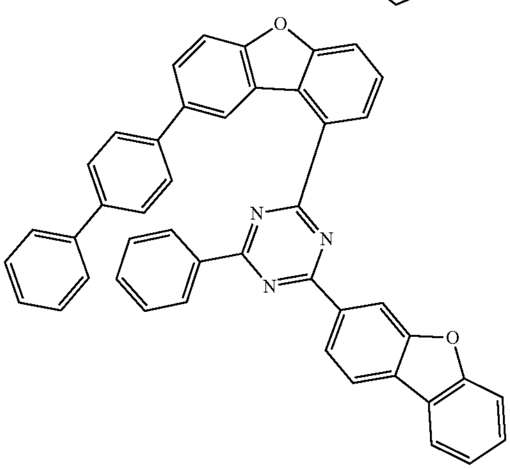
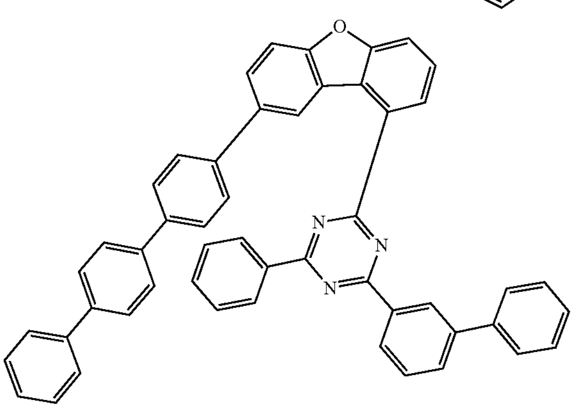
-continued
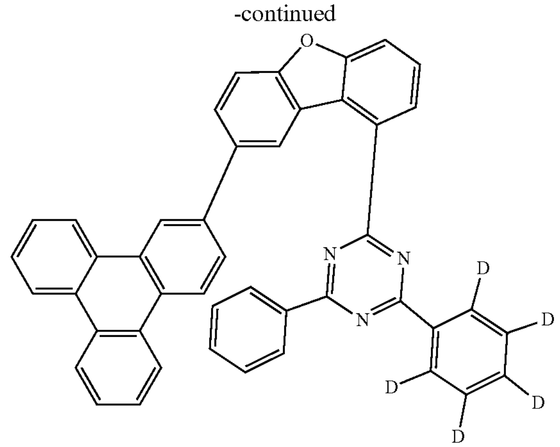
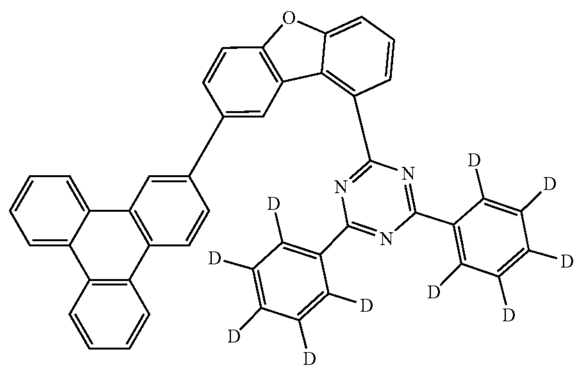
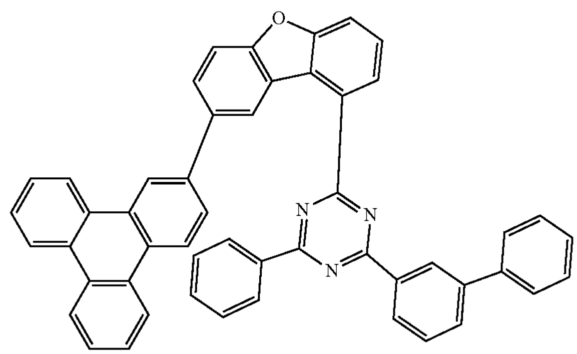
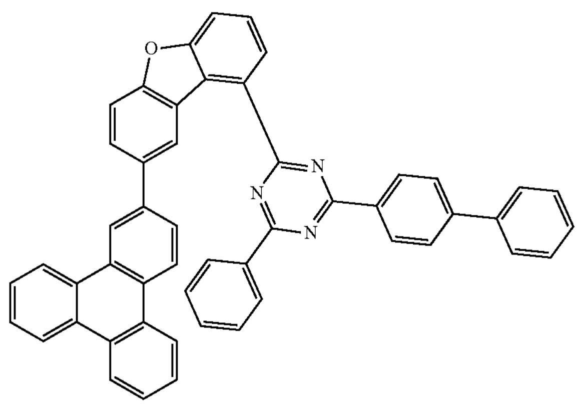

-continued
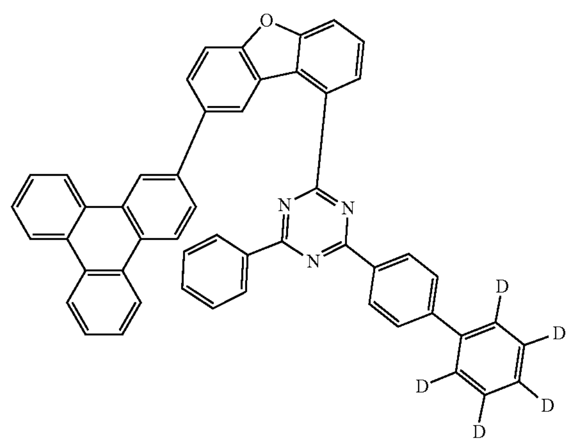
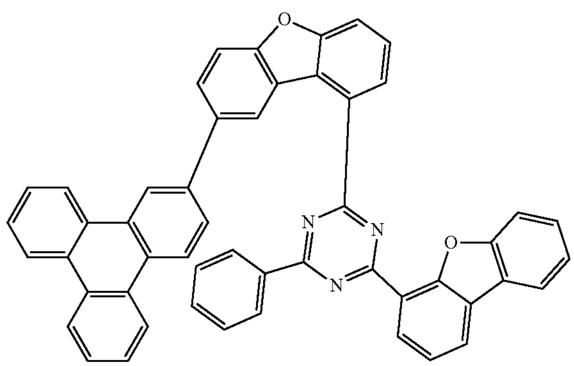
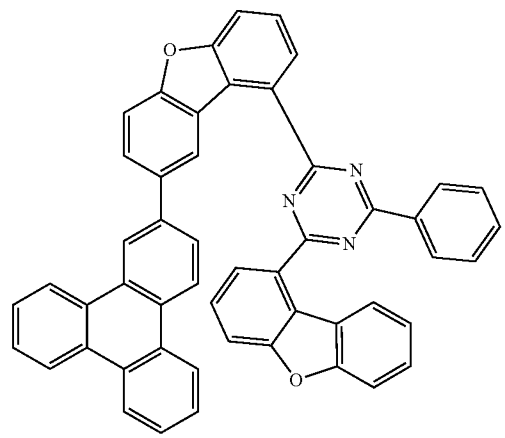
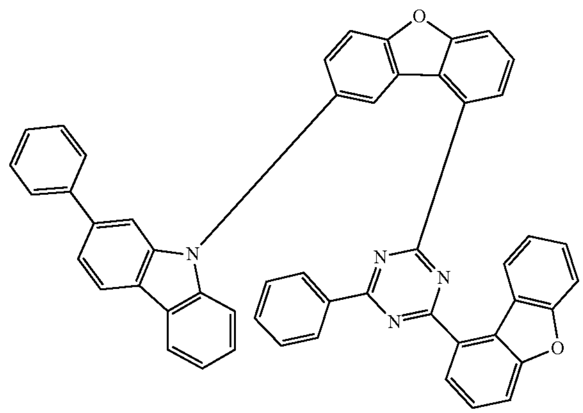
-continued
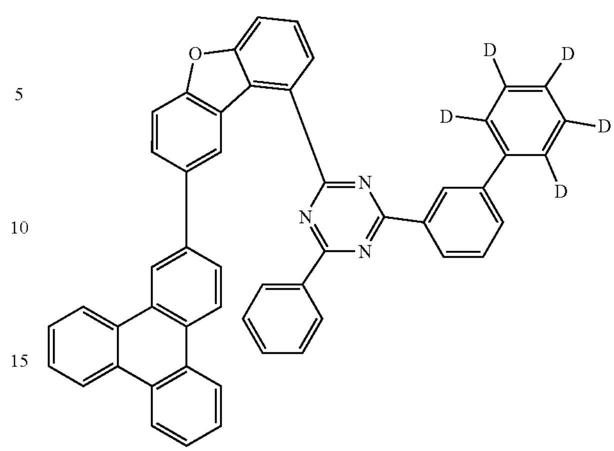
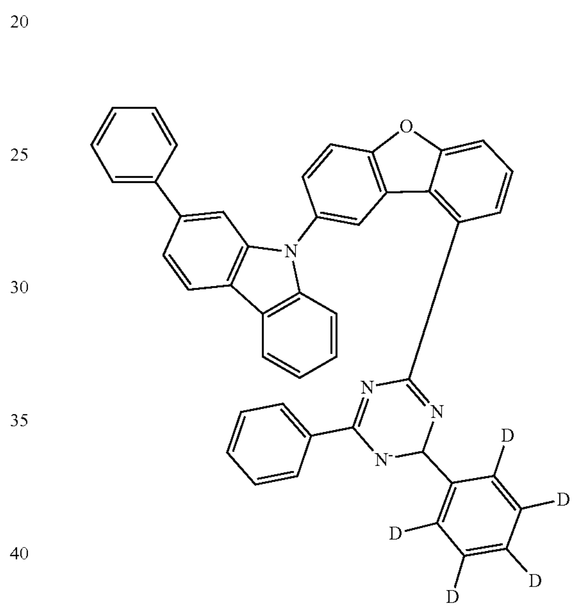
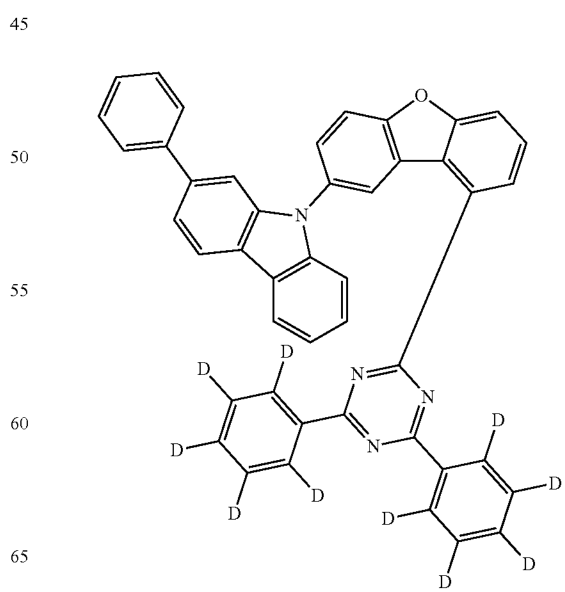

-continued
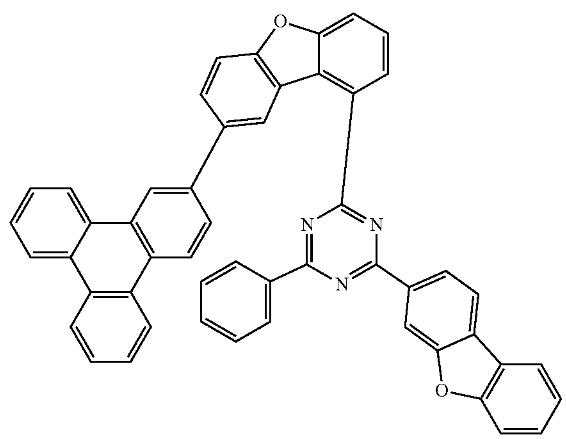
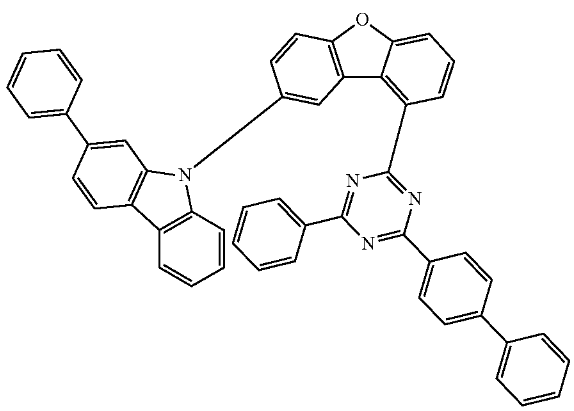
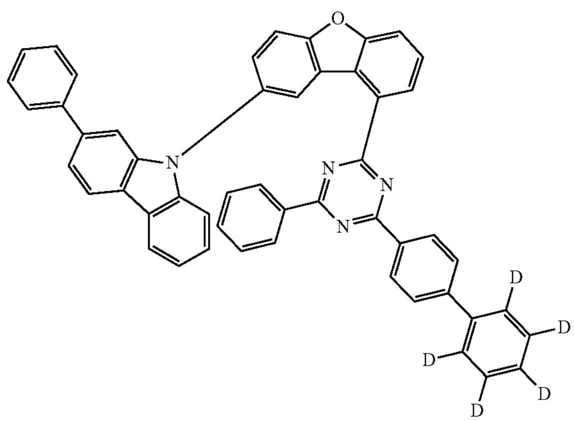
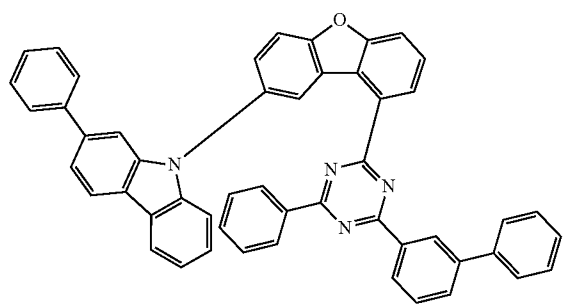
-continued
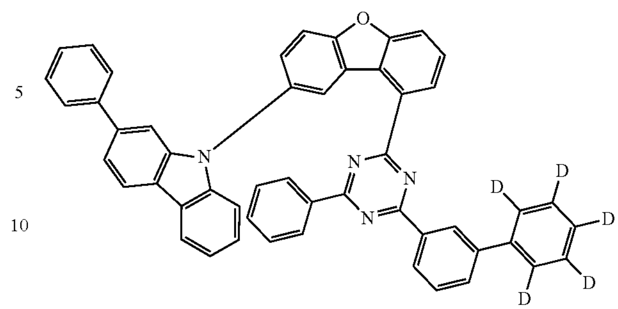
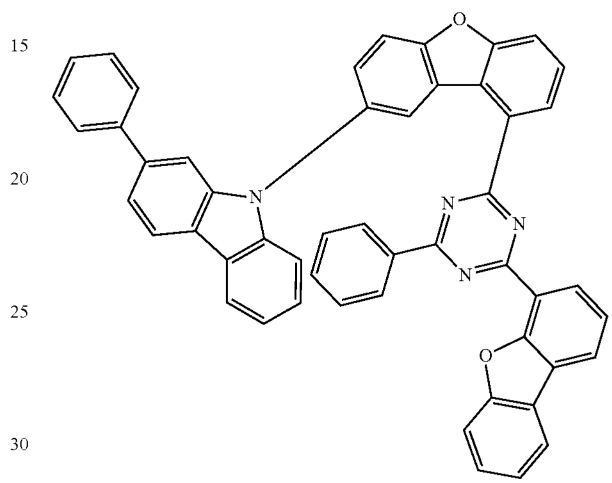
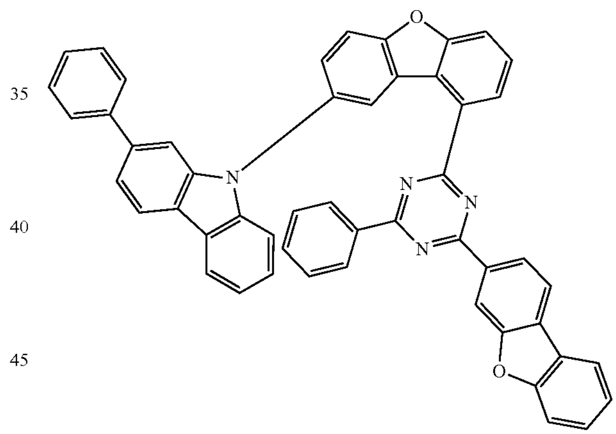
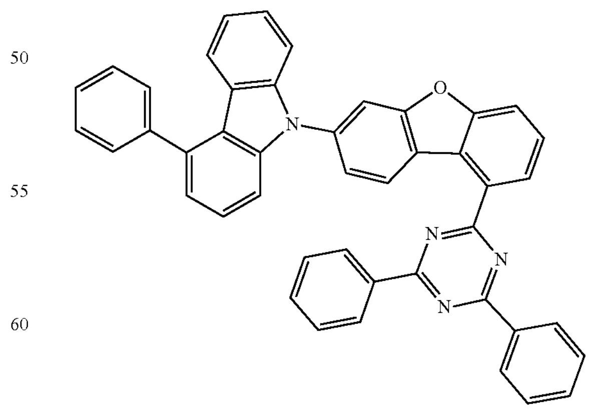

-continued
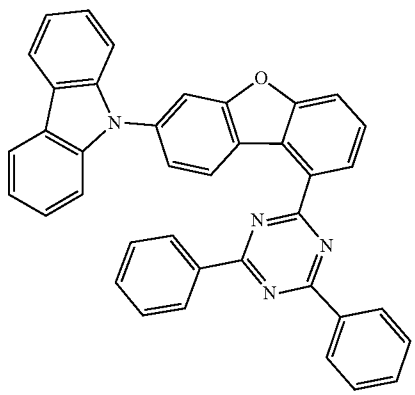
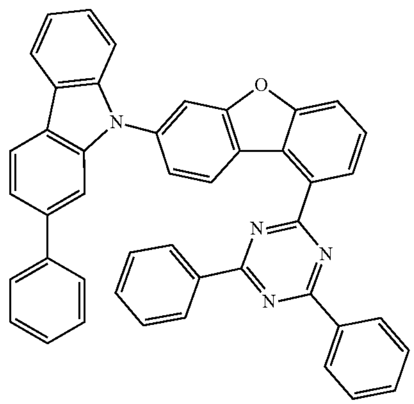
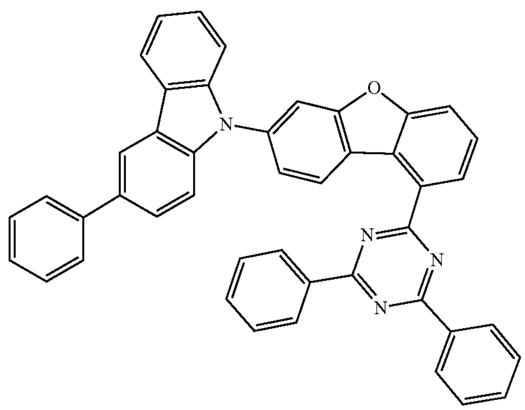
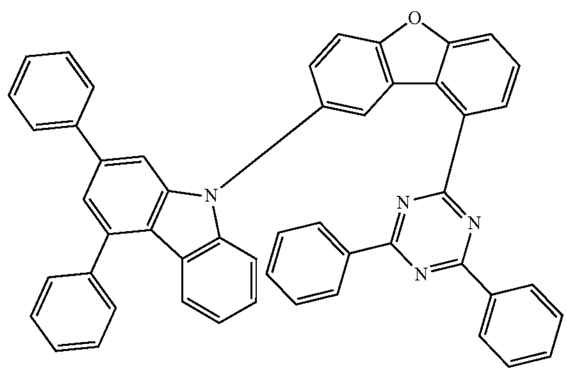
-continued
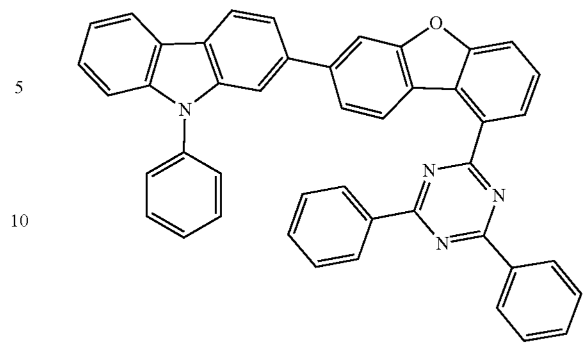
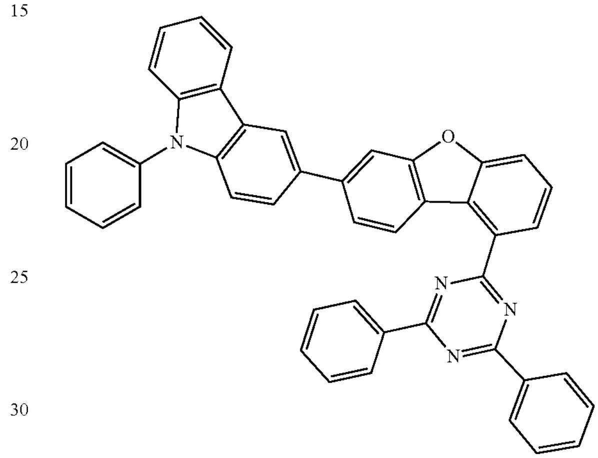
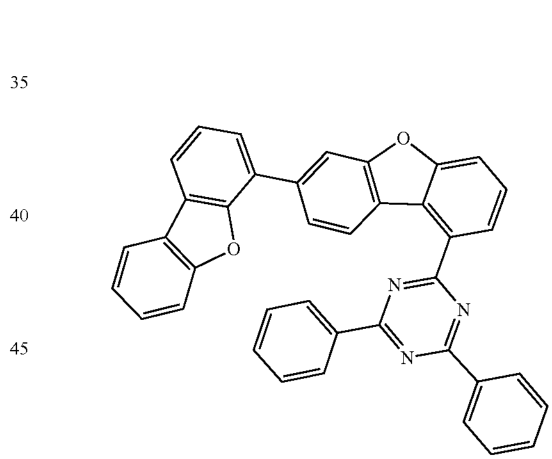
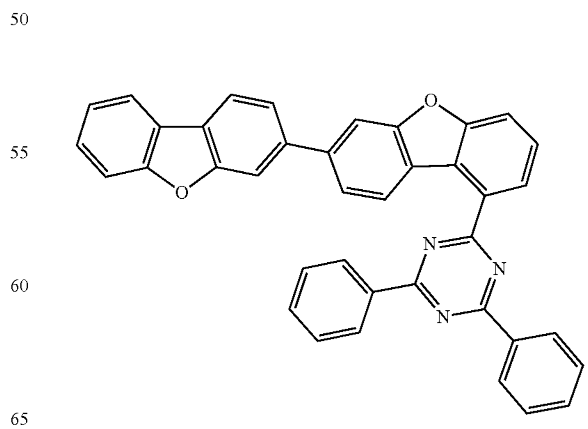

-continued
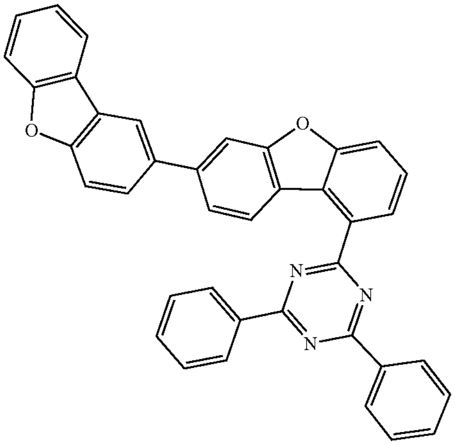
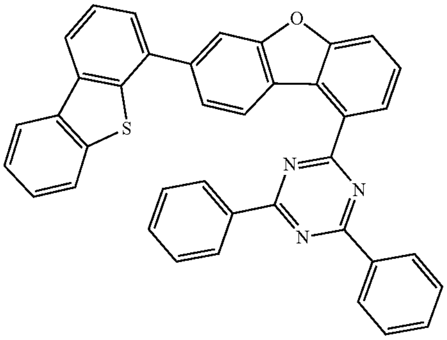
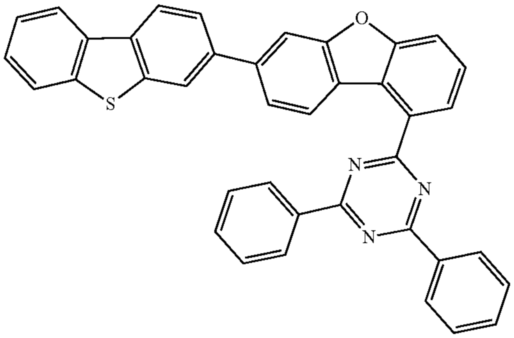
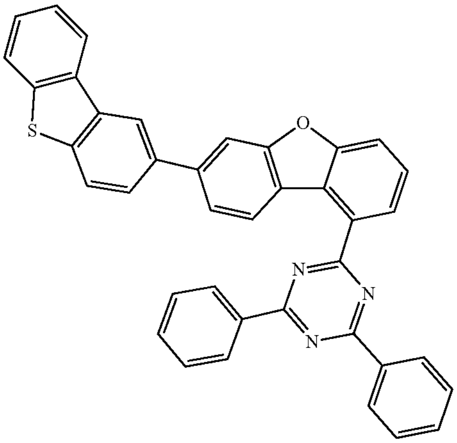
-continued
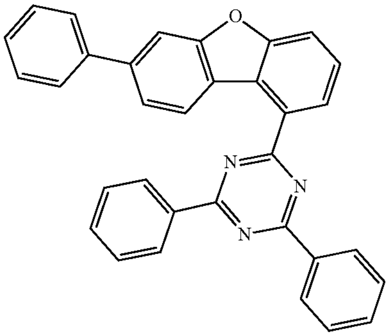
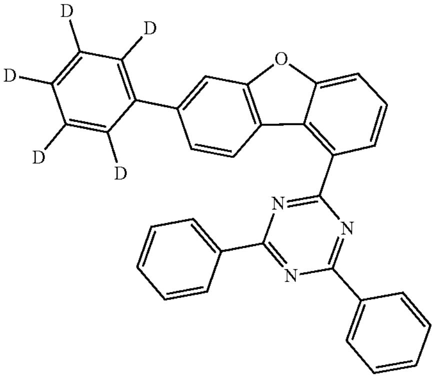
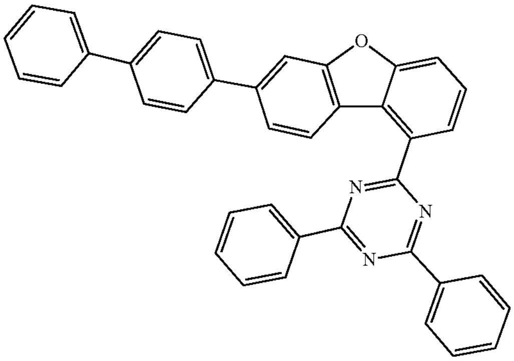
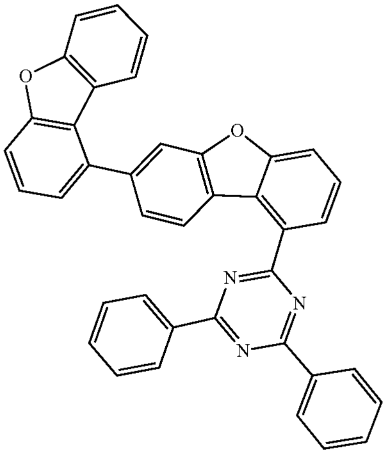

-continued
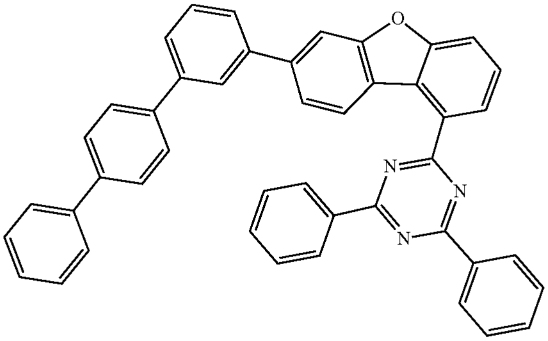
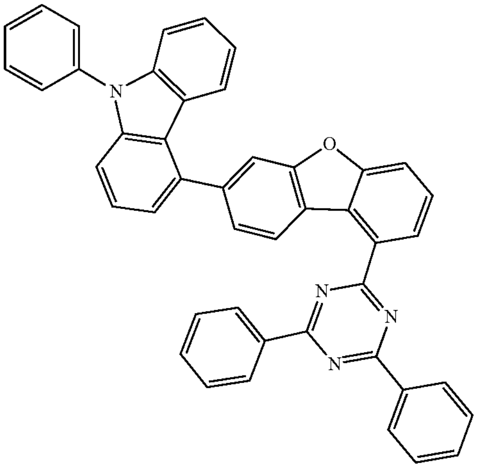
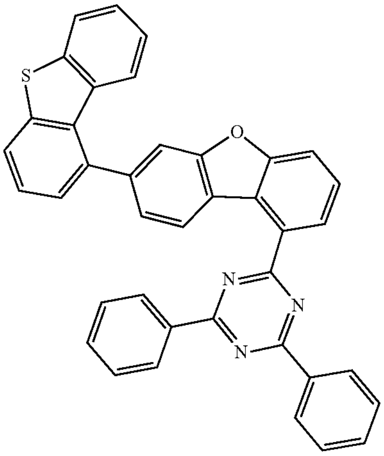
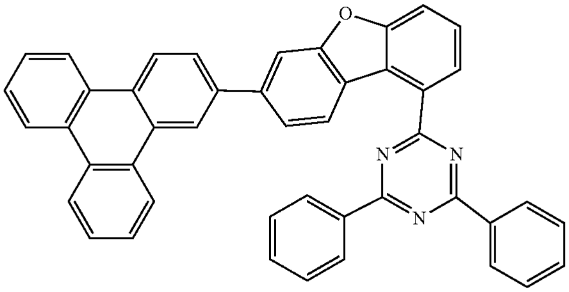
-continued
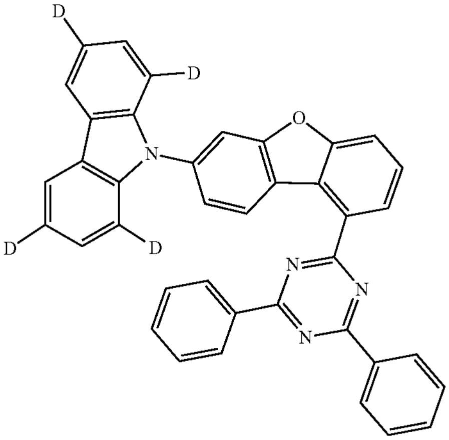
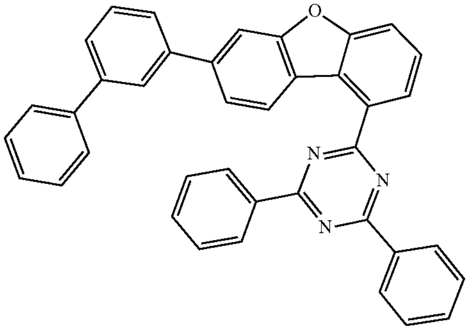
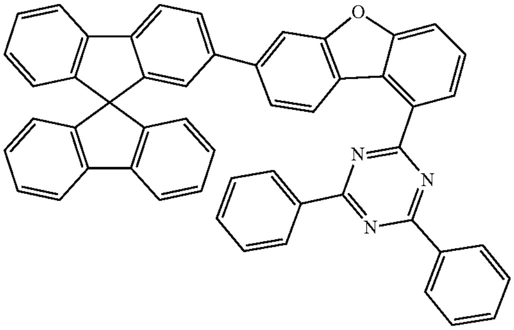
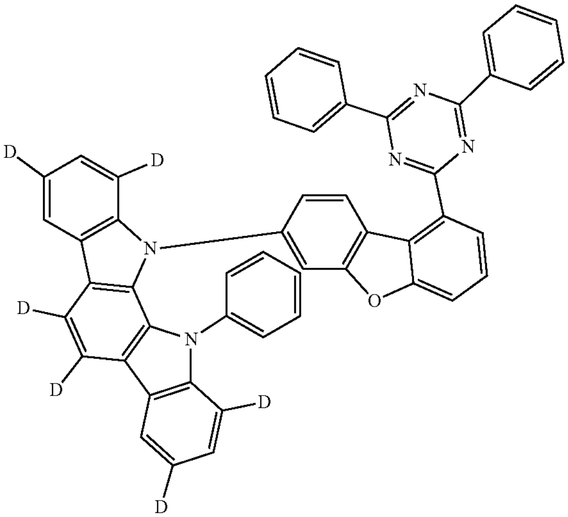

-continued
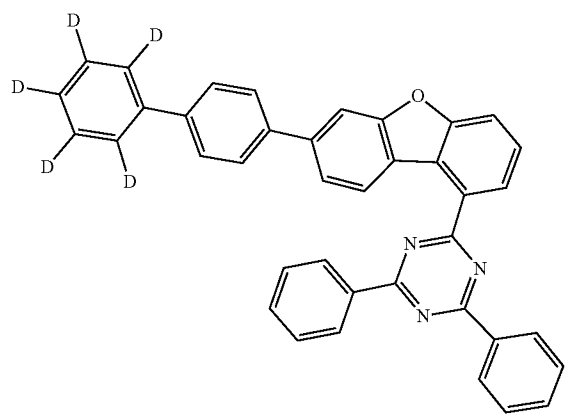
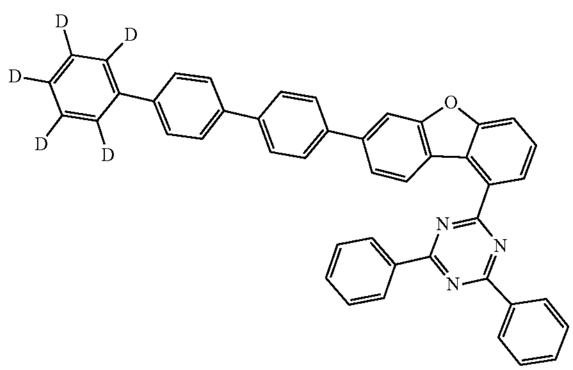
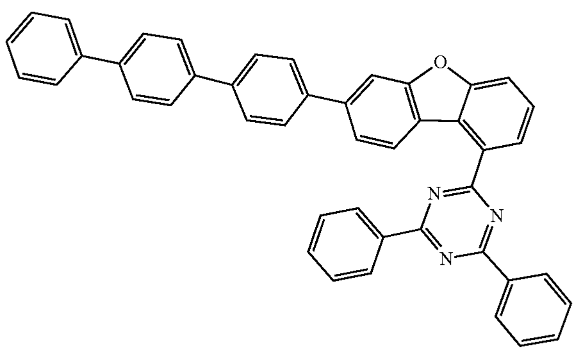
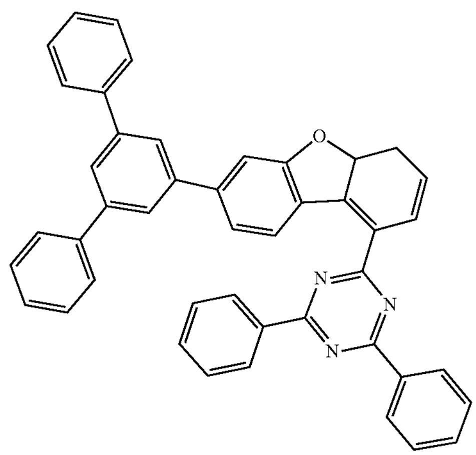
-continued
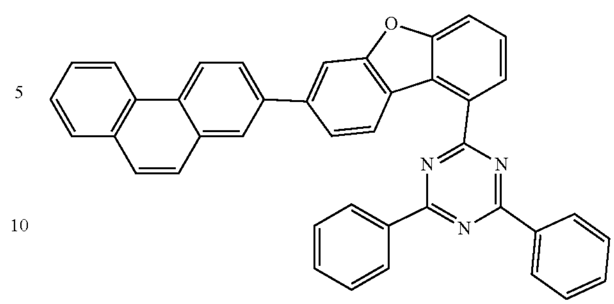
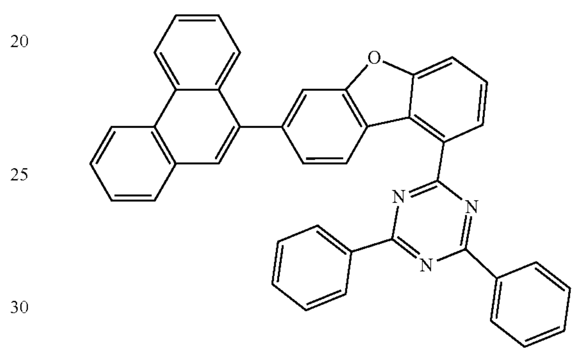
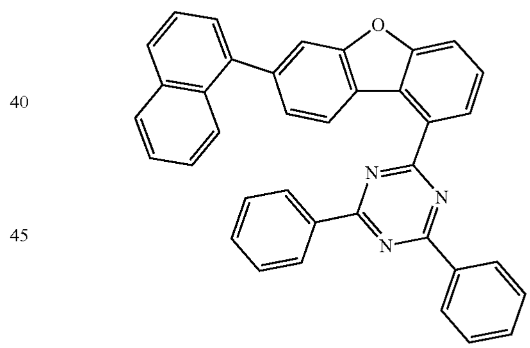
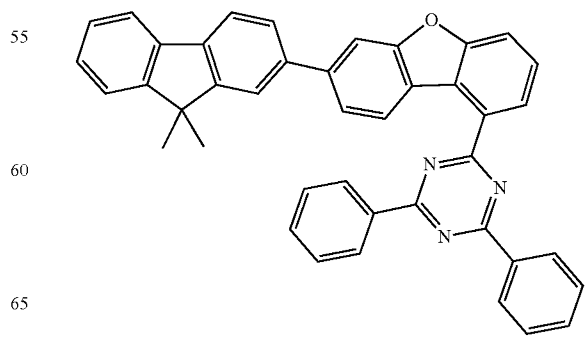

-continued
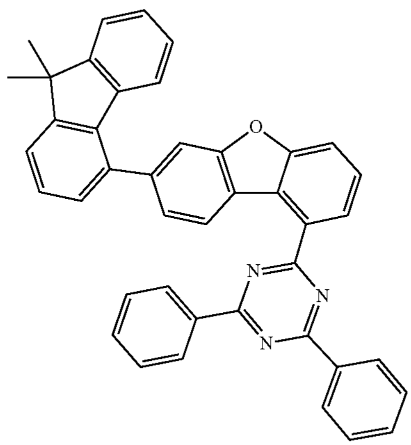
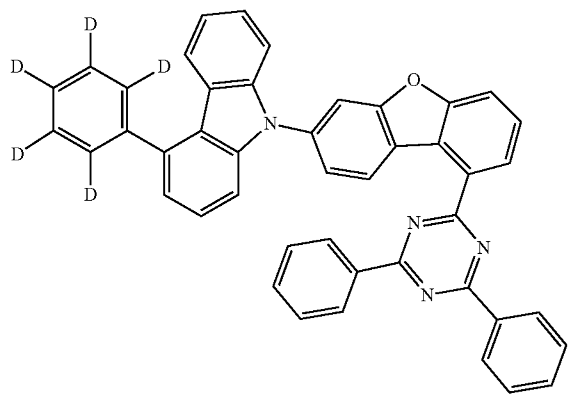
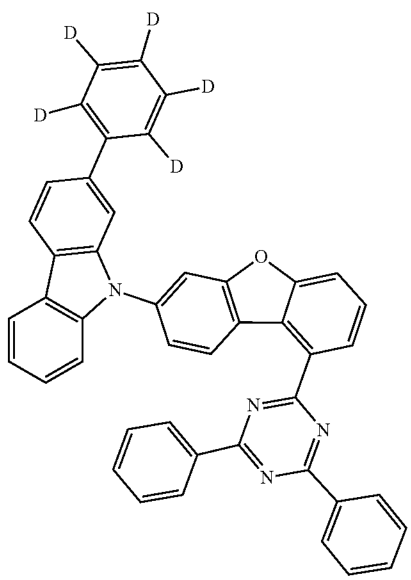
-continued
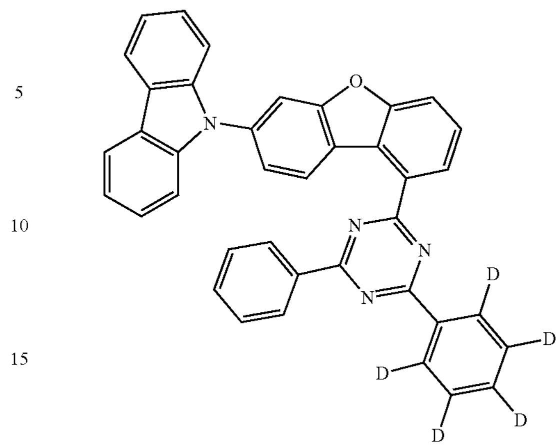
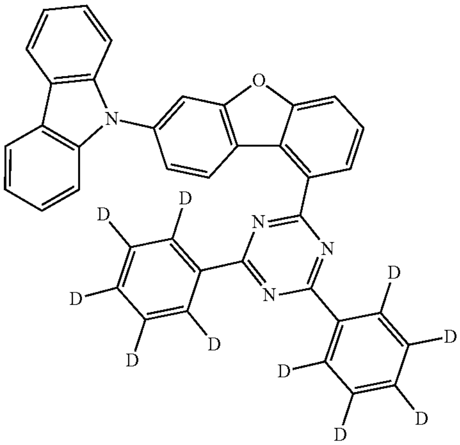
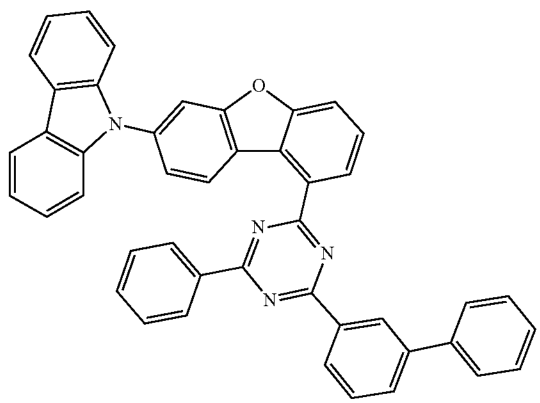

-continued
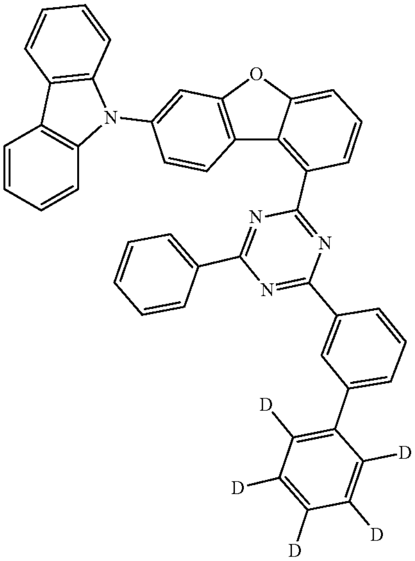
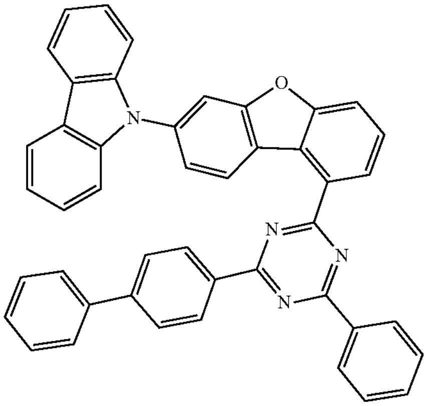
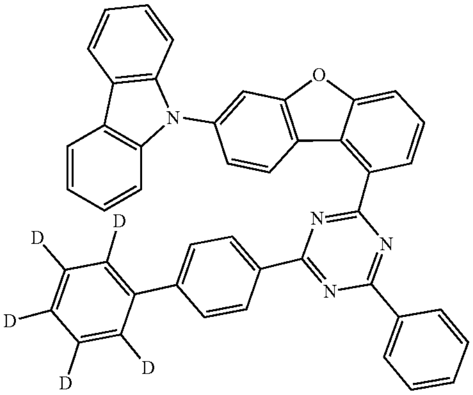
-continued
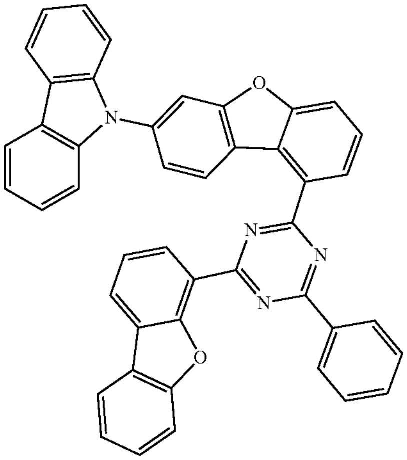
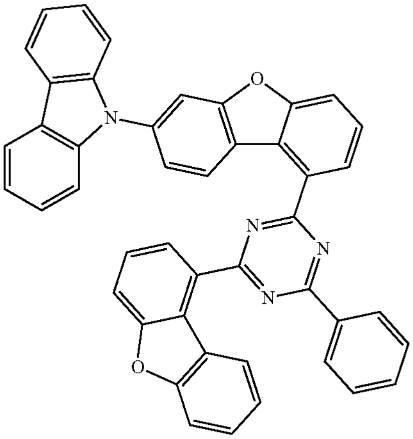
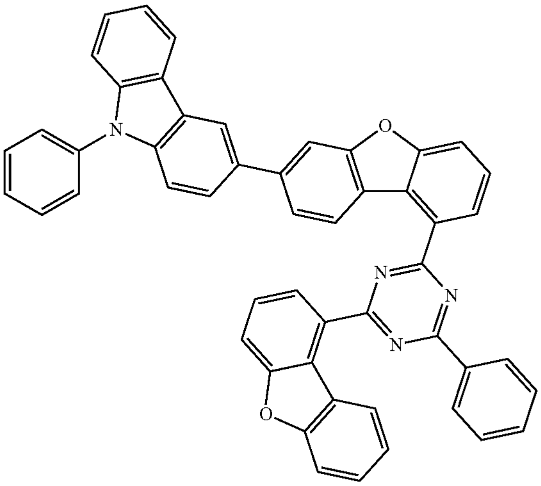

-continued
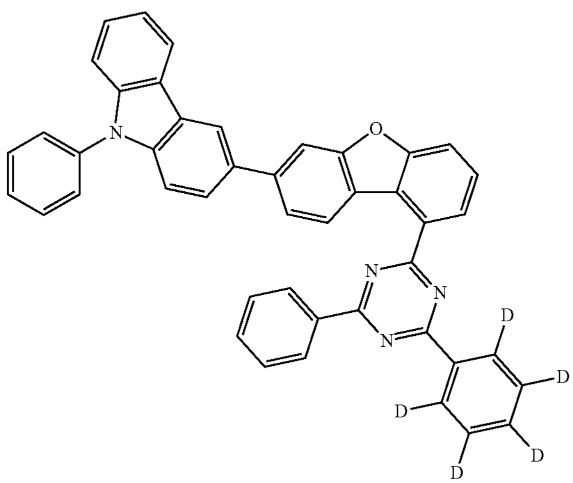
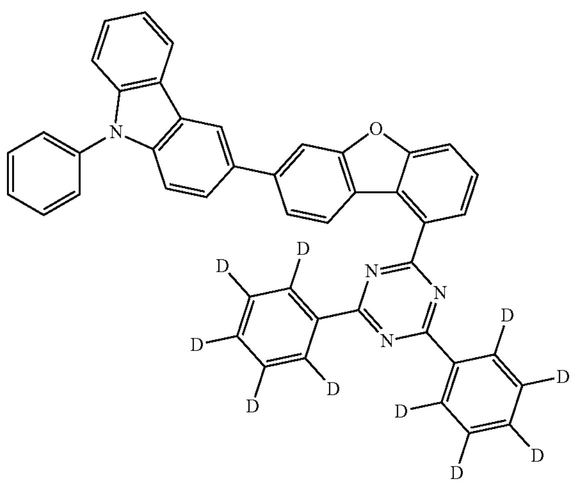
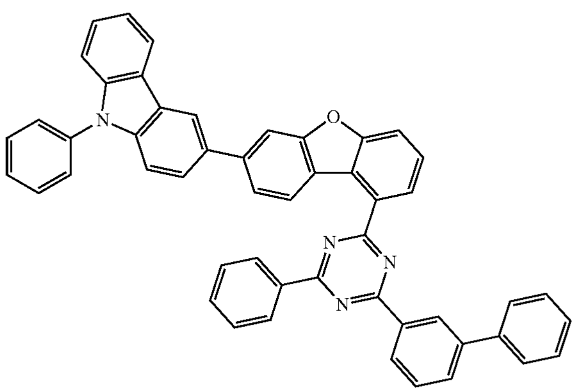
-continued
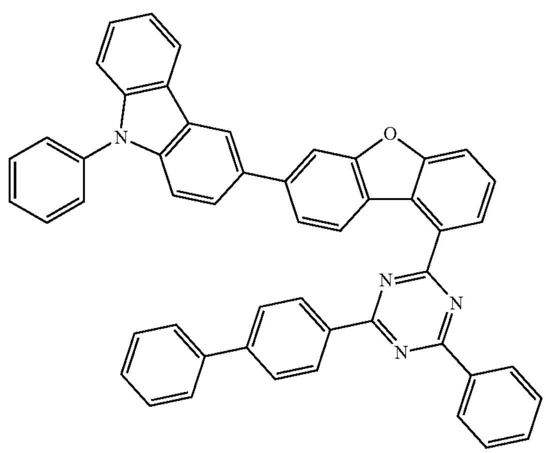
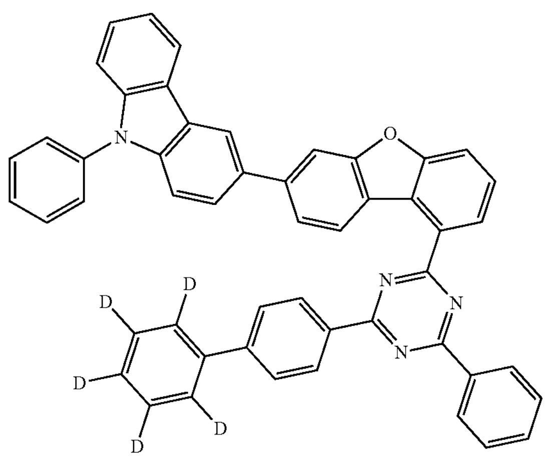
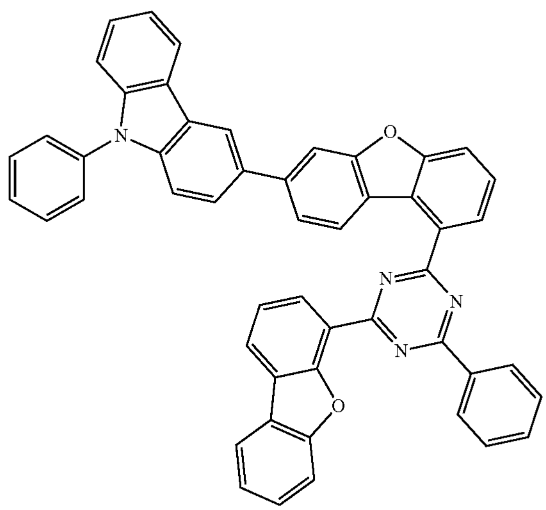

-continued
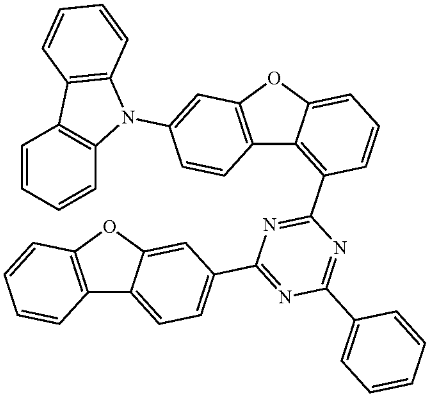
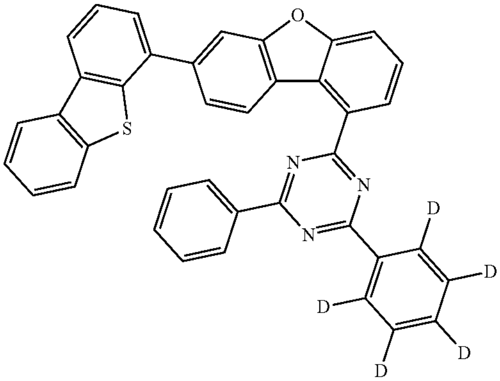
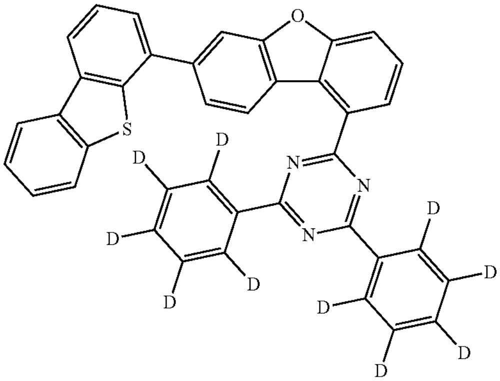
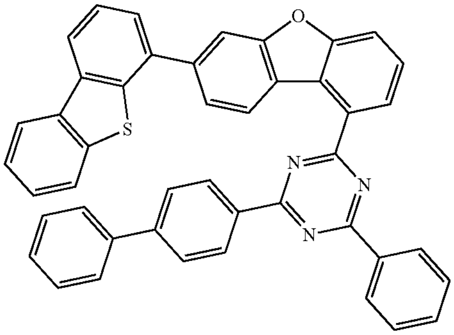
-continued
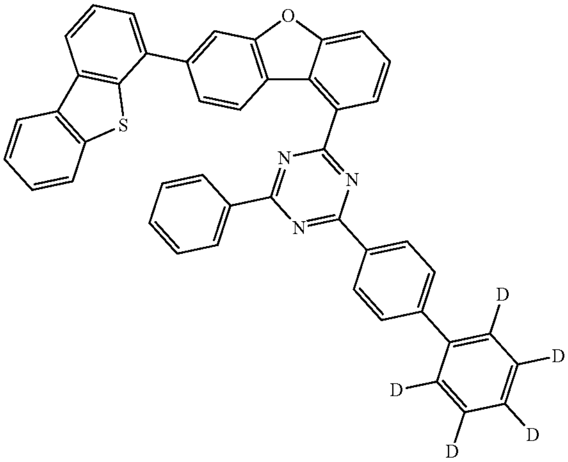
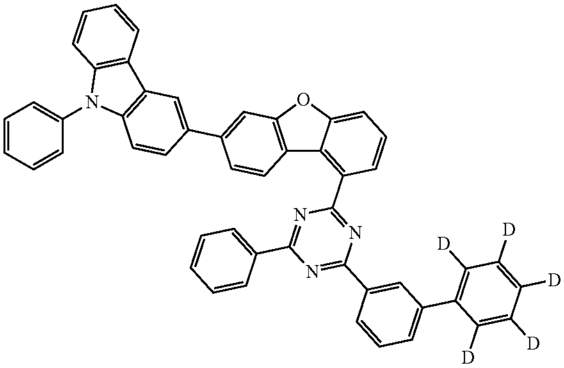
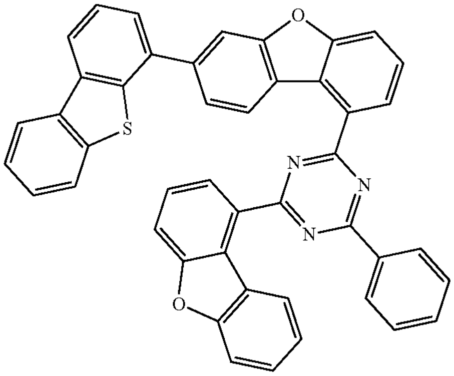
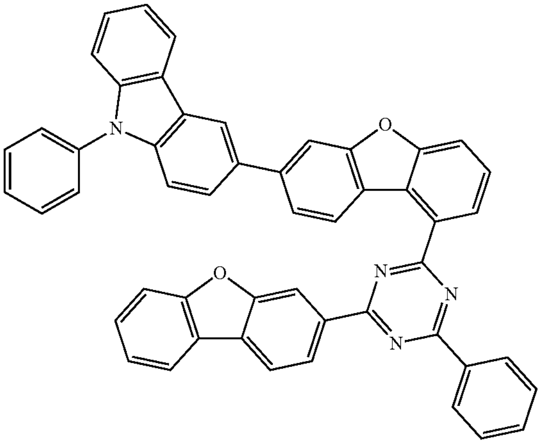

-continued
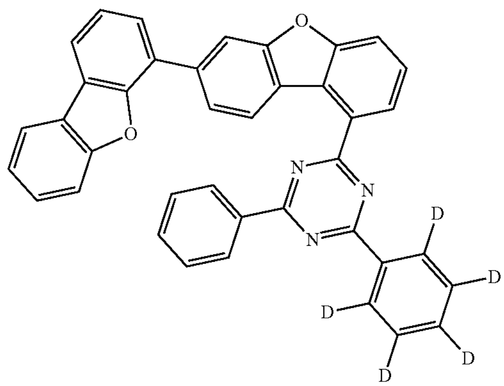
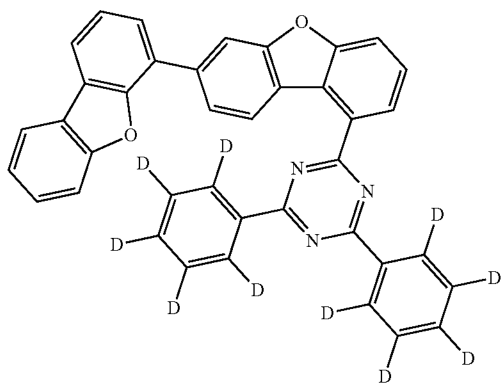
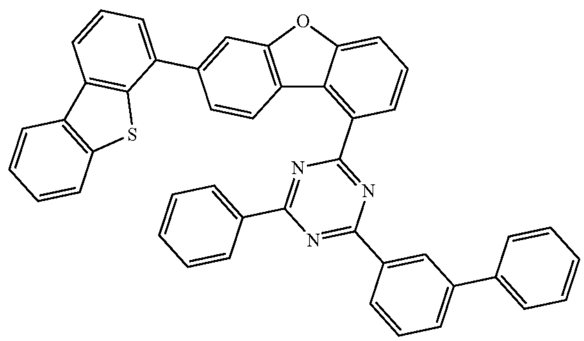
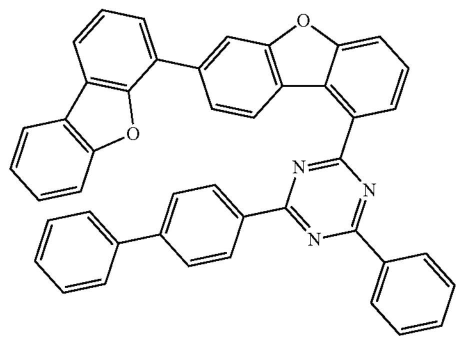
-continued
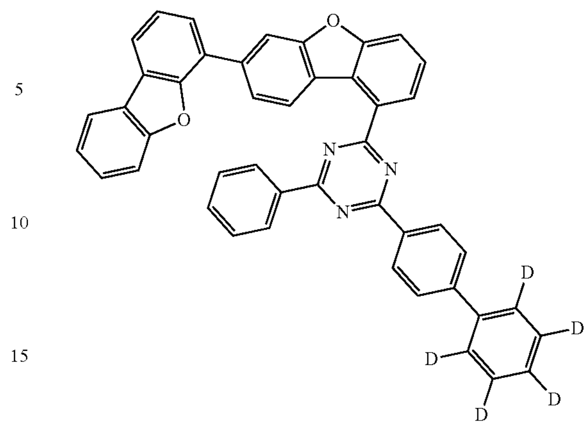
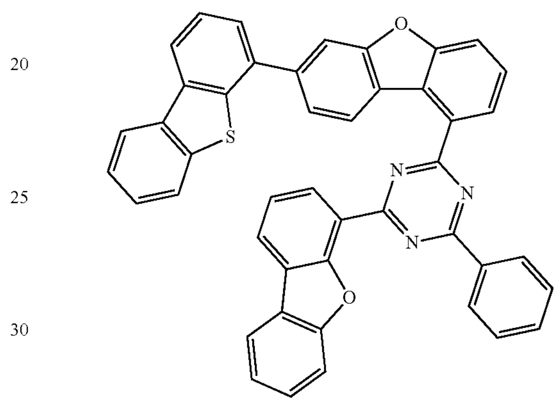
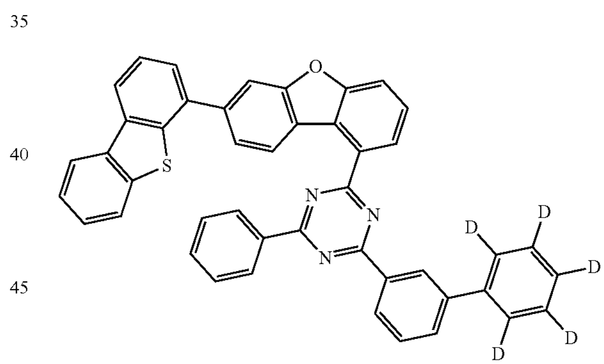
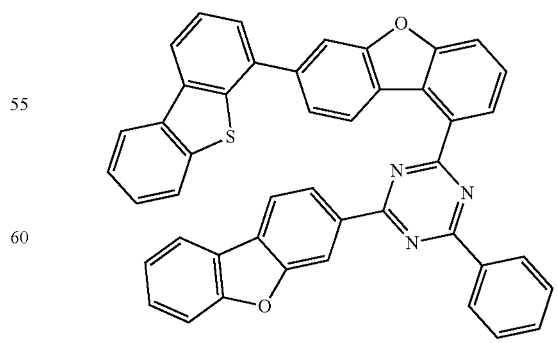

-continued
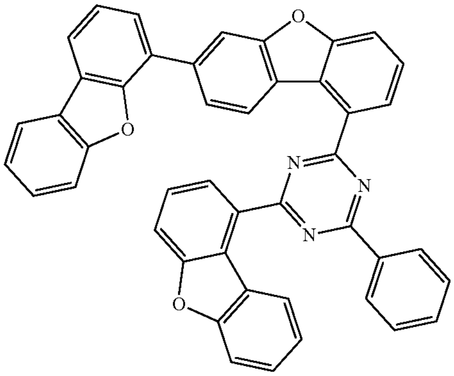
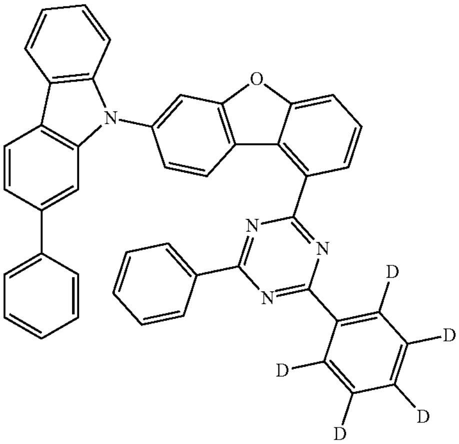
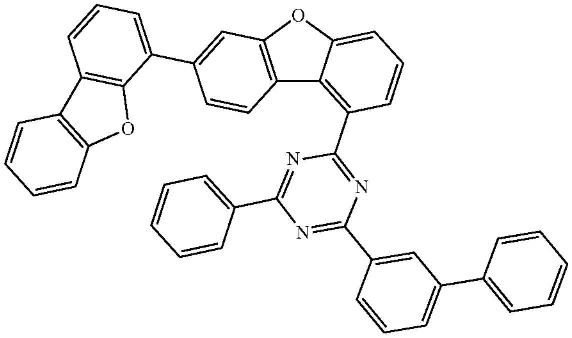
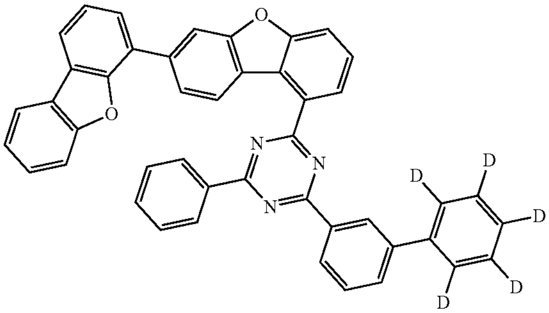
-continued
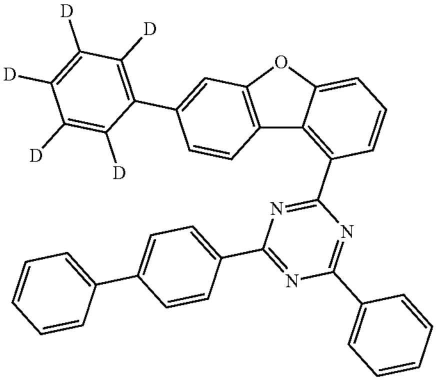
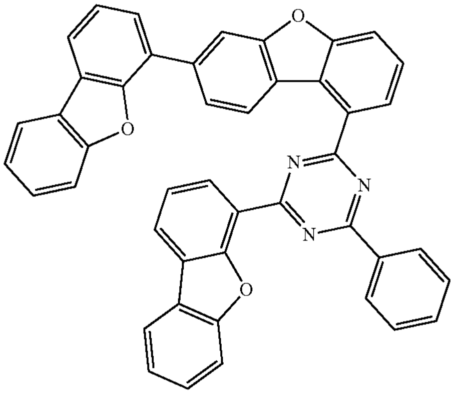
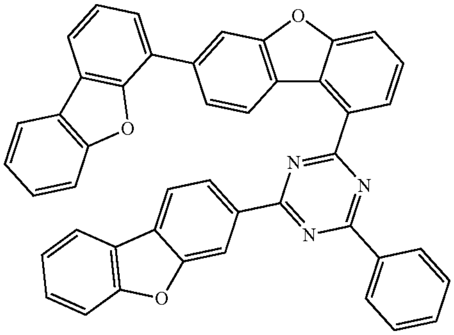
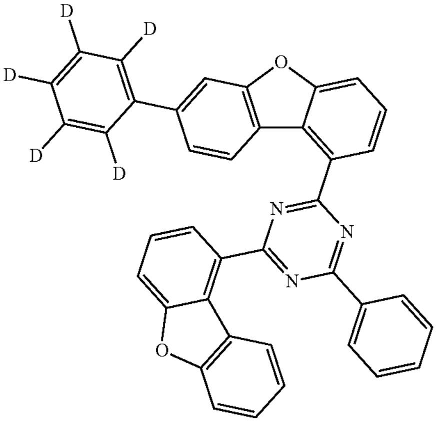

-continued
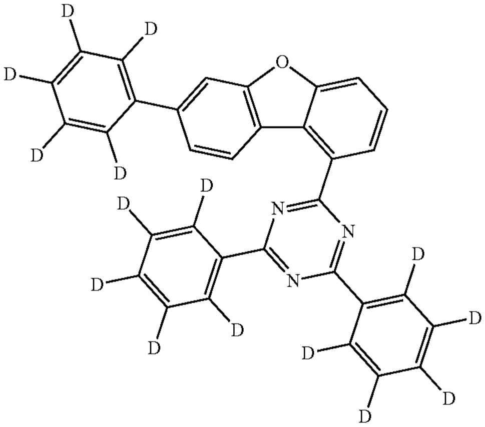
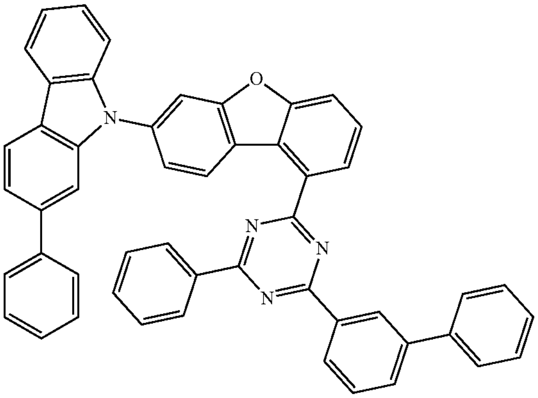
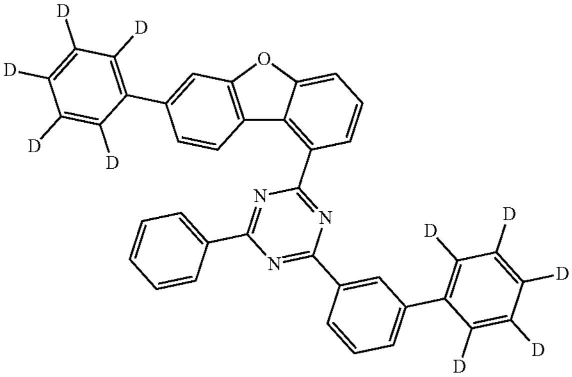
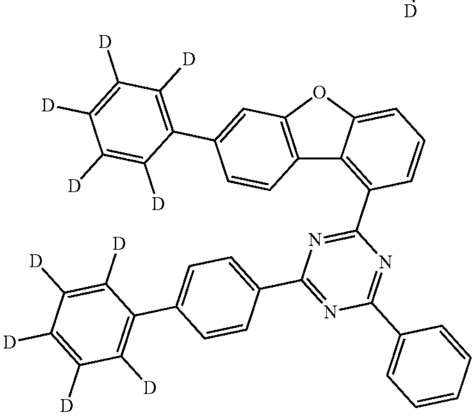
-continued
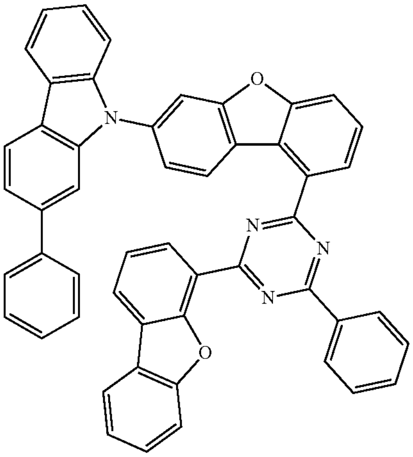
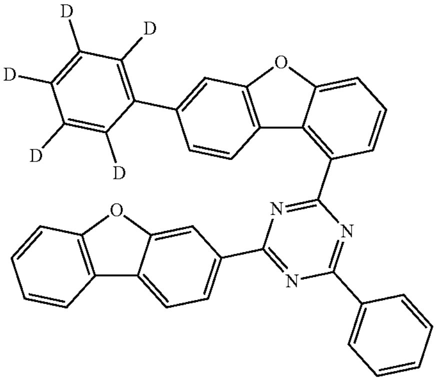
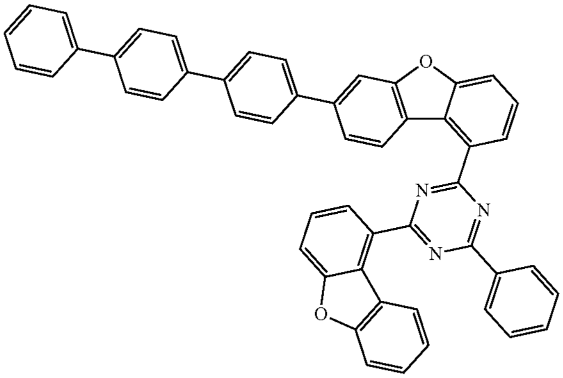
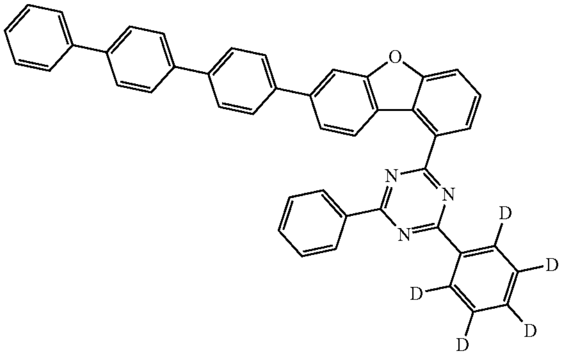 [SMILES: [2H]c1c([2H])c([2H])c(-c2nc(-c3ccccc3)nc(-c3cccc4oc5cc(-c6ccc(-c7ccc(-c8ccccc8)cc7)cc6)ccc5c34)n2)c([2H])c1[2H]]

-continued
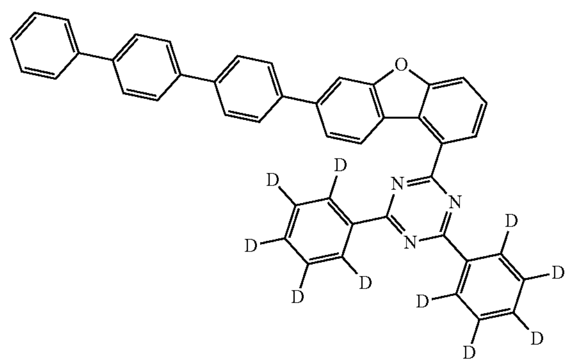
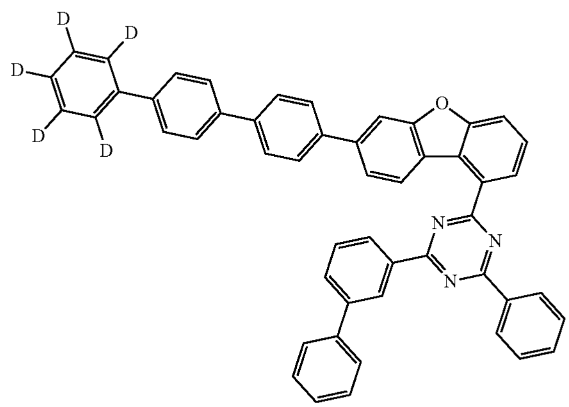
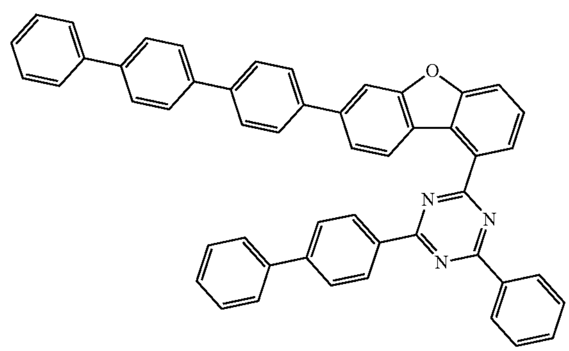
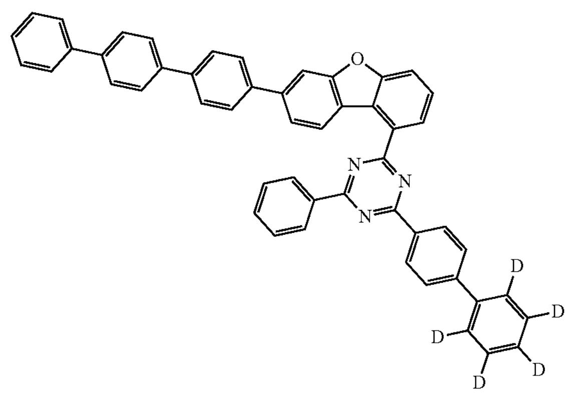
-continued
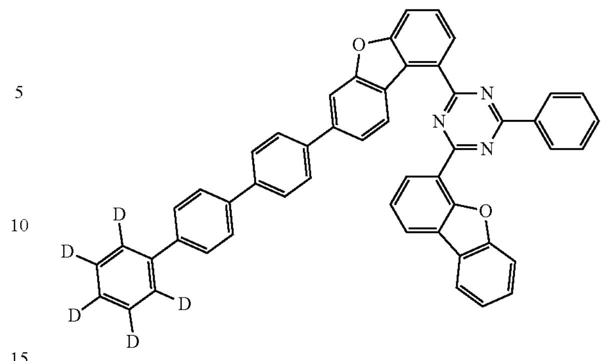
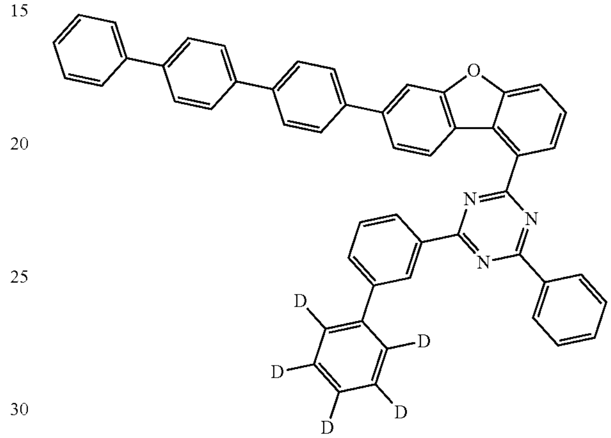
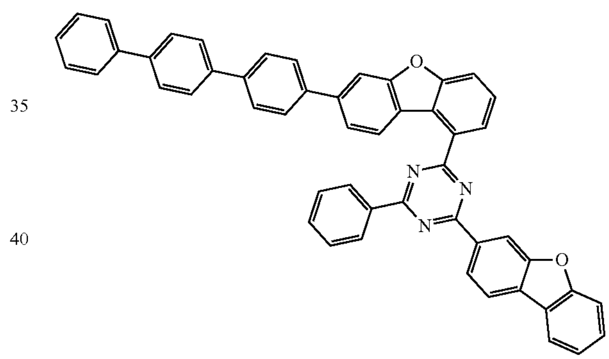
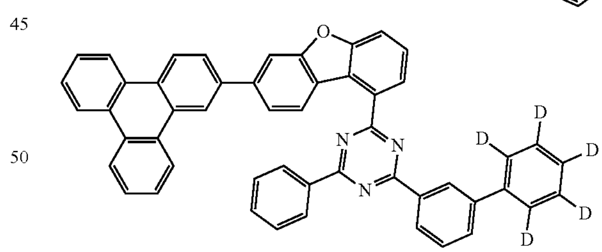
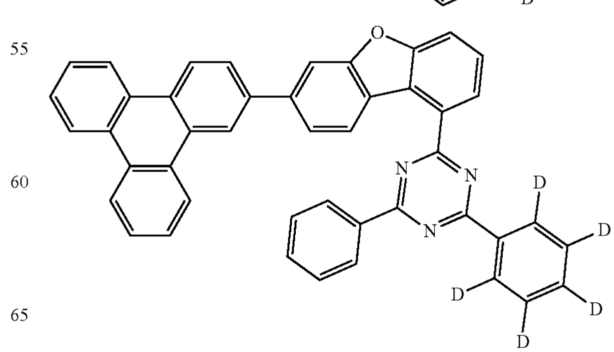

-continued
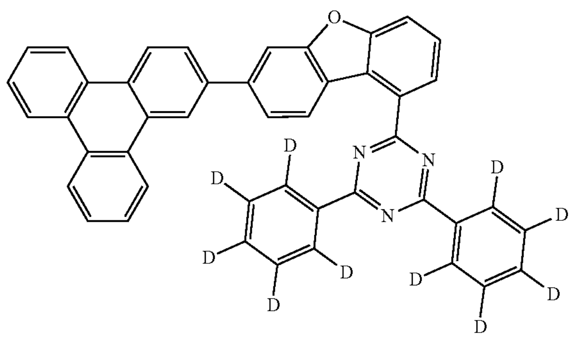
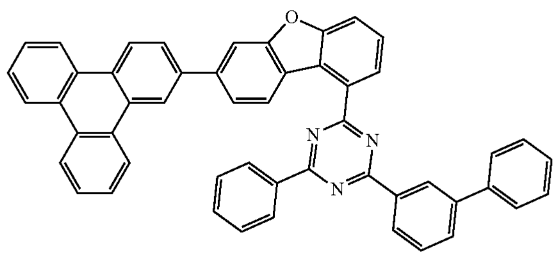
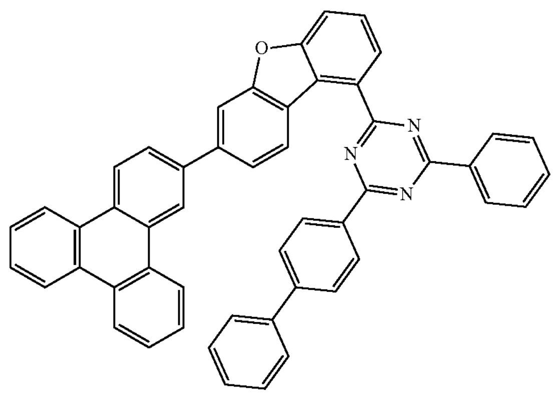
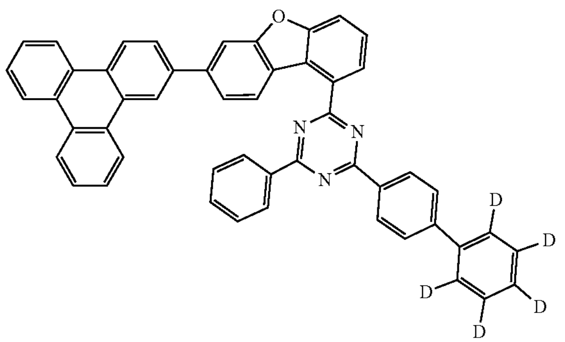
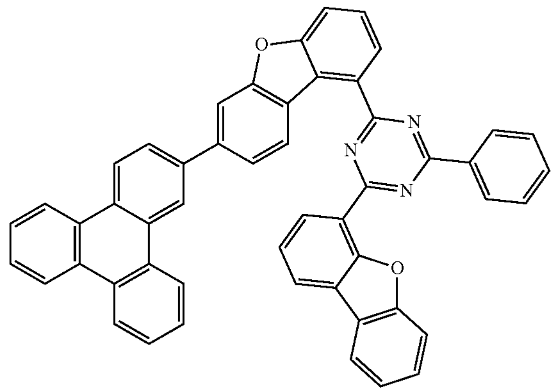
-continued
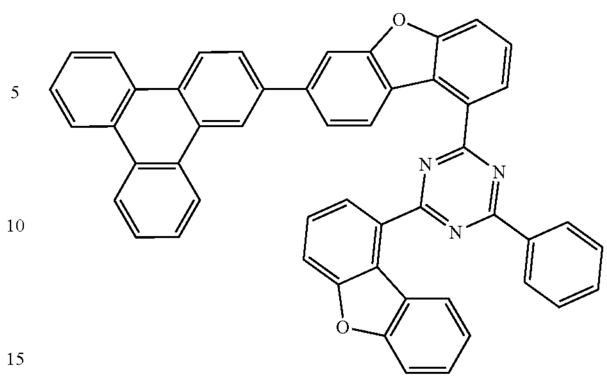
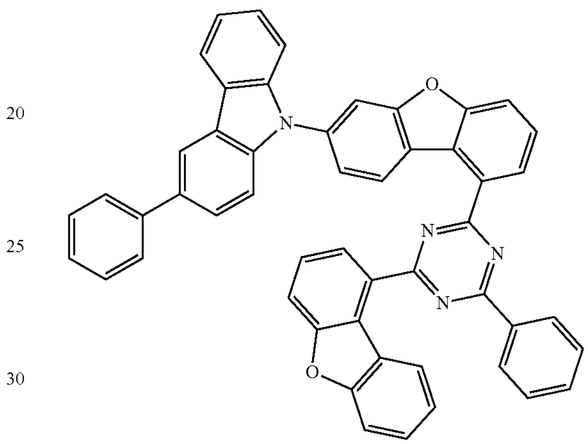
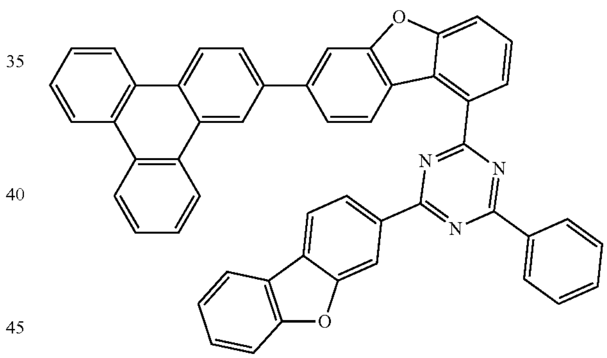
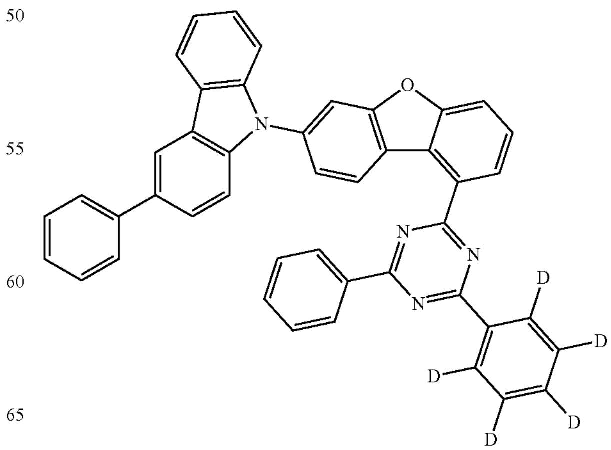

-continued
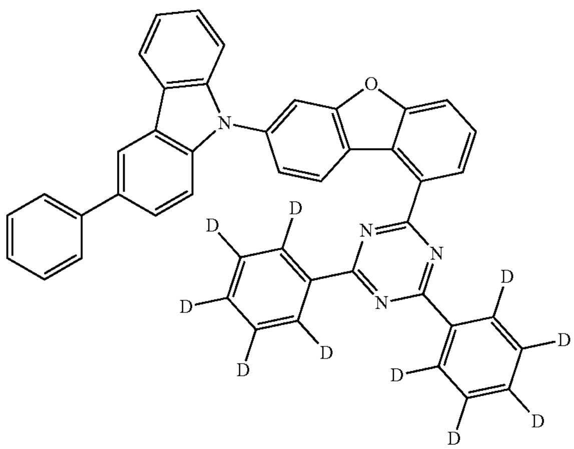
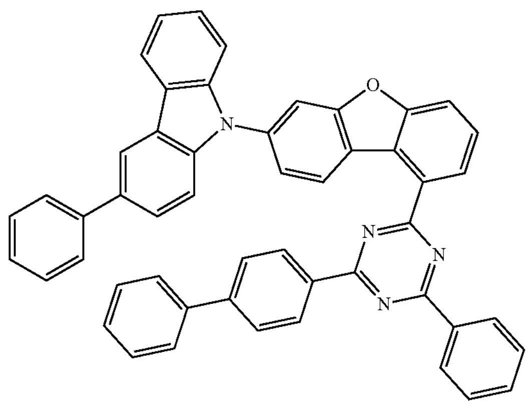
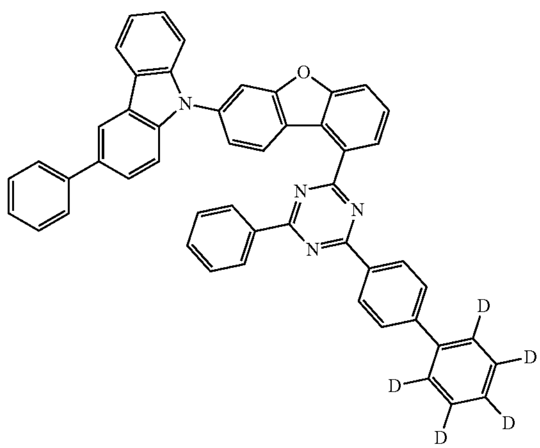
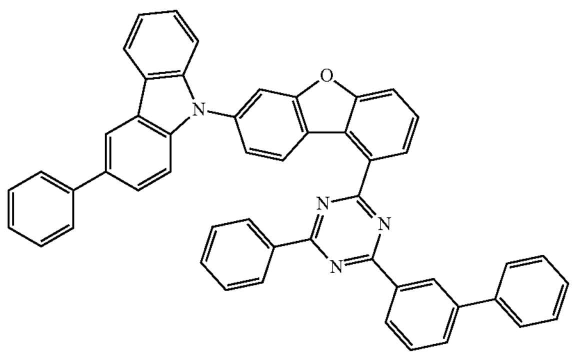
-continued
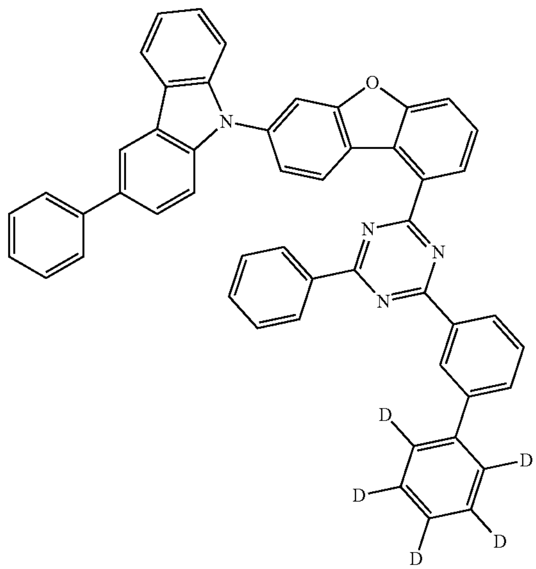
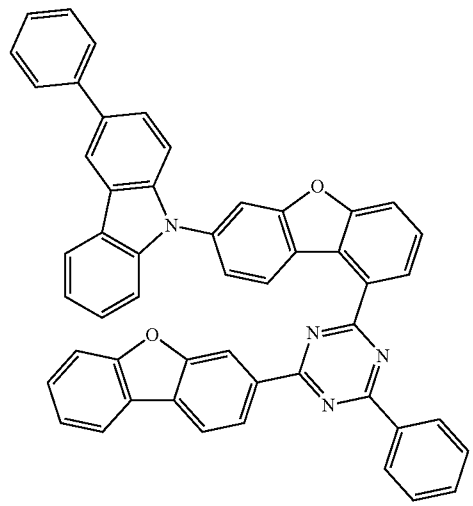
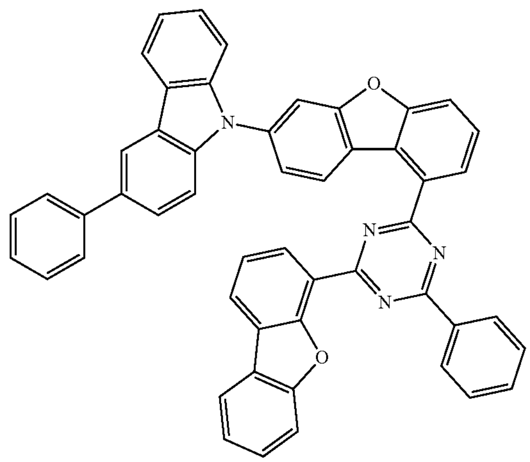

-continued
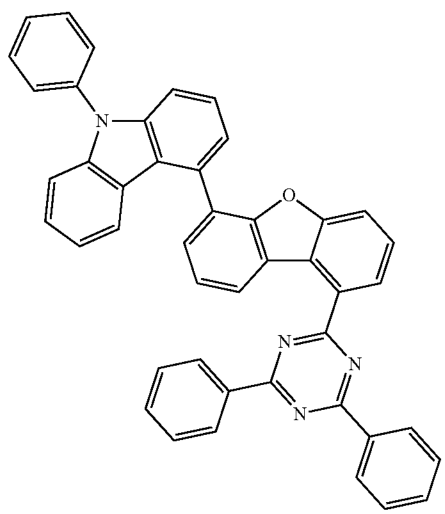
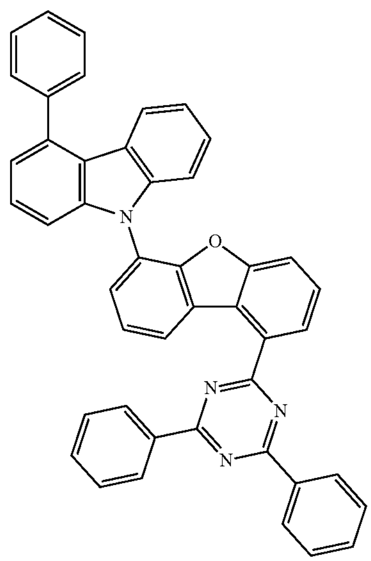
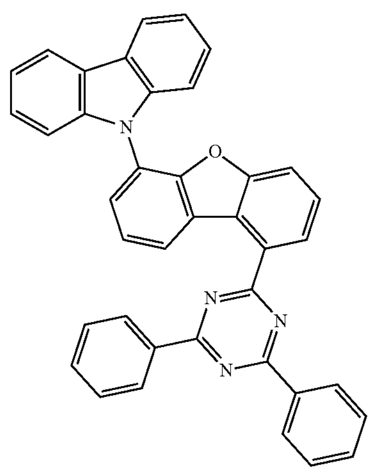
-continued
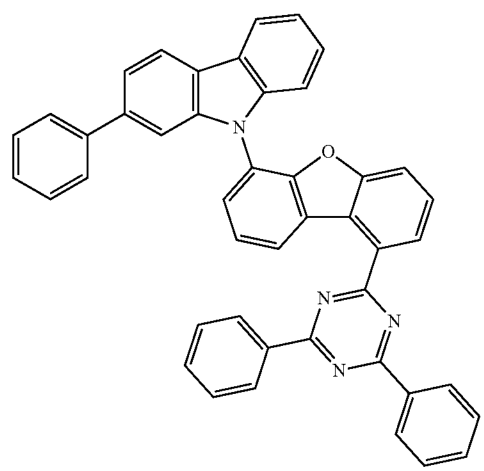
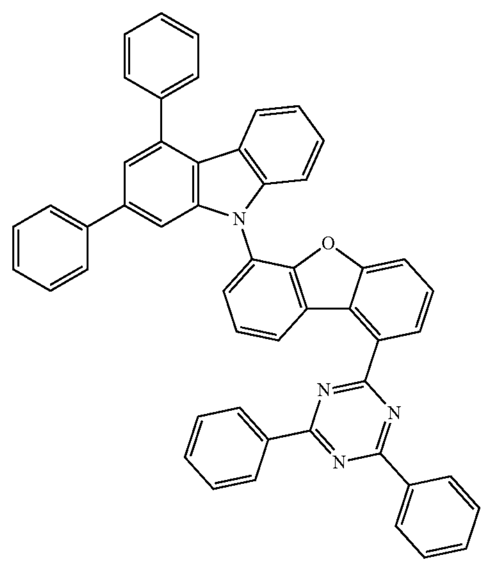
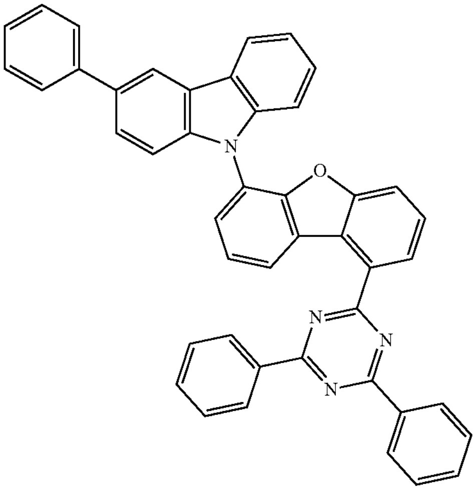

-continued
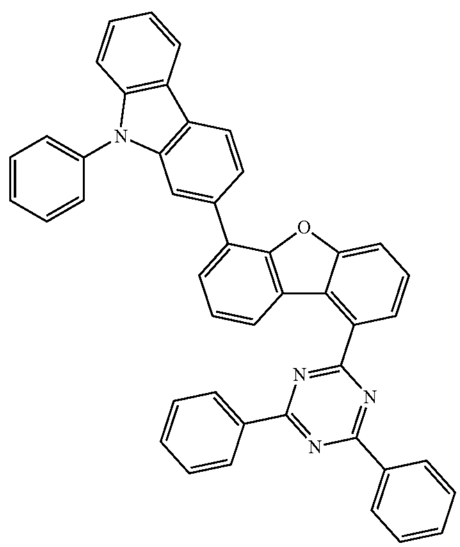
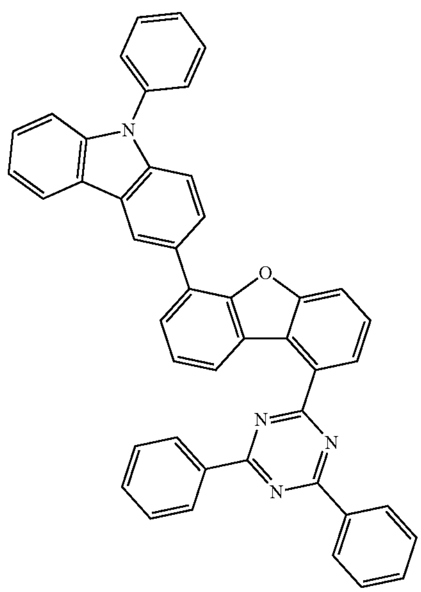
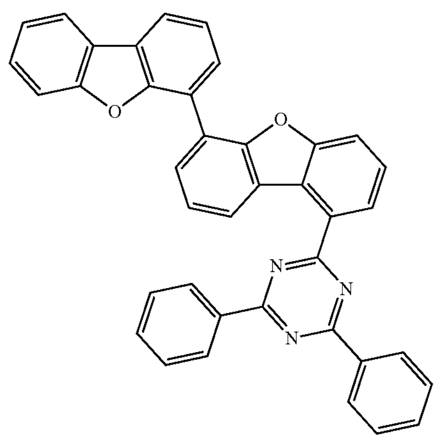
-continued
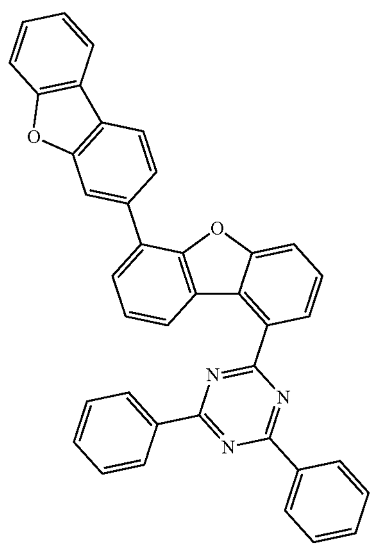
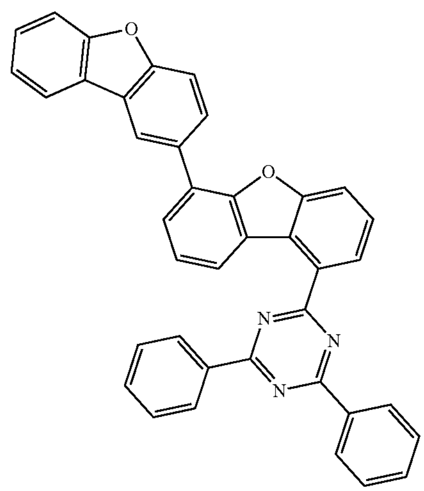
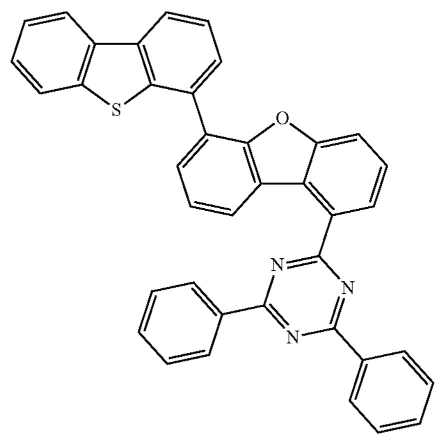

-continued
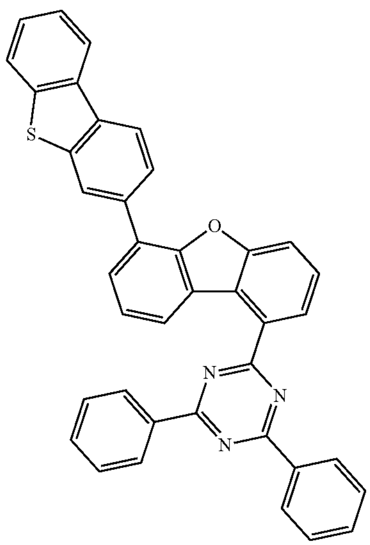
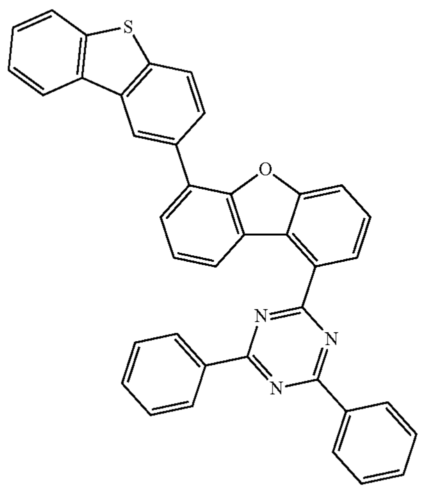
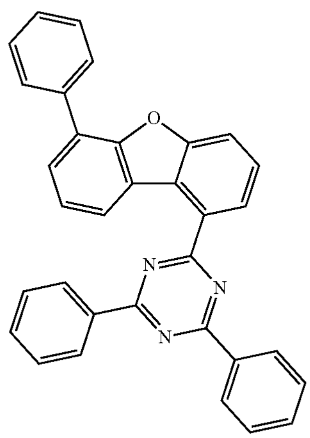
-continued
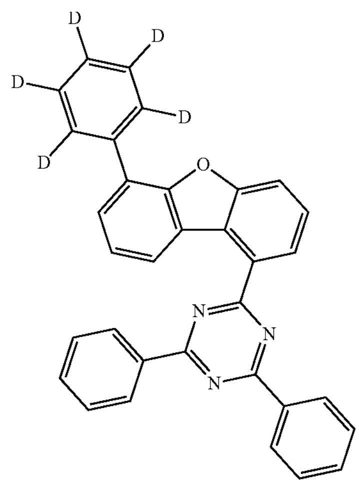
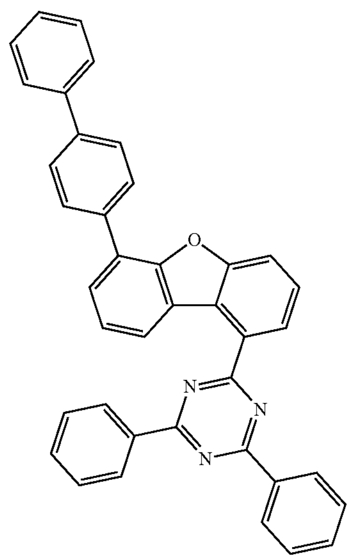 [SMILES: c1ccc(-c2ccc(-c3cccc4c3oc3cccc(-c5nc(-c6ccccc6)nc(-c6ccccc6)n5)c34)cc2)cc1]
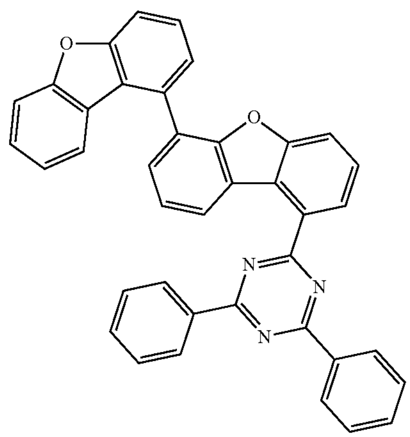

-continued
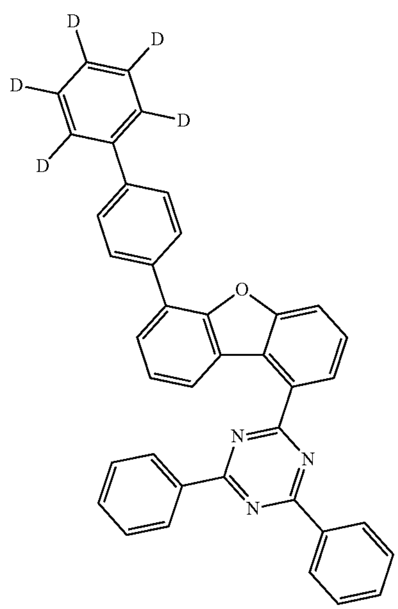
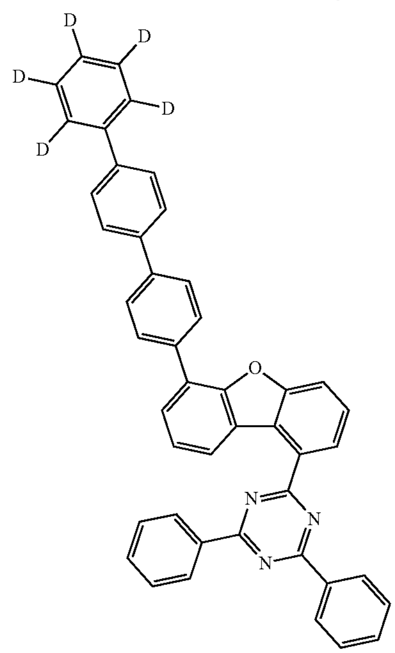
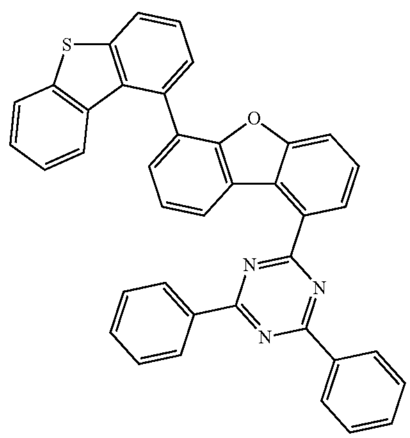
-continued
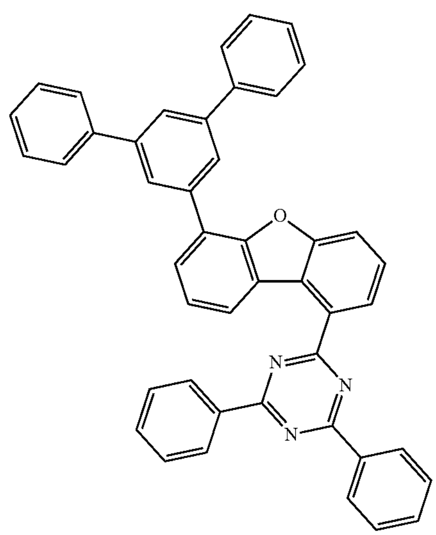
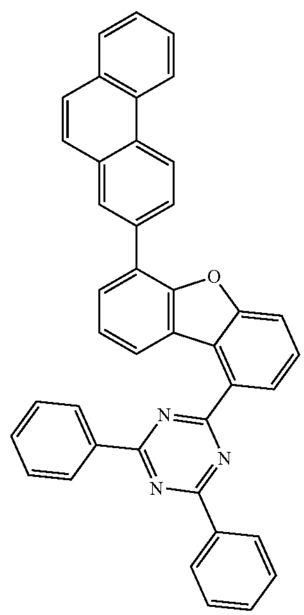
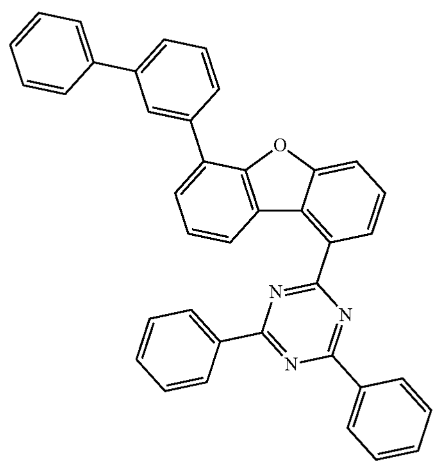

-continued
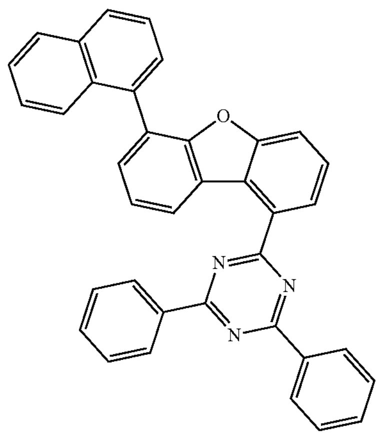
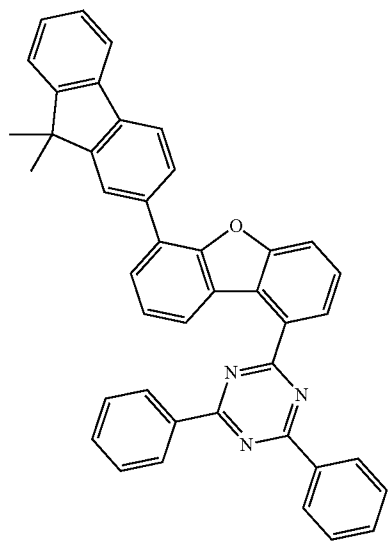
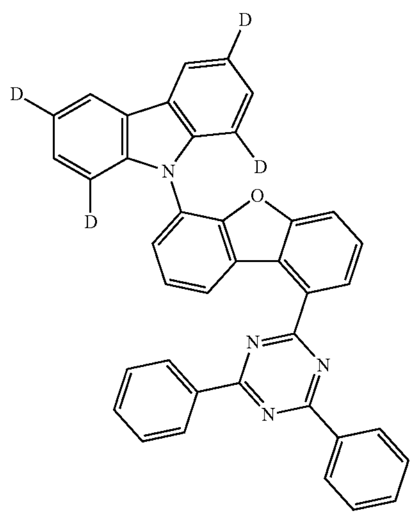
-continued
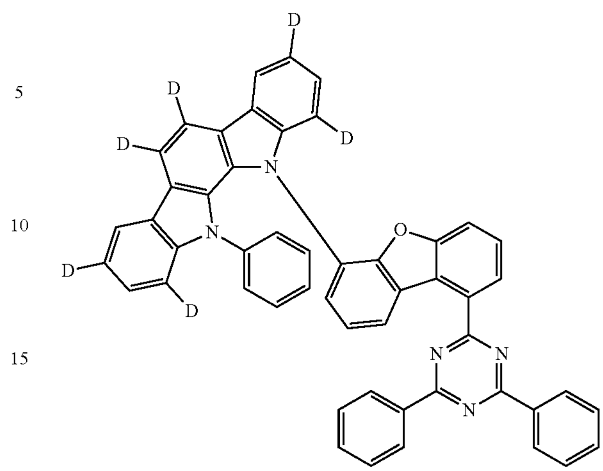
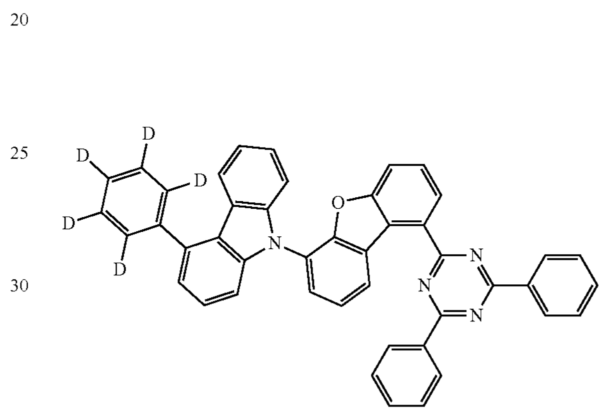
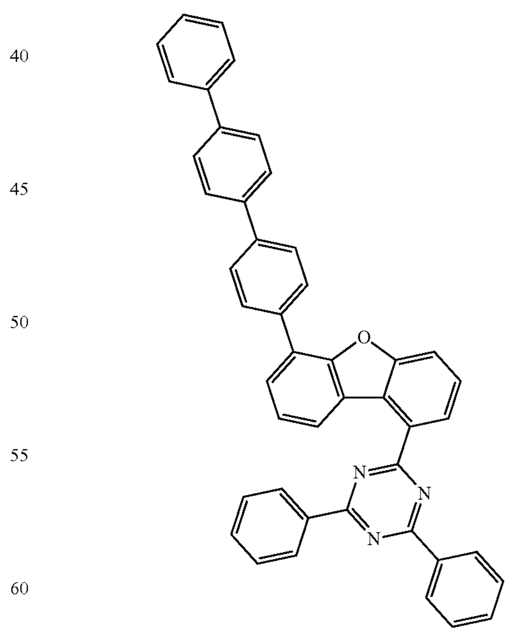

-continued
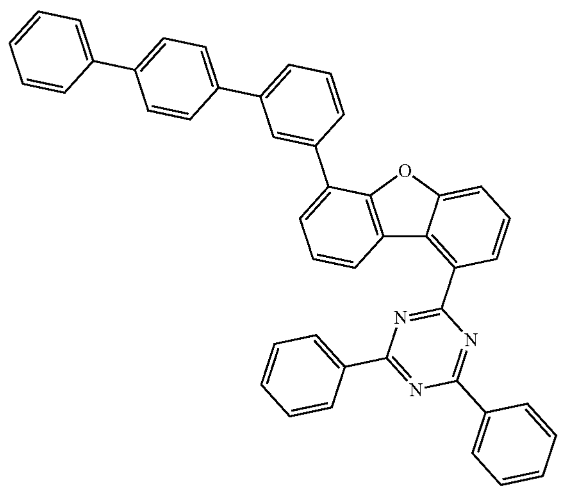
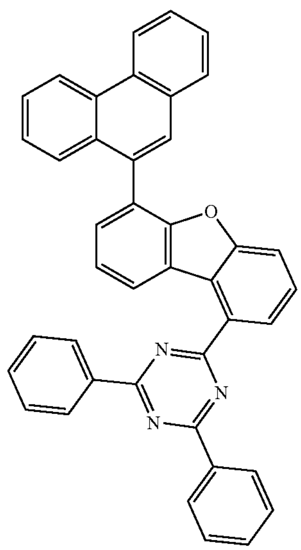
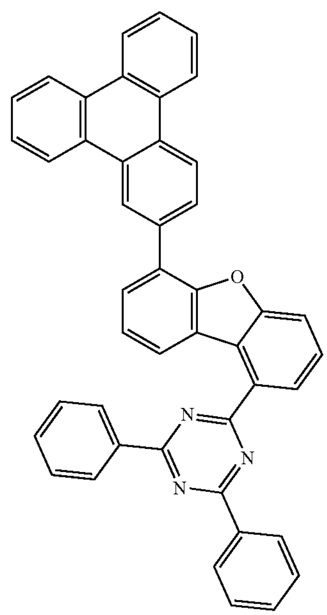
-continued
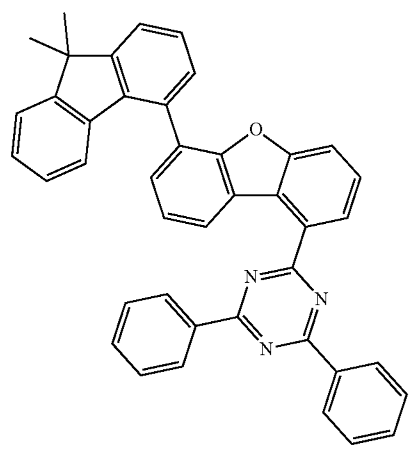
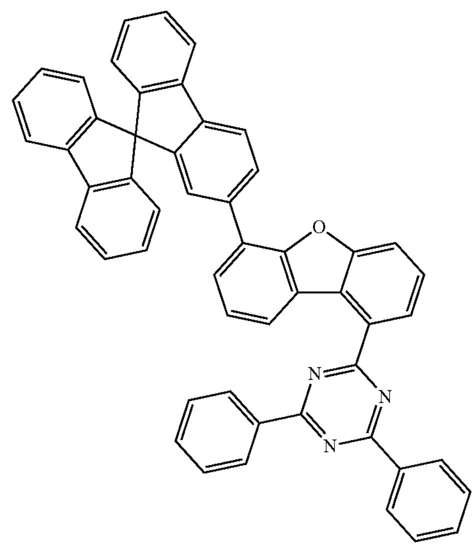
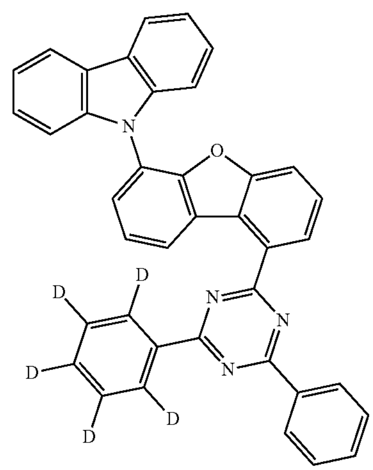

-continued
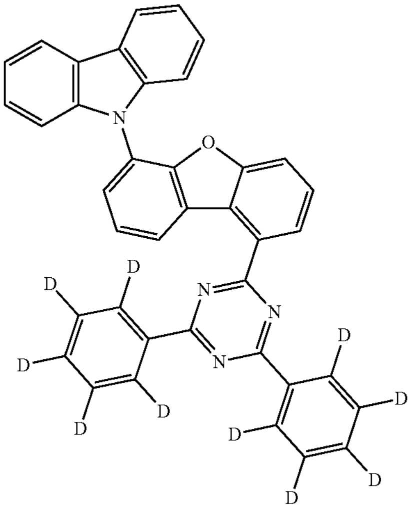
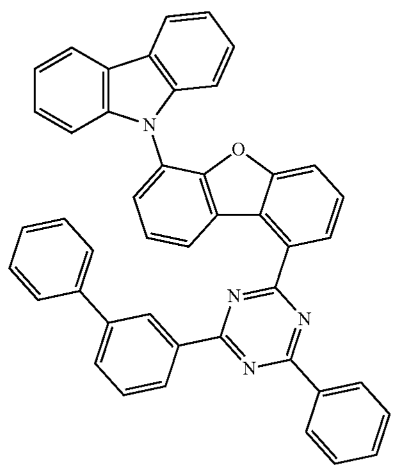
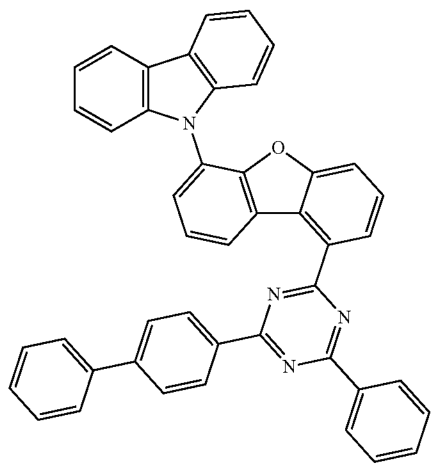
-continued
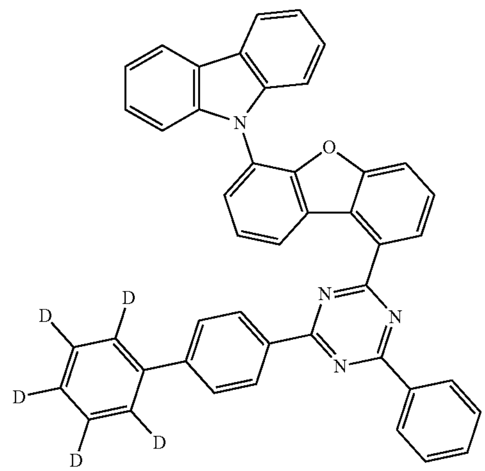
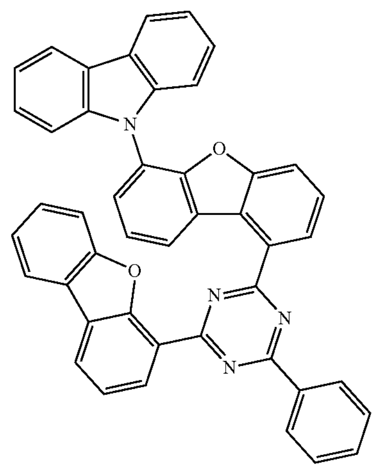
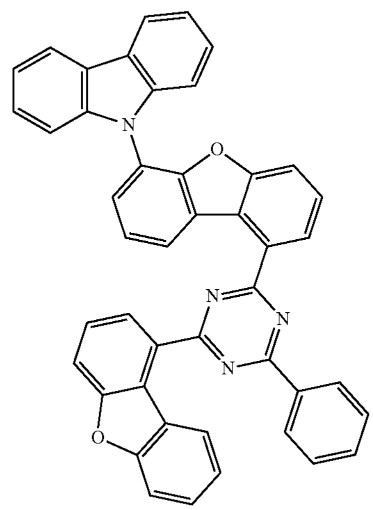

-continued
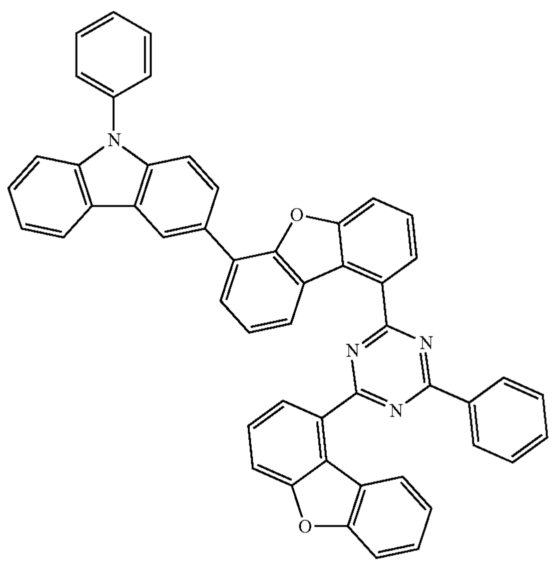
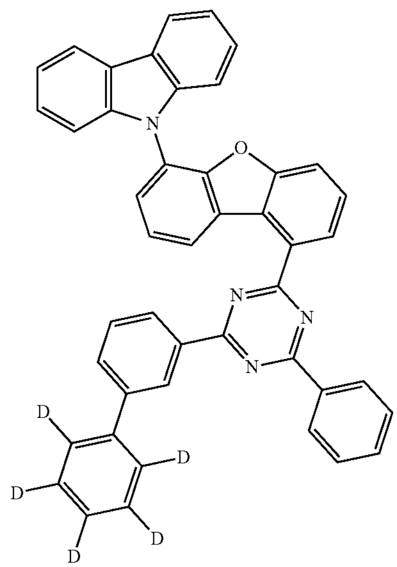
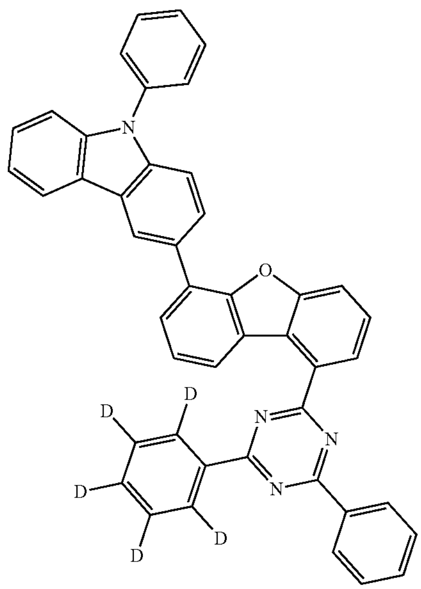
-continued
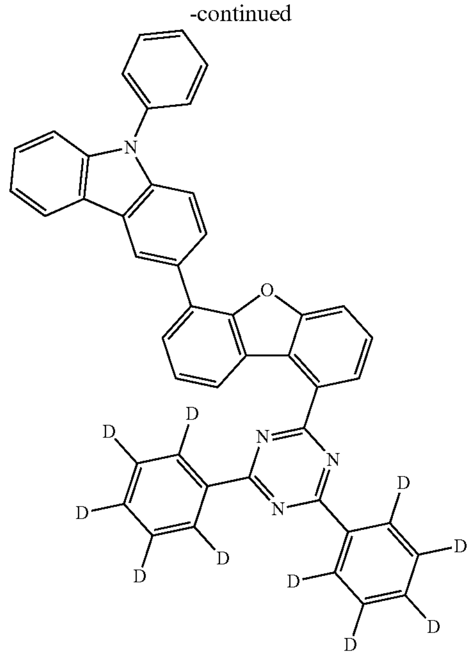
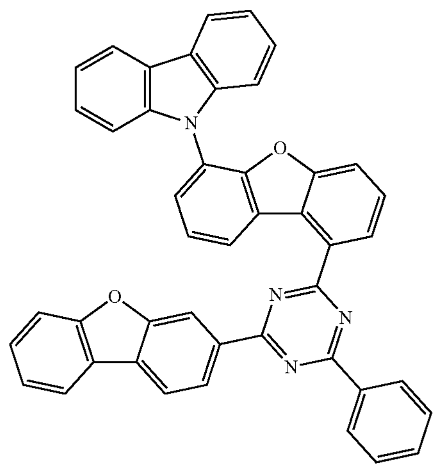
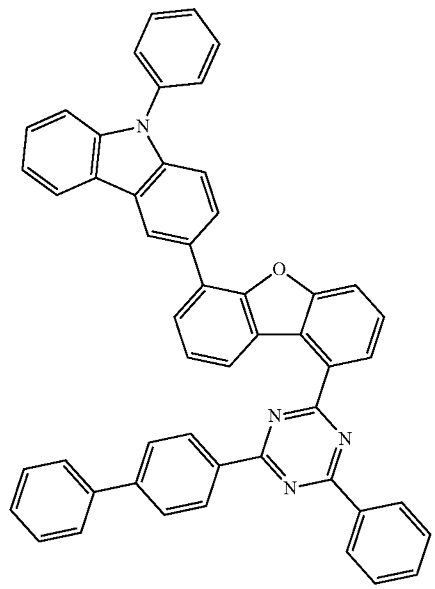

-continued
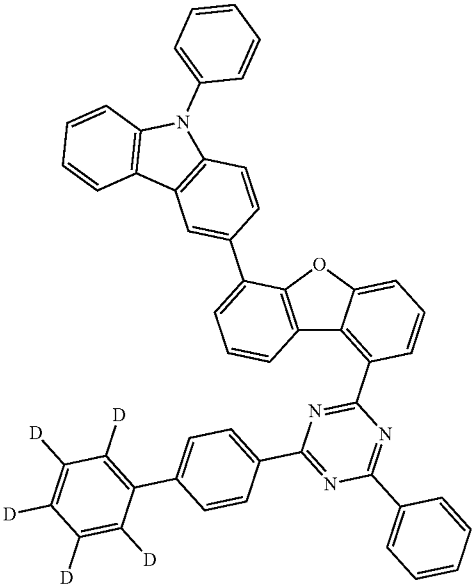
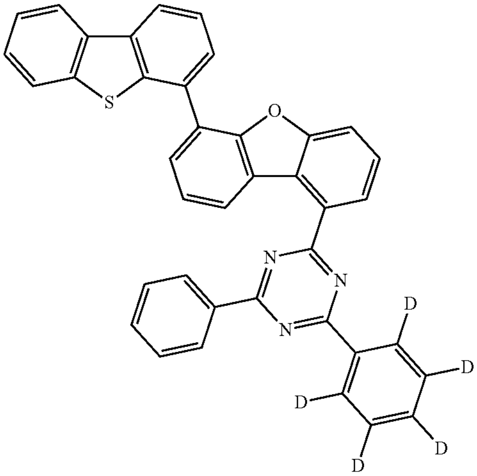
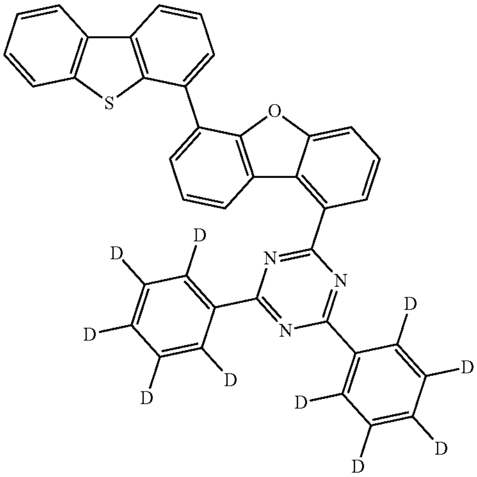
-continued
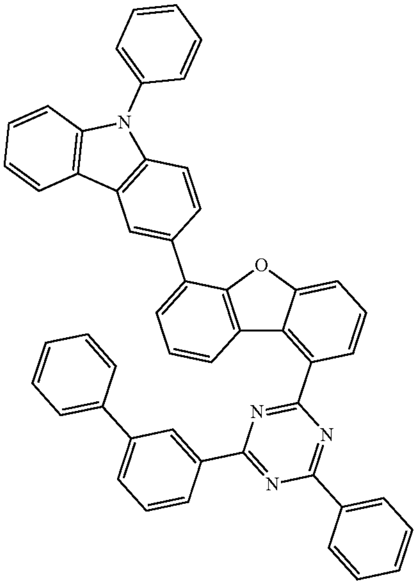
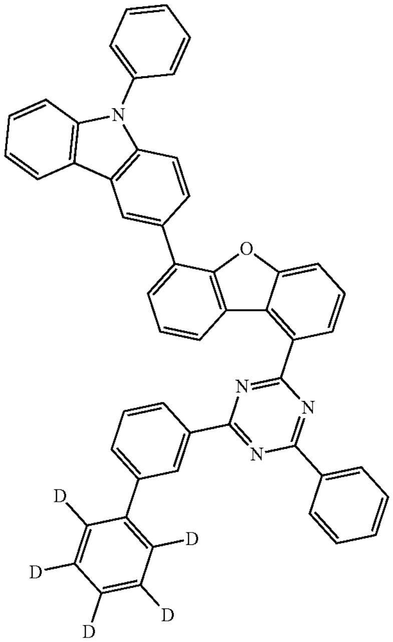
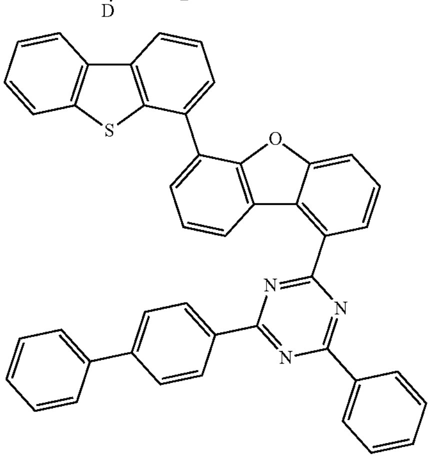

-continued
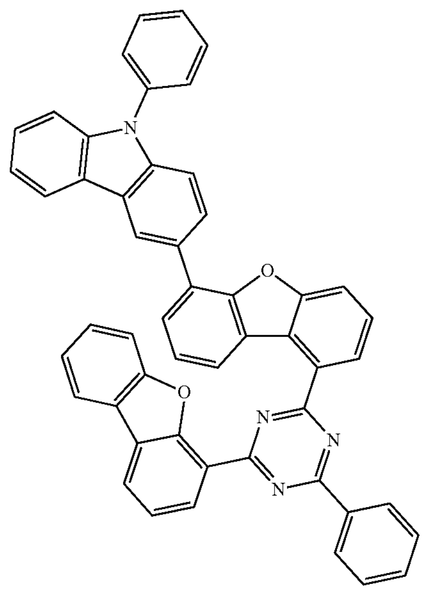
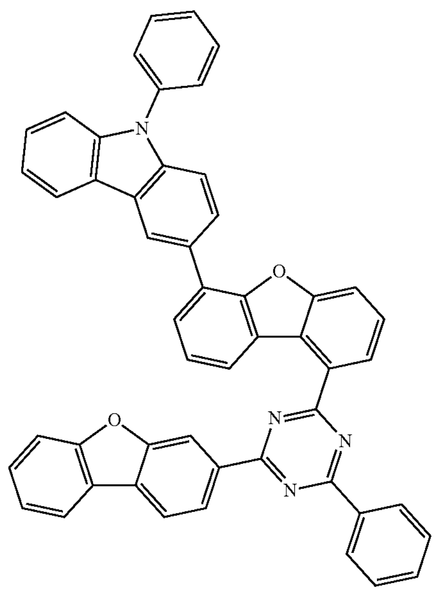
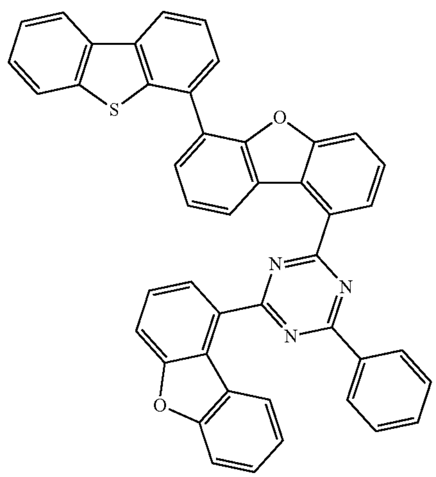
-continued
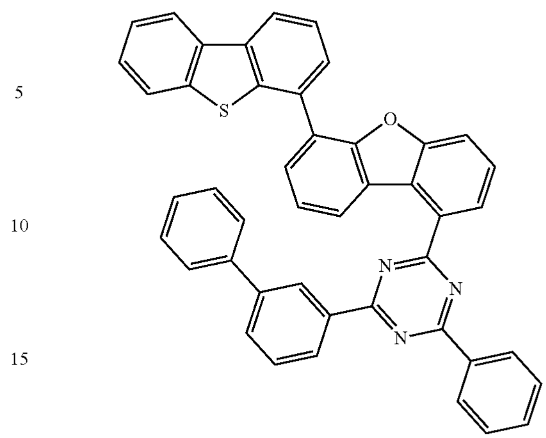
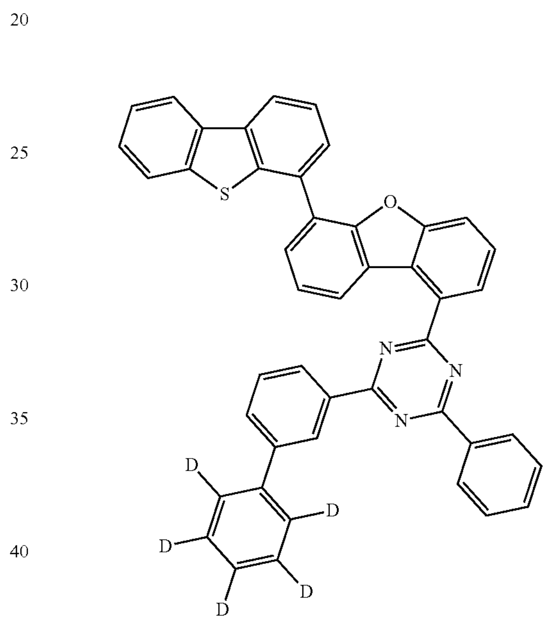
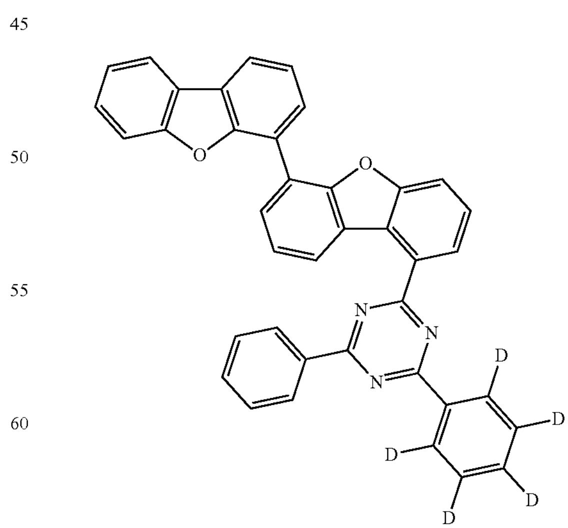

-continued
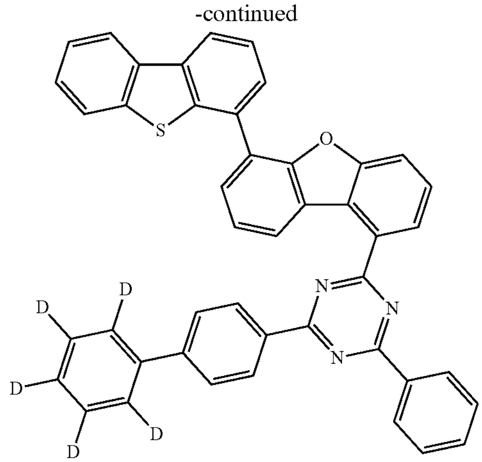
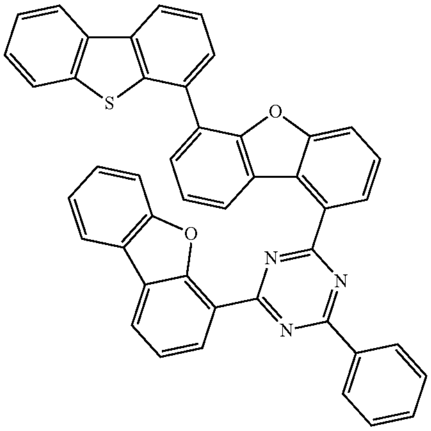
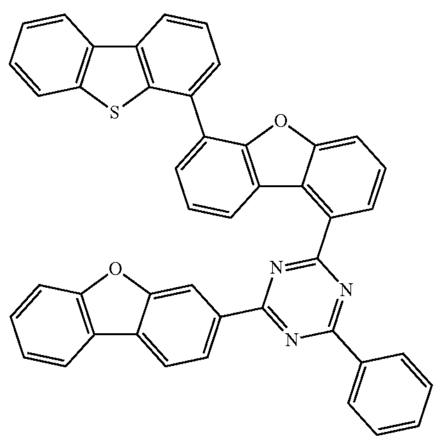
-continued
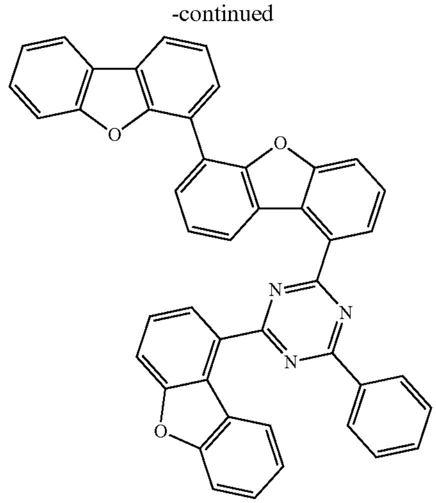
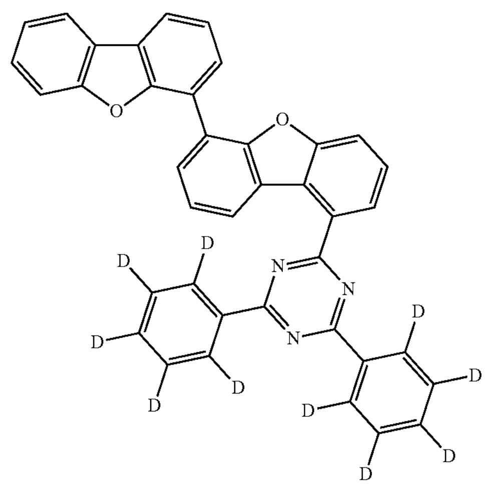
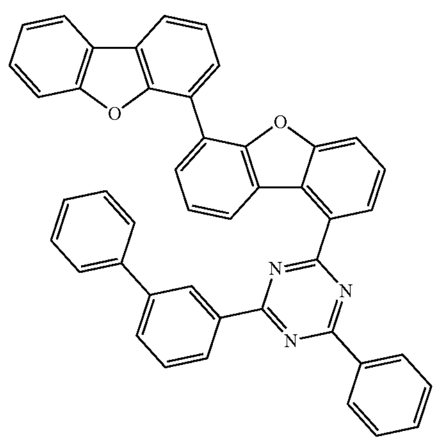

-continued
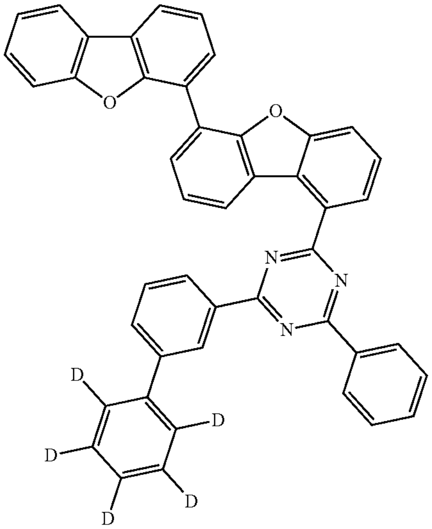
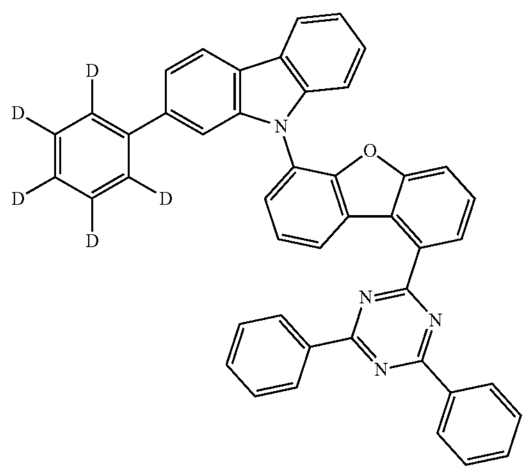
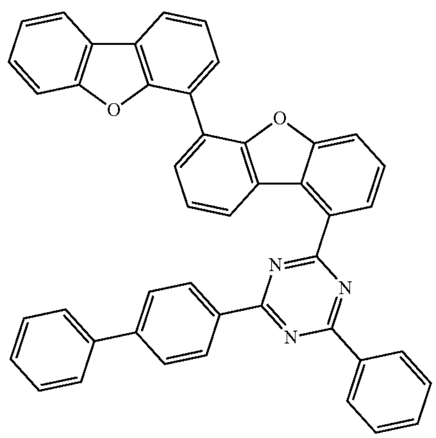
-continued
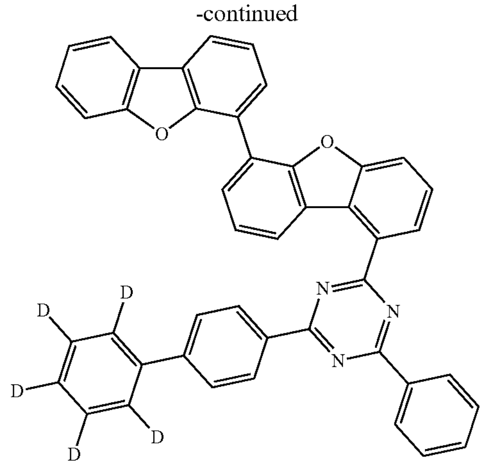
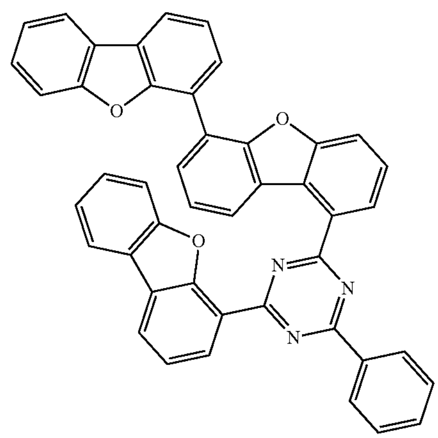
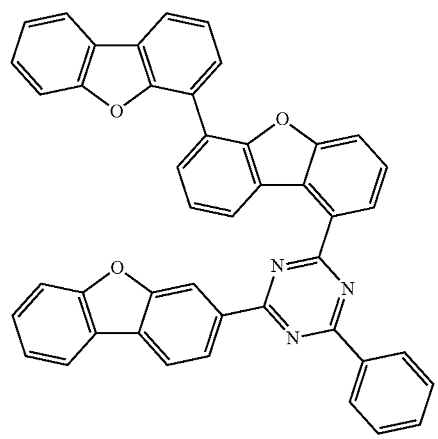

-continued
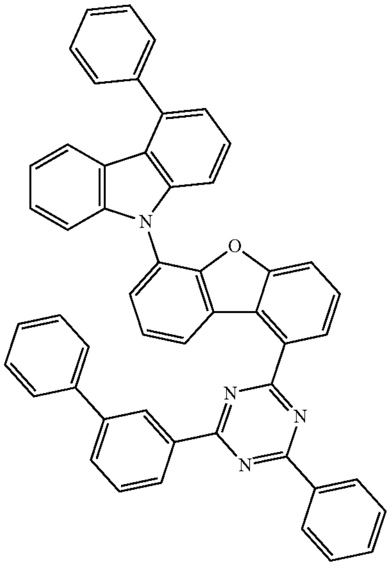
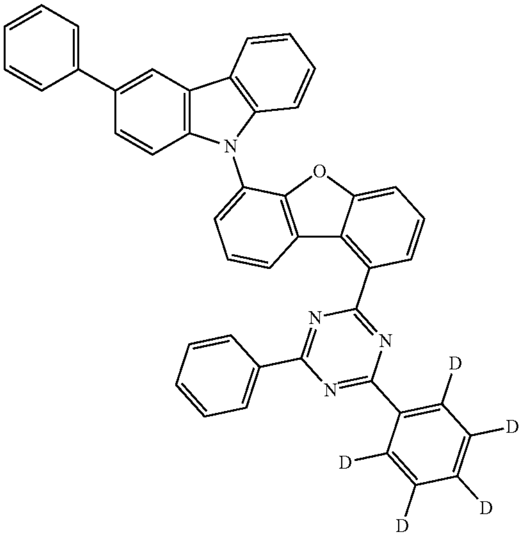
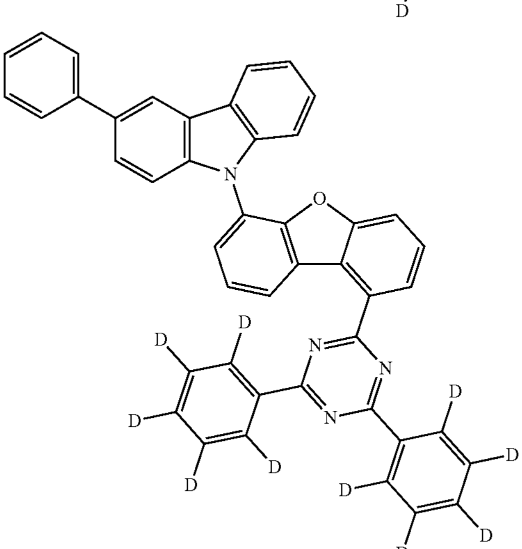
-continued
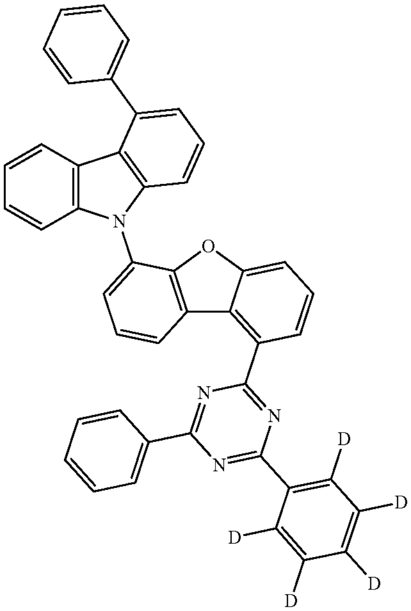
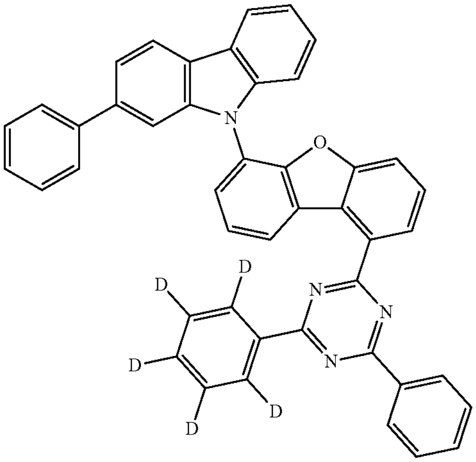
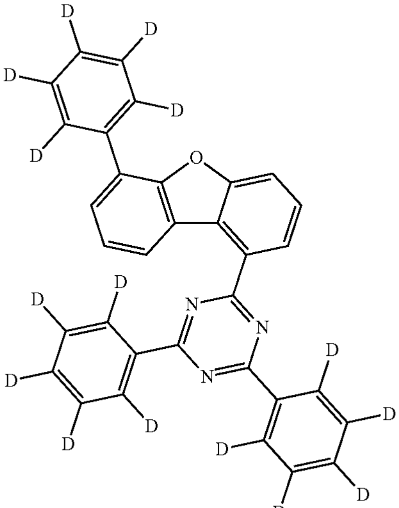

-continued
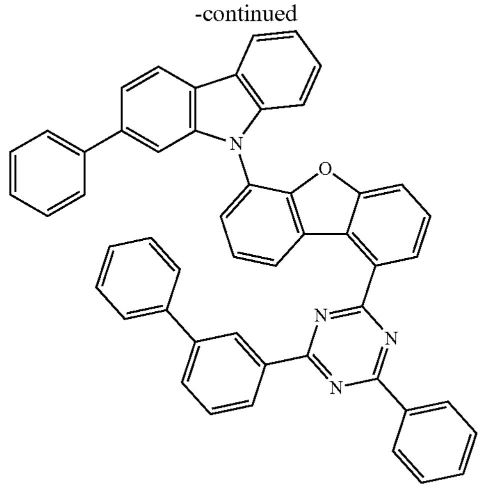
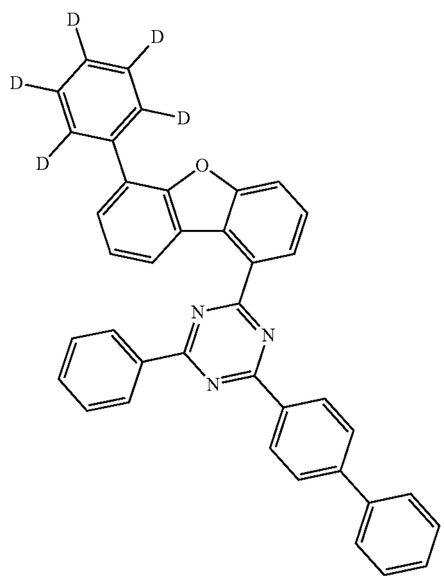
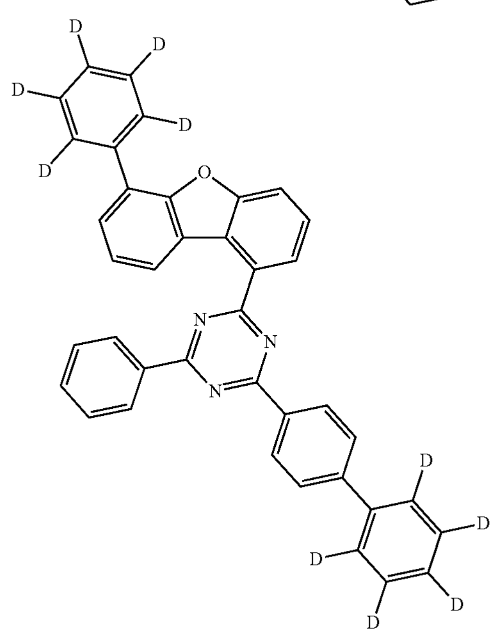
-continued
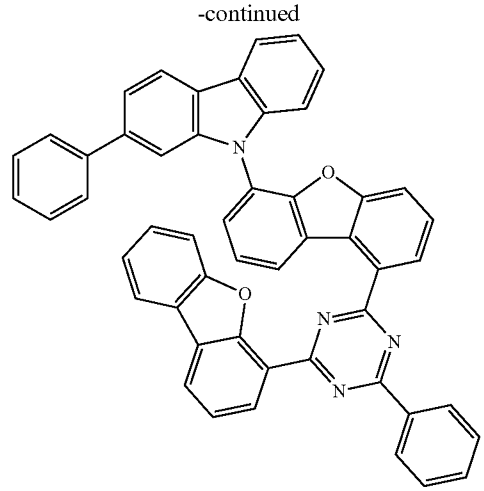
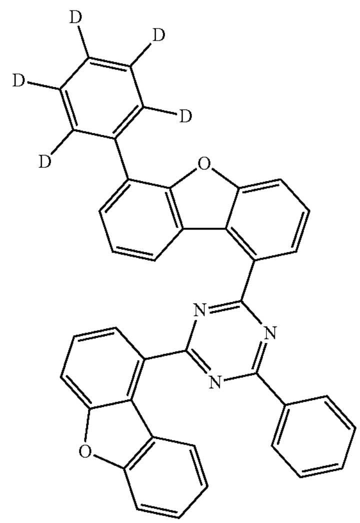
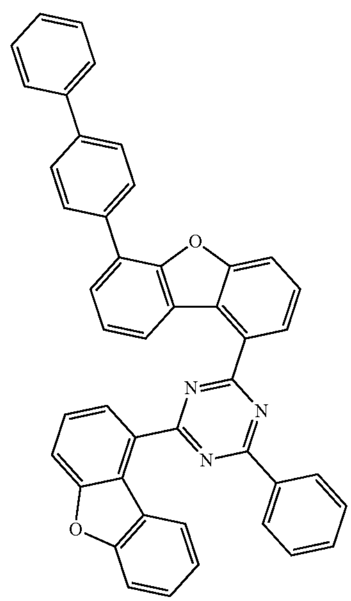

-continued
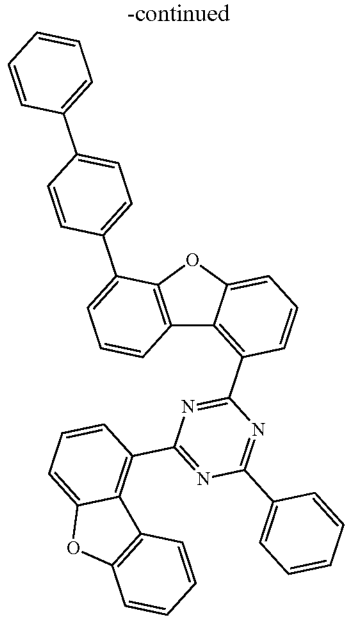
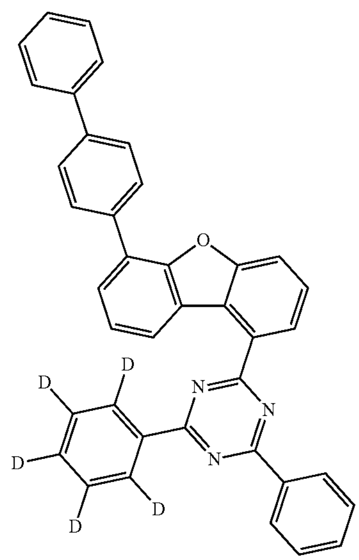
-continued
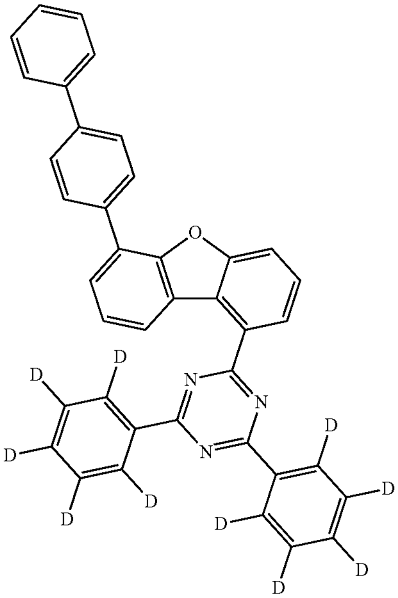
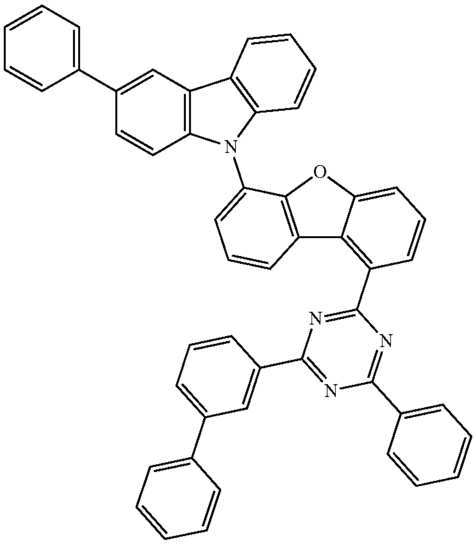
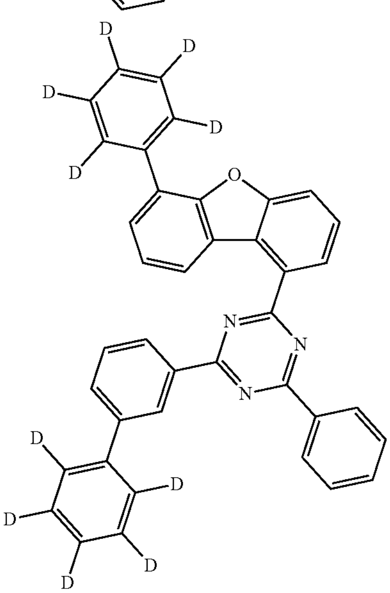

-continued
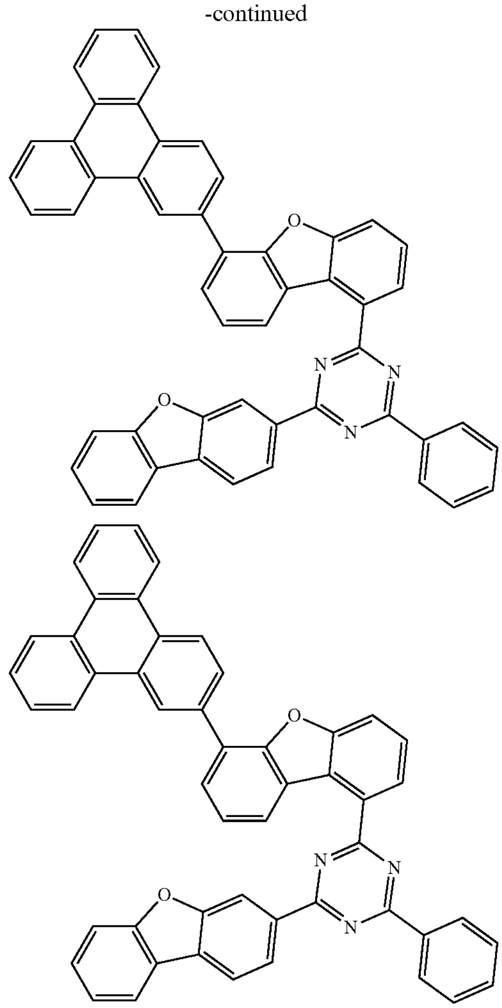
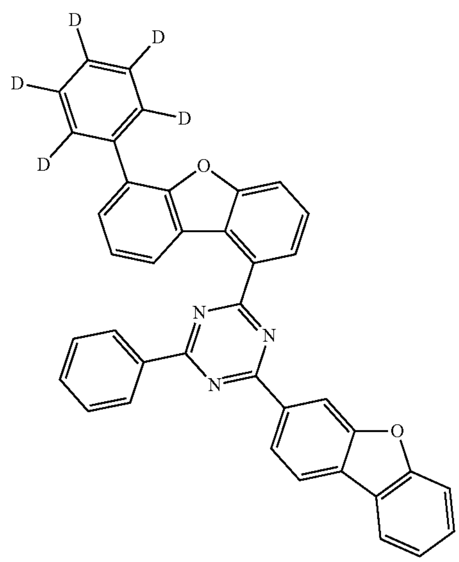
-continued
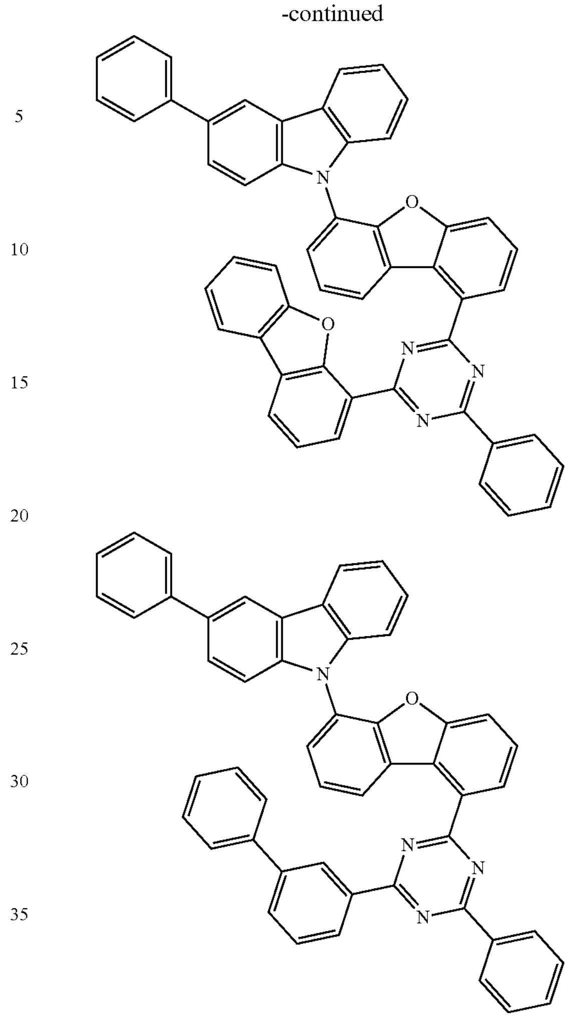
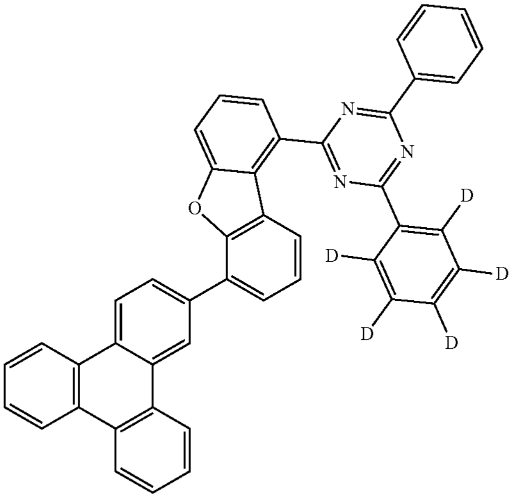

-continued
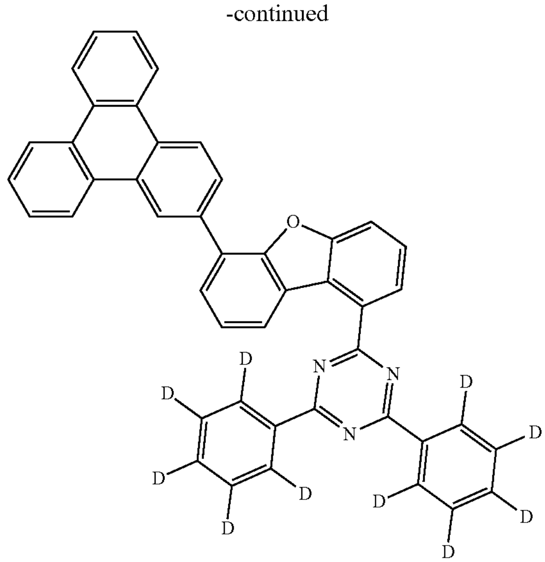
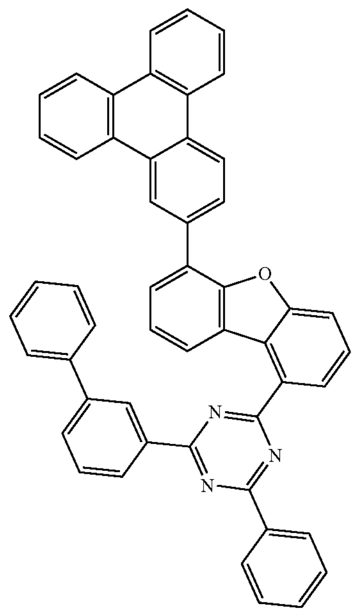
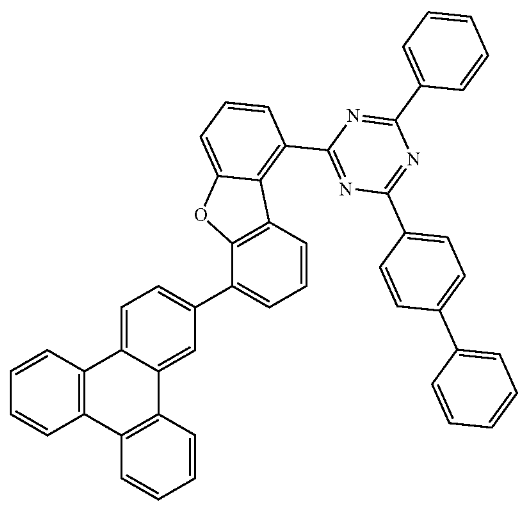
-continued
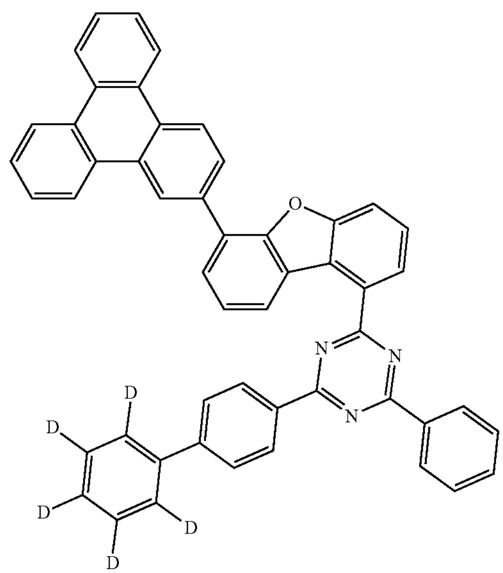
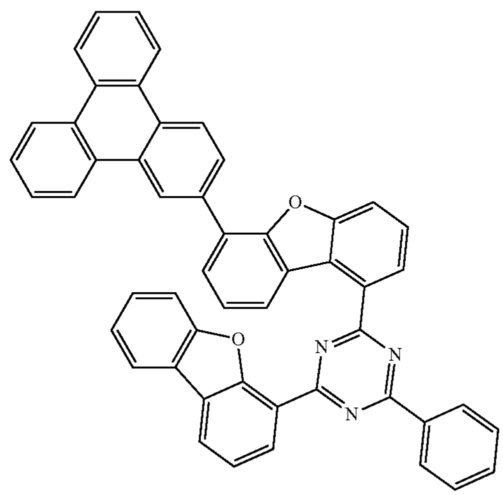
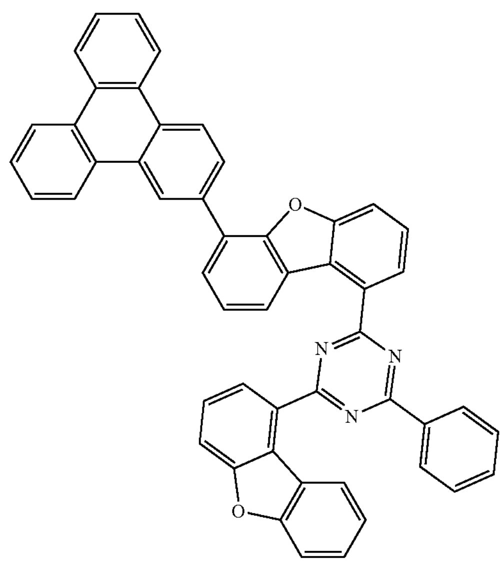

-continued
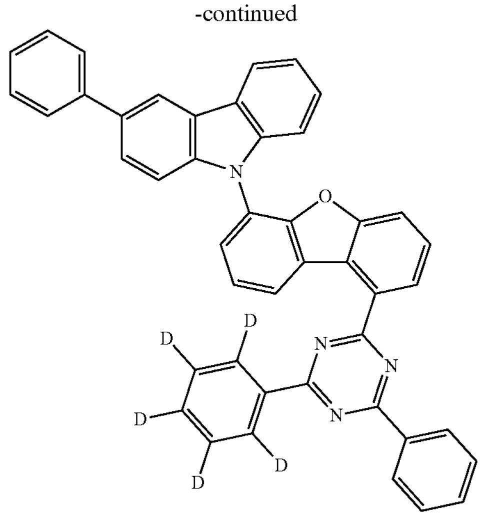
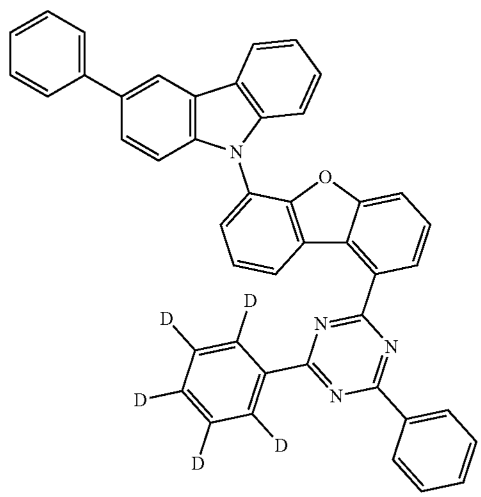
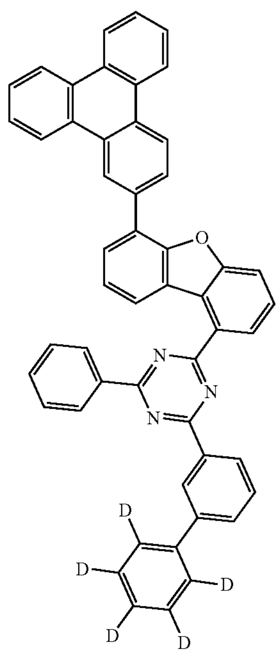
-continued
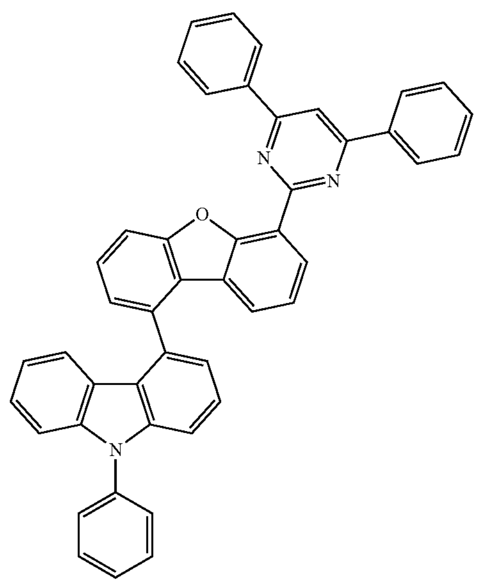
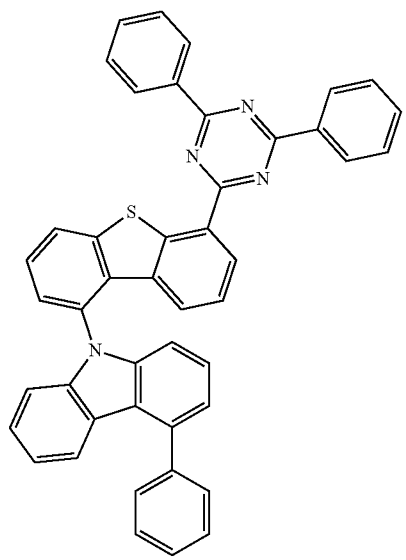
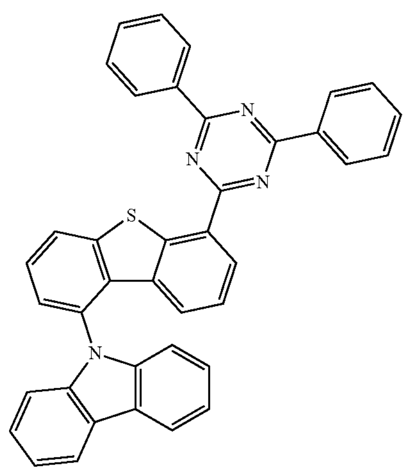

-continued
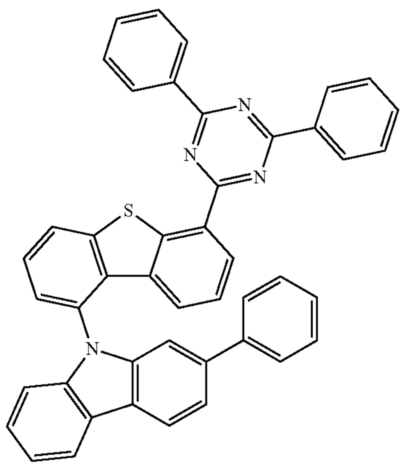
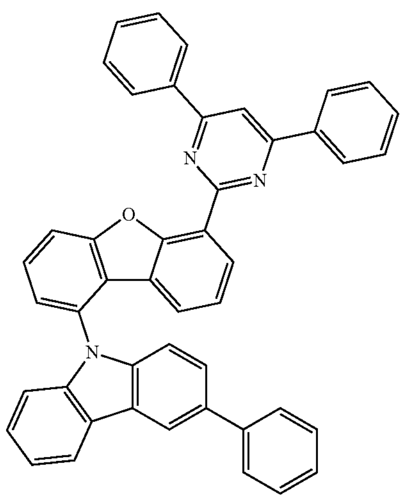
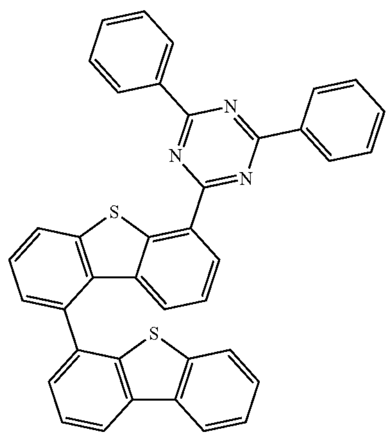
-continued
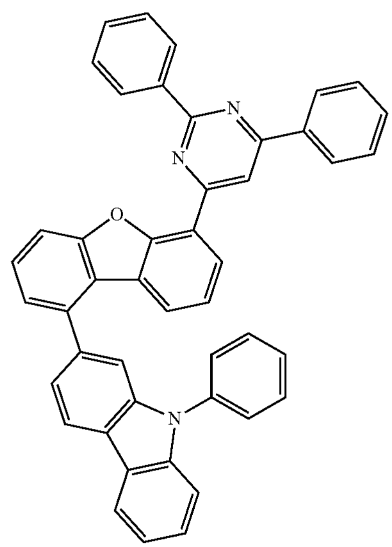
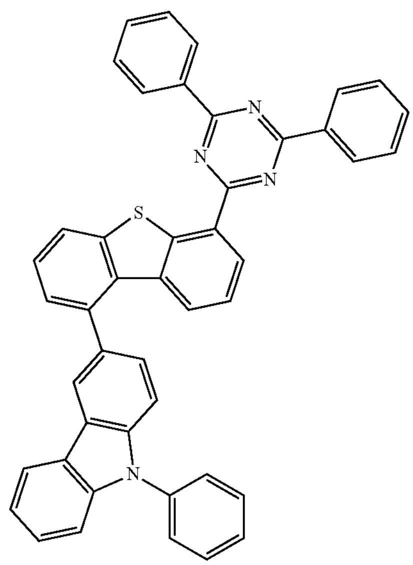
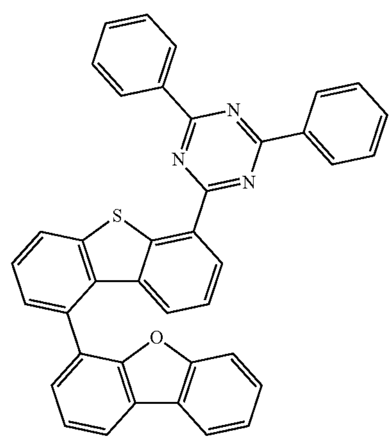

-continued
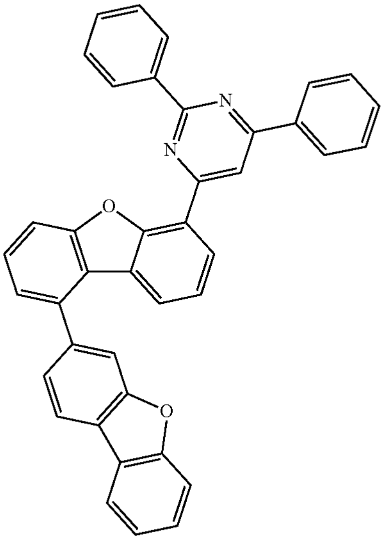
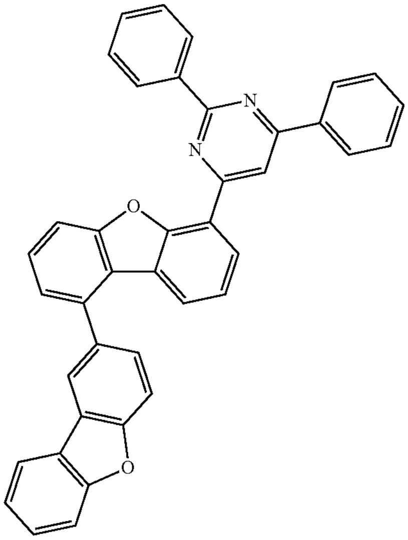
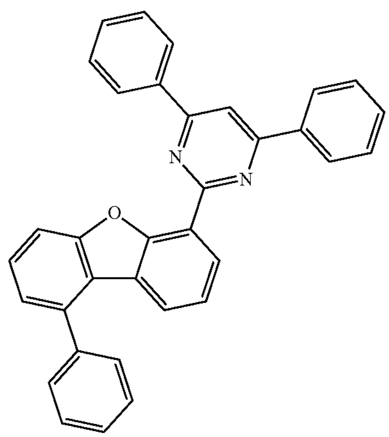
-continued
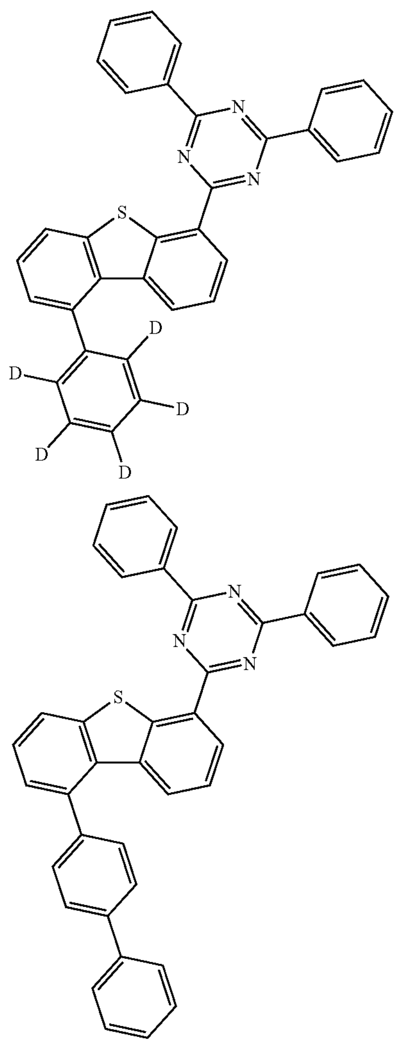
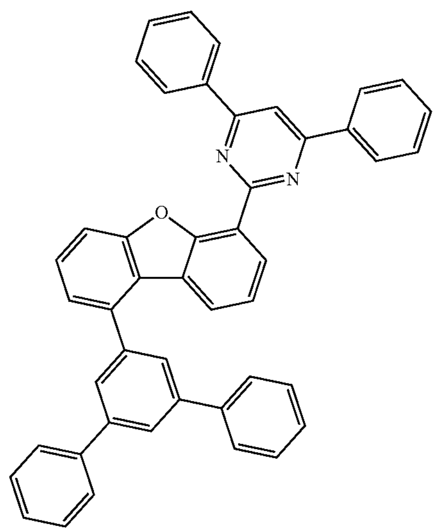

-continued
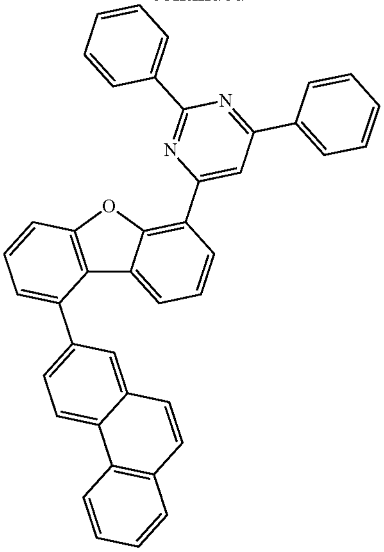
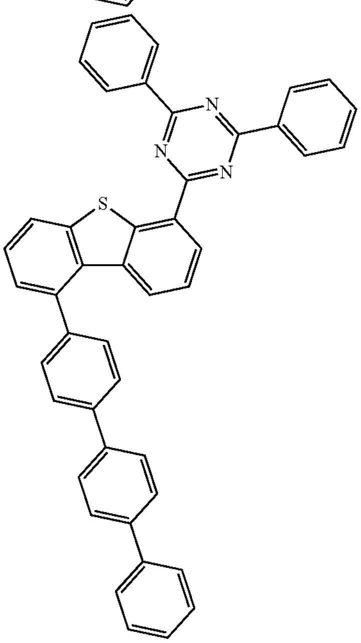
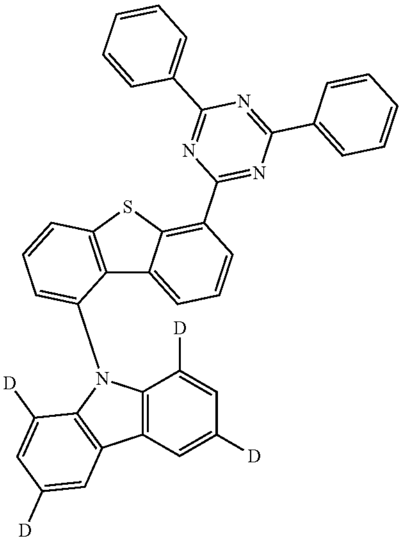
-continued
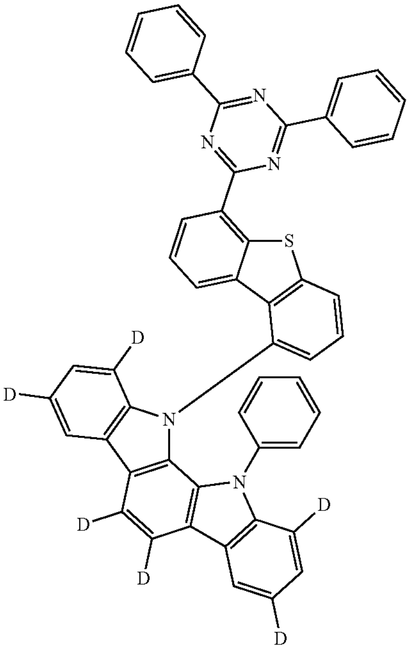
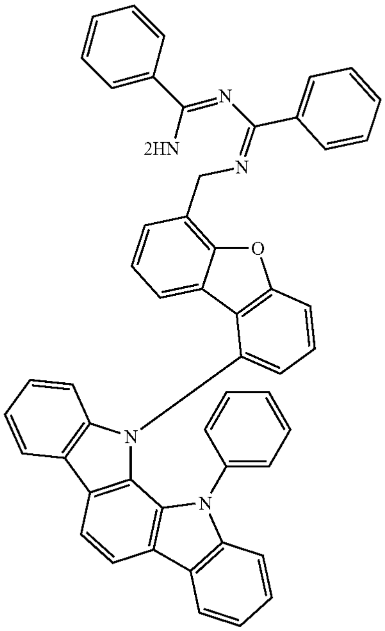

-continued
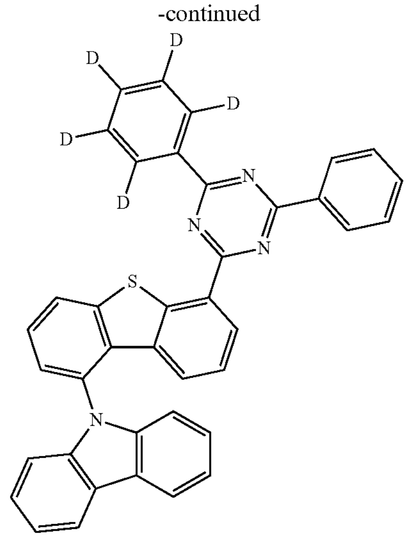
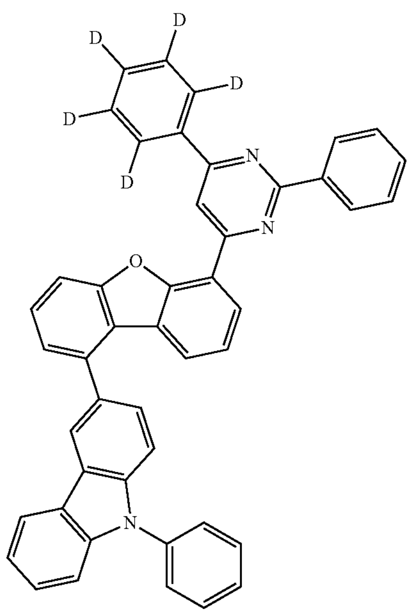
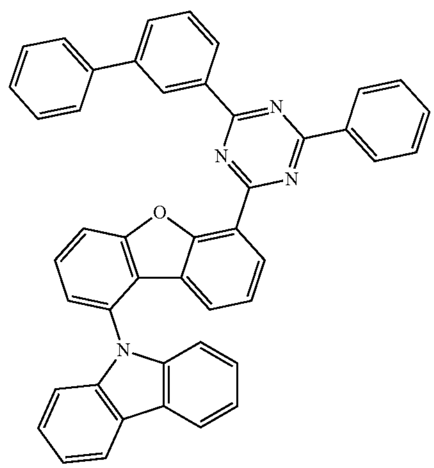
-continued
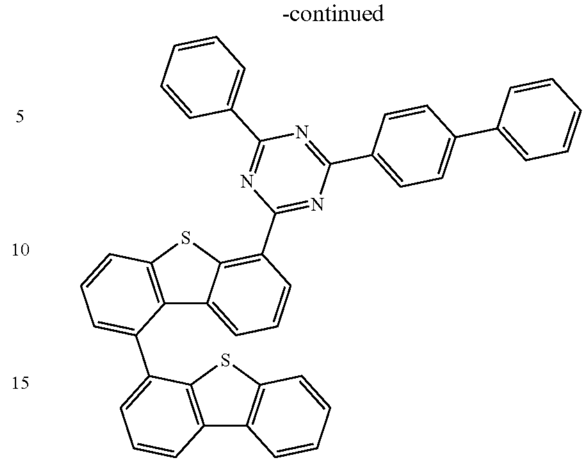
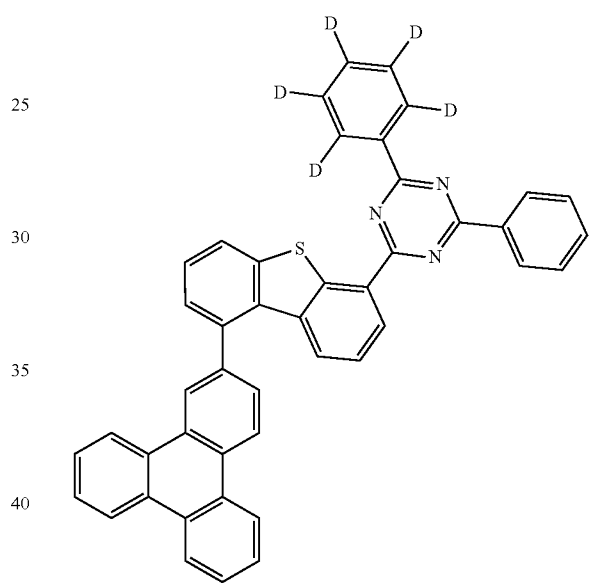
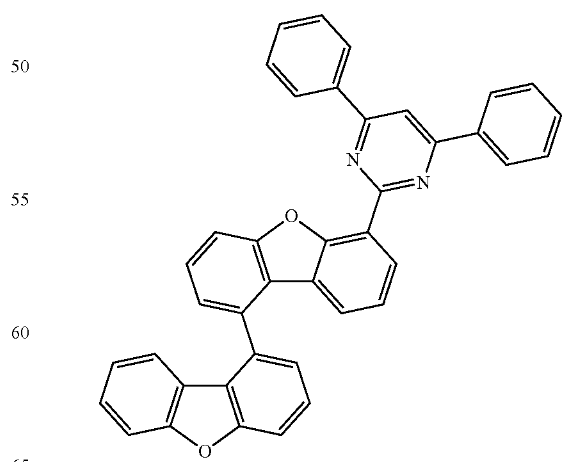

-continued
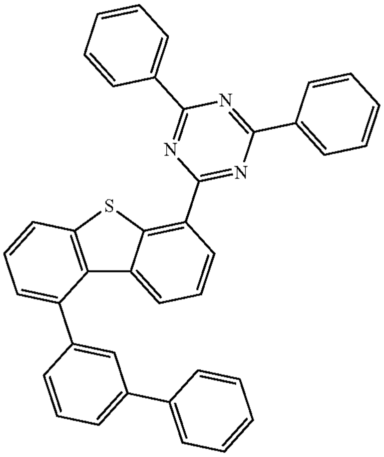
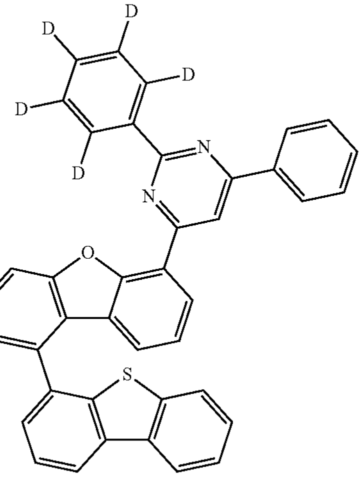
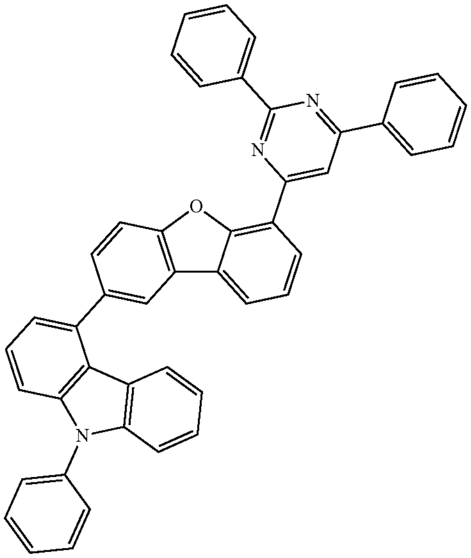
-continued
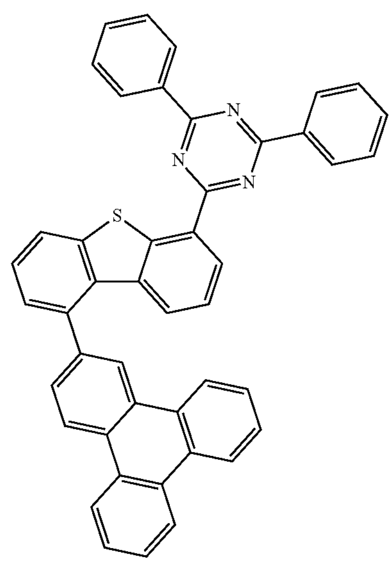
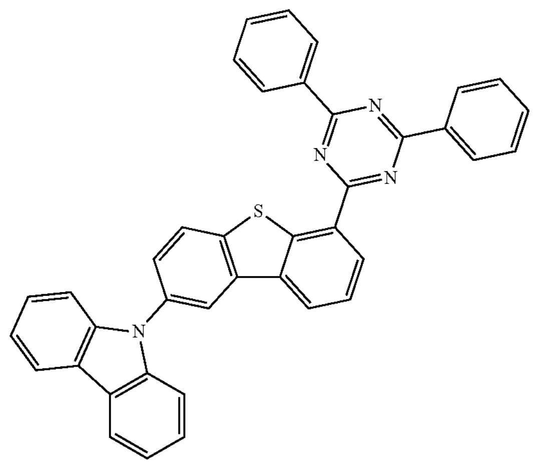
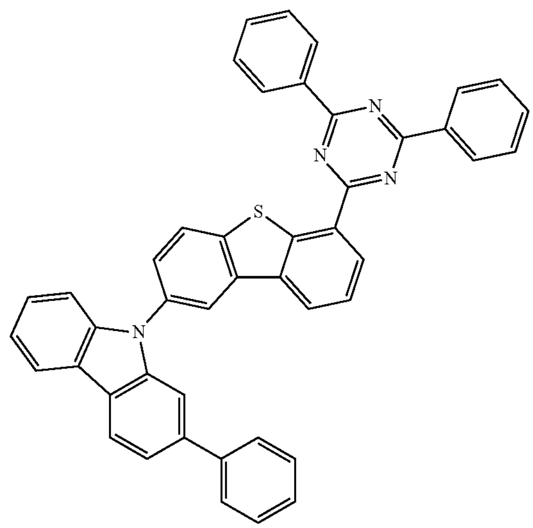

-continued
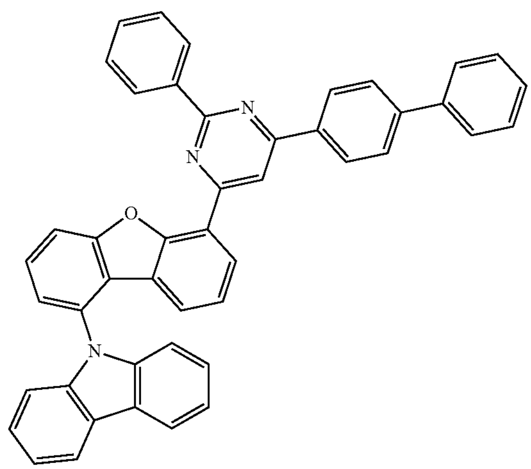
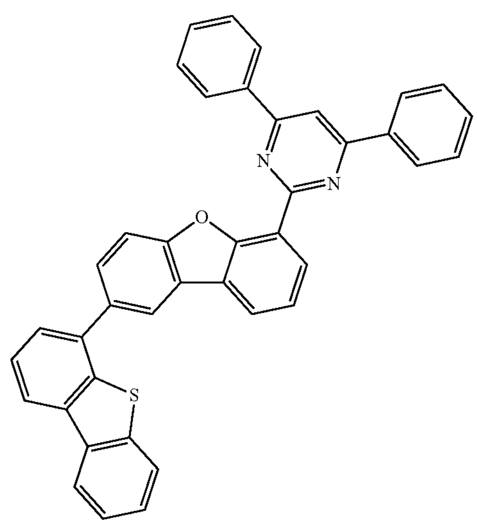
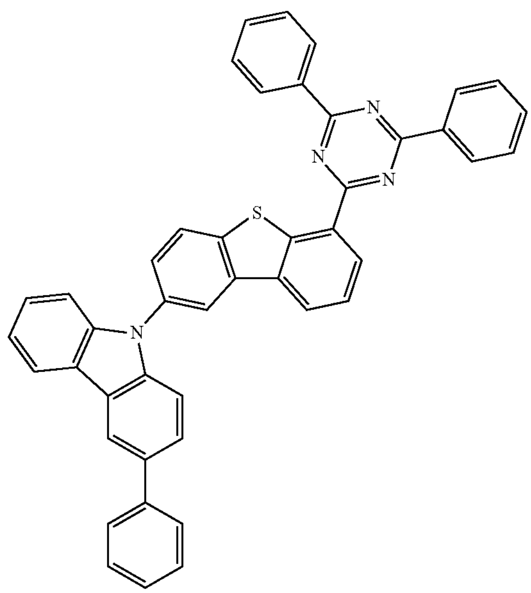
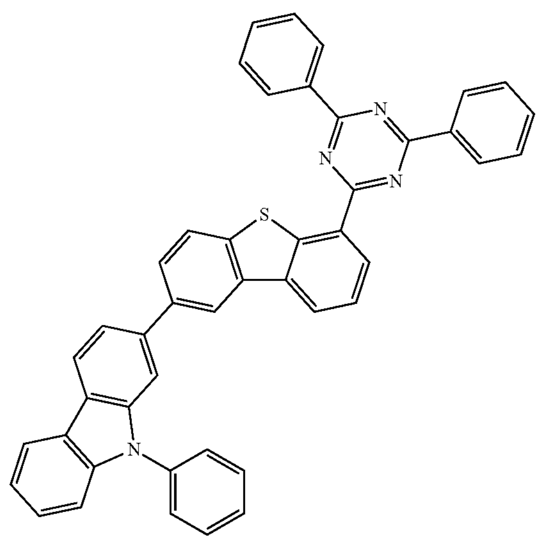
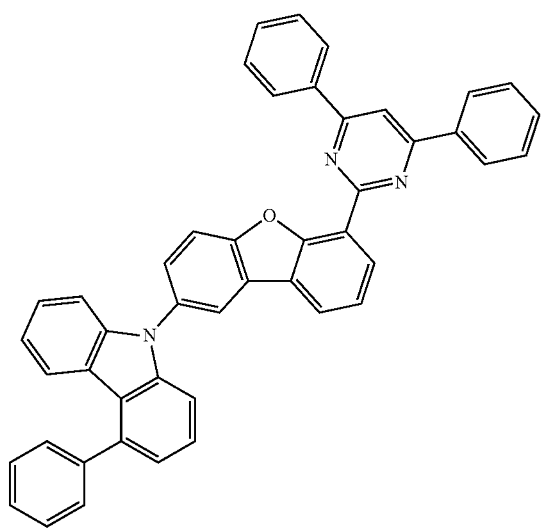
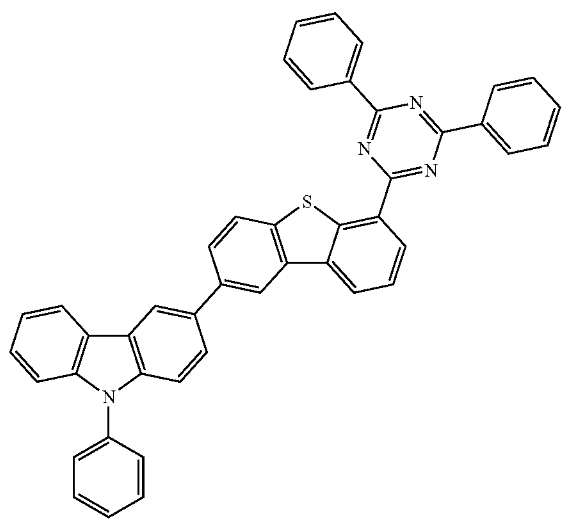

-continued
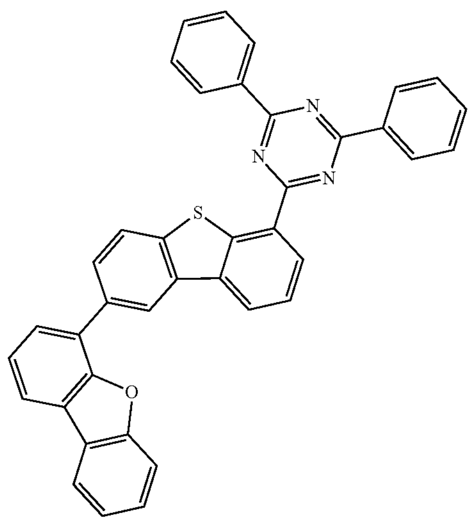
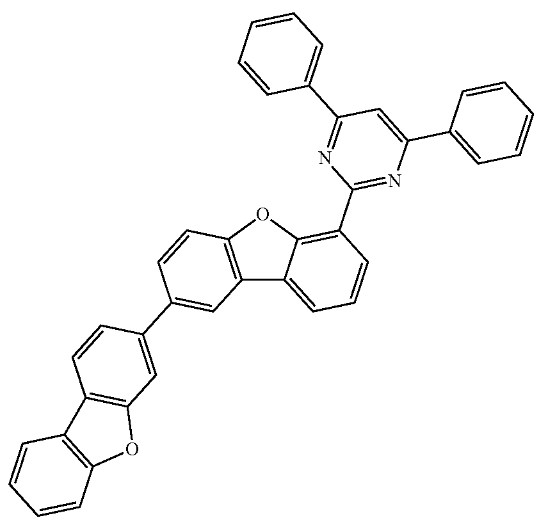
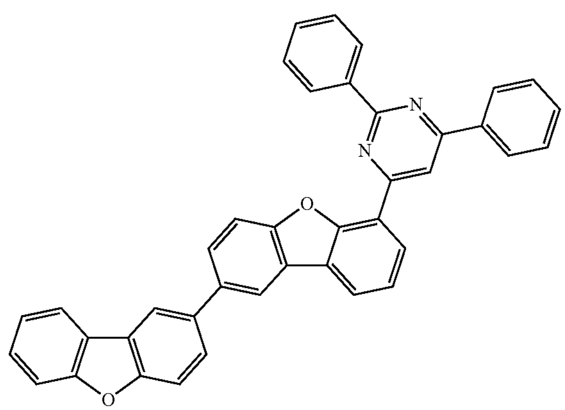
-continued
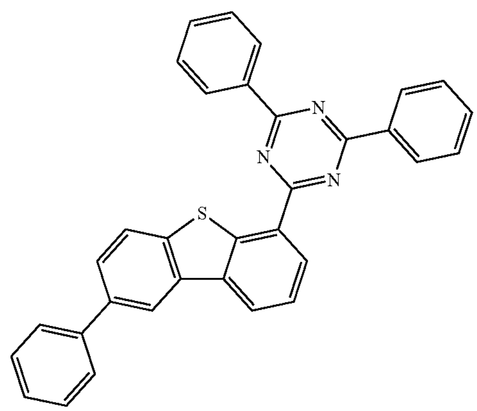
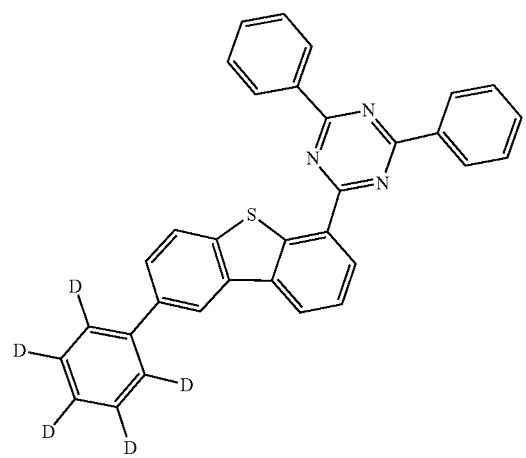
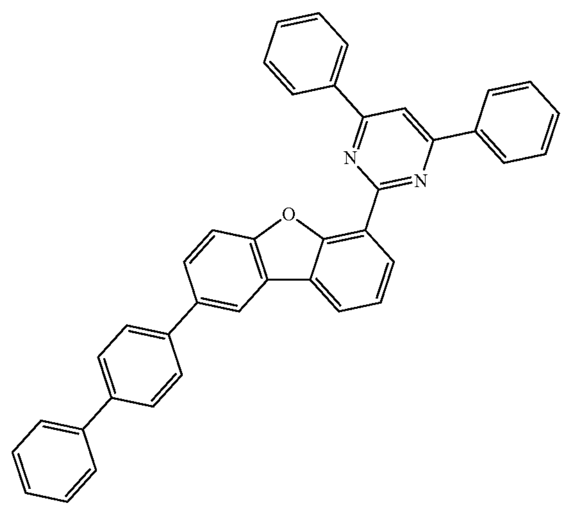

-continued
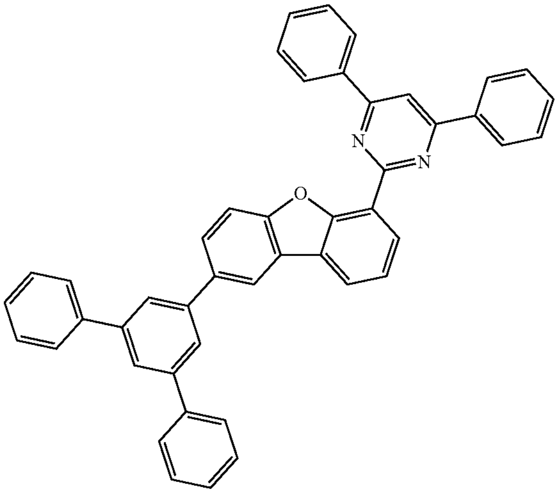
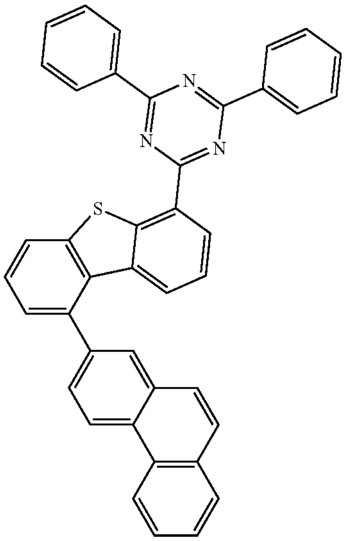
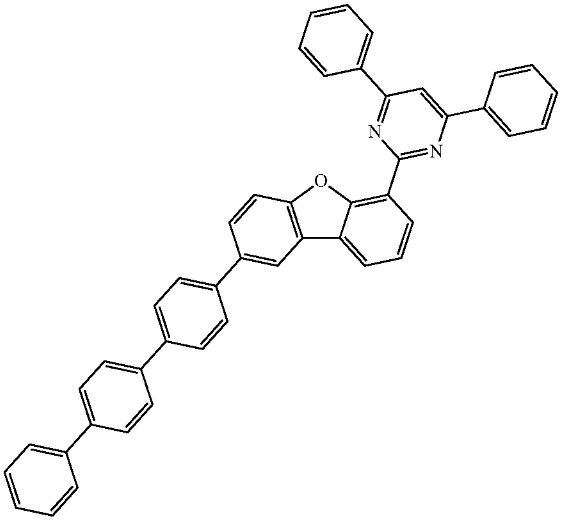
-continued
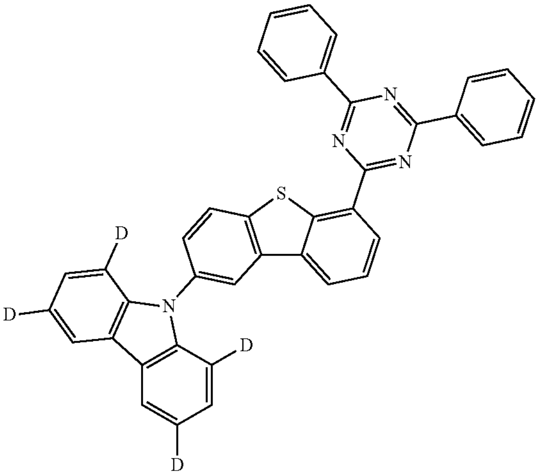
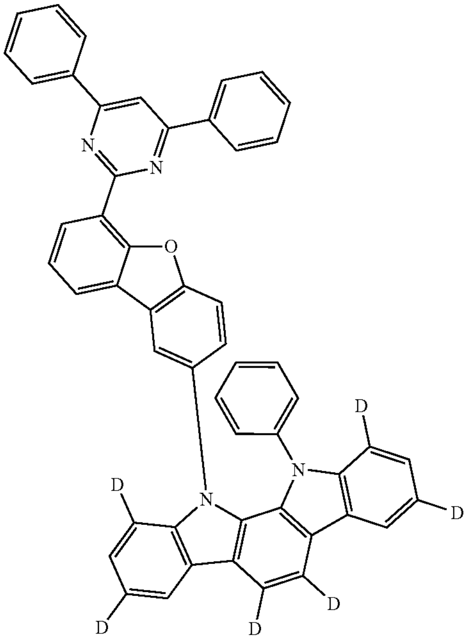

-continued
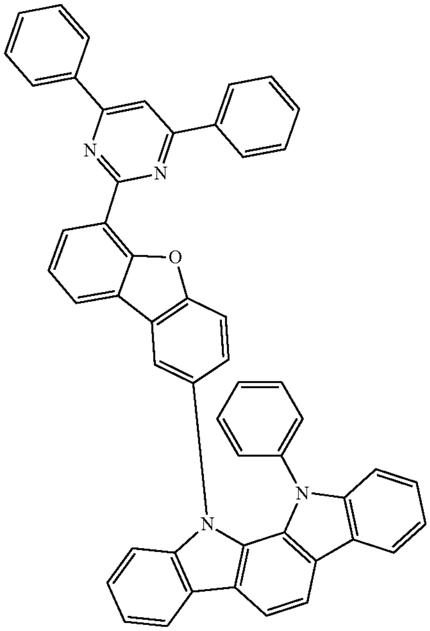
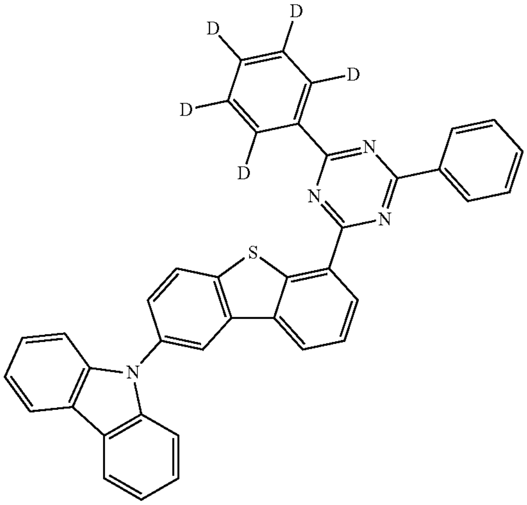
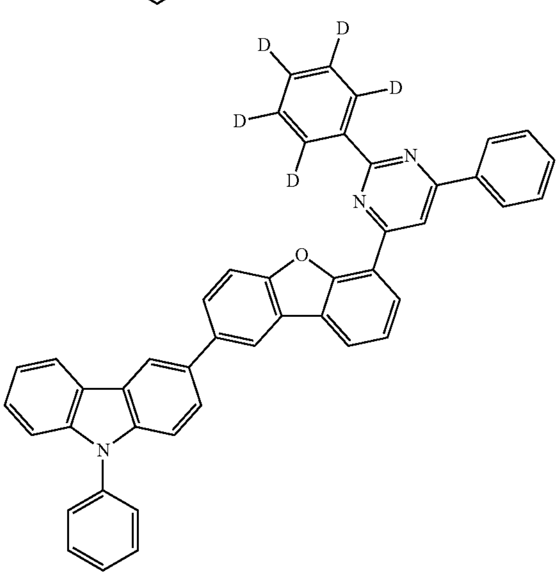
-continued
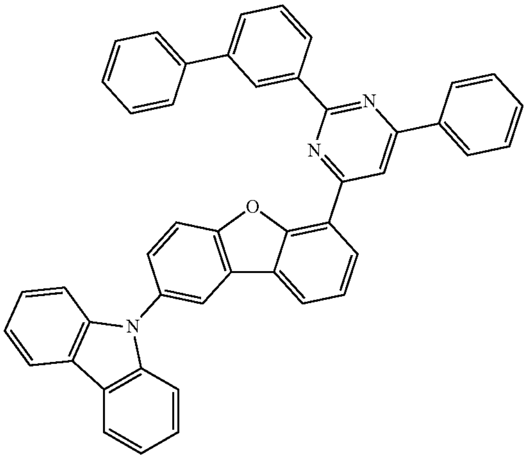
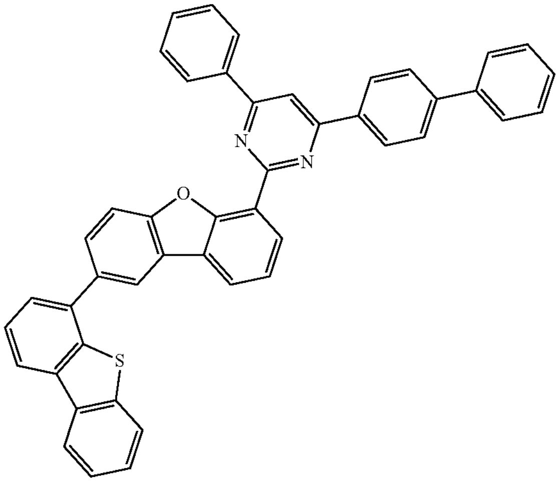
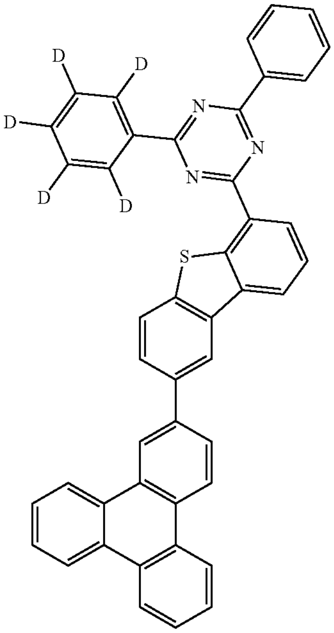

-continued
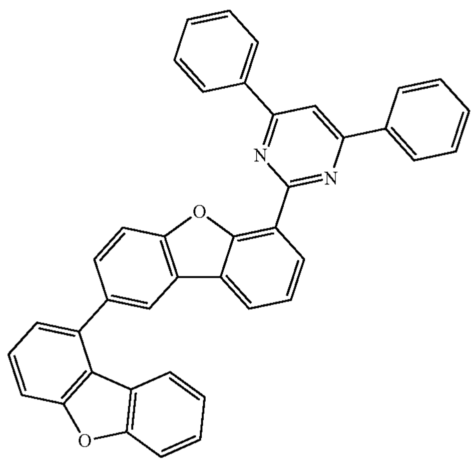
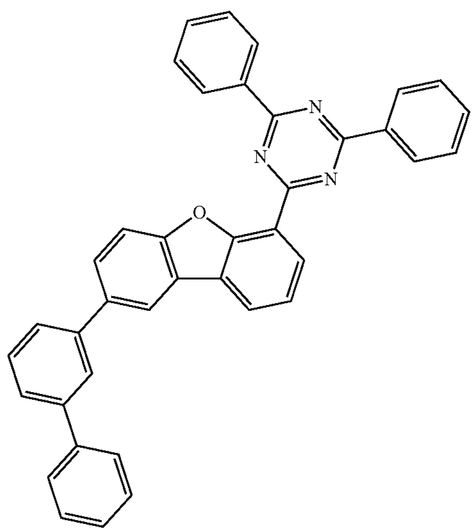
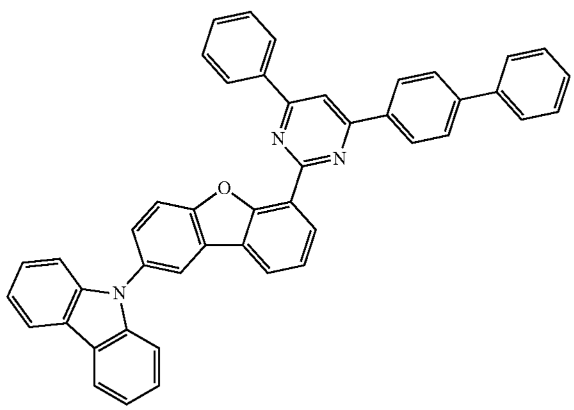
-continued
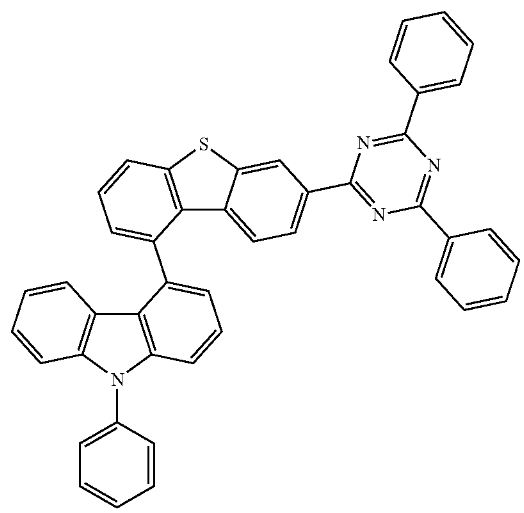
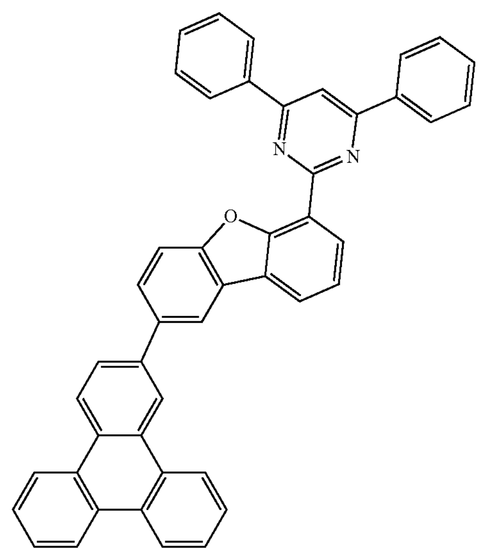
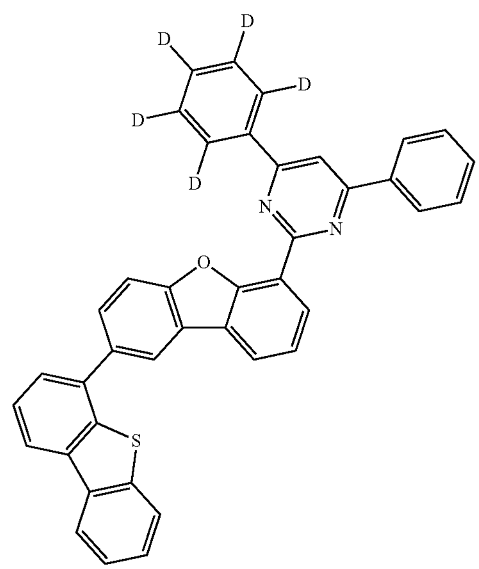

-continued
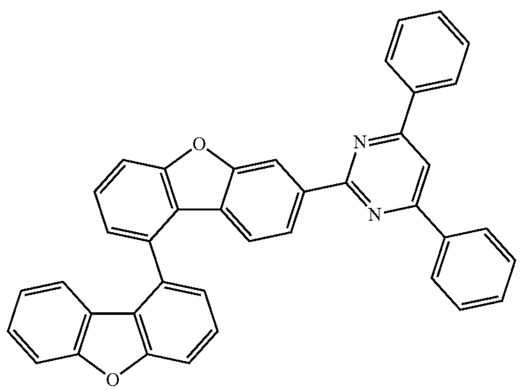
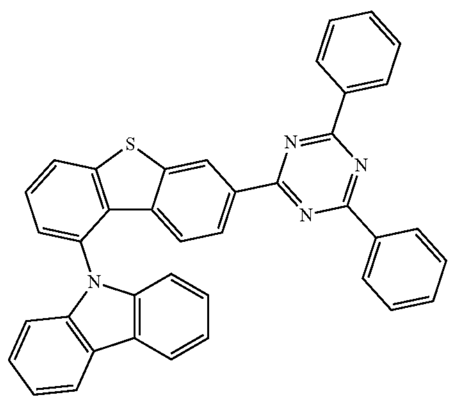
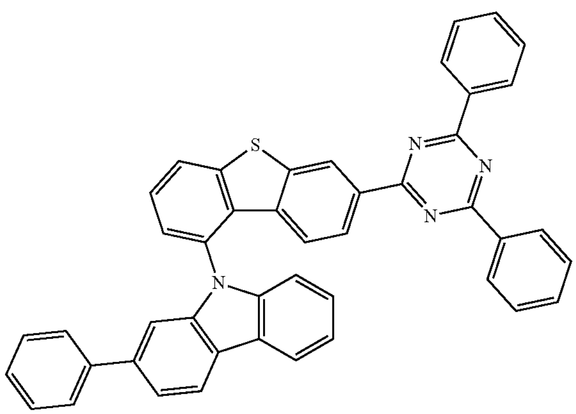
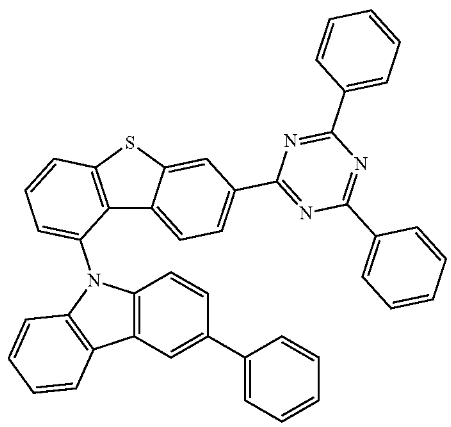
-continued
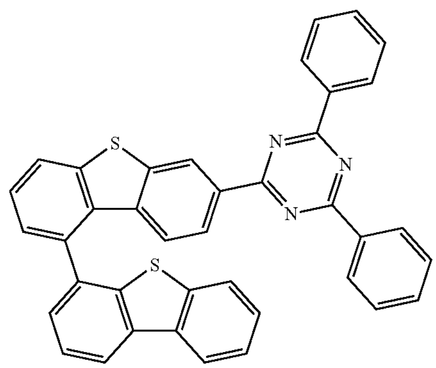
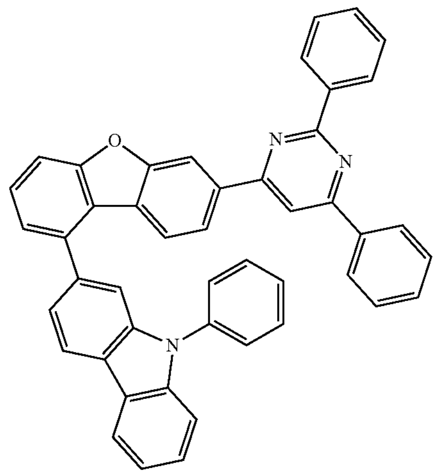
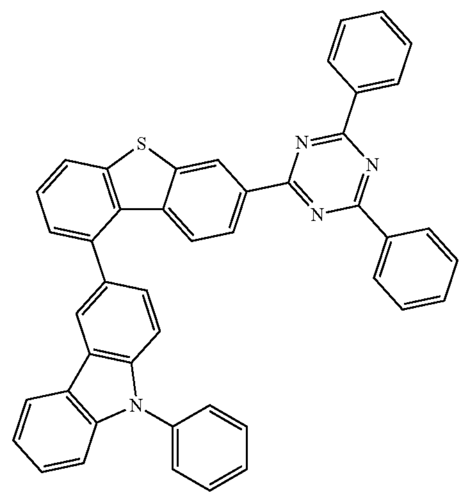
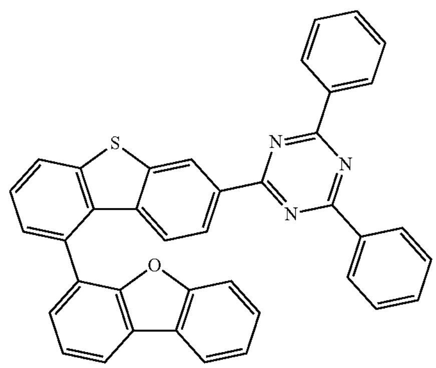

-continued
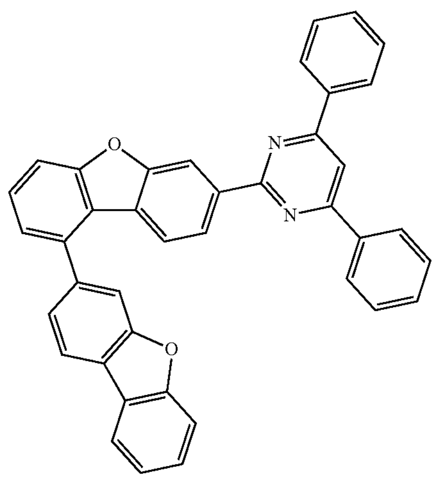
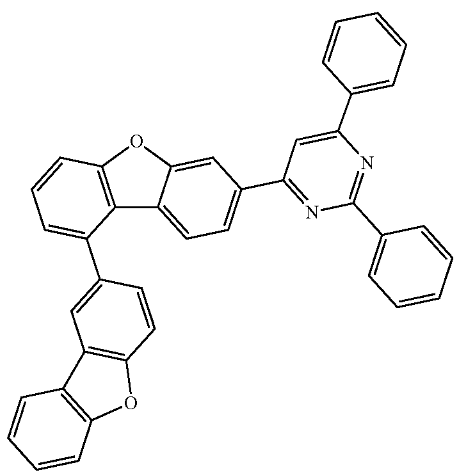
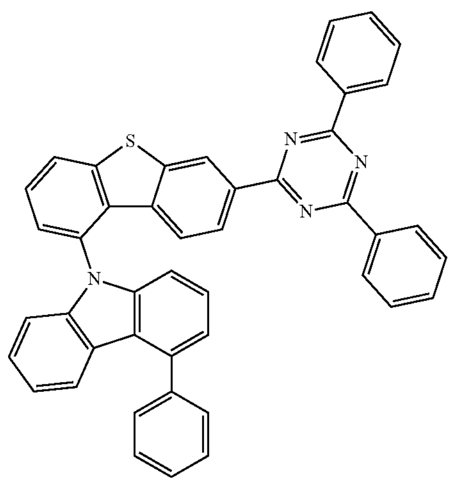
-continued
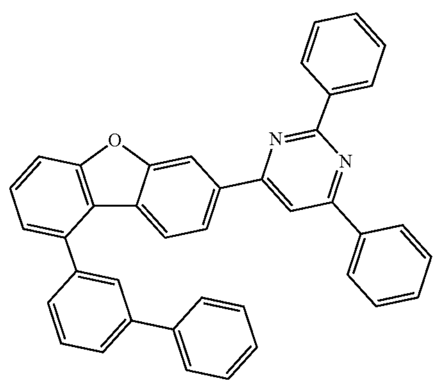
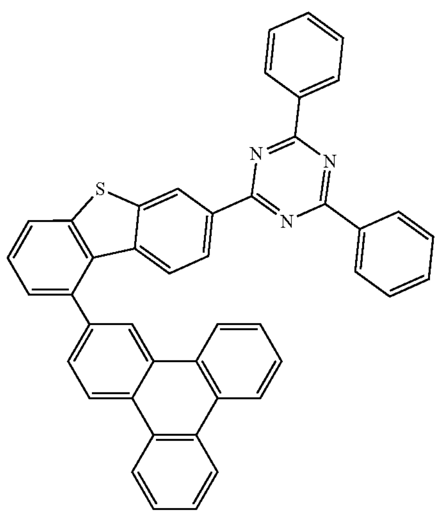
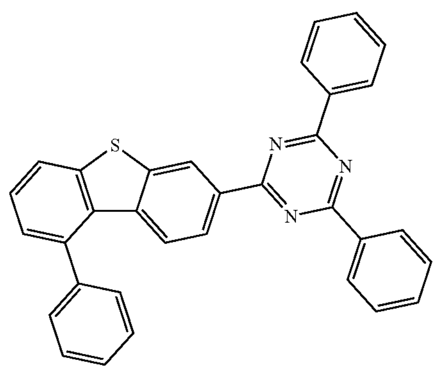
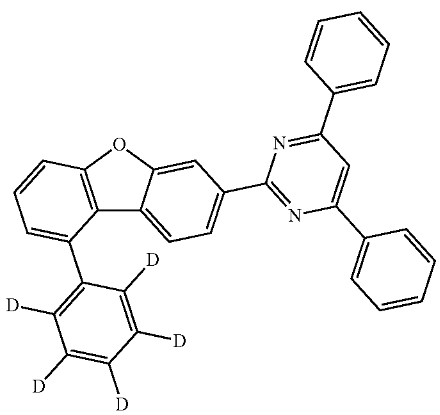

-continued
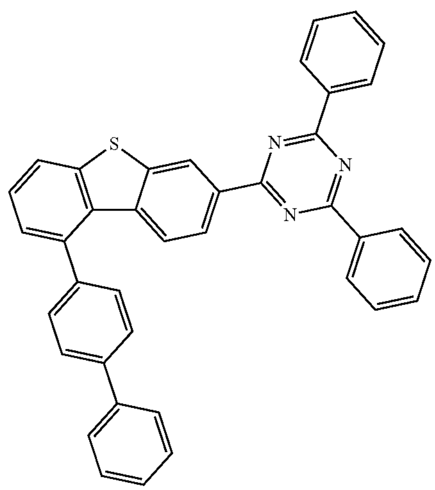
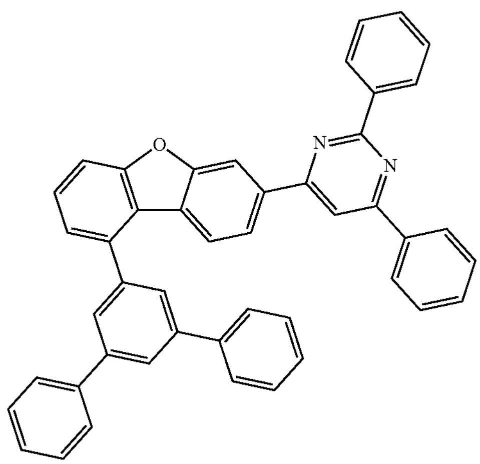
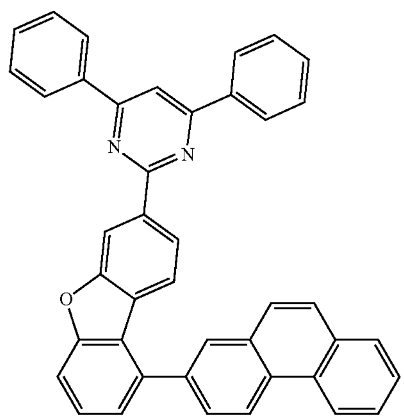
-continued
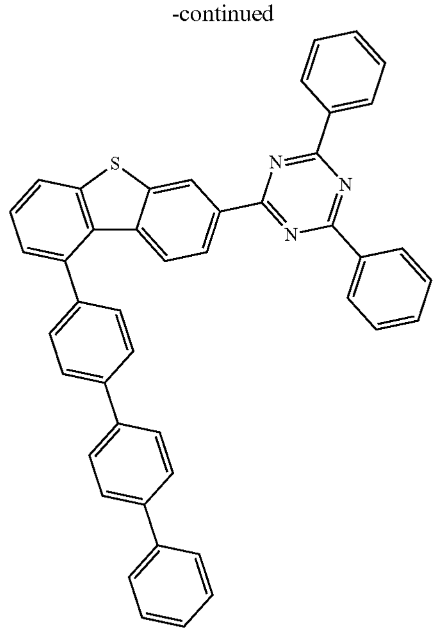
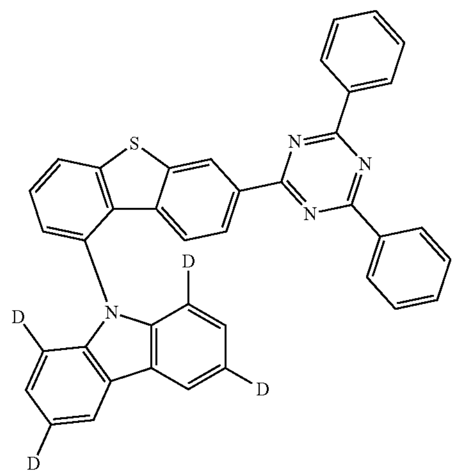
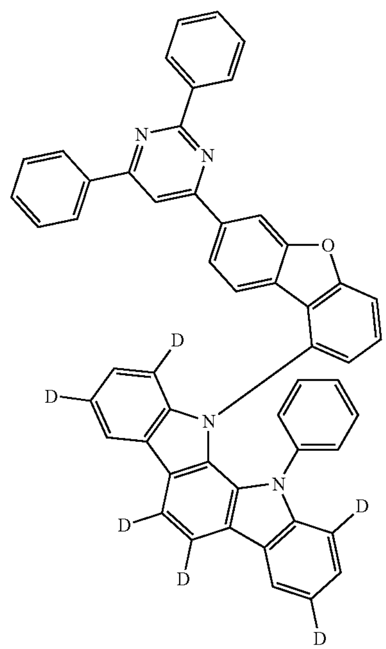

-continued
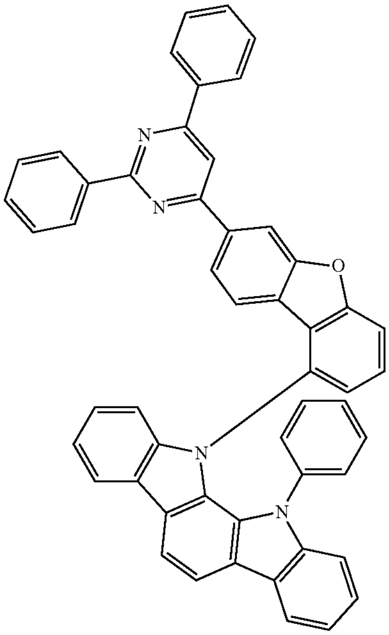
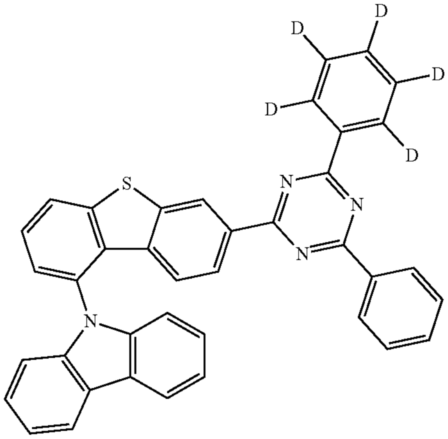
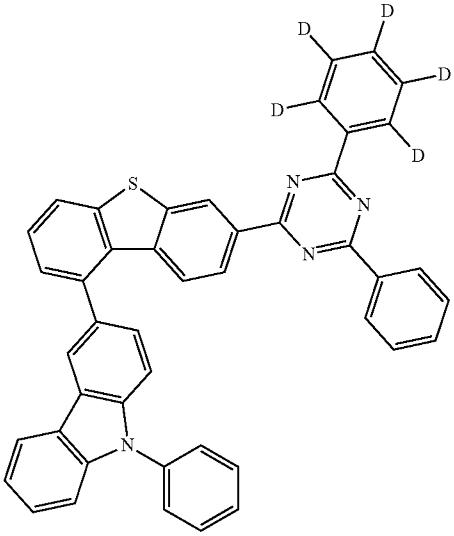
-continued
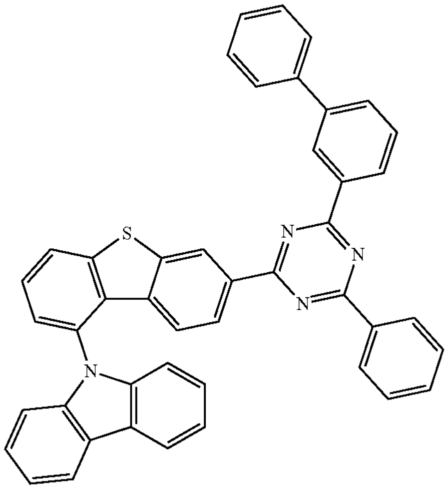
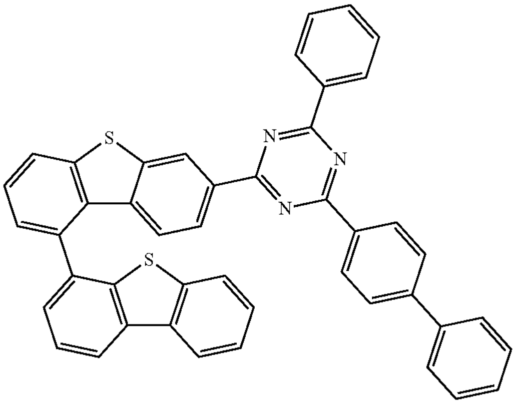
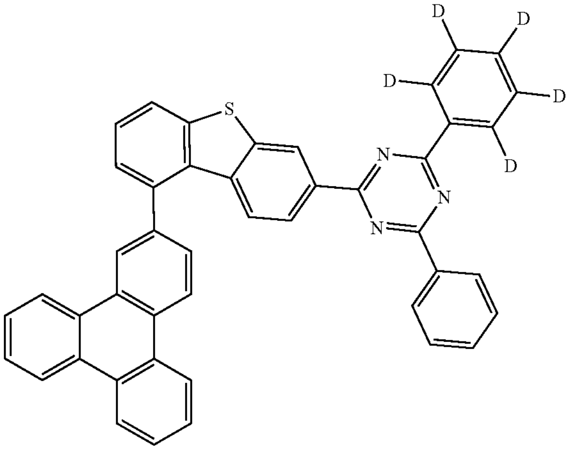

-continued
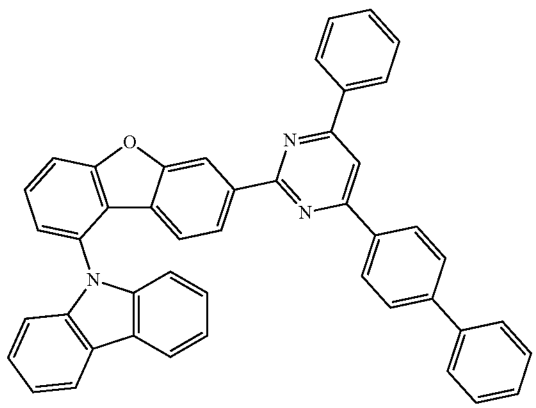
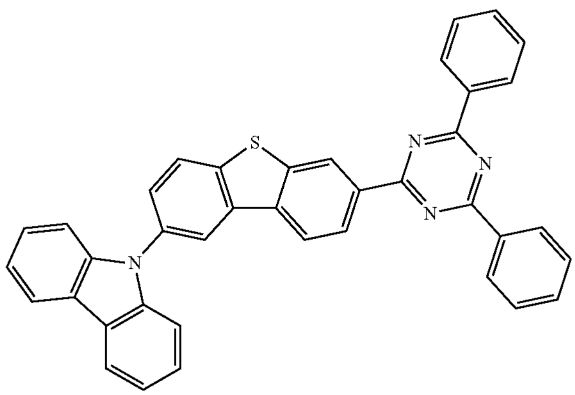
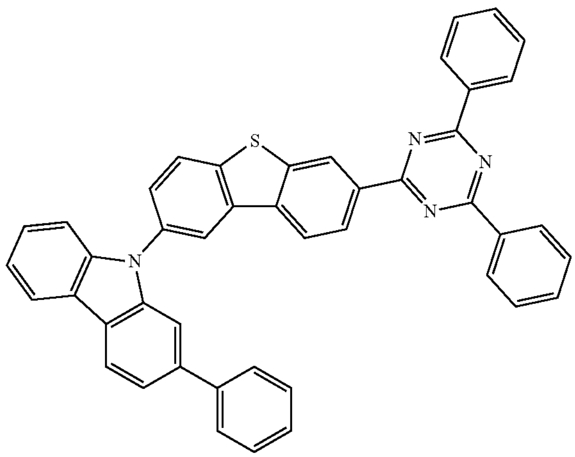
-continued
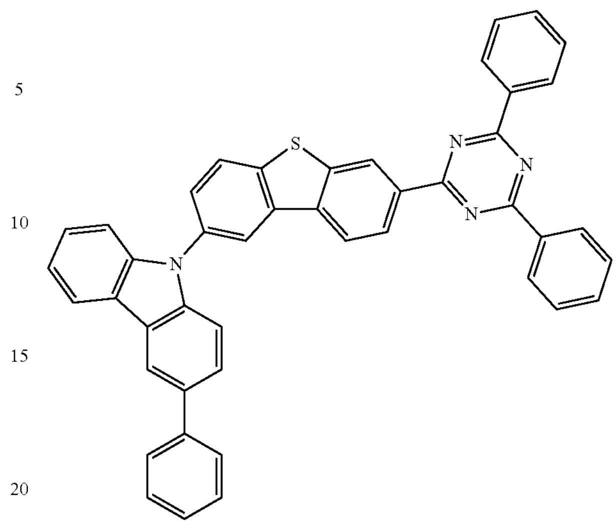
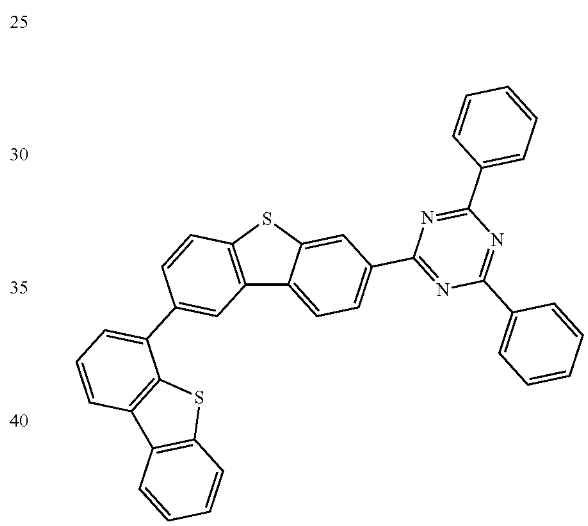
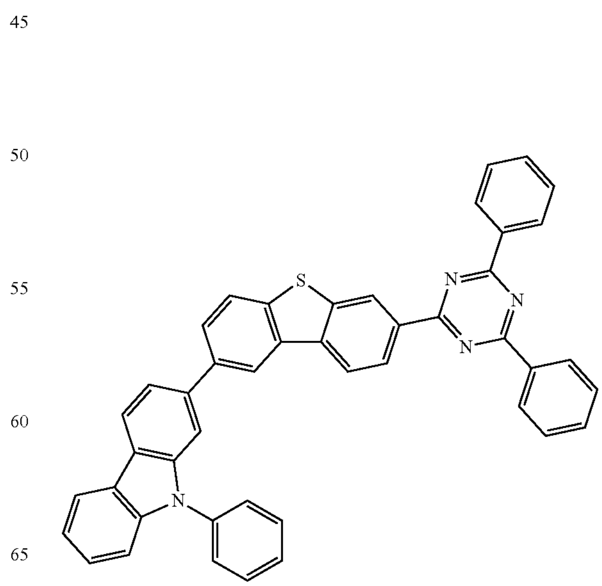

-continued
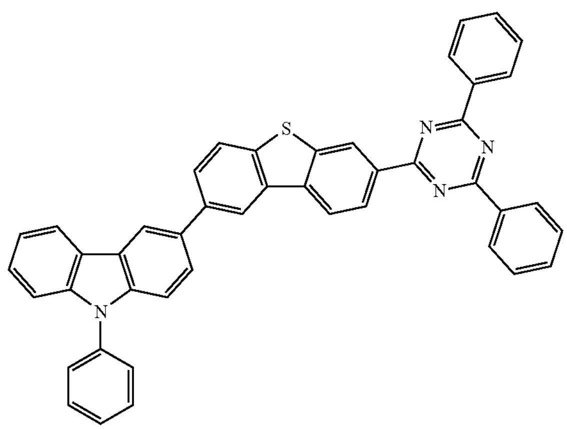
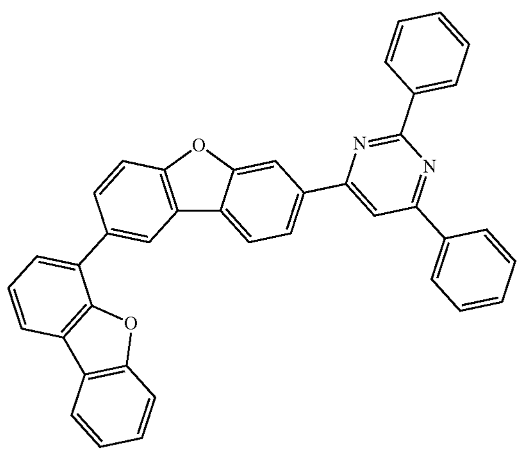
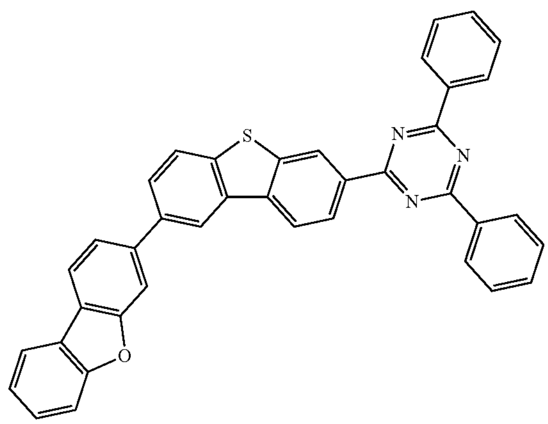
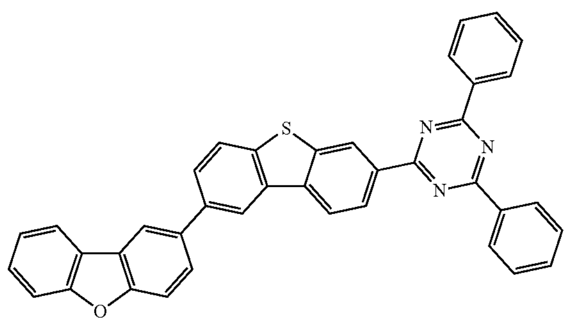
-continued
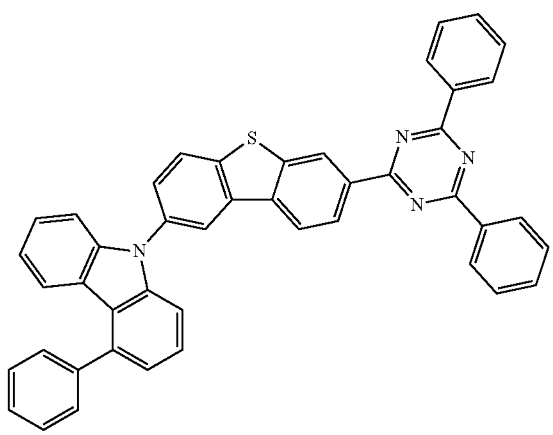
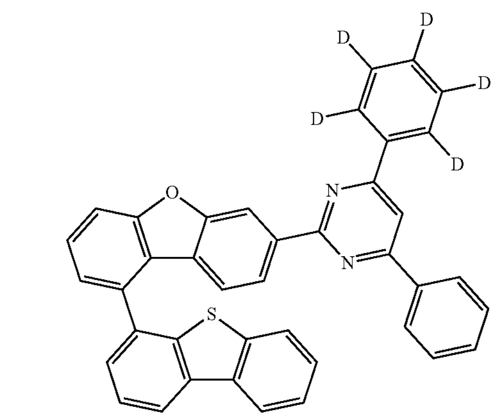
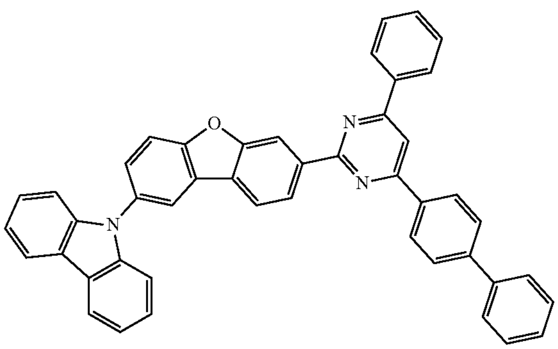
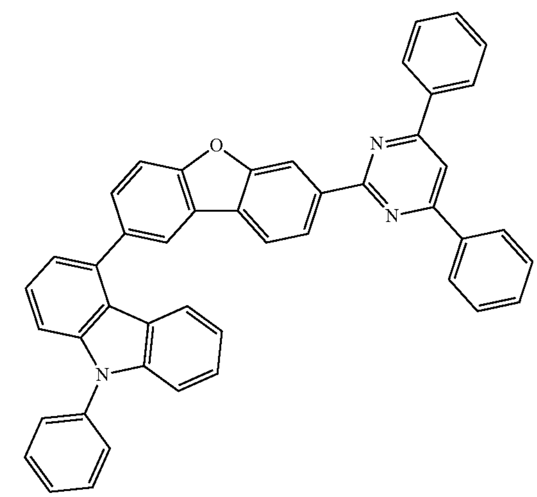

-continued
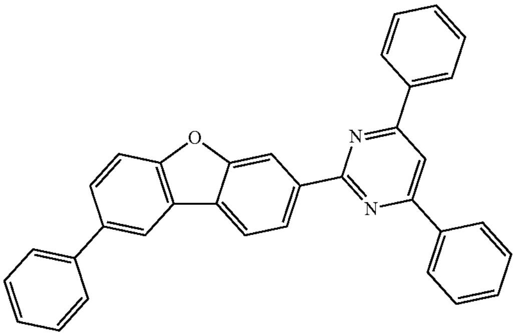
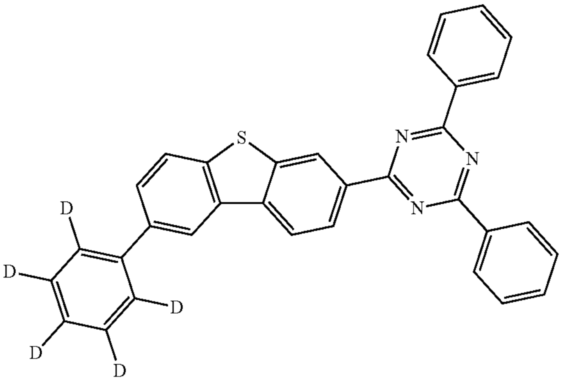
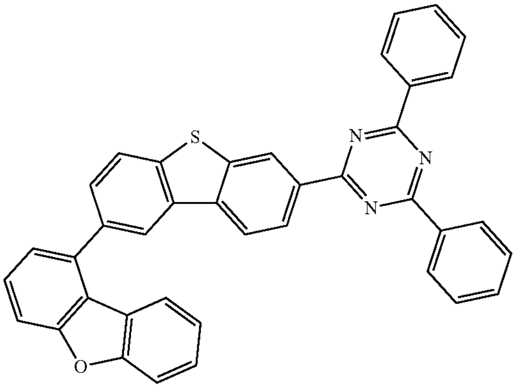
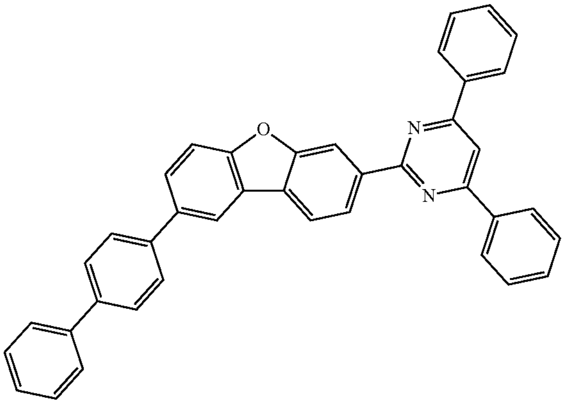
-continued
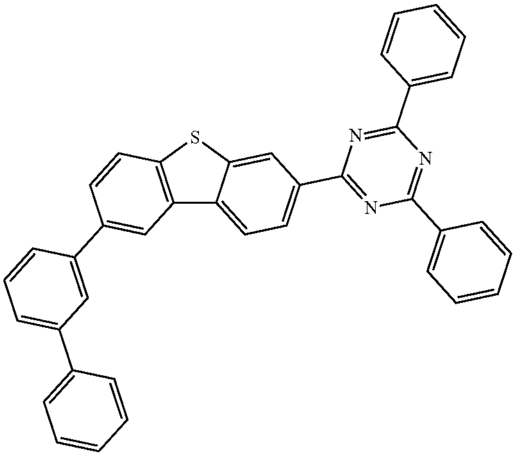
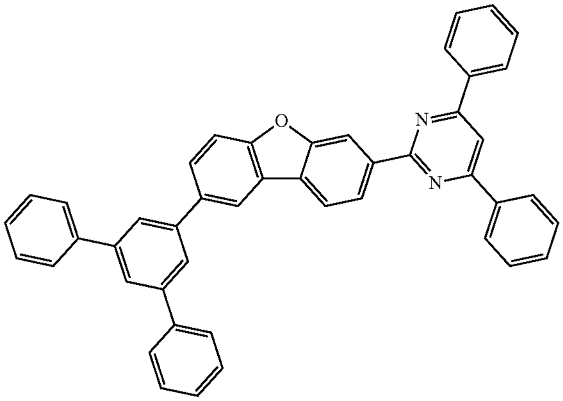
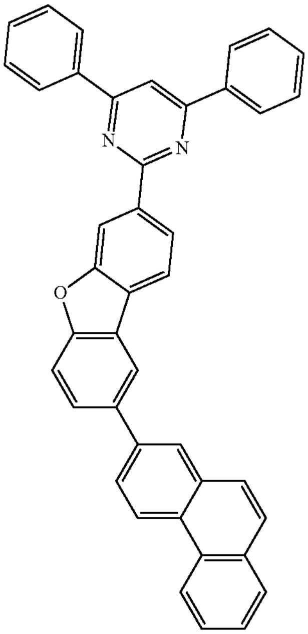

-continued
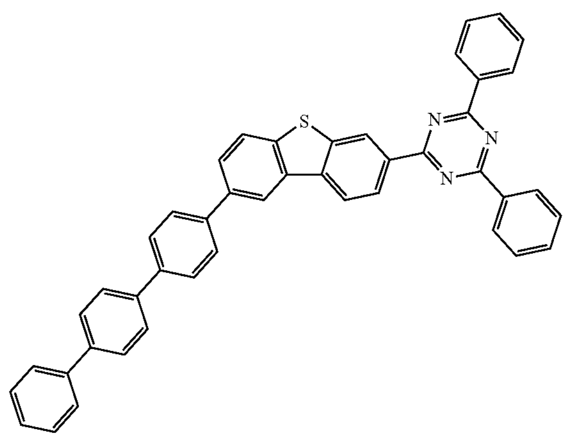
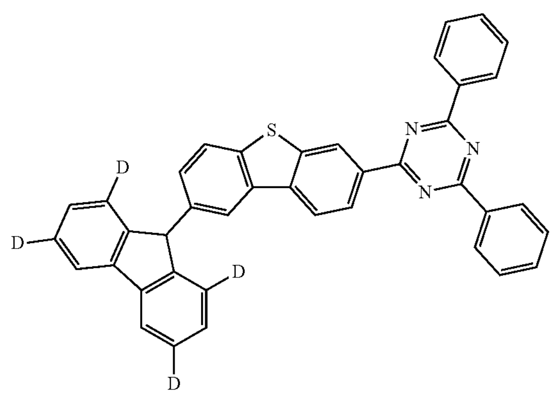
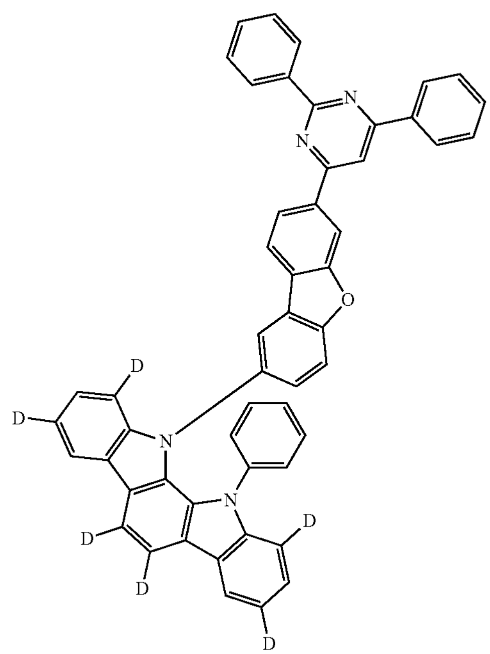
-continued
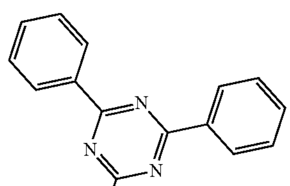
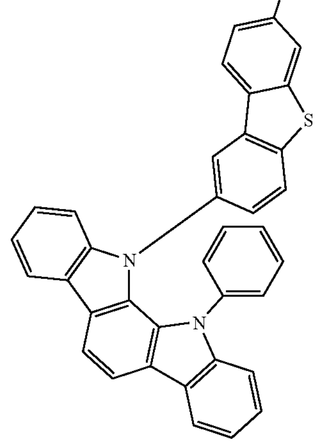
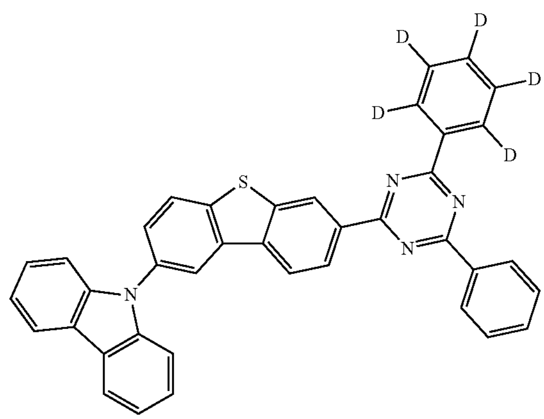
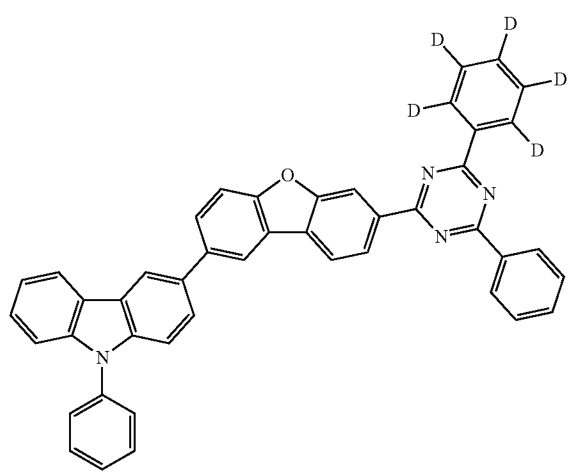

-continued
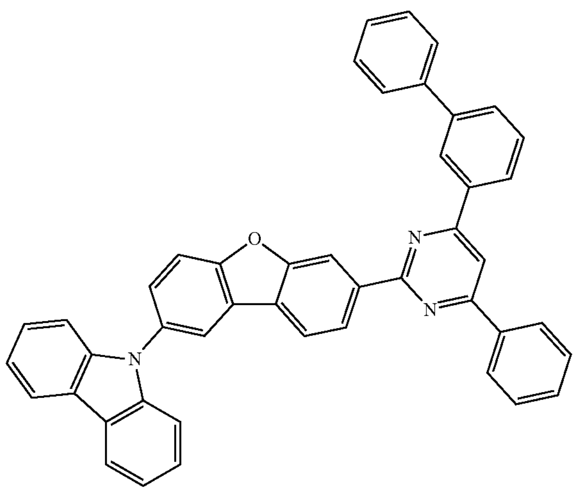
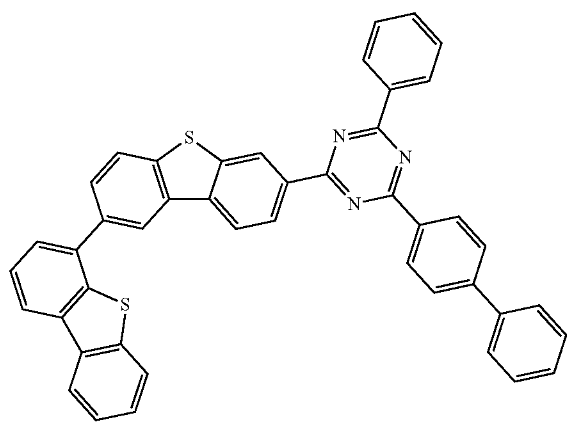
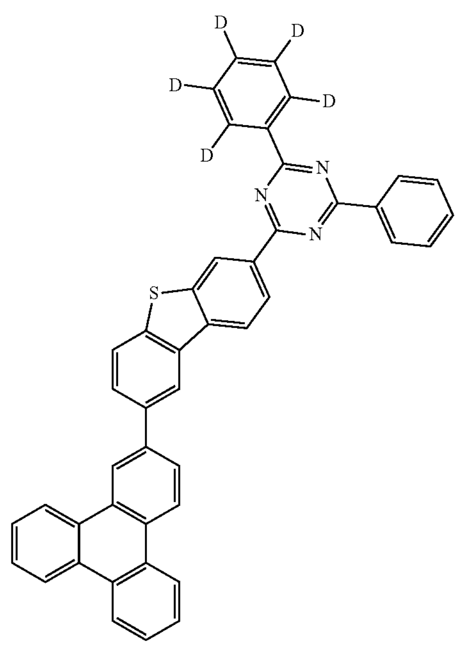
-continued
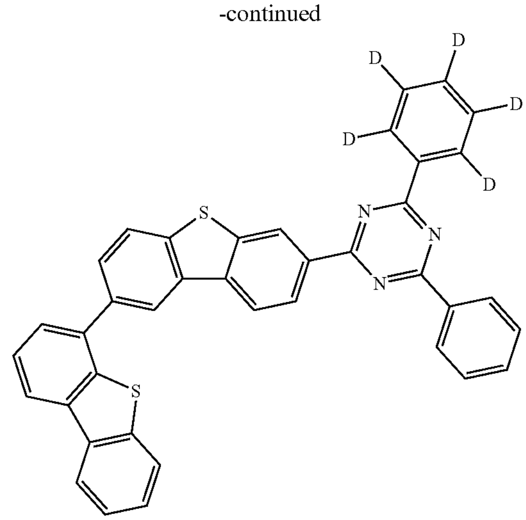
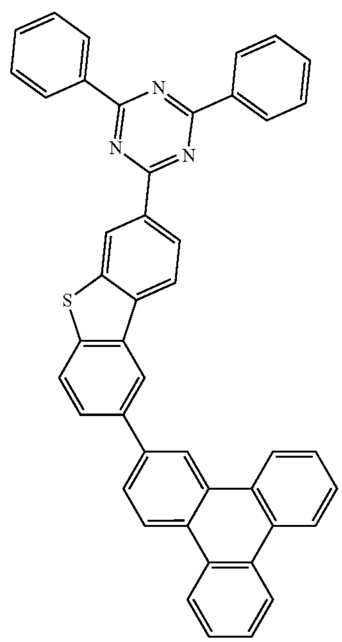
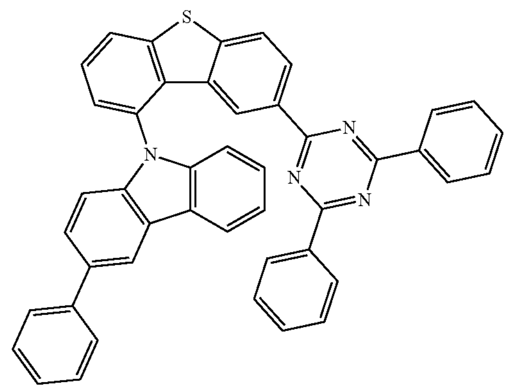

-continued
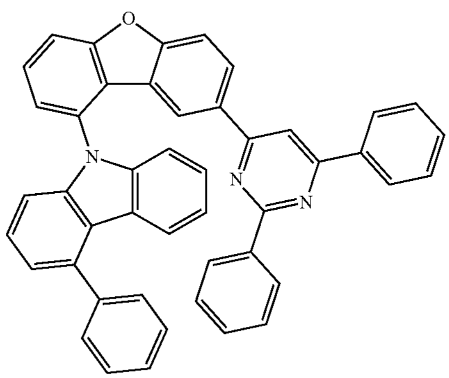
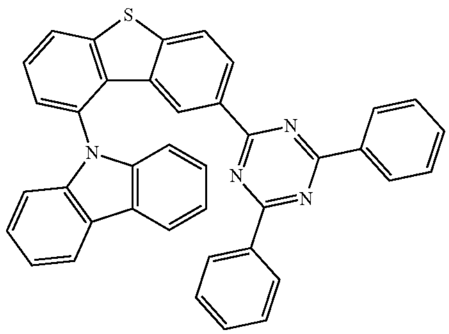
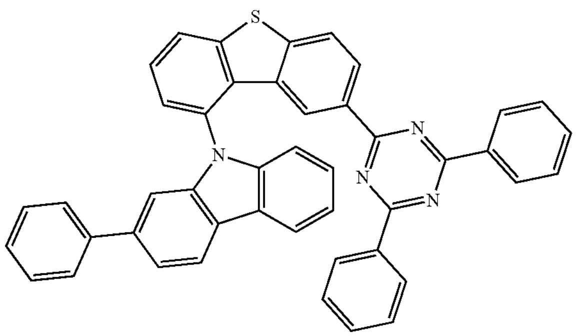
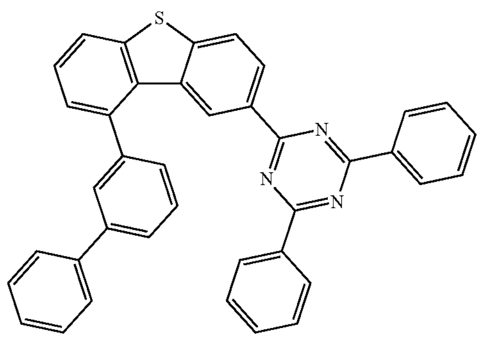
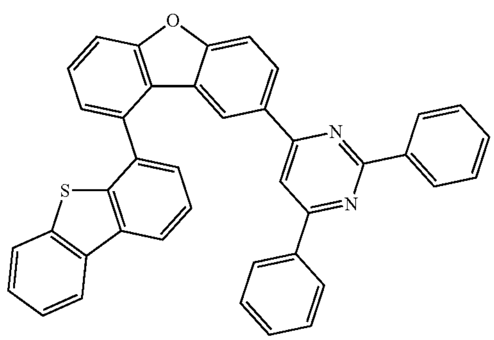
-continued
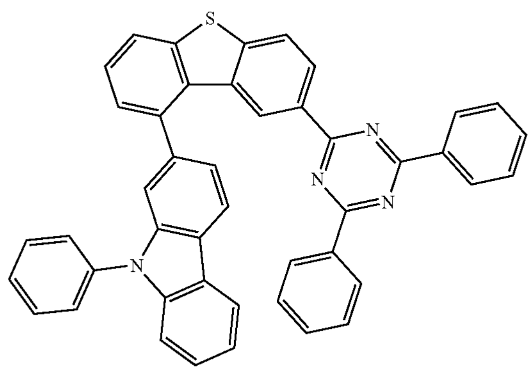
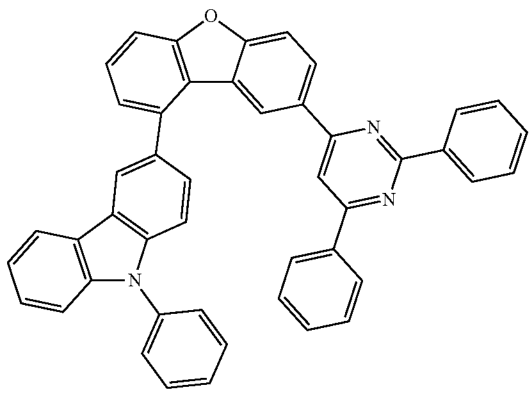
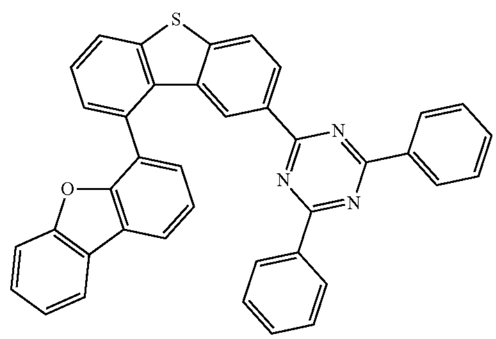
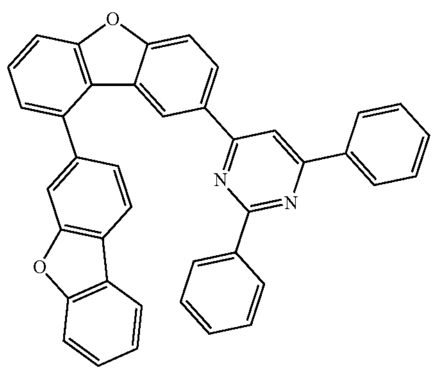

-continued
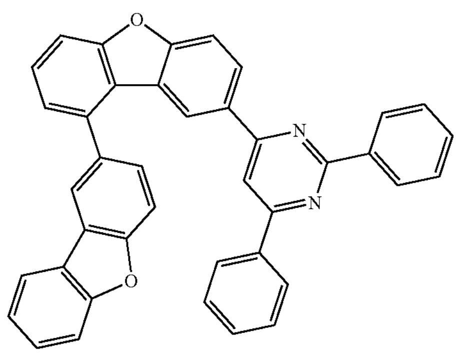
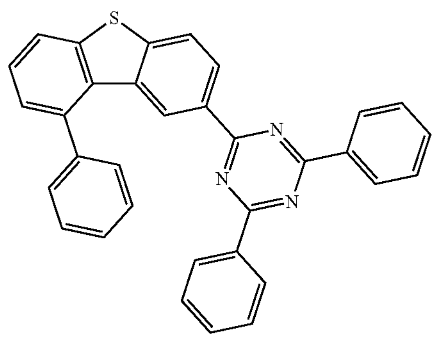
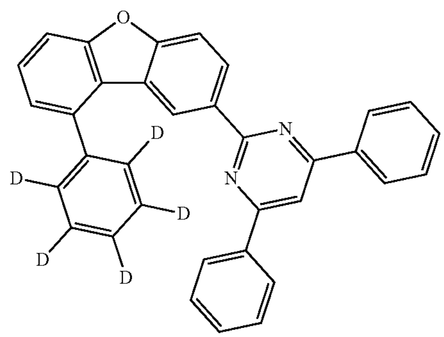
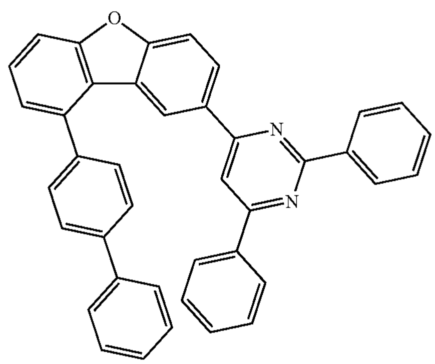
-continued
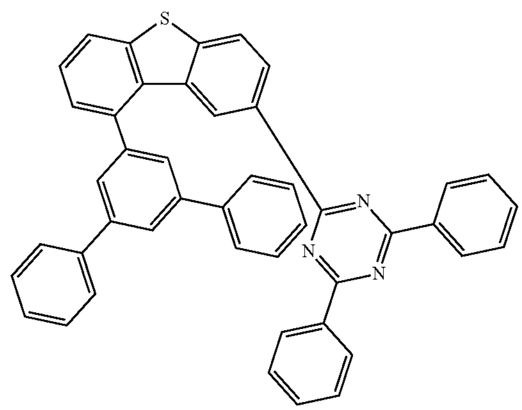
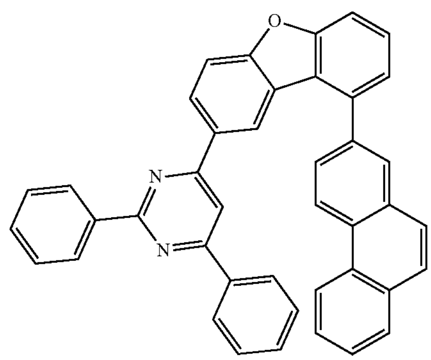
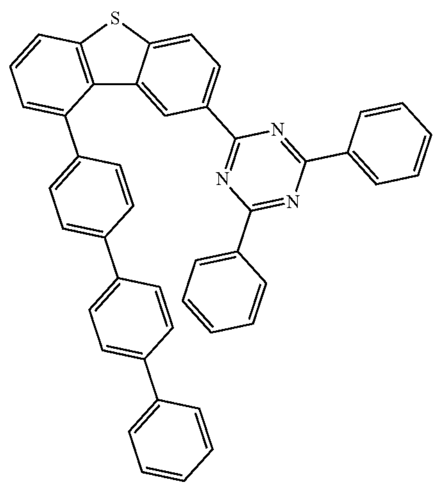
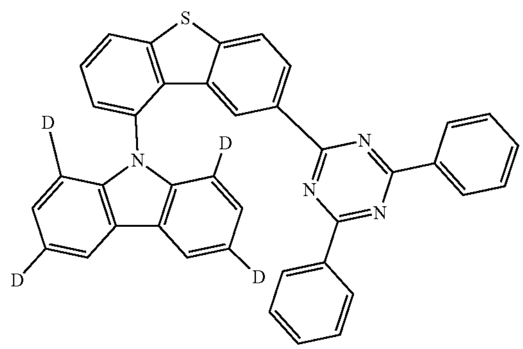

-continued
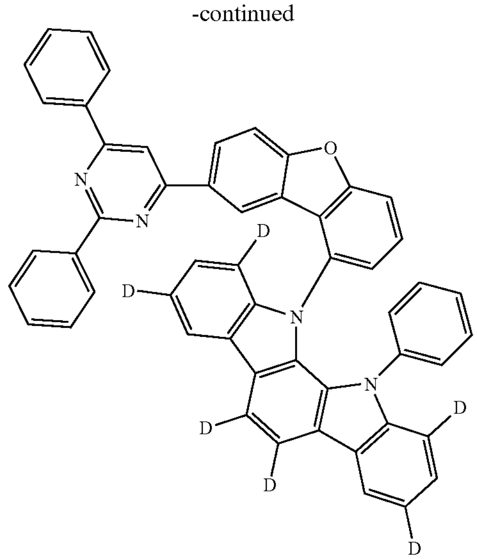
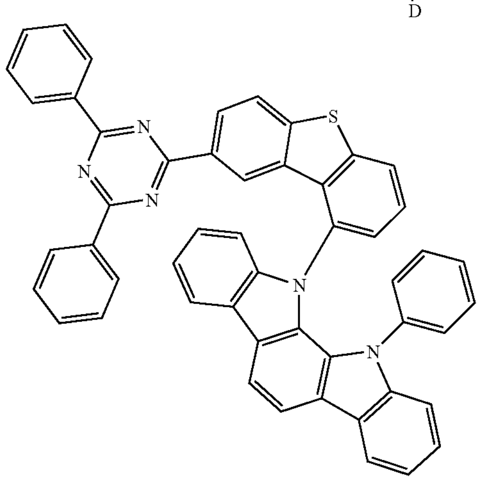
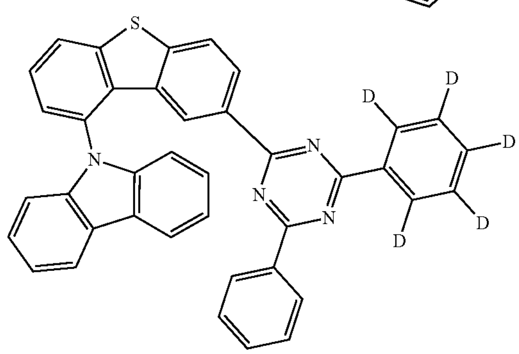
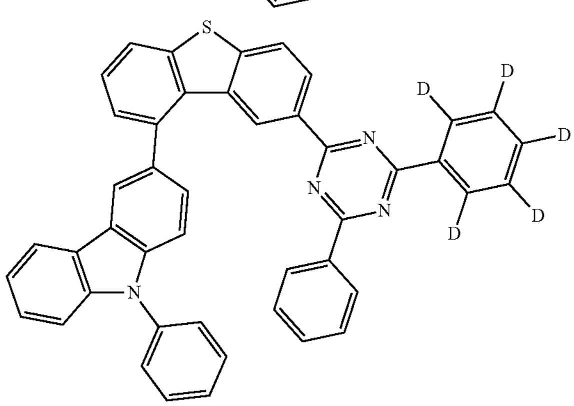
-continued
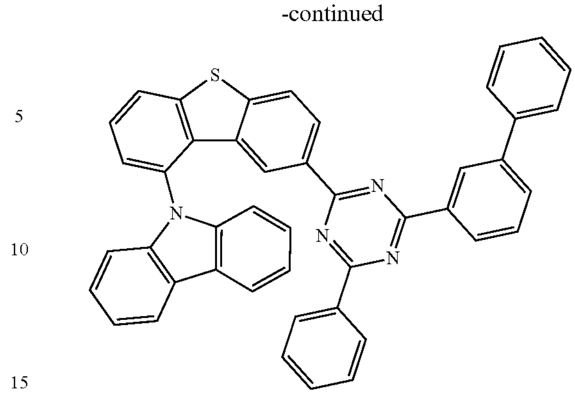
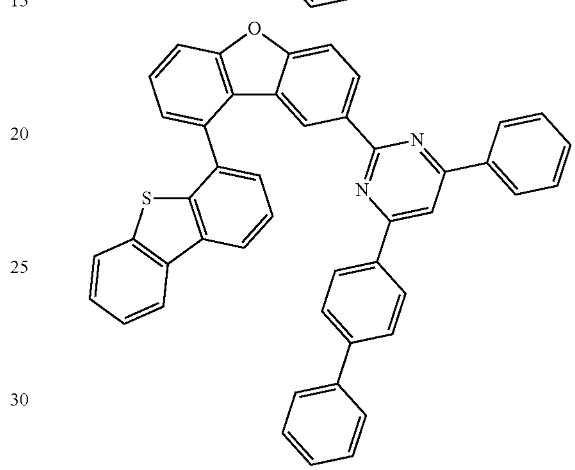
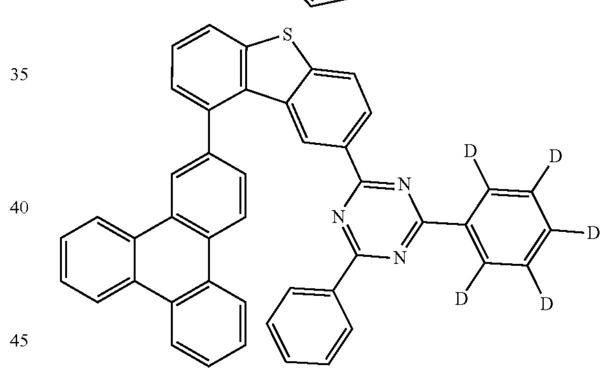
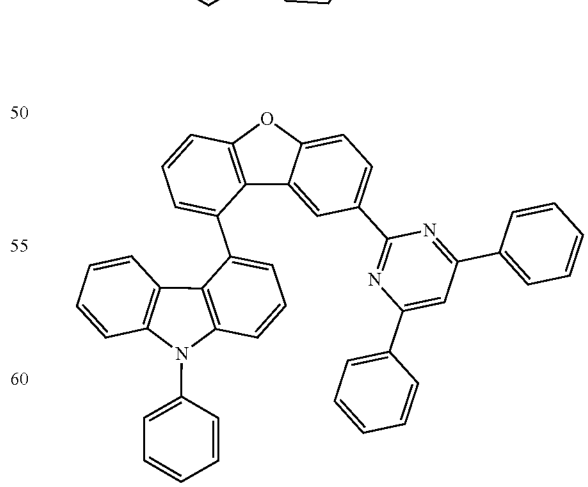

-continued
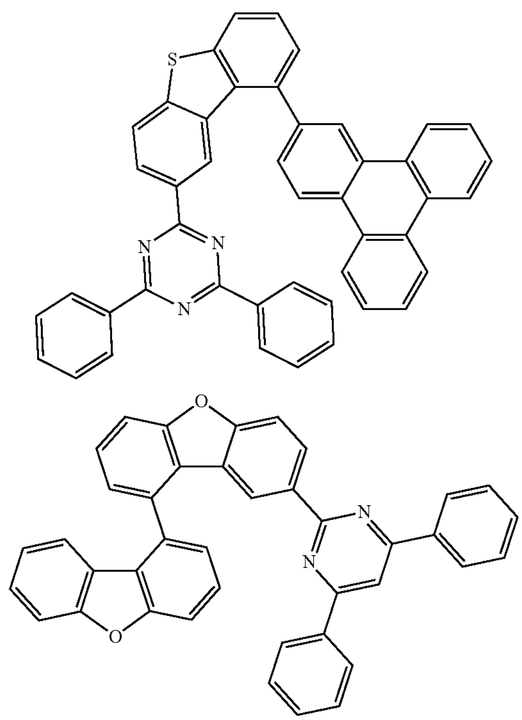
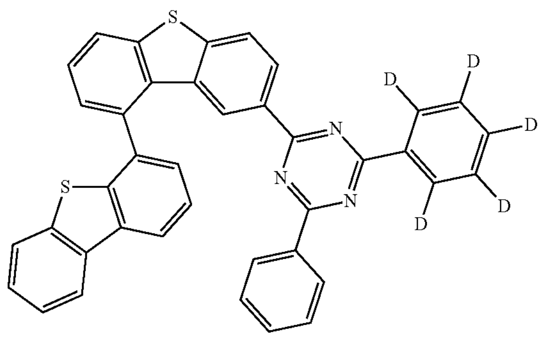
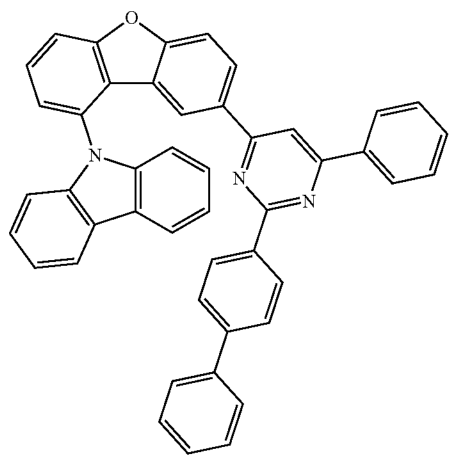
-continued
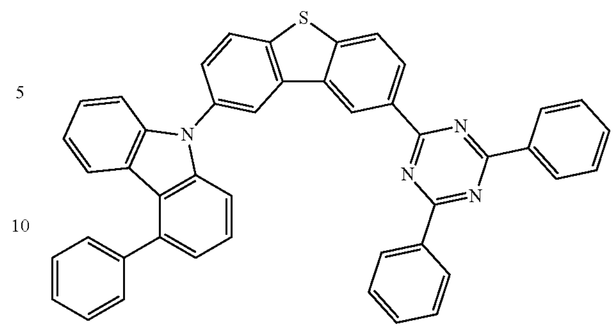
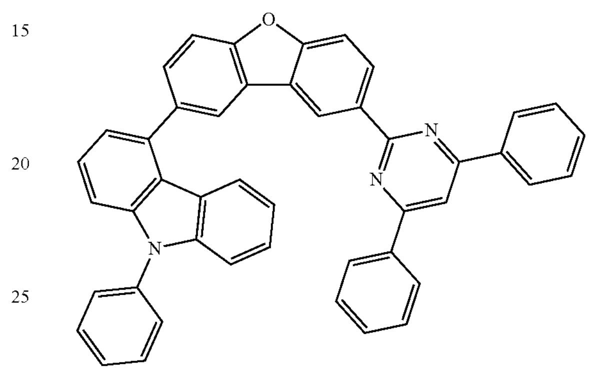
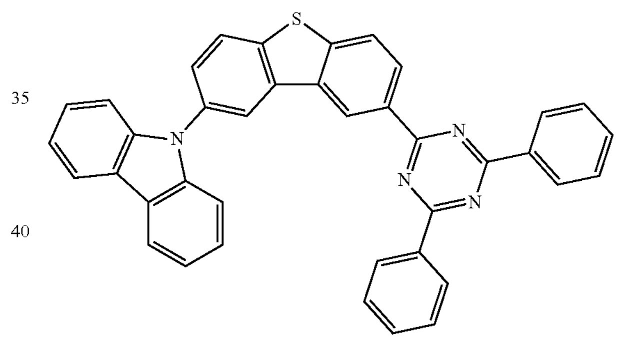
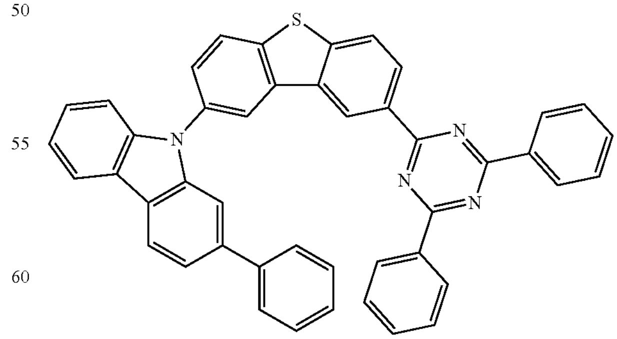

-continued
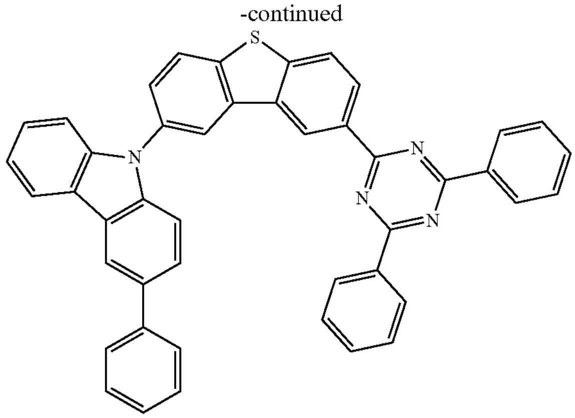
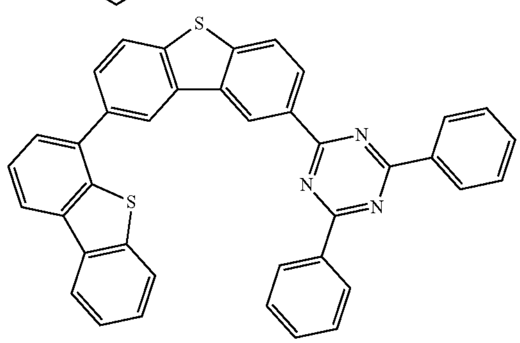
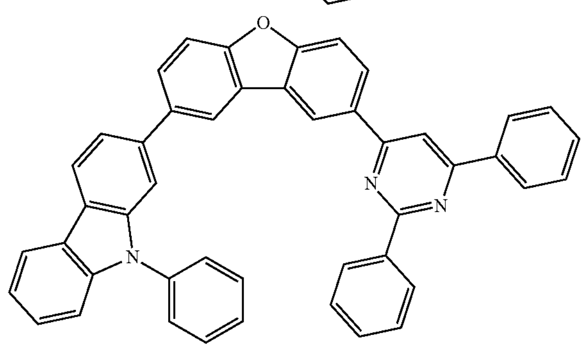
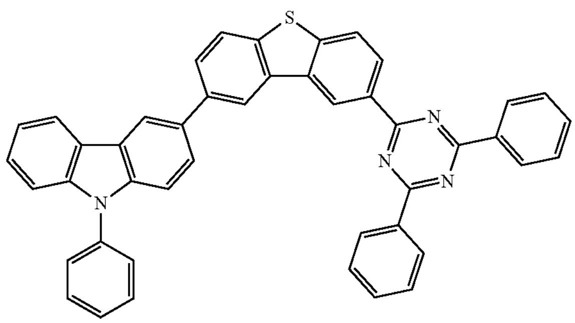
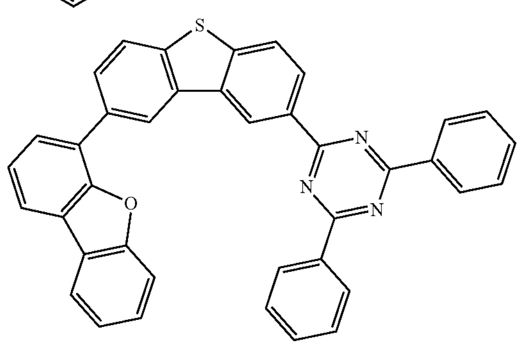
-continued
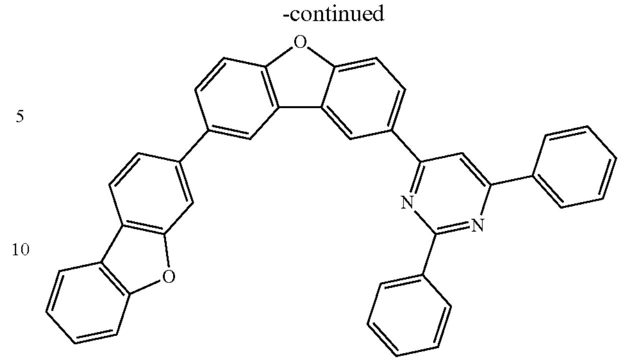
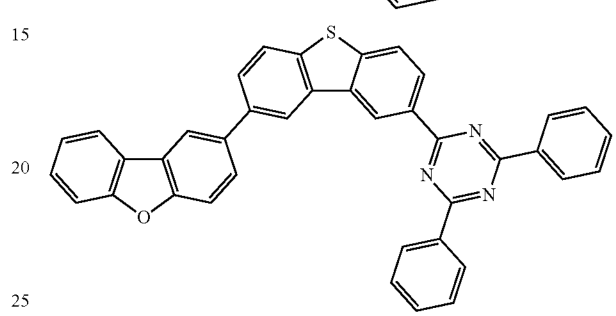
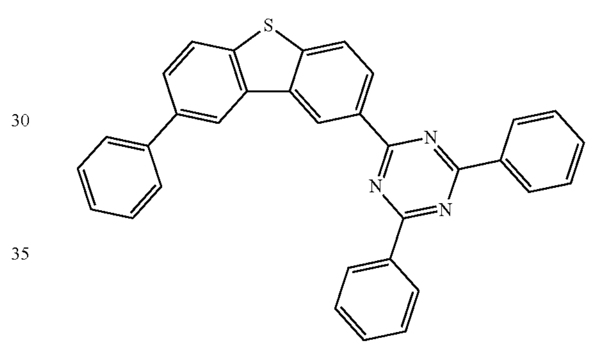
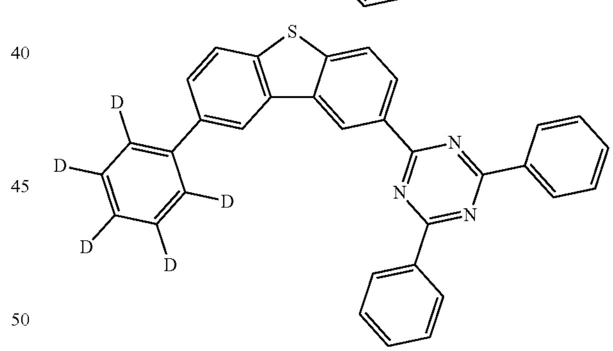
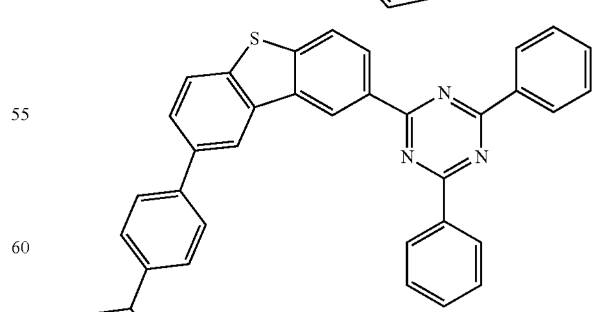

-continued
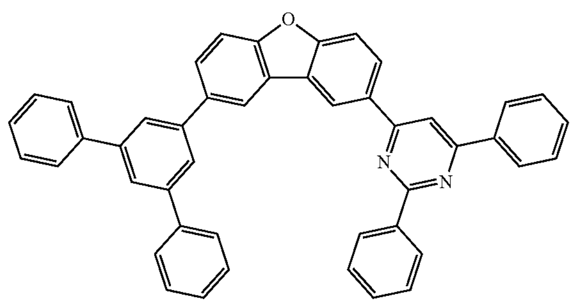
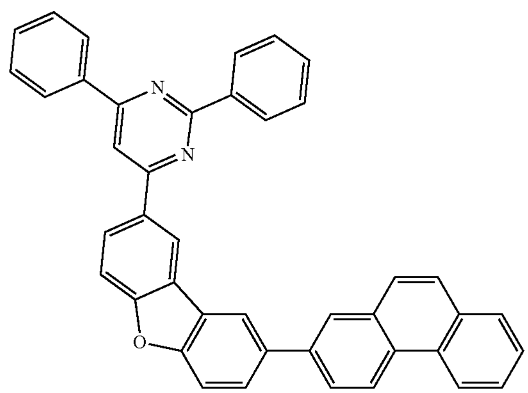
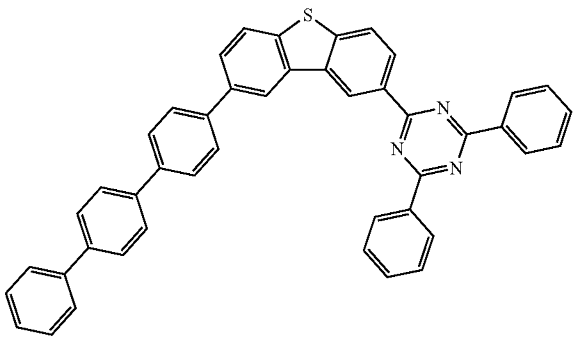
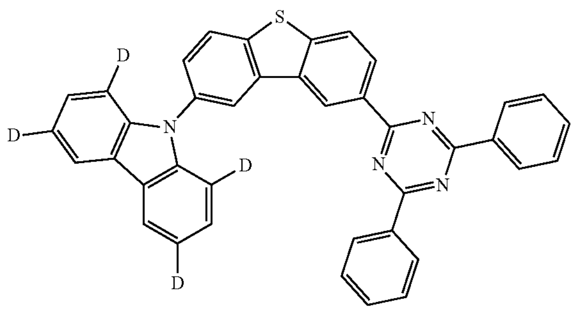
-continued
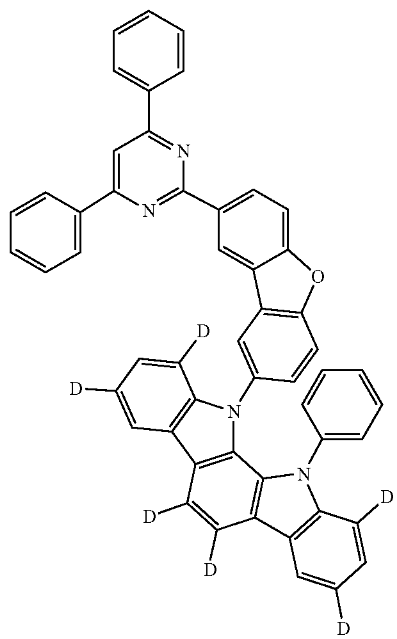
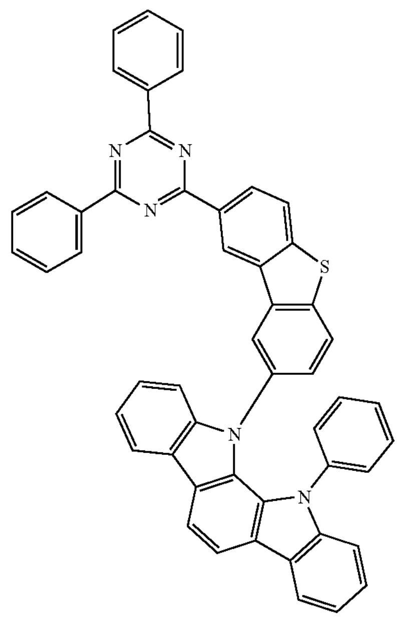
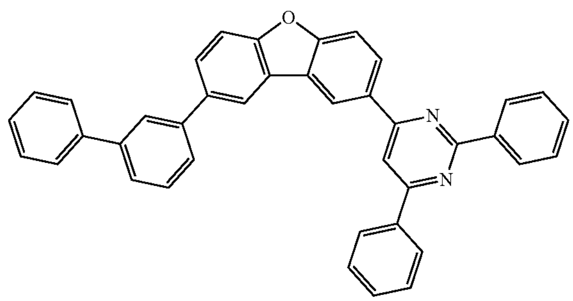

-continued
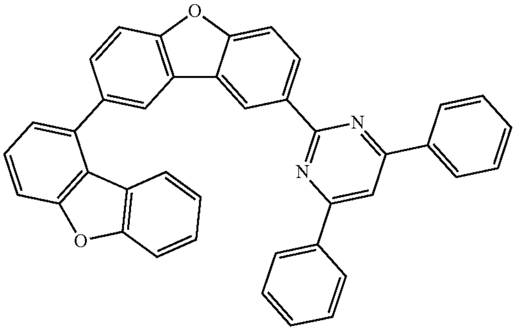
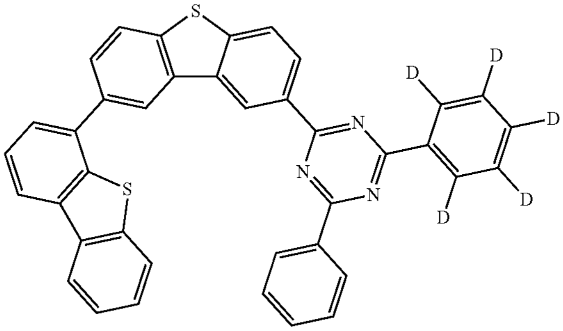
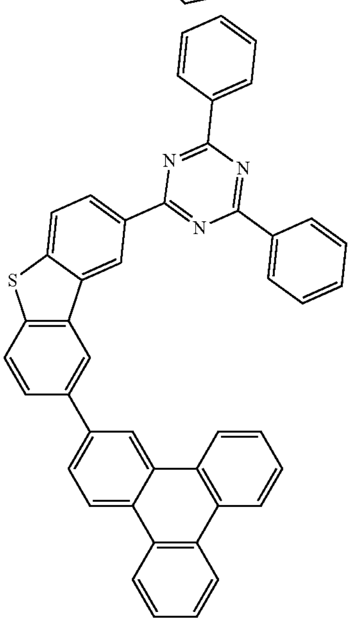
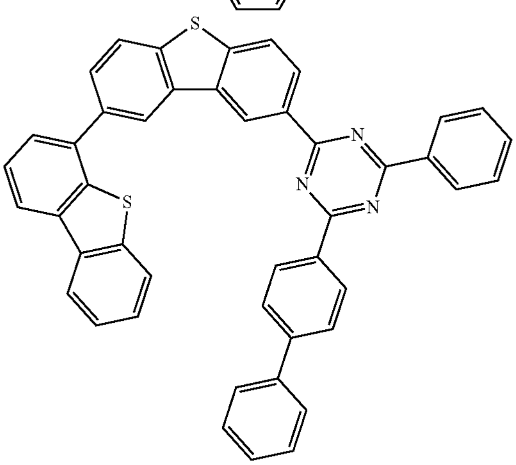
-continued
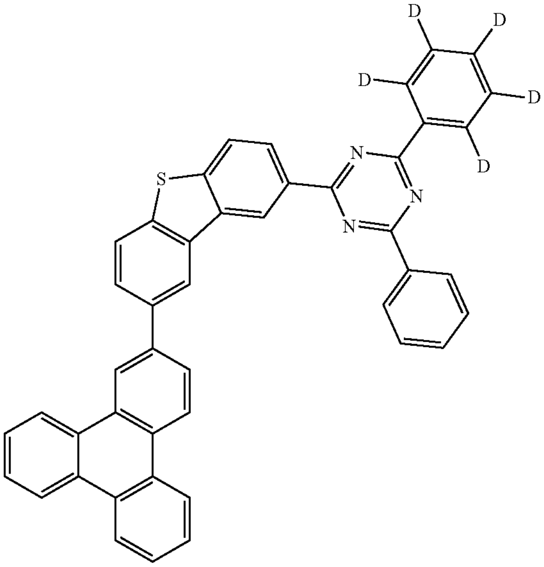
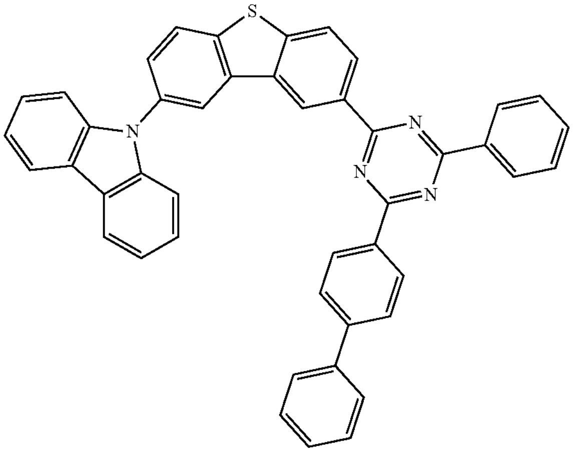
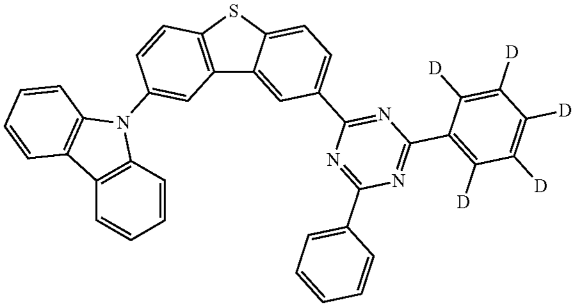
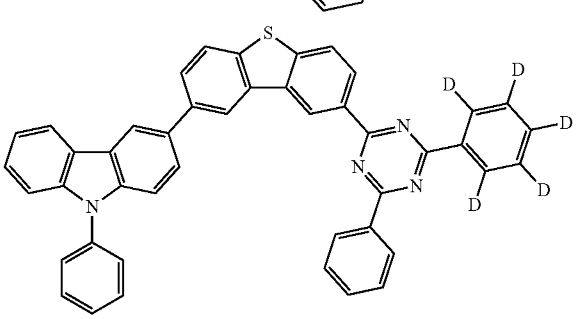

-continued
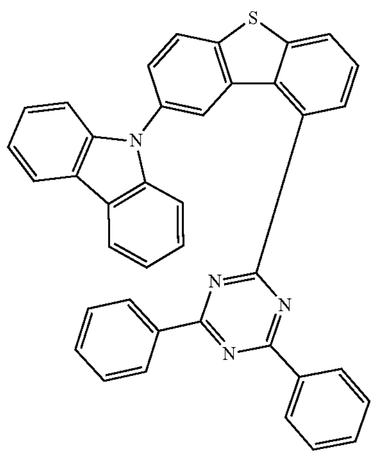
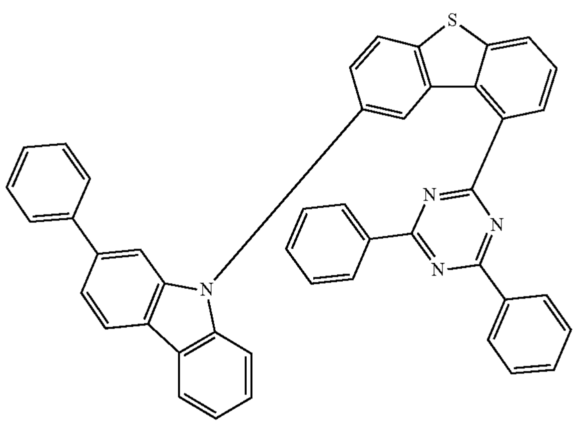
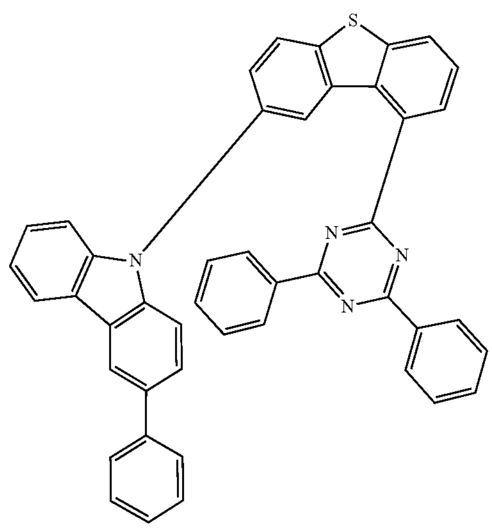
-continued
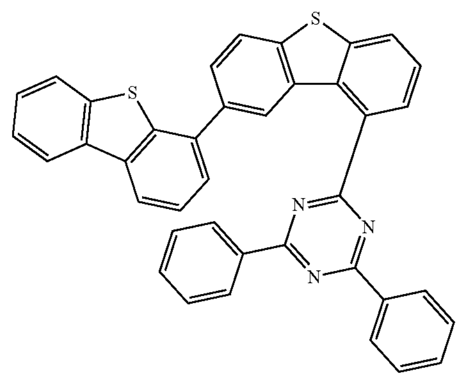
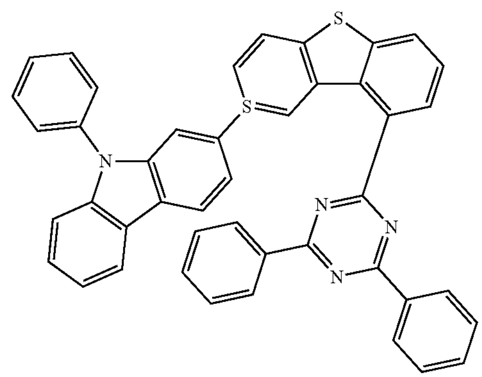
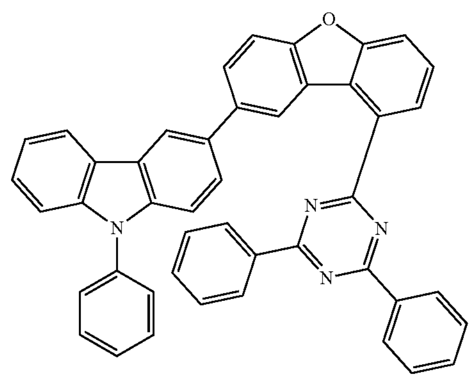
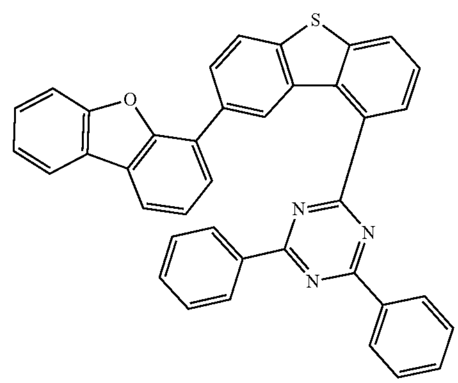

-continued
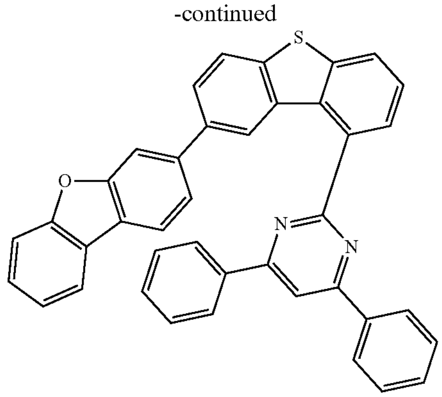
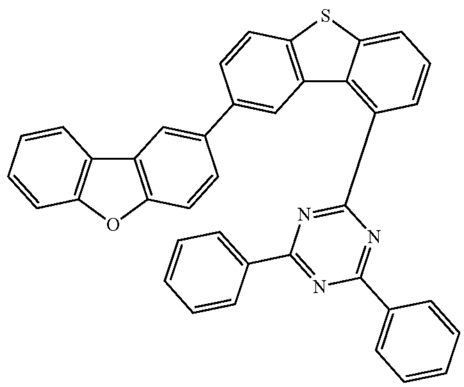
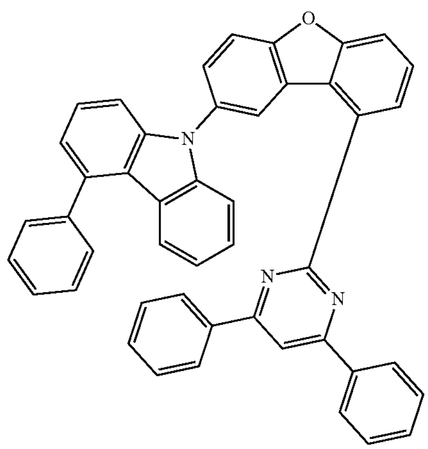
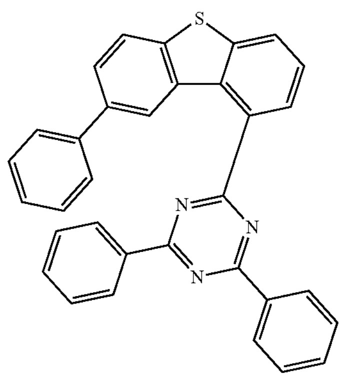
-continued
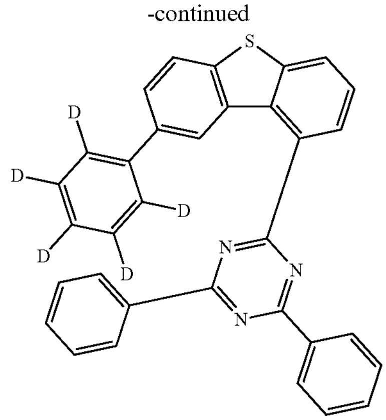
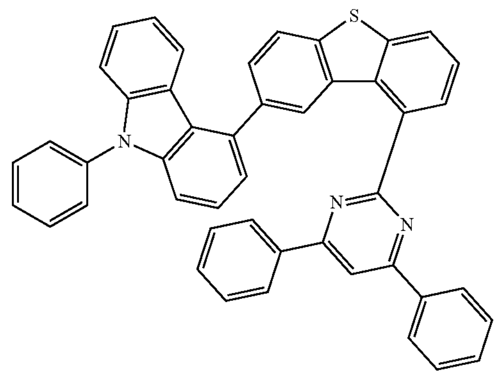
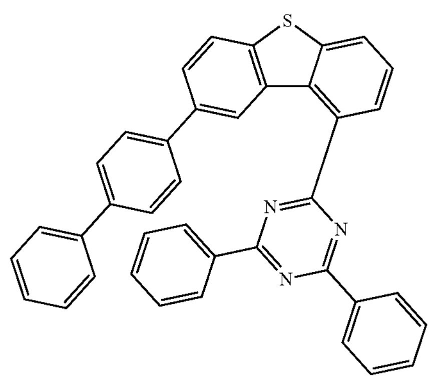
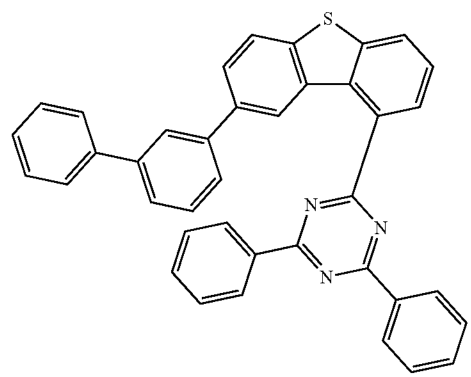

-continued
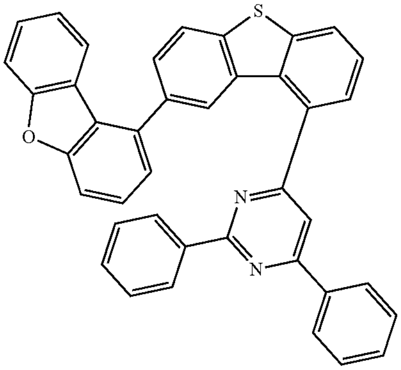
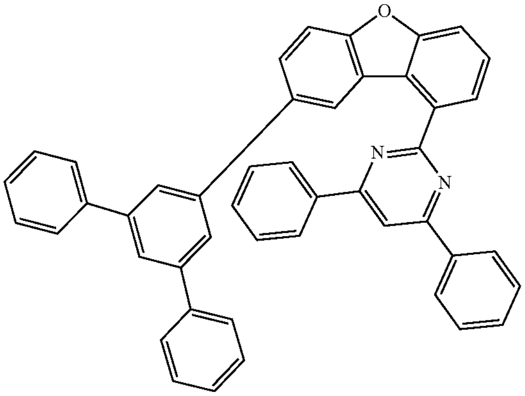
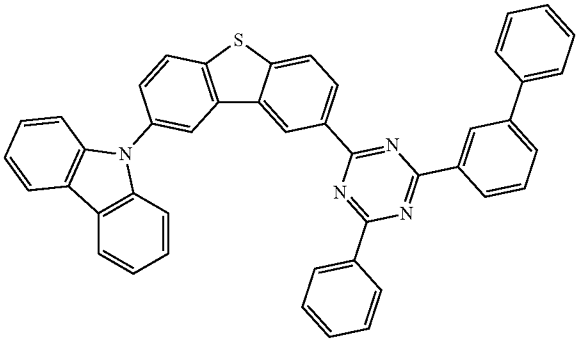
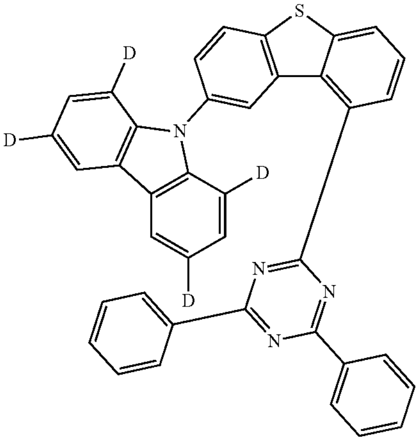
-continued
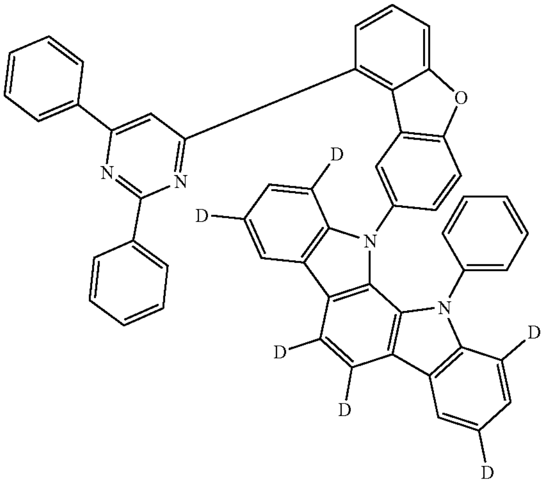
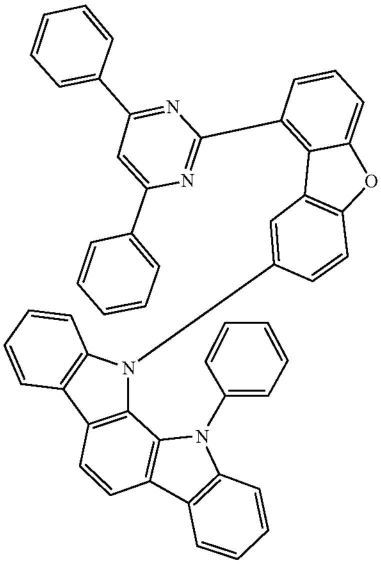
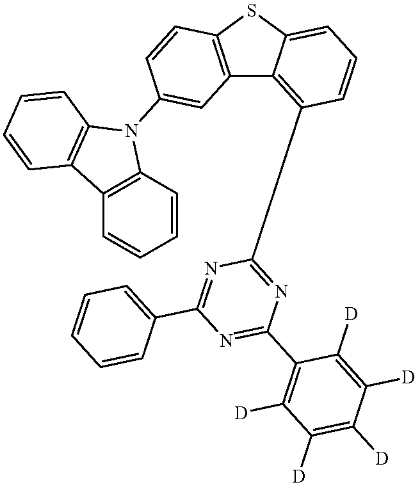

-continued
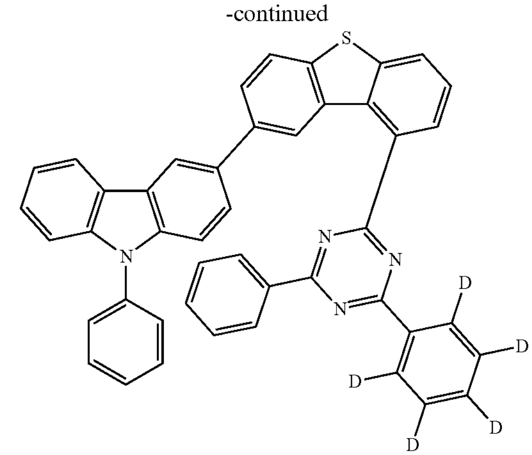
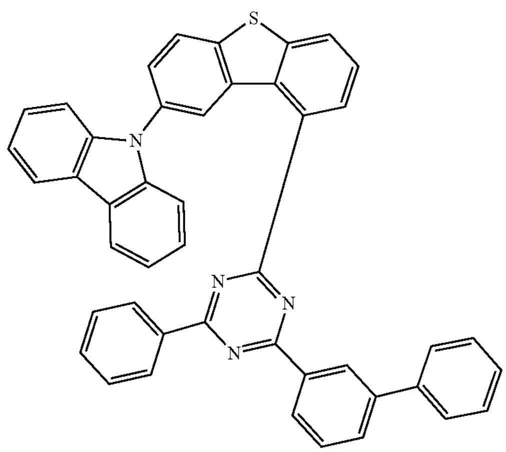
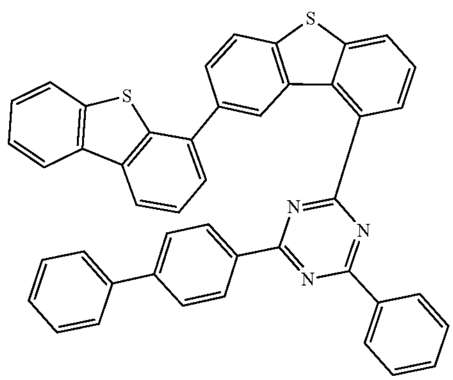
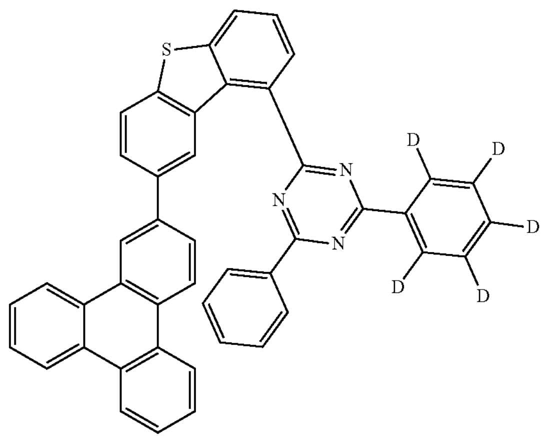
-continued
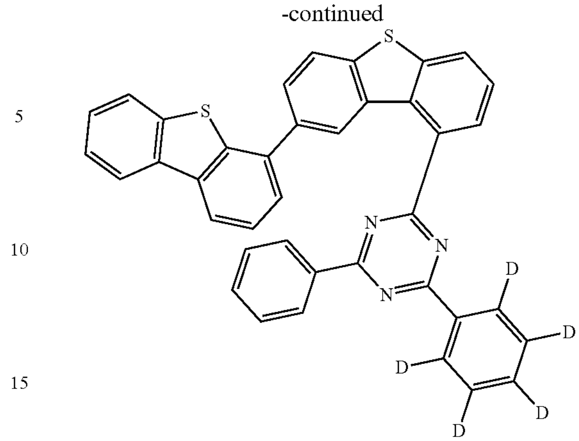
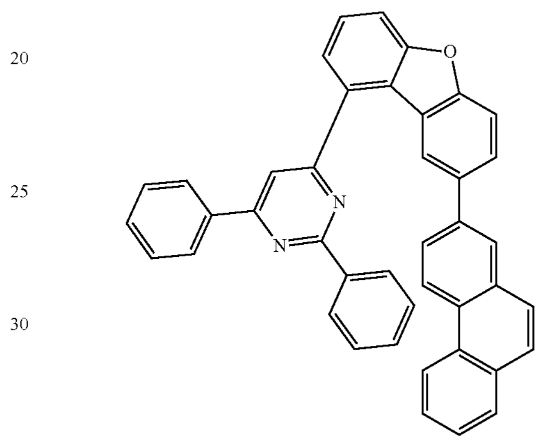
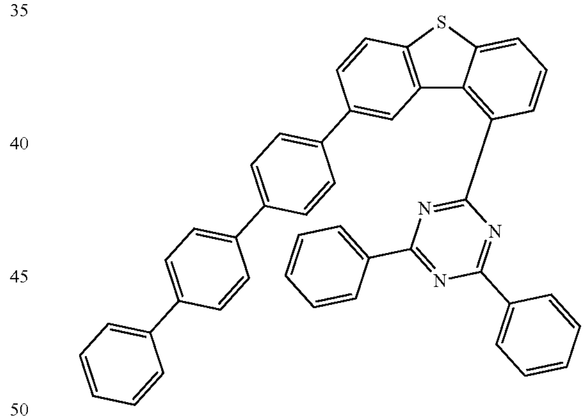
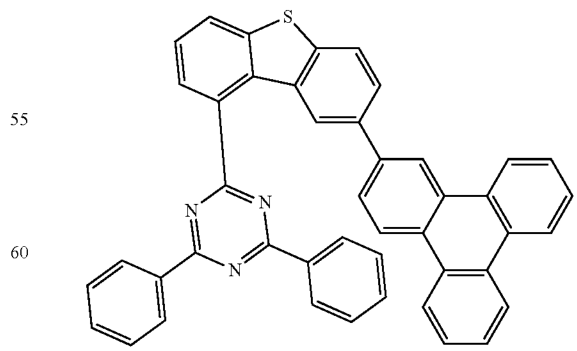

-continued
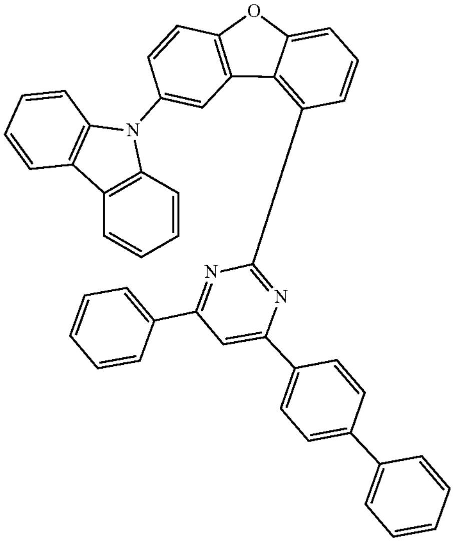
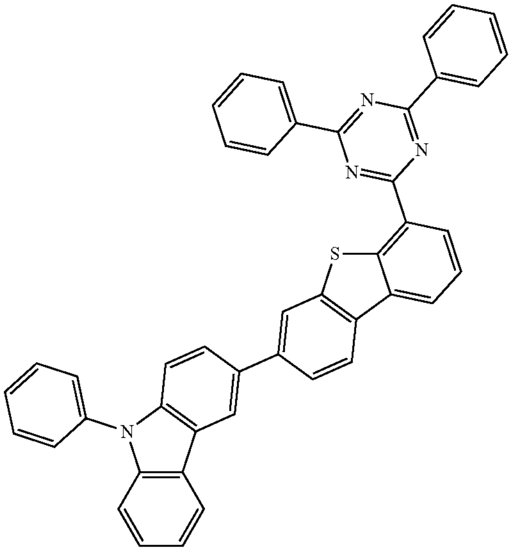
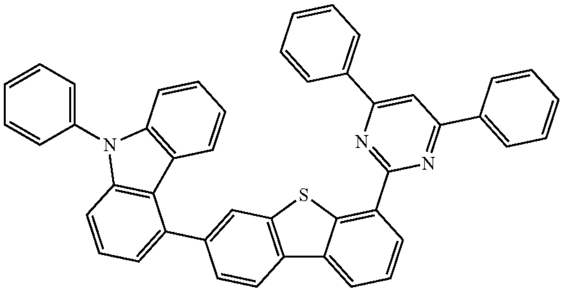
-continued
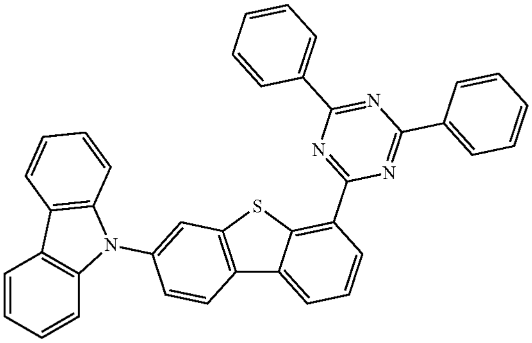
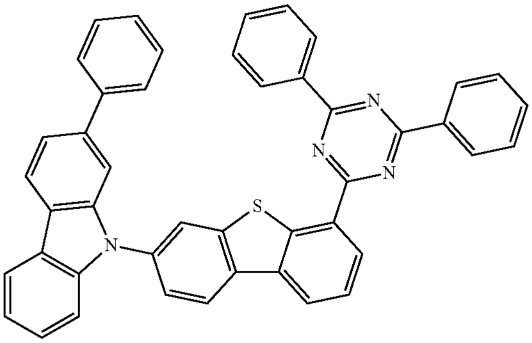
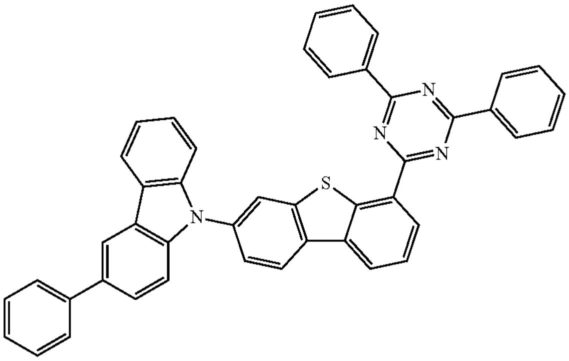
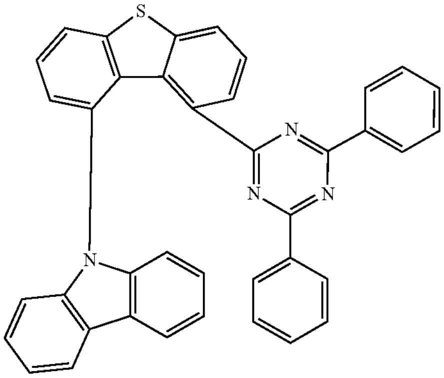

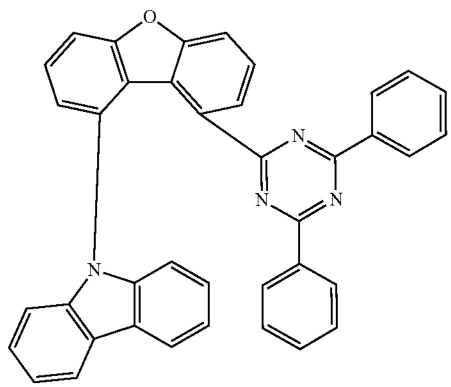
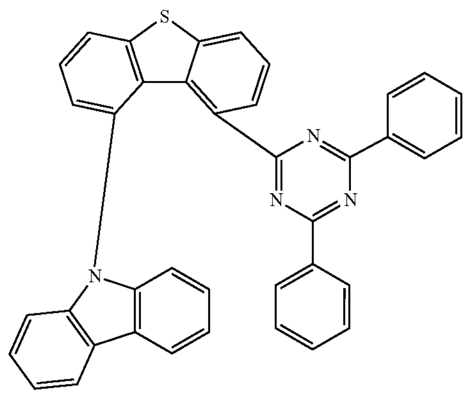
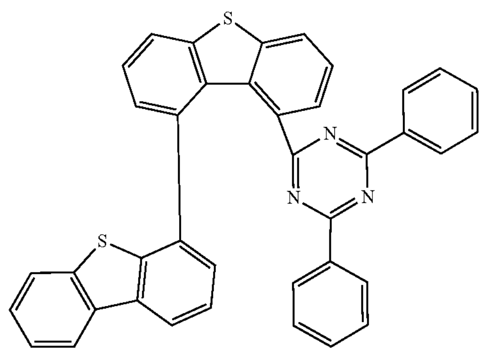
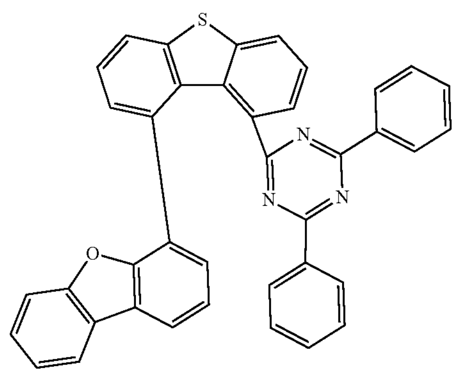
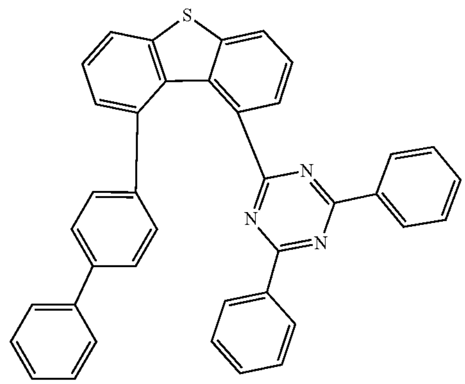
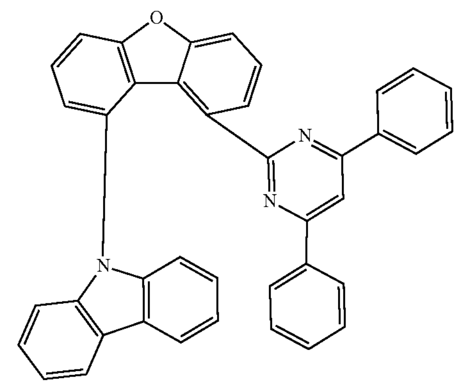
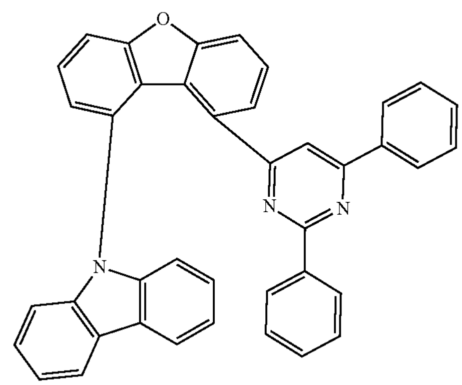
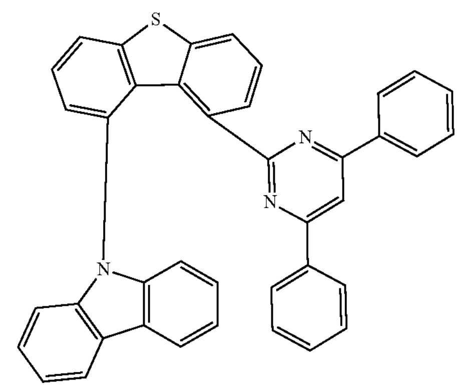

-continued
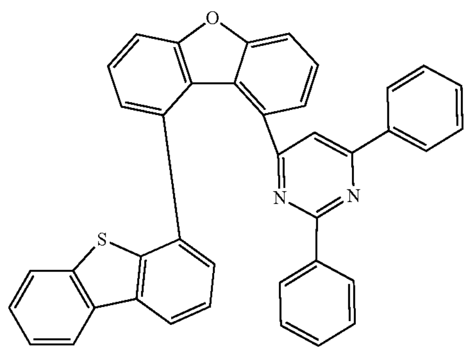
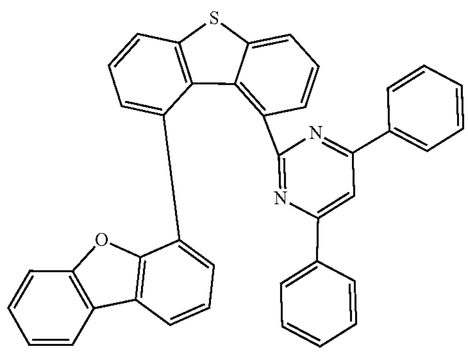
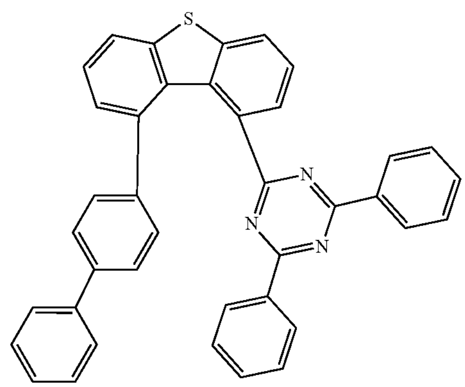
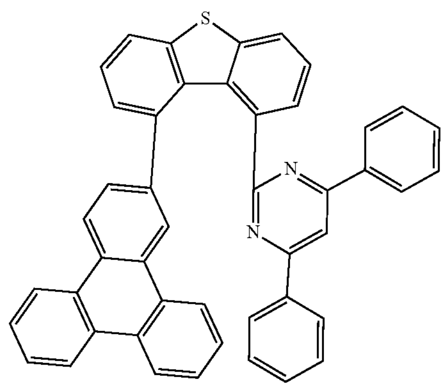
-continued
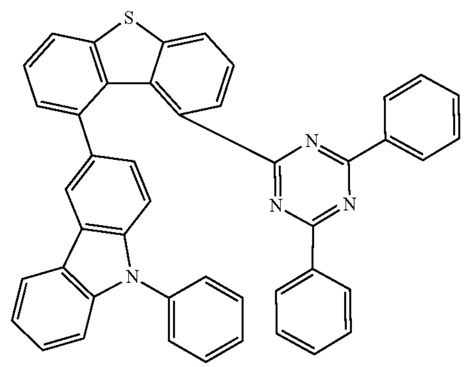
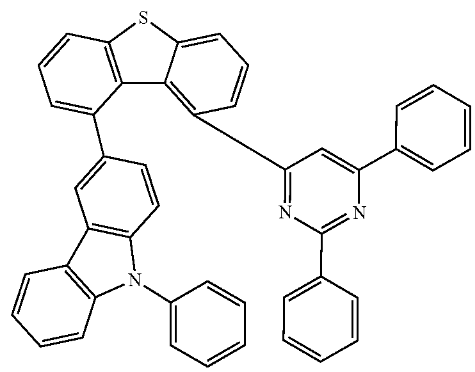
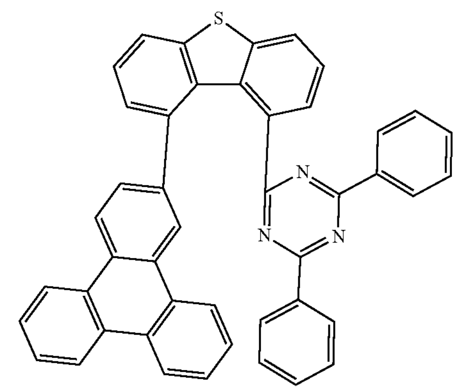
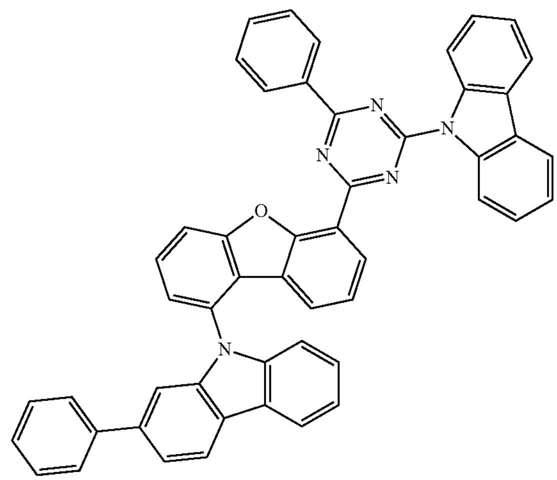

-continued
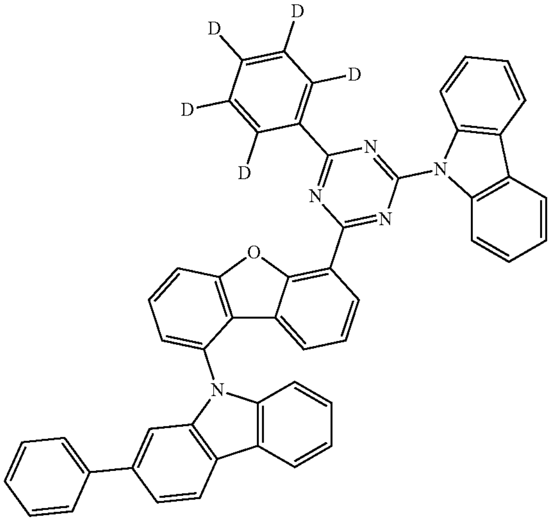
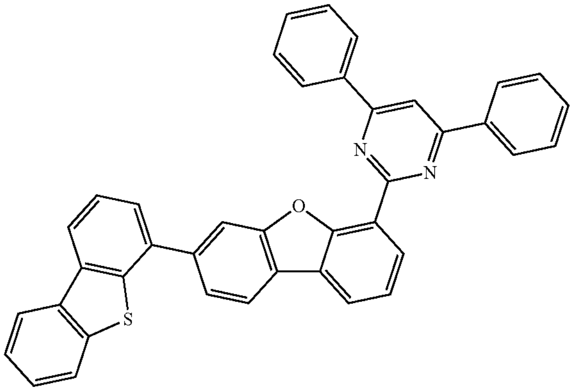
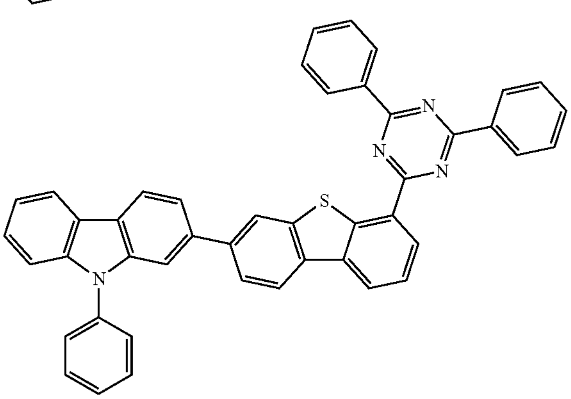
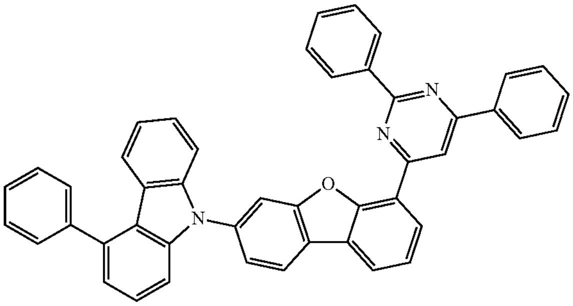
-continued
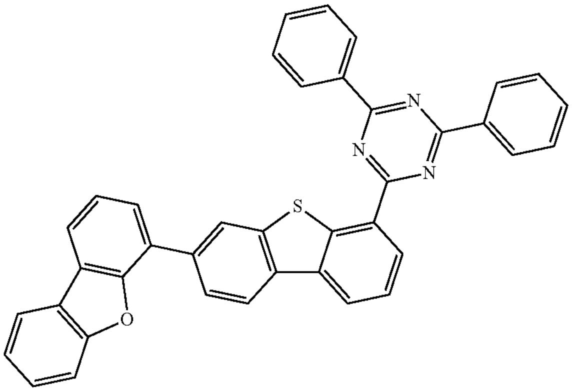
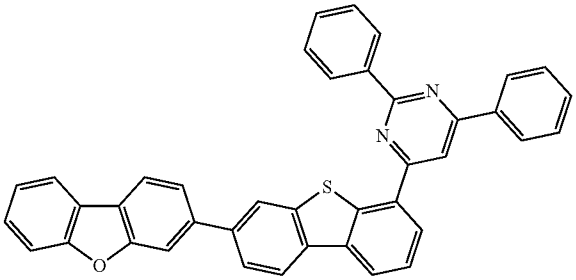
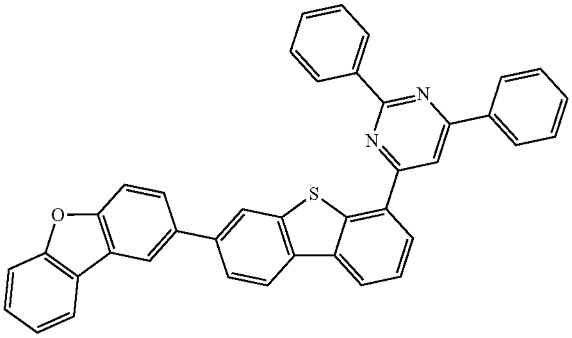
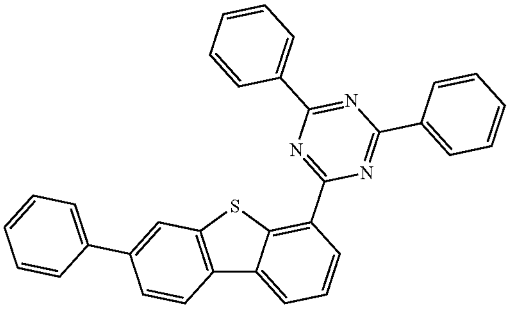
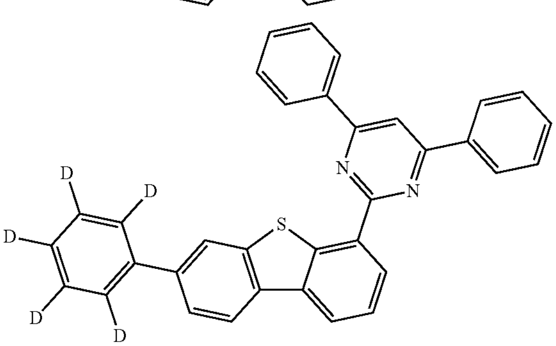

-continued
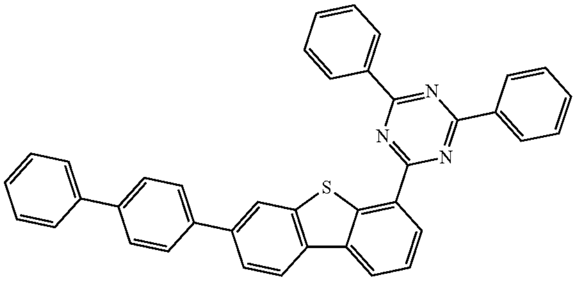
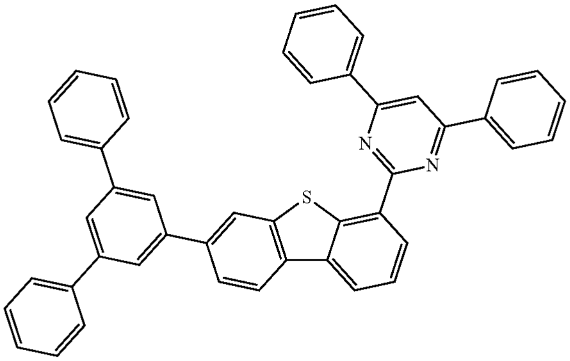
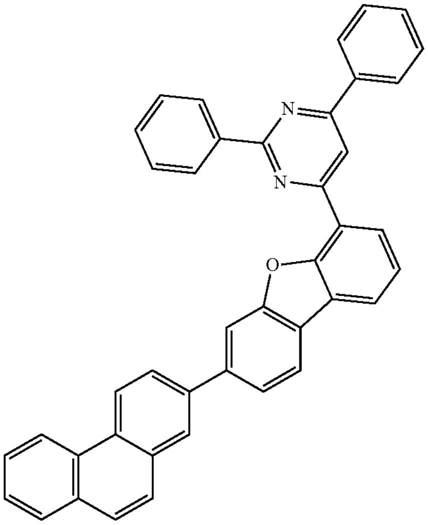
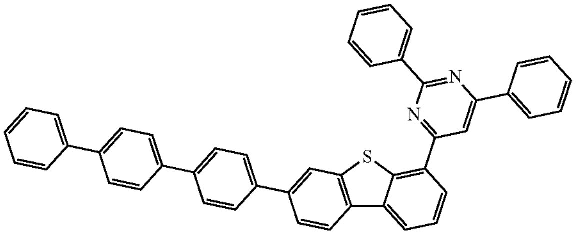
-continued
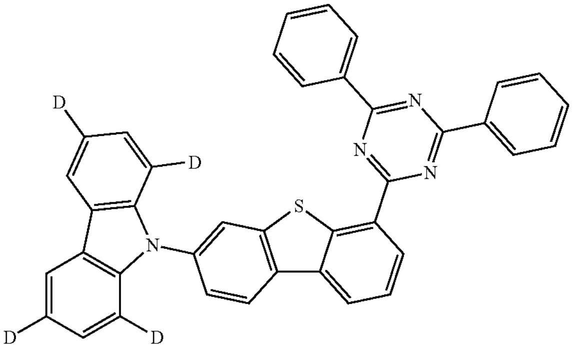
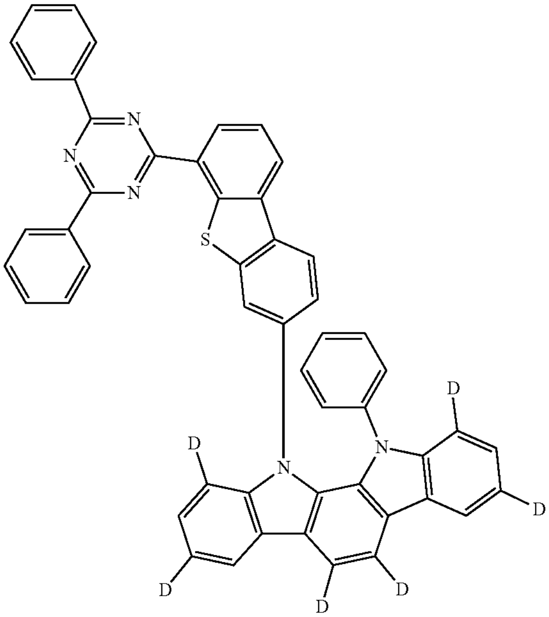
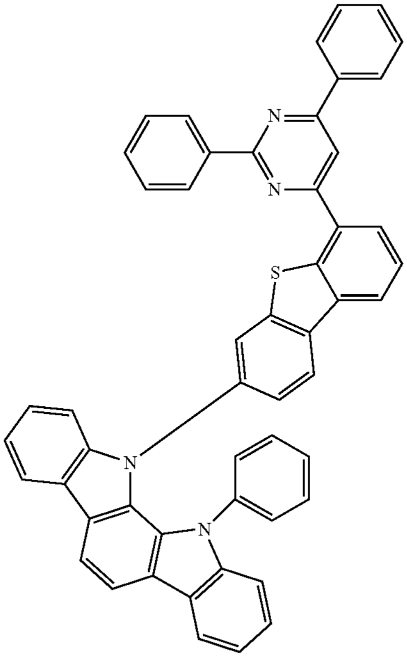

-continued
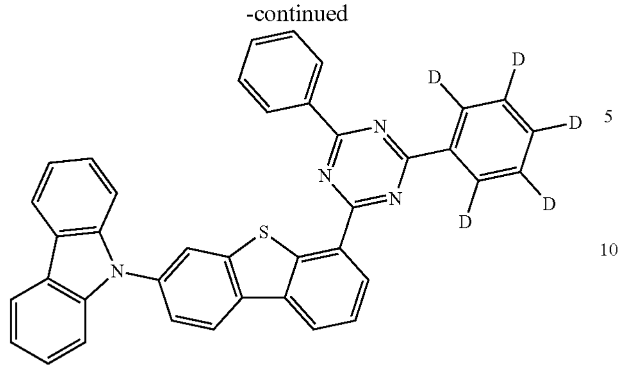
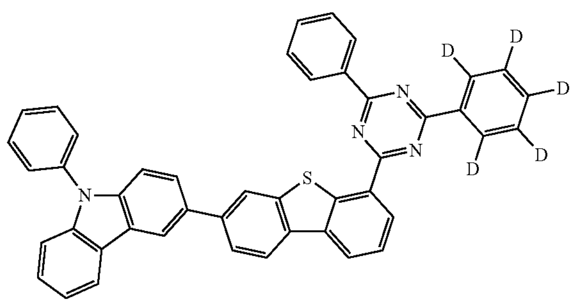
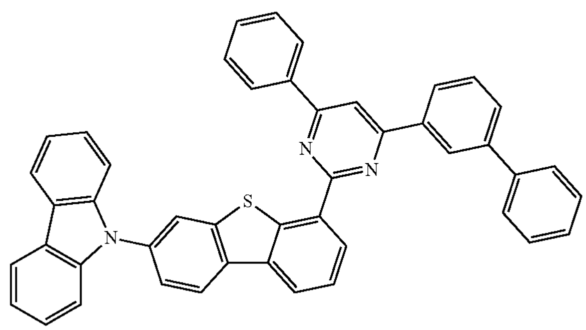
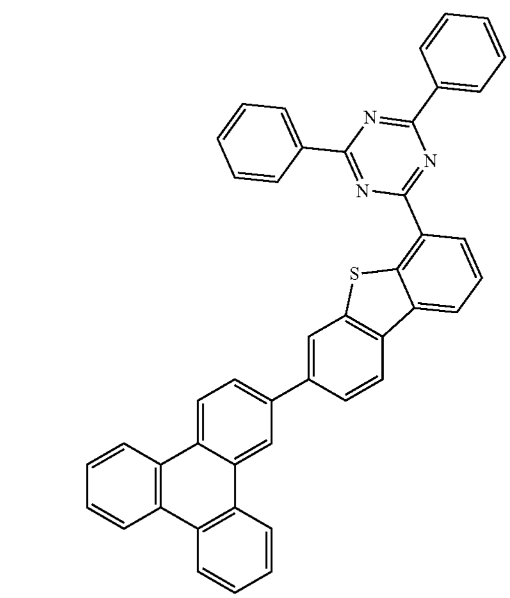
-continued
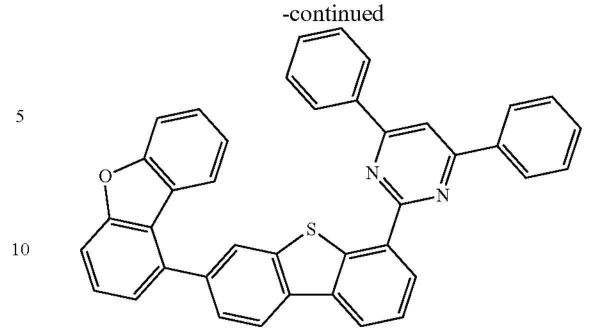
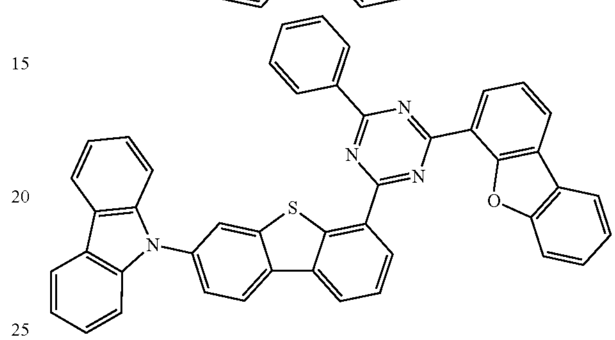
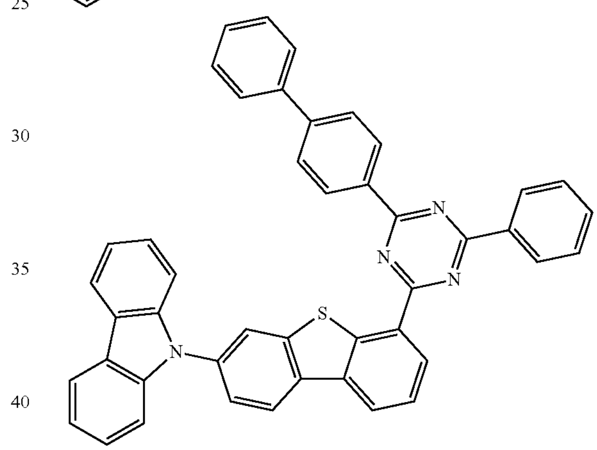
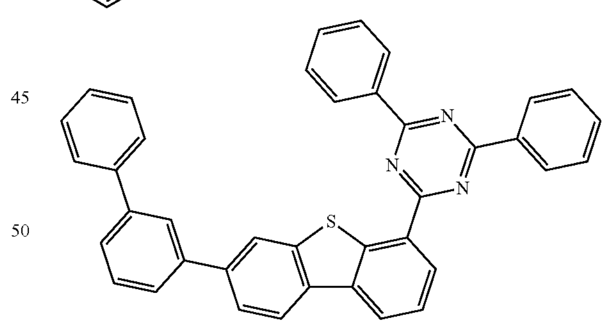
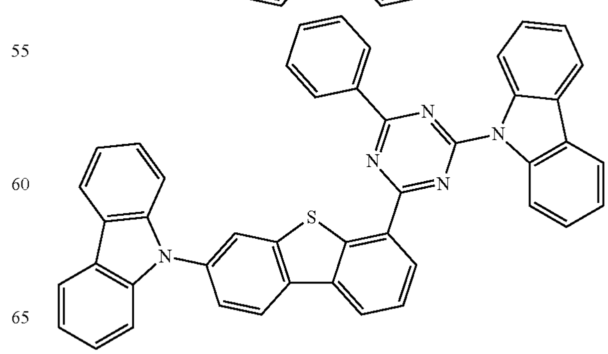
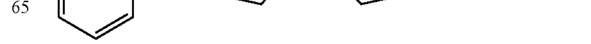
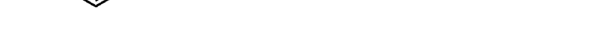
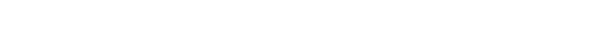
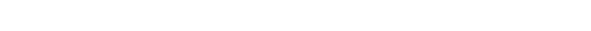

-continued
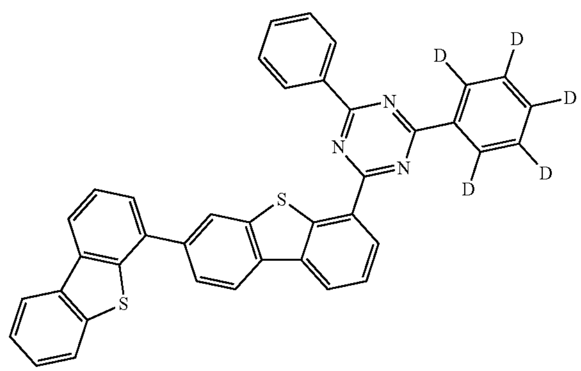
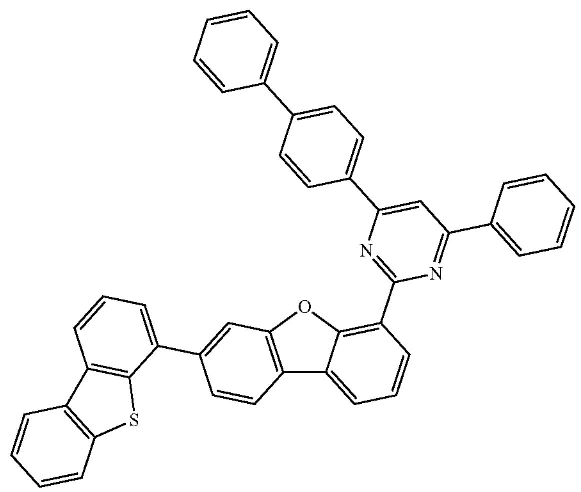
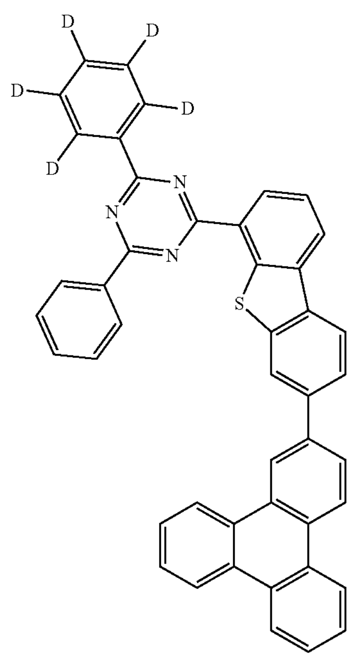 [SMILES: [2H]c1c([2H])c([2H])c(-c2nc(-c3ccccc3)nc(-c3cccc4c3sc3cc(-c5ccc6c7ccccc7c7ccccc7c6c5)ccc34)n2)c([2H])c1[2H]]
-continued
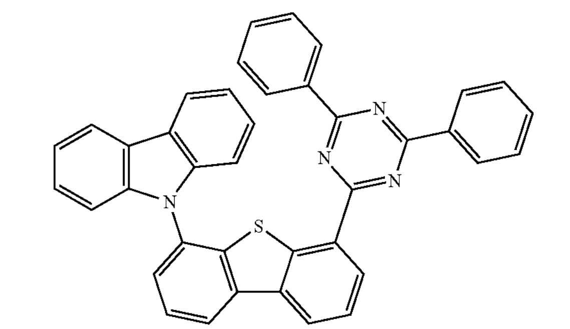
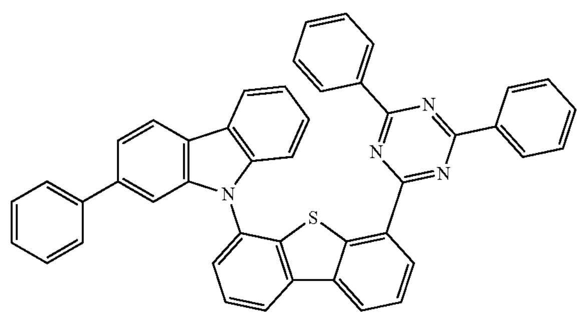
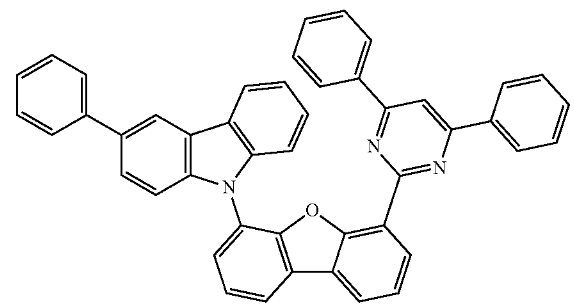
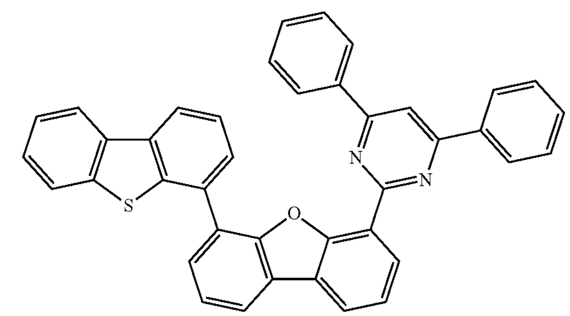
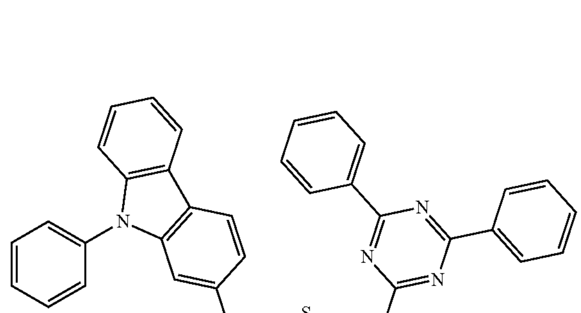
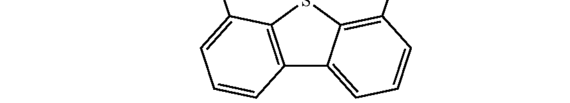

-continued
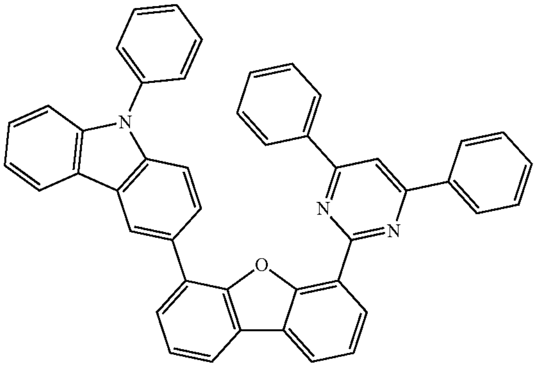
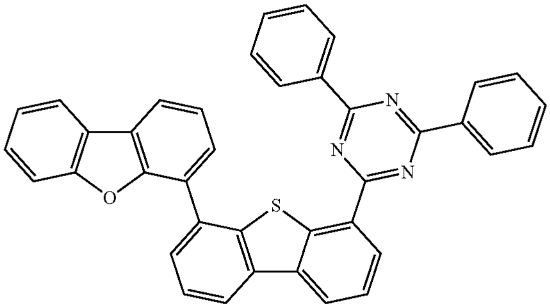
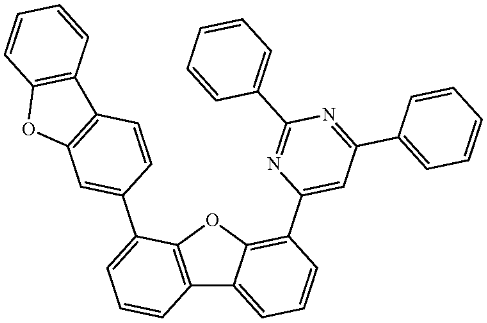
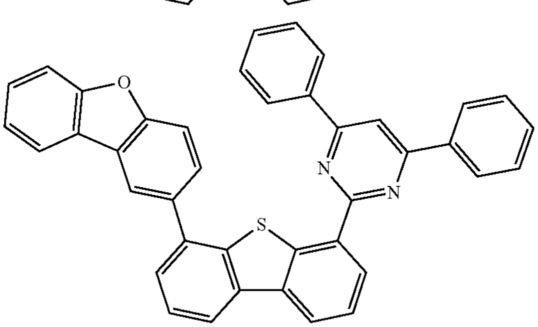
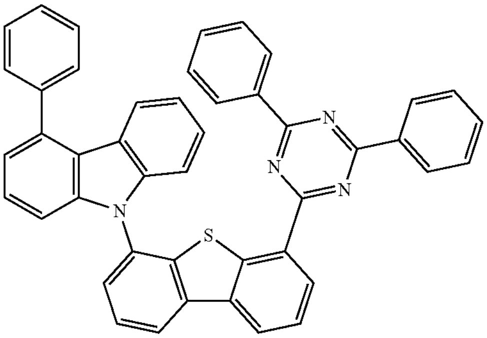
-continued
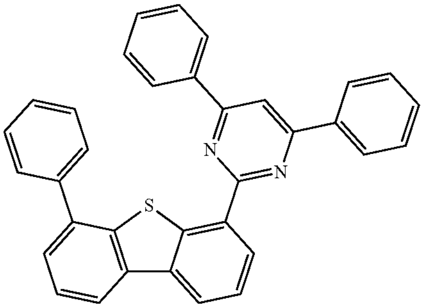
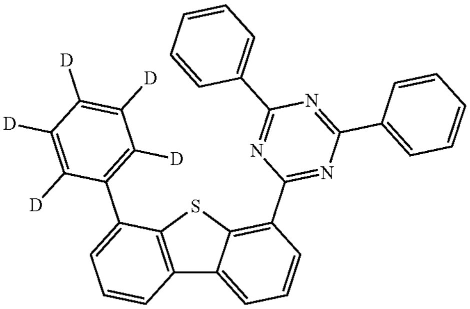
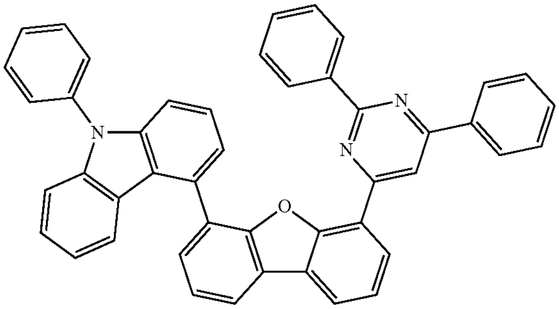
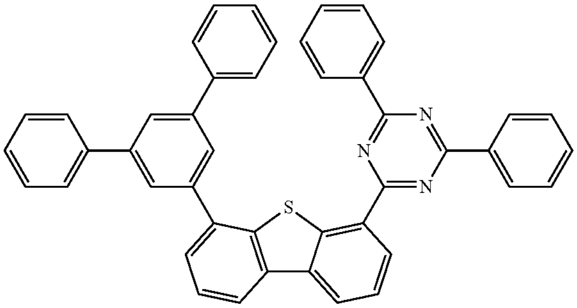
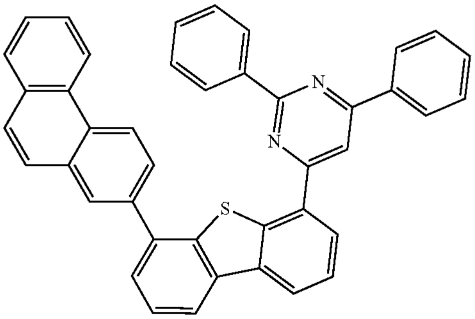

-continued
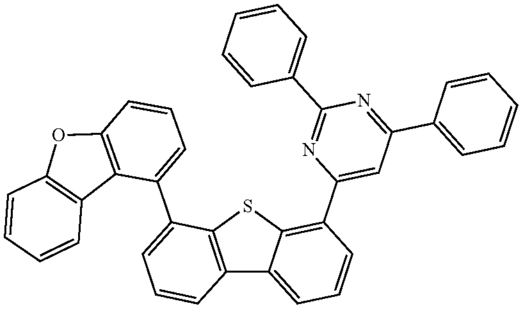
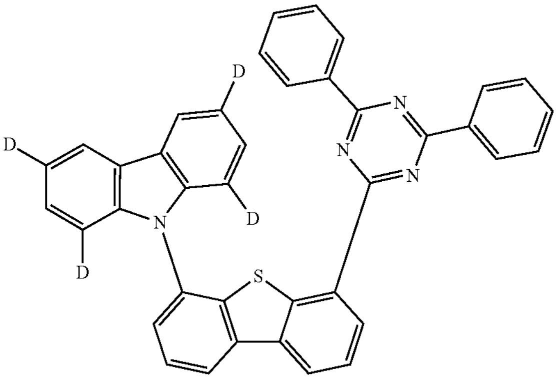
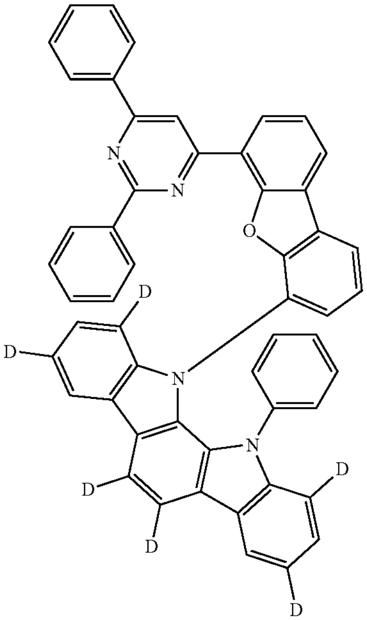
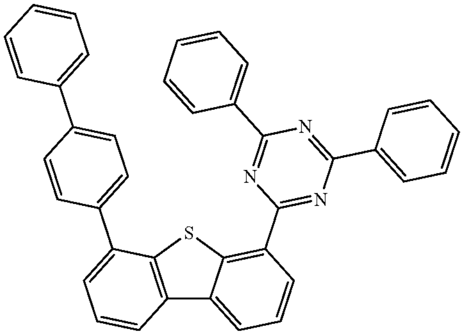
-continued
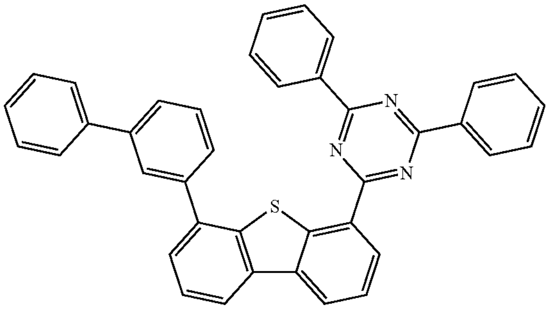
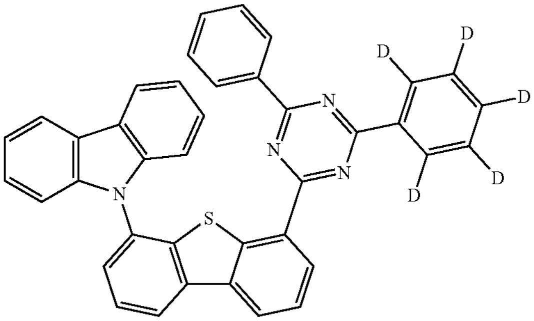
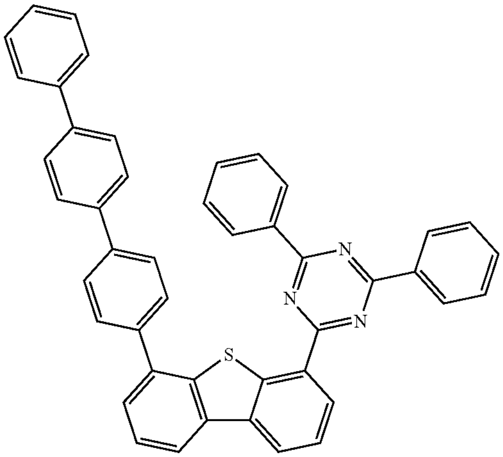
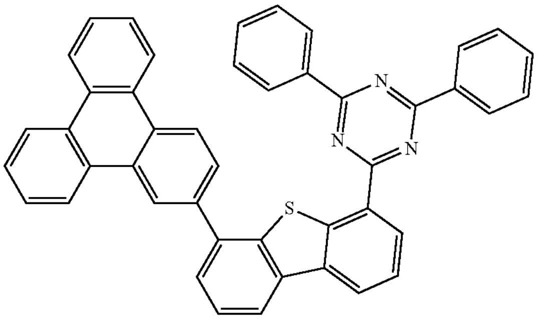

-continued
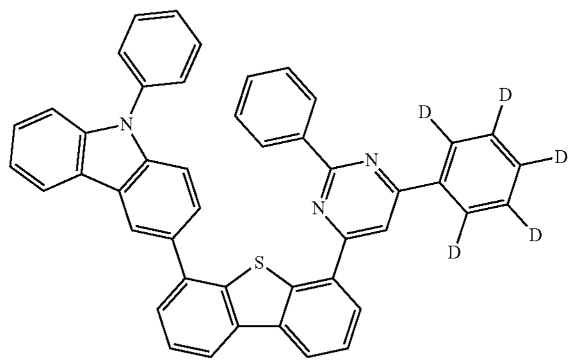
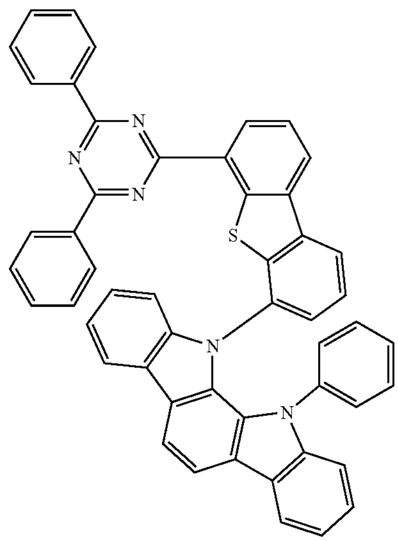
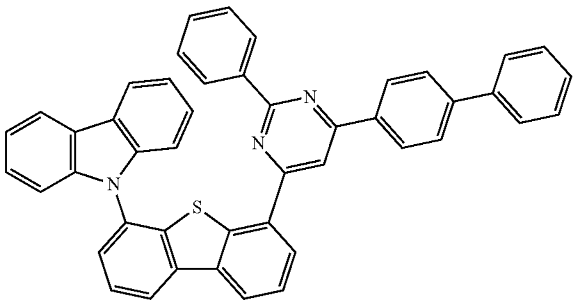
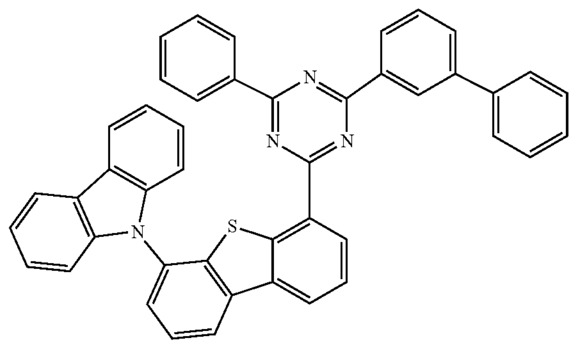
-continued
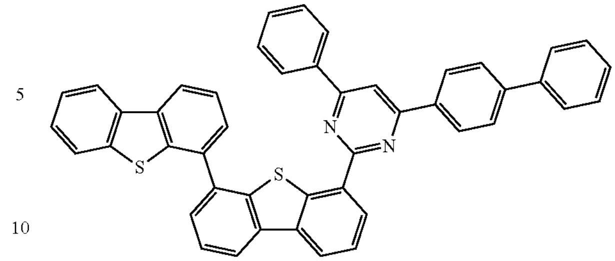
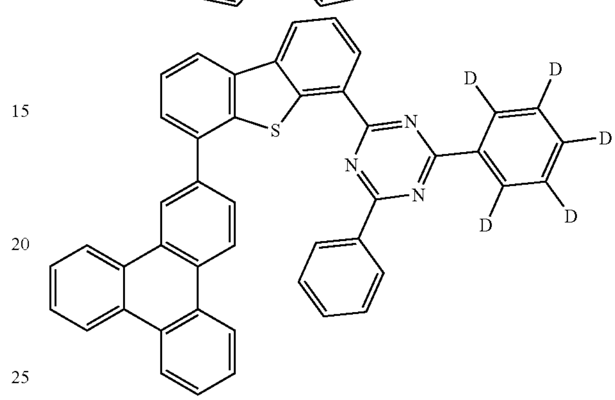
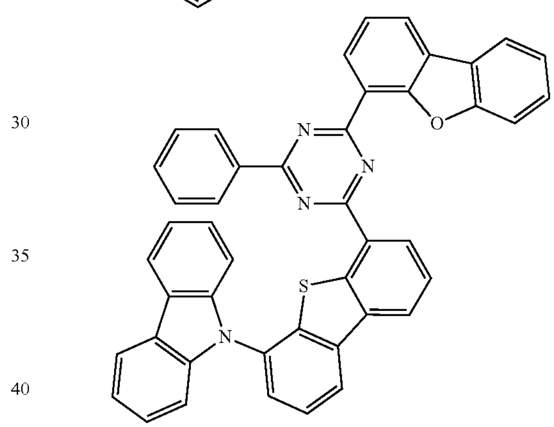
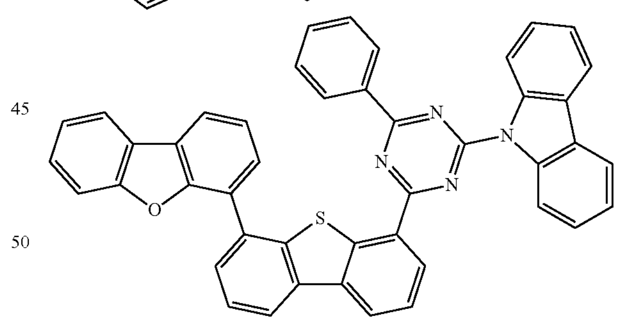
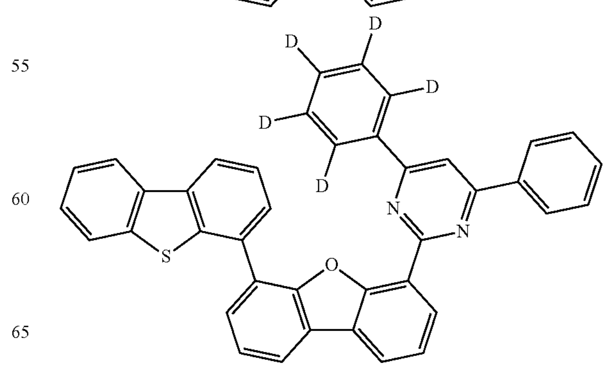

-continued
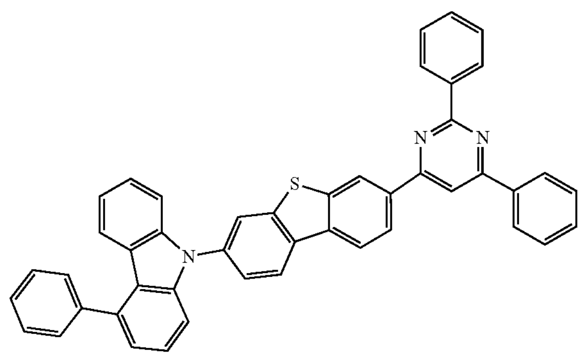
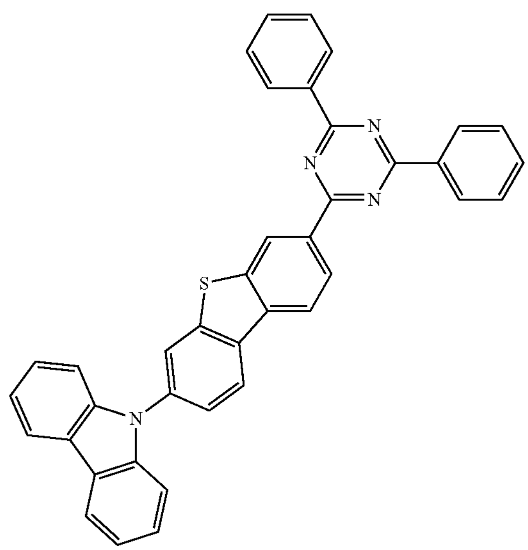
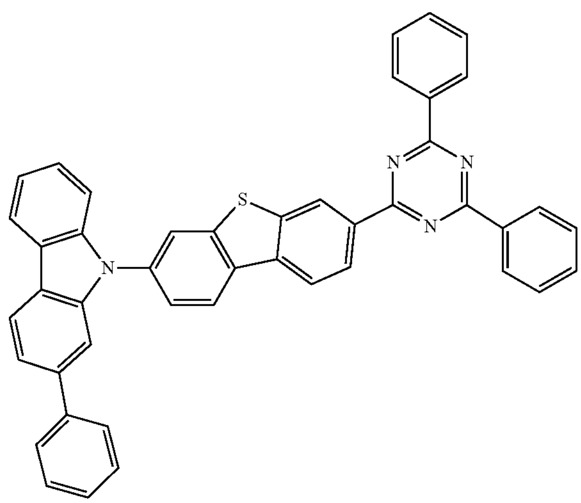
-continued
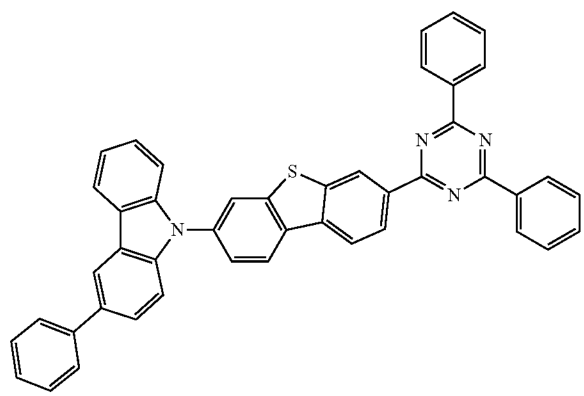
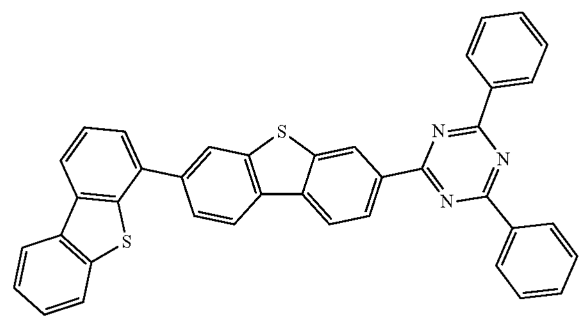
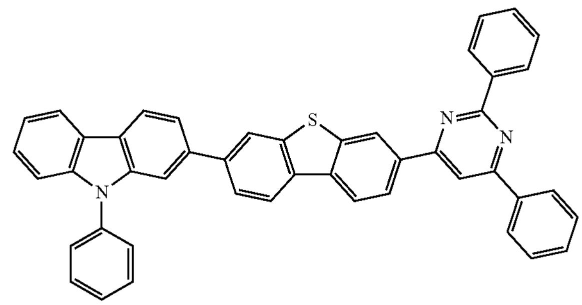
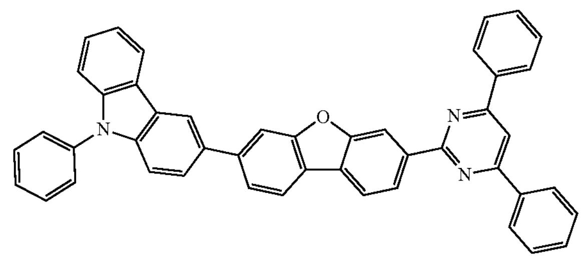
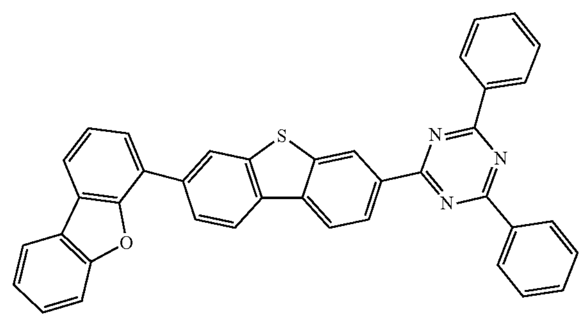

-continued
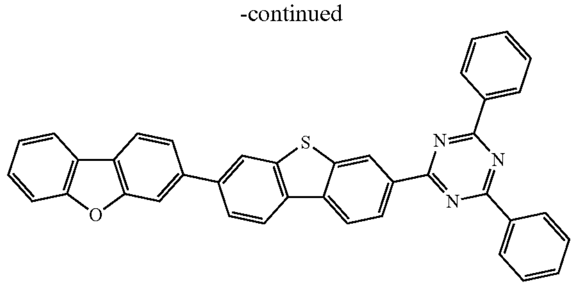
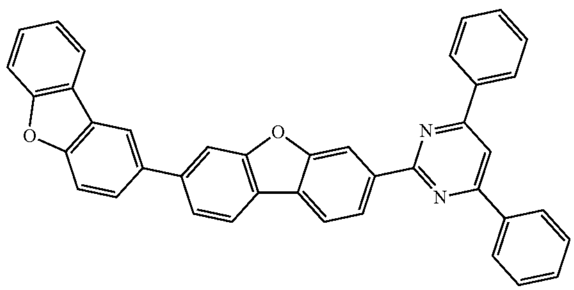
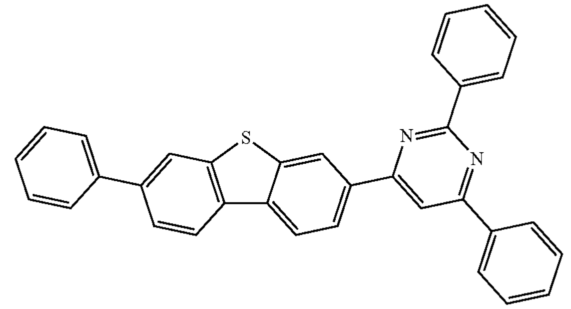
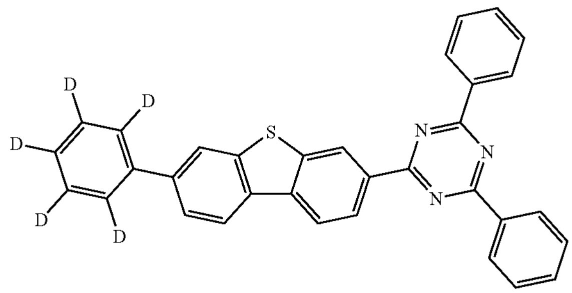
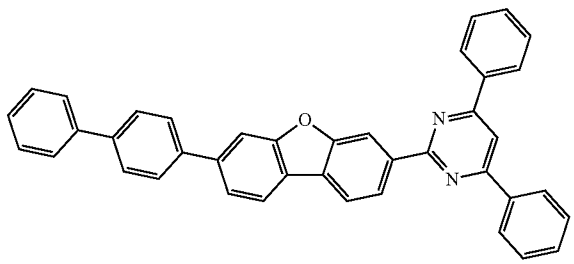
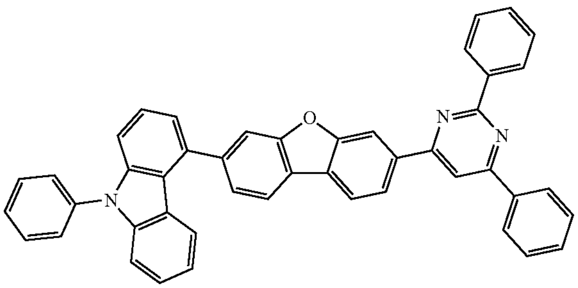
-continued
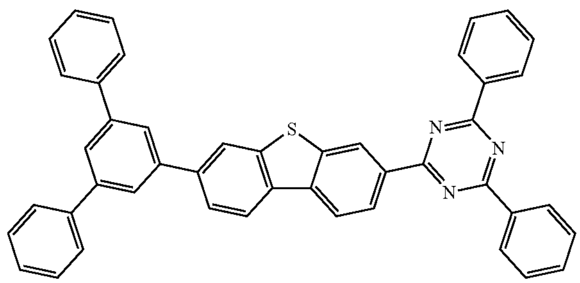
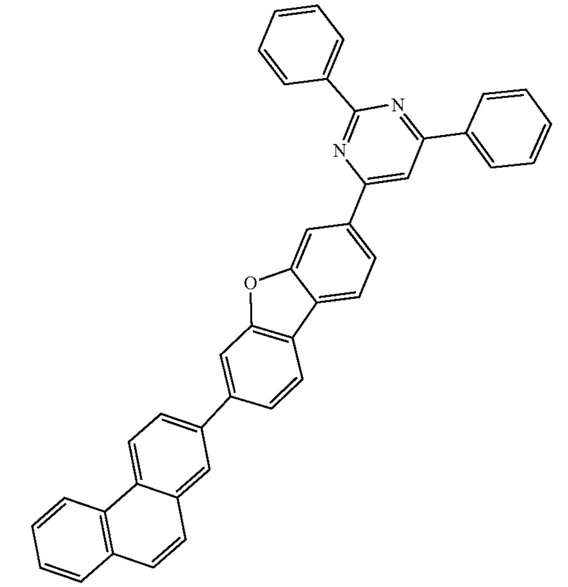
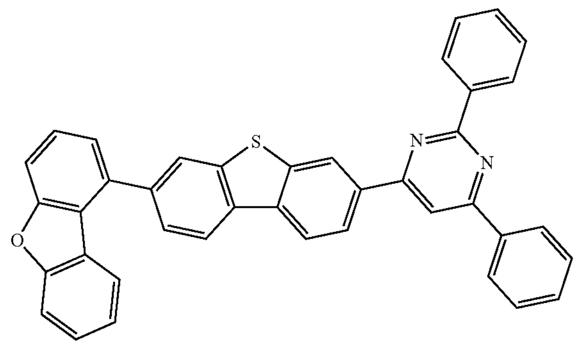
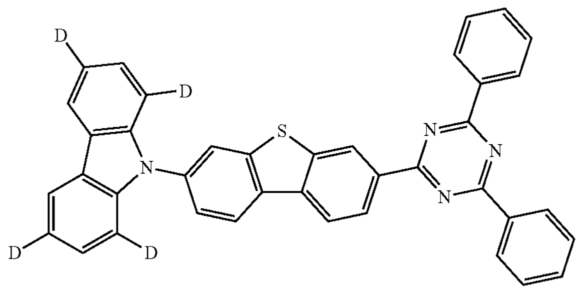

-continued
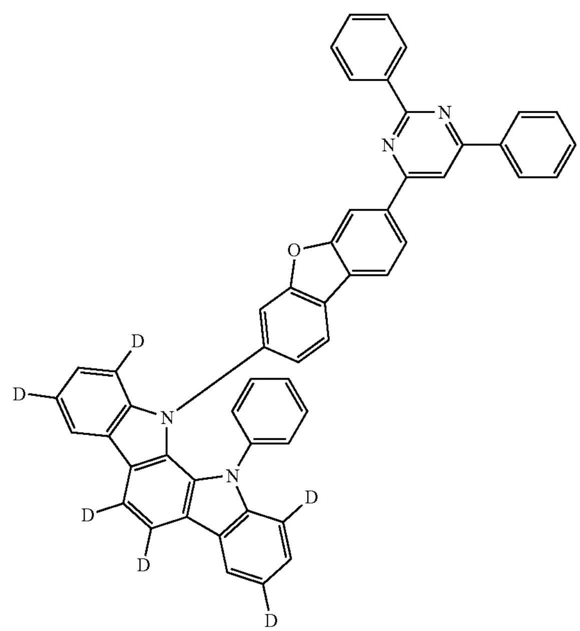
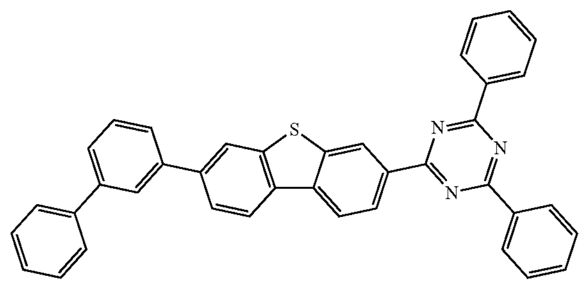
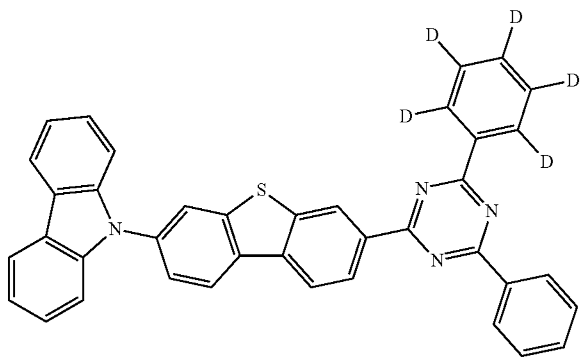
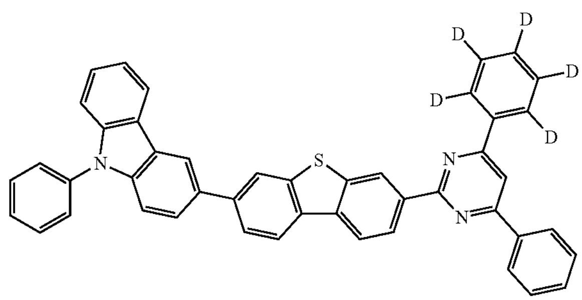
-continued
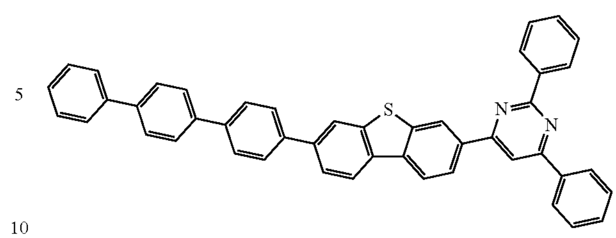
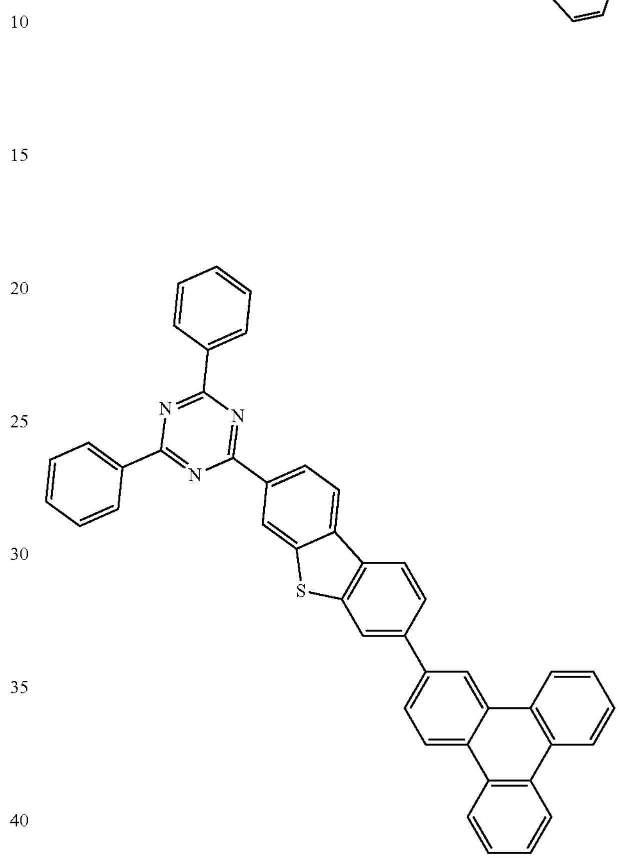
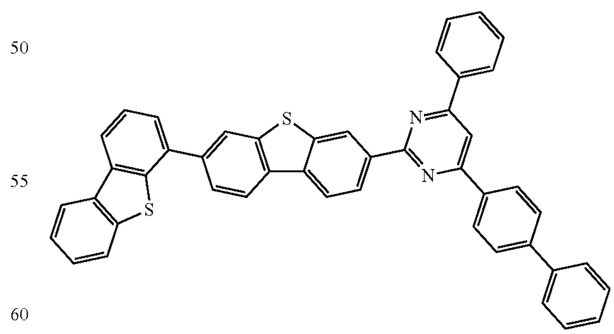

-continued
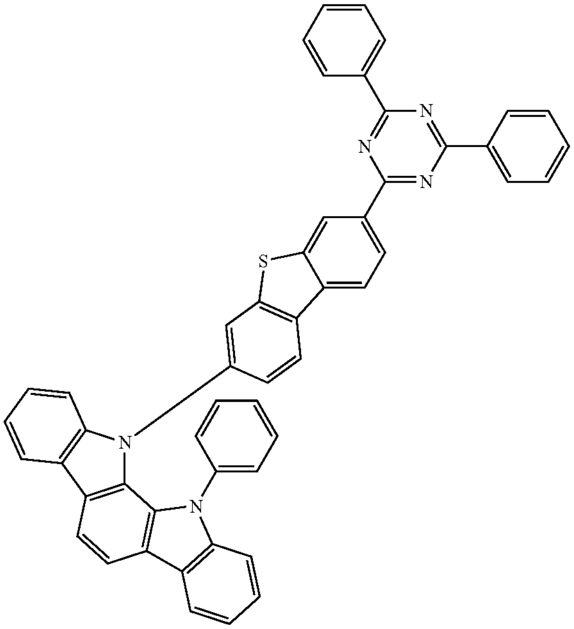
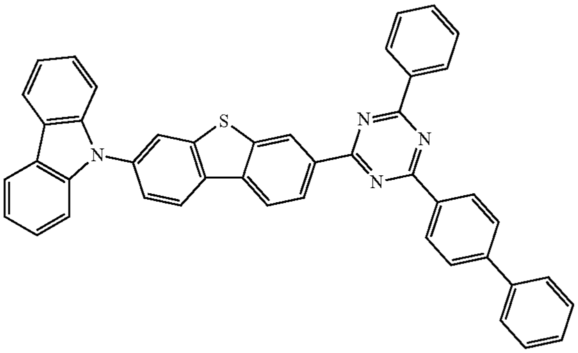
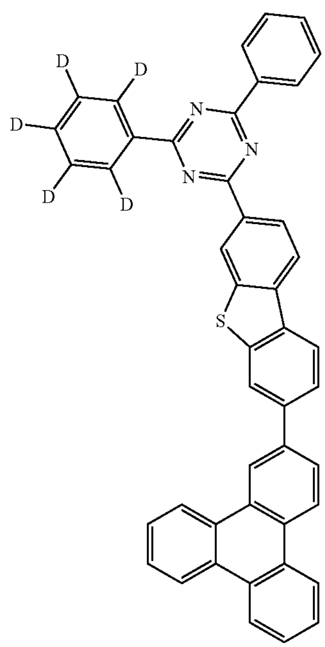
-continued
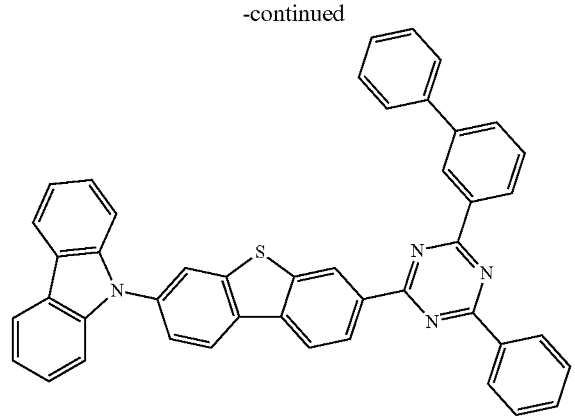
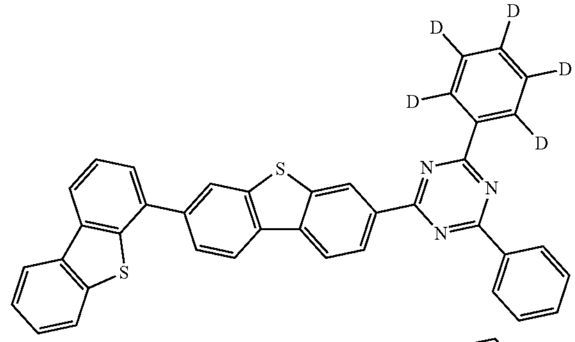
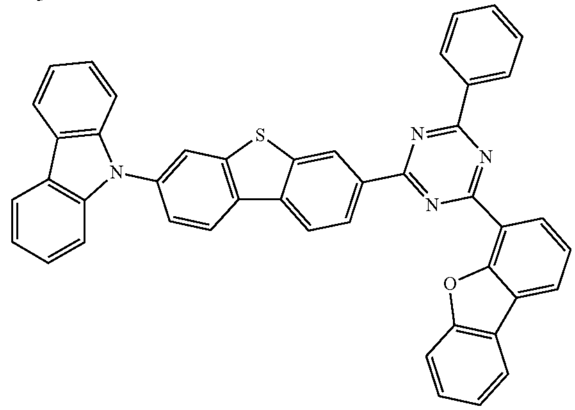
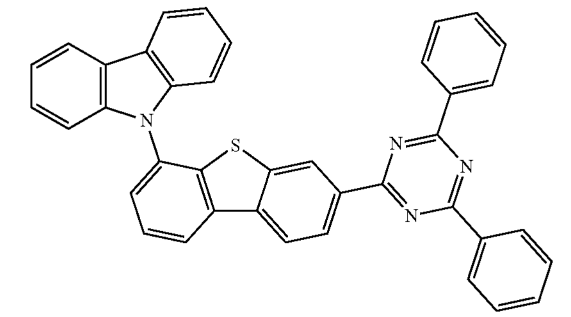
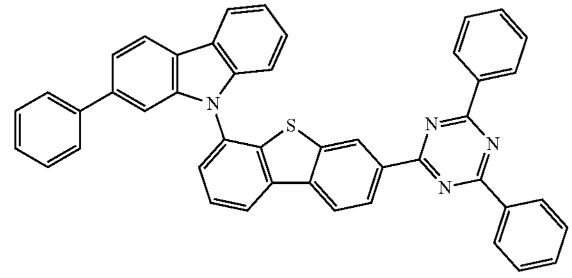

-continued
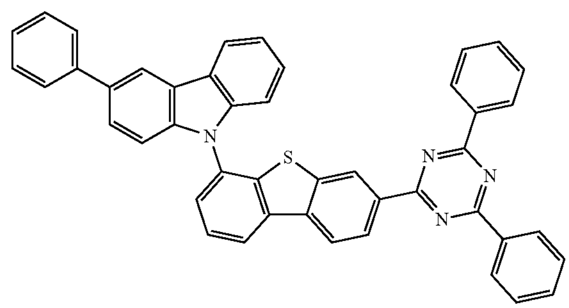
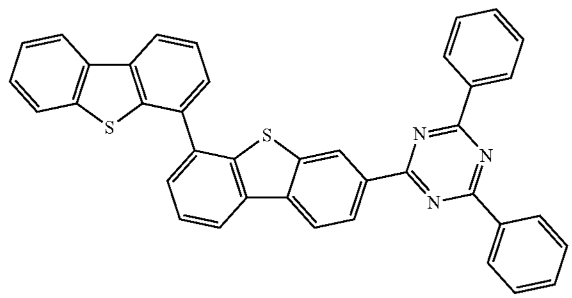
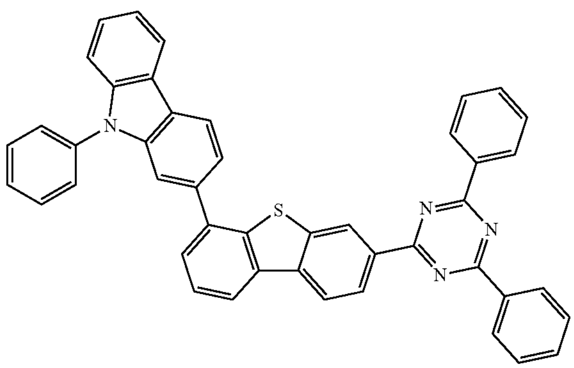
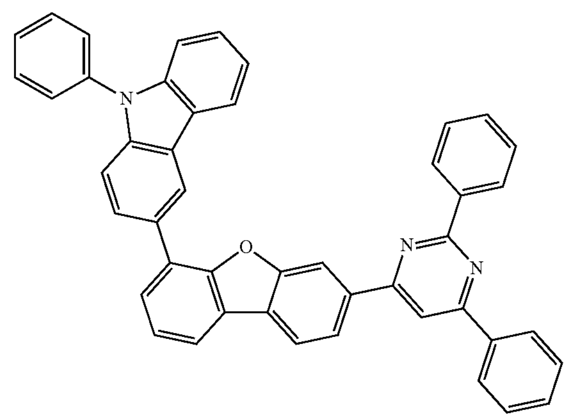
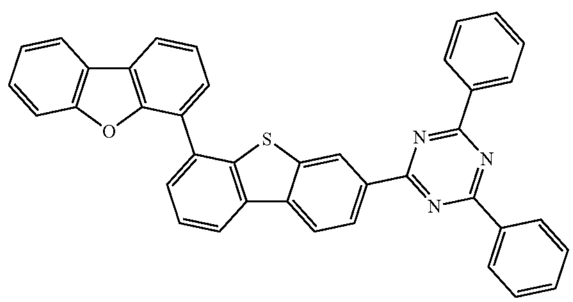
-continued
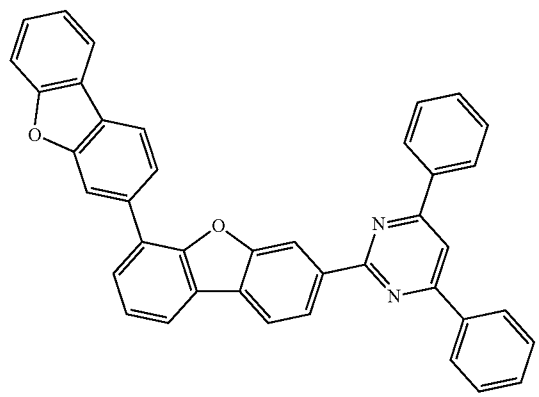
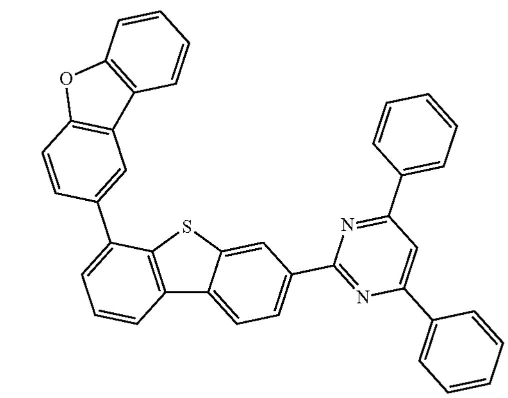
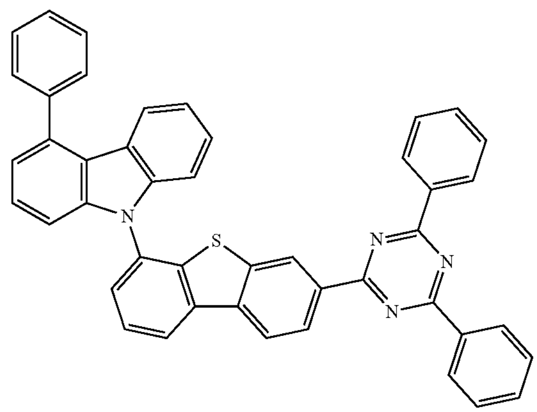
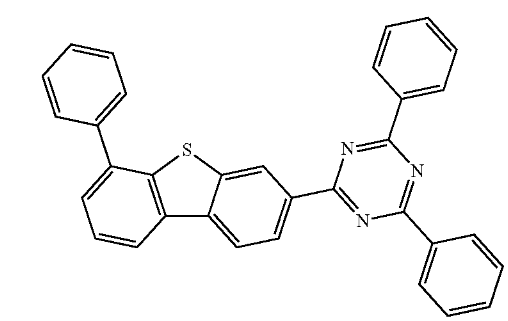

-continued
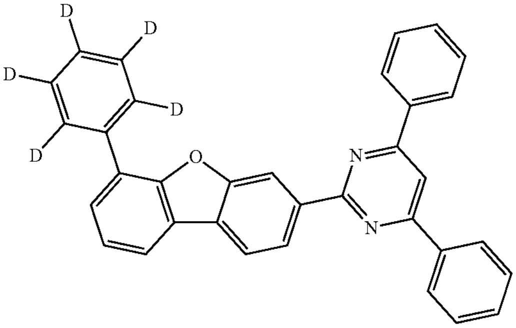
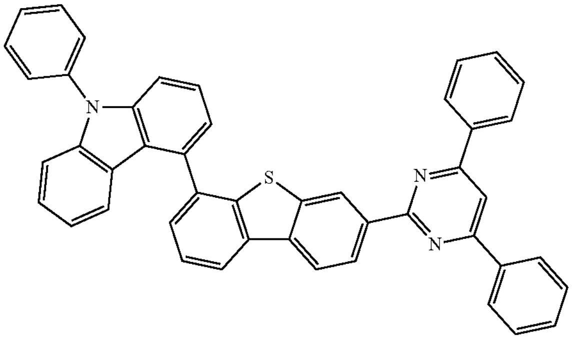
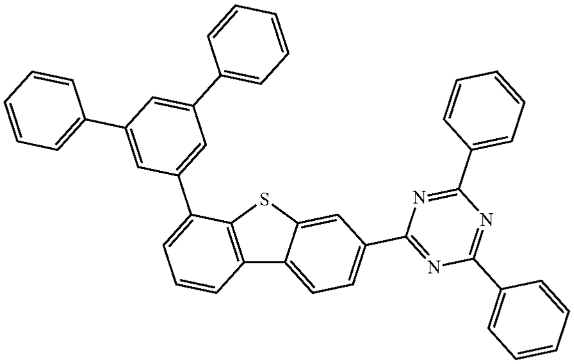
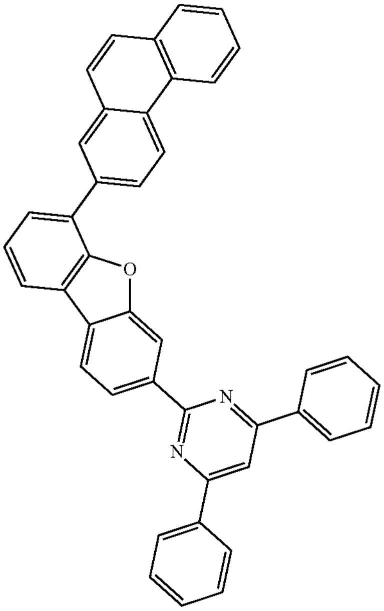
-continued
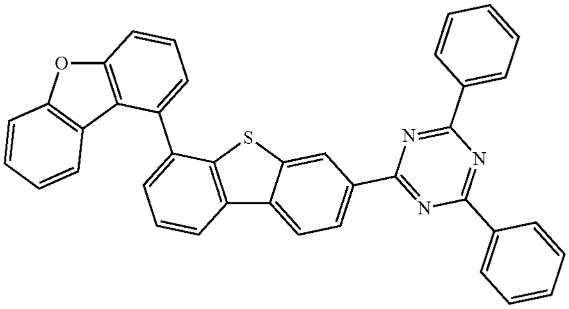
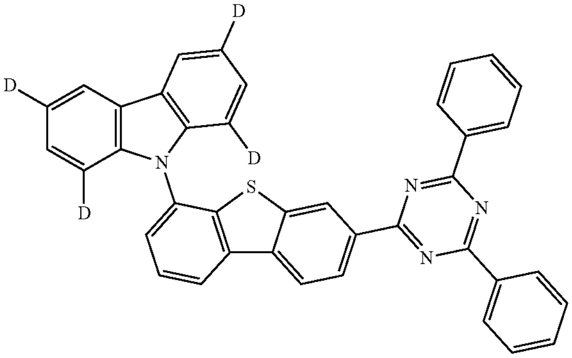
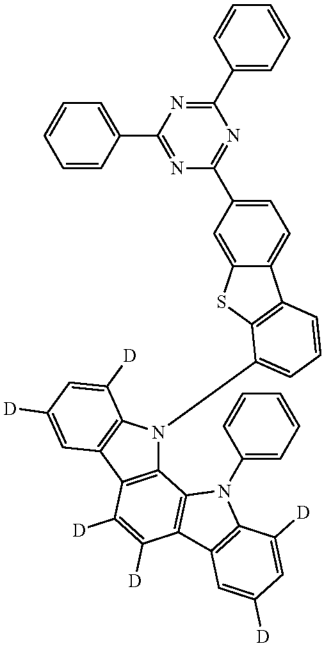
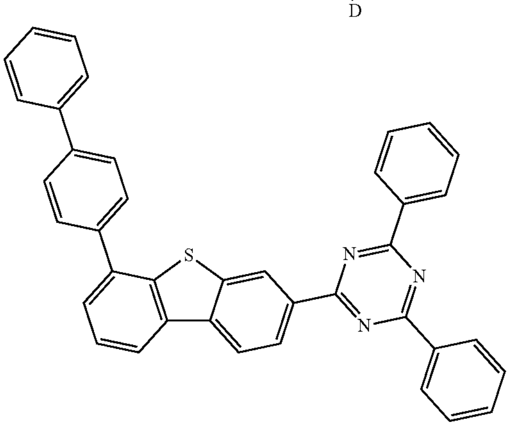

-continued
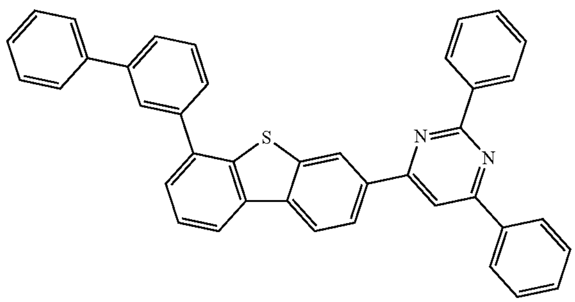
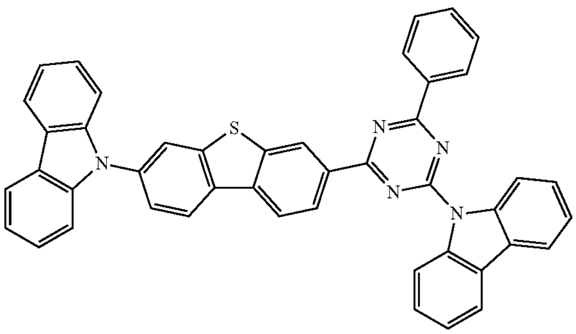
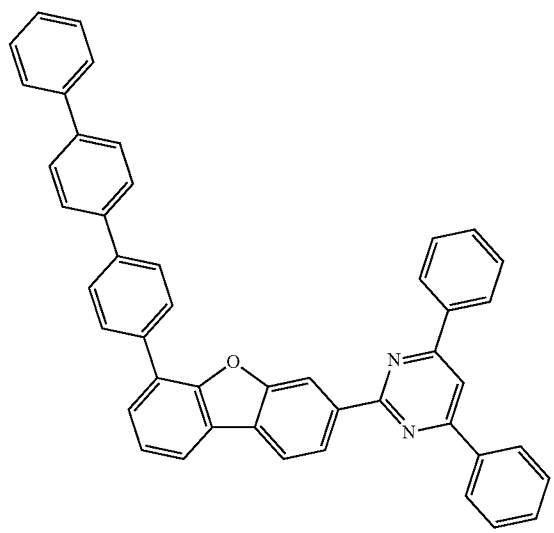
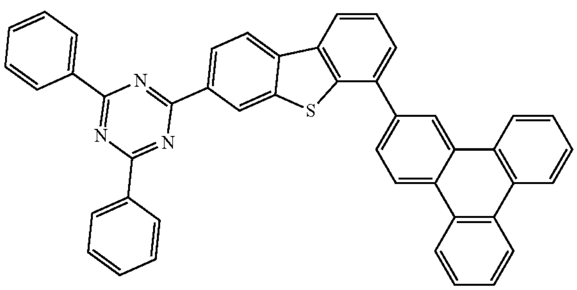
-continued
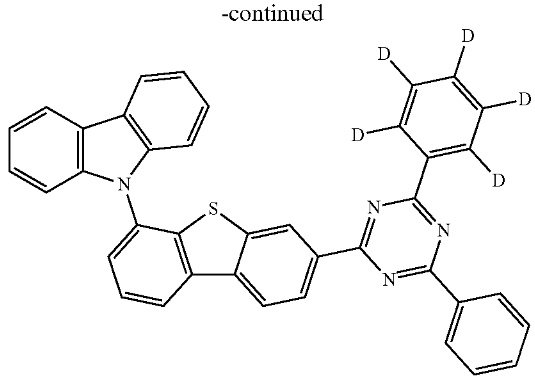
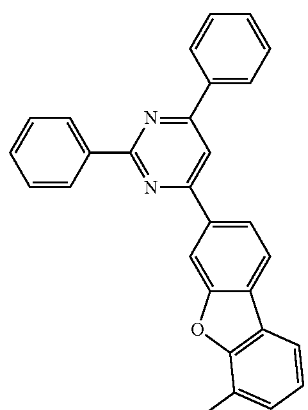
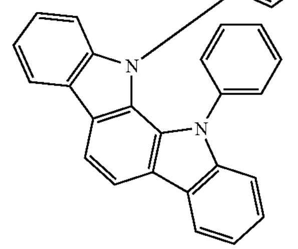
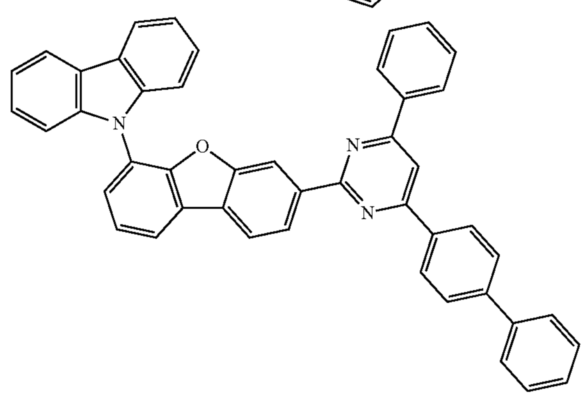
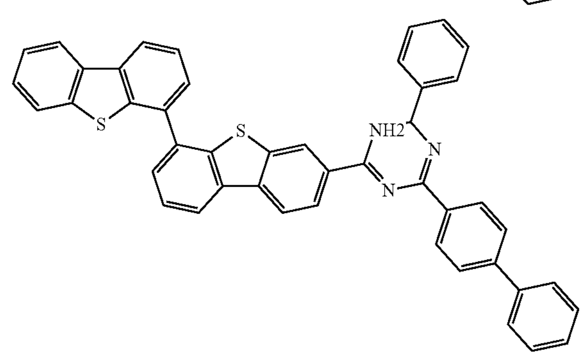

-continued
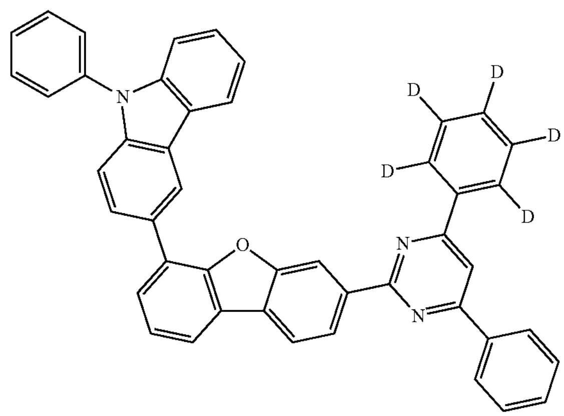
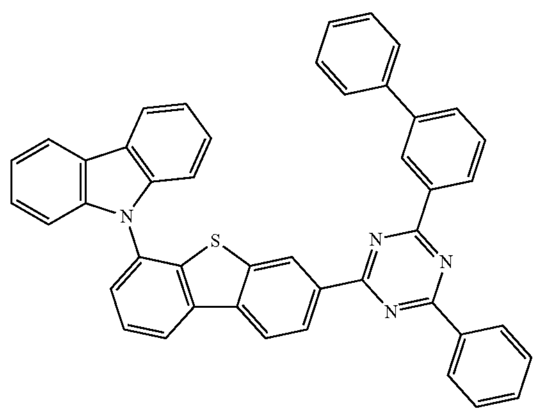
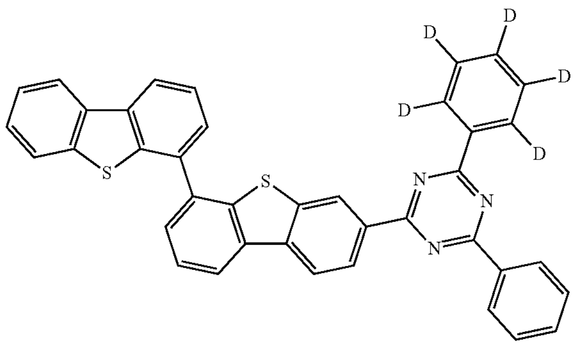
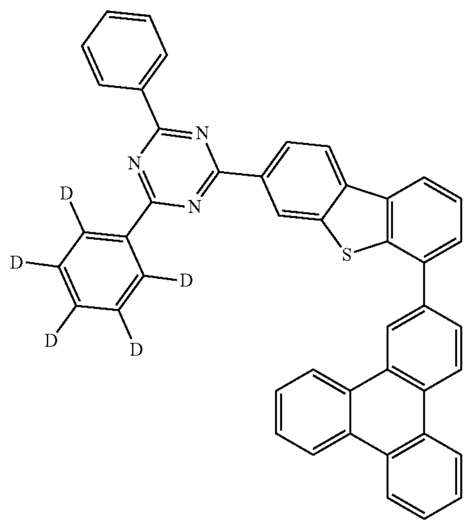
-continued
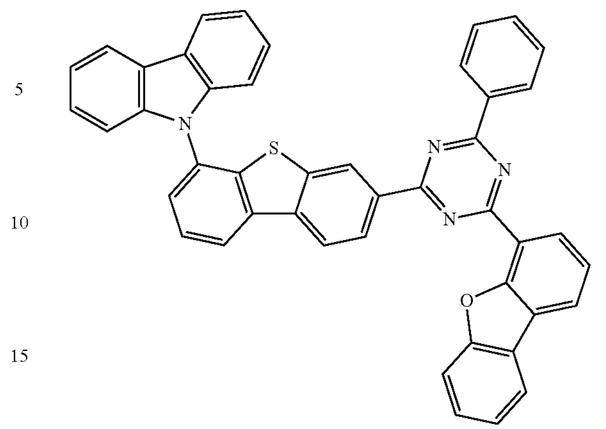
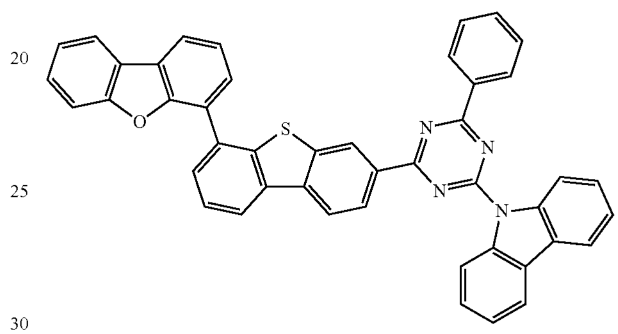
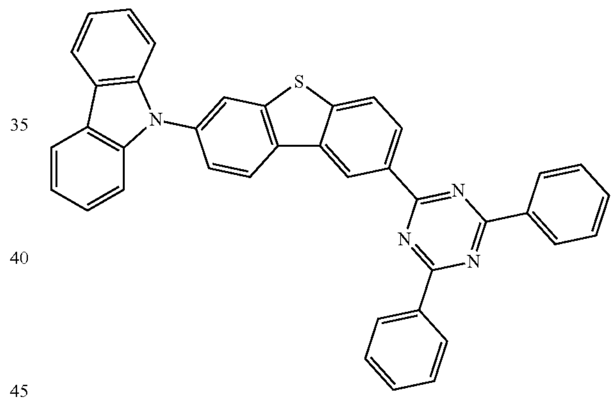
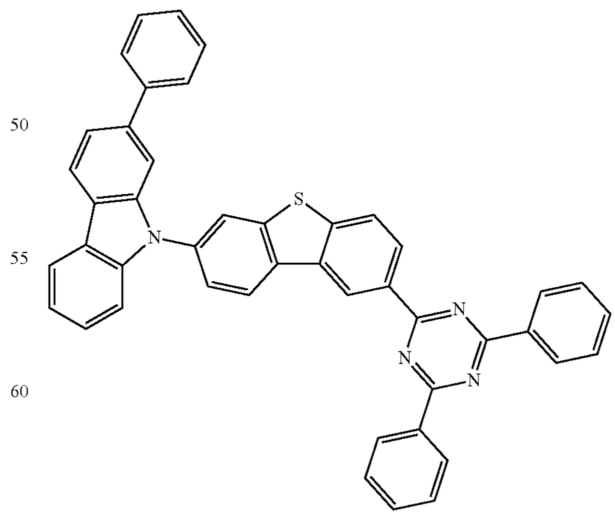

-continued
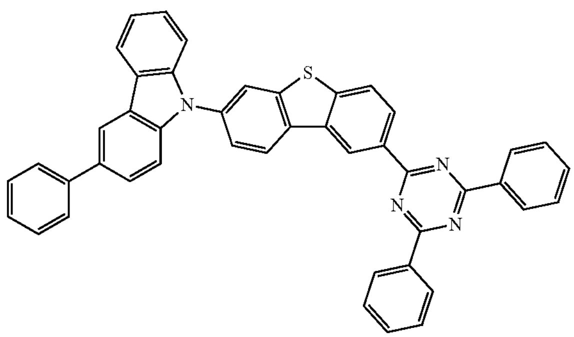
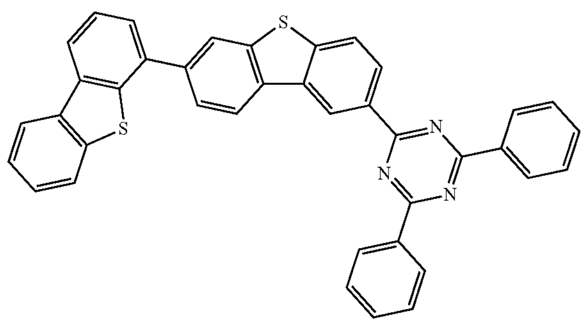
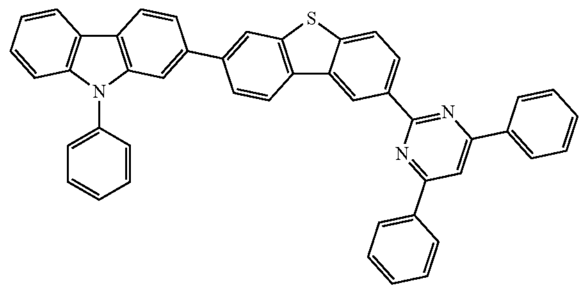
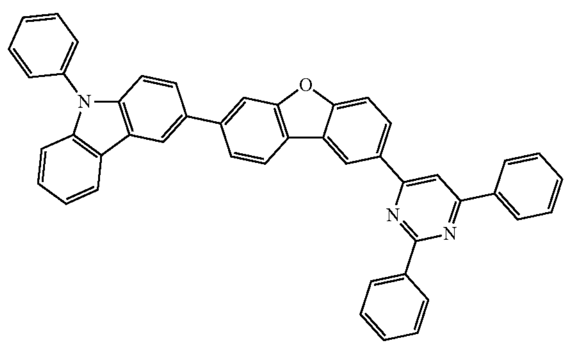
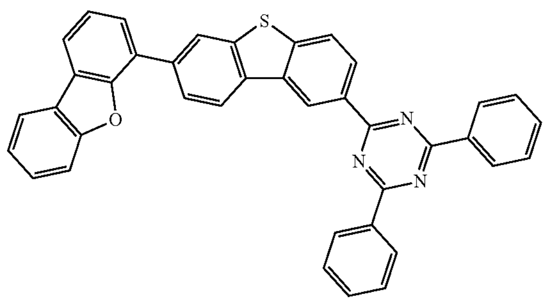
-continued
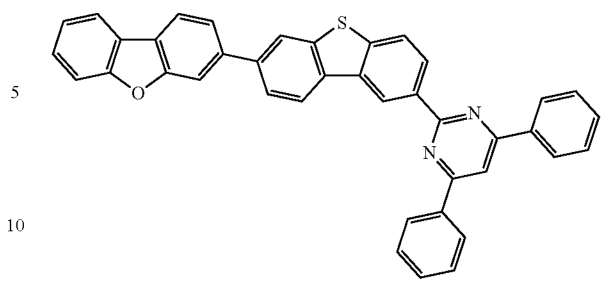
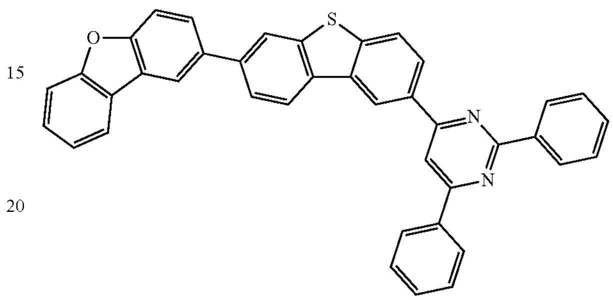
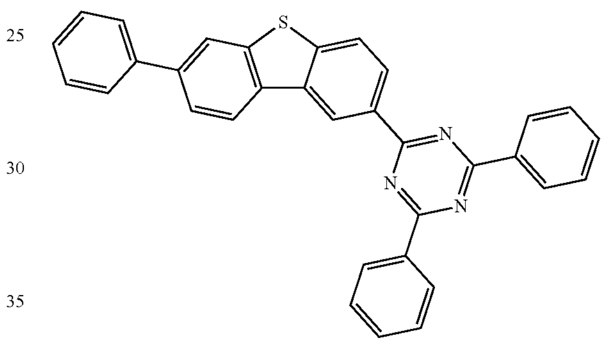
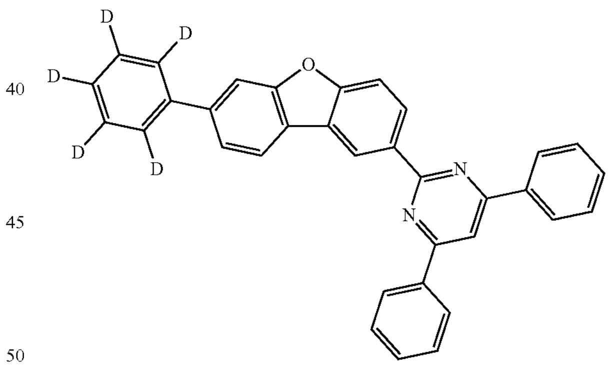
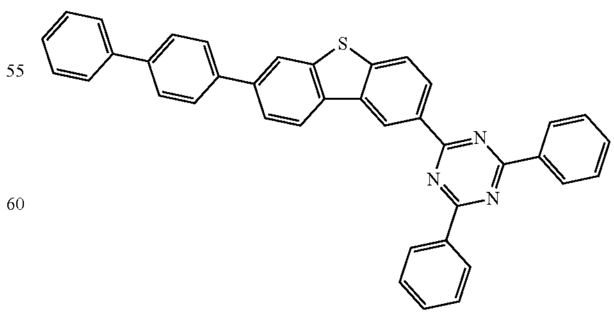

-continued
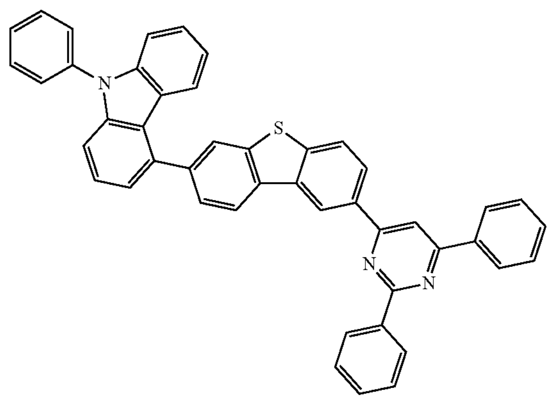
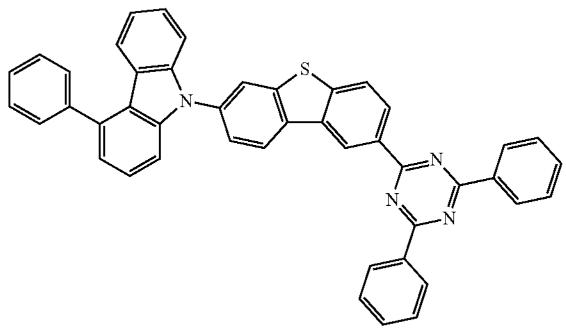
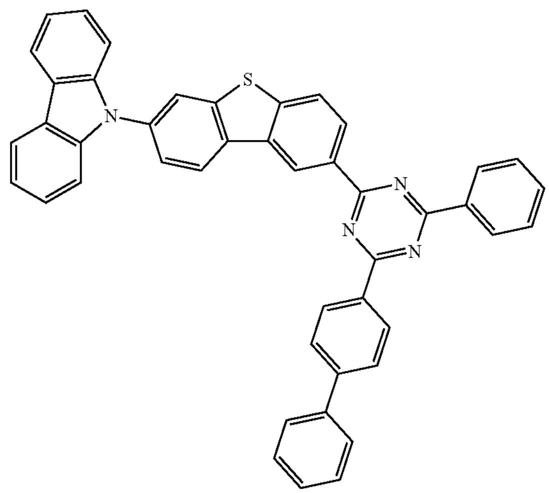
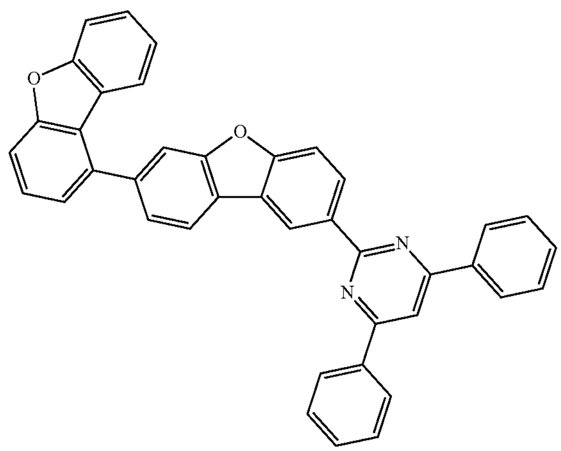
-continued
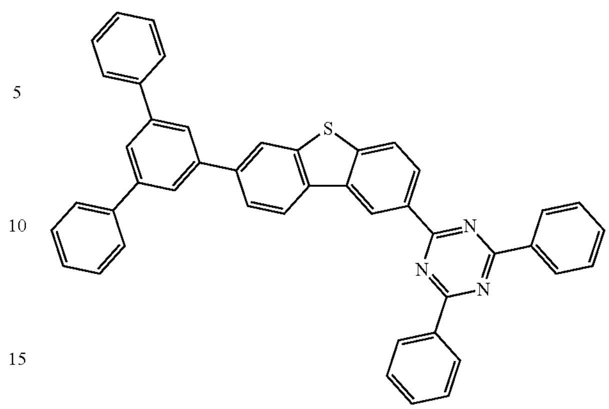
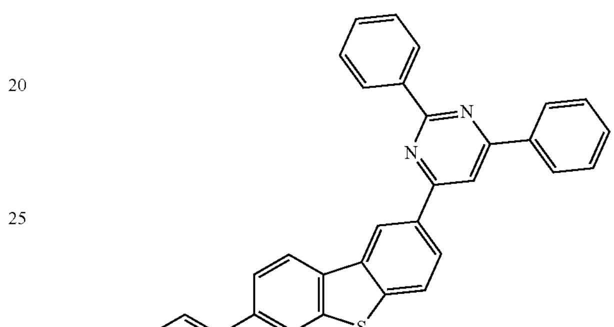
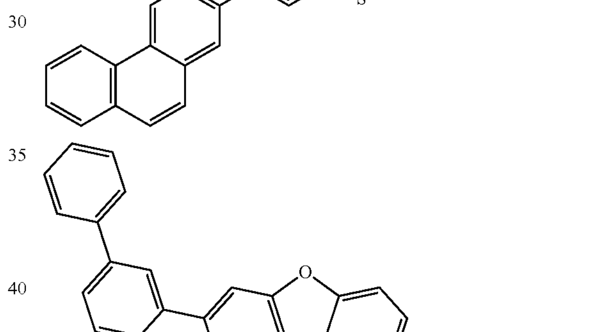
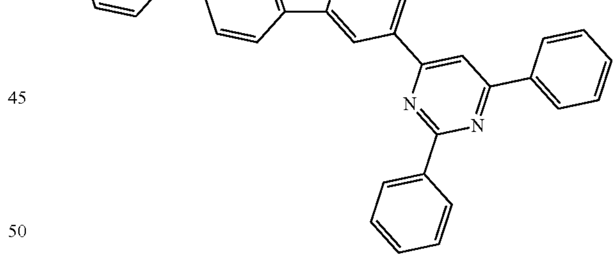
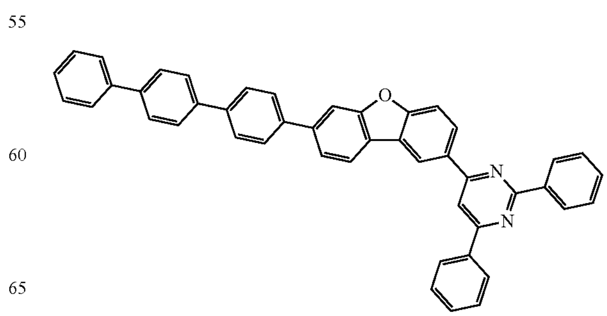

-continued
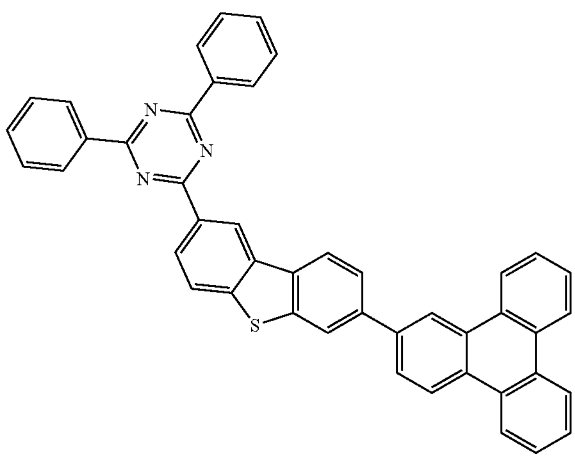
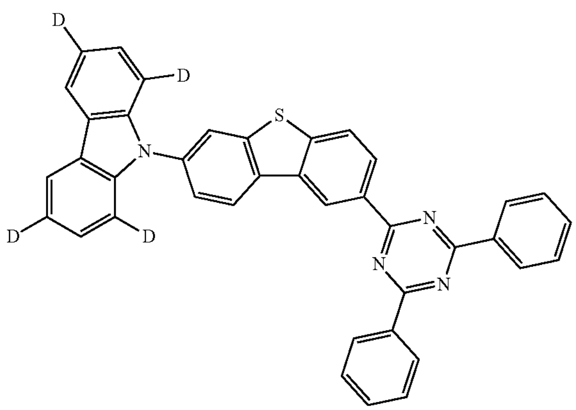
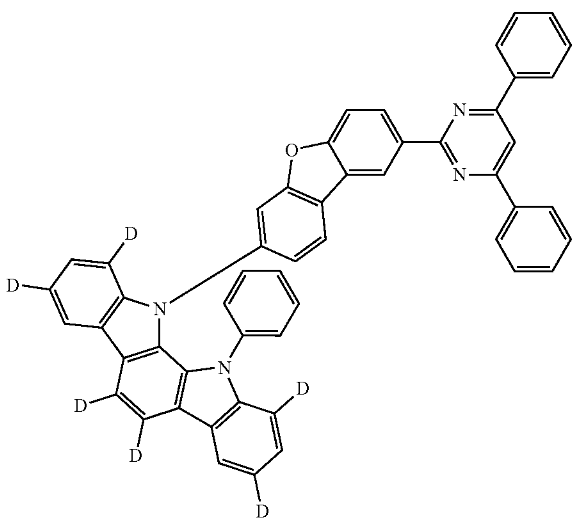
-continued
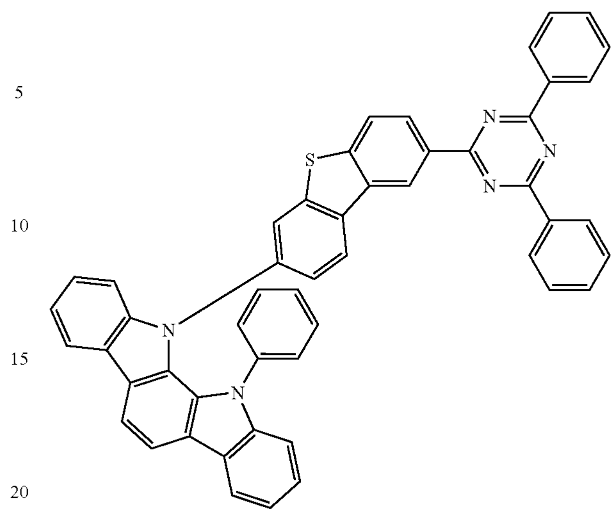
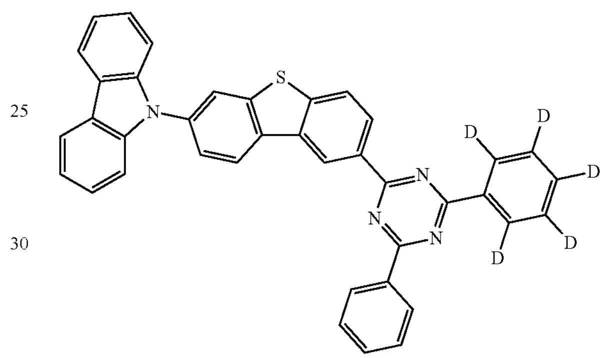
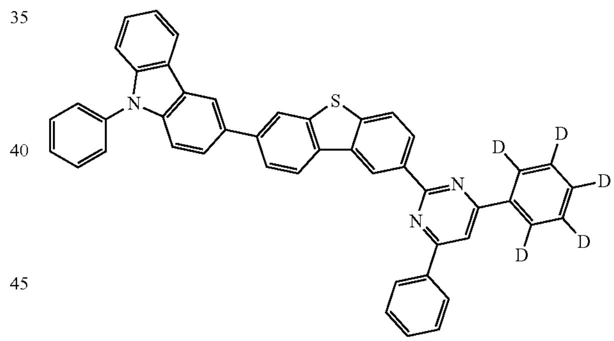
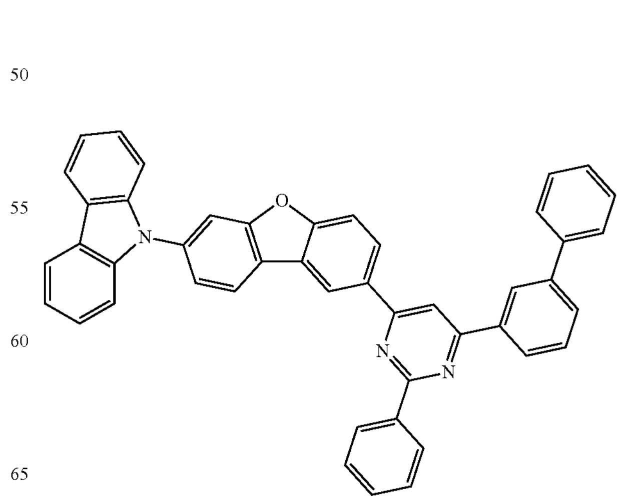

-continued
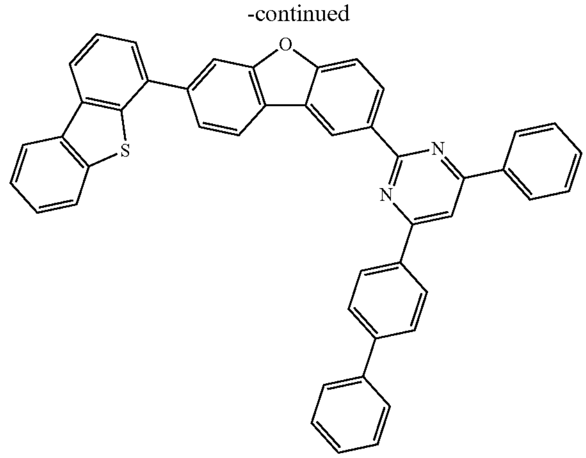
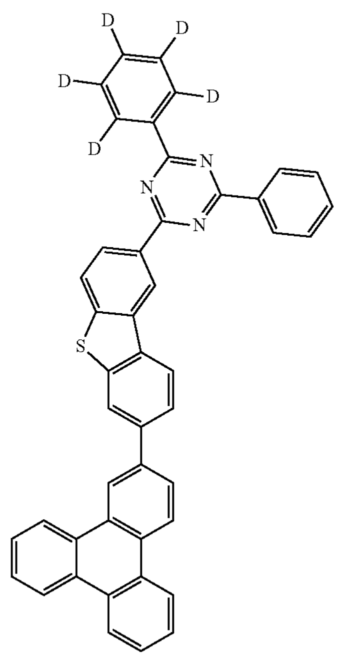
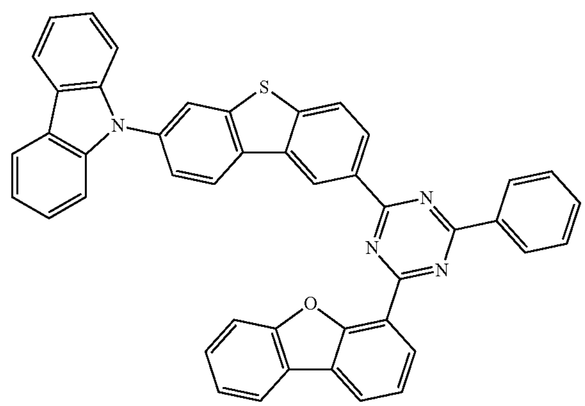
-continued
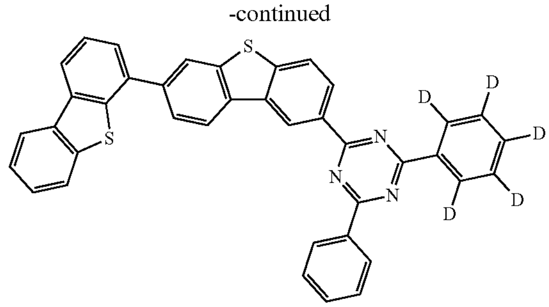
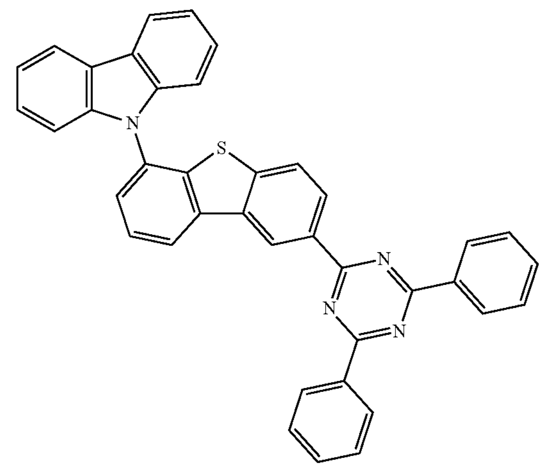
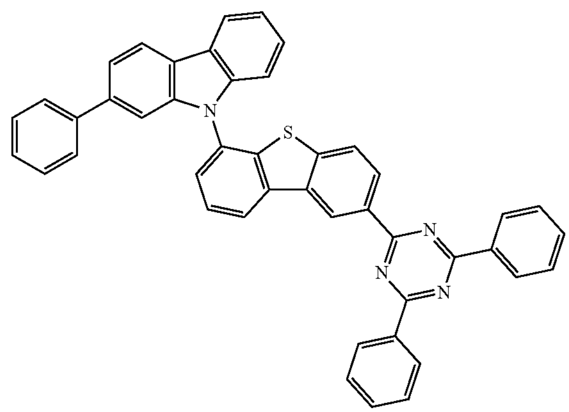
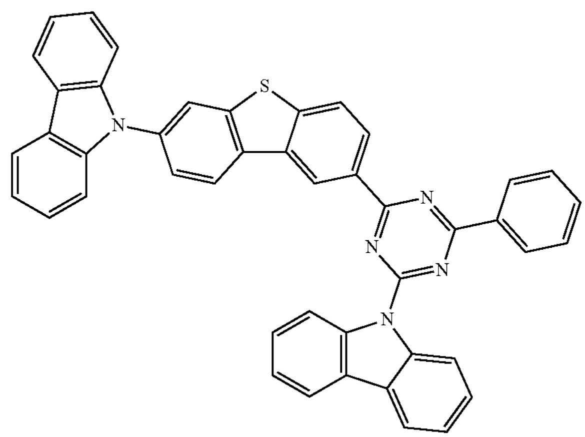

-continued
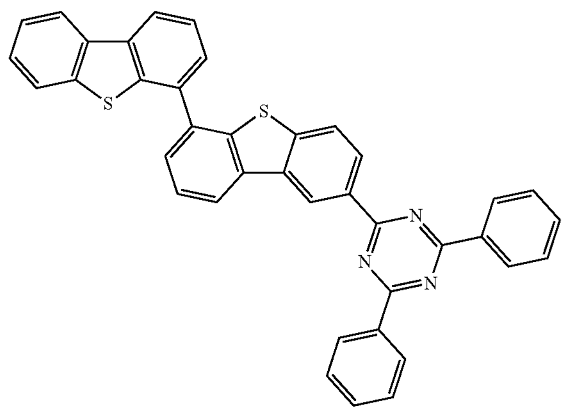
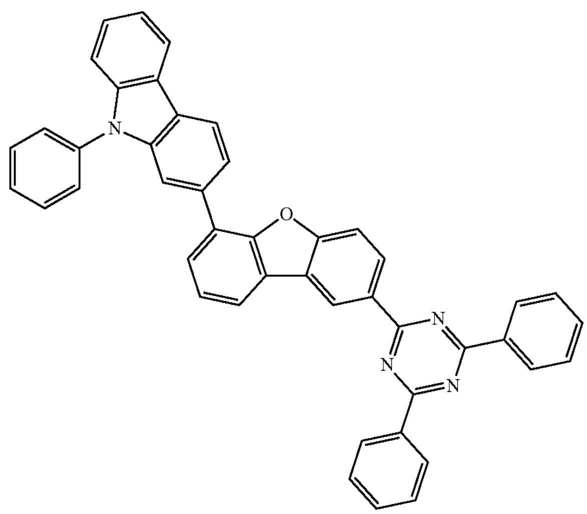
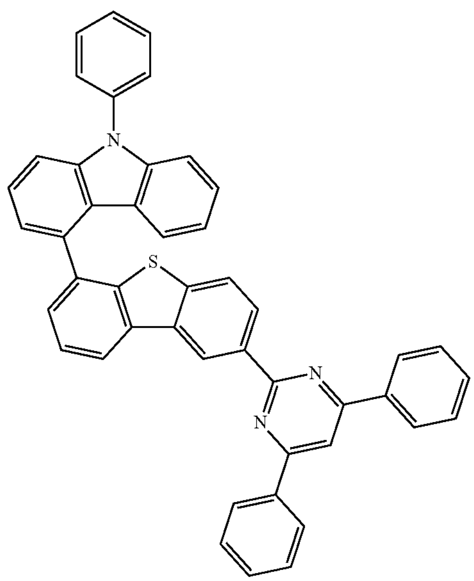
-continued
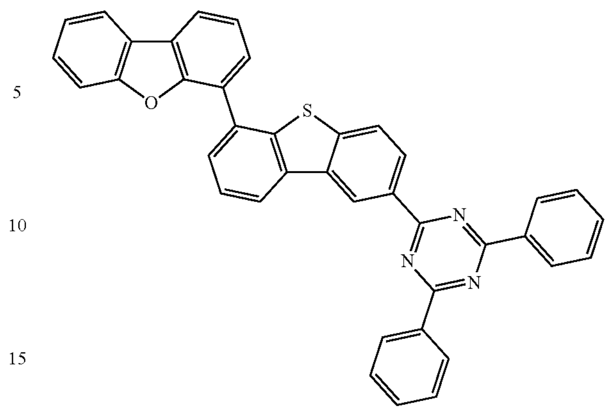
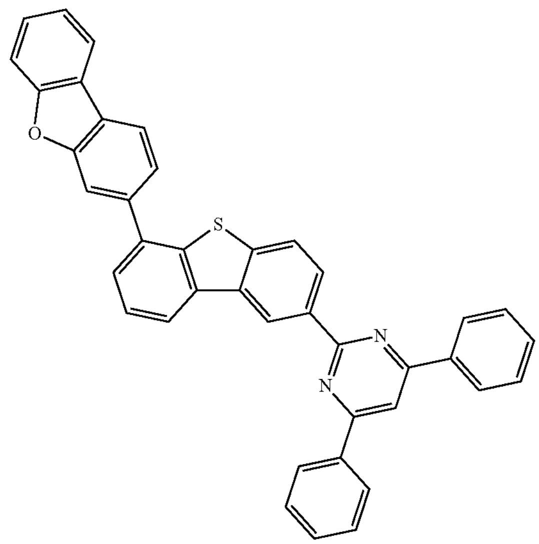
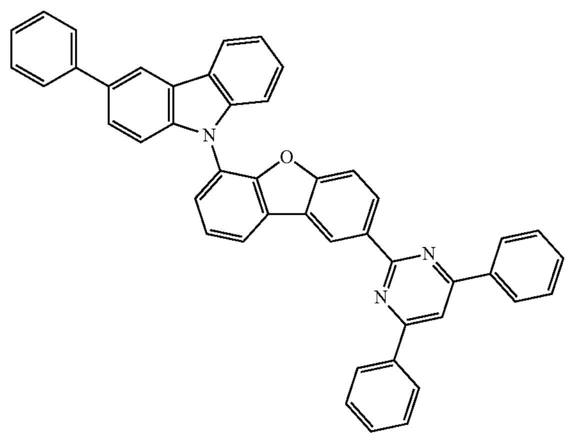

-continued
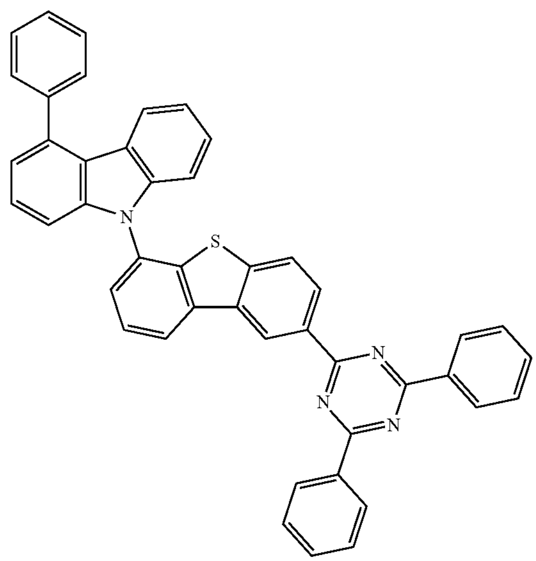
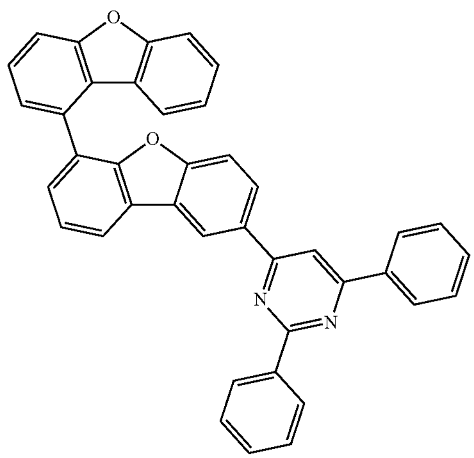
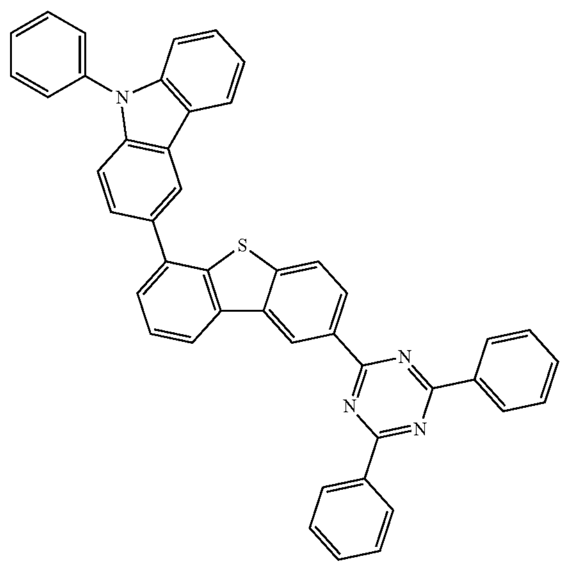
-continued
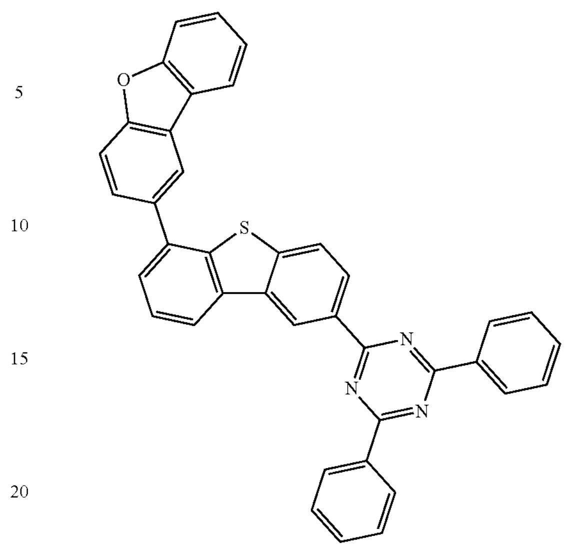
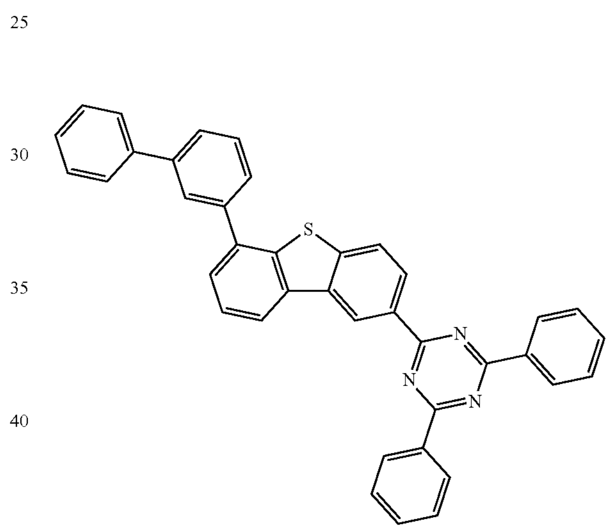
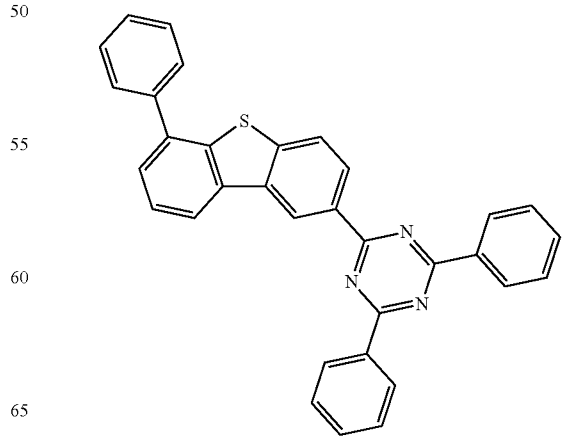

-continued
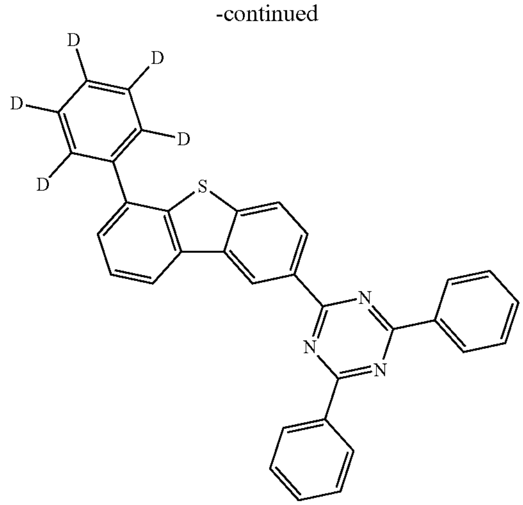
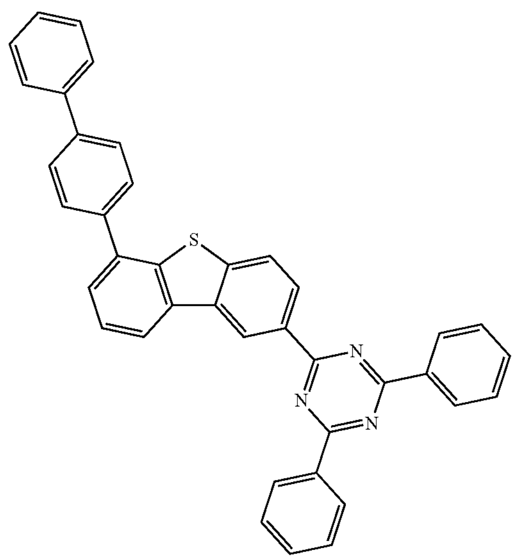
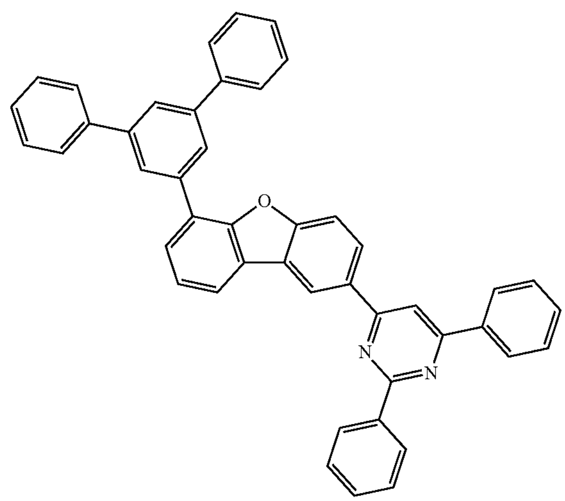
-continued
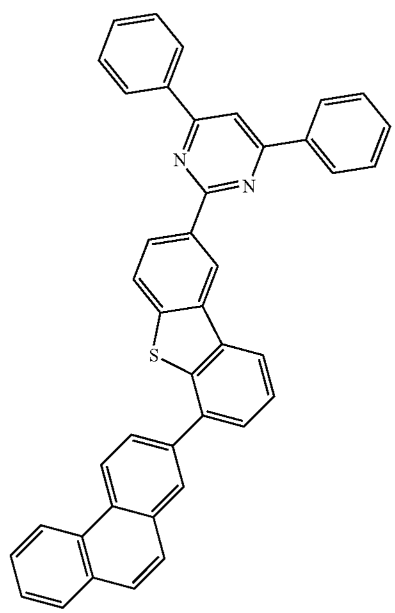
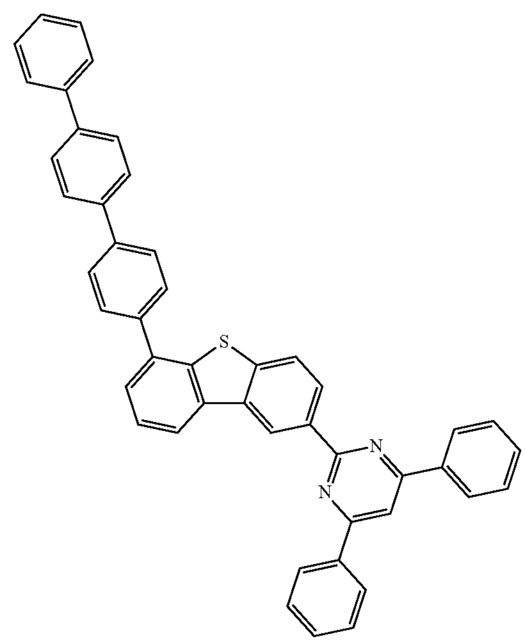

-continued
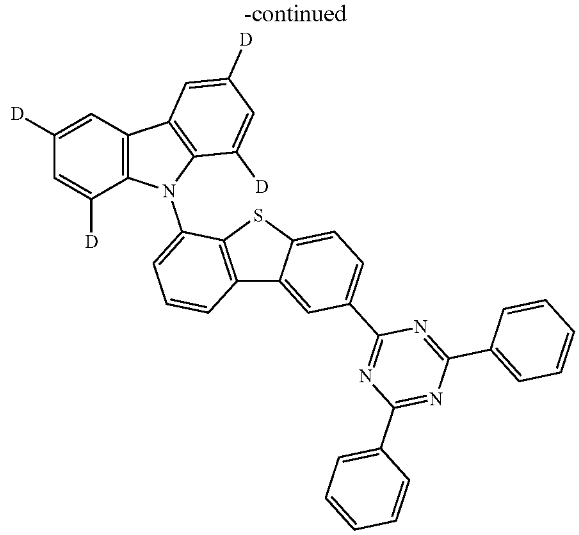
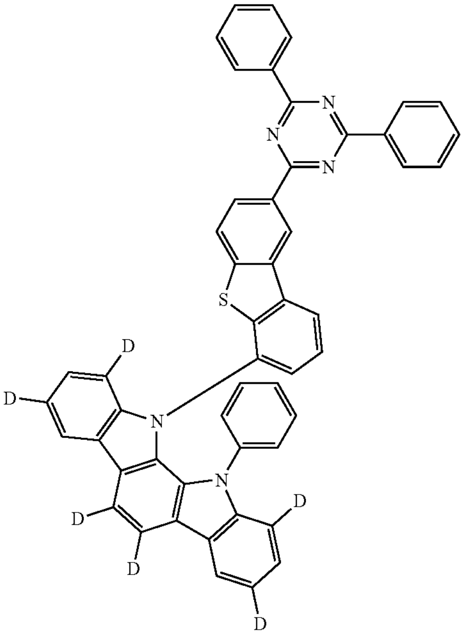
-continued
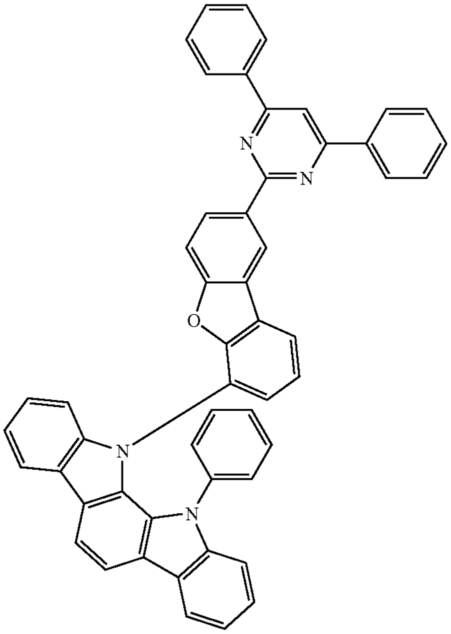
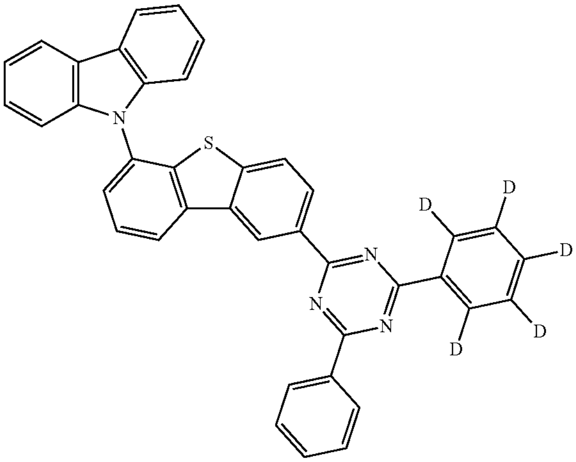
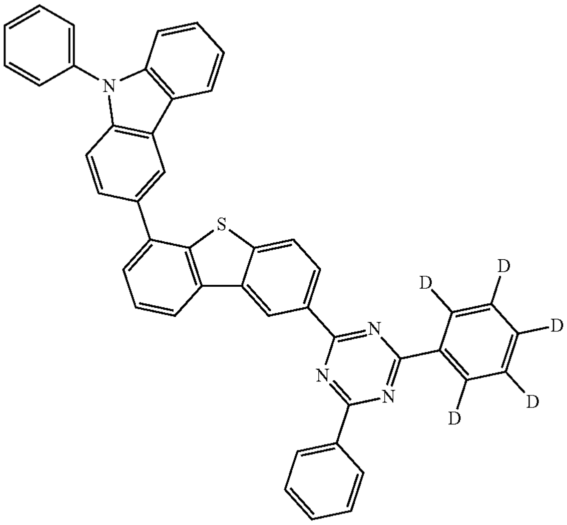

-continued
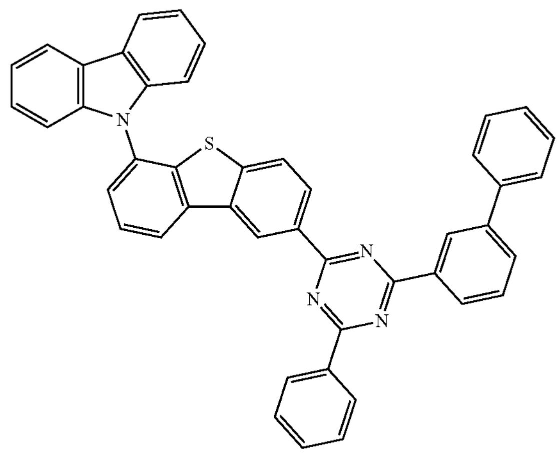
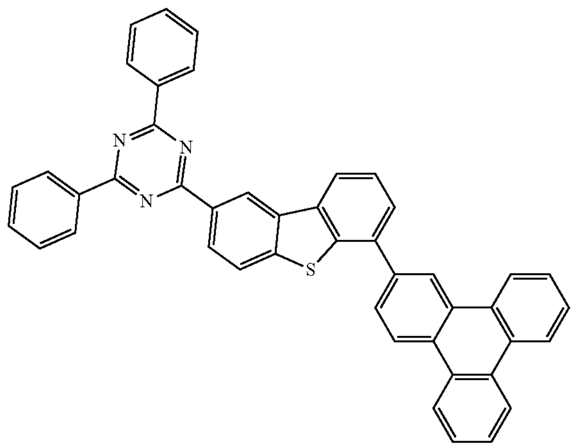
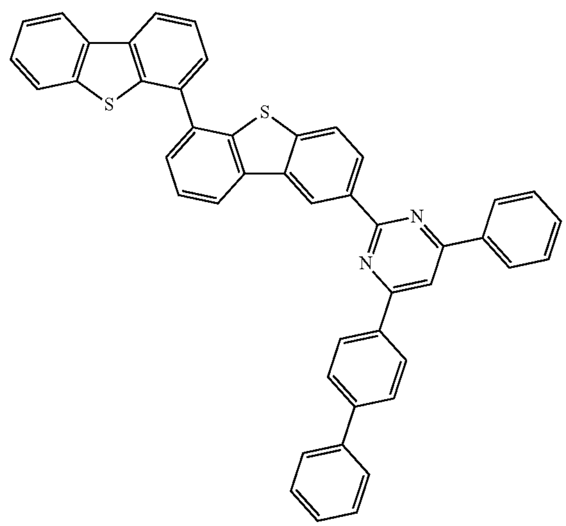
-continued
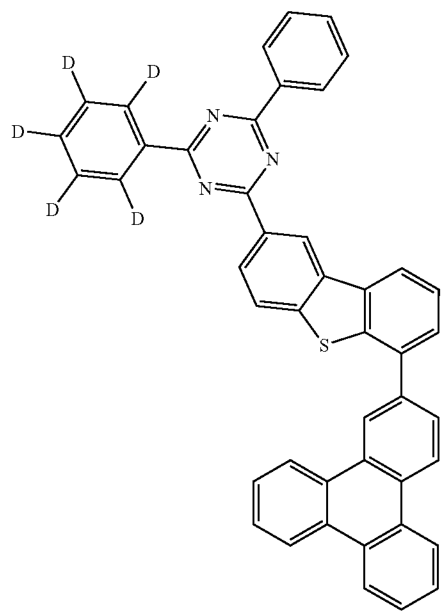
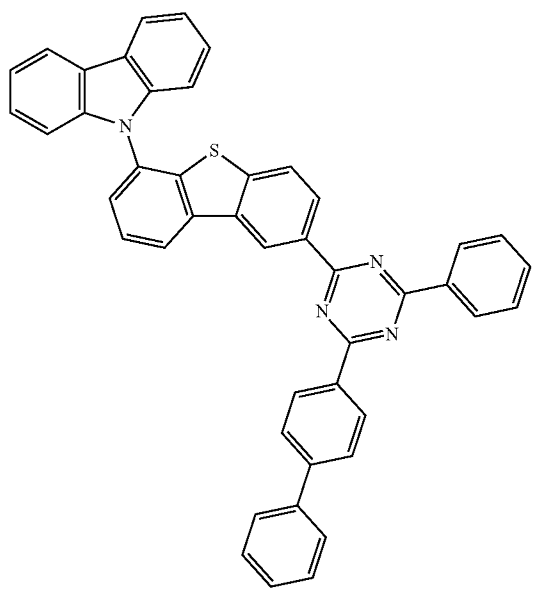
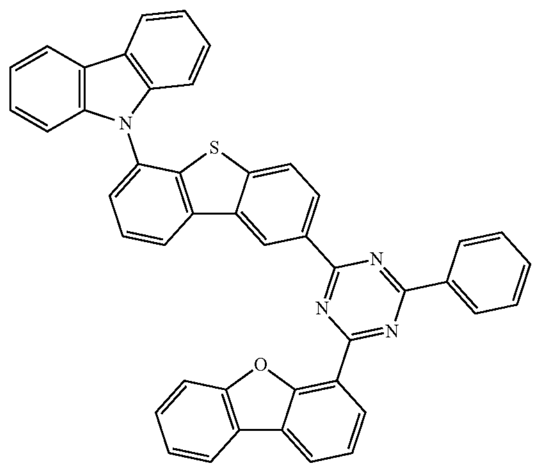

-continued
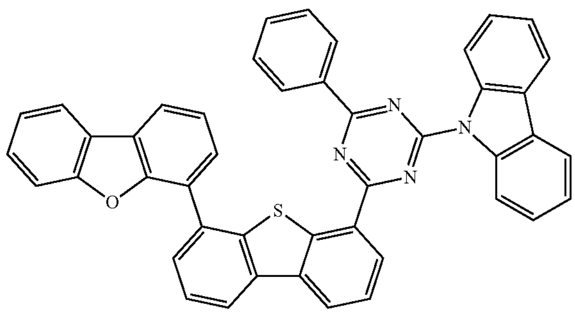
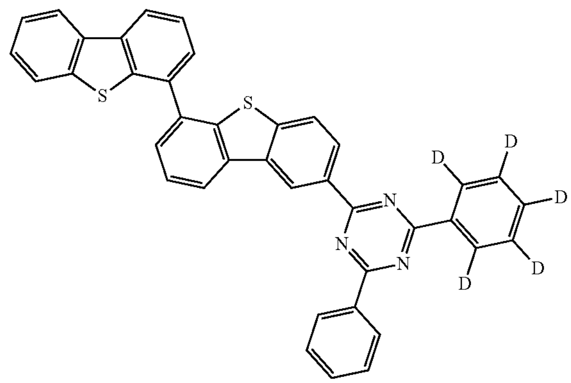
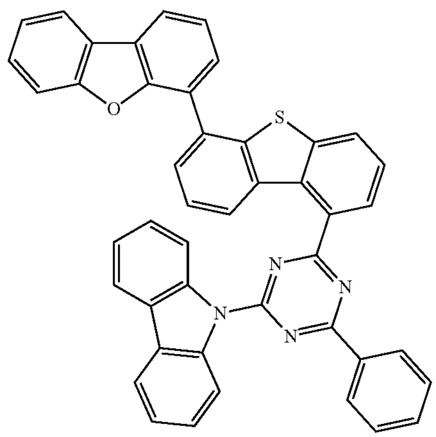
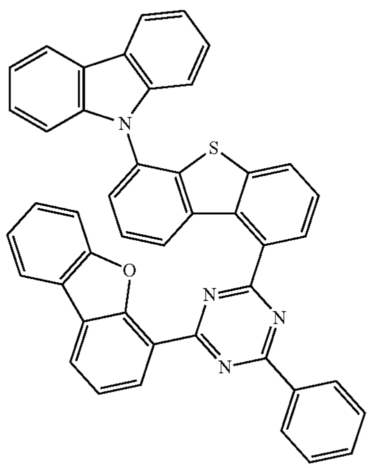
-continued
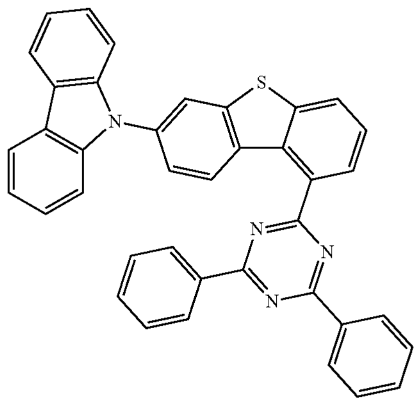
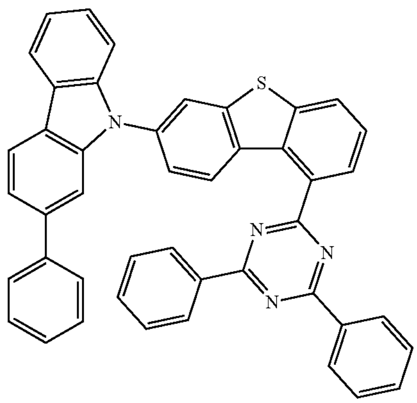
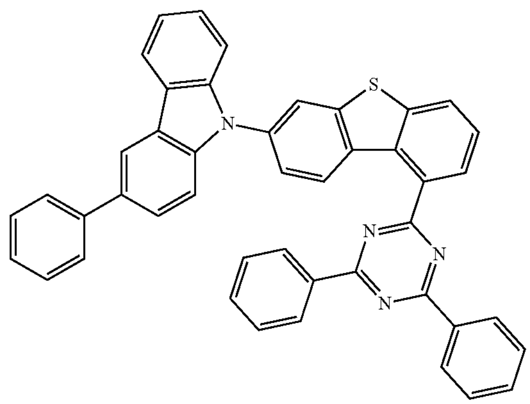
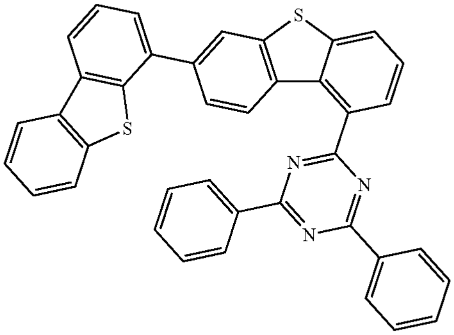

-continued
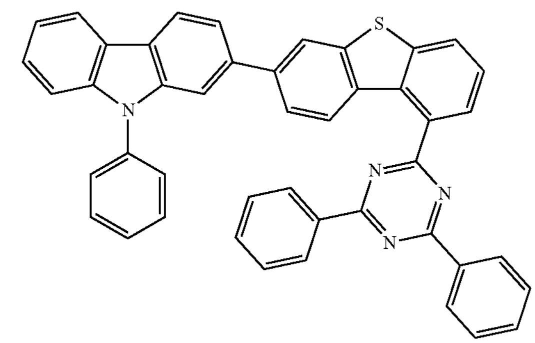
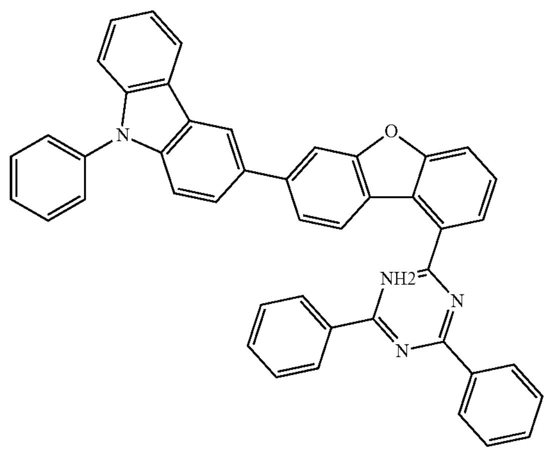
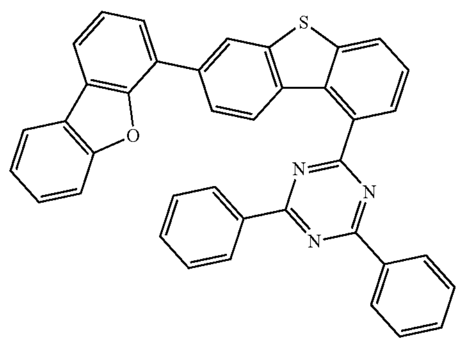
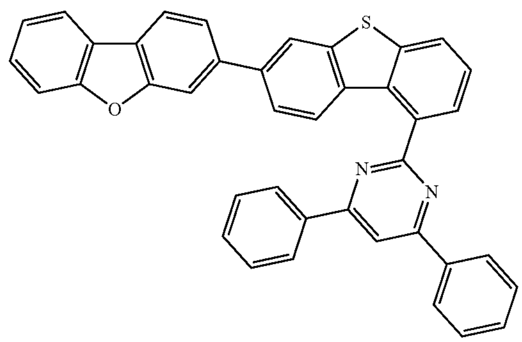
-continued
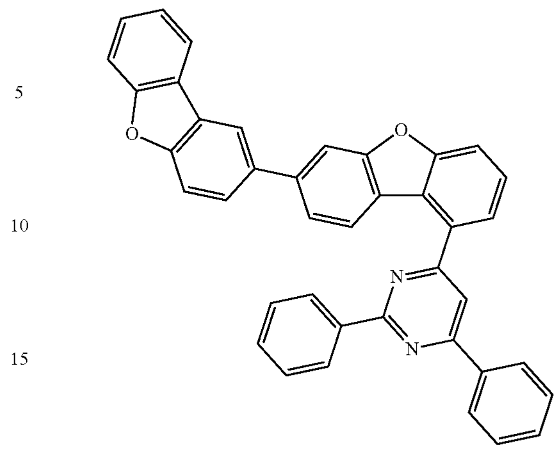
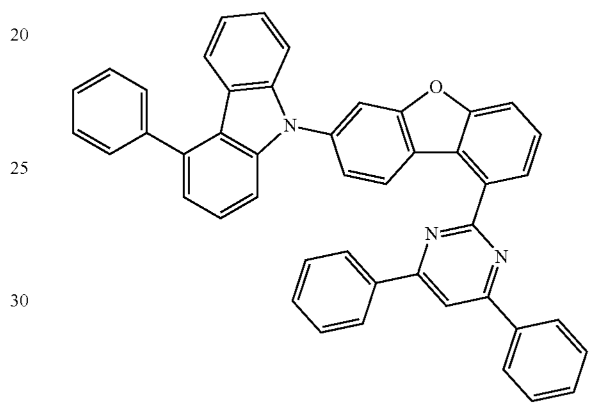
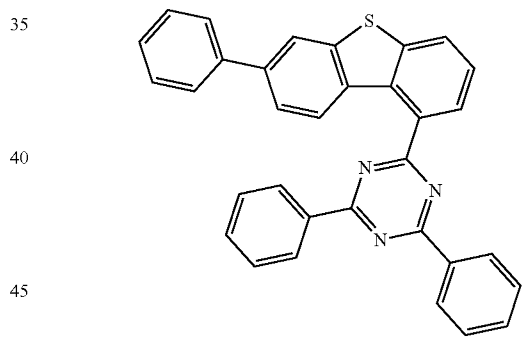
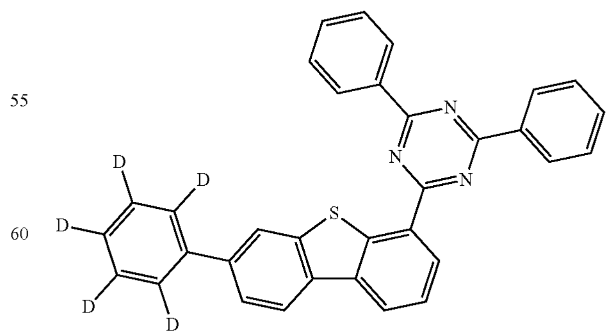

-continued
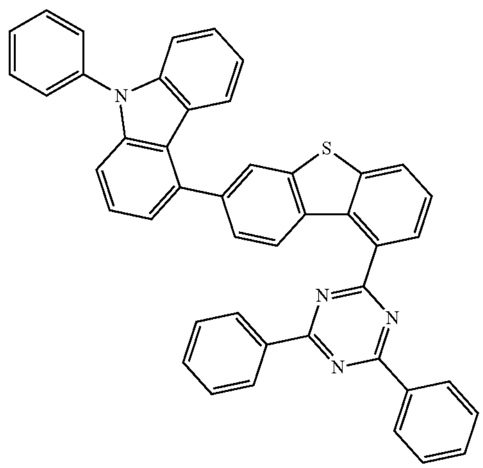
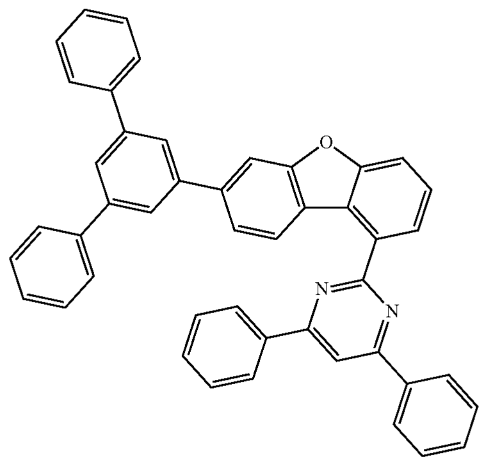
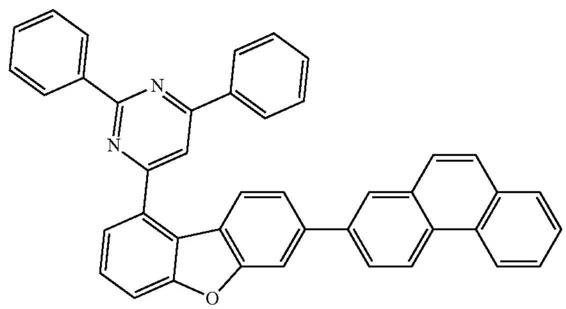
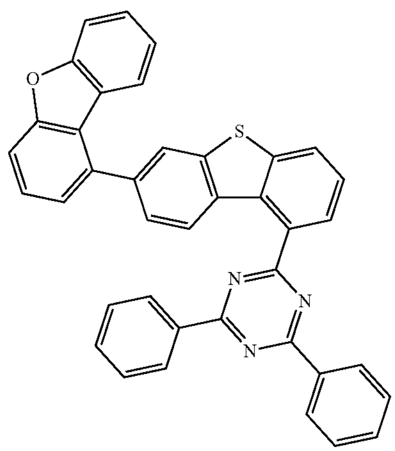
-continued
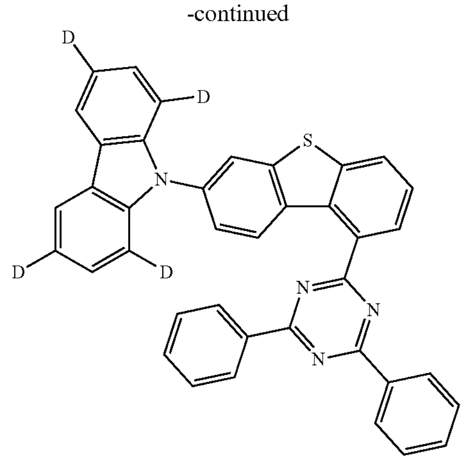
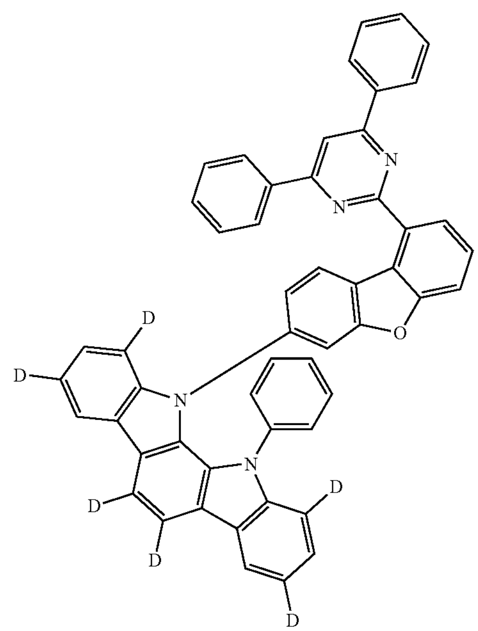
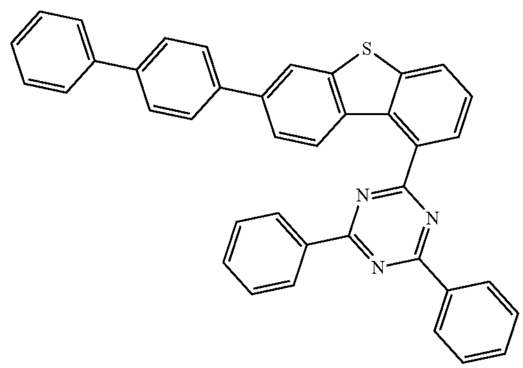

-continued
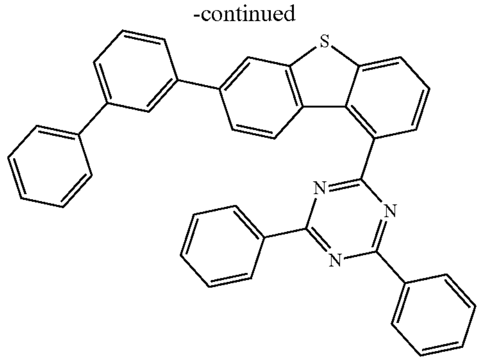
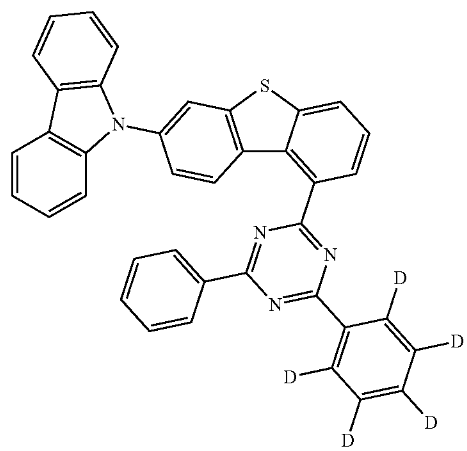
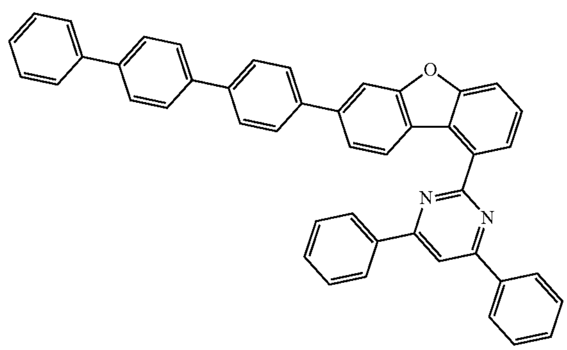
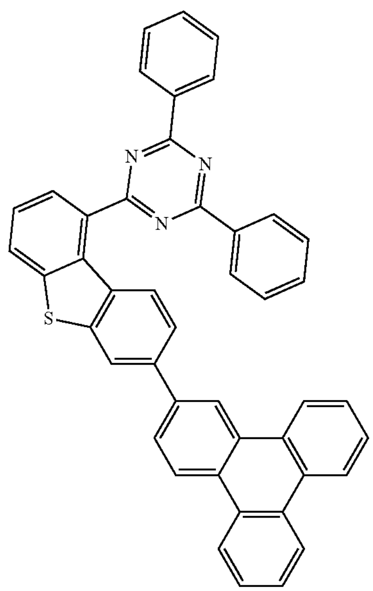
-continued
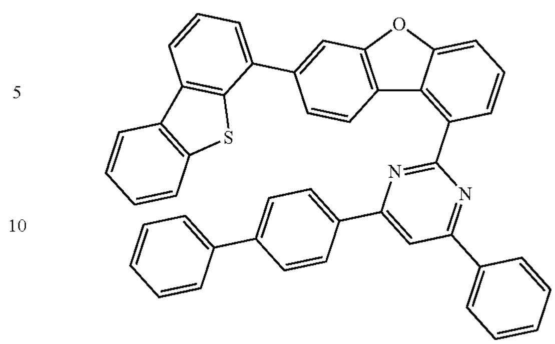
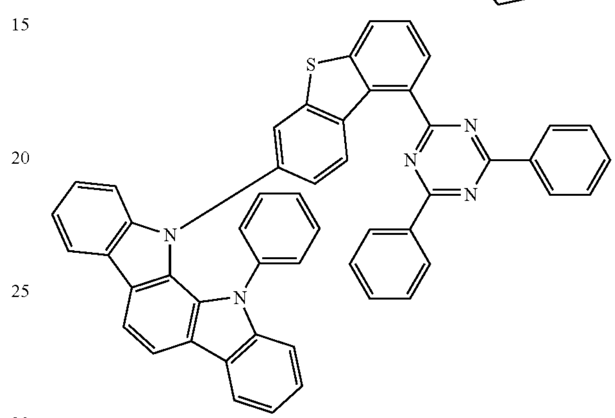
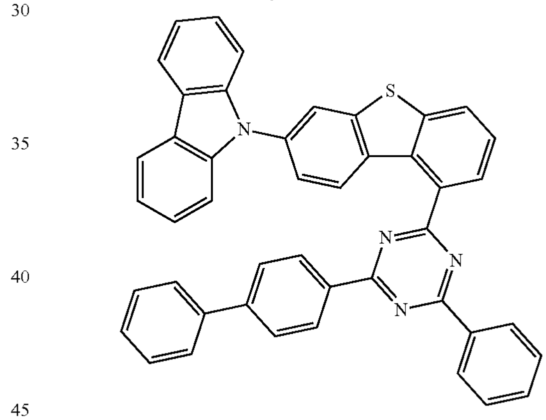
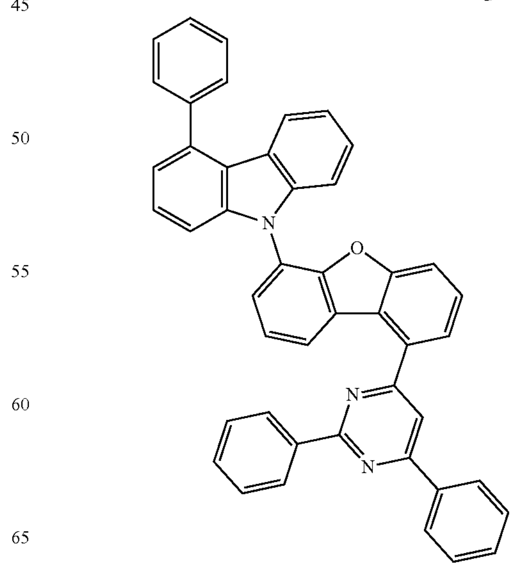

-continued
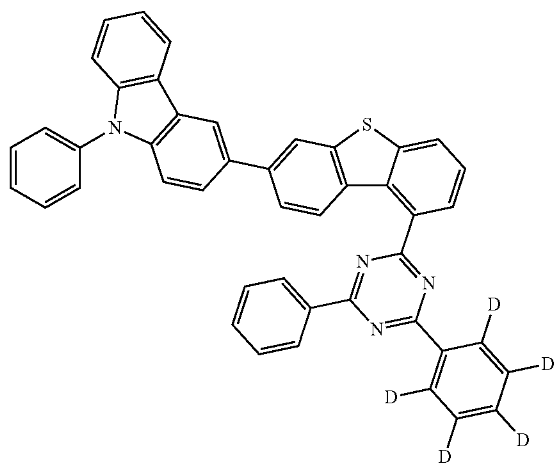
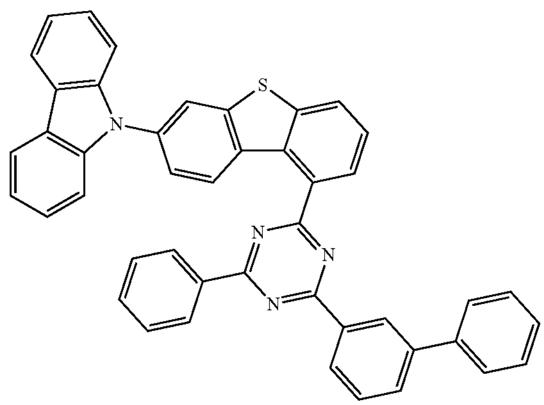
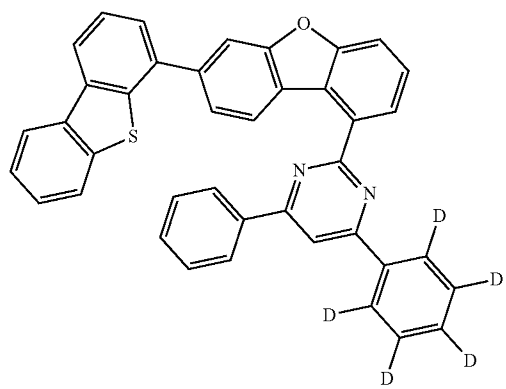
-continued
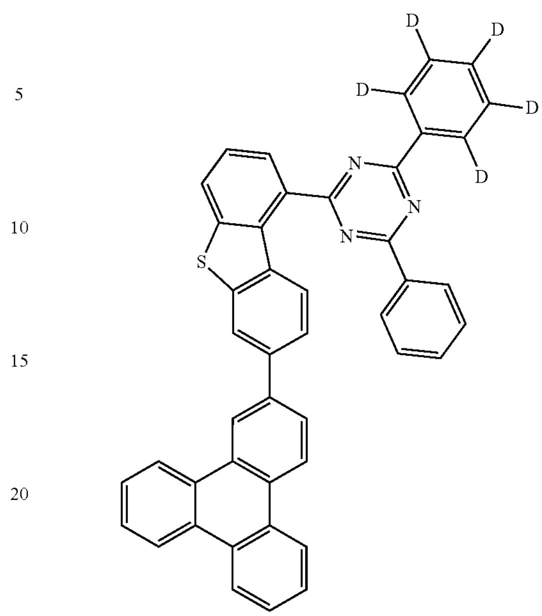
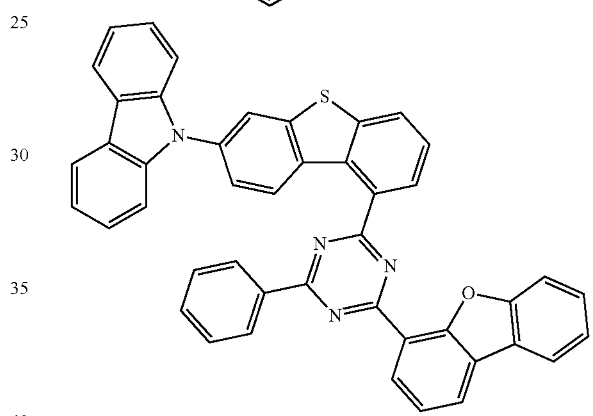
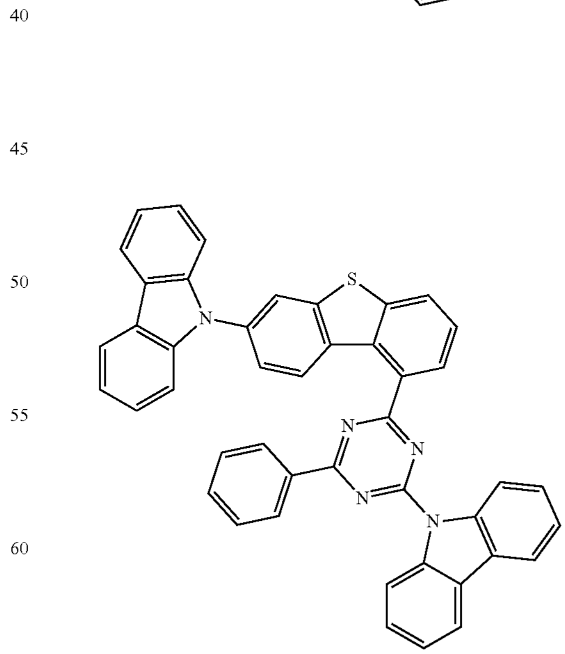

-continued
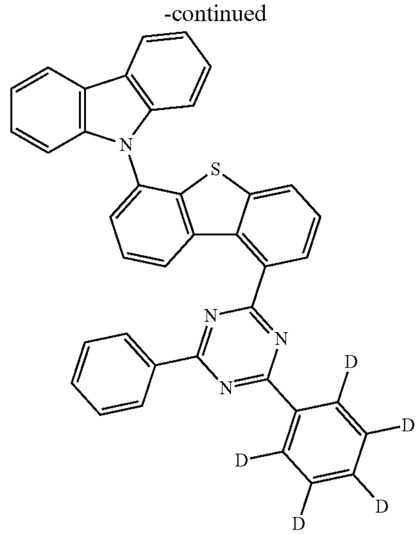
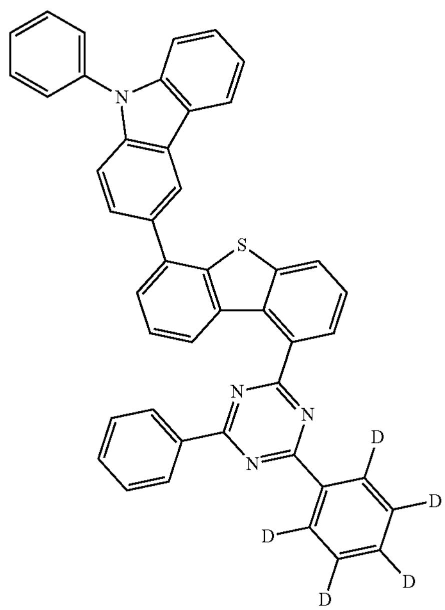
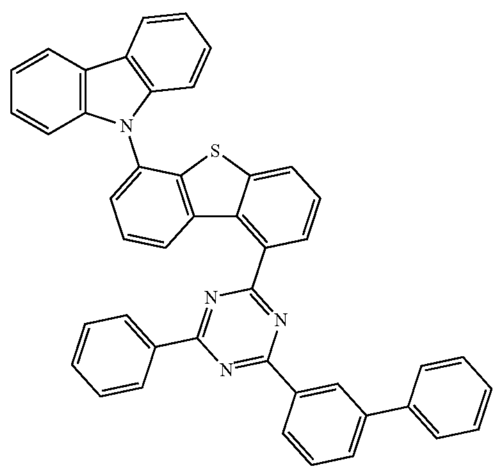
-continued
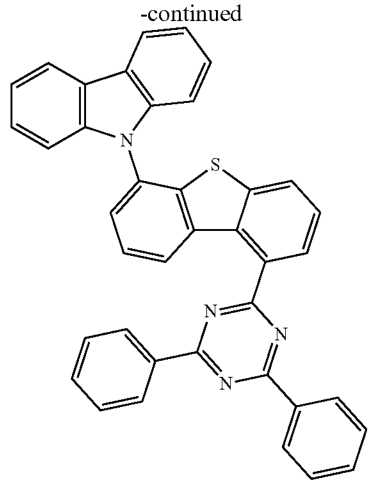
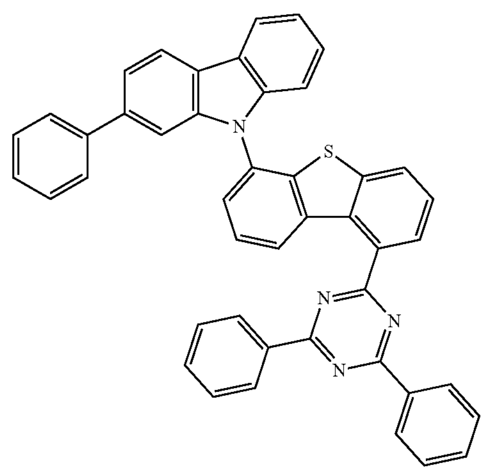
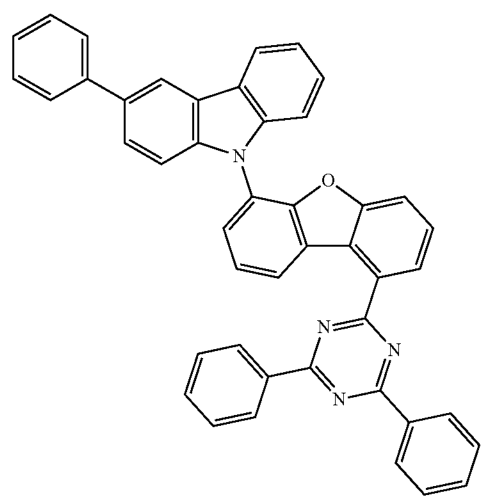

-continued
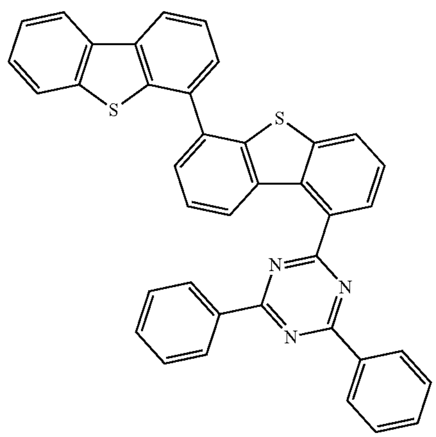
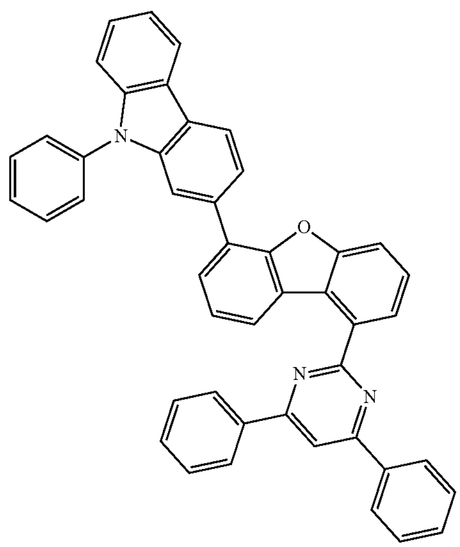
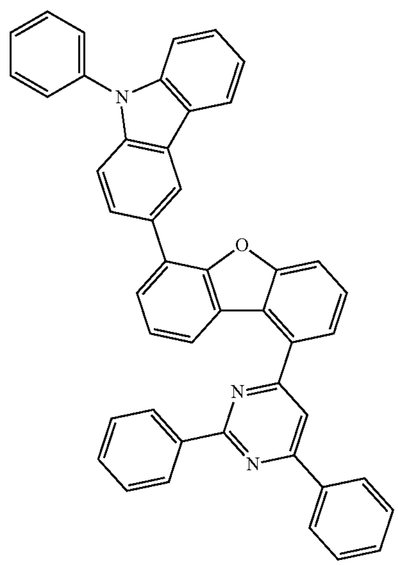
-continued
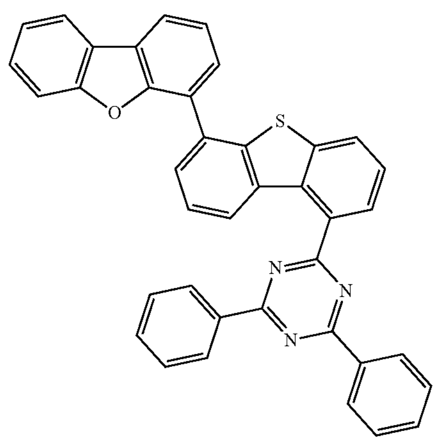
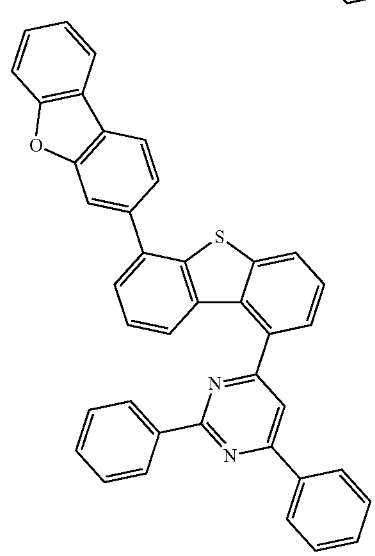
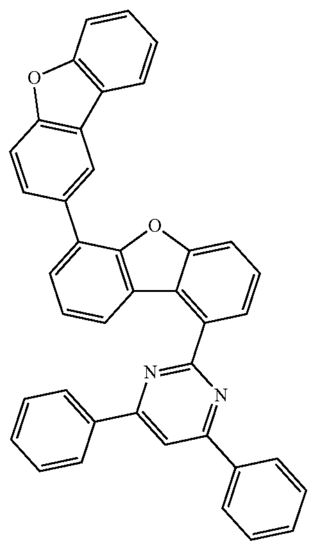

-continued
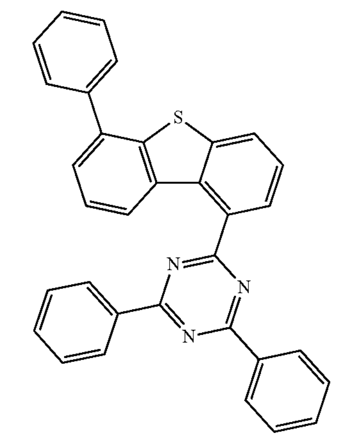
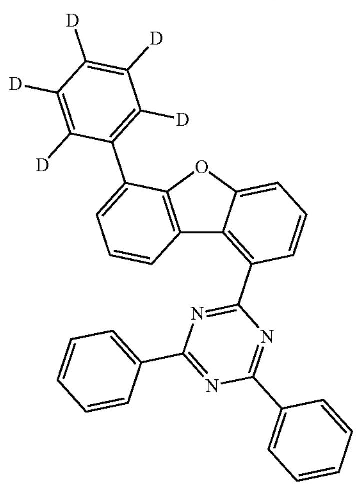
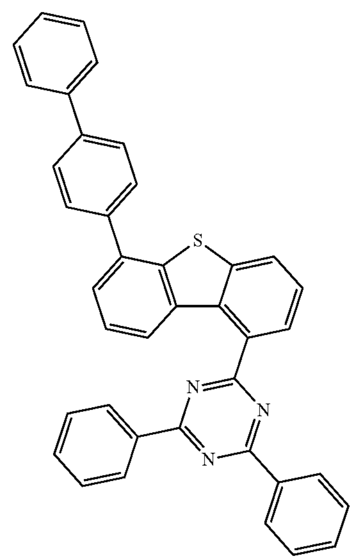
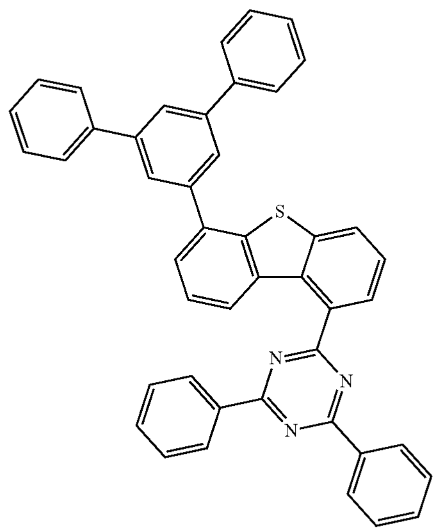
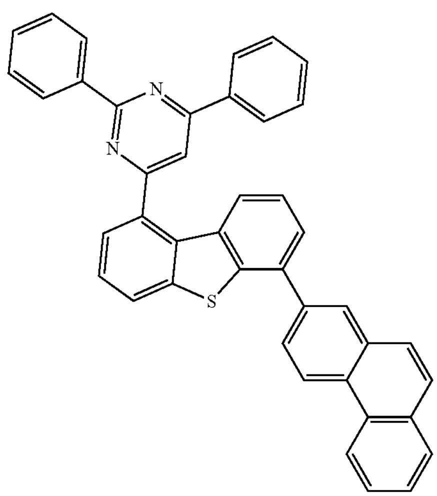
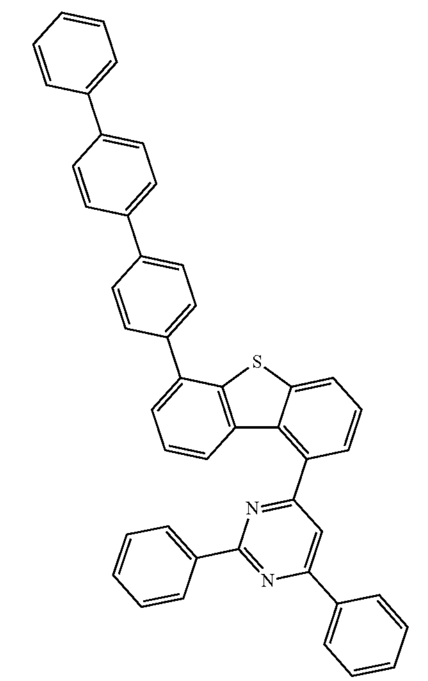

-continued
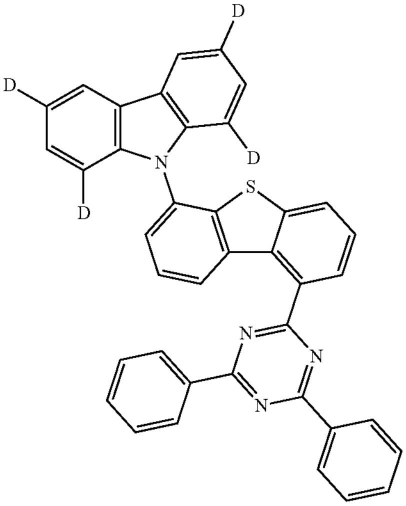
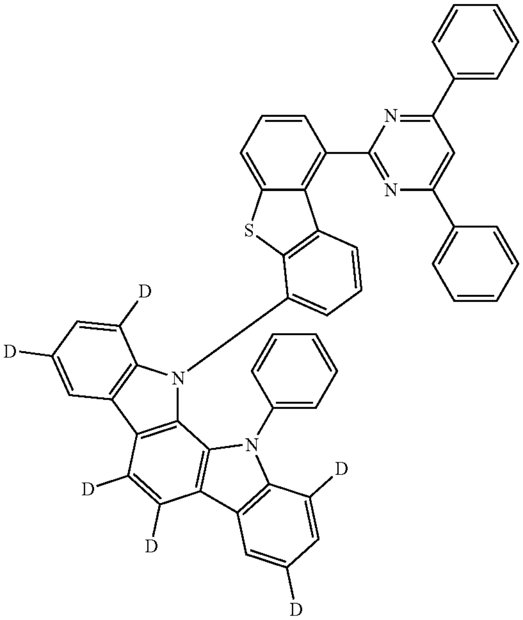
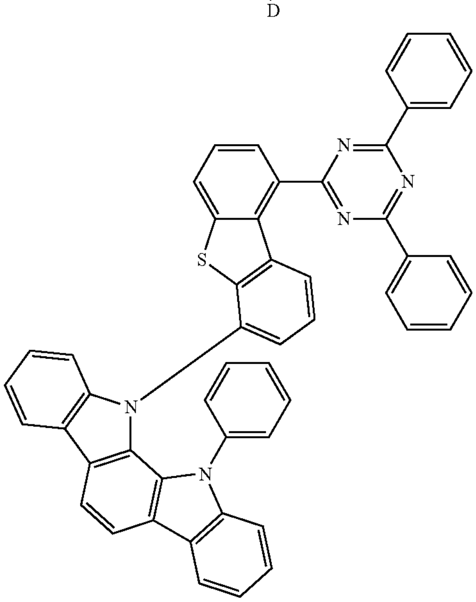
-continued
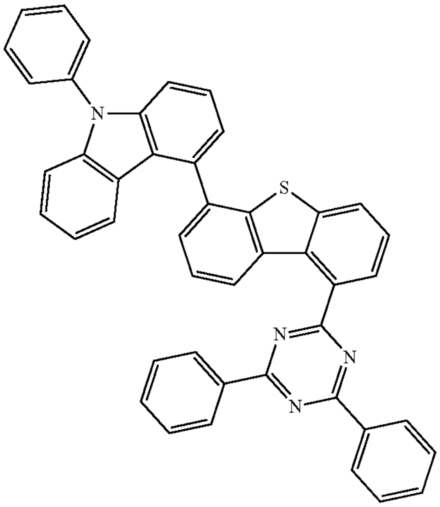
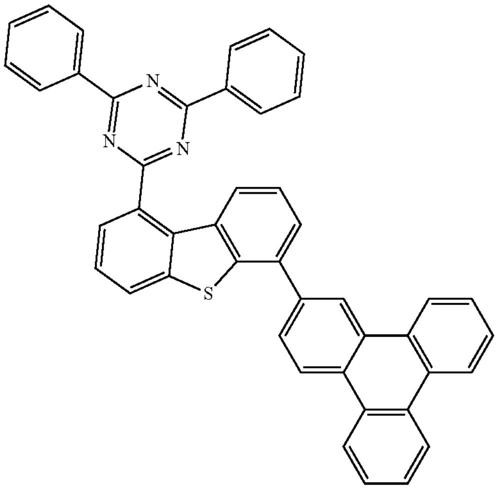
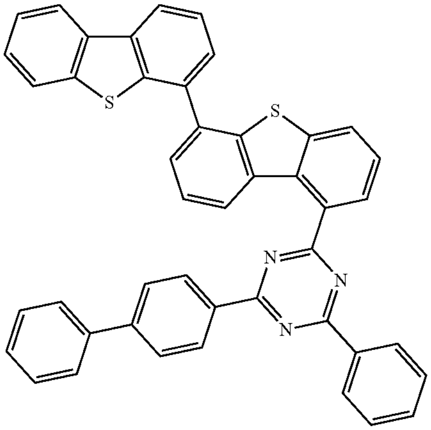

-continued
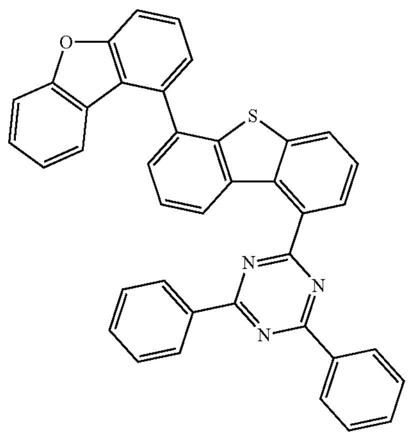
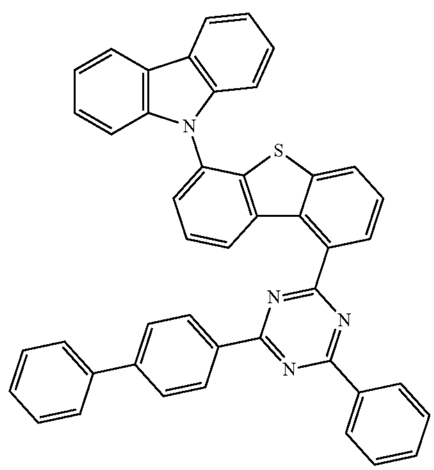
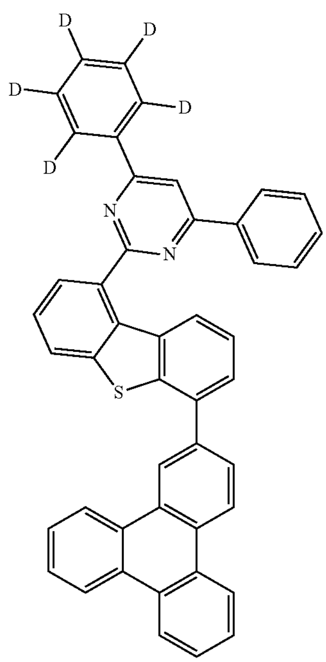
-continued
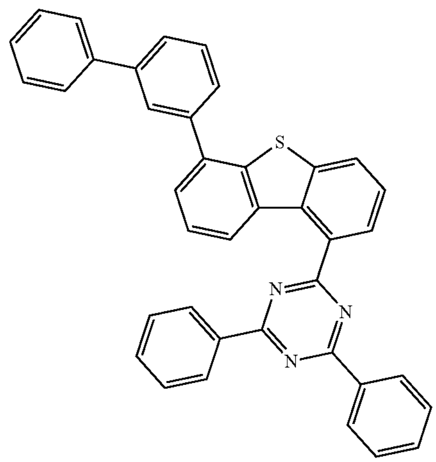
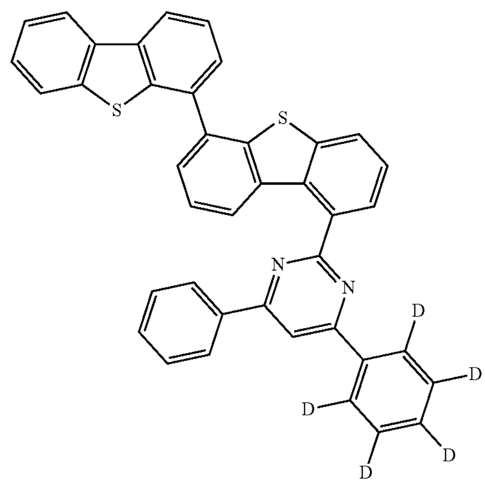
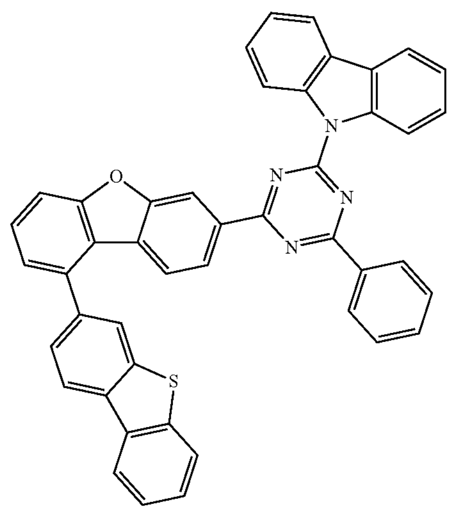

-continued
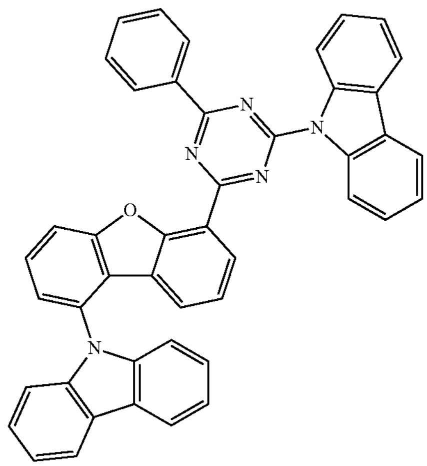
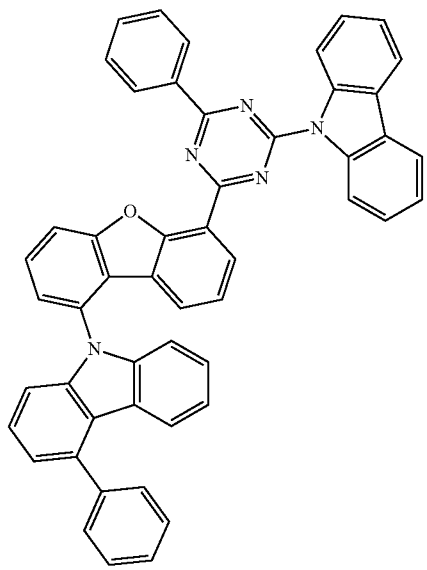
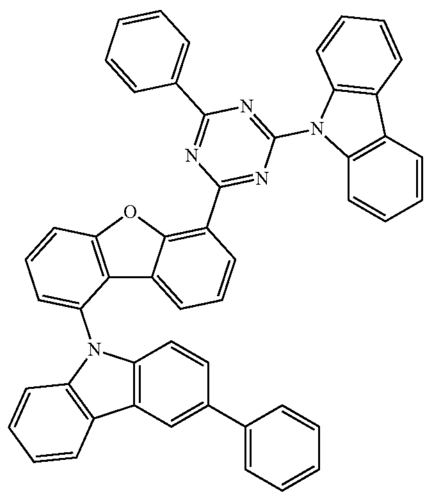
-continued
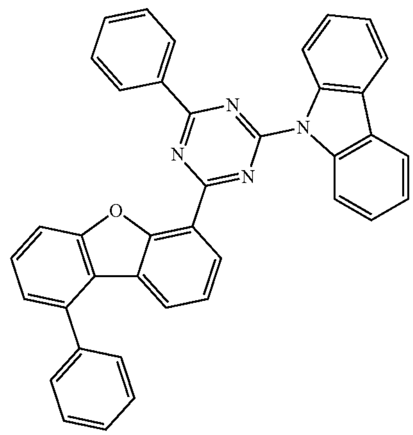
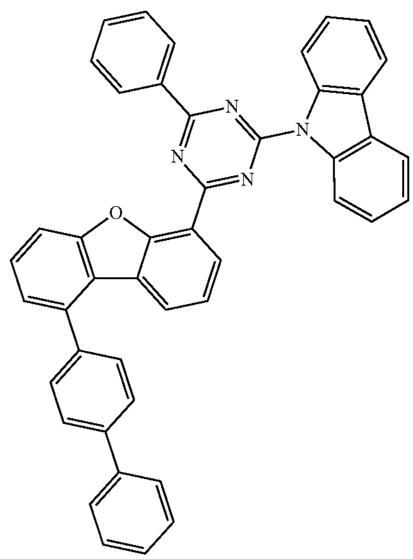
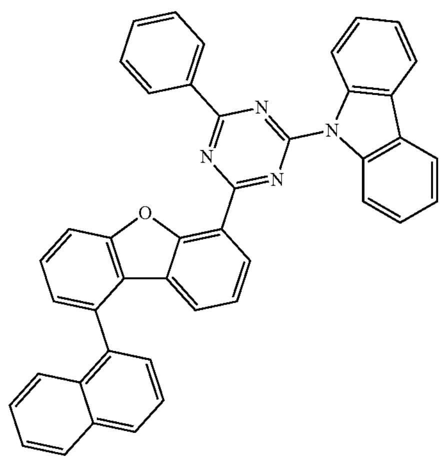

-continued
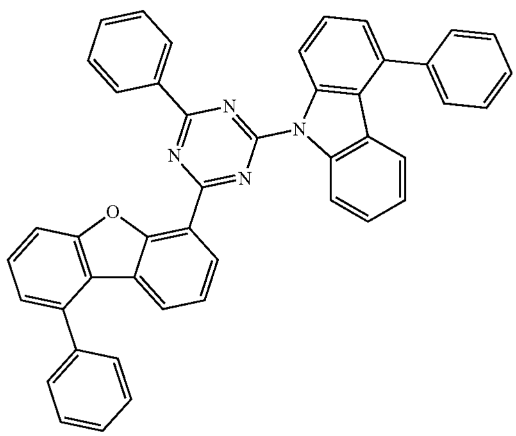
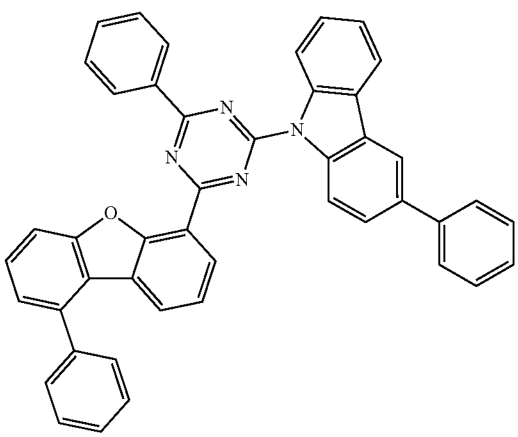
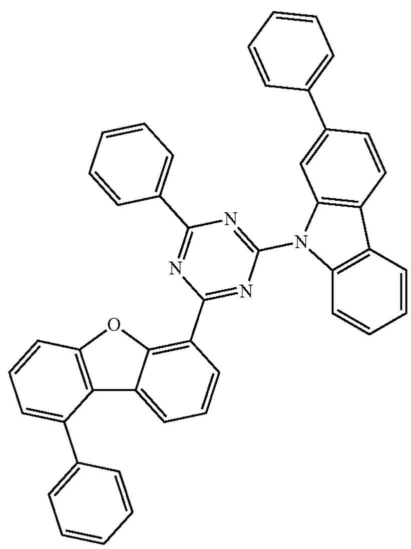
-continued
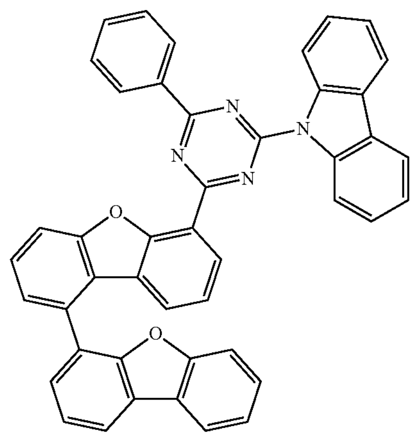
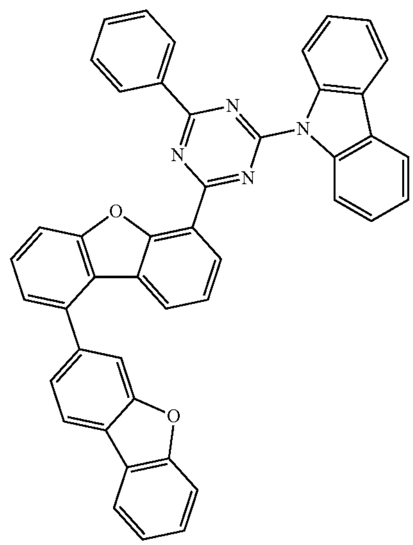
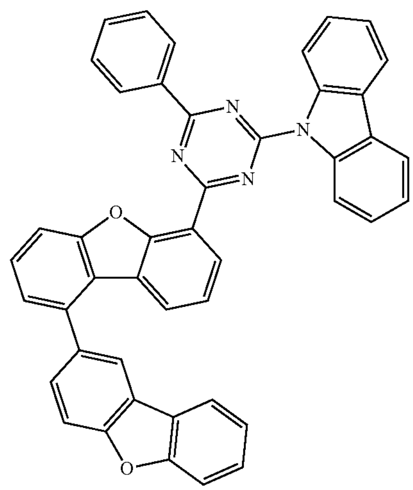

-continued
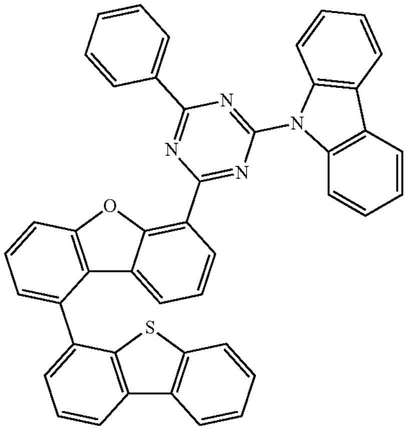
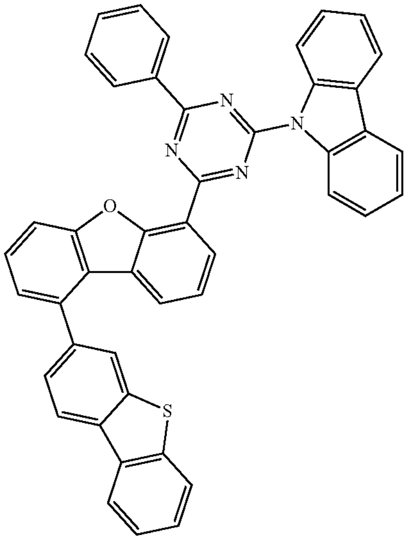
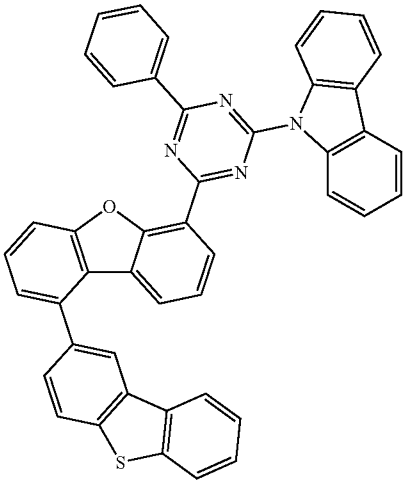
-continued
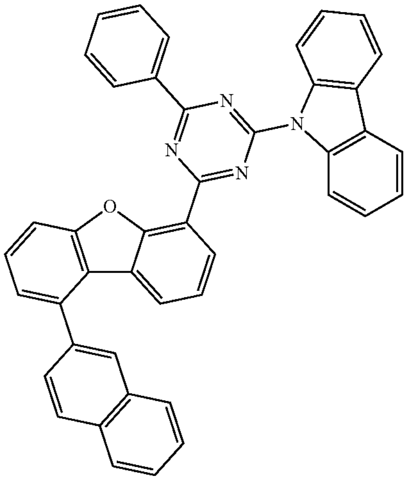
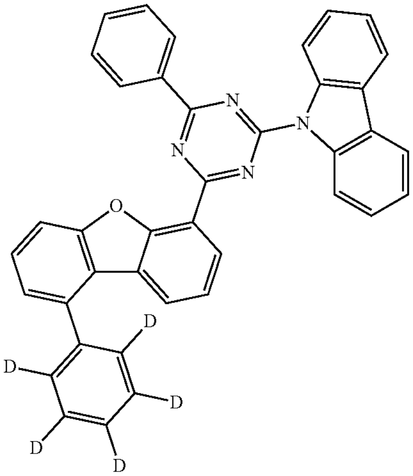
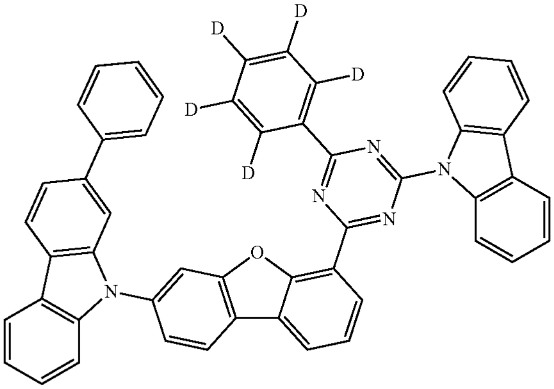
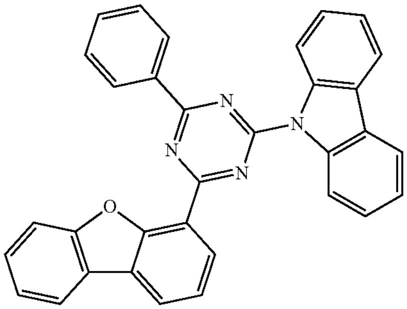

-continued
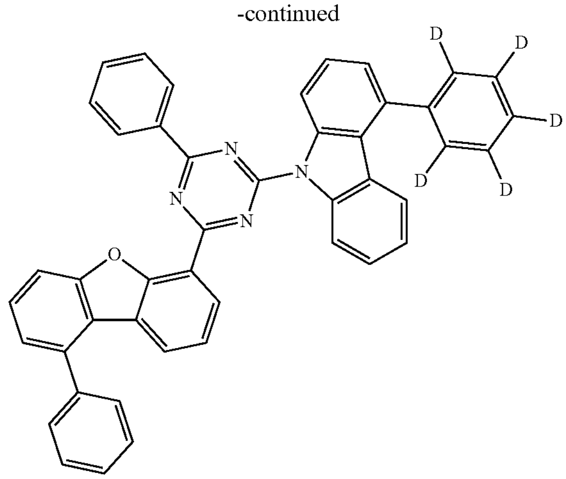
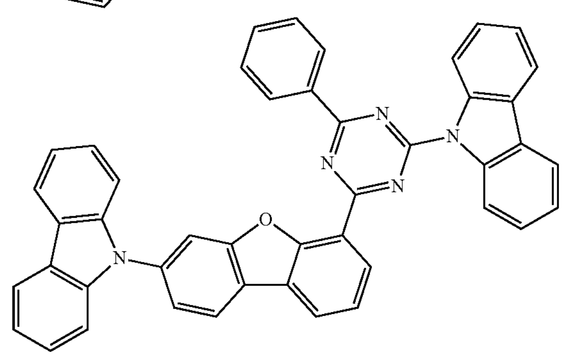
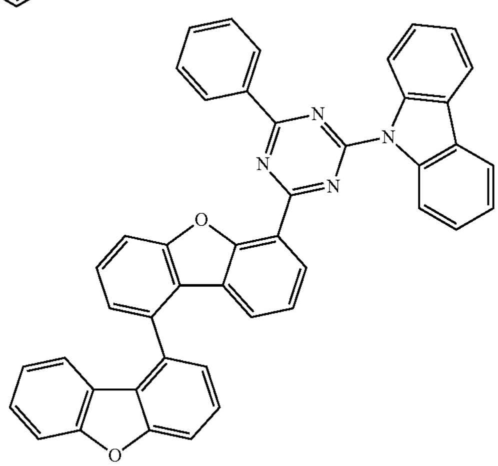
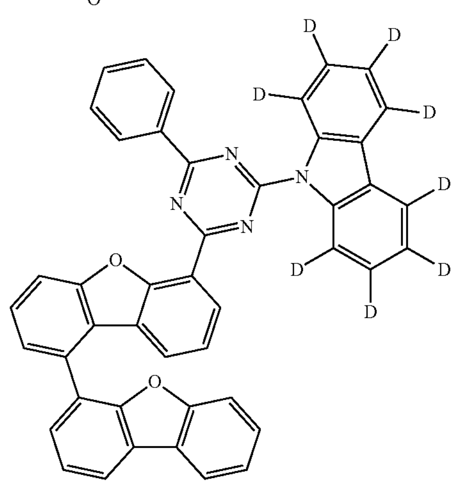
-continued
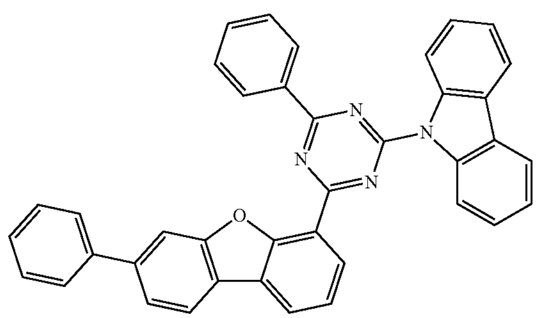
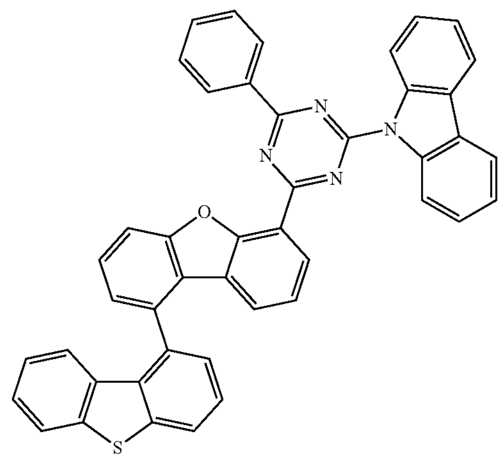
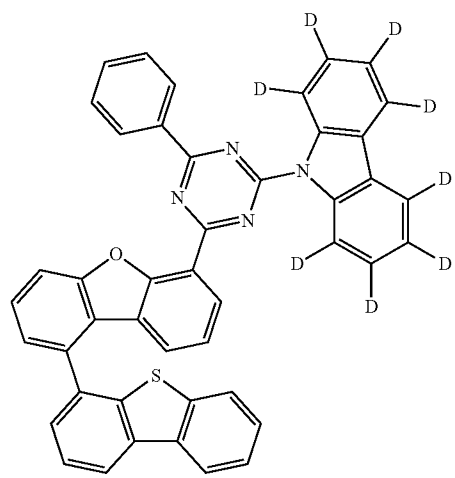
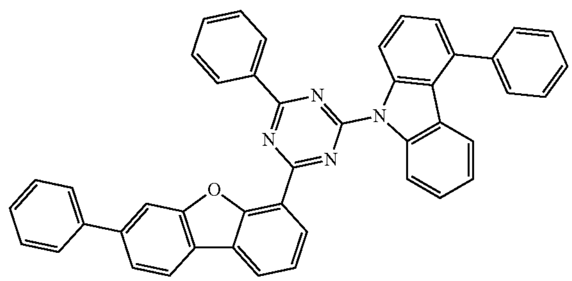

-continued
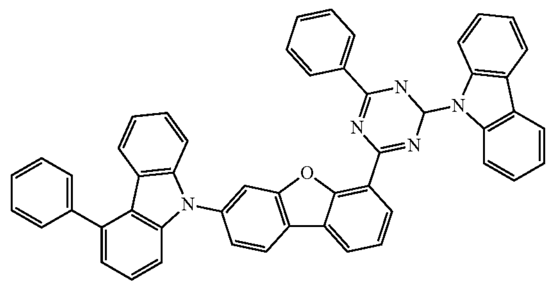
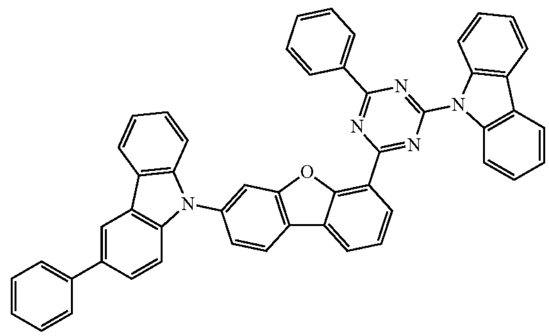
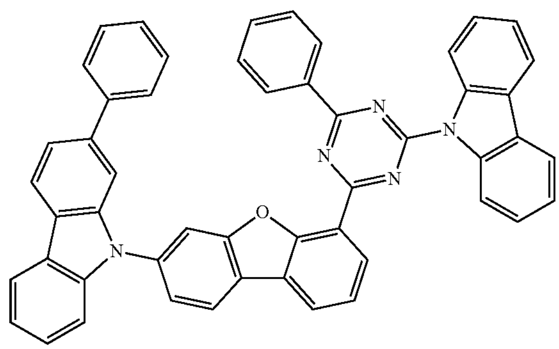
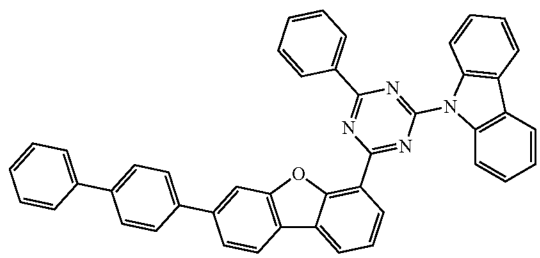
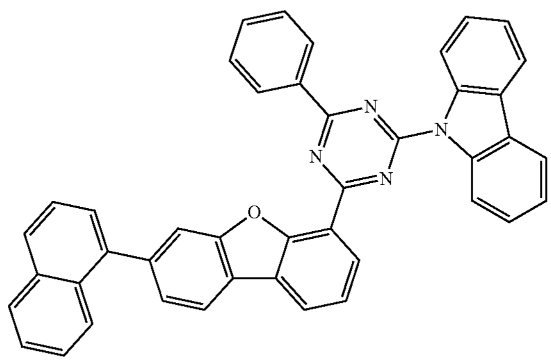
-continued
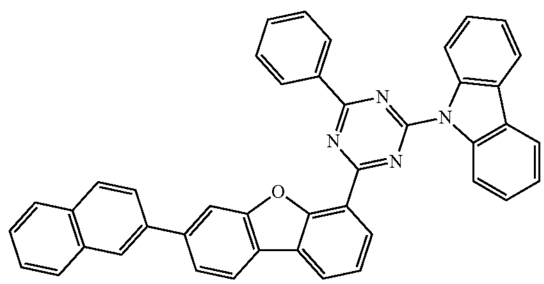
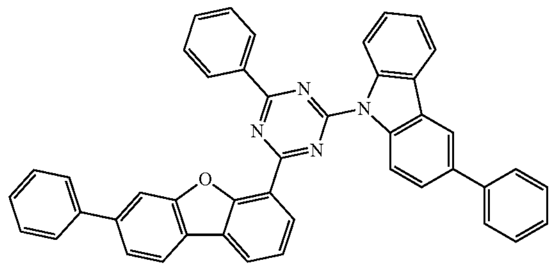
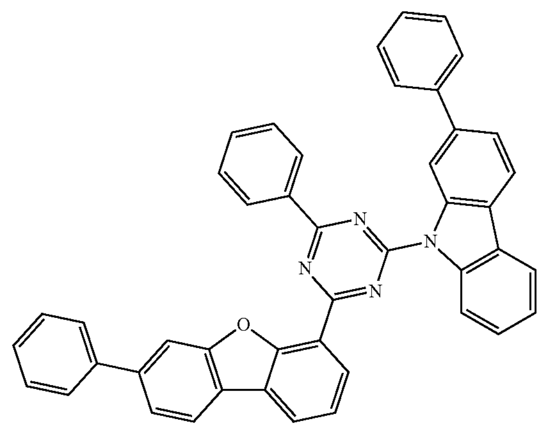
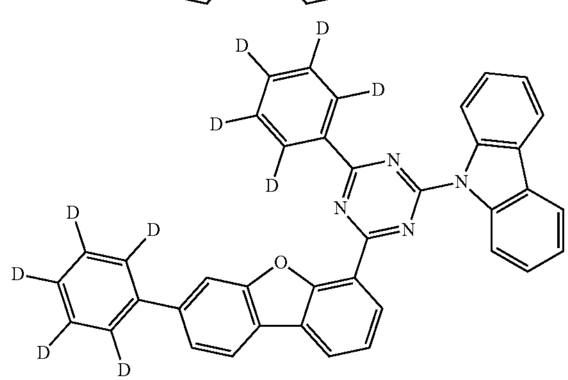
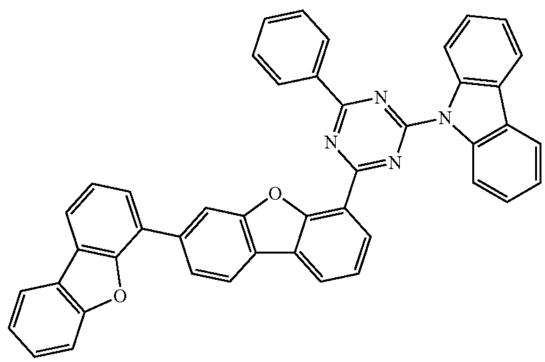

-continued
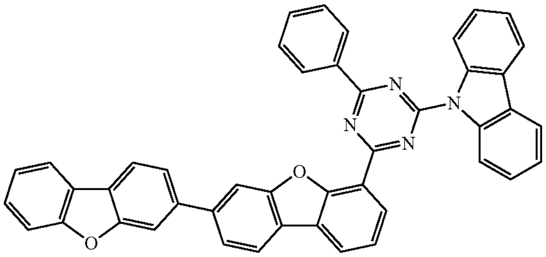
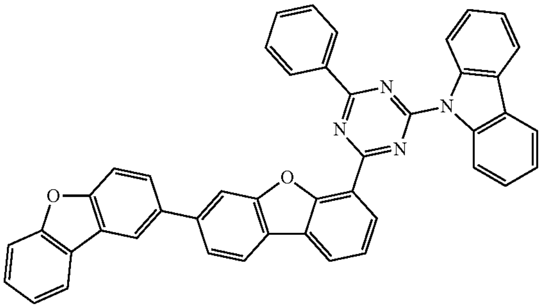
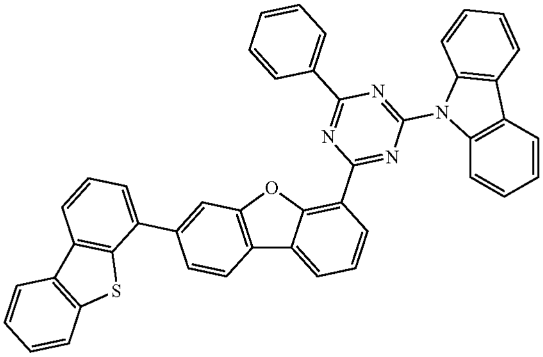
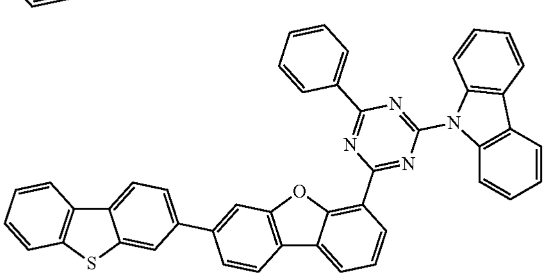
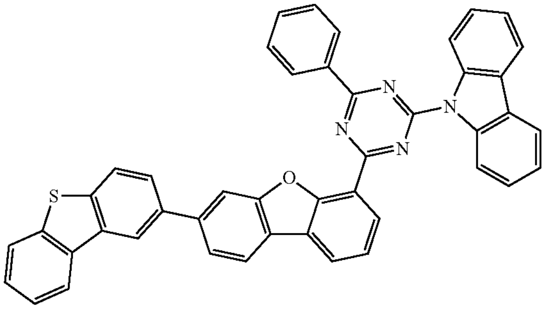
-continued
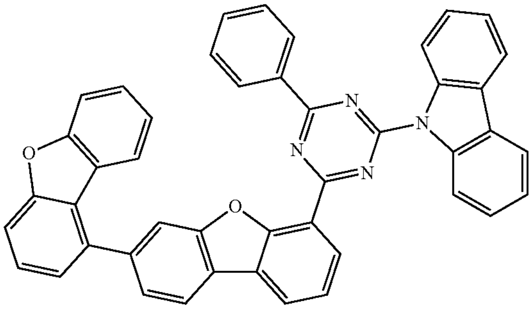
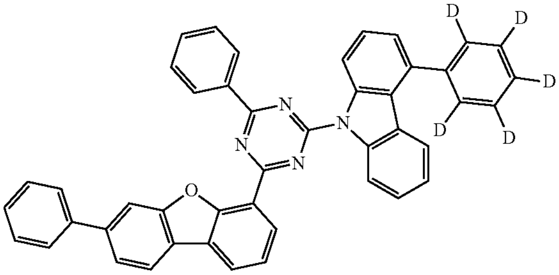
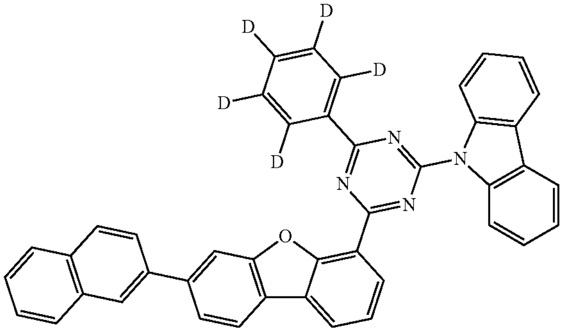
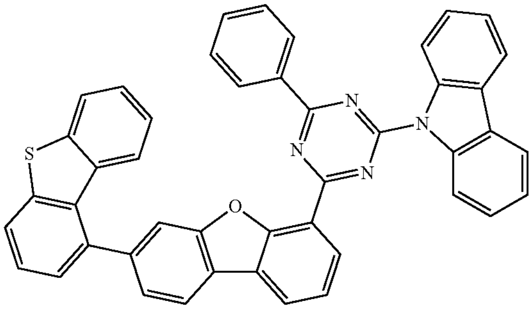
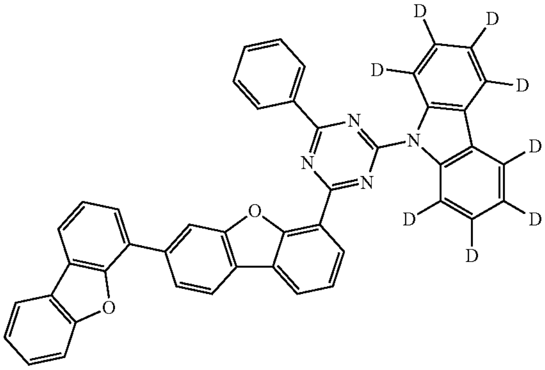

-continued
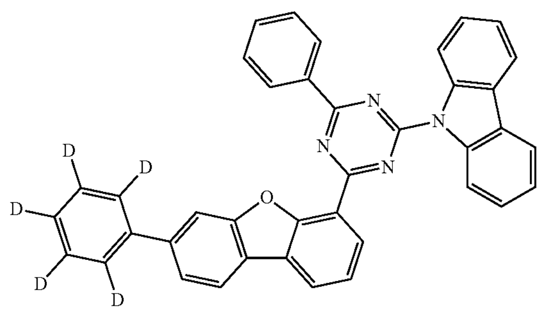
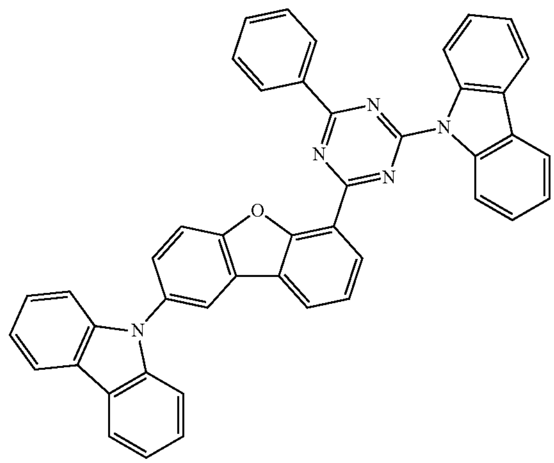
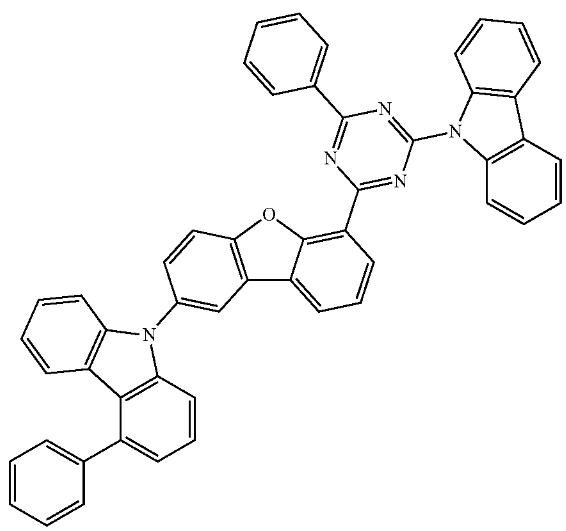
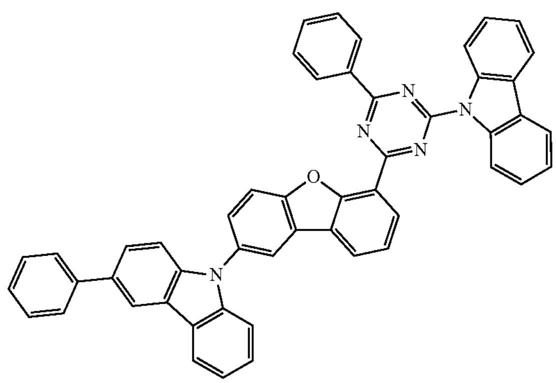
-continued
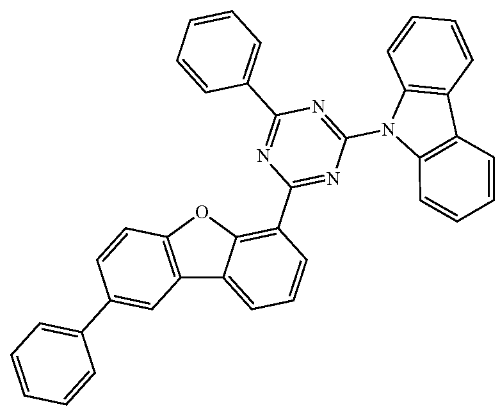
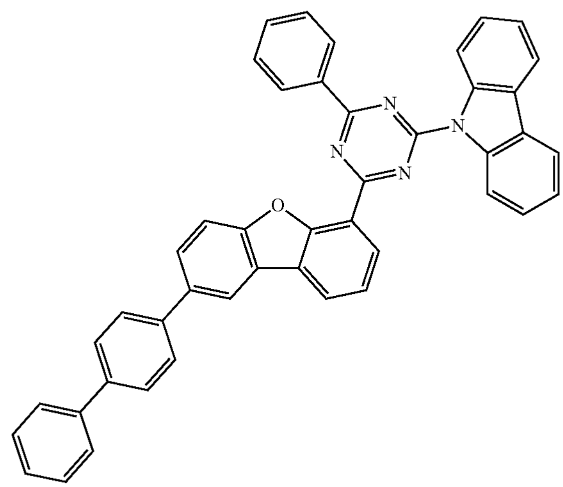
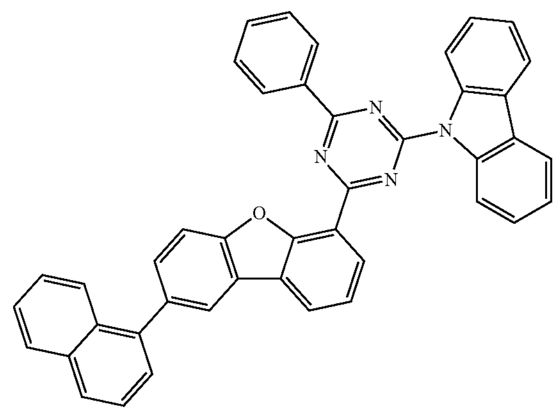
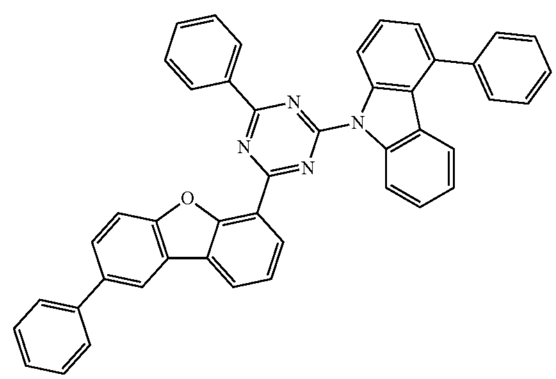

-continued
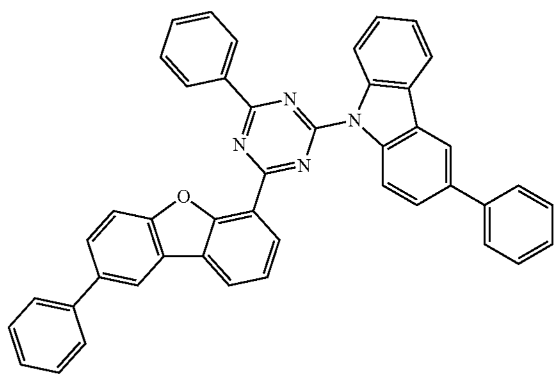
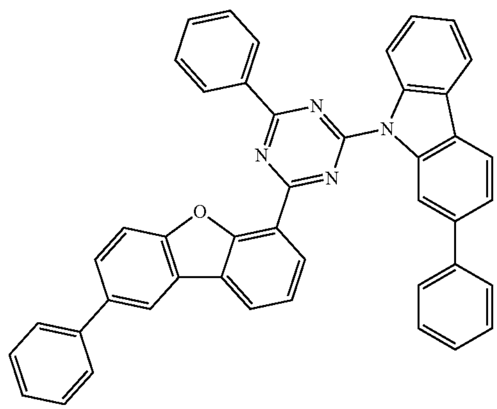
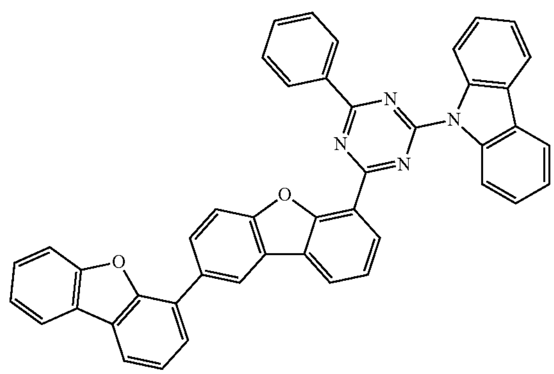
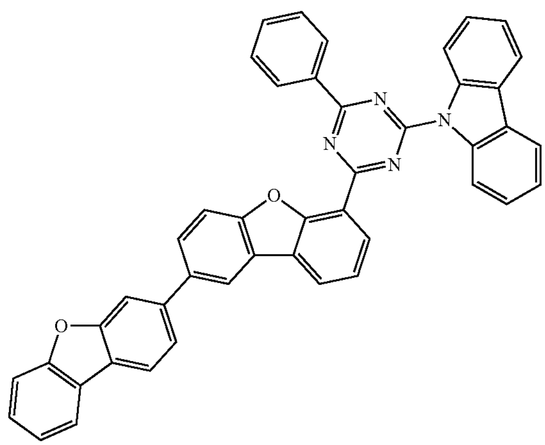
-continued
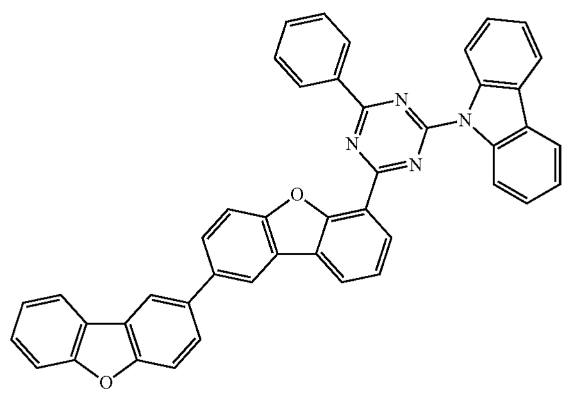
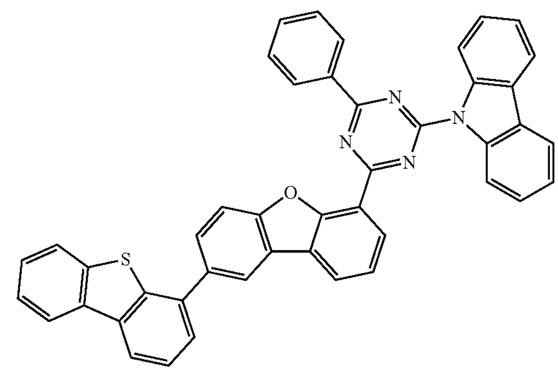
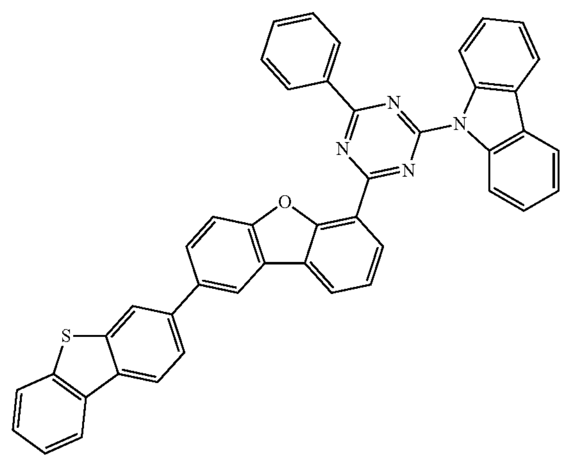
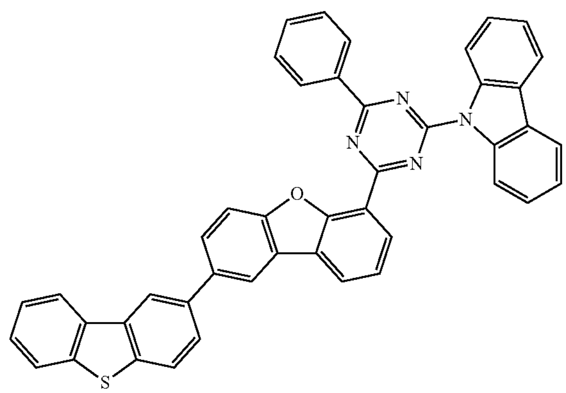

-continued
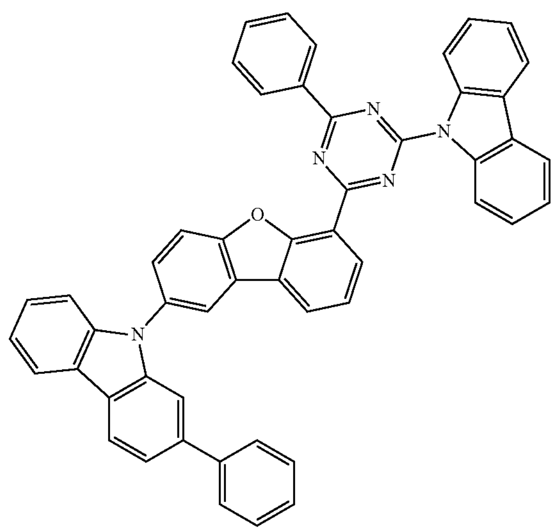
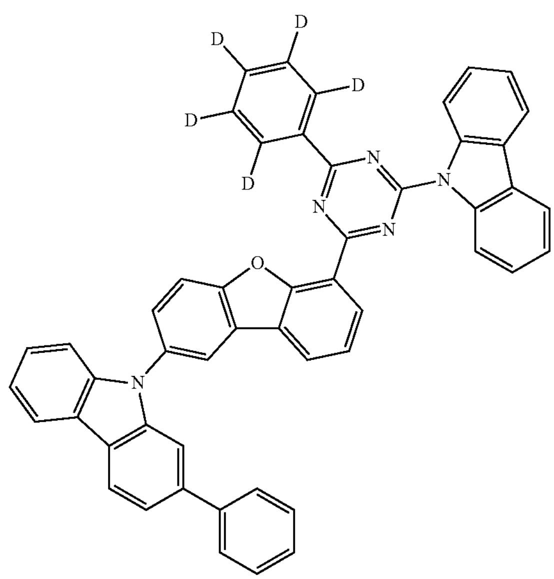
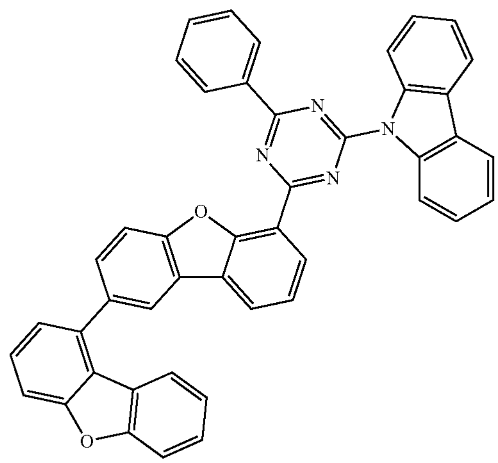
-continued
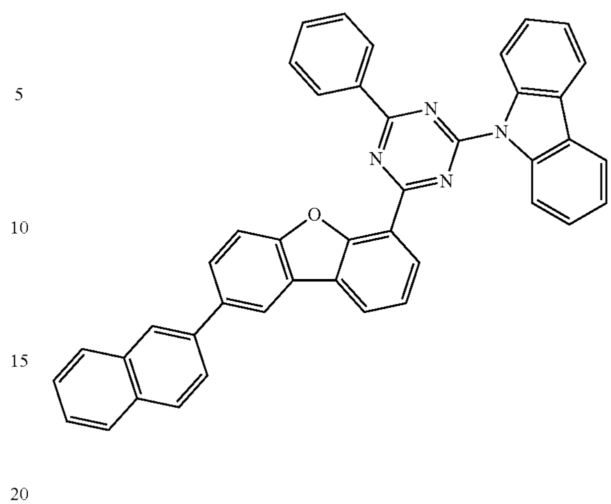
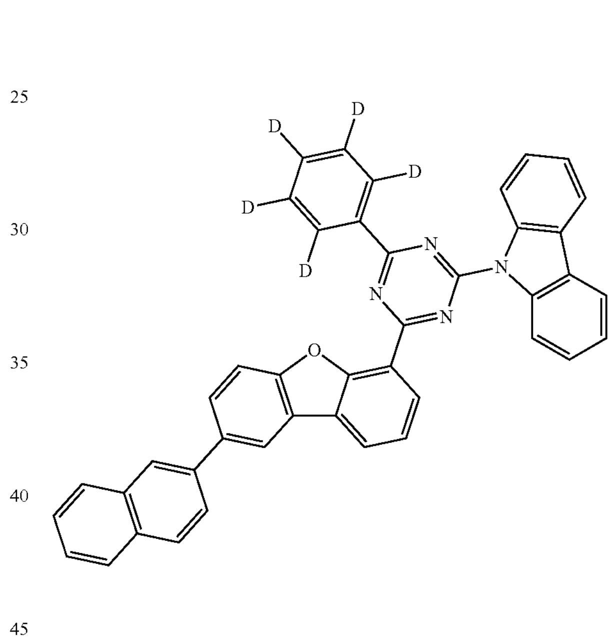
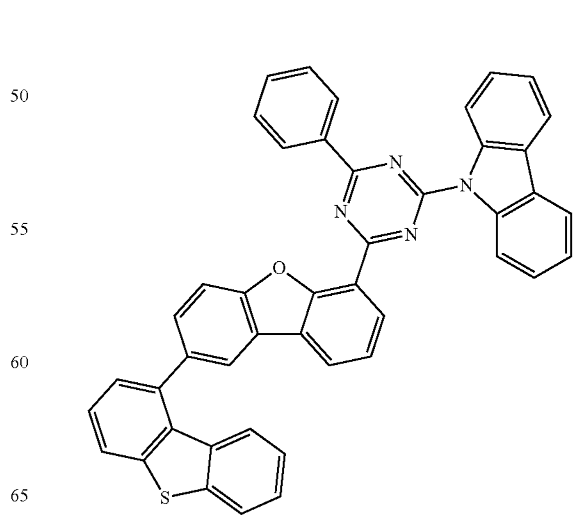

-continued
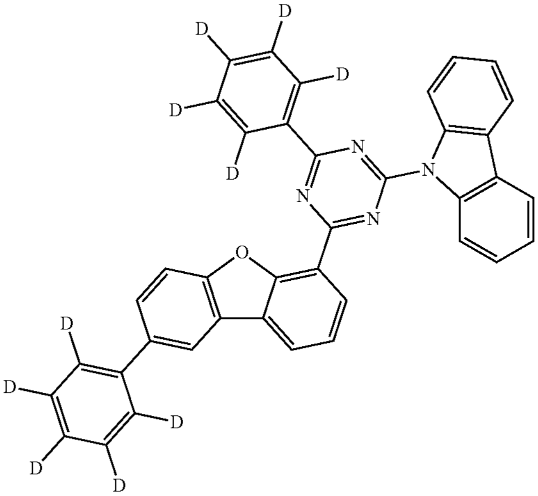
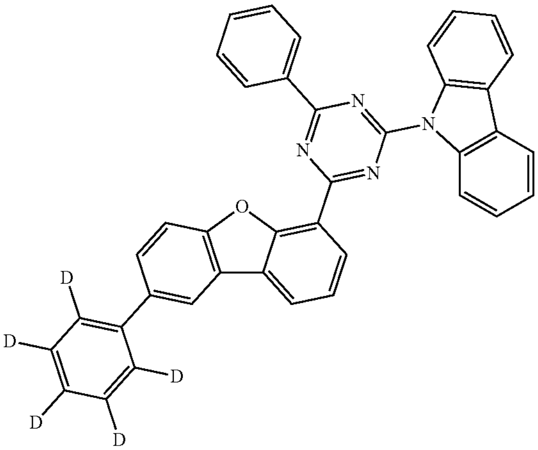
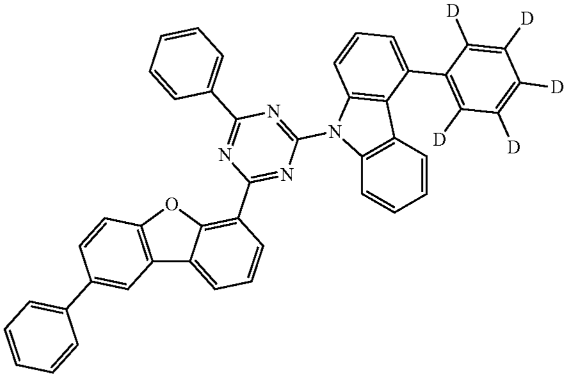
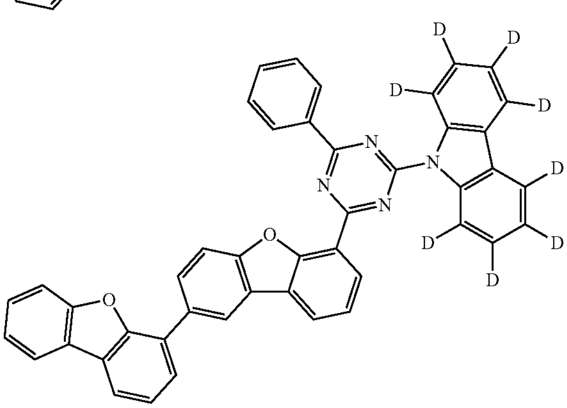
-continued
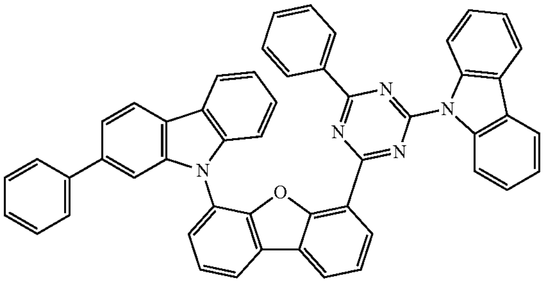
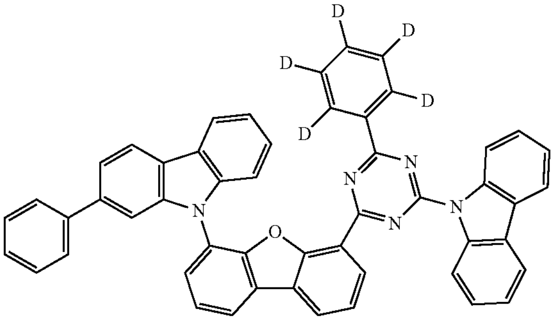
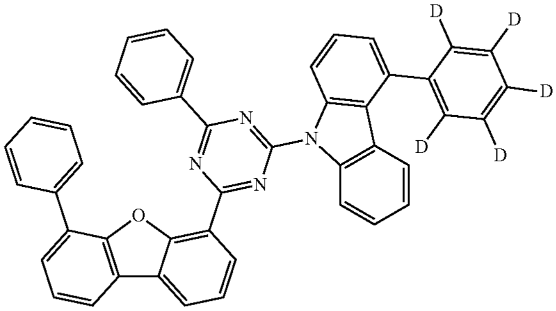
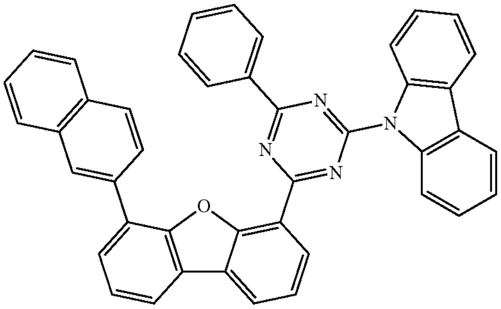
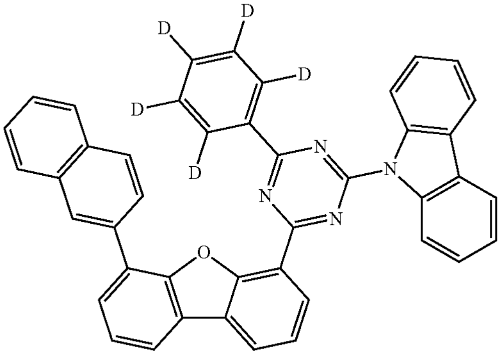

-continued
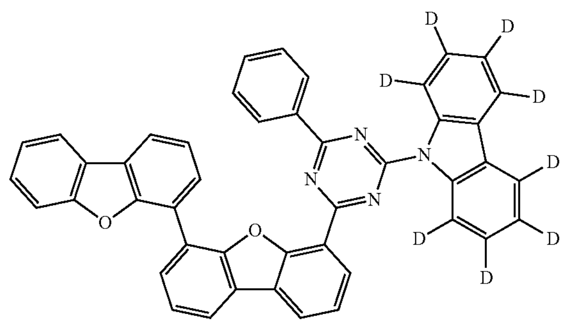
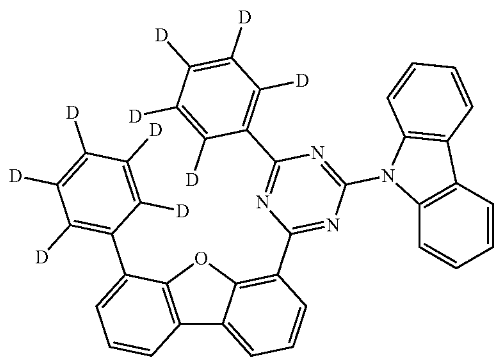
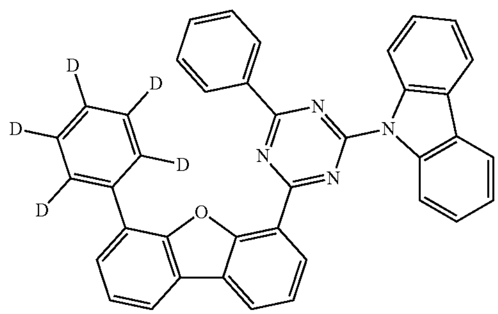
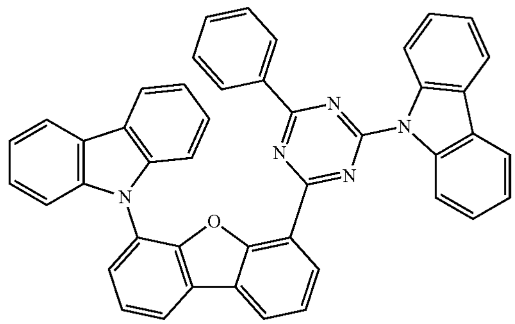
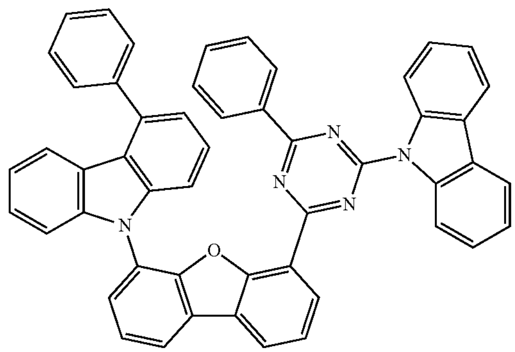
-continued
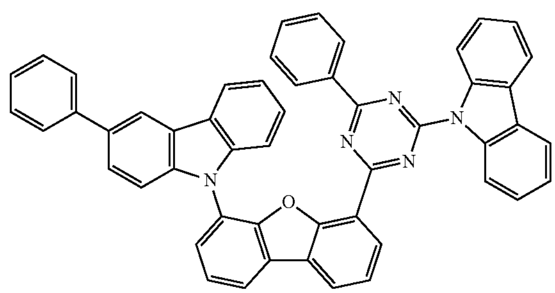
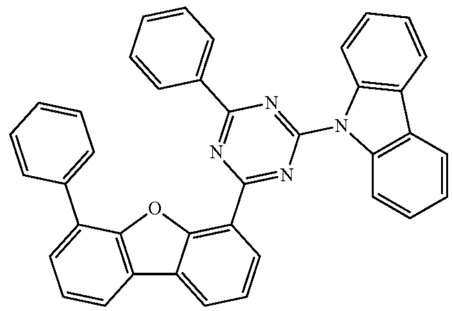
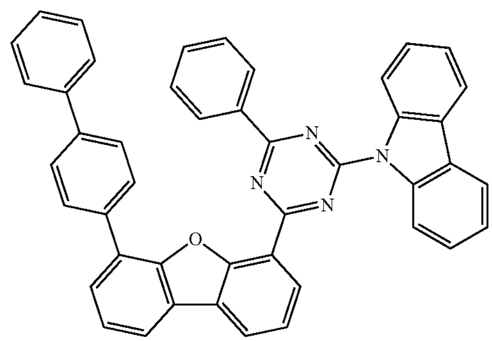
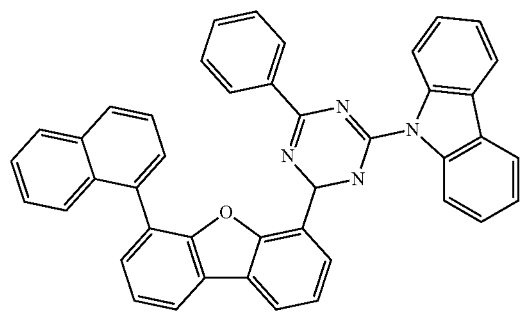
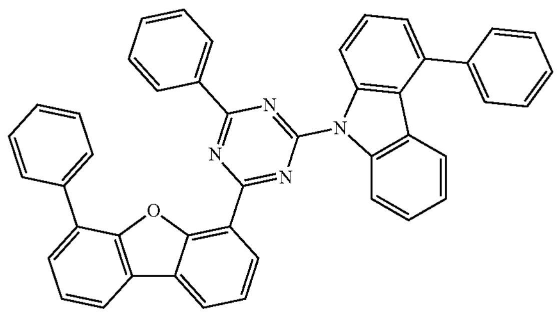

-continued
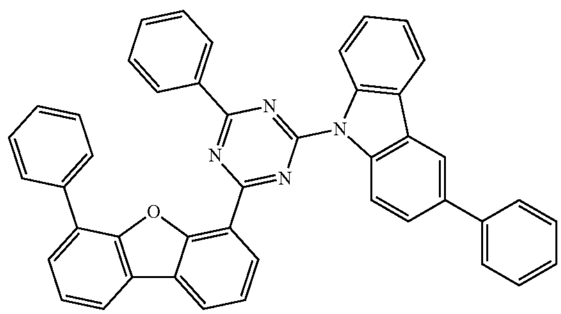
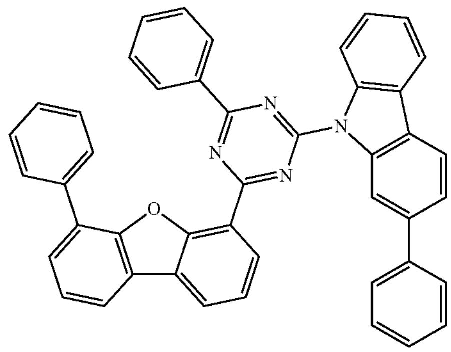
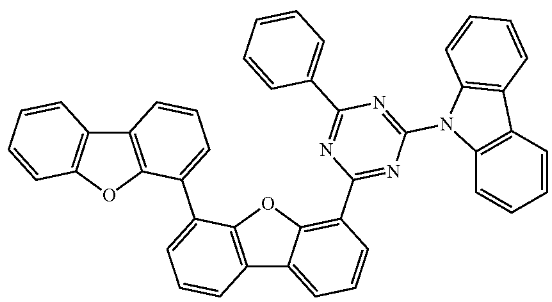
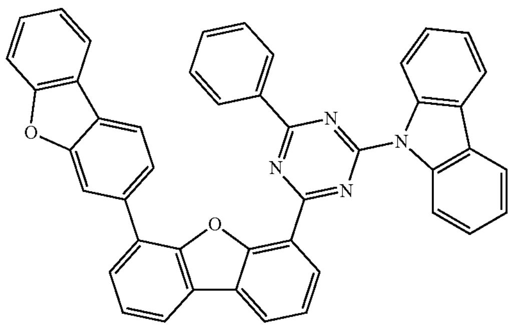
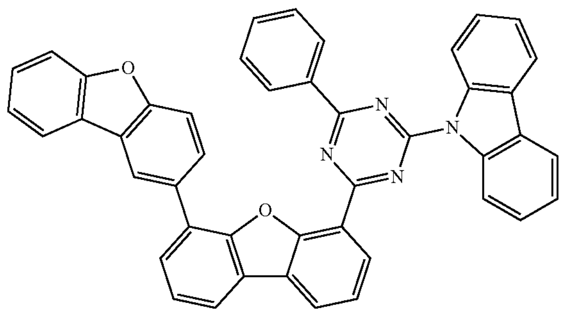
-continued
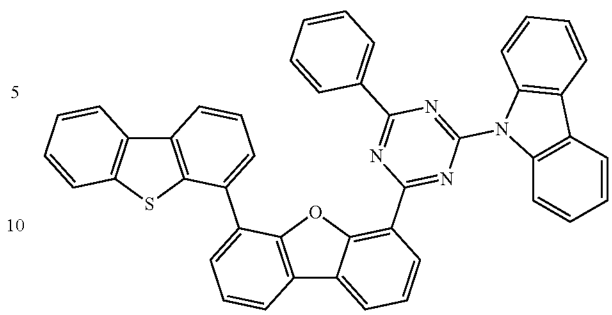
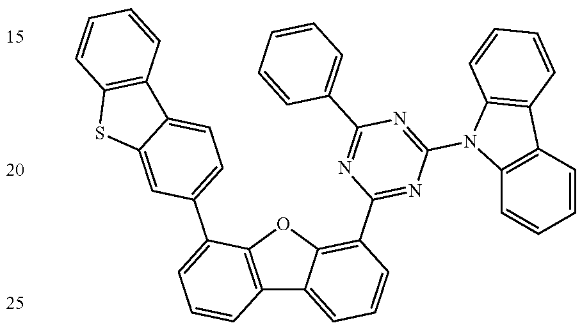
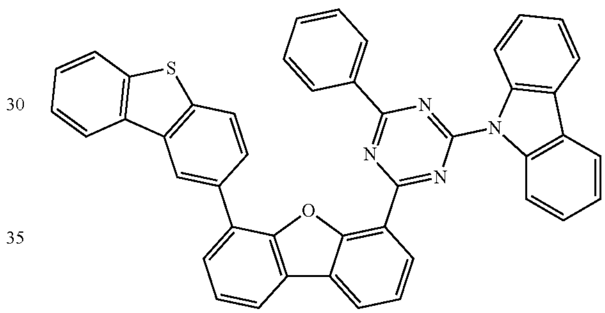
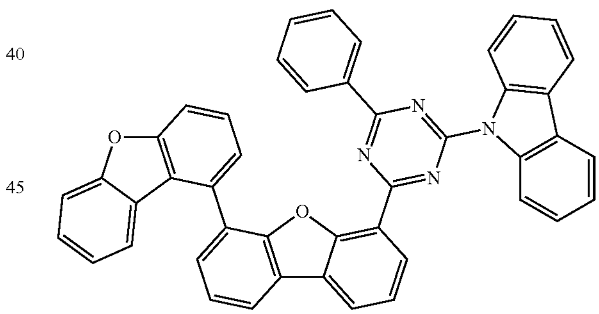
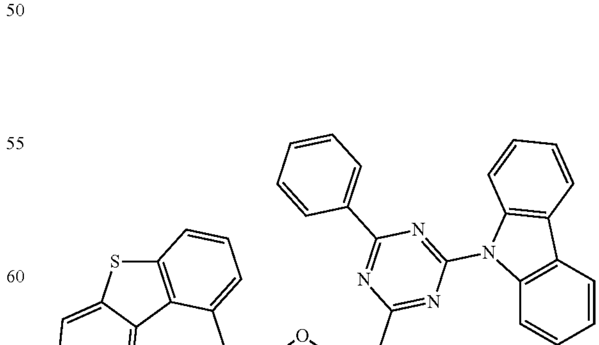

-continued
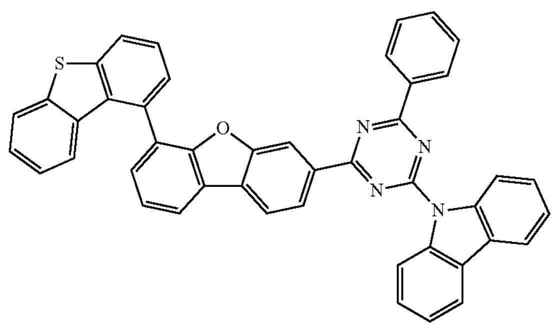
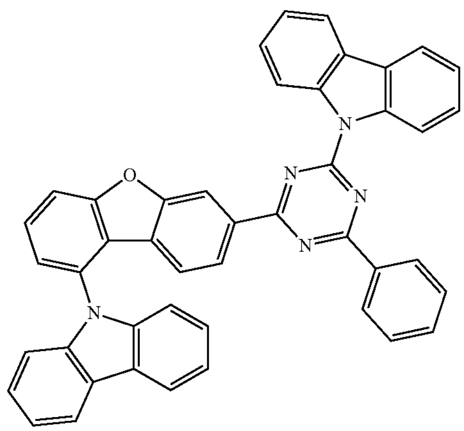
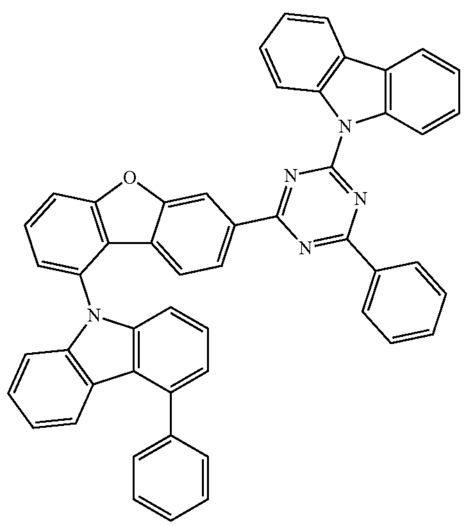
-continued
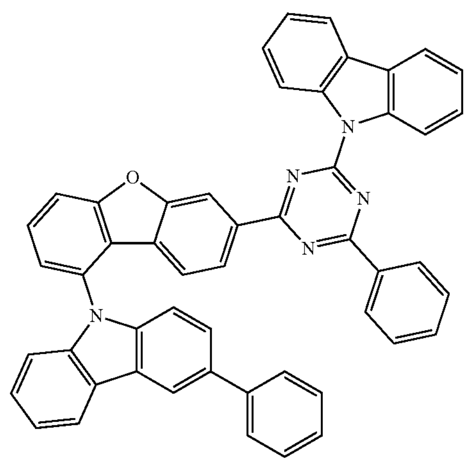
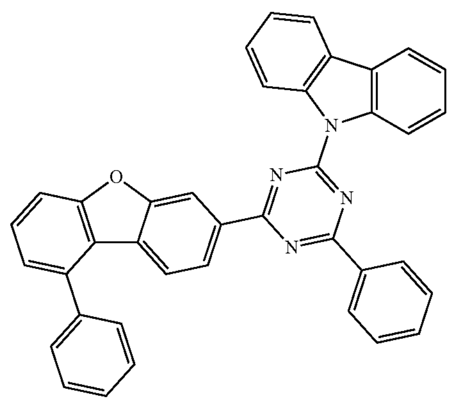
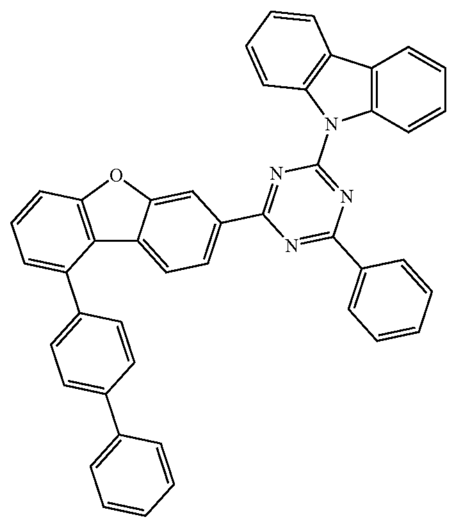

-continued
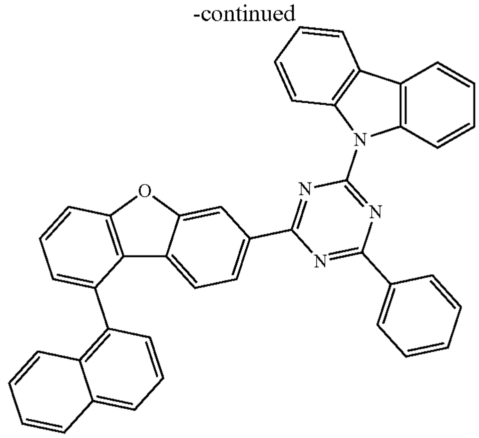
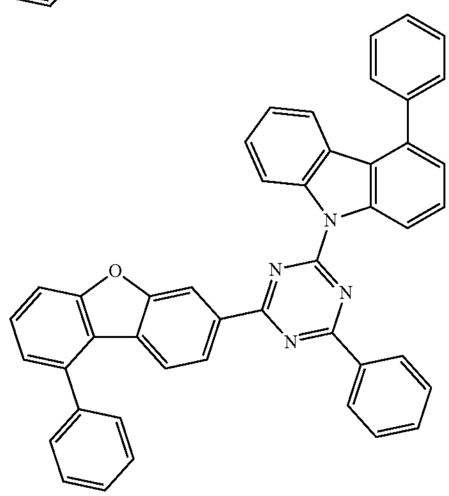
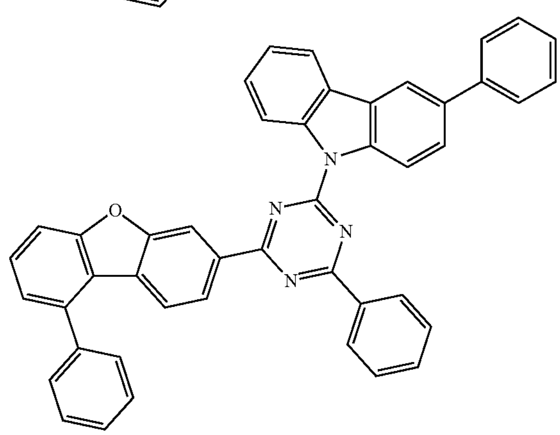
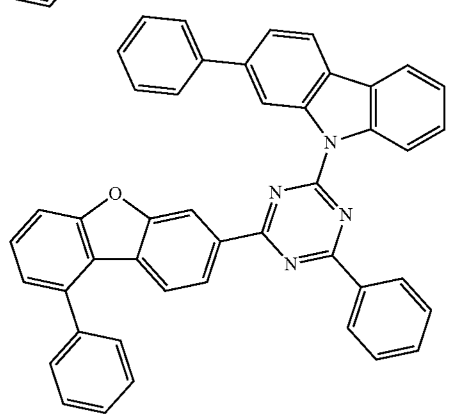
-continued
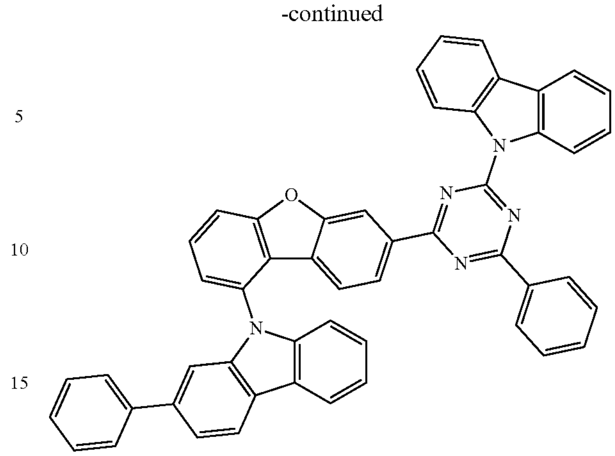
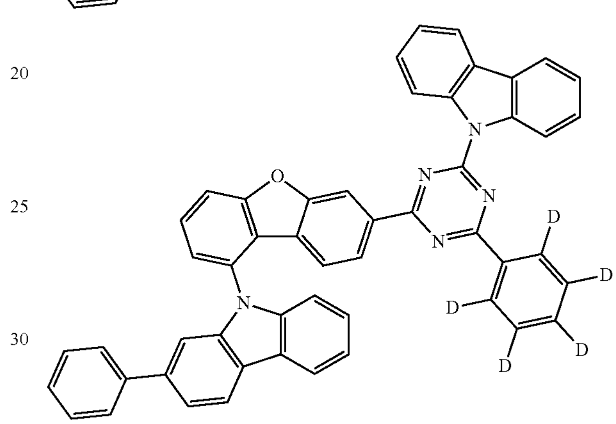
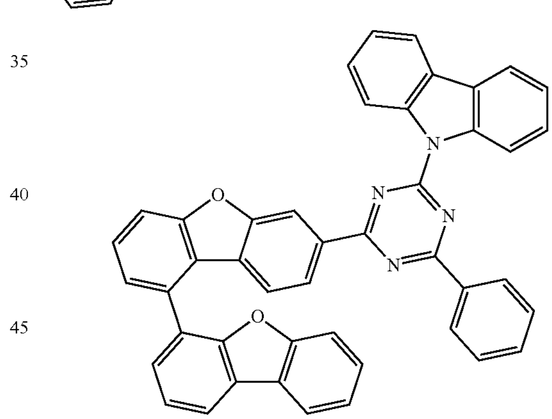
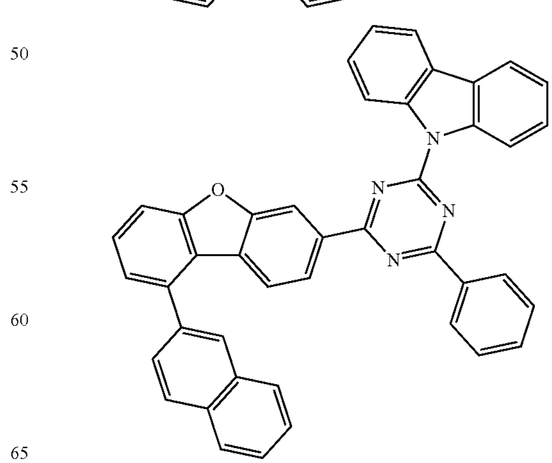

-continued
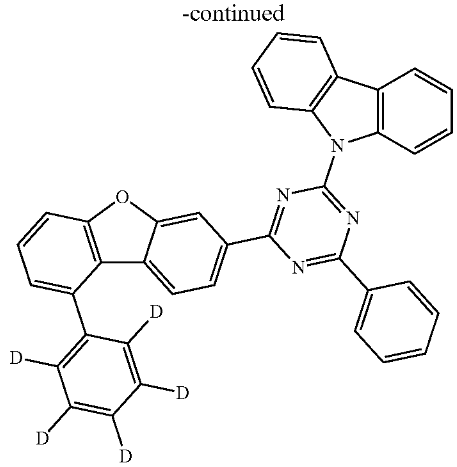
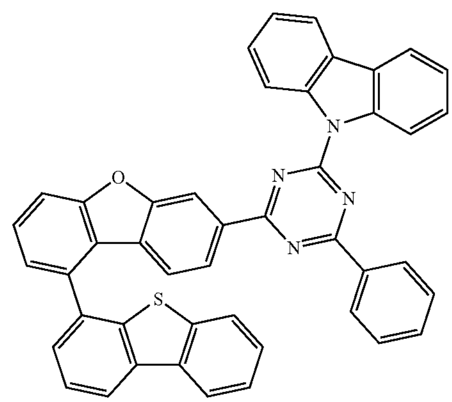
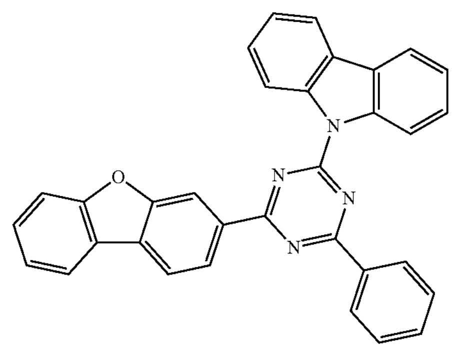
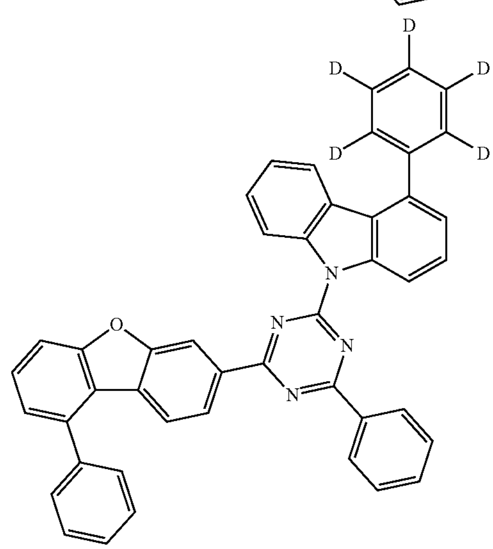
-continued
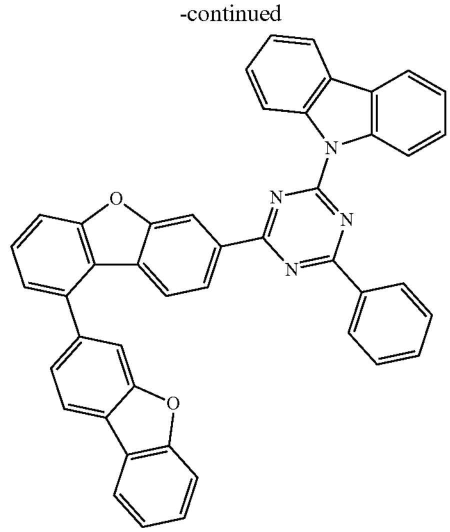
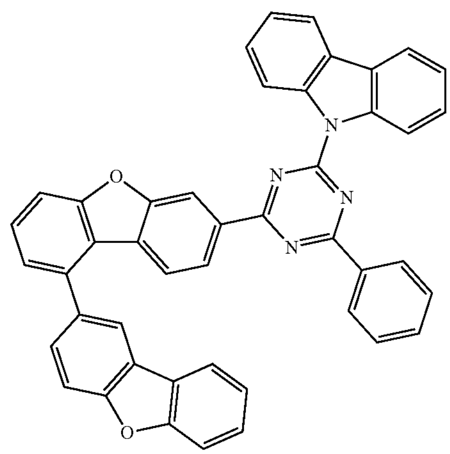
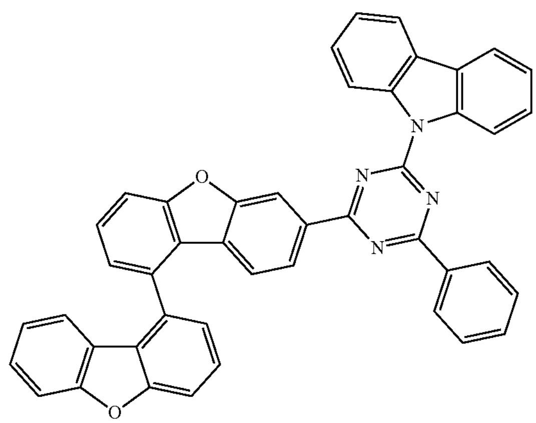

-continued
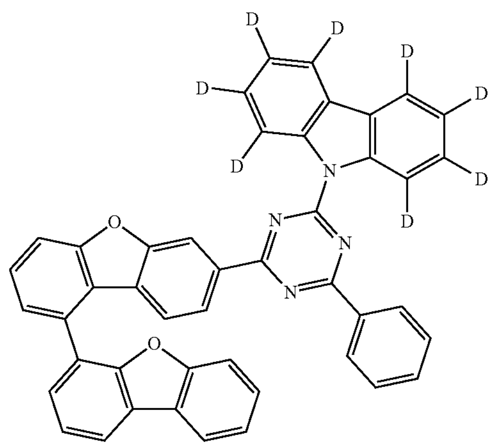
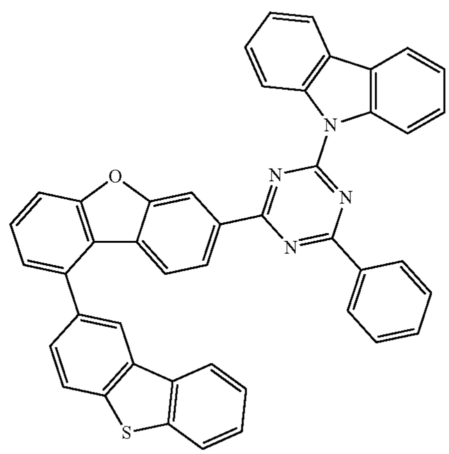
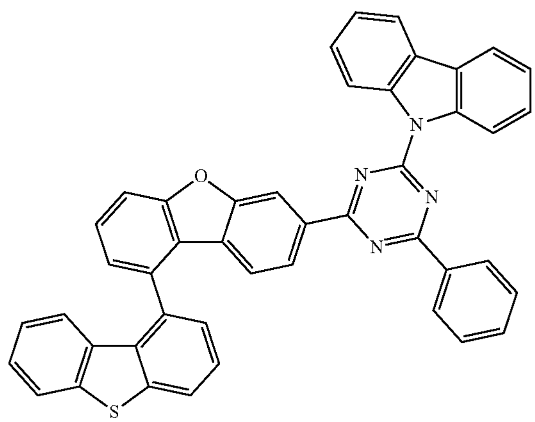
-continued
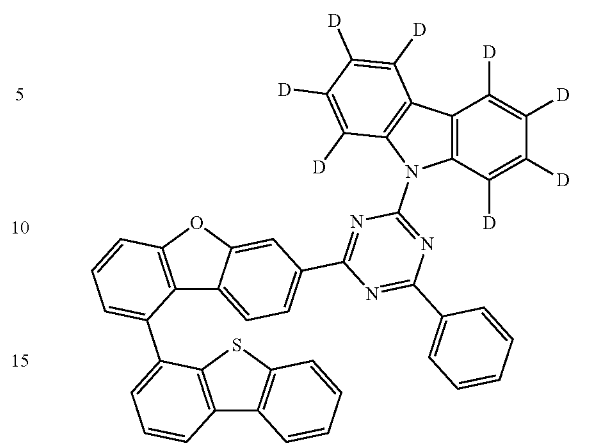
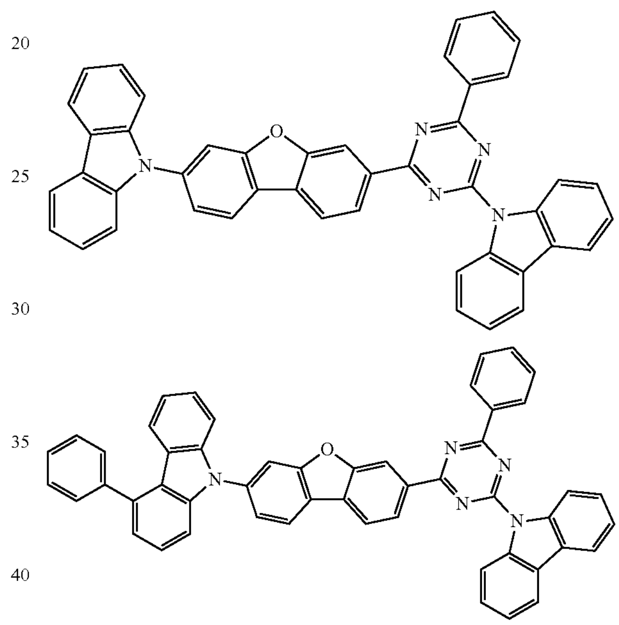
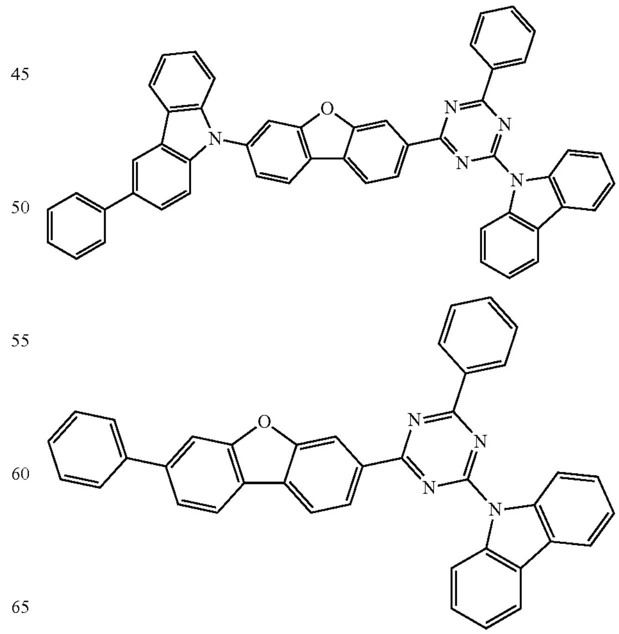

-continued
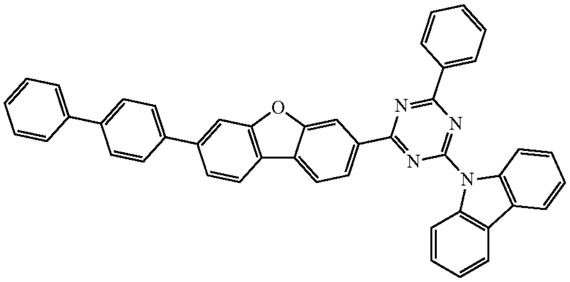
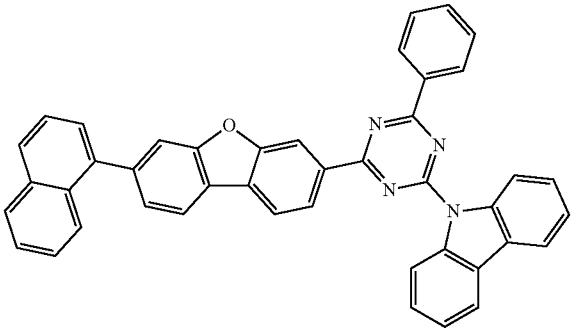
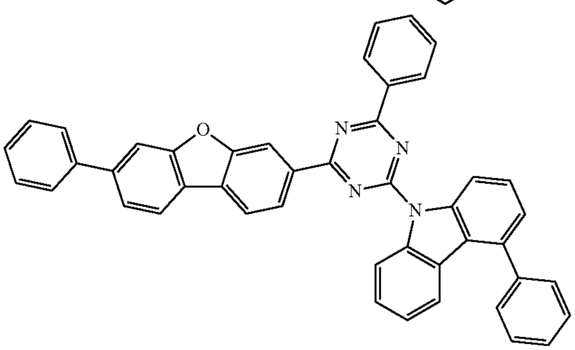
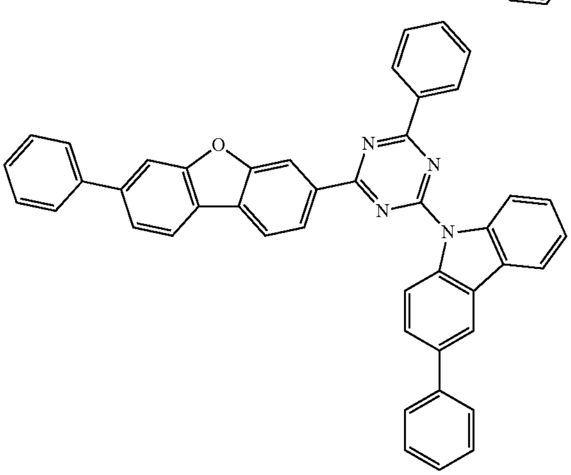
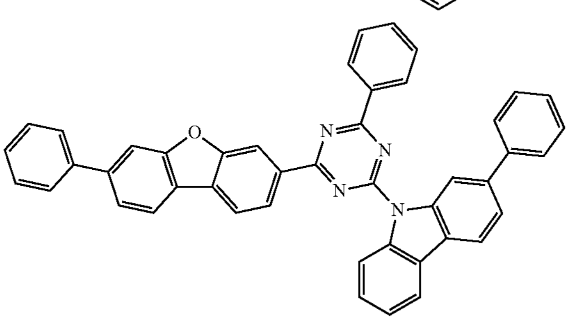
-continued
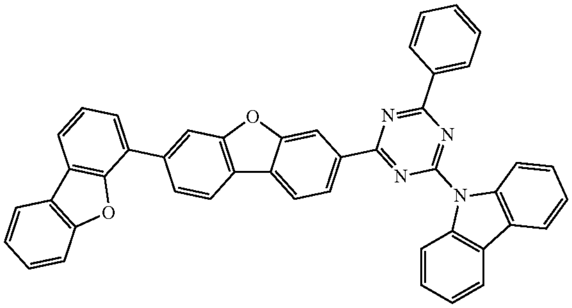
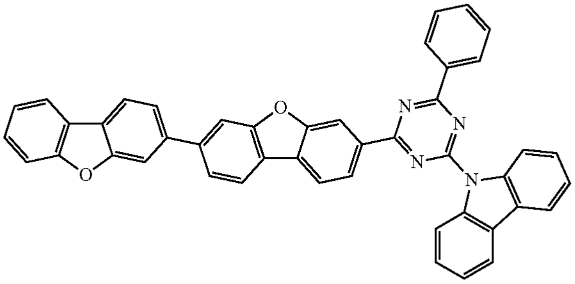
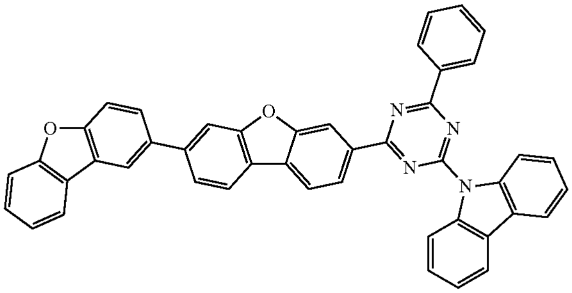
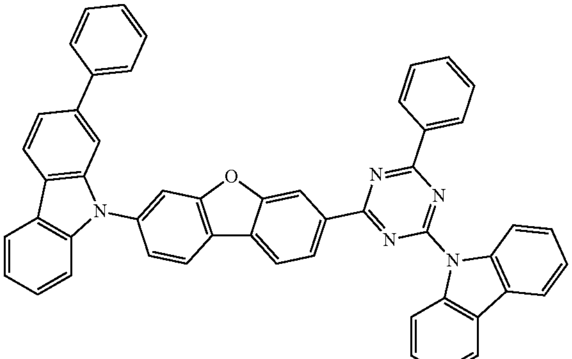
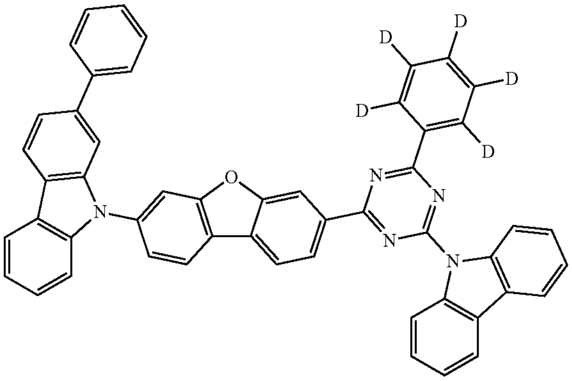

-continued
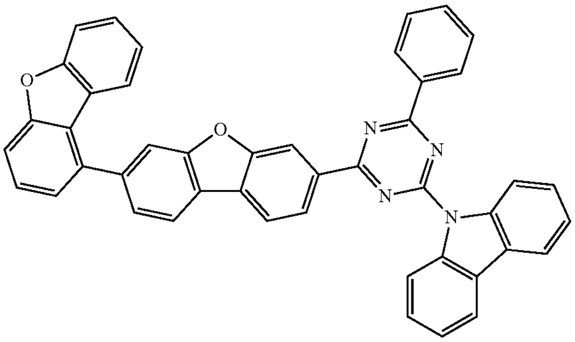
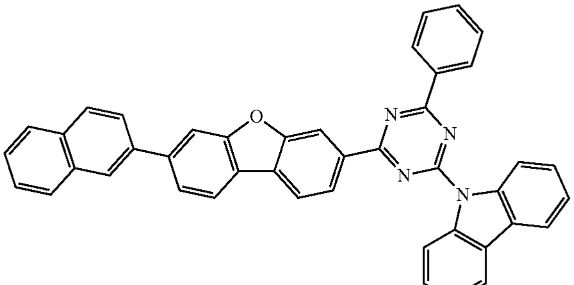
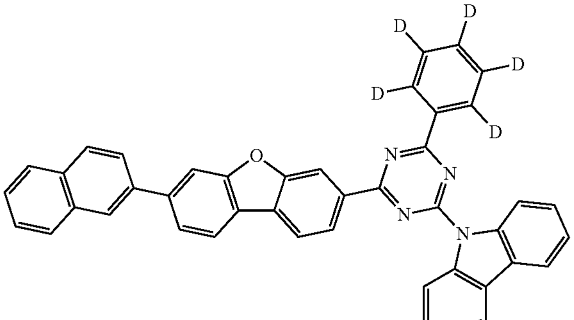
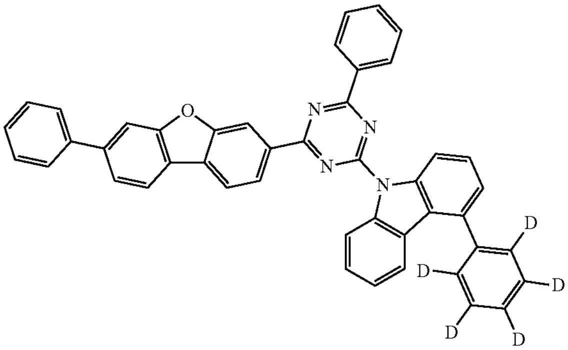
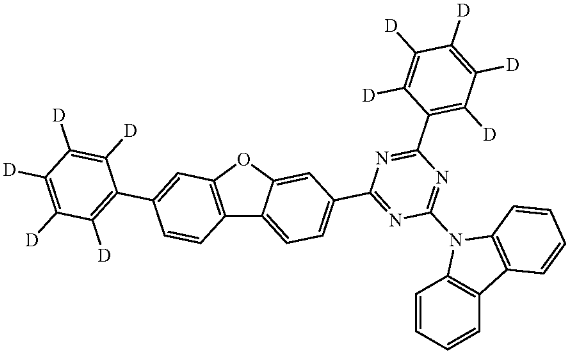
-continued
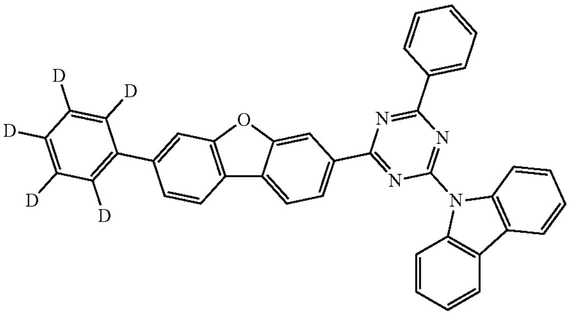
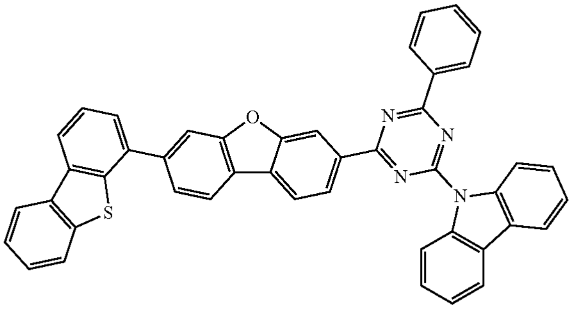
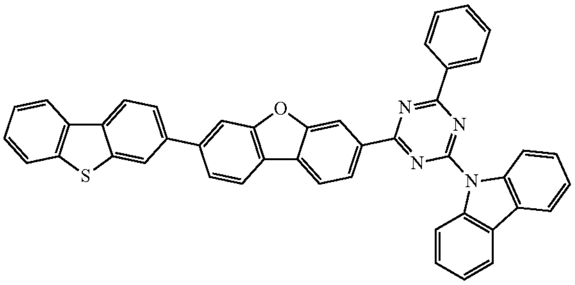
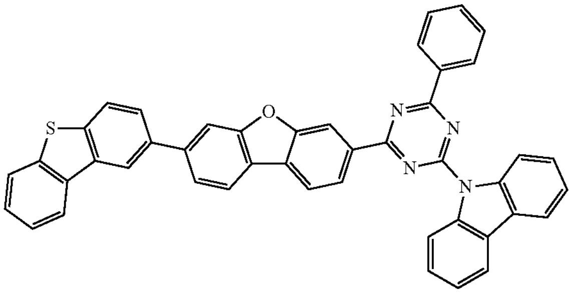
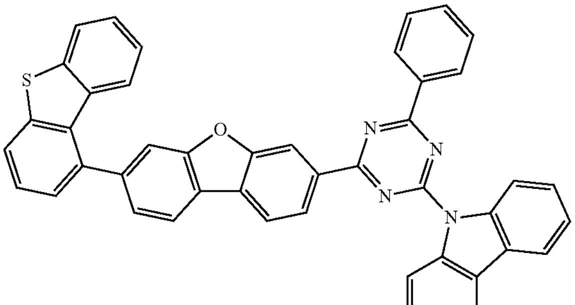

-continued
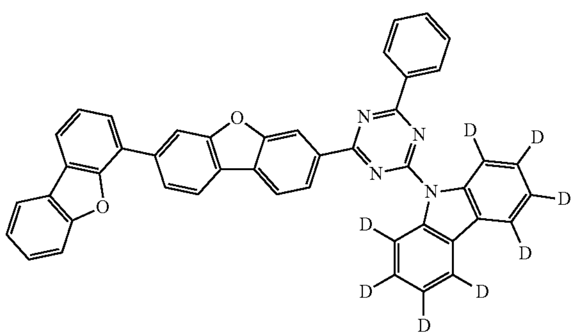
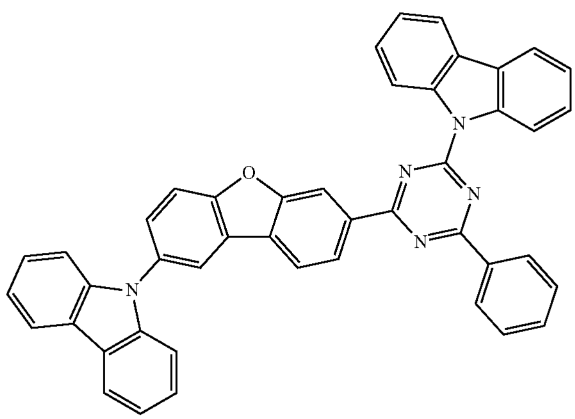
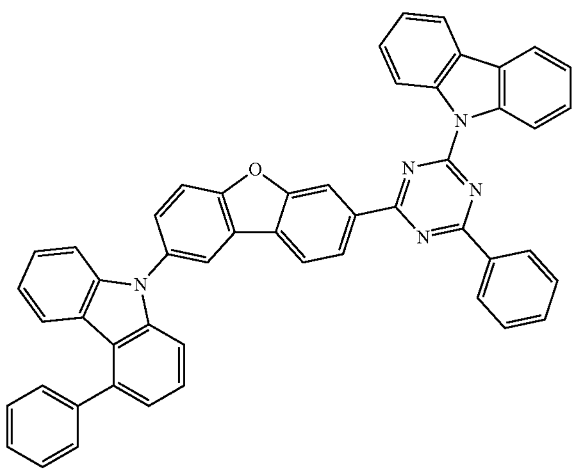
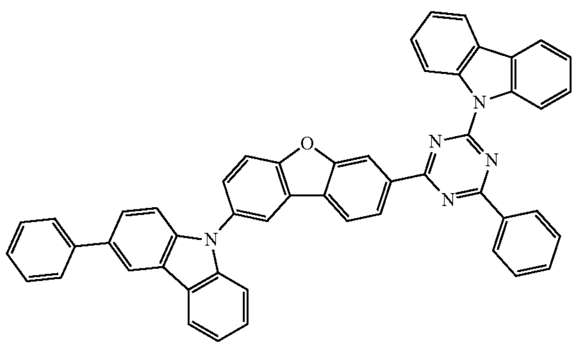
-continued
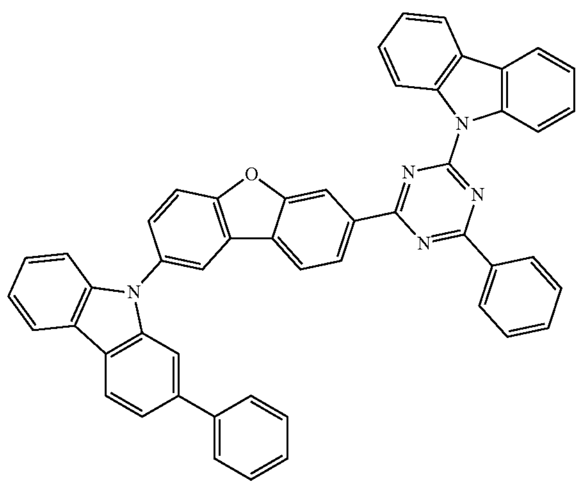
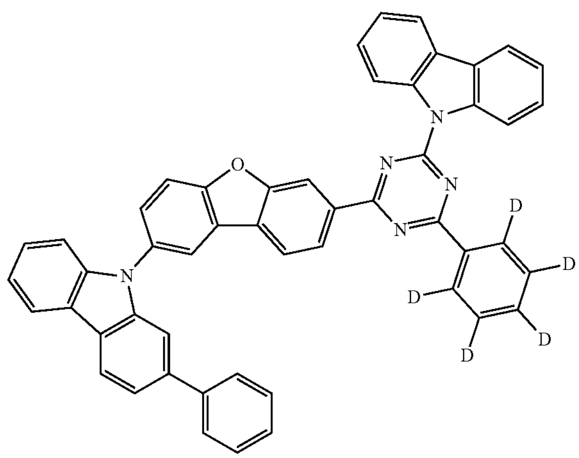
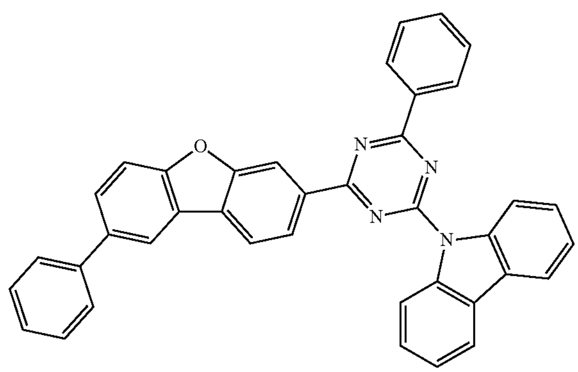
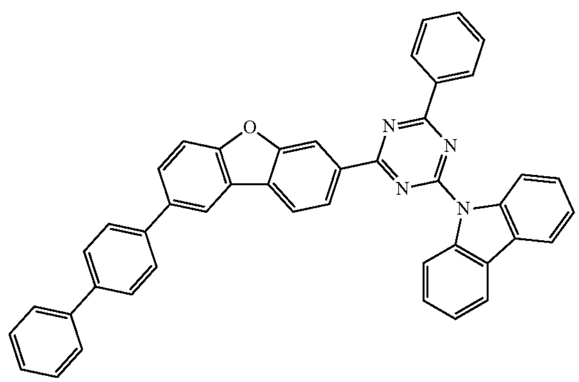

-continued
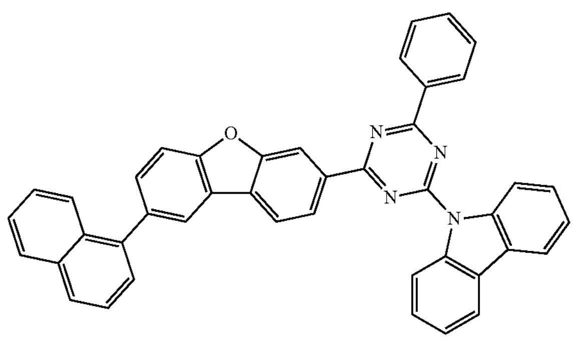
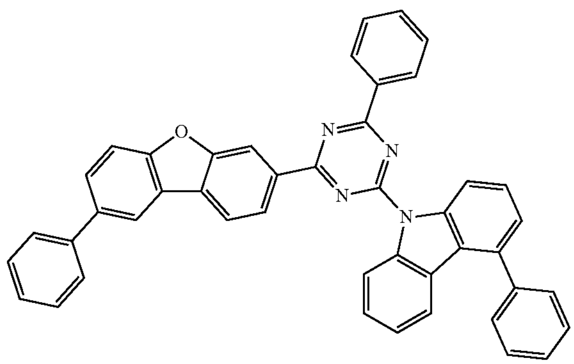
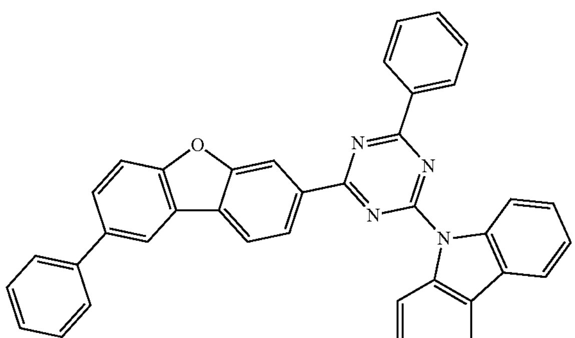
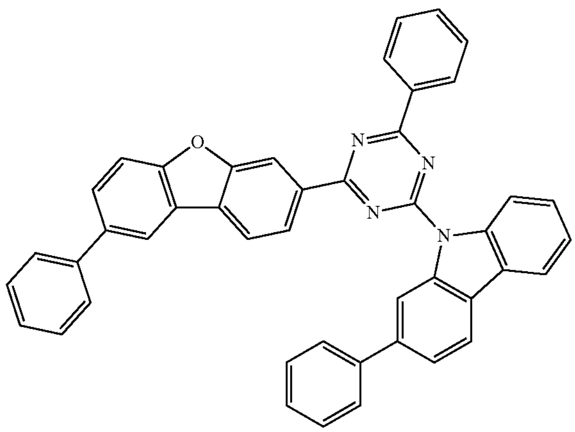
-continued
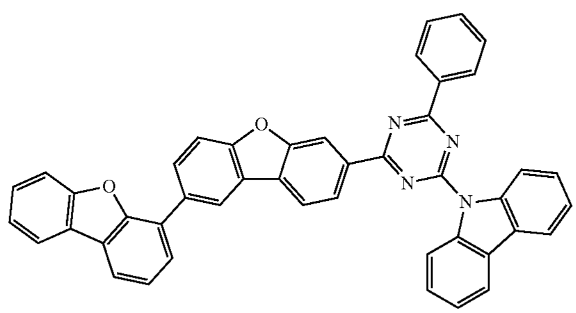
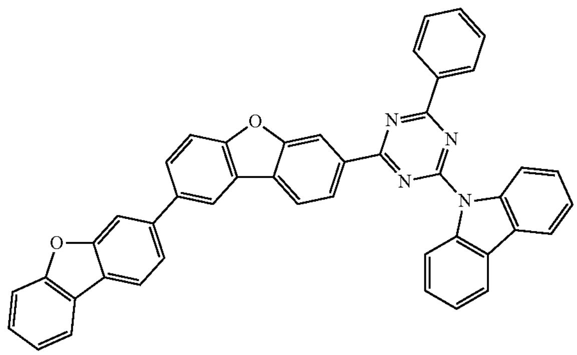
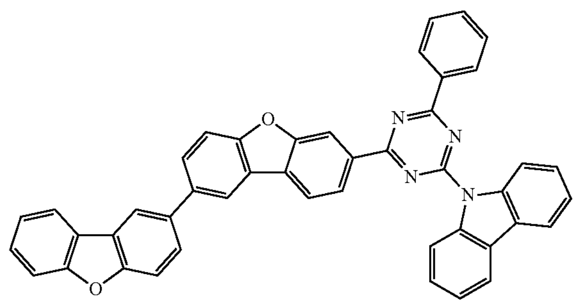
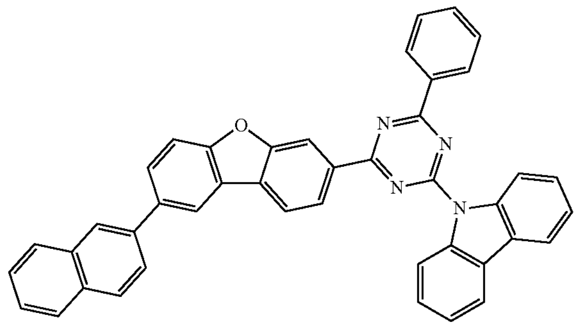
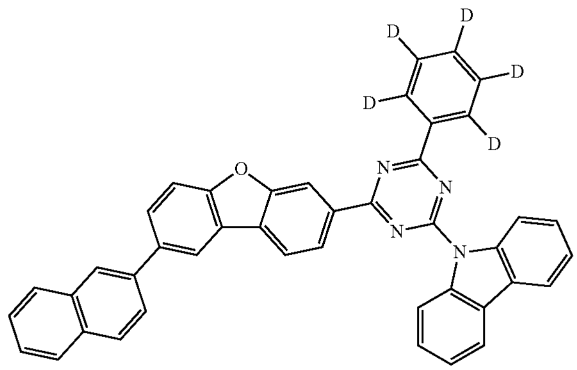

-continued
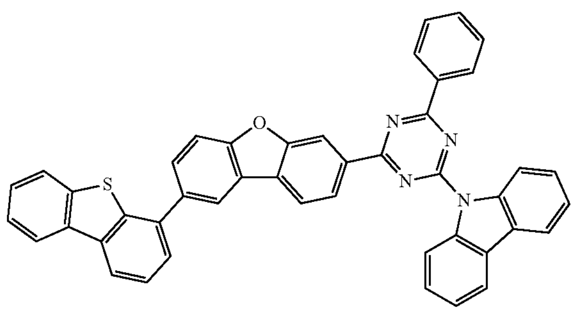
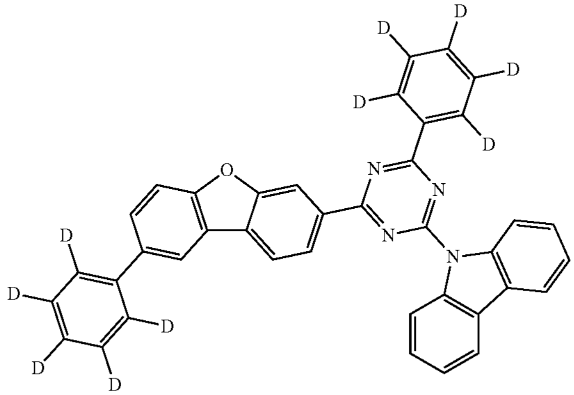
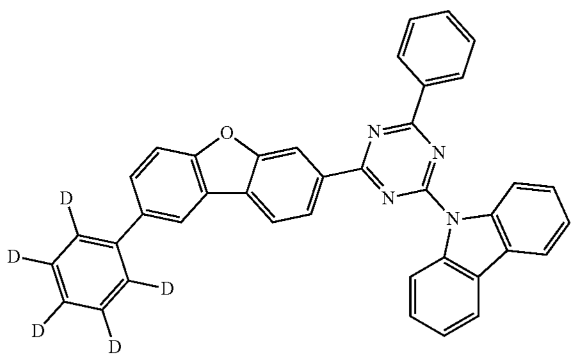
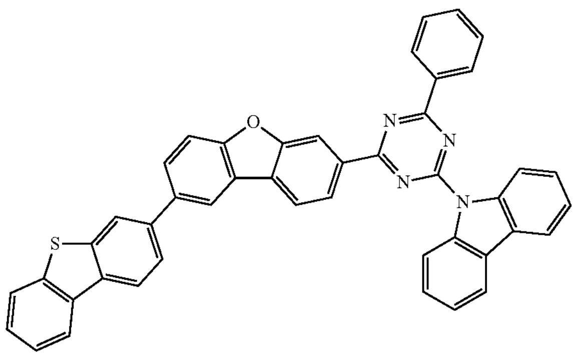
-continued
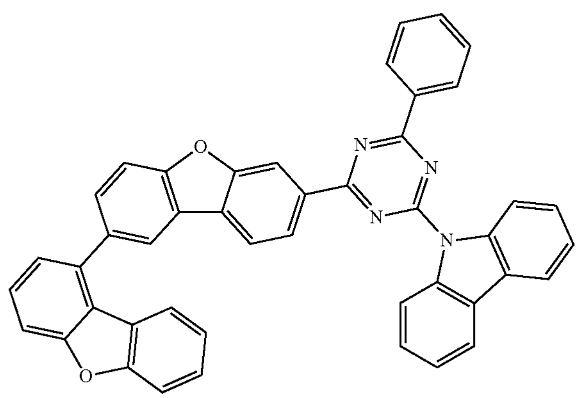
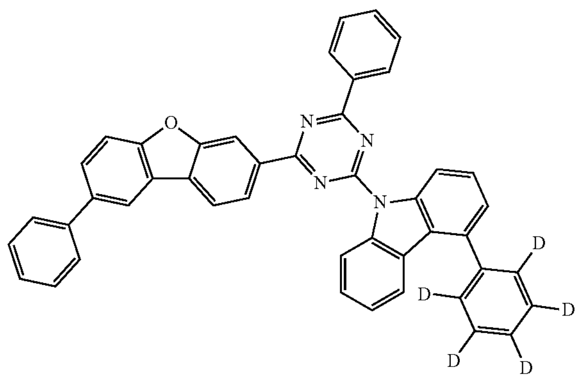
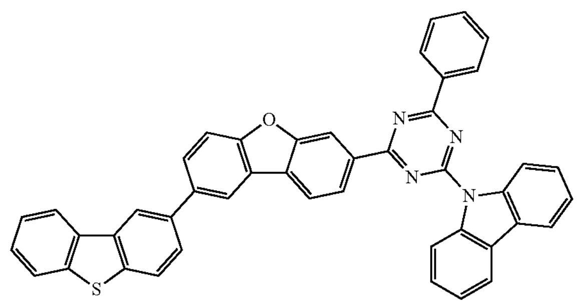
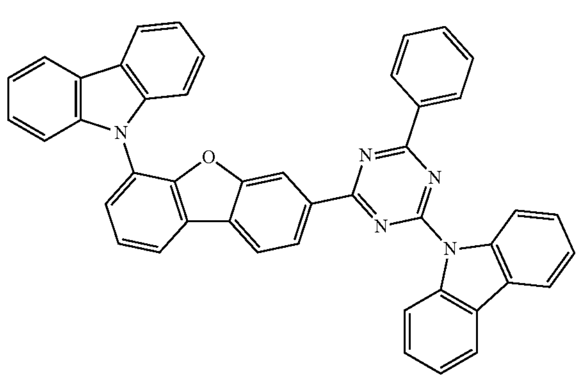

-continued
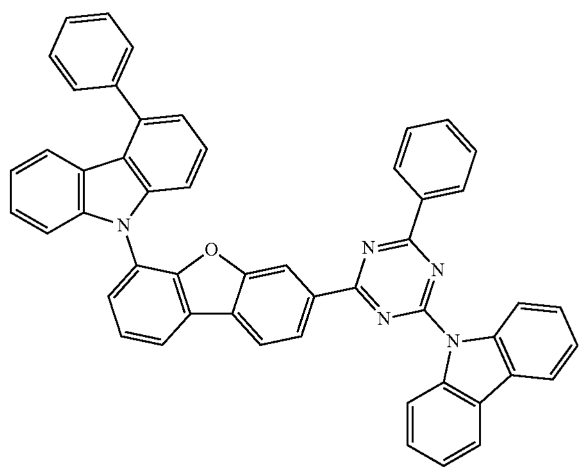
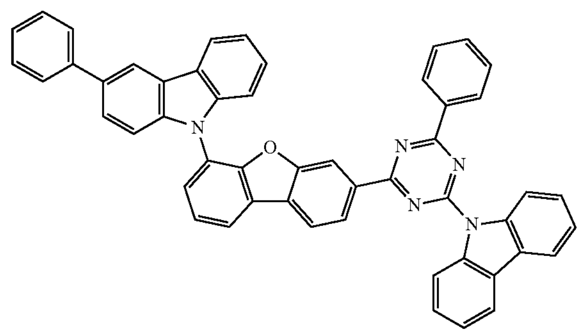
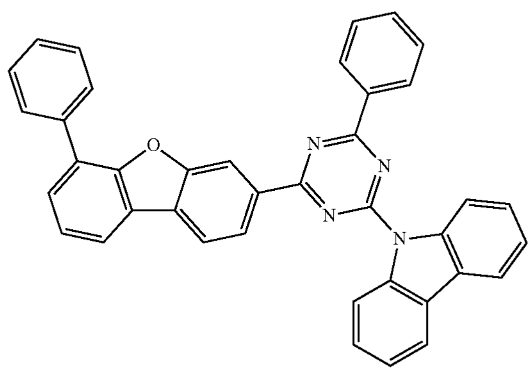
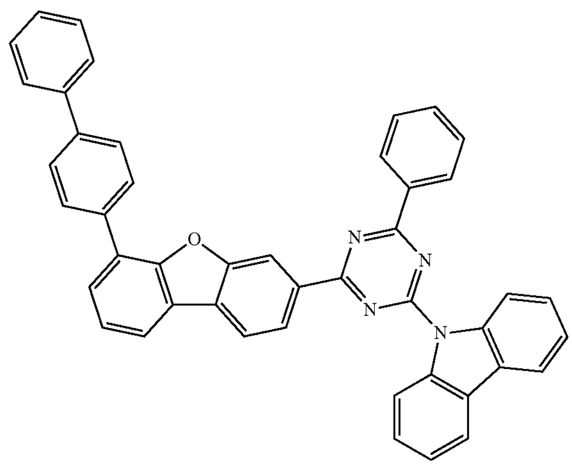
-continued
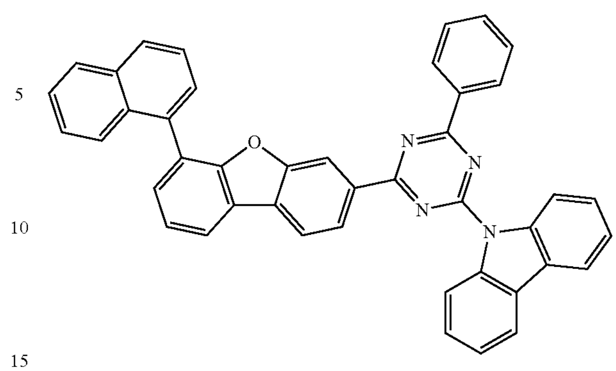
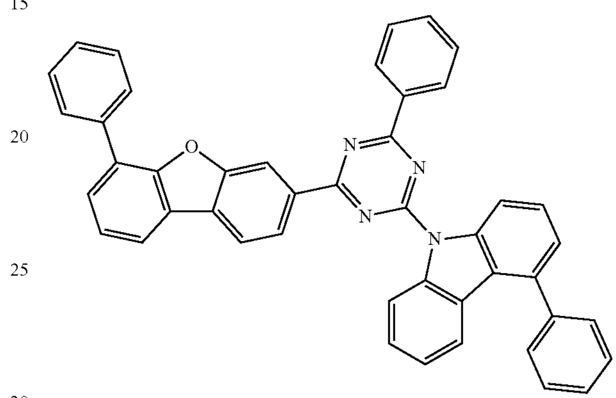
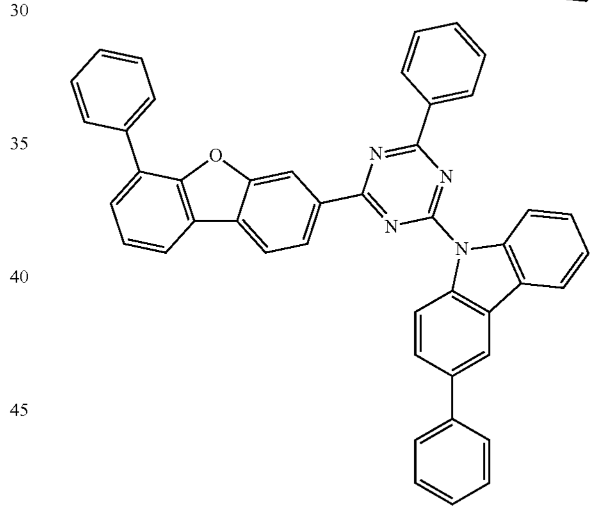
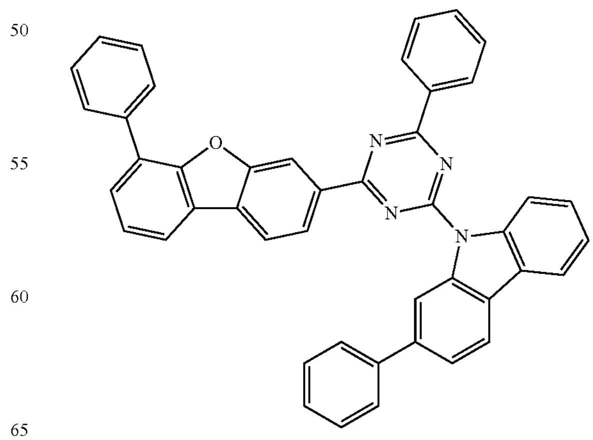

-continued
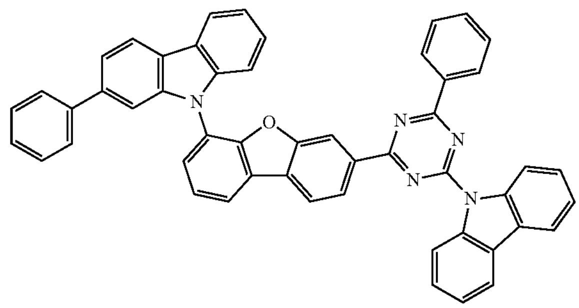
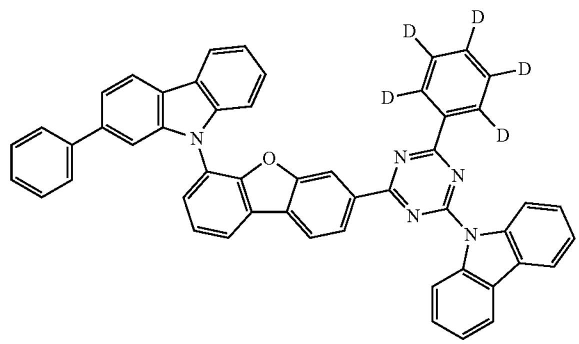
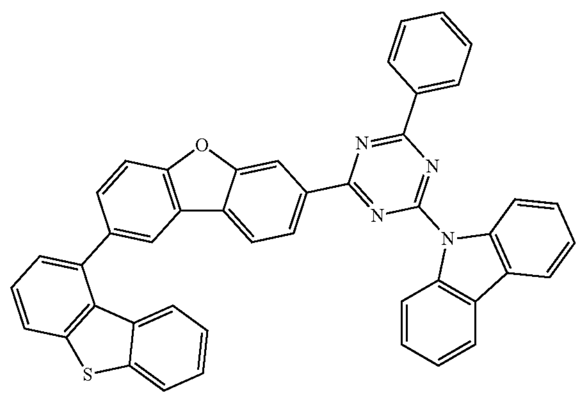
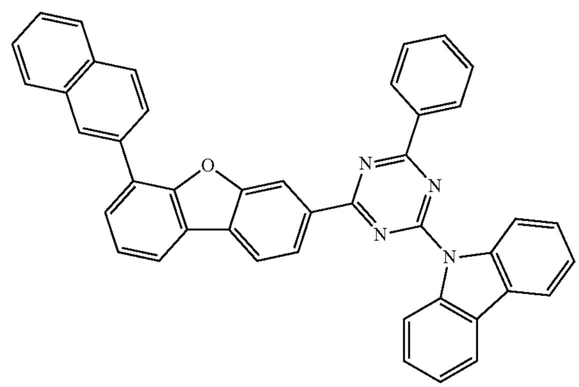
-continued
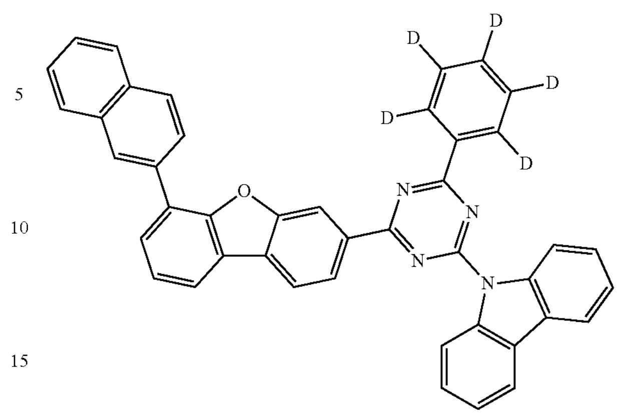
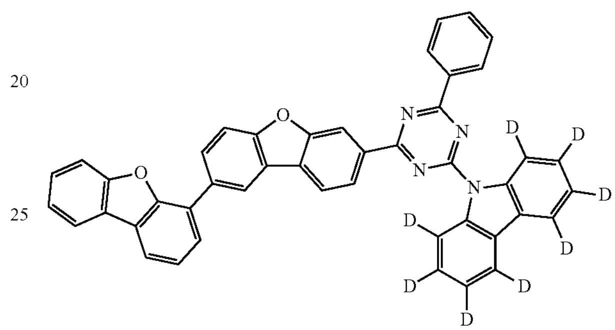
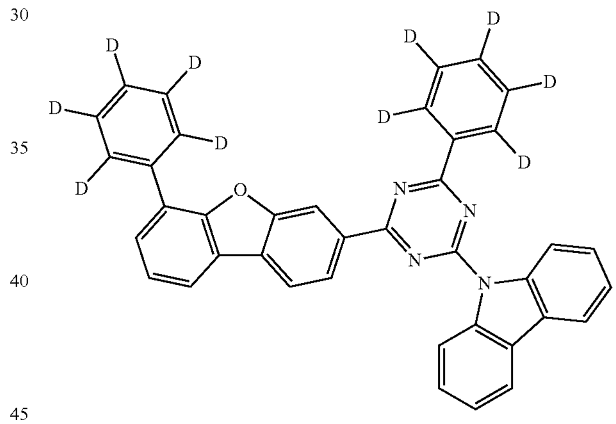
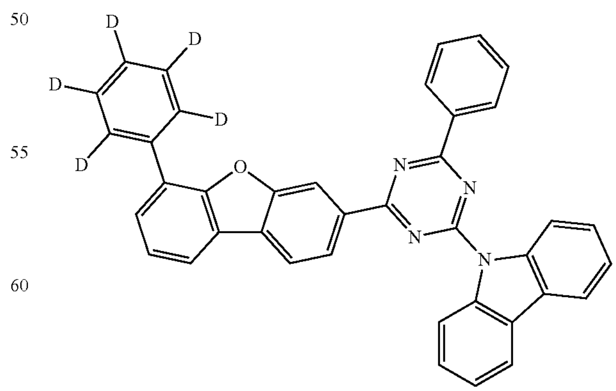

-continued
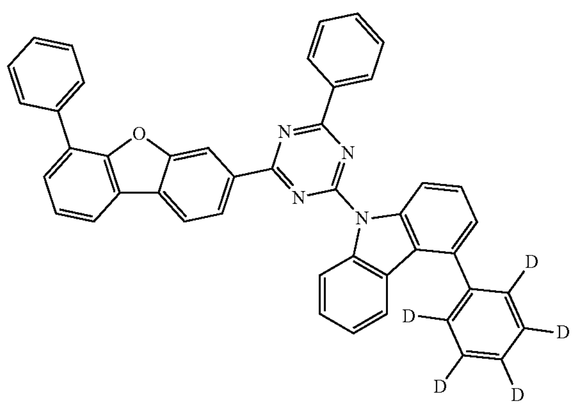
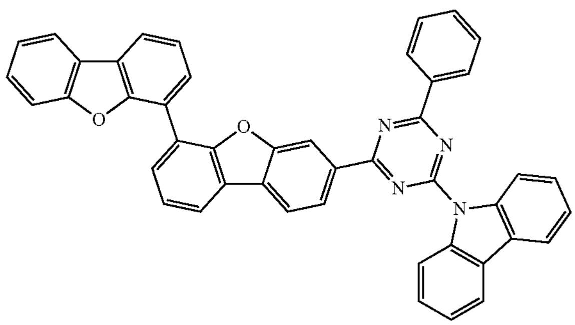
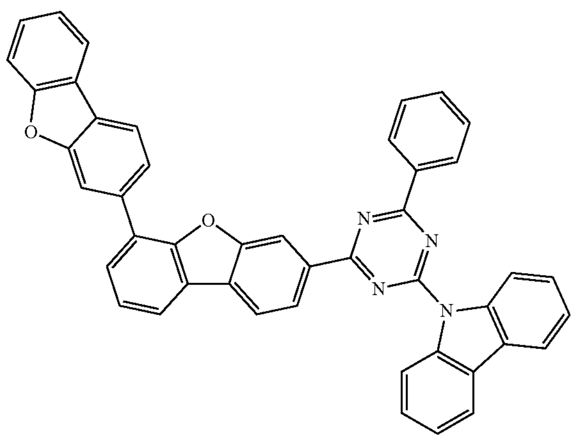
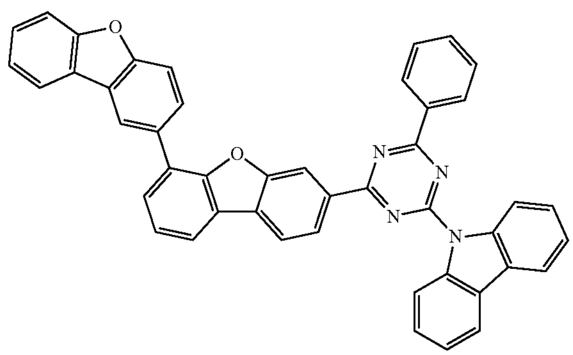
-continued
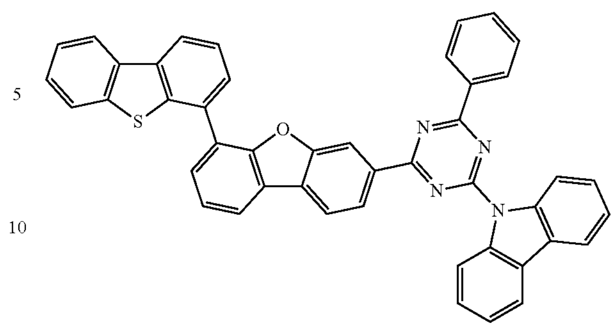
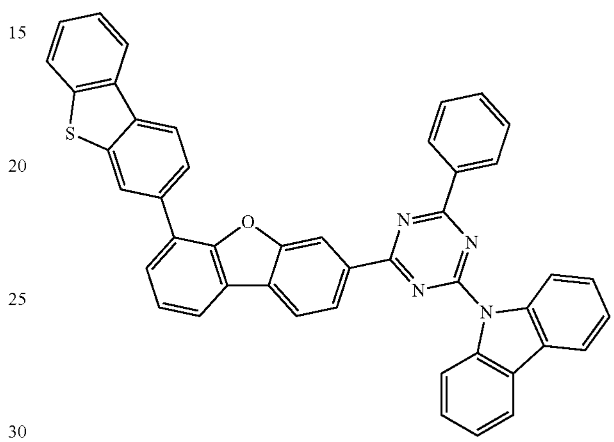
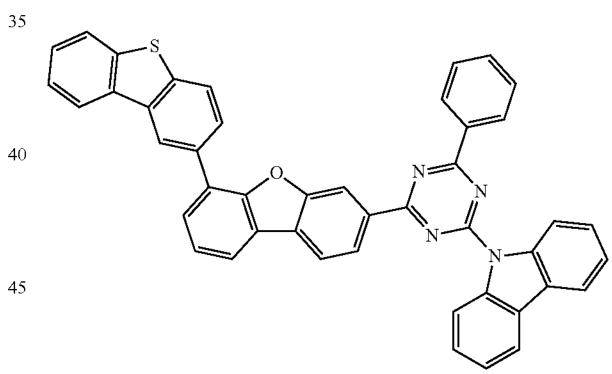
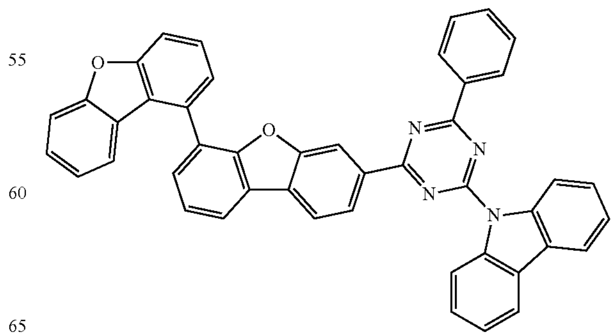

-continued
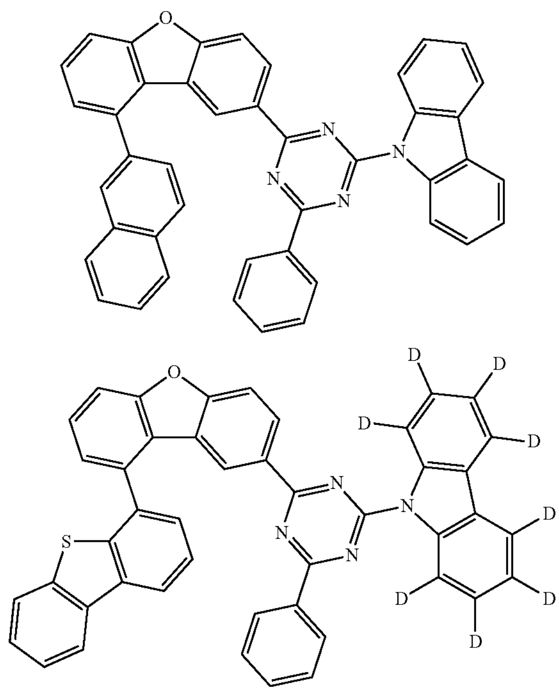
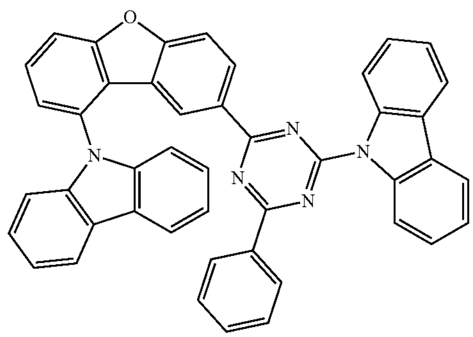
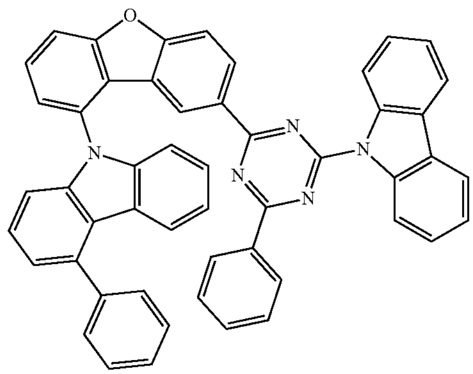
-continued
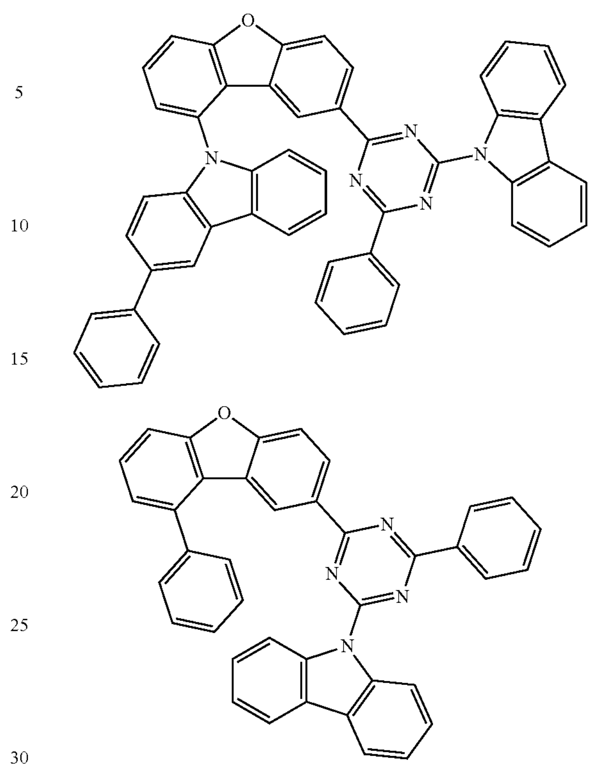
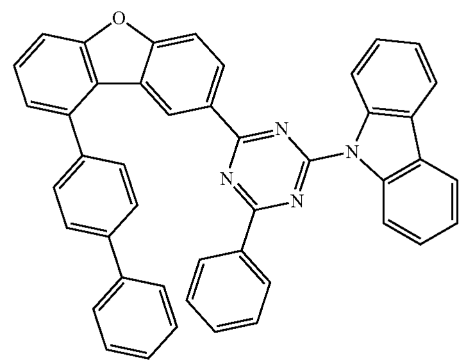
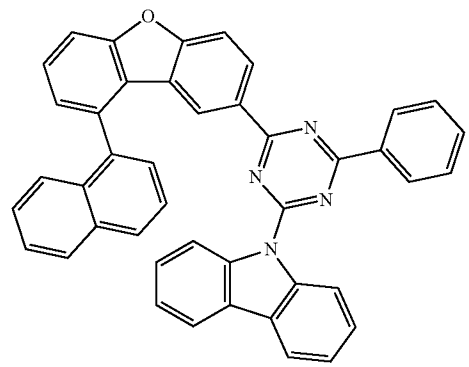

-continued
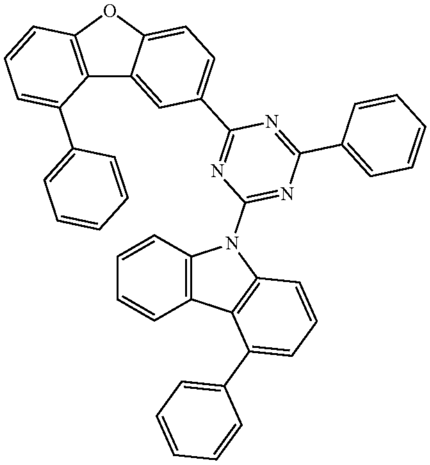
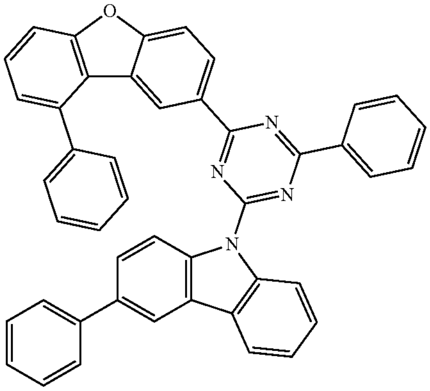
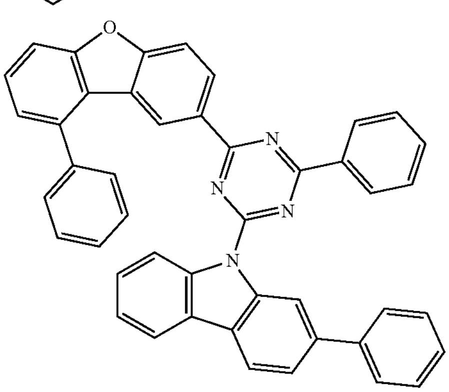
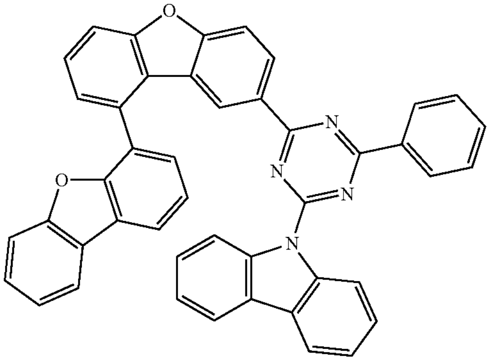
-continued
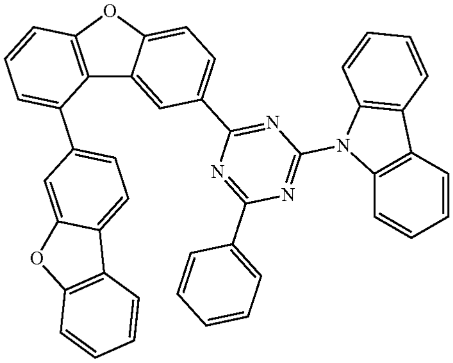
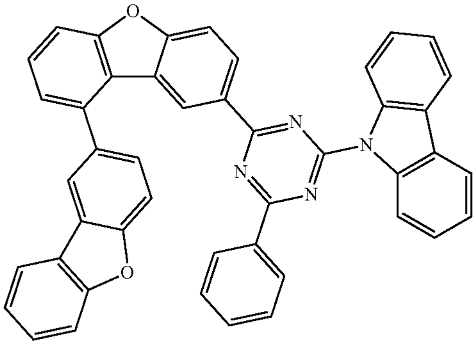
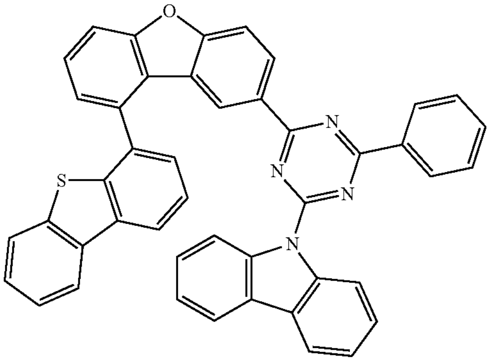
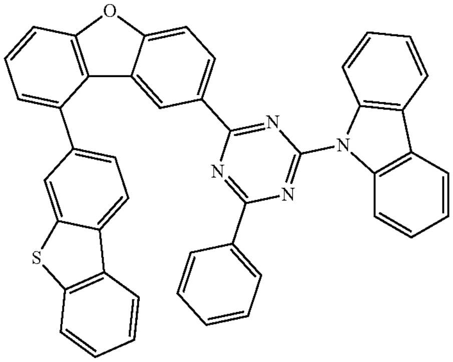

-continued
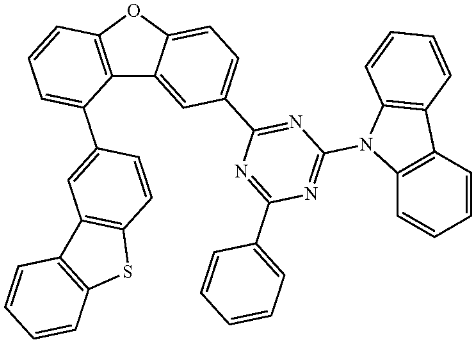
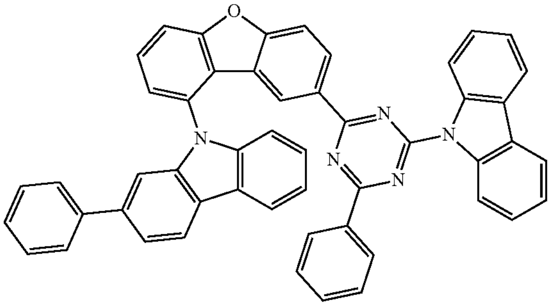
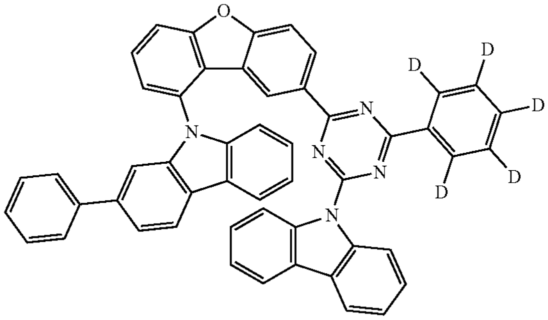
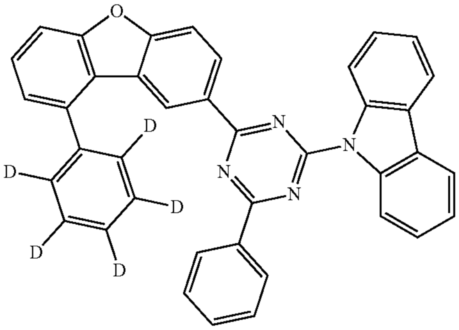
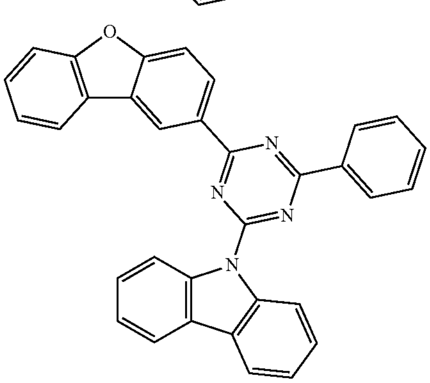
-continued
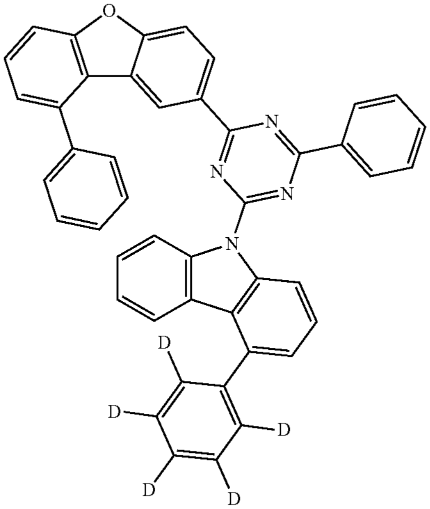
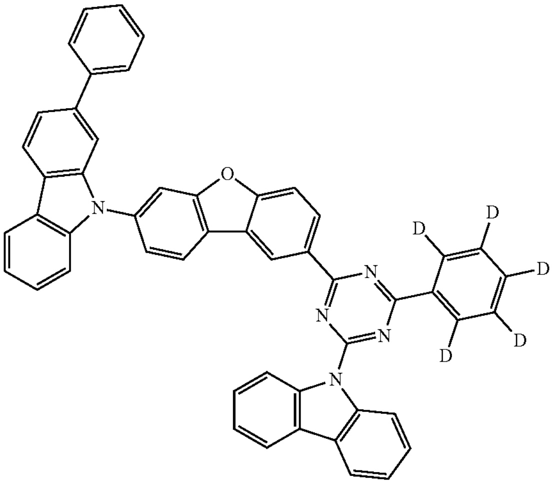
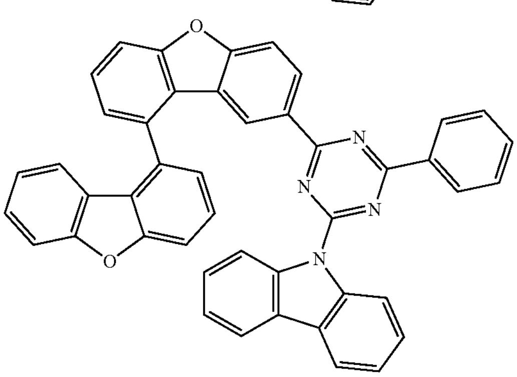
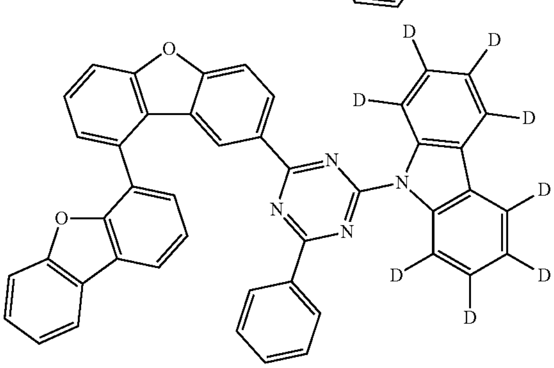

-continued
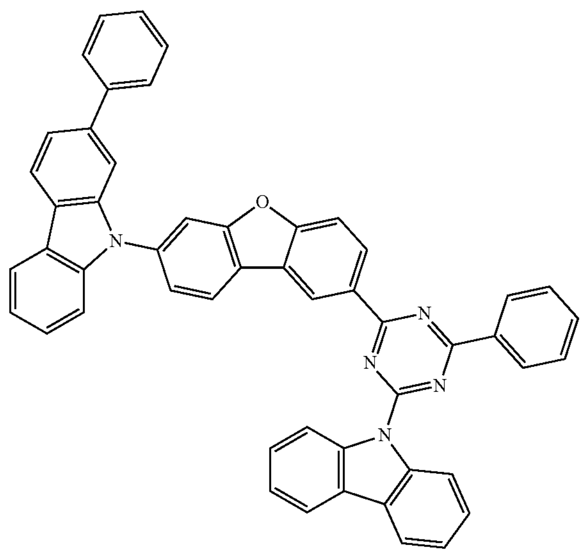
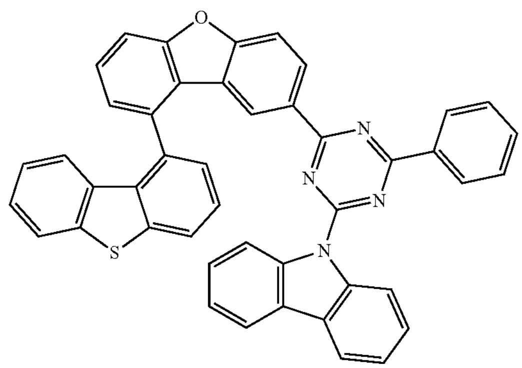
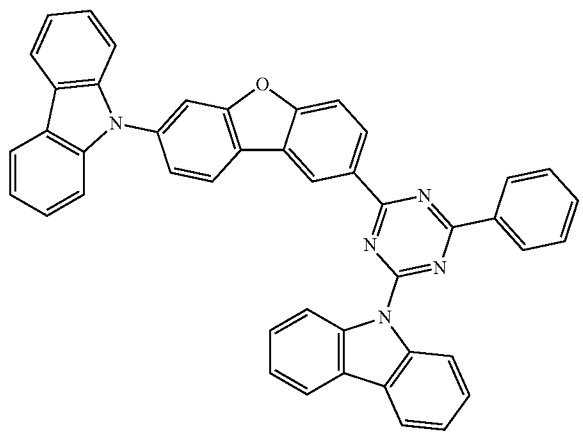
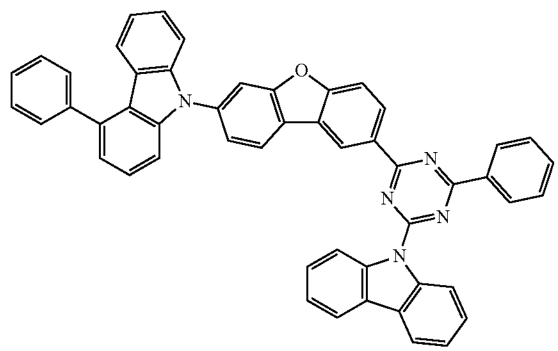
-continued
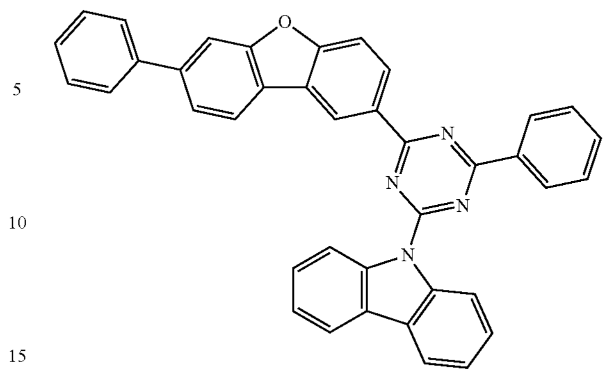
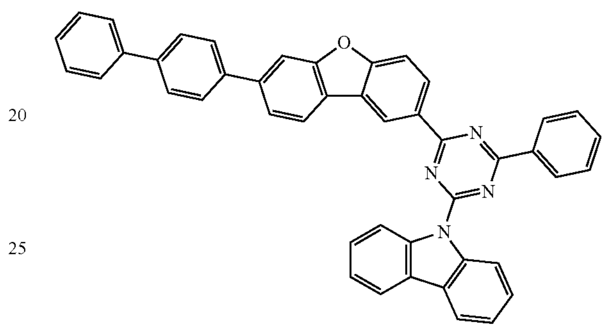
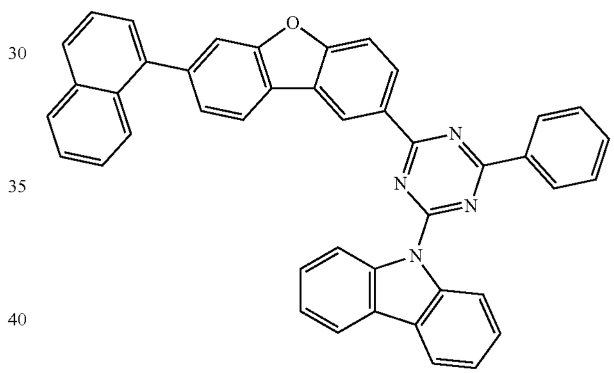
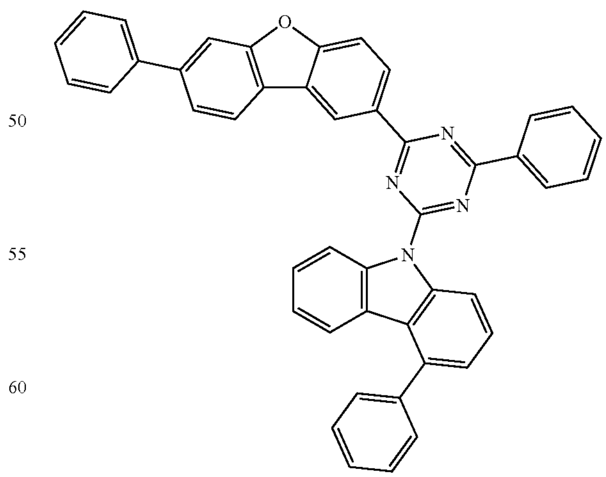

-continued
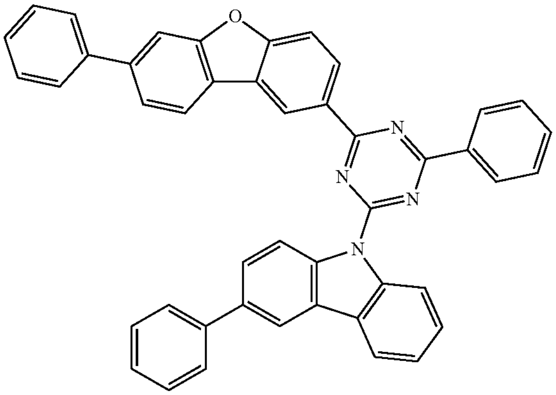
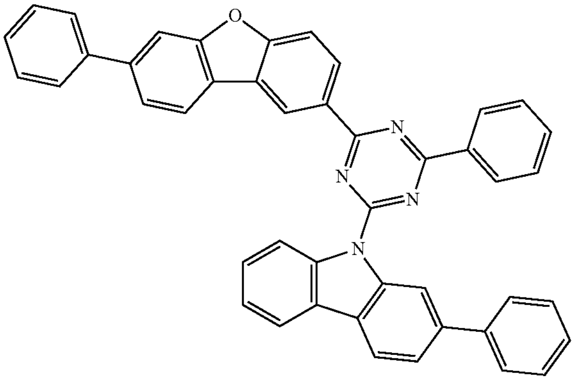
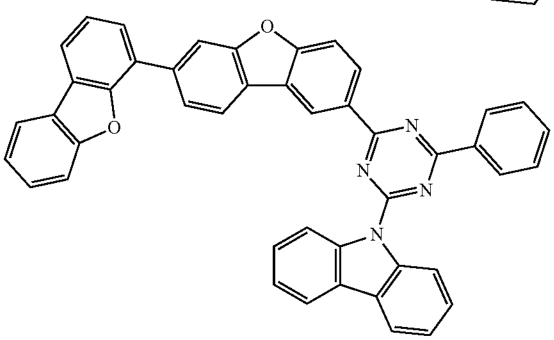
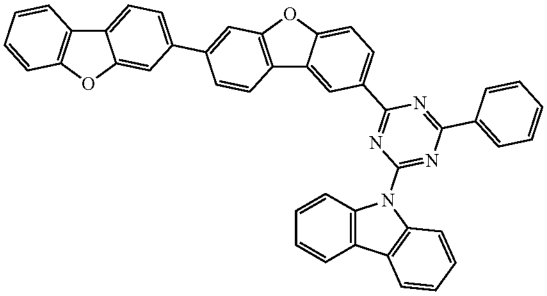
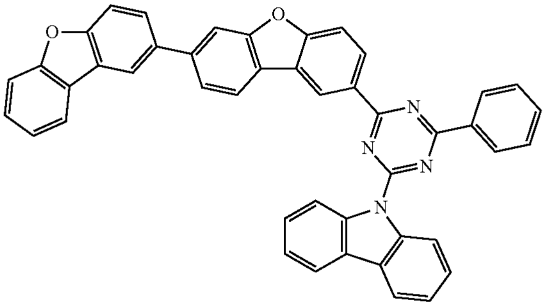
-continued
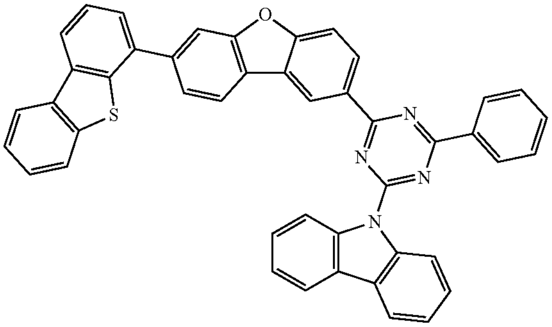
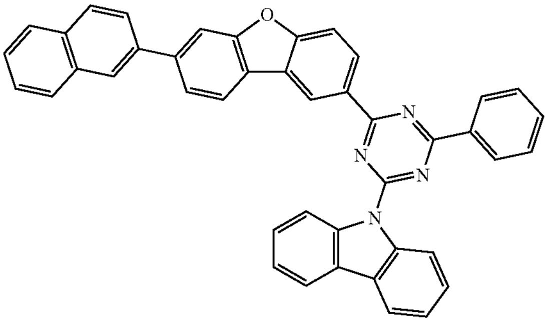
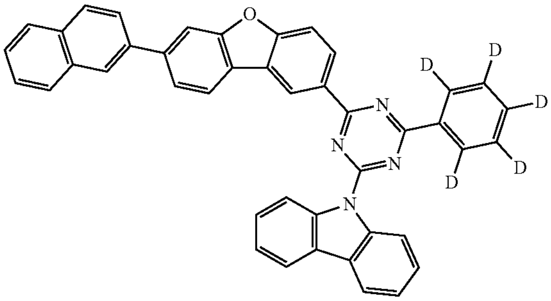
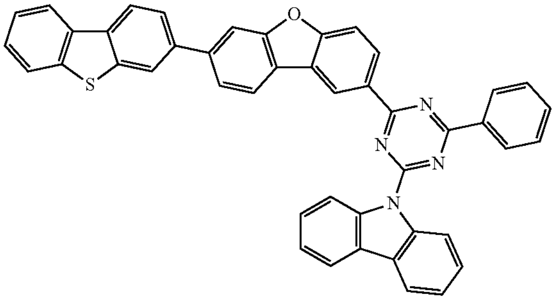
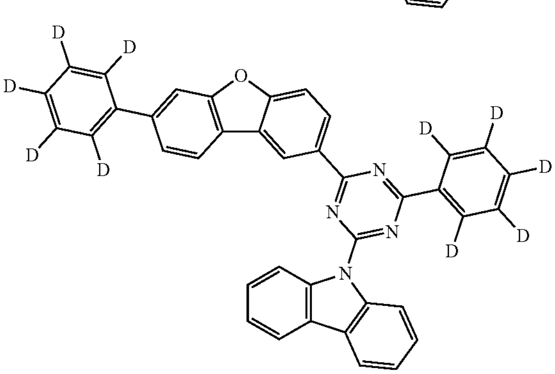

-continued
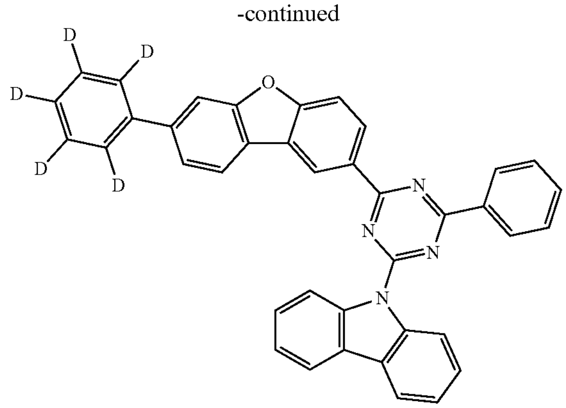
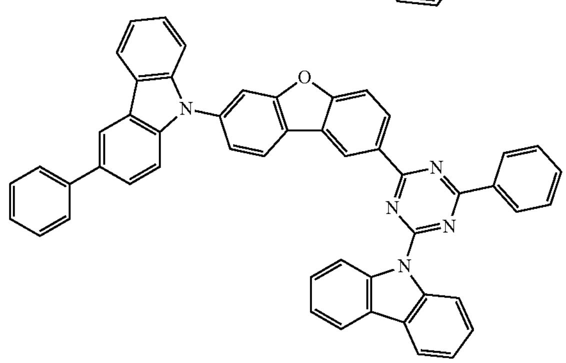
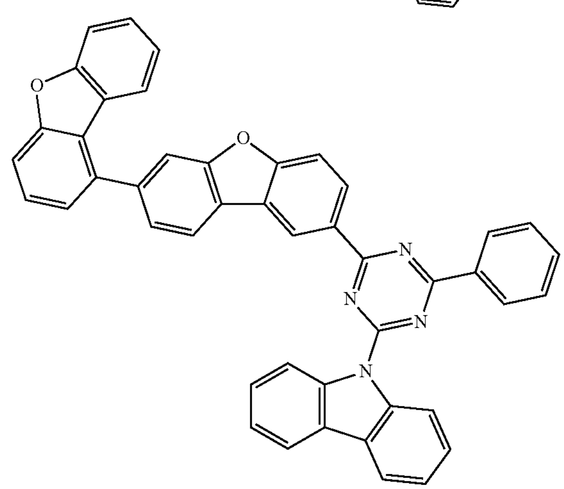
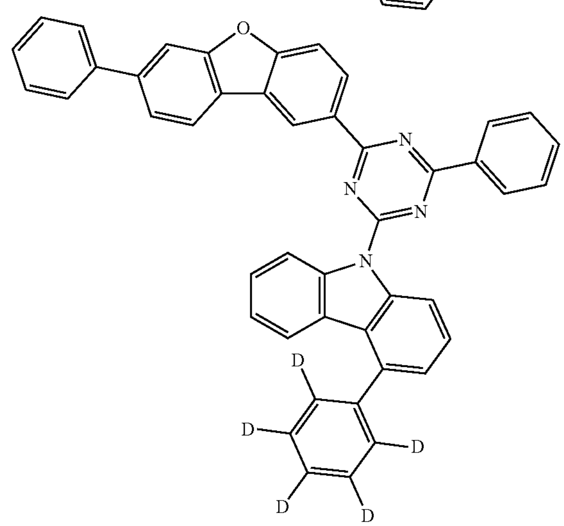
-continued
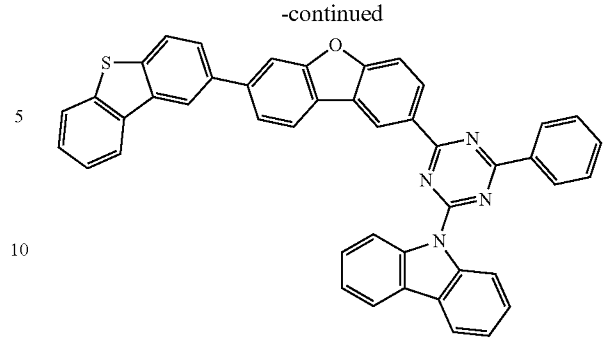
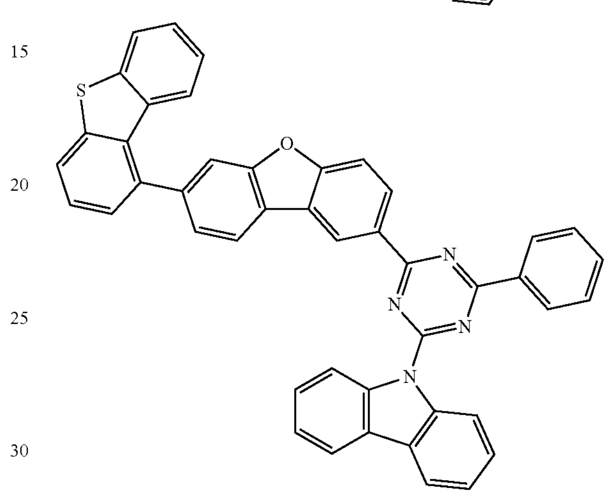
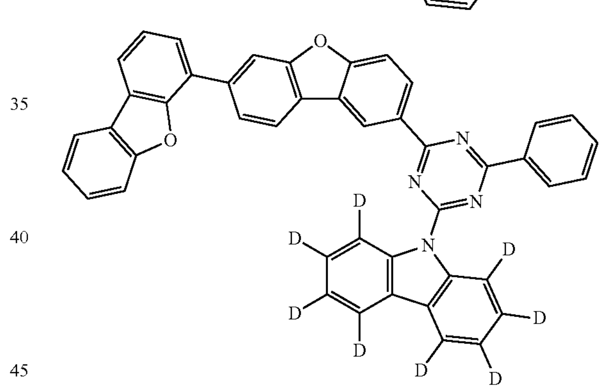
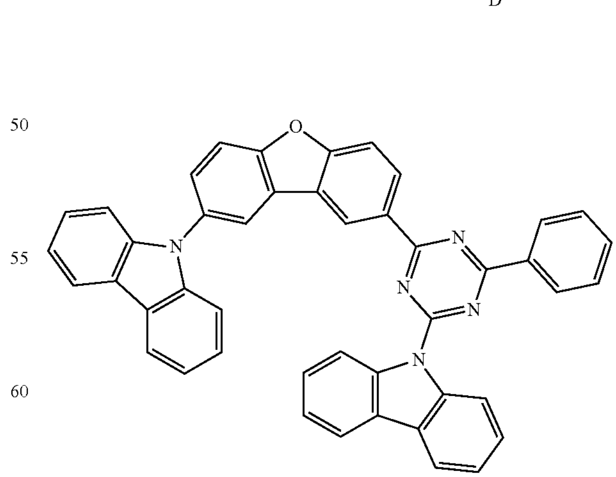
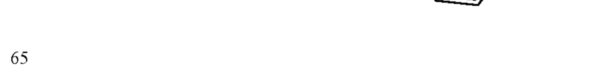

-continued
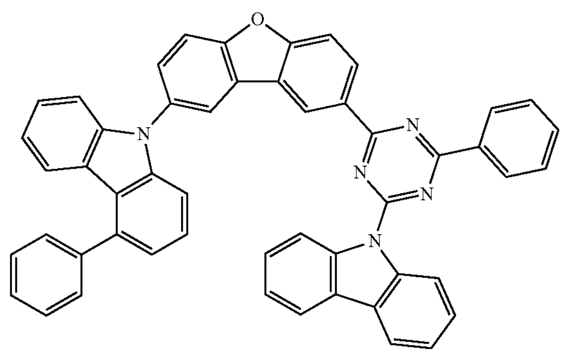
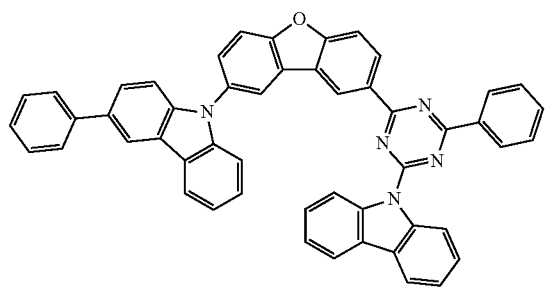
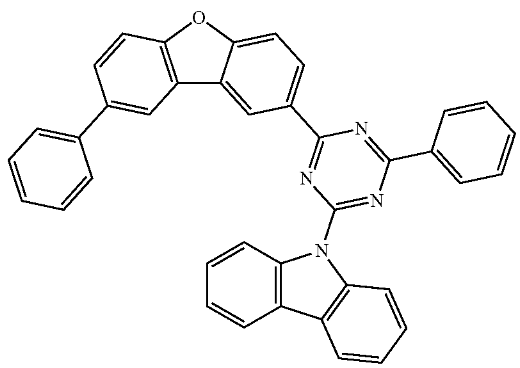
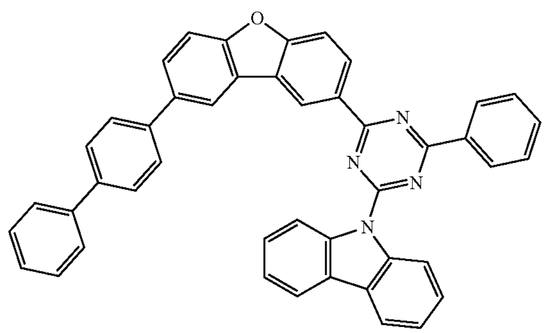
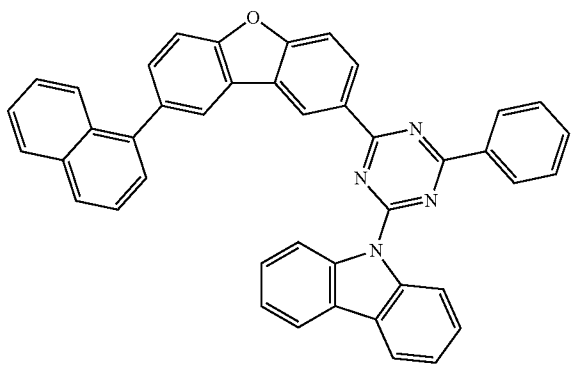
-continued
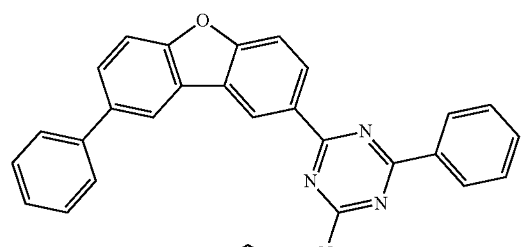
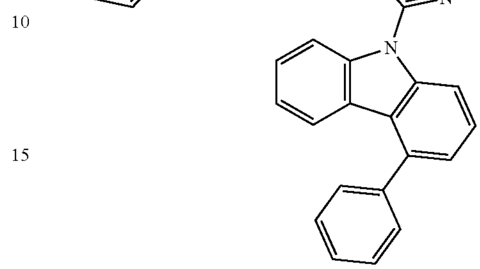
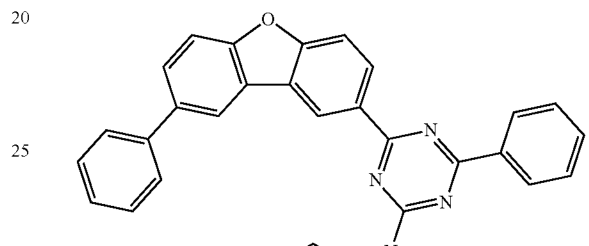
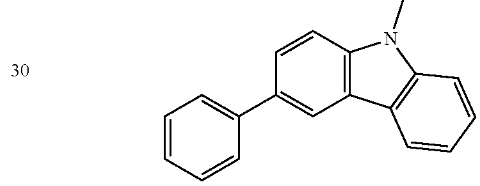
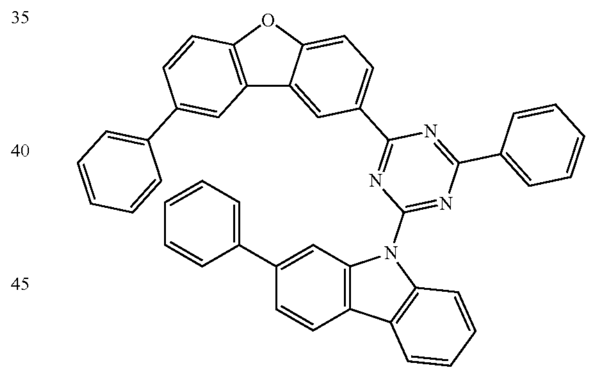
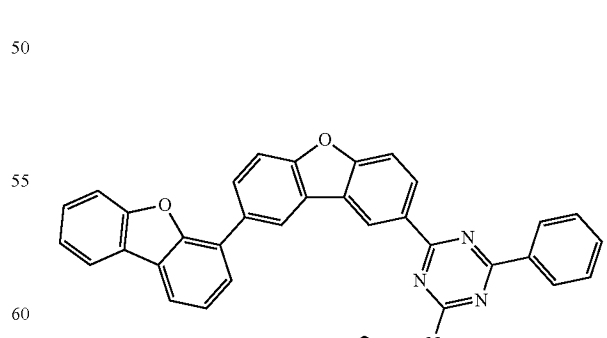
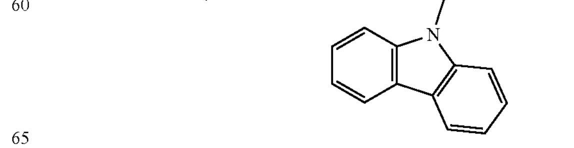

-continued
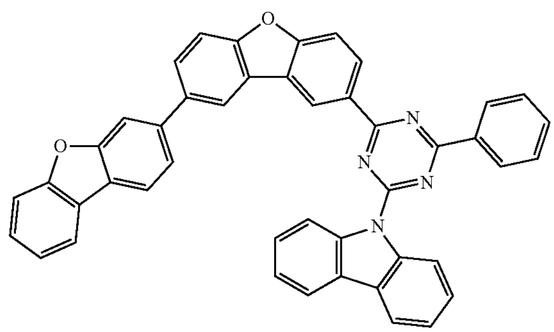
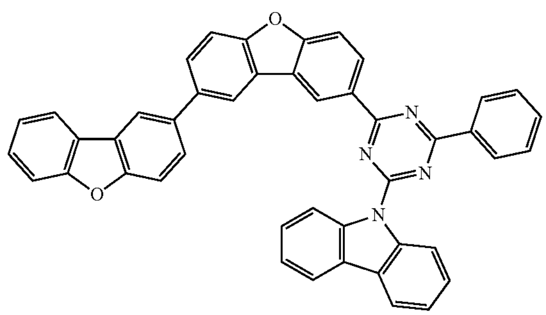
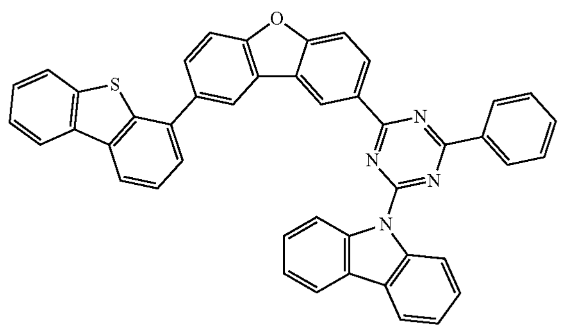
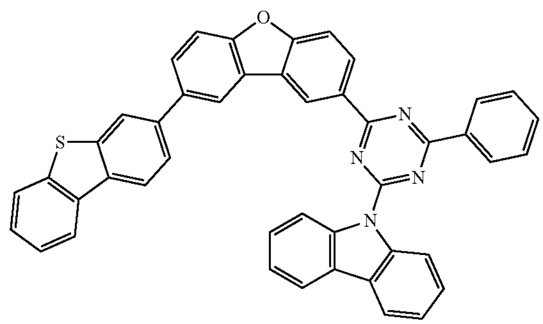
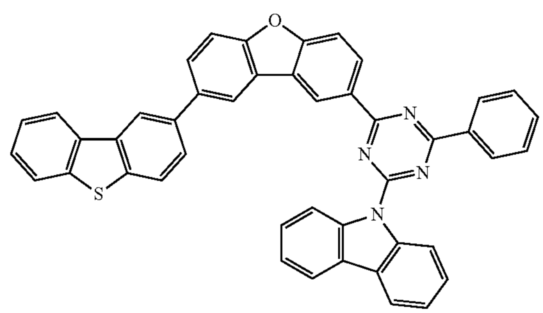
-continued
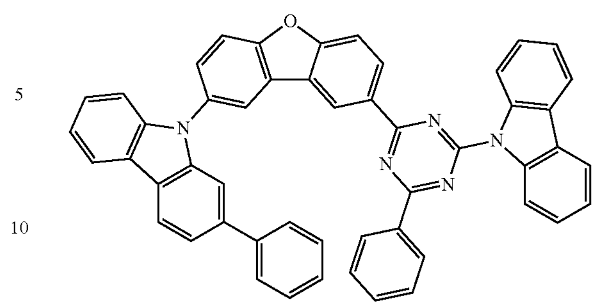
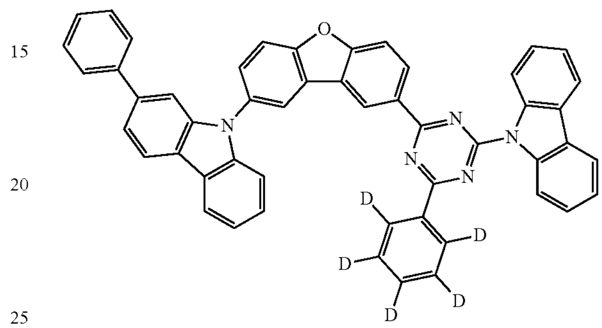
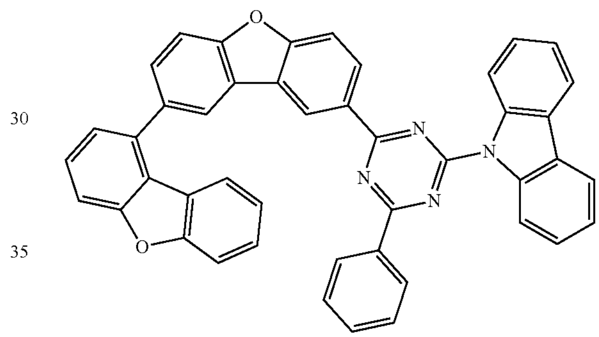
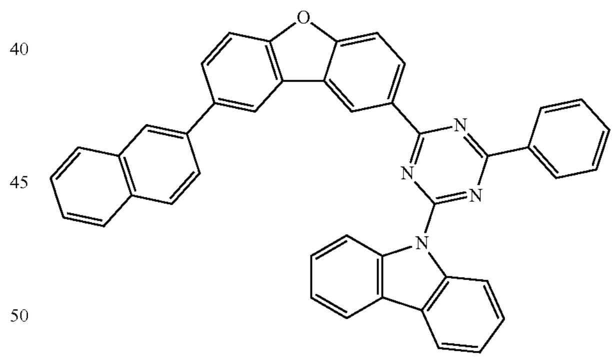
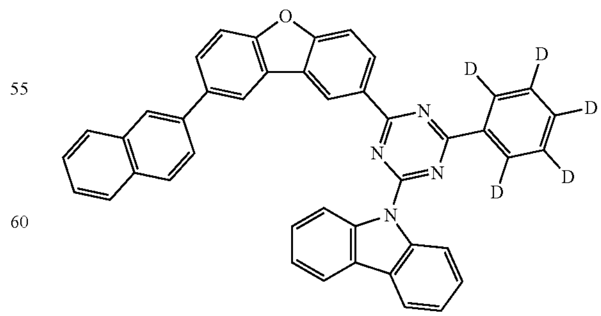

-continued
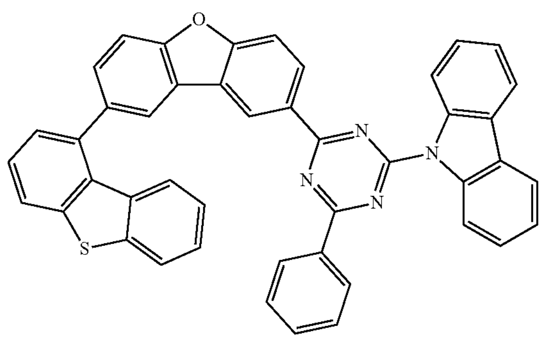
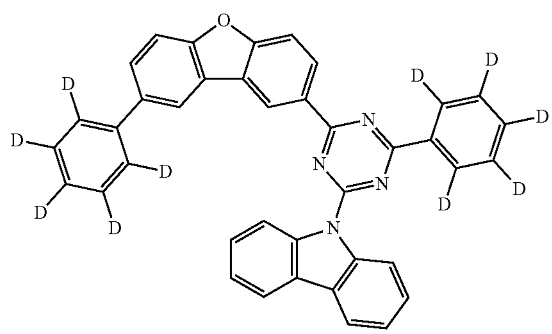
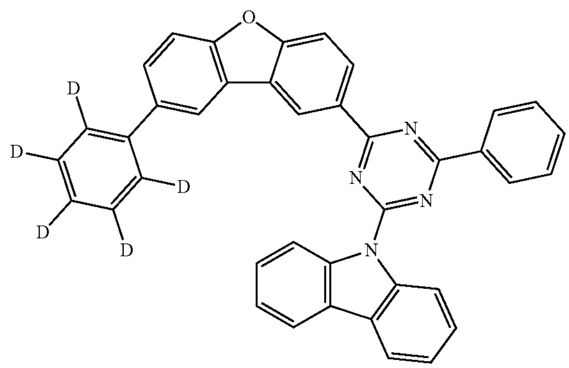
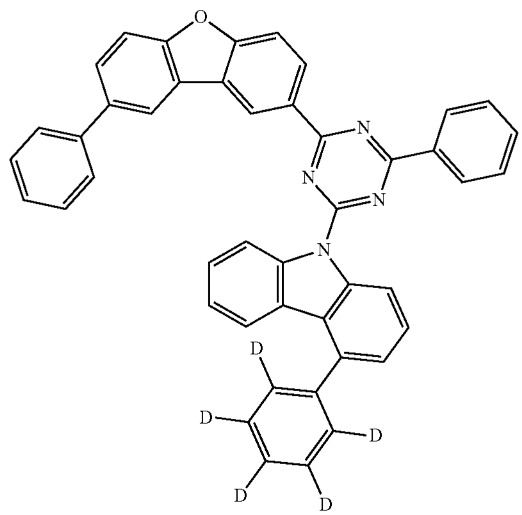
-continued
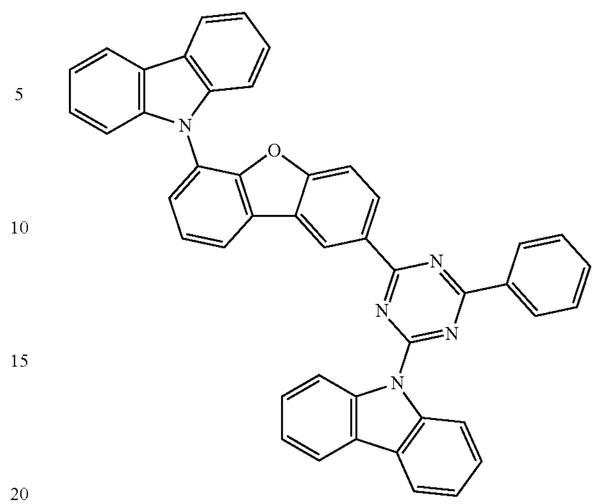
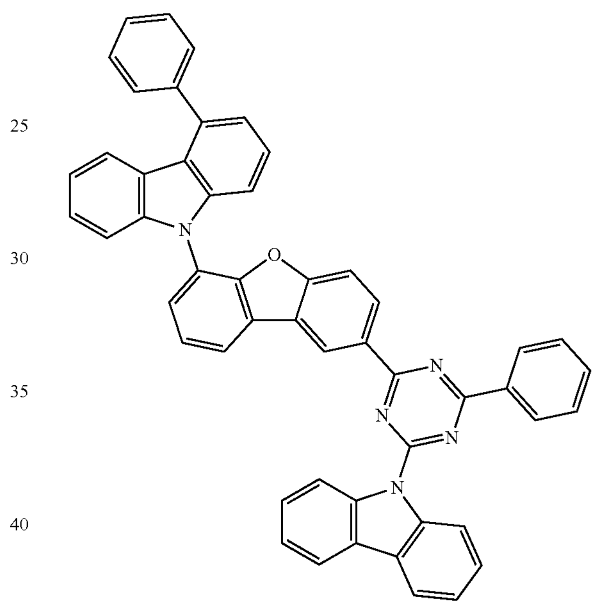
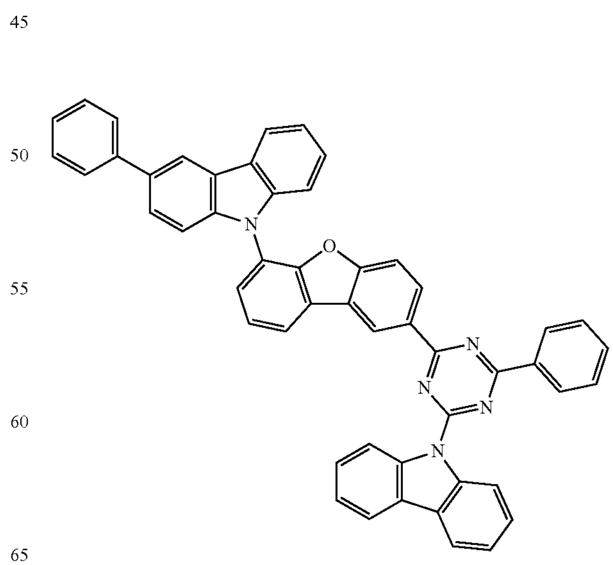

-continued
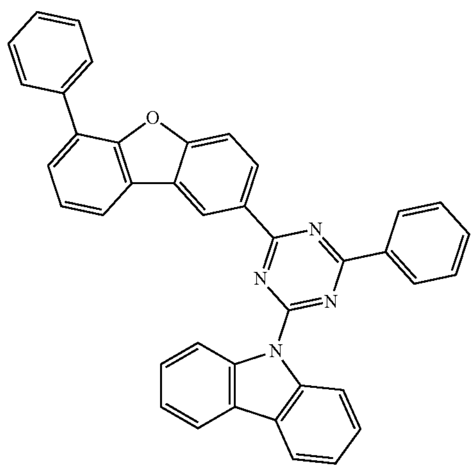
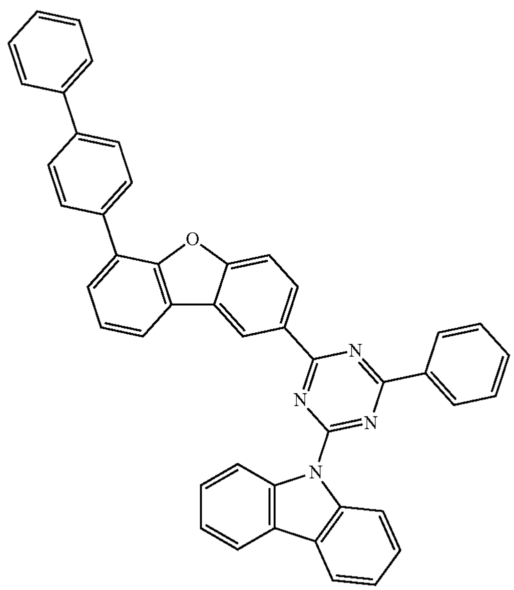
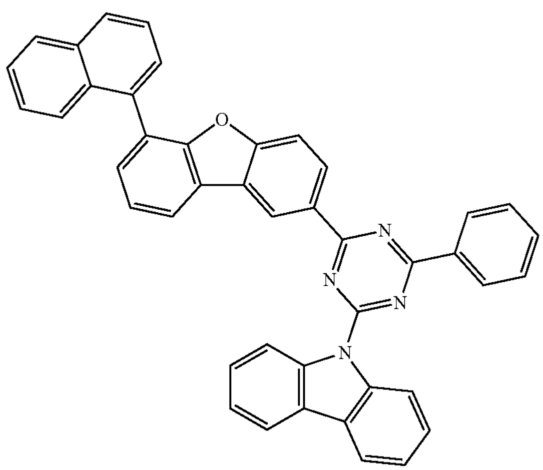
-continued
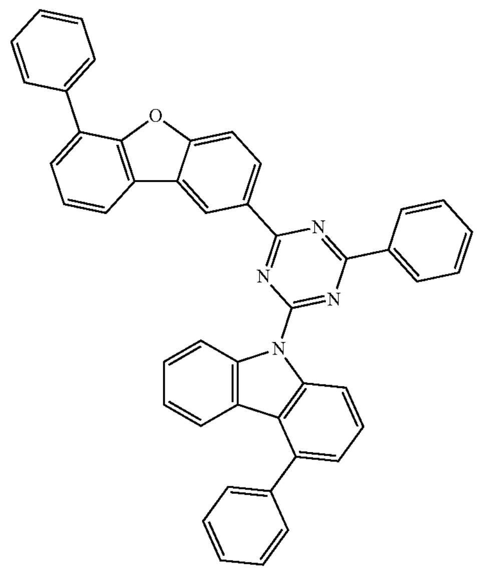
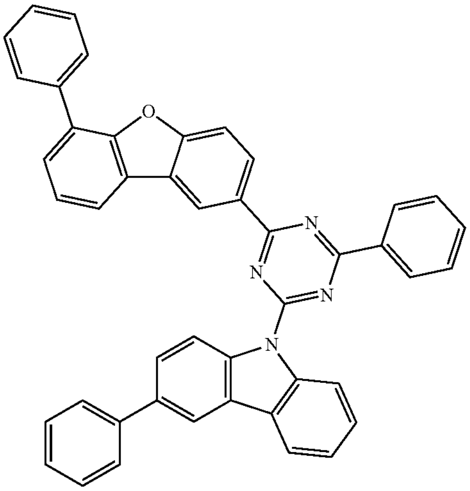
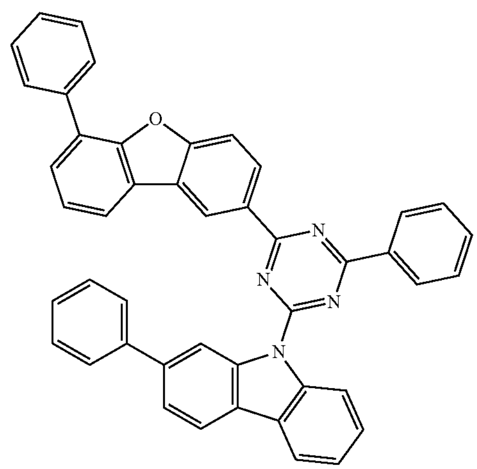

-continued
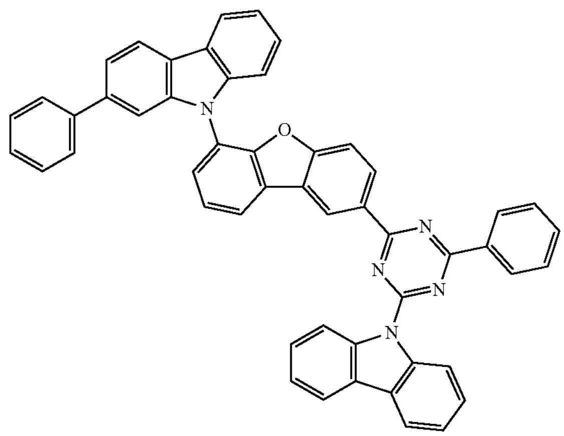
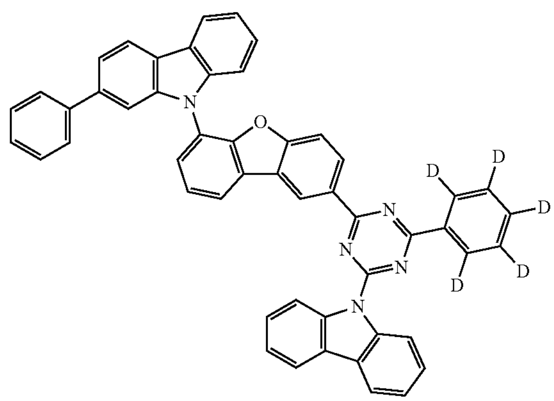
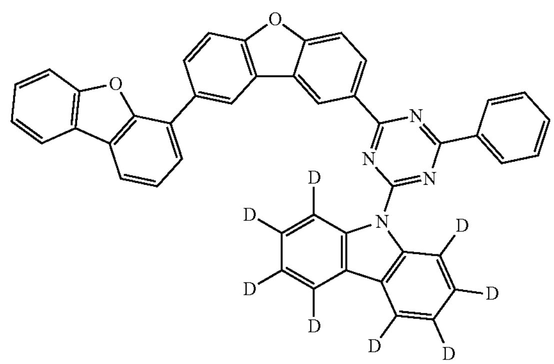
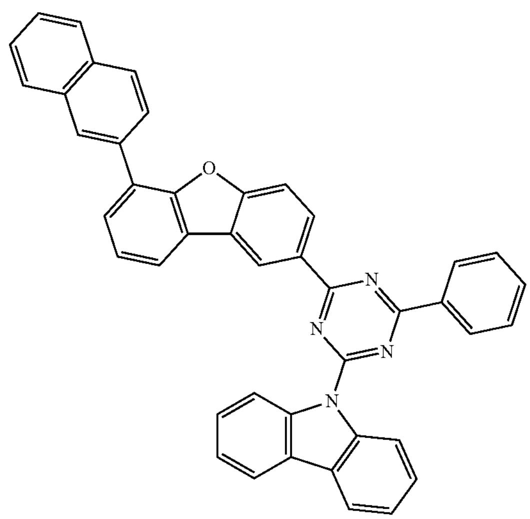
-continued
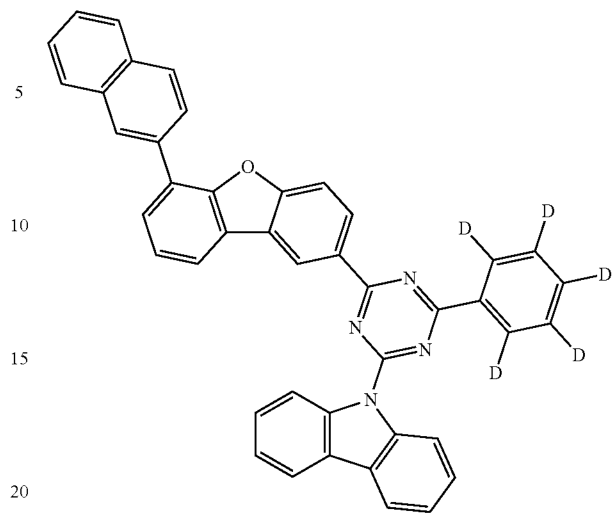
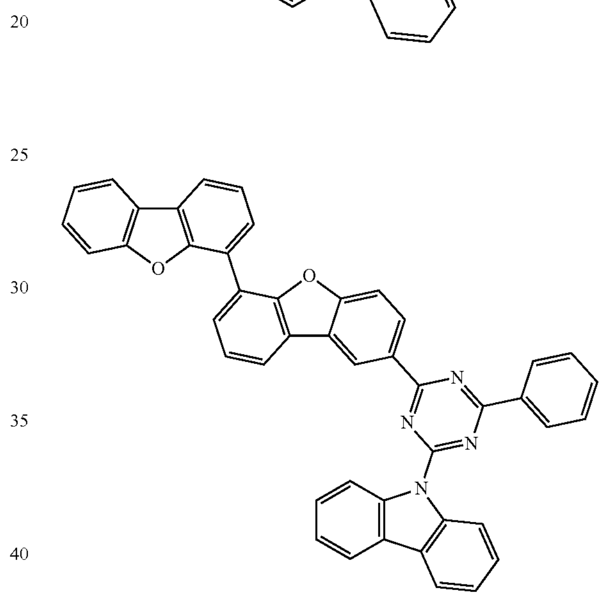
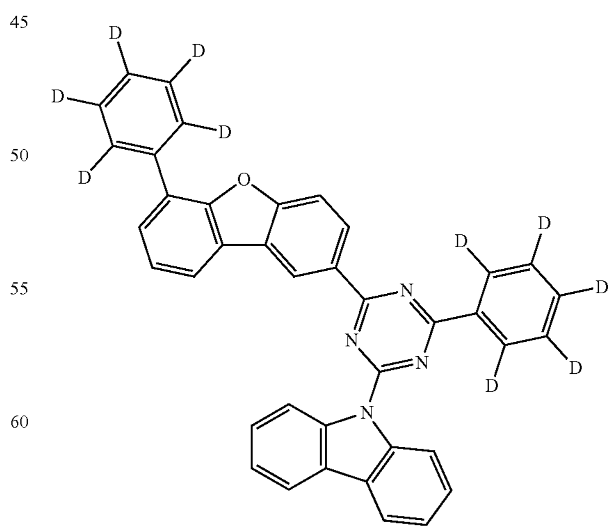

-continued
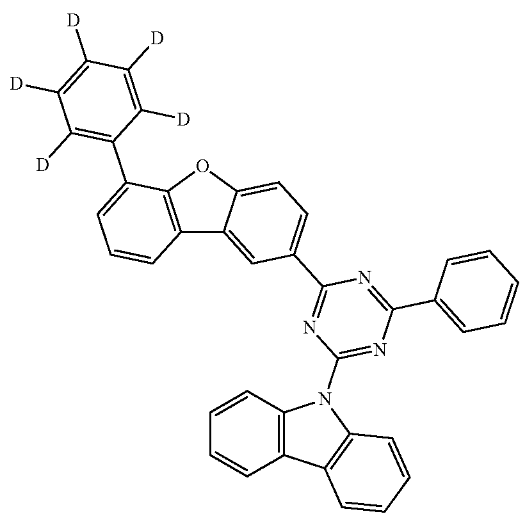
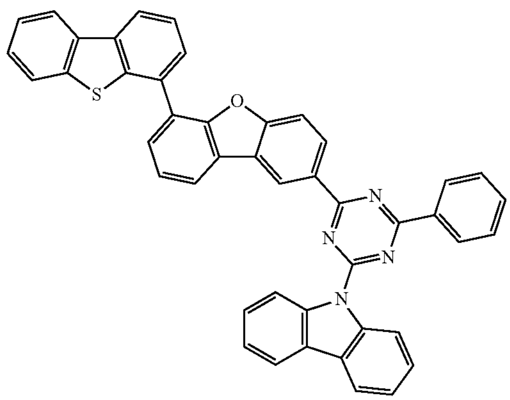
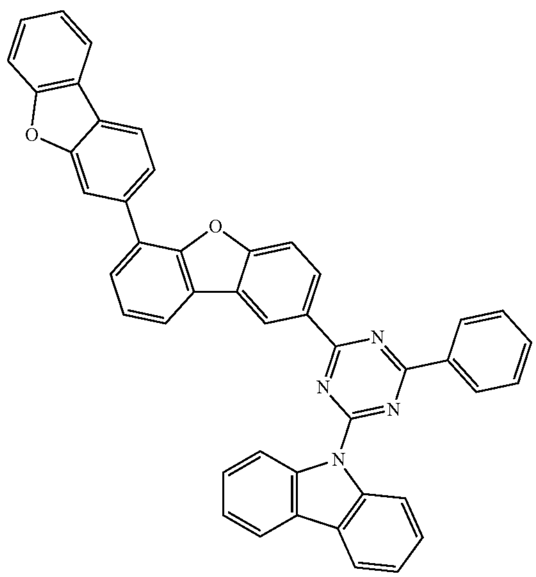
-continued
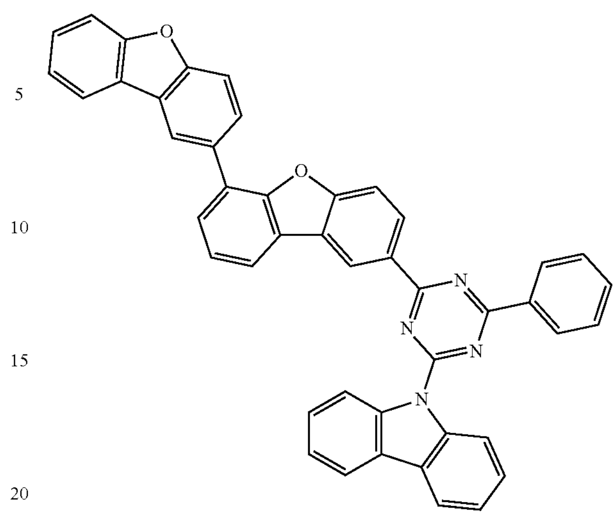
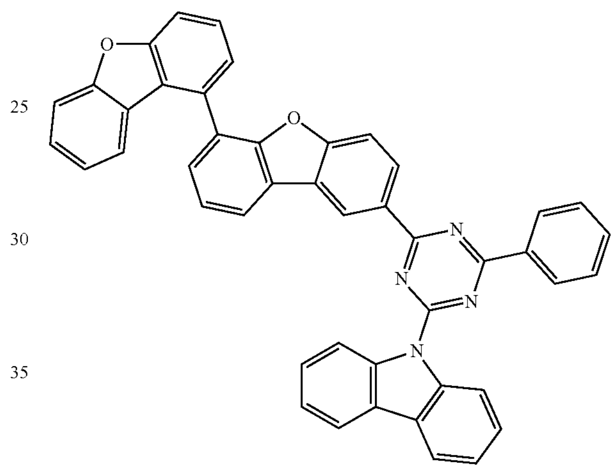
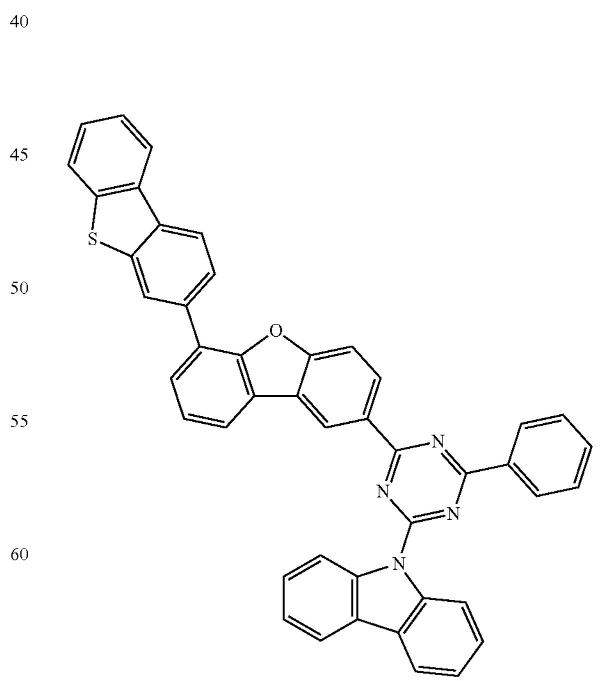

-continued
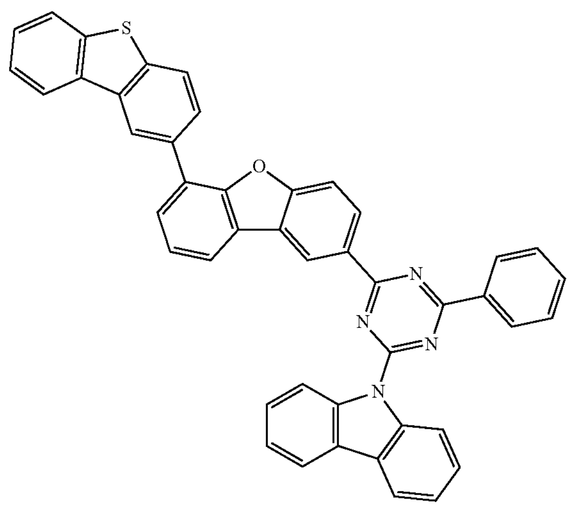
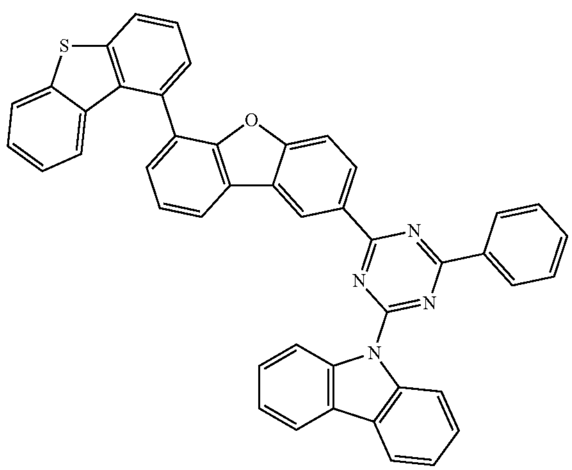
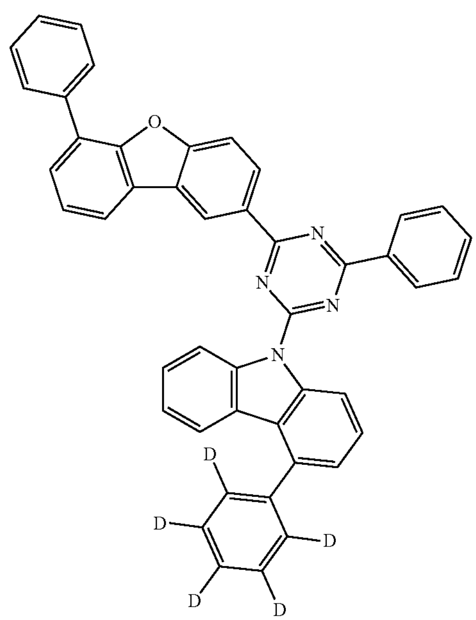
-continued
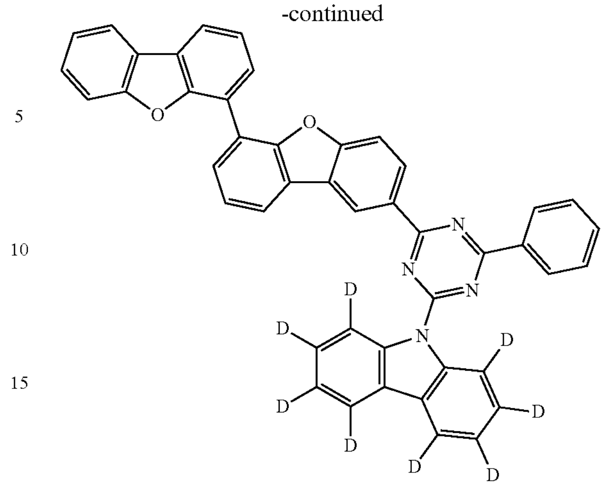
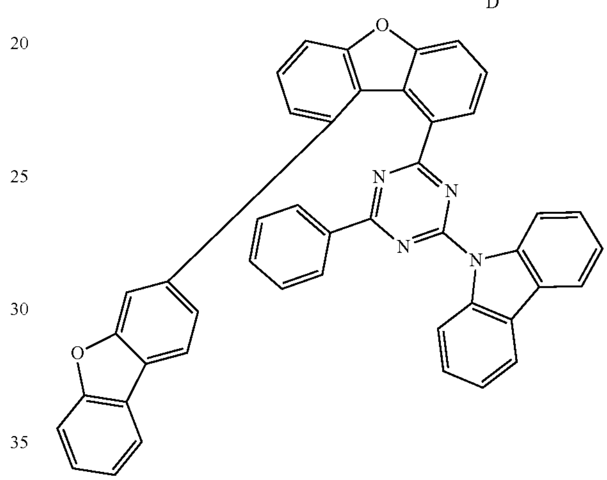
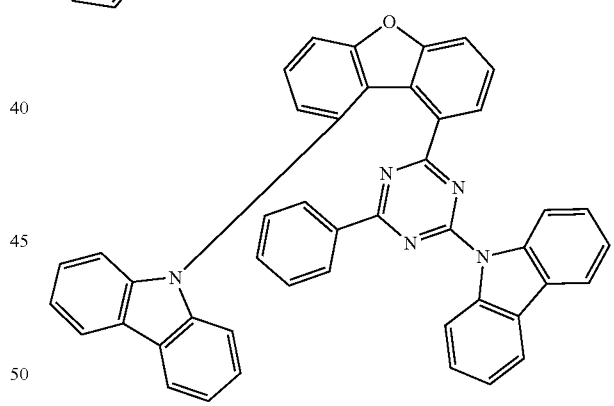
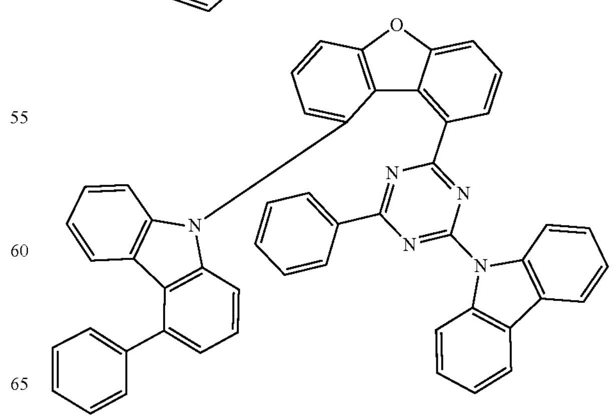

-continued
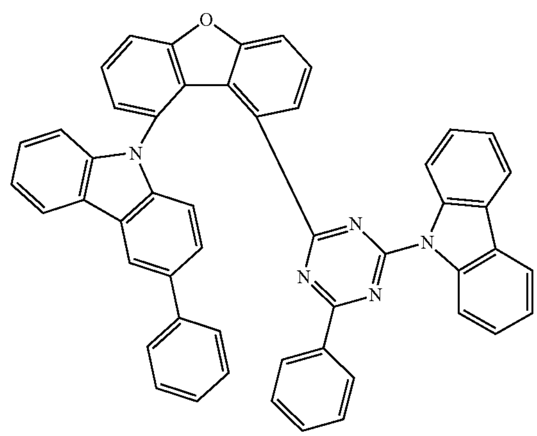
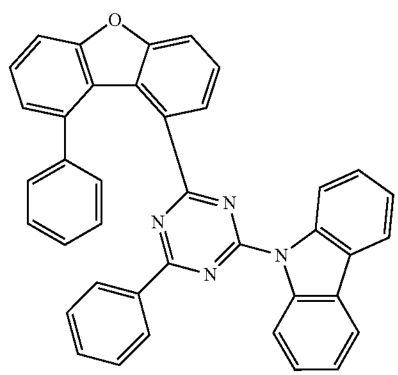
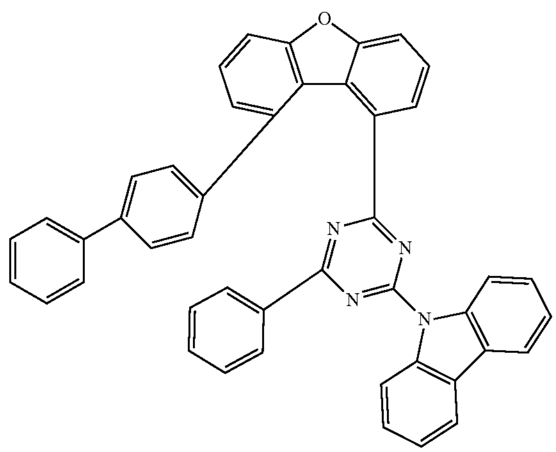
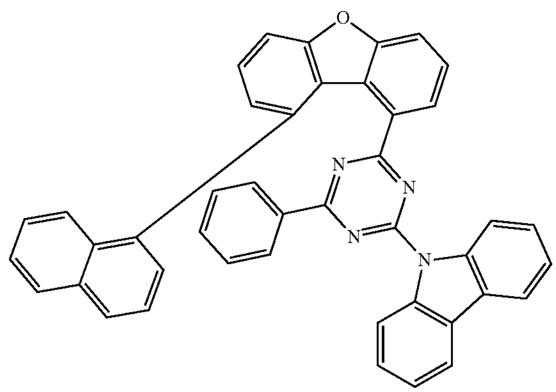
-continued
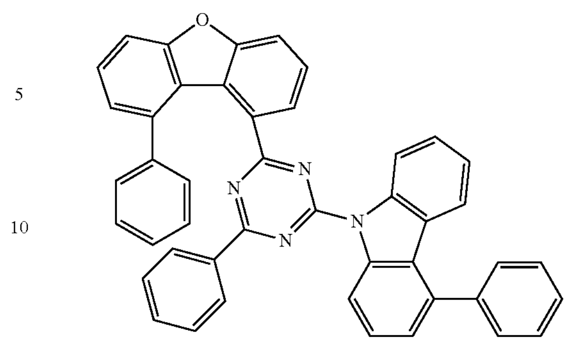
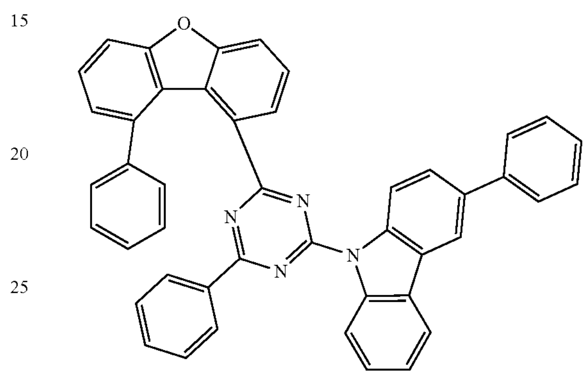
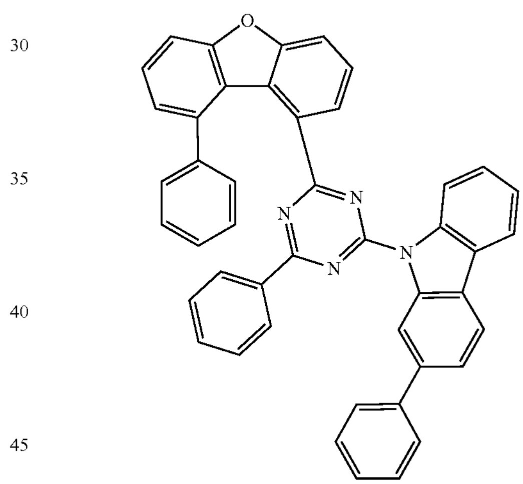
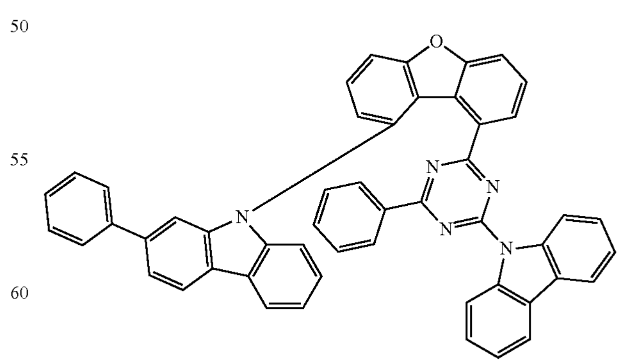

-continued
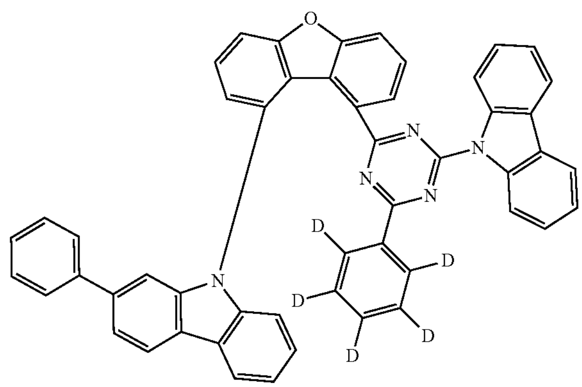
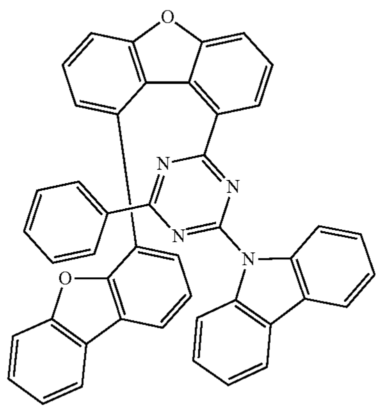
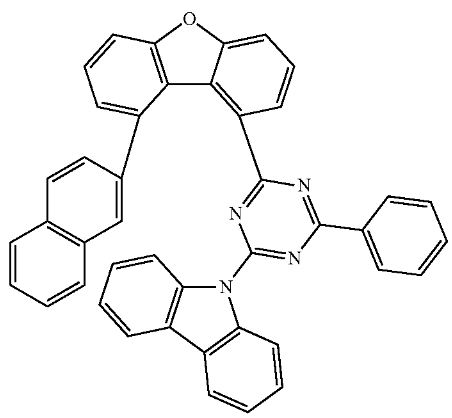
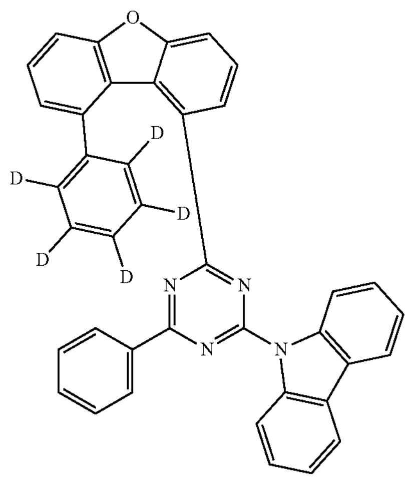
-continued
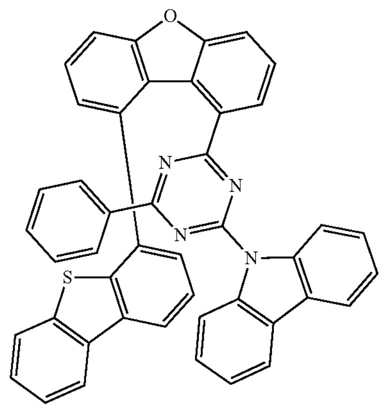
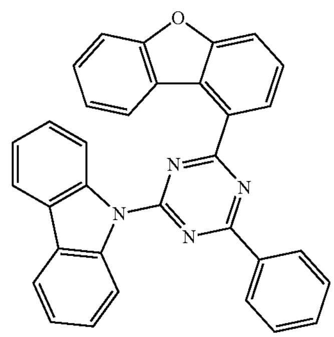
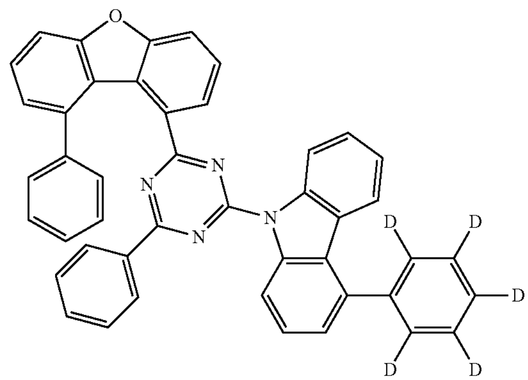
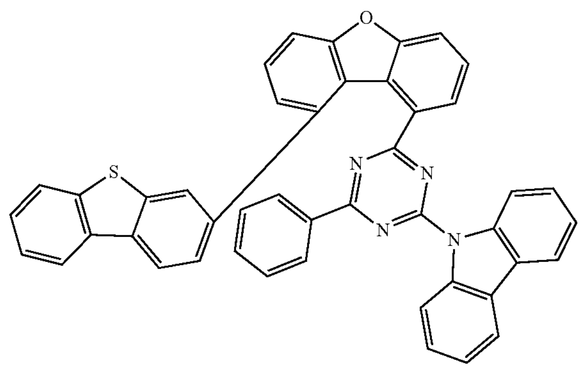

-continued
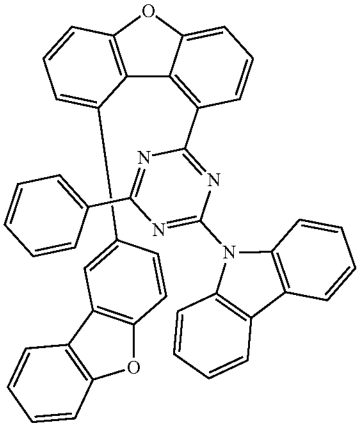
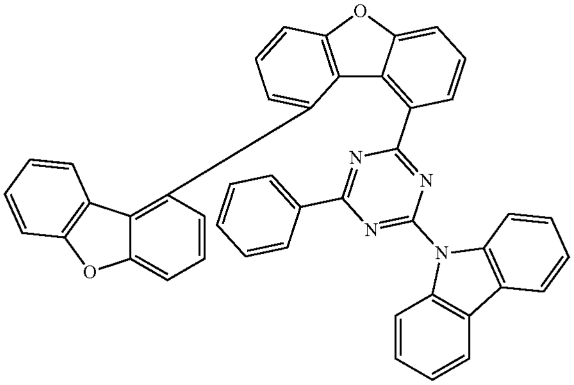
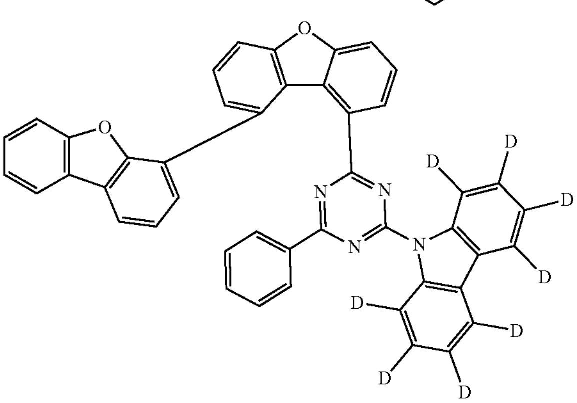
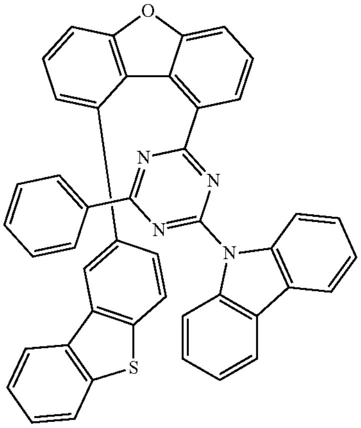
-continued
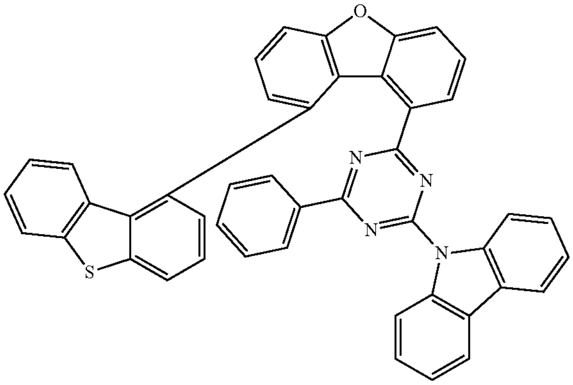
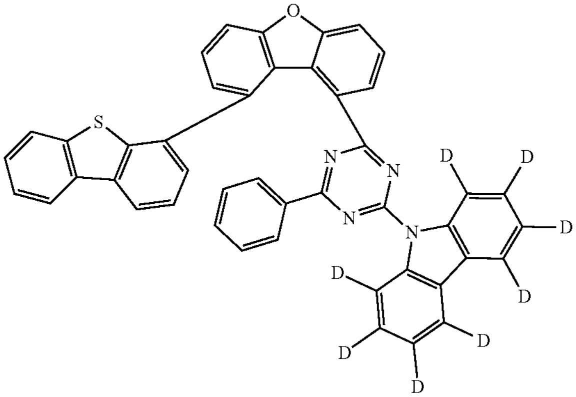
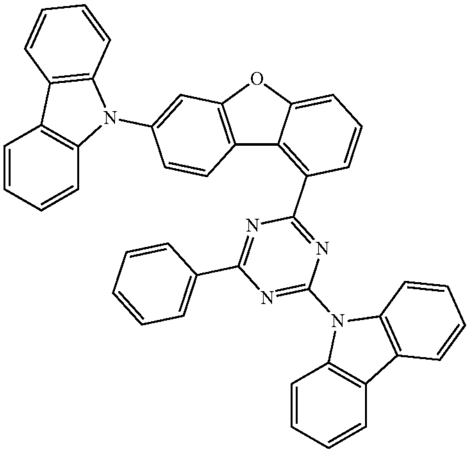
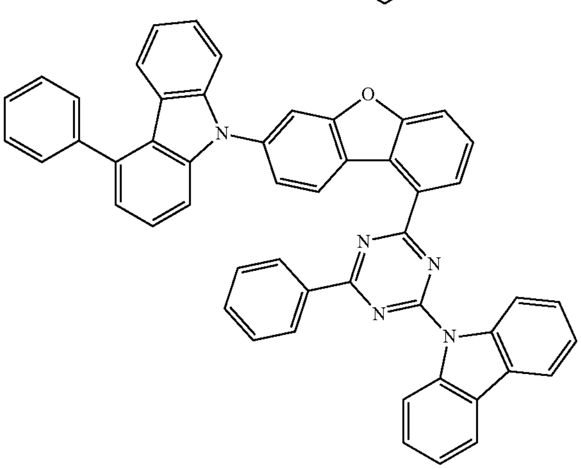

-continued
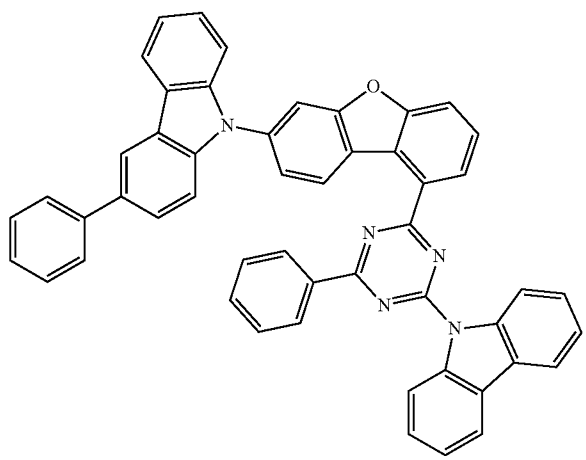
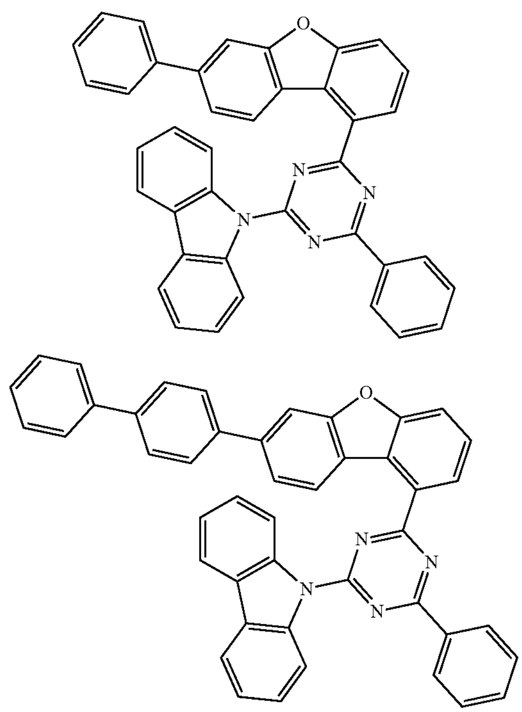
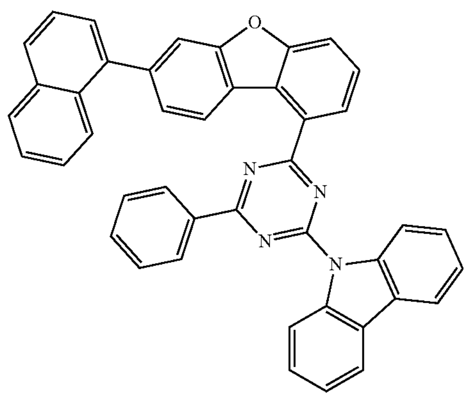
-continued
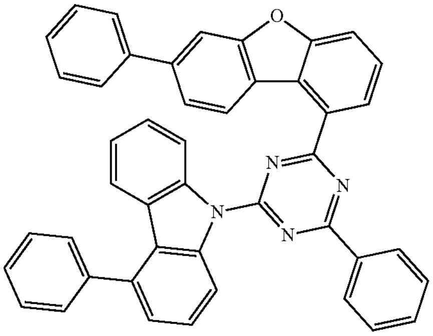
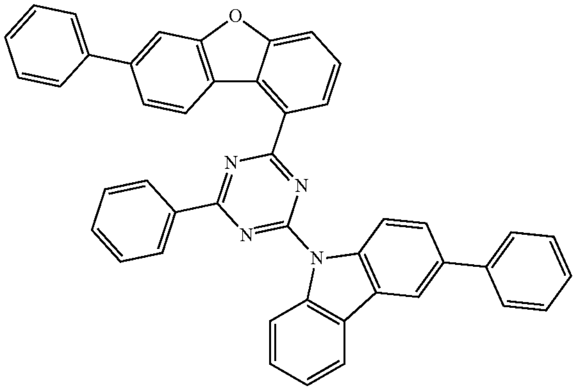
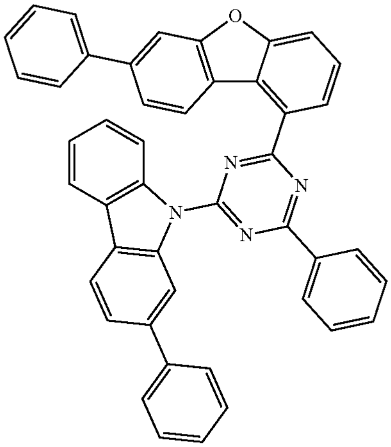
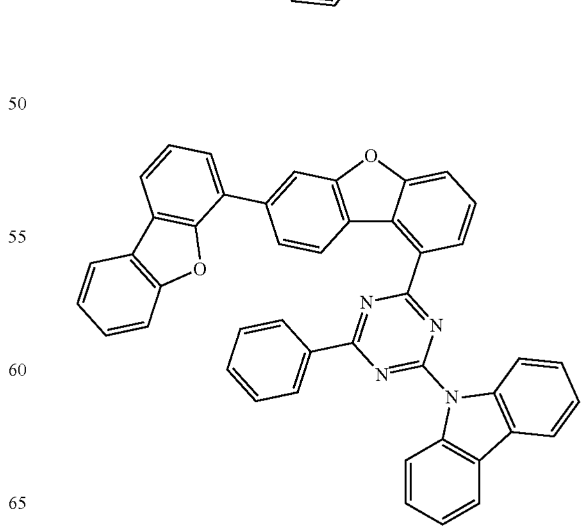

-continued
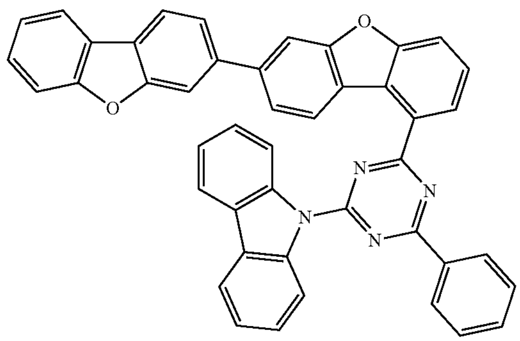
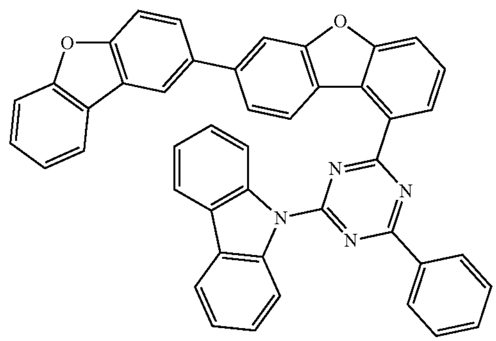
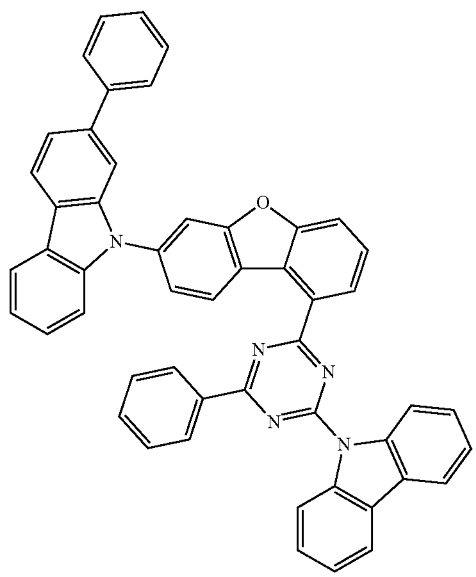
-continued
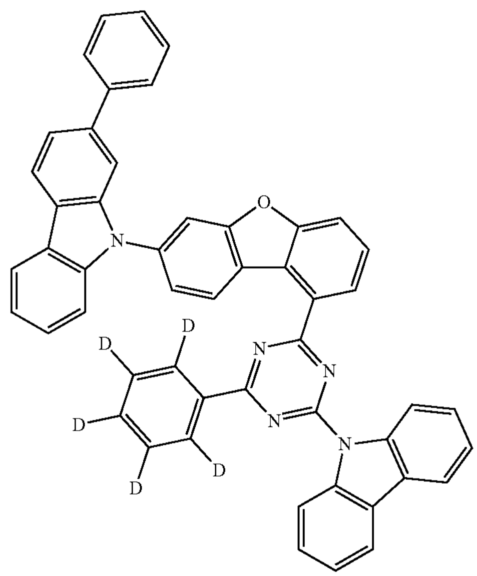
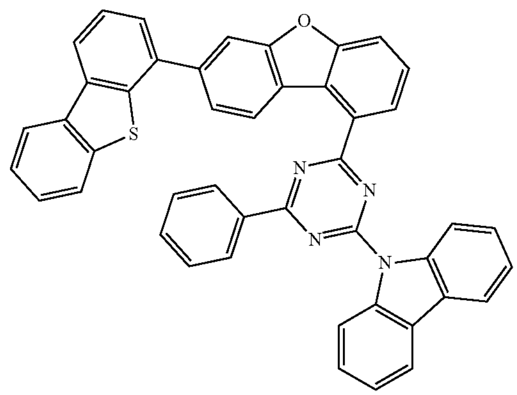
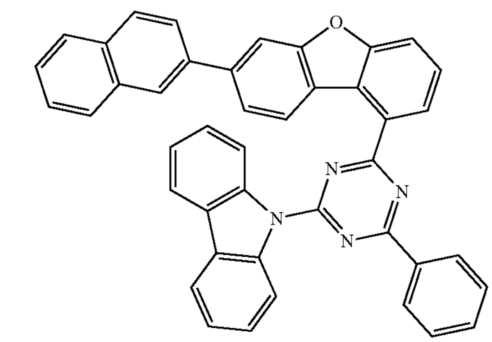
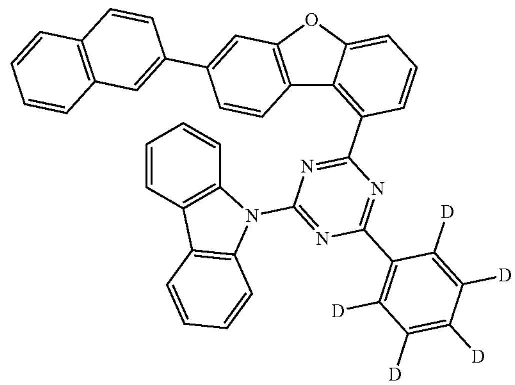

-continued
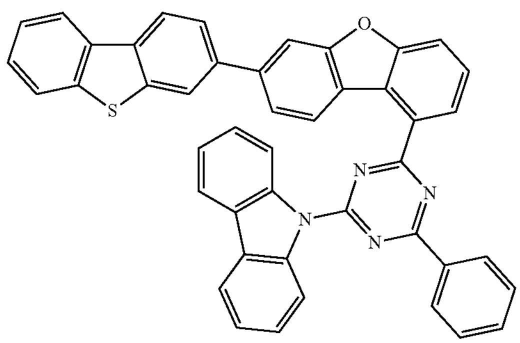
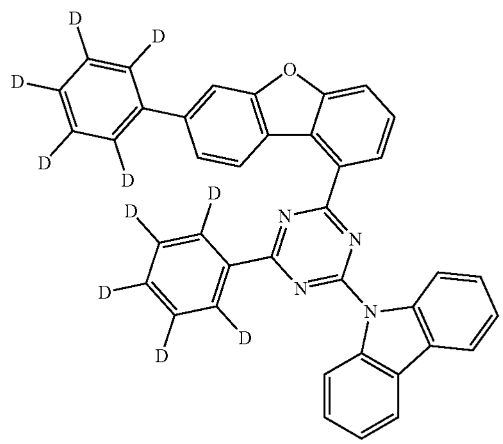
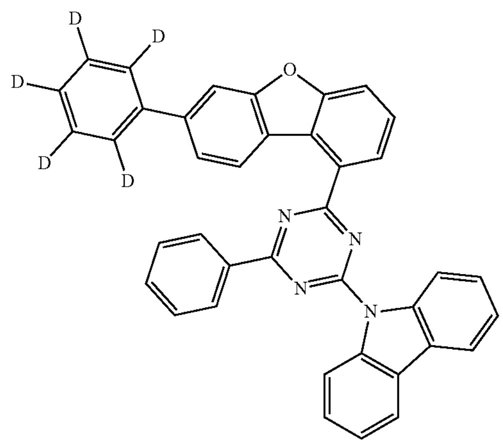
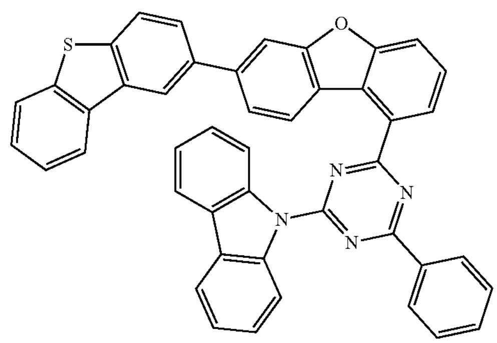
-continued
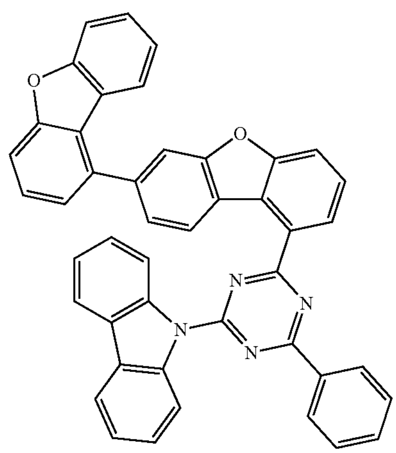
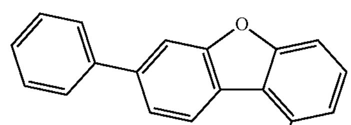
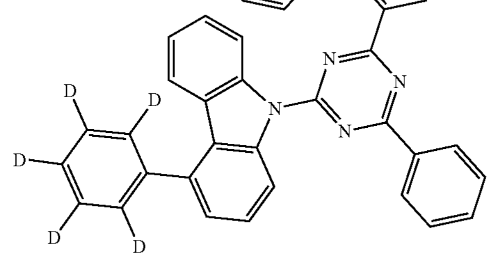
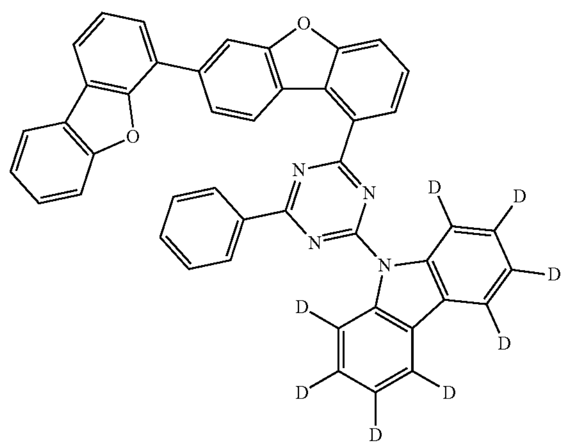
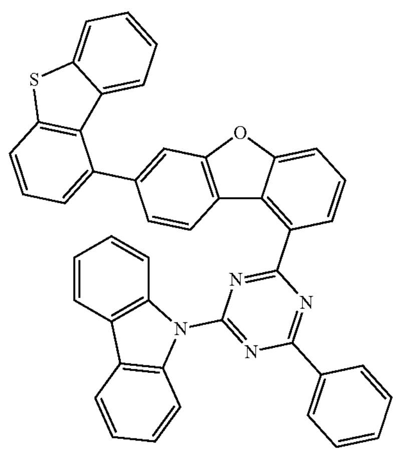

-continued
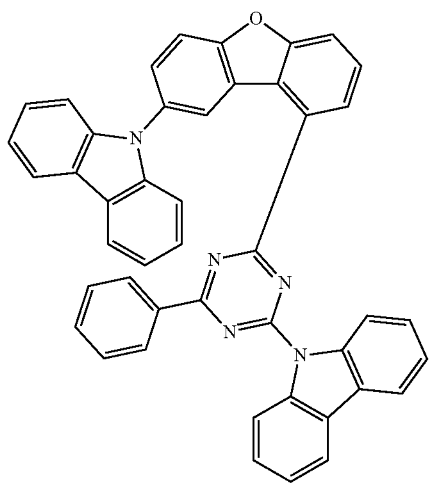
-continued
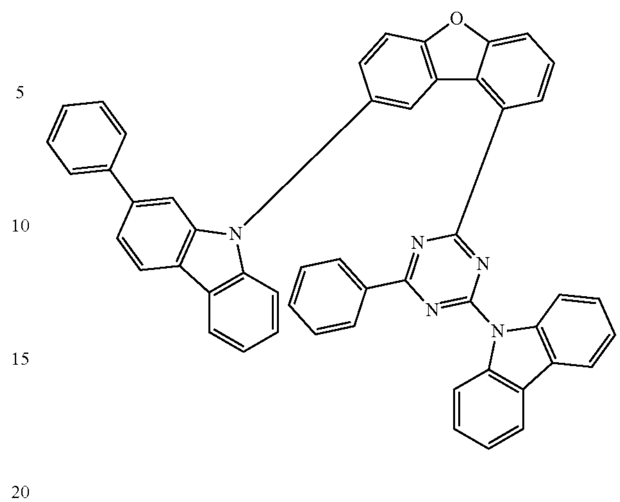
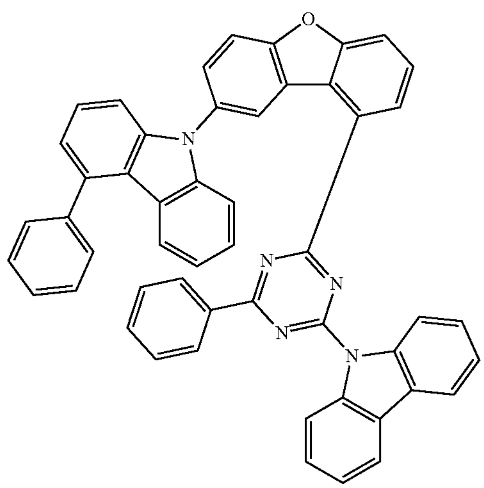
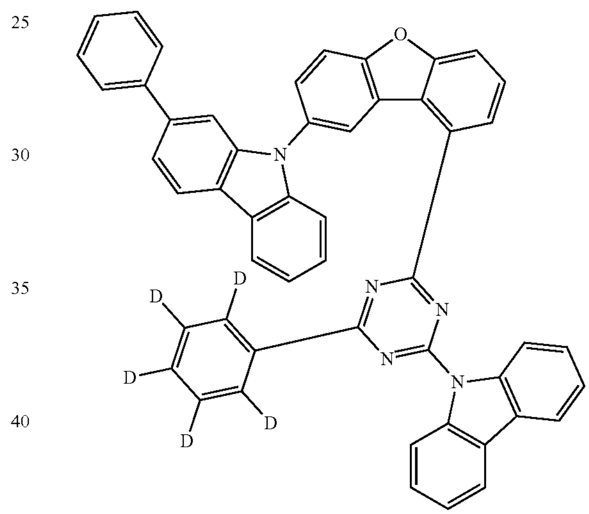
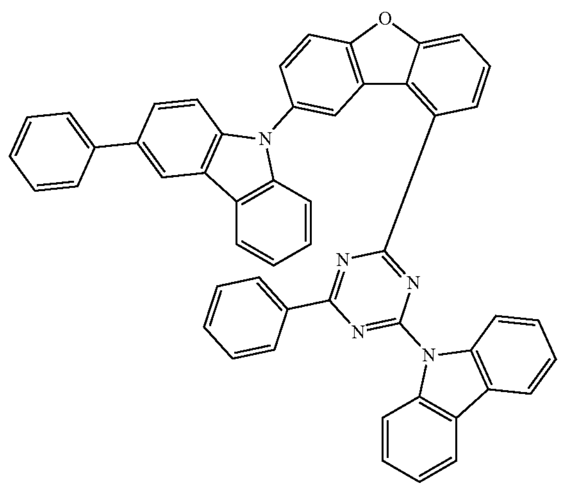
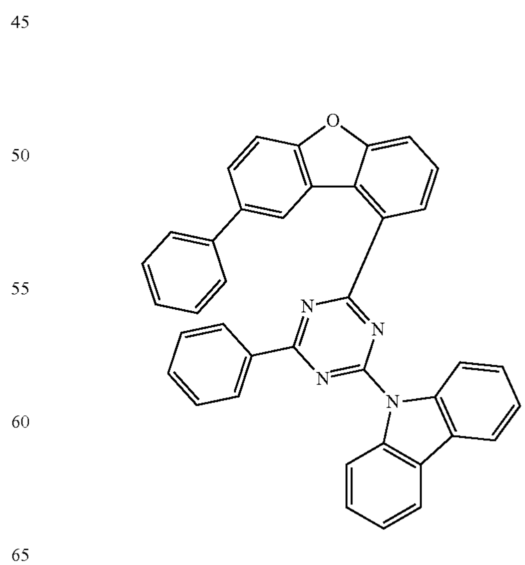

-continued
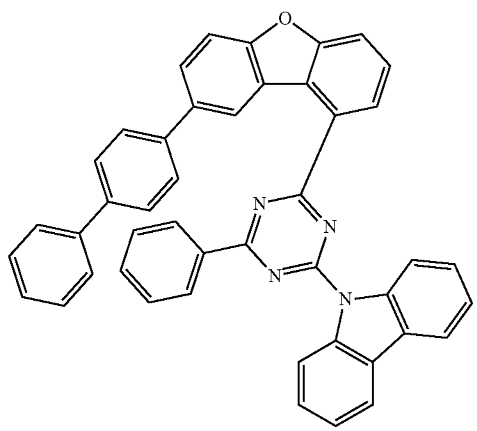
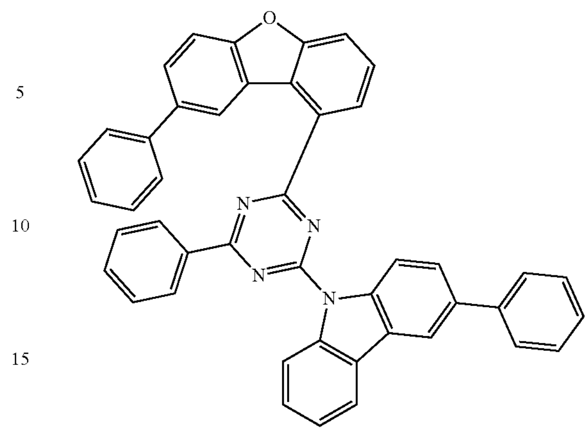
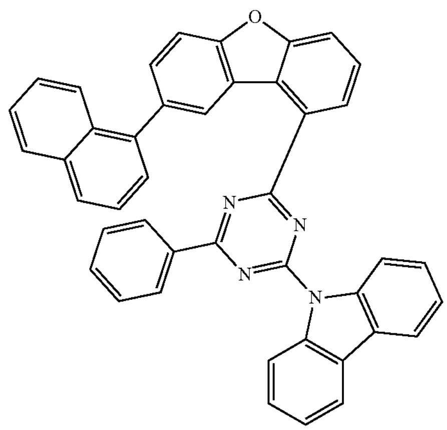
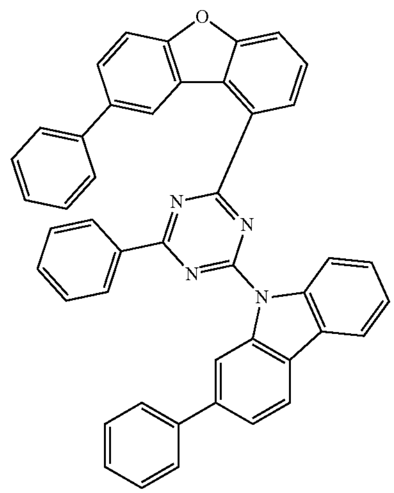
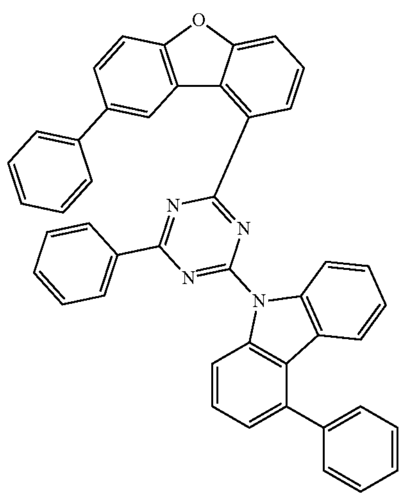
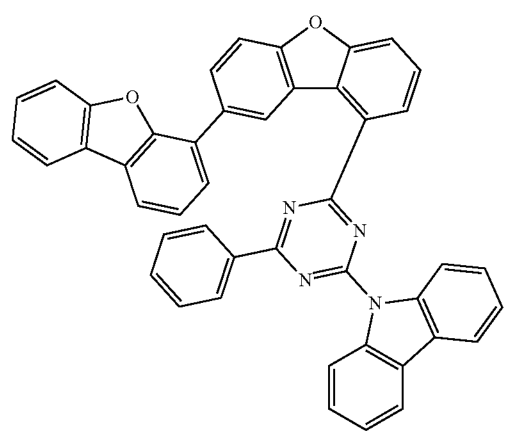
-continued -continued
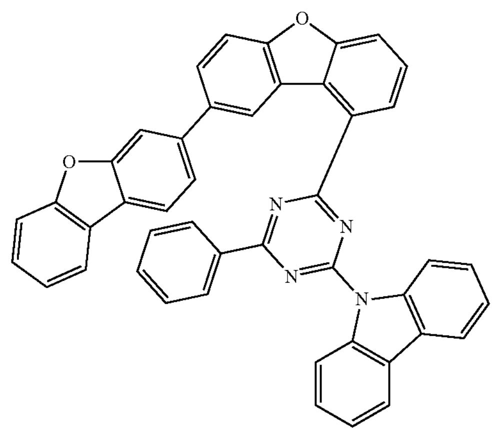
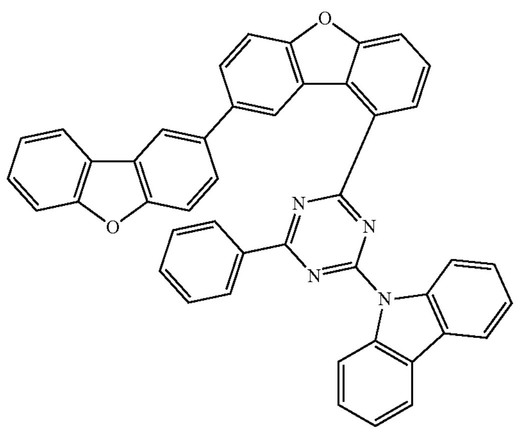
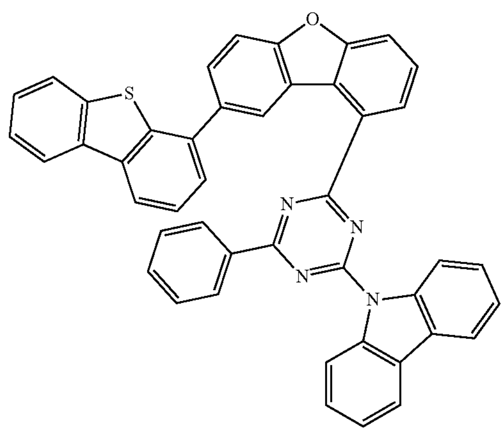
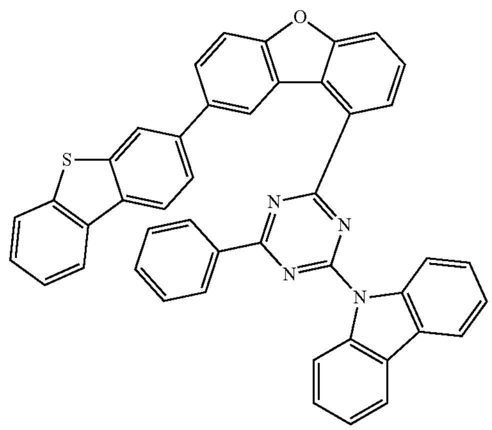
-continued
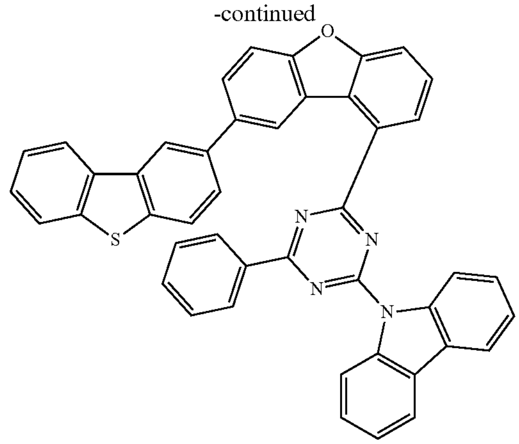
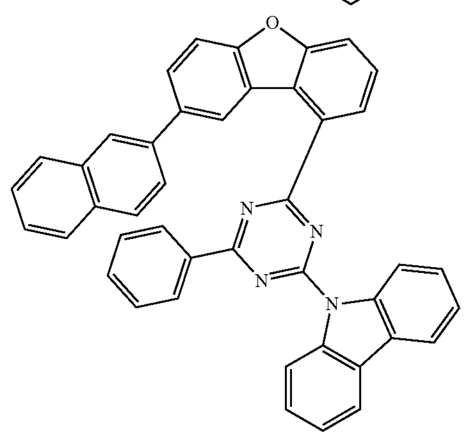
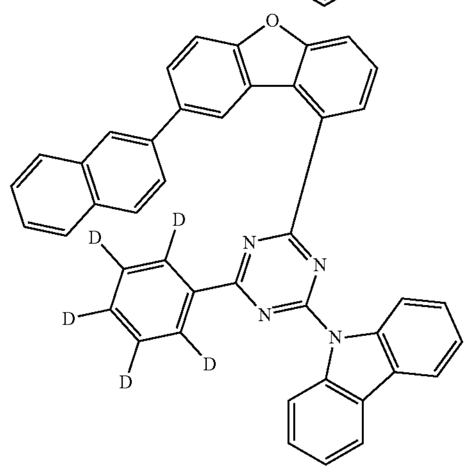
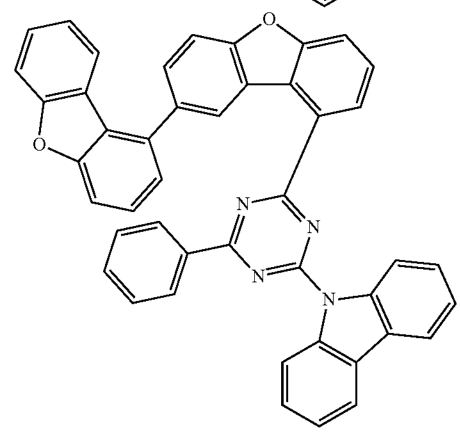

-continued
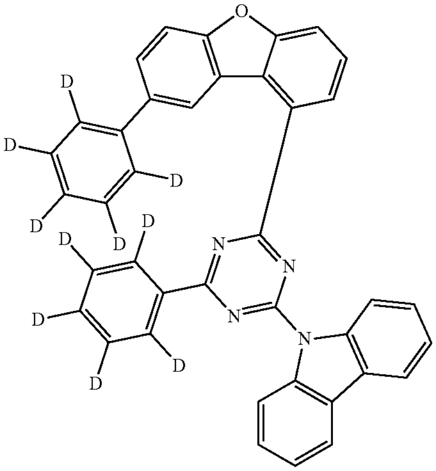
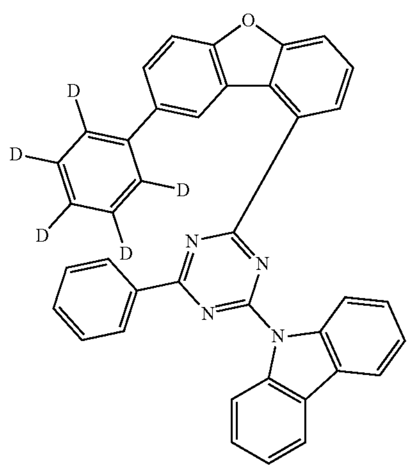
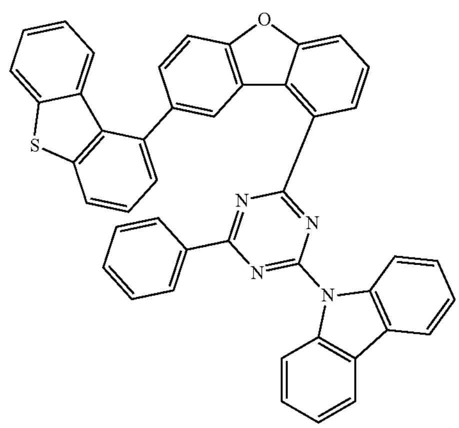
-continued
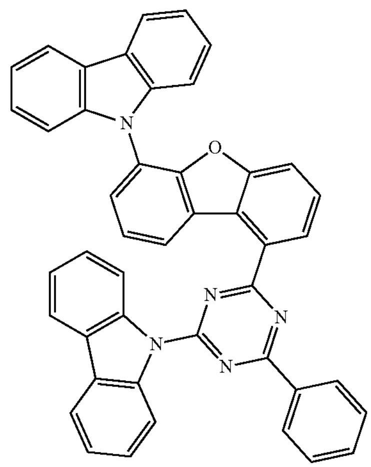
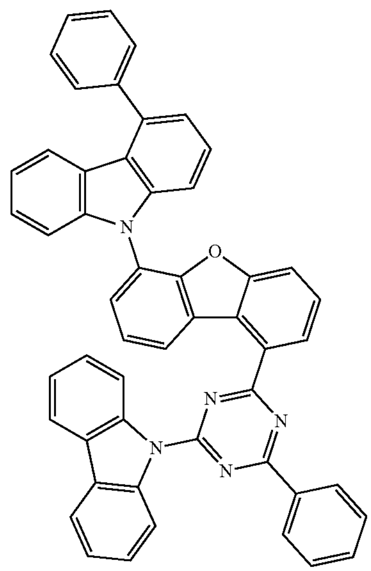
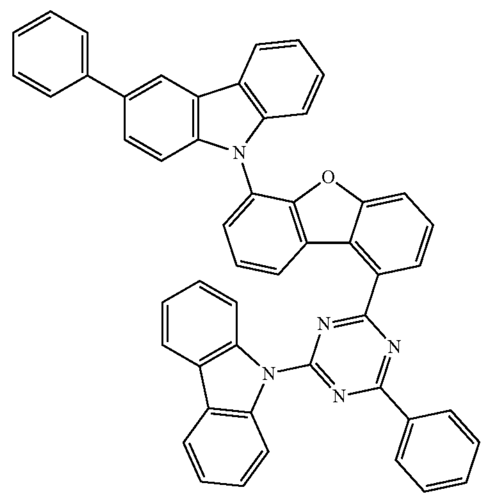

-continued
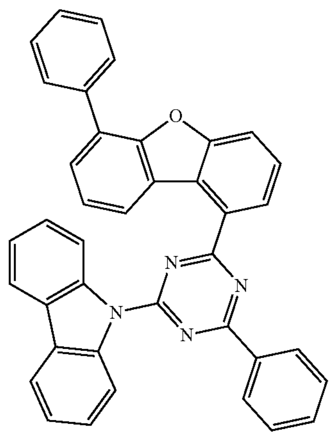
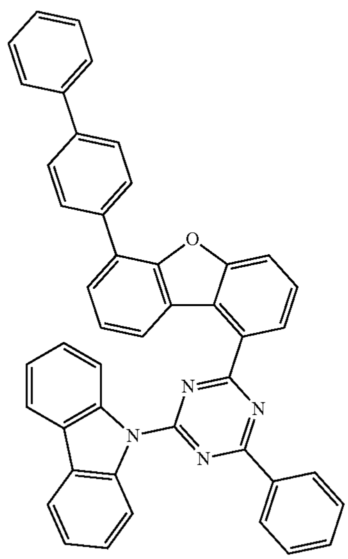
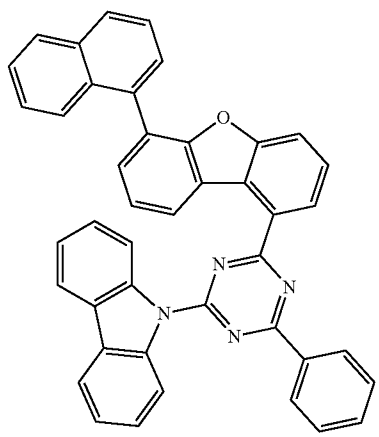
-continued
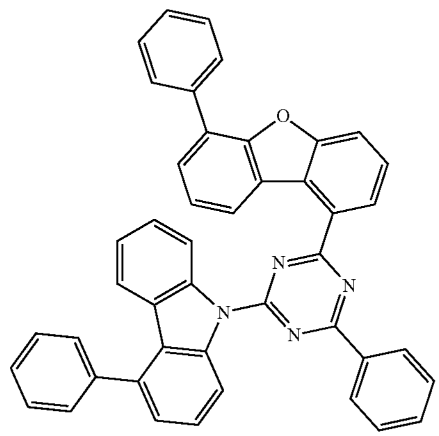
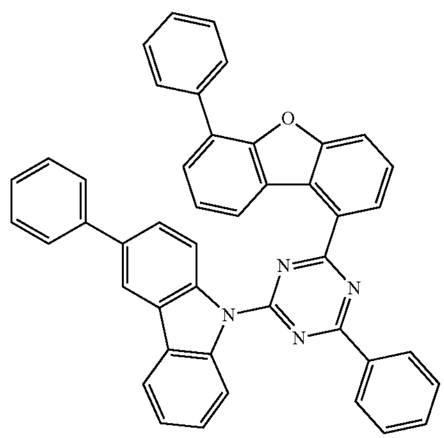
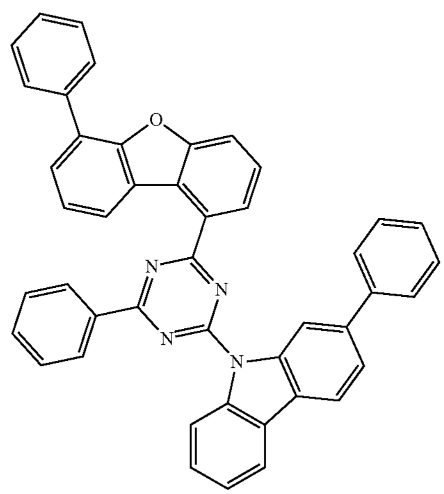

-continued
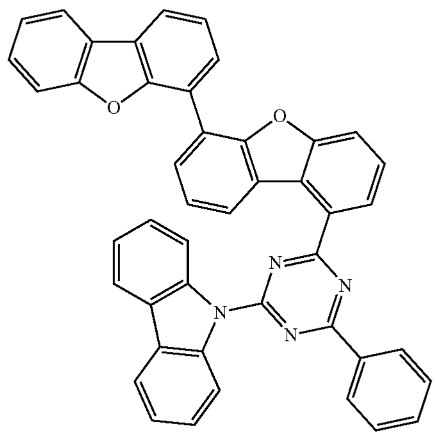
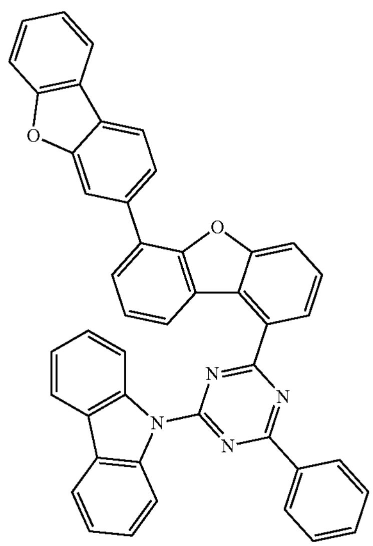
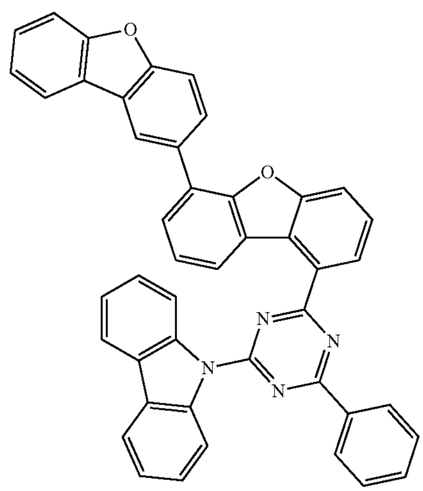
-continued
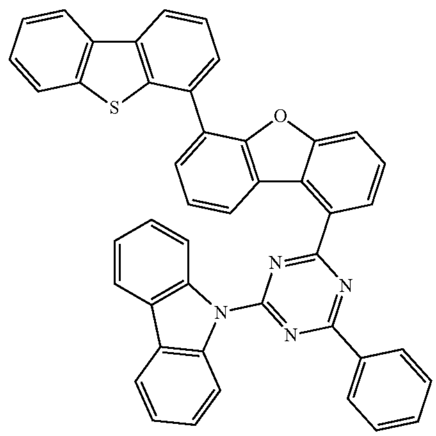
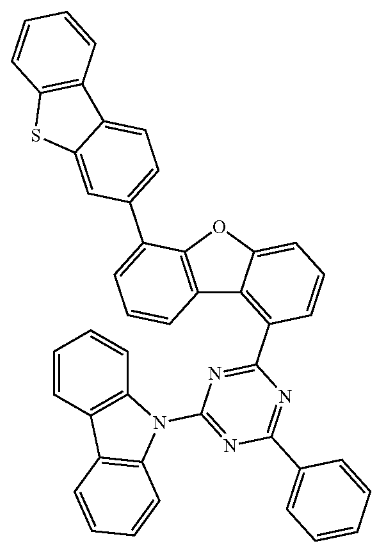
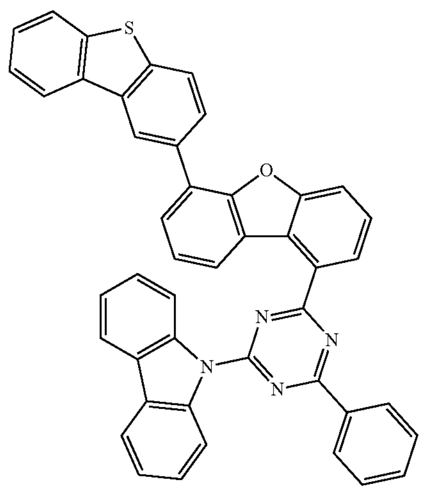

-continued
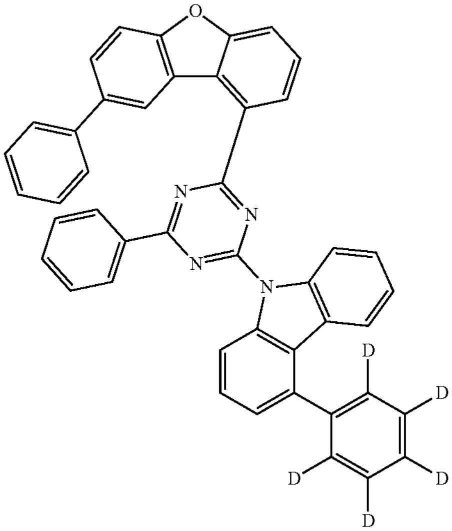
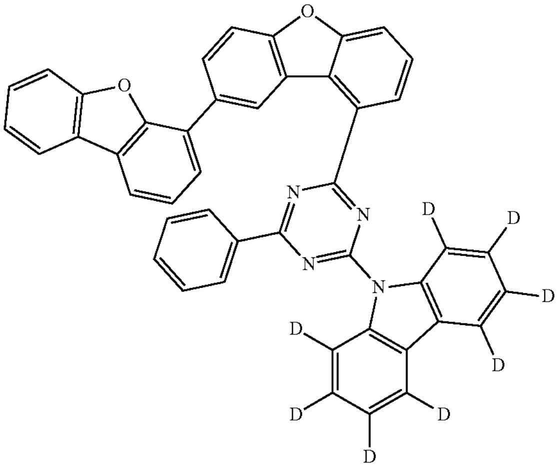
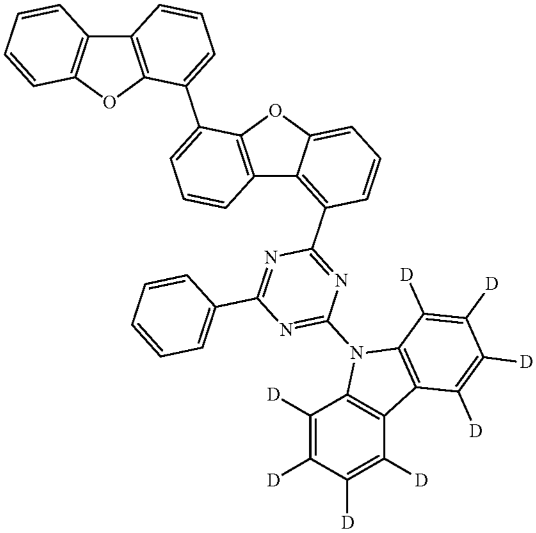
-continued
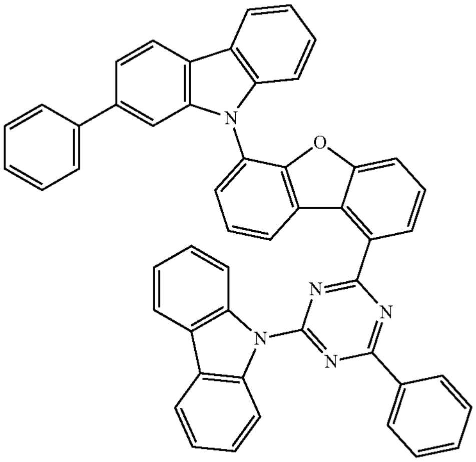
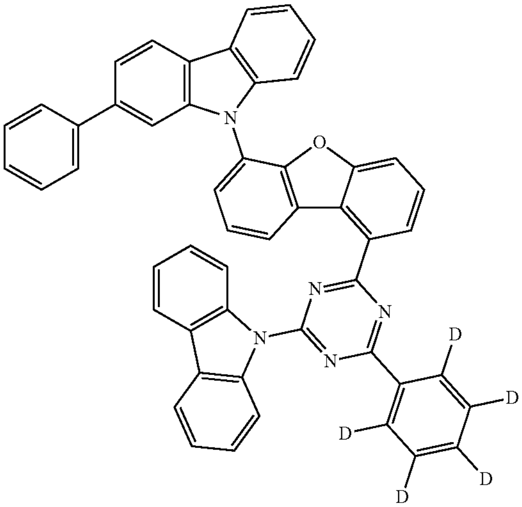
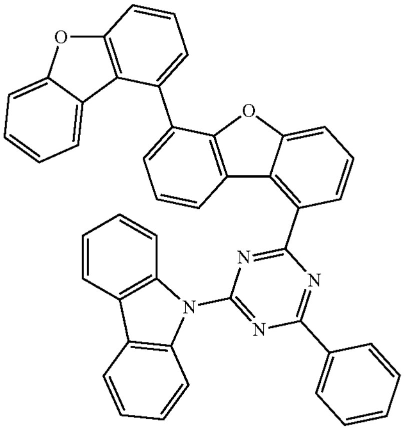

-continued
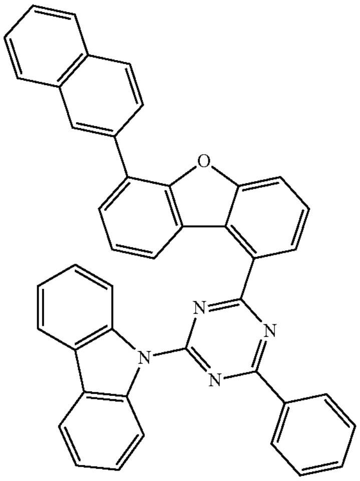
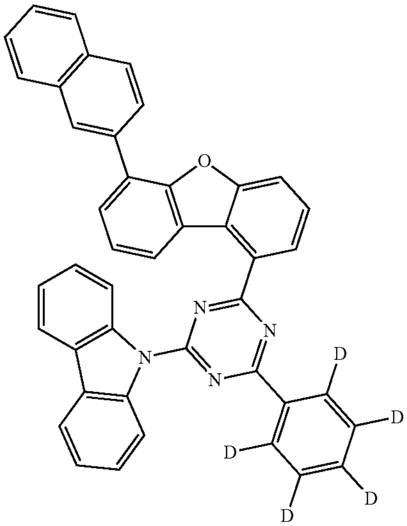
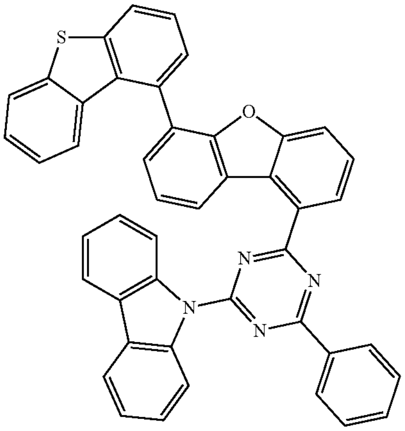
-continued
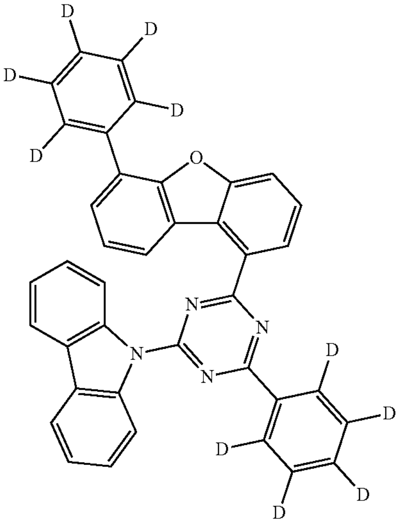
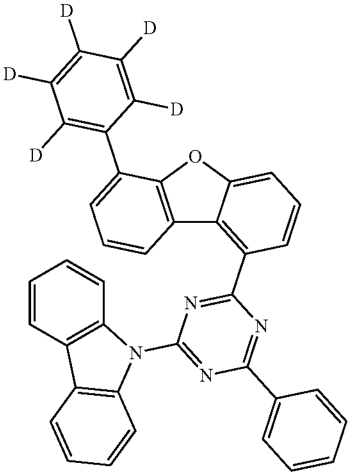
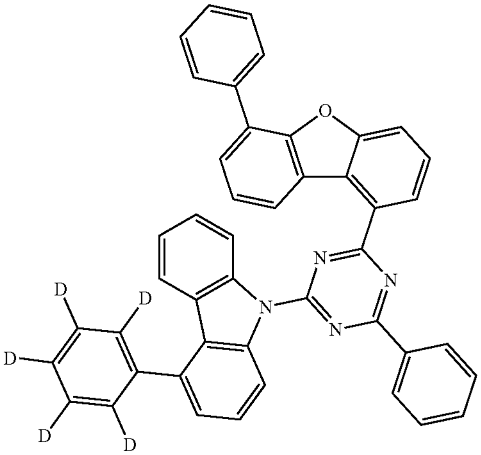

-continued
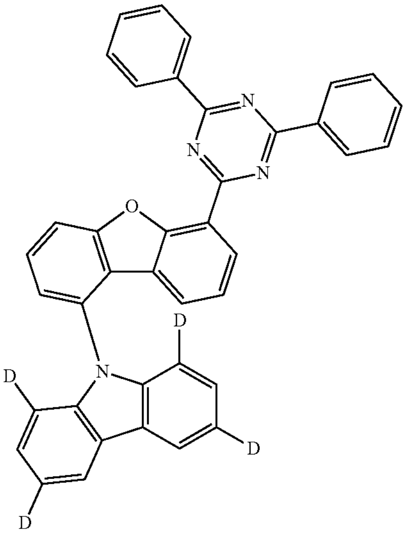
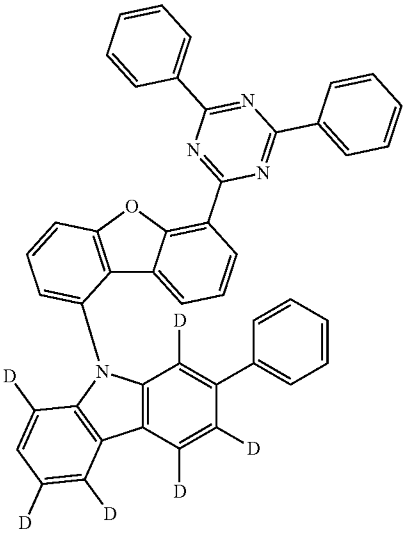
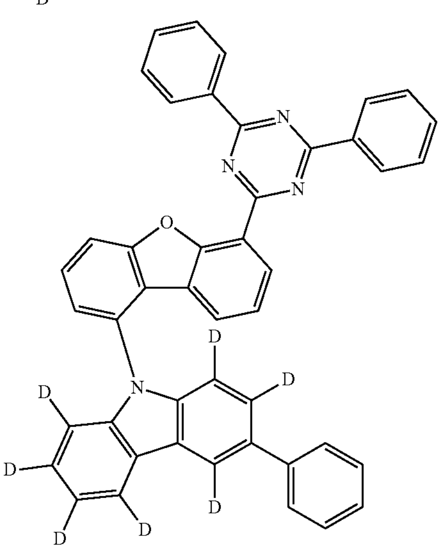
-continued
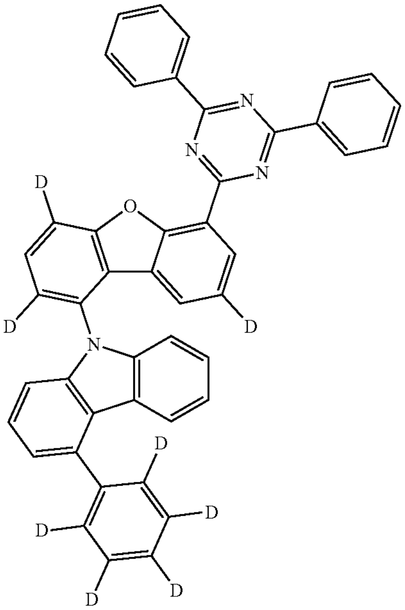
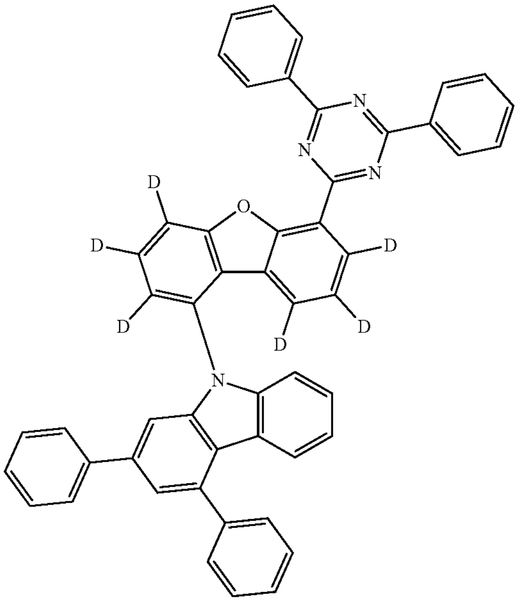

-continued
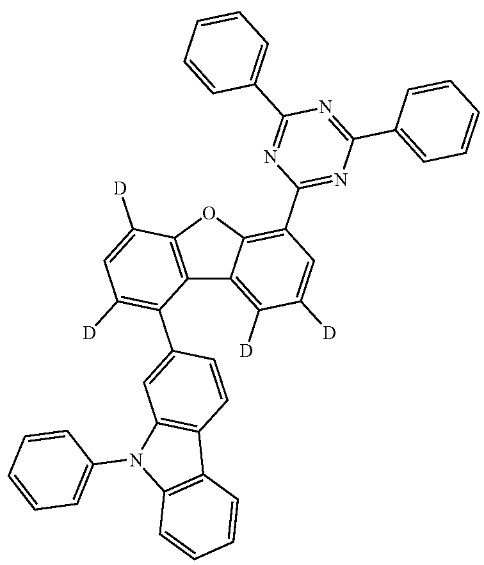
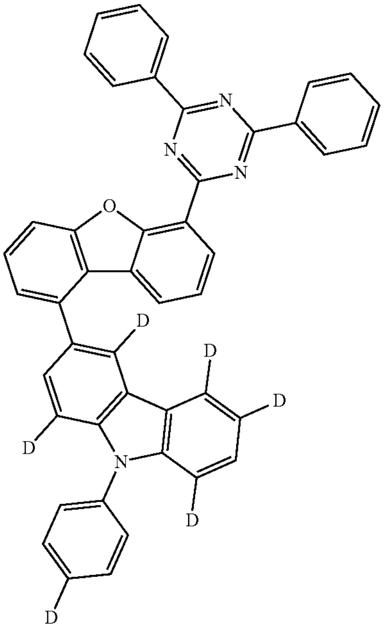
-continued
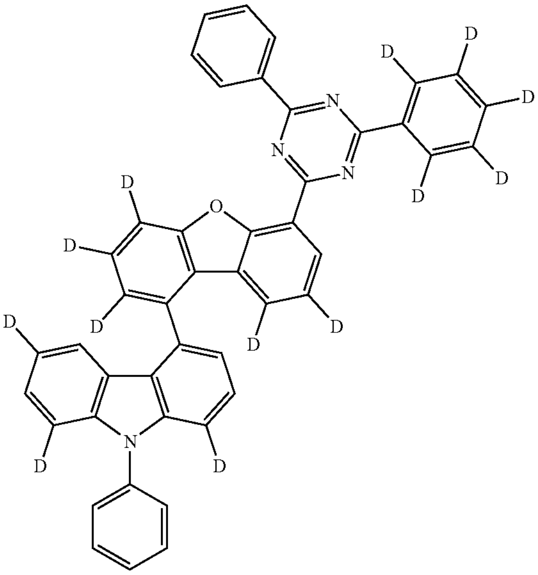
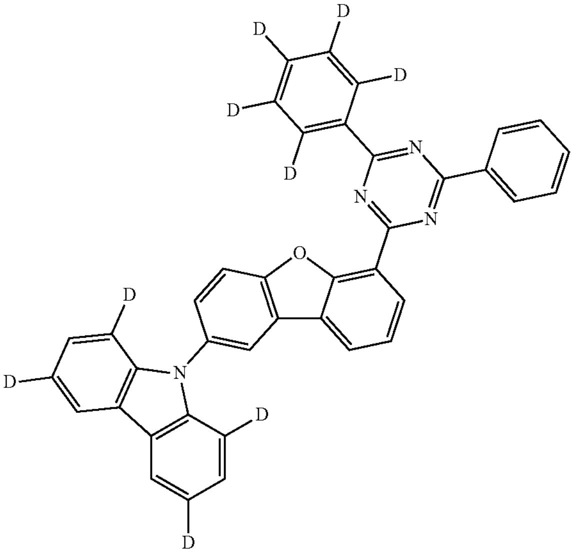
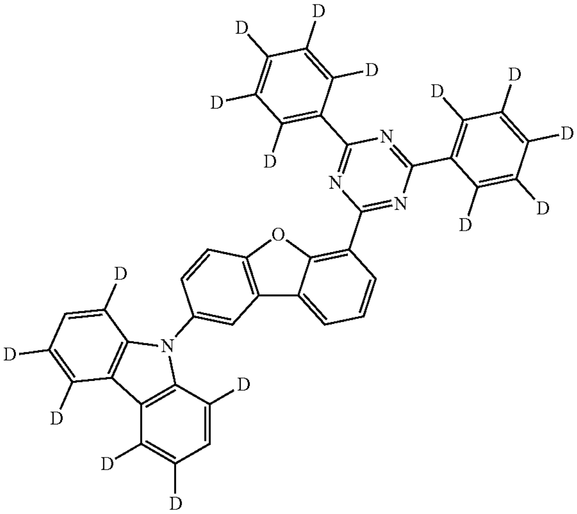

-continued
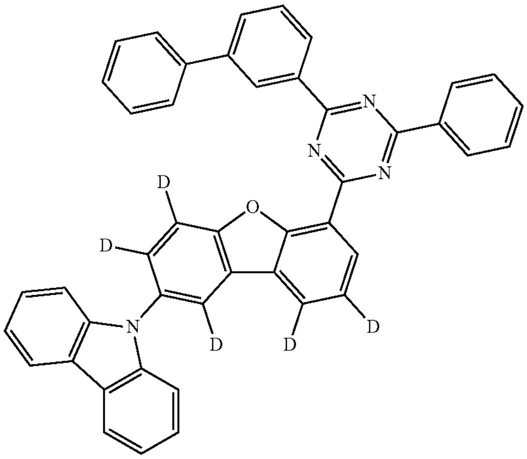
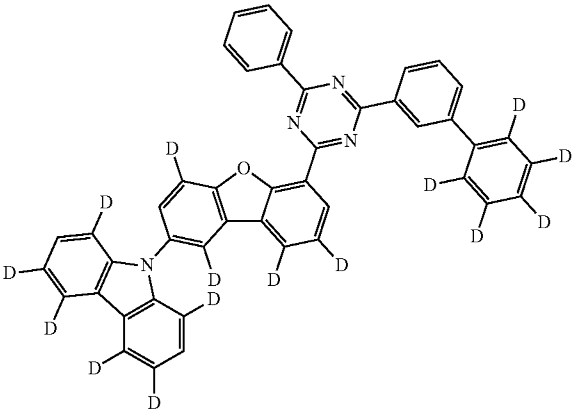
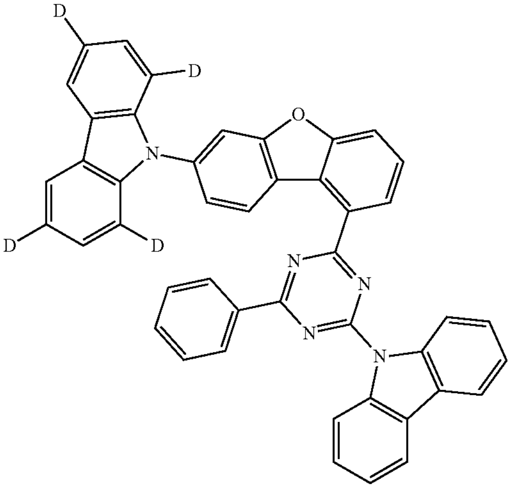
-continued
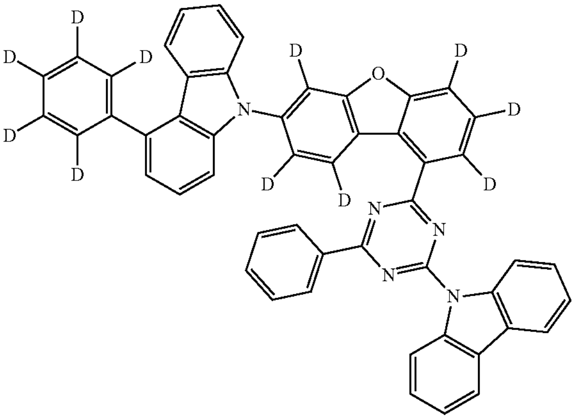
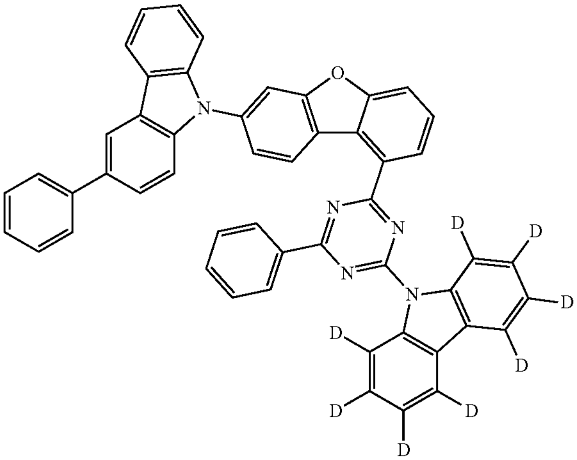
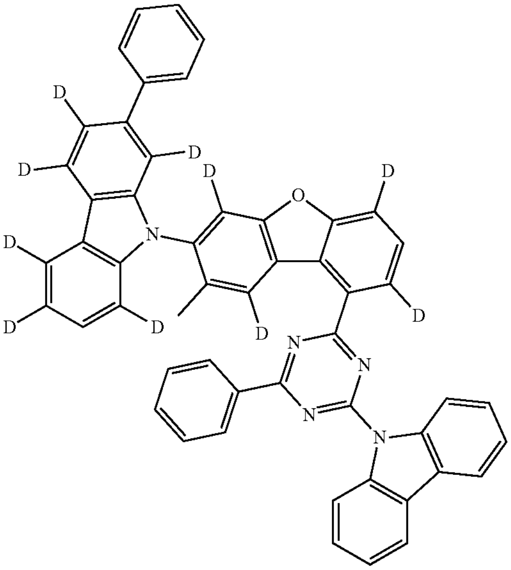

-continued
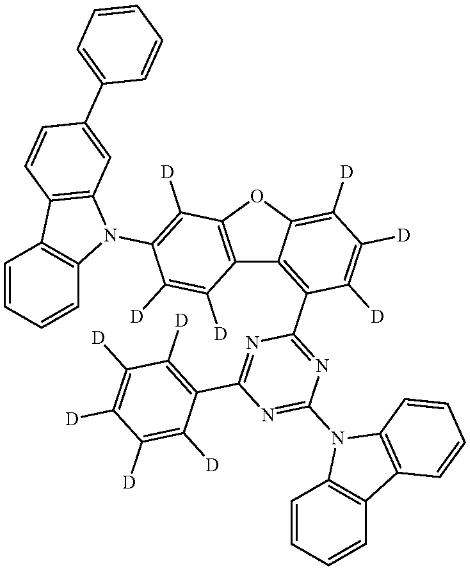
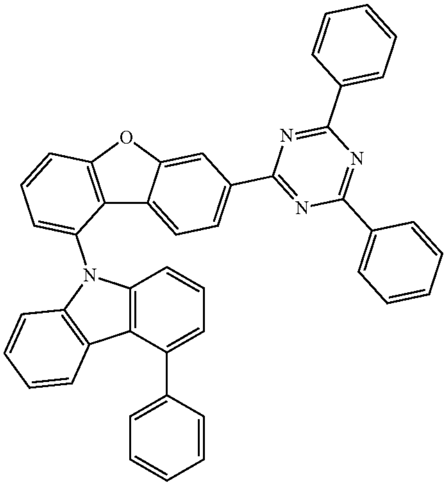
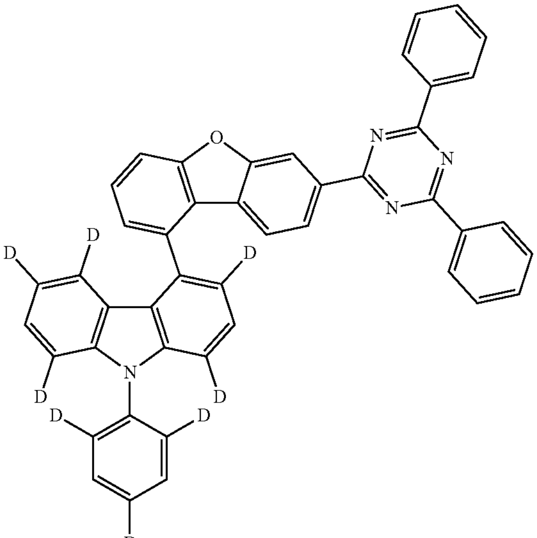
-continued
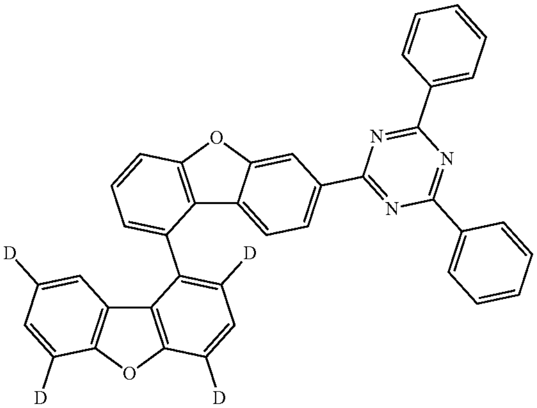
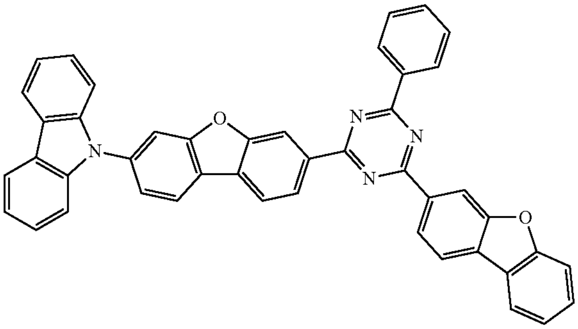
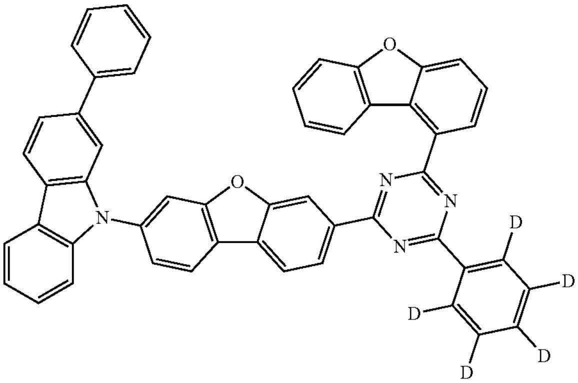
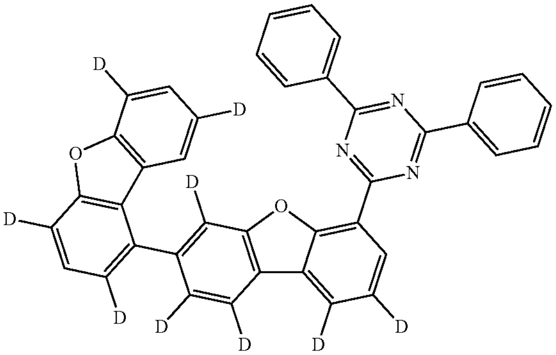

-continued

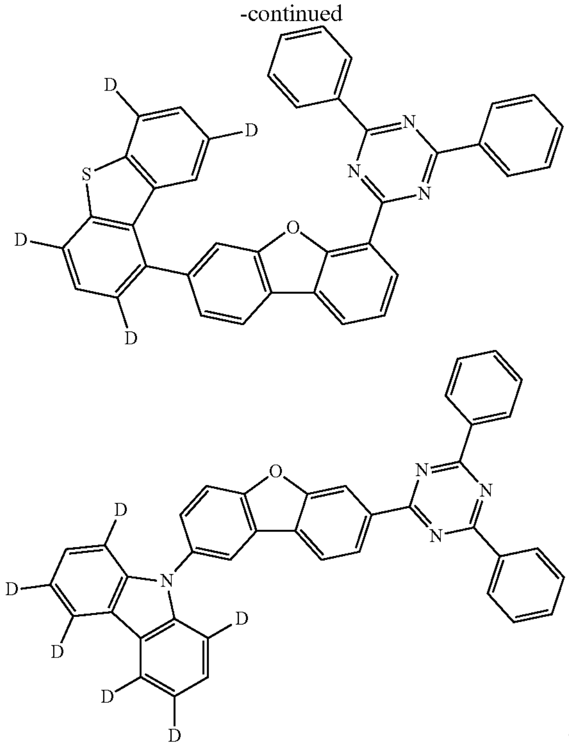

.

7. The organic light emitting device according to claim 1, wherein:

the Chemical Formula 2 is the following Chemical Formula 2-1:

[Chemical Formula 2-1]

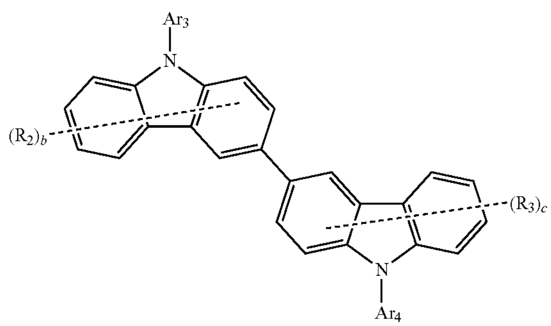

wherein in Chemical Formula 2-1;

$Ar_3$, $Ar_4$, $R_3$, $R_4$, b and c are as defined in claim 1.

8. The organic light emitting device according to claim 1, wherein:

$Ar_3$ and $Ar_4$ are each independently phenyl, biphenylyl, terphenylyl, naphthyl, dimethylfluorenyl, dibenzofuranyl, or dibenzothiophenyl.

9. The organic light emitting device according to claim 1, wherein:

$R_2$ and $R_3$ are each independently hydrogen or phenyl.

10. The organic light emitting device according to claim 9, wherein:

one of $R_2$ and $R_3$ is phenyl and the rest is hydrogen, or both $R_2$ and $R_3$ are hydrogen.

11. The organic light emitting device according to claim 1, wherein:

the compound of Chemical Formula 2 is any one compound selected from the group consisting of the following compounds:

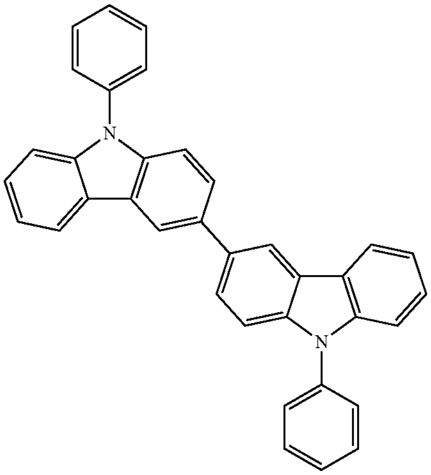

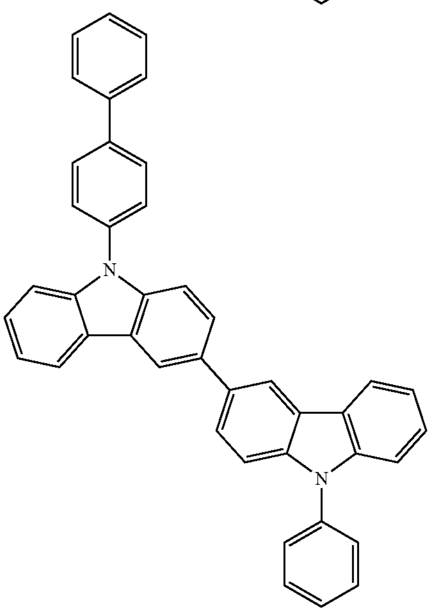

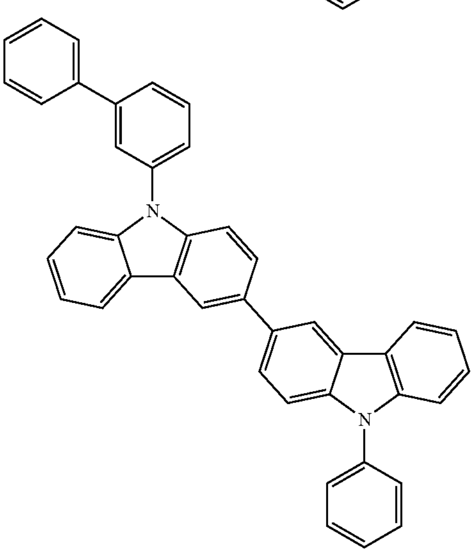

-continued
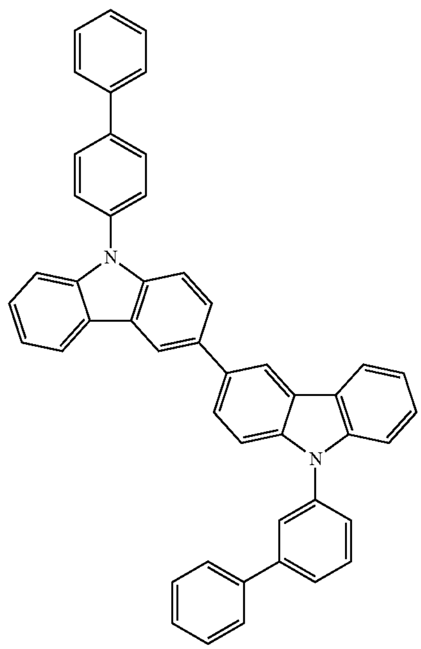
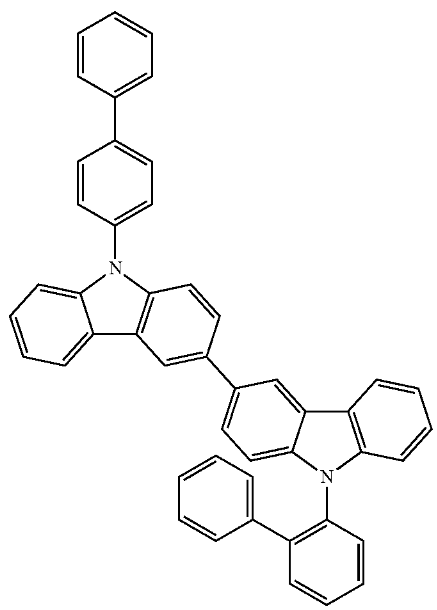
-continued
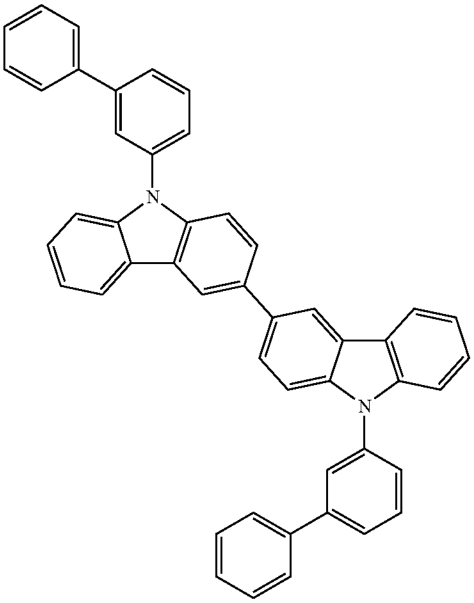
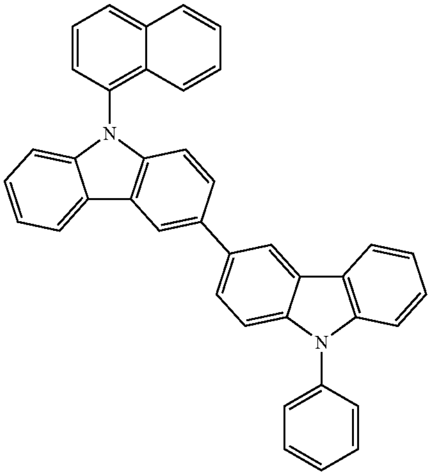
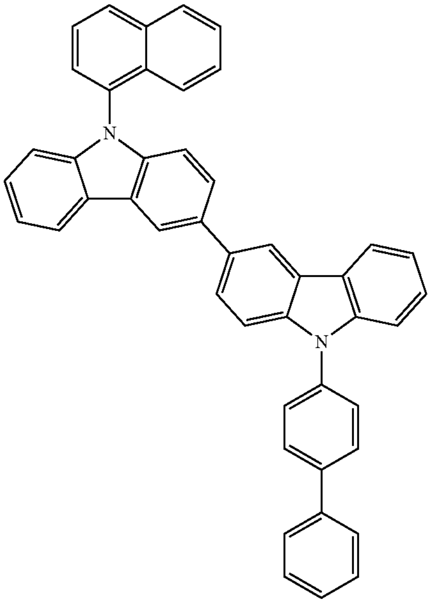

-continued
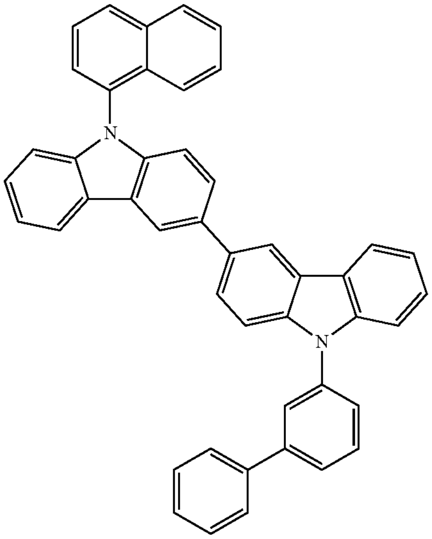
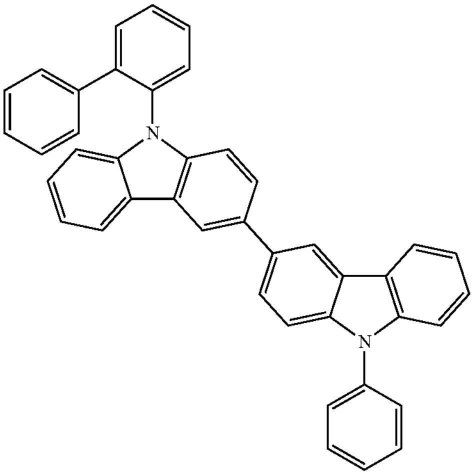
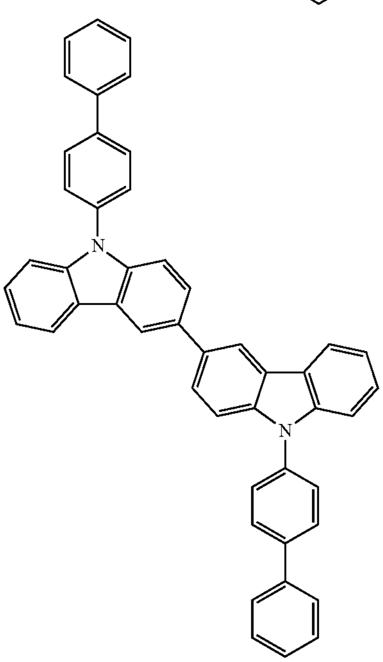
-continued
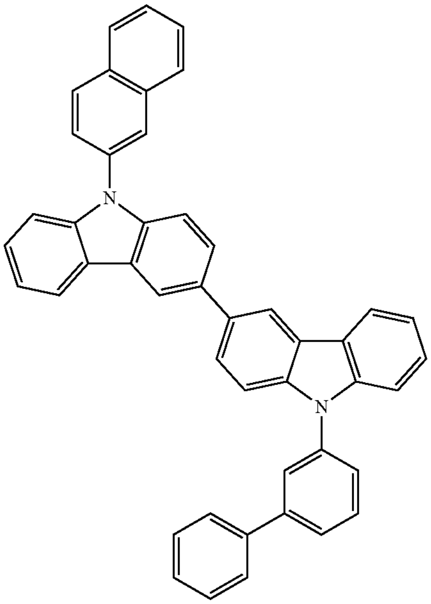
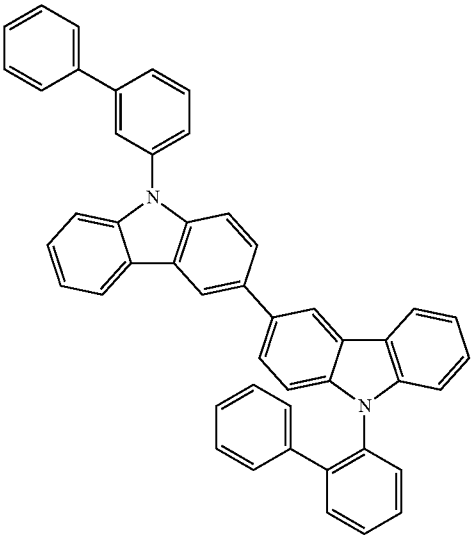
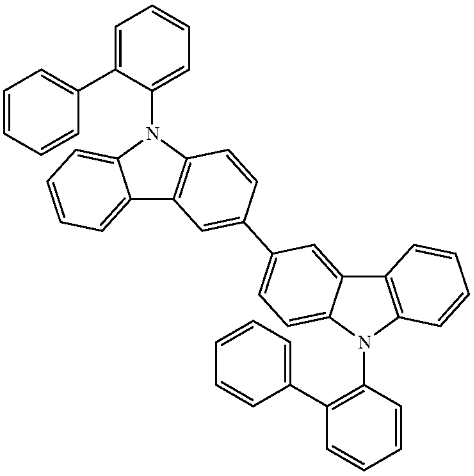

-continued
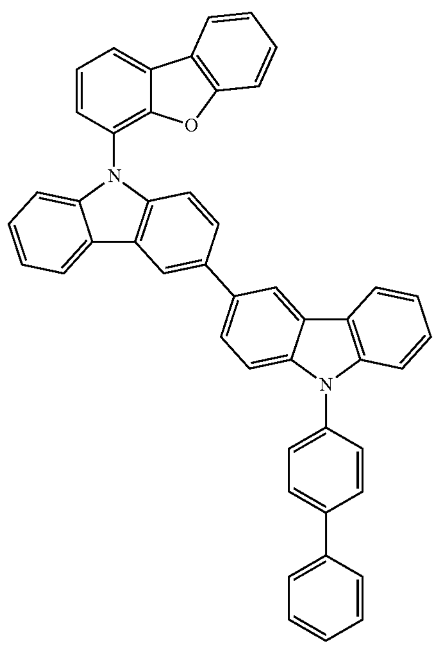
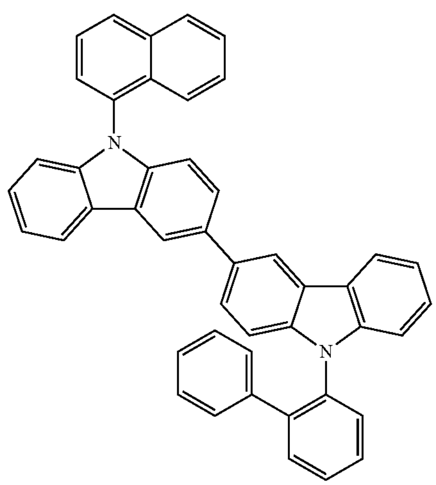
-continued
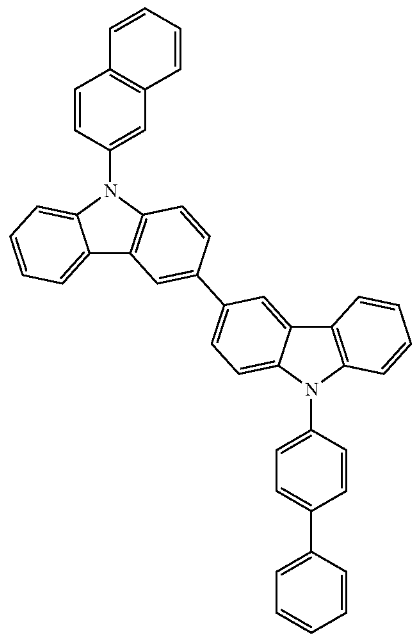
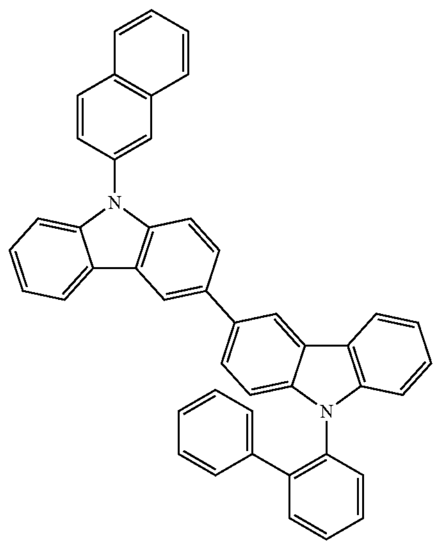
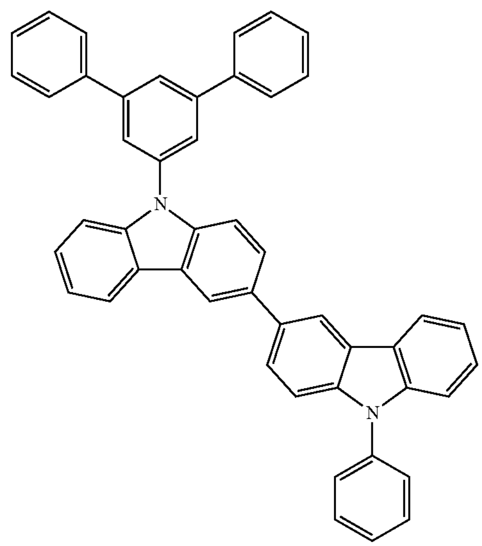

-continued
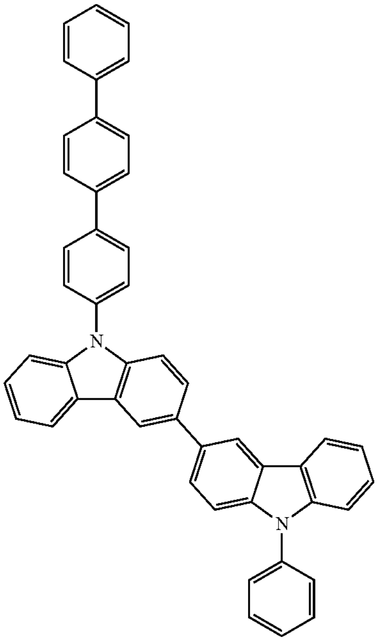
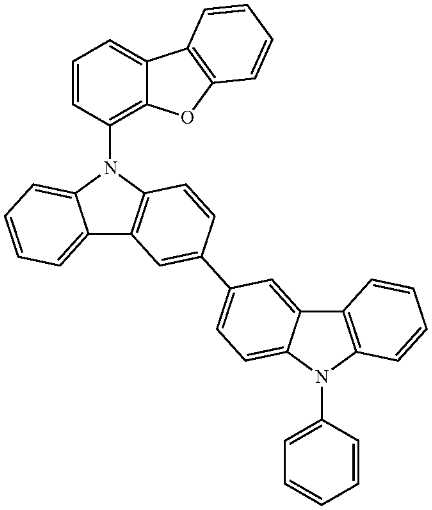
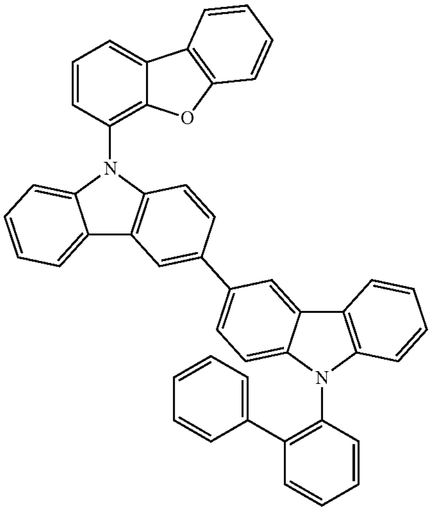
-continued
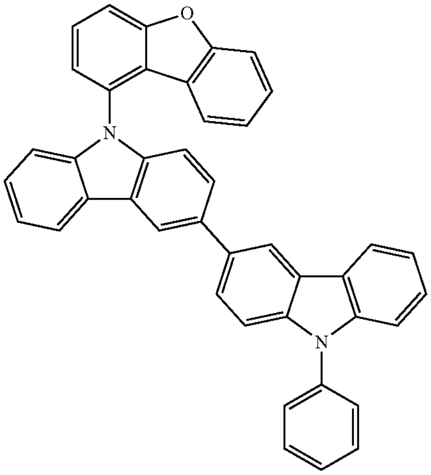
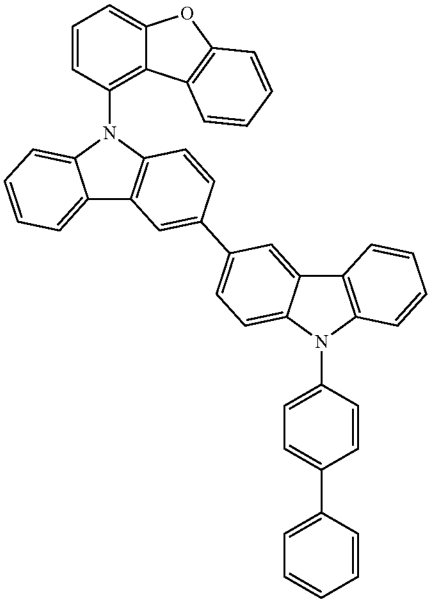
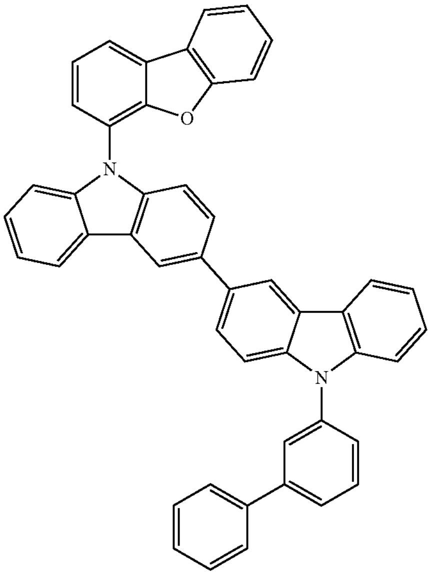

-continued
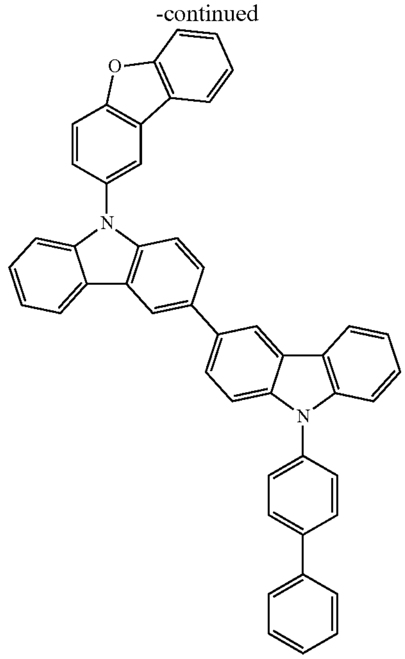
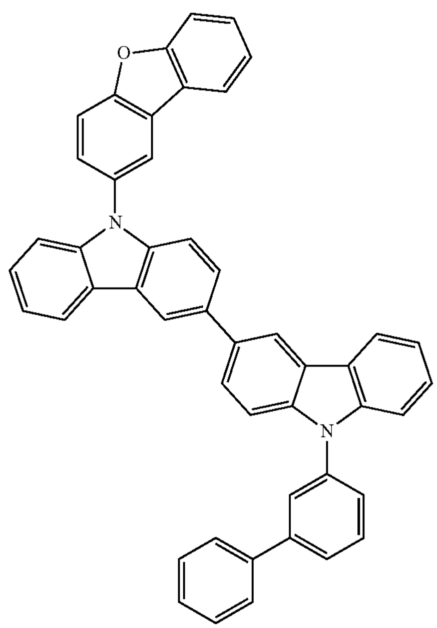
-continued
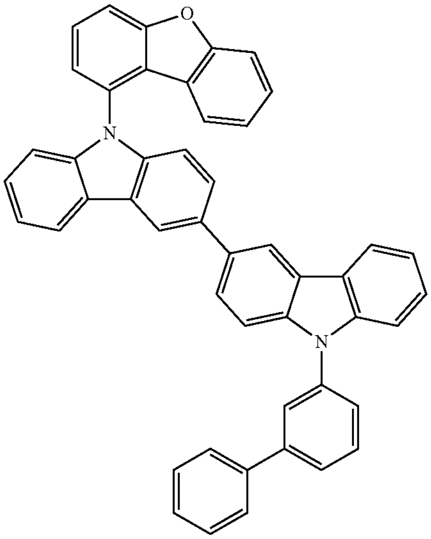
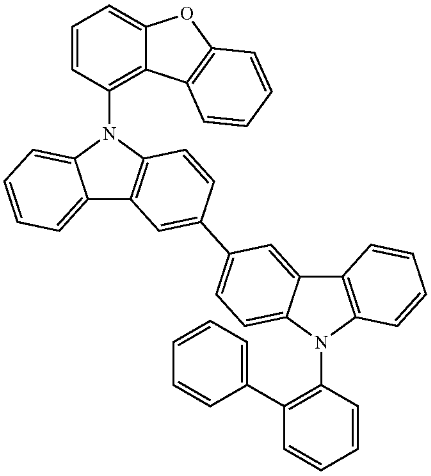
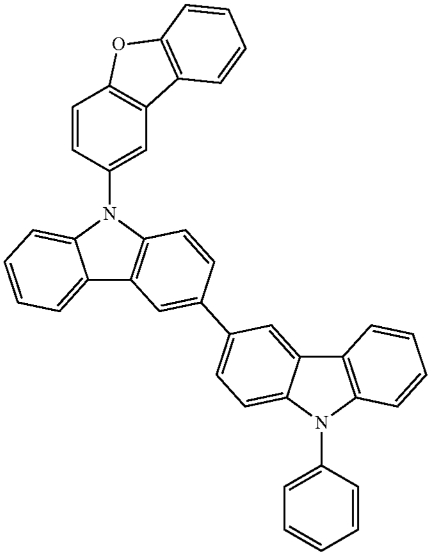

-continued
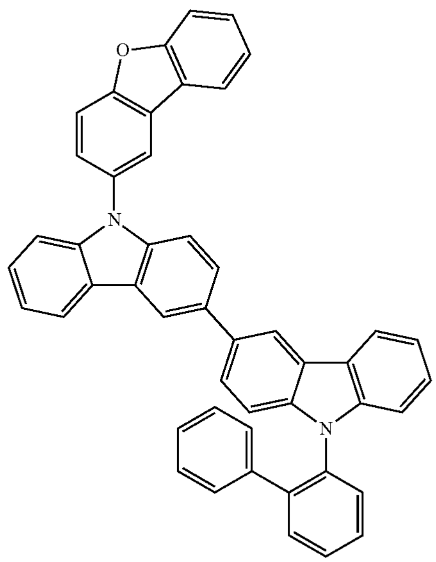
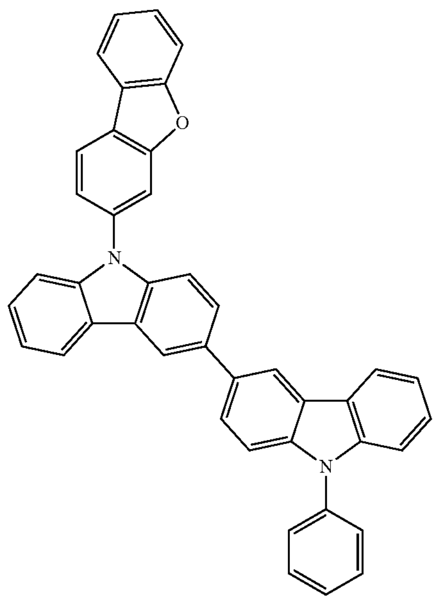
-continued
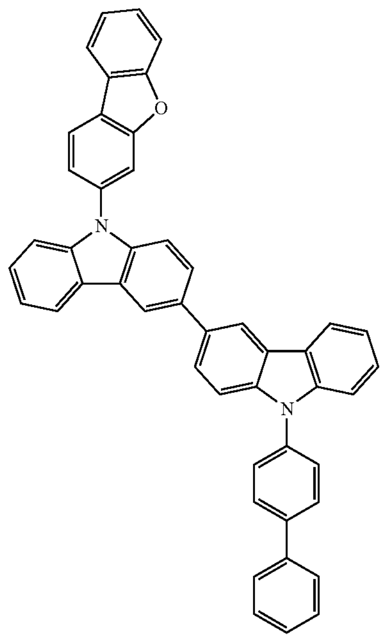
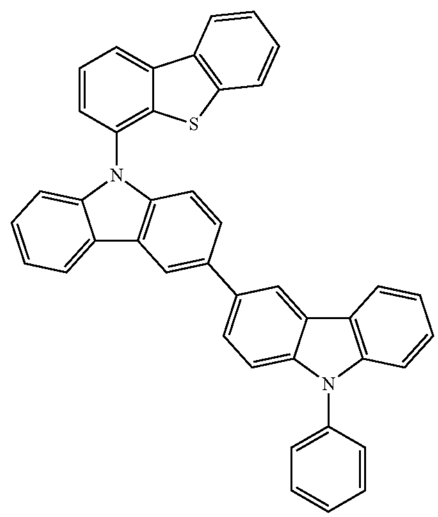

-continued
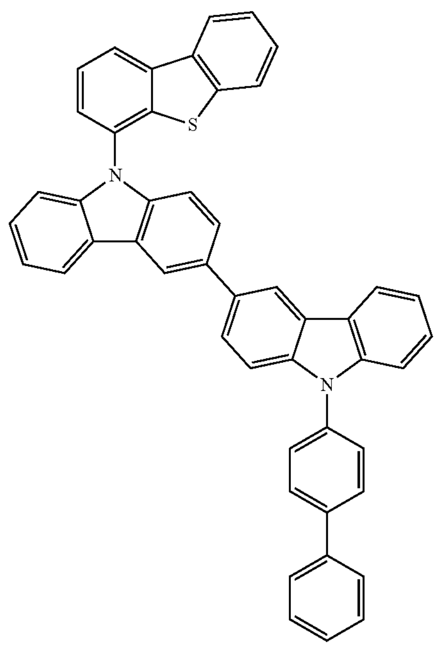
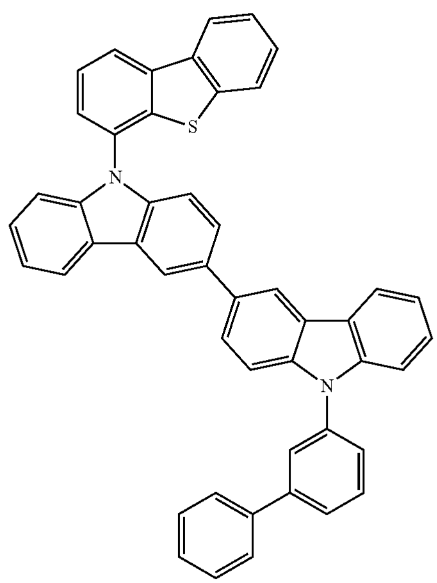
-continued
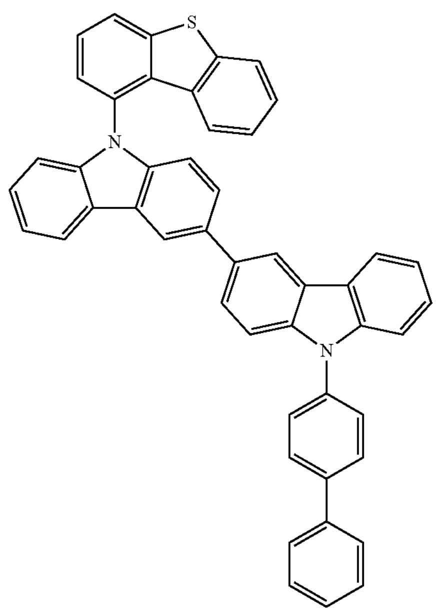
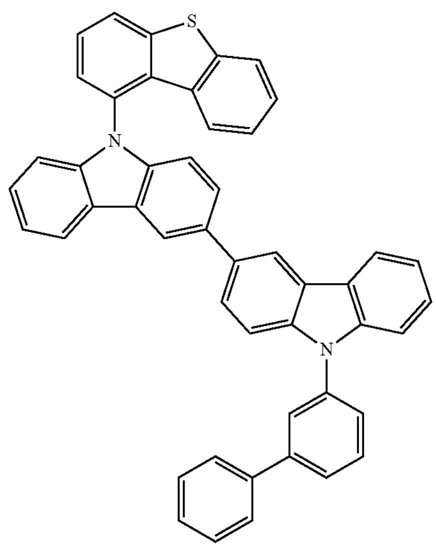
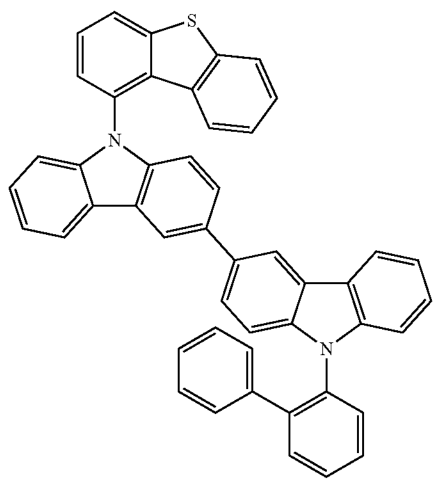

-continued
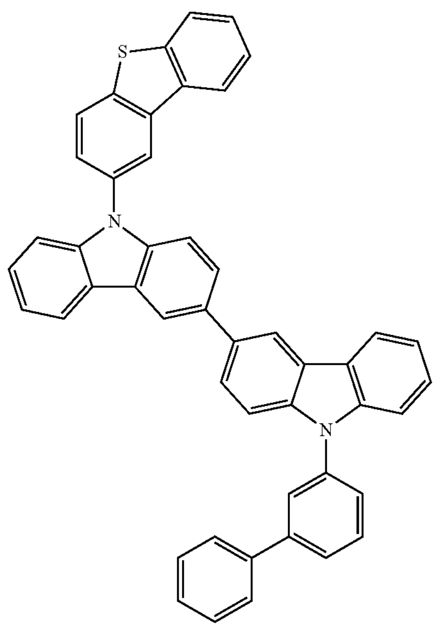
-continued
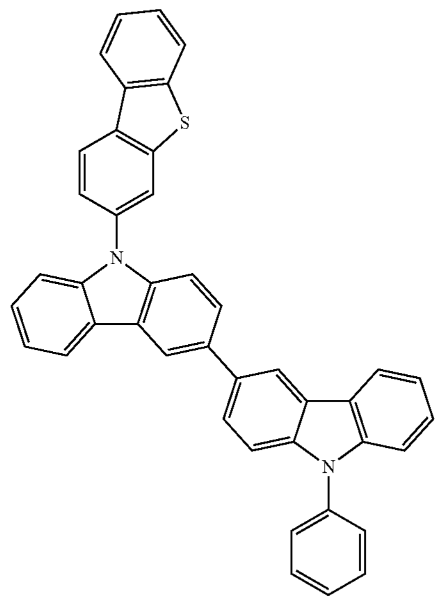
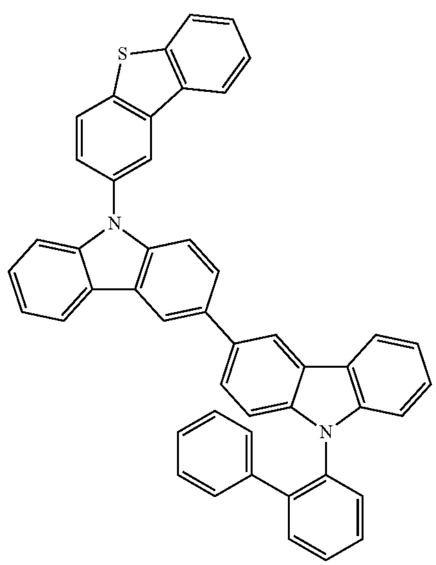
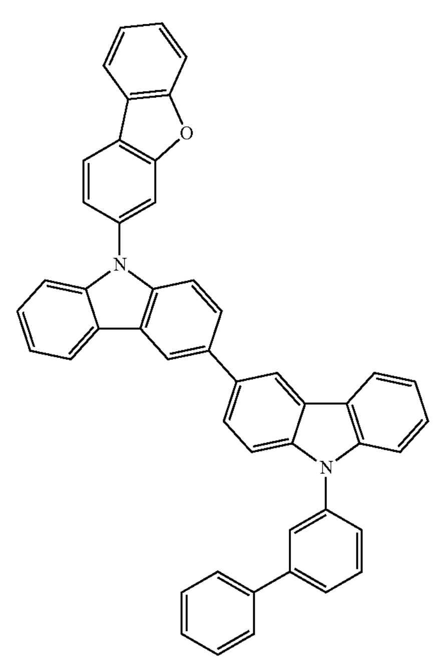

-continued
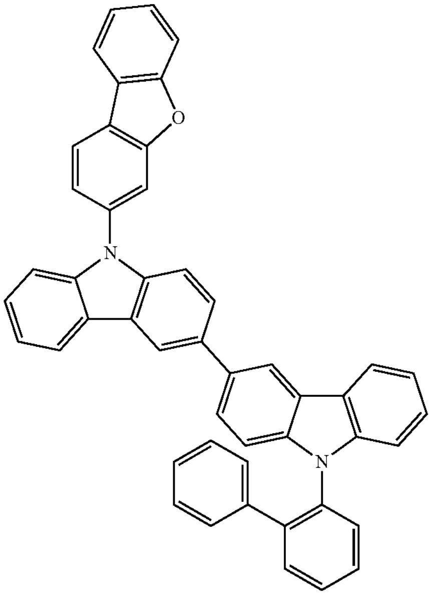
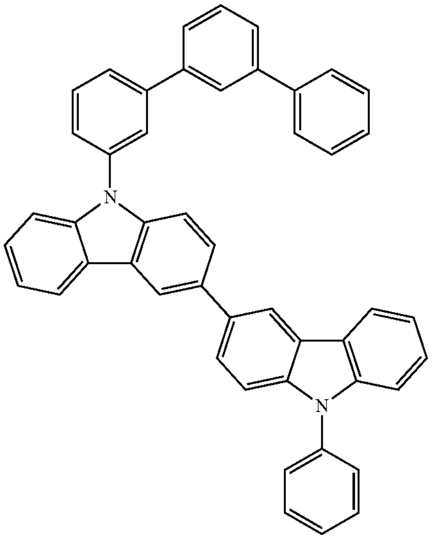
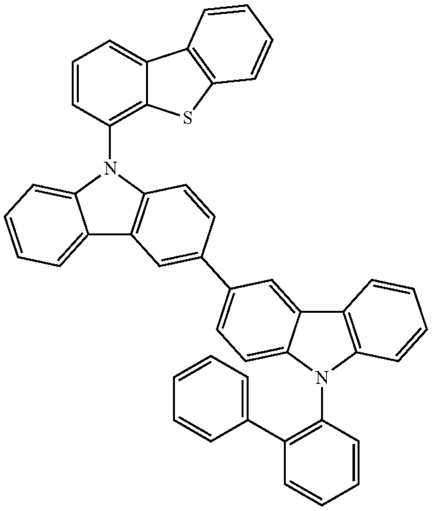
-continued
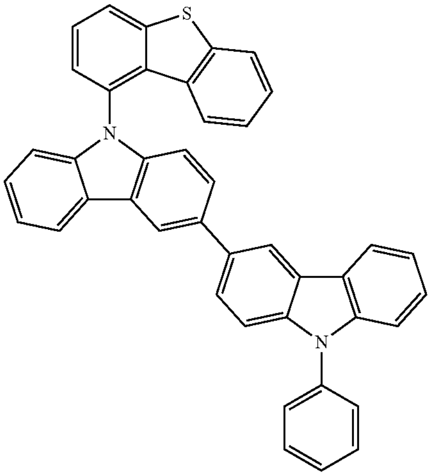
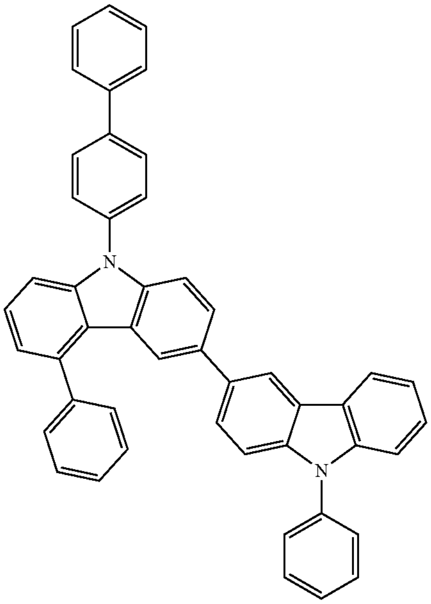
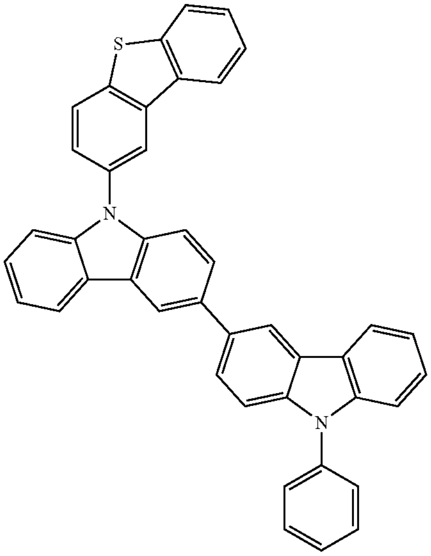

-continued
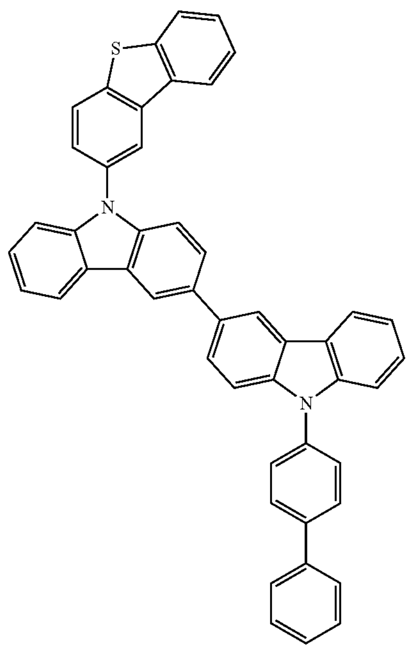
-continued
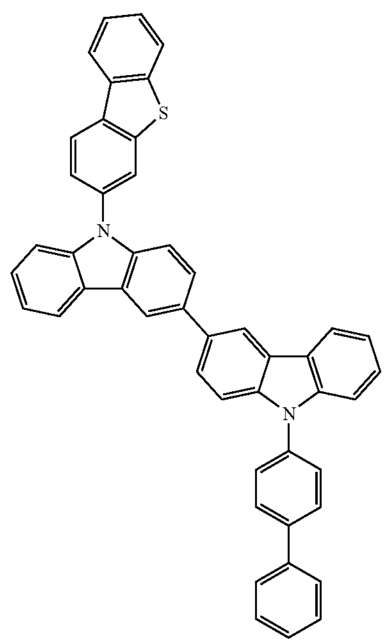
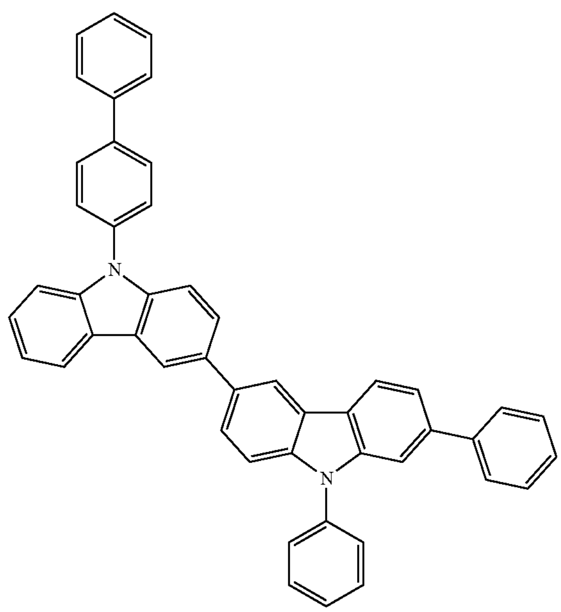
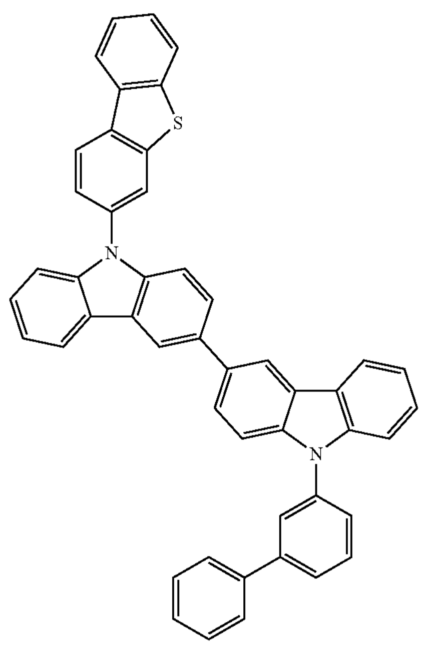

-continued
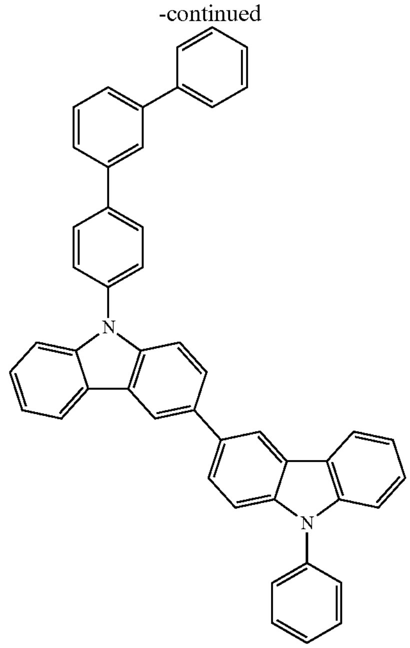
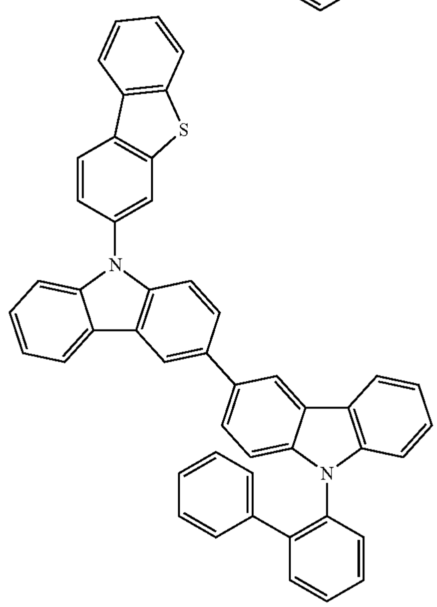
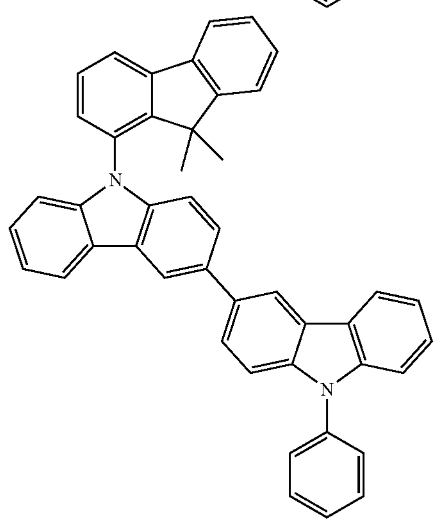
-continued
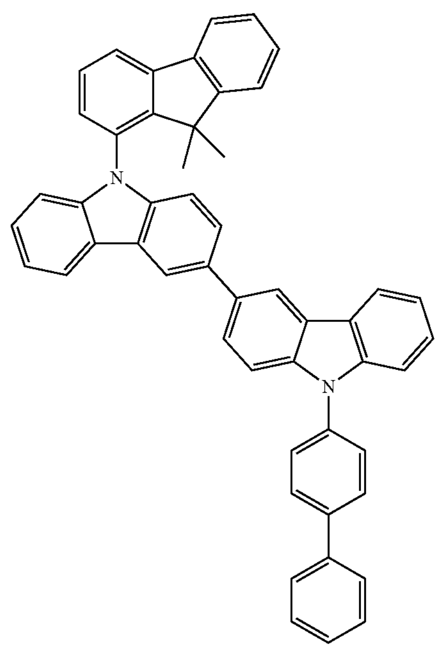
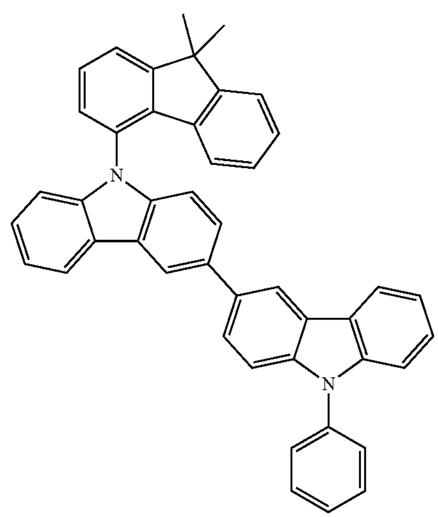

-continued
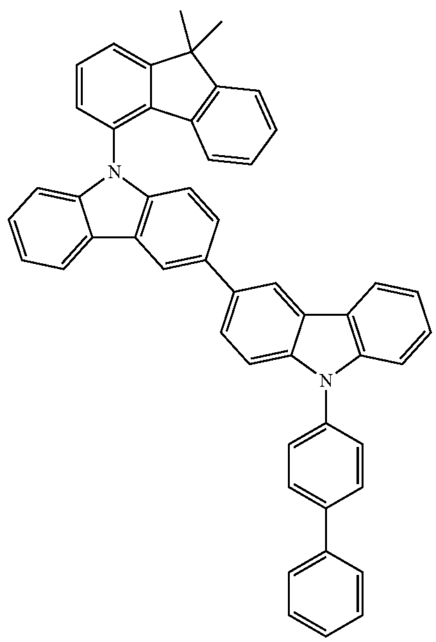
-continued
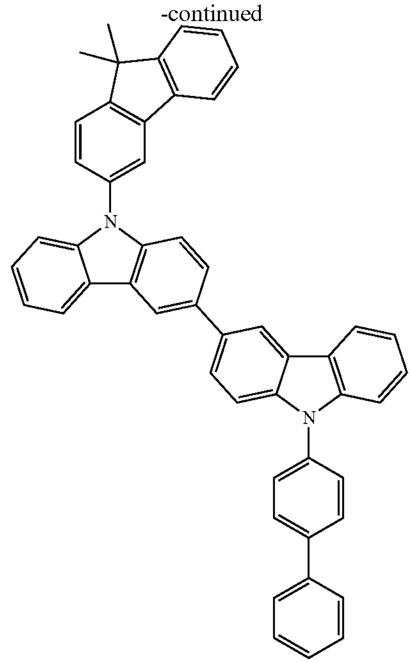
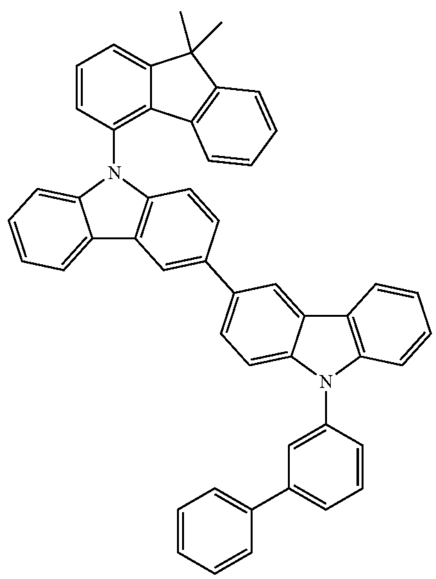
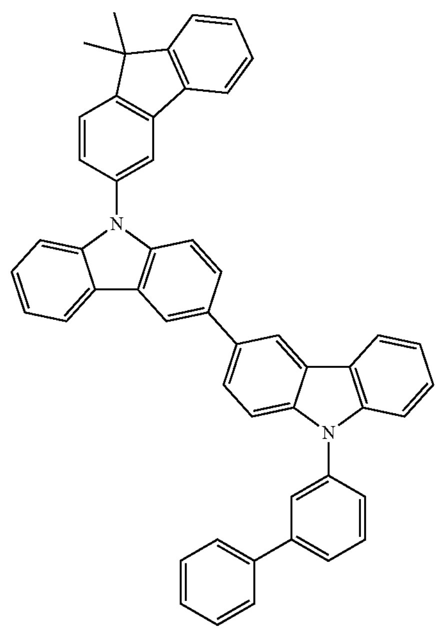

-continued
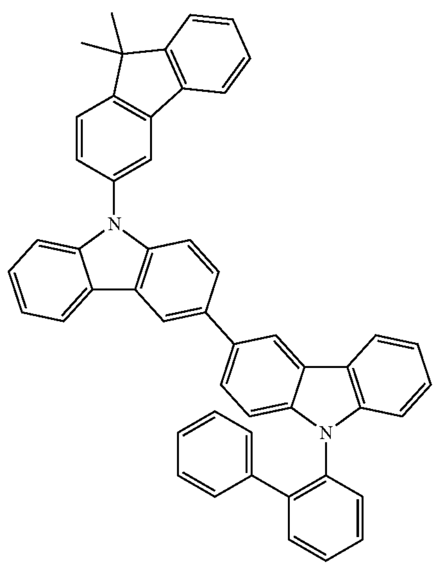
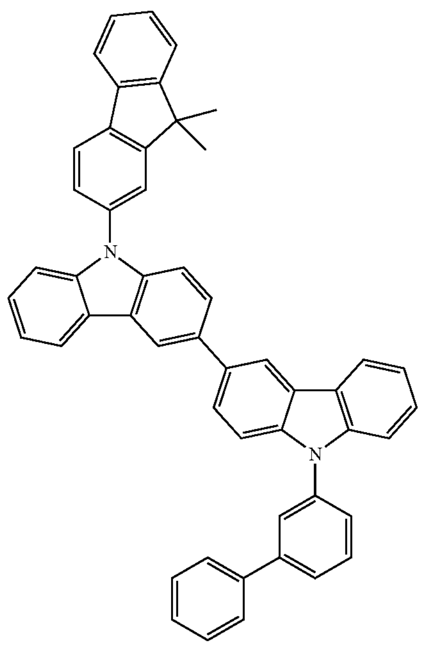
-continued
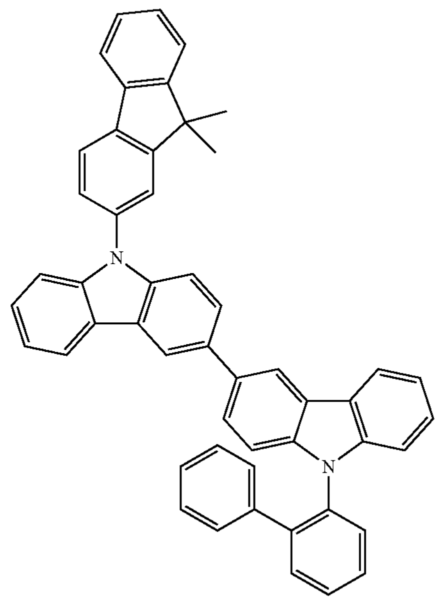
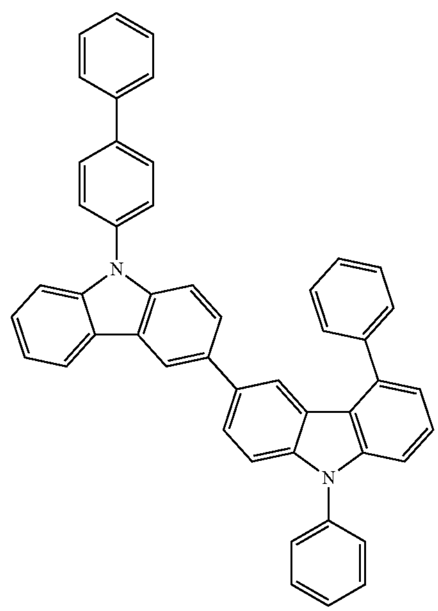

-continued
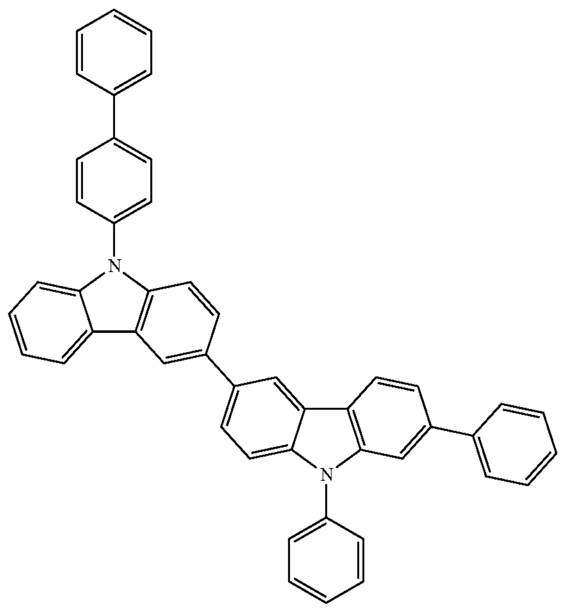
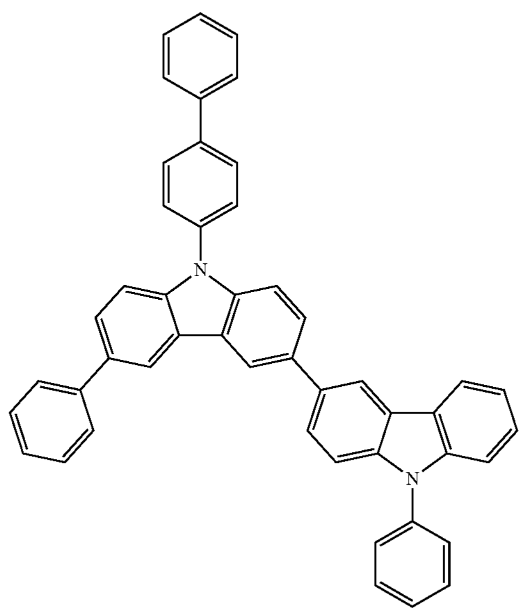
-continued
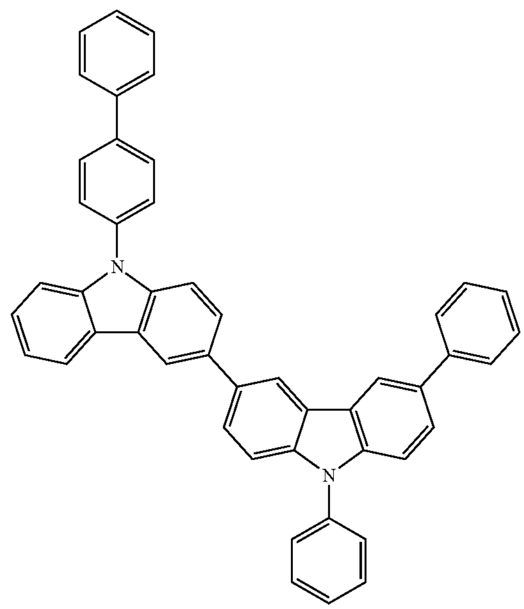
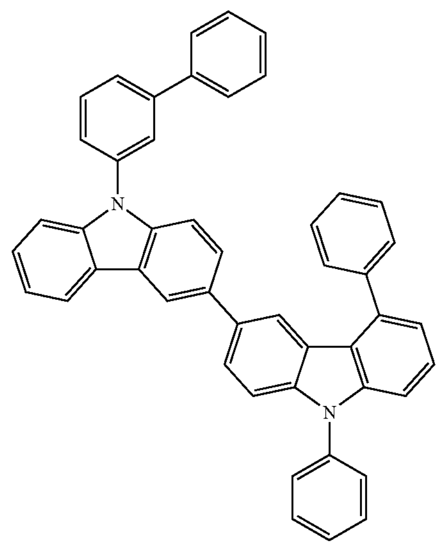
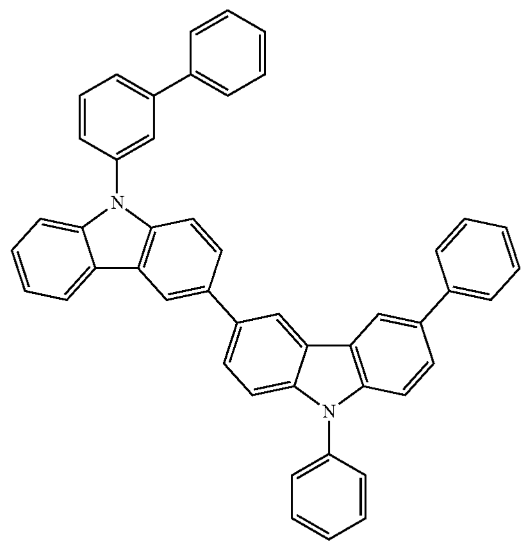

-continued
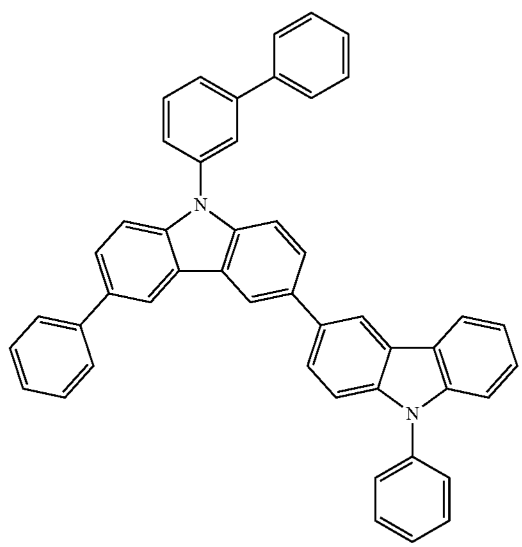
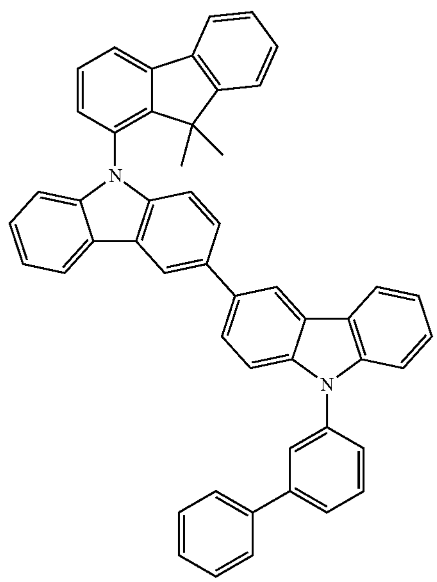
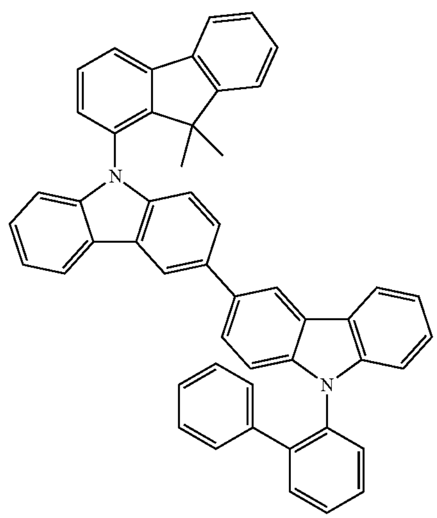
-continued
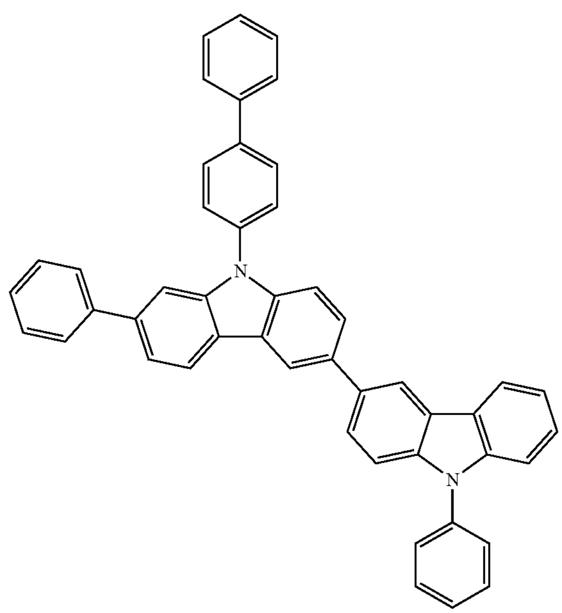
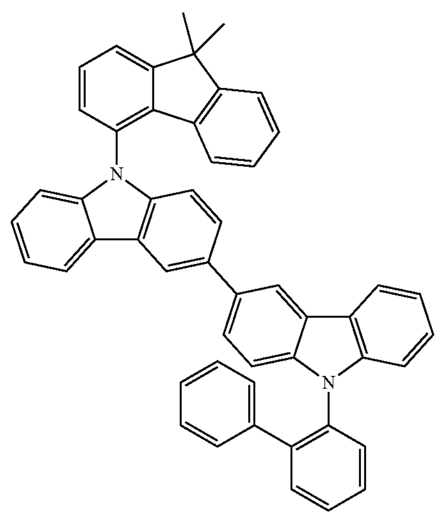
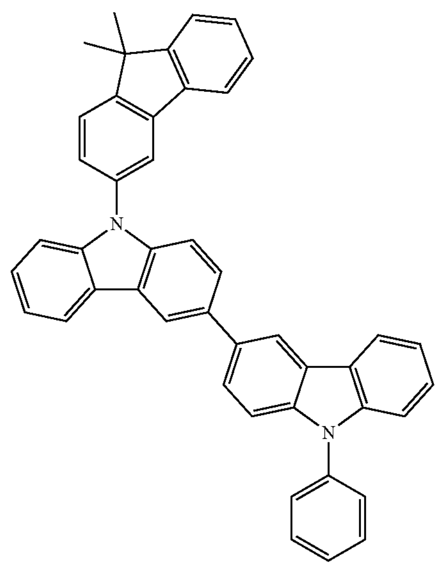

-continued
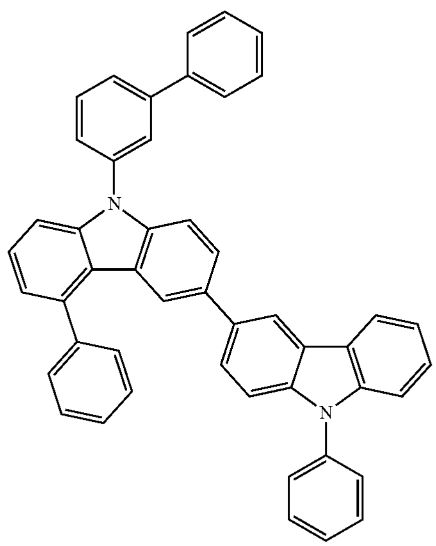
-continued
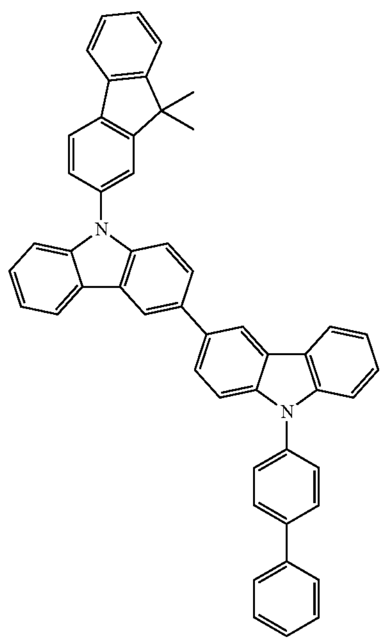
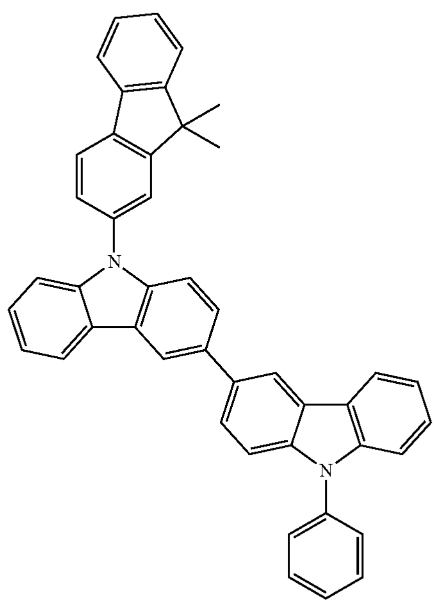
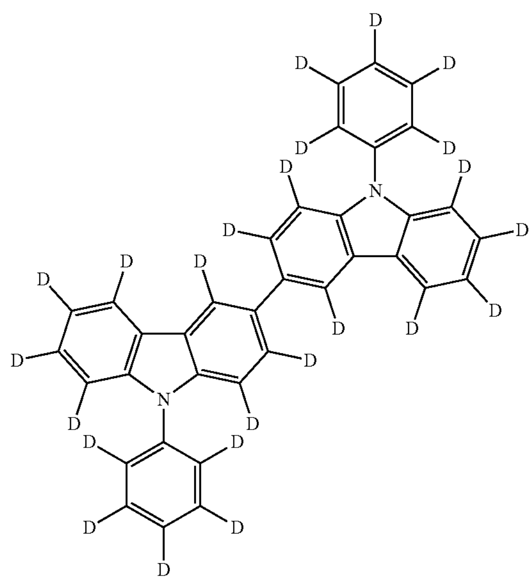

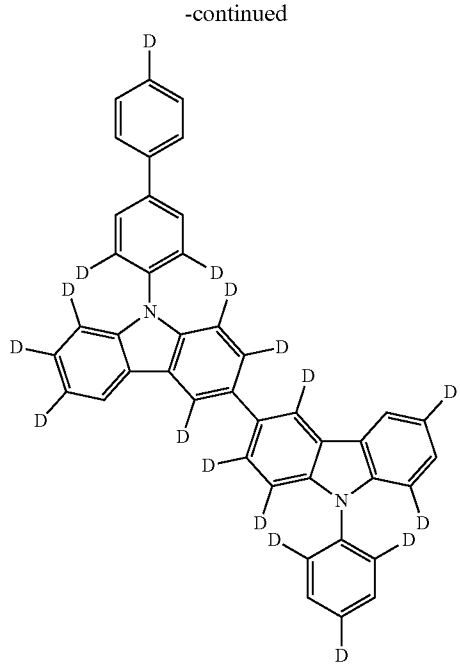
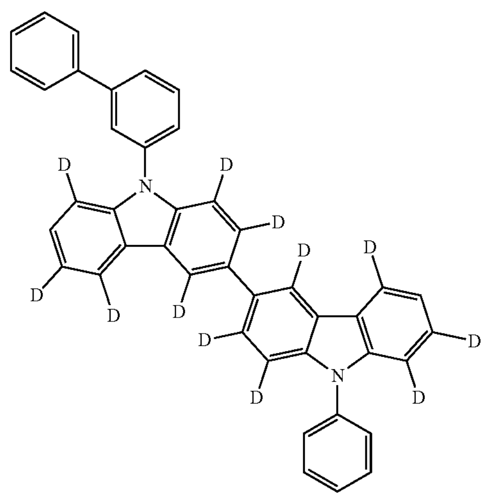
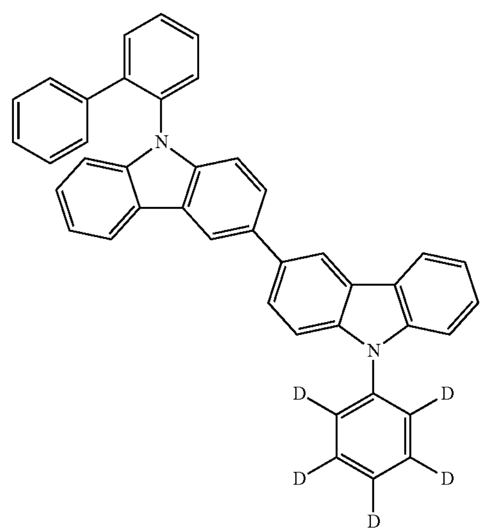
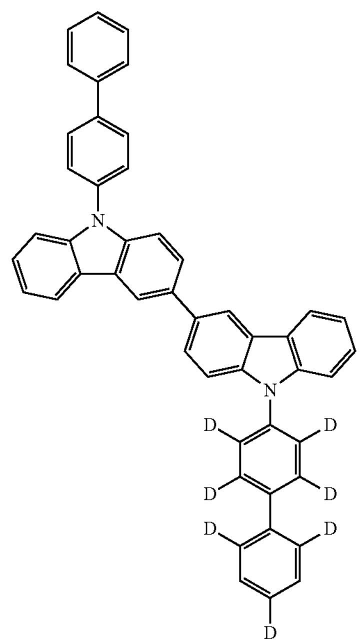
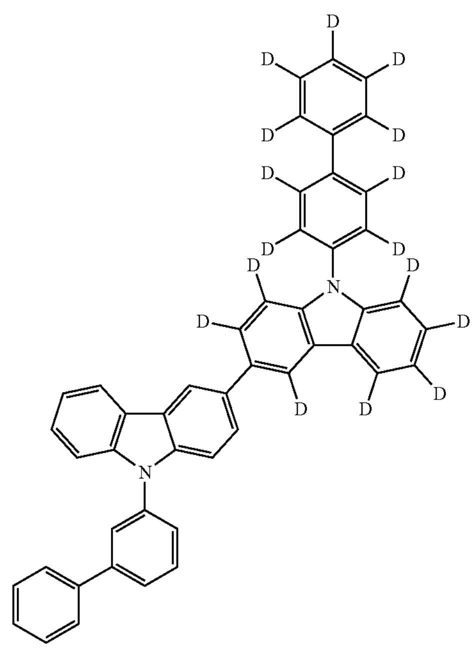

-continued
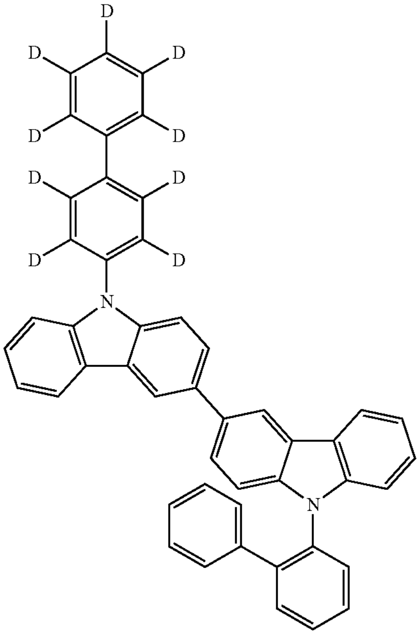
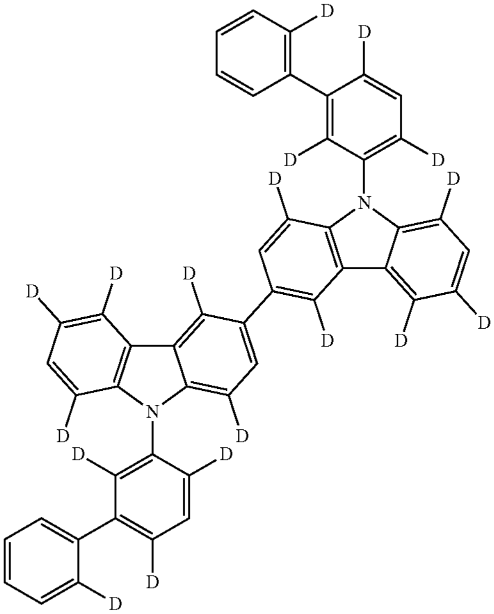
-continued
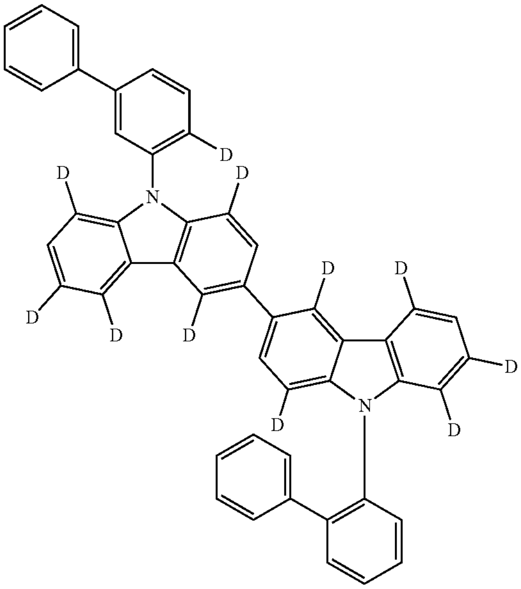
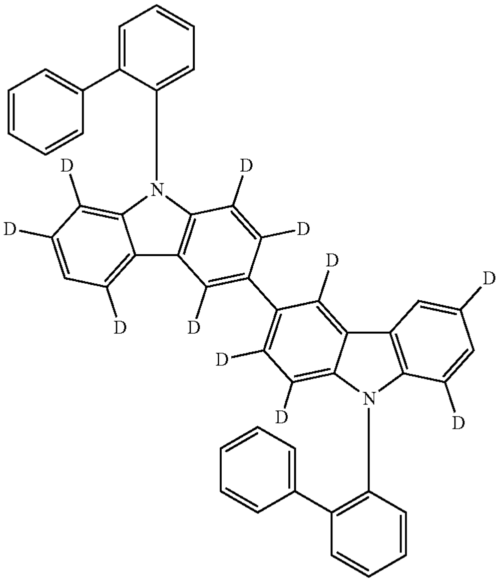

-continued
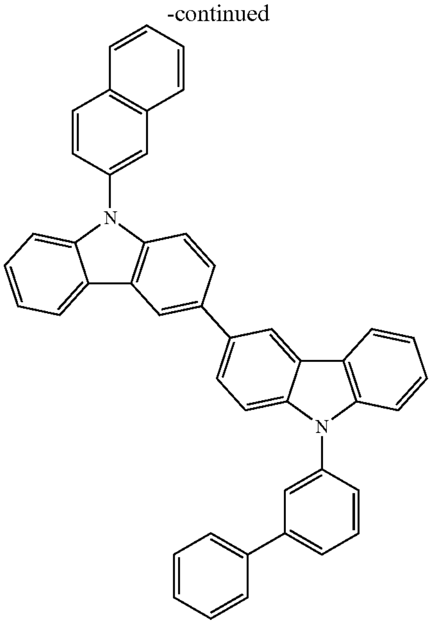
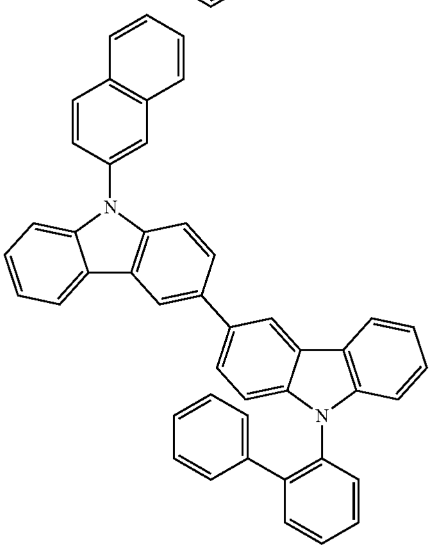
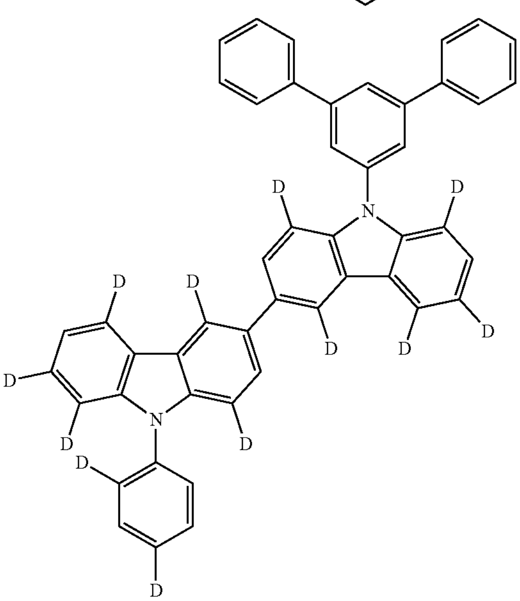
-continued
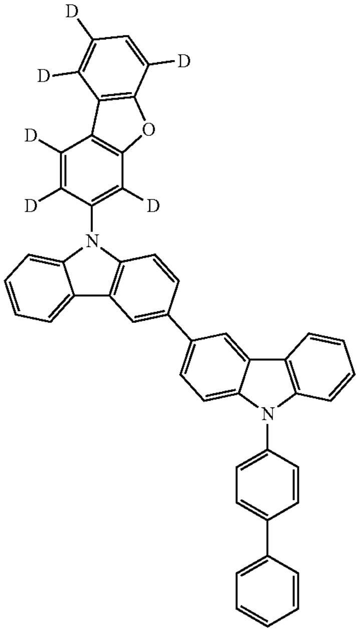
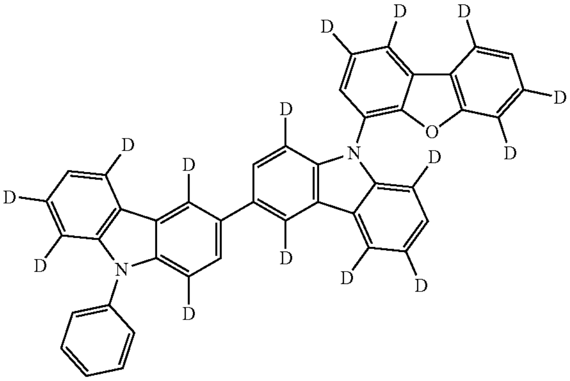
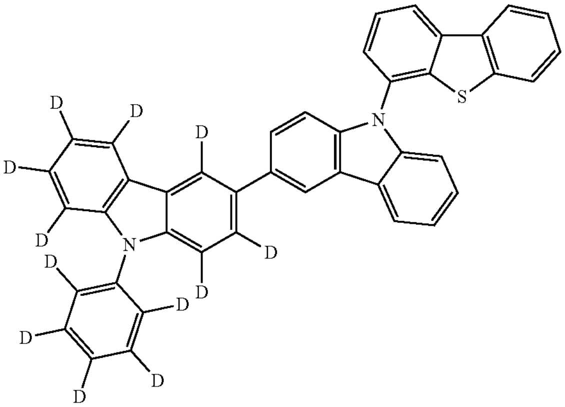

-continued

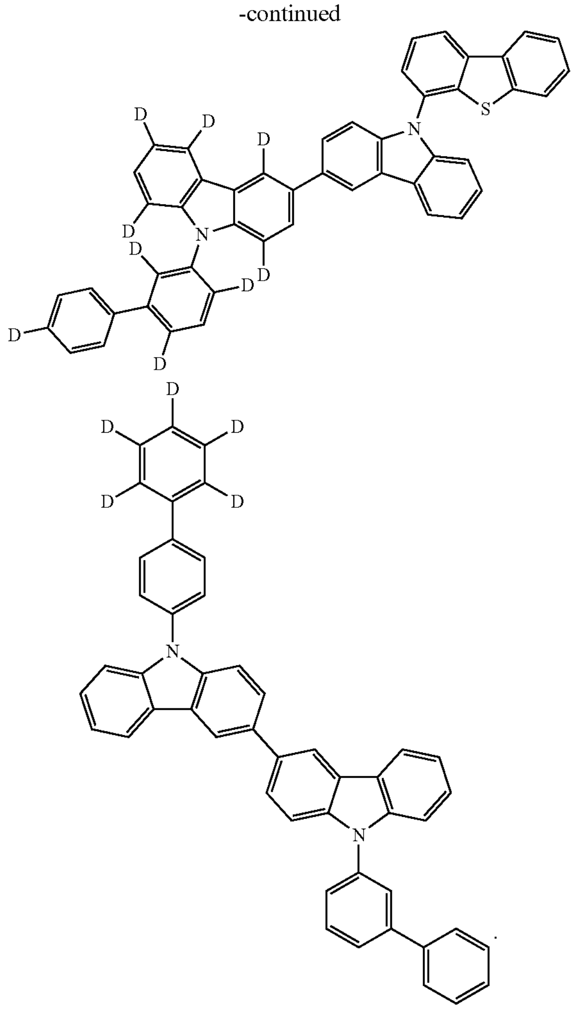

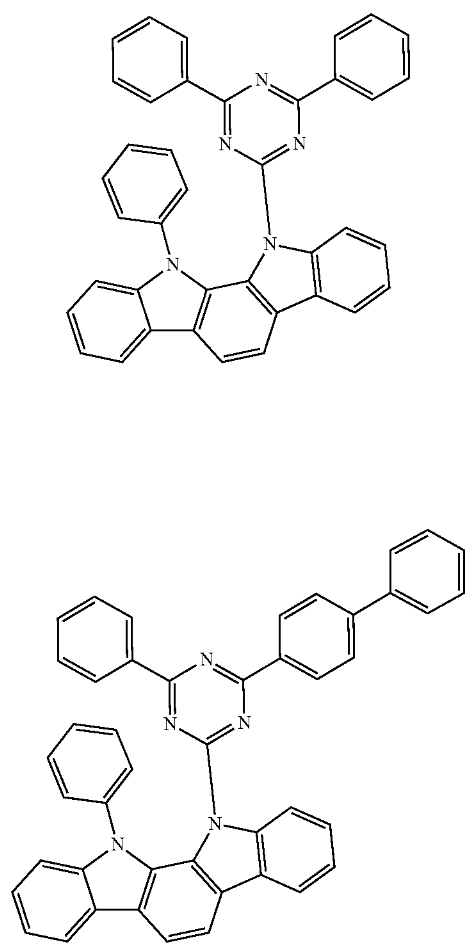

12. The organic light emitting device according to claim 1, wherein:

$Ar_5$ and $Ar_6$ are each independently phenyl, biphenylyl, (phenyl) biphenylyl, triphenylenyl, dimethylfluorenyl, dibenzofuranyl, dibenzothiophenyl, carbazol-9-yl, or 9-phenyl-9H-carbazolyl; and the $Ar_5$ and $Ar_6$ are each independently unsubstituted or substituted with at least one deuterium.

13. The organic light emitting device according to claim 1, wherein:

$Y_2$ is $C(CH_3)_2$, $C(C_6C_5)_2$, O, S, or $NAr_7$, wherein $Ar_7$ is phenyl, biphenylyl, terphenylyl, dibenzofuranyl, or dibenzothiophenyl, with the $Ar_7$ being unsubstituted or substituted with at least one deuterium.

14. The organic light emitting device according to claim 1, wherein:

$R_4$ is hydrogen or deuterium.

15. The organic light emitting device according to claim 1, wherein:

the compound of Chemical Formula 3 is any one compound selected from the group consisting of the following compounds:

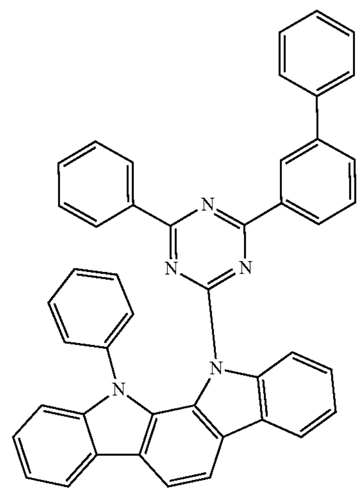

-continued
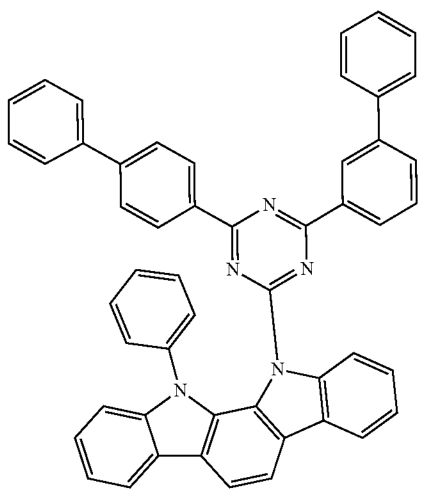
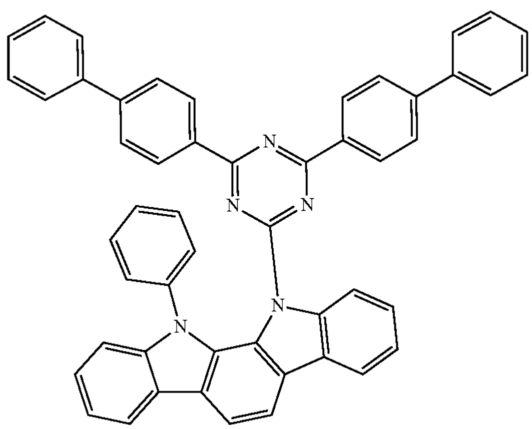
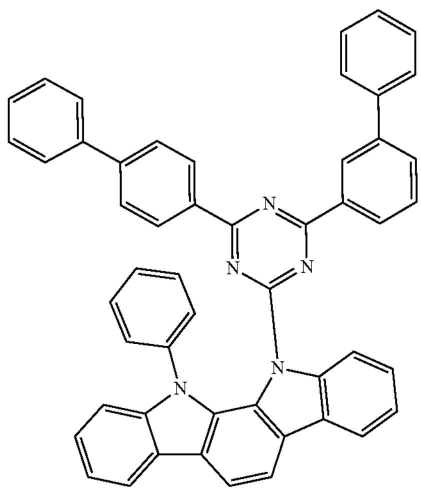
-continued
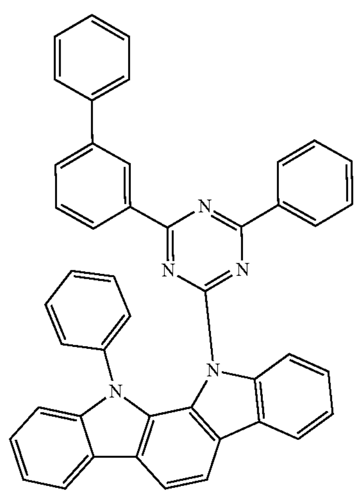
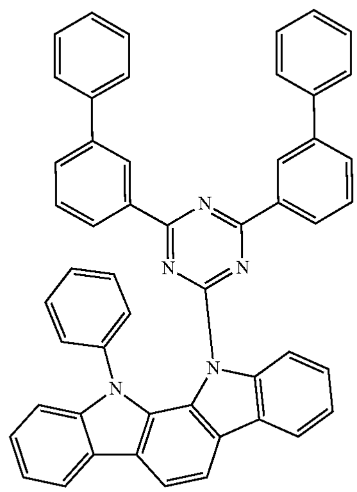
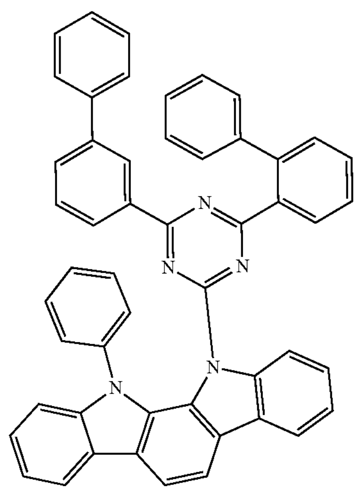

-continued
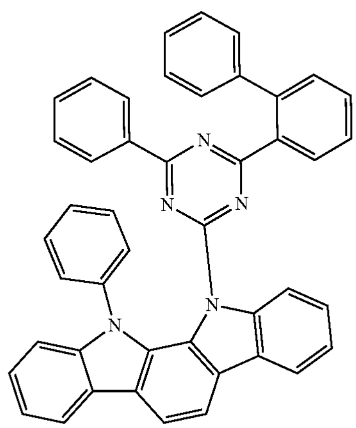
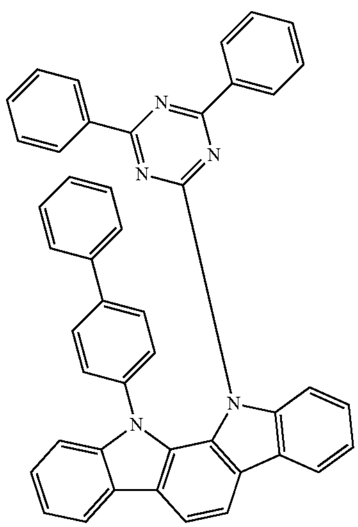
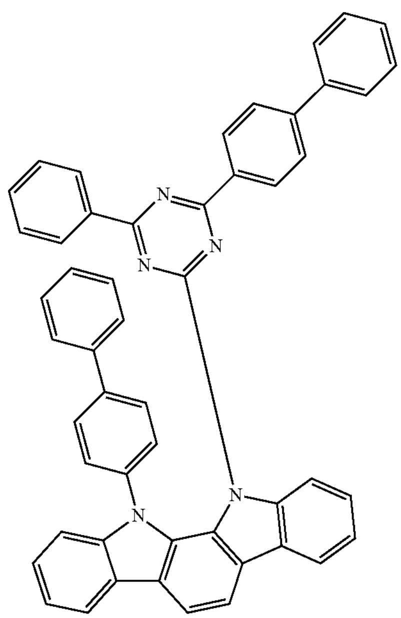
-continued
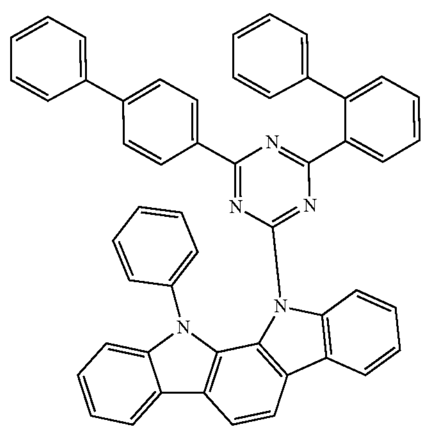
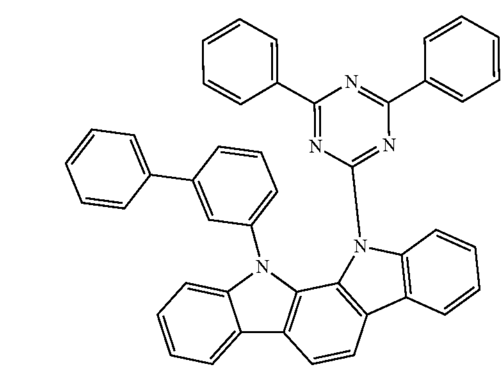
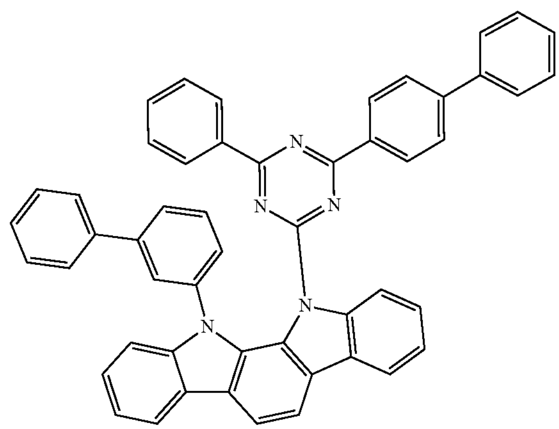
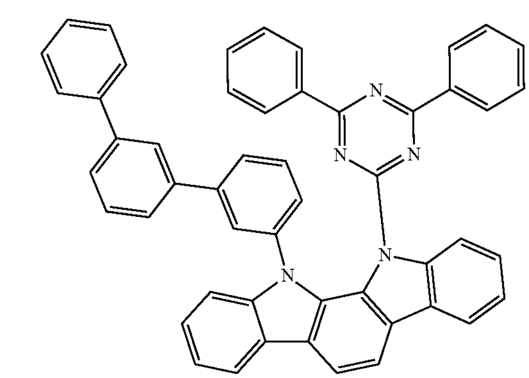

-continued
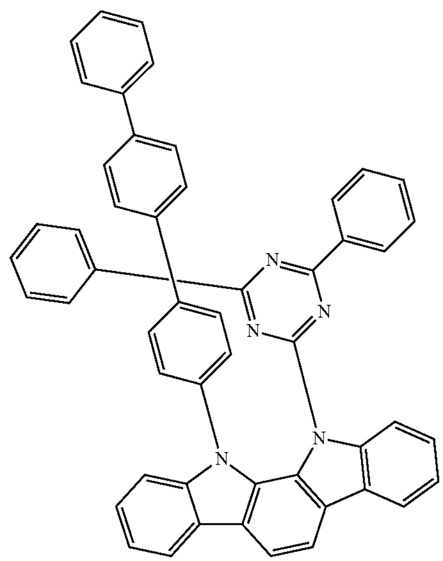
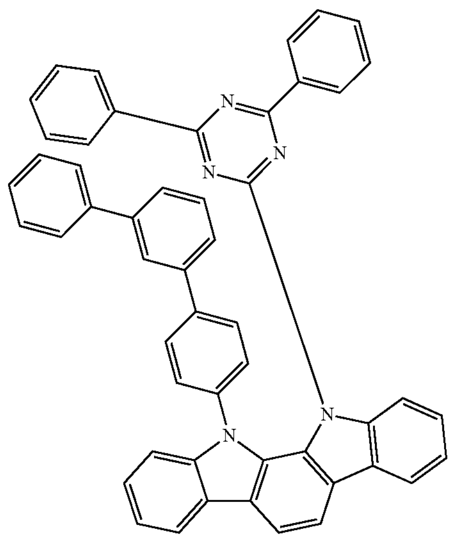
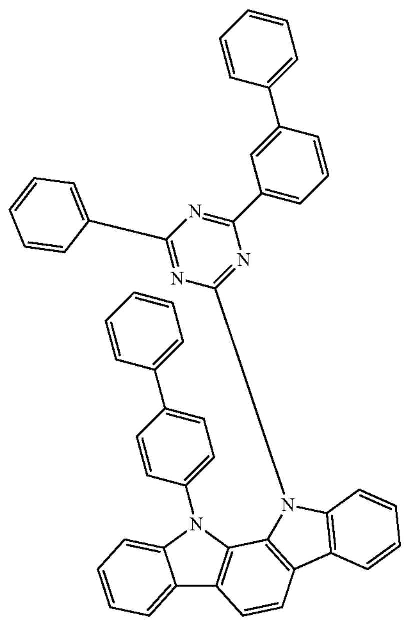
-continued
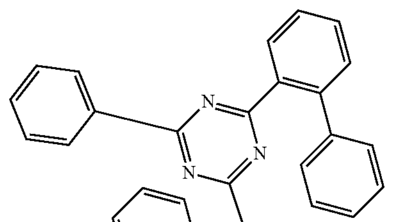
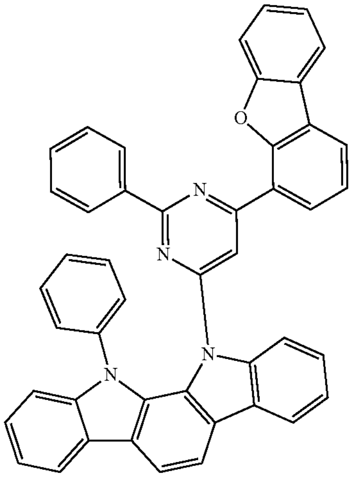
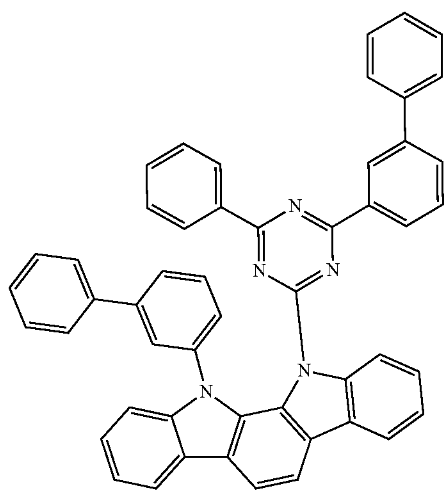

-continued
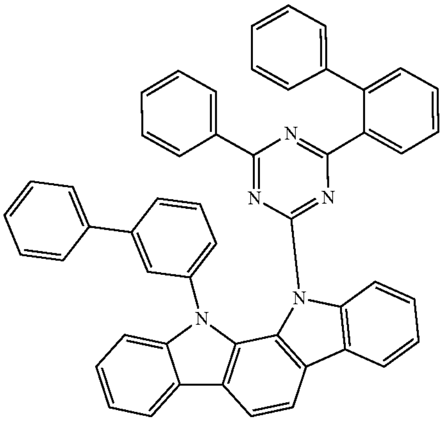
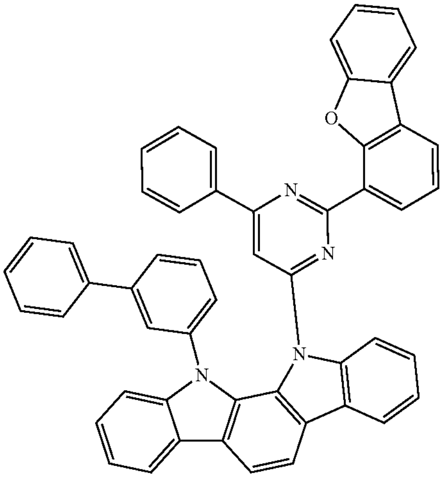
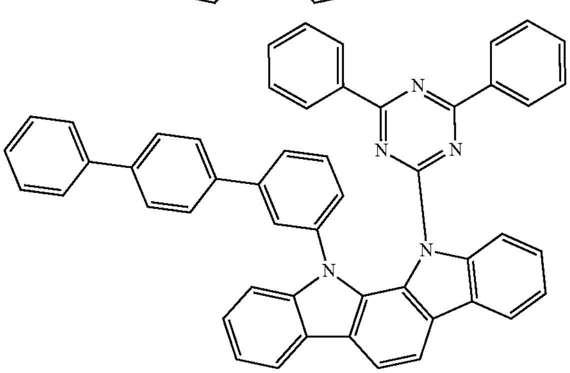
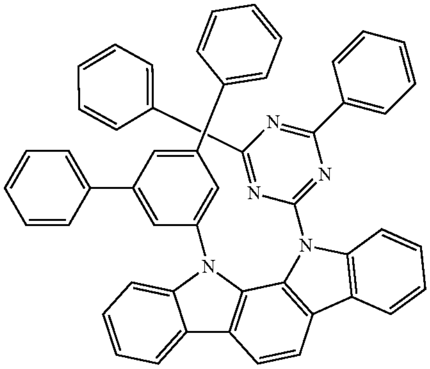
-continued
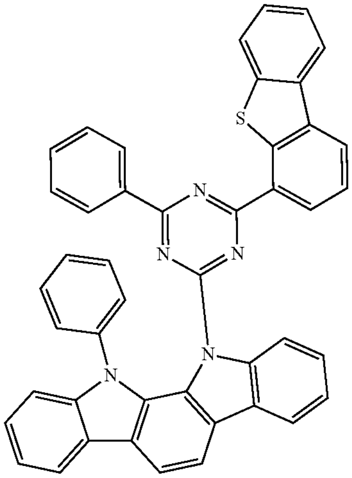
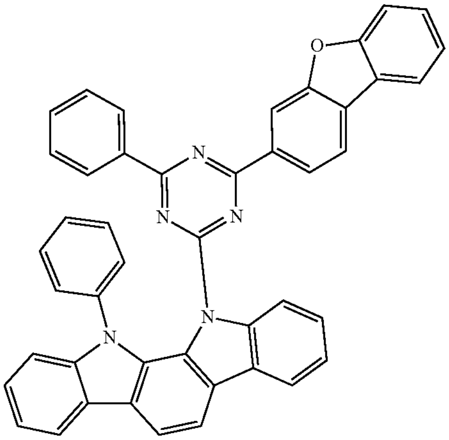
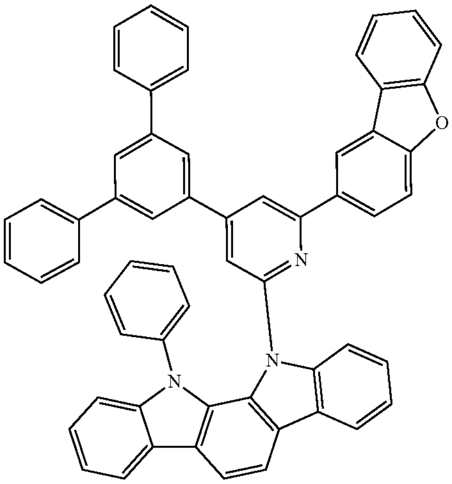

-continued
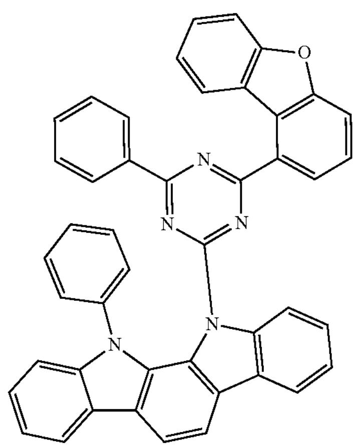
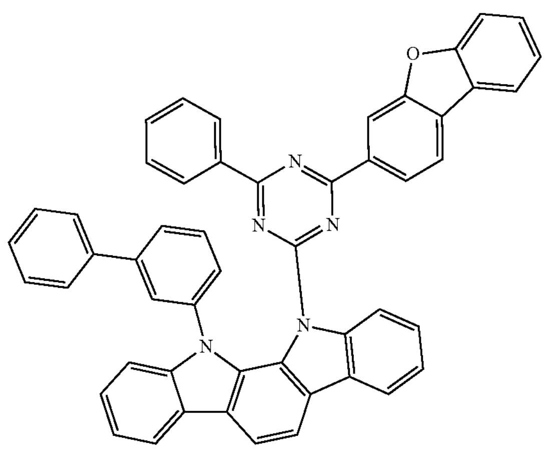
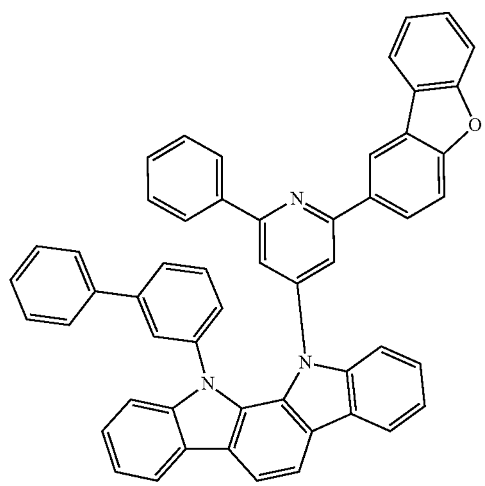
-continued
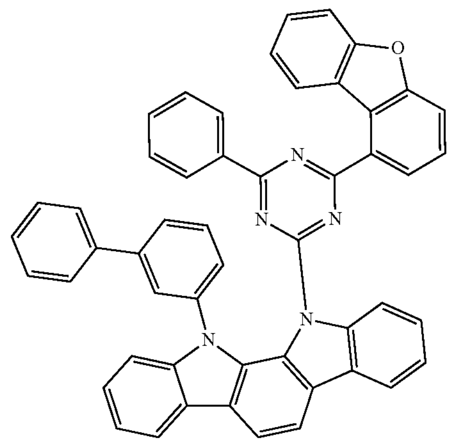
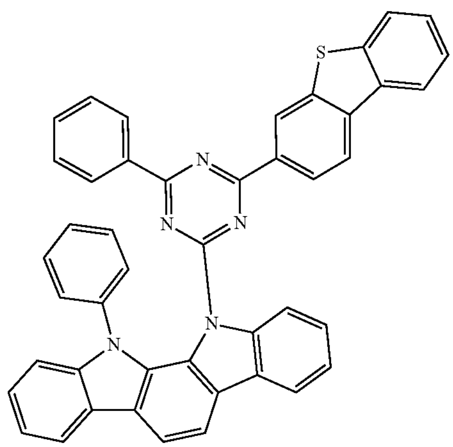
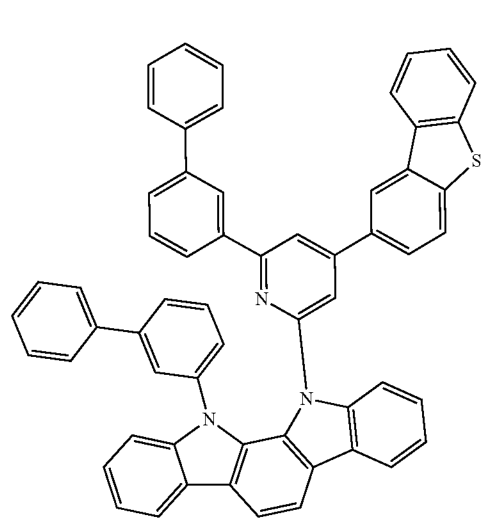

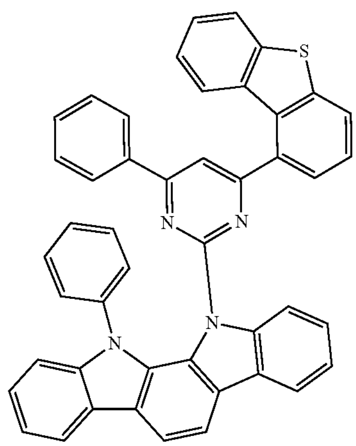
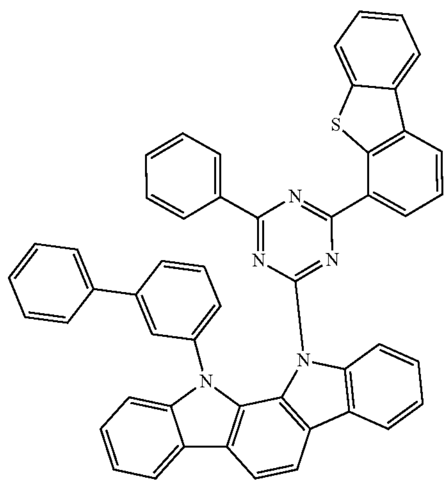
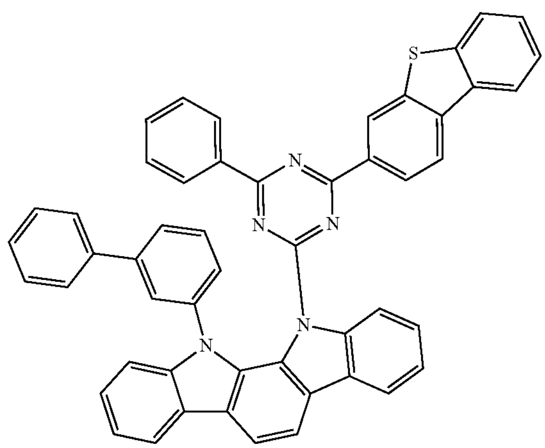
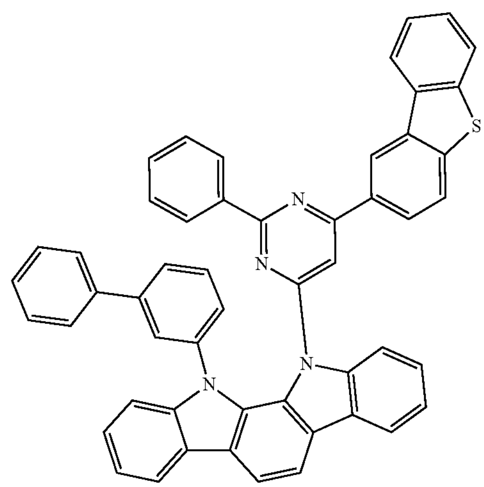
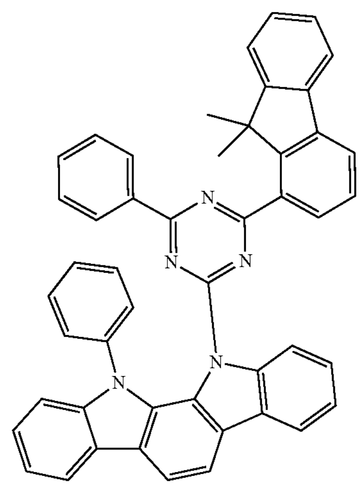
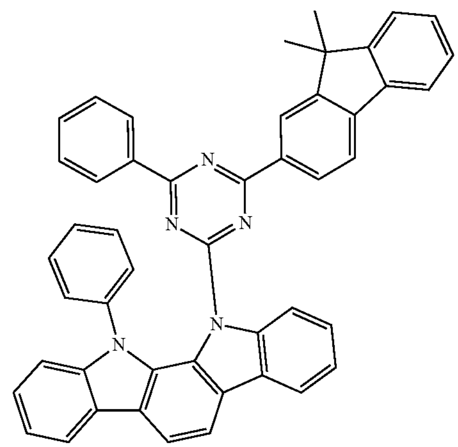

-continued
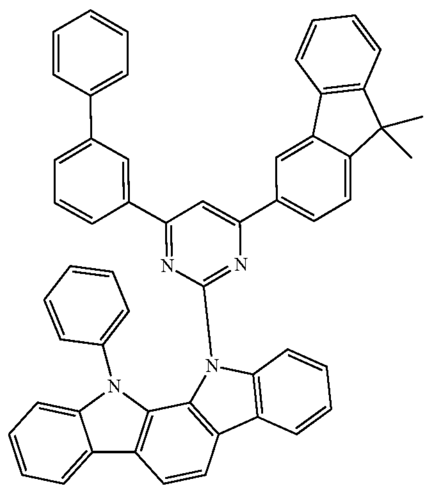
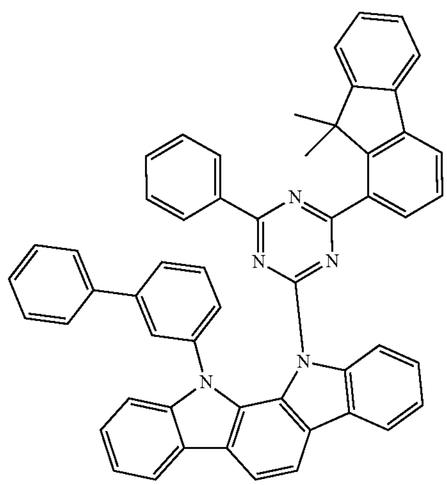
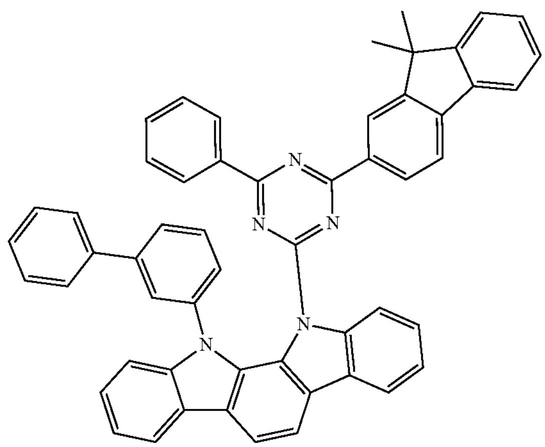
-continued
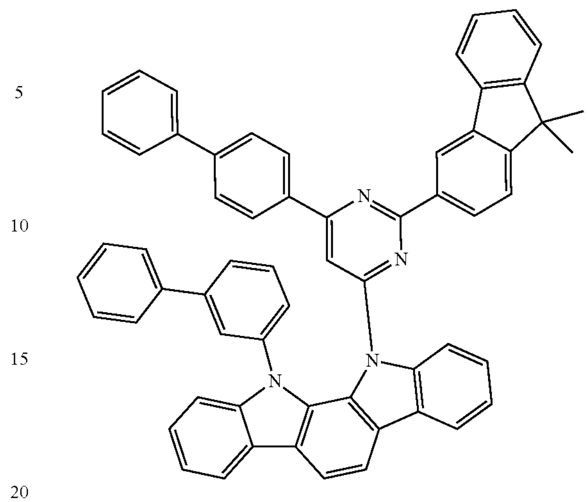
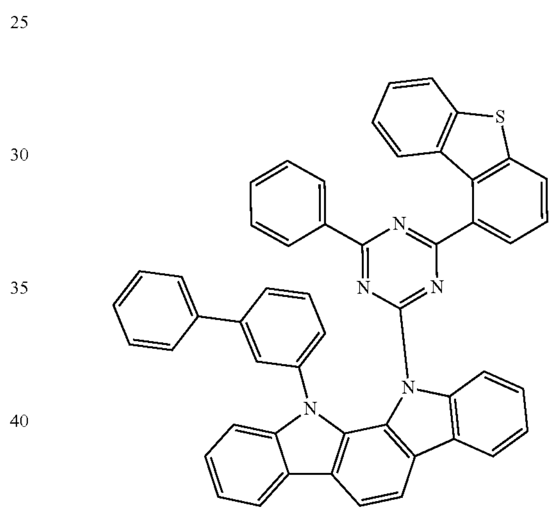
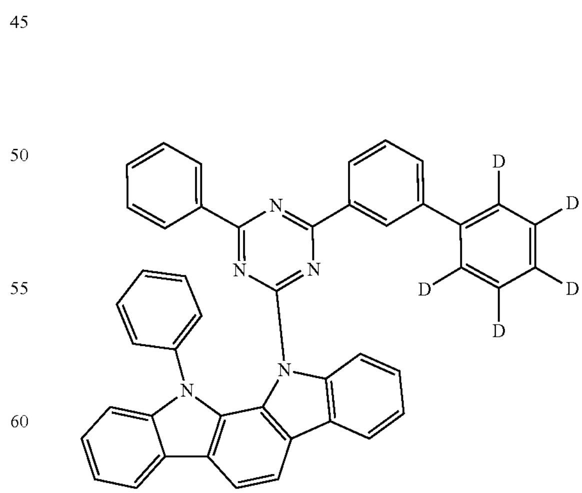

-continued
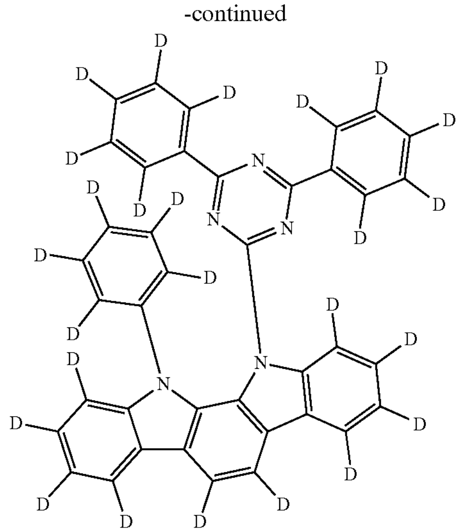
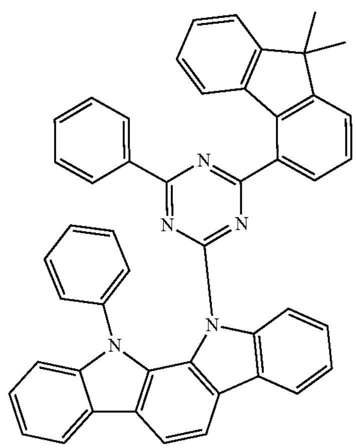
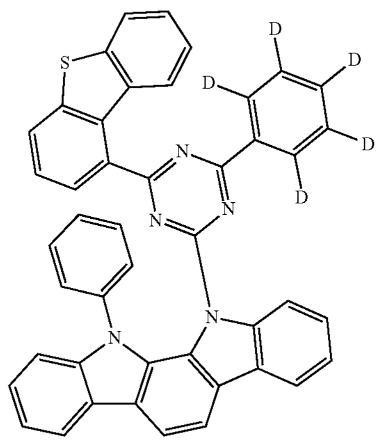
-continued
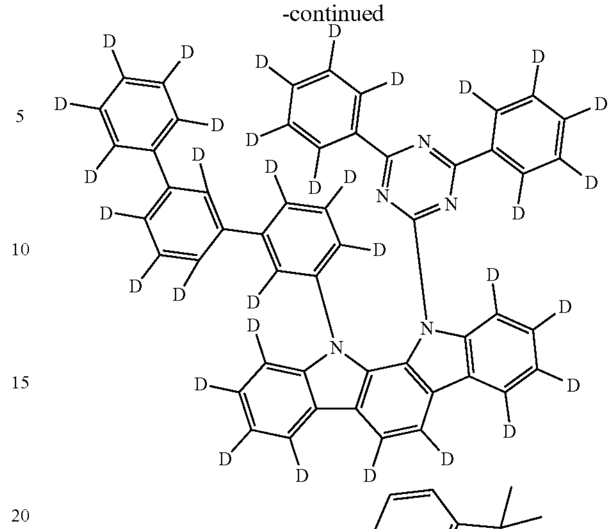
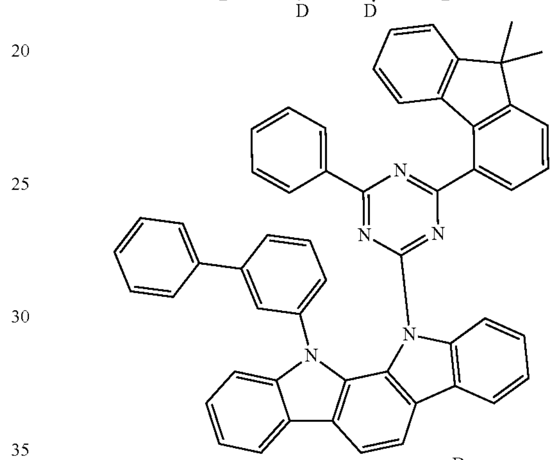
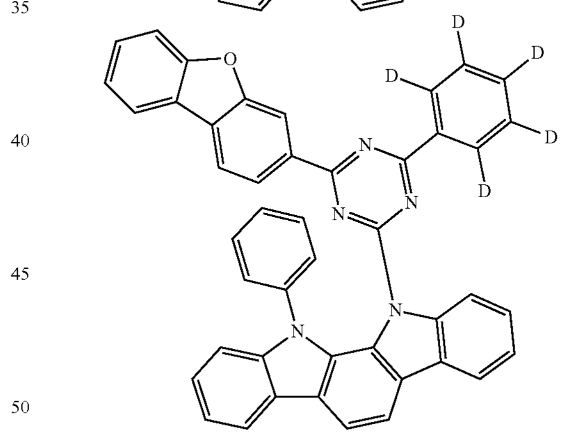
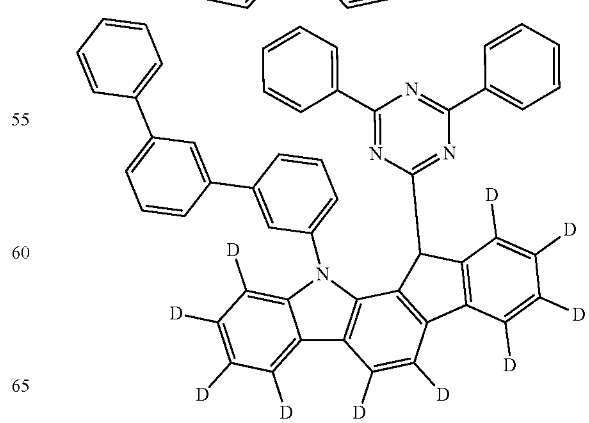

-continued
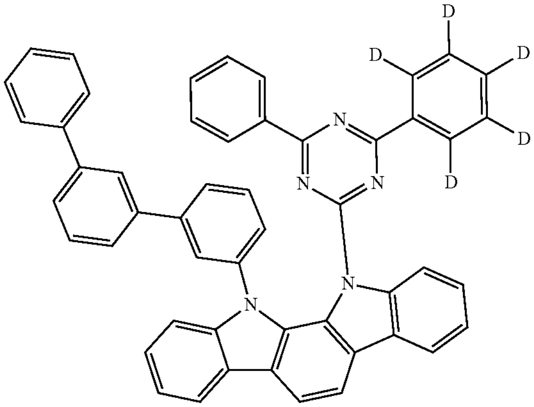
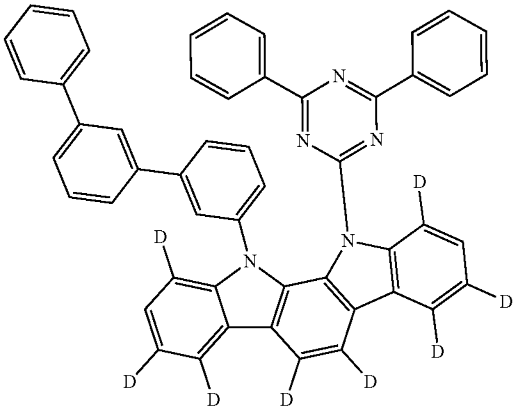
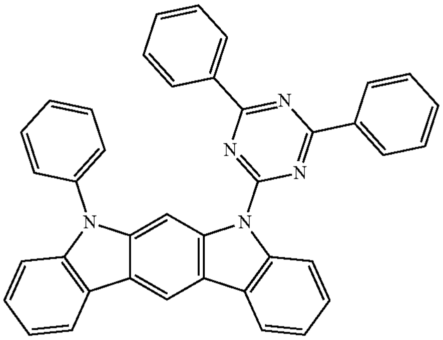
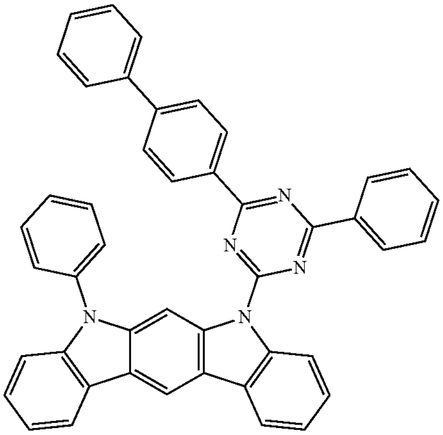
-continued
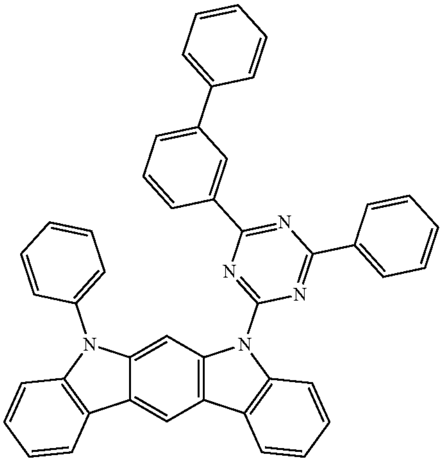
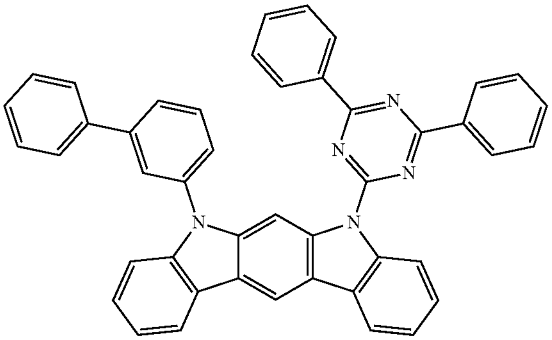
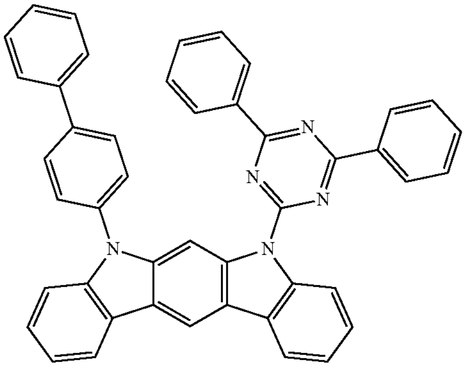
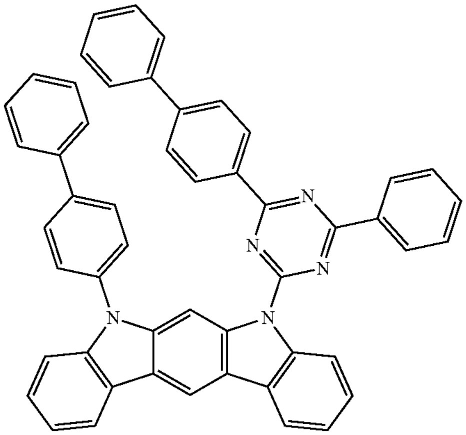

-continued
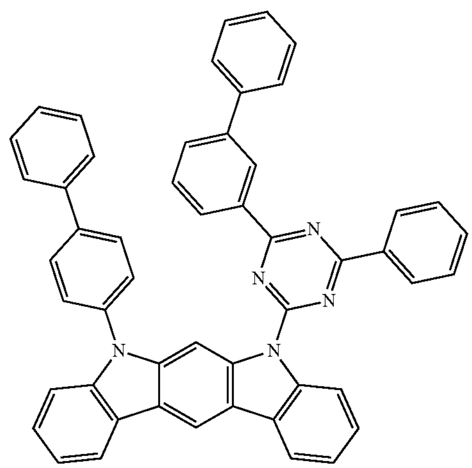
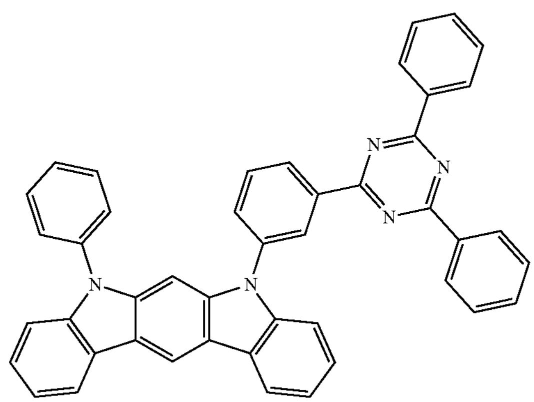
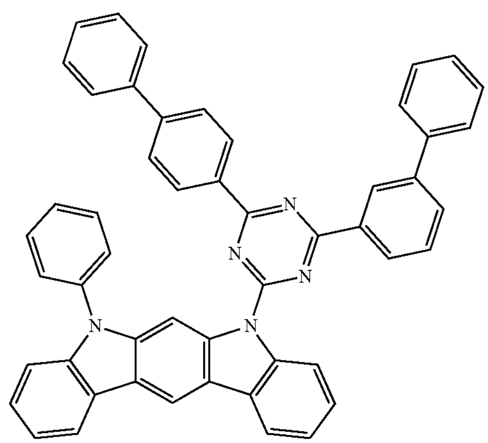
-continued
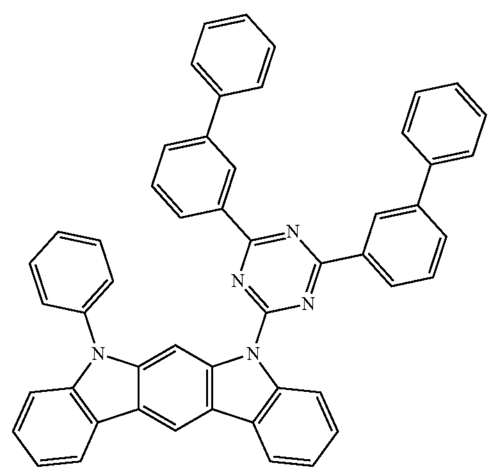
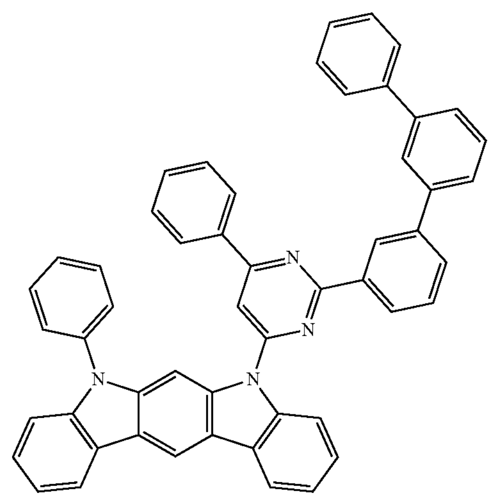
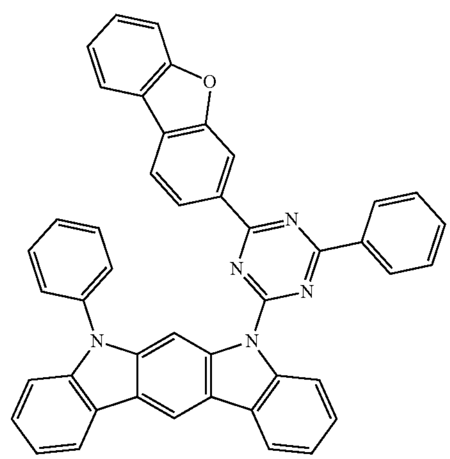

-continued
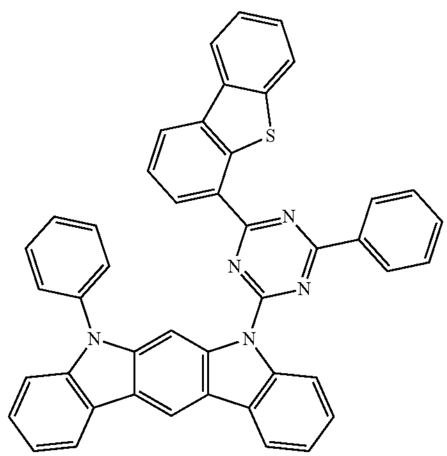
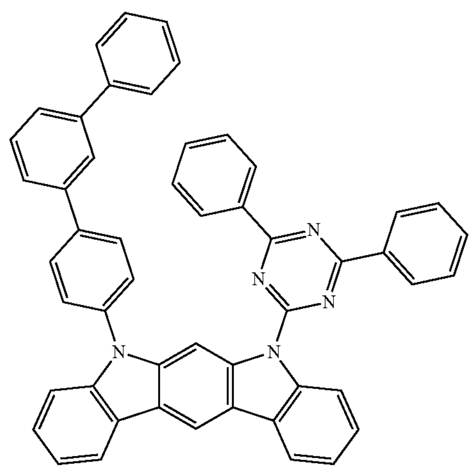
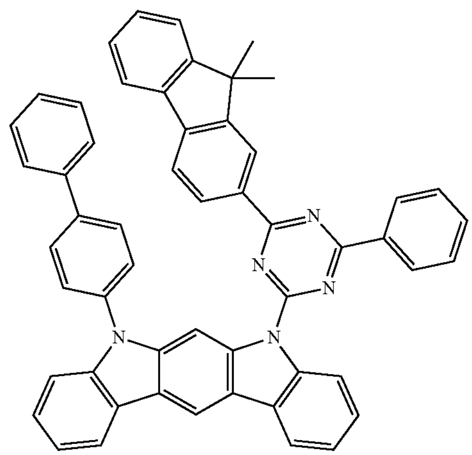
-continued
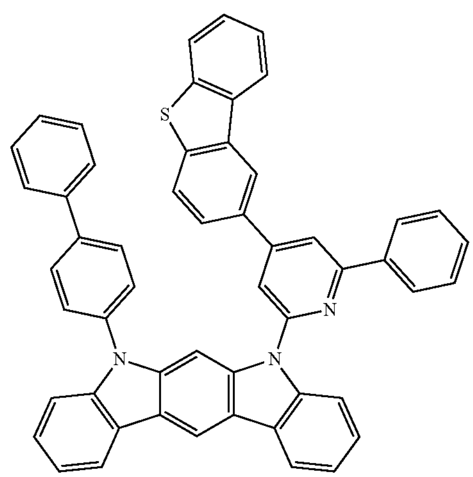
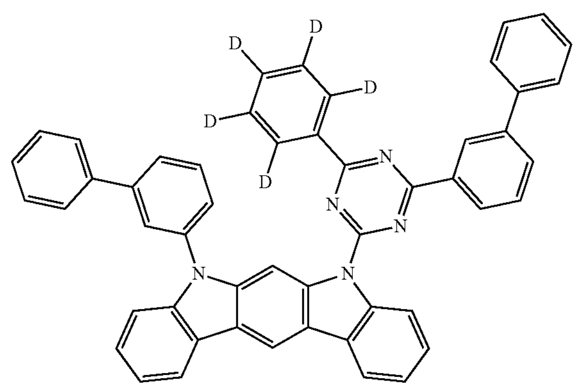
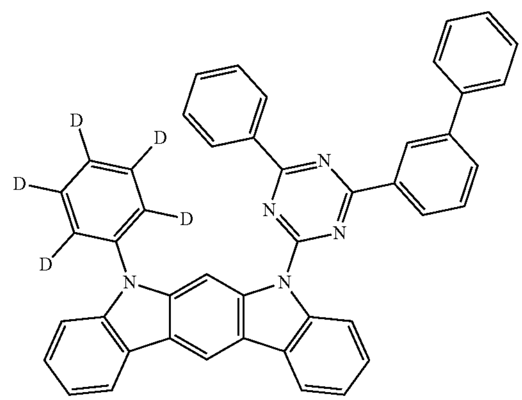

-continued
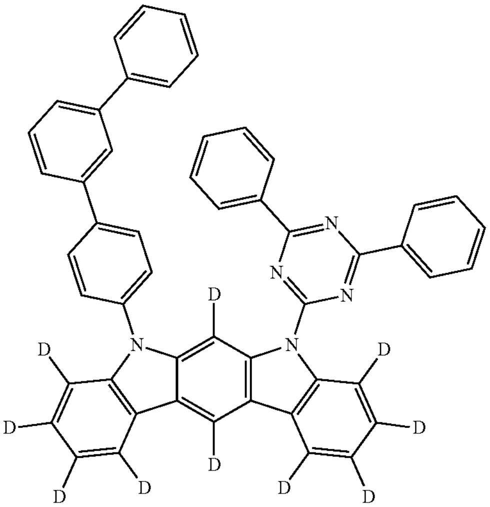
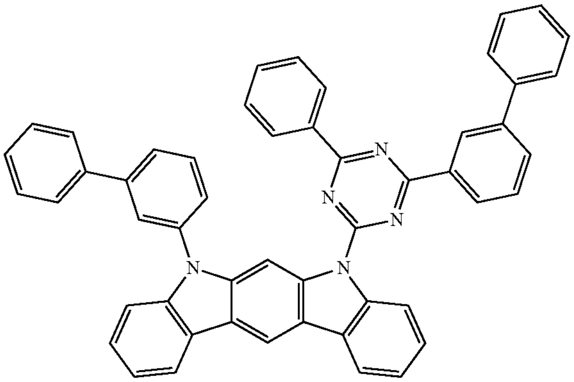
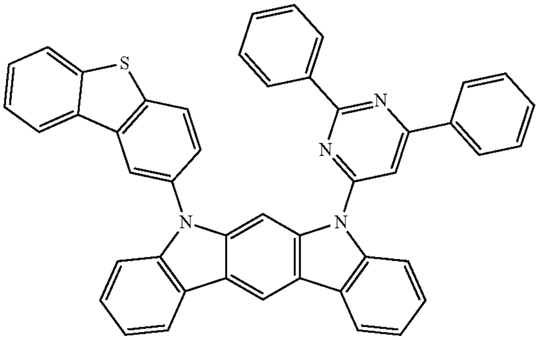
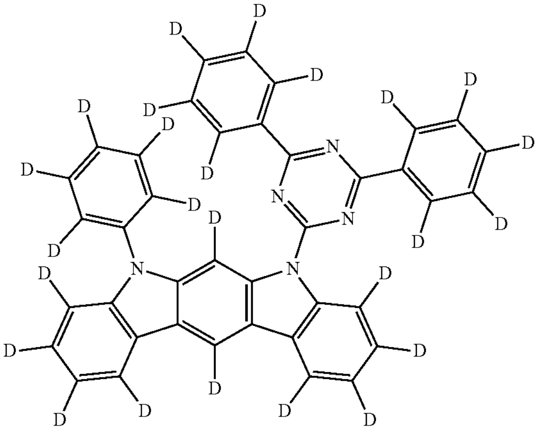
-continued
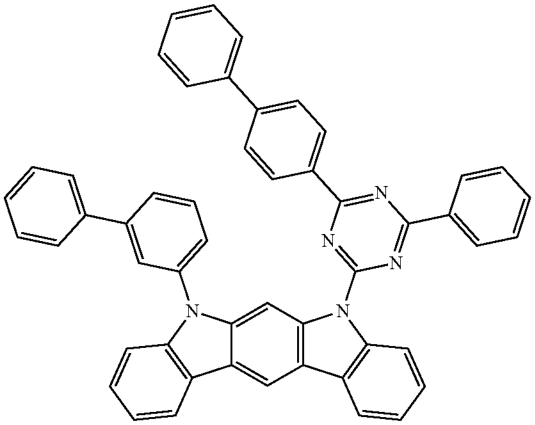
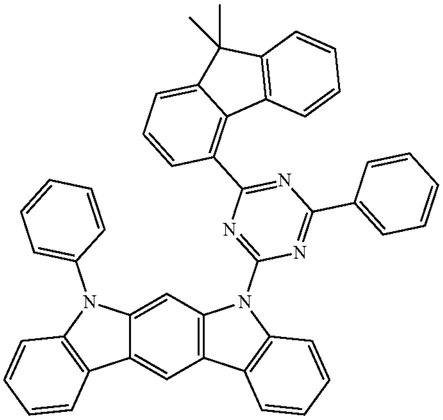
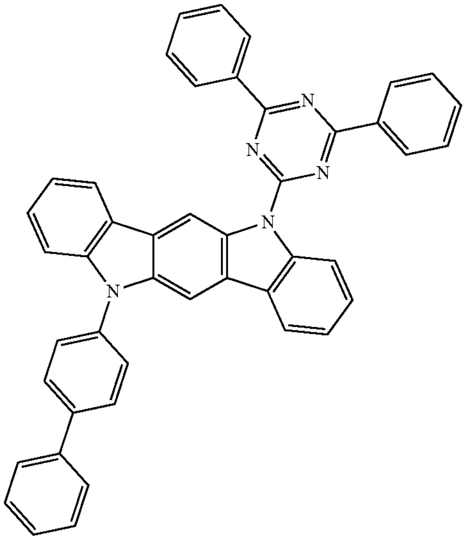

-continued
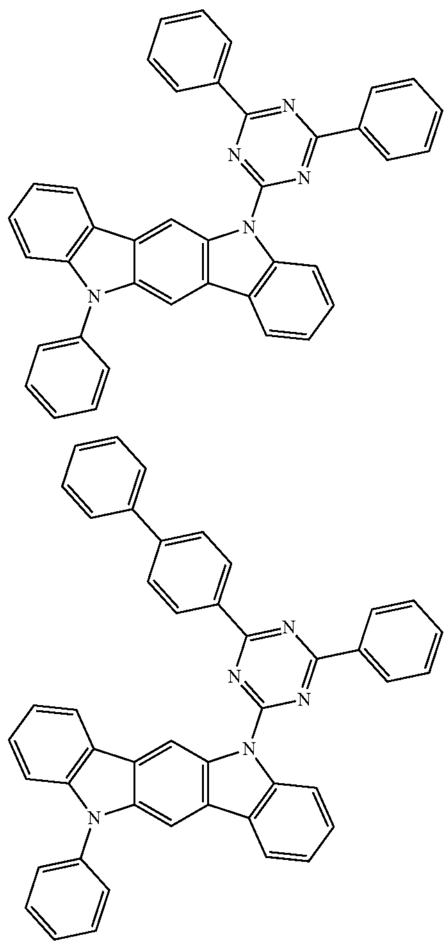
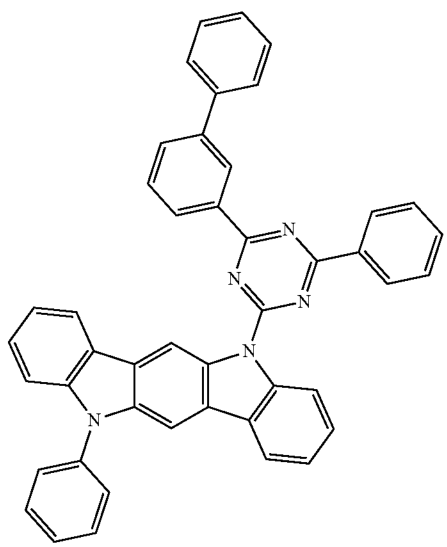
-continued
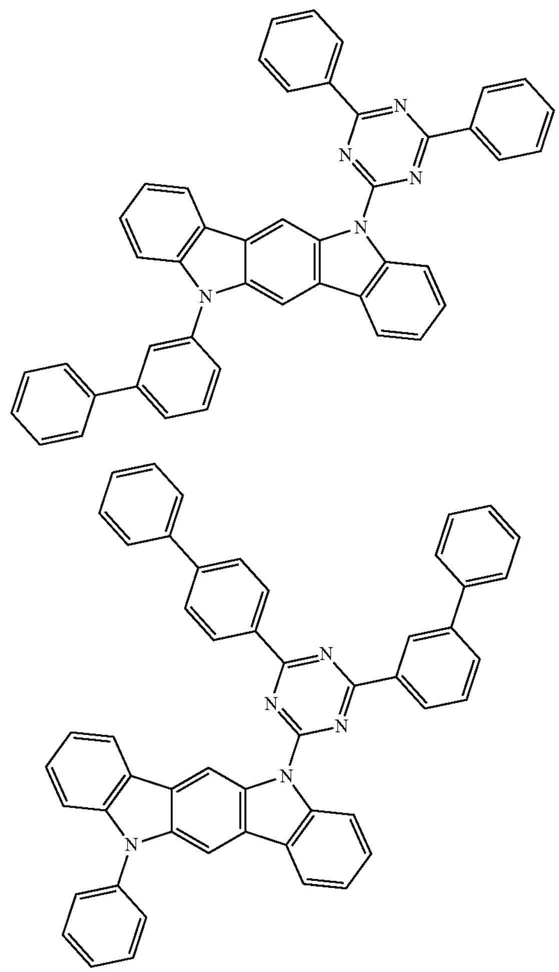
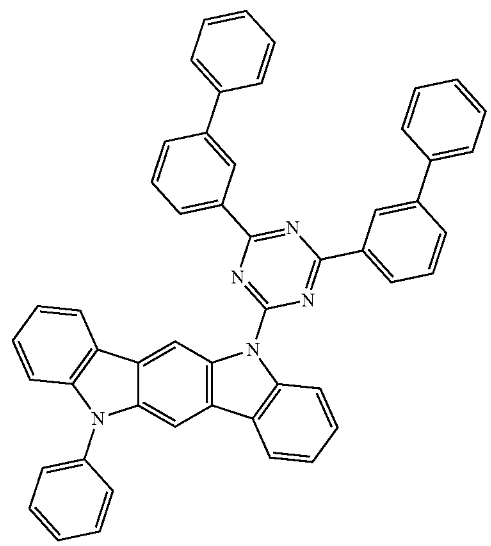

-continued
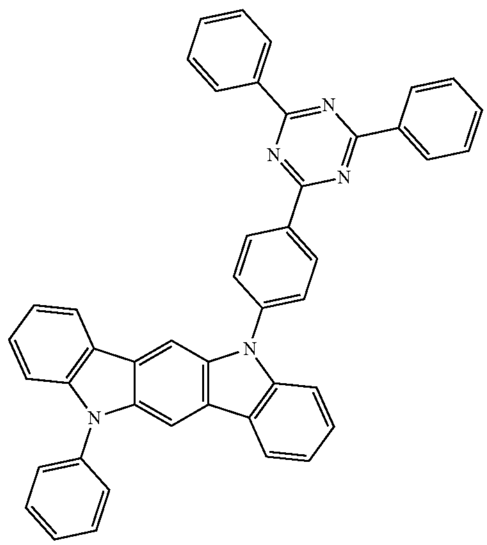
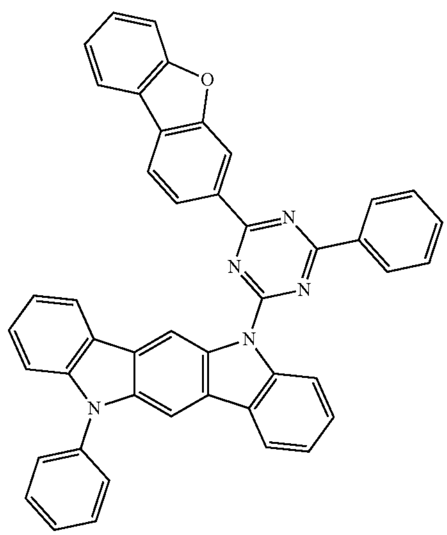
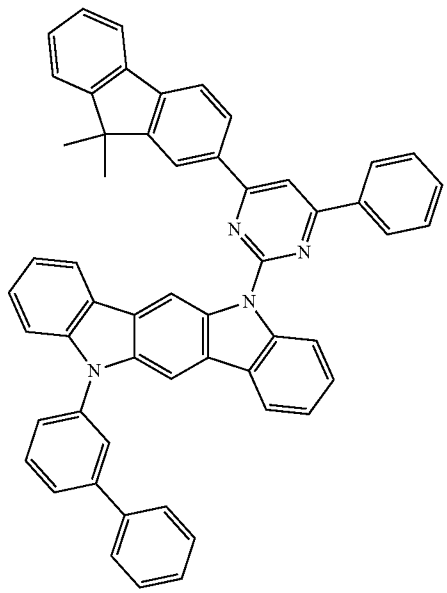
-continued
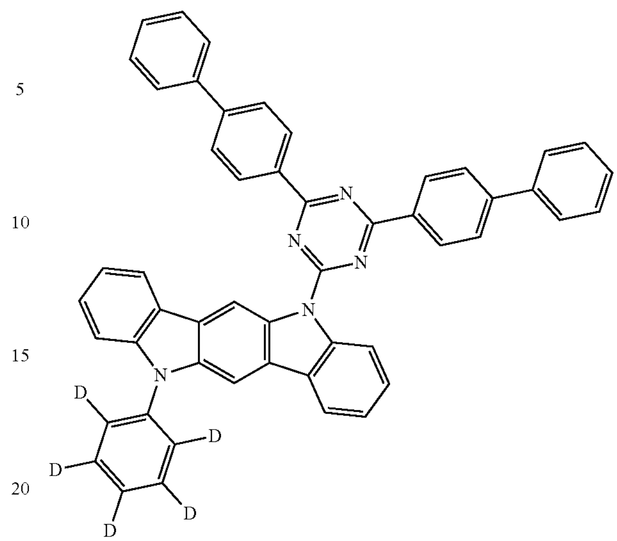
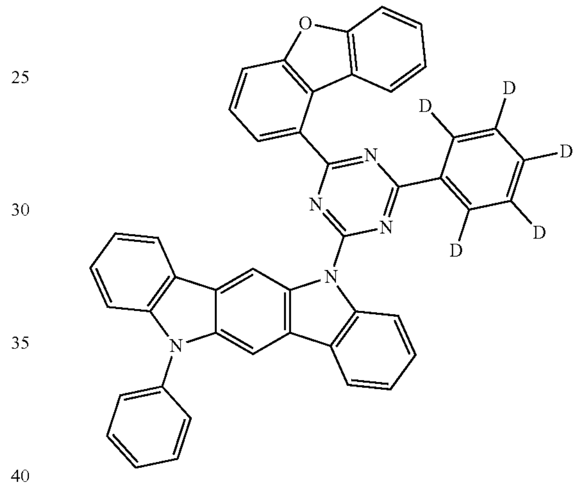
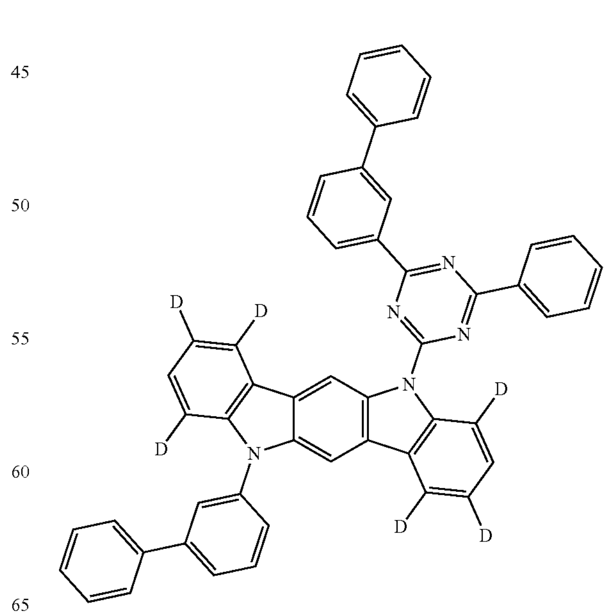

-continued
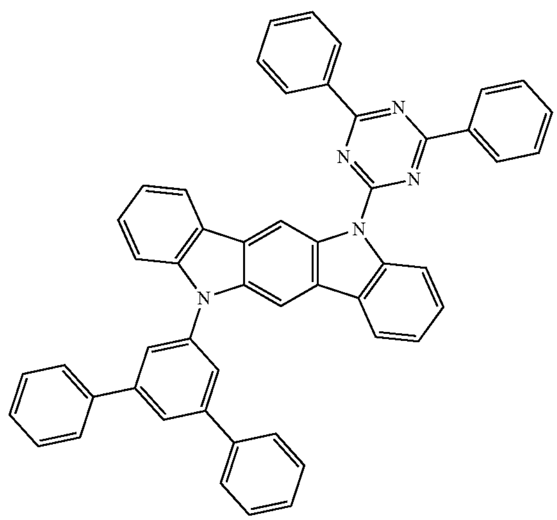
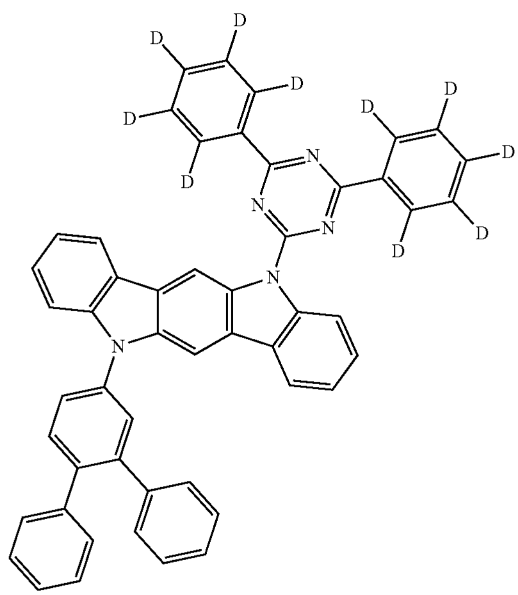
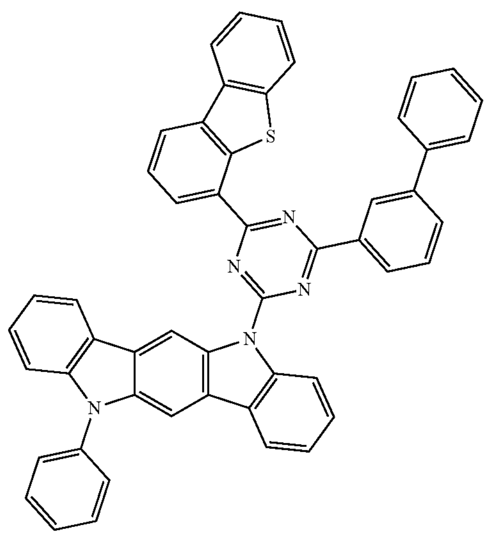
-continued
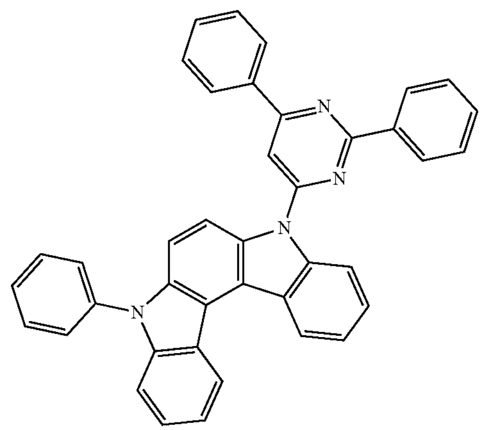
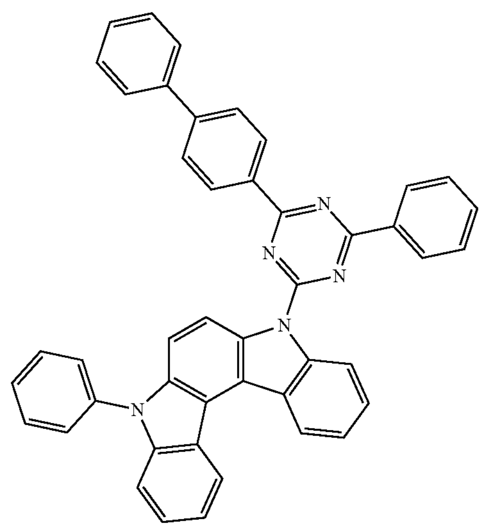
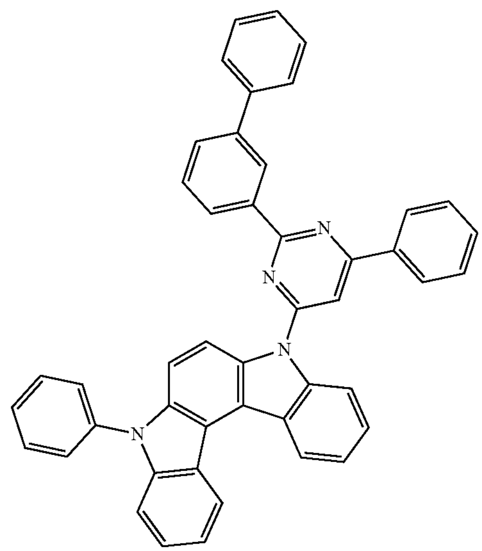

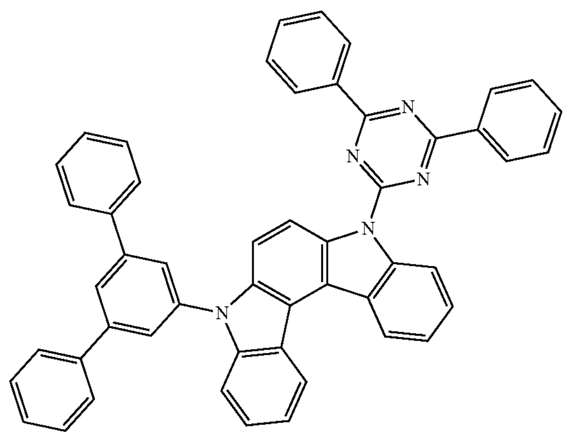
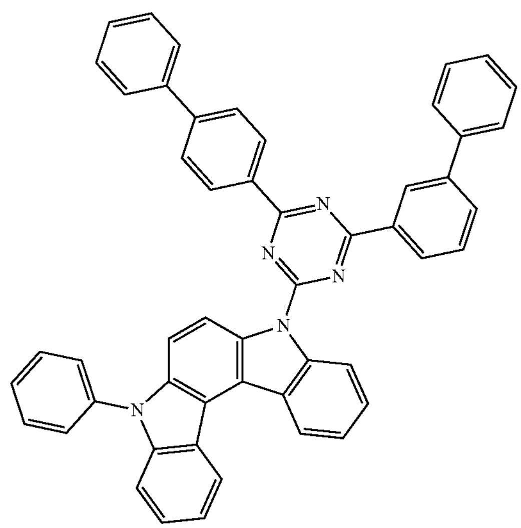
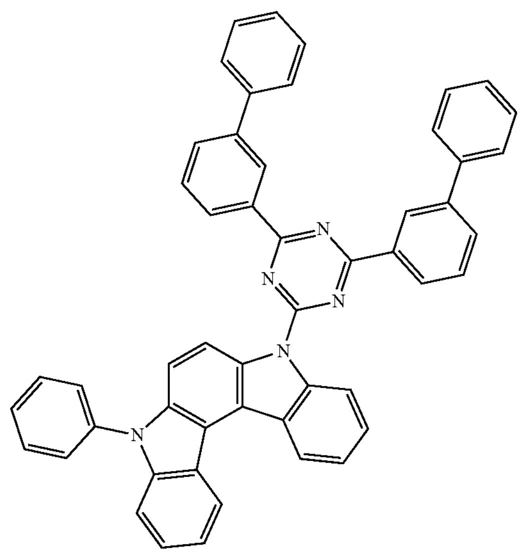
-continued
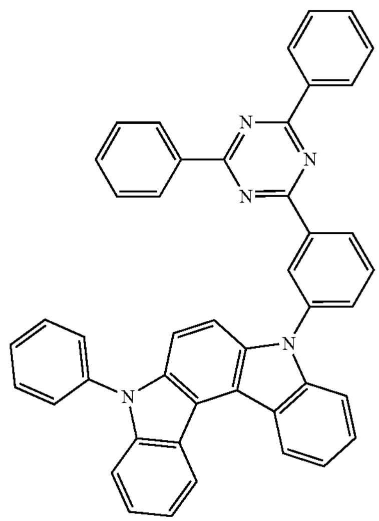
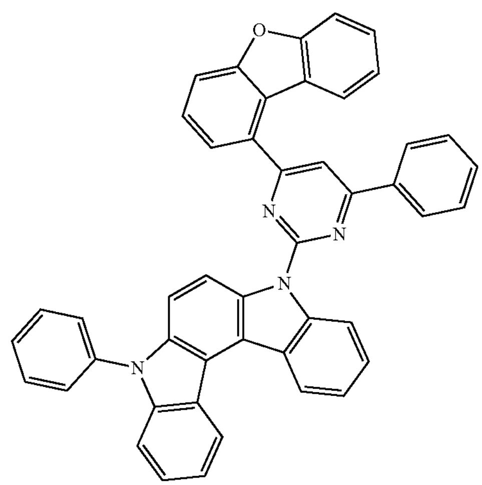
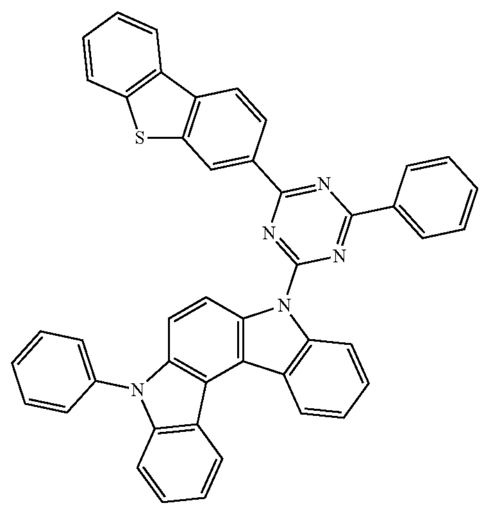

-continued
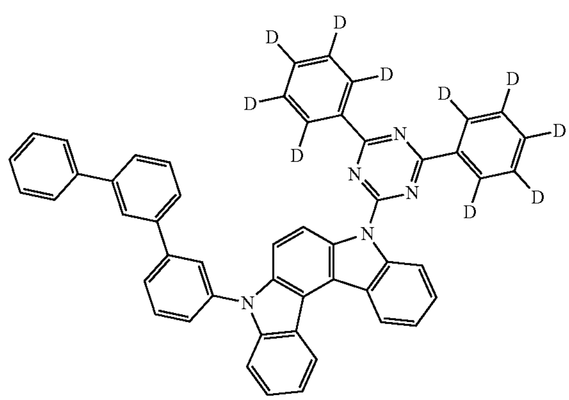
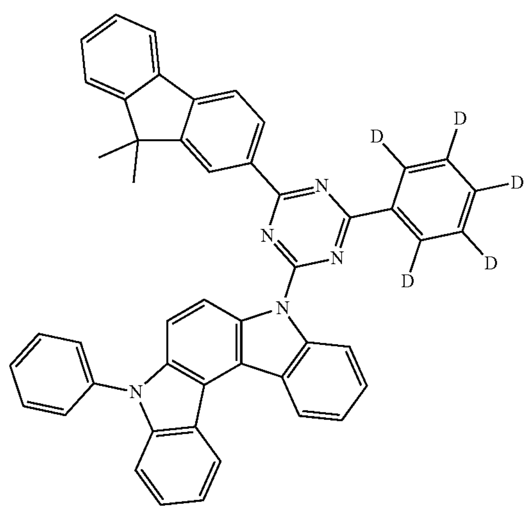
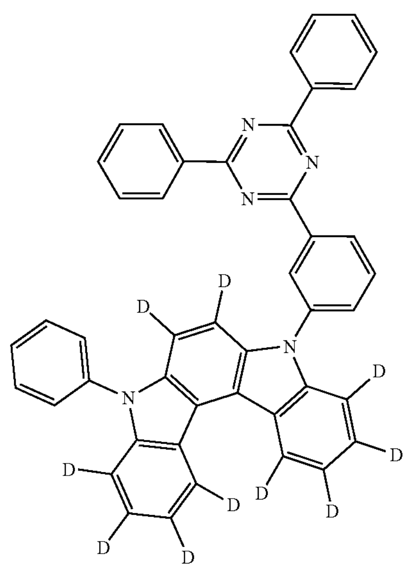
-continued
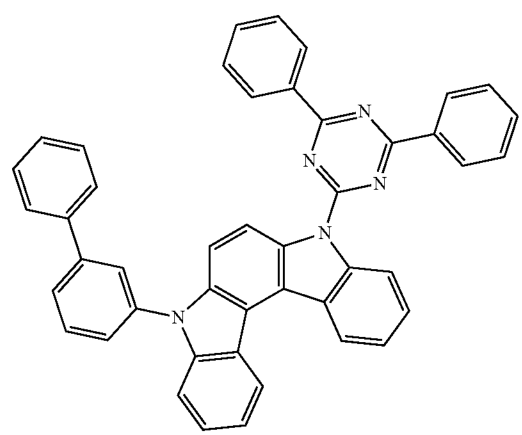
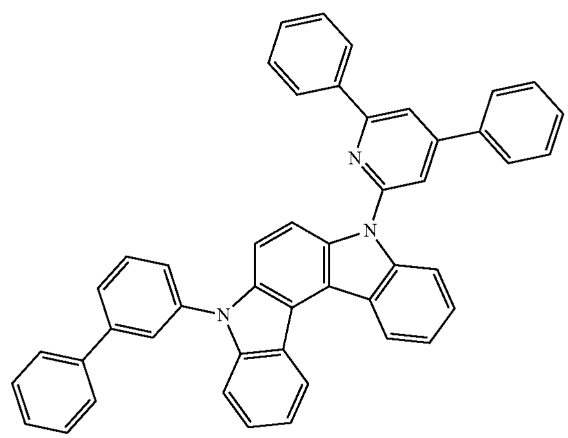
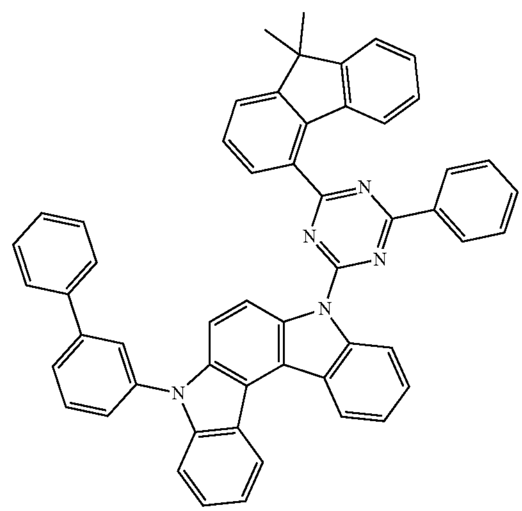

-continued
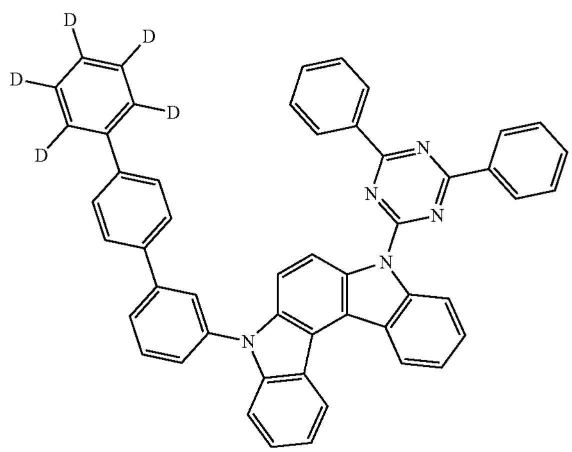
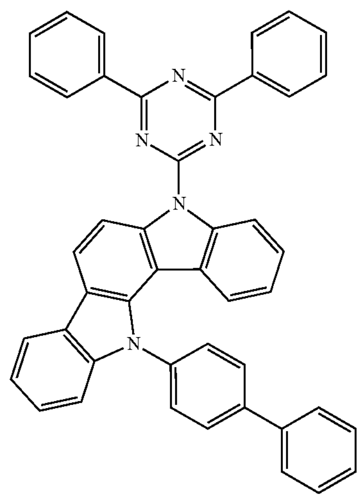
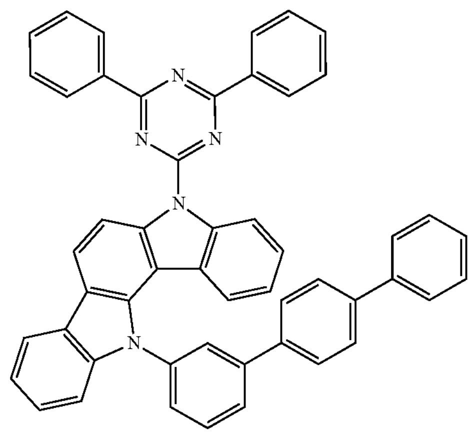
-continued
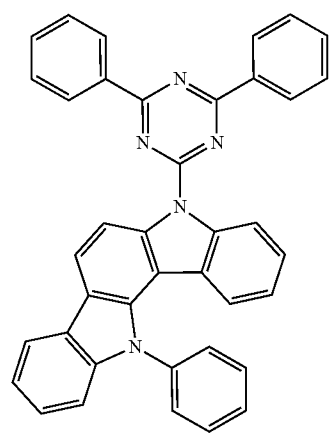
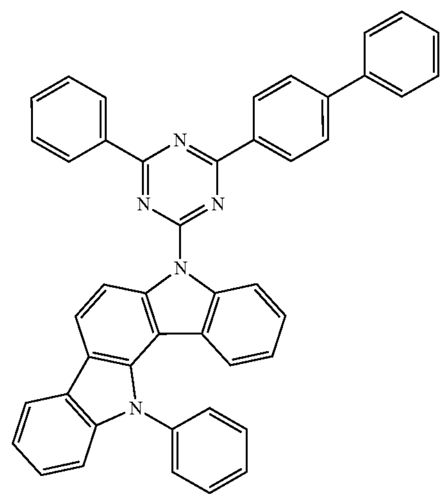
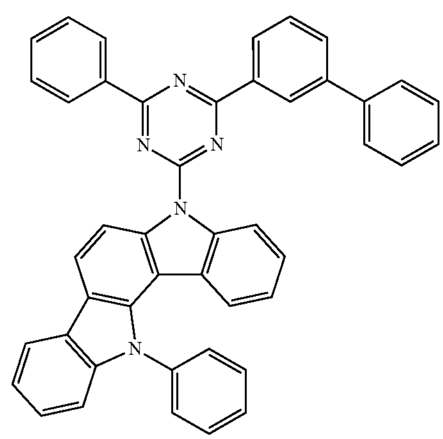

-continued
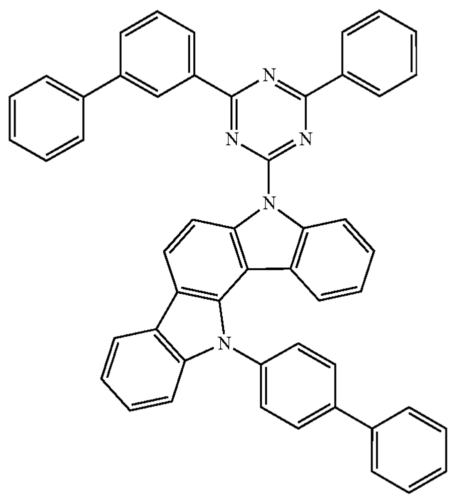
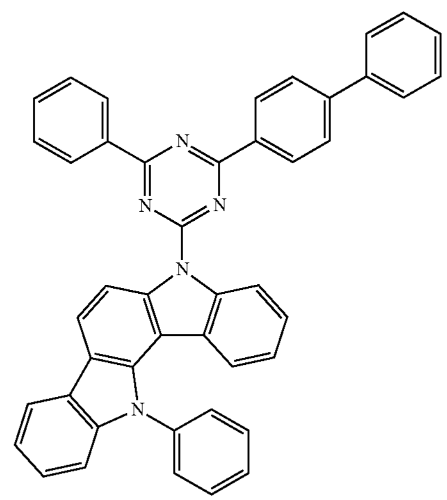
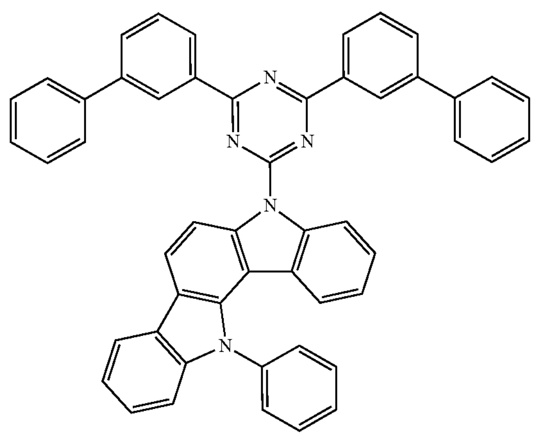
-continued
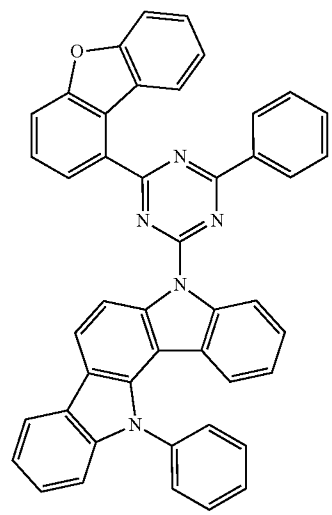
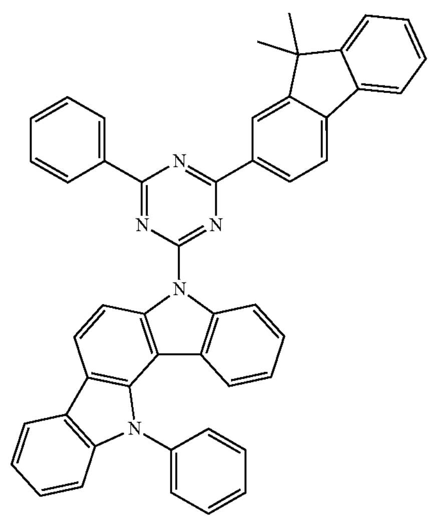
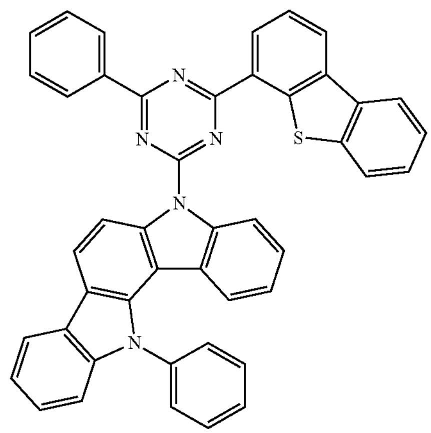

-continued
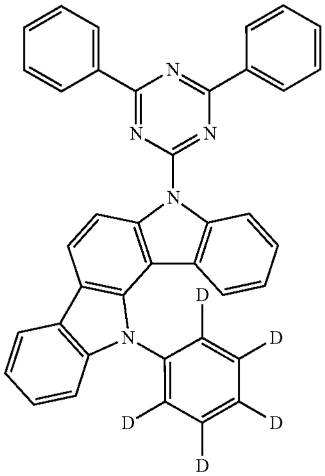
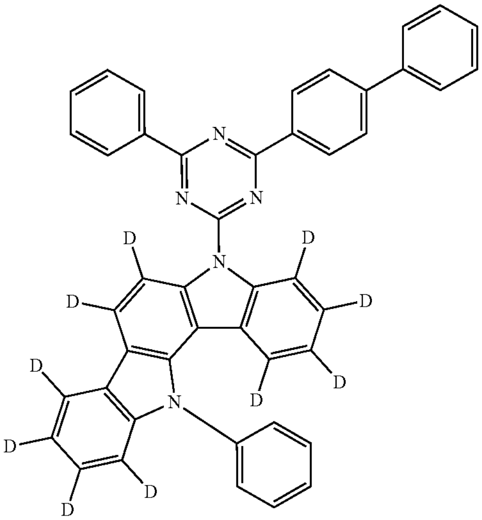
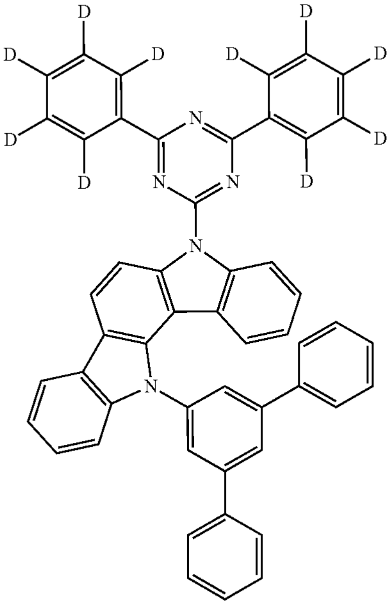
-continued
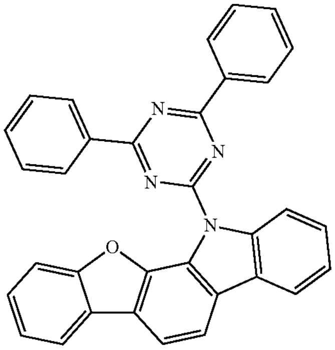
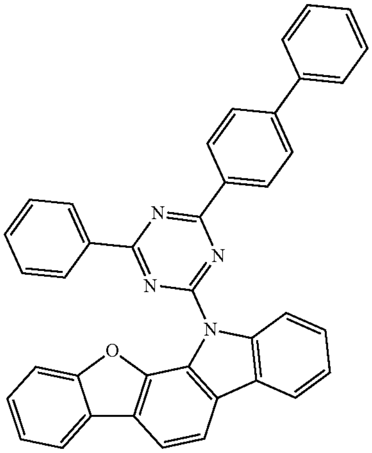
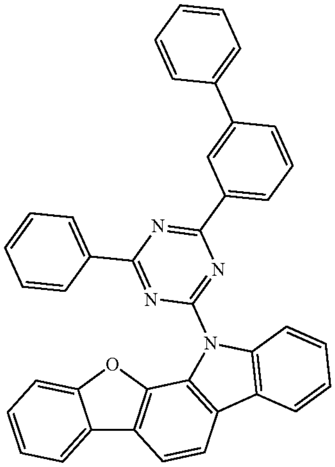

-continued
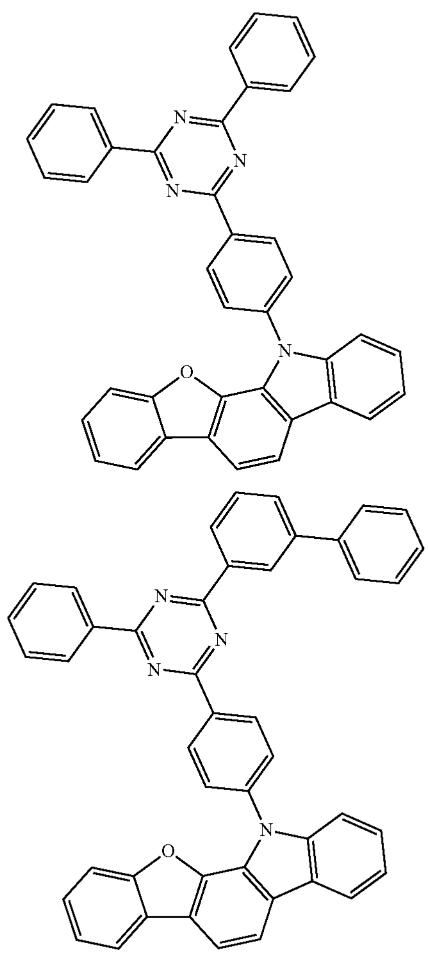
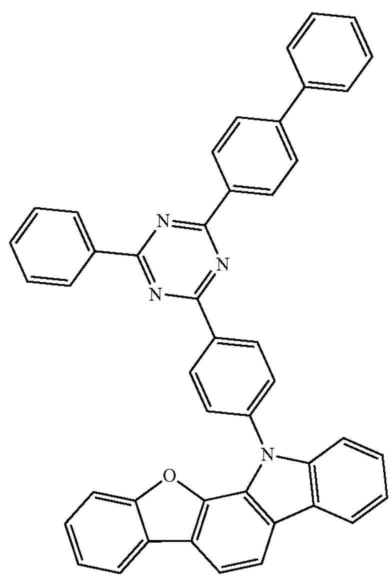
-continued
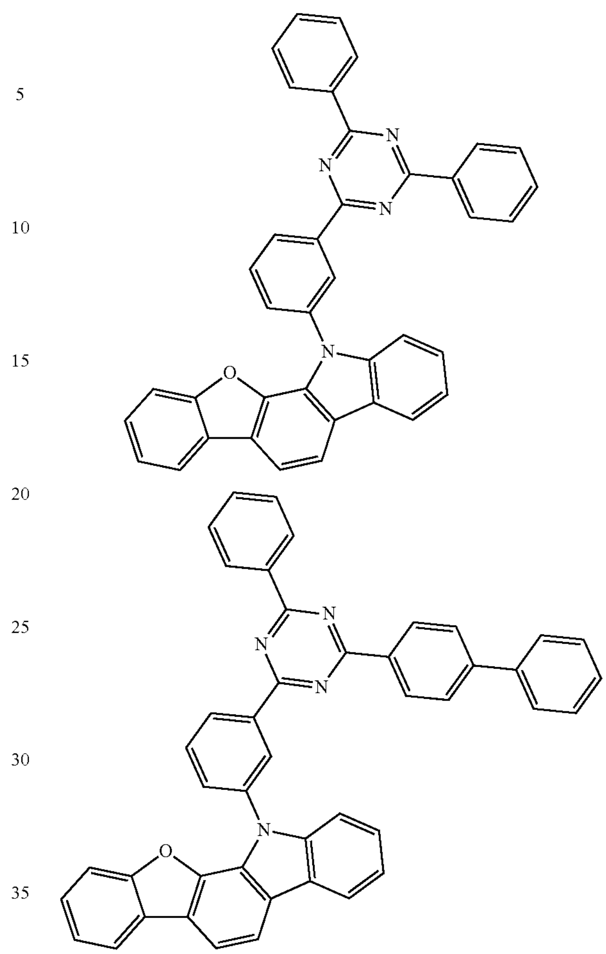
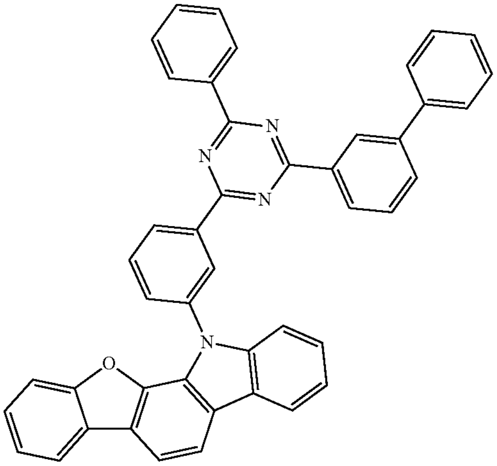

-continued
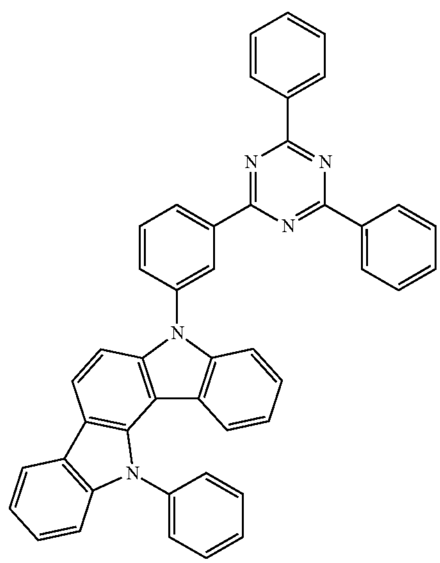
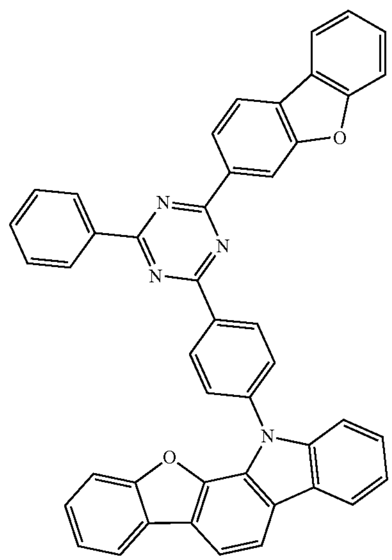
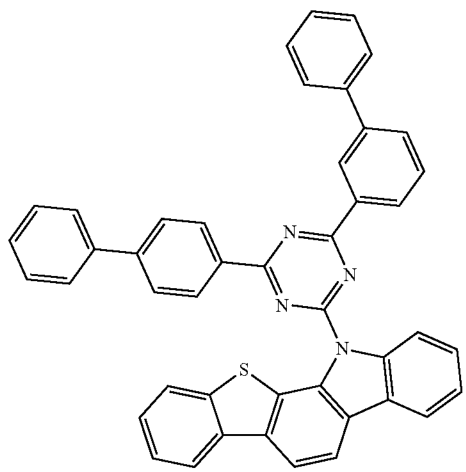
-continued
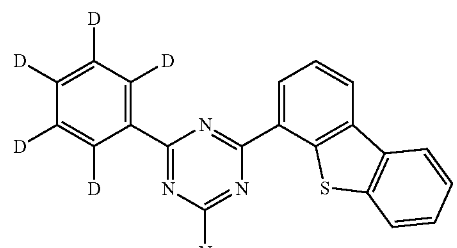
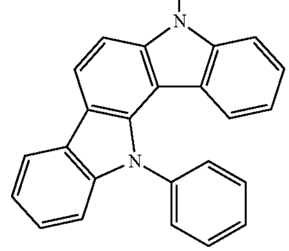
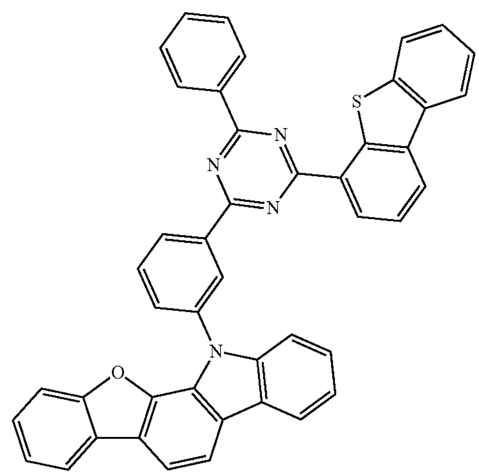
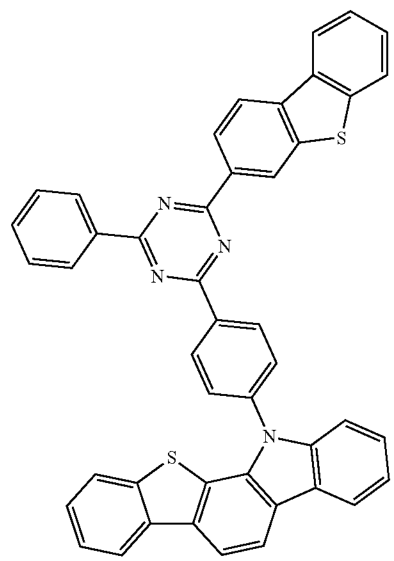

-continued
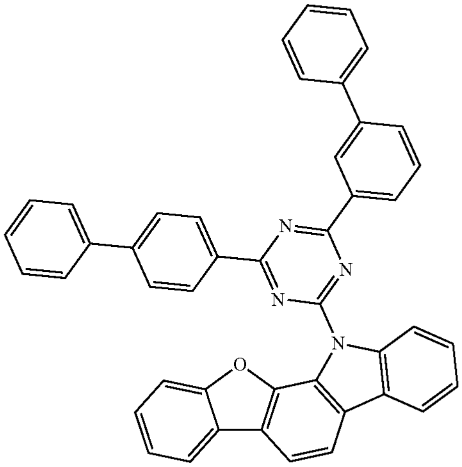
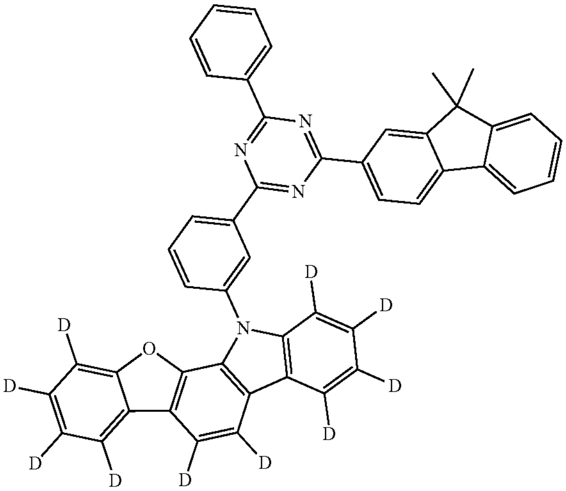
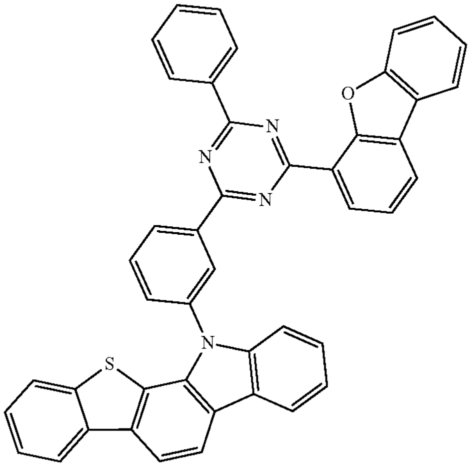
-continued
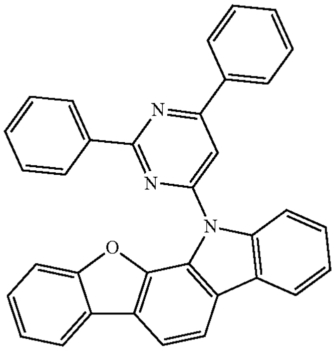
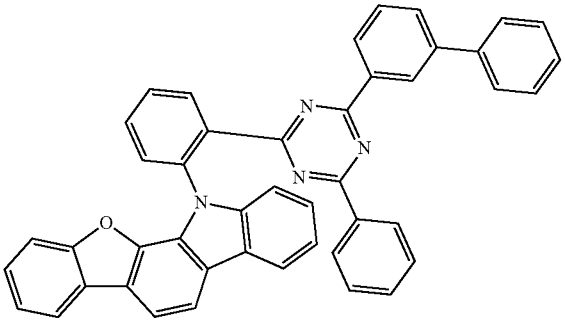
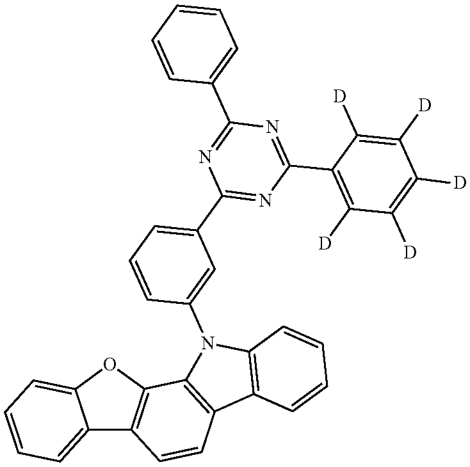
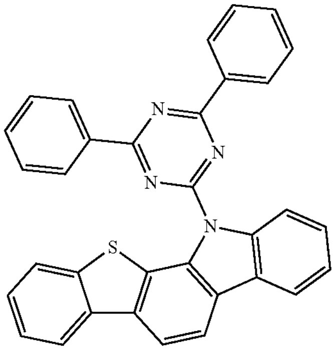

-continued
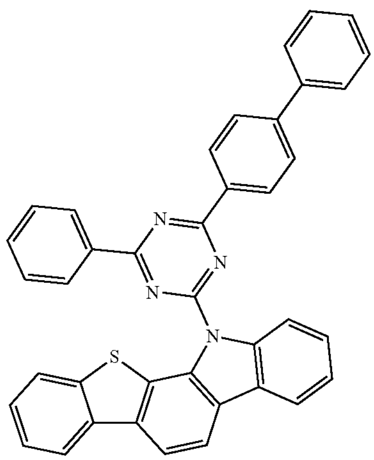
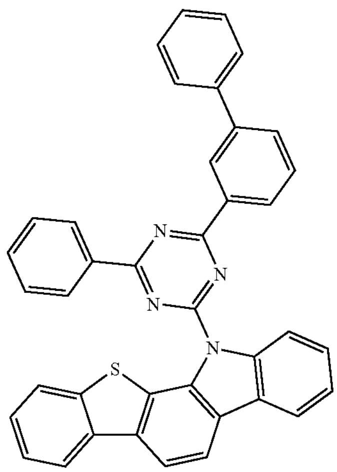
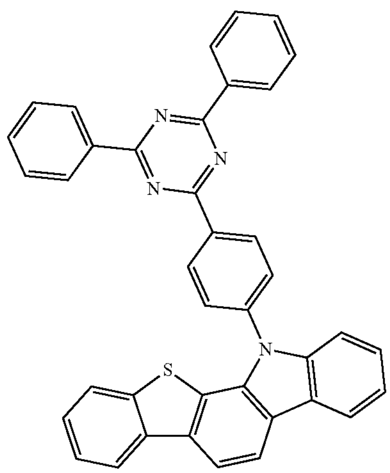
-continued
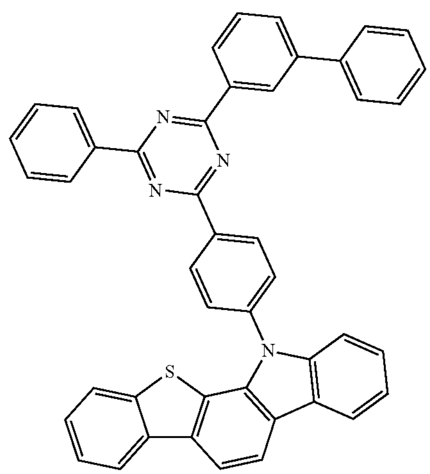
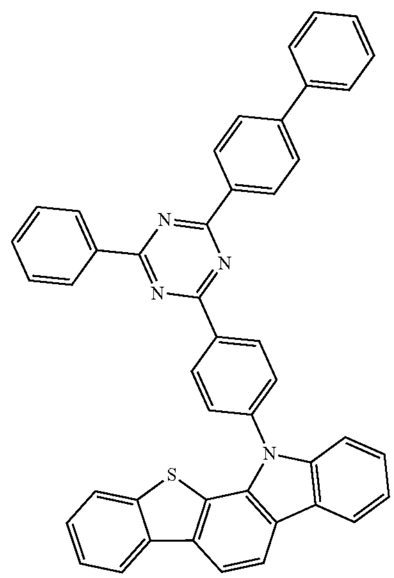
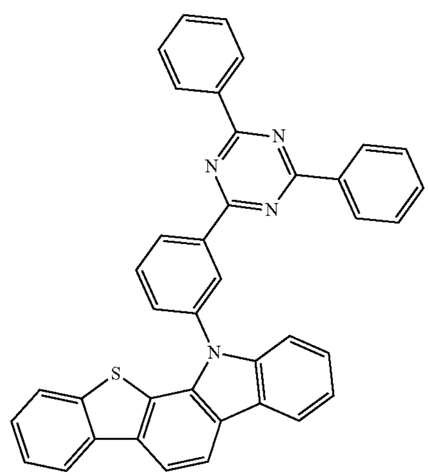

-continued
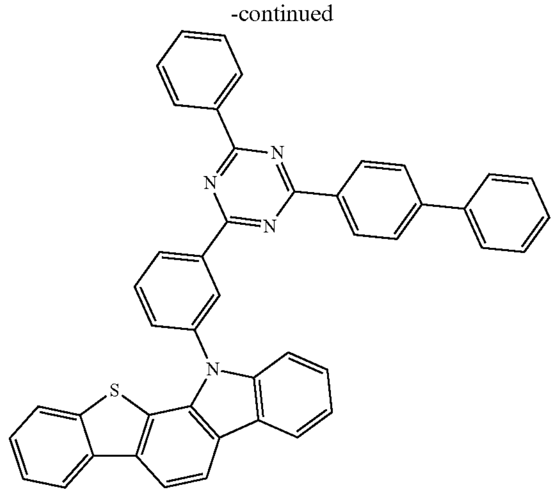
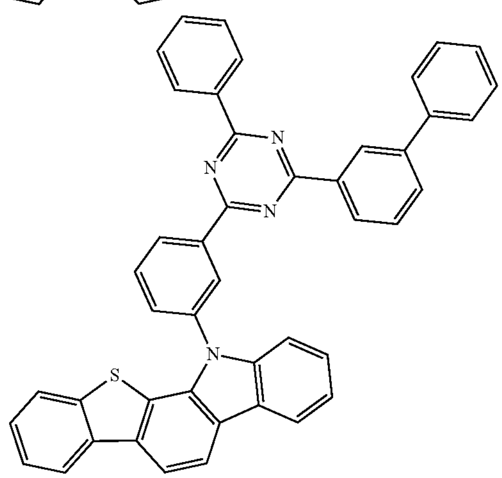
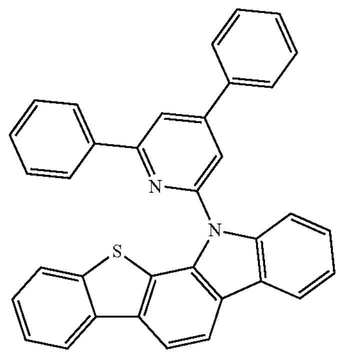
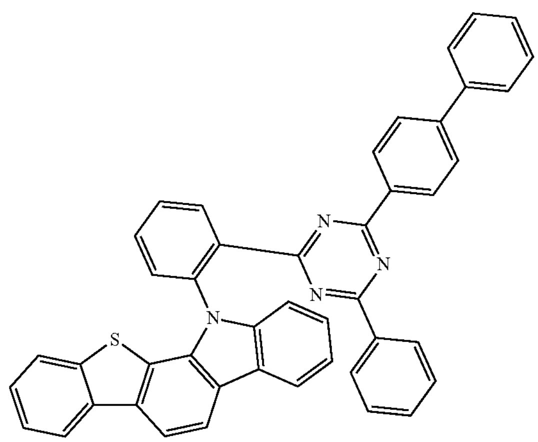
-continued
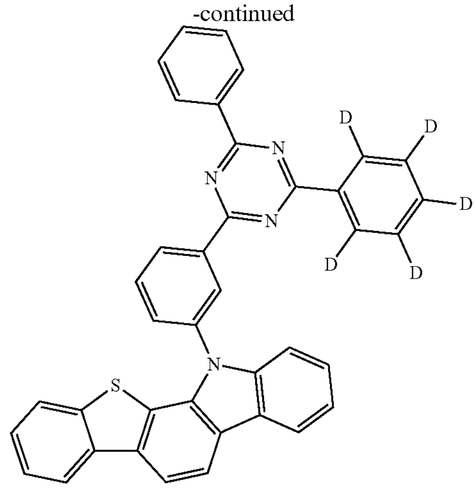
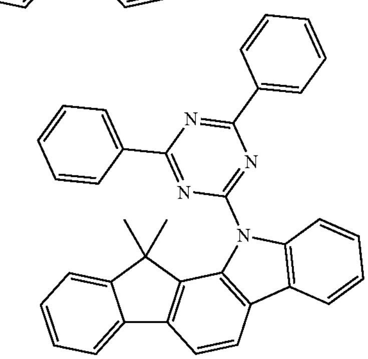
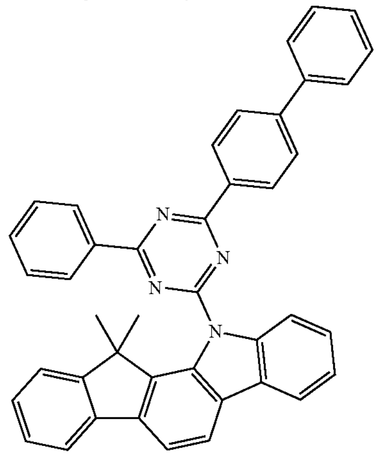
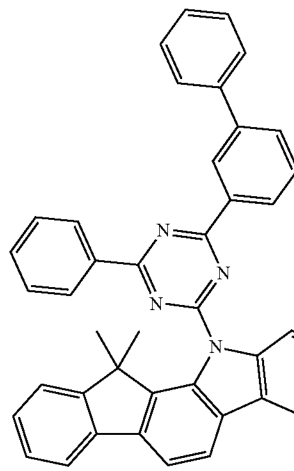

-continued
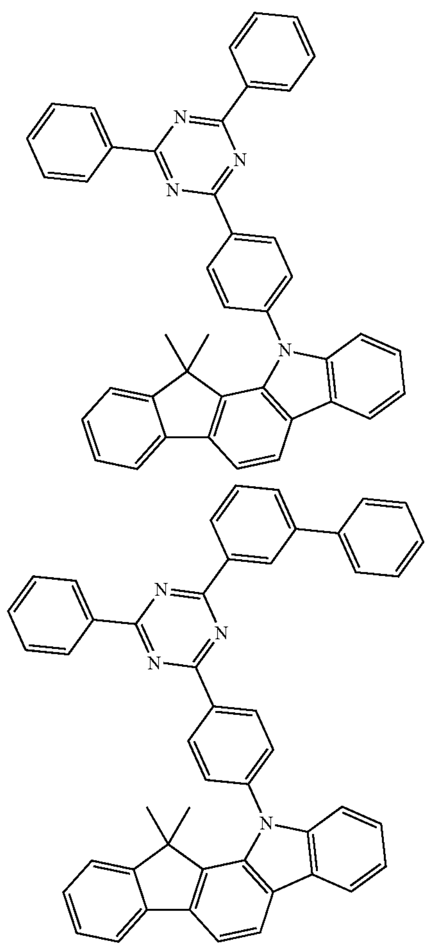
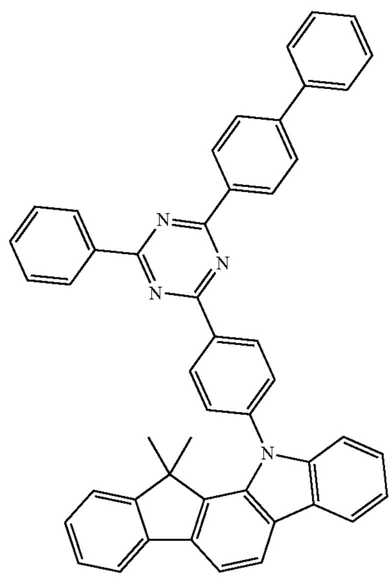
-continued
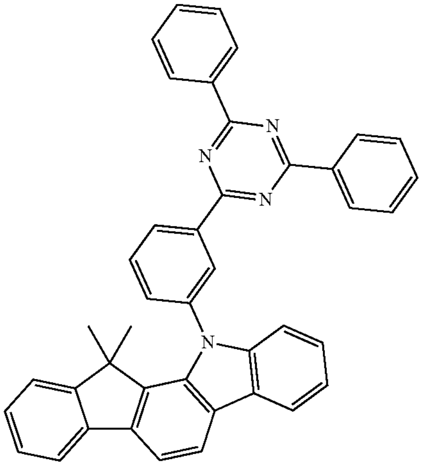
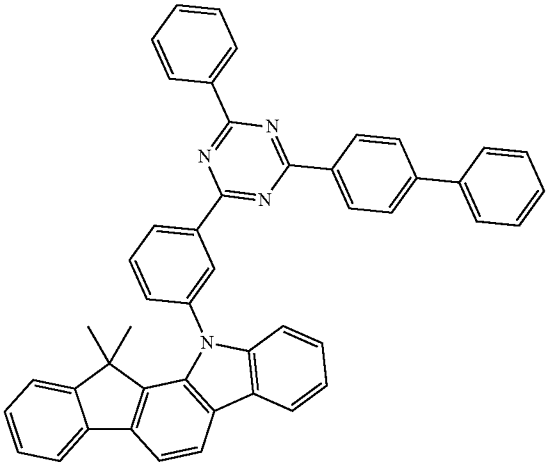
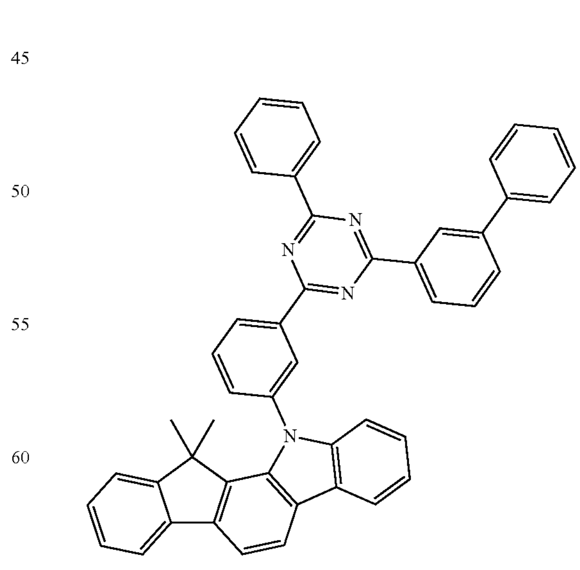

-continued
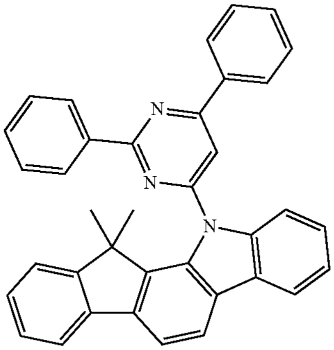
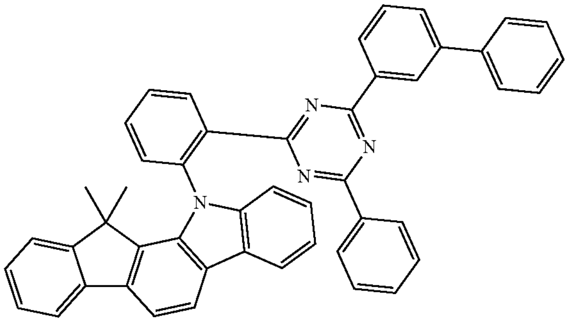
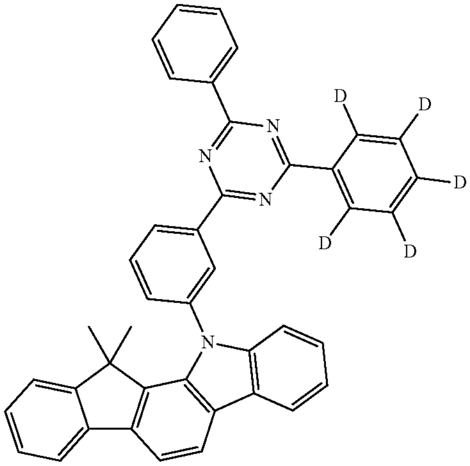
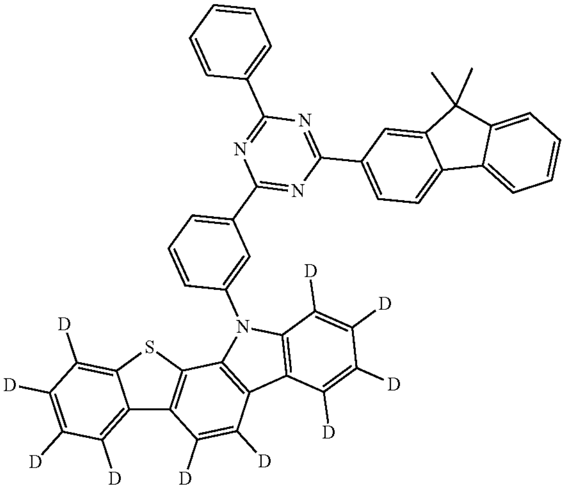
-continued
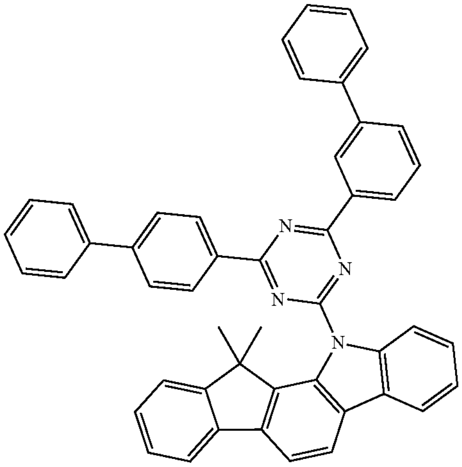
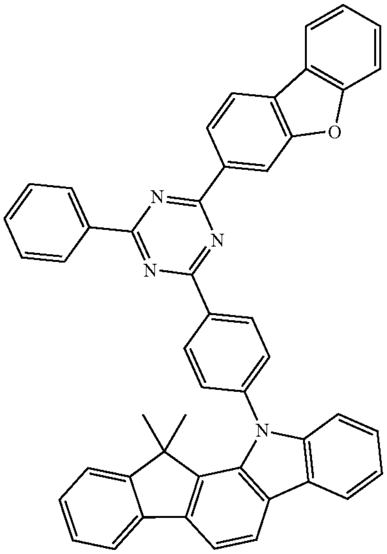
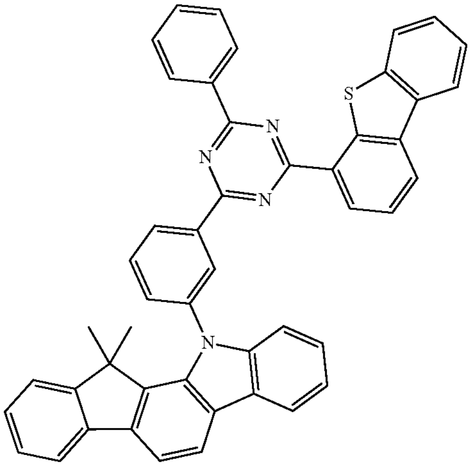

-continued
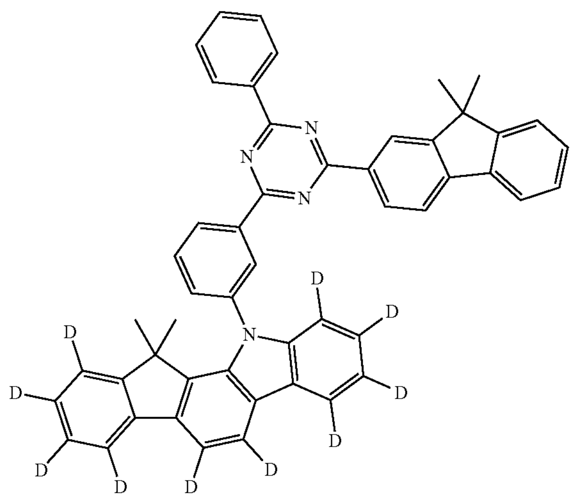
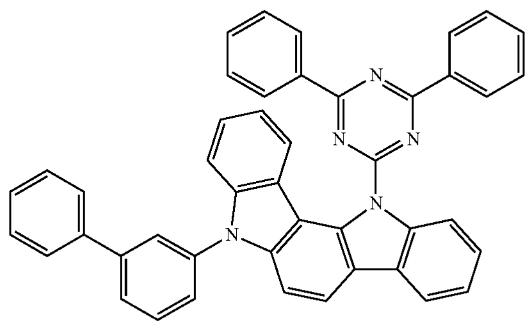
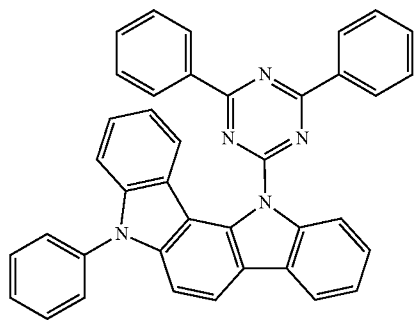
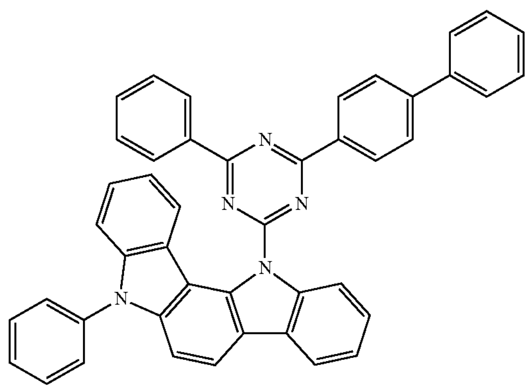
-continued
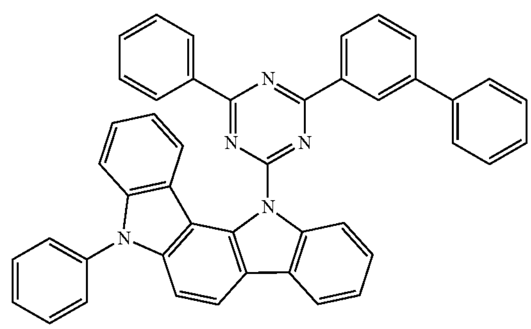
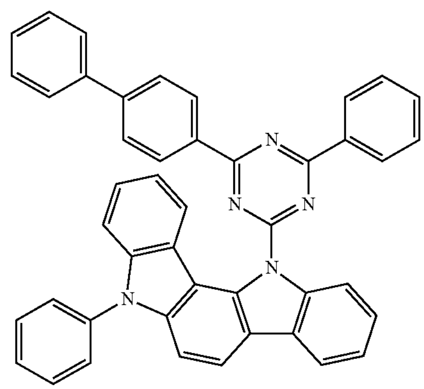
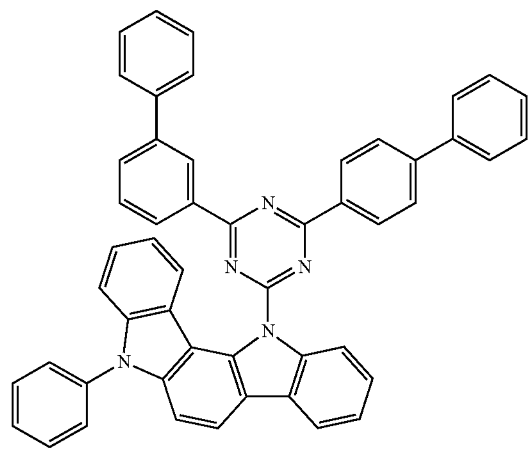
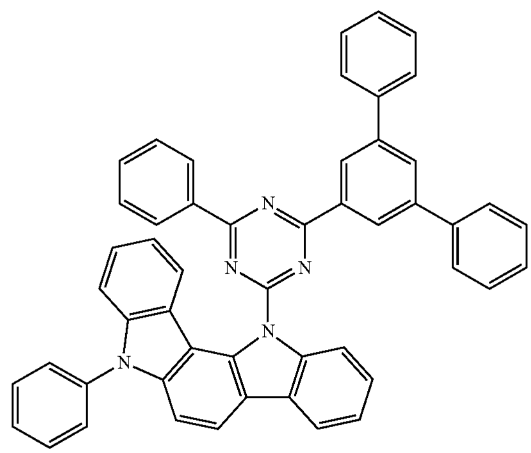

-continued
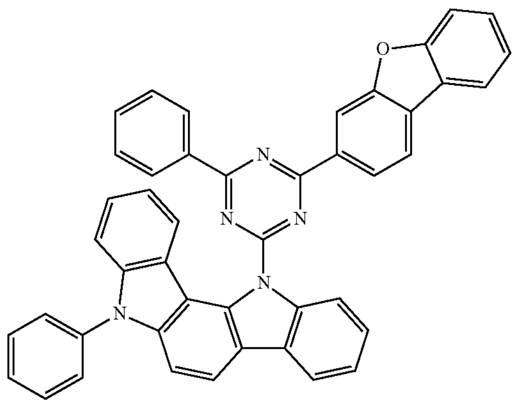
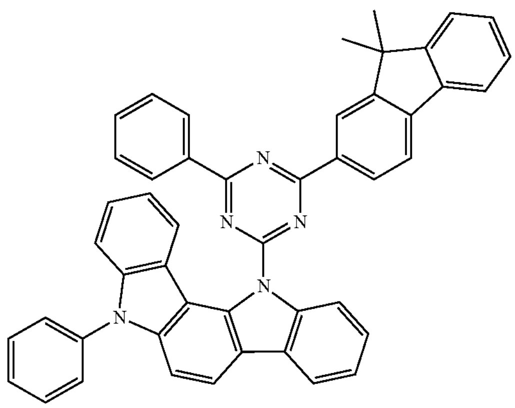
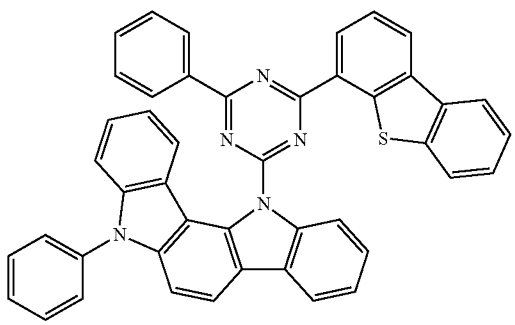
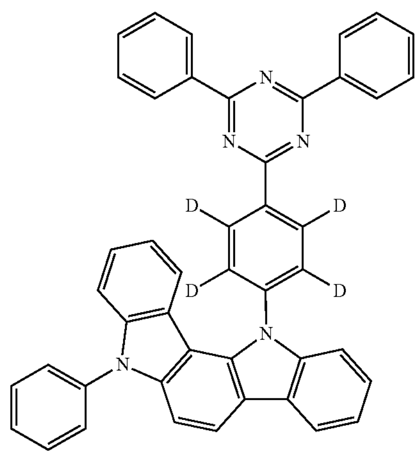
-continued
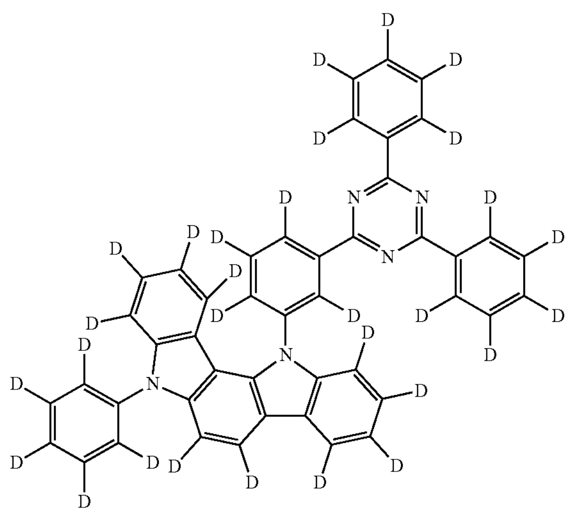
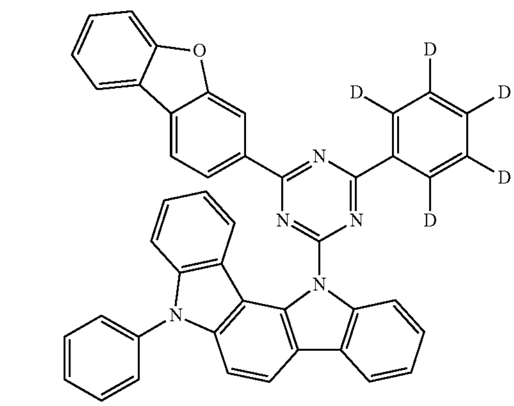
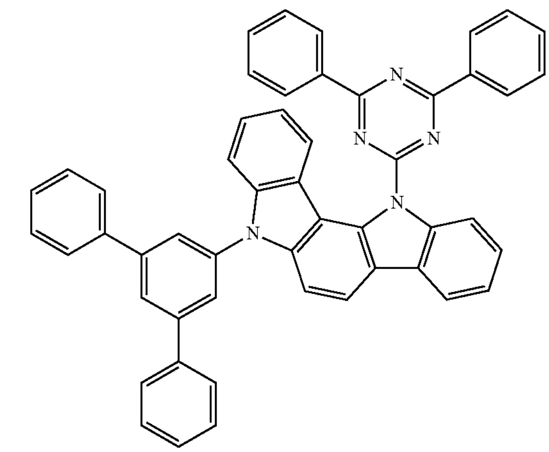
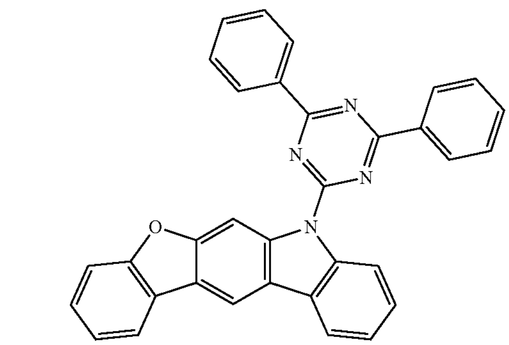

-continued
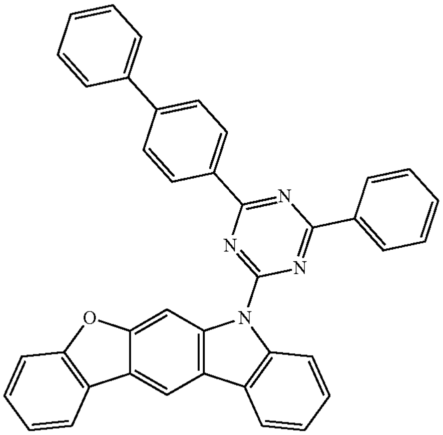
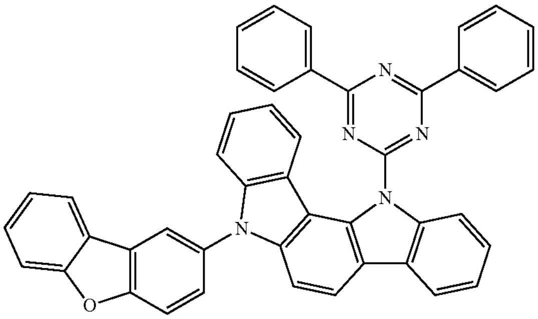
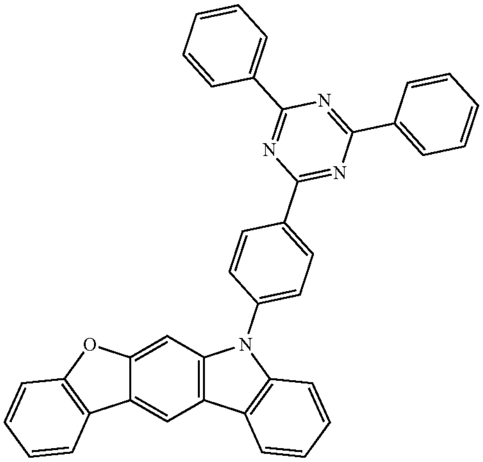
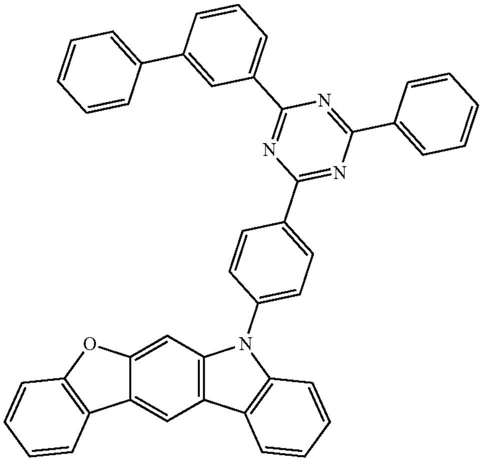
-continued
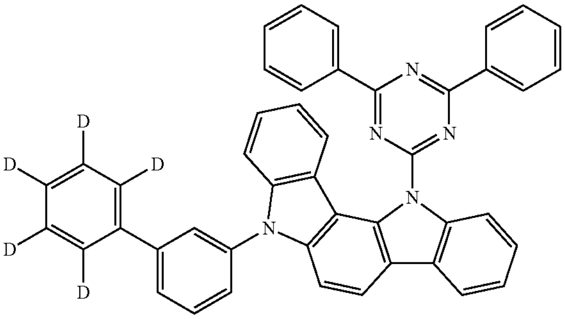
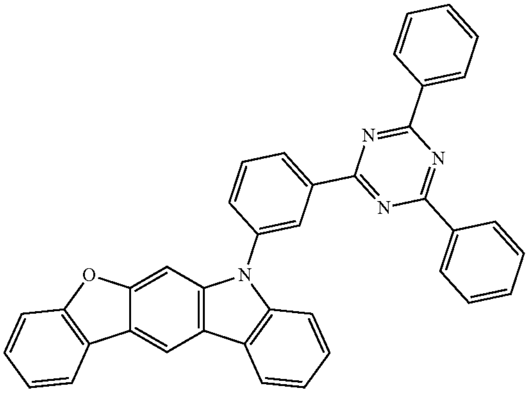
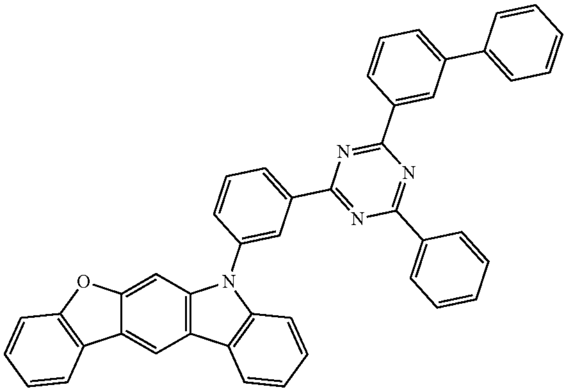
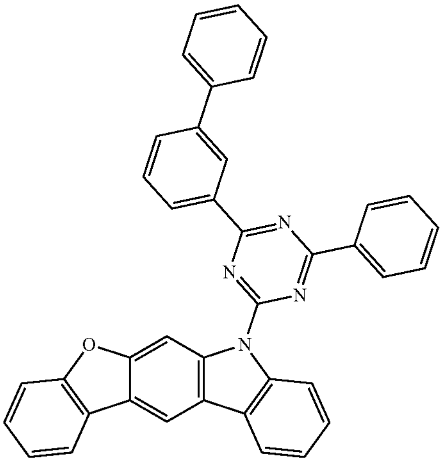

-continued
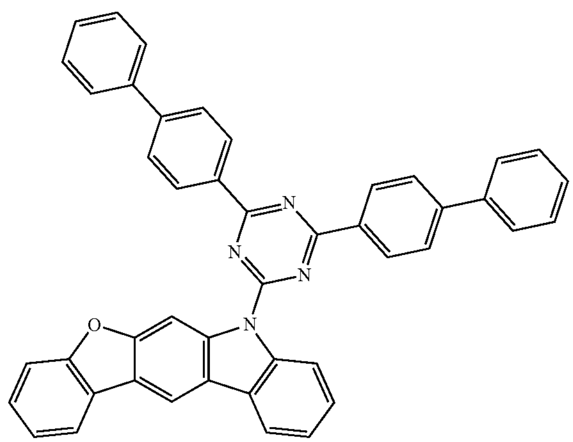
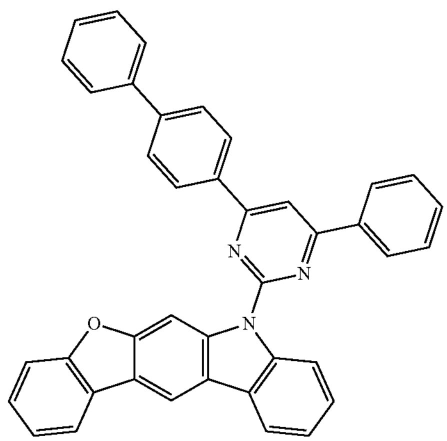
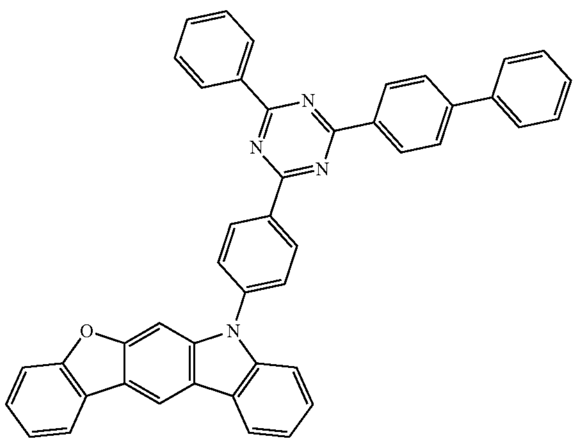
-continued
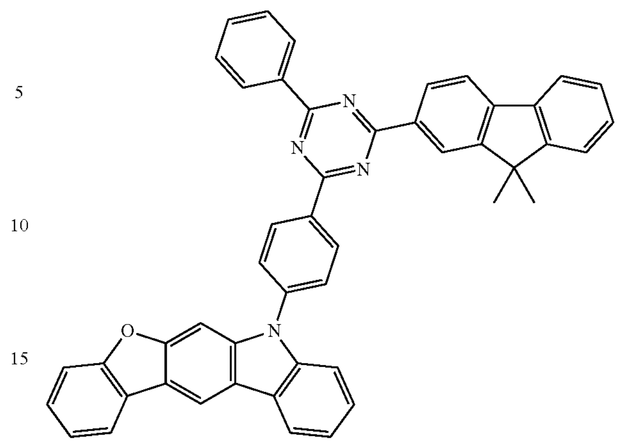
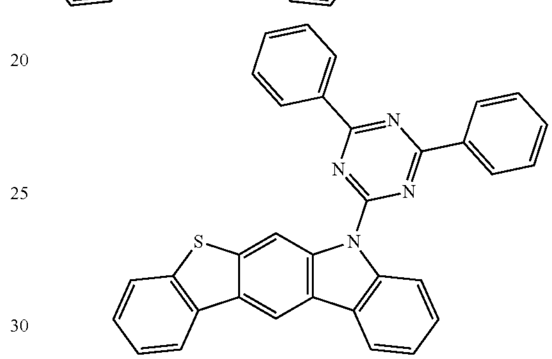
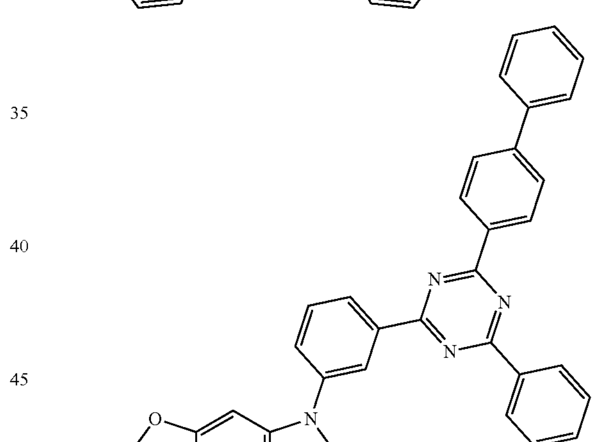
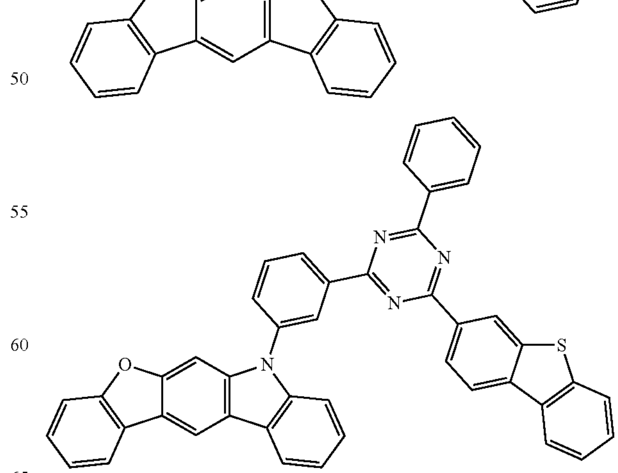

-continued
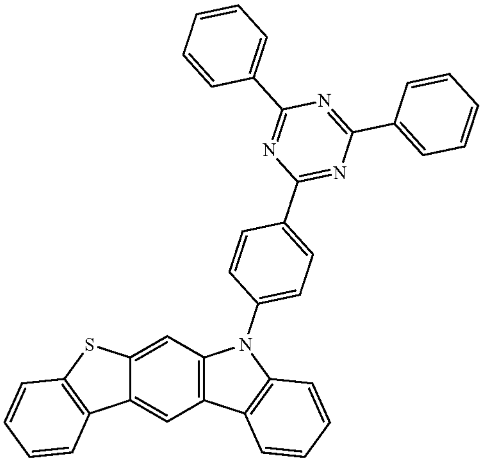
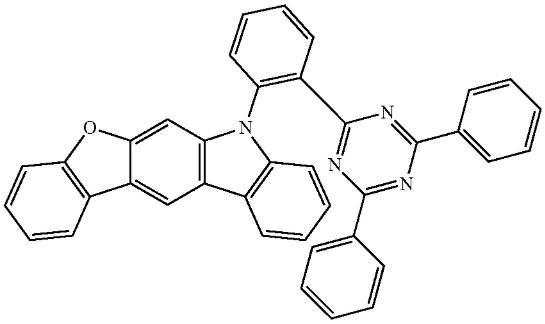
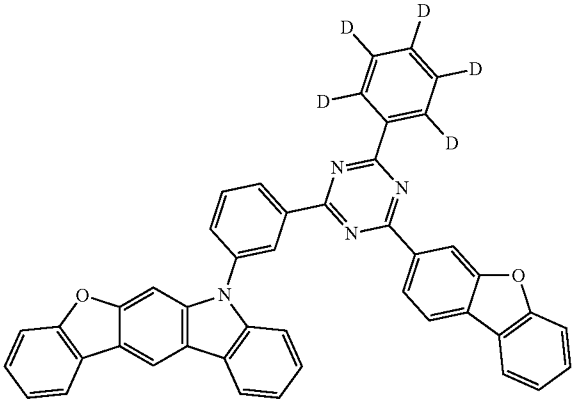
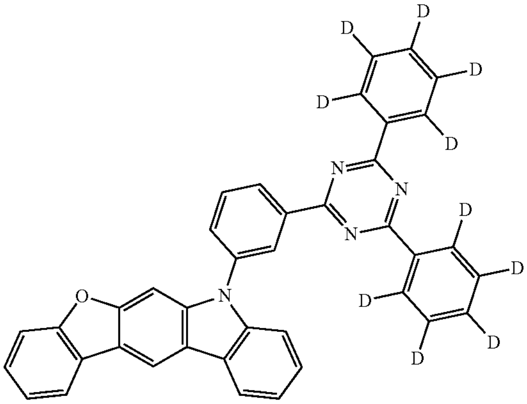
-continued
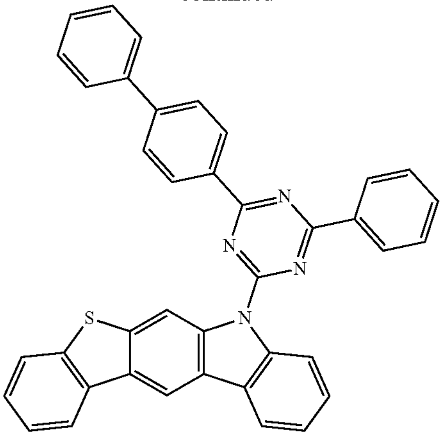
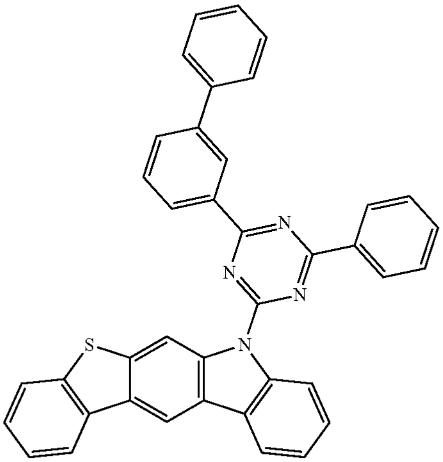
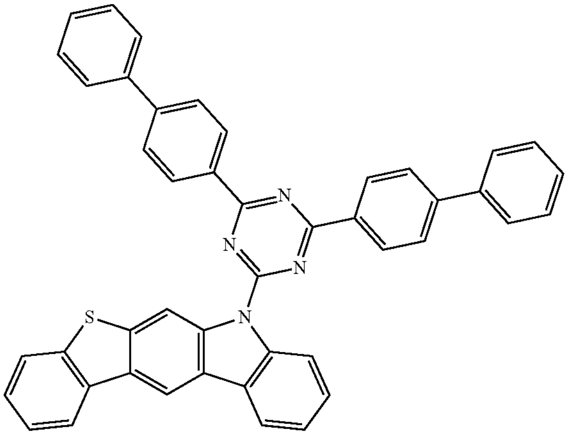

-continued
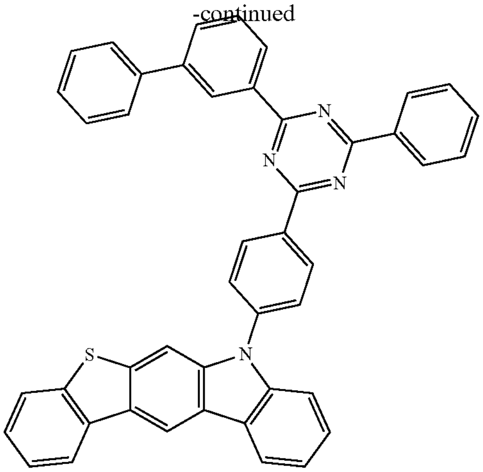
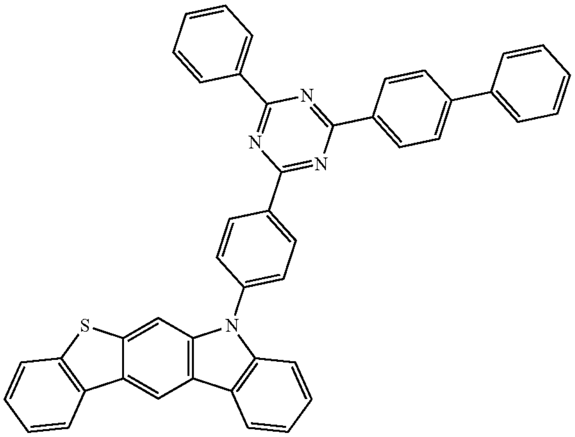
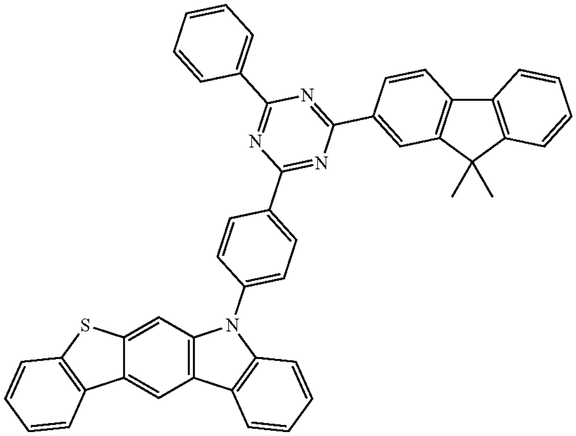
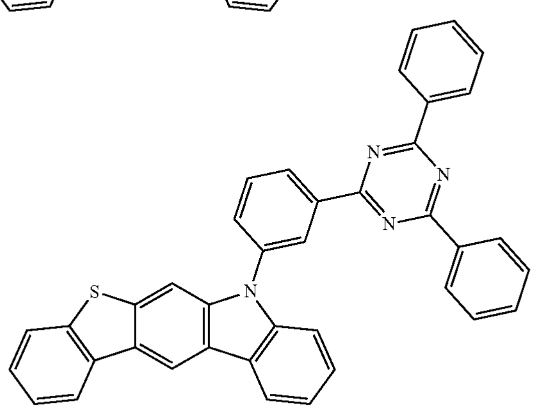
-continued
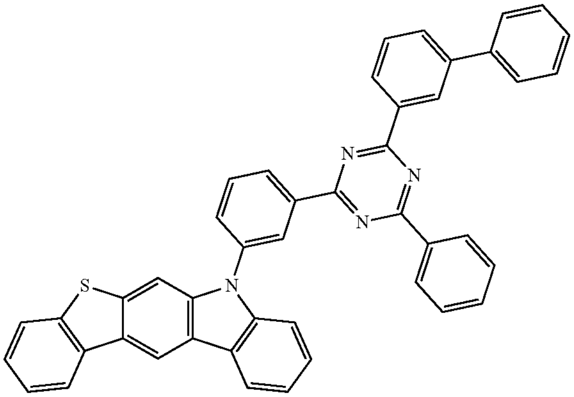
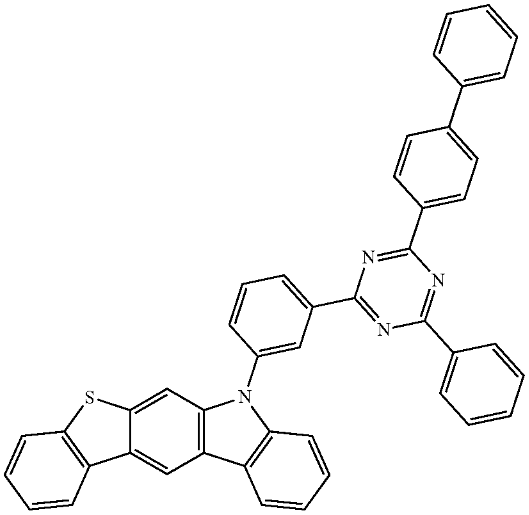
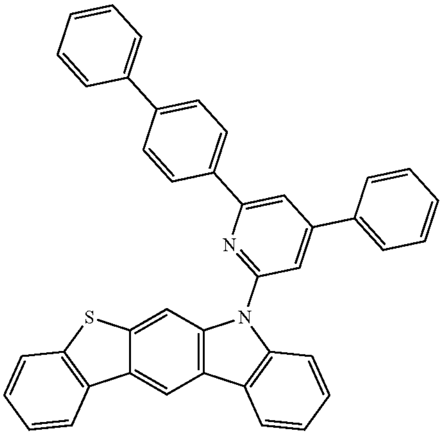
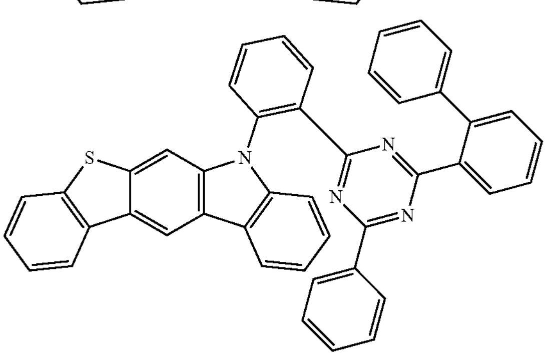

-continued
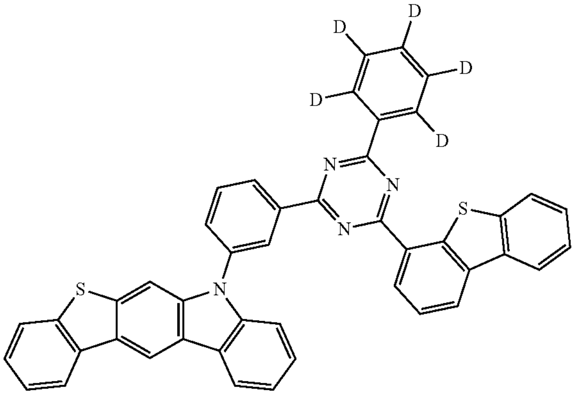
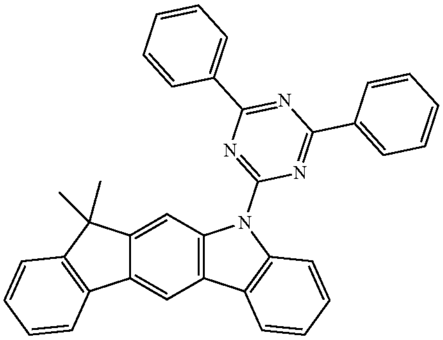
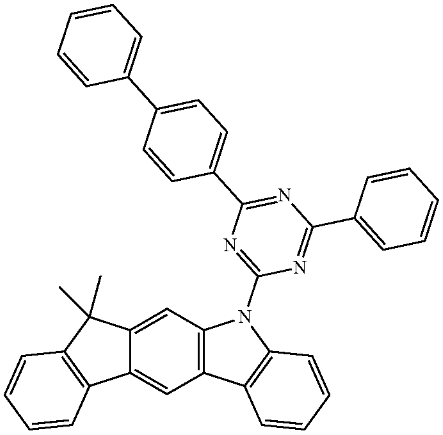
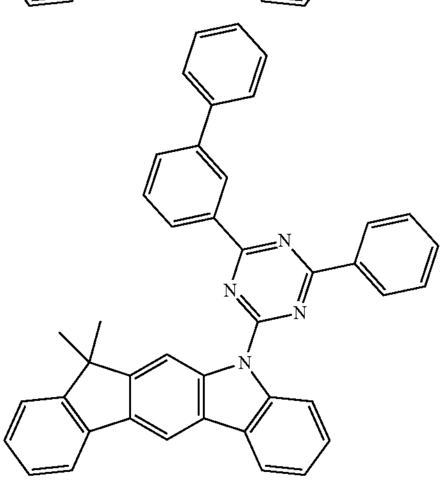
-continued
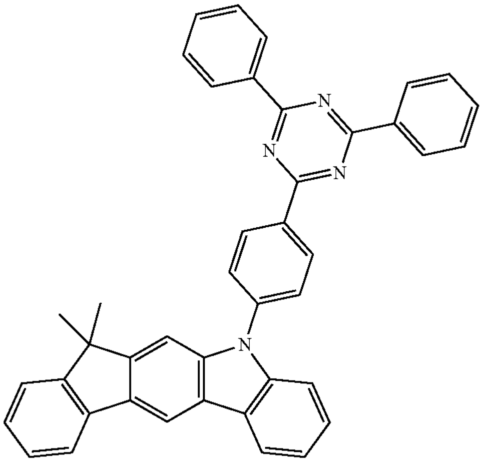
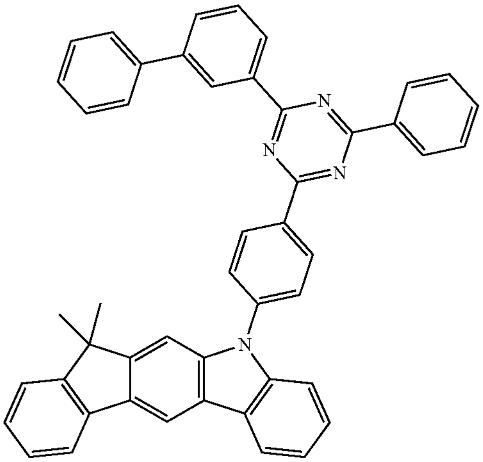
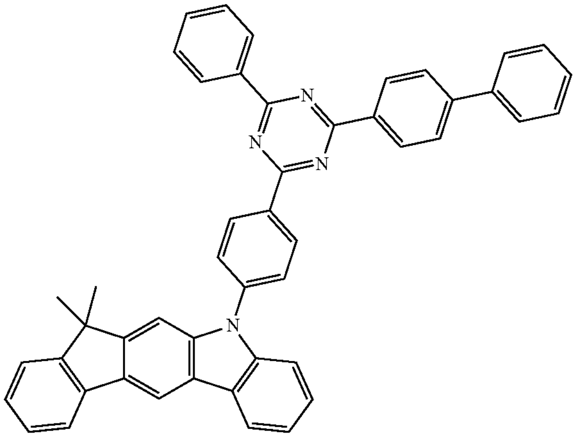

-continued
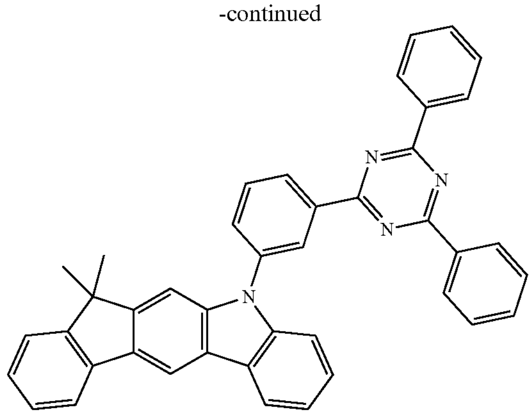
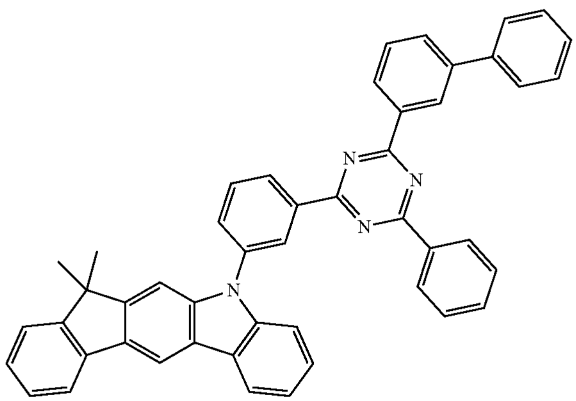
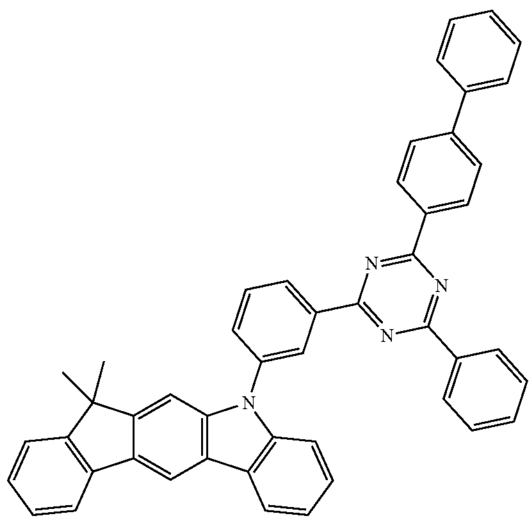
-continued
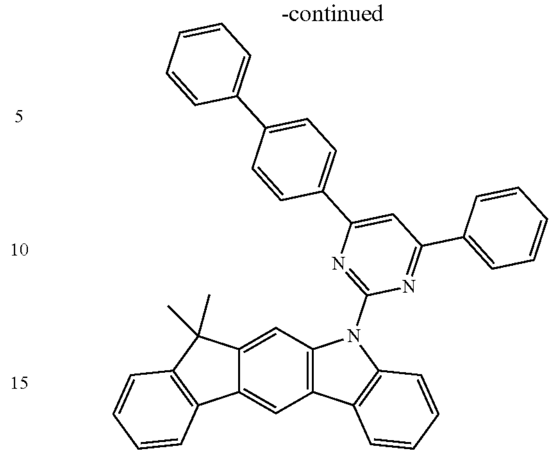
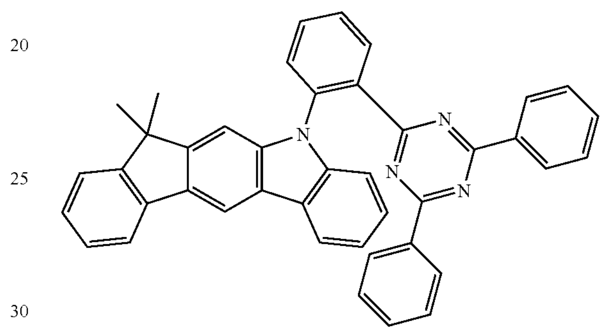
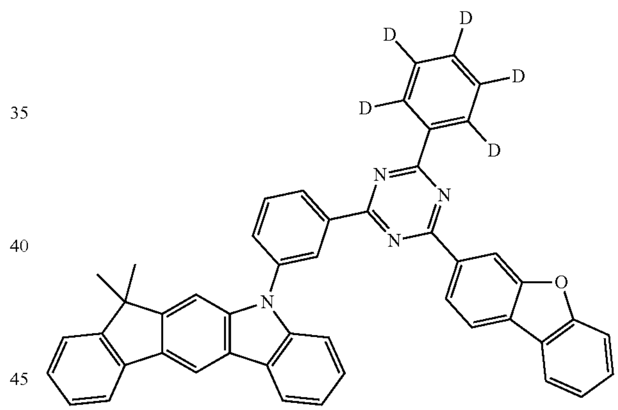
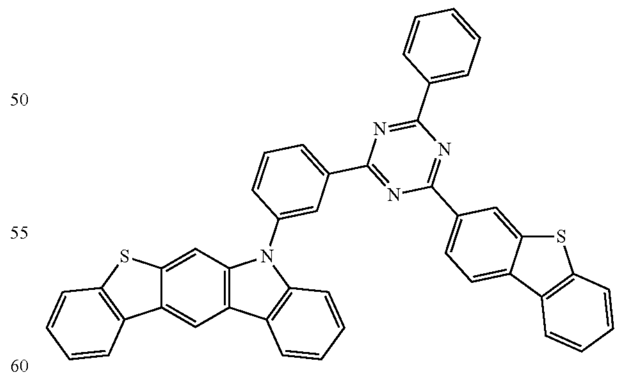

-continued
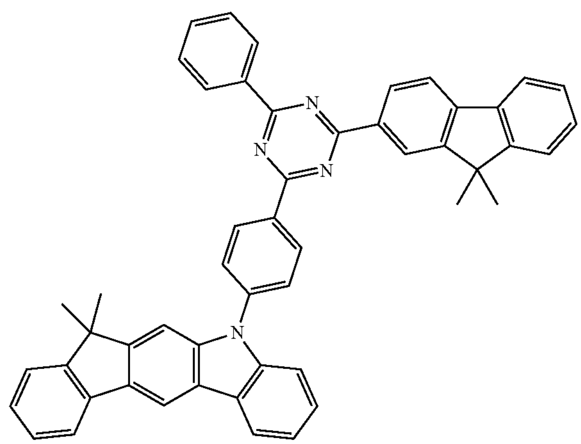
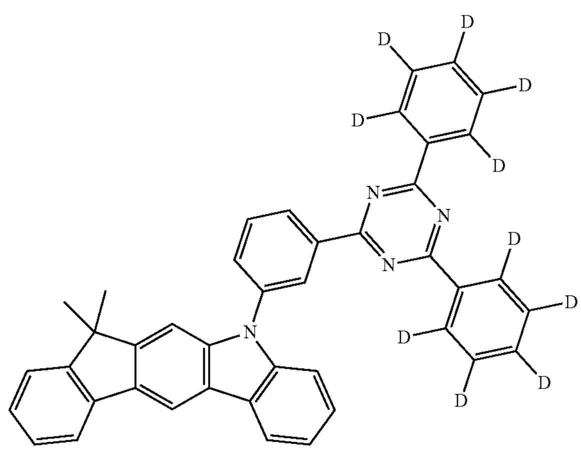
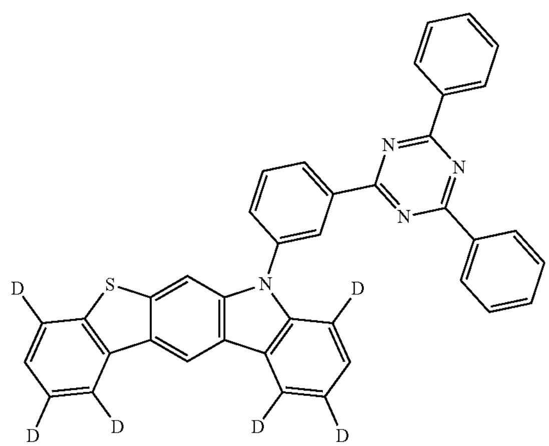
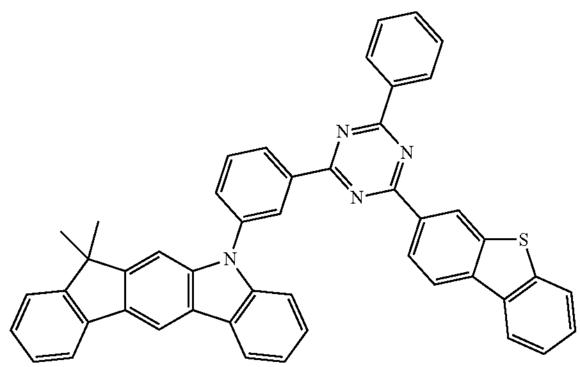
-continued
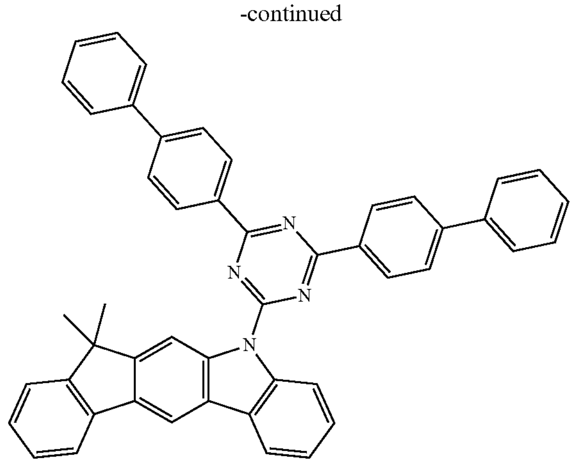
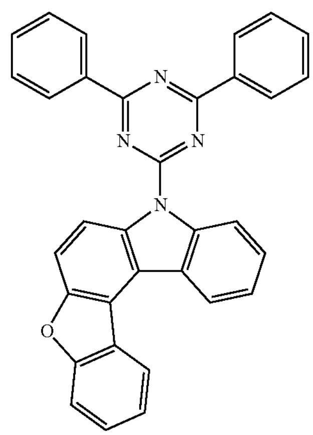
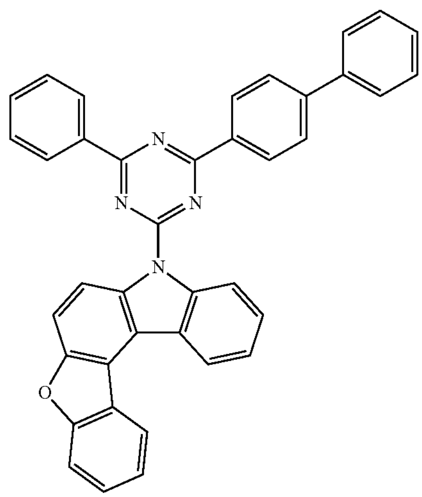

-continued
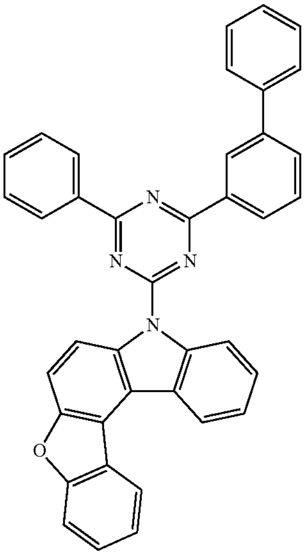
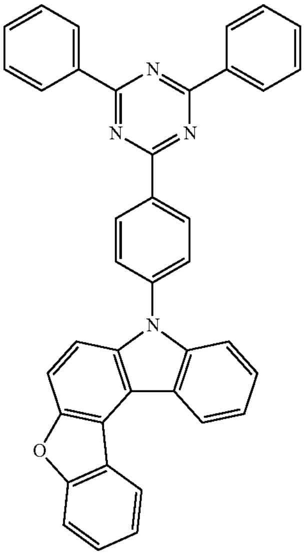
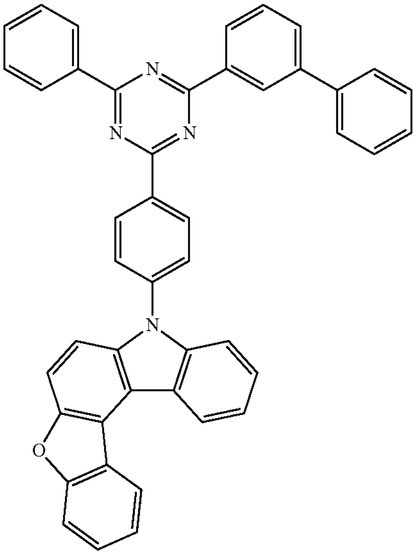
-continued
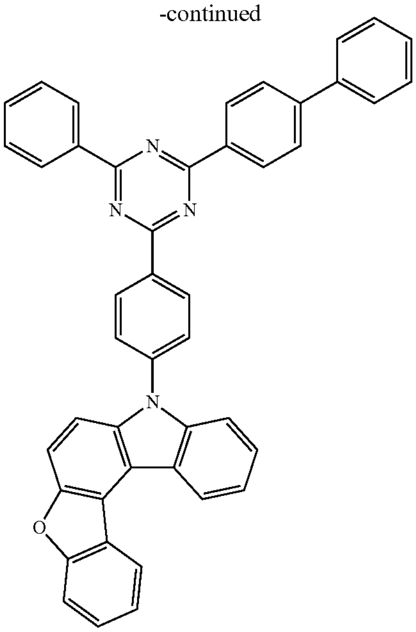
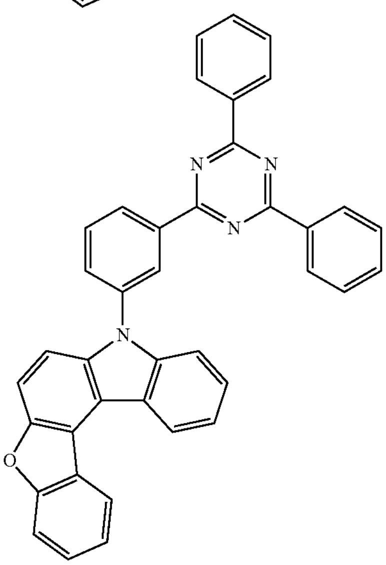
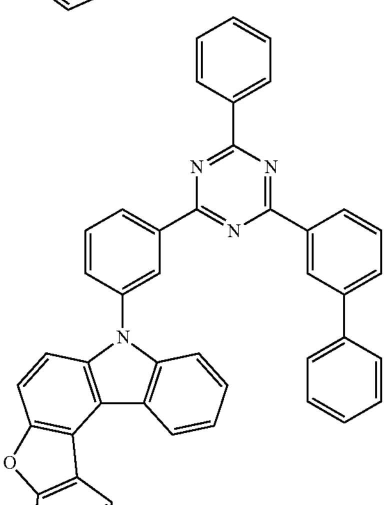

-continued
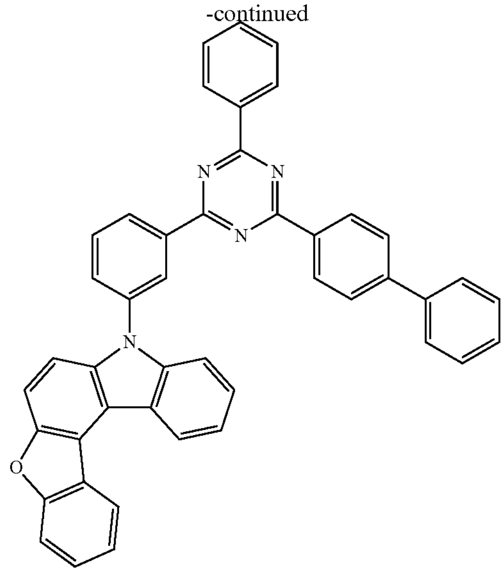
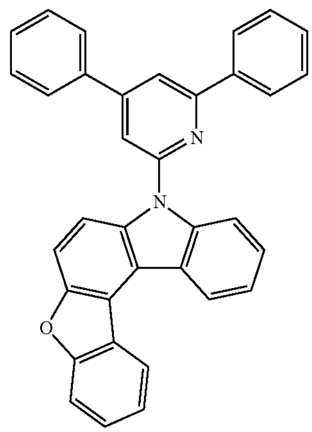
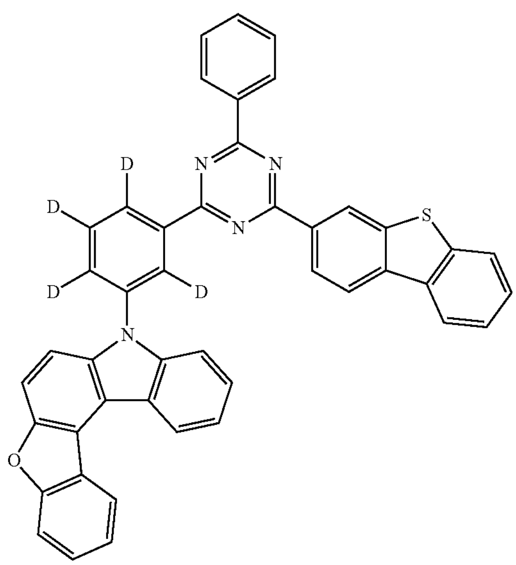
-continued
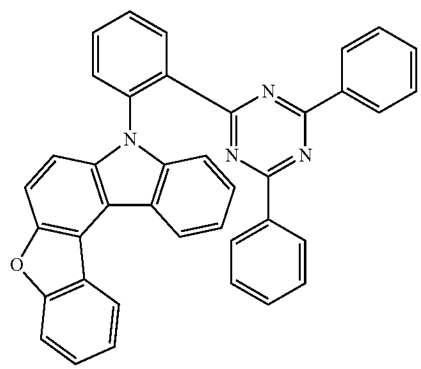
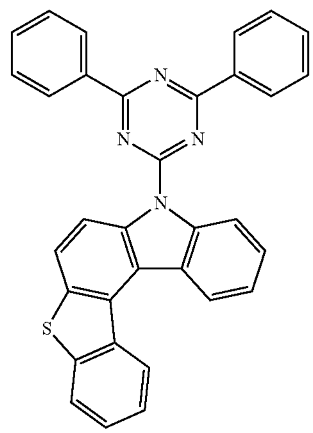
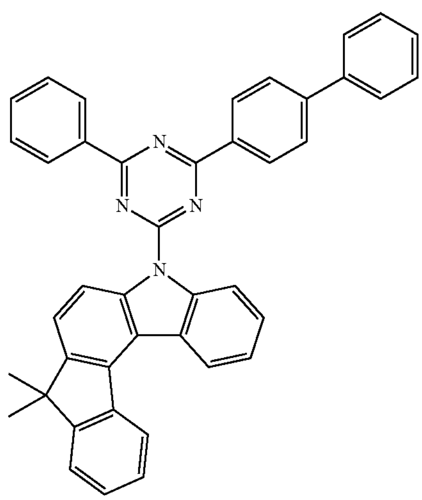

-continued
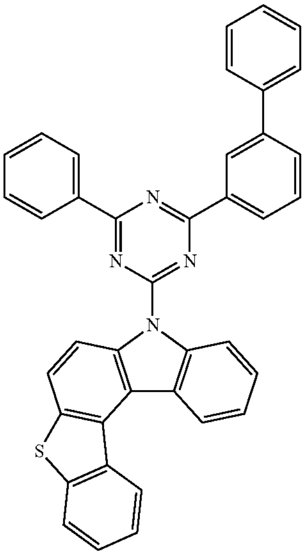
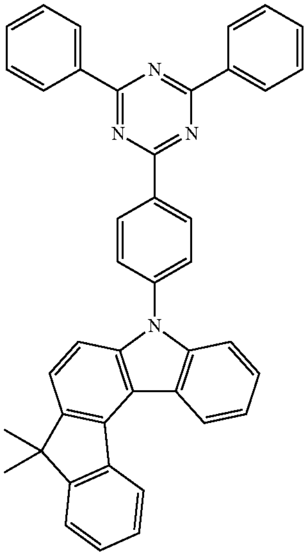
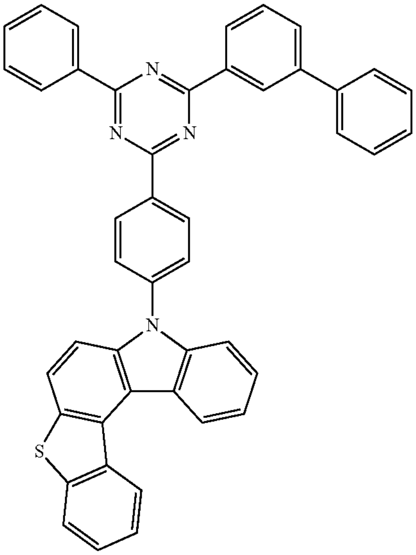
-continued
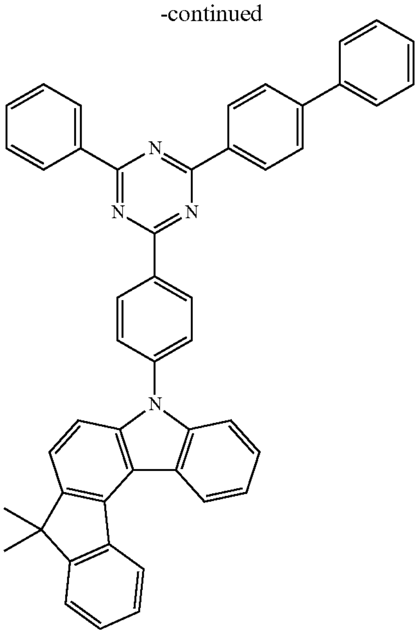
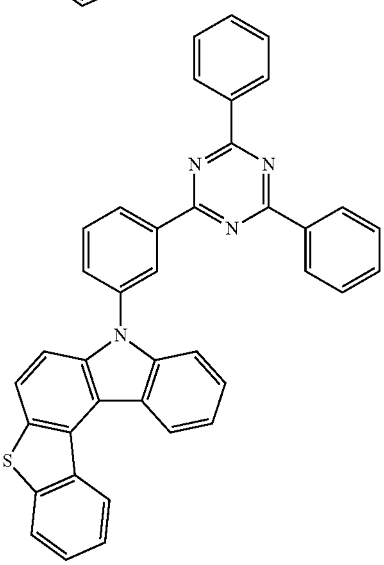
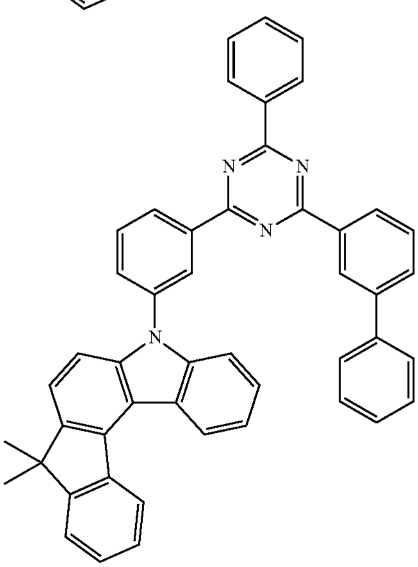

-continued
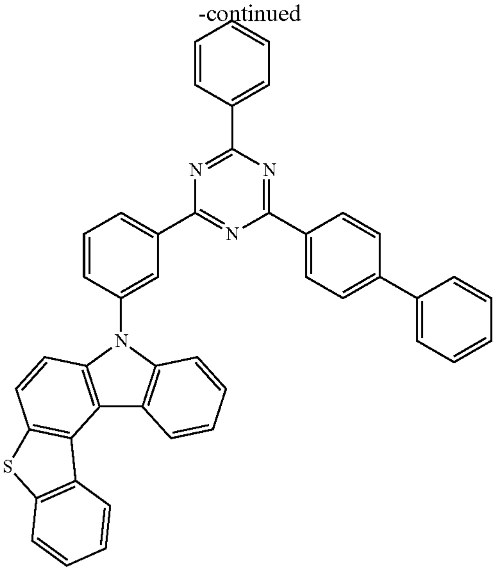
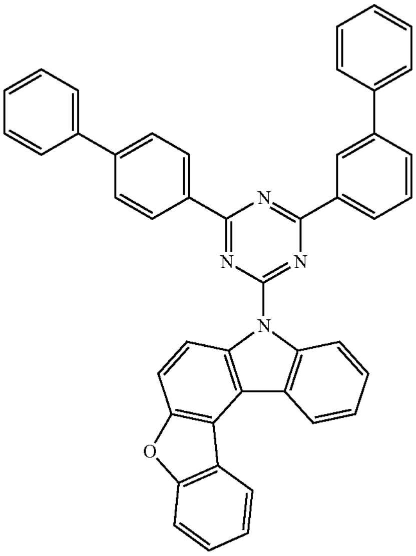
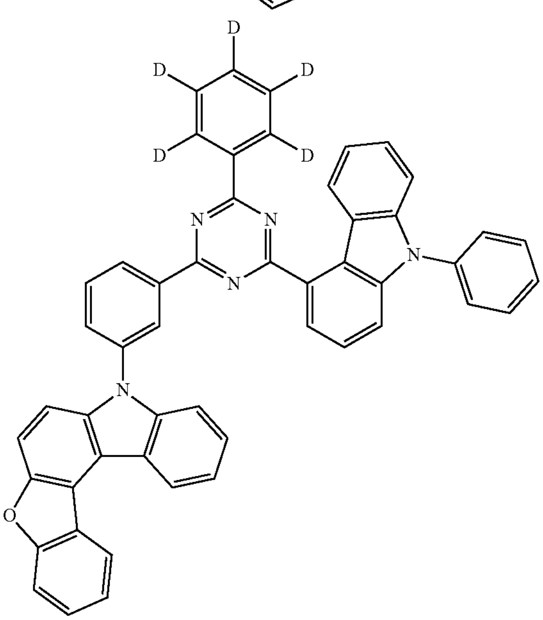
-continued
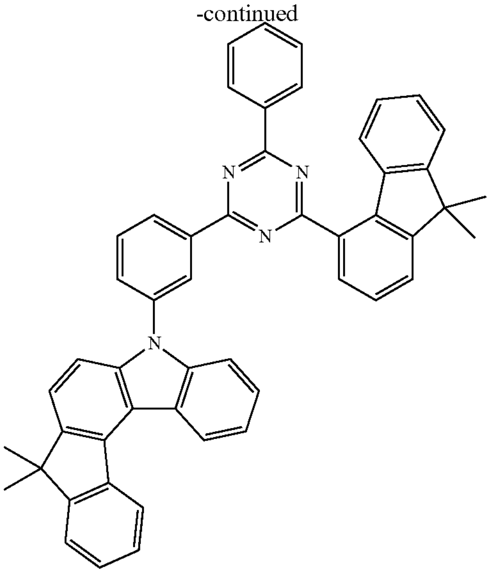
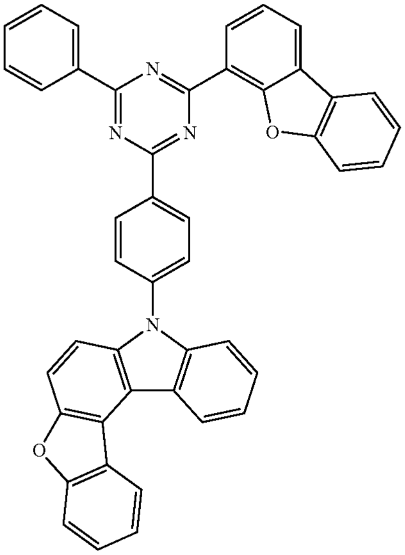
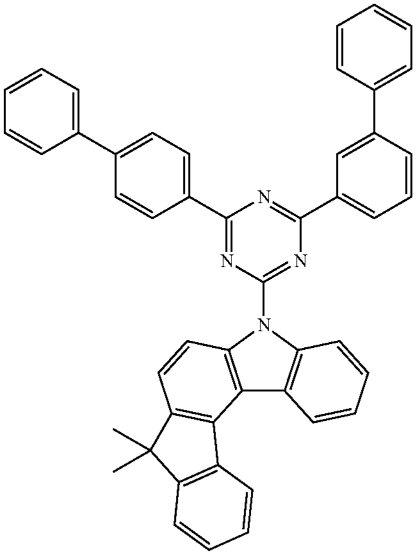

-continued
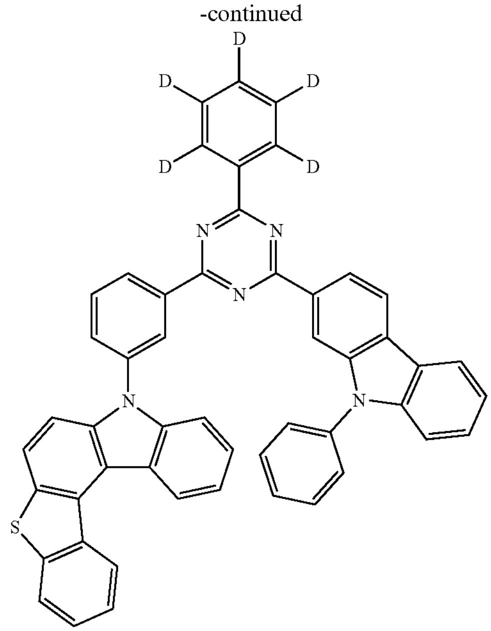
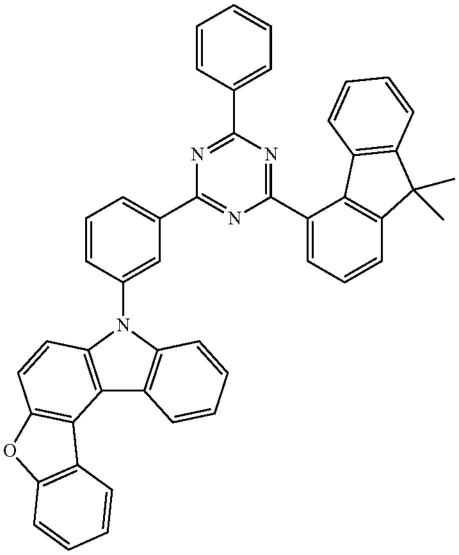
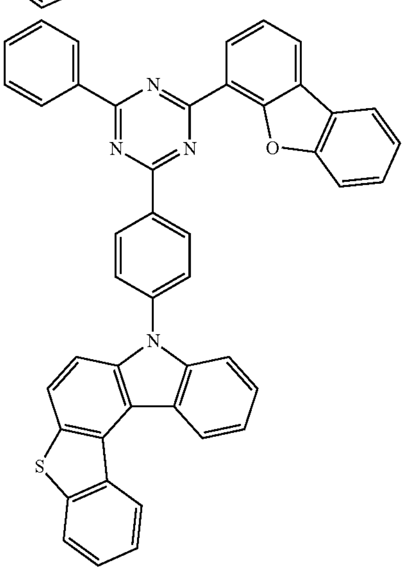
-continued
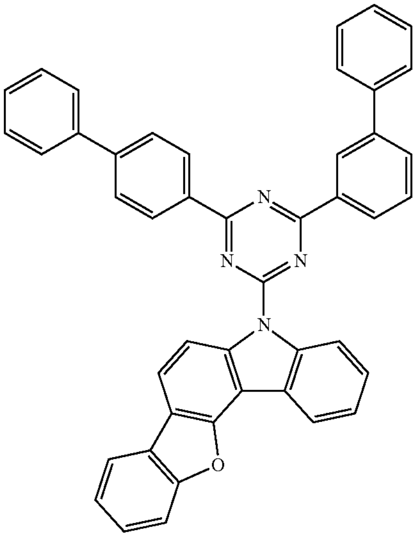
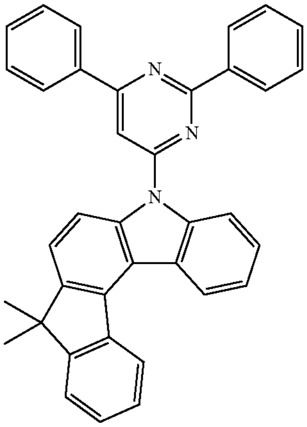
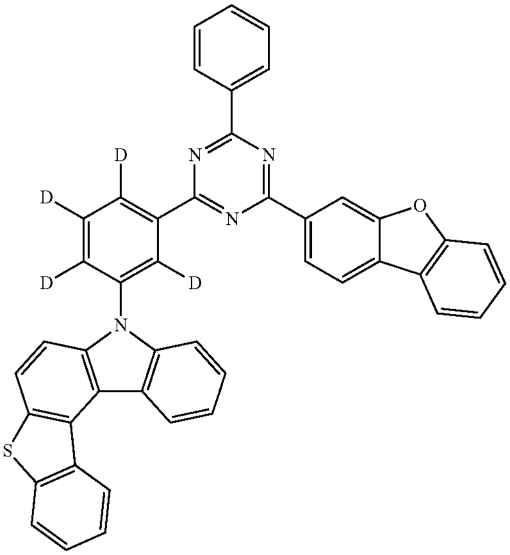

-continued
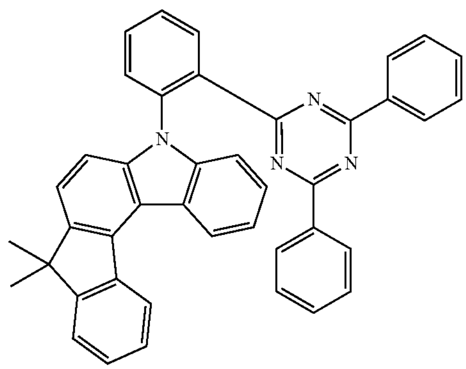
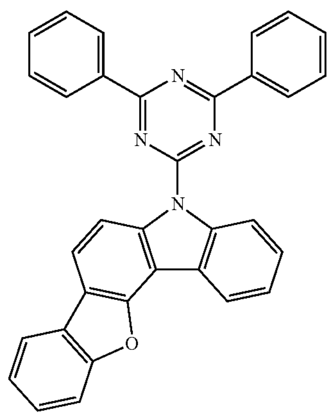
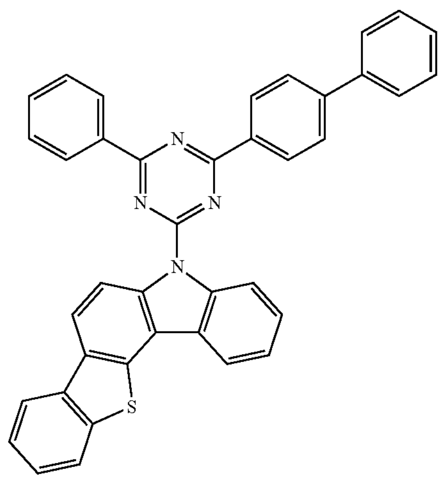
-continued
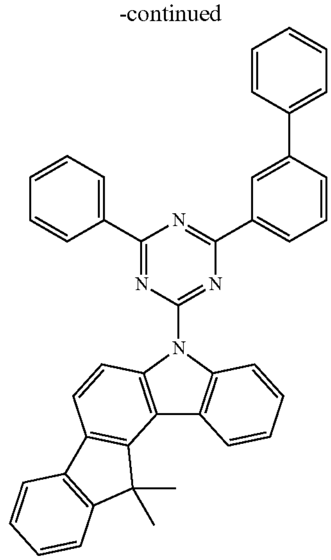
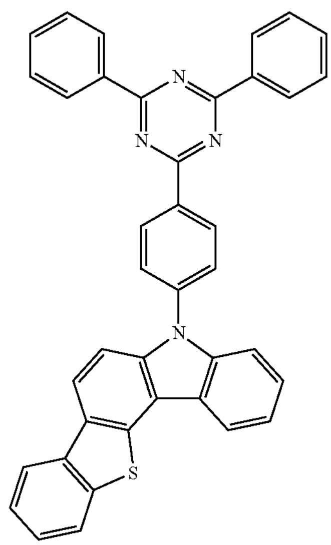
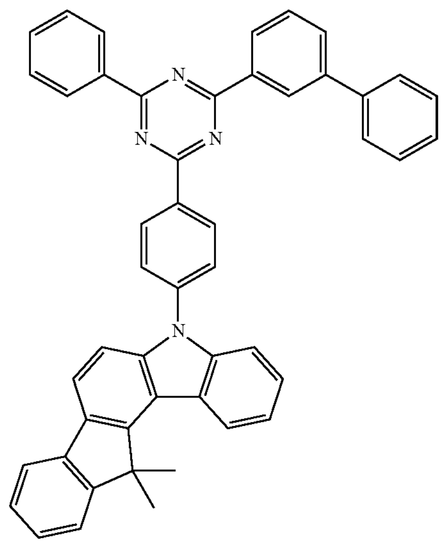

-continued
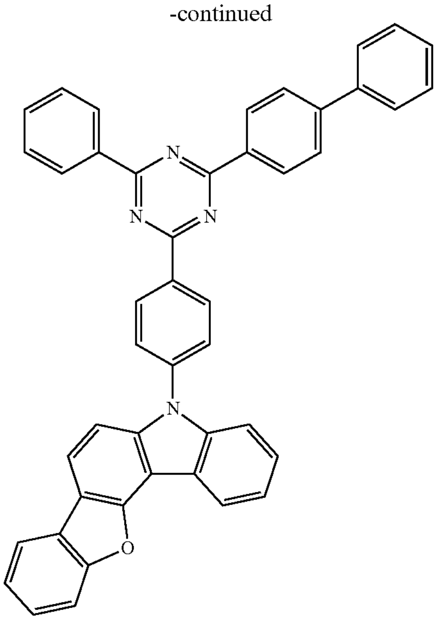
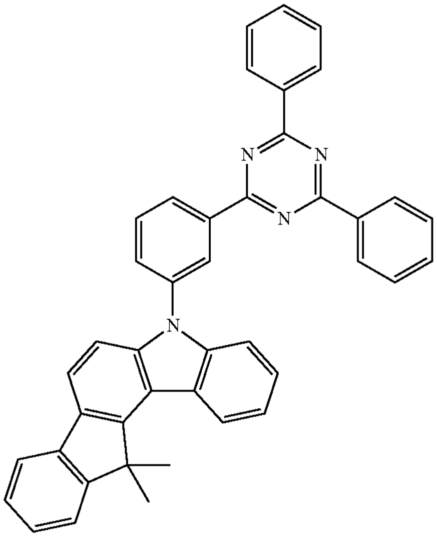
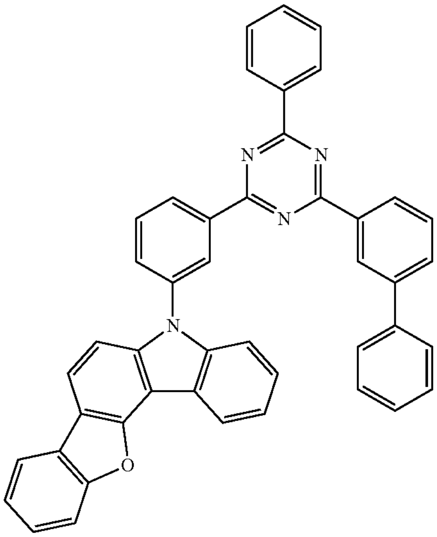
-continued
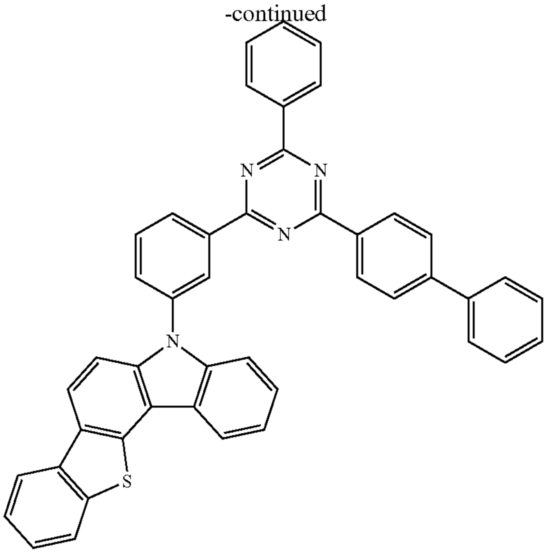
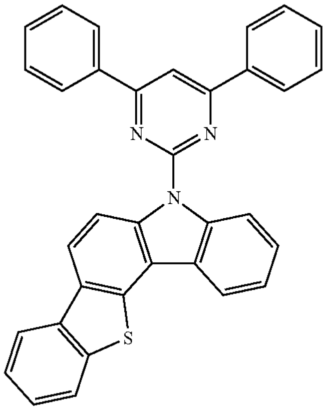
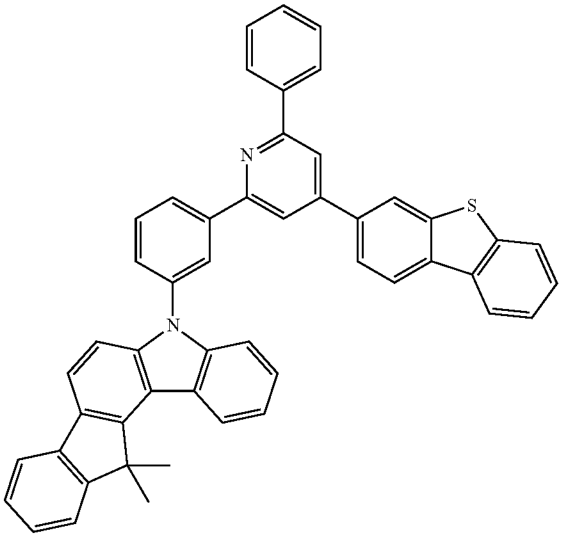

-continued
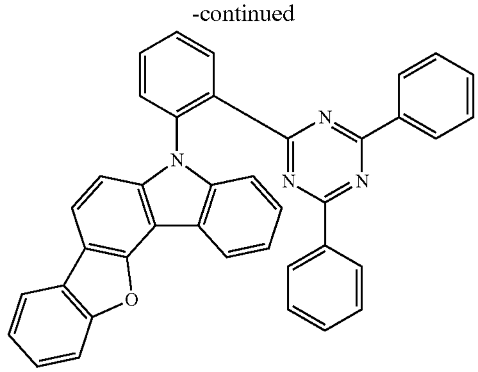
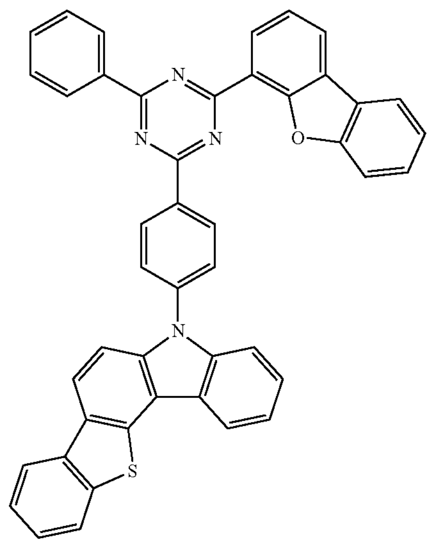
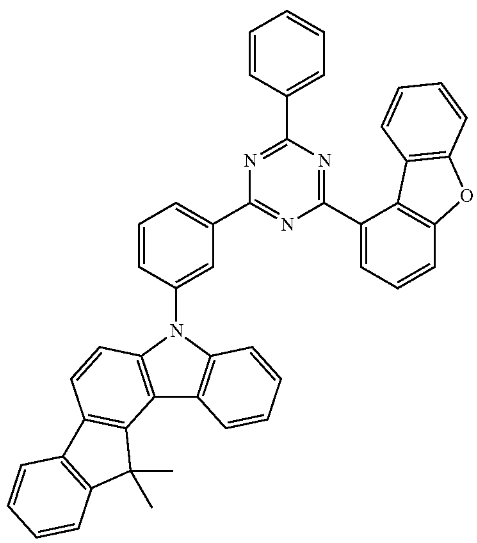
-continued
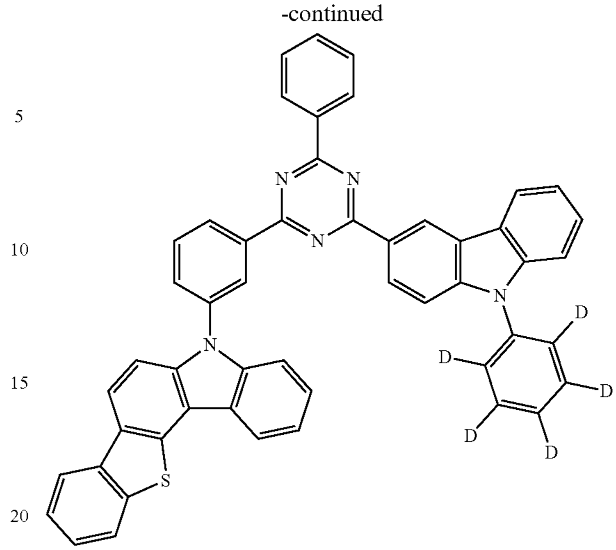
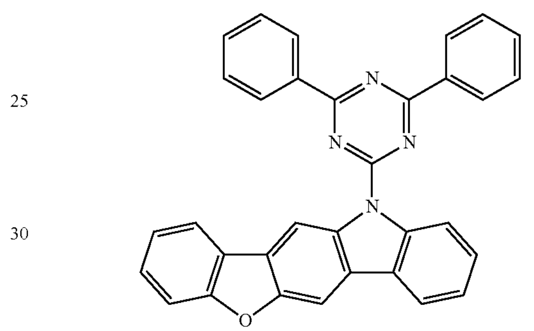
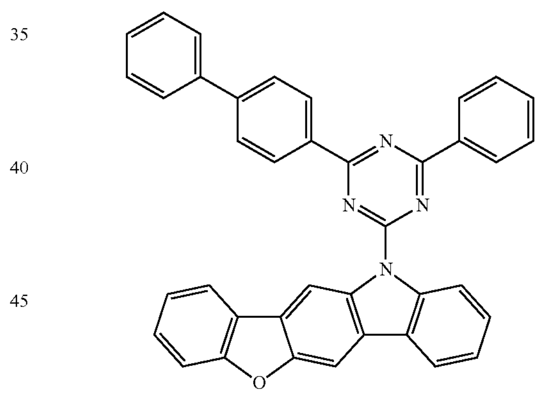
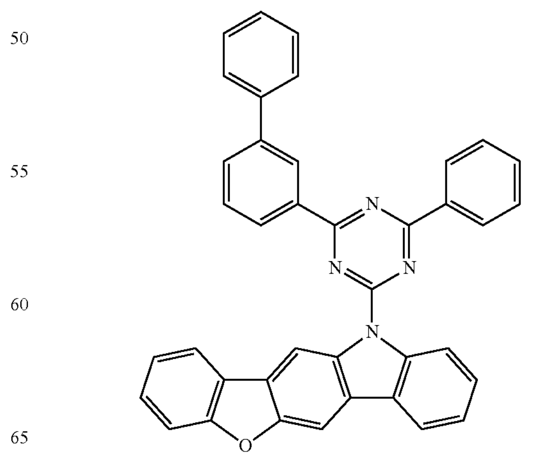

-continued
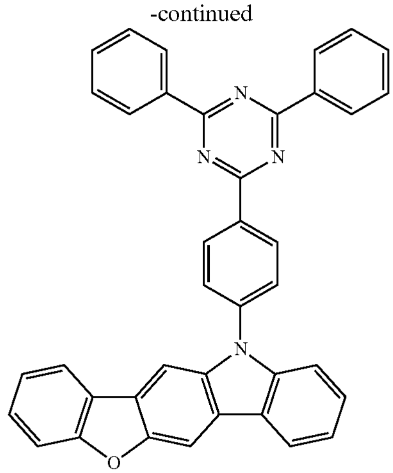
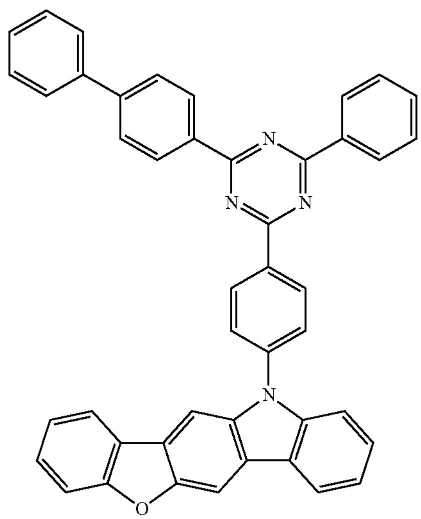
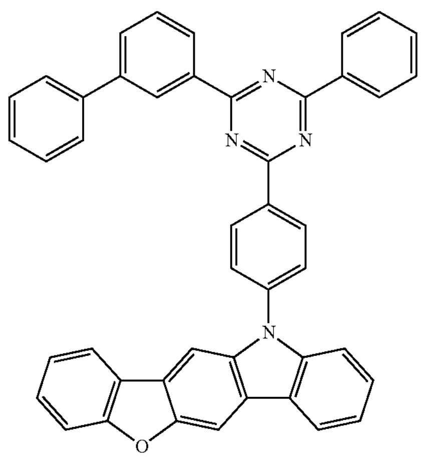
-continued
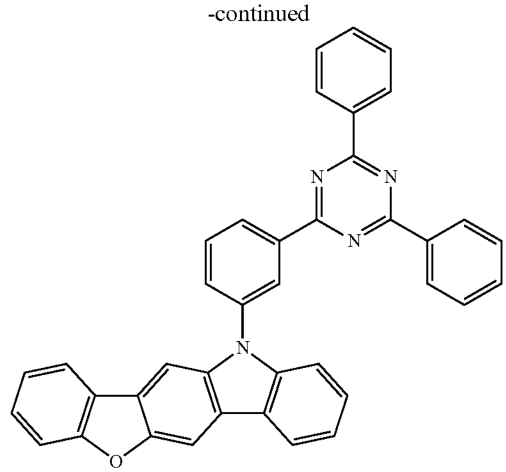
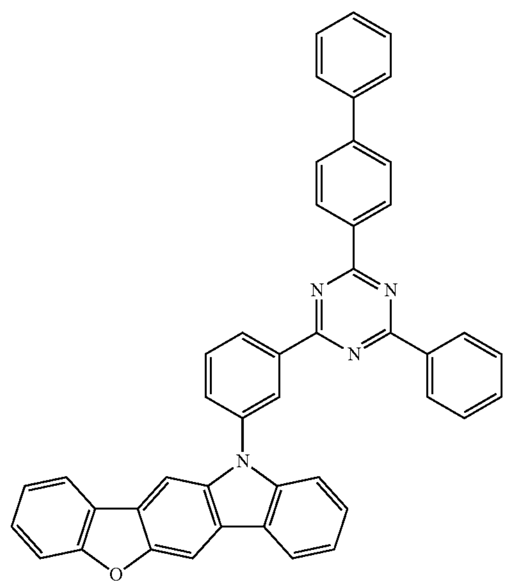
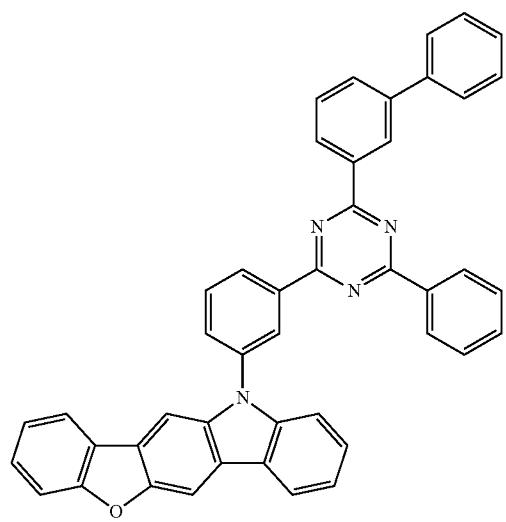

-continued
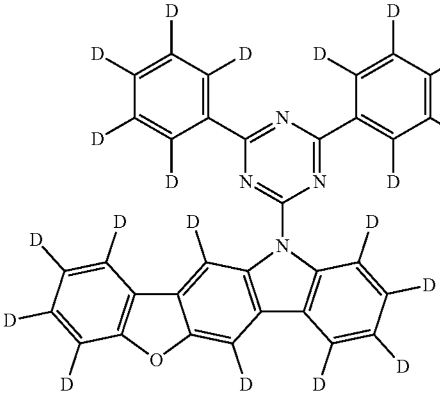
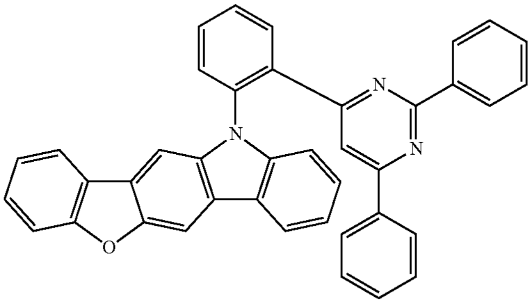
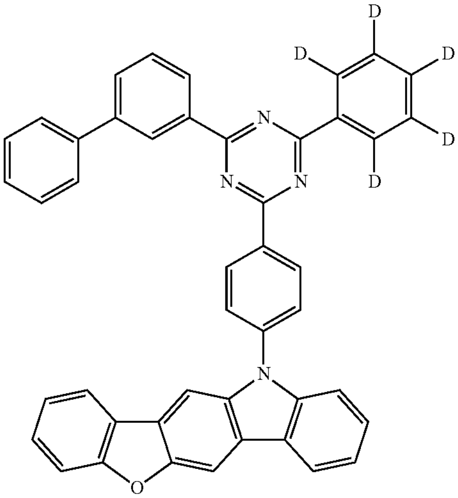
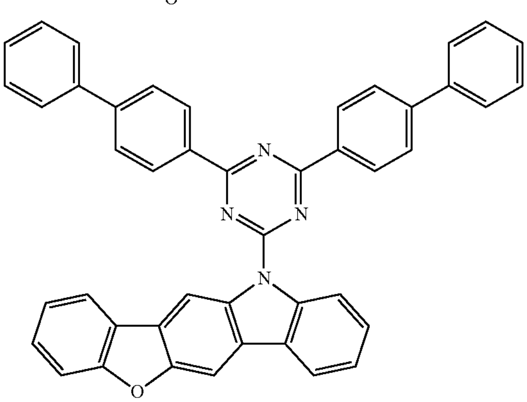
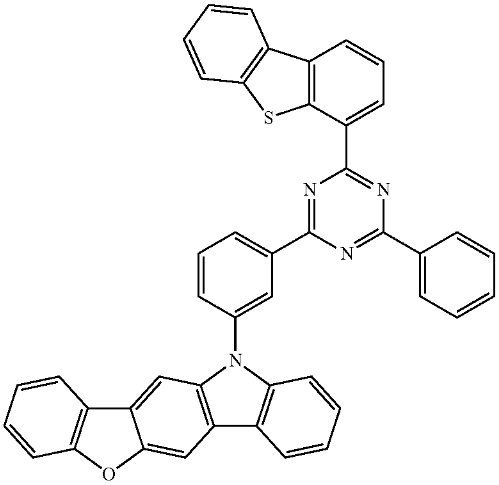
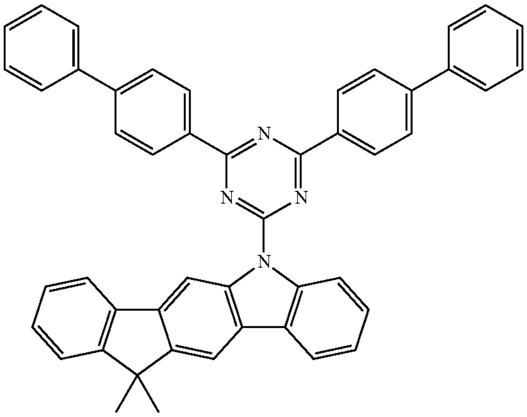
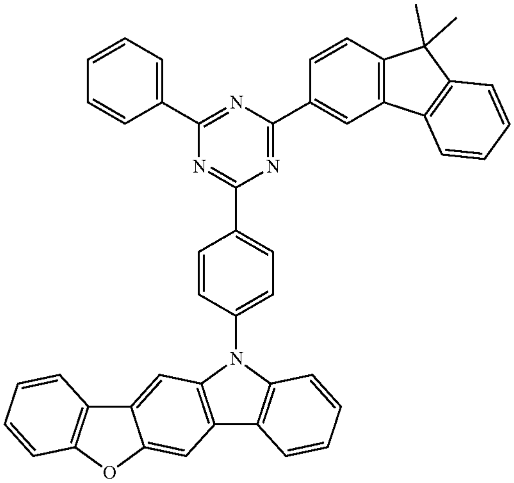

-continued
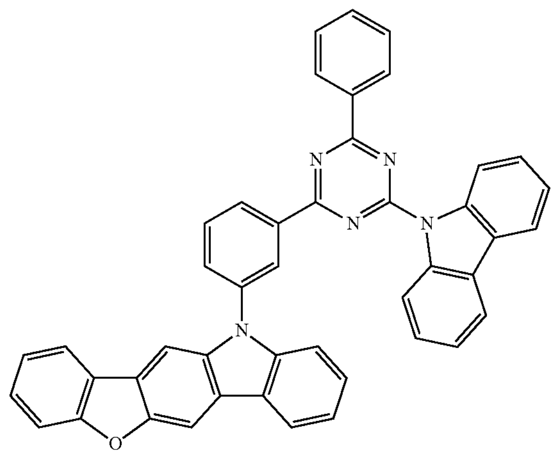
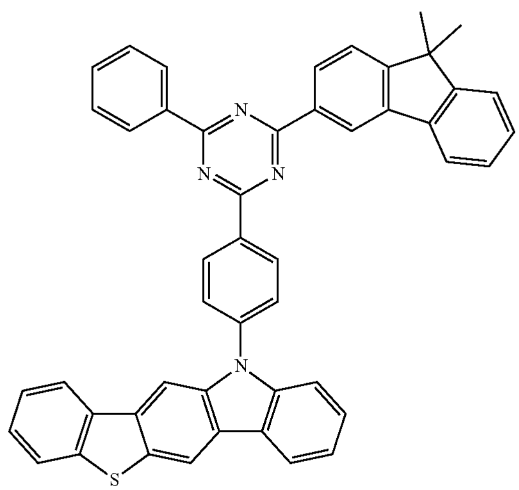
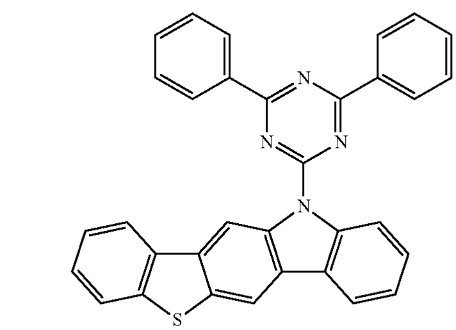
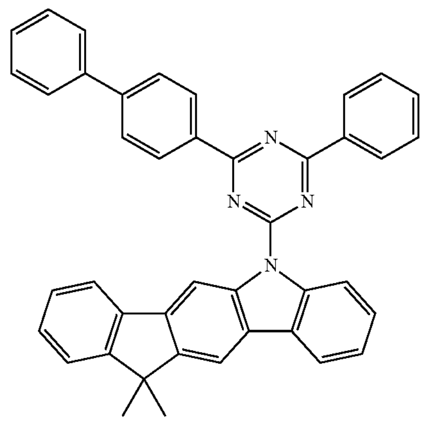
-continued
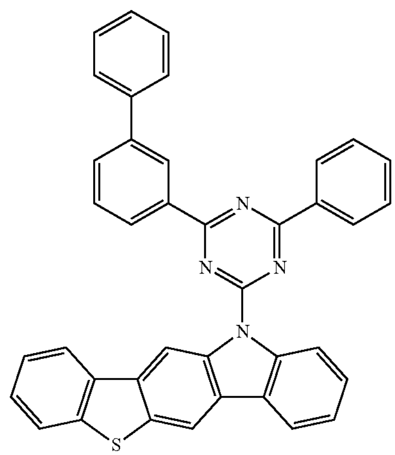
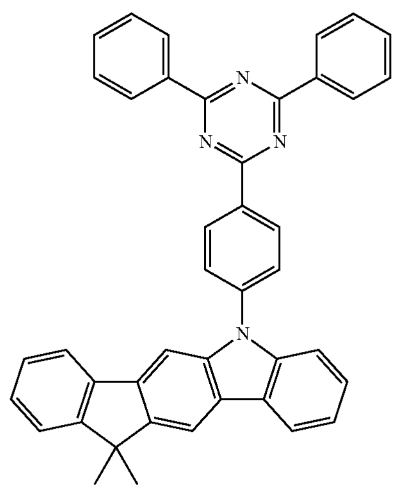
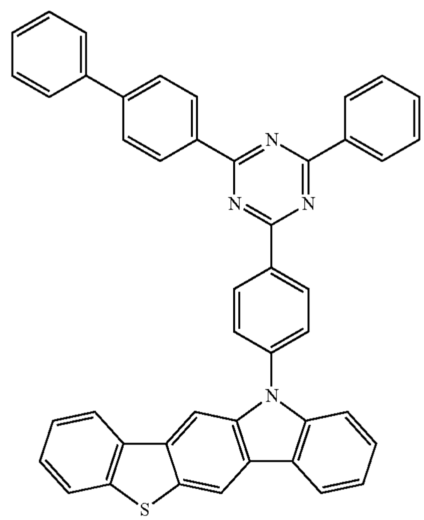

-continued
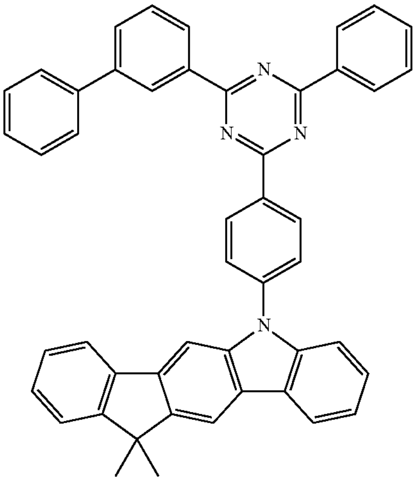
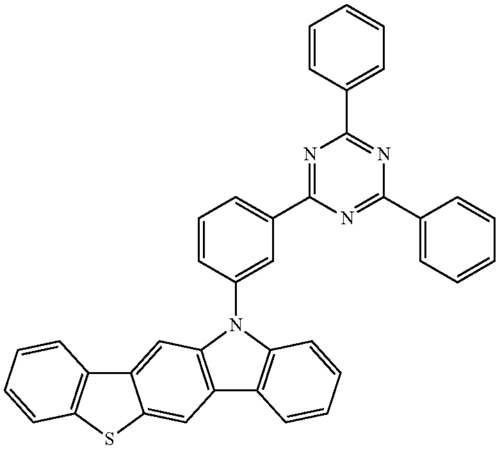
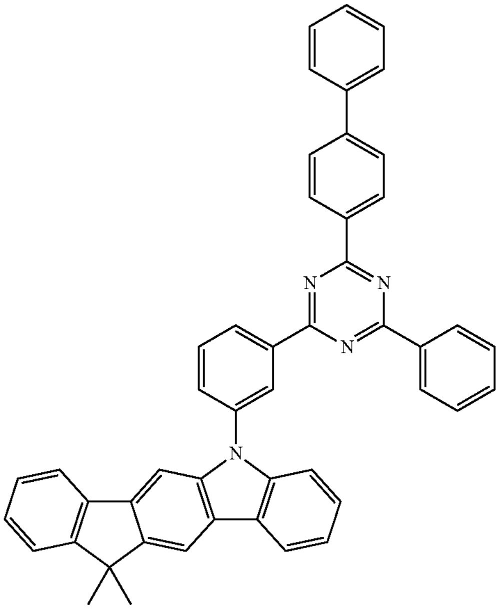
-continued
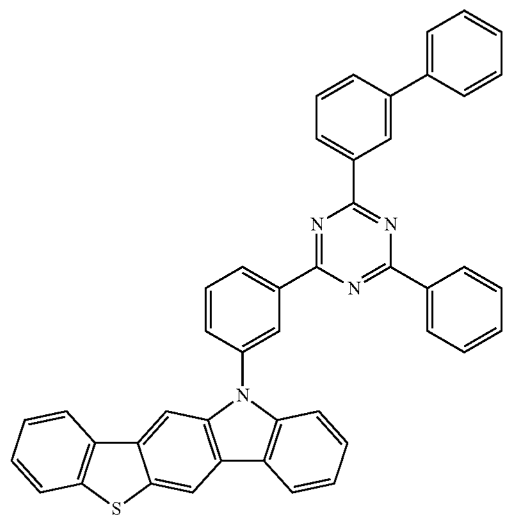
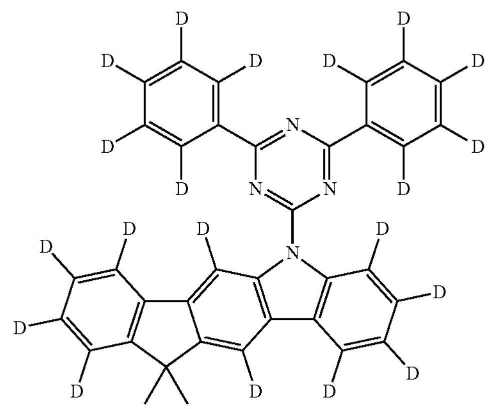
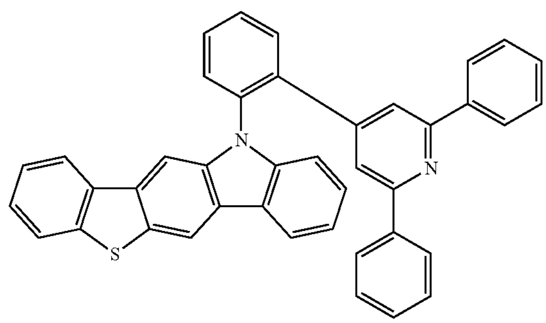

-continued
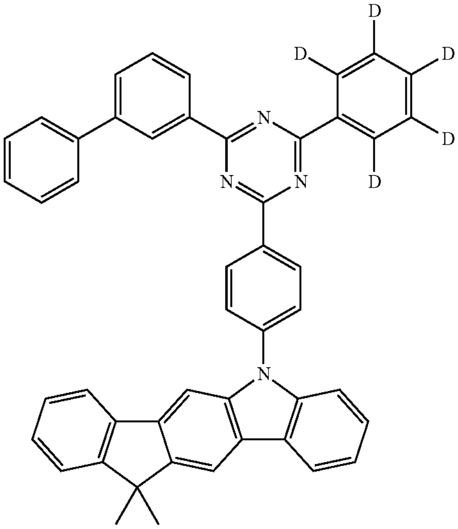
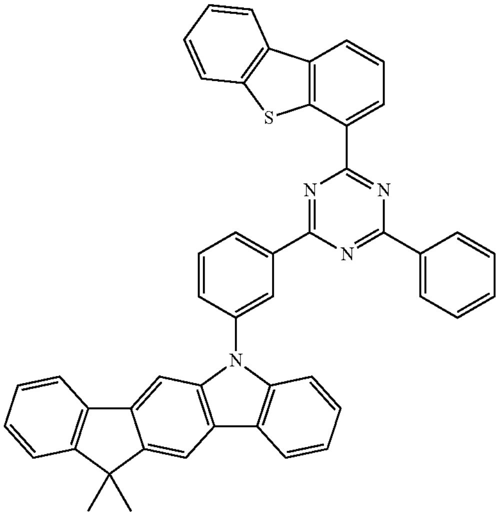
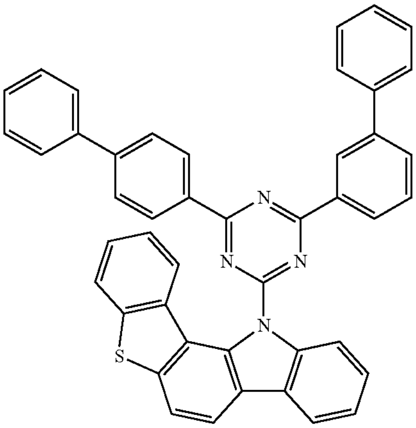
-continued
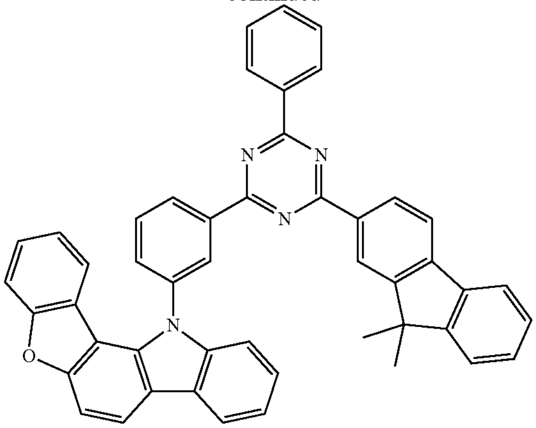
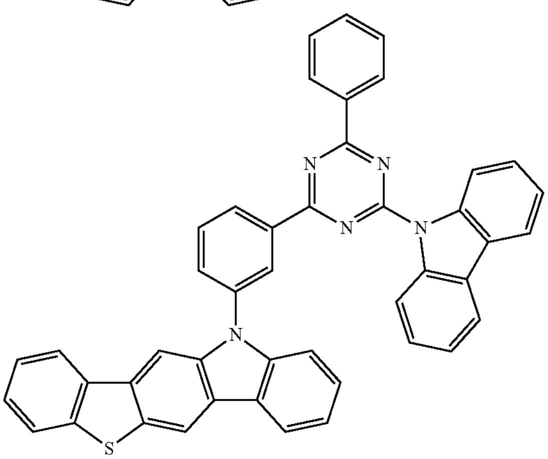
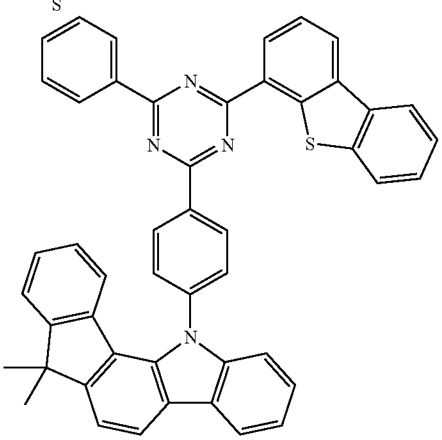
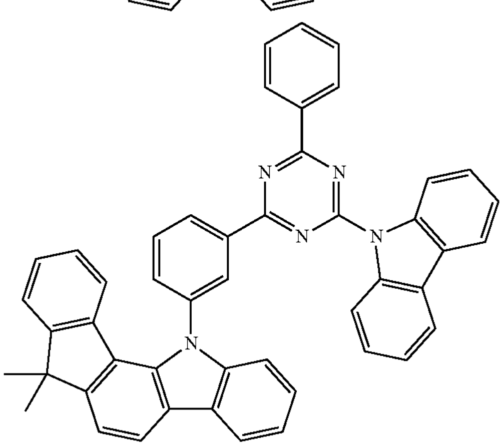

-continued
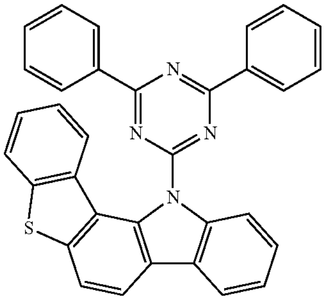
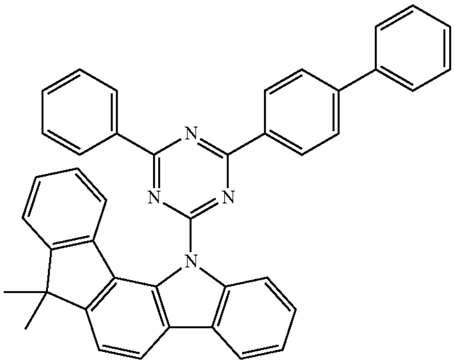
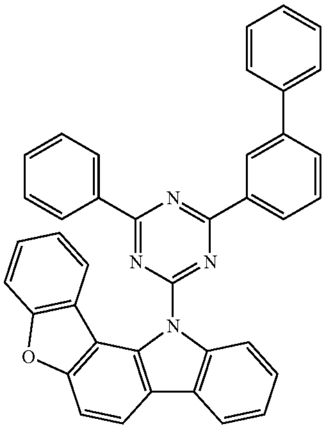
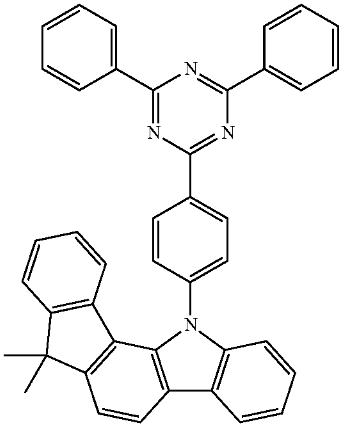
-continued
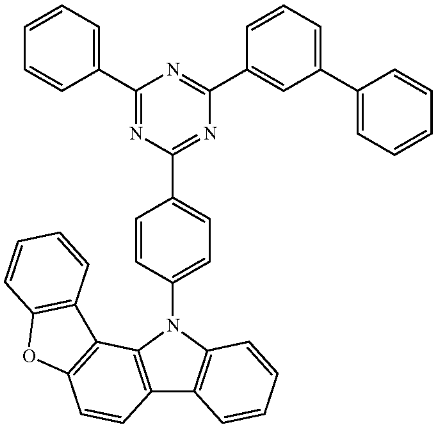
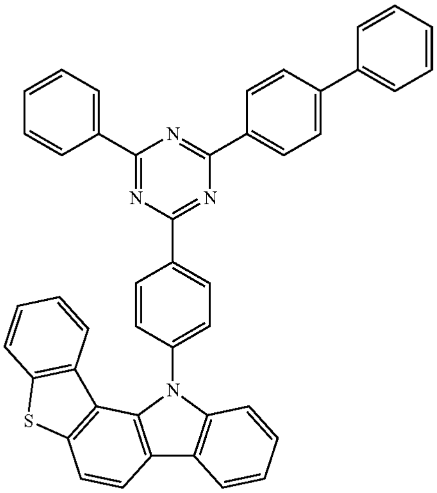
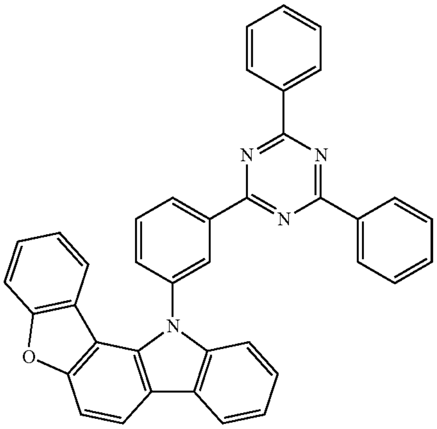

-continued
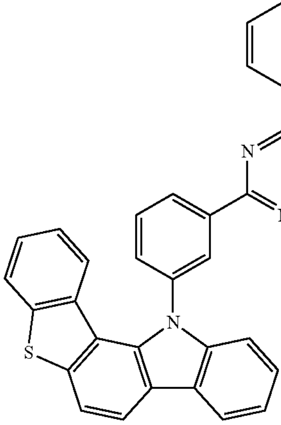
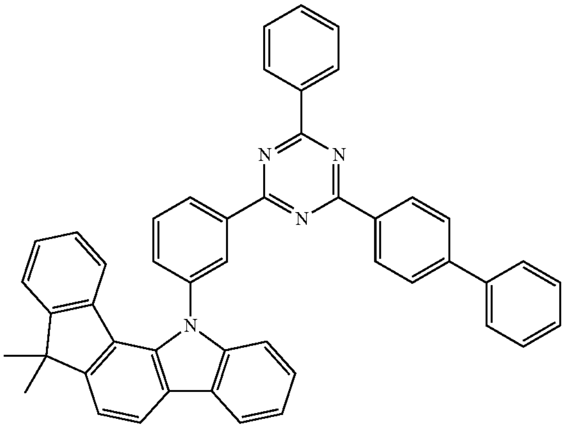
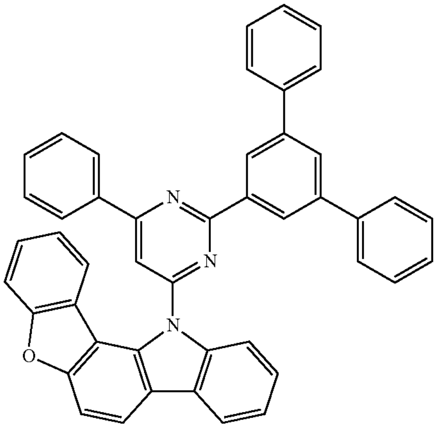
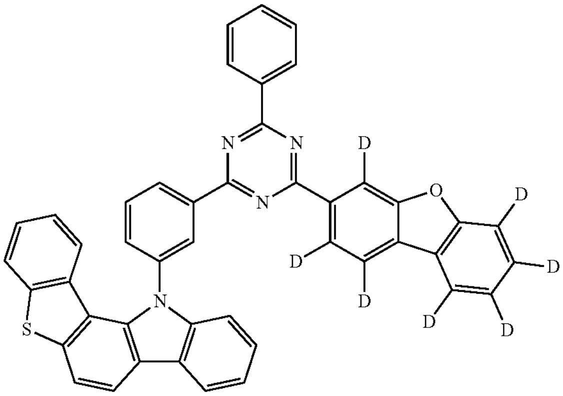
-continued
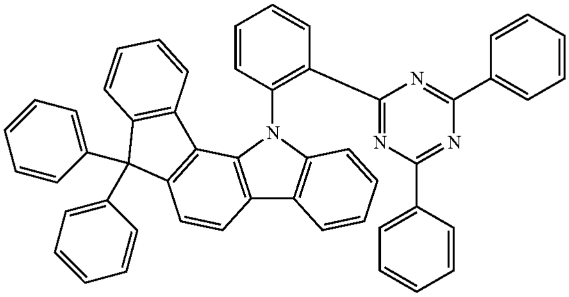
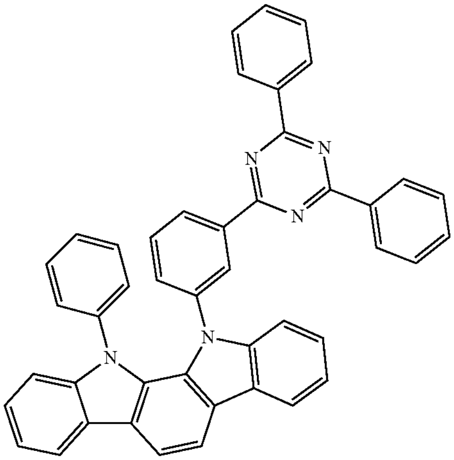
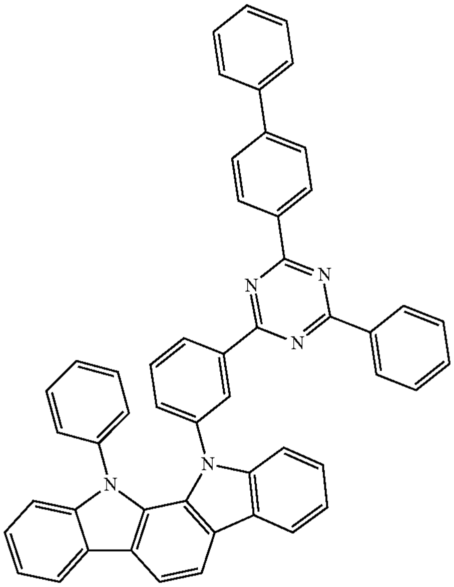

-continued
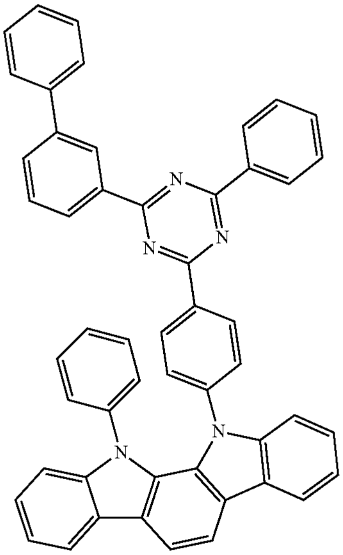 [SMILES: c1ccc(-c2cccc(-c3nc(-c4ccccc4)nc(-c4ccc(-n5c6ccccc6c6ccc7c8ccccc8n(-c8ccccc8)c7c65)cc4)n3)c2)cc1]
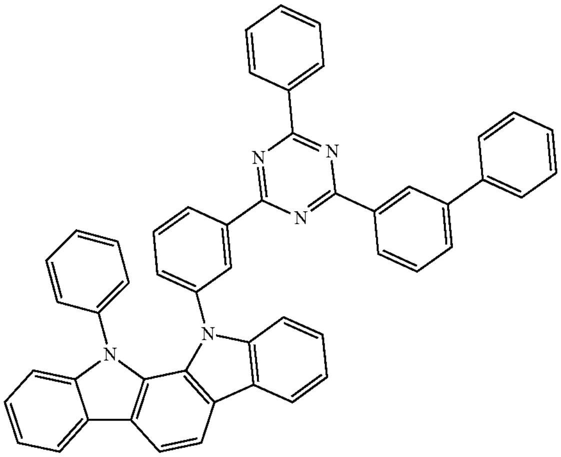
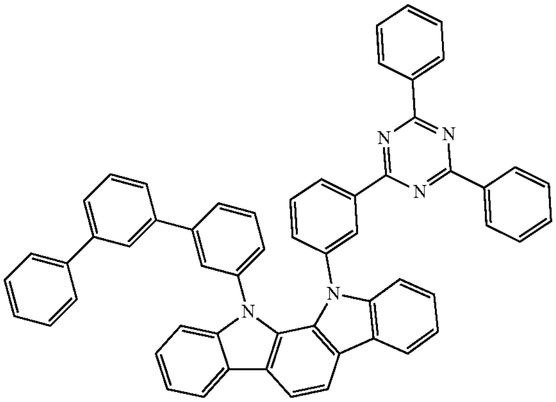
-continued
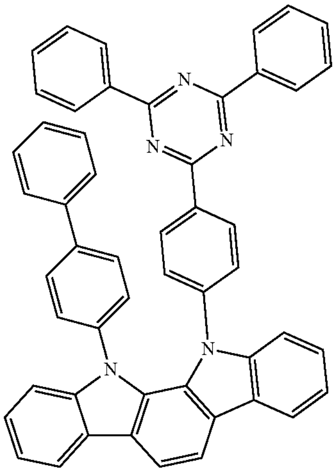
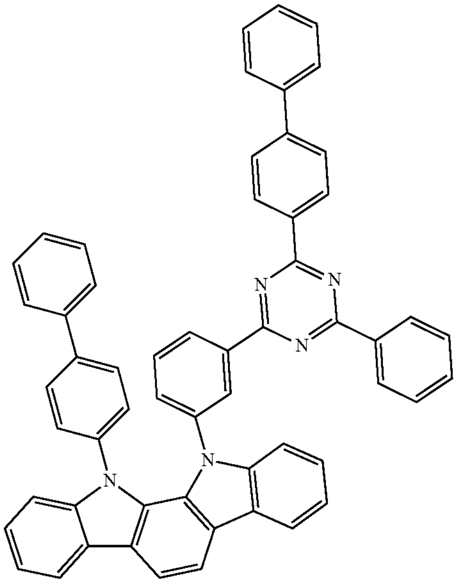
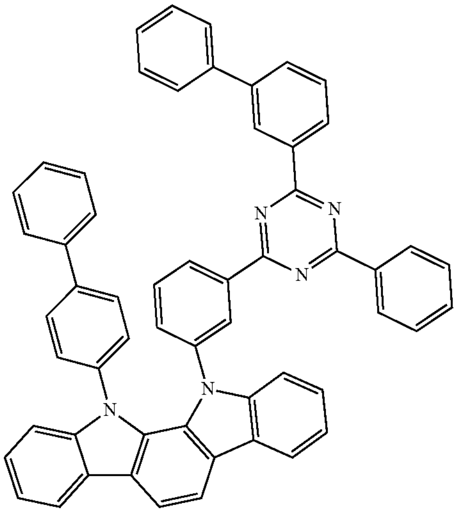

-continued
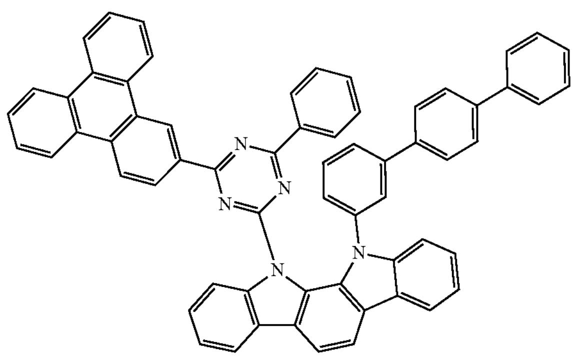
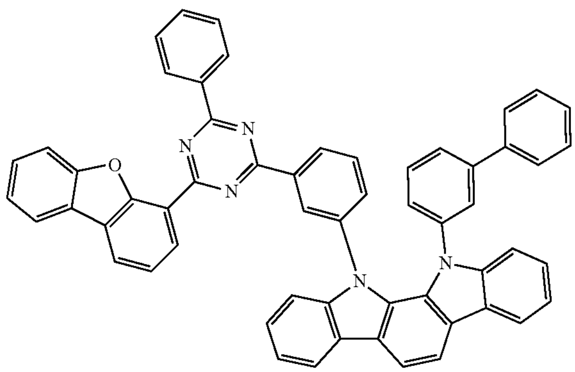
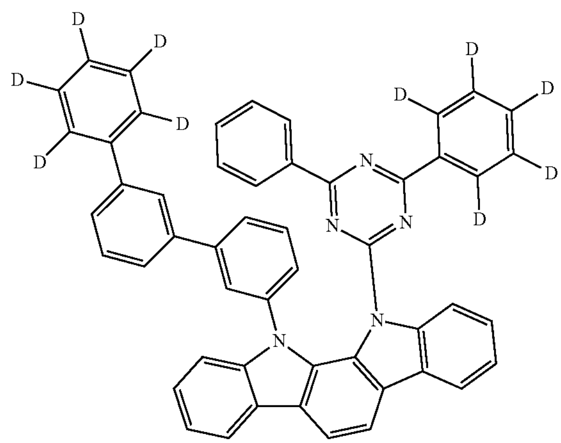
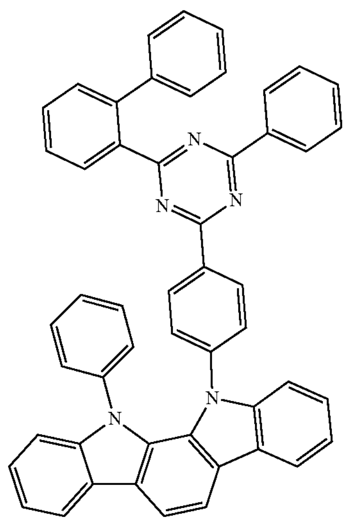
-continued
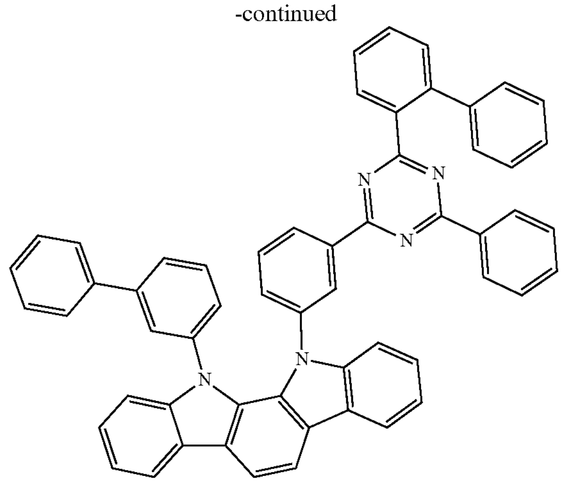
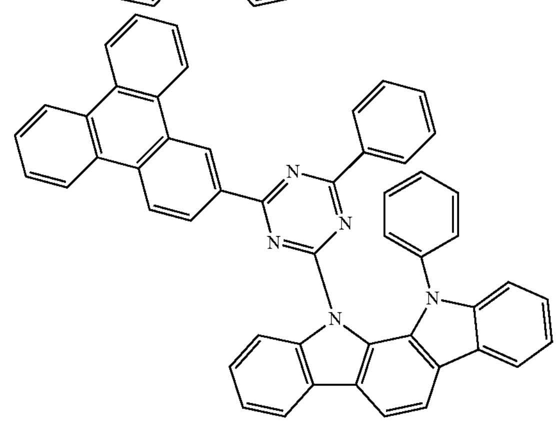
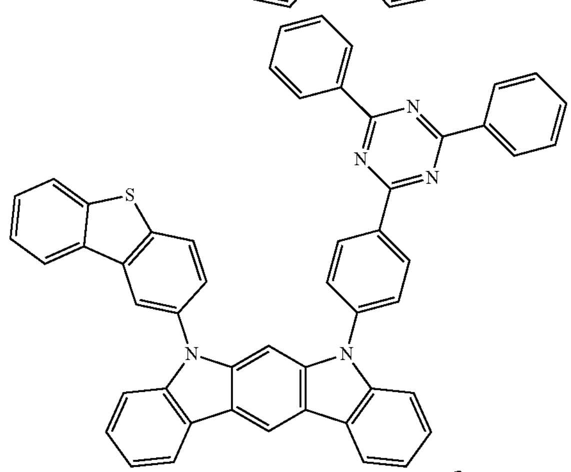
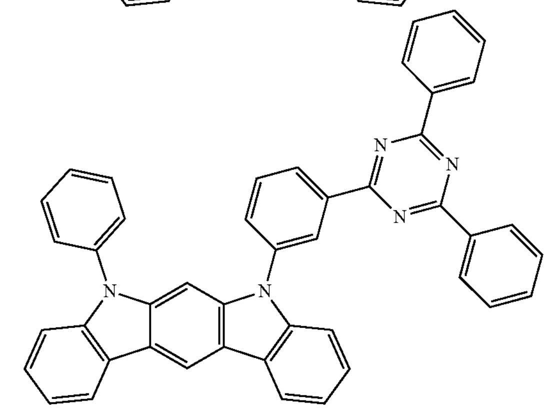

-continued
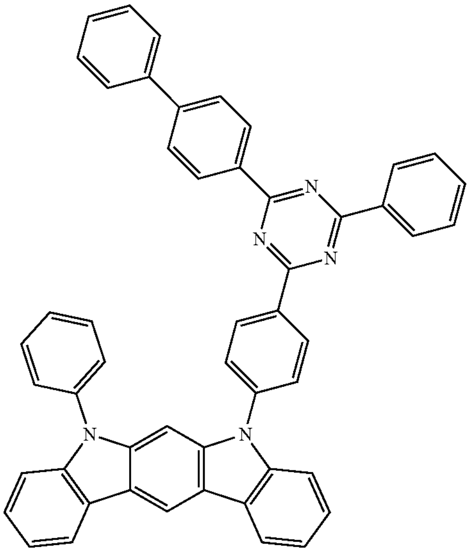
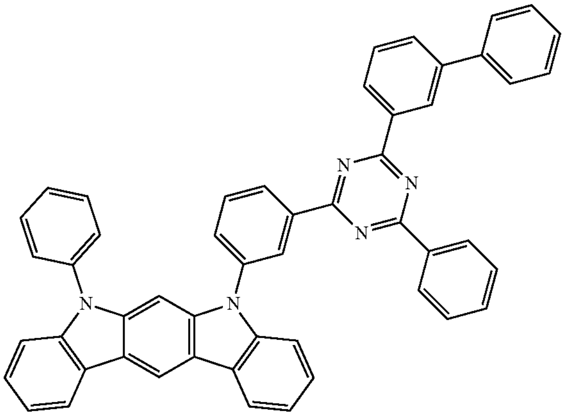
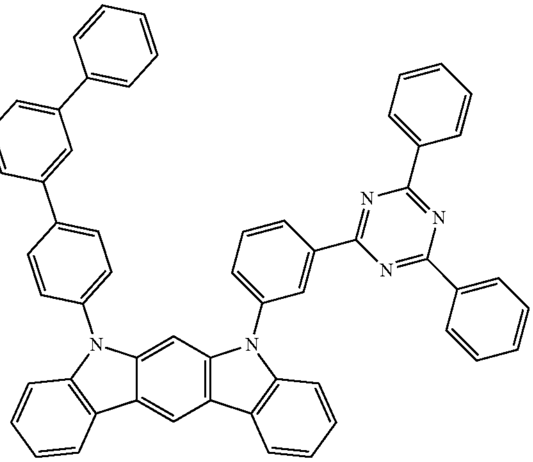
-continued
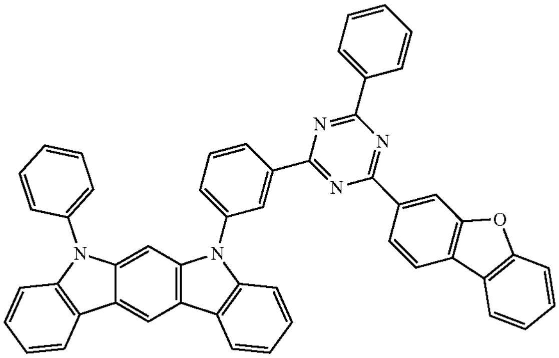
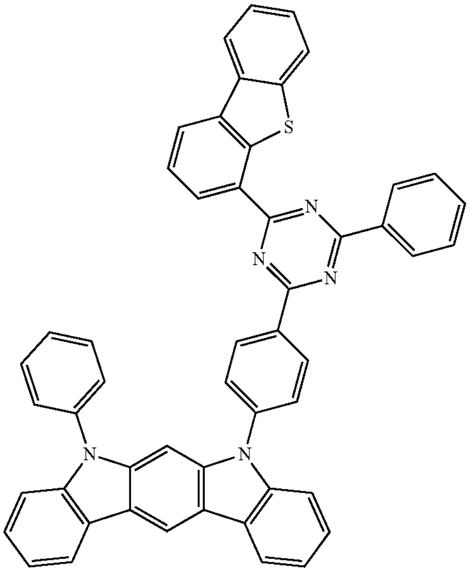
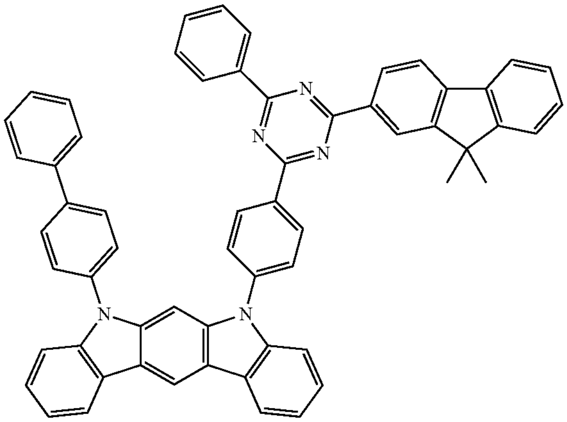

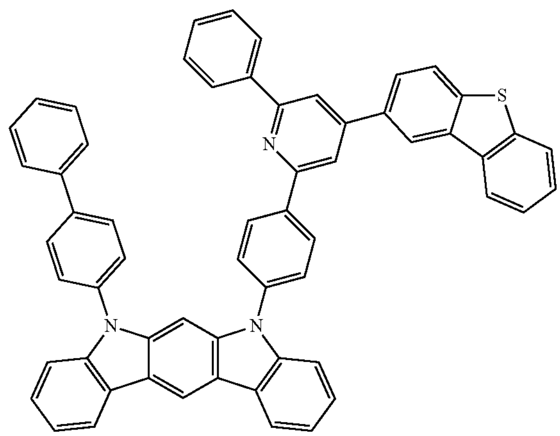
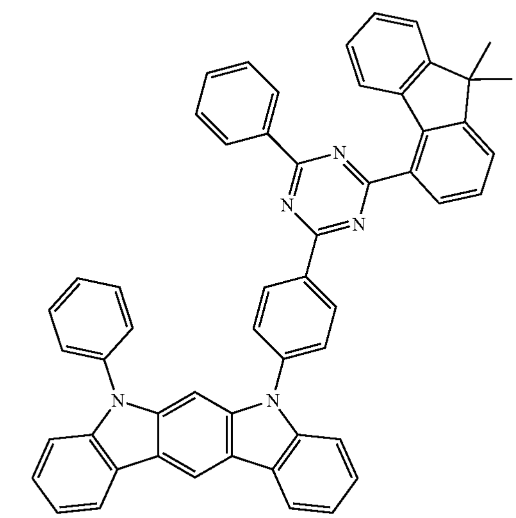
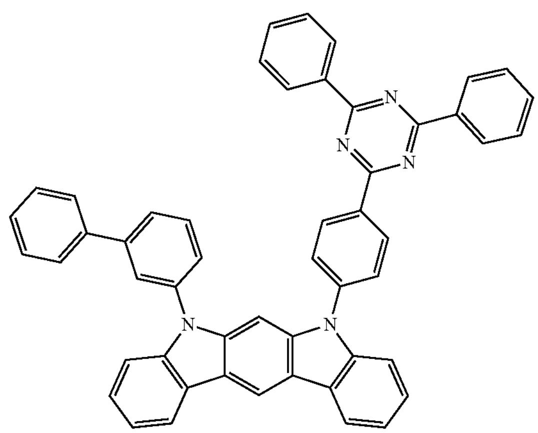
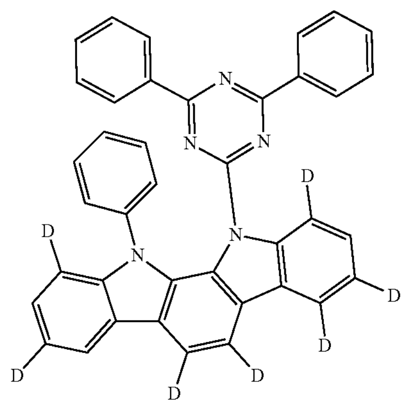
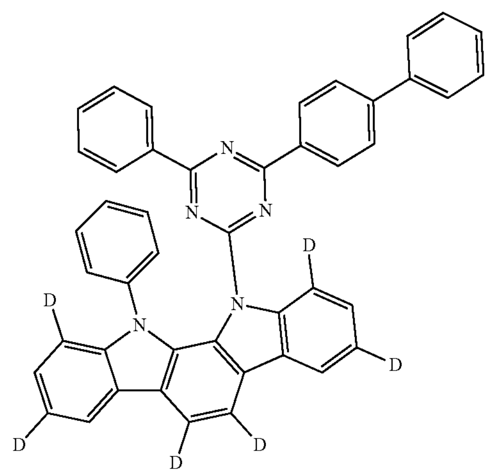
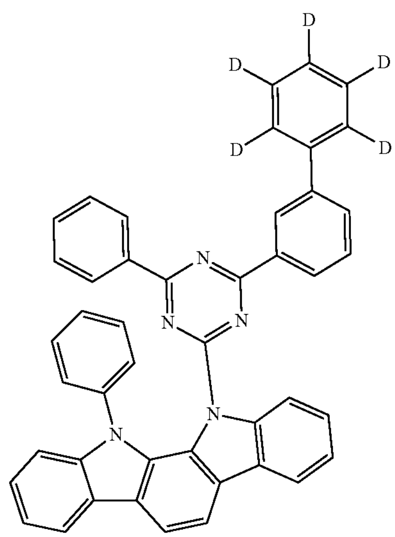

-continued
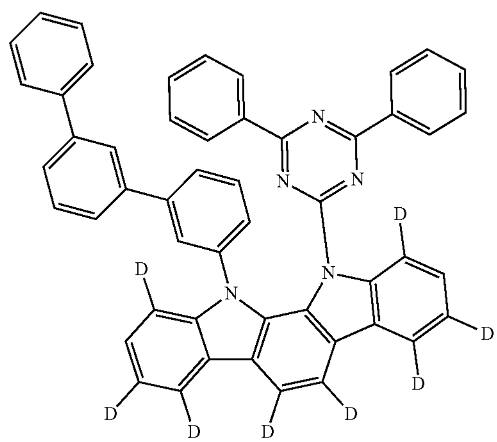
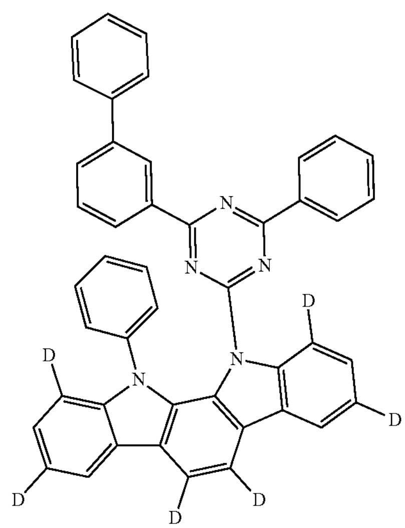
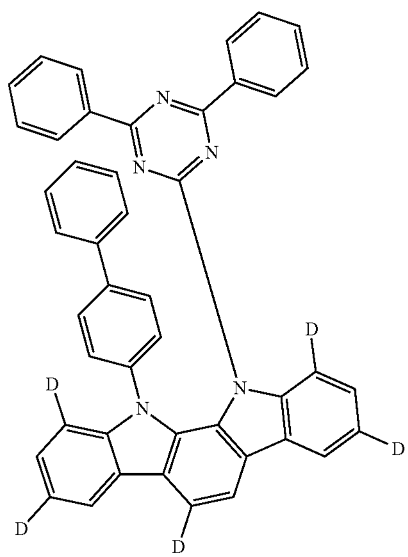
-continued
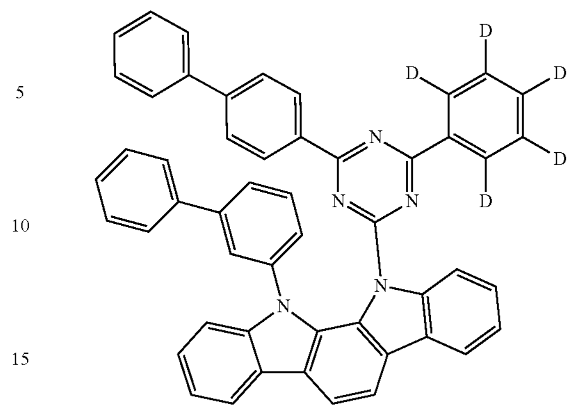
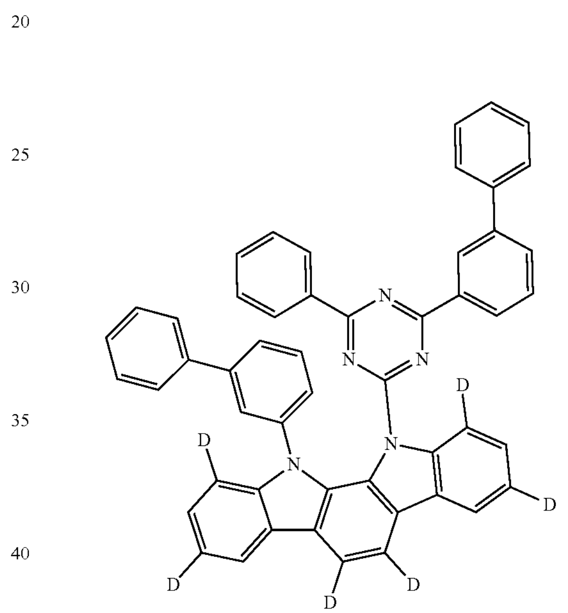
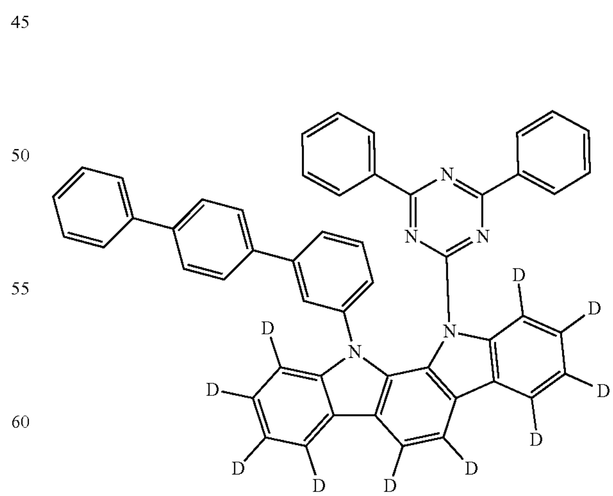

-continued
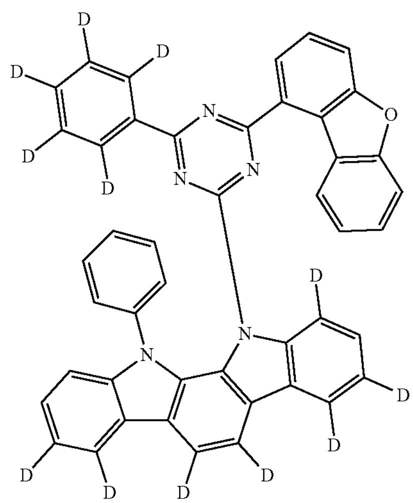
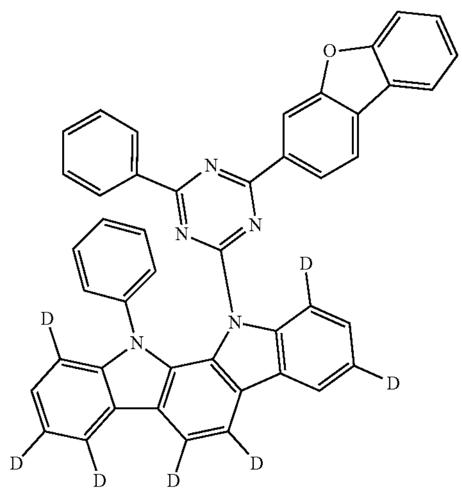
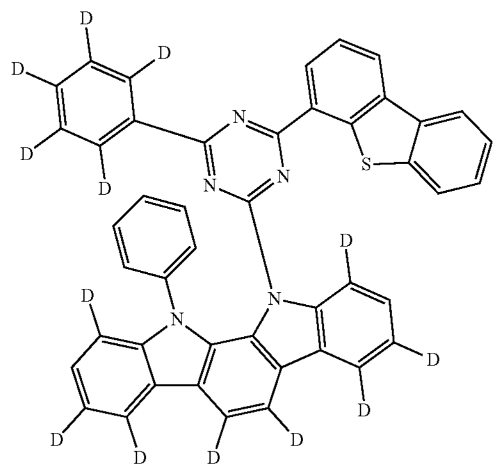
-continued
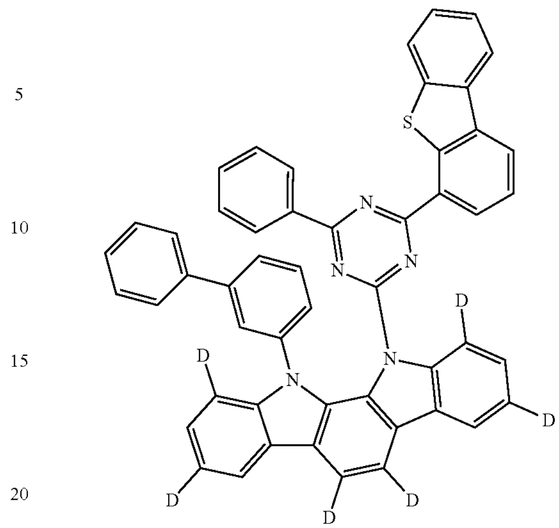
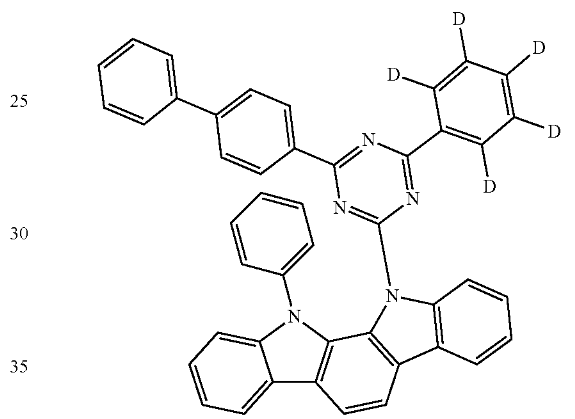
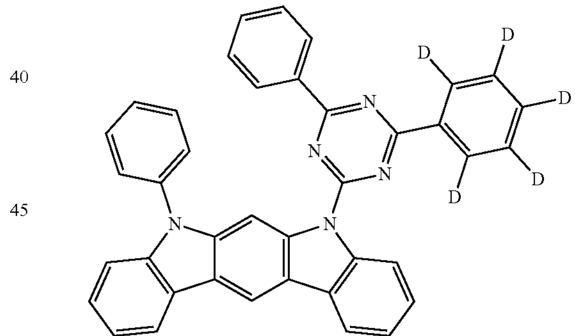
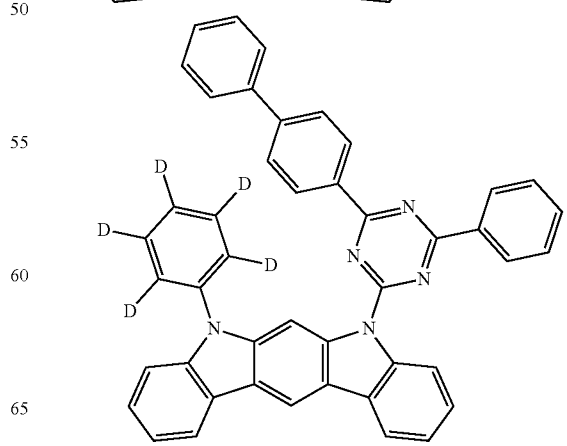

-continued
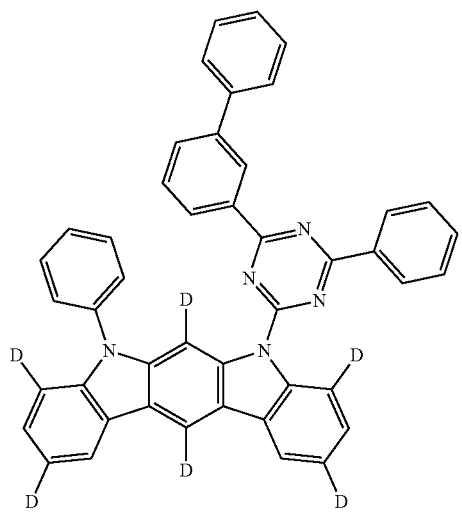
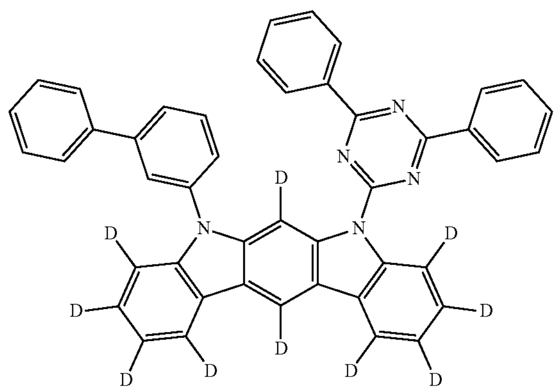
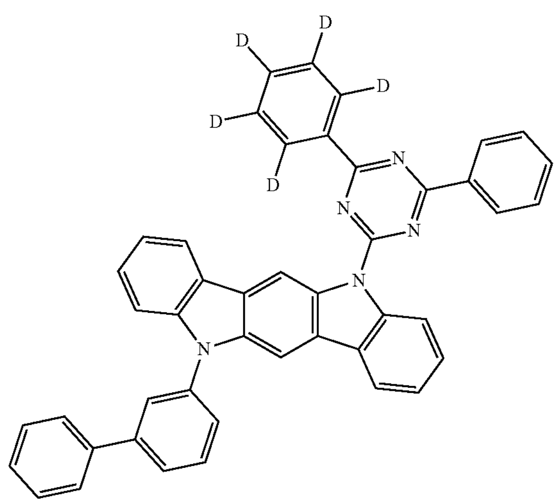
-continued
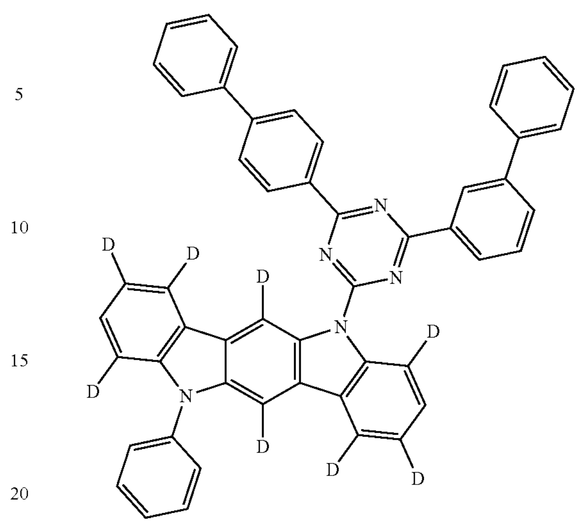
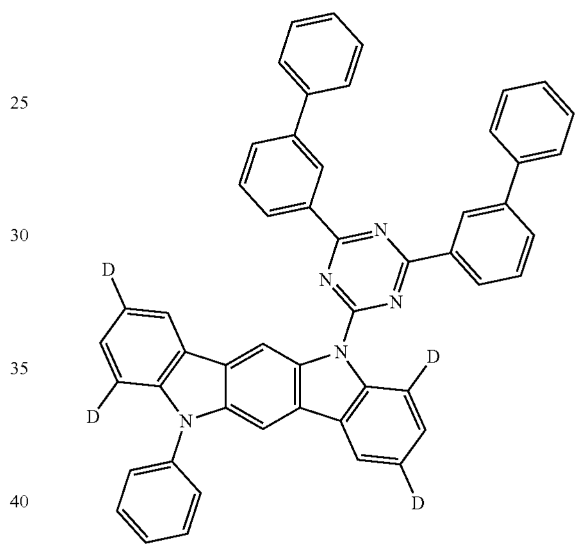
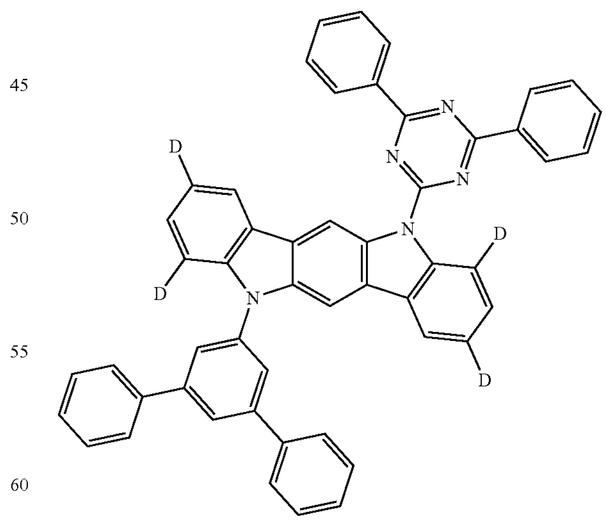
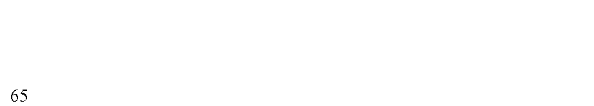

-continued
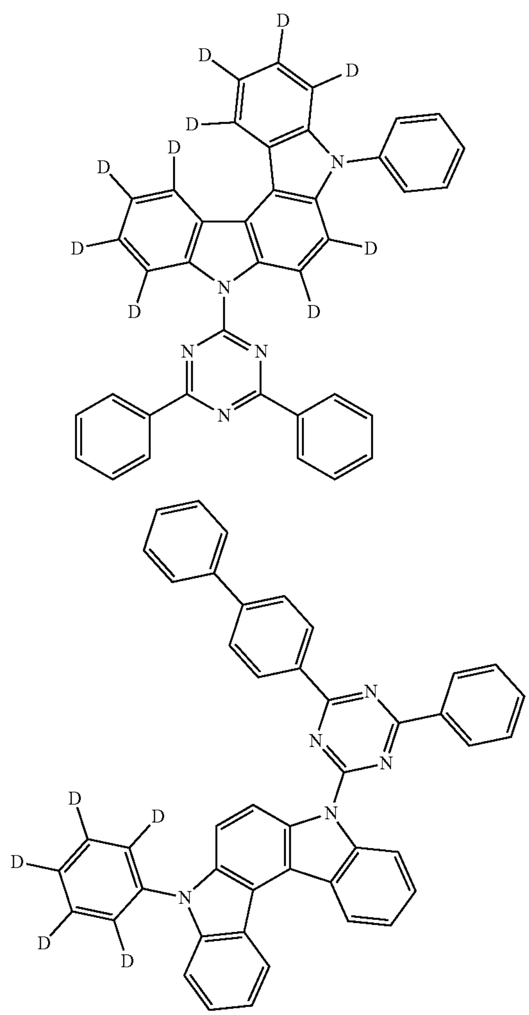
-continued
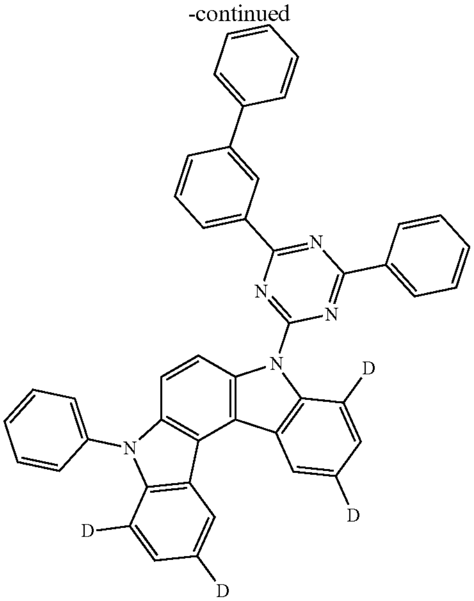
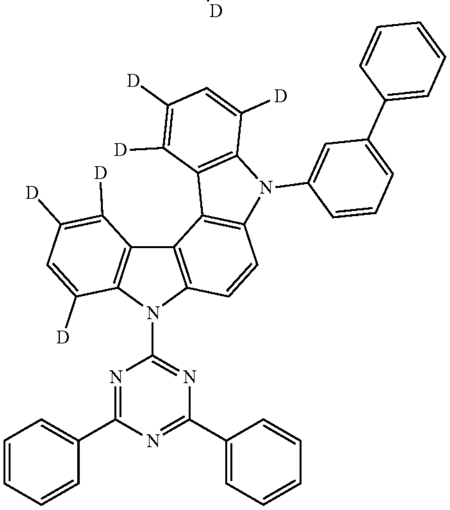
* * * * *